US011845761B2

(12) United States Patent
Feng et al.

(10) Patent No.: US 11,845,761 B2
(45) Date of Patent: Dec. 19, 2023

(54) TRICYCLIC PYRIDONES AND PYRIMIDONES

(71) Applicant: Erasca, Inc., San Diego, CA (US)

(72) Inventors: Jun Feng, San Diego, CA (US); Jean-Michel Vernier, San Diego, CA (US); Marcos Gonzalez-Lopez, San Diego, CA (US); Benjamin Jones, San Diego, CA (US); Nicholas A. Isley, San Diego, CA (US); Ping Chen, San Diego, CA (US)

(73) Assignee: Erasca, Inc., San Diego, CA (US)

( * ) Notice: Subject to any disclaimer, the term of this patent is extended or adjusted under 35 U.S.C. 154(b) by 0 days.

(21) Appl. No.: 18/063,626

(22) Filed: Dec. 8, 2022

(65) Prior Publication Data

US 2023/0159563 A1 May 25, 2023

Related U.S. Application Data

(63) Continuation of application No. 17/556,498, filed on Dec. 20, 2021, which is a continuation of application No. PCT/US2021/064356, filed on Dec. 20, 2021.

(60) Provisional application No. 63/211,549, filed on Jun. 16, 2021, provisional application No. 63/210,986, filed on Jun. 15, 2021, provisional application No. 63/259,894, filed on Dec. 18, 2020.

(51) Int. Cl.
*C07D 513/06* (2006.01)
*C07D 513/20* (2006.01)
*C07D 519/00* (2006.01)
*A61P 35/00* (2006.01)

(52) U.S. Cl.
CPC ............ *C07D 513/06* (2013.01); *A61P 35/00* (2018.01); *C07D 513/20* (2013.01); *C07D 519/00* (2013.01)

(58) Field of Classification Search
CPC .. C07D 513/06; C07D 513/20; C07D 519/00; A61P 35/00
See application file for complete search history.

(56) References Cited

U.S. PATENT DOCUMENTS

| | | | |
|---|---|---|---|
| 10,414,757 | B2 | 9/2019 | Li et al. |
| 10,633,381 | B2 | 4/2020 | Blake et al. |
| 11,008,334 | B2 | 5/2021 | Ostrem et al. |
| 2019/0233440 | A1 | 8/2019 | Planken et al. |
| 2019/0270743 | A1 | 9/2019 | Marx et al. |
| 2019/0284144 | A1 | 9/2019 | Li et al. |
| 2020/0331911 | A1 | 10/2020 | Marx et al. |
| 2021/0122764 | A1 | 4/2021 | Bharathan et al. |
| 2021/0130303 | A1 | 5/2021 | Koltun et al. |
| 2021/0130326 | A1 | 5/2021 | Aggen et al. |
| 2021/0130369 | A1 | 5/2021 | Koltun et al. |
| 2021/0230162 | A1 | 7/2021 | Zhao et al. |
| 2021/0355141 | A1 | 11/2021 | Hoang et al. |

FOREIGN PATENT DOCUMENTS

| | | | |
|---|---|---|---|
| CN | 110256421 | A1 | 9/2019 |
| CN | 111484477 | A1 | 8/2020 |
| CN | 112047937 | A1 | 12/2020 |
| CN | 112047948 | A1 | 12/2020 |
| CN | 112110918 | A1 | 12/2020 |
| CN | 112159405 | A1 | 1/2021 |
| CN | 112174950 | A1 | 1/2021 |
| CN | 112225734 | A1 | 1/2021 |
| CN | 112300153 | A1 | 2/2021 |
| CN | 112430234 | A1 | 3/2021 |
| CN | 112442029 | A1 | 3/2021 |
| CN | 112552295 | A1 | 3/2021 |
| CN | 112574199 | A1 | 3/2021 |
| CN | 112574224 | A1 | 3/2021 |
| CN | 112694475 | A1 | 4/2021 |
| CN | 112707905 | A1 | 4/2021 |
| CN | 112745335 | A1 | 5/2021 |
| CN | 112778284 | A1 | 5/2021 |
| CN | 112830928 | A1 | 5/2021 |
| CN | 112851663 | A1 | 5/2021 |
| CN | 112920183 | A1 | 6/2021 |
| CN | 113004269 | A1 | 6/2021 |
| CN | 113045565 | A1 | 6/2021 |
| CN | 113045570 | A1 | 6/2021 |
| CN | 113061132 | A1 | 7/2021 |
| CN | 113105448 | A1 | 7/2021 |
| CN | 113321654 | A1 | 8/2021 |
| CN | 113527293 | A1 | 10/2021 |
| CN | 113527294 | A1 | 10/2021 |
| CN | 113563323 | A1 | 10/2021 |
| CN | 113929681 | A1 | 1/2022 |
| CN | 113980032 | A1 | 1/2022 |
| CN | 113999226 | A1 | 2/2022 |
| CN | 114057743 | A1 | 2/2022 |
| CN | 114057744 | A1 | 2/2022 |
| CN | 114380827 | A1 | 4/2022 |
| CN | 2022083616 | A1 | 4/2022 |
| CN | 114621244 | A1 | 6/2022 |
| CN | 115073450 | A1 | 9/2022 |

(Continued)

OTHER PUBLICATIONS

Hallin et al. "Insight Towards Therapeutic Susceptibility of KRAS Mutant Cancers From MRTX1257, a Novel KRAS G12C Mutant-Selective Small Molecule Inhibitor" AACR Meeting Mar. 29-Apr. 3, 2019 Atlanta Georgia. Abstract LB-271.
Hallin et al. "Insight Towards Therapeutic Susceptibility of KRAS Mutant Cancers from MRTX1257: A Prototype Selective Inhibitor of KRAS G12C" AACR Meeting Mar. 29-Apr. 3, 2019 Atlanta Georgia. Abstract B23.
Fell et al. "Discovery of Tetrahydropyridopyrimidines as Irreversible Covalent Inhibitors of KRAS-G12C with In Vivo Activity" Med. Chem. Lett. 2018, 9(12), 1230-1234.

(Continued)

*Primary Examiner* — John M Mauro

(57) ABSTRACT

Compounds with KRAS G12C inhibitory active are disclosed and methods of using the same to treat a cancer comprising a K-Ras G12C mutation.

30 Claims, No Drawings

Specification includes a Sequence Listing.

(56) References Cited

FOREIGN PATENT DOCUMENTS

| | | | |
|---|---|---|---|
| WO | 2014152588 | A1 | 9/2014 |
| WO | 2015054572 | A1 | 4/2015 |
| WO | 2016049524 | A1 | 3/2016 |
| WO | 2016049565 | A1 | 3/2016 |
| WO | 2016049568 | A1 | 3/2016 |
| WO | 2016164675 | A1 | 10/2016 |
| WO | 2016168540 | A1 | 10/2016 |
| WO | 2017015562 | A1 | 1/2017 |
| WO | 2017058728 | A1 | 4/2017 |
| WO | 2017058768 | A1 | 4/2017 |
| WO | 2017058792 | A1 | 4/2017 |
| WO | 2017058805 | A1 | 4/2017 |
| WO | 2017058807 | A1 | 4/2017 |
| WO | 2017058902 | A1 | 4/2017 |
| WO | 2017058915 | A1 | 4/2017 |
| WO | 2017070256 | A2 | 4/2017 |
| WO | 2017087528 | A1 | 5/2017 |
| WO | 2017100546 | A1 | 6/2017 |
| WO | 2017172979 | A1 | 10/2017 |
| WO | 2017201161 | A1 | 11/2017 |
| WO | 2018064510 | A1 | 4/2018 |
| WO | 2018068017 | A1 | 4/2018 |
| WO | 2018119183 | A3 | 6/2018 |
| WO | 2018140512 | A1 | 8/2018 |
| WO | 2018140513 | A1 | 8/2018 |
| WO | 2018140514 | A1 | 8/2018 |
| WO | 2018140598 | A1 | 8/2018 |
| WO | 2018140599 | A1 | 8/2018 |
| WO | 2018140600 | A1 | 8/2018 |
| WO | 2018206539 | A1 | 11/2018 |
| WO | 2018217651 | A1 | 11/2018 |
| WO | 2018218069 | A1 | 11/2018 |
| WO | 2018218070 | A2 | 11/2018 |
| WO | 2018218071 | A1 | 11/2018 |
| WO | 2019051291 | A1 | 3/2019 |
| WO | 2019099524 | A1 | 5/2019 |
| WO | 2019110751 | A1 | 6/2019 |
| WO | 2019141250 | A1 | 7/2019 |
| WO | 2019155399 | A1 | 8/2019 |
| WO | 2019213516 | A1 | 11/2019 |
| WO | 2019215203 | A1 | 11/2019 |
| WO | 2019217307 | A1 | 11/2019 |
| WO | 2020027083 | A1 | 2/2020 |
| WO | 2020027084 | A1 | 2/2020 |
| WO | 2020028706 | A1 | 2/2020 |
| WO | 2020035031 | A1 | 2/2020 |
| WO | 2020047192 | A1 | 3/2020 |
| WO | 2020068867 | A1 | 4/2020 |
| WO | 2020068873 | A1 | 4/2020 |
| WO | 2020086739 | A1 | 4/2020 |
| WO | 2020097537 | A1 | 5/2020 |
| WO | 2020106640 | A1 | 5/2020 |
| WO | 2020118066 | A1 | 6/2020 |
| WO | 2020165732 | A1 | 8/2020 |
| WO | 2020178282 | A1 | 9/2020 |
| WO | 2020233592 | A1 | 11/2020 |
| WO | 2020234103 | A1 | 11/2020 |
| WO | 2020236940 | A1 | 11/2020 |
| WO | 2020238791 | A1 | 12/2020 |
| WO | 2020239077 | A1 | 12/2020 |
| WO | 2020239123 | A1 | 12/2020 |
| WO | 2021023247 | A1 | 2/2021 |
| WO | 2021027911 | A1 | 2/2021 |
| WO | 2021027943 | A1 | 2/2021 |
| WO | 2021055728 | A1 | 3/2021 |
| WO | 2021068898 | A1 | 4/2021 |
| WO | 2021081212 | A1 | 4/2021 |
| WO | 2021084765 | A1 | 5/2021 |
| WO | 2021085653 | A1 | 5/2021 |
| WO | 2021088938 | A1 | 5/2021 |
| WO | 2021093758 | A1 | 5/2021 |
| WO | 2021097212 | A1 | 5/2021 |
| WO | 2021098859 | A1 | 5/2021 |
| WO | 2021083167 | A1 | 6/2021 |
| WO | 2021104431 | A1 | 6/2021 |
| WO | 2021106230 | A1 | 6/2021 |
| WO | 2021118877 | A1 | 6/2021 |
| WO | 2021120045 | A1 | 6/2021 |
| WO | 2021120890 | A1 | 6/2021 |
| WO | 2021121330 | A1 | 6/2021 |
| WO | 2021121367 | A1 | 6/2021 |
| WO | 2021121371 | A1 | 6/2021 |
| WO | 2021139748 | A1 | 7/2021 |
| WO | 2021143693 | A1 | 7/2021 |
| WO | 2021147967 | A1 | 7/2021 |
| WO | 2021152149 | A1 | 8/2021 |
| WO | 2021155716 | A1 | 8/2021 |
| WO | 2021165456 | A1 | 8/2021 |
| WO | 2021168193 | A1 | 8/2021 |
| WO | 2021169963 | A1 | 9/2021 |
| WO | 2021169990 | A1 | 9/2021 |
| WO | 2021175199 | A1 | 9/2021 |
| WO | 2021180181 | A1 | 9/2021 |
| WO | 2021185233 | A1 | 9/2021 |
| WO | 2021190467 | A1 | 9/2021 |
| WO | 2021211864 | A1 | 10/2021 |
| WO | 2021216770 | A1 | 10/2021 |
| WO | 2021217019 | A1 | 10/2021 |
| WO | 2021219072 | A1 | 11/2021 |
| WO | 2021219090 | A1 | 11/2021 |
| WO | 2021228161 | A1 | 11/2021 |
| WO | 2021231526 | A1 | 11/2021 |
| WO | 2021239058 | A1 | 12/2021 |
| WO | 2021244603 | A1 | 12/2021 |
| WO | 2021245051 | A1 | 12/2021 |
| WO | 2021245055 | A1 | 12/2021 |
| WO | 2021248079 | A1 | 12/2021 |
| WO | 2021248082 | A1 | 12/2021 |
| WO | 2021248083 | A1 | 12/2021 |
| WO | 2021248090 | A1 | 12/2021 |
| WO | 2021248095 | A1 | 12/2021 |
| WO | 2021252339 | A1 | 12/2021 |
| WO | 2021259331 | A1 | 12/2021 |
| WO | 2022028492 | A1 | 2/2022 |
| WO | 2022037560 | A1 | 2/2022 |
| WO | 2022040469 | A1 | 2/2022 |
| WO | 2022047093 | A1 | 3/2022 |
| WO | 2022056307 | A1 | 3/2022 |
| WO | 2022067462 | A1 | 4/2022 |
| WO | 2022072783 | A1 | 4/2022 |
| WO | 2022081655 | A1 | 4/2022 |
| WO | 2022083569 | A1 | 4/2022 |
| WO | 2022087371 | A1 | 4/2022 |
| WO | 2022087375 | A1 | 4/2022 |
| WO | 2022087624 | A1 | 4/2022 |
| WO | 2022089604 | A1 | 5/2022 |
| WO | 2022093856 | A1 | 5/2022 |
| WO | 2022109485 | A1 | 5/2022 |
| WO | 2022109487 | A1 | 5/2022 |
| WO | 2022111527 | A1 | 6/2022 |
| WO | 2022111644 | A1 | 6/2022 |
| WO | 2022115439 | A1 | 6/2022 |
| WO | 2022117748 | A1 | 6/2022 |
| WO | 2022161489 | A1 | 8/2022 |
| WO | 2022193982 | A1 | 9/2022 |
| WO | 2022198904 | A1 | 9/2022 |
| WO | 2022221528 | A1 | 10/2022 |
| WO | 2022222871 | A1 | 10/2022 |
| WO | 2022223037 | A1 | 10/2022 |
| WO | 2022232318 | A1 | 11/2022 |
| WO | 2022232320 | A1 | 11/2022 |
| WO | 2022251576 | A1 | 12/2022 |

OTHER PUBLICATIONS

Marx et al. "Structure-Based Drug Discovery of MRTX1257, a Selective, Covalent KRAS G12C Inhibitor with Oral Activity in Animal Models of Cancer" Mol. Cancer Res. 2020, 18 (5_Supplement): B30.

Hallin et al. "The KRASG12C Inhibitor, MRTX849, Provides Insight Toward Therapeutic Susceptibility of KRAS Mutant Cancers in Mouse Models and Patients" Cancer Discov., 2020, 10(1), 54-71.

(56) References Cited

OTHER PUBLICATIONS

Kettle J.G.; Cassar, D.J. "Covalent inhibitors of the GTPase KRASG12C: a review of the patent literature" *Expert Opinion on Therapeutic Patents* 2020, 30(2), 103-120 DOI: 10.1080/13543776.2020.1709443.
Nnadi et al. "Novel K-Ras G12C Switch-II Covalent Binders Destabilize Ras and Accelerate Nucleotide Exchange;" J. Chem. Inf. Model. 2018; 58, 464-471.
Briere et al. "The KRASG12C Inhibitor MRTX849 Reconditions the Tumor Immune Microenvironment and Leads to Durable Complete Responses in Combination with Anti-PD-1 Therapy in a Syngeneic Mouse Model" AACR Meeting Mar. 29-Apr. 3, 2019 Atlanta Georgia. Abstract LB-C09.
Adrian Gill "Discovery of Small Molecule Inhibitors of Oncogenic Mutants of Ras," ACS Meeting Mar. 31-Apr. 4, 2019, Orlando, Florida.
Wang, Gena "Deep dive on KRAS G12C inhibitor—another drug class on the horizon" Barclays US, Feb. 5, 2019.
Lanman, B. "Discovery of AMG 510, a First-in-Human Covalent Inhibitor of KRASG12C for the Treatment of Solid Tumors" Presentation at AACR Annual Meeting, Atlanta, GA Apr. 2, 2019.
Lipford, J.R., "Pre-Clinical Development of AMG 510: the First Inhibitor of KRASG12C in Clinical Testing" Presentation at AACR, Mar. 31, 2018.
Lanman et al., "Discovery of a Covalent Inhibitor of KRASG12C (AMG 510) for the Treatment of Solid Tumors" J. Med. Chem. Dec. 10, 2019, Accepted Manuscript.
Reese at al., "Advancing a Portfolio of Novel, High-Potential Cancer Therapies" Presentation at ASCO, Jun. 3, 2019.
FDA, "NDA/BLA Multi-disciplinary Review and Evaluation {NDA 214665}: LUMAKRASTM™ (sotorasib)" Mar. 28, 2021.
Mirati Therapeutics, "Targeting the genetic and immunological drivers of cancer" Presentation at investor event, Sep. 20, 2021.
Sabari, et al. "Activity of Adagrasib (MRTX849) in Patients with $KRAS^{G12}$c-Mutated NSCLC and Active, Untreated CNS Metastases in the KRYSTAL-1 Trial" Presentation at ASCO, Jun. 6, 2022.
CAS No. 2206736-04-09.
CAS No. 2326521-71-3.

SEQUENCE LISTING

```
Sequence total quantity: 5
SEQ ID NO: 1          moltype = AA  length = 169
FEATURE               Location/Qualifiers
REGION                1..169
                      note = Synthetic polypeptide
source                1..169
                      mol_type = protein
                      organism = synthetic construct
SEQUENCE: 1
MTEYKLVVVG AGGVGKSALT IQLIQNHFVD EYDPTIEDSY RKQVVIDGET CLLDILDTAG  60
QEEYSAMRDQ YMRTGEGFLC VFAINNTKSF EDIHHYREQI KRVKDSEDVP MVLVGNKCDL  120
PSRTVDTKQA QDLARSYGIP FIETSAKTRQ GVDDAFYTLV REIRKHKEK             169

SEQ ID NO: 2          moltype = AA  length = 188
```

-continued

```
FEATURE                Location/Qualifiers
REGION                 1..188
                       note = Synthetic polypeptide
source                 1..188
                       mol_type = protein
                       organism = synthetic construct
SEQUENCE: 2
MTEYKLVVVG AGGVGKSALT IQLIQNHFVD EYDPTIEDSY RKQVVIDGET CLLDILDTAG  60
QEEYSAMRDQ YMRTGEGFLC VFAINNTKSF EDIHHYREQI KRVKDSEDVP MVLVGNKCDL  120
PSRTVDTKQA QDLARSYGIP FIETSAKTRQ GVDDAFYTLV REIRKHKEKM SKDGKKKKKK  180
SKTKCVIM                                                          188

SEQ ID NO: 3           moltype = AA  length = 188
FEATURE                Location/Qualifiers
REGION                 1..188
                       note = Synthetic polypeptide
source                 1..188
                       mol_type = protein
                       organism = synthetic construct
SEQUENCE: 3
MTEYKLVVVG AGGVGKSALT IQLIQNHFVD EYDPTIEDSY RKQVVIDGET CLLDILDTAG  60
QEEYSAMRDQ YMRTGEGFLC VFAINNTKSF EDIHHYREQI KRVKDSEDVP MVLVGNKCDL  120
PSRTVDTKQA QDLARSYGIP FIETSAKTRQ GVDDAFYTLV REIRKHKEKM SKDGKKKKKK  180
SKTKCVIM                                                          188

SEQ ID NO: 4           moltype = AA  length = 188
FEATURE                Location/Qualifiers
REGION                 1..188
                       note = Synthetic polypeptide
source                 1..188
                       mol_type = protein
                       organism = synthetic construct
SEQUENCE: 4
MAHHHHHHAG GAENLYFQSM TEYKLVVVGA CGVGKSALTI QLIQNHFVDE YDPTIEDSYR  60
KQVVIDGETC LLDILDTAGQ EEYSAMRDQY MRTGEGFLCV FAINNTKSFE DIHHYREQIK  120
RVKDSEDVPM VLVGNKCDLP SRTVDTKQAQ DLARSYGIPF IETSAKTRQG VDDAFYTLVR  180
EIRKHKEK                                                          188

SEQ ID NO: 5           moltype = AA  length = 170
FEATURE                Location/Qualifiers
REGION                 1..170
                       note = Synthetic polypeptide
source                 1..170
                       mol_type = protein
                       organism = synthetic construct
SEQUENCE: 5
SMTEYKLVVV GACGVGKSAL TIQLIQNHFV DEYDPTIEDS YRKQVVIDGE TCLLDILDTA  60
GQEEYSAMRD QYMRTGEGFL CVFAINNTKS FEDIHHYREQ IKRVKDSEDV PMVLVGNKCD  120
LPSRTVDTKQ AQDLARSYGI PFIETSAKTR QGVDDAFYTL VREIRKHKEK            170
```

TRICYCLIC PYRIDONES AND PYRIMIDONES

REFERENCE TO SEQUENCE LISTING

This application incorporates by reference a Computer Readable Form (CRF) of a Sequence Listing in ASCII text format submitted with this application, entitled 055745-502C05US_SequenceListing, was created on Dec. 8, 2022, and is 8,196 bytes in size.

BACKGROUND

Embodiments herein relate to compounds and methods for the treatment of RAS-mediated disease. In particular, embodiments herein relate to compounds and methods for treating diseases such as cancer via targeting oncogenic mutants of the K-RAS isoform.

Ras proteins are small guanine nucleotide-binding proteins that act as molecular switches by cycling between active GTP-bound and inactive GDP-bound conformations. Ras signaling is regulated through a balance between activation by guanine nucleotide exchange factors (GEFs), most commonly son of sevenless (SOS), and inactivation by GTPase-activating proteins (GAPs) such as neurofibromin or p120GAP. The Ras proteins play an important role in the regulation of cell proliferation, differentiation, and survival. Dysregulation of the Ras signaling pathway is almost invariably associated with disease. Hyper-activating somatic mutations in Ras are among the most common lesions found in human cancer. Most of these mutations have been shown to decrease the sensitivity of Ras to GAP stimulation and decrease its intrinsic GTPase activity, leading to an increase in the active GTP-bound population. Although mutation of any one of the three Ras isoforms (K-Ras, N-Ras, or H-Ras) has been shown to lead to oncogenic transformation, K-Ras mutations are by far the most common in human cancer. For example, K-Ras mutations are known to be often associated with pancreatic, colorectal and non-small-cell lung carcinomas. Similarly, H-Ras mutations are common in cancers such as papillary thyroid cancer, lung cancers and skin cancers. Finally, N-Ras mutations occur frequently in hepatocellular carcinoma.

There is a need for effective Ras inhibitors, which may provide a new class of anticancer compounds. These and other advantages will be apparent to those skilled in the art based upon embodiments and disclosures herein.

SUMMARY

In some aspects, embodiments disclosed herein relate to compounds of Formula (I)

(I)

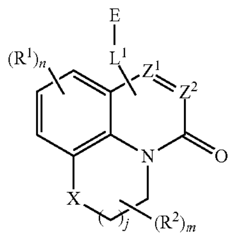

wherein:

X is $S(O)_p$, wherein p is an integer from 0 to 2;

j is an integer from 0 to 2;

$Z^1$ and $Z^2$ are independently $CR^6$ or N, with the proviso that at least one of $Z^1$ or $Z^2$ is $CR^6$ with $R^6$ being a bond to $L^1$;

$L^1$ is linking group comprising at least one nitrogen atom;

E is an electrophilic moiety, wherein E is bound to $L^1$ via the at least one nitrogen atom;

each $R^1$ is an optional substitution independently selected from the group consisting of alkyl, cyano, cycloalkyl, halo, haloalkyl, trifluoromethyl, alkoxy, aryl, heteroaryl, N-arylamino, N-aryl-N-alkylamino, aryloxy, and arylthio with the proviso that:

at least one $R^1$ is aryl, N-arylamino, N-aryl-N-alkylamino, aryloxy, arylthio, or heteroaryl, any of which is optionally substituted;

n is an integer from 1 to 3;

$R^2$ is selected from the group consisting of alkyl, alkylamino, dialkylamino alkylamidoalkyl, arylamidoalkyl, alkylsulfonamidoalkyl, arylsulfonamidoalkyl, N-alkyl aminoalkyl, N,N-dialkyl aminoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted;

m is an integer from 0 to 6;

$R^3$, $R^4$, and $R^5$ are each independently selected from the group consisting of hydrogen alkyl, halo, alkoxy, aryl, and heteroaryl, any of which are optionally substituted; and $R^6$ is selected from the group consisting of hydrogen, alkyl, haloakyl, cyano, halo, alkoxy, aryl, heteroaryl, trifluoromethyl and bond to $L^1$.

In some aspects, embodiments herein relate to compounds according to any one of the compound tables provided herein. In embodiments, the compound tables are Table 2a, Table 3, Table 4, Table 5, Table 7, Table 8, Table 11, 12, and Table 13.

In some aspects, embodiments herein relate to methods of treating cancer. In embodiments, the cancer comprises a K-RAs G12 mutation. In embodiments, the cancer is one or more of pancreatic, lung and colorectal cancer. In embodiments, the pancreatic cancer is pancreatic ductal adenocarcinoma (PDAC). In embodiments, the cancer is a CNS cancer. In embodiments, the CNS cancer comprises a primary cancer. In further embodiments, the primary cancer comprises one or more of a glioma, meningioma, medulloblastoma, ganblioglioma, schwannoma, and craniopharyngioma. In embodiments, the glioma comprises one or more of an astrocytoma, a glioblastoma, an oligodendroglioma, and a ependymoma. In embodiments, the CNS cancer comprises a metastatic or secondary cancer. In embodiments, the CNS cancer comprises a cancer metastasized from one or more of melanoma, breast cancer, colon cancer, kidney cancer, nasopharyngeal cancer, leukemia, lymphoma, myeloma, and other of unknown primary site. In embodiments, the CNS cancer comprises a RAS associated cancer.

In some aspects, the compounds used in the methods provided herein may include any of the compounds found in Table 2a, Table 3, Table 4, Table 5, Table 7, Table 8, Table 11, 12, and Table 13

DETAILED DESCRIPTION

I. General

Disclosed herein are potent and selective tricyclic quinazoline-2-ones compounds, which have been found to be useful as inhibitors of oncogenic mutants of RAS proteins. Among various advantages, the compounds disclosed herein are selective for oncogenic RAS mutants over wild-type RAS proteins. Further, compounds disclosed herein may exhibit selectivity for oncogenic mutants of K-RAS over other mutated K-RAS proteins, as well as mutants of the N-RAS and H-RAS isoforms. In particular, the compounds disclosed herein may exhibit selectivity for K-RAS, N-RAS, and H-RAS mutants having a common G12C mutation. Also disclosed herein are pharmaceutical compositions comprising these compounds, and their application in the treatment of disease, such as cancer. Methods of inhibition of oncogenic mutant K-RAS, N-RAS, and H-RAS activity are also provided, as well as methods for the treatment of oncogenic mutant RAS-mediated diseases, especially those involving elevated levels of oncogenic mutated RAS, in particular cancer. Accordingly, disclosed herein are uses of and methods of using the compounds described herein to treat one or more of the cancers described herein.

Disclosed herein is a class of compounds useful in treating oncogenic RAS-mediated disorders and conditions, defined by structural Formula (I):

(I)

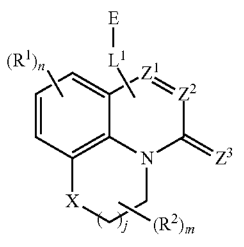

wherein:

X is $S(O)_p$, wherein p is an integer from 0 to 2;

j is an integer from 0 to 2;

$Z^1$ and $Z^2$ are independently $CR^6$ or N, with the proviso that at least one of $Z^1$ or $Z^2$ is $CR^6$ with $R^6$ being a bond to $L^1$; $Z^3$ is O;

$L^1$ is linking group comprising at least one nitrogen atom;

E is an electrophilic moiety, wherein E is bound to $L^1$ via the at least one nitrogen atom;

each $R^1$ is an optional substitution independently selected from the group consisting of alkyl, cyano, cycloalkyl, halo, haloalkyl, trifluoromethyl, alkoxy, aryl, heteroaryl, N-arylamino, N-aryl-N-alkylamino, aryloxy, and arylthio with the proviso that:

at least one $R^1$ is aryl, N-arylamino, N-aryl-N-alkylamino, aryloxy, arylthio, or heteroaryl, any of which is optionally substituted;

n is an integer from 1 to 3;

$R^2$ is selected from the group consisting of alkyl, alkylamino, alkylamidoalkyl, arylamidoalkyl, alkylsulfonamidoalkyl, arylsulfonamidoalkyl, N-alkyl aminoalkyl, N,N-dialkyl aminoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted;

m is an integer from 0 to 6;

$R^3$, $R^4$, and $R^5$ are each independently selected from the group consisting of hydrogen alkyl, halo, alkoxy, aryl, and heteroaryl, any of which are optionally substituted; and $R^6$ is selected from the group consisting of hydrogen, alkyl, haloakyl, cyano, halo, alkoxy, aryl, heteroaryl, trifluoromethyl and bond to $L^1$.

Compounds according to the various embodiments disclosed herein possess useful oncogenic mutant RAS inhibiting or modulating activity, and may be used in the treatment or prophylaxis of a disease or condition in which oncogenic mutant RAS plays an active role. Thus, in a broad aspect, embodiments disclosed herein also provide pharmaceutical compositions comprising one or more compounds disclosed herein together with a pharmaceutically acceptable carrier, as well as methods of making and using the compounds and compositions. Embodiments disclosed herein provide methods for selectively inhibiting the RAS that are oncogenic mutants having the G12C mutation. In some embodiments, there are provided methods for treating an oncogenic mutant K-RAS-mediated disorder in a subject, comprising administering to the subject a therapeutically effective amount of a compound or pharmaceutical composition according to the various embodiments disclosed herein. Related embodiments disclose the use of the compounds disclosed herein as therapeutic agents, for example, in treating cancer and other diseases involving elevated levels of oncogenic mutant K-RAS. The various embodiments disclosed herein also contemplate the use of the compounds disclosed herein for use in the manufacture of a medicament for the treatment of a disease or condition ameliorated by the inhibition of oncogenic mutant K-RAS. In some such embodiments, the disease or condition is cancer. Each of the aforementioned methods apply equally to the similar mutation in N-RAS and H-RAS bearing the G12C mutation.

Compounds of the various embodiments disclosed herein may be selective amongst the RAS oncogenic mutant forms in various ways. For example, compounds described herein may be selective for G12C mutants of K-RAS, N-RAS, or H-RAS. In certain embodiments, compounds of the various embodiments disclosed herein may be selective for K-RAS G12C over other K-RAS mutants and Wild Type K-RAS. Likewise, compounds of various embodiments disclosed herein may be selective for N-RAS and H-RAS bearing the same G12C mutation. Some embodiments relate to the use of the compounds described herein to treat cell proliferative disorders, such as cancer, of the central nervous system (CNS). CNS cancer can include any cancer of the CNS including cancer of the brain, spinal cord and nerves. Such CNS cancers can include, for example, primary cancers (e.g., those that start in the brain) and secondary or metastatic CNS cancers (those that do not start in the CNS but metastasize to the CNS). Any CNS cancer is contemplated including without limitation, for example, gliomas (including astrocytomas and glioblastomas, oligodendrogliomas, ependymomas), meningiomas, medulloblastomas, ganbliogliomas, schwannomas, and craniopharyngiomas. Any metastatic CNS cancer is contemplated, including without limitation, a cancer metastasized to the CNS via metastases of melanoma, breast cancer, colon cancer, kidney cancer, nasopharyngeal cancer, lymphoma, myeloma, leukemia, and other cancers of unknown primary site.

The various embodiments disclosed herein also relate to methods of inhibiting at least one RAS function comprising the step of contacting an oncogenic mutant RAS with a compound of Formula I or any of the compounds from the tables, as described herein. The cell phenotype, cell proliferation, activity of the mutant RAS, change in biochemical output produced by active mutant RAS, expression of mutant RAS, or binding of mutant RAS with a natural binding partner may be affected. Such methods may be embrace modes of treatment of disease, biological assays, cellular assays, biochemical assays, or the like.

IV. Definitions

A. General Definitions

As used herein, the terms below have the meanings indicated.

When ranges of number values are disclosed, and the notation "from $n_1$ . . . to $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 μM (micromolar)," which is intended to include 1 μM, 3 μM, and everything in between to any number of significant figures (e.g., 1.255 μM, 2.1 μM, 2.9999 μM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure, taking into account significant figures.

"A," "an," or "the" as used herein not only include aspects with one member, but also include aspects with more than one member. For instance, the singular forms "a," "an," and "the" include plural referents unless the context clearly dictates otherwise. Thus, for example, reference to "a cell" includes a plurality of such cells and reference to "the agent" includes reference to one or more agents known to those skilled in the art, and so forth.

B. Chemical Definitions

The following chemical functional group definitions are provided to give guidance in understanding their meaning and scope. Those skilled in the art will recognize that these functional groups are being used in a manner consistent with practice of the chemical arts. Any of the following chemical functional groups may be optionally substituted as defined below and each chemical functional group below may itself be an optional substitution.

The term "acyl," as used herein, alone or in combination, refers to a carbonyl (C═O) attached to an alkenyl, alkyl, aryl, cycloalkyl, heteroaryl, heterocycloalkyl, or any other moiety were the atom attached to the carbonyl is carbon. An "acetyl" group, which is a type of acyl, refers to a (—C(═O)$CH_3$) group. An "alkylcarbonyl" or "alkanoyl" group refers to an alkyl group attached to the parent molecular moiety through a carbonyl group. Examples of such groups include, without limitation, methylcarbonyl and ethylcarbonyl. Similarly, an "arylcarbonyl" or "aroyl" group refers to an aryl group attached to the parent molecular moiety through a carbonyl group. Examples of such groups include, without limitation, benzoyl and naphthoyl. Accordingly, generic examples of acyl groups include alkanoyl, aroyl, heteroaroyl, and so on. Specific examples of acyl groups include, without limitation, formyl, acetyl, acryloyl, benzoyl, trifluoroacetyl and the like.

The term "alkenyl," as used herein, alone or in combination, refers to a straight-chain or branched-chain hydrocarbon radical having one or more double bonds and containing from 2 to 20 carbon atoms. In certain embodiments, the alkenyl may comprise from 2 to 6 carbon atoms, or from 2 to 4 carbons, either of which may be referred to as "lower alkenyl." The term "alkenylene" refers to a carbon-carbon double bond system attached at two or more positions such as ethenylene (—CH═CH—). Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$, and so on up to 20 carbon atoms. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl. Alkenyl groups can be substituted or unsubstituted. Unless otherwise specified, the term "alkenyl" may include "alkenylene" groups.

The term "alkoxy," as used herein, alone or in combination, refers to an alkyl ether radical, wherein the term alkyl is as defined below. Alkoxy groups may have the general formula: alkyl-O—. As for alkyl group, alkoxy groups can have any suitable number of carbon atoms, such as $C_{1-6}$. Alkoxy groups include, for example, methoxy, ethoxy, propoxy, iso-propoxy, butoxy, 2-butoxy, iso-butoxy, sec-butoxy, tert-butoxy, pentoxy, hexoxy, and the like. The alkoxy groups can be further optionally substituted as defined herein.

The term "alkyl," as used herein, alone or in combination, (sometimes abbreviated Alk) refers to a straight-chain or branched-chain alkyl radical containing from 1 to 20 carbon atoms. In certain embodiments, the alkyl may comprise from 1 to 10 carbon atoms. In further embodiments, the alkyl may comprise from 1 to 6 carbon atoms, or from 1 to 4 carbon atoms. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc. Alkyl groups can be substituted or unsubstituted. The term "alkylene," as used herein, alone or in combination, refers to a saturated aliphatic group derived from a straight or branched chain saturated hydrocarbon attached at two or more positions, such as methylene (—$CH_2$—). Unless otherwise specified, the term "alkyl" may include "alkylene" groups. When the alkyl is methyl, it may be represented structurally as $CH_3$, Me, or just a single bond terminating with no end group substitution.

The term "alkylamino," as used herein, alone or in combination, refers to an alkyl group attached to the parent molecular moiety through an amino group. Suitable alkylamino groups may be mono- or dialkylated, forming groups such as, for example, N-methylamino (—NHMe), N-ethylamino (—NHEt), N,N-dimethylamino (—$NMe_2$), N,N-ethylmethylamino (—NMeEt) and the like. The term "aminoalkyl" refers to reverse orientation in which the amino group appears distal to the parent molecular moiety and attachment to the parent molecular moiety is through the alkyl group. For example, $NH_2(CH_2)_n$— describes an aminoalkyl group with a terminal amine at the end of an alkyl group attached to the parent molecular moiety. The two terms alkylamino and aminoalkyl can be combined to describe an "alkylaminoalkyl" group in which an alkyl group resides on a nitrogen atom distal to the parent molecular moiety, such as MeNH$(CH_2)_n$—. In a similar manner, an aryl group, as defined herein, may combine in a similar fashion providing an arylaminoalkyl group $ArNH(CH_2)_n$—. For additional clarity nomenclature may be provided where the group that is attached to nitrogen is indicated so by use of "N-" in the name, such as N-arylaminoalkyl, which is understood to mean that the aryl group is a substituent on the nitrogen atom of the aminoalkyl group, the alkyl being attached the parent molecular moiety.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (AlkS—) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like. Similarly, "arylthio" refers to arylthioether (ArS—) radical wherein the term aryl is as defined herein and wherein the sulfur may be singly or double oxidized.

The term "alkynyl," as used herein, alone or in combination, refers to a straight-chain or branched chain hydrocarbon radical having one or more triple bonds and containing from 2 to 20 carbon atoms. In certain embodiments, said alkynyl comprises from 2 to 6 carbon atoms. In further embodiments, said alkynyl comprises from 2 to 4 carbon atoms. The term "alkynylene" refers to a carbon-carbon triple bond attached at two positions such as ethynylene. Alkynyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Examples of alkynyl groups include, but are not limited to, acetylenyl, propynyl, 1-butynyl, 2-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl. Alkynyl groups can be substituted or unsubstituted. Unless otherwise specified, the term "alkynyl" may include "alkynylene" groups.

The terms "amido," as used herein, alone or in combination, refer to an amino group as described below attached to the parent molecular moiety through a carbonyl group. The term "C-amido" as used herein, alone or in combination, refers to a —C(═O)N$(R)_2$ group where is R as defined herein. The term "N-amido" as used herein, alone or in combination, refers to RC(═O)N(R')— group, with R and R' as defined herein. The term "acylamino" as used herein, alone or in combination, embraces an acyl group attached to the parent moiety through an amino group. An example of an "acylamino" group is acetylamino ($CH_3C(O)NH$—).

The term "amino," as used herein, alone or in combination, refers to —N(R)(R') or —$N^+$(R)(R')(R"), wherein R, R' and R" are independently selected from the group consisting of hydrogen, alkyl, acyl, heteroalkyl, aryl, cycloalkyl, heteroaryl, and heterocycloalkyl, any of which may themselves be optionally substituted.

The term "amino acid," as used herein, alone or in combination, means a substituent of the form —NRCH(R')C(O)OH, wherein R is typically hydrogen, but may be cyclized with N (for example, as in the case of the amino acid proline), and R' is selected from the group consisting of hydrogen, alkyl, heteroalkyl, cycloalkyl, heterocycloalkyl, aryl, heteroaryl, amino, amido, cycloalkylalkyl, heterocycloalkylalkyl, arylalkyl, heteroarylalkyl, aminoalkyl, amidoalkyl, hydroxyalkyl, thiol, thioalkyl, alkylthioalkyl, and alkylthio, any of which may be optionally substituted. The term "amino acid" includes all naturally occurring amino acids as well as synthetic analogues.

The term "aryl," as used herein, alone or in combination, means a carbocyclic aromatic system containing one, two or three rings wherein such rings may be attached together in a pendent manner or may be fused. The term "aryl" embraces aromatic radicals such as benzyl, phenyl, naphthyl, anthracenyl, phenanthryl, indanyl, indenyl, annulenyl, azulenyl, tetrahydronaphthyl, and biphenyl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl radical derived from an aryl-substituted alkanecarboxylic acid such as benzoyl, naphthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent radical $C_6H_4$— derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid (oxygen) end, and which may be optionally substituted as defined herein.

The term "O-carbamyl" as used herein, alone or in combination, refers to a —OC(O)NRR', group, with R and R' as defined herein.

The term "N-carbamyl" as used herein, alone or in combination, refers to a ROC(O)NR'— group, with R and R' as defined herein.

The term "carbonyl," as used herein, when alone includes formyl [—C(═O)H] and in combination is a —C(═O)— group.

The term "carboxyl" or "carboxyl," as used herein, refers to —C(═O)OH, O-carboxy, C-carboxy, or the corresponding "carboxylate" anion, such as is in a carboxylic acid salt. An "O-carboxy" group refers to a RC(═O)O— group, where R is as defined herein. A "C-carboxy" group refers to a —C(═O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl radical wherein each cyclic moiety contains from 3 to 12 carbon atom ring members and which may optionally be a benzo fused ring system which is optionally substituted as defined herein. In some embodiments, a cycloalkyl may comprise from 3 to 7 carbon atoms, or from 5 to 7 carbon atoms. Examples of such cycloalkyl radicals include cyclopropyl, cyclobutyl, cyclopentyl, cyclohexyl, cycloheptyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1.1.1]pentane, camphor, adamantane, and bicyclo [3.2.1]octane.

The term "electrophilic moiety," as used herein, is used in accordance with its plain ordinary chemical meaning and refers to a chemical group that is electrophilic. Exemplary electrophilic moieties include, without limitation, unsaturated carbonyl containing compounds such as acrylamides, acrylates, unsaturated (i.e., vinyl) sulfones or phosphates, epoxides, and vinyl epoxides.

The term "ester," as used herein, alone or in combination, refers to a carboxyl group bridging two moieties linked at carbon atoms (—CRR'C(═O)OCRR'—), where each R and R' are independent and defined herein.

The term "ether," as used herein, alone or in combination, typically refers to an oxy group bridging two moieties linked at carbon atoms. "Ether" may also include polyethers, such as, for example, $—RO(CH_2)_2O(CH_2)_2O(CH_2)_2OR'$, $—RO(CH_2)_2O(CH_2)_2OR'$, $—RO(CH_2)_2OR'$, and $—RO(CH_2)_2OH$.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl, trihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene ($—CF_2—$), chloromethylene (—CHCl—) and the like.

The term "heteroalkyl," as used herein, alone or in combination, refers to a stable straight or branched chain, or cyclic hydrocarbon radical, or combinations thereof, fully saturated or containing from 1 to 3 degrees of unsaturation, consisting of the stated number of carbon atoms and from one to three heteroatoms selected from the group consisting of O, N, and S, and wherein the nitrogen and sulfur atoms may optionally be oxidized and the nitrogen heteroatom may optionally be quaternized (i.e. bond to 4 groups). The heteroatom(s) O, N and S may be placed at any interior position of the heteroalkyl group. Up to two heteroatoms may be consecutive, such as, for example, $—CH_2NHOCH_3$. The term heteroalkyl may include ethers.

The term "heteroaryl," as used herein, alone or in combination, refers to 3 to 7 membered unsaturated heteromonocyclic rings, or fused polycyclic rings, each of which is 3 to 7 membered, in which at least one of the fused rings is unsaturated, wherein at least one atom is selected from the group consisting of O, S, and N. In some embodiments, a heteroaryl may comprise from 5 to 7 carbon atoms. The term also embraces fused polycyclic groups wherein heterocyclic radicals are fused with aryl radicals, wherein heteroaryl radicals are fused with other heteroaryl radicals, or wherein heteroaryl radicals are fused with cycloalkyl radicals. Non-limiting examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

Heteroaryl groups can include any number of ring atoms, such as, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted.

The heteroaryl groups can be linked via any position on the ring. For example, pyrrole includes 1-, 2- and 3-pyrrole, pyridine includes 2-, 3- and 4-pyridine, imidazole includes 1-, 2-, 4- and 5-imidazole, pyrazole includes 1-, 3-, 4- and 5-pyrazole, triazole includes 1-, 4- and 5-triazole, tetrazole includes 1- and 5-tetrazole, pyrimidine includes 2-, 4-, 5- and 6-pyrimidine, pyridazine includes 3- and 4-pyridazine, 1,2,3-triazine includes 4- and 5-triazine, 1,2,4-triazine includes 3-, 5- and 6-triazine, 1,3,5-triazine includes 2-triazine, thiophene includes 2- and 3-thiophene, furan includes 2- and 3-furan, thiazole includes 2-, 4- and 5-thiazole, isothiazole includes 3-, 4- and 5-isothiazole, oxazole includes 2-, 4- and 5-oxazole, isoxazole includes 3-, 4- and 5-isoxazole, indole includes 1-, 2- and 3-indole, isoindole includes 1- and 2-isoindole, quinoline includes 2-, 3- and 4-quinoline, isoquinoline includes 1-, 3- and 4-isoquinoline, quinazoline includes 2- and 4-quinoazoline, cinnoline includes 3- and 4-cinnoline, benzothiophene includes 2- and 3-benzothiophene, and benzofuran includes 2- and 3-benzofuran.

Some heteroaryl groups include those having from 5 to 10 ring members and from 1 to 3 ring atoms including N, O or S, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, isoxazole, indole, isoindole, quinoline, isoquinoline, quinoxaline, quinazoline, phthalazine, cinnoline, benzothiophene, and benzofuran. Other heteroaryl groups include those having from 5 to 8 ring members and from 1 to 3 heteroatoms, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, and isoxazole. Some other heteroaryl groups include those having from 9 to 12 ring members and from 1 to 3 heteroatoms, such as indole, isoindole, quinoline, isoquinoline, quinoxaline, quinazoline, phthalazine, cinnoline, benzothiophene, benzofuran and bipyridine. Still other heteroaryl groups include those having from 5 to 6 ring members and from 1 to 2 ring atoms including N, O or S, such as pyrrole, pyridine, imidazole, pyrazole, pyrazine, pyrimidine, pyridazine, thiophene, furan, thiazole, isothiazole, oxazole, and isoxazole.

The terms "heterocycloalkyl" and, interchangeably, "heterocycle," or "heterocyclyl" as used herein, alone or in combination, each refer to a saturated, partially unsaturated, or fully unsaturated monocyclic, bicyclic, or tricyclic heterocyclic radical containing at least one heteroatom as ring members, wherein each heteroatom may be independently selected from the group consisting of nitrogen, oxygen, and sulfur. In certain embodiments, a heterocycloalkyl may comprise from 1 to 4 heteroatoms as ring members. In further embodiments, a heterocycloalkyl may comprise from 1 to 2 heteroatoms ring members. In some embodiments, a heterocycloalkyl may comprise from 3 to 8 ring members in each ring. In further embodiments, a heterocycloalkyl may comprise from 3 to 7 ring members in each ring. In yet further embodiments, a heterocycloalkyl may comprise from 5 to 6 ring members in each ring. "Heterocycloalkyl" and "heterocycle" are intended to include sugars, sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycloalkyl groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihy-dropyridinyl, 1,3-dioxanyl, 1,4-dioxanyl, 1,3-dioxolanyl, epoxy, isoindolinyl, morpholinyl, piperazinyl, pyrrolidinyl, tetrahydropyridinyl, piperidinyl, thiomorpholinyl, and the like. The heterocycloalkyl groups may be optionally substituted unless specifically prohibited.

"Heterocycloalkyl" may refer to a saturated ring system having from 3 to 12 ring members and from 1 to 5 heteroatoms of N, O and S. The heteroatoms can also be oxidized, such as, but not limited to, S(O) and $S(O)_2$. Heterocycloalkyl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocycloalkyl groups, such as 1, 2, 3, 4, or 5, or 1 to 2, 1 to 3, 1 to 4, 1 to 5, 2 to 3, 2 to 4, 2 to 5, 3 to 4 or 3 to 5. The heterocycloalkyl group can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. The heterocycloalkyl group can include groups such as aziridine, azetidine, pyrrolidine, piperidine, azepane, diazepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. The heterocycloalkyl groups can also be fused to aromatic or non-aromatic ring systems to form members including, but not limited to, indoline, diazabicycloheptane, diazabicyclooctane, diazaspirooctane or diazaspirononane. Heterocycloalkyl groups can be unsubstituted or substituted. For example, heterocycloalkyl groups can be substituted with C1 6 alkyl or oxo (=O), among many others. Heterocycloalkyl groups can also include a double bond or a triple bond, such as, but not limited to dihydropyridine or 1,2,3,6-tetrahydropyridine.

The heterocycloalkyl groups can be linked via any position on the ring. For example, aziridine can be 1- or 2-aziridine, azetidine can be 1- or 2-azetidine, pyrrolidine can be 1-, 2- or 3-pyrrolidine, piperidine can be 1-, 2-, 3- or 4-piperidine, pyrazolidine can be 1-, 2-, 3-, or 4-pyrazolidine, imidazolidine can be 1-, 2-, 3- or 4-imidazolidine, piperazine can be 1-, 2-, 3- or 4-piperazine, tetrahydrofuran can be 1- or 2-tetrahydrofuran, oxazolidine can be 2-, 3-, 4- or 5-oxazolidine, isoxazolidine can be 2-, 3-, 4- or 5-isoxazolidine, thiazolidine can be 2-, 3-, 4- or 5-thiazolidine, isothiazolidine can be 2-, 3-, 4- or 5-isothiazolidine, and morpholine can be 2-, 3- or 4-morpholine.

When heterocycloalkyl includes 3 to 8 ring members and 1 to 3 heteroatoms, representative members include, but are not limited to, pyrrolidine, piperidine, tetrahydrofuran, oxane, tetrahydrothiophene, thiane, pyrazolidine, imidazolidine, piperazine, oxazolidine, isoxzoalidine, thiazolidine, isothiazolidine, morpholine, thiomorpholine, dioxane and dithiane. Heterocycloalkyl can also form a ring having 5 to 6 ring members and 1 to 2 heteroatoms, with representative members including, but not limited to, pyrrolidine, piperidine, tetrahydrofuran, tetrahydrothiophene, pyrazolidine, imidazolidine, piperazine, oxazolidine, isoxazolidine, thiazolidine, isothiazolidine, and morpholine.

The term "hydrazinyl" as used herein, alone or in combination, refers to two amino groups joined by a single bond, i.e., —N—N—. In general, the hydrazinyl group has optional substitution on at least one NH hydrogen to confer stability.

The term "hydroxamic acid" or its ester as used herein, refers to —C(O)ON(R)O(R'), wherein R and R' are as defined herein, or the corresponding "hydroxamate" anion, including any corresponding hydroxamic acid salt.

The term "hydroxy," as used herein, alone or in combination, refers to OH.

The term "hydroxyalkyl," as used herein, alone or in combination, refers to a hydroxy group attached to the parent molecular moiety through an alkyl group. "Hydroxyalkyl" or "alkylhydroxy" refers to an alkyl group, as defined above, where at least one of the hydrogen atoms is replaced with a hydroxy group. As for the alkyl group, hydroxyalkyl or alkylhydroxy groups can have any suitable number of carbon atoms, such as $C_{1-6}$. Exemplary $C_{1-4}$ hydroxyalkyl groups include, but are not limited to, hydroxymethyl, hydroxyethyl (where the hydroxy is in the 1- or 2-position), hydroxypropyl (where the hydroxy is in the 1-, 2- or 3-position), hydroxybutyl (where the hydroxy is in the 1-, 2-, 3- or 4-position), 1,2-dihydroxyethyl, and the like.

The term "imino," as used herein, alone or in combination, refers to C=NR.

The term "iminohydroxy," as used herein, alone or in combination, refers to C═N(OH) and it O-ether C═N—OR.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "linking group," as used herein refers to any nitrogen containing organic fragment that serves to connect the pyrimidine or pyridone core of the compounds disclosed herein to the electrophilic moiety E, as defined herein. Exemplary linking groups include piperazines, aminoalkyls, alkyl- or aryl-based diamines, aminocycloalkyls, amine-containing spirocyclics, any of which may be optionally substituted as defined herein. In some embodiments, linking groups may comprise the substructure L-Q-L'-E wherein Q is a monocyclic 4 to 7 membered ring or a bicyclic, bridged, or fused, or spiro 6-11 membered ring, any of which optionally include one or more nitrogen atoms, E is the electrophilic group, L is bond, $C_{1-6}$ alkylene, —O—$C_{0-5}$ alkylene, —S—$C_{0-5}$ alkylene, or —NH—$C_{0-5}$ alkylene, and for $C_{2-6}$ alkylene, —O—$C_{2-5}$ alkylene, —S—$C_{2-5}$ alkylene, and NH—$C_{2-5}$ alkylene, one carbon atom of any of the alkylene groups can optionally be replaced with O, S, or NH; and L' is bond when Q comprises a nitrogen to link to E, otherwise L' is NR, where R is hydrogen or alkyl.

The term "lower," as used herein, alone or in combination, means containing from 1 to and including 6 carbon atoms, or from 1 to 4 carbon atoms.

The term "mercaptyl" as used herein, alone or in combination, refers to an RS— group, where R is as defined herein.

The term "nitro," as used herein, alone or in combination, refers to —$NO_2$.

The terms "oxy" or "oxa," as used herein, alone or in combination, refer to —O—.

The term "oxo," as used herein, alone or in combination, refers to ═O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The term "phosphoamide" as used herein, alone or in combination, refers to a phosphate group [$(OH)_2$P(═O)O—] in which one or more of the hydroxyl groups has been replaced by nitrogen, amino, or amido.

The term "phosphonate" as used herein, alone or in combination, refers to a group of the form ROP(OR')(OR)O— wherein R and R' are selected from the group consisting of hydrogen, alkyl, acyl, heteroalkyl, aryl, cycloalkyl, heteroaryl, and heterocycloalkyl, any of which may themselves be optionally substituted. "Phosphonate" includes "phosphate [$(OH)_2$P(O)O—] and related phosphoric acid anions which may form salts.

The terms "sulfonate," "sulfonic acid," and "sulfonic," as used herein, alone or in combination, refers to the —$SO_3H$ group and its anion as the sulfonic acid is used in salt formation or sulfonate ester where OH is replaced by OR, where R is not hydrogen, but otherwise is as defined herein, and typically being alkyl or aryl.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —$S(O)_2$—.

The term "N-sulfonamido" refers to a RS(═O)$_2$NR'— group with R and R' as defined herein.

The term "S-sulfonamido" refers to a —S(═O)$_2$NRR', group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(═S)H and in combination is a —C(═S)— group.

The term "N-thiocarbamyl" refers to an ROC(═S)NR'— group, with R and R' as defined herein.

The term "O-thiocarbamyl" refers to a —OC(═S)NRR', group with R and R' as defined herein.

The term "thiocyanato" refers to a —CNS group.

The term "trihalomethanesulfonamido" refers to a $X_3$CS(═O)$_2$NR— group with X is a halogen and R as defined herein.

The term "trihalomethanesulfonyl" refers to a $X_3$CS(═O)$_2$— group where X is a halogen.

The term "trihalomethoxy" refers to a $X_3$CO— group where X is a halogen.

The term "trisubstituted silyl," as used herein, alone or in combination, refers to a silicone group substituted at its three free valences with groups as listed herein under the definition of substituted amino. Examples include trimethysilyl, tert-butyldimethylsilyl, triphenylsilyl and the like.

In embodiments of the invention, any one of the positions that is understood to have a hydrogen may also exist or understood to be isotopically enriched. In the compounds of this invention any atom not specifically designated as a particular isotope is meant to represent any stable isotope of that atom. Obtaining 100% deuteration at any relevant site of a compound in an amount of milligram or greater can be difficult. Therefore, it is understood that some percentage of hydrogen may still be present, even though a deuterium atom is specifically shown in a chemical structure. Thus, when a chemical structure contains a "D," the compound represented by the structure is deuterium-enriched at the site represented by "D." Unless otherwise stated, when a position is designated specifically as "H" or "hydrogen," the position is understood to have hydrogen at its natural abundance isotopic composition. Also unless otherwise stated, when a position is designated specifically as "D" or "deuterium," the position is understood to have deuterium at an abundance that is at least 3340 times greater than the natural abundance of deuterium, which is 0.015% (i.e., the term "D" or "deuterium" indicates at least 50.1% incorporation of deuterium). In embodiments, a benzene ring may be optionally exist as —$C_6D_5$, —$C_6DH_4$, —$C_6D_2H_3$, —$C_6D_3H_2$, and —$C_6D_4H$. In embodiments, a cyclohexyl group may optionally exist as —$C_6D_{11}$.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent. A "null" group occurring between two other group may also be understood to be a collapsing of flanking groups. For example, if in $—(CH_2)_xG^1G^2G^3$, the element $G^2$ were null, said group would become $—(CH_2)_x G^1G^3$.

The term "optionally substituted" means the anteceding group or groups may be substituted or unsubstituted. Groups constituting optional substitution may themselves be optionally substituted. For example, where an alkyl group is embraced by an optional substitution, that alkyl group itself may also be optionally substituted. When substituted, the substituents of an "optionally substituted" group may include, without limitation, one or more substituents independently selected from the following groups or a particular designated set of groups, alone or in combination: alkyl, alkenyl, alkynyl, alkanoyl, heteroalkyl, heterocycloalkyl, haloalkyl, haloalkenyl, haloalkynyl, lower perhaloalkyl, perhaloalkoxy, cycloalkyl, phenyl, aryl, aryloxy, alkoxy, haloalkoxy, oxo, acyloxy, carbonyl, carboxyl, alkylcarbonyl, carboxyester, carboxamido, cyano, hydrogen, halogen, hydroxy, amino, alkylamino, arylamino, amido, nitro, thiol, alkylthio, haloalkylthio, perhaloalkylthio, arylthio, sulfonate, sulfonic acid, trisubstituted silyl, $N_3$, SH, $SCH_3$, $C(O)CH_3$, $CO_2CH_3$, $CO_2H$, pyridinyl, thiophene, furanyl, carbamate, and urea. Particular subsets of optional substitution include, without limitation: (1) alkyl, halo, and alkoxy; (2) alkyl and halo; (3) alkyl and alkoxy; (4) alkyl, aryl, and heteroaryl; (5) halo and alkoxy; and (6) hydroxyl, alkyl, halo, alkoxy, and cyano. Where an optional substitution comprises a heteroatom-hydrogen bond (—NH—, SH, OH), further optional substitution of the heteroatom hydrogen is contemplated and includes, without limitation optional substitution with alkyl, acyl, alkoxymethyl, alkoxyethyl, arylsulfonyl, alkyl sulfonyl, any of which are further optionally substituted. These subsets of optional substitutions are intended to be merely exemplary and any combination of 2 to 5, or 2 to 10, or 2 to 20 of the groups recited above up to all the group recited above and any subrange in between are contemplated. "Optionally substituted" may include any of the chemical functional groups defined hereinabove and throughout this disclosure. Two optional substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., $—CH_2CH_3$), fully substituted (e.g., $—CF_2CF_3$), monosubstituted (e.g., $—CH_2CH_2F$) or substituted at a level anywhere in-between fully substituted and monosubstituted (e.g., $—CH_2CF_3$).

The various optional substitutions need not be the same and any combination of optional substituent groups may be combined. For example, a carbon chain may be substituted with an alkyl group, a halo group, and an alkoxy group. Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety selected from the group consisting of hydrogen, hydroxyl, halogen, alkyl, cycloalkyl, heteroalkyl, aryl, heteroaryl and heterocycloalkyl, any of which may be optionally substituted. Each such R and R' groups should be understood to be optionally substituted as defined herein. Each incidence of R and R' should be understood to be independent. Whether an R group has a number designation or not, every R group, including R, R' and $R^n$ where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. Thus, by way of example only, an unsymmetrical group such as —C(O)N(R)— may be attached to the parent moiety at either the carbon or the nitrogen.

Asymmetric centers, axial asymmetry (non-interchanging rotamers), or the like may exist in the compounds of the various embodiments disclosed herein. Such chirality may be designated by the symbols "R" or "S," depending on the configuration of substituents around the chiral carbon atom or the relevant axis. It should be understood that embodiments encompasses all stereochemical isomeric forms, including diastereomeric, enantiomeric, and epimeric forms, d-isomers and 1-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds of the various embodiments disclosed herein may exist as geometric isomers. The various embodiments disclosed herein includes all cis, trans, syn, anti, entgegen (E), and zusammen (Z) isomers as well as the appropriate mixtures thereof. Additionally, compounds may exist as tautomers, including keto-enol tautomers; all tautomeric isomers are embraced by the embodiments disclosed herein.

Additionally, the compounds of the various embodiments disclosed herein can exist in unsolvated as well as solvated forms with pharmaceutically acceptable solvents such as water, ethanol, and the like. In general, the solvated forms are considered equivalent to the unsolvated forms for the purposes of the various embodiments disclosed herein.

The term "bond" refers to a covalent linkage between two atoms, or two moieties when the atoms joined by the bond are considered part of larger substructure. A bond may be single, double, or triple unless otherwise specified. A dashed line between two atoms in a drawing of a molecule indicates that an additional bond may be present or absent at that position.

1. Salts of Compounds

The compounds disclosed herein can exist as pharmaceutically acceptable salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to Pharmaceutical Salts: Properties, Selection, and Use (Stahl, P. Heinrich. Wiley-VCHA, Zurich, Switzerland, 2002). It is understood that each of the compounds disclosed herein, and each embodiment of the compounds set forth herein, include pharmaceutically acceptable salts of such compounds.

The term "pharmaceutically acceptable salt," as used herein, represents salts or zwitterionic forms of the compounds disclosed herein which are water or oil-soluble or dispersible and pharmaceutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, paratoluenesulfonate (p-tosylate), and undecanoate. Also, basic groups in the compounds of the various embodiments disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form pharmaceutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the various embodiments disclosed herein contemplates sodium, potassium, magnesium, and calcium salts of the compounds disclosed herein, and the like.

Basic addition salts can be prepared during the final isolation and purification of the compounds by reacting a carboxyl group with a suitable base such as the hydroxide, carbonate, or bicarbonate of a metal cation or with ammonia or an organic primary, secondary, or tertiary amine. The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

C. Treatment-Related Definitions

The term "disease" as used herein is intended to be generally synonymous, and is used interchangeably with, the terms "disorder" and "condition" (as in medical condition), in that all reflect an abnormal condition of the body or of one of its parts that impairs normal functioning and is typically manifested by distinguishing signs and symptoms.

As used herein, the term "cancer" refers to all types of cancer, neoplasm or malignant tumors found in mammals (e.g., but not limited to, humans), including leukemia, lymphomas, carcinomas and sarcomas. In embodiments, the cancer is a metastatic cancer. A metastatic cancer is a cancer that has metastasized, e.g., the subject has developed a secondary malignant growth(s) at a distance from a primary (original) site of the cancer. The new, metastatic tumor is the same type of cancer as the primary tumor. In embodiments, metastasis occurs via the central nervous system and the compounds disclosed herein can ameliorate spread of the cancer via the CNS.

Exemplary cancers that may be treated with a compound or method provided herein include cancer of the thyroid, endocrine system, the central nervous system ("CNS," e.g., brain, spine and nerves), breast, cervix, colon, head & neck, liver, kidney, lung, non-small cell lung, melanoma, mesothelioma, ovary, sarcoma, stomach, uterus, Medulloblastoma, colorectal cancer, pancreatic cancer (specifically including pancreatic ductal adenocarcinoma (PDAC)). Additional examples include, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

As used herein, the term "lymphoma" refers to a group of cancers affecting hematopoietic and lymphoid tissues. It begins in lymphocytes, the blood cells that are found primarily in lymph nodes, spleen, thymus, and bone marrow. Two main types of lymphoma are non-Hodgkin lymphoma and Hodgkin's disease. Hodgkin's disease represents approximately 15% of all diagnosed lymphomas. This is a cancer associated with Reed-Sternberg malignant B lymphocytes. Non-Hodgkin's lymphomas (NHL) can be classified based on the rate at which cancer grows and the type of cells involved. There are aggressive (high grade) and indolent (low grade) types of NHL. Based on the type of cells involved, there are B-cell and T-cell NHLs. Exemplary B-cell lymphomas that may be treated with a compound or method provided herein include, but are not limited to, small lymphocytic lymphoma, Mantle cell lymphoma, follicular lymphoma, marginal zone lymphoma, extranodal (MALT) lymphoma, nodal (monocytoid B-cell) lymphoma, splenic lymphoma, diffuse large cell B-lymphoma, Burkitt's lymphoma, lymphoblastic lymphoma, immunoblastic large cell lymphoma, or precursor B-lymphoblastic lymphoma. Exemplary T-cell lymphomas that may be treated with a compound or method provided herein include, but are not limited to, cunateous T-cell lymphoma, peripheral T-cell lymphoma, anaplastic large cell lymphoma, mycosis fungoides, and precursor T-lymphoblastic lymphoma.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

Cancers of the central nervous system (CNS) are contemplated for treatment using the compounds described herein. CNS cancer can include any cancer of the CNS including cancer of the brain, spinal cord and nerves. Such CNS cancers can include, for example, primary cancers (e.g., those that start in the brain) and secondary or metastatic cancers CNS cancers (those that do not start in the CNS but metastasize to the CNS). Any CNS cancer is contemplated including without limitation, those listed elsewhere herein and gliomas (including astrocytomas and glioblastomas, oligodendrogliomas, ependymomas), meningiomas, medulloblastomas, ganbliogliomas, schwannomas, and craniopharyngiomas. Any metastatic CNS cancer is contemplated, including without limitation, a cancer metastasized to the CNS from metastases of melanoma, breast cancer, colon cancer, kidney cancer, nasopharyngeal cancer, and other of unknown primary site. Compounds described herein have the ability penetrate the CNS in order to treat CNS cancers, both primary and metastatic. Also, the treatments can include treating a cancer originated in the CNS that metastasizes to other parts of the CNS or outside of the CNS. Thus, compounds disclosed herein can also prevent or reduce metastatic pathways via the CNS.

"Ras associated cancer" (also referred to herein as "Ras related cancer") refers to a cancer caused by aberrant Ras activity or signaling. A "cancer associated with aberrant K-Ras activity" (also referred to herein as "K-Ras related cancer") is a cancer caused by aberrant K-Ras activity or signaling (e.g. a mutant K-Ras). K-Ras related cancers may include lung cancer, non-small cell lung cancer, breast cancer, leukemia, pancreatic cancer, colon cancer, colorectal cancer. Other cancers that are associated with aberrant activity of one or more of Ras, K-Ras, H-Ras, N-Ras, mutant K-Ras (including K-Ras G12C, K-Ras G12V, K-Ras G13C, K-Ras G12D, K-Ras G13D mutants), mutant N-Ras, and mutant H-Ras are well known in the art, including G12C in both N-Ras and H-Ras, and determining such cancers are within the skill of a person of skill in the art.

The term "administer (or administering) a Ras inhibitor" means administering a compound that inhibits the activity or level (e.g. amount) or level of a signaling pathway of one or more Ras proteins (e.g. a Ras inhibitor, K-Ras inhibitor, N-Ras inhibitor, H-Ras inhibitor, mutant K-Ras inhibitor, K-Ras G12C inhibitor, K-Ras G12V inhibitor, K-Ras G13C inhibitor, K-Ras G12D inhibitor, K-Ras G13D inhibitor) to a subject. Administration may include, without being limited by mechanism, allowing sufficient time for the Ras inhibitor to reduce the activity of one or more Ras proteins or for the Ras inhibitor to reduce one or more symptoms of a disease (e.g. cancer, wherein the Ras inhibitor may arrest the cell cycle, slow the cell cycle, reduce DNA replication, reduce cell replication, reduce cell growth, reduce metastasis, or cause cell death). The term "administer (or administering) a K-Ras inhibitor" means administering a compound that inhibits the activity or level (e.g. amount) or level of a signaling pathway of one or more K-Ras proteins (K-Ras, mutant K-Ras, K-Ras G12C, K-Ras G12V, K-Ras G12D, K-Ras G13C, K-Ras G13D). In embodiments, the administering does not include administration of any active agent other than the recited active agent.

The term "associated" or "associated with" in the context of a substance or substance activity or function associated with a disease (e.g. Ras (e.g., human K-Ras or human H-Ras) activity, a protein associated disease, a cancer associated with aberrant Ras activity, K-Ras associated cancer, mutant K-Ras associated cancer, activated K-Ras associated cancer, K-RasG12C associated cancer, K-Ras G12V associated cancer, K-Ras G13C associated cancer, K-Ras G12D associated cancer, K-Ras G13D associated cancer) means that the disease (e.g. cancer) is caused by (in whole or in part), or a symptom of the disease is caused by (in whole or inpart) the substance or substance activity or function. For example, a cancer associated with aberrant Ras activity or function may be a cancer that results (entirely or partially) from aberrant Ras activity or function (e.g. enzyme activity, protein-protein binding, signaling pathway) or a cancer wherein a particular symptom of the disease is caused (entirely or partially) by aberrant Ras activity or function. As used herein, what is described as being associated with a disease, if a causative agent, could be a target for treatment of the disease. For example, a cancer associated with aberrant Ras activity or function or a Ras associated cancer, may be treated with a Ras modulator or Ras inhibitor, in the instance where increased Ras activity or function (e.g., signaling pathway activity) causes the cancer. For example, a cancer associated with K-Ras G12C may be a cancer that a subject with K-Ras G12C is at higher risk of developing as compared to a subject without K-Ras G12C. For example, a cancer associated with K-Ras G12V may be a cancer that a subject with K-Ras G12V is at higher risk of developing as compared to a subject without K-Ras G12V.

The term "Ras" refers to one or more of the family of human Ras GTPase proteins (e.g. K-Ras, H-Ras, N-Ras). The term "K-Ras" refers to the nucleotide sequences or proteins of human K-Ras (e.g. human K-Ras4A (NP_203524.1), human K-Ras4B (NP_004976.2), or both K-Ras4A and K-Ras4B). The term "K-Ras" includes both the wild-type form of the nucleotide sequences or proteins as well as any mutants thereof. In some embodiments, "K-Ras" is wild-type K-Ras. In some embodiments, "K-Ras" is one or more mutant forms. The term "K-Ras" XYZ refers to a nucleotide sequence or protein of a mutant K-Ras wherein the Y numbered amino acid of K-Ras that has an X amino acid in the wildtype instead has a Z amino acid in the mutant (e.g. K-Ras G12C has a Gin wildtype protein but a C in the K-Ras G12C mutantprotein). In some embodiments K-Ras refers to K-Ras4A and K-Ras4B. In some embodiments, K-Ras refers to K-Ras4A. In some embodiments, K-Ras refers to K-Ras4B (e.g., NM_004985.4 or NP_004976.2). In some embodiments, K-Ras refers to the protein including (e.g., consisting of) the amino acid sequence below or including the sequence below with one or more mutations (e.g., G12C, G12V, or G13C):

```
                                              (SEQ ID NO: 1)
MTEYKLVVVGAGGVGKSALTIQLIQNHFVDEYDPTIEDSYRKQVVIDGET

CLLDILDTAGQEEYSAMRDQYMRTGEGFLCVFAINNTKSFEDIHHYREQI

KRVKDSEDVPMVLVGNKCDLPSRTVDTKQAQDLARSYGIPFIETSAKTRQ

GVDDAFYTLVREIRKHKEK
```

In some embodiments, K-Ras refers to the protein including (e.g., consisting of) the amino acid sequence below or including (e.g., consisting of) the sequence below with one or more mutations (e.g., G12C, G12V, or G13C):

```
                                              (SEQ ID NO: 2)
MTEYKLVVVGAGGVGKSALTIQLIQNHFVDEYDPTIEDSYRKQVVIDGET

CLLDILDTAGQEEYSAMRDQYMRTGEGFLCVFAINNTKSFEDIHHYREQI

KRVKDSEDVPMVLVGNKCDLPSRTVDTKQAQDLARSYGIPFIETSAKTRQ

GVDDAFYTLVREIRKHKEKMSKDGKKKKKKSKTKCVIM
```

1 mteyklvvvg aggvgksalt iqliqnhfvd eydptiedsy rkqvvidget clldildtag 61 qeeysamrdq ymrtgegflc vfainntksf edihhyreqi krvkdsedvp mvlvgnkcdl 121 psrtvdtkqa qdlarsygip fietsaktrq gvddafytiv reirkhkekm skdgkkkkkk 181 sktkcvim (SEQ ID NO:3)

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

"K-RAS inhibitor" is used herein to refer to a compound that exhibits an $IC_{50}$ with respect to K-RAS activity of no more than about 100 mM and more typically not more than about 50 mM, as measured in the K-RAS assay described generally hereinbelow. "$IC_{50}$" is that concentration of inhibitor that reduces the activity of an enzyme (e.g., K-RAS) to half-maximal level. Compounds of the various embodiments disclosed herein have been discovered to exhibit inhibition against oncogenic mutant K-RAS isoforms. In some embodiments, compounds will exhibit an $IC_{50}$ with respect to oncogenic mutant K-RAS of no more than about 10 mM; in further embodiments, compounds will exhibit an $IC_{50}$ with respect to K-RAS of no more than about 5 mM; in yet further embodiments, compounds will exhibit an $IC_{50}$ with respect to K-RAS of not more than about 1 mM, as measured in the K-RAS assay described herein. In yet further embodiments, compounds will exhibit an $IC_{50}$ with respect to K-RAS of not more than about 200 nM. Without being bound by theory, in some embodiments, the K-RAS inhibitor is an irreversible inhibitor by way of covalent bond formation to the cysteine at the G12C mutation site.

The phrase "therapeutically effective" is intended to qualify the amount of active ingredients used in the treatment of a disease or disorder. This amount will achieve the goal of reducing or eliminating the disease or disorder.

As used herein, reference to "treatment" of a subject is intended to include prophylaxis. The term "subject" means all mammals, including humans. Examples of subjects include humans, cows, dogs, cats, goats, sheep, pigs, and rabbits. In some embodiments, the subject is a human.

The term "prodrug" refers to a compound that is made active in vivo through chemical reaction in vivo thereby releasing an active compound. Compounds disclosed herein can be modified to exist as prodrugs, as described in Hydrolysis in Drug and Prodrug Metabolism: Chemistry, Biochemistry, and Enzymology (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the active compound. Additionally, prodrugs can be converted to the active compounds by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the active compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug is a compound which is administered as an ester (the "prodrug"), which is then metabolically hydrolyzed to the carboxylic acid, as the active entity. Additional examples include peptidyl derivatives of a compound. The term "therapeutically acceptable prodrug," refers to those prodrugs or zwitterions which are suitable for use in contact with the tissues of subjects without undue toxicity, irritation, and allergic response, are commensurate with a reasonable benefit/risk ratio, and are effective for their intended use.

V. Compound Embodiments

A. Genus I—General

In some embodiments, there are provided compounds of Formula (I):

(I)

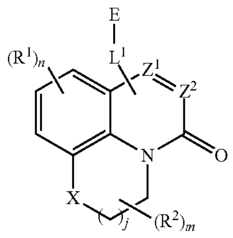

wherein:

X is $S(O)_p$, wherein p is an integer from 0 to 2;

j is an integer from 0 to 2;

$Z^1$ and $Z^2$ are independently $CR^6$ or N, with the proviso that at least one of $Z^1$ or $Z^2$ is $CR^6$ with $R^6$ being a bond to $L^1$;

$L^1$ is linking group comprising at least one nitrogen atom;

E is an electrophilic moiety, wherein E is bound to $L^1$ via the at least one nitrogen atom;

each $R^1$ is an optional substitution independently selected from the group consisting of alkyl, cyano, cycloalkyl, halo, haloalkyl, trifluoromethyl, alkoxy, aryl, heteroaryl, N-arylamino, N-aryl-N-alkylamino, aryloxy, and arylthio with the proviso that:

at least one $R^1$ is aryl, N-arylamino, N-aryl-N-alkylamino, aryloxy, arylthio, or heteroaryl, any of which is optionally substituted;

n is an integer from 1 to 3;

$R^2$ is selected from the group consisting of alkyl, alkylamino, dialkylamino alkylamidoalkyl, arylamidoalkyl, alkylsulfonamidoalkyl, arylsulfonamidoalkyl, N-alkyl aminoalkyl, N,N-dialkyl aminoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted;

m is an integer from 0 to 6;

$R^3$, $R^4$, and $R^5$ are each independently selected from the group consisting of hydrogen alkyl, halo, alkoxy, aryl, and heteroaryl, any of which are optionally substituted; and $R^6$ is selected from the group consisting of hydrogen, alkyl, haloakyl, cyano, halo, alkoxy, aryl, heteroaryl, trifluoromethyl and bond to $L^1$.

In one or more of the preceding embodiments, j is 1.

In one or more of the preceding embodiments, m is 0. In one or more of the preceding embodiments, m is 1.

In one or more of the preceding embodiments, $Z^1$ is $CR^6$ with $R^6$ being a bond to $L^1$.

In one or more of the preceding embodiments, $Z^2$ is N.

In one or more of the preceding embodiments, $L^1$ is

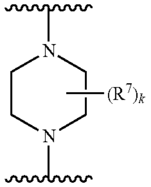

or

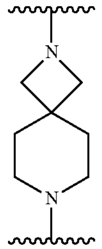

wherein k is an integer from 0 to 4; and each $R^7$ is independently selected from methyl, and cyanomethyl.

In one or more of the preceding embodiments, E is an acrylyl group having optional substitution R:

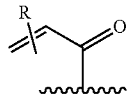

wherein R is selected from the group consisting of fluorine, methyl, and —$CH_2NR^aR^b$, wherein $R^a$ and $R^b$ are independently selected from hydrogen or alkyl; or $R^a$ and $R^b$ combine to form a $C_2$-$C_6$ nitrogen containing heterocycle.

B. Genus II—General Pyrimidone

In some embodiments, there are provided compounds of Formula (IIa):

(IIa)

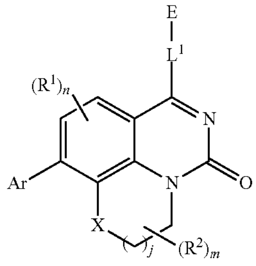

wherein:

X is $S(O)_p$, wherein p is an integer from 0 to 2;

j is an integer from 0 to 2;

$L^1$ is linking group comprising at least one nitrogen atom;

E is an electrophilic moiety, wherein E is bound to $L^1$ via the at least one nitrogen atom;

each $R^1$ is an optional substitution selected from the group consisting of alkyl, cyano, cycloalkyl, halo, haloalkyl, trifluoromethyl, and alkoxy;

n is an integer from 0 to 2;

$R^2$ is selected from the group consisting of alkyl, alkylamino, dialkylamino alkylamidoalkyl, arylamidoalkyl, alkylsulfonamidoalkyl, arylsulfonamidoalkyl, N-alkyl aminoalkyl, N,N-dialkyl aminoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted;

m is an integer from 0 to 6;

$R^3$, $R^4$, and $R^5$ are each independently selected from the group consisting of hydrogen alkyl, halo, alkoxy, aryl, and heteroaryl, any of which are optionally substituted; and Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted.

In one or more of the preceding embodiments, j is 1.

In one or more of the preceding embodiments, m is 0. In one or more of the preceding embodiments, m is 1.

In one or more of the preceding embodiments, $L^1$ is

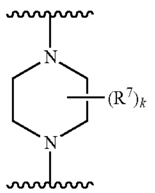

wherein k is an integer from 0 to 4; and each $R^7$ is independently selected from methyl, and cyanomethyl.

In one or more of the preceding embodiments, E is an acrylyl group having optional substitution R:

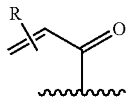

wherein R is selected from the group consisting of fluorine, methyl, and —$CH_2NR^aR^b$, wherein $R^a$ and $R^b$ are independently selected from hydrogen or alkyl; or $R^a$ and $R^b$ combine to form a $C_2$-$C_6$ nitrogen containing heterocycle.

In one or more of the preceding embodiments, Ar creates axial asymmetry.

In one or more of the preceding embodiments, the compound is a single rotamer.

In one or more of the preceding embodiments, Ar is:

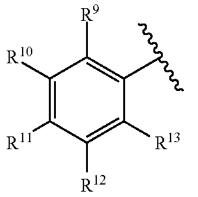

wherein $R^9$, $R^{10}$, $R^{11}$, $R^{12}$, and $R^{13}$ are each independently selected from the group consisting of hydrogen, halo, alkyl, alkoxy, haloalkyl, trifluoromethyl, cycloalkyl and any two adjacent $R^9$, $R^{10}$, $R^{11}$, $R^{12}$, and $R^{13}$ together combine to form a further fused ring that is an aromatic ring optionally comprising 1 to 3 heteroatoms independently selected from N, O or S, the further fused ring being optionally substituted.

C. Genus III-Pyrimidone Unsubstituted Ring Fusion

In some embodiments, there are provided compounds of Formula (III):

(III)

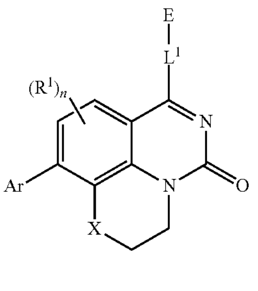

wherein:

X is O, $S(O)_p$, $CR^3R^4$, $NR^5$, or C(O), wherein p is an integer from 0 to 2;

$L^1$ is linking group comprising at least one nitrogen atom;

E is an electrophilic moiety, wherein E is bound to $L^1$ via the at least one nitrogen atom;

each $R^1$ is an optional substitution independently selected from the group consisting of hydrogen, alkyl, cyano, cycloalkyl, halo, haloalkyl, trifluoromethyl, and alkoxy;

n is an integer from 0 to 2;

$R^3$, $R^4$, and $R^5$ are each independently selected from the group consisting of hydrogen alkyl, halo, alkoxy, aryl, and heteroaryl, any of which are optionally substituted; and Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted.

In one or more of the preceding embodiments, X is O.

In one or more of the preceding embodiments, $L^1$ is

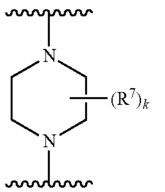

wherein k is an integer from 0 to 4; and each $R^7$ is independently selected from methyl and cyanomethyl;

In one or more of the preceding embodiments, E is an acrylyl group having optional substitution R:

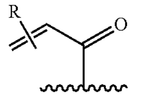

wherein R is selected from the group consisting of fluorine, methyl, and $—CH_2NR^aR^b$, wherein $R^a$ and $R^b$ are independently selected from hydrogen or alkyl; or $R^a$ and $R^b$ combine to form a $C_2$-$C_6$ nitrogen containing heterocycle.

In one or more of the preceding embodiments, optional substitution comprises monofluorination.

In one or more of the preceding embodiments, Ar creates axial asymmetry.

In one or more of the preceding embodiments, the compound is a single rotamer.

In one or more of the preceding embodiments, Ar is:

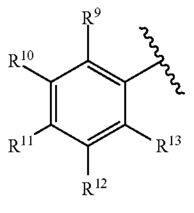

wherein $R^9$, $R^{10}$, $R^{11}$, $R^{12}$, and $R^{13}$ are each independently selected from the group consisting of hydrogen, halo, alkyl, alkoxy, haloalkyl, trifluoromethyl, cycloalkyl and any two adjacent $R^9$, $R^{10}$, $R^{11}$, $R^{12}$, and $R^{13}$ together combine to form a further fused ring that is an aromatic ring optionally comprising 1 to 3 heteroatoms independently selected from N, O or S, the further fused ring being optionally substituted.

D. Genus VI-Pyrimidone Acrylate Functionalized

In some embodiments, there are provided compounds of Formula (VI):

(VI)

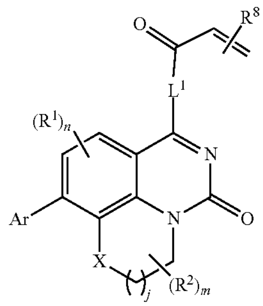

wherein:

X is $S(O)_p$, wherein p is an integer from 0 to 2;

j is an integer from 0 to 2;

$L^1$ is linking group comprising at least one nitrogen atom;

each $R^1$ is an optional substitution independently selected from the group consisting of alkyl, cyano, cycloalkyl, halo, haloalkyl, trifluoromethyl, and alkoxy;

n is an integer from 0 to 2;

$R^2$ is selected from the group consisting of alkyl, alkylamino, dialkylamino alkylamidoalkyl, arylamidoalkyl, alkylsulfonamidoalkyl, arylsulfonamidoalkyl, N-alkyl aminoalkyl, N,N-dialkyl aminoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted;

m is an integer from 0 to 6;

$R^3$, $R^4$, and $R^5$ are each independently selected from the group consisting of hydrogen alkyl, halo, alkoxy, aryl, and heteroaryl, any of which are optionally substituted;

$R^8$ is selected from the group consisting of fluorine, methyl, and $—CH_2NR^aR^b$, wherein $R^a$ and $R^b$ are independently selected from hydrogen or alkyl; or $R^a$ and $R^b$ combine to form a $C_2$-$C_6$ nitrogen containing heterocycle; and Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted.

E. Genus IX-Pyrimidone Heterocycle Linker Acrylate Functionalized

In some embodiments, there are provided compounds of Formula (IX):

(IX)

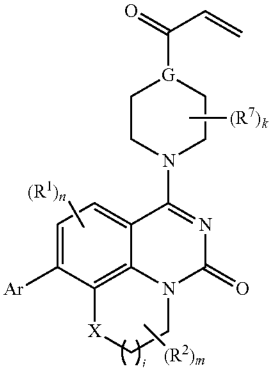

wherein:

X is O, $S(O)_p$, $CR^3R^4$, $NR^5$, or C(O), wherein p is an integer from 0 to 2;

j is an integer from 0 to 2;

G is selected from the group consisting of N, CH, and

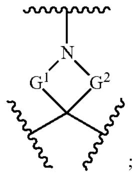

;

wherein $G^1$ and $G^2$ are independently $(CH_2)_q$, where q is 1 or 2;

each $R^1$ is an optional substitution independently selected from the group consisting of alkyl, cyano, cycloalkyl, halo, haloalkyl, trifluoromethyl, and alkoxy;

Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted;

n is an integer from 0 to 2;

$R^2$ is selected from the group consisting of alkyl, alkylamino, dialkylamino alkylamidoalkyl, arylamidoalkyl, alkylsulfonamidoalkyl, arylsulfonamidoalkyl, N-alkyl aminoalkyl, N,N-dialkyl aminoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted;

m is an integer from 0 to 6;

$R^3$, $R^4$, and $R^5$ are each independently selected from the group consisting of hydrogen alkyl, halo, alkoxy, aryl, and heteroaryl, any of which are optionally substituted;

wherein k is an integer from 0 to 4; and each $R^7$ is independently selected from methyl and cyanomethyl; and wherein the acrylyl moiety linked to G is optionally substituted.

F. Genus XX-Pyridone Acrylate Functionalized Arylated

In some embodiments, there are provided compounds of Formula (XX):

(XX)

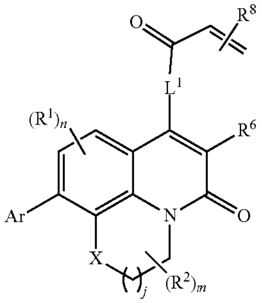

wherein:

X is $S(O)_p$, wherein p is an integer from 0 to 2;

j is an integer from 0 to 2;

$L^1$ is linking group comprising at least one nitrogen atom;

each $R^1$ is an optional substitution independently selected from the group consisting of alkyl, cyano, cycloalkyl, halo, haloalkyl, trifluoromethyl, and alkoxy;

n is an integer from 0 to 2;

$R^2$ is selected from the group consisting of alkyl, alkylamino, dialkylamino alkylamidoalkyl, arylamidoalkyl, alkylsulfonamidoalkyl, arylsulfonamidoalkyl, N-alkyl aminoalkyl, N,N-dialkyl aminoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted;

m is an integer from 0 to 6;

$R^3$, $R^4$, and $R^5$ are each independently selected from the group consisting of hydrogen alkyl, halo, alkoxy, aryl, and heteroaryl, any of which are optionally substituted;

$R^6$ is selected from the group consisting of hydrogen, alkyl, haloakyl, cyano, halo, alkoxy, aryl, heteroaryl, and trifluoromethyl;

$R^8$ is selected from the group consisting of fluorine, methyl, and $—CH_2NR^aR^b$, wherein $R^a$ and $R^b$ are independently selected from hydrogen or alkyl; or $R^a$ and $R^b$ combine to form a $C_2$-$C_6$ nitrogen containing heterocycle; and Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted.

In one or more of the preceding embodiments, j is 1.

In one or more of the preceding embodiments, m is 0. In one or more of the preceding embodiments, m is 1.

In one or more of the preceding embodiments, $L^1$ is

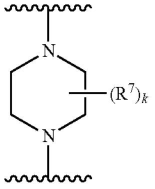

wherein k is an integer from 0 to 4; and each $R^7$ is independently selected from methyl and cyanomethyl;

In one or more of the preceding embodiments, Ar creates axial asymmetry.

In one or more of the preceding embodiments, the compound is a single rotamer.

In one or more of the preceding embodiments, Ar is:

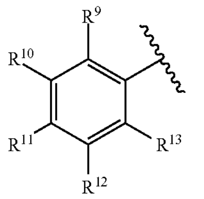

wherein $R^9$, $R^{10}$, $R^{11}$, $R^{12}$, and $R^{13}$ are each independently selected from the group consisting of hydrogen, halo, alkyl, alkoxy, haloalkyl, trifluoromethyl, cycloalkyl and any two adjacent $R^9$, $R^{10}$, $R^{11}$, $R^{12}$, and $R^{13}$ together combine to form a further fused ring that is an aromatic ring optionally comprising 1 to 3 heteroatoms independently selected from N, O or S, the further fused ring being optionally substituted.

In embodiments, there are provided compounds of formulas I, II, III, VI, IX, and XX characterized as being CNS penetrant as measured by a quantity in a rat brain model (when tested at 2 mg/kg after IV dosing) having a concentration value in the rat brain expressed in ng/g (ng of compound per gram of tissue). In embodiments, the concentration value in the rat brain is at least 60 ng/g. In embodiments, the concentration is in a range from about 40 ng/g to about 300 ng/g. In embodiments, the concentration is in a range from about 40 n/g to about 60 ng/g. In embodiments, the concentration is in a range from 50 ng/g to about 300 ng/g. In embodiments, the concentration is in a range from about 60 ng/g to about 300 ng/g. In embodiments, the concentration is in a range from about 100 ng/g to about 300 ng/g. In embodiments, the concentration is in a range from about 150 ng/g to about 300 ng/g. In embodiments, the concentration is from about 150 ng/g to about 275 ng/g.

G. Compound Tables

TABLE 3

| Ex. No. | Structure | MW | % CAF @ 10 uM, 1 h | Name |
|---|---|---|---|---|
| 63 | 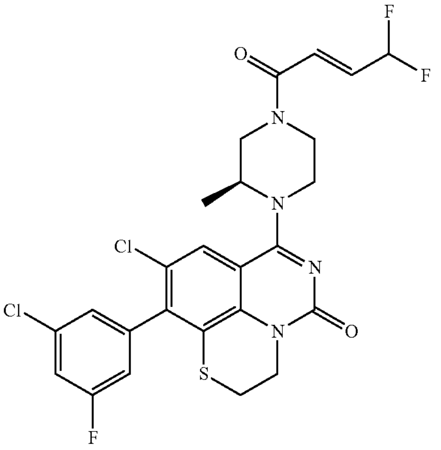 [SMILES: C[C@H]1CN(C(=O)/C=C/C(F)F)CCN1c1nc(=O)n2c3c(c(-c4cc(F)cc(Cl)c4)c(Cl)cc13)SCC2] | 569.43 | 67 | (S,E)-9-chloro-10-(3-chloro-5-fluorophenyl)-7-(4-(4,4-difluorobut-2-enoyl)-2-methylpiperazin-1-yl)-2,3-dihydro-5H-[1,4]thiazino[2,3,4-ij]quinazolin-5-one |
| 64 | 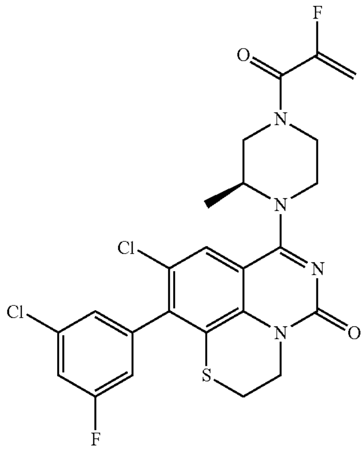 [SMILES: C=C(F)C(=O)N1CCN(c2nc(=O)n3c4c(c(-c5cc(F)cc(Cl)c5)c(Cl)cc24)SCC3)[C@@H](C)C1] | 537.41 | 75 | (S)-9-chloro-10-(3-chloro-5-fluorophenyl)-7-(4-(2-fluoroacryloyl)-2-methylpiperazin-1-yl)-2,3-dihydro-5H-[1,4]thiazino[2,3,4-ij]quinazolin-5-one |

TABLE 3-continued
| Ex. No. | Structure | MW | % CAF @ 10 uM, 1 h | Name |
|---|---|---|---|---|
| 65 | 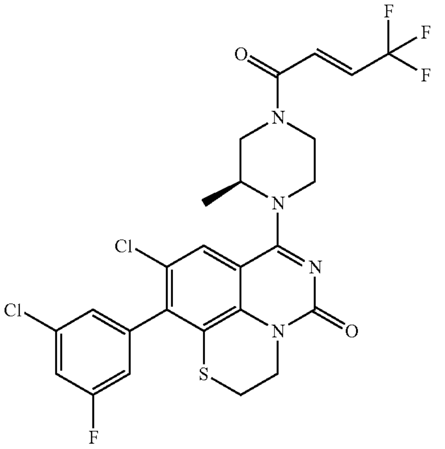 [SMILES: C[C@H]1CN(C(=O)/C=C/C(F)(F)F)CCN1c1nc(=O)n2c3c(c(-c4cc(F)cc(Cl)c4)c(Cl)cc13)SCC2] | 587.42 | 3 | (S)-9-chloro-10-(3-chloro-5-fluorophenyl)-7-(4-(2-fluoroacryloyl)-2-methylpiperazin-1-yl)-2,3-dihydro-5H-[1,4]thiazino[2,3,4-ij]quinazolin-5-one |
| 66 | 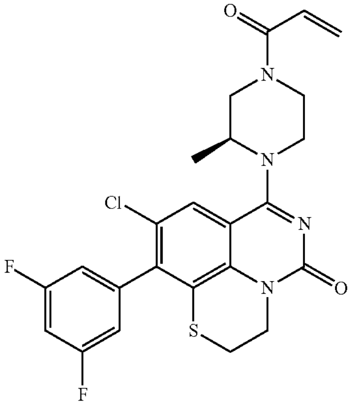 [SMILES: C=CC(=O)N1CCN(c2nc(=O)n3c4c(c(-c5cc(F)cc(F)c5)c(Cl)cc24)SCC3)[C@@H](C)C1] | 502.96 | 70 | (S)-7-(4-acryloyl-2-methylpiperazin-1-yl)-9-chloro-10-(3,5-difluorophenyl)-2,3-dihydro-5H-[1,4]thiazino[2,3,4-ij]quinazolin-5-one |
| 67 | 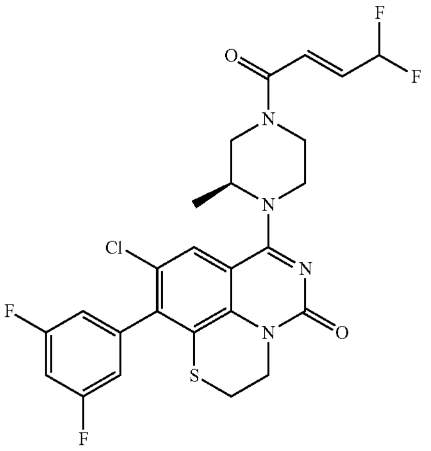 [SMILES: C[C@H]1CN(C(=O)/C=C/C(F)F)CCN1c1nc(=O)n2c3c(c(-c4cc(F)cc(F)c4)c(Cl)cc13)SCC2] | 552.97 | 91 | (S,E)-9-chloro-7-(4-(4,4-difluorobut-2-enoyl)-2-methylpiperazin-1-yl)-10-(3,5-difluorophenyl)-2,3-dihydro-5H-[1,4]thiazino[2,3,4-ij]quinazolin-5-one |

TABLE 3-continued
| Ex. No. | Structure | MW | % CAF @ 10 uM, 1 h | Name |
|---|---|---|---|---|
| 68 | 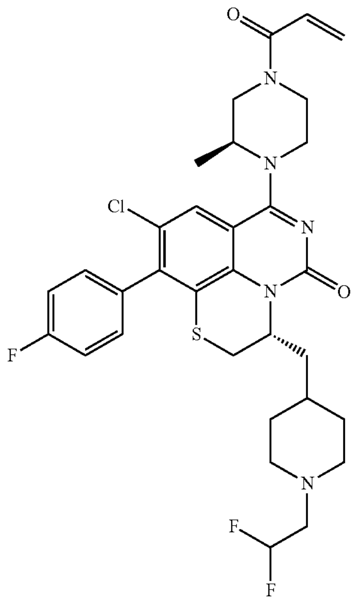 [SMILES: C=CC(=O)N1CCN(c2nc(=O)n3c4c(c(-c5ccc(F)cc5)c(Cl)cc24)SC[C@H]3CC2CCN(CC(F)F)CC2)[C@@H](C)C1] | 646.17 | 87 | (R)-7-((S)-4-acryloyl-2-methylpiperazin-1-yl)-9-chloro-3-((1-(2,2-difluoroethyl)piperidin-4-yl)methyl)-10-(4-fluorophenyl)-2,3-dihydro-5H-[1,4]thiazino[2,3,4-ij]quinazolin-5-one |
| 69 | 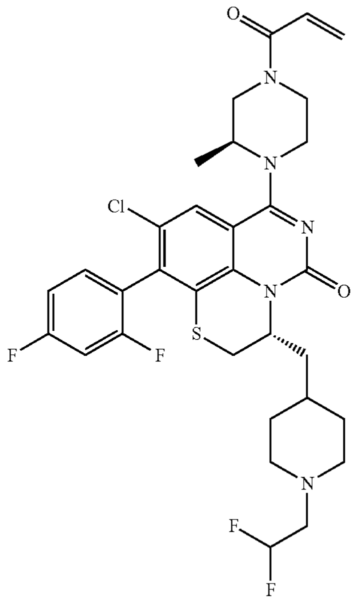 [SMILES: C=CC(=O)N1CCN(c2nc(=O)n3c4c(c(-c5ccc(F)cc5F)c(Cl)cc24)SC[C@H]3CN2CCN(CC(F)F)CC2)[C@@H](C)C1] | 664.16 | 96 | (3R)-7-((S)-4-acryloyl-2-methylpiperazin-1-yl)-9-chloro-3-((1-(2,2-difluoroethyl)piperidin-4-yl)methyl)-10-(2,4-difluorophenyl)-2,3-dihydro-5H-[1,4]thiazino[2,3,4-ij]quinazolin-5-one |

TABLE 3-continued

| Ex. No. | Structure | MW | % CAF @ 10 uM, 1 h | Name |
|---|---|---|---|---|
| 70 | 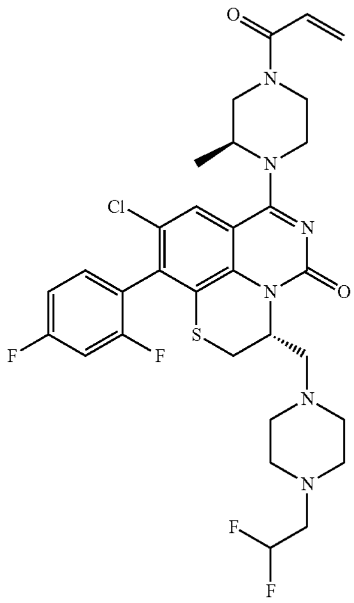 | 665.14 | 94 | (3R)-7-((S)-4-acryloyl-2-methylpiperazin-1-yl)-9-chloro-3-((1-(2,2-difluoroethyl)piperidin-4-yl)methyl)-10-(2,4-difluorophenyl)-2,3-dihydro-5H-[1,4]thiazino[2,3,4-ij]quinazolin-5-one |
| 71 | 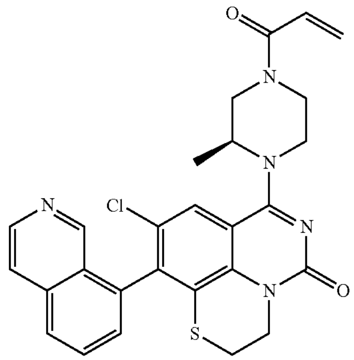 [SMILES: C=CC(=O)N1CCN(c2nc(=O)n3c4c(c(-c5cccc6ccncc56)c(Cl)cc24)SCC3)[C@@H](C)C1] | 518.03 | 87.8 | 7-((S)-4-acryloyl-2-methylpiperazin-1-yl)-9-chloro-10-(isoquinolin-8-yl)-2,3-dihydro-5H-[1,4]thiazino[2,3,4-ij]quinazolin-5-one |
| 72 | 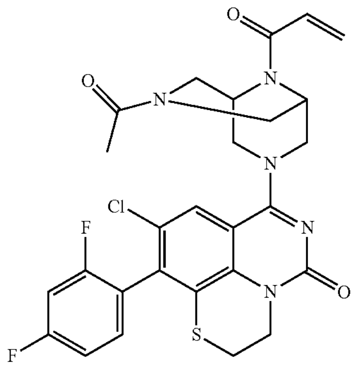 [SMILES: C=CC(=O)N1C2CN(C(C)=O)CC1CN(c1nc(=O)n3c4c(c(-c5ccc(F)cc5F)c(Cl)cc14)SCC3)C2] | 572.03 | 80.5 | 7-(7-acetyl-9-acryloyl-3,7,9-triazabicylco[3.3.1]nonan-3-yl)-9-chloro-10-(2,4-difluorophenyl)-2,3-dihydro-5H-[1,4]oxazino[2,3,4-ij]quinazolin-5-one |

TABLE 3-continued
| Ex. No. | Structure | MW | % CAF @ 10 uM, 1 h | Name |
|---|---|---|---|---|
| 73 | 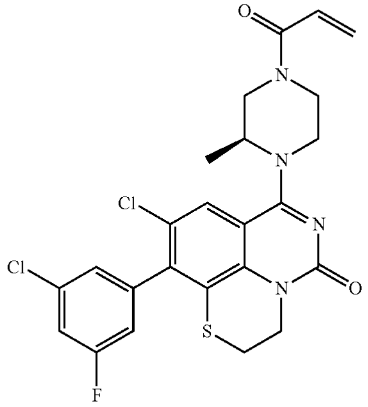 [SMILES: C=CC(=O)N1CCN(c2nc(=O)n3c4c(c(-c5cc(F)cc(Cl)c5)c(Cl)cc24)SCC3)[C@@H](C)C1] | 519.42 | 73 | (S)-7-(4-acryloyl-2-methylpiperazin-1-yl)-9-chloro-10-(3-chloro-5-fluorophenyl)-2,3-dihydro-5H-[1,4]thiazino[2,3,4-ij]quinazolin-5-one |
| 74 | 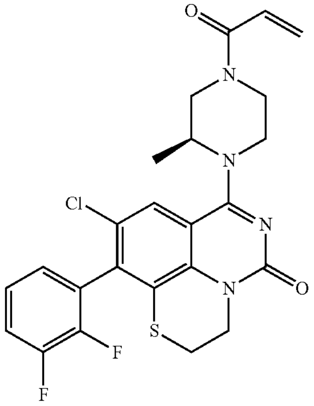 [SMILES: C=CC(=O)N1CCN(c2nc(=O)n3c4c(c(-c5cccc(F)c5F)c(Cl)cc24)SCC3)[C@@H](C)C1] | 502.96 | 95.6 | 7-((S)-4-acryloyl-2-methylpiperazin-1-yl)-9-chloro-10-(2,3-difluorophenyl)-2,3-dihydro-5H-[1,4]thiazino[2,3,4-ij]quinazolin-5-one |
| 75 | 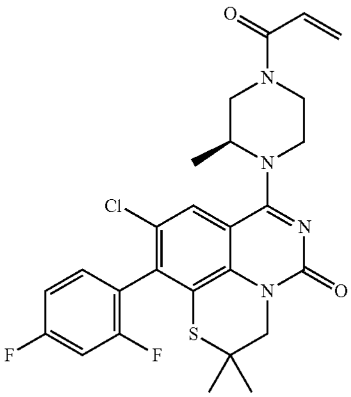 [SMILES: C=CC(=O)N1CCN(c2nc(=O)n3c4c(c(-c5ccc(F)cc5F)c(Cl)cc24)SC(C)(C)C3)[C@@H](C)C1] | 531.02 | 86.8 | 7-((S)-4-acryloyl-2-methylpiperazin-1-yl)-9-chloro-10-(2,4-difluorophenyl)-2,2-dimethyl-2,3-dihydro-5H-[1,4]thiazino[2,3,4-ij]quinazolin-5-one |

TABLE 3-continued

| Ex. No. | Structure | MW | % CAF @ 10 uM, 1 h | Name |
|---|---|---|---|---|
| 76 | 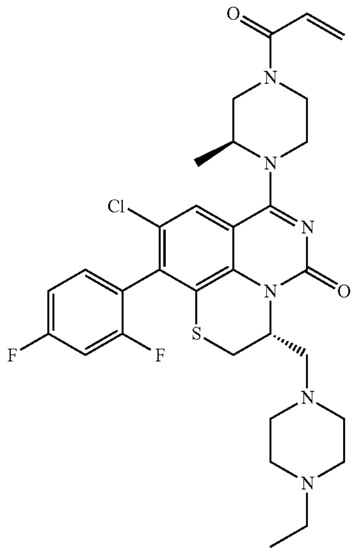 [SMILES: C=CC(=O)N1CCN(c2nc(=O)n3c4c(c(-c5ccc(F)cc5F)c(Cl)cc24)SC[C@H]3CN2CCN(CC)CC2)[C@@H](C)C1] | 629.16 | 79.3 | (3R)-7-((S)-4-acryloyl-2-methylpiperazin-1-yl)-9-chloro-10-(2,4-difluorophenyl)-3-((4-ethylpiperazin-1-yl)methyl)-2,3-dihydro-5H-[1,4]thiazino[2,3,4-ij]quinazolin-5-one |
| 77 | 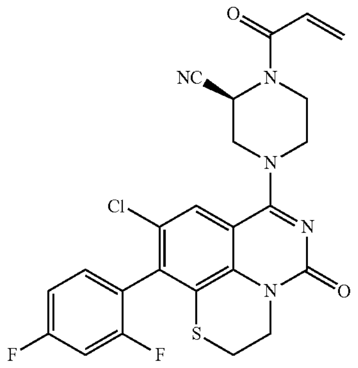 [SMILES: C=CC(=O)N1CCN(c2nc(=O)n3c4c(c(-c5ccc(F)cc5F)c(Cl)cc24)SCC3)C[C@H]1C#N] | 513.95 | 82 | (2S)-1-acryloyl-4-(9-chloro-10-(2,4-difluorophenyl)-5-oxo-2,3-dihydro-5H-[1,4]thiazino[2,3,4-ij]quinazolin-7-yl)piperazine-2-carbonitrile |
| 78 | 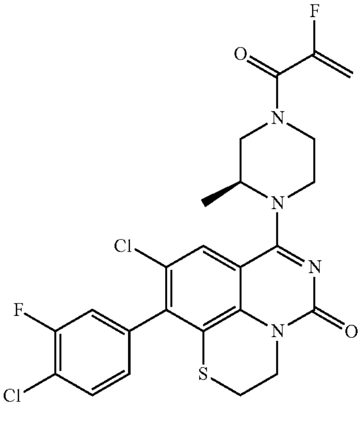 [SMILES: C=C(F)C(=O)N1CCN(c2nc(=O)n3c4c(c(-c5ccc(Cl)c(F)c5)c(Cl)cc24)SCC3)[C@@H](C)C1] | 537.41 | 6.7 | (S)-9-chloro-10-(4-chloro-3-fluorophenyl)-7-(4-(2-fluoroacryloyl)-2-methylpiperazin-1-yl)-2,3-dihydro-5H-[1,4]thiazino[2,3,4-ij]quinazolin-5-one |

TABLE 3-continued

| Ex. No. | Structure | MW | % CAF @ 10 uM, 1 h | Name |
|---|---|---|---|---|
| 79 | 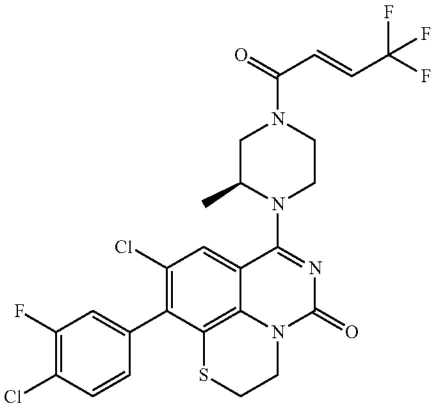 [SMILES: C[C@H]1CN(C(=O)/C=C/C(F)(F)F)CCN1c1nc(=O)n2c3c(c(-c4ccc(Cl)c(F)c4)c(Cl)cc13)SCC2] | 587.42 | 92 | (S,E)-9-chloro-10-(4-chloro-3-fluorophenyl)-7-(2-methyl-4-(4,4,4-trifluorobut-2-enoyl)piperazin-1-yl)-2,3-dihydro-5H-[1,4]thiazino[2,3,4-ij]quinazolin-5-one |
| 80 | 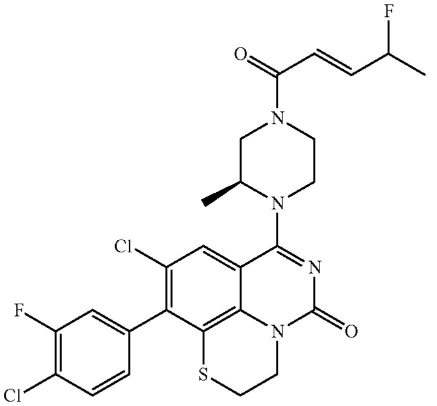 [SMILES: CC(F)/C=C/C(=O)N1CCN(c2nc(=O)n3c4c(c(-c5ccc(Cl)c(F)c5)c(Cl)cc24)SCC3)[C@@H](C)C1] | 569.43 | 93.5 | (S,E)-9-chloro-10-(4-chloro-3-fluorophenyl)-7-(4-(4,4-difluorobut-2-enoyl)-2-methylpiperazin-1-yl)-2,3-dihydro-5H-[1,4]thiazino[2,3,4-ij]quinazolin-5-one |
| 81 | 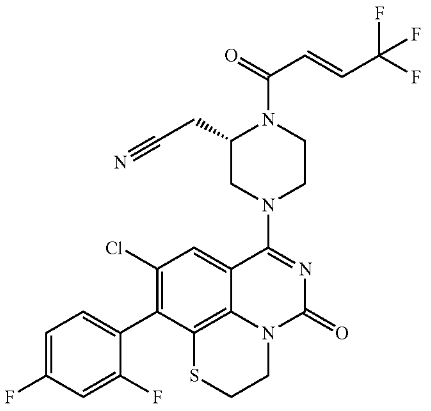 [SMILES: N#CC[C@H]1CN(c2nc(=O)n3c4c(c(-c5ccc(F)cc5F)c(Cl)cc24)SCC3)CCN1C(=O)/C=C/C(F)(F)F] | 595.97 | 89 | 2-((2S)-4-(9-chloro-10-(2,4-difluorophenyl)-5-oxo-2,3-dihydro-5H-[1,4]thiazino[2,3,4-ij]quinazolin-7-yl)-1-((E)-4,4,4-trifluorobut-2-enoyl)piperazin-2-yl)acetonitrile |

TABLE 3-continued

| Ex. No. | Structure | MW | % CAF @ 10 uM, 1 h | Name |
|---|---|---|---|---|
| 82 | 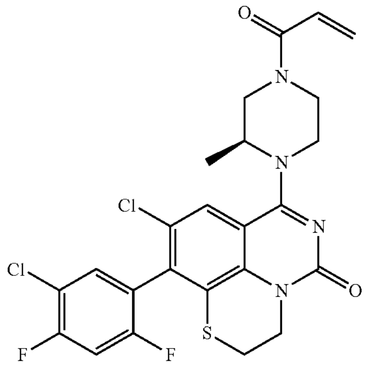 [SMILES: C=CC(=O)N1CCN(c2nc(=O)n3c4c(c(-c5cc(Cl)c(F)cc5F)c(Cl)cc24)SCC3)[C@@H](C)C1] | 537.41 | 85.8 | 7-((S)-4-acryloyl-2-methylpiperazin-1-yl)-9-chloro-10-(5-chloro-2,4-difluorophenyl)-2,3-dihydro-5H-[1,4]thiazino[2,3,4-ij]quinazolin-5-one |
| 83 | 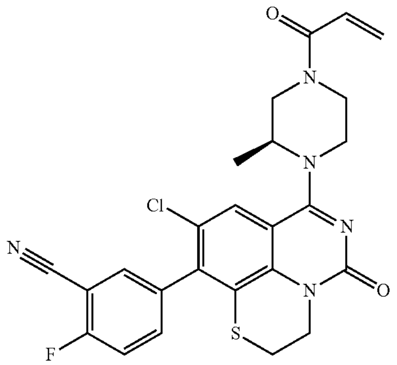 [SMILES: C=CC(=O)N1CCN(c2nc(=O)n3c4c(c(-c5ccc(F)c(C#N)c5)c(Cl)cc24)SCC3)[C@@H](C)C1] | 509.98 | 85.3 | (S)-5-(7-(4-acryloyl-2-methylpiperazin-1-yl)-9-chloro-5-oxo-2,3-dihydro-5H-[1,4]thiazino[2,3,4-ij]quinazolin-10-yl)-2-fluorobenzonitrile |
| 84 | 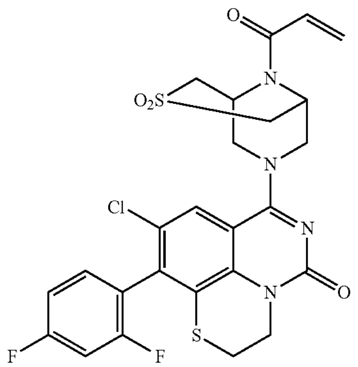 [SMILES: C=CC(=O)N1C2CN(c3nc(=O)n4c5c(c(-c6ccc(F)cc6F)c(Cl)cc35)SCC4)CC1CS(=O)(=O)C2] | 579.04 | 43.8 | 7-(9-acryloyl-3,3-dioxido-3-thia-7,9-diazabicyclo[3.3.1]nonan-7-yl)-9-chloro-10-(2,4-difluorophenyl)-2,3-dihydro-5H-[1,4]oxazino[2,3,4-ij]quinazolin-5-one |
| 85 | 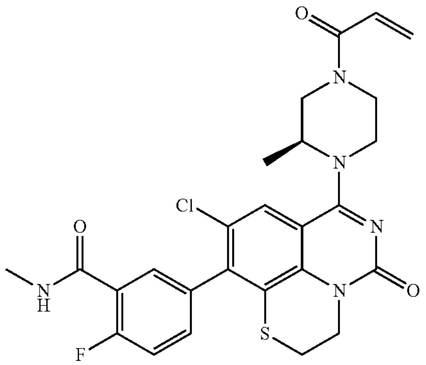 [SMILES: C=CC(=O)N1CCN(c2nc(=O)n3c4c(c(-c5ccc(F)c(C(=O)NC)c5)c(Cl)cc24)SCC3)[C@@H](C)C1] | 542.02 | 60.3 | (S)-5-(7-(4-acryloyl-2-methylpiperazin-1-yl)-9-chloro-5-oxo-2,3-dihydro-5H-[1,4]thiazino[2,3,4-ij]quinazolin-10-yl)-2-fluoro-N-methylbenzamide |

TABLE 3-continued

| Ex. No. | Structure | MW | % CAF @ 10 uM, 1 h | Name |
|---|---|---|---|---|
| 86 | 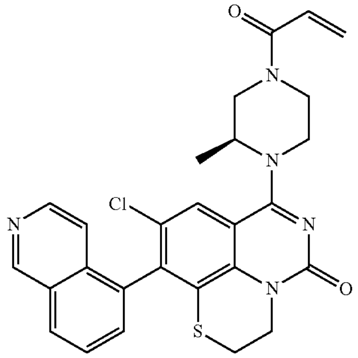 [SMILES: C=CC(=O)N1CCN(c2nc(=O)n3c4c(c(-c5cccc6cnccc56)c(Cl)cc24)SCC3)[C@@H](C)C1] | 518.03 | 76.1 | 7-((S)-4-acryloyl-2-methylpiperazin-1-yl)-9-chloro-10-(isoquinolin-5-yl)-2,3-dihydro-5H-[1,4]thiazino[2,3,4-ij]quinazolin-5-one |
| 87 | 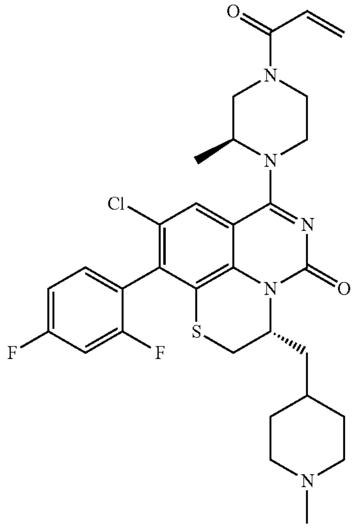 | 614.15 | 82.4 | (3R)-7-((S)-4-acryloyl-2-methylpiperazin-1-yl)-9-chloro-10-(2,4-difluorophenyl)-3-((1-methylpiperidin-4-yl)methyl)-2,3-dihydro-5H-[1,4]thiazino[2,3,4-ij]quinazolin-5-one |
| 88 | 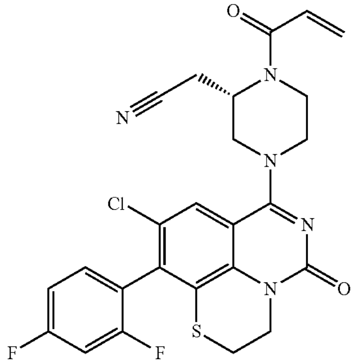 [SMILES: C=CC(=O)N1CCN(c2nc(=O)n3c4c(c(-c5ccc(F)cc5F)c(Cl)cc24)SCC3)C[C@@H]1CC#N] | 527.97 | 90.2 | 2-((2S)-1-acryloyl-4-(9-chloro-10-(2,4-difluorophenyl)-5-oxo-2,3-dihydro-5H-[1,4]thiazino[2,3,4-ij]quinazolin-7-yl)piperazin-2-yl)acetonitrile |

TABLE 3-continued

| Ex. No. | Structure | MW | % CAF @ 10 uM, 1 h | Name |
|---|---|---|---|---|
| 89 | 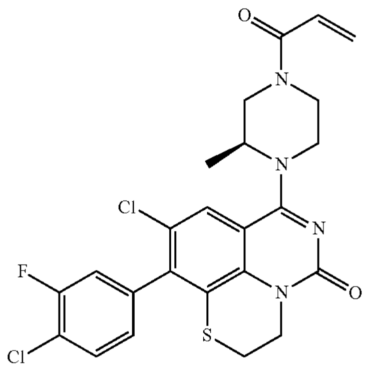 [SMILES: C=CC(=O)N1CCN(c2nc(=O)n3c4c(c(-c5ccc(Cl)c(F)c5)c(Cl)cc24)SCC3)[C@@H](C)C1] | 519.42 | 94.5 | (S)-7-(4-acryloyl-2-methylpiperazin-1-yl)-9-chloro-10-(4-chloro-3-fluorophenyl)-2,3-dihydro-5H-[1,4]thiazino[2,3,4-ij]quinazolin-5-one |
| 90 | 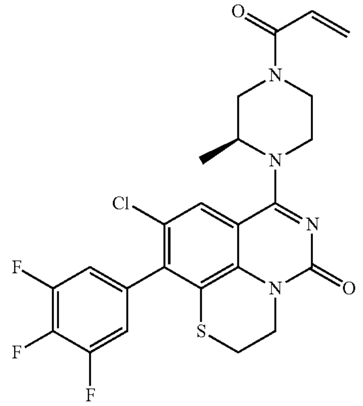 [SMILES: C=CC(=O)N1CCN(c2nc(=O)n3c4c(c(-c5cc(F)c(F)c(F)c5)c(Cl)cc24)SCC3)[C@@H](C)C1] | 520.95 | 78.8 | (S)-7-(4-acryloyl-2-methylpiperazin-1-yl)-9-chloro-10-(3,4,5-trifluorophenyl)-2,3-dihydro-5H-[1,4]thiazino[2,3,4-ij]quinazolin-5-one |
| 91 | 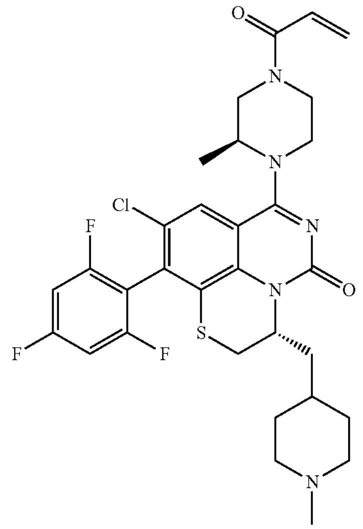 | 632.14 | 94.8 | (R)-7-((S)-4-acryloyl-2-methylpiperazin-1-yl)-9-chloro-3-((1-methylpiperidin-4-yl)methyl)-10-(2,4,6-trifluorophenyl)-2,3-dihydro-5H-[1,4]thiazino[2,3,4-ij]quinazolin-5-one |

TABLE 3-continued

| Ex. No. | Structure | MW | % CAF @ 10 uM, 1 h | Name |
|---|---|---|---|---|
| 92 | 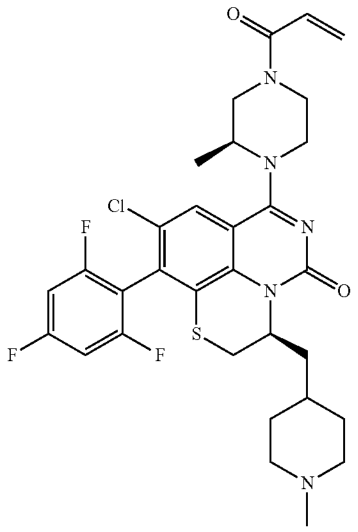 | 632.14 | 96.7 | (S)-7-((S)-4-acryloyl-2-methylpiperazin-1-yl)-9-chloro-3-((1-methylpiperidin-4-yl)methyl)-10-(2,4,6-trifluorophenyl)-2,3-dihydro-5H-[1,4]thiazino[2,3,4-ij]quinazolin-5-one |
| 93 | 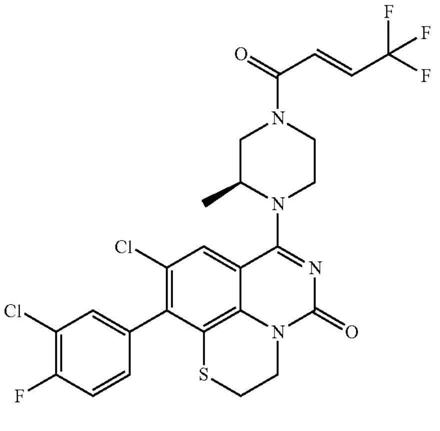 [SMILES: C[C@H]1CN(C(=O)/C=C/C(F)(F)F)CCN1c1nc(=O)n2c3c(c(-c4ccc(F)c(Cl)c4)c(Cl)cc13)SCC2] | 587.42 | 95 | (S,E)-9-chloro-10-(3-chloro-4-fluorophenyl)-7-(2-methyl-4-(4,4,4-trifluorobut-2-enoyl)piperazin-1-yl)-2,3-dihydro-5H-[1,4]thiazino[2,3,4-ij]quinazolin-5-one |
| 94 | 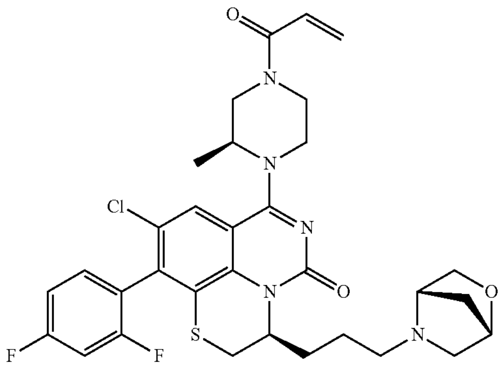 [SMILES: C=CC(=O)N1CCN(c2nc(=O)n3c4c(c(-c5ccc(F)cc5F)c(Cl)cc24)SC[C@@H]3CCCN2C[C@@H]3C[C@H]2CO3)[C@@H](C)C1] | 642.16 | 94.7 | (3S)-3-(3-((1S,4S)-2-oxa-5-azabicyclo[2.2.1]heptan-5-yl)propyl)-7-((S)-4-acryloyl-2-methylpiperazin-1-yl)-9-chloro-10-(2,4-difluorophenyl)-2,3-dihydro-5H-[1,4]thiazino[2,3,4-ij]quinazolin-5-one |

TABLE 3-continued

| Ex. No. | Structure | MW | % CAF @ 10 uM, 1 h | Name |
|---|---|---|---|---|
| 95 | 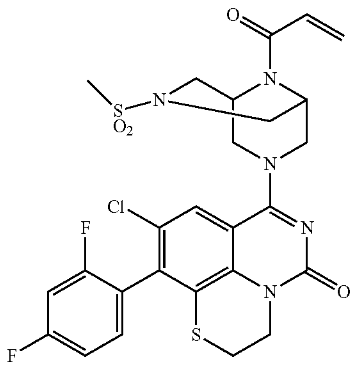 [SMILES: C=CC(=O)N1C2CN(c3nc(=O)n4c5c(c(-c6ccc(F)cc6F)c(Cl)cc35)SCC4)CC1CN(S(C)(=O)=O)C2] | 608.08 | 70.5 | 7-(9-acryloyl-7-(methylsulfonyl)-3,7,9-triazabicyclo[3.3.1]nonan-3-yl)-9-chloro-10-(2,4-difluorophenyl)-2,3-dihydro-5H-[1,4]thiazino[2,3,4-ij]quinazolin-5-one |
| 96 | 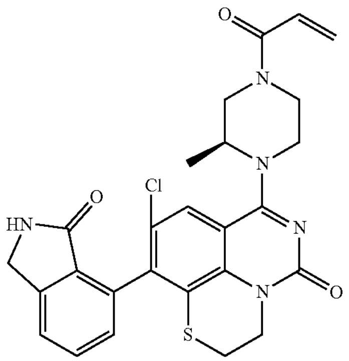 [SMILES: C=CC(=O)N1CCN(c2nc(=O)n3c4c(c(-c5cccc6c5C(=O)NC6)c(Cl)cc24)SCC3)[C@@H](C)C1] | 522.02 | 54 | 7-((S)-4-acryloyl-2-methylpiperazin-1-yl)-9-chloro-10-(3-oxoisoindolin-4-yl)-2,3-dihydro-5H-[1,4]thiazino[2,3,4-ij]quinazolin-5-one |
| 97 | 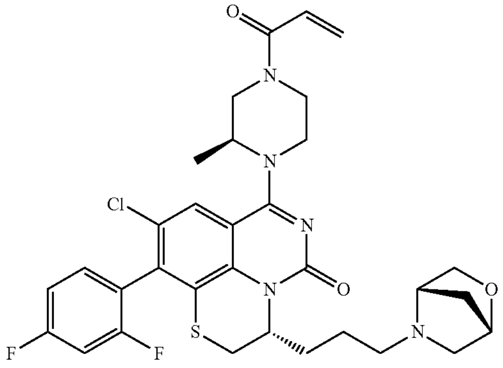 [SMILES: C=CC(=O)N1CCN(c2nc(=O)n3c4c(c(-c5ccc(F)cc5F)c(Cl)cc24)SC[C@H]3CCCN2C[C@@H]3C[C@H]2CO3)[C@@H](C)C1] | 642.16 | 96.5 | (3R)-3-(3-((1S,4S)-2-oxa-5-azabicyclo[2.2.1]heptan-5-yl)propyl)-7-((S)-4-acryloyl-2-methylpiperazin-1-yl)-9-chloro-10-(2,4-difluorophenyl)-2,3-dihydro-5H-[1,4]thiazino[2,3,4-ij]quinazolin-5-one |
| 98 | 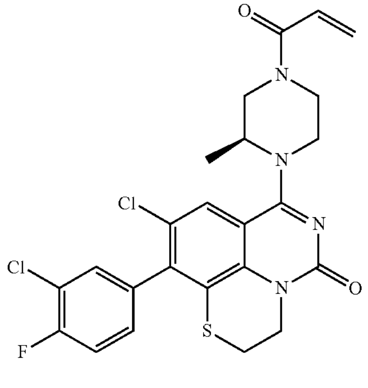 [SMILES: C=CC(=O)N1CCN(c2nc(=O)n3c4c(c(-c5ccc(F)c(Cl)c5)c(Cl)cc24)SCC3)[C@@H](C)C1] | 519.42 | 86.4 | (S)-7-(4-acryloyl-2-methylpiperazin-1-yl)-9-chloro-10-(3-chloro-4-fluorophenyl)-2,3-dihydro-5H-[1,4]thiazino[2,3,4-ij]quinazolin-5-one |

TABLE 3-continued

| Ex. No. | Structure | MW | % CAF @ 10 uM, 1 h | Name |
| --- | --- | --- | --- | --- |
| 99 | 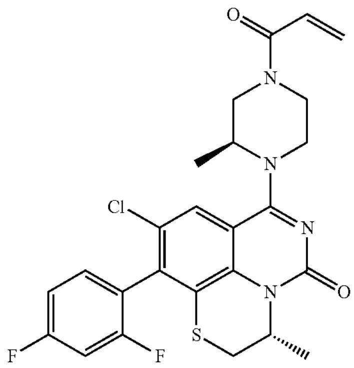 [SMILES: C=CC(=O)N1CCN(c2nc(=O)n3c4c(c(-c5ccc(F)cc5F)c(Cl)cc24)SC[C@H]3C)[C@@H](C)C1] | 516.99 | 87.2 | (3R)-7-((S)-4-acryloyl-2-methylpiperazin-1-yl)-9-chloro-10-(2,4-difluorophenyl)-3-methyl-2,3-dihydro-5H-[1,4]thiazino[2,3,4-ij]quinazolin-5-one |
| 100 | 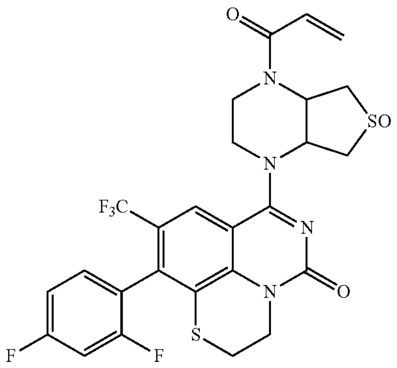 | 612.59 | 94 | 7-(4-acryloyl-6,6-dioxidohexahydrothieno[3,4-b]pyrazin-1(2H)-yl)-10-(2,4-difluorophenyl)-9-(trifluoromethyl)-2,3-dihydro-5H-[1,4]thiazino[2,3,4-ij]quinazolin-5-one |
| 101 | 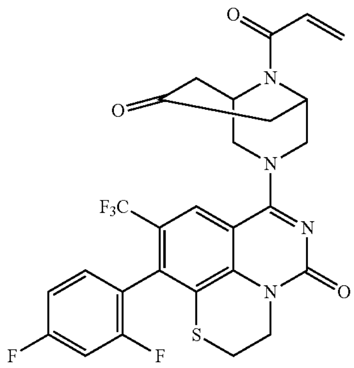 [SMILES: C=CC(=O)N1C2CC(=O)CC1CN(c1nc(=O)n3c4c(c(-c5ccc(F)cc5F)c(C(F)(F)F)cc14)SCC3)C2] | 576.54 | 96.5 | 7-(9-acryloyl-7-oxo-3,9-diazabicyclo[3.3.1]nonan-3-yl)-10-(2,4-difluorophenyl)-9-(trifluoromethyl)-2,3-dihydro-5H-[1,4]thiazino[2,3,4-ij]quinazolin-5-one |
| 102 | 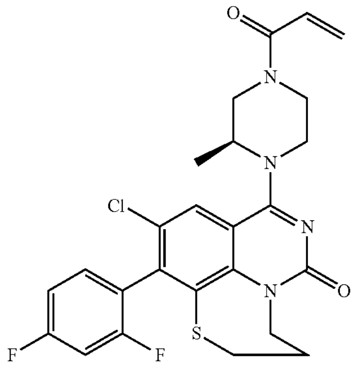 | 516.99 | 95.4 | 8-((S)-4-acryloyl-2-methylpiperazin-1-yl)-10-chloro-11-(2,4-difluorophenyl)-3,4-dihydro-2H,6H-[1,4]thiazepino[2,3,4-ij]quinazolin-6-one |

TABLE 3-continued

| Ex. No. | Structure | MW | % CAF @ 10 uM, 1 h | Name |
|---|---|---|---|---|
| 103 | 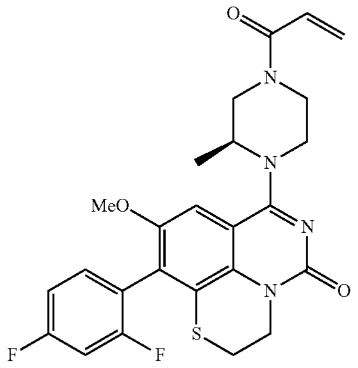 | 498.54 | 92.5 | 7-((S)-4-acryloyl-2-methylpiperazin-1-yl)-10-(2,4-difluorophenyl)-9-methoxy-2,3-dihydro-5H-[1,4]thiazino[2,3,4-ij]quinazolin-5-one |
| 104 | 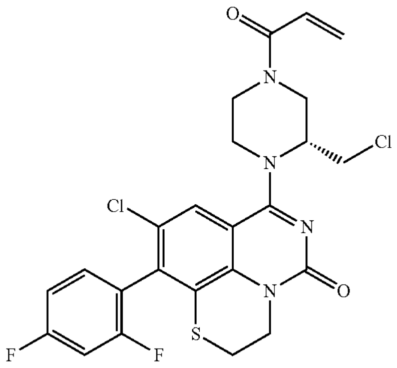 [SMILES: C=CC(=O)N1CCN(c2nc(=O)n3c4c(c(-c5ccc(F)cc5F)c(Cl)cc24)SCC3)[C@@H](CCl)C1] | 527.97 | 94.4 | 2-((2S)-4-acryloyl-1-(9-chloro-10-(2,4-difluorophenyl)-5-oxo-2,3-dihydro-5H-[1,4]thiazino[2,3,4-ij]quinazolin-7-yl)piperazin-2-yl)acetonitrile |
| 105 | 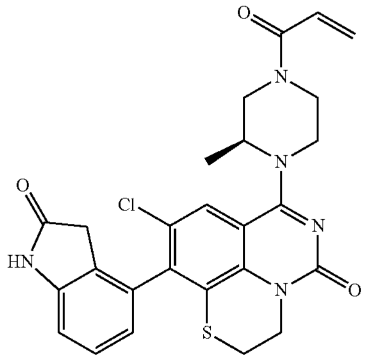 [SMILES: C=CC(=O)N1CCN(c2nc(=O)n3c4c(c(-c5cccc6c5CC(=O)N6)c(Cl)cc24)SCC3)[C@@H](C)C1] | 522.02 | 18.9 | 7-((S)-4-acryloyl-2-methylpiperazin-1-yl)-9-chloro-10-(2-oxoindolin-4-yl)-2,3-dihydro-5H-[1,4]thiazino[2,3,4-ij]quinazolin-5-one |
| 106 | 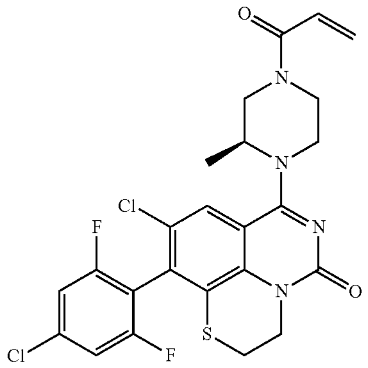 [SMILES: C=CC(=O)N1CCN(c2nc(=O)n3c4c(c(-c5c(F)cc(Cl)cc5F)c(Cl)cc24)SCC3)[C@@H](C)C1] | 537.41 | 45.2 | (S)-7-(4-acryloyl-2-methylpiperazin-1-yl)-9-chloro-10-(4-chloro-2,6-difluorophenyl)-2,3-dihydro-5H-[1,4]thiazino[2,3,4-ij]quinazolin-5-one |

TABLE 3-continued

| Ex. No. | Structure | MW | % CAF @ 10 uM, 1 h | Name |
|---|---|---|---|---|
| 107 | 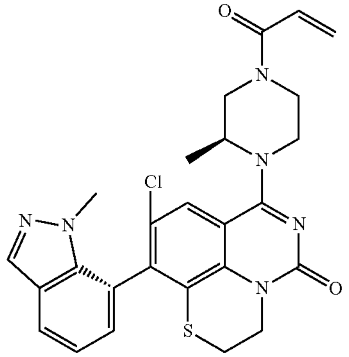 | 521.03 | 0 | (S)-7-((S)-4-acryloyl-2-methylpiperazin-1-yl)-9-chloro-10-(1-methyl-1H-indazol-7-yl)-2,3-dihydro-5H-[1,4]thiazino[2,3,4-ij]quinazolin-5-one |
| 108 | 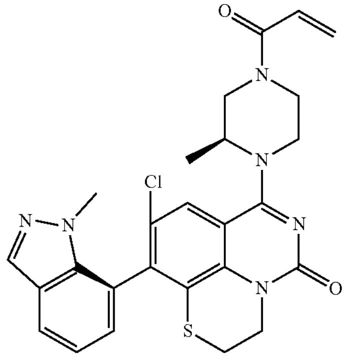 | 521.03 | 91.7 | (R)-7-((S)-4-acryloyl-2-methylpiperazin-1-yl)-9-chloro-10-(1-methyl-1H-indazol-7-yl)-2,3-dihydro-5H-[1,4]thiazino[2,3,4-ij]quinazolin-5-one |
| 109 | 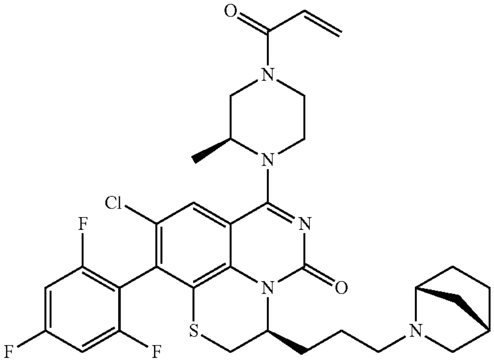 [SMILES: C=CC(=O)N1CCN(c2nc(=O)n3c4c(c(-c5c(F)cc(F)cc5F)c(Cl)cc24)SC[C@@H]3CCCN2C[C@H]3CC[C@@H]2C3)[C@@H](C)C1] | 660.15 | 96.9 | (S)-3-(3-((1S,4S)-2-oxa-5-azabicyclo[2.2.1]heptan-5-yl)propyl)-7-((S)-4-acryloyl-2-methylpiperazin-1-yl)-9-chloro-10-(2,4,6-trifluorophenyl)-2,3-dihydro-5H-[1,4]thiazino[2,3,4-ij]quinazolin-5-one |
| 110 | 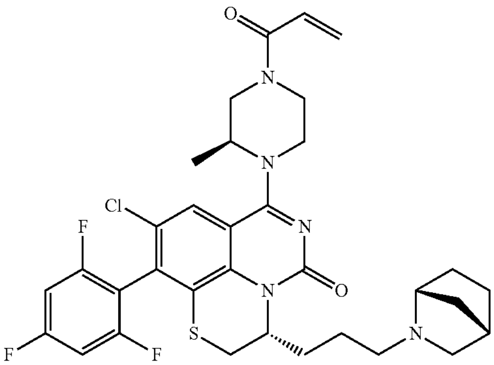 [SMILES: C=CC(=O)N1CCN(c2nc(=O)n3c4c(c(-c5c(F)cc(F)cc5F)c(Cl)cc24)SC[C@H]3CCCN2C[C@H]3CC[C@@H]2C3)[C@@H](C)C1] | 660.15 | 96.6 | (R)-3-(3-((1S,4S)-2-oxa-5-azabicyclo[2.2.1]heptan-5-yl)propyl)-7-((S)-4-acryloyl-2-methylpiperazin-1-yl)-9-chloro-10-(2,4,6-trifluorophenyl)-2,3-dihydro-5H-[1,4]thiazino[2,3,4-ij]quinazolin-5-one |

TABLE 3-continued

| Ex. No. | Structure | MW | % CAF @ 10 uM, 1 h | Name |
|---|---|---|---|---|
| 111 | 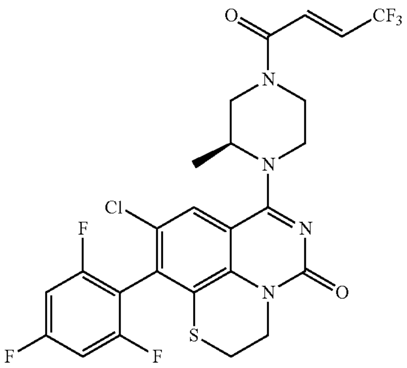 [SMILES: C[C@H]1CN(C(=O)/C=C/C(F)(F)F)CCN1c1nc(=O)n2c3c(c(-c4c(F)cc(F)cc4F)c(Cl)cc13)SCC2] | 588.95 | 95.2 | (S,E)-9-chloro-7-(2-methyl-4-(4,4,4-trifluorobut-2-enoyl)piperazin-1-yl)-10-(2,4,6-trifluorophenyl)-2,3-dihydro-5H-[1,4]thiazino[2,3,4-ij]quinazolin-5-one |
| 112 | 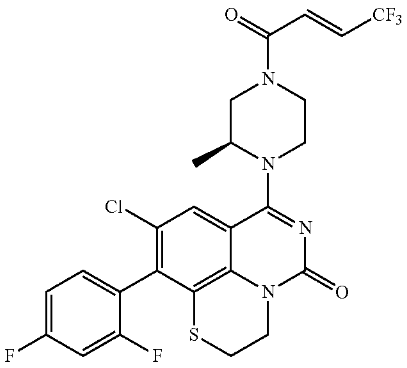 [SMILES: C[C@H]1CN(C(=O)/C=C/C(F)(F)F)CCN1c1nc(=O)n2c3c(c(-c4ccc(F)cc4F)c(Cl)cc13)SCC2] | 570.96 | 86.2 | 9-chloro-10-(2,4-difluorophenyl)-7-((S)-2-methyl-4-((E)-4,4,4-trifluorobut-2-enoyl)piperazin-1-yl)-2,3-dihydro-5H-[1,4]thiazino[2,3,4-ij]quinazolin-5-one |
| 113 | 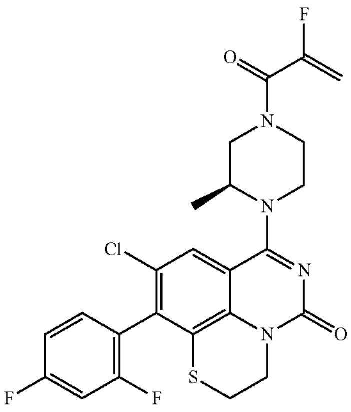 [SMILES: C=C(F)C(=O)N1CCN(c2nc(=O)n3c4c(c(-c5ccc(F)cc5F)c(Cl)cc24)SCC3)[C@@H](C)C1] | 520.95 | 21.7 | 9-chloro-10-(2,4-difluorophenyl)-7-((S)-4-(2-fluoroacryloyl)-2-methylpiperazin-1-yl)-2,3-dihydro-5H-[1,4]thiazino[2,3,4-ij]quinazolin-5-one |
| 114 | 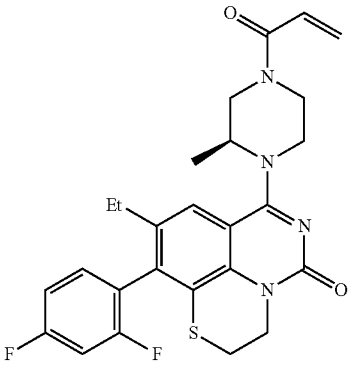 [SMILES: C=CC(=O)N1CCN(c2nc(=O)n3c4c(c(-c5ccc(F)cc5F)c(CC)cc24)SCC3)[C@@H](C)C1] | 496.57 | 92.8 | 7-((S)-4-acryloyl-2-methylpiperazin-1-yl)-10-(2,4-difluorophenyl)-9-ethyl-2,3-dihydro-5H-[1,4]thiazino[2,3,4-ij]quinazolin-5-one |

TABLE 3-continued

| Ex. No. | Structure | MW | % CAF @ 10 uM, 1 h | Name |
|---|---|---|---|---|
| 115 | 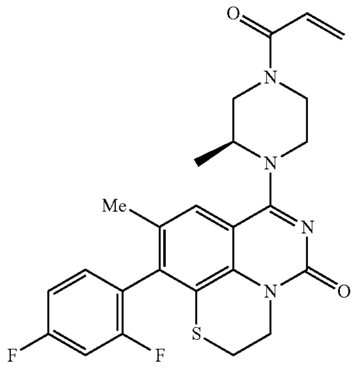 [SMILES: C=CC(=O)N1CCN(c2nc(=O)n3c4c(c(-c5ccc(F)cc5F)c(C)cc24)SCC3)[C@@H](C)C1] | 482.55 | 94.1 | 7-((S)-4-acryloyl-2-methylpiperazin-1-yl)-10-(2,4-difluorophenyl)-9-methyl-2,3-dihydro-5H-[1,4]thiazino[2,3,4-ij]quinazolin-5-one |
| 116 | 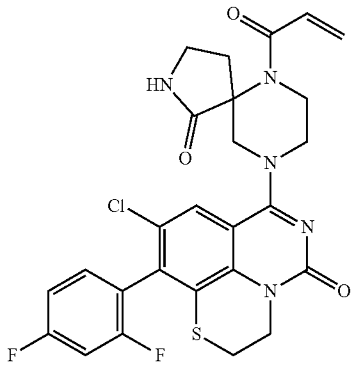 [SMILES: C=CC(=O)N1CCN(c2nc(=O)n3c4c(c(-c5ccc(F)cc5F)c(Cl)cc24)SCC3)CC12CCNC2=O] | 558 | 27.4 | 7-(6-acryloyl-1-oxo-2,6,9-triazaspiro[4.5]decan-9-yl)-9-chloro-10-(2,4-difluorophenyl)-2,3-dihydro-5H-[1,4]thiazino[2,3,4-ij]quinazolin-5-one |
| 117 | 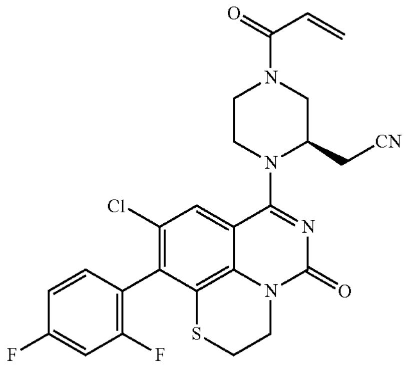 [SMILES: C=CC(=O)N1CCN(c2nc(=O)n3c4c(c(-c5ccc(F)cc5F)c(Cl)cc24)SCC3)[C@H](CC#N)C1] | 527.97 | 75.6 | 7-(6-acryloyl-1-oxo-2,6,9-triazaspiro[4.5]decan-9-yl)-9-chloro-10-(2,4-difluorophenyl)-2,3-dihydro-5H-[1,4]thiazino[2,3,4-ij]quinazolin-5-one |
| 118 | 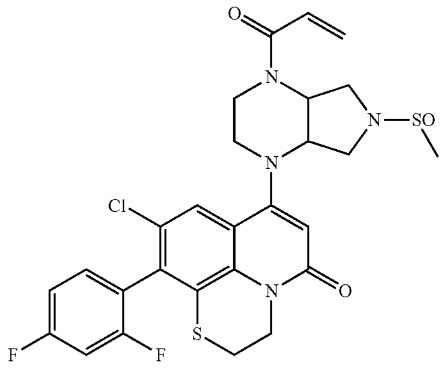 | 608.08 | 48.3 | 7-(4-acryloyl-6-(methylsulfonyl)octahydro-1H-pyrrolo[3,4-b]pyrazin-1-yl)-9-chloro-10-(2,4-difluorophenyl)-2,3-dihydro-5H-[1,4]thiazino[2,3,4-ij]quinazolin-5-one |

TABLE 3-continued

| Ex. No. | Structure | MW | % CAF @ 10 uM, 1 h | Name |
|---|---|---|---|---|
| 119 | 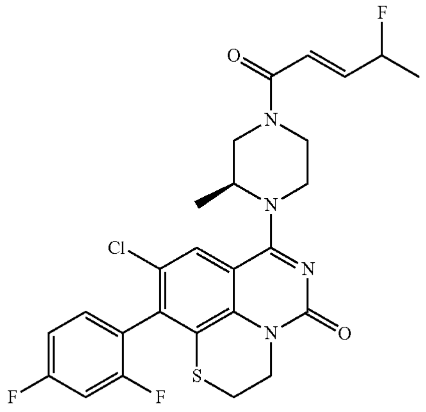 [SMILES: CC(F)/C=C/C(=O)N1CCN(c2nc(=O)n3c4c(c(-c5ccc(F)cc5F)c(Cl)cc24)SCC3)[C@@H](C)C1] | 552.97 | 97.1 | 9-chloro-7-((S)-4-((E)-4,4-difluorobut-2-enoyl)-2-methylpiperazin-1-yl)-10-(2,4-difluorophenyl)-2,3-dihydro-5H-[1,4]thiazino[2,3,4-ij]quinazolin-5-one |
| 120 | 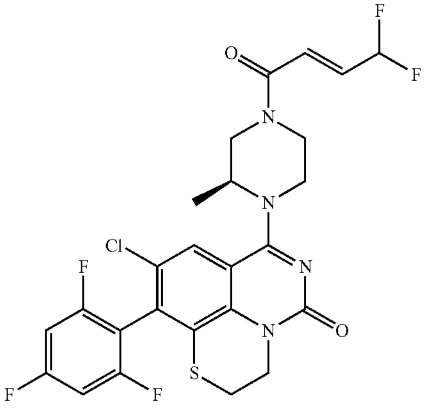 [SMILES: C[C@H]1CN(C(=O)/C=C/C(F)F)CCN1c1nc(=O)n2c3c(c(-c4c(F)cc(F)cc4F)c(Cl)cc13)SCC2] | 570.96 | 95.9 | (S,E)-9-chloro-7-(4-(4,4-difluorobut-2-enoyl)-2-methylpiperazin-1-yl)-10-(2,4,6-trifluorophenyl)-2,3-dihydro-5H-[1,4]thiazino[2,3,4-ij]quinazolin-5-one |
| 121 | 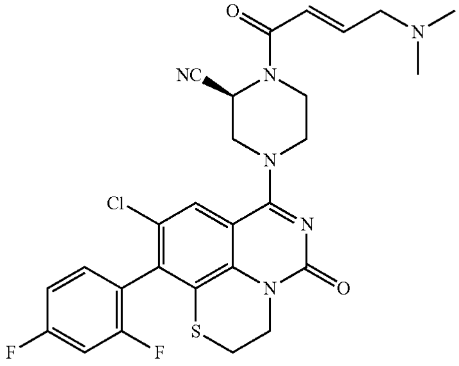 [SMILES: CN(C)C/C=C/C(=O)N1CCN(c2nc(=O)n3c4c(c(-c5ccc(F)cc5F)c(Cl)cc24)SCC3)C[C@H]1C#N] | 571.04 | 3.6 | (2S)-4-(9-chloro-10-(2,4-difluorophenyl)-5-oxo-2,3-dihydro-5H-[1,4]thiazino[2,3,4-ij]quinazolin-7-yl)-1-((E)-4-(dimethylamino)but-2-enoyl)piperazine-2-carbonitrile |
| 122 | 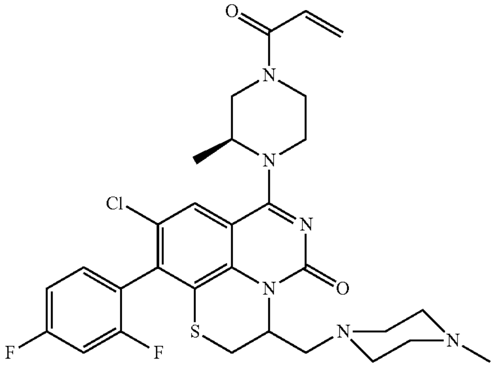 [SMILES: C=CC(=O)N1CCN(c2nc(=O)n3c4c(c(-c5ccc(F)cc5F)c(Cl)cc24)SCC3CN2CCN(C)CC2)[C@@H](C)C1] | 629.16 | 80.9 | 7-((S)-4-acryloyl-2-methylpiperazin-1-yl)-9-chloro-10-(2,4-difluorophenyl)-3-((4-ethylpiperazin-1-yl)methyl)-2,3-dihydro-5H-[1,4]thiazino[2,3,4-ij]quinazolin-5-one |

TABLE 3-continued

| Ex. No. | Structure | MW | % CAF @ 10 uM, 1 h | Name |
|---|---|---|---|---|
| 123 | 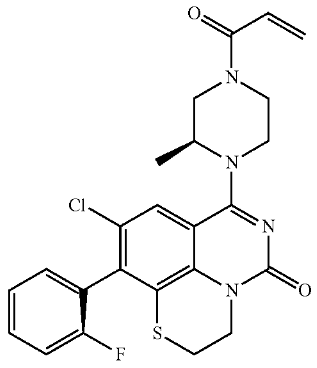 | 484.97 | 91.3 | (R)-7-((S)-4-acryloyl-2-methylpiperazin-1-yl)-9-chloro-10-(2-fluorophenyl)-2,3-dihydro-5H-[1,4]thiazino[2,3,4-ij]quinazolin-5-one |
| 124 | 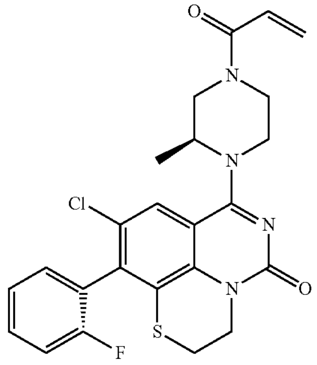 | 484.97 | 96 | (S)-7-((S)-4-acryloyl-2-methylpiperazin-1-yl)-9-chloro-10-(2-fluorophenyl)-2,3-dihydro-5H-[1,4]thiazino[2,3,4-ij]quinazolin-5-one |
| 125 | 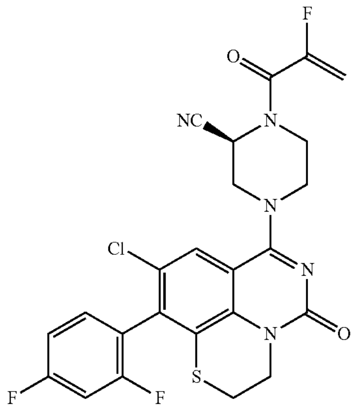 [SMILES: C=C(F)C(=O)N1CCN(c2nc(=O)n3c4c(c(-c5ccc(F)cc5F)c(Cl)cc24)SCC3)C[C@H]1C#N] | 531.94 | 94.5 | (2S)-4-(9-chloro-10-(2,4-difluorophenyl)-5-oxo-2,3-dihydro-5H-[1,4]thiazino[2,3,4-ij]quinazolin-7-yl)-1-(2-fluoroacryloyl)piperazine-2-carbonitrile |
| 126 | 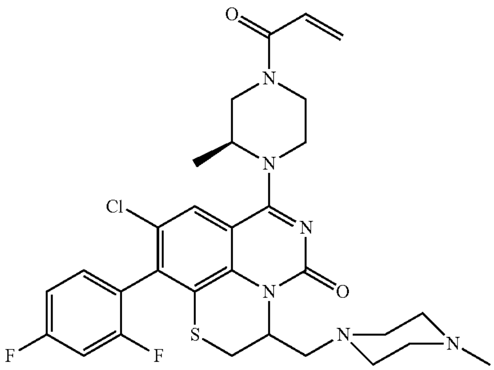 [SMILES: C=CC(=O)N1CCN(c2nc(=O)n3c4c(c(-c5ccc(F)cc5F)c(Cl)cc24)SCC3CN2CCN(C)CC2)[C@@H](C)C1] | 615.14 | 33.1 | 7-((S)-4-acryloyl-2-methylpiperazin-1-yl)-9-chloro-10-(2,4-difluorophenyl)-3-((4-methylpiperazin-1-yl)methyl)-2,3-dihydro-5H-[1,4]thiazino[2,3,4-ij]quinazolin-5-one |

TABLE 3-continued

| Ex. No. | Structure | MW | % CAF @ 10 uM, 1 h | Name |
|---|---|---|---|---|
| 127 | 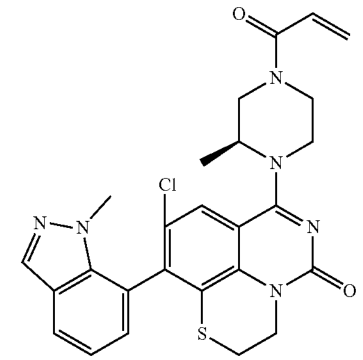 [SMILES: C=CC(=O)N1CCN(c2nc(=O)n3c4c(c(-c5cccc6cnn(C)c56)c(Cl)cc24)SCC3)[C@@H](C)C1] | 521.03 | 60 | 7-((S)-4-acryloyl-2-methylpiperazin-1-yl)-9-chloro-10-(1-methyl-1H-indazol-7-yl)-2,3-dihydro-5H-[1,4]thiazino[2,3,4-ij]quinazolin-5-one |
| 128 | 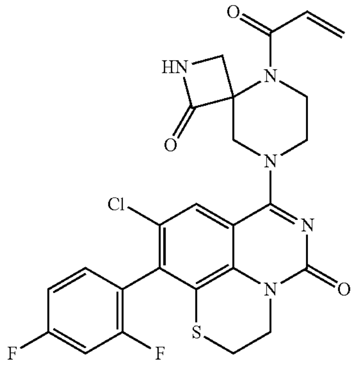 [SMILES: C=CC(=O)N1CCN(c2nc(=O)n3c4c(c(-c5ccc(F)cc5F)c(Cl)cc24)SCC3)CC12CNC2=O] | 543.97 | 62.7 | 7-(5-acryloyl-1-oxo-2,5,8-triazaspiro[3.5]nonan-8-yl)-9-chloro-10-(2,4-difluorophenyl)-2,3-dihydro-5H-[1,4]thiazino[2,3,4-ij]quinazolin-5-one |
| 129 | 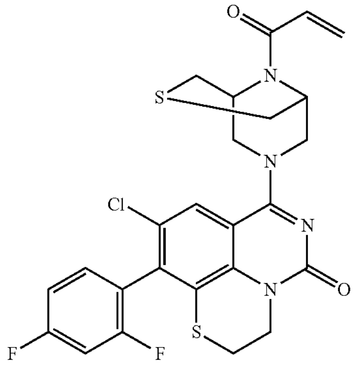 [SMILES: C=CC(=O)N1C2CSCC1CN(c1nc(=O)n3c4c(c(-c5ccc(F)cc5F)c(Cl)cc14)SCC3)C2] | 547.04 | 95.3 | 7-(9-acryloyl-3-thia-7,9-diazabicyclo[3.3.1]nonan-7-yl)-9-chloro-10-(2,4-difluorophenyl)-2,3-dihydro-5H-[1,4]thiazino[2,3,4-ij]quinazolin-5-one |
| 130 | 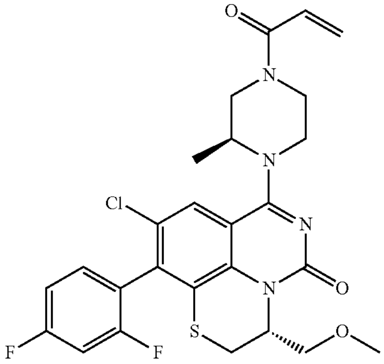 | 547.02 | 94.5 | (3R)-7-((S)-4-acryloyl-2-methylpiperazin-1-yl)-9-chloro-10-(2,4-difluorophenyl)-3-(methoxymethyl)-2,3-dihydro-5H-[1,4]thiazino[2,3,4-ij]quinazolin-5-one |

TABLE 3-continued

| Ex. No. | Structure | MW | % CAF @ 10 uM, 1 h | Name |
|---|---|---|---|---|
| 131 | 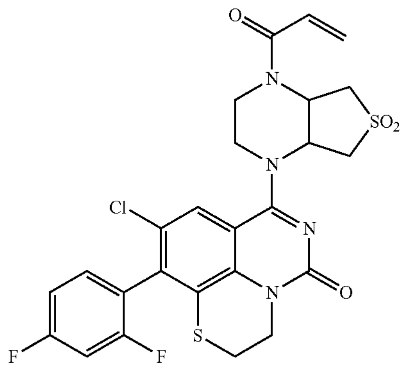 [SMILES: C=CC(=O)N1CCN(c2nc(=O)n3c4c(c(-c5ccc(F)cc5F)c(Cl)cc24)SCC3)C2CS(=O)(=O)CC21] | 579.04 | 82.2 | 7-(4-acryloyl-6,6-dioxidohexahydrothieno[3,4-b]pyrazin-1(2H)-yl)-9-chloro-10-(2,4-difluorophenyl)-2,3-dihydro-5H-[1,4]thiazino[2,3,4-ij]quinazolin-5-one |
| 132 | 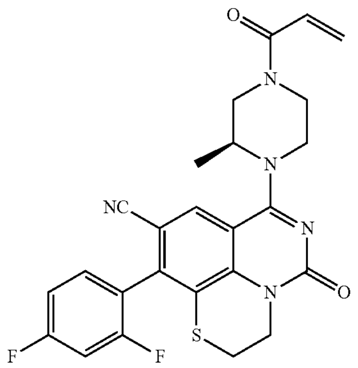 | 493.53 | 91.9 | 7-((S)-4-acryloyl-2-methylpiperazin-1-yl)-10-(2,4-difluorophenyl)-5-oxo-2,3-dihydro-5H-[1,4]thiazino[2,3,4-ij]quinazoline-9-carbonitrile |
| 133 | 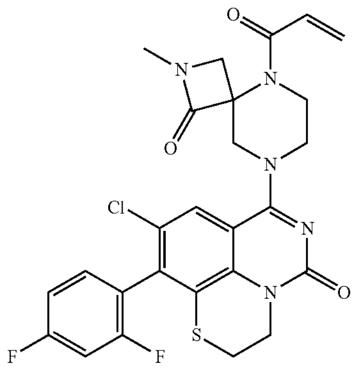 [SMILES: C=CC(=O)N1CCN(c2nc(=O)n3c4c(c(-c5ccc(F)cc5F)c(Cl)cc24)SCC3)CC12CN(C)C2=O] | 558 | 51.9 | 7-(5-acryloyl-2-methyl-1-oxo-2,5,8-triazaspiro[3.5]nonan-8-yl)-9-chloro-10-(2,4-difluorophenyl)-2,3-dihydro-5H-[1,4]thiazino[2,3,4-ij]quinazolin-5-one |
| 134 | 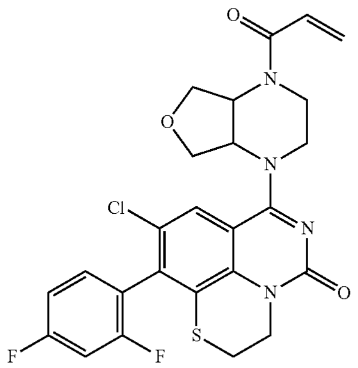 [SMILES: C=CC(=O)N1CCN(c2nc(=O)n3c4c(c(-c5ccc(F)cc5F)c(Cl)cc24)SCC3)C2COCC21] | 530.97 | 85 | 7-(4-acryloylhexahydrofuro[3,4-b]pyrazin-1(2H)-yl)-9-chloro-10-(2,4-difluorophenyl)-2,3-dihydro-5H-[1,4]thiazino[2,3,4-ij]quinazolin-5-one |

TABLE 3-continued

| Ex. No. | Structure | MW | % CAF @ 10 uM, 1 h | Name |
|---|---|---|---|---|
| 135 | 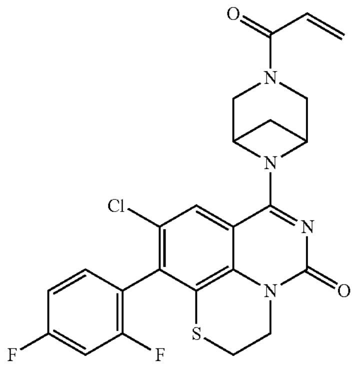 [SMILES: C=CC(=O)N1CC2CC(C1)N2c1nc(=O)n2c3c(c(-c4ccc(F)cc4F)c(Cl)cc13)SCC2] | 500.95 | 0 | 7-(3-acryloyl-3,6-diazabicyclo[3.1.1]heptan-6-yl)-9-chloro-10-(2,4-difluorophenyl)-2,3-dihydro-5H-[1,4]thiazino[2,3,4-ij]quinazolin-5-one |
| 136 | 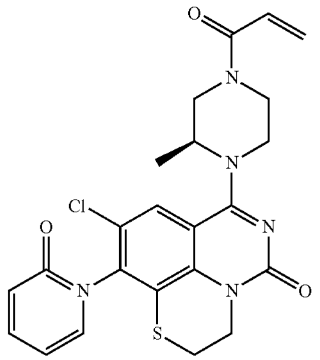 | 483.97 | 89.4 | 7-((S)-4-acryloyl-2-methylpiperazin-1-yl)-9-chloro-10-(2-oxopyridin-1(2H)-yl)-2,3-dihydro-5H-[1,4]thiazino[2,3,4-ij]quinazolin-5-one |
| 137 | 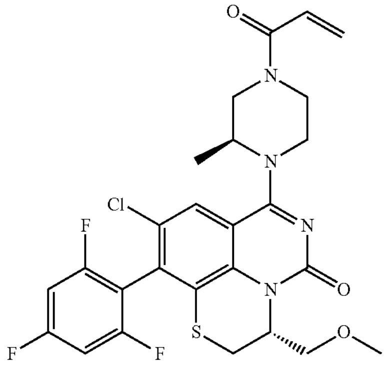 [SMILES: C=CC(=O)N1CCN(c2nc(=O)n3c4c(c(-c5c(F)cc(F)cc5F)c(Cl)cc24)SC[C@H]3COC)[C@@H](C)C1] | 565.01 | 86.8 | (R)-7-((S)-4-acryloyl-2-methylpiperazin-1-yl)-9-chloro-3-(methoxymethyl)-10-(2,4,6-trifluorophenyl)-2,3-dihydro-5H-[1,4]thiazino[2,3,4-ij]quinazolin-5-one |
| 138 | 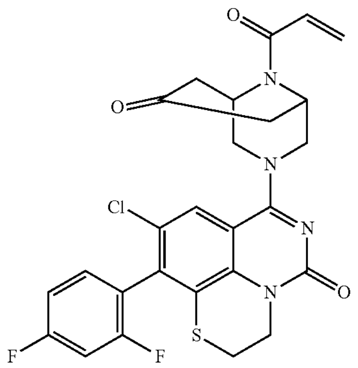 [SMILES: C=CC(=O)N1C2CC(=O)CC1CN(c1nc(=O)n3c4c(c(-c5ccc(F)cc5F)c(Cl)cc14)SCC3)C2] | 542.98 | 95.8 | 7-(9-acryloyl-7-oxo-3,9-diazabicyclo[3.3.1]nonan-3-yl)-9-chloro-10-(2,4-difluorophenyl)-2,3-dihydro-5H-[1,4]thiazino[2,3,4-ij]quinazolin-5-one |

TABLE 3-continued

| Ex. No. | Structure | MW | % CAF @ 10 uM, 1 h | Name |
|---|---|---|---|---|
| 139 | 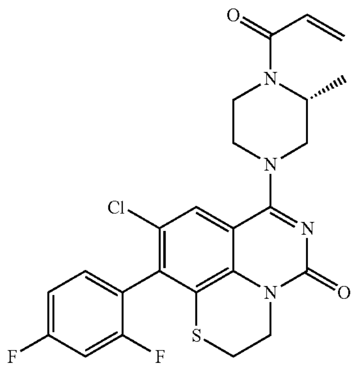 [SMILES: C=CC(=O)N1CCN(c2nc(=O)n3c4c(c(-c5ccc(F)cc5F)c(Cl)cc24)SCC3)C[C@H]1C] | 502.96 | 94.8 | 7-((R)-4-acryloyl-3-methylpiperazin-1-yl)-9-chloro-10-(2,4-difluorophenyl)-2,3-dihydro-5H-[1,4]thiazino[2,3,4-ij]quinazolin-5-one |
| 140 | 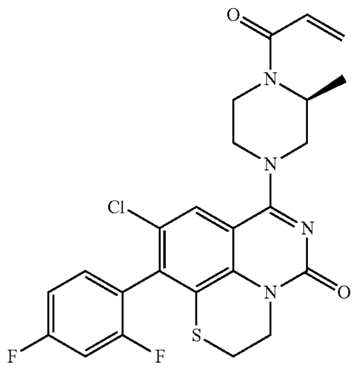 [SMILES: C=CC(=O)N1CCN(c2nc(=O)n3c4c(c(-c5ccc(F)cc5F)c(Cl)cc24)SCC3)C[C@@H]1C] | 502.96 | 90.6 | 7-((S)-4-acryloyl-3-methylpiperazin-1-yl)-9-chloro-10-(2,4-difluorophenyl)-2,3-dihydro-5H-[1,4]thiazino[2,3,4-ij]quinazolin-5-one |
| 141 | 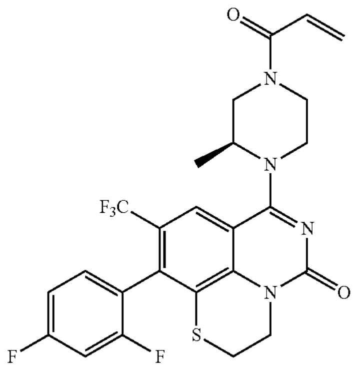 | 536.52 | 95.7 | 7-((S)-4-acryloyl-2-methylpiperazin-1-yl)-10-(2,4-difluorophenyl)-9-(trifluoromethyl)-2,3-dihydro-5H-[1,4]thiazino[2,3,4-ij]quinazolin-5-one |
| 142 | 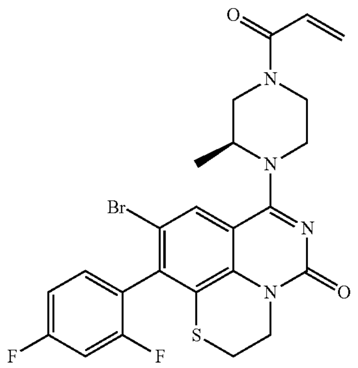 | 547.41 | 94.7 | 7-((S)-4-acryloyl-2-methylpiperazin-1-yl)-9-bromo-10-(2,4-difluorophenyl)-2,3-dihydro-5H-[1,4]thiazino[2,3,4-ij]quinazolin-5-one |

TABLE 3-continued

| Ex. No. | Structure | MW | % CAF @ 10 uM, 1 h | Name |
|---|---|---|---|---|
| 143 | 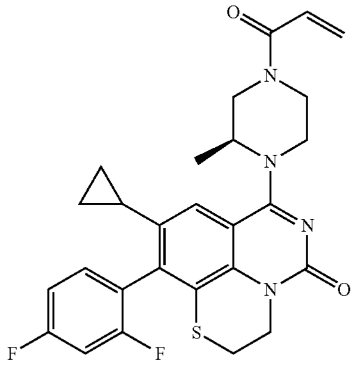 [SMILES: C=CC(=O)N1CCN(c2nc(=O)n3c4c(c(-c5ccc(F)cc5F)c(C5CC5)cc24)SCC3)[C@@H](C)C1] | 508.58 | 95.4 | 7-((S)-4-acryloyl-2-methylpiperazin-1-yl)-9-cyclopropyl-10-(2,4-difluorophenyl)-2,3-dihydro-5H-[1,4]thiazino[2,3,4-ij]quinazolin-5-one |
| 144 | 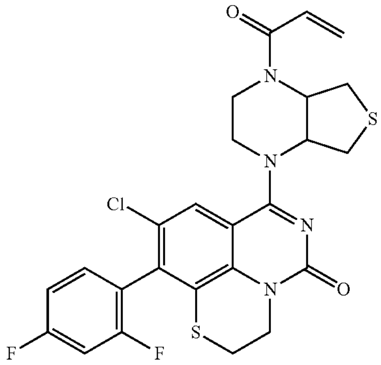 [SMILES: C=CC(=O)N1CCN(c2nc(=O)n3c4c(c(-c5ccc(F)cc5F)c(Cl)cc24)SCC3)C2CSCC21] | 547.04 | 64.9 | 7-(4-acryloylhexahydrothieno[3,4-b]pyrazin-1(2H)-yl)-9-chloro-10-(2,4-difluorophenyl)-2,3-dihydro-5H-[1,4]thiazino[2,3,4-ij]quinazolin-5-one |
| 145 | 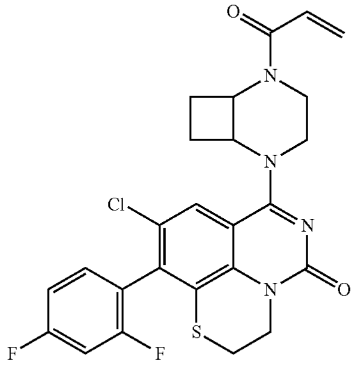 [SMILES: C=CC(=O)N1CCN(c2nc(=O)n3c4c(c(-c5ccc(F)cc5F)c(Cl)cc24)SCC3)C2CCC21] | 514.97 | 58 | 7-(5-acryloyl-2,5-diazabicyclo[4.2.0]octan-2-yl)-9-chloro-10-(2,4-difluorophenyl)-2,3-dihydro-5H-[1,4]thiazino[2,3,4-ij]quinazolin-5-one |
| 146 | 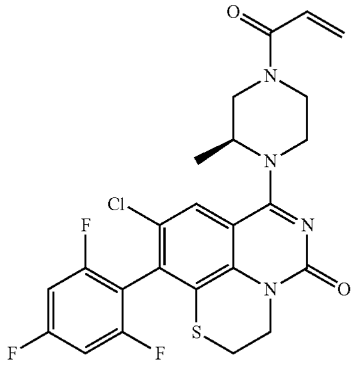 | 520.95 | 90.7 | (S)-7-(4-acryloyl-2-methylpiperazin-1-yl)-9-chloro-10-(2,4,6-trifluorophenyl)-2,3-dihydro-5H-[1,4]thiazino[2,3,4-ij]quinazolin-5-one |

TABLE 3-continued

| Ex. No. | Structure | MW | % CAF @ 10 uM, 1 h | Name |
|---|---|---|---|---|
| 147 | 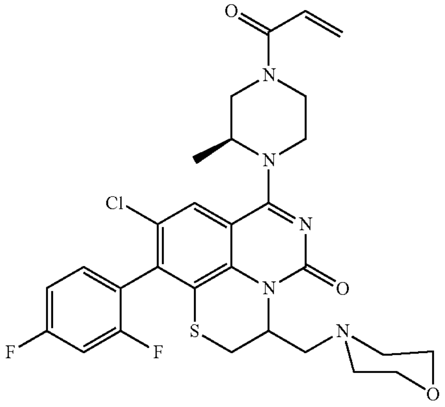 [SMILES: C=CC(=O)N1CCN(c2nc(=O)n3c4c(c(-c5ccc(F)cc5F)c(Cl)cc24)SCC3CN2CCOCC2)[C@@H](C)C1] | 602.1 | 44.6 | 7-((S)-4-acryloyl-2-methylpiperazin-1-yl)-9-chloro-10-(2,4-difluorophenyl)-3-(morpholinomethyl)-2,3-dihydro-5H-[1,4]thiazino[2,3,4-ij]quinazolin-5-one |
| 148 | 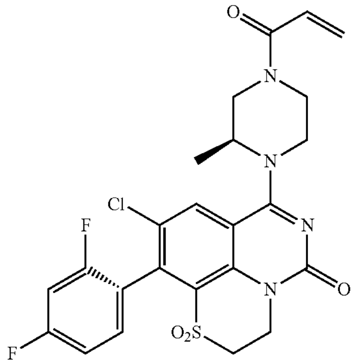 | 534.96 | 95.9 | (R)-7-((S)-4-acryloyl-2-methylpiperazin-1-yl)-9-chloro-10-(2,4-difluorophenyl)-2,3-dihydro-5H-[1,4]thiazino[2,3,4-ij]quinazolin-5-one 1,1-dioxide |
| 149 | 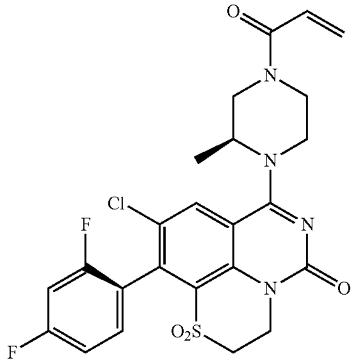 | 534.96 | 52.8 | (S)-7-((S)-4-acryloyl-2-methylpiperazin-1-yl)-9-chloro-10-(2,4-difluorophenyl)-2,3-dihydro-5H-[1,4]thiazino[2,3,4-ij]quinazolin-5-one 1,1-dioxide |
| 150 | 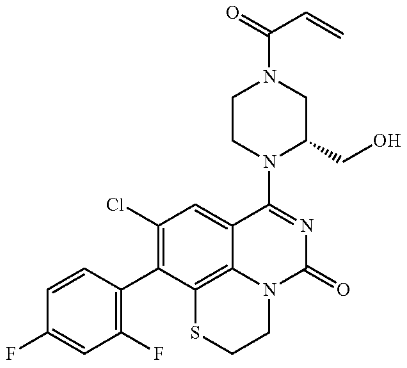 [SMILES: C=CC(=O)N1CCN(c2nc(=O)n3c4c(c(-c5ccc(F)cc5F)c(Cl)cc24)SCC3)[C@@H](CO)C1] | 518.96 | 59.9 | 7-((R)-4-acryloyl-2-(hydroxymethyl)piperazin-1-yl)-9-chloro-10-(2,4-difluorophenyl)-2,3-dihydro-5H-[1,4]thiazino[2,3,4-ij]quinazolin-5-one |

TABLE 3-continued

| Ex. No. | Structure | MW | % CAF @ 10 uM, 1 h | Name |
|---|---|---|---|---|
| 151 | 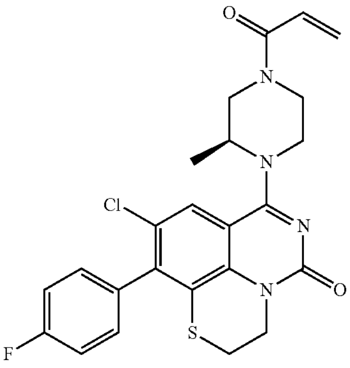 [SMILES: C=CC(=O)N1CCN(c2nc(=O)n3c4c(c(-c5ccc(F)cc5)c(Cl)cc24)SCC3)[C@@H](C)C1] | 484.97 | 94.1 | (S)-7-(4-acryloyl-2-methylpiperazin-1-yl)-9-chloro-10-(4-fluorophenyl)-2,3-dihydro-5H-[1,4]thiazino[2,3,4-ij]quinazolin-5-one |
| 152 | 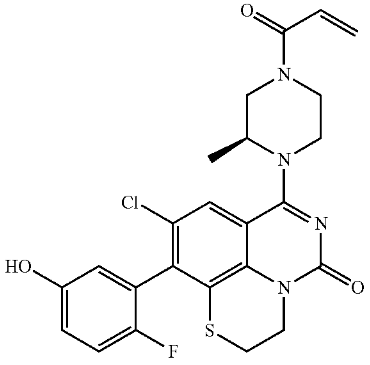 [SMILES: C=CC(=O)N1CCN(c2nc(=O)n3c4c(c(-c5cc(O)ccc5F)c(Cl)cc24)SCC3)[C@@H](C)C1] | 500.97 | 55.3 | 7-((S)-4-acryloyl-2-methylpiperazin-1-yl)-9-chloro-10-(2-fluoro-5-hydroxyphenyl)-2,3-dihydro-5H-[1,4]thiazino[2,3,4-ij]quinazolin-5-one |
| 153 | 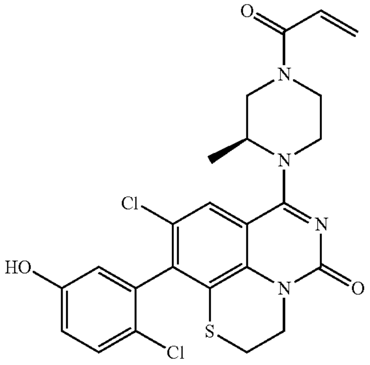 [SMILES: C=CC(=O)N1CCN(c2nc(=O)n3c4c(c(-c5cc(O)ccc5Cl)c(Cl)cc24)SCC3)[C@@H](C)C1] | 517.43 | 55.7 | 7-((S)-4-acryloyl-2-methylpiperazin-1-yl)-9-chloro-10-(2-fluoro-5-hydroxyphenyl)-2,3-dihydro-5H-[1,4]thiazino[2,3,4-ij]quinazolin-5-one |
| 154 | 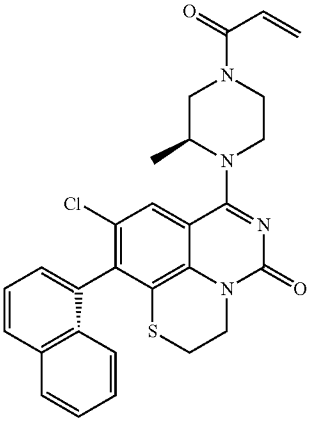 | 517.04 | 24 | (R)-7-((S)-4-acryloyl-2-methylpiperazin-1-yl)-9-chloro-10-(naphthalen-1-yl)-2,3-dihydro-5H-[1,4]thiazino[2,3,4-ij]quinazolin-5-one |

TABLE 3-continued

| Ex. No. | Structure | MW | % CAF @ 10 uM, 1 h | Name |
|---|---|---|---|---|
| 155 | 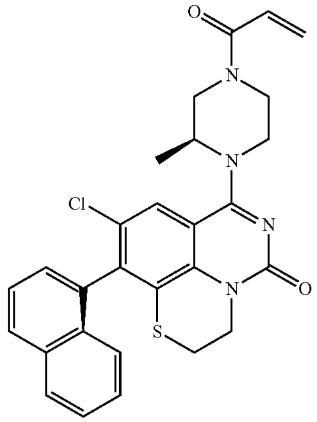 | 517.04 | 92.2 | (S)-7-((S)-4-acryloyl-2-methylpiperazin-1-yl)-9-chloro-10-(naphthalen-1-yl)-2,3-dihydro-5H-[1,4]thiazino[2,3,4-ij]quinazolin-5-one |
| 156 | 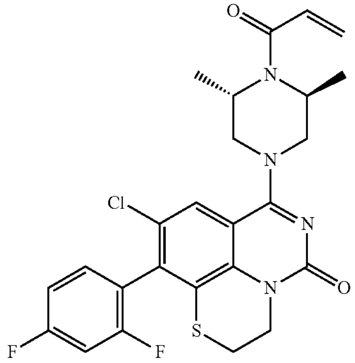 [SMILES: C=CC(=O)N1[C@@H](C)CN(c2nc(=O)n3c4c(c(-c5ccc(F)cc5F)c(Cl)cc24)SCC3)C[C@@H]1C] | 516.99 | 0 | 7-((3S,5S)-4-acryloyl-3,5-dimethylpiperazin-1-yl)-9-chloro-10-(2,4-difluorophenyl)-2,3-dihydro-5H-[1,4]thiazino[2,3,4-ij]quinazolin-5-one |
| 157 | 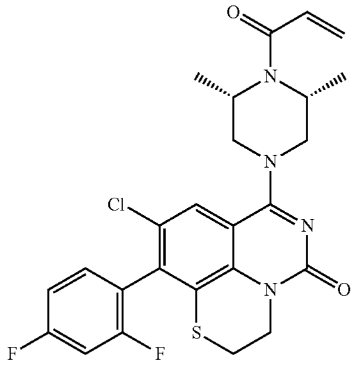 [SMILES: C=CC(=O)N1[C@H](C)CN(c2nc(=O)n3c4c(c(-c5ccc(F)cc5F)c(Cl)cc24)SCC3)C[C@@H]1C] | 516.99 | 95 | 7-((3R,5S)-4-acryloyl-3,5-dimethylpiperazin-1-yl)-9-chloro-10-(2,4-difluorophenyl)-2,3-dihydro-5H-[1,4]thiazino[2,3,4-ij]quinazolin-5-one |
| 158 | 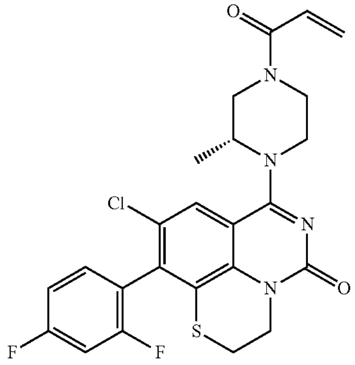 [SMILES: C=CC(=O)N1CCN(c2nc(=O)n3c4c(c(-c5ccc(F)cc5F)c(Cl)cc24)SCC3)[C@H](C)C1] | 502.96 | 64 | 7-((R)-4-acryloyl-2-methylpiperazin-1-yl)-9-chloro-10-(2,4-difluorophenyl)-2,3-dihydro-5H-[1,4]thiazino[2,3,4-ij]quinazolin-5-one |

TABLE 3-continued

| Ex. No. | Structure | MW | % CAF @ 10 uM, 1 h | Name |
|---|---|---|---|---|
| 159 | 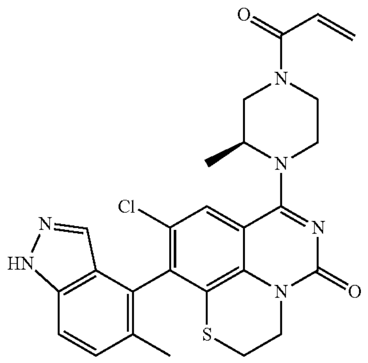 [SMILES: C=CC(=O)N1CCN(c2nc(=O)n3c4c(c(-c5c(C)ccc6[nH]ncc56)c(Cl)cc24)SCC3)[C@@H](C)C1] | 521.03 | 37.2 | 7-((S)-4-acryloyl-2-methylpiperazin-1-yl)-9-chloro-10-(5-methyl-1H-indazol-4-yl)-2,3-dihydro-5H-[1,4]thiazino[2,3,4-ij]quinazolin-5-one |
| 160 | 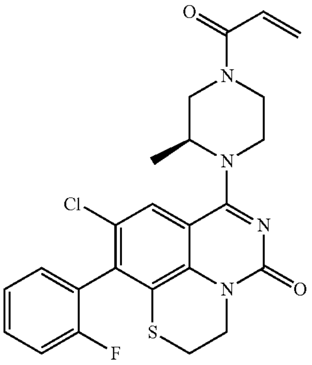 [SMILES: C=CC(=O)N1CCN(c2nc(=O)n3c4c(c(-c5ccccc5F)c(Cl)cc24)SCC3)[C@@H](C)C1] | 484.97 | 72.7 | 7-((S)-4-acryloyl-2-methylpiperazin-1-yl)-9-chloro-10-(2-fluorophenyl)-2,3-dihydro-5H-[1,4]thiazino[2,3,4-ij]quinazolin-5-one |
| 161 | 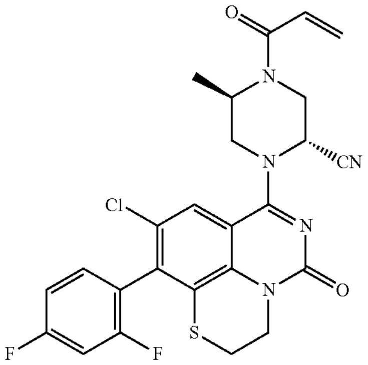 [SMILES: C=CC(=O)N1C[C@H](C#N)N(c2nc(=O)n3c4c(c(-c5ccc(F)cc5F)c(Cl)cc24)SCC3)C[C@H]1C] | 527.97 | 1 | (2R,5R)-4-acryloyl-1-(9-chloro-10-(2,4-difluorophenyl)-5-oxo-2,3-dihydro-5H-[1,4]thiazino[2,3,4-ij]quinazolin-7-yl)-5-methylpiperazine-2-carbonitrile |
| 162 | 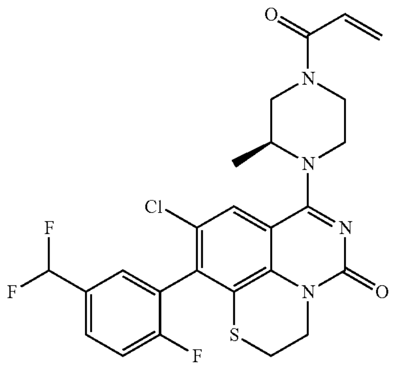 [SMILES: C=CC(=O)N1CCN(c2nc(=O)n3c4c(c(-c5cc(C(F)F)ccc5F)c(Cl)cc24)SCC3)[C@@H](C)C1] | 534.98 | 39 | 7-((S)-4-acryloyl-2-methylpiperazin-1-yl)-9-chloro-10-(5-(difluoromethyl)-2-fluorophenyl)-2,3-dihydro-5H-[1,4]thiazino[2,3,4-ij]quinazolin-5-one |

TABLE 3-continued

| Ex. No. | Structure | MW | % CAF @ 10 uM, 1 h | Name |
|---|---|---|---|---|
| 163 | 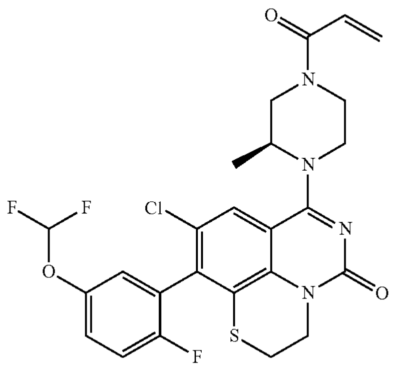 [SMILES: C=CC(=O)N1CCN(c2nc(=O)n3c4c(c(-c5cc(OC(F)F)ccc5F)c(Cl)cc24)SCC3)[C@@H](C)C1] | 550.98 | 41.4 | 7-((S)-4-acryloyl-2-methylpiperazin-1-yl)-9-chloro-10-(5-(difluoromethoxy)-2-fluorophenyl)-2,3-dihydro-5H-[1,4]thiazino[2,3,4-ij]quinazolin-5-one |
| 164 | 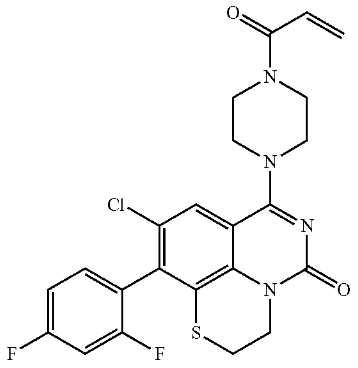 [SMILES: C=CC(=O)N1CCN(c2nc(=O)n3c4c(c(-c5ccc(F)cc5F)c(Cl)cc24)SCC3)CC1] | 488.94 | 95.1 | 7-(4-acryloylpiperazin-1-yl)-9-chloro-10-(2,4-difluorophenyl)-2,3-dihydro-5H-[1,4]thiazino[2,3,4-ij]quinazolin-5-one |
| 165 | 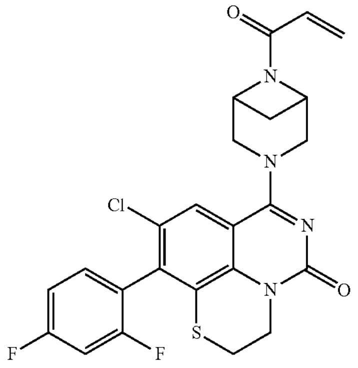 [SMILES: C=CC(=O)N1C2CC1CN(c1nc(=O)n3c4c(c(-c5ccc(F)cc5F)c(Cl)cc14)SCC3)C2] | 500.95 | 16.9 | 7-(6-acryloyl-3,6-diazabicyclo[3.1.1]heptan-3-yl)-9-chloro-10-(2,4-difluorophenyl)-2,3-dihydro-5H-[1,4]thiazino[2,3,4-ij]quinazolin-5-one |
| 166 | 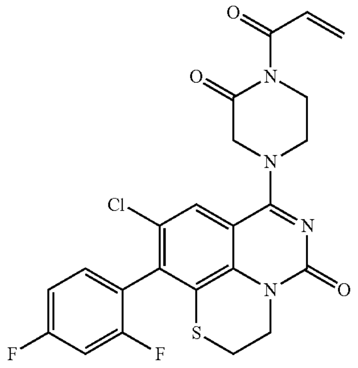 [SMILES: C=CC(=O)N1CCN(c2nc(=O)n3c4c(c(-c5ccc(F)cc5F)c(Cl)cc24)SCC3)CC1=O] | 502.92 | 65.5 | 7-(4-acryloyl-3-oxopiperazin-1-yl)-9-chloro-10-(2,4-difluorophenyl)-2,3-dihydro-5H-[1,4]thiazino[2,3,4-ij]quinazolin-5-one |

TABLE 3-continued

| Ex. No. | Structure | MW | % CAF @ 10 uM, 1 h | Name |
|---|---|---|---|---|
| 167 | 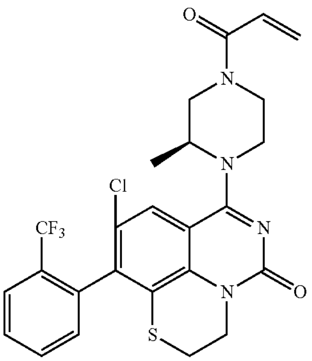 [SMILES: C=CC(=O)N1CCN(c2nc(=O)n3c4c(c(-c5ccccc5C(F)(F)F)c(Cl)cc24)SCC3)[C@@H](C)C1] | 534.98 | 69.8 | 7-((S)-4-acryloyl-2-methylpiperazin-1-yl)-9-chloro-10-(2-(trifluoromethyl)phenyl)-2,3-dihydro-5H-[1,4]thiazino[2,3,4-ij]quinazolin-5-one |
| 168 | 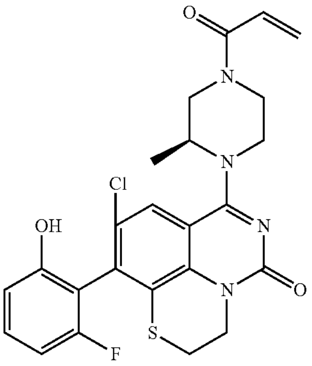 [SMILES: C=CC(=O)N1CCN(c2nc(=O)n3c4c(c(-c5c(O)cccc5F)c(Cl)cc24)SCC3)[C@@H](C)C1] | 500.97 | 30.6 | 7-((S)-4-acryloyl-2-methylpiperazin-1-yl)-9-chloro-10-(2-fluoro-6-hydroxyphenyl)-2,3-dihydro-5H-[1,4]thiazino[2,3,4-ij]quinazolin-5-one |
| 169 | 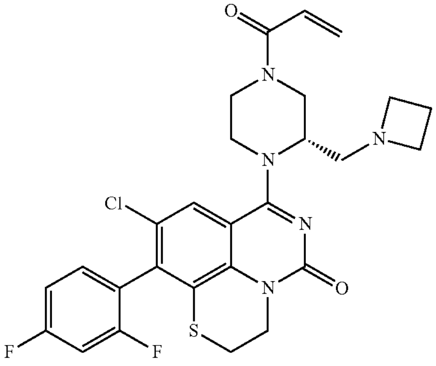 [SMILES: C=CC(=O)N1CCN(c2nc(=O)n3c4c(c(-c5ccc(F)cc5F)c(Cl)cc24)SCC3)[C@@H](CN2CCC2)C1] | 558.04 | 23.3 | 7-((S)-4-acryloyl-2-(azetidin-1-ylmethyl)piperazin-1-yl)-9-chloro-10-(2,4-difluorophenyl)-2,3-dihydro-5H-[1,4]thiazino[2,3,4-ij]quinazolin-5-one |
| 170 | 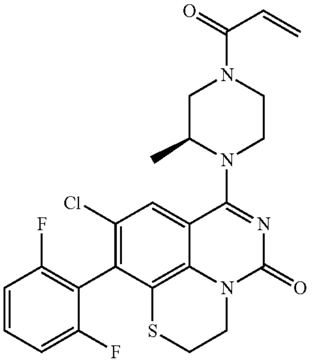 [SMILES: C=CC(=O)N1CCN(c2nc(=O)n3c4c(c(-c5c(F)cccc5F)c(Cl)cc24)SCC3)[C@@H](C)C1] | 502.96 | 75.9 | (S)-7-(4-acryloyl-2-methylpiperazin-1-yl)-9-chloro-10-(2,6-difluorophenyl)-2,3-dihydro-5H-[1,4]thiazino[2,3,4-ij]quinazolin-5-one |

TABLE 3-continued

| Ex. No. | Structure | MW | % CAF @ 10 uM, 1 h | Name |
|---|---|---|---|---|
| 171 | 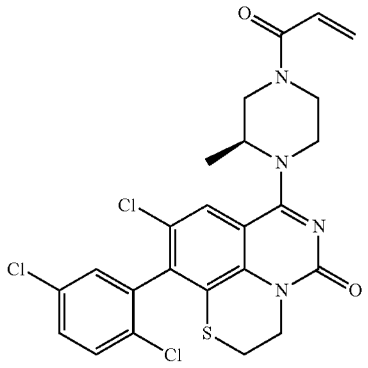 [SMILES: C=CC(=O)N1CCN(c2nc(=O)n3c4c(c(-c5cc(Cl)ccc5Cl)c(Cl)cc24)SCC3)[C@@H](C)C1] | 535.87 | 48.9 | 7-((S)-4-acryloyl-2-methylpiperazin-1-yl)-9-chloro-10-(2,5-dichlorophenyl)-2,3-dihydro-5H-[1,4]thiazino[2,3,4-ij]quinazolin-5-one |
| 172 | 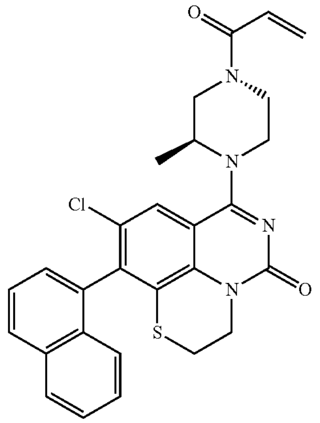 | 517.04 | 51.9 | 7-((S)-4-acryloyl-2-methylpiperazin-1-yl)-9-chloro-10-(naphthalen-1-yl)-2,3-dihydro-5H-[1,4]thiazino[2,3,4-ij]quinazolin-5-one |
| 173 | 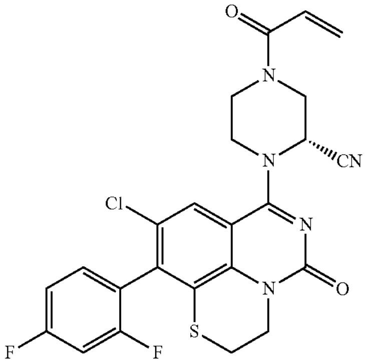 [SMILES: C=CC(=O)N1CCN(c2nc(=O)n3c4c(c(-c5ccc(F)cc5F)c(Cl)cc24)SCC3)[C@@H](C#N)C1] | 513.95 | 2.2 | (2R)-4-acryloyl-1-(9-chloro-10-(2,4-difluorophenyl)-5-oxo-2,3-dihydro-5H-[1,4]thiazino[2,3,4-ij]quinazolin-7-yl)piperazine-2-carbonitrile |
| 174 | 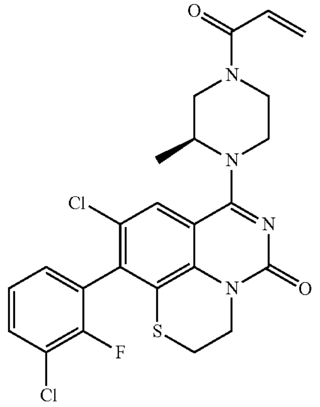 [SMILES: C=CC(=O)N1CCN(c2nc(=O)n3c4c(c(-c5cccc(Cl)c5F)c(Cl)cc24)SCC3)[C@@H](C)C1] | 519.42 | 93.8 | 7-((S)-4-acryloyl-2-methylpiperazin-1-yl)-9-chloro-10-(3-chloro-2-fluorophenyl)-2,3-dihydro-5H-[1,4]thiazino[2,3,4-ij]quinazolin-5-one |

TABLE 3-continued

| Ex. No. | Structure | MW | % CAF @ 10 uM, 1 h | Name |
|---|---|---|---|---|
| 175 | 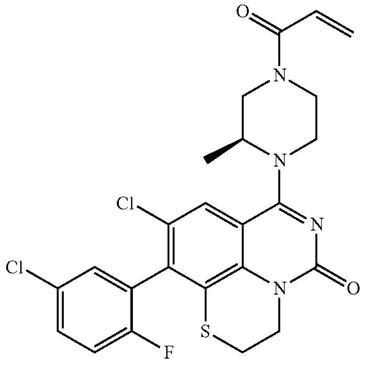 [SMILES: C=CC(=O)N1CCN(c2nc(=O)n3c4c(c(-c5cc(Cl)ccc5F)c(Cl)cc24)SCC3)[C@@H](C)C1] | 519.42 | 79.8 | 7-((S)-4-acryloyl-2-methylpiperazin-1-yl)-9-chloro-10-(5-chloro-2-fluorophenyl)-2,3-dihydro-5H-[1,4]thiazino[2,3,4-ij]quinazolin-5-one |
| 176 | 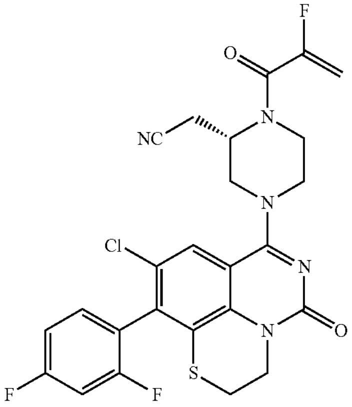 [SMILES: C=C(F)C(=O)N1CCN(c2nc(=O)n3c4c(c(-c5ccc(F)cc5F)c(Cl)cc24)SCC3)C[C@@H]1CC#N] | 545.96 | 40.5 | 2-((2S)-4-(9-chloro-10-(2,4-difluorophenyl)-5-oxo-2,3-dihydro-5H-[1,4]thiazino[2,3,4-ij]quinazolin-7-yl)-1-(2-fluoroacryloyl)piperazin-2-yl)acetonitrile |
| 177 | 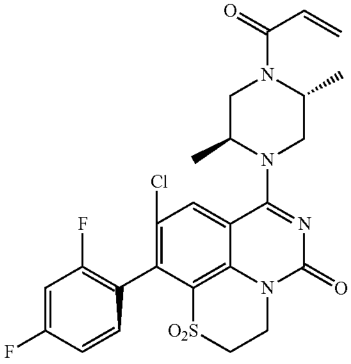 | 548.99 | 93.5 | (S)-7-((2S,5R)-4-acryloyl-2,5-dimethylpiperazin-1-yl)-9-chloro-10-(2,4-difluorophenyl)-2,3-dihydro-5H-[1,4]thiazino[2,3,4-ij]quinazolin-5-one 1,1-dioxide |
| 178 | 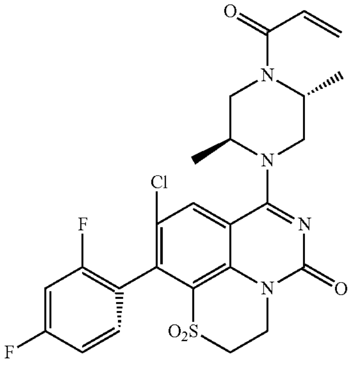 | 548.99 | 58.3 | (R)-7-((2S,5R)-4-acryloyl-2,5-dimethylpiperazin-1-yl)-9-chloro-10-(2,4-difluorophenyl)-2,3-dihydro-5H-[1,4]thiazino[2,3,4-ij]quinazolin-5-one 1,1-dioxide |

TABLE 3-continued

| Ex. No. | Structure | MW | % CAF @ 10 uM, 1 h | Name |
|---|---|---|---|---|
| 179 | 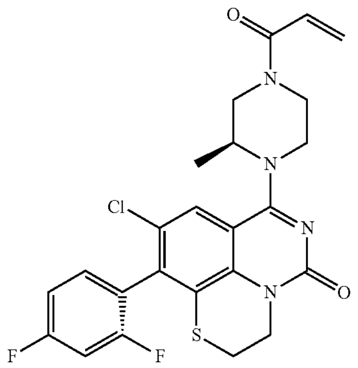 | 502.96 | 96 | (S)-7-((S)-4-acryloyl-2-methylpiperazin-1-yl)-9-chloro-10-(2,4-difluorophenyl)-2,3-dihydro-5H-[1,4]thiazino[2,3,4-ij]quinazolin-5-one |
| 180 | 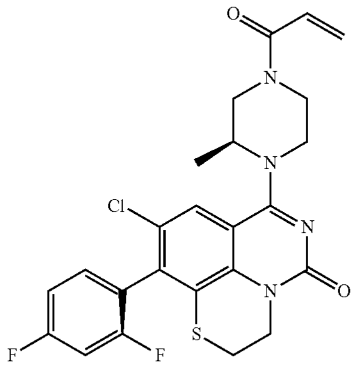 | 502.96 | 94.7 | (R)-7-((S)-4-acryloyl-2-methylpiperazin-1-yl)-9-chloro-10-(2,4-difluorophenyl)-2,3-dihydro-5H-[1,4]thiazino[2,3,4-ij]quinazolin-5-one |
| 181 | 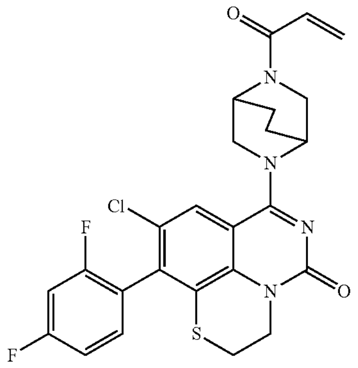 [SMILES: C=CC(=O)N1CC2CCC1CN2c1nc(=O)n2c3c(c(-c4ccc(F)cc4F)c(Cl)cc13)SCC2] | 514.97 | 28.7 | 7-(5-acryloyl-2,5-diazabicyclo[2.2.2]octan-2-yl)-9-chloro-10-(2,4-difluorophenyl)-2,3-dihydro-5H-[1,4]thiazino[2,3,4-ij]quinazolin-5-one |
| 182 | 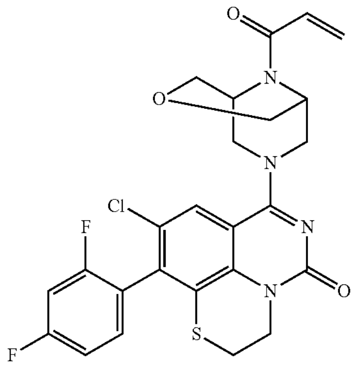 [SMILES: C=CC(=O)N1C2COCC1CN(c1nc(=O)n3c4c(c(-c5ccc(F)cc5F)c(Cl)cc14)SCC3)C2] | 530.97 | 94.4 | 7-(9-acryloyl-3-oxa-7,9-diazabicyclo[3.3.1]nonan-7-yl)-9-chloro-10-(2,4-difluorophenyl)-2,3-dihydro-5H-[1,4]thiazino[2,3,4-ij]quinazolin-5-one |

TABLE 3-continued

| Ex. No. | Structure | MW | % CAF @ 10 uM, 1 h | Name |
|---|---|---|---|---|
| 183 | 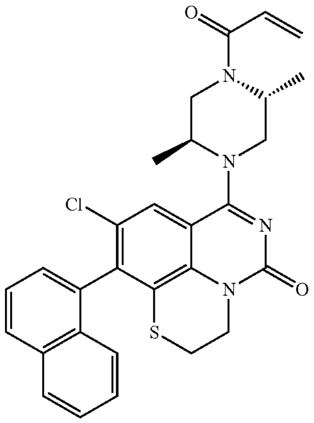 | 531.07 | 45.3 | 7-((2S,5R)-4-acryloyl-2,5-dimethylpiperazin-1-yl)-9-chloro-10-(naphthalen-1-yl)-2,3-dihydro-5H-[1,4]thiazino[2,3,4-ij]quinazolin-5-one |
| 184 | 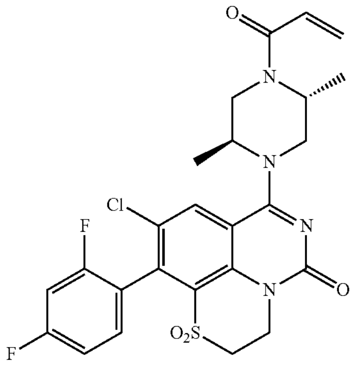 [SMILES: C=CC(=O)N1C[C@H](C)N(c2nc(=O)n3c4c(c(-c5ccc(F)cc5F)c(Cl)cc24)S(=O)(=O)CC3)C[C@H]1C] | 548.99 | 91.4 | 7-((2S,5R)-4-acryloyl-2,5-dimethylpiperazin-1-yl)-9-chloro-10-(2,4-difluorophenyl)-2,3-dihydro-5H-[1,4]thiazino[2,3,4-ij]quinazolin-5-one 1,1-dioxide |
| 185 | 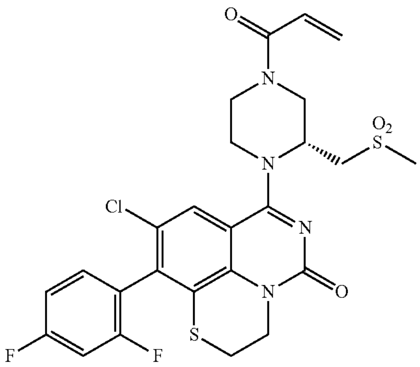 [SMILES: C=CC(=O)N1CCN(c2nc(=O)n3c4c(c(-c5ccc(F)cc5F)c(Cl)cc24)SCC3)[C@@H](CS(C)(=O)=O)C1] | 581.05 | 93.3 | 7-((R)-4-acryloyl-2-((methylsulfonyl)methyl)piperazin-1-yl)-9-chloro-10-(2,4-difluorophenyl)-2,3-dihydro-5H-[1,4]thiazino[2,3,4-ij]quinazolin-5-one |
| 186 | 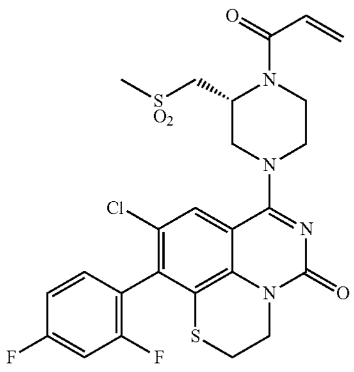 [SMILES: C=CC(=O)N1CCN(c2nc(=O)n3c4c(c(-c5ccc(F)cc5F)c(Cl)cc24)SCC3)C[C@@H]1CS(C)(=O)=O] | 581.05 | 92.6 | 7-((R)-4-acryloyl-3-((methylsulfonyl)methyl)piperazin-1-yl)-9-chloro-10-(2,4-difluorophenyl)-2,3-dihydro-5H-[1,4]thiazino[2,3,4-ij]quinazolin-5-one |

TABLE 3-continued

| Ex. No. | Structure | MW | % CAF @ 10 uM, 1 h | Name |
|---|---|---|---|---|
| 187 | 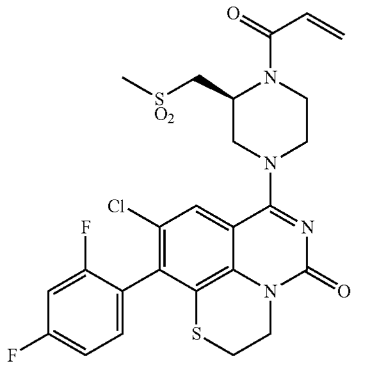 [SMILES: C=CC(=O)N1CCN(c2nc(=O)n3c4c(c(-c5ccc(F)cc5F)c(Cl)cc24)SCC3)C[C@H]1CS(C)(=O)=O] | 581.05 | 83.7 | 7-((S)-4-acryloyl-3-((methylsulfonyl)methyl)piperazin-1-yl)-9-chloro-10-(2,4-difluorophenyl)-2,3-dihydro-5H-[1,4]thiazino[2,3,4-ij]quinazolin-5-one |
| 188 | 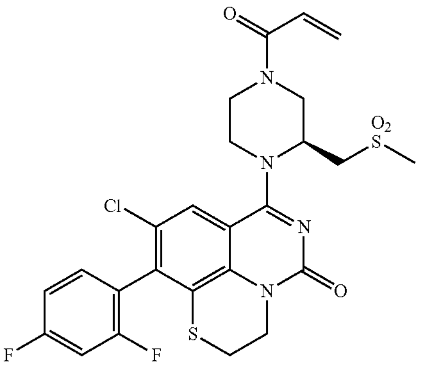 [SMILES: C=CC(=O)N1CCN(c2nc(=O)n3c4c(c(-c5ccc(F)cc5F)c(Cl)cc24)SCC3)[C@H](CS(C)(=O)=O)C1] | 581.05 | 89.2 | 7-((S)-4-acryloyl-2-((methylsulfonyl)methyl)piperazin-1-yl)-9-chloro-10-(2,4-difluorophenyl)-2,3-dihydro-5H-[1,4]thiazino[2,3,4-ij]quinazolin-5-one |
| 189 | 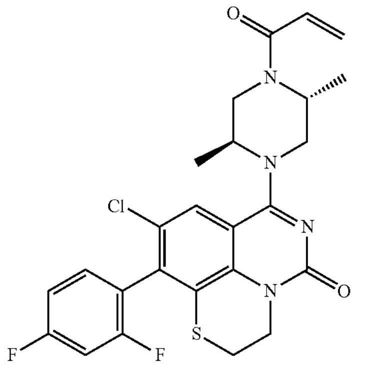 [SMILES: C=CC(=O)N1C[C@H](C)N(c2nc(=O)n3c4c(c(-c5ccc(F)cc5F)c(Cl)cc24)SCC3)C[C@H]1C] | 516.99 | 93.8 | 7-((2S,5R)-4-acryloyl-2,5-dimethylpiperazin-1-yl)-9-chloro-10-(2,4-difluorophenyl)-2,3-dihydro-5H-[1,4]thiazino[2,3,4-ij]quinazolin-5-one |
| 190 | 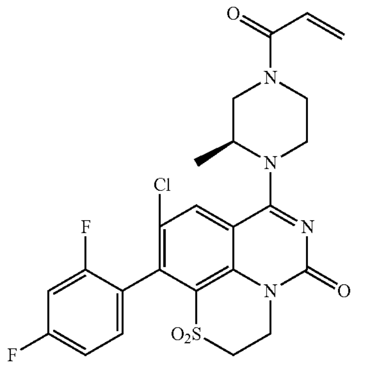 [SMILES: C=CC(=O)N1CCN(c2nc(=O)n3c4c(c(-c5ccc(F)cc5F)c(Cl)cc24)S(=O)(=O)CC3)[C@@H](C)C1] | 534.96 | 88.2 | 7-((S)-4-acryloyl-2-methylpiperazin-1-yl)-9-chloro-10-(2,4-difluorophenyl)-2,3-dihydro-5H-[1,4]thiazino[2,3,4-ij]quinazolin-5-one 1,1-dioxide |

TABLE 3-continued
| Ex. No. | Structure | MW | % CAF @ 10 uM, 1 h | Name |
|---|---|---|---|---|
| 191 | 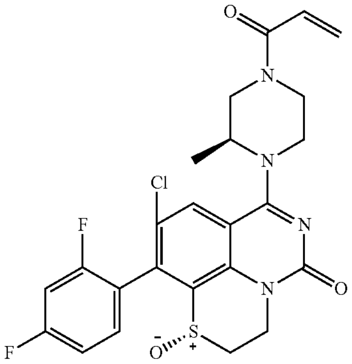 [SMILES: C=CC(=O)N1CCN(c2nc(=O)n3c4c(c(-c5ccc(F)cc5F)c(Cl)cc24)[S@@+]([O-])CC3)[C@@H](C)C1] | 518.96 | 26.6 | 7-((S)-4-acryloyl-2-methylpiperazin-1-yl)-9-chloro-10-(2,4-difluorophenyl)-2,3-dihydro-5H-[1,4]thiazino[2,3,4-ij]quinazolin-5-one 1-oxide |
| 192 | 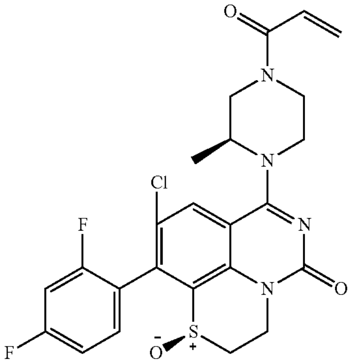 [SMILES: C=CC(=O)N1CCN(c2nc(=O)n3c4c(c(-c5ccc(F)cc5F)c(Cl)cc24)[S@+]([O-])CC3)[C@@H](C)C1] | 518.96 | 62.4 | 7-((S)-4-acryloyl-2-methylpiperazin-1-yl)-9-chloro-10-(2,4-difluorophenyl)-2,3-dihydro-5H-[1,4]thiazino[2,3,4-ij]quinazolin-5-one 1-oxide |
| 193 | 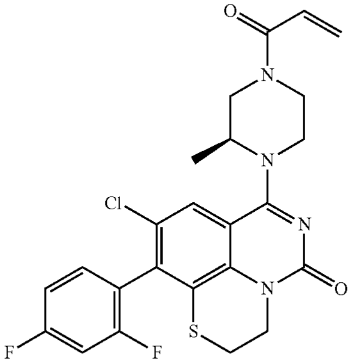 [SMILES: C=CC(=O)N1CCN(c2nc(=O)n3c4c(c(-c5ccc(F)cc5F)c(Cl)cc24)SCC3)[C@@H](C)C1] | 502.96 | 97 | 7-((S)-4-acryloyl-2-methylpiperazin-1-yl)-9-chloro-10-(2,4-difluorophenyl)-2,3-dihydro-5H-[1,4]thiazino[2,3,4]ij]quinazolin-5-one |

TABLE 4

| Ex. | Name | Structure | MW | % CAF @ 10 μM, 1 h |
|---|---|---|---|---|
| 338 | 8-(9-acryloyl-7-oxo-3,9-diazabicyclo[3.3.1]nonan-3-yl)-11-(2,4-difluorophenyl)-10-(trifluoromethyl)-3,4-dihydro-2H,6H-[1,4]oxazepino[2,3,4-ij]quinazolin-6-one | 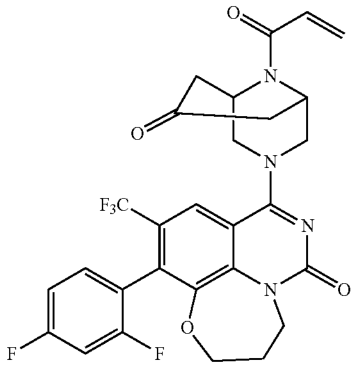 [SMILES: C=CC(=O)N1C2CC(=O)CC1CN(c1nc(=O)n3c4c(c(-c5ccc(F)cc5F)c(C(F)(F)F)cc14)OCCC3)C2] | 574.5 | 95.3 |
| 137 | (R)-7-((S)-4-acryloyl-2-methylpiperazin-1-yl)-9-chloro-3-(methoxymethyl)-10-(2,4,6-trifluorophenyl)-2,3-dihydro-5H-[1,4]thiazino[2,3,4-ij]quinazolin-5-one | 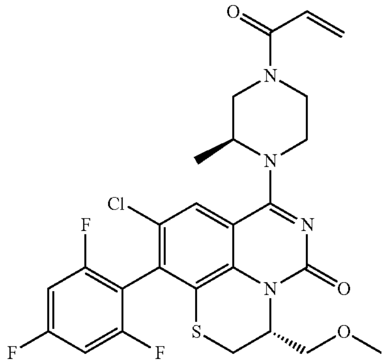 [SMILES: C=CC(=O)N1CCN(c2nc(=O)n3c4c(c(-c5c(F)cc(F)cc5F)c(Cl)cc24)SC[C@H]3COC)[C@@H](C)C1] | 565.1 | 86.8 |
| 130 | (3R)-7-((S)-4-acryloyl-2-methylpiperazin-1-yl)-9-chloro-10-(2,4-difluorophenyl)-3-(methoxymethyl)-2,3-dihydro-5H-[1,4]thiazino[2,3,4-ij]quinazolin-5-one | 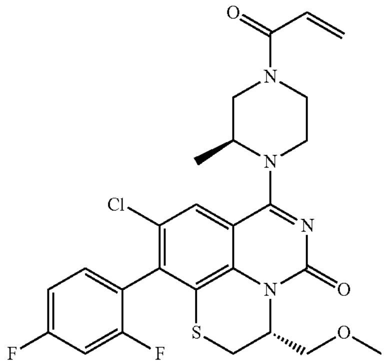 | 547.1 | 94.5 |
| 99 | (3R)-7-((S)-4-acryloyl-2-methylpiperazin-1-yl)-9-chloro-10-(2,4-difluorophenyl)-3-methyl-2H-[1,4]thiazino[2,3,4-ij]quinazolin-5(3H)-one | 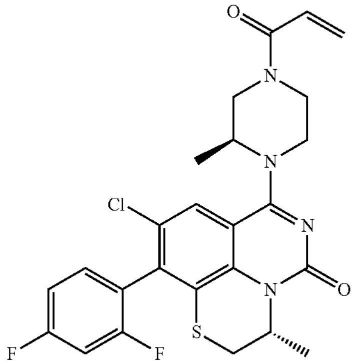 [SMILES: C=CC(=O)N1CCN(c2nc(=O)n3c4c(c(-c5ccc(F)cc5F)c(Cl)cc24)SC[C@H]3C)[C@@H](C)C1] | 517.1 | 87.2 |

TABLE 4-continued

| Ex. | Name | Structure | MW | % CAF @ 10 μM, 1 h |
|---|---|---|---|---|
| 339 | (R)-3-(3-((1S,4S)-2-oxa-5-azabicyclo[2.2.1]heptan-5-yl)propyl)-7-((S)-4-acryloyl-2-methylpiperazin-1-yl)-9-chloro-10-(2,4,6-trifluorophenyl)-2H-[1,4]thiazino[2,3,4-ij]quinazolin-5(3H)-one | 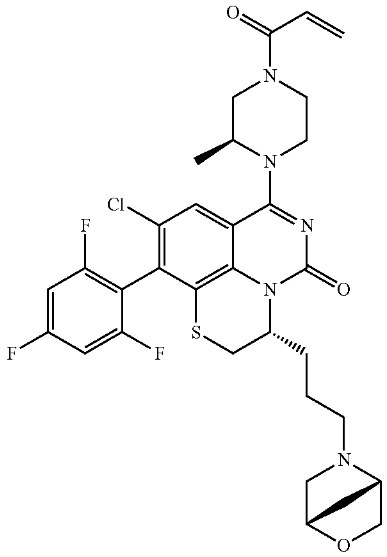 [SMILES: C=CC(=O)N1CCN(c2nc(=O)n3c4c(c(-c5c(F)cc(F)cc5F)c(Cl)cc24)SC[C@H]3CCCN2C[C@@H]3C[C@H]2CO3)[C@@H](C)C1] | 660.2 | 96.6 |
| 340 | (S)-3-(3-((1S,4S)-2-oxa-5-azabicyclo[2.2.1]heptan-5-yl)propyl)-7-((S)-4-acryloyl-2-methylpiperazin-1-yl)-9-chloro-10-(2,4,6-trifluorophenyl)-2H-[1,4]thiazino[2,3,4-ij]quinazolin-5(3H)-one | 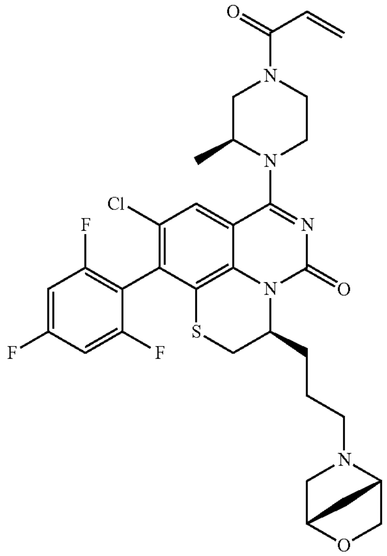 [SMILES: C=CC(=O)N1CCN(c2nc(=O)n3c4c(c(-c5c(F)cc(F)cc5F)c(Cl)cc24)SC[C@@H]3CCCN2C[C@@H]3C[C@H]2CO3)[C@@H](C)C1] | 660.2 | 96.9 |
| 341 | (3R)-3-(3-((1S,4S)-2-oxa-5-azabicyclo[2.2.1]heptan-5-yl)propyl)-7-((S)-4-acryloyl-2-methylpiperazin-1-yl)-9-chloro-10-(2,4-difluorophenyl)-2H-[1,4]thiazino[2,3,4-ij]quinazolin-5(3H)-one | 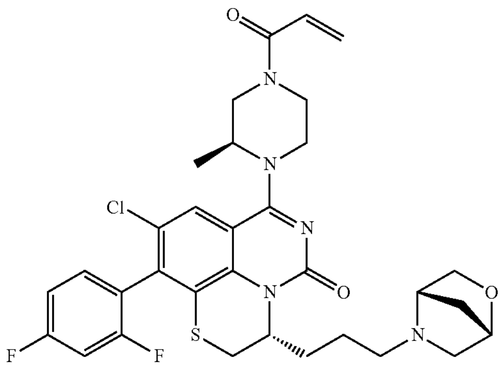 [SMILES: C=CC(=O)N1CCN(c2nc(=O)n3c4c(c(-c5ccc(F)cc5F)c(Cl)cc24)SC[C@H]3CCCN2C[C@@H]3C[C@H]2CO3)[C@@H](C)C1] | 642.3 | 96.5 |

TABLE 4-continued

| Ex. | Name | Structure | MW | % CAF @ 10 μM, 1 h |
|---|---|---|---|---|
| 342 | (3S)-3-(3-((1S,4S)-2-oxa-5-azabicyclo[2.2.1]heptan-5-yl)propyl)-7-((S)-4-acryloyl-2-methylpiperazin-1-yl)-9-chloro-10-(2,4-difluorophenyl)-2H-[1,4]thiazino[2,3,4-ij]quinazolin-5(3H)-one | 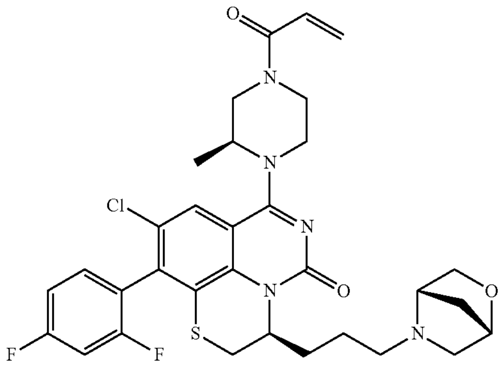 [SMILES: C=CC(=O)N1CCN(c2nc(=O)n3c4c(c(-c5ccc(F)cc5F)c(Cl)cc24)SC[C@@H]3CCCN2C[C@@H]3C[C@H]2CO3)[C@@H](C)C1] | 642.2 | 94.7 |
| 343 | (S)-7-((S)-4-acryloyl-2-methylpiperazin-1-yl)-9-chloro-3-((1-methylpiperidin-4-yl)methyl)-10-(2,4,6-trifluorophenyl)-2H-[1,4]thiazino[2,3,4-ij]quinazolin-5(3H)-one | 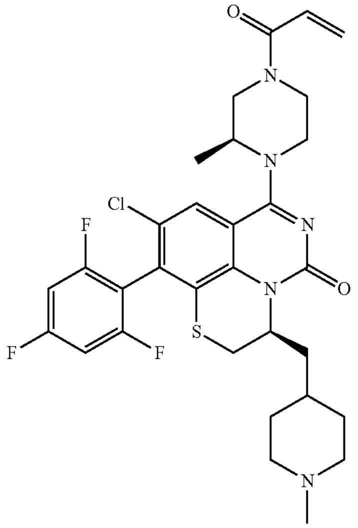 [SMILES: C=CC(=O)N1CCN(c2nc(=O)n3c4c(c(-c5c(F)cc(F)cc5F)c(Cl)cc24)SC[C@@H]3CC2CCN(C)CC2)[C@@H](C)C1] | 632.2 | 96.7 |
| 344 | (R)-7-((S)-4-acryloyl-2-methylpiperazin-1-yl)-9-chloro-3-((1-methylpiperidin-4-yl)methyl)-10-(2,4,6-trifluorophenyl)-2H-[1,4]thiazino[2,3,4-ij]quinazolin-5(3H)-one | 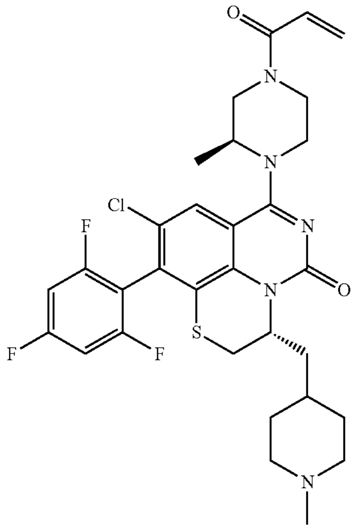 [SMILES: C=CC(=O)N1CCN(c2nc(=O)n3c4c(c(-c5c(F)cc(F)cc5F)c(Cl)cc24)SC[C@H]3CC2CCN(C)CC2)[C@@H](C)C1] | 632.2 | 94.8 |

TABLE 4-continued

| Ex. | Name | Structure | MW | % CAF @ 10 μM, 1 h |
|---|---|---|---|---|
| 345 | (3R)-7-((S)-4-acryloyl-2-methylpiperazin-1-yl)-9-chloro-10-(2,4-difluorophenyl)-3-((1-methylpiperidin-4-yl)methyl)-2H-[1,4]thiazino[2,3,4-ij]quinazolin-5(3H)-one | 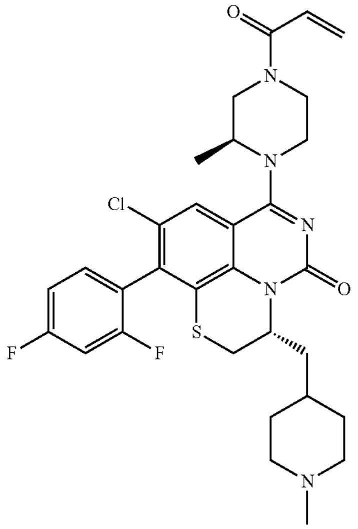 [SMILES: C=CC(=O)N1CCN(c2nc(=O)n3c4c(c(-c5ccc(F)cc5F)c(Cl)cc24)SC[C@H]3CC2CCN(C)CC2)[C@@H](C)C1] | 614.2 | 82.4 |
| 346 | (3R)-7-((S)-4-acryloyl-2-methylpiperazin-1-yl)-9-chloro-10-(2,4-difluorophenyl)-3-((4-ethylpiperazin-1-yl)methyl)-2H-[1,4]thiazino[2,3,4-ij]quinazolin-5(3H)-one | 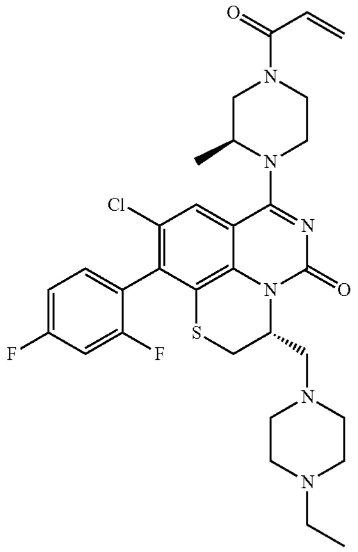 [SMILES: C=CC(=O)N1CCN(c2nc(=O)n3c4c(c(-c5ccc(F)cc5F)c(Cl)cc24)SC[C@H]3CN2CCN(CC)CC2)[C@@H](C)C1] | 629.3 | 79.3 |
| 76 | 7-((S)-4-acryloyl-2-methylpiperazin-1-yl)-9-chloro-10-(2,4-difluorophenyl)-2,2-dimethyl-2,3-dihydro-5H-[1,4]thiazino[2,3,4-ij]quinazolin-5-one | 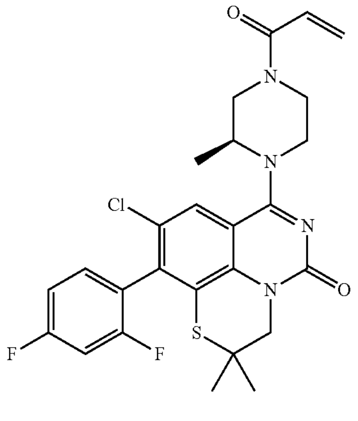 [SMILES: C=CC(=O)N1CCN(c2nc(=O)n3c4c(c(-c5ccc(F)cc5F)c(Cl)cc24)SC(C)(C)C3)[C@@H](C)C1] | 531.2 | 86.8 |

TABLE 4-continued
| Ex. | Name | Structure | MW | % CAF @ 10 μM, 1 h |
|---|---|---|---|---|
| 347 | (3R)-7-((S)-4-acryloyl-2-methylpiperazin-1-yl)-9-chloro-3-((4-(2,2-difluoroethyl)piperazin-1-yl)methyl)-10-(2,4-difluorophenyl)-2H-[1,4]thiazino[2,3,4-ij]quinazolin-5(3H)-one | 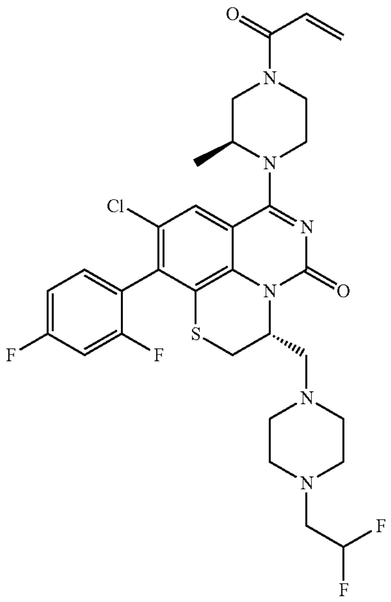 [SMILES: C=CC(=O)N1CCN(c2nc(=O)n3c4c(c(-c5ccc(F)cc5F)c(Cl)cc24)SC[C@H]3CN2CCN(CC(F)F)CC2)[C@@H](C)C1] | 665.2 | 82.5 |
| 348 | (3R)-7-((S)-4-acryloyl-2-methylpiperazin-1-yl)-9-chloro-3-((1-(2,2-difluoroethyl)piperidin-4-yl)methyl)-10-(2,4-difluorophenyl)-2H-[1,4]thiazino[2,3,4-ij]quinazolin-5(3H)-one | 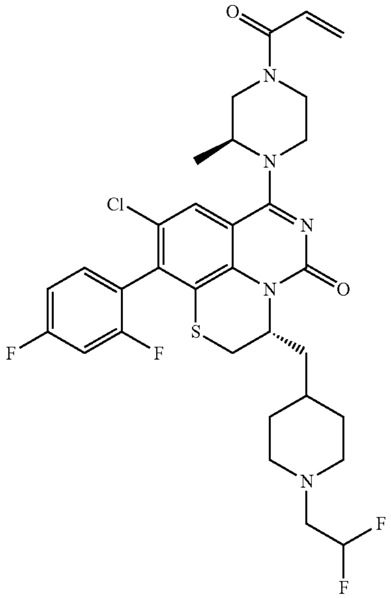 [SMILES: C=CC(=O)N1CCN(c2nc(=O)n3c4c(c(-c5ccc(F)cc5F)c(Cl)cc24)SC[C@H]3CC2CCN(CC(F)F)CC2)[C@@H](C)C1] | 664.3 | 92 |

TABLE 4-continued
| Ex. | Name | Structure | MW | % CAF @ 10 μM, 1 h |
|---|---|---|---|---|
| 349 | (R)-7-((S)-4-acryloyl-2-methylpiperazin-1-yl)-9-chloro-3-((1-(2,2-difluoroethyl)piperidin-4-yl)methyl)-10-(4-fluorophenyl)-2H-[1,4]thiazino[2,3,4-ij]quinazolin-5(3H)-one | 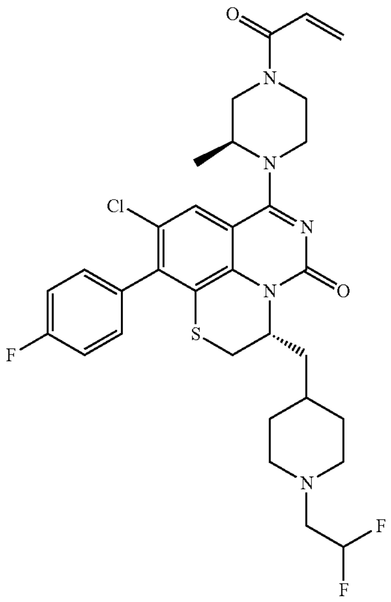 [SMILES: C=CC(=O)N1CCN(c2nc(=O)n3c4c(c(-c5ccc(F)cc5)c(Cl)cc24)SC[C@H]3CC2CCN(CC(F)F)CC2)[C@@H](C)C1] | 646.2 | 94 |
| 350 | (3S)-7-((S)-4-acryloyl-2-methylpiperazin-1-yl)-10-(2,4-difluorophenyl)-3-((4-ethylpiperazin-1-yl)methyl)-9-(trifluoromethyl)-2H-[1,4]thiazino[2,3,4-ij]quinazolin-5(3H)-one | 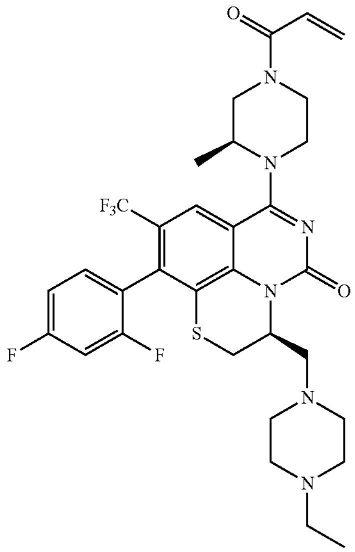 [SMILES: C=CC(=O)N1CCN(c2nc(=O)n3c4c(c(-c5ccc(F)cc5F)c(C(F)(F)F)cc24)SC[C@@H]3CN2CCN(CC)CC2)[C@@H](C)C1] | 663.3 | 95 |

TABLE 4-continued
| Ex. | Name | Structure | MW | % CAF @ 10 μM, 1 h |
|---|---|---|---|---|
| 351 | (S)-7-((S)-4-acryloyl-2-methylpiperazin-1-yl)-9-chloro-3-((4-ethylpiperazin-1-yl)methyl)-10-(2,4,6-trifluorophenyl)-2H-[1,4]thiazino[2,3,4-ij]quinazolin-5(3H)-one | 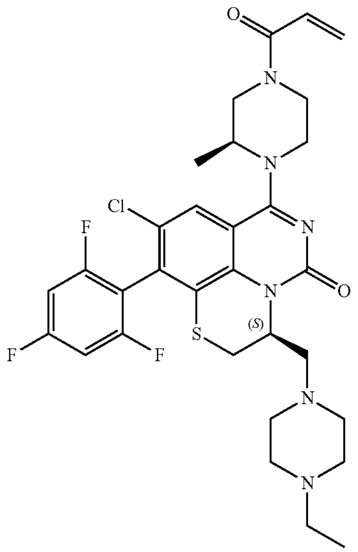 | 647.2 | 74 |
| 352 | (3S)-7-((S)-4-acryloyl-2-methylpiperazin-1-yl)-10-(2,4-difluorophenyl)-3-((4-(oxetan-3-yl)piperazin-1-yl)methyl)-9-(trifluoromethyl)-2H-[1,4]thiazino[2,3,4-ij]quinazolin-5(3H)-one | 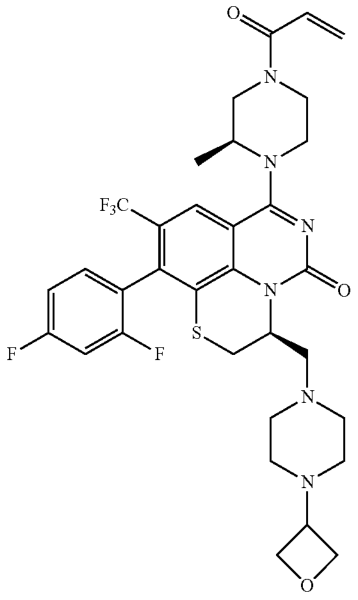 [SMILES: C=CC(=O)N1CCN(c2nc(=O)n3c4c(c(-c5ccc(F)cc5F)c(C(F)(F)F)cc24)SC[C@@H]3CN2CCN(C3COC3)CC2)[C@@H](C)C1] | 691.2 | 96 |

TABLE 4-continued
| Ex. | Name | Structure | MW | % CAF @ 10 μM, 1 h |
|---|---|---|---|---|
| 353 | (3S)-7-((S)-4-acryloyl-2-methylpiperazin-1-yl)-10-(2,4-difluorophenyl)-3-((1-ethylpiperidin-4-yl)methyl)-9-(trifluoromethyl)-2H-[1,4]thiazino[2,3,4-ij]quinazolin-5(3H)-one | 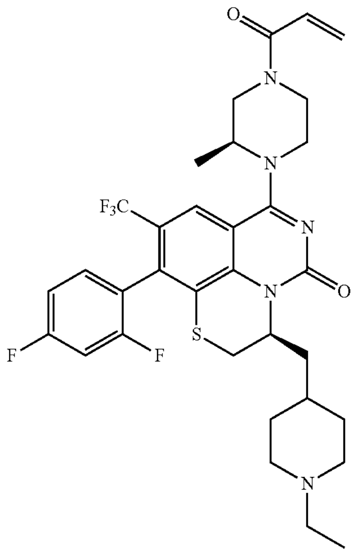 [SMILES: C=CC(=O)N1CCN(c2nc(=O)n3c4c(c(-c5ccc(F)cc5F)c(C(F)(F)F)cc24)SC[C@@H]3CC2CCN(CC)CC2)[C@@H](C)C1] | 662.2 | 97 |
| 354 | (3S)-7-((S)-4-acryloyl-2-methylpiperazin-1-yl)-9-chloro-10-(2,4-difluorophenyl)-3-((4-ethylpiperazin-1-yl)methyl)-2H-[1,4]thiazino[2,3,4-ij]quinazolin-5(3H)-one | 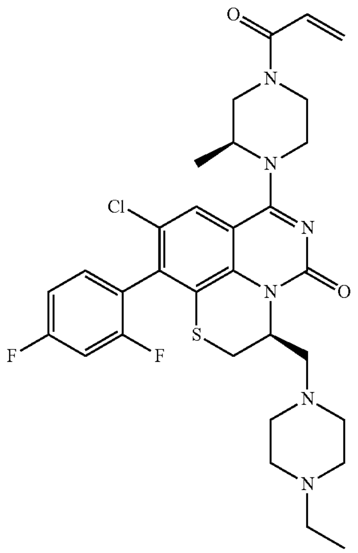 [SMILES: C=CC(=O)N1CCN(c2nc(=O)n3c4c(c(-c5ccc(F)cc5F)c(Cl)cc24)SC[C@@H]3CN2CCN(CC)CC2)[C@@H](C)C1] | 629.3 | 96 |

TABLE 4-continued
| Ex. | Name | Structure | MW | % CAF @ 10 μM, 1 h |
|---|---|---|---|---|
| 355 | (3S)-7-((S)-4-acryloyl-2-methylpiperazin-1-yl)-9-chloro-10-(2,4-difluorophenyl)-3-((4-(oxetan-3-yl)piperazin-1-yl)methyl)-2H-[1,4]thiazino[2,3,4-ij]quinazolin-5(3H)-one | 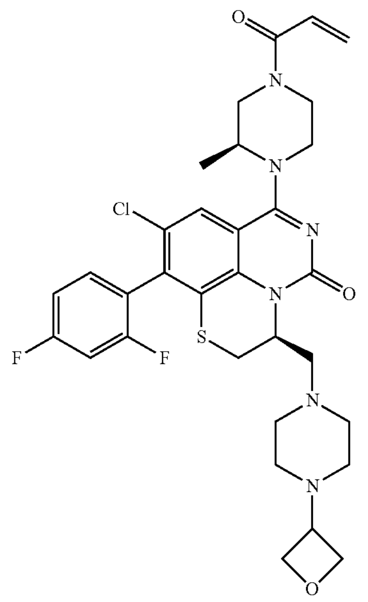 [SMILES: C=CC(=O)N1CCN(c2nc(=O)n3c4c(c(-c5ccc(F)cc5F)c(Cl)cc24)SC[C@@H]3CN2CCN(C3COC3)CC2)[C@@H](C)C1] | 657.3 | 96 |
| 356 | (3S)-7-((S)-4-acryloyl-2-methylpiperazin-1-yl)-9-chloro-3-((4-(2,2-difluoroethyl)piperazin-1-yl)methyl)-10-(2,4-difluorophenyl)-2H-[1,4]thiazino[2,3,4-ij]quinazolin-5(3H)-one | 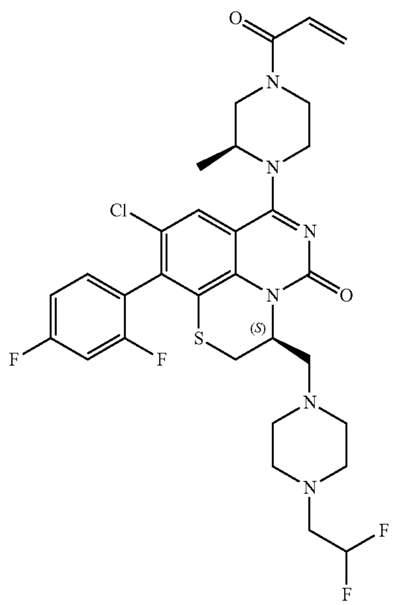 | 665.3 | 95 |

TABLE 4-continued
| Ex. | Name | Structure | MW | % CAF @ 10 μM, 1 h |
|---|---|---|---|---|
| 19 | (3S)-7-((S)-4-acryloyl-2-methylpiperazin-1-yl)-3-((4-(2,2-difluoroethyl)piperazin-1-yl)methyl)-10-(2,4-difluorophenyl)-9-(trifluoromethyl)-2H-[1,4]thiazino[2,3,4-ij]quinazolin-5(3H)-one | 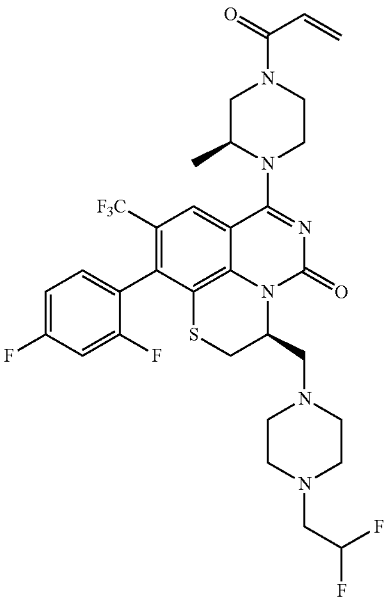 [SMILES: C=CC(=O)N1CCN(c2nc(=O)n3c4c(c(-c5ccc(F)cc5F)c(C(F)(F)F)cc24)SC[C@@H]3CN2CCN(CC(F)F)CC2)[C@@H](C)C1] | 699.6 | 96 |
In embodiments, there is provided a compound selected from:
(1100)
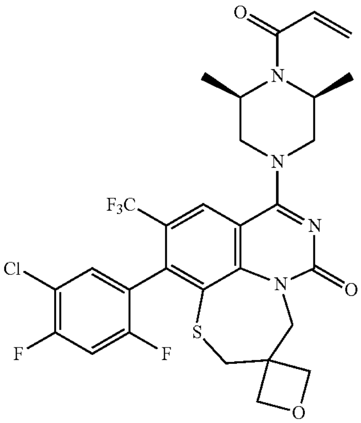
,
(1101)
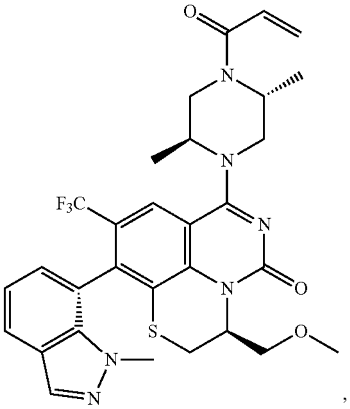
,
-continued
(1102)
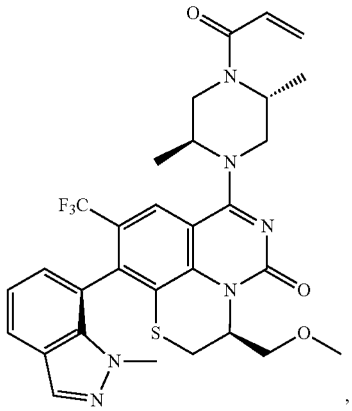
,
(1103)
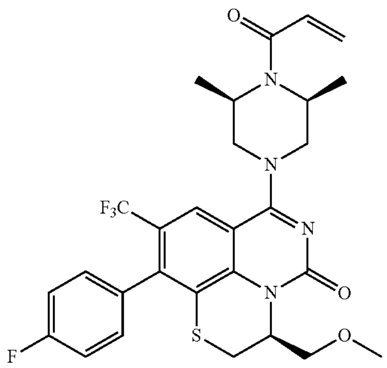
, -continued
(1104)
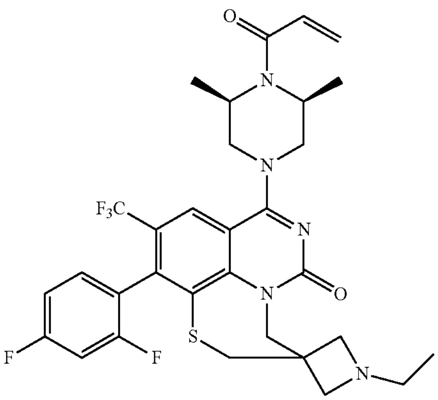
,
(1105)
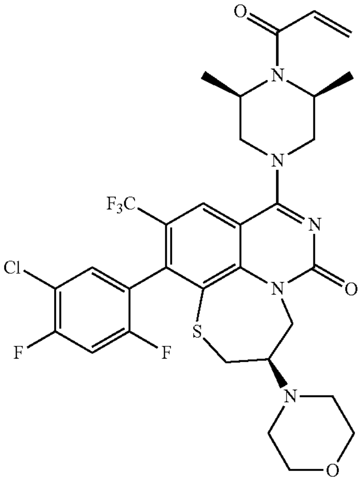
,
(1106)
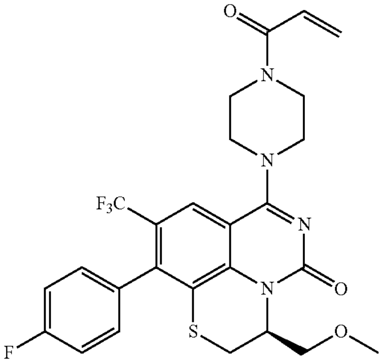
,
(1107)
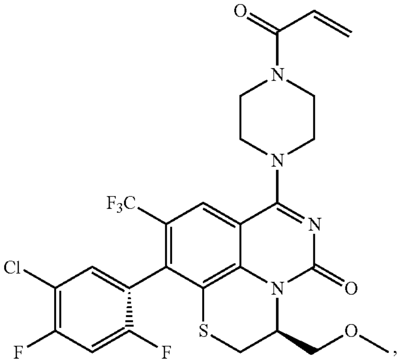
,
-continued
(1108)
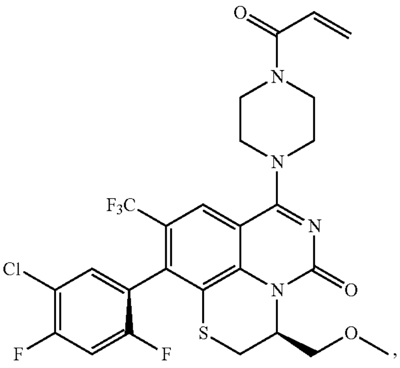
,
(1109)
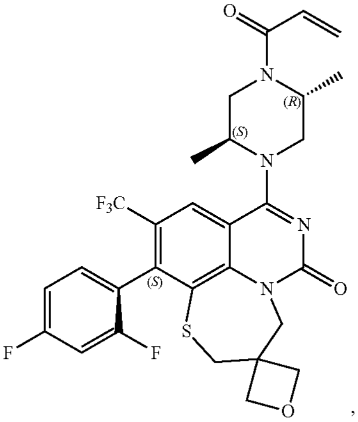
,
(1110)
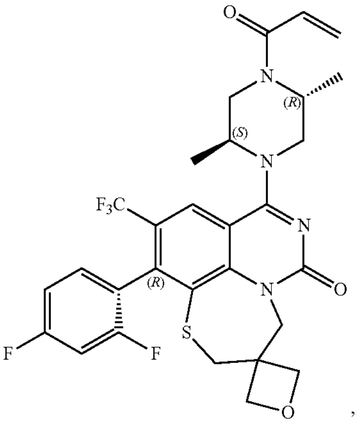
,
(1111)
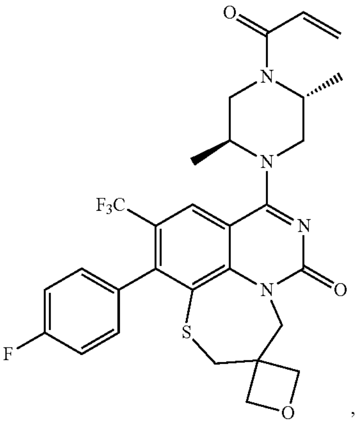
, (1112)
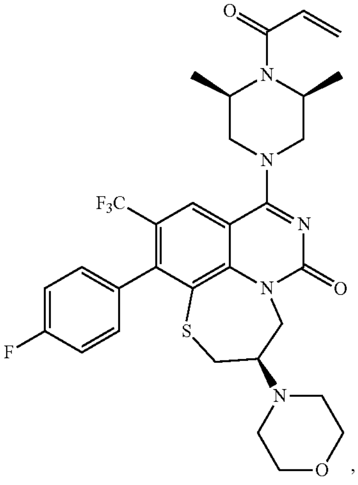
,
(1113)
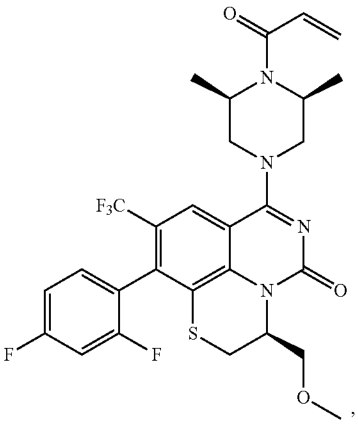
,
(1114)
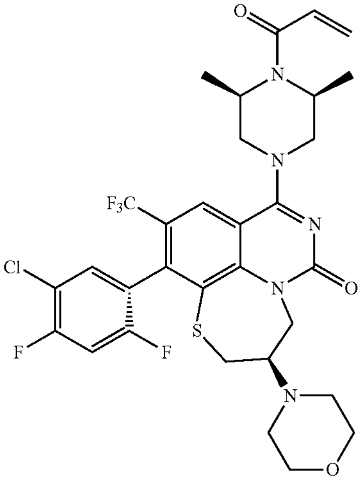
,
(1115)
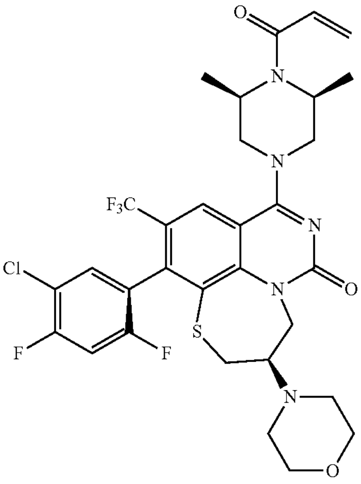
,
(1116)
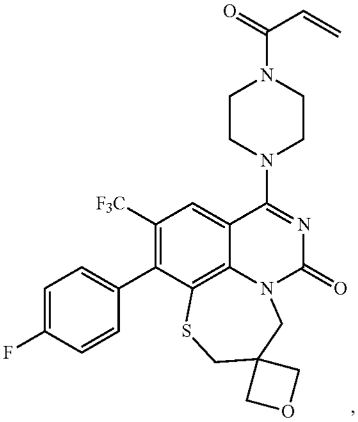
,
(1117)
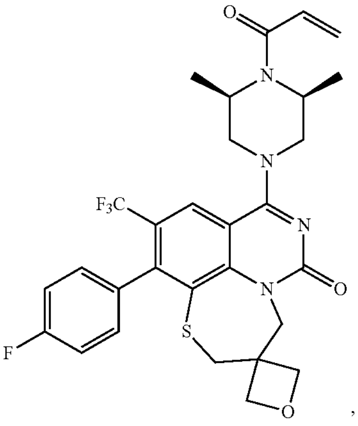
, -continued
(1118)
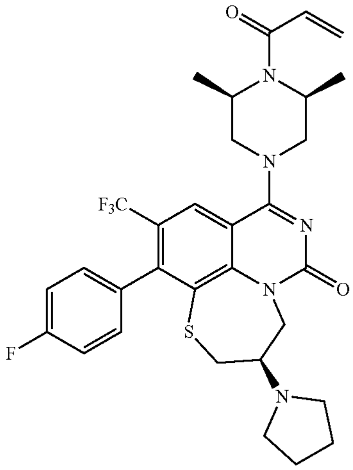
,
(1119)
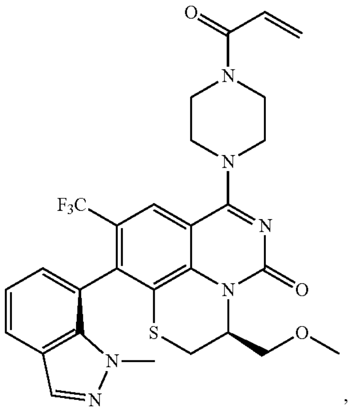
,
(1120)
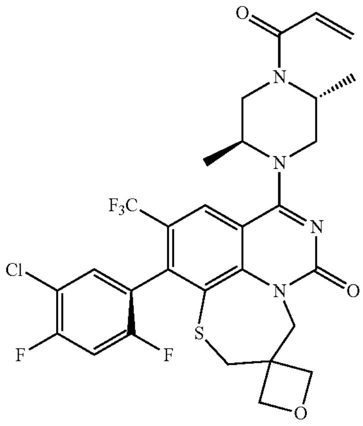
,
-continued
(1121)
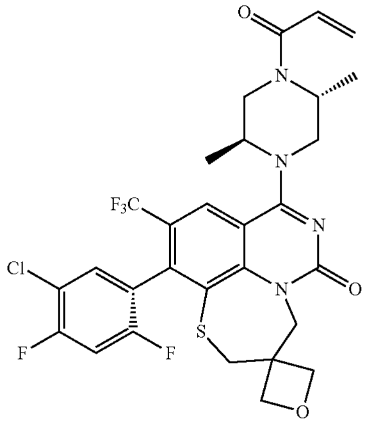
,
(1122)
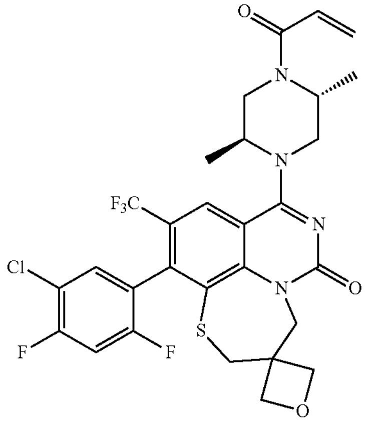
,
(1123)
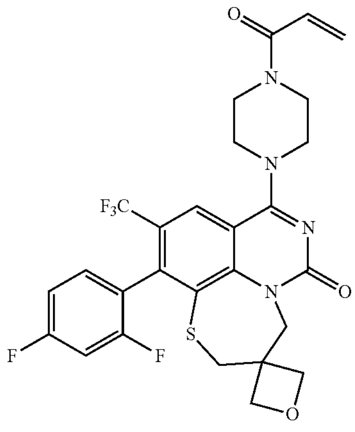
, -continued
(1124)
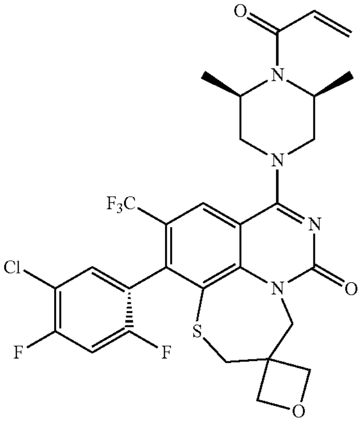
,
(1125)
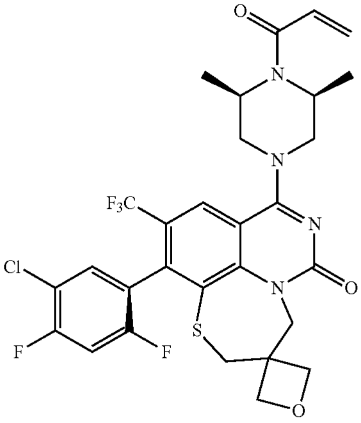
,
(1126)
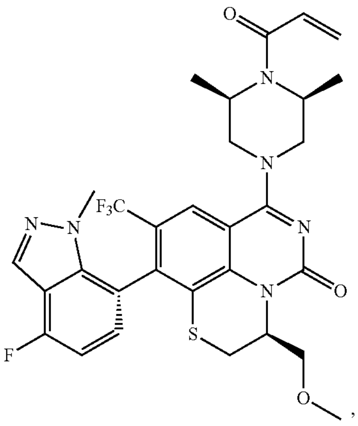
,
-continued
(1127)
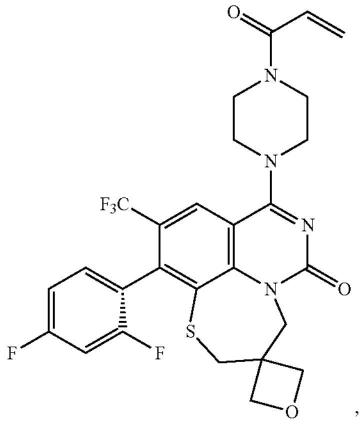
,
(1128)
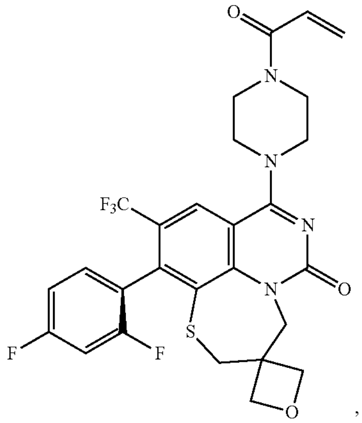
,
(1129)
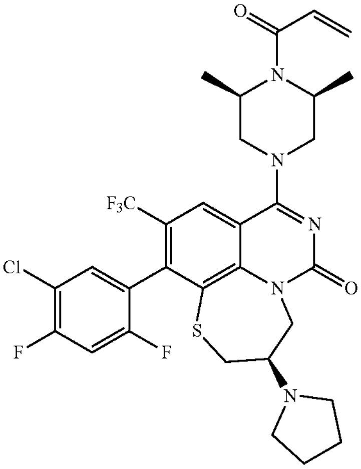
, -continued
(1130)
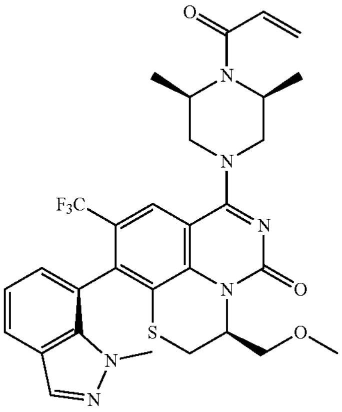
,
(1131)
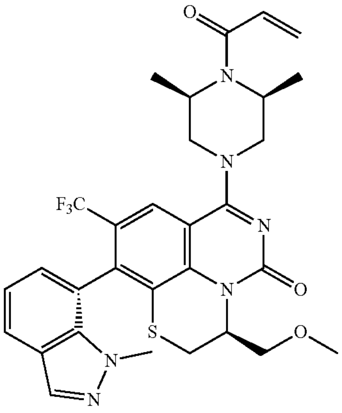
,
(1132)
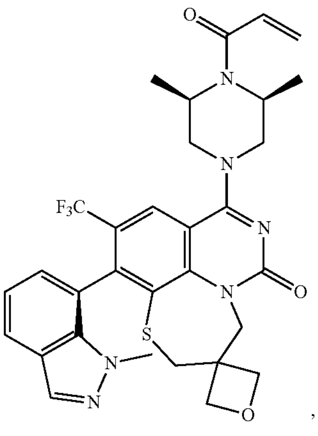
,
(1133)
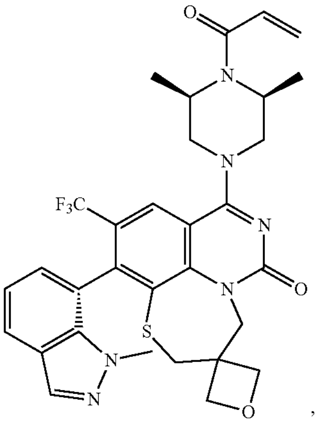
,
(1134)
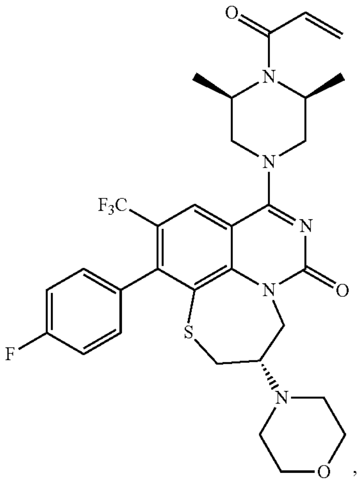
,
(1135)
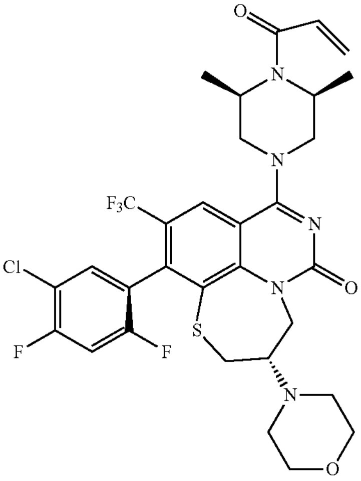
, -continued
(1136)
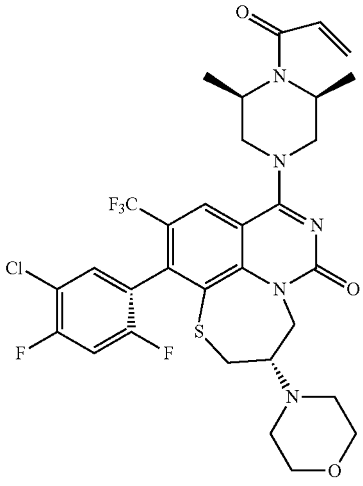
,
(1137)
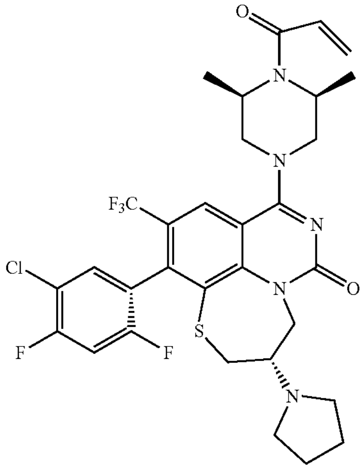
,
(1138)
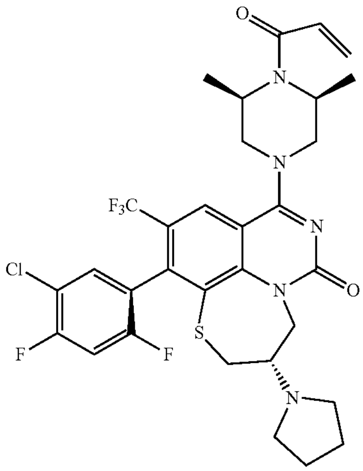
,
-continued
(1139)
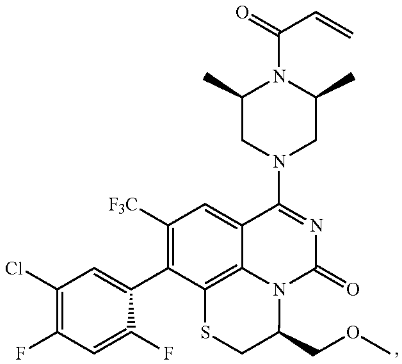
,
(1140)
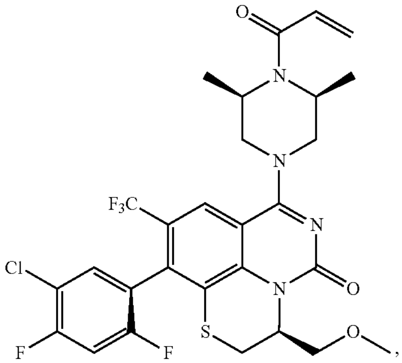
,
(1141)
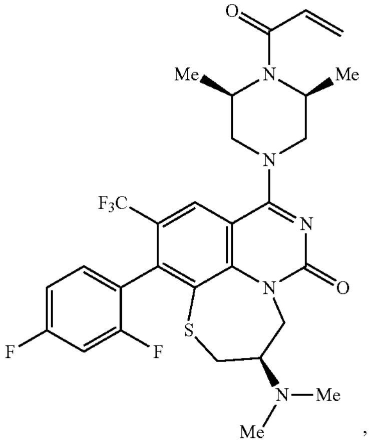
,
(1002)
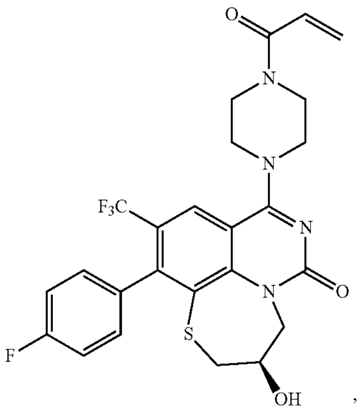
, (1003)
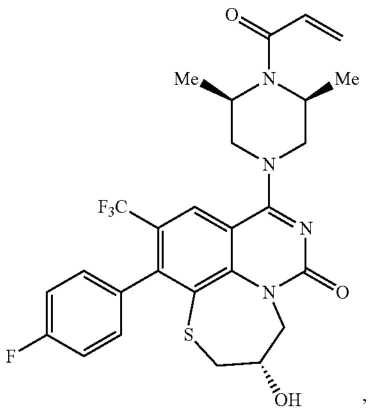
(1004)
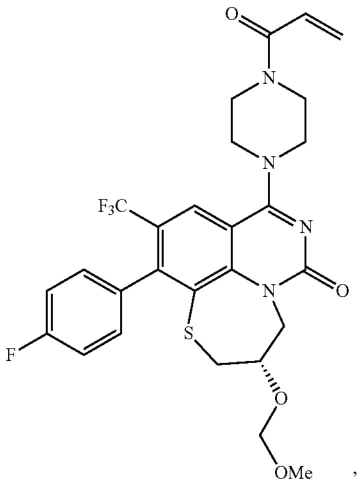
(1005)
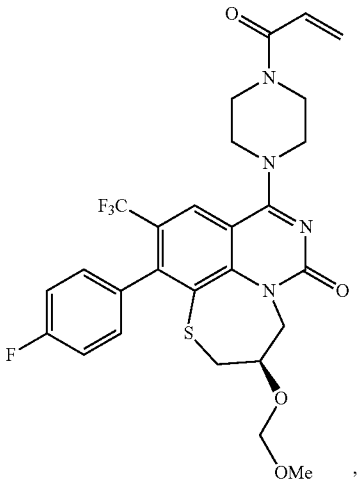
(1006)
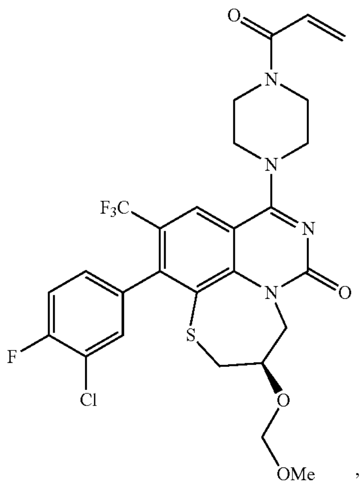
(1007)
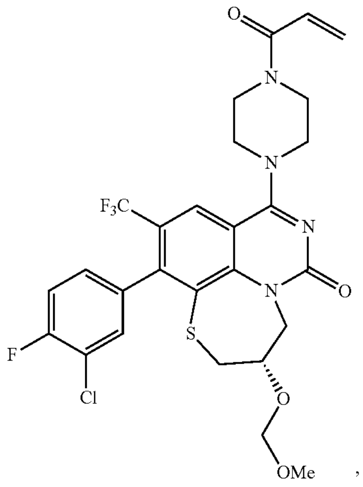
(1008)
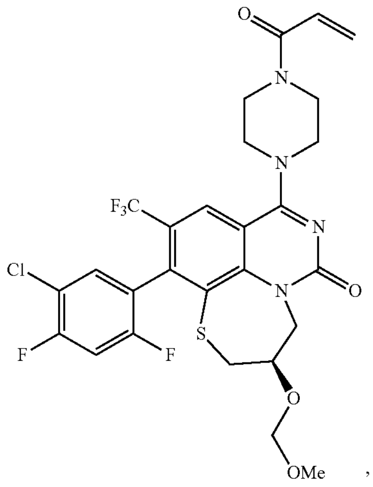

-continued
(1009)
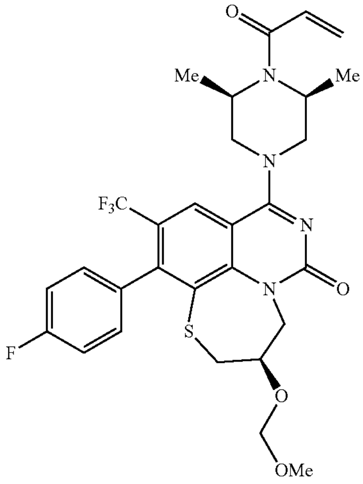
,
(1010)
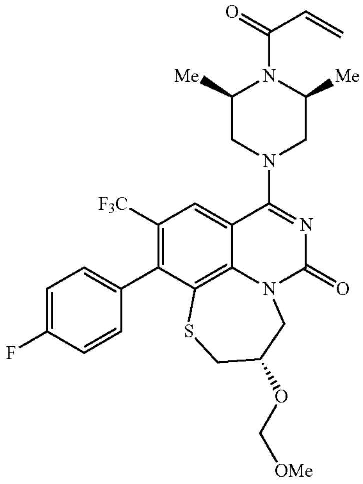
,
(1011)
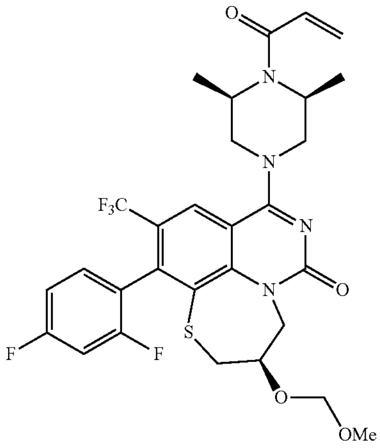
,
-continued
(1012)
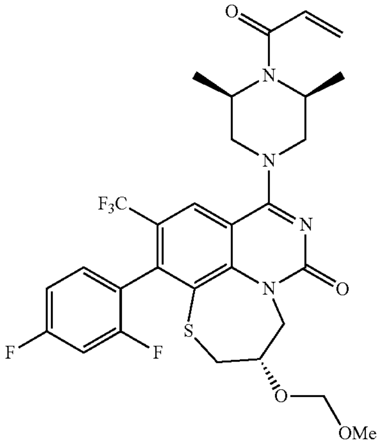
,
(1013)
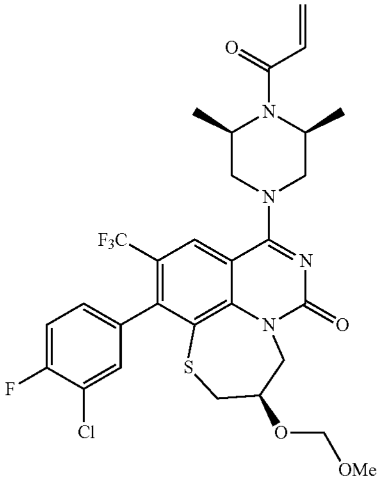
,
(1014)
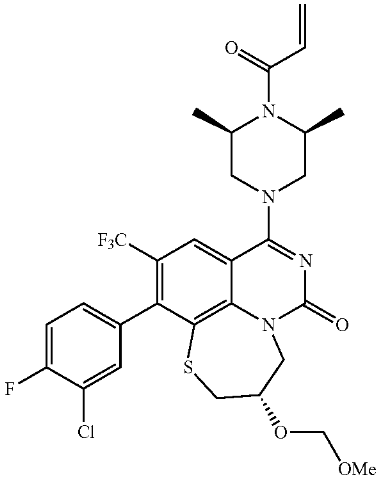
, -continued
(1015)
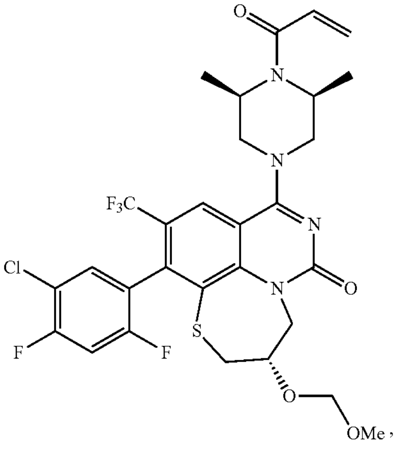
(1016)
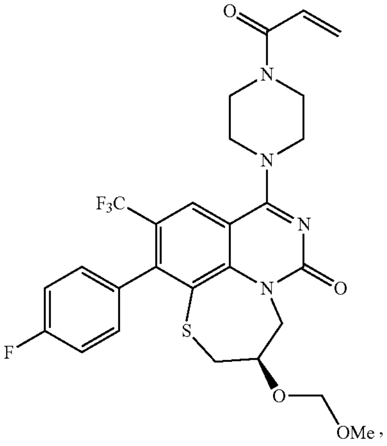
(1017)
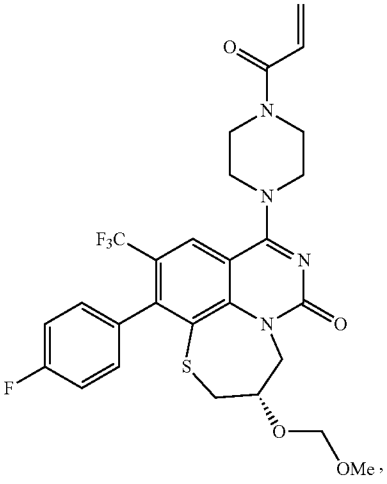
-continued
(1018)
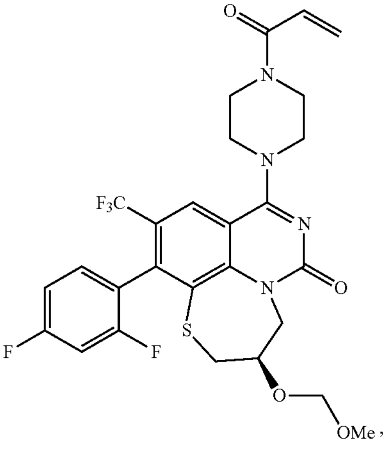
(1019)
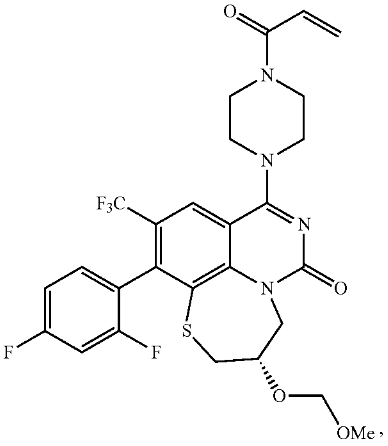
(1020)
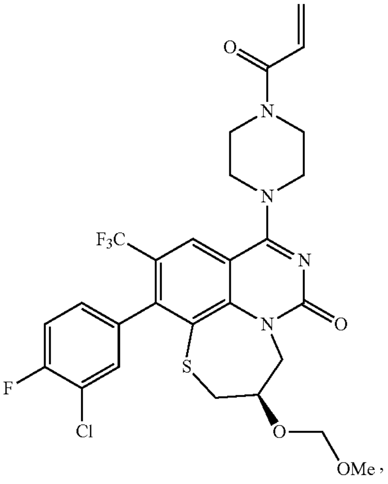

-continued
(1021)
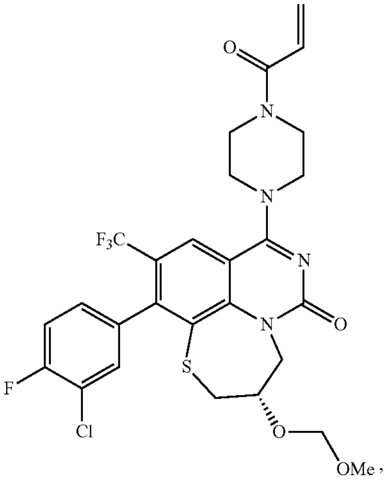
(1022)
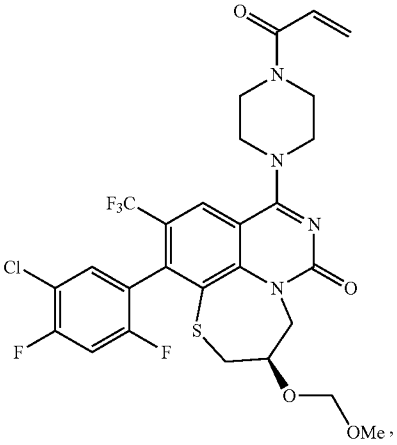
(1023)
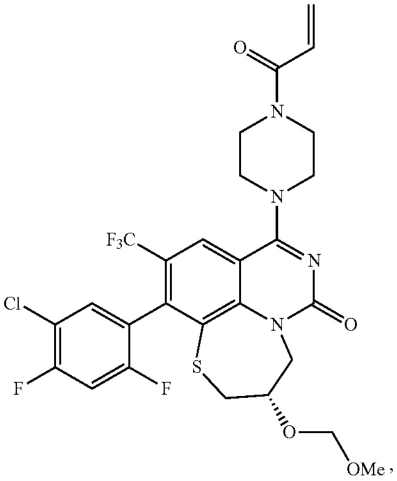
-continued
(1024)
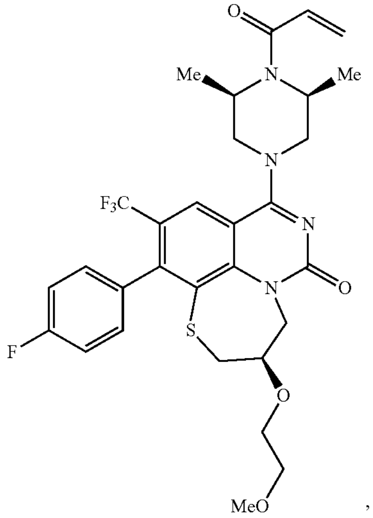
,
(1025)
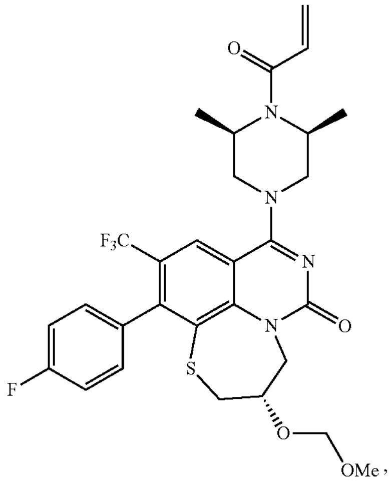
(1026)
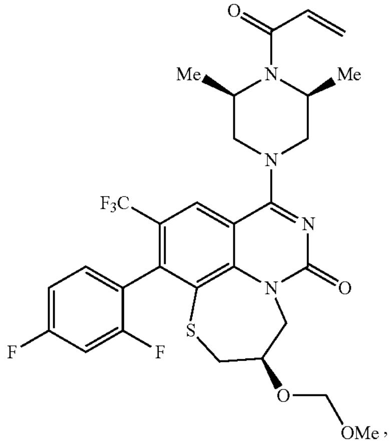

-continued
(1027)
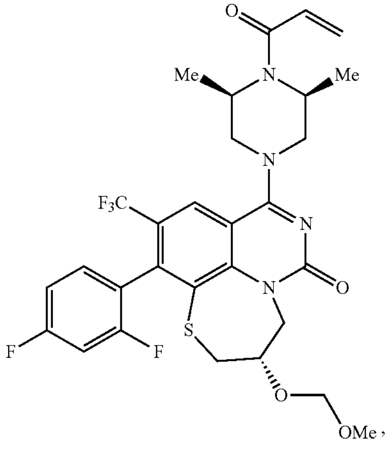
(1028)
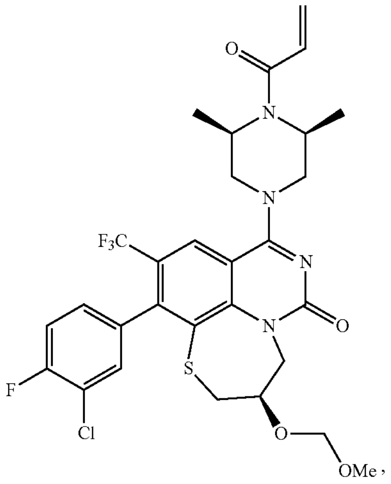
(1029)
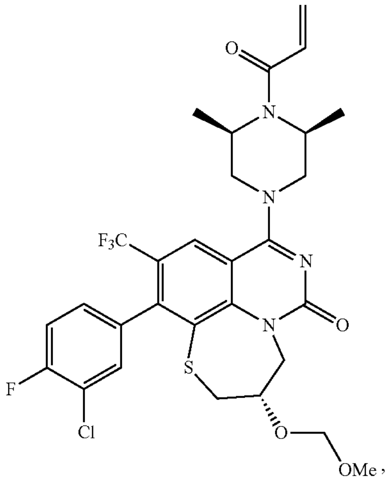
-continued
(1030)
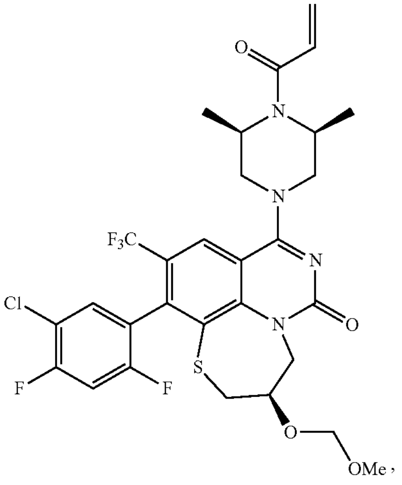
(1031)
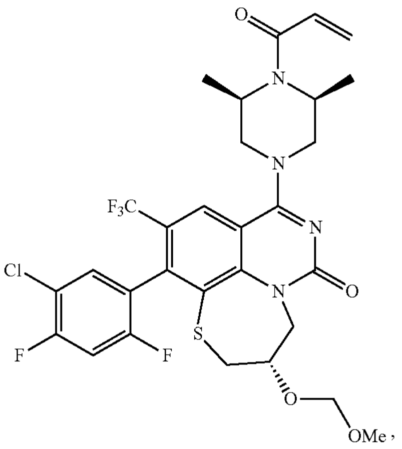
(1032)
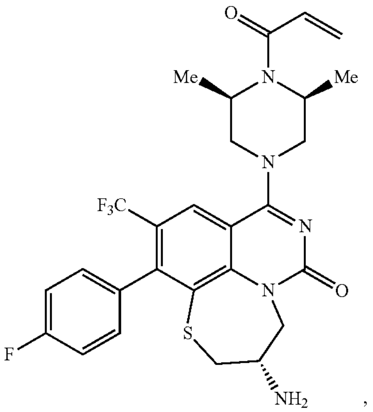

-continued
(1033)
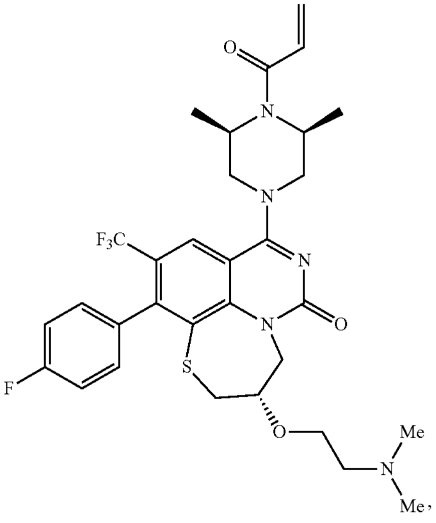
(1034)
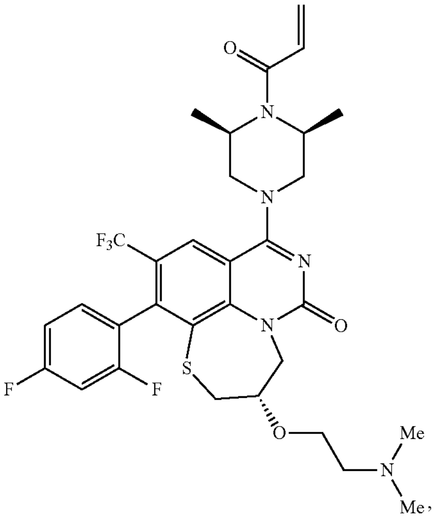
(1035)
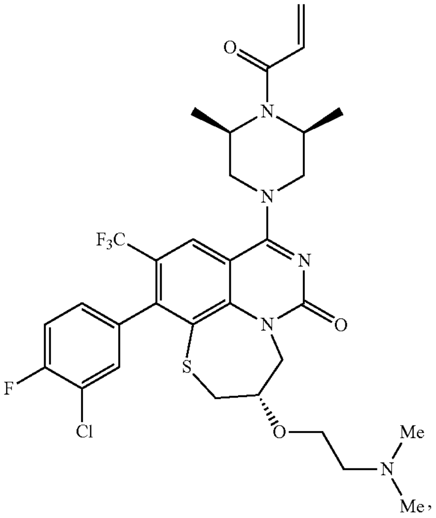
-continued
(1036)
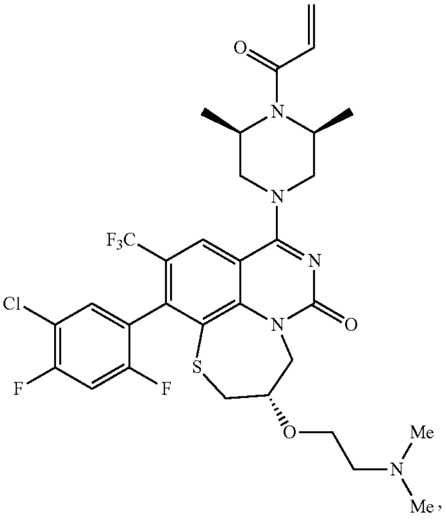
(1037)
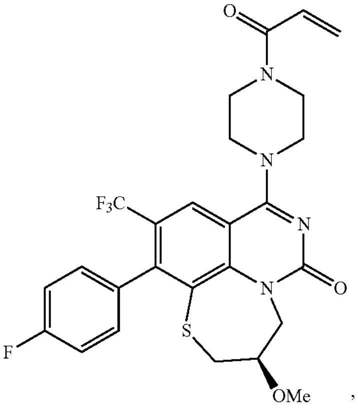
,
(1038)
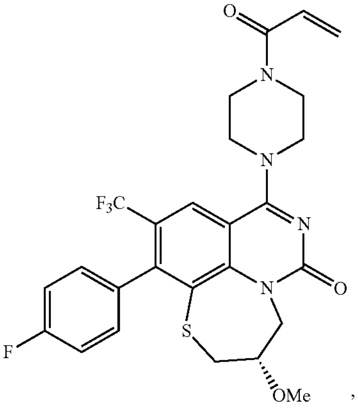
, -continued
(1039)
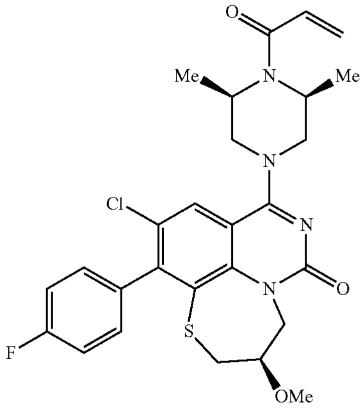
,
(1040)
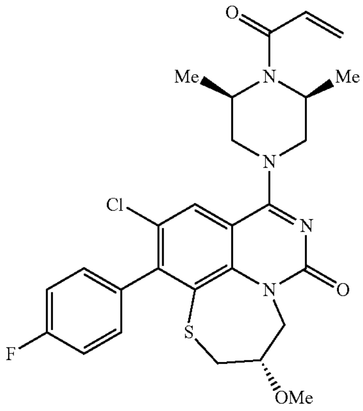
,
(1041)
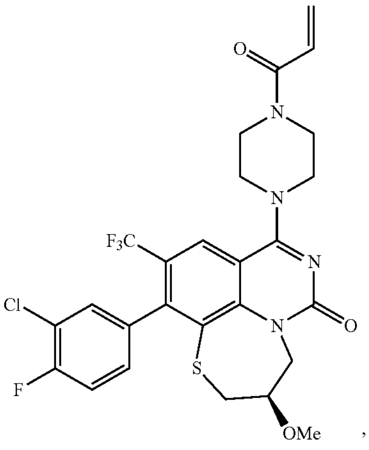
,
-continued
(1042)
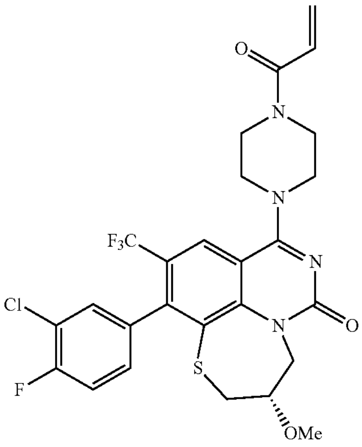
,
(1043)
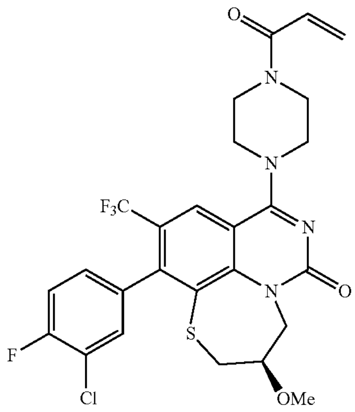
,
(1044)
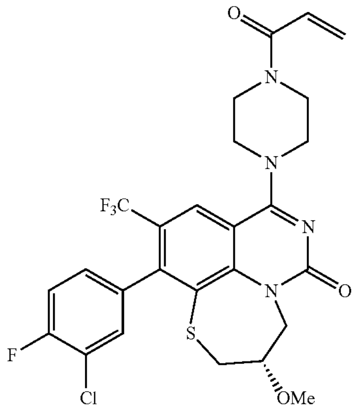
, -continued
(1045)
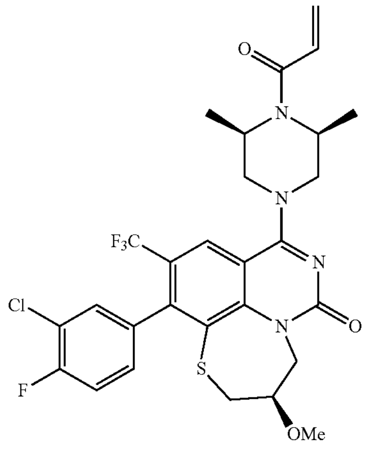
, and
(1046)
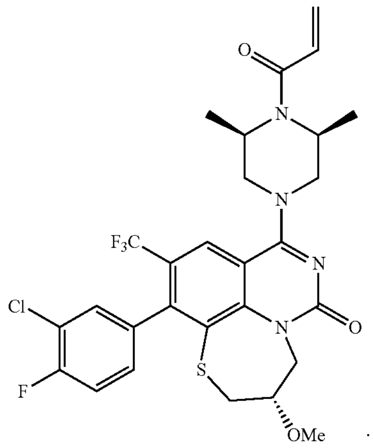
.
In embodiments, there are provided further compounds:
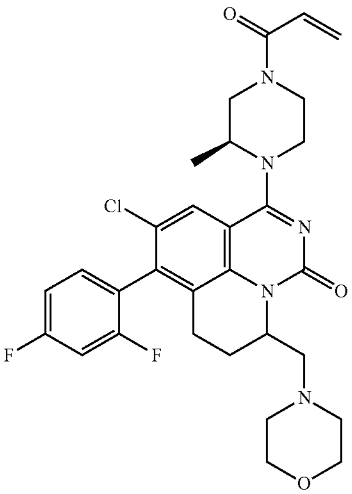
-continued
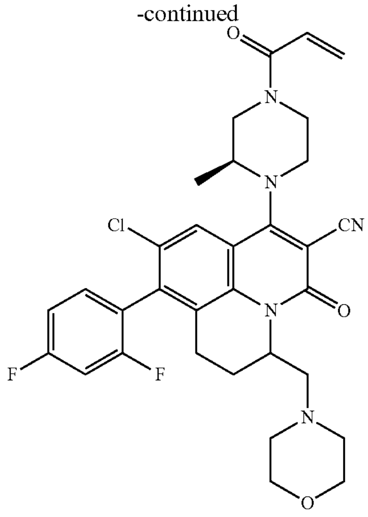
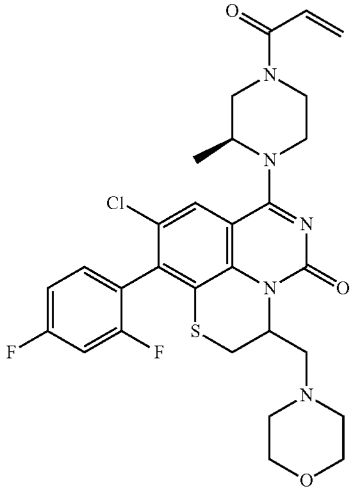
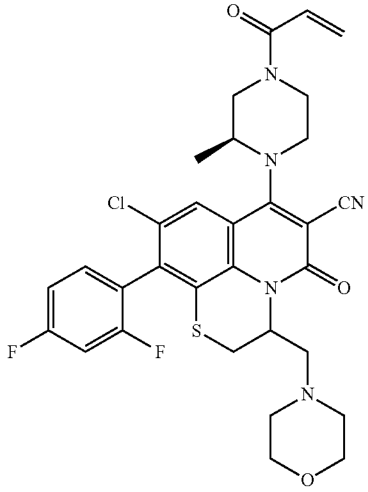

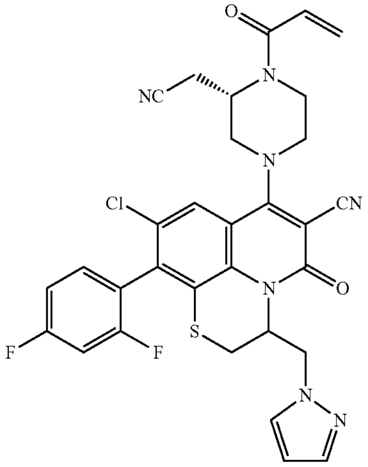
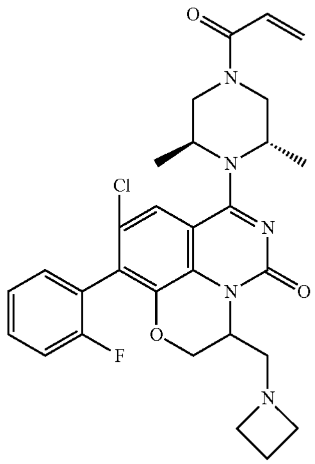
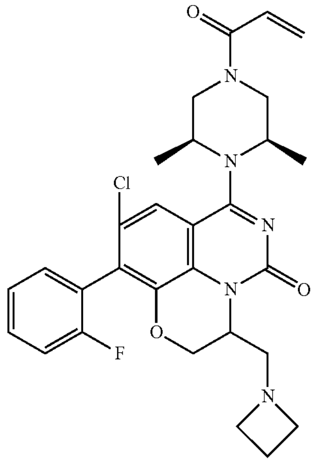
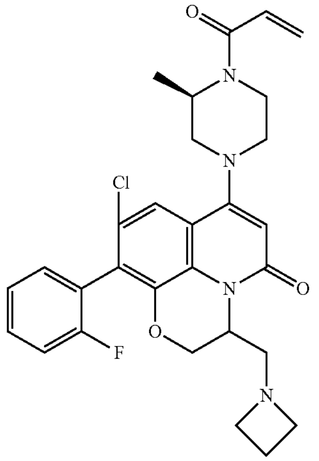
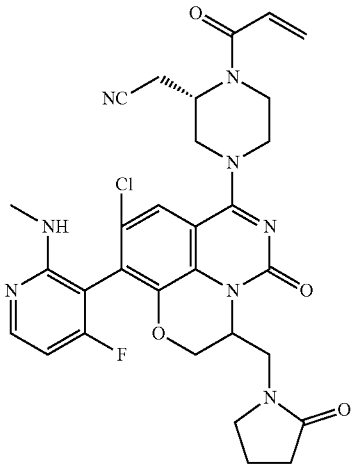
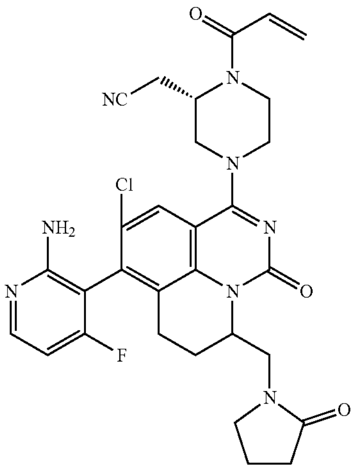

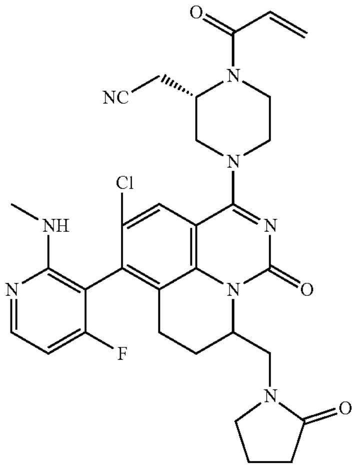
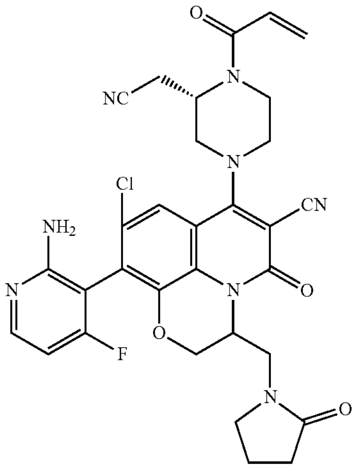
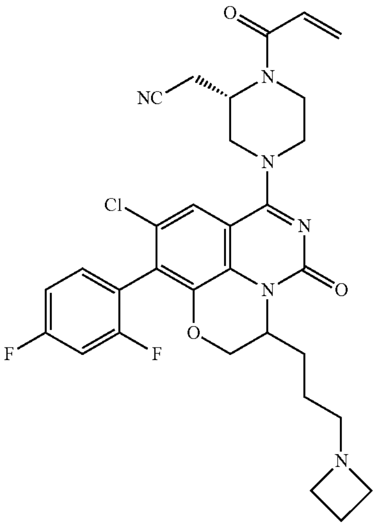
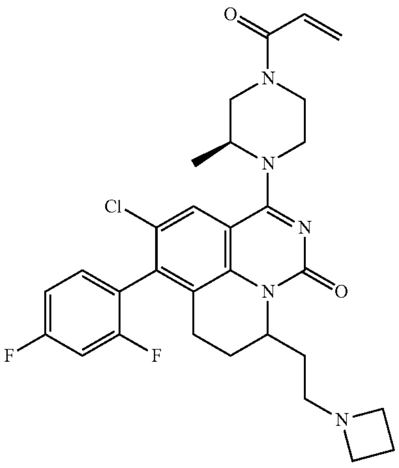
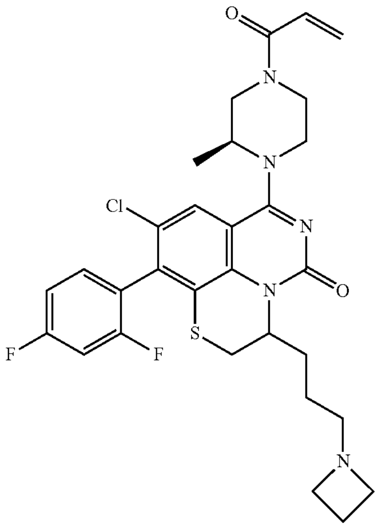
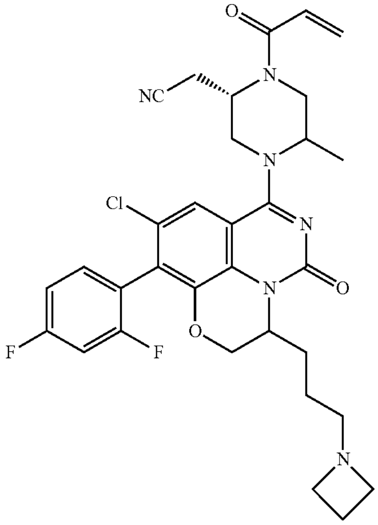

-continued

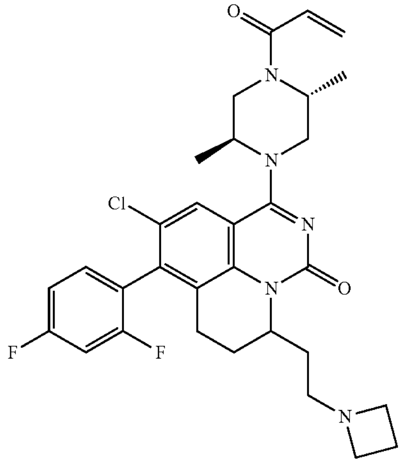

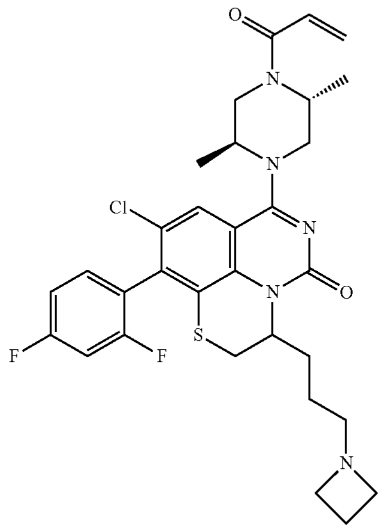

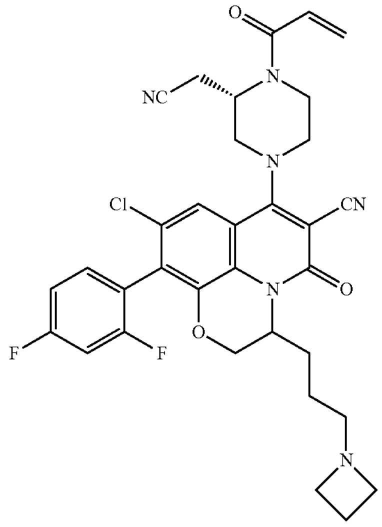

-continued

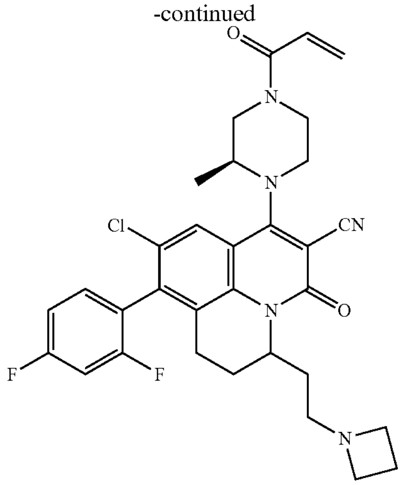

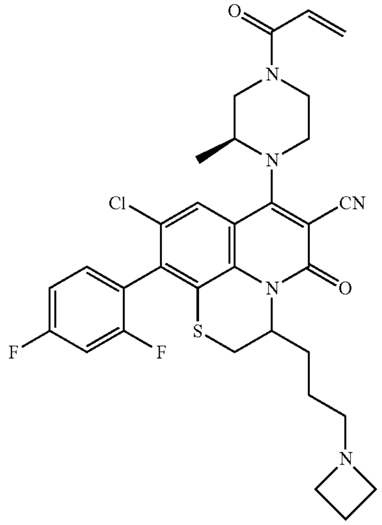

VI. General Synthetic Methods for Preparing Compounds

The following schemes can be used to practice the various embodiments disclosed herein. It will be understood that these schemes are merely exemplary and that they provide ready access to core structures with variable functionality.

VII. Modes of Administration

While it may be possible for the compounds disclosed herein to be administered as the raw chemical, it is also possible to present them as a pharmaceutical composition (i.e., as a formulation). Accordingly, provided herein are pharmaceutical compositions which comprise one or more of the compounds disclosed herein, or one or more pharmaceutically acceptable salts, esters, prodrugs, amides, or solvates thereof, together with one or more pharmaceutically acceptable carriers and optionally one or more other therapeutic ingredients. The carrier(s) should be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art; e.g., in Remington's Pharmaceutical Sciences. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The pharmaceutical compositions may include those suitable for oral, parenteral (including subcutaneous, intradermal, intramuscular, intravenous, intraarticular, and intramedullary), intraperitoneal, transmucosal, transdermal, rectal and topical (including dermal, buccal, sublingual and intraocular) administration although the most suitable route may depend upon for example the condition and disorder of the recipient. The pharmaceutical composition may conveniently be presented in unit dosage form and may be prepared by any of the methods well known in the art of pharmacy. Typically, these methods include the step of bringing into association a compound disclosed herein or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Pharmaceutical compositions of the various embodiments disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical compositions that can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated to provide slow or controlled release of the active ingredient therein. All formulations for oral administration should be in dosages suitable for such administration.

The compounds disclosed herein may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Dosage

The compounds disclosed herein may be administered orally or via injection at a dose of from 0.1 to 500 mg/kg per day. A common dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds disclosed herein can be administered in various modes, e.g. orally, topically, or by injection. The precise amount of compound administered to a subject will be the responsibility of the attendant physician. The specific dose level for any particular subject will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the compounds described herein (or a pharmaceutically acceptable salt, ester, or prodrug thereof) in combination with another therapeutic agent. In any case, regardless of the disease, disorder or condition being treated, the overall benefit experienced by the patient may simply be additive of the two therapeutic agents or the patient may experience a synergistic benefit.

In any case, the multiple therapeutic agents (at least one of which is a compound of the various embodiments disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

VIII. Methods of Treatment

Some embodiments relate to methods of using the compounds described herein to treat cell proliferative disorders, such as cancer. The cancer can be any cancer, including those described herein. The cancer can be, for example, a RAS associated cancer. The treatments can include the use of combination treatments as described herein.

In some aspects of the embodiments, the cancer is a cancer of the central nervous system (CNS). CNS cancer can include any cancer of the CNS including cancer of the brain, spinal cord and nerves. Such CNS cancers can include, for example, primary cancers (e.g., those that start in the brain) and secondary or metastatic CNS cancers (those that do not start in the CNS but metastasize to the CNS). The CNS cancer can be a RAS associated cancer. Any CNS cancer is contemplated including without limitation, for example, gliomas (including astrocytomas and glioblastomas, oligodendrogliomas, ependymomas), meningiomas, medulloblastomas, ganbliogliomas, schwannomas, and craniopharyngiomas. Any metastatic CNS cancer is contemplated, including without limitation, a cancer metastasized to the CNS via metastases of melanoma, breast cancer, colon cancer, kidney cancer, nasopharyngeal cancer, lymphoma, myeloma, leukemia, and other cancers of unknown primary site. Some embodiments relate to treating, reducing or preventing metastesis of a CNS cancer, for example, to another region of the CNS and/or outside of the CNS.

As mentioned, embodiments herein provide methods for treating a RAS associated cancer, for example, a K-RAS-mediated disorders in a human or animal subject in need of such treatment comprising administering to said subject an amount of a compound of the various embodiments disclosed herein effective to reduce or prevent said disorder in the subject in combination with at least one additional agent for the treatment of said disorder that is known in the art. In a related aspect, the various embodiments disclosed herein provides therapeutic compositions comprising at least one compound of the various embodiments disclosed herein in combination with one or more additional agents for the treatment of K-RAS-mediated disorders. In some such embodiments, the K-RAS-mediated disease is cancer and the K-RAS presents in an oncogenic mutated form.

Compounds disclosed herein may be useful in treating K-RAS-mediated disease, disorders and conditions. In some embodiments, the compounds disclosed herein may be used in treating cancer, as disclosed hereinabove. In some such embodiments, the type of cancer may depend on presentation of a particular type of oncogenic mutation of K-RAS. For example, in some embodiments oncogenic K-RAS mutations may be tied to human cancer of the pancreas, lung, and/or colon.

1. Combination Therapies

Compounds disclosed herein may be used in combination therapies. For example, the compounds disclosed herein may be used in combination with inhibitors of mammalian target of rapamycin (mTOR), insulin growth factor 1 receptor (IGF1R), and combinations thereof. Such combination therapies may be particularly suited to certain cancer types such as lung cancer. See Molinas-Arcas et al. *Sci. Trans. Med.* 18 Sep. 2019 11:510 eaaw7999 at stm.sciencemag.org/content/11/510/eaaw7999. Compounds disclosed herein may be combined with modulators the ULK family of proteins, which regulate autophagy. Other compounds of interest in combination therapy include inhibitors of SHP2. Other SHP2 inhibitors include those disclosed in WO2016/203404, WO2018/136264, WO2018/057884, WO2019/067843, WO2019/183367, WO2016/203405, WO2019/051084, WO2018/081091, WO2019/165073, WO2017/216706, WO2018/218133, WO2019/183364, WO 2020061103, and WO2020061101. All references and patent applications, including compositions, methods of using, and methods of making compounds disclosed therein are incorporated herein by reference in their entirety.

In embodiments, compounds disclosed herein may be combined with an EGFR inhibitor. In embodiments, the EGFR inhibitor is selective for a mutant EGFR, including, without limitation, C797X, L718Q, G724S, S768I, G719X, L792X, G796X, T263P, A289D/V, G598V, and EGFRvIII high expression. In embodiments, the combination therapy with EGFR agents tracked by mutation and indication are shown in Table 1 CT-1 below.

TABLE 1

CT-1

| Mutation | Indication | EGFR agent |
|---|---|---|
| mEGFR | NSCLC | osimertinib |
| mEGFR | NSCLC | afatinib |
| mEGFR | NSCLC | erlotinib |
| mEGFR | NSCLC | gefitinib |
| mEGFR | NSCLC | lazertinib |
| mEGFR | NSCLC | nazartinib |
| mEGFR | NSCLC | dacomitinib |
| mEGFR | NSCLC | BLU-945 |
| mEGFR | NSCLC | icotinib |
| wtEGFR | Esophageal/CRC | cetuximab |
| wtEGFR | CRC | paninitumab |
| wtEGFR | NSCLC | amivantamab |
| wtHER2/wtEGFR | Breast cancer | lapatinib |
| wtHER2/wtEGFR | Breast cancer | neratinib |
| wtEGFR | NSCLC | zorifertinib |
| mEGFR | NSCLC | mobicertinib |

EGFR inhibitors include those disclosed in U.S. Pat. Nos. 5,747,498, 8,946,235, and 9,732,058, WO2002030926, US 20040048880, US20050165035, and WO2019067543. All patents and applications, including compositions, methods of using, and methods of making compounds disclosed therein are incorporated herein by reference in their entirety.

Other combination therapies based on target biomarkers are shown below in Table 2: CT-2.

TABLE 2

CT-2

| Biomarker(s) | Cancer Type | Target | Combination Agent |
|---|---|---|---|
| KRAS G12C | Solid tumors | KRAS G12C | AMG 510 |
| KRAS G12C | Solid tumors | KRAS G12C | MRTX849 |
| KRAS G12C | Solid tumors | KRAS G12C | GDC-6036 |
| BRAF V600E | CRC/ NSCLC | BRAF V600E | encorafenib |
| BRAF V600E | CRC/ NSCLC | BRAF V600E | dabrafenib |
| BRAF V600E | CRC/ NSCLC | BRAF V600E and MEK | encorafenib and binimetinib |
| BRAF V600E | CRC/ NSCLC | BRAF V600E and MEK | dabrafenib and trametinib |
| RB1 functional | Solid tumors | CDK4 and CDK6 | palbociclib |
| RB1 functional | Solid tumors | CDK4 and CDK6 | abemaciclib |
| RB1 functional | Solid tumors | CDK4 and CDK6 | ribociclib |
| RTK and/or RAS Driven | Solid tumors | SHP2 | TNO155 |
| RTK and/or RAS Driven | Solid tumors | SHP2 | RMC-4630 |

TABLE 2-continued

| CT-2 | | | |
|---|---|---|---|
| Biomarker(s) | Cancer Type | Target | Combination Agent |
| RTK and/or RAS Driven | Solid tumors | SHP2 | JAB-3068 |
| RTK and/or RAS Driven | Solid tumors | SHP2 | JAB-3312 |
| RTK and/or RAS Driven | Solid tumors | SHP2 | RLY-1971 |
| RTK, RAS, BRAF, and/or MEK driven | Solid tumors | ERK | ulixertinib |
| RTK, RAS, BRAF, and/or MEK driven | Solid tumors | ERK | ASN007 |
| RTK, RAS, BRAF, and/or MEK driven | Solid tumors | ERK | LY3214996 |
| RTK, RAS, BRAF, and/or MEK driven | Solid tumors | ERK | LTT462 |
| RTK, RAS, and/or BRAF | Solid tumors | MEK | trametinib |
| RTK, RAS, and/or BRAF | Solid tumors | MEK | binimetinib |
| RTK, RAS, and/or BRAF | Solid tumors | MEK | cobimetinib |
| RTK, RAS, and/or BRAF | Solid tumors | MEK | selumetinib |
| MET-driven | Solid tumors | MET | capmatinib |
| MET-driven | Solid tumors | MET | crizotinib |
| MET-driven | Solid tumors | MET | savolitinib |

The second agent of the pharmaceutical combination formulation or dosing regimen may have complementary activities to the compounds disclosed herein such that they do not adversely affect each other. The compounds may be administered together in a unitary pharmaceutical composition or separately. In one embodiment a compound or a pharmaceutically acceptable salt can be co-administered with a cytotoxic agent to treat proliferative diseases and cancer.

The term "co-administering" refers to either simultaneous administration, or any manner of separate sequential administration, of a compound disclosed herein or a salt thereof, and a further active pharmaceutical ingredient or ingredients, including cytotoxic agents and radiation treatment. If the administration is not simultaneous, the compounds are administered in a close time proximity to each other. Furthermore, it does not matter if the compounds are administered in the same dosage form, e.g. one compound may be administered topically and another compound may be administered orally.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

In certain embodiments, compositions of this invention are formulated such that a dosage of between 0.01-100 mg/kg body weight/day of an inventive can be administered.

Typically, any agent that has activity against a disease or condition being treated may be co-administered. Examples of such agents can be found in Cancer Principles and Practice of Oncology by V. T. Devita and S. Hellman (editors), $6^{th}$ edition (Feb. 15, 2001), Lippincott Williams & Wilkins Publishers. A person of ordinary skill in the art would be able to discern which combinations of agents would be useful based on the particular characteristics of the drugs and the disease involved.

In one embodiment, the treatment method includes the co-administration of a compound disclosed herein or a pharmaceutically acceptable salt thereof and at least one cytotoxic agent. The term "cytotoxic agent" as used herein refers to a substance that inhibits or prevents a cellular function and/or causes cell death or destruction. Cytotoxic agents include, but are not limited to, radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); chemotherapeutic agents; growth inhibitory agents; enzymes and fragments thereof such as nucleolytic enzymes; and toxins such as small molecule toxins or enzymatically active toxins of bacterial, fungal, plant or animal origin, including fragments and/or variants thereof.

Exemplary cytotoxic agents can be selected from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, inhibitors of LDH-A; inhibitors of fatty acid biosynthesis; cell cycle signalling inhibitors; HDAC inhibitors, proteasome inhibitors; and inhibitors of cancer metabolism.

"Chemotherapeutic agent" includes chemical compounds useful in the treatment of cancer. Examples of chemotherapeutic agents include erlotinib (TARCEVA®, Genentech/OSI Pharm.), bortezomib (VELCADE®, Millennium Pharm.), disulfiram, epigallocatechin gallate, salinosporamide A, carfilzomib, 17-AAG(geldanamycin), radicicol, lactate dehydrogenase A (LDH-A), fulvestrant (FASLODEX®, AstraZeneca), sunitib (SUTENT®, Pfizer/Sugen), letrozole (FEMARA®, Novartis), imatinib mesylate (GLEEVEC®., Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafamib (SCH 66336), sorafenib (NEXAVAR®, Bayer Labs), gefitinib (IRESSA®, AstraZeneca), AG1478, alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including topotecan and irinotecan); bryostatin; callystatin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5α-reductases including finasteride and dutasteride); vorinostat, romidepsin, panobinostat, valproic acid, mocetinostat dolastatin; aldesleukin, talc duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γ1I and calicheamicin ω1I (*Angew Chem. Intl. Ed. Engl.* 1994 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Chemotherapeutic agent also includes (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, iodoxyfene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide and goserelin; buserelin, tripterelin, medroxyprogesterone acetate, diethylstilbestrol, premarin, fluoxymesterone, all transretionic acid, fenretinide, as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN®, rIL-2; a topoisomerase 1 inhibitor such as LURTOTECAN®; ABARELIX® rmRH; and (ix) pharmaceutically acceptable salts, acids and derivatives of any of the above.

Chemotherapeutic agent also includes antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories) which is a recombinant exclusively human-sequence, full-length $IgG_1\lambda$ antibody genetically modified to recognize interleukin-12 p40 protein.

Chemotherapeutic agent also includes "EGFR inhibitors," which refers to compounds that bind to or otherwise interact directly with EGFR and prevent or reduce its signaling activity, and is alternatively referred to as an "EGFR antagonist." Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No.

5,891,996; and human antibodies that bind EGFR, such as ABX-EGF or Panitumumab (see WO98/50433, Abgenix/Amgen); EMD 55900 (Stragliotto et al. *Eur. J. Cancer* 32A:636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as E1.1, E2.4, E2.5, E6.2, E6.4, E2.11, E6. 3 and E7.6. 3 and described in U.S. Pat. No. 6,235,883; MDX-447 (Medarex Inc); and mAb 806 or humanized mAb 806 (Johns et al., *J. Biol. Chem.* 279(29): 30375-30384 (2004)). The anti-EGFR antibody may be conjugated with a cytotoxic agent, thus generating an immunoconjugate (see, e.g., EP659,439A2, Merck Patent GmbH). EGFR antagonists include small molecules such as compounds described in U.S. Pat. Nos. 5,616,582, 5,457,105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO98/14451, WO98/50038, WO99/09016, and WO99/24037. Particular small molecule EGFR antagonists include OSI-774 (CP-358774, erlotinib, TARCEVA® Genentech/OSI Pharmaceuticals); PD 183805 (CI 1033, 2-propenamide, N-[4-[(3-chloro-4-fluorophenyl)amino]-7-[3-(4-morpholinyl) propoxy]-6-quinazolinyl]-, dihydrochloride, Pfizer Inc.); ZD1839, gefitinib (IRESSA®) 4-(3'-Chloro-4'-fluoroanilino)-7-methoxy-6-(3-morpholinopropoxy)quinazoline, AstraZeneca); ZM 105180 ((6-amino-4-(3-methylphenyl-amino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl)amino]-1H-pyrrolo[2,3-d]pyrimidin-6-yl]-phenol); (R)-6-(4-hydroxyphenyl)-4-[(1-phenylethyl)amino]-7H-pyrrolo[2,3-d]pyrimidine); CL-387785 (N-[4-[(3-bromophenyl)amino]-6-quinazolinyl]-2-butynamide); EKB-569 (N-[4-[(3-chloro-4-fluorophenyl)amino]-3-cyano-7-ethoxy-6-quinolinyl]-4-(dimethylamino)-2-butenamide) (Wyeth); AG1478 (Pfizer); AG1571 (SU 5271; Pfizer); dual EGFR/HER2 tyrosine kinase inhibitors such as lapatinib (TYKERB®, GSK572016 or N-[3-chloro-4-[(3 fluorophenyl)methoxy]phenyl]-6[5[[[2methylsulfonyp-ethyl]amino]methyl]-2-furanyl]-4-quinazolinamine).

Chemotherapeutic agents also include "tyrosine kinase inhibitors" including the EGFR-targeted drugs noted in the preceding paragraph; small molecule HER2 tyrosine kinase inhibitor such as TAK165 available from Takeda; CP-724,714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GSK572016; available from Glaxo-SmithKline), an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVEC®, available from Glaxo SmithKline); multi-targeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase I inhibitor CI-1040 (available from Pharmacia); quinazolines, such as PD 153035,4-(3-chloroandino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d]pyrimidines; curcumin (diferuloyl methane, 4,5-bis (4-fluoroanilino)phthalimide); tyrphostines containing nitrothiophene moieties; PD-0183805 (Warner-Lamber); antisense molecules (e.g. those that bind to HER-encoding nucleic acid); quinoxalines (U.S. Pat. No. 5,804,396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); imatinib mesylate (GLEEVEC®); PKI 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-1C11 (Imclone), rapamycin (sirolimus, RAPAMUNE®); or as described in any of the following patent publications: U.S. Pat. No. 5,804,396; WO 1999/09016 (American Cyanamid); WO 1998/43960 (American Cyanamid); WO 1997/38983 (Warner Lambert); WO 1999/06378 (Warner Lambert); WO 1999/06396 (Warner Lambert); WO 1996/30347 (Pfizer, Inc); WO 1996/33978 (Zeneca); WO 1996/3397 (Zeneca) and WO 1996/33980 (Zeneca).

Chemotherapeutic agents also include dexamethasone, interferons, colchicine, metoprine, cyclosporine, amphotericin, metronidazole, alemtuzumab, alitretinoin, allopurinol, amifostine, arsenic trioxide, asparaginase, BCG live, bevacuzimab, bexarotene, cladribine, clofarabine, darbepoetin alfa, denileukin, dexrazoxane, epoetin alfa, elotinib, filgrastim, histrelin acetate, ibritumomab, interferon alfa-2a, interferon alfa-2b, lenalidomide, levamisole, mesna, methoxsalen, nandrolone, nelarabine, nofetumomab, oprelvekin, palifermin, pamidronate, pegademase, pegaspargase, pegfilgrastim, pemetrexed disodium, plicamycin, porfimer sodium, quinacrine, rasburicase, sargramostim, temozolomide, VM-26, 6-TG, toremifene, tretinoin, ATRA, valrubicin, zoledronate, and zoledronic acid, and pharmaceutically acceptable salts thereof.

Chemotherapeutic agents also include hydrocortisone, hydrocortisone acetate, cortisone acetate, tixocortol pivalate, triamcinolone acetonide, triamcinolone alcohol, mometasone, amcinonide, budesonide, desonide, fluocinonide, fluocinolone acetonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate and fluprednidene acetate; immune selective anti-inflammatory peptides (ImSAIDs) such as phenylalanine-glutamine-glycine (FEG) and its D-isomeric form (feG) (IMULAN BioTherapeutics, LLC); anti-rheumatic drugs such as azathioprine, ciclosporin (cyclosporine A), D-penicillamine, gold salts, hydroxychloroquine, leflunomideminocycline, sulfasalazine, tumor necrosis factor alpha (TNFα) blockers such as etanercept (Enbrel), infliximab (Remicade), adalimumab (Humira), certolizumab pegol (Cimzia), golimumab (Simponi), Interleukin 1 (IL-1) blockers such as anakinra (Kineret), T cell costimulation blockers such as abatacept (Orencia), Interleukin 6 (IL-6) blockers such as tocilizumab (ACTEMERA®); Interleukin 13 (IL-13) blockers such as lebrikizumab; Interferon alpha (IFN) blockers such as Rontalizumab; Beta 7 integrin blockers such as rhuMAb Beta7; IgE pathway blockers such as Anti-M1 prime; Secreted homotrimeric LTa3 and membrane bound heterotrimer LTa1/β2 blockers such as Anti-lymphotoxin alpha (LTa); radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu); miscellaneous investigational agents such as thioplatin, PS-341, phenylbutyrate, ET-18-OCH3, or farnesyl transferase inhibitors (L-739749, L-744832); polyphenols such as quercetin, resveratrol, piceatannol, epigallocatechine gallate, theaflavins, flavanols, procyanidins, betulinic acid and derivatives thereof; autophagy inhibitors such as chloroquine; delta-9-tetrahydrocannabinol (dronabinol, MARINOL®); beta-lapachone; lapachol; colchicines; betulinic acid; acetylcamptothecin, scopolectin, and 9-aminocamptothecin); podophyllotoxin; tegafur (UFTORAL®); bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); and epidermal growth factor receptor (EGF-R); vaccines such as THERATOPE® vaccine; perifosine, COX-2 inhibitor (e.g. celecoxib or etoricoxib), proteosome inhibitor (e.g. PS341); CCI-779; tipifarnib (R11577); orafenib, ABT510; Bcl-2 inhibitor such as oblimersen sodium (GENASENSE®); pixantrone; farnesyltransferase inhibitors such as lonafarnib (SCH 6636, SARASAR™); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone; and FOLFOX, an abbreviation for a treatment regimen with oxaliplatin (ELOXATIN™) combined with 5-FU and leucovorin.

Chemotherapeutic agents also include non-steroidal anti-inflammatory drugs with analgesic, antipyretic and anti-inflammatory effects. NSAIDs include non-selective inhibitors of the enzyme cyclooxygenase. Specific examples of NSAIDs include aspirin, propionic acid derivatives such as ibuprofen, fenoprofen, ketoprofen, flurbiprofen, oxaprozin and naproxen, acetic acid derivatives such as indomethacin, sulindac, etodolac, diclofenac, enolic acid derivatives such as piroxicam, meloxicam, tenoxicam, droxicam, lornoxicam and isoxicam, fenamic acid derivatives such as mefenamic acid, meclofenamic acid, flufenamic acid, tolfenamic acid, and COX-2 inhibitors such as celecoxib, etoricoxib, lumiracoxib, parecoxib, rofecoxib, rofecoxib, and valdecoxib. NSAIDs can be indicated for the symptomatic relief of conditions such as rheumatoid arthritis, osteoarthritis, inflammatory arthropathies, ankylosing spondylitis, psoriatic arthritis, Reiter's syndrome, acute gout, dysmenorrhoea, metastatic bone pain, headache and migraine, postoperative pain, mild-to-moderate pain due to inflammation and tissue injury, pyrexia, ileus, and renal colic.

In certain embodiments, chemotherapeutic agents include, but are not limited to, doxorubicin, dexamethasone, vincristine, cyclophosphamide, fluorouracil, topotecan, interferons, platinum derivatives, taxanes (e.g., paclitaxel, docetaxel), vinca alkaloids (e.g., vinblastine), anthracyclines (e.g., doxorubicin), epipodophyllotoxins (e.g., etoposide), cisplatin, an mTOR inhibitor (e.g., a rapamycin), methotrexate, actinomycin D, dolastatin 10, colchicine, trimetrexate, metoprine, cyclosporine, daunorubicin, teniposide, amphotericin, alkylating agents (e.g., chlorambucil), 5-fluorouracil, campthothecin, cisplatin, metronidazole, and imatinib mesylate, among others. In other embodiments, a compound disclosed herein is administered in combination with a biologic agent, such as bevacizumab or panitumumab.

In certain embodiments, compounds disclosed herein, or a pharmaceutically acceptable composition thereof, are administered in combination with an antiproliferative or chemotherapeutic agent selected from any one or more of abarelix, aldesleukin, alemtuzumab, alitretinoin, allopurinol, altretamine, amifostine, anastrozole, arsenic trioxide, asparaginase, azacitidine, BCG live, bevacuzimab, fluorouracil, bexarotene, bleomycin, bortezomib, busulfan, calusterone, capecitabine, camptothecin, carboplatin, carmustine, cetuximab, chlorambucil, cladribine, clofarabine, cyclophosphamide, cytarabine, dactinomycin, darbepoetin alfa, daunorubicin, denileukin, dexrazoxane, docetaxel, doxorubicin (neutral), doxorubicin hydrochloride, dromostanolone propionate, epirubicin, epoetin alfa, elotinib, estramustine, etoposide phosphate, etoposide, exemestane, filgrastim, floxuridine, fludarabine, fulvestrant, gefitinib, gemcitabine, gemtuzumab, goserelin acetate, histrelin acetate, hydroxyurea, ibritumomab, idarubicin, ifosfamide, imatinib mesylate, interferon alfa-2a, interferon alfa-2b, irinotecan, lenalidomide, letrozole, leucovorin, leuprolide acetate, levamisole, lomustine, megestrol acetate, melphalan, mercaptopurine, 6-MP, mesna, methotrexate, methoxsalen, mitomycin C, mitotane, mitoxantrone, nandrolone, nelarabine, nofetumomab, oprelvekin, oxaliplatin, paclitaxel, palifermin, pamidronate, pegademase, pegaspargase, pegfilgrastim, pemetrexed disodium, pentostatin, pipobroman, plicamycin, porfimer sodium, procarbazine, quinacrine, rasburicase, rituximab, sargramostim, sorafenib, streptozocin, sunitinib maleate, talc, tamoxifen, temozolomide, teniposide, VM-26, testolactone, thioguanine, 6-TG, thiotepa, topotecan, toremifene, tositumomab, trastuzumab, tretinoin, ATRA, uracil mustard, valrubicin, vinblastine, vincristine, vinorelbine, zoledronate, or zoledronic acid.

Chemotherapeutic agents also include treatments for Alzheimer's Disease such as donepezil hydrochloride and rivastigmine; treatments for Parkinson's Disease such as L-DOPA/carbidopa, entacapone, ropinrole, pramipexole, bromocriptine, pergolide, trihexephendyl, and amantadine; agents for treating multiple sclerosis (MS) such as beta interferon (e.g., Avonex® and Rebif®, glatiramer acetate, and mitoxantrone; treatments for asthma such as albuterol and montelukast sodium; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

Additionally, chemotherapeutic agents include pharmaceutically acceptable salts, acids or derivatives of any of chemotherapeutic agents, described herein, as well as combinations of two or more of them.

Embodiments

A compound of Formula (XXI)

(XXI)

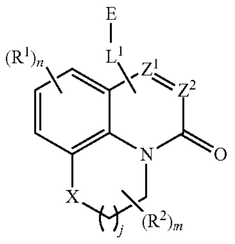

wherein:

X is $S(O)_p$, wherein p is an integer from 0 to 2;

j is an integer from 0 to 2;

$Z^1$ and $Z^2$ are independently $CR^6$ or N, with the proviso that at least one of $Z^1$ or $Z^2$ is $CR^6$ with $R^6$ being a bond to $L^1$;

$L^1$ is linking group comprising at least one nitrogen atom;

E is an electrophilic moiety, wherein E is bound to $L^1$ via the at least one nitrogen atom;

each $R^1$ is an optional substitution independently selected from the group consisting of alkyl, cyano, cycloalkyl, halo, haloalkyl, trifluoromethyl, alkoxy, aryl, heteroaryl, N-arylamino, N-aryl-N-alkylamino, aryloxy, and arylthio with the proviso that:

at least one $R^1$ is aryl, N-arylamino, N-aryl-N-alkylamino, aryloxy, arylthio, or heteroaryl, any of which is optionally substituted;

n is an integer from 1 to 3;

$R^2$ is selected from the group consisting of alkyl, amino, alkylamino, dialkylamino alkylamidoalkyl, arylamidoalkyl, alkylsulfonamidoalkyl, arylsulfonamidoalkyl, N-alkyl aminoalkyl, N,N-dialkyl aminoalkyl, alkoxy, alkoxyalkyl, cycloalkyl, alkylcycloalkyl, hydroxyalkyl, halo, haloalkyl, hydroxy, aryl, aralkyl, heteroaryl, heteroarylalkyl, heterocyclyl, heterocyclylalkyl, and oxo any of which are optionally substituted; or two $R^2$ together with the carbon atom to which they are attached form a spirocycle or heterocycle.

m is an integer from 0 to 6; and $R^6$ is selected from the group consisting of hydrogen, alkyl, haloakyl, cyano, halo, alkoxy, aryl, heteroaryl, trifluoromethyl and bond to $L^1$.

The compound wherein X is S.

The compound wherein X is S=O or $SO_2$.

The compound wherein j is 1.

The compound wherein m is 0.

The compound wherein m is 1.

The compound wherein $Z^1$ is $CR^6$ with $R^6$ being a bond to $L^1$.

The compound wherein $Z^2$ is N.

A compound of Formula (XXIIa):

(XXIIa)

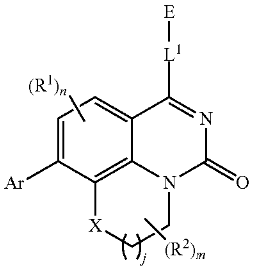

wherein:

X is $S(O)_p$, wherein p is an integer from 0 to 2;

j is an integer from 0 to 2;

$L^1$ is linking group comprising at least one nitrogen atom;

E is an electrophilic moiety, wherein E is bound to $L^1$ via the at least one nitrogen atom;

each $R^1$ is an optional substitution independently selected from the group consisting of alkyl, cyano, cycloalkyl, halo, haloalkyl, trifluoromethyl, and alkoxy;

n is an integer from 0 to 2;

$R^2$ is selected from the group consisting of alkyl, alkylamino, dialkylamino alkylamidoalkyl, arylamidoalkyl, alkylsulfonamidoalkyl, arylsulfonamidoalkyl, N-alkyl aminoalkyl, N,N-dialkyl aminoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted;

m is an integer from 0 to 6; and

Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted.

A compound of Formula (XXIII):

(XXIII)

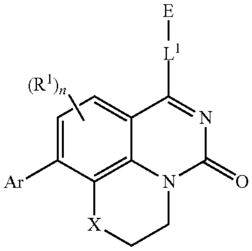

wherein:

X is $S(O)_p$, wherein p is an integer from 0 to 2;

$L^1$ is linking group comprising at least one nitrogen atom;

E is an electrophilic moiety, wherein E is bound to $L^1$ via the at least one nitrogen atom;

each $R^1$ is an optional substitution independently selected from the group consisting of alkyl, cyano, cycloalkyl, halo, haloalkyl, trifluoromethyl, and alkoxy;

n is an integer from 0 to 2; and

Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted.

A compound of Formula (XXIV):

(XXIV)

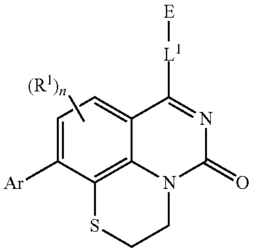

wherein:

$L^1$ is linking group comprising at least one nitrogen atom;

E is an electrophilic moiety, wherein E is bound to $L^1$ via the at least one nitrogen atom;

each $R^1$ is an optional substitution independently selected from the group consisting of alkyl, cyano, cycloalkyl, halo, haloalkyl, trifluoromethyl, and alkoxy; n is an integer from 0 to 2; and Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted.

210. A compound of Formula (XXV):

(XXV)

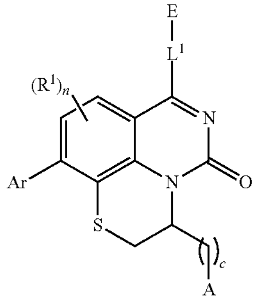

wherein:

$L^1$ is linking group comprising at least one nitrogen atom;

E is an electrophilic moiety, wherein E is bound to $L^1$ via the at least one nitrogen atom;

each $R^1$ is an optional substitution independently selected from the group consisting of alkyl, cyano, cycloalkyl, halo, haloalkyl, trifluoromethyl, and alkoxy;

n is an integer from 0 to 2;

c is an integer from 0 to 4;

A is selected from the group consisting of hydroxyl, amino, N-alkylamino, N,N-dialkylamino, cycloalkylamino, N-alkylaminoalkyl, N,N-dialkylaminoalkyl, cycloalkylaminoalkyl, alkylamidoalkyl, arylamidoalkyl, alkylsulfonamidoalkyl, arylsulfonamidoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted; and Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted.

217. A compound of Formula (XXVI):

(XXVI)

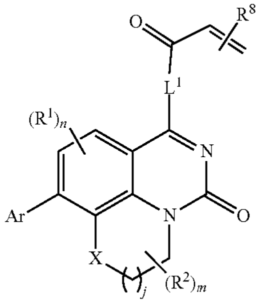

wherein:

X is $S(O)_p$, wherein p is an integer from 0 to 2;

j is an integer from 0 to 2;

$L^1$ is linking group comprising at least one nitrogen atom;

each $R^1$ is an optional substitution independently selected from the group consisting of alkyl, cyano, cycloalkyl, halo, haloalkyl, trifluoromethyl, and alkoxy;

n is an integer from 0 to 2;

$R^2$ is selected from the group consisting of alkyl, alkylamino, dialkylamino alkylamidoalkyl, arylamidoalkyl, alkylsulfonamidoalkyl, arylsulfonamidoalkyl, N-alkyl aminoalkyl, N,N-dialkyl aminoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted;

m is an integer from 0 to 6;

$R^8$ is selected from the group consisting of fluorine, methyl, and $—CH_2NR^aR^b$, wherein $R^a$ and $R^b$ are independently selected from hydrogen or alkyl; or $R^a$ and $R^b$ combine to form a $C_2$-$C_6$ nitrogen containing heterocycle; and Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted.

227. A compound of Formula (XXVII):

(XXVII)

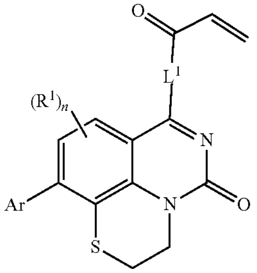

wherein:

$L^1$ is linking group comprising at least one nitrogen atom;

each $R^1$ is an optional substitution independently selected from the group consisting of alkyl, cyano, cycloalkyl, halo, haloalkyl, trifluoromethyl, and alkoxy;

n is an integer from 0 to 2; and

Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted.

232. A compound of Formula (XXVIII):

(XXVIII)

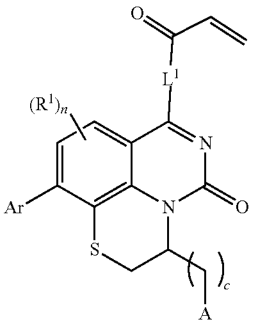

wherein:

$L^1$ is linking group comprising at least one nitrogen atom;

each $R^1$ is an optional substitution independently selected from the group consisting of alkyl, cyano, cycloalkyl, halo, haloalkyl, trifluoromethyl, and alkoxy;

n is an integer from 0 to 2;

c is an integer from 0 to 4;

A is selected from the group consisting of hydroxyl, amino, N-alkylamino, N,N-dialkylamino, cycloalkylamino, N-alkylaminoalkyl, N,N-dialkylaminoalkyl, cycloalkylaminoalkyl, alkylamidoalkyl, arylamidoalkyl, alkylsulfonamidoalkyl, arylsulfonamidoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted; and Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted.

237. A compound of Formula (XXIX):

(XXIX)

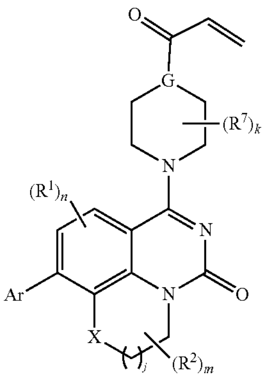

wherein:

X is $S(O)_p$, wherein p is an integer from 0 to 2;

j is an integer from 0 to 2;

G is selected from the group consisting of N, CH, and

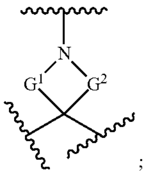

;

wherein $G^1$ and $G^2$ are independently $(CH_2)_q$, where q is 1 or 2;

each $R^1$ is an optional substitution independently selected from the group consisting of alkyl, cyano, cycloalkyl, halo, haloalkyl, trifluoromethyl, and alkoxy;

Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted;

n is an integer from 0 to 2;

$R^2$ is selected from the group consisting of alkyl, alkylamino, dialkylamino alkylamidoalkyl, arylamidoalkyl, alkylsulfonamidoalkyl, arylsulfonamidoalkyl, N-alkyl aminoalkyl, N,N-dialkyl aminoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted;

m is an integer from 0 to 6;

wherein k is an integer from 0 to 4; and each $R^7$ is independently selected from an alkyl group selected from methyl, ethyl, and propyl, any of which are optionally substituted with one or more fluorine atoms, $—CH_2(CH_3)C{=}CF_2$, cyano, propargyl, $—CH_2C(O)V$, wherein V is selected from methyl, OH, $NHR^i$ wherein $R^i$ is hydrogen or alkyl, and cyanomethyl; or any two $R^7$ may combine to form a fused-ring, spiro or bridging bicycle, wherein any one fused-ring or bridging atom is O, S, S═O, $SO_2$, or $NR^j$, wherein $R^j$ is H, methyl or trifluoromethyl; and wherein the acrylyl moiety linked to G is optionally substituted.

246. A compound of Formula (XXX):

(XXX)

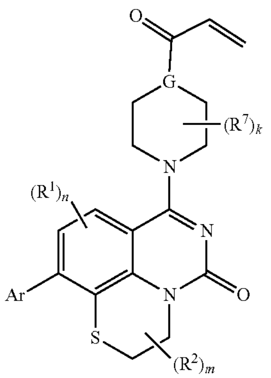

wherein:

G is selected from the group consisting of N, CH, and

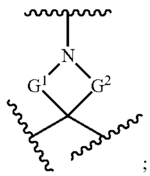

;

wherein $G^1$ and $G^2$ are independently $(CH_2)_q$, where q is 1 or 2;

each $R^1$ is an optional substitution independently selected from the group consisting of alkyl, cyano, cycloalkyl, halo, haloalkyl, trifluoromethyl, and alkoxy;

Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted;

n is an integer from 0 to 2;

$R^2$ is selected from the group consisting of alkyl, alkylamino, dialkylamino alkylamidoalkyl, arylamidoalkyl, alkylsulfonamidoalkyl, arylsulfonamidoalkyl, N-alkyl aminoalkyl, N,N-dialkyl aminoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted;

m is an integer from 0 to 4;

wherein k is an integer from 0 to 4; and each $R^7$ is independently selected from an alkyl group selected from methyl, ethyl, and propyl, any of which are optionally substituted with one or more fluorine atoms, $—CH_2(CH_3)C{=}CF_2$, cyano, propargyl, $—CH_2C(O)V$, wherein V is selected from methyl, OH, $NHR^i$ wherein $R^i$ is hydrogen or alkyl, and cyanomethyl; or any two $R^7$ may combine to form a fused-ring, spiro or bridging bicycle, wherein any one fused-ring or bridging atom is O, S, S=O, $SO_2$, or $NR^j$, wherein $R^j$ is H, methyl or trifluoromethyl; and wherein the acrylyl moiety linked to G is optionally substituted.

252. A compound of Formula (XXXI):

(XXXI)

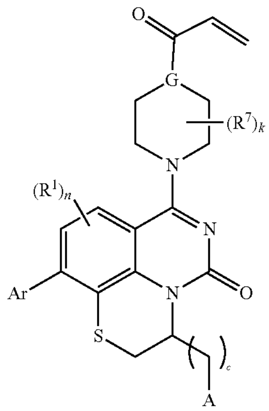

wherein:

G is selected from the group consisting of N, CH, and

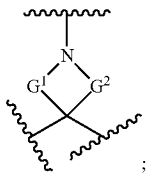

;

wherein $G^1$ and $G^2$ are independently $(CH_2)_q$, where q is 1 or 2;

each $R^1$ is an optional substitution independently selected from the group consisting of alkyl, cyano, cycloalkyl, halo, haloalkyl, trifluoromethyl, and alkoxy;

n is an integer from 0 to 2;

Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted;

c is an integer from 0 to 4;

A is selected from the group consisting of hydroxyl, amino, N-alkylamino, N,N-dialkylamino, cycloalkylamino, N-alkylaminoalkyl, N,N-dialkylaminoalkyl, cycloalkylaminoalkyl, alkylamidoalkyl, arylamidoalkyl, alkylsulfonamidoalkyl, arylsulfonamidoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted;

wherein k is an integer from 0 to 4; and each $R^7$ is independently selected from an alkyl group selected from methyl, ethyl, and propyl, any of which are optionally substituted with one or more fluorine atoms, $—CH_2(CH_3)C{=}CF_2$, cyano, propargyl, $—CH_2C(O)V$, wherein V is selected from methyl, OH, $NHR^i$ wherein $R^i$ is hydrogen or alkyl, and cyanomethyl; or any two $R^7$ may combine to form a fused-ring, spiro or bridging bicycle, wherein any one fused-ring or bridging atom is O, S, S=O, $SO_2$, or $NR^j$, wherein $R^j$ is H, methyl or trifluoromethyl; and wherein the acrylyl moiety linked to G is optionally substituted.

264. A compound of Formula (XXXIV):

(XXXIV)

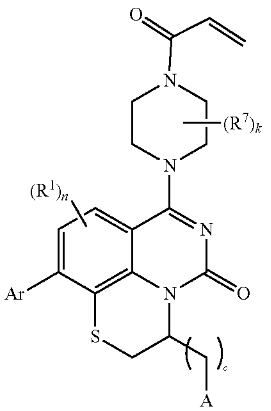

wherein:

each $R^1$ is an optional substitution independently selected from the group consisting of alkyl, cyano, cycloalkyl, halo, haloalkyl, trifluoromethyl, and alkoxy;

n is an integer from 0 to 2;

Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted;

c is an integer from 0 to 4;

A is selected from the group consisting of hydroxyl, amino, N-alkylamino, N,N-dialkylamino, cycloalkylamino, N-alkylaminoalkyl, N,N-dialkylaminoalkyl, cycloalkylaminoalkyl, alkylamidoalkyl, arylamidoalkyl, alkylsulfonamidoalkyl, arylsulfonamidoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted;

wherein k is an integer from 0 to 4; and each $R^7$ is independently selected from an alkyl group selected from methyl, ethyl, and propyl, any of which are optionally substituted with one or more fluorine atoms, $—CH_2(CH_3)C{=}CF_2$, cyano, propargyl, $—CH_2C(O)V$, wherein V is selected from methyl, OH, $NHR^i$ wherein $R^i$ is hydrogen or alkyl, and cyanomethyl; or any two $R^7$ may combine to form a fused-ring, spiro or bridging bicycle, wherein any one fused-ring or bridging atom is O, S, S═O, $SO_2$, or $NR^j$, wherein $R^j$ is H, methyl or trifluoromethyl; and wherein the acrylyl moiety linked to N is optionally substituted.

268. A compound of Formula (XXXV):

(XXXV)

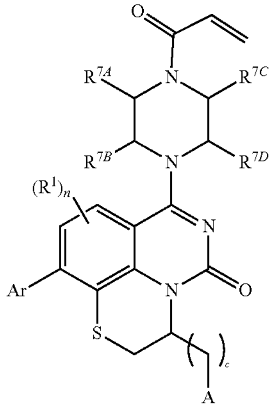

wherein:

each $R^1$ is an optional substitution independently selected from the group consisting of alkyl, cyano, cycloalkyl, halo, haloalkyl, trifluoromethyl, and alkoxy;

n is an integer from 0 to 2;

Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted;

c is an integer from 0 to 4;

A is selected from the group consisting of hydroxyl, amino, N-alkylamino, N,N-dialkylamino, cycloalkylamino, N-alkylaminoalkyl, N,N-dialkylaminoalkyl, cycloalkylaminoalkyl, alkylamidoalkyl, arylamidoalkyl, alkylsulfonamidoalkyl, arylsulfonamidoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted;

$R^{7A}$, $R^{7B}$, $R^{7C}$, and $R^{7D}$) are independently selected from hydrogen, alkyl, and cyanoalkyl; or any two $R^{7A-D}$ may combine to form a fused-ring or bridging bicycle, wherein any one fused-ring or bridging atom is O, S, S═O, or $SO_2$. and wherein the acrylyl moiety linked to N is optionally substituted.

282. A compound of Formula (XXXVI):

(XXXVI)

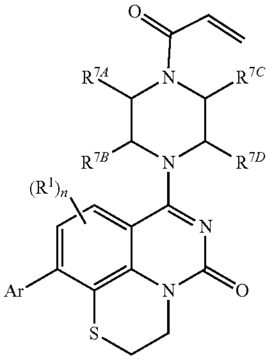

wherein:

each $R^1$ is an optional substitution independently selected from the group consisting of alkyl, cyano, cycloalkyl, halo, haloalkyl, trifluoromethyl, and alkoxy;

n is an integer from 0 to 2;

Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted;

$R^{7A}$, $R^{7B}$, $R^{7C}$, and $R^{7D}$ are independently selected from hydrogen, alkyl, and cyanoalkyl; or any two $R^{7A-D}$ may combine to form a fused-ring or bridging bicycle, wherein any one fused-ring or bridging atom is O, S, S═O, or $SO_2$; and wherein the acrylyl moiety linked to N is optionally substituted.

283. The compound wherein Ar creates axial asymmetry.

284. The compound wherein the compound is a single rotamer.

285. The compound wherein Ar is:

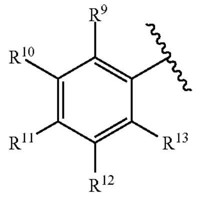

wherein $R^9$, $R^{10}$, $R^{11}$, $R^{12}$, and $R^{13}$ are each independently selected from the group consisting of hydrogen, halo, alkyl, alkoxy, haloalkyl, trifluoromethyl, cycloalkyl and any two adjacent $R^9$, $R^{10}$, $R^{11}$, $R^{12}$, and $R^{13}$ together combine to form a further fused ring that is an aromatic ring optionally comprising 1 to 3 heteroatoms independently selected from N, O or S, the further fused ring being optionally substituted.

286. The compound wherein $R^{7B}$ is methyl.

287. The compound wherein a stereogenic center created by the $R^{7B}$ methyl group is in the R-configuration.

288. The compound wherein a stereogenic center created by the $R^{7B}$ methyl group is in the S-configuration.

289. The compound wherein $R^{7C}$ is methyl.

290. The compound wherein a stereogenic center created by the $R^{7C}$ methyl group is in the R-configuration.

291. The compound wherein a stereogenic center created by the $R^{7C}$ methyl group is in the S-configuration.

292. The compound wherein $R^{7D}$ is hydrogen.

293. The compound wherein $R^{7A}$ is cyanomethyl.

294. The compound wherein a stereogenic center created by the cyanomethyl group is in the R-configuration.

295. The compound wherein a stereogenic center created by the cyanomethyl group is in the S-configuration.

296. A compound of Formula (XXXVII):

(XXXVII)

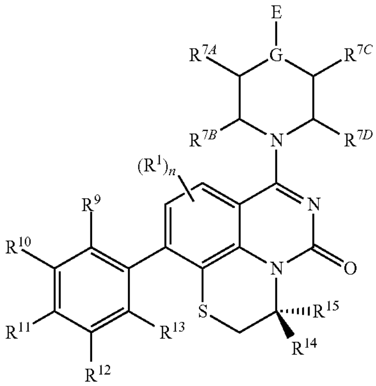

wherein:

E is an electrophilic moiety;

G is selected from the group consisting of N, CH, and

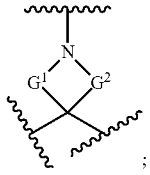

;

wherein $G^1$ and $G^2$ are independently $(CH_2)_q$, where q is 1 or 2;

each $R^1$ is an optional substitution independently selected from the group consisting of alkyl, cyano, cycloalkyl, halo, haloalkyl, trifluoromethyl, and alkoxy;

n is an integer from 0 to 2;

$R^{7A}$, $R^{7B}$, $R^{7C}$, and $R^{7D}$ are independently selected from hydrogen, alkyl, and cyanoalkyl; or any two $R^{7A-D}$ may combine to form a fused-ring or bridging bicycle, wherein any one fused-ring or bridging atom is O, S, S═O, or $SO_2$.

wherein $R^9$, $R^{10}$, $R^{11}$, $R^{12}$, and $R^{13}$ are each independently selected from the group consisting of hydrogen, halo, alkyl, alkoxy, haloalkyl, trifluoromethyl, cycloalkyl and any two adjacent $R^9$, $R^{10}$, $R^{11}$, $R^{12}$, and $R^{13}$ together combine to form a further fused ring that is an aromatic ring optionally comprising 1 to 3 heteroatoms independently selected from N, O or S, the further fused ring being optionally substituted;

wherein $R^{14}$ and $R^{15}$ are selected from the group consisting of hydrogen, hydroxyl, amino, N-alkylamino, dialkylamino, N-alkylamino alkyl, N,N-dialkylamino, N,N-dialkylamino alkyl, cycloalkylamino, cycloalkylaminoalkyl, alkylamidoalkyl, arylamidoalkyl, alkylsulfonamidoalkyl, arylsulfonamidoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted, with the proviso that one of $R^{14}$ or $R^{15}$ is hydrogen; and wherein E is optionally substituted.

309. The compound wherein the compound is a single rotamer of Formula (XXXVIIa):

(XXXVIIa)

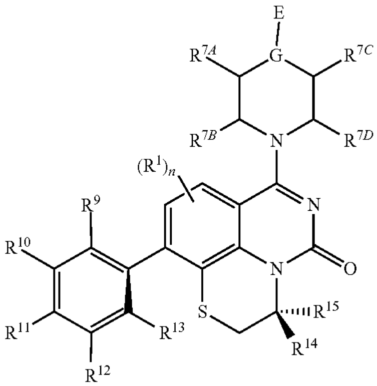

310. The compound wherein the compound is a single rotamer of Formula (XXXVIIb):

(XXXVIIb)

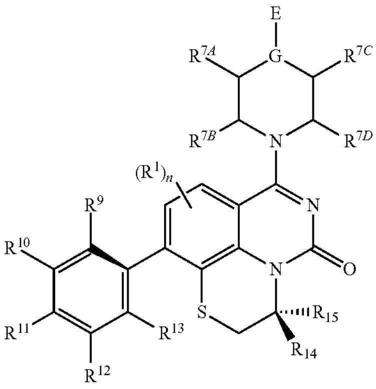

311. A compound of Formula (XXXVIII):

(XXXVIII)

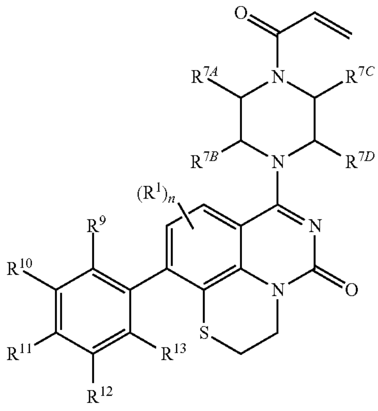

wherein:

each $R^1$ is an optional substitution independently selected from the group consisting of alkyl, cyano, cycloalkyl, halo, haloalkyl, trifluoromethyl, and alkoxy;

n is an integer from 0 to 2;

$R^{7A}$, $R^{7B}$, $R^{7C}$, and $R^{7D}$ are independently selected from hydrogen, alkyl, and cyanoalkyl; or any two $R^{7A-D}$ may combine to form a fused-ring or bridging bicycle, wherein any one fused-ring or bridging atom is O, S, S═O, or $SO_2$.

wherein $R^9$, $R^{10}$, $R^{11}$, $R^{12}$, and $R^{13}$ are each independently selected from the group consisting of hydrogen, halo, alkyl, alkoxy, haloalkyl, trifluoromethyl, cycloalkyl and any two adjacent $R^9$, $R^{10}$, $R^{11}$, $R^{12}$, and $R^{13}$ together combine to form a further fused ring that is an aromatic ring optionally comprising 1 to 3 heteroatoms independently selected from N, O or S, the further fused ring being optionally substituted.

wherein the acrylyl moiety linked to N is optionally substituted.

324. A compound of Formula (XXXIX):

(XXXIX)

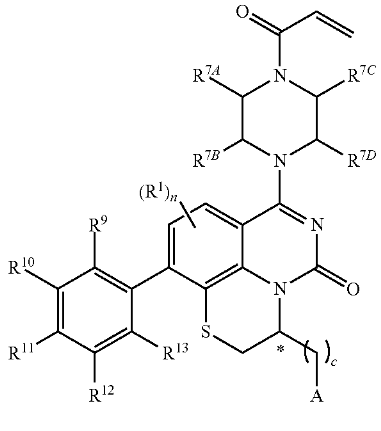

wherein * is a stereogenic center;

each $R^1$ is an optional substitution independently selected from the group consisting of alkyl, cyano, cycloalkyl, halo, haloalkyl, trifluoromethyl, and alkoxy;

n is an integer from 0 to 2;

$R^{7A}$, $R^{7B}$, $R^{7C}$, and $R^{7D}$ are independently selected from hydrogen, alkyl, and cyanoalkyl; or any two $R^{7A-D}$ may combine to form a fused-ring or bridging bicycle, wherein any one fused-ring or bridging atom is O, S, S═O, or $SO_2$.

wherein $R^9$, $R^{10}$, $R^{11}$, $R^{12}$, and $R^{13}$ are each independently selected from the group consisting of hydrogen, halo, alkyl, alkoxy, haloalkyl, trifluoromethyl, cycloalkyl and any two adjacent $R^9$, $R^{10}$, $R^{11}$, $R^{12}$, and $R^{13}$ together combine to form a further fused ring that is an aromatic ring optionally comprising 1 to 3 heteroatoms independently selected from N, O or S, the further fused ring being optionally substituted.

c is an integer from 0 to 4;

A is selected from the group consisting of hydroxyl, amino, N-alkylamino, N,N-dialkylamino, cycloalkylamino, N-alkylaminoalkyl, N,N-dialkylaminoalkyl, cycloalkylaminoalkyl, alkylamidoalkyl, arylamidoalkyl, alkylsulfonamidoalkyl, arylsulfonamidoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted; and wherein the acrylyl moiety linked to N is optionally substituted.

337. A compound of Formula (XL):

(XL)

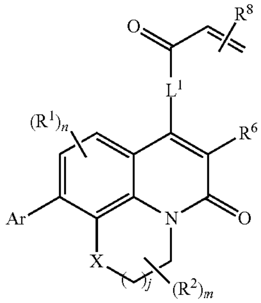

wherein:

X is $S(O)_p$, wherein p is an integer from 0 to 2;

j is an integer from 0 to 2;

$L^1$ is linking group comprising at least one nitrogen atom;

each $R^1$ is an optional substitution independently selected from the group consisting of alkyl, cyano, cycloalkyl, halo, haloalkyl, trifluoromethyl, and alkoxy;

n is an integer from 0 to 2;

$R^2$ is selected from the group consisting of alkyl, alkylamino, dialkylamino alkylamidoalkyl, arylamidoalkyl, alkylsulfonamidoalkyl, arylsulfonamidoalkyl, N-alkyl aminoalkyl, N,N-dialkyl aminoalkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted;

m is an integer from 0 to 6;

$R^6$ is selected from the group consisting of hydrogen, alkyl, haloakyl, cyano, halo, alkoxy, aryl, heteroaryl, and trifluoromethyl;

$R^8$ is selected from the group consisting of fluorine, methyl, and —$CH_2NR^aR^b$, wherein $R^a$ and $R^b$ are independently selected from hydrogen or alkyl; or $R^a$ and $R^b$ combine to form a $C_2$-$C_6$ nitrogen containing heterocycle; and Ar is aryl, N-arylamino, N-aryl-N-alkylamino, aryloxy, arylthio, heteroaryl, N-heteroarylamino, N-heteroaryl-N-alkylamino, heteroaryloxy, or heteroarylthio, any of which is optionally substituted.

347. The compound given by Formula XLI:

(XLI)

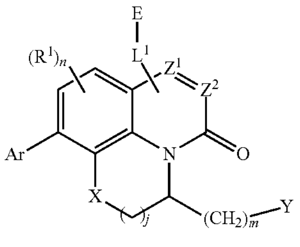

wherein:

Y is selected from the group consisting of hydrogen; N-linked heteroaromatic ring; N-linked azetidinyl optionally substituted with fluorine, CO—NR'R", or spiro-linked oxetane; $OR^a$; and $Z^3R^bR^c$;

R' and R" are independently hydrogen, alkyl or cycloalkyl;

$Z^3$ is CH, COH, or N;

m is an integer from 1 to 5;

$R^a$ is hydrogen, methyl, ethyl trifluoromethyl, heterocyclyl, or heterocyclylalkyl;

$R^b$ and $R^c$ are independently selected from alkyl, alkyl having one or more fluorine substitutions, cycloalkyl, oxetanyl, and N-methyl prolinyl; or $R^b$ and $R^c$ combine to form a cyclic structure A1:

A1

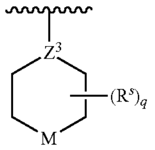

wherein q is an integer from 1 to 4; M is selected from a bond, O, S, SO, $SO_2$, $CH_2$, NH, NMe, N-ethyl, N-oxetanyl, and N-cyclopropyl, wherein each C—H of each alkylene, alkyl or cycloalkyl group is independently optionally substituted with a fluorine atom;

each $R^s$ is independently fluorine, oxo, alkoxy, or CO—NR'R", or any two RS combine to form a 1 to 3 carbon atom bridge, wherein the 1 to 3 carbon atom bridge is optionally substituted with one or more fluorine atoms;

each R' and R" is independently hydrogen, alkyl or cycloalkyl;

j is an integer from 0 to 2;

$Z^1$ and $Z^2$ are independently $CR^6$ or N, with the proviso that at least one of $Z^1$ or $Z^2$ is $CR^6$ with $R^6$ being a bond to $L^1$;

$L^1$ is linking group comprising at least one nitrogen atom;

E is an electrophilic moiety, wherein E is bound to $L^1$ via the at least one nitrogen atom;

each $R^1$ is independently selected from the group consisting of acyl, alkyl, carboxamide, cyano, cycloalkyl, halo, haloalkyl, trifluoromethyl, alkoxy, aryl, heteroaryl, N-arylamino, N-aryl-N-alkylamino, aryloxy, cycloalkyl, heterocyclyl, and arylthio with the proviso that at least one $R^1$ is aryl, N-arylamino, N-aryl-N-alkylamino, aryloxy, arylthio, or heteroaryl, any of which is optionally substituted;

n is an integer from 1 to 3;

m is an integer from 0 to 6;

$R^3$, $R^4$, and $R^5$ are each independently selected from the group consisting of hydrogen alkyl, halo, alkoxy, aryl, heteroaryl, and cycloalkyl, any of which are optionally substituted; and $R^6$ is selected from the group consisting of hydrogen, alkyl, haloakyl, cyano, halo, alkoxy, aryl, heteroaryl, trifluoromethyl and bond to $L^1$, and pharmaceutically acceptable salts thereof.

348. The compound having the formula XLII (XLII)

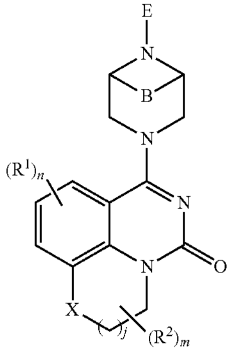

wherein:

X is $S(O)_p$, wherein p is an integer from 0 to 2;

j is an integer from 0 to 2;

B is bridging group comprising 1 to 3 carbon atoms, wherein any one carbon atom is optionally replaced by O, S, $SO_2$, or N-alkyl;

E is an electrophilic moiety;

each $R^1$ is independently selected from the group consisting of acyl, alkyl, carboxamide, cyano, cycloalkyl, halo, haloalkyl, trifluoromethyl, alkoxy, aryl, heteroaryl, N-arylamino, N-aryl-N-alkylamino, aryloxy, cycloalkyl, heterocyclyl, and arylthio with the proviso that:

at least one $R^1$ is aryl, N-arylamino, N-aryl-N-alkylamino, aryloxy, arylthio, or heteroaryl, any of which is optionally substituted;

n is an integer from 1 to 3;

$R^2$ is selected from the group consisting of alkyl, alkylamino, dialkylamino, alkylamidoalkyl, arylamidoalkyl, alkylsulfonamidoalkyl, arylsulfonamidoalkyl, N-alkyl aminoalkyl, N,N-dialkyl aminoalkyl, amido, amido alkyl, alkoxy, alkoxyalkyl, cycloalkyl, alkylcycloalkyl, hydroxyalkyl, halo, haloalkyl, aryl, aralkyl, heteroaryl, heteroarylalkyl, heterocyclyl, and heterocyclylalkyl, any of which are optionally substituted;

m is an integer from 0 to 6;

$R^3$, $R^4$, and $R^5$ are each independently selected from the group consisting of hydrogen alkyl, halo, alkoxy, aryl, heteroaryl, and cycloalkyl, any of which are optionally substituted, and pharmaceutically acceptable salts thereof.

349. A compound selected from Tables 1-7.

353. A compound of Formula (XLIII) or pharmaceutically acceptable salt thereof:

(XLIII)

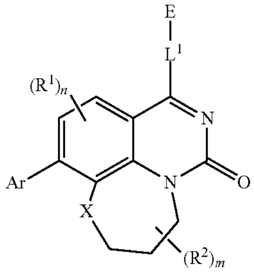

wherein:

X is O or S;

$L^1$ is linking group comprising at least one nitrogen atom;

E is an electrophilic moiety, wherein E is bound to $L^1$ via the at least one nitrogen atom;

each $R^1$ is an optional substitution independently selected from the group consisting of alkyl, cyano, cycloalkyl, halo, haloalkyl, trifluoromethyl, and alkoxy;

Ar is selected from the group consisting of aryl, N-arylamino, N-aryl-N-alkylamino, aryloxy, arylthio, or heteroaryl, any of which is optionally substituted; n is an integer from 1 to 2;

each $R^2$ is independently selected from the group consisting optionally substituted aryl, optionally substituted heteroaryl, optionally substituted heterocyclyl, —CHR'R", —OR', —SR', and —NR',R"; wherein each R' or R" is selected from the group consisting of hydrogen, alkyl, alkoxy, alkoxyalkyl, hydroxy, cycloalkoxy, cyano, cyanoalkyl, amido, amidoalkyl, N-alkylamido, N-alkylamidoalkyl, N,N-dialkylamido, N,N-dialkylamidoalkyl, amino, aminoalkyl, N-alkyl amino, N-alkyl aminoalkyl, N,N-dialkylamino, and N,N-dialkylaminoalkyl, any of which are optionally substituted; or any two R' and R" combine to form 3-7-membered ring, optionally comprising 1 or 2 heteroatoms selected from N, O, or S; or any two $R^2$ combine to form a spirocycle comprising 0 to 2 heteroatoms selected from N, O, or S; and m is an integer from 0 to 6.

360. A compound of Formula (XLIV) or pharmaceutically acceptable salt thereof:

(XLIV)

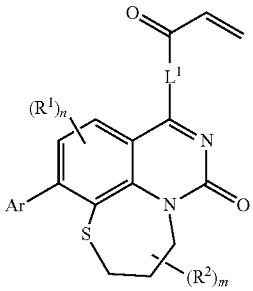

wherein:

$L^1$ is linking group comprising at least one nitrogen atom;

each $R^1$ is an optional substitution independently selected from the group consisting of alkyl, cyano, cyclopropyl, halo, haloalkyl, trifluoromethyl, alkoxy, n is 1 or 2;

each $R^2$ is independently selected from the group consisting optionally substituted aryl, optionally substituted heteroaryl, optionally substituted heterocyclyl, —CHR'R", —OR', —SR', and —NR',R"; wherein each R' or R" is selected from the group consisting of hydrogen, alkyl, alkoxy, alkoxyalkyl, hydroxy, cycloalkoxy, cyano, cyanoalkyl, amido, amidoalkyl, N-alkylamido, N-alkylamidoalkyl, N,N-dialkylamido, N,N-dialkylamidoalkyl, amino, aminoalkyl, N-alkyl amino, N-alkyl aminoalkyl, N,N-dialkylamino, and N,N-dialkylaminoalkyl, any of which are optionally substituted; or any two R' and R" combine to form 3-7-membered ring, optionally comprising 1 or 2 heteroatoms selected from N, O, or S; or any two $R^2$ combine to form a spirocycle comprising 0 to 2 heteroatoms selected from N, O, or S;

m is 1 or 2; and

Ar is a phenyl group optionally substituted with one or more alkyl, cycloalkyl, fluoro, chloro, bromo, iodo, trifluoromethyl or cyano.

365. A compound of Formula (XLV) or pharmaceutically acceptable salt thereof:

(XLV)

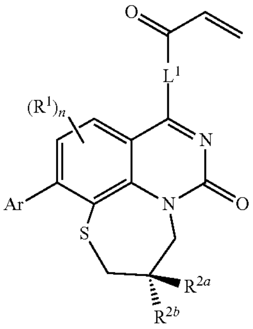

wherein:

$L^1$ is linking group comprising at least one nitrogen atom;

each $R^1$ is an optional substitution independently selected from the group consisting of alkyl, cyano, cyclopropyl, halo, haloalkyl, trifluoromethyl, alkoxy, n is 1 or 2;

$R^{2a}$ and $R^{2b}$ are independently selected from the group consisting of hydrogen, optionally substituted aryl, optionally substituted heteroaryl, optionally substituted heterocyclyl, —CHR'R", —OR', —SR', and —NR',R"; wherein each R' or R" is selected from the group consisting of hydrogen, alkyl, alkoxy, alkoxyalkyl, hydroxy, cycloalkoxy, cyano, cyanoalkyl, amido, amidoalkyl, N-alkylamido, N-alkylamidoalkyl, N,N-dialkylamido, N,N-dialkylamidoalkyl, amino, aminoalkyl, N-alkyl amino, N-alkyl aminoalkyl, N,N-dialkylamino, N,N-dialkylaminoalkyl, any of which are optionally substituted; or R' and R" combine to form 3-7-membered ring, optionally comprising 1 or 2 heteroatoms selected from N, O, or S, or $R^{2a}$ and $R^{2b}$ combine to form a spirocycle comprising 0 to 2 heteroatoms selected from N, O, or S; and Ar is a phenyl optionally substituted with one or more alkyl, cycloalkyl, fluoro, chloro, bromo, iodo, trifluoromethyl or cyano.

366. The compound wherein $L^1$ is

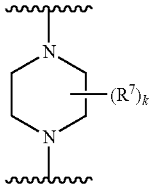

or

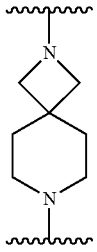

wherein k is an integer from 0 to 4; and each $R^7$ is independently selected from methyl, and cyanomethyl, or any two $R^7$ combine to form a bridge or spirocycle structure optionally comprising a heteroatom in the bridge or spirocycle selected from S, $SO_2$, O or N, and wherein the bridge or spirocycle structure is optionally substituted with oxo.

367. The compound of any of the preceding embodiments wherein n is 1 and $R^1$ is ortho to Ar.

368. The compound of any of the preceding embodiments wherein $R^1$ is chloro or trifluoromethyl.

369. The compound of any of the preceding embodiments wherein Ar is a phenyl ring comprising 1 to 3 fluorine substitutions.

370. The compound of any of the preceding embodiments wherein $R^{2a}$ is hydrogen and $R^{2b}$ is not hydrogen.

371. The compound of any of the preceding embodiments wherein $R^{2a}$ is hydrogen and $R^{2b}$ is not hydrogen.

372. The compound of any of the preceding embodiments wherein $R^{2a}$ and $R^{2b}$ combine to form a spirocyclic carbocycle or heterocycle.

373. The compound having the structure of formula XLVa or XLVb:

XLVa

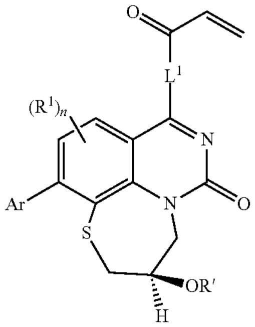

XLVb

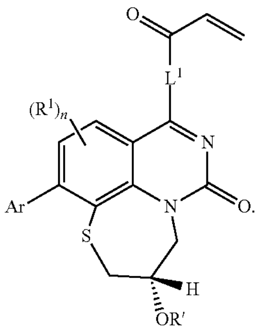

374. The compound having the structure of formula XLVc or XLVd:

XLVc

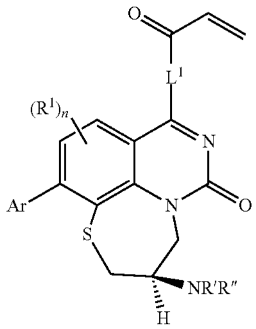

XLVd

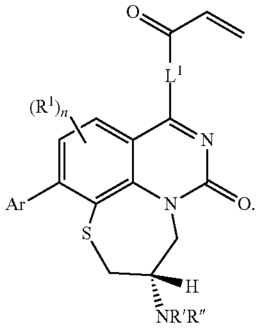

375. The compound having the structure of formula XLVe or XLVf:

XLVe

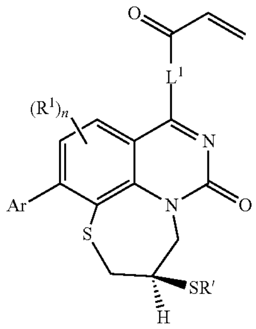

XLVf

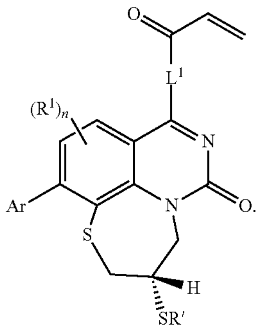

376. The compound having the structure of formula XLVg or XLVh:

XLVg
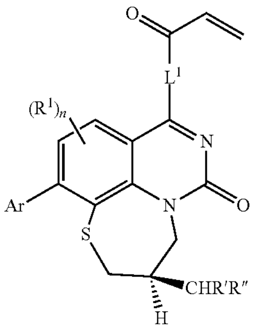
XLVh
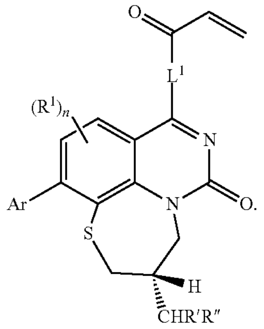
377. A compounds selected from:
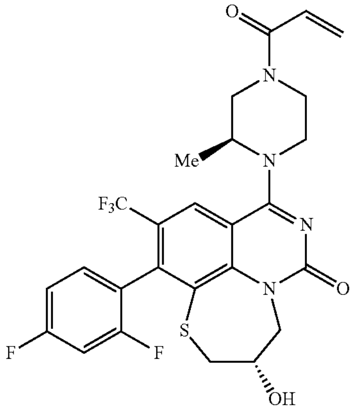
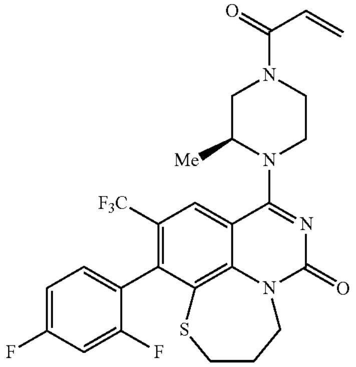
-continued
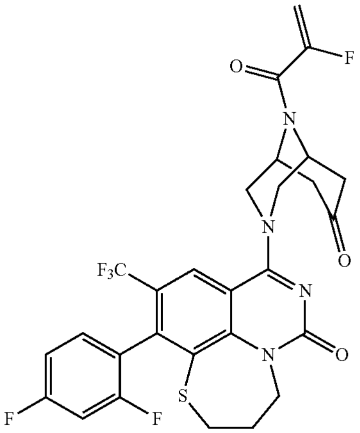
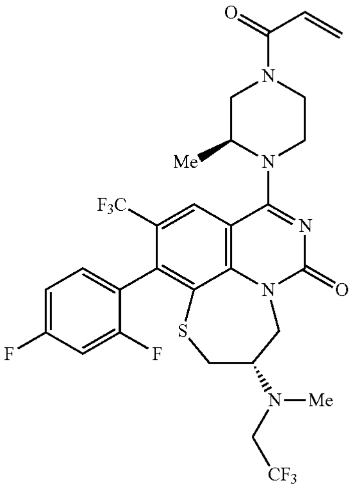
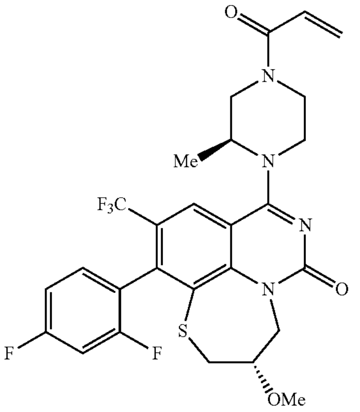

-continued
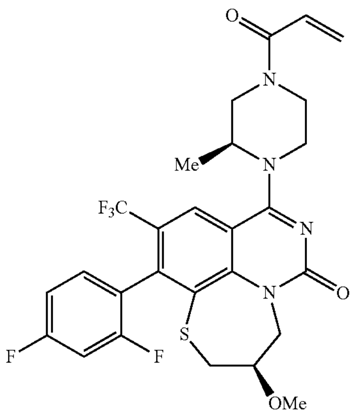
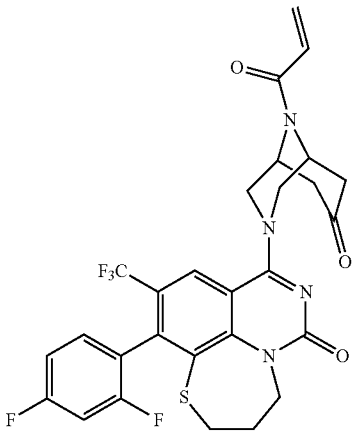
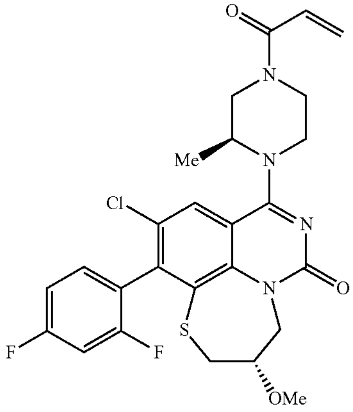
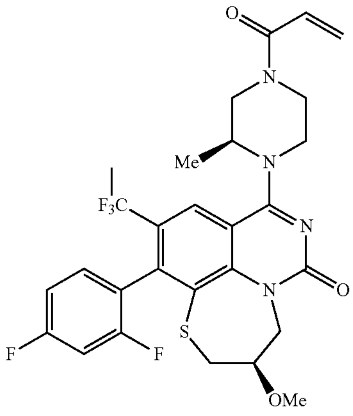
-continued
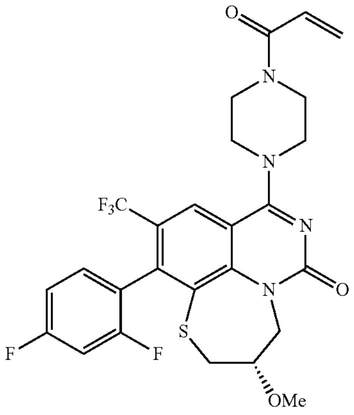
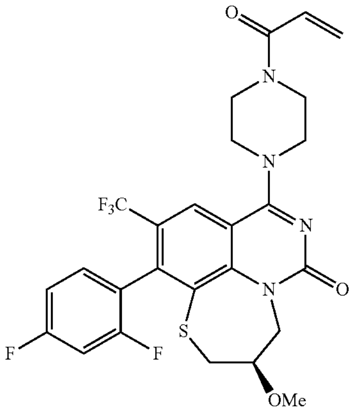
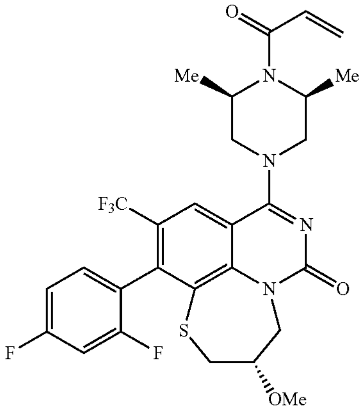
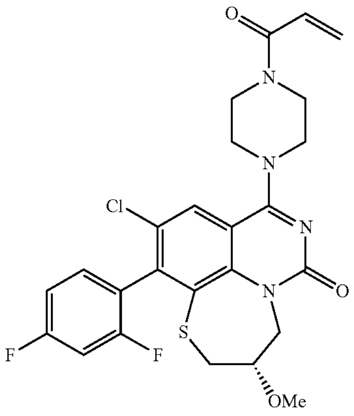

-continued
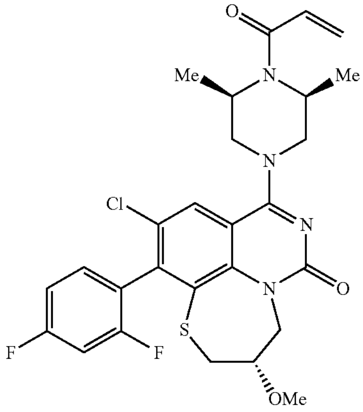
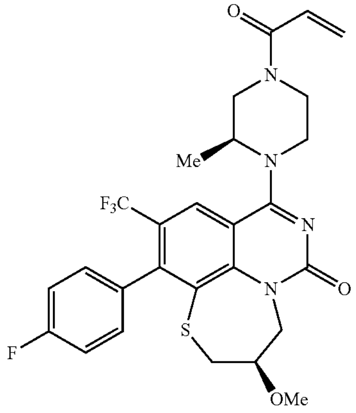
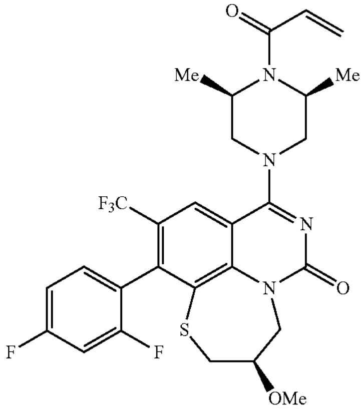
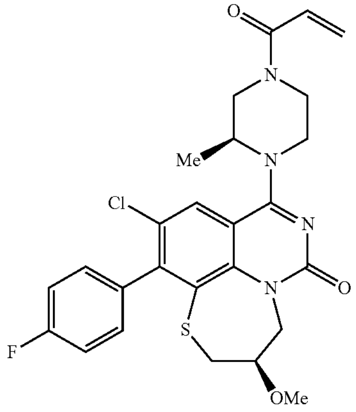
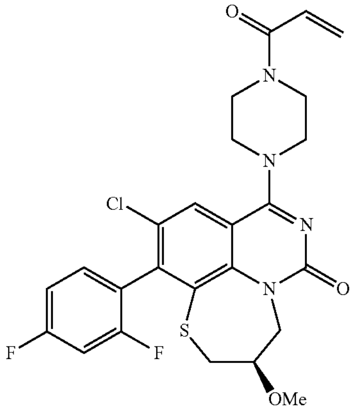
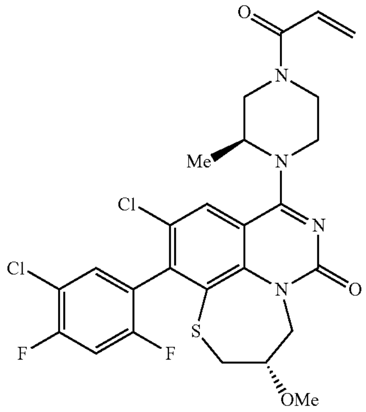
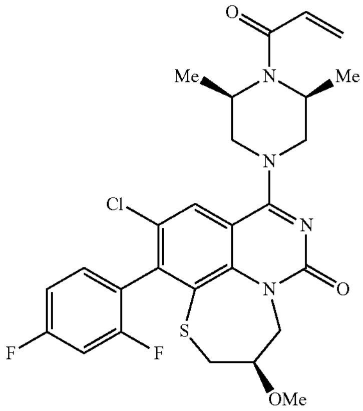
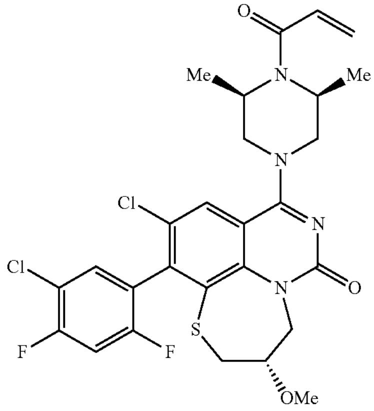

-continued
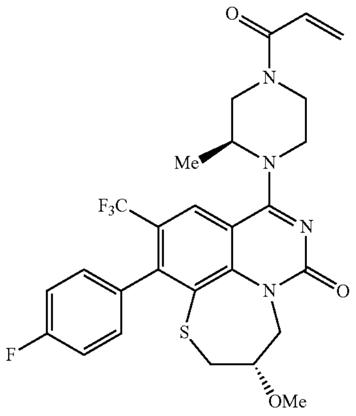
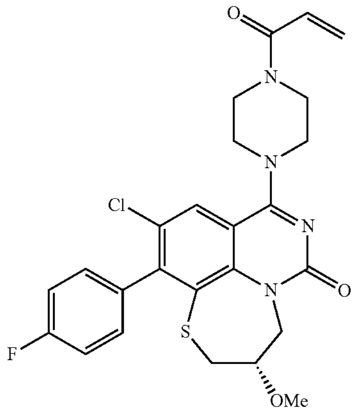
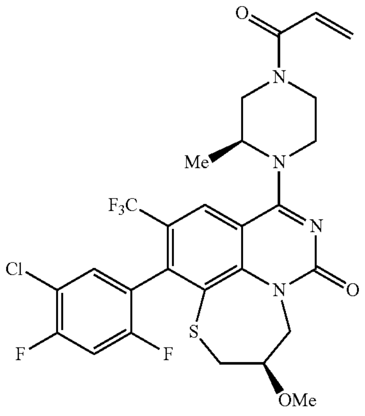
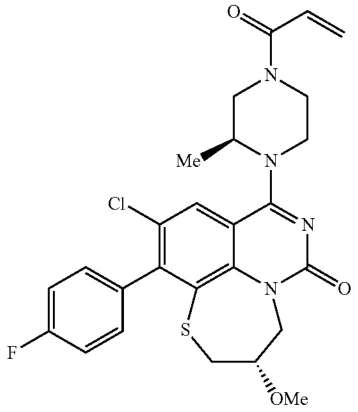
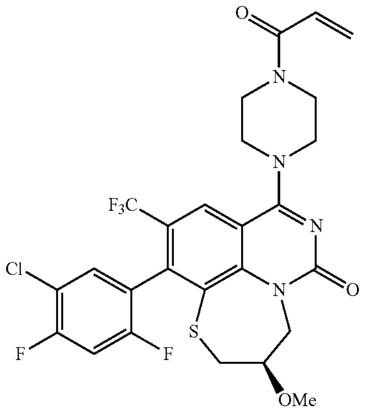
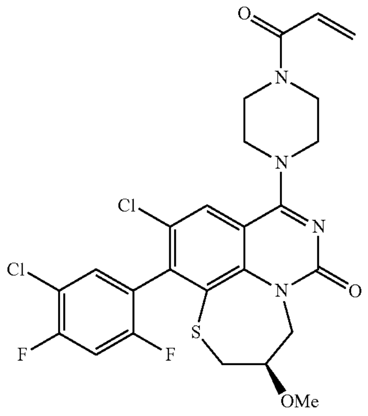
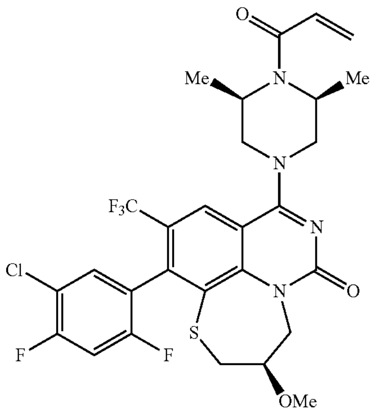
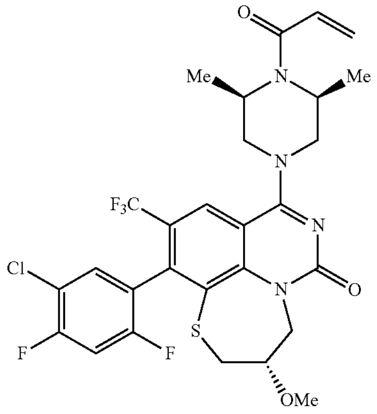

-continued
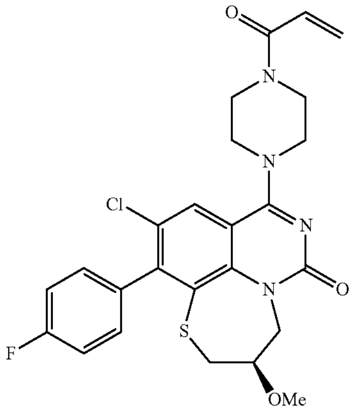
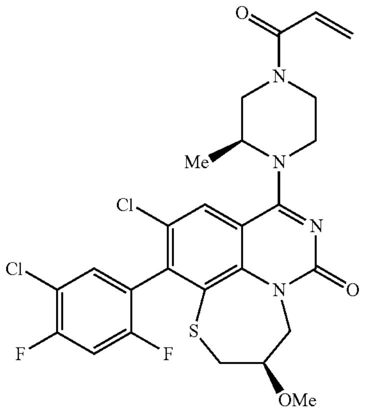
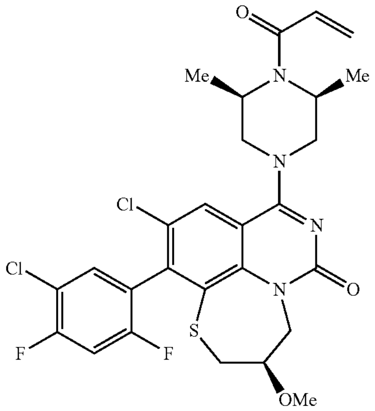
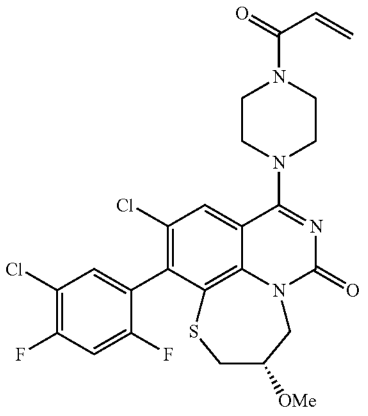
-continued
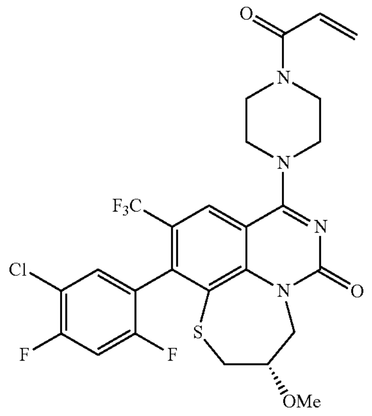
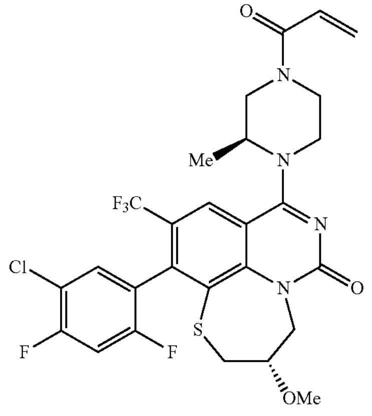
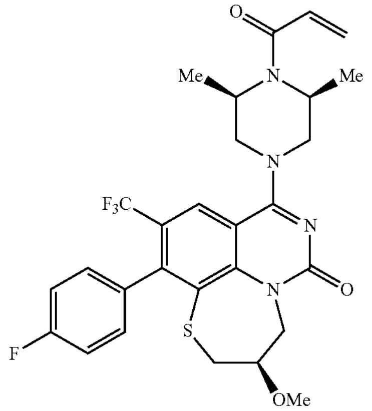
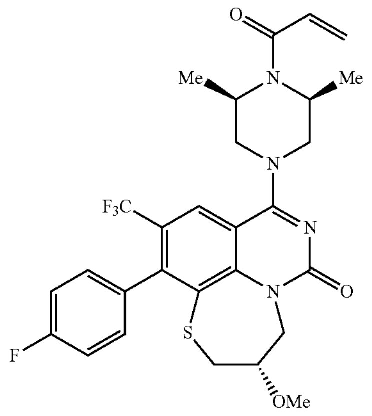

-continued
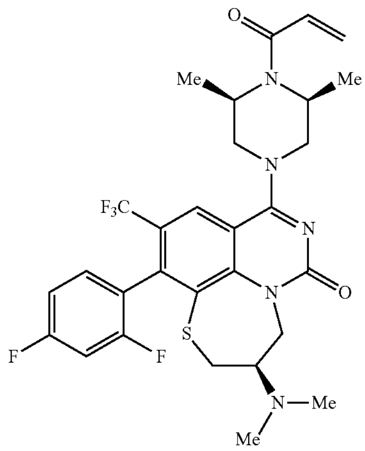
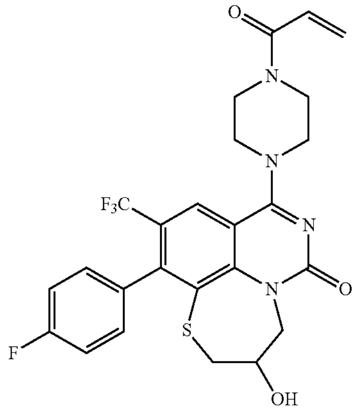
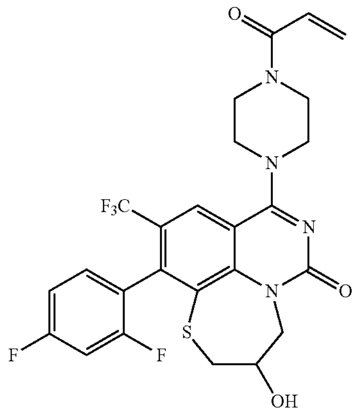
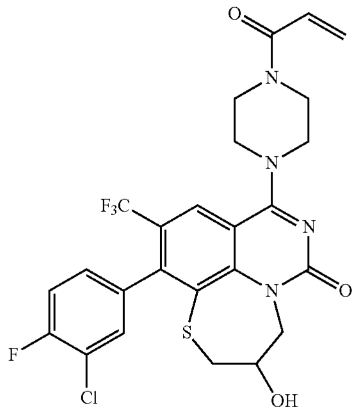
-continued
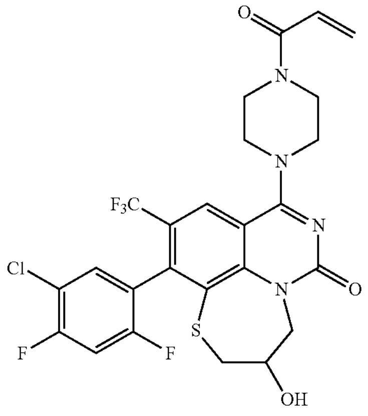
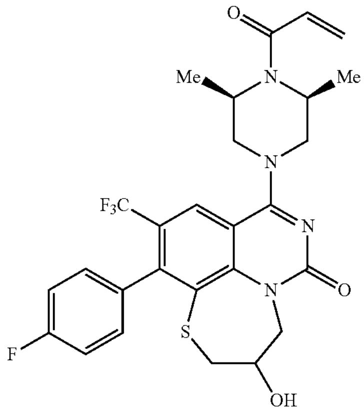
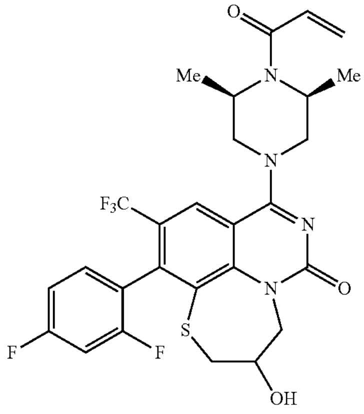
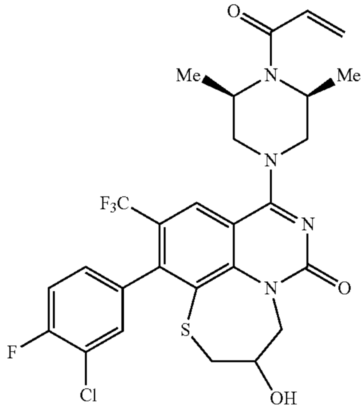

-continued
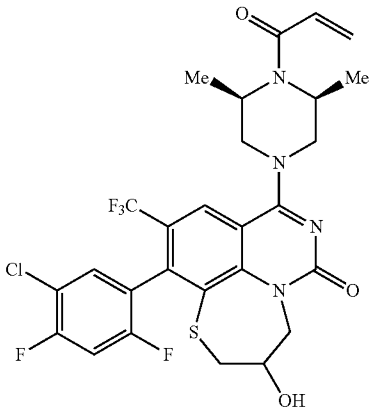
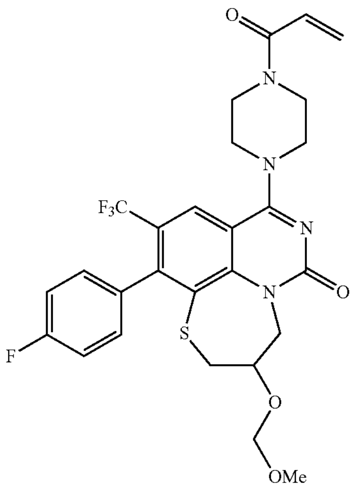
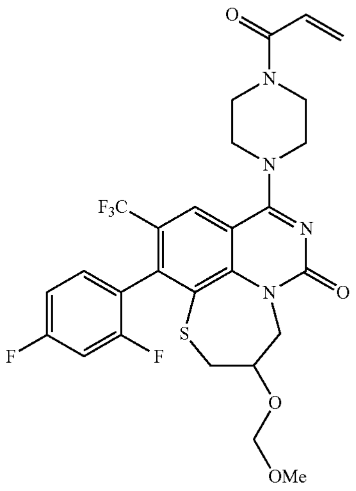
-continued
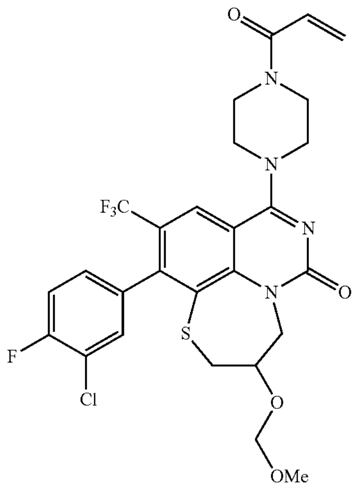
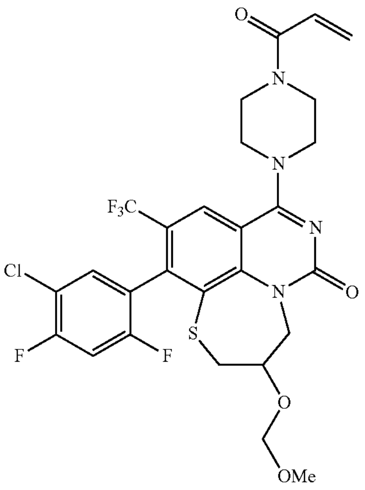
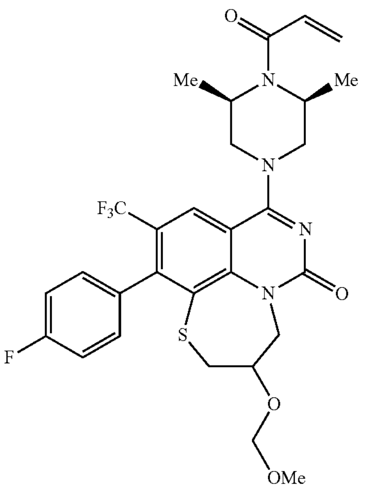

-continued
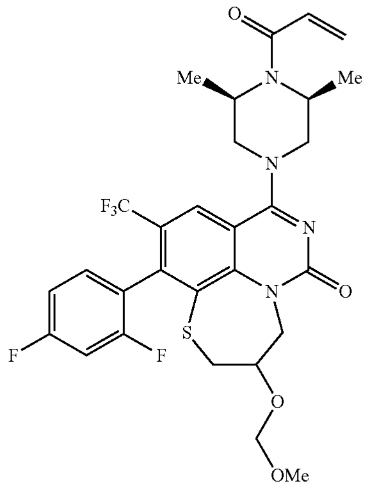
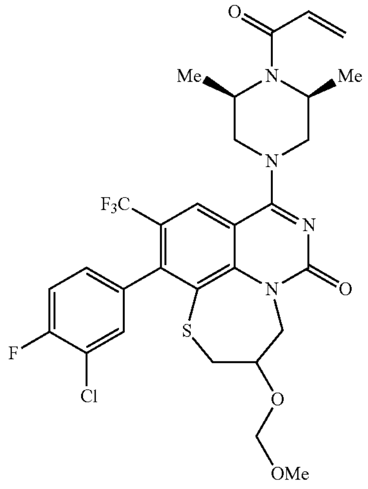
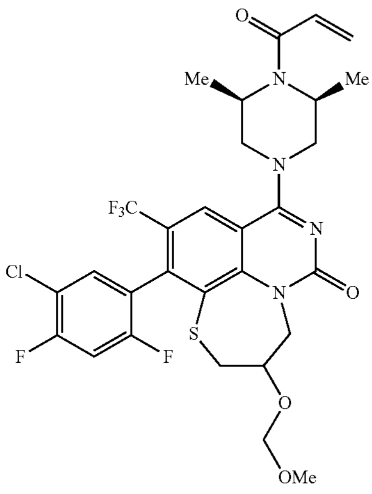
-continued
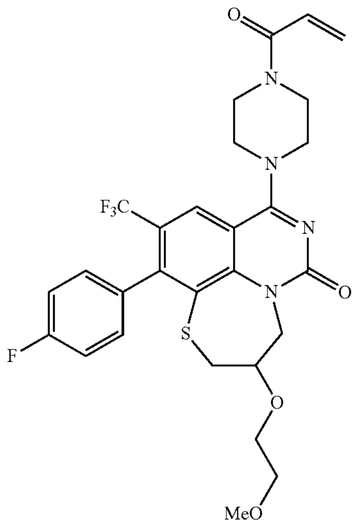
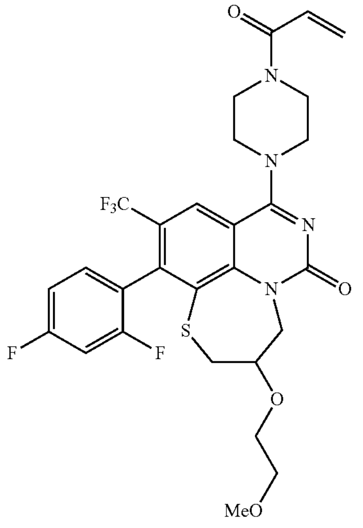
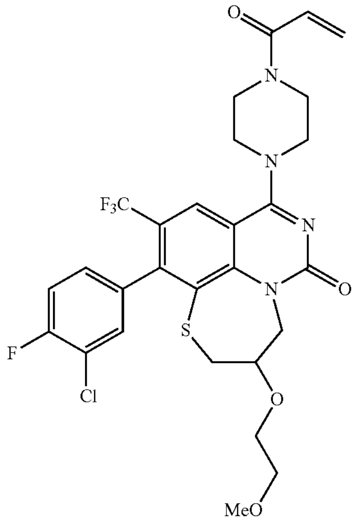

-continued
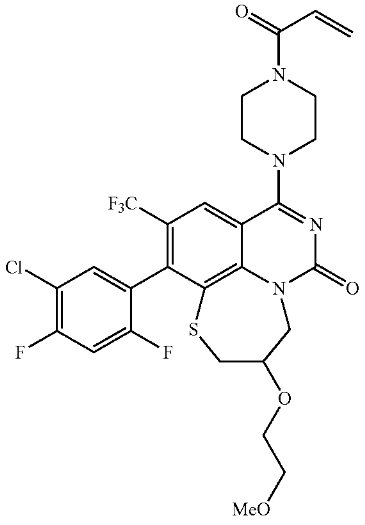
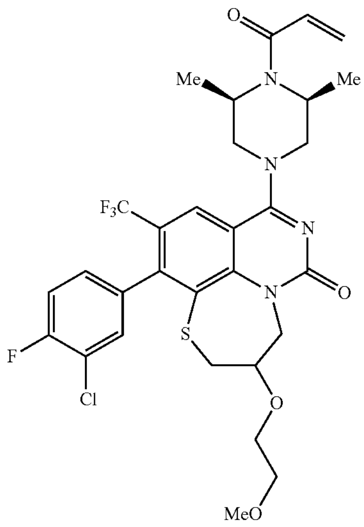
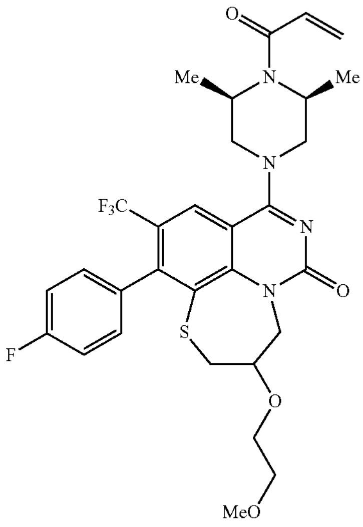
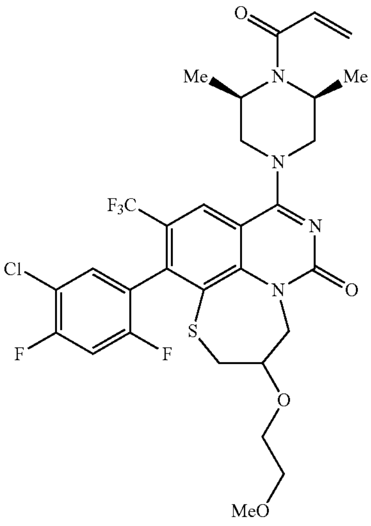
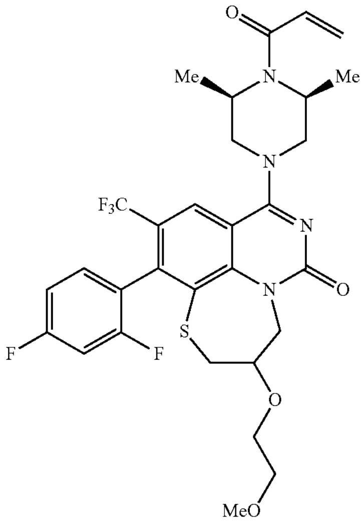
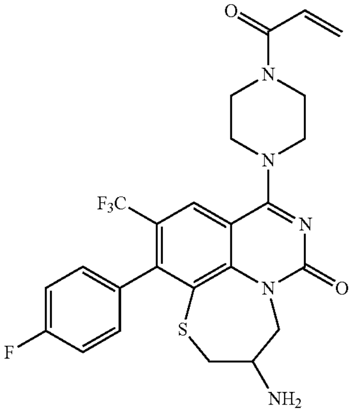

-continued
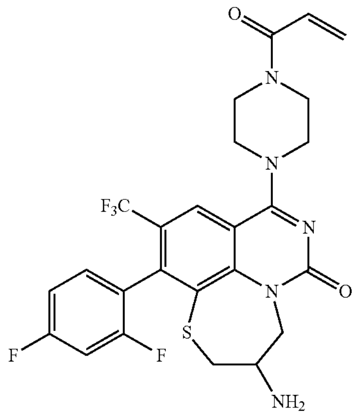
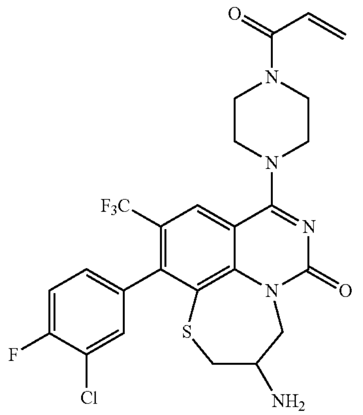
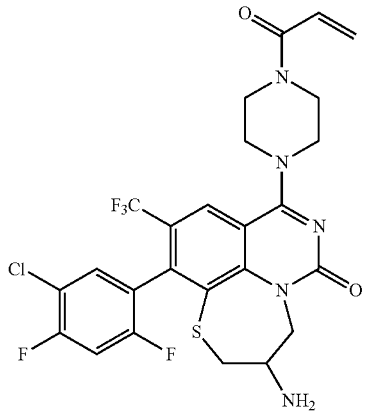
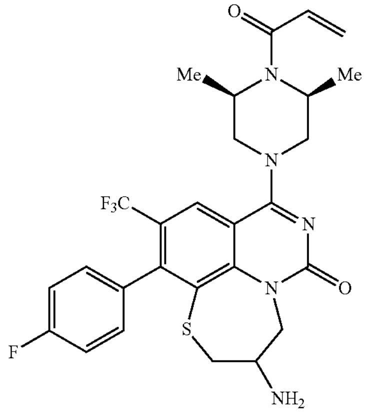
-continued
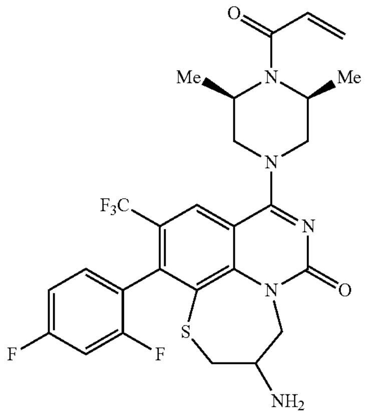
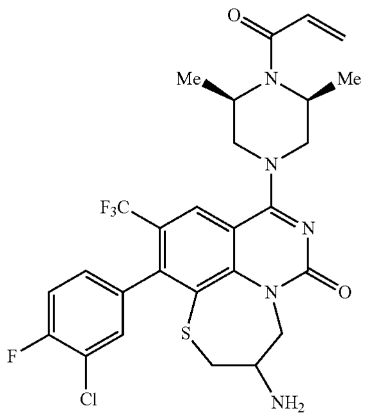
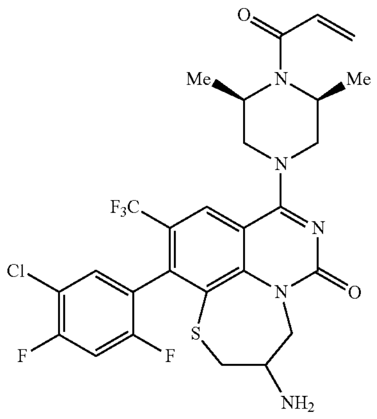

-continued
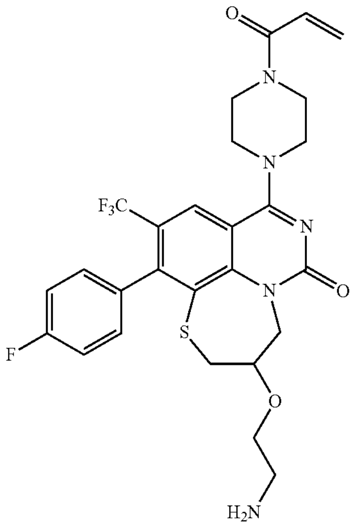
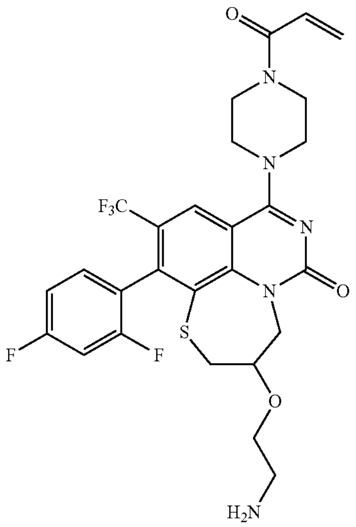
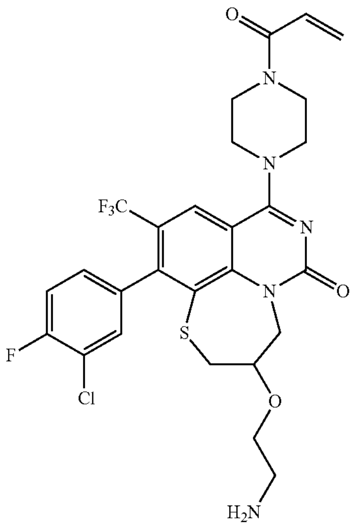
-continued
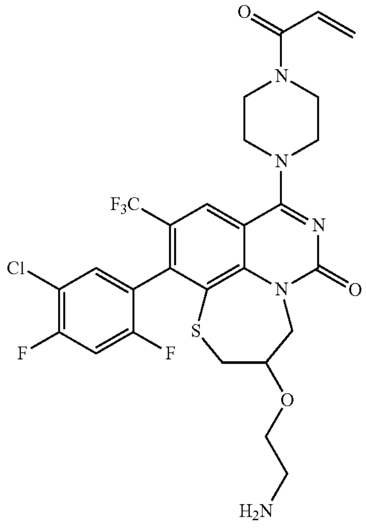
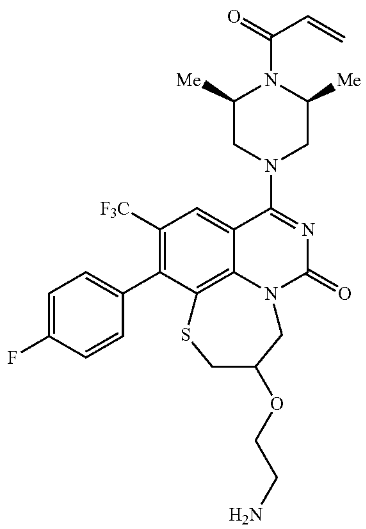
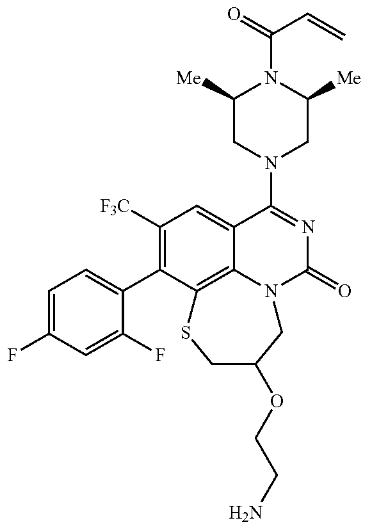

-continued
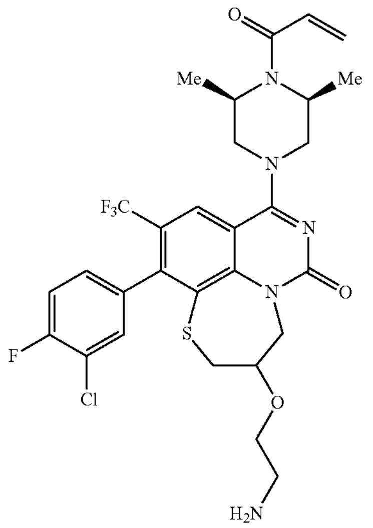
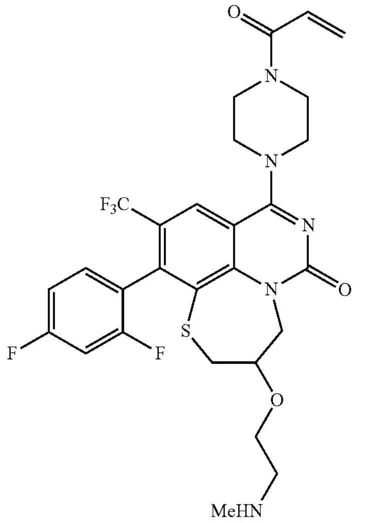
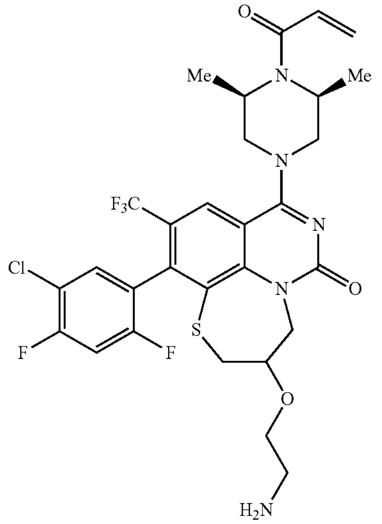
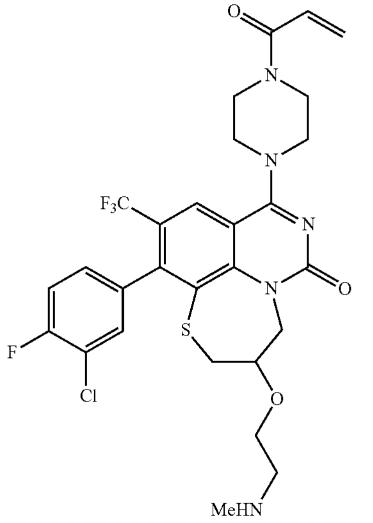
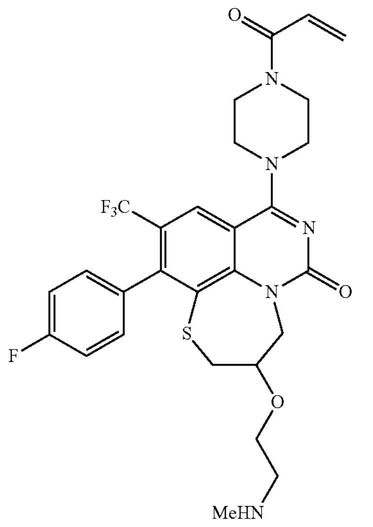
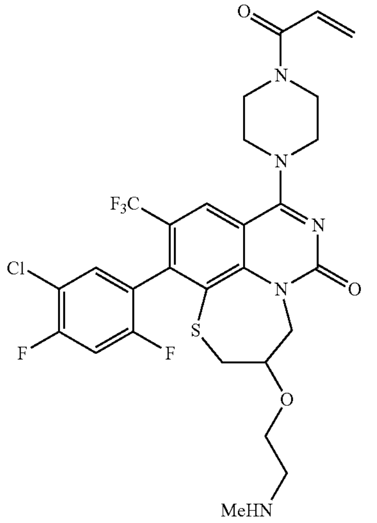
-continued -continued
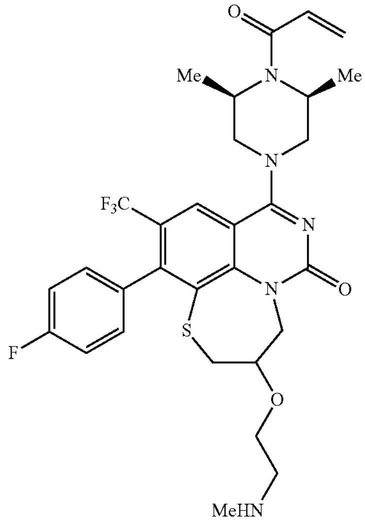
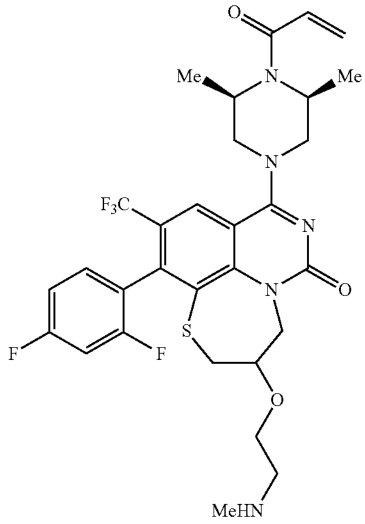
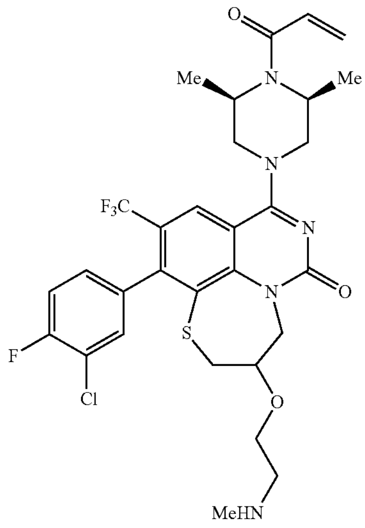
-continued
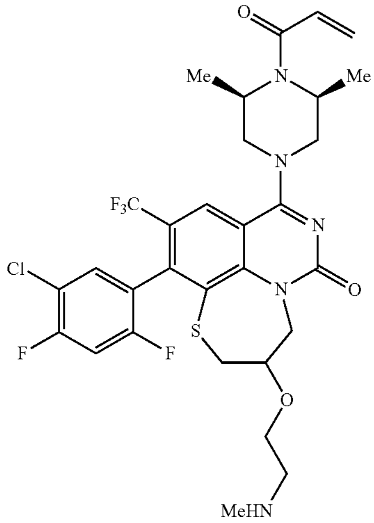
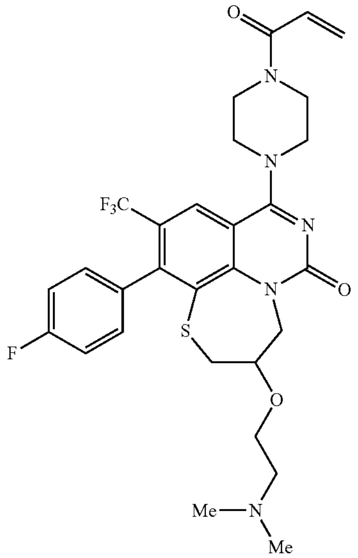
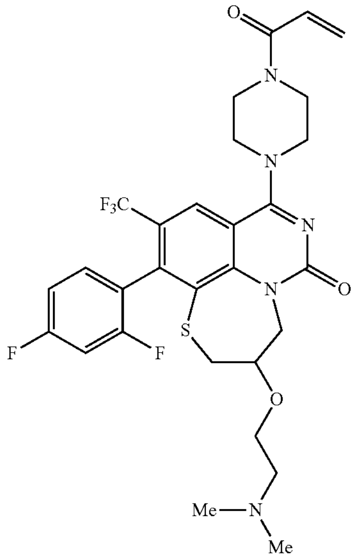

-continued
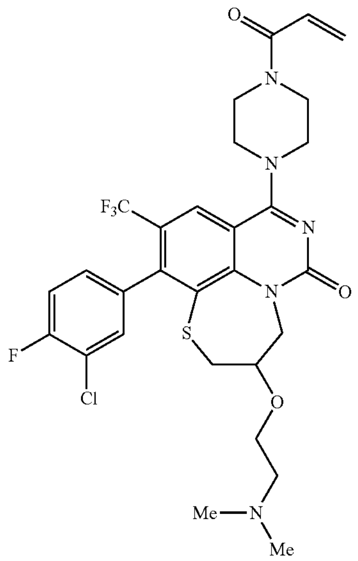
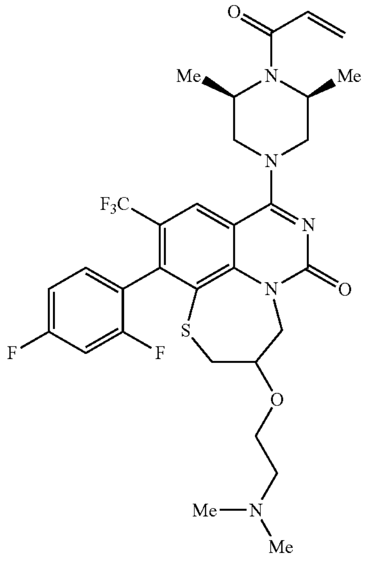
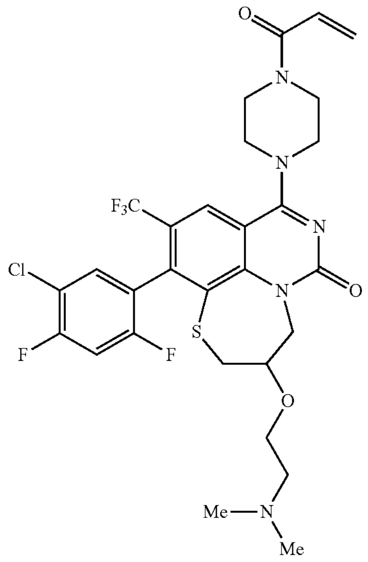
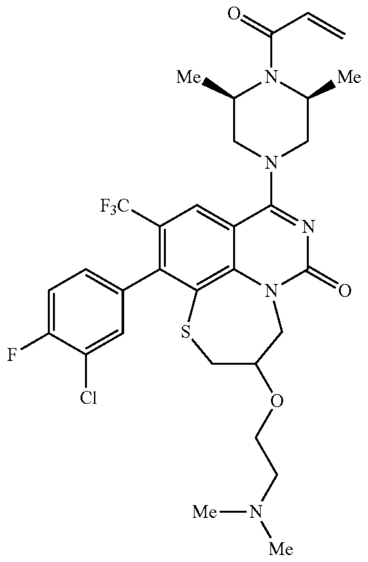
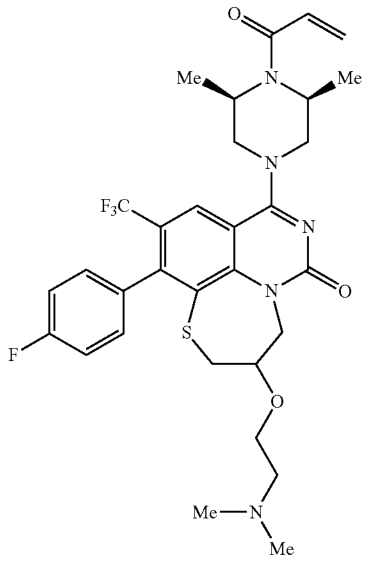
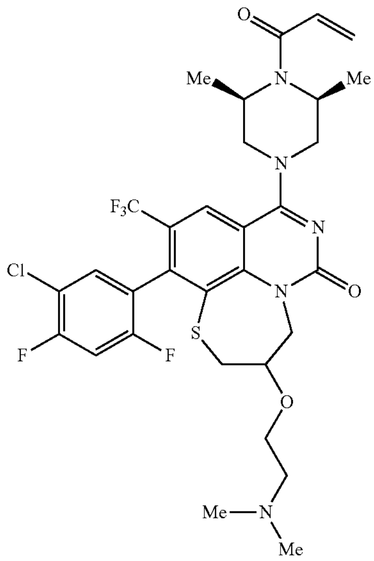

-continued
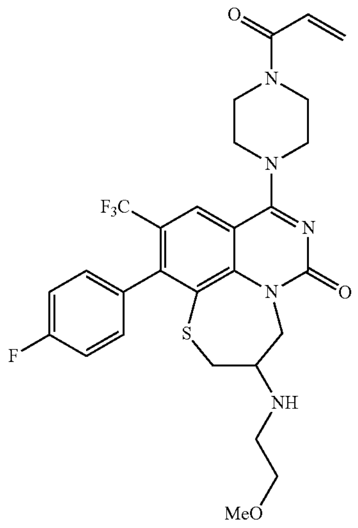
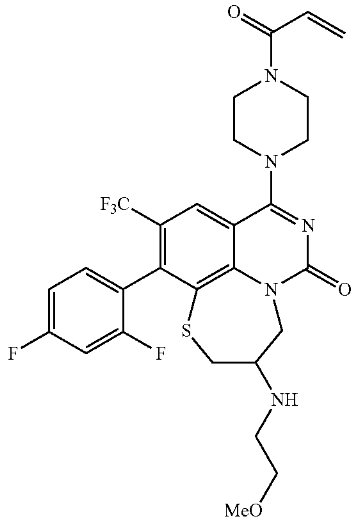
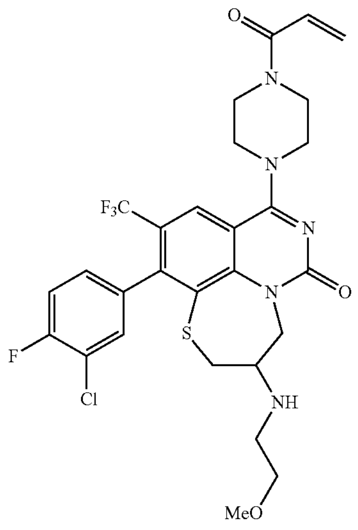
-continued
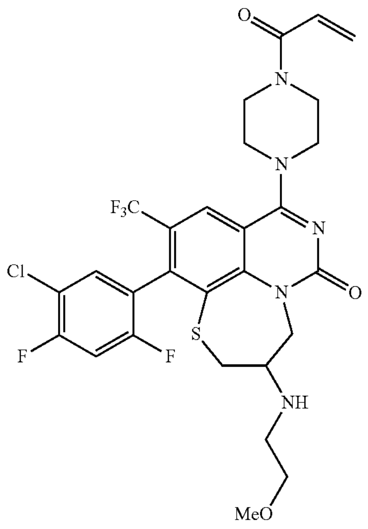
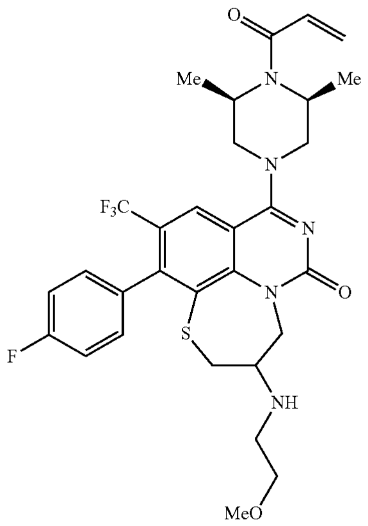
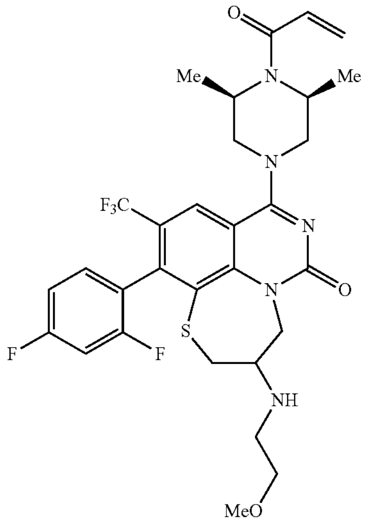

-continued
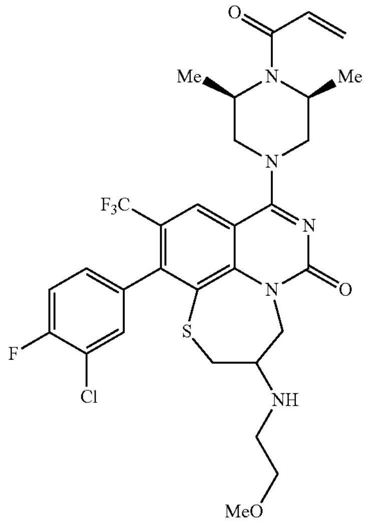
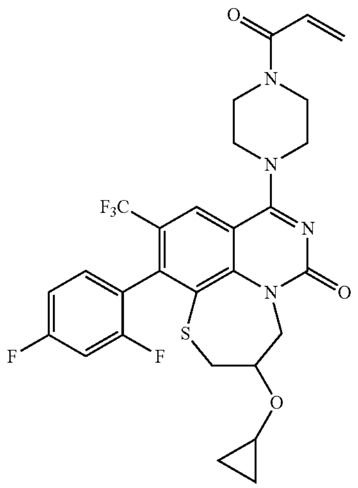
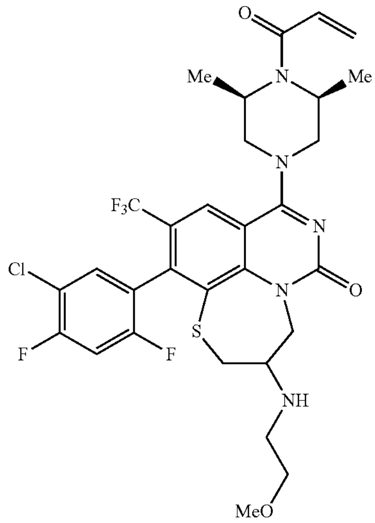
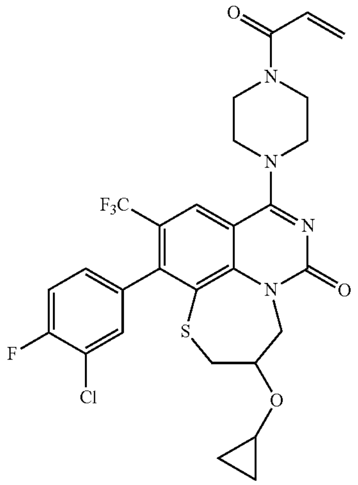
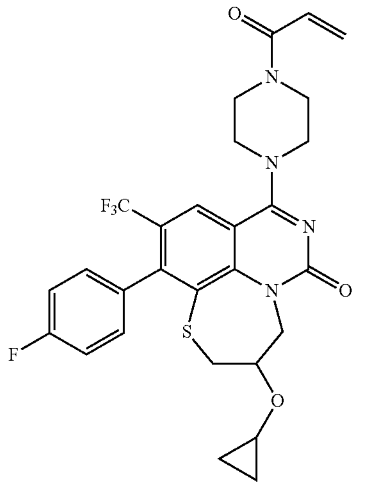
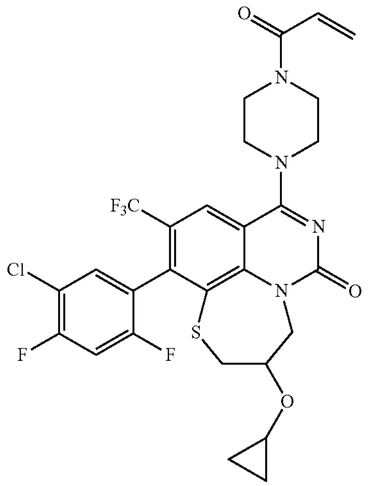

-continued
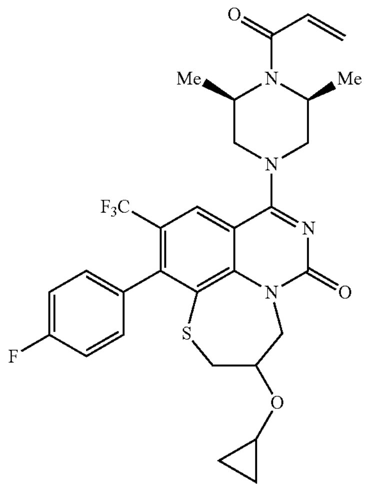
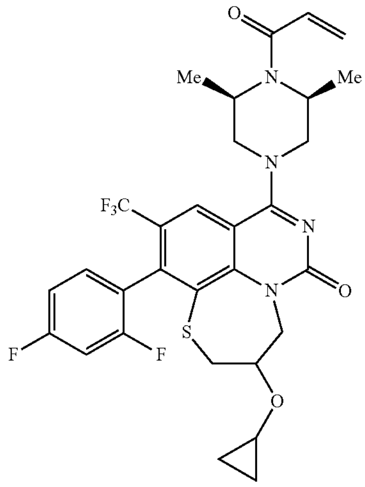
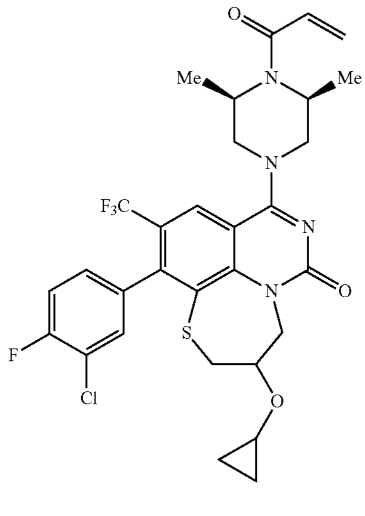
-continued
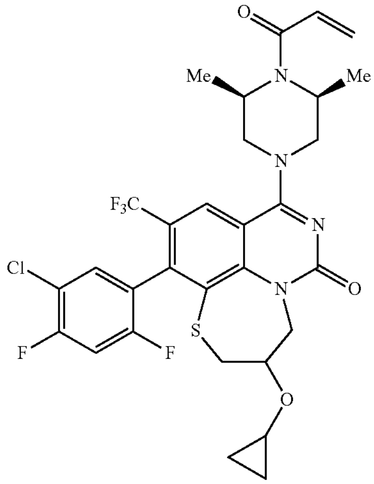
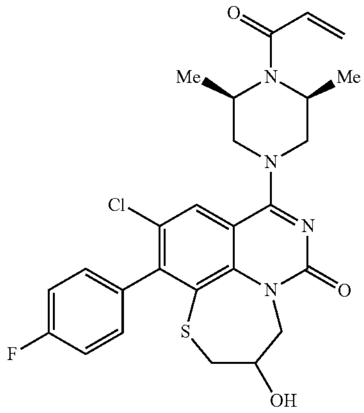
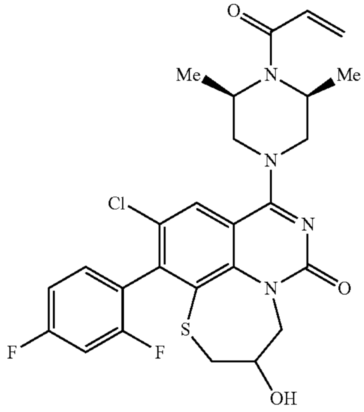
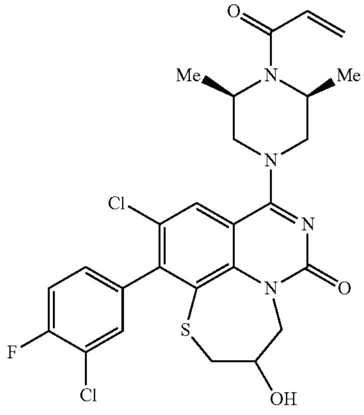

-continued
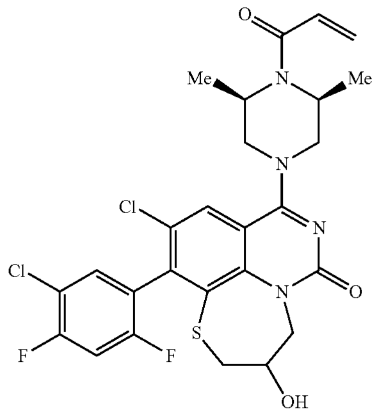
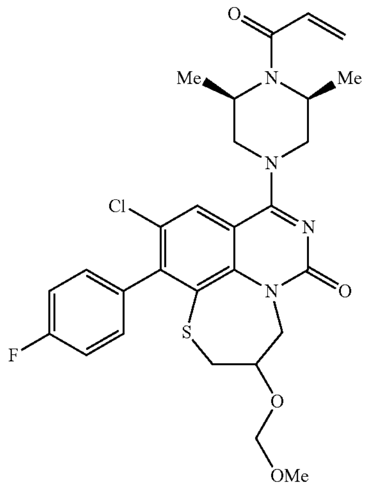
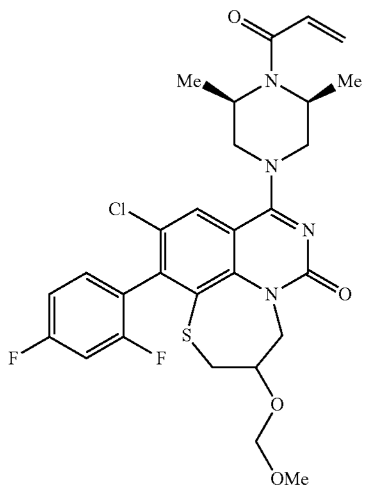
-continued
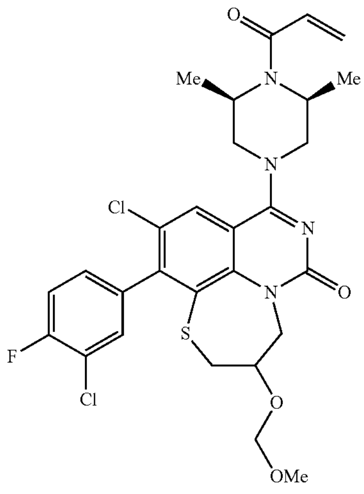
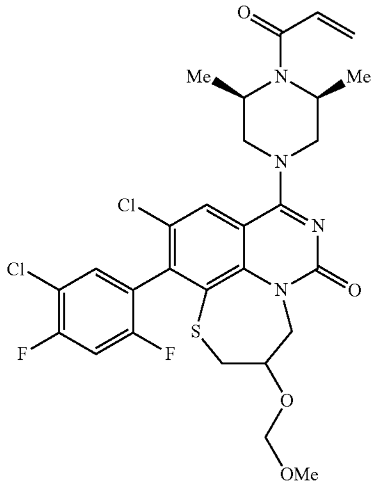
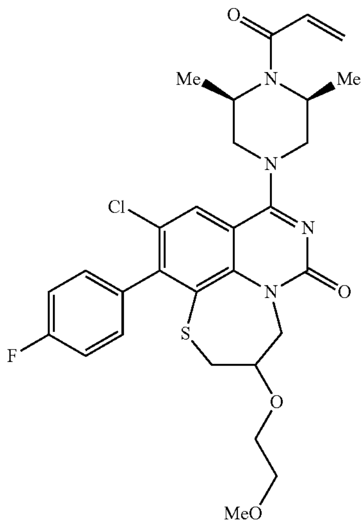

-continued
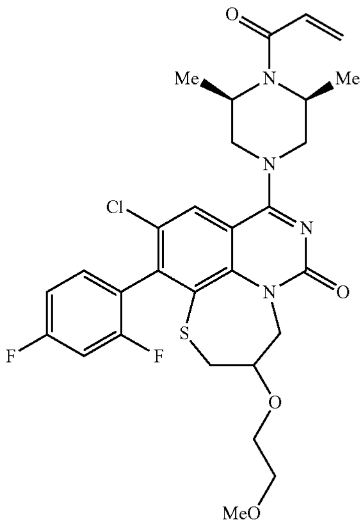
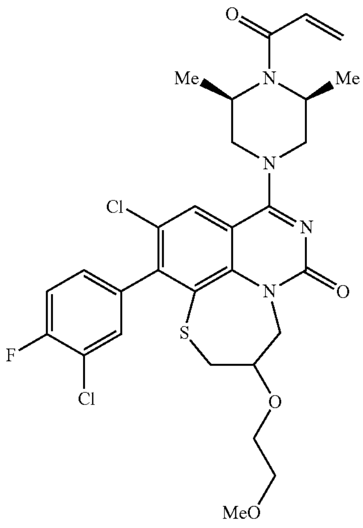
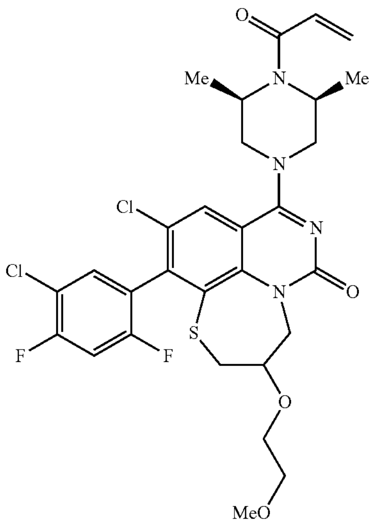
-continued
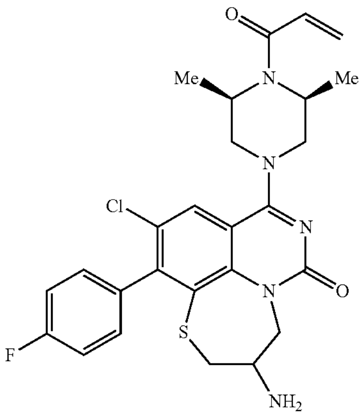
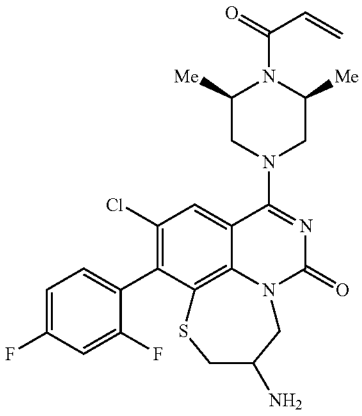
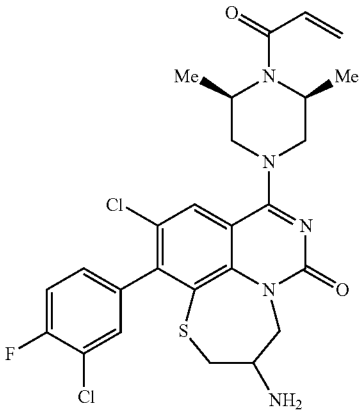
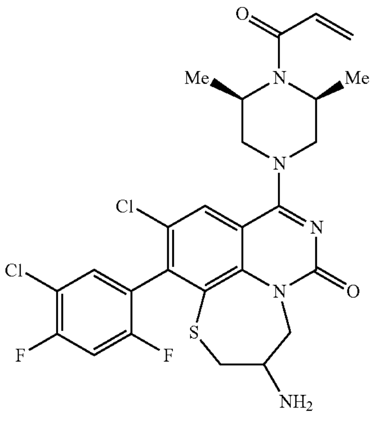

-continued
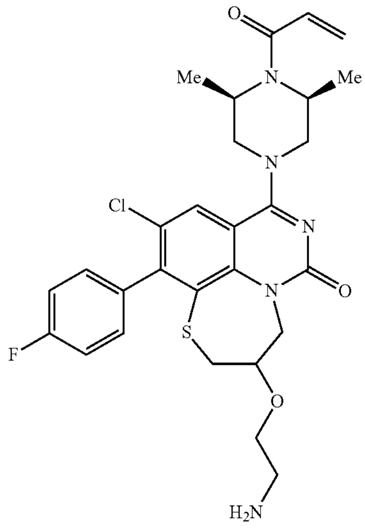
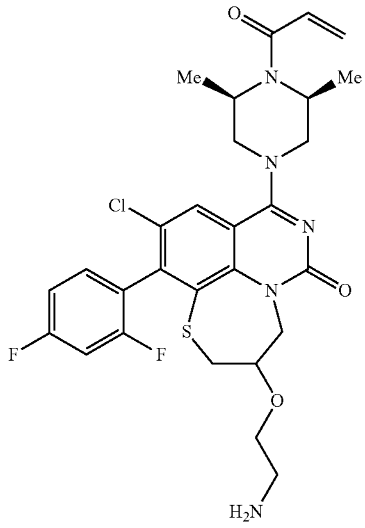
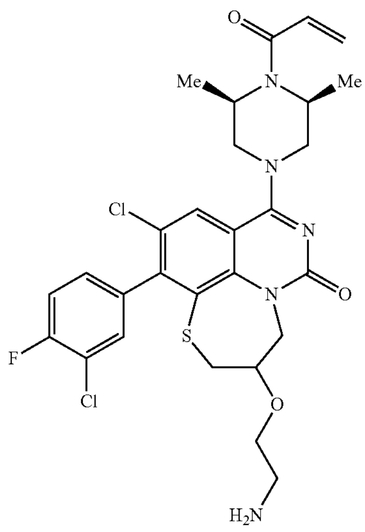
-continued
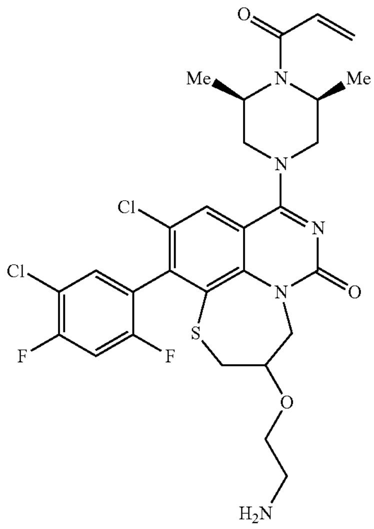
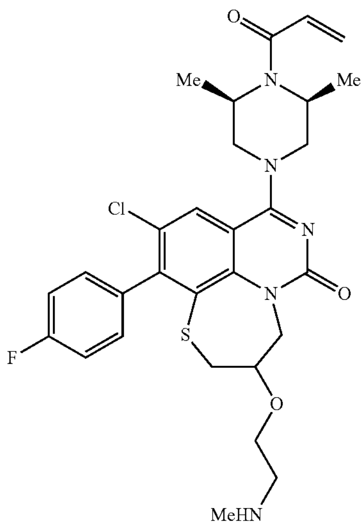
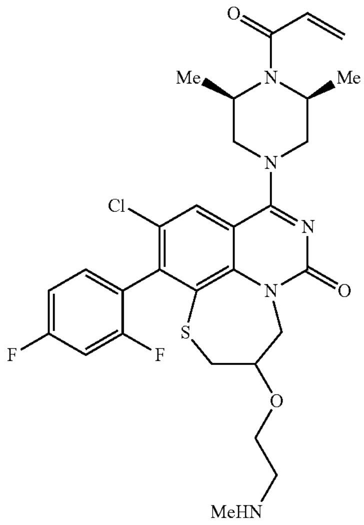

-continued
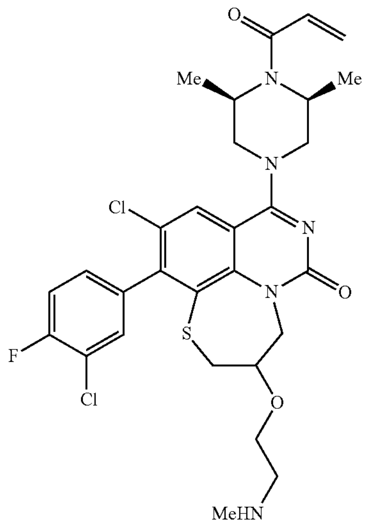
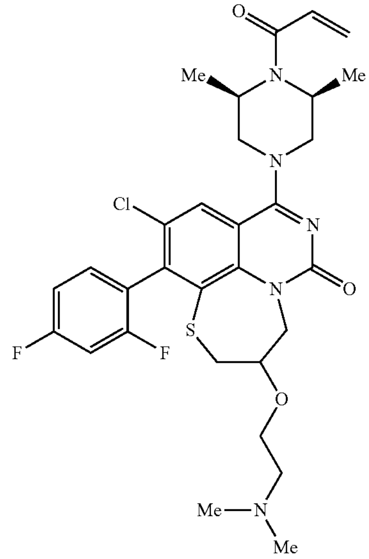
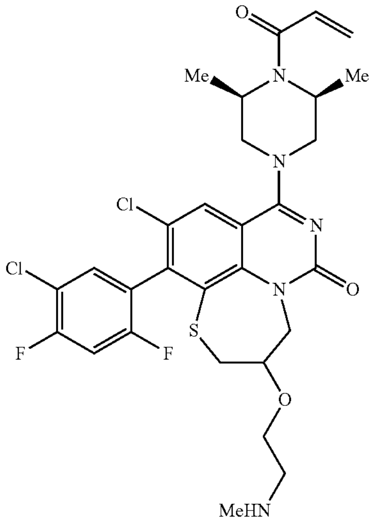
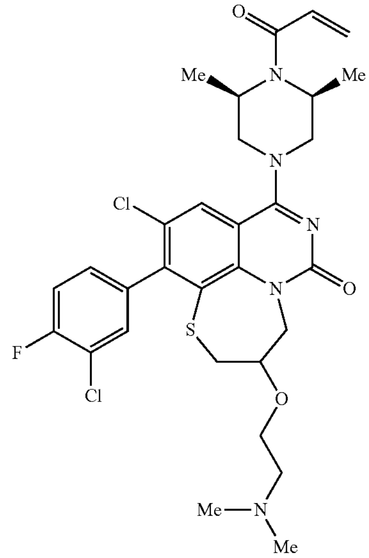
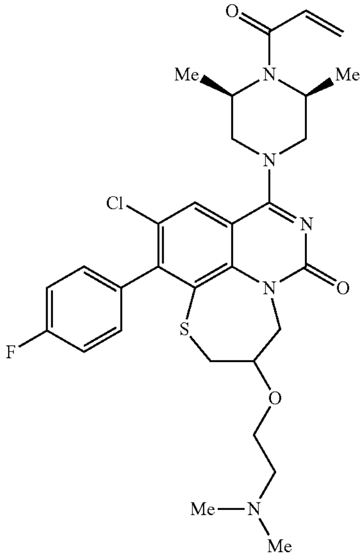
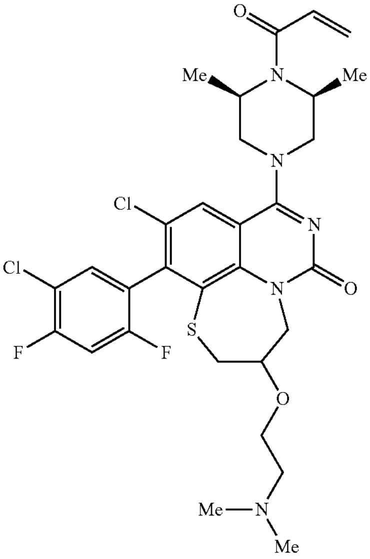
-continued -continued
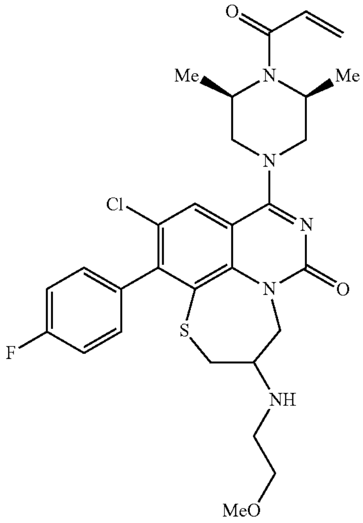
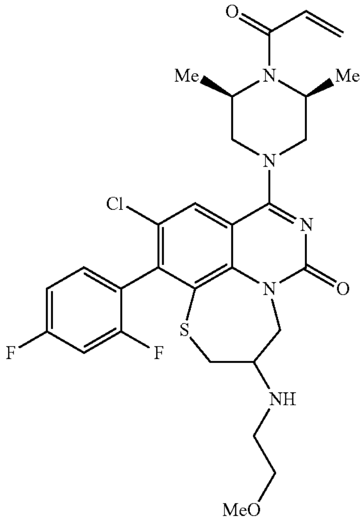
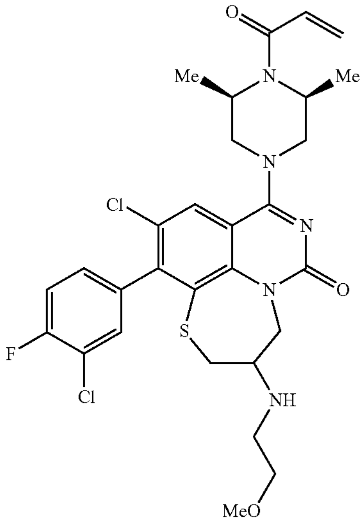
-continued
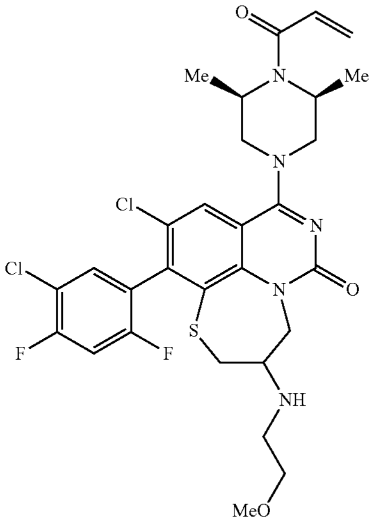
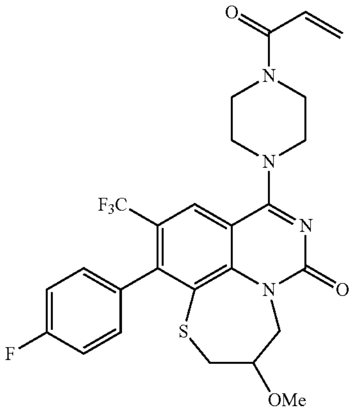
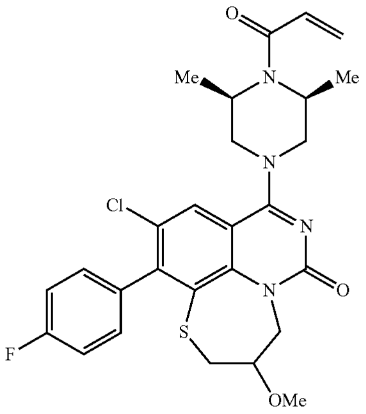

-continued
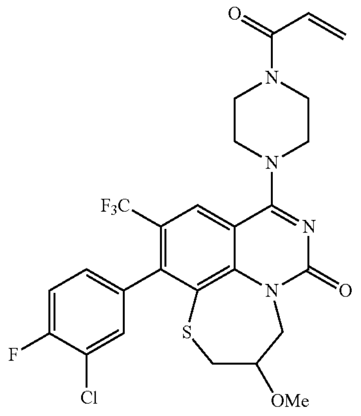
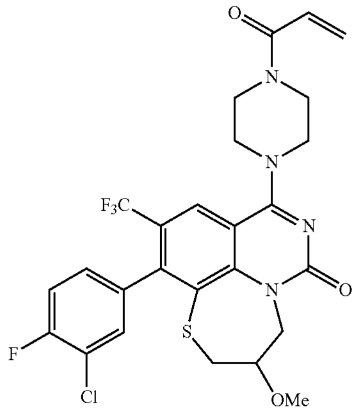
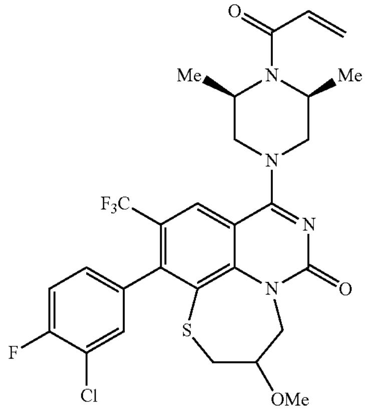
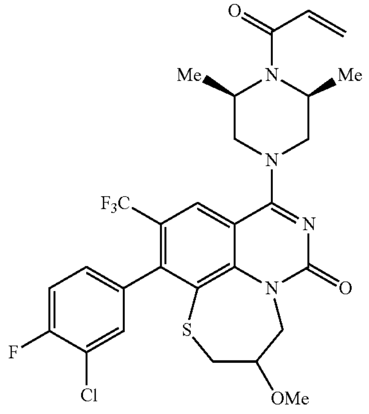
-continued
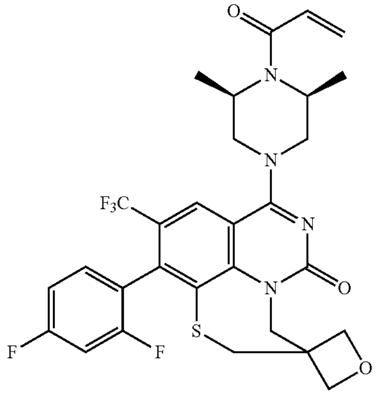
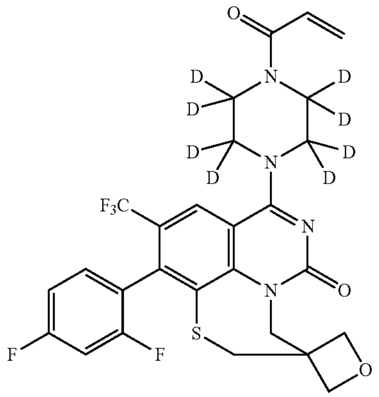
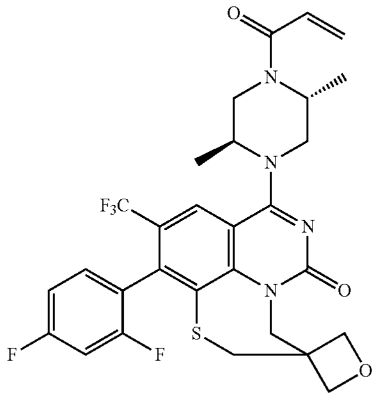
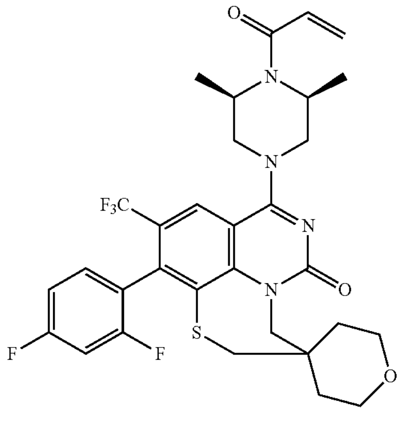

-continued
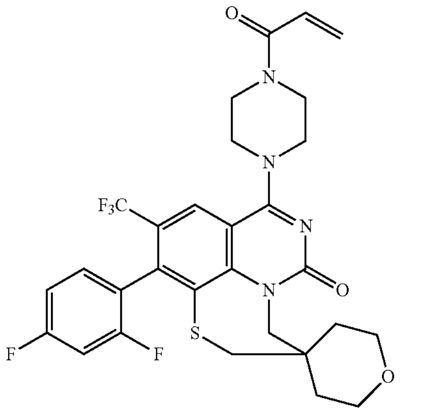
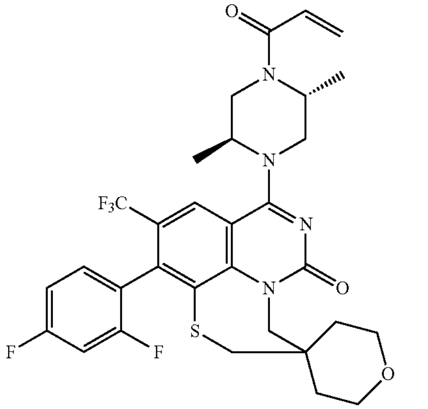
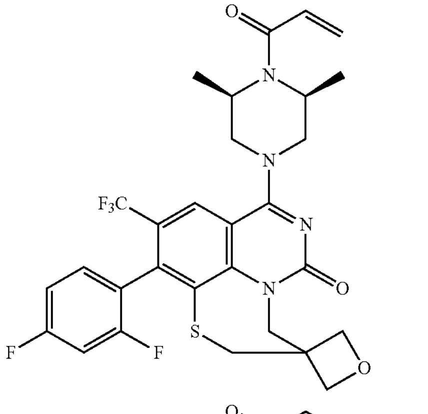
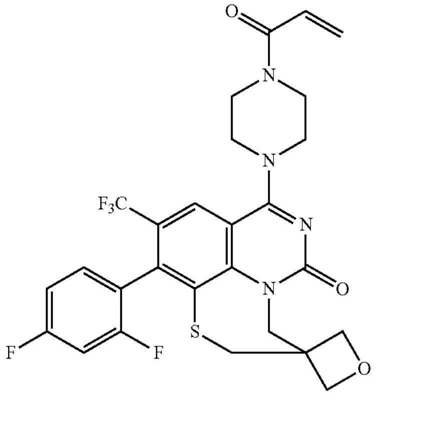
-continued
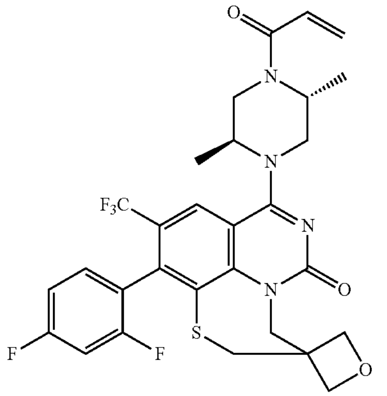
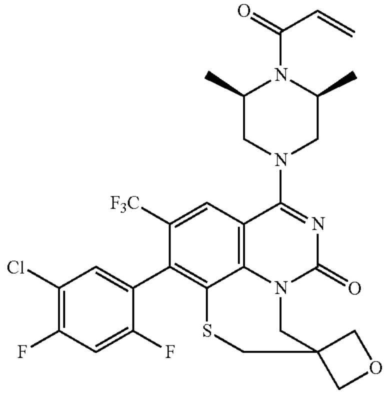
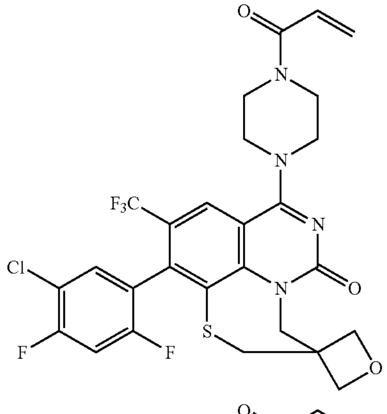
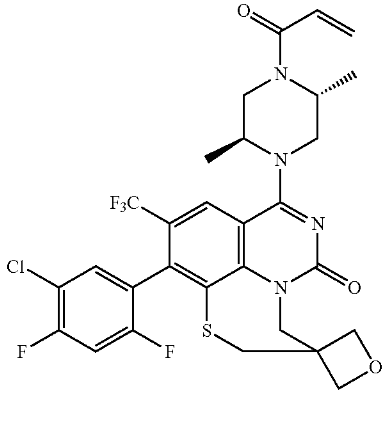

-continued
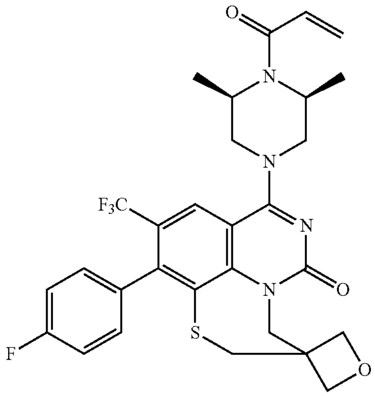
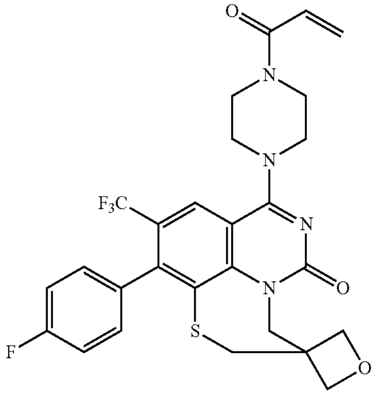
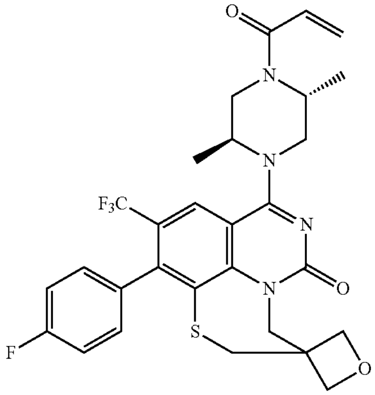
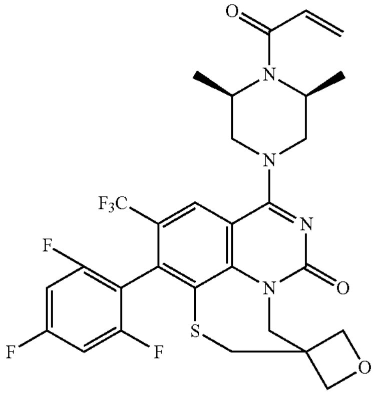
-continued
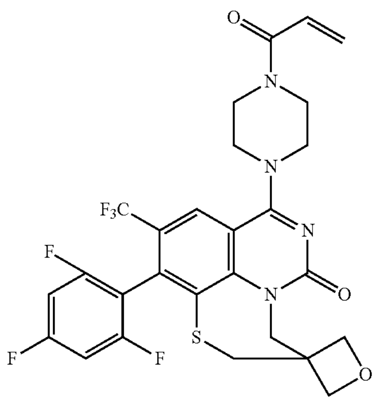
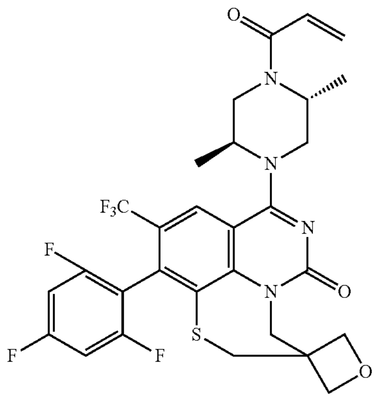
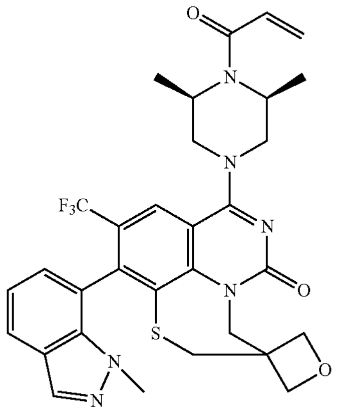
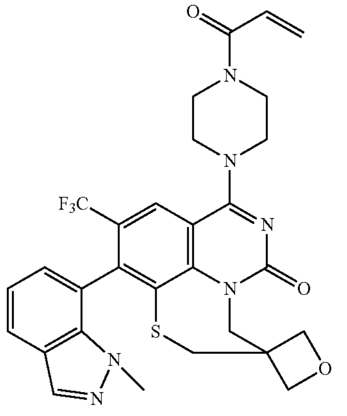

-continued
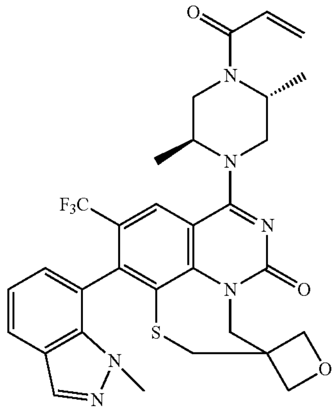
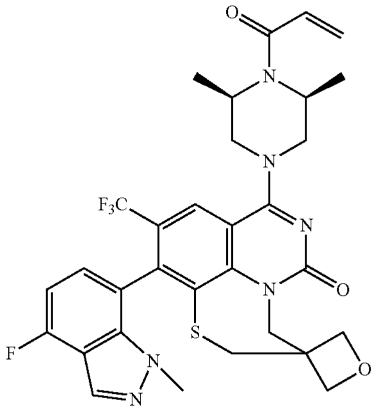
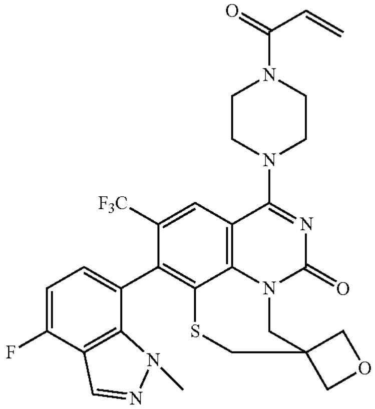
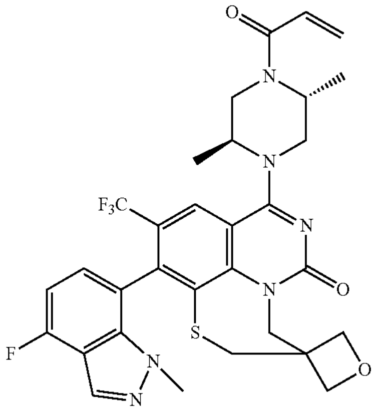
-continued
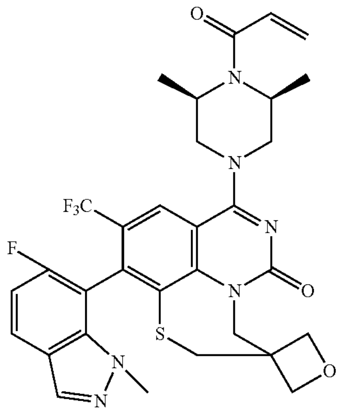
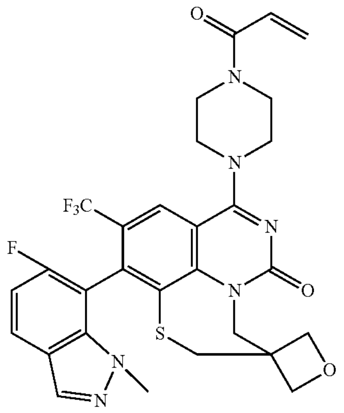
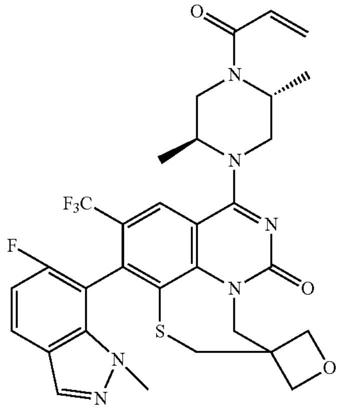
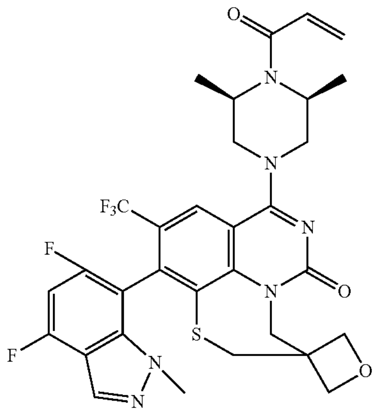

-continued
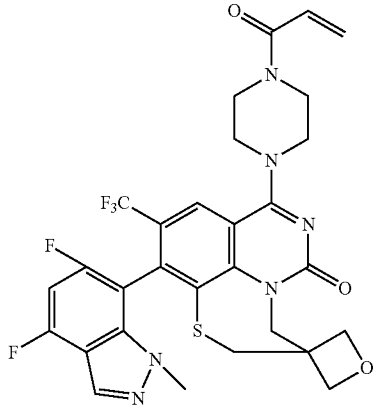
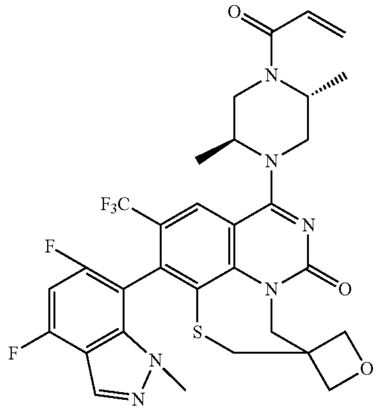
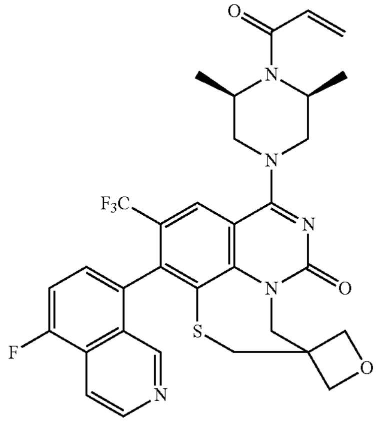
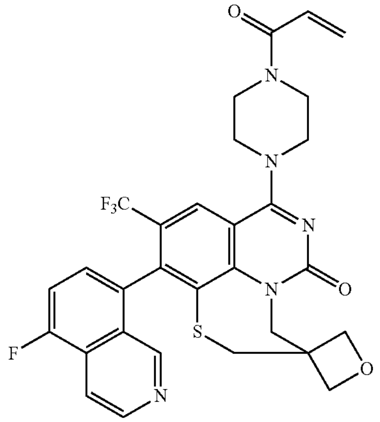
-continued
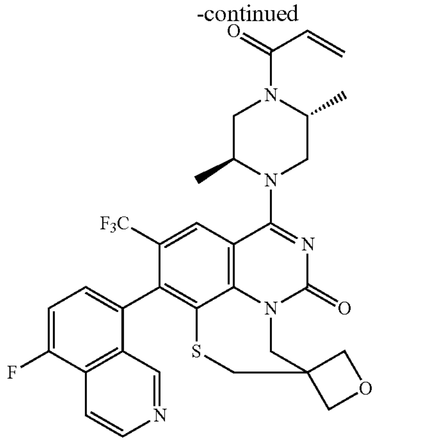
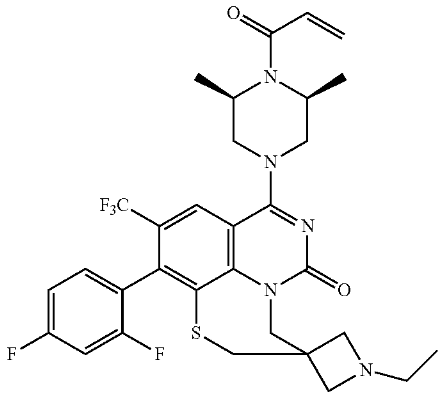
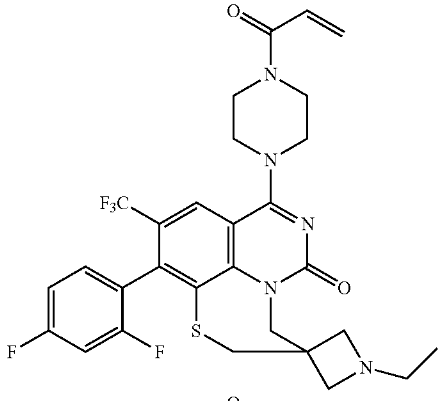
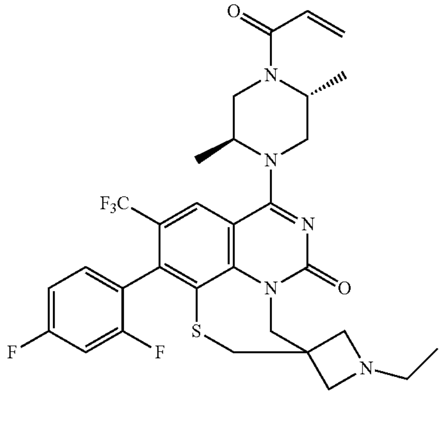

-continued
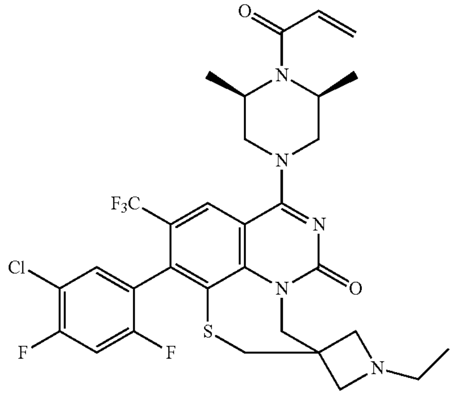
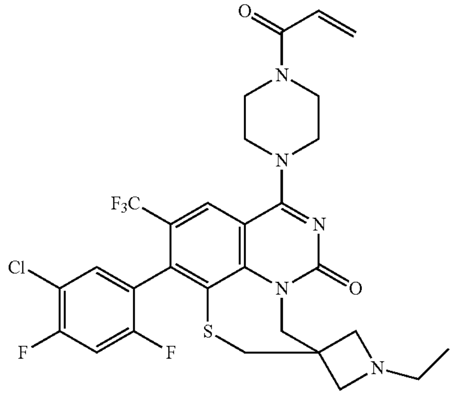
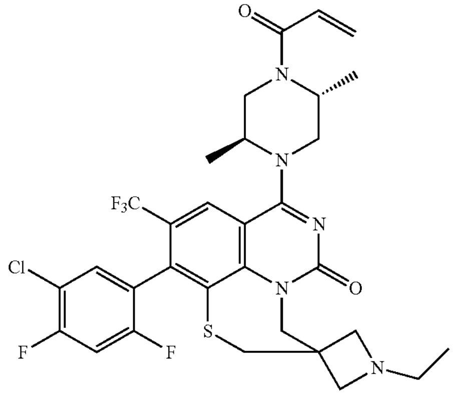
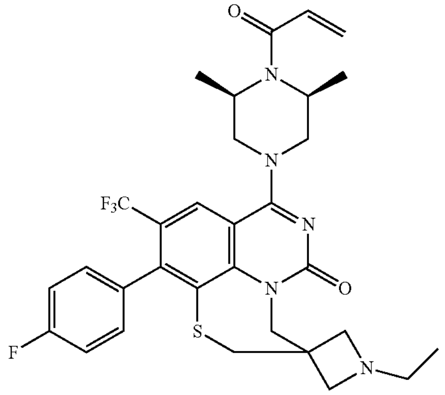
-continued
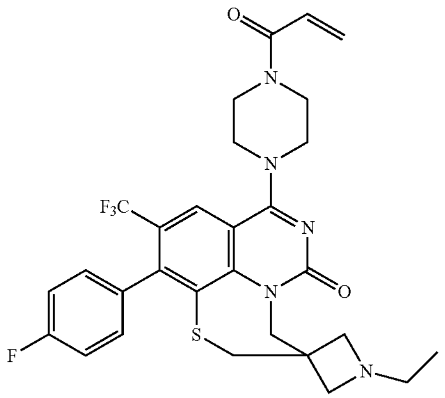
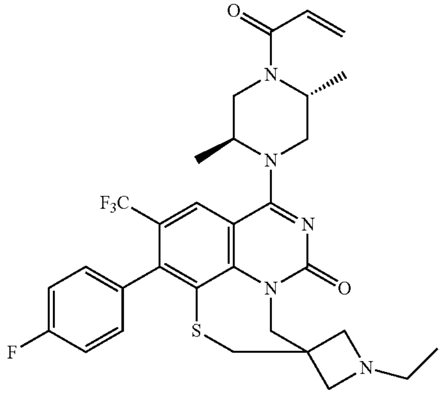
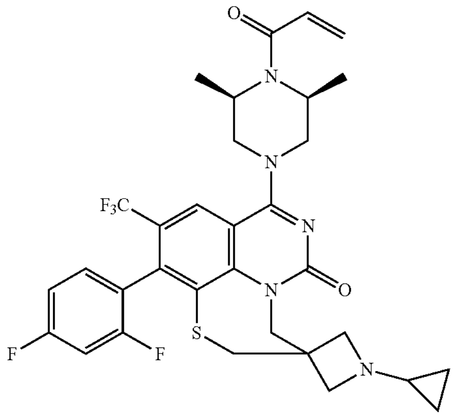
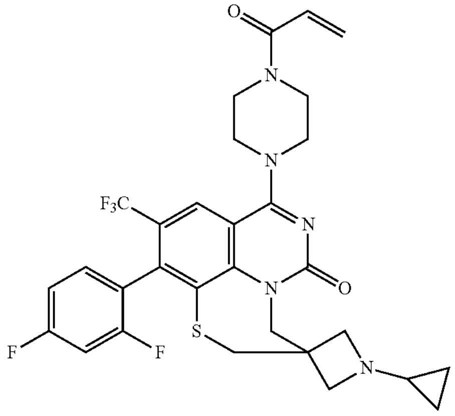

-continued
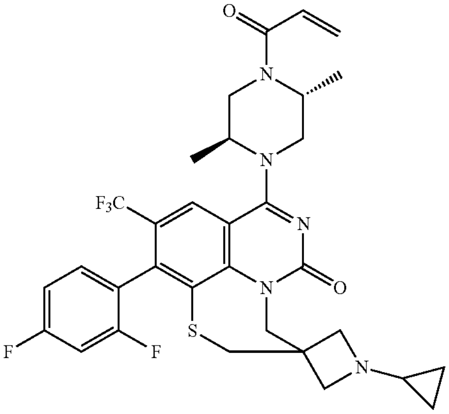
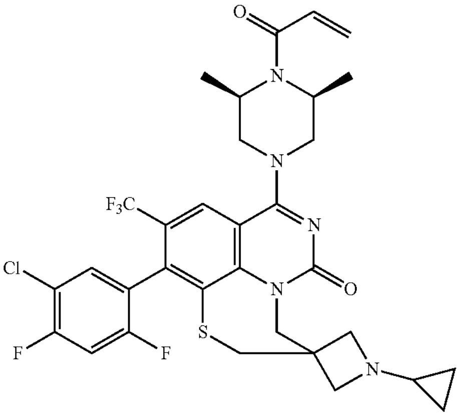
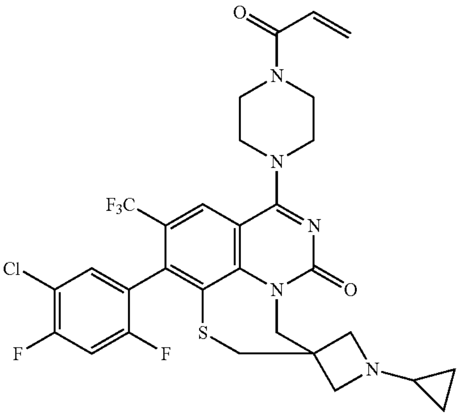
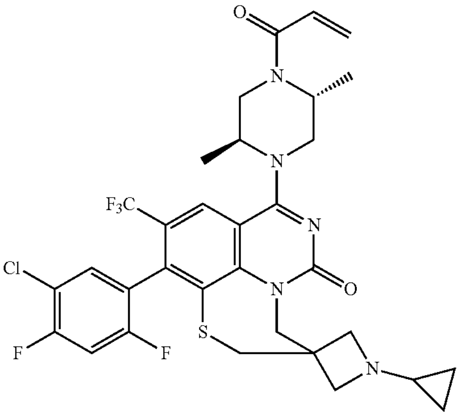
-continued
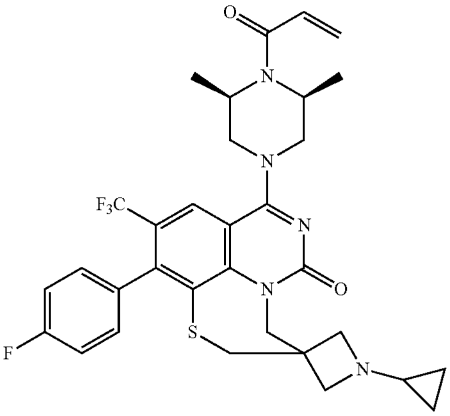
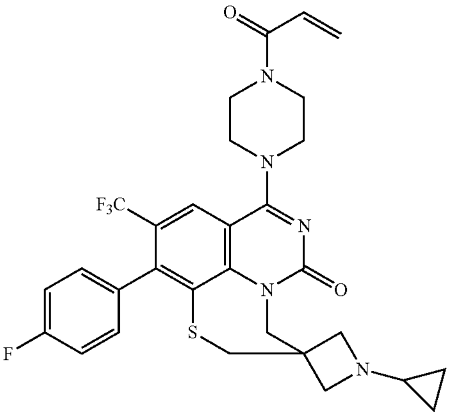
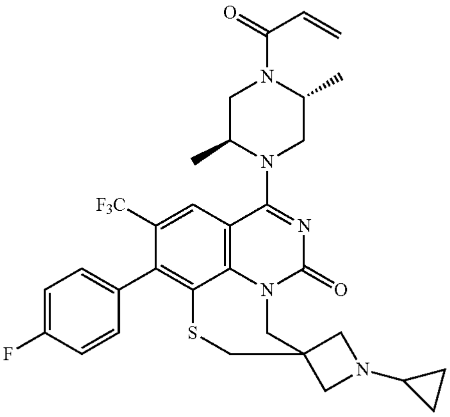
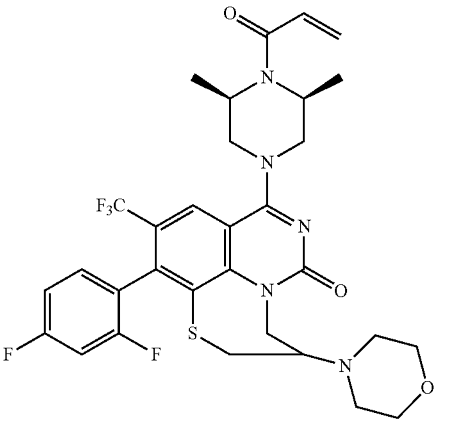

-continued
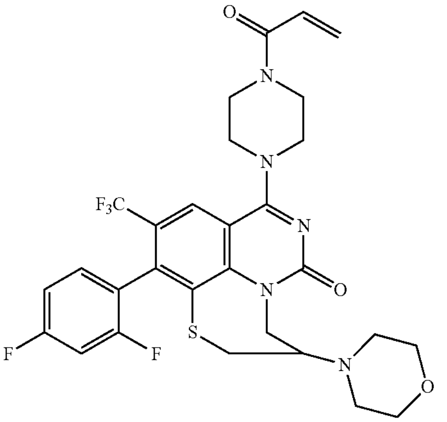
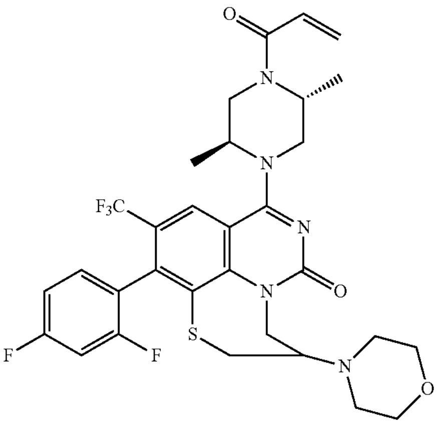
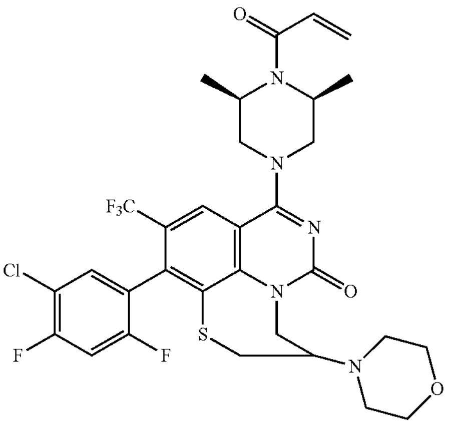
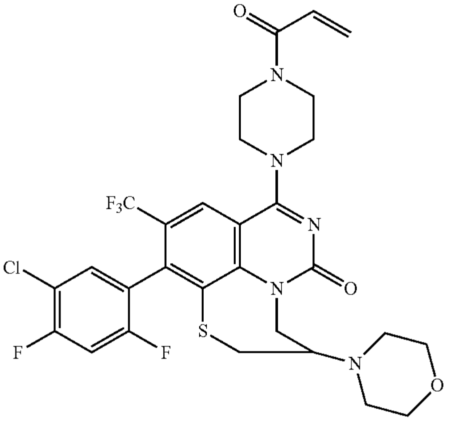
-continued
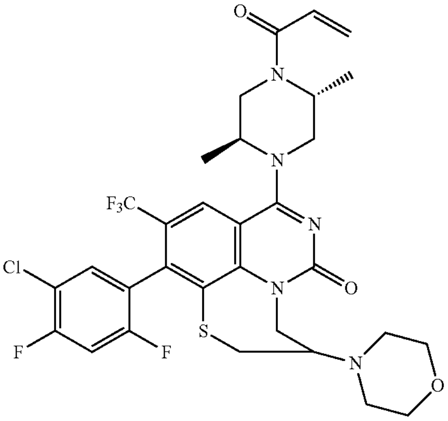
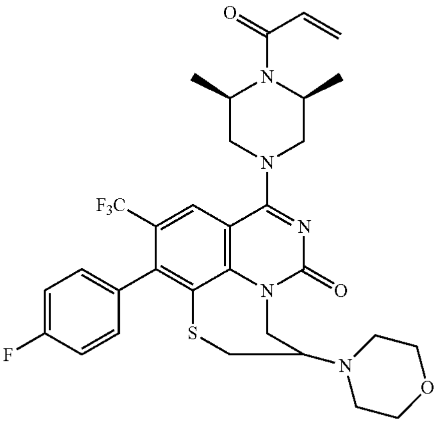
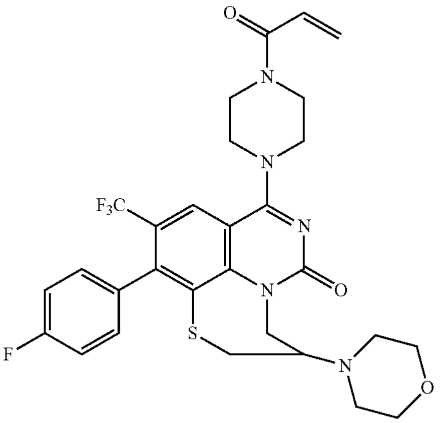
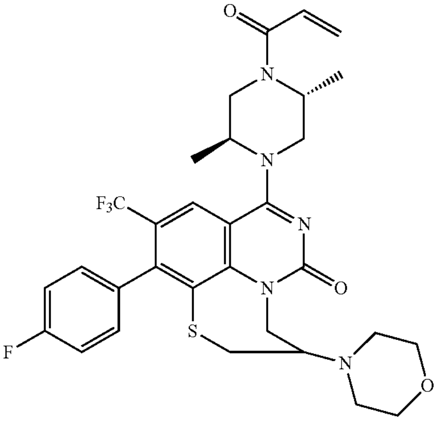

-continued
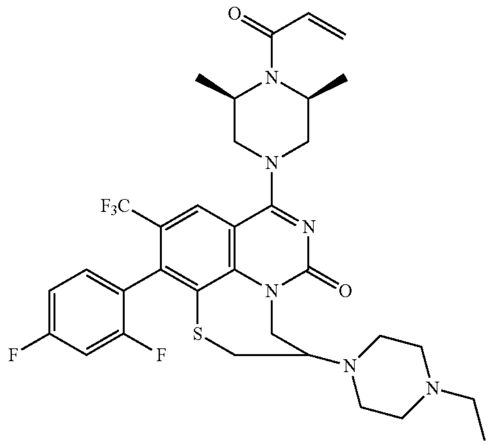
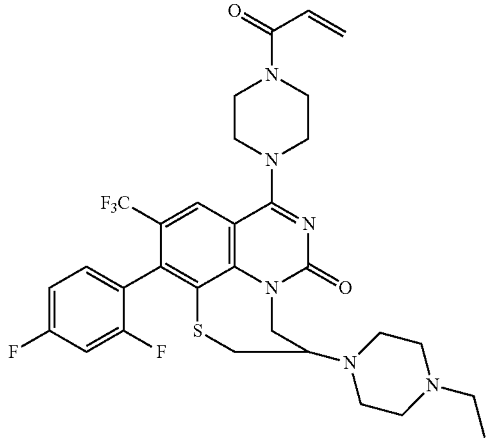
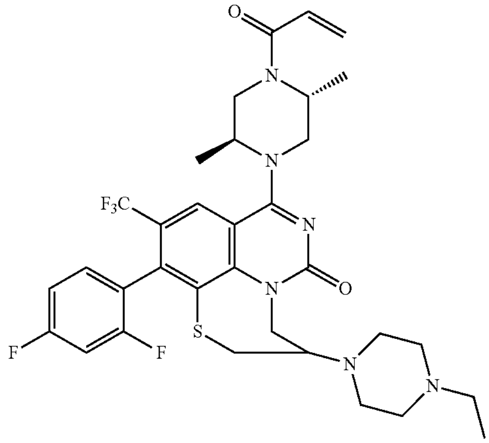
-continued
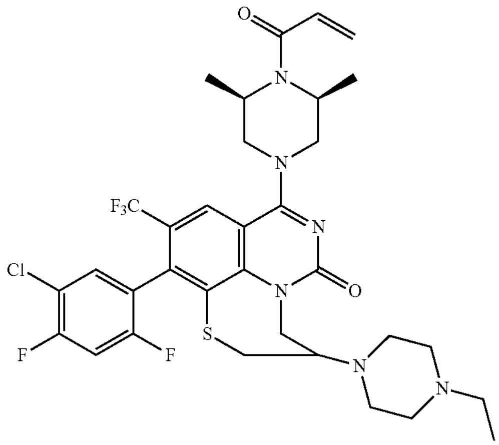
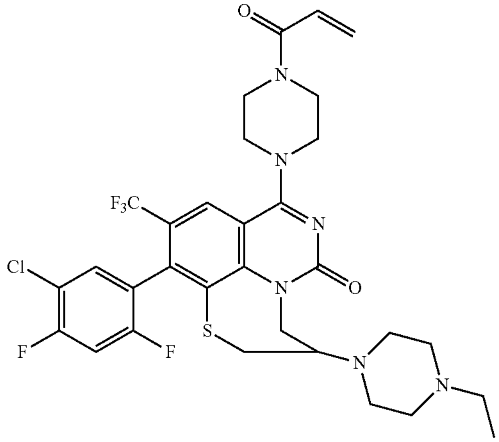
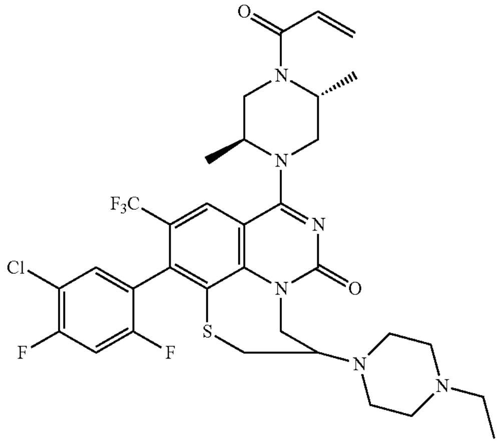

-continued
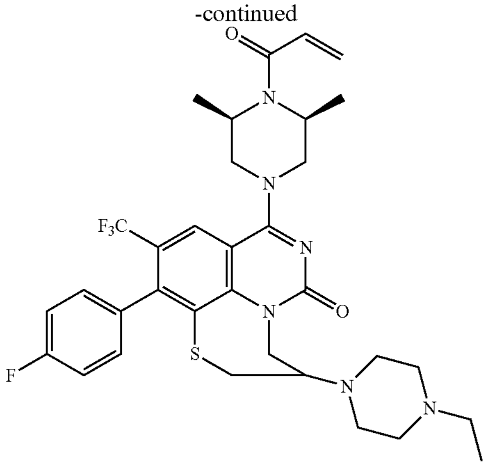
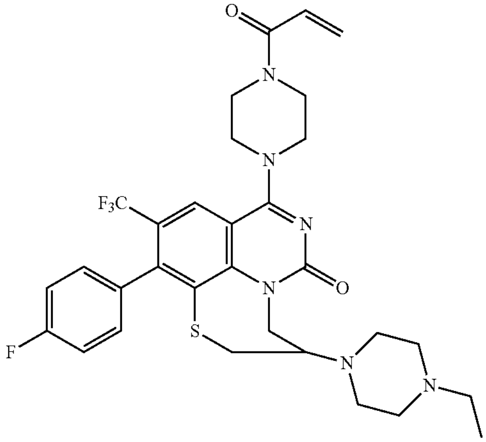
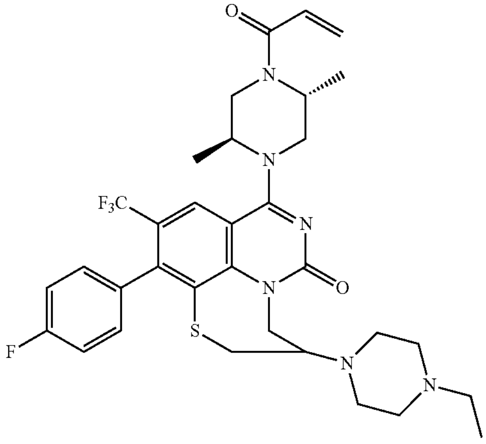
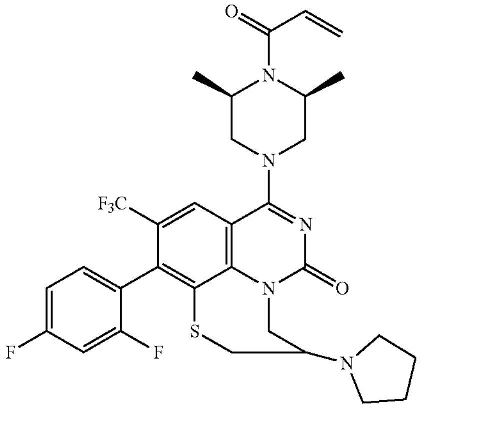
-continued
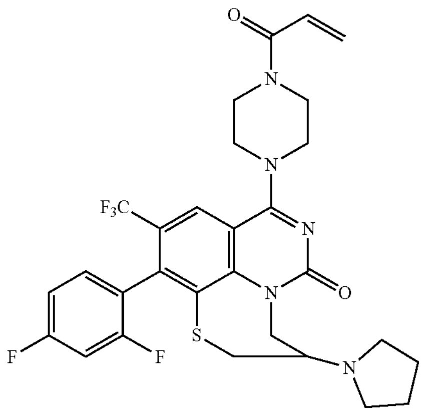
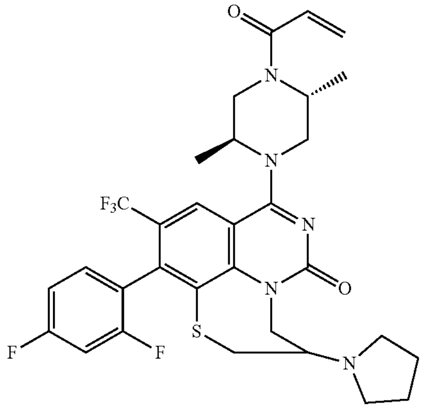
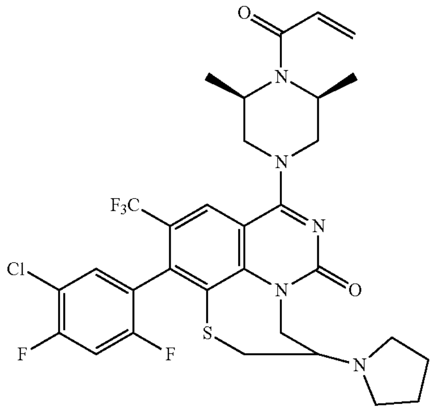
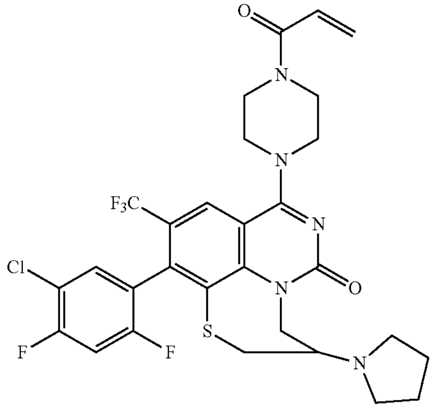

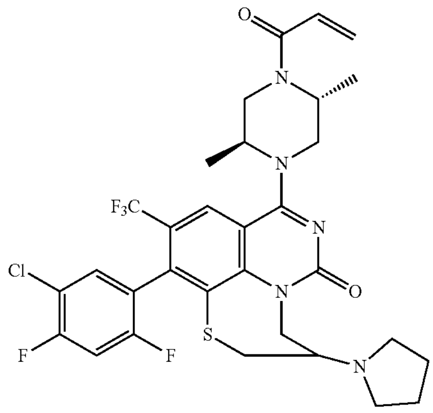
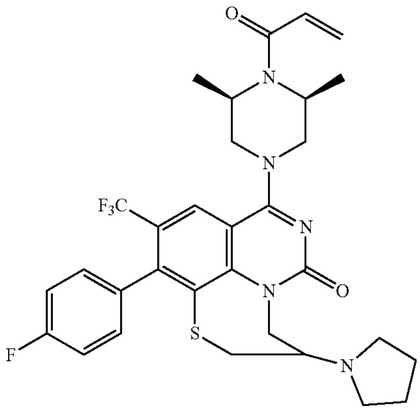
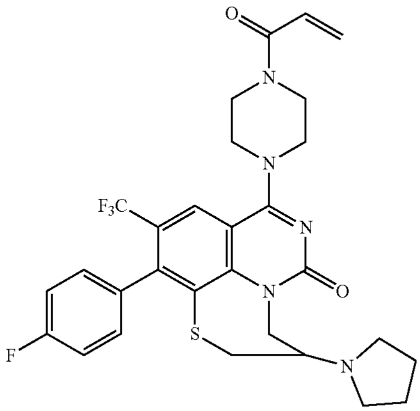
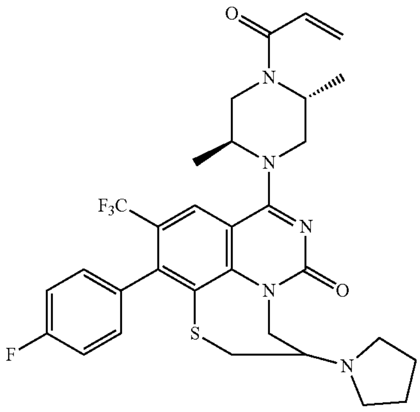
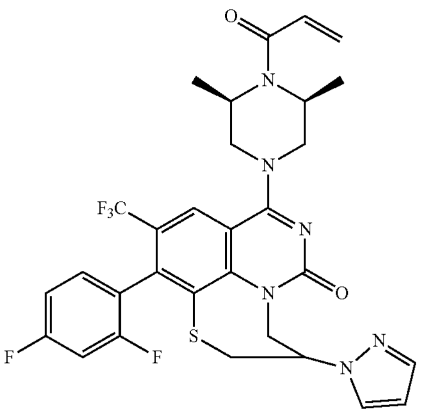
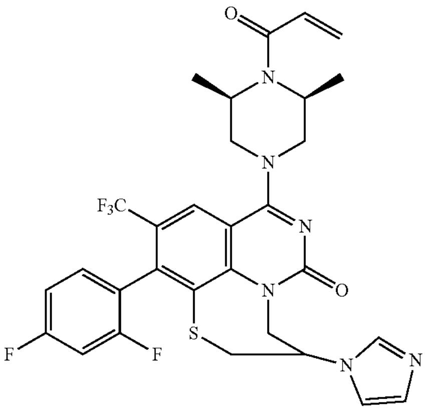
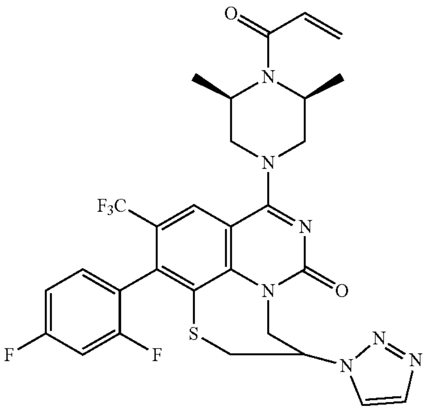
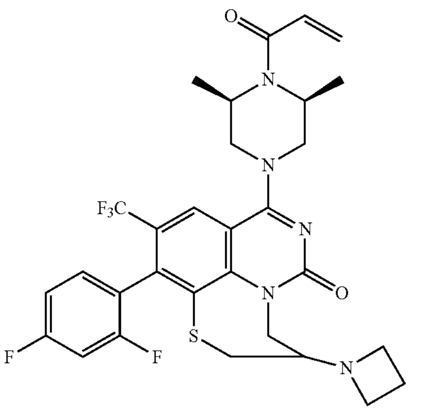

-continued
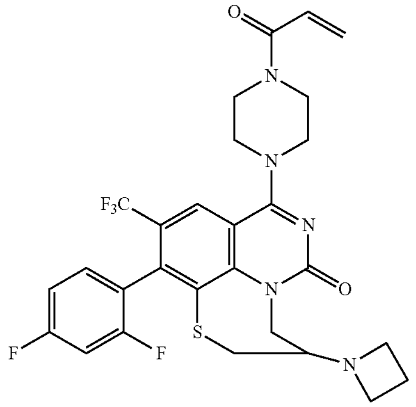
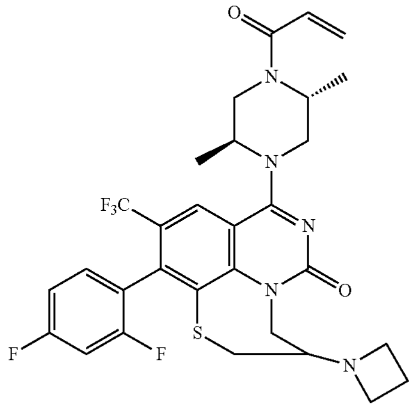
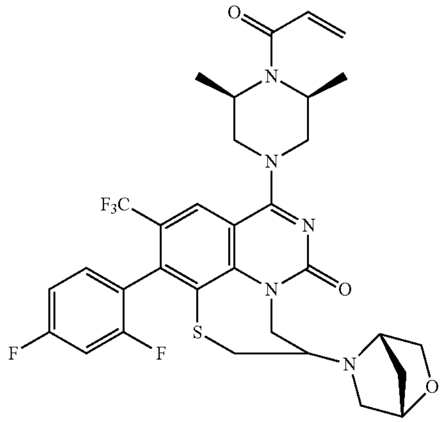
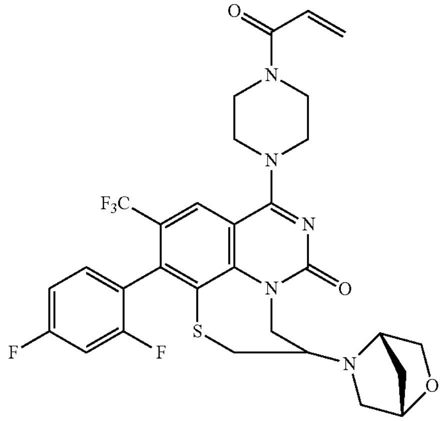
-continued
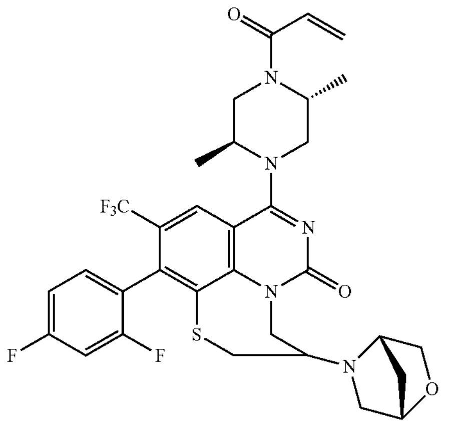
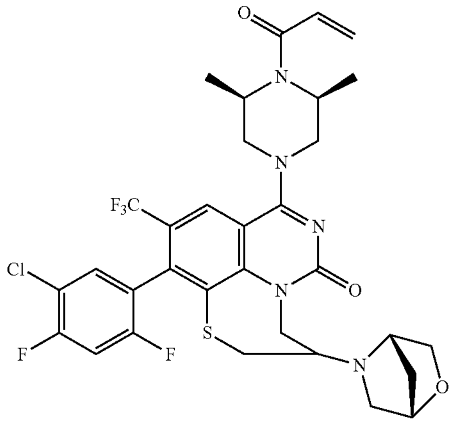
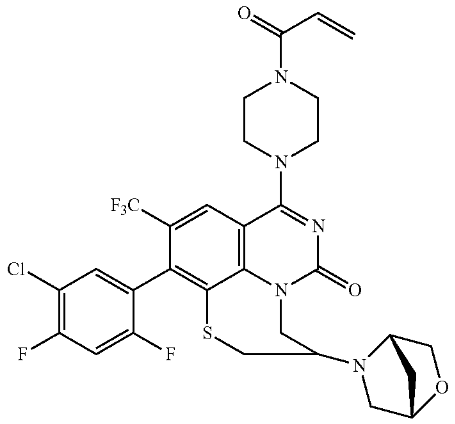
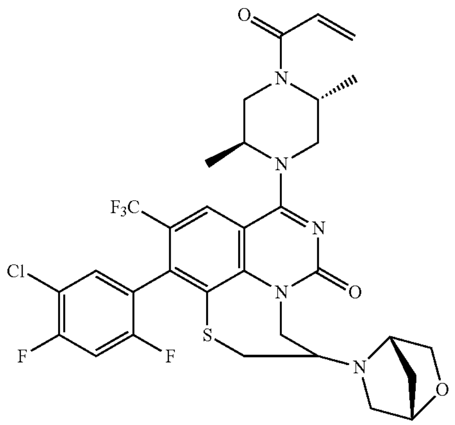

-continued
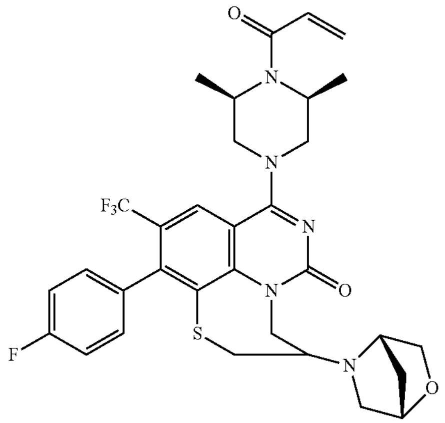
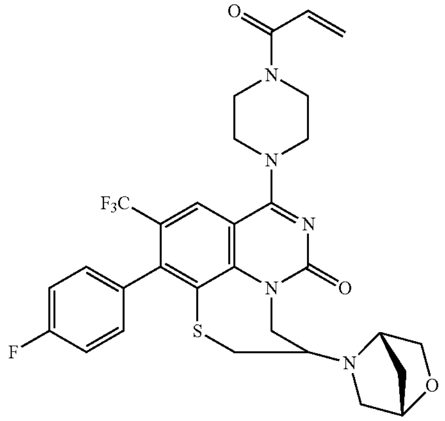
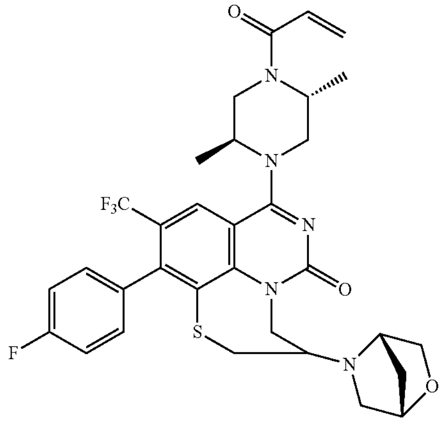
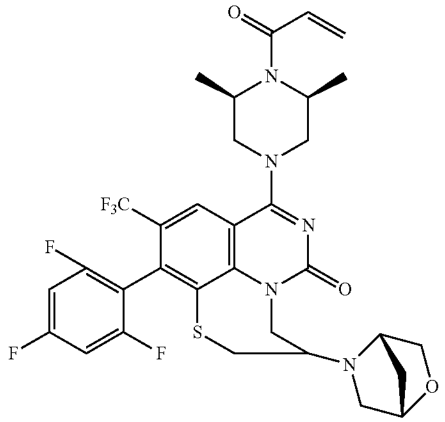
-continued
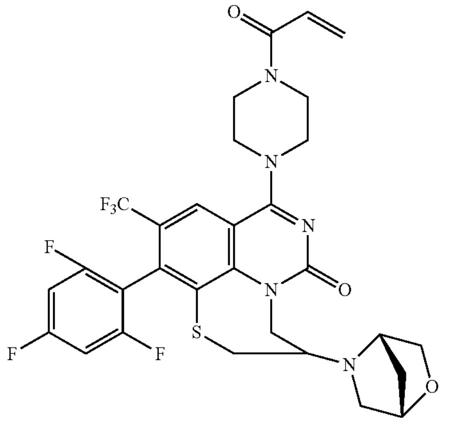
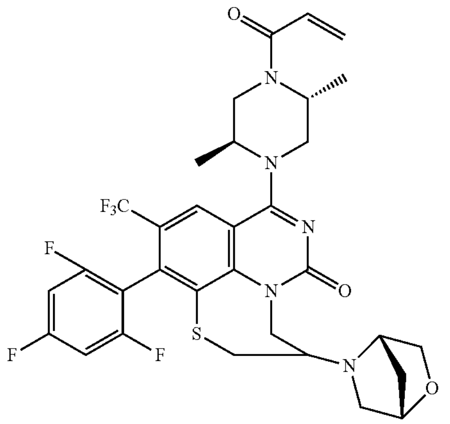
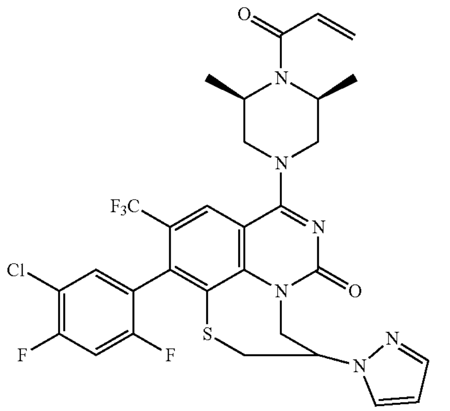
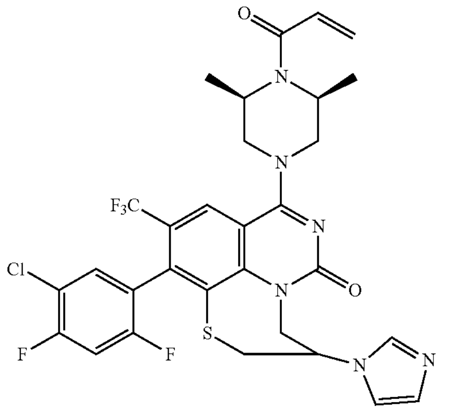

-continued

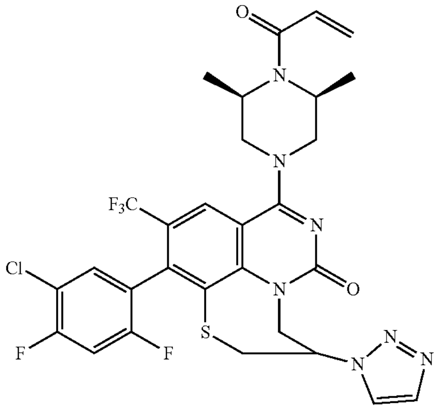

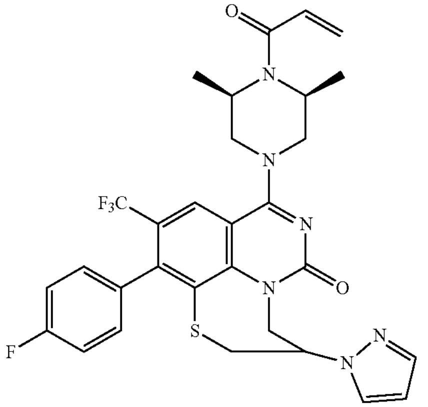

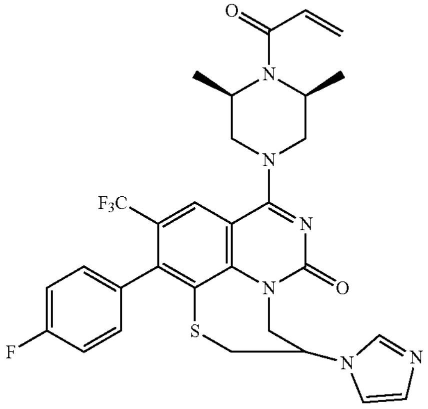

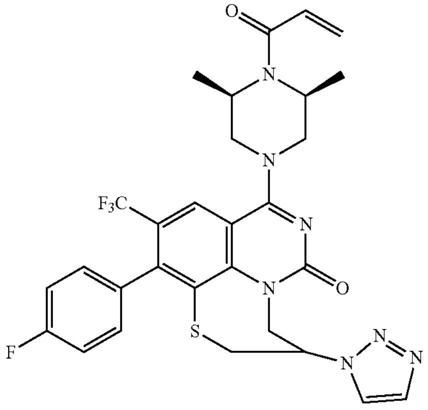

-continued

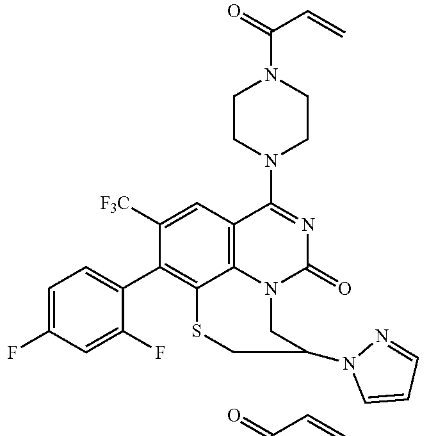

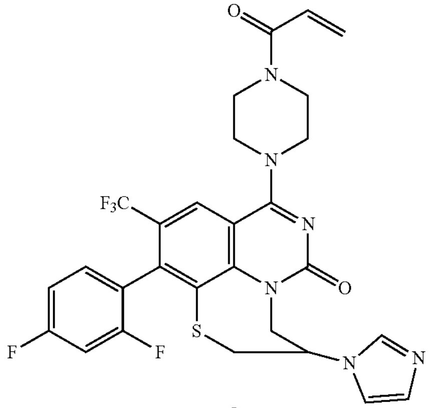

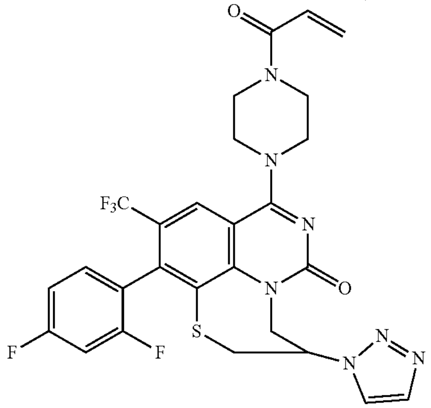

378. A pharmaceutical composition comprising a compound of embodiments 353 to 377.

379. A method of treating a subject with a cancer comprising a K-Ras G12C mutation comprising administering to the subject a compound of any one of embodiments 353 to 377 or pharmaceutical composition thereof 380. Use of a compound of any one of embodiments 353 to 377 in the manufacture of a medicament for the treatment of a cancer comprising a K-Ras G12C mutation.

381. A pharmaceutically acceptable salt of any one of the compounds of embodiments 1 to 377.

IX. Examples

The following Examples are provided to illustrate exemplary embodiments of the compounds disclosed herein and their preparation.

Various starting materials and other reagents were purchased from commercial suppliers, such as Aldrich Chemical Company, and used without further purification, unless indicated otherwise. Compounds are prepared according to the exemplary procedures provided herein and modifications thereof known to those of skill in the art. The following abbreviations are used throughout the Examples: "Ac" means acetyl, "AcO" or "OAc" means acetoxy, "ACN" means acetonitrile, "aq" means aqueous, "atm" means atmosphere(s), "BOC", "Boc" or "boc" means N-tert-butoxycarbonyl, "Bn" means benzyl, "Bu" means butyl, "nBu" means normal-butyl, "tBu" means tert-butyl, "Cbz" means benzyloxycarbonyl, "DBU" means 1,8-diazabicyclo[5.4.0]undec-7-ene, "DCM" ($CH_2Cl_2$) means methylene chloride/dichloromethane, "de" means diastereomeric excess, "DEA" means diethylamine, "DIPEA" means diisopropylethyl amine, "DMA" means N,N-dimethylacetamide, "DMAP" means 4-dimethylaminopyridine, "DMF" means N,N-dimethyl formamide, "DMSO" means dimethylsulfoxide, "DPPP" means 1,3-bis(diphenylphosphino)propane, "ee" means enantiomeric excess, "Et" means ethyl, "EtOAc" means ethyl acetate, "EtOH" means ethanol, "HATU" means 1-[bis(dimethylamino)methylene]-1H-1,2,3-triazolo [4,5-b]pyridinium 3-oxid hexafluorophosphate, "HOAc" or "AcOH" means acetic acid, "i-Pr" means isopropyl, "IPA" means isopropyl alcohol, "LDA" means lithium diisopropylamide, "LiHMDS" or "LHMDS" means lithium hexamethyldisilazide, "Me" means methyl, "MeOH" means methanol, "$MgSO_4$" means magnesium sulphate, "MS" means mass spectrometry, "MTBE" means methyl tert-butyl ether, $Na_2SO_4$" means sodium sulphate, "NMP" means 1-methyl 2-pyrrolidinone, "Ph" means phenyl, "sat." means saturated, "SFC" means supercritical fluid chromatography, "TBME" or "MTBE" means tert-butyl methyl ether, "TEA" means triethyl amine, "TFA" means trifluoroacetic acid, "THF" means tetrahydrofuran, "TLC" means thin layer chromatography, "RP" means retention fraction, "about" means approximately, "rt" means retention time, "RT" means room temperature, "h" means hours, "min" means minutes, "N" means Normal, "M" means molar, "mL" means milliliter, "mmol" means millimoles, "μmol" means micromoles, "eq." means equivalent, "° C." means degrees Celsius, and "Pa" means pascals. $^1$H-NMR spectra are reported in ppm, and were obtained as $CDCl_3$ solutions (7.25 ppm), DMSO-$D_6$ solutions (2.50 ppm), or $CD_3OD$ solutions (3.4 ppm and 4.8 ppm), any may have used internal tetramethylsilane (0.00 ppm) as an internal standard when appropriate. Other NMR solvents were used as needed. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Example Pyrimidone-Thiomorpholines-A

1. General Information

Synthetic Scheme 1

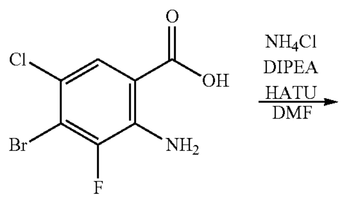

1

-continued

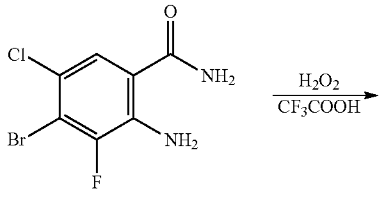

2

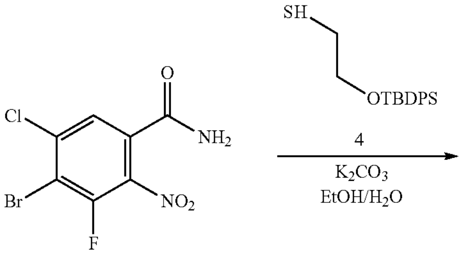

3

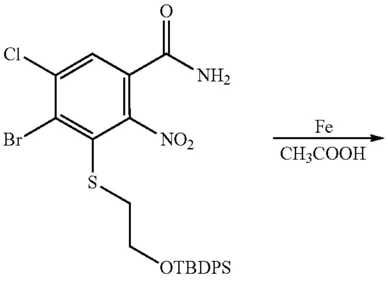

5

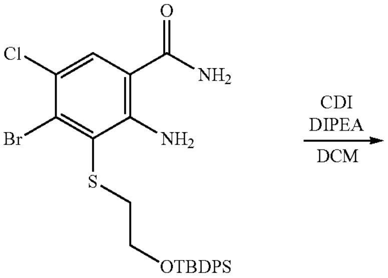

6

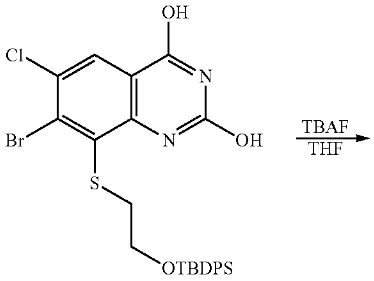

7

-continued

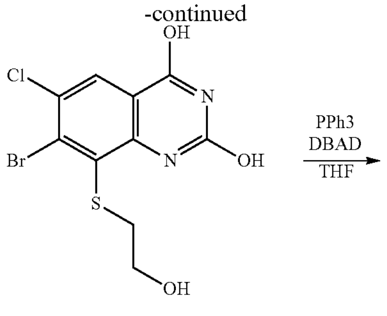

8

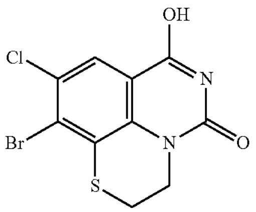

9

2. Preparation of Compound 2

To a solution of 2-amino-4-bromo-5-chloro-3-fluorobenzoic acid (2.68 g, 10 mmol, 1.0 eq.) in DMF (27 mL) was added DIPEA (6.45 g, 50 mmol, 10 eq.), $NH_4Cl$ (3.20 g, 60 mmol, 6 eq.) and HATU (7.6 g, 20 mmol, 2 eq.) under $N_2$ atmosphere at RT. Then the reaction mixture was stirred for 2 hours, diluted with MTBE (100 mL), washed with 0.5N HCl aq. (50 mL), brine (50 mL) and dried over $Na_2SO_4$. The organic layer was concentrated in vacuo. The residue obtained was purified by a chromatography (0-50% EtOAc/petroleum ether) to provide the product 2 as a yellow solid (2.3 g, yield: 86%). LC-MS: $[M+H]^+$=267

3. Preparation of Compound 3

To a solution of 2-amino-4-bromo-5-chloro-3-fluorobenzamide (2.67 g, 10 mmol, 1.0 eq.) in $CF_3COOH$ (27 mL) was added hydrogen peroxide (5.7 g, 50 mmol, 5 eq.). The reaction was stirred at 50° C. for 0.5 hour. Then diluted with MTBE (150 mL), washed with water (100 mL), brine (100 mL), and then dried over $Na_2SO_4$. The organic layer was concentrated in vacuo, the residue obtained was purified by a chromatography (0-100% EtOAc/petroleum ether) to provide the product 3 as a yellow solid (1.8 g, yield: 60%). LC-MS: $[M+H]^+$=297

4. Preparation of Compound 5

To a solution of 4-bromo-5-chloro-3-fluoro-2-nitrobenzamide (3.0 g, 10 mmol, 1.0 eq) in EtOH (30 ml) and water (6 mL) was added 2-((tert-butyldiphenylsilyl)oxy)ethane-1-thiol (3.2 g, 10 mmol, 1.0 eq), potassium carbonate (4.2 g, 30 mmol, 3.0 eq). Then the reaction mixture was stirred at 50° C. for 2 hours. The solvent was removed to afford 6.5 g of the crude product which was used in the subsequent step without further purification. LC-MS: $[M+H]^+$=593

5. Preparation of Compound 6

To a solution of compound 5 (6.5 g crude, 10 mmol, 1.0 eq.) in $CH_3COOH$ (120 mL) was added Iron powder (2.8 g, 50 mmol, Seq.). The reaction mixture was stirred at 50° C. for 2 h. After filtration, the collected solid was washed with EtOAc (500 mL). The organic phase was washed with water 300 mL, brine 300 mL and concentrated in vacuo. The residue obtained was purified by a chromatography (0-100% EtOAc/petroleum ether) to provide the product 6 as a yellow solid (2.8 g, yield: 50%). LC-MS: $[M+H]^+$=563

6. Preparation of Compound 7

To a solution of compound 6 (5.6 g, 10 mmol, 1.0 eq.) in DCM (110 mL) was added DIPEA (2.6 g, 20 mmol, 2 eq.), CDI (4.9 g, 30 mmol, 3.0 eq.) at rt. The reaction mixture was stirred for 16 hours. After filtration, the filter cake was washed with petroleum ether (50 mL) and dried to afford the product 7 as an off-white solid (4.7 g, yield: 80%). LC-MS: $[M+H]^+$=589

7. Preparation of Compound 8

To a solution of compound 7 (5.9 g, 10 mmol, 1.0 eq.) in THF (60 mL) was added tetrabutylammonium fluoride (10 mL, 10 mmol, 1.0 eq.). The reaction mixture was stirred for 3 hours. After diluted with EtOAc (150 mL), washed with $H_2O$ (50 mL) and brine (50 mL). The organic layer was dried over $Na_2SO_4$ and concentrated in vacuo to give the crude product 8 as an off-white solid (3.16 g, yield: 90%).

8. Preparation of Compound 9

To a solution of 7-bromo-6-chloro-8-((2-hydroxyethyl)thio)quinazoline-2,4-diol (3.5 g, 10 mmol, 1.0 eq.) in THF (100 mL) was added $PP_3$ (4.5 g, 17 mmol, 1.7 eq.), then DEAD (3.0 g, 17 mmol, 1.7 eq.) at −10~0° C. The reaction mixture was stirred for 1 hour. After diluted with EtOAc (100 mL), washed with water (100 mL), brine (100 mL). The organic layer was dried over $Na_2SO_4$ and concentrated in vacuo. The residue obtained was diluted with DCM (100 mL) and stirred for 2 hours. After filtration, the filter cake was washed with DCM (50 mL) and dried to give the product 9 as an off-white solid (1.5 g, yield: 45%). LC-MS: [M+H]+=333

Synthetic Scheme 2

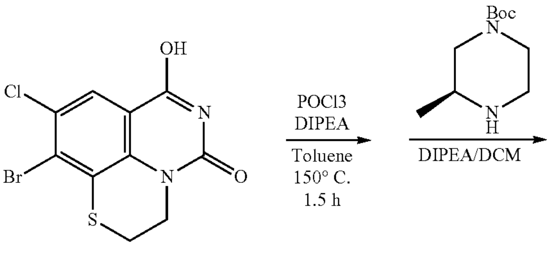

1

-continued

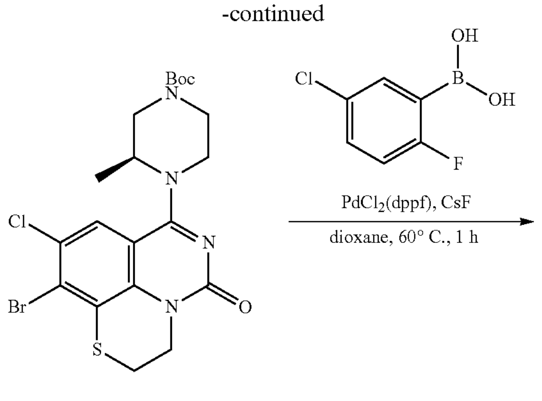

2

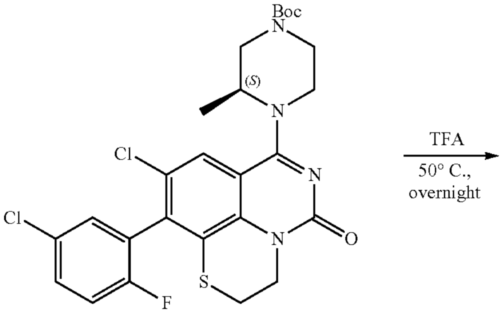

3

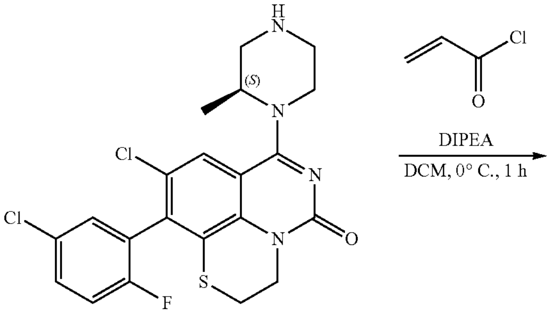

4

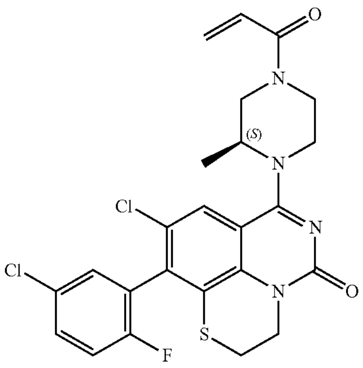

5

9. Preparation of Compound 2

To a solution of Compound 1 (1.2 mmol, 400 mg) was in toluene was added $POCl_3$ (3 mL), DIPEA (2.4 mmol, 309 mg) subsequently. The mixture was stirred at 120° C. for 1.5 hrs. The solvent was removed in vacuo. The crude product was used the next step without further purification.

To the solution of above crude product in DCM (10 mL) was added DIPEA (2.4 mmol, 309 mg), followed by addition of tert-butyl (S)-3-methylpiperazine-1-carboxylate (1.2 mmol, 187 mg). Then the reaction solution was stirred at rt for 1 hr. The mixture was diluted with DCM and washed with water. The organic phase was dried over $Na_2SO_4$. After filtration, the solvent was removed in vacuo. The residue was purified by a chromatography with (30-50% EtOAc/petroleum ether) to provide compound 2 as a yellow solid (400 mg, 65%). LC-MS: $[M+H]^+$=515.0/517.0, RT=1.735 min. $^1H$ NMR (400 MHz, $CDCl_3$) δ 7.44 (s, 1H), 4.64 (s, 1H), 4.40 (s, 2H), 4.07 (s, 1H), 3.89 (s, 1H), 3.52 (s, 1H), 3.26-3.19 (m, 3H), 3.11 (s, 2H), 1.49 (s, 9H), 1.40 (d, J=6.7 Hz, 3H).

10. Preparation of Compound 3

To a solution of Compound 2 (0.28 mmol, 150 mg) in dioxane (5 mL) was added (5-chloro-2-fluorophenyl)boronic acid (0.37 mmol, 63 mg), $Pd(dppf)Cl_2$ (0.056 mmol, 41 mg), and CsF (0.56 mmol, 85 mg) in $N_2$ atmosphere successively. After the reaction was finished, the mixture was filtered, diluted with EtOAc and washed with water. The organic phase was dried over $Na_2SO_4$ and concentrated in vacuo. The residue was purified by a chromatography with (30-50% EtOAc/petroleum ether) to afford compound 3 as light-yellow solid (110 mg, 67%). LC-MS: $[M+H]^+$=NO Signal, RT=1.836 min.

11. Preparation of Compound 5

Compound 3 (0.19 mmol, 110 mg) was dissolved in TFA (2 mL), and the mixture was stirred at rt overnight. After the reaction was finished, the mixture was washed with saturated aqueous sodium carbonate, diluted with brine and extracted with DCM. The organic phase was dried over $Na_2SO_4$. The solvent was removed in vacuo to give the crude product which was used to the next step without further purification.

To a solution of above product was in DCM (5 mL) was added DIPEA (1.0 mmol, 127 mg), followed by acryloyl chloride (0.24 mmol, 22 mg) at 0° C. Then the mixture was stirred for 1 h. The reaction mixture was washed with saturated aqueous sodium carbonate, brine and extracted with DCM. The organic phase was dried over $Na_2SO_4$, and the solvent was removed in vacuo. The residue was purified by pre-HPLC to give compound 5 (yield: 40%). LCMS: [M+H]+=521.0, RT=1.566 min. $^1H$ NMR (401 MHz, DMSO) δ 7.64 (d, J=10.8 Hz, 2H), 7.55-7.41 (m, 2H), 6.83 (d, J=10.2 Hz, 1H), 6.30-6.06 (m, 1H), 5.74 (dd, J=10.4, 2.0 Hz, 1H), 4.65 (d, J=31.4 Hz, 1H), 4.47-4.18 (m, 2H), 4.03 (dd, J=27.6, 13.3 Hz, 3H), 3.68-3.41 (m, 2H), 3.27-3.07 (m, 2H), 3.06-2.87 (m, 1H), 1.26 (dd, J=12.9, 6.2 Hz, 3H).

The different-alkyl intermediates were synthesized using corresponding boronic acid for Suzuki reaction and acid (acid chloride or anhydride) for amid formation. The other steps were conducted using the conditions described above.

TABLE 2a

| Summary of Examples | | | | | |
|---|---|---|---|---|---|
| Ex.# | Name | Structure | $^1$H NMR | MS | % CAF 10 uM @ 60 min |
| 62a | 7-((S)-4-acryloyl-2-methylpiperazin-1-yl)-9-chloro-10-(5-cyclopropyl-2-fluorophenyl)-2,3-dihydro-5H-[1,4]thiazino[2,3,4-ij]quinazolin-5-one | 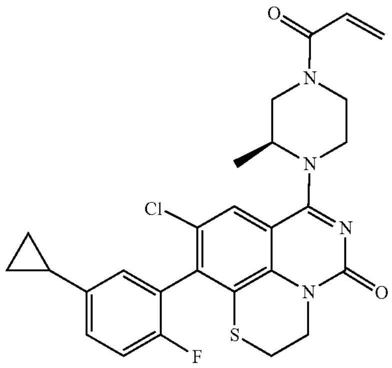 [SMILES: C=CC(=O)N1CCN(c2nc(=O)n3c4c(c(-c5cc(C6CC6)ccc5F)c(Cl)cc24)SCC3)[C@@H](C)C1] | $^1$H NMR (400 MHz, MeOH-d4) δ 7.66 (dd, J = 9.0 Hz, 1H), 7.26-7.18 (m, 1H), 7.11 (t, J = 9.1 Hz, 1H), 6.97-6.90 (m, 1H), 6.89-6.72 (m, 1H), 6.29 (dd, J = 16.8, 8.2 Hz, 1H), 5.81 (dd, J = 10.6, 1.9 Hz, 1H), 4.83-4.70 (m, 1H), 4.60-3.96 (m, 5H), 3.77-3.41 (m, 2H), 3.26-3.03 (m, 3H), 2.00-1.91 (m, 1H), 1.40 (dd, J = 21.1, 6.8 Hz, 3H), 1.03-0.95 (m, 2H), 0.72-0.64 (m, 2H): | 525.04 | 67 |
| 63 | (S,E)-9-chloro-10-(3-chloro-5-fluorophenyl)-7-(4-(4,4-difluorobut-2-enoyl)-2-methylpiperazin-1-yl)-2,3-dihydro-5H-[1,4]thiazino[2,3,4-ij]quinazolin-5-one | 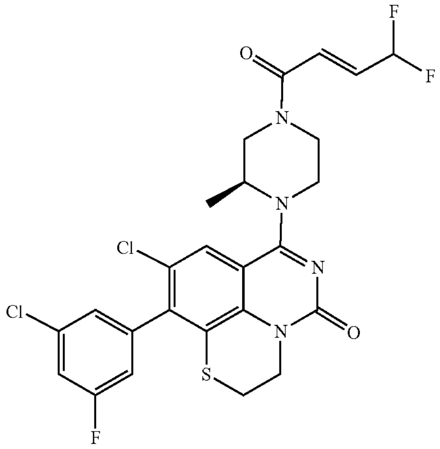 [SMILES: C[C@H]1CN(C(=O)/C=C/C(F)F)CCN1c1nc(=O)n2c3c(c(-c4cc(F)cc(Cl)c4)c(Cl)cc13)SCC2] | 1H NMR (400 MHz, $CDCl_3$) δ 7.47 (d, J = 6.8 Hz, 1H), 7.23-7.20 (m, 1H), 7.05-7.04 (m, 1H), 6.90-6.88 (m, 1H), 6.83-6.74 (m, 2H), 6.29 (t, J = 54.8 Hz, 1H), 4.87-4.14 (m, 5H), 3.93-3.52 (m, 3H), 3.13-3.01 (m, 3H), 1.45-1.40 (m, 3H). | 569.43 | 75 |
| 64 | (S)-9-chloro-10-(3-chloro-5-fluorophenyl)-7-(4-(2-fluoroacryloyl)-2-methylpiperazin-1-yl)-2,3-dihydro-5H-[1,4]thiazino[2,3,4-ij]quinazolin-5-one | 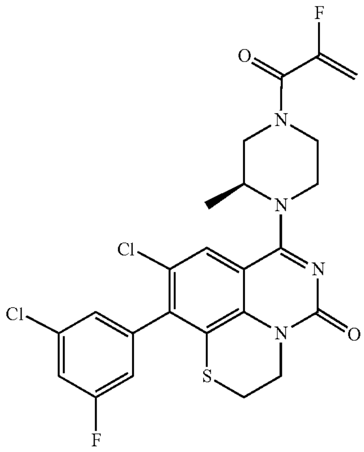 [SMILES: C=C(F)C(=O)N1CCN(c2nc(=O)n3c4c(c(-c5cc(F)cc(Cl)c5)c(Cl)cc24)SCC3)[C@@H](C)C1] | 1H NMR (400 MHz, $CDCl_3$) δ 7.47 (s, 1H), 7.23-7.20 (m, 1H), 7.05-7.04 (m, 1H), 6.90-6.88 (m, 1H), 5.37 (dd, J = 47.2 Hz, 3.2 Hz, 1H), 5.20 (dd, J = 16.8 Hz, 3.6 Hz, 1H), 4.78-4.74 (m, 1H), 4.50-3.80 (m, 5H), 3.64-3.56 (m, 2H), 3.09 (t, J = 4.8 Hz, 3H), , 1.44 (d, J = 6.8 Hz, 3H). | 537.41 | 3 |

TABLE 2a-continued

| Summary of Examples | | | | | |
|---|---|---|---|---|---|
| Ex.# | Name | Structure | $^1$H NMR | MS | % CAF 10 uM @ 60 min |
| 65 | (S)-9-chloro-10-(3-chloro-5-fluorophenyl)-7-(4-(2-fluoroacryloyl)-2-methylpiperazin-1-yl)-2,3-dihydro-5H-[1,4]thiazino[2,3,4-ij]quinazolin-5-one | 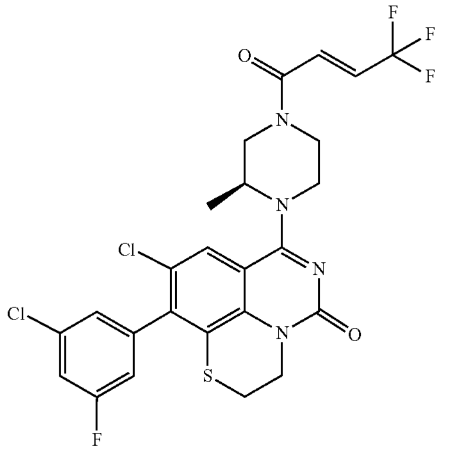 [SMILES: C[C@H]1CN(C(=O)/C=C/C(F)(F)F)CCN1c1nc(=O)n2c3c(c(-c4cc(F)cc(Cl)c4)c(Cl)cc13)SCC2] | 1H NMR (400 MHz, $CDCl_3$) δ 7.47-7.45 (d, J = 7.2 H, 1H), 7.23-7.20 (m, 1H), 7.05-7.04 (m, 1H), 6.99-6.95 (m, 1H), 6.90-6.88 (m, 1H), 4.87-3.91 (m, 5H), 3.75-3.53 (m, 2H), 3.17-2.99 (m, 3H), 1.45-1.40 (dd, J = 10.8 Hz, 6.4 Hz, 3H). | 587.42 | 70 |
| 66 | (S)-7-(4-acryloyl-2-methylpiperazin-1-yl)-9-chloro-10-(3,5-difluorophenyl)-2,3-dihydro-5H-[1,4]thiazino[2,3,4-ij]quinazolin-5-one | 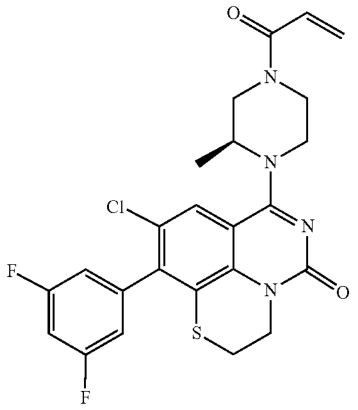 [SMILES: C=CC(=O)N1CCN(c2nc(=O)n3c4c(c(-c5cc(F)cc(F)c5)c(Cl)cc24)SCC3)[C@@H](C)C1] | 1H NMR (400 MHz, $CDCl_3$) δ 7.47 (s, 1H), 6.95-6.90 (m, 1H), 6.80-6.78 (m, 2H), 6.63-6.52 (m, 1H), 6.39-6.35 (m, 1H), 5.80-5.77 (d, J = 10.4 Hz, 1H), 4.88-4.85 (m, 0.5H), 4.70-4.62 (m, 1H), 4.43-4.28 (m, 3H), 4.16-3.96 (m, 1H), 3.84-3.80 (m, 0.5H), 3.66-3.47 (m, 2H), 3.12-2.94 (m, 3H), 1.49-1.41 (m, 3H). | 502.96 | 91 |
| 67 | (S,E)-9-chloro-7-(4-(4,4-difluorobut-2-enoyl)-2-methylpiperazin-1-yl)-10-(3,5-difluorophenyl)-2,3-dihydro-5H-[1,4]thiazino[2,3,4-ij]quinazolin-5-one | 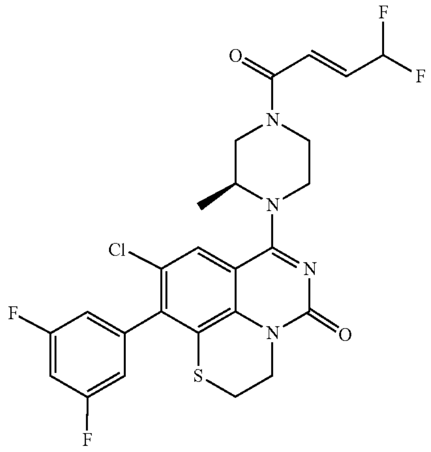 [SMILES: C[C@H]1CN(C(=O)/C=C/C(F)F)CCN1c1nc(=O)n2c3c(c(-c4cc(F)cc(F)c4)c(Cl)cc13)SCC2] | 1H NMR (400 MHz, $CDCl_3$) δ 7.46 (d, J = 6.8 Hz, 1H), 6.95-6.91 (m, 1H), 6.86-6.70 (m, 4H), 6.29 (t, J = 56 Hz, 1H), 4.87-4.86 (m, 0.5H), 4.68-4.65 (m, 1H), 4.47-4.32 (m, 3H), 4.17-3.92 (dd, J = 13.6 Hz, 1H), 3.77-3.74 (m, 0.5H), 3.66-3.51 (m, 2H), 3.16-3.00 (m, 3H), 1.45-1.40 (m, 3H). | 552.97 | 87 |

TABLE 2a-continued

| Ex.# | Name | Structure | $^1$H NMR | MS | % CAF 10 uM @ 60 min |
|---|---|---|---|---|---|
| Summary of Examples | | | | | |
| 71 | 7-((S)-4-acryloyl-2-methylpiperazin-1-yl)-9-chloro-10-(isoquinolin-8-yl)-2,3-dihydro-5H-[1,4]thiazino[2,3,4-ij]quinazolin-5-one | 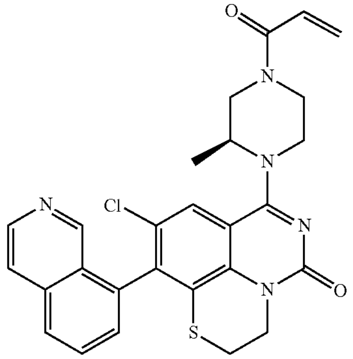 [SMILES: C=CC(=O)N1CCN(c2nc(=O)n3c4c(c(-c5cccc6ccncc56)c(Cl)cc24)SCC3)[C@@H](C)C1] | $^1$H NMR (400 MHz, MeOD) δ 8.84-8.14 (m, 2H), 8.00 (d, J = 8.3 Hz, 1H), 7.92-7.74 (m, 2H), 7.67 (d, J = 9.6 Hz, 1H), 7.46 (dt, J = 7.1, 1.4 Hz, 1H), 6.85-6.62 (m, 1H), 6.19 (ddd, J = 17.0, 7.3, 2.0 Hz, 1H), 5.72 (dd, J = 10.6, 1.9 Hz, 1H), 4.85 (d, J = 7.3 Hz, 1H), 4.78-4.68 (m, 1H), 4.52-3.86 (m, 5H), 3.73-3.33 (m, 2H), 3.20-2.92 (m, 3H), 1.35 (d, J = 6.7 Hz, 1H), 1.30 (d, J = 6.7 Hz, 1H) | 518.03 | 87.8 |
| 72 | 7-(7-acetyl-9-acryloyl-3,7,9-triazabicyclo[3.3.1]nonan-3-yl)-9-chloro-10-(2,4-difluorophenyl)-2,3-dihydro-5H-[1,4]oxazino[2,3,4-ij]quinazolin-5-one | 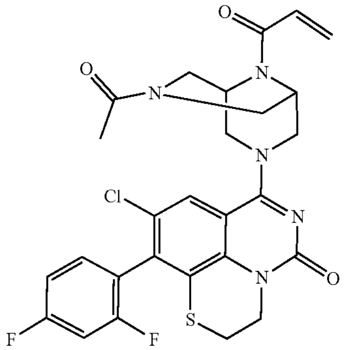 [SMILES: C=CC(=O)N1C2CN(C(C)=O)CC1CN(c1nc(=O)n3c4c(c(-c5ccc(F)cc5F)c(Cl)cc14)SCC3)C2] | $^1$H NMR (400 MHz, MeOD) δ 8.45 (s, 1H), 7.62-7.52 (m, 1H), 7.25-7.15 (m, 1H), 7.08-6.90 (m, 2H), 6.76 (td, J = 16.5, 10.6 Hz, 1H), 6.27 (d, J = 16.5 Hz, 1H), 5.78 (ddd, J = 10.6, 5.5, 1.9 Hz, 1H), 5.16-5.03 (m, 1H), 4.54-4.27 (m, 4H), 4.08 (dd, J = 13.3, 5.9 Hz, 1H), 4.01-3.79 (m, 2H), 3.43-3.27 (m, 2H), 3.19-2.99 (m, 3H), 2.77 (d, J = 16.1 Hz, 1H), 1.95 (d, J = 11.1 Hz, 2H) | 572.03 | 80.5 |
| 73 | (S)-7-(4-acryloyl-2-methylpiperazin-1-yl)-9-chloro-10-(3-chloro-5-fluorophenyl)-2,3-dihydro-5H-[1,4]thiazino[2,3,4-ij]quinazolin-5-one | 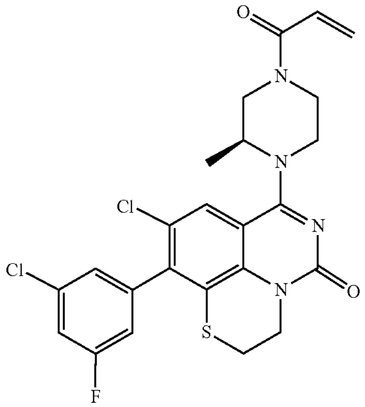 [SMILES: C=CC(=O)N1CCN(c2nc(=O)n3c4c(c(-c5cc(F)cc(Cl)c5)c(Cl)cc24)SCC3)[C@@H](C)C1] | 1H NMR (400 MHz, $CDCl_3$) δ 7.47 (s, 1H), 7.23-7.20 (m, 1H), 7.07-7.05 (m, 1H), 6.90-6.88 (m, 1H), 6.59 (m, 1H), 6.40-6.35(dd, 1H), 5.80-5.77 (d, 1H), 4.88-4.67 (m, 2H), 4.46-4.37 (m, 3H), 4.16-3.81 (m, 2H), 3.62-3.50 (m, 2H), 3.13-3.08 (m, 3H), 1.49 (s, 1H). | 519.42 | 73 |

TABLE 2a-continued

Summary of Examples

| Ex.# | Name | Structure | $^1$H NMR | MS | % CAF 10 uM @ 60 min |
|---|---|---|---|---|---|
| 74 | 7-((S)-4-acryloyl-2-methylpiperazin-1-yl)-9-chloro-10-(2,3-difluorophenyl)-2,3-dihydro-5H-[1,4]thiazino[2,3,4-ij]quinazolin-5-one | 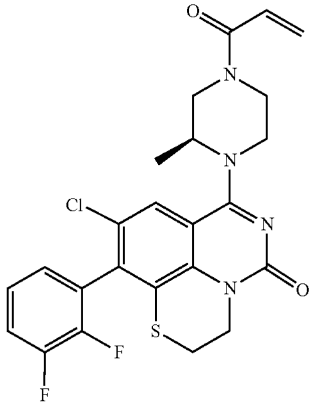 | $^1$H NMR (400 MHz, MeOH-$d_4$) δ 7.69 (d, J = 8.3 Hz, 1H), 7.42 (q, J = 8.2 Hz, 1H), 7.31 (td, J = 8.1, 8.0, 4.6 Hz, 1H), 7.06 (t, J = 6.3 Hz, 1H), 6.91-6.71 (m, 1H), 6.28 (dd, J = 16.8, 6.9 Hz, 1H), 5.80 (dd, J = 10.5, 1.9 Hz, 1H), 4.84-4.74 (m, 1H), 4.60-3.95 (m, 5H), 3.78-3.42 (m, 2H), 3.26-3.00 (m, 3H), 1.40 (dd, J = 20.2, 6.3 Hz, 3H) | 502.96 | 95.6 |
| 75 | 7-((S)-4-acryloyl-2-methylpiperazin-1-yl)-9-chloro-10-(2,4-difluorophenyl)-2,2-dimethyl-2,3-dihydro-5H-[1,4]thiazino[2,3,4-ij]quinazolin-5-one | 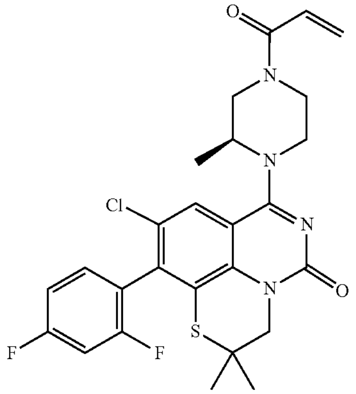 [SMILES: C=CC(=O)N1CCN(c2nc(=O)n3c4c(c(-c5ccc(F)cc5F)c(Cl)cc24)SC(C)(C)C3)[C@@H](C)C1] | | 531.02 | 86.8 |
| 77 | (2S)-1-acryloyl-4-(9-chloro-10-(2,4-difluorophenyl)-5-oxo-2,3-dihydro-5H-[1,4]thiazino[2,3,4-ij]quinazolin-7-yl)piperazine-2-carbonitrile | 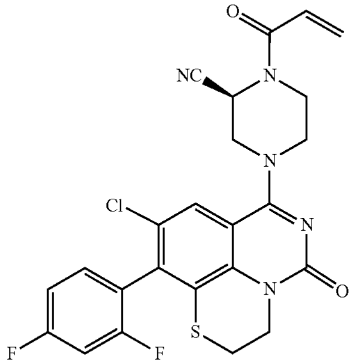 | 1H NMR (400 MHz, $CDCl_3$) δ 7.76-7.68 (d, 1H), 7.26-7.17 (brs, 1H), 7.06-6.97 (m, 2H), 6.61-6.45 (m, 2H), 5.93-5.90 (d, 1H), 4.65-4.36 (m, 4H), 4.20-3.84 (m, 3H), 3.47-3.39 (t, 1H), 3.22-3.04 (m, 3H). | 513.95 | 82 |

TABLE 2a-continued

| Summary of Examples | | | | | |
|---|---|---|---|---|---|
| Ex.# | Name | Structure | $^1$H NMR | MS | % CAF 10 uM @ 60 min |
| 78 | (S)-9-chloro-10-(4-chloro-3-fluorophenyl)-7-(4-(2-fluoroacryloyl)-2-methylpiperazin-1-yl)-2,3-dihydro-5H-[1,4]thiazino[2,3,4-ij]quinazolin-3-one | 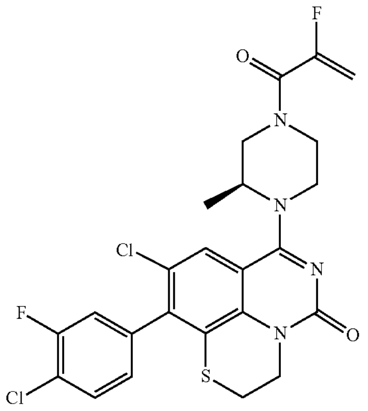 [SMILES: C=C(F)C(=O)N1CCN(c2nc(=O)n3c4c(c(-c5ccc(Cl)c(F)c5)c(Cl)cc24)SCC3)[C@@H](C)C1] | 1H NMR (400 MHz, $CDCl_3$) δ 7.54 (t, J = 8.0 Hz, 1H), 7.46 (s, 1H), 7.08-7.04 (m, 1H), 7.00-6.97 (m, 1H), 5.42-5.30 (m, 1H), 5.22-5.17 (m, 1H), 4.75 (br, 1H), 4.38-4.23 (m, 4H), 4.00-3.89 (m, 1H), 3.59-3.54 (m, 2H), 3.10-3.07 (m, 3H), 1.45-1.42 (m, 3H). | 537.41 | 6.7 |
| 79 | (S,E)-9-chloro-10-(4-chloro-3-fluorophenyl)-7-(2-methyl-4-(4,4,4-trifluorobut-2-enoyl)piperazin-1-yl)-2,3-dihydro-5H-[1,4]thiazino[2,3,4-ij]quinazolin-5-one | 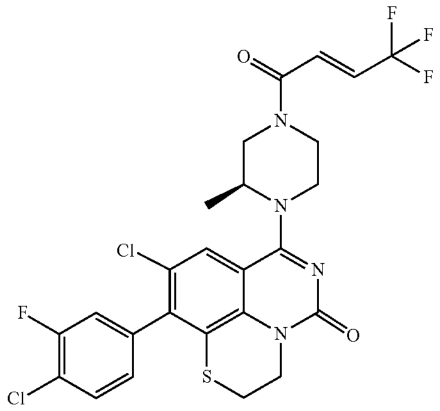 [SMILES: C[C@H]1CN(C(=O)/C=C/C(F)(F)F)CCN1c1nc(=O)n2c3c(c(-c4ccc(Cl)c(F)c4)c(Cl)cc13)SCC2] | 1H NMR (400 MHz, $CDCl_3$) δ 7.54 (t, J = 8.0 Hz, 1H), 7.47-7.45 (m, 1H), 7.07-7.04 (m, 1H), 6.99-6.90 (m, 2H), 6.84-6.76 (m, 1H), 4.88 (br, 0.5H), 4.68-4.64 (m, 1H), 4.48-4.32 (m, 3H), 4.19-3.90 (m, 1H), 3.52-3.74 (m, 2.5H), 3.19-2.97 (m, 3H), 1.45-1.40 (m, 3H). | 587.42 | 92 |
| 80 | (S,E)-9-chloro-10-(4-chloro-3-fluorophenyl)-7-(4-(4,4-difluorobut-2-enoyl)-2-methylpiperazin-1-yl)-2,3-dihydro-5H-[1,4]thiazino[2,3,4-ij]quinazolin-5-one | 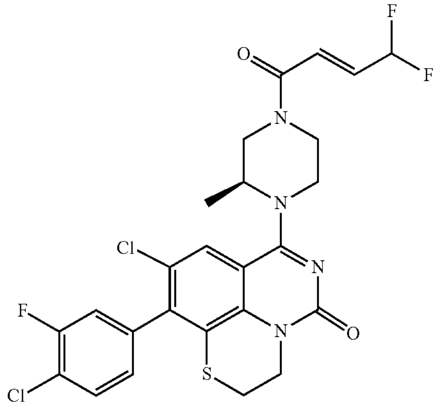 [SMILES: C[C@H]1CN(C(=O)/C=C/C(F)F)CCN1c1nc(=O)n2c3c(c(-c4ccc(Cl)c(F)c4)c(Cl)cc13)SCC2] | 1H NMR (400 MHz, $CDCl_3$) δ 7.54 (t, J = 7.6 Hz, 1H), 7.47-7.45 (m, 1H), 7.07-7.04 (m, 1H), 6.99-6.97 (m, 1H), 6.82-6.71 (m, 2H), 6.42-6.15 (m, 1H), 4.87 (br, 0.5H), 4.68-4.65 (m, 1H), 4.47-4.29 (m, 3H), 4.18-3.92 (m, 1H), 3.77-3.74 (m, 0.5H), 3.66-3.52 (m, 2H), 3.16-3.00 (m, 3H), 1.45-1.39 (m, 3H). | 569.43 | 93.5 |

TABLE 2a-continued

| Summary of Examples | | | | | |
|---|---|---|---|---|---|
| Ex.# | Name | Structure | $^1$H NMR | MS | % CAF 10 uM @ 60 min |
| 81 | 2-((2S)-4-(9-chloro-10-(2,4-difluorophenyl)-5-oxo-2,3-dihydro-5H-[1,4]thiazino[2,3,4-ij]quinazolin-7-yl)-1-((E)-4,4,4-trifluorobut-2-enoyl)piperazin-2-yl)acetonitrile | 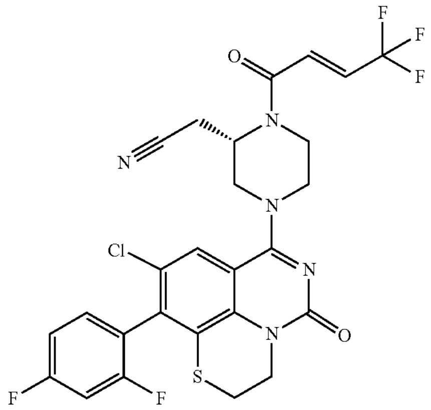 [SMILES: N#CC[C@H]1CN(c2nc(=O)n3c4c(c(-c5ccc(F)cc5F)c(Cl)cc24)SCC3)CCN1C(=O)/C=C/C(F)(F)F] | 1H NMR (400 MHz, $CDCl_3$) δ 7.59(s, 1H), 7.28-7.21 (m, 1H), 7.11-7.00 (m, 3H), 6.92-6.80 (m, 1H), 5.14(s, 0.6H), 4.74-4.63(m, 1H), 4.45-4.37 (m, 3H), 4.22-3.79(m, 3H), 3.60-3.49(m, 1.4H), 3.17-3.14(t, 2H), 3.00-2.80(m, 2H). | 595.97 | 89 |
| 82 | 7-((S)-4-acryloyl-2-methylpiperazin-1-yl)-9-chloro-10-(5-chloro-2,4-difluorophenyl)-2,3-dihydro-5H-[1,4]thiazino[2,3,4-ij]quinazolin-5-one | 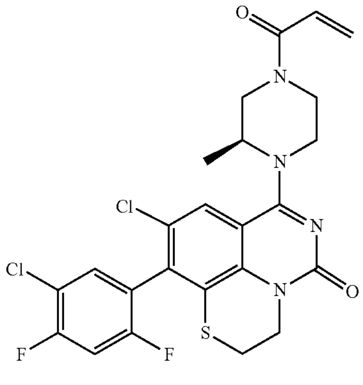 [SMILES: C=CC(=O)N1CCN(c2nc(=O)n3c4c(c(-c5cc(Cl)c(F)cc5F)c(Cl)cc24)SCC3)[C@@H](C)C1] | $^1$H NMR (400 MHz, MeOD) δ 8.45 (s, 1H), 7.59 (d, J = 7.3 Hz, 1H), 7.44-7.35 (m, 1H), 7.28 (t, J = 9.2 Hz, 1H), 6.79-6.65 (m, 1H), 6.18 (dd, J = 16.8, 7.0 Hz, 1H), 5.71 (dd, J = 10.6, 1.9 Hz, 1H), 4.69 (s, 1H), 4.51-3.87 (m, 5H), 3.65-3.35 (m, 2H), 3.20-2.83 (m, 4H), 1.30 (dd, J = 17.4, 6.7 Hz, 2H). | 537.41 | 85.8 |
| 83 | (S)-5-(7-(4-acryloyl-2-methylpiperazin-1-yl)-9-chloro-5-oxo-2,3-dihydro-5H-[1,4]thiazino[2,3,4-ij]quinazolin-10-yl)-2-fluorobenzonitrile | 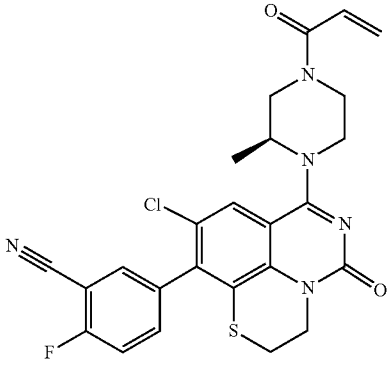 [SMILES: C=CC(=O)N1CCN(c2nc(=O)n3c4c(c(-c5ccc(F)c(C#N)c5)c(Cl)cc24)SCC3)[C@@H](C)C1] | $^1$H NMR (400 MHz, MeOD) δ 8.45 (s, 1H), 7.73-7.49 (m, 3H), 7.45 (t, J = 8.9 Hz, 1H), 6.82-6.65 (m, 1H), 6.19 (dd, J = 16.9, 7.1 Hz, 1H), 5.71 (dd, J = 10.5, 1.9 Hz, 1H), 4.73 (s, 1H), 4.46-3.91 (m, 5H), 3.48 (dt, J = 67.1, 13.4 Hz, 2H), 3.20-2.86 (m, 4H), 1.30 (d, J = 6.7 Hz, 2H). | 509.98 | 85.3 |

TABLE 2a-continued

Summary of Examples

| Ex.# | Name | Structure | $^1$H NMR | MS | % CAF 10 uM @ 60 min |
|---|---|---|---|---|---|
| 84 | | | | | |
| 85 | (S)-5-(7-(4-acryloyl-2-methylpiperazin-1-yl)-9-chloro-5-oxo-2,3-dihydro-5H-[1,4]thiazino[2,3,4-ij]quinazolin-10-yl)-2-fluoro-N-methylbenzamide | 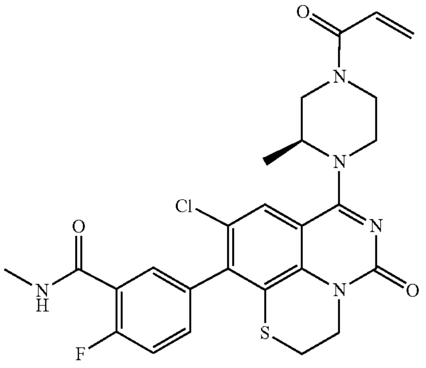 [SMILES: C=CC(=O)N1CCN(c2nc(=O)n3c4c(c(-c5ccc(F)c(C(=O)NC)c5)c(Cl)cc24)SCC3)[C@@H](C)C1] | $^1$H NMR (400 MHz, MeOD) δ 7.62-7.51 (m, 2H), 7.37-7.23 (m, 2H), 6.80-6.64 (m, 1H), 6.18 (dd, J = 16.8, 6.9 Hz, 1H), 5.71 (dd, J = 10.6, 2.0 Hz, 1H), 4.73 (s, 1H), 4.49-3.89 (m, 6H), 3.59-3.36 (m, 2H), 3.18-2.89 (m, 4H), 2.85 (s, 3H), 1.30 (dd, J = 6.8, 2.5 Hz, 2H). | 542.02 | 60.3 |
| 86 | 7-((S)-4-acryloyl-2-methylpiperazin-1-yl)-9-chloro-10-(isoquinolin-5-yl)-2,3-dihydro-5H-[1,4]thiazino[2,3,4-ij]quinazolin-5-one | 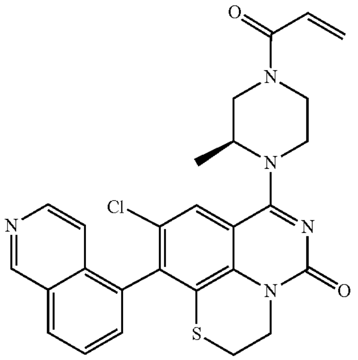 [SMILES: C=CC(=O)N1CCN(c2nc(=O)n3c4c(c(-c5cccc6cnccc56)c(Cl)cc24)SCC3)[C@@H](C)C1] | $^1$H NMR (400 MHz, MeOD) δ 9.26 (s, 1H), 8.63-8.24 (m, 2H), 8.17 (d, J = 8.2 Hz, 1H), 7.80-7.47 (m, 3H), 7.23 (d, J = 5.8 Hz, 1H), 6.74 (ddd, J = 21.1, 16.7, 10.6 Hz, 1H), 6.26-6.13 (m, 1H), 5.72 (dd, J = 10.6, 1.9 Hz, 1H), 4.61-3.86 (m, 6H), 3.68-3.39 (m, 2H), 3.17-2.93 (m, 3H), 1.34 (dd, J = 15.2, 6.7 Hz, 2H). | 518.03 | 76.1 |
| 88 | 2-((2S)-1-acryloyl-4-(9-chloro-10-(2,4-difluorophenyl)-5-oxo-2,3-dihydro-5H-[1,4]thiazino[2,3,4-ij]quinazolin-7-yl)piperazin-2-yl)acetonitrile | 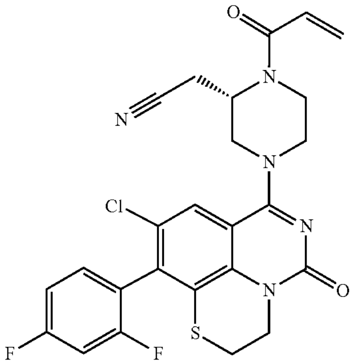 [SMILES: C=CC(=O)N1CCN(c2nc(=O)n3c4c(c(-c5ccc(F)cc5F)c(Cl)cc24)SCC3)C[C@@H]1CC#N] | 1H NMR (400 MHz, $CDCl_3$) δ 7.55 (m, 1H), 7.26-7.17 (m, 1H), 7.05-6.96 (m, 2H), 6.62-6.55 (m, 1H), 6.42-6.38(m, 1H), 5.85-5.83 (m, 1H), 5.03-4.97 (m, 1H), 4.67-4.64(m, 1H), 4.4-4.09(m, 3H), 4.02-4.01(m, 1H), 3.76-3.66(m, 2H), 3.54-3.43(m, 1H), 3.14-3.09(m, 2H), 2.94-2.75(m, 2H). | 527.97 | 90.2 |
| 89 | (S)-7-(4-acryloyl-2-methylpiperazin-1-yl)-9-chloro-10-(4-chloro-3-fluorophenyl)-2,3-dihydro-5H-[1,4]thiazino[2,3,4-ij]quinazolin-5-one | 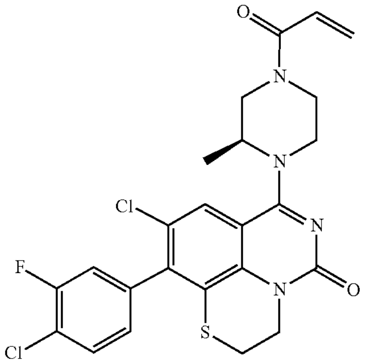 [SMILES: C=CC(=O)N1CCN(c2nc(=O)n3c4c(c(-c5ccc(Cl)c(F)c5)c(Cl)cc24)SCC3)[C@@H](C)C1] | 1H NMR (400 MHz, $CDCl_3$) δ 7.54 (t, J = 7.6 Hz, 1H), 7.47 (m, 1H), 7.08-7.04 (m, 1H), 6.99-6.97 (m, 1H), 6.66-6.52 (m, 1H), 6.39-6.35 (m, 1H), 5.78 (d, J = 11.2 Hz, 1H), 4.89-4.88 (m, 0.5H), 4.70-4.66 (m, 1H), 4.45-4.32 (m, 3H), 4.17-3.94 (m, 1H), 3.85-3.78 (m, 0.5H), 3.61-3.50 (m, 2H), 3.14-2.90 (m, 3H), 1.41 (s, 3H). | 519.42 | 94.5 |

TABLE 2a-continued

| Summary of Examples | | | | | |
|---|---|---|---|---|---|
| Ex.# | Name | Structure | $^1$H NMR | MS | % CAF 10 uM @ 60 min |
| 90 | (S)-7-(4-acryloyl-2-methylpiperazin-1-yl)-9-chloro-10-(3,4,5-trifluorophenyl)-2,3-dihydro-5H-[1,4]thiazino[2,3,4-ij]quinazolin-5-one | 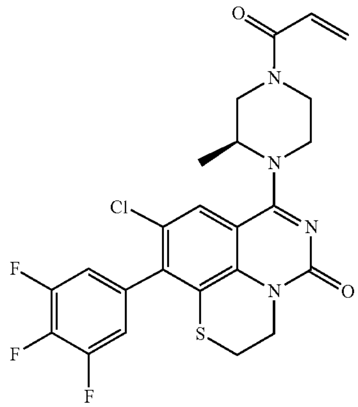 [SMILES: C=CC(=O)N1CCN(c2nc(=O)n3c4c(c(-c5cc(F)c(F)c(F)c5)c(Cl)cc24)SCC3)[C@@H](C)C1] | 1H NMR (400 MHz, $CDCl_3$) δ 7.46 (s, 1H), 6.89 (s, 2H), 6.67-6.63 (m, 1H), 6.49-6.39 (m, 1H), 5.80-5.77 (m, 1H), 4.89-4.86 (m, 0.5H), 4.72-4.60 (m, 1H), 4.49-4.33 (m, 3H), 4.15-3.97 (m, 1H), 3.84-3.82 (m, 0.5H), 3.65-3.50 (m, 2H), 3.11-2.88 (m, 3H), 1.41 (s, 3H). | 520.95 | 78.8 |
| 93 | (S,E)-9-chloro-10-(3-chloro-4-fluorophenyl)-7-(2-methyl-4-(4,4,4-trifluorobut-2-enoyl)piperazin-1-yl)-2,3-dihydro-5H-[1,4]thiazino[2,3,4-ij]quinazolin-5-one | 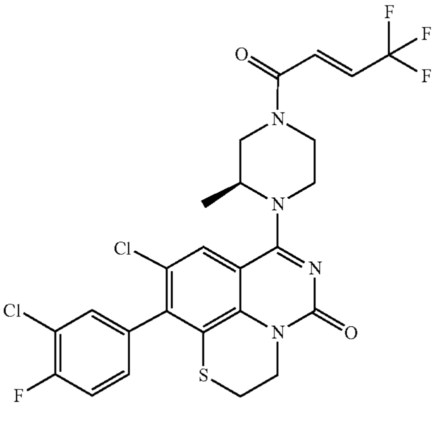 [SMILES: C[C@H]1CN(C(=O)/C=C/C(F)(F)F)CCN1c1nc(=O)n2c3c(c(-c4ccc(F)c(Cl)c4)c(Cl)cc13)SCC2] | 1H NMR (400 MHz, $CDCl_3$) δ 7.47-7.45 (m, 1H), 7.31-7.29 (m, 2H), 7.14-7.12 (m, 1H), 7.04-6.91 (m, 1H), 6.86-6.76 (m, 1H), 4.87 (s, 0.5H), 4.68-4.64 (m, 1H), 4.48-4.29 (m, 3H), 3.93-3.90 (m, 0.5H), 3.74-3.71 (m, 0.5H), 3.68-3.53 (m, 3H), 3.17-3.15 (m, 0.5H), 3.13-3.02 (m, 2H), 1.50-1.38 (m, 3H). | 587.42 | 95 |
| 95 | 7-(9-acryloyl-7-(methylsulfonyl)-3,7,9-triazabicyclo[3.3.1]nonan-3-yl)-9-chloro-10-(2,4-difluorophenyl)-2,3-dihydro-5H-[1,4]thiazino[2,3,4-ij]quinazolin-5-one | 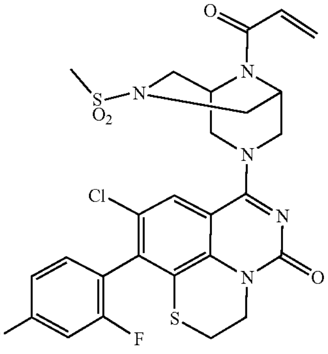 | $^1$H NMR (400 MHz, MeOD) δ 7.59 (s, 1H), 7.25-7.15 (m, 1H), 7.08-6.97 (m, 2H), 6.79-6.68 (m, 1H), 6.25 (dd, J = 16.7, 1.8 Hz, 1H), 5.77 (dd, J = 10.6, 1.9 Hz, 1H), 4.98-4.84 (m, 1H), 4.76 (s, 1H), 4.48-4.40 (m, 1H), 4.26-3.94 (m, 3H), 3.77-3.55 (m, 4H), 3.04 (h, J = 3.3 Hz, 2H), 2.97-2.79 (m, 2H), 2.55 (s, 3H). | 608.08 | 70.5 |

TABLE 2a-continued

Summary of Examples

| Ex.# | Name | Structure | $^1$H NMR | MS | % CAF 10 uM @ 60 min |
|---|---|---|---|---|---|
| 96 | 7-((S)-4-acryloyl-2-methylpiperazin-1-yl)-9-chloro-10-(3-oxoisoindolin-4-yl)-2,3-dihydro-5H-[1,4]thiazino[2,3,4-ij]quinazolin-5-one | 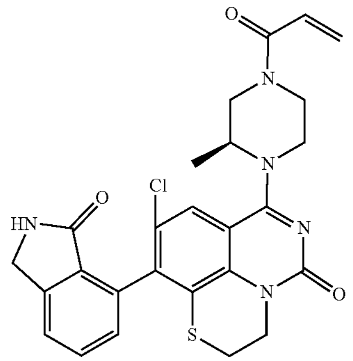 [SMILES: C=CC(=O)N1CCN(c2nc(=O)n3c4c(c(-c5cccc6c5C(=O)NC6)c(Cl)cc24)SCC3)[C@@H](C)C1] | $^1$H NMR (400 MHz, MeOH-$d_4$) δ 7.78-7.67 (m, 2H), 7.63 (d, J = 9.4 Hz, 1H), 7.27 (d, J = 5.3 Hz, 1H), 6.92-6.72 (m, 1H), 6.29 (dd, J = 15.6, 5.2 Hz, 1H), 5.81 (d, J = 10.6 Hz, 1H), 4.86-4.75 (m, 1H), 4.60-3.95 (m, 5H), 4.51 (s, 2H, overlap), 3.78-3.39 (m, 2H), 3.23-2.98 (m, 3H), 1.40 (dd, J = 23.6, 6.7 Hz, 3H) | 522.02 | 54 |
| 98 | (S)-7-(4-acryloyl-2-methylpiperazin-1-yl)-9-chloro-10-(3-chloro-4-fluorophenyl)-2,3-dihydro-5H-[1,4]thiazino[2,3,4-ij]quinazolin-5-one | 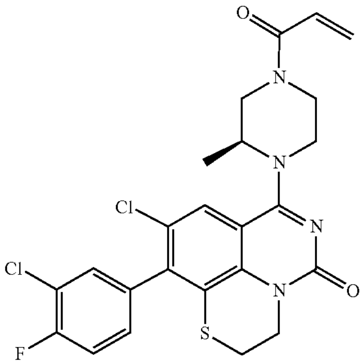 [SMILES: C=CC(=O)N1CCN(c2nc(=O)n3c4c(c(-c5ccc(F)c(Cl)c5)c(Cl)cc24)SCC3)[C@@H](C)C1] | 1H NMR (400 MHz, $CDCl_3$) δ 7.47 (s, 1H), 7.30-7.28 (m, 2H), 6.63-6.52 (m, 1H), 6.40-6.35 (m, 1H), 5.79 (d, J = 11.6 1H), 4.88-4.87 (m, 1H), 4.70-4.63 (m, 1H), 4.45-4.33 (m, 3H), 4.13-4.12 (m, 1H), 3.83-3.79 (m, 0.5H), 3.62-3.51(m, 2H), 3.11-2.95 (m, 3H), 1.58-1.25 (m, 3H). | 519.42 | 86.4 |
| 99 | (3R)-7-((S)-4-acryloyl-2-methylpiperazin-1-yl)-9-chloro-10-(2,4-difluorophenyl)-3-methyl-2,3-dihydro-5H-[1,4]thiazino[2,3,4-ij]quinazolin-5-one | 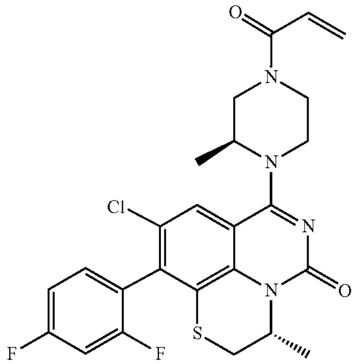 [SMILES: C=CC(=O)N1CCN(c2nc(=O)n3c4c(c(-c5ccc(F)cc5F)c(Cl)cc24)SC[C@H]3C)[C@@H](C)C1] | 1H NMR (400 MHz, $CDCl_3$) δ 7.51 (s, 1H), 7.25-7.19 (m, 1H), 7.07-6.97 (m, 2H), 6.59-6.57 (m, 1H), 6.39-6.36(d, 1H), 5.79-5.76(d, 1H), 5.42(s, 1H), 4.96-4.86(d, 1H), 4.64-4.62(d, 1H), 4.02-3.96(t, 1.5H), 3.83-3.67(m, 2H), 3.42-3.21(m, 2H), 2.92-2.87(m, 1.5H), 1.48-1.45(t, 3H), 1.33-1.31(d, 3H). | 516.99 | 87.2 |
| 105 | 7-((S)-4-acryloyl-2-methylpiperazin-1-yl)-9-chloro-10-(2-oxoindolin-4-yl)-2,3-dihydro-5H-[1,4]thiazino[2,3,4-ij]quinazolin-5-one | 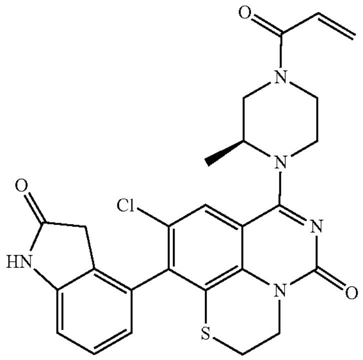 [SMILES: C=CC(=O)N1CCN(c2nc(=O)n3c4c(c(-c5cccc6c5CC(=O)N6)c(Cl)cc24)SCC3)[C@@H](C)C1] | $^1$H NMR (400 MHz, MeOH-$d_4$) δ 7.68 (d, J = 4.5 Hz, 1H), 7.36 (t, J = 7.8 Hz, 1H), 7.00 (d, J = 7.8 Hz, 1H), 6.91-6.75 (m, 2H), 6.29 (dd, J = 16.8, 5.7 Hz, 1H), 5.81 (dd, J = 10.6, 1.9 Hz, 1H), 4.85-4.76 (m, 1H), 4.65-3.98 (m, 5H), 3.75-3.43 (m, 2H), 3.31 (s, overlapped with $D_3COH$, 2H), 3.30-3.05 (m, 4H), 1.41 (dd, J = 11.0, 6.7 Hz, 3H) | 522.02 | 18.9 |

TABLE 2a-continued

Summary of Examples

| Ex.# | Name | Structure | $^1$H NMR | MS | % CAF 10 uM @ 60 min |
|---|---|---|---|---|---|
| 106 | (S)-7-(4-acryloyl-2-methylpiperazin-1-yl)-9-chloro-10-(4-chloro-2,6-difluorophenyl)-2,3-dihydro-5H-[1,4]thiazino[2,3,4-ij]quinazolin-5-one | 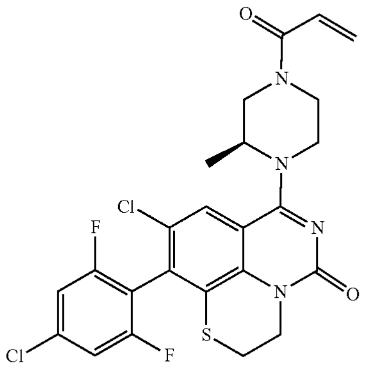 [SMILES: C=CC(=O)N1CCN(c2nc(=O)n3c4c(c(-c5c(F)cc(Cl)cc5F)c(Cl)cc24)SCC3)[C@@H](C)C1] | $^1$H NMR (400 MHz, MeOH-$d_4$) δ 8.52 (br s, 1H), 7.71 (s, 1H), 7.31 (d, J = 7.6 Hz, 2H), 6.82 (ddd, J = 21.7, 16.7, 10.6 Hz, 1H), 6.28 (dd, J = 17.1, 6.7 Hz, 1H), 5.81 (dd, J = 10.6, 2.0 Hz, 1H), 4.60-3.96 (m, 5H), 3.74-3.55 (m, 3H), 3.27-3.18 (m, 3H), 1.41 (d, J = 6.8 Hz, 3H) | 537.41 | 45.2 |
| 107 | (S)-7-((S)-4-acryloyl-2-methylpiperazin-1-yl)-9-chloro-10-(1-methyl-1H-indazol-7-yl)-2,3-dihydro-5H-[1,4]thiazino[2,3,4-ij]quinazolin-5-one | 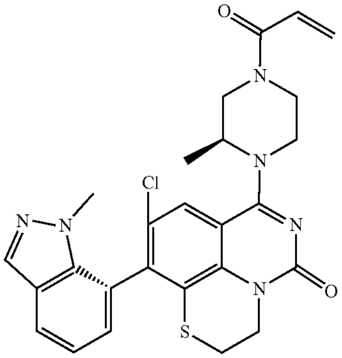 | $^1$H NMR (400 MHz, DMSO) δ 8.14 (s, 1H), 7.89 (d, J = 8.0 Hz, 1H), 7.68 (s, 1H), 7.26 (t, J = 7.4 Hz, 1H), 7.17 (s, 1H), 6.85 (dd, J = 27.2, 16.7 Hz, 1H), 6.20 (d, J = 15.8 Hz, 1H), 5.75 (d, J = 10.2 Hz, 1H), 4.70 (s, 1H), 4.45-4.22 (m, 2H), 4.11 (d, J = 39.6 Hz, 3H), 3.56 (s, 5H), 3.15 (s, 2H), 3.01 (s, 1H), 1.28 (s, 3H). | 521.03 | 0 |
| 108 | (R)-7-((S)-4-acryloyl-2-methylpiperazin-1-yl)-9-chloro-10-(1-methyl-1H-indazol-7-yl)-2,3-dihydro-5H-[1,4]thiazino[2,3,4-ij]quinazolin-5-one | 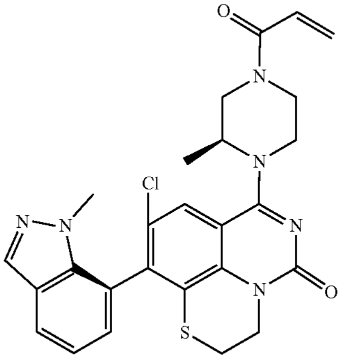 | $^1$H NMR (400 MHz, DMSO) δ 8.14 (s, 1H), 7.89 (d, J = 8.0 Hz, 1H), 7.68 (s, 1H), 7.26 (t, J = 7.4 Hz, 1H), 7.17 (s, 1H), 6.85 (dd, J = 27.2, 16.7 Hz, 1H), 6.20 (d, J = 15.8 Hz, 1H), 5.75 (d, J = 10.2 Hz, 1H), 4.70 (s, 1H), 4.45-4.22 (m, 2H), 4.11 (d, J = 39.6 Hz, 3H), 3.56 (s, 5H), 3.15 (s, 2H), 3.01 (s, 1H), 1.28 (s, 3H). | 521.03 | 91.7 |
| 111 | (S,E)-9-chloro-7-(2-methyl-4-(4,4,4-trifluorobut-2-enoyl)piperazin-1-yl)-10-(2,4,6-trifluorophenyl)-2,3-dihydro-5H-[1,4]thiazino[2,3,4-ij]quinazolin-5-one | 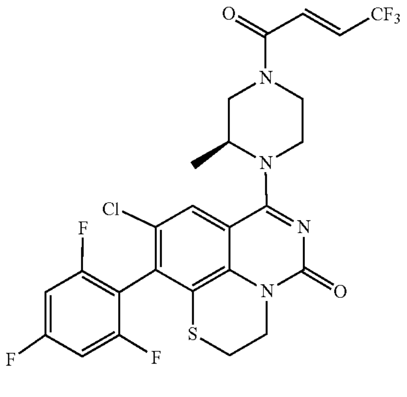 [SMILES: C[C@H]1CN(C(=O)/C=C/C(F)(F)F)CCN1c1nc(=O)n2c3c(c(-c4c(F)cc(F)cc4F)c(Cl)cc13)SCC2] | 1H NMR (400 MHz, $CDCl_3$) δ 7.49-7.47 (d, 1H), 7.04-6.90 (m, 1H), 6.86-6.76 (m, 3H), 4.87-4.48 (m, 2H), 4.45-4.16(m, 3H), 3.93-3.50(m, 3H), 3.18-3.00(m, 3H), 1.45-1.40(m, 3H). | 588.95 | 95.2 |

TABLE 2a-continued

| Summary of Examples | | | | | |
|---|---|---|---|---|---|
| Ex.# | Name | Structure | $^1$H NMR | MS | % CAF 10 uM @ 60 min |
| 112 | 9-chloro-10-(2,4-difluorophenyl)-7-((S)-2-methyl-4-((E)-4,4,4-trifluorobut-2-enoyl)piperazin-1-yl)-2,3-dihydro-5H-[1,4]thiazino[2,3,4-ij]quinazolin-5-one | 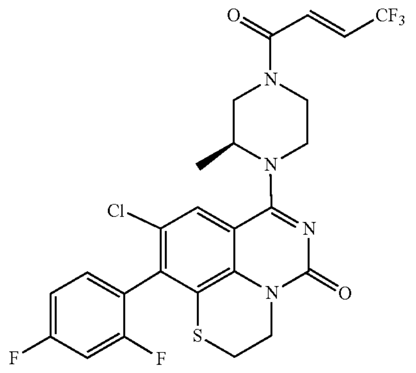 [SMILES: C[C@H]1CN(C(=O)/C=C/C(F)(F)F)CCN1c1nc(=O)n2c3c(c(-c4ccc(F)cc4F)c(Cl)cc13)SCC2] | 1H NMR (400 MHz, $CDCl_3$) δ 7.48-7.46 (brs, 1H), 7.24-7.17 (brs, 1H), 7.06-6.91 (m, 3H), 6.84-6.76 (m, 1H), 4.93-4.75(m, 1H), 4.71-4.55(m, 1H), 4.53-4.42(m, 1H), 4.39-4.10(m, 2H), 3.93-3.47(brs, 3H), 3.21-2.96(m, 3H), 1.53-1.38(m, 3H). | 570.96 | 86.2 |
| 113 | 9-chloro-10-(2,4-difluorophenyl)-7-((S)-4-(2-fluoroacryloyl)-2-methylpiperazin-1-yl)-2,3-dihydro-5H-[1,4]thiazino[2,3,4-ij]quinazolin-5-one | 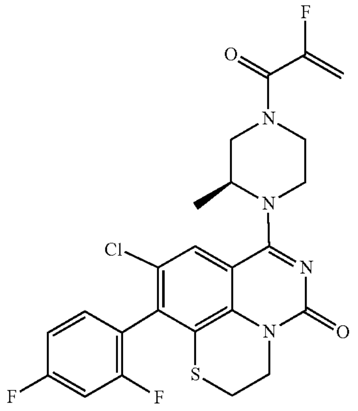 [SMILES: C=C(F)C(=O)N1CCN(c2nc(=O)n3c4c(c(-c5ccc(F)cc5F)c(Cl)cc24)SCC3)[C@@H](C)C1] | 1H NMR (400 MHz, $CDCl_3$) δ 7.47 (d, 1H), 7.21-7.19 (m, 1H), 7.05-6.97 (m, 2H), 5.42-5.29 (m, 1H), 5.22-5.17(m, 1H), 4.83-4.72(brs, 1H), 4.56-4.45(brs, 1H), 4.45-4.11(brs, 3H), 4.09-3.88(brs, 1H), 3.67-3.42(brs, 2H), 3.11-3.09(t, 3H), 1.47-1.40(m, 3H). | 520.95 | 21.7 |
| 119 | 9-chloro-7-((S)-4-((E)-4,4-difluorobut-2-enoyl)-2-methylpiperazin-1-yl)-10-(2,4-difluorophenyl)-2,3-dihydro-5H-[1,4]thiazino[2,3,4-ij]quinazolin-5-one | 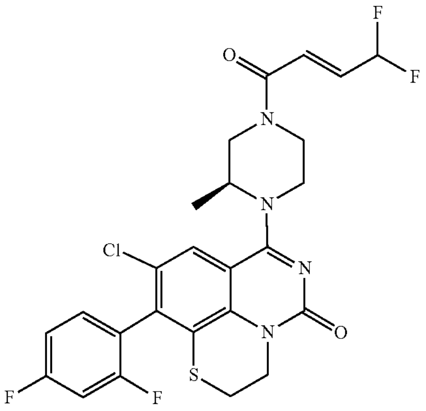 [SMILES: C[C@H]1CN(C(=O)/C=C/C(F)F)CCN1c1nc(=O)n2c3c(c(-c4ccc(F)cc4F)c(Cl)cc13)SCC2] | 1H NMR (400 MHz, $CDCl_3$) δ 7.47 (brs, 1H), 7.23-7.17 (m, 1H), 7.06-6.96 (m, 2H), 6.83-6.70 (m, 2H), 6.43-6.75(t, 1H), 4.93-4.57(m, 2H), 4.53-4.10(m, 3H), 3.95-3.48(m, 3H), 3.20-2.97(m, 3H), 1.59-1.38(m, 3H). | 552.97 | 97.1 |

TABLE 2a-continued

| Summary of Examples | | | | | |
|---|---|---|---|---|---|
| Ex.# | Name | Structure | $^1$H NMR | MS | % CAF 10 uM @ 60 min |
| 120 | (S,E)-9-chloro-7-(4-(4,4-difluorobut-2-enoyl)-2-methylpiperazin-1-yl)-10-(2,4,6-trifluorophenyl)-2,3-dihydro-5H-[1,4]thiazino[2,3,4-ij]quinazolin-5-one | 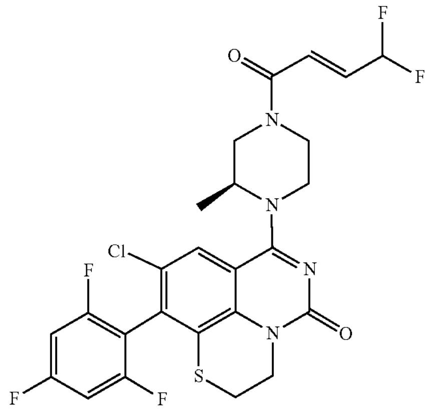 [SMILES: C[C@H]1CN(C(=O)/C=C/C(F)F)CCN1c1nc(=O)n2c3c(c(-c4c(F)cc(F)cc4F)c(Cl)cc13)SCC2] | $^1$H NMR (400 MHz, $CDCl_3$) δ 7.49-7.47 (m, 1H), 6.86-6.69 (m, 4H), 6.28 (t, J = 55.6 Hz, 1H), 4.87-4.65 (m, 1.5H), 4.48-4.32 (m, 3H), 4.19-4.15 (m, 0.5H), 3.95-3.92 (m, 0.5H), 3.77-3.54 (m, 2.5H), 3.15-2.98 (m, 3H), 1.45-1.40 (m, 3H). | 570.96 | 95.9 |
| 121 | (2S)-4-(9-chloro-10-(2,4-difluorophenyl)-5-oxo-2,3-dihydro-5H-[1,4]thiazino[2,3,4-ij]quinazolin-7-yl)-1-((E)-4-(dimethylamino)but-2-enoyl)piperazine-2-carbonitrile | 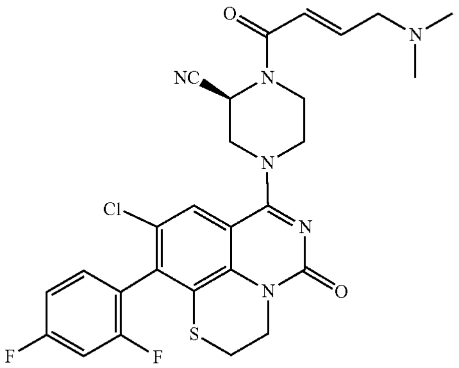 [SMILES: CN(C)C/C=C/C(=O)N1CCN(c2nc(=O)n3c4c(c(-c5ccc(F)cc5F)c(Cl)cc24)SCC3)C[C@H]1C#N] | 1H NMR (400 MHz, DMSO) δ 8.36 (s, 1H), 7.59-7.37 (m, 1H), 7.27 (dd, J = 22.3, 16.0 Hz, 1H), 6.75 (ddd, J = 43.5, 17.4, 10.3 Hz, 1H), 5.32 (p, J = 10.8 Hz, 1H), 4.43 (dd, J = 31.3, 19.2 Hz, 1H), 4.31-4.14 (m, 1H), 4.14-3.94 (m, 1H), 3.71 (s, 1H), 3.60 (s, 2H), 3.09 (d, J = 5.8 Hz, 2H), 2.21 (d, J = 27.5 Hz, 2H), 2.09-1.91 (m, 2H), 1.44 (dd, J = 17.1, 7.1 Hz, 2H), 1.24 (s, 6H). | 571.04 | 3.6 |
| 123 | (R)-7-((S)-4-acryloyl-2-methylpiperazin-1-yl)-9-chloro-10-(2-fluorophenyl)-2,3-dihydro-5H-[1,4]thiazino[2,3,4-ij]quinazolin-5-one | 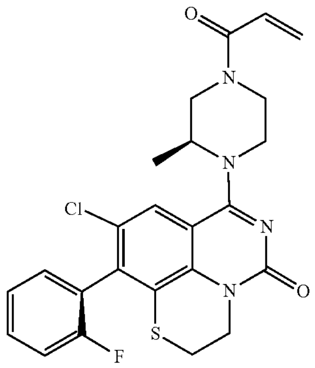 | $^1$H NMR (400 MHz, DMSO-$d_6$) δ 7.64 (s, 1H), 7.47-7.61 (m, 1H), 7.23-7.44 (m, 3H), 6.68-6.94 (m, 1H), 6.18 (dd, J = 7.07, 16.45 Hz, 1H), 5.74 (dd, J = 2.31, 10.44 Hz, 1H), 4.69 (br. s., 1H), 4.40 (d, J = 11.63 Hz, 1H), 4.27 (d, J = 12.51 Hz, 2H), 4.12 (d, J = 12.38 Hz, 1H), 4.00 (d, J = 12.88 Hz, 3H), 3.57 (br. s., 1H), 3.05-3.24 (m, 2H), 1.25 (d, J = 6.50 Hz, 3H) | 484.97 | 91.3 |
| 124 | (S)-7-((S)-4-acryloyl-2-methylpiperazin-1-yl)-9-chloro-10-(2-fluorophenyl)-2,3-dihydro-5H-[1,4]thiazino[2,3,4-ij]quinazolin-5-one | 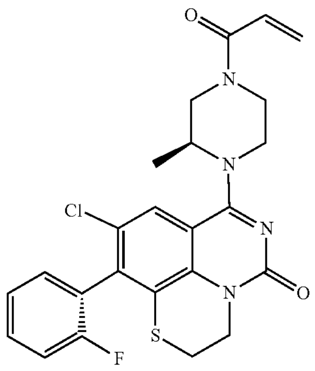 | $^1$H NMR (400 MHz, DMSO-$d_6$) δ 7.50-7.74 (m, 2H), 7.20-7.44 (m, 3H), 6.72-7.01 (m, 1H), 6.18 (dd, J = 6.00, 16.51 Hz, 1H), 5.66-5.80 (m, 1H), 4.63 (br. s., 1H), 4.41 (d, J = 12.63 Hz, 1H), 4.17-4.34 (m, 1H), 3.89-4.13 (m, 3H), 3.54 (d, J = 9.51 Hz, 1H), 3.10-3.21 (m, 3H), 3.07-2.88 (m, 1H), 1.22-1.35 (m, 3H) | 484.97 | 96 |

TABLE 2a-continued

Summary of Examples

| Ex.# | Name | Structure | $^1$H NMR | MS | % CAF 10 uM @ 60 min |
|---|---|---|---|---|---|
| 125 | (2S)-4-(9-chloro-10-(2,4-difluorophenyl)-5-oxo-2,3-dihydro-5H-[1,4]thiazino[2,3,4-ij]quinazolin-7-yl)-1-(2-fluoroacryloyl) piperazine-2-carbonitrile | 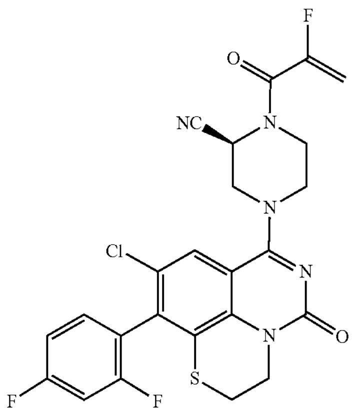 [SMILES: C=C(F)C(=O)N1CCN(c2nc(=O)n3c4c(c(-c5ccc(F)cc5F)c(Cl)cc24)SCC3)C[C@H]1C#N] | 1H NMR (400 MHz,) δ 7.78 (d, J = 11.2 Hz, 1H), 7.49 (td, J = 9.7, 2.4 Hz, 1H), 7.45-7.37 (m, 1H), 7.28 (td, J = 8.5, 2.4 Hz, 1H), 5.59 (d, J = 10.9 Hz, 1H), 5.54 (q, J = 4.4 Hz, 1H), 5.46 (dd, J = 37.9, 4.3 Hz, 1H), 4.54-4.42 (m, 1H), 4.37 (ddd, J = 13.7, 5.8, 2.5 Hz, 0.5H), 4.30-4.04 (m, 3H), 3.98 (ddd, J = 13.9, 8.9, 2.6 Hz, 0.5H), 3.68 (dd, J = 14.1, 3.5 Hz, 1H), 3.60 (dd, J = 14.2, 3.6 Hz, 1H), 3.28-3.06 (m, 3H). | 531.94 | 94.5 |
| 127 | 7-((S)-4-acryloyl-2-methylpiperazin-1-yl)-9-chloro-10-(1-methyl-1H-indazol-7-yl)-2,3-dihydro-5H-[1,4]thiazino[2,3,4-ij]quinazolin-5-one | 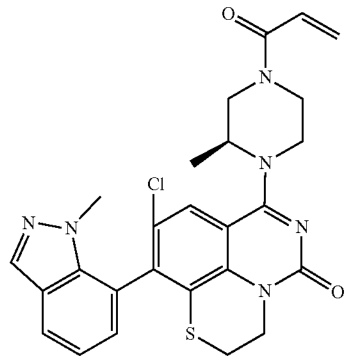 [SMILES: C=CC(=O)N1CCN(c2nc(=O)n3c4c(c(-c5cccc6cnn(C)c56)c(Cl)cc24)SCC3)[C@@H](C)C1] | $^1$H NMR (400 MHz, DMSO) δ 8.14 (s, 1H), 7.89 (d, J = 8.0 Hz, 1H), 7.68 (s, 1H), 7.26 (t, J = 7.4 Hz, 1H), 7.17 (s, 1H), 6.85 (dd, J = 27.2, 16.7 Hz, 1H), 6.20 (d, J = 15.8 Hz, 1H), 5.75 (d, J = 10.2 Hz, 1H), 4.70 (s, 1H), 4.45-4.22 (m, 2H), 4.11 (d, J = 39.6 Hz, 3H), 3.56 (s, 5H), 3.15 (s, 2H), 3.01 (s, 1H), 1.28 (s, 3H). | 521.03 | 60 |
| 130 | (3R)-7-((S)-4-acryloyl-2-methylpiperazin-1-yl)-9-chloro-10-(2,4-difluorophenyl)-3-(methoxymethyl)-2,3-dihydro-5H-[1,4]thiazino[2,3,4-ij]quinazolin-5-one | 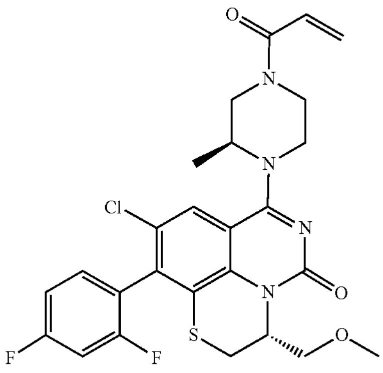 [SMILES: C=CC(=O)N1CCN(c2nc(=O)n3c4c(c(-c5ccc(F)cc5F)c(Cl)cc24)SC[C@H]3COC)[C@@H](C)C1] | | 547.02 | 94.5 |
| 134 | 7-(4-acryloylhexahydro-furo[3,4-b]pyrazin-1(2H)-yl)-9-chloro-10-(2,4-difluorophenyl)-2,3-dihydro-5H-[1,4]thiazino[2,3,4-ij]quinazolin-5-one | 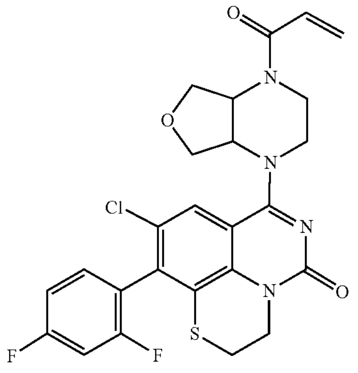 [SMILES: C=CC(=O)N1CCN(c2nc(=O)n3c4c(c(-c5ccc(F)cc5F)c(Cl)cc24)SCC3)C2COCC21] | $^1$H NMR (400 MHz, MeOD) δ 7.64 (d, J = 13.5 Hz, 1H), 7.26-7.15 (m, 1H), 7.10-6.97 (m, 2H), 6.78-6.61 (m, 1H), 6.17 (dd, J = 16.7, 1.9 Hz, 1H), 5.70 (dd, J = 10.5, 2.0 Hz, 1H), 4.97-4.82 (m, 2H), 4.40-4.18 (m, 2H), 4.14-3.41 (m, 8H), 3.16-3.01 (m, 2H) | 530.97 | 85 |

TABLE 2a-continued

| Summary of Examples | | | | | |
|---|---|---|---|---|---|
| Ex.# | Name | Structure | $^1$H NMR | MS | % CAF 10 uM @ 60 min |
| 135 | 7-(3-acryloyl-3,6-diazabicyclo[3.1.1]heptan-6-yl)-9-chloro-10-(2,4-difluorophenyl)-2,3-dihydro-5H-[1,4]thiazino[2,3,4-ij]quinazolin-5-one | 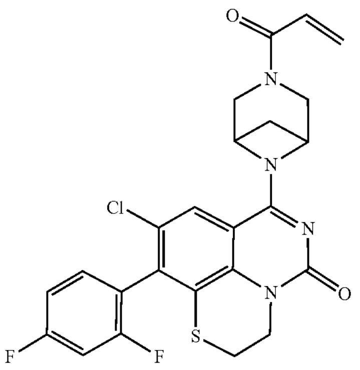 [SMILES: C=CC(=O)N1CC2CC(C1)N2c1nc(=O)n2c3c(c(-c4ccc(F)cc4F)c(Cl)cc13)SCC2] | $^1$H NMR (400 MHz, MeOD) δ 7.98 (d, J = 22.3 Hz, 1H), 7.19 (tdd, J = 8.7, 6.3, 1.9 Hz, 1H), 7.09-6.94 (m, 2H), 6.79-6.60 (m, 1H), 6.17-6.02 (m, 1H), 5.75-5.54 (m, 1H), 4.78-4.26 (m, 4H), 4.19-4.03 (m, 2H), 3.70-3.35 (m, 2H), 3.11-2.96 (m, 2H), 2.45-2.16 (m, 2H) | 500.95 | 0 |
| 136 | 7-((S)-4-acryloyl-2-methylpiperazin-1-yl)-9-chloro-10-(2-oxopyridin-1(2H)-yl)-2,3-dihydro-5H-[1,4]thiazino[2,3,4-ij]quinazolin-5-one | 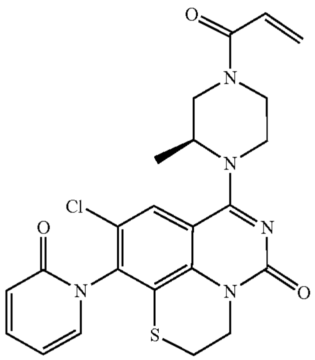 [SMILES: C=CC(=O)N1CCN(c2nc(=O)n3c4c(c(-n5ccccc5=O)c(Cl)cc24)SCC3)[C@@H](C)C1] | 1H NMR (400 MHz, DMSO) δ 8.09 (d, J = 4.7 Hz, 1H), 7.93 (t, J = 7.7 Hz, 1H), 7.62 (s, 1H), 7.27-7.13 (m, 2H), 7.01-6.65 (m, 1H), 6.18 (dd, J = 15.8, 7.0 Hz, 1H), 5.74 (d, J = 10.4 Hz, 1H), 4.63 (s, 1H), 4.33 (dd, J = 56.3, 12.7 Hz, 1H), 4.23-4.07 (m, 2H), 4.01 (d, J = 12.4 Hz, 2H), 3.55 (d, J = 12.7 Hz, 2H), 3.15 (d, J = 24.1 Hz, 2H), 2.98 (d, J = 12.5 Hz, 1H), 1.26 (d, J = 5.7 Hz, 3H). | 483.97 | 89.4 |
| 137 | (R)-7-((S)-4-acryloyl-2-methylpiperazin-1-yl)-9-chloro-3-(methoxymethyl)-10-(2,4,6-trifluorophenyl)-2,3-dihydro-5H-[1,4]thiazino[2,3,4-ij]quinazolin-5-one | 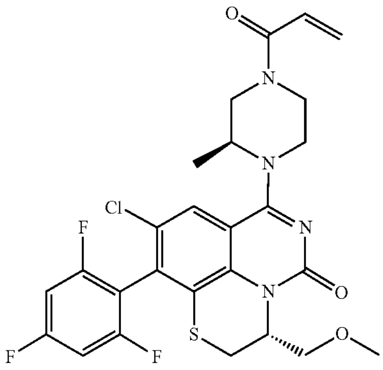 [SMILES: C=CC(=O)N1CCN(c2nc(=O)n3c4c(c(-c5c(F)cc(F)cc5F)c(Cl)cc24)SC[C@H]3COC)[C@@H](C)C1] | | 565.01 | 86.8 |
| 145 | 7-(5-acryloyl-2,5-diazabicyclo[4.2.0]octan-2-yl)-9-chloro-10-(2,4-difluorophenyl)-2,3-dihydro-5H-[1,4]thiazino[2,3,4-ij]quinazolin-5-one | 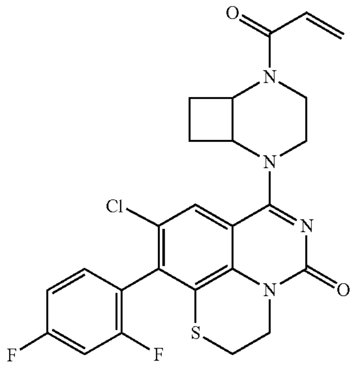 [SMILES: C=CC(=O)N1CCN(c2nc(=O)n3c4c(c(-c5ccc(F)cc5F)c(Cl)cc24)SCC3)C2CCC21] | $^1$H NMR (400 MHz, MeOD) δ 7.67 (d, J = 1.8 Hz, 1H), 7.28-7.13 (m, 1H), 7.09-6.91 (m, 2H), 6.34 (dd, J = 16.8, 10.3 Hz, 1H), 6.19 (dd, J = 16.8, 2.1 Hz, 1H), 5.67 (dd, J = 10.2, 2.1 Hz, 1H), 4.69-4.45 (m, 1H), 4.36-4.26 (m, 1H), 4.24-4.07 (m, 2H), 4.04-3.90 (m, 2H), 3.85-3.71 (m, 1H), 3.71-3.57 (m, 1H), 3.16-2.94 (m, 2H), 2.48-2.22 (m, 2H), 2.01-1.83 (m, 1H), 1.68-1.52 (m, 1H) | 514.97 | 58 |

TABLE 2a-continued

Summary of Examples

| Ex.# | Name | Structure | $^1$H NMR | MS | % CAF 10 uM @ 60 min |
|---|---|---|---|---|---|
| 146 | (S)-7-(4-acryloyl-2-methylpiperazin-1-yl)-9-chloro-10-(2,4,6-trifluorophenyl)-2,3-dihydro-5H-[1,4]thiazino[2,3,4-ij]quinazolin-5-one | 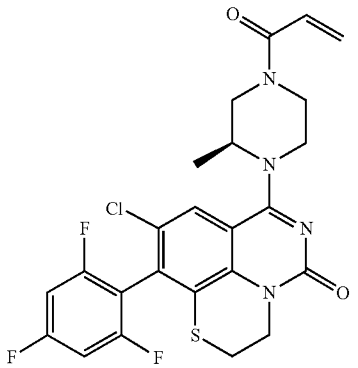 [SMILES: C=CC(=O)N1CCN(c2nc(=O)n3c4c(c(-c5c(F)cc(F)cc5F)c(Cl)cc24)SCC3)[C@@H](C)C1] | $^1$H NMR (400 MHz, DMSO) δ 7.67 (s, 1H), 7.47 (t, J = 8.8 Hz, 2H), 6.94-6.70 (m, 1H), 6.18 (dd, J = 16.7, 6.4 Hz, 1H), 5.74 (dd, J = 10.4, 2.0 Hz, 1H), 4.66 (s, 1H), 4.33 (dd, J = 54.2, 13.2 Hz, 1H), 4.22-3.91 (m, 4H), 3.55 (d, J = 13.7 Hz, 2H), 3.22 (t, J = 4.9 Hz, 2H), 3.17-2.92 (m, 1H), 1.26 (d, J = 6.4 Hz, 3H). | 520.95 | 90.7 |
| 148 | (R)-7-((S)-4-acryloyl-2-methylpiperazin-1-yl)-9-chloro-10-(2,4-difluorophenyl)-2,3-dihydro-5H-[1,4]thiazino[2,3,4-ij]quinazolin-3-one 1,1-dioxide | 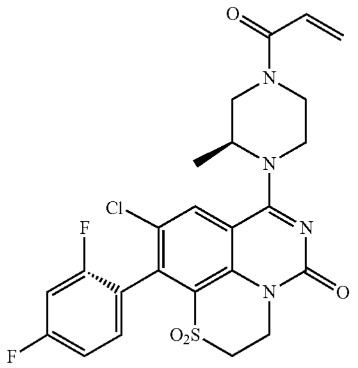 | 1H NMR (400 MHz, $CDCl_3$) δ 7.86 (s, 1H), 7.38-7.33 (m, 1H), 7.06-6.93 (m, 2H), 6.60-6.53 (m, 1H), 6.41-6.37, (m, 1H), 5.81-5.79 m, 1H), 5.05-5.01 2m, 1H), 4.78-4.71 (m, 1H), 4.59-4.35 (m, 3H), 4.01-3.85 (m, 1H), 3.62-3.44 (m, 4H), 3.04 (m, 1H), 1.45 (d, 3H). | 534.96 | 95.9 |
| 149 | (S)-7-((S)-4-acryloyl-2-methylpiperazin-1-yl)-9-chloro-10-(2,4-difluorophenyl)-2,3-dihydro-5H-[1,4]thiazino[2,3,4-ij]quinazolin-5-one 1,1-dioxide | 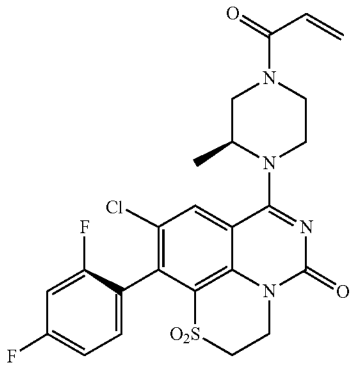 | $^1$H NMR (400 MHz, $CDCl_3$) δ 7.87 (s, 1H), 7.37-7.31 (m, 1H), 7.05-6.93 (m, 2H), 6.41-6.37 (m, 1H), 6.35-6.31, (m, 1H), 5.81-5.79 m, 1H), 5.06-5.01 (m, 1.5H), 4.78-4.71 (m, 1H), 4.51-4.07 (m, 3H), 3.98-3.44 (m, 4.5H), 3.21-2.91 (m, 1H), 1.41 (s, 3H). | 534.96 | 52.8 |
| 150 | 7-((R)-4-acryloyl-2-(hydroxymethyl) piperazin-1-yl)-9-chloro-10-(2,4-difluorophenyl)-2,3-dihydro-5H-[1,4]thiazino[2,3,4-ij]quinazolin-5-one | 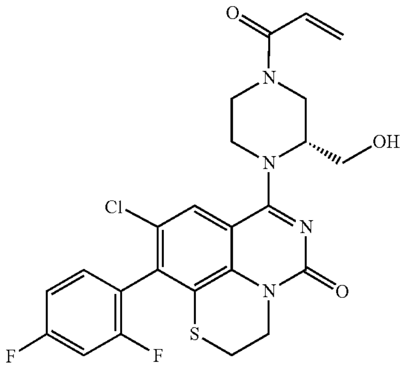 [SMILES: C=CC(=O)N1CCN(c2nc(=O)n3c4c(c(-c5ccc(F)cc5F)c(Cl)cc24)SCC3)[C@@H](CO)C1] | 1H NMR (400 MHz, DMSO) δ 7.90 (dd, J = 40.4, 14.2 Hz, 1H), 7.48 (td, J = 9.7, 2.5 Hz, 1H), 7.44-7.36 (m, 1H), 7.27 (td, J = 8.5, 2.4 Hz, 1H), 6.82 (ddd, J = 16.7, 10.5, 2.2 Hz, 1H), 6.16 (dd, J = 16.6, 2.1 Hz, 1H), 5.72 (dd, J = 10.4, 2.2 Hz, 1H), 5.11 (dd, J = 11.5, 5.8 Hz, 1H), 4.53 (s, 1H), 4.36-3.87 (m, 6H), 3.70-3.38 (m, 4H), 3.23-3.01 (m, 2H). | 518.96 | 59.9 |

TABLE 2a-continued

Summary of Examples

| Ex.# | Name | Structure | $^1$H NMR | MS | % CAF 10 uM @ 60 min |
|---|---|---|---|---|---|
| 151 | (S)-7-(4-acryloyl-2-methylpiperazin-1-yl)-9-chloro-10-(4-fluorophenyl)-2,3-dihydro-5H-[1,4]thiazino[2,3,4-ij]quinazolin-5-one | 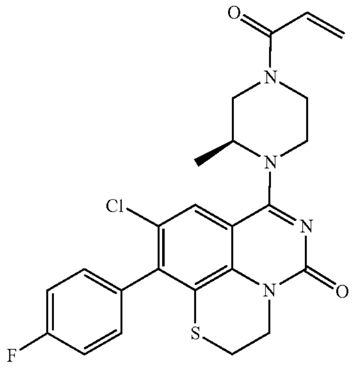 [SMILES: C=CC(=O)N1CCN(c2nc(=O)n3c4c(c(-c5ccc(F)cc5)c(Cl)cc24)SCC3)[C@@H](C)C1] | 1H NMR (400 MHz, DMSO) δ 7.61 (s, 1H), 7.45-7.21 (m, 4H), 6.93-6.75 (m, 1H), 6.18 (dd, J = 16.4, 7.3 Hz, 1H), 5.74 (dd, J = 10.4, 2.2 Hz, 1H), 4.65 (s, 1H), 4.34 (dd, J = 55.7, 12.7 Hz, 1H), 4.04 (dd, J = 40.6, 26.7 Hz, 4H), 3.54 (d, J = 14.0 Hz, 2H), 3.14 (t, J = 4.9 Hz, 2H), 2.96 (t, J = 11.7 Hz, 1H), 1.26 (d, J = 6.3 Hz, 3H). | 484.97 | 94.1 |
| 152 | 7-((S)-4-acryloyl-2-methylpiperazin-1-yl)-9-chloro-10-(2-fluoro-5-hydroxyphenyl)-2,3-dihydro-5H-[1,4]thiazino[2,3,4-ij]quinazolin-5-one | 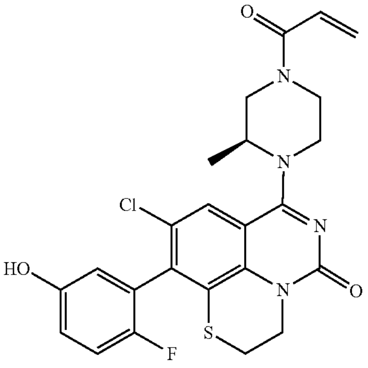 | 1H NMR (400 MHz, DMSO) δ 9.65 (s, 1H), 7.60 (d, J = 9.4 Hz, 1H), 7.17 (t, J = 9.1 Hz, 1H), 6.92-6.74 (m, 2H), 6.59 (dt, J = 5.3, 2.5 Hz, 1H), 6.18 (dd, J = 16.4, 6.0 Hz, 1H), 5.74 (dd, J = 10.4, 2.2 Hz, 1H), 4.65 (d, J = 25.8 Hz, 1H), 4.47-4.17 (m, 2H), 4.16-3.92 (m, 3H), 3.66-3.43 (m, 1H), 3.24-3.06 (m, 3H), 2.96 (d, J = 12.7 Hz, 1H), 1.26 (dd, J = 14.7, 6.1 Hz, 3H). | 500.97 | 55.3 |
| 153 | 7-((S)-4-acryloyl-2-methylpiperazin-1-yl)-9-chloro-10-(2-chloro-5-hydroxyphenyl)-2,3-dihydro-5H-[1,4]thiazino[2,3,4-ij]quinazolin-5-one | 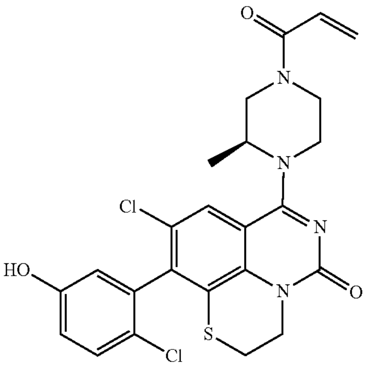 | 1H NMR (400 MHz, DMSO) δ 9.94 (s, 1H), 7.60 (s, 1H), 7.40 (d, J = 8.7 Hz, 1H), 6.89 (dd, J = 8.7, 2.9 Hz, 1H), 6.81 (dd, J = 17.7, 10.0 Hz, 1H), 6.62 (t, J = 2.6 Hz, 1H), 6.18 (dd, J = 16.4, 5.9 Hz, 1H), 5.74 (dd, J = 10.4, 2.3 Hz, 1H), 4.65 (s, 1H), 4.46-3.94 (m, 5H), 3.67-3.47 (m, 1H), 3.23-3.08 (m, 3H), 2.99 (d, J = 12.7 Hz, 1H), 1.25 (d, J = 6.7 Hz, 3H). | 517.43 | 55.7 |
| 154 | (R)-7-((S)-4-acryloyl-2-methylpiperazin-1-yl)-9-chloro-10-(naphthalen-1-yl)-2,3-dihydro-5H-[1,4]thiazino[2,3,4-ij]quinazolin-5-one | 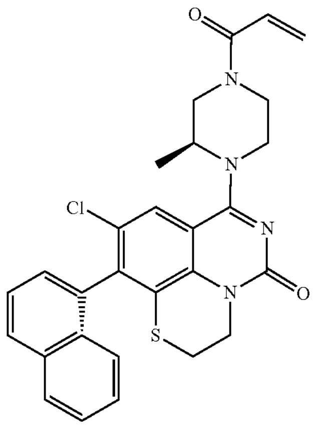 | $^1$H NMR (400 MHz, DMSO) δ 8.05 (t, J = 8.5 Hz, 2H), 7.66 (dd, J = 15.7, 8.5 Hz, 2H), 7.57 (t, J = 7.5 Hz, 1H), 7.47 (t, J = 7.6 Hz, 1H), 7.39 (dd, J = 6.1, 3.3 Hz, 1H),7.35 (dd, J = 8.3, 3.6 Hz, 1H), 6.95-6.75 (m, 1H), 6.26-6.11 (m, 1H), 5.75 (dd, J = 10.4, 2.3 Hz, 1H), 4.84-4.60 (m, 1H), 4.49-4.19 (m, 2H), 4.19-3.94 (m, 3H), 3.70-3.39 (m, 2H), 3.23-2.90 (m, 3H), 1.37-1.24 (m, 3H). | 517.04 | 24 |

TABLE 2a-continued

| Summary of Examples | | | | | |
|---|---|---|---|---|---|
| Ex.# | Name | Structure | $^1$H NMR | MS | % CAF 10 uM @ 60 min |
| 155 | (S)-7-((S)-4-acryloyl-2-methylpiperazin-1-yl)-9-chloro-10-(naphthalen-1-yl)-2,3-dihydro-5H-[1,4]thiazino[2,3,4-ij]quinazolin-5-one | 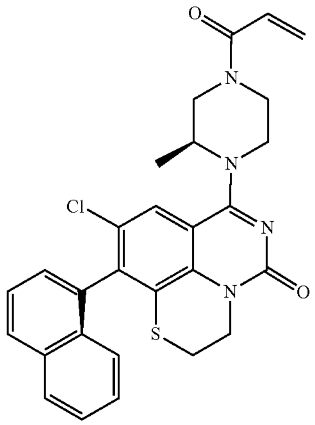 | $^1$H NMR (400 MHz, DMSO) δ 8.05 (t, J = 8.5 Hz, 2H), 7.66 (dd, J = 15.7, 8.5 Hz, 2H), 7.57 (t, J = 7.5 Hz, 1H), 7.47 (t, J = 7.6 Hz, 1H), 7.39 (dd, J = 6.1, 3.3 Hz, 1H), 7.35 (dd, J = 8.3, 3.6 Hz, 1H), 6.95-6.75 (m, 1H), 6.26-6.11 (m, 1H), 5.75 (dd, J = 10.4, 2.3 Hz, 1H), 4.84-4.60 (m, 1H), 4.49-4.19 (m, 2H), 4.19-3.94 (m, 3H), 3.70-3.39 (m, 2H), 3.23-2.9 0(m, 3H), 1.37-1.24 (m, 3H). | 517.04 | 92.2 |
| 159 | 7-((S)-4-acryloyl-2-methylpiperazin-1-yl)-9-chloro-10-(5-methyl-1H-indazol-4-yl)-2,3-dihydro-5H-[1,4]thiazino[2,3,4-ij]quinazolin-5-one | 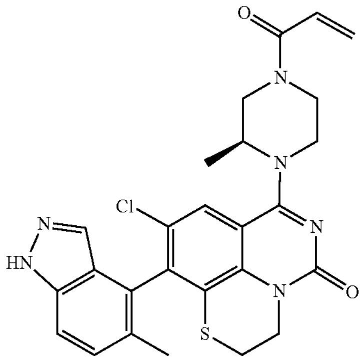 [SMILES: C=CC(=O)N1CCN(c2nc(=O)n3c4c(c(-c5c(C)ccc6[nH]ncc56)c(Cl)cc24)SCC3)[C@@H](C)C1] | 1H NMR (400 MHz, DMSO) δ 13.11 (s, 1H), 7.66 (s, 1H), 7.57-7.47 (m, 2H), 7.35 (d, J = 8.6 Hz, 1H), 6.93-6.75 (m, 1H), 6.19 (dd, J = 17.7, 6.2 Hz, 1H), 5.75 (dd, J = 10.4, 2.3 Hz, 1H), 4.70 (s, 1H), 4.50-4.21 (m, 1H), 4.21-3.92 (m, 4H), 3.58 (s, 1H), 3.23-2.86 (m, 4H), 2.12 (s, 3H), 1.29 (d, J = 5.8 Hz, 3H). | 521.03 | 37.2 |
| 160 | 7-((S)-4-acryloyl-2-methylpiperazin-1-yl)-9-chloro-10-(2-fluorophenyl)-2,3-dihydro-5H-[1,4]thiazino[2,3,4-ij]quinazolin-5-one | 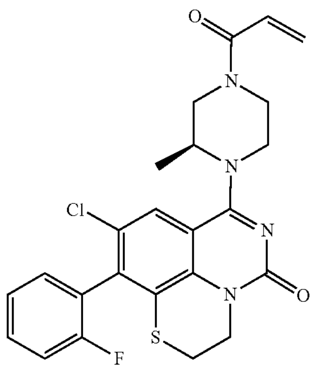 [SMILES: C=CC(=O)N1CCN(c2nc(=O)n3c4c(c(-c5ccccc5F)c(Cl)cc24)SCC3)[C@@H](C)C1] | 1H NMR (400 MHz, DMSO) δ 7.68-7.52 (m, 2H), 7.47-7.26 (m, 3H), 6.82 (s, 1H), 6.18 (dd, J = 16.9, 7.0 Hz, 1H), 5.74 (dd, J = 10.4, 2.3 Hz, 1H), 4.76-4.56 (m, 1H), 4.47-4.18 (m, 2H), 4.18-3.92 (m, 3H), 3.66-3.42 (m, 1H), 3.24-3.07 (m, 3H), 3.07-2.88 (m, 1H), 1.26 (dd, J = 13.3, 6.8 Hz, 3H). | 484.97 | 72.7 |

TABLE 2a-continued

Summary of Examples

| Ex.# | Name | Structure | $^1$H NMR | MS | % CAF 10 uM @ 60 min |
|---|---|---|---|---|---|
| 161 | (2R,5R)-4-acryloyl-1-(9-chloro-10-(2,4-difluorophenyl)-5-oxo-2,3-dihydro-5H-[1,4]thiazino[2,3,4-ij]quinazolin-7-yl)-5-methylpiperazine-2-carbonitrile | 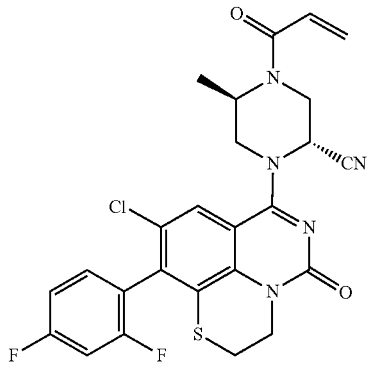 [SMILES: C=CC(=O)N1C[C@H](C#N)N(c2nc(=O)n3c4c(c(-c5ccc(F)cc5F)c(Cl)cc24)SCC3)C[C@H]1C] | $^1$H NMR (400 MHz, DMSO) δ 8.35 (s, 1H), 7.53 (td, J = 9.6, 2.2 Hz, 1H), 7.41 (td, J = 14.5, 8.0 Hz, 1H), 7.36-7.28 (m, 1H), 6.92 (s, 1H), 6.39-6.13 (m, 1H), 5.87 (d, J = 10.9 Hz, 1H), 5.19 (d, J = 16.6 Hz, 1H), 4.88 (dd, J = 22.7, 14.2 Hz, 1H), 4.61 (d, J = 10.7 Hz, 1H), 4.52-4.39 (m, 1H), 4.38-4.27 (m, 1H), 4.24-4.07 (m, 1H), 3.24-2.95 (m, 4H), 1.21 (s, 3H). | 527.97 | 1 |
| 162 | 7-((S)-4-acryloyl-2-methylpiperazin-1-yl)-9-chloro-10-(5-(difluoromethyl)-2-fluorophenyl)-2,3-dihydro-5H-[1,4]thiazino[2,3,4-ij]quinazolin-5-one | 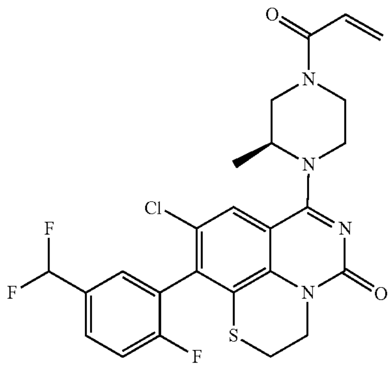 [SMILES: C=CC(=O)N1CCN(c2nc(=O)n3c4c(c(-c5cc(C(F)F)ccc5F)c(Cl)cc24)SCC3)[C@@H](C)C1] | $^1$H NMR (400 MHz, DMSO) δ 7.89-7.71 (m, 1H), 7.65 (d, J = 10.2 Hz, 1H), 7.62-7.53 (m, 2H), 7.12 (t, J = 55.6 Hz, 1H), 6.92-6.71 (m, 1H), 6.18 (dd, J = 16.4, 6.3 Hz, 1H), 5.74 (dd, J = 10.4, 2.3 Hz, 1H), 4.78-4.54 (m, 1H), 4.47-4.18 (m, 2H), 4.18-3.88 (m, 3H), 3.56 (d, J = 11.6 Hz, 2H), 3.27-3.08 (m, 2H), 3.05 2.89 (m, 1H), 1.26 (dd, J = 13.8, 6.5 Hz, 3H). | 534.98 | 39 |
| 163 | 7-((S)-4-acryloyl-2-methylpiperazin-1-yl)-9-chloro-10-(5-(difluoromethoxy)-2-fluorophenyl)-2,3-dihydro-5H-[1,4]thiazino[2,3,4-ij]quinazolin-5-one | 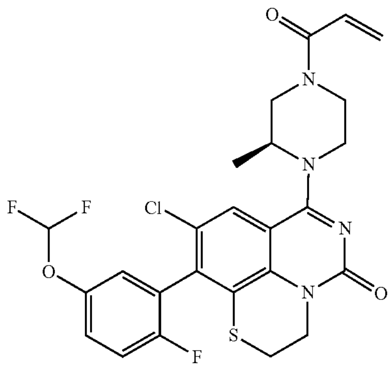 [SMILES: C=CC(=O)N1CCN(c2nc(=O)n3c4c(c(-c5cc(OC(F)F)ccc5F)c(Cl)cc24)SCC3)[C@@H](C)C1] | 1H NMR (400 MHz, DMSO) δ 7.64 (d, J = 8.1 Hz, 1H), 7.50 (t, J = 8.9 Hz, 1H), 7.42-7.36 (m, 1H), 7.27 (t, J = 73.6 Hz, 1H), 7.20 (td, J = 5.5, 3.0 Hz, 1H), 6.91-6.72 (m, 1H), 6.18 (dd, J = 15.9, 6.3 Hz, 1H), 5.74 (dd, J = 10.4, 2.3 Hz, 1H), 4.75-4.54 (m, 1H), 4.46-4.18 (m, 2H), 4.17-3.90 (m, 3H), 3.67-3.43 (m, 2H), 3.25-3.07 (m, 2H), 3.05 2.87 (m, 1H), 1.26 (dd, J = 10.3, 6.8 Hz, 3H). | 550.98 | 41.4 |
| 165 | 7-(6-acryloyl-3,6-diazabicyclo[3.1.1]heptan-3-yl)-9-chloro-10-(2,4-difluorophenyl)-2,3-dihydro-5H-[1,4]thiazino[2,3,4-ij]quinazolin-5-one | 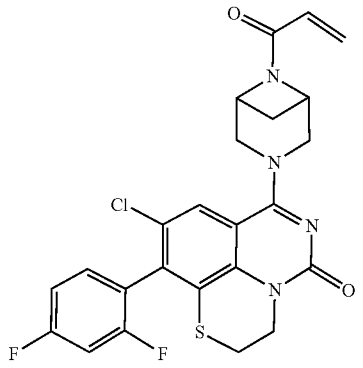 [SMILES: C=CC(=O)N1C2CC1CN(c1nc(=O)n3c4c(c(-c5ccc(F)cc5F)c(Cl)cc14)SCC3)C2] | $^1$H NMR (400 MHz, MeOD) δ 7.93 (d, J = 1.1 Hz, 1H), 7.25-7.15 (m, 1H), 7.09-6.93 (m, 2H), 6.39 (dd, J = 16.9, 10.3 Hz, 1H), 6.20 (dt, J = 16.9, 1.7 Hz, 1H), 5.69 (dd, J = 10.3, 1.8 Hz, 1H), 4.51-4.04 (m, 7H), 3.07 (dd, 2H), 2.69 (q, J = 6.6 Hz, 1H), 1.61 (d, J = 9.1 Hz, 1H) | 500.95 | 16.9 |

TABLE 2a-continued

Summary of Examples

| Ex.# | Name | Structure | $^1$H NMR | MS | % CAF 10 uM @ 60 min |
|---|---|---|---|---|---|
| 167 | 7-((S)-4-acryloyl-2-methylpiperazin-1-yl)-9-chloro-10-(2-(trifluoromethyl) phenyl)-2,3-dihydro-5H-[1,4]thiazino[2,3,4-ij]quinazolin-5-one | 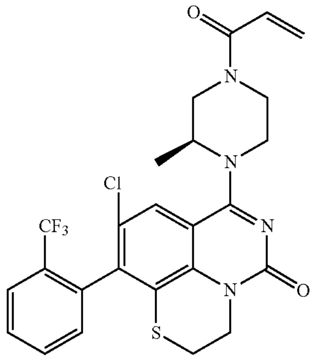 [SMILES: C=CC(=O)N1CCN(c2nc(=O)n3c4c(c(-c5ccccc5C(F)(F)F)c(Cl)cc24)SCC3)[C@@H](C)C1] | 1H NMR (400 MHz, DMSO) δ 7.92 (d, J = 8.0 Hz, 1H), 7.84 (t, J = 7.5 Hz, 1H), 7.73 (t, J = 7.6 Hz, 1H), 7.63 (s, 1H), 7.41-7.26 (m, 1H), 6.95-6.75 (m, 1H), 6.25-6.13 (m, 1H), 5.74 (dd, J = 10.4, 2.3 Hz, 1H), 4.77-4.57 (m, 1H), 4.47-4.22 (m, 1H), 4.21-3.95 (m, 4H), 3.66-3.37 (m, 2H), 3.20-3.08 (m, 2H), 3.05-2.91 (m, 1H), 1.26 (d, J = 6.8 Hz, 3H). | 534.98 | 69.8 |
| 168 | 7-((S)-4-acryloyl-2-methylpiperazin-1-yl)-9-chloro-10-(2-fluoro-6-hydroxyphenyl)-2,3-dihydro-5H-[1,4]thiazino[2,3,4-ij]quinazolin-5-one | 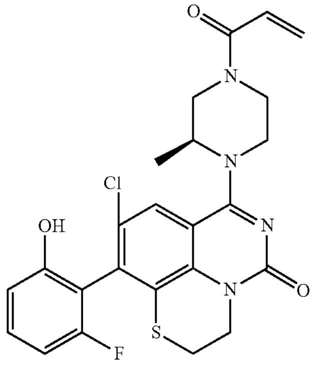 [SMILES: C=CC(=O)N1CCN(c2nc(=O)n3c4c(c(-c5c(O)cccc5F)c(Cl)cc24)SCC3)[C@@H](C)C1] | $^1$H NMR (400 MHz, DMSO) δ 10.08-10.05 (m, 1H), 7.59 (s, 1H), 7.31 (dd, J = 15.4, 8.3 Hz, 1H), 6.88-6.69 (m, 3H), 6.23-6.11 (m, 1H), 5.74 (dd, J = 10.4, 2.3 Hz, 1H), 4.71-4.56 (m, 1H), 4.45-4.23 (m, 1H), 4.21-3.91 (m, 4H), 3.60-3.45 (m, 2H), 3.16-3.11 (m, 2H), 3.03-2.90 (m, 1H), 1.26 (d, J = 6.0 Hz, 3H). | 500.97 | 30.6 |
| 169 | 7-((S)-4-acryloyl-2-(azetidin-1-ylmethyl)piperazin-1-yl)-9-chloro-10-(2,4-difluorophenyl)-2,3-dihydro-5H-[1,4]thiazino[2,3,4-ij]quinazolin-5-one | 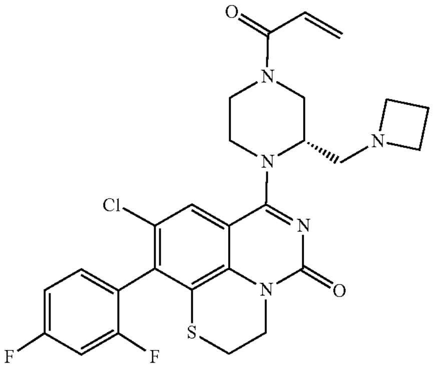 [SMILES: C=CC(=O)N1CCN(c2nc(=O)n3c4c(c(-c5ccc(F)cc5F)c(Cl)cc24)SCC3)[C@@H](CN2CCC2)C1] | $^1$H NMR (400 MHz, DMSO) δ 8.01 (d, J = 57.6 Hz, 1H), 7.56-7.44 (m, 1H), 7.40 (dd, J = 14.6, 7.8 Hz, 1H), 7.28 (td, J = 8.5, 2.5 Hz, 1H), 6.82 (d, J = 9.7 Hz, 1H), 6.17 (d, J = 16.8 Hz, 1H), 5.74 (s, 1H), 4.47-4.24 (m, 3H), 4.16-4.01 (m, 3H), 3.40 (dd, J = 12.4, 5.9 Hz, 1H), 3.35 (s, 1H), 3.30 (s, 1H), 3.15 (dd, J = 42.2, 31.1 Hz, 7H), 2.88 (dd, J = 21.5, 10.7 Hz, 1H), 1.93 (s, 2H). | 558.04 | 23.3 |
| 170 | (S)-7-(4-acryloyl-2-methylpiperazin-1-yl)-9-chloro-10-(2,6-difluorophenyl)-2,3-dihydro-5H-[1,4]thiazino[2,3,4-ij]quinazolin-5-one | 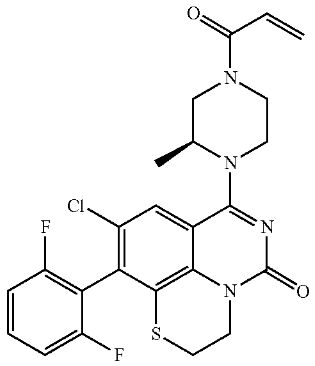 [SMILES: C=CC(=O)N1CCN(c2nc(=O)n3c4c(c(-c5c(F)cccc5F)c(Cl)cc24)SCC3)[C@@H](C)C1] | $^1$H NMR (400 MHz, DMSO) δ 7.71-7.61 (m, 2H), 7.32 (t, J = 8.4 Hz, 2H), 6.90-6.75 (m, 1H), 6.23-6.12 (m, 1H), 5.74 (dd, J = 10.4, 2.3 Hz, 1H), 4.74-4.60 (m, 1H), 4.45-3.95 (m, 5H), 3.64-3.48 (m, 2H), 3.21 (t, J = 5.1 Hz, 2H), 3.17-2.92 (m, 1H), 1.27 (d, J = 6.5 Hz, 3H). | 502.96 | 75.9 |

TABLE 2a-continued

| Summary of Examples | | | | | |
|---|---|---|---|---|---|
| Ex.# | Name | Structure | $^1$H NMR | MS | % CAF 10 uM @ 60 min |
| 171 | 7-((S)-4-acryloyl-2-methylpiperazin-1-yl)-9-chloro-10-(2,5-dichlorophenyl)-2,3-dihydro-5H-[1,4]thiazino[2,3,4-ij]quinazolin-5-one | 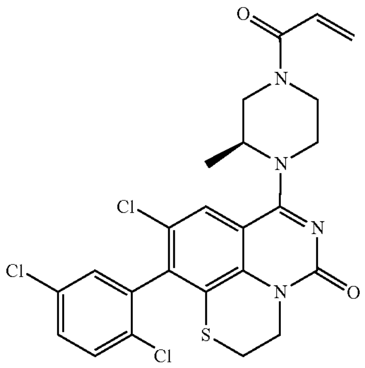 [SMILES: C=CC(=O)N1CCN(c2nc(=O)n3c4c(c(-c5cc(Cl)ccc5Cl)c(Cl)cc24)SCC3)[C@@H](C)C1] | $^1$H NMR (400 MHz, DMSO) δ 7.71 (d, J = 8.7 Hz, 1H), 7.65 (d, J = 4.1 Hz, 1H), 7.61 (dd, J = 8.7, 2.6 Hz, 1H), 7.48 (dd, J = 6.3, 2.5 Hz, 1H), 6.90-6.77 (m, 1H), 6.18 (dd, J = 17.3, 7.9 Hz, 1H), 5.74 (dd, J = 10.4, 2.3 Hz, 1H), 4.67 (s, 1H), 4.45-3.95 (m, 5H), 3.64 3.48 (m, 2H), 3.25-3.11 (m, 2H), 3.07-2.91 (m, 1H), 1.26 (d, J = 6.3 Hz, 3H). | 535.87 | 48.9 |
| 172 | 7-((S)-4-acryloyl-2-methylpiperazin-1-yl)-9-chloro-10-(naphthalen-1-yl)-2,3-dihydro-5H-[1,4]thiazino[2,3,4-ij]quinazolin-5-one | 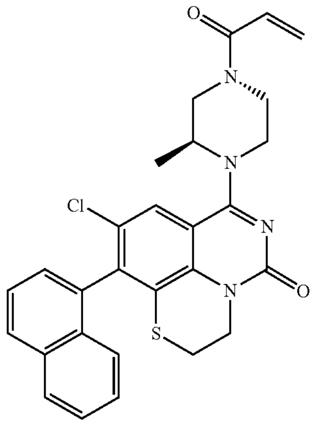 | $^1$H NMR (400 MHz, DMSO) δ 8.05 (t, J = 8.5 Hz, 2H), 7.66 (dd, J = 15.7, 8.5 Hz, 2H), 7.57 (t, J = 7.5 Hz, 1H), 7.47 (t, J = 7.6 Hz, 1H), 7.39 (dd, J = 6.1, 3.3 Hz, 1H), 7.35 (dd, J = 8.3, 3.6 Hz, 1H), 6.95-6.75 (m, 1H), 6.26-6.11 (m, 1H), 5.75 (dd, J = 10.4, 2.3 Hz, 1H), 4.84-4.60 (m, 1H), 4.49-4.19 (m, 2H), 4.19-3.94 (m, 3H), 3.70-3.39 (m, 2H), 3.23-2.90 (m, 3H), 1.37-1.24 (m, 3H). | 517.04 | 51.9 |
| 173 | (2R)-4-acryloyl-1-(9-chloro-10-(2,4-difluorophenyl)-5-oxo-2,3-dihydro-5H-[1,4]thiazino[2,3,4-ij]quinazolin-7-yl)piperazine-2-carbonitrile | 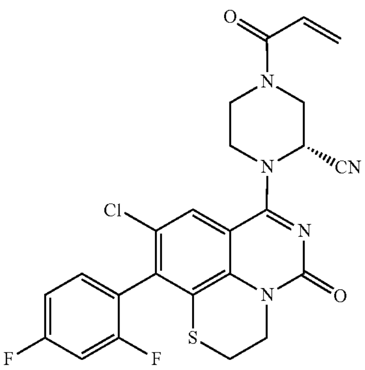 [SMILES: C=CC(=O)N1CCN(c2nc(=O)n3c4c(c(-c5ccc(F)cc5F)c(Cl)cc24)SCC3)[C@@H](C#N)C1] | $^1$H NMR (400 MHz, DMSO) δ 8.24 (s, 1H), 7.53 (td, J = 9.6, 2.3 Hz, 1H), 7.44-7.37 (m, 1H), 7.36-7.26 (m, 1H), 6.91 (s, 1H), 6.27 (d, J = 16.0 Hz, 1H), 5.86 (d, J = 11.0 Hz, 1H), 4.83 (d, J = 8.6 Hz, 2H), 4.61-4.48 (m, 1H), 4.35-4.00 (m, 3H), 3.03-2.78 (m, 5H). | 513.95 | 2.2 |

TABLE 2a-continued

Summary of Examples

| Ex.# | Name | Structure | $^1$H NMR | MS | % CAF 10 uM @ 60 min |
|---|---|---|---|---|---|
| 174 | 7-((S)-4-acryloyl-2-methylpiperazin-1-yl)-9-chloro-10-(3-chloro-2-fluorophenyl)-2,3-dihydro-5H-[1,4]thiazino[2,3,4-ij]quinazolin-5-one | 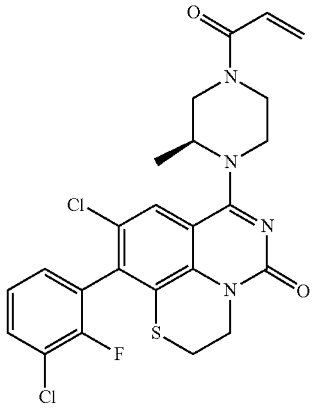 [SMILES: C=CC(=O)N1CCN(c2nc(=O)n3c4c(c(-c5cccc(Cl)c5F)c(Cl)cc24)SCC3)[C@@H](C)C1] | 1H NMR (400 MHz, DMSO) δ 7.79-7.73 (m, 1H), 7.65 (d, J = 8.4 Hz, 1H), 7.42 (t, J = 7.9 Hz, 1H), 7.33 (dddd, J = 7.8, 6.3, 4.6, 1.7 Hz, 1H), 6.94-6.75 (m, 1H), 6.18 (dd, J = 16.8, 6.3 Hz, 1H), 5.74 (dd, J = 10.4, 2.3 Hz, 1H), 4.66 (d, J = 25.0 Hz, 1H), 4.45-4.19 (m, 2H), 4.18-3.91 (m, 3H), 3.51 (dd, J = 43.2, 15.1 Hz, 2H), 3.26-3.09 (m, 2H), 2.97 (dd, J = 24.1, 11.9 Hz, 1H), 1.26 (dd, J = 12.0, 6.6 Hz, 3H). | 519.42 | 93.8 |
| 175 | 7-((S)-4-acryloyl-2-methylpiperazin-1-yl)-9-chloro-10-(5-chloro-2-fluorophenyl)-2,3-dihydro-5H-[1,4]thiazino[2,3,4-ij]quinazolin-5-one | 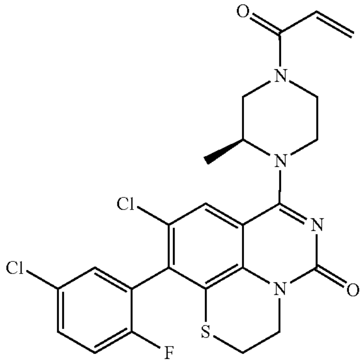 [SMILES: C=CC(=O)N1CCN(c2nc(=O)n3c4c(c(-c5cc(Cl)ccc5F)c(Cl)cc24)SCC3)[C@@H](C)C1] | 1H NMR (401 MHz, DMSO) δ 7.64 (d, J = 10.8 Hz, 2H), 7.55-7.41 (m, 2H), 6.83 (d, J = 10.2 Hz, 1H), 6.30-6.06 (m, 1H), 5.74 (dd, J = 10.4, 2.0 Hz, 1H), 4.65 (d, J = 31.4 Hz, 1H), 4.47-4.18 (m, 2H), 4.03 (dd, J = 27.6, 13.3 Hz, 3H), 3.68-3.41 (m, 2H), 3.27-3.07 (m, 2H), 3.06-2.87 (m, 1H), 1.26 (dd, J = 12.9, 6.2 Hz, 3H). | 519.42 | 79.8 |
| 176 | 2-((2S)-4-(9-chloro-10-(2,4-difluorophenyl)-5-oxo-2,3-dihydro-5H-[1,4]thiazino[2,3,4-ij]quinazolin-7-yl)-1-(2-fluoroacryloyl)piperazin-2-yl)acetonitrile | 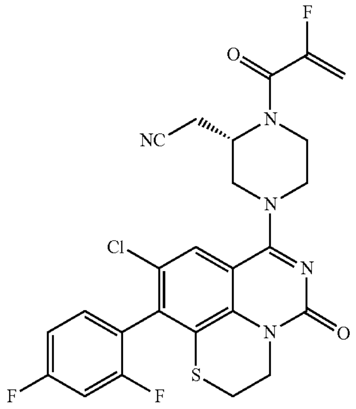 [SMILES: C=C(F)C(=O)N1CCN(c2nc(=O)n3c4c(c(-c5ccc(F)cc5F)c(Cl)cc24)SCC3)C[C@@H]1CC#N] | $^1$H NMR (400 MHz, DMSO) δ 7.85 (d, J = 15.6 Hz 1H), 7.54-7.36 (m, 2H), 7.29 (td, J = 8.5, 2.4 Hz, 1H), 5.42 (dd, J = 17.9, 4.0 Hz, 1H), 5.31 (d, J = 50.2 Hz, 1H), 4.88 (s, 1H), 4.45-4.35 (m, 1H), 4.26 (d, J = 13.8 Hz, 1H), 4.19 (d, J = 10.7 Hz, 2H), 3.93 (dd, J = 12.0, 8.8 Hz, 1H), 3.35-3.08 (m, 6H), 3.02 (dd, J = 17.1, 5.7 Hz, 1H). | 545.96 | 40.5 |

TABLE 2a-continued

| Summary of Examples | | | | | |
|---|---|---|---|---|---|
| Ex.# | Name | Structure | $^1$H NMR | MS | % CAF 10 uM @ 60 min |
| 177 | (S)-7-((2S,5R)-4-acryloyl-2,5-dimethylpiperazin-1-yl)-9-chloro-10-(2,4-difluorophenyl)-2,3-dihydro-5H-[1,4]thiazino[2,3,4-ij]quinazolin-5-one 1,1-dioxide | 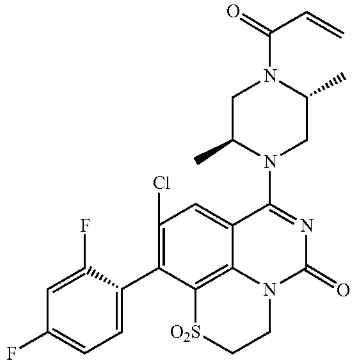 | $^1$H NMR (400 MHz, DMSO) δ 8.21-8.03 (m, 1H), 7.49-7.34 (m, 2H), 7.24 (td, J = 8.5, 2.3 Hz, 1H), 6.89-6.71 (m, 1H), 6.17 (dd, J = 16.7, 2.2 Hz, 1H), 5.74 (ddd, J = 10.4, 5.0, 2.2 Hz, 1H), 4.82-4.34 (m, 3H), 4.27-3.97 (m, 2H), 3.96-3.48 (m, 5H), 1.41-1.03 (m, 6H). | 548.99 | 93.5 |
| 178 | (R)-7-((2S,5R)-4-acryloyl-2,5-dimethylpiperazin-1-yl)-9-chloro-10-(2,4-difluorophenyl)-2,3-dihydro-5H-[1,4]thiazino[2,3,4-ij]quinazolin-5-one 1,1-dioxide | 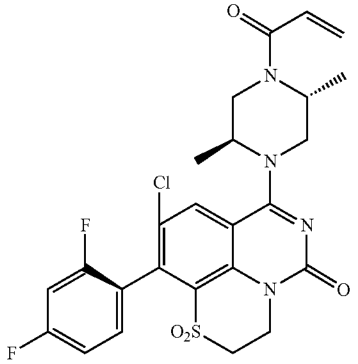 | $^1$H NMR (400 MHz, DMSO) δ 8.21-8.03 (m, 1H), 7.49-7.34 (m, 2H), 7.24 (td, J = 8.5, 2.3 Hz, 1H), 6.89-6.71 (m, 1H), 6.17 (dd, J = 16.7, 2.2 Hz, 1H), 5.74 (ddd, J = 10.4, 5.0, 2.2 Hz, 1H), 4.82-4.34 (m, 3H), 4.27-3.97 (m, 2H), 3.96-3.48 (m, 5H), 1.41-1.03 (m, 6H). | 548.99 | 58.3 |
| 179 | (S)-7-((S)-4-acryloyl-2-methylpiperazin-1-yl)-9-chloro-10-(2,4-difluorophenyl)-2,3-dihydro-5H-[1,4]thiazino[2,3,4-ij]quinazolin-5-one | 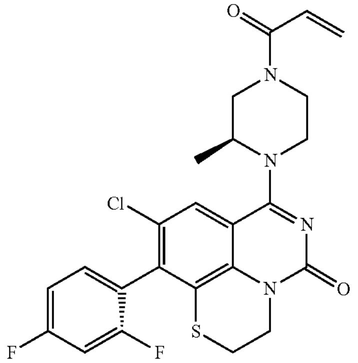 | 1H NMR (400 MHz, $CDCl_3$) δ 7.48 (s, 1H), 7.24-7.18 (m, 1H), 7.06-6.96 (m, 2H), 6.66-6.52 (m, 1H), 6.38 (dd, J = 16.8 Hz, 1.6 Hz, 1H), 5.78 (d, J = 10.8 Hz, 1H), 4.83-4.48 (m, 3H), 4.41-4.20 (m, 2H), 4.00-3.48 (m, 3H), 3.12-2.97 (m, 3H), 1.48-1.46 (m, 3H). | 502.96 | 96 |
| 180 | (R)-7-((S)-4-acryloyl-2-methylpiperazin-1-yl)-9-chloro-10-(2,4-difluorophenyl)-2,3-dihydro-5H-[1,4]thiazino[2,3,4-ij]quinazolin-5-one | 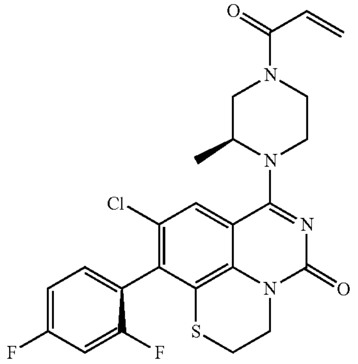 | 1H NMR (400 MHz, CDCl3) δ 7.48 (s, 1H), 7.23-7.17 (m, 1H), 7.06-6.96 (m, 2H), 6.66-6.51 (m, 1H), 6.38 (dd, J = 16.8 Hz, 1.6 Hz, 1H), 5.78 (d, J = 12.0 Hz, 1H) 4.95-4.45 (m, 3H), 4.34-3.98 (m, 3H), 3.80-3.47 (m, 2H), 3.17-2.91 (m, 3H), 1.39-1.38 (m, 3H). | 502.96 | 94.7 |

TABLE 2a-continued

Summary of Examples

| Ex.# | Name | Structure | $^1$H NMR | MS | % CAF 10 uM @ 60 min |
|---|---|---|---|---|---|
| 181 | 7-(5-acryloyl-2,5-diazabicyclo[2.2.2]octan-2-yl)-9-chloro-10-(2,4-difluorophenyl)-2,3-dihydro-5H-[1,4]thiazino[2,3,4-ij]quinazolin-5-one | 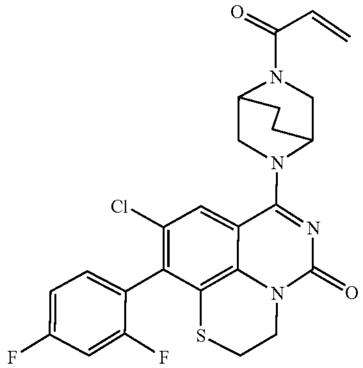 [SMILES: C=CC(=O)N1CC2CCC1CN2c1nc(=O)n2c3c(c(-c4ccc(F)cc4F)c(Cl)cc13)SCC2] | $^1$H NMR (400 MHz, MeOD) δ 7.84-7.69 (m, 1H), 7.20 (dtd, J = 10.5, 8.5, 6.3 Hz, 1H), 7.04 (qd, J = 6.8, 2.6 Hz, 2H), 6.60 (dddd, J = 44.5, 16.8, 10.5, 3.6 Hz, 1H), 6.27-6.13 (m, 1H), 5.77-5.62 (m, 1H), 4.93 (s, 1H), 4.70 (t, J = 2.9 Hz, 1H), 4.43 (ddt, J = 14.4, 6.1, 3.1 Hz, 1H), 4.23-3.63 (m, 5H), 3.14-2.98 (m, 2H), 2.37-2.21 (m, 1H), 2.04-1.77 (m, 3H) | 514.97 | 28.7 |
| 182 | 7-(9-acryloyl-3-oxa-7,9-diazabicyclo[3.3.1]nonan-7-yl)-9-chloro-10-(2,4-difluorophenyl)-2,3-dihydro-5H-[1,4]thiazino[2,3,4-ij]quinazolin-5-one | 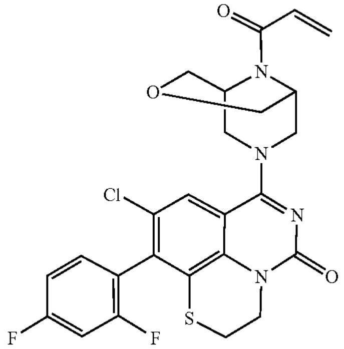 [SMILES: C=CC(=O)N1C2COCC1CN(c1nc(=O)n3c4c(c(-c5ccc(F)cc5F)c(Cl)cc14)SCC3)C2] | $^1$H NMR (400 MHz, MeOD) δ 7.65 (s, 1H), 7.20 (td, J = 8.5, 6.3 Hz, 1H), 7.09-6.98 (m, 2H), 6.72 (m, 1H), 6.25 (dd, J = 16.8, 1.9 Hz, 1H), 5.76 (dd, J = 10.5, 1.9 Hz, 1H), 4.92-4.80 (m, 1H), 4.71 (ddt, J = 16.8, 13.3, 1.9 Hz, 1H), 4.55-4.48 (m, 1H), 4.37-4.26 (m, 1H), 4.21 (s, 1H), 4.12-3.89 (m, 3H), 3.78-3.70 (m, 1H), 3.63 (m, 3H), 3.15-3.00 (m, 2H) | 530.97 | 94.4 |
| 183 | 7-((2S,5R)-4-acryloyl-2,5-dimethylpiperazin-1-yl)-9-chloro-10-(naphthalen-1-yl)-2,3-dihydro-5H-[1,4]thiazino[2,3,4-ij]quinazolin-5-one | 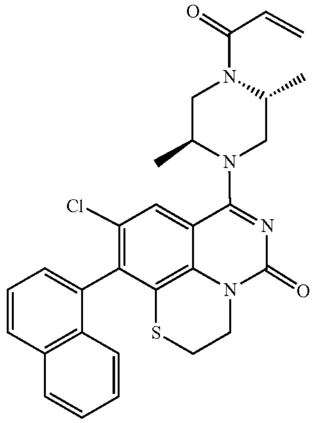 | $^1$H NMR (400 MHz, DMSO) δ 8.05 (t, J = 8.5 Hz, 2H), 7.72 (d, J = 4.5 Hz, 1H), 7.68-7.62 (m, 1H), 7.62-7.53 (m, 1H), 7.53-7.43 (m, 1H), 7.43-7.31 (m, 2H), 6.89-6.75 (m, 1H), 6.18 (dd, J = 16.6, 2.3 Hz, 1H), 5.80-5.69 (m, 1H), 4.82-4.40 (m, 2H), 4.40-4.08 (m, 2H), 4.08-3.38 (m, 4H), 3.21-2.94 (m, 2H), 1.37-1.12 (m, 6H). | 531.07 | 45.3 |
| 184 | 7-((2S,5R)-4-acryloyl-2,5-dimethylpiperazin-1-yl)-9-chloro-10-(2,4-difluorophenyl)-2,3-dihydro-5H-[1,4]thiazino[2,3,4-ij]quinazolin-5-one 1,1-dioxide | 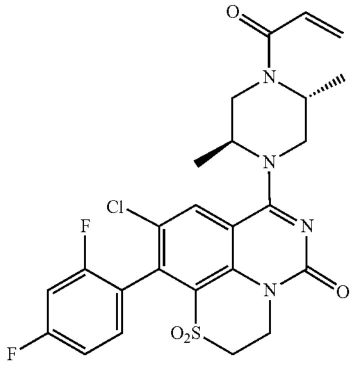 [SMILES: C=CC(=O)N1C[C@H](C)N(c2nc(=O)n3c4c(c(-c5ccc(F)cc5F)c(Cl)cc24)S(=O)(=O)CC3)C[C@H]1C] | $^1$H NMR (400 MHz, DMSO) δ 8.21-8.03 (m, 1H), 7.49-7.34 (m, 2H), 7.24 (td, J = 8.5, 2.3 Hz, 1H), 6.89-6.71 (m, 1H), 6.17 (dd, J = 16.7, 2.2 Hz, 1H), 5.74 (ddd, J = 10.4, 5.0, 2.2 Hz, 1H), 4.82-4.34 (m, 3H), 4.27-3.97 (m, 2H), 3.96-3.48 (m, 5H), 1.41-1.03 (m, 6H). | 548.99 | 91.4 |

TABLE 2a-continued

| Summary of Examples | | | | | |
|---|---|---|---|---|---|
| Ex.# | Name | Structure | $^1$H NMR | MS | % CAF 10 uM @ 60 min |
| 189 | 7-((2S,5R)-4-acryloyl-2,5-dimethylpiperazin-1-yl)-9-chloro-10-(2,4-difluorophenyl)-2,3-dihydro-5H-[1,4]thiazino[2,3,4-ij]quinazolin-5-one | 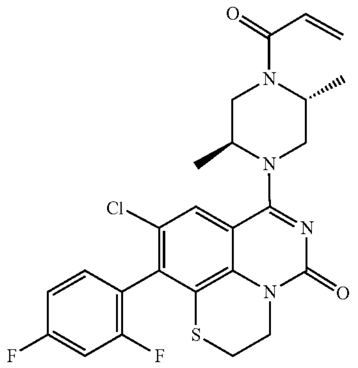 [SMILES: C=CC(=O)N1C[C@H](C)N(c2nc(=O)n3c4c(c(-c5ccc(F)cc5F)c(Cl)cc24)SCC3)C[C@H]1C] | $^1$H NMR (400 MHz, $CDCl_3$) δ 7.57-7.45 (m, 1H), 7.24-7.15 (m, 1H), 7.09-6.92 (m, 2H), 6.69-6.48 (m, 1H), 6.45-6.28 (m, 1H), 5.82-5.72 (m, 1H), 5.12-4.91 (m, 1H), 4.90-4.55 (m, 1H), 4.52-4.19 (m, 2H), 4.20-3.96 (m, 1H), 3.94-3.33 (m, 3H), 3.20-3.01 (m, 2H), 1.53-1.18 (m, 6H). | 516.99 | 93.8 |
| 190 | 7-((S)-4-acryloyl-2-methylpiperazin-1-yl)-9-chloro-10-(2,4-difluorophenyl)-2,3-dihydro-5H-[1,4]thiazino[2,3,4-ij]quinazolin-5-one 1,1-dioxide | 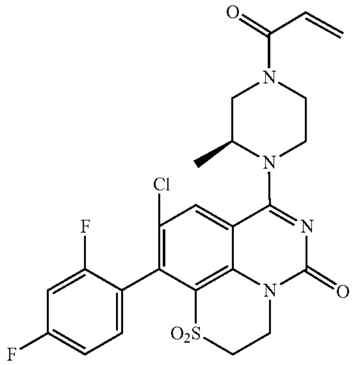 [SMILES: C=CC(=O)N1CCN(c2nc(=O)n3c4c(c(-c5ccc(F)cc5F)c(Cl)cc24)S(=O)(=O)CC3)[C@@H](C)C1] | $^1$H NMR (400 MHz, DMSO) δ: 7.88 (s, 1H), 7.30-7.40 (m, 1H), 6.94-7.08 (m, 2H), 6.49-6.19 (m, 1H), 6.39 (d, J = 16.8 Hz, 1H), 5.80 (d, J = 10.4 Hz, 1H), 4.49-5.10 (m, 1H), 4.10-4.48 (m, 4H), 2.80-4.10 (m, 6H), 1.39-1.50 (m, 3H). | 534.96 | 88.8 |
| 191 | 7-((S)-4-acryloyl-2-methylpiperazin-1-yl)-9-chloro-10-(2,4-difluorophenyl)-2,3-dihydro-5H-[1,4]thiazino[2,3,4-ij]quinazolin-5-one 1-oxide | 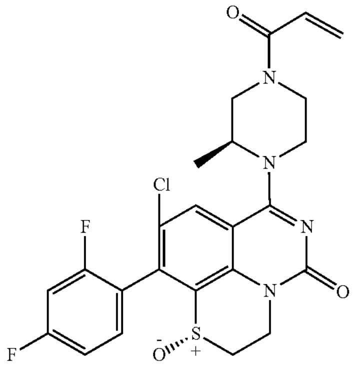 | $^1$H NMR (401 MHz, DMSO) δ: 7.89 (s, 1H), 7.11-7.20 (m, 1H), 7.03-7.10 (m, 2H), 6.49-6.19 (m, 1H), 6.39 (d, J = 16.4 Hz, 1H), 5.80 (d, J = 10.4 Hz, 1H), 4.38-5.20 (m, 3H), 3.30-4.30 (m, 6H), 2.78-3.35 (m, 2H), 1.39-1.42 (m, 3H). | 518.96 | 26.6 |
| 192 | 7-((S)-4-acryloyl-2-methylpiperazin-1-yl)-9-chloro-10-(2,4-difluorophenyl)-2,3-dihydro-5H-[1,4]thiazino[2,3,4-ij]quinazolin-5-one 1-oxide | 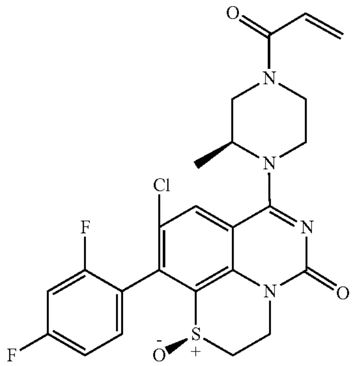 | $^1$H NMR (401 MHz, DMSO) δ: 7.90 (s, 1H), 7.47-7.55 (m, 1H), 6.98-7.18 (m, 2H), 6.49-6.19 (m, 1H), 6.39 (d, J = 16.4 Hz, 1H), 5.80 (d, J = 8.8 Hz, 1H), 4.40-5.20 (m, 3H), 3.35-4.35 (m, 6H), 2.78-3.33 (m, 2H), 1.39-1.41 (m, 3H). | 518.96 | 62.4 |

TABLE 2a-continued

Summary of Examples

| Ex.# | Name | Structure | $^1$H NMR | MS | % CAF 10 uM @ 60 min |
|---|---|---|---|---|---|
| 193 | 7-((S)-4-acryloyl-2-methylpiperazin-1-yl)-9-chloro-10-(2,4-difluorophenyl)-2,3-dihydro-5H-[1,4]thiazino[2,3,4-ij]quinazolin-5-one | 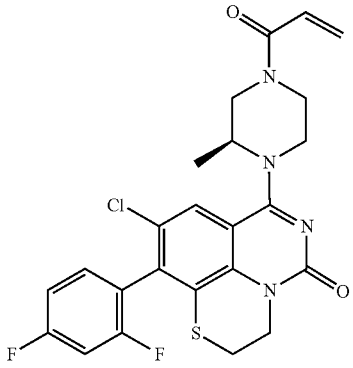 [SMILES: C=CC(=O)N1CCN(c2nc(=O)n3c4c(c(-c5ccc(F)cc5F)c(Cl)cc24)SCC3)[C@@H](C)C1] | $^1$H NMR (401 MHz, DMSO) δ: 7.48 (s, 1H), 7.16-7.23 (m, 1H), 6.95-7.08 (m, 2H), 6.48-6.69 (m, 1H), 6.38 (d, J-19.6 Hz, 1H), 5.78 (d, J = 10.0 Hz, 1H), 4.95-4.45 (m, 3H), 4.34-3.98 (m, 3H), 3.80-3.47 (m, 2H), 3.17-2.91 (m, 3H), 1.39-1.38 (m, 3H). | 502.96 | 97 |

Example 84: 7-(9-acryloyl-3,3-dioxido-3-thia-7,9-diazabicyclo[3.3.1]nonan-7-yl)-9-chloro-10-(2,4-difluorophenyl)-2,3-dihydro-5H-[1,4]thiazino[2,3,4-ij]quinazolin-5-one

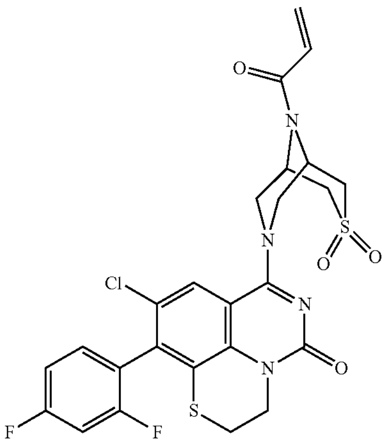 [SMILES: C=CC(=O)N1C2CN(c3nc(=O)n4c5c(c(-c6ccc(F)cc6F)c(Cl)cc35)SCC4)CC1CS(=O)(=O)C2]

Over a solution of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one (50 mg, 0.095 mmol) in dichloromethane (1 mL), triethylamine (54 mg, 0.57 mmol) and acryloyl chloride (17 mg, 0.19 mmol) were added at 0° C. The reaction mixture was stirred at room temperature for two hours. The solvent was removed in vacuo to obtain a residue that was purified by preparative HPLC to afford the desired product (9.2 mg, 15%) as an off-white solid.

m/z (ESI, +ve)=579.0 $(M+H)^+$.

$^1$H NMR (400 MHz, DMSO) δ 7.95 (s, 1H), 7.52-7.44 (m, 1H), 7.41-7.38 (m, 1H), 7.29-7.25 (m, 1H), 6.45-6.41 (m, 1H), 6.29-6.25 (m, 1H), 6.03 (d, J=12 Hz, 1H), 4.60-4.53 (m, 2H), 4.245-4.23 (m, 1H), 4.03-3.88 (m, 3H), 3.65-3.55 (m, 2H), 3.52-3.47 (m, 1H), 3.23-3.05 (m, 3H), 2.73 (s, 2H)

Step 1: N,N-dibromobenzenesulfonamide

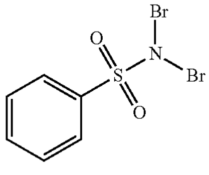 [SMILES: O=S(=O)(c1ccccc1)N(Br)Br]

A solution of benzenesulfonamide (100 g, 0.6362 mol) and KOH (103 g, 1.8357 mol) in water (700 mL) was stirred at room temperature for 30 min. Bromine (91 mL, 1.7766 mol) was added dropwise and the mixture stirred for 16 hours. The reaction was filtered and the solid was washed with water and dried under reduced pressure to afford N,N-dibromobenzenesulfonamide (240 g) as a yellow solid.

Step 2: diethyl 3,3'-((phenylsulfonyl)azanediyl)bis(2-bromopropanoate)

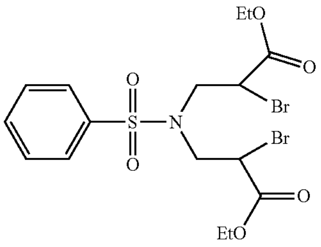 [SMILES: CCOC(=O)C(Br)CN(CC(Br)C(=O)OCC)S(=O)(=O)c1ccccc1]

Ethyl prop-2-enoate (119.2 g, 1.19 mol) was added to a solution of N,N-dibromobenzenesulfonamide (75 g, 0.24 mol) in dichloromethane (500 mL) at room temperature. The mixture was stirred at 45° C. under light for 4 hours. Volatiles were removed under reduced pressure and the crude material purified by silica gel column chromatography (ethyl acetate/hexanes=0-12%) to afford diethyl 3,3'-((phenylsulfonyl)azanediyl)bis(2-bromopropanoate) as a white solid.

m/z (ESI, +ve)=515.9/517.9 $(M+H)^+$.

Step 3: di ethyl-1-benzyl-4-(phenyl sulfonyl)piperazine-cis-2,6-dicarboxylate

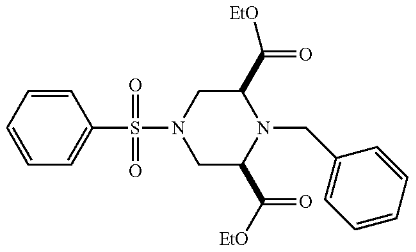 [SMILES: CCOC(=O)[C@H]1CN(S(=O)(=O)c2ccccc2)C[C@@H](C(=O)OCC)N1Cc1ccccc1]

To a solution of diethyl 3,3'-((phenylsulfonyl)azanediyl) bis(2-bromopropanoate) (50 g, 0.0970 mol) in toluene (150 mL) was added phenylmethanamine (52 g, 0.4853 mol). After stirring at 90° C. for 5 h, the mixture was cooled to room temperature and filtered. The filtrate was concentrated to afford a residue that was purified by silica gel chromatography (ethyl acetate/hexanes, 0-20%) to afford the desired product (26 g) as a white solid.

$^1$H NMR (400 MHz, $CDCl_3$) δ 7.78-7.74 (m, 2H), 7.65-7.60 (m, 1H), 7.56-7.52 (m, 2H), 7.30-7.20 (m, 5H), 4.03 (q, J=7.2 Hz, 4H), 3.93 (s, 2H), 3.42-3.38 (m, 2H), 3.36-3.31 (m, 2H), 3.18-3.13 (m, 2H), 1.23 (t, J=7.2 Hz, 6H).

Step 4: Cis-(1-benzyl-4-(phenylsulfonyl)piperazine-2,6-diyl)dimethanol

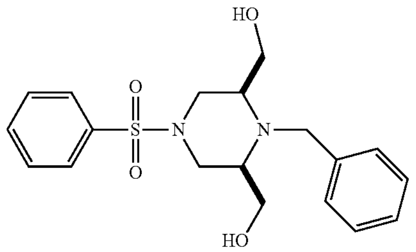 [SMILES: O=S(=O)(c1ccccc1)N1C[C@@H](CO)N(Cc2ccccc2)[C@@H](CO)C1]

To a solution of diethyl-1-benzyl-4-(phenylsulfonyl)piperazine-cis-2,6-dicarboxylate (20 g, 0.0434 mol) in THF (150 mL) was slowly added lithium aluminum hydride (5.8 g, 0.1528 mol) at 0° C. under nitrogen atmosphere. After stirring at 25° C. for 4 h, the mixture was quenched with water (6 mL) and diluted with $Na_2CO_3$ (1 L). The mixture was extracted with ethyl acetate (500 mL×4). The combined organic layer was washed with brine (500 mL), dried over $Na_2SO_4$ and concentrated under reduced pressure. The residue was dried by evaporation under reduced pressure to afford 4-(benzenesulfonyl)-1-benzyl-cis-[2,6-(hydroxymethyl)piperazin-2-yl]methanol (32.8 g) as a white solid.

$^1$H NMR (400 MHz, $CDCl_3$) δ 7.78-7.75 (m, 2H), 7.66-7.61 (m, 1H), 7.58-7.54 (m, 2H), 7.35-7.22 (m, 5H), 3.85 (s, 2H), 3.73-3.66 (m, 2H), 3.61-3.55 (m, 2H), 3.28-3.22 (m, 2H), 2.95-2.90 (m, 4H), 2.03 (m, 2H).

Step 5: 1-benzyl-cis-(2,6-bis(chloromethyl))-4-(phenylsulfonyl)piperazine

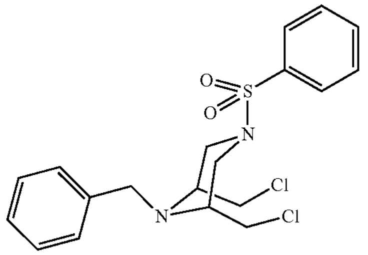 [SMILES: O=S(=O)(c1ccccc1)N1CC(CCl)N(Cc2ccccc2)C(CCl)C1]

To a solution of Cis-(1-benzyl-4-(phenylsulfonyl)piperazine-2,6-diyl)dimethanol (32.8 g, 0.0871 mol) in DMF (150 mL) was added thionyl chloride (32 mL, 0.4411) dropwise at 0° C. under nitrogen atmosphere. After stirring at room temperature for 4 hours, saturated aqueous sodium carbonate (900 mL) was added at 0° C. The mixture was extracted with ethyl acetate (500 mL×5) and the combined organic layers washed with water (500 mL×5), brine (500 mL), dried over $Na_2SO_4$ and concentrated under reduced pressure to afford the desired final product as a white solid.

$^1$H NMR (400 MHz, $CDCl_3$) δ 7.81-7.78 (m, 2H), 7.65-7.62 (m, 1H), 7.59-7.54 (m, 2H), 7.35-7.20 (m, 5H), 3.89 (s, 2H), 3.74-3.70 (m, 2H), 3.58-3.54 (m, 2H), 3.49-3.43 (m, 2H), 3.05-3.01 (m, 2H), 2.67-2.62 (m, 2H).

Step 6: 9-benzyl-7-(phenylsulfonyl)-3-thia-7,9-diazabicyclo[3.3.1]nonane

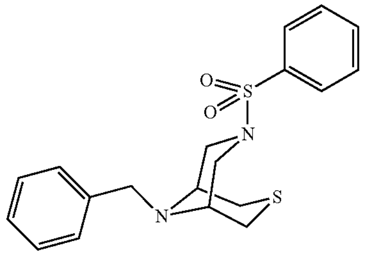 [SMILES: O=S(=O)(c1ccccc1)N1CC2CSCC(C1)N2Cc1ccccc1]

A mixture of 1-benzyl-cis-(2,6-bis(chloromethyl))-4-(phenylsulfonyl)piperazine 0.01 mol) and $Na_2S$ (4.7 g, 0.06 mol) in EtOH (30 mL) was stirred at 80° C. for 16 hours. The mixture was cooled to room temperature, concentrated and the resulting residue was taken up in water (100 mL) and extracted with ethyl acetate (50 mL×4). The combined organic layers were washed with brine (50 mL), dried over $Na_2SO_4$ and concentrated under reduced pressure. The crude material was purified by silica gel column (ethyl acetate: hexanes=0-20%) to afford 7-(benzenesulfonyl)-9-benzyl-3-thia-7,9-diazabicyclo[3.3.1]nonane (2.1 g) as a yellow solid.

$^1$H NMR (400 MHz, $CDCl_3$) δ7.82-7.79 (m, 2H), 7.62-7.53 (m, 3H), 7.29-7.23 (m, 5H), 3.89 (s, 2H), 3.77-3.72 (m, 2H), 3.44-3.39 (m, 2H), 3.03-2.98 (m, 4H), 2.30-2.26 (m, 2H).

Step 7: tert-butyl-9-benzyl-3-thia-7,9-diazabicyclo [3.3.1]nonane-7-carboxylate

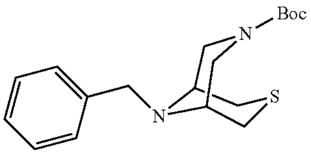 [SMILES: CC(C)(C)OC(=O)N1CC2CSCC(C1)N2Cc1ccccc1]

To a solution of 9-benzyl-7-(phenylsulfonyl)-3-thia-7,9-diazabicyclo[3.3.1]nonane (500 mg, 1.3 mmol) in THF (10 mL) was added $KPPh_2$ (0.5 M, 6.6 mL, 3.3 mmol) dropwise at −78° C. under nitrogen atmosphere. The solution was stirred at −78° C. for 3 hours and quenched with HCl (2 M, 5.2 mL, 10.4 mmol) followed by NaOH (2 M, 10.5 mL, 21 mmol). Boc anhydride (728 mg, 3.34 mmol) was added and the mixture was stirred at room temperature for 16 hours. The reaction was quenched with water (50 mL) and extracted with ethyl acetate (30 mL×3). The combined organic layers were washed with brine (30 mL) and concentrated to get a residue which was purified with preparative thin layer chromatography (ethyl acetate:hexanes=1:4, Rf=0.5) to afford tert-butyl 9-benzyl-3-thia-7,9-diazabicyclo [3.3.1]nonane-7-carboxylate (270 mg) as yellow solid.

$^1H$ NMR (400 MHz, $CDCl_3$) δ 7.38-7.25 (m, 5H), 4.23-1.18 (m, 1H), 4.10-4.05 (m, 1H), 3.95 (s, 2H), 3.48-3.32 (m, 4H), 2.88-2.83 (m, 2H), 2.31-2.26 (m, 1H), 2.19-2.13 (m, 1H), 1.49 (s, 9H).

Step 8: tert-butyl-9-benzyl-3-thia-7,9-diazabicyclo [3.3.1]nonane-7-carboxylate 3,3-dioxide

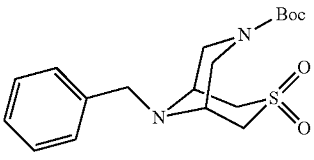 [SMILES: CC(C)(C)OC(=O)N1CC2CS(=O)(=O)CC(C1)N2Cc1ccccc1]

To a solution of tert-butyl-9-benzyl-3-thia-7,9-diazabicyclo[3.3.1]nonane-7-carboxylate (1 g, 3.0 mmol) in dichloromethane (20 ml) was added 3-chloroperoxybenzoic acid (1.29 g, 7.5 mmol) at 0° C. The reaction mixture was stirred at room temperature for 30 minutes and quenched with saturated $Na_2S_2O_3$ (50 mL) and extracted with dichloromethane (30 mL×3). The organic layers were combined, washed with brine (20 mL), dried over sodium sulphate and concentrated. The resulting residue was purified by silica gel chromatography to afford tert-butyl-9-benzyl-3-thia-7,9-diazabicyclo[3.3.1]nonane-7-carboxylate 3,3-dioxide (0.9 g, 90%) as a light yellow solid.

m/z (ESI, +ve)=367.1 $(M+H)^+$.

Step 9: tert-butyl-3-thia-7,9-diazabicyclo[3.3.1] nonane-7-carboxylate 3,3-dioxide

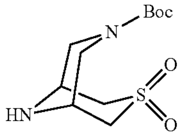 [SMILES: CC(C)(C)OC(=O)N1CC2CS(=O)(=O)CC(C1)N2]

A solution tert-butyl-9-benzyl-3-thia-7,9-diazabicyclo [3.3.1]nonane-7-carboxylate 3,3-dioxide (2.5 g, 0.27 mmol) $Pd/Ba_2SO_4$ (7.78 g) and HCl (5 drops) in methanol (30 mL) was hydrogenated at room temperature for 2 hours. The mixture was filtered and concentrated to afford tert-butyl-3-thia-7,9-diazabicyclo[3.3.1]nonane-7-carboxylate 3,3-dioxide (1.3 g, 72%) as a white solid after purification by flash chromatography.

m/z (ESI, +ve)=277.1 $(M+H)^+$.

Step 10: 3-thia-7,9-diazabicyclo[3.3.1]nonane 3,3-dioxide

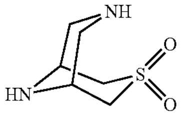 [SMILES: O=S1(=O)CC2CNCC(C1)N2]

A solution of tert-butyl-3-thia-7,9-diazabicyclo[3.3.1] nonane-7-carboxylate 3,3-dioxide (1.2 g) in dichloromethane/trifluoroacetic acid (5/1, 20 mL) was stirred at room temperature for 4 hours. The solution was concentrated and the resulting residue purified by reversed phase chromatography to afford 3-thia-7,9-diazabicyclo[3.3.1]nonane 3,3-dioxide (620 mg) as a white solid.

m/z (ESI, +ve)=177.1 $(M+H)^+$.

Step 11: methyl 2-amino-4-bromobenzoate

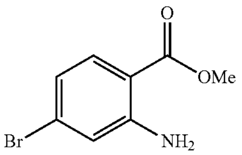 [SMILES: COC(=O)c1ccc(Br)cc1N]

A solution of 2-amino-4-bromobenzoic acid (100 g, 0.4628 mol) in thionyl chloride (400 mL) was stirred at 80° C. for 2 hours. The mixture was cooled to room temperature and concentrated under reduced pressure. The residue was dissolved in dichloromethane (500 mL) and cooled down to 0° C. Methanol (200 ml) was added and the mixture stirred at 0° C. for 1 hour. After that time, the reaction was quenched with saturated aqueous $NaHCO_3$ (400 mL) and extracted with dichloromethane (300 mL×3). The combined organic layers were washed with brine (300 mL), dried over sodium sulphate and concentrated to afford methyl 2-amino-4-bromobenzoate (100 g, 80%) as a yellowish green solid.

m/z (ESI, +ve)=230.0 $(M+H)^+$.

Step 12: methyl 2-acetamido-4-bromobenzoate

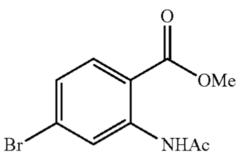 [SMILES: COC(=O)c1ccc(Br)cc1NC(C)=O]

To a solution of methyl 2-amino-4-bromobenzoate (60 g, 0.26 mol) in acetic acid (300 mL) at room temperature, was added acetic anhydride (26.6 g, 0.2608 mol). The mixture was stirred at 100° C. for 2 hours and cooled down to room temperature. Water was added (400 mL) and the resulting suspension was filtered to afford methyl 2-acetamido-4-bromobenzoate (58 g) as a yellow solid.

m/z (ESI, +ve)=272.0 $(M+H)^+$.

$^1$H NMR (400 MHz, DMSO) δ 10.63 (s, 1H), 8.53 (s, 1H), 7.83 (d, J=8.0 Hz, 1H), 7.39 (dd, J=8.0, 2.0, 1H), 3.86 (s, 3H), 2.15 (s, 3H).

Step 13: methyl 2-acetamido-4-bromo-5-chlorobenzoate

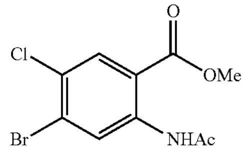 [SMILES: COC(=O)c1cc(Cl)c(Br)cc1NC(C)=O]

To a solution of methyl 2-acetamido-4-bromobenzoate (58 g, 0.21 mol) in DMF (250 mL), was added N-chlorosuccinimide (28.48 g, 0.21 mol) at room temperature. The mixture was stirred at 85° C. for 16 hours, diluted with water (250 mL) and extracted with ethyl acetate (250 mL×3). The combined organic layers were washed with brine (200 mL×4), dried over $Na_2SO_4$, filtered and concentrated to give a yellow oil which was purified by flash chromatography with ethyl acetate in hexanes (50-100%). The resulting material was dissolved in DMF (250 mL) and N-chlorosuccinimide (14.2 g, 0.1067 mol) was added. The mixture was stirred at 85° C. for 3 hours and quenched with water (250 mL). The solution was extracted with ethyl acetate (250 mL×3) and the combined organic layers were washed with brine (200 mL×4), dried over $Na_2SO_4$, filtered and concentrated to afford a residue that was purified by silica gel chromatography (ethyl acetate:hexanes=0-55%) to afford methyl 2-acetamido-4-bromo-5-chlorobenzoate (47 g, 72%) as a yellow solid.

m/z (ESI, +ve)=305.9 $(M+H)^+$.

Step 14: methyl 2-amino-4-bromo-5-chlorobenzoate

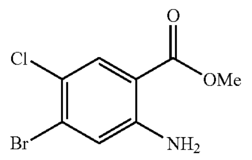 [SMILES: COC(=O)c1cc(Cl)c(Br)cc1N]

Methyl 4-bromo-5-chloro-2-acetamidobenzoate (47 g, 0.15 mol) was dissolved in a methanolic solution of HCl (5M, 500 mL) and the mixture stirred at 80° C. for 2 hours. The reaction was diluted with water (500 mL) and filtered to afford methyl 2-amino-4-bromo-5-chlorobenzoate (crude, 39 g, 90%) as a white solid.

m/z (ESI, +ve)=263.9 $(M+H)^+$.

Step 15: methyl 5-amino-2-chloro-2',4'-difluoro-[1,1'-biphenyl]-4-carboxylate

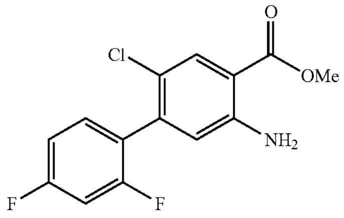 [SMILES: COC(=O)c1cc(Cl)c(-c2ccc(F)cc2F)cc1N]

To a mixture of methyl 2-amino-4-bromo-5-chlorobenzoate (39 g, 0.15 mol) in dioxane/$H_2O$ (240 mL) were added (2,4-difluorophenyl)boronic acid (23.69 g, 0.15 mol), 1,1'-bis(diphenylphosphino)ferrocene palladium dichloride (21.95 g, 0.03 mol) and $Cs_2CO_3$ (146.62 g, 0.45 mol). The mixture was stirred at 100° C. for 10 hours, quenched with $H_2O$ (200 mL) and extracted with ethyl acetate (100 mL×3). The combined organic layers were washed with brine (200 mL), dried over sodium sulphate and concentrated to afford a crude material that was purified by silica gel chromatography to afford methyl 5-amino-2-chloro-2',4'-difluoro-[1,1'-biphenyl]-4-carboxylate (27.1 g, 61%) as a yellow solid.

m/z (ESI, +ve)=298.1 $(M+H)^+$.

$^1$H NMR (400 MHz, DMSO) δ 7.78 (s, 1H), 7.47-7.36 (m, 2H), 7.23-7.18 (m, 1H), 6.85 (s, 2H), 6.82 (s, 1H), 3.83 (s, 3H).

Step 16: methyl 3-amino-6-chloro-2',4'-difluoro-2-iodo-[1,1'-biphenyl]-4-carboxylate

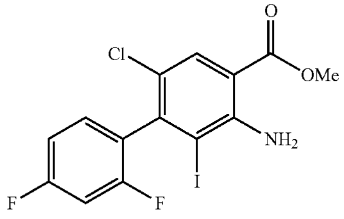 [SMILES: COC(=O)c1cc(Cl)c(-c2ccc(F)cc2F)c(I)c1N]

To a solution of methyl 5-amino-2-chloro-2',4'-difluoro-[1,1'-biphenyl]-4-carboxylate (27.1 g, 90.9 mmol) in AcOH (240 mL) was added N-iodosuccinamide (22.4 g, 99.5 mmol). The mixture was stirred at room temperature for 2 hours. The volatiles were removed under reduced pressure and the resulting residue was dissolved in ethyl acetate (30 mL) and washed with saturated aqueous $Na_2S_2O_3$ (20 mL×3), brine (20 mL×3), dried with $Na_2SO_4$ and filtered. The filtrate was concentrated and the crude material triturated in ethyl acetate (15 mL). The solid was collected by filtration and dried to afford methyl 3-amino-6-chloro-2',4'-difluoro-2-iodo-[1,1'-biphenyl]-4-carboxylate (22.1 g, 57%) as an off-white solid.

$^1$H NMR (400 MHz, DMSO) δ 7.92 (s, 1H), 7.46-7.40 (m, 1H), 7.34-7.22 (m, 2H), 6.92 (s, 2H), 3.87 (s, 3H).

Step 17: 3-amino-6-chloro-2',4'-difluoro-2-iodo-[1, 1'-biphenyl]-4-carboxylic acid

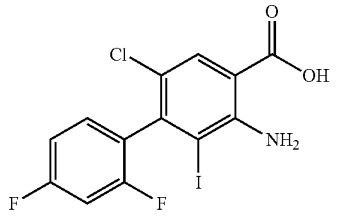 [SMILES: Nc1c(C(=O)O)cc(Cl)c(-c2ccc(F)cc2F)c1I]

To a solution of methyl 3-amino-6-chloro-2',4'-difluoro-2-iodo-[1,1'-biphenyl]-4-carboxylate (22.1 g, 52.1 mmol) in THF/methanol/water (75/75/35 mL) was added NaOH (21 g, 0.525 mol). The mixture was stirred at room temperature for 16 hours. The organic solvents were removed and the residue was acidified to pH=4-5 by addition of 5 M HCl and extracted with ethyl acetate (300 mL×3). The combined organic layers were washed with brine (200 mL), dried over $Na_2SO_4$ and concentrated to afford 3-amino-6-chloro-2',4'-difluoro-2-iodo-[1,1'-biphenyl]-4-carboxylic acid (20 g, 99%) as a yellow solid.

$^1$H NMR (400 MHz, DMSO) δ 7.92 (s, 1H), 7.43-7.19 (m, 5H).

Step 18: 6-chloro-7-(2,4-difluorophenyl)-8-iodoquinazoline-2,4(1H,3H)-dione

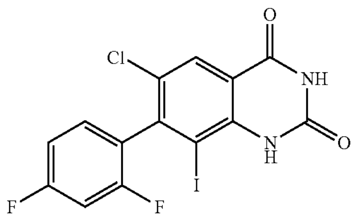

A mixture of 3-amino-6-chloro-2',4'-difluoro-2-iodo-[1, 1'-biphenyl]-4-carboxylic acid (20 g, 48.8 mmol) and urea (350 g, 5.8 mol) was stirred at 200° C. for 2 hours. The solid was taken up in ethyl acetate (4×500 mL) and washed with water (500 mL) and brine (300 mL). The organic layer was dried over $Na_2SO_4$, concentrated and the residue purified by silica gel chromatography (dichloromethane:methanol=9:1) to afford 6-chloro-7-(2,4-difluorophenyl)-8-iodoquinazoline-2,4(1H,3H)-dione (14 g, 66%) as a white solid.

$^1$H NMR (400 MHz, DMSO) δ 11.77 (s, 1H), 9.60 (s, 1H), 8.04 (s, 1H), 7.51-7.45 (m, 1H), 7.32-7.22 (m, 2H), 6.79 (s, 2H).

Step 19: 6-chloro-7-(2,4-difluorophenyl)-8-((2-hydroxyethyl)thio)quinazoline-2,4(1H,3H)-dione

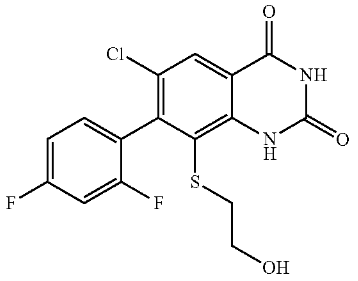 [SMILES: O=c1[nH]c(=O)c2cc(Cl)c(-c3ccc(F)cc3F)c(SCCO)c2[nH]1]

To a mixture of 6-chloro-7-(2,4-difluorophenyl)-8-iodoquinazoline-2,4(1H,3H)-dione (5 g, 11.5 mmol), CuI (437 mg, 2.3 mmol) and $K_2CO_3$ (4.8 g, 34.8 mmol) in isopropyl alcohol:ethylene glycol (100 mL:50 mL) was added 2-mercaptoethan-1-ol (3 mL, 38.5 mmol) at room temperature. The mixture was stirred at 90° C. for 16 hours. The reaction mixture was concentrated and the residue purified by reversed phase chromatography to afford 6-chloro-7-(2,4-difluorophenyl)-8-((2-hydroxyethyl)thio)quinazoline-2,4(1H,3H)-dione (3.2 g, 72%) as a white solid.

$^1$H NMR (400 MHz, DMSO) δ 11.73 (s, 1H), 10.33 (s, 1H), 8.06 (s, 1H), 7.45-7.38 (m, 2H), 7.28-7.22 (m, 1H), 5.37 (t, J=4.8 Hz, 1H), 3.38-3.36 (m, 2H), 2.65-2.61 (m, 2H).

Step 20: 9-chloro-10-(2,4-difluorophenyl)-2,3-dihydro-5H-[1,4]thiazino[2,3,4-ij]quinazoline-5,7(6H)-dione

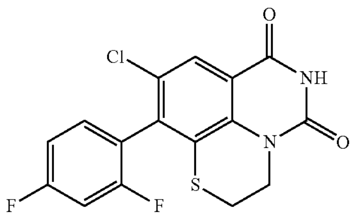 [SMILES: O=c1[nH]c(=O)n2c3c(c(-c4ccc(F)cc4F)c(Cl)cc13)SCC2]

To a solution of triphenylphosphine (4.6 g, 17.7 mmol) in THF (50 mL) was added DIAD (3.6 g, 17.7 mmol) at 0° C. under nitrogen atmosphere and the mixture stirred at 0° C. for 20 minutes. 6-chloro-7-(2,4-difluorophenyl)-8-((2-hydroxyethyl)thio)quinazoline-2,4(1H,3H)-dione (3.4 g, 8.83 mmol) was added and the reaction mixture was stirred at room temperature for 16 hours. The mixture was concentrated and the crude material purified by reversed phase chromatography to afford 9-chloro-10-(2,4-difluorophenyl)-2,3-dihydro-5H-[1,4]thiazino[2,3,4-ij]quinazoline-5,7(6H)-dione (1.6 g, 49%) as a white solid.

m/z (ESI, +ve)=367.0 $(M+H)^+$.

$^1$H NMR (400 MHz, DMSO-$d_6$) δ 11.90 (s, 1H), 7.86 (s, 1H), 7.51-7.46 (m, 1H), 7.41-7.35 (m, 1H), 7.30-7.25 (m, 1H), 4.39-4.33 (m, 1H), 4.10-4.03 (m, 1H), 3.20-3.10 (m, 2H).

Step 21: 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one

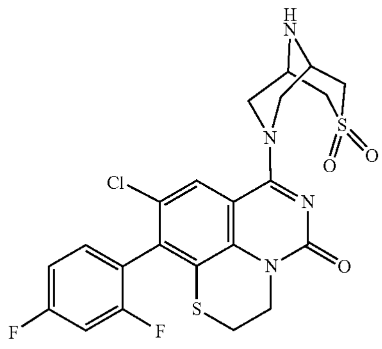 [SMILES: O=c1nc(N2CC3CS(=O)(=O)CC(C2)N3)c2cc(Cl)c(-c3ccc(F)cc3F)c3c2n1CCS3]

To a solution of 9-chloro-10-(2,4-difluorophenyl)-2,3-dihydro-5H-[1,4]thiazino[2,3,4-ij]quinazoline-5,7(6H)-dione (300 mg, 0.82 mmol) in toluene (5 mL) were added N,N-diisopropylethylamine (634 mg, 4.9 mmol) and $POCl_3$ (5 mL). The reaction mixture was stirred at 120° C. for 1.5 hours. The reaction mixture was concentrated and the residue redissolved in dichloroethane (5 mL) and added slowly over a solution of 3-thia-7,9-diazabicyclo[3.3.1]nonane 3,3-dioxide (577 mg, 3.27 mmol) and N,N-diisopropylethylamine (634 mg, 4.9 mmol) in dichloroethane (5 mL) at 0° C. The reaction mixture was stirred at room temperature for 1 hour, concentrated and the crude residue purified by preparative thin layer chromatography to afford 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one (150 mg, 34%) as a yellow solid.

m/z (ESI, +ve)=525.0 $(M+H)^+$.

$^1H$ NMR (400 MHz, DMSO) δ 8.76-8.71 (m, 1H), 7.94-7.89 (m, 1H), 7.50-7.45 (m, 1H), 7.41-7.38 (m, 1H), 7.29-7.25 (m, 1H), 4.53-4.40 (m, 1H), 4.26-4.21 (m, 1H), 4.18-4.05 (m, 1H), 4.00-3.90 (m, 2H), 3.62-3.48 (m, 5H), 3.24-3.08 (m, 4H), 3.00-2.85 (m, 1H).

Example 100: 7-(4-acryloyl-6,6-dioxidohexahydrothieno[3,4-b]pyrazin-1(2H)-yl)-10-(2,4-difluorophenyl)-9-(trifluoromethyl)-2,3-dihydro-5H-[1,4]thiazino[2,3,4-ij]quinazolin-5-one

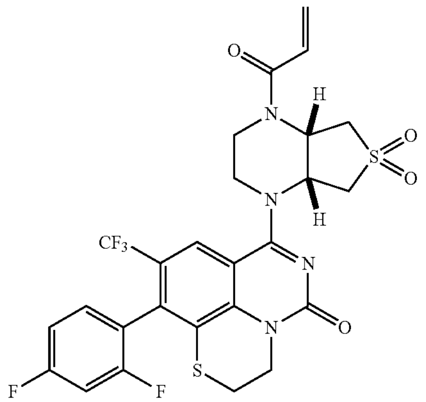

-continued

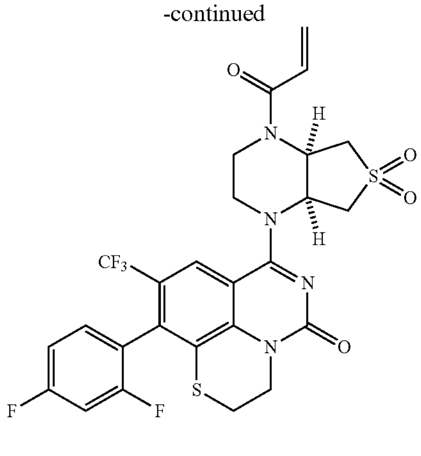

The title compound was prepared analogously to Example 84 where 10-(2,4-difluorophenyl)-7-(6,6-dioxidohexahydrothieno[3,4-b]pyrazin-1(2H)-yl)-9-(trifluoromethyl)-2,3-dihydro-5H-[1,4]thiazino[2,3,4-ij]quinazolin-5-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one.

m/z (ESI, +ve)=613.0 $(M+H)^+$.

Step 1: methyl 3-amino-2',4'-difluoro-[1,1'-biphenyl]-4-carboxylate

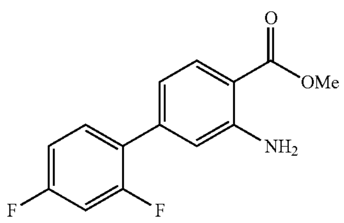 [SMILES: COC(=O)c1ccc(-c2ccc(F)cc2F)cc1N]

A solution of methyl 2-amino-4-bromobenzoate (11 g, 0.0478 mol) (2,4-difluorophenyl)boronic acid (8.3 g, 0.052 mol), 1,1'-bis(diphenylphosphino)ferrocene palladium dichloride (7.0 g, 0.0095 mol) and $Cs_2CO_3$ (46.7 g, 0.1434 mol) in dioxane:$H_2O$ (4:1, 220 mL) was stirred at 100° C. for 16 hours. The reaction was cooled to room temperature, diluted with water (100 mL) and extracted with ethyl acetate (3×100 mL). The organic layers were combined and washed with brine (200 mL), dried over $Na_2SO_4$ and concentrated. The residue was purified by silica gel chromatography to afford methyl 3-amino-2',4'-difluoro-[1,1'-biphenyl]-4-carboxylate (11 g, 86%) as a light yellow solid.

m/z (ESI, +ve)=264.1 $(M+H)^+$.

Step 2: methyl 5-amino-2',4'-difluoro-2-iodo-[1,1'-biphenyl]-4-carboxylate

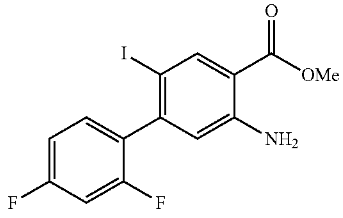 [SMILES: COC(=O)c1cc(I)c(-c2ccc(F)cc2F)cc1N]

A solution of methyl 3-amino-2',4'-difluoro-[1,1'-biphenyl]-4-carboxylate (11.7 g, 0.044 mol) and N-iodosuccinimide (10 g, 0.044 mmol) in DMF (100 mL) was stirred at room temperature for 16 hours. The solution was diluted with water (500 mL) and extracted with ethyl acetate (3×100 mL). The organic layer was washed with brine (300 mL), dried over $Na_2SO_4$ and concentrated to yield a residue that was purified by silica gel chromatography affording methyl 5-amino-2',4'-difluoro-2-iodo-[1,1'-biphenyl]-4-carboxylate (15.4 g, 89%) as a yellow solid.

m/z (ESI, +ve)=390.0 $(M+H)^+$.

Step 3: methyl 5-acetamido-2',4'-difluoro-2-iodo-[1,1'-biphenyl]-4-carboxylate

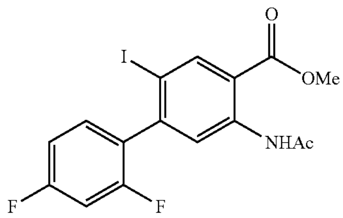 [SMILES: COC(=O)c1cc(I)c(-c2ccc(F)cc2F)cc1NC(C)=O]

To a solution of methyl 2-amino-4-(2,4-difluorophenyl)-5-iodobenzoate (22 g, 0.0565 mol) in AcOH (40 mL) was added acetic anhydride (5.77 g, 0.0565 mol), the mixture was stirred at 100° C. for 2 h. The mixture was quenched with water (1000 mL) and filtered, the filter cake was collected and dried under reduced pressure to afford methyl 5-acetamido-2',4'-difluoro-2-iodo-[1,1'-biphenyl]-4-carboxylate (5.26 g, 70%) as a white solid.

$^1H$ NMR (400 MHz, DMSO-d6) δ10.54 (s, 1H), 8.36 (s, 1H), 8.19 (s, 1H), 7.46-7.41 (m, 2H), 7.25-7.20 (m, 1H), 3.93 (s, 3H), 2.18 (s, 3H).

Step 4: methyl 5-acetamido-2',4'-difluoro-2-(trifluoromethyl)-[1,1'-biphenyl]-4-carboxylate

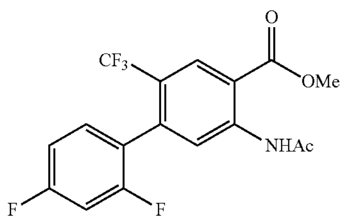 [SMILES: COC(=O)c1cc(C(F)(F)F)c(-c2ccc(F)cc2F)cc1NC(C)=O]

A solution of methyl 4-(2,4-difluorophenyl)-2-acetamido-5-iodobenzoate (8.7 mg, 20.2 mmol), copper(I) iodide (5.4 g, 28.4 mmol) and tetrabutylammonium iodide (3.7 g, 10.0 mmol) in HMPA (60 mL) was stirred at 90° C. for 20 minutes. Methyl 2,2-difluoro-2-(fluorosulfonyl)acetate (29 g, 151.0 mmol) was added and the resulting mixture stirred at 90° C. for 16 hours. The solution was cooled to room temperature, diluted with water (150 mL), extracted with ethyl acetate (3×150 mL) and the organic layers washed with brine (100 mL), dried over $Na_2SO_4$ and concentrated to afford a residue which was purified by silica gel chromatography (ethyl acetate:hexanes=0-25%). 5-acetamido-2',4'-difluoro-2-(trifluoromethyl)[1,1'-biphenyl]-4-carboxylate was isolated as a yellow solid in 70% yield.

$^1H$ NMR (400 MHz, DMSO-d6) δ10.81 (s, 1H), 8.33 (s, 1H), 8.26 (s, 1H), 7.46-7.41 (m, 2H), 7.25-7.20 (m, 1H), 3.93 (s, 3H), 2.18 (s, 3H).

Step 5: methyl 5-amino-2',4'-difluoro-2-(trifluoromethyl)-[1,1'-biphenyl]-4-carboxylate

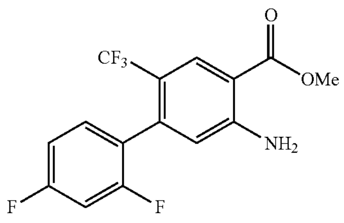 [SMILES: COC(=O)c1cc(C(F)(F)F)c(-c2ccc(F)cc2F)cc1N]

A solution of methyl 5-acetamido-2',4'-difluoro-2-(trifluoromethyl)-[1,1'-biphenyl]-4-carboxylate (5.26 g, 14.1 mmol) in a methanolic solution of HCl (100 mL) was stirred at 80° C. for 2 hours and concentrated to afford a residue that was dissolved in ethyl acetate (500 mL) and washed with water (2×100 mL). The organic layer was washed with brine (150 mL), dried over $Na_2SO_4$ and concentrated to afford methyl 5-amino-2',4'-difluoro-2-(trifluoromethyl)-[1,1'-biphenyl]-4-carboxylate (5.2 g) as brown oil.

m/z (ESI, +ve)=332.0 $(M+H)^+$.

Step 6: methyl 3-amino-2',4'-difluoro-2-iodo-6-(trifluoromethyl)-[1,1'-biphenyl]-4-carboxylate

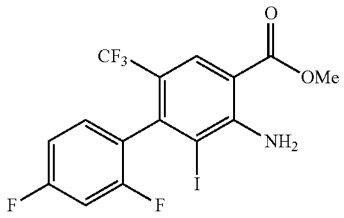 [SMILES: COC(=O)c1cc(C(F)(F)F)c(-c2ccc(F)cc2F)c(I)c1N]

To a solution of methyl 5-amino-2',4'-difluoro-2-(trifluoromethyl)[1,1'-biphenyl]-4-carboxylate (5.3 g, 16 mmol) in AcOH (35 mL) was added N-iodosuccinamide (3.4 g, 15 mmol) and stirred at 25° C. for 16 h. The solution was concentrated, the residue dissolved in ethyl acetate (400 mL) and washed with $Na_2S_2O_3/NaHCO_3$ (3×100 mL), brine (100 mL), dried over $Na_2SO_4$ and concentrated to afford methyl 3-amino-2',4'-difluoro-2-iodo-6-(trifluoromethyl)-[1,1'-biphenyl]-4-carboxylate (5 g) as a yellow solid.

m/z (ESI, +ve)=457.9 $(M+H)^+$.

Step 7: 3-amino-2',4'-difluoro-2-iodo-6-(trifluoromethyl)-[1,1'-biphenyl]-4-carboxylic acid

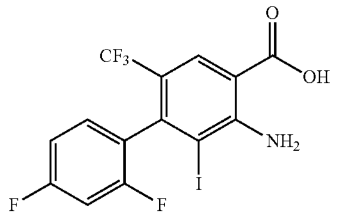

To a mixture of methyl 3-amino-2',4'-difluoro-2-iodo-6-(trifluoromethyl)-[1,1'-biphenyl]-4-carboxylate (10 g, 21.8 mmol) in THF (24 mL), methanol (16 mL) and water (16 mL) was added NaOH (8.72 g, 218 mmol). The reaction mixture was stirred at room temperature for 2 hours. The mixture was concentrated under reduced pressure to afford a residue. 1 M HCl was added over this crude material and the pH adjusted to 5-6, extracted with EtOAc (20 mL×3). The organic phases were combined, washed with brine (10 mL), dried over $Na_2SO_4$ and filtered. The filtrate was concentrated under reduced pressure to afford the 3-amino-2',4'-difluoro-2-iodo-6-(trifluoromethyl)-[1,1'-biphenyl]-4-carboxylic acid (9 g, 89%) as a pink solid.

m/z (ESI, +ve)=442.94 $(M+H)^+$.

Step 8: 7-(2,4-difluorophenyl)-8-iodo-6-(trifluoromethyl)quinazoline-2,4(1H,3H)-dione

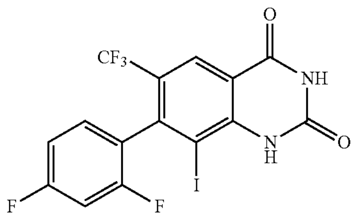 [SMILES: O=c1[nH]c(=O)c2cc(C(F)(F)F)c(-c3ccc(F)cc3F)c(I)c2[nH]1]

3-amino-2',4'-difluoro-2-iodo-6-(trifluoromethyl)-[1,1'-biphenyl]-4-carboxylic acid (13 g, 29.34 mmol) was added to urea (105.64 g, 1760.4 mmol). The reaction mixture was stirred at 100° C. for 2 h. The mixture was cooled to 100° C., water (500 mL) was added and stirred for 30 min, filtered and the filter cake was washed with EtOAc (1400 mL). The filtrate was collected and concentrated under reduced pressure to afford a solid that was washed with methanol (100 mL) to afford 7-(2,4-difluorophenyl)-8-iodo-6-(trifluoromethyl)quinazoline-2,4(1H,3H)-dione (5.8 g, 42%) as a yellow solid.

m/z (ESI, +ve)=467.94 $(M+H)^+$.

Step 9: 7-(2,4-difluorophenyl)-8-((2-hydroxyethyl)thio)-6-(trifluoromethyl)quinazoline-2,4(1H,3H)-dione

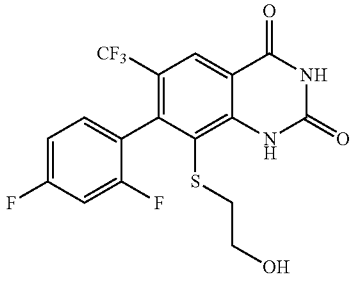 [SMILES: O=c1[nH]c(=O)c2cc(C(F)(F)F)c(-c3ccc(F)cc3F)c(SCCO)c2[nH]1]

To a solution of 7-(2,4-difluorophenyl)-8-iodo-6-(trifluoromethyl)quinazoline-2,4(1H,3H)-dione (5.8 g, 0.0124 mol), Cuprous iodide (470 mg, 0.0024 mol) and Potassium carbonate (5.14 g, 00.0372 mol) in isopropyl alcohol (30 ml) and ethylene glycol (60 ml) was added 2-mercaptoethan-1-ol (2.91 g, 0.0372 mol). The reaction mixture was stirred at 85° C. for 36 hours. The mixture was concentrated under reduced pressure and the crude material purified by reverse column chromatography (phase A: water (0.1% TFA), phase B: CAN, 0~41%) to afford 7-(2,4-difluorophenyl)-8-((2-hydroxyethyl)thio)-6-(trifluoromethyl)quinazoline-2,4(1H,3H)-dione (2.1 g, 39%) as a white solid.

m/z (ESI, +ve)=418.04 $(M+H)^+$.

Step 10: 10-(2,4-difluorophenyl)-9-(trifluoromethyl)-2,3-dihydro-5H-[1,4]thiazino[2,3,4-ij]quinazoline-5,7(6H)-dione

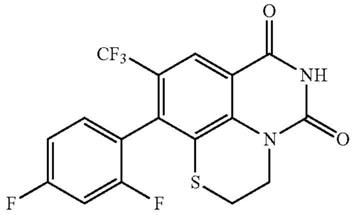 [SMILES: O=c1[nH]c(=O)n2c3c(c(-c4ccc(F)cc4F)c(C(F)(F)F)cc13)SCC2]

To a solution of Triphenylphosphine (1.69 g, 6.4 mmol) in THF (10 ml) cooled to 0° C. was added N,N-Diisopropylethylamine (1.30 g, 6.4 mmol) and stirred for 30 minutes. 7-(2,4-difluorophenyl)-8-((2-hydroxyethyl)thio)-6-(trifluoromethyl)quinazoline-2,4(1H,3H)-dione (1.8 g, 6.4 mmol) was added and stirred at 0° C. for 1 hour. The mixture was concentrated under reduced pressure and the residue purified by reverse column chromatography (phase A: water (0.1% TFA), phase B: ACN; 0-50%) to afford 10-(2,4-difluorophenyl)-9-(trifluoromethyl)-2,3-dihydro-5H-[1,4]thiazino[2,3,4-ij]quinazoline-5,7(6H)-dione (1.4 g, 77%) as a white solid.

m/z (ESI, +ve)=400.03 $(M+H)^+$.

$^1$H NMR (400 MHz, DMSO-d6) δ12.03 (s, 1H), 8.10 (s, 1H), 7.52-7.45 (m, 1H), 7.38-7.32 (m, 1H), 7.29-7.18 (m, 1H), 4.34-4.32 (m, 1H), 4.16-4.07 (m, 1H), 3.23-3.10 (m, 2H).

Step 11: diethyl pyrazine-2,3-dicarboxylate

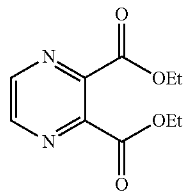 [SMILES: CCOC(=O)c1nccnc1C(=O)OCC]

To a solution of pyrazine-2,3-dicarboxylic acid (15 g, 0.03 mol) in EtOH (100 mL) was added thionyl chloride (10 mL) at 0° C. The mixture was stirred at 80° C. for 2 h. The solvent was removed to afford a residue that was purified by silica gel chromatography to afford diethyl pyrazine-2,3-dicarboxylate (18.5 g, 92%) as a light-yellow oil.

m/z (ESI, +ve)=225.1 $(M+H)^+$.

$^1H$ NMR (400 MHz, DMSO) δ 8.96 (s, 2H), 4.40 (d, J=8.0 Hz, 4H), 1.33 (t, J=8.0 Hz, 6H).

Step 12: syn-(diethyl-piperazine-2,3-dicarboxylate)

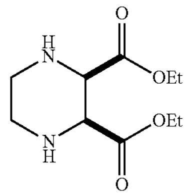

A mixture of diethyl pyrazine-2,3-dicarboxylate (13.8 g, 0.062 mol) and 10% palladium on carbon (2.4 g) in EtOH (50 ml) was stirred under hydrogen at 50 psi for 20 h. The suspension was filtered through a pad of celite and the filter cake was washed with EtOH. The filtrate was concentrated under reduced pressure to afford diethyl (2S,3R)-piperazine-2,3-dicarboxylate (13.8 g, 97%) as a brown oil.

m/z (ESI, +ve)=231.2 $(M+H)^+$.

Step 13: diethyl-1,4-dibenzylpiperazine-cis-2,3-dicarboxylate

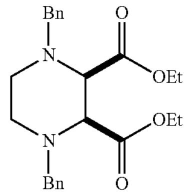

To a solution of cis-(diethyl-piperazine-2,3-dicarboxylate) (13.8 g, 0.06 mol) in ACN (60 mL) were added (bromomethyl)benzene (20.5 g, 0.12 mol) and potassium carbonate (24.9 g, 0.18 mol). The mixture was stirred at room temperature for 16 h. The solvent was removed, the residue was suspended in $H_2O$ (100 mL) and extracted with ethyl acetate (50 mL×3). The combined organic layers were washed with brine (50 mL), dried over sodium sulphate and concentrated in vacuo to afford a residue that was purified by silica gel chromatography to afford the desired product (14.8 g, 56%) as a light yellow oil.

m/z (ESI, +ve)=411.2 $(M+H)^+$.

$^1H$ NMR (400 MHz, DMSO) δ 7.34-7.23 (m, 10H), 4.21-4.00 (m, 4H), 3.83-3.78 (m, 2H), 3.49 (s, 2H), 3.44-3.41 (m, 2H), 3.00-2.98 (m, 2H), 2.27-2.23 (m, 2H), 1.19 (t, J=8.0 Hz, 6H).

Step 14: (1,4-dibenzylpiperazine-cis-2,3-diyl)dimethanol

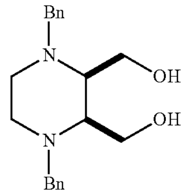

To a solution of diethyl-1,4-dibenzylpiperazine-cis-2,3-dicarboxylate (14.8 g, 0.036 mol) in THF (100 mL) was added $LiAlH_4$ (2.73 g, 0.072 mmol) at 0° C. The mixture was stirred at room temperature for 5 h and then quenched with 10% NaOH and extracted with ethyl acetate (30 mL×3). The combined organic layers were washed with brine (50 mL), dried over sodium sulphate and concentrated under reduced pressure to afford (1,4-dibenzylpiperazine-cis-2,3-diyl)dimethanol) (11.5 g, 97%) as a yellow solid.

m/z (ESI, +ve)=327.2 $(M+H)^+$.

$^1H$ NMR (400 MHz, DMSO) δ 7.32-7.26 (m, 8H), 7.31-7.19 (m, 2H), 4.69 (t, J=4.0 Hz, 2H), 3.96-3.92 (m, 2H), 3.81-3.76 (m, 2H), 3.66-3.63 (m, 2H), 3.44-3.41 (m, 2H), 2.74-2.73 (m, 2H), 2.55-2.51 (m, 2H), 2.23-2.18 (m, 2H).

Step 15: 1,4-di benzylpiperazine-cis-2,3-diyl-bis(methylene) dimethanesulfonate

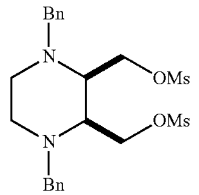

To a solution of (1,4-dibenzylpiperazine-cis-2,3-diyl)dimethanol (3.26 g, 10 mmol) in dichloromethane (30 mL) at 0° C. was added $Et_3N$ (3.03 g, 30 mmol), followed by MsCl (2.85 g, 25 mmol). The reaction mixture was stirred at 0° C. for 2 hours. Upon completion, the mixture was washed with brine (20 mL) three times. The organic layers were dried over anhydrous $Na_2SO_4$ and concentrated under reduced pressure to afford 1,4-dibenzylpiperazine-cis-2,3-diyl-bis (methylene) dimethanesulfonate (3.6 g, 75%) which was used directly in the next step.

Step 16: 1,4-dibenzyl-cis-octahydrothieno[3,4-b]pyrazine

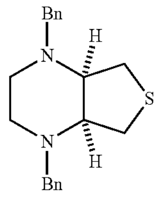 [SMILES: c1ccc(CN2CCN(Cc3ccccc3)[C@H]3CSC[C@H]32)cc1]

To a solution of 1,4-dibenzylpiperazine-cis-2,3-diyl-bis (methylene) dimethanesulfonate (3.6 g, 7.5 mmol) in EtOH (30 mL) was added $Na_2S$ (2.9 g, 37.5 mmol). The mixture was stirred at 80° C. for 16 hours, cooled down to room temperature and concentrated. The residue was diluted with water (30 mL) and extracted with EtOAc (30 mL×3). The combined organic layers were dried over anhydrous $Na_2SO_4$ and concentrated to afford a residue that was purified by column chromatography yielding the desired product as light yellow oil (1.8 g, 75%).

m/z (ESI, +ve)=325.0 $(M+H)^+$.

Step 17: cis-octahydrothieno[3,4-b]pyrazine

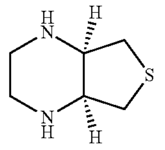

To a solution of 1,4-dibenzyl-cis-octahydrothieno[3,4-b]pyrazine (1 g, 3.1 mmol) in dichloroethane (10 mL) was added 1-chloroethyl chloroformate (4.43 g, 31 mmol). The reaction mixture was stirred at 80° C. for 16 hours, cooled down to room temperature and concentrated. The residue was dissolved in methanol (10 ml) and stirred at 80° C. for 4 hours. The resulting suspension was filtered and the filter cake was washed with methanol and dried to afford the desired product (0.44 g, 92%) as a white solid.

m/z (ESI, +ve)=145.2 $(M+H)^+$.

Step 18: dibenzyl-cis-hexahydrothieno[3,4-b]pyrazine-1,4-dicarboxylate

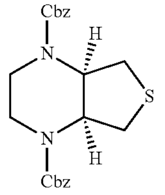 [SMILES: O=C(OCc1ccccc1)N1CCN(C(=O)OCc2ccccc2)[C@H]2CSC[C@H]21]

To a solution of cis-octahydrothieno[3,4-b]pyrazine (440 mg, 3.05 mmol) in dioxane/water (20 mL) at 0° C., benzyl chloroformate (1.1 g, 6.71 mmol) and $NaHCO_3$ (366 mg, 9.15 mmol) were added. The reaction mixture was stirred at room temperature for 16 hours. The solvent was removed, $H_2O$ (20 mL) was added and the mixture extracted with ethyl acetate (20 mL×3). The organic layers were combined, washed with brine (50 mL), dried over sodium sulphate and concentrated in vacuo to afford a residue that was purified by silica gel chromatography to afford dibenzyl-cis-hexahydrothieno[3,4-b]pyrazine-1,4-dicarboxylate (870 mg, 69%) as colorless oil.

m/z (ESI, +ve)=413.2 $(M+H)^+$.

Step 19: dibenzyl-cis-hexahydrothieno[3,4-b]pyrazine-1,4-dicarboxylate 6,6-dioxide

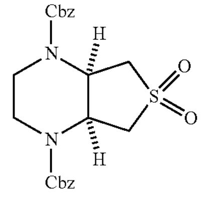 [SMILES: O=C(OCc1ccccc1)N1CCN(C(=O)OCc2ccccc2)[C@H]2CS(=O)(=O)C[C@H]21]

To a solution of dibenzyl-cis-hexahydrothieno[3,4-b]pyrazine-1,4-dicarboxylate (840 mg, 2.04 mmol) in dichloromethane (10 mL) at 0° C., was added 3-chloroperoxybenzoic acid (880 mg, 5.1 mmol). and the reaction mixture was stirred at room temperature for 4 hours. The reaction was quenched with $H_2O$ (20 mL) and extracted with dichloromethane (10 mL×3). The combined organic layers were washed with brine (20 mL), dried over sodium sulphate and concentrated to afford a residue that was purified by silica gel chromatography to afford dibenzyl-cis-hexahydrothieno[3,4-b]pyrazine-1,4-dicarboxylate 6,6-dioxide (920 mg, 91%) as a white solid.

m/z (ESI, +ve)=467.1 $(M+Na)^+$.

Step 20: cis-octahydrothieno[3,4-b]pyrazine 6,6-dioxide

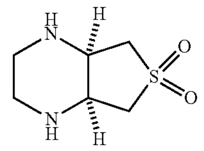 [SMILES: O=S1(=O)C[C@@H]2NCCN[C@@H]2C1]

To a solution of dibenzyl-cis-hexahydrothieno[3,4-b]pyrazine-1,4-dicarboxylate 6,6-dioxide (760 mg, 1.71 mmol) in acetic acid (20 ml) was added bromhidric acid (6 ml). The reaction mixture was stirred at 50° C. for 20 hours. The suspension was filtered, the solid washed with ethyl acetate and dried to afford cis-octahydrothieno[3,4-b]pyrazine 6,6-dioxide (340 mg, 74%) as a white solid.

m/z (ESI, +ve)=177.1 $(M+H)^+$.

$^1H$ NMR (400 MHz, $D_2O$) δ 4.43 (d, J=5.0 Hz, 2H), 3.70-3.66 (m, 4H), 3.38-3.28 (m, 4H).

Step 21: 10-(2,4-difluorophenyl)-7-(6,6-dioxidohexahydrothieno[3,4-b]pyrazin-1(2H)-yl)-9-(trifluoromethyl)-2,3-dihydro-5H-[1,4]thiazino[2,3,4-ij]quinazolin-5-one

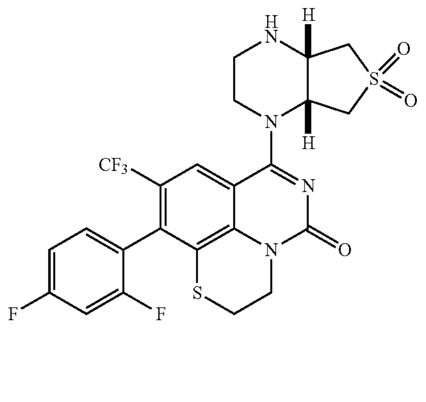

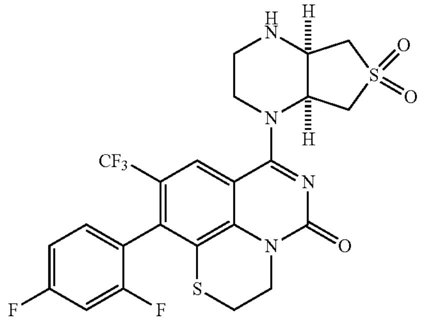

To a solution of 10-(2,4-difluorophenyl)-9-(trifluoromethyl)-2,3-dihydro-5H-[1,4]thiazino[2,3,4-ij]quinazoline-5,7(6H)-dione (70 mg, 0.05 mmol) in toluene (1 mL) were added N,N-diisopropylethylamine (135 mg, 1.0 mmol) and $POCl_3$ (1 mL). The reaction mixture was stirred at 120° C. for 1.5 hours, cooled down to room temperature and concentrated to afford a residue that was dissolved in dichloroethane (1 mL) and added to a solution of octahydrothieno[3,4-b]pyrazine 6,6-dioxide (118 mg, 0.35 mmol) and N,N-diisopropylethylamine (135 mg, 1.0 mmol) in dichloroethane (1 mL). The reaction mixture was stirred at room temperature for 1 hour, concentrated and the resulting solid purified by silica gel chromatography to afford 10-(2,4-difluorophenyl)-7-(6,6-dioxidohexahydrothieno[3,4-b]pyrazin-1(2H)-yl)-9-(trifluoromethyl)-2,3-dihydro-5H-[1,4]thiazino[2,3,4-ij]quinazolin-5-one (50 mg, 51%) as a yellow solid.

m/z (ESI, +ve)=559.1 $(M+H)^+$.

Example Pyrimidone-Thiomorpholines-B

12. Syntheses of intermediates for Substituted tricyclic thiomorpholine compounds 6-chloro-7-(2,4-difluorophenyl)-8-iodoquinazoline-2,4(1H,3H)-dione Reaction Scheme 1

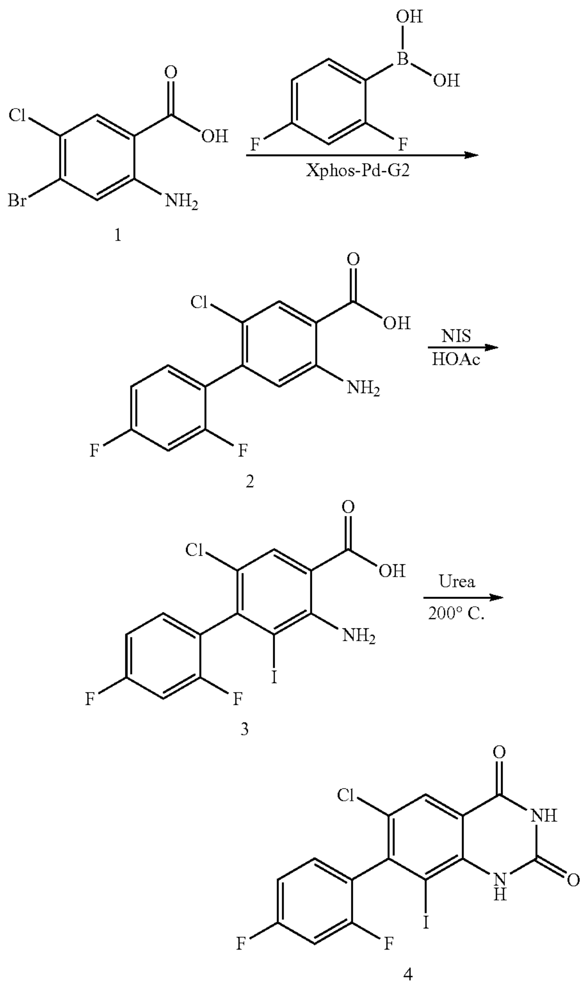

1
2
3
4

5-amino-2-chloro-2',4'-difluoro-[1,1'-biphenyl]-4-carboxylic acid (2)

To a mixture of 2-amino-4-bromo-5-chlorobenzoic acid (20 g, 79.7 mmol), (2,4-difluorophenyl)boronic acid (37.8 g, 239.1 mmol) and $K_2CO_3$ (33 g, 239.1 mmol) in dioxane/$H_2O$ (200 mL/40 mL) was added Xphos-Pd-G2 (4.7 g, 5.6 mmol). The reaction mixture was stirred at 80° C. under nitrogen atmosphere for 6 hours. The mixture was filtrated and diluted with $H_2O$. The pH was adjusted to 2 with 2N HCl, then extracted with EtOAc. The organic layer was washed with brine and then concentrated in vacuo. The solid obtained was washed with ACN to give 5-amino-2-chloro-2',4'-difluoro-[1,1'-biphenyl]-4-carboxylic acid (7.6 g+17 g crude) as an off white solid.

LC-MS: m/z 284.2 $[M+H]^+$ 3-amino-6-chloro-2',4'-difluoro-2-iodo-[1,1'-biphenyl]-4-carboxylic acid (3)

To a mixture of 5-amino-2-chloro-2',4'-difluoro-[1,1'-biphenyl]-4-carboxylic acid (21.6 g, 76.3 mmol) in AcOH (250 mL) was added NIS (25.7 g, 114.4 mmol) at 0° C. The reaction mixture was stirred at rt overnight. The reaction mixture was concentrated in vacuum and diluted with $H_2O$. The reaction was quenched by $Na_2S_2O_3$ (aq), then extracted with EtOAc (200 mL). The organic phase was washed with brine (150 mL), concentrated in vacuum to give the crude product 3-amino-6-chloro-2',4'-difluoro-2-iodo-[1,1'-biphenyl]-4-carboxylic acid (26 g crude) as brown solid.

LC-MS: m/z 409.9 $[M+H]^+$.

6-chloro-7-(2,4-difluorophenyl)-8-iodoquinazoline-2,4(1H,3H)-dione (4)

To a 250 mL glass pressure vessel equipped with stirring bar was charged 3-amino-6-chloro-2',4'-difluoro-2-iodo-[1,1'-biphenyl]-4-carboxylic acid (26 g, 63.56 mmol) and urea (38 g, 635.6 mol). The vessel was placed on a preheated block at 200° C. and the reaction was stirred for 4 h. The mixture reaction mixture was cooled to 80° C. and diluted with water. After filtration, the filter cake was washed with Petroleum Ether/EtOAc (30 mL/10 mL) to give 6-chloro-7-(2,4-difluorophenyl)-8-iodoquinazoline-2,4(1H,3H)-dione (7.6 g, yield: 27%) as a white solid.

LC-MS: m/z 433.1 $[M-H]^+$.

5-((tert-butyldiphenylsilyl)oxy)-1-mercaptopentan-2-ol

Reaction Scheme 2

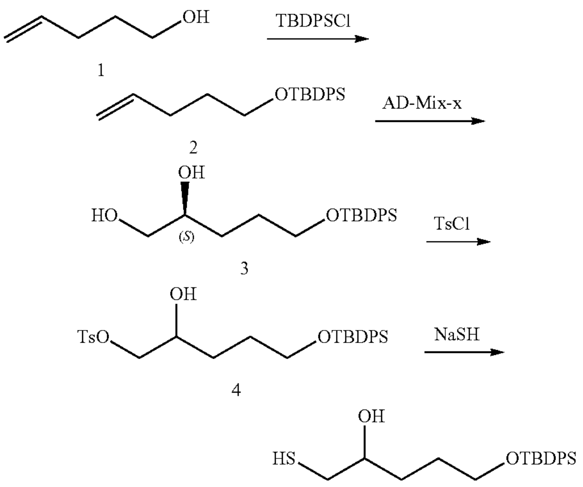

tert-butyl(pent-4-en-1-yloxy)diphenylsilane (2)

To a solution of pent-4-en-1-ol (25 g, 290 mmol) and imidazole (29 g, 435 mmol) in DMF (400 mL) was added TBDPSCl (95 g, 348 mmol) at 0° C. The mixture was stirred at rt for 16 hours. The mixture was concentrated to remove most of DMF followed by the addition of $H_2O$ (500 mL. The resulting mixture was extracted with EtOAc (500 mL×3). The organic layers were combined and concentrated under reduced pressure. The residue was purified by silica gel column with 1% EA in PE to afford the product (74 g, 79%) as light yellow oil. MS (ESI) m/z 325.2 $[M+H]^+$.

5-((tert-butyldiphenylsilyl)oxy)pentane-1,2-diol (3)

To a solution of tert-butyl(pent-4-en-1-yloxy)diphenylsilane (58 g, 179 mmol) in t-BuOH (300 mL) and $H_2O$ (300 mL) was added AD-mix-α (232 g) at 0° C. The mixture was stirred at rt for 16 hours. The reaction was quenched with $NaS_2O_3$ aqueous solution and stirred at rt for 2 h. Then the mixture was extracted with EtOAc (500 mL×3). The organic layer was concentrated, and the residue was purified by silica gel column with 5% MeOH in DCM to afford the product (55 g, 85%) as light yellow oil. MS (ESI) m/z 359.2 $[M+H]^+$.

5-((tert-butyldiphenylsilyl)oxy)-2-hydroxypentyl 4-methylbenzenesulfonate (4)

To a solution of 5-((tert-butyldiphenylsilyl)oxy)pentane-1,2-diol (54 g, 152 mmol) and TEA (43 mL, 304 mmol) in DCM (500 mL) was added TsCl (32 g, 167 mmol) at 0° C. The mixture was stirred at rt for 16 hours. 500 mL of $H_2O$ was added and extracted with DCM (500 mL×3). The organic layer was concentrated, and the residue was purified by silica gel column with 10% EtOAc in PE to afford the product (50 g, 64%) as light yellow oil. MS (ESI) m/z 513.2 $[M+H]^+$.

5-((tert-butyldiphenylsilyl)oxy)-1-mercaptopentan-2-ol (5)

To a solution of 5-((tert-butyldiphenylsilyl)oxy)-2-hydroxypentyl 4-methylbenzenesulfonate (44 g, 87 mmol) in the dry DMF (120 mL) was added NaSH (14 g, 260 mmol). The mixture was stirred at rt for 1 h. 500 mL $H_2O$ was added and extracted with EtOAc (400 mL×3). The organic layer was concentrated, and the residue was purified by silica gel column with 8% EtOAc in Petroleum Ether to afford the product (22 g, 67%) as light yellow oil. MS (ESI) m/z 375.1 $[M+H]^+$.

7-(2,4-difluorophenyl)-8-iodo-6-(trifluoromethyl)quinazoline-2,4(1H,3H)-dione

Reaction Scheme 3

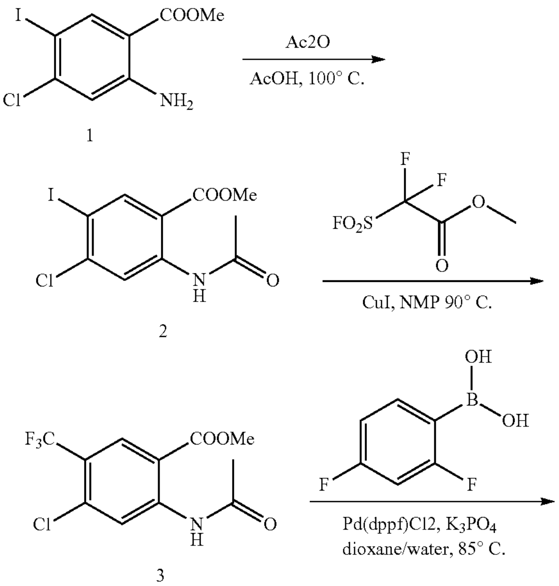

-continued

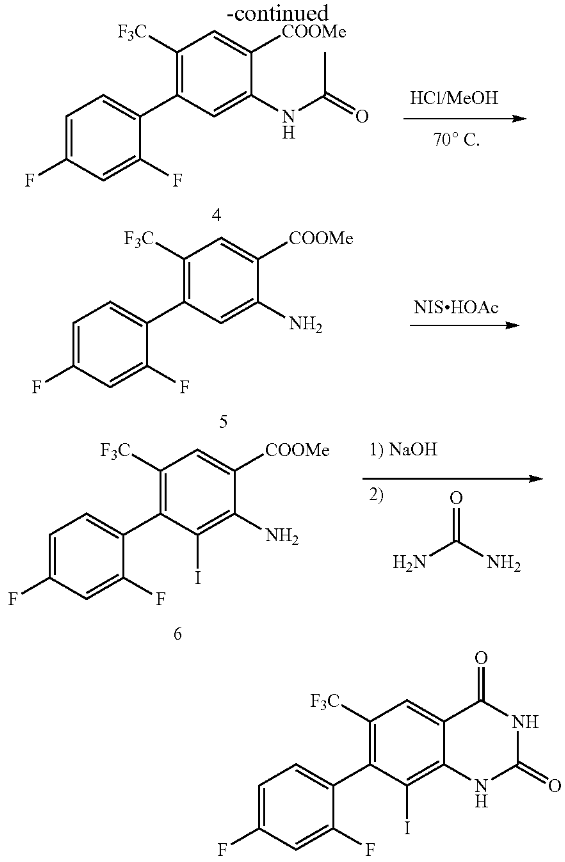

4

5

6

7 methyl 2-acetamido-4-chloro-5-iodobenzoate (2)

To a mixture of methyl 2-amino-4-chloro-5-iodobenzoate (50.00 g, 160.51 mmol) in AcOH (500 mL) was added $Ac_2O$ (19.66 g, 192.61 mmol). The mixture was stirred at 100° C. for 16 hours. After completion, the mixture was cooled to rt, filtered and washed with Petroleum Ether (200 mL) to afford crude product (35 g, yield: 62%) as white solid. MS (ESI) m/z 353.9 $[M+H]^+$.

Methyl 2-acetamido-4-chloro-5-(trifluoromethyl)benzoate (3)

To a mixture of methyl 2-acetamido-4-chloro-5-iodobenzoate (35.00 g, 98.98 mmol) in DMF (350 mL) was added methyl 2,2-difluoro-2-(fluorosulfonyl)acetate (70.09 g, 395.99 mmol), HMPA (70.98 g, 395.99 mmol) and CuI (15.05 g, 79.19 mmol). The mixture was stirred at 90° C. under $N_2$ for 16 hours. After completion, the mixture was poured into water (300 mL), extracted with EtOAc (200 mL×3). The combined organic phases were washed with brine (500 mL) and dried over $Na_2SO_4$, After filtration and concentration, the residue was purified by silica gel column with Petrolum Ether/EtOAc=100/1 to 20/1 to afford desired product (25.00 g, yield: 84%) as white solid. MS (ESI) m/z 296.0 $[M+H]^+$.

Methyl 5-acetamido-2',4'-difluoro-2-(trifluoromethyl)-[1,1'-biphenyl]-4-carboxylate (4)

To a mixture of methyl 2-acetamido-4-chloro-5-(trifluoromethyl)benzoate (20.00 g, 98.98 mmol) in dioxane (200 mL) and water (20 mL) was added (2,4-difluorophenyl) boronic acid (35.02 g, 202.95 mmol), $Pd(dppf)Cl_2$ (7.42 g, 10.14 mmol) and $K_3PO_4$ (43.08 g, 202.95 mmol). The mixture was stirred at 85° C. under $N_2$ for 2 h. (2,4-difluorophenyl)boronic acid (35.02 g, 202.95 mmol) was added to above solution, then the mixture was stirred at 85° C. under $N_2$ for 16 hours. After completion, the mixture was poured into water (200 mL), extracted with EtOAc (150 mL×3). The combined organic phases were washed with brine (300 mL) and dried over $Na_2SO_4$, After filtration and concentration, the residue was purified by silica gel column using a gradien of Petroleum Ether/EtOAc (50/1 to 15/1) to afford the desired product (16.60 g, yield: 62%) as white solid. MS (ESI) m/z 374.0 $[M+H]^+$ Methyl 5-amino-2',4'-difluoro-2-(trifluoromethyl)-[1,1'-biphenyl]-4-carboxylate (5)

A mixture of methyl 5-acetamido-2',4'-difluoro-2-(trifluoromethyl)-[1,1'-biphenyl]-4-carboxylate (26.00 g, 69.65 mmol) in HCl/MeOH (300 mL) was stirred at 70° C. for 2 h. The mixture was concentrated and a saturated aqueous solution of $NaHCO_3$ (100 mL) was added. The resulting mixture was extracted with EtOAc (50 mL×3). The combined organic phases were combined, washed with brine (100 mL) and dried over $Na_2SO_4$. The solvent was removed in vacuo to afford the crude product (23.00 g) as a yellow solid. MS (ESI) m/z 332.0 $[M+H]^+$ Methyl 3-amino-2',4'-difluoro-2-iodo-6-(trifluoromethyl)-[1,1'-biphenyl]-4-carboxylate (6)

To a mixture of methyl 5-amino-2',4'-difluoro-2-(trifluoromethyl)-[1,1'-biphenyl]-4-carboxylate (23.00 g, 69.44 mmol) in AcOH (200 mL) was added NIS (18.75 g, 83.32 mmol). The mixture was stirred at 50° C. for 2 h. After completion, the mixture was poured into water (200 mL), extracted with EtOAc (150 mL×3). The combined organic phases were washed with brine (300 mL) and dried over $Na_2SO_4$. After filtration and concentration, the residue was purified by silica gel column with Petroleum Ether/EtOAc=200/1 to 20/1 to afford the desired product (26.00 g, 62% yield) as white solid. MS (ESI) m/z 457.9 $[M+H]^+$ 7-(2,4-difluorophenyl)-8-iodo-6-(trifluoromethyl)quinazoline-2,4(1H,3H)-dione (7)

To a solution of methyl methyl 3-amino-2',4'-difluoro-2-iodo-6-(trifluoromethyl)-[1,1'-biphenyl]-4-carboxylate (25.00 g, 54.69 mmol) in dioxane (200 mL) and water (200 mL) was added NaOH (4.37 g, 109.38 mmol). The mixture was stirred at 90° C. for 3 h. After completion, the mixture was poured into water (200 mL). Adjusted pH=4-5 and extracted with EtOAc (150 mL×3). The combined organic phases were washed with brine (300 mL) and dried over $Na_2SO_4$. The solvent was removed in vacuo to give 3-amino-2',4'-difluoro-2-iodo-6-(trifluoromethyl)-[1,1'-biphenyl]-4-carboxylic acid (24 g, crude) as yellow solid.

A mixture of 3-amino-2',4'-difluoro-2-iodo-6-(trifluoromethyl)-[1,1'-biphenyl]-4-carboxylic acid (5.00 g, 11.28 mmol) and urea (13.55 g, 225.68 mmol) was stirred at 198° C. for 6 hours. After completion, the mixture was cooled to 80° C., water (200 mL) was added to the solution and stirred for 1 h. The mixture was filtrated to afford the desired product (3.00 g, 56% yield) as a white solid. MS (ESI) m/z 467.9 $[M+H]^+$ (R)-benzyl 4-(2-hydroxy-3-mercaptopropyl)piperidine-1-carboxylate Reaction Scheme 4

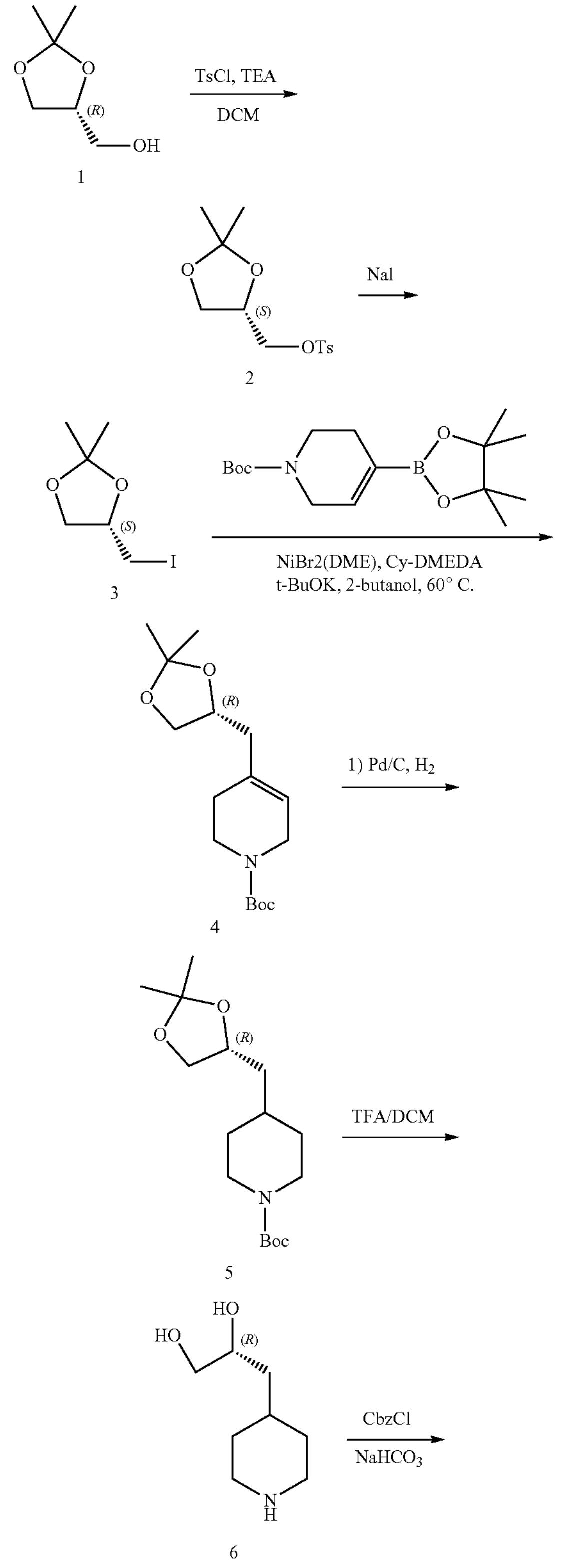

-continued

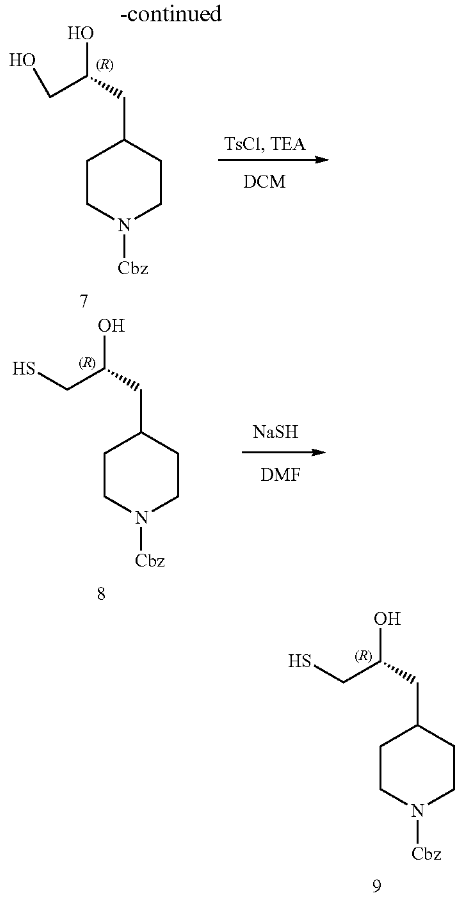

(S)-(2,2-dimethyl-1,3-dioxolan-4-yl)methyl 4-methylbenzenesulfonate (2)

To a mixture of (R)-(2,2-dimethyl-1,3-dioxolan-4-yl) methanol (50 g, 378 mmol), DMAP (6.0 g, 49 mmol) and TEA (105 mL, 755 mmol) in DCM (500 mL) was added TsCl (108.2 g, 567.5 mmol) at 0° C. The mixture was stirred at rt overnight. The reaction solution was poured into $NaHCO_3$ (aq) (1.2 L) and stirred for 1 h. The mixture was extracted with DCM (200 mL). The organic layer was washed with water (1 L), dried over $Na_2SO_4$, filtered and concentrated under reduced pressure to afford the title compound (119.3 g, crude) as a colorless oil, which was used to next step without further purification. MS (ESI) m/z 287.1 $[M+H]^+$.

(S)-4-(iodomethyl)-2,2-dimethyl-1,3-dioxolane (3)

To a mixture of (S)-(2,2-dimethyl-1,3-dioxolan-4-yl) methyl 4-methylbenzenesulfonate (119.3 g, 378.3 mmol) in acetone (900 mL) was added NaI (1.12 kg, 7.57 mol). The mixture was stirred at 75° C. overnight. The reaction solution was filtered and the solvent was removed in vacuo. The residue was redissolved with EtOAc (1 L) and the resulting solution was washed with water (1.5 L), $Na_2SO_3$ (aq, 500 mL) and brine (500 mL). The water phase was extracted with EtOAc (1 L). The combined organic phases were dried over $Na_2SO_4$, filtered and concentrated under reduced pressure. The residue was purified by silica gel chromatography (10% ethyl acetate in petroleum ether) to afford the title compound (81.4 g, 1.08 mmol, 83% yield) as yellow liquid. $^1H$ NMR (400 MHz, $CDCl_3$) δ 4.31-4.25 (m, 1H), 4.17-4.13 (m, 1H), 3.80-3.77 (m, 1H), 3.27-3.24 (m, 1H), 3.14 (t, J=8.8 Hz, 1H), 1.46 (s, 3H), 1.35 (s, 3H).

(R)-tert-butyl 4-((2,2-dimethyl-1,3-dioxolan-4-yl) methyl)-5,6-dihydropyridine-1(2H)-carboxylate (4)

To a mixture of tert-butyl 4-(4,4,5,5-tetramethyl-1,3,2-dioxaborolan-2-yl)-5,6-dihydropyridine-1(2H)-carboxylate (54 g, 174.8 mmol) in dioxane (550 ml) was added Ni(dme) $Br_2$ (5.4 g, 17.5 mmol), Cy-DMEDA (2.48 g, 17.5 mmol) and t-BuOK (39.2 g, 349.6 mmol) at 0° C. under $N_2$. The mixture was heated to 60° C. for 18 hours and was diluted with $H_2O$ and extracted with EtOAc. The organic layer was washed with water and brine. The solvent was removed in vacuo, and the residue was purified by column with a mixture of Petroleum Ether/EtOAc (10:1) to afford (R)-tert-butyl 4-((2,2-dimethyl-1,3-dioxolan-4-yl)methyl)-5,6-dihydropyridine-1(2H)-carboxylate (29.5 g, 57% yield) as a yellow oil; LC-MS:m/z 198.1. $[M+H-Boc]^+$.

(R)-tert-butyl 4-((2,2-dimethyl-1,3-dioxolan-4-yl) methyl)piperidine-1-carboxylate (5)

To a mixture of (R)-tert-butyl 4-((2,2-dimethyl-1,3-dioxolan-4-yl)methyl)-5,6-dihydropyridine-1(2H)-carboxylate (29.5 g, 99.3 mol) in MeOH (300 mL) was added Pd/C (7 g). The mixture was stirred at rt under $H_2$ for 4 h. The reaction was determined to be completed by LCMS and the mixture was filtered. The filtrate was concentrated under reduced pressure to afford (R)-tert-butyl 4-((2,2-dimethyl-1,3-dioxolan-4-yl)methyl)piperidine-1-carboxylate (22 g, crude) as yellow oil; LC-MS: m/z 200.2 $[M+H-Boc]^+$.

(R)-3-(piperidin-4-yl)propane-1,2-diol (6)

To a mixture of (R)-tert-butyl 4-((2,2-dimethyl-1,3-dioxolan-4-yl)methyl)piperidine-1-carboxylate (22 g, 73.6 mmol) in DCM (40 ml) at rt was added TFA (40 mL). Then the mixture was stirred at rt for 2 h. After completion, the pH was adjusted to 7~8 with $NH_3 \cdot H_2O$. The mixture was concentrated to afford crude compound 6 (R)-3-(piperidin-4-yl)propane-1,2-diol (13 g, crude) as pale yellow oil; LC-MS: m/z 160.1. $[M+H]^+$.

(R)-benzyl 4-(2,3-dihydroxypropyl)piperidine-1-carboxylate (7)

To a mixture of (R)-3-(piperidin-4-yl)propane-1,2-diol (12 g, 75.5 mol) and $Na_2CO_3$ (24 g, 226.5 mmol) in THF (90 mL) and $H_2O$ (90 mL) was added CbzCl (19.3 g, 113.2 mol) slowly at 0° C. Then the mixture was stirred at 0° C. for 3 h. The mixture was extracted with EA (500 mL), the organic phase was washed with brine (300 mL). The solvent was removed in vacuo, and the residue was purified by silica gel column with a mixture of DCM/MeOH (30/1) to afford the title (R)-benzyl 4-(2,3-dihydroxypropyl)piperidine-1-carboxylate (15 g, 68% yield) as colorless oil. LC-MS: m/z 294.1 $[M+H]^+$.

(R)-benzyl 4-(2-hydroxy-3-mercaptopropyl)piperidine-1-carboxylate (8)

To a solution of (R)-benzyl 4-(2,3-dihydroxypropyl)piperidine-1-carboxylate (15 g, 51.13 mmol) and TEA (10.3 g, 102.26 mmol) in DCM (150 mL) was added TsCl (8.77 g, 46.02 mmol) at 0° C. The mixture was stirred at rt for 4 hours and $H_2O$ (500 mL) was added. The reaction mixture was extracted with DCM (500 mL×3). The solvent was removed in vacuo, and the residue was purified by silica gel column with a mixture of DCM/MeOH (20/1) to afford the title product (13.6 g, 59%) as light yellow oil. MS (ESI) m/z 448.1 $[M+H]^+$.

(R)-benzyl 4-(2-hydroxy-3-mercaptopropyl)piperidine-1-carboxylate (9)

To a solution of (R)-benzyl 4-(2-hydroxy-3-mercaptopropyl)piperidine-1-carboxylate (13.6 g, 30.42 mmol) in the dry DMF (50 mL) was added NaSH (5.1 g, 91.28 mmol), the mixture was stirred at rt under $N_2$ for 1 hour. $H_2O$ (200 mL) was added and the resulting mixture was extracted with EA (200 mL×3). The solvent was removed in vacuo, and the residue was purified by silica gel column using a mixture of PE/EA (2/1) to afford the desired product (5.3 g, 56%) as light yellow oil. MS (ESI) m/z 310.1 $[M+H]^+$.

(R)-benzyl 4-(3-hydroxy-2-mercaptopropyl)piperazine-1-carboxylate

Reaction Scheme 5

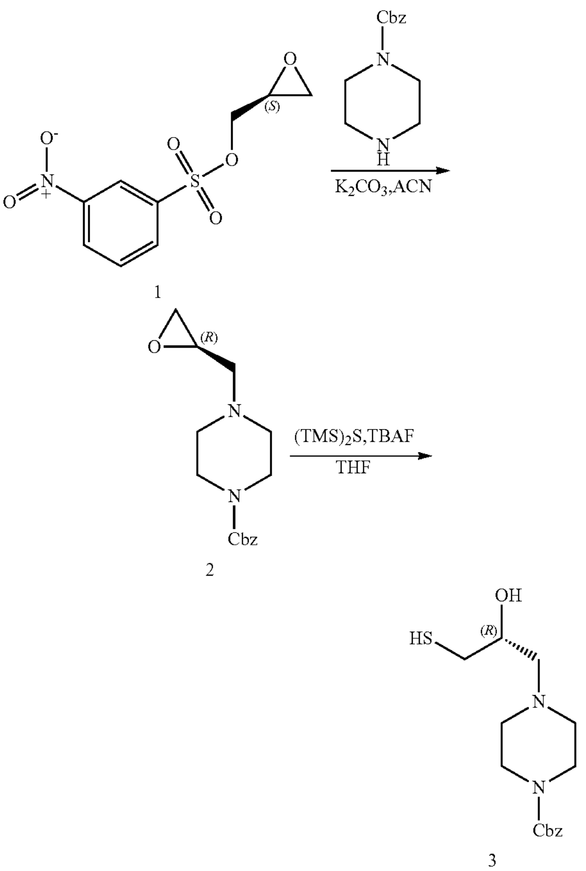

1

2

3

(R)-benzyl 4-(oxiran-2-ylmethyl)piperazine-1-carboxylate (2)

To a solution of (S)-oxiran-2-ylmethyl 3-nitrobenzenesulfonate (25 g, 96.52 mmol) in ACN (150 mL) was added benzyl piperazine-1-carboxylate (19.3 g, 75.75 mmol) and $K_2CO_3$ (24 g, 175.5 mmol) at 0° C. under nitrogen atmosphere. The mixture was stirred at room temperature for 22 hours. After completion, the solvent was removed in vacuo, and the residue was purified by silica gel column with a mixture of DCM/MeOH (50:1) to afford the desired crude product (24.5 g) as a light yellow oil. LC-MS: m/z 277.4 $[M+H]^+$.

(R)-benzyl 4-(3-hydroxy-2-mercaptopropyl)piperazine-1-carboxylate (3)

To a mixture of (R)-benzyl 4-(oxiran-2-ylmethyl)piperazine-1-carboxylate (24.5 g, 88.7 mmol) and triphenylphosphine (17.4 g, 97.5 mmol) in THF (250 mL) was slowly added TBAF (26.7 mL, 26.7 mmol, 1M in THF) at 0° C. under nitrogen atmosphere. The mixture was stirred at room temperature for 1 h. After completion, the solvent was removed in vacuo, and the residue was purified by silica gel column with a gradiant of DCM/MeOH=100:1-80:1 to afford the title product (20.8 g, 67 mmol, yield: 76%) as a colorless oil. $^1H$ NMR (400 MHz, $CDCl_3$) δ 7.36-7.31 (m, 5H), 5.13 (s, 2H), 3.80-3.78 (m, 1H), 3.54-3.50 (m, 4H), 3.39 (s, 1H), 2.66-2.57 (m, 4H), 2.46-2.40 (m, 4H), 1.57-1.52 (m, 1H); LC-MS: m/z 311.5 $[M+H]^+$.

6-chloro-7-(2,4,6-trifluorophenyl)-8-iodoquinazoline-2,4(1H,3H)-dione

Reaction Scheme 6

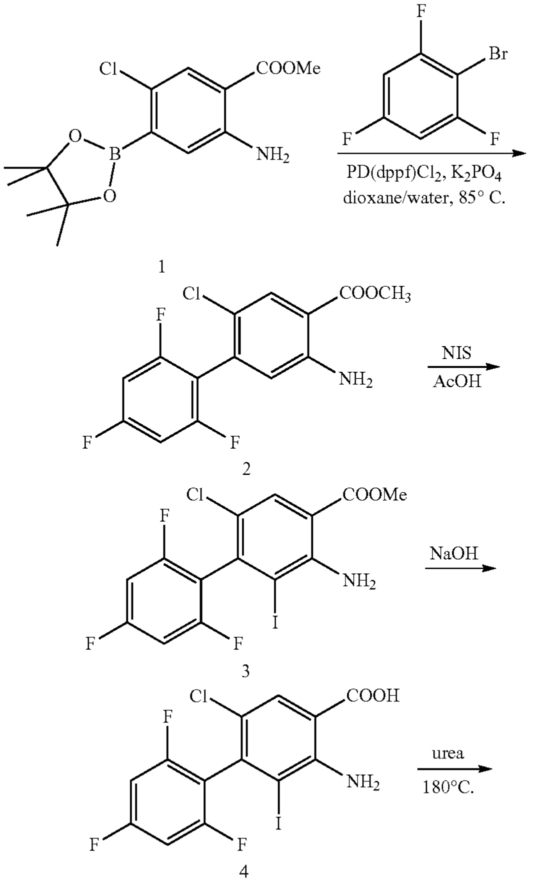

-continued

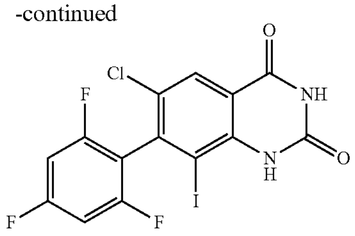

5 methyl 5-amino-2-chloro-2',4',6'-trifluoro-[1,1'-biphenyl]-4-carboxylate (2)

To a mixture of methyl 2-amino-5-chloro-4-(4,4,5,5-tetramethyl-1,3,2-dioxaborolan-2-yl)benzoate (11.00 g, 35.4 mmol) in THF (50 mL) and water (10 mL) was added 2-bromo-1,3,5-trifluorobenzene (22.39 g, 106.1 mmol), Xphos-Pd-$G_2$ (2.78 mg, 3.54 mmol) and $K_3PO_4$ (22.49 g, 106.1 mmol). The reaction mixture was stirred at 55° C. under $N_2$ for 15 h, After completion, the solvent was removed in vacuo, and the residue was purified by silica gel column with a gradiant of Petroleum Ether/EtOAc (20/1 to 2/1) to afford the desired product (10.8 g, 95% yield) as yellow solid. MS (ESI) m/z 316.0 $[M+H]^+$ methyl 3-amino-6-chloro-2',4',6'-trifluoro-2-iodo-[1,1'-biphenyl]-4-carboxylate (3)

To a mixture of methyl 5-amino-2-chloro-2',4',6'-trifluoro-[1,1'-biphenyl]-4-carboxylate (10.8 g, 34.18 mmol) in acetic acid (50 mL) was added NIS (11.54 g, 51.27 mmol). The mixture was stirred at 30° C. for 12 h. After completion, the mixture was concentrated and the residue was poured into sat.$NaHCO_3$ (100 mL), extracted with EtOAc (50 mL×3). The combined organic phases were washed with brine (100 mL), dried over $Na_2SO_4$, and concentrated to give the crude product (7.36 g, crude) as yellow solid.

3-amino-6-chloro-2',4',6'-trifluoro-2-iodo-[1,1'-biphenyl]-4-carboxylic acid (4)

To a mixture of methyl 3-amino-6-chloro-2',4',6'-trifluoro-2-iodo-[1,1'-biphenyl]-4-carboxylate (7.36 g, 16.70) in methanol (100 mL) and water (10 mL) was added NaOH (2.67 g, 66.76 mmol). The mixture was stirred at 70° C. for 3 h. After completion, the mixture was poured into water (200 mL), the pH was adjusted to 4-5 and the mixture was extracted with EtOAc (50 mL×3). The combined organic phases was washed with brine (50 mL), dried over $Na_2SO_4$, and concentrated to give the product (4.56 g, 46% yield) as yellow solid. MS (ESI) m/z 427.9 $[M+H]^+$ 6-chloro-8-iodo-7-(2,4,6-trifluorophenyl)quinazoline-2,4(1H,3H)-dione (5)

A mixture of 3-amino-6-chloro-2',4',6'-trifluoro-2-iodo-[1,1'-biphenyl]-4-carboxylic acid (4.56 g, 10.67 mmol) and urea (12.81 g, 213.58 mmol) was stirred at 180° C. for 6 h. After completion, the mixture was cooled to 80° C. Water (200 mL) was added to the mixture and stirred for 1 hour. The mixture was filtrated to give desired product (2.4 g, yield: 51%) as pale yellow solid. MS (ESI) m/z 452.9 $[M+H]^+$

Syntheses of Substituted Tricyclic Thiomorpholine Compounds

B. Example 99

(3R)-7-((8)-4-acryloyl-2-methylpiperazin-1-yl)-9-chloro-10-(2,4-difluorophenyl)-3-methyl-2H-[1,4]thiazino[2,3,4-ij]quinazolin-5 (3H)-one

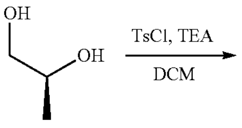

1

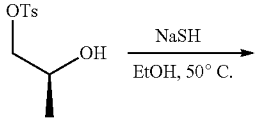

2

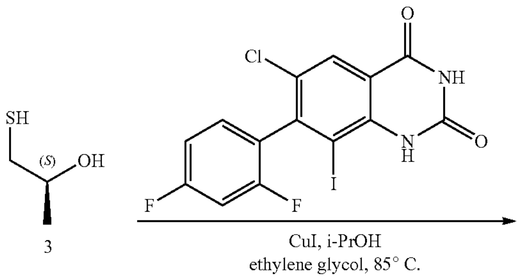

3

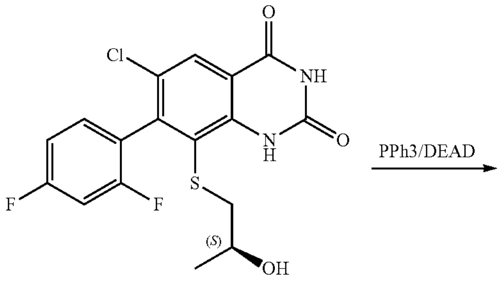

4

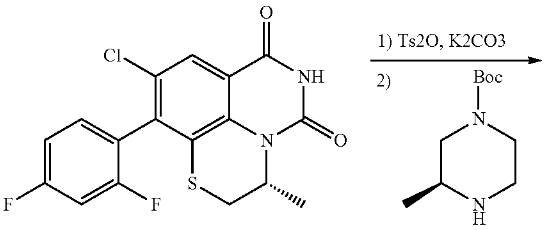

5

-continued

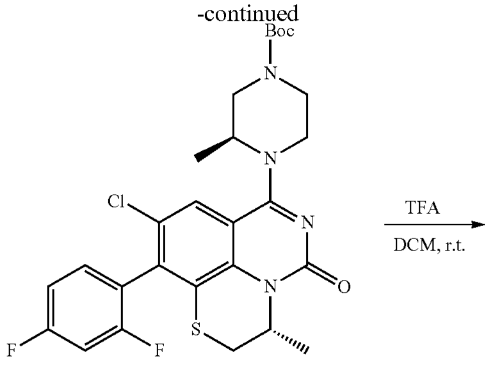

6

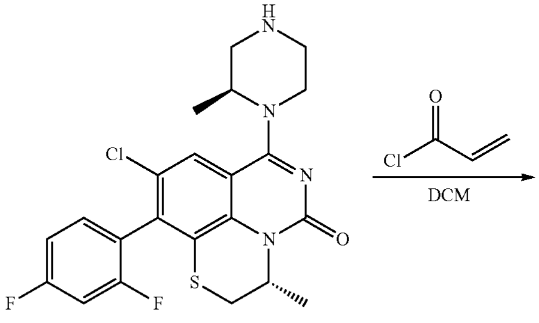

7

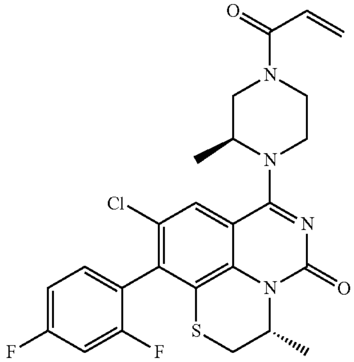

8

(S)-2-hydroxypropyl 4-methylbenzenesulfonate (2)

To a mixture of (S)-propane-1,2-diol (3.5 g, 46 mmol) and TEA (7.7 mL, 55.2 mmol) in DCM (30 mL) was added TsCl (8.78 g, 46 mmol) at 0° C. The mixture was stirred at rt for 2 hours. The solvent was evaporated and the residue was purified by silica gel chromatography (50% ethyl acetate in petroleum ether) to afford the title compound (3.0 g, 13 mmol, 28% yield) as colorless oil. MS (ESI) m/z 230.28 $[M+H]^+$.

(S)-1-mercaptopropan-2-ol (3)

To a mixture of (S)-2-hydroxypropyl 4-methylbenzene-sulfonate (1.5 g, 6.5 mmol) in EtOH (10 mL) was added NaHS (1.1 g, 19.5 mmol). The mixture was stirred at 50° C. for 0.5 h. The solvent was removed in vacuo, and the residue was diluted with DCM. The filtrate was concentrated under reduce pressure to give the title compound (599 mg, 6.5 mmol, crude) as colorless oil.

6-chloro-7-(2,4-difluorophenyl)-8-(((S)-2-hydroxy-propyl)thio)quinazoline-2,4(1H,3H)-dione (4)

The mixture of 6-chloro-7-(2,4-difluorophenyl)-8-iodo-quinazoline-2,4(1H,3H)-dione (1.5 g, 3.45 mmol), CuI (262 mg, 1.38 mmol), (S)-1-mercaptopropan-2-ol (599 mg, 3.45 mmol) and $K_2CO_3$ (1.43 g, 10.3 mmol) in iso-Propyl alcohol and ethylene glycol (15 mL, v/v=2:1) was stirred under nitrogen atmosphere at 85° C. for 5 hours. After completion, the mixture was concentrated and the residue was purified by silica gel column with a gradient of DCM/MeOH (50:1-30:1) to afford the desired product (311 mg, 0.78 mmol, 22% yield) as a light yellow solid. LC-MS: m/z 398.9 $[M-H]^+$.

(3R)-9-chloro-10-(2,4-difluorophenyl)-3-methyl-2H-[1,4]thiazino[2,3,4-ij]quinazoline-5,7(3H,6H)-dione (5)

To a mixture of 6-chloro-7-(2,4-difluorophenyl)-8-(((S)-2-hydroxypropyl)thio)quinazoline-2,4(1H,3H)-dione (321 mg, 0.8 mmol) and triphenylphosphine (1.26 g, 4.83 mmol) in THF (50 mL) was slowly added DEAD (842 mg, 4.83 mmol) at 0° C. under nitrogen atmosphere. The mixture was stirred at room temperature for 1 hour. DCM (50 mL) was added. The organic phase was washed with water (50 mL×2) and dried over $Na_2SO_4$. The solvent was removed in vacuo, and the residue was purified by silica gel column with a mixture of Petroleum Ether/EtOAc (0-50%) to afford the title product (100 mg, 0.26 mmol, 32% yield) as a yellow solid. LC-MS: m/z 380.9 $[M-H]^+$.

(3S)-tert-butyl 4-((3R)-9-chloro-10-(2,4-difluoro-phenyl)-3-methyl-5-oxo-3,5-dihydro-2H-[1,4]thi-azino[2,3,4-ij]quinazolin-7-yl)-3-methylpiperazine-1-carboxylate (6)

To a solution of (3R)-9-chloro-10-(2,4-difluorophenyl)-3-methyl-2H-[1,4]thiazino[2,3,4-ij]quinazoline-5,7(3H,6H)-dione (100 mg, 0.26 mmol) and $K_2CO_3$ (181 mg, 1.31 mmol), DMAP (4 mg, 0.02 mmol) in ACN (2 mL) was added $Ts_2O$ (128 mg, 0.39 mmol). The mixture was stirred at rt for 5 hours. Then (S)-tert-butyl 3-methylpiperazine-1-carboxylate (117 mg, 0.41 mmol) and TEA (0.1 mL, 0.78 mmol) was added to above mixture and stirred at rt for 2 h. After completion, the mixture was concentrated under reduced pressure, and the residue was purified by silica gel column with a gradient of PE/EA (20%-80%) to afford desired product (72 mg, yield: 49%) as yellow solid. LC-MS: m/z 563.0 $[M+H]^+$;

(3R)-9-chloro-10-(2,4-difluorophenyl)-3-methyl-7-((S)-2-methylpiperazin-1-yl)-2H[1,4]thiazino[2,3,4-ij]quinazolin-5(3H)-one (7)

To a solution of (3S)-tert-butyl 4-((3R)-9-chloro-10-(2,4-difluorophenyl)-3-methyl-5-oxo-3,5-dihydro-2H-[1,4]thi-azino[2,3,4-ij]quinazolin-7-yl)-3-methylpiperazine-1-carboxylate (72 mg, 0.12 mmol) in dichloromethane (2 mL) was added TFA (0.7 mL) at 0° C. The mixture was stirred at rt for 1 hour and concentrated to give the crude product (72 mg, crude) as yellow solid. LC-MS: m/z 463.0 $[M+H]^+$;

(3R)-7-((S)-4-acryloyl-2-methylpiperazin-1-yl)-9-chloro-10-(2,4-difluorophenyl)-3-methyl-2H-[1,4]thiazino[2,3,4-ij]quinazolin-5(3H)-one (8)

To a mixture of (3R)-9-chloro-10-(2,4-difluorophenyl)-3-methyl-7-((S)-2-methylpiperazin-1-yl)-2H-[1,4]thiazino[2,3,4-ij]quinazolin-5(3H)-one (72 mg, 0.12 mmol) and triethyl amine (65 mg, 0.64 mmol) in dichloromethane (3 mL) was added acrylic anhydride (32 mg, 0.25 mmol) at 0° C. The mixture was stirred at rt for 1 hour. The solvent was removed in vacuo, and the residue was purified by prep-HPLC to afford the desired product (25 mg, 38% yield) as yellow solid. LC-MS: m/z 517.1 $[M+H]^+$.

C. Example 341

(3R)-3-(3-((1S,4S)-2-oxa-5-azabicyclo[2.2.1]heptan-5-yl)propyl)-7-((S)-4-acryloyl-2-methylpiperazin-1-yl)-9-chloro-10-(2,4-difluorophenyl)-2H-[1,4]thi-azino[2,3,4-ij]quinazolin-5(3H)-one

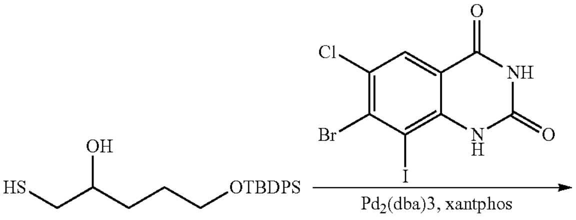

1

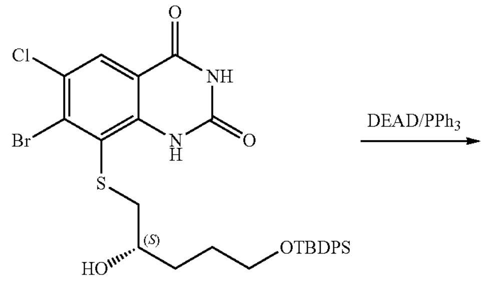

2

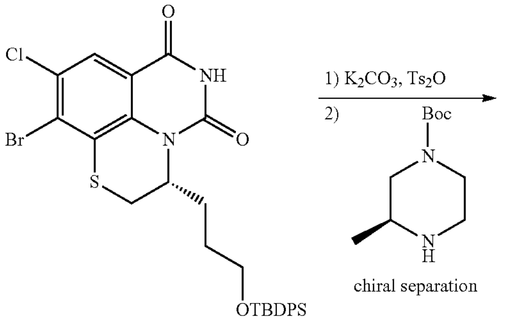

3

-continued

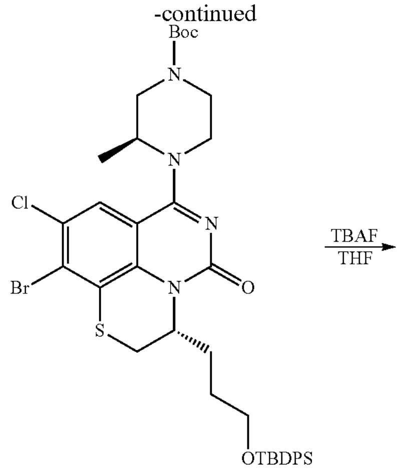

4

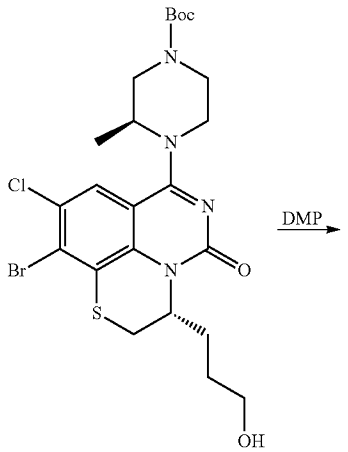

5

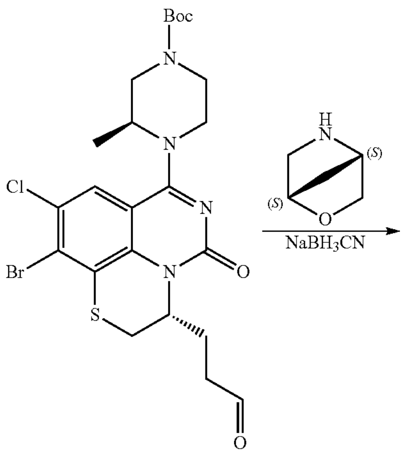

6

-continued

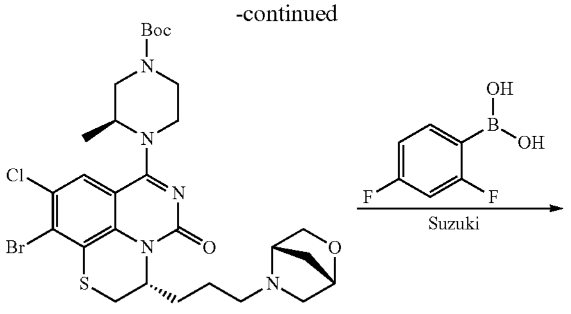

7

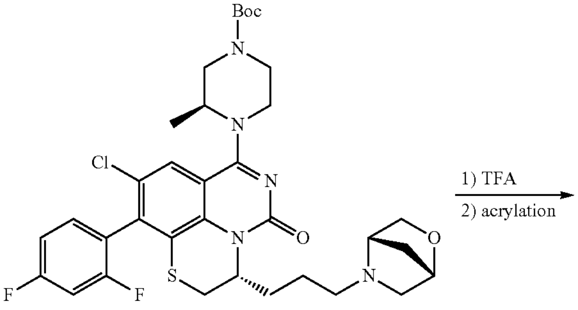

8

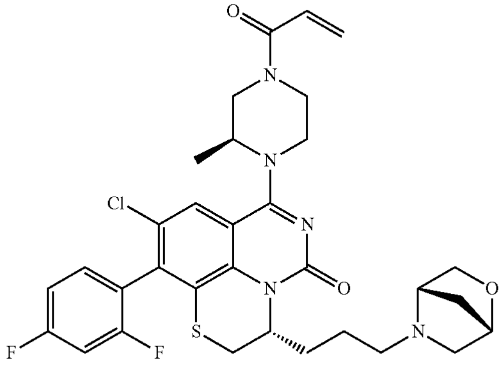

9

(S)-7-bromo-8-((5-((tert-butyldiphenylsilyl)oxy)-2-hydroxypentyl)thio)-6-chloroquinazoline-2,4(1H,3H)-dione (2)

To a mixture of 7-bromo-6-chloro-8-iodoquinazoline-2,4(1H,3H)-dione (572 mg, 1.42 mmol), Xantphos (123 mg, 0.21 mmol), $K_2CO_3$ (392 mg, 2.84 mmol) in dioxane (10 mL) was added 5-((tert-butyldiphenylsilyl)oxy)-1-mercaptopentan-2-ol (800 mg, 2.14 mmol) and $PD_2$ $(dba)_3$ (128 mg, 0.14 mmol) at rt. The reaction mixture was stirred at 50° C. under nitrogen atmosphere for 22 hours. After removing the solvent, the residue was purified by silica gel column chromatography (dichloromethane/methnol=100/1 to 50/1) to afford compound (2) (S)-7-bromo-8-((5-((tert-butyldiphenylsilypoxy)-2-hydroxypentyl)thio)-6-chloroquinazoline-2,4(1H,3H)-dione (510 mg, yield: 55%) as a light yellow solid.

LC-MS: m/z 647.6 $[M-H]^+$ (R)-10-bromo-3-(3-((tert-butyldiphenylsilypoxy)propyl)-9-chloro-2H-[1,4]thiazino[2,3,4-ij]quinazoline-5,7(3H,6H)-dione (3)

To a mixture of (S)-7-bromo-8-((5-((tert-butyldiphenylsilyl)oxy)-2-hydroxypentyl)thio)-6-chloroquinazoline-2,4

(1H,3H)-dione (1.0 g, 1.51 mmol) and triphenylphosphine (587.1 mg, 2.25 mmol) in THF (10 mL) was added DEAD (411.7 mg, 2.25 mmol) slowly at 0° C. under nitrogen atmosphere. The mixture was stirred at room temperature for 1 hour. The organic phase was washed with water (50 mL×2), dried over $Na_2SO_4$(S) and concentrated. The residue was purified by silica gel column with a gradient of PE/EA=0-50% to afford the product (788.1 mg, 1.25 mmol, yield: 83%) as a yellow solid. LC-MS: m/z=630.1 $[M-H]^+$.

(S)-tert-butyl 4-((R)-10-bromo-3-(3-((tert-butyldiphenylsilypoxy)propyl)-9-chloro-5-oxo-3,5-dihydro-2H-[1,4]thiazino[2,3,4-ij]quinazolin-7-yl)-3-methylpiperazine-1-carboxylate(4)

To a solution of (R)-10-bromo-3-(3-((tert-butyldiphenylsilypoxy)propyl)-9-chloro-2H-[1,4]thiazino[2,3,4-ij]quinazoline-5,7(3H,6H)-dione (1.68 mg, 2.67 mmol) and $K_2CO_3$ (1.84 g, 13.35 mmol) in ACN (20 mL) was added TPSCl (1.2 g, 4.05 mmol), the mixture was stirred at rt for 5 h. After the reaction was completed, (S)-tert-butyl 3-methylpiperazine-1-carboxylate (1.60 g, 8.01 mmol) was added. The resulting mixture was stirred at rt for 2 hours. After completion, the mixture was concentrated under reduced pressure and the residue was purified by silica gel column with a gradient of DCM/MeOH (30:1-20:1) to afford desired product (610 mg, 28% yield) as yellow solid. MS (ESI) m/z 813.2 $[M+H]^+$.

(S)-tert-butyl 4-((R)-10-bromo-9-chloro-3-(3-hydroxypropyl)-5-oxo-3,5-dihydro-2H-[1,4]thiazino[2,3,4-ij]quinazolin-7-yl)-3-methylpiperazine-1-carboxylate (5)

To a solution of (S)-tert-butyl 4-((R)-10-bromo-3-(3-((tert-butyldiphenylsilyl) oxy)propyl)-9-chloro-5-oxo-3,5-dihydro-2H-[1,4]thiazino[2,3,4-ij]quinazolin-7-yl)-3-methylpiperazine-1-carboxylate (610 mg, 0.75 mmol) in THF (5 mL) was added TBAF (1 mL, 1M in THF). The mixture was stirred at 20° C. for 2 hours. The reaction mixture was poured into water (50 mL) and extracted with EtOAc (20 mL×3). The combined organic phases were washed with brine (10 mL), dried over $Na_2SO_4$, and concentrated. The residue was purificatied by silica gel column with as gradient of DCM/MeOH (30:1-20:1) to give the product (320 mg, 0.56 mmol) as yellow solid. LC-MS: m/z 575.1 $[M+H]^+$ (S)-tert-butyl 4-((R)-10-bromo-9-chloro-5-oxo-3-(3-oxopropyl)-3,5-dihydro-2H-[1,4]thiazino[2,3,4-ij]quinazolin-7-yl)-3-methylpiperazine-1-carboxylate (6)

To a solution of 4-((R)-10-bromo-9-chloro-3-(3-hydroxypropyl)-5-oxo-3,5-dihydro-2H-[1,4]thiazino[2,3,4-ij]quinazolin-7-yl)-3-methylpiperazine-1-carboxylate(5) (290 mg, 0.5 mmol) in DCM (5 mL) was added Dess-martin reagent (318 mg, 0.75 mmol). The mixture was stirred at 20° C. under nitrogen atmosphere for 2 hours. After removing the solvent, the residue was purified by silica gel column chromatography (dichloromethane/methanol=30/1) to give the product (275 mg, 96% yield) as yellow solid. LC-MS: m/z 573.1 $[M+H]^+$ (S)-tert-butyl 4-((R)-3-(3-((1S,4S)-2-oxa-5-azabicyclo[2.2.1]heptan-5-yl)propyl)-10-bromo-9-chloro-5-oxo-3,5-dihydro-2H-[1,4]thiazino[2,3,4-ij]quinazolin-7-yl)-3-methylpiperazine-1-carboxylate (7)

To a solution of (S)-tert-butyl 4-((R)-10-bromo-9-chloro-5-oxo-3-(3-oxopropyl)-3,5-dihydro-2H-[1,4]thiazino[2,3,4-ij]quinazolin-7-yl)-3-methylpiperazine-1-carboxylate (275 mg, 0.50 mmol) and (1S,4S)-2-oxa-5-azabicyclo[2.2.1]heptane (150 mg, 1.5 mmol) in DCM was added sodium cyanoborohydride (150 mg, 0.75 mmol). The mixture was stirred at 20° C. for 2 hours. After removing the solvent, the residue was purified by silica gel column chromatography (dichloromethane/methanol=20/1) to give the desired product (300 mg, 90% yield) as yellow solid. LC-MS: m/z 656.2 $[M+H]^+$ (3S)-tert-butyl 4-((3R)-3-(3-((1S,4S)-2-oxa-5-azabicyclo[2.2.1]heptan-5-yl)propyl)-9-chloro-10-(2,4-difluorophenyl)-5-oxo-3,5-dihydro-2H-[1,4]thiazino[2,3,4-ij]quinazolin-7-yl)-3-methylpiperazine-1-carboxylate (8)

A mixture of (S)-tert-butyl 4-((R)-3-(3-((1S,4S)-2-oxa-5-azabicyclo[2.2.1]heptan-5-yl)propyl)-10-bromo-9-chloro-5-oxo-3,5-dihydro-2H-[1,4]thiazino[2,3,4-ij]quinazolin-7-yl)-3-methylpiperazine-1-carboxylate (140 mg, 0.21 mmol), (2,4-difluorophenyl)boronic acid (160 mg, 1.05 mmol), Pd(dppf)$Cl_2$ (15 mg, 0.02 mmol) and $K_3PO_4$ (125 mg, 0.63 mmol) in dioxane (5 mL) and $H_2O$ (0.8 mL) was heated to 85° C. under nitrogen atmosphere for 3 hours. The mixture was concentrated, and the residue was purified by silica gel column chromatography (dichloromethane/methanol=30/1) to give the crude product (130 mg, crude) as brown solid. LC-MS: m/z 688.2 $[M+H]^+$ (3R)-3-(3-((1S,4S)-2-oxa-5-azabicyclo[2.2.1]heptan-5-yl)propyl)-7-((S)-4-acryloyl-2-methylpiperazin-1-yl)-9-chloro-10-(2,4-difluorophenyl)-2H-[1,4]thiazino[2,3,4-ij]quinazolin-5(3H)-one (9)

The mixture of (3S)-tert-butyl 4-((3R)-3-(3-((1S,4S)-2-oxa-5-azabicyclo[2.2.1]heptan-5-yl)propyl)-9-chloro-10-(2,4-difluorophenyl)-5-oxo-3,5-dihydro-2H-[1,4]thiazino[2,3,4-ij]quinazolin-7-yl)-3-methylpiperazine-1-carboxylate (130 mg, 0.19 mmol) in DCM/TFA (3 mL/1 mL) was stirred at 20° C. for 1 hour. Removing solvent in vacuo gave the crude product as the TFA salt (160 mg, crude).

To the mixture of above product (160 mg, crude) and triethyl amine (57 mg, 0.57 mmol) in dichloromethane (3 mL) was added acrylic anhydride (47.8 mg, 0.38 mmol) slowly at 0° C. The mixture was stirred for 1 hour. After removing solvent in vacuo, the residue was purified by prep-HPLC to afford the desired product (60 mg, 50% yield) as white solid. LC-MS: m/z 642.2 $[M+H]^+$.

D. Example 76

7-((S)-4-acryloyl-2-methylpiperazin-1-yl)-9-chloro-10-(2,4-difluorophenyl)-2,2-dimethyl-2,3-dihydro-5H-[1,4]thiazino[2,3,4-ij]quinazolin-5-one

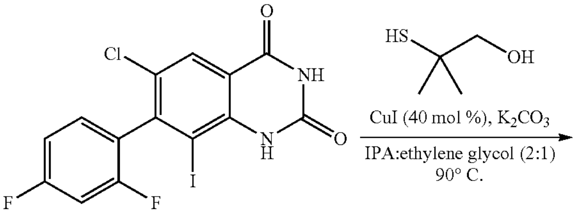

1

-continued

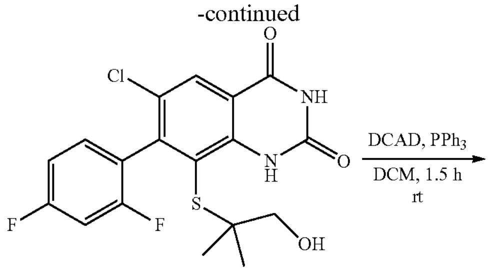

2

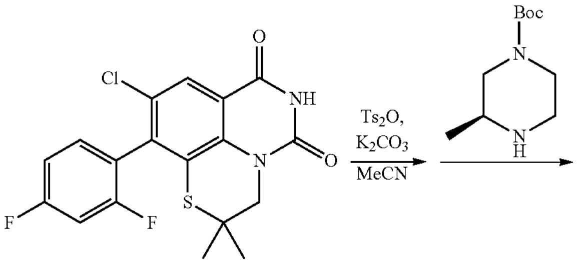

3

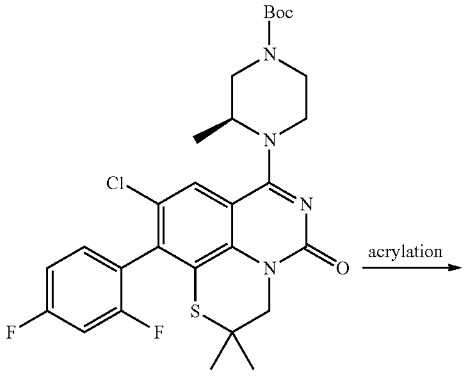

4

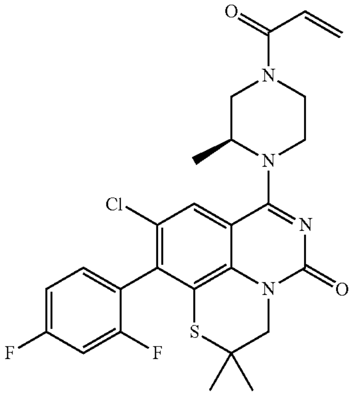

5

6-chloro-7-(2,4-difluorophenyl)-8-((l-hydroxy-2-methylpropan-2-yl)thio)quinazoline-2,4(1H,3H)-dione (2)

Compound 1 (50 mg, 0.123 mmol, 1 equiv) and 2-mercapto-2-methylpropan-1-ol (26 mg, 0.246 mmol, 2 equiv) was added to a 5 mL microwave vial and dissolved in 2-isopropyl alcohol (0.5 mL) and ethylene glycol (0.25 mL). Next, the solution was degassed with $N_2$ for 30 min and CuI (9.4 mg, 0.049 mmol, 0.4 equiv) and $K_2CO_3$ (53 mg, 0.381 mmol, 3 equiv) were added followed by additional degassing with $N_2$ for 20 min. The microwave vial was fitted with a crimp-top cap and placed on a heated block at 90° C. The resulting reaction mixture was heterogenous and light tan in color. After 33 hours, the vial was removed from the heating block, allowed to cool, and the solvent was removed under reduced pressure. This was performed in two separate batches (50 mg, each) and combined. The combined crude material was suspended in $CH_2Cl_2$ and filtered. The filtrate was collected, and the solvent was removed by rotary evaporation. The crude material was purified by flash column chromatography using an Isolera One Biotage instrument (0-4% MeOH/$CH_2Cl_2$, 10 g column, 0% (5 CV), 0-4% (20 CV), 4% (5 CV)) to provide a brown oil (45 mg) containing unknown impurities, but used in the subsequent step: TLC (3% MeOH/$CH_2Cl_2$) $R_f$=0.17; $^1$H NMR (400 MHz, $CDCl_3$) δ 8.27 (dd, J=8.8 Hz, 1H), 7.14-6.91 (m, 3H), 4.01-3.82 (m, 2H), 3.51-3.30 (m, 2H), 1.34 (s, 3H), 1.30 (s, 3H); LRMS-ESI (m/z) $[M+H]^+$ calculated for $C_{18}H_{16}ClF_2N_2O_3S$ 413.05, found 413.1.

9-chloro-10-(2,4-difluorophenyl)-2,2-dimethyl-2,3-dihydro-5H-[1,4]thiazino[2,3,4-ij]quinazoline-5,7(6H)-dione (3)

Compound 2 (20 mg, 0.048 mmol, 1 equiv) and $PPh_3$ (19 mg, 0.073 mmol, 1.5 equiv) was added to a 10 mL round-bottom flask under a $N_2$ atmosphere and dissolved in $CH_2Cl_2$ (1 mL, 0.05M). A solution of DCAD (27 mg, 0.073 mmol, 1.5 equiv) in $CH_2Cl_2$ (0.73 mL, 0.5M) was added dropwise to the reaction mixture at room temperature. After 1 h, the reaction reached 31% conversion determined by LC-MS. Additional DCAD (27 mg, 0.073 mmol, 1.5 equiv) and $PPh_3$ (19 mg, 0.073 mmol, 1.5 equiv) was added to the reaction mixture and after 15 min the reaction reached full conversion by LC-MS. The reaction mixture was diluted with $CH_2Cl_2$ (ca. 50 mL) and the precipitate filtered. The filtrate was collected, and the solvent was removed by rotary evaporation. The crude material was purified by preparative thin-layer chromatography (Silica Gel 60 $F_{254}$, 0.5 mm) using 3% MeOH/$CH_2Cl_2$ to provide compound 3 (13 mg, 68%) as a white solid: TLC (3% MeOH/$CH_2Cl_2$) $R_f$=0.51; $^1$H NMR (400 MHz, MeOH-$d_4$) δ 7.98 (s, 1H), 7.18-7.04 (m, 3H), 4.24 (d, J=13.4 Hz, 1H), 3.98 (d, J=13.4 Hz, 1H), 1.40 (s, 3H), 1.37 (s, 3H); LRMS-ESI (m/z) $[M-H]^-$ calculated for $C_{18}H_{12}ClF_2N_2O_2S$ 393.03, found 393.0.

tert-Butyl (3S)-4-(9-chloro-10-(2,4-difluorophenyl)-2,2-dimethyl-5-oxo-2,3-dihydro-5H-[1,4]thiazino[2,3,4-ij]quinazolin-7-yl)-3-methylpiperazine-1-carboxylate (4)

Compound 3 (13 mg, 0.033 mmol, 1 equiv) was dissolved in MeCN (0.4 mL, 0.1 M) under a $N_2$ atmosphere in a 1 dr vial. $K_2CO_3$ (13.7 mg, 0.099 mmol, 3 equiv) was added to the reaction mixture and the reaction mixture was briefly sonicated. p-Toluenesulfonic anhydride (22 mg, 0.066 mmol, 2 equiv) was added to the reaction mixture at room temperature. The reaction mixture was stirred for 14 h and reached near full conversion determined by LC-MS. Next, tert-butyl (S)-3-methylpiperazine-1-carboxylate (13.2 mg, 0.066 mmol, 2 equiv) and $K_2CO_3$ (13.2 mg, 0.066 mmol, 2 equiv) was added to the vial and stirred for 15 min at room temperature. The intermediate was determined to be fully consumed by LC-MS and the solvent was removed by under reduced pressure. The mixture was transferred with $CH_2Cl_2$ to a separatory funnel, washed with aqueous saturated $NH_4Cl$ (10 mL) and $H_2O$ (10 mL), extracted with $CH_2Cl_2$ (2×50 mL), dried over $Na_2SO_4$, and filtered. The solvent was removed by rotary evaporation to afford compound 4 (26 mg) as a yellow oil which contained starting material (~47%; determined by LC-MS) in addition to other minor unknown impurities. This material was used as is in the subsequent step: TLC (3% $MeOH/CH_2Cl_2$)$R_f$=0.32; LRMS-ESI (m/z) $[M+H]^+$ calculated for $C_{28}H_{32}ClF_2N_4O_3S$ 577.19, found 577.2.

7-((S)-4-acryloyl-2-methylpiperazin-1-yl)-9-chloro-10-(2,4-difluorophenyl)-2,2-dimethyl-2,3-dihydro-5H-[1,4]thiazino[2,3,4-ij]quinazolin-5-one (5)

Compound 4 (26 mg crude, 0.045 mmol, 1 equiv) was dissolved in anhydrous $CH_2Cl_2$ (3 mL) in a 20 dr vial followed by the addition of $CF_3COOH$ (1 mL) at room temperature and capped. After 15 min, the reaction was determined to be complete by LC-MS and the solvent was removed by rotary evaporation. The reaction mixture was dissolved in MeOH, loaded onto a HyperSep SCX plug, and flushed with MeOH (ca. 20 mL). Next, the desired intermediate was eluted with 1N $NH_3$ in MeOH (ca. 20 mL) and collected. The solvent was removed by rotary evaporation and the crude material was dissolved in anhydrous $CH_2Cl_2$ (3 mL) in a 20 dr vial and capped. Next, DIPEA (8 μL, 0.045 mmol, 1 equiv) was added by syringe to the reaction at room temperature followed by acryloyl chloride (3.6 μL, 0.045 mmol, 1 equiv) and capped. After 15 min, the reaction was determined to be complete by LC-MS and the solvent was removed by rotary evaporation. The crude material was dissolved in MeOH, filtered with a 0.45 μm PTFE plug, and purified by preparative RP-HPLC (Luna 5 μM C18(2) 100 Å, 100×30 mm, 5-95% MeCN+0.1% (v/v) HCOOH and $H_2O$+0.1% (v/v) HCOOH). The product fractions were collected, and the solvent was removed by rotary evaporation, followed by lyophilization (−91 to −71° C.; <0.01 mbar) in deionized water to afford compound 5 (1.46 mg) as a white solid: $^1H$ NMR (400 MHz, MeOH-$d_4$) δ 7.71 (d, J=4.5 Hz, 1H), 7.33-7.22 (m, 1H), 7.18-7.09 (m, 2H), 6.91-6.73 (m, 1H), 6.29 (dd, J=16.2. 7.2 Hz, 1H), 5.81 (dd, J=10.6. 1.9 Hz, 1H), 4.68-3.93 (m, 5H), 3.80-3.45 (m, 2H), 1.42 (s, 3H), 1.38 (s, 3H); LRMS-ESI (m/z) $[M+H]^+$ calculated for $C_{26}H_{26}ClF_2N_4O_2S$ 531.14, found 531.2.

E. Example 350

(3S)-7-((S)-4-acryloyl-2-methylpiperazin-1-yl)-10-(2,4-difluorophenyl)-3-((4-ethylpiperazin-1-yl)methyl)-9-(trifluoromethyl)-2H-[1,4]thiazino[2,3,4-ij]quinazolin-5(3H)-one

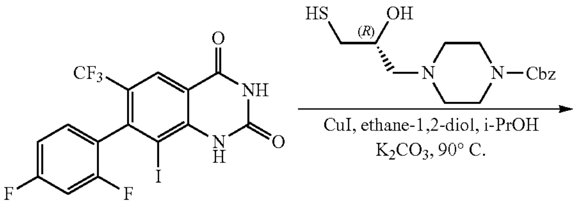

1

-continued

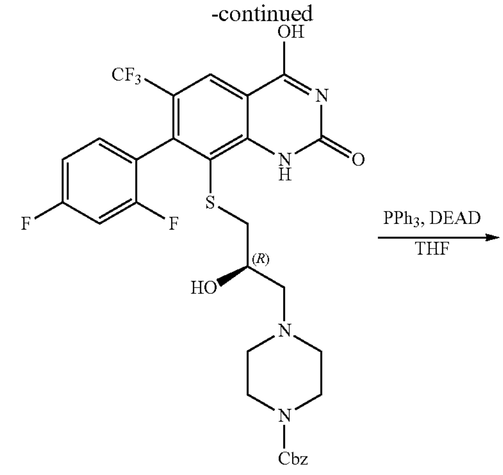

2

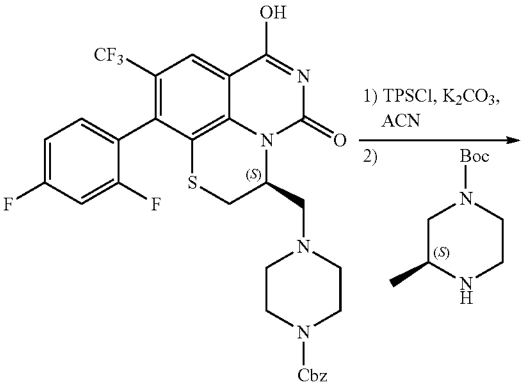

3

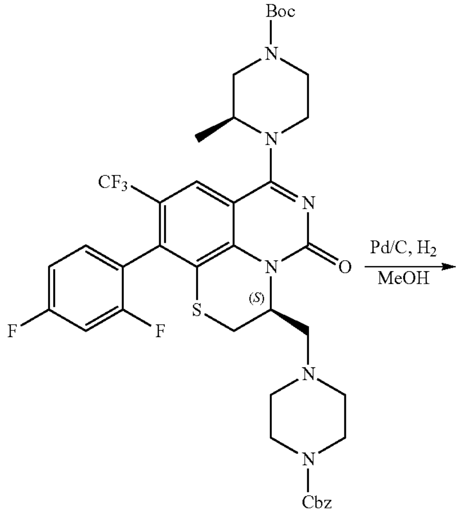

4

-continued

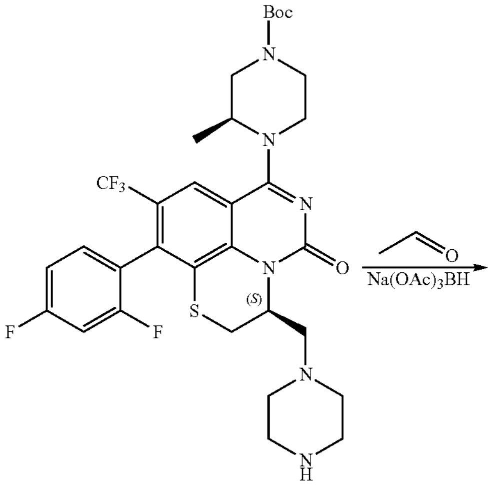

5

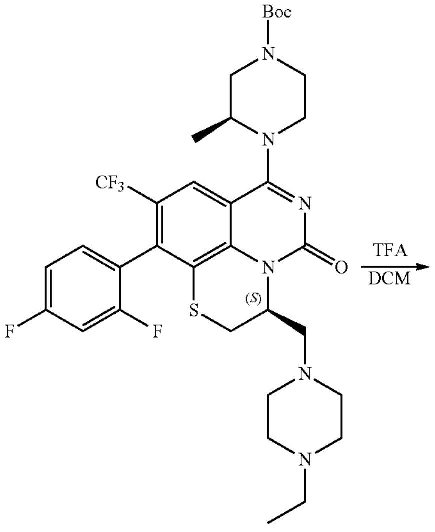

6

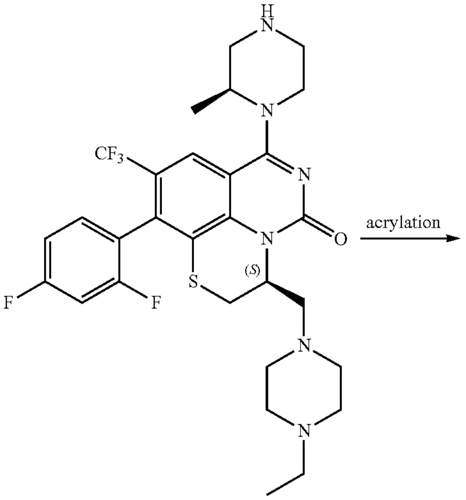

7

-continued

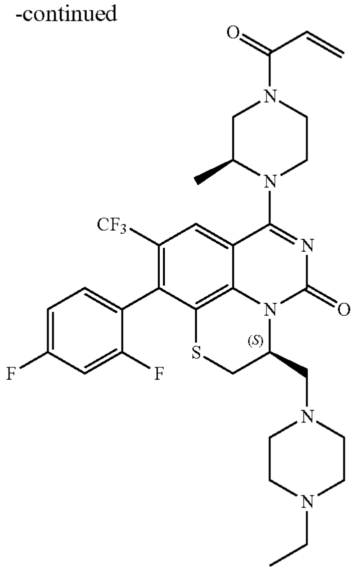

8 benzyl 4-((2R)-3-((7-(2,4-difluorophenyl)-4-hydroxy-2-oxo-6-(trifluoromethyl)-1,2-dihydroquinazolin-8-yl)thio)-2-hydroxypropyl)piperazine-1-carboxylate (2)

The mixture of 7-(2,4-difluorophenyl)-8-iodo-6-(trifluoromethyl)quinazoline-2,4(1H,3H)-dione (2.3 g, 4.91 mmol), (R)-benzyl 4-(2-hydroxy-3-mercaptopropyl)piperazine-1-carboxylate (2.28 g, 7.38 mmol), CuI (750 mg, 3.93 mmol) and $K_2CO_3$ (2.03 g, 14.73 mmol) in ethane-1,2-diol (30 mL) and i-PrOH (30 mL) was stirred under nitrogen atmosphere at 85° C. for 22 hours. After removing solvent in vacuo, the residue was purified by silica gel column using DCM/MeOH=50:1 as eluent to afford the title product (1.2 g, 1.84 mmol, 37% yield) as a light yellow solid. MS (ESI) m/z 651.5 $[M+H]^+$.

benzyl 4-(((3S)-10-(2,4-difluorophenyl)-7-hydroxy-5-oxo-9-(trifluoromethyl)-3,5-dihydro-2H-[1,4]thiazino[2,3,4-ij]quinazolin-3-yl)methyl)piperazine-1-carboxylate (3)

To a mixture of benzyl 4-((2R)-3-((7-(2,4-difluorophenyl)-4-hydroxy-2-oxo-6-(trifluoromethyl)-1,2-dihydroquinazolin-8-yl)thio)-2-hydroxypropyl)piperazine-1-carboxylate (1.2 g, 1.84 mmol) and triphenylphosphine (964 mmol, 3.68 mmol) in THF (30 mL) was added DEAD (640 mg, 3.68 mmol) slowly at 0° C. under nitrogen atmosphere. The mixture was stirred at room temperature for 1 h. DCM (50 mL) was added. The organic phase was washed with water (50 mL×2), dried over $Na_2SO_4$, filtered and concentrated. The residue was purified by silica gel column with a gradien of PE/EA (10:1-5:1 to afford the desired product (710 mg, 1.12 mmol, 61% yield) as a light yellow solid. MS (ESI) m/z 633.6 $[M+H]^+$.

(3S)-tert-butyl 4-((3S)-3-((4-((benzyloxy)carbonyl)piperazin-1-yl)methyl)-10-(2,4-difluorophenyl)-5-oxo-9-(trifluoromethyl)-3,5-dihydro-2H-[1,4]thiazino[2,3,4-ij]quinazolin-7-yl)-3-methylpiperazine-1-carboxylate (4)

To a mixture of benzyl 4-(((3S)-10-(2,4-difluorophenyl)-7-hydroxy-5-oxo-9-(trifluoromethyl)-3,5-dihydro-2H-[1,4]

thiazino[2,3,4-ij]quinazolin-3-yl)methyl)piperazine-1-carboxylate (710 mg, 1.20 mmol) and $K_2CO_3$ (497 mg, 3.61 mmol) in ACN (20 mL) was added TPSCl (543 mg, 1.8 mmol). The mixture was stirred at rt for 5 h. After the reaction was completed, (S)-tert-butyl 3-methylpiperazine-1-carboxylate (720 mg, 3.6 mmol) and TEA (370 mg, 3.6 mmol) was added. The resulting mixture was stirred at rt for 2 hours. The reaction mixture was concentrated under reduced pressure and the residue was purified by silica gel column with a gradient of PE/EA (20%-80%) to afford desired product (720 mg, yield: 68%) as yellow solid. MS (ESI) m/z 815.3 $[M+H]^+$.

(3S)-tert-butyl 4-((3S)-10-(2,4-difluorophenyl)-5-oxo-3-(piperazin-1-ylmethyl)-9-(trifluoromethyl)-3,5-dihydro-2H-[1,4]thiazino[2,3,4-ij]quinazolin-7-yl)-3-methylpiperazine-1-carboxylate (5)

The mixture of benzyl 4-(((3S)-10-(2,4-difluorophenyl)-7-hydroxy-5-oxo-9-(trifluoromethyl)-3,5-dihydro-2H-[1,4]thiazino[2,3,4-ij]quinazolin-3-yl)methyl)piperazine-1-carboxylate (640 mg, 0.78 mmol) and Pd/C (500 mg) in methanol was stirred under hydrogen atmosphere for 3 hours. After filtration, the solvent was removed in vacuo. The residue was purification by silica gel column with a gradien of DCM/MeOH (5%-10%) to afford desired product (410 mg, 77% yield) as yellow solid. MS (ESI) m/z 680.2 $[M+H]^+$.

(3S)-tert-butyl 4-((3S)-10-(2,4-difluorophenyl)-3-((4-ethylpiperazin-1-yl)methyl)-5-oxo-9-(trifluoromethyl)-3,5-dihydro-2H-[1,4]thiazino[2,3,4-ij]quinazolin-7-yl)-3-methylpiperazine-1-carboxylate (6)

To a mixture of (3S)-tert-butyl 4-((3S)-10-(2,4-difluorophenyl)-5-oxo-3-(piperazin-1-ylmethyl)-9-(trifluoromethyl)-3,5-dihydro-2H-[1,4]thiazino[2,3,4-ij]quinazolin-7-yl)-3-methylpiperazine-1-carboxylate (150 mg, 0.22 mmol) and acetaldehyde (0.5 mL, 40% in water) in EtOH was added sodium triacetoxyborohydride (88 mg, 0.44 mmol). The mixture was stirred at 20° C. for 2 hours. After removing solvent in vacuo, the residue was purified by silica gel column chromatography (dichloromethane/methanol=30/1) to give the product (118 mg, 75% yield) as yellow solid. MS (ESI) m/z 709.2 $[M+H]^+$ (3S)-10-(2,4-difluorophenyl)-3-((4-ethylpiperazin-1-yl)methyl)-7-((S)-2-methylpiperazin-1-yl)-9-(trifluoromethyl)-2H-[1,4]thiazino[2,3,4-ij]quinazolin-5(3H)-one (7)

To a solution of (3S)-tert-butyl 4-((3S)-10-(2,4-difluorophenyl)-3-((4-ethylpiperazin-1-yl)methyl)-5-oxo-9-(trifluoromethyl)-3,5-dihydro-2H-[1,4]thiazino[2,3,4-ij]quinazolin-7-yl)-3-methylpiperazine-1-carboxylate (110 mg, 0.16 mmol) in DCM (3 mL) was added TFA (0.8 mL). The mixture was stirred at 20° C. for 2 hours. The mixture was concentrated to give the crude product as the TFA salt which was used in next step without further purification.

(3S)-7-((S)-4-acryloyl-2-methylpiperazin-1-yl)-10-(2,4-difluorophenyl)-3-((4-ethylpiperazin-1-yl)methyl)-9-(trifluoromethyl)-2H-[1,4]thiazino[2,3,4-ij]quinazolin-5(3H)-one (8)

To a mixture of (3S)-10-(2,4-difluorophenyl)-3-((4-ethylpiperazin-1-yl)methyl)-7-((S)-2-methylpiperazin-1-yl)-9-(trifluoromethyl)-2H-[1,4]thiazino[2,3,4-ij]quinazolin-5(3H)-one (80 mg, 0.13 mmol) and triethyl amine (41 mg, 0.40 mmol) in DCM (3 mL) was added acrylic anhydride (124.5 mg, 0.187 mmol) at 0° C. The mixture was stirred at 0° C. for 1 hour. After concentration, the residue was urified by prep-HPLC (5%-95% ACN in $H_2O$) to afford the product (25 mg, 29% yield) as white powder. $^1H$ NMR (400 MHz, $CDCl_3$) δ 7.75 (s, 1H), 7.20-7.15 (m, 1H), 7.04-6.93 (m, 2H), 6.62-6.53 (m, 1H), 6.39-6.52 (m, 1H), 5.75 (d, J=9.2 Hz, 1H), 5.37-5.28 (m, 1H), 4.72-4.68 (m, 1H), 4.51-4.26 (m, 2H), 3.99-3.38 (m, 5H), 3.11-2.97 (m, 2H), 2.82-2.76 (m, 3H), 2.59-2.37 (m, 8H), 1.26-1.22 (m, 3H), 1.09 (t, J=7.2 Hz, 3H). MS (ESI) m/z 663.3 $[M+H]^+$ F. Example 352

(3S)-7-((S)-4-acryloyl-2-methylpiperazin-1-yl)-10-(2,4-difluorophenyl)-3-((4-(oxetan-3-yl)piperazin-1-yl)methyl)-9-(trifluoromethyl)-2H-[1,4]thiazino[2,3,4-ij]quinazolin-5(3H)-one

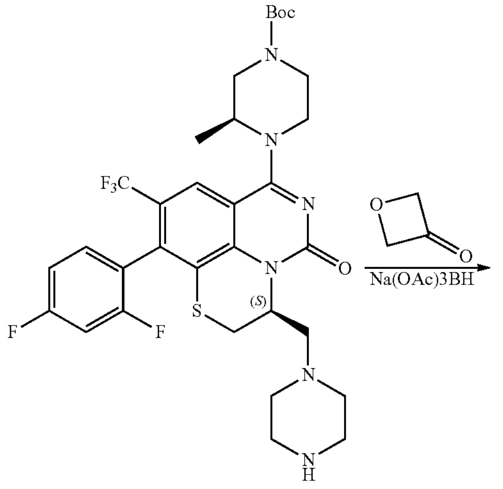

1

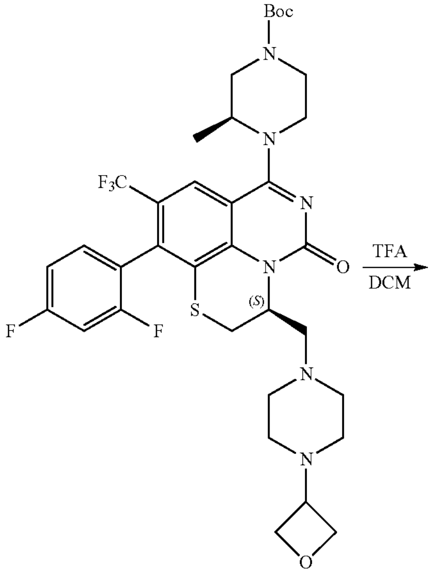

2

-continued

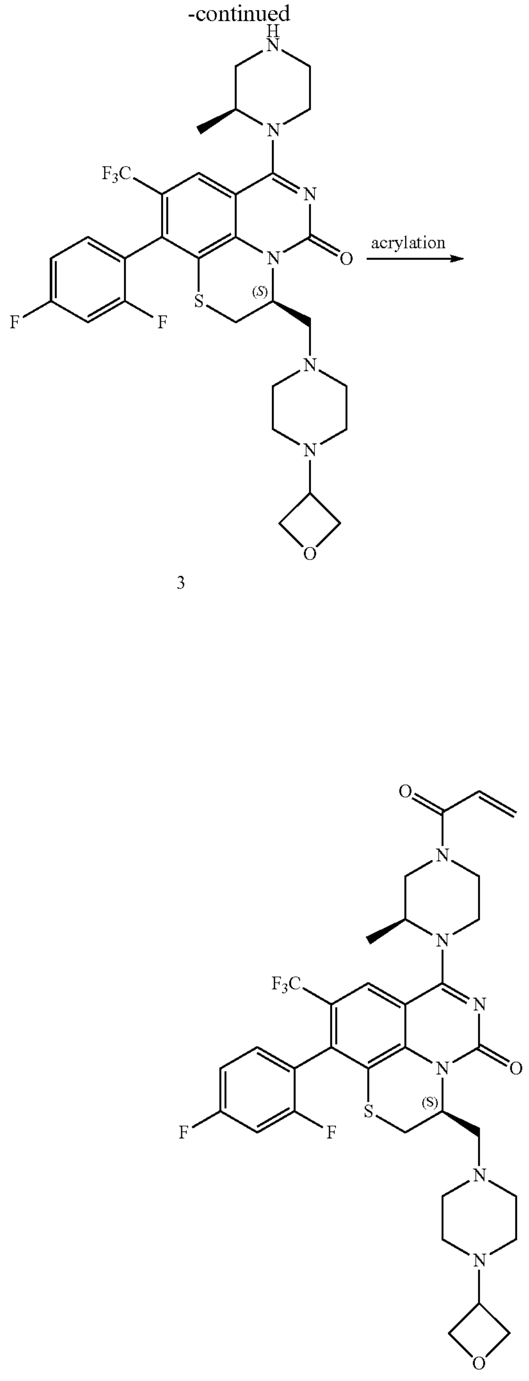

3

4

(3S)-tert-butyl4-((3S)-10-(2,4-difluorophenyl)-3-((4-(oxetan-3-yl)piperazin-1-yl)methyl)-5-oxo-9-(trifluoromethyl)-3,5-dihydro-2H-[1,4]thiazino[2,3,4-ij]quinazolin-7-yl)-3-methylpiperazine-1-carboxylate (2)

To a solution of (3S)-tert-butyl 4-((3S)-10-(2,4-difluorophenyl)-5-oxo-3-(piperazin-1-ylmethyl)-9-(trifluoromethyl)-3,5-dihydro-2H-[1,4]thiazino[2,3,4-ij]quinazolin-7-yl)-3-methylpiperazine-1-carboxylate (150 mg, 0.22 mmol) and oxetan-3-one (158 mg, 2.2 mmol) in DCM was added sodium triacetoxyborohydride (27 mg, 0.44 mmol). The mixture was stirred at 20° C. for 2 hours. After removing solvent in vacuo, the residue was purified by silica gel column chromatography (dichloromethane/methanol=30/1) to give the product (150 mg, crude) as yellow solid. MS (ESI) m/z 737.2 $[M+H]^+$ (3S)-10-(2,4-difluorophenyl)-7-((S)-2-methylpiperazin-1-yl)-3-((4-(oxetan-3-yl)piperazin-1-yl)methyl)-9-(trifluoromethyl)-2H-[1,4]thiazino[2,3,4-ij]quinazolin-5(3H)-one(3)

To a solution of (3S)-tert-butyl4-((3S)-10-(2,4-difluorophenyl)-3-((4-(oxetan-3-yl)piperazin-1-yl)methyl)-5-oxo-9-(trifluoromethyl)-3,5-dihydro-2H-[1,4]thiazino[2,3,4-ij]quinazolin-7-yl)-3-methylpiperazine-1-carboxylate (150 mg, crude) in DCM (3 mL) was added TFA (0.8 mL). The mixture was stirred at 20° C. for 1 hours. The mixture was concentrated to give the crude product as the TFA salt (160 mg, crude) which was used in next step without further purification.

(3S)-7-((S)-4-acryloyl-2-methylpiperazin-1-yl)-10-(2,4-difluorophenyl)-3-((4-(oxetan-3-yl)piperazin-1-yl)methyl)-9-(trifluoromethyl)-2H-[1,4]thiazino[2,3,4-ij]quinazolin-5(3H)-one(4)

To a solution of (3S)-10-(2,4-difluorophenyl)-7-((S)-2-methylpiperazin-1-yl)-3-((4-(oxetan-3-yl)piperazin-1-yl)methyl)-9-(trifluoromethyl)-2H-[1,4]thiazino[2,3,4-ij]quinazolin-5(3H)-one (130 mg, 0.18 mmol) and triethyl amine (61 mg, 0.60 mmol) in DCM (3 mL) was added acrylic anhydride (51.0 mg, 0.41 mmol) at 0° C. The mixture was stirred at 0° C. for 1 hour. After removing solvent in vacuo, the residue was purified by prep-HPLC (5%-95% ACN in $H_2O$) to afford the product (24 mg, 0.04 mmol) as white powder. 1H NMR (400 MHz, $CDCl_3$) δ 7.77 (s, 1H), 7.21-7.15 (m, 1H), 7.04-6.93 (m, 2H), 6.65-6.35 (m, 2H), 5.78 (d, J=8.4 Hz, 1H), 5.33-5.30 (m, 1H), 4.69-4.42 (m, 7H), 3.80-3.40 (m, 6H), 3.08-2.99 (m, 2H), 2.88-2.74 (m, 3H), 2.58-2.53 (m, 3H), 2.31-2.17 (m, 3H), 1.49-1.48 (m, 3H). MS (ESI) m/z 691.2 $[M+H]^+$ G. Example 353

(3S)-7-((S)-4-acryloyl-2-methylpiperazin-1-yl)-10-(2,4-difluorophenyl)-3-((1-ethylpiperidin-4-yl)methyl)-9-(trifluoromethyl)-2H-[1,4]thiazino[2,3,4-ij]quinazolin-5(3H)-one

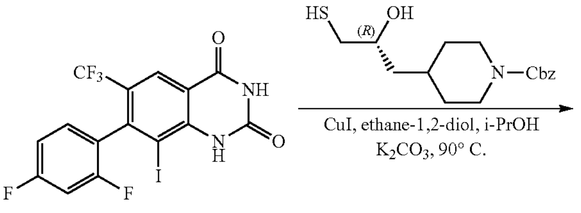

1

-continued
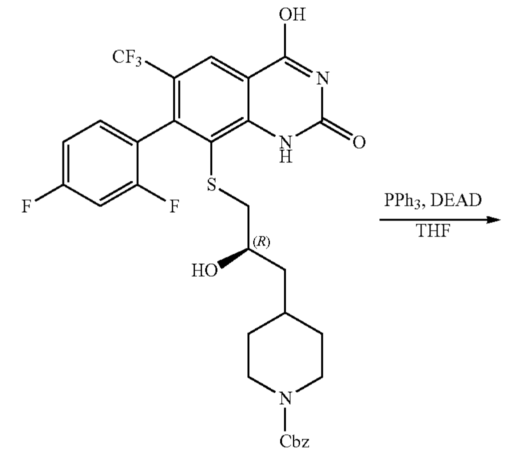
2
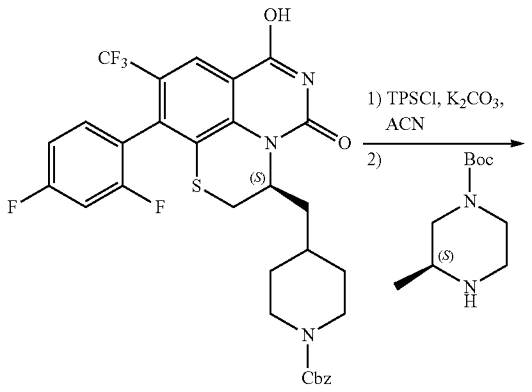
3
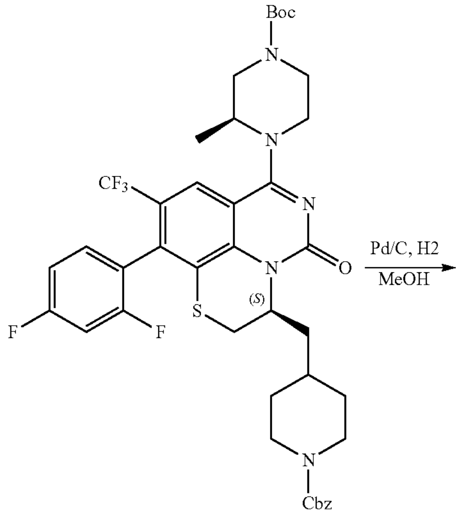
4
-continued
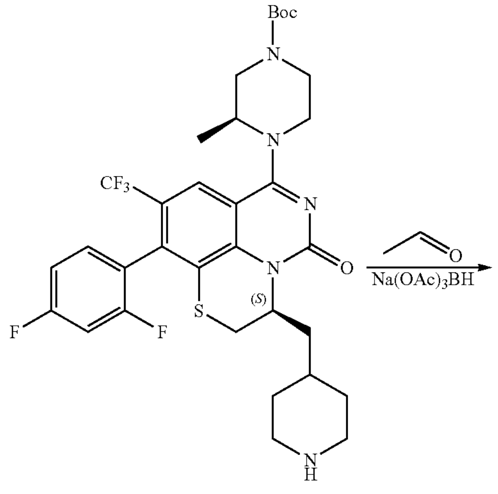
5
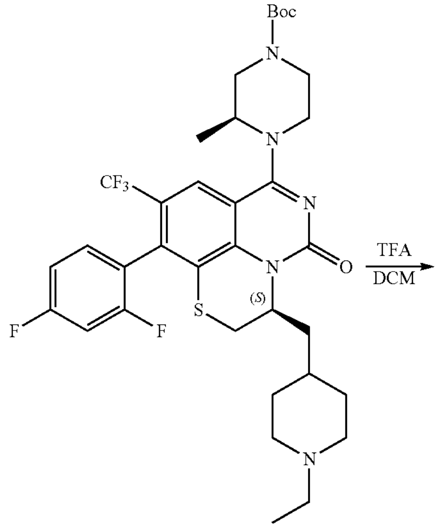
6
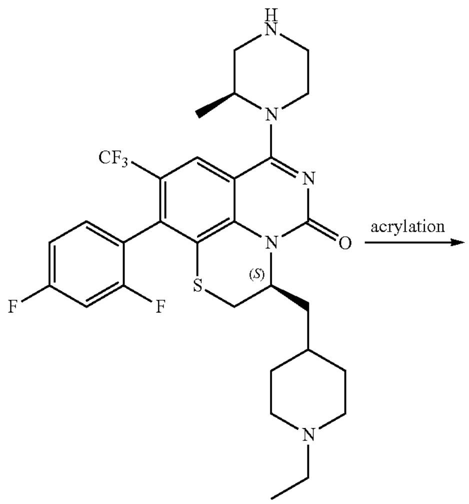
7

-continued

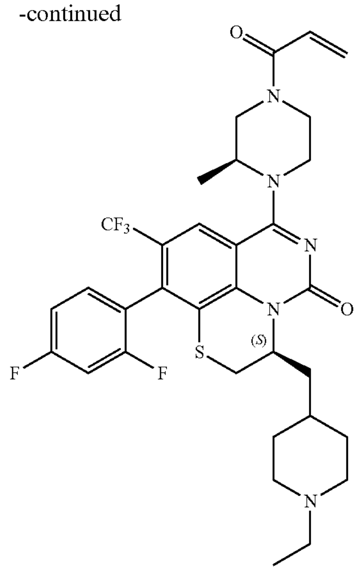

8 benzyl 4-((2R)-3-((7-(2,4-difluorophenyl)-4-hydroxy-2-oxo-6-(trifluoromethyl)-1,2-dihydroquinazolin-8-yl)thio)-2-hydroxypropyl)-5,6-dihydropyridine-1 (2H)-carboxylate (2)

A mixture of 7-(2,4-difluorophenyl)-8-iodo-6-(trifluoromethyl)quinazoline-2,4(1H,3H)-dione (1.17 g, 2.5 mmol), (R)-benzyl 4-(2-hydroxy-3-mercaptopropyl)-5,6-dihydropyridine-1(2H)-carboxylate (1.0 g, 3.25 mmol), CuI (381 mg, 2.0 mmol) and $K_2CO_3$ (1.04 g, 7.5 mmol) in ethane-1, 2-diol (10 mL) and i-PrOH (10 mL) was stirred under nitrogen atmosphere at 85° C. for 4 hours. After completion, the mixture was concentrated and the residue was purified by silica gel column using a mixture of DCM/EA (3:1) to afford the desired product (725 mg, 1.12 mmol, 44% yield) as a light yellow solid. MS (ESI) m/z 648.7 $[M+H]^+$.

benzyl 4-(((3S)-10-(2,4-difluorophenyl)-7-hydroxy-5-oxo-9-(trifluoromethyl)-3,5-dihydro-2H-[1,4]thiazino[2,3,4-ij]quinazolin-3-yl)methyl)-5,6-dihydropyridine-1(2H)-carboxylate (3)

To a solution of benzyl 4-((2R)-3-((7-(2,4-difluorophenyl)-4-hydroxy-2-oxo-6-(trifluoromethyl)-1,2-dihydroquinazolin-8-yl)thio)-2-hydroxypropyl)-5,6-dihydropyridine-1 (2H)-carboxylate (525 mg, 0.81 mmol) and triphenylphosphine (850 mmol, 3.25 mmol) in THF (150 mL) was added DEAD (566 mg, 3.25 mmol) slowly at 0° C. under nitrogen atmosphere. The mixture was stirred at room temperature for 1 h. EtOAc (150 mL) was added. The organic phase was washed with water (100 mL×2), dried over $Na_2SO_4$, filtered and concentrated. The residue was purified by C18 with 30-95% ACN in $H_2O$ to afford the desired product (390 mg, 0.62 mmol, yield: 77%) as a light yellow solid. MS (ESI) m/z 630.7 $[M+H]^+$.

(3S)-tert-butyl 4-((3S)-3-((1-((benzyloxy)carbonyl)-1,2,3,6-tetrahydropyridin-4-yl)methyl)-10-(2,4-difluorophenyl)-5-oxo-9-(trifluoromethyl)-3,5-dihydro-2H-[1,4]thiazino[2,3,4-ij]quinazolin-7-yl)-3-methylpiperazine-1-carboxylate (4)

To a solution of benzyl 4-(((3S)-10-(2,4-difluorophenyl)-7-hydroxy-5-oxo-9-(trifluoromethyl)-3,5-dihydro-2H-[1,4]thiazino[2,3,4-ij]quinazolin-3-yl)methyl)-5,6-dihydropyridine-1(2H)-carboxylate (390 mg, 0.62 mmol) and $K_2CO_3$ (856 mg, 6.2 mmol) in ACN (8 mL) was added $Ts_2O$ (304 mg, 0.93 mmol). The mixture was stirred at rt for 5 h. After the reaction was completed, (S)-tert-butyl 3-methylpiperazine-1-carboxylate (372 mg, 1.86 mmol) was added. The resulting mixture was stirred at rt for 20 min. After removing solvent in vacuo, the residue was purified by C18 with 30-95% ACN in $H_2O$ to afford desired product (280 mg, yield: 56%) as yellow solid. MS (ESI) m/z 812.2 $[M+H]^+$.

(3S)-tert-butyl 4-((3S)-10-(2,4-difluorophenyl)-5-oxo-3-(piperidin-4-ylmethyl)-9-(trifluoromethyl)-3,5-dihydro-2H-[1,4]thiazino[2,3,4-ij]quinazolin-7-yl)-3-methylpiperazine-1-carboxylate (5)

The mixture of (3S)-tert-butyl 4-((3S)-3-((1-((benzyloxy)carbonyl)-1,2,3,6-tetrahydropyridin-4-yl)methyl)-10-(2,4-difluorophenyl)-5-oxo-9-(trifluoromethyl)-3,5-dihydro-2H-[1,4]thiazino[2,3,4-ij]quinazolin-7-yl)-3-methylpiperazine-1-carboxylate (240 mg, 0.296 mmol) and Pd/C (500 mg) in EtOH was stirred under hydrogen atmosphere (50 psi) for 18 hours. After filtration, the filtrate was concentrated to afford crude product (200 mg, crude) as yellow solid. MS (ESI) m/z 680.1 $[M+H]^+$.

(3S)-tert-butyl 4-((3S)-10-(2,4-difluorophenyl)-3-((1-ethylpiperidin-4-yl)methyl)-5-oxo-9-(trifluoromethyl)-3,5-dihydro-2H-[1,4]thiazino[2,3,4-ij]quinazolin-7-yl)-3-methylpiperazine-1-carboxylate (6)

To a mixture of (3S)-tert-butyl 4-((3S)-10-(2,4-difluorophenyl)-5-oxo-3-(piperidin-4-ylmethyl)-9-(trifluoromethyl)-3,5-dihydro-2H-[1,4]thiazino[2,3,4-ij]quinazolin-7-yl)-3-methylpiperazine-1-carboxylate (200 mg, 0.296 mmol) and acetaldehyde (0.5 mL, 40% in water) in EtOH was added sodium triacetoxyborohydride (125 mg, 0.59 mmol). The mixture was stirred at 20° C. for 2 hours. After removing solvent in vacuo, the residue was purified by silica gel column chromatography (dichloromethane/methanol=30/1) to give the product (124 mg, 59% yield) as yellow solid. MS (ESI) m/z 708.2 $[M+H]^+$ (3S)-10-(2,4-difluorophenyl)-3-((1-ethylpiperidin-4-yl)methyl)-7-((S)-2-methylpiperazin-1-yl)-9-(trifluoromethyl)-2H-[1,4]thiazino[2,3,4-ij]quinazolin-5(3H)-one (7)

To the mixture of (3S)-tert-butyl 4-((3S)-10-(2,4-difluorophenyl)-3-((1-ethylpiperidin-4-yl)methyl)-5-oxo-9-(trifluoromethyl)-3,5-dihydro-2H-[1,4]thiazino[2,3,4-ij]quinazolin-7-yl)-3-methylpiperazine-1-carboxylate (124 mg, 0.17 mmol) in DCM (2 mL) was added TFA (2 mL). The mixture was stirred at 20° C. for 2 hours. The mixture was concentrated to give the crude product as the TFA salt which was used in next step without further purification.

(3S)-7-((S)-4-acryloyl-2-methylpiperazin-1-yl)-10-(2,4-difluorophenyl)-3-((1-ethylpiperidin-4-yl)methyl)-9-(trifluoromethyl)-2H-[1,4]thiazino[2,3,4-ij]quinazolin-5(3H)-one (8)

To a mixture of (3S)-10-(2,4-difluorophenyl)-3-((1-ethylpiperidin-4-yl)methyl)-7-((S)-2-methylpiperazin-1-yl)-9-(trifluoromethyl)-2H-[1,4]thiazino[2,3,4-ij]quinazolin-5(3H)-one (100 mg, 0.165 mmol) and triethyl amine (33 mg, 0.33 mmol) in DCM (2 mL) was added acrylic anhydride (21 mg, 0.165 mmol) at 0° C. The mixture was stirred at 0° C. for 1 hour. After removing solvent in vacuo, the residue was purified by silica gel column with DCM/MeOH (containing 5% $NH_3$)=30/1 to afford the product (40 mg, 37% yield) as white powder. $^1H$ NMR (400 MHz, $CDCl_3$) δ 7.79 (s, 1H), 7.29-7.15 (m, 1H), 7.06-6.95 (m, 2H), 6.61-6.53 (m, 1H), 6.37 (d, J=15.6 Hz, 1H), 5.78 (d, J=6.0 Hz, 1H), 5.43-5.38 (m, 1H), 4.71-4.69 (m, 1H), 4.52-4.27 (m, 2H), 3.98-3.95 (m, 0.5H), 3.83-3.80 (m, 0.5H), 3.61-3.43 (m, 2H), 3.13-2.92 (m, 5H), 2.42 (q, J=7.2 Hz, 2H), 2.01-1.90 (m, 3H), 1.78-1.72 (m, 3H), 1.52-1.32 (m, 6H), 1.09 (t, J=7.2 Hz, 3H). MS (ESI) m/z 662.2 [M+H]+.

H. Example 354

(3S)-7-((S)-4-acryloyl-2-methylpiperazin-1-yl)-9-chloro-10-(2,4-difluorophenyl)-3-((4-ethylpiperazin-1-yl)methyl)-2H-[1,4]thiazino[2,3,4-ij]quinazolin-5(3H)-one

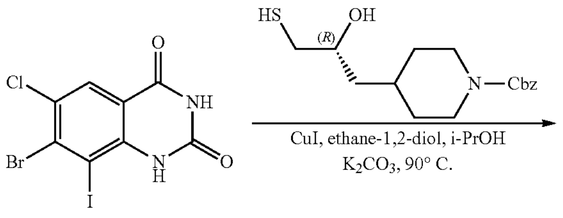

1

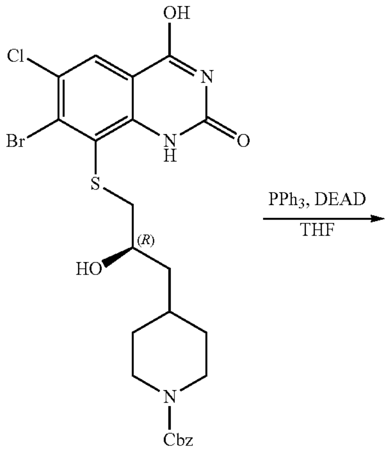

2

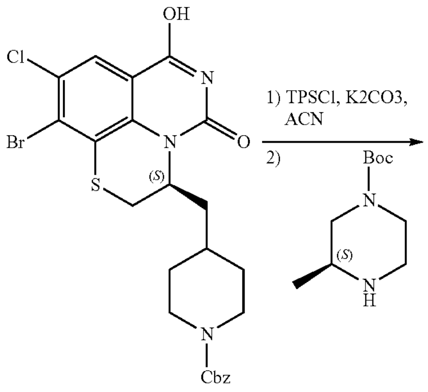

3

-continued

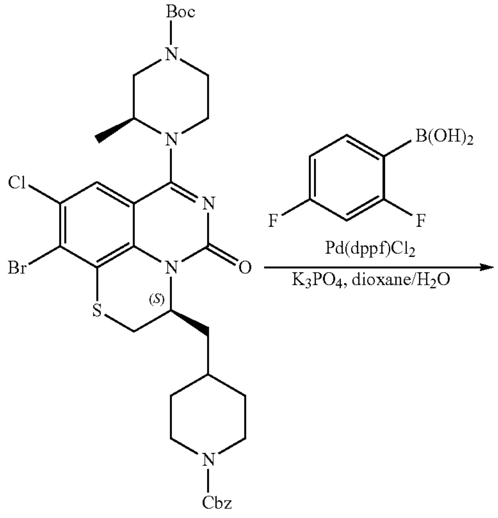

4

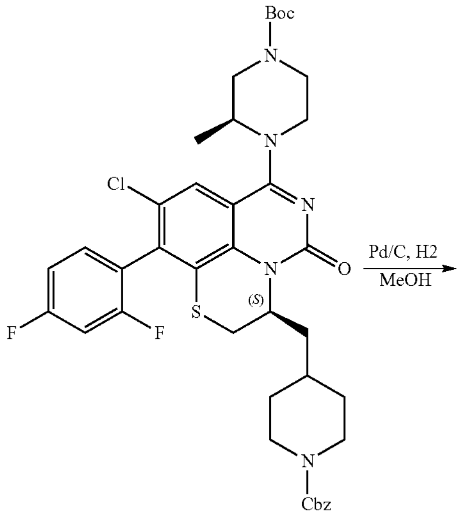

5

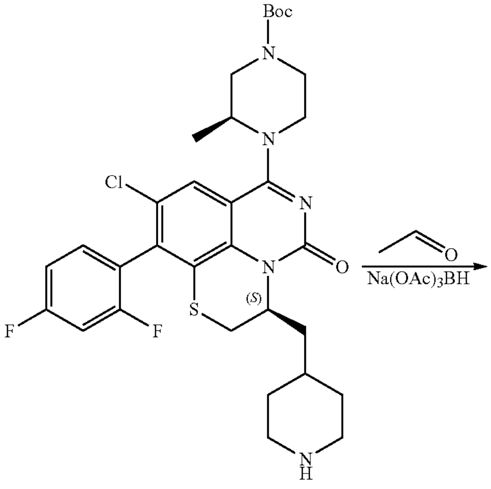

6

-continued

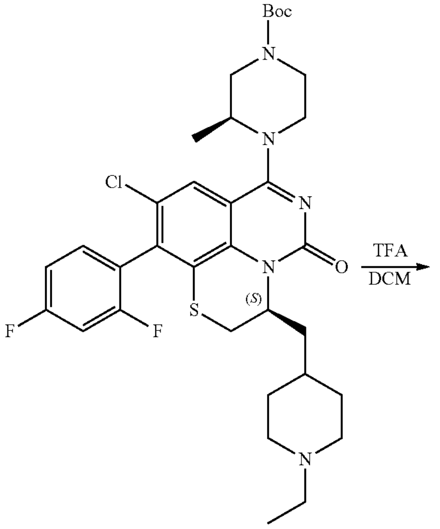

7

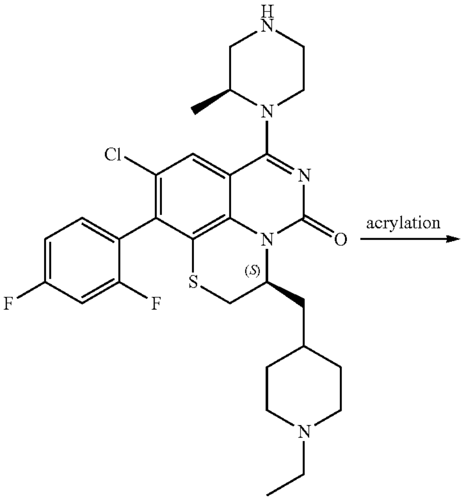

8

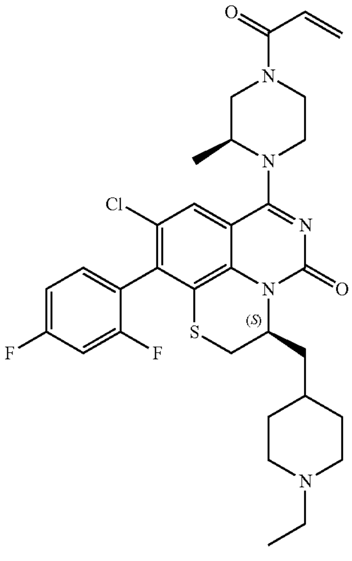

9

(R)-benzyl 4-(3-((7-bromo-6-chloro-4-hydroxy-2-oxo-1,2-dihydroquinazolin-8-yl)thio)-2-hydroxypropyl)piperidine-1-carboxylate (2)

The mixture of 7-bromo-6-chloro-8-iodoquinazoline-2,4 (1H,3H)-dione (4.9 g, 12.25 mmol), (R)-benzyl 4-(2-hydroxy-3-mercaptopropyl)piperidine-1-carboxylate (5.3 g, 17.15 mmol), $Pd_2(dba)_3$ (1.13 g, 1.23 mmol), XantPhos (1.06 g, 1.84 mmol) and $K_2CO_3$ (3.38 g, 24.5 mmol) in dioxane (60 mL) was stirred under nitrogen atmosphere at 50° C. for 18 hours. After removing solvent in vacuo, the residue was purified by silica gel column with a mixture of DCM/EA (3/1) to afford the product (3.8 g, yield: 54%) as a light yellow solid. MS (ESI) m/z 584.5 $[M+H]^+$.

(S)-benzyl 4-((10-bromo-9-chloro-7-hydroxy-5-oxo-3,5-dihydro-2H-[1,4]thiazino[2,3,4-ij]quinazolin-3-yl)methyl)piperidine-1-carboxylate (3)

To a mixture of (R)-benzyl 4-(3-((7-bromo-6-chloro-4-hydroxy-2-oxo-1,2-dihydroquinazolin-8-yl)thio)-2-hydroxypropyl)piperidine-1-carboxylate (3.38 g, 5.8 mmol) and triphenylphosphine (6.08 g, 23.2 mmol) in THF (1000 mL) was added DEAD (4.04 g, 23.2 mmol) slowly at 0° C. under nitrogen atmosphere. The mixture was stirred at room temperature for 1 h. The reaction mixture was concentrated and the residue was purified by C18 with 30-95% ACN in $H_2O$ to afford the product (2.4 g, 73% yield) as a light yellow solid. MS (ESI) m/z 566.5 $[M+H]^+$.

(S)-tert-butyl 4-((S)-3-((1-((benzyloxy)carbonyl) piperidin-4-yl)methyl)-10-bromo-9-chloro-5-oxo-3,5-dihydro-2H-[1,4]thiazino[2,3,4-ij]quinazolin-7-yl)-3-methylpiperazine-1-carboxylate (4)

To a solution of (S)-benzyl 4-((10-bromo-9-chloro-7-hydroxy-5-oxo-3,5-dihydro-2H-[1,4]thiazino[2,3,4-ij]quinazolin-3-yl)methyl)piperidine-1-carboxylate (1.2 g, 2.12 mmol) and $K_2CO_3$ (2.9 g, 21.2 mmol) in ACN (50 mL) was added $Ts_2O$ (1.38 g, 4.24 mmol). The mixture was stirred at rt for 5 h. After the reaction was completed, (S)-tert-butyl 3-methylpiperazine-1-carboxylate (1.2 g, 6.36 mmol) was added. The resulting mixture was stirred at rt for 20 min. After removing the solvent in vacuo, the residue was purified by C18 with 30-95% ACN in $H_2O$ to afford desired product (1.2 g, 80% yield) as yellow solid. MS (ESI) m/z 746.0 $[M+H]^+$.

(3S)-tert-butyl 4-((3S)-3-((1-((benzyloxy)carbonyl) piperidin-4-yl)methyl)-9-chloro-10-(2,4-difluorophenyl)-5-oxo-3,5-dihydro-2H-[1,4]thiazino[2,3,4-ij] quinazolin-7-yl)-3-methylpiperazine-1-carboxylate (5)

To a mixture of (S)-tert-butyl 4-((S)-3-((1-((benzyloxy) carbonyl)piperidin-4-yl)methyl)-10-bromo-9-chloro-5-oxo-3,5-dihydro-2H-[1,4]thiazino[2,3,4-ij]quinazolin-7-yl)-3-methylpiperazine-1-carboxylate (1.15 g, 1.5 mmol) and (2,4-difluorophenyl)boronic acid (1.2 g, 7.5 mmol) in dioxane (20 mL) and $H_2O$ (4 mL) was added $Pd(dppf)Cl_2$ (219 mg, 0.3 mmol) and $K_3PO_4$ (954 mg, 4.5 mmol). The mixture was stirred at 80° C. under $N_2$ for 12 hours. After filtration, the filtrate was concentrated to afford crude product (1.3 g, crude) as yellow solid. MS (ESI) m/z 780.1 $[M+H]^+$.

(3S)-tert-butyl 4-((3S)-9-chloro-10-(2,4-difluorophenyl)-5-oxo-3-(piperidin-4-ylmethyl)-3,5-dihydro-2H-[1,4]thiazino[2,3,4-ij]quinazolin-7-yl)-3-methylpiperazine-1-carboxylate (6)

The mixture of (3S)-tert-butyl 4-((3S)-3-((1-((benzyloxy)carbonyl)piperidin-4-yl)methyl)-9-chloro-10-(2,4-difluorophenyl)-5-oxo-3,5-dihydro-2H-[1,4]thiazino[2,3,4-ij]quinazolin-7-yl)-3-methylpiperazine-1-carboxylate (1.3 g, 1.6 mmol) and Pd/C (1.3 g) in EtOH was stirred under hydrogen atmosphere for 4 hours. After filtration, the filtrate was concentrated to afford crude product (850 mg, crude) as yellow solid. MS (ESI) m/z 646.8 $[M+H]^+$.

(3S)-tert-butyl 4-((3S)-9-chloro-10-(2,4-difluorophenyl)-3-((1-ethylpiperidin-4-yl)methyl)-5-oxo-3,5-dihydro-2H-[1,4]thiazino[2,3,4-ij]quinazolin-7-yl)-3-methylpiperazine-1-carboxylate (7)

To a mixture of (3S)-tert-butyl 4-((3S)-9-chloro-10-(2,4-difluorophenyl)-5-oxo-3-(piperidin-4-ylmethyl)-3,5-dihydro-2H-[1,4]thiazino[2,3,4-ij]quinazolin-7-yl)-3-methylpiperazine-1-carboxylate (200 mg, 0.3 mmol) and acetaldehyde (0.5 mL, 40% in water) in EtOH was added sodium triacetoxyborohydride (98 mg, 0.46 mmol). The mixture was stirred at 20° C. for 2 hours. After removing the solvent in vacuo, and the residue was purified by silica gel column chromatography (dichloromethane/methanol=10/1) to give the desired product (180 mg, 89% yield) as yellow solid. MS (ESI) m/z 674.2 $[M+H]^+$.

(3S)-9-chloro-10-(2,4-difluorophenyl)-3-((1-ethylpiperidin-4-yl)methyl)-7-((S)-2-methylpiperazin-1-yl)-2H-[1,4]thiazino[2,3,4-ij]quinazolin-5(3H)-one (8)

To the mixture of (3S)-tert-butyl 4-((3S)-9-chloro-10-(2,4-difluorophenyl)-3-((1-ethylpiperidin-4-yl)methyl)-5-oxo-3,5-dihydro-2H-[1,4]thiazino[2,3,4-ij]quinazolin-7-yl)-3-methylpiperazine-1-carboxylate (180 mg, 0.27 mmol) in DCM (2 mL) was added TFA (2 mL). The mixture was stirred at 20° C. for 2 hours. The reaction mixture was concentrated to give the crude product as the TFA salt, which was used in next step without further purification.

(3S)-7-((S)-4-acryloyl-2-methylpiperazin-1-yl)-9-chloro-10-(2,4-difluorophenyl)-3-((1-ethylpiperidin-4-yl)methyl)-2H-[1,4]thiazino[2,3,4-ij]quinazolin-5(3H)-one (9)

To a mixture of (3S)-10-(2,4-difluorophenyl)-3-((1-ethylpiperidin-4-yl)methyl)-7-((S)-2-methylpiperazin-1-yl)-9-(trifluoromethyl)-2H-[1,4]thiazino[2,3,4-ij]quinazolin-5(3H)-one (100 mg, 0.17 mmol) and triethyl amine (34 mg, 0.34 mmol) in DCM (2 mL) was added acrylic anhydride (22 mg, 0.17 mmol) at 0° C. The mixture was stirred at 0° C. for 1 hour. After removing solvent in vacuo, the residue was purified by prep-HPLC with a mixture of 5-95% ACN in $H_2O$ to afford the desired product (30 mg, 28% yield) as white powder. $^1H$ NMR (400 MHz, $CDCl_3$) δ 7.48 (s, 1H), 7.24-7.18 (m, 1H), 7.07-6.95 (m, 2H), 6.67-6.52 (m, 1H), 6.36 (d, J=16.8 Hz, 1H), 5.75 (d, J=10.4 Hz, 1H), 5.41-5.28 (m, 1H), 4.74-4.66 (m, 1H), 4.56-4.54 (m, 0.5H), 4.48-4.35 (m, 1H), 4.22-4.16 (m, 0.5H), 3.99-3.77 (m, 1H), 3.59-3.39 (m, 3H), 3.09-3.00 (m, 2H), 2.84-2.76 (m, 3H), 2.55-2.35 (m, 9H), 1.48-1.43 (m, 3H), 1.08-1.04 (m, 3H). MS (ESI) m/z 629.3 $[M+H]^+$.

I. Example 355

(3S)-7-((S)-4-acryloyl-2-methylpiperazin-1-yl)-9-chloro-10-(2,4-difluorophenyl)-3-((4-(oxetan-3-yl)piperazin-1-yl)methyl)-2H-[1,4]thiazino[2,3,4-ij]quinazolin-5(3H)-one

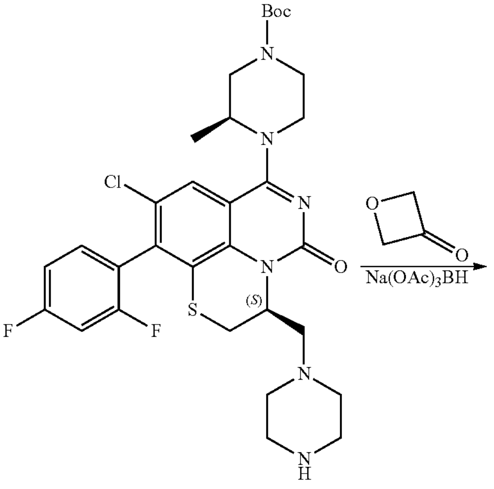

1

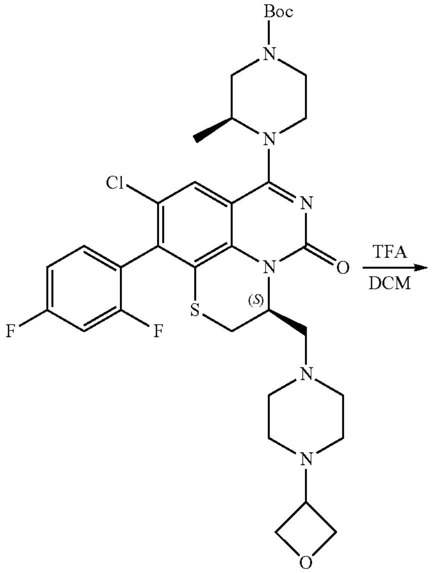

2

-continued

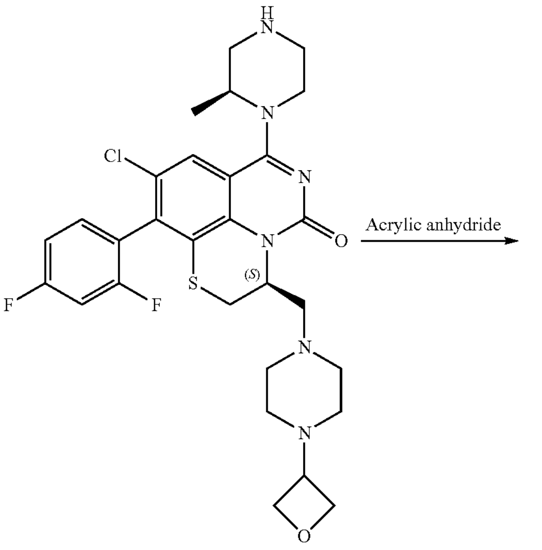

3

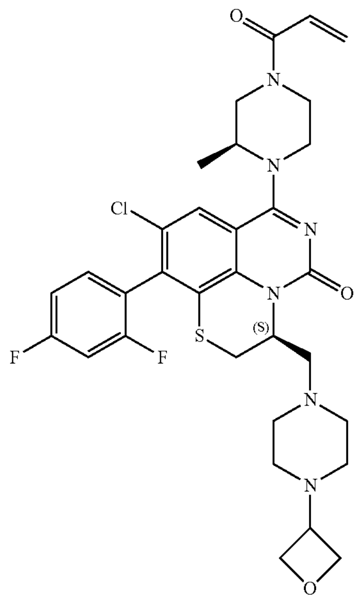

4

(3S)-tert-butyl 4-((3S)-9-chloro-10-(2,4-difluorophenyl)-3-((4-(oxetan-3-yl) piperazin-1-yl)methyl)-5-oxo-3,5-dihydro-2H-[1,4]thiazino[2,3,4-ij]quinazolin-7-yl)-3-methylpiperazine-1-carboxylate (2)

To a solution of (3S)-tert-butyl 4-((3S)-9-chloro-10-(2,4-difluorophenyl)-5-oxo-3-(piperazin-1-ylmethyl)-3,5-dihydro-2H-[1,4]thiazino[2,3,4-ij]quinazolin-7-yl)-3-methylpiperazine-1-carboxylate (200 mg, 0.31 mmol) and oxetan-3-one (1.5 mL) in DCM (1.5 mL) was added sodium triacetoxyborohydride (88 mg, 0.44 mmol). The mixture was stirred at 20° C. for 2 hours. After removing the solvent in vacuo, the residue was purified by silica gel column chromatography (dichloromethane/methanol=30/1) to give the desired product (120 mg, 55% yield) as yellow solid. MS (ESI) m/z 703.2 [M+H]$^+$ (3S)-9-chloro-10-(2,4-difluorophenyl)-7-((S)-2-methylpiperazin-1-yl)-3-((4-(oxetan-3-yl)piperazin-1-yl)methyl)-2H-[1,4]thiazino[2,3,4-ij]quinazolin-5(3H)-one (3)

To a solution of (3S)-tert-butyl 4-((3S)-9-chloro-10-(2,4-difluorophenyl)-3-((4-(oxetan-3-yl)piperazin-1-yl)methyl)-5-oxo-3,5-dihydro-2H-[1,4]thiazino[2,3,4-ij]quinazolin-7-yl)-3-methylpiperazine-1-carboxylate (120 mg, 0.17 mmol) in dichloromethane (3 mL) was added TFA (1 mL) at 0° C. After removing the solvent in vacuo, the residue was purified by silica gel column chromatography (dichloromethane/methanol=20/1) to give the desired product (100 mg, crude) as yellow solid. LC-MS: m/z 603.1 [M+H]$^+$;

(3S)-7-((S)-4-acryloyl-2-methylpiperazin-1-yl)-9-chloro-10-(2,4-difluorophenyl)-3-((4-(oxetan-3-yl)piperazin-1-yl)methyl)-2H-[1,4]thiazino[2,3,4-ij]quinazolin-5(3H)-one (4)

To a mixture of (3S)-9-chloro-10-(2,4-difluorophenyl)-7-((S)-2-methylpiperazin-1-yl)-3-((4-(oxetan-3-yl)piperazin-1-yl)methyl)-2H-[1,4]thiazino[2,3,4-ij]quinazolin-5(3H)-one (80 mg, 0.13 mmol) and triethyl amine (26 mg, 0.26 mmol) in dichloromethane (3 mL) was added acrylic anhydride (25 mg, 0.19 mmol) at 0° C. The mixture was stirred at rt for 1 hour. After removing the solvent in vacuo, the residue was purified by prep-HPLC to afford the desired product (35 mg, 41% yield) as yellow solid. LC-MS: m/z 657.1 [M+H]$^+$.

$^1$H NMR (400 MHz, $CDCl_3$) δ 7.48 (s, 1H), 7.24-7.18 (m, 1H), 7.07-6.95 (m, 2H), 6.66-6.51 (m, 1H), 6.37 (d, J=16.4 Hz, 1H), 5.77 (d, J=10.8 Hz, 1H), 5.40-5.27 (m, 1H), 4.71-4.58 (m, 5.5H), 4.52-4.36 (m, 1H), 4.20 (s, 0.5H), 3.99-3.77 (m, 1H), 3.57-3.37 (m, 4H), 3.09-3.01 (m, 2H), 2.85-2.87 (m, 3H), 2.57-2.55 (m, 3H), 2.35-2.31 (m, 4H), 1.48-1.43 (m, 3H).

J. Example 356

(3S)-7-((S)-4-acryloyl-2-methylpiperazin-1-yl)-9-chloro-3-((4-(2,2-difluoroethyl)piperazin-1-yl)methyl)-10-(2,4-difluorophenyl)-2H-[1,4]thiazino[2,3,4-ij]quinazolin-5(3H)-one

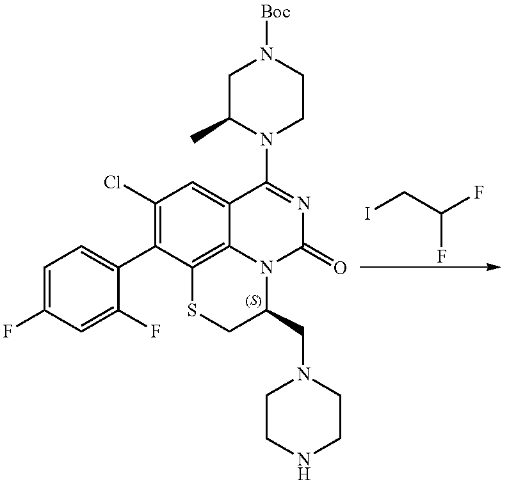

1

-continued

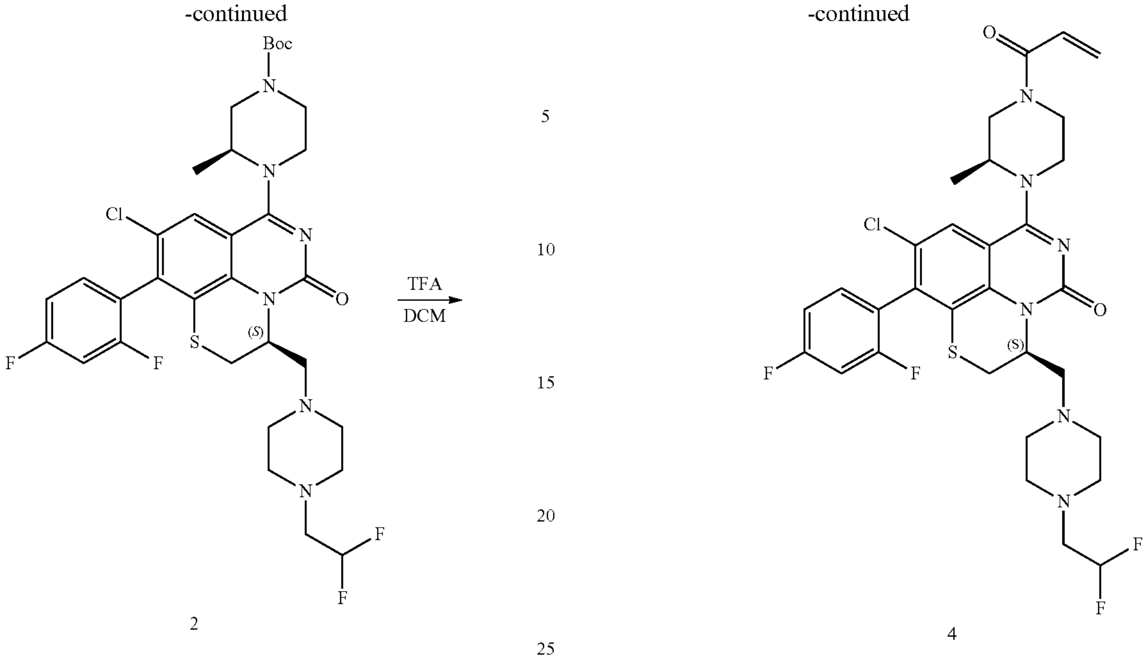

2

4

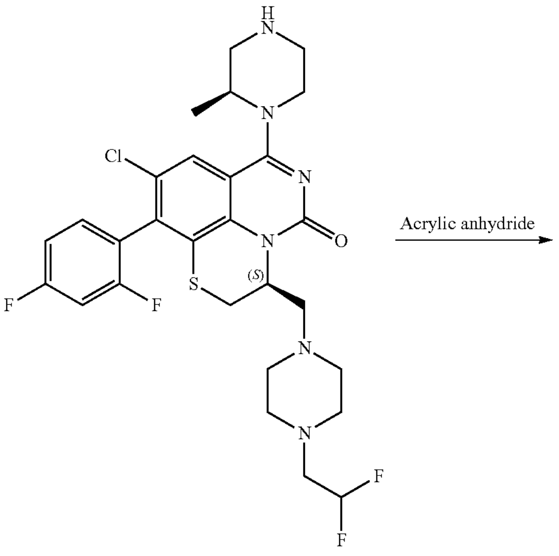

3

(3S)-tert-butyl 4-((3S)-9-chloro-3-((4-(2,2-difluoroethyl)piperazin-1-yl)methyl)-10-(2,4-difluorophenyl)-5-oxo-3,5-dihydro-2H-[1,4]thiazino[2,3,4-ij]quinazolin-7-yl)-3-methylpiperazine-1-carboxylate (2)

To a solution of (3S)-tert-butyl 4-((3S)-9-chloro-10-(2,4-difluorophenyl)-5-oxo-3-(piperidin-4-ylmethyl)-3,5-dihydro-2H-[1,4]thiazino[2,3,4-ij]quinazolin-7-yl)-3-methylpiperazine-1-carboxylate (210 mg, 0.32 mmol) and 1,1-difluoro-2-iodoethane (311 mg, 1.62 mmol) in ACN (10 mL) was added $K_2CO_3$ (224 mg, 1.62 mmol). The mixture stirred was at 85° C. for 16 hours. After removing solvent in vacuo, the residue was purified by silica gel column chromatography (dichloromethane/methanol=40/1) to give the desired product (130 mg, 56% yield) as yellow solid. MS (ESI) m/z 711.8 $[M+H]^+$ (3S)-9-chloro-3-((4-(2,2-difluoroethyl)piperazin-1-yl)methyl)-10-(2,4-difluorophenyl)-7-((S)-2-methylpiperazin-1-yl)-2H-[1,4]thiazino[2,3,4-ij]quinazolin-5(3H)-one (3)

To a solution of (3S)-tert-butyl 4-((3S)-9-chloro-3-((4-(2,2-difluoroethyl)piperazin-1-yl)methyl)-10-(2,4-difluorophenyl)-5-oxo-3,5-dihydro-2H-[1,4]thiazino[2,3,4-ij]quinazolin-7-yl)-3-methylpiperazine-1-carboxylate (130 mg, 0.18 mmol) in dichloromethane (3 mL) was added TFA (1 mL) at 0° C. After removing solvent in vacuo, the residue was purified by silica gel column chromatography (dichloromethane/methanol=20/1) to give the product (92 mg, 84% yield) as yellow solid. LC-MS: m/z 611.7 $[M+H]^+$;

(3S)-7-((S)-4-acryloyl-2-methylpiperazin-1-yl)-9-chloro-3-((4-(2,2-difluoroethyl)piperazin-1-yl)methyl)-10-(2,4-difluorophenyl)-2H-[1,4]thiazino[2,3,4-ij]quinazolin-5(3H)-one (4)

To a solution of (3S)-9-chloro-3-((4-(2,2-difluoroethyl)piperazin-1-yl)methyl)-10-(2,4-difluorophenyl)-7-((S)-2- methylpiperazin-1-yl)-2H-[1,4]thiazino[2,3,4-ij]quinazolin-5(3H)-one (70 mg, 0.11 mmol) and triethyl amine (22 mg, 0.22 mmol) in dichloromethane (3 mL) was added acrylic anhydride (25 mg, 0.19 mmol) at 0° C. The mixture was stirred at rt for 1 hour. After removing solvent in vacuo, the residue was purified by prep-HPLC to afford the product (41 mg, 42% yield) as yellow solid. LC-MS: m/z 665.8 $[M+H]^+$. $^1H$ NMR (400 MHz, $CDCl_3$) δ 7.48 (s, 1H), 7.24-7.18 (m, 1H), 7.07-6.95 (m, 2H), 6.66-6.51 (m, 1H), 6.36 (d, J=16.8 Hz, 1H), 6.00-5.70 (m, 2H), 5.40-5.32 (m, 1H), 4.71-4.65 (m, 1H), 4.56-4.35 (m, 1.5H), 4.23-4.17 (m, 0.5H), 3.99-3.78 (m, 1H), 3.64-3.37 (m, 3H), 3.08-3.00 (m, 2H), 2.84-2.67 (m, 5H), 2.58-2.52 (m, 7H), 1.48-1.43 (m, 3H).

K. Example 19

(3S)-7-((S)-4-acryloyl-2-methylpiperazin-1-yl)-3-((4-(2,2-difluoroethyl)piperazin-1-yl)methyl)-10-(2,4-difluorophenyl)-9-(trifluoromethyl)-2H-[1,4]thiazino[2,3,4-ij]quinazolin-5(3H)-one

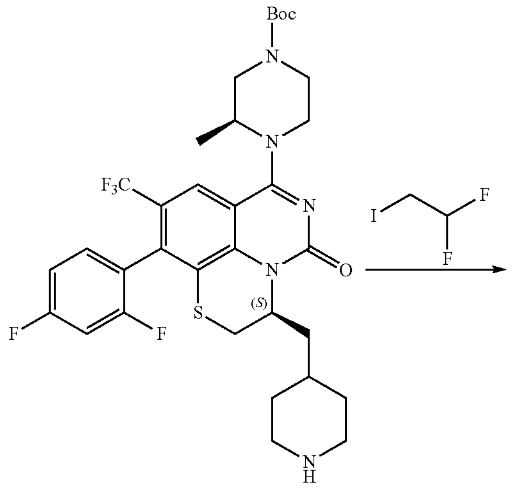

1

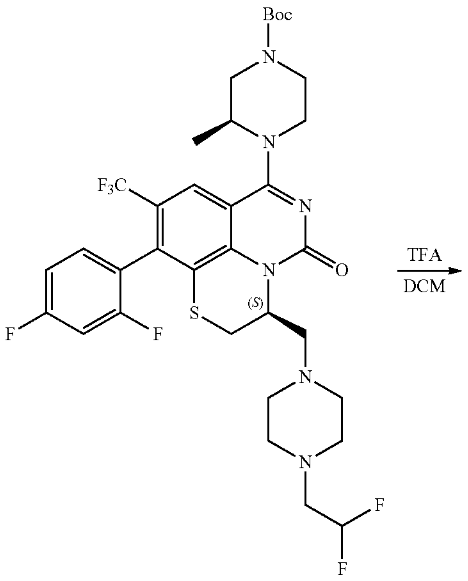

2

-continued

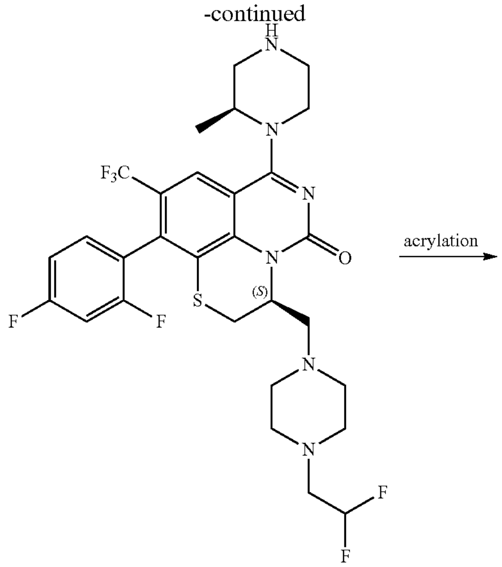

3

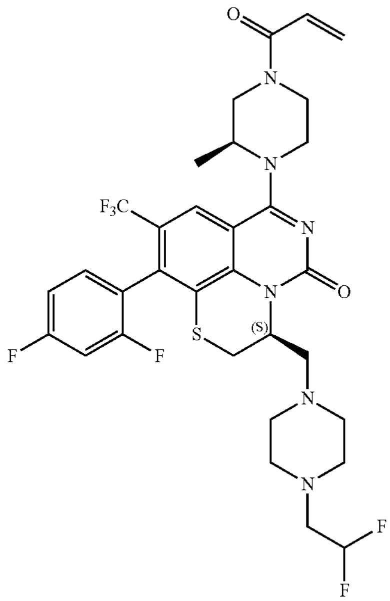

4

(3S)-tert-butyl 4-((3S)-3-((4-(2,2-difluoroethyl)piperazin-1-yl)methyl)-10-(2,4-difluorophenyl)-5-oxo-9-(trifluoromethyl)-3,5-dihydro-2H-[1,4]thiazino[2,3,4-ij]quinazolin-7-yl)-3-methylpiperazine-1-carboxylate (2)

To a mixture of (3S)-tert-butyl 4-((3S)-10-(2,4-difluorophenyl)-5-oxo-3-(piperidin-4-ylmethyl)-9-(trifluoromethyl)-3,5-dihydro-2H-[1,4]thiazino[2,3,4-ij]quinazolin-7-yl)-3-methylpiperazine-1-carboxylate (150 mg, 0.22 mmol), and 1,1-difluoro-2-iodoethane (211 mg, 1.1 mmol) in ACN (5 mL) was added $K_2CO_3$ (91 mg, 0.66 mmol). The mixture was stirred at 85° C. for 16 hours. After removing solvent in vacuo, the residue was purified by silica gel column chromatography (dichloromethane/methanol=40/1) to give the product (100 mg, 61% yield) as yellow solid. MS (ESI) m/z 745.1 $[M+H]^+$ (3S)-3-((4-(2,2-difluoroethyl)piperazin-1-yl)methyl)-10-(2,4-difluorophenyl)-7-((S)-2-methylpiperazin-1-yl)-9-(trifluoromethyl)-2H-[1,4]thiazino[2,3,4-ij]quinazolin-5(3H)-one (3)

To a solution of (3S)-tert-butyl 4-((3S)-3-((4-(2,2-difluoroethyl)piperazin-1-yl)methyl)-10-(2,4-difluorophenyl)-5-oxo-9-(trifluoromethyl)-3,5-dihydro-2H-[1,4]thiazino[2,3,4-ij]quinazolin-7-yl)-3-methylpiperazine-1-carboxylate (100 mg, 0.13 mmol) in dichloromethane (3 mL) was added TFA (1 mL) at 0° C. for 1 hour. After removing solvent in vacuo, the residue was purified by silica gel column chromatography (dichloromethane/methanol=20/1) to give the desired product (150 mg, crude) as yellow solid. LC-MS: m/z 645.1 $[M+H]^+$;

(3S)-7-((S)-4-acryloyl-2-methylpiperazin-1-yl)-3-((4-(2,2-difluoroethyl)piperazin-1-yl)methyl)-10-(2,4-difluorophenyl)-9-(trifluoromethyl)-2H-[1,4]thiazino[2,3,4-ij]quinazolin-5(3H)-one (4)

To a mixture of (3S)-3-((4-(2,2-difluoroethyl)piperazin-1-yl)methyl)-10-(2,4-difluorophenyl)-7-((S)-2-methylpiperazin-1-yl)-9-(trifluoromethyl)-2H-[1,4]thiazino[2,3,4-ij]quinazolin-5(3H)-one (100 mg, 0.15 mmol) and triethyl amine (38 mg, 0.3 mmol) in dichloromethane (3 mL) was added acrylic anhydride (25 mg, 0.19 mmol) at 0° C. The mixture was stirred at rt for 1 hour. After removing the solvent in vacuo, the residue was purified by prep-HPLC to afford the product (30 mg, 28% yield) as yellow solid. LC-MS: m/z 699.1 $[M+H]^+$; $^1H$ NMR (400 MHz, $CDCl_3$) δ 7.77 (s, 1H), 7.20-7.16 (m, 1H), 7.07-6.94 (m, 2H), 6.71-6.51 (m, 1H), 6.41-6.35 (m, 1H), 6.00-5.69 (m, 2H), 5.38-5.32 (m, 1H), 4.75-4.61 (m, 1H), 4.52-4.23 (m, 2H), 4.04-3.77 (m, 1H), 3.67-3.39 (m, 3H), 3.16-2.80 (m, 2H), 2.79-2.66 (m, 5H), 2.61-2.52 (m, 7H), 1.54-1.43 (m, 3H).

TABLE 5

Summary Table

| Ex. # | Name | Structure | $^1H$ NMR | MS $(M + H)^+$ |
|---|---|---|---|---|
| 137 | (R)-7-((S)-4-acryloyl-2-methylpiperazin-1-yl)-9-chloro-3-(methoxymethyl)-10-(2,4,6-trifluorophenyl)-2,3-dihydro-5H-[1,4]thiazino[2,3,4-ij]quinazolin-5-one | 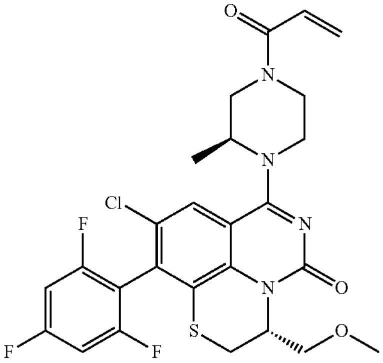 | $^1H$ NMR (400 MHz, $CDCl_3$) δ 7.52-7.49 (brs, 1H), 6.86-6.82 (m, 1H), 6.60-6.56 (m, 1H), 6.39-6.35 (m, 1H), 5.78 (d, J = 2.4 Hz, 1H), 5.44 (brs, 1H), 5.01-4.47 (m, 2H), 4.09-3.99 (m, 1.5H), 3.83-3.62 (m, 4H), 3.49-3.32 (m, 5H), 3.05-3.01 (m, 1H), 2.90-2.85 (m, 0.5H), 2.64-2.45 (m, 3H), 1.88-1.80 (m, 4H), 1.53-1.46 (m, 2H), 1.34 (d, J = 6.4 Hz, 3H). | 565.1 |
| 130 | (3R)-7-((S)-4-acryloyl-2-methylpiperazin-1-yl)-9-chloro-10-(2,4-difluorophenyl)-3-(methoxymethyl)-2,3-dihydro-5H-[1,4]thiazino[2,3,4-ij]quinazolin-5-one | 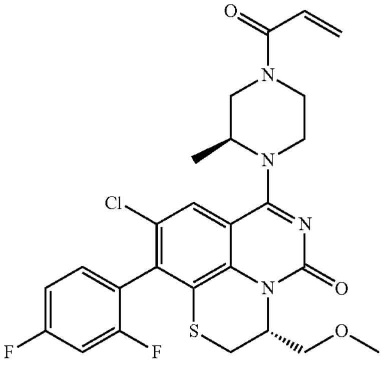 | $^1H$ NMR (400 MHz, $CDCl_3$) δ 7.52-7.49 (brs, 1H), 7.24-7.19 (m, 1H), 7.07-6.95(m, 2H), 6.59-6.57 (m, 1H), 6.39-6.32 (m, 1H), 5.78 (d, J = 2.4 Hz, 1H), 5.43-5.39 (m, 1H), 5.01-4.47 (m, 2H), 4.09-3.99 (m, 1.5H), 3.83-3.62 (m, 4H), 3.49-3.32 (m, 5H), 3.06-3.01 (m, 1H), 2.90-2.85 (m, 0.5H), 2.64-2.45 (m, 3H), 1.88-1.80 (m, 4H), 1.53-1.46 (m, 2H), 1.34 (d, J = 6.4 Hz, 3H). | 547.1 |

TABLE 5-continued

| Summary Table | | | | |
|---|---|---|---|---|
| Ex. # | Name | Structure | $^1$H NMR | MS (M + H)$^+$ |
| 99 | (3R)-7-((S)-4-acryloyl-2-methylpiperazin-1-yl)-9-chloro-10-(2,4-difluorophenyl)-3-methyl-2H-[1,4]thiazino[2,3,4-ij]quinazolin-5(3H)-one | 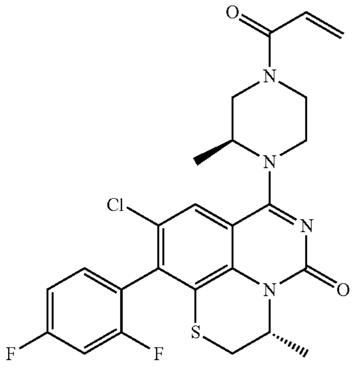 [SMILES: C=CC(=O)N1CCN(c2nc(=O)n3c4c(c(-c5ccc(F)cc5F)c(Cl)cc24)SC[C@H]3C)[C@@H](C)C1] | $^1$H NMR (400 MHz, $CDCl_3$) δ 7.51 (s, 1H), 7.25-7.19 (m, 1H), 7.07-6.97 (m, 2H), 6.59-6.57 (m, 1H), 6.39-6.36(d, 1H), 5.79-5.76(d, 1H), 5.42(s, 1H), 4.96-4.86(d, 1H), 4.64-4.62(d, 1H), 4.02-3.96(t, 1.5H), 3.83-3.67(m, 2H), 3.42-3.21(m, 2H), 2.92-2.87(m, 1.5H), 1.48-1.45(t, 3H),1.33-1.31(d, 3H). | 517.1 |
| 339 | (R)-3-(3-((1S,4S)-2-oxa-5-azabicyclo[2.2.1]heptan-5-yl)propyl)-7-((S)-4-acryloyl-2-methylpiperazin-1-yl)-9-chloro-10-(2,4,6-trifluorophenyl)-2H-[1,4]thiazino[2,3,4-ij]quinazolin-5(3H)-one | 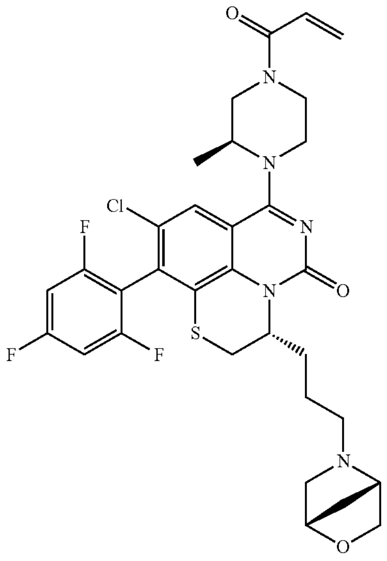 [SMILES: C=CC(=O)N1CCN(c2nc(=O)n3c4c(c(-c5c(F)cc(F)cc5F)c(Cl)cc24)SC[C@H]3CCCN2C[C@@H]3C[C@H]2CO3)[C@@H](C)C1] | $^1$H NMR (400 MHz, $CDCl_3$) δ 7.51 (brs, 1H), 6.84 (t, J = 8.0 Hz, 1H), 6.63-6.53(m, 1H), 6.39-6.35 (m, 1H), 5.78 (d, J = 11.2 Hz, 1H), 5.32 (brs, 1H), 4.94-4.75 (m, 1H), 4.67-4.55 (m, 1H), 4.38 (s, 1H), 4.09-4.00 (m, 2H), 3.83-3.44 (m, 5H), 3.24-3.05 (m, 2H), 2.71-2.51 (m, 3H), 1.95-1.88 (m, 4H), 1.58-1.53 (m, 2H), 1.36 (d, J = 7.2 Hz, 3H). | 660.2 |
| 340 | (S)-3-(3-((1S,4S)-2-oxa-5-azabicyclo[2.2.1]heptan-5-yl)propyl)-7-((S)-4-acryloyl-2-methylpiperazin-1-yl)-9-chloro-10-(2,4,6-trifluorophenyl)-2H-[1,4]thiazino[2,3,4-ij]quinazolin-5(3H)-one | 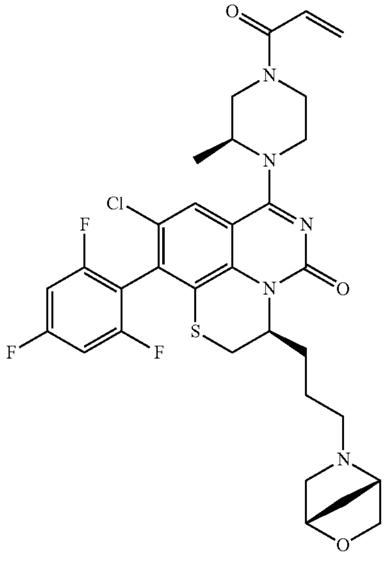 [SMILES: C=CC(=O)N1CCN(c2nc(=O)n3c4c(c(-c5c(F)cc(F)cc5F)c(Cl)cc24)SC[C@@H]3CCCN2C[C@@H]3C[C@H]2CO3)[C@@H](C)C1] | $^1$H NMR (400 MHz, $CDCl_3$) δ 7.50 (s, 1H), 6.84 (t, J = 8.0 Hz, 1H), 6.63-6.53(m, 1H), 6.39-6.35 (m, 1H), 5.78 (d, J = 11.2 Hz, 1H), 5.32 (brs, 1H), 4.70-4.25 (m, 4H), 4.09-3.96 (m, 2H), 3.61-3.41 (m, 4H), 3.26-2.93 (m, 4H), 2.71-2.51 (m, 3H), 1.95-1.84 (m, 4H), 1.52-1.45 (m, 3H). | 660.2 |

TABLE 5-continued

Summary Table

| Ex. # | Name | Structure | $^1$H NMR | MS (M + H)$^+$ |
|---|---|---|---|---|
| 341 | (3R)-3-(3-((1S,4S)-2-oxa-5-azabicyclo[2.2.1]heptan-5-yl)propyl)-7-((S)-4-acryloyl-2-methylpiperazin-1-yl)-9-chloro-10-(2,4-difluorophenyl)-2H-[1,4]thiazino[2,3,4-ij]quinazolin-5(3H)-one | 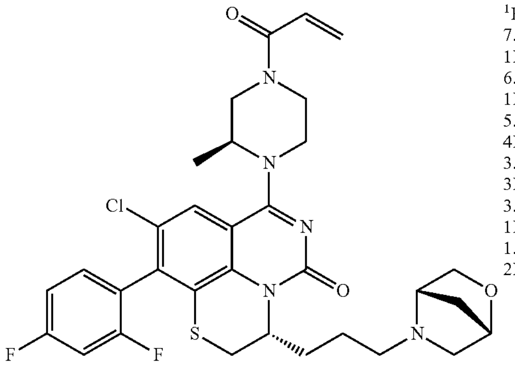 | $^1$H NMR (400 MHz, $CDCl_3$) δ 7.50 (brs, 1H), 7.24-7.19 (m, 1H), 7.07-6.96 (m, 2H), 6.59-6.52 (m, 1H), 6.39-6.32 (m, 1H), 5.78 (d, J = 2.4 Hz, 1H), 5.32 (brs, 1H), 4.93-4.63 (m, 4H), 4.37-4.36 (m, 2H), 4.09-3.98 (m, 2.5H), 3.83-3.57 (m, 3H), 3.45-3.25 (m, 2H), 3.14-3.04 (m, 2.5H), 2.90-2.87 (m, 1H), 2.64-2.45 (m, 3H), 1.88-1.80 (m, 4H), 1.53-1.46 (m, 2H), 1.34 (d, J = 6.8 Hz, 3H). | 642.3 |
| 342 | (3S)-3-(3-((1S,4S)-2-oxa-5-azabicyclo[2.2.1]heptan-5-yl)propyl)-7-((S)-4-acryloyl-2-methylpiperazin-1-yl)-9-chloro-10-(2,4-difluorophenyl)-2H-[1,4]thiazino[2,3,4-ij]quinazolin-5(3H)-one | 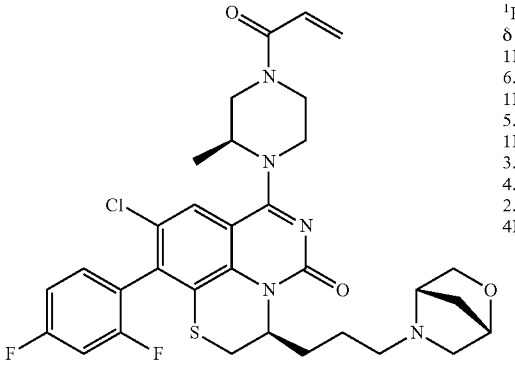 | $^1$H NMR (400 MHz, $CDCl_3$) δ 7.49 (s, 1H), 7.26-7.18 (m, 1H), 7.07-6.95 (m, 2H), 6.62-6.53 (m, 1H), 6.39-6.36 (d, 1H), 5.79-5.78 (d, 1H), 5.34-5.28 (m, 1H), 4.74-4.70 (m, 1H), 4.54-4.23 (m, 3H), 3.99-3.96 (dd, 1.5H), 3.81-3.45 (m, 4.5H), 3.09-2.86 (m, 4H), 2.7-2.46 (m, 3H), 1.92-1.75 (m, 4H),1.66-1.36 (m, 5H). | 642.2 |
| 343 | (S)-7-((S)-4-acryloyl-2-methylpiperazin-1-yl)-9-chloro-3-((1-methylpiperidin-4-yl)methyl)-10-(2,4,6-trifluorophenyl)-2H-[1,4]thiazino[2,3,4-ij]quinazolin-5(3H)-one | 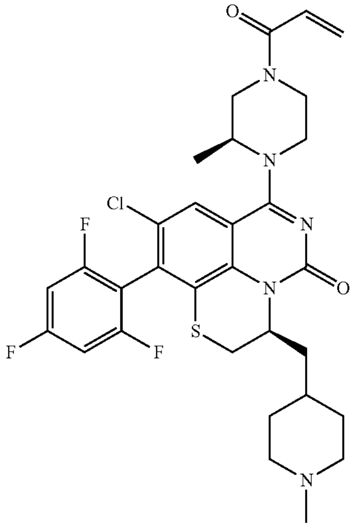 [SMILES: C=CC(=O)N1CCN(c2nc(=O)n3c4c(c(-c5c(F)cc(F)cc5F)c(Cl)cc24)SC[C@@H]3CC2CCN(C)CC2)[C@@H](C)C1] | $^1$H NMR (400 MHz, $CDCl_3$) δ 7.51 (s, 1H), 6.85 (t, J = 8.0 Hz, 2H), 6.63-6.54 (m, 1H), 6.40-6.36 (m, 1H), 5.78 (d, J = 9.6 Hz, 1H), 5.47-5.46 (m, 1H), 4.75-4.66 (m, 1H), 4.57-4.43 (m, 1H), 4.38-4.18 (m, 1H), 3.97-3.79 (m, 1H), 3.61-3.46 (m, 2H), 3.19-3.16 (m, 1H), 3.09-2.98 (m, 2H), 2.89-2.84 (m, 2H), 2.27 (s, 3H), 2.02-1.91 (m, 2.5H), 1.81-1.76 (m, 2.5H), 1.48-1.31 (m, 7H). | 632.2 |

TABLE 5-continued

| Ex. # | Name | Structure | $^1$H NMR | MS (M + H)$^+$ |
| --- | --- | --- | --- | --- |
| Summary Table | | | | |
| 344 | (R)-7-((S)-4-acryloyl-2-methylpiperazin-1-yl)-9-chloro-3-((1-methylpiperidin-4-yl)methyl)-10-(2,4,6-trifluorophenyl)-2H-[1,4]thiazino[2,3,4-ij]quinazolin-5(3H)-one | 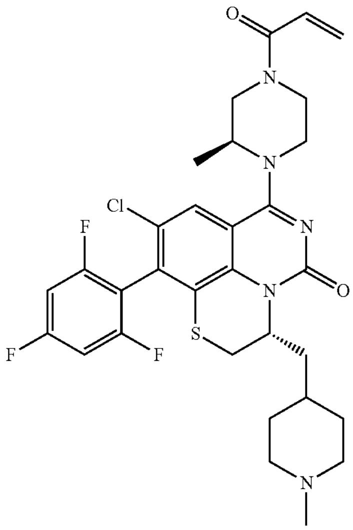 [SMILES: C=CC(=O)N1CCN(c2nc(=O)n3c4c(c(-c5c(F)cc(F)cc5F)c(Cl)cc24)SC[C@H]3CC2CCN(C)CC2)[C@@H](C)C1] | $^1$H NMR (400 MHz, $CDCl_3$) δ 7.52-7.51 (m, 1H), 6.85 (t, J = 8.0 Hz, 2H), 6.63-6.53 (m, 1H), 6.38 (dd, J = 16.8 Hz, 1.6 Hz, 1H), 5.78 (d, J = 10.8 Hz, 1H), 5.48-5.46 (m, 1H), 4.91-4.89 (m, 0.5H), 4.74-4.64 (m, 1H), 4.50-4.47 (m, 0.5H), 4.17-3.97 (m, 1.5H), 3.84-3.46 (m, 3H), 3.20-3.16 (m, 1.5H), 3.02-2.92 (m, 1.5H), 2.87-2.81 (m, 2H), 2.25 (s, 3H), 1.99-1.84 (m, 2.5H), 1.64-1.58 (m, 2H), 1.44-1.32 (m, 7H). | 632.2 |
| 345 | (3R)-7-((S)-4-acryloyl-2-methylpiperazin-1-yl)-9-chloro-10-(2,4-difluorophenyl)-3-((1-methylpiperidin-4-yl)methyl)-2H-[1,4]thiazino[2,3,4-ij]quinazolin-5(3H)-one | 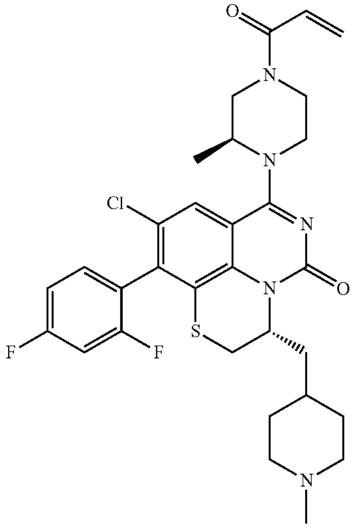 [SMILES: C=CC(=O)N1CCN(c2nc(=O)n3c4c(c(-c5ccc(F)cc5F)c(Cl)cc24)SC[C@H]3CC2CCN(C)CC2)[C@@H](C)C1] | $^1$H NMR (400 MHz, $CDCl_3$) δ 7.51 (s, 1H), 7.24-7.20 (m, 1H), 7.07-6.96 (m, 2H), 6.59-6.57 (m, 1H), 6.37 (d, J = 15.6 Hz, 1H), 5.78 (d, J = 10.8 Hz, 1H), 5.48-5.42 (m, 1H), 4.91-4.89 (m, 0.5H), 4.71-4.63 (m, 1H), 4.48-4.47 (m, 0.5H), 4.12-3.98 (m, 1.5H), 3.83-3.49 (m, 3H), 3.22-3.11 (m, 1.5H), 2.99-2.86 (m, 3.5H), 2.30 (s, 3H), 1.98-1.91 (m, 1.5H), 1.51-1.33 (m, 10H). | 614.2 |

TABLE 5-continued

| Summary Table | | | | |
|---|---|---|---|---|
| Ex. # | Name | Structure | $^1$H NMR | MS (M + H)$^+$ |
| 346 | (3R)-7-((S)-4-acryloyl-2-methylpiperazin-1-yl)-9-chloro-10-(2,4-difluorophenyl)-3-((4-ethylpiperazin-1-yl)methyl)-2H-[1,4]thiazino[2,3,4-ij]quinazolin-5(3H)-one | 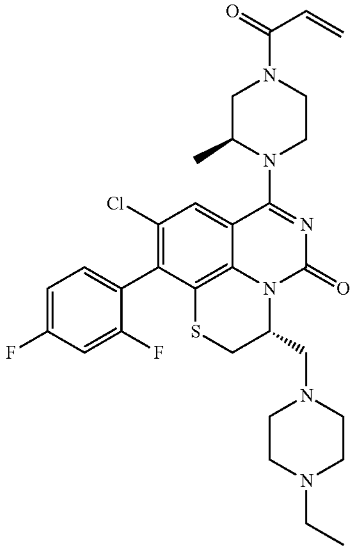 [SMILES: C=CC(=O)N1CCN(c2nc(=O)n3c4c(c(-c5ccc(F)cc5F)c(Cl)cc24)SC[C@H]3CN2CCN(CC)CC2)[C@@H](C)C1] | $^1$H NMR (400 MHz, $CDCl_3$) δ 7.51-7.49 (m, 1H), 7.24-7.18 (m, 1H), 7.07-6.95 (m, 2H), 6.61-6.53 (m, 1H), 5.78 (d, J = 11.2 Hz, 1H), 5.38-5.31 (m, 1H), 4.990-4.46 (m, 2H), 4.19-4.00 (m, 1.5H), 3.83-3.40 (m, 3.5H), 3.14-2.98 (m, 2H), 2.84-2.65 (m, 3H), 2.54-2.30 (m, 9H), 1.36 (d, J = 6.4 Hz, 2H), 1.08-1.02 (m, 3H). | 629.3 |
| 76 | 7-((5)-4-acryloyl-2-methylpiperazin-1-yl)-9-chloro-10-(2,4-difluorophenyl)-2,2-dimethyl-2,3-dihydro-5H-[1,4]thiazino[2,3,4-ij]quinazolin-5-one | 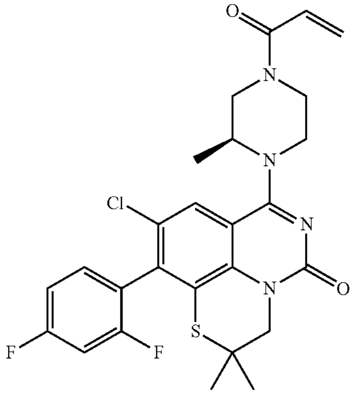 [SMILES: C=CC(=O)N1CCN(c2nc(=O)n3c4c(c(-c5ccc(F)cc5F)c(Cl)cc24)SC(C)(C)C3)[C@@H](C)C1] | $^1$H NMR (400 MHz, MeOH-$d_4$) δ 7.71 (d, J = 4.5 Hz, 1H), 7.33-7.22 (m, 1H), 7.18-7.09 (m, 2H), 6.91-6.73 (m, 1H), 6.29 (dd, J = 16.2. 7.2 Hz, 1H), 5.81 (dd, J = 10.6. 1.9 Hz, 1H), 4.68-3.93 (m, 5H), 3.80-3.45 (m, 2H), 1.42 (s, 3H), 1.38 (s, 3H) | 531.2 |
| 347 | (3R)-7-((S)-4-acryloyl-2-methylpiperazin-1-yl)-9-chloro-3-((4-(2,2-difluoroethyl)piperazin-1-yl)methyl)-10-(2,4-difluorophenyl)-2H-[1,4]thiazino[2,3,4-ij]quinazolin-5(3H)-one | 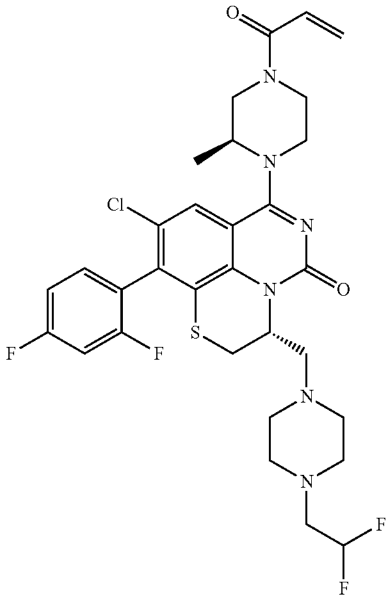 | $^1$H NMR (400 MHz, $CDCl_3$) δ 7.49 (brs, 1H), 7.23-7.17 (m, 1H), 7.07-6.95 (m, 2H), 6.62-6.55 (m, 1H), 6.39-6.34 ( m, 1H), 6.01-5.70 (m, 2H), 5.38-5.30 (m, 1H), 4.92-4.54(m, 2H),4.11-3.99 (m, 1.5H), 3.82-3.21(m, 4.5H), 3.02-2.83 (m, 2H), 2.74-2.67 (m, 5H), 2.60-2.52 (m, 7H), 1.45 (d, J = 6.8 Hz, 3H). | 665.2 |

TABLE 5-continued

Summary Table

| Ex. # | Name | Structure | ¹H NMR | MS (M + H)⁺ |
|---|---|---|---|---|
| 348 | (3R)-7-((S)-4-acryloyl-2-methylpiperazin-1-yl)-9-chloro-3-((1-(2,2-difluoroethyl)piperidin-4-yl)methyl)-10-(2,4-difluorophenyl)-2H-[1,4]thiazino[2,3,4-ij]quinazolin-5(3H)-one | 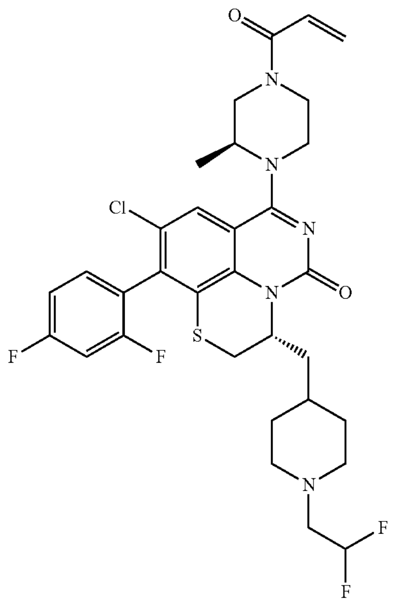 | $^1H$ NMR (400 MHz, $CDCl_3$) δ 7.51 (s, 1H), 7.24-7.20 (m, 1H), 7.07-6.96 (m, 2H), 6.62-6.53 (m, 1H), 6.37 (dd, J = 16.4 Hz, 1.2 Hz, 1H), 6.00-5.71 (m, 2H), 5.44-5.43 (m, 1H), 4.91-4.88 (m, 0.5 H), 4.72-4.63 (m, 1H), 4.48-4.45 (m, 0.5H), 4.13-3.96 (m, 1.5H), 3.83-3.62 (m, 1.5H), 3.59-3.45 (m, 1H), 3.23-3.20(m, 0.5H), 3.18-3.10 (m, 1H), 2.99-2.87 (m, 3.5H), 2.74-2.65 (m, 2H), 2.24-2.14 (m, 2H), 1.75-1.73 (m, 3H), 1.45-1.35 (m, 7H). | 664.3 |
| 349 | (R)-7-((S)-4-acryloyl-2-methylpiperazin-1-yl)-9-chloro-3-((1-(2,2-difluoroethyl)piperidin-4-yl)methyl)-10-(4-fluorophenyl)-2H-[1,4]thiazino[2,3,4-ij]quinazolin-5(3H)-one | 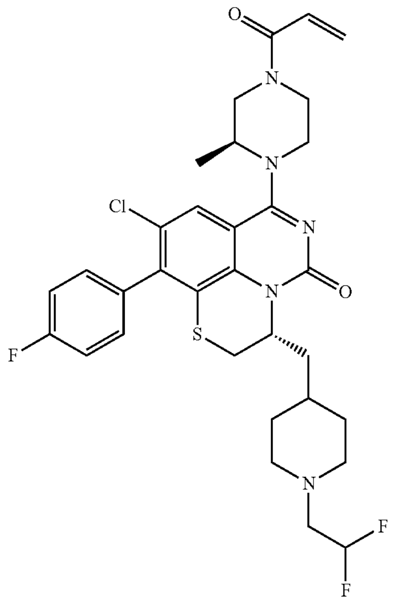 [SMILES: C=CC(=O)N1CCN(c2nc(=O)n3c4c(c(-c5ccc(F)cc5)c(Cl)cc24)SC[C@H]3CC2CCN(CC(F)F)CC2)[C@@H](C)C1] | $^1H$ NMR (400 MHz, $CDCl_3$) δ 7.51 (s, 1H), 7.25-7.19 (m, 4H), 6.63-6.52 (m, 1H), 6.37 (dd, J = 16.8 Hz, 1.6 Hz, 1H), 6.01-5.71 (m, 2H), 5.43-5.41 (m, 1H), 4.91-4.88 (m, 0.5 H), 4.71-4.63 (m, 1H), 4.49-4.46 (m, 0.5H), 4.15-4.00 (m, 1.5H), 3.83-3.64 (m, 1.5H), 3.61-3.47 (m, 1H), 3.23-3.21 (m, 0.5H), 3.10-3.06 (m, 1H), 2.96-2.89 (m, 3.5H), 2.75-2.66 (m, 2H), 2.23-2.13 (m, 2H), 1.87-1.74 (m, 4H), 1.47-1.33 (m, 6H). | 646.2 |

TABLE 5-continued

| Summary Table | | | | |
|---|---|---|---|---|
| Ex. # | Name | Structure | $^1$H NMR | MS (M + H)$^+$ |
| 350 | (3S)-7-((S)-4-acryloyl-2-methylpiperazin-1-yl)-10-(2,4-difluorophenyl)-3-((4-ethylpiperazin-1-yl)methyl)-9-(trifluoromethyl)-2H-[1,4]thiazino[2,3,4-ij]quinazolin-5(3H)-one | 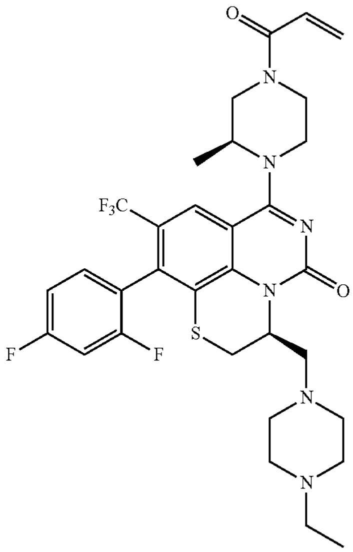 | $^1$H NMR (400 MHz, $CDCl_3$) δ 7.75 (s, 1H), 7.20-7.15 (m, 1H), 7.04-6.93 (m, 2H), 6.62-6.53 (m, 1H), 6.39-6.52 (m, 1H), 5.75 (d, J = 9.2 Hz, 1H), 5.37-5.28 (m, 1H), 4.72-4.68 (m, 1H), 4.51-4.26 (m, 2H), 3.99-3.38 (m, 5H), 3.11-2.97 (m, 2H), 2.82-2.76 (m, 3H), 2.59-2.37 (m, 8H), 1.26-1.22 (m, 3H), 1.09 (t, J = 7.2 Hz, 3H). | 663.3 |
| 351 | (S)-7-((S)-4-acryloyl-2-methylpiperazin-1-yl)-9-chloro-3-((4-ethylpiperazin-1-yl)methyl)-10-(2,4,6-trifluorophenyl)-2H-[1,4]thiazino[2,3,4-ij]quinazolin-5(3H)-one | 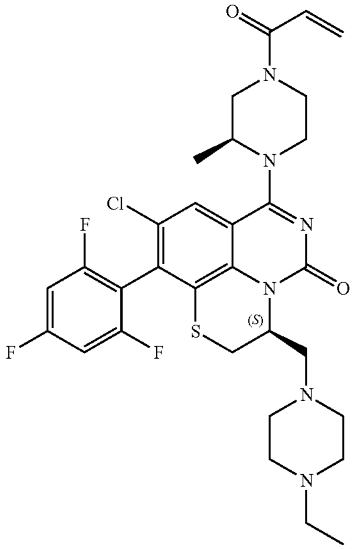 | $^1$H NMR (400 MHz, $CDCl_3$) δ 7.49 (s, 1H), 6.86-6.82 (m, 2H), 6.70-6.48 (m, 1H), 6.39-6.34 (m, 1H), 5.79-5.76 (m, 1H), 5.45-5.33 (m, 1H), 4.76-4.64 (m, 1H), 4.61-4.24 (m, 1.5H), 4.14-4.01 (m, 0.5H), 4.01-3.74 (m, 1H), 3.62-3.41 (m, 3H), 3.08-3.05 (m, 2H), 2.82-2.78 (m, 3H), 2.55-2.36 (m, 9H), 1.48-1.43 (m, 3H), 1.09-1.05 (m, 3H) | 647.2 |

TABLE 5-continued

| Summary Table | | | | |
|---|---|---|---|---|
| Ex. # | Name | Structure | $^1$H NMR | MS (M + H)$^+$ |
| 352 | (3S)-7-((S)-4-acryloyl-2-methylpiperazin-1-yl)-10-(2,4-difluorophenyl)-3-((4-(oxetan-3-yl)piperazin-1-yl)methyl)-9-(trifluoromethyl)-2H-[1,4]thiazino[2,3,4-ij]quinazolin-5(3H)-one | 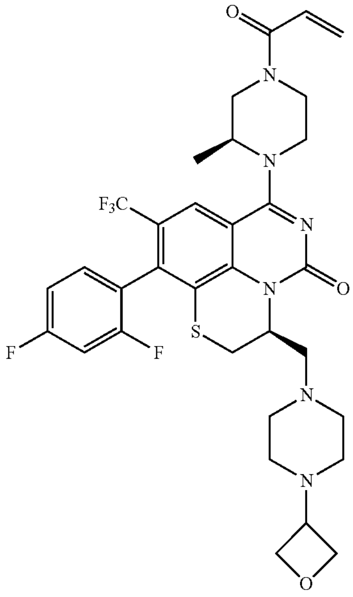 [SMILES: C=CC(=O)N1CCN(c2nc(=O)n3c4c(c(-c5ccc(F)cc5F)c(C(F)(F)F)cc24)SC[C@@H]3CN2CCN(C3COC3)CC2)[C@@H](C)C1] | $^1$H NMR (400 MHz, $CDCl_3$) δ 7.77 (s, 1H), 7.21-7.15 (m, 1H), 7.04-6.93 (m, 2H), 6.65-6.35 (m, 2H), 5.78 (d, J = 8.4 Hz, 1H), 5.33-5.30 (m, 1H), 4.69-4.42 (m, 7H), 3.80-3.40 (m, 6H), 3.08-2.99 (m, 2H), 2.88-2.74 (m, 3H), 2.58-2.53 (m, 3H), 2.31-2.17 (m, 3H), 1.49-1.48 (m, 3H). | 691.2 |
| 353 | (3S)-7-((S)-4-acryloyl-2-methylpiperazin-1-yl)-10-(2,4-difluorophenyl)-3-((1-ethylpiperidin-4-yl)methyl)-9-(trifluoromethyl)-2H-[1,4]thiazino[2,3,4-ij]quinazolin-5(3H)-one | 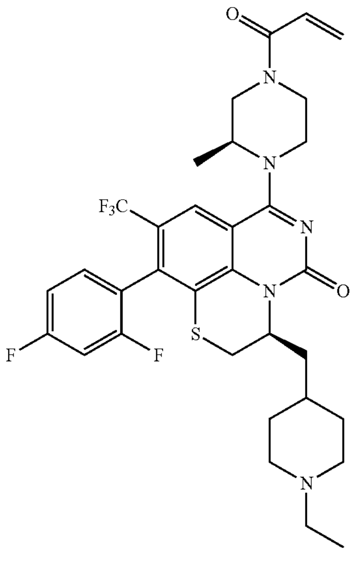 | $^1$H NMR (400 MHz, $CDCl_3$) δ 7.79 (s, 1H), 7.29-7.15 (m, 1H), 7.06-6.95 (m, 2H), 6.61-6.53 (m, 1H), 6.37 (d, J = 15.6 Hz, 1H), 5.78 (d, J = 6.0 Hz, 1H), 5.43-5.38 (m, 1H), 4.71-4.69 (m, 1H), 4.52-4.27 (m, 2H), 3.98-3.95 (m, 0.5H), 3.83-3.80 (m, 0.5H), 3.61-3.43 (m, 2H), 3.13-2.92 (m, 5H), 2.42 (q, J = 7.2 Hz, 2H), 2.01-1.90 (m, 3H), 1.78-1.72 (m, 3H), 1.52-1.32 (m, 6H), 1.09 (t, J = 7.2 Hz, 3H). | 662.2 |

TABLE 5-continued

| Summary Table | | | | |
|---|---|---|---|---|
| Ex. # | Name | Structure | $^1$H NMR | MS (M + H)$^+$ |
| 354 | (3S)-7-((S)-4-acryloyl-2-methylpiperazin-1-yl)-9-chloro-10-(2,4-difluorophenyl)-3-((4-ethylpiperazin-1-yl)methyl)-2H-[1,4]thiazino[2,3,4-ij]quinazolin-5(3H)-one | 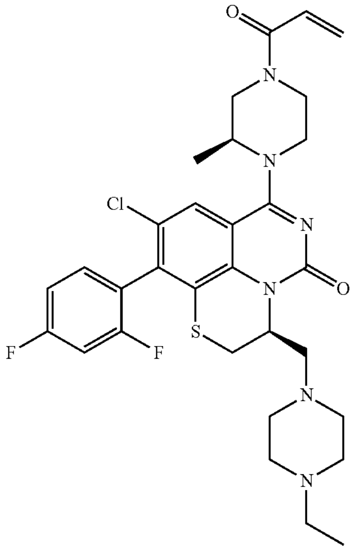 [SMILES: C=CC(=O)N1CCN(c2nc(=O)n3c4c(c(-c5ccc(F)cc5F)c(Cl)cc24)SC[C@@H]3CN2CCN(CC)CC2)[C@@H](C)C1] | $^1$H NMR (400 MHz, $CDCl_3$) δ 7.48 (s, 1H), 7.24-7.18 (m, 1H), 7.07-6.95 (m, 2H), 6.67-6.52 (m, 1H), 6.36 (d, J = 16.8 Hz, 1H), 5.75 (d, J = 10.4 Hz, 1H), 5.41-5.28 (m, 1H), 4.74-4.66 (m, 1H), 4.56-4.54 (m, 0.5H), 4.48-4.35 (m, 1H), 4.22-4.16 (m, 0.5H), 3.99-3.77 (m, 1H), 3.59-3.39 (m, 3H), 3.09-3.00 (m, 2H), 2.84-2.76 (m, 3H), 2.55-2.35 (m, 9H), 1.48-1.43 (m, 3H), 1.08-1.04 (m, 3H). | 629.3 |
| 355 | (3S)-7-((S)-4-acryloyl-2-methylpiperazin-1-yl)-9-chloro-10-(2,4-difluorophenyl)-3-((4-(oxetan-3-yl)piperazin-1-yl)methyl)-2H-[1,4]thiazino[2,3,4-ij]quinazolin-5(3H)-one | 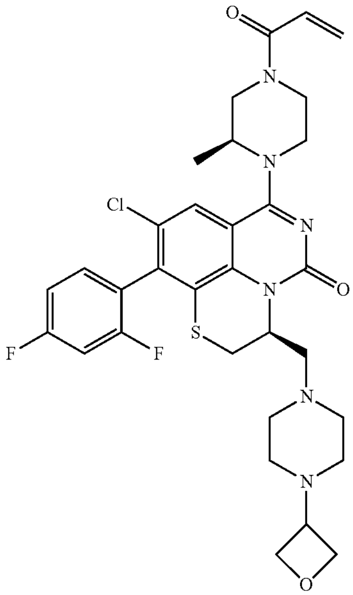 [SMILES: C=CC(=O)N1CCN(c2nc(=O)n3c4c(c(-c5ccc(F)cc5F)c(Cl)cc24)SC[C@@H]3CN2CCN(C3COC3)CC2)[C@@H](C)C1] | $^1$H NMR (400 MHz, $CDCl_3$) δ 7.48 (s, 1H), 7.24-7.18 (m, 1H), 7.07-6.95 (m, 2H), 6.66-6.51 (m, 1H), 6.37 (d, J = 16.4 Hz, 1H), 5.77 (d, J = 10.8 Hz, 1H), 5.40-5.27 (m, 1H), 4.71-4.58 (m, 5.5H), 4.52-4.36 (m, 1H), 4.20 (s, 0.5H), 3.99-3.77 (m, 1H), 3.57-3.37 (m, 4H), 3.09-3.01 (m, 2H), 2.85-2.87 (m, 3H), 2.57-2.55 (m, 3H), 2.35-2.31 (m, 4H), 1.48-1.43 (m, 3H). | 657.3 |

TABLE 5-continued

| Summary Table | | | | |
|---|---|---|---|---|
| Ex. # | Name | Structure | $^1$H NMR | MS (M + H)$^+$ |
| 356 | (3S)-7-((S)-4-acryloyl-2-methylpiperazin-1-yl)-9-chloro-3-((4-(2,2-difluoroethyl)piperazin-1-yl)methyl)-10-(2,4-difluorophenyl)-2H-[1,4]thiazino[2,3,4-ij]quinazolin-5(3H)-one | 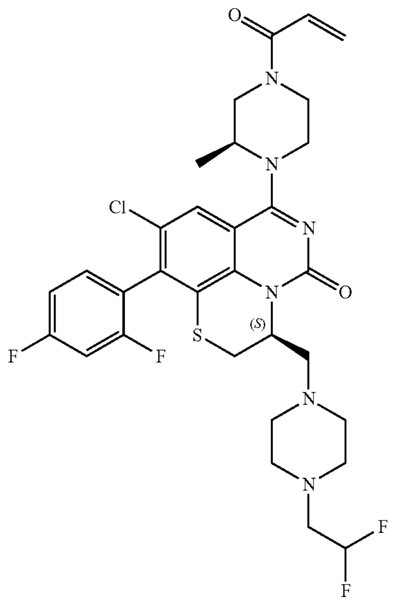 | $^1$H NMR (400 MHz, $CDCl_3$) δ 7.48 (s, 1H), 7.24-7.18 (m, 1H), 7.07-6.95 (m, 2H), 6.66-6.51 (m, 1H), 6.36 (d, J = 16.8 Hz, 1H), 6.00-5.70 (m, 2H), 5.40-5.32 (m, 1H), 4.71-4.65 (m, 1H), 4.56-4.35 (m, 1.5H), 4.23-4.17 (m, 0.5H), 3.99-3.78 (m, 1H), 3.64-3.37 (m, 3H), 3.08-3.00 (m, 2H), 2.84-2.67 (m, 5H), 2.58-2.52 (m, 7H), 1.48-1.43 (m, 3H). | 665.3 |
| 19 | (3S)-7-((S)-4-acryloyl-2-methylpiperazin-1-yl)-3-((4-(2,2-difluoroethyl)piperazin-1-yl)methyl)-10-(2,4-difluorophenyl)-9-(trifluoromethyl)-2H-[1,4]thiazino[2,3,4-ij]quinazolin-5(3H)-one | 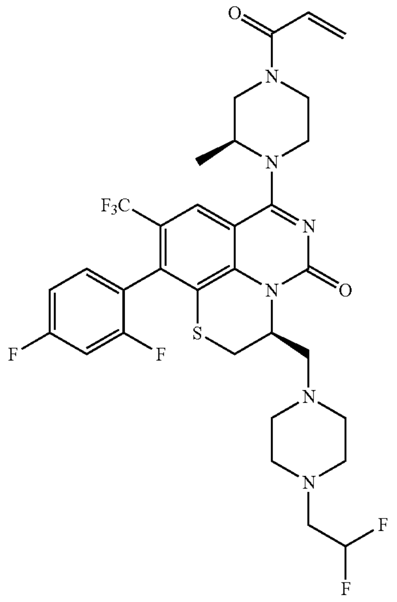 [SMILES: C=CC(=O)N1CCN(c2nc(=O)n3c4c(c(-c5ccc(F)cc5F)c(C(F)(F)F)cc24)SC[C@@H]3CN2CCN(CC(F)F)CC2)[C@@H](C)C1] | $^1$H NMR (400 MHz, $CDCl_3$) δ 7.77 (s, 1H), 7.20-7.16 (m, 1H), 7.07-6.94 (m, 2H), 6.71-6.51 (m, 1H), 6.41-6.35 (m, 1H), 6.00-5.69 (m, 2H), 5.38-5.32 (m, 1H), 4.75-4.61 (m, 1H), 4.52-4.23 (m, 2H), 4.04-3.77 (m, 1H), 3.67-3.39(m, 3H), 3.16-2.80 (m, 2H), 2.79-2.66(m, 5H), 2.61-2.52(m, 7H), 1.54-1.43(m, 3H). | 699.6 |

Syntheses of Intermediates

Reaction Scheme

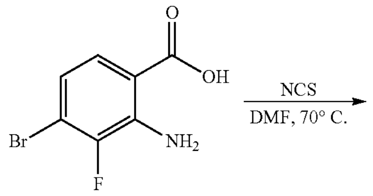

1

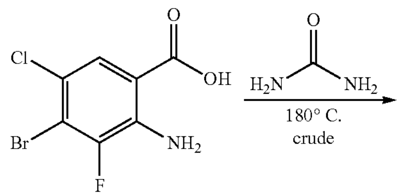

2

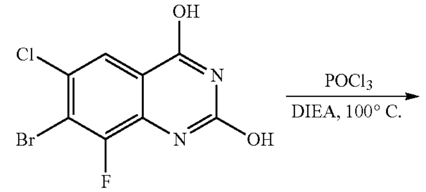

3

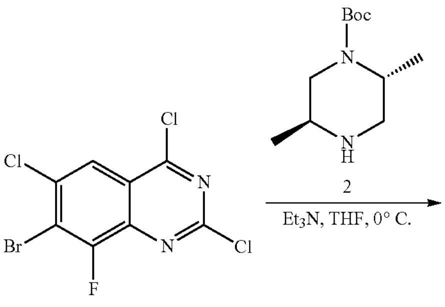

4

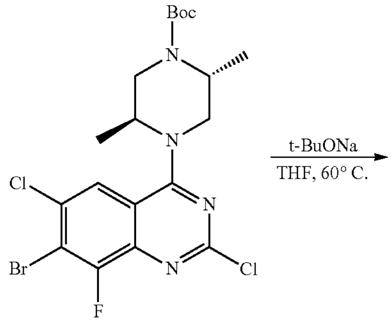

5

-continued

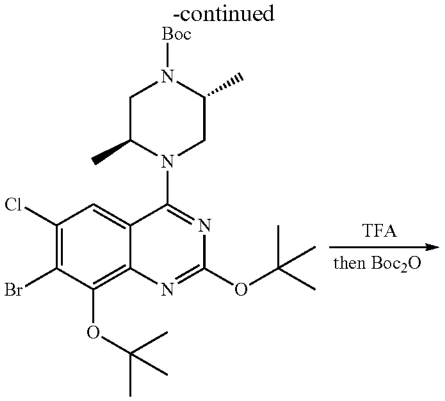

6

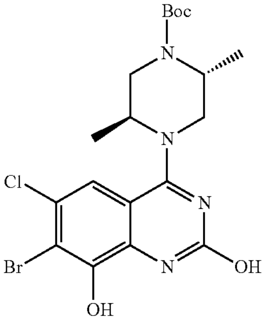

7

2-amino-4-bromo-5-chloro-3-fluorobenzoic acid (2)

To a solution of 2-amino-4-bromo-3-fluorobenzoic acid (100 g, 0.43 mol) in DMF (800 mL) was added NCS (68 g, 0.51 mol). Then the mixture was heated to 70° C. for 16 hours. After completion, the mixture was quenched with aqueous $H_2O$ (1.5 L) and extracted with EA (2 L), dried with $Na_2SO_4$ and concentrated to afford product (139 g, crude) as a grayness solid. LC-MS: m/z 268.1 $[M-H]^+$ 7-bromo-6-chloro-8-fluoroquinazoline-2,4-diol (3)

The mixture of 2-amino-4-bromo-5-chloro-3-fluorobenzoic acid (139 g, 0.51 mol) and urea (260 g, 4.33 mol) was heated to 180° C. for 6 h. After completion, the mixture was quenched with aqueous $H_2O$ (1.5 L), filtered through a Celite pad, and the filtrate was concentrated to give the crude product (130 g, crude) as a grayness solid. LC-MS: m/z 293.1 $[M-H]^+$ 7-bromo-2,4,6-trichloro-8-fluoroquinazoline (4)

The mixture of 7-bromo-6-chloro-8-fluoroquinazoline-2,4-diol (130 g, 0.51 mol) and $POCl_3$ (800 mL) was heated to 120° C. for 16 hours. After completion, the mixture was quenched with aqueous $H_2O$ (1.5 L), filtered through a Celite pad, and the filtrate was concentrated and purified by silica column with PE/EA=4:1 to afford product (59 g, 35% yield:) as a yellow solid. LC-MS: m/z 311.1 $[M-H-Cl]^+$ (2R,5S)-tert-butyl-4-(7-bromo-2,6-dichloro-8-fluoroquinazolin-4-yl)-2,5-dimethylpiperazine-1-carboxylate (5)

To a cooled mixture of 7-bromo-2,4,6-trichloro-8-fluoroquinazoline (25 g, 75.76 mmol) and $Et_3N$ (15.3 g, 151.5 mmol) in THF (200 mL) was added (2R,5S)-tert-butyl 2,5-dimethylpiperazine-1-carboxylate (16.2 g, 75.76 mmol) at 0° C. The mixture was stirred at room temperature for 4 hours. After completion, the mixture was dissolved with EtOAc (500 mL), washed with water (300 mL×3), dried over $Na_2SO_4$, filtered and concentrated to afford desired product (35.78 g, yield: 93%) as yellow solid, which was used to next step without further purification. LC-MS: m/z 509.3 [M+H].

(2R,5S)-tert-butyl-4-(7-bromo-2,8-di-tert-butoxy-6-chloroquinazolin-4-yl)-2,5-dimethyl-piperazine-1-carboxylate (6)

To a solution of (2R,5S)-tert-butyl 4-(7-bromo-2,6-dichloro-8-fluoroquinazolin-4-yl)-2,5-dimethyl piperazine-1-carboxylate (35.78 g, 70.4 mmol) in dry THF (180 mL) was added t-BuONa (16.9 g, 176.08 mmol). Then the mixture was heated to 60° C. for 4 hours. After completion, the mixture was quenched with aqueous $NH_4Cl$ and extracted with EtOAc, dried with $Na_2SO_4$ and concentrated. The residue was purified by silica using a mixture of PE:EA (15:1) as eluent to afford product (33 g, 78% yield) as a yellow solid. LC-MS: m/z 601.5 [M+H].

(2R,5S)-tert-butyl-4-(7-bromo-6-chloro-2,8-dihydroxyquinazolin-4-yl)-2,5-dimethyl piperazine-1-carboxylate (7)

To a solution of (2R,5S)-tert-butyl-4-(7-bromo-2,8-di-tert-butoxy-6-chloroquinazolin-4-yl)-2,5-dimethylpiperazine-1-carboxylate (33 g, 55.0 mmol) in DCM (70 mL) was added TFA (70 mL), the mixture was stirred at 25° C. for 3 hours. After completion, the mixture was concentrated under reduce pressure to afford the crude 7-bromo-6-chloro-4-((2S,5R)-2,5-dimethylpiperazin-1-yl) quinazoline-2,8-diol (30 g), which was used in the next step without further purification. To a solution of 7-bromo-6-chloro-4-((2S,5R)-2,5-dimethylpiperazin-1-yl)quinazoline-2,8-diol (33 g, 85.05 mmol) in DCM (150 mL) was added $(Boc)_2O$ (18.54 g, 85.05 mmol), the mixture was stirred at rt for 16 hours. After completion, the mixture was concentrated. The residue was purified by silica with a mixture of DCM/MeOH (5% $NH_3$) (40:1) to afford the desired product (24 g, 58% yield) as light green solid. LC-MS: m/z 489.3 [M+H].

TABLE 7

Table of Thiomorpholines

| Ex. # | Name | Structure | $^1$H NMR | MS (M + H)$^+$ |
|---|---|---|---|---|
| 408 | 7-((S)-4-acryloyl-2-methylpiperazin-1-yl)-9-chloro-10-(5-fluoro-1H-indazol-4-yl)-2,3-dihydro-5H-[1,4]thiazino[2,3,4-ij]quinazolin-5-one | 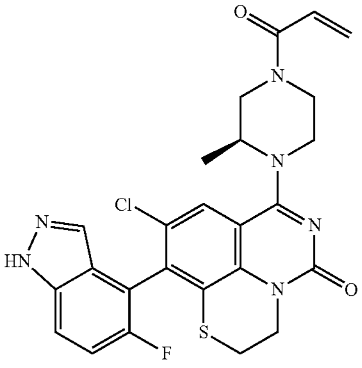 [SMILES: C=CC(=O)N1CCN(c2nc(=O)n3c4c(c(-c5c(F)ccc6[nH]ncc56)c(Cl)cc24)SCC3)[C@@H](C)C1] | $^1$H NMR (400 MHz, MeOH-$d_4$) δ 7.75 (br s, 1H), 7.72 (d, J = 7.4 Hz, 1H), 7.25 (dd, J = 10.9, 7.8 Hz, 1H), 7.00 (ddd, J = 7.9, 4.0, 1.8 Hz, 1H), 6.83 (ddd, J = 21.7, 16.7, 10.5 Hz, 1H), 6.29 (dd, J = 16.5, 6.6 Hz, 1H), 5.82 (dd, J = 10.6, 1.9 Hz, 1H), 4.85-4.78 (m, 1H), 4.63-3.99 (m, 5H), 3.78-3.44 (m, 2H), 3.25-3.02 (m, 2H), 1.44 (d, J = 6.7 Hz, 1.5H), 1.40 (d, J = 6.8 Hz, 1.5H). | 525.2 |
| 408a | 7-((S)-4-acryloyl-2-methylpiperazin-1-yl)-9-chloro-10-(3,5-difluoropyridin-2-yl)-2H-[1,4]thiazino[2,3,4-ij]quinazolin-5(3H)-one | 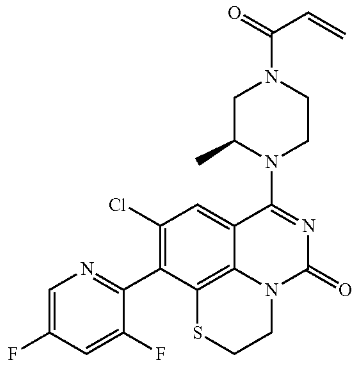 [SMILES: C=CC(=O)N1CCN(c2nc(=O)n3c4c(c(-c5ncc(F)cc5F)c(Cl)cc24)SCC3)[C@@H](C)C1] | $^1$H NMR (400 MHz, $CDCl_3$) δ 8.53 (d, J = 2 Hz, 1H), 7.49 (s, 1H), 7.42-7.38 (m, 1H), 6.61-6.52 (m, 1H), 6.40-6.36 (m, 1H), 5.78 (d, J = 10 Hz, 1H), 4.69 (s, 0.5H), 4.66-4.50 (m, 3H), 4.29-4.15(m, 2H), 3.99-3.96 (m, 0.5H), 3.83-3.79 (m, 0.5H), 3,64-3.47 (m, 2H), 3.14- 3.04 (m, 2.5H), 1.47-1.37 (m, 3H). | 504.1 |
| 409 | 7-((S)-4-acryloyl-2-methylpiperazin-1-yl)-9-chloro-10-(2,4,5-trifluorophenyl)-2,3-dihydro-5H-[1,4]thiazino[2,3,4-ij]quinazolin-5-one | | 1H NMR (400 MHz, MeOD) δ 7.59 (d, J = 6.9 Hz, 1H), 7.42-7.04 (m, 2H), 6.85-6.60 (m, 1H), 6.27-6.10 (m, 1H), 5.71 (dd, J = 10.6, 1.9 Hz, 1H), 4.68 (s, 1H), 4.53-4.25 (m, 2H), 4.23-3.84 (m, 3H), 3.68-3.31 (m, 2H), 3.18-2.85 (m, 3H), 1.30 (dd, J = 16.5, 6.7 Hz, 3H). | 521.1 |

TABLE 7-continued

| Table of Thiomorpholines | | | | |
|---|---|---|---|---|
| Ex. # | Name | Structure | $^1$H NMR | MS (M + H)$^+$ |
| 419 | 7-((S)-4-acryloyl-2-methylpiperazin-1-yl)-9-chloro-10-(7-fluoro-1H-indazol-4-yl)-2,3-dihydro-5H-[1,4]thiazino [2,3,4-ij]quinazolin-5-one | 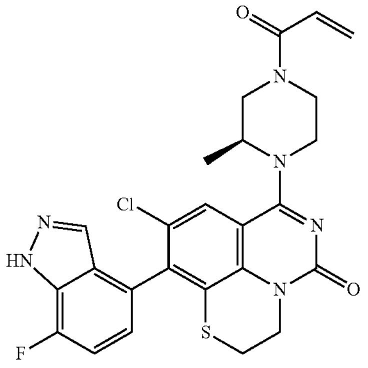 [SMILES: C=CC(=O)N1CCN(c2nc(=O)n3c4c(c(-c5ccc(F)c6[nH]ncc56)c(Cl)cc24)SCC3)[C@@H](C)C1] | $^1$H NMR (400 MHz, MeOH-$d_4$) δ 7.74 (d, J = 2.7 Hz, 1H), 7.72-7.65 (m, 3H), 7.35 (t, J = 9.3 Hz, 1H), 6.92-6.75 (m, 1H), 6.29 (dd, J = 16.7, 6.2 Hz, 1H), 5.82 (dd, J = 10.6, 1.9 Hz, 1H), 4.62-3.98 (m, 6H), 3.77-3.42 (m, 2H), 3.15 (t, J = 5.3 Hz, 3H), 1.43 (t, J = 6.8 Hz, 3H). | 525.2 |
| 419a | (2S)-4-(9-chloro-10-(2,4-difluorophenyl)-5-oxo-3,5-dihydro-2H-[1,4]thiazino[2,3,4-ij]quinazolin-7-yl)-1-(2-fluoroacryloyl)piperazine-2-carbonitrile | | $^1$H NMR (400 MHz, $CDCl_3$) δ 7.70 (d, J = 30.4, 1H), 7.23-7.18 (m, 1H), 7.06-6.97 (m, 2H), 5.82-5.47 (m, 2H), 5.36-5.31 (m, 1H), 4.70-4.45 (m, 2H), 4.42-4.19 (m, 3H), 3.87-3.69 (m, 1H), 3.52-3.43 (m, 1H), 3.27-3.19 (m, 1H), 3.13-3.08 (m, 2H). | 532.1 |
| 427 | 7-((S)-4-acryloyl-2-methylpiperazin-1-yl)-9-chloro-10-(2-chloro-4-fluorophenyl)-2,3-dihydro-5H-[1,4]thiazino[2,3,4-ij]quinazolin-5-one | 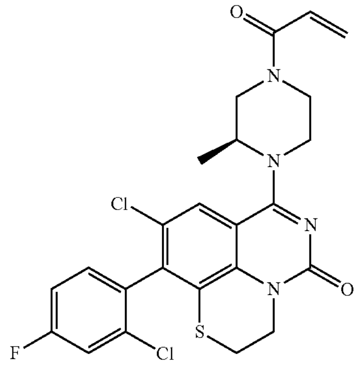 [SMILES: C=CC(=O)N1CCN(c2nc(=O)n3c4c(c(-c5ccc(F)cc5Cl)c(Cl)cc24)SCC3)[C@@H](C)C1] | $^1$H NMR (400 MHz, MeOH-$d_4$) δ 7.68 (d, J = 5.5 Hz, 1H), 7.43 (dd, J = 8.7, 2.4 Hz, 1H), 7.34-7.18 (m, 2H), 6.82 (dddd, J = 21.7, 16.5, 10.7, 2.5 Hz, 1H), 6.28 (dd, J = 16.8, 5.4 Hz, 1H), 5.81 (dd, J = 10.6, 1.9 Hz, 1H), 4.79 (br s, 1H), 4.60-3.97 (m, 6H), 3.76-3.41 (m, 2H), 3.26-3.03 (m, 3H), 1.43 (d, J = 6.7 Hz, 1.5H), 1.39 (d, J = 6.7 Hz, 1.5H). | 519.1. |
| 427a | 7-((S)-4-acryloyl-2-methylpiperazin-1-yl)-9-chloro-10-(5-chloro-2,4-difluorophenyl)-2H-[1,4]thiazino[2,3,4-ij]quinazolin-5(3H)-one | 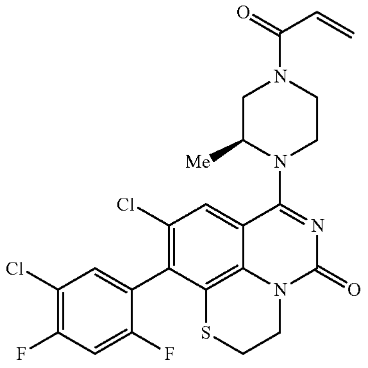 [SMILES: C=CC(=O)N1CCN(c2nc(=O)n3c4c(c(-c5cc(Cl)c(F)cc5F)c(Cl)cc24)SCC3)[C@@H](C)C1] | $^1$H NMR (400 MHz, $CD_3OD$) δ 6.78 (d, J = 6.8 Hz, 1H), 6.57 (t, J = 6.8 Hz, 1H), 6.48-6.44 (t, J = 9.6 Hz, 1H), 5.92-5.87 (m, 1H), 5.40-5.34 (m, 1H), 4.90 (d, J = 10.4 Hz, 1H), 3.88-3.87(m, 1H), 3.67-3.09 (m, 5H), 2.83-2.58(m, 2H), 2.31-2.28 (m, 3H), 0.52-0.46 (m, 3H) | 537.1 |

TABLE 7-continued

Table of Thiomorpholines

| Ex. # | Name | Structure | $^1$H NMR | MS $(M + H)^+$ |
|---|---|---|---|---|
| 441 | 7-((S)-4-acryloyl-2-methylpiperazin-1-yl)-9-chloro-10-(5-fluoroquinolin-8-yl)-2,3-dihydro-5H-[1,4]thiazino[2,3,4-ij]quinazolin-5-one | 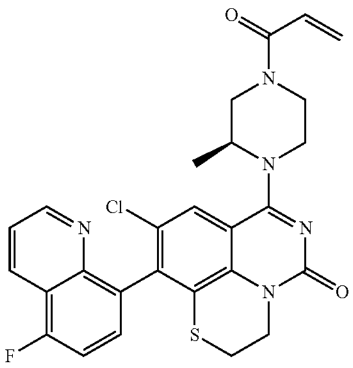 [SMILES: C=CC(=O)N1CCN(c2nc(=O)n3c4c(c(-c5ccc(F)c6cccnc56)c(Cl)cc24)SCC3)[C@@H](C)C1] | $^1$H NMR (400 MHz, MeOH-$d_4$) δ 8.83 (dd, J = 4.3, 1.7 Hz, 1H), 8.65 (dd, J = 8.6, 1.7 Hz, 1H), 7.77-7.60 (m, 3H), 7.49 (t, J = 9.6 Hz, 1H), 6.84 (ddd, J = 22.8, 16.8, 10.5 Hz, 1H), 6.29 (dd, J = 16.8, 6.7 Hz, 1H), 5.82 (dd, J = 10.5, 1.9 Hz, 1H), 4.82 (br s, 1H), 4.63-3.99 (m, 5H), 3.79-3.41 (m, 2H), 3.24-2.95 (m, 3H), 1.46 (d, J = 6.8 Hz, 1.5H), 1.38 (d, J = 6.7 Hz, 1.5H) | 536.2 |
| 410 | (S)-7-((S)-4-acryloyl-2-methylpiperazin-1-yl)-9-chloro-3((4-ethylpiperazin-1-yl)methyl)-10-(4-fluorophenyl)-2H-[1,4]thiazino[2,3,4-ij]quinazolin-5(3H)-one | 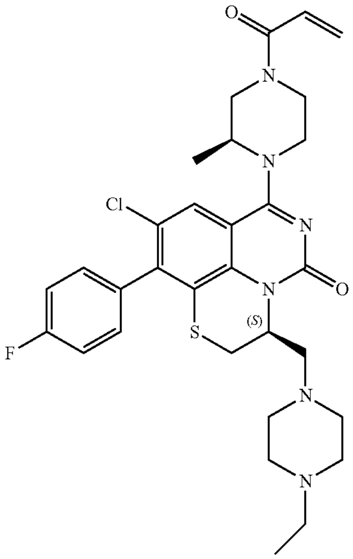 | $^1$H NMR (400 MHz, $CDCl_3$) δ 7.47 (s, 1H), 7.23-7.20 (m, 4H), 6.65-6.50 (m, 1H), 6.36 (d, J = 16.8 Hz, 1H), 5.77 (d, J = 10.8 Hz, 1H), 5.39-5.30 (m, 1H), 4.74-4.64 (m, 1H), 4.57-4.16 (m, 2H), 3.98-3.78 (m, 1H), 3.64-3.36 (m, 3H), 3.09-2.95 (m, 2H), 2.84-2.73 (m, 3H), 2.55-2.35 (m, 9H), 1.47-1.43 (m, 3H), 1.08-1.04 (m, 3H),. | 611.2 |
| 411 | (3S)-7-((S)-4-acryloyl-2-methylpiperazin-1-yl)-9-chloro-10-(2,4-difluorophenyl)-3-((4-methylpiperazin-1-yl)methyl)-2H-[1,4]thiazino[2,3,4-ij]quinazolin-5(3H)-one | 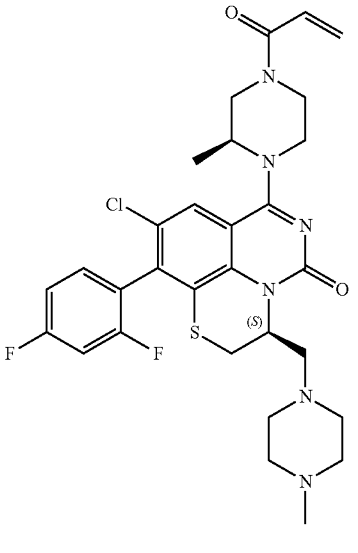 | $^1$H NMR (400 MHz, $CDCl_3$) δ 7.48 (s, 1H), 7.24-7.18 (m, 1H), 7.06-6.95 (m, 2H), 6.66-6.50 (m, 1H), 6.36 (d, J = 16.8 Hz, 1H), 5.77 (d, J = 10.4 Hz, 1H), 5.41-5.28 (m, 1H), 4.73-4.19 (m, 3H), 3.98-3.78 (m, 1H), 3.60-3.39 (m, 3H), 3.08-3.00 (m, 2H), 2.84-2.76 (m, 3H), 2.55-2.39 (m, 7H), 2.55 (m, 3H), 1.48-1.43 (m, 3H). | 615.2 |

TABLE 7-continued

| Table of Thiomorpholines | | | | |
|---|---|---|---|---|
| Ex. # | Name | Structure | $^1H$ NMR | MS $(M + H)^+$ |
| 412 | (3S)-7-((S)-4-acryloyl-2-methylpiperazin-1-yl)-9-chloro-10-(5-chloro-2,4-difluorophenyl)-3-((4-ethylpiperazin-1-yl)methyl)-2H-[1,4]thiazino[2,3,4-ij]quinazolin-5(3H)-one | 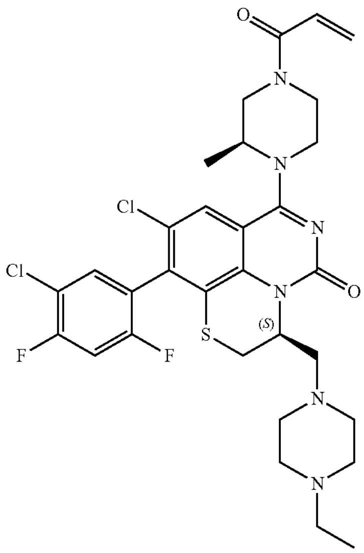 | $^1H$ NMR (400 MHz, $CDCl_3$) δ 7.48 (s, 1H), 7.30 (t, J = 7.6 Hz, 1H),7.12-7.07 (m, 1H), 6.66-6.52 (m, 1H), 6.39-6.35 (m, 1H), 5.78 (d, J = 10.8 Hz, 1H), 5.40-5.34 (m, 1H), 4.71-4.64 (m, 1H), 4.54-4.32 (m, 1.5H), 4.20-4.17 (m, 0.5H), 3.98-3.96 (m, 0.5H), 3.82-3.79 (m, 0.5H), 3.59-3.57 (m, 1.5H), 3.45-3.42 (m, 1.5H), 3.05-3.02 (m, 2H), 2.84-2.74 (m, 3H), 2.57-2.36 (m, 9H), 1.48-1.44 (m, 3H), 1.09-1.05 (m, 3H). | 663.2 |
| 413 | (3S)-7-((S)-4-acryloyl-2-methylpiperazin-1-yl)-9-chloro-10-(2,4-difluorophenyl)-3-((1-ethylpiperidin-4-yl)methyl)-2H-[1,4]thiazino[2,3,4-ij]quinazolin-5(3H)-one | 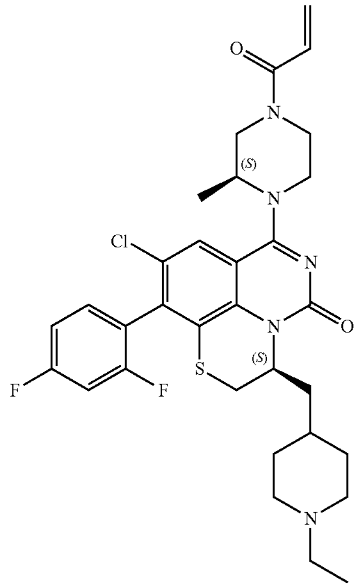 | $^1H$ NMR (400 MHz, $CDCl_3$) δ 7.49 (s, 1H), 7.24-7.18 (m, 1H), 7.07-6.96 (m, 2H), 6.61-6.52 (m, 1H), 5.79-5.76 (d, J = 11.2 Hz, 1H), 5.46 (s, 1H), 4.75-4.15 (m, 4H), 3.58-3.46 (m, 1H), 3.13-3.07(m, 2H), 3.02-2.89 (m, 3H), 2.39-2.37(dd, J = 2.0 Hz, 2H), 1.93-1.88 (m, 2H), 1.79-1.66 (m, 3H), 1.46-1.42(d, J = 14.4 Hz, 2H), 1.36-1.32 (m, 2H), 1.09-1.05 (m, 3H). | 628.3 |

TABLE 7-continued

| Table of Thiomorpholines | | | | |
|---|---|---|---|---|
| Ex. # | Name | Structure | $^1$H NMR | MS $(M + H)^+$ |
| 414 | (3S)-7-((S)-4-acryloyl-2-methylpiperazin-1-yl)-9-chloro-3-((1-(2,2-difluoroethyl)piperidin-4-yl)methyl)-10-(2,4-difluorophenyl)-2H-[1,4]thiazino[2,3,4-ij]quinazolin-5(3H)-one | 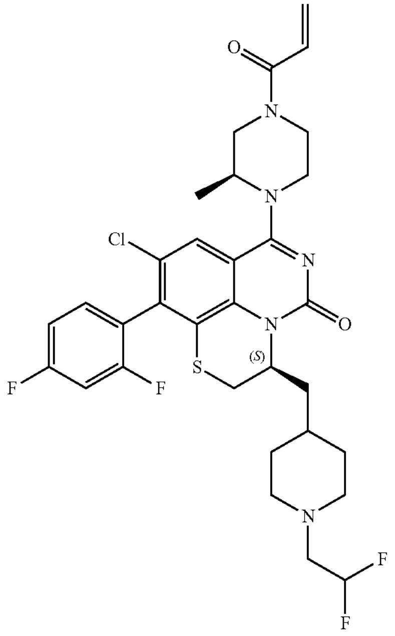 | $^1$H NMR (400 MHz, $CDCl_3$) δ 7.50 (s, 1H), 7.26-7.24(m, 1H), 7.07-6.97 (m, 2H), 6.67-6.51 (m, 1H), 6.35 (d, J = 23.6 Hz, 1H), 6.01-5.70 (m, 2H), 5.51-5.37 (m, 1H), 4.78-4.64 (m, 1H), 4.59-4.16 (m, 2H), 4.03-3.76 (m, 1H), 3.64-3.42 (m, 2H), 3.15-3.03 (m, 2H), 2.98-2.87 (m, 3H), 2.74-2.63 (m, 2H), 2.22-2.08 (m, 2H), 1.77-1.71 (m, 4H), 1.48-1.28 (m, 6H). | 664.3 |
| 415 | (3S)-7-((S)-4-acryloyl-2-methylpiperazin-1-yl)-9-chloro-10-(2,4-difluorophenyl)-3-((1-(oxetan-3-yl)piperidin-4-yl)methyl)-2H-[1,4]thiazino[2,3,4-ij]quinazolin-5(3H)-one | 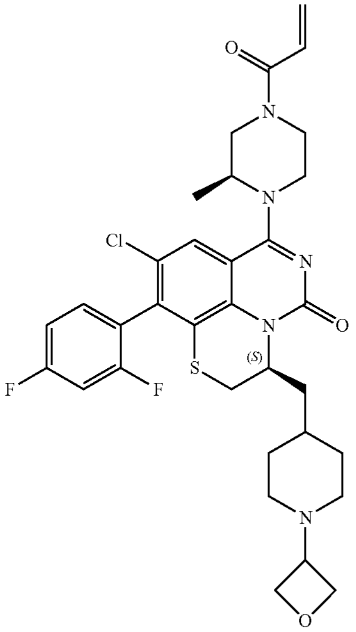 | $^1$H NMR (400 MHz, $CDCl_3$) δ 7.50 (s, 1H), 7.24-7.20 (m, 1H), 7.07-6.97 (m, 2H), 6.61-6.51 (m, 1H), 6.35 (d, J = 27.2 Hz, 1H), 5.79 (d, J = 18.4 Hz, 1H), 5.49-5.36 (m, 1H), 4.74-4.60 (m, 5H), 4.56-4.15 (m, 2H), 4.01-3.77 (m, 1H), 3.63-3.40 (m, 3H), 3.17-2.76 (m, 5H), 2.05-1.86 (m, 4H), 1.55-1.21 (m, 8H). | 656.3 |

TABLE 7-continued

| Ex. # | Name | Structure | $^1$H NMR | MS (M + H)$^+$ |
|---|---|---|---|---|
| | Table of Thiomorpholines | | | |
| 416 | (3S)-7-((S)-4-acryloyl-2-methylpiperazin-1-yl)-9-chloro-3-((4-ethylpiperazin-1-yl)methyl)-10-(2,4,5-trifluorophenyl)-2H-[1,4]thiazino[2,3,4-ij]quinazolin-5(3H)-one | 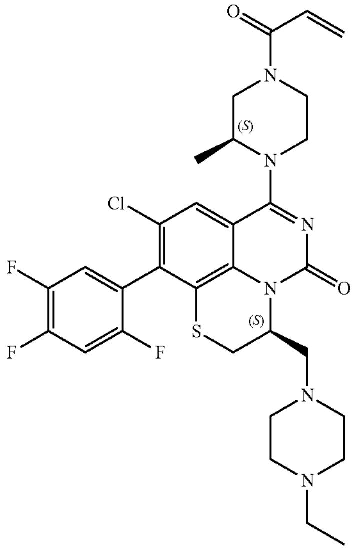 | $^1$H NMR (400 MHz, $CDCl_3$) δ 7.48 (s, 1H), 7.12-7.07 (m, 2H), 6.66-6.51 (m, 1H), 6.37 (d, J = 16.8 Hz, 1H), 5.78 (d, J = 10.8 Hz, 1H), 5.40-5.34 (m, 1H), 4.72-4.66 (m, 1H), 4.54-4.53 (m, 0.5H), 4.44-4.34 (m, 1H), 4.20-4.16 (m, 0.5H), 3.98-3.95 (m, 0.5H), 3.82-3.78 (m, 0.5H), 3.58-3.56 (m, 1.5H), 3.44-3.41 (m, 1.5H), 3.05-3.01 (m, 2H), 2.81-2.75 (m, 3H), 2.57-2.40 (m, 8H), 1.45 (d, J = 19.6 Hz, 4H), 1.25 (s, 3H), 1.10-1.06 (m, 3H). | 647.3 |
| 421 | (3S)-7-((S)-4-acryloyl-2-methylpiperazin-1-yl)-9-chloro-3-((1-(oxetan-3-yl)piperidin-4-yl)methyl)-10-(2,4,5-trifluorophenyl)-2H-[1,4]thiazino[2,3,4-ij]quinazolin-5(3H)-one | 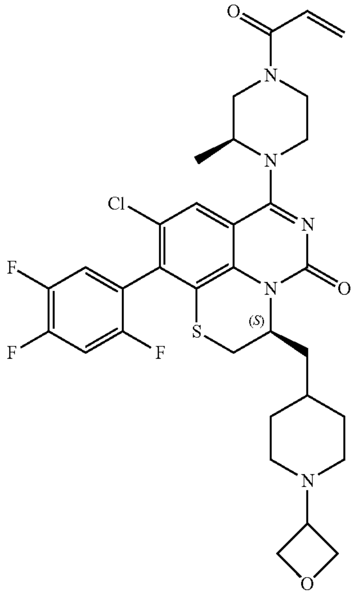 | $^1$H NMR (400 MHz, $CDCl_3$) δ 7.50 (s, 1H), 7.15-7.05 (m, 2H), 6.62-6.52 (m, 1H), 6.37 (d, J = 16.8 Hz, 1H), 5.78 (d, J = 10.8 Hz, 1H), 5.48-5.41 (m, 1H), 4.75-4.55 (m, 5.5H), 4.44-4.35 (m, 1H), 4.20-4.17 (m, 0.5H), 3.98-3.94 (m, 0.5H), 3.82-3.79 (m, 0.5H), 3.59-3.40 (m, 3H), 3.15-2.97 (m, 3H), 2.71-2.68 (m, 2H), 1.84-1.68 (m, 6H), 1.47-1.27 (m, 6H). | 674.3 |

TABLE 7-continued

| Table of Thiomorpholines | | | | |
|---|---|---|---|---|
| Ex. # | Name | Structure | $^1$H NMR | MS (M + H)$^+$ |
| 422 | (3S)-7-((S)-4-acryloyl-2-methylpiperazin-1-yl)-9-chloro-3((4-cyclopropylpiperazin-1-yl)methyl)-10-(2,4-difluorophenyl)-2H-[1,4]thiazino[2,3,4-ij]quinazolin-5(3H)-one | 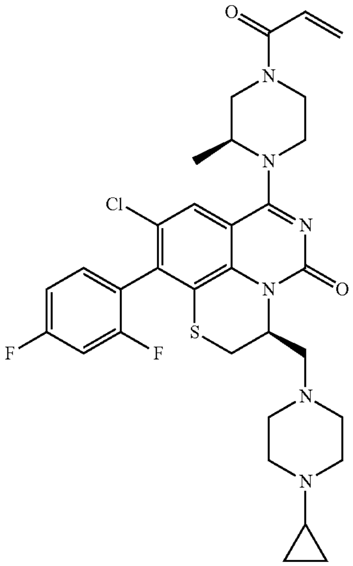 [SMILES: C=CC(=O)N1CCN(c2nc(=O)n3c4c(c(-c5ccc(F)cc5F)c(Cl)cc24)SC[C@@H]3CN2CCN(C3CC3)CC2)[C@@H](C)C1] | $^1$H NMR (400 MHz, $CDCl_3$) δ 7.48 (s, 1H), 7.24-7.18 (m, 1H), 7.06-6.95 (m, 2H), 6.66-6.50 (m, 1H), 6.36 (d, J = 16.4 Hz, 1H), 5.77 (d, J = 10.8 Hz, 1H), 5.40-5.31 (m, 1H), 4.73-4.68 (m, 1H), 4.55-4.15 (m, 2H), 3.99-3.77 (m, 1H), 3.59-3.41 (m, 3H), 3.08-3.00 (m, 2H), 2.83-2.48 (m, 10H), 1.48-1.43 (m, 3H), 1.26 (m, 1H), 0.42-0.39 (m, 4H). | 641.3 |
| 423 | (3S)-7-((S)-4-acryloyl-2-methylpiperazin-1-yl)-9-chloro-10-(2,4-difluorophenyl)-3-((1-methylpiperidin-4-yl)methyl)-2H-[1,4]thiazino[2,3,4-ij]quinazolin-5(3H)-one | 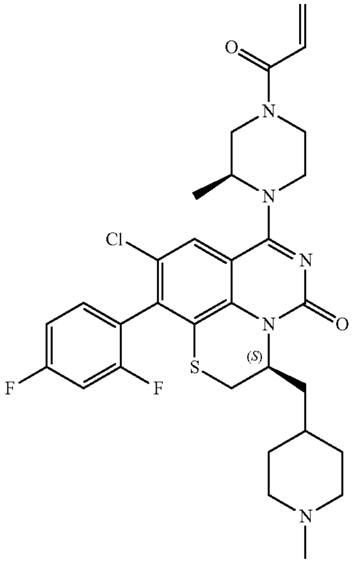 | $^1$H NMR (400 MHz, $CDCl_3$) δ 7.50 (s, 1H), 7.24-7.18 (m, 1H), 7.08-6.97 (m, 2H), 6.68-6.32 (m, 2H), 5.80-5.36 (m, 2H), 4.78-4.66 (m, 1H), 4.62-4.15 (m, 2H), 4.00-3.76 (m, 1H), 3.62-3.42 (m, 2H), 3.16-2.83 (m, 6H), 2.29 (s, 3H), 1.92-1.64 (m, 9H), 1.41-1.24 (m, 3H). | 614.3 |

TABLE 7-continued

| Table of Thiomorpholines | | | | |
|---|---|---|---|---|
| Ex. # | Name | Structure | $^1$H NMR | MS $(M + H)^+$ |
| 424 | (R)-7-((S)-4-acryloyl-2-methylpiperazin-1-yl)-9-chloro-3-((4-ethylpiperazin-1-yl)methyl)-10-(2,4,6-trifluorophenyl)-2H-[1,4]thiazino[2,3,4-ij]quinazolin-5(3H)-one | 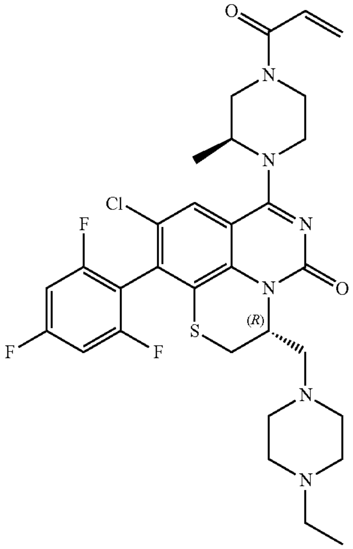 | $^1$H NMR (400 MHz, $CDCl_3$) δ 7.50 (s, 1H), 6.84 (t, J = 7.2 Hz, 2H), 6.59-6.55 (m, 1H), 6.39-6.35 (m, 1H), 6.79-6.77 (d, J = 10.2 Hz, 1H), 5.41-5.40 (m, 1H), 4.90-4.63 (m, 2H), 4.04-4.01 (m, 2H), 3.7-3.65(m, 2H), 3.46-3.43 (d, J = 12.8 Hz, 2H), 3.27-3.06 (m, 2H), 2.94-2.82 (m, 3H), 2.55-2.52 (m, 2H), 2.46-2.45 (m, 2H), 2.43-2.41 (m, 2H), 2.40-2.38 (m, 3H), 1.37-1.36 (d, J = 6.8 Hz, 3H), 1.10-1.06 (m, 3H). | 647.3 |
| 425 | (S)-7-((S)-4-acryloyl-2-methylpiperazin-1-fluorophenyl)-3-((1-(oxetan-3-yl)piperidin-4-yl)methyl)-9-(trifluoromethyl)-2H-[1,4]thiazino[2,3,4-ij]quinazolin-5(3H)-one | 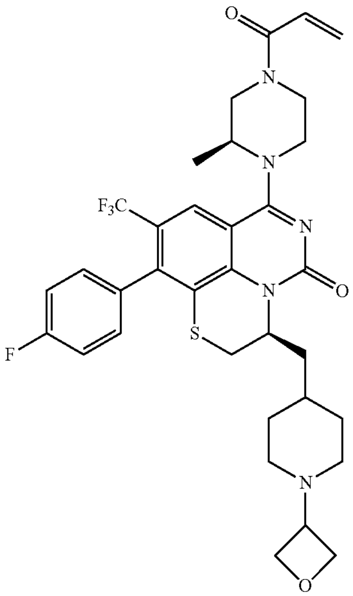 [SMILES: C=CC(=O)N1CCN(c2nc(=O)n3c4c(c(-c5ccc(F)cc5)c(C(F)(F)F)cc24)SC[C@@H]3CC2CCN(C3COC3)CC2)[C@@H](C)C1] | $^1$H NMR (400 MHz, $CDCl_3$) δ 7.78 (s, 1H), 7.25-7.16 (m, 4H), 6.62-6.53 (m, 1H), 6.39-6.35 (m, 1H), 5.79 (d, J = 10.4 Hz, 1H), 5.40-5.39 (m, 1H), 4.68-4.58 (m, 5H), 4.48-4.25 (m, 2H), 3.98-3.80 (m, 1H), 3.63-3.38 (m, 3H), 3.07-3.04 (m, 2H), 2.98-2.94 (m, 1H), 2.70 (t, J = 12.4 Hz, 2H), 1.84-1.69 (m, 6H), 1.52-1.40 (m, 4H), 1.39-1.26 (m, 2H). | 672.3 |

TABLE 7-continued

| Table of Thiomorpholines | | | | |
|---|---|---|---|---|
| Ex. # | Name | Structure | $^1$H NMR | MS $(M + H)^+$ |
| 426 | (3S)-7-((S)-4-acryloyl-2-methylpiperazin-1-yl)-9-chloro-10-(5-chloro-2,4-difluorophenyl)-3-((1-(oxetan-3-yl)piperidin-4-yl)methyl)-2H-[1,4]thiazino[2,3,4-ij]quinazolin-5(3H)-one | 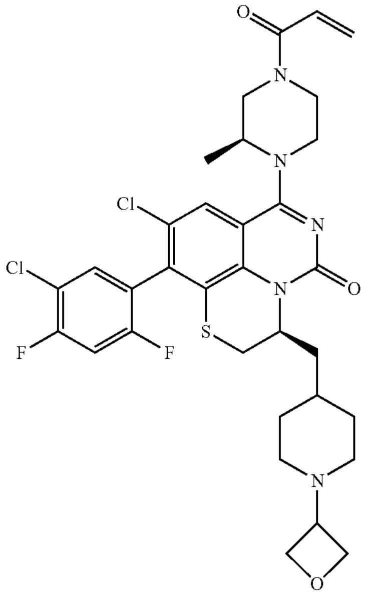 [SMILES: C=CC(=O)N1CCN(c2nc(=O)n3c4c(c(-c5cc(Cl)c(F)cc5F)c(Cl)cc24)SC[C@@H]3CC2CCN(C3COC3)CC2)[C@@H](C)C1] | $^1$H NMR (400 MHz, $CDCl_3$) δ 7.50 (s, 1H), 7.34-7.28 (m, 1H), 7.13-7.07 (m, 1H), 6.62-6.52 (m, 1H), 6.37 (d, J = 17.2 Hz, 1H), 5.78 (d, J = 10.8 Hz, 1H), 5.49-5.43 (m, 1H), 4.73-4.54 (m, 5.5H), 4.47-4.33 (m, 1H), 4.21-4.17 (m, 0.5H), 3.99-3.96 (m, 0.5H), 3.83-3.80 (m, 0.5H), 3.58-3.49 (m, 1.5H), 3.49-3.39 (m, 1.5H), 3.16-2.97 (m, 3H), 2.74-2.70 (m, 2H), 1.84-1.74 (m, 5H), 1.46-1.32 (m, 7H). | 690.3 |
| 428 | (S)-7-((S)-4-acryloyl-2-methylpiperazin-1-yl)-3-((1-(2,2-difluoroethyl)piperidin-4-yl)methyl)-10-(4-fluorophenyl)-9-(trifluoromethyl)-2H-[1,4]thiazino[2,3,4-ij]quinazolin-5(3H)-one | 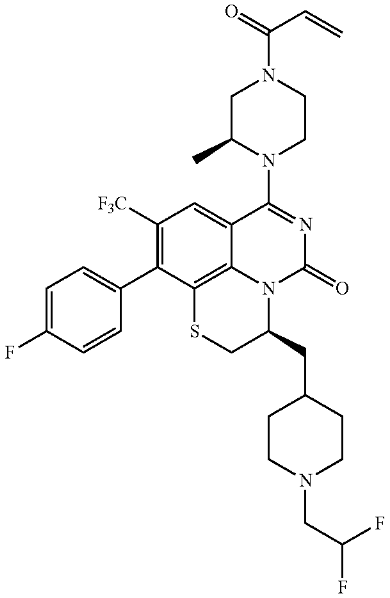 [SMILES: C=CC(=O)N1CCN(c2nc(=O)n3c4c(c(-c5ccc(F)cc5)c(C(F)(F)F)cc24)SC[C@@H]3CC2CCN(CC(F)F)CC2)[C@@H](C)C1] | $^1$H NMR (400 MHz, $CDCl_3$) δ 7.78 (s, 1H), 7.21-7.16 (m, 4H), 6.62-6.54 (m, 1H), 6.39 (d, J = 16.4 Hz, 1H), 6.00-5.70 (m, 2H), 5.39-5.37 (m, 1H), 4.68-4.66 (m, 1H), 4.48-4.39 (m, 1.5H), 4.29-4.25 (m, 0.5H), 3.98-3.95 (m, 0.5H), 3.83-3.80 (m, 0.5H), 3.63-3.44 (m, 2H), 3.07 (d, J = 13.2 Hz, 2H), 2.97-2.87 (m, 3H), 2.74-2.65 (m, 2H), 2.21-2.11 (m, 2H), 1.74-1.67 (m, 4H), 1.52-1.40 (m, 4H), 1.31-1.27 (m, 2H). | 680.3 |

TABLE 7-continued

| Table of Thiomorpholines | | | | |
|---|---|---|---|---|
| Ex. # | Name | Structure | $^1$H NMR | MS (M + H)$^+$ |
| 429 | (3S)-7-((S)-4-acryloyl-2-methylpiperazin-1-yl)-3-((1-(2,2-difluoroethyl)piperidin-4-yl)methyl)-10-(2,4-difluorophenyl)-9-(trifluoromethyl)-2H-[1,4]thiazino[2,3,4-ij]quinazolin-5(3H)-one 1,1-dioxide | 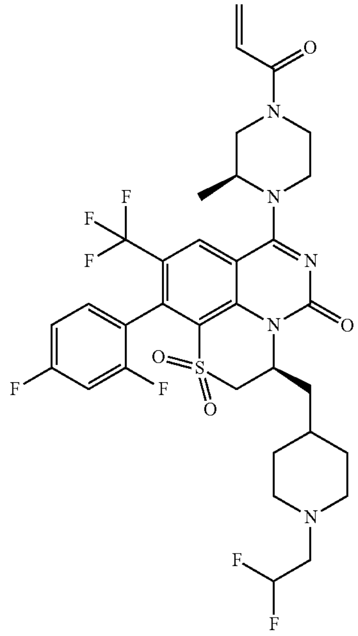 [SMILES: C=CC(=O)N1CCN(c2nc(=O)n3c4c(c(-c5ccc(F)cc5F)c(C(F)(F)F)cc24)S(=O)(=O)C[C@@H]3CC2CCN(CC(F)F)CC2)[C@@H](C)C1] | $^1$H NMR (400 MHz, $CDCl_3$) δ 8.15 (s, 1H), 7.43-7.26 (m, 1H), 7.02-6.89 (m, 2H), 6.56 (dd, J = 14.6 Hz, 1.6 Hz, 1H), 6.34 (d, J = 16.4 Hz, 1H), 6.00-5.70 (m, 2H), 5.08-5.04 (m, 1H), 5.04-4.30 (m, 3H), 4.14-3.77 (m, 2H), 3.72-3.43 (m, 3H), 3.33-3.07 (m, 1H), 2.96-2.89 (m, 2H), 2.74-2.65 (m, 2H), 2.22-2.07 (m, 3H), 1.78-1.62 (m, 4H), 1.45-1.25 (m, 5H) | 730.3 |
| 430 | (S)-7-((S)-4-acryloyl-2-methylpiperazin-1-yl)-10-(4-fluorophenyl)-9-(trifluoromethyl)-3-((3-(trifluoromethyl)-5,6-dihydro-[1,2,4]triazolo[4,3-a]pyrazin-7(8H)-yl)methyl)-2H-[1,4]thiazino[2,3,4-ij]quinazolin-5(3H)-one | 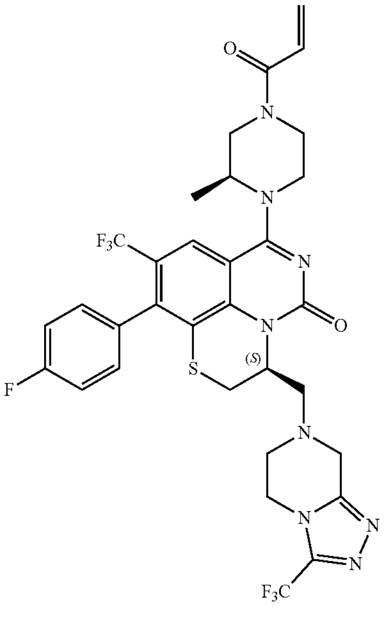 | $^1$H NMR (400 MHz, $CDCl_3$) δ 7.80 (s, 1H), 7.21-7.20 (m, 4H), 6.61-6.52 (m, 1H), 6.39-6.35 (m, 1H), 5.79 (d, J = 10.4 Hz, 1H), 5.35-5.31 (brs, 1H), 4.76-4.73 (m, 1H), 4.65-4.56 (m, 1H), 4.43-4.33 (m, 2H), 4.17-3.96 (m, 3H), 3.93-3.80 (m, 1H), 3.60-3.42 (m, 4H), 3.20-3.06 (m, 4H), 2.97-2.94 (m, 1H), 1.55-1.50 (m, 3H). | 723.3 |

TABLE 7-continued

| Table of Thiomorpholines | | | | |
|---|---|---|---|---|
| Ex. # | Name | Structure | $^1H$ NMR | MS $(M + H)^+$ |
| 432 | (3R)-7-((S)-4-acryloyl-2-methylpiperazin-1-yl)-9-chloro-10-(2,4-difluorophenyl)-3-(((1-ethylazetidin-3-yl)oxy)methyl)-2,3-dihydro-5H-[1,4]thiazino[2,3,4-ij]quinazolin-5-one | 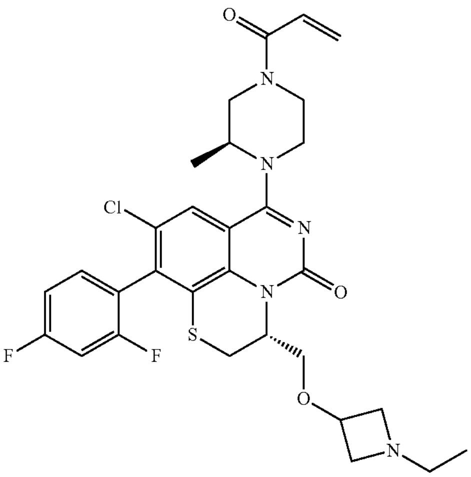 [SMILES: C=CC(=O)N1CCN(c2nc(=O)n3c4c(c(-c5ccc(F)cc5F)c(Cl)cc24)SC[C@H]3COC2CN(CC)C2)[C@@H](C)C1] | $^1H$ NMR (400 MHz, MeOH-$d_4$) δ 7.76 (s, 1H), 7.39-7.26 (m, 1H), 7.23-7.07 (m, 2H), 6.91-6.74 (m, 1H), 6.29 (dd, J = 16.6, 4.6 Hz, 1H), 5.81 (d, J = 10.6 Hz, 1H), 5.40-5.25 (m, 1H), 5.03-4.93 (m, 1H), 4.65-4.35 (m, 2H), 4.33-4.00 (m, 3H), 3.98-3.57 (m, 6H), 3.51-3.34 (m, 3H), 3.27-2.94 (m, 3H), 1.40-1.26 (m, 3H), 1.25-1.11 (m, 3H) | 616.2 |
| 433 | 7'-((S)-4-acryloyl-2-methylpiperazin-1-yl)-9'-chloro-10'-(2,4-difluorophenyl)-3'H,5'H-spiro[cyclopropane-1,2'-[1,4]thiazino[2,3,4-ij]quinazolin]-5'-one | 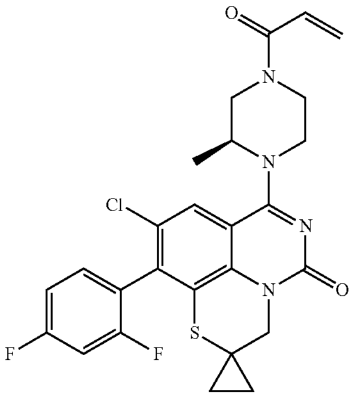 [SMILES: C=CC(=O)N1CCN(c2nc(=O)n3c4c(c(-c5ccc(F)cc5F)c(Cl)cc24)SC2(CC2)C3)[C@@H](C)C1] | $^1H$ NMR (400 MHz, MeOH-$d_4$) δ 7.61 (d, J = 6.6 Hz, 1H), 7.18 (tdd, J = 8.7, 6.3, 2.3 Hz, 1H), 7.09-6.96 (m, 2H), 6.72 (dddd, J = 20.7, 16.7, 10.5, 3.3 Hz, 1H), 6.19 (dd, J = 16.9, 6.2 Hz, 1H), 5.71 (dd, J = 10.6, 2.0 Hz, 1H), 5.04 (d, J = 8.6 Hz, 1H), 4.58-4.40 (m, 1H), 4.36-3.87 (m, 4H), 3.72-3.35 (m, 4H), 1.34 (d, J = 6.8 Hz, 1.5H), 1.29 (d, J = 6.7 Hz, 1.5H), 1.08-0.99 (m, 2H), 0.93-0.76 (m, 2H) | 529.2 |
| 434 | (3S)-7-((S)-4-acryloyl-2-methylpiperazin-1-yl)-10-(2,4-difluorophenyl)-3-((1-ethylpiperidin-4-yl)methyl)-9-(trifluoromethyl)-2H-[1,4]thiazino[2,3,4-ij]quinazolin-5(3H)-one 1,1-dioxide | 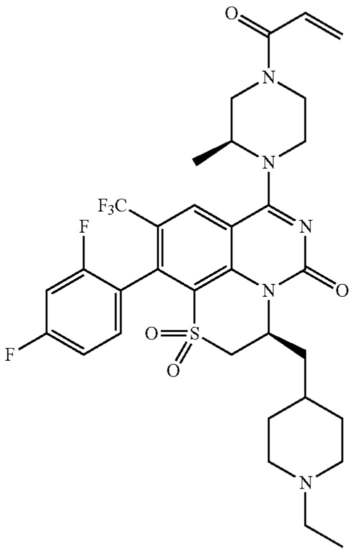 [SMILES: C=CC(=O)N1CCN(c2nc(=O)n3c4c(c(-c5ccc(F)cc5F)c(C(F)(F)F)cc24)S(=O)(=O)C[C@@H]3CC2CCN(CC)CC2)[C@@H](C)C1] | $^1H$ NMR (400 MHz, $CDCl_3$) δ 8.15 (s, 1H), 7.43-7.31 (m, 1H), 7.03-6.89 (m, 2H), 6.60-6.53 (m, 1H), 6.39 (dd, J = 1.2 Hz, 16.8 Hz, 1H), 5.81 (d, J = 10.4 Hz, 1H), 5.58-5.57 (m, 1H), 4.75-4.33 (m, 3H), 4.03-3.82 (m, 1H), 3.69-3.45 (m, 4H), 3.13-3.05 (m, 3H), 2.58-2.52 (m, 2H), 2.24-2.09 (m, 3H), 1.92-1.86 (m, 2H), 1.58-1.52 (m, 7H), 1.18 (t, J = 6.8 Hz, 3H). | 694.2 |

TABLE 7-continued

| Table of Thiomorpholines | | | | |
|---|---|---|---|---|
| Ex. # Name | Structure | $^1$H NMR | MS (M + H)$^+$ |
| 435 (3S)-7-((S)-4-acryloyl-2-methylpiperazin-1-yl)-10-(2,4-difluorophenyl)-3-(methoxymethyl)-9-(trifluoromethyl)-2H-[1,4]thiazino[2,3,4-ij]quinazolin-5(3H)-one | 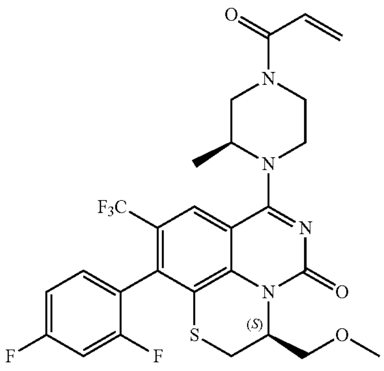 | $^1$H NMR (400 MHz, $CDCl_3$) δ 7.77 (s, 1H), 7.21-7.16 (m, 1H), 7.04-6.94 (m, 2H), 6.66-6.51 (m, 1H), 6.37 (d, J = 16.8 Hz, 1H), 5.78(d, J = 10.4 Hz, 1H), 5.40-5.38 (m, 1H), 4.74-4.29 (m, 3H), 3.99-3.80 (m, 1H), 3.67-3.34 (m, 8H), 3.11-2.99 (m, 2H), 1.55-1.50 (m, 3H). | 581.1 |
| 436 (3S)-7-((S)-4-acryloyl-2-methylpiperazin-1-yl)-10-(2,4-difluorophenyl)-3-(methoxymethyl)-9-(trifluoromethyl)-2H-[1,4]thiazino[2,3,4-ij]quinazolin-5(3H)-one 1,1-dioxide | 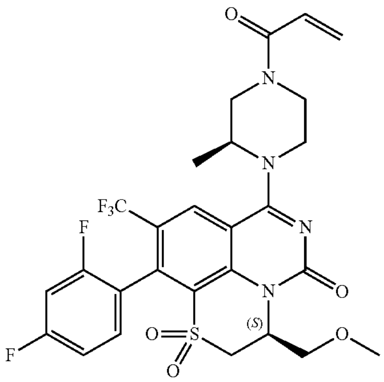 | $^1$H NMR (400 MHz, $CDCl_3$) δ 8.13 (s, 1H), 7.42-7.30 (m, 1H), 7.03-6.88 (m, 2H), 6.66-6.50 (m, 1H), 6.39 (dd, J = 1.6 Hz, 16.8 Hz, 1H), 5.80 (d, J = 10.4 Hz, 1H), 5.54-5.50 (m, 1H), 4.78-4.35 (m, 3H), 4.06-3.73 (m, 4H), 3.61-3.48 (m, 3H), 3.39 (d, J = 8.0 Hz, 3H), 3.10-3.03 (m, 1H), 1.58-1.46 (m, 3H). | 613.2 |
| 437 (3S)-7-((S)-4-acryloyl-2-methylpiperazin-1-yl)-10-(2,4-difluorophenyl)-3-((tetrahydro-2H-pyran-4-yl)methyl)-9-(trifluoromethyl)-2H-[1,4]thiazino[2,3,4-ij]quinazolin-5(3H)-one | 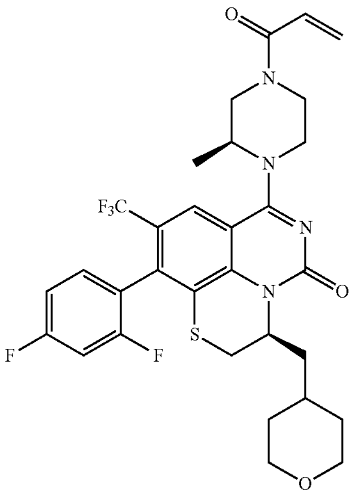 [SMILES: C=CC(=O)N1CCN(c2nc(=O)n3c4c(c(-c5ccc(F)cc5F)c(C(F)(F)F)cc24)SC[C@@H]3CC2CCOCC2)[C@@H](C)C1] | $^1$H NMR (400 MHz, $CDCl_3$) δ 7.79 (s, 1H), 7.23-7.15 (m, 1H), 7.05-6.95 (m, 2H), 6.62-6.55 (m, 1H), 6.39-6.35 (m, 1H), 5.79 (d, J = 10.4 Hz, 1H), 5.45-5.42 (m, 1H), 4.70-4.69 (m, 1H), 4.48-4.39(m, 1.5H), 4.31-4.28 (m, 0.5H), 3.94 (t, J = 11.6 Hz, 2.5H), 3.83-3.81 (m, 0.5H), 3.61-3.45 (m, 2H), 3.42-3.32 (m, 2H), 3.14-3.97 (m, 3H), 1.80-1.72 (m, 4H), 1.53-1.35(m, 5H), 1.32-1.26(m, 1H). | 635.2 |

TABLE 7-continued

| Table of Thiomorpholines | | | | |
|---|---|---|---|---|
| Ex. # | Name | Structure | $^1$H NMR | MS (M + H)$^+$ |
| 438 | (3S)-7-((S)-4-acryloyl-2-methylpiperazin-1-yl)-9-chloro-10-(2,4-difluorophenyl)-3-((tetrahydro-2H-pyran-4-yl)methyl)-2H-[1,4]thiazino[2,3,4-ij]quinazolin-5(3H)-one | 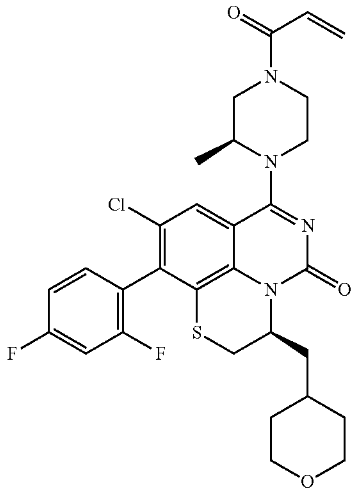 [SMILES: C=CC(=O)N1CCN(c2nc(=O)n3c4c(c(-c5ccc(F)cc5F)c(Cl)cc24)SC[C@@H]3CC2CCOCC2)[C@@H](C)C1] | $^1$H NMR (400 MHz, $CDCl_3$) δ 7.50 (s, 1H), 7.24-7.19 (m, 1H), 7.08-6.96 (m, 2H), 6.62-6.54 (m, 1H), 6.39 (d, J = 16 Hz, 1H), 5.79 (d, J = 10.8 Hz, 1H), 5.46 (s, 1H), 4.74-4.66 (m, 1H), 4.56 (s, 0.5H), 4.44-4.35 (m, 1H), 4.20 (s, 0.5H), 3.96-3.91 (m, 2.5H), 3.91-3.79 (m, 0.5H), 3.58 (s, 1.5H), 3.48-3.46 (m, 0.5H), 3.42-3.31 (m, 2H), 3.15-3.06(m, 2H), 2.99(d, J = 13.6 Hz, 1H), 1.77-1.62(m, 5H), 1.47(d, J = 12.8 Hz, 4H), 1.39-1.30(m, 1H). | 601.2 |
| 443 | (3S)-7-((2S,5R)-4-acryloyl-2,5-dimethylpiperazin-1-yl)-3-((4-(2,2-difluoroethyl)piperazin-1-yl)methyl)-9-(trifluoromethyl)-10-(2,4,5-trifluorophenyl)-2H-[1,4]thiazino[2,3,4-ij]quinazolin-5(3H)-one | 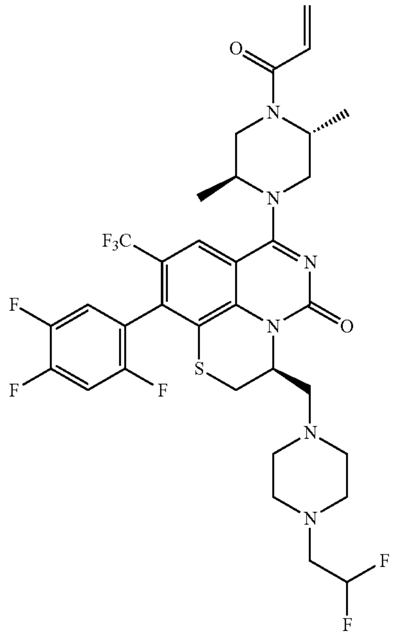 [SMILES: C=CC(=O)N1C[C@H](C)N(c2nc(=O)n3c4c(c(-c5cc(F)c(F)cc5F)c(C(F)(F)F)cc24)SC[C@@H]3CN2CCN(CC(F)F)CC2)C[C@H]1C] | $^1$H NMR (400 MHz, $CDCl_3$) δ 7.83 (s, 1H), 7.09-7.04 (m, 2H), 6.65-6.50 (m, 1H), 6.37 (t, J = 14.0 Hz, 1H), 6.01-5.70 (m, 2H), 5.37 (br, 1H), 5.04 (br, 0.5H), 4.08-4.65 (m, 1H), 4.44-4.33(m, 1.5H), 4.08-4.02 (m, 0.5H), 3.77-3.63 (m, 2H), 3.42-3.01 (m, 3H), 2.75-2.56 (m, 11.5H), 1.48-1.37 (m, 6H). | 731.3 |

TABLE 7-continued

Table of Thiomorpholines

| Ex. # | Name | Structure | $^1$H NMR | MS (M + H)$^+$ |
|---|---|---|---|---|
| 444 | (S)-7-((S)-4-acryloyl-2-methylpiperazin-1-yl)-9-chloro-10-(4-fluorophenyl)-3-((3-(trifluoromethyl)-5,6-dihydro-[1,2,4]triazolo[4,3-a]pyrazin-7(8H)-yl)methyl)-2H-[1,4]thiazino[2,3,4-ij]quinazolin-5(3H)-one | 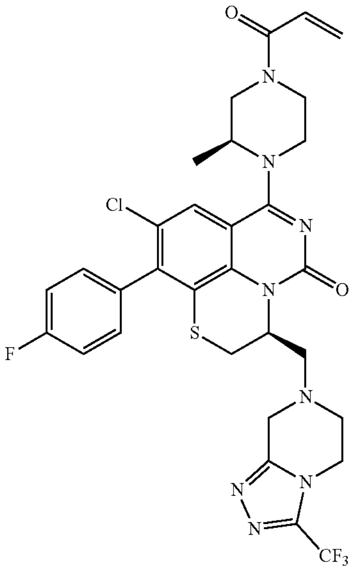 [SMILES: C=CC(=O)N1CCN(c2nc(=O)n3c4c(c(-c5ccc(F)cc5)c(Cl)cc24)SC[C@@H]3CN2CCn3c(nnc3C(F)(F)F)C2)[C@@H](C)C1] | $^1$H NMR (400 MHz, $CDCl_3$) δ 7.51 (s, 1H), 7.23 (d, J = 7.2 Hz, 4H), 6.64-6.49 (m, 1H), 6.39-6.35 (m, 1H), 5.79-5.76 (m, 1H), 5.33-5.29 (m, 1H), 4.73-4.24 (m, 4H), 4.16-3.79 (m, 4H), 3.60-3.40 (m, 3H), 3.33-3.29 (m, 1H), 3.17-3.05 (m, 3H), 2.94-2.90 (m, 1H), 1.47 (d, J = 14.0 Hz, 3H). | 689.2 |
| 445 | (S)-7-((2S,5R)-4-acryloyl-2,5-dimethylpiperazin-1-yl)-9-chloro-10-(4-fluorophenyl)-3-((3-(trifluoromethyl)-5,6-dihydro-[1,2,4]triazolo[4,3-a]pyrazin-7(8H)-yl)methyl)-2H-[1,4]thiazino[2,3,4-ij]quinazolin-5(3H)-one | 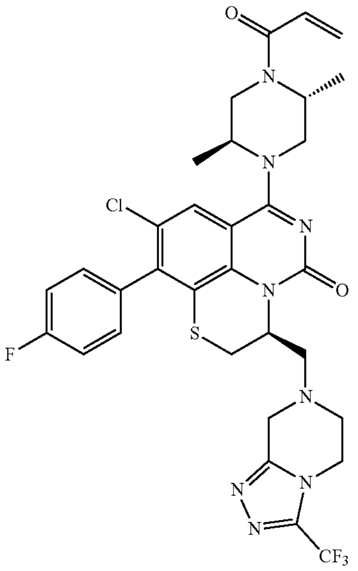 [SMILES: C=CC(=O)N1C[C@H](C)N(c2nc(=O)n3c4c(c(-c5ccc(F)cc5)c(Cl)cc24)SC[C@@H]3CN2CCn3c(nnc3C(F)(F)F)C2)C[C@H]1C] | $^1$H NMR (400 MHz, $CDCl_3$) δ 7.56 (d, J = 9.6 Hz, 1H), 7.23 (d, J = 6.8 Hz, 4H), 6.64-6.49 (m, 1H), 6.36 (t, J = 15.6 Hz, 1H), 5.77 (t, J = 7.6 Hz, 1H), 5.42-5.40 (m, 1H), 5.00-4.99 (m, 1H), 4.82-4.72(m, 1H), 4.38-3.99 (m, 6H), 3.79-3.66 (m, 2H), 3.35-3.19 (m, 3H), 3.10-3.07 (d, J = 11.6 Hz, 2H), 2.93 (d, J = 12.4 Hz, 1H), 1.45-1.38 (m, 3H), 1.31-1.28 (m, 3H). | 703.3 |
| 446 | (3S)-7-((S)-4-acryloyl-2-methylpiperazin-1-yl)-9-chloro-10-(5-chloro-2,4-difluorophenyl)-3-((methoxymethoxy)methyl)-2H-[1,4]thiazino[2,3,4-ij]quinazolin-5(3H)-one | 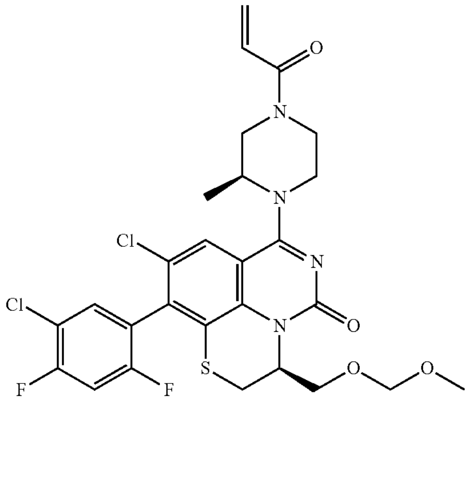 [SMILES: C=CC(=O)N1CCN(c2nc(=O)n3c4c(c(-c5cc(Cl)c(F)cc5F)c(Cl)cc24)SC[C@@H]3COCOC)[C@@H](C)C1] | $^1$H NMR (400 MHz, $CDCl_3$) δ 7.49 (s, 1H), 7.32-7.28 (m, 1H), 7.12-7.06 (m 1H), 6.72-6.45 (m, 1H), 6.39-6.35 (m, 1H), 5.78 (d, J = 10.4 Hz, 1H), 5.44 (brs, 1H), 4.98-4.97 (m, 1H), 4.69-4.62 (m, 2H), 4.15-3.95 (m, 1H), 3.82-3.76 (m, 3H), 3.40-3.35 (m, 4H), 3.35-2.78 (m, 2H), 1.65-1.63 (m, 3H), 1.35 (d, J = 6.8 Hz, 3H). | 611.1 |

TABLE 7-continued

| Table of Thiomorpholines | | | | |
|---|---|---|---|---|
| Ex. # | Name | Structure | $^1$H NMR | MS (M + H)$^+$ |
| 447 | (3S)-7-((S)-4-acryloyl-2-methylpiperazin-1-yl)-9-chloro-10-(5-chloro-2,4-difluorophenyl)-3-((3-(trifluoromethyl)-5,6-dihydro-[1,2,4]triazolo[4,3-a]pyrazin-7(8H)-yl)methyl)-2H-[1,4]thiazino[2,3,4-ij]quinazolin-5(3H)-one | 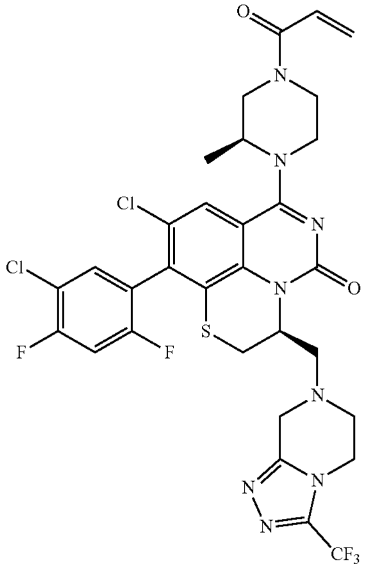 [SMILES: C=CC(=O)N1CCN(c2nc(=O)n3c4c(c(-c5cc(Cl)c(F)cc5F)c(Cl)cc24)SC[C@@H]3CN2CCn3c(nnc3C(F)(F)F)C2)[C@@H](C)C1] | $^1$H NMR (400 MHz, $CDCl_3$) δ 7.51 (s, 1H), 7.32-7.29 (m, 1H), 7.13-7.09 (m, 1H), 6.61-6.52 (m, 1H), 6.39-6.35 (m, 1H), 5.79 (d, J = 10.4 Hz, 1H), 5.37-5.36 (m, 1H), 4.69-4.67 (m, 1H), 4.57-4.31 (m, 3H), 4.27-3.95 (m, 4H), 3.60-3.35 (m, 4H), 3.19-2.90 (m, 5H), 1.47-1.41 (m, 3H). | 741.2 |
| 448 | (3S)-7-((2S,5R)-4-acryloyl-2,5-dimethylpiperazin-1-yl)-9-chloro-10-(5-chloro-2,4-difluorophenyl)-3-((3-(trifluoromethyl)-5,6-dihydro-[1,2,4]triazolo[4,3-a]pyrazin-7(8H)-yl)methyl)-2H-[1,4]thiazino[2,3,4-ij]quinazolin-5(3H)-one | 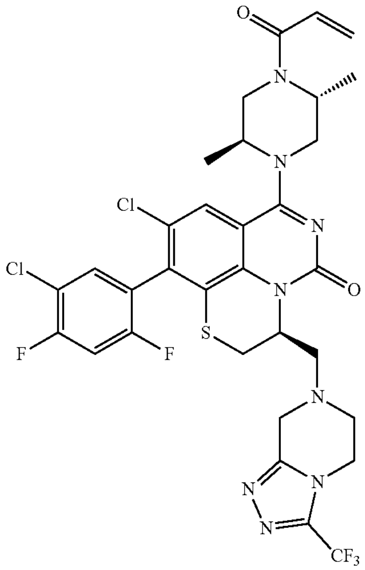 [SMILES: C=CC(=O)N1C[C@H](C)N(c2nc(=O)n3c4c(c(-c5cc(Cl)c(F)cc5F)c(Cl)cc24)SC[C@@H]3CN2CCn3c(nnc3C(F)(F)F)C2)C[C@H]1C] | $^1$H NMR (400 MHz, $CDCl_3$) δ 7.59-7.53 (m, 1H), 7.33-7.28 (m, 1H), 7.13-7.08 (m, 1H), 6.61-6.48 (m, 1H), 6.40-6.32 (m, 1H), 5.79-5.75 (m, 1H), 5.54-5.38 (m, 1H), 5.03-4.96 (m, 0.5 H), 4.80-4.70 (m, 1H), 4.38-4.09 (m, 2.5H), 4.07-3.96 (m, 3.5H), 3.71-3.65 (m, 2H), 3.30-3.08 (m, 5.5H), 2.96-2.91 (m, 1H), 1.46-1.38 (m, 3H), 1.32-1.25 (m, 3H). | 755.2 |

TABLE 7-continued

Table of Thiomorpholines

| Ex. # | Name | Structure | $^1$H NMR | MS (M + H)$^+$ |
|---|---|---|---|---|
| 449 | (3S)-3-(2-oxa-7-azaspiro[3.5]nonan-7-ylmethyl)-7-((2S,5R)-4-acryloyl-2,5-dimethylpiperazin-1-yl)-9-chloro-10-(5-chloro-2,4-difluorophenyl)-2H-[1,4]thiazino[2,3,4-ij]quinazolin-5(3H)-one | 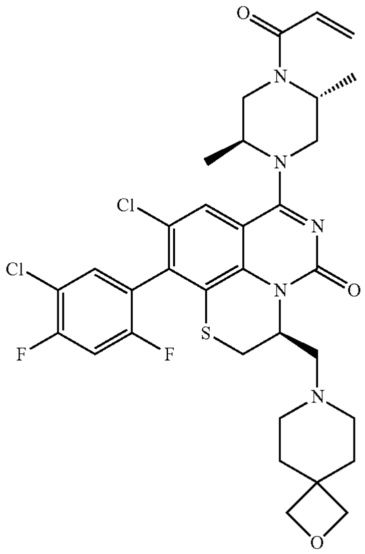 | $^1$H NMR (400 MHz, $CDCl_3$) δ 7.52 (s, 1H), 7.29-7.27 (m, 1H), 7.12-7.06 (m, 1H), 6.65-6.50 (m, 1H), 6.37 (t, J = 14.8 Hz, 1H), 5.79-5.75 (m, 1H), 5.42 (s, 1H), 5.00-4.68 (m, 2H), 4.38-3.97 (m, 6H), 3.78-3.65 (m, 2H), 3.36-3.35 (m, 1H), 3.05-3.00 (m, 1H), 2.71-2.37 (m, 6H), 1.81 (br, 4H), 1.39-1.25 (m, 6H). | 690.2 |
| 455 | (S)-8-(4-acryloyl-2-methylpiperazin-1-yl)-10-(trifluoromethyl)-11-(2,4,6-trifluorophenyl)-3,4-dihydro-2H,6H-[1,4]thiazepino[2,3,4-ij]quinazolin-6-one | 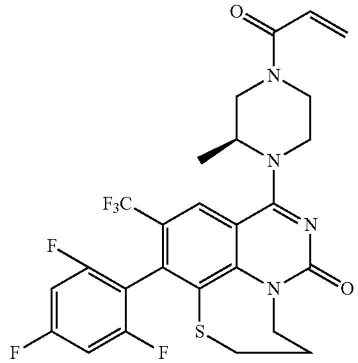 [SMILES: C=CC(=O)N1CCN(c2nc(=O)n3c4c(c(-c5c(F)cc(F)cc5F)c(C(F)(F)F)cc24)SCCC3)[C@@H](C)C1] | $^1$H NMR (400 MHz, MeOH-$d_4$) δ 7.64 (s, 1H), 6.96 (t, J = 8.5 Hz, 2H), 6.72 (ddd, J = 21.6, 16.6, 10.6 Hz, 1H), 6.18 (dd, J = 16.8, 6.3 Hz, 1H), 5.71 (dd, J = 10.6, 2.0 Hz, 1H), 5.13-4.99 (m, 2H), 4.60-4.48 (m, 4H), 4.33-3.84 (m, 2H), 3.63-3.45 (m, 3H), 2.18-2.03 (m, 2H), 1.31 (d, J = 6.8 Hz, 3H) | 535.2 |
| 456 | (3S)-3-(2-oxa-7-azaspiro[3.5]nonan-7-ylmethyl)-7((S)-4-acryloyl-2-methylpiperazin-1-yl)-9-chloro-10-(5-chloro-2,4-difluorophenyl)-2H-[1,4]thiazino[2,3,4-ij]quinazolin-5(3H)-one | 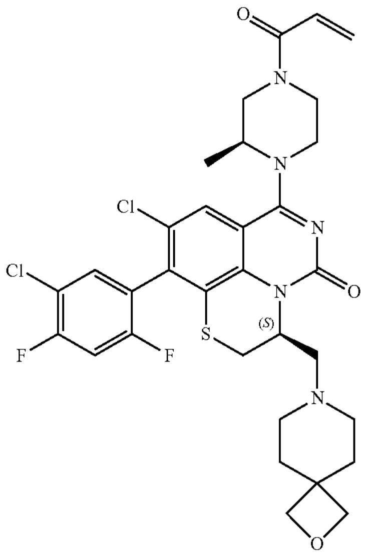 | $^1$H NMR (400 MHz, $CDCl_3$) δ 7.47 (s, 1H), 7.29 (t, J = 8.0 Hz, 1H), 7.12-7.06 (m, 1H), 6.65-6.50 (m, 1H), 6.39-6.34 (m, 1H), 5.77 (d, J = 11.2 Hz, 1H), 5.36-5.26 (m, 1H), 4.72-4.64 (m, 1H), 4.57-4.49 (m, 0.5H), 4.44-4.38 (m, 5H), 4.23-4.18 (m, 0.5H), 3.99-3.78 (m, 1H), 3.75-3.41 (m, 3H), 3.06-2.99 (m, 2H), 2.79-2.59 (m, 3H), 2.48-2.36 (m, 3H), 1.86-1.80 (m, 4H), 1.48-1.44 (m, 3H). | 676.3 |

TABLE 7-continued

Table of Thiomorpholines

| Ex. # | Name | Structure | $^1$H NMR | MS (M + H)$^+$ |
|---|---|---|---|---|
| 457 | (3S)-7-((S)-4-acryloyl-2-methylpiperazin-1-yl)-9-chloro-10-(5-chloro-2,4-difluorophenyl)-3-((4-(2,2-difluoroethyl)piperazin-1-yl)methyl)-2H-[1,4]thiazino[2,3,4-ij]quinazolin-5(3H)-one | 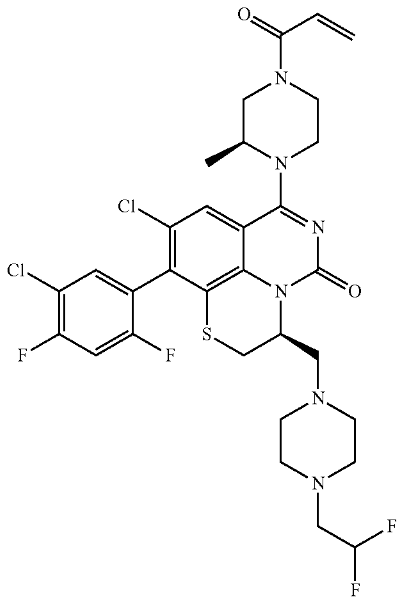 [SMILES: C=CC(=O)N1CCN(c2nc(=O)n3c4c(c(-c5cc(Cl)c(F)cc5F)c(Cl)cc24)SC[C@@H]3CN2CCN(CC(F)F)CC2)[C@@H](C)C1] | $^1$H NMR (400 MHz, $CDCl_3$) δ 7.48 (s, 1H), 7.31-7.28 (m, 1H), 7.10 (q, J = 8.4 Hz, 1H), 6.62-6,51 (m, 1H), 6.37 (d, J = 16.8 Hz, 1H), 6.00-5.72 (m, 2H), 5.40-5.29 (m, 1H), 4.80-4.70 (m, 1H), 4.64-4.61(m, 0.5H), 4.51-4.29 (m, 1H), 4.23-3.16 (m, 0.5H), 4.04-3.37 (m, 5H), 3.18-2.92 (m, 3H), 2.76-2.44 (m, 10H), 1.49-1.44 (m, 3H). | 699.2 |
| 458 | (3S)-7-((S)-4-acryloyl-2-methylpiperazin-1-yl)-9-chloro-10-(5-chloro-2,4-difluorophenyl)-3-((4-cyclopropylpiperazin-1-yl)methyl)-2H-[1,4]thiazino[2,3,4-ij]quinazolin-5(3H)-one | 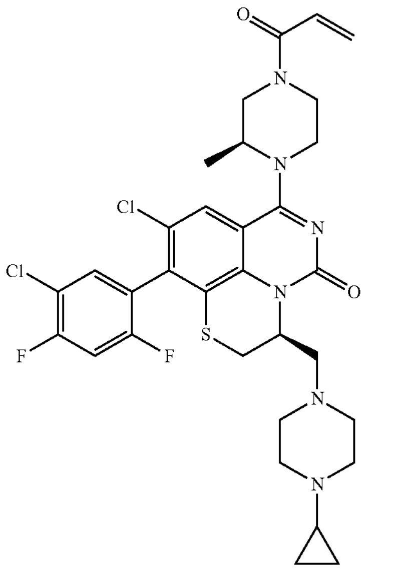 [SMILES: C=CC(=O)N1CCN(c2nc(=O)n3c4c(c(-c5cc(Cl)c(F)cc5F)c(Cl)cc24)SC[C@@H]3CN2CCN(C3CC3)CC2)[C@@H](C)C1] | $^1$H NMR (400 MHz, $CDCl_3$) δ 7.48 (s, 1H), 7.33-7.28 (m, 1H), 7.13-7.06 (m, 1H), 6.67-6.48 (m, 1H), 6.37 (d, J = 20.4 Hz, 1H), 5.77 (d, J = 17.6 Hz, 1H), 5.43-5.29 (m, 1H), 4.75-4.67 (m, 1H), 4.57-3.94 (m, 3H), 3.82-3.40 (m, 4H), 3.10-3.01 (m, 2H), 2.84-2.49 (m, 9H), 1.50-1.42 (m, 3H), 1.27-1.26 (m, 1H), 0.46-0.44 (m, 4H). | 675.2 |

TABLE 7-continued

Table of Thiomorpholines

| Ex. # | Name | Structure | $^1$H NMR | MS $(M + H)^+$ |
|---|---|---|---|---|
| 459 | (3S)-7-((2S,5R)-4-acryloyl-2,5-dimethylpiperazin-1-yl)-9-chloro-3-((3-(trifluoromethyl)-5,6-dihydro-[1,2,4]triazolo[4,3-a]pyrazin-7(8H)-yl)methyl)-10-(2,4,5-trifluorophenyl)-2H-[1,4]thiazino[2,3,4-ij]quinazolin-5(3H)-one | 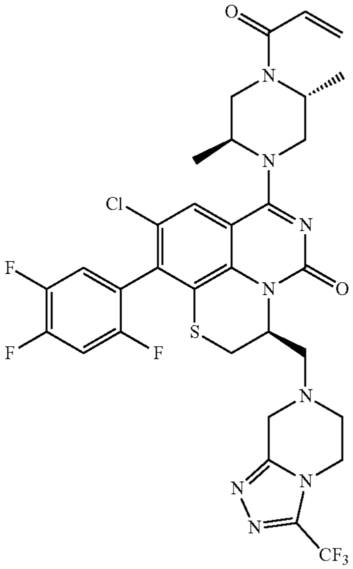 [SMILES: C=CC(=O)N1C[C@H](C)N(c2nc(=O)n3c4c(c(-c5cc(F)c(F)cc5F)c(Cl)cc24)SC[C@@H]3CN2CCn3c(nnc3C(F)(F)F)C2)C[C@H]1C] | $^1$H NMR (400 MHz, $CDCl_3$) δ 7.59-7.53 (m, 1H), 7.16-7.03 (m, 2H), 6.61-6.48 (m, 1H), 6.40-6.32 (m, 1H), 5.79-5.75 (m, 1H), 5.53-5.43 (brs, 1H), 5.04-4.96 (brs, 0.5 H), 4.83-4.71 (m, 1H), 4.36-4.03 (m, 6H), 3.75-3.66 (m, 2H), 3.33-3.03 (m, 5.5H), 2.94-2.88 (m, 1H), 1.46-1.36 (m, 3H), 1.32-1.26 (m, 3H) | 739.2 |
| 460 | 3S)-3-(2-oxa-7-azaspiro[3.5]nonan-7-ylmethyl)-7-((2S,5R)-4-acryloyl-2,5-dimethylpiperazin-1-yl)-9-chloro-10-(2,4,5-trifluorophenyl)-2H-[1,4]thiazino[2,3,4-ij]quinazolin-5(3H)-one | 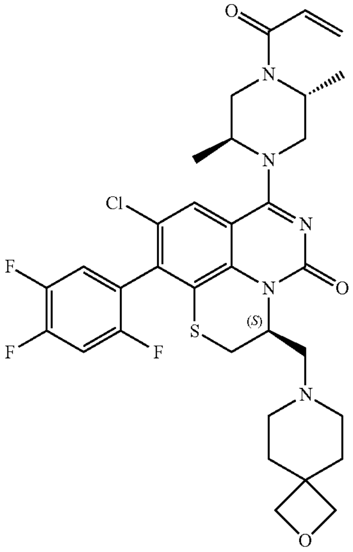 | $^1$H NMR (400 MHz, $CDCl_3$) δ 7.53 (s, 1H), 7.14-7.04 (m, 2H), 6.66-6.50 (m, 1H), 6.37 (t, J = 14.4 Hz, 1H), 5.77 (t, J = 7.6 Hz, 1H), 5.42-5.37 (m, 1H), 5.00-4.82 (m, 1H), 5.70-5.68 (m, 0.5H), 4.38-4.31 (m, 5H), 4.21-3.96 (m, 1H), 3.81-3.65 (m, 2.5H), 3.37-3.30 (m, 1H), 3.04-3.01 (m, 1H), 2.73-2.35 (m, 6H), 1.84-1.79 (m, 4H), 1.39-1.30 (m, 6H). | 674.3 |

TABLE 7-continued

| Ex. # | Name | Structure | $^1$H NMR | MS (M + H)$^+$ |
|---|---|---|---|---|
| | Table of Thiomorpholines | | | |
| 461 | (3S)-7-((2S,5R)-4-acryloyl-2,5-dimethylpiperazin-1-yl)-9-chloro-10-(5-chloro-2,4-difluorophenyl)-3-((1-(2,2-difluoroethyl)piperidin-4-yl)methyl)-2H-[1,4]thiazino[2,3,4-ij]quinazolin-5(3H)-one | 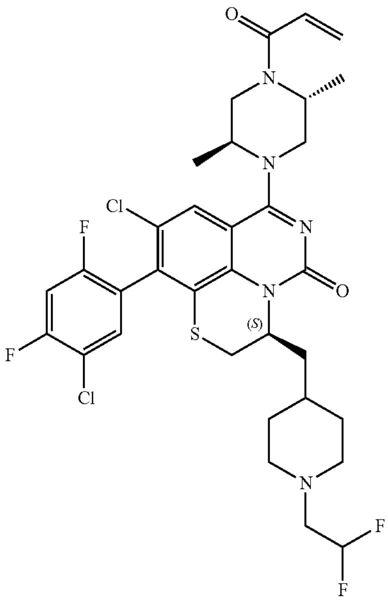 | $^1$H NMR (400 MHz, $CDCl_3$) δ 7.52-7.51 (m, 1H), 7.34-7.30 (m, 1H), 7.12-7.07 (m, 1H), 6.61-6.51 (m, 1H), 6.37 (t, J = 13.6 Hz, 1H), 5.99-5.70 (m, 1H), 5.78-5.75 (m, 1H), 5.53-5.50 (m, 1H), 4.97-4.90 (m, 1.5H), 4.75-4.73 (m, 0.5H), 4.38-4.29 (m, 1H), 4.20-4.17 (m, 0.5H), 3.98-3.81 (m, 2H), 3.74-3.65 (m, 1H), 3.40-3.38 (m, 0.5H), 3.18-3.12 (m, 1H), 2.97-2.88 (m, 3H), 2.72-2.63 (m, 2H), 2.18-2.08 (m, 2H), 1.85-1.83 (m, 1H), 1.71-1.65 (m, 2H), 1.40-1.38 (m, 5H), 1.30-1.25 (m, 4H). | 714.2 |
| 462 | (S)-3-(2-oxa-7-azaspiro[3.5]nonan-7-ylmethyl)-7-((S)-4-acryloyl-2-methylpiperazin-1-yl)-9-chloro-10-(4-fluorophenyl)-2H-[1,4]thiazino[2,3,4-ij]quinazolin-5(3H)-one | 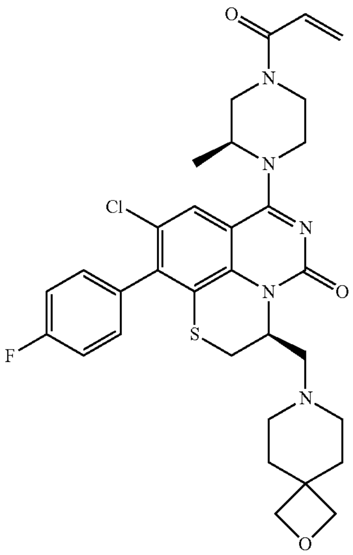 [SMILES: C=CC(=O)N1CCN(c2nc(=O)n3c4c(c(-c5ccc(F)cc5)c(Cl)cc24)SC[C@@H]3CN2CCC3(CC2)COC3)[C@@H](C)C1] | $^1$H NMR (400 MHz, $CDCl_3$) δ 7.48 (s, 1H), 7.23-7.18 (m, 4H), 6.62-6.52 (m, 1H), 6.36 (d, J = 18.0 Hz, 1H), 5.77 (d, J = 10.8 Hz, 1H), 5.29-5.27 (m, 1H), 4.74-4.70 (m, 1H), 4.64 (m, 0.5H), 4.54-4.38 (m, 5H), 4.21-4.19 (m, 0.5H), 3.96-3.95 (m, 0.5H), 3.81-3.77 (m, 0.5H), 3.62-3.49 (m, 2H), 3.37-3.36 (m, 1H), 3.12-3.07 (m, 1H), 3.00-2.94 (m, 1H), 2.79-2.73 (m, 1H), 2.65-2.55 (m, 2H), 2.49-2.47 (m, 1H), 2.43-2.35 (m, 2H), 1.88-1.75 (m, 4H), 1.48-1.44 (m, 3H). | 624.3 |

TABLE 7-continued

Table of Thiomorpholines

| Ex. # | Name | Structure | $^1$H NMR | MS (M + H)$^+$ |
|---|---|---|---|---|
| 463 | (3S)-7-((S)-4-acryloyl-2-methylpiperazin-1-yl)-9-chloro-3-((3-(trifluoromethyl)-5,6-dihydro-[1,2,4]triazolo[4,3-a]pyrazin-7(8H)-yl)methyl)-10-(2,4,5-trifluorophenyl)-2H-[1,4]thiazino[2,3,4-ij]quinazolin-5(3H)-one | 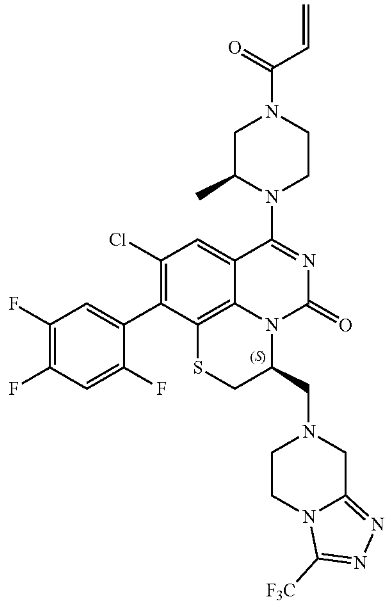 | $^1$H NMR (400 MHz, $CDCl_3$) δ 7.51 (s, 1H), 7.15-7.04 (m, 2H), 6.63-6.50 (m, 1H), 6.39-6.35 (m, 1H), 5.78 (d, J = 10.8 Hz, 1H), 5.37-5.35 (m, 1H), 4.70-4.68 (m, 1H), 4.55-4.27 (m, 3H), 4.18-3.78 (m, 4H), 3.51-3.77 (m, 4H), 3.18-2.90 (m, 5H), 1.52-1.44 (m, 3H). | 725.2 |
| 466 | (3R)-7-((S)-4-acryloyl-2-methylpiperazin-1-yl)-9-chloro-3-((methoxymethoxy)methyl)-10-(2,4,5-trifluorophenyl)-2H-[1,4]thiazino[2,3,4-ij]quinazolin-5(3H)-one | 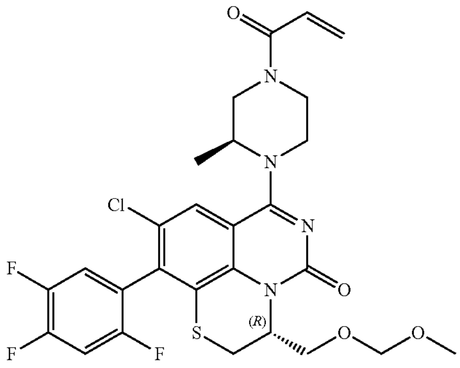 | $^1$H NMR (400 MHz, $CDCl_3$) δ 7.52-7.50 (m, 1H), 7.15-7.06 (m, 2H), 6.59-6.53 (m, 1H), 6.38 (d, J = 16.4 Hz, 1H), 5.78 (d, J = 10.0 Hz, 1H), 5.49-5.45 (m, 1H), 4.97-4.94 (m, 0.5H), 4.65 (dt, J = 16.0 Hz, 8.0 Hz, 3H), 4.52-4.46 (m, 0.5H), 4.10-3.96 (m, 1.5H), 3.82-3.60 (m, 4.5H), 3.45-3.35 (m, 4H), 3.26-3.19 (m, 0.5H), 3.19-3.10 (m, 1H), 2.92-2.87 (m, 0.5H), 1.35 (d, J = 6.4 Hz, 3H). | 595.1 |
| 467 | (3S)-7-((2S,5R)-4-acryloyl-2,5-dimethylpiperazin-1-yl)-9-chloro-10-(5-chloro-2,4-difluorophenyl)-3-((1-cyclopropylpiperidin-4-yl)methyl)-2H-[1,4]thiazino[2,3,4-ij]quinazolin-5(3H)-one | 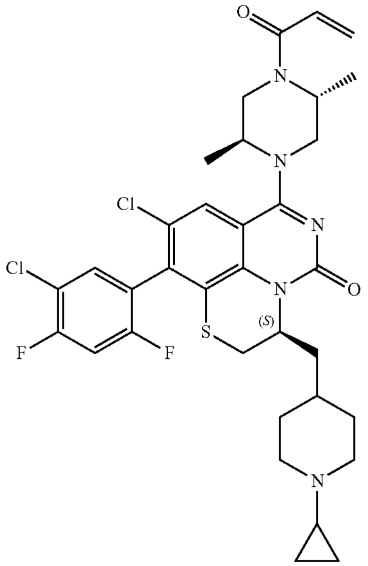 | $^1$H NMR (400 MHz, $CDCl_3$) δ 7.51-7.50 (m, 1H), 7.34-7.28 (m, 1H), 7.12-7.07 (m, 1H), 6.66-6.51 (m, 1H), 6.37 (t, J = 14.4 Hz, 1H), 5.78 (d, J = 10.0 Hz, 1H), 5.51-5.49 (m, 1H), 4.96-4.92 (m, 1H), 4.76-4.75 (m, 0.5H), 4.37-4.30 (m, 0.7H), 4.22-4.13 (m, 0.5H), 3.98-3.65 (m, 3H), 3.42-3.37 (m, 0.3H), 3.16-3.12 (m, 1H), 2.98-2.96 (m, 3H), 2.14-2.04 (m, 2H), 1.84-1.82(m, 1H), 1.51-1.49 (m, 2H), 1.39 (d, J = 6.4 Hz, 6H), 1.29-1.25 (m, 5H), 0.41-0.37 (m, 4H). | 688.2 |

TABLE 7-continued

| Table of Thiomorpholines | | | | |
|---|---|---|---|---|
| Ex. # | Name | Structure | $^1$H NMR | MS (M + H)$^+$ |
| 468 | (3S)-7-((2S,5R)-4-acryloyl-2,5-dimethylpiperazin-1-yl)-9-chloro-10-(2,4-difluorophenyl)-3-((3-(trifluoromethyl)-5,6-dihydro-[1,2,4]triazolo[4,3-a]pyrazin-7(8H)-yl)methyl)-2H-[1,4]thiazino[2,3,4-ij]quinazolin-5(3H)-one | 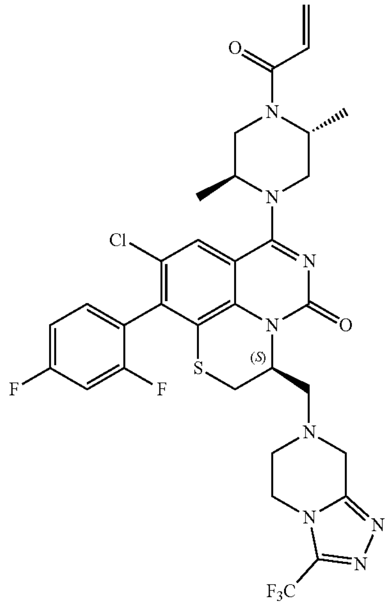 | $^1$H NMR (400 MHz, $CDCl_3$) δ 7.59-7.56 (m, 1H), 7.26-7.18 (m, 1H), 7.08-6.98 (m, 2H), 6.64-6.49 (m, 1H), 6.40-6.33 (m, 1H), 5.79-5.75 (m, 1H), 5.44-5.42 (m, 1H), 5.02-5.00 (m, 0.5H), 4.80-4.72 (m, 1H), 4.39-3.96 (m, 6.5H), 3.75-3.65 (m, 2H), 3.30-3.26 (m, 2H), 3.18-3.11 (m, 2H), 3.08-3.02 (m, 1H), 2.92-2.89 (m, 1H), 1.46-1.43 (m, 3H), 1.33-1.27 (m, 3H). | 721.3 |
| 469 | (3S)-3-(2-oxa-7-azaspiro[3.5]nonan-7-ylmethyl)-7-((S)-4-acryloyl-2-methylpiperazin-1-yl)-9-chloro-10-(2,4,5-trifluorophenyl)-2H-[1,4]thiazino[2,3,4-ij]quinazolin-5(3H)-one | 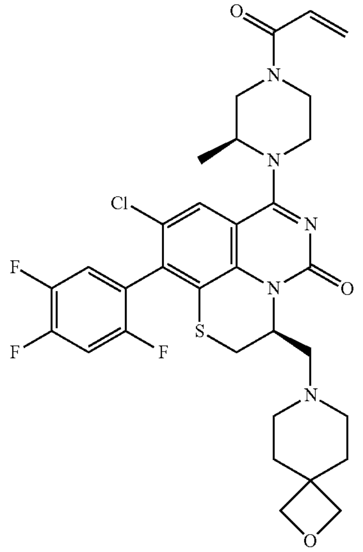 [SMILES: C=CC(=O)N1CCN(c2nc(=O)n3c4c(c(-c5cc(F)c(F)cc5F)c(Cl)cc24)SC[C@@H]3CN2CCC3(CC2)COC3)[C@@H](C)C1] | $^1$H NMR (400 MHz, $CDCl_3$) δ 7.47 (s, 1H), 7.14-7.04 (m, 2H), 6.61-6.51 (m, 1H), 6.39-6.34 (m, 1H), 5.77 (d, J = 11.6 Hz, 1H), 5.37-5.26 (m, 1H), 4.96-4.94 (m, 1H), 4.56-4.34 (m, 5.5H), 4.21-4.19 (m, 0.5H), 3.97-3.93 (m, 0.5H), 3.81-3.78 (m, 0.5H), 3.62-3.41 (m, 3H), 3.05-2.99 (m, 2H), 2.78-2.70 (m, 1H), 2.60-2.59 (m, 2H), 2.48-2.35 (m, 3H), 1.86-1.80 (m, 4H), 1.48-1.44 (m, 3H). | 660.2 |
| 470 | (3R)-7-((S)-4-acryloyl-2-methylpiperazin-1-yl)-10-(5-chloro-2,4-difluorophenyl)-3-((methoxymethoxy)methyl)-9-(trifluoromethyl)-2H-[1,4]thiazino[2,3,4-ij]quinazolin-5(3H)-one | 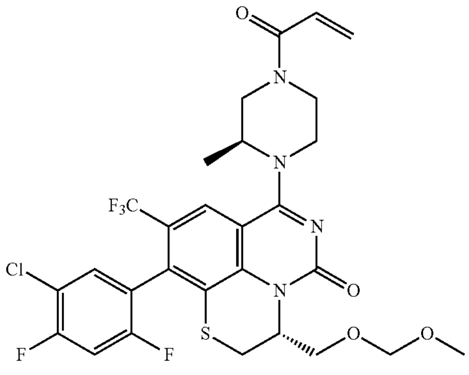 [SMILES: C=CC(=O)N1CCN(c2nc(=O)n3c4c(c(-c5cc(Cl)c(F)cc5F)c(C(F)(F)F)cc24)SC[C@H]3COCOC)[C@@H](C)C1] | $^1$H NMR (400 MHz, $CDCl_3$) δ 7.78-7.75 (m, 1H), 7.29-7.26 (m, 1H), 7.10 9-7.04 (m, 1H), 6.59-6.53 (m, 1H), 6.40-6.36 (m, 1H), 5.79 (dd, J = 10.0 Hz, 1.2 Hz, 1H), 5.52-5.44 (m, 1H), 5.05-4.95 (m, 0.5H), 4.99-4.62 (m, 3H), 4.11-4.00 (m, 1H), 3.85-3.68 (m, 3H), 3.67-3.45 (m, 1H), 3.41-3.05 (m, 5H), 3.10-3.05 (m, 1H), 2.90-2.86 (m, 0.5H), 1.38 (d, J = 6.8 Hz, 3H). | 645.1 |

TABLE 7-continued

| Table of Thiomorpholines | | | | |
|---|---|---|---|---|
| Ex. # Name | | Structure | $^1$H NMR | MS (M + H)$^+$ |
| 471 | (3R)-7-((S)-4-acryloyl-2-methylpiperazin-1-yl)-3-((methoxymethoxy)methyl)-9-(trifluoromethyl)-10-(2,4,5-trifluorophenyl)-2H-[1,4]thiazino[2,3,4-ij]quinazolin-5(3H)-one | 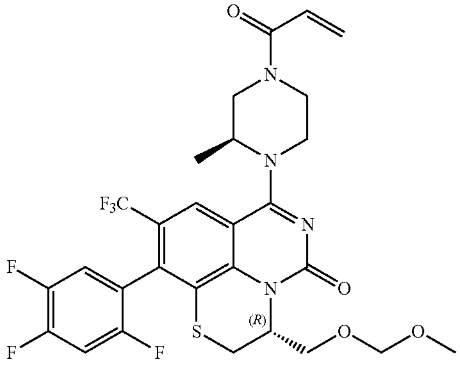 | $^1$H NMR (400 MHz, $CDCl_3$) δ 7.76 (s, 1H), 7.12-7.03 (m, 2H), 6.59-6.53 (m, 1H), 6.38 (dd, J = 16.8, 1.6 Hz, 1H), 5.79 (dd, J = 10.4, 1.2 Hz, 1H), 5.79 (brs, 1H), 5.00 (brs, 0.5H), 4.81-4.62 (m, 3H), 4.50-4.47 (m, 0.5H), 4.14-4.00 (m, 1.5H), 3.89-3.64 (m, 4.5H), 3.42-3.35 (m, 4.5H), 3.10-3.04 (m, 1H), 2.92-2.86 (m, 0.5H), 1.38 (d, J = 6.8 Hz, 3H). | 629.2 |
| 472 | (3S)-3-(2-oxa-7-azaspiro[3.5]nonan-7-ylmethyl)-7-((S)-4-acryloyl-2-methylpiperazin-1-yl)-9-chloro-10-(2,4-difluorophenyl)-2H-[1,4]thiazino[2,3,4-ij]quinazolin-5(3H)-one | 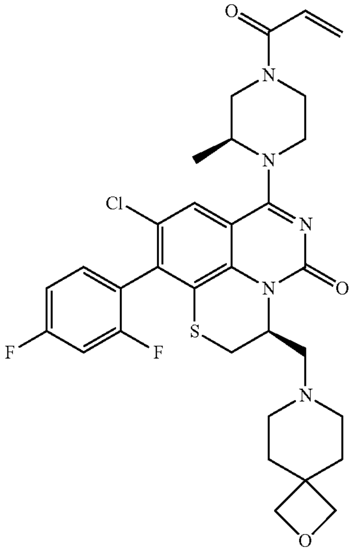 [SMILES: C=CC(=O)N1CCN(c2nc(=O)n3c4c(c(-c5ccc(F)cc5F)c(Cl)cc24)SC[C@@H]3CN2CCC3(CC2)COC3)[C@@H](C)C1] | $^1$H NMR (400 MHz, $CDCl_3$) δ 7.48 (s, 1H), 7.21 (q, J = 27.6 Hz, 1H), 7.07-6.95 (m, 2H), 6.66-6.50 (m, 1H), 6.37 (d, J = 18.4 Hz, 1H), 5.77 (d, J = 10.0 Hz, 1H), 5.38-5.26 (m, 1H), 4.73-4.69 (m, 1H), 4.62-4.59 (m, 0.5H), 4.38-4.35 (m, 5H), 4.21-4.17 (m, 0.5H), 3.98-3.78 (m, 1H), 3.65-3.54 (m, 2H), 3.50-3.03 (m, 4H), 2.81-2.67 (m, 1H), 2.59-2.50 (m, 2H), 2.48-2.30 (m, 2H), 2.00-1.71 (m, 4H), 1.49-1.39 (m, 3H). | 642.2 |
| 473 | (S)-3-(2-oxa-7-azaspiro[3.5]nonan-7-ylmethyl)-7-((2S,5R)-4-acryloyl-2,5-dimethylpiperazin-1-yl)-9-chloro-10-(4-fluorophenyl)-2H-[1,4]thiazino[2,3,4-ij]quinazolin-5(3H)-one | 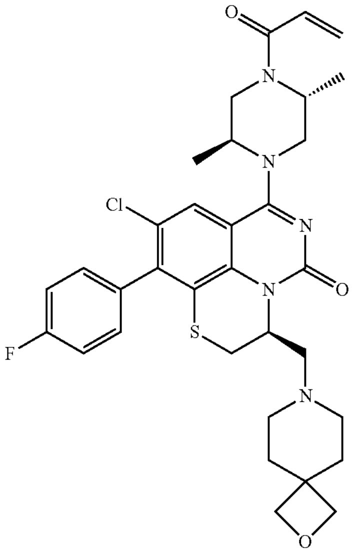 [SMILES: C=CC(=O)N1C[C@H](C)N(c2nc(=O)n3c4c(c(-c5ccc(F)cc5)c(Cl)cc24)SC[C@@H]3CN2CCC3(CC2)COC3)C[C@H]1C] | $^1$H NMR (400 MHz, $CDCl_3$) δ 7.53 (s, 1H), 7.23-7.19 (m, 4H), 6.66-6.50 (m, 1H), 6.37 (t, J = 14.4, 1H), 5.77 (t, J = 8.4 Hz, 1H), 5.44-5.29 (m, 1H), 4.98-4.66 (m, 2H), 4.55-4.46 (m, 1H), 4.38 (s, 4H), 4.32-4.19 (m, 1H), 3.99 (d, J = 13.6 Hz, 1H), 3.81-3.60 (m, 2H), 3.38-3.25 (m, 1H), 2.96 (d, J = 12.4 Hz, 1H), 2.76-2.37 (m, 6H), 1.84-1.80 (m, 3H), 1.39-1.26 (m, 6H). | 638.3 |

TABLE 7-continued

| Table of Thiomorpholines | | | | |
|---|---|---|---|---|
| Ex. # | Name | Structure | $^1$H NMR | MS $(M + H)^+$ |
| 474 | (3S)-7-((S)-4-acryloyl-2-methylpiperazin-1-yl)-9-chloro-10-(5-fluoroquinolin-8-yl)-3-(methoxymethyl)-2,3-dihydro-5H-[1,4]thiazino[2,3,4-ij]quinazolin-5-one | 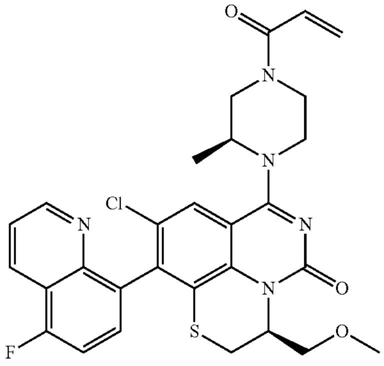 [SMILES: C=CC(=O)N1CCN(c2nc(=O)n3c4c(c(-c5ccc(F)c6cccnc56)c(Cl)cc24)SC[C@@H]3COC)[C@@H](C)C1] | $^1$H NMR (400 MHz, MeOH-$d_4$) δ 8.83 (dd, J = 4.3, 1.7 Hz, 1H), 8.66 (dd, J = 8.5, 1.8 Hz, 1H), 7.72 (d, J = 2.9 Hz, 1H), 7.66 (td, J = 8.6, 5.1 Hz, 2H), 7.56-7.47 (m, 1H), 6.83 (ddd, J = 27.5, 16.7, 10.5 Hz, 1H), 6.29 (dd, J = 16.8, 7.5 Hz, 1H), 5.82 (d, J = 9.8 Hz, 1H), 5.41-5.25 (m, 1H), 4.86-4.69 (m, 2H), 4.64-4.32 (m, 2H), 4.24-3.97 (m, 1H), 3.76-3.46 (m, 4H), 3.33 (s, 3H), 3.27-3.06 (m, 3H), 1.48 (dd, J = 7.0, 3.3 Hz, 3H) | 580.2 |
| 475 | (3S)-7-((2S,5R)-4-acryloyl-2,5-dimethylpiperazin-1-yl)-9-chloro-3-((1-cyclopropylpiperidin-4-yl)methyl)-10-(2,4,5-trifluorophenyl)-2H-[1,4]thiazino[2,3,4-ij]quinazolin-5(3H)-one | 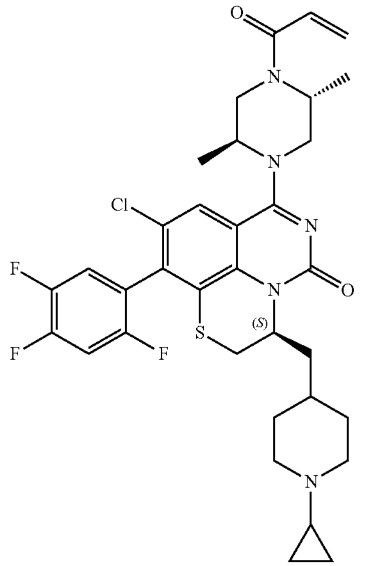 | $^1$H NMR (400 MHz, $CDCl_3$) δ 7.51-7.50 (m, 1H), 7.14-7.07 (m, 2H), 6.65-6.51 (m, 1H), 6.37 (t, J = 15.6 Hz, 1H), 5.78-5.75 (m, 1H), 5.54-5.50 (m, 1H), 4.96-4.90 (m, 1H), 4.76-4.74 (m, 0.5H), 4.38-4.30 (m, 1H), 4.20 (d, J = 10.4 Hz, 0.5H), 3.98-3.94 (m, 0.6H), 3.85-3.81 (m, 1H), 3.75-3.64 (m, 1H), 3.43-3.38 (m, 0.4H), 3.17-3.12 (m, 1H), 2.97-2.95 (m, 3H), 2.14-2.05 (m, 2H), 2.05-1.82 (m, 1H), 1.51-1.50 (m, 1H), 1.39-1.37 (m, 5H), 1.29-1.25 (m, 7H), 0.42-0.37 (m, 4H). | 672.3 |
| 476 | (3S)-7-((2S,5R)-4-acryloyl-2,5-dimethylpiperazin-1-yl)-9-chloro-3-((1-(2,2-difluoroethyl)piperidin-4-yl)methyl)-10-(2,4,5-trifluorophenyl)-2H-[1,4]thiazino[2,3,4-ij]quinazolin-5(3H)-one | 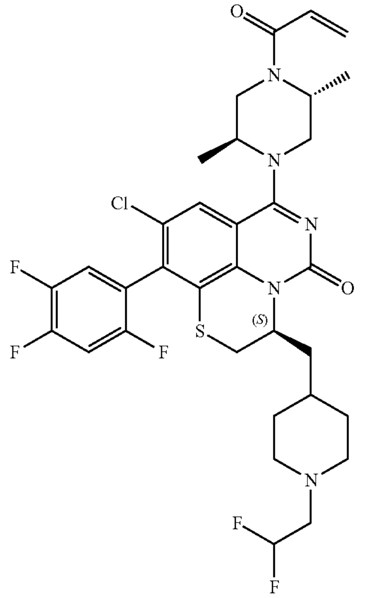 | $^1$H NMR (400 MHz, $CDCl_3$) δ 7.52 (s, 1H), 7.14-7.06 (m, 2H), 6.65-6.51 (m, (1H), 6.37 (t, J = 15.2 Hz, 1H), 5.98-5.70 (m, 2H), 5.53-5.51 (m, 1H), 4.98-4.89 (m, 1H), 4.75-4.73 (s, 0.5H), 4.37-4.29 (m, 1H), 4.22-4.19 (m, 0.5H), 3.99-3.95 (m, 0.5H), 3.84 (d, J = 13.2 Hz, 1H), 3.73-3.68 (m, 1H), 3.40-3.36 (m, 0.5H), 3.17-3.12 (m, 1H), 2.97-2.88 (m, 3H), 2.72-2.64 (m, 2H), 2.18-2.08 (m, 2H), 1.85-1.81 (m, 1H), 1.68-1.62 (m, 2H), 1.39 (d, J = 5.6 Hz, 6H), 1.27 (t, J = 7.6 Hz, 4H). | 696.2 |

TABLE 7-continued

Table of Thiomorpholines

| Ex. # | Name | Structure | $^1$H NMR | MS $(M + H)^+$ |
|---|---|---|---|---|
| 477 | (3S)-7-((2S,5R)-4-acryloyl-2,5-dimethylpiperazin-1-yl)-9-chloro-3-((1-(2,2-difluoroethyl)piperidin-4-yl)methyl)-10-(2,4-difluorophenyl)-2H-[1,4]thiazino[2,3,4-ij]quinazolin-5(3H)-one | 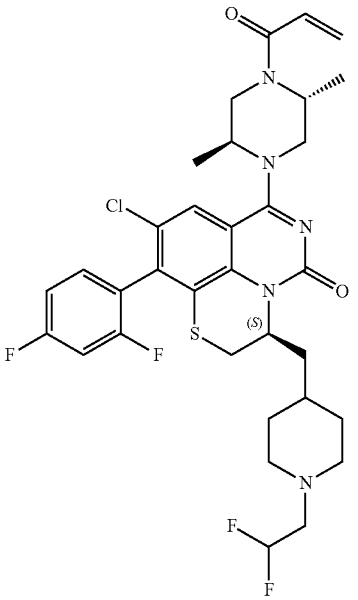 | $^1$H NMR (400 MHz, $CDCl_3$) δ 7.52 (s, 1H), 7.24-7.20 (m, 1H), 7.05-6.96 (m, 2H), 6.65-6.51 (m, 1H), 6.37 (t, J = 13.6 Hz, 1H), 5.99-5.69 (m, 2H), 5.52-5.50 (m, 1H), 4.98-4.91 (m, 1H), 4.76-4.74 (m, 0.5H), 4.38-4.30 (m, 1H), 4.23-4.19 (m, 0.5H), 4.00-3.97 (m, 0.5H), 3.82-3.64 (m, 2H), 3.41-3.37 (m, 0.5H), 3.15-3.11 (m, 1H), 2.94-2.87 (m, 3H), 2.68 (t, J = 14.8 Hz, 2H), 2.18-2.08 (m, 2H), 1.86-1.83 (m, 1H), 1.70-1.66 (m, 2H), 1.38-1.36 (m, 6H), 1.28 (t, J = 7.6 Hz, 4H). | 678.2 |
| 478 | (3S)-7-((2S,5R)-4-acryloyl-2,5-dimethylpiperazin-1-yl)-9-chloro-3-((1-cyclopropylpiperidin-4-yl)methyl)-10-(2,4-difluorophenyl)-2H-[1,4]thiazino[2,3,4-ij]quinazolin-5(3H)-one | 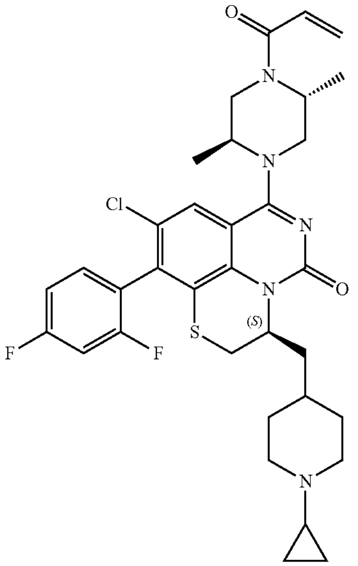 | $^1$H NMR (400 MHz, $CDCl_3$) δ 7.51 (s, 1H), 7.26-7.20 (m, 1H), 7.04-6.96 (m, 2H), 6.65-6.51 (m, 1H), 6.36 (t, J = 15.2 Hz, 1H), 5.77 (d, J = 10.4 Hz, 1H), 5.53-5.50 (m, 1H), 4.96-4.92 (m, 1H), 4.76-4.74 (m, 0.5H), 4.38-4.30 (m, 1H), 4.21-4.18 (m, 0.5H), 3.99-3.96 (m, 0.6H), 3.83-3.63 (m, 2H), 3.42-3.38 (m, 0.4H), 3.16-3.11 (m, 1H), 2.99-2.92 (m, 3H), 2.12-2.04 (m, 2H), 1.84-1.82 (m, 1H), 1.50-1.48 (m, 2H), 1.37-1.35 (m, 5H), 1.29-1.26 (m, 6H), 0.41-0.37 (m, 4H). | 654.2 |
| 479 | (3R)-7-((S)-4-acryloyl-2-methylpiperazin-1-yl)-9-chloro-10-(2,4-difluorophenyl)-3-((methoxymethoxy)methyl)-2H-[1,4]thiazino[2,3,4-ij]quinazolin-5(3H)-one | 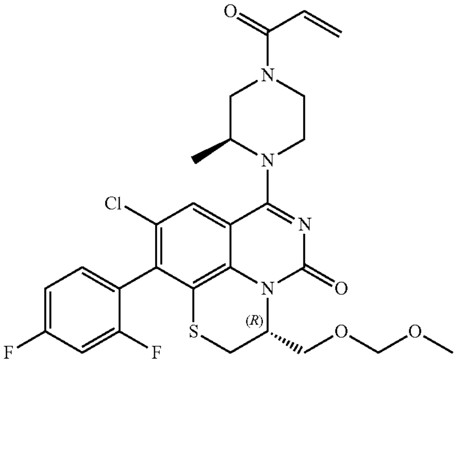 | $^1$H NMR (400 MHz, $CDCl_3$) δ 7.52-7.50 (m, 1H), 7.22 (m, 1H), 7.07-6.95 (m, 2H), 6.60-6.53 (m, 1H), 6.37 (dd, J = 16.8, 1.2 Hz, 1H), 5.77 (d, J = 10.4 Hz, 1H), 5.50-5.40 (m, 1H), 5.10-4.85 (m, 0.5H), 4.82-4.62 (m, 3H), 4.52-4.46 (m, 0.5H), 4.10-3.99 (m, 1.5H), 3.83-3.57 (m, 4H), 3.49-3.35 (m, 4.5H), 3.30-3.20 (m, 0.4H), 3.07 (d, J = 13.6 Hz, 1H), 2.95-2.85 (m, 0.6H), 1.34 (d, J = 6.4 Hz, 3H). | 577.2 |

TABLE 7-continued

| Ex. # | Name | Structure | $^1$H NMR | MS (M + H)$^+$ |
|---|---|---|---|---|
| | Table of Thiomorpholines | | | |
| 480 | (3S)-7-((S)-4-acryloyl-2-methylpiperazin-1-yl)-9-chloro-3-((4-(2,2-difluoroethyl)piperazin-1-yl)methyl)-10-(2,4,5-trifluorophenyl)-2H-[1,4]thiazino[2,3,4-ij]quinazolin-5(3H)-one | 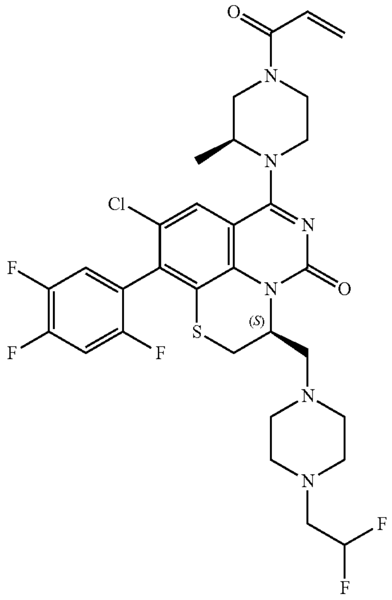 | $^1$H NMR (400 MHz, $CDCl_3$) δ 7.48 (s, 1H), 7.14-7.04 (m, 2H), 6.62-6.51 (m, 1H), 6.37 (d, J = 16.8 Hz, 1H), 6.00-5.72 (m, 2H), 5.34-5.33 (m, 1H), 4.74-4.65 (m, 1H), 4.53-4.36 (m, 1.5H), 4.21-4.16 (m, 0.5H), 3.97-3.95 (m, 0.5H), 3.81-3.77 (m, 0.5H), 3.57-3.50 (m, 1.5H), 3.42 (d, J = 13.2 Hz ,1.5H), 3.04-3.01 (m, 2H), 2.87-2.67 (m, 5H), 2.55-2.53 (m, 7H), 1.48-1.44 (m, 3H). | 683.2 |
| 481 | (S)-7-((2S,5R)-4-acryloyl-2,5-dimethylpiperazin-1-yl)-3-((1-(2,2-difluoroethyl)azetidin-3-yl)methyl)-10-(4-fluorophenyl)-9-(trifluoromethyl)-2H-[1,4]thiazino[2,3,4-ij]quinazolin-5(3H)-one | 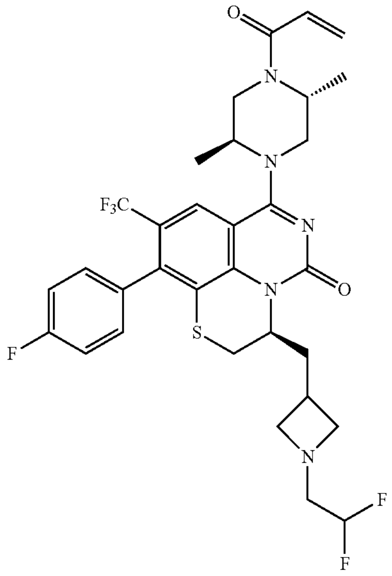 [SMILES: C=CC(=O)N1C[C@H](C)N(c2nc(=O)n3c4c(c(-c5ccc(F)cc5)c(C(F)(F)F)cc24)SC[C@@H]3CC2CN(CC(F)F)C2)C[C@H]1C] | $^1$H NMR (400 MHz, $CDCl_3$) δ 7.84 (s, 1H), 7.26-7.25 (m, 1H), 7.21-7.17 (m, 3H), 6.67-6.51 (m, 1H), 6.38 (t, J = 15.6 Hz, 1H), 5.84-5.54 (m, 2H), 5.27-5.26 (m, 1H), 5.06-5.01 (m, 0.5H), 4.84-4.83 (m, 0.5H), 4.71-4.70 (m, 0.5H), 4.42-4.32 (m, 1.5H), 4.06-4.03 (m, 0.5H), 3.80-3.67 (m, 2H), 3.59-3.52 (m, 2H), 3.33-3.29 (m, 0.5H), 3.06-2.97 (m, 3H), 2.88-2.84 (m, 1H), 2.79-2.70 (m, 2H), 2.61-2.53 (m, 1H), 2.06 (t, J = 6.8 Hz, 1H), 1.47-1.38 (m, 6H). | 666.3 |

TABLE 7-continued

Table of Thiomorpholines

| Ex. # | Name | Structure | $^1$H NMR | MS (M + H)$^+$ |
|---|---|---|---|---|
| 482 | (3S,10S)-3-((2-oxa-7-azaspiro[3.5]nonan-7-yl)methyl)-7-((S)-4-acryloyl-2-methylpiperazin-1-yl)-9-chloro-10-(5-chloro-2,4-difluorophenyl)-2,3-dihydro-5H-[1,4]thiazino[2,3,4-ij]quinazolin-5-one | 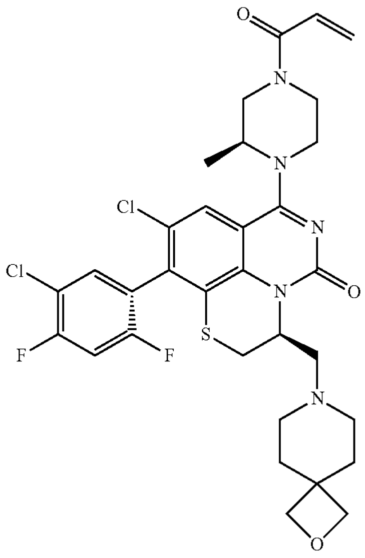 | $^1$H NMR (400 MHz, $CDCl_3$) δ 7.48 (s, 1H), 7.29 (t, J = 3.2 Hz, 1H), 7.10 (t, J = 8.8 Hz, 1H), 6.66-6.51 (m, 1H), 6.37 (d, J = 18 Hz, 1H), 5.77 (d, J = 10.8 Hz, 1H), 5.36-5.27 (m, 1H), 4.70-4.66 (m, 1H), 4.54-4.19 (m, 6H), 3.99-3.78 (m, 1H), 3.62-3.38 (m, 3H), 3.08-2.99 (m, 2H), 2.78-2.34 (m, 6H), 1.93-1.78 (m, 4H), 1.48-1.45 (m, 3H). | 676.3 |
| 483 | (3S,10R)-3-((2-oxa-7-azaspiro[3.5]nonan-7-yl)methyl)-7-((S)-4-acryloyl-2-methylpiperazin-1-yl)-9-chloro-10-(5-chloro-2,4-difluorophenyl)-2,3-dihydro-5H-[1,4]thiazino[2,3,4-ij]quinazolin-5-one | 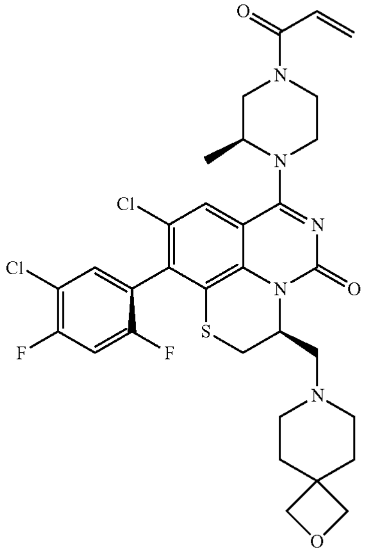 | $^1$H NMR (400 MHz, $CDCl_3$) δ 7.48 (s, 1H), 7.29 (t, J = 8.4 Hz, 1H), 7.09 (t, J = 8.4 Hz, 1H), 6.66-6.50 (m, 1H), 6.37 (d, J = 16.4 Hz, 1H), 5.77 (d, J = 10.4 Hz, 1H), 5.40-5.29 (m, 1H), 4.73-4.66 (m, 1H), 4.56-4.52 (m, 0.5H), 4.46-4.38 (m, 5H), 4.23-4.18 (m, 0.5H), 3.98-3.78 (m, 1H), 3.63-3.42 (m, 3H), 3.05-3.02 (m, 2H), 2.74-2.35 (m, 6H), 1.92-1.83 (m, 4H), 1.50-1.42 (m, 3H). | 676.3 |

TABLE 7-continued

Table of Thiomorpholines

| Ex. # | Name | Structure | $^1H$ NMR | MS $(M + H)^+$ |
|---|---|---|---|---|
| 484 | (3S,10S)-3-((2-oxa-7-azaspiro[3.5]nonan-7-yl)methyl)-7-((2S,5R)-4-acryloyl-2,5-dimethylpiperazin-1-yl)-9-chloro-10-(2,4,5-trifluorophenyl)-2,3-dihydro-5H-[1,4]thiazino[2,3,4-ij]quinazolin-5-one | 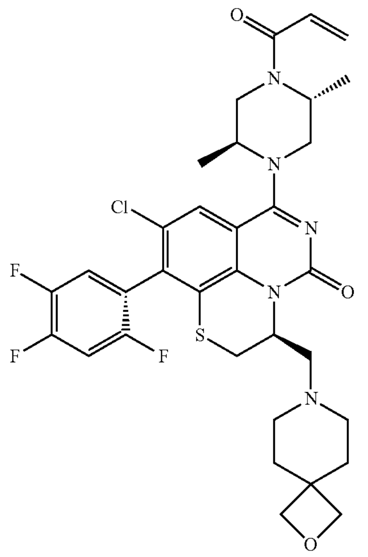 | $^1H$ NMR (400 MHz, $CDCl_3$) δ 7.52 (s, 1H), 7.14-7.05 (m, 2H), 6.66-6.50 (m, 1H), 6.37 (t, J = 14.4 Hz, 1H), 5.77 (t, J = 8.0 Hz, 1H), 5.42-5.34 (m, 1H), 5.00-4.83 (m, 1H), 4.73-4.68 (m, 0.5H), 4.38-4.23 (m, 5H), 4.01-3.98 (m, 0.5H), 3.81-3.65 (m, 2H), 3.38-3.31 (m, 1.5H), 3.16-3.00 (m, 1.5H), 2.74-2.38 (m, 6H), 1.85-1.80 (m, 4H), 1.41-1.38 (m, 6H). | 674.3 |
| 485 | (3S,10R)-3-((2-oxa-7-azaspiro[3.5]nonan-7-yl)methyl)-7-((2S,5R)-4-acryloyl-2,5-dimethylpiperazin-1-yl)-9-chloro-10-(2,4,5-trifluorophenyl)-2,3-dihydro-5H-[1,4]thiazino[2,3,4-ij]quinazolin-5-one | 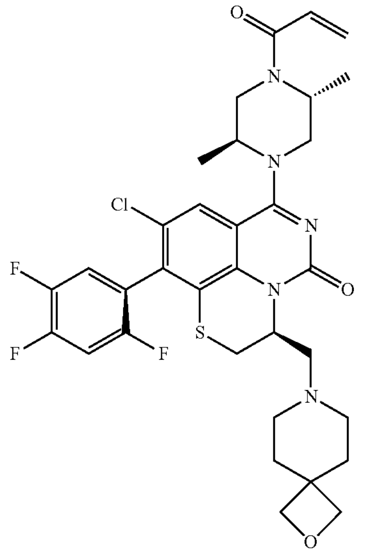 | $^1H$ NMR (400 MHz, $CDCl_3$) δ 7.53 (s, 1H), 7.13-7.04 (m, 2H), 6.66-6.50 (m, 1H), 6.37 (t, J = 14.0 Hz, 1H), 5.77 (t, J = 6.8 Hz, 1H), 5.42-5.36 (m, 1H), 4.99-4.84 (m, 1H), 4.75-4.70 (m, 0.5H), 4.37-4.23 (m, 5H), 4.01-3.98 (m, 0.5H), 3.81-3.65 (m, 2H), 3.39-3.31 (m, 1.5H), 3.16-3.01 (m, 1.5H), 2.72-2.35 (m, 6H), 1.85-1.81 (m, 4H), 1.41-1.32 (m, 6H). | 674.3 |
| 491 | (3S)-7-((2S,5R)-4-acryloyl-2,5-dimethylpiperazin-1-yl)-3-(methoxymethyl)-9-(trifluoromethyl)-10-(2,4,5-trifluorophenyl)-2H-[1,4]thiazino[2,3,4-ij]quinazolin-5(3H)-one | 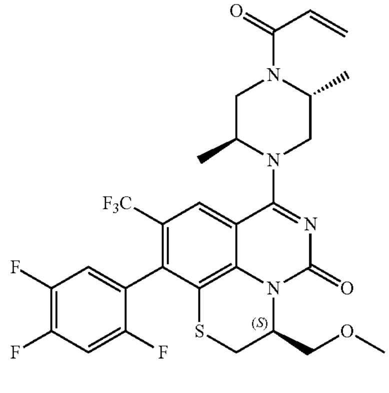 | $^1H$ NMR (400 MHz, $CDCl_3$) δ 7.86-7.83 (m, 1H), 7.11-7.02 (m, 2H), 6.66-6.50 (m, 1H), 6.37 (t, J = 14.4 Hz, 1H), 5.78 (t, J = 8.4 Hz, 1H), 5.43-5.39 (m, 1H), 5.07-5.04 (m, 0.6H), 4.80-4.66 (m, 1H), 4.43-4.33 (m, 1.4H), 4.13-4.07 (m, 0.5H), 3.75-3.62 (m, 4H), 3.40-3.34 (m, 4H), 3.26-3.21 (m, 0.5H), 3.05-3.02 (m, 1H), 1.49-1.41 (m, 6H). | 613.2 |

TABLE 7-continued

| Table of Thiomorpholines | | | | |
|---|---|---|---|---|
| Ex. # Name | Structure | $^1$H NMR | MS (M + H)$^+$ |
| 492 (3S)-7-((2S,5R)-4-acryloyl-2,5-dimethylpiperazin-1-yl)-10-(5-chloro-2,4-difluorophenyl)-3-(methoxymethyl)-9-(trifluoromethyl)-2H-[1,4]thiazino[2,3,4-ij]quinazolin-5(3H)-one | 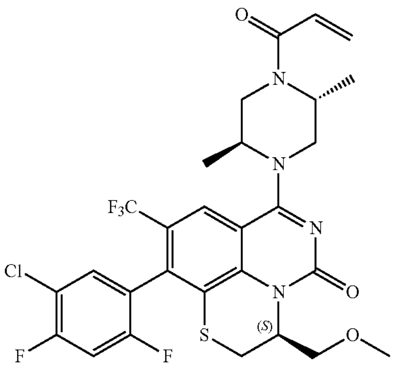 | $^1$H NMR (400 MHz, $CDCl_3$) δ 7.86-7.83 (m, 1H), 7.30-7.28 (m, 1H), 7.07 (t, J = 8.8 Hz, 1H), 6.66-6.50 (m, 1H), 6.37 (t, J = 14.4 Hz, 1H), 5.78 (t, J = 8.8 Hz , 1H), 5.45-5.41 (m, 1H), 5.08-5.04 (m, 0.6H), 4.79-4.67 (m, 1H), 4.44-4.33 (m, 1.4H), 4.12-4.06 (m, 0.5H), 3.72-3.62 (m, 4H), 3.41-3.34 (m, 4H), 3.27-3.20 (m, 0.5H), 3.05-3.02 (m, 1H), 1.49-1.40 (m, 6H). | 629.2 |
| 493 (3S)-7-((2S,5R)-4-acryloyl-2,5-dimethylpiperazin-1-yl)-10-(2,4-difluorophenyl)-3-(methoxymethyl)-9-(trifluoromethyl)-2H-[1,4]thiazino[2,3,4-ij]quinazolin-5(3H)-one | 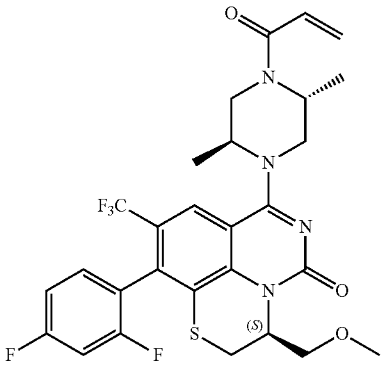 | $^1$H NMR (400 MHz, $CDCl_3$) δ 7.86-7.83 (m, 1H), 7.22-7.13 (m, 1H), 7.05-6.94 (m, 2H), 6.67-6.50 (m, 1H), 6.37 (t, J = 14.8 Hz, 1H), 5.77 (t, J = 8.8 Hz , 1H), 5.45-5.39 (m, 1H), 5.07-5.05 (m, 0.6H), 4.81-4.68 (m, 1H), 4.44-4.34 (m, 1.4H), 4.15-4.07 (m, 0.5H), 3.76-3.60 (m, 4H), 3.42-3.26 (m, 4.5H), 3.05-3.00 (m, 1H), 1.49-1.41 (m, 6H). | 595.2 |
| 494 (3S)-7-((2S,5R)-4-acryloyl-2,5-dimethylpiperazin-1-yl)-9-chloro-10-(2,4-difluorophenyl)-3-(methoxymethyl)-2H-[1,4]thiazino[2,3,4-ij]quinazolin-5(3H)-one | 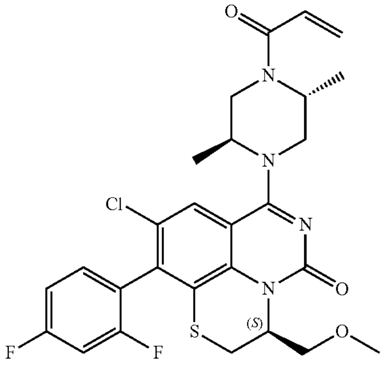 | $^1$H NMR (400 MHz, $CDCl_3$) δ 7.56 (s, 1H), 7.24-7.17 (m, 1H), 7.07-6.98 (m, 2H), 6.67-6.52 (m, 1H), 6.37 (t, J = 14.4 Hz, 1H), 5.79-5.75 (m, 1H), 5.52-5.46 (m, 1H), 5.10-5.02 (m, 0.6H), 4.84-4.71 (m, 1H), 4.40-4.32 (m, 1.4H), 4.08-4.02 (m, 0.6H), 3.79-3.55 (m, 4H), 3.49 (d, J = 6.4 Hz, 3H), 3.32-3.29 (m, 1.4H), 3.05-3.02 (m, 1H), 1.44-1.34 (m, 6H). | 561.2 |

TABLE 7-continued

| Table of Thiomorpholines | | | | |
|---|---|---|---|---|
| Ex. # | Name | Structure | $^1$H NMR | MS (M + H)$^+$ |
| 495 | (3S)-7-((2S,5R)-4-acryloyl-2,5-dimethylpiperazin-1-yl)-9-chloro-10-(5-chloro-2,4-difluorophenyl)-3-((4-(2,2-difluoroethyl)piperazin-1-yl)methyl)-2H-[1,4]thiazino[2,3,4-ij]quinazolin-5(3H)-one | 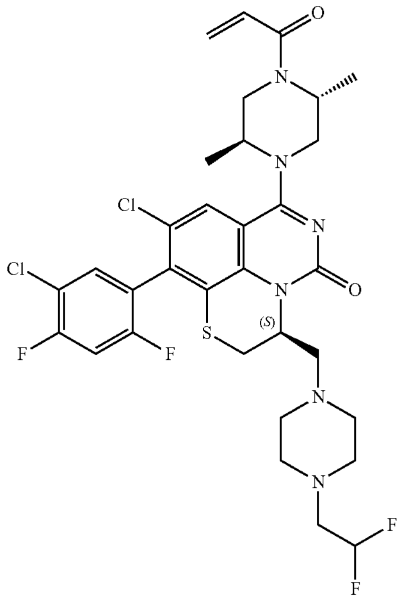 | $^1$H NMR (400 MHz, $CDCl_3$) δ 7.52 (s, 1H), 7.31-7.28 (m, 1H), 7.12-7.06 (m, 1H), 6.66-6.50 (m, 1H), 6.37 (t, J = 16 Hz, 1H), 6.00-5.70 (m, 2H), 5.43-5.36 (m, 1H), 4.99-4.69 (m, 1.5H), 4.40-4.21 (m, 1.5H), 3.98 (d, J = 14 Hz, 0.5H), 3.82-3.65 (m, 2H), 3.35-5.33 (m, 1.5H), 3.05-3.02 (m, 1H), 2.74-2.67 (m, 5H), 2.57-2.54 (m, 7H), 1.39-1.37 (m, 3H), 1.35-1.26 (m, 3H). | 713.2 |
| 496 | (3S)-7-((2S,5R)-4-acryloyl-2,5-dimethylpiperazin-1-yl)-9-chloro-10-(5-chloro-2,4-difluorophenyl)-3-(methoxymethyl)-2H-[1,4]thiazino[2,3,4-ij]quinazolin-5(3H)-one | 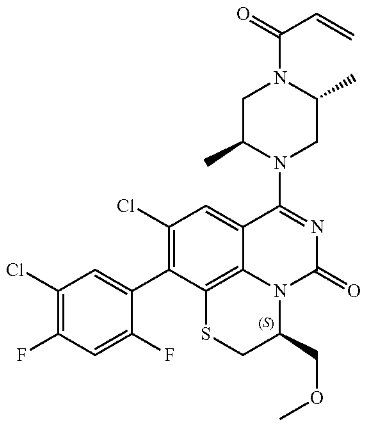 | $^1$H NMR (400 MHz, $CDCl_3$) δ 7.57-7.52 (m, 1H), 7.33-7.29 (m, 1H), 7.12-7.07 (m, 1H), 6.64-6.50 (m, 1H), 6.41-6.33 (m, 1H), 5.80-5.75 (m, 1H), 5.47 (s, 1H), 5.01 (s, 0.5H), 4.84(s, 0.5H), 4.70 (s, 0.5H), 4.38-4.30 (m, 1H), 4.06-4.03 (m, 0.5H), 3.80-3.57 (m, 4H), 3.41-3.37 (d, J = 16.0 Hz, 3H), 3.34-3.31 (m, 1H), 3.06-3.03 (m, 1H),1.43-1.34(m, 6H).1.25(s, 1H) | 595.1 |
| 497 | (S)-7-((2S,5R)-4-acryloyl-2,5-dimethylpiperazin-1-yl)-10-(4-fluorophenyl)-3-(methoxymethyl)-9-(trifluoromethyl)-2H-[1,4]thiazino[2,3,4-ij]quinazolin-5(3H)-one | 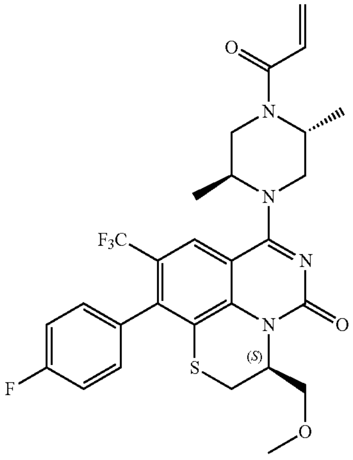 | $^1$H NMR (400 MHz, $CDCl_3$) δ 7.85-7.83 (d, J = 8.0 Hz, 1H), 7.24-7.15 (m, 4H), 6.67-6.51 (m, 1H), 6.41-6.34 (m, 1H), 5.80-5.76 (m, 1H), 5.41-5.40 (m, 1H), 5.06 (s, 0.5H), 4.81-4.79 (m, 0.5H), 4.46-4.34 (m, 1H), 4.13-4.09 (d, J = 16.0 Hz, 0.5H), 3.72-3.62 (m, 4H), 3.40 (s, 3H), 3.32-3.21 (m, 2H), 2.99-2.97 (d, J = 8.0 Hz, 0.5H),1.50-1.42 (m, 6H), 1.25 (m, 1H). | 577.2 |

TABLE 7-continued

Table of Thiomorpholines

| Ex. # | Name | Structure | $^1$H NMR | MS (M + H)$^+$ |
|---|---|---|---|---|
| 498 | (3S)-7-((2S,5R)-4-acryloyl-2,5-dimethylpiperazin-1-yl)-10-(2,4-difluorophenyl)-3-((2-methoxyethoxy)methyl)-9-(trifluoromethyl)-2H-[1,4]thiazino[2,3,4-ij]quinazolin-5(3H)-one | 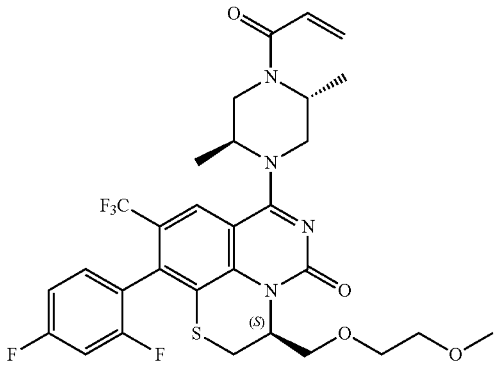 | $^1$H NMR (400 MHz, $CDCl_3$) δ 7.87-7.83 (m, 1H), 7.19-7.15 (m, 1H), 7.03-6.95 (m, 2H), 6.67-6.51 (m, 1H), 6.37 (t, J = 14.4 Hz, 1H), 5.78 (t, J = 9.2 Hz, 1H), 5.50-5.36 (m, 1H), 5.14-5.00 (m, 0.6H), 4.78-4.66 (m, 1H), 4.45-4.41(m, 1H), 4.41-4.34 (m, 0.4H), 4.16-4.08 (m, 0.6H), 3.78-3.63 (m, 6H), 3.52 (t, J = 4.8 Hz, 2H), 3.41-3.38 (m, 1H), 3.35 (s, 3H), 3.26-3.22 (m, 0.4H), 3.05-2.95 (m, 1H), 1.50-1.44 (m, 6H). | 639.3 |
| 499 | (3S)-7-((2S,5R)-4-acryloyl-2,5-dimethylpiperazin-1-yl)-9-chloro-10-(5-chloro-2,4-difluorophenyl)-3-((4-cyclopropylpiperazin-1-yl)methyl)-2H-[1,4]thiazino[2,3,4-ij]quinazolin-5(3H)-one | 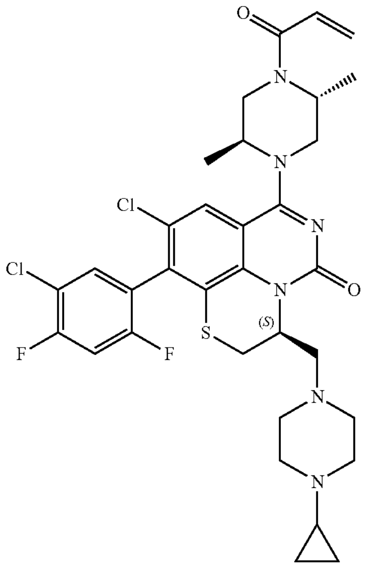 | $^1$H NMR (400 MHz, $CDCl_3$) δ 7.52 (s, 1H), 7.32-7.30 (m, 1H), 7.13-7.05 (m, 1H), 6.67-6.489 (m, 1H), 6.37 (t, J = 13.6 Hz, 1H), 5.79-5.75 (m, 1H), 5.48-5.37 (m, 1H), 5.01-4.67 (m, 2H), 4.42-3.95 (m, 2H), 3.84-3.66 (m, 2H), 3.40-3.31 (m, 1H), 3.10-3.08 (m, 1H), 2.82-2.48 (m, 10H), 1.46-1.24 (m, 7H), 0.57-0.40 (m, 4H). | 689.3 |
| 500 | (3S)-3-((1S,4S)-2-oxa-5-azabicyclo[2.2.1]heptan-5-ylmethyl)-7-((2S,5R)-4-acryloyl-2,5-dimethylpiperazin-1-yl)-9-chloro-10-(5-chloro-2,4-difluorophenyl)-2H-[1,4]thiazino[2,3,4-ij]quinazolin-5(3H)-one | 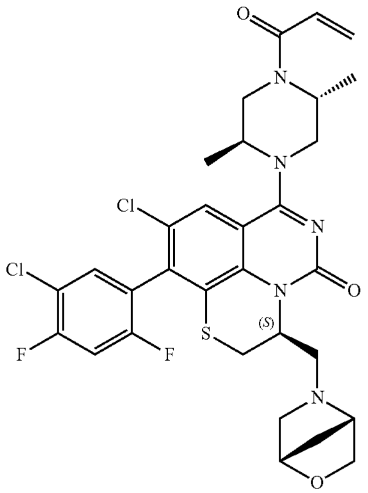 | $^1$H NMR (400 MHz, $CDCl_3$) δ 7.54-7.52 (m, 1H), 7.32-7.25 (m, 1H), 7.12-7.06 (m, 1H), 6.66-6.50 (m, 1H), 6.41-6.33 (m, 1H), 5.79-5.75 (m, 1H), 5.28-5.24 (m, 1H), 5.01-4.70 (m, 2H), 4.40-4.26 (m, 2H), 4.02-3.90 (m, 2H), 3.69-3.55 (m, 4H), 3.46-3.29 (m, 1H), 3.03-2.86 (m, 5H), 1.77-1.65 (m, 2H), 1.52-1.33 (m, 6H). | 662.3 |

TABLE 7-continued

| Table of Thiomorpholines | | | | |
|---|---|---|---|---|
| Ex. # | Name | Structure | $^1$H NMR | MS (M + H)$^+$ |
| 501 | (3S)-7-((2S,5R)-4-acryloyl-2,5-dimethylpiperazin-1-yl)-9-chloro-10-(2,4-difluorophenyl)-3-((2-methoxyethoxy)meth-yl)-2H-[1,4]thiazino[2,3,4-ij]quinazolin-5(3H)-one | 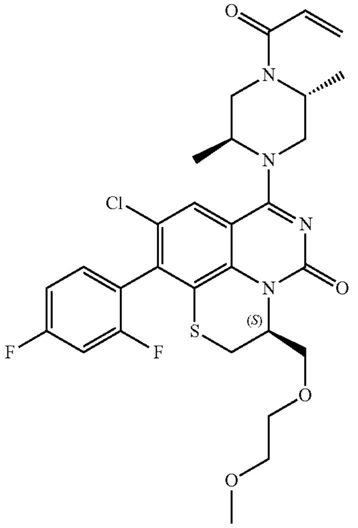 | $^1$H NMR (400 MHz, $CDCl_3$) δ 7.75-7.54 (m, 1H), 7.27-7.18 (m, 1H), 7.08-6.95 (m, 2H), 6.67-6.50 (m, 1H), 6.37 (t, J = 16.0 Hz, 1H), 5.80-5.75 (m, 1H), 5.50-5.47 (m, 1H), 5.03-5.00 (m, 0.5H), 4.83-4.69 (m, 1H), 4.41-4.32 (m, 1.5H), 4.10-4.03 (m, 0.5H), 3.82-3.62 (m, 6.5H), 3.54-3.50 (m, 2H), 3.38-3.35 (m, 4H), 3.05-3.02 (m, 1H), 1.45-1.36 (m, 6H). | 605.2 |
| 502 | (3S)-7-((2S,5R)-4-acryloyl-2,5-dimethylpiperazin-1-yl)-9-chloro-10-(5-chloro-2,4-difluorophenyl)-3-((2-methoxyethoxy)meth-yl)-2H-[1,4]thiazino[2,3,4-ij]quinazolin-5(3H)-one | 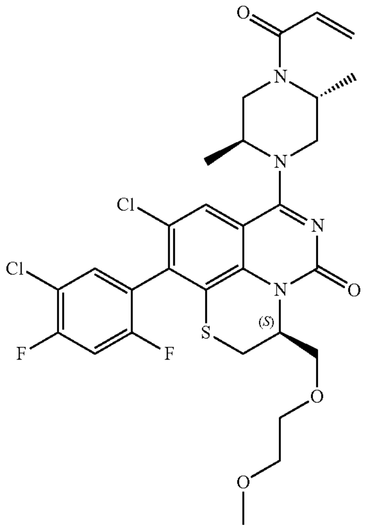 | $^1$H NMR (400 MHz, $CDCl_3$) δ 7.56-7.53 (m, 1H), 7.32-7.28 (m, 1H), 7.12-7.06 (m, 1H), 6.67-6.50(m, 1H), 6.37 (t, J = 14.4 Hz, 1H), 5.80-5.75 (m, 1H), 5.49-5.47 (m, 1H), 5.03-5.00 (m, 0.5H), 4.82-4.68 (m, 1H), 4.42-4.31 (m, 1.5H), 4.08-4.02 (m, 0.5H), 3.83-3.62 (m, 6.5H), 3.55-3.50 (m, 2H), 3.37-3.30 (m, 4H), 3.06-3.02 (m, 1H), 1.43-1.35 (m, 6H). | 639.2 |
| 506 | (3S)-7-((3S,5R)-4-acryloyl-3,5-dimethylpiperazin-1-yl)-9-chloro-3-(methoxymethyl)-10-(2,4,5-trifluorophenyl)-2,3-dihydro-5H-[1,4]thiazino[2,3,4-ij]quinazolin-5-one | 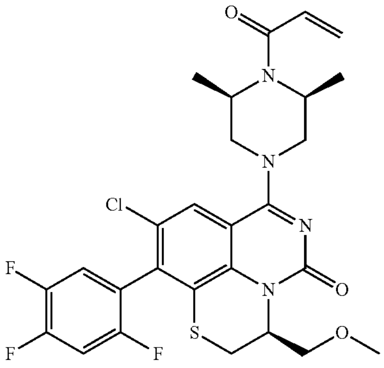 [SMILES: C=CC(=O)N1[C@H](C)CN(c2nc(=O)n3c4c(c(-c5cc(F)c(F)cc5F)c(Cl)cc24)SC[C@@H]3COC)C[C@@H]1C] | $^1$H NMR (400 MHz, MeOH-$d_4$) δ 7.90 (s, 1H), 7.46-7.27 (m, 2H), 6.83 (dd, J = 16.7, 10.6 Hz, 1H), 6.28 (dd, J = 16.7, 2.0 Hz, 1H), 5.80 (dd, J = 10.6, 2.0 Hz, 1H), 5.40-5.31 (m, 1H), 1.57-1.50 (m, 3H), 1.43-1.36 (m, 3H) | 579.2 |

TABLE 7-continued

Table of Thiomorpholines

| Ex. # | Name | Structure | $^1$H NMR | MS (M + H)$^+$ |
|---|---|---|---|---|
| 508 | (3S,10S)-7-((2S,5R)-4-acryloyl-2,5-dimethylpiperazin-1-yl)-10-(2,4-difluorophenyl)-3-(methoxymethyl)-9-(trifluoromethyl)-2,3-dihydro-5H-[1,4]thiazino[2,3,4-ij]quinazolin-5-one | 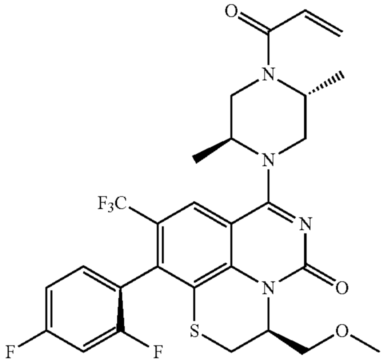 | $^1$H NMR (400 MHz, $CDCl_3$) δ 7.84 (d, J = 12 Hz, 1H), 7.16 (q, J = 7.6 Hz, 1H), 7.05-6.94 (m, 2H), 6.66-6.50 (m, 1H), 6.37 (t, J = 14.8 Hz, 1H), 5.78 (t, J = 8.4 Hz, 1H), 5.45-5.43 (m, 1H), 5.08-5.04 (m, 0.6H), 4.82-4.65 (m, 1H), 4.43-4.33 (m, 1.4H), 4.11-4.17 (m, 0.5H), 3.73-3.61 (m, 4H), 3.42-3.31 (m, 4H), 3.26-3.21 (m, 0.5H), 3.01 (d, J = 13.6 Hz, 1H), 1.50-1.41 (m, 6H). | 595.2 |
| 509 | (3S,10R)-7-((2S,5R)-4-acryloyl-2,5-dimethylpiperazin-1-yl)-10-(2,4-difluorophenyl)-3-(methoxymethyl)-9-(trifluoromethyl)-2,3-dihydro-5H-[1,4]thiazino[2,3,4-ij]quinazolin-5-one | 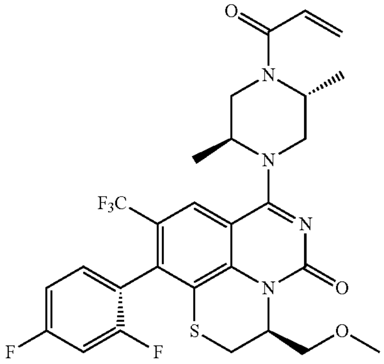 | $^1$H NMR (400 MHz, $CDCl_3$) δ 7.84 (d, J = 6.4 Hz, 1H), 7.19 (q, J = 8.0 Hz, 1H), 7.04-6.94 (m, 2H), 6.66-6.50 (m, 1H), 6.37 (t, J = 14.8 Hz, 1H), 5.77 (t, J = 9.2 Hz , 1H), 5.41-5.39 (m, 1H), 5.07-5.04 (m, 0.6H), 4.80-4.66 (m, 1H), 4.44-4.35 (m, 1.4H), 4.15-4.12 (m, 0.5H), 3.72-3.64 (m, 4H), 3.39-3.32 (m, 4H), 3.26-3.22 (m, 0.5H), 3.02 (d, J = 13.2 Hz, 1H), 1.49-1.43 (m, 6H). | 595.2 |
| 510 | (3S,10S)-7-((2S,5R)-4-acryloyl-2,5-dimethylpiperazin-1-yl)-10-(2,4-difluorophenyl)-3-((2-methoxyethoxy)methyl)-9-(trifluoromethyl)-2,3-dihydro-5H-[1,4]thiazino[2,3,4-ij]quinazolin-5-one | 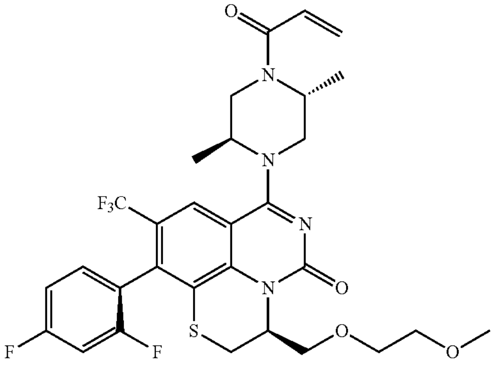 | $^1$H NMR (400 MHz, $CDCl_3$) δ 7.86-7.83 (m, 1H), 7.16 (q, J = 7.6 Hz, 1H), 7.05-7.01 (m, 1H), 6.98-6.93 (m, 1H), 6.67-6.51 (m, 1H), 6.37 (t, J = 14.8 Hz, 1H), 5.78(t, J = 8.4 Hz, 1H), 5.48-5.41 (m, 1H), 5.11-5.03 (m, 0.5H), 4.79-4.67 (m, 1H), 4.41-4..35 (m, 1.5H), 4.11-4.08 (m, 0.5H), 3.79-3.63 (m, 6H), 3.52 (t, J = 4.8 Hz, 2H), 3.42-3.38 (m, 1H), 3.35 (s, 3H), 3.25-3.22 (m, 0.5H), 3.03-2.99 (m, 1H), 1.50-1.42 (m, 6H). | 639.3 |
| 511 | (3S,10R)-7-((2S,5R)-4-acryloyl-2,5-dimethylpiperazin-1-yl)-10-(2,4-difluorophenyl)-3-((2-methoxyethoxy)methyl)-9-(trifluoromethyl)-2,3-dihydro-5H-[1,4]thiazino[2,3,4-ij]quinazolin-5-one | 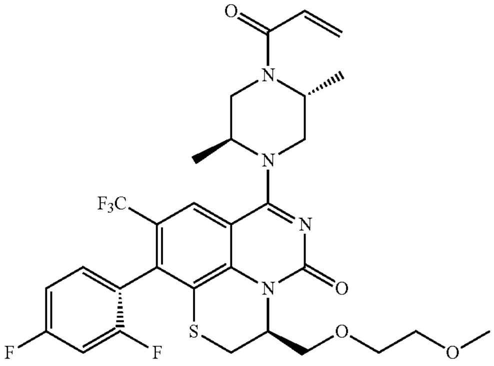 | $^1$H NMR (400 MHz, $CDCl_3$) δ 7.86-7.83 (m, 1H), 7.18 (q, J = 8.0 Hz, 1H), 7.04-6.94 (m, 2H), 6.67-6.50 (m, 1H), 6.37 (t, J = 15.6 Hz, 1H), 5.80-5.75 (m, 1H), 5.46-5.36 (m, 1H), 5.11-5.01 (m, 0.5H), 4.78-4.67 (m, 1H), 4.45-4.31 (m, 1.5H), 4.16-4.12 (m, 0.5H), 3.78-3.60 (m, 6H), 3.52 (t, J = 4.8 Hz, 2H), 3.41-3.38 (m, 1H), 3.35 (s, 3H), 3.26-3.22 (m, 0.5H), 3.03 (d, J = 13.2 Hz, 1H), 1.49-1.43 (m, 6H). | 639.2 |

TABLE 7-continued

Table of Thiomorpholines

| Ex. # | Name | Structure | $^1$H NMR | MS (M + H)$^+$ |
|---|---|---|---|---|
| 512 | (S)-7-((2S,5R)-4-acryloyl-2,5-dimethylpiperazin-1-yl)-10-(4-fluorophenyl)-3-((2-methoxyethoxy)methyl)-9-(trifluoromethyl)-2H-[1,4]thiazino[2,3,4-ij]quinazolin-5(3H)-one | 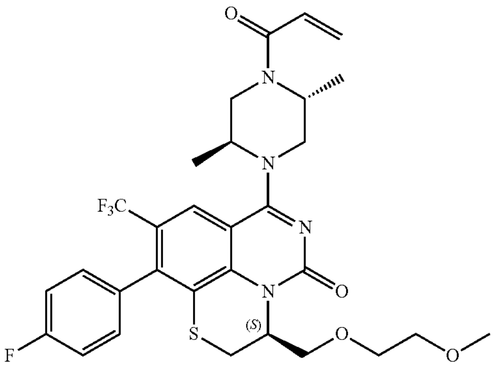 | $^1$H NMR (400 MHz, $CDCl_3$) δ 7.84 (d, J = 10.0 Hz, 1H), 7.26-7.12 (m, 4H), 6.70-6.48 (m, 1H), 6.37 (t, J = 15.0 Hz, 1H), 5.78 (t, J = 8.8 Hz, 1H), 5.46-5.36 (m, 1H), 5.12-5.04 (m, 0.5H), 4.78-4.67 (m, 1H), 4.42 (d, J = 13.6 Hz, 1H), 4.38-4.30 (m, 0.5H), 4.11 (m, 0.5H), 3.82-3.58 (m, 6H), 3.52 (t, J = 4,6 Hz, 2H), 3.40-3.32 (m, 4H), 3.28-3.20 (m, 0.5H), 3.02-2.92 (m, 1H), 1.52-1.40 (m, 6H). | 621.3 |
| 513 | (3S)-7-((3S,5R)-4-acryloyl-3,5-dimethylpiperazin-1-yl)-10-(2,4-difluorophenyl)-3-(methoxymethyl)-9-(trifluoromethyl)-2H-[1,4]thiazino[2,3,4-ij]quinazolin-5(3H)-one | 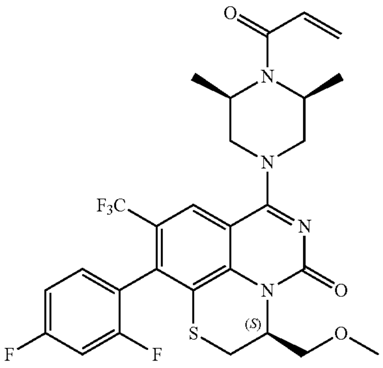 | $^1$H NMR (400 MHz, $CDCl_3$) δ 8.07 (s, 1H), 7.17 (q, J = 8.0 Hz, 1H), 7.06-6.93 (m, 2H), 6.62 (dd, J = 10.4 Hz, 16.8 Hz, 1H), 6.40 (dd, J = 2.0 Hz, 16.8 Hz, 1H), 5.77 (dd, J = 2.0 Hz, 10.4 Hz, 1H), 5.48-5.41 (m, 1H), 4.79-4.53 (m, 2H), 4.21-4.16 (m, 2H), 3.69-3.59 (m, 2H), 3.37-3.30 (m, 6H), 3.05-2.99 (m, 1H), 1.62 (d, J = 6.8 Hz, 3H), 1.47 (d, J = 6.8 Hz, 3H). | 595.2 |
| 514 | (3S)-7-(4-acryloylpiperazin-1-yl)-10-(2,4-difluorophenyl)-3-(methoxymethyl)-9-(trifluoromethyl)-2H-[1,4]thiazino[2,3,4-ij]quinazolin-5(3H)-one | 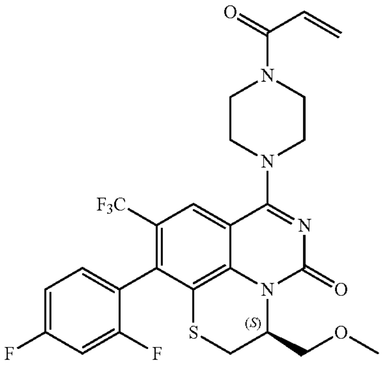 | $^1$H NMR (400 MHz, $CDCl_3$) δ 7.81 (s, 1H), 7.18 (q, J = 6.4 Hz, 1H), 7.05-6.93 (m, 2H), 6.59 (dd, J = 10.4 Hz, 16.8 Hz, 1H), 6.37 (dd, J = 2.0 Hz, 16.8 Hz, 1H), 5.78 (dd, J = 2.0 Hz, 10.4 Hz, 1H), 5.47-5.39 (m, 1H), 4.00-3.92 (m, 3H), 3.81-3.78 (m, 5H), 3.69-3.60 (m, 2H), 3.39 (s, 3H), 3.37-3.33 (m, 1H), 3.04-2.98 (m, 1H). | 567.2 |

TABLE 7-continued

Table of Thiomorpholines

| Ex. # | Name | Structure | $^1H$ NMR | MS $(M + H)^+$ |
|---|---|---|---|---|
| 515 | (S)-7-((2S,5R)-4-acryloyl-2,5-dimethylpiperazin-1-yl)-9-chloro-3-((4-(2,2-difluoroethyl)piperazin-1-yl)methyl)-10-(4-fluorophenyl)-2H-[1,4]thiazino[2,3,4-ij]quinazolin-5(3H)-one | 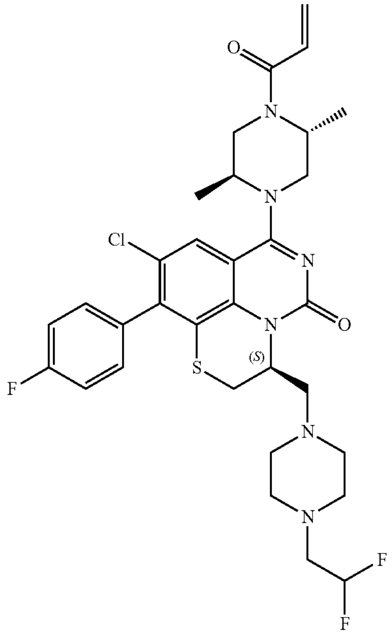 | $^1H$ NMR (400 MHz, $CDCl_3$) δ 7.52 (s, 1H), 7.26-7.16 (m, 4H), 6.66-6.51 (m, 1H), 6.40-6.33 (m, 1H), 5.99-5.70 (m, 2H), 5.41-5.36 (m, 1H), 4.98-4.72 (m, 1.5H), 4.39-4.22 (m, 1H), 4.00-3.97 (m, 0.5H), 3.83-3.65 (m, 2H), 3.36-3.27 (m, 1.5H), 3.00-2.96 (m, 1H), 2.80-2.61 (m, 5.5H), 2.61-2.50 (m, 7H), 1.39-1.30 (m, 6H). | 661.3 |
| 516 | (S)-7-((S)-4-acryloyl-2-methylpiperazin-1-yl)-10-(4-fluorophenyl)-3-((methoxymethoxy)methyl)-9-(trifluoromethyl)-2H-[1,4]thiazino[2,3,4-ij]quinazolin-5(3H)-one | 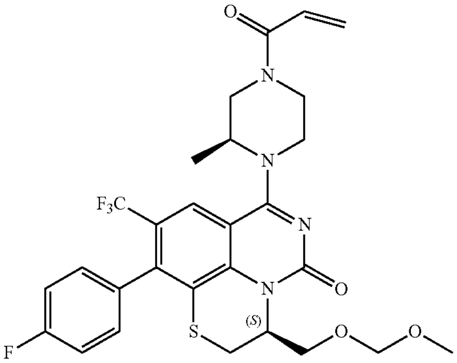 | $^1H$ NMR (400 MHz, $CDCl_3$) δ 7.77 (s, 1H), 7.21-7.14 (m, 4H), 6.66-6.51 (m, 1H), 6.39 (d, J = 16.8 Hz, 1H), 5.79 (d, J = 8 Hz, 1H), 5.41 (s, 1H), 4.68-4.62 (m, 3H), 4.53-4.30 (m, 2H), 3.99-3.94 (m, 1H), 3.83-3.79 (m, 2H), 3.65-3.43 (m, 2.5H), 3.37 (s, 3H), 3.35-3.33 (m, 0.5H), 3.09-2.98 (m, 2H), 1.55-1.49 (m, 3H). | 593.3 |
| 517 | (S)-7-((2S,5R)-4-acryloyl-2,5-dimethylpiperazin-1-yl)-9-chloro-3-((4-cyclopropylpiperazin-1-yl)methyl)-10-(4-fluorophenyl)-2H-[1,4]thiazino[2,3,4-ij]quinazolin-5(3H)-one | 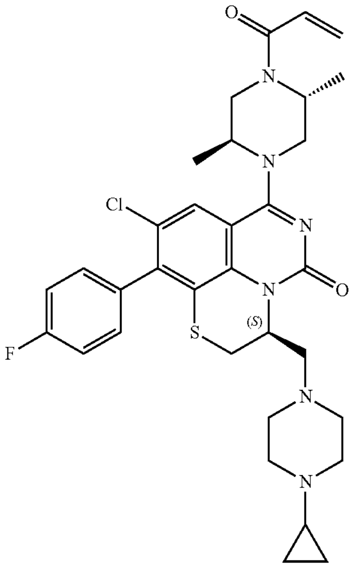 | $^1H$ NMR (400 MHz, $CDCl_3$) δ 7.52 (s, 1H), 7.24-7.19 (m, 4H), 6.67-6.49 (m, 1H), 6.36 (t, J = 14.4 Hz, 1H), 5.79-5.73 (m, 1H), 5.47-5.37 (m, 1H), 5.02-4.69 (m, 2H), 4.42-3.97 (m, 2H), 3.86-3.61 (m, 2H), 3.40-3.29 (m, 1H), 3.05-2.94 (m, 1H), 2.83-2.48 (m, 10H) , 1.39-1.24 (m, 7H), 0.57-0.36 (m, 4H). | 637.3 |

TABLE 7-continued

Table of Thiomorpholines

| Ex. # | Name | Structure | $^1$H NMR | MS (M + H)$^+$ |
|---|---|---|---|---|
| 518 | (3S)-7-((S)-4-acryloyl-2-methylpiperazin-1-yl)-10-(5-chloro-2,4-difluorophenyl)-3-((methoxymethoxy)methyl)-9-(trifluoromethyl)-2H-[1,4]thiazino[2,3,4-ij]quinazolin-5(3H)-one | 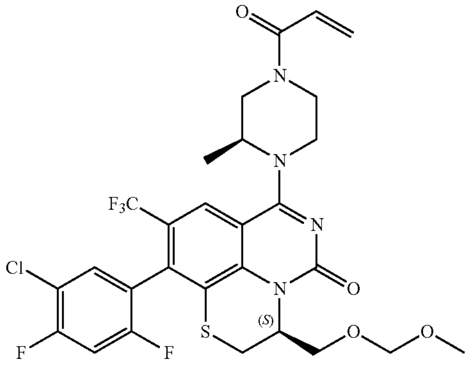 | $^1$H NMR (400 MHz, $CDCl_3$) δ 7.78 (s, 1H), 7.31-7.24 (m, 1H), 7.10-7.04 (m, 1H), 6.67-6.50 (m, 1H), 6.38 (dd, J = 16.8 Hz, 2.0 Hz, 1H), 5.79 (d, J = 10.4 Hz, 1H), 5.50-5.38 (m, 1H), 4.80-4.62 (m, 3H), 4.59-4.26 (m, 2H), 4.06-3.92 (m, 0.5H), 3.90-3.74 (m, 2.5H), 3.67-3.47 (m, 1.5H), 3.46-3.33 (m, 4.5H), 3.17-2.96 (m, 2H), 1.61-1.44 (m, 3H). | 645.2 |
| 519 | (3S)-3-((1S,4S)-2-oxa-5-azabicyclo[2.2.1]heptan-5-ylmethyl)-7-((2S,5R)-4-acryloyl-2,5-dimethylpiperazin-1-yl)-9-chloro-10-(2,4-difluorophenyl)-2H-[1,4]thiazino[2,3,4-ij]quinazolin-5(3H)-one | 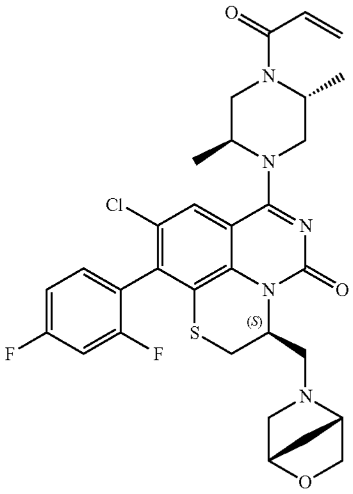 | $^1$H NMR (400 MHz, $CDCl_3$) δ 7.55-7.52 (m, 1H), 7.25-7.18 (m, 1H), 7.07-6.96 (m, 2H), 6.66-6.50 (m, 1H), 6.41-6.33 (m, 1H), 5.79-5.75 (m, 1H), 5.28-5.26 (m, 1H), 5.01-4.70 (m, 2H), 4.40-4.32 (m, 2H), 4.04-3.30 (m, 9H), 3.03-2.84 (m, 5H), 1.42-1.33 (m, 6H). | 628.2 |
| 520 | (3S)-7-((S)-4-acryloyl-2-methylpiperazin-1-yl)-9-chloro-3-((4-cyclopropylpiperazin-1-yl)methyl)-10-(2,4,5-trifluorophenyl)-2H-[1,4]thiazino[2,3,4-ij]quinazolin-5(3H)-one | 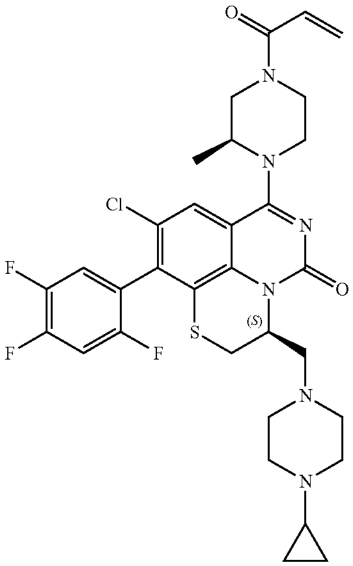 | $^1$H NMR (400 MHz, $CDCl_3$) δ 7.49 (s, 1H), 7.14-7.04 (m, 2H), 6.66-6.50 (m, 1H), 6.37 (dd, J = 2.0 Hz, J = 1.2 Hz, 1H) , 5.78 (d, J = 11.6 Hz, 1H), 5.41-5.31 (m, 1H), 4.76-3.79 (m, 5H), 3.56-3.39 (m, 4H), 3.09-3.04 (m, 3H), 2.95-2.52 (m, 8H), 1.50-1.43 (m, 4H), 0.87-0.35 (m, 3H). | 659.3 |

TABLE 7-continued

| Table of Thiomorpholines | | | | |
|---|---|---|---|---|
| Ex. # | Name | Structure | $^1$H NMR | MS $(M + H)^+$ |
| 521 | (3S)-7-((2S,5R)-4-acryloyl-2,5-dimethylpiperazin-1-yl)-10-(5-chloro-2,4-difluorophenyl)-3-((4-(2,2-difluoroethyl)piperazin-1-yl)methyl)-9-(trifluoromethyl)-2H-[1,4]thiazino[2,3,4-ij]quinazolin-5(3H)-one | 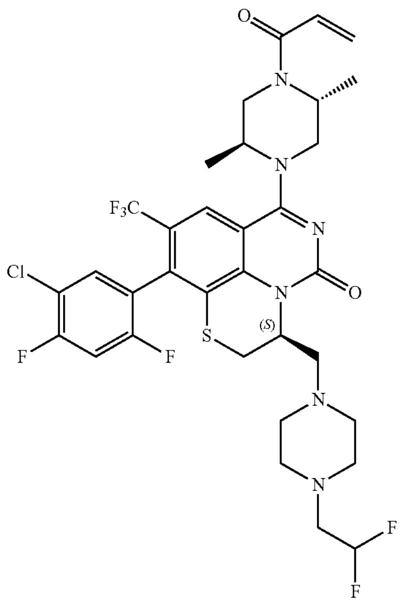 | $^1$H NMR (400 MHz, $CDCl_3$) δ 7.83 (s, 1H), 7.09-7.04 (m, 1H), 6.66-6.50 (m, 1H), 6.37 (t, J = 14.0 Hz, 1H), 6.00-5.72 (m, 2H), 5.42-5.31 (m, 1H), 5.08-4.64 (m, 2H), 4.43-4.33 (m, 1H), 4.12-4.01 (m, 1H), 3.72-3.64 (m, 3H), 3.41-3.01 (m, 4H), 2.79-2.53 (m, 10H), 1.47-1.37 (m, 6H). | 747.3 |
| 522 | (3S)-7-((S)-4-acryloyl-2-methylpiperazin-1-yl)-3-((methoxymethoxy)methyl)-9-(trifluoromethyl)-10-(2,4,5-trifluorophenyl)-2H-[1,4]thiazino[2,3,4-ij]quinazolin-5(3H)-one | 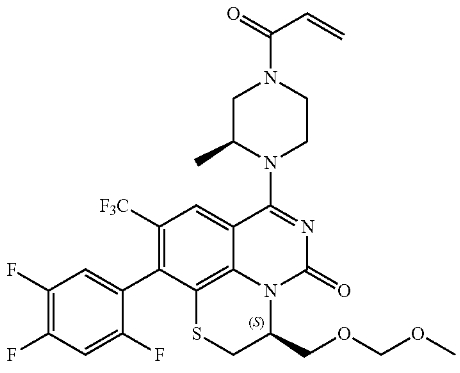 | $^1$H NMR (400 MHz, $CDCl_3$) δ 7.78 (s, 1H), 7.13-7.00 (m, 2H), 6.70-6.48 (m, 1H), 6.38 (dd, J = 16.8 Hz, 1.6 Hz, 1H), 5.79 (d, J = 10.4 Hz, 1H), 5.52-5.37 (m, 1H), 4.78-4.60 (m, 3H), 4.58-4.26 (m, 2H), 4.06-3.92 (m, 0.5H), 3.89-3.74 (m, 2.5H), 3.69-3.42 (m, 1.5H), 3.42-3.27 (m, 4.5H), 3.98-3.16 (m, 2H), 1.62-1.42 (m, 3H). | 629.2 |
| 523 | (3S)-7-(9-acryloyl-7,7-difluoro-3,9-diazabicyclo[3.3.1]nonan-3-yl)-10-(2,4-difluorophenyl)-3-(methoxymethyl)-9-(trifluoromethyl)-2H-[1,4]thiazino[2,3,4-ij]quinazolin-5(3H)-one | 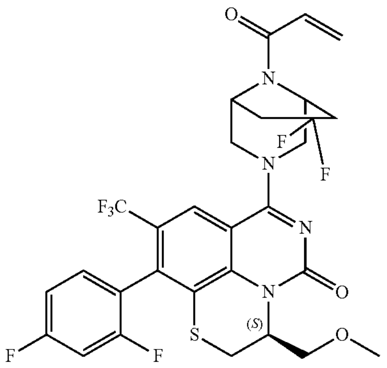 | $^1$H NMR (400 MHz, $CDCl_3$) δ 8.01-7.94 (m, 1H), 7.21-7.15 (m, 1H), 7.05-6.94 (m, 2H), 6.63-6.56 (m, 1H), 6.43 (dd, J = 1.6 Hz, 16.8 Hz, 1H), 5.86 (d, J = 10 Hz, 1H), 5.44-5.33 (m, 1H), 5.16-5.15 (m, 1H), 4.77-4.69 (m, 1H), 4.55-4.51 (m, 1H), 4.38-4.28 (m, 1H), 3.66-3.50 (m, 3H), 3.39-3.32 (m, 4H), 3.04-2.98 (m, 1H), 2.60-2.32 (m, 4H), 2.04-1.98 (m, 1H). | 643.2 |

TABLE 7-continued

| Table of Thiomorpholines | | | | |
|---|---|---|---|---|
| Ex. # | Name | Structure | $^1$H NMR | MS (M + H)$^+$ |
| 544 | (3S,10S)-7-((2S,5R)-4-acryloyl-2,5-dimethylpiperazin-1-yl)-10-(5-chloro-2,4-difluorophenyl)-3-(methoxymethyl)-9-(trifluoromethyl)-2,3-dihydro-5H-[1,4]thiazino[2,3,4-ij]quinazolin-5-one | 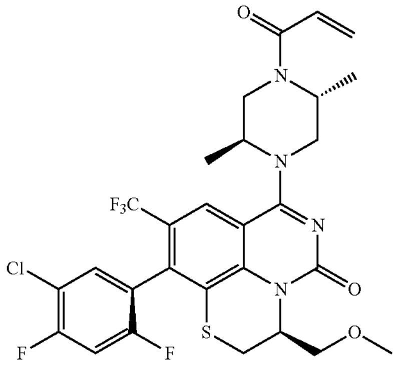 | $^1$H NMR (400 MHz, $CDCl_3$) δ 7.84 (d, J = 10.8 Hz, 1H), 7.26-7.23 (m, 1H), 7.07 (t, J = 8.8 Hz, 1H), 6.67-6.50 (m, 1H), 6.37 (t, J = 14.0 Hz, 1H), 5.78 (t, J = 8.8 Hz , 1H), 5.46-5.41 (m, 1H), 5.09-5.03 (m, 0.6H), 4.80-4.65 (m, 1H), 4.44-4.33 (m, 1.4H), 4.10-4.07 (m, 0.5H), 3.72-3.63 (m, 4H), 3.39-3.34 (m, 4H), 3.25-3.21 (m, 0.5H), 3.05-3.01 (m, 1H), 1.50-1.44 (m, 6H). | 629.2 |
| 545 | (3S,10R)-7-((2S,5R)-4-acryloyl-2,5-dimethylpiperazin-1-yl)-10-(5-chloro-2,4-difluorophenyl)-3-(methoxymethyl)-9-(trifluoromethyl)-2,3-dihydro-5H-[1,4]thiazino[2,3,4-ij]quinazolin-5-one | 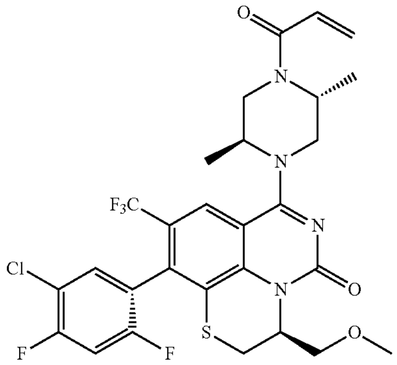 | $^1$H NMR (400 MHz, $CDCl_3$) δ 7.84-7.84 (m, 1H), 7.30-7.28 (m, 1H), 7.07 (t, J = 8.4 Hz, 1H), 6.66-6.50 (m, 1H), 6.37 (t, J = 14.0 Hz, 1H), 5.80-5.75 (m, 1H), 5.44-5.40 (m, 1H), 5.08-5.03 (m, 0.6H), 4.80-4.66 (m, 1H), 4.44-4.34 (m, 1.4H), 4.13-4.09 (m, 0.5H), 3.75-3.65 (m, 4H), 3.41-3.35 (m, 4H), 3.26-3.23 (m, 0.5H), 3.05-3.02 (m, 1H), 1.49-1.42 (m, 6H). | 629.2 |
| 546 | (3S,10S)-7-((3S,5R)-4-acryloyl-3,5-dimethylpiperazin-1-yl)-10-(2,4-difluorophenyl)-3-(methoxymethyl)-9-(trifluoromethyl)-2,3-dihydro-5H-[1,4]thiazino[2,3,4-ij]quinazolin-5-one | 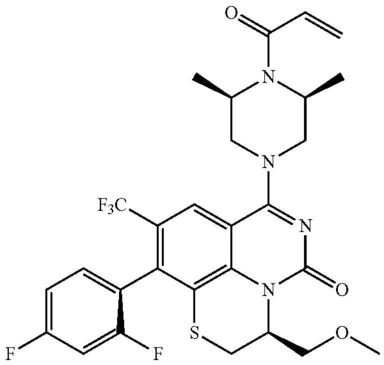 | $^1$H NMR (400 MHz, $CDCl_3$) δ 8.07 (s, 1H), 7.18 (q, J = 8.0 Hz, 1H), 7.05-6.93 (m, 2H), 6.62 (dd, J = 6.0 Hz, 16.4 Hz, 1H), 6.40 (dd, J = 1.6 Hz, 16.4 Hz, 1H), 5.77 (dd, J = 1.6 Hz, 10.4 Hz, 1H), 5.48-5.45 (m, 1H), 4.70-4.60 (m, 1H), 4.22-4.17 (m, 2H), 3.74-3.60 (m, 3H), 3.39-3.31 (m, 6H), 3.03-2.99 (m, 1H), 1.63-1.61 (m, 3H), 1.47 (d, J = 7.2 Hz, 3H). | 595.2 |
| 547 | (3S,10R)-7-((3S,5R)-4-acryloyl-3,5-dimethylpiperazin-1-yl)-10-(2,4-difluorophenyl)-3-(methoxymethyl)-9-(trifluoromethyl)-2,3-dihydro-5H-[1,4]thiazino[2,3,4-ij]quinazolin-5-one | 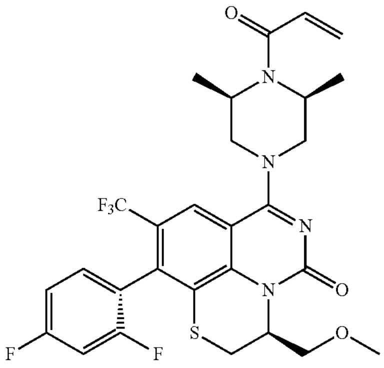 | $^1$H NMR (400 MHz, $CDCl_3$) δ 8.07 (s, 1H), 7.18 (q, J = 7.6 Hz, 1H), 7.04-6.94 (m, 2H), 6.62 (dd, J = 10.0 Hz, 16.8 Hz, 1H), 6.40 (dd, J = 2.0 Hz, 16.8 Hz, 1H), 5.77 (dd, J = 2.0 Hz, 10.8 Hz, 1H), 5.46-5.42 (m, 1H), 4.73-4.61 (m, 1H), 4.21-4.16 (m, 2H), 3.74-3.64 (m, 3H), 3.40-3.30 (m, 6H), 3.03 (dd, J = 2.4 Hz, 13.2 Hz, 1H), 1.63-1.61 (m, 3H), 1.47 (d, J = 7.2 Hz, 3H). | 595.2 |

TABLE 7-continued

| Table of Thiomorpholines | | | | |
|---|---|---|---|---|
| Ex. # | Name | Structure | $^1$H NMR | MS $(M + H)^+$ |
| 548 | (3S,10R)-7-((S)-4-acryloyl-2-methylpiperazin-1-yl)-10-(2,4-difluorophenyl)-3-((methoxymethoxy) methyl)-9-(trifluoromethyl)-2,3-dihydro-5H-[1,4]thiazino[2,3,4-ij]quinazolin-5-one | 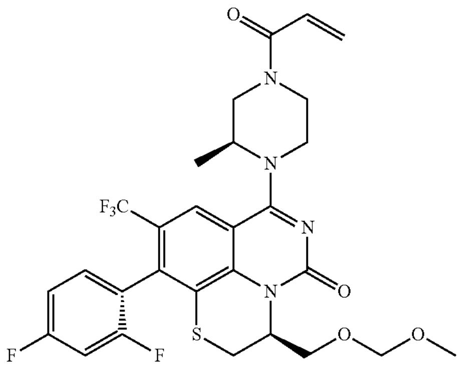 | $^1$H NMR (400 MHz, $CDCl_3$) δ 7.77 (s, 1H), 7.18 (q, J = 8.0 Hz, 1H), 7.04-6.95 (m, 2H), 6.66-6.51 (m, 1H), 6.40 (d, J = 16.8 Hz, 1H), 5.79 (d, J = 10.4 Hz, 1H), 5.427-5.425 (m, 1H), 4.71-4.62 (m, 3H), 4.54-4.34 (m, 2H), 4.02-3.96 (m, 1H), 3.81-3.79 (m, 2H), 3.63-3.60 (m, 1H), 3.52-3.39 (m, 2H), 3.35 (s, 3H), 3.09-3.01 (m, 2H), 1.58-1.51 (m, 3H). | 611.3 |
| 549 | (3S,10S)-7-((S)-4-acryloyl-2-methylpiperazin-1-yl)-10-(2,4-difluorophenyl)-3-((methoxymethoxy) methyl)-9-(trifluoromethyl)-2H-[1,4]thiazino[2,3,4-ij]quinazolin-5(3H)-one | 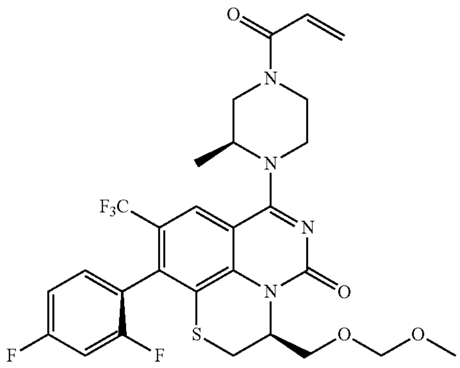 | $^1$H NMR (400 MHz, $CDCl_3$) δ 7.78 (s, 1H), 7.20-7.15 (m, 1H), 7.03 (t, J = 7.6 Hz, 1H), 6.98-6.93 (m, 1H), 6.64-6.51 (m, 1H), 6.39 (d, J = 16.4 Hz, 1H), 5.79 (d, J = 9.6 Hz, 1H), 5.46-5.45 (m, 1H), 4.72-4.62 (m, 3H), 4.51-4.28 (m, 2H), 3.97-3.94 (m, 1H), 3.82-3.78 (m, 2H), 3.64-3.53 (m, 1H), 3.49-3.38 (m, 2H), 3.38 (s, 3H), 3.07-3.05 (m, 2H), 1.56-1.50 (m, 3H). | 611.2 |
| 550 | (3S)-7-((2S,5R)-4-acryloyl-2,5-dimethylpiperazin-1-yl)-9-chloro-3-((4-(2,2-difluoroethyl)piperazin-1-yl)methyl)-10-(2,4-difluorophenyl)-2H-[1,4]thiazino[2,3,4-ij]quinazolin-5(3H)-one | 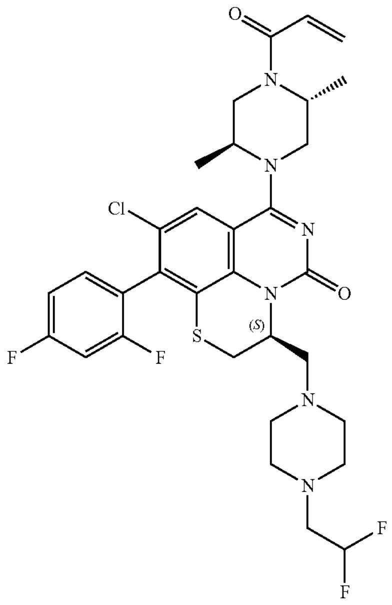 | $^1$H NMR (400 MHz, $CDCl_3$) δ 7.54 (s, 1H), 7.21 (q, J = 8.4 Hz, 1H), 7.07-6.95 (m, 2H), 6.66-6.50 (m, 1H), 6.37 (t, J = 14.8 Hz, 1H), 5.99-5.71 (m, 2H), 5.48-5.38 (m, 1H), 5.01-4.70 (m, 1.5H), 4.39-4.24 (m, 1.5H), 4.07-3.97 (m, 0.5H), 3.80-3.65 (m, 2.5H), 3.40-3.26 (m, 1.5H), 3.09-2.99 (m, 1.5H), 2.84-2.64 (m, 5.5H), 2.64-2.45 (m, 5.5H), 1.45-1.25 (m, 6H). | 679.2 |

TABLE 7-continued

| Table of Thiomorpholines | | | | |
|---|---|---|---|---|
| Ex. # Name | | Structure | $^1$H NMR | MS (M + H)$^+$ |
| 551 | (3S)-7-((2S,5R)-4-acryloyl-2,5-dimethylpiperazin-1-yl)-9-chloro-3-((4-cyclopropylpiperazin-1-yl)methyl)-10-(2,4-difluorophenyl)-2H-[1,4]thiazino[2,3,4-ij]quinazolin-5(3H)-one | 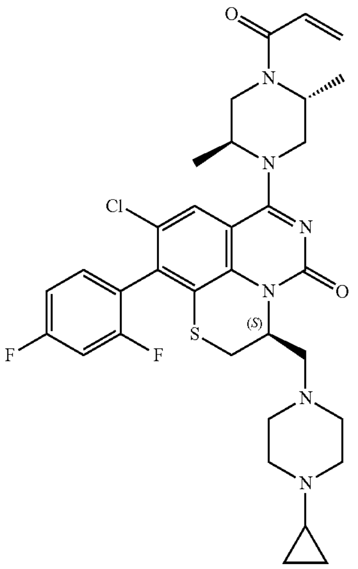 | $^1$H NMR (400 MHz, $CDCl_3$) δ 7.53 (s, 1H), 7.22 (q, J = 8.0 Hz, 1H), 7.07-6.95 (m, 2H), 6.66-6.50 (m, 1H), 6.37 (t, J = 16.8 Hz, 1H), 5.79-5.75 (m, 1H), 5.49-5.38 (m, 1H), 4.99-4.72 (m, 1.5H), 4.40-4.22 (m, 1.5H), 4.01-3.99 (m, 0.5H), 3.82-3.65 (m, 2.5H), 3.37-3.28 (m, 1H), 3.06-3.03 (m, 1H), 2.95-2.45 (m, 10H), 1.47-1.30 (m, 7H), 0.84-0.15 (m, 4H). | 655.3 |
| 552 | (3S,10R)-7-((S)-4-acryloyl-2-methylpiperazin-1-yl)-10-(5-chloro-2,4-difluorophenyl)-3-((methoxymethoxy)methyl)-9-(trifluoromethyl)-2,3-dihydro-5H-[1,4]thiazino[2,3,4-ij]quinazolin-5-one | 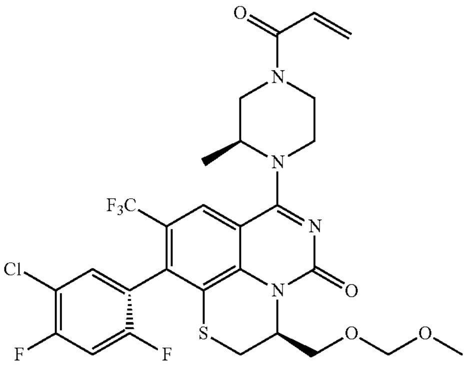 | $^1$H NMR (400 MHz, $CDCl_3$) δ 7.78 (m, 1H), 7.31-7.24 (m, 1H), 7.08 (t, J = 8.8 Hz, 1H), 6.67-6.50 (m, 1H), 6.38 (dd, J = 16.8 Hz, 2.0 Hz, 1H), 5.79 (d, J = 10.0 Hz, 1H), 5.50-5.38 (m, 1H), 4.80-4.62 (m, 3H), 4.59-4.29 (m, 2H), 4.06-3.92 (m, 0.5H), 3.89-3.75 (m, 2.5H), 3.67-3.47 (m, 1.5H), 3.46-3.32 (m, 4.5H), 3.15-2.97 (m, 2H), 1.58-1.46 (m, 3H). | 645.2 |
| 553 | (3S,10S)-7-((S)-4-acryloyl-2-methylpiperazin-1-yl)-10-(5-chloro-2,4-difluorophenyl)-3-((methoxymethoxy)methyl)-9-(trifluoromethyl)-2H-[1,4]thiazino[2,3,4-ij]quinazolin-5(3H)-one | 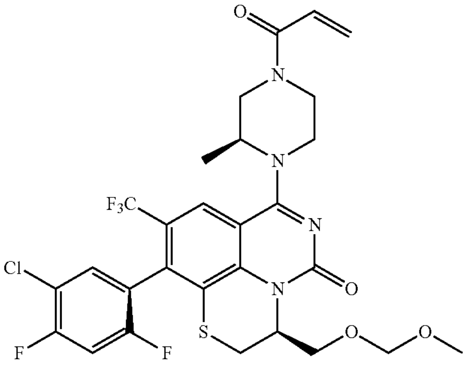 | $^1$H NMR (400 MHz, $CDCl_3$) δ 7.78 (m, 1H), 7.30-7.24 (m, 1H), 7.07 (td, J = 8.8 Hz, 2 Hz, 1H), 6.67-6.50 (m, 1H), 6.38 (d, J = 16.8 Hz, 1H), 5.79 (d, J = 10.4 Hz, 1H), 5.51-5.40 (m, 1H), 4.78-4.60 (m, 3H), 4.59-4.26 (m, 2H), 4.04-3.92 (m, 0.5H), 3.88-3.74 (m, 2.5H), 3.67-3.47 (m, 1.5H), 3.46-3.32 (m, 4.5H), 3.15-2.97 (m, 2H), 1.58-1.45 (m, 3H). | 645.2 |

TABLE 7-continued

Table of Thiomorpholines

| Ex. # | Name | Structure | $^1$H NMR | MS $(M + H)^+$ |
|---|---|---|---|---|
| 554 | (3S,10S)-7-((2S,5R)-4-acryloyl-2,5-dimethylpiperazin-1-yl)-10-(5-chloro-2,4-difluorophenyl)-3-((2-methoxyethoxy)methyl)-9-(trifluoromethyl)-2H-[1,4]thiazino[2,3,4-ij]quinazolin-5(3H)-one | 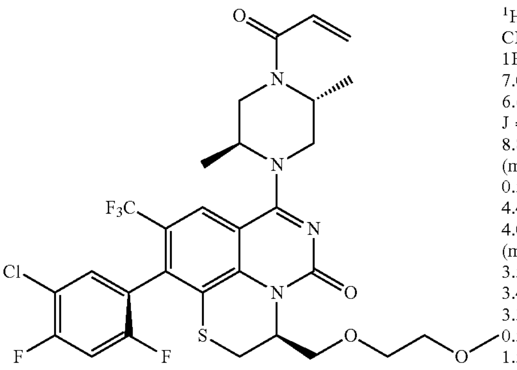 | $^1$H NMR (400 MHz, $CDCl_3$) δ 7.86-7.83 (m, 1H), 7.23-7.21 (m, 1H), 7.06 (t, J = 4.8 Hz, 1H), 6.67-6.51 (m, 1H), 6.38 (t, J = 14.4 Hz, 1H), 5.78 (t, J = 8.8 Hz, 1H), 5.48-5.40 (m, 1H), 5.10-5.02 (m, 0.5H), 4.77-4.65 (m, 1H), 4.44-4.34 (m, 1.5H), 4.11-4.07 (m, 0.5H), 3.76-3.70 (m, 4H), 3.68-3.61 (m, 2H), 3.52 (t, J = 4.8 Hz, 2H), 3.42 (d, J = 12.8 Hz, 1H), 3.36 (s, 3H), 3.24-3.21 (m, 0.5H), 3.04-3.00 (m, 1H), 1.50-1.42 (m, 6H). | 673.2 |
| 555 | (3S,10R)-7-((2S,5R)-4-acryloyl-2,5-dimethylpiperazin-1-yl)-10-(5-chloro-2,4-difluorophenyl)-3-((2-methoxyethoxy)methyl)-9-(trifluoromethyl)-2,3-dihydro-5H-[1,4]thiazino[2,3,4-ij]quinazolin-5-one | 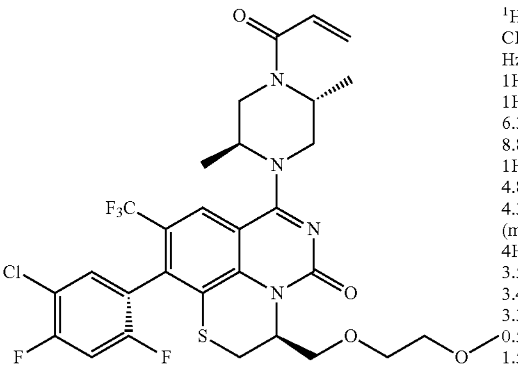 | $^1$H NMR (400 MHz, $CDCl_3$) δ 7.844 (d, J = 8.4 Hz, 1H), 7.293-7.27 (m, 1H), 7.07 (t, J = 4.8 Hz, 1H), 6.67-6.50 (m, 1H), 6.37 (m, 1H), 5.78 (t, J = 8.8 Hz, 1H), 5.48-5.40 (m, 1H), 5.11-5.00 (m, 0.5H), 4.81-4.77 (m, 1H), 4.44-4.31 (m, 1.5H), 4.13- 4.09 (m, 0.5H), 3.78-3.61 (m, 4H), 3.68-3.61 (m, 2H), 3.53 (t, J = 4.8 Hz, 2H), 3.43 (d, J = 13.6 Hz, 1H), 3.36 (s, 3H), 3.26-3.21 (m, 0.5H), 3.05-3.01 (m, 1H), 1.50-1.42 (m, 6H). | 673.2 |
| 556 | (3S,10R)-7-((2S,5R)-4-acryloyl-2,5-dimethylpiperazin-1-yl)-10-(5-chloro-2,4-difluorophenyl)-3-((4-(2,2-difluoroethyl)piperazin-1-yl)methyl)-9-(trifluoromethyl)-2H-[1,4]thiazino[2,3,4-ij]quinazolin-5(3H)-one | 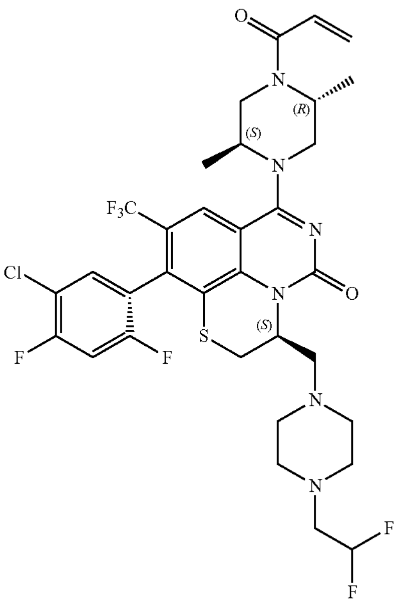 | $^1$H NMR (400 MHz, $CDCl_3$) δ 7.87(s, 1H), 7.10 (t, J = 11.6 Hz, 1H), 6.71-6.53 (m, 1H), 6.46-6.37 (m, 1H), 6.10-5.69 (m, 1H), 5.85-5.79 (m, 1H), 5.49-5.39 (m, 1H), 5.14-4.69 (m, 2H), 4.48-4.37 (m, 1H), 4.17-4.08 (m, 1H), 3.80-3.65 (m, 3H), 3.46-3.26 (m, 2H), 3.11-3.00 (m, 2H), 2.80-2.56 (m, 10H), 1.51-1.40 (m, 6H). | 747.3 |

TABLE 7-continued

| Table of Thiomorpholines | | | | |
|---|---|---|---|---|
| Ex. # | Name | Structure | $^1H$ NMR | MS (M + H)$^+$ |
| 557 | (3S,10S)-7-((2S,5R)-4-acryloyl-2,5-dimethylpiperazin-1-yl)-10-(5-chloro-2,4-difluorophenyl)-3-((4-(2,2-difluoroethyl)piperazin-1-yl)methyl)-9-(trifluoromethyl)-2H-[1,4]thiazino[2,3,4-ij]quinazolin-5(3H)-one | 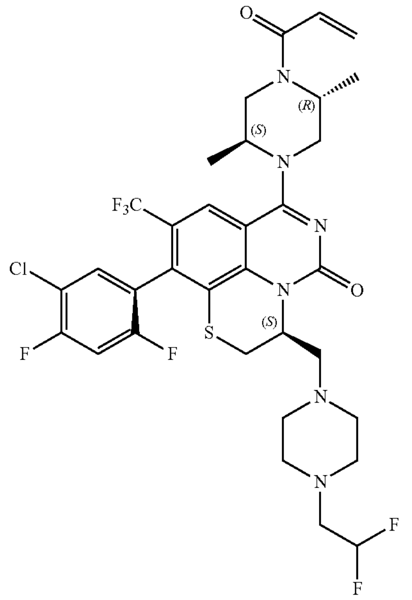 | $^1H$ NMR (400 MHz, $CDCl_3$) δ 7.90 (s, 1H), 7.14 (t, J = 12.0 Hz, 1H), 6.68-6.49 (m, 1H), 6.42-6.33 (m, 1H), 6.07-5.65 (m, 1H), 5.81-5.76 (m, 1H), 5.42-5.32 (m, 1H), 5.09-4.64 (m, 2H), 4.45-4.40 (m, 1H), 4.11-4.01 (m, 1H), 3.78-3.63(m, 3H), 3.43-3.24(m, 2H), 3.11-2.99(m, 2H), 2.78-2.54 (m, 10H), 1.51-1.45 (m, 6H). | 747.3 |
| 558 | (S)-7-((2S,5R)-4-acryloyl-2,5-dimethylpiperazin-1-yl)-9-chloro-10-(4-fluorophenyl)-3-((2-methoxyethoxy)methyl)-2H-[1,4]thiazino[2,3,4-ij]quinazolin-5(3H)-one | 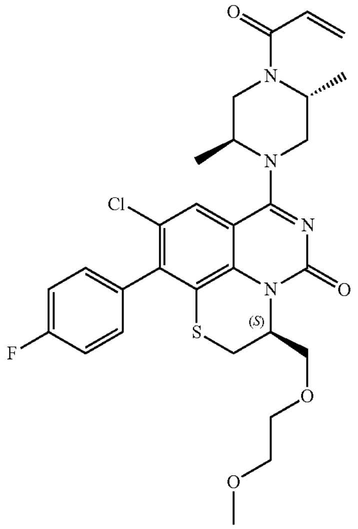 | $^1H$ NMR (400 MHz, $CDCl_3$) δ 7.56-7.53 (m, 1H), 7.24-7.17 (m, 4H), 6.67-6.50 (m, 1H), 6.41-6.33 (m, 1H), 5.80-5.75 (m, 1H), 5.50-5.45 (m, 1H), 5.04-4.98 (m, 0.5H), 4.86-4.68 (m, 1H), 4.41-4.33 (m, 1.5H), 4.08-4.03 (m, 0.5H), 3.83-3.64 (m, 6.5H), 3.54-3.51 (m, 2H), 3.36-3.19 (m, 4H), 3.01-2.97 (m, 1H), 1.44-1.36 (m, 6H). | 587.2 |
| 559 | (3S)-7-((3S,5R)-4-acryloyl-3,5-dimethylpiperazin-1-yl)-10-(5-chloro-2,4-difluorophenyl)-3-(methoxymethyl)-9-(trifluoromethyl)-2H-[1,4]thiazino[2,3,4-ij]quinazolin-5(3H)-one | 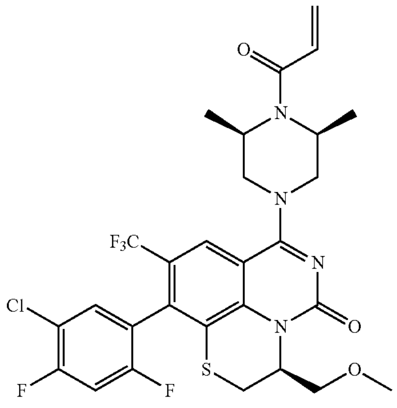 [SMILES: C=CC(=O)N1[C@H](C)CN(c2nc(=O)n3c4c(c(-c5cc(Cl)c(F)cc5F)c(C(F)(F)F)cc24)SC[C@@H]3COC)C[C@@H]1C] | $^1H$ NMR (400 MHz, $CDCl_3$) δ 8.06 (s, 1H), 7.28-7.24 (m, 1H), 7.09-7.04 (m, 1H), 6.65-6.59 (m, 1H), 6.40 (dd, J = 1.6 Hz, 16.8 Hz, 1H), 5.77 (dd, J = 1.6 Hz, 10.8 Hz, 1H), 5.50-5.43 (m, 1H), 4.75-4.59 (m, 2H), 4.21-4.15 (m, 2H), 3.67-3.62 (m, 2H), 3.41-3.30 (m, 6H), 3.05-3.01 (m, 1H), 1.62-1.61 (m, 3H), 1.49 (d, J = 7.2 Hz, 3H). | 629.1 |

TABLE 7-continued

| Table of Thiomorpholines | | | | |
|---|---|---|---|---|
| Ex. # | Name | Structure | $^1$H NMR | MS (M + H)$^+$ |
| 560 | (3S)-3-((1S,4S)-2-oxa-5-azabicyclo[2.2.1]heptan-5-ylmethyl)-7-((3S,5R)-4-acryloyl-3,5-dimethylpiperazin-1-yl)-10-(2,4-difluorophenyl)-9-(trifluoromethyl)-2H-[1,4]thiazino[2,3,4-ij]quinazolin-5(3H)-one | 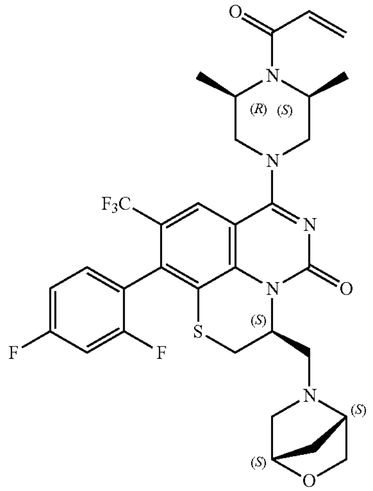 | $^1$H NMR (400 MHz, $CDCl_3$) δ 8.07 (s, 1H), 7.21-7.14 (m, 1H), 7.06-6.93 (m, 2H), 6.66-6.59 (m, 1H), 6.43-6.38 (m, 1H), 5.77 (d, J = 12.0 Hz, 1H), 5.28-5.24 (m, 1H), 4.74-4.60 (m, 2H), 4.43-4.37 (m, 1H), 4.19 (d, J = 13.6 Hz, 2H), 3.91-3.84 (m, 1H), 3.69-3.31 (m, 5.5H), 2.99-2.85 (m, 4.5H), 1.75-1.66 (m, 2H), 1.60-1.58 (m, 3H), 1.49-1.41 (m, 3H). | 662.3 |
| 561 | 2-(4-(((3S)-7-((2S,5R)-4-acryloyl-2,5-dimethylpiperazin-1-yl)-10-(2,4-difluorophenyl)-5-oxo-9-(trifluoromethyl)-3,5-dihydro-2H-[1,4]thiazino[2,3,4-ij]quinazolin-3-yl)methyl)piperazin-1-yl)acetonitrile | 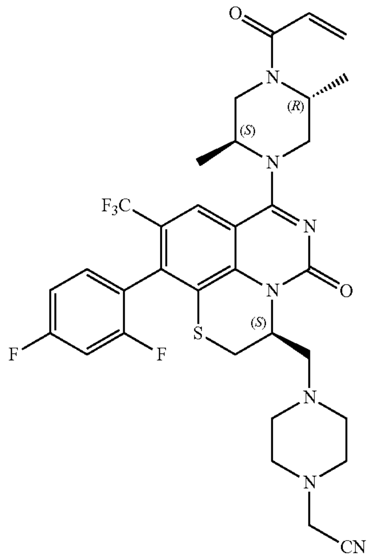 | $^1$H NMR (400 MHz, $CDCl_3$) δ 7.51 (d, J = 2.0 Hz, 1H), 7.24-7.18 (m, 1H), 7.06-6.96 (m, 2H), 5.50-5.43 (m, 1H), 4.63-4.54 (m, 1H), 4.18-4.12 (m, 1H), 3.59-3.47 (m, 1H), 3.14-2.84 (m, 8H), 2.40-2.34 (m, 2H), 1.95-1.69 (m, 7H), 1.52(dd, J = 1.6 Hz, 1.6 Hz, 3H), 1.44-1.31 (m, 3H), 1.08-1.04 (m, 3H). | 688.3 |

TABLE 7-continued

Table of Thiomorpholines

| Ex. # | Name | Structure | $^1H$ NMR | MS $(M + H)^+$ |
|---|---|---|---|---|
| 562 | (3S)-7-((2S,5R)-4-acryloyl-2,5-dimethylpiperazin-1-yl)-3-((4-(2,2-difluoroethyl)piperazin-1-yl)methyl)-10-(2,4-difluorophenyl)-9-(trifluoromethyl)-2H-[1,4]thiazino[2,3,4-ij]quinazolin-5(3H)-one | 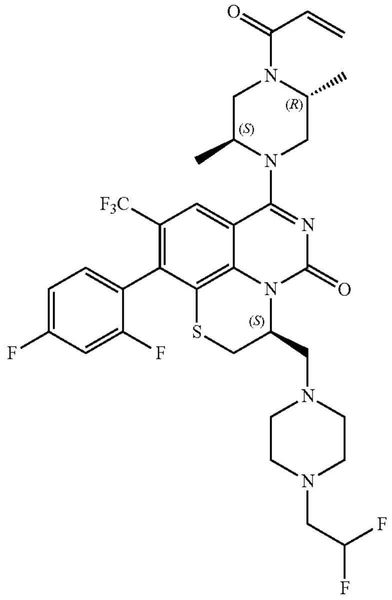 | $^1H$ NMR (400 MHz, $CDCl_3$) δ 7.87 (s, 1H), 7.26-7.17 (m, 1H), 7.10-6.98 (m, 2H), 6.76-6.54 (m, 1H), 6.46-6.38 (m, 1H), 6.11-5.70 (m, 1H), 5.85-5.79 (m, 1H), 5.47-5.35 (m, 1H), 5.13-5.07 (m, 0.5H), 4.85-4.70 (m, 1H), 4.48-4.37 (m, 1.5H), 4.19-4.05 (m, 1H), 3.79-3.64 (m, 2H), 3.44-5.28 (m, 2H), 3.11-3.02 (m, 1H), 2.79-2.53 (m, 11H), 1.51-1.42 (m, 6H). | 713.3 |
| 563 | (3S,10R)-7-((3S,5R)-4-acryloyl-3,5-dimethylpiperazin-1-yl)-10-(5-chloro-2,4-difluorophenyl)-3-(methoxymethyl)-9-(trifluoromethyl)-2,3-dihydro-5H-[1,4]thiazino[2,3,4-ij]quinazolin-5-one | 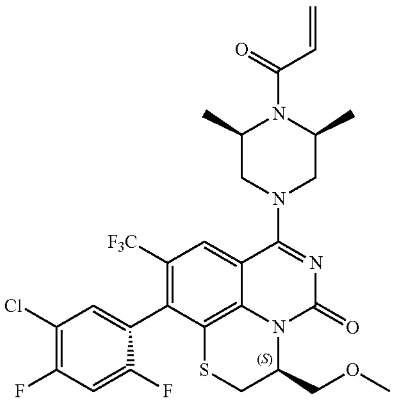 | $^1H$ NMR (400 MHz, $CDCl_3$) δ 8.06 (s, 1H), 7.28-7.24 (m, 1H), 7.07 (t, J = 8.8 Hz, 1H), 6.65-6.59 (m, 1H), 6.40 (dd, J = 1.6 Hz, 16.8 Hz, 1H), 5.77 (dd, J = 1.2 Hz, 10.0 Hz, 1H), 5.45-5.44 (m, 1H), 4.73-4.58 (m, 2H), 4.21-4.15 (m, 2H), 3.67-3.64 (m, 2H), 3.41-3.31 (m, 6H), 3.05-3.01 (m, 1H), 1.61 (m, J = 6.8 Hz, 3H), 1.47 (d J = 6.8 Hz, 3H). | 629.2 |
| 564 | (3S,10S)-7-((3S,5R)-4-acryloyl-3,5-dimethylpiperazin-1-yl)-10-(5-chloro-2,4-difluorophenyl)-3-(methoxymethyl)-9-(trifluoromethyl)-2,3-dihydro-5H-[1,4]thiazino[2,3,4-ij]quinazolin-5-one | 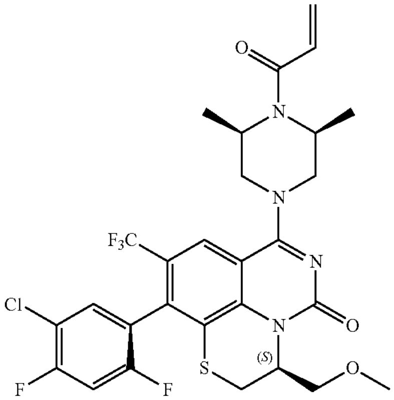 | $^1H$ NMR (400 MHz, $CDCl_3$) δ 8.07 (s, 1H), 7.28-7.25 (m, 1H), 7.07 (t, J = 8.8 Hz, 1H), 6.65-6.59 (m, 1H), 6.40 (dd, J = 1.6 Hz, 16.4 Hz, 1H), 5.77 (dd, J = 1.6 Hz, 10.4 Hz, 1H), 5.48-5.45 (m, 1H), 4.76-4.59 (m, 2H), 4.21-4.16 (m, 2H), 3.68-3.59 (m, 2H), 3.39-3.30 (m, 6H), 3.04-3.00 (m, 1H), 1.61-1.59 (m, 3H), 1.46 (d, J = 6.4 Hz, 3H). | 629.2 |

TABLE 7-continued

| Ex. # | Name | Structure | $^1H$ NMR | MS $(M + H)^+$ |
|---|---|---|---|---|
| | | Table of Thiomorpholines | | |
| 565 | (3S,10S)-3-((2-oxa-7-azaspiro[3.5]nonan-7-yl)methyl)-7-((3S,5R)-4-acryloyl-3,5-dimethylpiperazin-1-yl)-10-(5-chloro-2,4-difluorophenyl)-9-(trifluoromethyl)-2,3-dihydro-5H-[1,4]thiazino[2,3,4-ij]quinazolin-5-one | 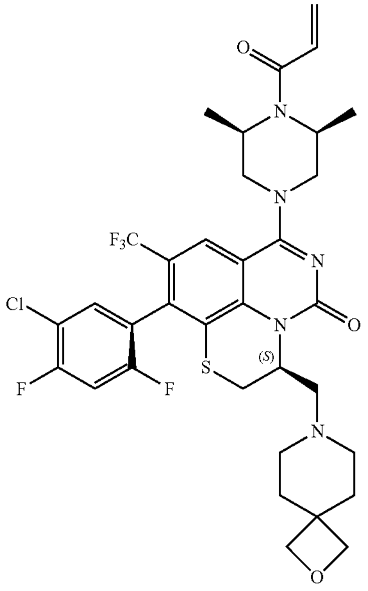 | $^1H$ NMR (400 MHz, $CDCl_3$) δ 8.06 (s, 1H), 7.28-7.27 (m, 1H), 7.07 (t, J = 8.4 Hz, 1H), 6.65-6.58 (m, 1H), 6.43-6.38 (dd, J = 1.6 Hz, 16.8 Hz, 1H), 5.79-5.76 (dd, J = 1.6 Hz, 10.4 Hz, 1H), 5.34-5.29 (m, 1H), 4.67-4.65 (m, 2H), 4.39-4.37 (m, 4H), 4.20-4.15 (m, 2H), 3.47-3.06 (m, 3H), 3.01-2.97 (m, 1H), 2.74-2.58 (m, 3H), 2.54-2.29 (m, 3H), 1.83-1.81 (m, 4H), 1.61-1.59 (m, 3H), 1.48-1.46 (m, 3H). | 724.2 |
| 566 | (3S,10R)-3-((2-oxa-7-azaspiro[3.5]nonan-7-yl)methyl)-7-((3S,5R)-4-acryloyl-3,5-dimethylpiperazin-1-yl)-10-(5-chloro-2,4-difluorophenyl)-9-(trifluoromethyl)-2,3-dihydro-5H-[1,4]thiazino[2,3,4-ij]quinazolin-5-one | 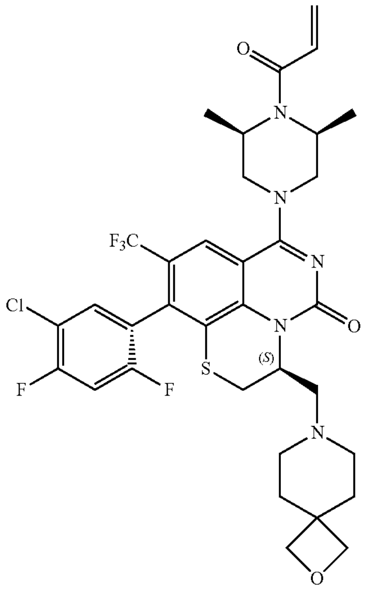 | $^1H$ NMR (400 MHz, $CDCl_3$) δ 8.06 (s, 1H), 7.28-7.27 (m, 1H), 7.07 (t, J = 8.8 Hz, 1H), 6.65-6.58 (m, 1H), 6.43-6.38 (dd, J = 1.6 Hz, 16.4 Hz, 1H), 5.78-5.76 (dd, J = 1.6 Hz, 10.4 Hz, 1H), 5.33-5.32 (m, 1H), 4.67-4.60 (m, 2H), 4.39-4.37 (m, 4H), 4.19-4.16 (m, 2H), 3.46-3.30 (m, 3H), 3.01-2.98 (m, 1H), 2.77-2.60 (m, 3H), 2.46-2.35 (m, 3H), 1.84-1.82 (m, 4H), 1.61-1.59 (m, 3H), 1.49-1.48 (m, 3H). | 724.2 |
| 567 | (3S)-7-((3S,5R)-4-acryloyl-3,5-dimethylpiperazin-1-yl)-10-(5-chloro-2,4-difluorophenyl)-3-((methoxymethoxy)methyl)-9-(trifluoromethyl)-2H-[1,4]thiazino[2,3,4-ij]quinazolin-5(3H)-one | 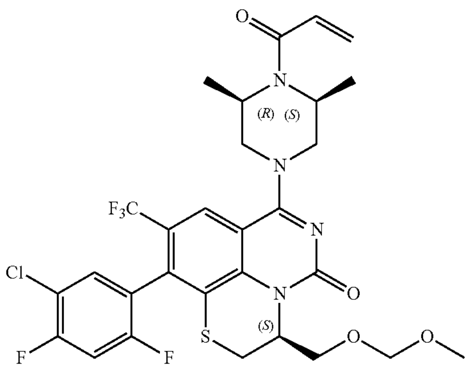 | $^1H$ NMR (400 MHz, $CDCl_3$) δ 8.06 (s, 1H), 7.29-7.27 (m, 1H), 7.10-7.04 (m, 1H), 6.65-6.59 (m, 1H), 6.42 (dd, J = 1.6 Hz, 16.4 Hz, 1H), 5.78 (dd, J = 1.6 Hz, 10.4 Hz, 1H), 5.50-5.46 (m, 1H), 4.68-4.62 (m, 4H), 4.214.17 (m, 2H), 3.80-3.76 (m, 2H), 3.42-3.32 (m, 6H), 3.09-3.04 (m, 1H), 1.59 (d, J = 2.8 Hz, 3H), 1.49-1.46 (m, 3H). | 659.3 |

TABLE 7-continued

| Ex. # | Name | Structure | $^1$H NMR | MS (M + H)$^+$ |
|---|---|---|---|---|
| | Table of Thiomorpholines | | | |
| 568 | (3S)-7-((3S,5R)-4-acryloyl-3,5-dimethylpiperazin-1-yl)-10-(5-chloro-2,4-difluorophenyl)-3-(hydroxymethyl)-9-(trifluoromethyl)-2H-[1,4]thiazino[2,3,4-ij]quinazolin-5(3H)-one | 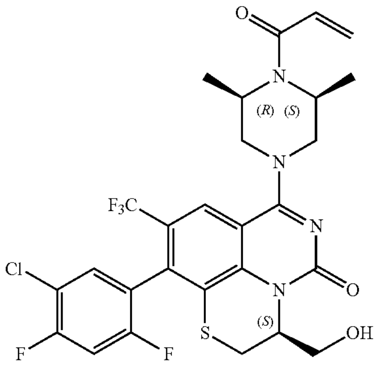 | $^1$H NMR (400 MHz, $CDCl_3$) δ 8.08 (s, 1H), 7.26-7.23 (m, 1H), 7.10-7.04 (m, 1H), 6.65-6.58 (m, 1H), 6.43 (dd, J = 1.2 Hz, 16.8 Hz, 1H), 5.79-5.76 (m, 1H), 5.37-5.34 (m, 1H), 4.73-4.61 (m, 2H), 4.23-4.20 (m, 2H), 4.00-3.87 (m, 2H), 3.45-3.31 (m, 3H), 3.09-3.05 (m, 1H), 1.80-1.73 (m, 1H), 1.63 (d, J = 7.2 Hz, 3H), 1.46-1.43 (m, 3H). | 615.3 |
| 569 | (3S,10R)-7-((2S,5R)-4-acryloyl-2,5-dimethylpiperazin-1-yl)-9-chloro-3-((4-(2,2-difluoroethyl)piperazin-1-yl)methyl)-10-(1-methyl-1H-indazol-7-yl)-2,3-dihydro-5H-[1,4]thiazino[2,3,4-ij]quinazolin-5-one | 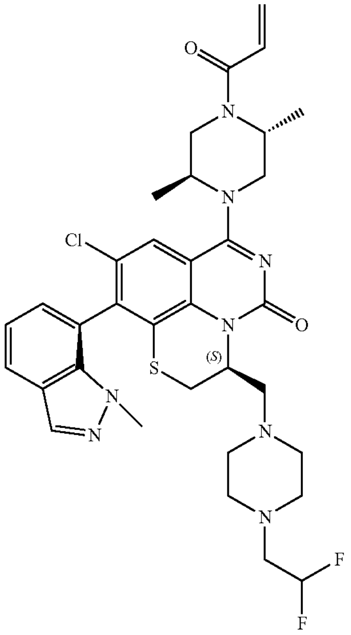 | $^1$H NMR (400 MHz, $CDCl_3$) δ 8.06 (s, 1H), 7.86 (d, J = 8.0 Hz, 1H), 7.62 (d, J = 12.8 Hz, 1H), 7.30-7.28 (m, 1H),7.15 (d, J = 6.8 Hz, 1H), 6.75-6.51 (m, 1H), 6.38 (t, J = 14.0 Hz, 1H), 5.99-5.69 (m, 2H), 5.37-5.33 (m, 1H), 5.07 (m, 0.5H), 4.82-4.70 (m, 1H), 4.45-4.35 (m, 1.5H), 4.15 (m, 0.5H), 3.78-3.61 (m, 5.5H), 3.33-3.24 (m, 2H), 3.07-3.05 (m, 1H), 2.73-2.51 (m, 11H), 1.50-1.43 (m, 6H). | 697.3 |

TABLE 7-continued

Table of Thiomorpholines

| Ex. # | Name | Structure | $^1$H NMR | MS (M + H)$^+$ |
|---|---|---|---|---|
| 570 | (3S,10S)-7-((2S,5R)-4-acryloyl-2,5-dimethylpiperazin-1-yl)-9-chloro-3-((4-(2,2-difluoroethyl)piperazin-1-yl)methyl)-10-(1-methyl-1H-indazol-7-yl)-2,3-dihydro-5H-[1,4]thiazino[2,3,4-ij]quinazolin-5-one | 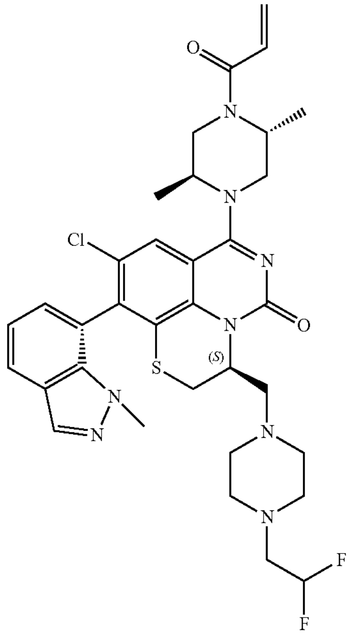 | $^1$H NMR (400 MHz, $CDCl_3$) δ 8.06 (s, 1H), 7.86 (d, J = 8.0 Hz, 1H), 7.59 (m, 1H), 7.24-7.22 (m, 1H), 7.12 (d, J = 6.8 Hz, 1H), 6.67-6.51 (m, 1H), 6.38 (t, J = 15.6 Hz, 1H), 5.99-5.71 (m, 2H), 5.51-5.45 (m, 1H), 5.01-4.77 (m, 1.5H), 4.42-4.35 (m, 1H), 3.84-3.62 (m, 6H), 3.42-3.23 (m, 2.5H), 3.01 (m, 2H), 2.73-2.56 (m, 10H), 1.42-1.32 (m, 6H). | 697.3 |
| 571 | (3S)-7-(9-acryloyl-7-oxo-3,9-diazabicyclo[3.3.1]nonan-3-yl)-10-(2,4-difluorophenyl)-3-(methoxymethyl)-9-(trifluoromethyl)-2H-[1,4]thiazino[2,3,4-ij]quinazolin-5(3H)-one | 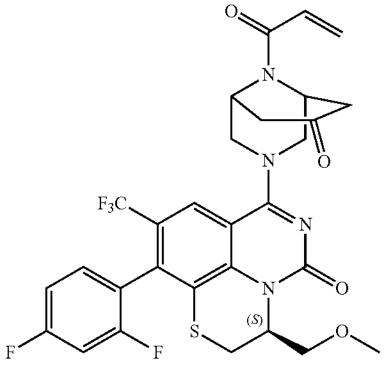 | $^1$H NMR (400 MHz, $CDCl_3$) δ 7.85 (s, 1H), 7.19-7.13 (m, 1H), 7.05-6.94 (m, 2H), 6.72-6.64 (m, 1H), 6.49-6.45 (m, 1H), 5.90 (d, J = 10.4 Hz, 1H), 5.50-5.36 (m, 2H), 4.78-4.73 (m, 1H), 4.26-4.14 (m, 2H), 3.67-3.57 (m, 2H), 3.36-3.22 (m, 6H), 3.04-2.98 (m, 1H), 2.90-2.75 (m, 3H), 2.67-2.57 (m, 1H). | 621.2 |
| 572 | (3S)-7-(4-acryloylpiperazin-1-yl)-10-(5-chloro-2,4-difluorophenyl)-3-(methoxymethyl)-9-(trifluoromethyl)-2H-[1,4]thiazino[2,3,4-ij]quinazolin-5(3H)-one | 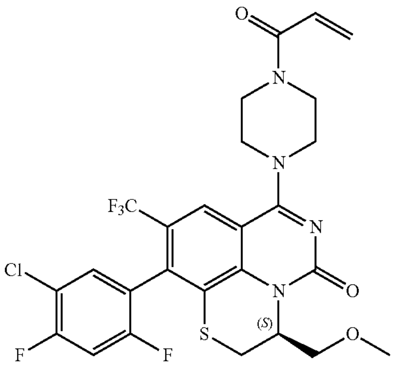 | $^1$H NMR (400 MHz, $CDCl_3$) δ 7.80 (s, 1H), 7.29-7.27 (m, 1H), 7.09-7.05 (m, 1H), 6.62-6.55 (m, 1H), 6.37 (dd, J = 1.6 Hz, 16.8 Hz, 1H), 5.90 (dd, J = 1.2 Hz, 10.4 Hz, 1H), 5.46-5.41 (m, 1H), 3.99-3.91 (m, 3H), 3.80-3.79 (m, 5H), 3.67-3.63 (m, 2H), 3.41-3.36 (m, 4H), 3.04-3.00 (m, 1H). | 601.1 |

TABLE 7-continued

| Table of Thiomorpholines | | | | |
|---|---|---|---|---|
| Ex. # | Name | Structure | $^1$H NMR | MS (M + H)$^+$ |
| 573 | (S)-7-((2S,5R)-4-acryloyl-2,5-dimethylpiperazin-1-yl)-9-chloro-10-(4-fluorophenyl)-3-(methoxymethyl)-2H-[1,4]thiazino[2,3,4-ij]quinazolin-5(3H)-one | 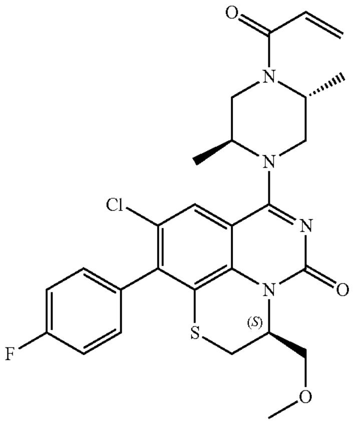 | $^1$H NMR (400 MHz, $CDCl_3$) δ 7.60 (s, 1H), 7.29-7.22 (m, 4H), 6.67-6.58 (m, 1H), 6.45-6.43 (m, 1H), 5.85-5.80 (m, 1H), 5.52-5.50 (m, 1H), 5.07-5.06 (m, 0.5H), 4.91-4.87 (m, 0.5H), 4.78-4.75 (m, 0.5H), 4.41-4.36 (m, 1H), 4.15-4.07 (m, 1H), 3.84-3.77 (m, 2H), 3.74-3.67 (m, 2H), 3.44 (s, 3H), 3.35-3.31(m, 1.5H) , 3.05-3.01 (m, 1H), 1.50-1.40 (m, 6H). | 543.2 |
| 574 | (S)-7-((2S,5R)-4-acryloyl-2,5-dimethylpiperazin-1-yl)-3-((4-(2,2-difluoroethyl)piperazin-1-yl)methyl)-10-(4-fluorophenyl)-9-(trifluoromethyl)-2H-[1,4]thiazino[2,3,4-ij]quinazolin-5(3H)-one | 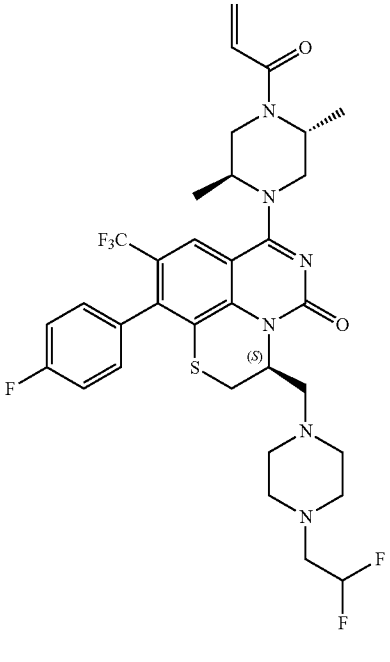 | $^1$H NMR (400 MHz, $CDCl_3$) δ 7.90 (s, 1H), 7.28-7.21 (m, 4H), 6.70-6.40 (m, 2H), 6.12-5.82 (m, 2H), 5.42-5.38 (m, 1H), 5.13-5.10 (m, 0.5H), 4.86-4.73 (m, 1H), 4.50-4.38 (m, 1.5H), 3.77-3.73 (m, 2H), 3.41-3.30 (m, 2H), 3.06-2.97(m, 1H), 2.91-2.80 (m, 4H) , 2.72-2.64 (m, 4H), 1.66-1.65 (m, 3H), 1.56-1.49 (m, 4H), 1.25-1.23 (m, 3H). | 659.3 |

TABLE 7-continued

Table of Thiomorpholines

| Ex. # | Name | Structure | $^1$H NMR | MS $(M + H)^+$ |
|---|---|---|---|---|
| 575 | 2-(4-(((3S)-7-((2S,5R)-4-acryloyl-2,5-dimethylpiperazin-1-yl)-10-(2,4-difluorophenyl)-5-oxo-9-(trifluoromethyl)-3,5-dihydro-2H-[1,4]thiazino[2,3,4-ij]quinazolin-3-yl)methyl)piperazin-1-yl)acetamide | 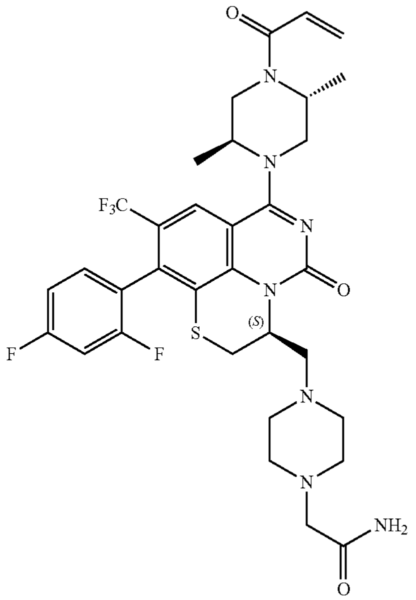 | $^1$H NMR (400 MHz, $CDCl_3$) δ 7.84 (s, 1H), 7.21-7.14 (m, 1H), 7.05-6.94 (m, 2H), 6.66-6.50 (m, 1H), 6.37 (t, J = 14.8 Hz, 1H), 5.78 (t, J = 8.4 Hz, 1H), 5.45-5.27 (m, 2H), 5.05-5.02 (m, 0.5H), 4.78-4.67 (m, 1H), 4.41-4.35 (m, 1.5H), 4.10-4.05 (m, 0.5H), 3.75-3.50 (m, 3H), 3.36-2.95 (m, 5.5H), 2.93-2.50 (m, 9H), 1.49-1.39 (m, 6H). | 706.3 |
| 576 | (3S,10S)-3-(2-oxa-7-azaspiro[3.5]nonan-7-ylmethyl)-7-((3S,5R)-4-acryloyl-3,5-dimethylpiperazin-1-yl)-10-(2,4-difluorophenyl)-9-(trifluoromethyl)-2H-[1,4]thiazino[2,3,4-ij]quinazolin-5(3H)-one | 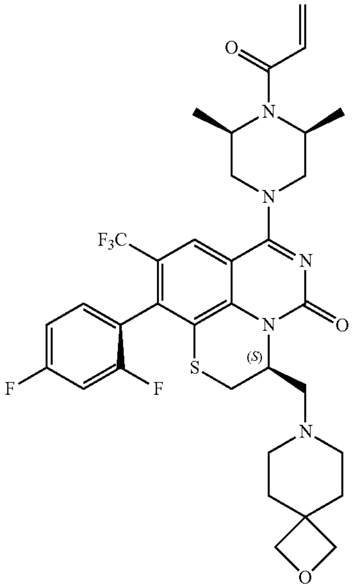 | $^1$H NMR (400 MHz, $CDCl_3$) δ 8.06 (s, 1H), 7.18 (q, J = 8.4 Hz, 1H), 7.06-6.94 (m, 2H), 6.65-6.59 (m, 1H), 6.40 (dd, J = 16.8 Hz, 2.0 Hz, 1H), 5.77 (dd, J = 10.4 Hz, 1.6 Hz, 1H), 5.37-5.35 (m, 1H), 4.72-4.65 (m, 2H), 4.46-4.32 (m, 4H), 4.20-4.17 (m, 2H), 3.48-3.30 (m, 3H), 3.00-2.96 (m, 1H), 2.76-2.66 (m, 1H), 2.65-2.51 (m, 2H), 2.47-2.28 (m, 3H), 1.82-1.81 (m, 4H), 1.61-1.60 (m, 3H), 1.48 (d, J = 6.4 Hz, 3H). | 690.2 |

TABLE 7-continued

| Table of Thiomorpholines | | | | |
|---|---|---|---|---|
| Ex. # | Name | Structure | $^1$H NMR | MS (M + H)$^+$ |
| 577 | (3S)-3-(2-oxa-7-azaspiro[3.5]nonan-7-ylmethyl)-7-((3S,5R)-4-acryloyl-3,5-dimethylpiperazin-1-yl)-10-(2,4-difluorophenyl)-9-(trifluoromethyl)-2H-[1,4]thiazino[2,3,4-ij]quinazolin-5(3H)-one | 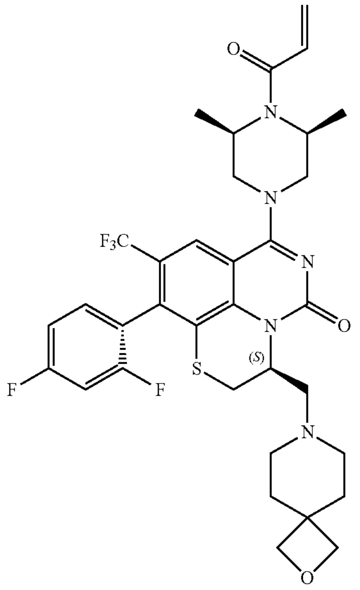 | $^1$H NMR (400 MHz, $CDCl_3$) δ 8.06 (s, 1H), 7.17 (q, J = 8.0 Hz, 1H), 7.04-6.95 (m, 2H), 6.65-6.59 (m, 1H), 6.42-6.38 (m, 1H), 5.78-5.76 (dd, J = 10.4 Hz, 1.6 Hz, 1H), 5.32-5.31 (m, 1H), 4.66-4.57 (m, 2H), 4.44-4.32 (m, 4H), 4.20-4.16 (m, 2H), 3.44-3.30 (m, 3H), 3.07-2.98 (m, 1H), 2.76-2.71 (m, 1H), 2.68-2.52 (m, 2H), 2.49-2.27 (m, 3H), 1.80-1.71 (m, 4H), 1.62-1.60 (m, 3H), 1.49-1.42 (m, 3H). | 690.3 |
| 578 | (3S,10R)-7-(4-acryloylpiperazin-1-yl)-10-(2,4-difluorophenyl)-3-(methoxymethyl)-9-(trifluoromethyl)-2,3-dihydro-5H-[1,4]thiazino[2,3,4-ij]quinazolin-5-one | 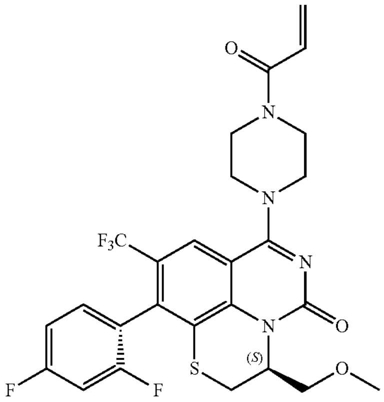 | $^1$H NMR (400 MHz, $CDCl_3$) δ 7.80 (s, 1H),7.18 (q, J = 8.0 Hz, 1H), 7.04-6.95 (m, 2H), 6.59 (dd, J = 10.8 Hz, 16.8 Hz, 1H), 6.37 (d, J = 15.6 Hz, 1H), 5.78 (dd, J = 1.2 Hz, 10.0 Hz, 1H), 5.44-5.39 (m, 1H), 4.01-3.91 (m, 3H), 3.80-3.78 (m, 5H), 3.66-3.64 (m, 2H), 3.39-3.33 (m, 4H), 3.04-3.00 (m, 1H). | 567.2 |
| 579 | (3S,10S)-7-(4-acryloylpiperazin-1-yl)-10-(2,4-difluorophenyl)-3-(methoxymethyl)-9-(trifluoromethyl)-2,3-dihydro-5H-[1,4]thiazino[2,3,4-ij]quinazolin-5-one | 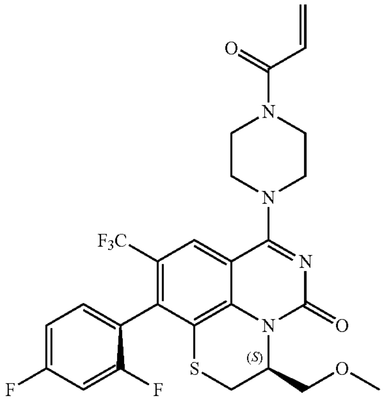 | $^1$H NMR (400 MHz, $CDCl_3$) δ 7.81 (s, 1H), 7.18 (q, J = 6.4 Hz, 1H), 7.05-6.93 (m, 2H), 6.59 (dd, J = 10.4 Hz, 16.8 Hz, 1H), 6.37 (dd, J = 2.0 Hz, 16.8 Hz, 1H), 5.78 (dd, J = 2.0 Hz, 10.4 Hz, 1H), 5.47-5.39 (m, 1H), 4.00-3.92 (m, 3H), 3.81-3.78 (m, 5H), 3.69-3.60 (m, 2H), 3.39 (s, 3H), 3.37-3.33 (m, 1H), 3.04-2.98 (m, 1H). | 567.2 |

TABLE 7-continued

Table of Thiomorpholines

| Ex. # | Name | Structure | $^1$H NMR | MS (M + H)$^+$ |
|---|---|---|---|---|
| 580 | (3S,10S)-7-((2S,5R)-4-acryloyl-2,5-dimethylpiperazin-1-yl)-3-((4-cyclopropylpiperazin-1-yl)methyl)-10-(2,4-difluorophenyl)-9-(trifluoromethyl)-2,3-dihydro-5H-[1,4]thiazino[2,3,4-ij]quinazolin-5-one | 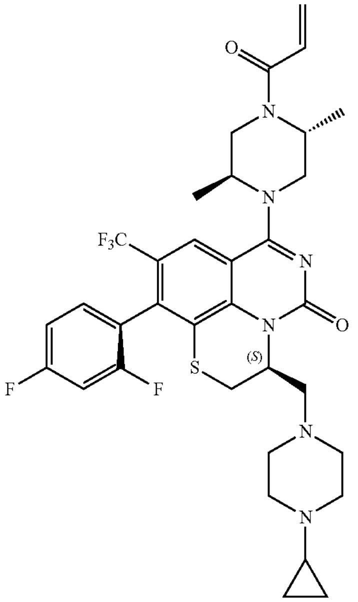 | $^1$H NMR (400 MHz, $CDCl_3$) δ 7.87 (d, J = 6.0, 1H), 7.31-7.27 (m, 1H), 7.16-7.10 (m, 2H), 6.73-6.55 (m, 1H), 6.46-6.37 (m, 1H), 5.84-5.79 (m, 1H), 5.44-5.42 (m, 1H), 5.13-4.70 (m, 1.5H), 4.47-4.36 (m, 1H), 4.11-3.70 (m, 3H), 3.52-3.32 (m, 1.5H), 3.11-3.03 (m, 1H), 2.84-2.55 (m, 10H), 1.52-1.43 (m, 7H), 0.57-0.42 (m, 4H). | 689.3 |
| 581 | (3S,10R)-7-((2S,5R)-4-acryloyl-2,5-dimethylpiperazin-1-yl)-3-((4-cyclopropylpiperazin-1-yl)methyl)-10-(2,4-difluorophenyl)-9-(trifluoromethyl)-2,3-dihydro-5H-[1,4]thiazino[2,3,4-ij]quinazolin-5-one | 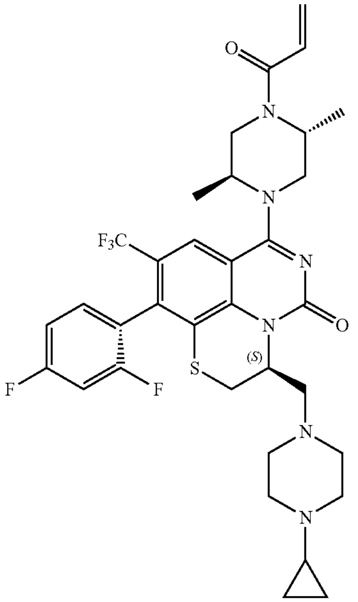 | $^1$H NMR (400 MHz, $CDCl_3$) δ 7.87 (s, 1H), 7.28-7.19 (m, 1H), 7.09-6.98 (m, 2H), 6.72-6.54 (m, 1H), 6.46-6.37 (m, 1H), 5.86-5.79 (m, 1H), 5.42-5.35 (m, 1H), 5.12-4.68 (m, 1.5H), 4.52-4.33 (m, 1H), 4.19-3.67 (m, 3H), 3.51-3.27 (m, 1.5H), 3.10-3.05 (m, 1H), 2.87-2.51 (m, 10H), 1.52-1.29 (m, 7H), 0.59-0.44 (m, 4H). | 689.3 |

TABLE 7-continued

Table of Thiomorpholines

| Ex. # | Name | Structure | $^1$H NMR | MS (M + H)$^+$ |
| --- | --- | --- | --- | --- |
| 587 | (3S)-7-((3S,5R)-4-acryloyl-3,5-dimethylpiperazin-1-yl)-10-(5-chloro-2,4-difluorophenyl)-3-((dimethylamino)methyl)-9-(trifluoromethyl)-2H-[1,4]thiazino[2,3,4-ij]quinazolin-5(3H)-one | 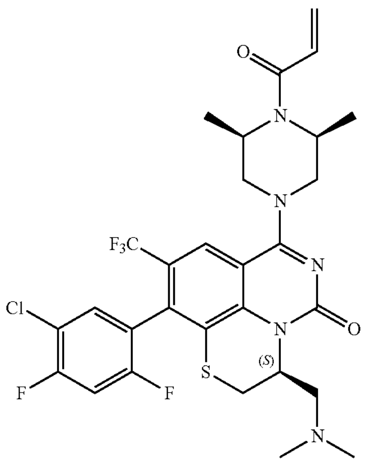 | $^1$H NMR (400 MHz, $CDCl_3$) δ 8.07 (s, 1H), 7.29-7.28 (m, 1H), 7.10-7.04 (m, 1H), 6.66-6.59 (m, 1H), 6.44-6.38 (m, 1H), 5.77 (dd, J = 10.4 Hz, 1.2 Hz, 1H), 5.42-5.36 (m, 1H), 4.68-4.64 (m, 2H), 4.18 (d, J = 13.2 Hz, 2H), 3.55-3.50 (m, 1H), 3.41-3.31 (m, 2H), 3.07-3.00 (m, 1H), 2.91-2.82 (m, 1H), 2.45-2.32 (m, 7H), 1.62-1.59 (m, 3H), 1.50-1.46 (m, 3H). | 642.2 |
| 588 | 8'-((2S,5R)-4-Acryloyl-2,5-dimethylpiperazin-1-yl)-11'-(2,4-difluorophenyl)-10'-(trifluoromethyl)-2'H,4'H,6'H-spiro[oxetane-3,3'-[1,4]thiazepino[2,3,4-ij]quinazolin]-6'-one | 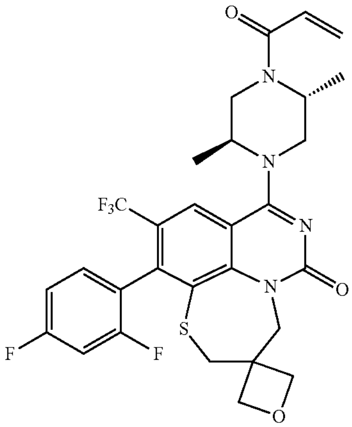 [SMILES: C=CC(=O)N1C[C@H](C)N(c2nc(=O)n3c4c(c(-c5ccc(F)cc5F)c(C(F)(F)F)cc24)SCC2(COC2)C3)C[C@H]1C] | $^1$H NMR (400 MHz, MeOH-$d_4$) δ 7.97 (d, J = 2.7 Hz, 1H), 7.30 (dq, J = 13.7, 7.6 Hz, 1H), 7.11 (t, J = 8.3 Hz, 2H), 6.90-6.72 (m, 1H), 6.28 (ddd, J = 16.7, 5.6, 2.0 Hz, 1H), 5.80 (ddd, J = 9.7, 7.2, 2.0 Hz, 1H), 4.87-4.60 (m, 3H), 4.55-4.36 (m, 3H), 4.34-3.69 (m, 4H), 3.62-3.40 (m, 3H), 1.49-1.25 (m, 6H) | 607.2 |
| 489 | 8'-(4-Acryloylpiperazin-1-yl-2,2,3,3,5,5,6,6-$d_8$)-11'-(2,4-difluorophenyl)-10'-(trifluoromethyl)-2'H,4'H,6'H-spiro[oxetane-3,3'-[1,4]thiazepino[2,3,4-ij]quinazolin]-6'-one | 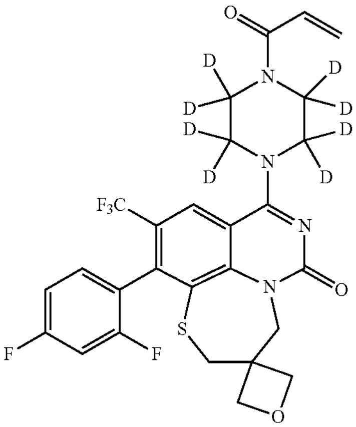 [SMILES: [2H]C1([2H])N(C(=O)C=C)C([2H])([2H])C([2H])([2H])N(c2nc(=O)n3c4c(c(-c5ccc(F)cc5F)c(C(F)(F)F)cc24)SCC2(COC2)C3)C1([2H])[2H]] | $^1$H NMR (400 MHz, MeOH-$d_4$) δ 8.00 (s, 1H), 7.30 (q, J = 7.7 Hz, 1H), 7.11 (t, J = 8.7 Hz, 2H), 6.80 (dd, J = 16.7, 10.6 Hz, 1H), 6.27 (dd, J = 16.7, 1.9 Hz, 1H), 5.80 (dd, J = 10.6, 2.0 Hz, 1H), 4.82-4.54 (m, 2H), 4.43 (d, J = 5.5 Hz, 2H), 3.61-3.46 (m, 2H), 3.23-3.11 (m, 2H) | 587.2 |

Syntheses of Intermediates:

7-chloro-8-iodo-6-(trifluoromethyl)quinazoline-2,4 (1H,3H)-dione

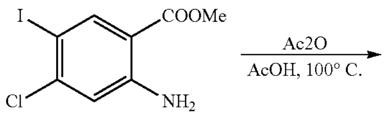

1

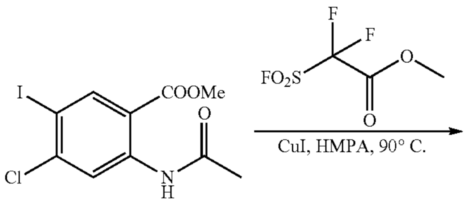

2

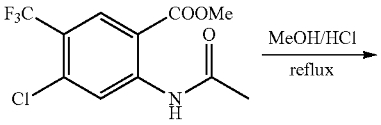

3

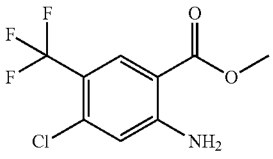

4

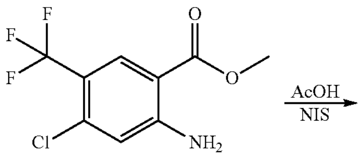

4

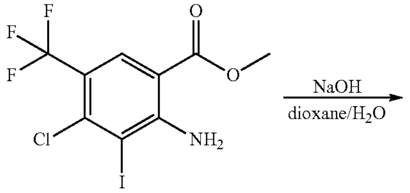

5

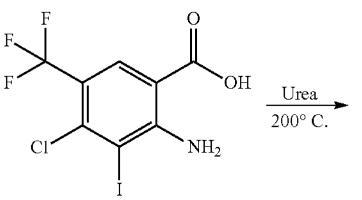

6

-continued

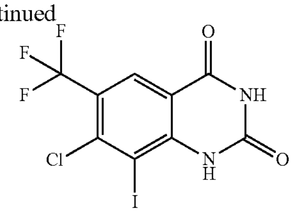

7

Methyl 2-acetamido-4-chloro-5-iodobenzoate (2)

To a mixture of methyl 2-amino-4-chloro-5-iodobenzoate (50.00 g, 160.51 mmol) in AcOH (500 mL) was added $Ac_2O$ (19.66 g, 192.61 mmol). The mixture was stirred at 100° C. for 16 hours. After completion, the mixture was cooled to room temperature, filtered and washed with Petroleum Ether (200 mL) to afford crude product (35 g, 62% yield) as white solid. MS (ESI) m/z: 353.9 $[M+H]^+$.

Methyl 2-acetamido-4-chloro-5-(trifluoromethyl)benzoate (3)

To a mixture of methyl 2-acetamido-4-chloro-5-iodobenzoate (35.00 g, 98.98 mmol) in DMF (350 mL) was added methyl 2,2-difluoro-2-(fluorosulfonyl)acetate (70.09 g, 395.99 mmol), HMPA (70.98 g, 395.99 mmol) and CuI (15.05 g, 79.19 mmol). The mixture was stirred at 90° C. under $N_2$ for 16 hours. After completion, the mixture was poured into water (300 mL), extracted with EtOAc (3×200 mL). The combined organic phase was washed with brine (500 mL) and dried over $Na_2SO_4$. After filtration and concentration, the residue was purified by silica gel column using a gradient of Petrolum Ether/EtOAc (100/1 to 20/1) to afford desired product (25.00 g, 84% yield) as white solid. MS (ESI) m/z: 296.0 $[M+H]^+$.

Methyl 2-amino-4-chloro-5-(trifluoromethyl)benzoate (4)

A mixture of methyl 2-acetamido-4-chloro-5-(trifluoromethyl)benzoate (20.00 g, 67.79 mmol) in HCl/MeOH (200 mL) was stirred at 70° C. for 2 hours. The mixture was concentrated and a saturated aqueous solution of $NaHCO_3$ (100 mL) was added. The resulting mixture was extracted with EtOAc (3×50 mL). The combined organic phase was washed with brine (100 mL) and dried over $Na_2SO_4$. The solvent was removed in vacuo to afford the crude product (18.00 g, crude) as a yellow solid. MS (ESI) m/z: 254.0 $[M+H]^+$ Methyl 2-amino-4-chloro-3-iodo-5-(trifluoromethyl) benzoate (5)

To a mixture of methyl 2-amino-4-chloro-5-(trifluoromethyl)benzoate (28.00 g, 110.23 mmol) in AcOH (280 mL) was added N-Iodosuccinimide (35.00 g, 143.29 mmol). The mixture was stirred at 50° C. for 16 hours. After completion, the mixture was poured into water (400 mL), extracted with EtOAc (3×250 mL). The combined organic phases were washed with brine (400 mL) and dried over $Na_2SO_4$. After filtration and concentration, the residue was washed with PE (200 mL) to afford the crude product (38.00 g, crude) as white solid. MS (ESI) m/z: 379.9 [M+H]$^+$ 2-amino-4-chloro-3-iodo-5-(trifluoromethyl)benzoic acid (6)

To a solution of methyl 2-amino-4-chloro-3-iodo-5-(trifluoromethyl)benzoate (25.00 g, 65.96 mmol) in dioxane (200 mL) and water (200 mL) was added NaOH (5.28 g, 131.92 mmol). The mixture was stirred at 90° C. for 3 hours. After completion, the mixture was poured into water (200 mL). The pH was adjusted to 4~5 and extracted with EtOAc (3×150 mL). The combined organic phase was washed with brine (300 mL) and dried over $Na_2SO_4$. The solvent was removed in vacuum to give 2-amino-4-chloro-3-iodo-5-(trifluoromethyl)benzoic acid (23 g, crude) as yellow solid. MS (ESI) m/z: 365.9 [M+H]$^+$ 7-chloro-8-iodo-6-(trifluoromethyl)quinazoline-2,4(1H,3H)-dione (7)

A mixture of 2-amino-4-chloro-3-iodo-5-(trifluoromethyl)benzoic acid (5 g, 13.71 mmol) and urea (16.45 g, 274.2 mmol) was stirred at 200° C. for 5 hours. After completion, the mixture was cooled to 80° C., water (100 mL) was added to the solution and stirred for 1 hour. The mixture was extracted with EtOAc (3×100 mL). The combined organic phase was washed with brine (100 mL) and dried over $Na_2SO_4$. After filtration and concentration, the residue was purified by silica gel column using a mixture of Petrolum Ether/EtOAc (4/1) to afford the desired product (1.76 g, 33% yield) as a white solid. MS (ESI) m/z: 388.8 [M−H]$^-$ 11'-Chloro-10'-(trifluoromethyl)-2'H,4'H,6'H-spiro[oxetane-3,3'-[1,4]thiazepino[2,3,4-ij]quinazoline]-6',8'(7'H)-dione

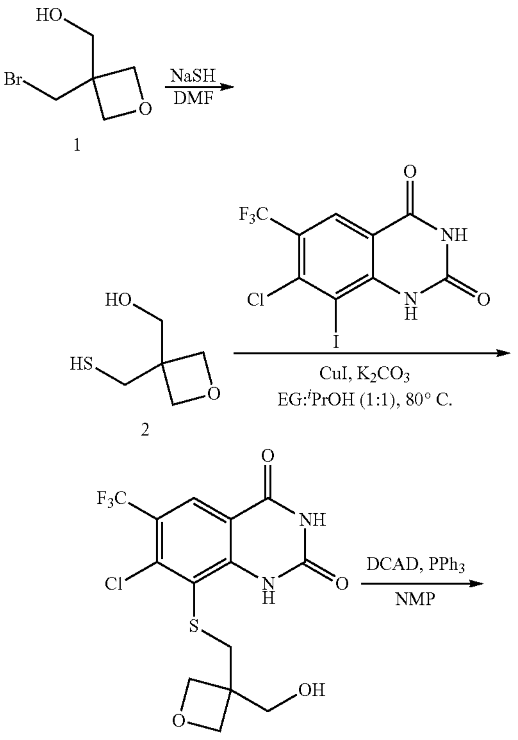

1

2

3

-continued

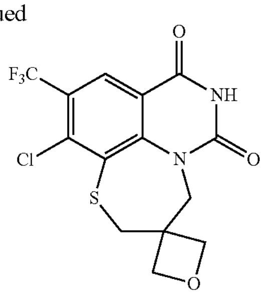

4

[3-(Sulfanylmethyl)oxetan-3-yl]methanol (2)

Sodium hydrosulfide hydrate (0.209 g, 2.82 mmol, 1.1 equiv) was suspended in anhydrous DMF (18 mL) and purged with argon. (3-(bromomethyl)oxetan-3-yl)methanol (0.3 mL, 2.57 mmol, 1.0 equiv) was dissolved in anhydrous DMF (1 mL) in a separated vial and purged with argon. After 15 min, the solution of (3-(bromomethyl)oxetan-3-yl)methanol was added to the sodium hydrosulfide suspension and the sealed vial was stirred at 45° C. for 2 hours under argon. After, the reaction mixture was used in the next step without characterization, work-up and purification (transferred to the vessel via syringe under argon atmosphere).

7-Chloro-8-({[3-(hydroxymethyl)oxetan-3-yl]methyl}sulfanyl)-6-(trifluoromethyl)-1,2,3,4-tetrahydroquinazoline-2,4-dione (3)

To the vial containing 7-chloro-8-iodo-6-(trifluoromethyl)-1,2,3,4-tetrahydroquinazoline-2,4-dione (1.0 g, 2.56 mmol, 1.0 equiv), $K_2CO_3$ (0.708 g, 5.12 mmol, 2.0 equiv) and copper(I) iodide (0.488 g, 2.56 mmol, 1.0 equiv) was added. Solvents, isopropanol (40 mL) and ethylene glycol (40 mL) were added, and the vial was purged with argon for 20 min. Next, crude [3-(sulfanylmethyl)oxetan-3-yl]methanol (0.344 g, 2.56 mmol, 1.0 equiv) was added to the reaction mixture via syringe under argon. The sealed vial was stirred at 80° C. overnight. According to UPLC, 15% of aryl iodide remained. Next, additional freshly prepared [3-(sulfanylmethyl)oxetan-3-yl]methanol (0.138 g, 1.02 mmol, 0.4 equiv) was added. The reaction vial was purged with argon, sealed, and stirred overnight at 80° C. According to UPLC, 6% of aryl iodide remained. Next, the reaction mixture was concentrated, and the obtained oil was suspended in a saturated aqueous $NH_4Cl$ solution then stirred vigorously for 20 min. The $NH_4Cl$ solution was washed with EtOAc (3×100 mL), then the combined organic layers were washed with saturated aqueous $NH_4Cl$ (1×100 mL) and dried over $MgSO_4$. The combined organic layers were concentrated by rotary evaporation. Purification by flash chromatography (Interchim puriFlash® F0120 silica gel column, MeOH/EtOAc=10:90, 60 min) afforded the title compound in poor purity. Re-purification by chromatography (Interchim, puriFlash® F0120 silica gel column) with EtOAc/acetone (1:1, 30 min) afforded the title compound as a white solid (0.535 g, 53% yield): $^1$H NMR (300 MHz, DMSO-$d_6$) δ 11.86 (s, 1H), 10.58 (s, 1H), 8.20 (s, 1H), 5.12 (t, J=5.4 Hz, 1H), 4.31 (s, 4H), 3.71 (d, J=5.1 Hz, 2H), 3.21 (s, 2H); LRMS-ESI (m/z) [M−H]$^-$ calculated for $C_{14}H_{11}ClF_3N_2O_4S$ 395.01, found 395.3.

11'-Chloro-10'-(trifluoromethyl)-2'H,4'H,6'H-spiro [oxetane-3,3'-[1,4]thiazepino[2,3,4-ij]quinazoline]-6',8'(7'H)-dione (4)

7-Chloro-8-({[3-(hydroxymethyl)oxetan-3-yl] methyl}sulfanyl)-6-(trifluoromethyl)-1,2,3,4-tetrahydroquinazoline-2,4-dione (0.485 g, 1.222 mmol, 1.0 eq) and triphenylphosphine (1.28 g, 4.89 mmol, 4.0 equiv) were dissolved in $CH_2C12$ (anhydrous, 19.4 mL) and cooled to 0° C. under argon over 15 minutes before dropwise addition of di-p-chlorobenzyl azodicarboxylate (Di-(4-chlorobenzyl) azodicarboxylate, 1.80 g, 4.89 mmol, 4.0 equiv) in anhydrous $CH_2Cl_2$ over 1 min. The reaction was allowed to stir at 0° C. under argon for 60 min. UPLC after 60 min indicated no remaining starting material. The precipitated solid was isolated by filtration under vacuum and washed with $CH_2Cl_2$. The filtrate was washed with saturated aqueous $NH_4Cl$. The layers were separated, and aqueous layer was washed with $CH_2Cl_2$ (2×25 mL). The combined organic layers were dried on a rotary evaporator. Purification by column chromatography (Interchim puriFlash® F0080 silica gel column), eluting with EtOAc/hexanes (3:2, 60 min) afforded the title compound. Fractions with the desired product were evaporated to dryness by rotary evaporation and the obtained material was suspended in mixture of hexanes/EtOAc (5:3) and vigorously stirred. The solid was filtered off and dried under vacuum. The title compound was obtained as a white solid (340 mg, 67% yield): $^1H$ NMR (300 MHz, DMSO-$d_6$) δ 12.01 (s, 1H), 8.04 (s, 1H), 7.46-7.40 (m, 2H), 5.08 (s, 2H), 4.39 (d, J=5.7 Hz, 2H), 3.72 (br s, 2H); $^{13}C$ NMR (75 MHz, DMOS-$d_6$) δ 160.7, 156.3, 151.6, 145.1, 135.6, 129.7, 128.6, 128.4, 123.0, 116.3, 77.5, 65.1, 51.4, 41.4, 37.6; LRMS-ESI (m/z) $[M-H]^-$ calculated for $C_{14}H_9ClF_3N_2O_3S$ 377.00, found 376.84.

L. Example 448

(3S)-7-((2S,5R)-4-acryloyl-2,5-dimethylpiperazin-1-yl)-9-chloro-10-(5-chloro-2,4-difluorophenyl)-3-((3-(trifluoromethyl)-5,6-dihydro-[1,2,4]triazolo[4,3-a]pyrazin-7(8H)-yl)methyl)-2,3-dihydro-5H-[1,4]thiazino[2,3,4-ij]quinazolin-5-one

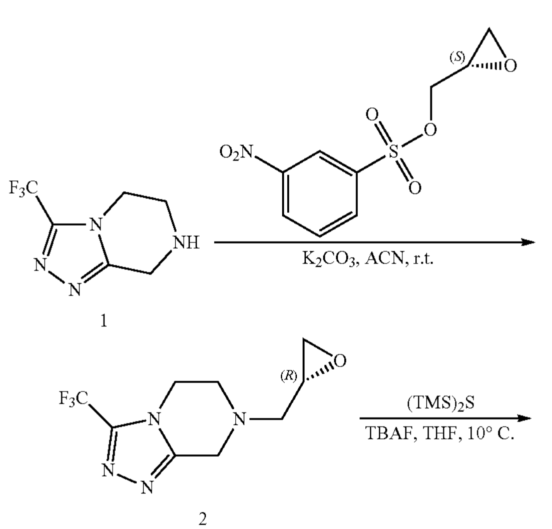

1

2

-continued

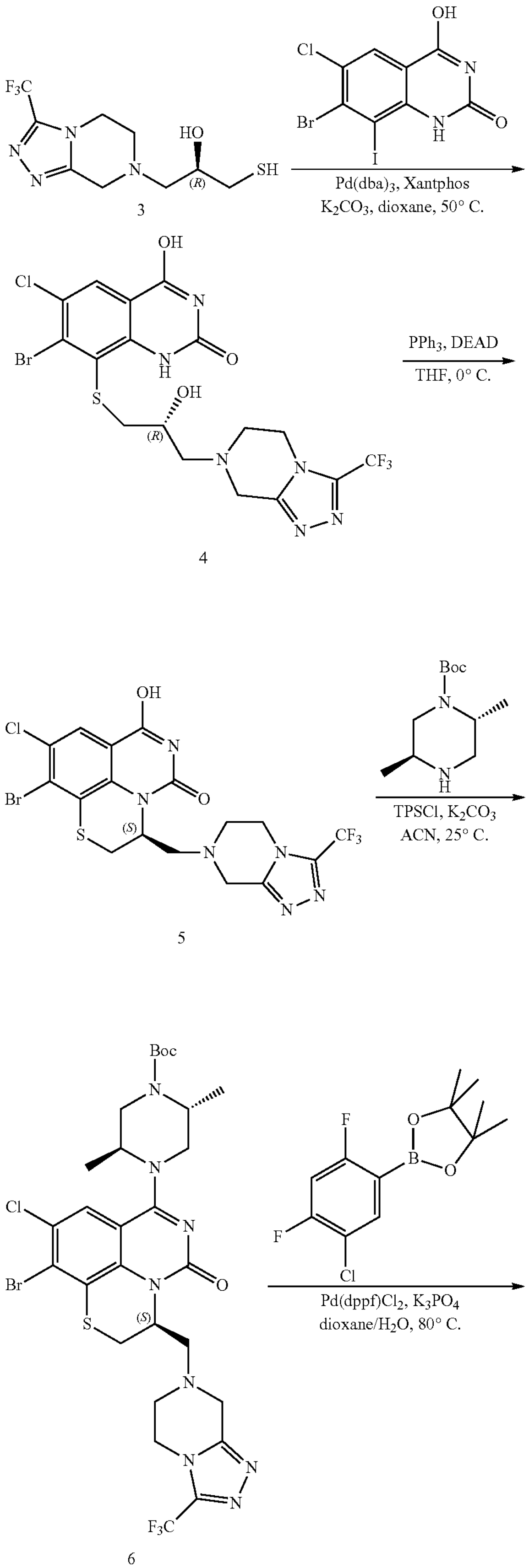

3

4

5

6

-continued

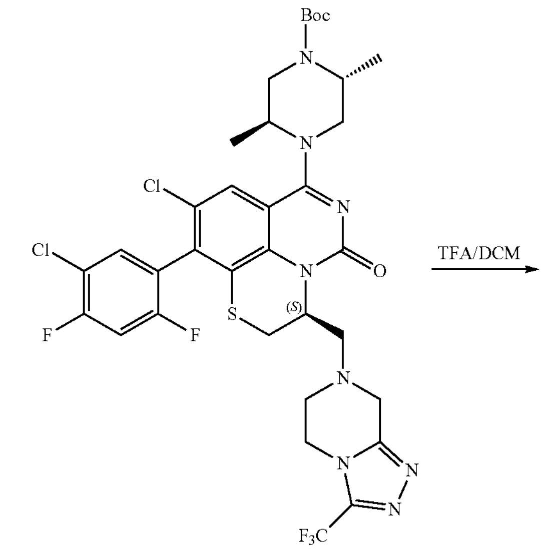

7

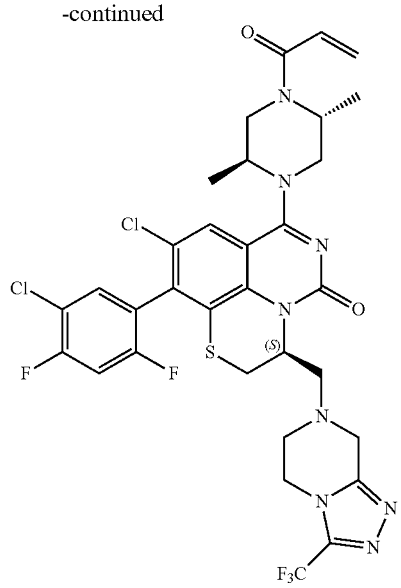

9

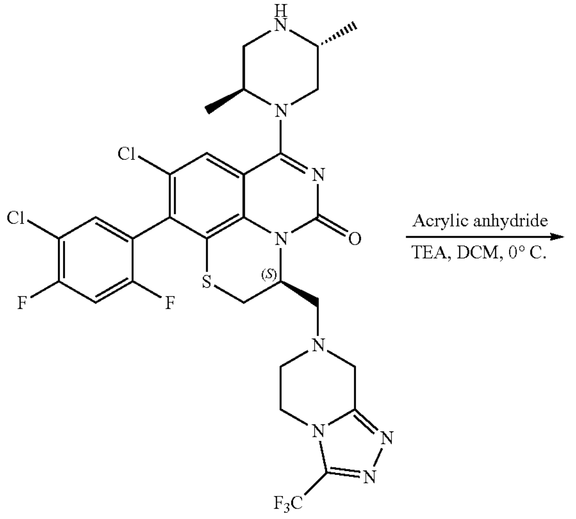

8

(R)-7-(oxiran-2-ylmethyl)-3-(trifluoromethyl)-5,6,7,8-tetrahydro-[1,2,4]triazolo[4,3-a]pyrazine (2)

To a mixture of (S)-oxiran-2-ylmethyl 3-nitrobenzenesulfonate (7.9, 30.7 mmol), 3-(trifluoromethyl)-5,6,7,8-tetrahydro-[1,2,4]triazolo[4,3-a]pyrazine (7.0 g, 30.7 mmol) in acetonitrile (50 mL) was added potassium carbonate (12.7 g, 92.1 mmol) at 20° C. under nitrogen atmosphere. The mixture was stirred under nitrogen atmosphere at room temperature for 20 hours. After completion, the mixture was concentrated. The residue was purified by silica gel column eluting with 2% methanol in dichloromethane to afford the product (6.2 g, 24.7 mmol) as a pale yellow oil. MS (ESI) m/z: 249.1 $[M+H]^+$.

(R)-1-mercapto-3-(3-(trifluoromethyl)-5,6-dihydro-[1,2,4]triazolo[4,3-a]pyrazin-7(8H)-yl)propan-2-ol (3)

To a mixture of (R)-7-(oxiran-2-ylmethyl)-3-(trifluoromethyl)-5,6,7,8-tetrahydro-[1,2,4]triazolo[4,3-a]pyrazine (6.1 g, 24.6 mmol) and tetrabutylammonium fluoride (30.7 mL, 30.7 mmol, 1.0 M in tetrahydrofuran,) in tetrahydrofuran (50 mL) was added 1,1,1,3,3,3-hexamethyldisilathiane (5.4 g, 30.7 mmol) at 0° C. The mixture was stirred at room temperature for 2 hrs. After completion, the mixture was poured into water (200 mL), extracted with ethyl acetate (3×200 mL). The combined organic phase was washed with brine (300 mL) and dried over anhydrous sodium sulfate. The mixture was concentrated and the residue was purified by silica gel column eluting with dichloromethane/methanol (50/1) to afford (R)-1-mercapto-3-(3-(trifluoromethyl)-5,6-dihydro-[1,2,4]triazolo[4,3-a]pyrazin-7(8H)-yl)propan-2-ol (4.8 g, 17.0 mmol, 70% yield) as a pale yellow oil. MS (ESI) m/z: 283.1 $[M+H]^+$.

(R)-7-bromo-6-chloro-4-hydroxy-8-((2-hydroxy-3-(3-(trifluoromethyl)-5,6-dihydro-[1,2,4]triazolo[4,3-a]pyrazin-7(8H)-yl)propyl)thio)quinazolin-2(1H)-one (4)

To a mixture of 7-bromo-6-chloro-4-hydroxy-8-iodoquinazolin-2(1H)-one (3.9 g, 10.0 mmol), potassium carbonate (4.14 g, 30.0 mmol), (R)-1-mercapto-3-(3-(trifluoromethyl)-5,6-dihydro-[1,2,4]triazolo[4,3-a]pyrazin-7(8H)-yl)propan-2-ol (3.1 g, 11.0 mmol) and 4,5-bis(diphenyl-phosphino)-9,9-dimethylxanthene (1.16 g, 2.0 mmol) in dioxane (128 mL) was added tris(dibenzylideneacetone) dipalladium (0.92 g, 1.0 mmol). The mixture was stirred at 55° C. under nitrogen atmosphere for 8 hrs. After completion, the mixture was filtered. The filtrate was concentrated and the residue was purified by silica gel column chromatography (1-5% methanol in dichloromethane) to afford (R)-7-bromo-6-chloro-4-hydroxy-8-((2-hydroxy-3-(3-(trifluoromethyl)-5,6-dihydro-[1,2,4]triazolo[4,3-a]pyrazin-7(8H)-yl)propyl)thio) quinazolin-2(1H)-one (3.5 g, 63% yield) as a yellow solid. MS (ESI) m/z: 557.0 $[M+H]^+$.

(S)-10-bromo-9-chloro-7-hydroxy-3-((3-(trifluoromethyl)-5,6-dihydro-[1,2,4]triazolo[4,3-a]pyrazin-7(8H)-yl)methyl)-2H-[1,4]thiazino[2,3,4-ij]quinazolin-5(3H)-one (5)

To a mixture of (R)-7-bromo-6-chloro-4-hydroxy-8-((2-hydroxy-3-(3-(trifluoromethyl)-5,6-dihydro-[1,2,4]triazolo[4,3-a]pyrazin-7(8H)-yl)propyl)thio)quinazolin-2(1H)-one (3.5 g, 6.3 mmol) and triphenylphosphine (2.0 g, 7.5 mmol) in tetrahydrofuran (25 mL) was added diethyl azodicarboxylate (1.6 g, 7.5 mmol) at 0° C. The mixture was stirred at 0° C. for 20 min. After completion, the mixture was concentrated. The residue was purified by flash chromatography column (C18, 5-95% acetonitrile in water) to afford (S)-10-bromo-9-chloro-7-hydroxy-3-((3-(trifluoromethyl)-5,6-dihydro-[1,2,4]triazolo[4,3-a]pyrazin-7(8H)-yl)methyl)-2H-[1,4]thiazino[2,3,4-ij]quinazolin-5(3H)-one as a pale yellow solid. MS (ESI): m/z: 539.0 $[M+H]^+$.

(2R,5S)-tert-butyl 4-((S)-10-bromo-9-chloro-5-oxo-3-((3-(trifluoromethyl)-5,6-dihydro-[1,2,4]triazolo[4,3-a]pyrazin-7(8H)-yl)methyl)-3,5-dihydro-2H-[1,4]thiazino[2,3,4-ij]quinazolin-7-yl)-2,5-dimethylpiperazine-1-carboxylate (6)

To a mixture of (S)-10-bromo-9-chloro-7-hydroxy-3-((3-(trifluoromethyl)-5,6-dihydro-[1,2,4]triazolo[4,3-a]pyrazin-7(8H)-yl)methyl)-2H-[1,4]thiazino[2,3,4-ij]quinazolin-5(3H)-one (1.05 g, 2.0 mmol) and $K_2CO_3$ (828 mg, 6.0 mmol) in acetonitrile (10 mL) was added 2,4,6-triisopropylbenzene-1-sulfonyl chloride (906 mg, 3.0 mmol). The mixture was stirred at 20° C. for 5 hours. To the mixture was added (2R,5S)-tert-butyl 2,5-dimethylpiperazine-1-carboxylate (1.28 g, 6.0 mmol) and stirred at 20° C. for another 3 hours. After completion, the mixture was concentrated under reduced pressure. The residue was purified by silica gel column with 1-5% methanol in dichloromethane as gradient to afford desired product (580 mg, 0.80 mmol, 40% yield) as yellow solid. LC-MS m/z: 735.1 $[M+H]^+$;

(2R,5S)-tert-butyl 4-((3S)-9-chloro-10-(5-chloro-2,4-difluorophenyl)-5-oxo-3-((3-(trifluoromethyl)-5,6-dihydro-[1,2,4]triazolo[4,3-a]pyrazin-7(8H)-yl)methyl)-3,5-dihydro-2H-[1,4]thiazino[2,3,4-ij]quinazolin-7-yl)-2,5-dimethylpiperazine-1-carboxylate (7)

To a mixture of (2R,5S)-tert-butyl 4-((S)-10-bromo-9-chloro-5-oxo-3-((3-(trifluoromethyl)-5,6-dihydro-[1,2,4]triazolo[4,3-a]pyrazin-7(8H)-yl)methyl)-3,5-dihydro-2H-[1,4]thiazino[2,3,4-ij]quinazolin-7-yl)-2,5-dimethylpiperazine-1-carboxylate (210 mg, 0.28 mmol) and tripotassium orthophosphate (178 mg, 0.84 mmol) in 1,4-dioxane (5 mL) and water (1 mL) were added [1,1'-bis(diphenylphosphino) ferrocene]dichloropalladium(II) (40.2 mg, 0.05 mmol) and 2-(5-chloro-2,4-difluorophenyl)-4,4,5,5-tetramethyl-1,3,2-dioxaborolane (391 mg, 1.4 mmol). The mixture was stirred at 90° C. for 3 hours. After completion, the mixture was concentrated and the residue was purified by silica gel column with 1-5% methanol in dichloromethane as gradient to afford (2R,5S)-tert-butyl 4-((3S)-9-chloro-10-(5-chloro-2,4-difluorophenyl)-5-oxo-3-((3-(trifluoromethyl)-5,6-dihydro-[1,2,4]triazolo[4,3-a]pyrazin-7(8H)-yl)methyl)-3,5-dihydro-2H-[1,4]thiazino[2,3,4-ij]quinazolin-7-yl)-2,5-dimethylpiperazine-1-carboxylate (203 mg, 0.25 mmol) as yellow solid. MS (ESI) m/z: 801.2 $[M+H]^+$.

(3S)-9-chloro-10-(5-chloro-2,4-difluorophenyl)-7-((2S,5R)-2,5-dimethylpiperazin-1-yl)-3-((3-(trifluoromethyl)-5,6-dihydro-[1,2,4]triazolo[4,3-a]pyrazin-7(8H)-yl)methyl)-2H-[1,4]thiazino[2,3,4-ij] quinazolin-5(3H)-one (8)

To a cooled mixture of (2R,5S)-tert-butyl 4-((3S)-9-chloro-10-(5-chloro-2,4-difluorophenyl)-5-oxo-3-((3-(trifluoromethyl)-5,6-dihydro-[1,2,4]triazolo[4,3-a]pyrazin-7(8H)-yl)methyl)-3,5-dihydro-2H-[1,4]thiazino[2,3,4-ij] quinazolin-7-yl)-2,5-dimethylpiperazine-1-carboxylate (203 mg, 0.25 mmol) in dichloromethane (3 ml) was added trifluoroacetic acid (1 mL) at 20° C. The reaction solution was stirred at room temperature for 1 hour. After completion, the mixture was concentrated. The residue was purified by silica gel column with 1-5% methanol in dichloromethane as gradient to afford (3S)-9-chloro-10-(5-chloro-2,4-difluorophenyl)-7-((2S,5R)-2,5-dimethylpiperazin-1-yl)-3-((3-(trifluoromethyl)-5,6-dihydro-[1,2,4]triazolo[4,3-a] pyrazin-7(8H)-yl)methyl)-2H-[1,4]thiazino[2,3,4-ij] quinazolin-5(3H)-one (116 mg, 0.165 mmol) as a yellow solid. MS (ESI) m/z: 701.2 $[M+H]^+$.

(3S)-7-((2S,5R)-4-acryloyl-2,5-dimethylpiperazin-1-yl)-9-chloro-10-(5-chloro-2,4-difluorophenyl)-3-((3-(trifluoromethyl)-5,6-dihydro-[1,2,4]triazolo[4,3-a] pyrazin-7(8H)-yl)methyl)-2H-[1,4]thiazino[2,3,4-ij] quinazolin-5(3H)-one (9)

To a mixture of (3S)-9-chloro-10-(5-chloro-2,4-difluorophenyl)-7-((2S,5R)-2,5-dimethylpiperazin-1-yl)-3-((3-(trifluoromethyl)-5,6-dihydro-[1,2,4]triazolo[4,3-a]pyrazin-7(8H)-yl)methyl)-2H-[1,4]thiazino[2,3,4-ij]quinazolin-5(3H)-one (116 mg, 0.165 mmol) and triethyl amine (100 mg, 1.0 mmol) in dichloromethane (5 mL) was added acrylic anhydride (31 mg, 0.25 mmol) at 0° C. The mixture was stirred at 0° C. for 1 h. After completion, the mixture was poured into ice-water (50 mL) and extracted with ethyl acetate (3×20 mL). The organic layer was dried over $Na_2SO_4$ and concentrated. The residue was purified by preparative High Performance Liquid Chromatography (10% to 95% acetonitrile in water) to afford the product as a white solid (43 mg, 0.06 mmol). $^1H$ NMR (400 MHz, $CDCl_3$) δ 7.59-7.53 (m, 1H), 7.33-7.28 (m, 1H), 7.13-7.08 (m, 1H), 6.61-6.48 (m, 1H), 6.40-6.32 (m, 1H), 5.79-5.75 (m, 1H), 5.54-5.38 (brs, 1H), 5.03-4.96 (brs, 0.5H), 4.80-4.70 (m, 1H), 4.38-4.09 (m, 2.5H), 4.07-3.96 (m, 3.5H), 3.71-3.65 (m, 2H), 3.30-3.08 (m, 5.5H), 2.96-2.91 (m, 1H), 2.90-2.83 (m, 2H), 1.46-1.38 (m, 3H), 1.32-1.25 (m, 3H). MS (ESI) m/z: 755.1 $[M+H]^+$.

M. Example 462
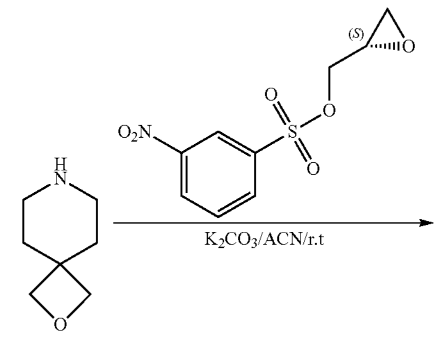
1
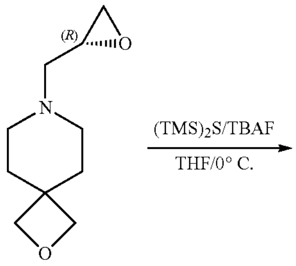
2
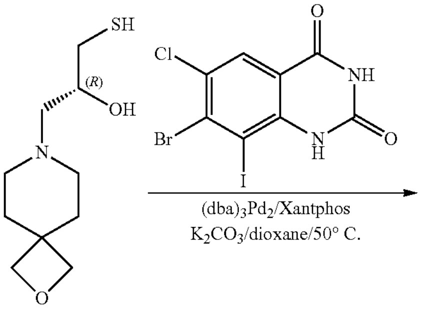
3
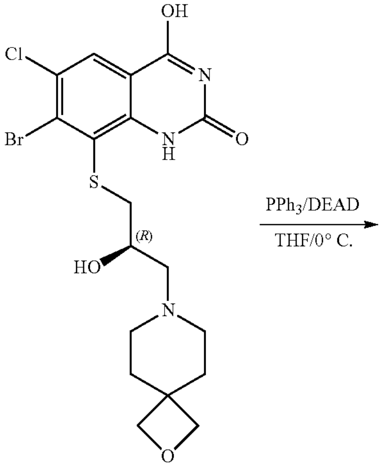
4
-continued
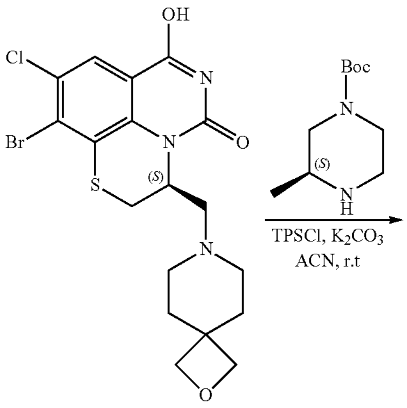
5
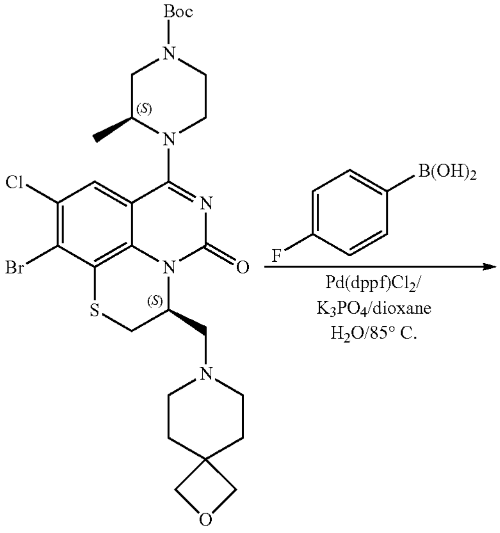
6
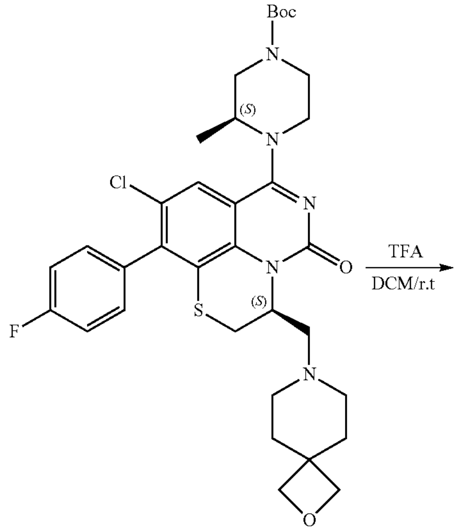
7

-continued

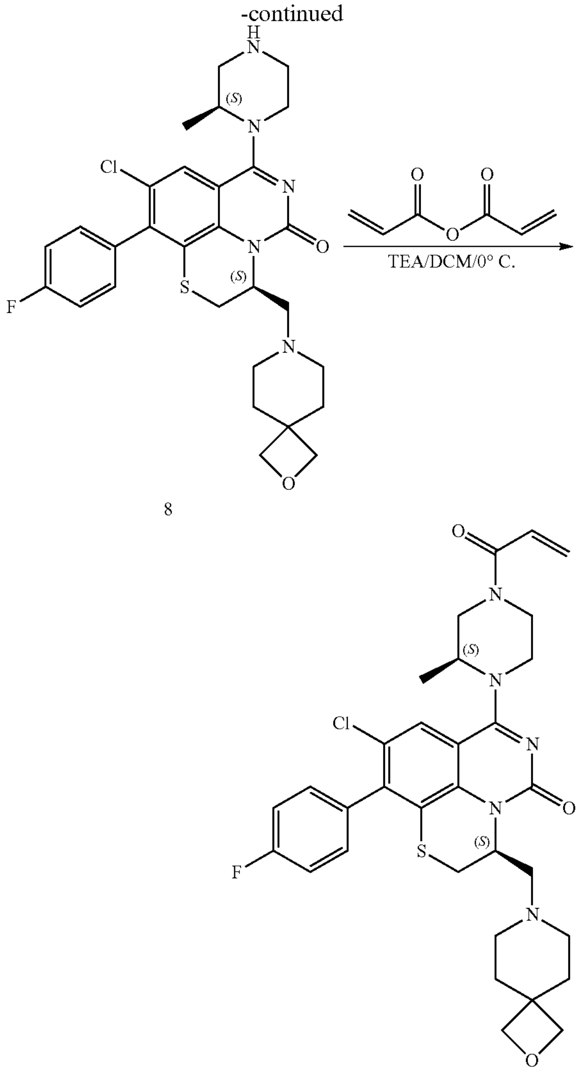

8

9

(R)-7-(oxiran-2-ylmethyl)-2-oxa-7-azaspiro[3.5]nonane (2)

To a mixture of (S)-oxiran-2-ylmethyl 3-nitrobenzenesulfonate (5.9 g, 22.8 mmol), 2-oxa-7-azaspiro[3.5]nonane oxalate (4.5 g, 20.7 mmol) in acetonitrile (60 mL) was added potassium carbonate (14.3 g, 103.6 mmol) at 0° C. under nitrogen atmosphere. The mixture was stirred at room temperature for 16 hours. After completion, the mixture was concentrated and the residue was purified by silica gel column eluting a mixture of dichloromethane/methanol (20/1) to afford (R)-7-(oxiran-2-ylmethyl)-2-oxa-7-azaspiro[3.5]nonane (3.45 g, 91% yield) as a brown oil. MS (ESI) m/z: 180.1 $[M+H]^+$.

(R)-1-mercapto-3-(2-oxa-7-azaspiro[3.5]nonan-7-yl)propan-2-ol (3)

To a mixture of (R)-7-(oxiran-2-ylmethyl)-2-oxa-7-azaspiro[3.5]nonane (3.74 g, 20.4 mmol) in tetrahydrofuran (70 mL) was added 1,1,1,3,3,3-hexamethyldisilathiane (5.45 g, 30.6 mmol) and tetrabutylammonium fluoride (1.0 M in tetrahydrofuran, 6.1 mL, 6.1 mmol) at 0° C. The resulting mixture was stirred at room temperature for 6 hours. After completion, the mixture was concentrated and the residue was purified by silica gel column eluting with dichloromethane/methanol (20/1) to afford (R)-1-mercapto-3-(2-oxa-7-azaspiro[3.5]nonan-7-yl)propan-2-ol (3.47 g, 78% yield) as a brown oil. MS (ESI) m/z: 218.2 $[M+H]^+$.

(R)-7-bromo-6-chloro-4-hydroxy-8-((2-hydroxy-3-(2-oxa-7-azaspiro[3.5]nonan-7-yl)propyl)thio)quinazolin-2(1H)-one (4)

To a solution of 7-bromo-6-chloro-8-iodoquinazoline-2,4(1H,3H)-dione (4.93 g, 12.3 mmol) in dioxane (50 mL) were added potassium carbonate (5.09 g, 36.8 mmol), (R)-1-mercapto-3-(2-oxa-7-azaspiro[3.5]nonan-7-yl)propan-2-ol (3.47 g, 16.0 mmol), 4,5-bis(diphenyl-phosphino)-9,9-dimethylxanthene (1.42 g, 2.45 mmol) and tris(dibenzylideneacetone) dipalladium (1.12 g, 1.23 mmol). The mixture was stirred at 50° C. under nitrogen atmosphere for 16 hours. After completion, the mixture was concentrated and the residue was purified by silica gel column eluting with dichloromethane/methanol (20/1) to afford (R)-7-bromo-6-chloro-4-hydroxy-8-((2-hydroxy-3-(2-oxa-7-azaspiro[3.5]nonan-7-yl)propyl)thio)quinazolin-2(1H)-one (4.47 g, 74% yield) as an orange solid. MS (ESI) m/z: 492.4 $[M+H]^+$.

(S)-3-(2-oxa-7-azaspiro[3.5]nonan-7-ylmethyl)-10-bromo-9-chloro-7-hydroxy-2H-[1,4]thiazino[2,3,4-ij]quinazolin-5(3H)-one (5)

To a mixture of (R)-7-bromo-6-chloro-4-hydroxy-8-((2-hydroxy-3-(2-oxa-7-azaspiro[3.5]nonan-7-yl)propyl)thio)quinazolin-2(1H)-one (3.9 g, 7.95 mmol) and triphenylphosphoranylidene (4.16 g, 15.9 mmol) in tetrahydrofuran (70 mL) was added diethyl azodicarboxylate (2.77 g, 15.9 mmol). The mixture was stirred at room temperature for 2 hours. After completion, the mixture was poured into ice-water (100 mL) and extracted with ethyl acetate (3×100 mL). The mixture was concentrated and the residue was purified by silica gel column eluting with dichloromethane/methanol (50/1) to afford (S)-3-(2-oxa-7-azaspiro[3.5]nonan-7-ylmethyl)-10-bromo-9-chloro-7-hydroxy-2H-[1,4]thiazino[2,3,4-ij]quinazolin-5(3H)-one (2.66 g, 71% yield) as a light yellow solid. MS (ESI) m/z: 474.4 $[M+H]^+$.

(S)-tert-butyl 4-((S)-3-(2-oxa-7-azaspiro[3.5]nonan-7-ylmethyl)-10-bromo-9-chloro-5-oxo-3,5-dihydro-2H-[1,4]thiazino[2,3,4-ij]quinazolin-7-yl)-3-methylpiperazine-1-carboxylate (6)

To a mixture of (S)-3-(2-oxa-7-azaspiro[3.5]nonan-7-ylmethyl)-10-bromo-9-chloro-7-hydroxy-2H-[1,4]thiazino[2,3,4-ij]quinazolin-5(3H)-one (1.20 g, 2.54 mmol) and potassium carbonate (1.63 g, 25.40 mmol) in acetonitrile (100 mL) was added 2,4,6-triisopropylbenzenesulfonyl chloride (2.30 g, 7.63 mmol) at 0° C. The mixture was stirred at 0° C. for 30 min and at 30° C. for 1 hour. After completion, (2R,5S)-tert-butyl 2,5-dimethylpiperazine-1-carboxylate (1.53 g, 7.63 mmol) was added into the reaction solution. The reaction mixture was stirred at 0° C. for another 1 hour. After completion, the mixture was poured into ice-water (300 mL) and extracted with ethyl acetate (3×200 mL). The mixture was concentrated and the residue was purified by flash chromatography column (C18, acetonitrile/water=20% to 95%) to afford (S)-tert-butyl 4-((S)-3-(2-oxa-7-azaspiro[3.5]nonan-7-ylmethyl)-10-bromo-9-chloro-5-oxo-3,5-dihydro-2H-[1,4]thiazino[2,3,4-ij]quinazolin-7-yl)-3-methylpiperazine-1-carboxylate (860 mg, 51% yield) as a pale-white solid. MS (ESI) m/z: 655.3 $[M+H]^+$.

(S)-tert-butyl 4-((S)-3-(2-oxa-7-azaspiro[3.5]nonan-7-ylmethyl)-9-chloro-10-(4-fluorophenyl)-5-oxo-3,5-dihydro-2H-[1,4]thiazino[2,3,4-ij]quinazolin-7-yl)-3-methylpiperazine-1-carboxylate (7)

To a mixture of (S)-tert-butyl 4-((S)-3-(2-oxa-7-azaspiro[3.5]nonan-7-ylmethyl)-10-bromo-9-chloro-5-oxo-3,5-dihydro-2H-[1,4]thiazino[2,3,4-ij]quinazolin-7-yl)-3-methylpiperazine-1-carboxylate (200 mg, 0.30 mmol) and tripotassium orthophosphate (325 mg, 1.53 mmol) in 1,4-dioxane (8 mL) and water (1 mL) was added [1,1'-bis(diphenylphosphino)ferrocene]dichloropalladium(II) (45 mg, 0.06 mmol) and (4-fluorophenyl)boronic acid (214 mg, 1.52 mmol). The mixture was stirred at 85° C. for 2 hours. After completion, the mixture was diluted with tetrahydrofuran (50 mL) and insoluble solid was filtered out. The mixture was concentrated and the residue was purified by silica gel column eluting with dichloromethane/methanol (50/1) to afford (S)-tert-butyl 4-((S)-3-(2-oxa-7-azaspiro[3.5]nonan-7-ylmethyl)-9-chloro-10-(4-fluorophenyl)-5-oxo-3,5-dihydro-2H-[1,4]thiazino[2,3,4-ij]quinazolin-7-yl)-3-methylpiperazine-1-carboxylate (214 mg, crude) as a light yellow oil. MS (ESI) m/z: 670.2 $[M+H]^+$.

(S)-3-(2-oxa-7-azaspiro[3.5]nonan-7-ylmethyl)-9-chloro-10-(4-fluorophenyl)-7-((S)-2-methylpiperazin-1-yl)-2H-[1,4]thiazino[2,3,4-ij]quinazolin-5(3H)-one (8)

To a mixture of (S)-tert-butyl 4-((S)-3-(2-oxa-7-azaspiro[3.5]nonan-7-ylmethyl)-9-chloro-10-(4-fluorophenyl)-5-oxo-3,5-dihydro-2H-[1,4]thiazino[2,3,4-ij]quinazolin-7-yl)-3-methylpiperazine-1-carboxylate (214 mg, 0.32 mmol) in dichloromethane (3 mL) was added trifluoroacetic acid (1 mL). The mixture was stirred at room temperature for 30 min. After completion, the mixture was purified by silica gel column eluting with dichloromethane/methanol (50/1) to afford (S)-3-(2-oxa-7-azaspiro[3.5]nonan-7-ylmethyl)-9-chloro-10-(4-fluorophenyl)-7-((S)-2-methylpiperazin-1-yl)-2H-[1,4]thiazino[2,3,4-ij]quinazolin-5(3H)-one (130 mg, 71% yield) as a yellow solid. MS (ESI) m/z: 570.1 $[M+H]^+$.

(S)-3-(2-oxa-7-azaspiro[3.5]nonan-7-ylmethyl)-7-((S)-4-acryloyl-2-methylpiperazin-1-yl)-9-chloro-10-(4-fluorophenyl)-2H-[1,4]thiazino[2,3,4-ij]quinazolin-5(3H)-one (9)

To a mixture of (S)-3-(2-oxa-7-azaspiro[3.5]nonan-7-ylmethyl)-9-chloro-10-(4-fluorophenyl)-7-((S)-2-methylpiperazin-1-yl)-2H-[1,4]thiazino[2,3,4-ij]quinazolin-5(3H)-one (100 mg, 0.17 mmol) and triethylamine (54 mg, 0.51 mmol) in dichloromethane (3 mL) was added acrylic anhydride (43 mg, 0.34 mmol) at 0° C. The mixture was stirred at 0° C. for 1 hour. After completion, the mixture was poured into ice-water (15 mL) and extracted with ethyl acetate (3×15 mL). After concentration, the residue was purified by preparative high performance liquid chromatography (20% to 95% acetonitrile in water as gradient) to afford the product (50 mg, 46% yield) as a light-yellow solid.

$^1H$ NMR (400 MHz, $CDCl_3$) δ 7.48 (s, 1H), 7.23-7.18 (m, 4H), 6.62-6.52 (m, 1H), 6.36 (d, J=18.0 Hz, 1H), 5.77 (d, J=10.8 Hz, 1H), 5.29-5.27 (m, 1H), 4.74-4.70 (m, 1H), 4.64 (m, 0.5H), 4.54-4.38 (m, 5H), 4.21-4.19 (m, 0.5H), 3.96-3.95 (m, 0.5H), 3.81-3.77 (m, 0.5H), 3.62-3.49 (m, 2H), 3.37-3.36 (m, 1H), 3.12-3.07 (m, 1H), 3.00-2.94 (m, 1H), 2.79-2.73 (m, 1H), 2.65-2.55 (m, 2H), 2.49-2.47 (m, 1H), 2.43-2.35 (m, 2H), 1.88-1.75 (m, 4H), 1.48-1.44 (m, 3H). MS (ESI) m/z: 624.1 $[M+H]^+$.

N. Example 481

(S)-7-((2S,5R)-4-acryloyl-2,5-dimethylpiperazin-1-yl)-3-((1-(2,2-difluoroethyl)azetidin-3-yl)methyl)-10-(4-fluorophenyl)-9-(trifluoromethyl)-2,3-dihydro-5H-[1,4]thiazino[2,3,4-ij]quinazolin-5-one

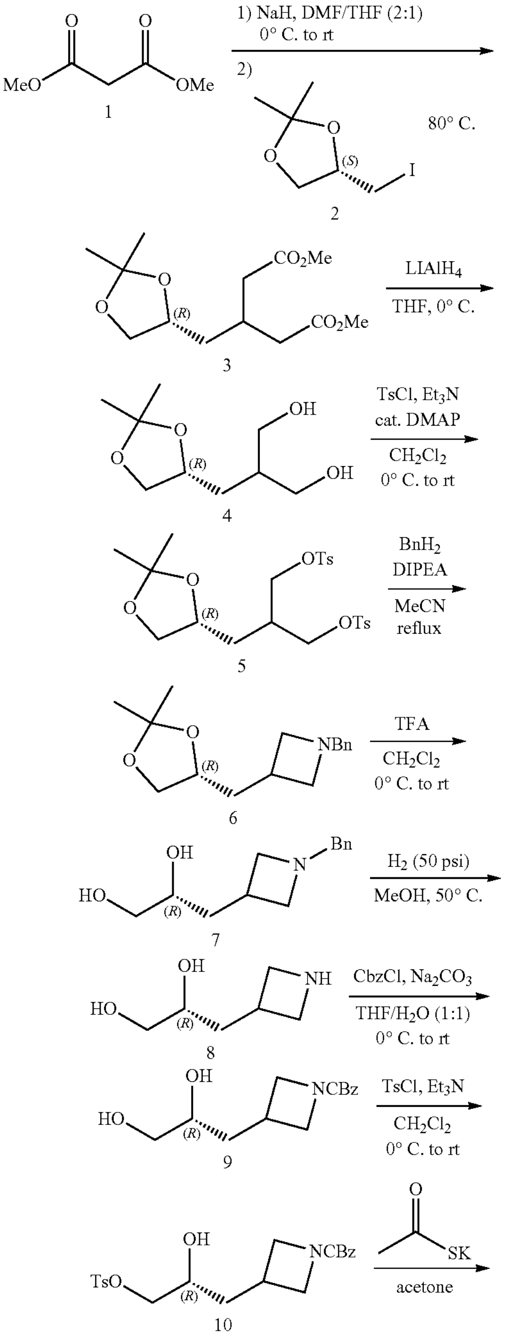

-continued
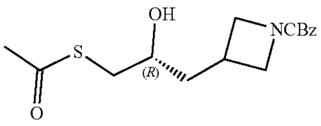
11
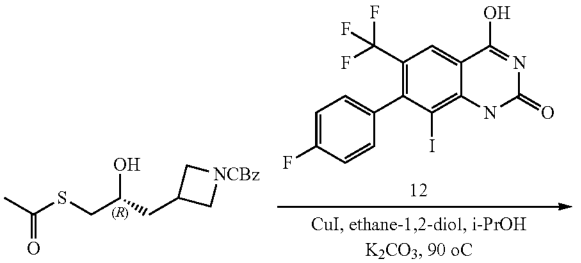
11
12
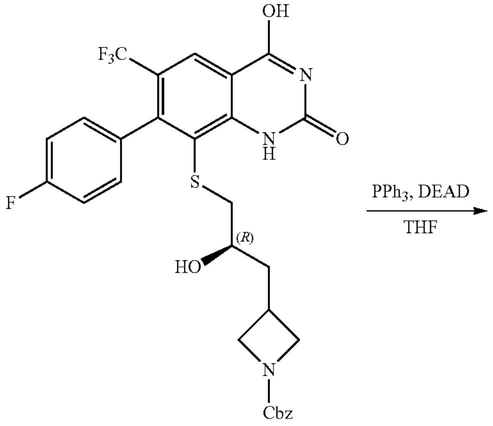
13
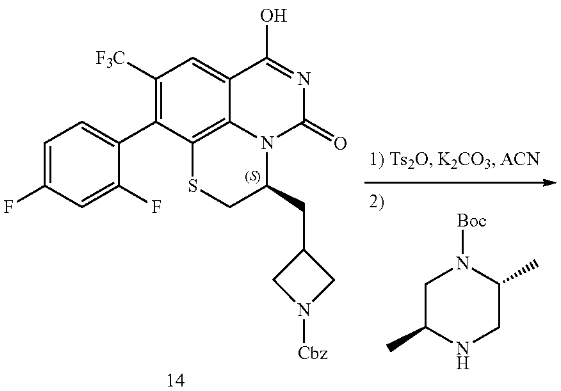
14
-continued
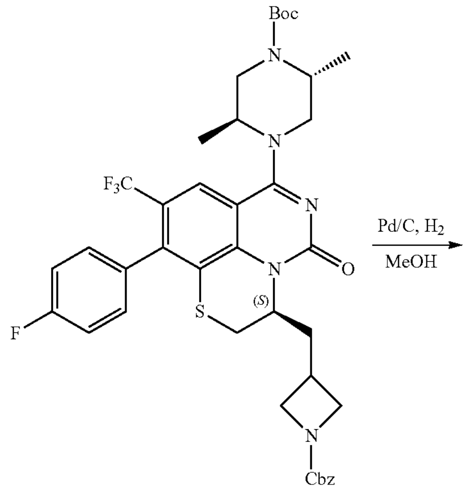
15
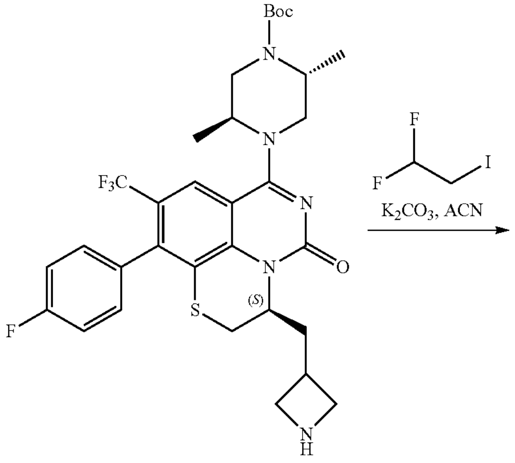
16
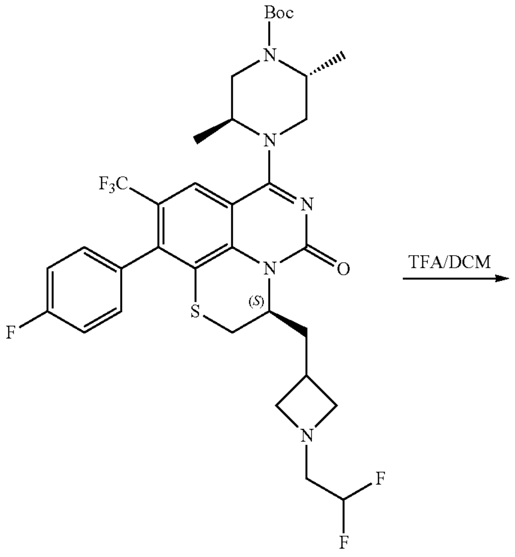
17

-continued

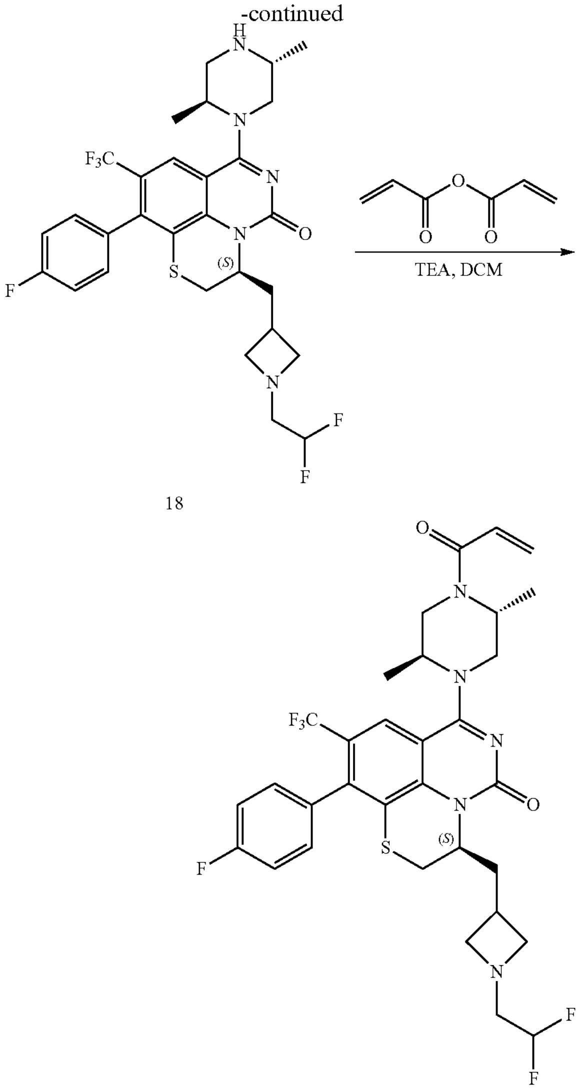

18

19

(R)-dimethyl 2-((2,2-dimethyl-1,3-dioxolan-4-yl)methyl)malonate (3)

To a mixture of sodium hydride (4.58 g, 190.87 mmol) in dimethylformide (208 mL) and tetrahydrofuran (104 mL) was added dimethyl malonate (21.6 g, 163.6 mmol) dropwise at 0° C. under nitrogen atmosphere. The mixture was allowed to warm up to room temperature for 1 hour, then (S)-4-(iodomethyl)-2,2-dimethyl-1,3-dioxolane (26.4 g, 109.07 mmol) was added dropwise. The mixture was heated to 80° C. and stirred overnight. After completion, the mixture was quenched with saturated aqueous ammonium chloride solution, the aqueous layer was extracted with ethyl acetate (2×500 mL). The organic layer was dried over anhydrous sodium sulfate, filtered and concentrated. The residue was purified by silica gel column eluting with petroleum ether/ethyl acetate (50/1) to afford (R)-dimethyl 2-((2,2-dimethyl-1,3-dioxolan-4-yl)methyl)malonate (18 g, 67% yield) as pale yellow liquid. $^1H$ NMR (400 MHz, $CDCl_3$) δ 4.16-4.10 (m, 1H), 4.08-4.04 (m, 1H), 3.76 (s, 3H), 3.74 (s, 3H), 3.63-3.56 (m, 2H), 2.24-2.18 (m, 1H), 2.13-2.06 (m, 1H), 1.39 (s, 3H), 1.32 (s, 3H).

(R)-2-((2,2-dimethyl-1,3-dioxolan-4-yl)methyl)propane-1,3-diol (4)

To a mixture of lithium aluminum hydride (4.07 g, 107.2 mmol) in tetrahydrofuran (150 mL) was added dropwise (R)-dimethyl 2-((2,2-dimethyl-1,3-dioxolan-4-yl)methyl) malonate (8.8 g, 35.74 mmol) at 0° C. under nitrogen atmosphere. The mixture was stirred at 0° C. to room temperature for 2 hours. After completion, the mixture was diluted with ether (100 mL) and cooled to 0° C., quenched with 4 mL water, then 4 mL 15% sodium hydroxide solution and 12 mL water. The organic layer was separated, dried over anhydrous sodium sulfate, filtered and concentrated to afford (R)-2-((2,2-dimethyl-1,3-dioxolan-4-yl)methyl)propane-1,3-diol (5.32 g, 78% yield) as colorless oil, which was used to next step without further purification. $^1H$ NMR (400 MHz, $CDCl_3$) δ 4.25-4.18 (m, 1H), 4.09 (t, J=6.8 Hz, 1H), 3.77-3.68 (m, 4H), 3.53 (t, J=7.6 Hz, 1H), 1.93-1.87 (m, 1H), 1.75-1.68 (m, 1H), 1.63-1.54 (m, 1H), 1.42 (s, 3H), 1.36 (s, 3H).

(R)-2-((2,2-dimethyl-1,3-dioxolan-4-yl)methyl)propane-1,3-diyl bis(4-methylbenzenesulfonate) (5)

To a solution of (R)-2-((2,2-dimethyl-1,3-dioxolan-4-yl) methyl)propane-1,3-diol (5.32 g, 27.96 mmol), 4-dimethylaminopyridine (444 mg, 3.63 mmol) and triethyl amine (11.3 g, 111.84 mmol) in dichloromethane (50 mL) was added 4-toluene sulfonyl chloride (18.98 g, 99.54 mmol) at 0° C. The mixture was stirred at room temperature overnight. 200 mL water was added and extracted with dichloromethane (3×200 mL). The organic phase was concentrated and the residue was purified by silica gel column eluting with petroleum ether/ethyl acetate=10/1 to afford (R)-2-((2,2-dimethyl-1,3-dioxolan-4-yl)methyl)propane-1,3-diyl bis (4-methylbenzenesulfonate) (10.16 g, 73% yield) as white solid. MS (ESI) m/z: 499.1 $[M+H]^+$.

(R)-1-benzyl-3-((2,2-dimethyl-1,3-dioxolan-4-yl)methyl)azetidine (6)

To a solution of (R)-2-((2,2-dimethyl-1,3-dioxolan-4-yl) methyl)propane-1,3-diyl bis(4-methylbenzenesulfonate) (9.9 g, 19.8 mmol), phenylmethanamine (7.6 mL, 69.44 mmol) in acetonitrile (90 mL) was added N,N-diisopropylethylamine (7.6 mL, 43.69 mmol) at room temperature. The mixture was heated to reflux overnight. After completion, 200 mL water was added and extracted with dichloromethane (3×200 mL). The organic phase was concentrated and the residue was purified by silica gel column eluting with petroleum ether/ethyl acetate=1/1 to afford (R)-1-benzyl-3-((2,2-dimethyl-1,3-dioxolan-4-yl)methyl)azetidine (2.84 g, 55% yield) as brown liquid. MS (ESI) m/z: 262.2 $[M+H]^+$.

(R)-3-(1-benzylazetidin-3-yl)propane-1,2-diol (7)

To a mixture of (R)-1-benzyl-3-((2,2-dimethyl-1,3-dioxolan-4-yl)methyl)azetidine (2.84 g, 10.88 mmol) in dichloromethane (28 mL) was added trifluoroacetic acid (14 mL) at room temperature. Then the mixture was stirred at room temperature for 2 hours. After completion, the mixture was concentrated and adjusted pH to 7~8 with ammonia solution, then concentrated to afford (R)-3-(1-benzylazetidin-3-yl) propane-1,2-diol (9.4 g, crude) as yellow solid, which was used to next step without further purification. MS (ESI) m/z: 222.1 $[M+H]^+$.

(R)-3-(azetidin-3-yl)propane-1,2-diol (8)

To a solution of (R)-3-(1-benzylazetidin-3-yl)propane-1,2-diol (4.577 g, 20.7 mmol) in methanol (30 mL) was added palladium on charcoal (10%) (400 mg) at room temperature. The mixture was stirred under hydrogen protection at 50° C. overnight. After completion, the mixture was filtered and concentrated to afford (R)-3-(azetidin-3-yl)propane-1,2-diol (4.2 g, crude) as yellow oil, which was used to next step without further purification. MS (ESI) m/z: 132.1 $[M+H]^+$.

(R)-benzyl 3-(2,3-dihydroxypropyl)azetidine-1-carboxylate (9)

To a mixture of (R)-3-(azetidin-3-yl)propane-1,2-diol (1.43 g, 10.88 mol) and sodium carbonate (3.46 g, 32.64 mmol) in tetrahydrofuran (28 mL) and water (28 mL) was added benzyl carbonochloridate (2.23 g, 13.06 mol) slowly at 0° C. The mixture was stirred at 0° C. overnight. After completion, the mixture was extracted with ethyl acetate (100 mL), the organic phase was washed with brine (100 mL×2), dried over anhydrous sodium sulfate, filtered and concentrated. The residue was purified by silica gel column eluting with dichloromethane/methanol=50/1 to afford (R)-benzyl 3-(2,3-dihydroxypropyl)azetidine-1-carboxylate (1.6 g, 55% yield for 2 steps) as colorless oil; MS (ESI) m/z: 266.1 $[M+H]^+$.

(R)-benzyl 3-(2-hydroxy-3-(tosyloxy)propyl)azetidine-1-carboxylate (10)

To a solution of (R)-benzyl 3-(2,3-dihydroxypropyl)azetidine-1-carboxylate (1.6 g, 6.03 mmol) and triethyl amine (1.22 g, 12.06 mmol) in dichloromethane (30 mL) was added 4-toluene sulfochloride (1.03 g, 5.43 mmol) at 0° C. The mixture was stirred at room temperature for 4 hours. After completion, the mixture was concentrated and the residue was purified by silica gel column eluting with dichloromethane/methanol (50/1) to afford the (R)-benzyl 3-(2-hydroxy-3-(tosyloxy)propyl)azetidine-1-carboxylate (1.7 g, 67% yield) as pale yellow oil. MS (ESI) m/z: 420.1 $[M+H]^+$.

(R)-benzyl 3-(3-(acetylthio)-2-hydroxypropyl)azetidine-1-carboxylate (11)

To a mixture of (R)-benzyl 3-(2-hydroxy-3-(tosyloxy)propyl)azetidine-1-carboxylate (1.4 g, 3.34 mmol) in acetone (20 mL) was added potassium ethanethioate (1.14 g, 10.02 mmol). The mixture was stirred at 50° C. under nitrogen atmosphere for 1 hour. After completion, the mixture was filtered, and the filtrate was concentrated. The residue was purified by silica gel column eluting with dichloromethane/methanol (60/1) to afford (R)-benzyl 3-(3-(acetylthio)-2-hydroxypropyl)azetidine-1-carboxylate (800 mg, 74% yield) as colorless oil. MS (ESI) m/z: 324.1 $[M+H]^+$.

(R)-benzyl 3-(3-((7-(4-fluorophenyl)-4-hydroxy-2-oxo-6-(trifluoromethyl)-1,2-dihydroquinazolin-8-yl)thio)-2-hydroxypropyl)azetidine-1-carboxylate (13)

The mixture of 7-(4-fluorophenyl)-4-hydroxy-8-iodo-6-(trifluoromethyl)quinazolin-2(1H)-one (927 mg, 2.06 mmol), (R)-benzyl 3-(3-(acetylthio)-2-hydroxypropyl)azetidine-1-carboxylate (800 mg, 2.48 mmol), copper (I) iodide (197 mg, 1.03 mmol) and potassium carbonate (853 mg, 6.18 mmol) in ethane-1,2-diol (12 mL) and i-PrOH (12 mL) was stirred under nitrogen atmosphere at 85° C. for 18 hours. After completion, ethyl acetate (200 mL) was added, the organic phase was washed with water (2×150 mL), dried over anhydrous sodium sulfate, filtered and concentrated. The residue was purified by silica gel column with dichloromethane/ethyl acetate (3/1) to afford (R)-benzyl 3-(3-((7-(4-fluorophenyl)-4-hydroxy-2-oxo-6-(trifluoromethyl)-1,2-dihydroquinazolin-8-yl)thio)-2-hydroxypropyl)azetidine-1-carboxylate (320 mg, crude) as yellow solid. MS (ESI) m/z: 604.0 $[M+H]^+$.

Benzyl 3-(((3S)-10-(2,4-difluorophenyl)-7-hydroxy-5-oxo-9-(trifluoromethyl)-3,5-dihydro-2H-[1,4]thiazino[2,3,4-ij]quinazolin-3-yl)methyl)azetidine-1-carboxylate (14)

To a mixture of (R)-benzyl 3-(3-((7-(4-fluorophenyl)-4-hydroxy-2-oxo-6-(trifluoromethyl)-1,2-dihydroquinazolin-8-yl)thio)-2-hydroxypropyl)azetidine-1-carboxylate (258 mg, 0.43 mmol) and triphenylphosphoranylidene (448 mg, 1.71 mmol) in tetrahydrofuran (80 mL) was added 1,2-bis[(4-chlorophenyl)methyl] ester (627 mg, 1.71 mmol) at 0° C. The mixture was stirred at 0° C. for 45 min. After completion, the mixture was poured into ice-water (100 mL) and extracted with ethyl acetate (3×50 mL). The mixture was concentrated and the residue was purified by C18 column with 30-95% acetonitrile in water as gradient to afford benzyl 3-(((3S)-10-(2,4-difluorophenyl)-7-hydroxy-5-oxo-9-(trifluoromethyl)-3,5-dihydro-2H-[1,4]thiazino[2,3,4-ij]quinazolin-3-yl)methyl)azetidine-1-carboxylate (117 mg, 47% yield) as white solid. MS (ESI) m/z: 586.0 $[M+H]^+$.

(2R,5S)-tert-butyl 4-((S)-3-((1-((benzyloxy)carbonyl)azetidin-3-yl)methyl)-10-(4-fluorophenyl)-5-oxo-9-(trifluoromethyl)-3,5-dihydro-2H-[1,4]thiazino[2,3,4-ij]quinazolin-7-yl)-2,5-dimethylpiperazine-1-carboxylate (15)

To a solution of benzyl 3-(((3S)-10-(2,4-difluorophenyl)-7-hydroxy-5-oxo-9-(trifluoromethyl)-3,5-dihydro-2H-[1,4]thiazino[2,3,4-ij]quinazolin-3-yl)methyl)azetidine-1-carboxylate (75 mg, 0.128 mmol) and potassium carbonate (177 mg, 1.282 mmol) in acetonitrile (6 mL) was added 4-methylbenzenesulfonic anhydride (104 mg, 0.320 mmol) in portions at room temperature. The mixture was stirred at room temperature under nitrogen atmosphere for 5 hours. After completion, (2R,5S)-tert-butyl 2,5-dimethylpiperazine-1-carboxylate (110 mg, 0.512 mmol) was added into the reaction solution. The mixture was stirred at room temperature for anther 0.5 hour. After completion, the mixture was poured into ice-water (50 mL) and extracted with ethyl acetate (3×50 mL), dried over $Na_2SO_4$ and concentrated. The residue was purified by Flash chromatography column (C18, acetonitrile/water=30% to 95%) to afford (2R,5S)-tert-butyl 4-((S)-3-((1-((benzyloxy)carbonyl)azetidin-3-yl)methyl)-10-(4-fluorophenyl)-5-oxo-9-(trifluoromethyl)-3,5-dihydro-2H-[1,4]thiazino[2,3,4-ij]quinazolin-7-yl)-2,5-dimethylpiperazine-1-carboxylate (60 mg, 60% yield) as a pale yellow solid. MS (ESI) m/z: 782.9 $[M+H]^+$.

(2R,5S)-tert-butyl 4-((S)-3-(azetidin-3-ylmethyl)-10-(4-fluorophenyl)-5-oxo-9-(trifluoromethyl)-3,5-dihydro-2H-[1,4]thiazino[2,3,4-ij]quinazolin-7-yl)-2,5-dimethylpiperazine-1-carboxylate (16)

To solution of (2R,5S)-tert-butyl 4-((S)-3-((1-((benzyloxy)carbonyl)azetidin-3-yl)methyl)-10-(4-fluorophenyl)-5- oxo-9-(trifluoromethyl)-3,5-dihydro-2H-[1,4]thiazino[2,3,4-ij]quinazolin-7-yl)-2,5-dimethylpiperazine-1-carboxylate (60 mg, 0.077 mmol) in methanol (2 mL) was added palladium on charcoal (10%) (50 mg) at room temperature. The mixture was stirred under hydrogen at room temperature for 3 hours. After completion, the mixture was filtered and concentrated to afford (2R,5S)-tert-butyl 4-((S)-3-(azetidin-3-ylmethyl)-10-(4-fluorophenyl)-5-oxo-9-(trifluoromethyl)-3,5-dihydro-2H-[1,4]thiazino[2,3,4-ij]quinazolin-7-yl)-2,5-dimethylpiperazine-1-carboxylate (47 mg, 94% yield) as pale yellow solid. MS (ESI) m/z: 648.8 $[M+H]^+$.

(2R,5S)-tert-butyl 4-((S)-3-((1-(2,2-difluoroethyl)azetidin-3-yl)methyl)-10-(4-fluorophenyl)-5-oxo-9-(trifluoromethyl)-3,5-dihydro-2H-[1,4]thiazino[2,3,4-ij]quinazolin-7-yl)-2,5-dimethylpiperazine-1-carboxylate (17)

To solution of (2R,5S)-tert-butyl 4-((S)-3-(azetidin-3-ylmethyl)-10-(4-fluorophenyl)-5-oxo-9-(trifluoromethyl)-3,5-dihydro-2H-[1,4]thiazino[2,3,4-ij]quinazolin-7-yl)-2,5-dimethylpiperazine-1-carboxylate (47 mg, 0.07 mmol) and 1,1-difluoro-2-iodoethane (42 mg, 0.22 mmol) in acetonitrile (1 mL) was added potassium carbonate (30 mg, 0.22 mmol). The mixture was stirred at 90° C. under nitrogen protection overnight. After completed, the mixture was concentrated and purified by silica gel column eluting with dichloromethane/ammonia-methanol (40/1) to afford the (2R,5S)-tert-butyl 4-((S)-3-((1-(2,2-difluoroethyl)azetidin-3-yl)methyl)-10-(4-fluorophenyl)-5-oxo-9-(trifluoromethyl)-3,5-dihydro-2H-[1,4]thiazino[2,3,4-ij]quinazolin-7-yl)-2,5-dimethylpiperazine-1-carboxylate (40 mg, 78% yield) as pale yellow solid. MS (ESI) m/z: 712.8 $[M+H]^+$.

(S)-3-((1-(2,2-difluoroethyl)azetidin-3-yl)methyl)-7-((2S,5R)-2,5-dimethylpiperazin-1-yl)-10-(4-fluorophenyl)-9-(trifluoromethyl)-2H-[1,4]thiazino[2,3,4-ij]quinazolin-5(3H)-one (18)

To a solution of (2R,5S)-tert-butyl 4-((S)-3-((1-(2,2-difluoroethyl)azetidin-3-yl)methyl)-10-(4-fluorophenyl)-5-oxo-9-(trifluoromethyl)-3,5-dihydro-2H-[1,4]thiazino[2,3,4-ij]quinazolin-7-yl)-2,5-dimethylpiperazine-1-carboxylate (40 mg, 0.056 mmol) in dichloromethane (1 mL) was added trifluoroacetic acid (1 mL) at 0° C. The reaction solution was stirred at room temperature for 1 hour. After completion, the mixture was concentrated and adjusted pH to 8-9 by ammonia in methanol. The mixture was concentrated and purified by silica gel column eluting with dichloromethane/methanol (containing 0.5% ammonia) (20/1) to afford the (S)-3-((1-(2,2-difluoroethyl)azetidin-3-yl)methyl)-7-((2S,5R)-2,5-dimethylpiperazin-1-yl)-10-(4-fluorophenyl)-9-(trifluoromethyl)-2H-[1,4]thiazino[2,3,4-ij]quinazolin-5(3H)-one (33 mg, 96% yield) as pale yellow solid. MS (ESI) m/z: 612.7 $[M+H]^+$.

(S)-7-((2S,5R)-4-acryloyl-2,5-dimethylpiperazin-1-yl)-3-((1-(2,2-difluoroethyl)azetidin-3-yl)methyl)-10-(4-fluorophenyl)-9-(trifluoromethyl)-2H-[1,4]thiazino[2,3,4-ij]quinazolin-5(3H)-one (19)

To a mixture of (S)-3-((1-(2,2-difluoroethyl)azetidin-3-yl)methyl)-7-((2S,5R)-2,5-dimethylpiperazin-1-yl)-10-(4-fluorophenyl)-9-(trifluoromethyl)-2H-[1,4]thiazino[2,3,4-ij]quinazolin-5(3H)-one (33 mg, 0.054 mmol) and triethyl amine (11 mg, 0.108 mmol) in dichloromethane (1 mL) was added acrylic anhydride (7 mg, 0.054 mmol) at 0° C. The mixture was stirred at 0° C. for 1 hour. After completion, the mixture was poured into ice-water (20 mL) and extracted with dichloromethane (3×15 mL), dried over $Ns_2SO_4$, and concentrated. The residue was purified by preparative high Performance liquid chromatography (20% to 95% acetonitrile in water as gradient) to afford (S)-7-((2S,5R)-4-acryloyl-2,5-dimethylpiperazin-1-yl)-3-((1-(2,2-difluoroethyl)azetidin-3-yl)methyl)-10-(4-fluorophenyl)-9-(trifluoromethyl)-2H-[1,4]thiazino[2,3,4-ij]quinazolin-5(3H)-one (14 mg, 39% yield) as a white solid. MS (ESI) m/z: 666.3 $[M+H]^+$.

$^1H$ NMR (400 MHz, $CDCl_3$) δ 7.84 (s, 1H), 7.26-7.25 (m, 1H), 7.21-7.17 (m, 3H), 6.67-6.51 (m, 1H), 6.38 (t, J=15.6 Hz, 1H), 5.84-5.54 (m, 2H), 5.27-5.26 (m, 1H), 5.06-5.01 (m, 0.5H), 4.84-4.83 (m, 0.5H), 4.71-4.70 (m, 0.5H), 4.42-4.32 (m, 1.5H), 4.06-4.03 (m, 0.5H), 3.80-3.67 (m, 2H), 3.59-3.52 (m, 2H), 3.33-3.29 (m, 0.5H), 3.06-2.97 (m, 3H), 2.88-2.84 (m, 1H), 2.79-2.70 (m, 2H), 2.61-2.53 (m, 1H), 2.06 (t, J=6.8 Hz, 1H), 1.47-1.38 (m, 6H).

O. Example 496

(3S)-7-((2S,5R)-4-acryloyl-2,5-dimethylpiperazin-1-yl)-9-chloro-10-(5-chloro-2,4-difluorophenyl)-3-(methoxymethyl)-2H-[1,4]thiazino[2,3,4-ij]quinazolin-5(3H)-one (8)

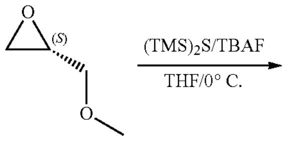

1

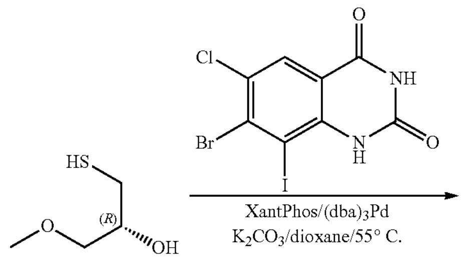

2

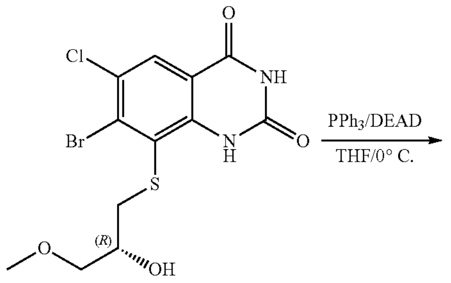

3

-continued

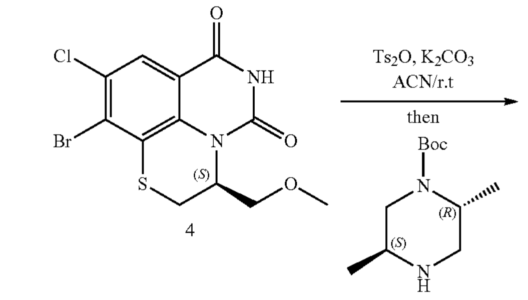

4

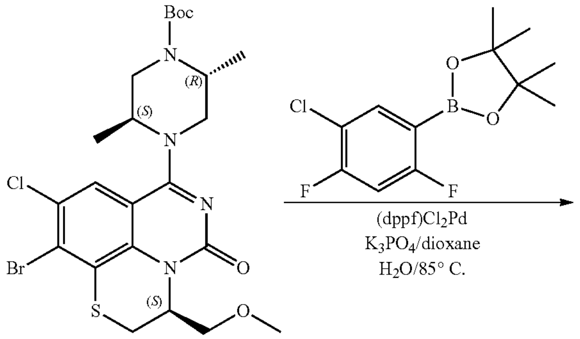

5

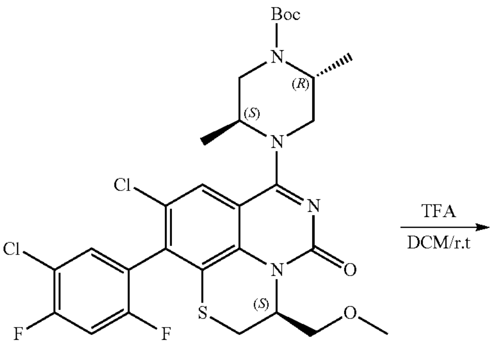

6

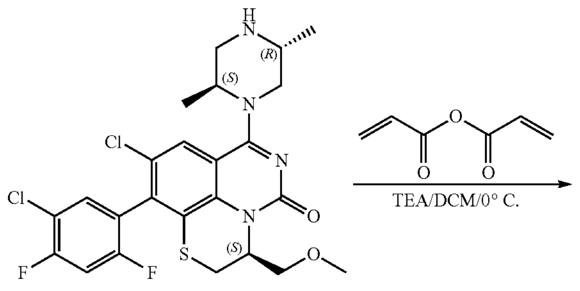

7

-continued

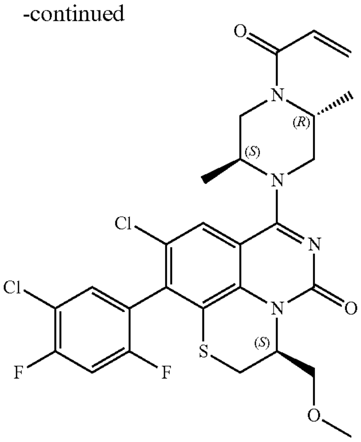

8

(R)-1-mercapto-3-methoxypropan-2-ol (2)

To a mixture of (S)-2-(methoxymethyl)oxirane (10.00 g, 113.6 mmol) in tetrahydrofuran (150 mL) was added 1,1,1,3,3,3-hexamethyldisilathiane (30.33 g, 170.4 mmol) and tetrabutylammonium fluoride (1.0 M in tetrahydrofuran, 34.1 mL, 34.1 mmol) at 0° C. The mixture was stirred at room temperature for 2 hrs. After completion, the mixture was poured into water (300 mL), extracted with ethyl acetate (3×200 mL). The combined organic phase was washed with brine (300 mL) and dried over anhydrous sodium sulfate. After filtration and concentration, the residue was purified by silica gel column eluting with petroleum ether/ethyl acetate (3/1) to afford (R)-1-mercapto-3-methoxypropan-2-ol (17.0 g, crude) as a colorless oil.

$^1$H NMR (300 MHz, $CDCl_3$) δ 3.86-3.82 (m, 1H), 3.49-3.46 (m, 1H), 3.41-3.37 (m, 4H), 2.71-2.64 (m, 1H), 1.55-1.50 (m, 1H).

(R)-7-bromo-6-chloro-8-((2-hydroxy-3-methoxypropyl)thio)quinazoline-2,4(1H,3H)-dione (3)

To a solution of 7-bromo-6-chloro-8-iodoquinazoline-2,4(1H,3H)-dione (4.00 g, 9.97 mmol) in dioxane (100 mL) were added potassium carbonate (4.13 g, 29.91 mmol), (R)-1-mercapto-3-methoxypropan-2-ol (2.43 g, 19.94 mmol), 4,5-bis(diphenyl-phosphino)-9,9-dimethylxanthene (1.15 g, 1.99 mmol) and tris(dibenzylideneacetone) dipalladium (915 mg, 1.0 mmol). The mixture was stirred at 55° C. under nitrogen atmosphere for 18 hrs. After completion, the mixture was diluted with tetrahydrofuran (300 mL) and filtered. After concentration, the residue was purified by silica gel column chromatography eluting with dichloromethane/methanol (100/1) to afford (R)-7-bromo-6-chloro-8-((2-hydroxy-3-methoxypropyl)thio)quinazoline-2,4(1H,3H)-dione (3.15 g, 80% yield) as a white solid. MS (ESI) m/z: 387.0 [M+H]$^+$.

(S)-10-bromo-9-chloro-3-(methoxymethyl)-2H-[1,4]thiazino[2,3,4-ij]quinazoline-5,7(3H,6H)-dione (4)

To a mixture of (R)-7-bromo-6-chloro-8-((2-hydroxy-3-methoxypropyl)thio)quinazoline-2,4(1H,3H)-dione (3.15 g, 8.16 mmol) and triphenylphosphoranylidene (4.28 g, 16.32 mmol) in tetrahydrofuran (160 mL) was added diethyl azodicarboxylate (2.84 g, 16.32 mmol) at 0° C. The mixture was stirred at 0° C. for 45 min. After completion, the mixture was poured into ice-water (300 mL) and extracted with ethyl acetate (3×500 mL). After concentration, the residue was purified by Flash chromatography column (C18, acetonitrile/water=30% to 95% as gradient) to afford (S)-10-bromo-9-chloro-3-(methoxymethyl)-2H-[1,4]thiazino[2,3,4-ij]quinazoline-5,7(3H,6H)-dione (1.84 g, 60% yield) as a white solid. MS (ESI) m/z: 378.0 [M+H]$^+$.

(2R,5S)-tert-butyl 4-((S)-10-bromo-9-chloro-3-(methoxymethyl)-5-oxo-3,5-dihydro-2H-[1,4]thiazino[2,3,4-ij]quinazolin-7-yl)-2,5-dimethylpiperazine-1-carboxylate (5)

To a mixture of (S)-10-bromo-9-chloro-3-(methoxymethyl)-2H-[1,4]thiazino[2,3,4-ij]quinazoline-5,7(3H,6H)-dione (1.84 g, 4.88 mmol) and potassium carbonate (6.73 g, 48.8 mmol) in acetonitrile (100 mL) was added 4-methylbenzenesulfonic anhydride (3.18 g, 9.76 mmol) at 0° C. The mixture was stirred at 0° C. for 30 min and at 30° C. for 1 hour. After completion, (2R,5S)-tert-butyl 2,5-dimethylpiperazine-1-carboxylate (2.09 g, 9.76 mmol) was added into the reaction solution. The reaction mixture was stirred at 0° C. for 1 hour. After completion, the mixture was poured into ice-water (300 mL) and extracted with ethyl acetate (3×200 mL). After concentration, the residue was purified by Flash chromatography column (C18, acetonitrile/water=20% to 95%) to afford (2R,5S)-tert-butyl 4-((S)-10-bromo-9-chloro-3-(methoxymethyl)-5-oxo-3,5-dihydro-2H-[1,4]thiazino[2,3,4-ij]quinazolin-7-yl)-2,5-dimethylpiperazine-1-carboxylate (1.56 g, 56% yield) as a pale-white solid. MS (ESI) m/z: 575.1 [M+H]$^+$.

(2R,5S)-tert-butyl 4-((3S)-9-chloro-10-(5-chloro-2,4-difluorophenyl)-3-(methoxymethyl)-5-oxo-3,5-dihydro-2H-[1,4]thiazino[2,3,4-ij]quinazolin-7-yl)-2,5-dimethylpiperazine-1-carboxylate (6)

To a solution of (2R,5S)-tert-butyl 4-((S)-10-bromo-9-chloro-3-(methoxymethyl)-5-oxo-3,5-dihydro-2H-[1,4]thiazino[2,3,4-ij]quinazolin-7-yl)-2,5-dimethylpiperazine-1-carboxylate (250 mg, 0.44 mmol) in 1,4-dioxane (8 mL) and water (1 mL) were added tripotassium phosphate (373 mg, 1.76 mmol), 2-(5-chloro-2,4-difluorophenyl)-4,4,5,5-tetramethyl-1,3,2-dioxaborolane (724 mg, 2.64 mmol), and [1'1-bis(diphenylphosphino)ferrocene] dichloro palladiuM (II) (29 mg, 0.04 mmol). The mixture was stirred at 85° C. under nitrogen atmosphere for 10 hours. After completion, the mixture was diluted with tetrahydrofuran (300 mL) and filtered. After concentration, the residue was purified by silica gel column chromatography eluting with a gradient of dichloromethane/methanol 100/1 to 30/1 to afford (2R,5S)-tert-butyl 4-((3S)-9-chloro-10-(5-chloro-2,4-difluorophenyl)-3-(methoxymethyl)-5-oxo-3,5-dihydro-2H-[1,4]thiazino[2,3,4-ij]quinazolin-7-yl)-2,5-dimethylpiperazine-1-carboxylate (260 mg, crude) as a yellow solid. MS (ESI) m/z: 641.6 [M+H]$^+$.

(3S)-9-chloro-10-(5-chloro-2,4-difluorophenyl)-7-((2S,5R)-2,5-dimethylpiperazin-1-yl)-3-(methoxymethyl)-2H-[1,4]thiazino[2,3,4-ij]quinazolin-5(3H)-one (7)

To a cooled mixture of (2R,5S)-tert-butyl 4-((3S)-9-chloro-10-(5-chloro-2,4-difluorophenyl)-3-(methoxymethyl)-5-oxo-3,5-dihydro-2H-[1,4]thiazino[2,3,4-ij]quinazolin-7-yl)-2,5-dimethylpiperazine-1-carboxylate (260 mg, 0.44 mmol) in dichloromethane (5 ml) was added trifluoroacetic acid (2 mL) at 0° C. The reaction solution was stirred at room temperature for 1 h. After completion, the mixture was concentrated, the residue was purified by column using a mixture of dichloromethane/methanol (15:1) to afford (3S)-9-chloro-10-(5-chloro-2,4-difluorophenyl)-7-((2S,5R)-2,5-dimethylpiperazin-1-yl)-3-(methoxymethyl)-2H-[1,4]thiazino[2,3,4-ij]quinazolin-5(3H)-one (160 mg, crude) as a yellow-brown solid. MS (ESI) m/z: 541.1 [M+H]$^+$.

(3S)-7-((2S,5R)-4-acryloyl-2,5-dimethylpiperazin-1-yl)-9-chloro-10-(5-chloro-2,4-difluorophenyl)-3-(methoxymethyl)-2H-[1,4]thiazino[2,3,4-ij]quinazolin-5(3H)-one (8)

To a mixture of (3S)-9-chloro-10-(5-chloro-2,4-difluorophenyl)-7-((2S,5R)-2,5-dimethylpiperazin-1-yl)-3-(methoxymethyl)-2H-[1,4]thiazino[2,3,4-ij]quinazolin-5(3H)-one (130 mg, 0.24 mmol) and triethyl amine (49 mg, 0.48 mmol) in dichloromethane (5 ml) was added acrylic anhydride (45 mg, 0.36 mmol) at 0° C. The mixture was stirred at 0° C. for 1 h. After completion, the mixture was poured into ice-water (50 mL) and extracted with ethyl acetate (3×20 mL). After concentration, the residue was purified by preparative High Performance Liquid Chromatography (20% to 95% acetonitrile in water) to afford (3S)-7-((2S,5R)-4-acryloyl-2,5-dimethylpiperazin-1-yl)-9-chloro-10-(5-chloro-2,4-difluorophenyl)-3-(methoxymethyl)-2H-[1,4]thiazino[2,3,4-ij]quinazolin-5(3H)-one (50 mg, 35% yield) as a white solid. $^1$H NMR (400 MHz, $CDCl_3$) δ 7.55-7.54 (m, 1H), 7.33-7.29 (m, 1H), 7.11-7.06 (m, 1H), 6.66-6.50 (m, 1H), 6.37 (t, J=15.6 Hz, 1H), 5.77 (t, J=7.6 Hz, 1H), 5.51-5.44 (m, 1H), 5.04-4.99 (m, 0.6H), 4.85-4.69 (m, 1H), 4.42-4.30 (m, 1.4H), 4.07-4.01 (m, 0.5H), 3.80-3.57 (m, 4H), 3.41-3.33 (m, 4.5H), 3.06-3.01 (m, 1H), 1.42-1.33 (m, 6H). MS (ESI) m/z: 595.1 [M+H]$^+$.

P. Example 498

(3S)-7-((2S,5R)-4-acryloyl-2,5-dimethylpiperazin-1-yl)-10-(2,4-difluorophenyl)-3-((2-methoxyethoxy)methyl)-9-(trifluoromethyl)-2H-[1,4]thiazino[2,3,4-ij]quinazolin-5(3H)-one

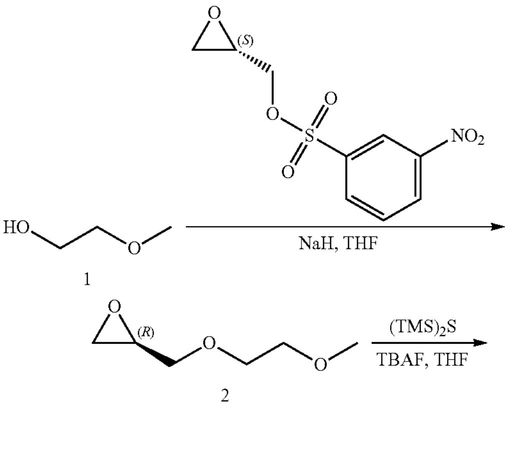

1
2

-continued
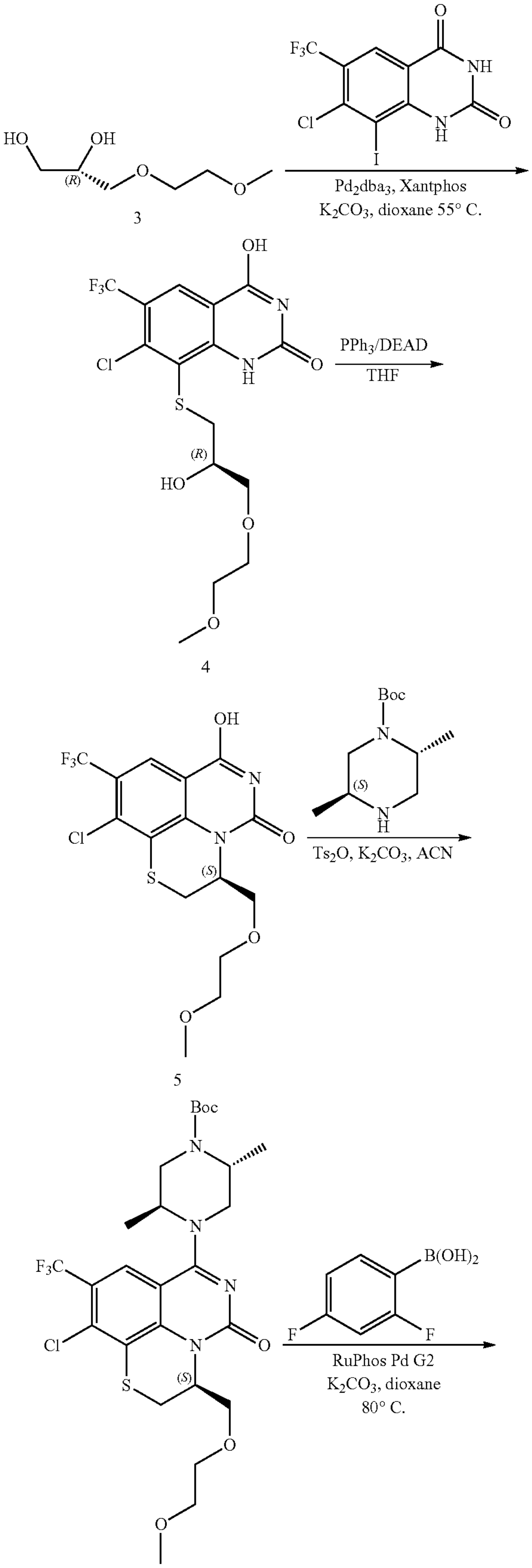
3
4
5
6
-continued
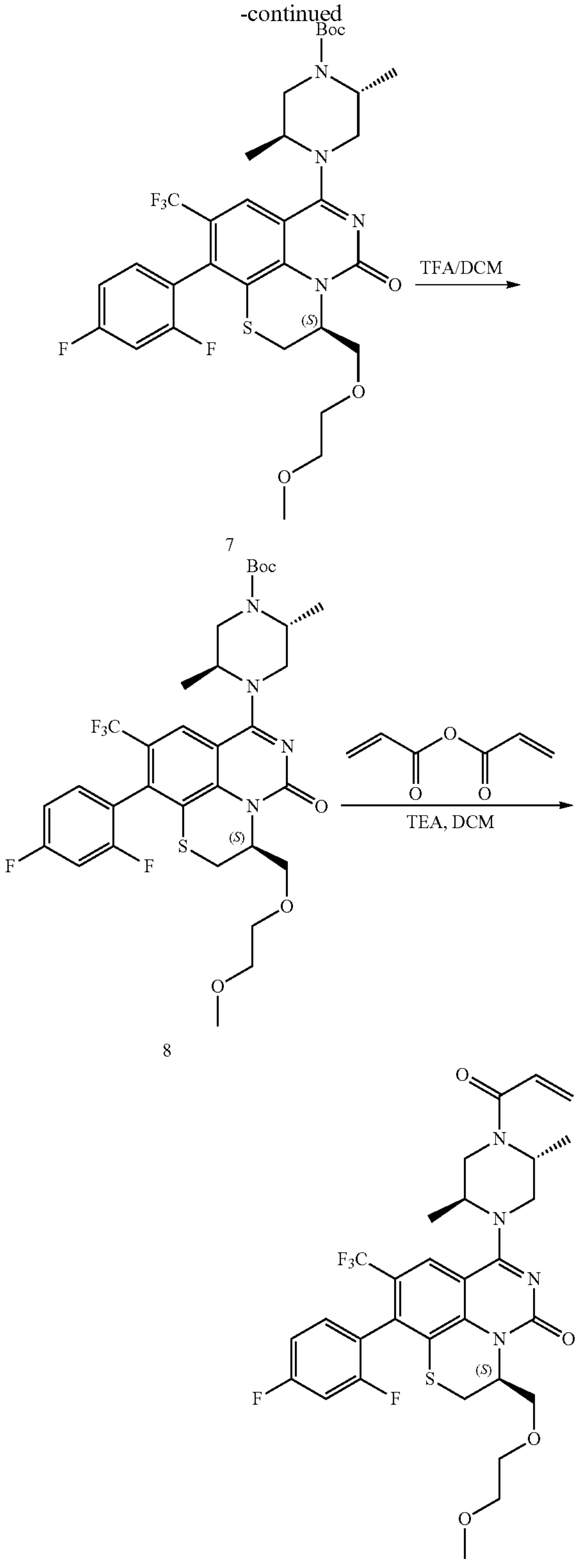
7
8
9
(R)-2-((2-methoxyethoxy)methyl)oxirane (2)
To a mixture of 2-methoxyethanol (40.00 g, 525.66 mmol) in tetrahydro-furan (3200 mL) was added sodium hydride (60% dispersed in mineral oil, 37.8 g, 946.20 mmol). The mixture was stirred at 0° C. for 1 hour. Then (S)-oxiran-2-ylmethyl 3-nitrobenzenesulfonate (40.00 g, 525.66 mmol) was added to the above solution, the mixture was stirred at room temperature for 3 hours. After completion, the mixture was poured into water (3200 mL), extracted with ethyl acetate (3×1000 mL). The combined organic phase was washed with brine (1000 mL) and dried over anhydrous sodium sulfate. After filtration and concentration, the residue was purified by silica gel column with petroleum ether to afford (R)-2-((2-methoxyethoxy)methyl) oxirane (27.00 g, crude) as colorless oil.

$^1$H NMR (400 MHz, $CDCl_3$) δ 3.82-3.77 (m, 1H), 3.71-3.64 (m, 2H), 3.58-3.54 (m, 2H), 3.46-3.38 (m, 4H), 3.18-3.16 (m, 1H), 2.81-2.78 (m, 1H), 2.62-2.59 (m, 1H).

(R)-1-mercapto-3-(2-methoxyethoxy)propan-2-ol (3)

To a mixture of (R)-2-((2-methoxyethoxy)methyl)oxirane (27.00 g, 204.3 mmol) in tetrahydrofuran (300 mL) was added 1,1,1,3,3,3-hexamethyldisilathiane (40.10 g, 224.7 mmol) and tetrabutylammonium fluoride (1.0 M in tetrahydrofuran, 15.17 mL, 224.7 mmol) at 0° C. The mixture was stirred at room temperature for 2 hours. After completion, the mixture was poured into water (300 mL), extracted with ethyl acetate (3×200 mL). The combined organic phase was washed with brine (300 mL) and dried over anhydrous sodium sulfate. After filtration and concentration, the residue was purified by silica gel column eluting with a mixture of petroleum ether/ethyl acetate (3/1) to afford (R)-1-mercapto-3-(2-methoxyethoxy)propan-2-ol (7.2 g, 21% yield) as a colorless oil.

$^1$H NMR (400 MHz, $CDCl_3$) δ 3.86-3.83 (m, 1H), 3.69-3.65 (m, 2H), 3.57-3.51 (m, 3H), 3.40-3.39 (m, 3H), 3.08-2.98 (m, 1H), 2.70-2.63 (m, 2H), 1.53 (t, J=1.2 Hz, 1H).

(R)-7-chloro-4-hydroxy-8-((2-hydroxy-3-(2-methoxyethoxy)propyl)thio)-6-(trifluoromethyl)quinazolin-2(1H)-one (4)

To a solution of 7-chloro-8-iodo-6-(trifluoromethyl)quinazoline-2,4(1H, 3H)-dione (4.00 g, 10.24 mmol) in dioxane (100 mL) were added potassium carbonate (4.25 g, 30.73 mmol), (R)-7-chloro-4-hydroxy-8-((2-hydroxy-3-(2-methoxyethoxy)propyl)thio)-6-(trifluoromethyl)quinazolin-2(1H)-one (2.55 g, 15.37 mmol), 4,5-bis(diphenyl-phosphino)-9,9-dimethylxanthene (0.89 g, 1.54 mmol) and tris (dibenzylideneacetone) dipalladium (0.94 g, 1.02 mmol). The mixture was stirred at 55° C. under nitrogen atmosphere for 18 hours. After completion, the mixture was diluted with tetrahydrofuran (300 mL) and filtered. After concentration, the residue was purified by silica gel column chromatography eluting with a gradient of dichloromethane/methanol (100/1 to 8/1) to afford the title product (S)-10-chloro-7-hydroxy-3-((2-methoxyethoxy) methyl)-9-(trifluoromethyl)-2H-[1,4]thiazino[2,3,4-ij]quinazolin-5(3H)-one (2.15 g, 49% yield) as a white solid. MS (ESI) m/z: 429.0 [M+H]$^+$.

(S)-10-chloro-7-hydroxy-3-((2-methoxyethoxy) methyl)-9-(trifluoromethyl)-2H-[1,4]thiazino[2,3,4-ij]quinazolin-5(3H)-one (5)

To a mixture of (S)-10-chloro-7-hydroxy-3-((2-methoxyethoxy)methyl)-9-(trifluoromethyl)-2H-[1,4]thiazino[2,3,4-ij]quinazolin-5(3H)-one (2.09 g, 4.88 mmol) and triphenylphosphoranylidene (5.12 g, 19.51 mmol) in tetrahydrofuran (700 ml) was added 2,5-dichloro-2,5-dimethylhexane (7.16 g, 19.51 mmol) at 0° C. The mixture was stirred at 0° C. for 45 min. After completion, the mixture was poured into ice-water (1500 mL) and extracted with ethyl acetate (3×500 mL). After concentration, the residue was purified by Flash chromatography column (C18, acetonitrile/water=30% to 95%) to afford (S)-10-chloro-7-hydroxy-3-((2-methoxyethoxy) methyl)-9-(trifluoromethyl)-2H-thiazino[2,3,4-ij] quinazolin-5(3H)-one (1.58 g, 79% yield) as a white solid. MS (ESI) m/z: 411.0 [M+H]$^+$.

(2R,5S)-tert-butyl 4-((S)-10-chloro-3-((2-methoxyethoxy)methyl)-5-oxo-9-(trifluoromethyl)-3,5-dihydro-2H-[1,4]thiazino[2,3,4-ij]quinazolin-7-yl)-2,5-dimethylpiperazine-1-carboxylate (6)

To a mixture of (S)-10-chloro-7-hydroxy-3-((2-methoxyethoxy) methyl)-9-(trifluoromethyl)-2H-[1,4]thiazino[2,3,4-ij]quinazolin-5(3H)-one (1.58 g, 3.85 mmol) and potassium carbonate (5.32 g, 38.49 mmol) in acetonitrile (100 mL) was added 4-methylbenzenesulfonic anhydride (3.77 g, 11.55 mmol) at 0° C. The mixture was stirred at 0° C. for 30 min and at 30° C. for 1 hour. After completion, (2R,5S)-tert-butyl 2,5-dimethylpiperazine-1-carboxylate (3.30 g, 15.40 mmol) was added into the reaction solution. The reaction mixture was stirred at 0° C. for 1 hour. After completion, the mixture was poured into ice-water (300 mL) and extracted with ethyl acetate (3×200 mL). After concentration, the residue was purified by Flash chromatography column (C18, acetonitrile/water=20% to 95%) to afford (2R,5S)-tert-butyl 4-((S)-10-chloro-3-((2-methoxyethoxy)methyl)-5-oxo-9-(trifluoromethyl)-3,5-dihydro-2H-[1,4]thiazino[2,3,4-ij] quinazolin-7-yl)-2,5-dimethylpiperazine-1-carboxylate (1.97 g, 85% yield) as a yellow solid. MS (ESI) m/z: 607.1 [M+H]$^+$.

(2R, 5S)-tert-butyl 4-((3S)-10-(2,4-difluorophenyl)-3-((2-methoxyethoxy) methyl)-5-oxo-9-(trifluoromethyl)-3,5-dihydro-2H-[1,4]thiazino[2,3,4-ij]quinazolin-7-yl)-2,5-dimethylpiperazine-1-carboxylate (7)

To a solution of (2R,5S)-tert-butyl 4-((S)-10-chloro-3-((2-methoxyethoxy) methyl)-5-oxo-9-(trifluoromethyl)-3,5-dihydro-2H-[1,4]thiazino[2,3,4-ij]quinazolin-7-yl)-2,5-dimethylpiperazine-1-carboxylate (350 mg, 0.58 mmol) in 1,4-dioxane (6 mL) and water (1 mL) were added tripotassium phosphate (734 mg, 3.46 mmol), (2,4-difluorophenyl) boronic acid (456 mg, 2.89 mmol), and chloro(2-dicyclohexylphosphino-2', 6'-diisopropoxy-1,1'-biphenyl)[2-(2'-amino-1,1'-biphenyl)]palladium(II) (45 mg, 0.058 mmol). The mixture was stirred at 85° C. under nitrogen atmosphere for 4 hours. After completion, the mixture was diluted with tetrahydrofuran (300 mL) and filtered. After concentration, the residue was purified by silica gel column chromatography using a gradient of dichloromethane/methanol (100/1 to 8/1) to afford (2R,5S)-tert-butyl 4-((3S)-10-(2,4-difluorophenyl)-3-((2-methoxyethoxy) methyl)-5-oxo-9-(trifluoromethyl)-3,5-dihydro-2H-[1,4]thiazino[2,3,4-ij]quinazolin-7-yl)-2,5-dimethylpiperazine-1-carboxylate (2.15 g, 49% yield) as a white solid. MS (ESI) m/z: 685.1 [M+H]$^+$.

(3S)-10-(2,4-difluorophenyl)-7-((2S,5R)-2,5-dimethylpiperazin-1-yl)-3-((2-methoxyethoxy)methyl)-9-(trifluoromethyl)-2H-[1,4]thiazino[2,3,4-ij]quinazolin-5(3H)-one (8)

To a cooled mixture of (2R,5S)-tert-butyl 4-((3S)-10-(2,4-difluorophenyl)-3-((2-methoxyethoxy)methyl)-5-oxo-9-

(trifluoromethyl)-3,5-dihydro-2H-[1,4]thiazino[2,3,4-ij]quinazolin-7-yl)-2,5-dimethylpiperazine-1-carboxylate (410 mg, 0.58 mmol) in dichloromethane (5 ml) was added trifluoroacetic acid (5 mL) at 0° C. The reaction solution was stirred at room temperature for 1 hour. After completion, the mixture was concentrated, the residue was purified by column eluting with dichloromethane/methanol (5/1) to afford (3S)-10-(2,4-difluorophenyl)-7-((2S, 5R)-2,5-dimethylpiperazin-1-yl)-3-((2-methoxyethoxy)methyl)-9-(trifluoromethyl)-2H-[1,4]thiazino[2,3,4-ij]quinazolin-5(3H)-one (701 mg, crude) as a yellow-brown solid. MS (ESI) m/z: 585.1 [M+H]+.

(3S)-7-((2S,5R)-4-acryloyl-2,5-dimethylpiperazin-1-yl)-10-(2,4-difluorophenyl)-3-((2-methoxyethoxy) methyl)-9-(trifluoromethyl)-2H-[1,4]thiazino[2,3,4-ij]quinazolin-5(3H)-one (9)

To a mixture of (3S)-10-(2,4-difluorophenyl)-7-((2S, 5R)-2,5-dimethylpiperazin-1-yl)-3-((2-methoxyethoxy)methyl)-9-(trifluoromethyl)-2H-[1,4]thiazino[2,3,4-ij]quinazolin-5 (3H)-one (655 mg, 0.54 mmol) and triethyl amine (164 mg, 1.62 mmol) in dichloromethane (10 ml) was added acrylic anhydride (68 mg, 0.54 mmol) at 0° C. The mixture was stirred at 0° C. for 1 hour. After completion, the mixture was poured into ice-water (50 mL) and extracted with ethyl acetate (3×20 mL). After concentration, the residue was purified by preparative High Performance Liquid Chromatography (20% to 95% acetonitrile in water) to afford (3S)-7-((2S,5R)-4-acryloyl-2,5-dimethylpiperazin-1-yl)-10-(2,4-difluorophenyl)-3-((2-methoxyethoxy) methyl)-9-(trifluoromethyl)-2H-[1,4]thiazino[2,3,4-ij]quinazolin-5(3H)-one (113 mg, 33% yield) as a white solid. MS (ESI) m/z: 639.1 [M+H]+.

$^1$H NMR (400 MHz, $CDCl_3$) δ 7.87-7.83 (m, 1H), 7.19-7.15 (m, 1H), 7.03-6.95 (m, 2H), 6.67-6.51 (m, 1H), 6.37 (t, J=14.4 Hz, 1H), 5.78 (t, J=9.2 Hz, 1H), 5.50-5.36 (m, 1H), 5.14-5.00 (m, 0.6H), 4.78-4.66 (m, 1H), 4.45-4.41 (m, 1H), 4.41-4.34 (m, 0.4H), 4.16-4.08 (m, 0.6H), 3.78-3.63 (m, 6H), 3.52 (t, J=4.8 Hz, 2H), 3.41-3.38 (m, 1H), 3.35 (s, 3H), 3.26-3.22 (m, 0.4H), 3.05-2.95 (m, 1H), 1.50-1.44 (m, 6H).

Q. Example 500

(3S)-3-((1S,4S)-2-oxa-5-azabicyclo[2.2.1]heptan-5-ylmethyl)-7-((2S,5R)-4-acryloyl-2,5-dimethylpiperazin-1-yl)-9-chloro-10-(5-chloro-2,4-difluorophenyl)-2H-[1,4]thiazino[2,3,4-ij]quinazolin-5(3H)-one

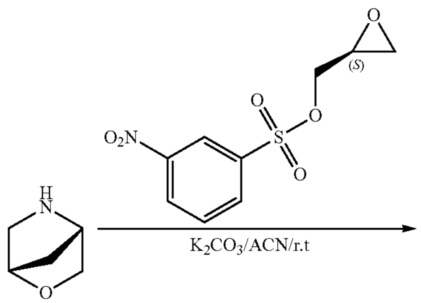

1

-continued

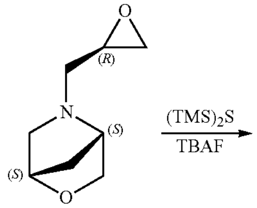

2

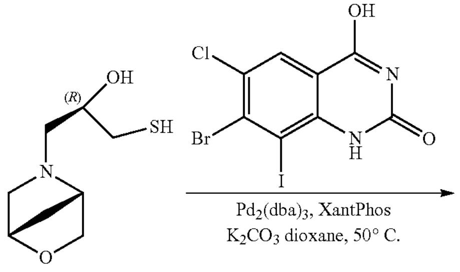

3

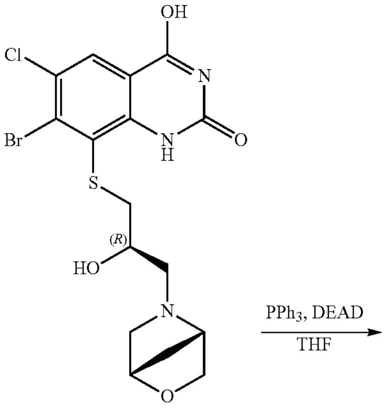

4

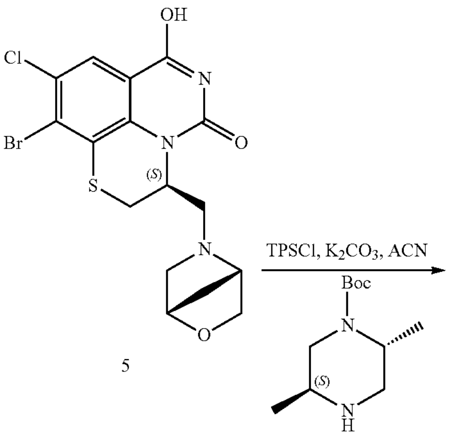

5

-continued

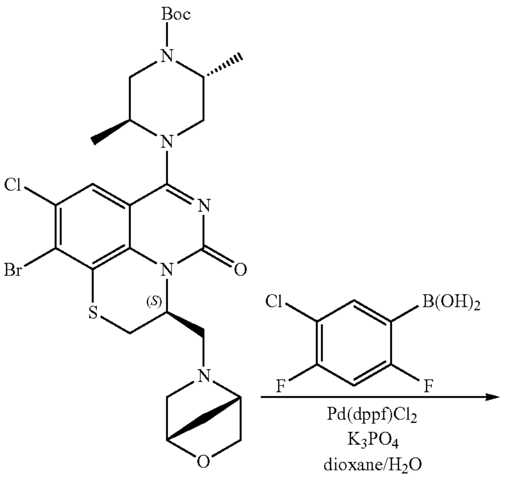

6

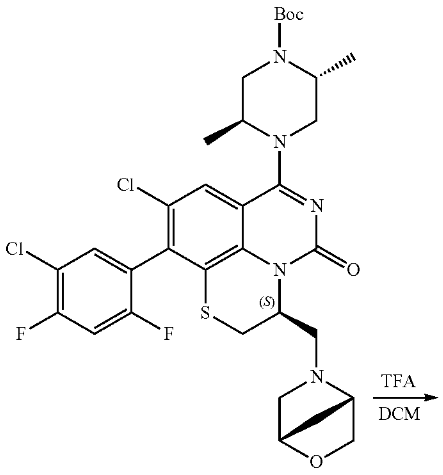

7

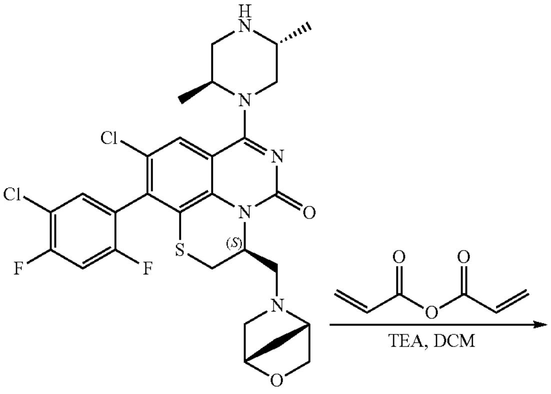

8

-continued

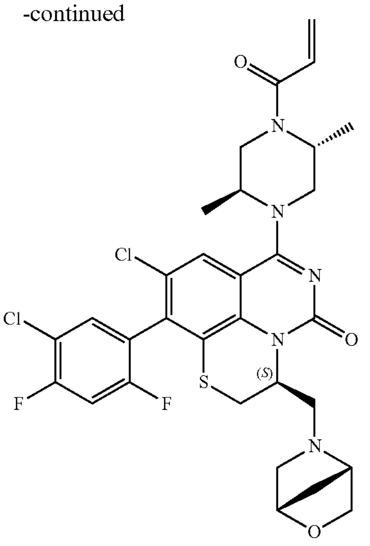

9

(1S,4S)-5-((R)-oxiran-2-ylmethyl)-2-oxa-5-azabicyclo[2.2.1]heptanes (2)

To a mixture of (S)-oxiran-2-ylmethyl 3-nitrobenzenesulfonate (38.2 g, 147.5 mmol) and (1S,4S)-2-oxa-5-azabicyclo[2.2.1]heptane (20.0 g, 147.5 mmol) in acetonitrile (300 mL) was added potassium carbonate (61 g, 442.5 mmol) at 0° C. under nitrogen atmosphere. The mixture was stirred at 0° C. for 16 hours. After completion, the mixture was concentrated and the residue was purified by silica gel column eluting with a mixture of dichloromethane/methanol (20/1) to afford the product (15.0 g, 66% yield) as a yellow oil. MS (ESI) m/z: 156.1 $[M+H]^+$.

(R)-1-((1S,4S)-2-oxa-5-azabicyclo[2.2.1]heptan-5-yl)-3-mercaptopropan-2-ol (3)

To a mixture of (1S,4S)-5-((R)-oxiran-2-ylmethyl)-2-oxa-5-azabicyclo[2.2.1]heptane (6 g, 38.7 mmol) in tetrahydrofuran (60 mL) were added 1,1,1,3,3,3-hexamethyldisilathiane (8.9 g, 50.3 mmol) and tetrabutylammonium fluoride (1.0 M in tetrahydrofuran, 11.6 mL, 11.6 mmol) at 0° C. The mixture was stirred at room temperature for 2 hours. After completion, the mixture was poured into water (60 mL), extracted with ethyl acetate (3×100 mL). The organic phase was washed with brine (200 mL) and dried over anhydrous sodium sulfate. After filtration and concentration, the residue was purified by silica gel column eluting with a mixture of dichloromethane/methanol (50/1) to afford (R)-1-((1S,4S)-2-oxa-5-azabicyclo[2.2.1]heptan-5-yl)-3-mercaptopropan-2-ol (2.6 g, 35% yield) as a colorless oil. MS (ESI) m/z: 190.1 $[M+H]^+$.

8-(((R)-3-((1S,4S)-2-oxa-5-azabicyclo[2.2.1]heptan-5-yl)-2-hydroxypropyl)thio)-7-bromo-6-chloro-4-hydroxyquinazolin-2(1H)-one (4)

To a solution of 7-bromo-6-chloro-4-hydroxy-8-iodoquinazolin-2(1H)-one (1.00 g, 2.5 mmol) in dioxane (30 mL) were added potassium carbonate (1.38 g, 10.0 mmol), (R)-1-((1S,4S)-2-oxa-5-azabicyclo[2.2.1]heptan-5-yl)-3-mercaptopropan-2-ol (742.5 mg, 3.75 mmol), 4,5-bis(diphenylphosphino)-9,9-dimethylxanthene (289 mg, 0.5 mmol) and tris(dibenzylideneacetone) dipalladium (421 mg, 0.46 mmol). The mixture was stirred at 55° C. under nitrogen atmosphere for 16 hours. After completion, the mixture was diluted with tetrahydrofuran (100 mL) and filtered. The filtrate was concentrated and the residue was purified by silica gel column chromatography using a gradient of dichloromethane/methanol (100/1 to 20/1) to afford 8-(((R)-3-((1S,4S)-2-oxa-5-azabicyclo[2.2.1]heptan-5-yl)-2-hydroxypropyl)thio)-7-bromo-6-chloro-4-hydroxyquinazolin-2(1H)-one (560 mg, 48% yield) as a yellow solid. MS (ESI) m/z: 462.1 $[M+H]^+$.

(S)-3-((1S,4S)-2-oxa-5-azabicyclo[2.2.1]heptan-5-ylmethyl)-10-bromo-9-chloro-7-hydroxy-2H-[1,4]thiazino[2,3,4-ij]quinazolin-5(3H)-one (5)

To a mixture of 8-(((R)-3-((1S,4S)-2-oxa-5-azabicyclo[2.2.1]heptan-5-yl)-2-hydroxypropyl)thio)-7-bromo-6-chloro-4-hydroxyquinazolin-2(1H)-one (560 mg, 1.21 mmol) and triphenylphosphine (579 mg, 1.5 mmol) in tetrahydrofuran (200 mL) was added diethyl azodicarboxylate (810 mg, 1.5 mmol) at 0° C. The mixture was stirred at 0° C. for 45 min. After completion, the mixture was poured into ice-water (50 mL) and extracted with ethyl acetate (3×50 mL). The mixture was concentrated and the residue was purified by flash chromatography column (C18, acetonitrile/water=30% to 95%) to afford (S)-3-((1S,4S)-2-oxa-5-azabicyclo[2.2.1]heptan-5-ylmethyl)-10-bromo-9-chloro-7-hydroxy-2H-[1,4]thiazino[2,3,4-ij]quinazolin-5(3H)-one (500 mg, 85% yield) as a white solid. MS (ESI): m/z: 444.3 $[M+H]^+$.

(2R,5S)-tert-butyl 4-((S)-3-((1S,4S)-2-oxa-5-azabicyclo[2.2.1]heptan-5-ylmethyl)-10-bromo-9-chloro-5-oxo-3,5-dihydro-2H-[1,4]thiazino[2,3,4-ij]quinazolin-7-yl)-2,5-dimethylpiperazine-1-carboxylate (6)

To a mixture of (S)-3-((1R,4S)-2-oxa-5-azabicyclo[2.2.1]heptan-5-ylmethyl)-9-bromo-10-chloro-7-hydroxy-2H-[1,4]thiazino[2,3,4-ij]quinazolin-5(3H)-one (500 mg, 1.12 mmol) and potassium carbonate (1.5 g, 11.2 mmol) in acetonitrile (20 mL) was added benzenesulphonyl chloride (678 mg, 2.24 mmol) at 25° C. The mixture was stirred at 25° C. for 1 hour. Then (2R,5S)-tert-butyl 2,5-dimethylpiperazine-1-carboxylate (720 mg, 3.36 mmol) was added and the resulting mixture was stirred at 25° C. for 1 hour. After completion, the mixture was poured into ice-water (30 mL) and extracted with ethyl acetate (3×30 mL). After concentration, the residue was purified by Flash chromatography column (C18, acetonitrile/water=20% to 95%) to afford (2R,5S)-tert-butyl 4-((S)-3-((1S,4S)-2-oxa-5-azabicyclo[2.2.1]heptan-5-ylmethyl)-10-bromo-9-chloro-5-oxo-3,5-dihydro-2H-[1,4]thiazino[2,3,4-ij]quinazolin-7-yl)-2,5-dimethylpiperazine-1-carboxylate (233 mg, 33% yield) as a yellow solid. MS (ESI) m/z: 640.6 $[M+H]^+$.

(2R,5S)-tert-butyl 4-((3S)-3-((1S,4S)-2-oxa-5-azabicyclo[2.2.1]heptan-5-ylmethyl)-9-chloro-10-(5-chloro-2,4-difluorophenyl)-5-oxo-3,5-dihydro-2H-[1,4]thiazino[2,3,4-ij]quinazolin-7-yl)-2,5-dimethylpiperazine-1-carboxylate (7)

To a solution of (2R,5S)-tert-butyl 4-((S)-3-((1S,4S)-2-oxa-5-azabicyclo[2.2.1]heptan-5-ylmethyl)-10-bromo-9-chloro-5-oxo-3,5-dihydro-2H-[1,4]thiazino[2,3,4-ij]quinazolin-7-yl)-2,5-dimethylpiperazine-1-carboxylate (233 mg, 0.36 mmol) in 1,4-dioxane (5 mL) and water (1 mL), tripotassium phosphate (230 mg, 1.08 mmol), (5-chloro-2,4-difluorophenyl)boronic acid (794 mg, 2.88 mmol), and [1,1'-bis(diphenylphosphino)ferrocene]dichloropalladium (II) (53 mg, 0.072 mmol) were added. The mixture was stirred at 85° C. under nitrogen atmosphere for 4 hours. After completion, the mixture was diluted with tetrahydrofuran (50 mL) and the insoluble solid was removed by filtration. The mixture was concentrated and the residue was purified by silica gel column chromatography (dichloromethane/methanol=100/1 to 30/1 as gradient) to afford (2R,5S)-tert-butyl 4-((3S)-3-((1S,4S)-2-oxa-5-azabicyclo[2.2.1]heptan-5-ylmethyl)-9-chloro-10-(5-chloro-2,4-difluorophenyl)-5-oxo-3,5-dihydro-2H-[1,4]thiazino[2,3,4-ij]quinazolin-7-yl)-2,5-dimethylpiperazine-1-carboxylate (180 mg, 75% yield) as a yellow oil. MS (ESI) m/z: 708.7 $[M+H]^+$.

(2R,5S)-tert-butyl 4-((3S)-3-((1S,4S)-2-oxa-5-azabicyclo[2.2.1]heptan-5-ylmethyl)-9-chloro-10-(5-chloro-2,4-difluorophenyl)-5-oxo-3,5-dihydro-2H-[1,4]thiazino[2,3,4-ij]quinazolin-7-yl)-2,5-dimethylpiperazine-1-carboxylate (8)

To a cooled mixture of (2R,5S)-tert-butyl 4-((3S)-3-((1S,4S)-2-oxa-5-azabicyclo[2.2.1]heptan-5-ylmethyl)-9-chloro-10-(5-chloro-2,4-difluorophenyl)-5-oxo-3,5-dihydro-2H-[1,4]thiazino[2,3,4-ij]quinazolin-7-yl)-2,5-dimethylpiperazine-1-carboxylate (180 mg, 0.25 mmol) in dichloromethane (5 mL) was added trifluoroacetic acid (1 mL) at 0° C. The reaction solution was stirred at room temperature for 1 hour. After completion, the mixture was concentrated and the residue was purified by silica gel column chromatography using a mixture of dichloromethane/methanol (15/1) to afford (2R,5S)-tert-butyl 4-((3S)-3-((1S,4S)-2-oxa-5-azabicyclo[2.2.1]heptan-5-ylmethyl)-9-chloro-10-(5-chloro-2,4-difluorophenyl)-5-oxo-3,5-dihydro-2H-[1,4]thiazino[2,3,4-ij]quinazolin-7-yl)-2,5-dimethylpiperazine-1-carboxylate (120 mg, 85% yield) as a yellow solid. MS (ESI) m/z: 608.5 $[M+H]^+$.

$^1H$ NMR (400 MHz, $CDCl_3$) δ 7.65-7.64 (m, 1H), 7.32-7.26 (m, 1H), 7.12-7.06 (m, 1H), 5.37-5.27 (m, 1H), 4.40-4.37 (m, 1H), 4.19-4.18 (m, 1H), 3.92-3.88 (m, 1H), 3.72-3.55 (m, 4H), 3.47-3.45 (m, 2H), 3.34-3.30 (m, 2H), 3.04-2.92 (m, 4H), 2.89-2.78 (m, 3H), 1.80-1.69 (m, 3H), 1.45-1.26 (m, 3H).

(3S)-3-((1S,4S)-2-oxa-5-azabicyclo[2.2.1]heptan-5-ylmethyl)-7-((2S,5R)-4-acryloyl-2,5-dimethylpiperazin-1-yl)-9-chloro-10-(5-chloro-2,4-difluorophenyl)-2H-[1,4]thiazino[2,3,4-ij]quinazolin-5(3H)-one (9)

To a mixture of (2R,5S)-tert-butyl 4-((3S)-3-((1S,4S)-2-oxa-5-azabicyclo[2.2.1]heptan-5-ylmethyl)-9-chloro-10-(5-chloro-2,4-difluorophenyl)-5-oxo-3,5-dihydro-2H-[1,4]thiazino[2,3,4-ij]quinazolin-7-yl)-2,5-dimethylpiperazine-1-carboxylate (120 mg, 0.20 mmol) and triethylamine (41 mg, 0.40 mmol) in dichloromethane (5 mL) was added acrylic anhydride (25 mg, 0.20 mmol) at 0° C. The mixture was stirred at 0° C. for 1 hour. After completion, the mixture was poured into ice-water (15 mL) and extracted with ethyl acetate (3×15 mL). After concentration, the residue was purified by preparative high performance liquid chromatography (20% to 95% acetonitrile in water) to afford (3S)-3-((1S,4S)-2-oxa-5-azabicyclo[2.2.1]heptan-5-ylmethyl)-7-((2S,5R)-4-acryloyl-2,5-dimethylpiperazin-1-yl)-9-chloro- 10-(5-chloro-2,4-difluorophenyl)-2H-[1,4]thiazino[2,3,4-ij]quinazolin-5(3H)-one (48 mg, 37% yield) as a yellow solid. MS (ESI) m/z: 662.1 $[M+H]^+$. $^1H$ NMR (400 MHz, $CDCl_3$) δ 7.54-7.52 (m, 1H), 7.32-7.25 (m, 1H), 7.12-7.06 (m, 1H), 6.66-6.50 (m, 1H), 6.41-6.33 (m, 1H), 5.79-5.75 (m, 1H), 5.28-5.24 (m, 1H), 5.01-4.70 (m, 2H), 4.40-4.26 (m, 2H), 4.02-3.90 (m, 2H), 3.69-3.55 (m, 4H), 3.46-3.29 (m, 1H), 3.03-2.86 (m, 5H), 1.77-1.65 (m, 2H), 1.52-1.33 (m, 6H).
R. Example 518
(3S)-7-((S)-4-acryloyl-2-methylpiperazin-1-yl)-10-(5-chloro-2,4-difluorophenyl)-3-((methoxymethoxy)methyl)-9-(trifluoromethyl)-2H-[1,4]thiazino[2,3,4-ij]quinazolin-5(3H)-one
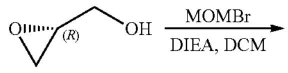
1
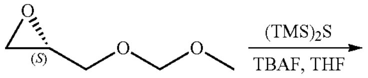
2
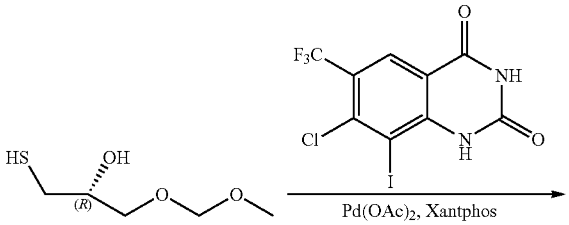
3
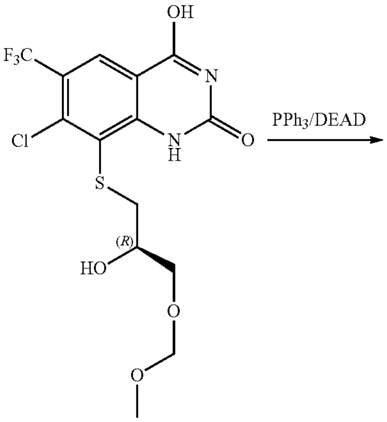
4
-continued
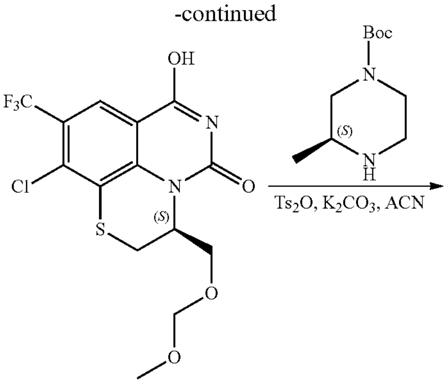
5
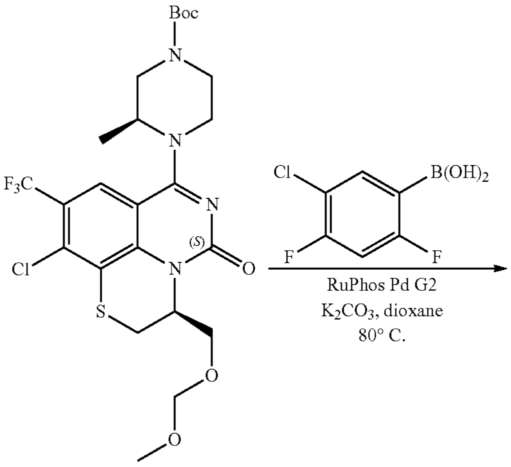
6
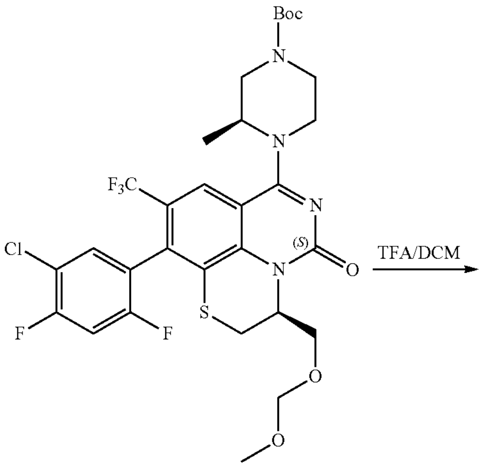
7

-continued

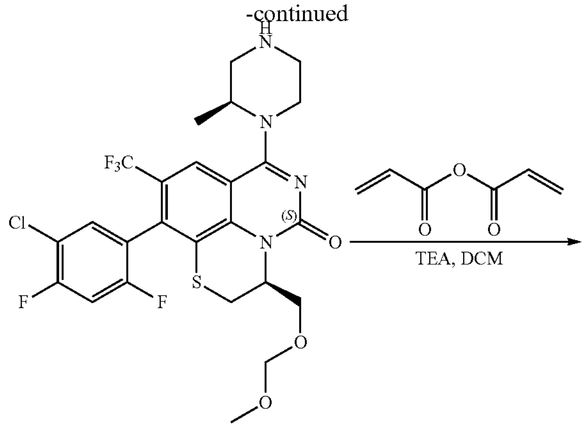

8

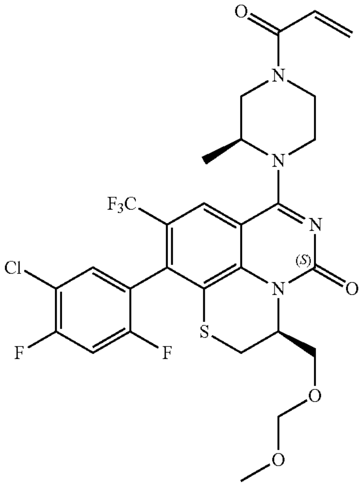

9

(S)-2-((methoxymethoxy)methyl)oxirane (2)

To a mixture of (R)-oxiran-2-ylmethanol (15 g, 202.7 mmol) and N,N-diisopropylethylamine (52.3 g, 405.4 mmol) in dichloromethane (200 mL) was added bromo (methoxy)methane (32.7 g, 263.5 mmol) at 0° C. The mixture was allowed to warm to room temperature and stirred for 5 hours. After completion, the mixture was poured into dichloromethane (300 mL), washed with water (3×200 mL). The organic phase was washed with brine (100 mL) and dried over anhydrous sodium sulfate. After filtration and concentration, the residue was purified by silica gel column with petroleum ether to afford (S)-2-((methoxymethoxy) methyl)oxirane (25.00 g, crude) as colorless oil; $^1$H NMR (400 MHz, $CDCl_3$) δ 4.66 (d, J=1.2 Hz, 2H), 3.79 (dd, J=11.6 Hz, 3.2 Hz, 1H), 3.51 (dd, J=11.6 Hz, 2.0 Hz, 1H), 3.38 (s, 3H), 3.20-3.16 (m, 1H), 2.83-2.80 (m, 1H), 2.64 (dd, J=5.2 Hz, 2.8 Hz, 1H).

(R)-1-mercapto-3-(methoxymethoxy)propan-2-ol (3)

To a mixture of (S)-2-((methoxymethoxy)methyl)oxirane (10 g, 84.7 mmol) in tetrahydrofuran (250 mL) was added 1,1,1,3,3,3-hexamethyldisilathiane (16.63 g, 93.2 mmol) and tetrabutylammonium fluoride (1.0 M in tetrahydrofuran, 25 mL, 25 mmol) at 0° C. The mixture was stirred at room temperature for 2 hours. After completion, the mixture concentrated under reduced pressure, the residue was purified by silica gel column eluting with petroleum ether/ethyl acetate=4/1 to afford (R)-1-mercapto-3-(methoxymethoxy) propan-2-ol (2 g, 16% yield) as a colorless oil. $^1$H NMR (400 MHz, $CDCl_3$) δ 4.66 (s, 2H), 3.85-3.82 (m, 1H), 3.69-3.60 (m, 2H), 3.39 (s, 3H), 2.88 (brs, 1H), 2.71-2.65 (m, 2H), 1.51 (t, J=8.8 Hz, 1H).

(R)-7-chloro-4-hydroxy-8-((2-hydroxy-3-(methoxymethoxy)propyl)thio)-6-(trifluoromethyl) quinazolin-2(1H)-one (4)

To a solution of 7-chloro-8-iodo-6-(trifluoromethyl)quinazoline-2,4(1H,3H)-dione (1.86 g, 4.77 mmol) in dioxane (40 mL) were added potassium carbonate (1.32 g, 9.54 mmol), (R)-1-mercapto-3-(methoxymethoxy)propan-2-ol (1.09 g, 7.15 mmol), 4,5-bis(diphenyl-phosphino)-9,9-dimethylxanthene (413 mg, 0.72 mmol) and Tris(dibenzylideneacetone) dipalladium (439 g, 0.48 mmol). The mixture was stirred at 60° C. under nitrogen atmosphere for 18 hours. After completion, the mixture was concentrated under reduced pressure. The residue was purified by silica gel column chromatography eluting with dichloromethane/methanol=60/1 to afford (R)-7-chloro-4-hydroxy-8-((2-hydroxy-3-(methoxymethoxy)propyl)thio)-6-(trifluoromethyl) quinazolin-2(1H)-one (1.33 g, 67% yield) as pale yellow solid. MS (ESI) m/z: 415.0 $[M+H]^+$.

(S)-10-chloro-7-hydroxy-3-((methoxymethoxy) methyl)-9-(trifluoromethyl)-2H-[1,4]thiazino[2,3,4-ij]quinazolin-5(3H)-one (5)

To a mixture of (R)-7-chloro-4-hydroxy-8-((2-hydroxy-3-(methoxymethoxy)propyl)thio)-6-(trifluoromethyl)quinazolin-2(1H)-one (1.33 g, 3.21 mmol) and triphenylphosphoranylidene (3.37 g, 12.85 mmol) in tetrahydrofuran (500 ml) was added 1,2-bis[(4-chlorophenyl)methyl] ester (4.71 g, 12.85 mmol) at 0° C. The mixture was stirred at 0° C. for 45 min. After completion, the mixture was poured into ice-water (200 mL) and extracted with ethyl acetate (200 mL×3). Concentrated and the residue was purified by C18 with gradient of 30-95% acetonitrile in water to afford (S)-10-chloro-7-hydroxy-3-((methoxymethoxy)methyl)-9-(trifluoromethyl)-2H-[1,4]thiazino[2,3,4-ij]quinazolin-5 (3H)-one (1.1 g, 87% yield) as a pale yellow solid. MS (ESI) m/z: 397.0 $[M+H]^+$.

(S)-tert-butyl 4-((S)-10-chloro-3-((methoxymethoxy)methyl)-5-oxo-9-(trifluoromethyl)-3,5-dihydro-2H-[1,4]thiazino[2,3,4-ij]quinazolin-7-yl)-3-methylpiperazine-1-carboxylate (6)

To a mixture of (S)-10-chloro-7-hydroxy-3-((methoxymethoxy)methyl)-9-(trifluoromethyl)-2H-[1,4] thiazino[2,3,4-ij]quinazolin-5(3H)-one (1.1 g, 2.78 mmol) and potassium carbonate (3.84 g, 27.8 mmol) in acetonitrile (50 mL) was added 4-methylbenzenesulfonic anhydride (1.81 g, 5.56 mmol) at 0° C. The mixture was stirred at room temperature for 4 hours. After completion, (S)-tert-butyl 3-methylpiperazine-1-carboxylate (1.95 g, 8.33 mmol) was added into the reaction solution. The reaction mixture was stirred at 0° C. for 1 hour. After completion, the mixture was poured into ice-water (200 mL) and extracted with ethyl acetate (100 mL×3). After concentration, the residue was purified by C18 column with gradient of 20-95% acetonitrile in water to afford (S)-tert-butyl 4-((S)-10-chloro-3-((methoxymethoxy)methyl)-5-oxo-9-(trifluoromethyl)-3,5- dihydro-2H-[1,4]thiazino[2,3,4-ij]quinazolin-7-yl)-3-methylpiperazine-1-carboxylate (1 g, 59% yield) as a pale yellow solid. MS (ESI) m/z: 613.1 $[M+H]^+$.

(3S)-tert-butyl 4-((3S)-10-(5-chloro-2,4-difluorophenyl)-3-((methoxymethoxy)methyl)-5-oxo-9-(trifluoromethyl)-3,5-dihydro-2H-[1,4]thiazino[2,3,4-ij]quinazolin-7-yl)-3-methylpiperazine-1-carboxylate (7)

To a solution of (S)-tert-butyl 4-((S)-10-chloro-3-((methoxymethoxy)methyl)-5-oxo-9-(trifluoromethyl)-3,5-dihydro-2H-[1,4]thiazino[2,3,4-ij]quinazolin-7-yl)-3-methylpiperazine-1-carboxylate (250 mg, 0.408 mmol) in 1,4-dioxane (6 mL) and water (1 mL) were added tripotassium phosphate (260 mg, 1.224 mmol), (5-chloro-2,4-difluorophenyl)boronic acid (560 mg, 2.04 mmol), and Chloro(2-dicyclohexylphosphino-2', 6'-diisopropoxy-1,1'-biphenyl)[2-(2'-amino-1,1'-biphenyl)]palladium(II) (32 mg, 0.04 mmol). The mixture was stirred at 80° C. under nitrogen atmosphere for 4 hours. After completion, the mixture was concentrated under reduced pressure, the residue was purified by silica gel column chromatography eluting with dichloromethane/methanol=50/1 to afford (3S)-tert-butyl 4-((3S)-10-(5-chloro-2,4-difluorophenyl)-3-((methoxymethoxy)methyl)-5-oxo-9-(trifluoromethyl)-3,5-dihydro-2H-[1,4]thiazino[2,3,4-ij]quinazolin-7-yl)-3-methylpiperazine-1-carboxylate (398 mg, crude) as a yellow solid. MS (ESI) m/z: 725.7 $[M+H]^+$.

(3S)-10-(5-chloro-2,4-difluorophenyl)-3-((methoxymethoxy)methyl)-7-((S)-2-methylpiperazin-1-yl)-9-(trifluoromethyl)-2H-[1,4]thiazino[2,3,4-ij]quinazolin-5(3H)-one (8)

To a mixture of (3S)-tert-butyl 4-((3S)-10-(5-chloro-2,4-difluorophenyl)-3-((methoxymethoxy)methyl)-5-oxo-9-(trifluoromethyl)-3,5-dihydro-2H-[1,4]thiazino[2,3,4-ij]quinazolin-7-yl)-3-methylpiperazine-1-carboxylate (398 mg, 0.55 mmol) in methanol (15 ml) was added palladium on charcoal (10%) (148 mg). The reaction solution was stirred at room temperature under hydrogen atmosphere for 1 hour. After completion, the mixture was filtered and concentrated, the residue was purified by column (dichloromethane/methanol=5:1) to afford (3S)-10-(2,4-difluorophenyl)-7-((2S, 5R)-2,5-dimethylpiperazin-1-yl)-3-((2-methoxyethoxy)methyl)-9-(trifluoromethyl)-2H-[1,4]thiazino[2,3,4-ij]quinazolin-5(3H)-one (701 mg, impure) as a yellow-brown solid. MS (ESI) m/z: 591.5 $[M+H]^+$.

(3S)-7-((S)-4-acryloyl-2-methylpiperazin-1-yl)-10-(5-chloro-2,4-difluorophenyl)-3-((methoxymethoxy)methyl)-9-(trifluoromethyl)-2H-[1,4]thiazino[2,3,4-ij]quinazolin-5(3H)-one (9)

To a mixture of (3S)-10-(2,4-difluorophenyl)-7-((2S, 5R)-2,5-dimethylpiperazin-1-yl)-3-((2-methoxyethoxy)methyl)-9-(trifluoromethyl)-2H-[1,4]thiazino[2,3,4-ij]quinazolin-5(3H)-one (272 mg, 0.46 mmol) and triethyl amine (93 mg, 0.92 mmol) in dichloromethane (5 ml) was added acrylic anhydride (70 mg, 0.55 mmol) at 0° C. The mixture was stirred at 0° C. for 1 hour. After completion, the mixture was poured into ice-water (30 mL) and extracted with dichloromethane (30 mL×3). After concentration, the residue was purified by preparative High Performance Liquid Chromatography with gradient of 20% to 95% acetonitrile in water to afford (3S)-7-((S)-4-acryloyl-2-methylpiperazin-1-yl)-10-(5-chloro-2,4-difluorophenyl)-3-((methoxymethoxy)methyl)-9-(trifluoromethyl)-2H-[1,4]thiazino[2,3,4-ij]quinazolin-5(3H)-one (73.6 mg, 25% yield) as a white solid. MS (ESI) m/z: 645.2 $[M+H]^+$.

$^1H$ NMR (400 MHz, $CDCl_3$) δ 7.78 (s, 1H), 7.31-7.24 (m, 1H), 7.10-7.04 (m, 1H), 6.67-6.50 (m, 1H), 6.38 (dd, J=16.8 Hz, 2.0 Hz, 1H), 5.79 (d, J=10.4 Hz, 1H), 5.50-5.38 (m, 1H), 4.80-4.62 (m, 3H), 4.59-4.26 (m, 2H), 4.06-3.92 (m, 0.5H), 3.90-3.74 (m, 2.5H), 3.67-3.47 (m, 1.5H), 3.46-3.33 (m, 4.5H), 3.17-2.96 (m, 2H), 1.61-1.44 (m, 3H).

S. Example 531

8'-((2S,5R)-4-Acryloyl-2,5-dimethylpiperazin-1-yl)-11'-(2,4-difluorophenyl)-10'-(trifluoromethyl)-2'H,4'H,6'H-spiro[oxetane-3,3'-[1,4]thiazepino[2,3,4-ij]quinazolin]-6'-one

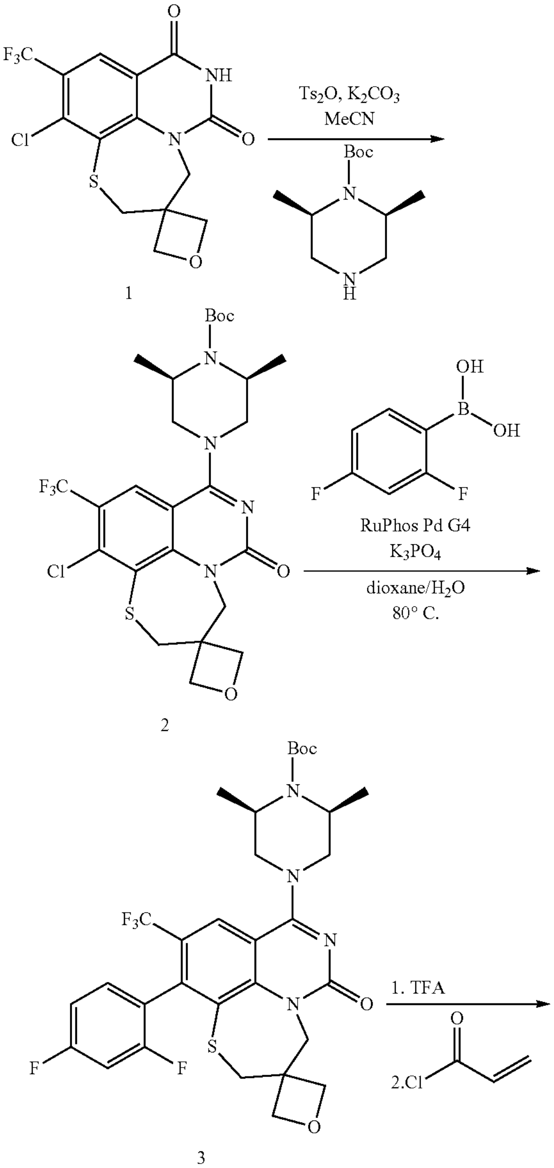

1

2

3

-continued

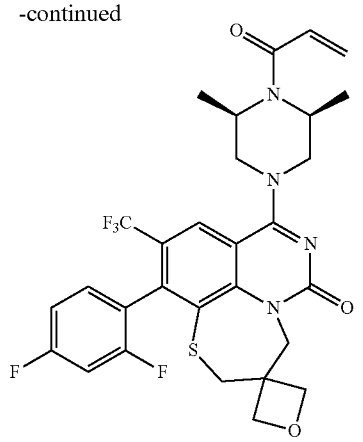

4 tert-Butyl (2S,6R)-4-(11'-chloro-6'-oxo-10'-(trifluoromethyl)-2'H,4'H,6'H-spiro[oxetane-3,3'-[1,4]thiazepino[2,3,4-ij]quinazolin]-8'-yl)-2,6-dimethylpiperazine-1-carboxylate (2)

Compound 1 (30 mg, 0.08 mmol, 1 equiv) was dissolved in MeCN (1.6 mL, 0.05 M) under a $N_2$ atmosphere in a 5 mL microwave vial. Potassium carbonate (33 mg, 0.24 mmol, 3 equiv) was added to the reaction mixture and the reaction mixture was briefly sonicated. p-Toluenesulfonic anhydride (52 mg, 0.16 mmol, 2 equiv) was added to the vial at room temperature. The reaction mixture was stirred for 21 hours and reached 65% conversion (determined by LC-MS). Next, tert-butyl (2R,6S)-2,6-dimethylpiperazine-1-carboxylate (34 mg, 0.16 mmol, 2 equiv) and $K_2CO_3$ (22 mg, 0.16 mmol, 2 equiv) were added to the vial and stirred for 30 min at room temperature. The intermediate was determined to be fully consumed by LC-MS and the solvent was removed by rotary evaporation. The mixture was transferred with $CH_2Cl_2$ to a separatory funnel, washed with saturated aqueous $NH_4Cl$ (20 mL), extracted with $CH_2Cl_2$ (2×50 mL), dried over $Na_2SO_4$, and filtered. The solvent was removed by rotary evaporation. The crude material was partially purified by flash column chromatography using an Isolera One Biotage instrument (0-6% $MeOH/CH_2Cl_2$, 10 g column, 0% (5 CV), 0-6% (15 CV), 6% (5 CV)), to provide compound 2 (44 mg, impure) as a yellow solid. This impure material was used as is in the subsequent step: TLC (5% $MeOH/CH_2Cl_2$) $R_f$=0.43; LRMS-ESI (m/z) $[M+H]^+$ calculated for $C_{25}H_{31}ClF_3N_4O_4S$ 575.17, found 575.2.

tert-Butyl (2S,6R)-4-(11'-(2,4-difluorophenyl)-6'-oxo-10'-(trifluoromethyl)-2'H,4'H,6'H-spiro[oxetane-3,3'-[1,4]thiazepino[2,3,4-ij]quinazolin]-8'-yl)-2,6-dimethylpiperazine-1-carboxylate (3)

Compound 2 (44 mg, impure ~0.08 mmol, 1 equiv) was dissolved in 1,4-dioxane and $H_2O$ (1.3 mL, 0.3 mL, respectively, 0.05 M). The resulting mixture was purged with $N_2$ for 30 min prior to the addition of RuPhos Pd G4 (6.8 mg, 0.008 mmol, 10 mol %), $K_3PO_4$ (51 mg, 0.24 mmol, 3 equiv), and (2,4-difluorophenyl)boronic acid (63 mg, 0.4 mmol, 5 equiv). The microwave vial was fitted with a crimp-top cap, bubbled with $N_2$ for an additional 5 min, and placed on a heated block at 80° C. The resulting reaction mixture was homogenous and orange. After 1 h, the vial was removed from the heating block, allowed to cool, and the solvent was removed by rotary evaporation (full conversion determined by LC-MS). The crude material was partially purified by flash column chromatography using an Isolera One Biotage instrument (0-6% $MeOH/CH_2Cl_2$, 10 g column, 0% (5 CV), 0-6% (15 CV), 6% (5 CV)) to afford the desired product (3) as a brown oil (38 mg). The material was used as is in the subsequent step: TLC (3% $MeOH/CH_2Cl_2$) $R_f$=0.19; LRMS-ESI (m/z) $[M+H]^+$ calculated for $C_{31}H_{34}F_5N_4O_4S$ 653.22, found 653.3.

8'-((3S,5R)-4-Acryloyl-3,5-dimethylpiperazin-1-yl)-11'-(2,4-difluorophenyl)-10'-(trifluoromethyl)-2'H,4'H,6'H-spiro[oxetane-3,3'-[1,4]thiazepino[2,3,4-ij]quinazolin]-6'-one (4)

Standard deBoc and acrylation conditions: 0.054 mmol scale, 8.7 mg off-white solid, 27% yield:

$^1H$ NMR (400 MHz, MeOH-$d_4$) δ 8.16 (s, 1H), 7.31 (q, J=7.6 Hz, 1H), 7.11 (t, J=8.6 Hz, 2H), 6.84 (dd, J=16.7, 10.6 Hz, 1H), 6.29 (dd, J=16.7, 2.0 Hz, 1H), 5.80 (dd, J=10.5, 2.0 Hz, 1H), 5.37-4.95 (m, 2H), 4.87-4.50 (m, 4H), 4.43 (dd, J=6.3, 1.6 Hz, 2H), 4.25 (d, J=13.5 Hz, 2H), 3.65-3.36 (m, 4H), 1.52 (d, J=6.6 Hz, 3H), 1.48 (d, J=6.8 Hz, 3H); LRMS-ESI (m/z) $[M+H]^+$ calculated for $C29H_{28}F_5N_4O_3S$ 607.18, found 607.3.

T. Example 588

8'-((2S,5R)-4-Acryloyl-2,5-dimethylpiperazin-1-yl)-11'-(2,4-difluorophenyl)-10'-(trifluoromethyl)-2'H,4'H,6'H-spiro[oxetane-3,3'-[1,4]thiazepino[2,3,4-ij]quinazolin]-6'-one

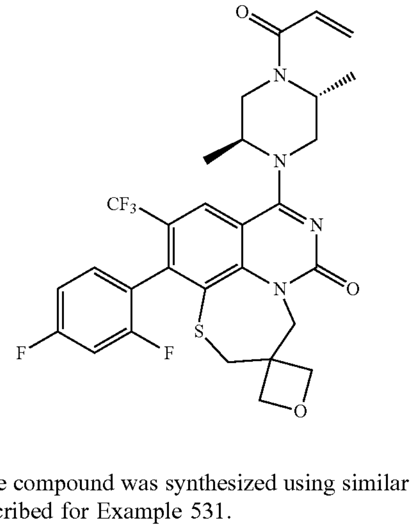

The title compound was synthesized using similar procedures described for Example 531.

$^1H$ NMR (400 MHz, MeOH-$d_4$) δ 7.97 (d, J=2.7 Hz, 1H), 7.30 (dq, J=13.7, 7.6 Hz, 1H), 7.11 (t, J=8.3 Hz, 2H), 6.90-6.72 (m, 1H), 6.28 (ddd, J=16.7, 5.6, 2.0 Hz, 1H), 5.80 (ddd, J=9.7, 7.2, 2.0 Hz, 1H), 4.87-4.60 (m, 3H), 4.55-4.36 (m, 3H), 4.34-3.69 (m, 4H), 3.62-3.40 (m, 3H), 1.49-1.25 (m, 6H); LRMS-ESI (m/z) $[M+H]^+$ calculated for $C_{29}H_{28}F_5N_4O_3S$ 607.18, found 607.2.

U. Example 589

8'-(4-Acryloylpiperazin-1-yl-2,2,3,3,5,5,6,6-d)-11'-(2,4-difluorophenyl)-10'-(trifluoromethyl)-2'H,4'H,6'H-spiro[oxetane-3,3'-[1,4]thiazepino[2,3,4-ij]quinazolin]-6'-one

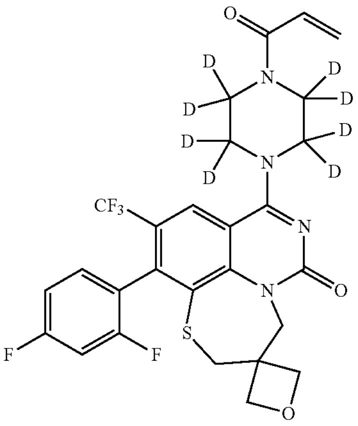 [SMILES: [2H]C1([2H])N(C(=O)C=C)C([2H])([2H])C([2H])([2H])N(c2nc(=O)n3c4c(c(-c5ccc(F)cc5F)c(C(F)(F)F)cc24)SCC2(COC2)C3)C1([2H])[2H]]

The title compound was synthesized via similar methods described for Example 531.

$^1$H NMR (400 MHz, MeOH-$d_4$) δ 8.00 (s, 1H), 7.30 (q, J=7.7 Hz, 1H), 7.11 (t, J=8.7 Hz, 2H), 6.80 (dd, J=16.7, 10.6 Hz, 1H), 6.27 (dd, J=16.7, 1.9 Hz, 1H), 5.80 (dd, J=10.6, 2.0 Hz, 1H), 4.82-4.54 (m, 2H), 4.43 (d, J=5.5 Hz, 2H), 3.61-3.46 (m, 2H), 3.23-3.11 (m, 2H); LRMS-ESI (m/z) [M+H]$^+$ calculated for $C_{27}H_{16}D_8F_5N_4O_3S$ 587.20, found 587.2.

V. Examples 546 and 547

(3S,10S)-7-((3S,5R)-4-acryloyl-3,5-dimethylpiperazin-1-yl)-10-(2,4-difluorophenyl)-3-(methoxymethyl)-9-(trifluoromethyl)-2,3-dihydro-5H-[1,4]thiazino[2,3,4-ij]quinazolin-5-one and (3S,10R)-7-((3S,5R)-4-acryloyl-3,5-dimethylpiperazin-1-yl)-10-(2,4-difluorophenyl)-3-(methoxymethyl)-9-(trifluoromethyl)-2,3-dihydro-5H-[1,4]thiazino[2,3,4-ij]quinazolin-5-one

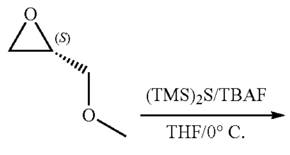

1

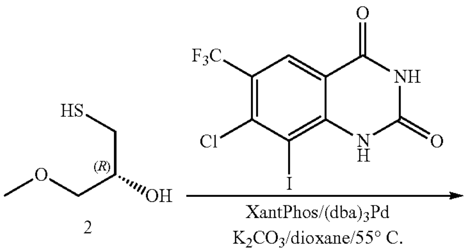

2

-continued

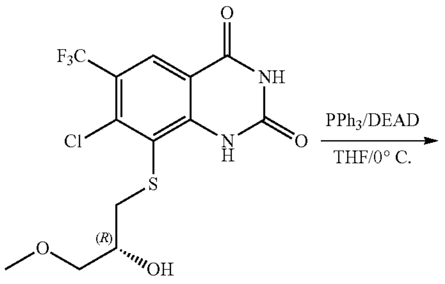

3

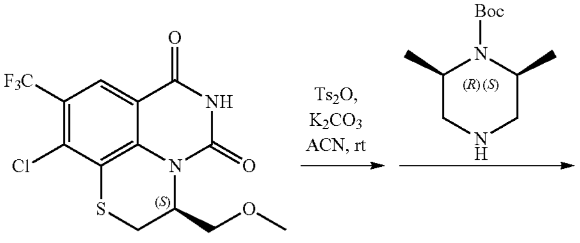

4

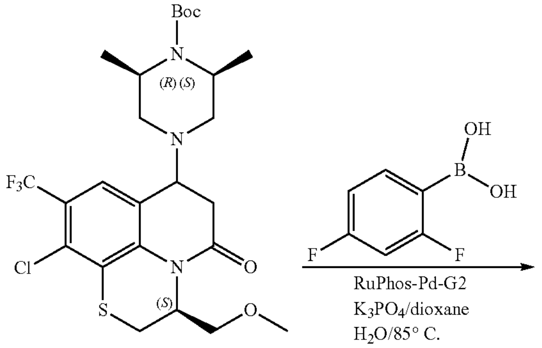

5

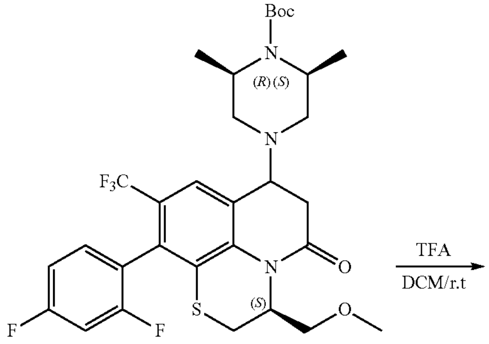

6

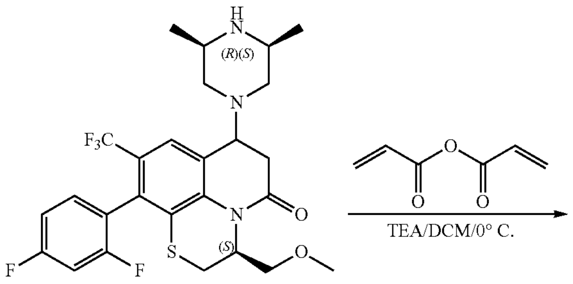

7

-continued

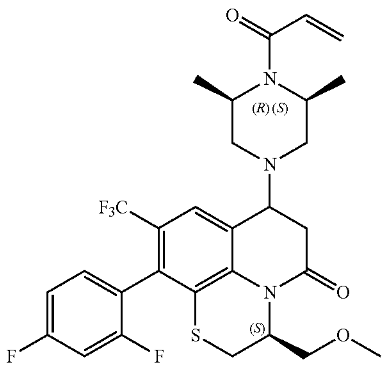

8

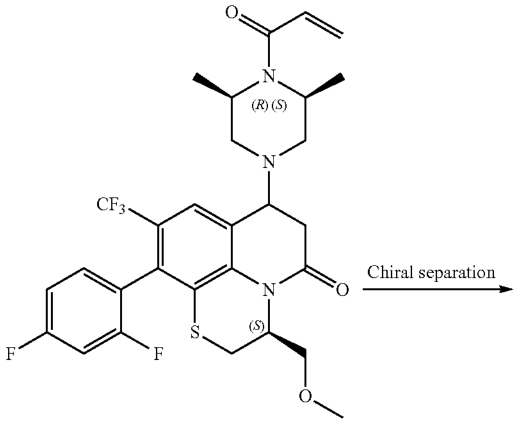

8

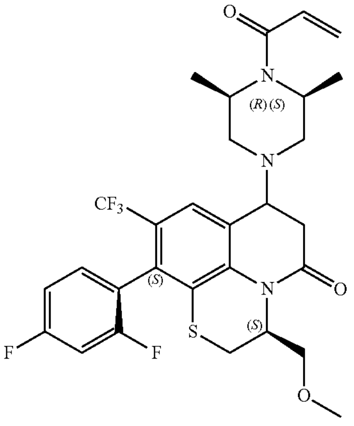

+

P1

-continued

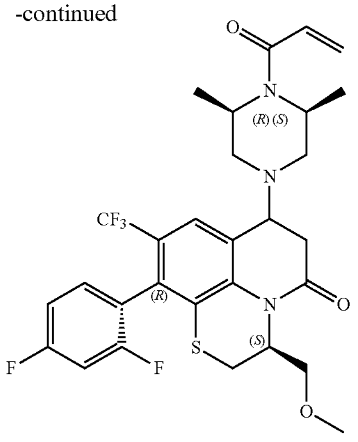

P2

(R)-1-mercapto-3-methoxypropan-2-ol (2)

To a mixture of(S)-2-(methoxymethyl)oxirane (10.00 g, 113.6 mmol) in tetrahydrofuran (150 mL) was added 1,1,1,3,3,3-hexamethyldisilathiane (30.33 g, 170.4 mmol) and tetrabutylammonium fluoride (1.0 M in tetrahydrofuran, 34.1 mL, 34.1 mmol) at 0° C. The mixture was stirred at room temperature for 2 hours. After completion, the mixture was poured into water (300 mL), extracted with ethyl acetate (3×200 mL). The combined organic phase was washed with brine (300 mL) and dried over anhydrous sodium sulfate. After filtration and concentration, the residue was purified by silica gel column eluting with petroleum ether/ethyl acetate (3/1) to afford (R)-1-mercapto-3-methoxypropan-2-ol (17.0 g, crude) as a colorless oil.

$^{1}$H NMR (300 MHz, $CDCl_3$) δ 3.86-3.82 (m, 1H), 3.49-3.46 (m, 1H), 3.41-3.37 (m, 4H), 2.71-2.64 (m, 1H), 1.55-1.50 (m, 1H).

(R)-7-chloro-8-((2-hydroxy-3-methoxypropyl)thio)-6-(trifluoromethyl)quinazoline-2,4(1H,3H)-dione (3)

To a solution of 7-chloro-8-iodo-6-(trifluoromethyl)quinazoline-2,4(1H,3H)-dione (4.00 g, 10.24 mmol) in dioxane (100 mL) were added potassium carbonate (4.25 g, 30.73 mmol), (R)-1-mercapto-3-methoxypropan-2-ol (2.50 g, 20.48 mmol), 4,5-bis(diphenyl-phosphino)-9,9-dimethylxanthene (0.89 g, 1.54 mmol) and tris(dibenzylideneacetone) dipalladium (0.94 g, 1.02 mmol). The mixture was stirred at 55° C. under nitrogen atmosphere for 18 hours. After completion, the mixture was diluted with tetrahydrofuran (300 mL) and filtered. After concentration, the residue was purified by silica gel column chromatography with a gradient of dichloromethane/methanol=100/1 to 30/1 to afford (R)-7-chloro-8-((2-hydroxy-3-methoxypropyl)thio)-6-(trifluoromethyl)quinazoline-2,4(1H,3H)-dione (3.15 g, 80% yield) as a white solid. MS (ESI) m/z: 385.0 [M+H]$^{+}$.

(S)-10-chloro-3-(methoxymethyl)-9-(trifluoromethyl)-2H-[1,4]thiazino[2,3,4-ij]quinazoline-5,7(3H,6H)-dione (4)

To a mixture of (R)-7-chloro-8-((2-hydroxy-3-methoxypropyl)thio)-6-(trifluoromethyl)quinazoline-2,4(1H,3H)-dione (3.15 g, 8.20 mmol) and triphenylphosphoranylidene (4.29 g, 16.40 mmol) in tetrahydrofuran (160 mL) was added diethyl azodicarboxylate (2.85 g, 16.40 mmol) at 0°

C. The mixture was stirred at 0° C. for 45 min. After completion, the mixture was poured into ice-water (300 mL) and extracted with ethyl acetate (500 mL×3). After concentration, the residue was purified by Flash chromatography column (C18, acetonitrile/water=30% to 95%) to afford (S)-10-chloro-3-(methoxymethyl)-9-(trifluoromethyl)-2H-[1,4]thiazino[2,3,4-ij]quinazoline-5,7(3H,6H)-dione (2.10 g, 70% yield) as a white solid. MS (ESI): m/z: 367.0 $[M+H]^+$.

(2S,6R)-tert-butyl 4-((S)-10-chloro-3-(methoxymethyl)-5-oxo-9-(trifluoromethyl)-3,5-dihydro-2H-[1,4]thiazino[2,3,4-ij]quinazolin-7-yl)-2,6-dimethylpiperazine-1-carboxylate (5)

To a mixture of (S)-10-chloro-3-(methoxymethyl)-9-(trifluoromethyl)-2H-[1,4]thiazino[2,3,4-ij]quinazoline-5,7(3H,6H)-dione (200 mg, 0.55 mmol) and potassium carbonate (759 mg, 5.50 mmol) in acetonitrile (25 mL) was added 4-methylbenzenesulfonic anhydride (534 mg, 1.65 mmol) at 0° C. The mixture was stirred at 0° C. for 30 min and 30° C. for 1 hour. After completion, (2S,6R)-tert-butyl 2,6-dimethylpiperazine-1-carboxylate (353 mg, 1.65 mmol) was added into the reaction solution. The reaction mixture was stirred at 0° C. for 1 hour. After completion, the mixture was poured into ice-water (300 mL) and extracted with ethyl acetate (3×200 mL). After concentration, the residue was purified by Flash chromatography column (C18, acetonitrile/water=20% to 95%) to afford (2S,6R)-tert-butyl 4-((S)-10-chloro-3-(methoxymethyl)-5-oxo-9-(trifluoromethyl)-3,5-dihydro-2H-[1,4]thiazino[2,3,4-ij]quinazolin-7-yl)-2,6-dimethylpiperazine-1-carboxylate (230 mg, 74% yield) as a pale-white solid. MS (ESI) m/z: 563.5 $[M+H]^+$.

(2S,6R)-tert-butyl 4-((3S)-10-(2,4-difluorophenyl)-3-(methoxymethyl)-5-oxo-9-(trifluoromethyl)-3,5-dihydro-2H-[1,4]thiazino[2,3,4-ij]quinazolin-7-yl)-2,6-dimethylpiperazine-1-carboxylate (6)

To a solution of (2S,6R)-tert-butyl 4-((S)-10-chloro-3-(methoxymethyl)-5-oxo-9-(trifluoromethyl)-3,5-dihydro-2H-[1,4]thiazino[2,3,4-ij]quinazolin-7-yl)-2,6-dimethylpiperazine-1-carboxylate (230 mg, 0.41 mmol) in 1,4-dioxane (8 mL) and water (1 mL) were added tripotassium phosphate (348 mg, 1.64 mmol), (2,4-difluorophenyl)boronic acid (385 mg, 2.45 mmol), and Chloro(2-dicyclohexylphosphino-2',6'-diisopropoxy-1,1'-biphenyl)[2-(2'-amino-1,1'-biphenyl)] palladium(II) (64 mg, 0.08 mmol). The mixture was stirred at 85° C. under nitrogen atmosphere for 4 hours. After completion, the mixture was diluted with tetrahydrofuran (300 mL) and filtered. Then After concentration, the residue was purified by silica gel column chromatography with a gradient of dichloromethane/methanol (100/1 to 30/1) to afford (2S,6R)-tert-butyl 4-((3S)-10-(2,4-difluorophenyl)-3-(methoxymethyl)-5-oxo-9-(trifluoromethyl)-3,5-dihydro-2H-[1,4]thiazino[2,3,4-ij]quinazolin-7-yl)-2,6-dimethylpiperazine-1-carboxylate (220 mg, crude) as a yellow solid. MS (ESI) m/z: 641.6 $[M+H]^+$.

(3S)-10-(2,4-difluorophenyl)-7-((3S,5R)-3,5-dimethylpiperazin-1-yl)-3-(methoxymethyl)-9-(trifluoromethyl)-2H-[1,4]thiazino[2,3,4-ij]quinazolin-5(3H)-one (7)

To a mixture of (2S,6R)-tert-butyl 4-((3S)-10-(2,4-difluorophenyl)-3-(methoxymethyl)-5-oxo-9-(trifluoromethyl)-3,5-dihydro-2H-[1,4]thiazino[2,3,4-ij]quinazolin-7-yl)-2,6-dimethylpiperazine-1-carboxylate (220 mg, 0.34 mmol) in dichloromethane (5 ml) was added trifluoroacetic acid (2 mL) at 0° C. The reaction solution was stirred at room temperature for 1 hour. After completion, the mixture was concentrated. The residue was purified by column chromatography (eluting with dichloromethane/methanol (15:1) to afford (3S)-10-(2,4-difluorophenyl)-7-((3S,5R)-3,5-dimethylpiperazin-1-yl)-3-(methoxymethyl)-9-(trifluoromethyl)-2H-[1,4]thiazino[2,3,4-ij]quinazolin-5(3H)-one (140 mg, 76% yield) as a yellow solid. MS (ESI) m/z: 541.6 $[M+H]^+$.

(3S)-7-((3S,5R)-4-acryloyl-3,5-dimethylpiperazin-1-yl)-10-(2,4-difluorophenyl)-3-(methoxymethyl)-9-(trifluoromethyl)-2H-[1,4]thiazino[2,3,4-ij]quinazolin-5(3H)-one (8)

To a mixture of (3S)-10-(2,4-difluorophenyl)-7-((3S,5R)-3,5-dimethylpiperazin-1-yl)-3-(methoxymethyl)-9-(trifluoromethyl)-2H-[1,4]thiazino[2,3,4-ij]quinazolin-5(3H)-one (120 mg, 0.22 mmol) and triethyl amine (44 mg, 0.44 mmol) in dichloromethane (5 ml) was added acrylic anhydride (42 mg, 0.33 mmol) at 0° C. The mixture was stirred at 0° C. for 1 hour. After completion, the mixture was poured into ice-water (50 mL) and extracted with ethyl acetate (20 mL×3). The organic layer was dried over $Na_2SO_4$ and filtered. After concentration, the residue was purified by preparative High Performance Liquid Chromatography (20% to 95% acetonitrile in water) to afford (3S)-7-((3S,5R)-4-acryloyl-3,5-dimethylpiperazin-1-yl)-10-(2,4-difluorophenyl)-3-(methoxymethyl)-9-(trifluoromethyl)-2H-[1,4]thiazino[2,3,4-ij]quinazolin-5(3H)-one (100 mg, 76% yield) as a white solid. $^1H$ NMR (400 MHz, $CDCl_3$) δ 8.07 (s, 1H), 7.17 (q, J=8.0 Hz, 1H), 7.06-6.93 (m, 2H), 6.62 (dd, J=10.4 Hz, 16.8 Hz, 1H), 6.40 (dd, J=2.0 Hz, 16.8 Hz, 1H), 5.77 (dd, J=2.0 Hz, 10.4 Hz, 1H), 5.48-5.41 (m, 1H), 4.79-4.53 (m, 2H), 4.21-4.16 (m, 2H), 3.69-3.59 (m, 2H), 3.37-3.30 (m, 6H), 3.05-2.99 (m, 1H), 1.62 (d, J=6.8 Hz, 3H), 1.47 (d, J=6.8 Hz, 3H). MS (ESI) m/z: 595.6 $[M+H]^+$.

The above racemate (72 mg) was dissolved in EtOH (5 mL) and separated by chiral supercritical fluid chromatography (separation condition: Column:Chiralpak AD-H 5 μm 20×250 mm; Mobile Phase: $CO_2$:EtOH=70:30 at 25 mL/min; Temp: 25° C.; Wavelength: 254 nm) to afford two atropisomers of the title compounds P1 (30.0 mg, 41% yield, 100% de), and P2 (35.0 mg, 48% yield, 100% de); Chiral HPLC Analytical: on CHIRALPAK® AD-H was using 5 μm 4.6×250 mm column, Mobile Phase: $CO_2$:EtOH=70:30 at 2.5 mL/min; Temp: 25° C.; Wavelength: 254 nm).

P1: $^1H$ NMR (400 MHz, $CDCl_3$) δ 8.07 (s, 1H), 7.18 (q, J=8.0 Hz, 1H), 7.05-6.93 (m, 2H), 6.62 (dd, J=6.0 Hz, 16.4 Hz, 1H), 6.40 (dd, J=1.6 Hz, 16.4 Hz, 1H), 5.77 (dd, J=1.6 Hz, 10.4 Hz, 1H), 5.48-5.45 (m, 1H), 4.70-4.60 (m, 1H), 4.22-4.17 (m, 2H), 3.74-3.60 (m, 3H), 3.39-3.31 (m, 6H), 3.03-2.99 (m, 1H), 1.63-1.61 (m, 3H), 1.47 (d, J=7.2 Hz, 3H); Chiral SFC fraction 1: d.e.=100%, Rt=4.14 min.

P2: $^1H$ NMR (400 MHz, $CDCl_3$) δ 8.07 (s, 1H), 7.18 (q, J=7.6 Hz, 1H), 7.04-6.94 (m, 2H), 6.62 (dd, J=10.0 Hz, 16.8 Hz, 1H), 6.40 (dd, J=2.0 Hz, 16.8 Hz, 1H), 5.77 (dd, J=2.0 Hz, 10.8 Hz, 1H), 5.46-5.42 (m, 1H), 4.73-4.61 (m, 1H), 4.21-4.16 (m, 2H), 3.74-3.64 (m, 3H), 3.40-3.30 (m, 6H), 3.03 (dd, J=2.4 Hz, 13.2 Hz, 1H), 1.63-1.61 (m, 3H), 1.47 (d, J=7.2 Hz, 3H); Chiral SFC fraction 1: d.e.=100%, Rt=4.29 min.

W. Example 560
(3S)-3-(((1S,4S)-2-oxa-5-azabicyclo[2.2.1]heptan-5-yl)methyl)-7-((3S,5R)-4-acryloyl-3,5-dimethylpiperazin-1-yl)-10-(2,4-difluorophenyl)-9-(trifluoromethyl)-2,3-dihydro-5H-[1,4]thiazino[2,3,4-ij]quinazolin-5-one
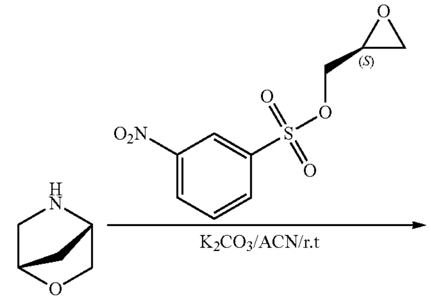
1
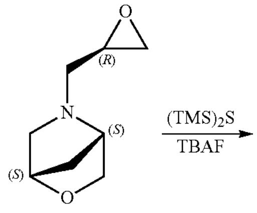
2
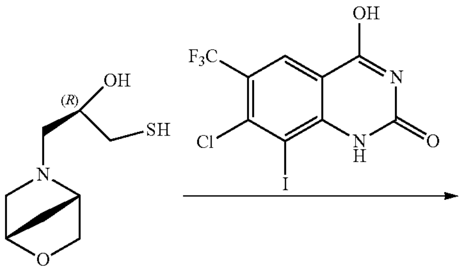
3
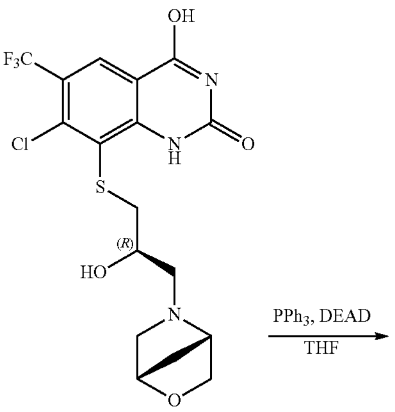
4
-continued
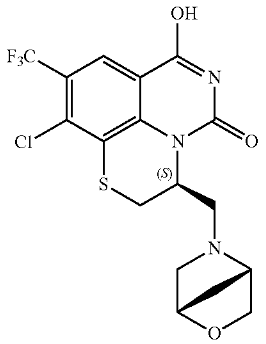
5
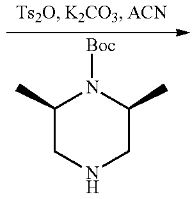
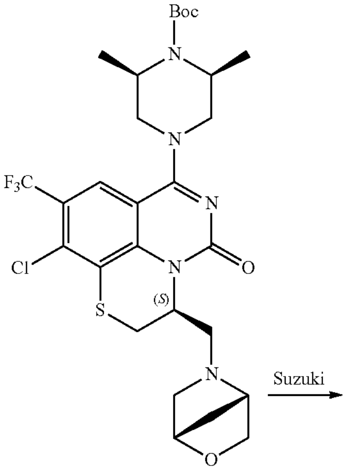
6
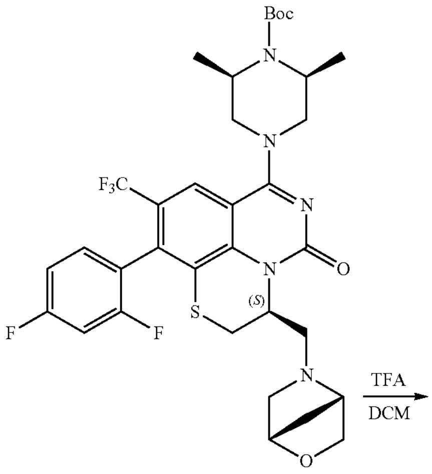
7

-continued

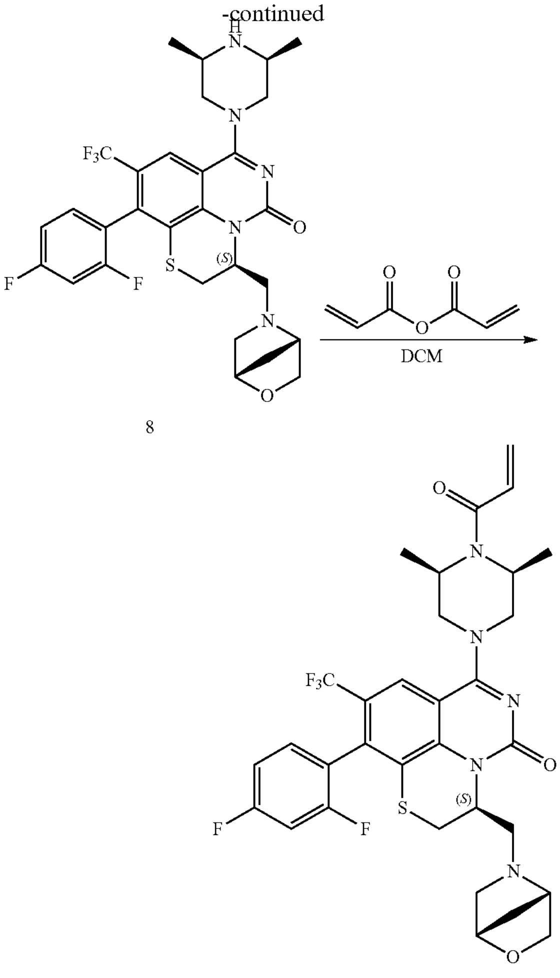

8

9

(1S,4S)-5-((R)-oxiran-2-ylmethyl)-2-oxa-5-azabicyclo[2.2.1]heptanes (2)

To a mixture of (S)-oxiran-2-ylmethyl 3-nitrobenzenesulfonate (38.2 g, 147.5 mmol), (1S,4S)-2-oxa-5-azabicyclo[2.2.1]heptane (20.0 g, 147.5 mmol) in acetonitrile (300 mL) was added potassium carbonate (61 g, 442.5 mmol) at 0° C. under nitrogen atmosphere. The mixture was stirred under nitrogen atmosphere at room temperature for 16 hours. After completion, the mixture was concentrated. The residue was purified by silica gel column eluting with dichloromethane/methanol (20/1) to afford the product (15.0 g, 66% yield) as a yellow oil. MS (ESI) m/z: 156.1 $[M+H]^+$.

(R)-1-((1S,4S)-2-oxa-5-azabicyclo[2.2.1]heptan-5-yl)-3-mercaptopropan-2-ol (3)

To a mixture of (1S,4S)-5-((R)-oxiran-2-ylmethyl)-2-oxa-5-azabicyclo[2.2.1]heptane (6 g, 38.7 mmol) in tetrahydrofuran (60 mL) were added 1,1,1,3,3,3-hexamethyldisilathiane (8.9 g, 50.3 mmol) and tetrabutylammonium fluoride (1.0 M in tetrahydrofuran, 11.6 mL, 11.6 mmol) at 0° C. The mixture was stirred at room temperature for 2 hours. After completion, the mixture was poured into water (60 mL), extracted with ethyl acetate (3×100 mL). The organic phase was washed with brine (200 mL) and dried over anhydrous sodium sulfate. After filtration and concentration, the residue was purified by silica gel column eluting with dichloromethane/methanol (50/1) to afford (R)-1-((1S,4S)-2-oxa-5-azabicyclo[2.2.1]heptan-5-yl)-3-mercaptopropan-2-ol (2.6 g, 35% yield) as a colorless oil. MS (ESI) m/z: 190.1 [M+H]+.

8-(((R)-3-((1S,4S)-2-oxa-5-azabicyclo[2.2.1]heptan-5-yl)-2-hydroxypropyl)thio)-7-chloro-4-hydroxy-6-(trifluoromethyl)quinazolin-2(1H)-one (4)

To a solution of 7-chloro-4-hydroxy-8-iodo-6-(trifluoromethyl)quinazolin-2(1H)-one (4.00 g, 9.10 mmol) in dioxane (100 mL) were added potassium carbonate (3.70 g, 27.3 mmol), (R)-1-((1S,4S)-2-oxa-5-azabicyclo[2.2.1]heptan-5-yl)-3-mercaptopropan-2-ol (2.57 g, 13.6 mmol), 4,5-bis(diphenyl-phosphino)-9,9-dimethylxanthene (1.05 g, 1.82 mmol) and tris(dibenzylideneacetone) dipalladium (0.823 g, 0.91 mmol). The mixture was stirred at 55° C. under nitrogen atmosphere for 8 hours. After completion, the mixture was diluted with tetrahydrofuran (200 mL) and filtered. The filtrate was concentrated and the residue was purified by silica gel column chromatography (dichloromethane/methanol=100/1 to 20/1 as gradient) to afford 8-(((R)-3-((1S,4S)-2-oxa-5-azabicyclo[2.2.1]heptan-5-yl)-2-hydroxypropyl)thio)-7-chloro-4-hydroxy-6-(trifluoromethyl)quinazolin-2(1H)-one (4.00 g, 97% yield) as a yellow solid. MS (ESI) m/z: 452.5 $[M+H]^+$.

(S)-3-((1S,4S)-2-oxa-5-azabicyclo[2.2.1]heptan-5-ylmethyl)-10-chloro-7-hydroxy-9-(trifluoromethyl)-2H-[1,4]thiazino[2,3,4-ij]quinazolin-5(3H)-one (5)

To a mixture of 8-(((R)-3-((1S,4S)-2-oxa-5-azabicyclo[2.2.1]heptan-5-yl)-2-hydroxypropyl)thio)-7-chloro-4-hydroxy-6-(trifluoromethyl)quinazolin-2(1H)-one (3.50 g, 7.70 mmol) and triphenylphosphine (3.00 g, 11.6 mmol) in tetrahydrofuran (50 mL) was added diethyl azodicarboxylate (2.60 g, 15.4 mmol) at 0° C. The mixture was stirred at 0° C. for 45 min. After completion, the mixture was poured into ice-water (200 mL) and extracted with ethyl acetate (200 mL×3). After concentration, the residue was purified by flash chromatography column (C18, acetonitrile/water=30% to 95%) to afford (S)-3-((1S,4S)-2-oxa-5-azabicyclo[2.2.1]heptan-5-ylmethyl)-10-chloro-7-hydroxy-9-(trifluoromethyl)-2H-[1,4]thiazino[2,3,4-ij]quinazolin-5(3H)-one (3.14 g, 70% yield) as a white solid. MS (ESI) m/z: 434.4 $[M+H]^+$.

(2S,6R)-tert-butyl 4-((S)-3-((1S,4S)-2-oxa-5-azabicyclo[2.2.1]heptan-5-ylmethyl)-10-chloro-5-oxo-9-(trifluoromethyl)-3,5-dihydro-2H-[1,4]thiazino[2,3,4-ij]quinazolin-7-yl)-2,6-dimethylpiperazine-1-carboxylate (6)

To a mixture of (S)-3-((1S,4S)-2-oxa-5-azabicyclo[2.2.1]heptan-5-ylmethyl)-10-chloro-7-hydroxy-9-(trifluoromethyl)-2H-[1,4]thiazino[2,3,4-ij]quinazolin-5(3H)-one (700 mg, 1.60 mmol) and potassium carbonate (2.20 g, 16.0 mmol) in acetonitrile (20 mL) was added 4-methylbenzenesulfonic anhydride (782 mg, 2.40 mmol) at 25° C. The mixture was stirred at 25° C. for 3 hours. (2R,6S)-tert-butyl 2,6-dimethylpiperazine-1-carboxylate (684 mg, 3.20 mmol) was added into the reaction solution. The reaction mixture was stirred at 25° C. for 1 hour. After completion, the mixture was poured into ice-water (50 mL) and extracted with ethyl acetate (3×50 mL). The mixture was concentrated and the residue was purified by flash chromatography column (C18, acetonitrile/water=20% to 95%) to afford (2S, 6R)-tert-butyl 4-((S)-3-((1S,4S)-2-oxa-5-azabicyclo[2.2.1]heptan-5-ylmethyl)-10-chloro-5-oxo-9-(trifluoromethyl)-3,5-dihydro-2H-[1,4]thiazino[2,3,4-ij]quinazolin-7-yl)-2,6-dimethylpiperazine-1-carboxylate (800 mg, 80% yield) as a yellow solid. MS (ESI) m/z: 630.6 [M+H]$^+$.

(2S,6R)-tert-butyl 4-((3S)-3-((1S,4S)-2-oxa-5-azabicyclo[2.2.1]heptan-5-ylmethyl)-10-(2,4-difluorophenyl)-5-oxo-9-(trifluoromethyl)-3,5-dihydro-2H-[1,4]thiazino[2,3,4-ij]quinazolin-7-yl)-2,6-dimethylpiperazine-1-carboxylate (7)

To a solution of (2S,6R)-tert-butyl 4-((S)-3-((1S,4S)-2-oxa-5-azabicyclo[2.2.1]heptan-5-ylmethyl)-10-chloro-5-oxo-9-(trifluoromethyl)-3,5-dihydro-2H-[1,4]thiazino[2,3,4-ij]quinazolin-7-yl)-2,6-dimethylpiperazine-1-carboxylate (300 mg, 0.476 mmol) in 1,4-dioxane (10 mL) and water (2 mL) were added tripotassium phosphate (404 mg, 1.90 mmol), (2,4-difluorophenyl)boronic acid (602 mg, 3.81 mmol), and chloro(2-dicyclohexylphosphino-2', 6'-diisopropoxy-1,1'-biphenyl)[2-(2'-amino-1,1'-biphenyl)]palladium(II) (74 mg, 0.095 mmol). The mixture was stirred at 85° C. under nitrogen atmosphere for 4 hours. After completion, the mixture was diluted with tetrahydrofuran (50 mL) and filtered. The filtrate was concentrated and the residue was purified by silica gel column chromatography with gradient of dichloromethane/methanol=100/1 to 30/1 to afford (2S,6R)-tert-butyl 4-((3S)-3-((1S,4S)-2-oxa-5-azabicyclo[2.2.1]heptan-5-ylmethyl)-10-(2,4-difluorophenyl)-5-oxo-9-(trifluoromethyl)-3,5-dihydro-2H-[1,4]thiazino[2,3,4-ij]quinazolin-7-yl)-2,6-dimethylpiperazine-1-carboxylate (252 mg, 75% yield) as a yellow solid. MS (ESI) m/z: 708.4 [M+H]$^+$.

(3S)-3-((1S,4S)-2-oxa-5-azabicyclo[2.2.1]heptan-5-ylmethyl)-10-(2,4-difluorophenyl)-7-((3S,5R)-3,5-dimethylpiperazin-1-yl)-9-(trifluoromethyl)-2H-[1,4]thiazino[2,3,4-ij]quinazolin-5(3H)-one (8)

To a mixture of (2S,6R)-tert-butyl 4-((3S)-3-((1S,4S)-2-oxa-5-azabicyclo[2.2.1]heptan-5-ylmethyl)-10-(2,4-difluorophenyl)-5-oxo-9-(trifluoromethyl)-3,5-dihydro-2H-[1,4]thiazino[2,3,4-ij]quinazolin-7-yl)-2,6-dimethylpiperazine-1-carboxylate (252 mg, 0.36 mmol) in dichloromethane (5 mL) was added trifluoroacetic acid (1 mL) at 0° C. The reaction solution was stirred at room temperature for 1 hour. After completion, the mixture was concentrated and the residue was purified by silica gel column chromatography eluting with dichloromethane/methanol (15:1) to afford (3S)-3-((1S,4S)-2-oxa-5-azabicyclo[2.2.1]heptan-5-ylmethyl)-10-(2,4-difluorophenyl)-7-((3S,5R)-3,5-dimethylpiperazin-1-yl)-9-(trifluoromethyl)-2H-[1,4]thiazino[2,3,4-ij]quinazolin-5(3H)-one (185 mg, 85% yield) as a yellow solid. MS (ESI) m/z: 608.1 [M+H]+.

(3S)-3-((1S,4S)-2-oxa-5-azabicyclo[2.2.1]heptan-5-ylmethyl)-7-((3S,5R)-4-acryloyl-3,5-dimethylpiperazin-1-yl)-10-(2,4-difluorophenyl)-9-(trifluoromethyl)-2H-[1,4]thiazino[2,3,4-ij]quinazolin-5(3H)-one (9)

To a mixture of (3S)-3-((1S,4S)-2-oxa-5-azabicyclo[2.2.1]heptan-5-ylmethyl)-10-(2,4-difluorophenyl)-7-((3S,5R)-3,5-dimethylpiperazin-1-yl)-9-(trifluoromethyl)-2H-[1,4]thiazino[2,3,4-ij]quinazolin-5(3H)-one (160 mg, 0.26 mmol) and triethyl amine (40 mg, 0.39 mmol) in dichloromethane (5 mL) was added acrylic anhydride (40 mg, 0.31 mmol) at 0° C. The mixture was stirred at 0° C. for 1 hour. After completion, the mixture was poured into ice-water (50 mL) and extracted with ethyl acetate (3×20 mL). The mixture was concentrated and the residue was purified by preparative high performance liquid chromatography (20% to 95% acetonitrile in water) to afford (3S)-3-((1S,4S)-2-oxa-5-azabicyclo[2.2.1]heptan-5-ylmethyl)-7-((3S,5R)-4-acryloyl-3,5-dimethylpiperazin-1-yl)-10-(2,4-difluorophenyl)-9-(trifluoromethyl)-2H-[1,4]thiazino[2,3,4-ij]quinazolin-5(3H)-one (103 mg, 59% yield) as a white solid.

$^1$H NMR (400 MHz, $CDCl_3$) δ 8.07 (s, 1H), 7.21-7.14 (m, 1H), 7.06-6.93 (m, 2H), 6.66-6.59 (m, 1H), 6.43-6.38 (m, 1H), 5.77 (d, J=12.0 Hz, 1H), 5.28-5.24 (m, 1H), 4.74-4.60 (m, 2H), 4.43-4.37 (m, 1H), 4.19 (d, J=13.6 Hz, 2H), 3.91-3.84 (m, 1H), 3.69-3.31 (m, 5.5H), 2.99-2.85 (m, 4.5H), 1.75-1.66 (m, 2H), 1.60-1.58 (m, 3H), 1.49-1.41 (m, 3H). MS (ESI) m/z: 662.1 [M+H]$^+$.

X. Example 576 and 577

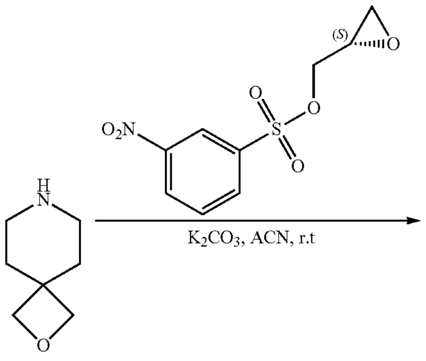

1

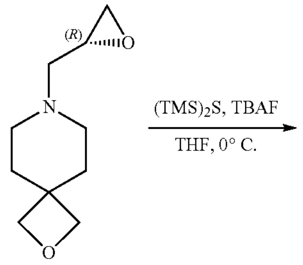

2

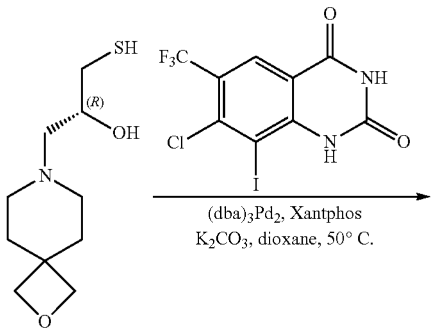

3

-continued
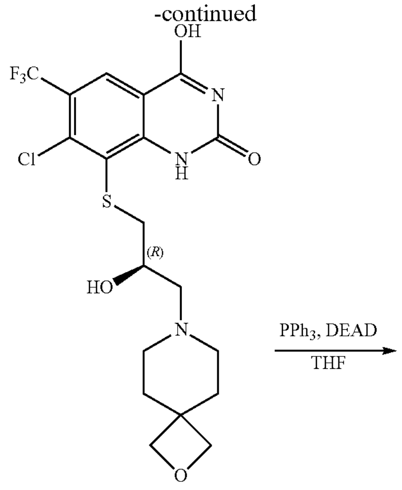
4
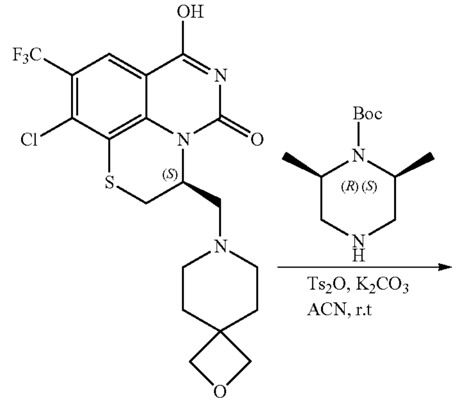
5
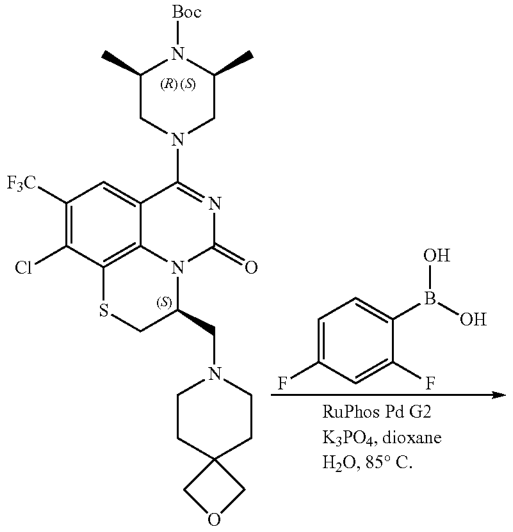
6
-continued
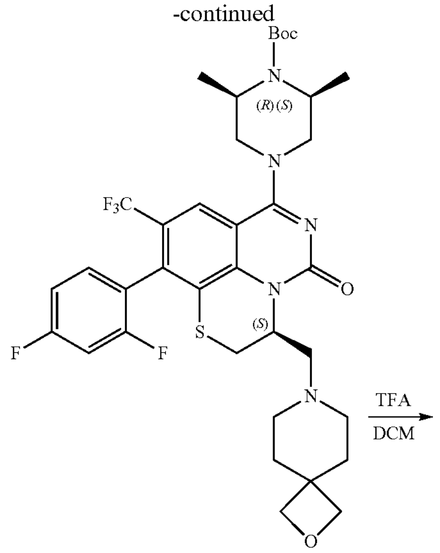
7
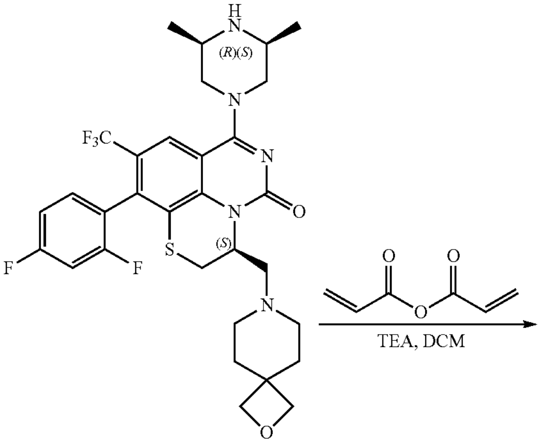
8
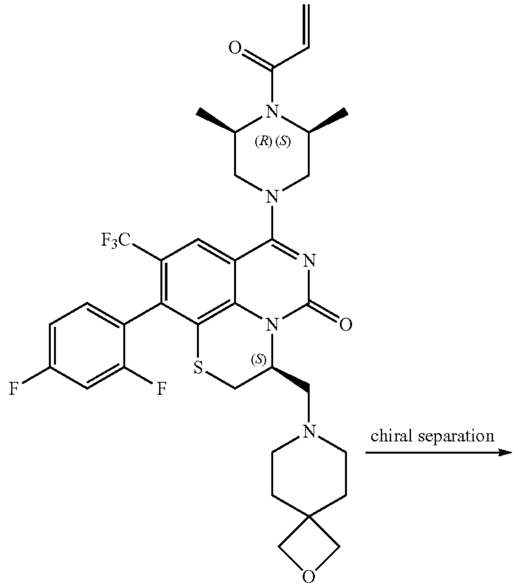
9

-continued

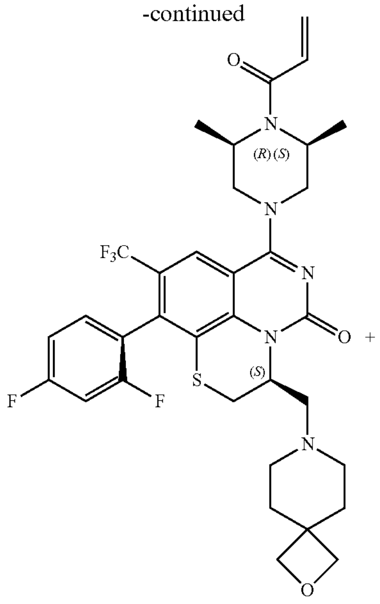

P1

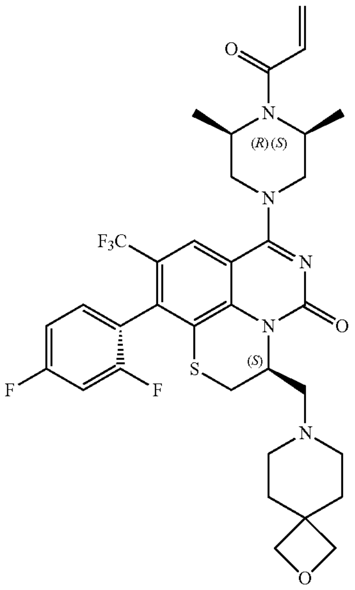

P2

(R)-7-(oxiran-2-ylmethyl)-2-oxa-7-azaspiro[3.5] nonane (2)

To a mixture of (S)-oxiran-2-ylmethyl 3-nitrobenzenesulfonate (5.9 g, 22.8 mmol), 2-oxa-7-azaspiro[3.5]nonane oxalate (4.5 g, 20.7 mmol) in acetonitrile (60 mL) was added potassium carbonate (14.3 g, 103.6 mmol) at 0° C. The mixture was stirred under nitrogen atmosphere at room temperature for 16 hours. After completion, the mixture was concentrated and the residue was purified by silica gel column eluting with dichloromethane/methanol (20/1) to afford (R)-7-(oxiran-2-ylmethyl)-2-oxa-7-azaspiro[3.5] nonane (3.45 g, 91% yield) as a brown oil. MS (ESI) m/z: 180.1 [M+H]$^+$.

(R)-1-mercapto-3-(2-oxa-7-azaspiro[3.5]nonan-7-yl) propan-2-ol (3)

To a mixture of (R)-7-(oxiran-2-ylmethyl)-2-oxa-7-azaspiro[3.5]nonane (3.74 g, 20.4 mmol) in tetrahydrofuran (70 mL) was added 1,1,1,3,3,3-hexamethyldisilathiane (5.45 g, 30.6 mmol) and tetrabutylammonium fluoride (1.0 M in tetrahydrofuran, 6.1 mL, 6.1 mmol) at 0° C. The mixture was stirred at room temperature for 6 hours. After completion, the mixture was concentrated and the residue was purified by silica gel column eluting with dichloromethane/methanol (20/1) to afford (R)-1-mercapto-3-(2-oxa-7-azaspiro[3.5]nonan-7-yl)propan-2-ol (3.47 g, 78% yield) as a brown oil. MS (ESI) m/z: 218.2 [M+H]$^+$.

(R)-7-chloro-4-hydroxy-8-((2-hydroxy-3-(2-oxa-7-azaspiro[3.5]nonan-7-yl)propyl)thio)-6-(trifluoromethyl)quinazolin-2(1H)-one (4)

To a solution of 7-chloro-8-iodo-6-(trifluoromethyl)quinazoline-2,4(1H,3H)-dione (2.0 g, 4.59 mmol) in dioxane (50 mL) were added potassium carbonate (2.5 g, 18.36 mmol), (R)-1-mercapto-3-(2-oxa-7-azaspiro[3.5]nonan-7-yl)propan-2-ol (1.5 g, 6.88 mmol), 4,5-bis(diphenyl-phosphino)-9,9-dimethylxanthene (526 mg, 0.9 mmol) and tris (dibenzylideneacetone) dipalladium (421 mg, 0.45 mmol). The mixture was stirred at 50° C. under nitrogen atmosphere for 16 hours. After completion, the mixture was concentrated and the residue was purified by flash chromatography column (C18, acetonitrile/water=30% to 95%) to afford (R)-7-chloro-4-hydroxy-8-((2-hydroxy-3-(2-oxa-7-azaspiro [3.5]nonan-7-yl)propyl)thio)-6-(trifluoromethyl)quinazolin-2(1H)-one (2.16 g, 98% yield) as a yellow solid. MS (ESI) m/z: 480.4 [M+H]$^+$.

(S)-3-(2-oxa-7-azaspiro[3.5]nonan-7-ylmethyl)-10-chloro-7-hydroxy-9-(trifluoromethyl)-2H-[1,4]thiazino[2,3,4-ij]quinazolin-5(3H)-one (5)

To a mixture of (R)-7-chloro-4-hydroxy-8-((2-hydroxy-3-(2-oxa-7-azaspiro[3.5]nonan-7-yl)propyl)thio)-6-(trifluoromethyl)quinazolin-2(1H)-one (2.16 g, 4.5 mmol) and triphenylphosphoranylidene (1.77 g, 6.75 mmol) in tetrahydrofuran (800 mL) was added diethyl azodicarboxylate (1.18 g, 6.75 mmol). The mixture was stirred at room temperature for 2 hours. After completion, the mixture was poured into ice-water (100 mL) and extracted with ethyl acetate (100 mL×3). The organic layer was dried over $Na_2SO_4$. After concentration, the residue was purified by flash chromatography column (C18, acetonitrile/water=20% to 95%) to afford (S)-3-(2-oxa-7-azaspiro[3.5]nonan-7-ylmethyl)-10-chloro-7-hydroxy-9-(trifluoromethyl)-2H-[1,4] thiazino[2,3,4-ij]quinazolin-5(3H)-one (1.45 g, 70% yield) as a white solid. MS (ESI) m/z: 462.1 [M+H]$^+$.

(2S,6R)-tert-butyl 4-((S)-3-(2-oxa-7-azaspiro[3.5] nonan-7-ylmethyl)-10-chloro-5-oxo-9-(trifluoromethyl)-3,5-dihydro-2H-[1,4]thiazino[2,3,4-ij]quinazolin-7-yl)-2,6-dimethylpiperazine-1-carboxylate (6)

To a mixture of (S)-3-(2-oxa-7-azaspiro[3.5]nonan-7-ylmethyl)-10-chloro-7-hydroxy-9-(trifluoromethyl)-2H-[1,4] thiazino[2,3,4-ij]quinazolin-5(3H)-one (700 mg, 1.52 mmol) and potassium carbonate (2.1 g, 15.2 mmol) in acetonitrile (60 mL) was added 4-methylbenzenesulfonic anhydride (992 mg, 3.04 mmol) at 0° C. The mixture was stirred at 0° C. for 30 minute and at room temperature for 2 hours. After completion, (2S,6R)-tert-butyl 2,6-dimethylpiperazine-1-carboxylate (977 mg, 4.56 mmol) was added into the reaction solution. The mixture was stirred at room temperature for 1 hour. After completion, the mixture was poured into ice-water (50 mL) and extracted with ethyl acetate (3x50 mL). After concentration, the residue was purified by Flash chromatography column (C18, acetonitrile/water=20% to 95%) to afford (2S,6R)-tert-butyl 4-((S)-3-(2-oxa-7-azaspiro[3.5]nonan-7-ylmethyl)-10-chloro-5-oxo-9-(trifluoromethyl)-3,5-dihydro-2H-[1,4]thiazino[2,3,4-ij]quinazolin-7-yl)-2,6-dimethylpiperazine-1-carboxylate (710 mg, 71% yield) as a yellow solid. MS (ESI) m/z: 658.7 $[M+H]^+$.

(2S,6R)-tert-butyl 4-((3S)-3-(2-oxa-7-azaspiro[3.5]nonan-7-ylmethyl)-10-(2,4-difluorophenyl)-5-oxo-9-(trifluoromethyl)-3,5-dihydro-2H-[1,4]thiazino[2,3,4-ij]quinazolin-7-yl)-2,6-dimethylpiperazine-1-carboxylate (7)

To a mixture of (2S,6R)-tert-butyl 4-((S)-3-(2-oxa-7-azaspiro[3.5]nonan-7-ylmethyl)-10-chloro-5-oxo-9-(trifluoromethyl)-3,5-dihydro-2H-[1,4]thiazino[2,3,4-ij]quinazolin-7-yl)-2,6-dimethylpiperazine-1-carboxylate (200 mg, 0.30 mmol) and tripotassium orthophosphate (194 mg, 0.91 mmol) in 1,4-dioxane (5 mL) and water (1 mL) was added Chloro(2-dicyclohexylphosphino-2', 6'-diisopropoxy-1,1'-biphenyl)[2-(2'-amino-1,1'-biphenyl)]palladium(II) (24 mg, 0.03 mmol) and (2,4-difluorophenyl)boronic acid (480 mg, 3.04 mmol). The mixture was stirred at 80° C. for 4 hours. After completion, the mixture was purified by silica gel column eluting with dichloromethane/methanol (20/1) to afford the (2S,6R)-tert-butyl 4-((3S)-3-(2-oxa-7-azaspiro[3.5]nonan-7-ylmethyl)-10-(2,4-difluorophenyl)-5-oxo-9-(trifluoromethyl)-3,5-dihydro-2H-[1,4]thiazino[2,3,4-ij]quinazolin-7-yl)-2,6-dimethylpiperazine-1-carboxylate (215 mg, 96% yield) as a yellow solid. MS (ESI) m/z: 736.9 $[M+H]^+$.

(3S)-3-(2-oxa-7-azaspiro[3.5]nonan-7-ylmethyl)-10-(2,4-difluorophenyl)-7-((3S,5R)-3,5-dimethylpiperazin-1-yl)-9-(trifluoromethyl)-2H-[1,4]thiazino[2,3,4-ij]quinazolin-5(3H)-one (8)

To a mixture of (3S)-3-(2-oxa-7-azaspiro[3.5]nonan-7-ylmethyl)-10-(2,4-difluorophenyl)-7-((3S,5R)-3,5-dimethylpiperazin-1-yl)-9-(trifluoromethyl)-2H-[1,4]thiazino[2,3,4-ij]quinazolin-5(3H)-one (215 mg, 0.29 mmol) in dichloromethane (3 mL) was added trifluoroacetic acid (1 mL). The mixture was stirred at room temperature for 2 hours. After completion, the mixture was concentrated and the residue was purified by silica gel column eluting with dichloromethane/methanol (20/1) to afford the (3S)-3-(2-oxa-7-azaspiro[3.5]nonan-7-ylmethyl)-10-(2,4-difluorophenyl)-7-((3S,5R)-3,5-dimethylpiperazin-1-yl)-9-(trifluoromethyl)-2H-[1,4]thiazino[2,3,4-ij]quinazolin-5(3H)-one (120 mg, 65% yield) as a yellow solid. MS (ESI) m/z: 636.7 $[M+H]^+$.

(3S)-3-(2-oxa-7-azaspiro[3.5]nonan-7-ylmethyl)-7-((3S,5R)-4-acryloyl-3,5-dimethylpiperazin-1-yl)-10-(2,4-difluorophenyl)-9-(trifluoromethyl)-2H-[1,4]thiazino[2,3,4-ij]quinazolin-5(3H)-one (9)

To a mixture of (3S)-3-(2-oxa-7-azaspiro[3.5]nonan-7-ylmethyl)-10-(2,4-difluorophenyl)-7-((3S,5R)-3,5-dimethylpiperazin-1-yl)-9-(trifluoromethyl)-2H-[1,4]thiazino[2,3,4-ij]quinazolin-5(3H)-one (100 mg, 0.16 mmol) and triethylamine (32 mg, 0.32 mmol) in dichloromethane (8 mL) was added acrylic anhydride (20.1 mg, 0.16 mmol) at 0° C. The mixture was stirred at 0° C. for 2 hours. After completion, the mixture was purified by preparative high performance liquid chromatography (20% to 95% acetonitrile in water as gradient) to afford the product (50 mg, 46% yield) as a light yellow solid. MS (ESI) m/z: 690.1 $[M+H]^+$.

The above racemate (50 mg, 0.07 mmol) was dissolved in ethanol (5 mL) and separated by chiral supercritical fluid chromatography (separation condition: Column: AD-H 5 μm 20*250 mm; Mobile Phase: CO2:IPA=60:40 at 15 mL/min; Temp: 25° C.; Wavelength: 254 nm) to afford two atropisomers of the title compounds (P1: 15.6 mg with 100% de and P2: 18.4 mg with 100% de); Chiral SFC Analytical condition: on AD-H was using 5 μm 4.6x250 mm column, Mobile Phase: $CO_2$:IPA=60:40 at 1 mL/min; Temp: 25° C.; Wavelength: 254 nm).

P1: $^1H$ NMR (400 MHz, $CDCl_3$) δ 8.06 (s, 1H), 7.21-7.15 (m, 1H), 7.06-6.94 (m, 2H), 6.65-6.59 (m, 1H), 6.43-6.38 (m, 1H), 5.79-5.76 (dd, J=10.4 Hz, 1.6 Hz, 1H), 5.37-5.35 (m, 1H), 4.72-4.65 (m, 2H), 4.46-4.32 (m, 4H), 4.20-4.17 (m, 2H), 3.48-3.30 (m, 3H), 3.00-2.96 (m, 1H), 2.76-2.66 (m, 1H), 2.65-2.51 (m, 2H), 2.47-2.28 (m, 3H), 1.82-1.81 (m, 4H), 1.61-1.60 (m, 3H), 1.48-1.47 (m, 3H); Chiral SFC fraction 1: d.e.=100%, Rt=5.82 min.

P2: $^1H$ NMR (400 MHz, $CDCl_3$) δ 8.06 (s, 1H), 7.23-7.14 (m, 1H), 7.04-6.95 (m, 2H), 6.65-6.59 (m, 1H), 6.42-6.38 (m, 1H), 5.78-5.76 (dd, J=10.4 Hz, 1.6 Hz, 1H), 5.32-5.31 (m, 1H), 4.66-4.57 (m, 2H), 4.44-4.32 (m, 4H), 4.20-4.16 (m, 2H), 3.44-3.30 (m, 3H), 3.07-2.98 (m, 1H), 2.76-2.71 (m, 1H), 2.68-2.52 (m, 2H), 2.49-2.27 (m, 3H), 1.80-1.71 (m, 4H), 1.62-1.60 (m, 3H), 1.49-1.42 (m, 3H); Chiral SFC fraction 2: d.e.=99.8%, Rt=6.76 min.

Y. Example 580 and 581

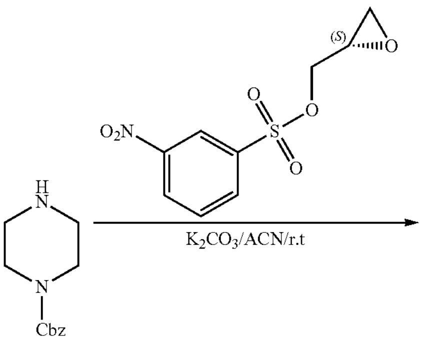

1

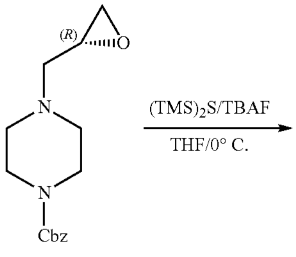

2

-continued
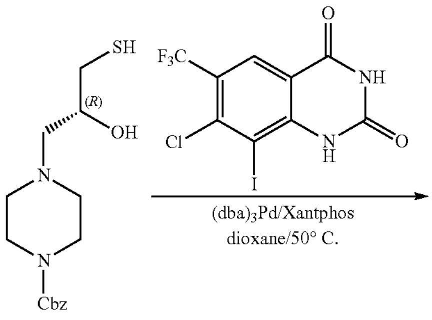
3
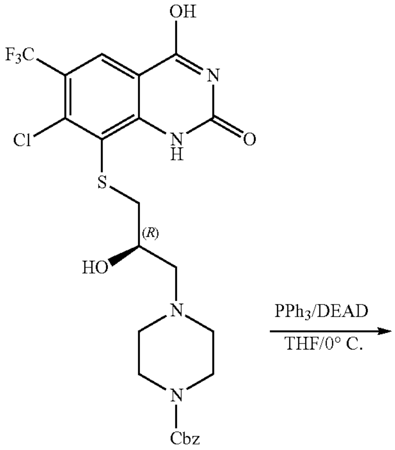
4
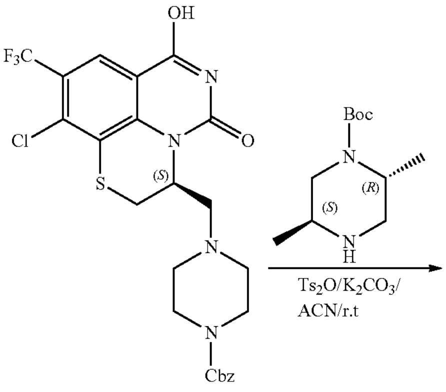
5
-continued
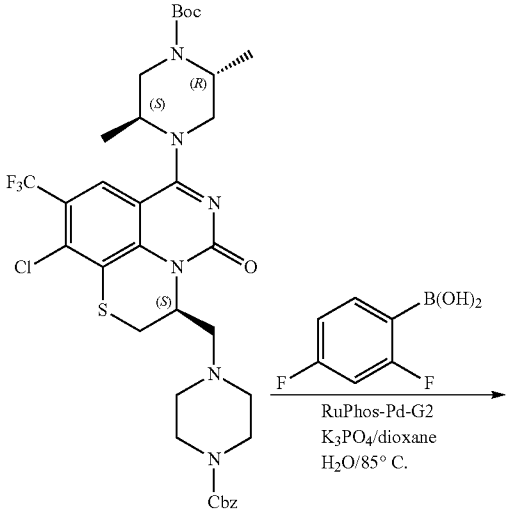
6
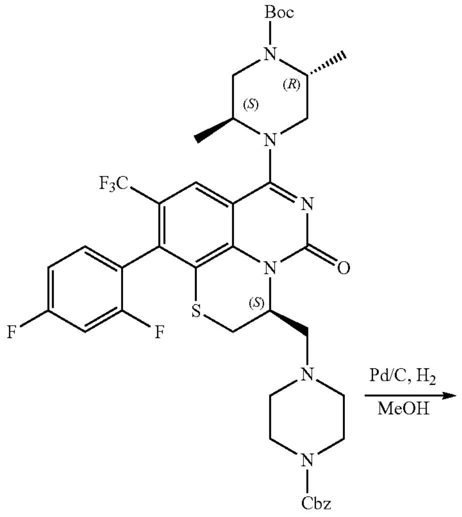
7
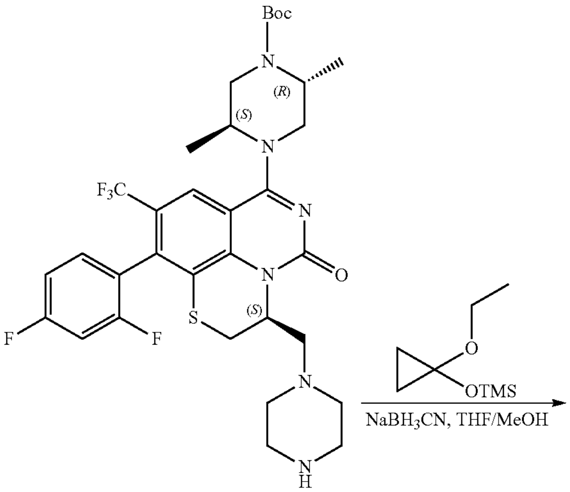
8

-continued

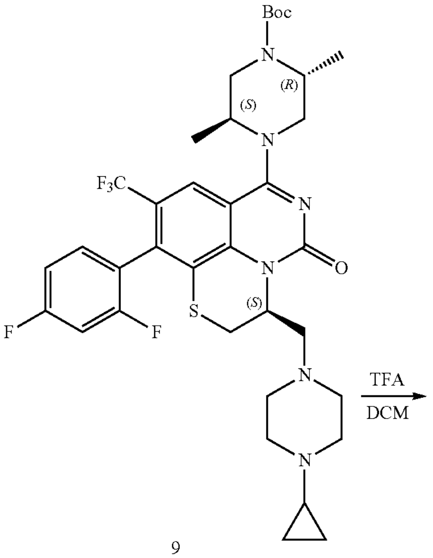

9

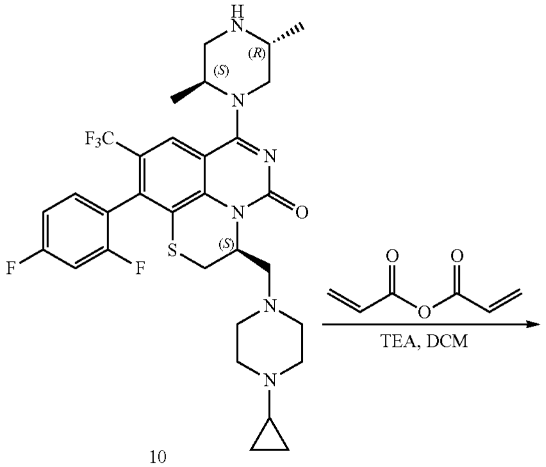

10

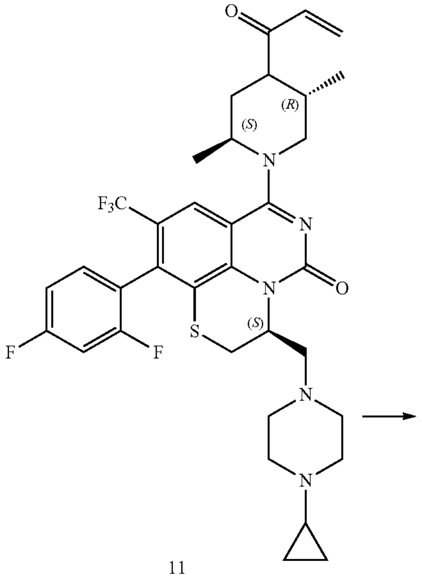

11

-continued

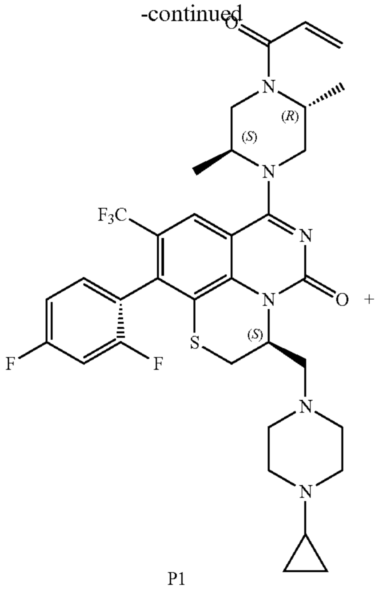

P1

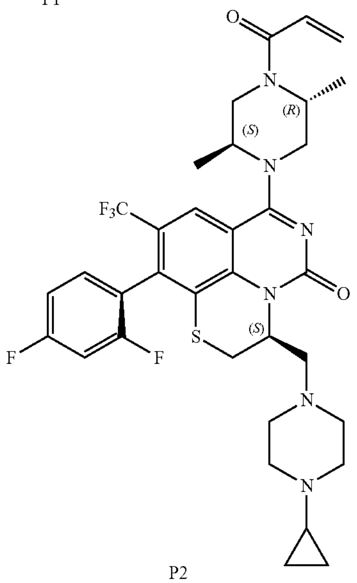

P2

(R)-benzyl 4-(oxiran-2-ylmethyl)piperazine-1-carboxylate (2)

To a mixture of (S)-oxiran-2-ylmethyl 3-nitrobenzenesulfonate (25.0 g, 96.5 mmol) and benzyl piperazine-1-carboxylate (19.3 g, 75.8 mmol) in acetonitrile (150 mL) was added potassium carbonate (24.0 g, 176 mmol) at 0° C. The mixture was stirred under nitrogen atmosphere at room temperature for 22 hours. After completion, the mixture was concentrated and the residue was purified by silica gel column eluting with dichloromethane/methanol (50/1) to afford (R)-benzyl 4-(oxiran-2-ylmethyl)piperazine-1-carboxylate (24.5 g, crude) as a light yellow oil. MS (ESI) m/z: 277.4 $[M+H]^+$.

(R)-benzyl 4-(3-hydroxy-2-mercaptopropyl)piperazine-1-carboxylate (3)

To a mixture of (R)-benzyl 4-(oxiran-2-ylmethyl)piperazine-1-carboxylate (24.5 g, 88.7 mmol) in tetrahydrofuran (300 mL) were added 1,1,1,3,3,3-hexamethyldisilathiane (17.4 g, 97.5 mmol) and tetrabutylammonium fluoride (1.0 M in tetrahydrofuran, 26.7 mL, 26.7 mmol) at 0° C. The mixture was stirred at room temperature for 2 hours. After completion, the mixture was poured into water (300 mL), extracted with ethyl acetate (3×200 mL). The organic phase was washed with brine (300 mL) and dried over anhydrous sodium sulfate. After filtration and concentration, the residue was purified by silica gel column eluting with dichloromethane/methanol (50/1) to afford (R)-benzyl 4-(3-hydroxy-2-mercaptopropyl)piperazine-1-carboxylate (20.8 g, 76% yield) as a colorless oil. $^1$H NMR (400 MHz, $CDCl_3$) δ 7.36-7.31 (m, 5H), 5.13 (s, 2H), 3.80-3.78 (m, 1H), 3.54-3.50 (m, 4H), 3.39 (s, 1H), 2.66-2.57 (m, 4H), 2.46-2.40 (m, 4H), 1.57-1.52 (m, 1H). MS (ESI) m/z: 311.5 [M+H]$^+$.

(R)-benzyl 4-(3-((7-chloro-4-hydroxy-2-oxo-6-(trifluoromethyl)-1,2-dihydroquinazolin-8-yl)thio)-2-hydroxypropyl)piperazine-1-carboxylate (4)

To a solution of 7-chloro-8-iodo-6-(trifluoromethyl)quinazoline-2,4(1H,3H)-dione (5.00 g, 12.8 mmol) in dioxane (128 mL) were added potassium carbonate (5.29 g, 38.4 mmol), (R)-benzyl 4-(2-hydroxy-3-mercaptopropyl)piperazine-1-carboxylate (3.97 g, 12.8 mmol), 4,5-bis(diphenylphosphino)-9,9-dimethylxanthene (1.47 g, 2.56 mmol) and tris(dibenzylideneacetone) dipalladium (1.20 g, 1.28 mmol). The mixture was stirred at 55° C. under nitrogen atmosphere for 8 hours. After completion, the mixture was diluted with tetrahydrofuran (300 mL) and filtered. The filtrate was concentrated and the residue was purified by silica gel column chromatography with a gradient of dichloromethane/methanol=100/1 to 20/1 to afford (R)-benzyl 4-(3-((7-chloro-4-hydroxy-2-oxo-6-(trifluoromethyl)-1,2-dihydroquinazolin-8-yl)thio)-2-hydroxypropyl)piperazine-1-carboxylate (5.70 g, 78% yield) as a yellow solid. MS (ESI) m/z: 573.5 [M+H]$^+$.

(S)-benzyl 4-((10-chloro-7-hydroxy-5-oxo-9-(trifluoromethyl)-3,5-dihydro-2H-[1,4]thiazino[2,3,4-ij]quinazolin-3-yl)methyl)piperazine-1-carboxylate (5)

To a mixture of (R)-benzyl 4-(3-((7-chloro-4-hydroxy-2-oxo-6-(trifluoromethyl)-1,2-dihydroquinazolin-8-yl)thio)-2-hydroxypropyl)piperazine-1-carboxylate (4.66 g, 8.1 mmol) and triphenylphosphine (4.26 g, 16.2 mmol) in tetrahydrofuran (81 mL) was added diethyl azodicarboxylate (2.81 g, 16.2 mmol) at 0° C. The mixture was stirred at 0° C. for 45 min. After completion, the mixture was poured into ice-water (300 mL) and extracted with ethyl acetate (3×200 mL). After concentration, the residue was purified by flash chromatography column (C18, acetonitrile/water=30% to 95%) to afford (S)-benzyl 4-((10-chloro-7-hydroxy-5-oxo-9-(trifluoromethyl)-3,5-dihydro-2H-[1,4]thiazino[2,3,4-ij]quinazolin-3-yl)methyl)piperazine-1-carboxylate (3.14 g, 70% yield) as a white solid. MS (ESI) m/z: 555.5 [M+H]$^+$.

(2R,5S)-tert-butyl 4-((S)-3-((4-((benzyloxy)carbonyl)piperazin-1-yl)methyl)-10-chloro-5-oxo-9-(trifluoromethyl)-3,5-dihydro-2H-[1,4]thiazino[2,3,4-ij]quinazolin-7-yl)-2,5-dimethylpiperazine-1-carboxylate (6)

To a mixture of (S)-benzyl 4-((10-chloro-7-hydroxy-5-oxo-9-(trifluoromethyl)-3,5-dihydro-2H-[1,4]thiazino[2,3,4-ij]quinazolin-3-yl)methyl)piperazine-1-carboxylate (1.77 g, 3.19 mmol) and potassium carbonate (4.40 g, 3.19 mmol) in acetonitrile (106 mL) was added 4-methylbenzenesulfonic anhydride (2.08 g, 6.38 mmol) at 25° C. The mixture was stirred at 25° C. for 3 hours. After completion, (2R,5S)-tert-butyl 2,5-dimethylpiperazine-1-carboxylate (1.36 g, 6.38 mmol) was added into the reaction solution. The reaction mixture was stirred at 25° C. for 1 hour. After completion, the mixture was poured into ice-water (300 mL) and extracted with ethyl acetate (200 mL×3). After concentration, the residue was purified by flash chromatography column (C18, acetonitrile/water=20% to 95%) to afford (2R,5S)-tert-butyl 4-((S)-3-((4-((benzyloxy)carbonyl)piperazin-1-yl)methyl)-10-chloro-5-oxo-9-(trifluoromethyl)-3,5-dihydro-2H-[1,4]thiazino[2,3,4-ij]quinazolin-7-yl)-2,5-dimethylpiperazine-1-carboxylate (1.43 g, 60% yield) as a pale-white solid. MS (ESI) m/z: 751.1 [M+H]$^+$.

(2R,5S)-tert-butyl 4-((3S)-3-((4-((benzyloxy)carbonyl)piperazin-1-yl)methyl)-10-(2,4-difluorophenyl)-5-oxo-9-(trifluoromethyl)-3,5-dihydro-2H-[1,4]thiazino[2,3,4-ij]quinazolin-7-yl)-2,5-dimethylpiperazine-1-carboxylate (7)

To a solution of (2R,5S)-tert-butyl 4-((S)-3-((4-((benzyloxy)carbonyl)piperazin-1-yl)methyl)-10-chloro-5-oxo-9-(trifluoromethyl)-3,5-dihydro-2H-[1,4]thiazino[2,3,4-ij]quinazolin-7-yl)-2,5-dimethylpiperazine-1-carboxylate (1 g, 1.3 mmol) in 1,4-dioxane (15 mL) and water (3 mL) were added tripotassium phosphate (1.1 g, 5.2 mmol), (2,4-difluorophenyl)boronic acid (1.67 g, 10.6 mmol) and Chloro (2-dicyclohexylphosphino-2', 6'-diisopropoxy-1,1'-biphenyl)[2-(2'-amino-1,1'-biphenyl)]palladium(II) (202 mg, 0.26 mmol). The mixture was stirred at 85° C. under nitrogen atmosphere for 4 hours. After completion, the mixture was diluted with tetrahydrofuran (300 mL) and filtered. The filtrate was concentrated and the residue was purified by silica gel column chromatography with a gradient of dichloromethane/methanol=100/1 to 30/1 to afford (2R,5S)-tert-butyl 4-((3S)-3-((4-((benzyloxy)carbonyl)piperazin-1-yl)methyl)-10-(2,4-difluorophenyl)-5-oxo-9-(trifluoromethyl)-3,5-dihydro-2H-[1,4]thiazino[2,3,4-ij]quinazolin-7-yl)-2,5-dimethylpiperazine-1-carboxylate (1.00 g, 93% yield) as a yellow solid. MS (ESI) m/z: 829.5 [M+H]$^+$.

(2R,5S)-tert-butyl 4-((3S)-10-(2,4-difluorophenyl)-5-oxo-3-(piperazin-1-ylmethyl)-9-(trifluoromethyl)-3,5-dihydro-2H-[1,4]thiazino[2,3,4-ij]quinazolin-7-yl)-2,5-dimethylpiperazine-1-carboxylate (8)

To a mixture of (2R,5S)-tert-butyl 4-((3S)-3-((4-((benzyloxy)carbonyl)piperazin-1-yl)methyl)-10-(2,4-difluorophenyl)-5-oxo-9-(trifluoromethyl)-3,5-dihydro-2H-[1,4]thiazino[2,3,4-ij]quinazolin-7-yl)-2,5-dimethylpiperazine-1-carboxylate (1.00 g, 1.20 mmol) in ethanol (15 ml) was added Pd/C (0.300 g, 30% w/w). The mixture was stirred at room temperature under hydrogen atmosphere for 1 hour. After completion, the mixture was filtered and concentrated. The residue was purified by silica gel column chromatography eluting with dichloromethane/methanol (15/1) to afford (2R,5S)-tert-butyl 4-((3S)-10-(2,4-difluorophenyl)-5-oxo-3-(piperazin-1-ylmethyl)-9-(trifluoromethyl)-3,5-dihydro-2H-[1,4]thiazino[2,3,4-ij]quinazolin-7-yl)-2,5-dimethylpiperazine-1-carboxylate (600 mg, 71% yield) as a yellow solid. MS (ESI) m/z: 695.7 [M+H]$^+$.

(2R,5S)-tert-butyl 4-((3S)-3-((4-cyclopropylpiperazin-1-yl)methyl)-10-(2,4-difluorophenyl)-5-oxo-9-(trifluoromethyl)-3,5-dihydro-2H-[1,4]thiazino[2,3,4-ij]quinazolin-7-yl)-2,5-dimethylpiperazine-1-carboxylate (9)

To a mixture of (2R,5S)-tert-butyl 4-((3S)-10-(2,4-difluorophenyl)-5-oxo-3-(piperazin-1-ylmethyl)-9-(trifluoromethyl)-3,5-dihydro-2H-[1,4]thiazino[2,3,4-ij]quinazolin-7-yl)-2,5-dimethylpiperazine-1-carboxylate (400 mg, 0.57 mmol) and sodium cyanoborohydride (359 mg, 5.70 mmol) in tetrahydrofuran (5 mL) and methanol (5 mL) was added (1-ethoxycyclopropoxy)trimethylsilane (991 mg, 5.70 mmol) at 25° C. under nitrogen atmosphere. The reaction solution was heated to 85° C. for 12 hours. After completion, the mixture was filtered and concentrated. the residue was purified by silica gel column chromatography eluting with dichloromethane/methanol (30/1) to afford (2R,5S)-tert-butyl 4-((3S)-3-((4-cyclopropylpiperazin-1-yl)methyl)-10-(2,4-difluorophenyl)-5-oxo-9-(trifluoromethyl)-3,5-dihydro-2H-[1,4]thiazino[2,3,4-ij]quinazolin-7-yl)-2,5-dimethylpiperazine-1-carboxylate (300 mg, 71% yield) as a yellow solid. MS (ESI) m/z: 735.9 $[M+H]^+$.

(3S)-3-((4-cyclopropylpiperazin-1-yl)methyl)-10-(2,4-difluorophenyl)-7-((2S,5R)-2,5-dimethylpiperazin-1-yl)-9-(trifluoromethyl)-2H-[1,4]thiazino[2,3,4-ij]quinazolin-5(3H)-one (10)

To a cooled mixture of (2R,5S)-tert-butyl 4-((3S)-3-((4-cyclopropylpiperazin-1-yl)methyl)-10-(2,4-difluorophenyl)-5-oxo-9-(trifluoromethyl)-3,5-dihydro-2H-[1,4]thiazino[2,3,4-ij]quinazolin-7-yl)-2,5-dimethylpiperazine-1-carboxylate (300 mg, 0.40 mmol) in dichloromethane (5 mL) was added trifluoroacetic acid (1 mL) at 0° C. The reaction solution was stirred at room temperature for 1 hour. After completion, the mixture was concentrated and the residue was purified by silica gel column chromatography eluting with dichloromethane/methanol (15/1) to afford (3S)-3-((4-cyclopropylpiperazin-1-yl)methyl)-10-(2,4-difluorophenyl)-7-((2S,5R)-2,5-dimethylpiperazin-1-yl)-9-(trifluoromethyl)-2H-[1,4]thiazino[2,3,4-ij]quinazolin-5(3H)-one (200 mg, 78% yield) as a yellow solid. MS (ESI) m/z: 635.8 $[M+H]^+$.

(3S)-7-((2S,5R)-4-acryloyl-2,5-dimethylpiperazin-1-yl)-3-((4-cyclopropylpiperazin-1-yl)methyl)-10-(2,4-difluorophenyl)-9-(trifluoromethyl)-2H-[1,4]thiazino[2,3,4-ij]quinazolin-5(3H)-one (11)

To a mixture of (3S)-3-((4-cyclopropylpiperazin-1-yl)methyl)-10-(2,4-difluorophenyl)-7-((2S,5R)-2,5-dimethylpiperazin-1-yl)-9-(trifluoromethyl)-2H-[1,4]thiazino[2,3,4-ij]quinazolin-5(3H)-one (180 mg, 0.28 mmol) and triethyl amine (56 mg, 0.56 mmol) in dichloromethane (5 mL) was added acrylic anhydride (70 mg, 0.56 mmol) at 0° C. The mixture was stirred at 0° C. for 1 hour. After completion, the mixture was poured into ice-water (50 mL) and extracted with ethyl acetate (3×20 mL). After concentration, the residue was purified by preparative high performance liquid chromatography (20% to 95% acetonitrile in water) to afford (3S)-7-((2S,5R)-4-acryloyl-2,5-dimethylpiperazin-1-yl)-3-((4-cyclopropylpiperazin-1-yl)methyl)-10-(2,4-difluorophenyl)-9-(trifluoromethyl)-2H-[1,4]thiazino[2,3,4-ij]quinazolin-5(3H)-one (130 mg, 67% yield) as a white solid. MS (ESI) m/z: 689.8 $[M+H]^+$.

The above racemate (130 mg) was dissolved with EtOH (10 mL) and separated by chiral supercritical fluid chromatography (separation condition: Column:Chiralpak AD-H, 5 μm 20×250 mm; Mobile Phase: $CO_2$:EtOH=60:40 at 25 mL/min; Temp: 25° C.; Wavelength: 254 nm) to afford two atropisomers of the title compounds (P1: 54.0 mg with 100% de and P2: 76.0 mg with 100% de); Chiral SFC Analytical condition: on CHIRALPAK® AD-H was using 5 μm 4.6×250 mm column, Mobile Phase: $CO_2$:EtOH=60:40 at 2.5 mL/min; Temp: 25° C.; Wavelength: 254 nm).

P1: $^1$H NMR (400 MHz, $CDCl_3$) δ 7.87 (d, J=6.0, 1H), 7.31-7.27 (m, 1H), 7.16-7.10 (m, 2H), 6.73-6.55 (m, 1H), 6.46-6.37 (m, 1H), 5.84-5.79 (m, 1H), 5.44 (s, 1H), 5.13-4.70 (m, 1.5H), 4.47-4.36 (m, 1H), 4.11-3.70 (m, 3H), 3.52-3.32 (m, 1.5H), 3.11-3.03 (m, 1H), 2.84-2.55 (m, 10H), 1.52-1.43 (m, 7H), 0.57-0.42 (m, 4H); Chiral SFC fraction 1: e.e. =100%, Rt=4.96 min.

P2: $^1$H NMR (400 MHz, $CDCl_3$) δ 7.87 (s, 1H), 7.28-7.19 (m, 1H), 7.09-6.98 (m, 2H), 6.72-6.54 (m, 1H), 6.46-6.37 (m, 1H), 5.86-5.79 (m, 1H), 5.42-5.35 (m, 1H), 5.12-4.68 (m, 1.5H), 4.52-4.33 (m, 1H), 4.19-3.67 (m, 3H), 3.51-3.27 (m, 1.5H), 3.10-3.05 (m, 1H), 2.87-2.51 (m, 10H), 1.52-1.29 (m, 7H), 0.59-0.44 (m, 4H); Chiral SFC fraction 2: e.e. =99.9%, Rt=5.50 min.

Example 417: 7-(9-acryloyl-7,9-diazaspiro[bicyclo[3.3.1]nonane-3,3'-oxetan]-7-yl)-10-(2,4-difluorophenyl)-9-(trifluoromethyl)-2,3-dihydro-5H-[1,4]thiazino[2,3,4-ij]quinazolin-5-one

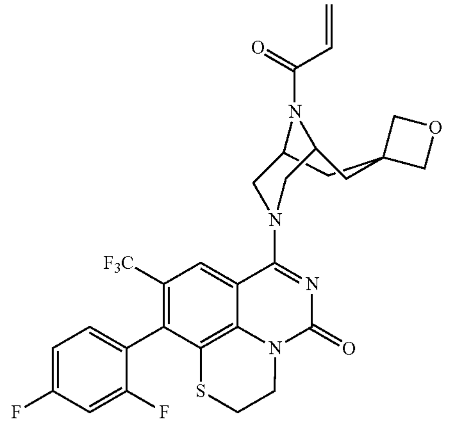 [SMILES: C=CC(=O)N1C2CN(c3nc(=O)n4c5c(c(-c6ccc(F)cc6F)c(C(F)(F)F)cc35)SCC4)CC1CC1(COC1)C2]

The title compound was prepared analogously to Example 84 where 10-(2,4-difluorophenyl)-7-(7,9-diazaspiro[bicyclo[3.3.1]nonane-3,3'-oxetan]-7-yl)-9-(trifluoromethyl)-2,3-dihydro-5H-[1,4]thiazino[2,3,4-ij]quinazolin-5-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 10% yield as a white solid.

m/z (ESI, +ve)=605.2 $(M+H)^+$.

$^1$H NMR (400 MHz, DMSO-d6) δ 7.89 (s, 1H), 7.48-7.43 (m, 1H), 7.32-7.25 (m, 2H), 6.38-6.34 (m, 1H), 6.20-6.14 (m, 1H), 5.99-5.97 (m, 1H), 4.55-4.43 (m, 2H), 4.33-4.27 (m, 3H), 4.12-4.04 (m, 3H), 3.65-3.52 (m, 3H), 3.19-3.14 (m, 2H), 2.14-2.12 (m, 3H), 1.66-1.57 (m, 2H).

Step 1: (1R,5S)-Diethyl-9-benzyl-3-(phenylsulfonyl)-3,9-diazabicyclo[3.3.1]nonane-7,7-dicarboxylate

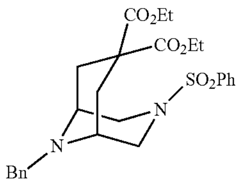

A solution of (1R,5S)-4-(benzenesulfonyl)-2,6-bis(chloromethyl)-1-(1-methylphenyl)piperazine (2 g, 4.8 mmol), 1,3-diethyl propanedioate (800 mg, 5 mmol), tetrabutylammonium bromide (160 mg, 0.5 mmol) and potassium carbonate (1.93 g, 14 mmol) in DMF (20 mL) was stirred at 100° C. for 16 hours. The solution was cooled to room temperature, diluted with water and extracted with ethyl acetate three times. The combined organic layers were washed with brine, dried over sodium sulfate, filtered and concentrated under reduced pressure to obtain a residue that was purified by silica gel chromatography (0-20% ethyl acetate in hexanes) to afford the title compound in 99% yield as colorless oil.

m/z (ESI, +ve)=501.2 $(M+H)^+$.

Step 2: (1R,5S)-(9-benzyl-3-(phenylsulfonyl)-3,9-diazabicyclo[3.3.1]nonane-7,7-diyl)dimethanol

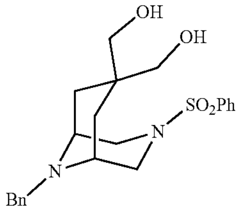

To a solution of (1R,5S)-diethyl 9-benzyl-3-(phenylsulfonyl)-3,9-diazabicyclo[3.3.1]nonane-7,7-dicarboxylate (900 mg, 1.79 mmol) in THF (10 mL) was added lithium aluminum hydride (250 mg, 6.58 mmol) and the mixture was stirred at 0° C. for 2 hours. The reaction was quenched with 15% aqueous NaOH (1 mL), dried over magnesium sulfate and filtered. The filtrate was concentrated under reduced pressure to afford the title compound (700 mg) as colorless oil.

m/z (ESI, +ve)=417.2 $(M+H)^+$.

Step 3: (1R,5S)-9-benzyl-7-(phenylsulfonyl)-7,9-diazaspiro[bicyclo[3.3.1]nonane-3,3'-oxetane]

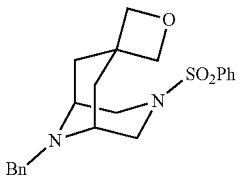

A solution of (1R,5S)-(9-benzyl-3-(phenylsulfonyl)-3,9-diazabicyclo[3.3.1]nonane-7,7-diyl)dimethanol (660 mg, 1.58 mmol), tosyl chloride (383 mg, 2.01 mmol) and triethyl amine (0.8 mL, 5.74 mmol) in toluene (5 mL) was stirred at 100° C. for 2 hours. The solution was cooled down to room temperature and concentrated under reduced pressure to obtain a residue that was purified by reverse phase chromatography to afford the title compound (410 mg) as colorless oil.

m/z (ESI, +ve)=399.1 $(M+H)^+$.

Step 4: (1R,5S)-7,9-dibenzyl-7,9-diazaspiro[bicyclo[3.3.1]nonane-3,3'-oxetane]

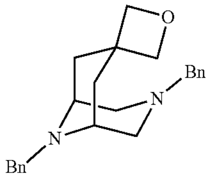 [SMILES: c1ccc(CN2CC3CC4(COC4)CC(C2)N3Cc2ccccc2)cc1]

To a solution of 9-benzyl-7-(phenylsulfonyl)-7,9-diazaspiro[bicyclo[3.3.1]nonane-3,3'-oxetane] (1.36 g, 3.40 mmol) in THF (15 mL) at −78° C. was added $KPPh_2$ (0.5 M solution in THF, 17 mL, 8.5 mmol) dropwise. The mixture was stirred at −78° C. for 3 hours. The reaction was quenched with 1M aqueous HCl (9 mL) and the aqueous phase was separated and concentrated under reduced pressure. The residue was taken up in acetonitrile (15 mL) and potassium carbonate (1.4 g, 10.14 mmol) and benzyl bromide (822 mg, 5.10 mmol) were added. The resulting mixture was stirred at room temperature for 16 hours. The solids were removed by filtration and the filtrate was concentrated and purified by reverse phase chromatography to afford the title compound (1.1 g) as colorless oil.

m/z (ESI, +ve)=349.2 $(M+H)^+$.

Step 5: (1R,5S)-7,9-diazaspiro[bicyclo[3.3.1]nonane-3,3'-oxetane]

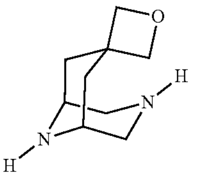 [SMILES: C1NCC2CC3(COC3)CC1N2]

A mixture of (1R,5S)-7,9-dibenzyl-7,9-diazaspiro[bicyclo[3.3.1]nonane-3,3'-oxetane] (1.1 g, 4.26 mol) and 10% palladium on activated carbon (2 g) in methanol/ammonium hydroxide (10/1 mL) was stirred at 25° C. for 16 h under hydrogen atmosphere. The mixture was filtered through celite and the filtrate was concentrated to afford (1R,5S)-7,9-diazaspiro[bicyclo[3.3.1]nonane-3,3'-oxetane] (700 mg, 50%) as colorless oil.

m/z (ESI, +ve)=169.2 $(M+H)^+$.

Step 6: 10-(2,4-difluorophenyl)-7-(7,9-diazaspiro[bicyclo[3.3.1]nonane-3,3'-oxetan]-7-yl)-9-(trifluoromethyl)-2,3-dihydro-5H-[1,4]thiazino[2,3,4-ij]quinazolin-5-one

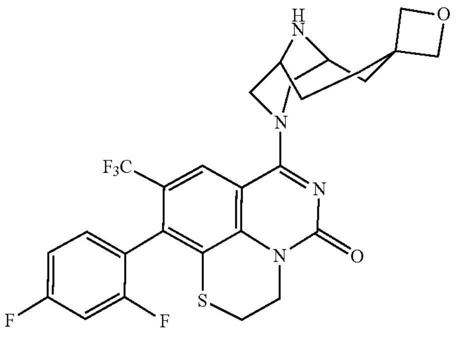 [SMILES: O=c1nc(N2CC3CCC4(COC4)CC(C2)N3)c2cc(C(F)(F)F)c(-c3ccc(F)cc3F)c3c2n1CCS3]

To a solution of 10-(2,4-difluorophenyl)-9-(trifluoromethyl)-2,3-dihydro-5H-[1,4]thiazino[2,3,4-ij]quinazoline-5,7(6H)-dione (100 mg, 0.25 mmol) and N,N-diisopropylethylamine (0.55 mL, 3.08 mmol) in toluene (1 mL), was added $POCl_3$ (1 mL) and the reaction mixture was stirred at 120° C. for 1.5 hours. The solution was concentrated to obtain a residue that was dissolved in dichloroethane (1.5 mL) and a solution of (1R,5S)-7,9-diazaspiro[bicyclo[3.3.1]nonane-3,3'-oxetane] (400 mg) and diisopropylethylamine (0.55 mL, 3.08 mL) in DMF (1.5 mL) was added at 0° C. under nitrogen atmosphere. The mixture was stirred at 0° C. for 1 hours. The crude reaction mixture was purified by reverse phase chromatography to afford the title compound (25 mg) as a yellow solid.

m/z (ESI, +ve)=551.1 $(M+H)^+$.

Example 418: 10-(2,4-difluorophenyl)-7-(9-(2-fluoroacryloyl)-7-oxo-3,9-diazabicyclo[3.3.1]nonan-3-yl)-9-(trifluoromethyl)-2,3-dihydro-5H-[1,4]thiazino[2,3,4-ij]quinazolin-5-one

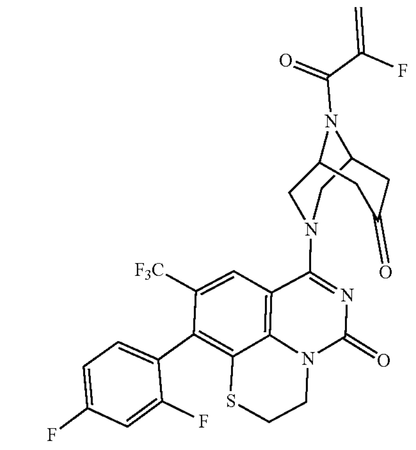 [SMILES: C=C(F)C(=O)N1C2CC(=O)CC1CN(c1nc(=O)n3c4c(c(-c5ccc(F)cc5F)c(C(F)(F)F)cc14)SCC3)C2]

To a solution of 2-fluoroacrylic acid (34 mg, 0.38 mmol) in DMF (3 mL) were added N,N,N',N'-tetramethyl-O-(7-azabenzotriazol-1-yl)uronium (160 mg, 0.42 mmol) and N,N-diisopropylethylamine (99 mg, 0.76 mmol). After 5 minutes, 10-(2,4-difluorophenyl)-7-(7-oxo-3,9-diazabicyclo[3.3.1]nonan-3-yl)-9-(trifluoromethyl)-2,3-dihydro-5H-[1,4]thiazino[2,3,4-ij]quinazolin-5-one (100 mg, 0.19 mmol) was added and stirring was continued at room temperature for two additional hours. The solvent was removed under reduced pressure to afford a residue that was purified by preparative HPLC. The title compound was isolated n 12% yield as a light yellow solid.

m/z (ESI, +ve)=595.1 $(M+H)^+$.

$^1H$ NMR (400 MHz, DMSO-d6) δ 7.77 (s, 1H), 7.50-7.45 (m, 1H), 7.40-7.34 (m 1H), 7.30-7.25 (m, 1H), 5.47 (s, 1H), 5.48-5.27 (m, 1H), 5.29-5.18 (m, 1H), 5.10-5.06 (m, 1H), 4.86-4.79 (m, 2H), 4.39-4.30 (m, 1H), 4.20-3.96 (m, 3H), 3.123-3.13 (m, 4H), 2.98-2.89 (m, 2H).

Example 420: (E)-10-(2,4-difluorophenyl)-7-(9-(4-(dimethylamino)but-2-enoyl)-7-oxo-3,9-diazabicyclo[3.3.1]nonan-3-yl)-9-(trifluoromethyl)-2,3-dihydro-5H-[1,4]thiazino[2,3,4-ij]quinazolin-5-one

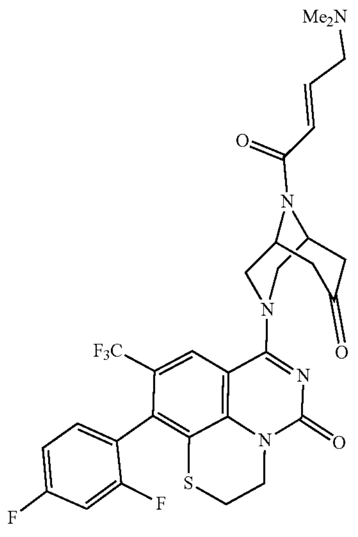

To a solution of (E)-4-(dimethylamino)but-2-enoic acid (148 mg, 1.146 mmol) in DMF (3 mL), N,N,N',N'-tetramethyl-O-(7-azabenzotriazol-1-yl)uronium (457 mg, 1.20 mmol) and N,N-diisopropylethylamine (247 mg, 1.91 mmol) were added. After 5 minutes, 10-(2,4-difluorophenyl)-7-(7-oxo-3,9-diazabicyclo[3.3.1]nonan-3-yl)-9-(trifluoromethyl)-2,3-dihydro-5H-[1,4]thiazino[2,3,4-ij]quinazolin-5-one (100 mg, 0.19 mmol) was added over the reaction mixture and stirring was continued for another 2 hours. The solvent was removed under reduced pressure obtaining a residue that was purified by preparative HPLC to afford the title compound (2.7 mg, 2%) as a white solid.

m/z (ESI, +ve)=634.2 $(M+H)^+$.

$^1H$ NMR (400 MHz, DMSO-d6) δ 7.77 (s, 1H), 7.51-7.46 (m, 1H), 7.43-7.33 (m, 1H), 7.32-7.24 (m, 1H), 6.75 (s, 1H), 5.15 (s, 1H), 4.92 (s, 1H), 4.41-4.25 (m, 2H), 4.17-3.90 (m, 4H), 3.27-3.02 (m, 5H), 2.89-2.69 (m, 4H), 2.46-2.37 (m, 3H), 2.18 (s, 3H).

Example 431: (3S)-8-((S)-4-acryloyl-2-methylpiperazin-1-yl)-11-(2,4-difluorophenyl)-3-hydroxy-10-(trifluoromethyl)-3,4-dihydro-2H,6H-[1,4]thiazepino[2,3,4-ij]quinazolin-6-one

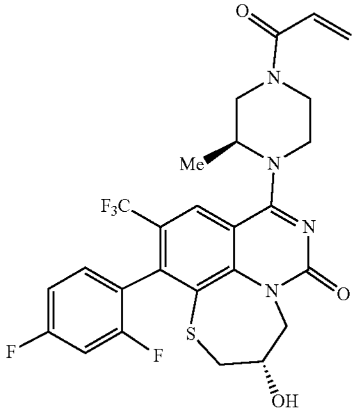 [SMILES: C=CC(=O)N1CCN(c2nc(=O)n3c4c(c(-c5ccc(F)cc5F)c(C(F)(F)F)cc24)SC[C@@H](O)C3)[C@@H](C)C1]

To a mixture of (3S)-11-(2,4-difluorophenyl)-3-hydroxy-8-((S)-2-methylpiperazin-1-yl)-10-(trifluoromethyl)-3,4-dihydro-2H,6H-[1,4]thiazepino[2,3,4-ij]quinazolin-6-one (50 mg, 0.09 mmol) and N,N-diisopropylethylamine (25 mg, 0.19 mmol) in dichloromethane (2 mL), was added prop-2-enoyl prop-2-enoate (19 mg, 0.15 mmol). The reaction mixture was stirred at room temperature for 1 hour. The mixture was concentrated under reduced pressure affording a residue that was purified by preparative HPLC. The title compound was isolated in 4% yield as a white solid.

m/z (ESI, +ve)=567.2 $(M+H)^+$.

$^1H$ NMR (400 MHz, methanol-d4) δ 7.92 (s, 1H), 7.31-7.26 (m, 1H), 7.12-7.06 (m, 2H), 6.87-6.75 (m, 1H), 6.29-6.25 (m, 1H), 5.81 (d, J=12.0 Hz Hz, 1H), 4.41-4.33 (m, 2H), 4.18-4.11 (m, 1H), 4.04-3.99 (m, 1H), 3.77-3.37 (m, 6H), 3.22-2.92 (m, 2H), 1.44-1.34 (m, 3H).

Step 1: (R)-3-(tritylthio)propane-1,2-diol

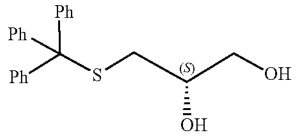

Potassium tert-butoxide (18.3 g, 0.18 mol) was added over a solution of triphenylmethyl mercaptan (25 g, 0.091 mol) and (2R)-3-chloropropane-1,2-diol (10 g, 0.091 mol) in DMF (200 mL) at room temperature. The mixture was stirred for 16 hours and after that time it was quenched with water. The resulting mixture was extracted with ethyl acetate three times and the organic layers were combined and washed with brine, dried over sodium sulfate and filtered. Evaporation of volatiles under reduced pressure afforded a residue that was purified by column chromatography on silica gel (0-50% ethyl acetate in hexanes). The title compound was isolated in 66% yield as yellow oil.

m/z (ESI, +ve)=373.1 $(M+Na)^+$.

Step 2: (S)-1-((tert-butyldimethylsilyl)oxy)-3-(tritylthio)propan-2-ol

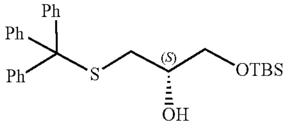

Imidazole (9.71 g, 0.14 mol) and tert-butyldimethylsilyl chloride (9.47 g, 0.063 mol) were added over a solution of (2S)-3-[(triphenylmethyl)sulfanyl] propane-1,2-diol (20 g, 0.057 mol) in DMF (250 mL) at room temperature. After 16 hours, the reaction was quenched by addition of water. The mixture was extracted with ethyl acetate three times and the combined organic layers were washed with brine, dried over sodium sulfate and filtered to afford a residue that was purified by silica gel chromatography (0-15% ethyl acetate in hexanes) to afford the title compound in 60% yield as a yellow oil.

m/z (ESI, +ve)=487.2 $(M+Na)^+$.

Step 3: (S)-(2-(benzyloxy)-3-(tritylthio)propoxy)(tert-butyl)dimethylsilane

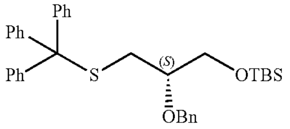

Sodium hydride (2.2 g, 0.090 mol) was added to a mixture of tert-butyl[(2S)-2-hydroxy-3-[(triphenylmethyl)sulfanyl] propoxy] dimethylsilane (28 g, 0.060 mol) in THF (200 mL) at 0° C. The mixture was stirred at 0° C. for 30 minutes and benzyl bromide (11.3 g, 0.066 mol) was added. The resulting solution was stirred at room temperature for 16 hours. The reaction was cooled down to 0° C. and quenched by the addition of saturated aqueous ammonium chloride (100 mL) followed by extraction with ethyl acetate. The combined organic layers were washed with brine, dried over sodium sulfate and filtered. Elimination of volatiles by reduced pressure and purification of the resulting residue by column chromatography on silica gel (0-10% ethyl acetate in hexanes) afforded the title compound in 71% yield as colorless oil.

m/z (ESI, +ve)=577.2 $(M+Na)^+$.

Step 4: (S)-2-(benzyloxy)-3-mercaptopropan-1-ol

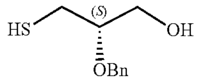

To a mixture of [(2S)-2-(benzyloxy)-3-[(triphenylmethyl)sulfanyl] propoxy](tert-butyl) dimethylsilane (26.5 g, 0.0478 mol) in dichloromethane/TFA (40 mL, 3:1 ratio) at 0° C., was added triethylsilane (16.7 g, 0.14 mol). The mixture was stirred at room temperature for 20 min and after that time the volatiles were removed under reduced pressure at 40° C. The resulting residue was redissolved with saturated sodium bicarbonate and extracted three times with ethyl acetate. The combined organic layers were washed with brine, dried over sodium sulfate and filtered. The crude solution was concentrated under reduced pressure and the resulting crude material purified by column chromatography on silica gel (0-12% methanol in dichloromethane) to afford the title compound in 22% yield as colorless oil.

Step 5: 8-(((S)-2-(benzyloxy)-3-hydroxypropyl)thio)-7-(2,4-difluorophenyl)-6-(trifluoromethyl)quinazoline-2,4(1H,3H)-dione

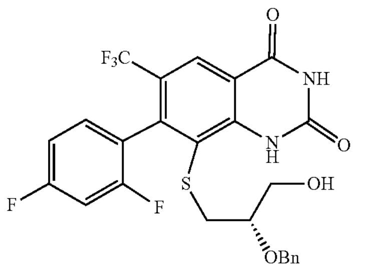 [SMILES: O=c1[nH]c(=O)c2cc(C(F)(F)F)c(-c3ccc(F)cc3F)c(SC[C@H](CO)OCc3ccccc3)c2[nH]1]

The title compound was prepared analogously to Example 100, step 9 where (S)-2-(benzyloxy)-3-mercaptopropan-1-ol was substituted in place of 2-mercaptoethan-1-ol. The title compound was isolated in 53% yield as a white solid.

m/z (ESI, +ve)=539.1 $(M+H)^+$.

Step 6: (3S)-3-(benzyloxy)-11-(2,4-difluorophenyl)-10-(trifluoromethyl)-3,4-dihydro-2H,6H-[1,4]thiazepino[2,3,4-ij]quinazoline-6,8(7H)-dione

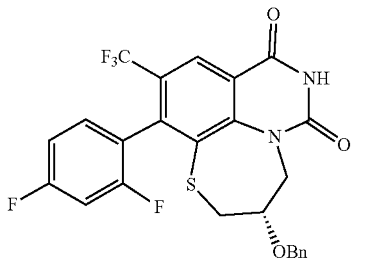 [SMILES: O=c1[nH]c(=O)n2c3c(c(-c4ccc(F)cc4F)c(C(F)(F)F)cc13)SC[C@@H](OCc1ccccc1)C2]

The title compound was prepared analogously to Example 100, step 10 where 8-(((S)-2-(benzyloxy)-3-hydroxypropyl)thio)-7-(2,4-difluorophenyl)-6-(trifluoromethyl)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione. The title compound was isolated in 65% yield as a yellow solid.

m/z (ESI, +ve)=421.0 $(M+H)^+$.

Step 7: tert-butyl (3S)-4-((3S)-3-(benzyloxy)-11-(2,4-difluorophenyl)-6-oxo-10-(trifluoromethyl)-3,4-dihydro-2H,6H-[1,4]thiazepino[2,3,4-ij]quinazolin-8-yl)-3-methylpiperazine-1-carboxylate

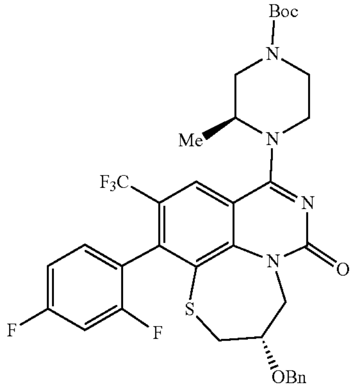 [SMILES: C[C@H]1CN(C(=O)OC(C)(C)C)CCN1c1nc(=O)n2c3c(c(-c4ccc(F)cc4F)c(C(F)(F)F)cc13)SC[C@@H](OCc1ccccc1)C2]

The title compound was prepared analogously to Example 100, step 21 where (3S)-3-(benzyloxy)-11-(2,4-difluorophenyl)-10-(trifluoromethyl)-3,4-dihydro-2H,6H-[1,4]thiazepino[2,3,4-ij]quinazoline-6,8(7H)-dione and tert-butyl (S)-3-methylpiperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 73% yield as a yellow solid m/z (ESI, +ve)=703.2 $(M+H)^+$.

Step 8: (3S)-11-(2,4-difluorophenyl)-3-hydroxy-8-((S)-2-methylpiperazin-1-yl)-10-(trifluoromethyl)-3,4-dihydro-2H,6H-[1,4]thiazepino[2,3,4-ij]quinazolin-6-one

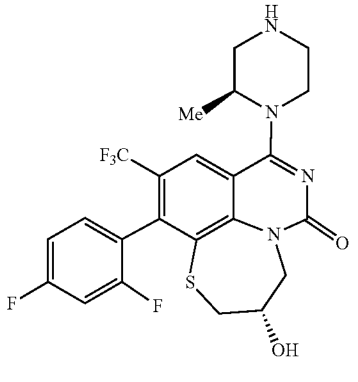 [SMILES: C[C@H]1CNCCN1c1nc(=O)n2c3c(c(-c4ccc(F)cc4F)c(C(F)(F)F)cc13)SC[C@@H](O)C2]

A 1M solution of boron tribromide in dichloromethane (1.1 mL) was added over a solution of tert-butyl (3S)-4-((3S)-3-(benzyloxy)-11-(2,4-difluorophenyl)-6-oxo-10-(trifluoromethyl)-3,4-dihydro-2H,6H-[1,4]thiazepino[2,3,4-ij]quinazolin-8-yl)-3-methylpiperazine-1-carboxylate (200 mg, 0.28 mmol) in dichloromethane (20 mL) precooled to −70° C. The reaction mixture was stirred at −70° C. for 1 hour and quenched by the addition of saturated sodium bicarbonate. The insoluble materials were removed by filtration and the filtrate was concentrated under reduced pressure to afford a residue that was purified by HPLC. The title compound was isolated in 61% yield as a yellow solid.

m/z (ESI, +ve)=513.1 $(M+H)^+$.

Example 439: (E)-7-(9-(4,4-difluorobut-2-enoyl)-7-oxo-3,9-diazabicyclo[3.3.1]nonan-3-yl)-10-(2,4-difluorophenyl)-9-(trifluoromethyl)-2,3-dihydro-5H-[1,4]thiazino[2,3,4-ij]quinazolin-5-one

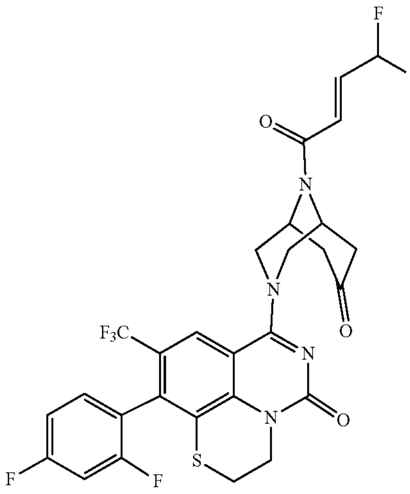

To a solution of (E)-4,4-difluorobut-2-enoic acid (63 mg, 0.516 mmol) in dichloromethane (3 mL), N,N,N',N'-tetramethylchloroformamidinium hexafluorophosphate (58 mg, 0.21 mmol) and N-methylimidazole (47 mg, 0.57 mmol) were added. After 5 minutes, 10-(2,4-difluorophenyl)-7-(7-oxo-3,9-diazabicyclo[3.3.1]nonan-3-yl)-9-(trifluoromethyl)-2,3-dihydro-5H-[1,4]thiazino[2,3,4-ij]quinazolin-5-one (90 mg, 0.17 mmol) was added and the reaction mixture was stirred at room temperature for 2 hours. The solvent was removed under reduced pressure to afford a residue that was purified by preparative HPLC. The title compound was isolated in 4% yield as a white solid.

m/z (ESI, +ve)=627.1 $(M+H)^+$.

$^1$H NMR (400 MHz, DMSO-d6) δ 7.77 (s, 1H), 7.50-7.46 (m, 1H), 7.38-7.35 (m, 1H), 7.31-7.24 (m, 1H), 6.81-6.46 (m, 3H), 5.17 (s, 1H), 4.88 (s, 1H), 4.37-4.33 (m, 1H), 4.31-4.21 (m, 1H), 4.18-3.94 (m, 3H), 3.32-3.10 (m, 5H), 2.97-2.74 (m, 2H).

Example 440: (E)-10-(2,4-difluorophenyl)-7-(7-oxo-9-(4,4,4-trifluorobut-2-enoyl)-3,9-diazabicyclo[3.3.1]nonan-3-yl)-9-(trifluoromethyl)-2,3-dihydro-5H-[1,4]thiazino[2,3,4-ij]quinazolin-5-one

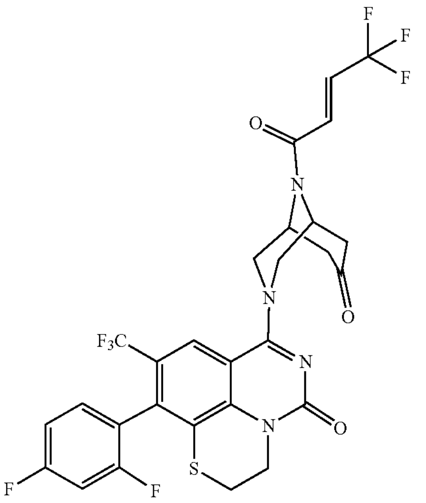 [SMILES: O=C1CC2CN(c3nc(=O)n4c5c(c(-c6ccc(F)cc6F)c(C(F)(F)F)cc35)SCC4)CC(C1)N2C(=O)/C=C/C(F)(F)F]

To a solution of (2E)-4,4,4-trifluorobut-2-enoic acid (43 mg, 0.31 mmol) in dichloromethane (1 mL) were added oxalyl chloride (59 mg, 0.45 mmol) and 2 drops of DMF. The reaction mixture was stirred at room temperature for 30 minutes and after that time a solution of 10-(2,4-difluorophenyl)-7-(7-oxo-3,9-diazabicyclo[3.3.1]nonan-3-yl)-9-(trifluoromethyl)-2,3-dihydro-5H-[1,4]thiazino[2,3,4-ij]quinazolin-5-one (80 mg, 0.15 mmol) and triethylamine (93 mg, 0.92 mmol) in dichloromethane (1 mL) was added. The mixture stirred at room temperature for 1 hour. The solvent was removed under reduced pressure to afford a residue that was purified by preparative HPLC. The title compound was isolated in 4% yield as a white solid.

m/z (ESI, +ve)=645.1 $(M+H)^+$.

$^1$H NMR (400 MHz, DMSO-d6) δ 7.77 (s, 1H), 7.59-7.43 (m, 2H), 7.37 (s, 1H), 7.30-7.26 (m, 1H), 6.93-6.89 (m, 1H), 5.17 (m, 1H), 4.92 (m, 1H), 4.33-4.17 (m, 2H), 4.17-3.97 (m, 3H), 3.30-3.14 (m, 5H), 3.09-2.96 (m, 1H), 2.79-2.72 (m, 1H).

Example 442: (2S)-7-((S)-4-acryloyl-2-methylpiperazin-1-yl)-10-(2,4-difluorophenyl)-2-((dimethylamino)methyl)-9-(trifluoromethyl)-2,3-dihydro-5H-[1,4]thiazino[2,3,4-ij]quinazolin-5-one

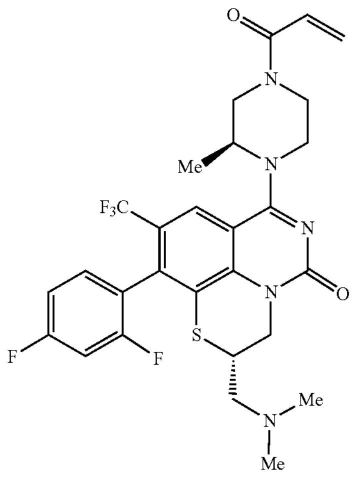 [SMILES: C=CC(=O)N1CCN(c2nc(=O)n3c4c(c(-c5ccc(F)cc5F)c(C(F)(F)F)cc24)S[C@@H](CN(C)C)C3)[C@@H](C)C1]

Over a solution of (2S)-10-(2,4-difluorophenyl)-2-((dimethylamino)methyl)-7-((S)-2-methylpiperazin-1-yl)-9-(trifluoromethyl)-2,3-dihydro-5H-[1,4]thiazino[2,3,4-ij]quinazolin-5-one (38 mg) in acetonitrile (2 mL), triethylamine (0.11 mL) and acryloyl chloride (0.014 mL) were added. The mixture was stirred at room temperature for 30 minutes and at that time quenched by the addition of water. The mixture was extracted with ethyl acetate, dried over sodium sulfate and concentrated to afford a residue that was purified by HPLC. The title compound was isolated as a white solid in 49% yield m/z (ESI, +ve)=594.2 $(M+H)^+$.

Step 1: tert-Butyl (3S)-4-((3S)-11-(2,4-difluorophenyl)-3-hydroxy-6-oxo-10-(trifluoromethyl)-3,4-dihydro-2H,6H-[1,4]thiazepino[2,3,4-ij]quinazolin-8-yl)-3-methylpiperazine-1-carboxylate

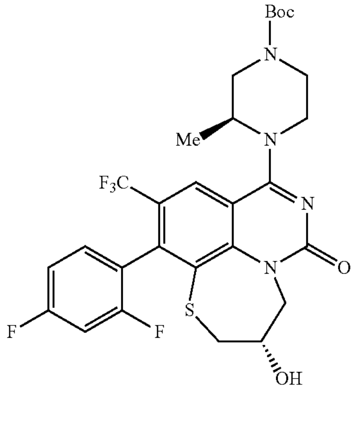 [SMILES: C[C@H]1CN(C(=O)OC(C)(C)C)CCN1c1nc(=O)n2c3c(c(-c4ccc(F)cc4F)c(C(F)(F)F)cc13)SC[C@@H](O)C2]

A solution of tert-butyl (3S)-4-((3S)-3-(benzyloxy)-11-(2,4-difluorophenyl)-6-oxo-10-(trifluoromethyl)-3,4-dihydro-2H,6H-[1,4]thiazepino[2,3,4-ij]quinazolin-8-yl)-3-methylpiperazine-1-carboxylate (100 mg) in 2 mL of isopropanol was hydrogenated at atmospheric pressure in the presence of 75 mg of 10% palladium on activated carbon. After 12 hours, the reaction was filtered through celite and the volatiles removed under reduced pressure to afford a solid that was hydrogenated for a second time in 2 mL of isopropanol and 75 mg of 10% palladium on activated carbon. The reaction was filtered through celite and the volatiles removed under reduced pressure to afford the title compound as an orange solid.

m/z (ESI, +ve)=613.2 $(M+H)^+$.

Step 2: tert-butyl (3S)-4-((3S)-11-(2,4-difluorophenyl)-3-((methylsulfonyl)oxy)-6-oxo-10-(trifluoromethyl)-3,4-dihydro-2H,6H-[1,4]thiazepino[2,3,4-ij]quinazolin-8-yl)-3-methylpiperazine-1-carboxylate

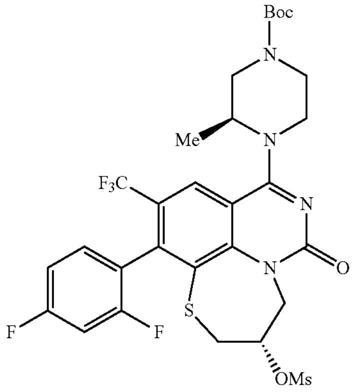 [SMILES: C[C@H]1CN(C(=O)OC(C)(C)C)CCN1c1nc(=O)n2c3c(c(-c4ccc(F)cc4F)c(C(F)(F)F)cc13)SC[C@@H](OS(C)(=O)=O)C2]

Over a solution of tert-Butyl (3S)-4-((3S)-11-(2,4-difluorophenyl)-3-hydroxy-6-oxo-10-(trifluoromethyl)-3,4-dihydro-2H,6H-[1,4]thiazepino[2,3,4-ij]quinazolin-8-yl)-3-methylpiperazine-1-carboxylate (368 mg) in dichloromethane (6 mL) at room temperature, N,N-diisopropylethylamine (0.50 mL) and methanesulfonyl chloride (0.12 mL) were added. The reaction was stirred for 3 hours, diluted with dichloromethane and washed with water. The organic layer was dried with sodium sulfate and concentrated under reduced pressure to afford an orange solid that was used in the next step without further purification.

m/z (ESI, +ve)=691.2 $(M+H)^+$.

Step 3: tert-Butyl (3S)-4-((2R)-10-(2,4-difluorophenyl)-2-((dimethylamino)methyl)-5-oxo-9-(trifluoromethyl)-2,3-dihydro-5H-[1,4]thiazino[2,3,4-ij]quinazolin-7-yl)-3-methylpiperazine-1-carboxylate

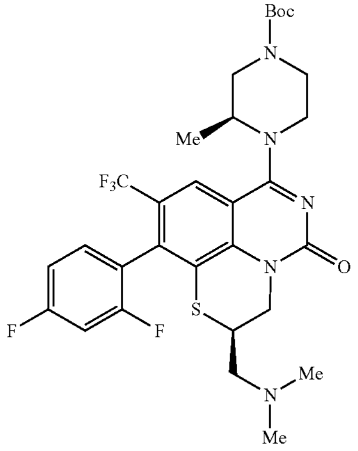 [SMILES: C[C@H]1CN(C(=O)OC(C)(C)C)CCN1c1nc(=O)n2c3c(c(-c4ccc(F)cc4F)c(C(F)(F)F)cc13)S[C@H](CN(C)C)C2]

tert-Butyl (3S)-4-((3S)-11-(2,4-difluorophenyl)-3-((methylsulfonyl)oxy)-6-oxo-10-(trifluoromethyl)-3,4-dihydro-2H,6H-[1,4]thiazepino[2,3,4-ij]quinazolin-8-yl)-3-methylpiperazine-1-carboxylate obtained in the previous step was taken up in 0.5 M solution of N-methylamine in dioxane (2 mL) and heated at 100° C. in microwave reactor for two hours. The volatiles were removed under reduced pressure and the crude residue purified by chromatography in silica gel (0-10% methanol in ethyl acetate) to afford the title compound in 32% yield as a orange oil.

m/z (ESI, +ve)=640.2 $(M+H)^+$.

Step 4: (2R)-10-(2,4-difluorophenyl)-2-((dimethylamino)methyl)-7-((S)-2-methylpiperazin-1-yl)-9-(trifluoromethyl)-2,3-dihydro-5H-[1,4]thiazino[2,3,4-ij]quinazolin-5-one

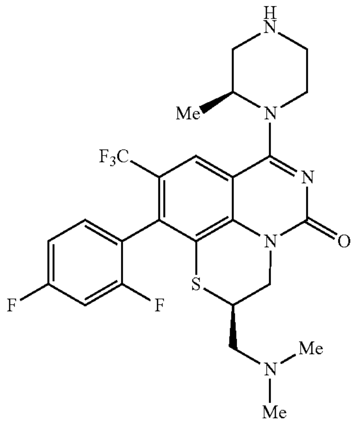 [SMILES: C[C@H]1CNCCN1c1nc(=O)n2c3c(c(-c4ccc(F)cc4F)c(C(F)(F)F)cc13)S[C@H](CN(C)C)C2]

Over a solution of tert-butyl (3S)-4-((2R)-10-(2,4-difluorophenyl)-2-((dimethylamino)methyl)-5-oxo-9-(trifluoromethyl)-2,3-dihydro-5H-[1,4]thiazino[2,3,4-ij]quinazolin-7-yl)-3-methylpiperazine-1-carboxylate (37 mg) in dichloromethane (1 mL), TFA (0.2 mL) was added. The mixture was stirred at room temperature for 4 hours and at that time all volatiles were removed under reduced pressure to afford a solid that was used in the next step without further purification.

m/z (ESI, +ve)=539.2 $(M+H)^+$.

Example 450: 8-((S)-4-acryloyl-2-methylpiperazin-1-yl)-11-(2,4-difluorophenyl)-10-(trifluoromethyl)-3,4-dihydro-2H,6H-[1,4]thiazepino[2,3,4-ij]quinazolin-6-one

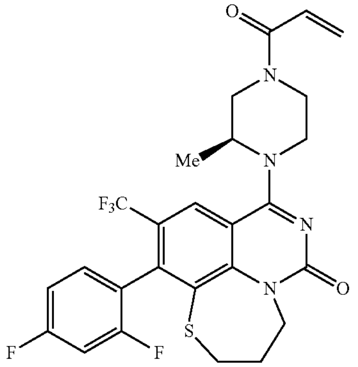 [SMILES: C=CC(=O)N1CCN(c2nc(=O)n3c4c(c(-c5ccc(F)cc5F)c(C(F)(F)F)cc24)SCCC3)[C@@H](C)C1]

The title compound was prepared analogously to Example 84 where 11-(2,4-difluorophenyl)-8-((S)-2-methylpiperazin-1-yl)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one in 51% yield as a yellow solid m/z (ESI, +ve)=551.1 (M+H)+.

$^1$H NMR (400 MHz, DMSO-d6) δ 7.81 (d, J=4.0 Hz, 1H), 7.50-7.33 (m, 2H), 7.26-7.23 (m, 1H), 6.91-6.75 (m, 1H), 6.21-6.15 (m, 1H), 5.74 (d, J=8 Hz, 1H), 4.57-4.47 (m, 3H), 4.42-4.24 (m, 1H), 4.10-3.98 (m, 2H), 3.62-3.48 (m, 1H), 3.46-2.92 (m, 4H), 2.11-1.86 (m, 2H), 1.33-1.28 (m, 3H).

Step 1: 7-(2,4-difluorophenyl)-8-((3-hydroxypropyl)thio)-6-(trifluoromethyl)quinazoline-2,4(1H,3H)-dione

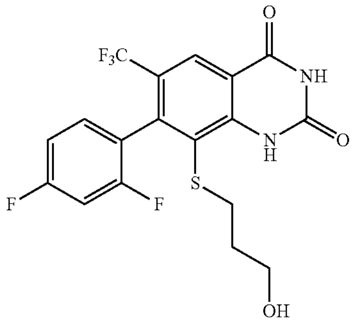 [SMILES: O=c1[nH]c(=O)c2cc(C(F)(F)F)c(-c3ccc(F)cc3F)c(SCCCO)c2[nH]1]

The title compound was prepared analogously to Example 100, step 9 where 3-mercaptopropan-1-ol was substituted in place of 2-mercaptoethan-1-ol in 56% yield as a white solid m/z (ESI, +ve)=433.1 $(M+H)^+$.

Step 2: 11-(2,4-difluorophenyl)-10-(trifluoromethyl)-3,4-dihydro-2H,6H-[1,4]thiazepino[2,3,4-ij]quinazoline-6,8(7H)-dione

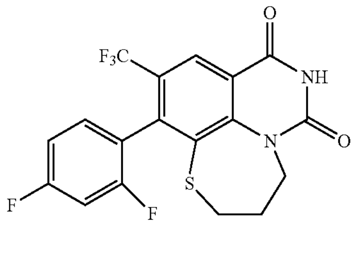 [SMILES: O=c1[nH]c(=O)n2c3c(c(-c4ccc(F)cc4F)c(C(F)(F)F)cc13)SCCC2]

The title compound was prepared analogously to Example 100, step 10 where 7-(2,4-difluorophenyl)-8-((3-hydroxypropyl)thio)-6-(trifluoromethyl)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 52% yield as a white solid m/z (ESI, +ve)=415.1 $(M+H)^+$.

Step 3: tert-butyl (3S)-4-(11-(2,4-difluorophenyl)-6-oxo-10-(trifluoromethyl)-3,4-dihydro-2H,6H-[1,4]thiazepino[2,3,4-ij]quinazolin-8-yl)-3-methylpiperazine-1-carboxylate

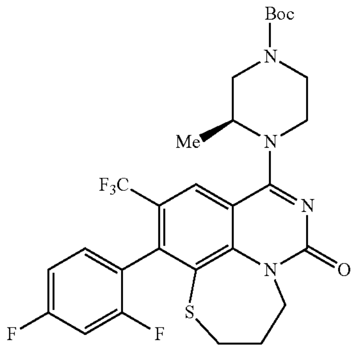 [SMILES: C[C@H]1CN(C(=O)OC(C)(C)C)CCN1c1nc(=O)n2c3c(c(-c4ccc(F)cc4F)c(C(F)(F)F)cc13)SCCC2]

The title compound was prepared analogously to Example 100, step 21 where 11-(2,4-difluorophenyl)-10-(trifluoromethyl)-3,4-dihydro-2H,6H-[1,4]thiazepino[2,3,4-ij]quinazoline-6,8(7H)-dione and tert-butyl (S)-3-methylpiperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 85% yield as a yellow solid.

m/z (ESI, +ve)=597.1 $(M+H)^+$.

Step 4: 11-(2,4-difluorophenyl)-8-((S)-2-methylpiperazin-1-yl)-10-(trifluoromethyl)-3,4-dihydro-2H,6H-[1,4]thiazepino[2,3,4-ij]quinazolin-6-one

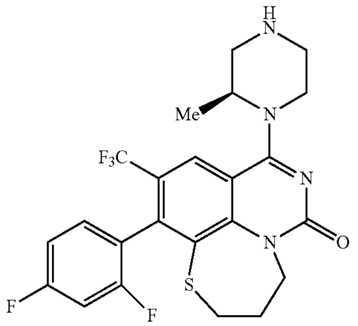 [SMILES: C[C@H]1CNCCN1c1nc(=O)n2c3c(c(-c4ccc(F)cc4F)c(C(F)(F)F)cc13)SCCC2]

The title compound was prepared analogously to Example 102, step 4, where (3S)-4-(11-(2,4-difluorophenyl)-6-oxo-10-(trifluoromethyl)-3,4-dihydro-2H,6H-[1,4]thiazepino[2,3,4-ij]quinazolin-8-yl)-3-methylpiperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 92% yield as a yellow oil.

m/z (ESI, +ve)=497.1 (M+H)+.

Example 451: 11-(2,4-difluorophenyl)-8-(9-(2-fluoroacryloyl)-7-oxo-3,9-diazabicyclo[3.3.1]nonan-3-yl)-10-(trifluoromethyl)-3,4-dihydro-2H,6H-[1,4]thiazepino[2,3,4-ij]quinazolin-6-one

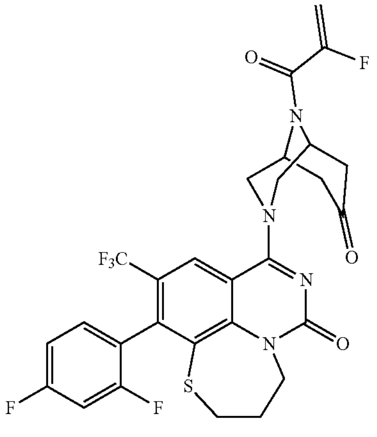 [SMILES: C=C(F)C(=O)N1C2CC(=O)CC1CN(c1nc(=O)n3c4c(c(-c5ccc(F)cc5F)c(C(F)(F)F)cc14)SCCC3)C2]

To a solution of 2-fluoroacrylic acid (34 mg, 0.38 mmol) in DMF (3 mL), N,N,N',N'-tetramethyl-O-(7-azabenzotriazol-1-yl)uronium (160 mg, 0.42 mmol) and N,N-diisopropylethylamine (99 mg, 0.76 mmol) were added. After 5 minutes, 11-(2,4-difluorophenyl)-8-(7-oxo-3,9-diazabicyclo[3.3.1]nonan-3-yl)-10-(trifluoromethyl)-3,4-dihydro-2H,6H-[1,4]thiazepino[2,3,4-ij]quinazolin-6-one (120 mg, 0.19 mmol) was added and the resulting solution stirred at room temperature for another 2 hours. The solvent was removed under reduced pressure to afford a residue that was purified by preparative HPLC. The title compound was isolated in 15% as a light yellow solid.

m/z (ESI, +ve)=609.1 $(M+H)^+$.

$^1$H NMR (400 MHz, DMSO-d6) δ7.77 (s, 1H), 7.44-7.36 (m, 2H), 7.28-7.24 (m, 1H), 5.47 (s, 1H), 5.38 (dd, J=24.0 Hz, 4.0 Hz, 1H), 5.06 (s, 1H), 4.79 (s, 1H), 4.55-4.45 (m, 2H), 4.16-4.01 (m, 2H), 3.32-3.06 (m, 4H), 3.00-2.73 (m, 2H), 2.55-2.52 (m, 2H), 2.14-1.89 (m, 2H).

Step 1: 11-(2,4-difluorophenyl)-8-(7-oxo-3,9-diazabicyclo[3.3.1]nonan-3-yl)-10-(trifluoromethyl)-3,4-dihydro-2H,6H-[1,4]thiazepino[2,3,4-ij]quinazolin-6-one

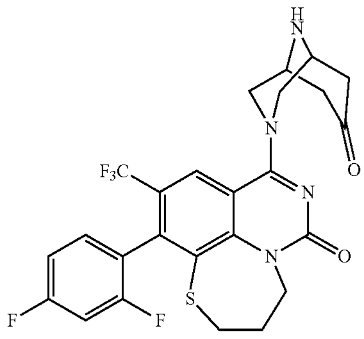 [SMILES: O=C1CC2CN(c3nc(=O)n4c5c(c(-c6ccc(F)cc6F)c(C(F)(F)F)cc35)SCCC4)CC(C1)N2]

The title compound was prepared analogously to Example 101, step 7 where 11-(2,4-difluorophenyl)-10-(trifluoromethyl)-3,4-dihydro-2H,6H-[1,4]thiazepino[2,3,4-ij]quinazoline-6,8(7H)-dione was substituted in place of 10-(2,4-difluorophenyl)-9-(trifluoromethyl)-2,3-dihydro-5H-[1,4]thiazino[2,3,4-ij]quinazoline-5,7(6H)-dione. The title compound was isolated in 8% yield as a pale yellow solid.

m/z (ESI, +ve)=537.0 $(M+H)^+$.

$^1$H NMR (400 MHz, DMSO-d6) δ 7.77 (s, 1H), 7.44-7.40 (m, 2H), 7.27-7.23 (m, 1H), 4.50-4.44 (m, 2H), 3.87-3.83 (m, 2H), 3.65 (s, 2H), 3.27-3.13 (m, 4H), 2.76-2.67 (m, 2H), 2.43-2.34 (m, 2H), 2.08-1.96 (m, 2H), 1.23 (s, 1H).

Example 452: (E)-7-(9-(but-2-enoyl)-7-oxo-3,9-diazabicyclo[3.3.1]nonan-3-yl)-10-(2,4-difluorophenyl)-9-(trifluoromethyl)-2,3-dihydro-5H-[1,4]thiazino[2,3,4-ij]quinazolin-5-one

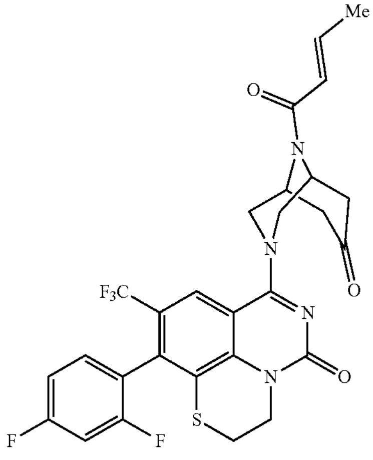 [SMILES: C/C=C/C(=O)N1C2CC(=O)CC1CN(c1nc(=O)n3c4c(c(-c5ccc(F)cc5F)c(C(F)(F)F)cc14)SCC3)C2]

To a solution of (E)-but-2-enoic acid (13 mg, 0.15 mmol) in acetonitrile (2 mL) were added N,N,N',N'-tetramethylchloroformamidinium hexafluorophosphate (38 mg, 0.14 mmol) and N-methylimidazole (33 mg, 0.40 mmol). After 5 minutes, 10-(2,4-difluorophenyl)-7-(7-oxo-3,9-diazabicyclo[3.3.1]nonan-3-yl)-9-(trifluoromethyl)-2,3-dihydro-5H-[1,4]thiazino[2,3,4-ij]quinazolin-5-one (60 mg, 0.11 mmol) was added. The reaction mixture was stirred at room temperature for 2 hours. The solvent was removed under reduced pressure to afford a residue that was purified by preparative HPLC. The title compound was isolated in 5% yield as a white solid.

m/z (ESI, +ve)=591.1 $(M+H)^+$.

$^1$H NMR (400 MHz, DMSO-d6) δ 7.78 (s, 1H), 7.48-7.47 (m, 1H), 7.38-7.37 (m, 1H), 7.30-7.28 (m, 1H), 6.87-6.80 (m, 1H), 6.68-6.64 (m, 1H), 5.76 (s, 1H), 5.15 (s, 1H), 4.95 (s, 1H), 4.32-4.24 (m, 2H), 4.16-3.97 (m, 3H), 3.21-3.18 (m, 4H), 2.84-2.69 (m, 2H), 1.91-1.89 (m, 3H).

Example 453: 7-(9-(but-2-ynoyl)-7-oxo-3,9-diazabicyclo[3.3.1]nonan-3-yl)-10-(2,4-difluorophenyl)-9-(trifluoromethyl)-2,3-dihydro-5H-[1,4]thiazino[2,3,4-ij]quinazolin-5-one

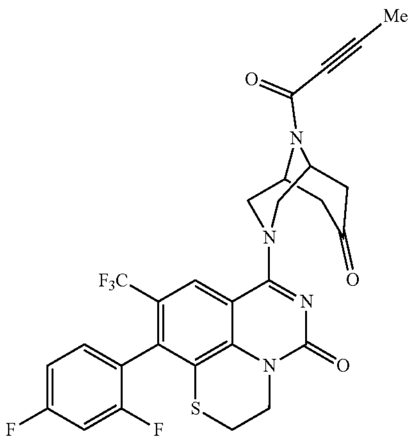 [SMILES: CC#CC(=O)N1C2CC(=O)CC1CN(c1nc(=O)n3c4c(c(-c5ccc(F)cc5F)c(C(F)(F)F)cc14)SCC3)C2]

The title compound was prepared analogously to Example 452, where but-2-ynoic acid was substituted in place of (E)-but-2-enoic acid. The title compound was isolated in 18% yield as a white solid m/z (ESI, +ve)=589.1 $(M+H)^+$.

$^1$H NMR (400 MHz, DMSO-d6) δ 7.76 (s, 1H), 7.50-7.46 (m, 1H), 7.38-7.34 (m, 1H), 7.30-7.26 (m, 1H), 5.05 (s, 2H), 4.31-4.30 (m, 1H), 4.13-4.04 (m, 3H), 3.30-3.07 (m, 5H), 2.87-2.76 (m, 3H), 2.09-2.05 (m, 3H).

Example 454: (3S)-8-((S)-4-acryloyl-2-methylpiperazin-1-yl)-11-(2,4-difluorophenyl)-3-(methyl(2,2,2-trifluoroethyl)amino)-10-(trifluoromethyl)-3,4-dihydro-2H,6H-[1,4]thiazepino[2,3,4-ij]quinazolin-6-one

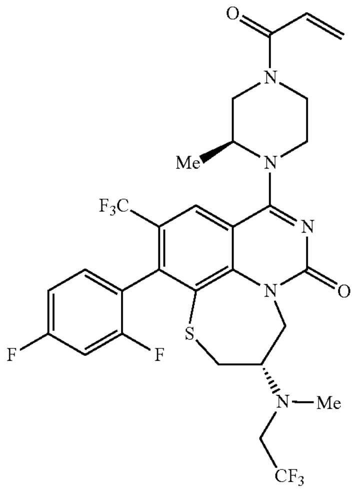 [SMILES: C=CC(=O)N1CCN(c2nc(=O)n3c4c(c(-c5ccc(F)cc5F)c(C(F)(F)F)cc24)SC[C@@H](N(C)CC(F)(F)F)C3)[C@@H](C)C1]

To a stirred solution of (3S)-11-(2,4-difluorophenyl)-3-(methyl(2,2,2-trifluoroethyl)amino)-8-((S)-2-methylpiperazin-1-yl)-10-(trifluoromethyl)-3,4-dihydro-2H,6H-[1,4] thiazepino[2,3,4-ij]quinazolin-6-one (8.5 mg, 0.01 mmol) at 0° C. in acetonitrile (2 mL), N,N-diisopropylethylamine (21 uL, 0.12 mmol) and prop-2-enoyl chloride (2.87 uL, 0.040 mmol) were added. The reaction was stirred for 5 minutes at 0° C., diluted with ethyl acetate and washed with water and brine. The organic layer was dried with sodium sulfate and concentrated to afford a yellow residue that was purified by silica (0-5% methanol in dichloromethane) isolating the title compound as a light yellow solid in 90% yield.

m/z (ESI, +ve)=662.2

$^1$H NMR (400 MHz, CDCl3) δ 7.75 (d, J=12.1 Hz, 1H), 7.15 (q, J=7.8 Hz, 1H), 7.07-6.77 (m, 2H), 6.71-6.47 (m, 1H), 6.39 (dd, J=16.8, 1.9 Hz, 1H), 5.79 (dd, J=10.4, 1.9 Hz, 1H), 5.10-4.58 (m, 2H), 4.58-4.08 (m, 2H), 4.07-3.71 (m, 2H), 3.67-3.37 (m, 2H), 3.22-2.99 (m, 2H), 2.90 (t, J=8.5 Hz, 1H), 2.75 (dd, J=13.3, 7.7 Hz, 1H), 2.47 (d, J=3.9 Hz, 2H), 1.60-1.35 (m, 3H), 1.35-1.10 (m, 3H).

Step 1: (R)-1-(benzyloxy)-3-(tritylthio)propan-2-ol

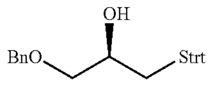

To a vigorously stirred solution of triphenylmethanethiol (7.0 g, 25.33 mmol) and (2R)-2-(benzyloxymethyl)oxirane (2.99 mL, 19.49 mmol) in THF (100 mL) at 0° C., sodium hydride (29 mmol) was added in three portions over five minutes. The reaction was left in an ice bath to slowly warm to room temperature overnight. The reaction was diluted with ethyl acetate (200 mL) and washed with water (X2) and brine. The organic layer was collected, dried with sodium sulfate, and concentrated to afford a tan oil. This oil was purified via column chromatography (5-50% ethyl acetate in hexanes) isolating the title compound in 71% yield a colorless oil.

$^1$H NMR (400 MHz, CDCl3) δ 7.26-7.23 (m, 5H), 7.23-6.96 (m, 15H), 4.28 (s, 2H), 3.35 (qd, J=6.6, 3.6 Hz, 1H), 3.23-3.05 (m, 2H), 2.31-2.15 (m, 2H).

Step 2: (R)-1-(benzyloxy)-3-(tritylthio)propan-2-yl methanesulfonate

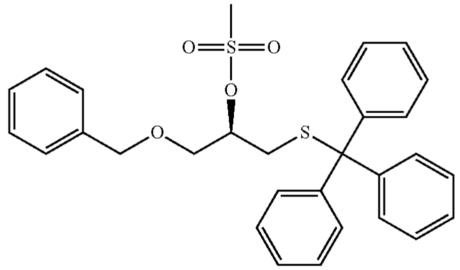 [SMILES: CS(=O)(=O)O[C@H](COCc1ccccc1)CSC(c1ccccc1)(c1ccccc1)c1ccccc1]

To a stirred solution of (R)-1-(benzyloxy)-3-(tritylthio) propan-2-ol (3.5 g, 7.94 mmol) and triethylamine (23.8 mmol) in acetonitrile (100 mL) cooled down to 0° C., methanesulfonyl chloride (2.13 mL) was added. The reaction was stirred at 0° C. for 30 minutes and let it warm up to ambient temperature afterwards. After 2 hours, the reaction was diluted with ethyl acetate, washed with water and brine and the organic layer dried over sodium sulfate and concentrated to afford a brown oil. This oil was purified via column chromatography (5-40% ethyl acetate in hexanes) isolating the title compound in 91% yield as a thick colorless oil.

$^1$H NMR (400 MHz, CDCl3) δ 7.45-7.42 (m, 5H), 7.34-7.24 (m, 15H), 4.52-4.41 (m, 2H), 4.33 (qd, J=6.4, 4.8 Hz, 1H), 3.55-3.43 (m, 2H), 2.95 (s, 3H), 2.64 (qd, J=13.4, 6.5 Hz, 2H).

Step 3: (S)-1-(benzyloxy)-N-methyl-N-(2,2,2-trifluoroethyl)-3-(tritylthio)propan-2-amine

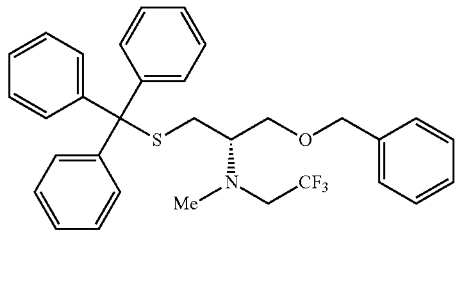 [SMILES: CN(CC(F)(F)F)[C@@H](COCc1ccccc1)CSC(c1ccccc1)(c1ccccc1)c1ccccc1]

To a stirred solution of (R)-1-(benzyloxy)-3-(tritylthio) propan-2-yl methanesulfonate (1 g, 1.93 mmol) and DMA (6.4 mL) in a 20 mL microwave vial was added 2,2,2-trifluoro-N-methyl-ethanamine (5.45 mL, 38.56 mmol). The vial was capped and heated at 50° C. for 13 hours. The crude reaction mixture was concentrated to afford light yellow oil. This crude oil was purified via chromatography (5-45% ethyl acetate in hexanes) isolating the title compound in 24% yield as a colorless oil.

$^{1}H$ NMR (400 MHz, CDCl3) δ 7.44 (dd, J=7.7, 1.8 Hz, 5H), 7.25-7.07 (m, 15H), 4.40-4.28 (m, 2H), 3.31 (ddd, J=37.9, 9.5, 4.0 Hz, 2H), 2.71-2.49 (m, 3H), 2.32-2.24 (m, 1H), 2.17-2.00 (m, 4H).

Step 4: (S)-3-(benzyloxy)-2-(methyl(2,2,2-trifluoroethyl)amino)propane-1-thiol

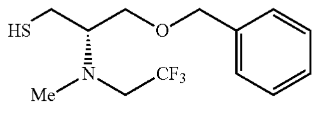 [SMILES: CN(CC(F)(F)F)[C@H](CS)COCc1ccccc1]

(S)-1-(benzyloxy)-N-methyl-N-(2,2,2-trifluoroethyl)-3-(tritylthio)propan-2-amine (150 mg, 0.28 mmol) was dissolved in a mixture of dichloromethane (1 mL) and TFA (1 mL) and treated with triethylsilane (1.12 g, 9.64 mmol) at ambient temperature. The reaction was stirred for 2 hours. The crude reaction mixture was concentrated under reduced pressure to afford the title compound that was used in the next step without further purification.

Step 5: 8-(((S)-3-(benzyloxy)-2-(methyl(2,2,2-trifluoroethyl)amino)propyl)thio)-7-(2,4-difluorophenyl)-6-(trifluoromethyl)quinazoline-2,4(1H,3H)-dione

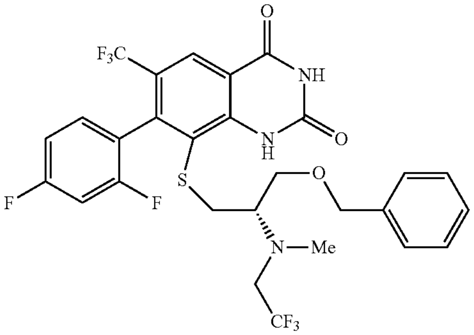 [SMILES: CN(CC(F)(F)F)[C@@H](COCc1ccccc1)CSc1c(-c2ccc(F)cc2F)c(C(F)(F)F)cc2c(=O)[nH]c(=O)[nH]c12]

A mixture of (S)-3-(benzyloxy)-2-(methyl(2,2,2-trifluoroethyl)amino)propane-1-thiol (65.8 mg, 0.22 mmol), potassium carbonate (62.mg, 0.45 mmol), ethylene glycol (0.1 mL), isopropanol (0.68 mL), and 7-(2,4-difluorophenyl)-8-iodo-6-(trifluoromethyl)-1H-quinazoline-2,4-dione (70 mg, 0.15 mmol) was degassed by bubbling nitrogen gas for 5 minutes. Copper iodide was then added (2.85 mg, 0.0100 mmol) and the mixture degassed again for another 3 minutes. The reaction was heated at 85° C. overnight. The reaction was cooled to ambient temperature, diluted with ethyl acetate, and washed with water and brine. The organic layer was dried with sodium sulfate and concentrated to afford a crude oil that was purified by silica gel chromatography (0-10% methanol in ethyl acetate) to afford the title compound in 95% yield as a white solid.

m/z (ESI, +ve)=634.2, RT: 5.25 min

Step 6: 7-(2,4-difluorophenyl)-8-(((S)-3-hydroxy-2-(methyl(2,2,2-trifluoroethyl)amino)propyl)thio)-6-(trifluoromethyl)quinazoline-2,4(1H,3H)-dione

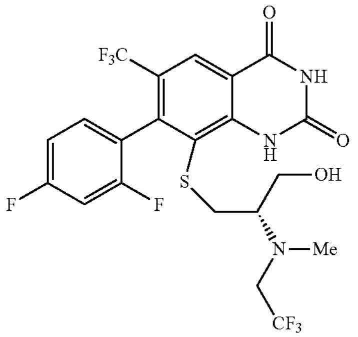 [SMILES: CN(CC(F)(F)F)[C@@H](CO)CSc1c(-c2ccc(F)cc2F)c(C(F)(F)F)cc2c(=O)[nH]c(=O)[nH]c12]

A solution of 8-(((S)-3-(benzyloxy)-2-(methyl(2,2,2-trifluoroethyl)amino)propyl)thio)-7-(2,4-difluorophenyl)-6-(trifluoromethyl)quinazoline-2,4(1H,3H)-dione (90.mg, 0.14 mmol) and 30 mg of 10% palladium on carbon in isopropanol was hydrogenated for 18 hours. The reaction was filtered through celite and concentrated to afford the title compound as a semisolid in 82% yield.

m/z (ESI, +ve)=544.1

Step 7: (3S)-11-(2,4-difluorophenyl)-3-(methyl(2,2,2-trifluoroethyl)amino)-10-(trifluoromethyl)-3,4-dihydro-2H,6H-[1,4]thiazepino[2,3,4-ij]quinazoline-6,8(7H)-dione

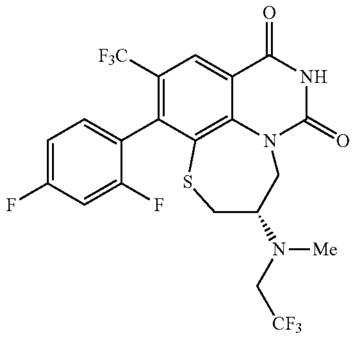 [SMILES: CN(CC(F)(F)F)[C@@H]1CSc2c(-c3ccc(F)cc3F)c(C(F)(F)F)cc3c(=O)[nH]c(=O)n(c23)C1]

A solution of triphenylphosphine (76 mg, 0.29 mmol) and (4-chlorophenyl)methyl (NE)-N-[(4-chlorophenyl)methoxycarbonylimino]carbamate (106 mg, 0.29 mmol) in 2 mL of THF was stirred at −10° C. for 10 minutes. To this mixture, a solution of 7-(2,4-difluorophenyl)-8-(((S)-3-hydroxy-2-(methyl(2,2,2-trifluoroethyl)amino)propyl)thio)-6-(trifluoromethyl)quinazoline-2,4(1H,3H)-dione (63 mg, 0.12 mmol) in 2 mL THF was added dropwise over 3 minutes. The reaction was stirred for 1 hour at 0° C. An additional equivalent of (4-chlorophenyl)methyl (NE)-N-[(4-chlorophenyl)methoxycarbonylimino]carbamate and triphenylphosphine in 0.5 mL of THF were added and the mixture stirred for another 30 min. The reaction was diluted with ethyl acetate and washed with water and brine. The organic layer was dried with sodium sulfate and concentrated to a residue that was purified by column chromatography (10-60% ethyl acetate in hexanes) to afford the title compound as a white solid in 82% yield.

m/z (ESI, +ve)=526.1

Step 8: tert-butyl (3S)-4-((3S)-11-(2,4-difluorophenyl)-3-(methyl(2,2,2-trifluoroethyl)amino)-6-oxo-10-(trifluoromethyl)-3,4-dihydro-2H,6H-[1,4]thiazepino[2,3,4-ij]quinazolin-8-yl)-3-methylpiperazine-1-carboxylate

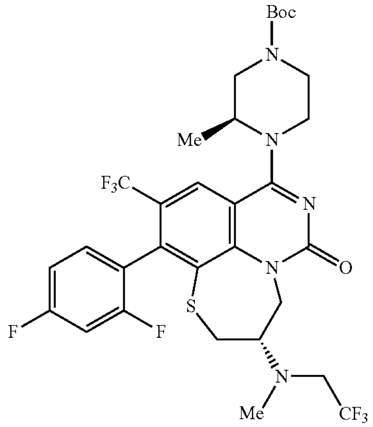 [SMILES: C[C@H]1CN(C(=O)OC(C)(C)C)CCN1c1nc(=O)n2c3c(c(-c4ccc(F)cc4F)c(C(F)(F)F)cc13)SC[C@@H](N(C)CC(F)(F)F)C2]

The title compound was prepared analogously to Example 100, step 21 where (3S)-11-(2,4-difluorophenyl)-3-(methyl(2,2,2-trifluoroethyl)amino)-10-(trifluoromethyl)-3,4-dihydro-2H,6H-[1,4]thiazepino[2,3,4-ij]quinazoline-6,8(7H)-dione and tert-butyl (S)-3-methylpiperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 12% yield as a white solid m/z (ESI, +ve)=708.3 $(M+H)^+$.

Step 9: (3S)-11-(2,4-difluorophenyl)-3-(methyl(2,2,2-trifluoroethyl)amino)-8-((S)-2-methylpiperazin-1-yl)-10-(trifluoromethyl)-3,4-dihydro-2H,6H-[1,4]thiazepino[2,3,4-ij]quinazolin-6-one

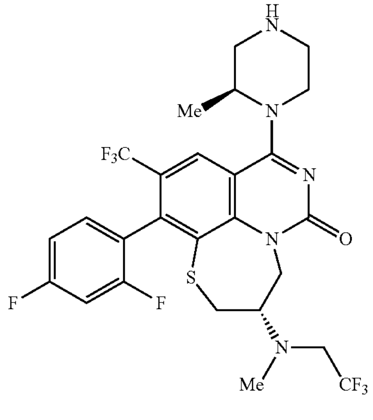 [SMILES: C[C@H]1CNCCN1c1nc(=O)n2c3c(c(-c4ccc(F)cc4F)c(C(F)(F)F)cc13)SC[C@@H](N(C)CC(F)(F)F)C2]

The title compound was prepared analogously to Example 102, step 4, where tert-butyl (3S)-4-((3S)-11-(2,4-difluorophenyl)-3-(methyl(2,2,2-trifluoroethyl)amino)-6-oxo-10-(trifluoromethyl)-3,4-dihydro-2H,6H-[1,4]thiazepino[2,3,4-ij]quinazolin-8-yl)-3-methylpiperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 99% yield as a colorless oil Mass Spectrum (ESI) m/z=608.2 (M+H)+.

Example 464: (3S)-8-((S)-4-acryloyl-2-methylpiperazin-1-yl)-11-(2,4-difluorophenyl)-3-methoxy-10-(trifluoromethyl)-3,4-dihydro-2H,6H-[1,4]thiazepino[2,3,4-ij]quinazolin-6-one

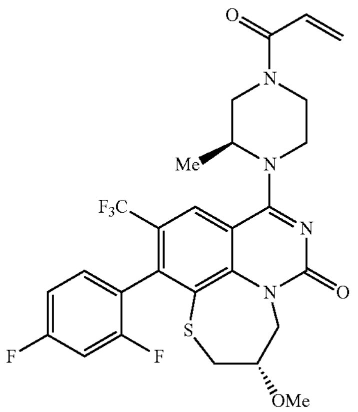 [SMILES: C=CC(=O)N1CCN(c2nc(=O)n3c4c(c(-c5ccc(F)cc5F)c(C(F)(F)F)cc24)SC[C@@H](OC)C3)[C@@H](C)C1]

The title compound was prepared analogously to Example 84 where (3S)-11-(2,4-difluorophenyl)-3-methoxy-8-((S)-2-methylpiperazin-1-yl)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one in 41% yield as a yellow solid m/z (ESI, +ve)=581.1 $(M+H)^+$.

$^1H$ NMR (400 MHz, DMSO-d6) δ 7.80 (d, J=8.0 Hz, 1H), 7.50-7.33 (m, 2H), 7.28-7.24 (m, 1H), 6.87-6.78 (m, 1H), 6.20-6.16 (m, 1H), 5.80-5.69 (m, 1H), 4.67-4.44 (m, 4H), 4.26-4.24 (m, 1H), 4.17-4.13 (m, 1H), 4.01-3.97 (m, 1H), 3.86-3.82 (m, 1H), 3.55-3. (m, 2H), 3.36-3.31 (m, 3H), 3.24-3.07 (m, 1H), 3.01 (s, 1H), 1.26-1.20 (m, 3H).

Step 1: (S)-3-(tritylthio)propane-1,2-diol

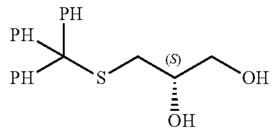

Potassium tert-butoxide (18.3 g, 0.18 mol) was added over a solution of triphenylmethyl mercaptan (25 g, 0.091 mol) and (2S)-3-chloropropane-1,2-diol (10 g, 0.091 mol) in DMF (200 mL) at 25° C. The mixture was stirred at room temperature for 16 hours and after that time it was quenched with water. The resulting mixture was extracted with ethyl acetate three times and the organic layers were combined and washed with brine, dried over sodium sulfate and filtered. Evaporation of volatiles under reduced pressure afforded a residue that was purified by column chromatography on silica gel (0-50% ethyl acetate in hexanes). The title compound was isolated in 66% yield as yellow oil.

m/z (ESI, +ve)=373.1 $(M+Na)^+$.

Step 2: (S)-1-((tert-butyldimethylsilyl)oxy)-3-(tritylthio)propan-2-ol

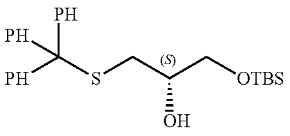

Imidazole (9.71 g, 0.14 mol) and tert-butyldimethylsilyl chloride (9.47 g, 0.063 mol) were added over a solution of (2S)-3-[(triphenylmethyl)sulfanyl] propane-1,2-diol (20 g, 0.057 mol) in DMF (250 mL) at room temperature. After 16 hours, the reaction was quenched by the addition of water. The mixture was extracted with ethyl acetate three times and the combined organic layers were washed with brine, dried over sodium sulfate and filtered to afford a residue that was purified by silica gel chromatography (0-15% ethyl acetate in hexanes). The title compound was isolated in 60% yield as a yellow oil.

m/z (ESI, +ve)=487.2 $(M+Na)^+$.

Step 3: (S)-tert-butyl(2-methoxy-3-(tritylthio)propoxy)dimethylsilane

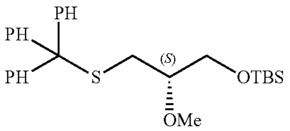

To a solution of tert-butyl[(2S)-2-hydroxy-3-[(triphenylmethyl)sulfanyl]propoxy]dimethylsilane (21 g, 0.045 mol) in THF (200 mL) at 0° C., sodium hydride (1.62 g, 0.068 mol) was added. After 30 minutes at 0° C., iodomethane (9.62 g, 0.067 mol) was added and stirring was prolonged for another 3.5 hours. The reaction was quenched by addition of water and extracted with ethyl acetate three times. The combined organic layers were washed with brine, dried over sodium sulfate and filtered to afford a residue that was purified by silica gel chromatography. The tile compound was isolated in 86% yield as a colorless oil.

m/z (ESI, +ve)=501.2 $(M+Na)^+$.

Step 4: (S)-3-Mercapto-2-methoxypropan-1-ol

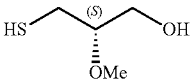

To a solution of tert-butyl[(2S)-2-methoxy-3-[(triphenylmethyl)sulfanyl]propoxy]dimethylsilane (18.7 g, 0.039 mol) in 180 mL of dichloromethane/TFA (3:1 ratio) at room temperature, was added triethylsilane (9.06 g, 0.078 mol). The mixture was stirred at room temperature for 30 minutes. The reaction was quenched by addition of water and extracted with dichloromethane three times. The combined organic layers were washed with brine, dried over sodium sulfate and filtered to afford a residue that was purified by silica gel chromatography. The tile compound was isolated in 90% yield as a colorless oil.

Step 5: 7-(2,4-difluorophenyl)-8-(((S)-3-hydroxy-2-methoxypropyl)thio)-6-(trifluoromethyl)quinazoline-2,4(1H,3H)-dione

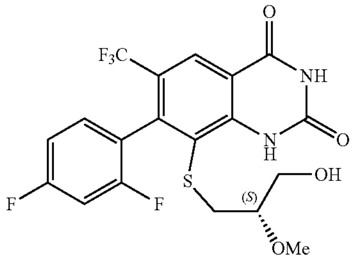

The title compound was prepared analogously to Example 100, step 9 where (S)-3-mercapto-2-methoxypropan-1-ol was substituted in place of 2-mercaptoethan-1-ol in 73% yield as a yellow solid m/z (ESI, +ve)=463.1 $(M+H)^+$.

Step 4: (3S)-11-(2,4-difluorophenyl)-3-methoxy-10-(trifluoromethyl)-3,4-dihydro-2H,6H-[1,4]thiazepino[2,3,4-ij]quinazoline-6,8(7H)-dione

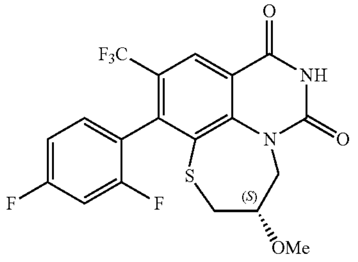

The title compound was prepared analogously to Example 100, step 10 where 7-(2,4-difluorophenyl)-8-(((S)-3-hydroxy-2-methoxypropyl)thio)-6-(trifluoromethyl)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 65% yield as a yellow solid m/z (ESI, +ve)=445.1 $(M+H)^+$.

Step 5: tert-butyl (3S)-4-((3S)-11-(2,4-difluorophenyl)-3-methoxy-6-oxo-10-(trifluoromethyl)-3,4-dihydro-2H,6H-[1,4]thiazepino[2,3,4-ij]quinazolin-8-yl)-3-methylpiperazine-1-carboxylate

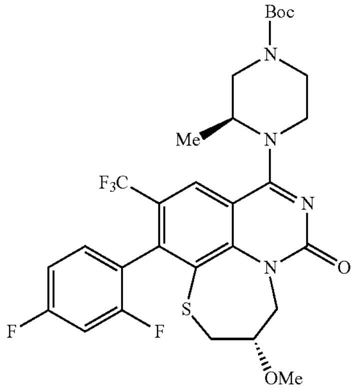 [SMILES: CO[C@@H]1CSc2c(-c3ccc(F)cc3F)c(C(F)(F)F)cc3c(N4CCN(C(=O)OC(C)(C)C)C[C@@H]4C)nc(=O)n(c23)C1]

The title compound was prepared analogously to Example 100, step 21 where (3S)-11-(2,4-difluorophenyl)-3-methoxy-10-(trifluoromethyl)-3,4-dihydro-2H,6H-[1,4]thiazepino[2,3,4-ij]quinazoline-6,8(7H)-dione and tert-butyl (S)-3-methylpiperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 56% yield as a yellow solid m/z (ESI, +ve)=627.1 $(M+H)^+$.

Step 6: (3S)-11-(2,4-difluorophenyl)-3-methoxy-8-((S)-2-methylpiperazin-1-yl)-10-(trifluoromethyl)-3,4-dihydro-2H,6H-[1,4]thiazepino[2,3,4-ij]quinazolin-6-one

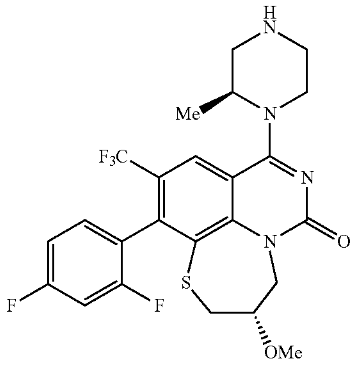 [SMILES: CO[C@@H]1CSc2c(-c3ccc(F)cc3F)c(C(F)(F)F)cc3c(N4CCNC[C@@H]4C)nc(=O)n(c23)C1]

The title compound was prepared analogously to Example 102, step 4, where tert-butyl (3S)-4-((3S)-11-(2,4-difluorophenyl)-3-methoxy-6-oxo-10-(trifluoromethyl)-3,4-dihydro-2H,6H-[1,4]thiazepino[2,3,4-ij]quinazolin-8-yl)-3-methylpiperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 95% yield as a yellow solid m/z (ESI, +ve)=527.0 $(M+H)^+$.

Example 465: (3R)-8-((S)-4-acryloyl-2-methylpiperazin-1-yl)-11-(2,4-difluorophenyl)-3-methoxy-10-(trifluoromethyl)-3,4-dihydro-2H,6H-[1,4]thiazepino[2,3,4-ij]quinazolin-6-one

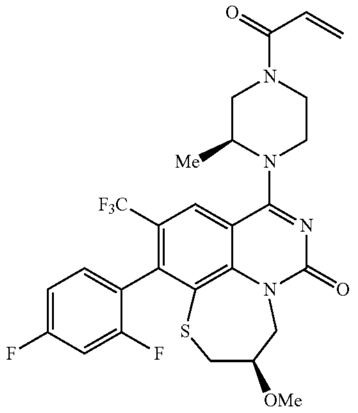 [SMILES: C=CC(=O)N1CCN(c2nc(=O)n3c4c(c(-c5ccc(F)cc5F)c(C(F)(F)F)cc24)SC[C@H](OC)C3)[C@@H](C)C1]

The title compound was prepared analogously to Example 84 where (3R)-11-(2,4-difluorophenyl)-3-methoxy-8-((S)-2-methylpiperazin-1-yl)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 10% yield as a yellow solid m/z (ESI, +ve)=581.1 $(M+H)^+$.

$^1$H NMR (400 MHz, DMSO-d6) δ 7.81 (d, J=4.0 Hz, 1H), 7.51-7.36 (m, 2H), 7.28-7.24 (m, 1H), 6.89-6.76 (m, 1H), 6.20-6.15 (m, 1H), 5.76-5.70 (m, 1H), 4.53-4.21 (m, 3H), 4.17-3.95 (m, 2H), 3.84 (s, 1H), 3.68-3.42 (m, 3H), 3.35 (s, 3H), 3.21-3.07 (m, 2H), 3.01-2.91 (m, 1H), 1.32-1.27 (m, 3H).

Step 1: (R)-3-(tritylthio)propane-1,2-diol

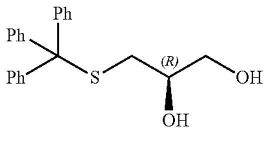

Potassium tert-butoxide (18.3 g, 0.18 mol) was added to a solution of triphenylmethyl mercaptan (25 g, 0.091 mol) and (2R)-3-chloropropane-1,2-diol (10 g, 0.091 mol) in DMF (200 mL) at room temperature. The mixture was stirred for 16 hours and stopped by the addition of water. The resulting mixture was extracted with ethyl acetate three times and the organic layers were combined and washed with brine, dried over sodium sulfate and filtered. Evaporation of volatiles under reduced pressure afforded a residue that was purified by column chromatography on silica gel (0-50% ethyl acetate in hexanes). The title compound was isolated in 51% yield as a yellow oil.

m/z (ESI, +ve)=373.1 $(M+Na)^+$.

Step 2: (R)-1-((tert-butyldimethylsilyl)oxy)-3-(tritylthio)propan-2-ol

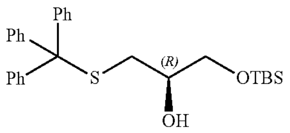

The titled compound was prepared analogously to example 464, step 2, where (2R)-3-[(triphenylmethyl)sulfanyl] propane-1,2-diol was substituted in place of (2S)-3-[(triphenylmethyl)sulfanyl] propane-1,2-diol. The title compound was isolated in 80% yield as a yellow oil.

m/z (ESI, +ve)=487.2 $(M+Na)^+$.

Step 3: (R)-tert-butyl(2-methoxy-3-(tritylthio)propoxy)dimethylsilane

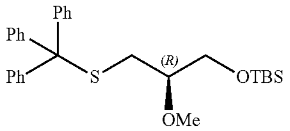

The titled compound was prepared analogously to example 464, step 3 where tert-butyl[(2R)-2-hydroxy-3-[(triphenylmethyl)sulfanyl]propoxy]dimethylsilane was substituted in place of tert-butyl[(2S)-2-hydroxy-3-[(triphenylmethyl)sulfanyl]propoxy]dimethylsilane. The title compound was isolated in 90% yield as a colorless oil.

m/z (ESI, +ve)=501.2 $(M+Na)^+$.

Step 4: (R)-3-Mercapto-2-methoxypropan-1-ol

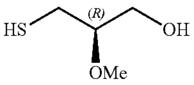

The titled compound was prepared analogously to example 464, step 4, where (R)-tert-butyl(2-methoxy-3-(tritylthio)propoxy)dimethylsilane was substituted for tert-butyl[(2S)-2-methoxy-3-[(triphenylmethyl)sulfanyl]propoxy]dimethylsilane. The title compound was isolated in 85% as a colorless oil.

Step 5: 7-(2,4-difluorophenyl)-8-(((R)-3-hydroxy-2-methoxypropyl)thio)-6-(trifluoromethyl)quinazoline-2,4(1H,3H)-dione

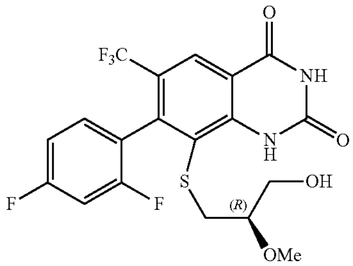

The title compound was prepared analogously to Example 100, step 9 where (R)-3-mercapto-2-methoxypropan-1-ol was substituted in place of 2-mercaptoethan-1-ol. The title compound was isolated in 54% yield as a yellow oil.

m/z (ESI, +ve)=463.0 $(M+H)^+$.

$^1$H NMR (400 MHz, DMSO-d6) δ 11.87 (s, 1H), 10.42 (d, J=18.4 Hz, 1H), 8.28 (s, 1H), 7.49-7.33 (m, 2H), 7.25-7.19 (m, 1H), 4.84 (s, 1H), 3.40-3.35 (m, 2H), 3.28 (d, J=10.8 Hz, 3H), 3.25-3.19 (m, 1H), 2.68-2.65 (m, 1H), 2.35-2.31 (m, 1H).

Step 6: (3R)-11-(2,4-difluorophenyl)-3-methoxy-10-(trifluoromethyl)-3,4-dihydro-2H,6H-[1,4]thiazepino[2,3,4-ij]quinazoline-6,8(7H)-dione

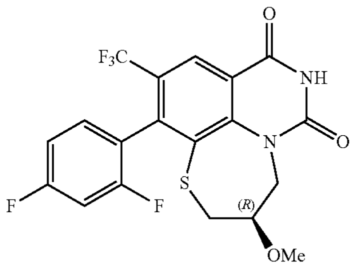

The title compound was prepared analogously to Example 100, step 10, where 7-(2,4-difluorophenyl)-8-(((R)-3-hydroxy-2-methoxypropyl)thio)-6-(trifluoromethyl)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione. The title compound was isolated in 56% yield as a white solid m/z (ESI, +ve)=445.0 $(M+H)^+$.

$^1$H NMR (400 MHz, DMSO-d6) δ 11.94 (d, J=4.0 Hz, 1H), 8.11 (d, J=7.2 Hz, 1H), 7.47-7.24 (m, 3H), 4.39-4.17 (m, 2H), 3.87-3.78 (m, 1H), 3.67-3.58 (m, 1H), 3.31 (d, J=8.8 Hz, 3H), 3.21-3.15 (m, 1H).

Step 7: tert-butyl (3S)-4-((3R)-11-(2,4-difluorophenyl)-3-methoxy-6-oxo-10-(trifluoromethyl)-3,4-dihydro-2H,6H-[1,4]thiazepino[2,3,4-ij]quinazolin-8-yl)-3-methylpiperazine-1-carboxylate

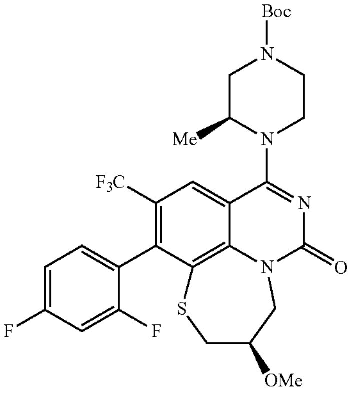 [SMILES: CO[C@H]1CSc2c(-c3ccc(F)cc3F)c(C(F)(F)F)cc3c(N4CCN(C(=O)OC(C)(C)C)C[C@@H]4C)nc(=O)n(c23)C1]

The title compound was prepared analogously to Example 100, step 21 where (3R)-11-(2,4-difluorophenyl)-3-methoxy-10-(trifluoromethyl)-3,4-dihydro-2H,6H-[1,4]thiazepino[2,3,4-ij]quinazoline-6,8(7H)-dione and tert-butyl (S)-3-methylpiperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 95% yield as a yellow solid m/z (ESI, +ve)=627.2 $(M+H)^+$.

Step 8: (3R)-11-(2,4-difluorophenyl)-3-methoxy-8-((S)-2-methylpiperazin-1-yl)-10-(trifluoromethyl)-3,4-dihydro-2H,6H-[1,4]thiazepino[2,3,4-ij]quinazolin-6-one

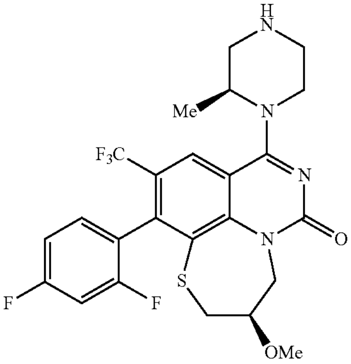 [SMILES: CO[C@H]1CSc2c(-c3ccc(F)cc3F)c(C(F)(F)F)cc3c(N4CCNC[C@@H]4C)nc(=O)n(c23)C1]

The title compound was prepared analogously to Example 102, step 4, where tert-butyl (3S)-4-((3R)-11-(2,4-difluorophenyl)-3-methoxy-6-oxo-10-(trifluoromethyl)-3,4-dihydro-2H,6H-[1,4]thiazepino[2,3,4-ij]quinazolin-8-yl)-3-methylpiperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 95% yield as a yellow solid m/z (ESI, +ve)=527.2 $(M+H)^+$.

Example 486: 8-(9-acryloyl-7-oxo-3,9-diazabicyclo[3.3.1]nonan-3-yl)-11-(2,4-difluorophenyl)-10-(trifluoromethyl)-3,4-dihydro-2H,6H-[1,4]thiazepino[2,3,4-ij]quinazolin-6-one

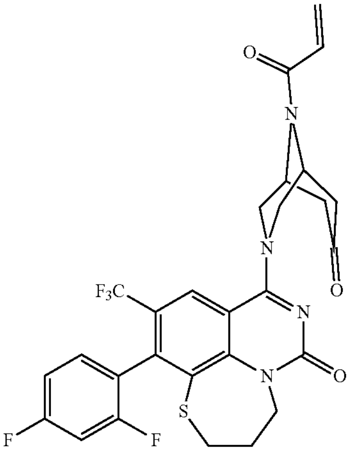 [SMILES: C=CC(=O)N1C2CC(=O)CC1CN(c1nc(=O)n3c4c(c(-c5ccc(F)cc5F)c(C(F)(F)F)cc14)SCCC3)C2]

The title compound was prepared analogously to Example 84 where 11-(2,4-difluorophenyl)-8-(7-oxo-3,9-diazabicyclo[3.3.1]nonan-3-yl)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 5% yield as a yellow solid m/z (ESI, +ve)=591.2 (M+H)+.

$^1$H NMR (400 MHz, DMSO-d6) δ 7.88-7.78 (m, 1H), 7.47-7.39 (m, 2H), 7.28-7.24 (m, 1H), 6.98-6.67 (m, 1H), 6.29-6.06 (m, 1H), 5.85-5.70 (m, 1H), 5.16 (s, 1H), 4.93 (s, 1H), 4.75 (s, 1H), 4.54-4.49 (m, 2H), 4.06-3.96 (m, 1H), 3.23-3.06 (m, 4H), 2.87-2.72 (m, 2H), 2.45-2.41 (m, 2H), 2.06-1.97 (m, 2H).

Example 487: (3S)-8-((S)-4-acryloyl-2-methylpiperazin-1-yl)-10-chloro-11-(2,4-difluorophenyl)-3-methoxy-3,4-dihydro-2H,6H-[1,4]thiazepino[2,3,4-ij]quinazolin-6-one

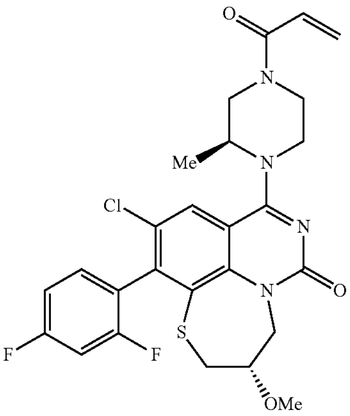 [SMILES: C=CC(=O)N1CCN(c2nc(=O)n3c4c(c(-c5ccc(F)cc5F)c(Cl)cc24)SC[C@@H](OC)C3)[C@@H](C)C1]

The title compound was prepared analogously to Example 84 where (3S)-10-chloro-11-(2,4-difluorophenyl)-3- methoxy-8-((S)-2-methylpiperazin-1-yl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 66% yield as a yellow solid.

m/z (ESI, +ve)=547.1 $(M+H)^+$.

$^1$H NMR (400 MHz, DMSO-d6) δ 7.64 (d, J=12.0 Hz, 1H), 7.49-7.44 (m, 2H), 7.30-7.25 (m, 1H), 6.86-6.77 (m, 1H), 6.21-6.15 (m, 1H), 5.76-5.73 (m, 1H), 4.69-4.20 (m, 4H), 4.18-4.03 (m, 1H), 3.96 (s, 1H), 3.88-3.80 (m, 1H), 3.64-3.38 (m, 3H), 3.35 (s, 3H), 3.11-2.97 (m, 2H), 1.31-1.24 (m, 3H).

Step 1: 6-chloro-7-(2,4-difluorophenyl)-8-(((S)-3-hydroxy-2-methoxypropyl)thio)quinazoline-2,4(1H,3H)-dione

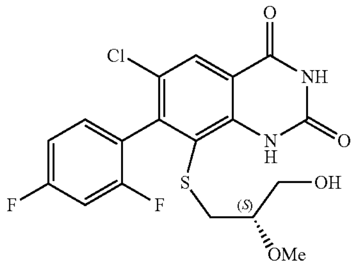

The title compound was prepared analogously to Example 100, step 9 where (S)-3-mercapto-2-methoxypropan-1-ol was substituted in place of 2-mercaptoethan-1-ol in 81% yield as a yellow solid m/z (ESI, +ve)=429.1 $(M+H)^+$.

Step 2: (3S)-10-chloro-11-(2,4-difluorophenyl)-3-methoxy-3,4-dihydro-2H,6H-[1,4]thiazepino[2,3,4-ij]quinazoline-6,8(7H)-dione

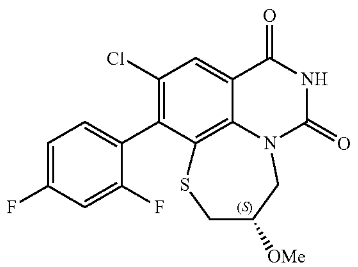

The title compound was prepared analogously to Example 100, step 10 where 6-chloro-7-(2,4-difluorophenyl)-8-(((S)-3-hydroxy-2-methoxypropyl)thio)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 74% yield as a yellow solid m/z (ESI, +ve)=411.0 $(M+H)^+$.

Step 3: tert-butyl (3S)-4-((3S)-10-chloro-11-(2,4-difluorophenyl)-3-methoxy-6-oxo-3,4-dihydro-2H,6H-[1,4]thiazepino[2,3,4-ij]quinazolin-8-yl)-3-methylpiperazine-1-carboxylate

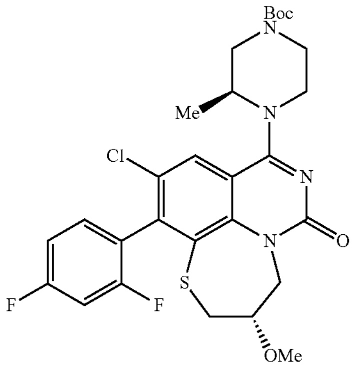 [SMILES: CO[C@@H]1CSc2c(-c3ccc(F)cc3F)c(Cl)cc3c(N4CCN(C(=O)OC(C)(C)C)C[C@@H]4C)nc(=O)n(c23)C1]

The title compound was prepared analogously to Example 100, step 21 where (3S)-10-chloro-11-(2,4-difluorophenyl)-3-methoxy-3,4-dihydro-2H,6H-[1,4]thiazepino[2,3,4-ij]quinazoline-6,8(7H)-dione and tert-butyl (S)-3-methylpiperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 69% yield as a yellow solid m/z (ESI, +ve)=593.2 $(M+H)^+$.

Step 4: (3S)-10-chloro-11-(2,4-difluorophenyl)-3-methoxy-8-((S)-2-methylpiperazin-1-yl)-3,4-dihydro-2H,6H-[1,4]thiazepino[2,3,4-ij]quinazolin-6-one

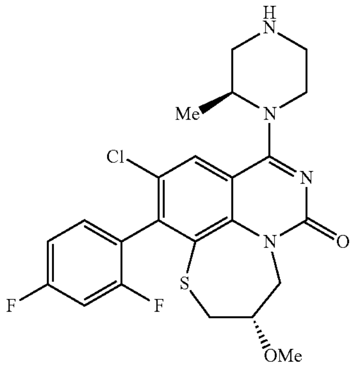 [SMILES: CO[C@@H]1CSc2c(-c3ccc(F)cc3F)c(Cl)cc3c(N4CCNC[C@@H]4C)nc(=O)n(c23)C1]

The title compound was prepared analogously to Example 102, step 4, where tert-butyl (3S)-4-((3S)-10-chloro-11-(2,4-difluorophenyl)-3-methoxy-6-oxo-3,4-dihydro-2H,6H-[1,4]thiazepino[2,3,4-ij]quinazolin-8-yl)-3-methylpiperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 67% yield as a yellow solid m/z (ESI, +ve)=493.1 $(M+H)^+$.

Example 488: (3R)-8-((S)-4-acryloyl-2-methylpiperazin-1-yl)-10-chloro-11-(2,4-difluorophenyl)-3-methoxy-3,4-dihydro-2H,6H-[1,4]thiazepino[2,3,4-ij]quinazolin-6-one

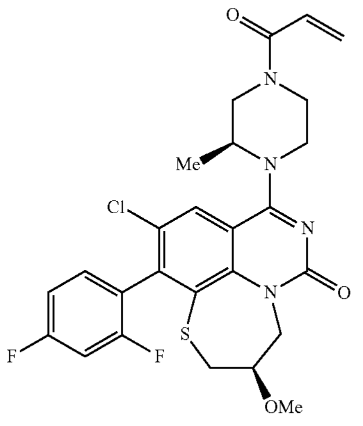 [SMILES: C=CC(=O)N1CCN(c2nc(=O)n3c4c(c(-c5ccc(F)cc5F)c(Cl)cc24)SC[C@H](OC)C3)[C@@H](C)C1]

The title compound was prepared analogously to Example 84 where (3R)-10-chloro-11-(2,4-difluorophenyl)-3-methoxy-8-((S)-2-methylpiperazin-1-yl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 22% yield as a yellow solid.

m/z (ESI, +ve)=547.1 $(M+H)^+$.

$^1$H NMR (400 MHz, DMSO-d6) δ 7.67 (d, J=16.0 Hz, 1H), 7.51-7.38 (m, 2H), 7.29-7.24 (m, 1H), 6.91-6.75 (m, 1H), 6.18 (dd, J=16.0, 4.0 Hz, 1H), 5.74 (dd, J=12.0, 4.0 Hz, 1H), 4.78-4.56 (m, 2H), 4.45-4.34 (m, 2H), 4.29-4.07 (m, 1H), 4.03-3.79 (m, 3H), 3.71-3.49 (m, 2H), 3.46-3.35 (m, 3H), 3.17-3.07 (m, 1H), 2.99-2.88 (m, 1H), 1.29-1.20 (m, 3H).

Step 1: 6-chloro-7-(2,4-difluorophenyl)-8-(((R)-3-hydroxy-2-methoxypropyl)thio)quinazoline-2,4(1H,3H)-dione

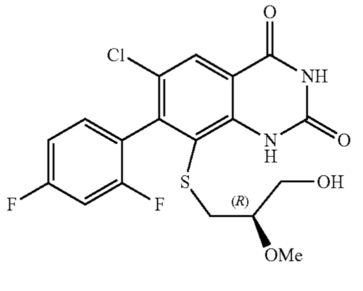

The title compound was prepared analogously to Example 100, step 9 where 6-chloro-7-(2,4-difluorophenyl)-8-iodoquinazoline-2,4(1H,3H)-dione and (R)-3-mercapto-2-methoxypropan-1-ol were substituted in place of 7-(2,4-difluorophenyl)-8-iodo-6-(trifluoromethyl)quinazoline-2,4(1H,3H)-dione and 2-mercaptoethan-1-ol in 49% yield as a yellow solid m/z (ESI, +ve)=429.0 $(M+H)^+$.

$^1$H NMR (400 MHz, DMSO-d6) δ 11.75 (s, 1H), 10.16 (d, J=12 Hz, 1H), 8.05 (s, 1H), 7.48-7.34 (m, 2H), 7.29-7.23 (m, 1H), 4.79 (s, 1H), 3.25 (d, J=6.4 Hz, 3H), 3.22-3.14 (m, 1H), 2.84-2.77 (m, 1H), 2.73-2.64 (m, 1H), 2.57-2.52 (m, 1H), 2.47-2.34 (m, 1H).

Step 2: (3R)-10-chloro-11-(2,4-difluorophenyl)-3-methoxy-3,4-dihydro-2H,6H-[1,4]thiazepino[2,3,4-ij]quinazoline-6,8(7H)-dione

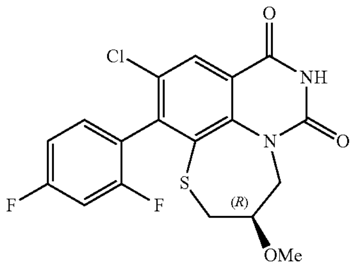

The title compound was prepared analogously to Example 100, step 10 where 6-chloro-7-(2,4-difluorophenyl)-8-(((R)-3-hydroxy-2-methoxypropyl)thio)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 90% yield as a white solid m/z (ESI, +ve)=411.0 $(M+H)^+$.

$^1$H NMR (400 MHz, DMSO-d6) δ 11.81 (d, J=4.8 Hz, 1H), 7.87 (d, J=8.8 Hz, 1H), 7.52-7.32 (m, 2H), 7.28-7.19 (m, 1H), 4.35-2.25 (m, 1H), 3.86-3.79 (m, 1H), 3.58 (d, J=13.8 Hz, 1H), 3.31 (d, J=10.0 Hz, 3H), 3.18-3.06 (m, 2H).

Step 3: tert-butyl (3S)-4-((3R)-10-chloro-11-(2,4-difluorophenyl)-3-methoxy-6-oxo-3,4-dihydro-2H,6H-[1,4]thiazepino[2,3,4-ij]quinazolin-8-yl)-3-methylpiperazine-1-carboxylate

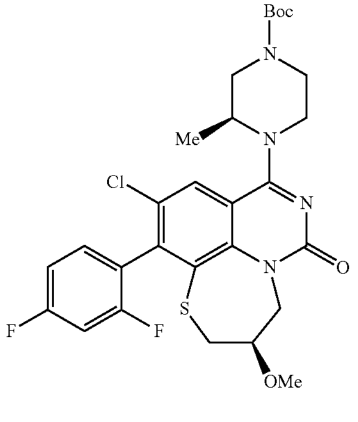 [SMILES: CO[C@H]1CSc2c(-c3ccc(F)cc3F)c(Cl)cc3c(N4CCN(C(=O)OC(C)(C)C)C[C@@H]4C)nc(=O)n(c23)C1]

The title compound was prepared analogously to Example 100, step 21 where (3R)-10-chloro-11-(2,4-difluorophenyl)-3-methoxy-3,4-dihydro-2H,6H-[1,4]thiazepino[2,3,4-ij]quinazoline-6,8(7H)-dione and tert-butyl (S)-3-methylpiperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 88% yield as a yellow solid m/z (ESI, +ve)=593.2 $(M+H)^+$.

Step 4: (3R)-10-chloro-11-(2,4-difluorophenyl)-3-methoxy-8-((S)-2-methylpiperazin-1-yl)-3,4-dihydro-2H,6H-[1,4]thiazepino[2,3,4-ij]quinazolin-6-one

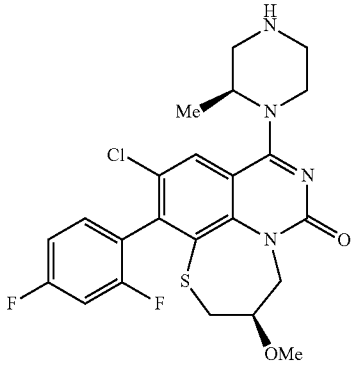 [SMILES: CO[C@H]1CSc2c(-c3ccc(F)cc3F)c(Cl)cc3c(N4CCNC[C@@H]4C)nc(=O)n(c23)C1]

The title compound was prepared analogously to Example 102, step 4, where tert-butyl (3S)-4-((3R)-10-chloro-11-(2,4-difluorophenyl)-3-methoxy-6-oxo-3,4-dihydro-2H,6H-[1,4]thiazepino[2,3,4-ij]quinazolin-8-yl)-3-methylpiperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 81% yield as a yellow oil m/z (ESI, +ve)=493.1 $(M+H)^+$.

Example 489: (3S)-8-(4-acryloylpiperazin-1-yl)-11-(2,4-difluorophenyl)-3-methoxy-10-(trifluoromethyl)-3,4-dihydro-2H,6H-[1,4]thiazepino[2,3,4-ij]quinazolin-6-one

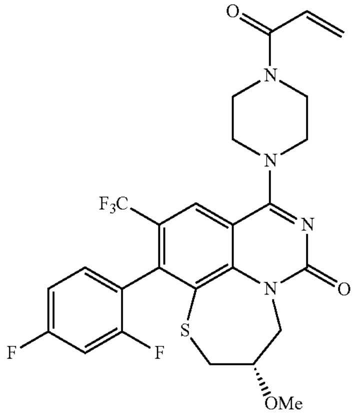 [SMILES: C=CC(=O)N1CCN(c2nc(=O)n3c4c(c(-c5ccc(F)cc5F)c(C(F)(F)F)cc24)SC[C@@H](OC)C3)CC1]

The title compound was prepared analogously to Example 84 where (3S)-11-(2,4-difluorophenyl)-3-methoxy-8-(piperazin-1-yl)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 6% yield as a yellow solid.

m/z (ESI, +ve)=567.1 (M+H)+.

$^1$H NMR (400 MHz, DMSO-d6) δ 7.89 (s, 1H), 7.44-7.42 (m, 2H), 7.28-7.24 (m, 1H), 6.85-6.78 (m, 1H), 6.17 (d, J=16.0 Hz 1H), 5.75-5.72 (m, 1H), 4.50-4.47 (m, 1H), 3.79-3.73 (m, 8H), 3.45-3.43 (m, 1H), 3.35 (s, 3H), 3.20-3.11 (m, 1H), 2.53-2.51 (m, 2H).

Step 1: (3S)-11-(2,4-difluorophenyl)-3-methoxy-8-(piperazin-1-yl)-10-(trifluoromethyl)-3,4-dihydro-2H,6H-[1,4]thiazepino[2,3,4-ij]quinazolin-6-one

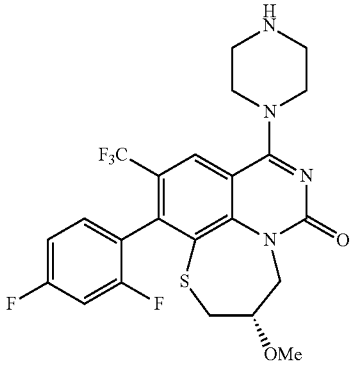 [SMILES: CO[C@@H]1CSc2c(-c3ccc(F)cc3F)c(C(F)(F)F)cc3c(N4CCNCC4)nc(=O)n(c23)C1]

The title compound was prepared analogously to Example 102, step 4, where (3S)-11-(2,4-difluorophenyl)-3-methoxy-10-(trifluoromethyl)-3,4-dihydro-2H,6H-[1,4]thiazepino[2,3,4-ij]quinazoline-6,8(7H)-dione was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 92% yield as a yellow oil m/z (ESI, +ve)=513.1 (M+H)+.

Example 490: (3R)-8-(4-acryloylpiperazin-1-yl)-11-(2,4-difluorophenyl)-3-methoxy-10-(trifluoromethyl)-3,4-dihydro-2H,6H-[1,4]thiazepino[2,3,4-ij]quinazolin-6-one

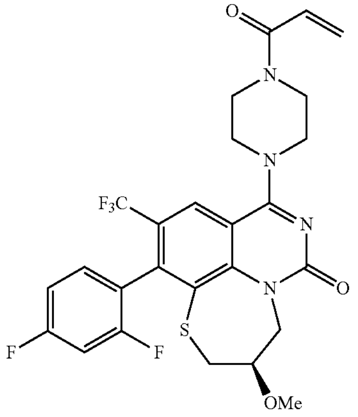 [SMILES: C=CC(=O)N1CCN(c2nc(=O)n3c4c(c(-c5ccc(F)cc5F)c(C(F)(F)F)cc24)SC[C@H](OC)C3)CC1]

The title compound was prepared analogously to Example 84 where (3R)-11-(2,4-difluorophenyl)-3-methoxy-8-(piperazin-1-yl)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3- thia-7,9-diazabicyclo[3.3.1]nonan-7-yl)-2,3-dihydro-5H-[1,4]thiazino[2,3,4-ij]quinazolin-5-one. The title compound was isolated in 26% yield as a yellow solid m/z (ESI, +ve)=567.0 $(M+H)^+$.

$^1$H NMR (400 MHz, DMSO-d6) δ 7.89 (s, 1H), 7.48-7.37 (m, 2H), 7.26 (t, J=12.0 Hz, 1H), 6.82 (dd, J=20.0, 12.0 Hz, 1H), 6.17 (dd, J=16.0, 4.0 Hz, 1H), 5.74 (dd, J=12.0, 4.0 Hz, 1H), 4.50-4.46 (m, 1H), 3.95-3.62 (m, 9H), 3.52-3.40 (m, 3H), 3.20-3.11 (m, 1H), 2.57-2.55 (m, 2H).

Step 1: tert-butyl 4-((3R)-11-(2,4-difluorophenyl)-3-methoxy-6-oxo-10-(trifluoromethyl)-3,4-dihydro-2H,6H-[1,4]thiazepino[2,3,4-ij]quinazolin-8-yl)piperazine-1-carboxylate

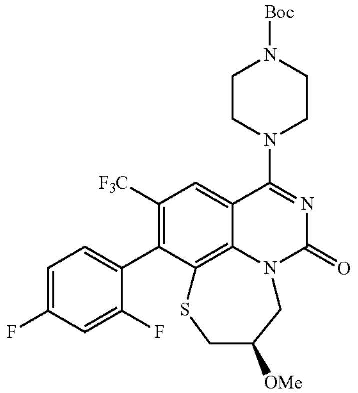 [SMILES: CO[C@H]1CSc2c(-c3ccc(F)cc3F)c(C(F)(F)F)cc3c(N4CCN(C(=O)OC(C)(C)C)CC4)nc(=O)n(c23)C1]

The title compound was prepared analogously to Example 100, step 21 where (3R)-11-(2,4-difluorophenyl)-3-methoxy-10-(trifluoromethyl)-3,4-dihydro-2H,6H-[1,4]thiazepino[2,3,4-ij]quinazoline-6,8(7H)-dione and tert-butyl piperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 97% yield as a yellow solid m/z (ESI, +ve)=613.1 $(M+H)^+$.

Step 2: (3R)-11-(2,4-difluorophenyl)-3-methoxy-8-(piperazin-1-yl)-10-(trifluoromethyl)-3,4-dihydro-2H,6H-[1,4]thiazepino[2,3,4-ij]quinazolin-6-one

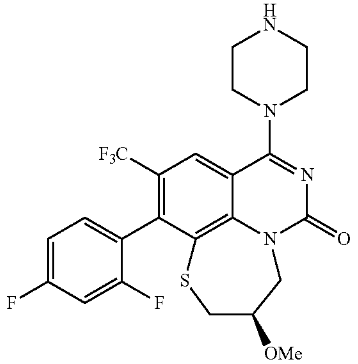 [SMILES: CO[C@H]1CSc2c(-c3ccc(F)cc3F)c(C(F)(F)F)cc3c(N4CCNCC4)nc(=O)n(c23)C1]

The title compound was prepared analogously to Example 102, step 4, where tert-butyl 4-((3R)-11-(2,4-difluorophenyl)-3-methoxy-6-oxo-10-(trifluoromethyl)-3,4-dihydro-2H,6H-[1,4]thiazepino[2,3,4-ij]quinazolin-8-yl)piperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 86% yield as a yellow oil.

m/z (ESI, +ve)=513.1 $(M+H)^+$.

Example 503: (3S)-8-((3S,5R)-4-acryloyl-3,5-dimethylpiperazin-1-yl)-11-(2,4-difluorophenyl)-3-methoxy-10-(trifluoromethyl)-3,4-dihydro-2H,6H-[1,4]thiazepino[2,3,4-ij]quinazolin-6-one

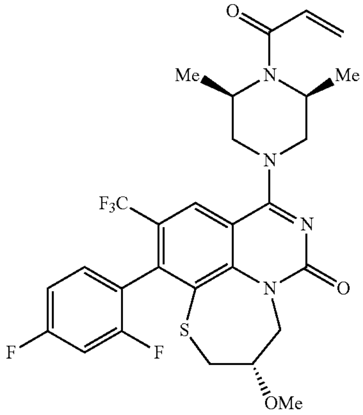 [SMILES: C=CC(=O)N1[C@H](C)CN(c2nc(=O)n3c4c(c(-c5ccc(F)cc5F)c(C(F)(F)F)cc24)SC[C@@H](OC)C3)C[C@@H]1C]

The title compound was prepared analogously to Example 84 where (3S)-11-(2,4-difluorophenyl)-8-((3S,5R)-3,5-dimethylpiperazin-1-yl)-3-methoxy-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 32% yield as a yellow solid.

m/z (ESI, +ve)=595.2 $(M+H)^+$.

$^1$H NMR (400 MHz, DMSO-d6) δ 8.04 (s, 1H), 7.47-7.39 (m, 2H), 7.2 (m, 1H), 6.81 (dd, J=16.0, 8.0 Hz, 1H), 6.19 (d, J=16.0 Hz, 1H), 5.74 (d, J=8.0 Hz, 1H), 4.59 (m, 2H), 4.49-4.47 (m, 1H), 4.06 (d, J=12 Hz, 2H), 3.86 (s, 1H), 3.46 (s, 1H), 3.35 (s, 2H), 3.31-3.06 (m, 4H), 2.52 (s, 1H), 1.51-1.25 (m, 6H).

Step 1: tert-butyl (2S,6R)-4-((3S)-11-(2,4-difluorophenyl)-3-methoxy-6-oxo-10-(trifluoromethyl)-3,4-dihydro-2H,6H-[1,4]thiazepino[2,3,4-ij]quinazolin-8-yl)-2,6-dimethylpiperazine-1-carboxylate

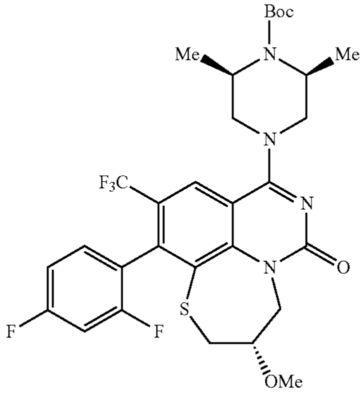 [SMILES: CO[C@@H]1CSc2c(-c3ccc(F)cc3F)c(C(F)(F)F)cc3c(N4C[C@@H](C)N(C(=O)OC(C)(C)C)[C@@H](C)C4)nc(=O)n(c23)C1]

The title compound was prepared analogously to Example 100, step 21 where (3S)-11-(2,4-difluorophenyl)-8-hydroxy-3-methoxy-10-(trifluoromethyl)-3,4-dihydro-2H,6H-[1,4]thiazepino[2,3,4-ij]quinazolin-6-one and (2R,6S)-2,6-dimethylpiperazine were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 69% yield as a yellow solid m/z (ESI, +ve)=541.1 $(M+H)^+$.

Step 2: (3S)-11-(2,4-difluorophenyl)-8-((3S,5R)-3,5-dimethylpiperazin-1-yl)-3-methoxy-10-(trifluoromethyl)-3,4-dihydro-2H,6H-[1,4]thiazepino[2,3,4-ij]quinazolin-6-one

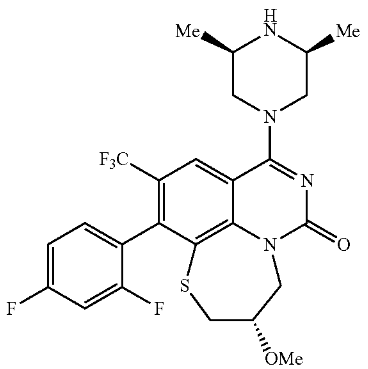 [SMILES: CO[C@@H]1CSc2c(-c3ccc(F)cc3F)c(C(F)(F)F)cc3c(N4C[C@@H](C)N[C@@H](C)C4)nc(=O)n(c23)C1]

The title compound was prepared analogously to Example 102, step 4, where tert-butyl (2S,6R)-4-((3S)-11-(2,4-difluorophenyl)-3-methoxy-6-oxo-10-(trifluoromethyl)-3,4-dihydro-2H,6H-[1,4]thiazepino[2,3,4-ij]quinazolin-8-yl)-2,6-dimethylpiperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 32% yield as a yellow solid Example 504: (3S)-8-(4-acryloylpiperazin-1-yl)-10-chloro-11-(2,4-difluorophenyl)-3-methoxy-3,4-dihydro-2H,6H-[1,4]thiazepino[2,3,4-ij]quinazolin-6-one

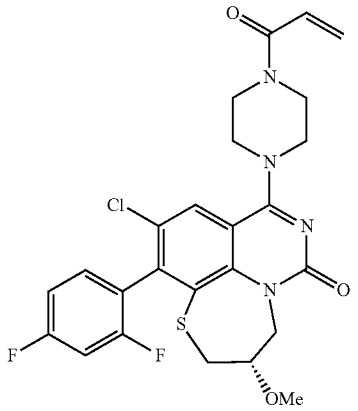 [SMILES: C=CC(=O)N1CCN(c2nc(=O)n3c4c(c(-c5ccc(F)cc5F)c(Cl)cc24)SC[C@@H](OC)C3)CC1]

The title compound was prepared analogously to Example 84 where (3S)-10-chloro-11-(2,4-difluorophenyl)-3-methoxy-8-(piperazin-1-yl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 39% yield as a yellow solid m/z (ESI, +ve)=532.1 $(M+H)^+$.

$^1$H NMR (400 MHz, DMSO-d6) δ 7.74 (s, 1H), 7.48-7.44 (m, 2H), 7.29-7.25 (m, 1H), 6.82 (dd, J=16.0, 8.0 Hz, 1H), 6.17 (d, J=16.0 Hz, 1H), 5.74 (d, J=8.0 Hz, 1H), 4.49-4.40 (m, 1H), 3.90-3.64 (m, 8H), 3.44-3.40 (m, 1H), 3.35 (s, 3H), 3.31-3.29 (m, 1H), 3.17-3.08 (m, 1H), 2.52 (m, 1H).

Step 1: tert-butyl 4-((3S)-10-chloro-11-(2,4-difluorophenyl)-3-methoxy-6-oxo-3,4-dihydro-2H,6H-[1,4]thiazepino[2,3,4-ij]quinazolin-8-yl)piperazine-1-carboxylate

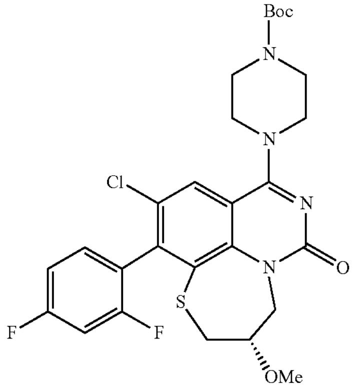 [SMILES: CO[C@@H]1CSc2c(-c3ccc(F)cc3F)c(Cl)cc3c(N4CCN(C(=O)OC(C)(C)C)CC4)nc(=O)n(c23)C1]

The title compound was prepared analogously to Example 100, step 21 where (3S)-10-chloro-11-(2,4-difluorophenyl)-8-hydroxy-3-methoxy-3,4-dihydro-2H,6H-[1,4]thiazepino[2,3,4-ij]quinazolin-6-one and tert-butyl piperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 89% yield as a yellow solid m/z (ESI, +ve)=579.1 $(M+H)^+$.

Step 2: (3S)-10-chloro-11-(2,4-difluorophenyl)-3-methoxy-8-(piperazin-1-yl)-3,4-dihydro-2H,6H-[1,4]thiazepino[2,3,4-ij]quinazolin-6-one

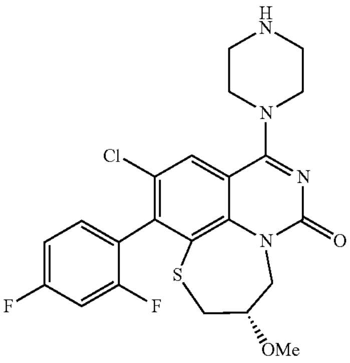 [SMILES: CO[C@@H]1CSc2c(-c3ccc(F)cc3F)c(Cl)cc3c(N4CCNCC4)nc(=O)n(c23)C1]

The title compound was prepared analogously to Example 102, step 4, where tert-butyl 4-((3S)-10-chloro-11-(2,4-difluorophenyl)-3-methoxy-6-oxo-3,4-dihydro-2H,6H-[1,4]thiazepino[2,3,4-ij]quinazolin-8-yl)piperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 89% yield as a yellow solid m/z (ESI, +ve)=479.1 $(M+H)^+$.

Example 505: (3S)-8-((3S,5R)-4-acryloyl-3,5-dimethylpiperazin-1-yl)-10-chloro-11-(2,4-difluorophenyl)-3-methoxy-3,4-dihydro-2H,6H-[1,4]thiazepino[2,3,4-ij]quinazolin-6-one

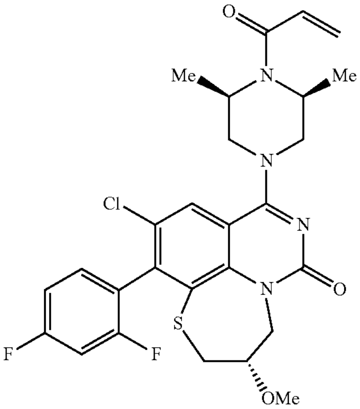 [SMILES: C=CC(=O)N1[C@H](C)CN(c2nc(=O)n3c4c(c(-c5ccc(F)cc5F)c(Cl)cc24)SC[C@@H](OC)C3)C[C@@H]1C]

The title compound was prepared analogously to Example 84 where (3S)-10-chloro-11-(2,4-difluorophenyl)-8-((3S,5R)-3,5-dimethylpiperazin-1-yl)-3-methoxy-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 16% yield as a yellow solid.

m/z (ESI, +ve)=561.1 (M+H)+.

$^1$H NMR (400 MHz, DMSO-d6) δ 7.81 (s, 1H), 7.50-7.41 (m, 2H), 7.30-7.25 (m, 1H), 6.84-6.77 (m, 1H), 6.21-6.16 (m, 1H), 5.75-5.72 (m, 1H), 4.56 (s, 2H), 4.46-4.43 (m, 1H), 4.08-4.03 (m, 2H), 3.87-3.86 (m, 1H), 3.46-3.43 (m, 2H), 3.35-3.28 (m, 3H), 3.17-3.10 (m, 1H), 2.52-2.51 (m, 2H), 1.43-1.34 (m, 6H).

Step 1: (3S)-10-chloro-11-(2,4-difluorophenyl)-8-((3S,5R)-3,5-dimethylpiperazin-1-yl)-3-methoxy-3,4-dihydro-2H,6H-[1,4]thiazepino[2,3,4-ij]quinazolin-6-one

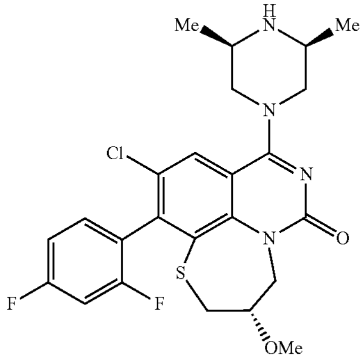 [SMILES: CO[C@@H]1CSc2c(-c3ccc(F)cc3F)c(Cl)cc3c(N4C[C@@H](C)N[C@@H](C)C4)nc(=O)n(c23)C1]

The title compound was prepared analogously to Example 100, step 21 where (3S)-10-chloro-11-(2,4-difluorophenyl)-8-hydroxy-3-methoxy-3,4-dihydro-2H,6H-[1,4]thiazepino[2,3,4-ij]quinazolin-6-one and (2S,6R)-2,6-dimethylpiperazine were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 89% yield as a yellow solid m/z (ESI, +ve)=507.1 $(M+H)^+$.

Example 507: (2S)-7-((S)-4-acryloyl-2-methylpiperazin-1-yl)-10-(2,4-difluorophenyl)-2-(methoxymethyl)-9-(trifluoromethyl)-2,3-dihydro-5H-[1,4]thiazino[2,3,4-ij]quinazolin-5-one

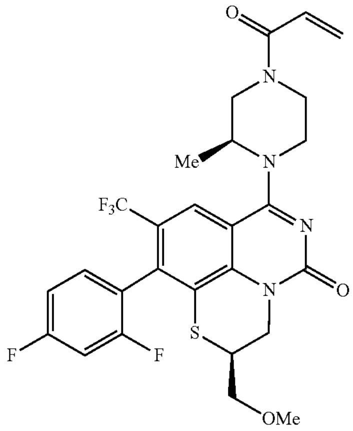 [SMILES: C=CC(=O)N1CCN(c2nc(=O)n3c4c(c(-c5ccc(F)cc5F)c(C(F)(F)F)cc24)S[C@H](COC)C3)[C@@H](C)C1]

Over a solution of (2S)-10-(2,4-difluorophenyl)-2-(methoxymethyl)-7-((S)-2-methylpiperazin-1-yl)-9-(trifluoromethyl)-2,3-dihydro-5H-[1,4]thiazino[2,3,4-ij]quinazolin-5-one (32 mg) in acetonitrile (1 mL), triethylamine (0.11 mL) and acryloyl chloride (0.014 mL) were added. The mixture was stirred at room temperature for 30 minutes and at that time quenched by the addition of water. The mixture was extracted with ethyl acetate, dried over sodium sulfate and concentrated to afford a residue that was purified by HPLC. The title compound was isolated as a white solid in 32% yield m/z (ESI, +ve)=581.2 $(M+H)^+$.

Step 1: tert-butyl (3S)-4-((2S)-10-(2,4-difluorophenyl)-2-(((methylsulfonyl)oxy)methyl)-5-oxo-9-(trifluoromethyl)-2,3-dihydro-5H-[1,4]thiazino[2,3,4-ij]quinazolin-7-yl)-3-methylpiperazine-1-carboxylate

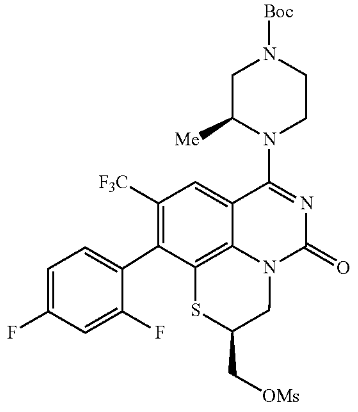 [SMILES: C[C@H]1CN(C(=O)OC(C)(C)C)CCN1c1nc(=O)n2c3c(c(-c4ccc(F)cc4F)c(C(F)(F)F)cc13)S[C@H](COS(C)(=O)=O)C2]

Over a solution of tert-butyl (3S)-4-((3S)-11-(2,4-difluorophenyl)-3-hydroxy-6-oxo-10-(trifluoromethyl)-3,4-dihydro-2H,6H-[1,4]thiazepino[2,3,4-ij]quinazolin-8-yl)-3-methylpiperazine-1-carboxylate (391 mg) in 3 mL of dichloroethane at room temperature, N,N-diisopropylethylamine (1.0 mL) and methanesulfonyl chloride (0.34 mL) were added and the mixture heated at 80° C. for three hours. The reaction was cooled down to room temperature and diluted with dichloromethane and water. The organic layer was separated and the aqueous layer extracted with dichloromethane twice. Evaporation of volatiles under reduced pressure afforded a crude residue that was purified by silica gel chromatography (0-3% methanol in ethyl acetate). The title compound was isolated in 43% yield.

m/z (ESI, +ve)=691.2 $(M+H)^+$.

Step 2: tert-Butyl (3S)-4-((2S)-10-(2,4-difluorophenyl)-2-(methoxymethyl)-5-oxo-9-(trifluoromethyl)-2,3-dihydro-5H-[1,4]thiazino[2,3,4-ij]quinazolin-7-yl)-3-methylpiperazine-1-carboxylate

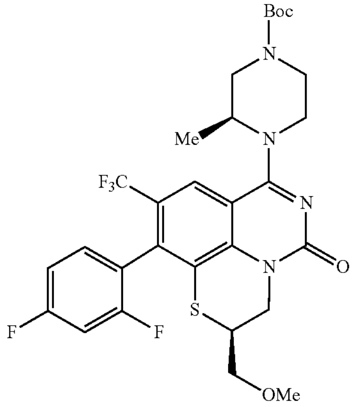

tert-butyl (3S)-4-((2S)-10-(2,4-difluorophenyl)-2-(((methylsulfonyl)oxy)methyl)-5-oxo-9-(trifluoromethyl)-2,3-dihydro-5H-[1,4]thiazino[2,3,4-ij]quinazolin-7-yl)-3-methylpiperazine-1-carboxylate (95 mg) was dissolved in methanol (2 mL) and heated at 70° C. for three hours. The methanol was removed under reduced pressure and the crude material purified by chromatography in silica gel to afford the title compound in 43% yield as an orange solid.

m/z (ESI, +ve)=627.2 $(M+H)^+$.

Step 3: (2S)-10-(2,4-difluorophenyl)-2-(methoxymethyl)-7-((S)-2-methylpiperazin-1-yl)-9-(trifluoromethyl)-2,3-dihydro-5H-[1,4]thiazino[2,3,4-ij]quinazolin-5-one

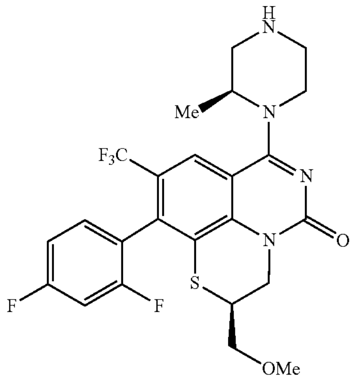 [SMILES: COC[C@@H]1Cn2c(=O)nc(N3CCNC[C@@H]3C)c3cc(C(F)(F)F)c(-c4ccc(F)cc4F)c(c32)S1]

Over a solution of tert-butyl (3S)-4-((2S)-10-(2,4-difluorophenyl)-2-(methoxymethyl)-5-oxo-9-(trifluoromethyl)-2,3-dihydro-5H-[1,4]thiazino[2,3,4-ij]quinazolin-7-yl)-3-methylpiperazine-1-carboxylate (37 mg) in dichloromethane (1 mL), TFA (0.2 mL) was added. The mixture was stirred at room temperature for 4 hours and at that time all volatiles were removed under reduced pressure to afford a solid that was used in the next step without further purification.

m/z (ESI, +ve)=627.2 $(M+H)^+$.

Example 524: (3R)-8-((3S,5R)-4-acryloyl-3,5-dimethylpiperazin-1-yl)-11-(2,4-difluorophenyl)-3-methoxy-10-(trifluoromethyl)-3,4-dihydro-2H,6H-[1,4]thiazepino[2,3,4-ij]quinazolin-6-one

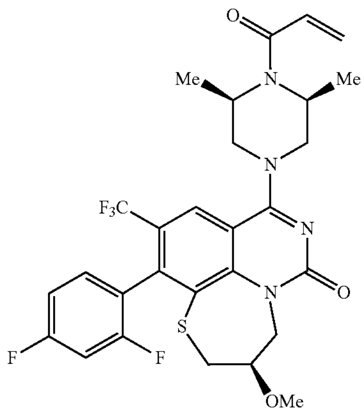 [SMILES: C=CC(=O)N1[C@H](C)CN(c2nc(=O)n3c4c(c(-c5ccc(F)cc5F)c(C(F)(F)F)cc24)SC[C@H](OC)C3)C[C@@H]1C]

The title compound was prepared analogously to Example 84 where (3R)-11-(2,4-difluorophenyl)-8-((3S,5R)-3,5-dimethylpiperazin-1-yl)-3-methoxy-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 25% yield as a white solid m/z (ESI, +ve)=595.0 $(M+H)^+$.

$^1$H NMR (400 MHz, DMSO-d6) δ 8.04 (s, 1H), 7.52-7.39 (m, 2H), 7.30-7.23 (m, 1H), 6.81 (dd, J=16.0, 8.0 Hz, 1H), 6.19 (dd, J=16.0, 2.0 Hz, 1H), 5.74 (dd, J=16.0, 2.0 Hz, 1H), 4.78-4.40 (m, 4H), 4.17-4.09 (m, 2H), 3.86-3.81 (m, 1H), 3.57-3.35 (m, 4H), 3.29-3.09 (m, 3H), 1.52-1.26 (m, 6H).

Step 1: (3R)-11-(2,4-difluorophenyl)-8-((3S,5R)-3,5-dimethylpiperazin-1-yl)-3-methoxy-10-(trifluoromethyl)-3,4-dihydro-2H,6H-[1,4]thiazepino[2,3,4-ij]quinazolin-6-one

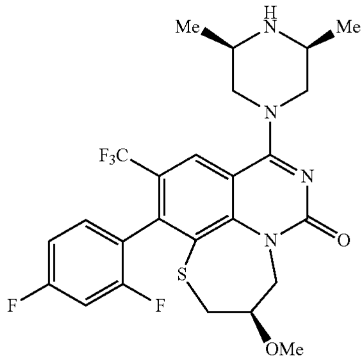 [SMILES: CO[C@H]1CSc2c(-c3ccc(F)cc3F)c(C(F)(F)F)cc3c(N4C[C@@H](C)N[C@@H](C)C4)nc(=O)n(c23)C1]

The title compound was prepared analogously to Example 100, step 21 where (3R)-11-(2,4-difluorophenyl)-8-hydroxy-3-methoxy-10-(trifluoromethyl)-3,4-dihydro-2H,6H-[1,4]thiazepino[2,3,4-ij]quinazolin-6-one and (2S,6R)-2,6-dimethylpiperazine were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 90% yield as a yellow solid m/z (ESI, +ve)=541.1 $(M+H)^+$.

Example 525: (3R)-8-(4-acryloylpiperazin-1-yl)-10-chloro-11-(2,4-difluorophenyl)-3-methoxy-3,4-dihydro-2H,6H-[1,4]thiazepino[2,3,4-ij]quinazolin-6-one

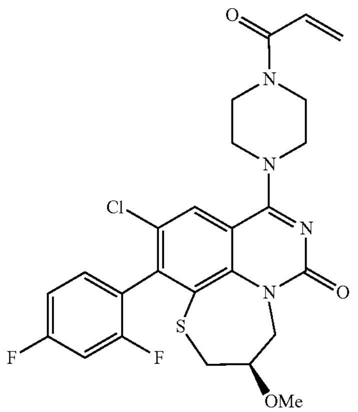 [SMILES: C=CC(=O)N1CCN(c2nc(=O)n3c4c(c(-c5ccc(F)cc5F)c(Cl)cc24)SC[C@H](OC)C3)CC1]

The title compound was prepared analogously to Example 84 where (3R)-10-chloro-11-(2,4-difluorophenyl)-3-methoxy-8-(piperazin-1-yl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 19% yield as a yellow solid m/z (ESI, +ve)=533.0 $(M+H)^+$.

$^1$H NMR (400 MHz, DMSO-d6) δ 7.74 (s, 1H), 7.50-7.43 (m, 2H), 7.30-7.25 (m, 1H), 6.82 (dd, J=16.0, 8.0 Hz, 1H), 6.19 (dd, J=16.0, 2.0 Hz, 1H), 5.74 (dd, J=16.0, 2.0 Hz, 1H), 4.49-4.41 (m, 1H), 3.90-3.63 (m, 9H), 3.46-3.35 (m, 2H), 3.32-3.26 (m, 3H), 3.17-3.08 (m, 1H).

Step 1: tert-butyl 4-((3R)-10-chloro-11-(2,4-difluorophenyl)-3-methoxy-6-oxo-3,4-dihydro-2H,6H-[1,4]thiazepino[2,3,4-ij]quinazolin-8-yl)piperazine-1-carboxylate

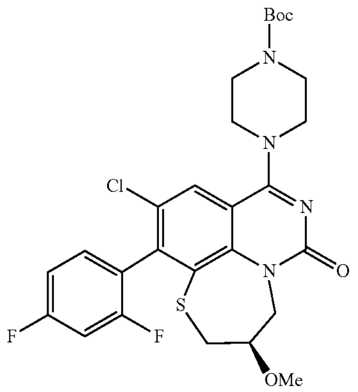 [SMILES: CO[C@H]1CSc2c(-c3ccc(F)cc3F)c(Cl)cc3c(N4CCN(C(=O)OC(C)(C)C)CC4)nc(=O)n(c23)C1]

The title compound was prepared analogously to Example 100, step 21 where (3R)-10-chloro-11-(2,4-difluorophenyl)-8-hydroxy-3-methoxy-3,4-dihydro-2H,6H-[1,4]thiazepino[2,3,4-ij]quinazolin-6-one and tert-butyl piperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 72% yield as a yellow solid m/z (ESI, +ve)=579.0 $(M+H)^+$.

Step 2: (3R)-10-chloro-11-(2,4-difluorophenyl)-3-methoxy-8-(piperazin-1-yl)-3,4-dihydro-2H,6H-[1,4]thiazepino[2,3,4-ij]quinazolin-6-one

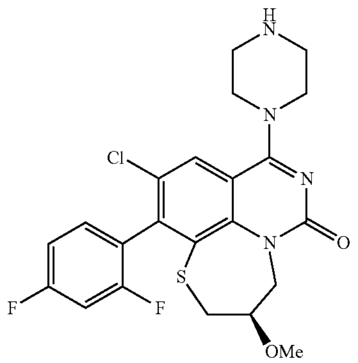 [SMILES: CO[C@H]1CSc2c(-c3ccc(F)cc3F)c(Cl)cc3c(N4CCNCC4)nc(=O)n(c23)C1]

The title compound was prepared analogously to Example 102, step 4, where tert-butyl 4-((3R)-10-chloro-11-(2,4-difluorophenyl)-3-methoxy-6-oxo-3,4-dihydro-2H,6H-[1,4]thiazepino[2,3,4-ij]quinazolin-8-yl)piperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 89% yield as a yellow solid m/z (ESI, +ve)=479.1 $(M+H)^+$.

Example 526: (3R)-8-((3S,5R)-4-acryloyl-3,5-dimethylpiperazin-1-yl)-10-chloro-11-(2,4-difluorophenyl)-3-methoxy-3,4-dihydro-2H,6H-[1,4]thiazepino[2,3,4-ij]quinazolin-6-one

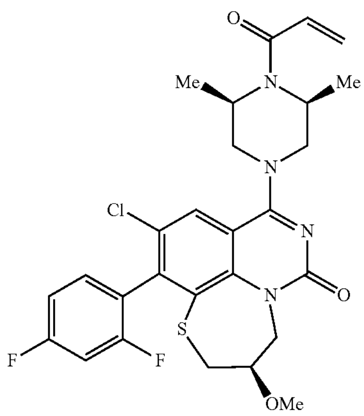 [SMILES: C=CC(=O)N1[C@H](C)CN(c2nc(=O)n3c4c(c(-c5ccc(F)cc5F)c(Cl)cc24)SC[C@H](OC)C3)C[C@@H]1C]

The title compound was prepared analogously to Example 84 where (3R)-10-chloro-11-(2,4-difluorophenyl)-8-((3S,5R)-3,5-dimethylpiperazin-1-yl)-3-methoxy-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 24% yield as a yellow solid m/z (ESI, +ve)=561.1 $(M+H)^+$.

$^1H$ NMR (400 MHz, DMSO-d6) δ 7.81 (s, 1H), 7.50-7.45 (m, 2H), 7.30-7.25 (m, 1H), 6.80 (dd, J=16.0, 8.0 Hz, 1H), 6.19 (dd, J=16.0, 2.0 Hz, 1H), 5.74 (dd, J=16.0, 2.0 Hz, 1H), 4.68-4.39 (m, 4H), 4.14-3.97 (m, 2H), 3.88-3.86 (m, 1H), 3.50-3.35 (m, 3H), 3.30-3.06 (m, 4H), 1.47-1.17 (m, 6H).

Step 1: (3R)-10-chloro-11-(2,4-difluorophenyl)-8-((3S,5R)-3,5-dimethylpiperazin-1-yl)-3-methoxy-3,4-dihydro-2H,6H-[1,4]thiazepino[2,3,4-ij]quinazolin-6-one

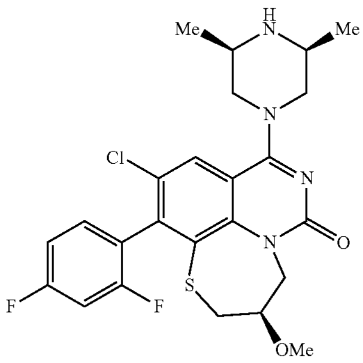 [SMILES: CO[C@H]1CSc2c(-c3ccc(F)cc3F)c(Cl)cc3c(N4C[C@@H](C)N[C@@H](C)C4)nc(=O)n(c23)C1]

The title compound was prepared analogously to Example 100, step 21 where (3R)-10-chloro-11-(2,4-difluorophenyl)-8-hydroxy-3-methoxy-3,4-dihydro-2H,6H-[1,4]thiazepino[2,3,4-ij]quinazolin-6-one and (2R,6S)-2,6-dimethylpiperazine were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 61% yield as a yellow solid m/z (ESI, +ve)=507.1 $(M+H)^+$.

Example 527: (R)-8-((S)-4-acryloyl-2-methylpiperazin-1-yl)-11-(4-fluorophenyl)-3-methoxy-10-(trifluoromethyl)-3,4-dihydro-2H,6H-[1,4]thiazepino[2,3,4-ij]quinazolin-6-one

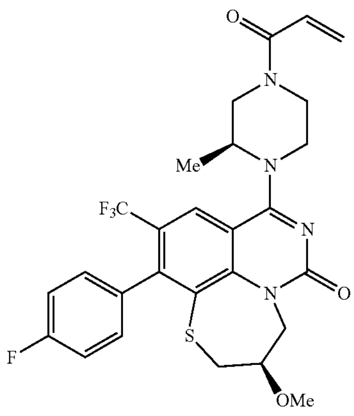 [SMILES: C=CC(=O)N1CCN(c2nc(=O)n3c4c(c(-c5ccc(F)cc5)c(C(F)(F)F)cc24)SC[C@H](OC)C3)[C@@H](C)C1]

The title compound was prepared analogously to Example 84 where (R)-11-(4-fluorophenyl)-3-methoxy-8-((S)-2-methylpiperazin-1-yl)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 9% yield as a yellow solid m/z (ESI, +ve)=563.2 (M+H)+.

$^1$H NMR (400 MHz, DMSO) δ 7.78 (s, 1H), 7.35-7.34 (m, 4H), 6.90-6.78 (m, 1H), 6.18 (6.21-6.15, 1H), 5.76-5.73 (m, 1H), 4.64-4.60 (m, 1H), 4.53-4.49 (m, 1H), 4.42-4.38 (m, 1H), 4.30-4.25 (m, 1H), 4.12-3.99 (m, 2H), 3.81-3.80 (m, 1H), 3.56-3.54 (m, 2H), 3.33 (s, 3H), 3.13-2.97 (m, 3H), 1.30 (s, 3H).

Step 1: Methyl 3-amino-4'-fluoro-[1,1'-biphenyl]-4-carboxylate

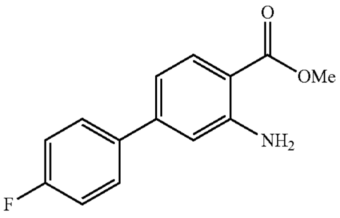 [SMILES: COC(=O)c1ccc(-c2ccc(F)cc2)cc1N]

The title compound was synthesized analogously to example 100, step 1 where 4-fluorophenylboronic acid was substituted in place of (2,4-difluorophenyl)boronic acid. The title compound was isolated in 99% yield as a brown solid m/z (ESI, +ve)=246.1 $(M+H)^+$.

Step 2: Methyl 5-amino-4'-fluoro-2-iodo-[1,1'-biphenyl]-4-carboxylate

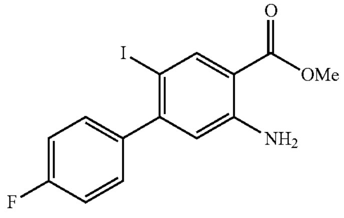 [SMILES: COC(=O)c1cc(I)c(-c2ccc(F)cc2)cc1N]

The title compound was synthesized analogously to example 100, step 2 where Methyl 3-amino-4'-fluoro-[1,1'-biphenyl]-4-carboxylate was substituted in place of methyl 3-amino-2',4'-difluoro-[1,1'-biphenyl]-4-carboxylate. The title compound was isolated in 90% yield as a brown solid m/z (ESI, +ve)=372.0 $(M+H)^+$.

Step 3: Methyl 5-acetamido-4'-fluoro-2-iodo-[1,1'-biphenyl]-4-carboxylate

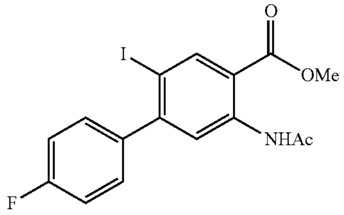 [SMILES: COC(=O)c1cc(I)c(-c2ccc(F)cc2)cc1NC(C)=O]

The title compound was synthesized analogously to example 100, step 3 where methyl 5-amino-4'-fluoro-2-iodo-[1,1'-biphenyl]-4-carboxylate was substituted in place of 2-amino-4-(2,4-difluorophenyl)-5-iodobenzoate. The title compound was isolated in 98% yield as a brown solid m/z (ESI, +ve)=414.0 $(M+H)^+$.

Step 4: Methyl 5-acetamido-4'-fluoro-2-(trifluoromethyl)-[1,1'-biphenyl]-4-carboxylate

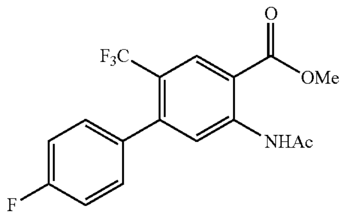 [SMILES: COC(=O)c1cc(C(F)(F)F)c(-c2ccc(F)cc2)cc1NC(C)=O]

The title compound was synthesized analogously to example 100, step 4 where methyl 5-acetamido-4'-fluoro-2-iodo-[1,1'-biphenyl]-4-carboxylate was substituted in place of methyl 4-(2,4-difluorophenyl)-2-acetamido-5-iodobenzoate. The title compound was isolated in 62% yield as a brown solid m/z (ESI, +ve)=356.1 $(M+H)^+$.

Step 5: Methyl 5-amino-4'-fluoro-2-(trifluoromethyl)-[1,1'-biphenyl]-4-carboxylate

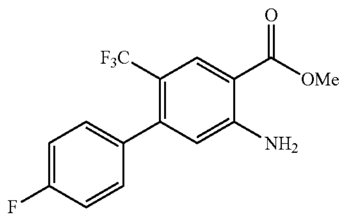 [SMILES: COC(=O)c1cc(C(F)(F)F)c(-c2ccc(F)cc2)cc1N]

The title compound was synthesized analogously to example 100, step 5 where methyl 5-acetamido-4'-fluoro-2-(trifluoromethyl)-[1,1'-biphenyl]-4-carboxylate was substituted in place of methyl 5-acetamido-2',4'-difluoro-2-(trifluoromethyl)-[1,1'-biphenyl]-4-carboxylate. The title compound was isolated in 87% yield as a white solid m/z (ESI, +ve)=314.1 $(M+H)^+$.

Step 6: Methyl 3-amino-4'-fluoro-2-iodo-6-(trifluoromethyl)-[1,1'-biphenyl]-4-carboxylate

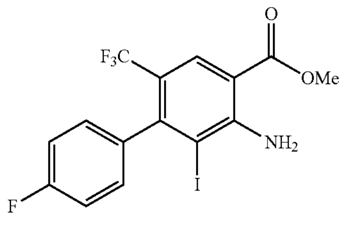 [SMILES: COC(=O)c1cc(C(F)(F)F)c(-c2ccc(F)cc2)c(I)c1N]

The title compound was synthesized analogously to example 100, step 6 where methyl 5-amino-4'-fluoro-2-(trifluoromethyl)-[1,1'-biphenyl]-4-carboxylate was substituted in place of methyl 5-amino-2',4'-difluoro-2-(trifluoromethyl)-[1,1'-biphenyl]-4-carboxylate. The title compound was isolated in 74% yield as a white solid m/z (ESI, +ve)=440.0 $(M+H)^+$.

Step 7: 3-Amino-4'-fluoro-2-iodo-6-(trifluoromethyl)-[1,1'-biphenyl]-4-carboxylic acid

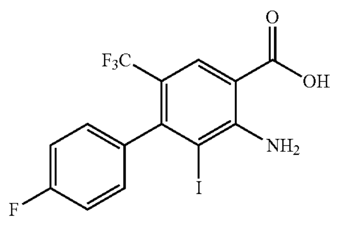 [SMILES: Nc1c(C(=O)O)cc(C(F)(F)F)c(-c2ccc(F)cc2)c1I]

The title compound was synthesized analogously to example 100, step 7 where methyl 3-amino-4'-fluoro-2-iodo-6-(trifluoromethyl)-[1,1'-biphenyl]-4-carboxylate was substituted in place of methyl 3-amino-2',4'-difluoro-2-iodo-6-(trifluoromethyl)-[1,1'-biphenyl]-4-carboxylate. The title compound was isolated in 94% yield as a white solid $^1$H NMR (400 MHz, DMSO-d6) δ8.18 (s, 1H), 7.29 (t, 2H), 7.16 (m, 2H).

Step 8: 7-(4-fluorophenyl)-8-iodo-6-(trifluoromethyl)quinazoline-2,4(1H,3H)-dione

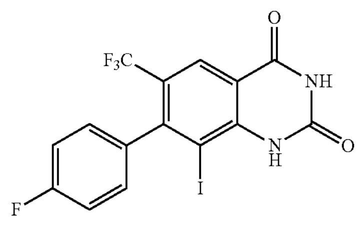

The title compound was synthesized analogously to example 100, step 8 where 3-Amino-4'-fluoro-2-iodo-6-(trifluoromethyl)-[1,1'-biphenyl]-4-carboxylic acid was substituted in place of 3-amino-2',4'-difluoro-2-iodo-6-(trifluoromethyl)-[1,1'-biphenyl]-4-carboxylic acid. The title compound was isolated in 70% yield as a white solid. m/z (ESI, +ve)=451.0 (M+H)+. $^1$H NMR (400 MHz, DMSO-d6) δ 11.89 (s, 1H), 9.75 (s, 1H), 8.23 (s, 1H), 7.41-7.31 (m, 2H), 7.21-7.11 (m, 2H).

Step 9: (R)-7-(4-fluorophenyl)-8-((3-hydroxy-2-methoxypropyl)thio)-6-(trifluoromethyl)quinazoline-2,4(1H,3H)-dione

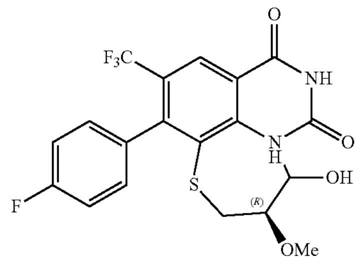

The title compound was synthesized analogously to example 100, step 9 where 7-(4-fluorophenyl)-8-iodo-6-(trifluoromethyl)quinazoline-2,4(1H,3H)-dione and (R)-3-mercapto-2-methoxypropan-1-ol was substituted in place of 7-(2,4-difluorophenyl)-8-iodo-6-(trifluoromethyl)quinazoline-2,4(1H,3H)-dione and 2-mercaptoethan-1-ol. The title compound was isolated in 58% yield as a white solid. m/z (ESI, +ve)=445.1 $(M+H)^+$.

Step 10: (R)-11-(4-fluorophenyl)-3-methoxy-10-(trifluoromethyl)-3,4-dihydro-2H,6H-[1,4]thiazepino[2,3,4-ij]quinazoline-6,8(7H)-dione

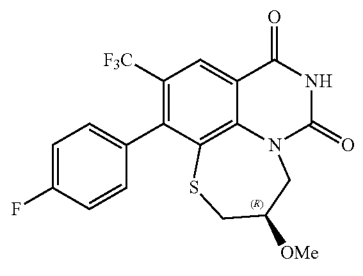

The title compound was prepared analogously to Example 100, step 10 where (R)-7-(4-fluorophenyl)-8-((3-hydroxy-2-methoxypropyl)thio)-6-(trifluoromethyl)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 53% yield as a yellow solid m/z (ESI, +ve)=427.0 $(M+H)^+$.

Step 11: tert-butyl (S)-4-((R)-11-(4-fluorophenyl)-3-methoxy-6-oxo-10-(trifluoromethyl)-3,4-dihydro-2H,6H-[1,4]thiazepino[2,3,4-ij]quinazolin-8-yl)-3-methylpiperazine-1-carboxylate

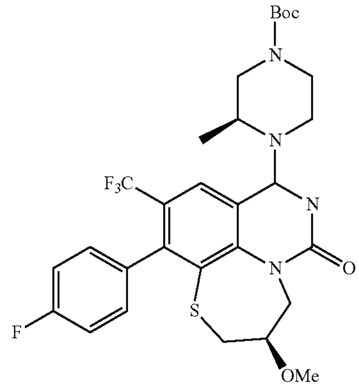 [SMILES: CO[C@H]1CSc2c(-c3ccc(F)cc3)c(C(F)(F)F)cc3c2N(C1)C(=O)NC3N1CCN(C(=O)OC(C)(C)C)C[C@@H]1C]

The title compound was prepared analogously to Example 100, step 21 where (R)-11-(4-fluorophenyl)-3-methoxy-10-(trifluoromethyl)-3,4-dihydro-2H,6H-[1,4]thiazepino[2,3,4-ij]quinazoline-6,8(7H)-dione and tert-butyl (S)-3-methylpiperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 76% yield as a yellow solid m/z (ESI, +ve)=609.2 $(M+H)^+$.

Step 12: (R)-11-(4-fluorophenyl)-3-methoxy-8-((S)-2-methylpiperazin-1-yl)-10-(trifluoromethyl)-3,4-dihydro-2H,6H-[1,4]thiazepino[2,3,4-ij]quinazolin-6-one

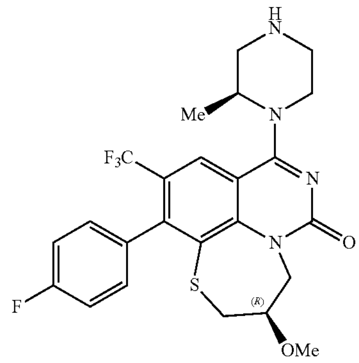

The title compound was prepared analogously to Example 102, step 4, where tert-butyl (S)-4-((R)-11-(4-fluorophenyl)-3-methoxy-6-oxo-10-(trifluoromethyl)-3,4-dihydro-2H,6H-[1,4]thiazepino[2,3,4-ij]quinazolin-8-yl)-3-methylpiperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 84% yield as a yellow solid m/z (ESI, +ve)=509.1 (M+H)+.

Example 528: (R)-8-((S)-4-acryloyl-2-methylpiperazin-1-yl)-10-chloro-11-(4-fluorophenyl)-3-methoxy-3,4-dihydro-2H,6H-[1,4]thiazepino[2,3,4-ij]quinazolin-6-one

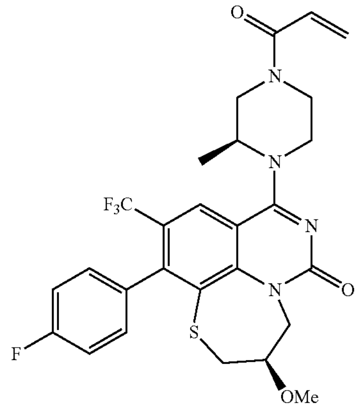 [SMILES: C=CC(=O)N1CCN(c2nc(=O)n3c4c(c(-c5ccc(F)cc5)c(C(F)(F)F)cc24)SC[C@H](OC)C3)[C@@H](C)C1]

The title compound was prepared analogously to Example 84 where (R)-10-chloro-11-(4-fluorophenyl)-3-methoxy-8-((S)-2-methylpiperazin-1-yl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 9% yield as a yellow solid m/z (ESI, +ve)=529.2 $(M+H)^+$.

$^1H$ NMR (400 MHz, DMSO-d6) δ 7.64 (s, 1H), 7.42-7.28 (m, 4H), 6.91-6.76 (m, 1H), 6.18 (dd, J=16.0 Hz, 8.0 Hz, 1H), 5.74 (d, J=8.0 Hz, 1H), 4.73-4.58 (m, 1H), 4.49-4.34 (m, 2H), 4.29-4.20 (m, 0.5H), 4.16-4.07 (m, 0.5H), 4.06-3.89 (m, 2H), 3.88-3.80 (m, 1H), 3.68-3.47 (m, 2H), 3.33 (s, 4H), 3.19-3.13 (m, 0.5H), 3.13-3.03 (m, 1H), 3.00-2.89 (m, 0.5H), 1.27-1.23 (m, 3H).

Step 1: Methyl 5-amino-2-chloro-4'-fluoro-[1,1'-biphenyl]-4-carboxylate

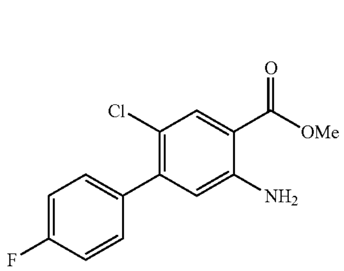 [SMILES: COC(=O)c1cc(Cl)c(-c2ccc(F)cc2)cc1N]

The title compound was prepared analogously to Example 84, step 15 where 4-fluorophenylboronic acid was substituted in place of (2,4-difluorophenyl)boronic acid. The title compound was isolated in 57% yield as a yellow solid m/z (ESI, +ve)=280.1 $(M+H)^+$.

Step 2: Methyl 3-amino-6-chloro-4'-fluoro-2-iodo-[1,1'-biphenyl]-4-carboxylate

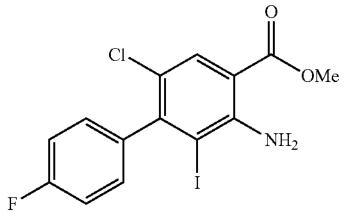 [SMILES: COC(=O)c1cc(Cl)c(-c2ccc(F)cc2)c(I)c1N]

The title compound was prepared analogously to Example 84, step 16 where Methyl 5-amino-2-chloro-4'-fluoro-[1,1'-biphenyl]-4-carboxylate was substituted in place of methyl 5-amino-2-chloro-2',4'-difluoro-[1,1'-biphenyl]-4-carboxylate. The title compound was isolated in 85% yield as a white solid m/z (ESI, +ve)=405.9 $(M+H)^+$.

Step 3: 3-Amino-6-chloro-4'-fluoro-2-iodo-[1,1'-biphenyl]-4-carboxylic acid

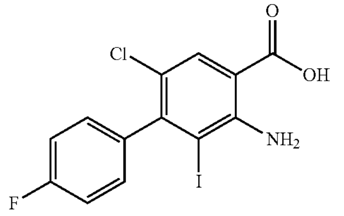 [SMILES: Nc1c(C(=O)O)cc(Cl)c(-c2ccc(F)cc2)c1I]

The title compound was prepared analogously to Example 84, step 17 where methyl 3-amino-6-chloro-4'-fluoro-2-iodo-[1,1'-biphenyl]-4-carboxylate was substituted in place of methyl 3-amino-6-chloro-2',4'-difluoro-2-iodo-[1,1'-biphenyl]-4-carboxylate. The title compound was isolated in 95% yield as a yellow solid m/z (ESI, +ve)=391.9 $(M+H)^+$.

Step 4: 6-Chloro-7-(4-fluorophenyl)-8-iodoquinazoline-2,4(1H,3H)-dione

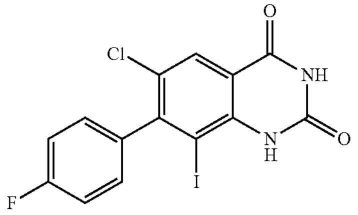

The title compound was prepared analogously to Example 84, step 18 where 3-amino-6-chloro-4'-fluoro-2-iodo-[1,1'-biphenyl]-4-carboxylic acid was substituted in place of 3-amino-6-chloro-2',4'-difluoro-2-iodo-[1,1'-biphenyl]-4-carboxylic acid. The title compound was isolated in 60% yield as a yellow solid m/z (ESI, +ve)=416.9 $(M+H)^+$.

$^1$H NMR (400 MHz, DMSO-d6) δ=11.76 (s, 1H), 9.47 (s, 1H), 8.00 (s, 1H), 7.45-7.31 (m, 2H), 7.29-7.16 (m, 2H).

Step 5: (R)-6-chloro-7-(4-fluorophenyl)-8-((3-hydroxy-2-methoxypropyl)thio)quinazoline-2,4(1H,3H)-dione

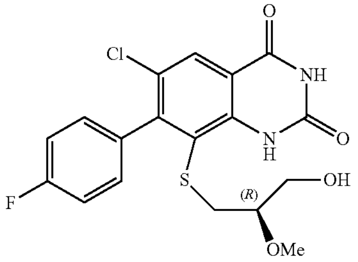

The title compound was prepared analogously to Example 100, step 9 where 6-Chloro-7-(4-fluorophenyl)-8-iodoquinazoline-2,4(1H,3H)-dione and (R)-3-mercapto-2-methoxypropan-1-ol were substituted in place of 7-(2,4-difluorophenyl)-8-iodo-6-(trifluoromethyl)quinazoline-2,4(1H,3H)-dione and 2-mercaptoethan-1-ol. The title compound was isolated in 60% yield as a white solid m/z (ESI, +ve)=411 $(M+H)^+$.

Step 6: (R)-10-chloro-11-(4-fluorophenyl)-3-methoxy-3,4-dihydro-2H,6H-[1,4]thiazepino[2,3,4-ij]quinazoline-6,8(7H)-dione

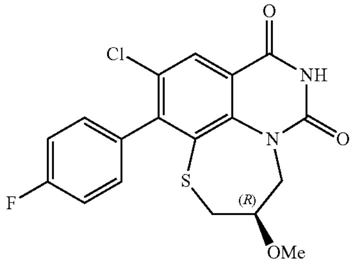

The title compound was prepared analogously to Example 100, step 10 where (R)-6-chloro-7-(4-fluorophenyl)-8-((3-hydroxy-2-methoxypropyl)thio)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 90% yield as a yellow solid m/z (ESI, +ve)=393.0 $(M+H)^+$.

Step 7: tert-butyl (S)-4-((R)-10-chloro-11-(4-fluorophenyl)-3-methoxy-6-oxo-3,4-dihydro-2H,6H-[1,4]thiazepino[2,3,4-ij]quinazolin-8-yl)-3-methylpiperazine-1-carboxylate

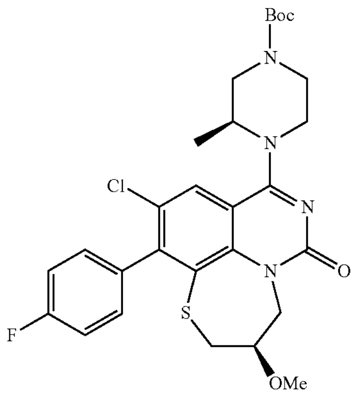 [SMILES: CO[C@H]1CSc2c(-c3ccc(F)cc3)c(Cl)cc3c(N4CCN(C(=O)OC(C)(C)C)C[C@@H]4C)nc(=O)n(c23)C1]

The title compound was prepared analogously to Example 100, step 21 where (R)-10-chloro-11-(4-fluorophenyl)-3-methoxy-3,4-dihydro-2H,6H-[1,4]thiazepino[2,3,4-ij]quinazoline-6,8(7H)-dione and tert-butyl (S)-3-methylpiperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 90% yield as a yellow solid m/z (ESI, +ve)=575.2 $(M+H)^+$.

Step 8: (R)-10-chloro-11-(4-fluorophenyl)-3-methoxy-8-((S)-2-methylpiperazin-1-yl)-3,4-dihydro-2H,6H-[1,4]thiazepino[2,3,4-ij]quinazolin-6-one

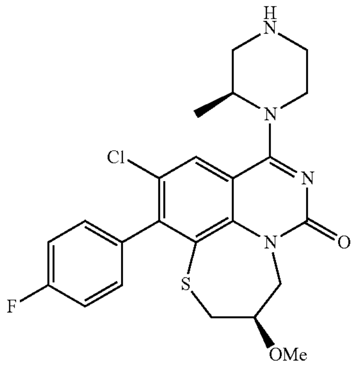 [SMILES: CO[C@H]1CSc2c(-c3ccc(F)cc3)c(Cl)cc3c(N4CCNC[C@@H]4C)nc(=O)n(c23)C1]

The title compound was prepared analogously to Example 102, step 4, where tert-butyl (S)-4-((R)-10-chloro-11-(4-fluorophenyl)-3-methoxy-6-oxo-3,4-dihydro-2H,6H-[1,4]thiazepino[2,3,4-ij]quinazolin-8-yl)-3-methylpiperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 67% yield as a yellow solid m/z (ESI, +ve)=475.1 $(M+H)^+$.

Example 529: (3S)-8-((S)-4-acryloyl-2-methylpiperazin-1-yl)-10-chloro-11-(5-chloro-2,4-difluorophenyl)-3-methoxy-3,4-dihydro-2H,6H-[1,4]thiazepino[2,3,4-ij]quinazolin-6-one

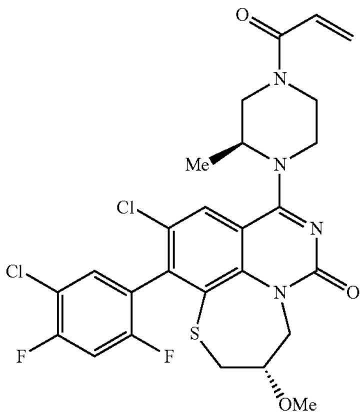 [SMILES: C=CC(=O)N1CCN(c2nc(=O)n3c4c(c(-c5cc(Cl)c(F)cc5F)c(Cl)cc24)SC[C@@H](OC)C3)[C@@H](C)C1]

The title compound was prepared analogously to Example 84 where (3S)-10-chloro-11-(5-chloro-2,4-difluorophenyl)-3-methoxy-8-((S)-2-methylpiperazin-1-yl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 14% yield as a yellow solid m/z (ESI, +ve)=580.0 $(M+H)^+$.

$^1$H NMR (400 MHz, DMSO-d6) δ7.84-7.77 (m, 2H), 7.68-7.64 (m, 1H), 6.93-6.74 (m, 1H), 6.20-6.16 (m, 1H), 5.76-5.72 (m, 1H), 4.62-4.40 (m, 3H), 4.30-4.02 (m, 2H), 4.02-3.82 (m, 2H), 3.65-3.40 (m, 2H), 3.38-3.33 (m, 4H), 3.24-2.91 (m, 2H), 1.31-1.24 (m, 3H).

Step 1: Methyl 2-amino-5-chloro-4-(4,4,5,5-tetramethyl-1,3,2-dioxaborolan-2-yl)benzoate

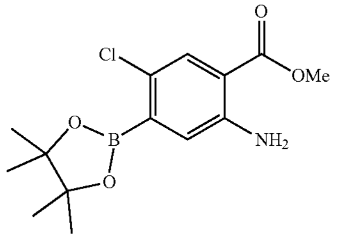 [SMILES: COC(=O)c1cc(Cl)c(B2OC(C)(C)C(C)(C)O2)cc1N]

To a mixture of methyl 2-amino-4-bromo-5-chlorobenzoate (40 g, 0.1512 mol) in dioxane (200 mL), bis(pinacolato)diboron (57.6 g, 0.2268 mol), Pd(dppf)$Cl_2$ (5.52 g, 0.0076 mol) and potassium acetate (44.12 g, 0.4536 mol) were added. The mixture was stirred at 100° C. for 16 hours and the solids removed by filtration. Evaporation of volatiles under reduced pressure afforded a residue that was purified by silica gel chromatography. The title compound was isolated in 74% yield as a yellow solid.

m/z (ESI, +ve)=312.1 $(M+H)^+$.

Step 2: Methyl 5-amino-2,5'-dichloro-2',4'-difluoro-[1,1'-biphenyl]-4-carboxylate

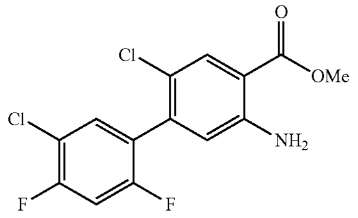 [SMILES: COC(=O)c1cc(Cl)c(-c2cc(Cl)c(F)cc2F)cc1N]

To a mixture of methyl 2-amino-5-chloro-4-(4,4,5,5-tetramethyl-1,3,2-dioxaborolan-2-yl)benzoate (25.5 g, 0.0818 mol) in 300 mL of dioxane/water (5:1 ratio) was added 1-bromo-5-chloro-2,4-difluorobenzene (15.5 g, 0.0682 mol), cesium carbonate (66.66 g, 0.2046 mol) and Pd(dppf)$Cl_2$ (2.5 g, 0.0034 mol). The resulting mixture was stirred at 100° C. for 1.5 hours and after that time the solids were removed by filtration. The reaction mixture was diluted with water and extracted with ethyl acetate three times. The combined organic layers were washed with brine, dried over sodium sulfate and concentrated under reduced pressure to afford a residue that was purified by silica gel chromatography. A second purification by chromatography on C18 column using acetonitrile in water (0-100%) as mobile phase afforded the title compound in 90% yield as a yellow oil.

m/z (ESI, +ve)=332.0 $(M+H)^+$.

Step 3: Methyl 3-amino-5',6-dichloro-2',4'-difluoro-2-iodo-[1,1'-biphenyl]-4-carboxylate

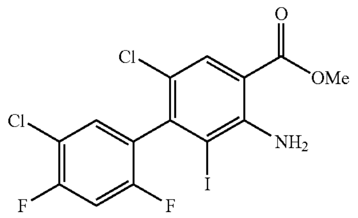 [SMILES: COC(=O)c1cc(Cl)c(-c2cc(Cl)c(F)cc2F)c(I)c1N]

The title compound was prepared analogously to Example 84, step 16 where methyl 5-amino-2,5'-dichloro-2',4'-difluoro-[1,1'-biphenyl]-4-carboxylate was substituted in place of methyl 5-amino-2-chloro-2',4'-difluoro-[1,1'-biphenyl]-4-carboxylate. The title compound was isolated in 80% yield as a white solid.

m/z (ESI, +ve)=457.9 $(M+H)^+$.

Step 4: 3-Amino-5',6-dichloro-2',4'-difluoro-2-iodo-[1,1'-biphenyl]-4-carboxylic acid

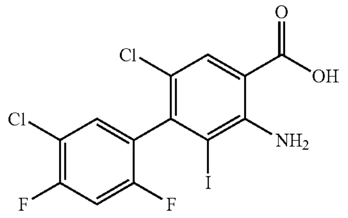 [SMILES: Nc1c(C(=O)O)cc(Cl)c(-c2cc(Cl)c(F)cc2F)c1I]

The title compound was prepared analogously to Example 84, step 17 where Methyl 3-amino-5',6-dichloro-2',4'-difluoro-2-iodo-[1,1'-biphenyl]-4-carboxylate was substituted in place of methyl 3-amino-6-chloro-2',4'-difluoro-2-iodo-[1,1'-biphenyl]-4-carboxylate. The title compound was isolated in 95% yield as a yellow solid m/z (ESI, +ve)=443.9 $(M+H)^+$.

Step 5: 6-chloro-7-(5-chloro-2,4-difluorophenyl)-8-iodoquinazoline-2,4(1H,3H)-dione

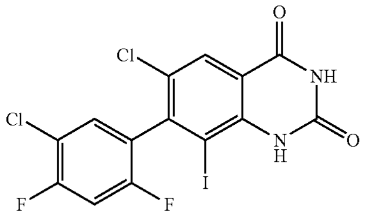 [SMILES: O=c1[nH]c(=O)c2cc(Cl)c(-c3cc(Cl)c(F)cc3F)c(I)c2[nH]1]

The title compound was prepared analogously to Example 84, step 18 where 3-Amino-5',6-dichloro-2',4'-difluoro-2-iodo-[1,1'-biphenyl]-4-carboxylic acid was substituted in place of 3-amino-6-chloro-2',4'-difluoro-2-iodo-[1,1'-biphenyl]-4-carboxylic acid. The title compound was isolated in 86% yield as a yellow solid m/z (ESI, +ve)=468.9 $(M+H)^+$.

$^1$H NMR (400 MHz, DMSO-d6) δ=11.79 (s, 1H), 11.17 (s, 1H), 8.05 (s, 1H), 7.8 (t, J=8.0 Hz, 1H), 7.72 (t, J=8.0 Hz, 1H).

Step 6: 6-chloro-7-(5-chloro-2,4-difluorophenyl)-8-(((S)-3-hydroxy-2-methoxypropyl)thio)quinazoline-2,4(1H,3H)-dione

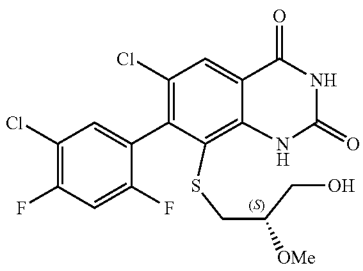

The title compound was prepared analogously to Example 100, step 9 where 6-chloro-7-(5-chloro-2,4-difluorophenyl)-8-iodoquinazoline-2,4(1H,3H)-dione and (S)-3-mercapto-2-methoxypropan-1-ol were substituted in place of 7-(2,4-difluorophenyl)-8-iodo-6-(trifluoromethyl)quinazoline-2,4(1H,3H)-dione and 2-mercaptoethan-1-ol in 61% yield as a yellow solid m/z (ESI, +ve)=463.0 $(M+H)^+$.

Step 7: (3S)-10-chloro-11-(5-chloro-2,4-difluorophenyl)-3-methoxy-3,4-dihydro-2H,6H-[1,4]thiazepino[2,3,4-ij]quinazoline-6,8(7H)-dione

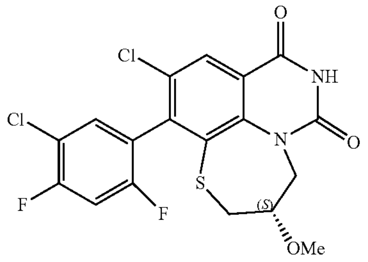

The title compound was prepared analogously to Example 100, step 10 where 6-chloro-7-(5-chloro-2,4-difluorophenyl)-8-(((S)-3-hydroxy-2-methoxypropyl)thio)quinazoline-2,4(1H,3H)-dione was substituted in place of 7-(2,4-difluorophenyl)-8-((2-hydroxyethyl)thio)-6-(trifluoromethyl) quinazoline-2,4(1H,3H)-dione in 60% yield as a yellow solid m/z (ESI, +ve)=445.0 $(M+H)^+$.

Step 8: tert-butyl (3S)-4-((3S)-10-chloro-11-(5-chloro-2,4-difluorophenyl)-3-methoxy-6-oxo-3,4-dihydro-2H,6H-[1,4]thiazepino[2,3,4-ij]quinazolin-8-yl)-3-methylpiperazine-1-carboxylate

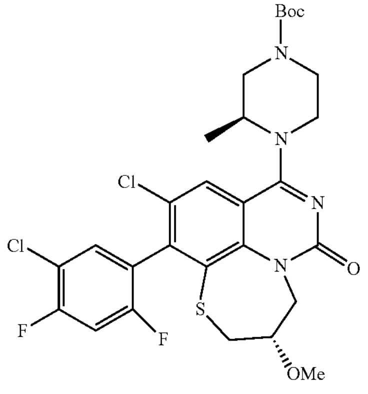 [SMILES: CO[C@@H]1CSc2c(-c3cc(Cl)c(F)cc3F)c(Cl)cc3c(N4CCN(C(=O)OC(C)(C)C)C[C@@H]4C)nc(=O)n(c23)C1]

The title compound was prepared analogously to Example 100, step 21 where (3S)-10-chloro-11-(5-chloro-2,4-difluorophenyl)-3-methoxy-3,4-dihydro-2H,6H-[1,4]thiazepino [2,3,4-ij]quinazoline-6,8(7H)-dione and tert-butyl (S)-3-methylpiperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 73% yield as a yellow solid m/z (ESI, +ve)=627.1 $(M+H)^+$.

Step 9: (3S)-10-chloro-11-(5-chloro-2,4-difluorophenyl)-3-methoxy-8-((S)-2-methylpiperazin-1-yl)-3,4-dihydro-2H,6H-[1,4]thiazepino[2,3,4-ij]quinazolin-6-one

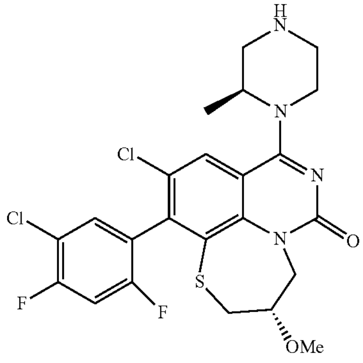 [SMILES: CO[C@@H]1CSc2c(-c3cc(Cl)c(F)cc3F)c(Cl)cc3c(N4CCNC[C@@H]4C)nc(=O)n(c23)C1]

The title compound was prepared analogously to Example 102, step 4, where tert-butyl (3S)-4-((3S)-10-chloro-11-(5-chloro-2,4-difluorophenyl)-3-methoxy-6-oxo-3,4-dihydro-2H,6H-[1,4]thiazepino[2,3,4-ij]quinazolin-8-yl)-3-methylpiperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 74% yield as a yellow solid m/z (ESI, +ve)=527.0 $(M+H)^+$.

Example 530: (3S)-8-((3S,5R)-4-acryloyl-3,5-dimethylpiperazin-1-yl)-10-chloro-11-(5-chloro-2,4-difluorophenyl)-3-methoxy-3,4-dihydro-2H,6H-[1,4]thiazepino[2,3,4-ij]quinazolin-6-one

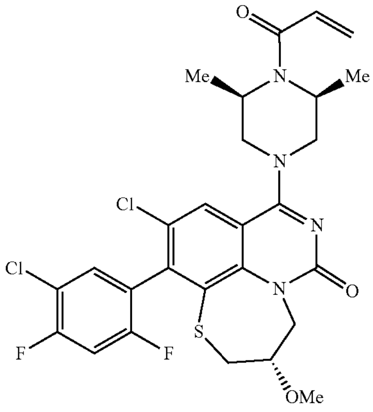 [SMILES: C=CC(=O)N1[C@H](C)CN(c2nc(=O)n3c4c(c(-c5cc(Cl)c(F)cc5F)c(Cl)cc24)SC[C@@H](OC)C3)C[C@@H]1C]

The title compound was prepared analogously to Example 84 where (3S)-10-chloro-11-(5-chloro-2,4-difluorophenyl)-8-((3S,5R)-3,5-dimethylpiperazin-1-yl)-3-methoxy-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 37% yield as a yellow solid m/z (ESI, +ve)=595.1 $(M+H)^+$.

$^1$H NMR (400 MHz, DMSO-d6) δ 7.93-7.67 (m, 3H), 6.80 (dd, J=16.0 Hz, 8.0 Hz, 1H), 6.19 (d, J=16.0 Hz, 1H), 5.74 (d, J=8.0 Hz, 1H), 4.56 (s, 2H), 4.48-4.44 (m, 2H), 4.09-4.00 (m, 2H), 3.88 (s, 1H), 3.54-3.37 (m, 1H), 3.35 (s, 3H), 3.28 (s, 2H), 3.18-3.16 (d, J=12.0 Hz, 1H), 1.50-1.24 (m, 6H).

Step 1: (3S)-10-chloro-11-(5-chloro-2,4-difluorophenyl)-8-((3S,5R)-3,5-dimethylpiperazin-1-yl)-3-methoxy-3,4-dihydro-2H,6H-[1,4]thiazepino[2,3,4-ij]quinazolin-6-one

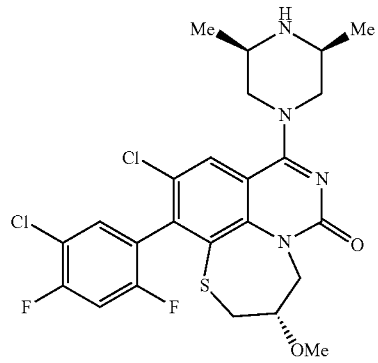 [SMILES: CO[C@@H]1CSc2c(-c3cc(Cl)c(F)cc3F)c(Cl)cc3c(N4C[C@@H](C)N[C@@H](C)C4)nc(=O)n(c23)C1]

The title compound was prepared analogously to Example 100, step 21 where (3S)-10-chloro-11-(5-chloro-2,4-difluorophenyl)-3-methoxy-3,4-dihydro-2H,6H-[1,4]thiazepino[2,3,4-ij]quinazoline-6,8(7H)-dione and (2S,6R)-2,6-dimethylpiperazine were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 61% yield as a yellow solid m/z (ESI, +ve)=541.0 $(M+H)^+$.

Example 532: (S)-8-((S)-4-acryloyl-2-methylpiperazin-1-yl)-11-(4-fluorophenyl)-3-methoxy-10-(trifluoromethyl)-3,4-dihydro-2H,6H-[1,4]thiazepino[2,3,4-ij]quinazolin-6-one

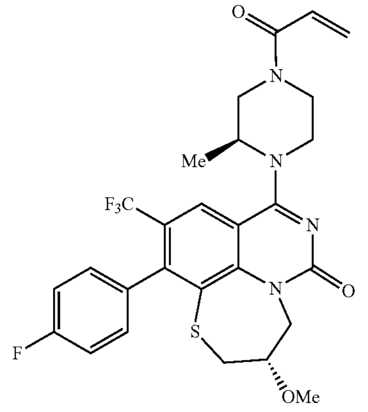 [SMILES: C=CC(=O)N1CCN(c2nc(=O)n3c4c(c(-c5ccc(F)cc5)c(C(F)(F)F)cc24)SC[C@@H](OC)C3)[C@@H](C)C1]

The title compound was prepared analogously to Example 84 where (S)-11-(4-fluorophenyl)-3-methoxy-8-((S)-2-methylpiperazin-1-yl)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 30% yield as a white solid m/z (ESI, +ve)=563.1 $(M+H)^+$.

$^1$H NMR (400 MHz, DMSO-d6) δ 7.78 (s, 1H), 7.34 (d, J=8.0 Hz, 4H), 6.92-6.76 (m, 1H), 6.18 (dd, J=16.0, 8.0 Hz, 1H), 5.74 (dd, J=12.0, 4.0 Hz, 1H), 4.70-4.39 (m, 3H), 4.28-4.24 (m, 1H), 4.16-3.97 (m, 2H), 3.83-3.79 (m, 1H), 3.56-3.51 (m, 2H), 3.34 (s, 3H), 3.13-2.98 (m, 3H), 1.33-1.29 (m, 3H).

Step 1: (S)-7-(4-fluorophenyl)-8-((3-hydroxy-2-methoxypropyl)thio)-6-(trifluoromethyl)quinazoline-2,4(1H,3H)-dione

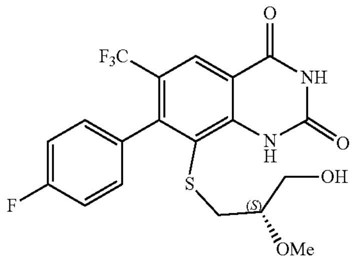

The title compound was prepared analogously to Example 100, step 9 where 7-(4-fluorophenyl)-8-iodo-6-(trifluoromethyl)quinazoline-2,4(1H,3H)-dione and (S)-3-mercapto-2-methoxypropan-1-ol were substituted in place of 7-(2,4-difluorophenyl)-8-iodo-6-(trifluoromethyl)quinazoline-2,4(1H,3H)-dione and 2-mercaptoethan-1-ol. The title compound was isolated in 50% yield as a yellow solid m/z (ESI, +ve)=445.0 (M+H)+.

Step 2: (S)-11-(4-fluorophenyl)-3-methoxy-10-(trifluoromethyl)-3,4-dihydro-2H,6H-[1,4]thiazepino[2,3,4-ij]quinazoline-6,8(7H)-dione

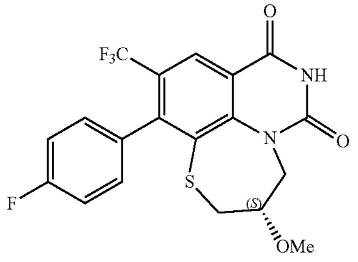

The title compound was prepared analogously to Example 100, step 10 where (S)-7-(4-fluorophenyl)-8-((3-hydroxy-2-methoxypropyl)thio)-6-(trifluoromethyl)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 66% yield as a yellow solid m/z (ESI, +ve)=427.1 (M+H)+.

Step 3: tert-butyl (S)-4-((S)-11-(4-fluorophenyl)-3-methoxy-6-oxo-10-(trifluoromethyl)-3,4-dihydro-2H,6H-[1,4]thiazepino[2,3,4-ij]quinazolin-8-yl)-3-methylpiperazine-1-carboxylate

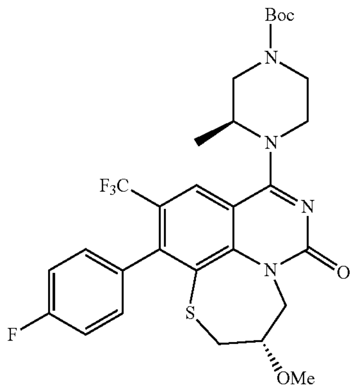 [SMILES: CO[C@@H]1CSc2c(-c3ccc(F)cc3)c(C(F)(F)F)cc3c(N4CCN(C(=O)OC(C)(C)C)C[C@@H]4C)nc(=O)n(c23)C1]

The title compound was prepared analogously to Example 100, step 21 where (S)-11-(4-fluorophenyl)-3-methoxy-10-(trifluoromethyl)-3,4-dihydro-2H,6H-[1,4]thiazepino[2,3,4-ij]quinazoline-6,8(7H)-dione and tert-butyl (S)-3-methylpiperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 59% yield as a yellow solid m/z (ESI, +ve)=609.2 $(M+H)^+$.

Step 4: (S)-11-(4-fluorophenyl)-3-methoxy-8-((S)-2-methylpiperazin-1-yl)-10-(trifluoromethyl)-3,4-dihydro-2H,6H-[1,4]thiazepino[2,3,4-ij]quinazolin-6-one

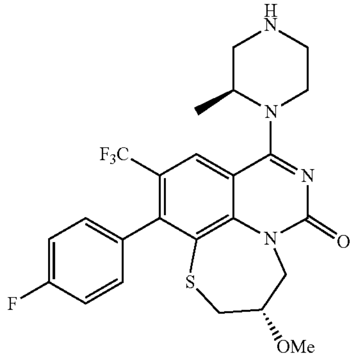 [SMILES: CO[C@@H]1CSc2c(-c3ccc(F)cc3)c(C(F)(F)F)cc3c(N4CCNC[C@@H]4C)nc(=O)n(c23)C1]

The title compound was prepared analogously to Example 102, step 4, where tert-butyl (S)-4-((S)-11-(4-fluorophenyl)-3-methoxy-6-oxo-10-(trifluoromethyl)-3,4-dihydro-2H,6H-[1,4]thiazepino[2,3,4-ij]quinazolin-8-yl)-3-methylpiperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 86% yield as a yellow solid m/z (ESI, +ve)=509.1 (M+H)+.

Example 533: (3R)-8-((S)-4-acryloyl-2-methylpiperazin-1-yl)-11-(5-chloro-2,4-difluorophenyl)-3-methoxy-10-(trifluoromethyl)-3,4-dihydro-2H,6H-[1,4]thiazepino[2,3,4-ij]quinazolin-6-one

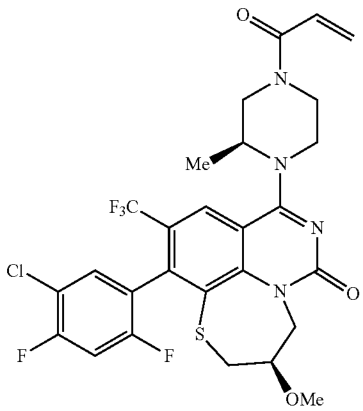 [SMILES: C=CC(=O)N1CCN(c2nc(=O)n3c4c(c(-c5cc(Cl)c(F)cc5F)c(C(F)(F)F)cc24)SC[C@H](OC)C3)[C@@H](C)C1]

The title compound was prepared analogously to Example 84 where (3R)-11-(5-chloro-2,4-difluorophenyl)-3-methoxy-8-((S)-2-methylpiperazin-1-yl)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 34% yield as a yellow solid m/z (ESI, +ve)=615.0 $(M+H)^+$.

$^1$H NMR (400 MHz, DMSO-d6) δ=7.83-7.66 (m, 3H), 6.91-6.74 (m, 1H), 6.19 (dd, J=16.0, 4.0 Hz, 1H), 5.74 (dd, J=16.0, 4.0 Hz, 1H), 4.80-4.31 (m, 4H), 4.17 (m, 3H), 3.85 (s, 1H), 3.54 (s, 2H), 3.37-3.32 (m, 3H), 3.22-3.18 (m, 2H), 1.33-1.28 (m, 3H).

Step 1: methyl 3-amino-5'-chloro-2',4'-difluoro-[1,1'-biphenyl]-4-carboxylate

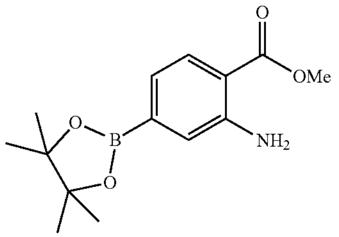 [SMILES: COC(=O)c1ccc(B2OC(C)(C)C(C)(C)O2)cc1N]

A mixture of methyl 2-amino-4-bromobenzoate (30 g, 0.130 mol), 4,4,4',4',5,5,5',5'-octamethyl-2,2'-bi(1,3,2-dioxaborolane) (50 g, 0.197 mol), $Pd(dppf)Cl_2$ (9.5 g, 13 mmol) and KOAc (38 g, 0.388 mol) in 1,4-dioxane (400 mL) was stirred at 100° C. for 16 hours. After that time, the mixture was filtered and the filtrate was concentrated under reduced pressure to afford a residue that was purified by silica gel column with ethyl acetate in hexanes (0-10%). The title compound was isolated in quantitative yield as a white solid.

m/z (ESI, +ve)=278.2 $(M+H)^+$.

$^1$H NMR (400 MHz, DMSO-d6) δ=7.68 (d, J=8.0 Hz, 1H), 7.18 (s, 1H), 6.79 (d, J=8.0 Hz, 1H), 6.63 (s, 2H), 3.79 (s, 3H), 1.29 (s, 12H).

Step 2: methyl 3-amino-5'-chloro-2',4'-difluoro-[1,1'-biphenyl]-4-carboxylate

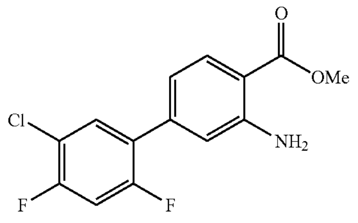 [SMILES: COC(=O)c1ccc(-c2cc(Cl)c(F)cc2F)cc1N]

A mixture of methyl 2-amino-4-(4,4,5,5-tetramethyl-1,3,2-dioxaborolan-2-yl)benzoate (36 g, 0.121 mol), 1-bromo-5-chloro-2,4-difluorobenzene (27 g, 0.119 mol), Pd(dppf) $Cl_2$ (17 g, 23.3 mmol) and $Cs_2CO_3$ (116 g, 0.356 mol) in 1,4-dioxane-water (300:60 mL) was stirred at 100° C. for 2 hours. The solution was cooled down to room temperature and filtered. The filtrate was concentrated under reduced pressure to afford a residue that was purified by silica gel chromatography with ethyl acetate in hexanes (0-8%). The title compound was isolated as a white solid in 83% yield.

m/z (ESI, +ve)=298.0 $(M+H)^+$.

$^1$H NMR (400 MHz, DMSO-d6) δ=7.79-7.74 (m, 2H), 7.70-7.65 (m, 1H), 6.96 (s, 1H), 6.77 (s, 2H), 6.71-6.68 (m, 1H), 3.81 (s, 3H).

Step 3: methyl 5-amino-5'-chloro-2',4'-difluoro-2-iodo-[1,1'-biphenyl]-4-carboxylate

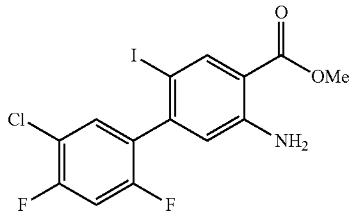 [SMILES: COC(=O)c1cc(I)c(-c2cc(Cl)c(F)cc2F)cc1N]

N-Iodosuccinamide (30 g, 0.133 mol) was added to a solution of methyl 3-amino-5'-chloro-2',4'-difluoro-[1,1'-biphenyl]-4-carboxylate (38 g, 0.128 mol) in DMF (200 mL) at room temperature. The mixture was stirred for 36 hours and after that time ethyl acetate (1 L) was added. The organic mixture was washed with sequentially washed with aqueous $Na_2S_2O_3$, water and brine. The organic layer was dried over sodium sulfate and filtered to afford a residue that was purified by silica gel chromatography (ethyl acetate in hexanes). The title compound was isolated in 87% yield as a yellow solid.

m/z (ESI, +ve)=423.9 $(M+H)^+$.

$^1$H NMR (400 MHz, DMSO-d6) δ=8.15 (s, 1H), 7.68-7.61 (m, 2H), 6.87 (s, 2H), 6.81 (s, 1H), 3.83 (s, 3H).

Step 4: methyl 5-acetamido-5'-chloro-2',4'-difluoro-2-iodo-[1,1'-biphenyl]-4-carboxylate

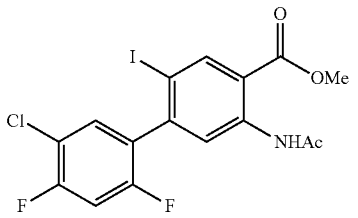 [SMILES: COC(=O)c1cc(I)c(-c2cc(Cl)c(F)cc2F)cc1NC(C)=O]

To a solution of methyl 5-amino-5'-chloro-2',4'-difluoro-2-iodo-[1,1'-biphenyl]-4-carboxylate (47 g, 0.111 mol) in AcOH (200 mL), acetic anhydride (14.5 g, 0.144 mol) was added and the resulting mixture was stirred at 100° C. for 2 hours. The reaction was cooled to room temperature and quenched by the addition of water (200 mL) inducing the precipitation of the desired final product. This solid was filtered and dried under reduced pressure to afford the title compound in 99% yield as an off-white solid.

m/z (ESI, +ve)=465.9 $(M+H)^+$.

$^1$H NMR (400 MHz, DMSO-d6) δ=10.52 (s, 1H), 8.36 (s, 1H), 8.18 (s, 1H), 7.75-7.66 (m, 2H), 3.83 (s, 3H), 2.12 (s, 3H).

Step 5: methyl 5-acetamido-5'-chloro-2',4'-difluoro-2-(trifluoromethyl)-[1,1'-biphenyl]-4-carboxylate

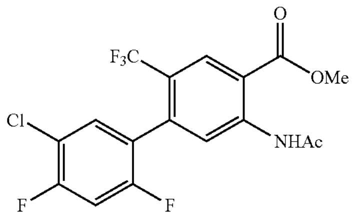 [SMILES: COC(=O)c1cc(C(F)(F)F)c(-c2cc(Cl)c(F)cc2F)cc1NC(C)=O]

To a solution of methyl 5-acetamido-5'-chloro-2',4'-difluoro-2-iodo-[1,1'-biphenyl]-4-carboxylate (10 g, 21.5 mmol), CuI (5.7 g, 30.0 mmol) and TBAI (4 g, 10.8 mmol) in HMPA (50 mL) at 90° C., was added methyl 2,2-difluoro-2-(fluorosulfonyl)acetate (41.2 g, 214.6 mmol). The mixture was stirred at 90° C. for 16 hours and after being cooled down to room temperature, water was added followed by filtration of the solids. The aqueous filtrate was extracted with ethyl acetate three times and the combined organic layers washed with water, brine and dried over sodium sulfate. Filtration and evaporation of volatiles under reduced pressure afforded a residue that was purified by silica gel chromatography (0-15% ethyl acetate in hexanes). The tile compound was isolated in 82% yield as a yellow solid.

m/z (ESI, +ve)=408.0 $(M+H)^+$.

$^1$H NMR (400 MHz, DMSO-d6) δ=10.81 (s, 1H), 8.34 (s, 1H), 8.26 (s, 1H), 7.78-7.61 (m, 2H), 3.93 (s, 3H), 2.18 (s, 3H).

Step 6: methyl 5-amino-5'-chloro-2',4'-difluoro-2-(trifluoromethyl)-[1,1'-biphenyl]-4-carboxylate

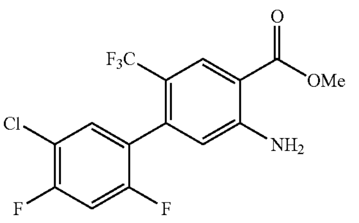 [SMILES: COC(=O)c1cc(C(F)(F)F)c(-c2cc(Cl)c(F)cc2F)cc1N]

The title compound was synthesized analogously to example 100, step 5 where methyl 5-acetamido-5'-chloro-2',4'-difluoro-2-(trifluoromethyl)-[1,1'-biphenyl]-4-carboxylate was substituted in place of methyl 5-acetamido-2',4'-difluoro-2-(trifluoromethyl)-[1,1'-biphenyl]-4-carboxylate. The title compound was isolated in 92% yield as a white solid m/z (ESI, +ve)=366.0 $(M+H)^+$.

Step 7: methyl 3-amino-5'-chloro-2',4'-difluoro-2-iodo-6-(trifluoromethyl)-[1,1'-biphenyl]-4-carboxylate

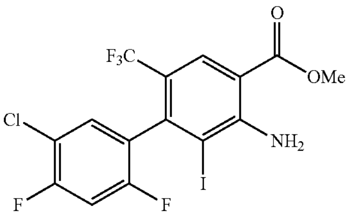 [SMILES: COC(=O)c1cc(C(F)(F)F)c(-c2cc(Cl)c(F)cc2F)c(I)c1N]

The title compound was synthesized analogously to example 100, step 6 where methyl 5-amino-5'-chloro-2',4'-difluoro-2-(trifluoromethyl)-[1,1'-biphenyl]-4-carboxylate was substituted in place of methyl 5-amino-2',4'-difluoro-2-(trifluoromethyl)-[1,1'-biphenyl]-4-carboxylate. The title compound was isolated in 86% yield as a white solid m/z (ESI, +ve)=491.9 $(M+H)^+$.

$^1$H NMR (400 MHz, DMSO-d6) δ=8.19 (s, 1H), 7.76-7.73 (m, 1H), 7.67-7.63 (m, 1H), 7.48-7.44 (m, 2H), 3.90 (s, 3H).

Step 8: 3-amino-5'-chloro-2',4'-difluoro-2-iodo-6-(trifluoromethyl)-[1,1'-biphenyl]-4-carboxylic acid

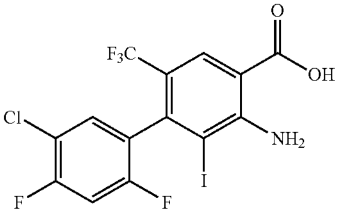 [SMILES: Nc1c(C(=O)O)cc(C(F)(F)F)c(-c2cc(Cl)c(F)cc2F)c1I]

The title compound was synthesized analogously to example 100, step 7 where methyl 3-amino-5'-chloro-2',4'-difluoro-2-iodo-6-(trifluoromethyl)-[1,1'-biphenyl]-4-carboxylate was substituted in place of methyl 3-amino-2',4'-difluoro-2-iodo-6-(trifluoromethyl)-[1,1'-biphenyl]-4-carboxylate. The title compound was isolated in 99% yield as a white solid m/z (ESI, +ve)=477.8 $(M+H)^+$.

$^1$H NMR (400 MHz, DMSO-d6) δ=13.60 (s, 1H), 8.19 (s, 1H), 7.77-7.72 (m, 1H), 7.67-7.63 (m, 1H), 7.57-7.48 (m, 2H).

Step 9: 7-(5-chloro-2,4-difluorophenyl)-8-iodo-6-(trifluoromethyl)quinazoline-2,4(1H,3H)-dione

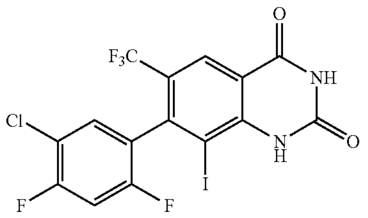 [SMILES: O=c1[nH]c(=O)c2cc(C(F)(F)F)c(-c3cc(Cl)c(F)cc3F)c(I)c2[nH]1]

The title compound was synthesized analogously to example 100, step 8 where 3-Amino-4'-fluoro-2-iodo-6-(trifluoromethyl)-[1,1'-biphenyl]-4-carboxylic acid was substituted in place of 3-amino-2',4'-difluoro-2-iodo-6-(trifluoromethyl)-[1,1'-biphenyl]-4-carboxylic acid. The title compound was isolated in 57% yield as a white solid.

m/z (ESI, +ve)=502.9 $(M+H)^+$.

$^1$H NMR (400 MHz, DMSO-d6) δ=11.93 (s, 1H), 9.99 (s, 1H), 8.27 (s, 1H), 7.83-7.78 (m, 1H), 7.72-7.68 (m, 1H).

Step 11: 7-(5-chloro-2,4-difluorophenyl)-8-(((R)-3-hydroxy-2-methoxypropyl)thio)-6-(trifluoromethyl)quinazoline-2,4(1H,3H)-dione

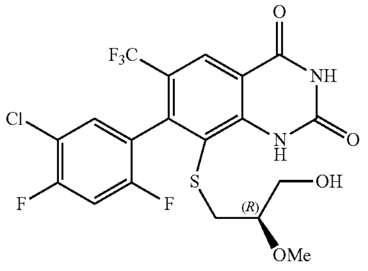

The title compound was synthesized analogously to example 100, step 9 where 7-(5-chloro-2,4-difluorophenyl)-8-iodo-6-(trifluoromethyl)quinazoline-2,4(1H,3H)-dione and (R)-3-mercapto-2-methoxypropan-1-ol was substituted in place of 7-(2,4-difluorophenyl)-8-iodo-6-(trifluoromethyl)quinazoline-2,4(1H,3H)-dione and 2-mercaptoethan-1-ol. The title compound was isolated in 70% yield as a white solid.

m/z (ESI, +ve)=497.0 $(M+H)^+$.

Step 12: (3R)-11-(5-chloro-2,4-difluorophenyl)-3-methoxy-10-(trifluoromethyl)-3,4-dihydro-2H,6H-[1,4]thiazepino[2,3,4-ij]quinazoline-6,8(7H)-dione

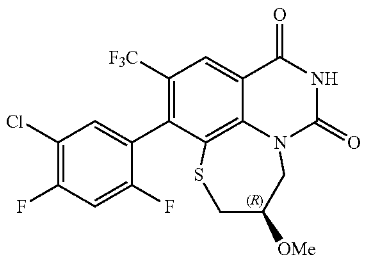

The title compound was prepared analogously to Example 100, step 10 where 7-(5-chloro-2,4-difluorophenyl)-8-(((R)-3-hydroxy-2-methoxypropyl)thio)-6-(trifluoromethyl)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 55% yield as a yellow solid Step 13: tert-butyl (3S)-4-((3R)-11-(5-chloro-2,4-difluorophenyl)-3-methoxy-6-oxo-10-(trifluoromethyl)-3,4-dihydro-2H,6H-[1,4]thiazepino[2,3,4-ij]quinazolin-8-yl)-3-methylpiperazine-1-carboxylate

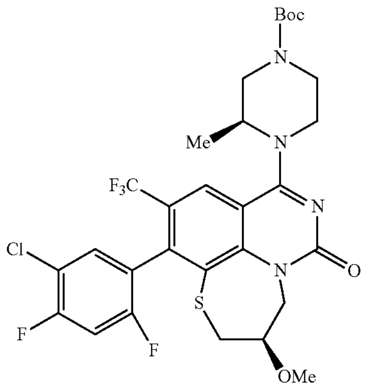 [SMILES: CO[C@H]1CSc2c(-c3cc(Cl)c(F)cc3F)c(C(F)(F)F)cc3c(N4CCN(C(=O)OC(C)(C)C)C[C@@H]4C)nc(=O)n(c23)C1]

The title compound was prepared analogously to Example 100, step 21 where (3R)-11-(5-chloro-2,4-difluorophenyl)-3-methoxy-10-(trifluoromethyl)-3,4-dihydro-2H,6H-[1,4]thiazepino[2,3,4-ij]quinazoline-6,8(7H)-dione and tert-butyl (S)-3-methylpiperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 61% yield as a yellow solid m/z (ESI, +ve)=661.0 $(M+H)^+$.

Step 14: (3R)-11-(5-chloro-2,4-difluorophenyl)-3-methoxy-8-((S)-2-methylpiperazin-1-yl)-10-(trifluoromethyl)-3,4-dihydro-2H,6H-[1,4]thiazepino[2,3,4-ij]quinazolin-6-one

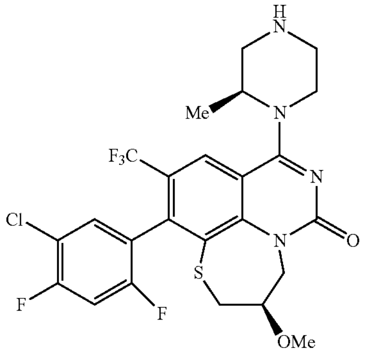 [SMILES: CO[C@H]1CSc2c(-c3cc(Cl)c(F)cc3F)c(C(F)(F)F)cc3c(N4CCNC[C@@H]4C)nc(=O)n(c23)C1]

The title compound was prepared analogously to Example 102, step 4, where tert-butyl (3S)-4-((3R)-11-(5-chloro-2,4-difluorophenyl)-3-methoxy-6-oxo-10-(trifluoromethyl)-3,4-dihydro-2H,6H-[1,4]thiazepino[2,3,4-ij]quinazolin-8-yl)-3-methylpiperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated as a yellow oil m/z (ESI, +ve)=561.0 $(M+H)^+$.

Example 534: (3R)-8-(4-acryloylpiperazin-1-yl)-11-(5-chloro-2,4-difluorophenyl)-3-methoxy-10-(trifluoromethyl)-3,4-dihydro-2H,6H-[1,4]thiazepino[2,3,4-ij]quinazolin-6-one

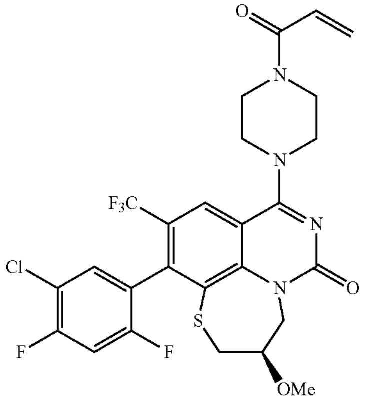 [SMILES: C=CC(=O)N1CCN(c2nc(=O)n3c4c(c(-c5cc(Cl)c(F)cc5F)c(C(F)(F)F)cc24)SC[C@H](OC)C3)CC1]

The title compound was prepared analogously to Example 84 where (3R)-11-(5-chloro-2,4-difluorophenyl)-3-methoxy-8-(piperazin-1-yl)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 27% yield as a yellow solid m/z (ESI, +ve)=601.0 $(M+H)^+$.

$^1H$ NMR (400 MHz, DMSO-d6) δ=7.90 (s, 1H), 7.80-7.76 (m, 2H), 6.82 (dd, J=16.0, 8.0 Hz, 1H), 6.17 (dd,

J=16.0, 4.0 Hz, 1H), 5.74 (dd, J=16.0, 4.0 Hz, 1H), 4.51-4.47 (m, 1H), 3.84-3.80 (m, 9H), 3.47-3.43 (m, 1H), 3.40-3.35 (m, 3H), 3.22-3.18 (m, 2H).

Step 1: tert-butyl 4-((3R)-11-(5-chloro-2,4-difluorophenyl)-3-methoxy-6-oxo-10-(trifluoromethyl)-3,4-dihydro-2H,6H-[1,4]thiazepino[2,3,4-ij]quinazolin-8-yl)piperazine-1-carboxylate

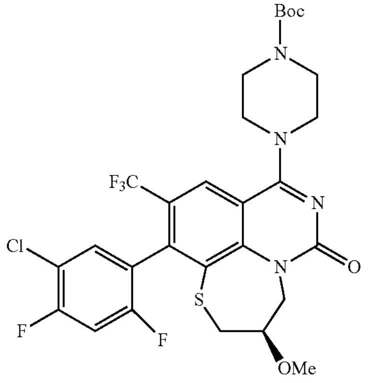 [SMILES: CO[C@H]1CSc2c(-c3cc(Cl)c(F)cc3F)c(C(F)(F)F)cc3c(N4CCN(C(=O)OC(C)(C)C)CC4)nc(=O)n(c23)C1]

The title compound was prepared analogously to Example 100, step 21 (3R)-11-(5-chloro-2,4-difluorophenyl)-3-methoxy-10-(trifluoromethyl)-3,4-dihydro-2H,6H-[1,4]thiazepino[2,3,4-ij]quinazoline-6,8(7H)-dione and tert-butyl piperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 68% yield as a yellow solid m/z (ESI, +ve)=647.1 $(M+H)^+$.

Step 2: (3R)-11-(5-chloro-2,4-difluorophenyl)-3-methoxy-8-(piperazin-1-yl)-10-(trifluoromethyl)-3,4-dihydro-2H,6H-[1,4]thiazepino[2,3,4-ij]quinazolin-6-one

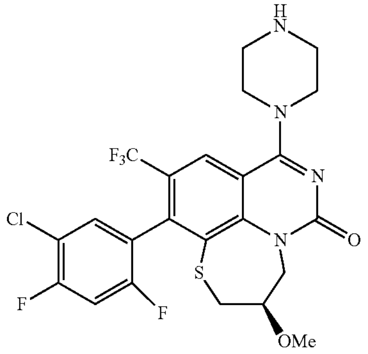 [SMILES: CO[C@H]1CSc2c(-c3cc(Cl)c(F)cc3F)c(C(F)(F)F)cc3c(N4CCNCC4)nc(=O)n(c23)C1]

The title compound was prepared analogously to Example 102, step 4, where tert-butyl 4-((3R)-11-(5-chloro-2,4-difluorophenyl)-3-methoxy-6-oxo-10-(trifluoromethyl)-3,4-dihydro-2H,6H-[1,4]thiazepino[2,3,4-ij]quinazolin-8-yl)piperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 70% yield as a yellow solid m/z (ESI, +ve)=547.0 $(M+H)^+$.

Example 535: (3R)-8-((3S,5R)-4-acryloyl-3,5-dimethylpiperazin-1-yl)-11-(5-chloro-2,4-difluorophenyl)-3-methoxy-10-(trifluoromethyl)-3,4-dihydro-2H,6H-[1,4]thiazepino[2,3,4-ij]quinazolin-6-one

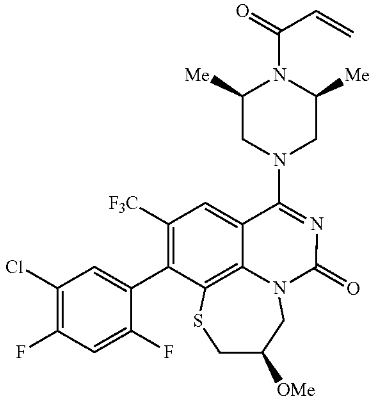 [SMILES: C=CC(=O)N1[C@H](C)CN(c2nc(=O)n3c4c(c(-c5cc(Cl)c(F)cc5F)c(C(F)(F)F)cc24)SC[C@H](OC)C3)C[C@@H]1C]

The title compound was prepared analogously to Example 84 where (3R)-11-(5-chloro-2,4-difluorophenyl)-8-((3S,5R)-3,5-dimethylpiperazin-1-yl)-3-methoxy-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 32% yield as a yellow solid m/z (ESI, +ve)=629.0 $(M+H)^+$.

$^1$H NMR (400 MHz, DMSO-d6) δ=8.04 (s, 1H), 7.87-7.69 (m, 2H), 6.81 (dd, J=16.0, 8.0 Hz, 1H), 6.19 (dd, J=16.0, 4.0 Hz, 1H), 5.74 (dd, J=16.0, 4.0 Hz, 1H), 4.67-4.46 (m, 3H), 4.08-4.04 (m, 2H), 3.88-3.84 (m, 1H), 3.49-3.44 (m, 1H), 3.35 (s, 3H), 3.32-3.21 (m, 3H), 3.17 (s, 1H), 1.53-1.27 (m, 6H).

Step 1: (3R)-11-(5-chloro-2,4-difluorophenyl)-8-((3S,5R)-3,5-dimethylpiperazin-1-yl)-3-methoxy-10-(trifluoromethyl)-3,4-dihydro-2H,6H-[1,4]thiazepino[2,3,4-ij]quinazolin-6-one

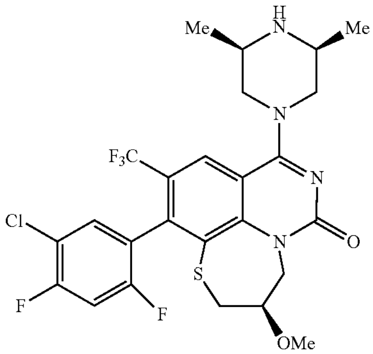 [SMILES: CO[C@H]1CSc2c(-c3cc(Cl)c(F)cc3F)c(C(F)(F)F)cc3c(N4C[C@@H](C)N[C@@H](C)C4)nc(=O)n(c23)C1]

The title compound was prepared analogously to Example 100, step 21 where (3R)-11-(5-chloro-2,4-difluorophenyl)-3-methoxy-10-(trifluoromethyl)-3,4-dihydro-2H,6H-[1,4]thiazepino[2,3,4-ij]quinazoline-6,8(7H)-dione and (2R,6S)-2,6-dimethylpiperazine were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 63% yield as a yellow solid m/z (ESI, +ve)=575.0 $(M+H)^+$.

Example 536: (S)-8-(4-acryloylpiperazin-1-yl)-10-chloro-11-(4-fluorophenyl)-3-methoxy-3,4-dihydro-2H,6H-[1,4]thiazepino[2,3,4-ij]quinazolin-6-one

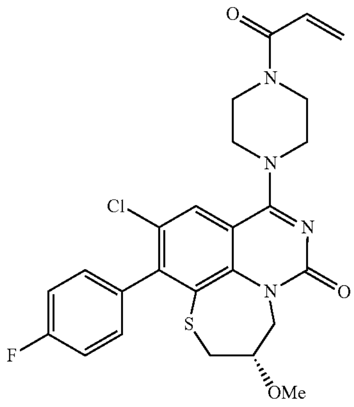 [SMILES: C=CC(=O)N1CCN(c2nc(=O)n3c4c(c(-c5ccc(F)cc5)c(Cl)cc24)SC[C@@H](OC)C3)CC1]

The title compound was prepared analogously to Example 84 where (S)-10-chloro-11-(4-fluorophenyl)-3-methoxy-8-(piperazin-1-yl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 27% yield as a yellow solid m/z (ESI, +ve)=515.0 $(M+H)^+$.

$^1$H NMR (400 MHz, DMSO-d6) δ 7.72 (s, 1H), 7.41-7.30 (m, 4H), 6.83 (dd, J=16.0, 8.0 Hz, 1H), 6.17 (dd, J=16.0, 4.0 Hz, 1H), 5.74 (dd, J=16.0, 4.0 Hz, 1H), 4.49-4.44 (m, 1H), 3.80-3.76 (m, 10H), 3.35-3.31 (m, 3H), 3.32-3.28 (m, 1H), 3.10-3.06 (m, 1H).

Step 1: (S)-6-chloro-7-(4-fluorophenyl)-8-((3-hydroxy-2-methoxypropyl)thio)quinazoline-2,4(1H,3H)-dione

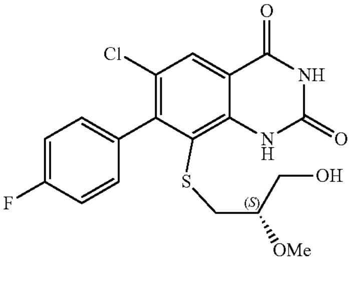

The title compound was prepared analogously to Example 100, step 9 where 6-Chloro-7-(4-fluorophenyl)-8-iodoquinazoline-2,4(1H,3H)-dione and (S)-3-mercapto-2-methoxypropan-1-ol were substituted in place of 7-(2,4-difluorophenyl)-8-iodo-6-(trifluoromethyl)quinazoline-2,4(1H,3H)-dione and 2-mercaptoethan-1-ol. The title compound was isolated in 76% yield as a yellow solid m/z (ESI, +ve)=411.0 (M+H)+.

Step 2: (S)-10-chloro-11-(4-fluorophenyl)-3-methoxy-3,4-dihydro-2H,6H-[1,4]thiazepino[2,3,4-ij]quinazoline-6,8(7H)-dione

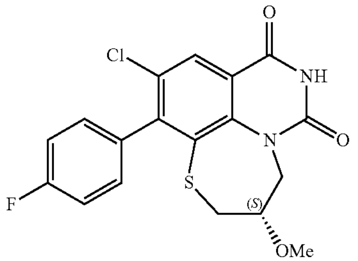

The title compound was prepared analogously to Example 100, step 10 where (S)-6-chloro-7-(4-fluorophenyl)-8-((3-hydroxy-2-methoxypropyl)thio)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 61% yield as a yellow solid m/z (ESI, +ve)=393.0 $(M+H)^+$.

Step 3: tert-butyl (S)-4-(10-chloro-11-(4-fluorophenyl)-3-methoxy-6-oxo-3,4-dihydro-2H,6H-[1,4]thiazepino[2,3,4-ij]quinazolin-8-yl)piperazine-1-carboxylate

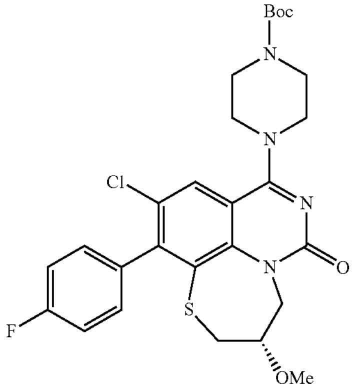 [SMILES: CO[C@@H]1CSc2c(-c3ccc(F)cc3)c(Cl)cc3c(N4CCN(C(=O)OC(C)(C)C)CC4)nc(=O)n(c23)C1]

The title compound was prepared analogously to Example 100, step 21 where (S)-10-chloro-11-(4-fluorophenyl)-3-methoxy-3,4-dihydro-2H,6H-[1,4]thiazepino[2,3,4-ij]quinazoline-6,8(7H)-dione and tert-butyl piperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 66% yield as a yellow solid m/z (ESI, +ve)=561.2 $(M+H)^+$.

Step 4: (S)-10-chloro-11-(4-fluorophenyl)-3-methoxy-8-(piperazin-1-yl)-3,4-dihydro-2H,6H-[1,4]thiazepino[2,3,4-ij]quinazolin-6-one

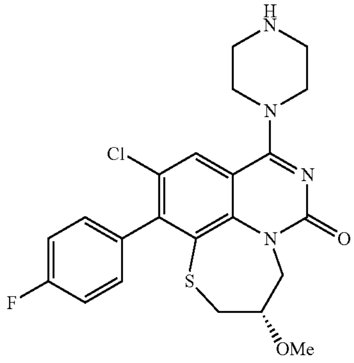 [SMILES: CO[C@@H]1CSc2c(-c3ccc(F)cc3)c(Cl)cc3c(N4CCNCC4)nc(=O)n(c23)C1]

The title compound was prepared analogously to Example 102, step 4, where tert-butyl (S)-4-(10-chloro-11-(4-fluorophenyl)-3-methoxy-6-oxo-3,4-dihydro-2H,6H-[1,4]thiazepino[2,3,4-ij]quinazolin-8-yl)piperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 79% yield as a yellow solid m/z (ESI, +ve)=461.0 (M+H)+.

Example 537: (S)-8-((S)-4-acryloyl-2-methylpiperazin-1-yl)-10-chloro-11-(4-fluorophenyl)-3-methoxy-3,4-dihydro-2H,6H-[1,4]thiazepino[2,3,4-ij]quinazolin-6-one

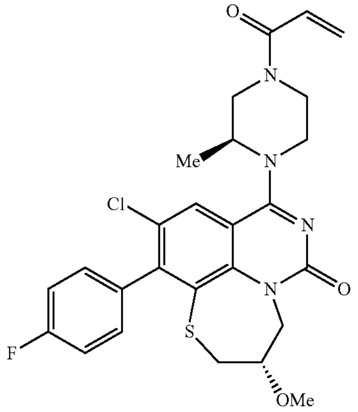 [SMILES: C=CC(=O)N1CCN(c2nc(=O)n3c4c(c(-c5ccc(F)cc5)c(Cl)cc24)SC[C@@H](OC)C3)[C@@H](C)C1]

The title compound was prepared analogously to Example 84 where (S)-10-chloro-11-(4-fluorophenyl)-3-methoxy-8-((S)-2-methylpiperazin-1-yl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 31% yield as a yellow solid m/z (ESI, +ve)=529.1 $(M+H)^+$.

$^1H$ NMR (400 MHz, DMSO-d6) δ 7.62 (s, 1H), 7.36 (d, J=8.0 Hz, 4H), 6.92-6.76 (m, 1H), 6.18 (dd, J=16.0, 4.0 Hz, 1H), 5.74 (dd, J=16.0, 4.0 Hz, 1H), 4.59-4.55 (m, 1H), 4.46-4.42 (m, 2H), 4.33-3.90 (m, 3H), 3.88-3.78 (m, 1H), 3.57-3.53 (m, 2H), 3.33 (s, 3H), 3.25-2.84 (m, 3H), 1.29-1.25 (m, 3H).

Step 1: tert-butyl (S)-4-((S)-10-chloro-11-(4-fluorophenyl)-3-methoxy-6-oxo-3,4-dihydro-2H,6H-[1,4]thiazepino[2,3,4-ij]quinazolin-8-yl)-3-methylpiperazine-1-carboxylate

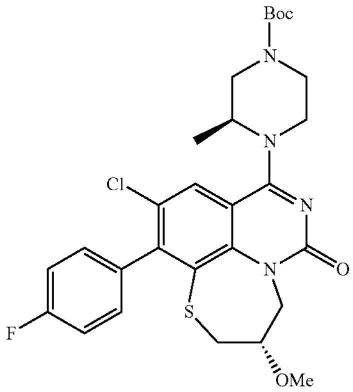 [SMILES: CO[C@@H]1CSc2c(-c3ccc(F)cc3)c(Cl)cc3c(N4CCN(C(=O)OC(C)(C)C)C[C@@H]4C)nc(=O)n(c23)C1]

The title compound was prepared analogously to Example 100, step 21 where (S)-10-chloro-11-(4-fluorophenyl)-3-methoxy-3,4-dihydro-2H,6H-[1,4]thiazepino[2,3,4-ij]quinazoline-6,8(7H)-dione and tert-butyl (S)-3-methylpiperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 68% yield as a yellow solid m/z (ESI, +ve)=575.1 $(M+H)^+$.

Step 2: (S)-10-chloro-11-(4-fluorophenyl)-3-methoxy-8-((S)-2-methylpiperazin-1-yl)-3,4-dihydro-2H,6H-[1,4]thiazepino[2,3,4-ij]quinazolin-6-one

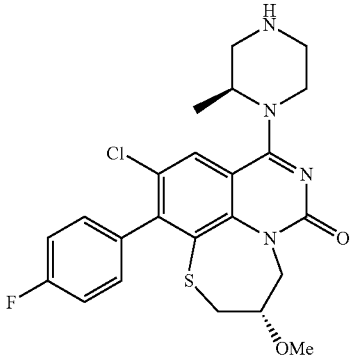 [SMILES: CO[C@@H]1CSc2c(-c3ccc(F)cc3)c(Cl)cc3c(N4CCNC[C@@H]4C)nc(=O)n(c23)C1]

The title compound was prepared analogously to Example 102, step 4, where tert-butyl (S)-4-((S)-10-chloro-11-(4-fluorophenyl)-3-methoxy-6-oxo-3,4-dihydro-2H,6H-[1,4]thiazepino[2,3,4-ij]quinazolin-8-yl)-3-methylpiperazine-1-carboxylate was substituted in place of tert-butyl (3S)-4-(10-chloro-11-(2,4-difluorophenyl)-6-oxo-3,4-dihydro-2H, 6H-[1,4]thiazepino[2,3,4-ij]quinazolin-8-yl)-3-methylpiperazine-1-carboxylate. The title compound was isolated in 76% yield as a yellow solid m/z (ESI, +ve)=475.1 (M+H)+.

Example 538: (3R)-8-(4-acryloylpiperazin-1-yl)-10-chloro-11-(5-chloro-2,4-difluorophenyl)-3-methoxy-3,4-dihydro-2H,6H-[1,4]thiazepino[2,3,4-ij]quinazolin-6-one

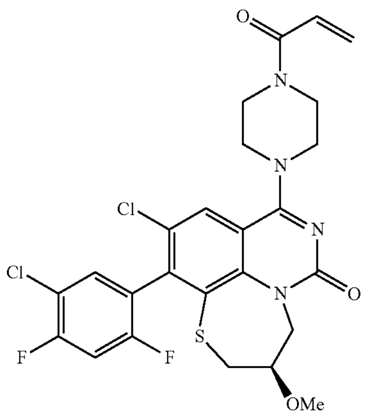 [SMILES: C=CC(=O)N1CCN(c2nc(=O)n3c4c(c(-c5cc(Cl)c(F)cc5F)c(Cl)cc24)SC[C@H](OC)C3)CC1]

The title compound was prepared analogously to Example 84 where (3R)-10-chloro-11-(5-chloro-2,4-difluorophenyl)-3-methoxy-8-(piperazin-1-yl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 36% yield as a yellow solid m/z (ESI, +ve)=567.0 $(M+H)^+$.

$^1$H NMR (400 MHz, DMSO-d6) δ 7.90-7.76 (m, 3H), 6.82 (dd, J=16.0, 8.0 Hz, 1H), 6.17 (dd, J=16.0, 4.0 Hz, 1H), 5.74 (dd, J=16.0, 4.0 Hz, 1H), 4.52-4.36 (m, 1H), 3.91-3.61 (m, 8H), 3.53-3.45 (m, 3H), 3.35-3.30 (m, 3H), 3.20-3.09 (m, 1H).

Step 1: 6-chloro-7-(5-chloro-2,4-difluorophenyl)-8-(((R)-3-hydroxy-2-methoxypropyl)thio)quinazoline-2,4(1H,3H)-dione

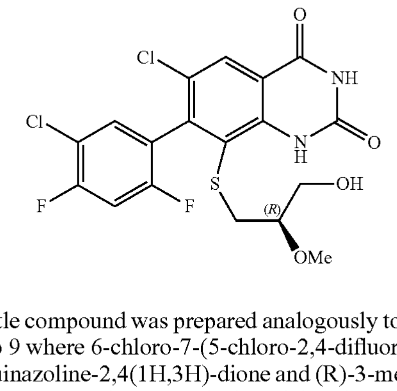

The title compound was prepared analogously to Example 100, step 9 where 6-chloro-7-(5-chloro-2,4-difluorophenyl)-8-iodoquinazoline-2,4(1H,3H)-dione and (R)-3-mercapto-2-methoxypropan-1-ol were substituted in place of 7-(2,4-difluorophenyl)-8-iodo-6-(trifluoromethyl)quinazoline-2,4(1H,3H)-dione and 2-mercaptoethan-1-ol in 50% yield as a yellow solid m/z (ESI, +ve)=463.0 $(M+H)^+$.

Step 2: (3R)-10-chloro-11-(5-chloro-2,4-difluorophenyl)-3-methoxy-3,4-dihydro-2H,6H-[1,4]thiazepino[2,3,4-ij]quinazoline-6,8(7H)-dione

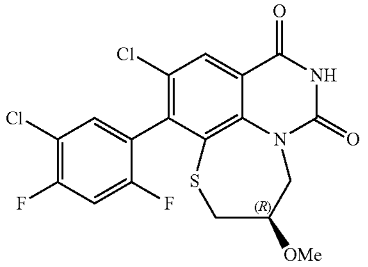

The title compound was prepared analogously to Example 100, step 10 where 6-chloro-7-(5-chloro-2,4-difluorophenyl)-8-(((R)-3-hydroxy-2-methoxypropyl)thio)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 65% yield as a yellow solid m/z (ESI, +ve)=445.0 $(M+H)^+$.

Step 3: tert-butyl 4-((3R)-10-chloro-11-(5-chloro-2,4-difluorophenyl)-3-methoxy-6-oxo-3,4-dihydro-2H,6H-[1,4]thiazepino[2,3,4-ij]quinazolin-8-yl)piperazine-1-carboxylate

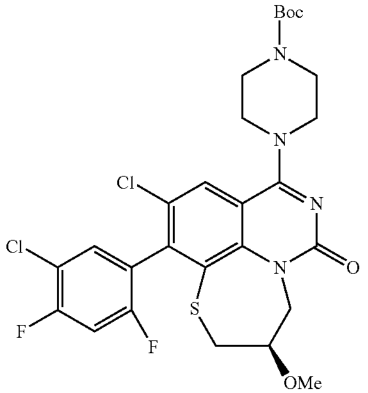 [SMILES: CO[C@H]1CCSc2c(-c3cc(Cl)c(F)cc3F)c(Cl)cc3c(N4CCN(C(=O)OC(C)(C)C)CC4)nc(=O)n(c23)C1]

The title compound was prepared analogously to Example 100, step 21 where (3R)-10-chloro-11-(5-chloro-2,4-difluorophenyl)-3-methoxy-3,4-dihydro-2H,6H-[1,4]thiazepino[2,3,4-ij]quinazoline-6,8(7H)-dione and tert-butyl piperazine-1-carboxylate were substituted in place of 10-(2,4-difluorophenyl)-9-(trifluoromethyl)-2,3-dihydro-5H-thiazino[2,3,4-ij]quinazoline-5,7(6H)-dione and octahydrothieno[3,4-b]pyrazine 6,6-dioxide. The title compound was isolated in 78% yield as a yellow solid m/z (ESI, +ve)=613.2 $(M+H)^+$.

Step 4: (3R)-10-chloro-11-(5-chloro-2,4-difluorophenyl)-3-methoxy-8-(piperazin-1-yl)-3,4-dihydro-2H,6H-[1,4]thiazepino[2,3,4-ij]quinazolin-6-one

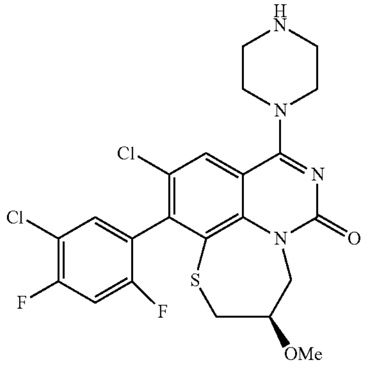 [SMILES: CO[C@H]1CCSc2c(-c3cc(Cl)c(F)cc3F)c(Cl)cc3c(N4CCNCC4)nc(=O)n(c23)C1]

The title compound was prepared analogously to Example 102, step 4, where tert-butyl 4-((3R)-10-chloro-11-(5-chloro-2,4-difluorophenyl)-3-methoxy-6-oxo-3,4-dihydro-2H,6H-[1,4]thiazepino[2,3,4-ij]quinazolin-8-yl)piperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 92% yield as a yellow solid m/z (ESI, +ve)=513.0 $(M+H)^+$.

Example 539: (3S)-8-((3S,5R)-4-acryloyl-3,5-dimethylpiperazin-1-yl)-11-(5-chloro-2,4-difluorophenyl)-3-methoxy-10-(trifluoromethyl)-3,4-dihydro-2H,6H-[1,4]thiazepino[2,3,4-ij]quinazolin-6-one

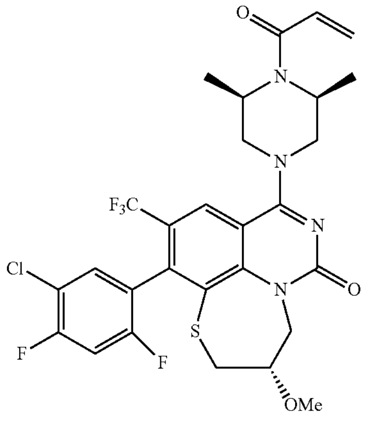 [SMILES: C=CC(=O)N1[C@H](C)CN(c2nc(=O)n3c4c(c(-c5cc(Cl)c(F)cc5F)c(C(F)(F)F)cc24)SCC[C@@H](OC)C3)C[C@@H]1C]

The title compound was prepared analogously to Example 84 where (3S)-11-(5-chloro-2,4-difluorophenyl)-8-((3S,5R)-3,5-dimethylpiperazin-1-yl)-3-methoxy-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 33% yield as a yellow solid m/z (ESI, +ve)=629.1 (M+H)+.

$^1$H NMR (400 MHz, DMSO-d6) δ 8.04 (s, 1H), 7.80-7.72 (m, 2H), 6.81 (dd, J=16.0, 8.0 Hz, 1H), 6.19 (dd, J=16.0, 4.0 Hz, 1H), 5.74 (dd, J=16.0, 4.0 Hz, 1H), 4.80-4.30 (m, 4H), 4.15-3.98 (m, 2H), 3.92-3.80 (m, 1H), 3.61-3.40 (m, 1H), 3.35 (s, 3H), 3.30-3.12 (m, 3H), 1.43-1.20 (m, 6H).

Step 1: 7-(5-chloro-2,4-difluorophenyl)-8-(((S)-3-hydroxy-2-methoxypropyl)thio)-6-(trifluoromethyl)quinazoline-2,4(1H,3H)-dione

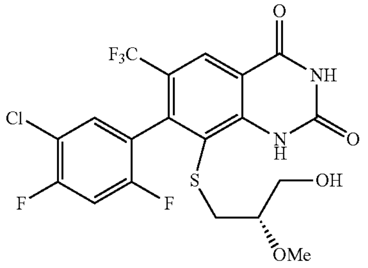 [SMILES: CO[C@@H](CO)CSc1c(-c2cc(Cl)c(F)cc2F)c(C(F)(F)F)cc2c(=O)[nH]c(=O)[nH]c12]

The title compound was synthesized analogously to example 100, step 9 where 7-(5-chloro-2,4-difluorophenyl)-8-iodo-6-(trifluoromethyl)quinazoline-2,4(1H,3H)-dione and (S)-2-methoxybutane-1-thiol was substituted in place of 7-(2,4-difluorophenyl)-8-iodo-6-(trifluoromethyl)quinazoline-2,4(1H,3H)-dione and 2-mercaptoethan-1-ol. The title compound was isolated in 49% yield as a white solid.

m/z (ESI, +ve)=497.0 $(M+H)^+$.

Step 2: (3S)-11-(5-chloro-2,4-difluorophenyl)-3-methoxy-10-(trifluoromethyl)-3,4-dihydro-2H,6H-[1,4]thiazepino[2,3,4-ij]quinazoline-6,8(7H)-dione

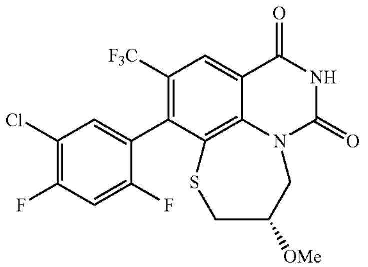 [SMILES: CO[C@@H]1CCSc2c(-c3cc(Cl)c(F)cc3F)c(C(F)(F)F)cc3c(=O)[nH]c(=O)n(c23)C1]

The title compound was prepared analogously to Example 100, step 10 where 7-(5-chloro-2,4-difluorophenyl)-8-(((S)-3-hydroxy-2-methoxypropyl)thio)-6-(trifluoromethyl)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 53% yield as a yellow solid m/z (ESI, +ve)=478.9 $(M+H)^+$.

Step 3: (3S)-11-(5-chloro-2,4-difluorophenyl)-8-((3S,5R)-3,5-dimethylpiperazin-1-yl)-3-methoxy-10-(trifluoromethyl)-3,4-dihydro-2H,6H-[1,4]thiazepino[2,3,4-ij]quinazolin-6-one

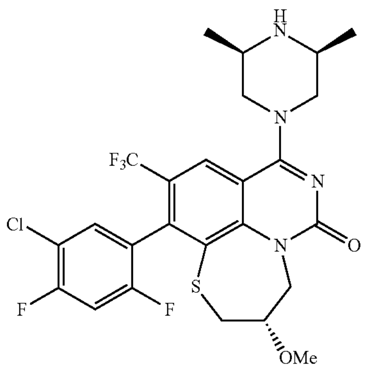 [SMILES: CO[C@@H]1CSc2c(-c3cc(Cl)c(F)cc3F)c(C(F)(F)F)cc3c(N4C[C@@H](C)N[C@@H](C)C4)nc(=O)n(c23)C1]

The title compound was prepared analogously to Example 100, step 21 where ((3S)-11-(5-chloro-2,4-difluorophenyl)-3-methoxy-10-(trifluoromethyl)-3,4-dihydro-2H,6H-[1,4]thiazepino[2,3,4-ij]quinazoline-6,8(7H)-dione and (2R,6S)-2,6-dimethylpiperazine were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 74% yield as a yellow solid m/z (ESI, +ve)=575.0 $(M+H)^+$.

Example 540: (R)-8-(4-acryloylpiperazin-1-yl)-10-chloro-11-(4-fluorophenyl)-3-methoxy-3,4-dihydro-2H,6H-[1,4]thiazepino[2,3,4-ij]quinazolin-6-one

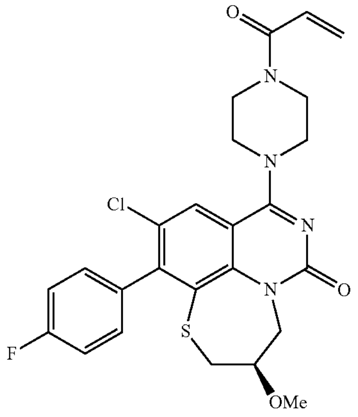 [SMILES: C=CC(=O)N1CCN(c2nc(=O)n3c4c(c(-c5ccc(F)cc5)c(Cl)cc24)SC[C@H](OC)C3)CC1]

The title compound was prepared analogously to Example 84 where (R)-10-chloro-11-(4-fluorophenyl)-3-methoxy-8-(piperazin-1-yl)-3,4-dihydro-2H,6H-[1,4]thiazepino[2,3,4-ij]quinazolin-6-one. The title compound was isolated in 32% yield as a yellow solid m/z (ESI, +ve)=515.1 $(M+H)^+$.

$^1H$ NMR (400 MHz, DMSO-d6) δ 7.72 (s, 1H), 7.45-7.28 (m, 4H), 6.83 (dd, J=16.0, 8.0 Hz, 1H), 6.17 (dd, J=16.0, 4.0 Hz, 1H), 5.74 (dd, J=16.0, 4.0 Hz, 1H), 4.49-4.45 (m, 1H), 3.86-3.66 (m, 8H), 3.34-3.29 (m, 6H), 3.10-3.06 (m, 1H).

Step 1: tert-butyl (R)-4-(10-chloro-11-(4-fluorophenyl)-3-methoxy-6-oxo-3,4-dihydro-2H,6H-[1,4]thiazepino[2,3,4-ij]quinazolin-8-yl)piperazine-1-carboxylate

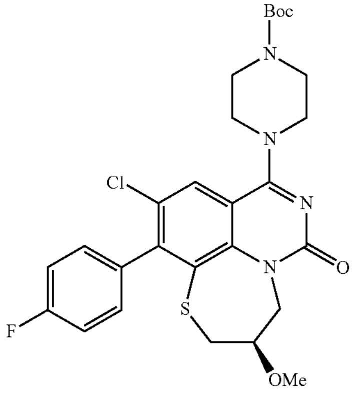 [SMILES: CO[C@H]1CSc2c(-c3ccc(F)cc3)c(Cl)cc3c(N4CCN(C(=O)OC(C)(C)C)CC4)nc(=O)n(c23)C1]

The title compound was prepared analogously to Example 100, step 21 where (R)-10-chloro-11-(4-fluorophenyl)-3-methoxy-3,4-dihydro-2H,6H-[1,4]thiazepino[2,3,4-ij]quinazoline-6,8(7H)-dione and tert-butyl piperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 90% yield as a yellow solid m/z (ESI, +ve)=561.1 $(M+H)^+$.

Step 2: (R)-10-chloro-11-(4-fluorophenyl)-3-methoxy-8-(piperazin-1-yl)-3,4-dihydro-2H,6H-[1,4]thiazepino[2,3,4-ij]quinazolin-6-one

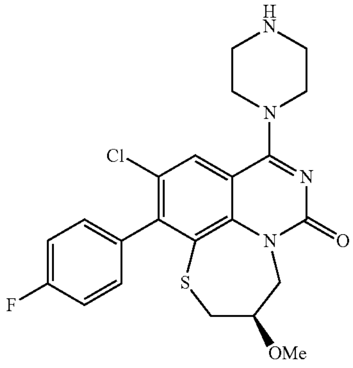 [SMILES: CO[C@H]1CSc2c(-c3ccc(F)cc3)c(Cl)cc3c(N4CCNCC4)nc(=O)n(c23)C1]

The title compound was prepared analogously to Example 102, step 4, where tert-butyl (R)-4-(10-chloro-11-(4-fluorophenyl)-3-methoxy-6-oxo-3,4-dihydro-2H,6H-[1,4]thiazepino[2,3,4-ij]quinazolin-8-yl)piperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 88% yield as a yellow solid m/z (ESI, +ve)=461.1 $(M+H)^+$.

Example 541: (3R)-8-((S)-4-acryloyl-2-methylpiperazin-1-yl)-10-chloro-11-(5-chloro-2,4-difluorophenyl)-3-methoxy-3,4-dihydro-2H,6H-[1,4]thiazepino[2,3,4-ij]quinazolin-6-one

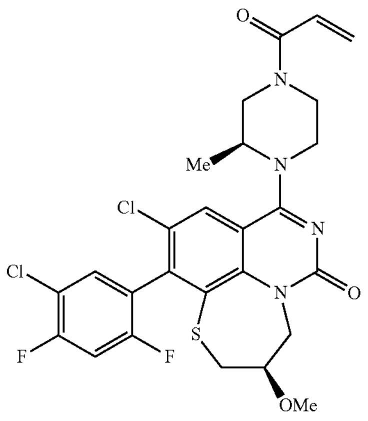 [SMILES: C=CC(=O)N1CCN(c2nc(=O)n3c4c(c(-c5cc(Cl)c(F)cc5F)c(Cl)cc24)SC[C@H](OC)C3)[C@@H](C)C1]

The title compound was prepared analogously to Example 84 where (3R)-10-chloro-11-(5-chloro-2,4-difluorophenyl)-3-methoxy-8-((S)-2-methylpiperazin-1-yl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 33% yield as a yellow solid m/z (ESI, +ve)=581.1 $(M+H)^+$.

$^1$H NMR (400 MHz, DMSO-d6) δ 7.85-7.74 (m, 2H), 7.72-7.65 (m, 1H), 6.92-6.78 (m, 1H), 6.23-6.18 (dd, J=16.0, 4.0 Hz, 1H), 5.76-5.72 (dd, J=16.0, 4.0 Hz, 1H), 4.85-4.52 (m, 2H), 4.48-4.37 (m, 2H), 4.30-4.09 (m, 1H), 4.05-3.96 (m, 1H), 3.94-3.84 (m, 1H), 3.78-3.43 (m, 3H), 3.42-3.34 (m, 3H), 3.25-3.17 (m, 1H), 3.08-2.86 (m, 1H), 1.31-1.15 (m, 3H).

Step 1: tert-butyl (3S)-4-((3R)-10-chloro-11-(5-chloro-2,4-difluorophenyl)-3-methoxy-6-oxo-3,4-dihydro-2H,6H-[1,4]thiazepino[2,3,4-ij]quinazolin-8-yl)-3-methylpiperazine-1-carboxylate

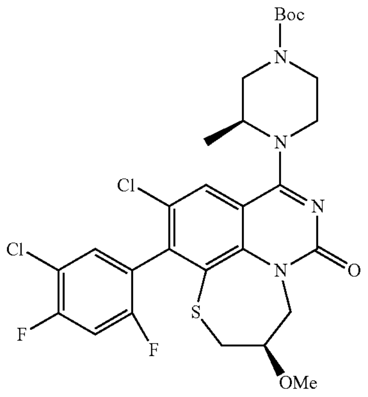 [SMILES: CO[C@H]1CSc2c(-c3cc(Cl)c(F)cc3F)c(Cl)cc3c(N4CCN(C(=O)OC(C)(C)C)C[C@@H]4C)nc(=O)n(c23)C1]

The title compound was prepared analogously to Example 100, step 21 where (3R)-10-chloro-11-(5-chloro-2,4-difluorophenyl)-3-methoxy-3,4-dihydro-2H,6H-[1,4]thiazepino[2,3,4-ij]quinazoline-6,8(7H)-dione and tert-butyl (S)-3-methylpiperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 65% yield as a yellow solid m/z (ESI, +ve)=627.1 $(M+H)^+$.

Step 2: (3R)-10-chloro-11-(5-chloro-2,4-difluorophenyl)-3-methoxy-8-((S)-2-methylpiperazin-1-yl)-3,4-dihydro-2H,6H-[1,4]thiazepino[2,3,4-ij]quinazolin-6-one

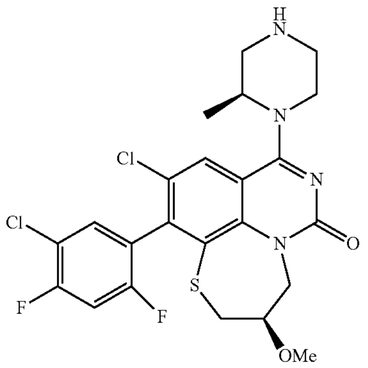 [SMILES: CO[C@H]1CSc2c(-c3cc(Cl)c(F)cc3F)c(Cl)cc3c(N4CCNC[C@@H]4C)nc(=O)n(c23)C1]

The title compound was prepared analogously to Example 102, step 4, where tert-butyl (3S)-4-((3R)-10-chloro-11-(5-chloro-2,4-difluorophenyl)-3-methoxy-6-oxo-3,4-dihydro-2H,6H-[1,4]thiazepino[2,3,4-ij]quinazolin-8-yl)-3-methylpiperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 99% yield as a yellow solid m/z (ESI, +ve)=527.0 $(M+H)^+$.

Example 542: (3R)-8-((3S,5R)-4-acryloyl-3,5-dimethylpiperazin-1-yl)-10-chloro-11-(5-chloro-2,4-difluorophenyl)-3-methoxy-3,4-dihydro-2H,6H-[1,4]thiazepino[2,3,4-ij]quinazolin-6-one

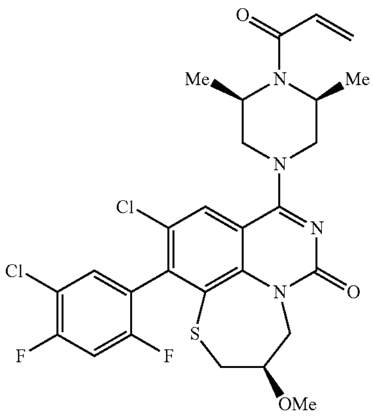 [SMILES: C=CC(=O)N1[C@H](C)CN(c2nc(=O)n3c4c(c(-c5cc(Cl)c(F)cc5F)c(Cl)cc24)SC[C@H](OC)C3)C[C@@H]1C]

The title compound was prepared analogously to Example 84 where (3R)-10-chloro-11-(5-chloro-2,4-difluorophenyl)-8-((3S,5R)-3,5-dimethylpiperazin-1-yl)-3-methoxy-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 22% yield as a yellow solid m/z (ESI, +ve)=595.1 $(M+H)^+$.

$^1H$ NMR (400 MHz, DMSO-d6) δ 7.84-7.73 (m, 3H), 6.80 (dd, J=16.0, 8.0 Hz, 1H), 6.19 (dd, J=16.0, 4.0 Hz, 1H), 5.74 (dd, J=16.0, 4.0 Hz, 1H), 4.65-4.36 (m, 4H), 4.09-3.98 (m, 2H), 3.92-3.83 (m, 1H), 3.52-3.45 (m, 1H), 3.39-3.34 (m, 3H), 3.32-3.27 (m, 2H), 3.19-3.10 (m, 1H), 1.46-1.29 (m, 6H).

Step 1: (3R)-10-chloro-11-(5-chloro-2,4-difluorophenyl)-8-((3S,5R)-3,5-dimethylpiperazin-1-yl)-3-methoxy-3,4-dihydro-2H,6H-[1,4]thiazepino[2,3,4-ij]quinazolin-6-one

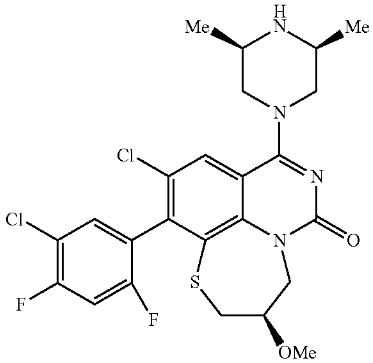 [SMILES: CO[C@H]1CSc2c(-c3cc(Cl)c(F)cc3F)c(Cl)cc3c(N4C[C@@H](C)N[C@@H](C)C4)nc(=O)n(c23)C1]

The title compound was prepared analogously to Example 100, step 21 where (3R)-10-chloro-11-(5-chloro-2,4-difluorophenyl)-3-methoxy-3,4-dihydro-2H,6H-[1,4]thiazepino[2,3,4-ij]quinazoline-6,8(7H)-dione and (2R,6S)-2,6-dimethylpiperazine were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 76% yield as a yellow solid m/z (ESI, +ve)=541.1 $(M+H)^+$+.

Example 543: (3S)-8-(4-acryloylpiperazin-1-yl)-10-chloro-11-(5-chloro-2,4-difluorophenyl)-3-methoxy-3,4-dihydro-2H,6H-[1,4]thiazepino[2,3,4-ij]quinazolin-6-one

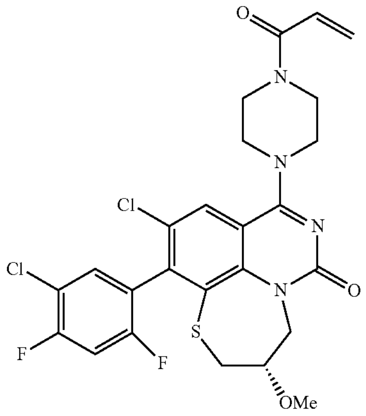 [SMILES: C=CC(=O)N1CCN(c2nc(=O)n3c4c(c(-c5cc(Cl)c(F)cc5F)c(Cl)cc24)SC[C@@H](OC)C3)CC1]

The title compound was prepared analogously to Example 84 where (3S)-10-chloro-11-(5-chloro-2,4-difluorophenyl)-3-methoxy-8-(piperazin-1-yl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 22% yield as a yellow solid m/z (ESI, +ve)=567.1 $(M+H)^+$.

$^1H$ NMR (400 MHz, DMSO-d6) δ 7.87-7.72 (m, 3H), 6.82 (dd, J=16.0 Hz, 8.0 Hz, 1H), 6.17 (dd, J=16.0 Hz, 4.0 Hz 1H), 5.74 (dd, J=16.0 Hz, 4.0 Hz, 1H), 4.48-4.44 (m, 1H), 3.91-3.63 (m, 9H), 3.48-3.44 (m, 1H), 3.32 (s, 4H), 3.21-3.09 (m, 1H).

Step 1: 6-chloro-7-(5-chloro-2,4-difluorophenyl)-8-(((S)-3-hydroxy-2-methoxypropyl)thio)quinazoline-2,4(1H,3H)-dione

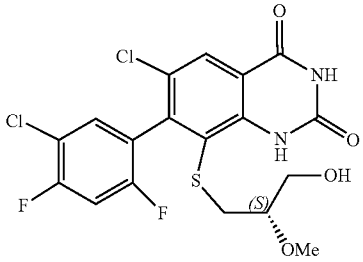

The title compound was prepared analogously to Example 100, step 9 where 6-chloro-7-(5-chloro-2,4-difluorophenyl)-8-iodoquinazoline-2,4(1H,3H)-dione and (S)-3-mercapto-2-methoxypropan-1-ol were substituted in place of 7-(2,4-difluorophenyl)-8-iodo-6-(trifluoromethyl)quinazoline-2,4(1H,3H)-dione and 2-mercaptoethan-1-ol in 61% yield as a yellow solid m/z (ESI, +ve)=462.9 $(M+H)^+$.

Step 2: (3S)-10-chloro-11-(5-chloro-2,4-difluorophenyl)-3-methoxy-3,4-dihydro-2H,6H-[1,4]thiazepino[2,3,4-ij]quinazoline-6,8(7H)-dione

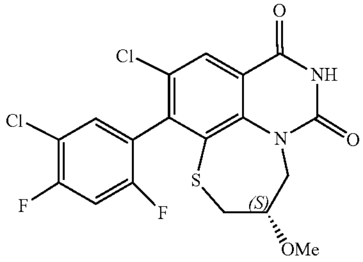

The title compound was prepared analogously to Example 100, step 10 where 6-chloro-7-(5-chloro-2,4-difluorophenyl)-8-(((S)-3-hydroxy-2-methoxypropyl)thio)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 58% yield as a yellow solid m/z (ESI, +ve)=445.0 $(M+H)^+$.

Step 3: tert-butyl 4-((3S)-10-chloro-11-(5-chloro-2,4-difluorophenyl)-3-methoxy-6-oxo-3,4-dihydro-2H,6H-[1,4]thiazepino[2,3,4-ij]quinazolin-8-yl)piperazine-1-carboxylate

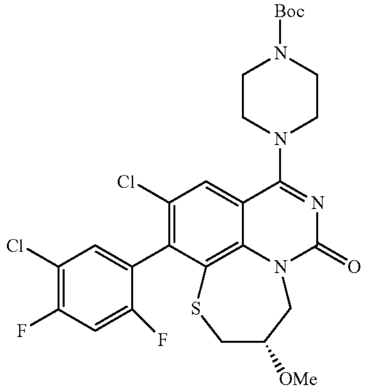 [SMILES: CO[C@@H]1CSc2c(-c3cc(Cl)c(F)cc3F)c(Cl)cc3c(N4CCN(C(=O)OC(C)(C)C)CC4)nc(=O)n(c23)C1]

The title compound was prepared analogously to Example 100, step 21 where (3S)-10-chloro-11-(5-chloro-2,4-difluorophenyl)-3-methoxy-3,4-dihydro-2H,6H-[1,4]thiazepino[2,3,4-ij]quinazoline-6,8(7H)-dione and tert-butyl piperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 89% yield as a yellow solid m/z (ESI, +ve)=613.1 $(M+H)^+$.

Step 4: (3S)-10-chloro-11-(5-chloro-2,4-difluorophenyl)-3-methoxy-8-(piperazin-1-yl)-3,4-dihydro-2H,6H-[1,4]thiazepino[2,3,4-ij]quinazolin-6-one

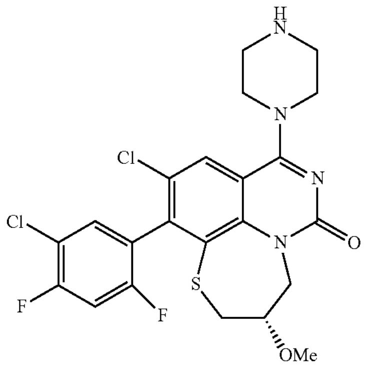 [SMILES: CO[C@@H]1CSc2c(-c3cc(Cl)c(F)cc3F)c(Cl)cc3c(N4CCNCC4)nc(=O)n(c23)C1]

The title compound was prepared analogously to Example 102, step 4, where tert-butyl 4-((3S)-10-chloro-11-(5-chloro-2,4-difluorophenyl)-3-methoxy-6-oxo-3,4-dihydro-2H,6H-[1,4]thiazepino[2,3,4-ij]quinazolin-8-yl)piperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 75% yield as a yellow solid m/z (ESI, +ve)=513.0 $(M+H)^+$.

Example 582: (3S)-8-(4-acryloylpiperazin-1-yl)-11-(5-chloro-2,4-difluorophenyl)-3-methoxy-10-(trifluoromethyl)-3,4-dihydro-2H,6H-[1,4]thiazepino[2,3,4-ij]quinazolin-6-one

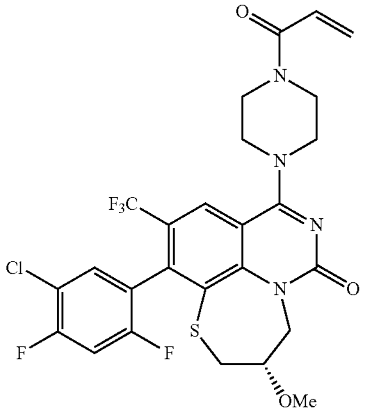 [SMILES: C=CC(=O)N1CCN(c2nc(=O)n3c4c(c(-c5cc(Cl)c(F)cc5F)c(C(F)(F)F)cc24)SC[C@@H](OC)C3)CC1]

The title compound was prepared analogously to Example 84 where (3S)-11-(5-chloro-2,4-difluorophenyl)-3-methoxy-8-(piperazin-1-yl)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 13% yield as a yellow solid m/z (ESI, +ve)=601.1 (M+H)+.

$^1$H NMR (400 MHz, DMSO-d6) δ 7.90 (s, 1H), 7.80-7.75 (m, 2H), 6.82 (dd, J=16.0, 8.0 Hz, 1H), 6.17 (dd, J=16.0, 4.0 Hz, 1H), 5.74 (dd, J=16.0, 4.0 Hz, 1H), 4.50-4.48 (m, 1H), 3.84-3.74 (m, 8H), 3.51-3.35 (m, 4H), 3.27-3.18 (m, 3H).

Step 1: tert-butyl 4-((3S)-11-(5-chloro-2,4-difluorophenyl)-3-methoxy-6-oxo-10-(trifluoromethyl)-3,4-dihydro-2H,6H-[1,4]thiazepino[2,3,4-ij]quinazolin-8-yl)piperazine-1-carboxylate

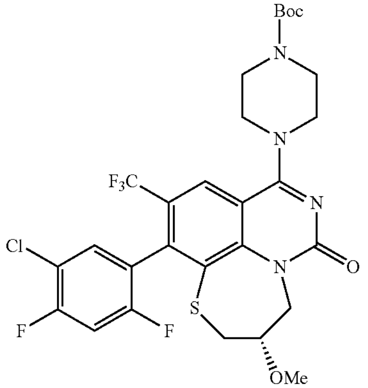 [SMILES: CO[C@@H]1CSc2c(-c3cc(Cl)c(F)cc3F)c(C(F)(F)F)cc3c(N4CCN(C(=O)OC(C)(C)C)CC4)nc(=O)n(c23)C1]

The title compound was prepared analogously to Example 100, step 21 where (3S)-11-(5-chloro-2,4-difluorophenyl)-3-methoxy-10-(trifluoromethyl)-3,4-dihydro-2H,6H-[1,4]thiazepino[2,3,4-ij]quinazoline-6,8(7H)-dione and tert-butyl piperazine-1-carboxylate were substituted in place of 10-(2, 4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 70% yield as a yellow solid m/z (ESI, +ve)=647.0 $(M+H)^+$.

Step 2: (3S)-11-(5-chloro-2,4-difluorophenyl)-3-methoxy-8-(piperazin-1-yl)-10-(trifluoromethyl)-3,4-dihydro-2H,6H-[1,4]thiazepino[2,3,4-ij]quinazolin-6-one

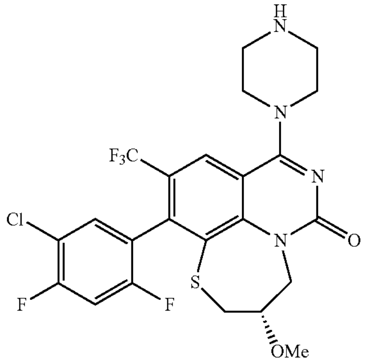 [SMILES: CO[C@@H]1CSc2c(-c3cc(Cl)c(F)cc3F)c(C(F)(F)F)cc3c(N4CCNCC4)nc(=O)n(c23)C1]

The title compound was prepared analogously to Example 102, step 4, where tert-butyl 4-((3S)-11-(5-chloro-2,4-difluorophenyl)-3-methoxy-6-oxo-10-(trifluoromethyl)-3,4-dihydro-2H,6H-[1,4]thiazepino[2,3,4-ij]quinazolin-8-yl)piperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 91% yield as a yellow solid m/z (ESI, +ve)=547.1 (M+H)+.

Example 583: (3S)-8-((S)-4-acryloyl-2-methylpiperazin-1-yl)-11-(5-chloro-2,4-difluorophenyl)-3-methoxy-10-(trifluoromethyl)-3,4-dihydro-2H,6H-[1,4]thiazepino[2,3,4-ij]quinazolin-6-one

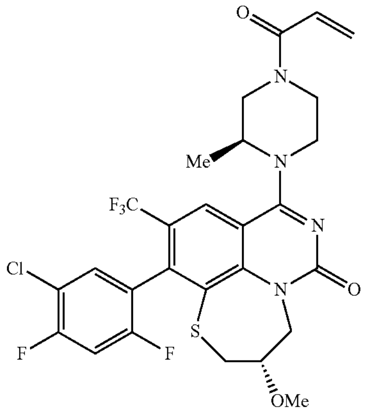 [SMILES: C=CC(=O)N1CCN(c2nc(=O)n3c4c(c(-c5cc(Cl)c(F)cc5F)c(C(F)(F)F)cc24)SC[C@@H](OC)C3)[C@@H](C)C1]

The title compound was prepared analogously to Example 84 where (3S)-11-(5-chloro-2,4-difluorophenyl)-3-methoxy-8-((S)-2-methylpiperazin-1-yl)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 41% yield as a yellow solid m/z (ESI, +ve)=615.1 (M+H)+.

$^1$H NMR (400 MHz, DMSO-d6) δ 7.80-7.77 (m, 3H), 6.87-6.83 (m, 1H), 6.19 (dd, J=16.0, 4.0 Hz, 1H), 5.74 (dd, J=16.0, 4.0 Hz, 1H), 4.67-4.63 (m, 1H), 4.49-4.41 (m, 2H), 4.28-4.15 (m, 2H), 3.99-3.85 (m, 2H), 3.59-3.36 (m, 5H), 3.27-3.02 (m, 3H), 1.31 (dd, J=16.0, 4.0 Hz, 3H).

Step 1: (3S)-4-((3S)-11-(5-chloro-2,4-difluorophenyl)-3-methoxy-6-oxo-10-(trifluoromethyl)-3,4-dihydro-2H,6H-[1,4]thiazepino[2,3,4-ij]quinazolin-8-yl)-3-methylpiperazine-1-carboxylate

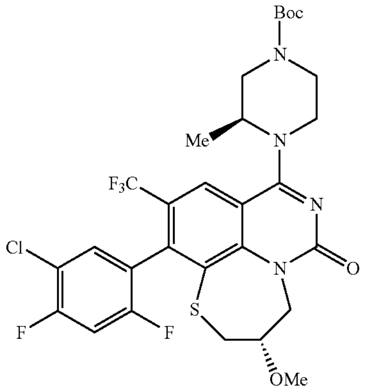 [SMILES: CO[C@@H]1CSc2c(-c3cc(Cl)c(F)cc3F)c(C(F)(F)F)cc3c(N4CCN(C(=O)OC(C)(C)C)C[C@@H]4C)nc(=O)n(c23)C1]

The title compound was prepared analogously to Example 100, step 21 where (3S)-11-(5-chloro-2,4-difluorophenyl)-3-methoxy-10-(trifluoromethyl)-3,4-dihydro-2H,6H-[1,4]thiazepino[2,3,4-ij]quinazoline-6,8(7H)-dione and tert-butyl (S)-3-methylpiperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 69% yield as a yellow solid m/z (ESI, +ve)=661.1 $(M+H)^+$.

Step 2: (3S)-11-(5-chloro-2,4-difluorophenyl)-3-methoxy-8-((S)-2-methylpiperazin-1-yl)-10-(trifluoromethyl)-3,4-dihydro-2H,6H-[1,4]thiazepino[2,3,4-ij]quinazolin-6-one

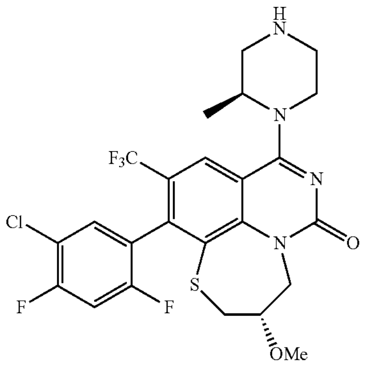 [SMILES: CO[C@@H]1CSc2c(-c3cc(Cl)c(F)cc3F)c(C(F)(F)F)cc3c(N4CCNC[C@@H]4C)nc(=O)n(c23)C1]

The title compound was prepared analogously to Example 102, step 4, where (3S)-4-((3S)-11-(5-chloro-2,4-difluorophenyl)-3-methoxy-6-oxo-10-(trifluoromethyl)-3,4-dihydro-2H,6H-[1,4]thiazepino[2,3,4-ij]quinazolin-8-yl)-3-methylpiperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 90% yield as a yellow solid m/z (ESI, +ve)=561.1 (M+H)+.

Example 584: (R)-8-((3S,5R)-4-acryloyl-3,5-dimethylpiperazin-1-yl)-11-(4-fluorophenyl)-3-methoxy-10-(trifluoromethyl)-3,4-dihydro-2H,6H-[1,4]thiazepino[2,3,4-ij]quinazolin-6-one

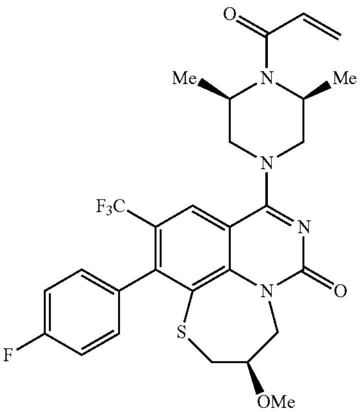 [SMILES: C=CC(=O)N1[C@H](C)CN(c2nc(=O)n3c4c(c(-c5ccc(F)cc5)c(C(F)(F)F)cc24)SC[C@H](OC)C3)C[C@@H]1C]

The title compound was prepared analogously to Example 84 where (R)-8-((3S,5R)-3,5-dimethylpiperazin-1-yl)-11-(4-fluorophenyl)-3-methoxy-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 39% yield as a yellow solid m/z (ESI, +ve)=577.2 $(M+H)^+$.

$^1$H NMR (400 MHz, DMSO-d6) δ 8.01 (s, 1H), 7.36-7.32 (m, 4H), 6.81 (dd, J=16.0, 8.0 Hz, 1H), 6.19 (dd, J=16.0, 4.0 Hz, 1H), 5.74 (dd, J=12.0, 4.0 Hz, 1H), 4.65-4.44 (m, 3H), 4.09-4.05 (m, 2H), 3.84-3.80 (m, 1H), 3.35-3.30 (m, 5H), 3.28-3.24 (m, 2H), 3.11-3.07 (m, 1H), 1.40 (s, 6H).

Step 1: (R)-7-(4-fluorophenyl)-8-((3-hydroxy-2-methoxypropyl)thio)-6-(trifluoromethyl)quinazoline-2,4(1H,3H)-dione

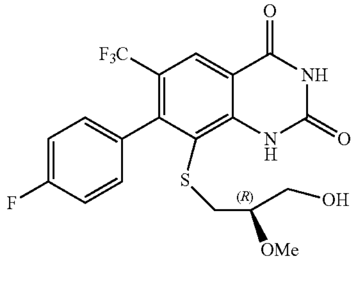

The title compound was prepared analogously to Example 100, step 9 where 7-(4-fluorophenyl)-8-iodo-6-(trifluoromethyl)quinazoline-2,4(1H,3H)-dione and (R)-3-mercapto-2-methoxypropan-1-ol were substituted in place of 7-(2,4-difluorophenyl)-8-iodo-6-(trifluoromethyl)quinazoline-2,4(1H,3H)-dione and 2-mercaptoethan-1-ol. The title compound was isolated in 90% yield as a yellow solid m/z (ESI, +ve)=445.1 (M+H)+.

Step 2: (R)-11-(4-fluorophenyl)-3-methoxy-10-(trifluoromethyl)-3,4-dihydro-2H,6H-[1,4]thiazepino[2,3,4-ij]quinazoline-6,8(7H)-dione

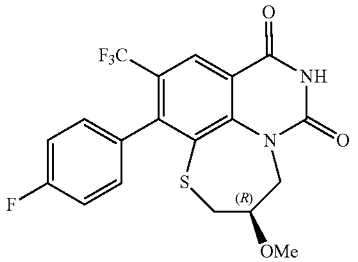

The title compound was prepared analogously to Example 100, step 10 where (R)-7-(4-fluorophenyl)-8-((3-hydroxy-2-methoxypropyl)thio)-6-(trifluoromethyl)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 82% yield as a yellow solid m/z (ESI, +ve)=427.1 (M+H)+.

Step 3: (R)-8-((3S,5R)-3,5-dimethylpiperazin-1-yl)-11-(4-fluorophenyl)-3-methoxy-10-(trifluoromethyl)-3,4-dihydro-2H,6H-[1,4]thiazepino[2,3,4-ij]quinazolin-6-one

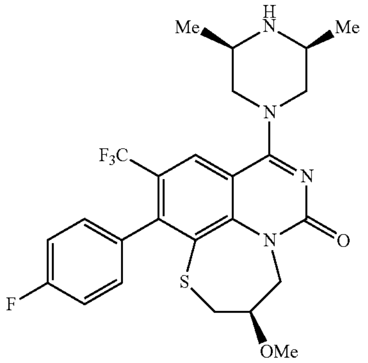 [SMILES: CO[C@H]1CSc2c(-c3ccc(F)cc3)c(C(F)(F)F)cc3c(N4C[C@@H](C)N[C@@H](C)C4)nc(=O)n(c23)C1]

The title compound was prepared analogously to Example 100, step 21 where (R)-11-(4-fluorophenyl)-3-methoxy-10-(trifluoromethyl)-3,4-dihydro-2H,6H-[1,4]thiazepino[2,3,4-ij]quinazoline-6,8(7H)-dione and (2R,6S)-2,6-dimethylpiperazine were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 73% yield as a yellow solid m/z (ESI, +ve)=523.2 $(M+H)^+$.

Example 585: (S)-8-((3S,5R)-4-acryloyl-3,5-dimethylpiperazin-1-yl)-11-(4-fluorophenyl)-3-methoxy-10-(trifluoromethyl)-3,4-dihydro-2H,6H-[1,4]thiazepino[2,3,4-ij]quinazolin-6-one

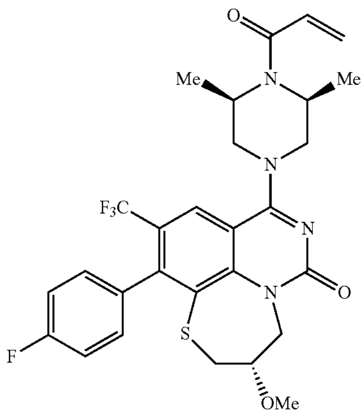 [SMILES: C=CC(=O)N1[C@H](C)CN(c2nc(=O)n3c4c(c(-c5ccc(F)cc5)c(C(F)(F)F)cc24)SC[C@@H](OC)C3)C[C@@H]1C]

The title compound was prepared analogously to Example 84 where (S)-8-((3S,5R)-3,5-dimethylpiperazin-1-yl)-11-(4-fluorophenyl)-3-methoxy-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 47% yield as a white solid m/z (ESI, +ve)=577.1 $(M+H)^+$.

$^1H$ NMR (400 MHz, DMSO-d6) δ=8.02 (s, 1H), 7.36-7.34 (m, 4H), 6.82 (dd, J=16.0, 8.0 Hz, 1H), 6.19 (dd, J=16.0, 4.0 Hz, 1H), 5.74 (dd, J=16.0, 4.0 Hz, 1H), 4.59-4.48 (m, 3H), 4.09-4.05 (m, 2H), 3.84-3.82 (m, 1H), 3.33-3.32 (m, 5H), 3.28-3.24 (m, 2H), 3.12-3.08 (m, 1H), 1.40 (m, 6H).

Step 1: (S)-7-(4-fluorophenyl)-8-((3-hydroxy-2-methoxypropyl)thio)-6-(trifluoromethyl)quinazoline-2,4(1H,3H)-dione

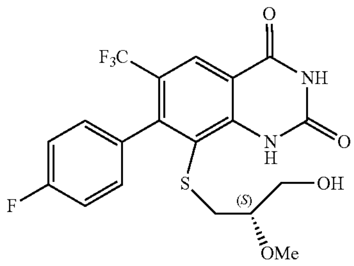

The title compound was prepared analogously to Example 100, step 9 where (S)-8-((3S,5R)-3,5-dimethylpiperazin-1-yl)-11-(4-fluorophenyl)-3-methoxy-10-(trifluoromethyl)-3,4-dihydro-2H,6H-[1,4]thiazepino[2,3,4-ij]quinazolin-6-one and (S)-3-mercapto-2-methoxypropan-1-ol were substituted in place of 7-(2,4-difluorophenyl)-8-iodo-6-(trifluoromethyl)quinazoline-2,4(1H,3H)-dione and 2-mercaptoethan-1-ol. The title compound was isolated in 90% yield as a yellow solid m/z (ESI, +ve)=445.1 (M+H)+.

Step 2: (S)-11-(4-fluorophenyl)-3-methoxy-10-(trifluoromethyl)-3,4-dihydro-2H,6H-[1,4]thiazepino[2,3,4-ij]quinazoline-6,8(7H)-dione

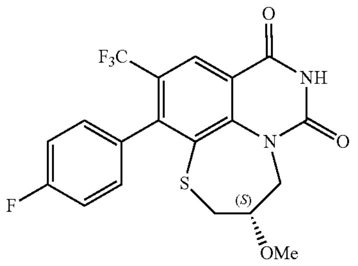

The title compound was prepared analogously to Example 100, step 10 where (S)-7-(4-fluorophenyl)-8-((3-hydroxy-2-methoxypropyl)thio)-6-(trifluoromethyl)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 72% yield as a yellow solid m/z (ESI, +ve)=427.1 (M+H)+.

Step 3: (S)-8-((3S,5R)-3,5-dimethylpiperazin-1-yl)-11-(4-fluorophenyl)-3-methoxy-10-(trifluoromethyl)-3,4-dihydro-2H,6H-[1,4]thiazepino[2,3,4-ij]quinazolin-6-one

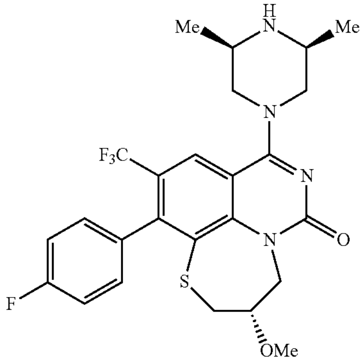 [SMILES: CO[C@@H]1CSc2c(-c3ccc(F)cc3)c(C(F)(F)F)cc3c(N4C[C@@H](C)N[C@@H](C)C4)nc(=O)n(c23)C1]

The title compound was prepared analogously to Example 100, step 21 where (S)-11-(4-fluorophenyl)-3-methoxy-10-(trifluoromethyl)-3,4-dihydro-2H,6H-[1,4]thiazepino[2,3,4-ij]quinazoline-6,8(7H)-dione and (2R,6S)-2,6-dimethylpiperazine were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 53% yield as a yellow solid m/z (ESI, +ve)=523.1 $(M+H)^+$.

Example 586: (3R)-8-((3S,5R)-4-acryloyl-3,5-dimethylpiperazin-1-yl)-11-(2,4-difluorophenyl)-3-(dimethylamino)-10-(trifluoromethyl)-3,4-dihydro-2H,6H-[1,4]thiazepino[2,3,4-ij]quinazolin-6-one

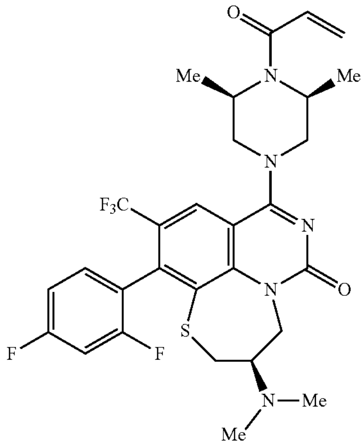 [SMILES: C=CC(=O)N1[C@H](C)CN(c2nc(=O)n3c4c(c(-c5ccc(F)cc5F)c(C(F)(F)F)cc24)SC[C@H](N(C)C)C3)C[C@@H]1C]

The title compound was prepared analogously to Example 454, where (12R)-8-(2,4-difluorophenyl)-12-(dimethylamino)-4-[(3S,5R)-3,5-dimethylpiperazin-1-yl]-7-(trifluoromethyl)-10-thia-1,3-diazatricyclo[7.4.1.05,14]tetradeca-3,5(14),6,8-tetraen-2-one was substituted in place of (3S)-11-(2,4-difluorophenyl)-3-(methyl(2,2,2-trifluoroethyl)amino)-8-((S)-2-methylpiperazin-1-yl)-10-(trifluoromethyl)-3,4-dihydro-2H,6H-[1,4]thiazepino[2,3,4-ij]quinazolin-6-one. The title compound was isolated in 35% yield as a white solid m/z (ESI, +ve)=608.2

1H NMR (400 MHz, MeOD): δ 8.12 (d, J=2.1 Hz, 1H), 7.34-7.24 (m, 1H), 7.13 (ddt, J=10.8, 8.4, 2.9 Hz, 2H), 6.84 (dd, J=16.7, 10.6 Hz, 1H), 6.29 (dd, J=16.6, 2.1 Hz, 1H), 5.80 (dd, J=10.6, 2.0 Hz, 1H), 4.76 (dd, J=13.7, 2.5 Hz, 1H), 4.64-4.57 (m, 1H), 4.40-4.27 (m, 2H), 3.79-3.71 (m, 1H), 3.65-3.58 (m, 1H), 3.53-3.41 (m, 2H), 3.21-3.10 (m, 1H), 2.64-2.48 (m, 2H), 2.23 (d, J=1.9 Hz, 6H), 1.54 (dd, J=14.0, 7.0 Hz, 3H), 1.44 (dd, J=13.2, 6.9 Hz, 3H).

Step 1: (2S)-1-benzyloxy-3-tritylsulfanyl-propan-2-ol

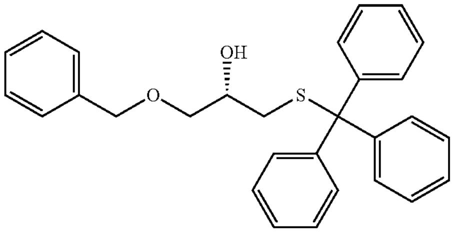 [SMILES: O[C@@H](COCc1ccccc1)CSC(c1ccccc1)(c1ccccc1)c1ccccc1]

The title compound was prepared analogously to Example 454, step 1, where (2S)-2-(benzyloxymethyl)oxirane was substituted in place of (2R)-2-(benzyloxymethyl)oxirane. The title compound was isolated in 95% yield as a colorless oil 1H NMR (400 MHz, DMSO) δ 7.38-7.19 (m, 20H), 5.04 (s, 1H), 4.39 (s, 2H), 3.54 (q, J=5.9 Hz, 1H), 3.25 (ddd, J=31.3, 9.8, 5.4 Hz, 2H), 2.33-2.15 (m, 2H).

Step 2: [(1S)-1-(benzyloxymethyl)-2-tritylsulfanyl-ethyl] methanesulfonate

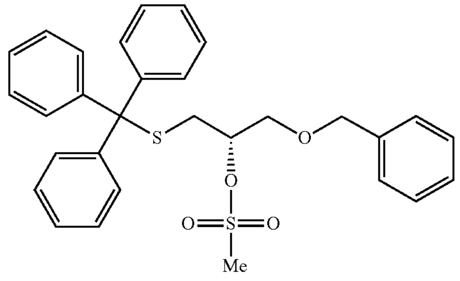 [SMILES: CS(=O)(=O)O[C@@H](COCc1ccccc1)CSC(c1ccccc1)(c1ccccc1)c1ccccc1]

The title compound was prepared analogously to Example 454, step 2, where (2S)-2-(benzyloxymethyl)oxirane was substituted in place of (2R)-2-(benzyloxymethyl)oxirane. The title compound was isolated in 52% yield as a colorless oil 1H NMR (400 MHz, CDCl3) δ 7.45-7.42 (m, 5H), 7.34-7.24 (m, 15H), 4.52-4.41 (m, 2H), 4.33 (qd, J=6.4, 4.8 Hz, 1H), 3.55-3.43 (m, 2H), 2.95 (s, 3H), 2.64 (qd, J=13.4, 6.5 Hz, 2H).

Step 3: (2R)-1-benzyloxy-N,N-dimethyl-3-tritylsulfanyl-propan-2-amine

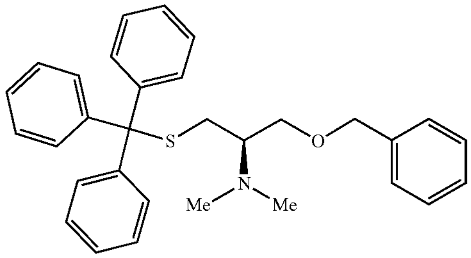 [SMILES: CN(C)[C@H](COCc1ccccc1)CSC(c1ccccc1)(c1ccccc1)c1ccccc1]

The title compound was prepared analogously to Example 454, step 3, where [(1S)-1-(benzyloxymethyl)-2-tritylsulfanyl-ethyl] methanesulfonate was substituted in place of (R)-1-(benzyloxy)-3-(tritylthio)propan-2-yl methanesulfonate. The title compound was isolated in 9% yield as a pale yellow oil m/z (ESI, +ve)=468.2

Step 4: (2R)-3-Benzyloxy-2-(dimethylamino)propane-1-thiol

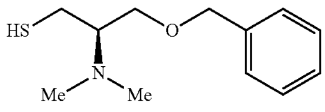 [SMILES: CN(C)[C@@H](CS)COCc1ccccc1]

The title compound was prepared analogously to Example 454, step 4, where (2R)-1-benzyloxy-N,N-dimethyl-3-tritylsulfanyl-propan-2-amine was substituted in place of (S)-1-(benzyloxy)-N-methyl-N-(2,2,2-trifluoroethyl)-3-(tritylthio)propan-2-amine. The title compound was immediately used in the next step without further purification Step 5: 8-[(2R)-3-benzyloxy-2-(dimethylamino)propyl]sulfanyl-7-(2,4-difluorophenyl)-6-(trifluoromethyl)-1H-quinazoline-2,4-dione

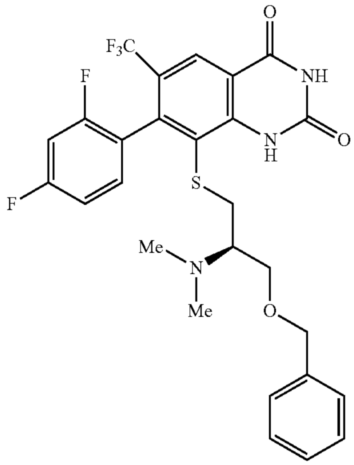 [SMILES: CN(C)[C@H](COCc1ccccc1)CSc1c(-c2ccc(F)cc2F)c(C(F)(F)F)cc2c(=O)[nH]c(=O)[nH]c12]

The title compound was prepared analogously to Example 454, step 5, where (2R)-3-Benzyloxy-2-(dimethylamino)propane-1-thiol was substituted in place of (2R)-3-benzyloxy-2-(dimethylamino)propane-1-thiol. The title compound was isolated in 71% yield as a yellow semisolid m/z (ESI, +ve)=566.1

Step 6: 7-(2,4-difluorophenyl)-8-[(2R)-2-(dimethylamino)-3-hydroxy-propyl]sulfanyl-6-(trifluoromethyl)-1H-quinazoline-2,4-dione

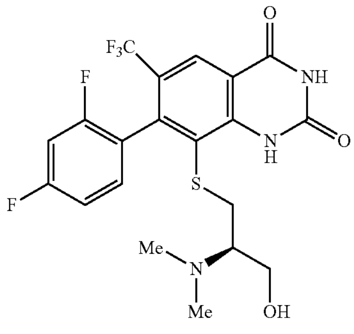 [SMILES: CN(C)[C@H](CO)CSc1c(-c2ccc(F)cc2F)c(C(F)(F)F)cc2c(=O)[nH]c(=O)[nH]c12]

To a solution of 8-[(2R)-3-benzyloxy-2-(dimethylamino)propyl]sulfanyl-7-(2,4-difluorophenyl)-6-(trifluoromethyl)-1H-quinazoline-2,4-dione (45 mg, 0.08 mmol) in dichloromethane (1 mL) precooled at −78° C. (1 mL), 0.16 mL of boron tribromide (1M in dichloromethane) was added dropwise. The reaction was stirred at −78° C. for 1 hour and after that time quenched by the addition of methanol (3 mL) and a small scoop of sodium sulfite powder. The reaction was stirred at room temperature for 10 minutes and diluted with 5 additional mL of methanol. The solids were separated by filtration and the filtrate concentrated under reduced pressure to afford the title compound which was used in the next step without further purification.

m/z (ESI, +ve)=476.1

Step 7: (12R)-8-(2,4-difluorophenyl)-12-(dimethylamino)-7-(trifluoromethyl)-10-thia-1,3-diazatricyclo[7.4.1.05,14]tetradeca-5(14),6,8-triene-2,4-dione

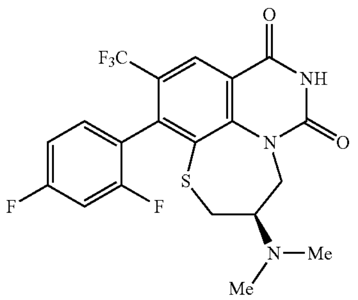 [SMILES: CN(C)[C@H]1CSc2c(-c3ccc(F)cc3F)c(C(F)(F)F)cc3c(=O)[nH]c(=O)n(c23)C1]

The title compound was prepared analogously to Example 454, step 7, where 7-(2,4-difluorophenyl)-8-[(2R)-2-(dimethylamino)-3-hydroxy-propyl]sulfanyl-6-(trifluoromethyl)-1H-quinazoline-2,4-dione was substituted in place of 7-(2,4-difluorophenyl)-8-(((S)-3-hydroxy-2-(methyl(2,2,2-trifluoroethyl)amino)propyl)thio)-6-(trifluoromethyl)quinazoline-2,4(1H,3H)-dione. The title compound was isolated in 82% yield as a white solid m/z (ESI, +ve)=458.2

Step 8: tert-butyl (2S,6R)-4-[(12R)-8-(2,4-difluorophenyl)-12-(dimethylamino)-2-oxo-7-(trifluoromethyl)-10-thia-1,3-diazatricyclo[7.4.1.05,14]tetradeca-3,5,7,9(14)-tetraen-4-yl]-2,6-dimethylpiperazine-1-carboxylate

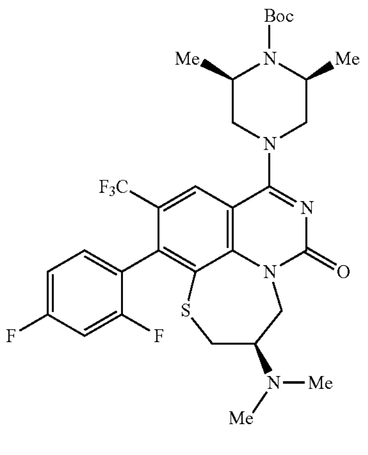 [SMILES: C[C@@H]1CN(c2nc(=O)n3c4c(c(-c5ccc(F)cc5F)c(C(F)(F)F)cc24)SC[C@H](N(C)C)C3)C[C@H](C)N1C(=O)OC(C)(C)C]

The title compound was prepared analogously to Example 100, step 21 where (12R)-8-(2,4-difluorophenyl)-12-(dimethylamino)-7-(trifluoromethyl)-10-thia-1,3-diazatricyclo[7.4.1.05,14]tetradeca-5(14),6,8-triene-2,4-dione and tert-butyl (2S,6R)-2,6-dimethylpiperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 31% yield as a tan solid m/z (ESI, +ve)=654.2

Step 9: (12R)-8-(2,4-difluorophenyl)-12-(dimethylamino)-4-[(3S,5R)-3,5-dimethylpiperazin-1-yl]-7-(trifluoromethyl)-10-thia-1,3-diazatricyclo[7.4.1.05,14]tetradeca-3,5(14),6,8-tetraen-2-one

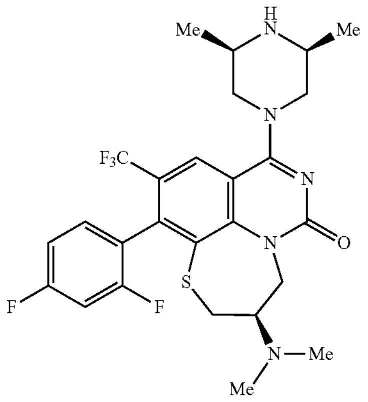 [SMILES: C[C@@H]1CN(c2nc(=O)n3c4c(c(-c5ccc(F)cc5F)c(C(F)(F)F)cc24)SC[C@H](N(C)C)C3)C[C@H](C)N1]

The title compound was prepared analogously to Example 102, step 4, where tert-butyl (2S,6R)-4-[(12R)-8-(2,4-difluorophenyl)-12-(dimethylamino)-2-oxo-7-(trifluoromethyl)-10-thia-1,3-diazatricyclo[7.4.1.05,14]tetradeca-3,5,7,9(14)-tetraen-4-yl]-2,6-dimethyl-piperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 99% yield as a brown solid m/z (ESI, +ve)=554.2.

Select CAF data (see Example 7 below for assay) for various compounds are tabulated below:

TABLE 6

CAF data for compounds 408 to 589

| Example Number | IUPAC Name | MW | % CAF @ 10 uM, 1 h |
|---|---|---|---|
| 408 | 7-((S)-4-acryloyl-2-methylpiperazin-1-yl)-9-chloro-10-(5-fluoro-1H-indazol-4-yl)-2,3-dihydro-5H-[1,4]thiazino[2,3,4-ij]quinazolin-5-one | 525 | 39.3 |
| 409 | 7-((S)-4-acryloyl-2-methylpiperazin-1-yl)-9-chloro-10-(2,4,5-trifluorophenyl)-2,3-dihydro-5H-[1,4]thiazino[2,3,4-ij]quinazolin-5-one | 520.95 | 94 |
| 410 | (S)-7-((S)-4-acryloyl-2-methylpiperazin-1-yl)-9-chloro-3-((4-ethylpiperazin-1-yl)methyl)-10-(4-fluorophenyl)-2,3-dihydro-5H-[1,4]thiazino[2,3,4-ij]quinazolin-5-one | 611.17 | 83.9 |
| 411 | (3S)-7-((S)-4-acryloyl-2-methylpiperazin-1-yl)-9-chloro-10-(2,4-difluorophenyl)-3-((4-methylpiperazin-1-yl)methyl)-2,3-dihydro-5H-[1,4]thiazino[2,3,4-ij]quinazolin-5-one | 615.14 | 93.3 |
| 412 | (3S)-7-((S)-4-acryloyl-2-methylpiperazin-1-yl)-9-chloro-10-(5-chloro-2,4-difluorophenyl)-3-((4-ethylpiperazin-1-yl)methyl)-2,3-dihydro-5H-[1,4]thiazino[2,3,4-ij]quinazolin-5-one | 663.61 | 73.6 |
| 413 | (3S)-7-((S)-4-acryloyl-2-methylpiperazin-1-yl)-9-chloro-10-(2,4-difluorophenyl)-3-((1-ethylpiperidin-4-yl)methyl)-2,3-dihydro-5H-[1,4]thiazino[2,3,4-ij]quinazolin-5-one | 628.18 | 86.6 |
| 414 | (3S)-7-((S)-4-acryloyl-2-methylpiperazin-1-yl)-9-chloro-3-((1-(2,2-difluoroethyl)piperidin-4-yl)methyl)-10-(2,4-difluorophenyl)-2H-[1,4]thiazino[2,3,4-ij]quinazolin-5(3H)-one | 664.16 | 92 |
| 415 | (3S)-7-((S)-4-acryloyl-2-methylpiperazin-1-yl)-9-chloro-10-(2,4-difluorophenyl)-3-((1-(oxetan-3-yl)piperidin-4-yl)methyl)-2,3-dihydro-5H-[1,4]thiazino[2,3,4-ij]quinazolin-5-one | 656.19 | 85.4 |
| 416 | (3S)-7-((S)-4-acryloyl-2-methylpiperazin-1-yl)-9-chloro-3-((4-ethylpiperazin-1-yl)methyl)-10-(2,4,5-trifluorophenyl)-2,3-dihydro-5H-[1,4]thiazino[2,3,4-ij]quinazolin-5-one | 647.15 | 91.2 |
| 417 | 7-(9-acryloyl-7,9-diazaspiro[bicyclo[3.3.1]nonane-3,3'-oxetan]-7-yl)-10-(2,4-difluorophenyl)-9-(trifluoromethyl)-2,3-dihydro-5H-[1,4]thiazino[2,3,4-ij]quinazolin-5-one | 604.59 | 2 |
| 418 | 10-(2,4-difluorophenyl)-7-(9-(2-fluoroacryloyl)-7-oxo-3,9-diazabicyclo[3.3.1]nonan-3-yl)-9-(trifluoromethyl)-2,3-dihydro-5H-[1,4]thiazino[2,3,4-ij]quinazolin-5-one | 594.53 | 58 |

TABLE 6-continued

| Example Number | IUPAC Name | MW | % CAF @ 10 uM, 1 h |
|---|---|---|---|
| | CAF data for compounds 408 to 589 | | |
| 419 | 7-((S)-4-acryloyl-2-methylpiperazin-1-yl)-9-chloro-10-(7-fluoro-1H-indazol-4-yl)-2,3-dihydro-5H-[1,4]thiazino[2,3,4-ij]quinazolin-5-one | 525 | 54.3 |
| 420 | (E)-10-(2,4-difluorophenyl)-7-(9-(4-(dimethylamino)but-2-enoyl)-7-oxo-3,9-diazabicyclo[3.3.1]nonan-3-yl)-9-(trifluoromethyl)-2,3-dihydro-5H-[1,4]thiazino[2,3,4-ij]quinazolin-5-one | 633.63 | 93 |
| 421 | (3S)-7-((S)-4-acryloyl-2-methylpiperazin-1-yl)-9-chloro-3-((1-(oxetan-3-yl)piperidin-4-yl)methyl)-10-(2,4,5-trifluorophenyl)-2,3-dihydro-5H-[1,4]thiazino[2,3,4-ij]quinazolin-5-one | 674.18 | 85.1 |
| 422 | (3S)-7-((S)-4-acryloyl-2-methylpiperazin-1-yl)-9-chloro-3-((4-cyclopropylpiperazin-1-yl)methyl)-10-(2,4-difluorophenyl)-2,3-dihydro-5H-[1,4]thiazino[2,3,4-ij]quinazolin-5-one | 641.17 | 84.2 |
| 423 | (3S)-7-((S)-4-acryloyl-2-methylpiperazin-1-yl)-9-chloro-10-(2,4-difluorophenyl)-3-((1-methylpiperidin-4-yl)methyl)-2,3-dihydro-5H-[1,4]thiazino[2,3,4-ij]quinazolin-5-one | 614.15 | 34.1 |
| 424 | (R)-7-((S)-4-acryloyl-2-methylpiperazin-1-yl)-9-chloro-3-((1-ethylpiperidin-4-yl)methyl)-10-(2,4,6-trifluorophenyl)-2,3-dihydro-5H-[1,4]thiazino[2,3,4-ij]quinazolin-5-one | 646.17 | 13.9 |
| 425 | (S)-7-((S)-4-acryloyl-2-methylpiperazin-1-yl)-10-(4-fluorophenyl)-3-((1-(oxetan-3-yl)piperidin-4-yl)methyl)-9-(trifluoromethyl)-2,3-dihydro-5H-[1,4]thiazino[2,3,4-ij]quinazolin-5-one | 671.75 | 94.7 |
| 426 | (3S)-7-((S)-4-acryloyl-2-methylpiperazin-1-yl)-9-chloro-10-(5-chloro-2,4-difluorophenyl)-3-((1-(oxetan-3-yl)piperidin-4-yl)methyl)-2,3-dihydro-5H-[1,4]thiazino[2,3,4-ij]quinazolin-5-one | 690.63 | 82.8 |
| 427 | 7-((S)-4-acryloyl-2-methylpiperazin-1-yl)-9-chloro-10-(2-chloro-4-fluorophenyl)-2,3-dihydro-5H-[1,4]thiazino[2,3,4-ij]quinazolin-5-one | 519.42 | 63.5 |
| 428 | (S)-7-((S)-4-acryloyl-2-methylpiperazin-1-yl)-3-((1-(2,2-difluoroethyl)piperidin-4-yl)methyl)-10-(4-fluorophenyl)-9-(trifluoromethyl)-2,3-dihydro-5H-[1,4]thiazino[2,3,4-ij]quinazolin-5-one | 679.72 | 79.6 |
| 429 | (3S)-7-((S)-4-acryloyl-2-methylpiperazin-1-yl)-3-((1-(2,2-difluoroethyl)piperidin-4-yl)methyl)-10-(2,4-difluorophenyl)-9-(trifluoromethyl)-2,3-dihydro-5H-[1,4]thiazino[2,3,4-ij]quinazolin-5-one 1,1-dioxide | 729.71 | 61 |
| 430 | (S)-7-((S)-4-acryloyl-2-methylpiperazin-1-yl)-10-(4-fluorophenyl)-9-(trifluoromethyl)-3-((3-(trifluoromethyl)-5,6-dihydro-[1,2,4]triazolo[4,3-a]pyrazin-7(8H)-yl)methyl)-2,3-dihydro-5H-[1,4]thiazino[2,3,4-ij]quinazolin-5-one | 722.68 | 90.9 |
| 431 | (3S)-8-((S)-4-acryloyl-2-methylpiperazin-1-yl)-11-(2,4-difluorophenyl)-3-hydroxy-10-(trifluoromethyl)-3,4-dihydro-2H,6H-[1,4]thiazepino[2,3,4-ij]quinazolin-6-one | 566.54 | 90 |
| 432 | (3R)-7-((S)-4-acryloyl-2-methylpiperazin-1-yl)-9-chloro-10-(2,4-difluorophenyl)-3-(((1-ethylazetidin-3-yl)oxy)methyl)-2,3-dihydro-5H-[1,4]thiazino[2,3,4-ij]quinazolin-5-one | 616.12 | 2.6 |
| 433 | 7'-((S)-4-acryloyl-2-methylpiperazin-1-yl)-9'-chloro-10'-(2,4-difluorophenyl)-3'H,5'H-spiro[cyclopropane-1,2'-[1,4]thiazino[2,3,4-ij]quinazolin]-5'-one | 529 | 25.3 |
| 434 | (3S)-7-((S)-4-acryloyl-2-methylpiperazin-1-yl)-10-(2,4-difluorophenyl)-3-((1-ethylpiperidin-4-yl)methyl)-9-(trifluoromethyl)-2,3-dihydro-5H-[1,4]thiazino[2,3,4-ij]quinazolin-5-one 1,1-dioxide | 693.73 | 51.5 |
| 435 | (3S)-7-((S)-4-acryloyl-2-methylpiperazin-1-yl)-10-(2,4-difluorophenyl)-3-(methoxymethyl)-9-(trifluoromethyl)-2,3-dihydro-5H-[1,4]thiazino[2,3,4-ij]quinazolin-5-one | 580.57 | 95.8 |
| 436 | (3S)-7-((S)-4-acryloyl-2-methylpiperazin-1-yl)-10-(2,4-difluorophenyl)-3-(methoxymethyl)-9-(trifluoromethyl)-2,3-dihydro-5H-[1,4]thiazino[2,3,4-ij]quinazolin-5-one 1,1-dioxide | 612.57 | 72.5 |
| 437 | (3S)-7-((S)-4-acryloyl-2-methylpiperazin-1-yl)-10-(2,4-difluorophenyl)-3-((tetrahydro-2H-pyran-4-yl)methyl)-9-(trifluoromethyl)-2,3-dihydro-5H-[1,4]thiazino[2,3,4-ij]quinazolin-5-one | 634.66 | 95.7 |
| 438 | (3S)-7-((S)-4-acryloyl-2-methylpiperazin-1-yl)-9-chloro-10-(2,4-difluorophenyl)-3-((tetrahydro-2H- | 601.11 | 92.8 |

TABLE 6-continued

CAF data for compounds 408 to 589

| Example Number | IUPAC Name | MW | % CAF @ 10 uM, 1 h |
|---|---|---|---|
| | pyran-4-yl)methyl)-2,3-dihydro-5H-[1,4]thiazino[2,3,4-ij]quinazolin-5-one | | |
| 439 | (E)-7-(9-(4,4-difluorobut-2-enoyl)-7-oxo-3,9-diazabicyclo[3.3.1]nonan-3-yl)-10-(2,4-difluorophenyl)-9-(trifluoromethyl)-2,3-dihydro-5H-[1,4]thiazino [2,3,4-ij]quinazolin-5-one | 626.55 | 97 |
| 440 | (E)-10-(2,4-difluorophenyl)-7-(7-oxo-9-(4,4,4-trifluorobut-2-enoyl)-3,9-diazabicyclo[3.3.1]nonan-3-yl)-9-(trifluoromethyl)-2,3-dihydro-5H-[1,4]thiazino[2,3,4-ij]quinazolin-5-one | 644.54 | 96 |
| 441 | 7-((S)-4-acryloyl-2-methylpiperazin-1-yl)-9-chloro-10-(5-fluoroquinolin-8-yl)-2,3-dihydro-5H-[1,4]thiazino[2,3,4-ij]quinazolin-5-one | 536.02 | 78.5 |
| 442 | (2S)-7-((S)-4-acryloyl-2-methylpiperazin-1-yl)-10-(2,4-difluorophenyl)-2-((dimethylamino)methyl)-9-(trifluoromethyl)-2,3-dihydro-5H-[1,4]thiazino[2,3,4-ij]quinazolin-5-one | 593.61 | 87 |
| 443 | (3S)-7-((2S,5R)-4-acryloyl-2,5-dimethylpiperazin-1-yl)-3-((4-(2,2-difluoroethyl)piperazin-1-yl)methyl)-9-(trifluoromethyl)-10-(2,4,5-trifluorophenyl)-2,3-dihydro-5H-[1,4]thiazino[2,3,4-ij]quinazolin-5-one | 730.71 | 48.2 |
| 444 | (S)-7-((S)-4-acryloyl-2-methylpiperazin-1-yl)-9-chloro-10-(4-fluorophenyl)-3-((3-(trifluoromethyl)-5,6-dihydro-[1,2,4]triazolo[4,3-a]pyrazin-7(8H)-yl)methyl)-2,3-dihydro-5H-[1,4]thiazino[2,3,4-ij]quinazolin-5-one | 689.13 | 24.1 |
| 445 | (S)-7-((2S,5R)-4-acryloyl-2,5-dimethylpiperazin-1-yl)-9-chloro-10-(4-fluorophenyl)-3-((3-(trifluoromethyl)-5,6-dihydro-[1,2,4]triazolo[4,3-a]pyrazin-7(8H)-yl)methyl)-2,3-dihydro-5H-[1,4]thiazino[2,3,4-ij]quinazolin-5-one | 703.15 | 68.2 |
| 446 | (3R)-7-((S)-4-acryloyl-2-methylpiperazin-1-yl)-9-chloro-10-(5-chloro-2,4 -difluorophenyl)-3-((methoxymethoxy)methyl)-2,3-dihydro-5H-[1,4]thiazino[2,3,4-ij]quinazolin-5-one | 611.49 | 38 |
| 447 | (3S)-7-((S)-4-acryloyl-2-methylpiperazin-1-yl)-9-chloro-10-(5-chloro-2,4-difluorophenyl)-3-((3-(trifluoromethyl)-5,6-dihydro-[1,2,4]triazolo[4,3-a]pyrazin-7(8H)-yl)methyl)-2,3-dihydro-5H-[1,4]thiazino[2,3,4-ij]quinazolin-5-one | 741.56 | 63.3 |
| 448 | (3S)-7-((2S,5R)-4-acryloyl-2,5-dimethylpiperazin-1-yl)-9-chloro-10-(5-chloro-2,4-difluorophenyl)-3-((3-(trifluoromethyl)-5,6-dihydro-[1,2,4]triazolo[4,3-a]pyrazin-7(8H)-yl)methyl)-2,3-dihydro-5H-[1,4]thiazino[2,3,4-ij]quinazolin-5-one | 755.59 | 55 |
| 449 | (3S)-3-((2-oxa-7-azaspiro[3.5]nonan-7-yl)methyl)-7-((2S,5R)-4-acryloyl-2,5-dimethylpiperazin-1-yl)-9-chloro-10-(5-chloro-2,4-difluorophenyl)-2,3-dihydro-5H-[1,4]thiazino[2,3,4-ij]quinazolin-5-one | 690.63 | 51.6 |
| 450 | 8-((S)-4-acryloyl-2-methylpiperazin-1-yl)-11-(2,4-difluorophenyl)-10-(trifluoromethyl)-3,4-dihydro-2H,6H-[1,4]thiazepino[2,3,4-ij]quinazolin-6-one | 550.54 | 61 |
| 451 | 11-(2,4-difluorophenyl)-8-(9-(2-fluoroacryloyl)-7-oxo-3,9-diazabicyclo[3.3.1]nonan-3-yl)-10-(trifluoromethyl)-3,4-dihydro-2H,6H-[1,4]thiazepino[2,3,4-ij]quinazolin-6-one | 608.55 | 61 |
| 452 | (E)-7-(9-(but-2-enoyl)-7-oxo-3,9-diazabicyclo[3.3.1]nonan-3-yl)-10-(2,4-difluorophenyl)-9-(trifluoromethyl)-2,3-dihydro-5H-[1,4]thiazino[2,3,4-ij]quinazolin-5-one | 590.56 | 63 |
| 453 | 7-(9-(but-2-ynoyl)-7-oxo-3,9-diazabicyclo[3.3.1]nonan-3-yl)-10-(2,4-difluorophenyl)-9-(trifluoromethyl)-2,3-dihydro-5H-[1,4]thiazino[2,3,4-ij]quinazolin-5-one | | 37 |
| 454 | (3S)-8-((S)-4-acryloyl-2-methylpiperazin-1-yl)-11-(2,4-difluorophenyl)-3-(methyl(2,2,2-trifluoroethyl)amino)-10-(trifluoromethyl)-3,4-dihydro-2H,6H-[1,4]thiazepino[2,3,4-ij]quinazolin-6-one | 661.61 | 61 |
| 455 | (S)-8-(4-acryloyl-2-methylpiperazin-1-yl)-10-(trifluoromethyl)-11-(2,4,6-trifluorophenyl)-3,4-dihydro-2H,6H-[1,4]thiazepino[2,3,4-ij]quinazolin-6-one | 534.98 | 21 |
| 456 | (3S)-3-((2-oxa-7-azaspiro[3.5]nonan-7-yl)methyl)-7-((S)-4-acryloyl-2-methylpiperazin-1-yl)-9-chloro-10-(5-chloro-2,4-difluorophenyl)-2,3-dihydro-5H-[1,4]thiazino[2,3,4-ij]quinazolin-5-one | 676.6 | 77.6 |

TABLE 6-continued

| CAF data for compounds 408 to 589 | | | |
|---|---|---|---|
| Example Number | IUPAC Name | MW | % CAF @ 10 uM, 1 h |
| 457 | (3S)-3-((2-oxa-7-azaspiro[3.5]nonan-7-yl)methyl)-7-((S)-4-acryloyl-2-methylpiperazin-1-yl)-9-chloro-10-(5-chloro-2,4-difluorophenyl)-2,3-dihydro-5H-[1,4]thiazino[2,3,4-ij]quinazolin-5-one | 699.59 | 76.8 |
| 458 | (3S)-7-((S)-4-acryloyl-2-methylpiperazin-1-yl)-9-chloro-10-(5-chloro-2,4-difluorophenyl)-3-((4-cyclopropylpiperazin-1-yl)methyl)-2,3-dihydro-5H-[1,4]thiazino[2,3,4-ij]quinazolin-5-one | 675.62 | 55.6 |
| 459 | (3S)-7-((S)-4-acryloyl-2-methylpiperazin-1-yl)-9-chloro-3-((3-(trifluoromethyl)-5,6-dihydro-[1,2,4]triazolo[4,3-a]pyrazin-7(8H)-yl)methyl)-10-(2,4,5-trifluorophenyl)-2,3-dihydro-5H-[1,4]thiazino[2,3,4-ij]quinazolin-5-one | 739.13 | 82.2 |
| 460 | (3S)-3-((2-oxa-7-azaspiro[3.5]nonan-7-yl)methyl)-7-((2S,5R)-4-acryloyl-2,5-dimethylpiperazin-1-yl)-9-chloro-10-(2,4,5-trifluorophenyl)-2,3-dihydro-5H-[1,4]thiazino[2,3,4-ij]quinazolin-5-one | 674.18 | 79.7 |
| 461 | (3S)-7-((2S,5R)-4-acryloyl-2,5-dimethylpiperazin-1-yl)-9-chloro-10-(5-chloro-2,4-difluorophenyl)-3-((1-(2,2-difluoroethyl)piperidin-4-yl)methyl)-2,3-dihydro-5H-[1,4]thiazino[2,3,4-ij]quinazolin-5-one | 712.63 | 79.5 |
| 462 | (S)-3-((2-oxa-7-azaspiro[3.5]nonan-7-yl)methyl)-7-((S)-4-acryloyl-2-methylpiperazin-1-yl)-9-chloro-10-(4-fluorophenyl)-2,3-dihydro-5H-[1,4]thiazino[2,3,4-ij]quinazolin-5-one | 624.17 | 87.8 |
| 463 | (3S)-7-((S)-4-acryloyl-2-methylpiperazin-1-yl)-9-chloro-3-((3-(trifluoromethyl)-5,6-dihydro-[1,2,4]triazolo[4,3-a]pyrazin-7(8H)-yl)methyl)-10-(2,4,5-trifluorophenyl)-2,3-dihydro-5H-[1,4]thiazino[2,3,4-ij]quinazolin-5-one | 725.11 | 69 |
| 464 | (3S)-8-((S)-4-acryloyl-2-methylpiperazin-1-yl)-11-(2,4-difluorophenyl)-3-methoxy-10-(trifluoromethyl)-3,4-dihydro-2H,6H-[1,4]thiazepino[2,3,4-ij]quinazolin-6-one | 580.57 | 95 |
| 465 | (3R)-8-((S)-4-acryloyl-2-methylpiperazin-1-yl)-11-(2,4-difluorophenyl)-3-methoxy-10-(trifluoromethyl)-3,4-dihydro-2H,6H-[1,4]thiazepino[2,3,4-ij]quinazolin-6-one | 580.57 | 96 |
| 466 | (3R)-7-((S)-4-acryloyl-2-methylpiperazin-1-yl)-9-chloro-3-((methoxymethoxy)methyl)-10-(2,4,5-trifluorophenyl)-2,3-dihydro-5H-[1,4]thiazino[2,3,4-ij]quinazolin-5-one | 595.03 | 22.6 |
| 467 | (3S)-7-((2S,5R)-4-acryloyl-2,5-dimethylpiperazin-1-yl)-9-chloro-10-(5-chloro-2,4-difluorophenyl)-3-((1-cyclopropylpiperidin-4-yl)methyl)-2,3-dihydro-5H-[1,4]thiazino[2,3,4-ij]quinazolin-5-one | 688.66 | 44.3 |
| 468 | (3S)-7-((2S,5R)-4-acryloyl-2,5-dimethylpiperazin-1-yl)-9-chloro-10-(2,4-difluorophenyl)-3-((3-(trifluoromethyl)-5,6-dihydro-[1,2,4]triazolo[4,3-a]pyrazin-7(8H)-yl)methyl)-2,3-dihydro-5H-[1,4]thiazino[2,3,4-ij]quinazolin-5-one | 721.14 | 68.6 |
| 469 | (3S)-3-((2-oxa-7-azaspiro[3.5]nonan-7-yl)methyl)-7-((S)-4-acryloyl-2-methylpiperazin-1-yl)-9-chloro-10-(2,4,5-trifluorophenyl)-2,3-dihydro-5H-[1,4]thiazino[2,3,4-ij]quinazolin-5-one | 660.15 | 57.8 |
| 470 | (3R)-7-((S)-4-acryloyl-2-methylpiperazin-1-yl)-10-(5-chloro-2,4-difluorophenyl)-3-((methoxymethoxy)methyl)-9-(trifluoromethyl)-2,3-dihydro-5H-[1,4]thiazino[2,3,4-ij]quinazolin-5-one | 645.04 | 35 |
| 471 | (3R)-7-((S)-4-acryloyl-2-methylpiperazin-1-yl)-3-((methoxymethoxy)methyl)-9-(trifluoromethyl)-10-(2,4,5-trifluorophenyl)-2,3-dihydro-5H-[1,4]thiazino[2,3,4-ij]quinazolin-5-one | 628.59 | 23.9 |
| 472 | (3S)-3-((2-oxa-7-azaspiro[3.5]nonan-7-yl)methyl)-7-((S)-4-acryloyl-2-methylpiperazin-1-yl)-9-chloro-10-(2,4-difluorophenyl)-2,3-dihydro-5H-[1,4]thiazino[2,3,4-ij]quinazolin-5-one | 642.16 | 72.3 |
| 473 | (S)-3-((2-oxa-7-azaspiro[3.5]nonan-7-yl)methyl)-7-((2S,5R)-4-acryloyl-2,5-dimethylpiperazin-1-yl)-9-chloro-10-(4-fluorophenyl)-2,3-dihydro-5H-[1,4]thiazino[2,3,4-ij]quinazolin-5-one | 638.2 | 65.8 |
| 474 | (3S)-7-((S)-4-acryloyl-2-methylpiperazin-1-yl)-9-chloro-10-(5-fluoroquinolin-8-yl)-3-(methoxymethyl)-2,3-dihydro-5H-[1,4]thiazino[2,3,4-ij]quinazolin-5-one | 580.07 | 73.3 |

TABLE 6-continued

| Example Number | IUPAC Name | MW | % CAF @ 10 uM, 1 h |
|---|---|---|---|
| | CAF data for compounds 408 to 589 | | |
| 475 | (3S)-7-((2S,5R)-4-acryloyl-2,5-dimethylpiperazin-1-yl)-9-chloro-3-((1-cyclopropylpiperidin-4-yl)methyl)-10-(2,4,5-trifluorophenyl)-2,3-dihydro-5H-[1,4]thiazino[2,3,4-ij]quinazolin-5-one | 672.2 | 49.8 |
| 476 | (3S)-7-((2S,5R)-4-acryloyl-2,5-dimethylpiperazin-1-yl)-9-chloro-3-((1-(2,2-difluoroethyl)piperidin-4-yl)methyl)-10-(2,4,5-trifluorophenyl)-2,3-dihydro-5H-[1,4]thiazino[2,3,4-ij]quinazolin-5-one | 696.17 | 53.8 |
| 477 | (3S)-7-((2S,5R)-4-acryloyl-2,5-dimethylpiperazin-1-yl)-9-chloro-3-((1-(2,2-difluoroethyl)piperidin-4-yl)methyl)-10-(2,4-difluorophenyl)-2,3-dihydro-5H-[1,4]thiazino[2,3,4-ij]quinazolin-5-one | 678.18 | 63.5 |
| 478 | (3S)-7-((2S,5R)-4-acryloyl-2,5-dimethylpiperazin-1-yl)-9-chloro-3-((1-cyclopropylpiperidin-4-yl)methyl)-10-(2,4-difluorophenyl)-2,3-dihydro-5H-[1,4]thiazino[2,3,4-ij]quinazolin-5-one | 654.21 | 70.7 |
| 479 | (3R)-7-((S)-4-acryloyl-2-methylpiperazin-1-yl)-9-chloro-10-(2,4-difluorophenyl)-3-((methoxymethoxy)methyl)-2,3-dihydro-5H-[1,4]thiazino[2,3,4-ij]quinazolin-5-one | 577.04 | 42 |
| 480 | (3S)-7-((S)-4-acryloyl-2-methylpiperazin-1-yl)-9-chloro-3-((4-(2,2-difluoroethyl)piperazin-1-yl)methyl)-10-(2,4,5-trifluorophenyl)-2,3-dihydro-5H-[1,4]thiazino[2,3,4-ij]quinazolin-5-one | 683.13 | 61.2 |
| 481 | (S)-7-((2S,5R)-4-acryloyl-2,5-dimethylpiperazin-1-yl)-3-((1-(2,2-difluoroethyl)azetidin-3-yl)methyl)-10-(4-fluorophenyl)-9-(trifluoromethyl)-2,3-dihydro-5H-[1,4]thiazino[2,3,4-ij]quinazolin-5-one | 665.69 | 59.4 |
| 482 | (3S,10S)-3-((2-oxa-7-azaspiro[3.5]nonan-7-yl)methyl)-7-((S)-4-acryloyl-2-methylpiperazin-1-yl)-9-chloro-10-(5-chloro-2,4-difluorophenyl)-2,3-dihydro-5H-[1,4]thiazino[2,3,4-ij]quinazolin-5-one | 676.6 | 90 |
| 483 | (3S,10R)-3-((2-oxa-7-azaspiro[3.5]nonan-7-yl)methyl)-7-((S)-4-acryloyl-2-methylpiperazin-1-yl)-9-chloro-10-(5-chloro-2,4-difluorophenyl)-2,3-dihydro-5H-[1,4]thiazino[2,3,4-ij]quinazolin-5-one | 676.6 | 15.7 |
| 484 | (3S,10S)-3-((2-oxa-7-azaspiro[3.5]nonan-7-yl)methyl)-7-((2S,5R)-4-acryloyl-2,5-dimethylpiperazin-1-yl)-9-chloro-10-(2,4,5-trifluorophenyl)-2,3-dihydro-5H-[1,4]thiazino[2,3,4-ij]quinazolin-5-one | 674.18 | 77.9 |
| 485 | (3S,10R)-3-((2-oxa-7-azaspiro[3.5]nonan-7-yl)methyl)-7-((2S,5R)-4-acryloyl-2,5-dimethylpiperazin-1-yl)-9-chloro-10-(2,4,5-trifluorophenyl)-2,3-dihydro-5H-[1,4]thiazino[2,3,4-ij]quinazolin-5-one | 674.18 | 45 |
| 486 | 8-(9-acryloyl-7-oxo-3,9-diazabicyclo[3.3.1]nonan-3-yl)-11-(2,4-difluorophenyl)-10-(trifluoromethyl)-3,4-dihydro-2H,6H-[1,4]thiazepino[2,3,4-ij]quinazolin-6-one | 590.56 | 95 |
| 487 | (3S)-8-((S)-4-acryloyl-2-methylpiperazin-1-yl)-10-chloro-11-(2,4-difluorophenyl)-3-methoxy-3,4-dihydro-2H,6H-[1,4]thiazepino[2,3,4-ij]quinazolin-6-one | 547.02 | 96 |
| 488 | (3R)-8-((S)-4-acryloyl-2-methylpiperazin-1-yl)-10-chloro-11-(2,4-difluorophenyl)-3-methoxy-3,4-dihydro-2H,6H-[1,4]thiazepino[2,3,4-ij]quinazolin-6-one | 547.02 | 96 |
| 489 | (3S)-8-(4-acryloylpiperazin-1-yl)-11-(2,4-difluorophenyl)-3-methoxy-10-(trifluoromethyl)-3,4-dihydro-2H,6H-[1,4]thiazepino[2,3,4-ij]quinazolin-6-one | 566.54 | 96 |
| 490 | (3R)-8-(4-acryloylpiperazin-1-yl)-11-(2,4-difluorophenyl)-3-methoxy-10-(trifluoromethyl)-3,4-dihydro-2H,6H-[1,4]thiazepino[2,3,4-ij]quinazolin-6-one | 566.54 | |
| 491 | (3S)-7-((2S,5R)-4-acryloyl-2,5-dimethylpiperazin-1-yl)-3-(methoxymethyl)-9-(trifluoromethyl)-10-(2,4,5-trifluorophenyl)-2,3-dihydro-5H-[1,4]thiazino[2,3,4-ij]quinazolin-5-one | 612.59 | 60 |
| 492 | (3S)-7-((2S,5R)-4-acryloyl-2,5-dimethylpiperazin-1-yl)-10-(5-chloro-2,4-difluorophenyl)-3-(methoxymethyl)-9-(trifluoromethyl)-2,3-dihydro-5H-[1,4]thiazino[2,3,4-ij]quinazolin-5-one | 629.04 | 63.2 |
| 493 | (3S)-7-((2S,5R)-4-acryloyl-2,5-dimethylpiperazin-1-yl)-10-(2,4-difluorophenyl)-3-(methoxymethyl)-9-(trifluoromethyl)-2,3-dihydro-5H-[1,4]thiazino[2,3,4-ij]quinazolin-5-one | 594.6 | 78.6 |

TABLE 6-continued

CAF data for compounds 408 to 589

| Example Number | IUPAC Name | MW | % CAF @ 10 uM, 1 h |
|---|---|---|---|
| 494 | (3S)-7-((2S,5R)-4-acryloyl-2,5-dimethylpiperazin-1-yl)-9-chloro-10-(2,4-difluorophenyl)-3-(methoxymethyl)-2,3-dihydro-5H-[1,4]thiazino[2,3,4-ij]quinazolin-5-one | 561.04 | 68.7 |
| 495 | (3S)-7-((2S,5R)-4-acryloyl-2,5-dimethylpiperazin-1-yl)-9-chloro-10-(5-chloro-2,4-difluorophenyl)-3-((4-(2,2-difluoroethyl)piperazin-1-yl)methyl)-2,3-dihydro-5H-[1,4]thiazino[2,3,4-ij]quinazolin-5-one | 713.62 | 50.8 |
| 496 | (3S)-7-((2S,5R)-4-acryloyl-2,5-dimethylpiperazin-1-yl)-9-chloro-10-(5-chloro-2,4-difluorophenyl)-3-(methoxymethyl)-2,3-dihydro-5H-[1,4]thiazino[2,3,4-ij]quinazolin-5-one | 595.49 | 65.3 |
| 497 | (S)-7-((2S,5R)-4-acryloyl-2,5-dimethylpiperazin-1-yl)-10-(4-fluorophenyl)-3-(methoxymethyl)-9-(trifluoromethyl)-2,3-dihydro-5H-[1,4]thiazino[2,3,4-ij]quinazolin-5-one | 576.61 | 85.1 |
| 498 | (3S)-7-((2S,5R)-4-acryloyl-2,5-dimethylpiperazin-1-yl)-10-(2,4-difluorophenyl)-3-((2-methoxyethoxy)methyl)-9-(trifluoromethyl)-2,3-dihydro-5H-[1,4]thiazino[2,3,4-ij]quinazolin-5-one | 638.65 | 81.2 |
| 499 | (3S)-7-((2S,5R)-4-acryloyl-2,5-dimethylpiperazin-1-yl)-9-chloro-10-(5-chloro-2,4-difluorophenyl)-3-((4-cyclopropylpiperazin-1-yl)methyl)-2,3-dihydro-5H-[1,4]thiazino[2,3,4-ij]quinazolin-5-one | 689.65 | 28 |
| 500 | (3S)-3-(((1S,4S)-2-oxa-5-azabicyclo[2.2.1]heptan-5-yl)methyl)-7-((2S,5R)-4-acryloyl-2,5-dimethylpiperazin-1-yl)-9-chloro-10-(5-chloro-2,4-difluorophenyl)-2,3-dihydro-5H-[1,4]thiazino[2,3,4-ij]quinazolin-5-one | 662.58 | 50.6 |
| 501 | (3S)-7-((2S,5R)-4-acryloyl-2,5-dimethylpiperazin-1-yl)-9-chloro-10-(2,4-difluorophenyl)-3-((2-methoxyethoxy)methyl)-2,3-dihydro-5H-[1,4]thiazino[2,3,4-ij]quinazolin-5-one | 605.1 | 66.8 |
| 502 | (3S)-7-((2S,5R)-4-acryloyl-2,5-dimethylpiperazin-1-yl)-9-chloro-10-(5-chloro-2,4-difluorophenyl)-3-((2-methoxyethoxy)methyl)-2,3-dihydro-5H-[1,4]thiazino[2,3,4-ij]quinazolin-5-one | 639.54 | 65.1 |
| 503 | (3S)-8-((3S,5R)-4-acryloyl-3,5-dimethylpiperazin-1-yl)-11-(2,4-difluorophenyl)-3-methoxy-10-(trifluoromethyl)-3,4-dihydro-2H,6H-[1,4]thiazepino[2,3,4-ij]quinazolin-6-one | 594.6 | 96 |
| 504 | (3S)-8-(4-acryloylpiperazin-1-yl)-10-chloro-11-(2,4-difluorophenyl)-3-methoxy-3,4-dihydro-2H,6H-[1,4]thiazepino[2,3,4-ij]quinazolin-6-one | 532.99 | 96 |
| 505 | (3S)-8-((3S,5R)-4-acryloyl-3,5-dimethylpiperazin-1-yl)-10-chloro-11-(2,4-difluorophenyl)-3-methoxy-3,4-dihydro-2H,6H-[1,4]thiazepino[2,3,4-ij]quinazolin-6-one | 561.04 | 95 |
| 506 | (3S)-7-((3S,5R)-4-acryloyl-3,5-dimethylpiperazin-1-yl)-9-chloro-3-(methoxymethyl)-10-(2,4,5-trifluorophenyl)-2,3-dihydro-5H-[1,4]thiazino[2,3,4-ij]quinazolin-5-one | 579.03 | 17.5 |
| 507 | (2S)-7-((S)-4-acryloyl-2-methylpiperazin-1-yl)-10-(2,4-difluorophenyl)-2-(methoxymethyl)-9-(trifluoromethyl)-2,3-dihydro-5H-[1,4]thiazino[2,3,4-ij]quinazolin-5-one | 580.57 | 71 |
| 508 | (3S,10S)-7-((2S,5R)-4-acryloyl-2,5-dimethylpiperazin-1-yl)-10-(2,4-difluorophenyl)-3-(methoxymethyl)-9-(trifluoromethyl)-2,3-dihydro-5H-[1,4]thiazino[2,3,4-ij]quinazolin-5-one | 594.6 | 92 |
| 509 | (3S,10R)-7-((2S,5R)-4-acryloyl-2,5-dimethylpiperazin-1-yl)-10-(2,4-difluorophenyl)-3-(methoxymethyl)-9-(trifluoromethyl)-2,3-dihydro-5H-[1,4]thiazino[2,3,4-ij]quinazolin-5-one | 594.6 | 96.5 |
| 510 | (3S,10S)-7-((2S,5R)-4-acryloyl-2,5-dimethylpiperazin-1-yl)-10-(2,4-difluorophenyl)-3-((2-methoxyethoxy)methyl)-9-(trifluoromethyl)-2,3-dihydro-5H-[1,4]thiazino[2,3,4-ij]quinazolin-5-one | 638.65 | 72.9 |
| 511 | (3S,10R)-7-((2S,5R)-4-acryloyl-2,5-dimethylpiperazin-1-yl)-10-(2,4-difluorophenyl)-3-((2-methoxyethoxy)methyl)-9-(trifluoromethyl)-2,3-dihydro-5H-[1,4]thiazino[2,3,4-ij]quinazolin-5-one | 638.65 | 80.6 |
| 512 | S)-7-((2S,5R)-4-acryloyl-2,5-dimethylpiperazin-1-yl)-10-(4-fluorophenyl)-3-((2-methoxyethoxy)methyl)-9-(trifluoromethyl)-2,3-dihydro-5H-[1,4]thiazino[2,3,4-ij]quinazolin-5-one | 620.66 | 66.1 |
| 513 | (3S)-7-((3S,5R)-4-acryloyl-3,5-dimethylpiperazin-1-yl)-10-(2,4-difluorophenyl)-3-(methoxymethyl)-9- | 594.6 | 96.2 |

TABLE 6-continued

| CAF data for compounds 408 to 589 | | | |
|---|---|---|---|
| Example Number | IUPAC Name | MW | % CAF @ 10 uM, 1 h |
| | (trifluoromethyl)-2,3-dihydro-5H-[1,4]thiazino[2,3,4-ij]quinazolin-5-one | | |
| 514 | (3S)-7-(4-acryloylpiperazin-1-yl)-10-(2,4-difluorophenyl)-3-(methoxymethyl)-9-(trifluoromethyl)-2,3-dihydro-5H-[1,4]thiazino[2,3,4-ij]quinazolin-5-one | 566.54 | 96.1 |
| 515 | (S)-7-((2S,5R)-4-acryloyl-2,5-dimethylpiperazin-1-yl)-9-chloro-3-((4-(2,2-difluoroethyl)piperazin-1-yl)methyl)-10-(4-fluorophenyl)-2,3-dihydro-5H-[1,4]thiazino[2,3,4-ij]quinazolin-5-one | 661.18 | 55.1 |
| 516 | (S)-7-((S)-4-acryloyl-2-methylpiperazin-1-yl)-10-(4-fluorophenyl)-3-((methoxymethoxy)methyl)-9-(trifluoromethyl)-2,3-dihydro-5H-[1,4]thiazino[2,3,4-ij]quinazolin-5-one | 592.6 | 74.4 |
| 517 | (S)-7-((2S,5R)-4-acryloyl-2,5-dimethylpiperazin-1-yl)-9-chloro-3-((4-cyclopropylpiperazin-1-yl)methyl)-10-(4-fluorophenyl)-2,3-dihydro-5H-[1,4]thiazino[2,3,4-ij]quinazolin-5-one | 637.21 | 59.5 |
| 518 | (3S)-7-((S)-4-acryloyl-2-methylpiperazin-1-yl)-10-(5-chloro-2,4-difluorophenyl)-3-((methoxymethoxy)methyl)-9-(trifluoromethyl)-2,3-dihydro-5H-[1,4]thiazino[2,3,4-ij]quinazolin-5-one | 645.04 | |
| 519 | (3S)-3-(((1S,4S)-2-oxa-5-azabicyclo[2.2.1]heptan-5-yl)methyl)-7-((2S,5R)-4-acryloyl-2,5-dimethylpiperazin-1-yl)-9-chloro-10-(2,4-difluorophenyl)-2,3-dihydro-5H-[1,4]thiazino[2,3,4-ij]quinazolin-5-one | 628.13 | 61.3 |
| 520 | (3S)-7-((S)-4-acryloyl-2-methylpiperazin-1-yl)-9-chloro-3-((4-cyclopropylpiperazin-1-yl)methyl)-10-(2,4,5-trifluorophenyl)-2,3-dihydro-5H-[1,4]thiazino[2,3,4-ij]quinazolin-5-one | 659.16 | 51.1 |
| 521 | (3S)-7-((2S,5R)-4-acryloyl-2,5-dimethylpiperazin-1-yl)-10-(5-chloro-2,4-difluorophenyl)-3-((4-(2,2-difluoroethyl)piperazin-1-yl)methyl)-9-(trifluoromethyl)-2,3-dihydro-5H-[1,4]thiazino[2,3,4-ij]quinazolin-5-one | 747.17 | 40.6 |
| 522 | (3S)-7-((S)-4-acryloyl-2-methylpiperazin-1-yl)-3-((methoxymethoxy)methyl)-9-(trifluoromethyl)-10-(2,4,5-trifluorophenyl)-2,3-dihydro-5H-[1,4]thiazino[2,3,4-ij]quinazolin-5-one | 628.59 | 72.4 |
| 523 | (3S)-7-(9-acryloyl-7,7-difluoro-3,9-diazabicyclo[3.3.1]nonan-3-yl)-10-(2,4-difluorophenyl)-3-(methoxymethyl)-9-(trifluoromethyl)-2,3-dihydro-5H-[1,4]thiazino[2,3,4-ij]quinazolin-5-one | 642.59 | 68.9 |
| 524 | (3R)-8-((3S,5R)-4-acryloyl-3,5-dimethylpiperazin-1-yl)-11-(2,4-difluorophenyl)-3-methoxy-10-(trifluoromethyl)-3,4-dihydro-2H,6H-[1,4]thiazepino[2,3,4-ij]quinazolin-6-one | 594.6 | 95 |
| 525 | (3R)-8-(4-acryloylpiperazin-1-yl)-10-chloro-11-(2,4-difluorophenyl)-3-methoxy-3,4-dihydro-2H,6H-[1,4]thiazepino[2,3,4-ij]quinazolin-6-one | 532.99 | 86 |
| 526 | (3R)-8-((3S,5R)-4-acryloyl-3,5-dimethylpiperazin-1-yl)-10-chloro-11-(2,4-difluorophenyl)-3-methoxy-3,4-dihydro-2H,6H-[1,4]thiazepino[2,3,4-ij]quinazolin-6-one | 561.04 | 93 |
| 527 | (R)-8-((S)-4-acryloyl-2-methylpiperazin-1-yl)-11-(4-fluorophenyl)-3-methoxy-10-(trifluoromethyl)-3,4-dihydro-2H,6H-[1,4]thiazepino[2,3,4-ij]quinazolin-6-one | 562.58 | 97 |
| 528 | (R)-8-((S)-4-acryloyl-2-methylpiperazin-1-yl)-10-chloro-11-(4-fluorophenyl)-3-methoxy-3,4-dihydro-2H,6H-[1,4]thiazepino[2,3,4-ij]quinazolin-6-one | 529.03 | 98 |
| 529 | (3S)-8-((S)-4-acryloyl-2-methylpiperazin-1-yl)-10-chloro-11-(5-chloro-2,4-difluorophenyl)-3-methoxy-3,4-dihydro-2H,6H-[1,4]thiazepino[2,3,4-ij]quinazolin-6-one | 581.46 | 95 |
| 530 | (3S)-8-((3S,5R)-4-acryloyl-3,5-dimethylpiperazin-1-yl)-10-chloro-11-(5-chloro-2,4-difluorophenyl)-3-methoxy-3,4-dihydro-2H,6H-[1,4]thiazepino[2,3,4-ij]quinazolin-6-one | 595.49 | 92 |
| 531 | 8'-((3S,5R)-4-acryloyl-3,5-dimethylpiperazin-1-yl)-11'-(2,4-difluorophenyl)-10'-(trifluoromethyl)-2'H,4'H,6'H-spiro[oxetane-3,3'-[1,4]thiazepino[2,3,4-ij]quinazolin]-6'-one | 606.61 | 88.6 |
| 532 | (S)-8-((S)-4-acryloyl-2-methylpiperazin-1-yl)-11-(4 -fluorophenyl)-3-methoxy-10-(trifluoromethyl)-3,4- | 562.58 | 97 |

TABLE 6-continued

| Example Number | IUPAC Name | MW | % CAF @ 10 uM, 1 h |
|---|---|---|---|
| CAF data for compounds 408 to 589 | | | |
| | dihydro-2H,6H-[1,4]thiazepino[2,3,4-ij]quinazolin-6-one | | |
| 533 | (3R)-8-((S)-4-acryloyl-2-methylpiperazin-1-yl)-11-(5-chloro-2,4-difluorophenyl)-3-methoxy-10-(trifluoromethyl)-3,4-dihydro-2H,6H-[1,4]thiazepino[2,3,4-ij]quinazolin-6-one | 615.01 | 96 |
| 534 | (3R)-8-(4-acryloylpiperazin-1-yl)-11-(5-chloro-2,4-difluorophenyl)-3-methoxy-10-(trifluoromethyl)-3,4-dihydro-2H,6H-[1,4]thiazepino[2,3,4-ij]quinazolin-6-one | 600.99 | 97 |
| 535 | (3R)-8-((3S,5R)-4-acryloyl-3,5-dimethylpiperazin-1-yl)-11-(5-chloro-2,4-difluorophenyl)-3-methoxy-10-(trifluoromethyl)-3,4-dihydro-2H,6H-[1,4]thiazepino[2,3,4-ij]quinazolin-6-one | 629.04 | 96 |
| 536 | (S)-8-(4-acryloylpiperazin-1-yl)-10-chloro-11-(4-fluorophenyl)-3-methoxy-3,4-dihydro-2H,6H-[1,4]thiazepino[2,3,4-ij]quinazolin-6-one | 515 | 97 |
| 537 | (S)-8-((S)-4-acryloyl-2-methylpiperazin-1-yl)-10-chloro-11-(4-fluorophenyl)-3-methoxy-3,4-dihydro-2H,6H-[1,4]thiazepino[2,3,4-ij]quinazolin-6-one | 529.03 | 96 |
| 538 | (3R)-8-(4-acryloylpiperazin-1-yl)-10-chloro-11-(5-chloro-2,4-difluorophenyl)-3-methoxy-3,4-dihydro-2H,6H-[1,4]thiazepino[2,3,4-ij]quinazolin-6-one | 567.43 | 97 |
| 539 | (3S)-8-((3S,5R)-4-acryloyl-3,5-dimethylpiperazin-1-yl)-11-(5-chloro-2,4-difluorophenyl)-3-methoxy-10-(trifluoromethyl)-3,4-dihydro-2H,6H-[1,4]thiazepino[2,3,4-ij]quinazolin-6-one | | 96 |
| 540 | (R)-8-(4-acryloylpiperazin-1-yl)-10-chloro-11-(4-fluorophenyl)-3-methoxy-3,4-dihydro-2H,6H-[1,4]thiazepino[2,3,4-ij]quinazolin-6-one | | 98 |
| 541 | (3R)-8-((S)-4-acryloyl-2-methylpiperazin-1-yl)-10-chloro-11-(5-chloro-2,4-difluorophenyl)-3-methoxy-3,4-dihydro-2H,6H-[1,4]thiazepino[2,3,4-ij]quinazolin-6-one | | 96 |
| 542 | (3R)-8-((3S,5R)-4-acryloyl-3,5-dimethylpiperazin-1-yl)-10-chloro-11-(5-chloro-2,4-difluorophenyl)-3-methoxy-3,4-dihydro-2H,6H-[1,4]thiazepino[2,3,4-ij]quinazolin-6-one | | 96 |
| 543 | (3S)-8-(4-acryloylpiperazin-1-yl)-10-chloro-11-(5-chloro-2,4-difluorophenyl)-3-methoxy-3,4-dihydro-2H,6H-[1,4]thiazepino[2,3,4-ij]quinazolin-6-one | | 97 |
| 544 | (3S,10S)-7-((2S,5R)-4-acryloyl-2,5-dimethylpiperazin-1-yl)-10-(5-chloro-2,4-difluorophenyl)-3-(methoxymethyl)-9-(trifluoromethyl)-2,3-dihydro-5H-[1,4]thiazino[2,3,4-ij]quinazolin-5-one | 629.04 | 48.8 |
| 545 | (3S,10R)-7-((2S,5R)-4-acryloyl-2,5-dimethylpiperazin-1-yl)-10-(5-chloro-2,4-difluorophenyl)-3-(methoxymethyl)-9-(trifluoromethyl)-2,3-dihydro-5H-[1,4]thiazino[2,3,4-ij]quinazolin-5-one | 629.04 | 94.1 |
| 546 | (3S,10S)-7-((3S,5R)-4-acryloyl-3,5-dimethylpiperazin-1-yl)-10-(2,4-difluorophenyl)-3-(methoxymethyl)-9-(trifluoromethyl)-2,3-dihydro-5H-[1,4]thiazino[2,3,4-ij]quinazolin-5-one | 594.6 | 94.3 |
| 547 | (3S,10R)-7-((3S,5R)-4-acryloyl-3,5-dimethylpiperazin-1-yl)-10-(2,4-difluorophenyl)-3-(methoxymethyl)-9-(trifluoromethyl)-2,3-dihydro-5H-[1,4]thiazino[2,3,4-ij]quinazolin-5-one | 594.6 | 96.7 |
| 548 | (3S,10R)-7-((S)-4-acryloyl-2-methylpiperazin-1-yl)-10-(2,4-difluorophenyl)-3-((methoxymethoxy)methyl)-9-(trifluoromethyl)-2,3-dihydro-5H-[1,4]thiazino[2,3,4-ij]quinazolin-5-one | 610.6 | 95.7 |
| 549 | (3S,10S)-7-((S)-4-acryloyl-2-methylpiperazin-1-yl)-10-(2,4-difluorophenyl)-3-((methoxymethoxy)methyl)-9-(trifluoromethyl)-2,3-dihydro-5H-[1,4]thiazino[2,3,4-ij]quinazolin-5-one | 610.6 | 80.2 |
| 550 | (3S)-7-((2S,5R)-4-acryloyl-2,5-dimethylpiperazin-1-yl)-9-chloro-3-((4-(2,2-difluoroethyl)piperazin-1-yl)methyl)-10-(2,4-difluorophenyl)-2,3-dihydro-5H-[1,4]thiazino[2,3,4-ij]quinazolin-5-one | 679.17 | 91.6 |
| 551 | (3S)-7-((2S,5R)-4-acryloyl-2,5-dimethylpiperazin-1-yl)-9-chloro-3-((4-cyclopropylpiperazin-1-yl)methyl)-10-(2,4-difluorophenyl)-2,3-dihydro-5H-[1,4]thiazino[2,3,4-ij]quinazolin-5-one | 655.2 | 53.4 |
| 552 | (3S,10R)-7-((S)-4-acryloyl-2-methylpiperazin-1-yl)-10-(5-chloro-2,4-difluorophenyl)-3- | 645.04 | 62.2 |

TABLE 6-continued

| CAF data for compounds 408 to 589 | | | |
|---|---|---|---|
| Example Number | IUPAC Name | MW | % CAF @ 10 uM, 1 h |
| | ((methoxymethoxy)methyl)-9-(trifluoromethyl)-2,3-dihydro-5H-[1,4]thiazino[2,3,4-ij]quinazolin-5-one | | |
| 553 | (3S,10S)-7-((S)-4-acryloyl-2-methylpiperazin-1-yl)-10-(5-chloro-2,4-difluorophenyl)-3-((methoxymethoxy)methyl)-9-(trifluoromethyl)-2,3-dihydro-5H-[1,4]thiazino[2,3,4-ij]quinazolin-5-one | 645.04 | 37 |
| 554 | (3S,10S)-7-((2S,5R)-4-acryloyl-2,5-dimethylpiperazin-1-yl)-10-(5-chloro-2,4 -difluorophenyl)-3-((2-methoxyethoxy)methyl)-9-(trifluoromethyl)-2,3-dihydro-5H-[1,4]thiazino[2,3,4-ij]quinazolin-5-one | 673.09 | 11.3 |
| 555 | (3S,10R)-7-((2S,5R)-4-acryloyl-2,5-dimethylpiperazin-1-yl)-10-(5-chloro-2,4 -difluorophenyl)-3-((2-methoxyethoxy)methyl)-9-(trifluoromethyl)-2,3-dihydro-5H-[1,4]thiazino[2,3,4-ij]quinazolin-5-one | 673.09 | 67.6 |
| 556 | (3S,10R)-7-((2S,5R)-4-acryloyl-2,5-dimethylpiperazin-1-yl)-10-(5-chloro-2,4-difluorophenyl)-3-((4-(2,2-difluoroethyl)piperazin-1-yl)methyl)-9-(trifluoromethyl)-2,3-dihydro-5H-[1,4]thiazino[2,3,4-ij]quinazolin-5-one | 747.17 | 73.1 |
| 557 | (3S,10S)-7-((2S,5R)-4-acryloyl-2,5-dimethylpiperazin-1-yl)-10-(5-chloro-2,4-difluorophenyl)-3-((4-(2,2-difluoroethyl)piperazin-1-yl)methyl)-9-(trifluoromethyl)-2,3-dihydro-5H-[1,4]thiazino[2,3,4-ij]quinazolin-5-one | 747.17 | 21.2 |
| 558 | (S)-7-((2S,5R)-4-acryloyl-2,5-dimethylpiperazin-1-yl)-9-chloro-10-(4-fluorophenyl)-3-((2-methoxyethoxy)methyl)-2,3-dihydro-5H-[1,4]thiazino[2,3,4-ij]quinazolin-5-one | 587.11 | 64.3 |
| 559 | (3S)-7-((3S,5R)-4-acryloyl-3,5-dimethylpiperazin-1-yl)-10-(5-chloro-2,4-difluorophenyl)-3-(methoxymethyl)-9-(trifluoromethyl)-2,3-dihydro-5H-[1,4]thiazino[2,3,4-ij]quinazolin-5-one | 629.04 | 83.8 |
| 560 | (3S)-3-(((1S,4S)-2-oxa-5-azabicyclo[2.2.1]heptan-5-yl)methyl)-7-((3S,5R)-4-acryloyl-3,5-dimethylpiperazin-1-yl)-10-(2,4-difluorophenyl)-9-(trifluoromethyl)-2,3-dihydro-5H-[1,4]thiazino[2,3,4-ij]quinazolin-5-one | 661.69 | 95.6 |
| 561 | 2-(4-(((3S)-7-((2S,5R)-4-acryloyl-2,5-dimethylpiperazin-1-yl)-10-(2,4-difluorophenyl)-5-oxo-9-(trifluoromethyl)-2,3-dihydro-5H-[1,4]thiazino[2,3,4-ij]quinazolin-3-yl)methyl)piperazin-1-yl)acetonitrile | 687.73 | 10.4 |
| 562 | (3S)-7-((2S,5R)-4-acryloyl-2,5-dimethylpiperazin-1-yl)-3-((4-(2,2-difluoroethyl)piperazin-l-yl)methyl)-10-(2,4-difluorophenyl)-9-(trifluoromethyl)-2,3-dihydro-5H-[1,4]thiazino[2,3,4-ij]quinazolin-5-one | 712.72 | 83.6 |
| 563 | (3S,10R)-7-((3S,5R)-4-acryloyl-3,5-dimethylpiperazin-l -yl)-10-(5-chloro-2,4-difluorophenyl)-3-(methoxymethyl)-9-(trifluoromethyl)-2,3-dihydro-5H-[1,4]thiazino[2,3,4-ij]quinazolin-5-one | 629.04 | 93.9 |
| 564 | (3S,10S)-7-((3S,5R)-4-acryloyl-3,5-dimethylpiperazin-1-yl)-10-(5-chloro-2,4-difluorophenyl)-3-(methoxymethyl)-9-(trifluoromethyl)-2,3-dihydro-5H-[1,4]thiazino[2,3,4-ij]quinazolin-5-one | 629.04 | 80.8 |
| 565 | (3S,10S)-3-((2-oxa-7-azaspiro[3.5]nonan-7-yl)methyl)-7-((3S,5R)-4-acryloyl-3,5-dimethylpiperazin-1-yl)-10-(5-chloro-2,4-difluorophenyl)-9-(trifluoromethyl)-2,3-dihydro-5H-[1,4]thiazino[2,3,4 -ij]quinazolin-5-one | 724.18 | 48.3 |
| 566 | (3S,10R)-3-((2-oxa-7-azaspiro[3.5]nonan-7-yl)methyl)-7-((3S,5R)-4-acryloyl-3,5-dimethylpiperazin-1-yl)-10-(5-chloro-2,4-difluorophenyl)-9-(trifluoromethyl)-2,3-dihydro-5H-[1,4]thiazino[2,3,4-ij]quinazolin-5-one | 724.18 | 77.7 |
| 567 | (3S)-7-((3S,5R)-4-acryloyl-3,5-dimethylpiperazin-1-yl)-10-(5-chloro-2,4-difluorophenyl)-3-((methoxymethoxy)methyl)-9-(trifluoromethyl)-2,3-dihydro-5H-[1,4]thiazino[2,3,4-ij]quinazolin-5-one | 659.07 | 64.4 |
| 568 | (3S)-7-((3S,5R)-4-acryloyl-3,5-dimethylpiperazin-1-yl)-10-(5-chloro-2,4-difluorophenyl)-3-(hydroxymethyl)-9-(trifluoromethyl)-2,3-dihydro-5H-[1,4]thiazino[2,3,4-ij]quinazolin-5-one | 615.01 | 52.3 |
| 569 | (3S,10R)-7-((2S,5R)-4-acryloyl-2,5-dimethylpiperazin-l -yl)-9-chloro-3-((4-(2,2-difluoroethyl)piperazin-1-yl)methyl)-10-(1-methyl-1H-indazol-7 -yl)-2,3-dihydro-5H-[1,4]thiazino[2,3,4-ij]quinazolin-5-one | 697.24 | 93.4 |
| 570 | (3S,10S)-7-((2S,5R)-4-acryloyl-2,5-dimethylpiperazin-1-yl)-9-chloro-3-((4-(2,2-difluoroethyl)piperazin-1- | 697.24 | 0 |

TABLE 6-continued

CAF data for compounds 408 to 589

| Example Number | IUPAC Name | MW | % CAF @ 10 uM, 1 h |
|---|---|---|---|
| | yl)methyl)-10-(1-methyl-1H-indazol-7-yl)-2,3-dihydro-5H-[1,4]thiazino[2,3,4-ij]quinazolin-5-one | | |
| 571 | (3S)-7-(9-acryloyl-7-oxo-3,9-diazabicyclo[3.3.1]nonan-3-yl)-10-(2,4-difluorophenyl)-3-(methoxymethyl)-9-(trifluoromethyl)-2,3-dihydro-5H-[1,4]thiazino[2,3,4-ij]quinazolin-5-one | 620.59 | 95.2 |
| 572 | (3S)-7-(4-acryloylpiperazin-1-yl)-10-(5-chloro-2,4-difluorophenyl)-3-(methoxymethyl)-9-(trifluoromethyl)-2,3-dihydro-5H-[1,4]thiazino[2,3,4-ij]quinazolin-5-one | 600.99 | 93.6 |
| 573 | (S)-7-((2S,5R)-4-acryloyl-2,5-dimethylpiperazin-1-yl)-9-chloro-10-(4-fluorophenyl)-3-(methoxymethyl)-2,3-dihydro-5H-[1,4]thiazino[2,3,4-ij]quinazolin-5-one | 543.05 | 76.4 |
| 574 | S)-7-((2S,5R)-4-acryloyl-2,5-dimethylpiperazin-1-yl)-3-((4-(2,2-difluoroethyl)piperazin-1-yl)methyl)-10-(4-fluorophenyl)-9-(trifluoromethyl)-2,3-dihydro-5H-[1,4]thiazino[2,3,4-ij]quinazolin-5-one | 694.73 | 83.2 |
| 575 | 2-(4-(((3S)-7-((2S,5R)-4-acryloyl-2,5-dimethylpiperazin-1-yl)-10-(2,4-difluorophenyl)-5-oxo-9-(trifluoromethyl)-2,3-dihydro-5H-[1,4]thiazino[2,3,4-ij]quinazolin-3-yl)methyl)piperazin-1-yl)acetamide | 705.74 | 89.5 |
| 576 | (3S,10S)-3-((2-oxa-7-azaspiro[3.5]nonan-7-yl)methyl)-7-((3S,5R)-4-acryloyl-3,5-dimethylpiperazin-1-yl)-10-(2,4-difluorophenyl)-9-(trifluoromethyl)-2,3-dihydro-5H-[1,4]thiazino[2,3,4-ij]quinazolin-5-one | 689.74 | 80.5 |
| 577 | (3S,10R)-3-((2-oxa-7-azaspiro[3.5]nonan-7-yl)methyl)-7-((3S,5R)-4-acryloyl-3,5-dimethylpiperazin-1-yl)-10-(2,4-difluorophenyl)-9-(trifluoromethyl)-2,3-dihydro-5H-[1,4]thiazino[2,3,4-ij]quinazolin-5-one | 689.74 | 74.8 |
| 578 | (3S,10R)-7-(4-acryloylpiperazin-1-yl)-10-(2,4-difluorophenyl)-3-(methoxymethyl)-9-(trifluoromethyl)-2,3-dihydro-5H-[1,4]thiazino[2,3,4-ij]quinazolin-5-one | 566.54 | 98 |
| 579 | (3S,10S)-7-(4-acryloylpiperazin-1-yl)-10-(2,4-difluorophenyl)-3-(methoxymethyl)-9-(trifluoromethyl)-2,3-dihydro-5H-[1,4]thiazino[2,3,4-ij]quinazolin-5-one | 566.54 | 96.9 |
| 580 | (3S,10S)-7-((2S,5R)-4-acryloyl-2,5-dimethylpiperazin-1-yl)-3-((4-cyclopropylpiperazin-1-yl)methyl)-10-(2,4-difluorophenyl)-9-(trifluoromethyl)-2,3-dihydro-5H-[1,4]thiazino[2,3,4-ij]quinazolin-5-one | 688.75 | 91.5 |
| 581 | (3S,10R)-7-((2S,5R)-4-acryloyl-2,5-dimethylpiperazin-1-yl)-3-((4-cyclopropylpiperazin-1-yl)methyl)-10-(2,4-difluorophenyl)-9-(trifluoromethyl)-2,3-dihydro-5H-[1,4]thiazino[2,3,4-ij]quinazolin-5-one | 688.75 | 97.4 |
| 582 | (3S)-8-(4-acryloylpiperazin-1-yl)-11-(5-chloro-2,4-difluorophenyl)-3-methoxy-10-(trifluoromethyl)-3,4-dihydro-2H,6H-[1,4]thiazepino[2,3,4-ij]quinazolin-6-one | 600.99 | 88 |
| 583 | (3S)-8-((S)-4-acryloyl-2-methylpiperazin-l-yl)-11-(5-chloro-2,4-difluorophenyl)-3-methoxy-10-(trifluoromethyl)-3,4-dihydro-2H,6H-[1,4]thiazepino[2,3,4-ij]quinazolin-6-one | 615.01 | 91 |
| 584 | (R)-8-((3S,5R)-4-acryloyl-3,5-dimethylpiperazin-1-yl)-11-(4-fluorophenyl)-3-methoxy-10-(trifluoromethyl)-3,4-dihydro-2H,6H-[1,4]thiazepino[2,3,4-ij]quinazolin-6-one | 576.61 | 97 |
| 585 | (S)-8-((3S,5R)-4-acryloyl-3,5-dimethylpiperazin-1-yl)-11-(4-fluorophenyl)-3-methoxy-10-(trifluoromethyl)-3,4-dihydro-2H,6H-[1,4]thiazepino[2,3,4-ij]quinazolin-6-one | 576.61 | 97 |
| 586 | (3R)-8-((3S,5R)-4-acryloyl-3,5-dimethylpiperazin-1-yl)-11-(2,4-difluorophenyl)-3-(dimethylamino)-10-(trifluoromethyl)-3,4-dihydro-2H,6H-[1,4]thiazepino[2,3,4-ij]quinazolin-6-one | 607.64 | 40 |
| 587 | (3S)-7-((3S,5R)-4-acryloyl-3,5-dimethylpiperazin-1-yl)-10-(5-chloro-2,4-difluorophenyl)-3-((dimethylamino)methyl)-9-(trifluoromethyl)-2,3-dihydro-5H-[1,4]thiazino[2,3,4-ij]quinazolin-5-one | | 58.9 |
| 588 | 8'-((2S,5R)-4-acryloyl-2,5-dimethylpiperazin-1-yl)-11'-(2,4-difluorophenyl)-10'-(trifluoromethyl)-2'H,4'H,6'H-spiro[oxetane-3,3'-[1,4]thiazepino[2,3,4-ij]quinazolin]-6'-one | 607.18 | 95.9 |
| 589 | 8'-(4-acryloylpiperazin-1-yl-2,2,3,3,5,5,6,6-d8)-11'-(2,4-difluorophenyl)-10'-(trifluoromethyl)-2'H,4'H,6'H-spiro[oxetane-3,3'-[1,4]thiazepino[2,3,4-ij]quinazolin]-6'-one | 587.2 | 92.9 |

In embodiments, there also provides the following further compounds:
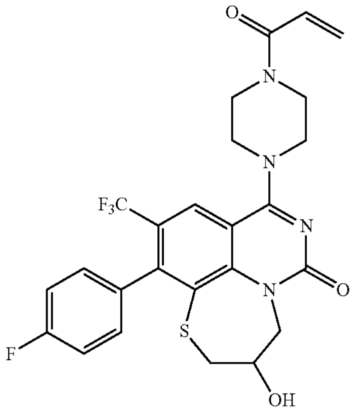
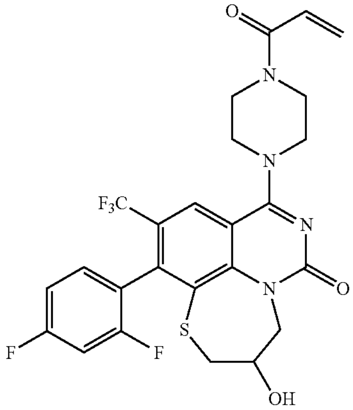
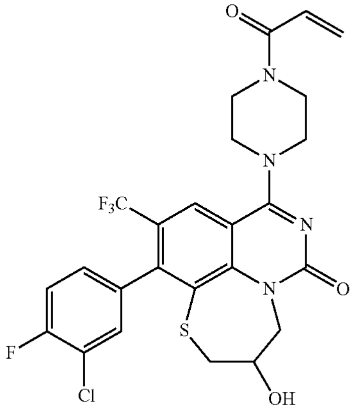
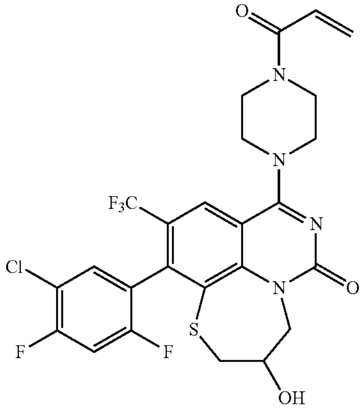
-continued
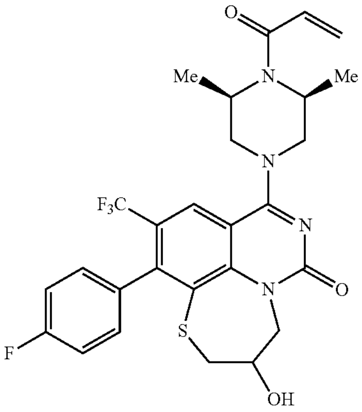
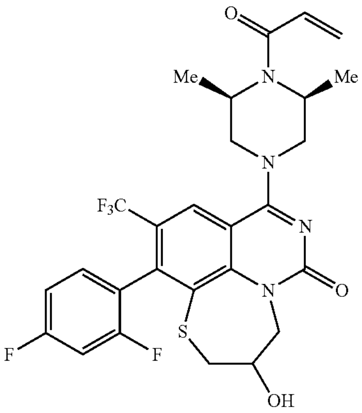
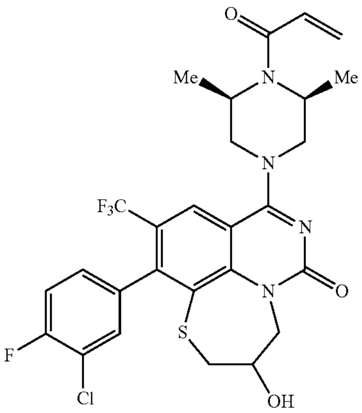
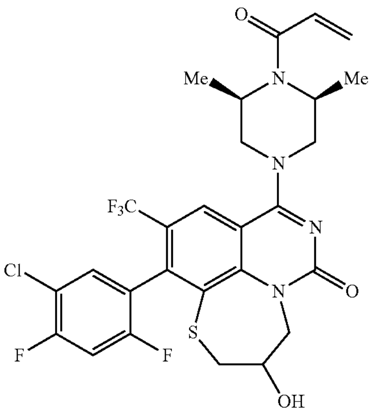

-continued
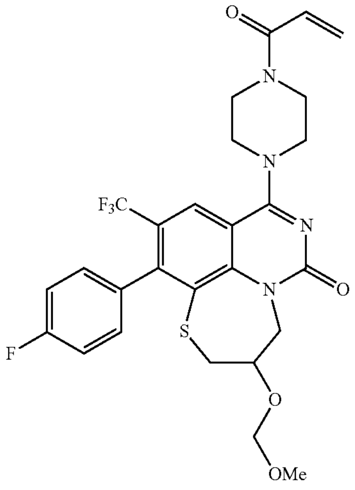
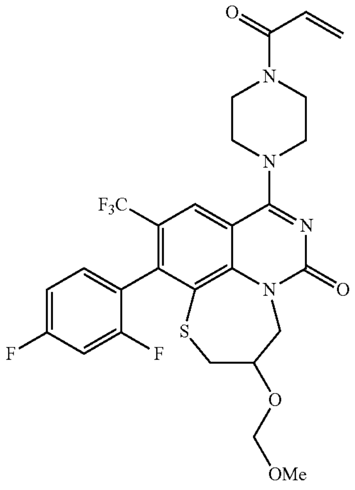
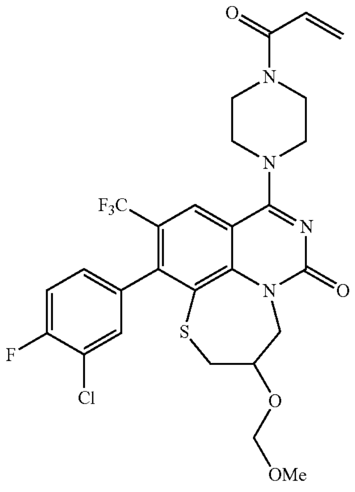
-continued
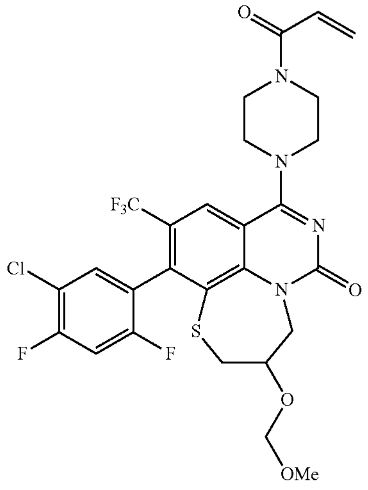
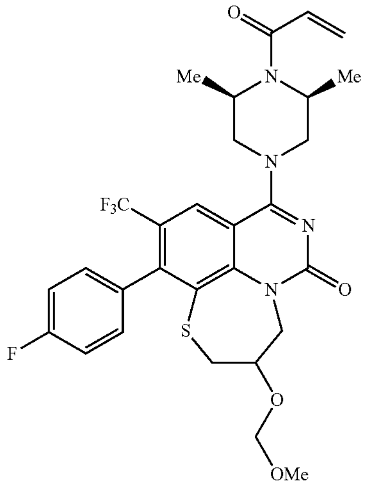
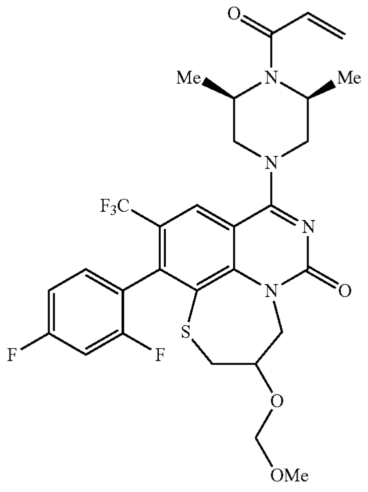

-continued
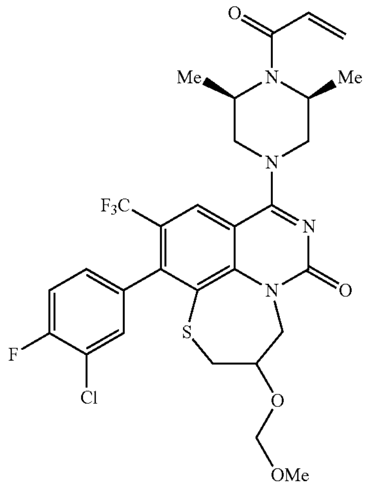
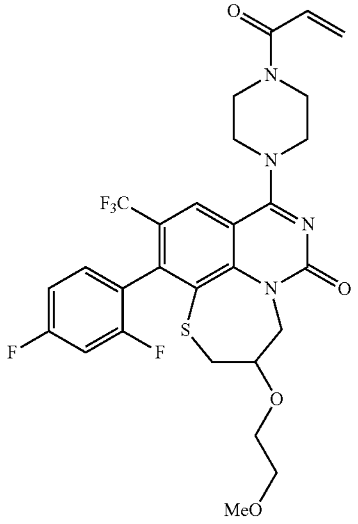
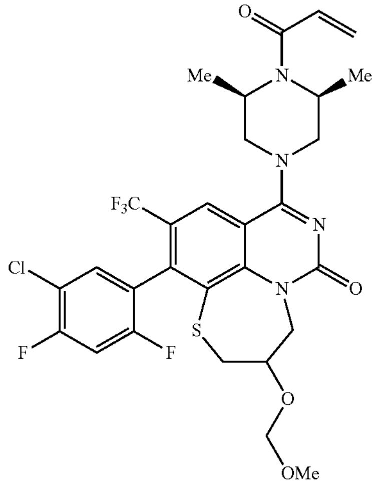
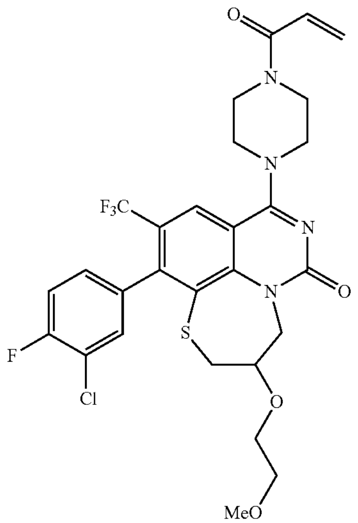
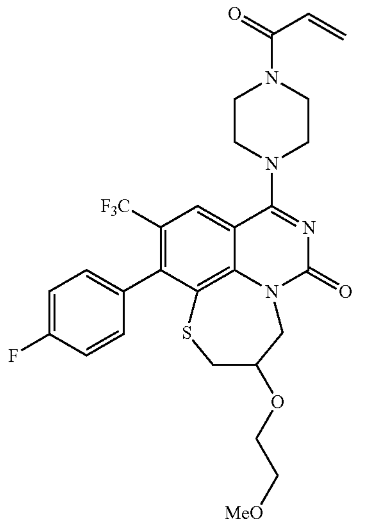
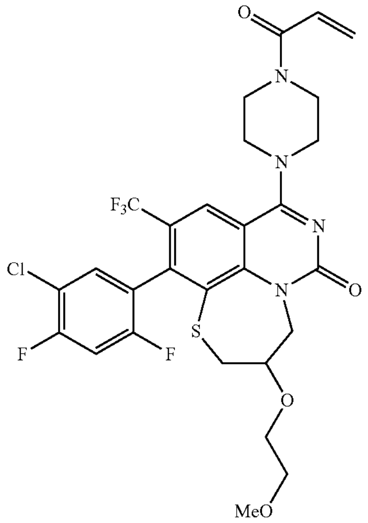
-continued -continued
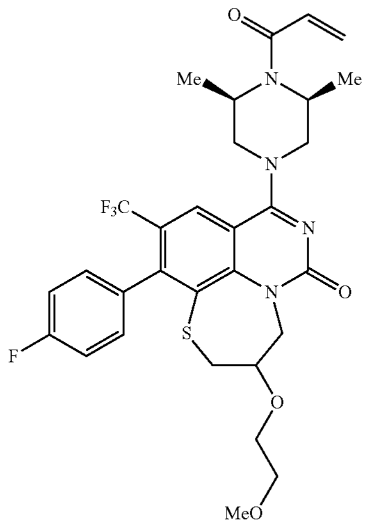
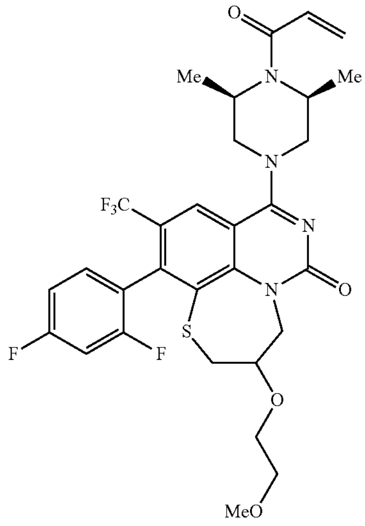
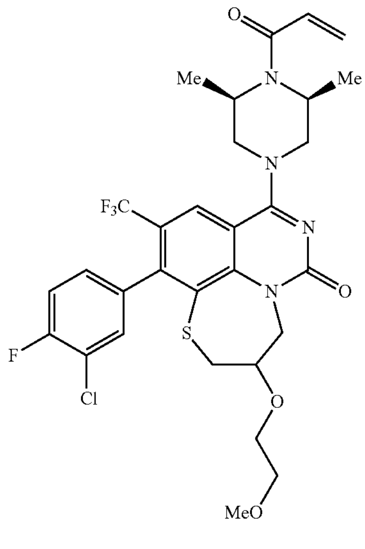
-continued
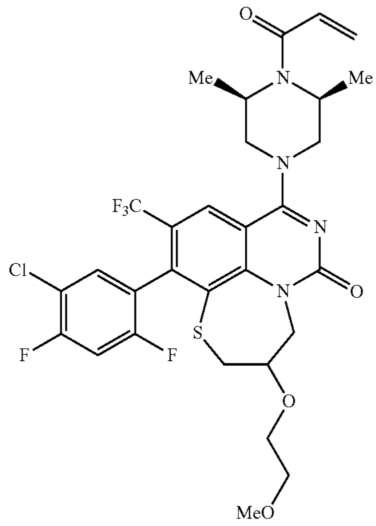
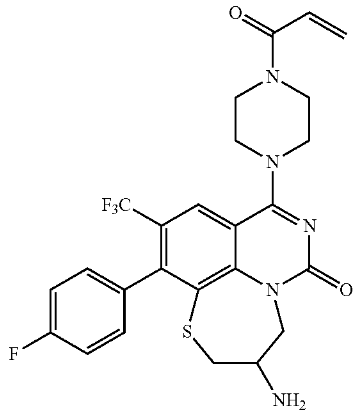
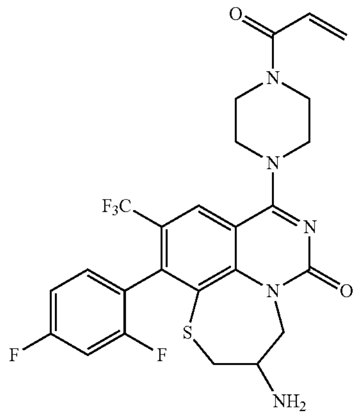

-continued
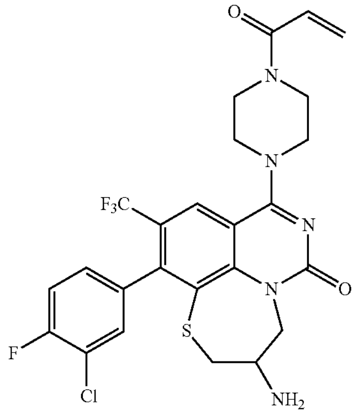
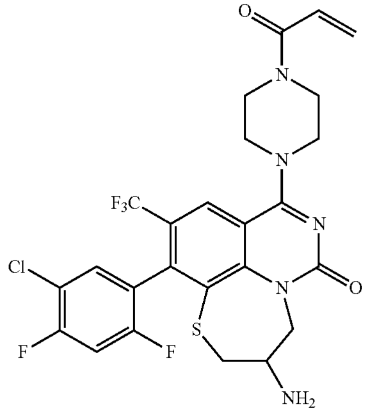
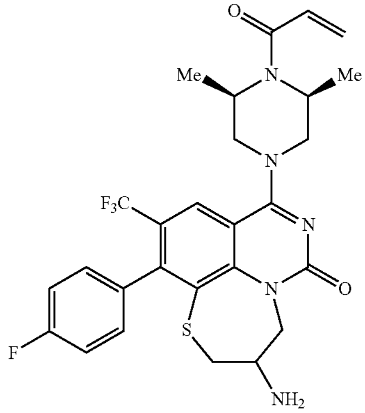
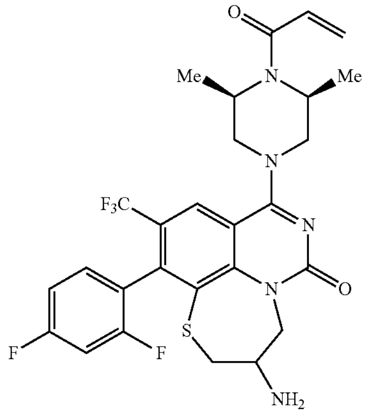
-continued
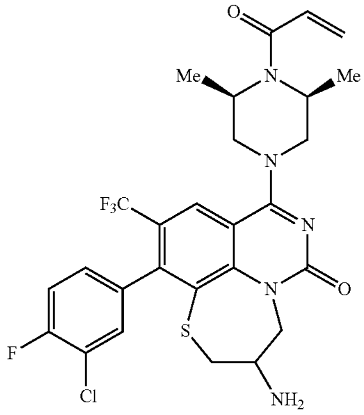
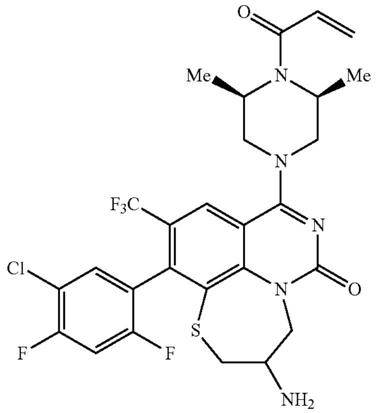
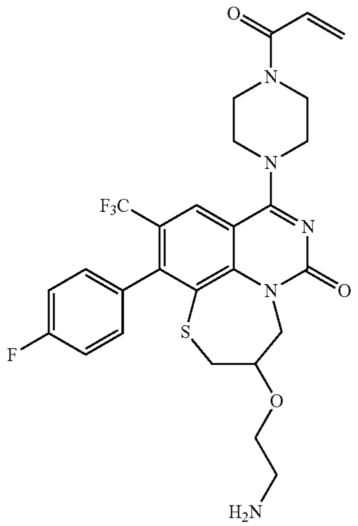

-continued
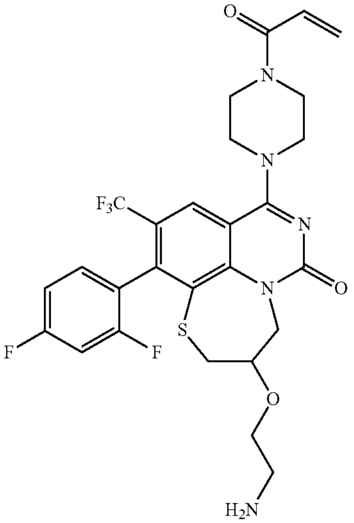
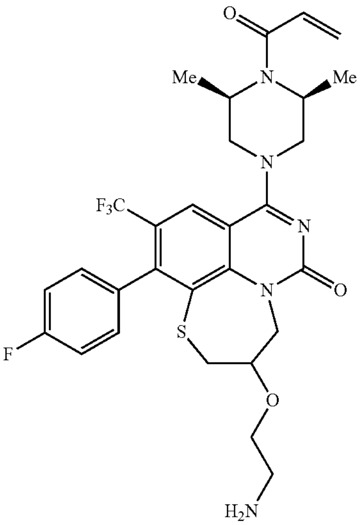
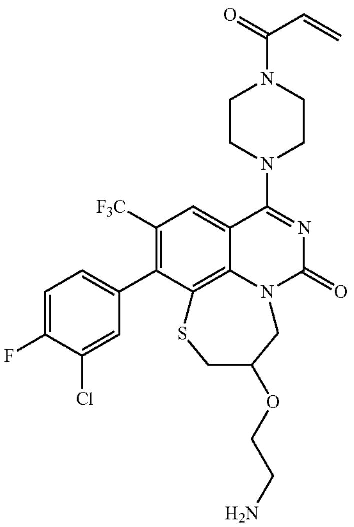
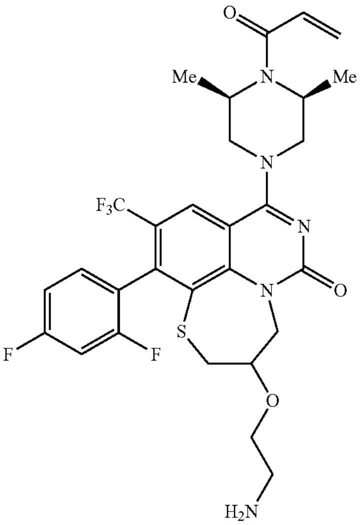
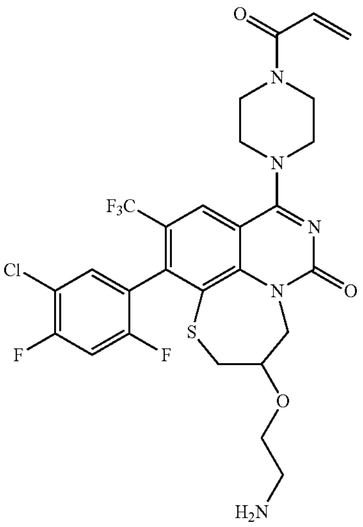
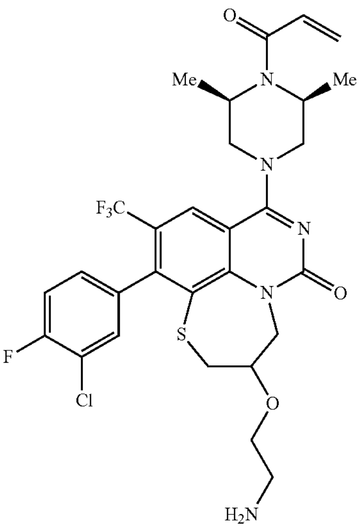

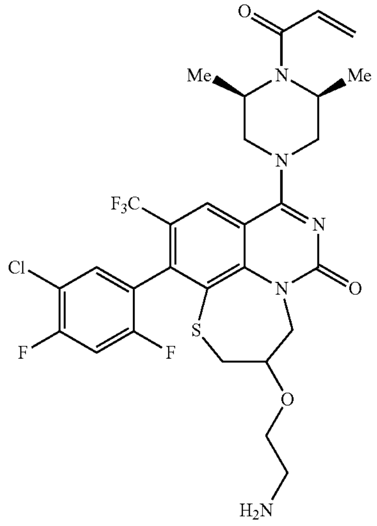
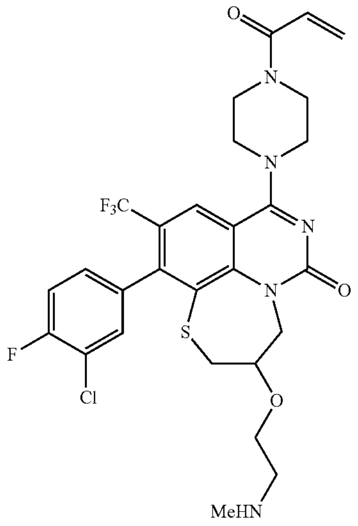
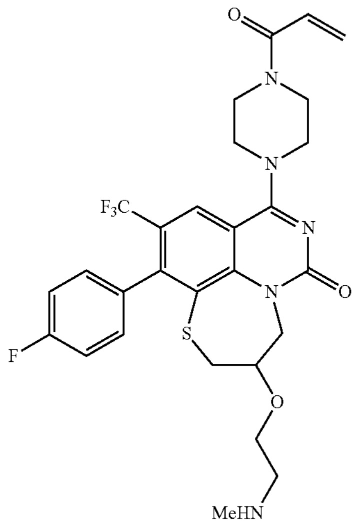
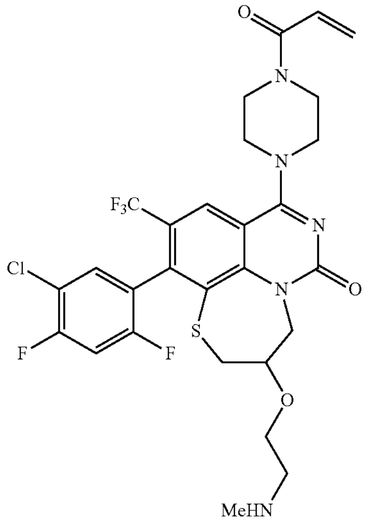
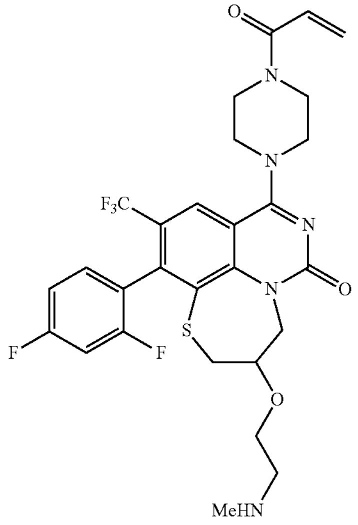
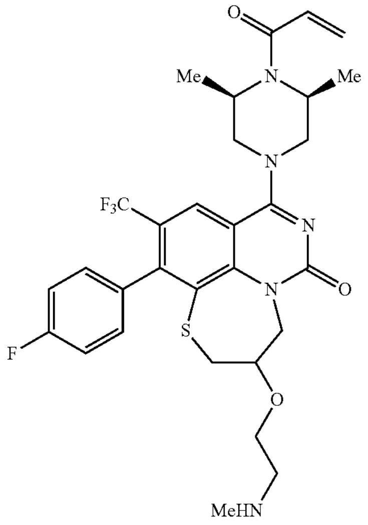

-continued
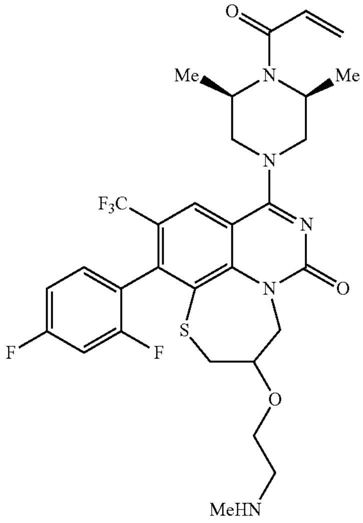
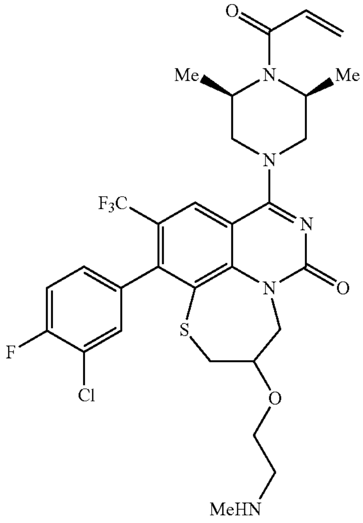
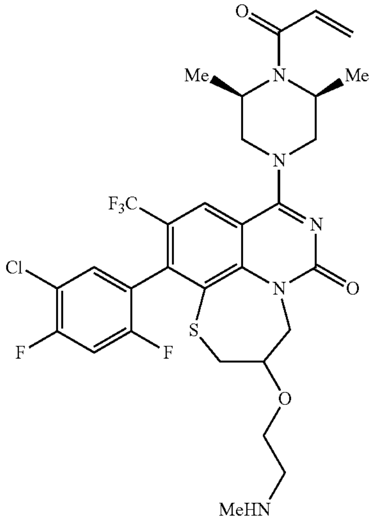
-continued
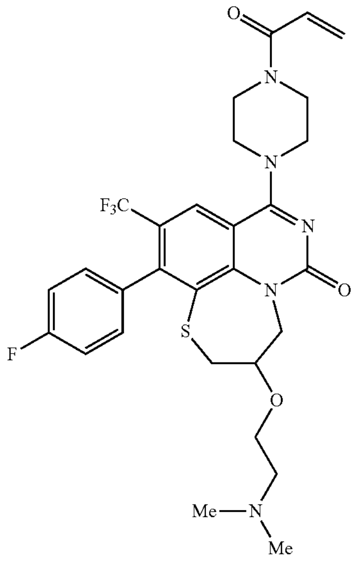
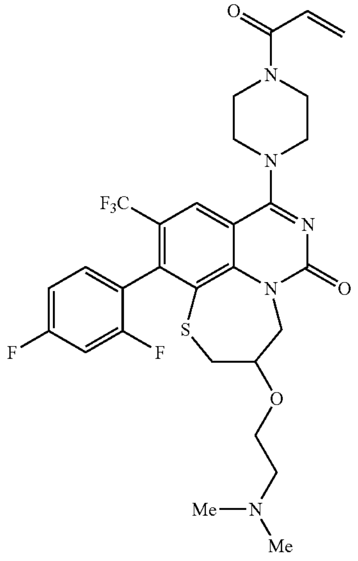
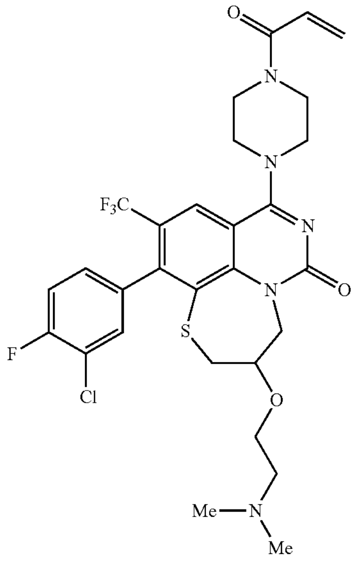

-continued
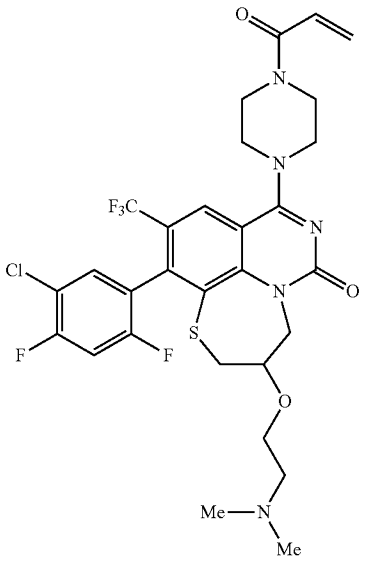
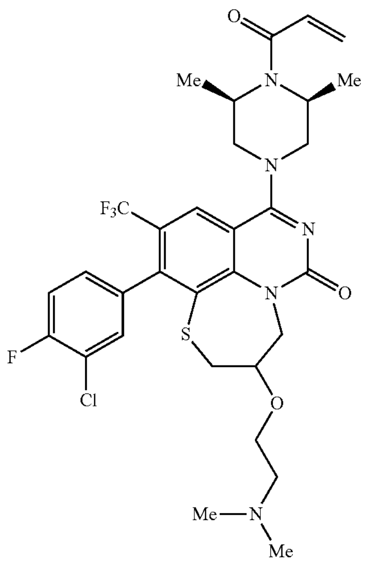
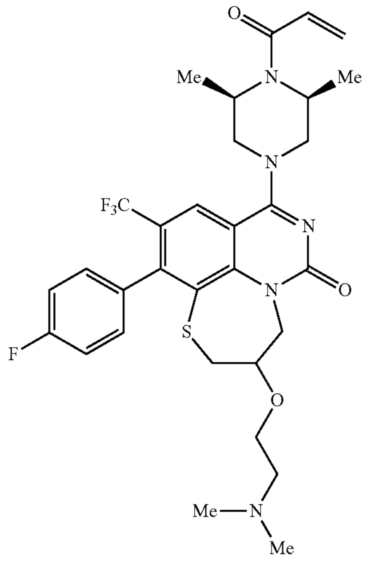
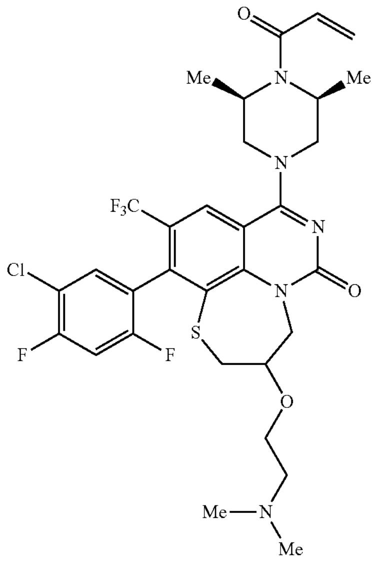
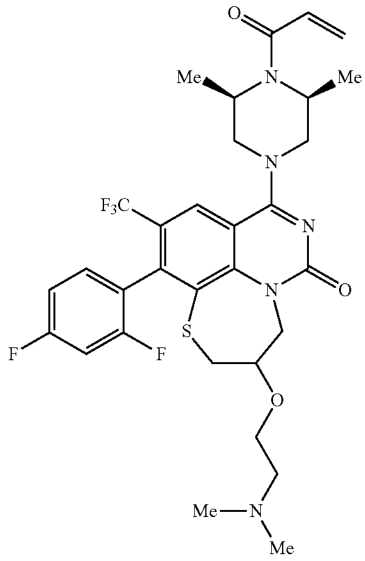
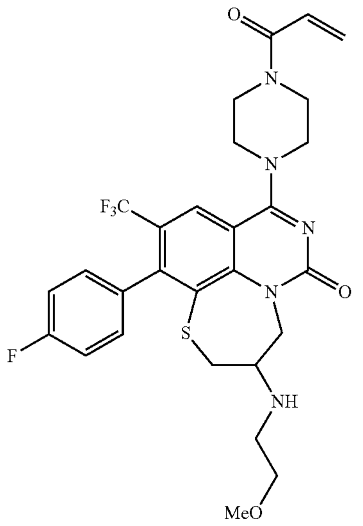
-continued -continued
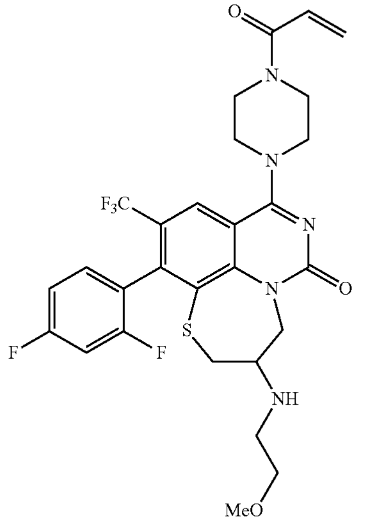
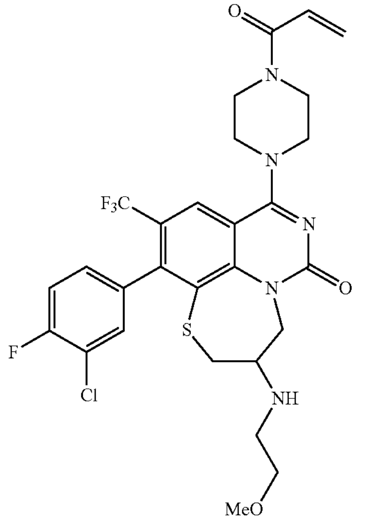
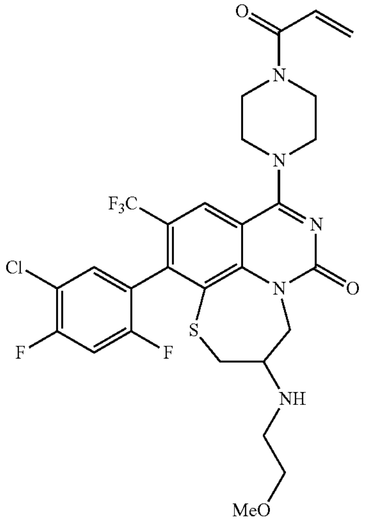
-continued
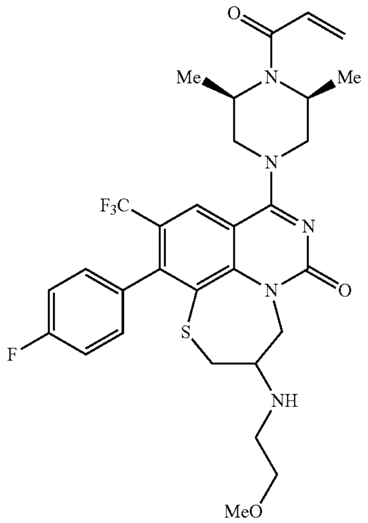
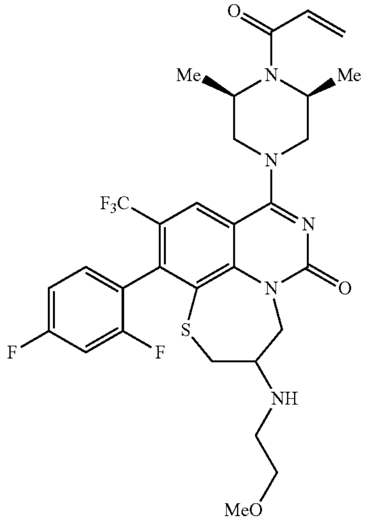
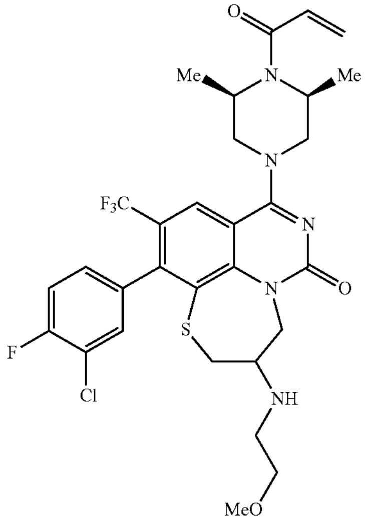

-continued
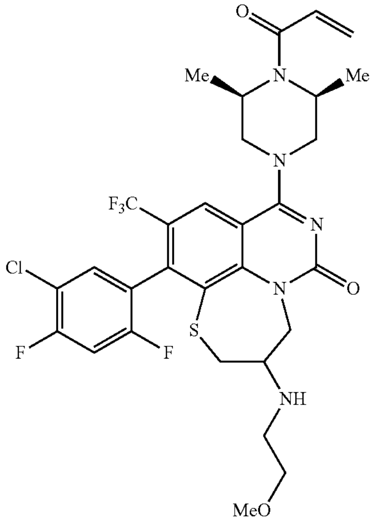
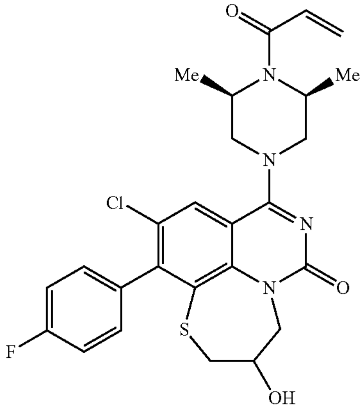
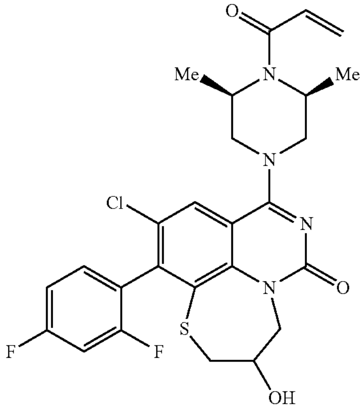
-continued
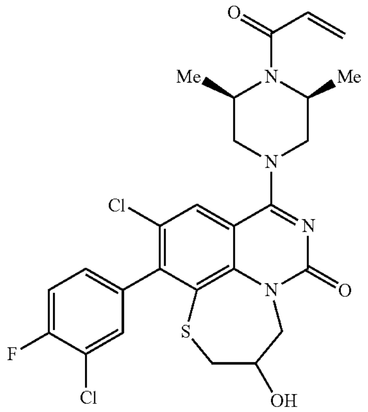
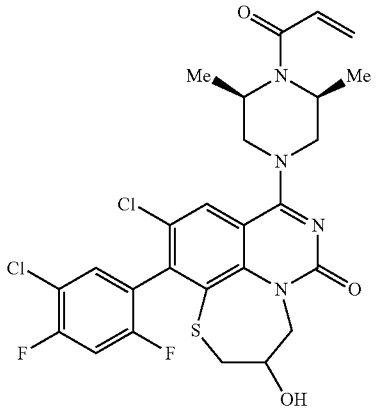
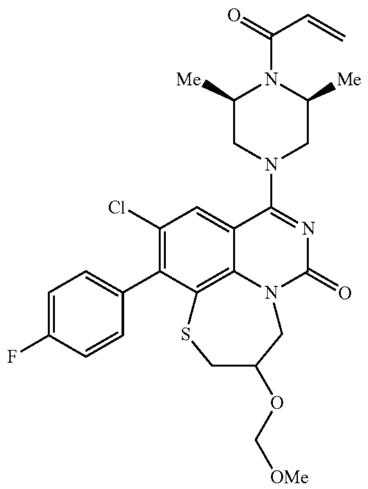

-continued
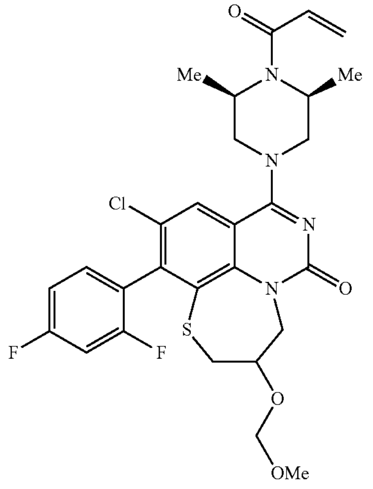
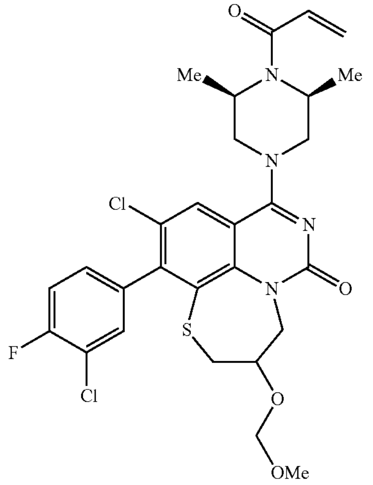
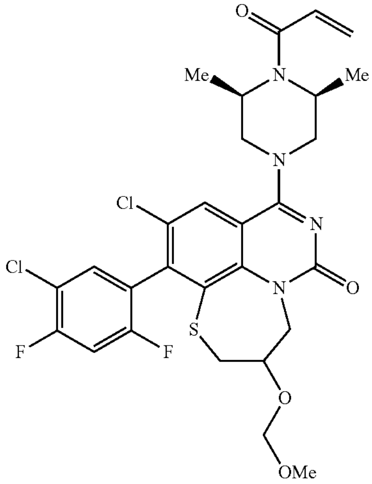
-continued
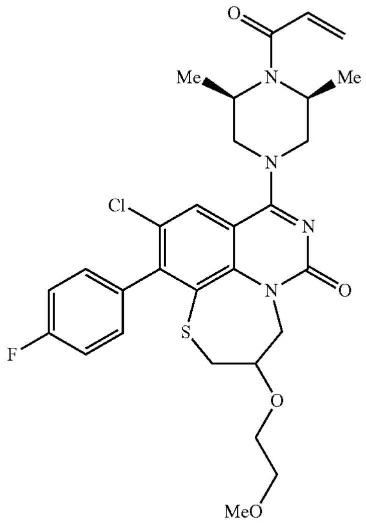
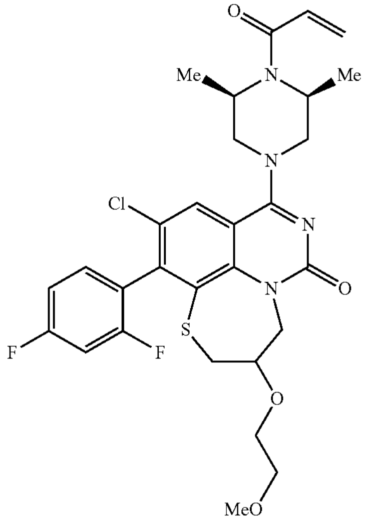
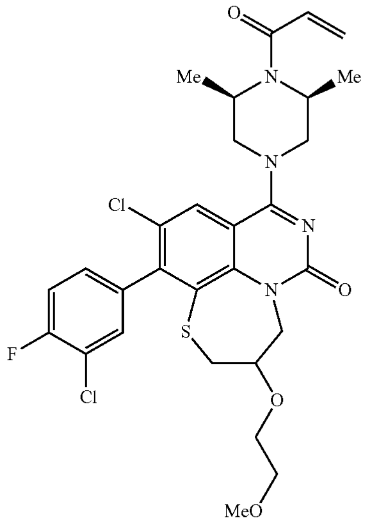

-continued
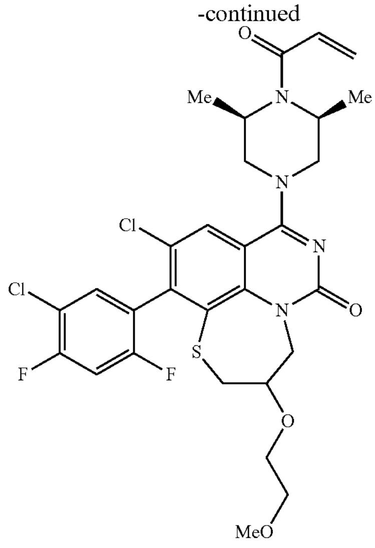
-continued
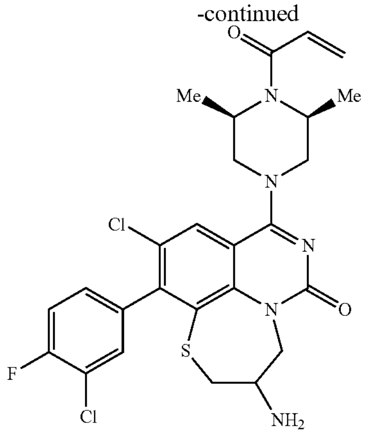
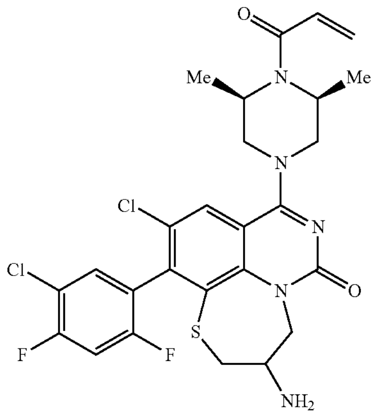
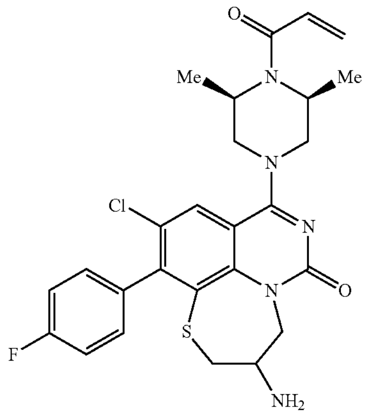
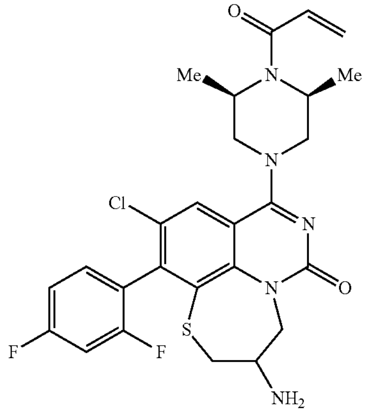
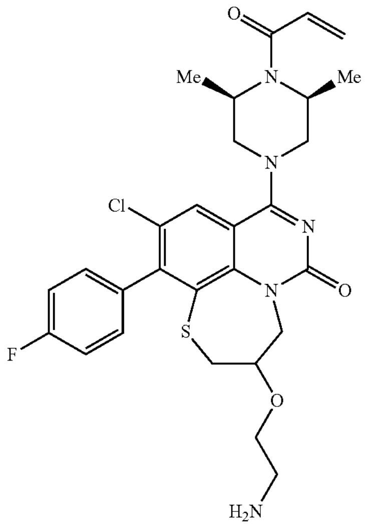

-continued
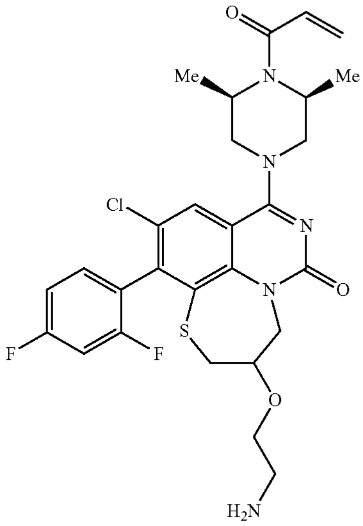
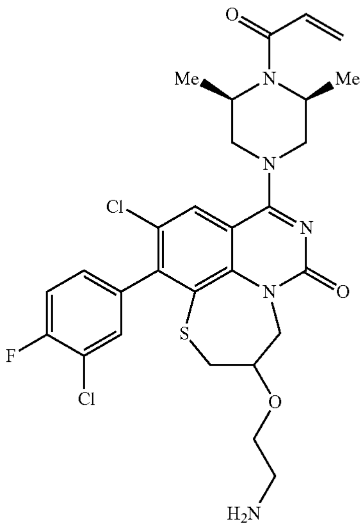
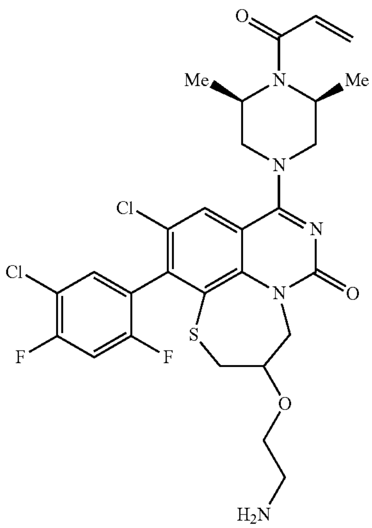
-continued
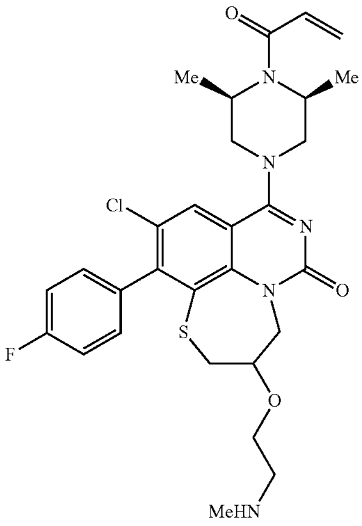
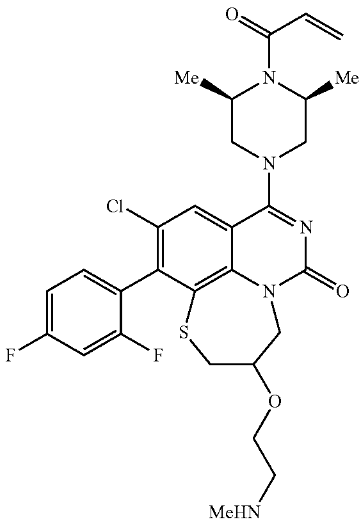
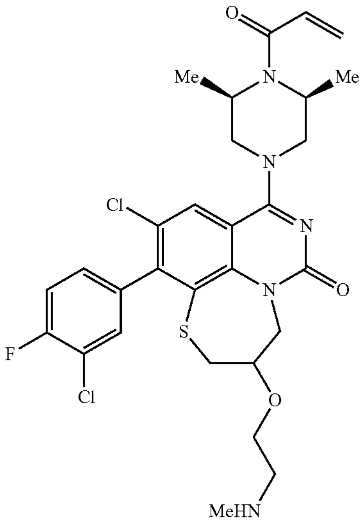

-continued
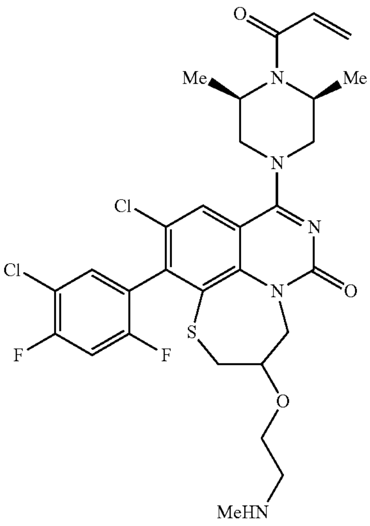
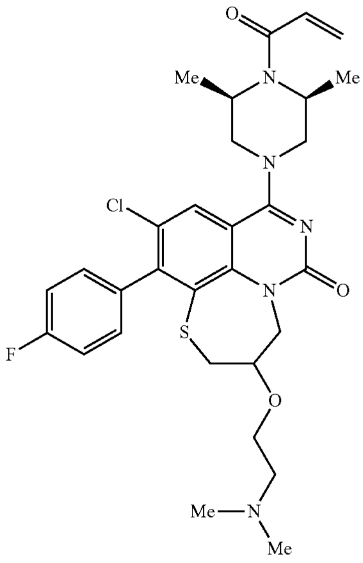
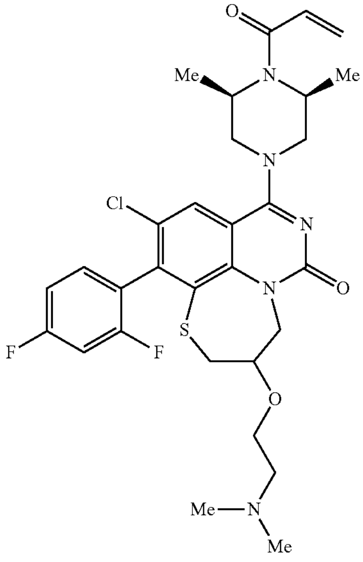
-continued
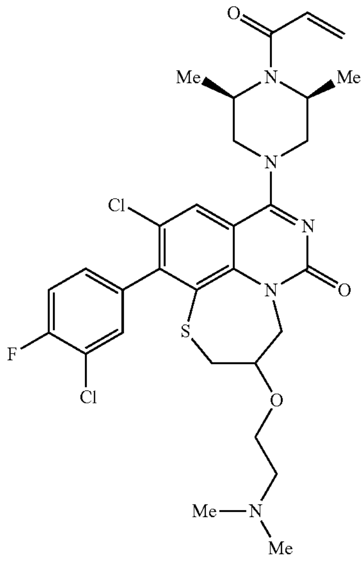
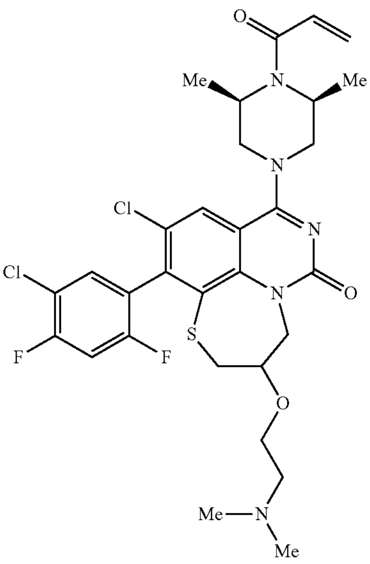
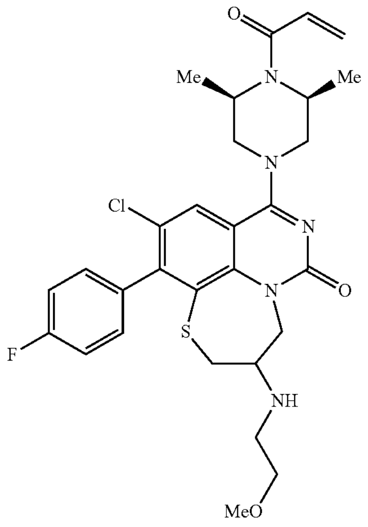

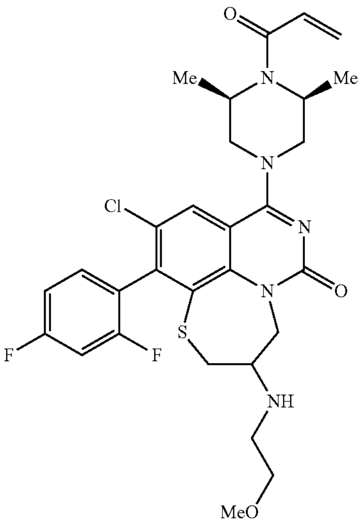
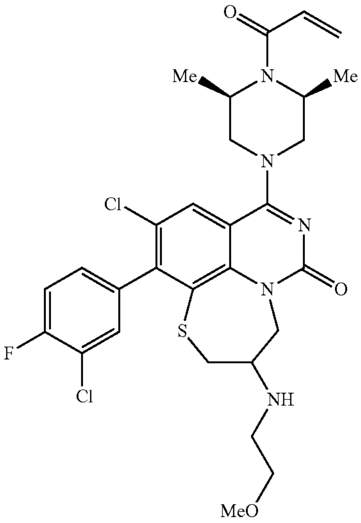
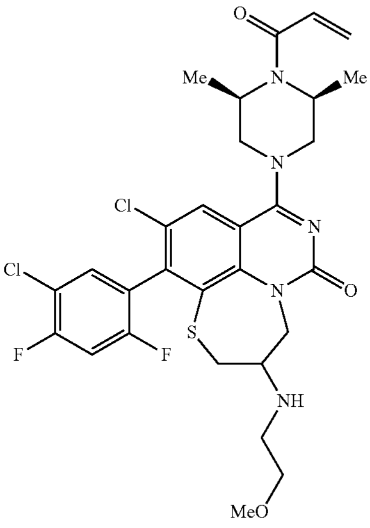
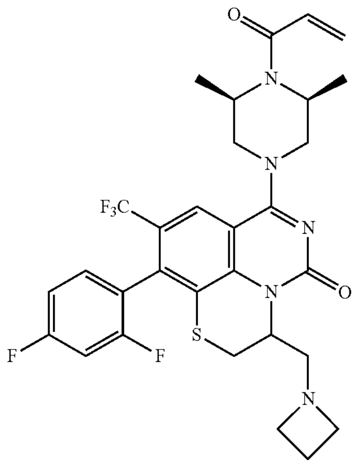
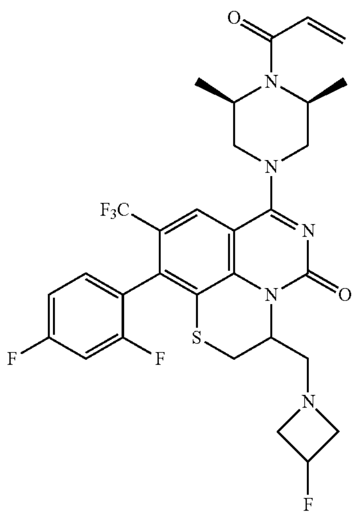
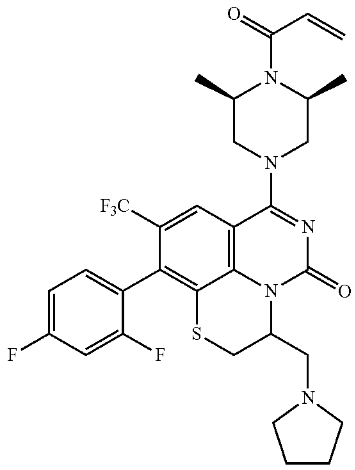

-continued
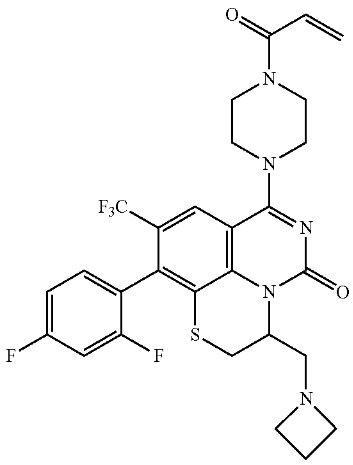
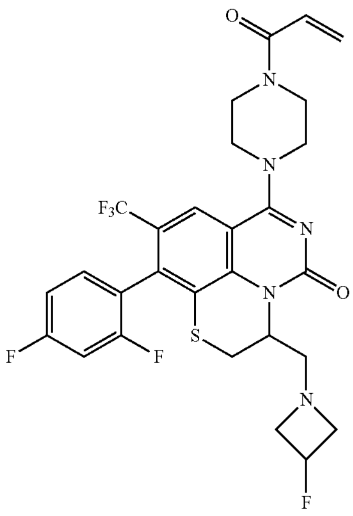
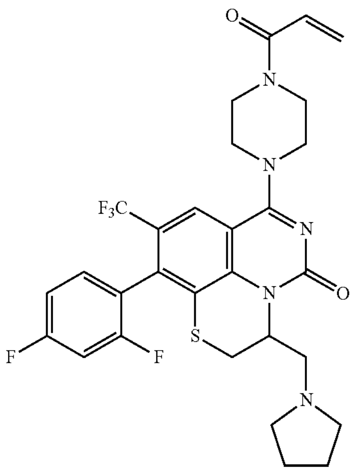
-continued
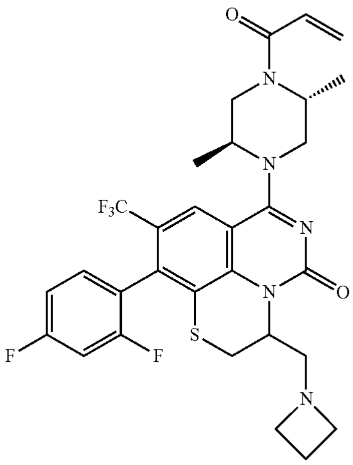
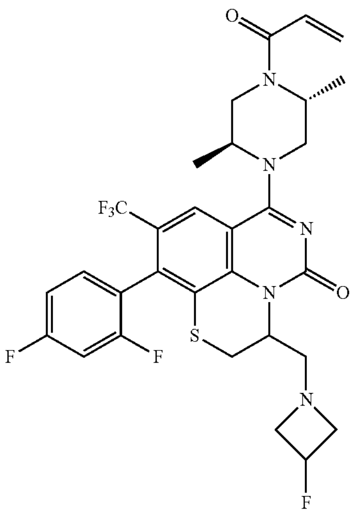
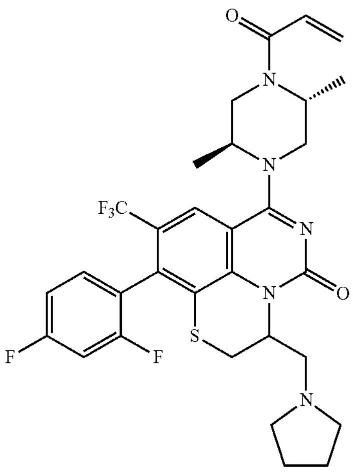

-continued
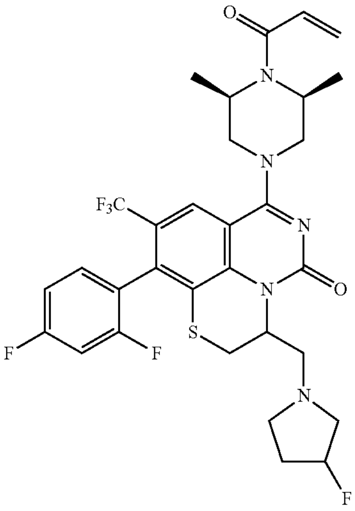
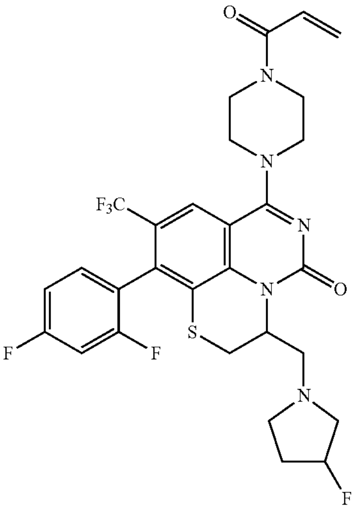
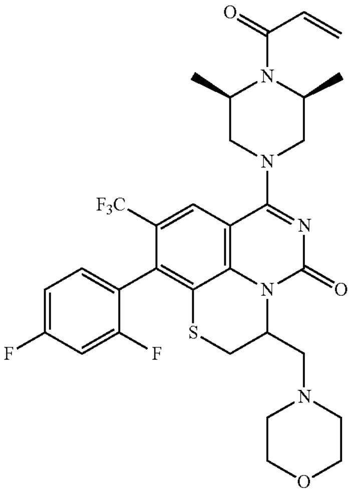
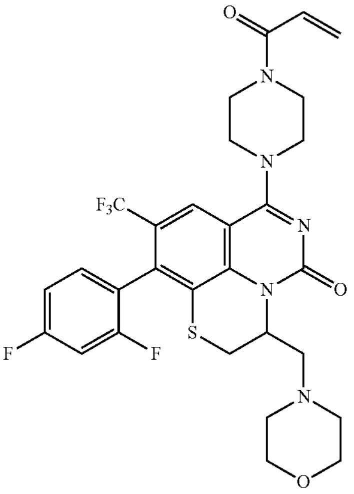
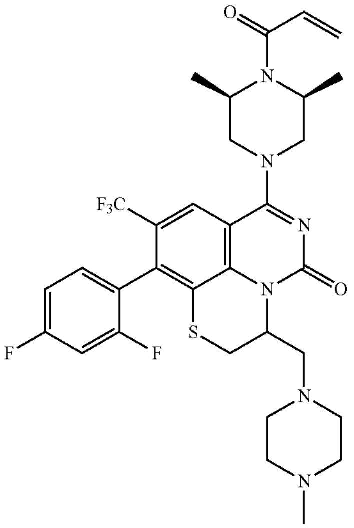
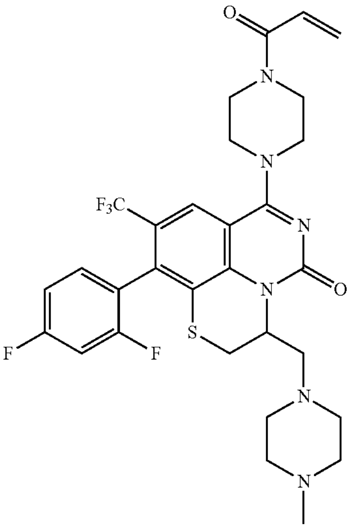

-continued
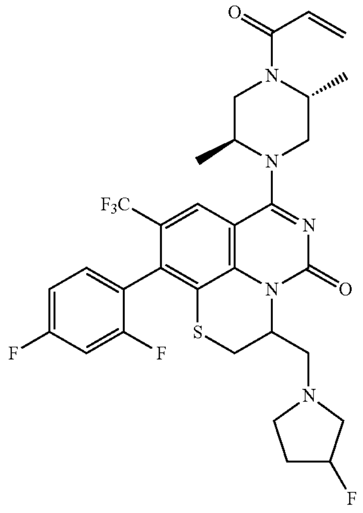
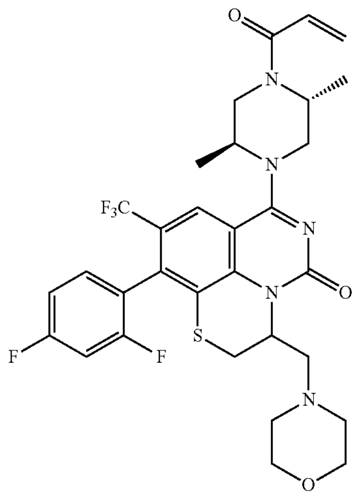
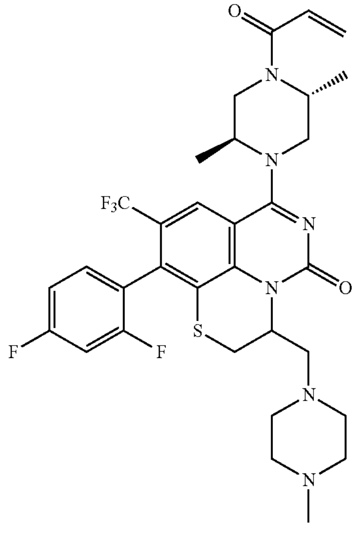
-continued
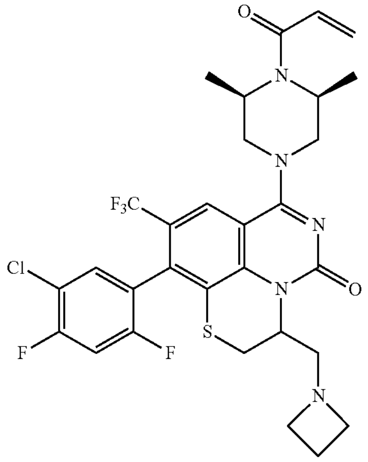
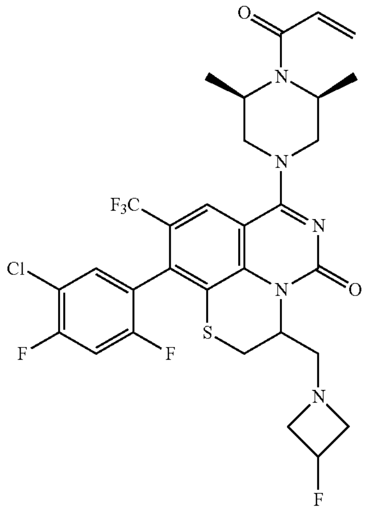
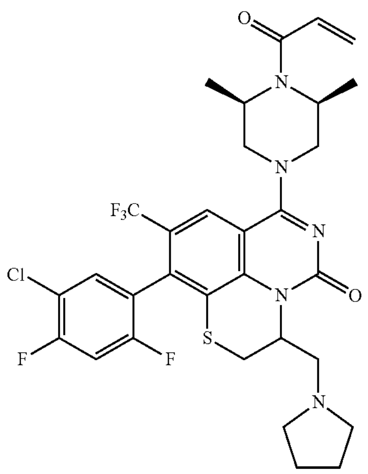

-continued
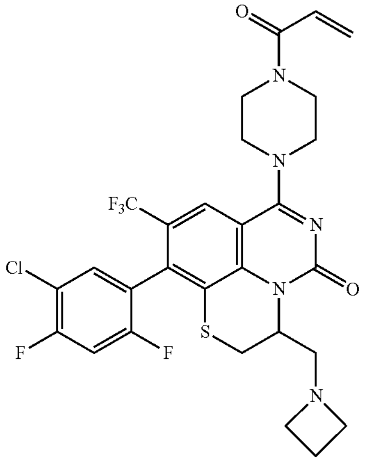
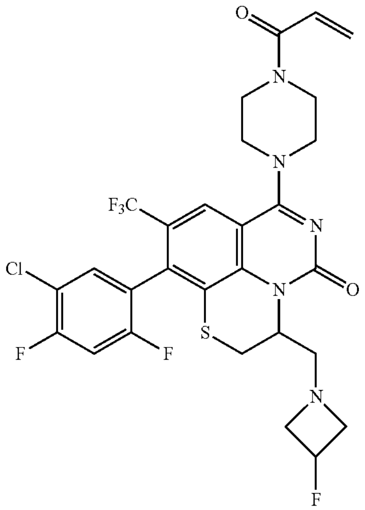
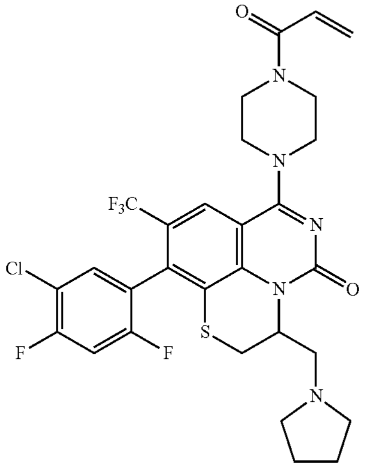
-continued
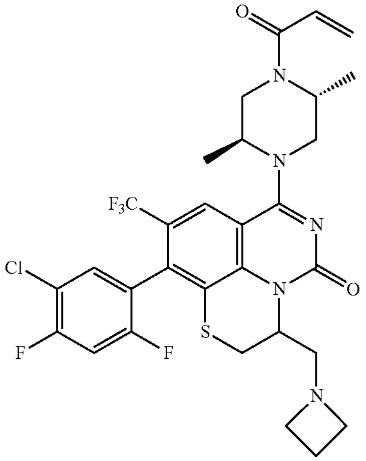
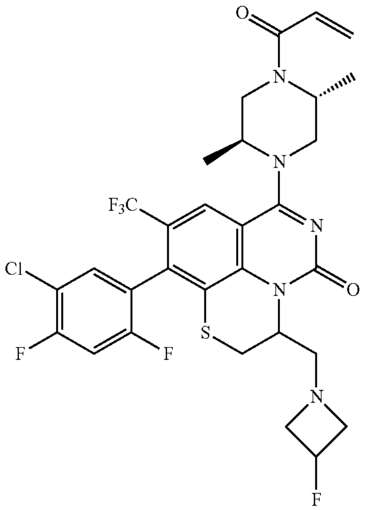
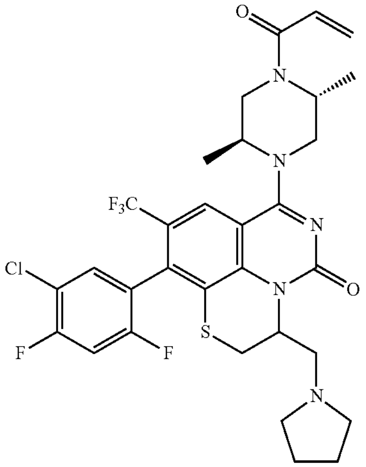

-continued
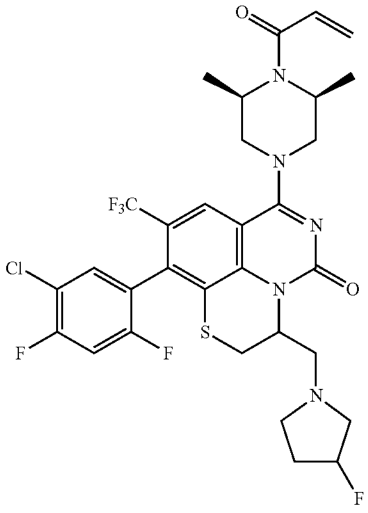
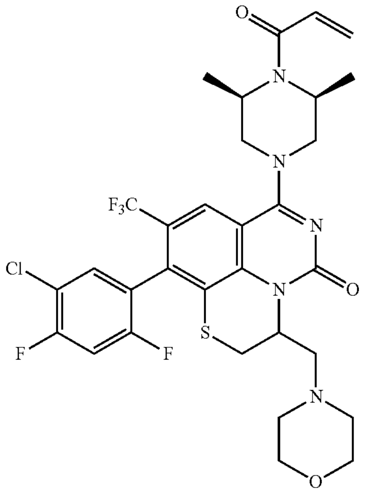
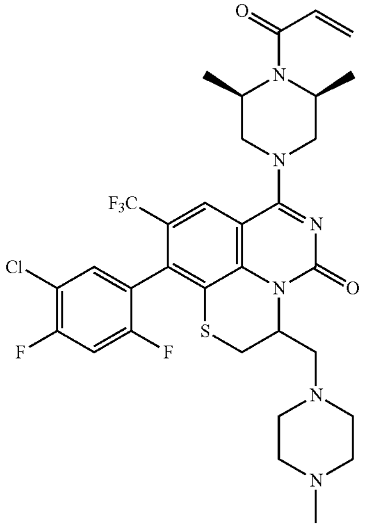
-continued
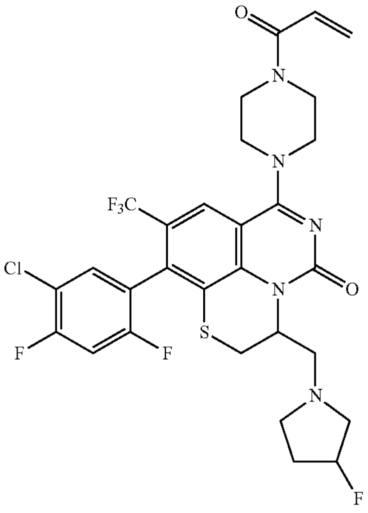
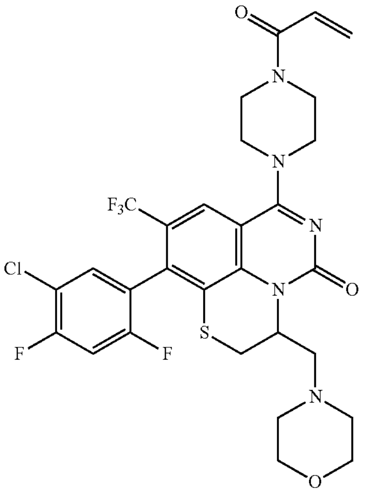
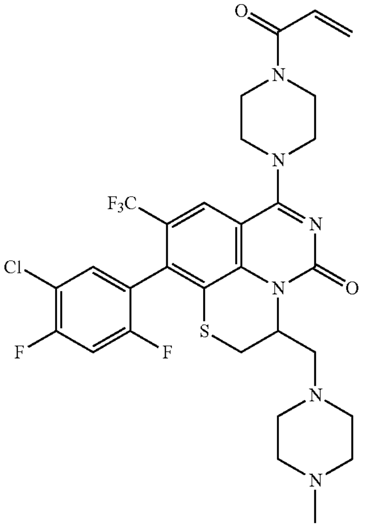

-continued
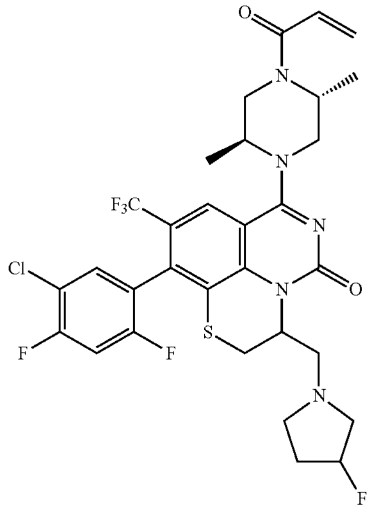
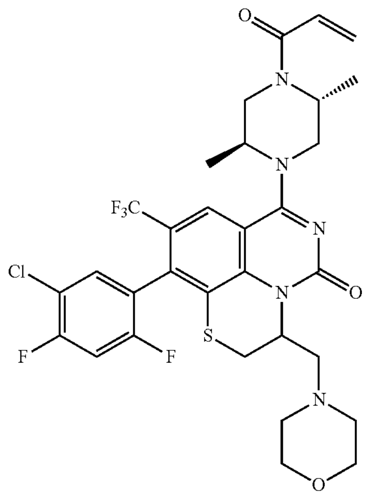
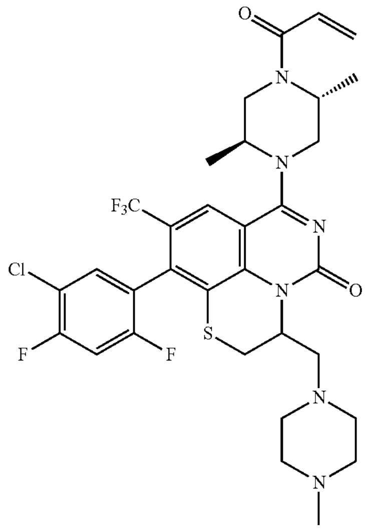
-continued
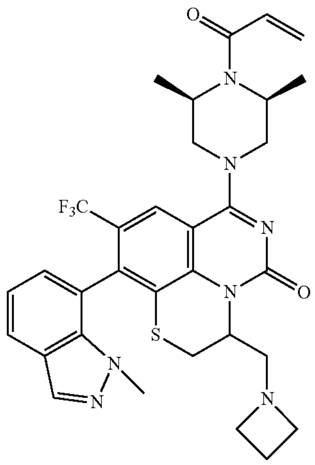
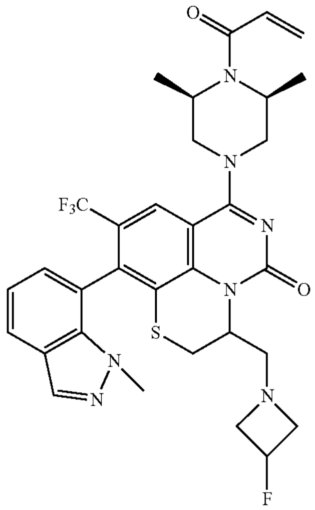
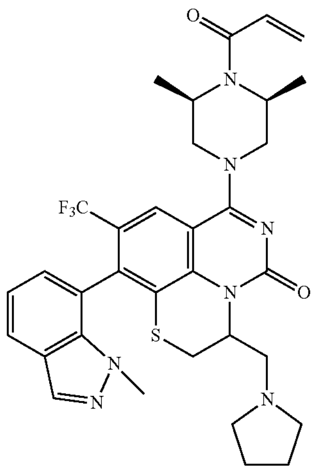

-continued
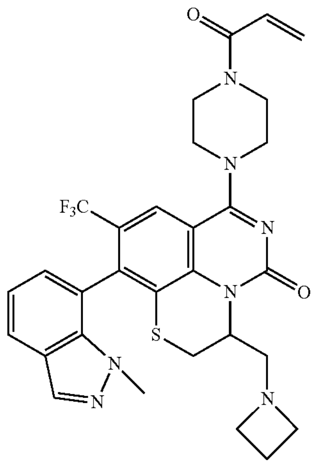
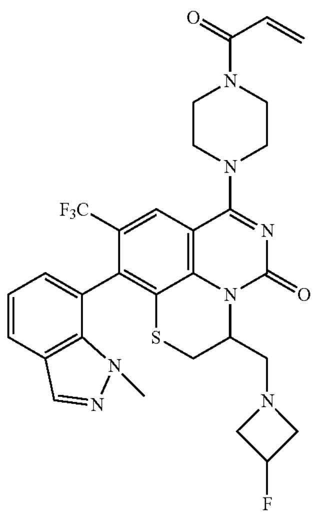
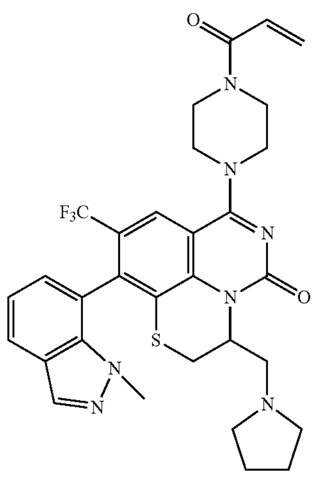
-continued
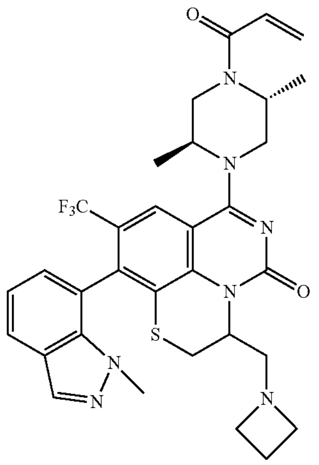
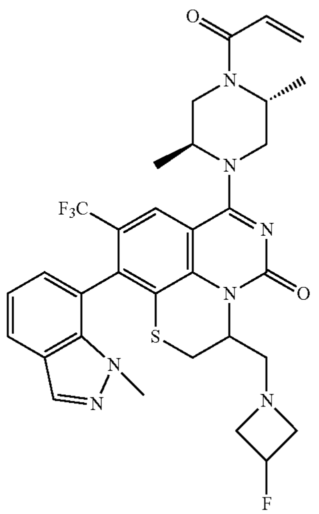
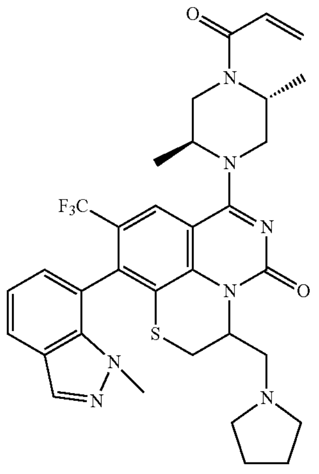

-continued
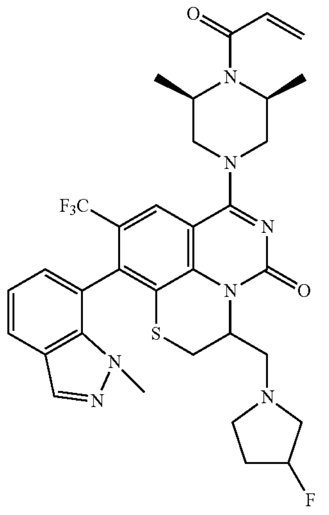
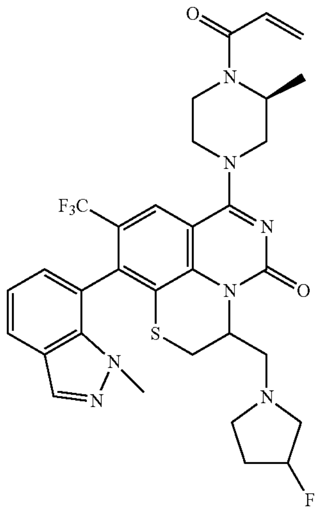
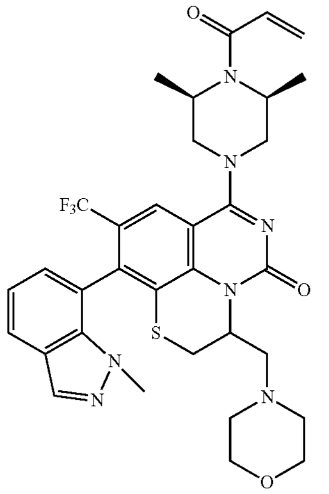
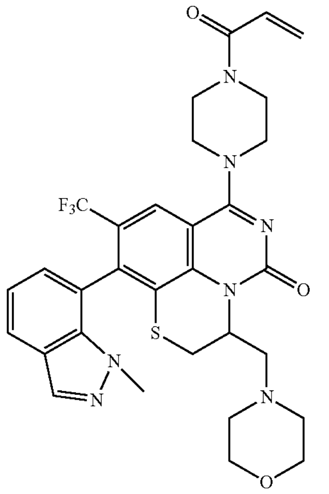
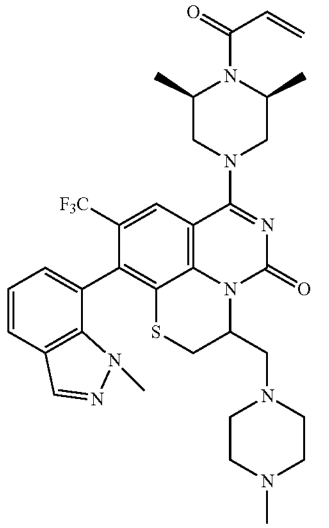
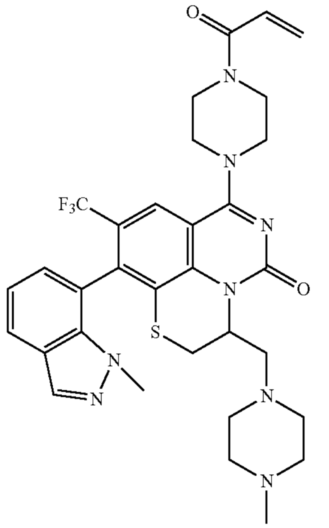

-continued
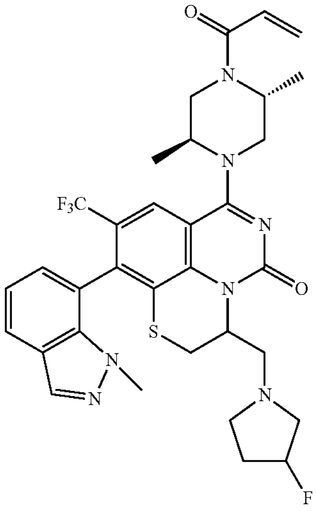
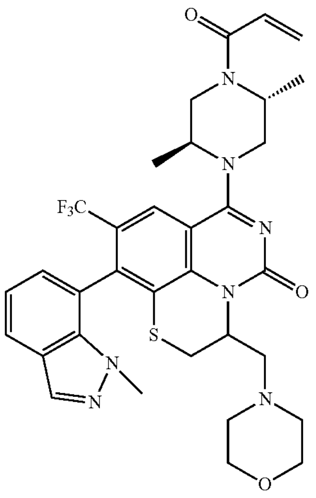
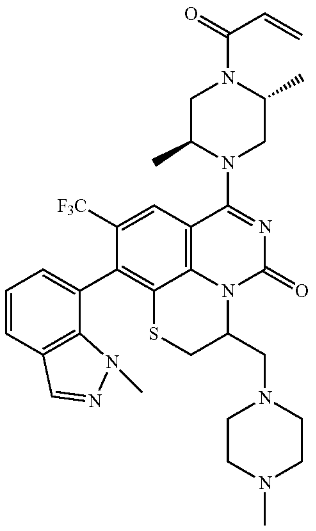
-continued
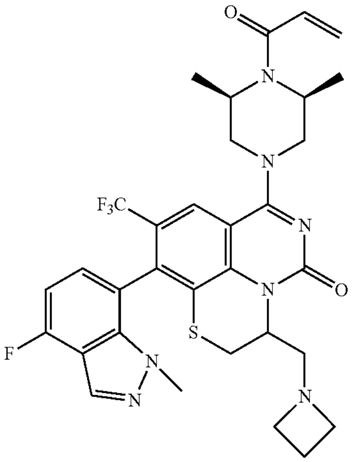
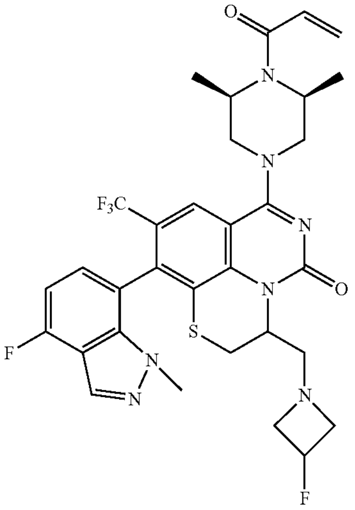
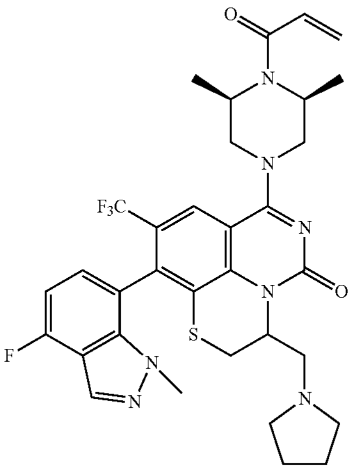

-continued
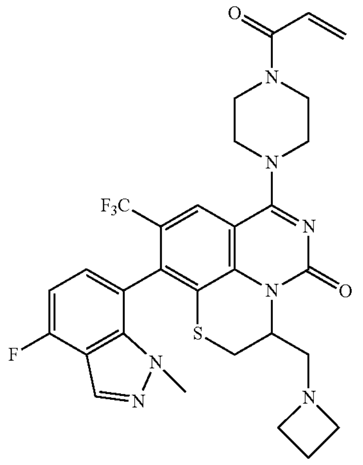
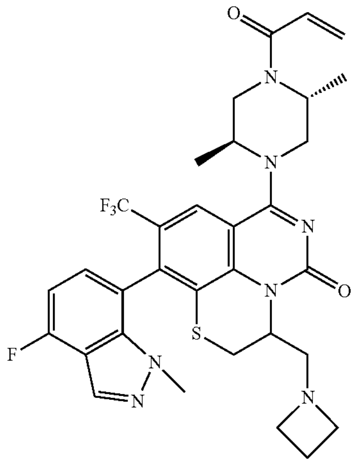
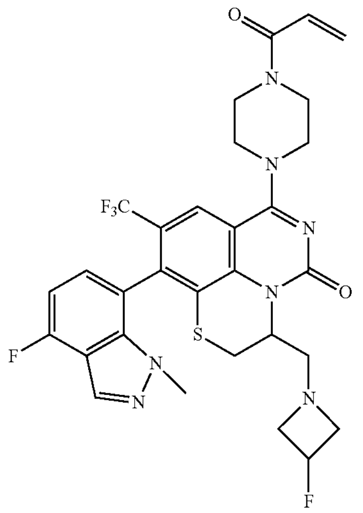
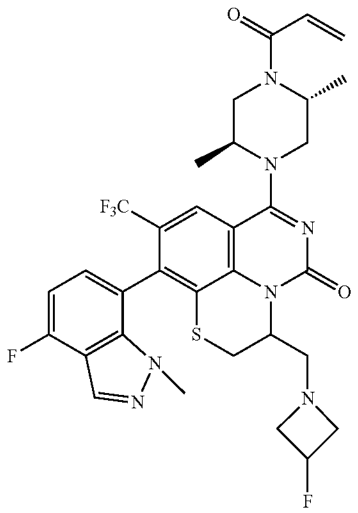
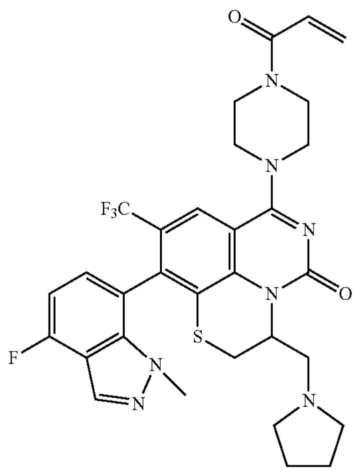
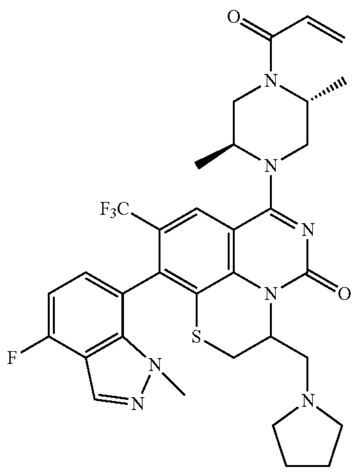

-continued
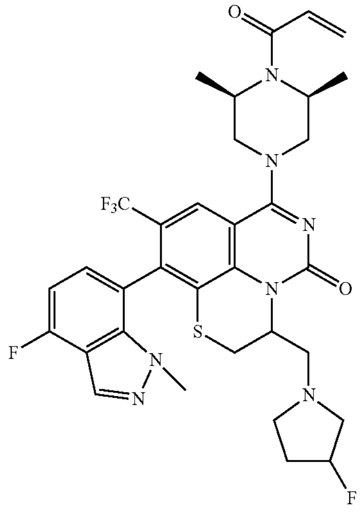
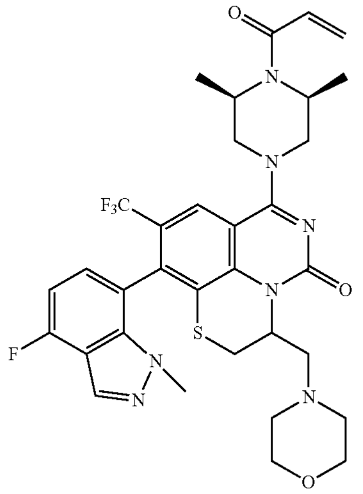
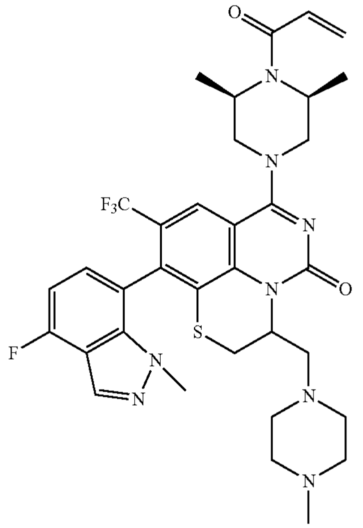
-continued
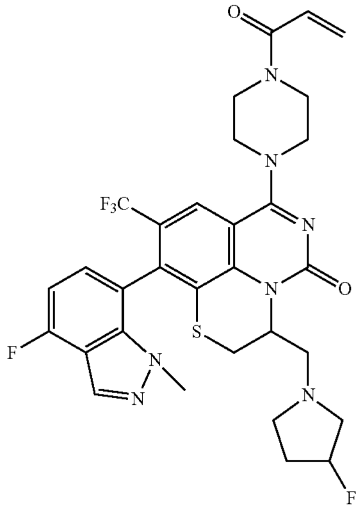
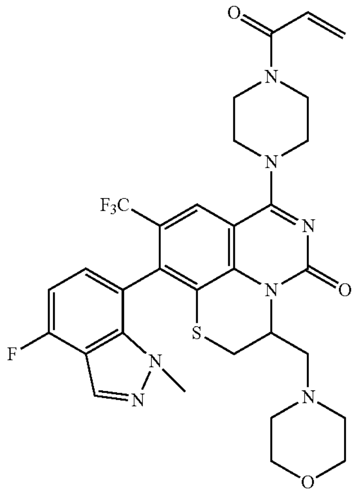
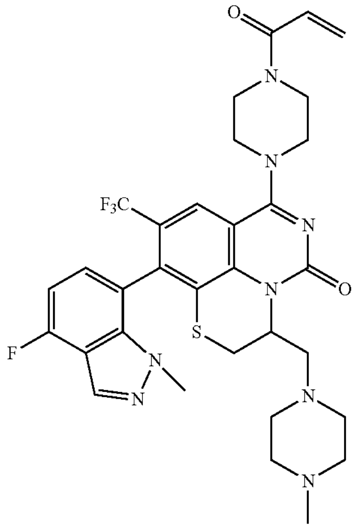

-continued
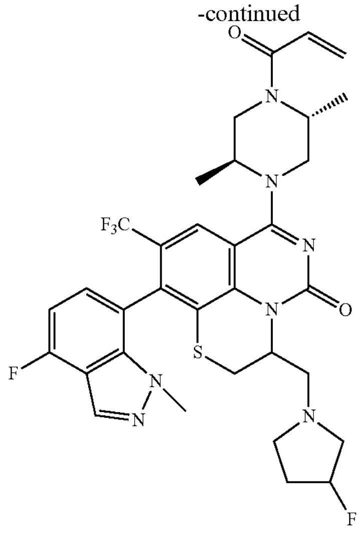
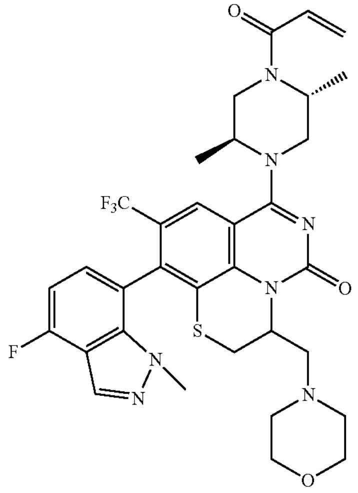
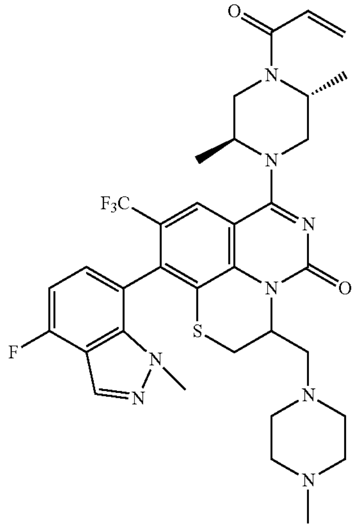
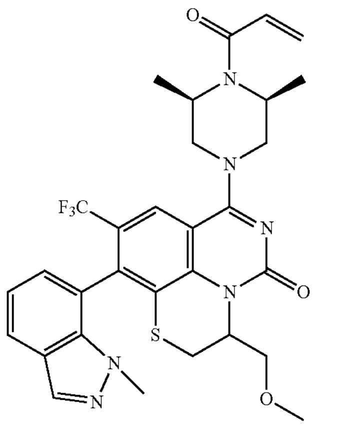
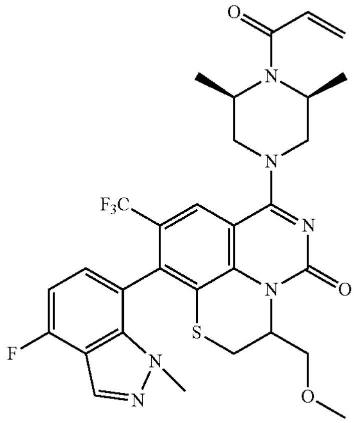
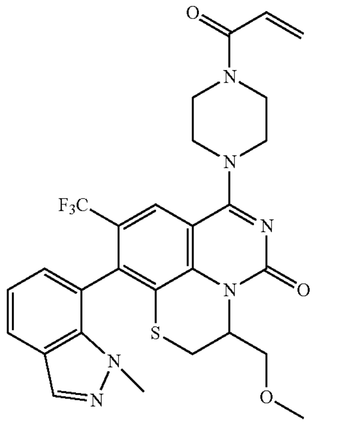
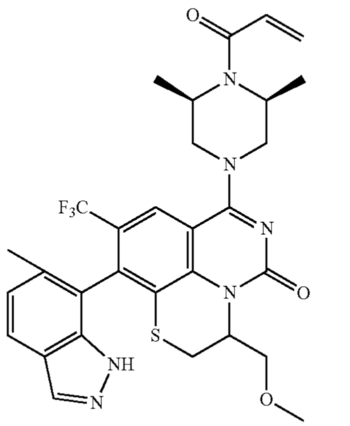

-continued
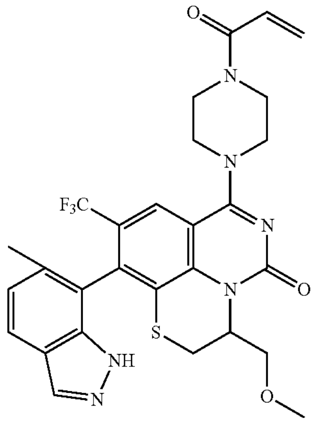
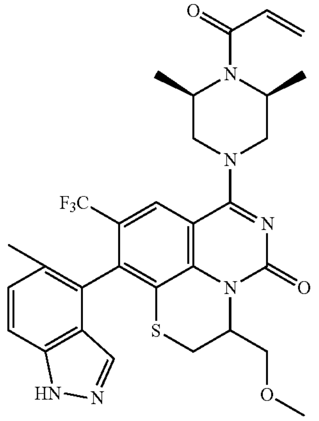
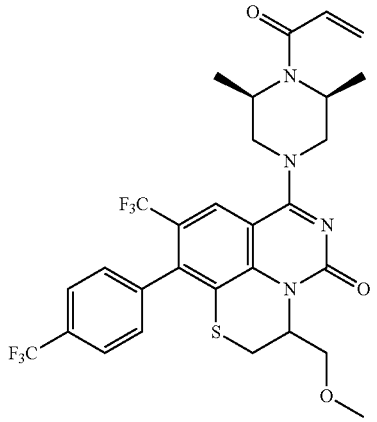
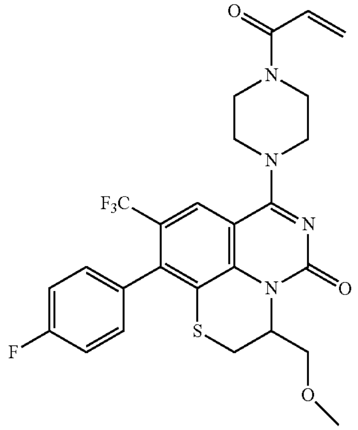
-continued
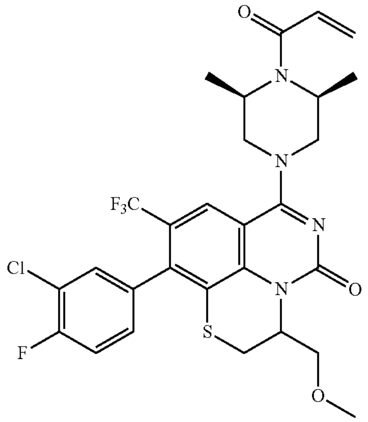
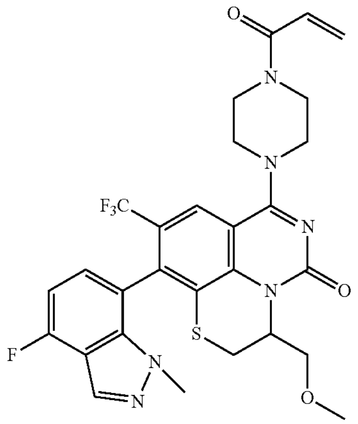
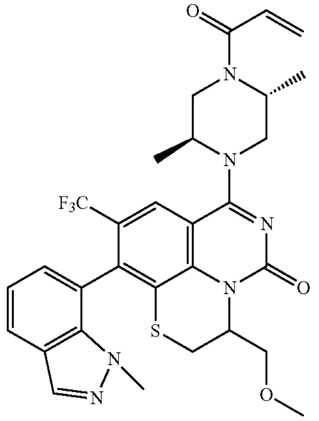
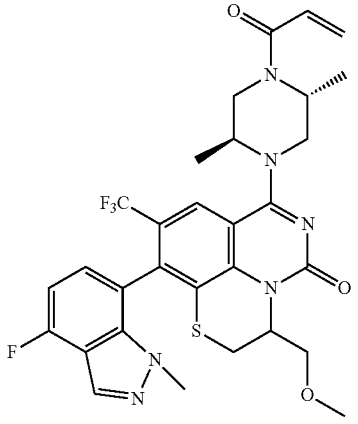

-continued
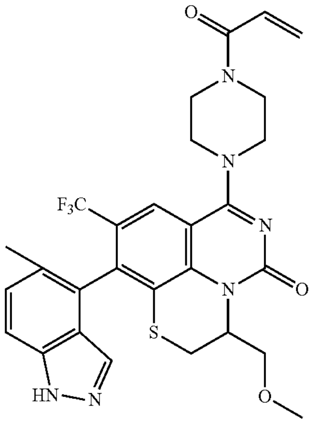
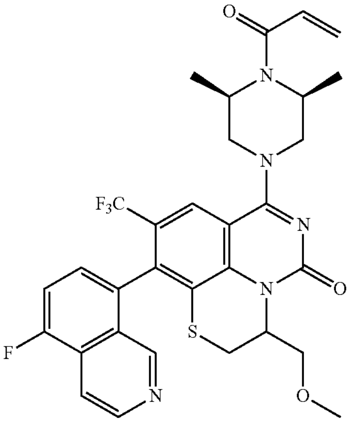
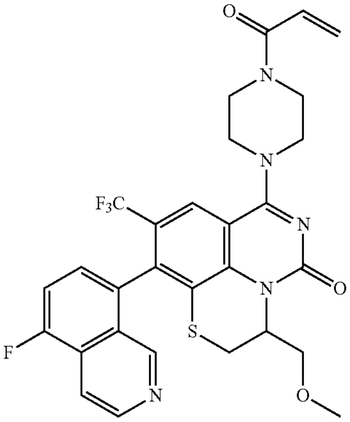
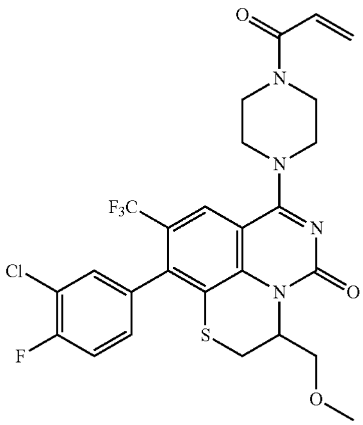
-continued
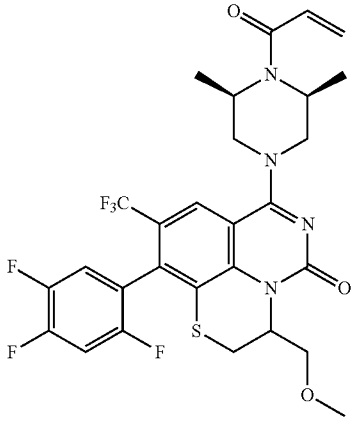
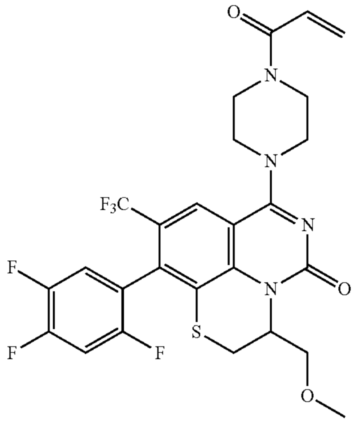
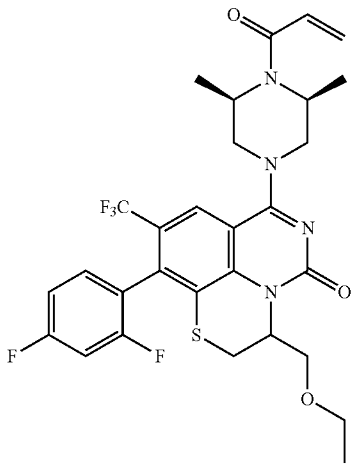

-continued
-continued
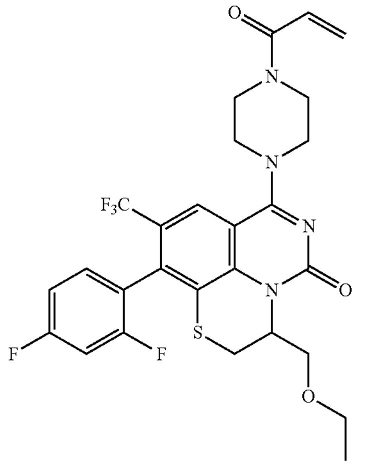
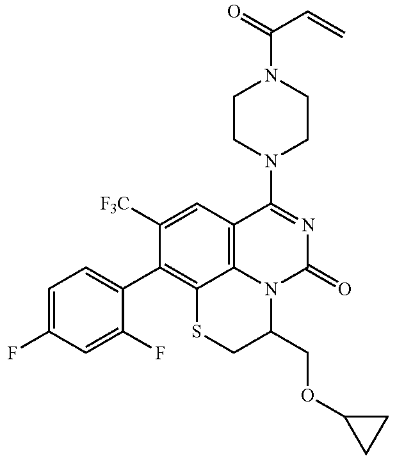
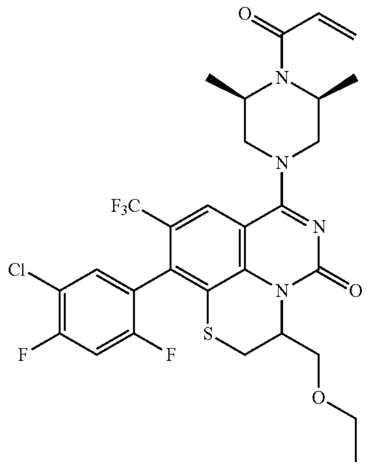
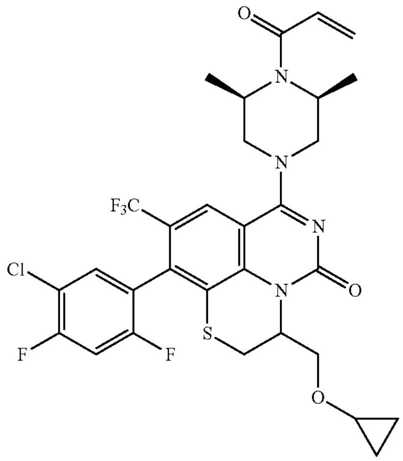
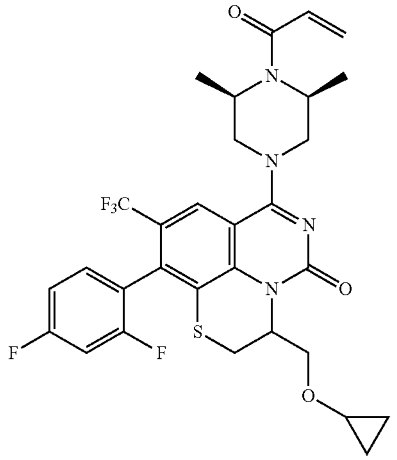
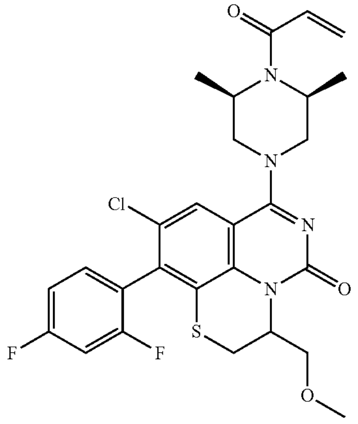

-continued
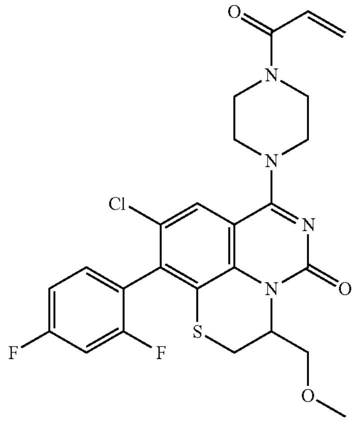
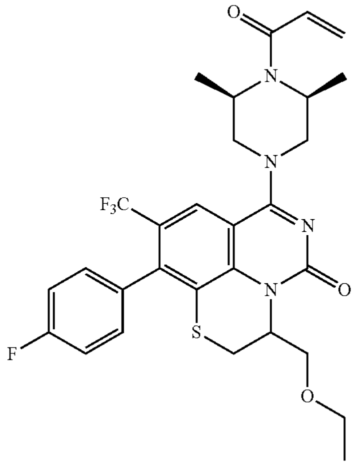
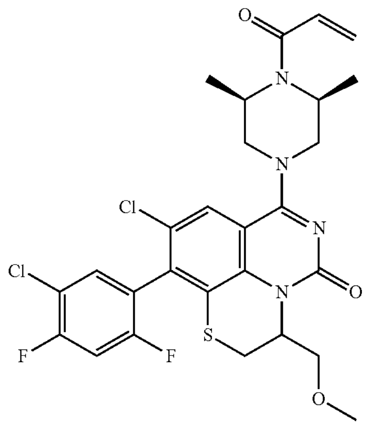
-continued
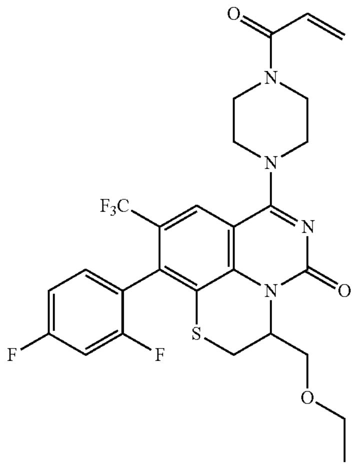
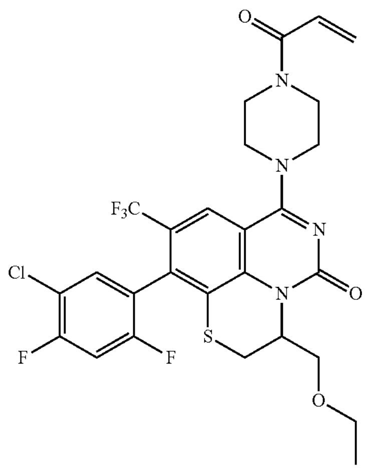
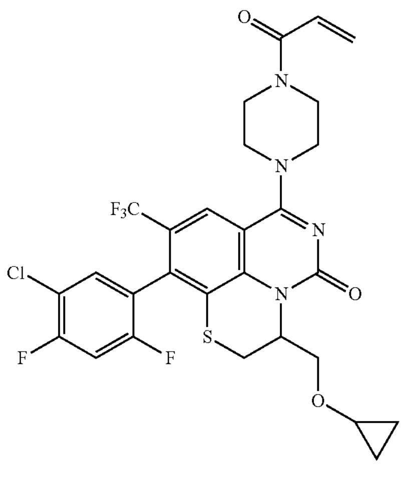

-continued
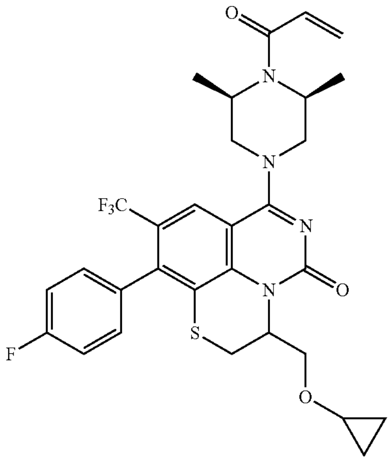
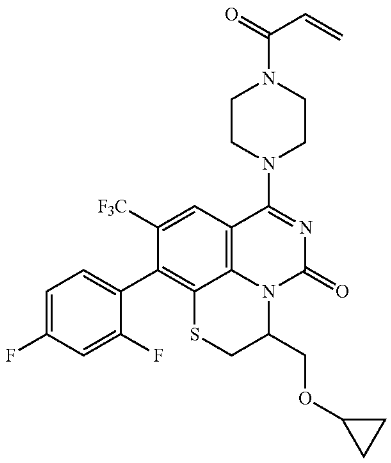
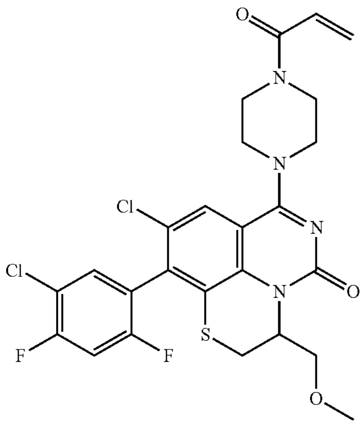
-continued
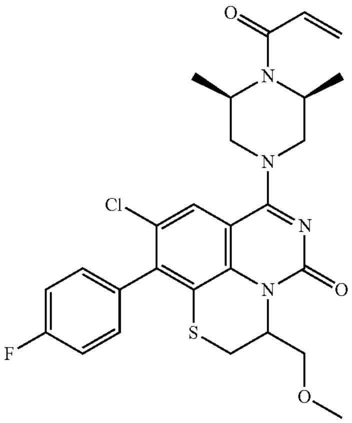
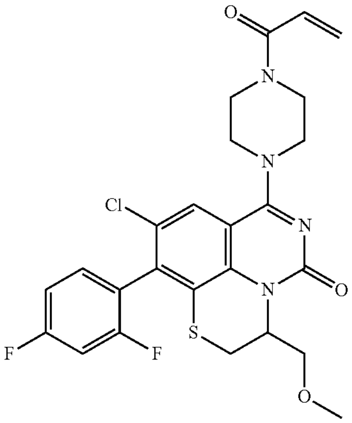
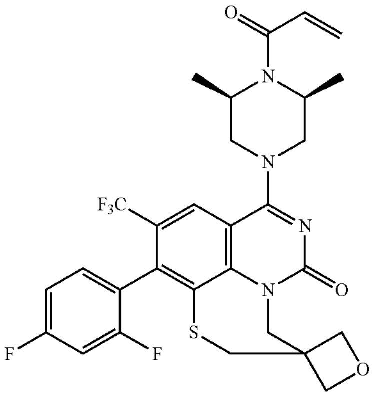
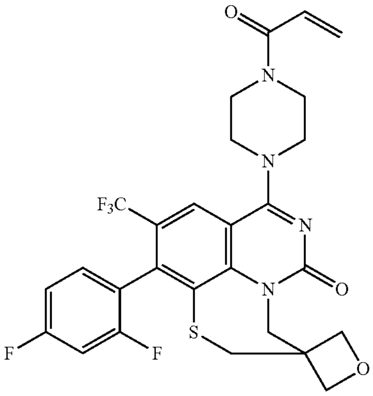

-continued
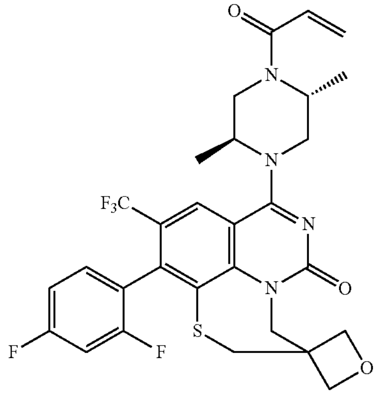
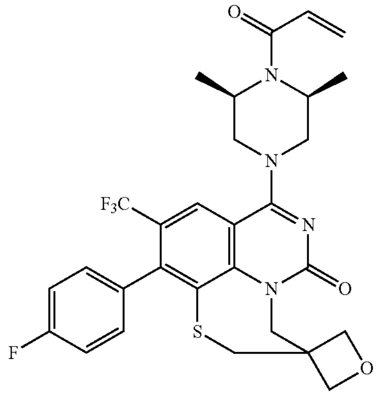
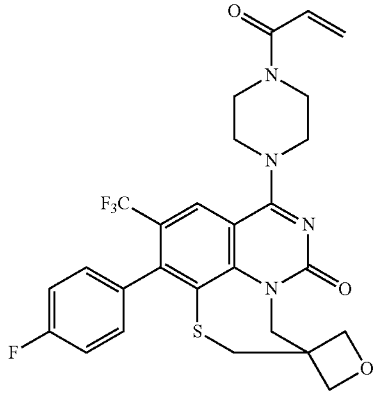
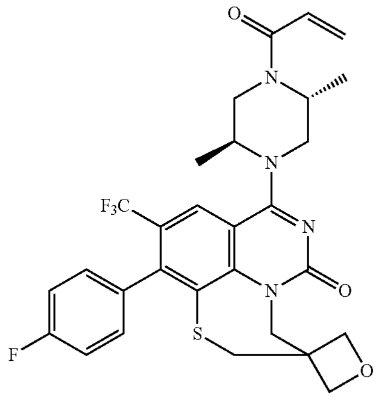
-continued
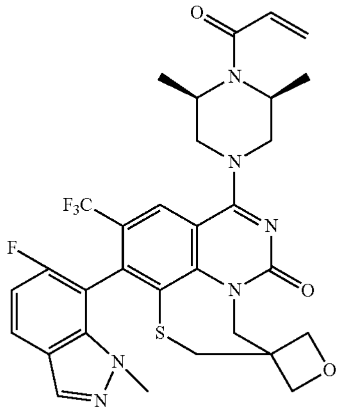
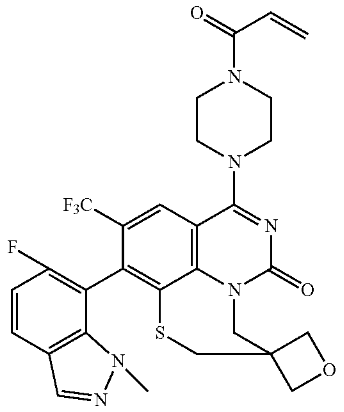
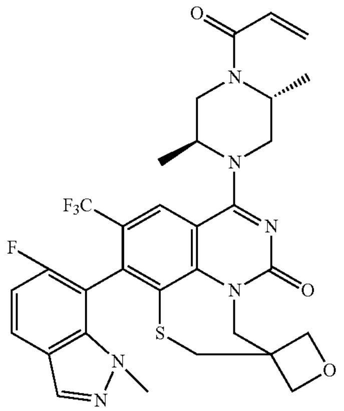
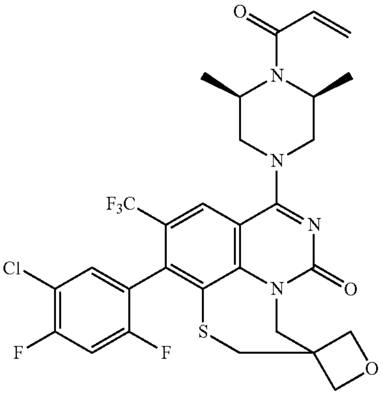

-continued
-continued
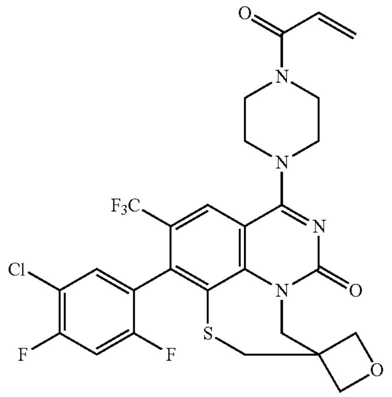
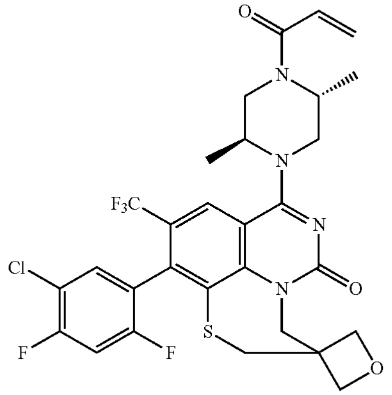
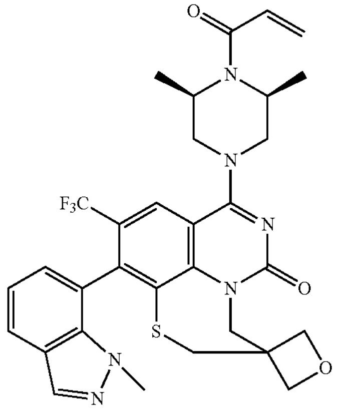
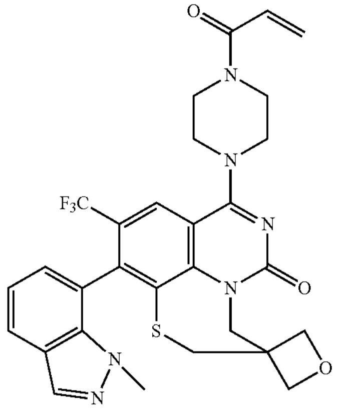
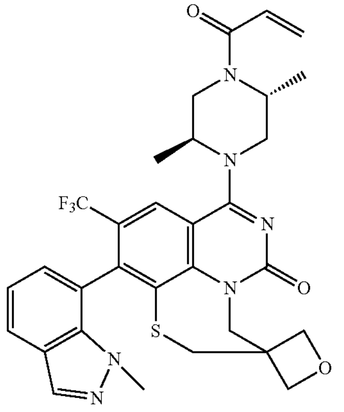
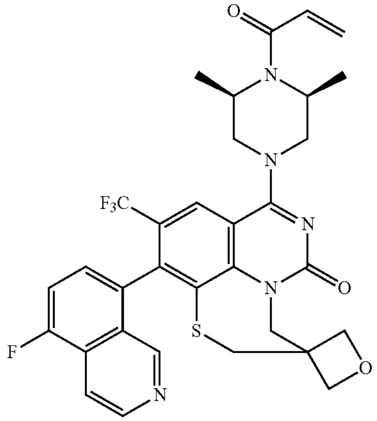
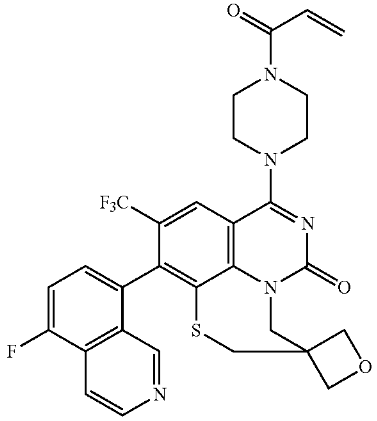
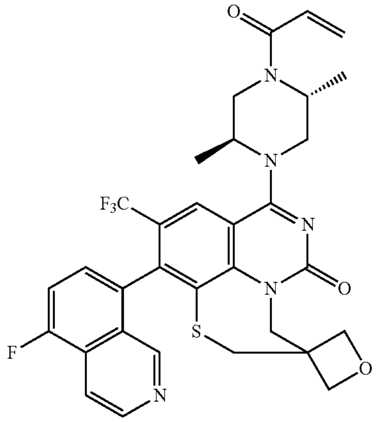

-continued
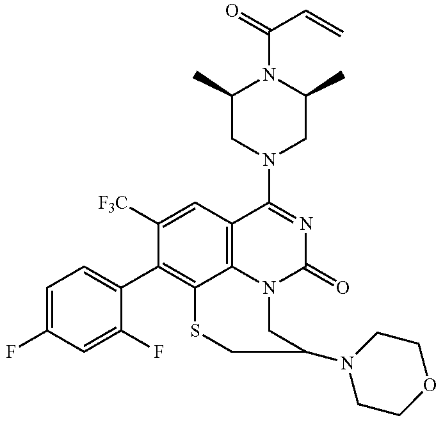
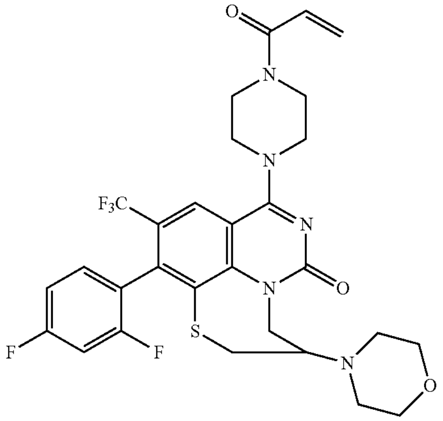
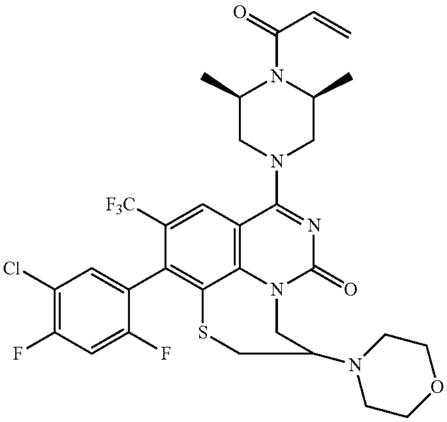
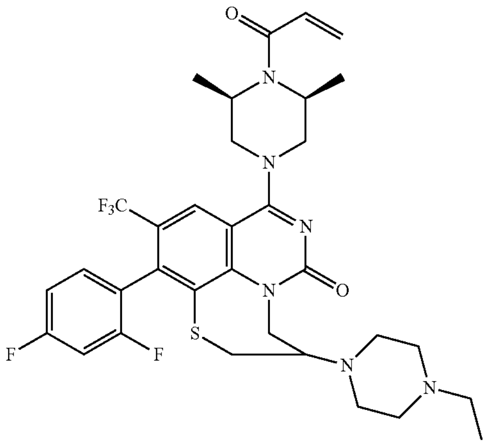
-continued
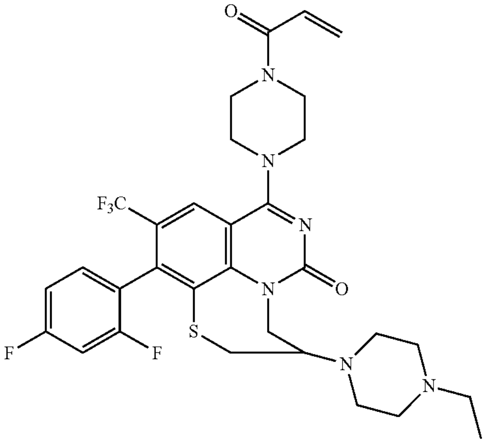
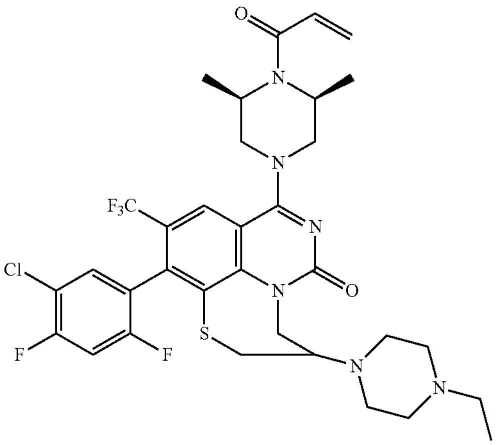
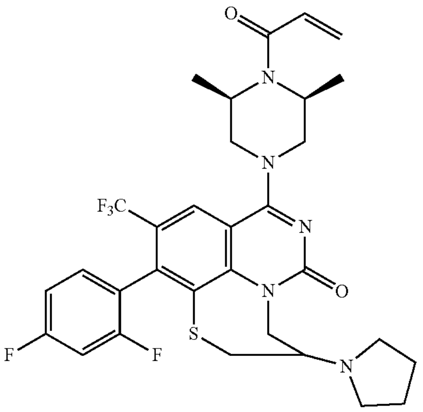
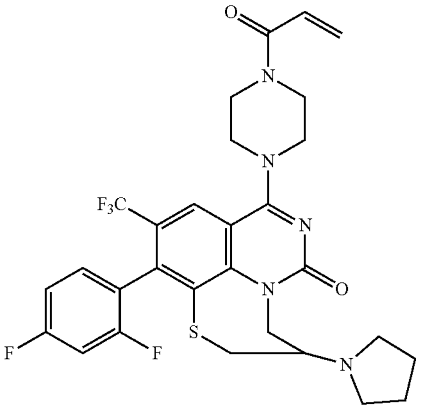

-continued
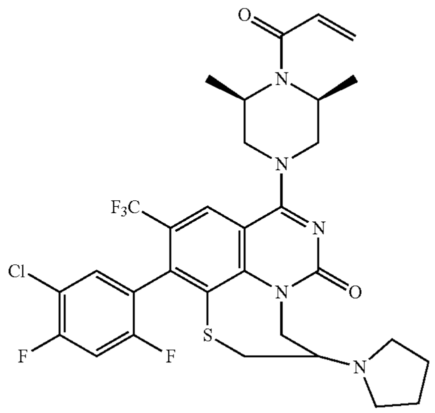
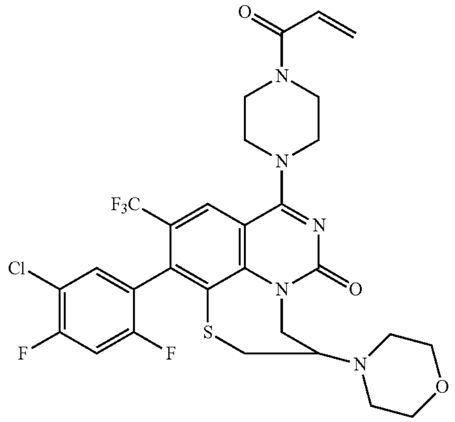
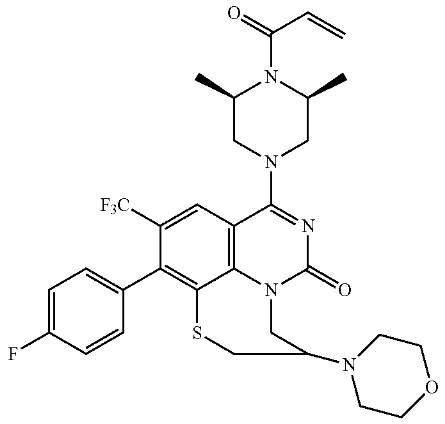
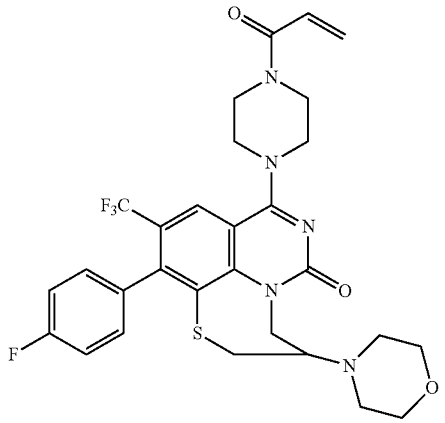
-continued
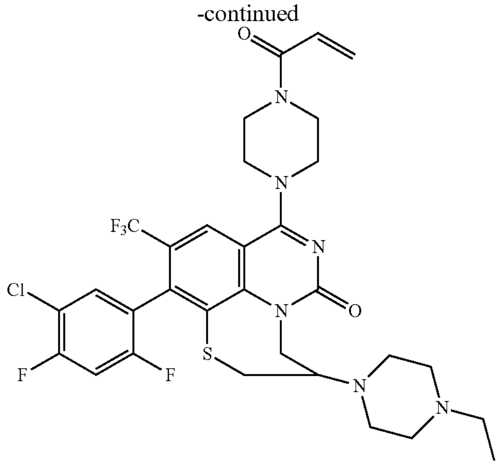
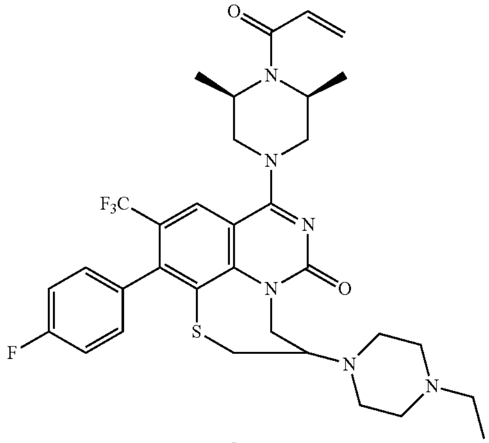
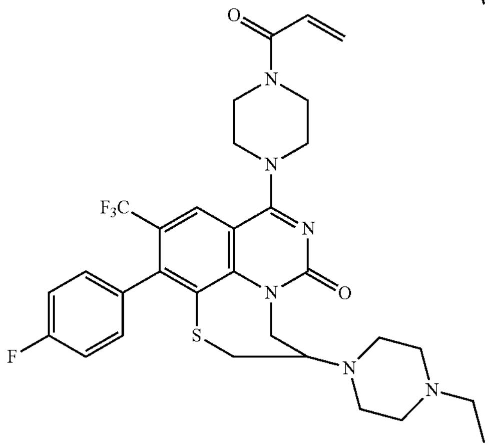
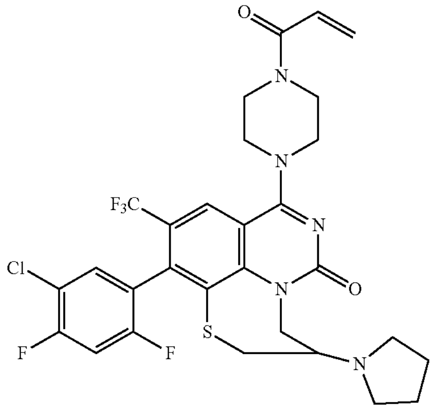

-continued
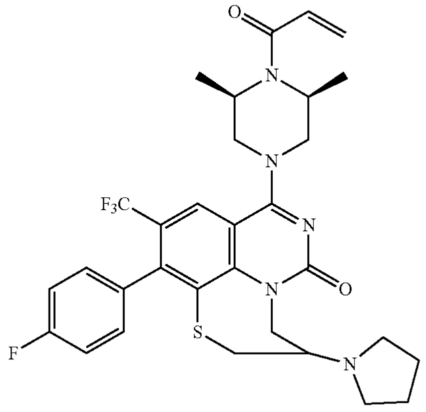
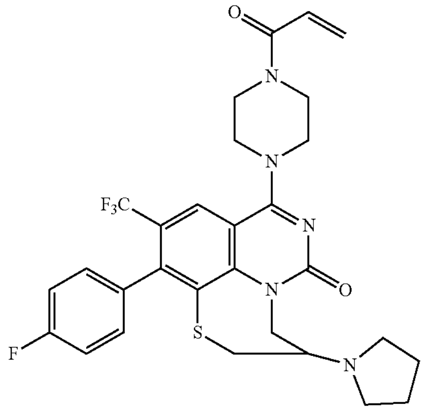
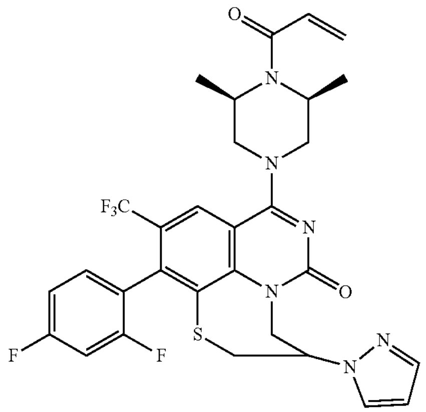
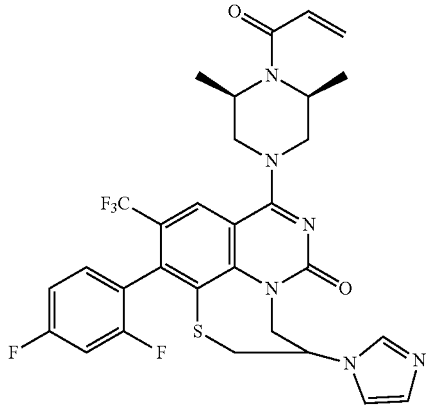
-continued
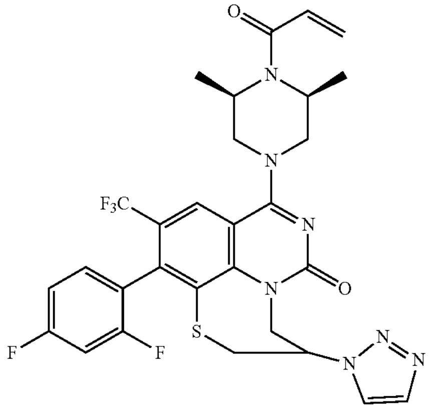
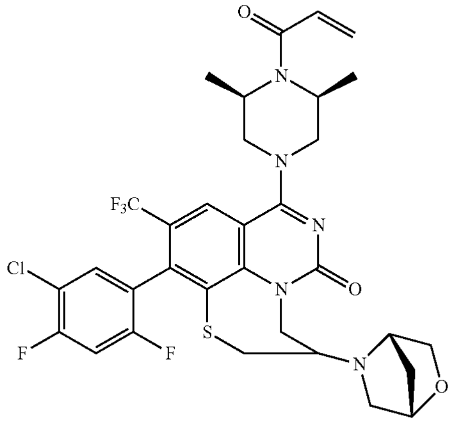
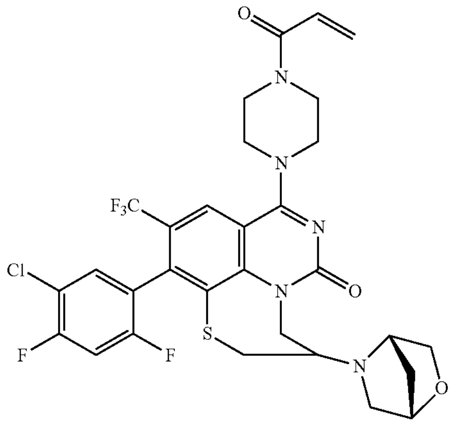
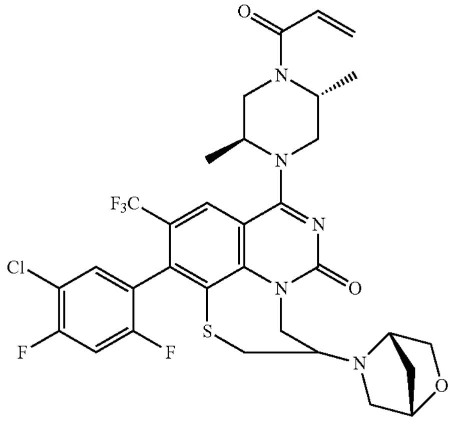

-continued
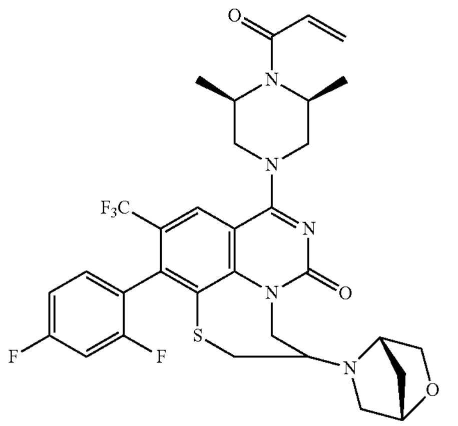
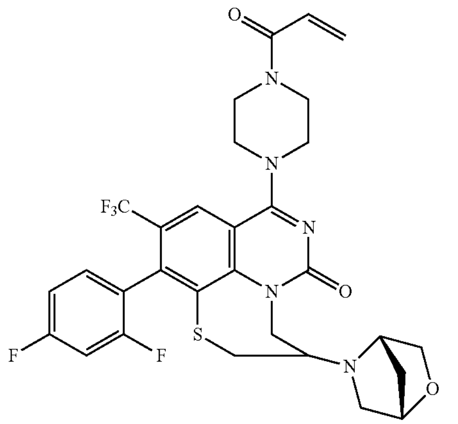
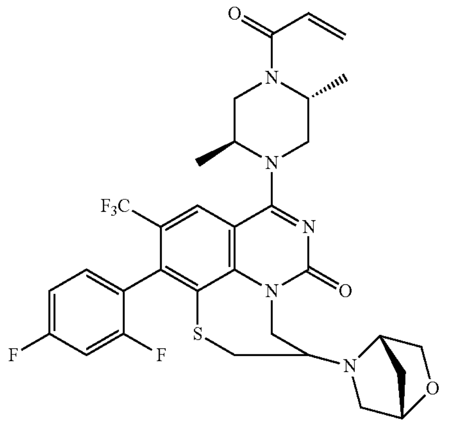
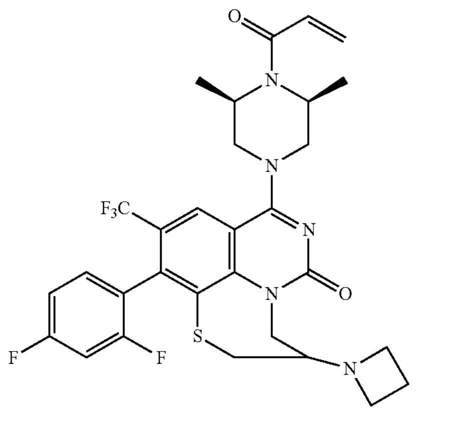
-continued
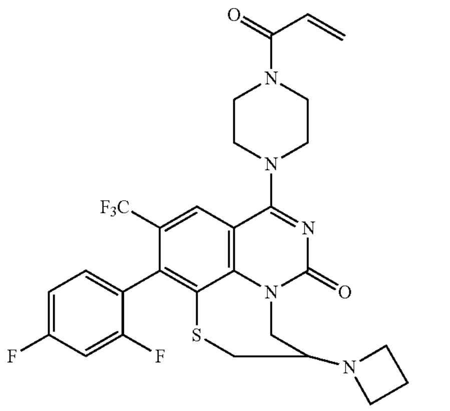
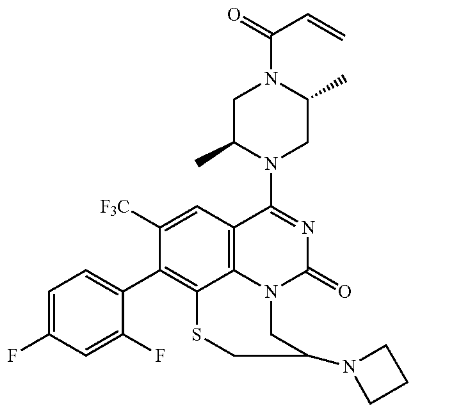
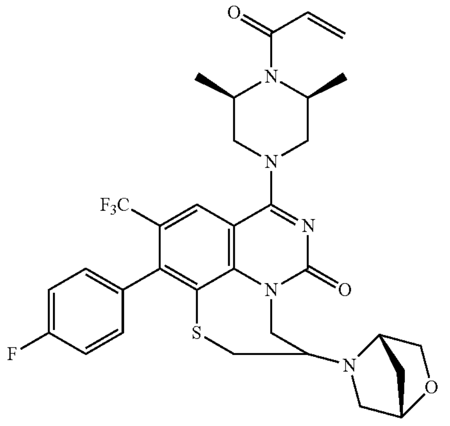
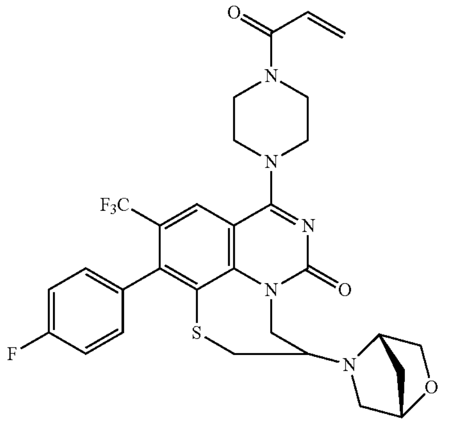

-continued

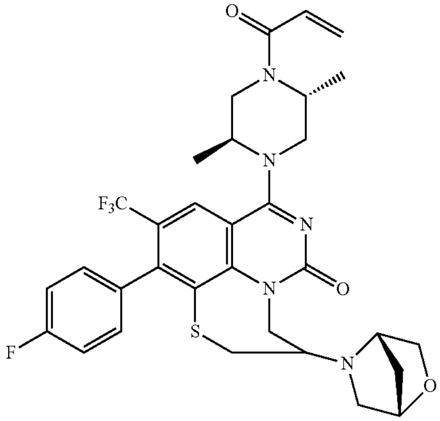

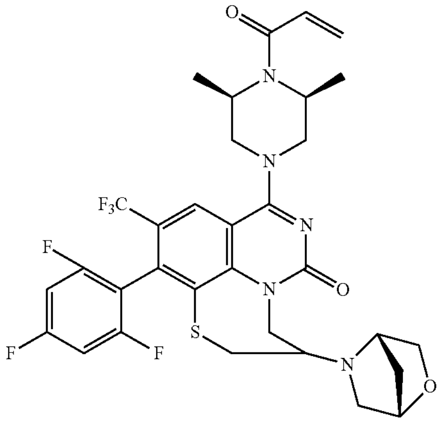

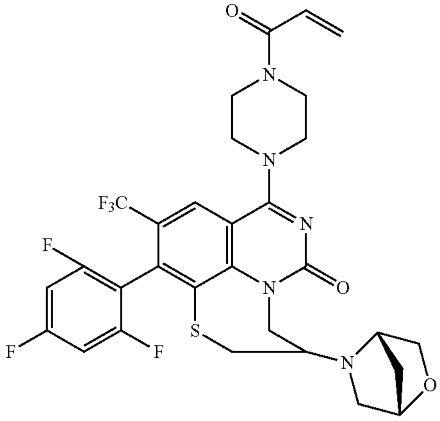

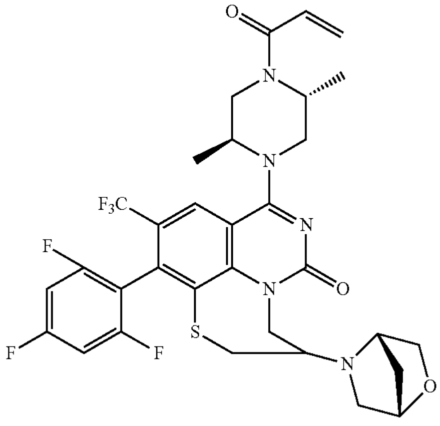

It will be appreciated by those skilled in the art that the compounds above possess chiral centers as well potential axial asymmetry, i.e., atropisomers. Each of the compounds may be provided as a mixture of diastereomers or in any diasteromerically pure form. Representative experimental examples of the above follow.

Example 1139 and 1140

(3S,10S)-7-((3S,5R)-4-acryloyl-3,5-dimethylpiperazin-1-yl)-10-(5-chloro-2,4-difluorophenyl)-3-(methoxymethyl)-9-(trifluoromethyl)-2,3-dihydro-5H-[1,4]thiazino[2,3,4-ij]quinazolin-5-one (P1) and (3S,10R)-7-((3S,5R)-4-acryloyl-3,5-dimethylpiperazin-1-yl)-10-(5-chloro-2,4-difluorophenyl)-3-(methoxymethyl)-9-(trifluoromethyl)-2,3-dihydro-5H-[1,4]thiazino[2,3,4-ij]quinazolin-5-one (P2)

P1

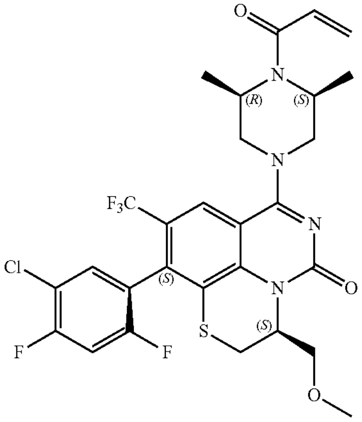

P2

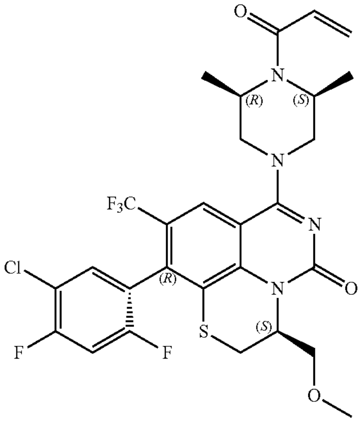

Reaction Scheme

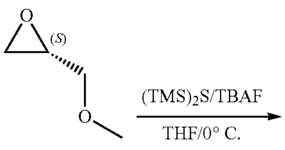

1

-continued
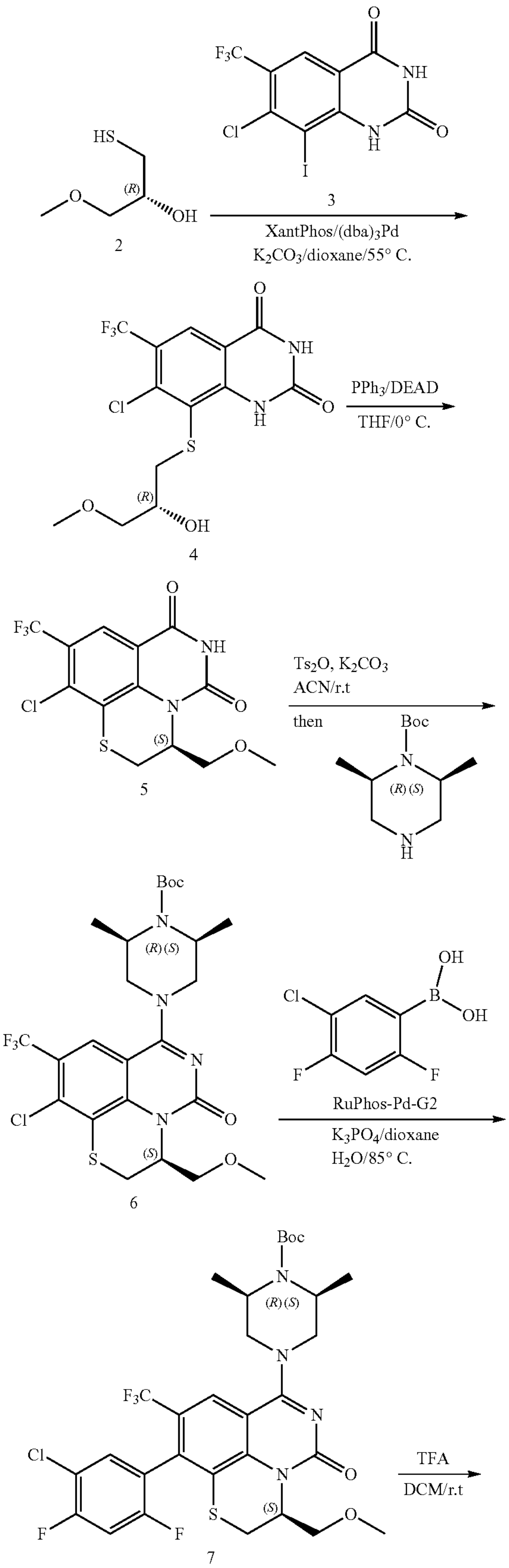
-continued
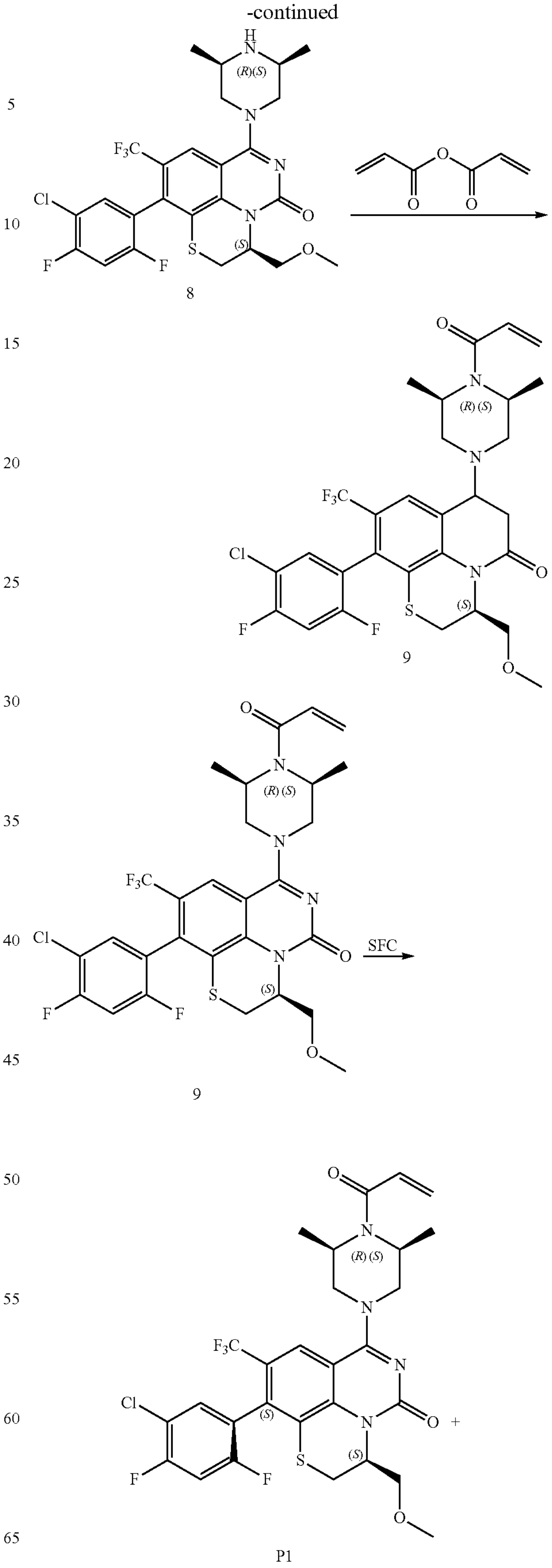

-continued

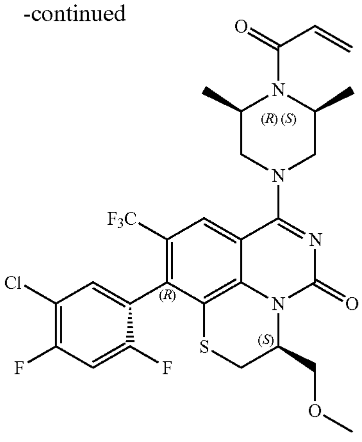

P2

(R)-1-mercapto-3-methoxypropan-2-ol (2)

To a mixture of (S)-2-(methoxymethyl)oxirane (50 g, 568.2 mmol) in tetrahydrofuran (800 mL) was added 1,1,1,3,3,3-hexamethyldisilathiane (119.4 g, 681.8 mmol) and tetrabutylammonium fluoride (1.0 M in tetrahydrofuran, 170.6 mL, 170.5 mmol) at 0° C. The mixture was stirred at room temperature for 2 hours. After completion, the mixture was poured into water (3000 mL), extracted with ethyl acetate (3×800 mL). The combined organic phases were washed with brine (800 mL) and dried over anhydrous sodium sulfate. After filtration and concentration, the residue was purified by silica gel column with petroleum ether/ethyl acetate=3/1 to afford (R)-1-mercapto-3-methoxypropan-2-ol (70.0 g, crude) as a colorless oil. $^1$H NMR (300 MHz, $CDCl_3$) δ 3.86-3.82 (m, 1H), 3.49-3.46 (m, 1H), 3.41-3.37 (m, 4H), 2.71-2.64 (m, 1H), 1.55-1.50 (m, 1H).

(R)-7-chloro-8-((2-hydroxy-3-methoxypropyl)thio)-6-(trifluoromethyl)quinazoline-2,4(1H,3H)-dione (4)

To a solution of 7-chloro-8-iodo-6-(trifluoromethyl)quinazoline-2,4(1H,3H)-dione (2) (20 g, 51.2 mmol) in dioxane (800 mL), potassium carbonate (21.2 g, 153.6 mmol), (R)-1-mercapto-3-methoxypropan-2-ol (11.26 g, 92.1 mmol), 4,5-Bis(diphenyl-phosphino)-9,9-dimethylxanthene (5.93 g, 10.24 mmol) and Tris(dibenzylideneacetone) dipalladium (4.7 g, 5.1 mmol) were added. The mixture was stirred at 55° C. under nitrogen atmosphere for 18 hours. After completion, the insoluble was filtered out. After concentration, the residue was adjusted to pH=4 with acetic acid and extracted with ethyl acetate (1000 mL), washed with brine (500 mL). The organic phase was concentrated and recrystallized (dichloromethane/methanol=1/10). The mixture was filtered and collected filter cake to afford (R)-7-chloro-8-((2-hydroxy-3-methoxypropyl)thio)-6-(trifluoromethyl)quinazoline-2,4(1H,3H)-dione (14 g, yield: 71%) as a white solid. MS (ESI) m/z 385.0 [M+H]$^+$.

(S)-10-chloro-3-(methoxymethyl)-9-(trifluoromethyl)-2H-[1,4]thiazino[2,3,4-ij]quinazoline-5,7(3H,6H)-dione (5)

To a mixture of (R)-7-chloro-8-((2-hydroxy-3-methoxypropyl)thio)-6-(trifluoromethyl)quinazoline-2,4(1H,3H)-dione (34.4 g, 89.5 mmol) and triphenylphosphoranylidene (35.2 g, 134.3 mmol) in tetrahydrofuran (500 mL) was added diethyl azodicarboxylate (23.3 g, 134.3 mmol) at 0° C. The mixture was stirred at 0° C. for 45 min. After completion, the mixture was poured into ice-water (300 mL) and extracted with ethyl acetate (3×500 mL). After concentration, the residue was recrystallized (dichloromethane/methanol=1/10). The mixture was filtered and collected filter cake to afford (S)-10-chloro-3-(methoxymethyl)-9-(trifluoromethyl)-2H-[1,4]thiazino[2,3,4-ij]quinazoline-5,7(3H,6H)-dione (5) (24.0 g, 73% yield) as a white solid. MS (ESI): m/z 367.0 [M+H]$^+$.

(2S,6R)-tert-butyl 4-((S)-10-chloro-3-(methoxymethyl)-5-oxo-9-(trifluoromethyl)-3,5-dihydro-2H-[1,4]thiazino[2,3,4-ij]quinazolin-7-yl)-2,6-dimethylpiperazine-1-carboxylate (6)

To a mixture of (S)-10-chloro-3-(methoxymethyl)-9-(trifluoromethyl)-2H-[1,4]thiazino[2,3,4-ij]quinazoline-5,7(3H,6H)-dione (5) (10 g, 27.32 mmol) and potassium carbonate (37.7 g, 273.2 mmol) in acetonitrile (500 mL) was added 4-methylbenzenesulfonic anhydride (13.4 g, 40.98 mmol) at 0° C. The mixture was stirred at 0° C. for 30 min and at 30° C. for 4 hours. After completion, (2S,6R)-tert-butyl 2,6-dimethylpiperazine-1-carboxylate (11.7 g, 54.64 mmol) was added into the reaction solution. The reaction mixture was stirred at 0° C. for 2 hour. After completion, the mixture was filtered through a Celite pad. After concentration, the residue was purified by chromatography column (dichloromethane/methanol=100/1 to 30/1) to afford (2S,6R)-tert-butyl 4-((S)-10-chloro-3-(methoxymethyl)-5-oxo-9-(trifluoromethyl)-3,5-dihydro-2H-[1,4]thiazino[2,3,4-ij]quinazolin-7-yl)-2,6-dimethylpiperazine-1-carboxylate (6) (15 g, crude) as a pale-white solid. MS (ESI) m/z 563.5 [M+H]$^+$.

(2S,6R)-tert-butyl 4-((3S)-10-(5-chloro-2,4-difluorophenyl)-3-(methoxymethyl)-5-oxo-9-(trifluoromethyl)-3,5-dihydro-2H-[1,4]thiazino[2,3,4-ij]quinazolin-7-yl)-2,6-dimethylpiperazine-1-carboxylate (7)

To a solution of (2S,6R)-tert-butyl 4-((S)-10-chloro-3-(methoxymethyl)-5-oxo-9-(trifluoromethyl)-3,5-dihydro-2H-[1,4]thiazino[2,3,4-ij]quinazolin-7-yl)-2,6-dimethylpiperazine-1-carboxylate (40 g, 71.0 mmol) in 1,4-dioxane (500 mL) and water (50 mL), tripotassium phosphate (16.9 g, 213 mmol), (5-chloro-2,4-difluorophenyl)boronic acid (24.4 g, 142 mmol), and Chloro(2-dicyclohexylphosphino-2',6'-diisopropoxy-1,1'-biphenyl)[2-(2'-amino-1,1'-biphenyl)]palladium(II) (8.27 g, 10.7 mmol) were added. The mixture was stirred at 85° C. under nitrogen atmosphere for 4 hours. After completion, the mixture was diluted with tetrahydrofuran (3 L) and the insoluble was filtered out. After concentration, the residue was purified by silica gel column chromatography (dichloromethane/methanol=100/1 to 30/1) to afford ((2S,6R)-tert-butyl 4-((3S)-10-(5-chloro-2,4-difluorophenyl)-3-(methoxymethyl)-5-oxo-9-(trifluoromethyl)-3,5-dihydro-2H-[1,4]thiazino[2,3,4-ij]quinazolin-7-yl)-2,6-dimethylpiperazine-1-carboxylate (7) (45 g, crude) as a yellow solid. MS (ESI) m/z 674.6 [M+H]$^+$.

(3S)-10-(5-chloro-2,4-difluorophenyl)-7-((3S,5R)-3,5-dimethylpiperazin-1-yl)-3-(methoxymethyl)-9-(trifluoromethyl)-2H-[1,4]thiazino[2,3,4-ij]quinazolin-5(3H)-one (8)

To a cooled mixture of (((2S,6R)-tert-butyl 4-((3S)-10-(5-chloro-2,4-difluorophenyl)-3-(methoxymethyl)-5-oxo-9-

(trifluoromethyl)-3,5-dihydro-2H-[1,4]thiazino[2,3,4-ij]quinazolin-7-yl)-2,6-dimethylpiperazine-1-carboxylate (45 g, 71.0 mmol) in dichloromethane (300 ml) was added trifluoroacetic acid (100 mL) at 0° C. The reaction solution was stirred at room temperature for 3 hours. After completion, the mixture was concentrated. The residue was redissolved in dichloromethane and washed with saturated $NaHCO_3$. The organic layer was dried over $Na_2SO_4$ and concentrated. The residue was purified by column (dichloromethane/methanol=15:1) to afford (3S)-10-(5-chloro-2,4-difluorophenyl)-7-((3S,5R)-3,5-dimethylpiperazin-1-yl)-3-(methoxymethyl)-9-(trifluoromethyl)-2H-[1,4]thiazino[2,3,4-ij]quinazolin-5(3H)-one (8) (25 g, yield: 62%) as a yellow solid. MS (ESI) m/z 575.6 $[M+H]^+$.

(3S)-7-((3S,5R)-4-acryloyl-3,5-dimethylpiperazin-1-yl)-10-(5-chloro-2,4-difluorophenyl)-3-(methoxymethyl)-9-(trifluoromethyl)-2H-[1,4]thiazino[2,3,4-ij]quinazolin-5(3H)-one (9)

To a mixture of (3S)-10-(5-chloro-2,4-difluorophenyl)-7-((3S,5R)-3,5-dimethylpiperazin-1-yl)-3-(methoxymethyl)-9-(trifluoromethyl)-2H-[1,4]thiazino[2,3,4-ij]quinazolin-5(3H)-one (8) (25 g, 43.6 mmol) and triethyl amine (13.2 g, 130 mmol) in dichloromethane (300 ml) was added acrylic anhydride (8.23 g, 65.3 mmol) at 0° C. The mixture was stirred at 0° C. for 3 hours. After completion, the mixture was poured into ice-water (800 mL) and extracted with ethyl acetate (3×800 mL). After concentration, the residue was purified by chromatography column (dichloromethane/methanol=60/1 to 30/1) to afford (3S)-7-((3S,5R)-4-acryloyl-3,5-dimethylpiperazin-1-yl)-10-(5-chloro-2,4-difluorophenyl)-3-(methoxymethyl)-9-(trifluoromethyl)-2H-[1,4]thiazino[2,3,4-ij]quinazolin-5(3H)-one (9) (14 g, yield: 52%) as a white solid. MS (ESI) m/z 629.6 $[M+H]^+$. $^1H$ NMR (400 MHz, $CDCl_3$) δ 8.06 (s, 1H), 7.28-7.24 (m, 1H), 7.09-7.04 (m, 1H), 6.65-6.59 (m, 1H), 6.40 (dd, J=1.6 Hz, 16.8 Hz, 1H), 5.77 (dd, J=1.6 Hz, 10.8 Hz, 1H), 5.50-5.43 (m, 1H), 4.75-4.59 (m, 2H), 4.21-4.15 (m, 2H), 3.67-3.62 (m, 2H), 3.41-3.30 (m, 6H), 3.05-3.01 (m, 1H), 1.62-1.61 (m, 3H), 1.49-1.46 (m, 3H).

The above diastereomers (14 g) were dissolved with EtOH (1500 mL), separated by chiral Prep. HPLC (separation condition: Column:Chiralpak AS-H 5 μm 20×250 mm; Mobile Phase: $CO_2$:EtOH=70:30 at 25 mL/min; Temp: 25° C.; Wavelength: 254 nm) to afford the title compounds P1 (7.62 g, 54% yield, 100% de), and P2 (4.25 g, 30% yield, 98.1% de); Chiral HPLC Analytical: on CHIRALPAK® AS-H was using 5 μm 4.6×250 mm column, Mobile Phase: $CO_2$:EtOH=70:30 at 2.5 mL/min; Temp: 25° C.; Wavelength: 254 nm).

P1: $^1H$ NMR (400 MHz, $CDCl_3$) δ 8.06 (s, 1H), 7.28-7.24 (m, 1H), 7.07 (t, J=8.8 Hz, 1H), 6.65-6.59 (m, 1H), 6.40 (dd, J=1.6 Hz, 16.8 Hz, 1H), 5.77 (dd, J=1.2 Hz, 10.0 Hz, 1H), 5.45-5.44 (m, 1H), 4.73-4.58 (m, 2H), 4.21-4.15 (m, 2H), 3.67-3.64 (m, 2H), 3.41-3.31 (m, 6H), 3.05-3.01 (m, 1H), 1.61 (m, J=6.8 Hz, 3H), 1.47 (d, J=6.8 Hz, 3H); Chiral HPLC Analytical: on AD-H was using 4.6×150 mm column, Mobile Phase: $CO_2$:EtOH=70:30 at 2.5 mL/min; Temp: 25° C.; Wavelength: 254 nm), Peak 1: e.e. =100%, Rt=3.76 min.

P2: $^1H$ NMR (400 MHz, $CDCl_3$) δ 8.07 (s, 1H), 7.28-7.25 (m, 1H), 7.07 (t, J=8.8 Hz, 1H), 6.65-6.59 (m, 1H), 6.40 (dd, J=1.6 Hz, 16.4 Hz, 1H), 5.77 (dd, J=1.6 Hz, 10.4 Hz, 1H), 5.48-5.45 (m, 1H), 4.76-4.59 (m, 2H), 4.21-4.16 (m, 2H), 3.68-3.59 (m, 2H), 3.39-3.30 (m, 6H), 3.04-3.00 (m, 1H), 1.61-1.59 (m, 3H), 1.46 (d, J=6.4 Hz, 3H); Chiral HPLC Analytical: on AD-H was using 4.6×150 mm column, Mobile Phase: $CO_2$: EtOH=70:30 at 2.5 mL/min; Temp: 25° C.; Wavelength: 254 nm), Peak 2: e.e. =98.1%, Rt=4.30 min.

Example 1103

(S)-7-((3S,5R)-4-acryloyl-3,5-dimethylpiperazin-1-yl)-10-(4-fluorophenyl)-3-(methoxymethyl)-9-(trifluoromethyl)-2H-[1,4]thiazino[2,3,4-ij]quinazolin-5(3H)-one

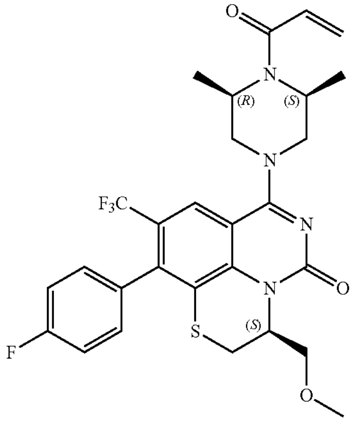

Reaction Scheme

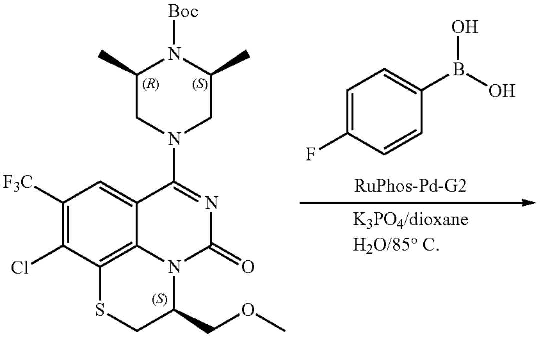

1

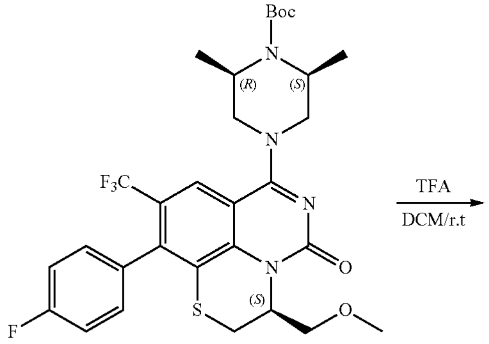

2

-continued

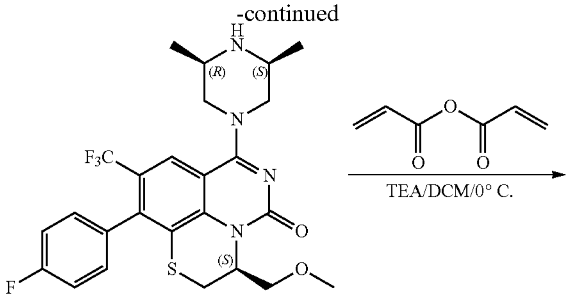

3

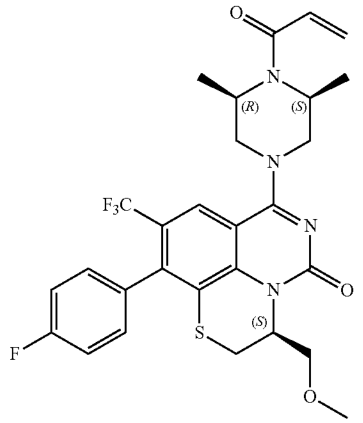

4

(2S,6R)-tert-butyl 4-((S)-10-(4-fluorophenyl)-3-(methoxymethyl)-5-oxo-9-(trifluoromethyl)-3,5-dihydro-2H-[1,4]thiazino[2,3,4-ij]quinazolin-7-yl)-2,6-dimethylpiperazine-1-carboxylate (2)

To a solution of (2S,6R)-tert-butyl 4-((S)-10-chloro-3-(methoxymethyl)-5-oxo-9-(trifluoromethyl)-3,5-dihydro-2H-[1,4]thiazino[2,3,4-ij]quinazolin-7-yl)-2,6-dimethylpiperazine-1-carboxylate (1) (8.0 g, 14.2 mmol) in 1,4-dioxane (200 mL) and water (25 mL), tripotassium phosphate (18.9 g, 71 mmol), (4-fluorophenyl)boronic acid (9.94 g, 71 mmol), and Chloro(2-dicyclohexylphosphino-2', 6'-diisopropoxy-1,1'-biphenyl)[2-(2'-amino-1,1'-biphenyl)]palladium(II) (2.2 g, 2.84 mmol) were added. The mixture was stirred at 85° C. under nitrogen atmosphere for 4 hours. After completion, the mixture was diluted with tetrahydrofuran (3 L) and the insoluble was filtered out. After concentration, the residue was purified by silica gel column chromatography (dichloromethane/methanol=100/1 to 30/1) to afford (2S, 6R)-tert-butyl 4-((S)-10-(4-fluorophenyl)-3-(methoxymethyl)-5-oxo-9-(trifluoromethyl)-3,5-dihydro-2H-[1,4]thiazino[2,3,4-ij]quinazolin-7-yl)-2,6-dimethylpiperazine-1-carboxylate (13 g, crude) as a yellow solid. MS (ESI) m/z 623.4 $[M+H]^+$.

(S)-7-((3S,5R)-3,5-dimethylpiperazin-1-yl)-10-(4-fluorophenyl)-3-(methoxymethyl)-9-(trifluoromethyl)-2H-[1,4]thiazino[2,3,4-ij]quinazolin-5(3H)-one (3)

To a cooled mixture of (2S,6R)-tert-butyl 4-((S)-10-(4-fluorophenyl)-3-(methoxymethyl)-5-oxo-9-(trifluoromethyl)-3,5-dihydro-2H-[1,4]thiazino[2,3,4-ij]quinazolin-7-yl)-2,6-dimethylpiperazine-1-carboxylate (13 g, 20.9 mmol) in dichloromethane (200 ml) was added trifluoroacetic acid (60 mL) at 0° C. The reaction solution was stirred at room temperature for 3 hrs. After completion, the mixture was concentrated. The residue was redissolved in dichloromethane and washed with saturated $NaHCO_3$. The organic layer was dried over $Na_2SO_4$ and concentrated. The residue was purified by column (dichloromethane/methanol=15:1) to afford (S)-7-((3S,5R)-3,5-dimethylpiperazin-1-yl)-10-(4-fluorophenyl)-3-(methoxymethyl)-9-(trifluoromethyl)-2H-[1,4]thiazino[2,3,4-ij]quinazolin-5(3H)-one (3) (5.14 g, yield: 47%) as a yellow solid. MS (ESI) m/z 523.4 [M+H]+.

(S)-7-((3S,5R)-4-acryloyl-3,5-dimethylpiperazin-1-yl)-10-(4-fluorophenyl)-3-(methoxymethyl)-9-(trifluoromethyl)-2H-[1,4]thiazino[2,3,4-ij]quinazolin-5(3H)-one (4)

To a mixture of (S)-7-((3S,5R)-3,5-dimethylpiperazin-1-yl)-10-(4-fluorophenyl)-3-(methoxymethyl)-9-(trifluoromethyl)-2H-[1,4]thiazino[2,3,4-ij]quinazolin-5(3H)-one (5.14 g, 9.84 mmol) and triethyl amine (2.98 g, 29.5 mmol) in dichloromethane (100 ml) was added acrylic anhydride (1.48 g, 11.8 mmol) at 0° C. The mixture was stirred at 0° C. for 3 h. After completion, the mixture was poured into ice-water (100 mL) and extracted with ethyl acetate (100 mL×3). Concentrated and the residue was purified by chromatography column (dichloromethane/methanol=60/1 to 30/1) to afford (S)-7-((3S,5R)-4-acryloyl-3,5-dimethylpiperazin-1-yl)-10-(4-fluorophenyl)-3-(methoxymethyl)-9-(trifluoromethyl)-2H-[1,4]thiazino[2,3,4-ij]quinazolin-5(3H)-one (4) (3.3 g yield: 58%) as a white solid. MS (ESI) m/z 577.4 [M+H]+.

1H NMR (400 MHz, $CDCl_3$) δ 8.06 (s, 1H), 7.23-7.15 (m, 4H), 6.66-6.59 (m, 1H), 6.40 (dd, J=16.8 Hz, J=1.6 Hz, 1H), 5.77 (dd, J=10.4 Hz, J=2.0 Hz, 1H), 5.47-5.42 (m, 1H), 4.84-4.51 (m, 2H), 4.21-4.16 (m, 2H), 3.70-3.57 (m, 2H), 3.43-3.22 (m, 6H), 2.96 (dd, J=3.2 Hz, J=2.8 Hz, 1H), 1.62 (d, J=7.2 Hz, 3H), 1.47 (d, J=7.2 Hz, 3H).

Example 1104

8-((3S,5R)-4-acryloyl-3,5-dimethylpiperazin-1-yl)-11-(2,4-difluorophenyl)-1'-ethyl-10-(trifluoromethyl)-2H-spiro[[1,4]thiazepino[2,3,4-ij]quinazoline-3,3'-azetidin]-6(4H)-one

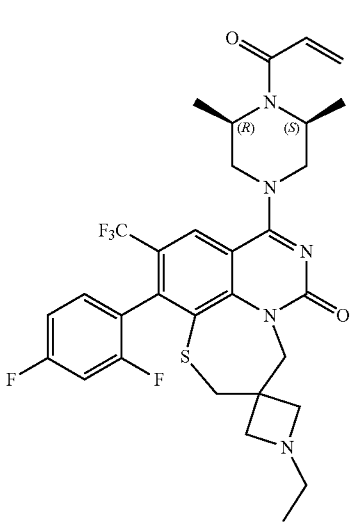

Reaction Scheme
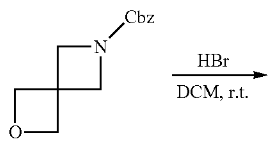
1
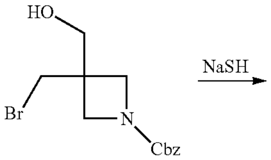
2
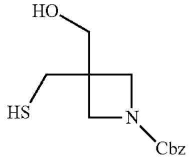
3
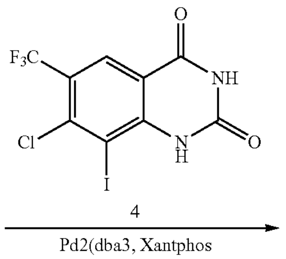
4
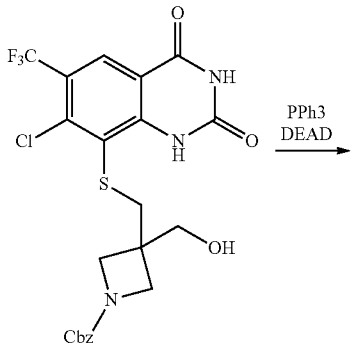
5
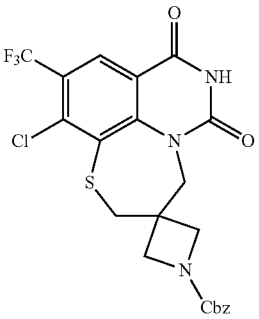
6
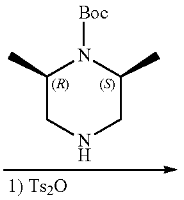
-continued
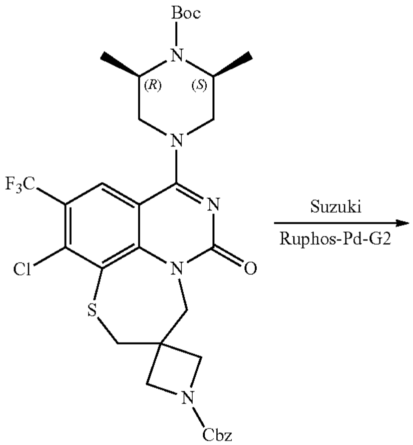
7
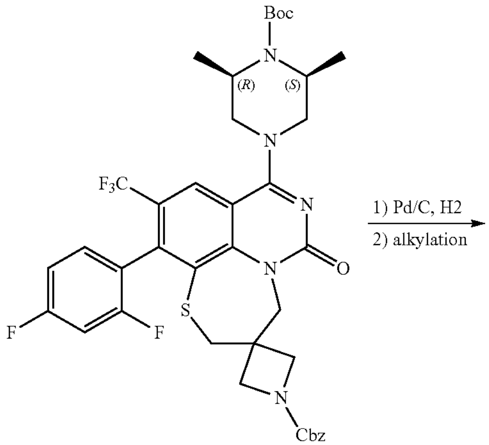
8
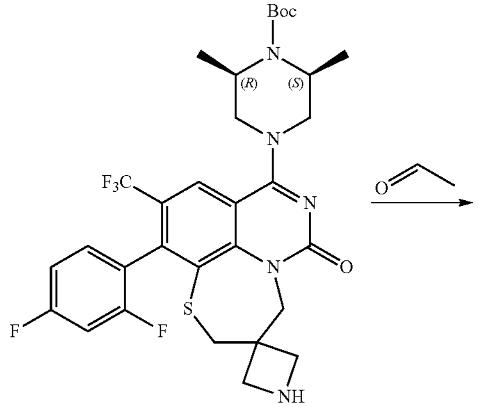
9

-continued

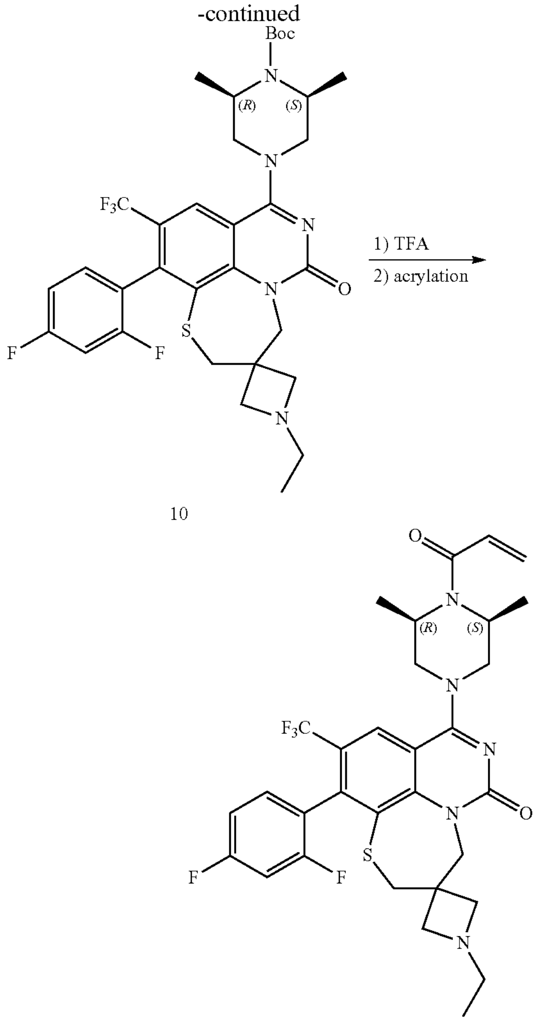

10

11

Benzyl 3-(bromomethyl)-3-(hydroxymethyl)azetidine-1-carboxylate (2)

To a solution of benzyl 2-oxa-6-azaspiro[3.3]heptane-6-carboxylate (9.4 g, 40.3 mmol) in DCM (100 mL) was added HBr (48% in AcOH; 60.5 mL) dropwise over 20 min. After completion, the resulting mixture was quenched with Saturated ammonium chloride aqueous solution. The aqueous layer was extracted with DCM (2x100 mL), and the combined organic layer was washed with brine, dried over anhydrous sodium sulfate and concenrated. The residue was purified by silica column (with 0.2%-1% methanol in dichloromethane) to afford product (2) (9.7 g, 30.9 mmol) as pale-yellow oil. MS (ESI) m/z 314.0, 316.0 $[M+H]^+$.

Benzyl 3-(hydroxymethyl)-3-(mercaptomethyl)azetidine-1-carboxylate (3)

To a solution of benzyl 3-(bromomethyl)-3-(hydroxymethyl)azetidine-1-carboxylate (2) (2.5 g, 7.9 mmol) in ethanol (25 mL) was added sodium hydrosulfide (885 mg, 15.8 mmol, 70% purity) at 0° C. The mixture was stirred at room temperature under nitrogen atmosphere for 5 hours. After completion, the mixture was filtered and concentrated. The residue was purified by silica gel column with dichloromethane/methanol=100/1 to afford the product (3) (1.43 g, yield: 59%) as a pale-yellow oil.

Benzyl 3-(((7-chloro-2,4-dioxo-6-(trifluoromethyl)-1,2,3,4-tetrahydroquinazolin-8-yl)thio)methyl)-3-(hydroxymethyl)azetidine-1-carboxylate (5)

To a solution of 7-chloro-8-iodo-6-(trifluoromethyl)quinazoline-2,4(1H,3H)-dione (3) (1.35 g, 3.5 mmol) in dioxane (20 mL) were added potassium carbonate (1.5 g, 10.5 mmol), benzyl 3-(hydroxymethyl)-3-(mercaptomethyl) azetidine-1-carboxylate (1.4 g, 5.0 mmol), 4,5-Bis(diphenyl-phosphino)-9,9-dimethylxanthene (578 mg, 1 mmol) and tris(dibenzylideneacetone) dipalladium (685 mg, 0.75 mmol). The mixture was stirred at 65° C. under nitrogen atmosphere for 16 hours. After completion, the mixture was filtered and the solid was washed with dichloromethane (10 mL). After concentration, the residue was purified by silica gel column with dichloromethane/methanol=100/1 to afford the product (5) (1.1 g, crude) as a pale yellow solid. MS (ESI) m/z 530.1 $[M+H]^+$.

Benzyl 11-chloro-6,8-dioxo-10-(trifluoromethyl)-4,6,7,8-tetrahydro-2H-spiro[[1,4]thiazepino[2,3,4-ij] quinazoline-3,3'-azetidine]-1'-carboxylate (6)

To a mixture of benzyl 3-(((7-chloro-2,4-dioxo-6-(trifluoromethyl)-1,2,3,4-tetrahydroquinazolin-8-yl)thio)methyl)-3-(hydroxymethyl)azetidine-1-carboxylate (1.1 g, 2.07 mmol) and tributylphosphine (0.811 g, 3.11 mmol) in tetrahydrofuran (20 mL) was added diethyl azodicarboxylate (0.54 g, 3.11 mmol) at 0° C. under nitrogen atmosphere. The mixture was stirred at room temperature for 3 hours. After completion, the mixture was poured into ice-water (2 L) and extracted with ethyl acetate (3x2 L). The organic solvent was removed under vacuum, and the residue was purified by silica column (with 0.2%-1% methanol in dichloromethane) to afford the crude product (6) (670 mg, yield: 67%) as a pale yellow solid. MS (ESI) m/z 512.1 [M+H]+.

Benzyl 8-((3S,5R)-4-(tert-butoxycarbonyl)-3,5-dimethylpiperazin-1-yl)-11-chloro-6-oxo-10-(trifluoromethyl)-4,6-dihydro-2H-spiro[[1,4]thiazepino[2,3,4-ij] quinazoline-3,3'-azetidine]-1'-carboxylate (7)

To a mixture of benzyl 11-chloro-6,8-dioxo-10-(trifluoromethyl)-4,6,7,8-tetrahydro-2H-spiro[[1,4]thiazepino[2,3,4-ij]quinazoline-3,3'-azetidine]-1'-carboxylate (6) (600 mg, 1.13 mmol) and potassium carbonate (470 mg, 3.4 mmol) in mixed solvent of acetonitrile (10 mL) and dichloromethane (10 mL) was added 4-Methylbenzenesulfonic anhydride (552 mg, 1.69 mmol) at 25° C. The mixture was stirred at 25° C. for 6 hours. (2S,6R)-tert-butyl 2,6-dimethylpiperazine-1-carboxylate (726 mg, 3.40 mmol) was added into the reaction solution. The reaction mixture was stirred at 25° C. for 1 hour. After completion, the mixture was poured into ice-water (600 mL) and extracted with ethyl acetate (3x600 mL). The organic solvent was removed under vacuum. The residue was purified by flash silica column (with 0.2%-1% methanol in dichloromethane) to afford the product (7) (565 mg, yield: 70%) as a yellow solid. MS (ESI) m/z 708.2 $[M+H]^+$.

Benzyl 8-((3S,5R)-4-(tert-butoxycarbonyl)-3,5-dimethylpiperazin-1-yl)-11-(2,4-difluorophenyl)-6-oxo-10-(trifluoromethyl)-4,6-dihydro-2H-spiro[[1,4]thiazepino[2,3,4-ij]quinazoline-3,3'-azetidine]-1'-carboxylate (8)

To a solution of benzyl 8-((3S,5R)-4-(tert-butoxycarbonyl)-3,5-dimethylpiperazin-1-yl)-11-chloro-6-oxo-10-(trifluoromethyl)-4,6-dihydro-2H-spiro[[1,4]thiazepino[2,3,4-ij]quinazoline-3,3'-azetidine]-1'-carboxylate (450 mg, 0.64 mmol) in a solution of 1,4-dioxane (5 mL) and water (1 mL) were added tripotassium phosphate (407 mg, 1.92 mmol), (2,4-difluorophenyl)boronic acid (505 mg, 3.26 mmol), and Chloro(2-dicyclohexylphosphino-2', 6'-diisopropoxy-1,1'-biphenyl)[2-(2'-amino-1,1'-biphenyl)]palladium(II) (39 mg, 0.06 mmol). The mixture was stirred at 80° C. under nitrogen atmosphere for 2 hours. After completion, the mixture was concentrated under reduced pressure. The residue was purified by silica gel column chromatography (dichloromethane/methanol=20/1) to afford the product (8) (520 mg, crude) as a yellow solid. MS (ESI) m/z 786.3 $[M+H]^+$.

(2S,6R)-tert-butyl4-(11-(2,4-difluorophenyl)-6-oxo-10-(trifluoromethyl)-4,6-dihydro-2H-spiro[[1,4]thiazepino[2,3,4-ij]quinazoline-3,3'-azetidin]-8-yl)-2,6-dimethylpiperazine-1-carboxylate (9)

To a solution of benzyl 8-((3S,5R)-4-(tert-butoxycarbonyl)-3,5-dimethylpiperazin-1-yl)-11-(2,4-difluorophenyl)-6-oxo-10-(trifluoromethyl)-4,6-dihydro-2H-spiro[[1,4]thiazepino[2,3,4-ij]quinazoline-3,3'-azetidine]-1'-carboxylate (8) (520 mg, crude) in methanol (10 mL) was added Pd/C (100 mg, 50% w/w) at room temperature. The mixture was stirred at room temperature under hydrogen atmosphere for 1 hour. After completion, the mixture was filtered and concentrated to afford crude product (9) (315 mg, crude) as a yellow solid which can used in next step without further purification. MS (ESI) m/z 652.2 $[M+H]^+$.

(2S,6R)-tert-butyl 4-(11-(2,4-difluorophenyl)-1'-ethyl-6-oxo-10-(trifluoromethyl)-4,6-dihydro-2H-spiro[[1,4]thiazepino[2,3,4-ij]quinazoline-3,3'-azetidin]-8-yl)-2,6-dimethylpiperazine-1-carboxylate (10)

To a mixture of (2S,6R)-tert-butyl 4-(11-(2,4-difluorophenyl)-6-oxo-10-(trifluoromethyl)-4,6-dihydro-2H-spiro[[1,4]thiazepino[2,3,4-ij]quinazoline-3,3'-azetidin]-8-yl)-2,6-dimethylpiperazine-1-carboxylate (9) (315 mg, 0.54 mmol) in methanol (5 mL) was added sodium cyanoborohydride (51 mg, 0.81 mmol). The mixture was stirred at 20° C. for 2 hours. After completion, the mixture was concentrated under reduced pressure, the residue was purified by silica gel column chromatography (dichloromethane/methanol=20/1) to afford the product (10) (281 mg, 0.46 mmol) as a yellow solid. MS (ESI) m/z 680.3 $[M+H]^+$.

8-((3S,5R)-4-acryloyl-3,5-dimethylpiperazin-1-yl)-11-(2,4-difluorophenyl)-1'-ethyl-10-(trifluoromethyl)-2H-spiro[[1,4]thiazepino[2,3,4-ij]quinazoline-3,3'-azetidin]-6(4H)-one (11)

To a solution of (2S,6R)-tert-butyl 4-(11-(2,4-difluorophenyl)-1'-ethyl-6-oxo-10-(trifluoromethyl)-4,6-dihydro-2H-spiro[[1,4]thiazepino[2,3,4-ij]quinazoline-3,3'-azetidin]-8-yl)-2,6-dimethylpiperazine-1-carboxylate (10) (281 mg, 0.46 mmol) in dichloromethane (4 mL) was added trifluoroacetic acid (1 mL) at 0° C. The reaction solution was stirred at room temperature for 1 hour. After completion, the mixture was concentrated. The residue was redissolved in dichloromethane and washed with saturated $NaHCO_3$. The organic layer was dried over $Na_2SO_4$ and concentrated. The residue was purified by silica gel column chromatography (dichloromethane/methanol=15/1) to afford the product (154 mg, 0.3 mmol) as a yellow solid. MS (ESI) m/z 580.2 $[M+H]^+$.

To a mixture of above product (154 mg, 0.30 mmol) and triethyl amine (90 mg, 0.90 mmol) in dichloromethane (5 mL) was added acrylic anhydride (57 mg, 0.45 mmol) at 0° C. The mixture was stirred at 0° C. for 1 hour. After completion, the mixture was poured into ice-water (50 mL) and extracted with ethyl acetate (3×20 mL). After concentration, the residue was purified by preparative high performance liquid chromatography (20% to 95% acetonitrile in water) to afford the product (11) (28 mg, yield: 15%) as a white solid. MS (ESI) m/z 634.2 [M+H]; $^1H$ NMR (400 MHz, $CDCl_3$) δ 8.11 (s, 1H), 7.21-7.15 (m, 1H), 7.09-6.96 (m, 2H), 6.71-6.62 (m, 1H), 6.48-6.42 (m, 1H), 5.82 (dd, J=14.0 Hz, 2.4 Hz, 1H), 4.70-4.65 (m, 4H), 4.21-4.18 (m, 2H), 3.55-3.31 (m, 8H), 2.67-2.61 (m, 2H), 1.58-1.50 (m, 6H), 1.05 (t, J=7.2 Hz, 3H).

Example 1109 and 1110

(S)-8'-((2S,5R)-4-acryloyl-2,5-dimethylpiperazin-1-yl)-11'-(2,4-difluorophenyl)-10'-(trifluoromethyl)-2'H,4'H,6'H-spiro[oxetane-3,3'-[1,4]thiazepino[2,3,4-ij]quinazolin]-6'-one (P1) and (R)-8'-((2S,5R)-4-acryloyl-2,5-dimethylpiperazin-1-yl)-11'-(2,4-difluorophenyl)-10'-(trifluoromethyl)-2'H,4'H,6'H-spiro[oxetane-3,3'-[1,4]thiazepino[2,3,4-ij]quinazolin]-6'-one (P2)

P1

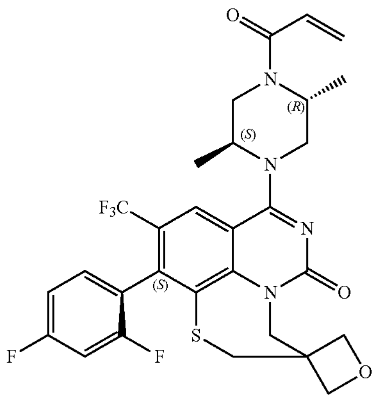

P2

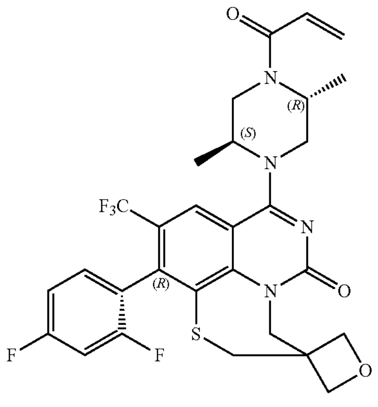

Reaction Scheme
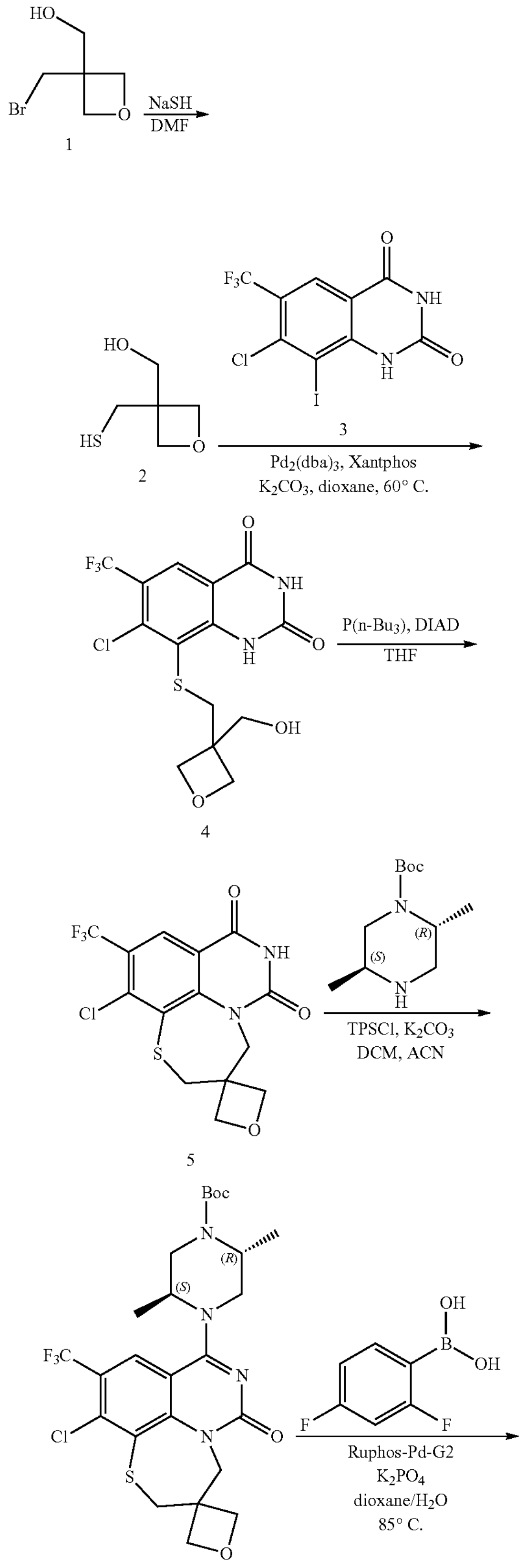
1
2
3
4
5
6
-continued
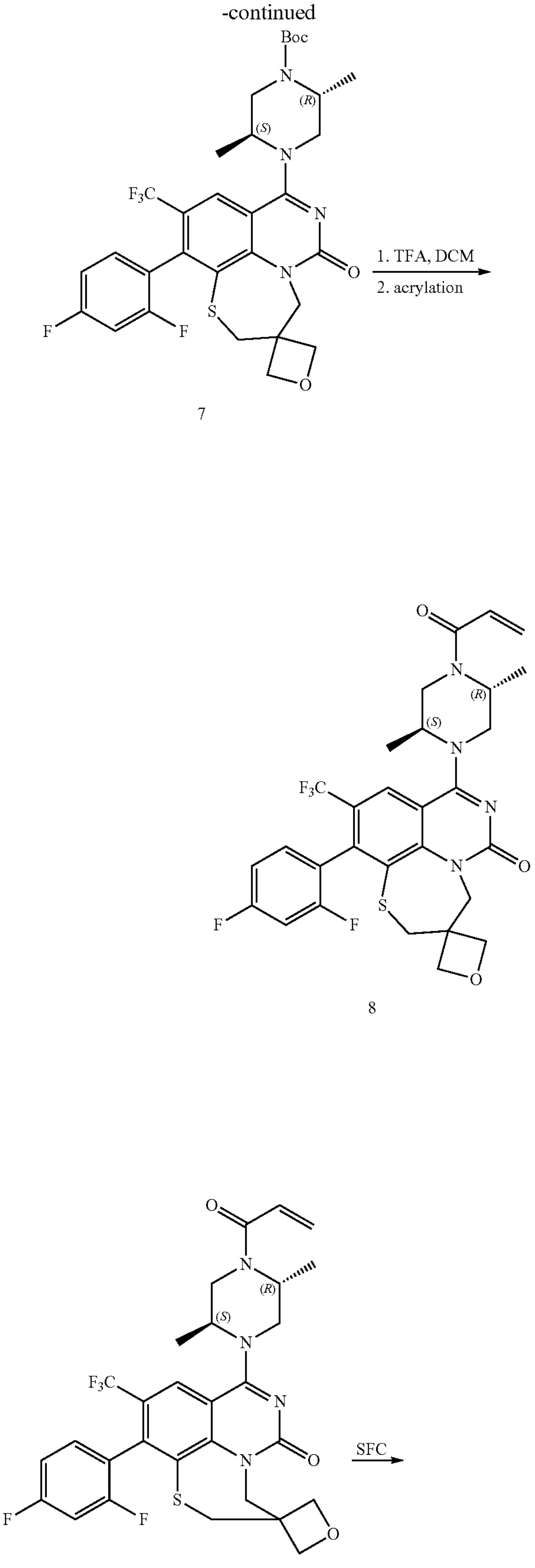
7
8
8

-continued

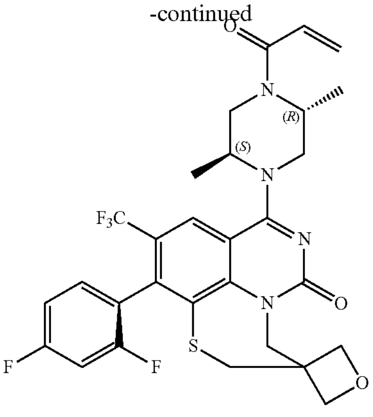

+

P1

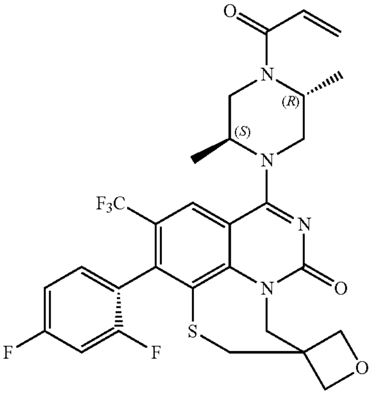

P2

(3-(mercaptomethyl)oxetan-3-yl)methanol (2)

To a solution of (3-(bromomethyl)oxetan-3-yl)methanol (200 g, 1.105 mmol) in ethanol (1.8 L) was added sodium hydrosulfide (176.8 g, 2.210 mmol, 70% purity) at 0° C. The mixture was stirred at room temperature under nitrogen atmosphere for 2 hours. After completion, the mixture was filtered and the filtrate was concentrated to afford the crude product which was purified by silica gel column with dichloromethane/methanol=100/1 to afford (3-(mercaptomethyl)oxetan-3-yl) methanol (64.2 g, yield: 43%) as a pale yellow oil.

$^1$H NMR (400 MHz, $CDCl_3$) δ 4.49-4.41 (m, 4H), 3.95 (s, 2H), 2.96 (d, J=8.4 Hz, 2H), 2.06 (brs, 1H), 1.36 (t, J=8.4 Hz, 1H).

7-chloro-8-(((3-(hydroxymethyl)oxetan-3-yl)methyl) thio)-6-(trifluoromethyl)quinazoline-2,4(1H,3H)-dione (4)

To a solution of 7-chloro-8-iodo-6-(trifluoromethyl)quinazoline-2,4(1H,3H)-dione (3) (71.40 g, 182.85 mmol) in dioxane (2200 mL) were added potassium carbonate (75.82 g, 548.56 mmol), (3-(mercaptomethyl)oxetan-3-yl)methanol (2) (49.08 g, 365.70 mmol), 4,5-Bis(diphenyl-phosphino)-9,9-dimethylxanthene (15.87 g, 27.43 mmol) and Tris(dibenzylideneacetone) dipalladium (16.75 g, 18.29 mmol). The mixture was stirred at 65° C. under nitrogen atmosphere for 16 hours. After completion, the mixture was filtered and the solid was washed with dichloromethane (1 L). (CAUTION! The organic phase contained only little product.) Then the solid was washed with tetrahydrofuran until the product was little by TLC. The tetrahydrofuran phase was concentrated and the residue was beat with tetrahydrofuran/petroleum ether (200 mL/50 mL) to afford the crude product 7-chloro-8-(((3-(hydroxymethyl)oxetan-3-yl) methyl)thio)-6-(trifluoromethyl)quinazoline-2,4(1H, 3H)-dione (4) (72.7 g, crude) as a pale yellow solid.

MS (ESI) m/z 397.0 [M+H]$^+$.

11-chloro-10-(trifluoromethyl)-2H-spiro[[1,4]thiazepino[2,3,4-ij]quinazoline-3,3'-oxetane]-6,8(4H,7H)-dione (5)

To a mixture of 7-chloro-8-(((3-(hydroxymethyl)oxetan-3-yl)methyl)thio)-6-(trifluoromethyl)quinazoline-2,4(1H, 3H)-dione (72.7 g, 183.23 mmol) and tributylphosphine (96.12 g, 366.46 mmol) in tetrahydrofuran (7000 mL) was added diisopropylazodicarboxylate (74.10 g, 366.46 mmol) at 0° C. under nitrogen atmosphere. The mixture was stirred at room temperature for 18 hours. After completion, the mixture was poured into ice-water (7000 mL) and extracted with ethyl acetate (3×7000 mL). The organic phase was concentrated and the residue was purified by silica column (with 0.2%-1% methanol in dichloromethane) to afford the crude product 11-chloro-10-(trifluoromethyl)-2H-spiro[[1, 4]thiazepino[2,3,4-ij] quinazoline-3,3'-oxetane]-6,8(4H, 7H)-dione (5) (34.10 g, yield:49%) as a pale yellow solid.

MS (ESI) m/z 376.9 [M−H]$^-$.

(2R,5S)-tert-butyl 4-(11-chloro-6-oxo-10-(trifluoromethyl)-4,6-dihydro-2H-spiro[[1,4]thiazepino[2,3,4-ij]quinazoline-3,3'-oxetan]-8-yl)-2,5-dimethylpiperazine-1-carboxylate (6)

To a mixture of 11-chloro-10-(trifluoromethyl)-2H-spiro[[1,4]thiazepino[2,3,4-ij] quinazoline-3,3'-oxetane]-6,8(4H, 7H)-dione (31.00 g, 81.85 mmol) and potassium carbonate (113.15 g, 818.68 mmol) in acetonitrile (1860 mL) and dichloromethane (930 mL) was added 2,4,6-Triisopropylbenzenesulfonyl chloride (36.20 g, 119.53 mmol) at 25° C. The mixture was stirred at 25° C. for 6 hours. (2S,5R)-tert-butyl 2,5-dimethylpiperazine-1-carboxylate (52.70 g, 245.91 mmol) was added into the reaction solution. The reaction mixture was stirred at 25° C. for 1 hour. After completion, the mixture was poured into ice-water (2000 mL) and extracted with ethyl acetate (4×800 mL). The organic phase was concentrated and the residue was purified by flash silica column (with 0.2%-1% methanol in dichloromethane) to afford (2R,5S)-tert-butyl 4-(11-chloro-6-oxo-10-(trifluoromethyl)-4,6-dihydro-2H-spiro[[1,4] thiazepino [2,3,4-ij]quinazoline-3,3'-oxetan]-8-yl)-2,5-dimethylpiperazine-1-carboxylate (6) (29.50 g, yield: 62%) as a pale-white solid.

MS (ESI) m/z 575.2 [M+H]$^+$.

(2R,5S)-tert-butyl 4-(11-(2,4-difluorophenyl)-6-oxo-10-(trifluoromethyl)-4,6-dihydro-2H-spiro[[1,4]thiazepino[2,3,4-ij]quinazoline-3,3'-oxetan]-8-yl)-2,5-dimethylpiperazine-1-carboxylate (7)

To a solution of (2R,5S)-tert-butyl 4-(11-chloro-6-oxo-10-(trifluoromethyl)-4,6-dihydro-2H-spiro[[1,4]thiazepino [2,3,4-ij]quinazoline-3,3'-oxetan]-8-yl)-2,6-dimethylpiperazine-1-carboxylate (6) (10.4 g, 18.12 mmol) in 1,4-dioxane (90 mL) and water (15 mL) were added tripotassium phosphate trihydrate (14.46 g, 54.36 mmol), (2,4-difluorophenyl) boronic acid (11.45 g, 72.48 mmol), and Chloro(2-dicyclohexylphosphino-2', 6'-diisopropoxy-1,1'-biphenyl)[2-(2'-amino-1,1'-biphenyl)]palladium(II) (1.41 g, 1.81 mmol). The mixture was stirred at 85° C. under nitrogen atmosphere for 3 hours. After completion, the mixture was concentrated and the residue was purified by silica gel column chromatography (with 1%-3% methanol in dichloromethane) to afford (2R,5S)-tert-butyl 4-(11-(2,4-difluorophenyl)-6-oxo-10-(trifluoromethyl)-4,6-dihydro-2H-spiro[[1,4]thiazepino[2,3,4-ij]quinazoline-3,3'-oxetan]-8-yl)-2,5-dimethylpiperazine-1-carboxylate (7) (9.9 g, yield: 84%) as a yellow solid. MS (ESI) m/z 653.1 $[M+H]^+$.

11-(2,4-difluorophenyl)-8-((2S,5R)-2,5-dimethylpiperazin-1-yl)-10-(trifluoromethyl)-2H-spiro[[1,4]thiazepino[2,3,4-ij]quinazoline-3,3'-oxetan]-6(4H)-one To a cooled mixture of (2R,5S)-tert-butyl 4-(11-(2,4-difluorophenyl)-6-oxo-10-(trifluoromethyl)-4,6-dihydro-2H-spiro[[1,4]thiazepino[2,3,4-ij]quinazoline-3,3'-oxetan]-8-yl)-2,5-dimethylpiperazine-1-carboxylate (7) (9.9 g, 15.18 mmol) in dichloromethane (50 mL) was added trifluoroacetic acid (25 mL) at 0° C. The reaction solution was stirred at room temperature for 1 hour. After completion, the mixture was concentrated. The residue was redissolved in dichloromethane and washed with saturated $NaHCO_3$. The organic layer was dried over $Na_2SO_4$ and concentrated. The residue was purified by silica gel column chromatography (with 7% methanol in dichloromethane) to afford 11-(2,4-difluorophenyl)-8-((2S,5R)-2,5-dimethylpiperazin-1-yl)-10-(trifluoromethyl)-2H-spiro[[1,4]thiazepino[2,3,4-ij]quinazoline-3,3'-oxetan]-6(4H)-one (8.1 g, yield: 96%) as a yellow solid. MS (ESI) m/z 552.3 $[M+H]^+$.

8-((2S,5R)-4-acryloyl-2,5-dimethylpiperazin-1-yl)-11-(2,4-difluorophenyl)-10-(trifluoromethyl)-2H-spiro[[1,4]thiazepino[2,3,4-ij]quinazoline-3,3'-oxetan]-6(4H)-one (8)

To a mixture of 11-(2,4-difluorophenyl)-8-((2S,5R)-2,5-dimethylpiperazin-1-yl)-10-(trifluoromethyl)-2H-spiro[[1,4]thiazepino[2,3,4-ij]quinazoline-3,3'-oxetan]-6(4H)-one (8.1 g, 14.67 mmol) and triethyl amine (2.96 g, 29.34 mmol) in dichloromethane (70 mL) was added acrylic anhydride (2.77 g, 22 mmol) at 0° C. The mixture was stirred at 0° C. for 1 hour. After completion, the mixture was poured into ice-water (200 mL) and extracted with ethyl acetate (3×200 mL). The organic phase was concentrated and the residue was purified by silica gel column chromatography (with 2% methanol in dichloromethane) to afford 8-((2S,5R)-4-acryloyl-2,5-dimethylpiperazin-1-yl)-11-(2,4-difluorophenyl)-10-(trifluoromethyl)-2H-spiro[[1,4]thiazepino[2,3,4-ij]quinazoline-3,3'-oxetan]-6(4H)-one (8) (6.9 g, yield: 78%) as a pale-yellow solid. MS (ESI) m/z 607.0 $[M+H]^+$.

$^1H$ NMR (400 MHz, $CDCl_3$) δ 8.87-8.70 (m, 1H), 7.22-7.11 (m, 1H), 7.05-6.91 (m, 2H), 6.67-6.48 (m, 1H), 6.43-6.32 (m, 1H), 5.82-5.74 (m, 1H), 5.20-4.88 (m, 5.5H), 4.44-4.26 (m, 3H), 4.00-3.64 (m, 3H), 3.50-3.31 (m, 2.5H), 1.45-1.24 (m, 6H).

The above racemate (15.4 g) was dissolved in EtOH (150 mL) and separated by chiral supercritical fluid chromatography (separation condition: Column:Chiralpak AD-H 5 μm 20×250 mm; Mobile Phase: $CO_2$:IPA=70:30 at 25 mL/min; Temp: 25° C.; Wavelength: 254 nm) to afford the first atropisomer P1 (6.8 g, 44% yield, 99.38% de) and the second atropisomer P2 (6.5 g, 42% yield, 98.52% de); Chiral HPLC Analytical: on CHIRALPAK® AD-H was using 5 μm 4.6×250 mm column, Mobile Phase: $CO_2$: IPA=70:30 at 2.5 mL/min; Temp: 25° C.; Wavelength: 254 nm).

The first atropisomer P1:

$^1H$ NMR (400 MHz, $CDCl_3$) δ 8.83 (s, 1H), 7.19-7.11 (m, 1H), 7.04-6.92 (m, 2H), 6.67-6.49 (m, 1H), 6.43-6.32 (m, 1H), 5.81-5.74 (m, 1H), 5.10-4.69 (m, 5H), 4.41-4.28 (m, 3H), 4.18-4.03 (m, 0.5H), 3.93-3.65 (m, 3H), 3.48-3.36 (m, 2.5H), 1.42-1.28 (m, 6H); Chiral SFC fraction 1: e.e. =99.38%, Rt=4.07 min.

The second atropisomer P2:

$^1H$ NMR (400 MHz, $CDCl_3$) δ 7.84 (s, 1H), 7.21-7.13 (m, 1H), 7.05-6.92 (m, 2H), 6.67-6.49 (m, 1H), 6.44-6.32 (m, 1H), 5.82-5.73 (m, 1H), 5.13-4.64 (m, 5H), 4.45-4.28 (m, 3H), 4.23-4.11 (m, 0.5H), 4.01-3.87 (m, 1H), 3.83-3.64 (m, 2H), 3.51-3.32 (m, 2.5H), 1.45-1.30 (m, 6H); Chiral SFC fraction 1: e.e. =98.52%, Rt=4.39 min.

Example 1120 and 1121

(S)-8'-((2S,5R)-4-acryloyl-2,5-dimethylpiperazin-1-yl)-11'-(5-chloro-2,4-difluorophenyl)-10'-(trifluoromethyl)-2'H,4'H,6'H-spiro[oxetane-3,3'-[1,4]thiazepino[2,3,4-ij]quinazolin]-6'-one (P1) and (R)-8'-((2S,5R)-4-acryloyl-2,5-dimethylpiperazin-1-yl)-11'-(5-chloro-2,4-difluorophenyl)-10'-(trifluoromethyl)-2'H,4'H,6'H-spiro[oxetane-3,3'-[1,4]thiazepino[2,3,4-ij]quinazolin]-6'-one (P2)

P1

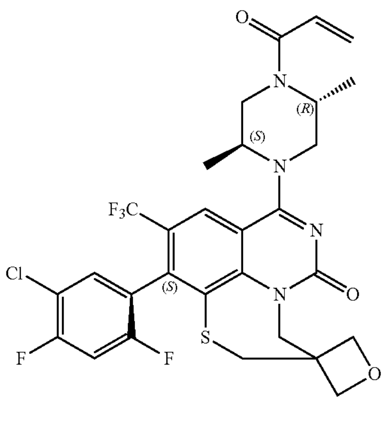

P2

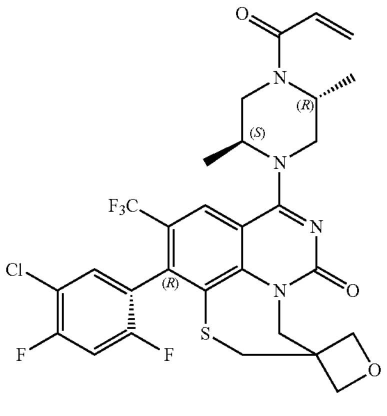

Reaction Scheme
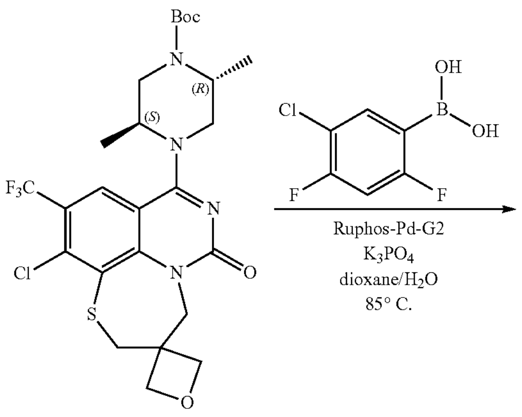
1
-continued
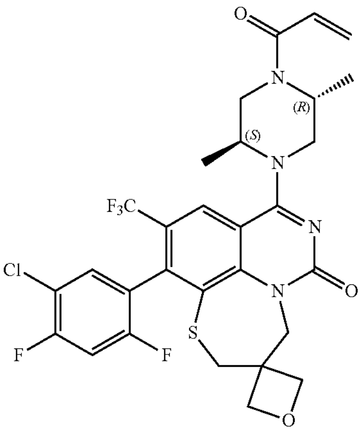
4
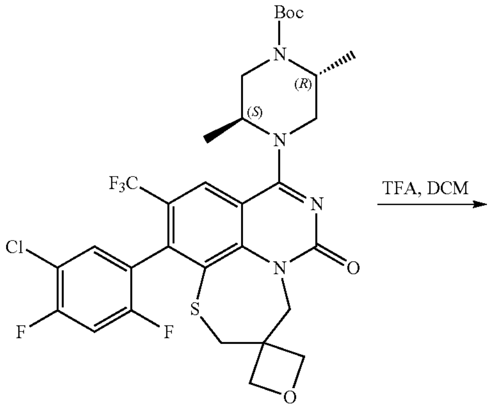
2
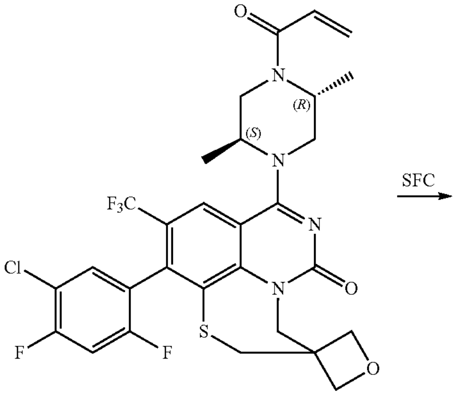
9
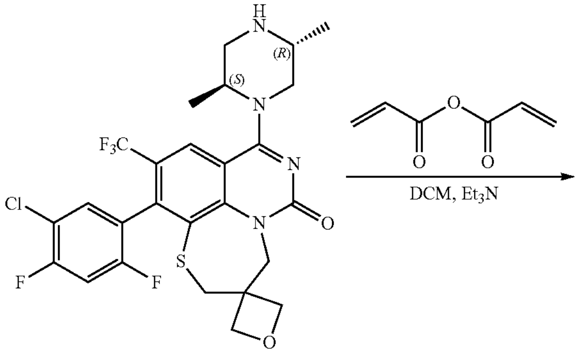
3
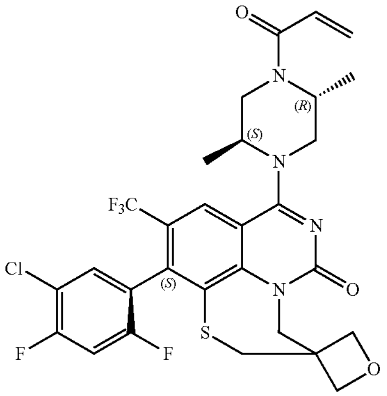
P1
+

-continued

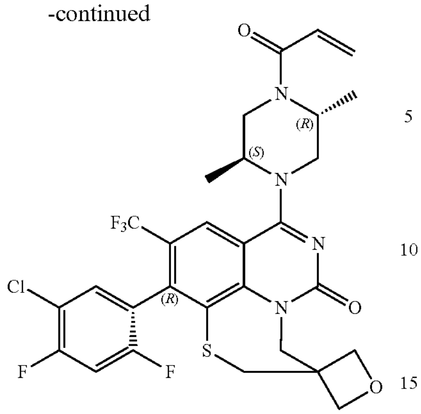

P2

((2R,5S)-tert-butyl 4-(11-(5-chloro-2,4-difluorophenyl)-6-oxo-10-(trifluoromethyl)-4,6-dihydro-2H-spiro[[1,4]thiazepino[2,3,4-ij]quinazoline-3,3'-oxetan]-8-yl)-2,5-dimethylpiperazine-1-carboxylate (2)

To a solution of (2S,5R)-tert-butyl 4-(11-chloro-6-oxo-10-(trifluoromethyl)-4,6-dihydro-2H-spiro[[1,4]thiazepino[2,3,4-ij]quinazoline-3,3'-oxetan]-8-yl)-2,5-dimethylpiperazine-1-carboxylate (26.00 g, 45.21 mmol) in 1,4-dioxane (550 mL) and water (130 mL) were added tripotassium phosphate trihydrate (28.80 g, 135.68 mmol), (5-chloro-2, 4-difluorophenyl) boronic acid (18.40 g, 95.65 mmol), and Chloro(2-dicyclohexylphosphino-2', 6'-diisopropoxy-1,1'-biphenyl)[2-(2'-amino-1,1'-biphenyl)]palladium(II) (7.03 g, 9.04 mmol). The mixture was stirred at 85° C. under nitrogen atmosphere for 3 hours. After completion, the mixture was concentrated and the residue was purified by silica gel column chromatography (with 1%-3% methanol in dichloromethane) to afford (2R,5S)-tert-butyl 4-(11-(5-chloro-2,4-difluorophenyl)-6-oxo-10-(trifluoromethyl)-4,6-dihydro-2H-spiro[[1,4]thiazepino[2,3,4-ij]quinazoline-3,3'-oxetan]-8-yl)-2,5-dimethylpiperazine-1-carboxylate (2) (33.00 g, crude) as a yellow solid. MS (ESI) m/z 687.6 $[M+H]^+$.

11-(5-chloro-2,4-difluorophenyl)-8-((2S,5R)-2,5-dimethylpiperazin-1-yl)-10-(trifluoromethyl)-2H-spiro[[1,4]thiazepino[2,3,4-ij]quinazoline-3,3'-oxetan]-6(4H)-one (3)

To a cooled mixture of (2R,5S)-tert-butyl 4-(11-(5-chloro-2,4-difluorophenyl)-6-oxo-10-(trifluoromethyl)-4,6-dihydro-2H-spiro[[1,4]thiazepino[2,3,4-ij]quinazoline-3,3'-oxetan]-8-yl)-2,5-dimethylpiperazine-1-carboxylate (2) (33.00 g, 45.21 mmol) in dichloromethane (60 mL) was added trifluoroacetic acid (30 mL) at 0° C. The reaction solution was stirred at room temperature for 1 hour. After completion, the mixture was concentrated. The residue was redissolved in dichloromethane and washed with saturated $NaHCO_3$. The organic layer was dried over $Na_2SO_4$ and concentrated. The residue was purified by silica gel column chromatography (with 7% methanol in dichloromethane) and removed palladium with Sulfhydryl-silica-gel to afford 11-(5-chloro-2,4-difluorophenyl)-8-((2S,5R)-2,5-dimethylpiperazin-1-yl)-10-(trifluoromethyl)-2H-spiro[[1,4]thiazepino[2,3,4-ij]quinazoline-3,3'-oxetan]-6(4H)-one (3) (31.4 g, crude) as a yellow solid. MS (ESI) m/z 587.1 [M+H]+.

8-((2S,5R)-4-acryloyl-2,5-dimethylpiperazin-1-yl)-11-(5-chloro-2,4-difluorophenyl)-10-(trifluoromethyl)-2H-spiro[[1,4]thiazepino[2,3,4-ij]quinazoline-3,3'-oxetan]-6(4H)-one (4)

To a mixture of 11-(5-chloro-2,4-difluorophenyl)-8-((2S, 5R)-2,5-dimethylpiperazin-1-yl)-10-(trifluoromethyl)-2H-spiro[[1,4]thiazepino[2,3,4-ij]quinazoline-3,3'-oxetan]-6 (4H)-one (3) (31.40 g, 45.21 mmol) and triethyl amine (18.00 g, 177.88 mmol) in dichloromethane (900 mL) was added acrylic anhydride (7.00 g, 55.51 mmol) at 0° C. The mixture was stirred at 0° C. for 1 hour. After completion, the mixture was poured into ice-water (200 mL) and extracted with dichloromethane (3×500 mL). The organic phase was concentrated and the residue was purified by silica gel column chromatography (with 2% methanol in dichloromethane) to afford 8-((2S,5R)-4-acryloyl-2,5-dimethylpiperazin-1-yl)-11-(5-chloro-2,4-difluorophenyl)-10-(trifluoromethyl)-2H-spiro[[1,4]thiazepino[2,3,4-ij]quinazoline-3,3'-oxetan]-6(4H)-one (4) (21.10 g, yield: 72.8%) as a pale-yellow solid. MS (ESI) m/z 641.1 $[M+H]^+$.

The above racemate (21.1 g) was dissolved in EtOH (150 mL) and separated by chiral supercritical fluid chromatography (separation condition: Column:Chiralpak AS-H 2 μm 20×250 cm; Mobile Phase: $CO_2$:EtOH (0.1 DEA)=70:30 at 25 mL/min; Temp: 25° C.; Wavelength: 254 nm) to afford the title compounds P1 (9.69 g, 46% yield, 98.62% de) and P2 (8.04 g, 41% yield, 99.46% de);

Chiral HPLC Analytical: on CHIRALPAK® AD-H was using 2 μm 0.46×15 cm column, Mobile Phase: $CO_2$ EtOH (0.1 DEA)=70:30 at 2.5 mL/min; Temp: 25° C.; Wavelength: 254 nm).

P1:

$^1$H NMR (400 MHz, $CDCl_3$) δ 7.83 (s, 1H), 7.26-7.21 (m, 1H), 7.06 (t, J=8.8 Hz, 1H), 6.61-6.50 (m, 1H), 6.41-6.34 (m, 1H), 5.80-5.76 (m, 1H), 5.75-4.50 (m, 6H), 4.38-4.35 (m, 3H), 4.17-3.67 (m, 3H), 3.44-3.40 (m, 2H), 1.39-1.25 (m, 6H);

Chiral SFC fraction 1: e.e. =98.62%, Rt=3.22 min.

P2:

$^1$H NMR (400 MHz, $CDCl_3$) 7.84 (s, 1H), 7.29-7.26 (m, 1H), 7.08 (t, J=8.8 Hz, 1H), 6.63-6.51 (m, 1H), 6.42-6.38 (m, 1H), 5.80-5.76 (m, 1H), 5.75-4.50 (m, 6H), 4.42-4.36 (m, 3H), 4.17-3.67 (m, 3H), 3.49-3.39 (m, 2H), 1.40-1.34 (m, 6H).

Chiral SFC fraction 2: e.e. =99.46%, Rt=3.43 min.

Example 1134
(2S,6R)-tert-butyl 4-((S)-11-(4-fluorophenyl)-3-morpholino-6-oxo-10-(trifluoromethyl)-2,3,4,6-tetrahydro-[1,4]thiazepino[2,3,4-ij]quinazolin-8-yl)-2,6-dimethylpiperazine-1-carboxylate
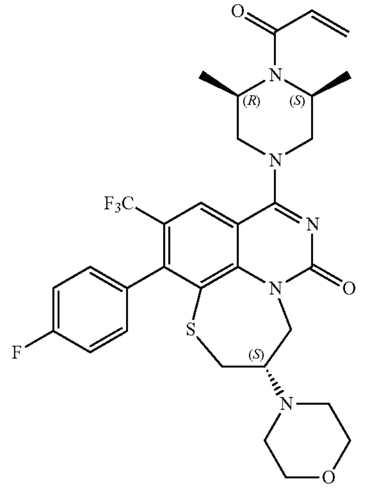
Reaction Scheme
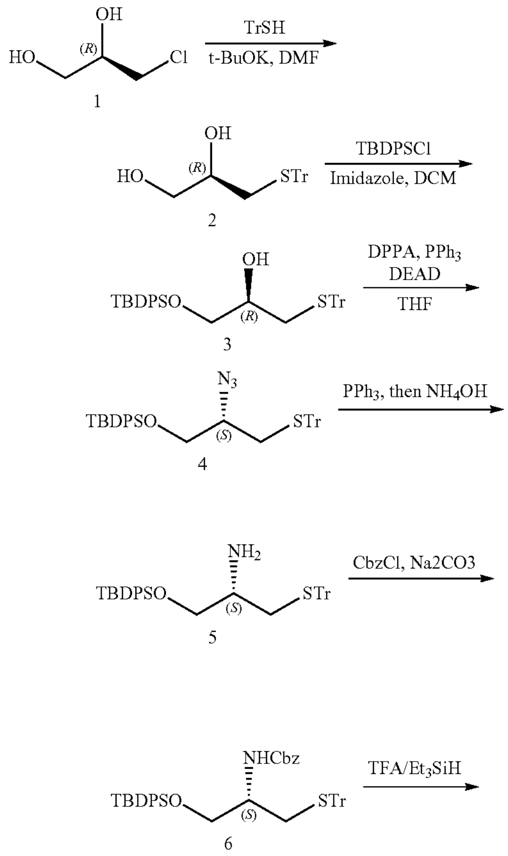
-continued
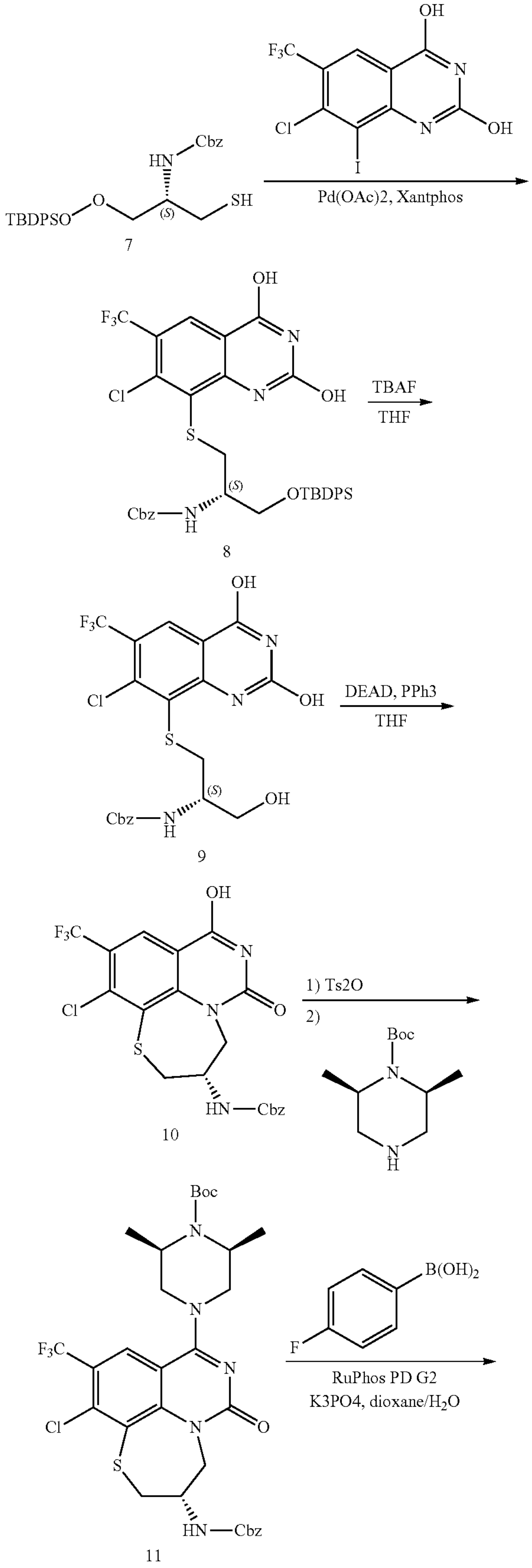

-continued

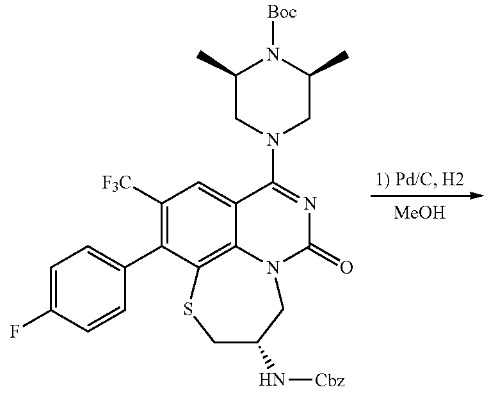

12

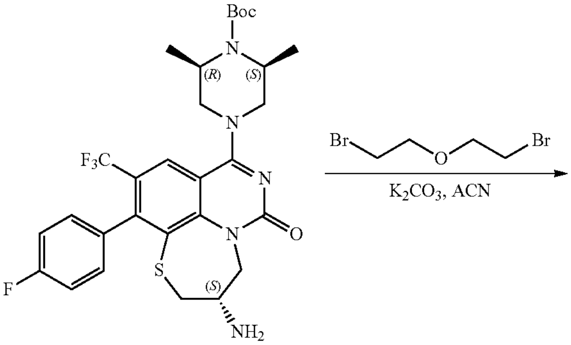

13

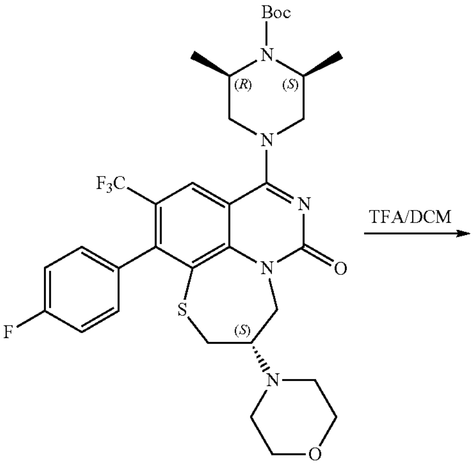

14

-continued

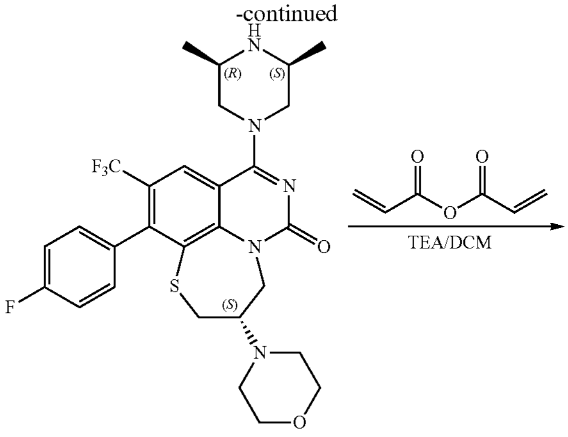

15

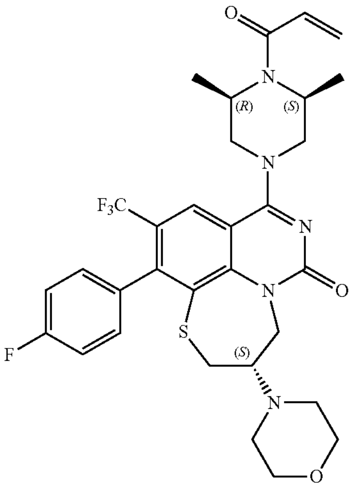

16

(R)-1-((tert-butyldiphenylsilyl)oxy)-3-chloropropan-2-ol (2)

To a mixture of (R)-3-chloropropane-1,2-diol (17 g, 153.8 mmol) and potassium t-butoxide (34.4 g, 307.6 mmol) in dimethylformide (400 mL) was added triphenylmethanethiol (46.8 g, 169.2 mmol). The mixture was stirred at room temperature for 18 hours. After completion, the mixture was concentrated under reduced pressure. The crude product was poured into water (300 mL), extracted with ethyl acetate (3×200 mL). The combined organic phase was washed with brine (300 mL) and dried over anhydrous sodium sulfate. After filtration and concentration, the residue was purified by silica gel column with dichloromethane/methanol=3/1 to afford (R)-1-((tert-butyldiphenylsilyl)oxy)-3-(tritylthio)propan-2-ol (2) (34 g, 63% yield) as a yellow oil. MS (ESI) m/z 373.2 $[M+Na]^+$.

(R)-1-((tert-butyldiphenylsilyl)oxy)-3-(tritylthio)propan-2-ol (3)

To a mixture of (S)-1-((tert-butyldiphenylsilyl)oxy)-3-(tritylthio)propan-2-ol (34 g, 97.0 mmol) and imidazole (13.2 g, 194.0 mmol) in dichloromethane (270 mL) was added tert-butylchlorodiphenylsilane (24 mL, 92.2 mmol) at 0° C. The mixture was stirred at room temperature for 18 hours. After completion, the mixture was concentrated under reduced pressure and the residue was purified by silica gel column with petroleum ether/ethyl acetate=20/1 to afford (R)-1-((tert-butyldiphenylsilyl)oxy)-3-(tritylthio)propan-2-ol (3) (36.3 g, 64% yield) as a colorless oil. MS (ESI) m/z 611.3 $[M+Na]^+$.

(S)-(2-azido-3-(tritylthio)propoxy)(tert-butyl)diphenylsilane (4)

To a mixture of (R)-1-((tert-butyldiphenylsilyl)oxy)-3-(tritylthio)propan-2-ol (3) (36.3 g, 61.73 mmol) and triphenylphosphine (32.35 g, 123.46 mmol) in tetrahydrofuran (200 mL) was added diethyl azodicarboxylate (21.48 g, 123.46 mmol) at 0° C. under nitrogen atmosphere. The mixture was warmed to room temperature, then was added diphehyl azidophosphate (20.37 g, 74.08 mmol) slowly and stirred at room temperature for 18 hours. After completion, the mixture was concentrated under reduced pressure and the residue was purified by silica gel column with petroleum ether/ethyl acetate=100/1 to afford to afford (S)-(2-azido-3-(tritylthio)propoxy)(tert-butyl)diphenylsilane (4) (31.5 g, 84% yield) as a colorless oil. MS (ESI): m/z 636.4 $[M+Na]^+$.

(S)-1-((tert-butyldiphenylsilyl)oxy)-3-(tritylthio)propan-2-amine (5)

To a solution of (S)-(2-azido-3-(tritylthio)propoxy)(tert-butyl)diphenylsilane (4) (31.5 g, 51.6 mmol) in tetrahydrofuran (230 mL) and water (25 mL) were added triphenylphosphine (27 g, 103.2 mmol). The mixture was stirred at 70° C. for 5 hours. After completion, the mixture was concentrated under reduced pressure and the residue was purified by silica gel column with petroleum ether/ethyl acetate (contained 2% methanol)=10/1 to afford to afford (S)-1-((tert-butyldiphenylsilyl)oxy)-3-(tritylthio)propan-2-amine (5) (9.3 g, 31% yield) as a colorless oil. MS (ESI): m/z 588.4 $[M+Na]^+$.

(S)-benzyl (1-((tert-butyldiphenylsilyl)oxy)-3-(tritylthio)propan-2-yl)carbamate (6)

To a mixture of (S)-1-((tert-butyldiphenylsilyl)oxy)-3-(tritylthio)propan-2-amine (5) (9.0 g, 15.33 mmol) and sodium carbonate (4.87 g, 45.99 mmol) in tetrahydrofuran (45 mL) and water (45 mL) was added benzyl carbonochloridate (3.14 g, 18.39 mmol). The mixture was stirred at room temperature for 18 hours. After completion, the mixture was poured into ice-water (300 mL) and extracted with ethyl acetate (3×150 mL). After concentration, the residue was purified by silica gel column with petroleum ether/ethyl acetate=10/1 to afford to afford (S)-benzyl (1-((tert-butyldiphenylsilyl)oxy)-3-(tritylthio)propan-2-yl)carbamate (6) (10.5 g, 95% yield) as a colorless oil. $^1H$ NMR (400 MHz, DMSO-d6) δ 7.51-7.18 (m, 30H), 5.04-4.96 (m, 2H), 3.73-3.68 (m, 1H), 3.45-3.41 (m, 1H), 3.29-3.25 (m, 1H), 2.44-2.40 (m, 1H), 2.33-2.27 (m, 1H), 0.88 (s, 9H).

(S)-benzyl (1-((tert-butyldiphenylsilyl)oxy)-3-mercaptopropan-2-yl)carbamate (7)

To a mixture of (S)-benzyl (1-((tert-butyldiphenylsilyl)oxy)-3-(tritylthio)propan-2-yl)carbamate (6) (10.5 g, 14.56 mmol) and triethylsilane (3.88 g, 33.49 mmol) in dichloromethane (110 mL) was added trifluoroacetic acid (11 mL, 147.84 mmol). The mixture was stirred at room temperature for 4 hours. After completion, the mixture was concentrated and adjusted pH=7~8 at 0° C. After concentration, the residue was purified by silica gel column with petroleum ether/ethyl acetate=10/1 to afford to afford (S)-benzyl (1-((tert-butyldiphenylsilyl)oxy)-3-mercaptopropan-2-yl)carbamate (7) (4.32 g, 61% yield) as a colorless oil. MS (ESI): m/z 502 $[M+Na]^+$.

(S)-benzyl (1-((tert-butyldiphenylsilyl)oxy)-3-((7-chloro-2,4-dihydroxy-6-(trifluoromethyl)quinazolin-8-yl)thio)propan-2-yl)carbamate (8)

To a solution of 7-chloro-8-iodo-6-(trifluoromethyl)quinazoline-2,4-diol (1.95 g, 5.0 mmol) in 1,4-dioxane (50 mL), potassium carbonate (2.07 g, 15.0 mmol), (S)-benzyl (1-((tert-butyldiphenylsilyl)oxy)-3-mercaptopropan-2-yl) carbamate (7) (4.32 g, 9.0 mmol), 4,5-Bis(diphenyl-phosphino)-9,9-dimethylxanthene (434 mg, 0.75 mmol) and Tris (dibenzylideneacetone) dipalladium (458 g, 0.5 mmol) were added. The mixture was stirred at 60° C. under nitrogen atmosphere for 18 hours. After completion, the mixture was concentrated under reduced pressure, the residue was purified by silica gel column chromatography (dichloromethane/methanol=30/1) to afford (S)-benzyl (1-((tert-butyldiphenylsilyl)oxy)-3-((7-chloro-2,4-dihydroxy-6-(trifluoromethyl) quinazolin-8-yl)thio)propan-2-yl)carbamate (8) (2.42 g, yield: 65%) as pale yellow solid. MS (ESI) m/z 743 $[M+H]^+$.

(S)-benzyl (1-((7-chloro-2,4-dihydroxy-6-(trifluoromethyl)quinazolin-8-yl)thio)-3-hydroxypropan-2-yl)carbamate (9)

To a solution of (S)-benzyl (1-((tert-butyldiphenylsilyl) oxy)-3-((7-chloro-2,4-dihydroxy-6-(trifluoromethyl)quinazolin-8-yl)thio)propan-2-yl)carbamate (8) (2.42 g, 3.26 mmol) in Tetrahydrofuran (36 mL) was added Tetrabutylammonium fluoride (4.9 mL, 4.9 mmol) at room temperature and stirred at room temperature for 18 hours. After completion, the mixture was extracted with ethyl acetate (3×60 mL). The combined organic phase was washed with brine (60 mL) and dried over anhydrous sodium sulfate. After filtration and concentration, the residue was purified by silica gel column with dichloromethane/methanol=20/1 to afford (S)-benzyl (1-((7-chloro-2,4-dihydroxy-6-(trifluoromethyl)quinazolin-8-yl)thio)-3-hydroxypropan-2-yl)carbamate (9) (780 mg, 47% yield) as a yellow solid. MS (ESI) m/z 504 $[M+H]^+$.

(S)-benzyl (11-chloro-8-hydroxy-6-oxo-10-(trifluoromethyl)-2,3,4,6-tetrahydro-[1,4]thiazepino[2,3,4-ij]quinazolin-3-yl)carbamate (10)

To a mixture of (S)-benzyl (1-((7-chloro-2,4-dihydroxy-6-(trifluoromethyl)quinazolin-8-yl)thio)-3-hydroxypropan-2-yl)carbamate (9) (2.87 g, 5.7 mmol) and triphenylphosphoranylidene (5.97 g, 22.8 mmol) in tetrahydrofuran (840 mL) was added Diethyl azodicarboxylate (3.97 g, 22.8 mmol) at 0° C. The mixture was stirred at 0° C. for 45 min. After completion, the mixture was poured into ice-water (200 mL) and extracted with ethyl acetate (3×200 mL). Concentrated and the residue was purified by C18 with 30-95% acetonitrile in water to afford (S)-benzyl (11-chloro-8-hydroxy-6-oxo-10-(trifluoromethyl)-2,3,4,6-tetrahydro-[1,4]thiazepino[2,3,4-ij]quinazolin-3-yl)carbamate (10) (1.35 g, yield: 49%) as a white solid. MS (ESI) m/z 486.1 $[M+H]^+$.

(2S,6R)-tert-butyl 4-((S)-3-(((benzyloxy)carbonyl) amino)-11-chloro-6-oxo-10-(trifluoromethyl)-2,3,4,6-tetrahydro-[1,4]thiazepino[2,3,4-ij]quinazolin-8-yl)-2,6-dimethylpiperazine-1-carboxylate (11)

To a mixture of (S)-benzyl (11-chloro-8-hydroxy-6-oxo-10-(trifluoromethyl)-2,3,4,6-tetrahydro-[1,4]thiazepino[2,3, 4-ij]quinazolin-3-yl)carbamate (10) (1.35 g, 2.78 mmol) and potassium carbonate (3.83 g, 27.8 mmol) in acetonitrile (50 mL) was added 4-methylbenzenesulfonic anhydride (2.27 g, 6.95 mmol) at 0° C. The mixture was stirred at room temperature for 4 hours. After completion, (2S,6R)-tert-butyl 2,6-dimethylpiperazine-1-carboxylate (2.38 g, 11.12 mmol) was added into the reaction solution. The reaction mixture was stirred at 0° C. for 1 hour. After completion, the mixture was poured into ice-water (200 mL) and extracted with ethyl acetate (3×100 mL). Concentrated and the residue was purified by C18 column with 20-95% acetonitrile in water to afford (2S,6R)-tert-butyl 4-((S)-3-(((benzyloxy)carbonyl)amino)-11-chloro-6-oxo-10-(trifluoromethyl)-2,3,4,6-tetrahydro-[1,4]thiazepino[2,3,4-ij]quinazolin-8-yl)-2,6-dimethylpiperazine-1-carboxylate (11) (1.15 g, yield: 60%) as a pale yellow solid. MS (ESI) m/z 683.3 [M+H]$^+$.

(2S,6R)-tert-butyl 4-((S)-3-(((benzyloxy)carbonyl)amino)-11-(4-fluorophenyl)-6-oxo-10-(trifluoromethyl)-2,3,4,6-tetrahydro-[1,4]thiazepino[2,3,4-ij]quinazolin-8-yl)-2,6-dimethylpiperazine-1-carboxylate (12)

To a solution of (2S,6R)-tert-butyl 4-((S)-3-(((benzyloxy)carbonyl)amino)-11-chloro-6-oxo-10-(trifluoromethyl)-2,3,4,6-tetrahydro-[1,4]thiazepino[2,3,4-ij]quinazolin-8-yl)-2,6-dimethylpiperazine-1-carboxylate (11) (250 mg, 0.37 mmol) in 1,4-dioxane (10 mL) and water (2 mL), tripotassium phosphate (290 mg, 1.11 mmol), (4-fluorophenyl)boronic acid (292 mg, 1.85 mmol), and Chloro(2-dicyclohexylphosphino-2', 6'-diisopropoxy-1,1'-biphenyl)[2-(2'-amino-1,1'-biphenyl)]palladium(II) (29 mg, 0.04 mmol) were added. The mixture was stirred at 80° C. under nitrogen atmosphere for 1 hour. After completion, the mixture was concentrated under reduced pressure, the residue was purified by silica gel column chromatography (dichloromethane/methanol=20/1) to afford (2S,6R)-tert-butyl 4-((S)-3-(((benzyloxy)carbonyl)amino)-11-(4-fluorophenyl)-6-oxo-10-(trifluoromethyl)-2,3,4,6-tetrahydro-[1,4]thiazepino[2,3,4-ij]quinazolin-8-yl)-2,6-dimethylpiperazine-1-carboxylate (12) (160 mg, yield: 58%) as a yellow solid. MS (ESI) m/z 742.3 [M+H]$^+$.

(2S,6R)-tert-butyl 4-((S)-3-amino-11-(4-fluorophenyl)-6-oxo-10-(trifluoromethyl)-2,3,4,6-tetrahydro-[1,4]thiazepino[2,3,4-ij]quinazolin-8-yl)-2,6-dimethylpiperazine-1-carboxylate (13)

To a solution of (2S,6R)-tert-butyl 4-((S)-3-(((benzyloxy)carbonyl)amino)-11-(4-fluorophenyl)-6-oxo-10-(trifluoromethyl)-2,3,4,6-tetrahydro-[1,4]thiazepino[2,3,4-ij]quinazolin-8-yl)-2,6-dimethylpiperazine-1-carboxylate (12) (160 mg, 0.21 mmol) in methanol (10 mL) was added Pd/C (80 mg, 50% w/w) at room temperature. The mixture was stirred at room temperature for 1 hour. After completion, the mixture was filtered and concentrated to afford (2S,6R)-tert-butyl 4-((S)-3-amino-1-(4-fluorophenyl)-6-oxo-10-(trifluoromethyl)-2,3,4,6-tetrahydro-[1,4]thiazepino[2,3,4-ij]quinazolin-8-yl)-2,6-dimethylpiperazine-1-carboxylate (13) (130 mg, crude) as a yellow solid. MS (ESI) m/z 608.3 [M+H]$^+$.

(2S,6R)-tert-butyl 4-((S)-11-(4-fluorophenyl)-3-morpholino-6-oxo-10-(trifluoromethyl)-2,3,4,6-tetrahydro-[1,4]thiazepino[2,3,4-ij]quinazolin-8-yl)-2,6-dimethylpiperazine-1-carboxylate (14)

To a mixture of (2S,6R)-tert-butyl 4-((S)-3-amino-11-(4-fluorophenyl)-6-oxo-10-(trifluoromethyl)-2,3,4,6-tetrahydro-[1,4]thiazepino[2,3,4-ij]quinazolin-8-yl)-2,6-dimethylpiperazine-1-carboxylate (13) (130 mg, crude) in acetonitrile (3 mL) was added Potassium carbonate (91 mg, 0.66 mmol) and 1-bromo-2-(2-bromoethoxy)ethane (102 mg, 0.44 mmol) at room temperature. The reaction solution was stirred at 90° C. under nitrogen atmosphere for 18 hours. After completion, the mixture was extracted with ethyl acetate (3×30 mL). The combined organic phase was washed with brine (30 mL) and dried over anhydrous sodium sulfate, which was filtered and concentrated to afford (2S,6R)-tert-butyl 4-((S)-11-(4-fluorophenyl)-3-morpholino-6-oxo-10-(trifluoromethyl)-2,3,4,6-tetrahydro-[1,4]thiazepino[2,3,4-ij]quinazolin-8-yl)-2,6-dimethylpiperazine-1-carboxylate (14) (220 mg, crude). MS (ESI) m/z 678.3 [M+H]$^+$.

(2S,6R)-tert-butyl 4-((S)-11-(4-fluorophenyl)-3-morpholino-6-oxo-10-(trifluoromethyl)-2,3,4,6-tetrahydro-[1,4]thiazepino[2,3,4-ij]quinazolin-8-yl)-2,6-dimethylpiperazine-1-carboxylate (15)

To a cooled mixture of (2S,6R)-tert-butyl 4-((S)-11-(4-fluorophenyl)-3-morpholino-6-oxo-10-(trifluoromethyl)-2,3,4,6-tetrahydro-[1,4]thiazepino[2,3,4-ij]quinazolin-8-yl)-2,6-dimethylpiperazine-1-carboxylate (14) (220 mg, crude) in dichloromethane (5 mL) was added trifluoroacetic acid (1.5 mL) at 0° C. The reaction solution was stirred at room temperature for 1 hour. After completion, the mixture was concentrated. The residue was redissolved in dichloromethane and washed with saturated $NaHCO_3$. The organic layer was dried over $Na_2SO_4$ and concentrated. The residue was purified by silica gel column chromatography (dichloromethane/methanol=15/1) to afford (2S,6R)-tert-butyl 4-((S)-11-(4-fluorophenyl)-3-morpholino-6-oxo-10-(trifluoromethyl)-2,3,4,6-tetrahydro-[1,4]thiazepino[2,3,4-ij]quinazolin-8-yl)-2,6-dimethylpiperazine-1-carboxylate (15) (49 mg, three steps yield: 38%) as a yellow solid. MS (ESI) m/z 578.3 [M+H]$^+$.

(2S,6R)-tert-butyl 4-((S)-11-(4-fluorophenyl)-3-morpholino-6-oxo-10-(trifluoromethyl)-2,3,4,6-tetrahydro-[1,4]thiazepino[2,3,4-ij]quinazolin-8-yl)-2,6-dimethylpiperazine-1-carboxylate (16)

To a mixture of (2S,6R)-tert-butyl 4-((S)-11-(4-fluorophenyl)-3-morpholino-6-oxo-10-(trifluoromethyl)-2,3,4,6-tetrahydro-[1,4]thiazepino[2,3,4-ij]quinazolin-8-yl)-2,6-dimethylpiperazine-1-carboxylate (15) (47.0 mg, 0.08 mmol) and triethyl amine (24 mg, 0.24 mmol) in dichloromethane (5 ml) was added acrylic anhydride (15 mg, 0.12 mmol) at 0° C. The mixture was stirred at 0° C. for 1 h. After completion, the mixture was poured into ice-water (30 mL) and extracted with dichloromethane (3×30 mL). After concentration, the residue was purified by preparative High Performance Liquid Chromatography (20% to 95% acetonitrile in water) to afford (2S,6R)-tert-butyl 4-((S)-11-(4-fluorophenyl)-3-morpholino-6-oxo-10-(trifluoromethyl)-2,3,4,6-tetrahydro-[1,4]thiazepino[2,3,4-ij]quinazolin-8-yl)-2,6-dimethylpiperazine-1-carboxylate (16) (14.0 mg, yield: 28%) as a white solid. MS (ESI) m/z 632.3 [M+H]$^+$.

$^1$H NMR (400 MHz, $CDCl_3$) δ 8.06 (s, 1H), 7.21-7.15 (m, 4H), 6.66-6.59 (i, 1H), 6.42 (dd, J=2.0 Hz, 16.4 Hz, 1H), 5.78 (dd, J=1.6 Hz, 10.4 Hz, 1H), 4.75-4.72 (m, 3H), 4.15 (t, J=10.8 Hz, 2H), 3.72-3.66 (1, 4H), 3.37-3.08 (i, 5H), 2.70-2.64 (1, 4H), 1.57-1.49 (m, 6H), 1.31-1.25 (m, 1H).

TABLE 8

| Examples 1100 to 1140 | | | | | |
|---|---|---|---|---|---|
| Ex. # | Name | Structure | $^1$H NMR | MS (M + H)$^+$ | % CAF 10 uM @ 60 min |
| 1100 | 8'-((3S,5R)-4-acryloyl-3,5-dimethylpiperazin-1-yl)-11'-(5-chloro-2,4-difluorophenyl)-10'-(trifluoromethyl)-2'H,4'H,6'H-spiro[oxetane-3,3'-[1,4]thiazepino[2,3,4-ij]quinazolin]-6'-one | 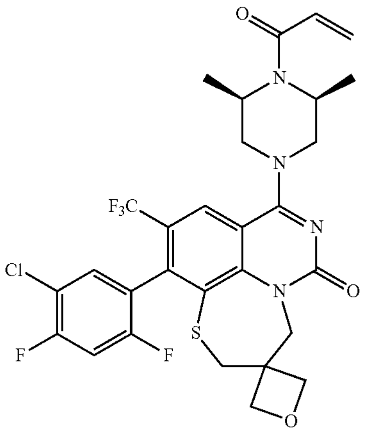 | $^1$H NMR (400 MHz, $CDCl_3$) δ 8.08 (s, 1H), 7.26-7.22 (m, 1H), 7.06 (t, J = 8.4 Hz, 1H), 6.62 (dd, J = 16.8 Hz, 10.8 Hz, 1H), 6.41 (dd, J = 16.4 Hz, 1.6 Hz, 1H), 5.78 (dd, J = 10.4 Hz, 2.0 Hz, 1H), 5.25-4.52 (m, 6H), 4.35 (dd, J = 6.4 Hz, 2.0 Hz, 2H), 4.18-4.10 (m, 2H), 3.47-3.42 (m, 2H), 3.41-3.33 (m, 2H), 1.56-1.49 (m, 6H). | 641.2 | 88.8 |
| 1101 | (3S,10R)-7-((2S,5R)-4-acryloyl-2,5-dimethylpiperazin-1-yl)-3-(methoxymethyl)-10-(1-methyl-1H-indazol-7-yl)-9-(trifluoromethyl)-2,3-dihydro-5H-[1,4]thiazino[2,3,4-ij]quinazolin-5-one | 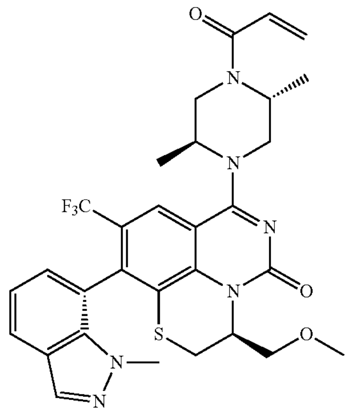 | $^1$H NMR (400 MHz, $CDCl_3$) δ 8.05 (s, 1H), 7.91-7.85 (m, 2H), 7.25-7.21 (m, 1H), 7.14 (d, J = 6.8 Hz, 1H), 6.67-6.51 (m, 1H), 6.38 (t, J = 14.8 Hz, 1H), 5.78 (t, J = 8.0 Hz, 1H), 5.45-5.41 (m, 1H), 5.10-5.05 (m, 0.5H), 4.85-4.71 (m, 1H), 4.47-4.44 (m, 0.5H), 4.37-4.34 (m, 1H), 4.10-4.06 (m, 0.5H), 3.81-3.64 (m, 4H), 3.56-3.54 (m, 3H), 3.37-3.24 (m, 4.5H), 3.00-2.97 (m, 1H), 1.48-1.42 (m, 6H). | 613.2 | 0 |
| 1102 | (3S,10S)-7-((2S,5R)-4-acryloyl-2,5-dimethylpiperazin-1-yl)-3-(methoxymethyl)-10-(1-methyl-1H-indazol-7-yl)-9-(trifluoromethyl)-2,3-dihydro-5H-[1,4]thiazino[2,3,4-ij]quinazolin-5-one | 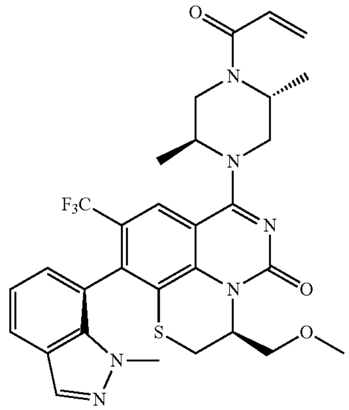 | $^1$H NMR (400 MHz, $CDCl_3$) δ 8.06 (s, 1H), 7.94 (d, J = 15.6 Hz, 1H), 7.87 (d, J = 8.0 Hz, 1H), 7.27-7.23 (m, 1H), 7.13 (d, J = 7.2 Hz, 1H), 6.68-6.51 (m, 1H), 6.38 (t, J = 14.8 Hz, 1H), 5.78 (t, J = 8.8 Hz, 1H), 5.39-5.36 (m, 1H), 5.12-5.09 (m, 0.5H), 4.81-4.68 (m, 1H), 4.55-4.44 (m, 1H), 4.39-4.36 (m, 0.5H), 4.21-4.18 (m, 0.5H), 3.72-3.56 (m, 7H), 3.35 (s, 3H), 3.28-3.19 (m, 1.5H), 3.03-2.99 (m, 1H), 1.55-1.46 (m, 6H). | 613.2 | 94.5 |

TABLE 8-continued

Examples 1100 to 1140

| Ex. # | Name | Structure | $^1$H NMR | MS (M + H)$^+$ | % CAF 10 uM @ 60 min |
|---|---|---|---|---|---|
| 1103 | (S)-7-((3S,5R)-4-acryloyl-3,5-dimethylpiperazin-1-yl)-10-(4-fluorophenyl)-3-(methoxymethyl)-9-(trifluoromethyl)-2,3-dihydro-5H-[1,4]thiazino[2,3,4-ij]quinazolin-5-one | 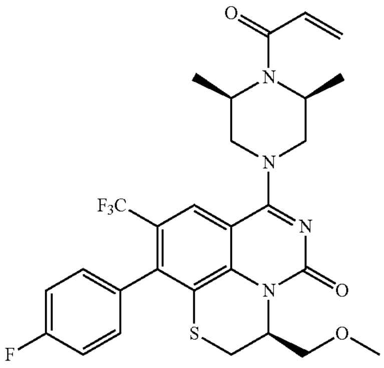 [SMILES: C=CC(=O)N1[C@H](C)CN(c2nc(=O)n3c4c(c(-c5ccc(F)cc5)c(C(F)(F)F)cc24)SC[C@@H]3COC)C[C@@H]1C] | $^1$H NMR (400 MHz, $CDCl_3$) δ 8.06 (s, 1H), 7.23-7.15 (m, 4H), 6.66-6.59 (m, 1H), 6.40 (dd, J = 2.0 Hz, 16.8 Hz, 1H), 5.77 (dd, J = 2.0 Hz, 10.8 Hz, 1H), 5.44-5.43 (m, 1H), 4.76-4.57 (m, 2H), 4.21-4.16 (m, 2H), 3.70-3.62 (m, 2H), 3.40-3.30 (m, 6H), 2.98-2.94 (m, 1H), 1.62 (d, J = 7.2 Hz, 3H), 1.47 (d, J = 7.2 Hz, 3H). | 577.3 | 98 |
| 1104 | 8-((3S,5R)-4-acryloyl-3,5-dimethylpiperazin-1-yl)-11-(2,4-difluorophenyl)-1'-ethyl-10-(trifluoromethyl)-2H-spiro[[1,4]thiazepino[2,3,4-ij]quinazoline-3,3'-azetidin]-6(4H)-one | 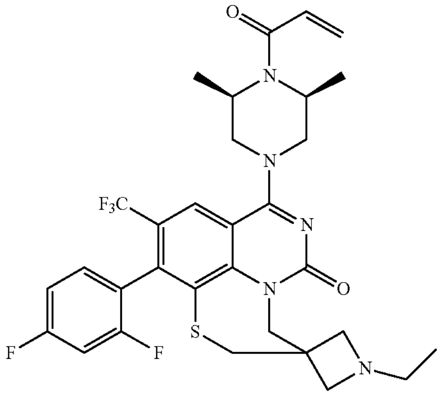 [SMILES: C=CC(=O)N1[C@H](C)CN(c2nc(=O)n3c4c(c(-c5ccc(F)cc5F)c(C(F)(F)F)cc24)SCC2(CN(CC)C2)C3)C[C@@H]1C] | $^1$H NMR (400 MHz, $CDCl_3$) δ 8.11 (s, 1H), 7.21-7.15 (m, 1H), 7.09-6.96 (m, 2H), 6.71-6.62 (m, 1H), 6.48-6.42 (m, 1H), 5.82 (dd, J = 14.0 Hz, 2.4 Hz, 1H), 4.70-4.65 (m, 4H), 4.21-4.18 (m, 2H), 3.55-3.31(m, 8H), 2.67-2.61 (m, 2H), 1.58-1.50 (m, 6H), 1.05 (t, J = 7.2 Hz, 3H). | 634.3 | 97.2 |
| 1105 | (3R)-8-((3S,5R)-4-acryloyl-3,5-dimethylpiperazin-1-yl)-11-(5-chloro-2,4-difluorophenyl)-3-morpholino-10-(trifluoromethyl)-3,4-dihydro-2H,6H-[1,4]thiazepino[2,3,4-ij]quinazolin-6-one | 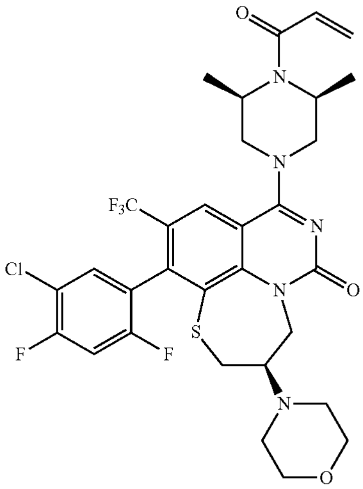 | $^1$H NMR (400 MHz, $CDCl_3$) δ 8.12 (s, 1H), 7.33-7.29 (m, 1H), 7.13-7.07 (m, 1H), 6.72-6.63 (m, 1H), 6.49-6.43 (m, 1H), 5.83 (dd, J = 14.0 Hz, 2.8 Hz, 1H), 4.79-4.69 (m, 4H), 4.22-4.17 (m, 2H), 3.83-3.70 (m, 4H), 3.42-3.19 (m, 5H), 2.72-2.65 (m, 4H), 1.61-1.57 (m, 6H). | 684.2 | 95.6 |

TABLE 8-continued

| Ex. # | Name | Structure | $^1$H NMR | MS (M + H)$^+$ | % CAF 10 uM @ 60 min |
|---|---|---|---|---|---|
| | Examples 1100 to 1140 | | | | |
| 1106 | (S)-7-(4-acryloylpiperazin-1-yl)-10-(4-fluorophenyl)-3-(methoxymethyl)-9-(trifluoromethyl)-2,3-dihydro-5H-[1,4]thiazino[2,3,4-ij]quinazolin-5-one | 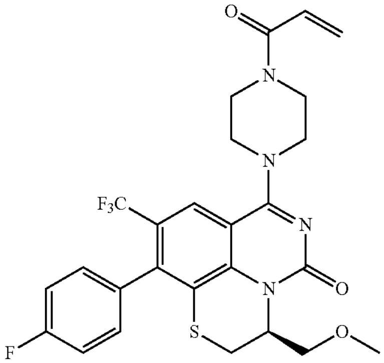 [SMILES: C=CC(=O)N1CCN(c2nc(=O)n3c4c(c(-c5ccc(F)cc5)c(C(F)(F)F)cc24)SC[C@@H]3COC)CC1] | $^1$H NMR (300 MHz, $CDCl_3$) δ 7.85 (s, 1H), 7.26-7.19 (m, 4H), 6.69-6.60 (m, 1H), 6.41 (d, J = 21.0 Hz, 1H), 5.83 (d, J = 12.0 Hz, 1H), 5.48-5.44 (m, 1H), 4.07-3.96 (m, 3H), 3.91-3.76 (m, 5H), 3.73-3.70 (m, 2H), 3.45 (s, 3H), 3.37 (d, J = 15.0 Hz, 1H), 3.00 (d, J = 15.0 Hz, 1H). | 549.2 | 98.2 |
| 1107 | (3S,10R)-7-(4-acryloylpiperazin-1-yl)-10-(5-chloro-2,4-difluorophenyl)-3-(methoxymethyl)-9-(trifluoromethyl)-2,3-dihydro-5H-[1,4]thiazino[2,3,4-ij]quinazolin-5-one | 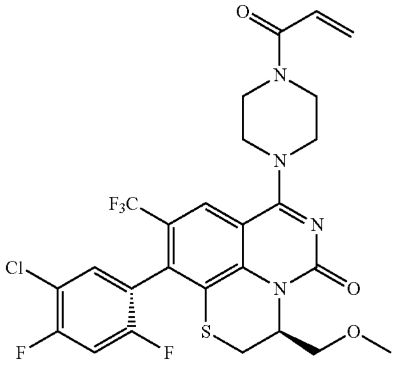 | $^1$H NMR (400 MHz, $CDCl_3$) δ 7.80 (s, 1H), 7.29-7.27 (m, 1H), 7.09-7.05 (m, 1H), 6.62-6.55 (m, 1H), 6.39-6.34 (m, 1H), 5.79 (dd, J = 10.4 Hz, 2.0 Hz, 1H), 5.45-5.40 (m, 1H), 3.97-3.88 (m, 3H), 3.80-3.78 (m, 5H), 3.66 (d, J = 7.2 Hz, 2H), 3.42-3.36 (m, 4H), 3.03 (dd, J = 13.6 Hz, 2.8 Hz, 1H). | 601.1 | 97 |
| 1108 | (3S,10S)-7-(4-acryloylpiperazin-1-yl)-10-(5-chloro-2,4-difluorophenyl)-3-(methoxymethyl)-9-(trifluoromethyl)-2,3-dihydro-5H-[1,4]thiazino[2,3,4-ij]quinazolin-5-one | 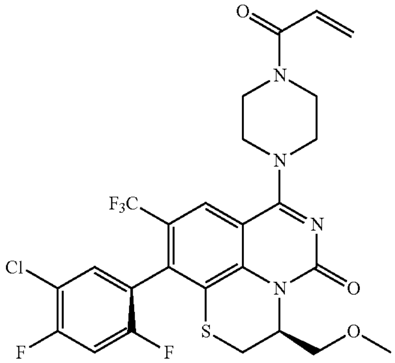 | $^1$H NMR (400 MHz, $CDCl_3$) δ 7.80 (s, 1H), 7.28-7.26 (m, 1H), 7.07 (t, J = 8.8 Hz, 1H), 6.62-6.55 (m, 1H), 6.39-6.35 (m, 1H), 5.79 (dd, J = 10.4 Hz, 1.6 Hz, 1H), 5.47-5.43 (m, 1H), 4.00-3.90 (m, 3H), 3.80-3.73 (m, 5H), 3.67-3.61 (m, 2H), 3.39-3.35 (m, 4H), 3.02 (dd, J = 13.6 Hz, 2.8 Hz, 1H). | 601.1 | 85 |

TABLE 8-continued

| Ex. # | Name | Structure | $^1H$ NMR | MS $(M + H)^+$ | % CAF 10 uM @ 60 min |
|---|---|---|---|---|---|
| | Examples 1100 to 1140 | | | | |
| 1109 | (S)-8'-((2S,5R)-4-acryloyl-2,5-dimethylpiperazin-1-yl)-11'-(2,4-difluorophenyl)-10'-(trifluoromethyl)-2'H,4'H,6'H-spiro[oxetane-3,3'-[1,4]thiazepino[2,3,4-ij]quinazolin]-6'-one | 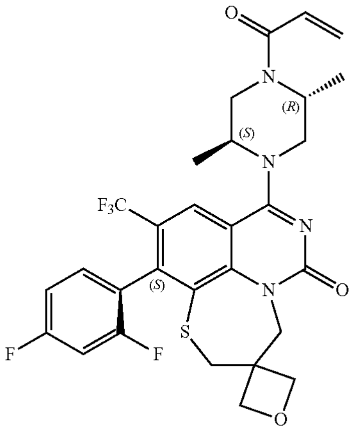 | $^1H$ NMR (400 MHz, $CDCl_3$) δ 8.83 (s, 1H), 7.19-7.11 (m, 1H), 7.04-6.92 (m, 2H), 6.67-6.49 (m, 1H), 6.43-6.32 (m, 1H), 5.81-5.74 (m, 1H), 5.10-4.69 (m, 5H), 4.41-4.28 (m, 3H), 4.18-4.03 (m, 0.5H), 3.93-3.65 (m, 3H), 3.48-3.36 (m, 2.5H), 1.42-1.28 (m, 6H). | 607.3 | 93 |
| 1110 | (R)-8'-((2S,5R)-4-acryloyl-2,5-dimethylpiperazin-1-yl)-11'-(2,4-difluorophenyl)-10'-(trifluoromethyl)-2'H,4'H,6'H-spiro[oxetane-3,3'-[1,4]thiazepino[2,3,4-ij]quinazolin]-6'-one | 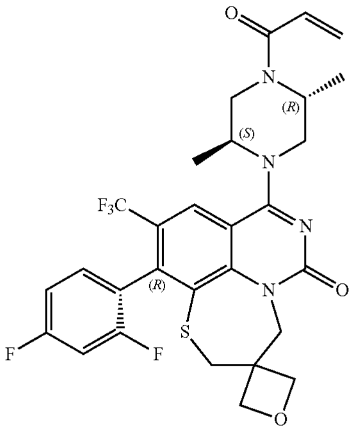 | $^1H$ NMR (400 MHz, $CDCl_3$) δ 7.84 (s, 1H), 7.21-7.13 (m, 1H), 7.05-6.92 (m, 2H), 6.67-6.49 (m, 1H), 6.44-6.32 (m, 1H), 5.82-5.73 (m, 1H), 5.13-4.64 (m, 5H), 4.45-4.28 (m, 3H), 4.23-4.11 (m, 0.5H), 4.01-3.87 (m, 1H), 3.83-3.64 (m, 2H), 3.51-3.32 (m, 2.5H), 1.45-1.30 (m, 6H). | 607.3 | 96.1 |
| 1111 | 8'-((2S,5R)-4-acryloyl-2,5-dimethylpiperazin-1-yl)-11'-(4-fluorophenyl)-10'-(trifluoromethyl)-2'H,4'H,6'H-spiro[oxetane-3,3'-[1,4]thiazepino[2,3,4-ij]quinazolin]-6'-one | 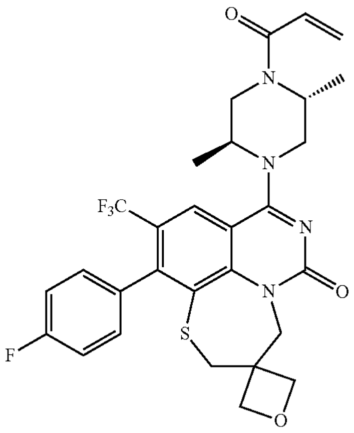 [SMILES: C=CC(=O)N1C[C@H](C)N(c2nc(=O)n3c4c(c(-c5ccc(F)cc5)c(C(F)(F)F)cc24)SCC2(COC2)C3)C[C@H]1C] | $^1H$ NMR (400 MHz, $CDCl_3$) δ 7.82 (s, 1H), 7.26-7.15 (m, 4H), 6.63-6.51 (m, 1H), 6.38 (t, J = 15.2 Hz, 1H), 5.80-5.76 (m, 1H), 5.01-4.70 (m, 5H), 4.41-4.30 (m, 4H), 3.91-3.67 (m, 3H), 3.42-3.33 (m, 2H), 1.39-1.25 (m, 6H). | 589.3 | 95.4 |

TABLE 8-continued

| Ex. # | Name | Structure | ¹H NMR | MS (M + H)⁺ | % CAF 10 uM @ 60 min |
|---|---|---|---|---|---|
| Examples 1100 to 1140 | | | | | |
| 1112 | (R)-8-((3S,5R)-4-acryloyl-3,5-dimethylpiperazin-1-yl)-11-(4-fluorophenyl)-3-morpholino-10-(trifluoromethyl)-3,4-dihydro-2H,6H-[1,4]thiazepino[2,3,4-ij]quinazolin-6-one | 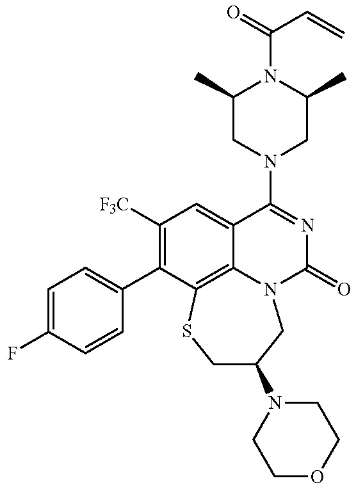 [SMILES: C=CC(=O)N1[C@H](C)CN(c2nc(=O)n3c4c(c(-c5ccc(F)cc5)c(C(F)(F)F)cc24)SC[C@H](N2CCOCC2)C3)C[C@@H]1C] | $^1$H NMR (400 MHz, $CDCl_3$) δ 8.06 (s, 1H), 7.24-7.15 (m, 4H), 6.66-6.59 (m, 1H), 6.41 (dd, J = 16.8 Hz, 2.0 Hz, 1H), 5.77 (dd, J = 10.4 Hz, 2.0 Hz, 1H), 4.75-4.64 (m, 4H), 4.18-4.16 (m, 2H), 3.70-3.67 (m, 4H), 3.37-3.09 (m, 5H), 2.66-2.60 (m, 4H), 1.57-1.54 (m, 6H). | 632.4 | 92.4 |
| 1113 | (3S)-7-((3S,5R)-4-acryloyl-3,5-dimethylpiperazin-1-yl)-9-chloro-10-(2,4-difluorophenyl)-3-(methoxymethyl)-2,3-dihydro-5H-[1,4]thiazino[2,3,4-ij]quinazolin-5-one | 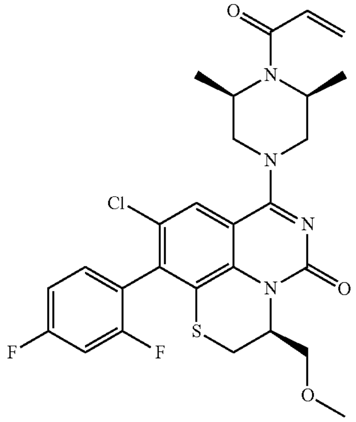 [SMILES: C=CC(=O)N1[C@H](C)CN(c2nc(=O)n3c4c(c(-c5ccc(F)cc5F)c(Cl)cc24)SC[C@@H]3COC)C[C@@H]1C] | $^1$H NMR (400 MHz, MeOH-$d_4$) δ 7.90 (s, 1H), 7.42-7.26 (m, 1H), 7.22-7.10 (m, 2H), 6.83 (dd, J = 16.7, 10.6 Hz, 1H), 6.28 (dd, J = 16.7, 2.0 Hz, 1H), 5.41-5.31 (m, 1H), 4.80-4.52 (m, 2H), 4.44-4.31 (m, 1H), 4.25 (d, J = 13.5 Hz, 1H), 3.79-3.64 (m, 1H), 3.63-3.50 (m, 2H), 3.49-3.41 (m, 2H), 3.39 (s, 3H), 3.38-3.33 (m, 1H), 3.15 (td, J = 13.2, 3.0 Hz, 1H), 1.54 (dd, J = 7.0, 2.6 Hz, 3H), 1.40 (dd, J = 7.0, 3.2 Hz, 3H); | 561.2 | 96.8 |
| 1114 | (3R,11R)-8-((3S,5R)-4-acryloyl-3,5-dimethylpiperazin-1-yl)-11-(5-chloro-2,4-difluorophenyl)-3-morpholino-10-(trifluoromethyl)-3,4-dihydro-2H,6H-[1,4]thiazepino[2,3,4-ij]quinazolin-6-one | 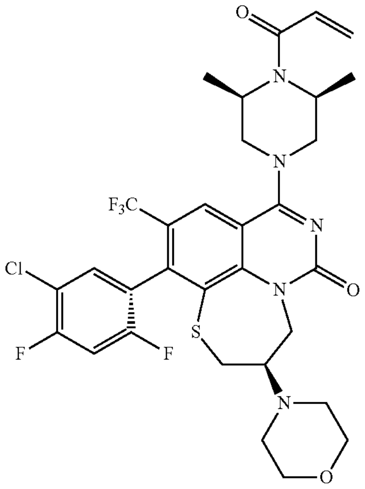 | $^1$H NMR (400 MHz, $CDCl_3$) δ 8.08 (s, 1H), 7.28-7.24 (m, 1H), 7.05 (t, J = 8.8 Hz, 1H), 6.66-6.59 (m, 1H), 6.43-6.39 (m, 1H), 5.78 (dd, J = 10.4 Hz, 1.6 Hz, 1H), 4.76-4.62 (m, 4H), 4.17-4.14 (m, 2H), 3.81-3.66 (m, 4H), 3.38-3.17 (m, 5H), 2.77-2.58 (m, 4H), 1.58-1.54 (m, 6H). | 684.3 | 71.7 |

TABLE 8-continued

Examples 1100 to 1140

| Ex. # | Name | Structure | $^1$H NMR | MS (M + H)$^+$ | % CAF 10 uM @ 60 min |
|---|---|---|---|---|---|
| 1115 | (3R,11S)-8-((3S,5R)-4-acryloyl-3,5-dimethylpiperazin-1-yl)-11-(5-chloro-2,4-difluorophenyl)-3-morpholino-10-(trifluoromethyl)-3,4-dihydro-2H,6H-[1,4]thiazepino[2,3,4-ij]quinazolin-6-one | 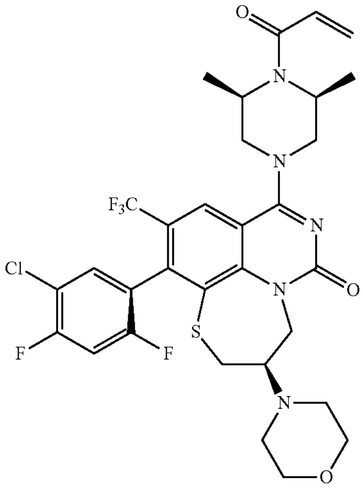 | $^1$H NMR (400 MHz, $CDCl_3$) δ 8.07 (s, 1H), 7.26-7.24 (m, 1H), 7.06 (t, J = 8.8 Hz, 1H), 6.66-6.59 (m, 1H), 6.43-6.39 (m, 1H), 5.78 (dd, J = 10.4 Hz, 2.0 Hz, 1H), 4.74-4.64 (m, 3H), 4.19-4.13 (m, 3H), 3.78-3.65 (m, 4H), 3.38-3.18 (m, 5H), 2.73-2.63 (m, 4H), 1.57-1.53 (m, 6H). | 684.3 | 42.5 |
| 1116 | 8'-(4-acryloylpiperazin-1-yl)-11'-(4-fluorophenyl)-10'-(trifluoromethyl)-2'H,4'H,6'H-spiro[oxetane-3,3'-[1,4]thiazepino[2,3,4-ij]quinazolin]-6'-one | 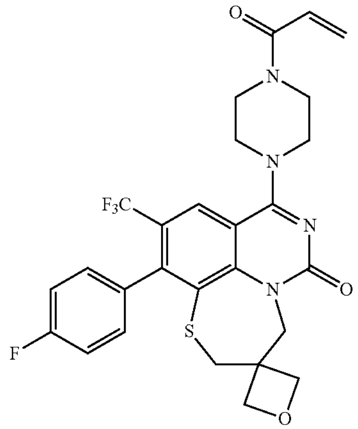 [SMILES: C=CC(=O)N1CCN(c2nc(=O)n3c4c(c(-c5ccc(F)cc5)c(C(F)(F)F)cc24)SCC2(COC2)C3)CC1] | $^1$H NMR | 561.0 | 98.4 |
| 1117 | 8'-((3S,5R)-4-acryloyl-3,5-dimethylpiperazin-1-yl)-11'-(4-fluorophenyl)-10'-(trifluoromethyl)-2'H,4'H,6'H-spiro[oxetane-3,3'-[1,4]thiazepino[2,3,4-ij]quinazolin]-6'-one | 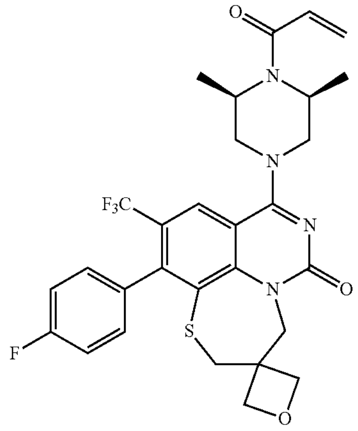 [SMILES: C=CC(=O)N1[C@H](C)CN(c2nc(=O)n3c4c(c(-c5ccc(F)cc5)c(C(F)(F)F)cc24)SCC2(COC2)C3)C[C@@H]1C] | $^1$H NMR (400 MHz, $CDCl_3$) δ 8.08 (s, 1H), 7.22-7.15 (m, 4H), 6.66-6.59 (m, 1H), 6.43-6.39 (m, 1H), 5.78 (dd, J = 10.4 Hz, 1.6 Hz, 1H), 4.79-4.60 (m, 6H), 4.34 (d, J = 6.8 Hz, 2H), 4.17-4.14 (m, 2H), 3.39-3.35 (m, 4H), 1.57-1.54 (m, 6H). | 589.4 | 96.9 |

TABLE 8-continued

Examples 1100 to 1140

| Ex. # | Name | Structure | $^1$H NMR | MS (M + H)$^+$ | % CAF 10 uM @ 60 min |
|---|---|---|---|---|---|
| 1118 | (R)-8-((3S,5R)-4-acryloyl-3,5-dimethylpiperazin-1-yl)-11-(4-fluorophenyl)-3-(pyrrolidin-1-yl)-10-(trifluoromethyl)-3,4-dihydro-2H,6H-[1,4]thiazepino[2,3,4-ij]quinazolin-6-one | 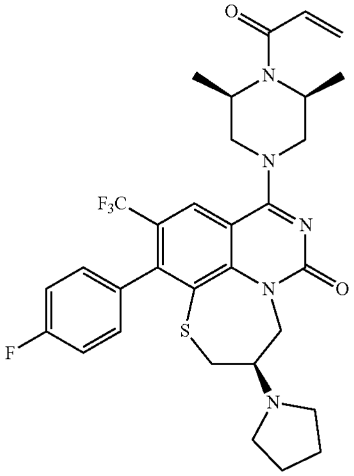 [SMILES: C=CC(=O)N1[C@H](C)CN(c2nc(=O)n3c4c(c(-c5ccc(F)cc5)c(C(F)(F)F)cc24)SC[C@H](N2CCCC2)C3)C[C@@H]1C] | $^1$H NMR (400 MHz, $CDCl_3$) δ 8.04 (s, 1H), 7.24-7.13 (m, 4H), 6.60-6.59 (m, 1H), 6.43-6.38 (m, 1H), 5.77 (dd, J = 10.4 Hz, 1.6 Hz, 1H), 4.83-4.61 (m, 4H), 4.18-4.14 (m, 2H), 3.36-3.09 (m, 5H), 2.78-2.65 (m, 4H), 1.84-1.81 (m, 4H), 1.55-1.47 (m, 6H). | 616.2 | 95.7 |
| 1119 | (3S,10S)-7-(4-acryloylpiperazin-1-yl)-3-(methoxymethyl)-10-(1-methyl-1H-indazol-7-yl)-9-(trifluoromethyl)-2,3-dihydro-5H-[1,4]thiazino[2,3,4-ij]quinazolin-5-one | 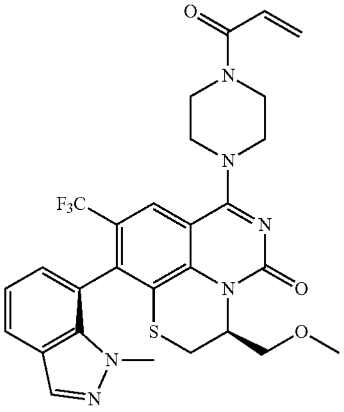 | $^1$H NMR (400 MHz, $CDCl_3$) δ 8.05 (s, 1H), 7.88-7.86 (m, 2H), 7.25-7.23 (m, 1H), 7.15-7.13 (d, J = 7.2 Hz, 1H), 6.63-6.57 (m, 1H), 6.40-6.35 (m, 1H), 5.80 (dd, J = 8.4 Hz, 2 Hz, 1H), 5.42-5.39 (m, 1H), 4.04-4.03 (m, 3H), 3.79-3.75 (m, 5H), 3.69-3.66 (m, 1H), 3.61-3.57 (m, 4H), 3.35 (s, 3H), 3.28 (dd, J = 13.2 Hz, J = 2.8 Hz, 1H), 3.00 (dd, J = 13.2 Hz, 2.4 Hz, 1H). | 585.6 | 99.4 |
| 1120 | (S)-8'-((2S,5R)-4-acryloyl-2,5-dimethylpiperazin-1-yl)-11'-(5-chloro-2,4-difluorophenyl)-10'-(trifluoromethyl)-2'H,4'H,6'H-spiro[oxetane-3,3'-[1,4]thiazepino[2,3,4-ij]quinazolin]-6'-one | 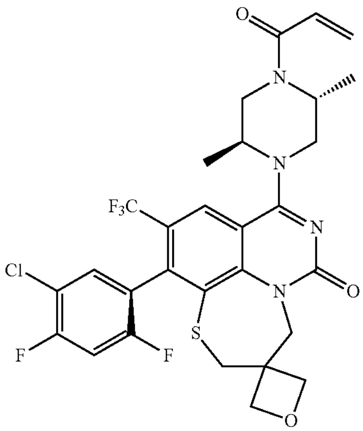 | $^1$H NMR (400 MHz, $CDCl_3$) δ 7.82 (s, 1H), 7.26-7.21 (m, 1H), 7.06 (t, J = 8.8 Hz, 1H), 6.61-6.50 (m, 1H), 6.41-6.33 (m, 1H), 5.80-5.76 (m, 1H), 5.00-4.74 (m, 5H), 4.41-4.34 (m, 3H), 4.17-3.67 (m, 3.5H), 3.43-3.40 (m, 2.5H), 1.39-1.32 (m, 6H). | 641.1 | 64.9 |

TABLE 8-continued

| Ex. # | Name | Structure | $^1$H NMR | MS $(M + H)^+$ | % CAF 10 uM @ 60 min |
|---|---|---|---|---|---|
| | Examples 1100 to 1140 | | | | |
| 1121 | (R)-8'-((2S,5R)-4-acryloyl-2,5-dimethylpiperazin-1-yl)-11'-(5-chloro-2,4-difluorophenyl)-10'-(trifluoromethyl)-2'H,4'H,6'H-spiro[oxetane-3,3'-[1,4]thiazepino [2,3,4-ij]quinazolin]-6'-one | 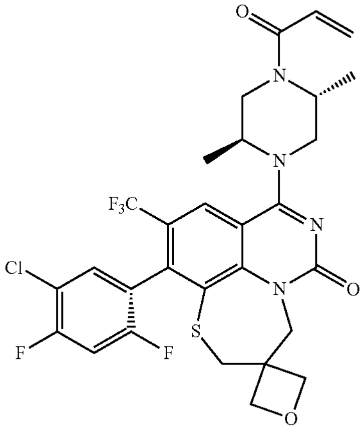 | $^1$H NMR (400 MHz, $CDCl_3$) δ 7.82 (s, 1H), 7.28-7.25 (m, 1H), 7.06 (t, J = 8.8 Hz, 1H), 6.65-6.50 (m, 1H), 6.41-6.33 (m, 1H), 5.80-5.76 (m, 1H), 5.01-4.71 (m, 5H), 4.42-4.35 (m, 3H), 3.93-3.67 (m, 3.5H), 3.49-3.39 (m, 2.5H), 1.40-1.25 (m, 6H). | 641.1 | 95.5 |
| 1122 | 8'-((2S,5R)-4-acryloyl-2,5-dimethylpiperazin-1-yl)-11'-(5-chloro-2,4-difluorophenyl)-10'-(trifluoromethyl)-2'H,4'H,6'H-spiro[oxetane-3,3'-[1,4]thiazepino [2,3,4-ij]quinazolin]-6'-one | 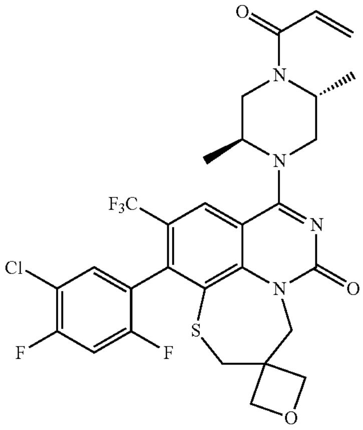 [SMILES: C=CC(=O)N1C[C@H](C)N(c2nc(=O)n3c4c(c(-c5cc(Cl)c(F)cc5F)c(C(F)(F)F)cc24)SCC2(COC2)C3)C[C@H]1C] | $^1$H NMR (400 MHz, MeOH-$d_4$) δ 7.97 (s, 1H), 7.50 (dd, J = 15.3, 7.8 Hz, 1H), 7.34 (td, J = 9.1, 3.3 Hz, 1H), 6.91-6.72 (m, 1H), 6.34-6.22 (m, 1H), 5.81 (ddd, J = 9.8, 7.3, 1.9 Hz, 1H), 4.88-4.59 (m, 3H), 4.45 (d, J = 6.3 Hz, 2H), 3.99-3.71 (m, 1H), 3.71-3.46 (m, 2H), 1.43 (dd, J = 16.2, 6.6 Hz, 3H); | 641.2 | 74.3 |
| 1123 | 8'-(4-acryloylpiperazin-1-yl)-11'-(2,4-difluorophenyl)-10'-(trifluoromethyl)-2'H,4'H,6'H-spiro[oxetane-3,3'-[1,4]thiazepino [2,3,4-ij]quinazolin]-6'-one | 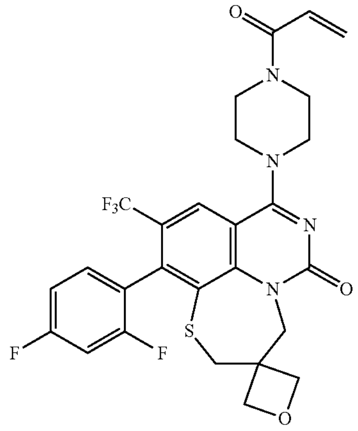 [SMILES: C=CC(=O)N1CCN(c2nc(=O)n3c4c(c(-c5ccc(F)cc5F)c(C(F)(F)F)cc24)SCC2(COC2)C3)CC1] | $^1$H NMR (400 MHz, $CDCl_3$) δ 7.82 (s, 1H), 7.16 (q, J = 7.6 Hz, 1H), 7.04-6.92 (m, 2H), 6.62-6.55 (m, 1H), 6.39-6.35 (m, 1H), 5.80-5.77 (m, 1H), 5.15-4.55 (m, 4H), 4.35 (t, J = 6.4 Hz, 2H), 3.96-3.73 (m, 8H), 3.43-3.39 (m, 2H). | 579.2 | 95.2 |

TABLE 8-continued

Examples 1100 to 1140

| Ex. # | Name | Structure | $^1H$ NMR | MS $(M + H)^+$ | % CAF 10 uM @ 60 min |
|---|---|---|---|---|---|
| 1124 | (R)-8'-((3S,5R)-4-acryloyl-3,5-dimethylpiperazin-1-yl)-11'-(5-chloro-2,4-difluorophenyl)-10'-(trifluoromethyl)-2'H,4'H,6'H-spiro[oxetane-3,3'-[1,4]thiazepino[2,3,4-ij]quinazolin]-6'-one | 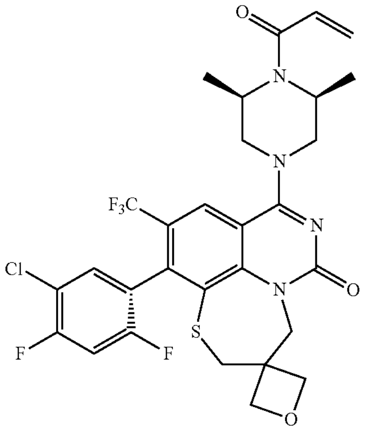 | $^1H$ NMR (400 MHz, MeOH-$d_4$) δ 8.18 (s, 1H), 7.52 (t, J = 7.5 Hz, 1H), 7.37 (t, J = 9.1 Hz, 1H), 6.85 (dd, J = 16.7, 10.6 Hz, 1H), 6.31 (dd, J = 16.7, 2.0 Hz, 1H), 5.82 (dd, J = 10.6, 2.0 Hz, 1H), 4.88-4.58 (m, 4H), 4.46 (dd, J = 6.4, 2.4 Hz, 2H), 4.27 (d, J = 13.5 Hz, 2H), 3.58 (d, J = 6.6 Hz, 2H), 3.46 (dt, J = 13.7, 4.5 Hz, 2H), 1.59-1.46 (m, 6H). | 641.1 | 96.2 |
| 1125 | (S)-8'-((3S,5R)-4-acryloyl-3,5-dimethylpiperazin-1-yl)-11'-(5-chloro-2,4-difluorophenyl)-10'-(trifluoromethyl)-2'H,4'H,6'H-spiro[oxetane-3,3'-[1,4]thiazepino[2,3,4-ij]quinazolin]-6'-one | 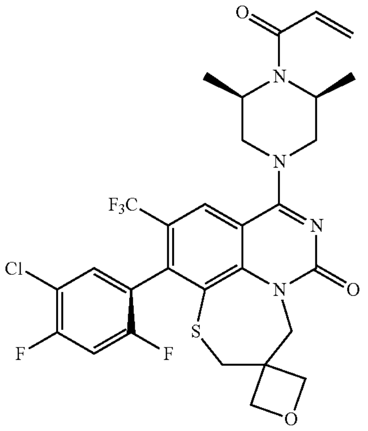 | $^1H$ NMR (400 MHz, MeOH-$d_4$) δ 8.16 (s, 1H), 7.50 (t, J = 7.7 Hz, 1H), 7.34 (t, J = 9.1 Hz, 1H), 6.83 (dd, J = 16.7, 10.6 Hz, 1H), 6.29 (dd, J = 16.6, 2.0 Hz, 1H), 5.80 (dd, J = 10.6, 2.0 Hz, 1H), 4.88-4.54 (m, 4H), 4.44 (dd, J = 6.4, 2.4 Hz, 2H), 4.25 (d, J = 13.5 Hz, 2H), 3.56 (d, J = 6.6 Hz, 2H), 3.44 (dt, J = 13.9, 4.5 Hz, 2H), 1.55-1.41 (m, 6H) | 641.1 | 92.1 |
| 1126 | (3S,10S)-7-((3S,5R)-4-acryloyl-3,5-dimethylpiperazin-1-yl)-10-(4-fluoro-1-methyl-1H-indazol-7-yl)-3-(methoxymethyl)-9-(trifluoromethyl)-2,3-dihydro-5H-[1,4]thiazino[2,3,4-ij]quinazolin-5-one | 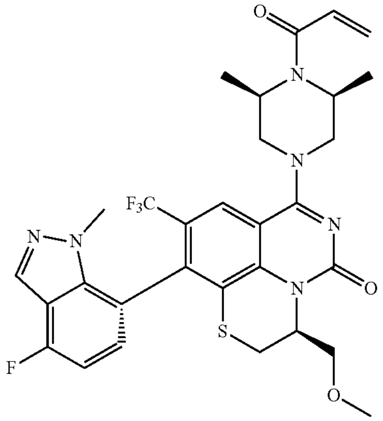 | $^1H$ NMR (400 MHz, MeOH-$d_4$) δ 8.22 (s, 1H), 8.16 (s, 1H), 7.18 (dd, J = 8.0, 4.8 Hz, 1H), 6.98 (dd, J = 9.7, 7.9 Hz, 1H), 6.85 (dd, J = 16.7, 10.6 Hz, 1H), 6.30 (dd, J = 16.6, 2.0 Hz, 1H), 5.81 (dd, J = 10.6, 2.0 Hz, 1H), 5.41-5.31 (m, 1H), 4.84-4.55 (m, 2H), 4.39 (d, J = 13.6 Hz, 1H), 4.30 (d, J = 13.6 Hz, 1H), 3.74-3.60 (m, 3H), 3.56 (s, 3H), 3.55-3.37 (m, 3H), 3.36 (s, 3H), 3.35-3.33 (m, 1H), 3.15 (dd, J = 13.7, 3.0 Hz, 1H), 1.60 (d, J = 6.9 Hz, 3H), 1.42 (d, J = 7.0 Hz, 3H) | 631.3 | 46.8 |

TABLE 8-continued

| Examples 1100 to 1140 | | | | | |
|---|---|---|---|---|---|
| Ex. # | Name | Structure | $^1H$ NMR | MS $(M + H)^+$ | % CAF 10 uM @ 60 min |
| 1127 | (R)-8'-(4-acryloylpiperazin-1-yl)-11'-(2,4-difluorophenyl)-10'-(trifluoromethyl)-2'H,4'H,6'H-spiro[oxetane-3,3'-[1,4]thiazepino [2,3,4-ij]quinazolin]-6'-one | 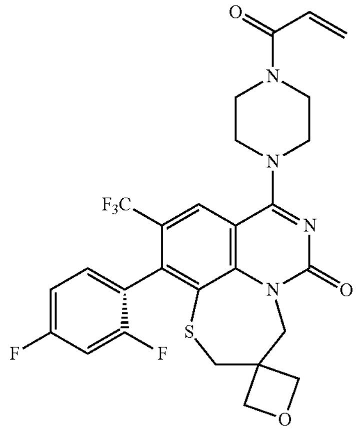 | $^1H$ NMR (400 MHz, $CDCl_3$) δ 7.82 (s, 1H), 7.16 (q, J = 7.6 Hz, 1H), 7.04-6.92 (m, 2H), 6.62-6.55 (m, 1H), 6.39-6.35 (m, 1H), 5.80-5.77 (m, 1H), 5.08-4.53 (m, 4H), 4.35 (t, J = 6.4 Hz, 2H), 3.97-3.74 (m, 8H), 3.46-3.38 (m, 2H). | 579.2 | 95.3 |
| 1128 | (S)-8'-(4-acryloylpiperazin-1-yl)-11'-(2,4-difluorophenyl)-10'-(trifluoromethyl)-2'H,4'H,6'H-spiro[oxetane-3,3'-[1,4]thiazepino [2,3,4-ij]quinazolin]-6'-one | 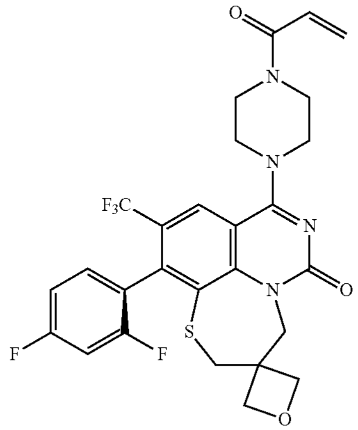 | $^1H$ NMR (400 MHz, $CDCl_3$) δ 7.82 (s, 1H), 7.16 (q, J = 7.6 Hz, 1H), 7.04-6.92 (m, 2H), 6.62-6.55 (m, 1H), 6.39-6.35 (m, 1H), 5.80-5.77 (m, 1H), 5.23-4.51 (m, 4H), 4.35 (t, J = 6.4 Hz, 2H), 3.97-3.68 (m, 8H), 3.43 (s, 2H). | 579.2 | 65.8 |
| 1129 | (3R)-8-((3S,5R)-4-acryloyl-3,5-dimethylpiperazin-1-yl)-11-(5-chloro-2,4-difluorophenyl)-3-(pyrrolidin-1-yl)-10-(trifluoromethyl)-3,4-dihydro-2H,6H-[1,4]thiazepino [2,3,4-ij]quinazolin-6-one | 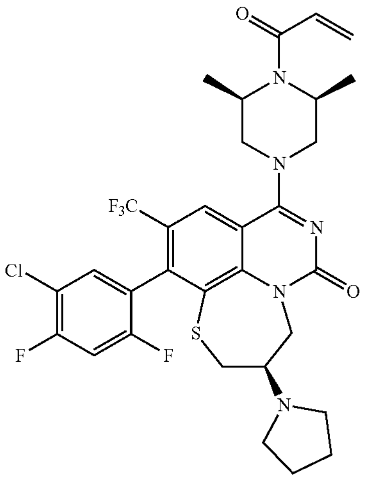 [SMILES: C=CC(=O)N1[C@H](C)CN(c2nc(=O)n3c4c(c(-c5cc(Cl)c(F)cc5F)c(C(F)(F)F)cc24)SC[C@H](N2CCCC2)C3)C[C@@H]1C] | $^1H$ NMR (400 MHz, $CDCl_3$) δ 8.05 (s, 1H), 7.25-7.23 (m, 1H), 7.04 (t, J = 16 Hz, 1H), 6.66-6.59 (m, 1H), 6.43-6.38 (m, 1H), 5.77 (dd, J = 10.4 Hz, 2.0 Hz, 1H), 4.82-4.65 (m, 4H), 4.18-4.14 (m, 2H), 3.39-3.14 (m, 5H), 2.79-2.66 (m, 4H), 1.87-1.76 (m, 4H), 1.58-1.46 (m, 6H). | 668.2 | 69 |

TABLE 8-continued

Examples 1100 to 1140

| Ex. # | Name | Structure | $^1$H NMR | MS (M + H)$^+$ | % CAF 10 uM @ 60 min |
|---|---|---|---|---|---|
| 1130 | (3S,10S)-7-((3S,5R)-4-acryloyl-3,5-dimethylpiperazin-1-yl)-3-(methoxymethyl)-10-(1-methyl-1H-indazol-7-yl)-9-(trifluoromethyl)-2,3-dihydro-5H-[1,4]thiazino[2,3,4-ij]quinazolin-5-one | 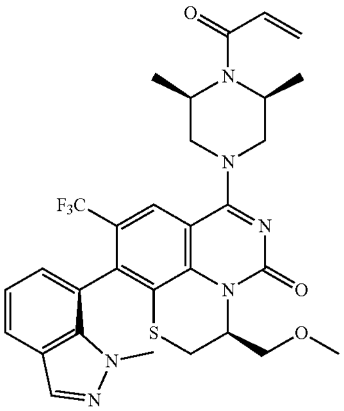 | $^1$H NMR (400 MHz, $CDCl_3$) δ 8.13 (s, 1H), 8.05 (s, 1H), 7.85 (d, J = 8.0 Hz, 1H), 7.25-7.21 (m, 1H), 7.12 (d, J = 6.8 Hz, 1H), 6.66-6.60 (m, 1H), 6.42 (d, J = 8.4 Hz, 1H), 5.78 (d, J = 10.4 Hz, 1H), 5.48-5.45 (m, 1H), 4.85-4.56 (m, 2H), 4.20 (t, J = 12.8 Hz, 2H), 3.69-3.55 (m, 5H), 3.43-3.25 (m, 6H), 2.98 (d, J = 12.4 Hz, 1H), 1.62 (d, J = 6.8 Hz, 3H), 1.50 (d, J = 6.4 Hz, 3H). | 613.3 | 95.6 |
| 1131 | (3S,10R)-7-((3S,5R)-4-acryloyl-3,5-dimethylpiperazin-1-yl)-3-(methoxymethyl)-10-(1-methyl-1H-indazol-7-yl)-9-(trifluoromethyl)-2,3-dihydro-5H-[1,4]thiazino[2,3,4-ij]quinazolin-5-one | 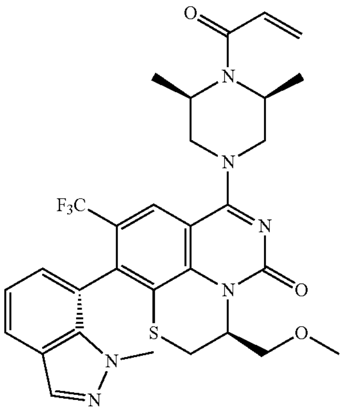 | $^1$H NMR (400 MHz, $CDCl_3$) δ 8.13 (s, 1H), 8.06 (s, 1H), 7.87 (dd, J = 0.8 Hz, 8.0 Hz, 1H), 7.28-7.24 (m, 1H), 7.14 (d, J = 7.2 Hz, 1H), 6.67-6.60 (m, 1H), 6.45-6.39 (m, 1H), 5.78 (dd, J = 10.0 Hz, 2.0 Hz, 1H), 5.45-5.40 (m, 1H), 4.86-4.55 (m, 2H), 4.25-4.20 (m, 2H), 3.68-3.55 (m, 5H), 3.45-3.35 (m, 5H), 3.29-3.25 (m, 1H), 3.03-2.98 (m, 1H), 1.65 (d, J = 7.2 Hz, 3H), 1.48 (d, J = 6.8 Hz, 3H). | 613.3 | 18.2 |
| 1132 | (S)-8'-((3S,5R)-4-acryloyl-3,5-dimethylpiperazin-1-yl)-11'-(1-methyl-1H-indazol-7-yl)-10'-(trifluoromethyl)-2'H,4'H,6'H-spiro[oxetane-3,3'-[1,4]thiazepino[2,3,4-ij]quinazolin]-6'-one | 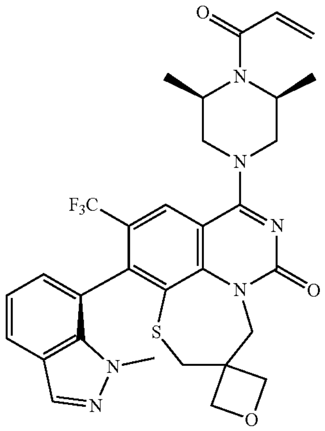 | $^1$H NMR (400 MHz, $CDCl_3$) δ 8.14 (s, 1H), 8.06 (s, 1H), 7.86 (d, J = 8.0 Hz, 1H), 7.25-7.22 (m, 1H), 7.11 (d, J = 7.2 Hz, 1H), 6.62-6.60 (m, 1H), 6.44-6.40 (m, 1H), 5.79 (dd, J = 10.4 Hz, 1.6 Hz, 1H), 5.34-4.47 (m, 6H), 4.32-4.28 (m, 2H), 4.20-4.14 (m, 2H), 3.56 (s, 3H), 3.44-3.38 (m, 4H), 1.31-1.25 (m, 6H). | 625.4 | 85.6 |

TABLE 8-continued

| Examples 1100 to 1140 | | | | | |
|---|---|---|---|---|---|
| Ex. # | Name | Structure | $^1$H NMR | MS (M + H)$^+$ | % CAF 10 uM @ 60 min |
| 1133 | (R)-8'-((3S,5R)-4-acryloyl-3,5-dimethylpiperazin-1-yl)-11'-(1-methyl-1H-indazol-7-yl)-10'-(trifluoromethyl)-2'H,4'H,6'H-spiro[oxetane-3,3'-[1,4]thiazepino[2,3,4-ij]quinazolin]-6'-one | 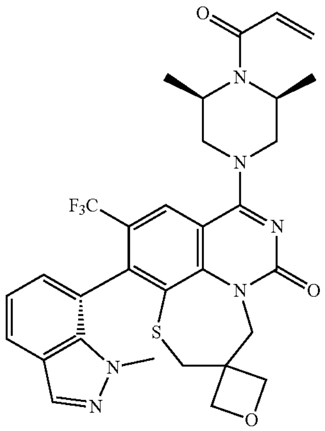 | $^1$H NMR (400 MHz, $CDCl_3$) δ 8.14 (s, 1H), 8.06 (s, 1H), 7.86 (dd, J = 8.4 Hz, 3.2 Hz, 1H), 7.25-7.22 (m, 1H), 7.11 (d, J = 6.0 Hz, 1H), 6.68-6.60 (m, 1H), 6.44-6.40 (m, 1H), 5.79 (d, J = 9.6 Hz, 1H), 5.34-4.53 (m, 6H), 4.35-4.28 (m, 2H), 4.20-4.14 (m, 2H), 3.59 (s, 3H), 3.44-3.34 (m, 4H), 1.31-1.26 (m, 6H). | 625.4 | 54.1 |
| 1134 | (S)-8-((3S,5R)-4-acryloyl-3,5-dimethylpiperazin-1-yl)-11-(4-fluorophenyl)-3-morpholino-10-(trifluoromethyl)-3,4-dihydro-[1,4]thiazepino[2,3,4-ij]quinazolin-6(2H)-one | 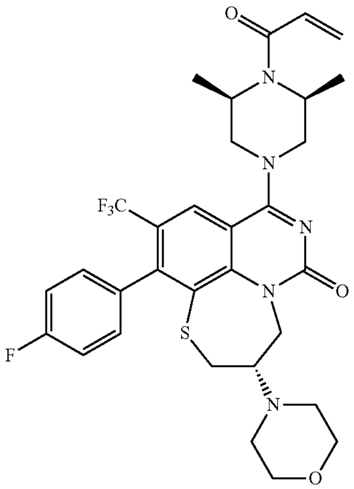 [SMILES: C=CC(=O)N1[C@H](C)CN(c2nc(=O)n3c4c(c(-c5ccc(F)cc5)c(C(F)(F)F)cc24)SC[C@@H](N2CCOCC2)C3)C[C@@H]1C] | $^1$H NMR (400 MHz, $CDCl_3$) δ 8.06 (s, 1H), 7.21-7.15 (m, 4H), 6.66-6.59 (m, 1H), 6.42 (dd, J = 2.0 Hz, 16.4 Hz, 1H), 5.78 (dd, J = 1.6 Hz, 10.4 Hz, 1H), 4.75-4.72 (m, 3H), 4.15 (t, J = 10.8 Hz, 2H), 3.72-3.66 (m, 4H), 3.37-3.08 (m, 5H), 2.70-2.64 (m, 4H), 1.57-1.49 (m, 6H), 1.31-1.25 (m, 1H). | 632.4 | 76.8 |
| 1135 | (3S,11S)-8-((3S,5R)-4-acryloyl-3,5-dimethylpiperazin-1-yl)-11-(5-chloro-2,4-difluorophenyl)-3-morpholino-10-(trifluoromethyl)-3,4-dihydro-2H,6H-[1,4]thiazepino[2,3,4-ij]quinazolin-6-one | 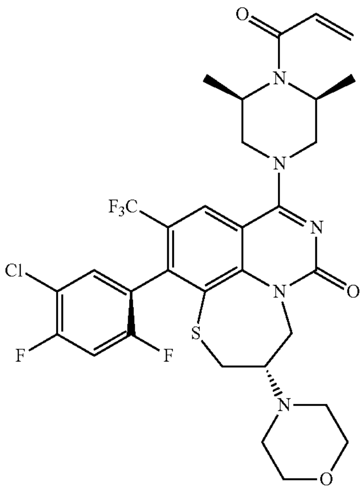 | $^1$H NMR (400 MHz, $CDCl_3$) δ 8.07 (s, 1H), 7.27-7.23 (m, 1H), 7.05 (t, J = 8.8 Hz, 1H), 6.65-6.59 (m, 1H), 6.43 (dd, J = 1.6 Hz, 16.8 Hz, 1H), 5.78 (dd, J = 1.6 Hz, 10.4 Hz, 1H), 4.81-4.60 (m, 4H), 4.16 (d, J = 12.8 Hz, 2H), 3.72-3.71 (m, 4H), 3.36-3.18 (m, 5H), 2.69-2.67 (m, 4H), 1.64-1.53 (m, 6H). | 684.3 | 72.7 |

TABLE 8-continued

| Ex. # | Name | Structure | $^1H$ NMR | MS (M + H)$^+$ | % CAF 10 uM @ 60 min |
|---|---|---|---|---|---|
| Examples 1100 to 1140 | | | | | |
| 1136 | (3S,11R)-8-((3S,5R)-4-acryloyl-3,5-dimethylpiperazin-1-yl)-11-(5-chloro-2,4-difluorophenyl)-3-morpholino-10-(trifluoromethyl)-3,4-dihydro-2H,6H-[1,4]thiazepino[2,3,4-ij]quinazolin-6-one | 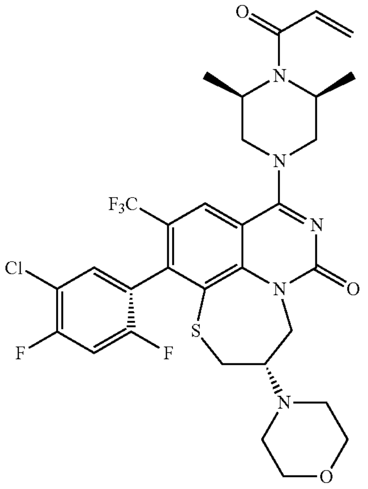 | $^1H$ NMR (400 MHz, $CDCl_3$) δ 8.07 (s, 1H), 7.27-7.23 (m, 1H), 7.05 (t, J = 8.8 Hz, 1H), 6.65-6.59 (m, 1H), 6.43 (dd, J = 2.0 Hz, 16.8 Hz, 1H), 5.78 (dd, J = 2.0 Hz, 10.4 Hz, 1H), 4.84-4.59 (m, 4H), 4.14 (t, J = 15.6 Hz, 2H), 3.73-3.68 (m, 4H), 3.38-3.15 (m, 5H), 2.72-2.58 (m, 4H), 1.54-1.52 (m, 6H). | 684.3 | 82.7 |
| 1137 | (3S,11R)-8-((3S,5R)-4-acryloyl-3,5-dimethylpiperazin-1-yl)-11-(5-chloro-2,4-difluorophenyl)-3-(pyrrolidin-1-yl)-10-(trifluoromethyl)-3,4-dihydro-2H,6H-[1,4]thiazepino[2,3,4-ij]quinazolin-6-one | 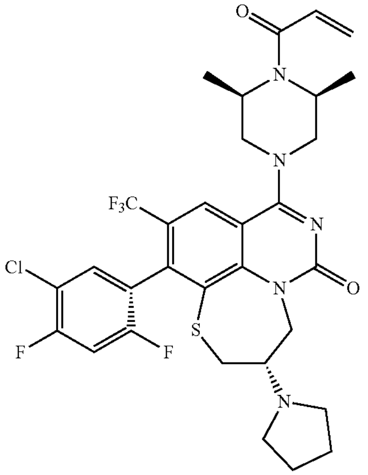 | $^1H$ NMR (400 MHz, $CDCl_3$) δ: 8.06 (s, 1H), 7.29-7.24 (m, 1H), 7.04 (t, J = 8.4 Hz, 1H), 6.66-6.59 (m, 1H), 6.44-6.38 (m, 1H), 5.78 (dd, J = 16.8 Hz, 2.0 Hz, 1H), 4.81-4.51 (m, 4H), 4.17-4.13 (m, 2H), 3.35-3.30 (m, 3H), 3.19-3.14 (m, 2H), 2.76-2.67 (m, 4H), 1.83-1.78 (m, 4H), 1.58-1.51 (m, 6H). | 668.3 | 83.4 |
| 1138 | (3S,11S)-8-((3S,5R)-4-acryloyl-3,5-dimethylpiperazin-1-yl)-11-(5-chloro-2,4-difluorophenyl)-3-(pyrrolidin-1-yl)-10-(trifluoromethyl)-3,4-dihydro-2H,6H-[1,4]thiazepino[2,3,4-ij]quinazolin-6-one | 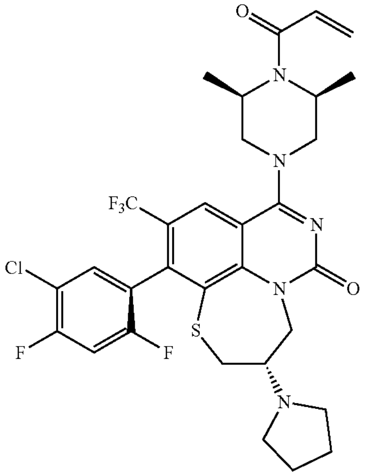 | $^1H$ NMR (400 MHz, $CDCl_3$) δ: 8.17 (s, 1H), 8.08 (s, 1H), 7.90 (d, J = 8.8 Hz, 1H), 7.26-7.24 (m, 1H), 7.15 (d, J = 7.2 Hz, 1H), 6.67-6.60 (m, 1H), 6.44-6,39 (m, 1H), 5.81 (d, J = 12.4 Hz, 1H), 5.47 (s, 1H), 4.27 (d, J = 13.6 Hz, 2H), 3.57-3.39 (m, 5H), 3.22-3.07 (m, 5H), 3.01-3.96 (m, 11H), 1.66 (d, J = 6.8 Hz, 3H), 1.49 (d, J = 6.8 Hz, 3H), 1.36 (t, J = 7.2 Hz, 3H). | 668.3 | 50.5 |

TABLE 8-continued

Examples 1100 to 1140

| Ex. # | Name | Structure | $^1$H NMR | MS (M + H)$^+$ | % CAF 10 uM @ 60 min |
|---|---|---|---|---|---|
| 1139 | (3S,10R)-7-((3S,5R)-4-acryloyl-3,5-dimethylpiperazin-1-yl)-10-(5-chloro-2,4-difluorophenyl)-3-(methoxymethyl)-9-(trifluoromethyl)-2,3-dihydro-5H-[1,4]thiazino[2,3,4-ij]quinazolin-5-one | 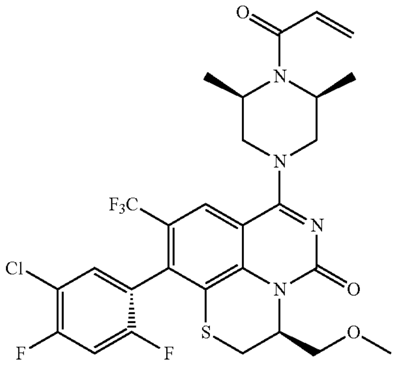 | $^1$H NMR (400 MHz, $CDCl_3$) δ 8.06 (s, 1H), 7.28-7.24 (m, 1H), 7.07 (t, J = 8.8 Hz, 1H), 6.65-6.59 (m, 1H), 6.40 (dd, J = 1.6 Hz, 16.8 Hz, 1H), 5.77 (dd, J = 1.2 Hz, 10.0 Hz, 1H), 5.45-5.44 (m, 1H), 4.73-4.58 (m, 2H), 4.21-4.15 (m, 2H), 3.67-3.64 (m, 2H), 3.41-3.31 (m, 6H), 3.05-3.01 (m, 1H), 1.61 (m, J = 6.8 Hz, 3H), 1.47 (d, J = 6.8 Hz, 3H). | 629.2 | 95.9 |
| 1140 | (3S,10S)-7-((3S,5R)-4-acryloyl-3,5-dimethylpiperazin-1-yl)-10-(5-chloro-2,4-difluorophenyl)-3-(methoxymethyl)-9-(trifluoromethyl)-2,3-dihydro-5H-[1,4]thiazino[2,3,4-ij]quinazolin-5-one | 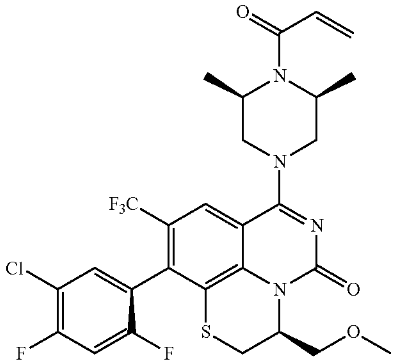 | $^1$H NMR (400 MHz, $CDCl_3$) δ: 8.07 (s, 1H), 7.28-7.25 (m, 1H), 7.07 (t, J = 8.8 Hz, 1H), 6.65-6.59 (m, 1H), 6.40 (dd, J = 1.6 Hz, 16.4 Hz, 1H), 5.77 (dd, J = 1.6 Hz, 10.4 Hz, 1H), 5.48-5.45 (m, 1H), 4.76-4.59 (m, 2H), 4.21-4.16 (m, 2H), 3.68-3.59 (m, 2H), 3.39-3.30 (m, 6H), 3.04-3.00 (m, 1H), 1.61-1.59 (m, 3H), 1.46 (d, J = 6.4 Hz, 3H). | 629.2 | 93.9 |

Example 1001: (3R)-8-((3S,5R)-4-acryloyl-3,5-dimethylpiperazin-1-yl)-11-(2,4-difluorophenyl)-3-(dimethylamino)-10-(trifluoromethyl)-3,4-dihydro-2H,6H-[1,4]thiazepino[2,3,4-ij]quinazolin-6-one

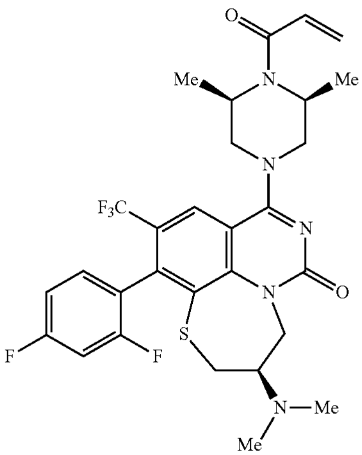 [SMILES: C=CC(=O)N1[C@H](C)CN(c2nc(=O)n3c4c(c(-c5ccc(F)cc5F)c(C(F)(F)F)cc24)SC[C@H](N(C)C)C3)C[C@@H]1C]

The title compound was prepared analogously to Example 84 where (3R)-11-(2,4-difluorophenyl)-3-(dimethylamino)-8-((3S,5R)-3,5-dimethylpiperazin-1-yl)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 38% yield as a white solid. m/z (ESI, +ve)=608.2 [M+H]$^+$ 1H NMR (400 MHz, DMSO-d6) δ 8.12 (s, 1H), 7.34-7.24 (m, 1H), 7.13 (m, 2H), 6.84 (dd, J=16.6, 10.6 Hz), 6.29 (dd, J=16.6, 2.0 Hz), 5.80 (dd, J=10.6, 2.0 Hz), 4.76-4.57 (m, 2H), 4.40-4.27 (m, 2H), 3.79-3.71 (m, 1H), 3.65-3.58 (m, 1H), 3.53-3.41 (m, 2H), 3.21-3.10 (m, 1H), 2.64-2.48 (m, 2H), 2.23 (s, 6H), 1.54-1.44 (m, 6H)

Step 1: (S)-1-(benzyloxy)-3-(tritylthio)propan-2-ol

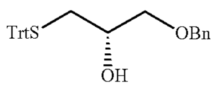

The title compound was prepared analogously to Example 454, step 1, where (2S)-2-(benzyloxymethyl)oxirane was substituted in place of (2R)-2-(benzyloxymethyl)oxirane. The title compound was isolated in 70% yield as a colorless oil. m/z (ESI, +ve)=663.2 [M+Na]

Step 2: (S)-1-(benzyloxy)-3-(tritylthio)propan-2-yl methanesulfonate

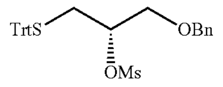

The title compound was prepared analogously to Example 454, step 2, where (S)-1-(benzyloxy)-3-(tritylthio)propan-2-ol was substituted in place of (R)-1-(benzyloxy)-3-(tritylthio)propan-2-ol. The title compound was isolated in 52% yield as a colorless oil.

1H NMR (400 MHz, CDCl3) δ 7.45-7.42 (m, 5H), 7.34-7.24 (m, 15H), 4.52-4.41 (m, 2H), 4.33 (qd, J=6.4, 4.8 Hz, 1H), 3.55-3.43 (m, 2H), 2.95 (s, 3H), 2.64 (qd, J=13.4, 6.5 Hz, 2H).

Step 3: (R)-3-(benzyloxy)-2-(dimethylamino)propane-1-thiol

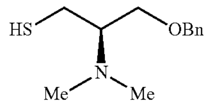

A solution of (S)-1-(benzyloxy)-3-(tritylthio)propan-2-yl methanesulfonate (6 g, 11.6 mmol) in 115 mL of N,N-dimethylamine was stirred at 70° C. overnight. The mixture was cooled to room temperature and the volatiles were removed under reduced pressure to afford a residue that was purified by silica gel chromatography (0-10% MeOH in dichloromethane). The title compound was isolated in 9% yield as a pale yellow oil. m/z (ESI, +ve)=226.2 $[M+H]^+$ Step 4: 8-(((R)-3-(benzyloxy)-2-(dimethylamino)propyl)thio)-7-(2,4-difluorophenyl)-6-(trifluoromethyl)quinazoline-2,4(1H,3H)-dione

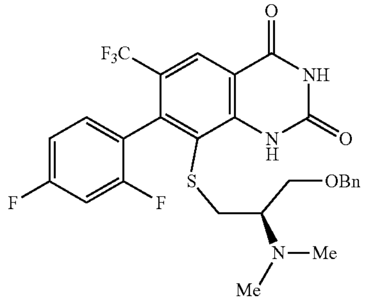 [SMILES: CN(C)[C@H](COCc1ccccc1)CSc1c(-c2ccc(F)cc2F)c(C(F)(F)F)cc2c(=O)[nH]c(=O)[nH]c12]

The title compound was prepared analogously to Example 100, step 9 where (R)-3-(benzyloxy)-2-(dimethylamino)propane-1-thiol was substituted in place of 2-mercaptoethan-1-ol. The title compound was isolated in 65% yield as a pale yellow oil. m/z (ESI, +ve)=566.1 $[M+H]^+$ Step 5: 7-(2,4-difluorophenyl)-8-(((R)-2-(dimethylamino)-3-hydroxypropyl)thio)-6-(trifluoromethyl)quinazoline-2,4(1H,3H)-dione

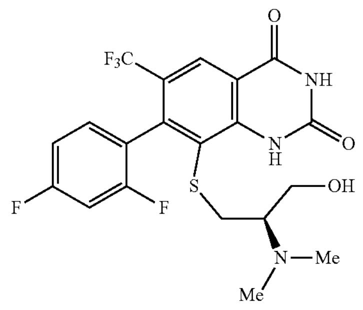 [SMILES: CN(C)[C@H](CO)CSc1c(-c2ccc(F)cc2F)c(C(F)(F)F)cc2c(=O)[nH]c(=O)[nH]c12]

A 1M solution of Boron tribromide in dichloromethane (0.32 mL) was added over a solution of 8-(((R)-3-(benzyloxy)-2-(dimethylamino)propyl)thio)-7-(2,4-difluorophenyl)-6-(trifluoromethyl)quinazoline-2,4(1H,3H)-dione in 3 mL of dichloromethane cooled down to −78° C. The reaction was stirred at that temperature for one hour and quenched with an aqueous saturated solution of $NaHCO_3$, followed by extraction with ethyl acetate three times. The organic layers were combined, dried with sodium sulfate and the volatiles removed under reduced pressure to afford a residue that was purified by silica gel chromatography (0-15% MeOH in dichloromethane). The title compound was isolated in 12% yield as colorless oil. m/z (ESI, +ve)=476.1 $[M+H]^+$ Step 6: (3R)-11-(2,4-difluorophenyl)-3-(dimethylamino)-10-(trifluoromethyl)-3,4-dihydro-2H,6H-[1,4]thiazepino[2,3,4-ij]quinazoline-6,8(7H)-dione

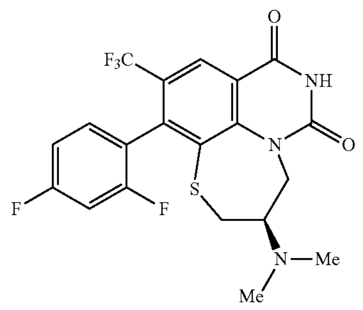 [SMILES: CN(C)[C@H]1CSc2c(-c3ccc(F)cc3F)c(C(F)(F)F)cc3c(=O)[nH]c(=O)n(c23)C1]

The title compound was prepared analogously to Example 100, step 10 where (3R)-11-(2,4-difluorophenyl)-3-(dimethylamino)-10-(trifluoromethyl)-3,4-dihydro-2H,6H-[1,4]thiazepino[2,3,4-ij]quinazoline-6,8(7H)-dione was substituted in place of 7-(2,4-difluorophenyl)-8-((2-hydroxyethyl)thio)-6-(trifluoromethyl)quinazoline-2,4(1H,3H)-dione. The title compound was isolated in 86% yield as a white solid. m/z (ESI, +ve)=458.1 $[M+H]^+$ Step 7: tert-butyl (2S,6R)-4-((3R)-11-(2,4-difluorophenyl)-3-(dimethylamino)-6-oxo-10-(trifluoromethyl)-3,4-dihydro-2H,6H-[1,4]thiazepino[2,3,4-ij]quinazolin-8-yl)-2,6-dimethylpiperazine-1-carboxylate

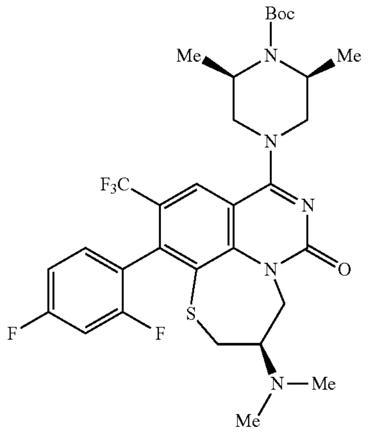 [SMILES: C[C@@H]1CN(c2nc(=O)n3c4c(c(-c5ccc(F)cc5F)c(C(F)(F)F)cc24)SC[C@H](N(C)C)C3)C[C@H](C)N1C(=O)OC(C)(C)C]

The title compound was prepared analogously to Example 100, step 21 where 7-(2,4-difluorophenyl)-8-(((R)-2-(dimethylamino)-3-hydroxypropyl)thio)-6-(trifluoromethyl)quinazoline-2,4(1H,3H)-dione and (2R,6S)-2,6-dimethylpiperazine were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 21% yield as a yellow oil. m/z (ESI, +ve)=654.2 $[M+H]^+$ Step 8: (3R)-11-(2,4-difluorophenyl)-3-(dimethylamino)-8-((3S,5R)-3,5-dimethylpiperazin-1-yl)-10-(trifluoromethyl)-3,4-dihydro-2H,6H-[1,4]thiazepino[2,3,4-ij]quinazolin-6-one

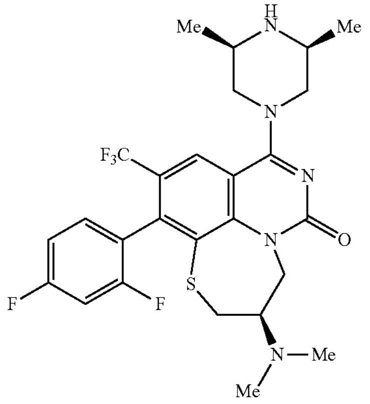 [SMILES: C[C@@H]1CN(c2nc(=O)n3c4c(c(-c5ccc(F)cc5F)c(C(F)(F)F)cc24)SC[C@H](N(C)C)C3)C[C@H](C)N1]

The title compound was prepared analogously to Example 102, step 4, where tert-butyl (2S,6R)-4-((3R)-11-(2,4-difluorophenyl)-3-(dimethylamino)-6-oxo-10-(trifluoromethyl)-3,4-dihydro-2H,6H-[1,4]thiazepino[2,3,4-ij]quinazolin-8-yl)-2,6-dimethylpiperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. m/z (ESI, +ve)=554.2 $[M+H]^+$ Example 1002: (R)-8-(4-acryloylpiperazin-1-yl)-11-(4-fluorophenyl)-3-hydroxy-10-(trifluoromethyl)-3,4-dihydro-2H,6H-[1,4]thiazepino[2,3,4-ij]quinazolin-6-one

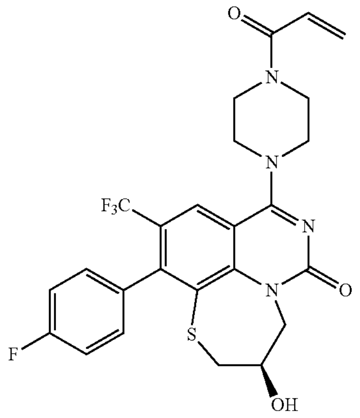 [SMILES: C=CC(=O)N1CCN(c2nc(=O)n3c4c(c(-c5ccc(F)cc5)c(C(F)(F)F)cc24)SC[C@H](O)C3)CC1]

A 1M solution of Boron tribromide in dichloromethane (0.06 mL) was added over a solution of (R)-8-(4-acryloylpiperazin-1-yl)-3-(benzyloxy)-11-(4-fluorophenyl)-10-(trifluoromethyl)-3,4-dihydro-2H,6H-[1,4]thiazepino[2,3,4-ij]quinazolin-6-one (10 mg) in 1 mL of dichloromethane cooled down to −78° C. The reaction was stirred at that temperature for one hour and quenched with an aqueous saturated solution of $NaHCO_3$, followed by extraction with ethyl acetate three times. The organic layers were combined, dried with sodium sulfate and the volatiles removed under reduced pressure to afford the title compound in 23% yield as white solid. m/z (ESI, +ve)=535.2 $[M+H]^+$ Step 1: (R)-2-(benzyloxy)-3-mercaptopropan-1-ol

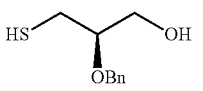 [SMILES: OC[C@H](CS)OCc1ccccc1]

The title compound was synthesized analogously to example 431, steps 1-4, where (2S)-3-chloropropane-1,2-diol was substituted in place of (2R)-3-chloropropane-1,2-diol Step 2: (R)-3-(benzyloxy)-11-(4-fluorophenyl)-10-(trifluoromethyl)-3,4-dihydro-2H,6H-[1,4]thiazepino[2,3,4-ij]quinazoline-6,8(7H)-dione

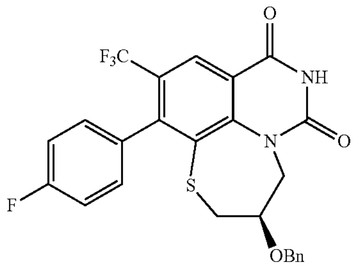 [SMILES: O=c1[nH]c(=O)n2c3c(c(-c4ccc(F)cc4)c(C(F)(F)F)cc13)SC[C@H](OCc1ccccc1)C2]

The title compound was synthesized analogously to example 100, step 9 where 7-(4-fluorophenyl)-8-iodo-6-(trifluoromethyl)quinazoline-2,4(1H,3H)-dione and (R)-2-(benzyloxy)-3-mercaptopropan-1-ol were substituted in place of 7-(2,4-difluorophenyl)-8-iodo-6-(trifluoromethyl)quinazoline-2,4(1H,3H)-dione and 2-mercaptoethan-1-ol. The title compound was isolated in 58% yield as a white solid. m/z (ESI, +ve)=503.1 $[M+H]^+$ Step 3: tert-butyl (R)-4-(3-(benzyloxy)-11-(4-fluorophenyl)-6-oxo-10-(trifluoromethyl)-3,4-dihydro-2H,6H-[1,4]thiazepino[2,3,4-ij]quinazolin-8-yl)piperazine-1-carboxylate

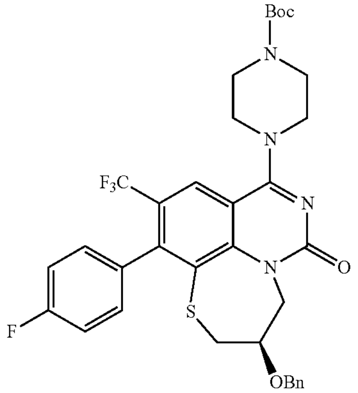 [SMILES: CC(C)(C)OC(=O)N1CCN(c2nc(=O)n3c4c(c(-c5ccc(F)cc5)c(C(F)(F)F)cc24)SC[C@H](OCc2ccccc2)C3)CC1]

The title compound was prepared analogously to Example 100, step 21 where (R)-3-(benzyloxy)-11-(4-fluorophenyl)-10-(trifluoromethyl)-3,4-dihydro-2H,6H-[1,4]thiazepino[2,3,4-ij]quinazoline-6,8(7H)-dione and tert-butyl piperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 95% yield as a yellow solid. m/z (ESI, +ve)=671.2 $[M+H]^+$ Step 4: (R)-3-(benzyloxy)-11-(4-fluorophenyl)-8-(piperazin-1-yl)-10-(trifluoromethyl)-3,4-dihydro-2H,6H-[1,4]thiazepino[2,3,4-ij]quinazolin-6-one

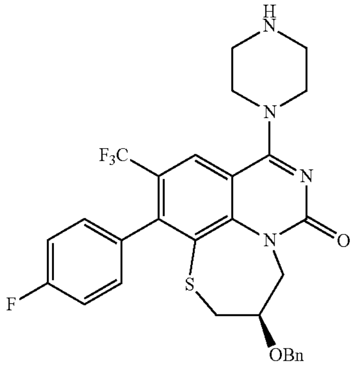 [SMILES: O=c1nc(N2CCNCC2)c2cc(C(F)(F)F)c(-c3ccc(F)cc3)c3c2n1C[C@@H](OCc1ccccc1)CS3]

The title compound was prepared analogously to Example 102, step 4, where tert-butyl (R)-4-(3-(benzyloxy)-11-(4-fluorophenyl)-6-oxo-10-(trifluoromethyl)-3,4-dihydro-2H,6H-[1,4]thiazepino[2,3,4-ij]quinazolin-8-yl)piperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. m/z (ESI, +ve)=571.2 $[M+H]^+$ Step 5: (R)-8-(4-acryloylpiperazin-1-yl)-3-(benzyloxy)-11-(4-fluorophenyl)-10-(trifluoromethyl)-3,4-dihydro-2H,6H-[1,4]thiazepino[2,3,4-ij]quinazolin-6-one The title compound was prepared analogously to Example 84 where (R)-3-(benzyloxy)-11-(4-fluorophenyl)-8-(piperazin-1-yl)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 29% yield as a white solid.

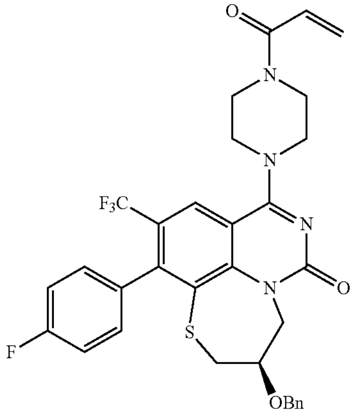 [SMILES: C=CC(=O)N1CCN(c2nc(=O)n3c4c(c(-c5ccc(F)cc5)c(C(F)(F)F)cc24)SC[C@H](OCc2ccccc2)C3)CC1]

m/z (ESI, +ve)=625.2 $[M+H]^+$

Example 1003: (S)-8-((3S,5R)-4-acryloyl-3,5-dimethylpiperazin-1-yl)-11-(4-fluorophenyl)-3-hydroxy-10-(trifluoromethyl)-3,4-dihydro-2H,6H-[1,4]thiazepino[2,3,4-ij]quinazolin-6-one

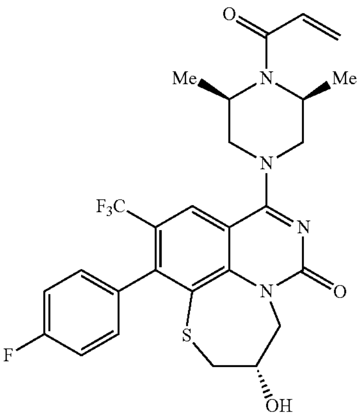 [SMILES: C=CC(=O)N1[C@H](C)CN(c2nc(=O)n3c4c(c(-c5ccc(F)cc5)c(C(F)(F)F)cc24)SC[C@@H](O)C3)C[C@@H]1C]

The title compound was prepared analogously to Example 2, where (S)-8-((3S,5R)-4-acryloyl-3,5-dimethylpiperazin-1-yl)-3-(benzyloxy)-11-(4-fluorophenyl)-10-(trifluoromethyl)-3,4-dihydro-2H,6H-[1,4]thiazepino[2,3,4-ij]quinazolin-6-one was substituted in place of (R)-8-(4-acryloylpiperazin-1-yl)-3-(benzyloxy)-11-(4-fluorophenyl)-10-(trifluoromethyl)-3,4-dihydro-2H,6H-[1,4]thiazepino[2,3,4-ij]quinazolin-6-one. The title compound was isolated in 22% yield as a yellow solid. m/z (ESI, +ve)=563.2 $[M+H]^+$ 1H NMR (400 MHz, DMSO-d6) δ 8.02 (s, 1H), 7.33-7.29 (m, 4H), 6.82 (dd, J=16.0, 8.0 Hz, 1H), 6.19 (dd, J=16.0, 4.0 Hz, 1H), 5.74 (dd, J=16.0, 4.0 Hz, 1H), 5.41 (s, 1H), 4.61-4.41 (m, 3H), 4.19-4.03 (m, 3H), 3.33-3.18 (m, 4H), 2.86-2.82 (m, 1H), 1.44-1.23 (m, 6H).

Step 1: (S)-8-((2-(benzyloxy)-3-hydroxypropyl)thio)-7-(4-fluorophenyl)-6-(trifluoromethyl)quinazoline-2,4(1H,3H)-dione

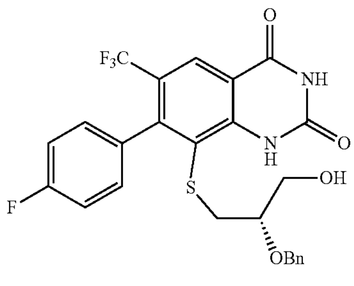 [SMILES: O=c1[nH]c(=O)c2cc(C(F)(F)F)c(-c3ccc(F)cc3)c(SC[C@H](CO)OCc3ccccc3)c2[nH]1]

The title compound was synthesized analogously to example 527, step 9 where (S)-2-(benzyloxy)-3-mercaptopropan-1-ol was substituted in place of 2-mercaptoethan-1-ol. The title compound was isolated in 86% yield as a yellow solid. m/z (ESI, +ve)=521.1 $[M+H]^+$ Step 2: (S)-3-(benzyloxy)-11-(4-fluorophenyl)-10-(trifluoromethyl)-3,4-dihydro-2H,6H-[1,4]thiazepino[2,3,4-ij]quinazoline-6,8(7H)-dione

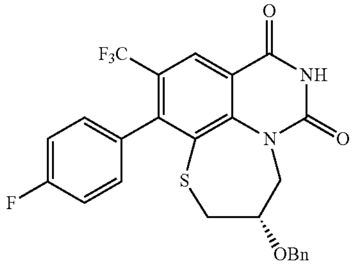 [SMILES: O=c1[nH]c(=O)n2c3c(c(-c4ccc(F)cc4)c(C(F)(F)F)cc13)SC[C@@H](OCc1ccccc1)C2]

The title compound was synthesized analogously to example 527, step 10 where ((S)-8-((2-(benzyloxy)-3-hydroxypropyl)thio)-7-(4-fluorophenyl)-6-(trifluoromethyl)quinazoline-2,4(1H,3H)-dione was substituted in place of (R)-7-(4-fluorophenyl)-8-((3-hydroxy-2-methoxypropyl)thio)-6-(trifluoromethyl)quinazoline-2,4(1H,3H)-dione. The title compound was isolated in 65% yield as a yellow solid. m/z (ESI, +ve)=503.0 $[M+H]^+$ Step 3: (S)-3-(benzyloxy)-8-((3S,5R)-3,5-dimethylpiperazin-1-yl)-11-(4-fluorophenyl)-10-(trifluoromethyl)-3,4-dihydro-2H,6H-[1,4]thiazepino[2,3,4-ij]quinazolin-6-one

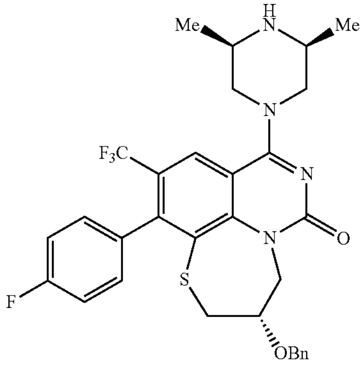 [SMILES: C[C@@H]1CN(c2nc(=O)n3c4c(c(-c5ccc(F)cc5)c(C(F)(F)F)cc24)SC[C@@H](OCc2ccccc2)C3)C[C@H](C)N1]

The title compound was prepared analogously to Example 100, step 21 where (S)-3-(benzyloxy)-11-(4-fluorophenyl)-10-(trifluoromethyl)-3,4-dihydro-2H,6H-[1,4]thiazepino[2,3,4-ij]quinazoline-6,8(7H)-dione and (2R,6S)-2,6-dimethylpiperazine were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 95% yield as a yellow solid. m/z (ESI, +ve)=599.2 $[M+H]^+$ Step 4: (S)-8-((3S,5R)-4-acryloyl-3,5-dimethylpiperazin-1-yl)-3-(benzyloxy)-11-(4-fluorophenyl)-10-(trifluoromethyl)-3,4-dihydro-2H,6H-[1,4]thiazepino[2,3,4-ij]quinazolin-6-one

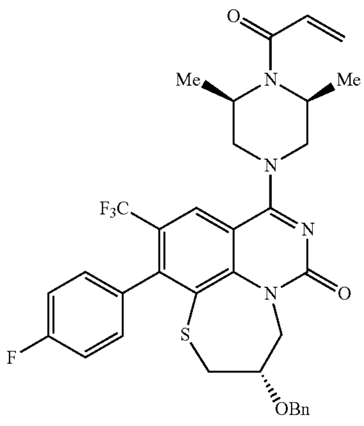 [SMILES: C=CC(=O)N1[C@H](C)CN(c2nc(=O)n3c4c(c(-c5ccc(F)cc5)c(C(F)(F)F)cc24)SC[C@@H](OCc2ccccc2)C3)C[C@@H]1C]

The title compound was prepared analogously to Example 84 where (S)-3-(benzyloxy)-8-((3S,5R)-3,5-dimethylpiperazin-1-yl)-11-(4-fluorophenyl)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 35% yield as a yellow solid. m/z (ESI, +ve)=653.2 $[M+H]^+$ Example 1004: (S)-8-(4-acryloylpiperazin-1-yl)-11-(4-fluorophenyl)-3-(methoxymethoxy)-10-(trifluoromethyl)-3,4-dihydro-2H,6H-[1,4]thiazepino[2,3,4-ij]quinazolin-6-one

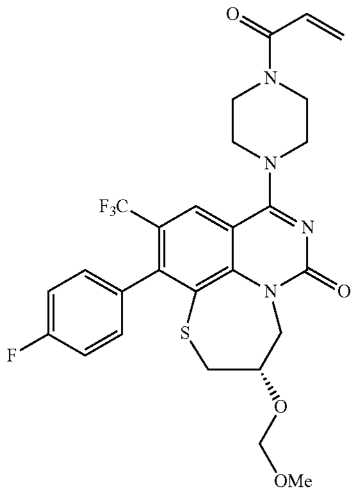 [SMILES: C=CC(=O)N1CCN(c2nc(=O)n3c4c(c(-c5ccc(F)cc5)c(C(F)(F)F)cc24)SC[C@@H](OCOC)C3)CC1]

The title compound was prepared analogously to Example 100, step 21 where (S)-7-(4-fluorophenyl)-8-((3-hydroxy-2-(methoxymethoxy)propyl)thio)-6-(trifluoromethyl)quinazoline-2,4(1H,3H)-dione and 1-(piperazin-1-yl)prop-2-en-1-one were substituted in place of 10-(2,4-difluorophenyl)-9-(trifluoromethyl)-2,3-dihydro-5H-[1,4]thiazino[2,3,4-ij]

quinazoline-5,7(6H)-dione and octahydrothieno[3,4-b]pyrazine 6,6-dioxide. The title compound was isolated in 48% yield as a pale yellow solid. m/z (ESI, +ve)=579.2 $[M+H]^+$ 1H NMR (400 MHz, DMSO-d6) δ 7.93 (s, 1H), 7.402-7.38 (m, 4H), 6.88 (dd, J=16.0, 8.0 Hz, 1H), 6.23 (dd, J=16.0, 4.0 Hz, 1H), 5.80 (dd, J=16.0, 4.0 Hz, 1H), 4.82-4.72 (m, 2H), 4.64-4.59 (m, 1H), 4.2.4-418 (m, 1H), 3.93-3.68 (m, 8H), 3.34 (s, 3H), 3.16-3.12 (m, 1H).

Step 1: (S)-1-((tert-butyldimethylsilyl)oxy)-3-(tritylthio)propan-2-ol

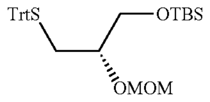

To a mixture of tert-butyl[(2S)-2-hydroxy-3-[(triphenylmethyl)sulfanyl]propoxy]dimethylsilane (25 g, 0.054 mol) and N, N-Diisopropylethylamine (20.9 g, 0.16 mol) in THF (250 mL) was slowly added bromo(methoxy)methane (13.4 g, 0.11 mol) at 0 C under N2. The mixture was stirred at 0° C. for 0.5 hours. The mixture was stirred at 50° C. for 6 hours, filtered off and the resulting filter cake was washed with ethyl acetate. The resulting organic solution was concentrated under reduced pressure to afford a residue that was purified by column chromatography on silica gel (0 to 70% ethyl acetate in hexanes) to afford the title compound in 70% yield as a yellow oil. m/z (ESI, +ve)=531.2 [M+Na]

Step 2: (S)-3-mercapto-2-(methoxymethoxy)propan-1-ol

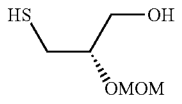

To a mixture of (5S)-8,8,9,9-tetramethyl-5-{[(triphenylmethyl)sulfanyl]methyl}-2,4,7-trioxa-8-siladecane (10 g, 0.020 mol) and triethylsilane (7.08 g, 0.061 mol) in dichloromethane (150 mL) was slowly added trifluoroacetic acid at 0° C. for an hour until the starting material was completely consumed. The reaction mixture was diluted with water and extracted with dichloromethane twice. The combined organic layers were washed with brine, dried over sodium sulfate and filtered. After evaporation of volatiles under reduced pressure, the crude product was purified by column chromatography on silica gel (0 to 15% methanol in dichloromethane) to afford the title compound in 58% yield as a colorless liquid.

$^1$H NMR (400 MHz, DMSO) δ=5.33 (s, 1H), 4.66-4.62 (m, 2H), 3.56-3.51 (m, 1H), 3.50-3.45 (m, 2H), 3.31-3.27 (m, 3H), 2.71-2.67 (m, 1H), 2.59-2.55 (m, 1H), 2.24-2.20 (m, 1H).

Step 3: (S)-7-(4-fluorophenyl)-8-((3-hydroxy-2-(methoxymethoxy)propyl)thio)-6-(trifluoromethyl)quinazoline-2,4(1H,3H)-dione

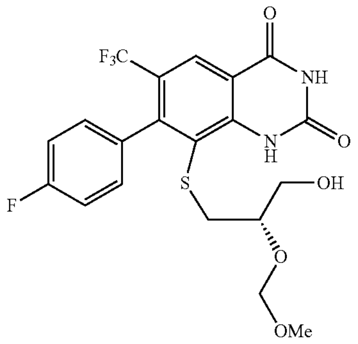 [SMILES: COCO[C@@H](CO)CSc1c(-c2ccc(F)cc2)c(C(F)(F)F)cc2c(=O)[nH]c(=O)[nH]c12]

The title compound was synthesized analogously to example 100, step 9 where 7-(4-fluorophenyl)-8-iodo-6-(trifluoromethyl)quinazoline-2,4(1H,3H)-dione and (S)-3-mercapto-2-(methoxymethoxy)propan-1-ol were substituted in place of 7-(2,4-difluorophenyl)-8-iodo-6-(trifluoromethyl)quinazoline-2,4(1H,3H)-dione and 2-mercaptoethan-1-ol. The title compound was isolated in 67% yield as a yellow solid. m/z (ESI, +ve)=497.0 [M+Na]

Step 4: (S)-11-(4-fluorophenyl)-3-(methoxymethoxy)-10-(trifluoromethyl)-3,4-dihydro-2H,6H-[1,4]thiazepino[2,3,4-ij]quinazoline-6,8(7H)-dione

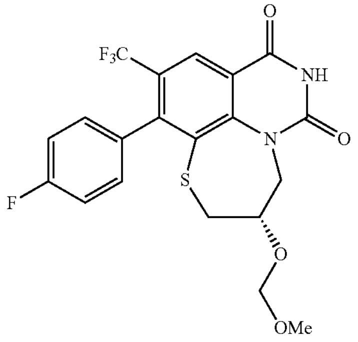 [SMILES: COCO[C@@H]1CSc2c(-c3ccc(F)cc3)c(C(F)(F)F)cc3c(=O)[nH]c(=O)n(c23)C1]

The title compound was prepared analogously to Example 100, step 10 where (S)-7-(4-fluorophenyl)-8-((3-hydroxy-2-(methoxymethoxy)propyl)thio)-6-(trifluoromethyl)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 80-% yield as a yellow solid. m/z (ESI, +ve)=557.2 $[M+H]^+$ Example 1005: (R)-8-(4-acryloylpiperazin-1-yl)-11-(4-fluorophenyl)-3-(methoxymethoxy)-10-(trifluoromethyl)-3,4-dihydro-2H,6H-[1,4]thiazepino[2,3,4-ij]quinazolin-6-one

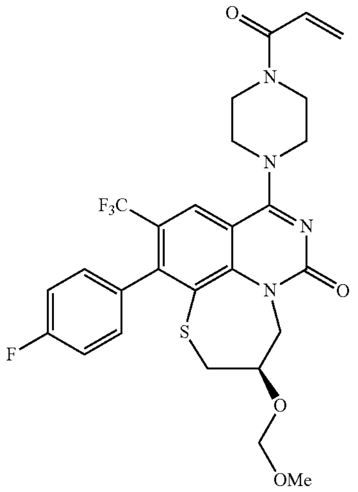 [SMILES: C=CC(=O)N1CCN(c2nc(=O)n3c4c(c(-c5ccc(F)cc5)c(C(F)(F)F)cc24)SC[C@H](OCOC)C3)CC1]

The title compound was prepared analogously to Example 100, step 21 where (R)-7-(4-fluorophenyl)-8-((3-hydroxy-2-(methoxymethoxy)propyl)thio)-6-(trifluoromethyl)quinazoline-2,4(1H,3H)-dione and 1-(piperazin-1-yl)prop-2-en-1-one were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 3% yield as a pale yellow solid. m/z (ESI, +ve)=579.2 $[M+H]^+$ 1H NMR (400 MHz, DMSO) δ 7.87 (s, 1H), 7.36-7.32 (m, 4H), 6.82 (dd, J=16.0, 8.0 Hz, 1H), 6.17 (dd, J=16.0, 4.0 Hz, 1H), 5.74 (dd, 16.0, 4.0 Hz, 1H), 4.74-4.63 (m, 2H), 4.61-4.51 (m, 1H), 4.15-4.12 (m, 1H), 3.88-3.65 (m, 7H), 3.48-3.36 (m, 1H), 3.32 (s, 3H), 3.32-3.28 (m, 3H), 3.10-3.06 (m, 1H).

Step 1: (R)-11-(4-fluorophenyl)-3-(methoxymethoxy)-10-(trifluoromethyl)-3,4-dihydro-2H,6H-[1,4]thiazepino[2,3,4-ij]quinazoline-6,8(7H)-dione

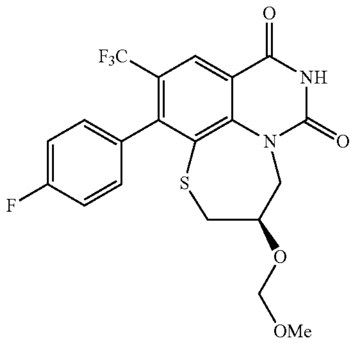 [SMILES: COCO[C@H]1CSc2c(-c3ccc(F)cc3)c(C(F)(F)F)cc3c(=O)[nH]c(=O)n(c23)C1]

The title compound was synthesized analogously to example 4, steps 1~4 where tert-butyl[(2R)-2-hydroxy-3-

[(triphenylmethyl)sulfanyl]propoxy]dimethylsilane in step 1 was substituted in place of tert-butyl[(2S)-2-hydroxy-3-[(triphenylmethyl)sulfanyl]propoxy]dimethylsilane. m/z (ESI, +ve)=557.2 [M+H]$^+$ Example 1006: (R)-8-(4-acryloylpiperazin-1-yl)-11-(3-chloro-4-fluorophenyl)-3-(methoxymethoxy)-10-(trifluoromethyl)-3,4-dihydro-2H,6H-[1,4]thiazepino[2,3,4-ij]quinazolin-6-one

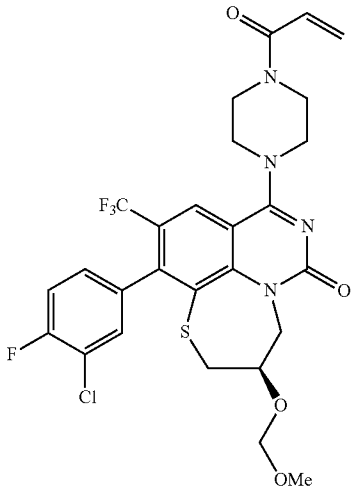 [SMILES: C=CC(=O)N1CCN(c2nc(=O)n3c4c(c(-c5ccc(F)c(Cl)c5)c(C(F)(F)F)cc24)SC[C@H](OCOC)C3)CC1]

The title compound was prepared analogously to Example 100, step 21 where (R)-11-(3-chloro-4-fluorophenyl)-3-(methoxymethoxy)-10-(trifluoromethyl)-3,4-dihydro-2H,6H-[1,4]thiazepino[2,3,4-ij]quinazoline-6,8(7H)-dione and 1-(piperazin-1-yl)prop-2-en-1-one were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 30% yield as a pale yellow solid. m/z (ESI, +ve)=613.2 [M+H]$^+$ $^1$H NMR (400 MHz, DMSO-$d_6$) δ 7.88 (s, 1H), 7.66-7.56 (m, 2H), 7.39-7.31 (m, 1H), 6.83 (dd, J=16.0, 8.0 Hz, 1H), 6.17 (dd, J=16.0, 4.0 Hz, 1H), 5.74 (dd, J=16.0, 4.0 Hz, 1H), 4.69-4.65 (m, 2H), 4.51-4.54 (m, 1H), 4.18-4.14 (m, 1H), 3.80-3.37 (m, 10H), 3.28-3.23 (m, 3H), 3.15-3.08 (m, 1H).

Step 1: Methyl 3-amino-3'-chloro-4'-fluoro-[1,1'-biphenyl]-4-carboxylate

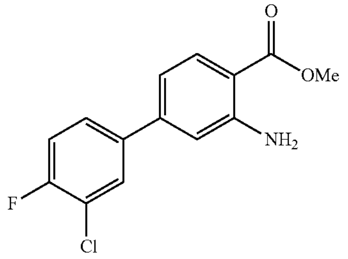 [SMILES: COC(=O)c1ccc(-c2ccc(F)c(Cl)c2)cc1N]

The title compound was synthesized analogously to example 100, step 1 where (3-chloro-4-fluorophenyl)boronic acid was substituted in place of (2,4-difluorophenyl)

boronic acid. The title compound was isolated in 92% yield as a brown solid. m/z (ESI, +ve)=280.1 [M+H]$^+$ Step 2: Methyl 5-amino-3'-chloro-4'-fluoro-2-iodo-[1,1'-biphenyl]-4-carboxylate

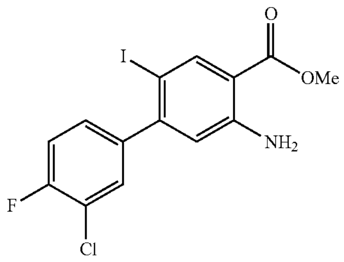 [SMILES: COC(=O)c1cc(I)c(-c2ccc(F)c(Cl)c2)cc1N]

The title compound was synthesized analogously to example 100, step 2 where Methyl 3-amino-3'-chloro-4'-fluoro-[1,1'-biphenyl]-4-carboxylate was substituted in place of methyl 3-amino-2',4'-difluoro-[1,1'-biphenyl]-4-carboxylate. The title compound was isolated in 91% yield as a brown solid. m/z (ESI, +ve)=406.0 [M+H]$^+$ Step 3: Methyl 5-acetamido-3'-chloro-4'-fluoro-2-iodo-[1,1'-biphenyl]-4-carboxylate

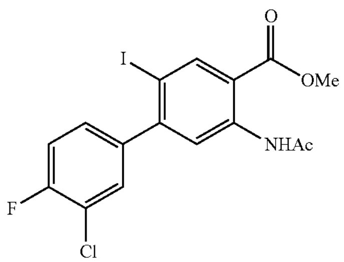 [SMILES: COC(=O)c1cc(I)c(-c2ccc(F)c(Cl)c2)cc1NC(C)=O]

The title compound was synthesized analogously to example 100, step 3 where methyl 5-amino-3'-chloro-4'-fluoro-2-iodo-[1,1'-biphenyl]-4-carboxylate was substituted in place of 2-amino-4-(2,4-difluorophenyl)-5-iodobenzoate. The title compound was isolated in 98% yield as a brown solid. m/z (ESI, +ve)=414.0 [M+H]$^+$ Step 4: Methyl 5-acetamido-3'-chloro-4'-fluoro-2-(trifluoromethyl)-[1,1'-biphenyl]-4-carboxylate

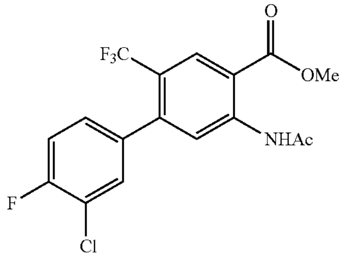 [SMILES: COC(=O)c1cc(C(F)(F)F)c(-c2ccc(F)c(Cl)c2)cc1NC(C)=O]

The title compound was synthesized analogously to example 100, step 4 where methyl 5-acetamido-3'-chloro- 4'-fluoro-2-iodo-[1,1'-biphenyl]-4-carboxylate was substituted in place of methyl 4-(2,4-difluorophenyl)-2-acetamido-5-iodobenzoate. The title compound was isolated in 41% yield as a yellow solid. m/z (ESI, +ve)=390.0 $[M+H]^+$ Step 5: methyl 5-amino-3'-chloro-4'-fluoro-2-(trifluoromethyl)-[1,1'-biphenyl]-4-carboxylate

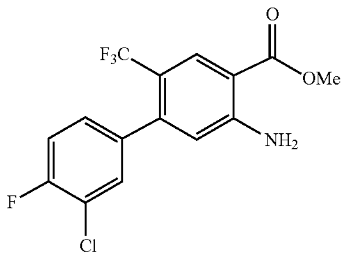 [SMILES: COC(=O)c1cc(C(F)(F)F)c(-c2ccc(F)c(Cl)c2)cc1N]

The title compound was synthesized analogously to example 100, step 5 where Methyl 5-acetamido-3'-chloro-4'-fluoro-2-(trifluoromethyl)-[1,1'-biphenyl]-4-carboxylate was substituted in place of methyl 5-acetamido-2',4'-difluoro-2-(trifluoromethyl)-[1,1'-biphenyl]-4-carboxylate. The title compound was isolated in 97% yield as a white solid. m/z (ESI, +ve)=348.0 $[M+H]^+$ Step 6: methyl 3-amino-3'-chloro-4'-fluoro-2-iodo-6-(trifluoromethyl)-[1,1'-biphenyl]-4-carboxylate

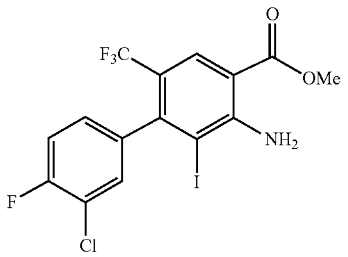 [SMILES: COC(=O)c1cc(C(F)(F)F)c(-c2ccc(F)c(Cl)c2)c(I)c1N]

The title compound was synthesized analogously to example 100, step 6 where methyl 5-amino-3'-chloro-4'-fluoro-2-(trifluoromethyl)-[1,1'-biphenyl]-4-carboxylate was substituted in place of methyl 5-amino-2',4'-difluoro-2-(trifluoromethyl)-[1,1'-biphenyl]-4-carboxylate. The title compound was isolated in 75% yield as a white solid. m/z (ESI, +ve)=473.9 $[M+H]^+$ Step 7: 3-amino-3'-chloro-4'-fluoro-2-iodo-6-(trifluoromethyl)-[1,1'-biphenyl]-4-carboxylic acid

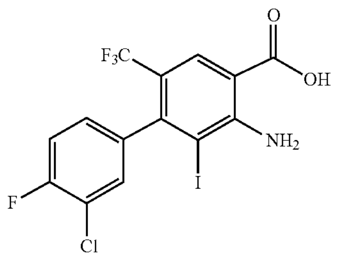 [SMILES: Nc1c(C(=O)O)cc(C(F)(F)F)c(-c2ccc(F)c(Cl)c2)c1I]

The title compound was synthesized analogously to example 100, step 7 where methyl 3-amino-3'-chloro-4'-fluoro-2-iodo-6-(trifluoromethyl)-[1,1'-biphenyl]-4-carboxylate was substituted in place of methyl 3-amino-2',4'-difluoro-2-iodo-6-(trifluoromethyl)-[1,1'-biphenyl]-4-carboxylate. The title compound was isolated in 95% yield as a brown solid. m/z (ESI, +ve)=459.9 $[M+H]^+$ Step 8: 7-(3-chloro-4-fluorophenyl)-8-iodo-6-(trifluoromethyl)quinazoline-2,4(1H,3H)-dione

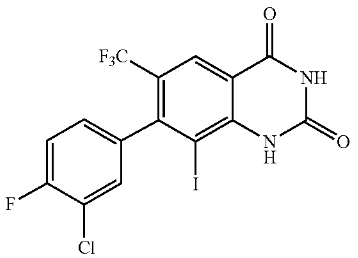 [SMILES: O=c1[nH]c(=O)c2cc(C(F)(F)F)c(-c3ccc(F)c(Cl)c3)c(I)c2[nH]1]

The title compound was synthesized analogously to example 100, step 8 where 3-amino-3'-chloro-4'-fluoro-2-iodo-6-(trifluoromethyl)-[1,1'-biphenyl]-4-carboxylic acid was substituted in place of 3-amino-2',4'-difluoro-2-iodo-6-(trifluoromethyl)-[1,1'-biphenyl]-4-carboxylic acid. The title compound was isolated in 45% yield as a pale brown solid. m/z (ESI, +ve)=484.7 $[M+H]^+$ Step 9: (R)-7-(3-chloro-4-fluorophenyl)-8-((3-hydroxy-2-(methoxymethoxy)propyl)thio)-6-(trifluoromethyl)quinazoline-2,4(1H,3H)-dione

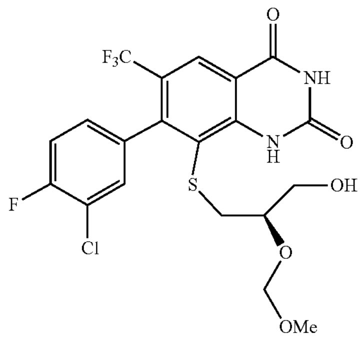 [SMILES: COCO[C@H](CO)CSc1c(-c2ccc(F)c(Cl)c2)c(C(F)(F)F)cc2c(=O)[nH]c(=O)[nH]c12]

The title compound was synthesized analogously to example 100, step 9 where 7-(3-chloro-4-fluorophenyl)-8-iodo-6-(trifluoromethyl)quinazoline-2,4(1H,3H)-dione and (R)-3-mercapto-2-(methoxymethoxy)propan-1-ol was substituted in place of 7-(2,4-difluorophenyl)-8-iodo-6-(trifluoromethyl)quinazoline-2,4(1H,3H)-dione and 2-mercaptoethan-1-ol. The title compound was isolated in 85% yield as a white solid. m/z (ESI, +ve)=509.0 $[M+H]^+$ Step 10: (R)-11-(3-chloro-4-fluorophenyl)-3-(methoxymethoxy)-10-(trifluoromethyl)-3,4-dihydro-2H,6H-[1,4]thiazepino[2,3,4-ij]quinazoline-6,8(7H)-dione

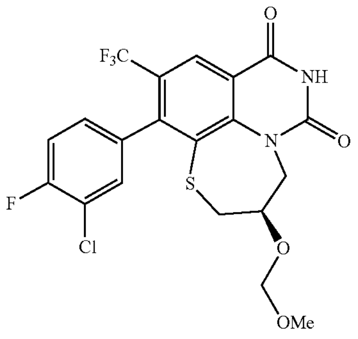 [SMILES: COCO[C@H]1CSc2c(-c3ccc(F)c(Cl)c3)c(C(F)(F)F)cc3c(=O)[nH]c(=O)n(c23)C1]

The title compound was prepared analogously to Example 100, step 10 where (R)-7-(3-chloro-4-fluorophenyl)-8-((3-hydroxy-2-(methoxymethoxy)propyl)thio)-6-(trifluoromethyl)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 50% yield as a yellow solid. m/z (ESI, +ve)=491.0 $[M+H]^+$ Example 1007: (S)-8-(4-acryloylpiperazin-1-yl)-11-(3-chloro-4-fluorophenyl)-3-(methoxymethoxy)-10-(trifluoromethyl)-3,4-dihydro-2H,6H-[1,4]thiazepino[2,3,4-ij]quinazolin-6-one

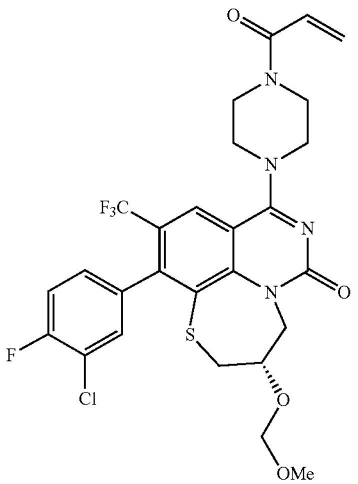 [SMILES: C=CC(=O)N1CCN(c2nc(=O)n3c4c(c(-c5ccc(F)c(Cl)c5)c(C(F)(F)F)cc24)SC[C@@H](OCOC)C3)CC1]

The title compound was prepared analogously to Example 100, step 21 where (S)-11-(3-chloro-4-fluorophenyl)-3-(methoxymethoxy)-10-(trifluoromethyl)-3,4-dihydro-2H,6H-[1,4]thiazepino[2,3,4-ij]quinazoline-6,8(7H)-dione and 1-(piperazin-1-yl)prop-2-en-1-one were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 40% yield as a pale yellow solid. m/z (ESI, +ve)=613.2 $[M+H]^+$ 1H NMR (400 MHz, DMSO) δ 7.88 (s, 1H), 7.72-7.51 (m, 2H), 7.38-7.32 (m, 1H), 6.82 (dd, J=16.0, 8.0 Hz, 1H), 6.17 (d, J=16.0, 4.0 Hz, 1H), 5.74 (dd, J=16.0, 4.0 Hz, 1H), 4.77-4.63 (m, 2H), 4.58-4.54 (m, 1H), 4.18-4.14 (m, 1H), 3.87-3.68 (m, 7H), 3.53-3.54 (m, 1H), 3.35-3.18 (m, 5H), 3.17-3.04 (m, 1H).

Step 1: (S)-7-(3-chloro-4-fluorophenyl)-8-((3-hydroxy-2-(methoxymethoxy)propyl)thio)-6-(trifluoromethyl)quinazoline-2,4(1H,3H)-dione

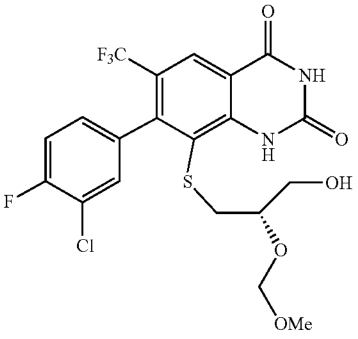 [SMILES: COCO[C@@H](CO)CSc1c(-c2ccc(F)c(Cl)c2)c(C(F)(F)F)cc2c(=O)[nH]c(=O)[nH]c12]

The title compound was synthesized analogously to example 100, step 9 where 7-(3-chloro-4-fluorophenyl)-8-iodo-6-(trifluoromethyl)quinazoline-2,4(1H,3H)-dione and (S)-3-mercapto-2-(methoxymethoxy)propan-1-ol was substituted in place of 7-(2,4-difluorophenyl)-8-iodo-6-(trifluoromethyl)quinazoline-2,4(1H,3H)-dione and 2-mercaptoethan-1-ol. The title compound was isolated in 85% yield as a white solid. m/z (ESI, +ve)=509.0 $[M+H]^+$ Step 2: (S)-11-(3-chloro-4-fluorophenyl)-3-(methoxymethoxy)-10-(trifluoromethyl)-3,4-dihydro-2H,6H-[1,4]thiazepino[2,3,4-ij]quinazoline-6,8(7H)-dione

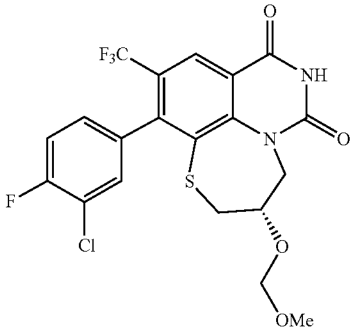 [SMILES: COCO[C@@H]1CSc2c(-c3ccc(F)c(Cl)c3)c(C(F)(F)F)cc3c(=O)[nH]c(=O)n(c23)C1]

The title compound was prepared analogously to Example 100, step 10 where (S)-7-(3-chloro-4-fluorophenyl)-8-((3-hydroxy-2-(methoxymethoxy)propyl)thio)-6-(trifluoromethyl)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 80% yield as a yellow solid. m/z (ESI, +ve)=491.0 $[M+H]^+$ Example 1008: (3R)-8-(4-acryloylpiperazin-1-yl)-11-(5-chloro-2,4-difluorophenyl)-3-(methoxymethoxy)-10-(trifluoromethyl)-3,4-dihydro-2H,6H-[1,4]thiazepino[2,3,4-ij]quinazolin-6-one

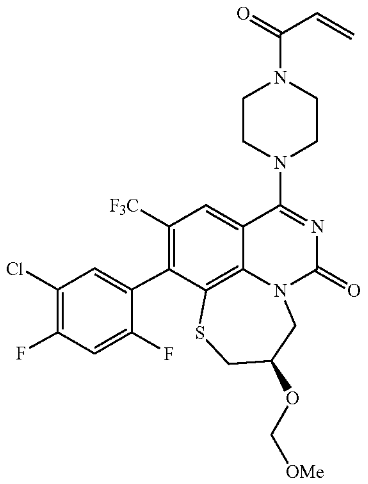 [SMILES: C=CC(=O)N1CCN(c2nc(=O)n3c4c(c(-c5cc(Cl)c(F)cc5F)c(C(F)(F)F)cc24)SC[C@H](OCOC)C3)CC1]

The title compound was prepared analogously to Example 100, step 21 where (3R)-11-(5-chloro-2,4-difluorophenyl)-3-(methoxymethoxy)-8-methylene-10-(trifluoromethyl)-3,4,7,8-tetrahydro-2H,6H-[1,4]thiazepino[2,3,4-ij]quinazolin-6-one and 1-(piperazin-1-yl)prop-2-en-1-one were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 13% yield as a pale yellow solid. m/z (ESI, +ve)=631.1 [M+H]$^+$ $^1$H NMR (400 MHz, DMSO-$d_6$) δ 7.91 (s, 1H), 7.81-7.75 (m, 2H), 6.82 (dd, J=16.0, 8.0 Hz, 1H), 6.17 (dd, J=16.0, 4.0 Hz, 1H), 5.74 (dd, J=16.0, 4.0 Hz, 1H), 4.74-4.66 (m, 2H), 4.55-4.52 (m, 1H), 4.20-4.16 (m, 1H), 3.92-3.66 (m, 8H), 3.31-3.27 (m, 4H), 3.20-3.13 (m, 1H).

Step 1: 7-(5-chloro-2,4-difluorophenyl)-8-(((R)-3-hydroxy-2-(methoxymethoxy)propyl)thio)-6-(trifluoromethyl)quinazoline-2,4(1H,3H)-dione

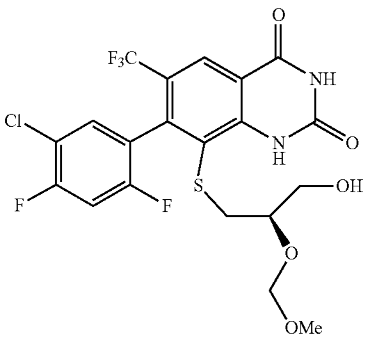 [SMILES: COCO[C@H](CO)CSc1c(-c2cc(Cl)c(F)cc2F)c(C(F)(F)F)cc2c(=O)[nH]c(=O)[nH]c12]

The title compound was synthesized analogously to example 100, step 9 where 7-(5-chloro-2,4-difluorophenyl)-8-iodo-6-(trifluoromethyl)quinazoline-2,4(1H,3H)-dione (R)-3-mercapto-2-(methoxymethoxy)propan-1-ol were substituted in place of 7-(2,4-difluorophenyl)-8-iodo-6-(trifluoromethyl)quinazoline-2,4(1H,3H)-dione and 2-mercaptoethan-1-ol. The title compound was isolated in 80% yield as a white solid. m/z (ESI, +ve)=527.0 [M+H]$^+$ Step 2: (3R)-11-(5-chloro-2,4-difluorophenyl)-3-(methoxymethoxy)-10-(trifluoromethyl)-3,4-dihydro-2H,6H-[1,4]thiazepino[2,3,4-ij]quinazoline-6,8(7H)-dione

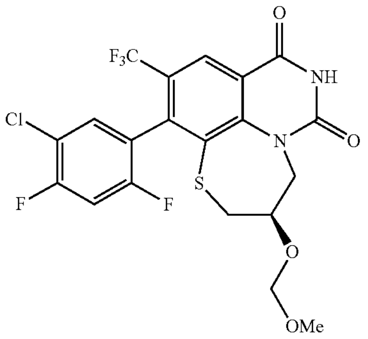 [SMILES: COCO[C@H]1CSc2c(-c3cc(Cl)c(F)cc3F)c(C(F)(F)F)cc3c(=O)[nH]c(=O)n(c23)C1]

The title compound was prepared analogously to Example 100, step 10 where 7-(5-chloro-2,4-difluorophenyl)-8-(((R)-3-hydroxy-2-(methoxymethoxy)propyl)thio)-6-(trifluoromethyl)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 71% yield as a yellow solid. m/z (ESI, +ve)=509.1 [M+H]$^+$ Example 1009: (R)-8-((3S,5R)-4-acryloyl-3,5-dimethylpiperazin-1-yl)-11-(4-fluorophenyl)-3-(methoxymethoxy)-10-(trifluoromethyl)-3,4-dihydro-2H,6H-[1,4]thiazepino[2,3,4-ij]quinazolin-6-one

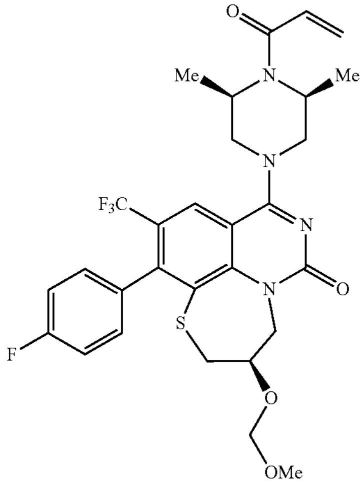 [SMILES: C=CC(=O)N1[C@H](C)CN(c2nc(=O)n3c4c(c(-c5ccc(F)cc5)c(C(F)(F)F)cc24)SC[C@H](OCOC)C3)C[C@@H]1C]

The title compound was prepared analogously to Example 84 where (R)-8-((3S,5R)-3,5-dimethylpiperazin-1-yl)-11-(4-fluorophenyl)-3-(methoxymethoxy)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 82% yield as a yellow solid. m/z (ESI, +ve)=553.2 [M+H]$^+$ Step 1: (R)-8-((3S,5R)-3,5-dimethylpiperazin-1-yl)-11-(4-fluorophenyl)-3-(methoxymethoxy)-10-(trifluoromethyl)-3,4-dihydro-2H,6H-[1,4]thiazepino[2,3,4-ij]quinazolin-6-one

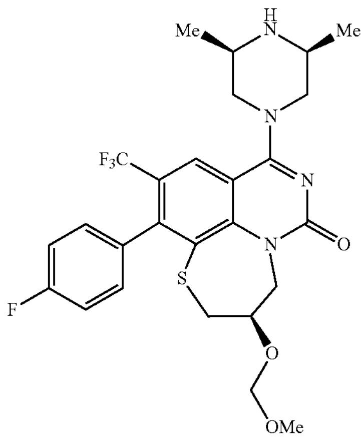 [SMILES: COCO[C@H]1CSc2c(-c3ccc(F)cc3)c(C(F)(F)F)cc3c(N4C[C@@H](C)N[C@@H](C)C4)nc(=O)n(c23)C1]

The title compound was prepared analogously to Example 100, step 21 where 7-(4-fluorophenyl)-8-iodo-6-(trifluoromethyl)quinazoline-2,4(1H,3H)-dione and (2R,6S)-2,6-dimethylpiperazine were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 82% yield as a yellow solid. m/z (ESI, +ve)=553.2 [M+H]$^+$ Example 1010: (S)-8-((3S,5R)-4-acryloyl-3,5-dimethylpiperazin-1-yl)-11-(4-fluorophenyl)-3-(methoxymethoxy)-10-(trifluoromethyl)-3,4-dihydro-2H,6H-[1,4]thiazepino[2,3,4-ij]quinazolin-6-one

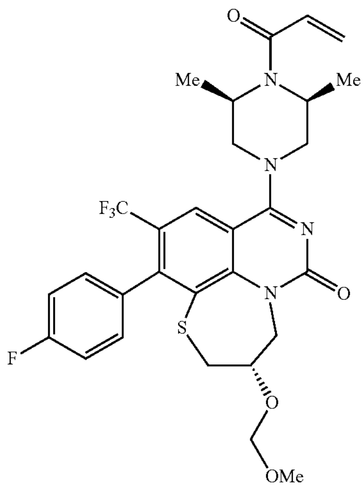 [SMILES: C=CC(=O)N1[C@H](C)CN(c2nc(=O)n3c4c(c(-c5ccc(F)cc5)c(C(F)(F)F)cc24)SC[C@@H](OCOC)C3)C[C@@H]1C]

The title compound was prepared analogously to Example 84 where (R)-8-((3S,5R)-3,5-dimethylpiperazin-1-yl)-11-(4-fluorophenyl)-3-(methoxymethoxy)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 82% yield as a yellow solid. m/z (ESI, +ve)=607.0 [M+H]$^+$ 1H NMR (400 MHz, DMSO) δ 8.02 (s, 1H), 7.51-7.16 (m, 4H), 6.81 (dd, J=16.0, 8.0 Hz, 1H), 6.19 (dd, J=16.0, 4.0 Hz, 1H), 5.74 (dd, J=16.0, 4.0 Hz, 1H), 4.69-4.65 (m, 2H), 4.65-4.49 (m, 3H), 4.19-4.15 (m, 1H), 4.09-4.05 (m, 2H), 3.37-3.32 (m, 3H), 3.29-3.26 (m, 3H), 3.26-3.21 (m, 1H), 3.10-3.05 (m, 1H), 1.40 (s, 6H).

Step 1: (S)-8-((3S,5R)-3,5-dimethylpiperazin-1-yl)-11-(4-fluorophenyl)-3-(methoxymethoxy)-10-(trifluoromethyl)-3,4-dihydro-2H,6H-[1,4]thiazepino[2,3,4-ij]quinazolin-6-one

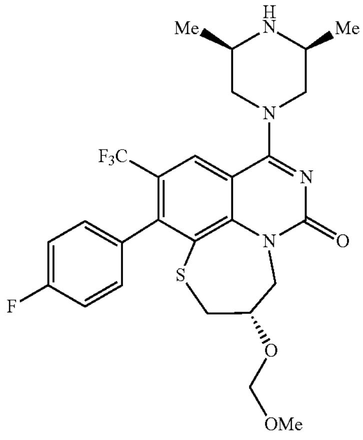 [SMILES: COCO[C@@H]1CSc2c(-c3ccc(F)cc3)c(C(F)(F)F)cc3c(N4C[C@@H](C)N[C@@H](C)C4)nc(=O)n(c23)C1]

The title compound was prepared analogously to Example 100, step 21 where (S)-11-(4-fluorophenyl)-3-(methoxymethoxy)-10-(trifluoromethyl)-3,4-dihydro-2H,6H-[1,4]thiazepino[2,3,4-ij]quinazoline-6,8(7H)-dione and (2R,6S)-2,6-dimethylpiperazine were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 70% yield as a yellow solid. m/z (ESI, +ve)=553.1 [M+H]$^+$ Example 1011: (3R)-8-((3S,5R)-4-acryloyl-3,5-dimethylpiperazin-1-yl)-11-(2,4-difluorophenyl)-3-(methoxymethoxy)-10-(trifluoromethyl)-3,4-dihydro-2H,6H-[1,4]thiazepino[2,3,4-ij]quinazolin-6-one

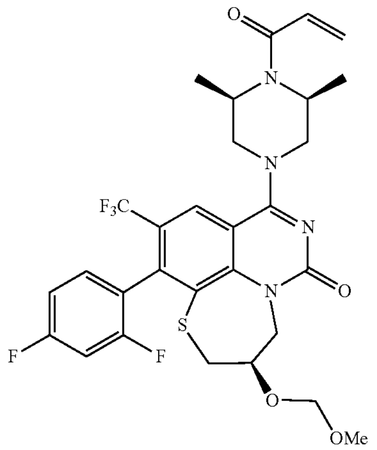 [SMILES: C=CC(=O)N1[C@H](C)CN(c2nc(=O)n3c4c(c(-c5ccc(F)cc5F)c(C(F)(F)F)cc24)SC[C@H](OCOC)C3)C[C@@H]1C]

The title compound was prepared analogously to Example 84 where (3R)-11-(2,4-difluorophenyl)-8-((3S,5R)-3,5-dimethylpiperazin-1-yl)-3-(methoxymethoxy)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 10% yield as a white solid. m/z (ESI, +ve)=625.2 $[M+H]^+$ 1H NMR (400 MHz, DMSO) δ 8.05 (s, 1H), 7.51-7.33 (m, 2H), 7.29-7.25 (m, 1H), 6.81 (dd, J=16.0, 8.0 Hz, 1H), 6.19 (dd, J=16.0, 4.0 Hz, 1H), 5.74 (dd, J=16.0, 4.0 Hz, 1H), 4.60-4.55 (m, 5H), 4.21-4.17 (m, 1H), 4.09-4.05 (m, 2H), 3.36-3.32 (m, 3H), 3.30-3.26 (m, 3H), 3.26-3.22 (m, 1H), 3.15-3.11 (m, 1H), 1.43-1.37 (m, 6H).

Step 1: 7-(2,4-difluorophenyl)-8-(((R)-3-hydroxy-2-(methoxymethoxy)propyl)thio)-6-(trifluoromethyl)quinazoline-2,4(1H,3H)-dione

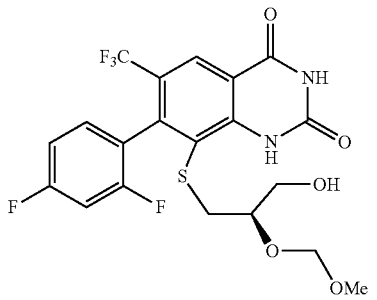 [SMILES: COCO[C@H](CO)CSc1c(-c2ccc(F)cc2F)c(C(F)(F)F)cc2c(=O)[nH]c(=O)[nH]c12]

The title compound was prepared analogously to Example 100, step 9 where 7-(2,4-difluorophenyl)-8-iodo-6-(trifluoromethyl)quinazoline-2,4(1H,3H)-dione and (R)-3-mercapto-2-(methoxymethoxy)propan-1-ol were substituted in place of 7-(2,4-difluorophenyl)-8-iodo-6-(trifluoromethyl)quinazoline-2,4(1H,3H)-dione and 2-mercaptoethan-1-ol. The title compound was isolated in 75% yield as a yellow solid. m/z (ESI, +ve)=493.1 $[M+H]^+$ Step 2: (3R)-11-(2,4-difluorophenyl)-3-(methoxymethoxy)-10-(trifluoromethyl)-3,4-dihydro-2H,6H-[1,4]thiazepino[2,3,4-ij]quinazoline-6,8(7H)-dione

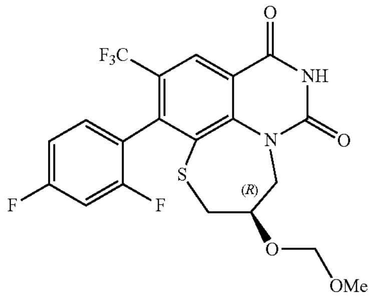

The title compound was prepared analogously to Example 100, step 10 where 7-(2,4-difluorophenyl)-8-(((R)-3-hydroxy-2-(methoxymethoxy)propyl)thio)-6-(trifluoromethyl)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 87% yield as a yellow solid. m/z (ESI, +ve)=475.0 $[M+H]^+$ Step 3: (3R)-11-(2,4-difluorophenyl)-8-((3S,5R)-3,5-dimethylpiperazin-1-yl)-3-(methoxymethoxy)-10-(trifluoromethyl)-3,4-dihydro-2H,6H-[1,4]thiazepino[2,3,4-ij]quinazolin-6-one

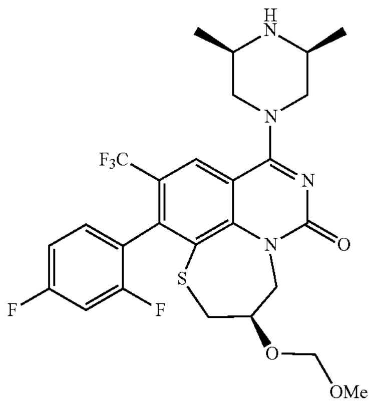 [SMILES: COCO[C@H]1CSc2c(-c3ccc(F)cc3F)c(C(F)(F)F)cc3c(N4C[C@@H](C)N[C@@H](C)C4)nc(=O)n(c23)C1]

The title compound was prepared analogously to Example 100, step 21 where (3R)-11-(2,4-difluorophenyl)-3-(methoxymethoxy)-10-(trifluoromethyl)-3,4-dihydro-2H,6H-[1,4]thiazepino[2,3,4-ij]quinazoline-6,8(7H)-dione and (2R,6S)-2,6-dimethylpiperazine were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 45% yield as a yellow solid. m/z (ESI, +ve)=571.2 $[M+H]^+$ Example 1012: (3S)-8-((3S,5R)-4-acryloyl-3,5-dimethylpiperazin-1-yl)-11-(2,4-difluorophenyl)-3-(methoxymethoxy)-10-(trifluoromethyl)-3,4-dihydro-2H,6H-[1,4]thiazepino[2,3,4-ij]quinazolin-6-one

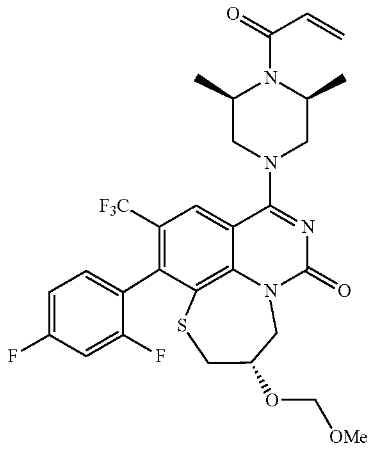 [SMILES: C=CC(=O)N1[C@H](C)CN(c2nc(=O)n3c4c(c(-c5ccc(F)cc5F)c(C(F)(F)F)cc24)SC[C@@H](OCOC)C3)C[C@@H]1C]

The title compound was prepared analogously to Example 84 where (3S)-11-(2,4-difluorophenyl)-3-(methoxymethoxy)-10-(trifluoromethyl)-3,4-dihydro-2H,6H-[1,4]thiazepino[2,3,4-ij]quinazoline-6,8(7H)-dione was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 31% yield as a white solid. m/z (ESI, +ve)=625.1 $[M+H]^+$ 1H NMR (400 MHz, DMSO) δ 8.05 (s, 1H), 7.53-7.35 (m, 2H), 7.29-7.25 (m, 1H), 6.81 (dd, J=16.0, 8.0 Hz, 1H), 6.19 (dd, J=16.0, 4.0 Hz, 1H), 5.74 (dd, J=16.0, 4.0 Hz, 1H), 4.60-4.55 (m, 6H), 4.19 (s, 1H), 4.10-4.05 (m, 2H), 3.61-3.57 (m, 1H), 3.30-3.26 (m, 5H), 3.15-3.11 (m, 1H), 1.40 (d, J=12.0 Hz, 6H).

Step 1: 7-(2,4-difluorophenyl)-8-(((S)-3-hydroxy-2-(methoxymethoxy)propyl)thio)-6-(trifluoromethyl)quinazoline-2,4(1H,3H)-dione

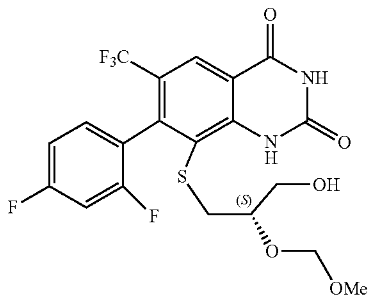

The title compound was prepared analogously to Example 100, step 9 where 7-(2,4-difluorophenyl)-8-iodo-6-(trifluoromethyl)quinazoline-2,4(1H,3H)-dione and (S)-3-mercapto-2-(methoxymethoxy)propan-1-ol were substituted in place of 7-(2,4-difluorophenyl)-8-iodo-6-(trifluoromethyl)quinazoline-2,4(1H,3H)-dione and 2-mercaptoethan-1-ol. The title compound was isolated in 68% yield as a yellow solid. m/z (ESI, +ve)=493.1 $[M+H]^+$ Step 2: (3S)-11-(2,4-difluorophenyl)-8-((3S,5R)-3,5-dimethylpiperazin-1-yl)-3-(methoxymethoxy)-10-(trifluoromethyl)-3,4-dihydro-2H,6H-[1,4]thiazepino[2,3,4-ij]quinazolin-6-one

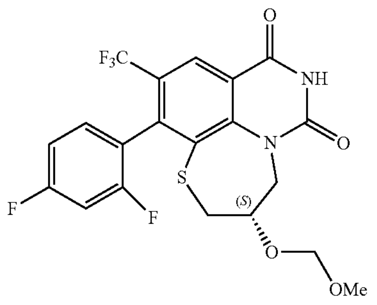

The title compound was prepared analogously to Example 100, step 10 where 7-(2,4-difluorophenyl)-8-(((S)-3-hydroxy-2-(methoxymethoxy)propyl)thio)-6-(trifluoromethyl)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 69% yield as a yellow solid. m/z (ESI, +ve)=475.1 $[M+H]^+$ Step 3: (3S)-11-(2,4-difluorophenyl)-3-(methoxymethoxy)-10-(trifluoromethyl)-3,4-dihydro-2H,6H-[1,4]thiazepino[2,3,4-ij]quinazoline-6,8(7H)-dione

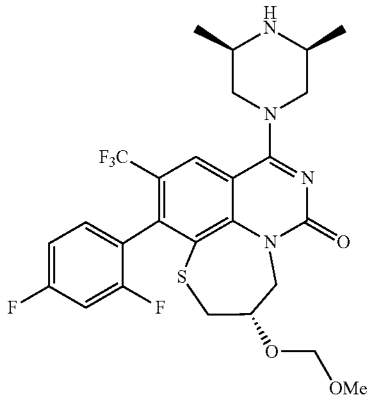 [SMILES: COCO[C@@H]1CSc2c(-c3ccc(F)cc3F)c(C(F)(F)F)cc3c(N4C[C@@H](C)N[C@@H](C)C4)nc(=O)n(c23)C1]

The title compound was prepared analogously to Example 100, step 21 where (3S)-11-(2,4-difluorophenyl)-8-((3S,5R)-3,5-dimethylpiperazin-1-yl)-3-(methoxymethoxy)-10-(trifluoromethyl)-3,4-dihydro-2H,6H-[1,4]thiazepino[2,3,4-ij]quinazolin-6-one (2R,6S)-2,6-dimethylpiperazine were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 62% yield as a yellow solid. m/z (ESI, +ve)=571.1 $[M+H]^+$ Example 1013: (R)-8-((3S,5R)-4-acryloyl-3,5-dimethylpiperazin-1-yl)-11-(3-chloro-4-fluorophenyl)-3-(methoxymethoxy)-10-(trifluoromethyl)-3,4-dihydro-2H,6H-[1,4]thiazepino[2,3,4-ij]quinazolin-6-one

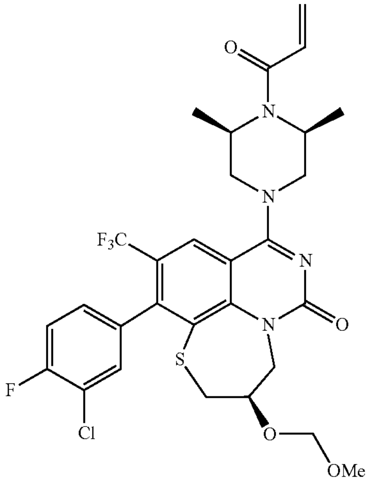 [SMILES: C=CC(=O)N1[C@H](C)CN(c2nc(=O)n3c4c(c(-c5ccc(F)c(Cl)c5)c(C(F)(F)F)cc24)SC[C@H](OCOC)C3)C[C@@H]1C]

The title compound was prepared analogously to Example 84 where (R)-11-(3-chloro-4-fluorophenyl)-8-((3S,5R)-3,5-dimethylpiperazin-1-yl)-3-(methoxymethoxy)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 27% yield as a pale yellow solid. m/z (ESI, +ve)=641.2 $[M+H]^+$ $^1H$ NMR (400 MHz, DMSO-$d_6$) δ 8.03 (s, 1H), 7.65-7.56 (m, 2H), 7.39-7.31 (m, 1H), 6.82 (dd, J=16.0, 8.0 Hz, 1H), 6.20 (dd, J=16.0, 4.0 Hz, 1H), 5.75 (dd, J=16.0, 4.0 Hz, 1H), 4.68-4.52 (m, 6H), 4.21-4.17 (m, 1H), 4.09-4.05 (m, 2H), 3.28-3.26 (m, 6H), 3.15-3.07 (m, 1H), 1.40 (s, 6H).

Step 1: (R)-11-(3-chloro-4-fluorophenyl)-8-((3S,5R)-3,5-dimethylpiperazin-1-yl)-3-(methoxymethoxy)-10-(trifluoromethyl)-3,4-dihydro-2H,6H-[1,4]thiazepino[2,3,4-ij]quinazolin-6-one

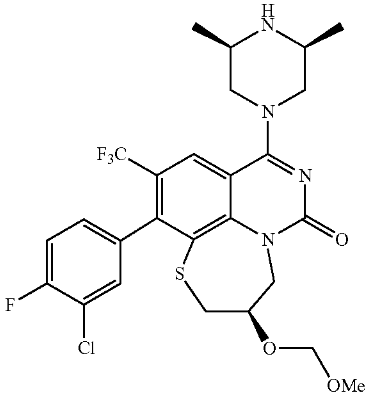 [SMILES: COCO[C@H]1CSc2c(-c3ccc(F)c(Cl)c3)c(C(F)(F)F)cc3c(N4C[C@@H](C)N[C@@H](C)C4)nc(=O)n(c23)C1]

The title compound was prepared analogously to Example 100, step 21 where (R)-11-(3-chloro-4-fluorophenyl)-3-(methoxymethoxy)-10-(trifluoromethyl)-3,4-dihydro-2H,6H-[1,4]thiazepino[2,3,4-ij]quinazoline-6,8(7H)-dione and (2R,6S)-2,6-dimethylpiperazine were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 82% yield as a pale yellow solid. m/z (ESI, +ve)=587.1 $[M+H]^+$ Example 1014: (S)-8-((3S,5R)-4-acryloyl-3,5-dimethylpiperazin-1-yl)-11-(3-chloro-4-fluorophenyl)-3-(methoxymethoxy)-10-(trifluoromethyl)-3,4-dihydro-2H,6H-[1,4]thiazepino[2,3,4-ij]quinazolin-6-one

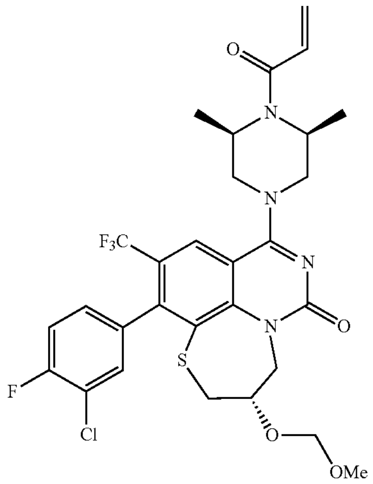 [SMILES: C=CC(=O)N1[C@H](C)CN(c2nc(=O)n3c4c(c(-c5ccc(F)c(Cl)c5)c(C(F)(F)F)cc24)SC[C@@H](OCOC)C3)C[C@@H]1C]

The title compound was prepared analogously to Example 84 where (S)-8-((3S,5R)-4-acryloyl-3,5-dimethylpiperazin-1-yl)-11-(3-chloro-4-fluorophenyl)-3-(methoxymethoxy)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 55% yield as a yellow solid. m/z (ESI, +ve)=641.2 $[M+H]^+$ 1H NMR (400 MHz, DMSO) δ=8.02 (s, 1H), 7.70-7.49 (m, 2H), 7.38-7.33 (m, 1H), 6.82 (dd, J=16.0, 8.0 Hz, 1H), 6.19 (dd, J=16.0, 4.0 Hz, 1H), 5.74 (dd, J=16.0, 4.0 Hz, 1H), 4.69-4.65 (m, 2H), 4.58-4.54 (m, 3H), 4.20-4.16 (m, 1H), 4.10-4.05 (m, 2H), 3.32-3.32 (m, 3H), 3.29-3.27 (m, 3H), 3.27-3.23 (m, 1H), 3.12-3.08 (m, 1H), 1.40 (s, 6H).

Step 1: (S)-8-((3S,5R)-4-acryloyl-3,5-dimethylpiperazin-1-yl)-11-(3-chloro-4-fluorophenyl)-3-(methoxymethoxy)-10-(trifluoromethyl)-3,4-dihydro-2H,6H-[1,4]thiazepino[2,3,4-ij]quinazolin-6-one

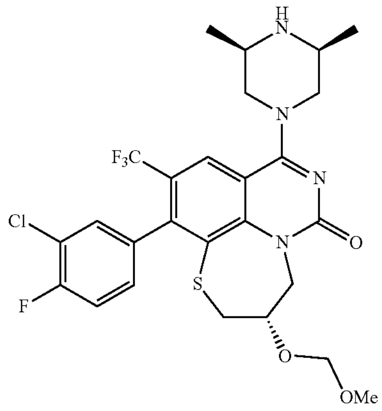 [SMILES: COCO[C@@H]1CSc2c(-c3ccc(F)c(Cl)c3)c(C(F)(F)F)cc3c(N4C[C@@H](C)N[C@@H](C)C4)nc(=O)n(c23)C1]

The title compound was prepared analogously to Example 100, step 21 where (S)-11-(3-chloro-4-fluorophenyl)-3-(methoxymethoxy)-10-(trifluoromethyl)-3,4-dihydro-2H,6H-[1,4]thiazepino[2,3,4-ij]quinazoline-6,8(7H)-dione and (2R,6S)-2,6-dimethylpiperazine were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 55% yield as a pale yellow solid. m/z (ESI, +ve)=587.1 $[M+H]^+$ Example 1015: (3S)-8-((3S,5R)-4-acryloyl-3,5-dimethylpiperazin-1-yl)-11-(5-chloro-2,4-difluorophenyl)-3-(methoxymethoxy)-10-(trifluoromethyl)-3,4-dihydro-2H,6H-[1,4]thiazepino[2,3,4-ij]quinazolin-6-one

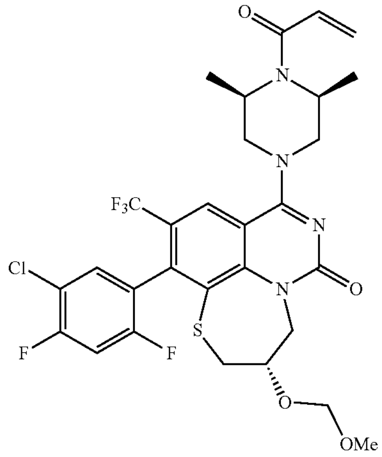 [SMILES: C=CC(=O)N1[C@H](C)CN(c2nc(=O)n3c4c(c(-c5cc(Cl)c(F)cc5F)c(C(F)(F)F)cc24)SC[C@@H](OCOC)C3)C[C@@H]1C]

The title compound was prepared analogously to Example 84 where (S)-11-(3-chloro-4-fluorophenyl)-8-((3S,5R)-3,5-dimethylpiperazin-1-yl)-3-(methoxymethoxy)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 53% yield as a yellow solid. m/z (ESI, +ve)=659.1 $[M+H]^+$ 1H NMR (400 MHz, DMSO-d6) δ 8.05 (s, 1H), 7.83-7.60 (m, 2H), 6.81 (dd, J=16.0, 8.0 Hz, 1H), 6.19 (dd, J=16.0, 4.0 Hz, 1H), 5.74 (dd, J=16.0, 4.0 Hz, 1H), 4.70-4.52 (m, 6H), 4.21 (s, 1H), 4.07 (d, J=12.0 Hz, 2H), 3.62-3.46 (m, 1H), 3.30-3.10 (m, 6H), 1.53-1.30 (m, 6H).

Step 1: 7-(5-chloro-2,4-difluorophenyl)-8-(((S)-3-hydroxy-2-(methoxymethoxy)propyl)thio)-6-(trifluoromethyl)quinazoline-2,4(1H,3H)-dione

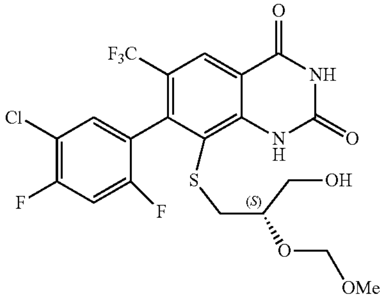

The title compound was synthesized analogously to example 100, step 9 where 7-(5-chloro-2,4-difluorophenyl)-8-iodo-6-(trifluoromethyl)quinazoline-2,4(1H,3H)-dione and (S)-3-mercapto-2-(methoxymethoxy)propan-1-ol were substituted in place of 7-(2,4-difluorophenyl)-8-iodo-6-(trifluoromethyl)quinazoline-2,4(1H,3H)-dione and 2-mercaptoethan-1-ol. The title compound was isolated in 71% yield as a pale yellow solid. m/z (ESI, +ve)=527.1 $[M+H]^+$ Step 2: (3S)-11-(5-chloro-2,4-difluorophenyl)-3-(methoxymethoxy)-10-(trifluoromethyl)-3,4-dihydro-2H,6H-[1,4]thiazepino[2,3,4-ij]quinazoline-6,8(7H)-dione

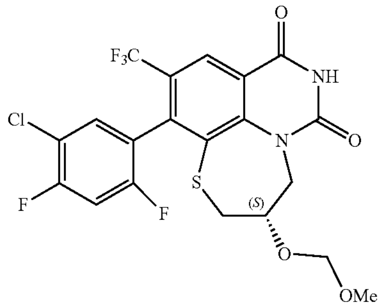

The title compound was prepared analogously to Example 100, step 10 7-(5-chloro-2,4-difluorophenyl)-8-(((S)-3-hydroxy-2-(methoxymethoxy)propyl)thio)-6-(trifluoromethyl)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 80% yield as a yellow solid. m/z (ESI, +ve)=509.0 $[M+H]^+$ Step 3: (S)-11-(3-chloro-4-fluorophenyl)-8-((3S,5R)-3,5-dimethylpiperazin-1-yl)-3-(methoxymethoxy)-10-(trifluoromethyl)-3,4-dihydro-2H,6H-[1,4]thiazepino[2,3,4-ij]quinazolin-6-one

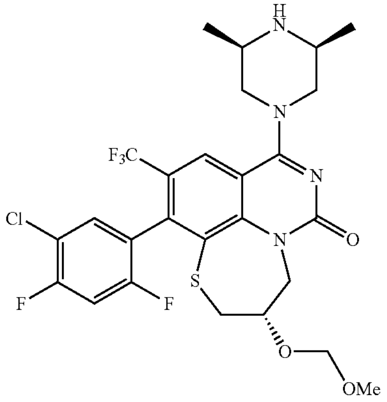 [SMILES: COCO[C@@H]1CSc2c(-c3cc(Cl)c(F)cc3F)c(C(F)(F)F)cc3c(N4C[C@@H](C)N[C@@H](C)C4)nc(=O)n(c23)C1]

The title compound was prepared analogously to Example 100, step 21 where (3S)-11-(5-chloro-2,4-difluorophenyl)-3-(methoxymethoxy)-10-(trifluoromethyl)-3,4-dihydro-2H,6H-[1,4]thiazepino[2,3,4-ij]quinazoline-6,8(7H)-dione and (2R,6S)-2,6-dimethylpiperazine were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 82% yield as a yellow solid. m/z (ESI, +ve)=605.1 [M+H]$^+$ Example 1016: (R)-8-(4-acryloylpiperazin-1-yl)-11-(4-fluorophenyl)-3-(2-methoxyethoxy)-10-(trifluoromethyl)-3,4-dihydro-2H,6H-[1,4]thiazepino[2,3,4-ij]quinazolin-6-one

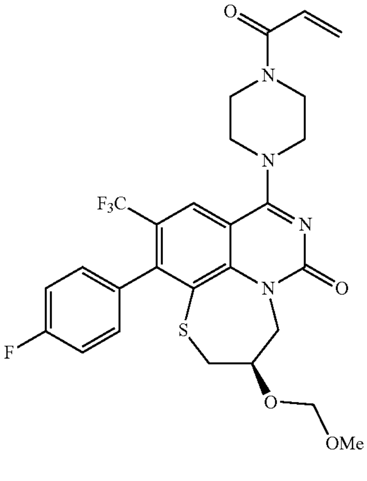 [SMILES: C=CC(=O)N1CCN(c2nc(=O)n3c4c(c(-c5ccc(F)cc5)c(C(F)(F)F)cc24)SC[C@H](OCOC)C3)CC1]

The title compound was prepared analogously to Example 84 where (R)-11-(4-fluorophenyl)-3-(2-methoxyethoxy)-10-(trifluoromethyl)-3,4-dihydro-2H,6H-[1,4]thiazepino[2,3,4-ij]quinazoline-6,8(7H)-dione was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 26% yield as a yellow solid. m/z (ESI, +ve)=593.2 [M+H]$^+$ 1H NMR (400 MHz, DMSO) δ 7.86 (s, 1H), 7.36-7.34 (m, 4H), 6.83 (dd, J=16.0, 8.0 Hz, 1H), 6.17 (dd, J=16.0, 4.0 Hz, 1H), 5.74 (dd, J=16.0, 4.0 Hz, 1H), 4.51-4.48 (m, 1H), 3.94-3.51 (m, 12H), 3.48-3.39 (m, 2H), 3.29-3.08 (m, 5H).

Step 1: (R)-9,9,10,10-tetramethyl-6-((tritylthio)methyl)-2,5,8-trioxa-9-silaundecane

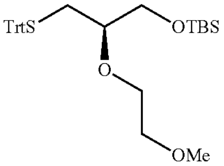

To a suspension of NaH (0.17 mol) in THF (60 mL) at 0° C. was added a solution of (R)-1-((tert-butyldimethylsilyl)oxy)-3-(tritylthio)propan-2-ol (0.13 mol) in THF (60 mL). The mixture was stirred at 0° C. for 30 minutes. DMF (120 mL) was added followed by 1-bromo-2-methoxyethane (0.32 mol). The mixture was stirred at room temperature for 5 hours, quenched with water and extracted with ethyl acetate twice. The combined organic layers were washed with brine, dried over sodium sulfate and concentrated to afford a residue that was purified with silica gel chromatography (0-15% ethyl acetate in hexanes). The title compound was isolated in 83% yield as yellow oil. m/z (ESI, +ve)=545.3 [M+Na]$^+$ Step 2: (R)-3-mercapto-2-(2-methoxyethoxy)propan-1-ol

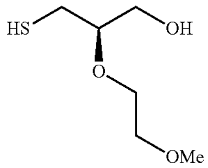

To 0° C. mixture of (R)-9,9,10,10-tetramethyl-6-((tritylthio)methyl)-2,5,8-trioxa-9-silaundecane (0.11 mol) in dichloromethane/TFA (60/20 mL) was added triethyl silane (0.34 mol). The mixture was stirred at room temperature for 30 m mutes, diluted with water and extracted with dichloromethane five times. The combined organic layers were concentrated to afford a residue that was purified by silica gel column chromatography (0-7% methanol in dichloromethane) to afford the title compound in 75% yield as yellow oil Step 3: (R)-7-(4-fluorophenyl)-8-((3-hydroxy-2-(2-methoxyethoxy)propyl)thio)-6-(trifluoromethyl)quinazoline-2,4(1H,3H)-dione

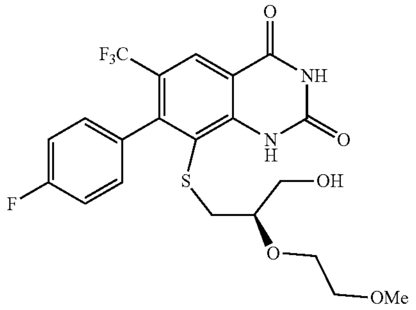 [SMILES: COCCO[C@H](CO)CSc1c(-c2ccc(F)cc2)c(C(F)(F)F)cc2c(=O)[nH]c(=O)[nH]c12]

The title compound was synthesized analogously to example 100, step 9 where 7-(4-fluorophenyl)-8-iodo-6-(trifluoromethyl)quinazoline-2,4(1H,3H)-dione and (R)-3-mercapto-2-(2-methoxyethoxy)propan-1-ol were substituted in place of 7-(2,4-difluorophenyl)-8-iodo-6-(trifluoromethyl)quinazoline-2,4(1H,3H)-dione and 2-mercaptoethan-1-ol. The title compound was isolated in 92% yield as a yellow solid. m/z (ESI, +ve)=489.1 $[M+H]^+$ Step 4: (R)-11-(4-fluorophenyl)-3-(2-methoxyethoxy)-10-(trifluoromethyl)-3,4-dihydro-2H,6H-[1,4]thiazepino[2,3,4-ij]quinazoline-6,8(7H)-dione

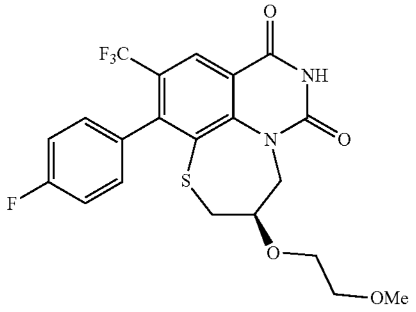 [SMILES: COCCO[C@H]1CSc2c(-c3ccc(F)cc3)c(C(F)(F)F)cc3c(=O)[nH]c(=O)n(c23)C1]

The title compound was prepared analogously to Example 100, step 10 where (R)-7-(4-fluorophenyl)-8-((3-hydroxy-2-(2-methoxyethoxy)propyl)thio)-6-(trifluoromethyl)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 83% yield as a yellow solid. m/z (ESI, +ve)=471.1 $[M+H]^+$ Step 5: (R)-11-(4-fluorophenyl)-3-(2-methoxyethoxy)-8-(piperazin-1-yl)-10-(trifluoromethyl)-3,4-dihydro-2H,6H-[1,4]thiazepino[2,3,4-ij]quinazolin-6-one

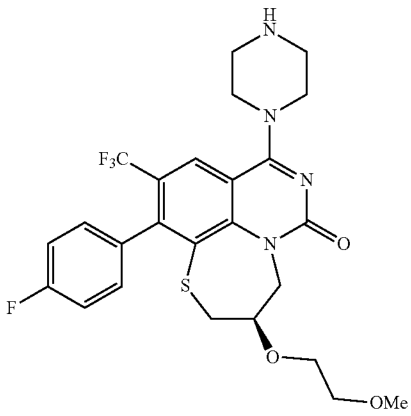 [SMILES: COCCO[C@H]1CSc2c(-c3ccc(F)cc3)c(C(F)(F)F)cc3c(N4CCNCC4)nc(=O)n(c23)C1]

The title compound was prepared analogously to Example 100, step 21 where (R)-11-(4-fluorophenyl)-3-(2-methoxyethoxy)-10-(trifluoromethyl)-3,4-dihydro-2H,6H-[1,4]thiazepino[2,3,4-ij]quinazoline-6,8(7H)-dione and piperazine were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 82% yield as a pale yellow solid. m/z (ESI, +ve)=639.2 $[M+H]^+$ Example 1017: (S)-8-(4-acryloylpiperazin-1-yl)-11-(4-fluorophenyl)-3-(2-methoxyethoxy)-10-(trifluoromethyl)-3,4-dihydro-2H,6H-[1,4]thiazepino[2,3,4-ij]quinazolin-6-one

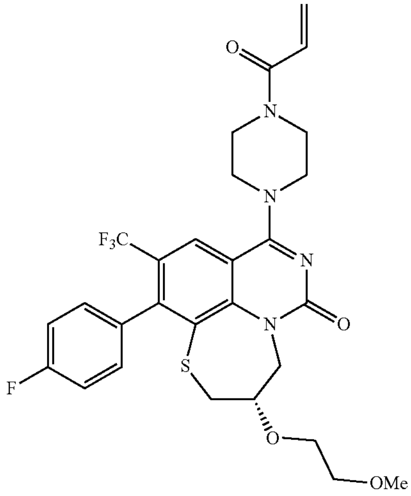 [SMILES: C=CC(=O)N1CCN(c2nc(=O)n3c4c(c(-c5ccc(F)cc5)c(C(F)(F)F)cc24)SC[C@@H](OCCOC)C3)CC1]

The title compound was prepared analogously to Example 84 where (S)-11-(4-fluorophenyl)-3-(2-methoxyethoxy)-8-(piperazin-1-yl)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1, 4]thiazino[2,3,4-ij]quinazolin-5-one. The title compound was isolated in 21% yield as a yellow solid. m/z (ESI, +ve)=593.2 [M+H]$^+$ 1H NMR (400 MHz, DMSO) δ 7.86 (s, 1H), 7.36-7.34 (m, 4H), 6.82 (dd, J=16.0, 8.0 Hz, 1H), 6.17 (dd, J=16.0, 4.0 Hz, 1H), 5.74 (dd, J=16.0, 4.0 Hz, 1H), 4.51-4.48 (m, 1H), 3.94-3.61 (m, 11H), 3.44-3.37 (m, 4H), 3.28-3.23 (m, 3H), 3.11-3.08 (m, 1H).

Step 1: (S)-7-(4-fluorophenyl)-8-((3-hydroxy-2-(2-methoxyethoxy)propyl)thio)-6-(trifluoromethyl)quinazoline-2,4(1H,3H)-dione

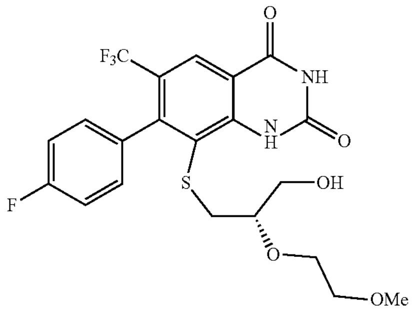 [SMILES: COCCO[C@@H](CO)CSc1c(-c2ccc(F)cc2)c(C(F)(F)F)cc2c(=O)[nH]c(=O)[nH]c12]

The title compound was synthesized analogously to example 527, step 9 where (S)-3-mercapto-2-(2-methoxyethoxy)propan-1-ol was substituted in place of 2-mercaptoethan-1-ol. The title compound was isolated in 82% yield as a pale yellow solid. m/z (ESI, +ve)=489.1 [M+H]$^+$ Step 2: (S)-11-(4-fluorophenyl)-3-(2-methoxyethoxy)-10-(trifluoromethyl)-3,4-dihydro-2H,6H-[1,4]thiazepino[2,3,4-ij]quinazoline-6,8(7H)-dione

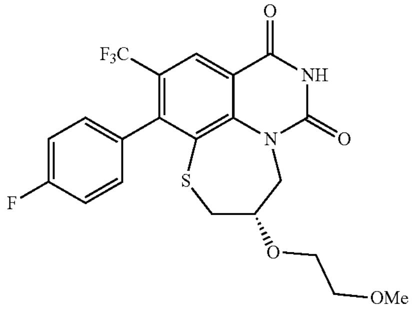 [SMILES: COCCO[C@@H]1CSc2c(-c3ccc(F)cc3)c(C(F)(F)F)cc3c(=O)[nH]c(=O)n(c23)C1]

The title compound was synthesized analogously to example 527, step 10 where (S)-7-(4-fluorophenyl)-8-((3-hydroxy-2-(2-methoxyethoxy)propyl)thio)-6-(trifluoromethyl)quinazoline-2,4(1H,3H)-dione was substituted in place of (R)-7-(4-fluorophenyl)-8-((3-hydroxy-2-methoxypropyl)thio)-6-(trifluoromethyl)quinazoline-2,4(1H,3H)-dione. The title compound was isolated in 63% yield as a yellow solid. m/z (ESI, +ve)=471.1 [M+H]$^+$ Step 3: tert-butyl (S)-4-(11-(4-fluorophenyl)-3-(2-methoxyethoxy)-6-oxo-10-(trifluoromethyl)-3,4-dihydro-2H,6H-[1,4]thiazepino[2,3,4-ij]quinazolin-8-yl)piperazine-1-carboxylate

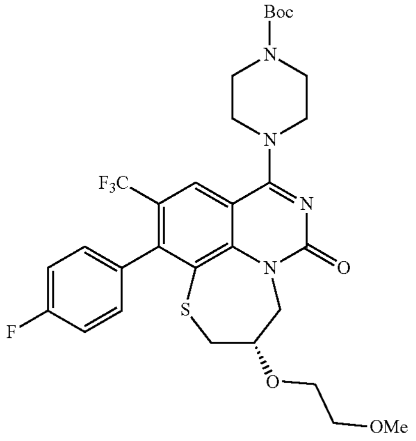 [SMILES: COCCO[C@@H]1CSc2c(-c3ccc(F)cc3)c(C(F)(F)F)cc3c(N4CCN(C(=O)OC(C)(C)C)CC4)nc(=O)n(c23)C1]

The title compound was prepared analogously to Example 100, step 21 where (S)-11-(4-fluorophenyl)-3-(2-methoxyethoxy)-10-(trifluoromethyl)-3,4-dihydro-2H,6H-[1,4]thiazepino[2,3,4-ij]quinazoline-6,8(7H)-dione and tert-butyl piperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 71% yield as a yellow solid. m/z (ESI, +ve)=639.2 [M+H]$^+$ Step 4: (S)-11-(4-fluorophenyl)-3-(2-methoxyethoxy)-8-(piperazin-1-yl)-10-(trifluoromethyl)-3,4-dihydro-2H,6H-[1,4]thiazepino[2,3,4-ij]quinazolin-6-one

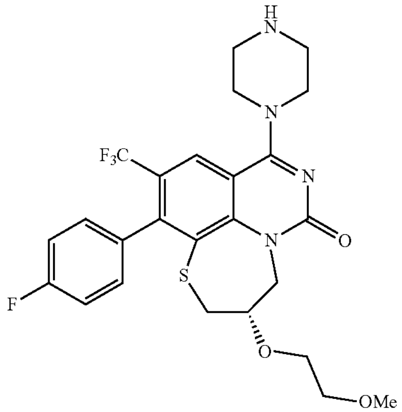 [SMILES: COCCO[C@@H]1CSc2c(-c3ccc(F)cc3)c(C(F)(F)F)cc3c(N4CCNCC4)nc(=O)n(c23)C1]

The title compound was prepared analogously to Example 102, step 4, where tert-butyl (S)-4-(11-(4-fluorophenyl)-3-(2-methoxyethoxy)-6-oxo-10-(trifluoromethyl)-3,4-dihydro-2H,6H-[1,4]thiazepino[2,3,4-ij]quinazolin-8-yl)piperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3- methylpiperazine-1-carboxylate. The title compound was isolated in 91% yield as a yellow solid. m/z (ESI, +ve) =539.2 [M+H]$^+$ Example 1018: (3R)-8-(4-acryloylpiperazin-1-yl)-11-(2,4-difluorophenyl)-3-(2-methoxyethoxy)-10-(trifluoromethyl)-3,4-dihydro-2H,6H-[1,4]thiazepino[2,3,4-ij]quinazolin-6-one

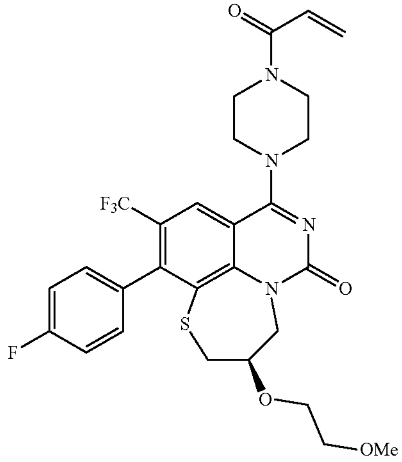 [SMILES: C=CC(=O)N1CCN(c2nc(=O)n3c4c(c(-c5ccc(F)cc5)c(C(F)(F)F)cc24)SC[C@H](OCCOC)C3)CC1]

The title compound was prepared analogously to Example 84 where (3R)-11-(2,4-difluorophenyl)-3-(2-methoxyethoxy)-8-(piperazin-1-yl)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 34% yield as a yellow solid. m/z (ESI, +ve)=611.0 [M+H]$^+$ 1H NMR (400 MHz, DMSO) δ 7.89 (s, 1H), 7.46-7.42 (m, 2H), 7.28-7.24 (m, 1H), 6.82 (dd, J=16.0, 8.0 Hz, 1H), 6.17 (dd, J=16.0, 4.0 Hz, 1H), 5.74 (dd, J=16.0, 4.0 Hz, 1H), 4.49-4.45 (m, 1H), 3.80-3.76 (m, 11H), 3.45-3.41 (m, 2H), 3.35-3.31 (m, 2H), 3.25-3.21 (m, 3H), 3.19-3.10 (m, 1H).

Step 1: 7-(2,4-difluorophenyl)-8-(((R)-3-hydroxy-2-(2-methoxyethoxy)propyl)thio)-6-(trifluoromethyl)quinazoline-2,4(1H,3H)-dione

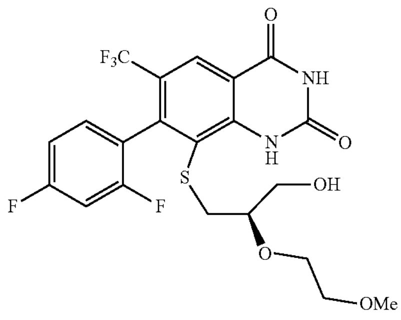 [SMILES: COCCO[C@H](CO)CSc1c(-c2ccc(F)cc2F)c(C(F)(F)F)cc2c(=O)[nH]c(=O)[nH]c12]

The title compound was prepared analogously to Example 100, step 9 where 7-(2,4-difluorophenyl)-8-iodo-6-(trifluoromethyl)quinazoline-2,4(1H,3H)-dione and (R)-3-mercapto-2-(2-methoxyethoxy)propan-1-ol were substituted in place of 7-(2,4-difluorophenyl)-8-iodo-6-(trifluoromethyl)quinazoline-2,4(1H,3H)-dione and 2-mercaptoethan-1-ol. The title compound was isolated in 66% yield as a white solid. m/z (ESI, +ve)=507.1 [M+H]$^+$ Step 2: (3R)-11-(2,4-difluorophenyl)-3-(2-methoxyethoxy)-10-(trifluoromethyl)-3,4-dihydro-2H,6H-[1,4]thiazepino[2,3,4-ij]quinazoline-6,8(7H)-dione

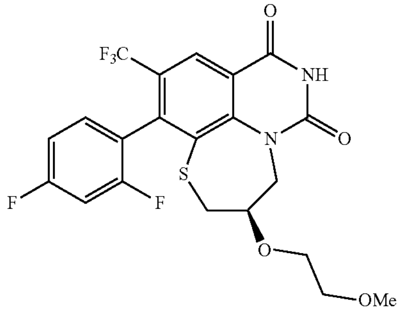 [SMILES: COCCO[C@H]1CSc2c(-c3ccc(F)cc3F)c(C(F)(F)F)cc3c(=O)[nH]c(=O)n(c23)C1]

The title compound was synthesized analogously to example 527, step 10 where 7-(2,4-difluorophenyl)-8-(((R)-3-hydroxy-2-(2-methoxyethoxy)propyl)thio)-6-(trifluoromethyl)quinazoline-2,4(1H,3H)-dione was substituted in place of (R)-7-(4-fluorophenyl)-8-((3-hydroxy-2-methoxypropyl)thio)-6-(trifluoromethyl)quinazoline-2,4(1H,3H)-dione. The title compound was isolated in 65% yield as a yellow solid. m/z (ESI, +ve)=489.1 [M+H]$^+$ Step 3: tert-butyl 4-((3R)-11-(2,4-difluorophenyl)-3-(2-methoxyethoxy)-6-oxo-10-(trifluoromethyl)-3,4-dihydro-2H,6H-[1,4]thiazepino[2,3,4-ij]quinazolin-8-yl)piperazine-1-carboxylate

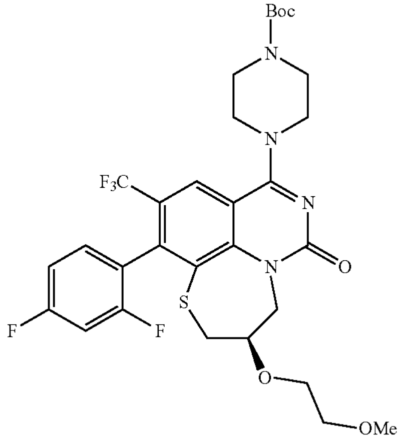 [SMILES: COCCO[C@H]1CSc2c(-c3ccc(F)cc3F)c(C(F)(F)F)cc3c(N4CCN(C(=O)OC(C)(C)C)CC4)nc(=O)n(c23)C1]

The title compound was prepared analogously to Example 100, step 21 where (3R)-11-(2,4-difluorophenyl)-3-(2-methoxyethoxy)-10-(trifluoromethyl)-3,4-dihydro-2H,6H-[1,4]thiazepino[2,3,4-ij]quinazoline-6,8(7H)-dione and tert-butyl piperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 52% yield as a yellow solid. m/z (ESI, +ve)=489.1 $[M+H]^+$ Step 4: (3R)-11-(2,4-difluorophenyl)-3-(2-methoxyethoxy)-8-(piperazin-1-yl)-10-(trifluoromethyl)-3,4-dihydro-2H,6H-[1,4]thiazepino[2,3,4-ij]quinazolin-6-one

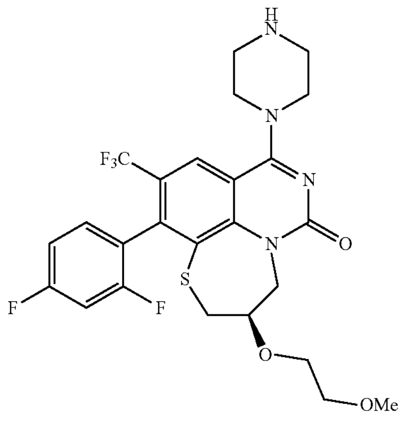 [SMILES: COCCO[C@H]1CSc2c(-c3ccc(F)cc3F)c(C(F)(F)F)cc3c(N4CCNCC4)nc(=O)n(c23)C1]

The title compound was prepared analogously to Example 102, step 4, where tert-butyl (S)-4-(11-(4-fluorophenyl)-3-methoxy-6-oxo-10-(trifluoromethyl)-3,4-dihydro-2H,6H-[1,4]thiazepino[2,3,4-ij]quinazolin-8-yl)piperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 94% yield as a yellow solid. m/z (ESI, +ve)=557.2 $[M+H]^+$ Example 1019: (3S)-8-(4-acryloylpiperazin-1-yl)-11-(2,4-difluorophenyl)-3-(2-methoxyethoxy)-10-(trifluoromethyl)-3,4-dihydro-2H,6H-[1,4]thiazepino[2,3,4-ij]quinazolin-6-one

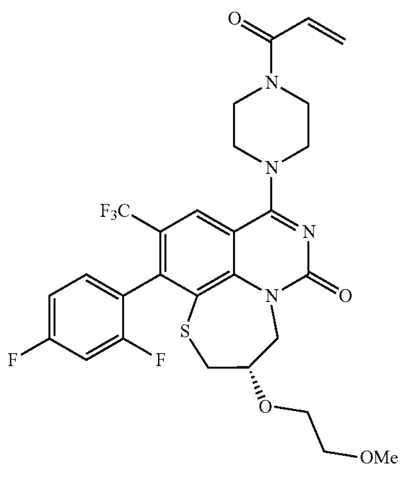 [SMILES: C=CC(=O)N1CCN(c2nc(=O)n3c4c(c(-c5ccc(F)cc5F)c(C(F)(F)F)cc24)SC[C@@H](OCCOC)C3)CC1]

The title compound was prepared analogously to Example 84 where (3S)-11-(2,4-difluorophenyl)-3-(2-methoxyethoxy)-8-(piperazin-1-yl)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 19% yield as a yellow solid. m/z (ESI, +ve)=611.2 $[M+H]^+$ $^1H$ NMR (400 MHz, DMSO-d6) δ 7.89 (s, 1H), 7.47-7.37 (m, 2H), 7.28-7.26 (m, 1H), 6.82 (dd, J=16.0, 8.0 Hz, 1H), 6.17 (dd, J=16.0, 4.0 Hz, 1H), 5.74 (d, J=16.0, 4.0 Hz, 1H), 4.48-4.44 (m, 1H), 3.97-3.62 (m, 11H), 3.44-3.43 (m, 2H), 3.38-3.33 (m, 2H), 3.23 (s, 2H), 3.18-3.15 (m, 2H).

Step 1: 7-(2,4-difluorophenyl)-8-(((S)-3-hydroxy-2-(2-methoxyethoxy)propyl)thio)-6-(trifluoromethyl)quinazoline-2,4(1H,3H)-dione

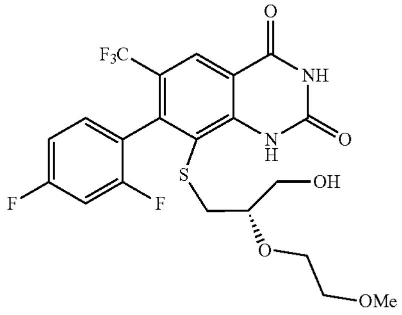 [SMILES: COCCO[C@@H](CO)CSc1c(-c2ccc(F)cc2F)c(C(F)(F)F)cc2c(=O)[nH]c(=O)[nH]c12]

The title compound was synthesized analogously to example 100, step 9 where 7-(2,4-difluorophenyl)-8-iodo-6-(trifluoromethyl)quinazoline-2,4(1H,3H)-dione and (S)-3-mercapto-2-(2-methoxyethoxy)propan-1-ol were substituted in place of 7-(2,4-difluorophenyl)-8-iodo-6-(trifluoromethyl)quinazoline-2,4(1H,3H)-dione and 2-mercaptoethan-1-ol. The title compound was isolated in 56% yield as a yellow solid. m/z (ESI, +ve)=507.1 $[M+H]^+$ Step 2: (3S)-11-(2,4-difluorophenyl)-3-(2-methoxyethoxy)-10-(trifluoromethyl)-3,4-dihydro-2H,6H-[1,4]thiazepino[2,3,4-ij]quinazoline-6,8(7H)-dione

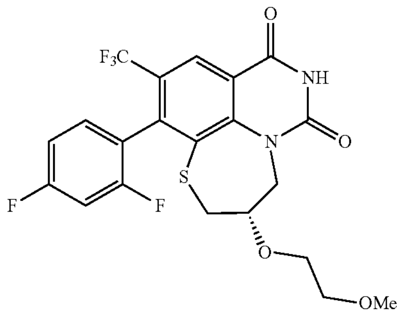 [SMILES: COCCO[C@@H]1CSc2c(-c3ccc(F)cc3F)c(C(F)(F)F)cc3c(=O)[nH]c(=O)n(c23)C1]

The title compound was prepared analogously to Example 100, step 10 where 7-(2,4-difluorophenyl)-8-(((S)-3-hydroxy-2-(2-methoxyethoxy)propyl)thio)-6-(trifluoromethyl)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 86% yield as a yellow solid. m/z (ESI, +ve)=489.1 $[M+H]^+$ Step 3: tert-butyl 4-((3S)-11-(2,4-difluorophenyl)-3-(2-methoxyethoxy)-6-oxo-10-(trifluoromethyl)-3,4-dihydro-2H,6H-[1,4]thiazepino[2,3,4-ij]quinazolin-8-yl)piperazine-1-carboxylate

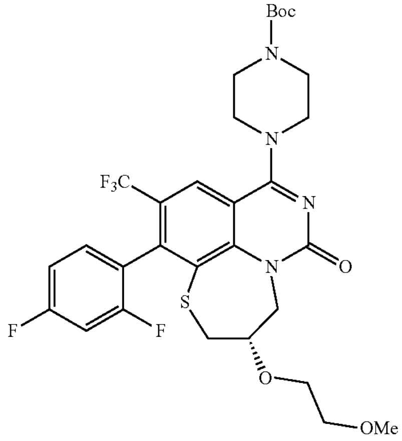 [SMILES: COCCO[C@@H]1CSc2c(-c3ccc(F)cc3F)c(C(F)(F)F)cc3c(N4CCN(C(=O)OC(C)(C)C)CC4)nc(=O)n(c23)C1]

The title compound was prepared analogously to Example 100, step 21 where (3S)-11-(2,4-difluorophenyl)-3-(2-methoxyethoxy)-10-(trifluoromethyl)-3,4-dihydro-2H,6H-[1,4]thiazepino[2,3,4-ij]quinazoline-6,8(7H)-dione and tert-butyl piperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 83% yield as a yellow solid. m/z (ESI, +ve)=657.2 $[M+H]^+$ Step 4: (3S)-11-(2,4-difluorophenyl)-3-(2-methoxyethoxy)-8-(piperazin-1-yl)-10-(trifluoromethyl)-3,4-dihydro-2H,6H-[1,4]thiazepino[2,3,4-ij]quinazolin-6-one

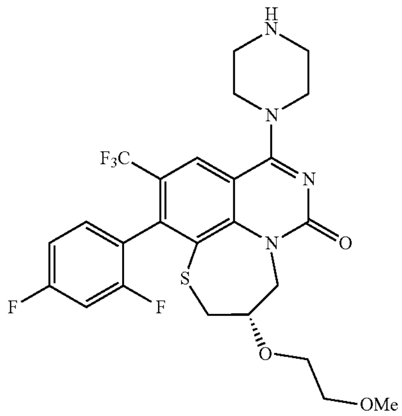 [SMILES: COCCO[C@@H]1CSc2c(-c3ccc(F)cc3F)c(C(F)(F)F)cc3c(N4CCNCC4)nc(=O)n(c23)C1]

The title compound was prepared analogously to Example 102, step 4, where tert-butyl 4-((3S)-11-(2,4-difluorophenyl)-3-(2-methoxyethoxy)-6-oxo-10-(trifluoromethyl)-3,4-dihydro-2H,6H-[1,4]thiazepino[2,3,4-ij]quinazolin-8-yl) piperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 92% yield as a yellow oil. m/z (ESI, +ve)=557.2 $[M+H]^+$ Example 1020: (R)-8-(4-acryloylpiperazin-1-yl)-11-(3-chloro-4-fluorophenyl)-3-(2-methoxyethoxy)-10-(trifluoromethyl)-3,4-dihydro-2H,6H-[1,4]thiazepino[2,3,4-ij]quinazolin-6-one

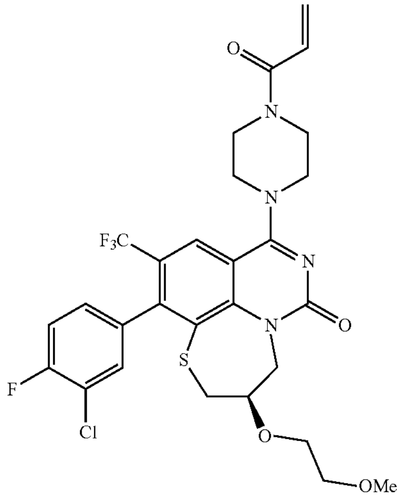 [SMILES: C=CC(=O)N1CCN(c2nc(=O)n3c4c(c(-c5ccc(F)c(Cl)c5)c(C(F)(F)F)cc24)SC[C@H](OCCOC)C3)CC1]

Step 1: (R)-7-(3-chloro-4-fluorophenyl)-8-((3-hydroxy-2-(2-methoxyethoxy)propyl)thio)-6-(trifluoromethyl)quinazoline-2,4(1H,3H)-dione

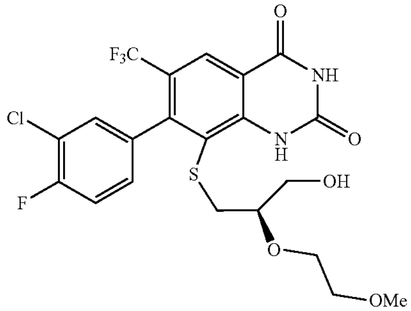 [SMILES: COCCO[C@H](CO)CSc1c(-c2ccc(F)c(Cl)c2)c(C(F)(F)F)cc2c(=O)[nH]c(=O)[nH]c12]

The title compound was synthesized analogously to example 100, step 9 where 7-(3-chloro-4-fluorophenyl)-8-iodo-6-(trifluoromethyl)quinazoline-2,4(1H,3H)-dione and (R)-3-mercapto-2-(2-methoxyethoxy)propan-1-ol were substituted in place of 7-(2,4-difluorophenyl)-8-iodo-6-(trifluoromethyl)quinazoline-2,4(1H,3H)-dione and 2-mercaptoethan-1-ol. The title compound was isolated in 76% yield as a white solid. m/z (ESI, +ve)=523 $[M+H]^+$ Step 2: (R)-11-(3-chloro-4-fluorophenyl)-3-(2-methoxyethoxy)-10-(trifluoromethyl)-3,4-dihydro-2H,6H-[1,4]thiazepino[2,3,4-ij]quinazoline-6,8(7H)-dione

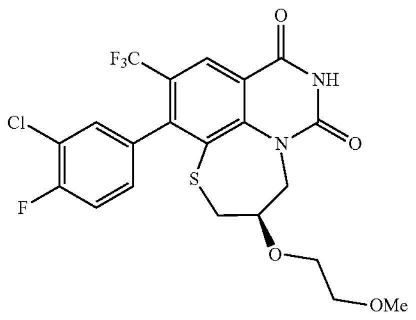 [SMILES: COCCO[C@H]1CSc2c(-c3ccc(F)c(Cl)c3)c(C(F)(F)F)cc3c(=O)[nH]c(=O)n(c23)C1]

The title compound was prepared analogously to Example 100, step 10 where (R)-7-(3-chloro-4-fluorophenyl)-8-((3-hydroxy-2-(2-methoxyethoxy)propyl)thio)-6-(trifluoromethyl)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 52% yield as a yellow solid. m/z (ESI, +ve)=506.0 [M+H]$^+$ Step 3: tert-butyl (R)-4-(11-(3-chloro-4-fluorophenyl)-3-(2-methoxyethoxy)-6-oxo-10-(trifluoromethyl)-3,4-dihydro-2H,6H-[1,4]thiazepino[2,3,4-ij]quinazolin-8-yl)piperazine-1-carboxylate

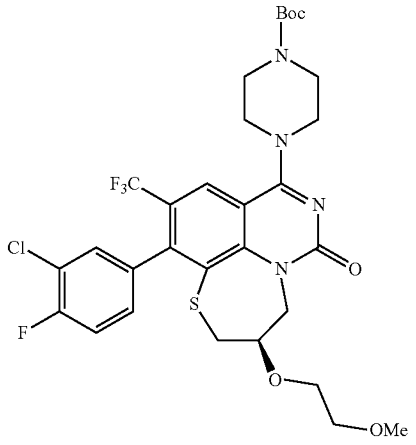 [SMILES: COCCO[C@H]1CSc2c(-c3ccc(F)c(Cl)c3)c(C(F)(F)F)cc3c(N4CCN(C(=O)OC(C)(C)C)CC4)nc(=O)n(c23)C1]

The title compound was prepared analogously to Example 100, step 21 where (R)-11-(3-chloro-4-fluorophenyl)-3-(2-methoxyethoxy)-10-(trifluoromethyl)-3,4-dihydro-2H,6H-[1,4]thiazepino[2,3,4-ij]quinazoline-6,8(7H)-dione and tert-butyl piperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 74% yield as a yellow solid. m/z (ESI, +ve)=673.2 [M+H]$^+$ Step 4: (R)-11-(3-chloro-4-fluorophenyl)-3-(2-methoxyethoxy)-8-(piperazin-1-yl)-10-(trifluoromethyl)-3,4-dihydro-2H,6H-[1,4]thiazepino[2,3,4-ij]quinazolin-6-one

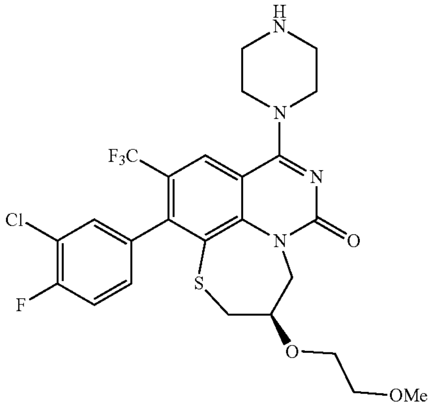 [SMILES: COCCO[C@H]1CSc2c(-c3ccc(F)c(Cl)c3)c(C(F)(F)F)cc3c(N4CCNCC4)nc(=O)n(c23)C1]

The title compound was prepared analogously to Example 102, step 4, where tert-butyl (R)-4-(11-(3-chloro-4-fluorophenyl)-3-(2-methoxyethoxy)-6-oxo-10-(trifluoromethyl)-3,4-dihydro-2H,6H-[1,4]thiazepino[2,3,4-ij]quinazolin-8-yl)piperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 98% yield as a yellow solid. m/z (ESI, +ve)=539.2 [M+H]$^+$ Example 1021: (S)-8-(4-acryloylpiperazin-1-yl)-11-(3-chloro-4-fluorophenyl)-3-(2-methoxyethoxy)-10-(trifluoromethyl)-3,4-dihydro-2H,6H-[1,4]thiazepino[2,3,4-ij]quinazolin-6-one

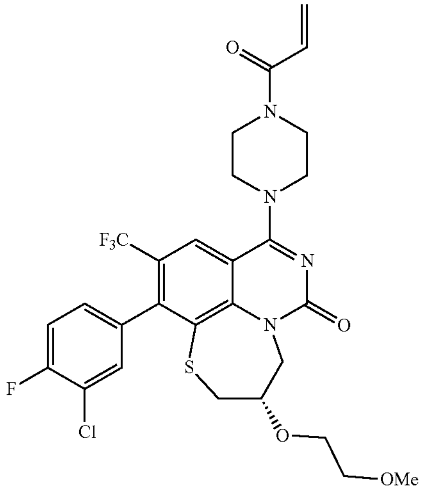 [SMILES: C=CC(=O)N1CCN(c2nc(=O)n3c4c(c(-c5ccc(F)c(Cl)c5)c(C(F)(F)F)cc24)SC[C@@H](OCCOC)C3)CC1]

The title compound was prepared analogously to Example 84 where (S)-11-(3-chloro-4-fluorophenyl)-3-(2-methoxyethoxy)-8-(piperazin-1-yl)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-

(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 51% yield as a yellow solid. m/z (ESI, +ve)=627.2 [M+H]$^+$ 1H NMR (400 MHz, DMSO-$d_6$) δ 7.87 (s, 1H), 7.61-7.57 (m, 2H), 7.36 (s, 1H), 6.83 (dd, J=16.0, 8.0 Hz, 1H), 6.17 (dd, J=16.0, 4.0 Hz, 1H), 5.74 (dd, J=16.0, 4.0 Hz, 1H), 4.53-4.49 (m, 1H), 3.98-3.60 (m, 11H), 3.46-3.42 (m, 2H), 3.38-3.34 (m, 3H), 3.26-3.22 (m, 3H), 3.14-3.10 (m, 1H).

Step 1: (S)-7-(3-chloro-4-fluorophenyl)-8-((3-hydroxy-2-(2-methoxyethoxy)propyl)thio)-6-(trifluoromethyl)quinazoline-2,4(1H,3H)-dione

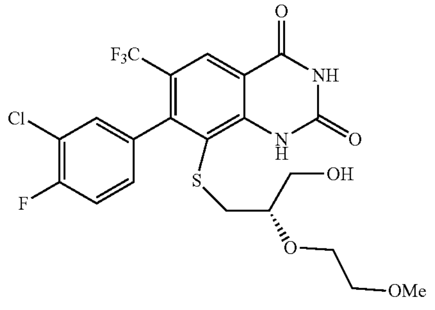 [SMILES: COCCO[C@@H](CO)CSc1c(-c2ccc(F)c(Cl)c2)c(C(F)(F)F)cc2c(=O)[nH]c(=O)[nH]c12]

The title compound was synthesized analogously to example 100, step 9 where 7-(3-chloro-4-fluorophenyl)-8-iodo-6-(trifluoromethyl)quinazoline-2,4(1H,3H)-dione and (S)-3-mercapto-2-(2-methoxyethoxy)propan-1-ol were substituted in place of 7-(2,4-difluorophenyl)-8-iodo-6-(trifluoromethyl)quinazoline-2,4(1H,3H)-dione and 2-mercaptoethan-1-ol. The title compound was isolated in 78% yield as a white solid. m/z (ESI, +ve)=523.0 [M+H]$^+$ Step 2: (S)-11-(3-chloro-4-fluorophenyl)-3-(2-methoxyethoxy)-10-(trifluoromethyl)-3,4-dihydro-2H,6H-[1,4]thiazepino[2,3,4-ij]quinazoline-6,8(7H)-dione

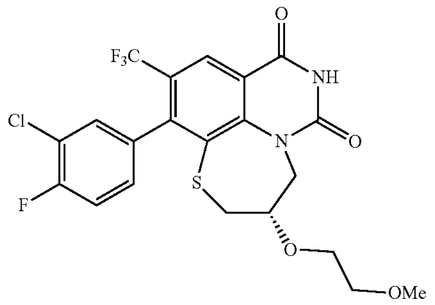 [SMILES: COCCO[C@@H]1CSc2c(-c3ccc(F)c(Cl)c3)c(C(F)(F)F)cc3c(=O)[nH]c(=O)n(c23)C1]

The title compound was prepared analogously to Example 100, step 10 where (S)-7-(3-chloro-4-fluorophenyl)-8-((3-hydroxy-2-(2-methoxyethoxy)propyl)thio)-6-(trifluoromethyl)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 76% yield as a yellow solid. m/z (ESI, +ve)=527.0 [M+H]$^+$ Step 3: tert-butyl (S)-4-(11-(3-chloro-4-fluorophenyl)-3-(2-methoxyethoxy)-6-oxo-10-(trifluoromethyl)-3,4-dihydro-2H,6H-[1,4]thiazepino[2,3,4-ij]quinazolin-8-yl)piperazine-1-carboxylate

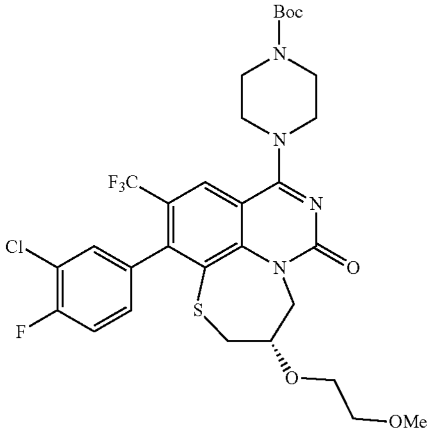 [SMILES: COCCO[C@@H]1CSc2c(-c3ccc(F)c(Cl)c3)c(C(F)(F)F)cc3c(N4CCN(C(=O)OC(C)(C)C)CC4)nc(=O)n(c23)C1]

The title compound was prepared analogously to Example 100, step 21 where (S)-11-(3-chloro-4-fluorophenyl)-3-(2-methoxyethoxy)-10-(trifluoromethyl)-3,4-dihydro-2H,6H-[1,4]thiazepino[2,3,4-ij]quinazoline-6,8(7H)-dione and tert-butyl piperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 49% yield as a yellow solid. m/z (ESI, +ve)=673.2 [M+H]$^+$ Step 4: (S)-11-(3-chloro-4-fluorophenyl)-3-(2-methoxyethoxy)-8-(piperazin-1-yl)-10-(trifluoromethyl)-3,4-dihydro-2H,6H-[1,4]thiazepino[2,3,4-ij]quinazolin-6-one

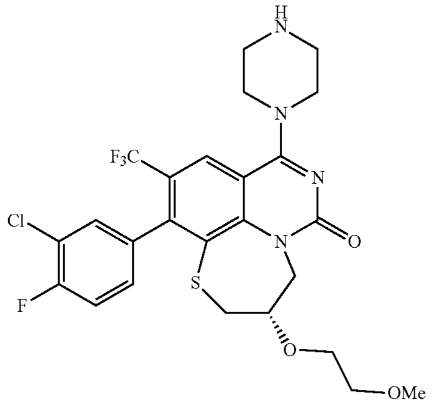 [SMILES: COCCO[C@@H]1CSc2c(-c3ccc(F)c(Cl)c3)c(C(F)(F)F)cc3c(N4CCNCC4)nc(=O)n(c23)C1]

The title compound was prepared analogously to Example 102, step 4, where tert-butyl (S)-4-(11-(3-chloro-4-fluorophenyl)-3-(2-methoxyethoxy)-6-oxo-10-(trifluoromethyl)-3,4-dihydro-2H,6H-[1,4]thiazepino[2,3,4-ij]quinazolin-8-yl)piperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3- methylpiperazine-1-carboxylate. The title compound was isolated in 94% yield as a yellow solid. m/z (ESI, +ve)= 573.1 [M+H]$^+$ Example 1022: (3R)-8-(4-acryloylpiperazin-1-yl)-11-(5-chloro-2,4-difluorophenyl)-3-(2-methoxyethoxy)-10-(trifluoromethyl)-3,4-dihydro-2H,6H-[1,4]thiazepino[2,3,4-ij]quinazolin-6-one

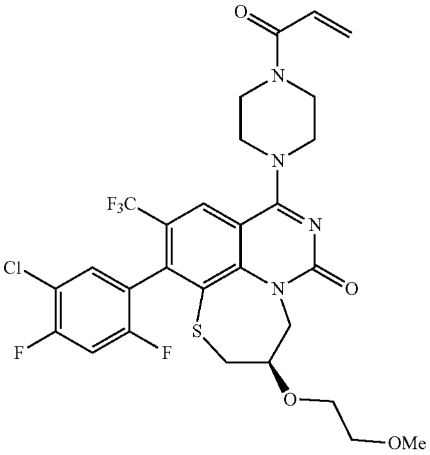 [SMILES: C=CC(=O)N1CCN(c2nc(=O)n3c4c(c(-c5cc(Cl)c(F)cc5F)c(C(F)(F)F)cc24)SC[C@H](OCCOC)C3)CC1]

The title compound was prepared analogously to Example 84 where (3R)-11-(5-chloro-2,4-difluorophenyl)-3-(2-methoxyethoxy)-8-(piperazin-1-yl)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in XX % yield as a yellow solid. m/z (ESI, +ve)=645.1 [M+H]$^+$ 1H NMR (400 MHz, DMSO) δ 7.90 (s, 1H), 7.81-7.75 (m, 2H), 6.82 (dd, J=16.0, 8.0 Hz, 1H), 6.17 (d, J=16.0, 4.0 Hz, 1H), 5.74 (dd, J=16.0, 4.0 Hz, 1H), 4.54-4.42 (m, 1H), 3.98 (s, 1H), 3.91-3.54 (m, 10H), 3.43-3.41 (m, 2H), 3.37-3.33 (m, 2H), 3.24 (s, 3H), 3.22-3.14 (m, 1H).

Step 1: 7-(5-chloro-2,4-difluorophenyl)-8-(((R)-3-hydroxy-2-(2-methoxyethoxy)propyl)thio)-6-(trifluoromethyl)quinazoline-2,4(1H,3H)-dione

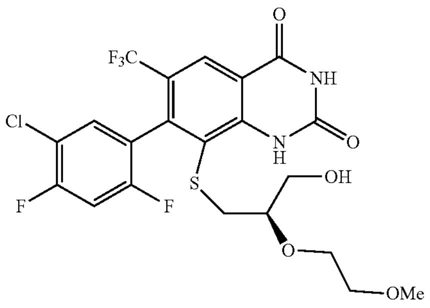 [SMILES: COCCO[C@H](CO)CSc1c(-c2cc(Cl)c(F)cc2F)c(C(F)(F)F)cc2c(=O)[nH]c(=O)[nH]c12]

The title compound was synthesized analogously to example 100, step 9 where 7-(5-chloro-2,4-difluorophenyl)-8-iodo-6-(trifluoromethyl)quinazoline-2,4(1H,3H)-dione and (R)-3-mercapto-2-(2-methoxyethoxy)propan-1-ol were substituted in place of 7-(2,4-difluorophenyl)-8-iodo-6-(trifluoromethyl)quinazoline-2,4(1H,3H)-dione and 2-mercaptoethan-1-ol. The title compound was isolated in 63% yield as a white solid. m/z (ESI, +ve)=541.0 [M+H]$^+$ Step 2: (3R)-11-(5-chloro-2,4-difluorophenyl)-3-(2-methoxyethoxy)-10-(trifluoromethyl)-3,4-dihydro-2H,6H-[1,4]thiazepino[2,3,4-ij]quinazoline-6,8(7H)-dione

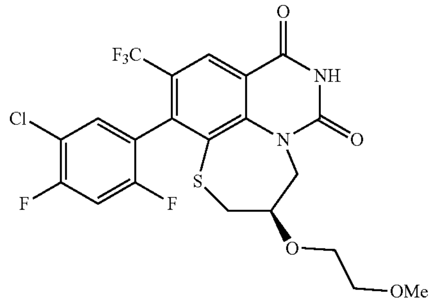 [SMILES: COCCO[C@H]1CSc2c(-c3cc(Cl)c(F)cc3F)c(C(F)(F)F)cc3c(=O)[nH]c(=O)n(c23)C1]

The title compound was prepared analogously to Example 100, step 10 where 7-(5-chloro-2,4-difluorophenyl)-8-(((R)-3-hydroxy-2-(2-methoxyethoxy)propyl)thio)-6-(trifluoromethyl)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 75% yield as a yellow solid. m/z (ESI, +ve)=523.0 [M+H]$^+$ Step 3: tert-butyl 4-((3R)-11-(5-chloro-2,4-difluorophenyl)-3-(2-methoxyethoxy)-6-oxo-10-(trifluoromethyl)-3,4-dihydro-2H,6H-[1,4]thiazepino[2,3,4-ij]quinazolin-8-yl)piperazine-1-carboxylate

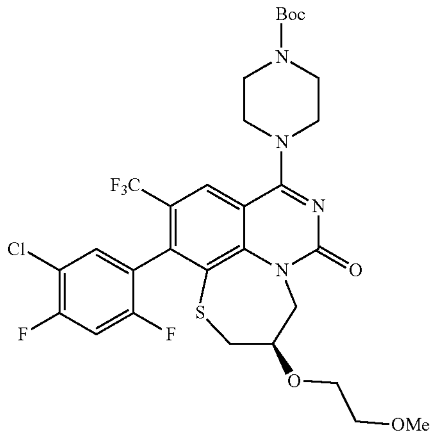 [SMILES: COCCO[C@H]1CSc2c(-c3cc(Cl)c(F)cc3F)c(C(F)(F)F)cc3c(N4CCN(C(=O)OC(C)(C)C)CC4)nc(=O)n(c23)C1]

The title compound was prepared analogously to Example 100, step 21 where (3R)-11-(5-chloro-2,4-difluorophenyl)-3-(2-methoxyethoxy)-10-(trifluoromethyl)-3,4-dihydro-2H,6H-[1,4]thiazepino[2,3,4-ij]quinazoline-6,8(7H)-dione and tert-butyl piperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 90% yield as a yellow solid. m/z (ESI, +ve)=691.2 [M+H]$^+$ Step 4: (3R)-11-(5-chloro-2,4-difluorophenyl)-3-(2-methoxyethoxy)-8-(piperazin-1-yl)-10-(trifluoromethyl)-3,4-dihydro-2H,6H-[1,4]thiazepino[2,3,4-ij]quinazolin-6-one

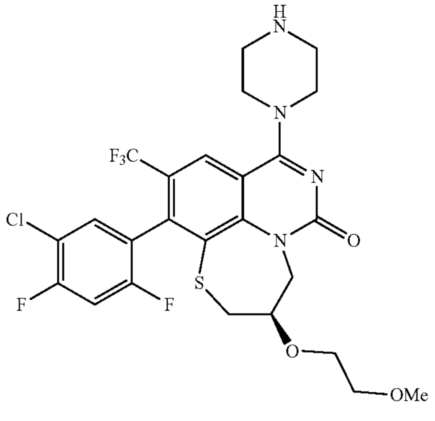 [SMILES: COCCO[C@H]1CSc2c(-c3cc(Cl)c(F)cc3F)c(C(F)(F)F)cc3c(N4CCNCC4)nc(=O)n(c23)C1]

The title compound was prepared analogously to Example 102, step 4, where tert-butyl 4-((3R)-11-(5-chloro-2,4-difluorophenyl)-3-(2-methoxyethoxy)-6-oxo-10-(trifluoromethyl)-3,4-dihydro-2H,6H-[1,4]thiazepino[2,3,4-ij]quinazolin-8-yl)piperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 88% yield as a yellow solid. m/z (ESI, +ve)=591.1 $[M+H]^+$ Example 1023: (3S)-8-(4-acryloylpiperazin-1-yl)-11-(5-chloro-2,4-difluorophenyl)-3-(2-methoxyethoxy)-10-(trifluoromethyl)-3,4-dihydro-2H,6H-[1,4]thiazepino[2,3,4-ij]quinazolin-6-one

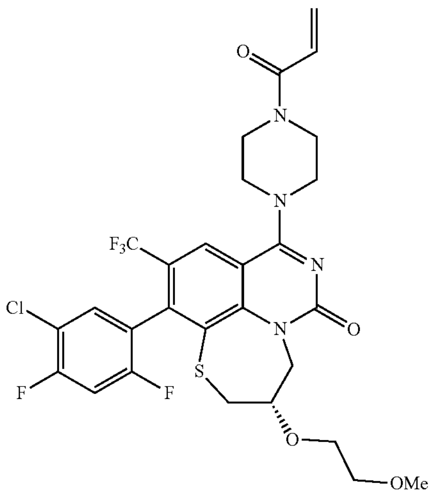 [SMILES: C=CC(=O)N1CCN(c2nc(=O)n3c4c(c(-c5cc(Cl)c(F)cc5F)c(C(F)(F)F)cc24)SC[C@@H](OCCOC)C3)CC1]

The title compound was prepared analogously to Example 84 where (3S)-11-(5-chloro-2,4-difluorophenyl)-3-(2-methoxyethoxy)-8-(piperazin-1-yl)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 36% yield as a yellow solid. m/z (ESI, +ve)=645.2 $[M+H]^+$ $^1$H NMR (400 MHz, DMSO-d6) δ 7.90 (s, 1H), 7.80-7.75 (m, 2H), 6.82 (dd, J=16.0, 8.0 Hz, 1H), 6.17 (dd, J=16.0, 4.0 Hz, 1H), 5.74 (dd, J=16.0, 4.0 Hz, 1H), 4.49-4.46 (m, 1H), 4.03-3.94 (m, 1H), 3.92-3.56 (m, 10H), 3.46-3.42 (m, 2H), 3.40-3.35 (m, 1H), 3.33-3.30 (m, 1H), 3.24 (s, 3H), 3.21-3.16 (m, 1H)

Step 1: 7-(5-chloro-2,4-difluorophenyl)-8-(((S)-3-hydroxy-2-(2-methoxyethoxy)propyl)thio)-6-(trifluoromethyl)quinazoline-2,4(1H,3H)-dione

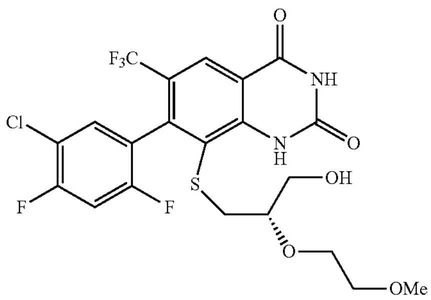 [SMILES: COCCO[C@@H](CO)CSc1c(-c2cc(Cl)c(F)cc2F)c(C(F)(F)F)cc2c(=O)[nH]c(=O)[nH]c12]

The title compound was synthesized analogously to example 100, step 9 where 7-(5-chloro-2,4-difluorophenyl)-8-iodo-6-(trifluoromethyl)quinazoline-2,4(1H,3H)-dione and (S)-3-mercapto-2-(2-methoxyethoxy)propan-1-ol were substituted in place of 7-(2,4-difluorophenyl)-8-iodo-6-(trifluoromethyl)quinazoline-2,4(1H,3H)-dione and 2-mercaptoethan-1-ol. The title compound was isolated in 86% yield as a white solid. m/z (ESI, +ve)=541.1 $[M+H]^+$.

Step 2: (3S)-11-(5-chloro-2,4-difluorophenyl)-3-(2-methoxyethoxy)-10-(trifluoromethyl)-3,4-dihydro-2H,6H-[1,4]thiazepino[2,3,4-ij]quinazoline-6,8(7H)-dione

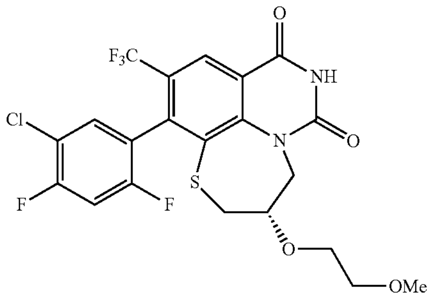 [SMILES: COCCO[C@@H]1CSc2c(-c3cc(Cl)c(F)cc3F)c(C(F)(F)F)cc3c(=O)[nH]c(=O)n(c23)C1]

The title compound was prepared analogously to Example 100, step 10 where 7-(5-chloro-2,4-difluorophenyl)-8-(((S)-3-hydroxy-2-(2-methoxyethoxy)propyl)thio)-6-(trifluoromethyl)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 70% yield as a yellow solid. m/z (ESI, +ve)=523.1 $[M+H]^+$ Step 3: tert-butyl 4-((3S)-11-(5-chloro-2,4-difluorophenyl)-3-(2-methoxyethoxy)-6-oxo-10-(trifluoromethyl)-3,4-dihydro-2H,6H-[1,4]thiazepino[2,3,4-ij]quinazolin-8-yl)piperazine-1-carboxylate N1

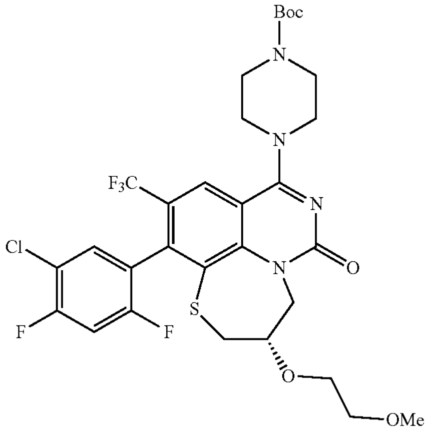 [SMILES: COCCO[C@@H]1CSc2c(-c3cc(Cl)c(F)cc3F)c(C(F)(F)F)cc3c(N4CCN(C(=O)OC(C)(C)C)CC4)nc(=O)n(c23)C1]

The title compound was prepared analogously to Example 100, step 21 where (3S)-11-(5-chloro-2,4-difluorophenyl)-3-(2-methoxyethoxy)-10-(trifluoromethyl)-3,4-dihydro-2H,6H-[1,4]thiazepino[2,3,4-ij]quinazoline-6,8(7H)-dione and tert-butyl piperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 84% yield as a yellow solid. m/z (ESI, +ve)=691.2 [M+H]$^+$ Step 4: (3S)-11-(5-chloro-2,4-difluorophenyl)-3-(2-methoxyethoxy)-8-(piperazin-1-yl)-10-(trifluoromethyl)-3,4-dihydro-2H,6H-[1,4]thiazepino[2,3,4-ij]quinazolin-6-one

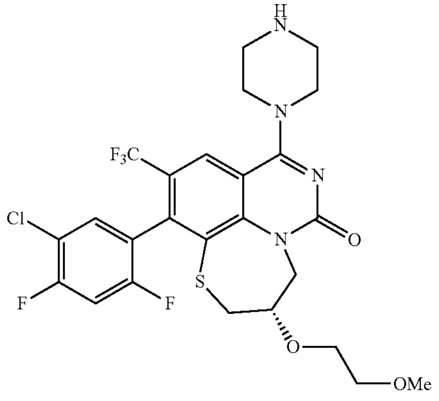 [SMILES: COCCO[C@@H]1CSc2c(-c3cc(Cl)c(F)cc3F)c(C(F)(F)F)cc3c(N4CCNCC4)nc(=O)n(c23)C1]

The title compound was prepared analogously to Example 102, step 4, where tert-butyl 4-((3S)-11-(5-chloro-2,4-difluorophenyl)-3-(2-methoxyethoxy)-6-oxo-10-(trifluoromethyl)-3,4-dihydro-2H,6H-[1,4]thiazepino[2,3,4-ij]quinazolin-8-yl)piperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 92% yield as a yellow solid. m/z (ESI, +ve)=591.1 [M+H]$^+$ Example 1024: (R)-8-((3S,5R)-4-acryloyl-3,5-dimethylpiperazin-1-yl)-11-(4-fluorophenyl)-3-(2-methoxyethoxy)-10-(trifluoromethyl)-3,4-dihydro-2H,6H-[1,4]thiazepino[2,3,4-ij]quinazolin-6-one

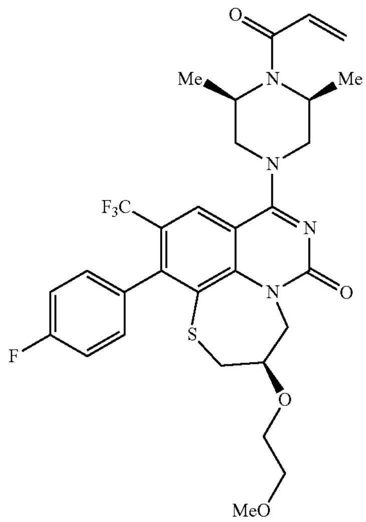 [SMILES: C=CC(=O)N1[C@H](C)CN(c2nc(=O)n3c4c(c(-c5ccc(F)cc5)c(C(F)(F)F)cc24)SC[C@H](OCCOC)C3)C[C@@H]1C]

The title compound was prepared analogously to Example 84 where (R)-8-((3S,5R)-3,5-dimethylpiperazin-1-yl)-11-(4-fluorophenyl)-3-(2-methoxyethoxy)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 31% yield as a yellow solid. m/z (ESI, +ve)=621.2 [M+H]$^+$ 1H NMR (400 MHz, DMSO) δ 8.02 (s, 1H), 7.35-7.32 (m, 4H), 6.82 (dd, J=16.0, 8.0 Hz, 1H), 6.19 (dd, J=16.0, 4.0 Hz, 1H), 5.74 (dd, J=16.0, 4.0 Hz, 1H), 4.61-4.57 (m, 2H), 4.49-4.46 (m, 1H), 4.09-4.04 (m, 2H), 3.96-3.94 (m, 1H), 3.61 (s, 1H), 3.43-3.41 (m, 2H), 3.32-3.25 (m, 5H), 3.25-3.21 (m, 3H), 3.11-3.05 (m, 1H), 1.40 (s, 6H).

Step 1: tert-butyl (2S,6R)-4-((R)-11-(4-fluorophenyl)-3-(2-methoxyethoxy)-6-oxo-10-(trifluoromethyl)-3,4-dihydro-2H,6H-[1,4]thiazepino[2,3,4-ij]quinazolin-8-yl)-2,6-dimethylpiperazine-1-carboxylate

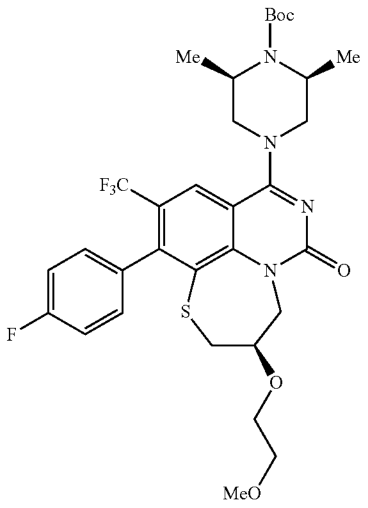 [SMILES: COCCO[C@H]1CSc2c(-c3ccc(F)cc3)c(C(F)(F)F)cc3c(N4C[C@@H](C)N(C(=O)OC(C)(C)C)[C@@H](C)C4)nc(=O)n(c23)C1]

The title compound was prepared analogously to Example 100, step 21 where (R)-11-(4-fluorophenyl)-3-(2-methoxyethoxy)-10-(trifluoromethyl)-3,4-dihydro-2H,6H-[1,4]thiazepino[2,3,4-ij]quinazoline-6,8(7H)-dione and tert-butyl (2S,6R)-2,6-dimethylpiperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 73% yield as a yellow solid. m/z (ESI, +ve)=667.2 [M+H]$^+$ Step 2: (R)-8-((3S,5R)-3,5-dimethylpiperazin-1-yl)-11-(4-fluorophenyl)-3-(2-methoxyethoxy)-10-(trifluoromethyl)-3,4-dihydro-2H,6H-[1,4]thiazepino[2,3,4-ij]quinazolin-6-one

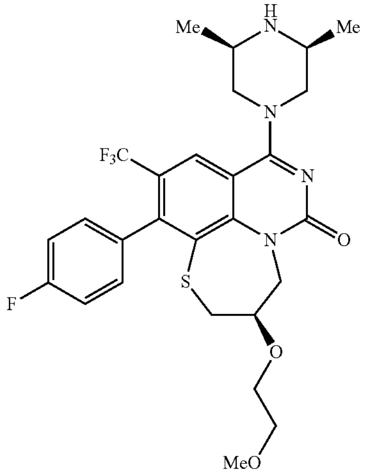 [SMILES: COCCO[C@H]1CSc2c(-c3ccc(F)cc3)c(C(F)(F)F)cc3c(N4C[C@@H](C)N[C@@H](C)C4)nc(=O)n(c23)C1]

The title compound was prepared analogously to Example 102, step 4, where tert-butyl (2S,6R)-4-((R)-11-(4-fluorophenyl)-3-(2-methoxyethoxy)-6-oxo-10-(trifluoromethyl)-3,4-dihydro-2H,6H-[1,4]thiazepino[2,3,4-ij]quinazolin-8-yl)-2,6-dimethylpiperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 95% yield as a yellow solid. m/z (ESI, +ve)=567.0 [M+H]$^+$ Example 1025: (S)-8-((3S,5R)-4-acryloyl-3,5-dimethylpiperazin-1-yl)-11-(4-fluorophenyl)-3-(2-methoxyethoxy)-10-(trifluoromethyl)-3,4-dihydro-2H,6H-[1,4]thiazepino[2,3,4-ij]quinazolin-6-one

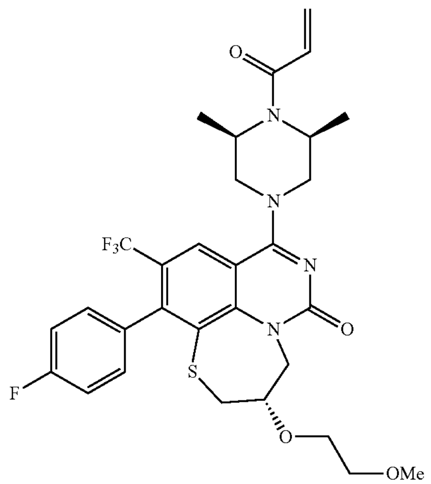 [SMILES: C=CC(=O)N1[C@H](C)CN(c2nc(=O)n3c4c(c(-c5ccc(F)cc5)c(C(F)(F)F)cc24)SC[C@@H](OCCOC)C3)C[C@@H]1C]

The title compound was prepared analogously to Example 84 where (S)-8-((3S,5R)-3,5-dimethylpiperazin-1-yl)-11-(4-fluorophenyl)-3-(2-methoxyethoxy)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 69% yield as a yellow solid. m/z (ESI, +ve)=667.2 [M+H]$^+$ Step 1: tert-butyl (2S,6R)-4-((S)-11-(4-fluorophenyl)-3-(2-methoxyethoxy)-6-oxo-10-(trifluoromethyl)-3,4-dihydro-2H,6H-[1,4]thiazepino[2,3,4-ij]quinazolin-8-yl)-2,6-dimethylpiperazine-1-carboxylate

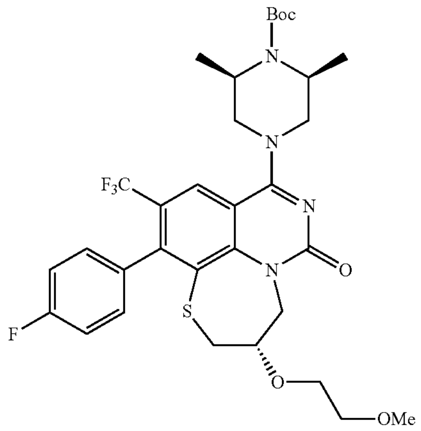 [SMILES: COCCO[C@@H]1CSc2c(-c3ccc(F)cc3)c(C(F)(F)F)cc3c(N4C[C@@H](C)N(C(=O)OC(C)(C)C)[C@@H](C)C4)nc(=O)n(c23)C1]

The title compound was prepared analogously to Example 100, step 21 where (S)-11-(4-fluorophenyl)-3-(2-methoxyethoxy)-10-(trifluoromethyl)-3,4-dihydro-2H,6H-[1,4]thiazepino[2,3,4-ij]quinazoline-6,8(7H)-dione and (2R,6S)-2,6-dimethylpiperazine were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 69% yield as a yellow solid. m/z (ESI, +ve)=667.2 $[M+H]^+$ Step 2: (S)-8-((3S,5R)-3,5-dimethylpiperazin-1-yl)-11-(4-fluorophenyl)-3-(2-methoxyethoxy)-10-(trifluoromethyl)-3,4-dihydro-2H,6H-[1,4]thiazepino[2,3,4-ij]quinazolin-6-one

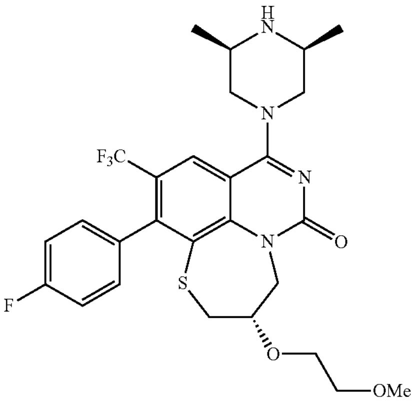 [SMILES: COCCO[C@@H]1CSc2c(-c3ccc(F)cc3)c(C(F)(F)F)cc3c(N4C[C@@H](C)N[C@@H](C)C4)nc(=O)n(c23)C1]

The title compound was prepared analogously to Example 102, step 4, where tert-butyl (2S,6R)-4-((S)-11-(4-fluorophenyl)-3-(2-methoxyethoxy)-6-oxo-10-(trifluoromethyl)-3,4-dihydro-2H,6H-[1,4]thiazepino[2,3,4-ij]quinazolin-8-yl)-2,6-dimethylpiperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 92% yield as a yellow solid. m/z (ESI, +ve)=567.2 $[M+H]^+$ Example 1026: (3R)-8-((3S,5R)-4-acryloyl-3,5-dimethylpiperazin-1-yl)-11-(2,4-difluorophenyl)-3-(2-methoxyethoxy)-10-(trifluoromethyl)-3,4-dihydro-2H,6H-[1,4]thiazepino[2,3,4-ij]quinazolin-6-one

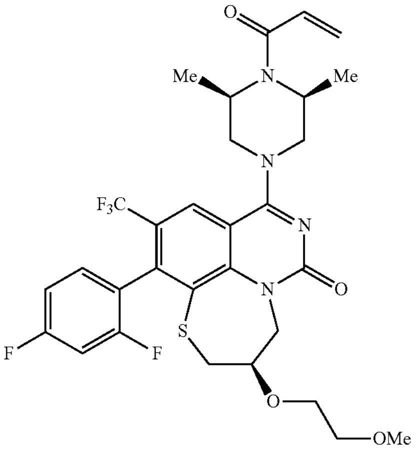 [SMILES: C=CC(=O)N1[C@H](C)CN(c2nc(=O)n3c4c(c(-c5ccc(F)cc5F)c(C(F)(F)F)cc24)SC[C@H](OCCOC)C3)C[C@@H]1C]

The title compound was prepared analogously to Example 84 where (3R)-11-(2,4-difluorophenyl)-8-((3S,5R)-3,5-dimethylpiperazin-1-yl)-3-(2-methoxyethoxy)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 26% yield as a yellow solid. m/z (ESI, +ve)=639.2 $[M+H]^+$ 1H NMR (400 MHz, DMSO) δ 8.04 (s, 1H), 7.46-7.42 (m, 2H), 7.29-7.25 (m, 1H), 6.81 (dd, J=16.0, 8.0 Hz, 1H), 6.19 (dd, J=16.0, 4.0 Hz, 1H), 5.74 (dd, J=16.0, 4.0 Hz, 1H), 4.66-4.38 (m, 3H), 4.15-3.93 (m, 3H), 3.64-3.60 (m, 2H), 3.45-3.40 (m, 2H), 3.35-3.31 (m, 3H), 3.25-3.21 (m, 4H), 3.17-3.13 (m, 1H), 1.42-1.38 (m, 6H).

Step 1: tert-butyl (2S,6R)-4-((3R)-11-(2,4-difluorophenyl)-3-(2-methoxyethoxy)-6-oxo-10-(trifluoromethyl)-3,4-dihydro-2H,6H-[1,4]thiazepino[2,3,4-ij]quinazolin-8-yl)-2,6-dimethylpiperazine-1-carboxylate

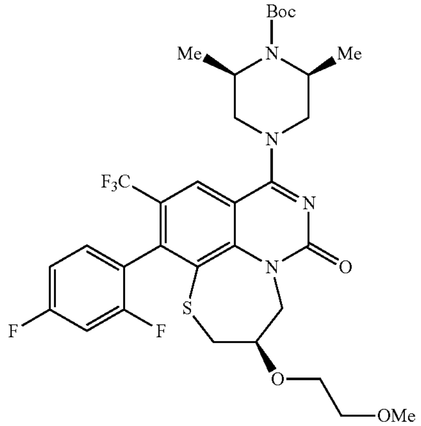 [SMILES: COCCO[C@H]1CSc2c(-c3ccc(F)cc3F)c(C(F)(F)F)cc3c(N4C[C@@H](C)N(C(=O)OC(C)(C)C)[C@@H](C)C4)nc(=O)n(c23)C1]

The title compound was prepared analogously to Example 100, step 21 where (3R)-11-(2,4-difluorophenyl)-3-(2-methoxyethoxy)-10-(trifluoromethyl)-3,4-dihydro-2H,6H-[1,4]thiazepino[2,3,4-ij]quinazoline-6,8(7H)-dione and tert-butyl (2R,6S)-2,6-dimethylpiperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 79% yield as a yellow solid. m/z (ESI, +ve)=685.2 $[M+H]^+$ Step 2: (3R)-11-(2,4-difluorophenyl)-8-((3S,5R)-3,5-dimethylpiperazin-1-yl)-3-(2-methoxyethoxy)-10-(trifluoromethyl)-3,4-dihydro-2H,6H-[1,4]thiazepino[2,3,4-ij]quinazolin-6-one

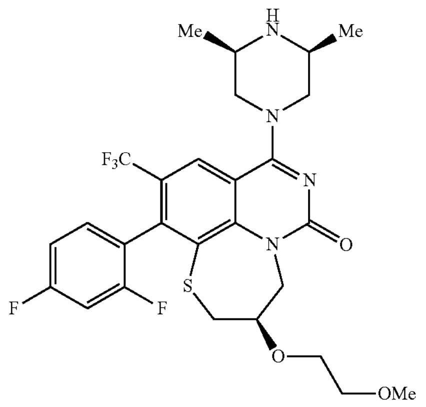 [SMILES: COCCO[C@H]1CSc2c(-c3ccc(F)cc3F)c(C(F)(F)F)cc3c(N4C[C@@H](C)N[C@@H](C)C4)nc(=O)n(c23)C1]

The title compound was prepared analogously to Example 102, step 4, where tert-butyl (2S,6R)-4-((3R)-11-(2,4-difluorophenyl)-3-(2-methoxyethoxy)-6-oxo-10-(trifluoromethyl)-3,4-dihydro-2H,6H-[1,4]thiazepino[2,3,4-ij]quinazolin-8-yl)-2,6-dimethylpiperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 94% yield as a yellow solid. m/z (ESI, +ve)=585.2 $[M+H]^+$ Example 1027: (3S)-8-((3S,5R)-4-acryloyl-3,5-dimethylpiperazin-1-yl)-11-(2,4-difluorophenyl)-3-(2-methoxyethoxy)-10-(trifluoromethyl)-3,4-dihydro-2H,6H-[1,4]thiazepino[2,3,4-ij]quinazolin-6-one 3,4-dihydro-2H,6H-[1,4]thiazepino[2,3,4-ij]quinazolin-6-one

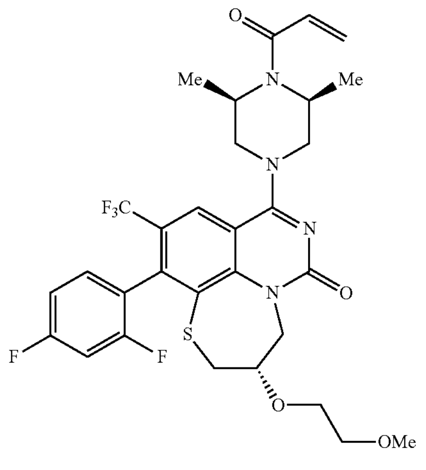 [SMILES: C=CC(=O)N1[C@H](C)CN(c2nc(=O)n3c4c(c(-c5ccc(F)cc5F)c(C(F)(F)F)cc24)SC[C@@H](OCCOC)C3)C[C@@H]1C]

The title compound was prepared analogously to example 84 where (3S)-11-(2,4-difluorophenyl)-3-(2-methoxyethoxy)-8-(piperazin-1-yl)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated as yellow solid in 18% yield. m/z (ESI, +ve)=639.2 $[M+H]^+$ 1H NMR (400 MHz, DMSO-d6) δ 8.04 (s, 1H), 7.52-7.33 (m, 2H), 7.29-7.22 (m, 1H), 6.81 (dd, J=16.0, 8.0 Hz, 1H), 6.19 (dd, J=16.0, 4.0 Hz, 1H), 5.74 (dd, J=16.0, 4.0 Hz, 1H), 4.77-4.23 (m, 4H), 4.18-3.90 (m, 3H), 3.79-3.55 (m, 2H), 3.50-3.36 (m, 3H), 3.34-3.30 (m, 1H), 3.28-3.25 (m, 1H), 3.24-3.19 (m, 3H), 3.18-3.09 (m, 1H), 1.60-1.13 (m, 6H).

Step 1: tert-butyl 4-((3S)-11-(2,4-difluorophenyl)-3-(2-methoxyethoxy)-6-oxo-10-(trifluoromethyl)-3,4-dihydro-2H,6H-[1,4]thiazepino[2,3,4-ij]quinazolin-8-yl)piperazine-1-carboxylate

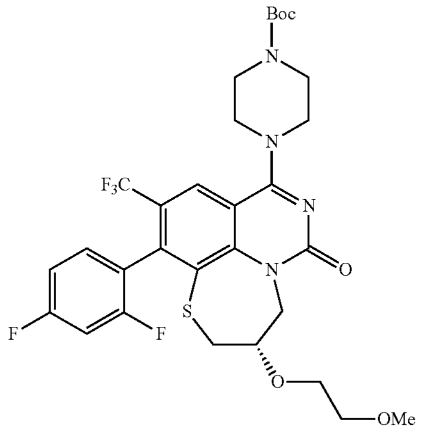 [SMILES: COCCO[C@@H]1CSc2c(-c3ccc(F)cc3F)c(C(F)(F)F)cc3c(N4CCN(C(=O)OC(C)(C)C)CC4)nc(=O)n(c23)C1]

The title compound was prepared analogously to Example 100, step 21 where (3S)-11-(2,4-difluorophenyl)-3-(2-methoxyethoxy)-10-(trifluoromethyl)-3,4-dihydro-2H,6H-[1,4]thiazepino[2,3,4-ij]quinazoline-6,8(7H)-dione and tert-butyl piperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 75% yield as a yellow solid. m/z (ESI, +ve)=685.2 $[M+H]^+$ Step 2: (3S)-11-(2,4-difluorophenyl)-3-(2-methoxyethoxy)-8-(piperazin-1-yl)-10-(trifluoromethyl)-3,4-dihydro-2H,6H-[1,4]thiazepino[2,3,4-ij]quinazolin-6-one

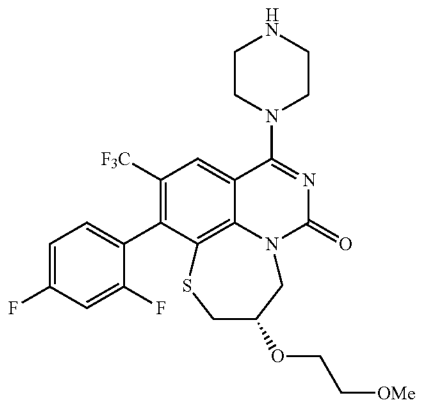 [SMILES: COCCO[C@@H]1CSc2c(-c3ccc(F)cc3F)c(C(F)(F)F)cc3c(N4CCNCC4)nc(=O)n(c23)C1]

The title compound was prepared analogously to Example 102, step 4, where tert-butyl 4-((3S)-11-(2,4-difluorophenyl)-3-(2-methoxyethoxy)-6-oxo-10-(trifluoromethyl)-3,4-dihydro-2H,6H-[1,4]thiazepino[2,3,4-ij]quinazolin-8-yl) piperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 97% yield as a yellow solid. m/z (ESI, +ve) =585.1 $[M+H]^+$ Example 1028: (R)-8-((3S,5R)-4-acryloyl-3,5-dimethylpiperazin-1-yl)-11-(3-chloro-4-fluorophenyl)-3-(2-methoxyethoxy)-10-(trifluoromethyl)-3,4-dihydro-2H,6H-[1,4]thiazepino[2,3,4-ij]quinazolin-6-one

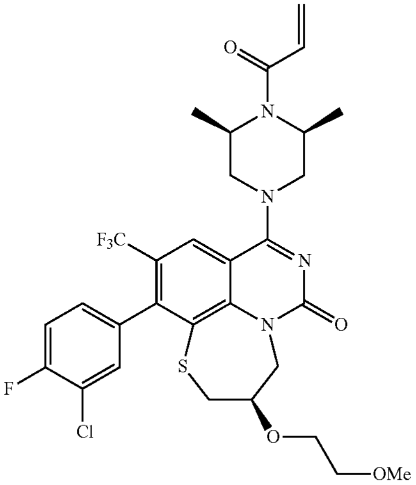 [SMILES: C=CC(=O)N1[C@H](C)CN(c2nc(=O)n3c4c(c(-c5ccc(F)c(Cl)c5)c(C(F)(F)F)cc24)SC[C@H](OCCOC)C3)C[C@@H]1C]

The title compound was prepared analogously to Example 84 where (R)-11-(3-chloro-4-fluorophenyl)-8-((3S,5R)-3,5-dimethylpiperazin-1-yl)-3-(2-methoxyethoxy)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo [3.3.1]nonan-7-yl)-2,3-dihydro-5H-[1,4]thiazino[2,3,4-ij] quinazolin-5-one. The title compound was isolated in 88% yield as a yellow solid. m/z (ESI, +ve)=655.2 $[M+H]^+$ 1H NMR (400 MHz, DMSO) δ 8.02 (s, 1H), 7.61-7.56 (m, 2H), 7.37-7.32 (m, 1H), 6.82 (dd, J=16.0, 8.0 Hz, 1H), 6.19 (dd, J=16.0, 4.0 Hz, 1H), 5.74 (dd, J=16.0, 4.0 Hz, 1H), 4.61-4.57 (m, 2H), 4.51-4.47 (m, 1H), 4.09-4.04 (m, 2H), 4.02-3.97 (m, 1H), 3.64-3.60 (m, 2H), 3.43-3.39 (m, 3H), 3.27-3.24 (m, 5H), 3.12-3.09 (m, 2H), 1.40 (s, 6H).

Step 1: (R)-11-(3-chloro-4-fluorophenyl)-8-((3S,5R)-3,5-dimethylpiperazin-1-yl)-3-(2-methoxyethoxy)-10-(trifluoromethyl)-3,4-dihydro-2H,6H-[1,4]thiazepino[2,3,4-ij]quinazolin-6-one

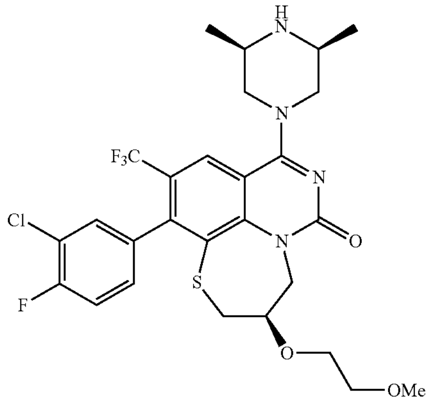 [SMILES: COCCO[C@H]1CSc2c(-c3ccc(F)c(Cl)c3)c(C(F)(F)F)cc3c(N4C[C@@H](C)N[C@@H](C)C4)nc(=O)n(c23)C1]

The title compound was prepared analogously to Example 100, step 21 where (R)-11-(3-chloro-4-fluorophenyl)-3-(2-methoxyethoxy)-10-(trifluoromethyl)-3,4-dihydro-2H,6H-[1,4]thiazepino[2,3,4-ij]quinazoline-6,8(7H)-dione and (2R,6S)-2,6-dimethylpiperazine were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 88% yield as a yellow solid. m/z (ESI, +ve)=601.2 $[M+H]^+$ Example 1029: (S)-8-((3S,5R)-4-acryloyl-3,5-dimethylpiperazin-1-yl)-11-(3-chloro-4-fluorophenyl)-3-(2-methoxyethoxy)-10-(trifluoromethyl)-3,4-dihydro-2H,6H-[1,4]thiazepino[2,3,4-ij]quinazolin-6-one

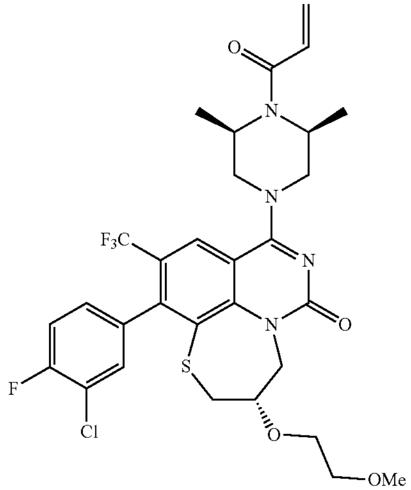 [SMILES: C=CC(=O)N1[C@H](C)CN(c2nc(=O)n3c4c(c(-c5ccc(F)c(Cl)c5)c(C(F)(F)F)cc24)SC[C@@H](OCCOC)C3)C[C@@H]1C]

The title compound was prepared analogously to Example 84 where (S)-11-(3-chloro-4-fluorophenyl)-8-((3S,5R)-3,5-dimethylpiperazin-1-yl)-3-(2-methoxyethoxy)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo [3.3.1]nonan-7-yl)-2,3-dihydro-5H-[1,4]thiazino[2,3,4-ij]

quinazolin-5-one. The title compound was isolated in 88% yield as a yellow solid. m/z (ESI, +ve)=655.2 [M+H]+

1H NMR (400 MHz, DMSO) δ 8.02 (s, 1H), 7.60-7.56 (m, 2H), 7.37 (s, 1H), 6.82 (dd, J=16.0, 8.0 Hz, 1H), 6.19 (dd, J=16.0, 4.0 Hz, 1H), 5.74 (dd, J=16.0, 4.0 Hz, 1H), 4.65-4.44 (m, 3H), 4.07-4.01 (m, 3H), 3.64-3.60 (m, 2H), 3.45-3.41 (m, 2H), 3.37-3.32 (m, 3H), 3.31-3.27 (m, 1H), 3.25-3.21 (m, 3H), 3.17-3.05 (m, 1H), 1.39 (s, 6H).

Step 1: (S)-11-(3-chloro-4-fluorophenyl)-8-((3S, 5R)-3,5-dimethylpiperazin-1-yl)-3-(2-methoxy-ethoxy)-10-(trifluoromethyl)-3,4-dihydro-2H,6H-[1, 4]thiazepino[2,3,4-ij]quinazolin-6-one

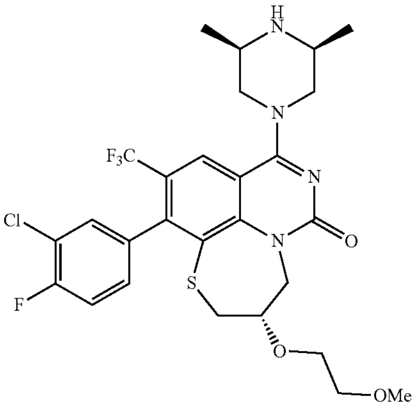 [SMILES: COCCO[C@@H]1CSc2c(-c3ccc(F)c(Cl)c3)c(C(F)(F)F)cc3c(N4C[C@@H](C)N[C@@H](C)C4)nc(=O)n(c23)C1]

The title compound was prepared analogously to Example 100, step 21 where (S)-11-(3-chloro-4-fluorophenyl)-3-(2-methoxyethoxy)-10-(trifluoromethyl)-3,4-dihydro-2H,6H-[1,4]thiazepino[2,3,4-ij]quinazoline-6,8(7H)-dione and (2R, 6S)-2,6-dimethylpiperazine were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 65% yield as a yellow solid. m/z (ESI, +ve)=601.2 [M+H]+

Example 1030: (3R)-8-((3S,5R)-4-acryloyl-3,5-dimethylpiperazin-1-yl)-11-(5-chloro-2,4-difluorophenyl)-3-(2-methoxyethoxy)-10-(trifluoromethyl)-3,4-dihydro-2H,6H-[1,4]thiazepino[2,3,4-ij]quinazolin-6-one

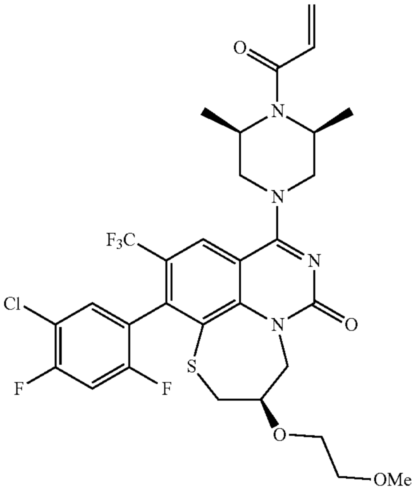 [SMILES: C=CC(=O)N1[C@H](C)CN(c2nc(=O)n3c4c(c(-c5cc(Cl)c(F)cc5F)c(C(F)(F)F)cc24)SC[C@H](OCCOC)C3)C[C@@H]1C]

The title compound was prepared analogously to Example 84 where (3R)-11-(5-chloro-2,4-difluorophenyl)-8-((3S, 5R)-3,5-dimethylpiperazin-1-yl)-3-(2-methoxyethoxy)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 28% yield as a yellow solid. m/z (ESI, +ve)=673.2 [M+H]+

1H NMR (400 MHz, DMSO-$d_6$) δ 8.04 (s, 1H), 7.80-7.76 (m, 2H), 6.81 (dd, J=16.0, 8.0 Hz, 1H), 6.19 (d, J=16.0, 4.0 Hz, 1H), 5.74 (d, J=16.0, 4.0 Hz, 1H), 4.65-4.54 (m, 2H), 4.51-4.43 (m, 1H), 4.13-3.95 (m, 3H), 3.69-3.54 (m, 2H), 3.44-3.42 (m, 2H), 3.35-3.32 (m, 2H), 3.31-3.13 (m, 6H), 1.52-1.28 (m, 6H).

Step 1: tert-butyl (2S,6R)-4-((3R)-11-(5-chloro-2,4-difluorophenyl)-3-(2-methoxyethoxy)-6-oxo-10-(trifluoromethyl)-3,4-dihydro-2H,6H-[1,4]thiazepino[2,3,4-ij]quinazolin-8-yl)-2,6-dimethylpiperazine-1-carboxylate

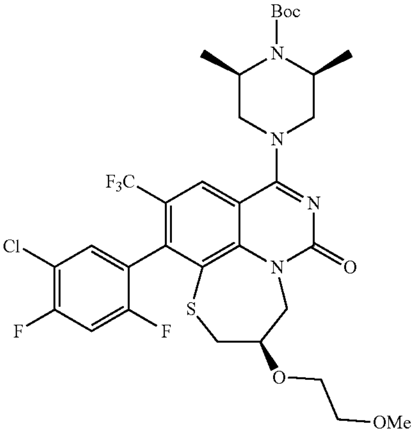 [SMILES: COCCO[C@H]1CSc2c(-c3cc(Cl)c(F)cc3F)c(C(F)(F)F)cc3c(N4C[C@@H](C)N(C(=O)OC(C)(C)C)[C@@H](C)C4)nc(=O)n(c23)C1]

The title compound was prepared analogously to Example 100, step 21 where 3R)-11-(5-chloro-2,4-difluorophenyl)-3-(2-methoxyethoxy)-10-(trifluoromethyl)-3,4-dihydro-2H, 6H-[1,4]thiazepino[2,3,4-ij]quinazoline-6,8(7H)-dione and tert-butyl (2S,6R)-2,6-dimethylpiperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 93% yield as a yellow solid. m/z (ESI, +ve)=719.2 [M+H]+

Step 2: (3R)-11-(5-chloro-2,4-difluorophenyl)-8-((3S,5R)-3,5-dimethylpiperazin-1-yl)-3-(2-methoxyethoxy)-10-(trifluoromethyl)-3,4-dihydro-2H,6H-[1,4]thiazepino[2,3,4-ij]quinazolin-6-one

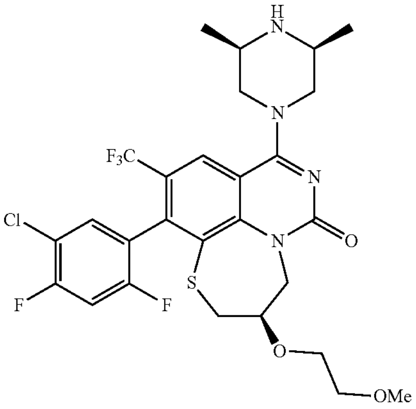 [SMILES: COCCO[C@H]1CSc2c(-c3cc(Cl)c(F)cc3F)c(C(F)(F)F)cc3c(N4C[C@@H](C)N[C@@H](C)C4)nc(=O)n(c23)C1]

The title compound was prepared analogously to Example 102, step 4, where tert-butyl (2S,6R)-4-((3R)-11-(5-chloro-2,4-difluorophenyl)-3-(2-methoxyethoxy)-6-oxo-10-(trifluoromethyl)-3,4-dihydro-2H,6H-[1,4]thiazepino[2,3,4-ij]quinazolin-8-yl)-2,6-dimethylpiperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 90% yield as a yellow solid. m/z (ESI, +ve)=619.1 $[M+H]^+$ Example 1031: (3S)-8-((3S,5R)-4-acryloyl-3,5-dimethylpiperazin-1-yl)-11-(5-chloro-2,4-difluorophenyl)-3-(2-methoxyethoxy)-10-(trifluoromethyl)-3,4-dihydro-2H,6H-[1,4]thiazepino[2,3,4-ij]quinazolin-6-one

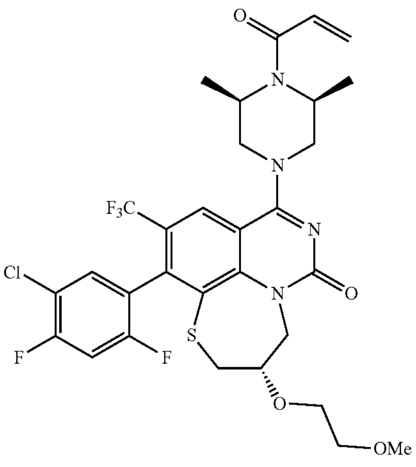 [SMILES: C=CC(=O)N1[C@H](C)CN(c2nc(=O)n3c4c(c(-c5cc(Cl)c(F)cc5F)c(C(F)(F)F)cc24)SC[C@@H](OCCOC)C3)C[C@@H]1C]

The title compound was prepared analogously to example 84 where (3S)-11-(5-chloro-2,4-difluorophenyl)-8-((3S,5R)-3,5-dimethylpiperazin-1-yl)-3-(2-methoxyethoxy)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated as a pale yellow solid in 21% yield. m/z (ESI, +ve)=673.0 $[M+H]^+$ 1H NMR (400 MHz, DMSO-$d_6$) δ 8.04 (s, 1H), 7.80-7.76 (m, 2H), 6.81 (dd, J=16.0, 8.0 Hz, 1H), 6.19 (dd, J=16.0, 4.0 Hz, 1H), 5.74 (dd, J=16.0, 4.0 Hz, 1H), 4.68-4.42 (m, 3H), 4.13-3.98 (m, 3H), 3.65-3.61 (m, 2H), 3.45-3.41 (m, 2H), 3.36-3.30 (m, 4H), 3.25-3.22 (m, 3H), 3.19-3.15 (m, 1H), 1.43-1.37 (m, 6H).

Step 1: tert-butyl (2S,6R)-4-((3S)-11-(5-chloro-2,4-difluorophenyl)-3-(2-methoxyethoxy)-6-oxo-10-(trifluoromethyl)-3,4-dihydro-2H,6H-[1,4]thiazepino[2,3,4-ij]quinazolin-8-yl)-2,6-dimethylpiperazine-1-carboxylate

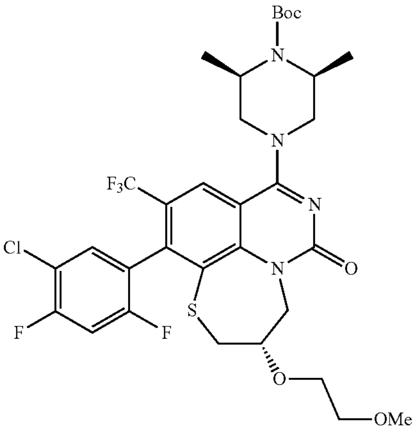 [SMILES: COCCO[C@@H]1CSc2c(-c3cc(Cl)c(F)cc3F)c(C(F)(F)F)cc3c(N4C[C@@H](C)N(C(=O)OC(C)(C)C)[C@@H](C)C4)nc(=O)n(c23)C1]

The title compound was prepared analogously to Example 100, step 21 where (3S)-11-(5-chloro-2,4-difluorophenyl)-3-(2-methoxyethoxy)-10-(trifluoromethyl)-3,4-dihydro-2H,6H-[1,4]thiazepino[2,3,4-ij]quinazoline-6,8(7H)-dione and tert-butyl (2S,6R)-2,6-dimethylpiperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 60% yield as a yellow solid. m/z (ESI, +ve)=719.3 $[M+H]^+$ Step 2: (3S)-11-(5-chloro-2,4-difluorophenyl)-8-((3S,5R)-3,5-dimethylpiperazin-1-yl)-3-(2-methoxy-ethoxy)-10-(trifluoromethyl)-3,4-dihydro-2H,6H-[1,4]thiazepino[2,3,4-ij]quinazolin-6-one

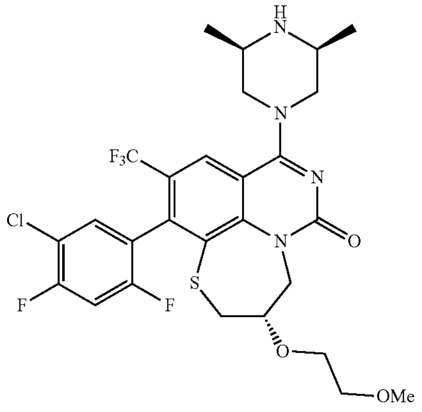 [SMILES: COCCO[C@@H]1CSc2c(-c3cc(Cl)c(F)cc3F)c(C(F)(F)F)cc3c(N4C[C@@H](C)N[C@@H](C)C4)nc(=O)n(c23)C1]

The title compound was prepared analogously to Example 102, step 4, where tert-butyl (2S,6R)-4-((3S)-11-(5-chloro-2,4-difluorophenyl)-3-(2-methoxyethoxy)-6-oxo-10-(trifluoromethyl)-3,4-dihydro-2H,6H-[1,4]thiazepino[2,3,4-ij]quinazolin-8-yl)-2,6-dimethylpiperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 95% yield as a yellow solid. m/z (ESI, +ve)=619.1 $[M+H]^+$ Example 1032: (S)-8-((3S,5R)-4-acryloyl-3,5-dimethylpiperazin-1-yl)-3-amino-11-(4-fluorophenyl)-10-(trifluoromethyl)-3,4-dihydro-2H,6H-[1,4]thiazepino[2,3,4-ij]quinazolin-6-one

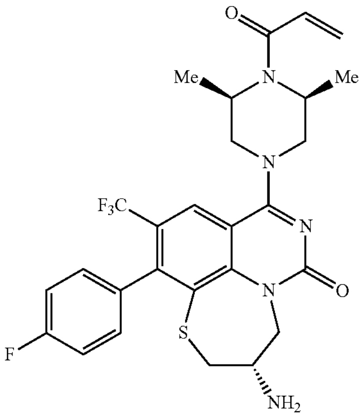

Over a solution of tert-butyl ((S)-8-((3S,5R)-4-acryloyl-3,5-dimethylpiperazin-1-yl)-11-(4-fluorophenyl)-6-oxo-10-(trifluoromethyl)-3,4-dihydro-2H,6H-[1,4]thiazepino[2,3,4-ij]quinazolin-3-yl)carbamate (0.03 mmol) in dichloromethane (1 mL) was added trifluoroacetic acid (0.3 mL) and the resulting mixture stirred at room temperature for one hour. The reaction was quenched with water and extracted with dichloromethane three times. The organic layers were combined, washed with brine and dried over sodium sulfate. The volatiles were removed under reduced pressure to afford a residue that was purified by preparative HPLC to afford the title compound as a yellow solid. m/z (ESI, +ve)=562.2 $[M+H]^+$ $^1H$ NMR (400 MHz, DMSO-$d_6$) δ 8.02 (s, 1H), 7.43-7.25 (m, 4H), 6.82 (dd, J=16.0, 8.0 Hz, 1H), 6.19 (dd, J=16.0, 4.0 Hz, 1H), 5.74 (dd, J=8.0, 4.0 Hz, 1H), 4.61-4.57 (m, 2H), 4.42-4.38 (m, 1H), 4.05 (d, J=12.0 Hz, 2H), 3.27-3.17 (m, 5H), 2.79 (s, 1H), 1.44-1.37 (m, 6H).

Step 1: (R)-1-((tert-butyldiphenylsilyl)oxy)-3-(tritylthio)propan-2-ol

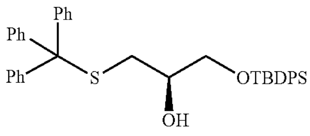

TBDPSCl (56.7 mmol) was added over a 0° C. solution of (2R)-3-[(triphenylmethyl)sulfanyl]propane-1,2-diol (57.1 mmol) and imidazole (141.2 mmol) in DMF (100 mL). The mixture was stirred at room temperature for 16 hours and diluted with water. The reaction mixture was extracted with ethyl acetate three times and the combined organic layers dried over sodium sulfate to afford a residue that was purified by silica gel chromatography (0-15% ethyl acetate in hexanes). The title compound was isolated as a colorless oil in 98% yield. m/z (ESI, +ve)=611.2 $[M+H]^+$ Step 2: (S)-(2-azido-3-(tritylthio)propoxy)(tert-butyl)diphenylsilane

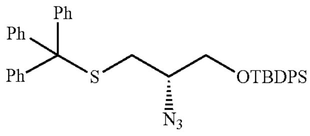

Over a 0° C. solution of (R)-1-((tert-butyldiphenylsilyl)oxy)-3-(tritylthio)propan-2-ol (52.6 mmol) and triphenyl phosphine (105 mmol) in THF (300 mL) was added DEAD (105.2 mmol). After 20 minutes, diphenylphosphoryl azide (69.1 mmol) was slowly added and the mixture stirred at room temperature for 16 hours. The reaction was quenched by the addition of water and the resulting mixture was extracted with ethyl acetate three times. The combined organic layers were dried over sodium sulfate to afford a residue that was purified by silica gel chromatography (0-10% ethyl acetate in hexanes). The title compound was isolated as a colorless oil in 90% yield as a colorless oil.

Step 3: (S)-2-azido-3-((tert-butyldiphenylsilyl)oxy)propane-1-thiol

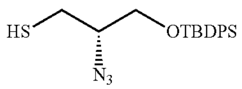

Triethylsilane (0.15 mmol) was added over a solution of (S)-(2-azido-3-(tritylthio)propoxy)(tert-butyl)diphenylsilane (53.8 mmol) in dichloromethane (150 mL) and trifluoroacetic acid (35 mL) at room temperature. After 20 minutes, the reaction was quenched with water and extracted with dichloromethane three times. The combined organic layers were washed with brine and dried over sodium sulfate to afford a residue that was purified by silica gel chromatography (0-8% methanol in dichloromethane). The title compound was isolated as a colorless oil in 50% yield as a yellow oil.

Step 4: (S)-8-((2-amino-3-((tert-butyldiphenylsilyl)oxy)propyl)thio)-7-(4-fluorophenyl)-6-(trifluoromethyl)quinazoline-2,4(1H,3H)-dione

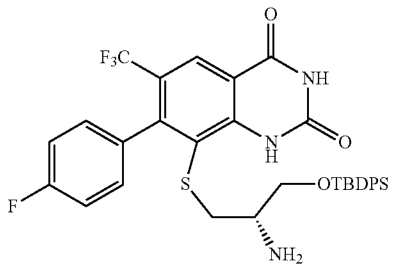

The title compound was synthesized analogously to example 100, step 9 where (S)-8-((2-amino-3-((tert-butyldiphenylsilyl)oxy)propyl)thio)-7-(4-fluorophenyl)-6-(trifluoromethyl)quinazoline-2,4(1H,3H)-dione and (S)-2-azido-3-((tert-butyldiphenylsilyl)oxy)propane-1-thiol were substituted in place of 7-(2,4-difluorophenyl)-8-iodo-6-(trifluoromethyl)quinazoline-2,4(1H,3H)-dione and 2-mercaptoethan-1-ol. The title compound was isolated in 37% yield as a green solid. m/z (ESI, +ve)=668.0 $[M+H]^+$ Step 5: tert-butyl (S)-(1-((tert-butyldiphenylsilyl)oxy)-3-((7-(4-fluorophenyl)-2,4-dioxo-6-(trifluoromethyl)-1,2,3,4-tetrahydroquinazolin-8-yl)thio)propan-2-yl)carbamate

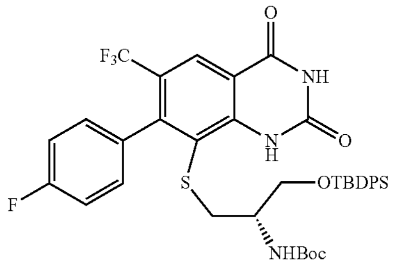

Boc anhydride (1.66 mmol) and triethylamine (3.27 mmol) were added over a solution of (S)-8-((2-amino-3-((tert-butyldiphenylsilyl)oxy)propyl)thio)-7-(4-fluorophenyl)-6-(trifluoromethyl)quinazoline-2,4(1H,3H)-dione (1.11 mmol) in THF (15 mL). The mixture was stirred at room temperature for 16 hours and the volatiles were removed under reduced pressure. The resulting residue was purified by reverse phase chromatography (70-98% acetonitrile in water with 0.10% TFA) to afford the title compounds as a colorless oil in 52% yield. m/z (ESI, +ve)=789.9 $[M+H]^+$ Step 6: tert-butyl (S)-(1-((7-(4-fluorophenyl)-2,4-dioxo-6-(trifluoromethyl)-1,2,3,4-tetrahydroquinazolin-8-yl)thio)-3-hydroxypropan-2-yl)carbamate

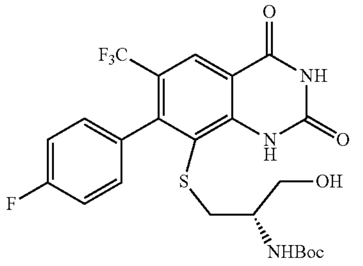 [SMILES: CC(C)(C)OC(=O)N[C@@H](CO)CSc1c(-c2ccc(F)cc2)c(C(F)(F)F)cc2c(=O)[nH]c(=O)[nH]c12]

A 1M THF solution of tetrabutylammonium fluoride (0.85 mmol) was added was added over a solution of tert-butyl (S)-(1-((tert-butyldiphenylsilyl)oxy)-3-((7-(4-fluorophenyl)-2,4-dioxo-6-(trifluoromethyl)-1,2,3,4-tetrahydroquinazolin-8-yl)thio)propan-2-yl)carbamate (0.57 mmol) in THF (8 mL) at room temperature. After 30 minutes the mixture was concentrated under reduced pressure and the resulting residue was purified by reverse phase chromatography (40-70% acetonitrile in water with 0.1% TFA) to afford the title compounds as a white solid in 99% yield. m/z (ESI, +ve)=552.0 $[M+H]^+$ Step 7: tert-butyl (S)-(11-(4-fluorophenyl)-6,8-dioxo-10-(trifluoromethyl)-3,4,7,8-tetrahydro-2H,6H-[1,4]thiazepino[2,3,4-ij]quinazolin-3-yl)carbamate

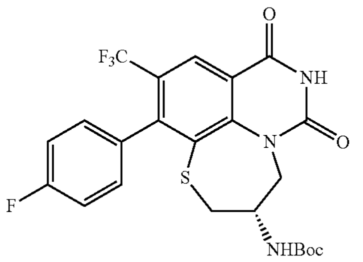 [SMILES: CC(C)(C)OC(=O)N[C@@H]1CSc2c(-c3ccc(F)cc3)c(C(F)(F)F)cc3c(=O)[nH]c(=O)n(c23)C1]

The title compound was prepared analogously to Example 100, step 10 where tert-butyl (S)-(1-((7-(4-fluorophenyl)-2,4-dioxo-6-(trifluoromethyl)-1,2,3,4-tetrahydroquinazolin-8-yl)thio)-3-hydroxypropan-2-yl)carbamate was substituted in place of 7-(2,4-difluorophenyl)-8-((2-hydroxyethyl)thio)-6-(trifluoromethyl)quinazoline-2,4(1H,3H)-dione in 85% yield as a white solid after purification by reverse phase chromatography (30-60% acetonitrile in water with 0.1% TFA). m/z (ESI, +ve)=534.0 $[M+H]^+$ Step 8: tert-butyl ((S)-8-((3S,5R)-4-acryloyl-3,5-dimethylpiperazin-1-yl)-11-(4-fluorophenyl)-6-oxo-10-(trifluoromethyl)-3,4-dihydro-2H,6H-[1,4]thiazepino[2,3,4-ij]quinazolin-3-yl)carbamate

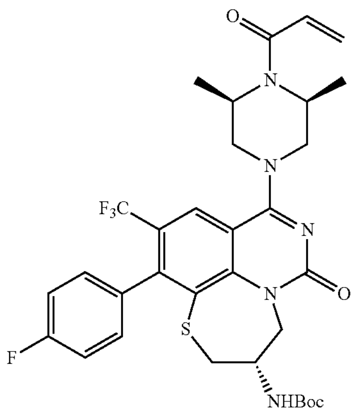 [SMILES: C=CC(=O)N1[C@H](C)CN(c2nc(=O)n3c4c(c(-c5ccc(F)cc5)c(C(F)(F)F)cc24)SC[C@@H](NC(=O)OC(C)(C)C)C3)C[C@@H]1C]

The title compound was prepared analogously to Example 100, step 21 where tert-butyl (S)-(11-(4-fluorophenyl)-6,8-dioxo-10-(trifluoromethyl)-3,4,7,8-tetrahydro-2H,6H-[1,4]thiazepino[2,3,4-ij]quinazolin-3-yl)carbamate and 1-((2S,6R)-2,6-dimethylpiperazin-1-yl)prop-2-en-1-one were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated a yellow oil. m/z (ESI, +ve)=291.1 $[M+H]^+$ Example 1033: (S)-8-((3S,5R)-4-acryloyl-3,5-dimethylpiperazin-1-yl)-3-(2-(dimethylamino)ethoxy)-11-(4-fluorophenyl)-10-(trifluoromethyl)-3,4-dihydro-2H,6H-[1,4]thiazepino[2,3,4-ij]quinazolin-6-one

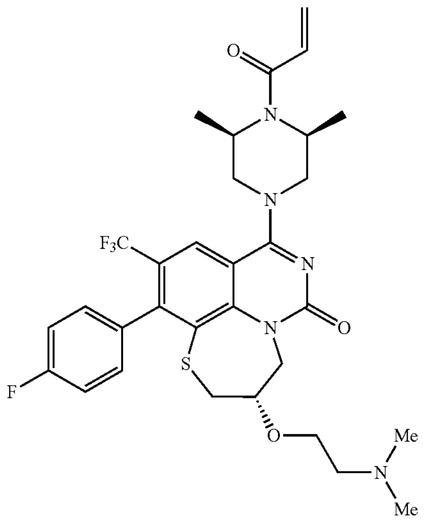 [SMILES: C=CC(=O)N1[C@H](C)CN(c2nc(=O)n3c4c(c(-c5ccc(F)cc5)c(C(F)(F)F)cc24)SC[C@@H](OCCN(C)C)C3)C[C@@H]1C]

The title compound was prepared analogously to Example 84 where (S)-3-(2-(dimethylamino)ethoxy)-8-((3S,5R)-3,5-dimethylpiperazin-1-yl)-11-(4-fluorophenyl)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 7% yield as a white solid. m/z (ESI, +ve)=634.3 $[M+H]^+$ 1H NMR (400 MHz, DMSO) δ 8.02 (s, 1H), 7.35 (d, J=8.0 Hz, 4H), 6.82 (dd, J=16.0, 8.0 Hz, 1H), 6.19 (dd, J=16.0, 4.0 Hz, 1H), 5.74 (dd, J=16.0, 4.0 Hz, 1H), 4.64-4.44 (m, 3H), 4.09-4.05 (m, 2H), 3.97-3.93 (m, 1H), 3.55-3.51 (m, 2H), 3.35-3.31 (m, 4H), 3.12-3.08 (m, 1H), 2.43-2.40 (m, 2H), 2.16 (s, 6H), 1.40 (s, 3H), 1.27-1.16 (m, 3H).

Step 1: (S)-2-((1-((tert-butyldimethylsilyl)oxy)-3-(tritylthio)propan-2-yl)oxy)-N,N-dimethylethane-1-amine

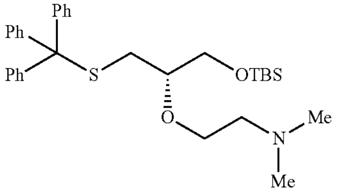 [SMILES: CN(C)CCO[C@@H](CO[Si](C)(C)C(C)(C)C)CSC(c1ccccc1)(c1ccccc1)c1ccccc1]

Sodium hydride (0.11 mmol) was added over a solution of tert-butyl[(2S)-2-hydroxy-3-[(triphenylmethyl)sulfanyl]propoxy]dimethylsilane (0.011 mmol) in dioxane (50 mL) at room temperature. After 30 minutes (2-bromoethyl)dimethylamine hydrobromide (0.04 mmol) was added and the mixture was stirred at 95° C. for two additional hours. The reaction was stopped by the addition of water and extracted with dichloromethane three times. The organic layers were combined, washed with brine and dried over sodium sulfate. Evaporation of volatiles under reduced pressure afforded a residue that was purified by silica gel chromatography to afford the title compound as a yellow oil in 65% yield.

Step 2: (S)-2-(2-(dimethylamino)ethoxy)-3-mercaptopropan-1-ol

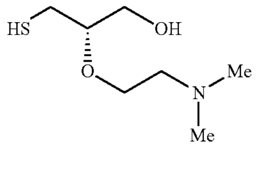 [SMILES: CN(C)CCO[C@@H](CO)CS]

Triethylsilane (0.022 mmol) was added over a solution of (S)-2-((1-((tert-butyldimethylsilyl)oxy)-3-(tritylthio)propan-2-yl)oxy)-N,N-dimethylethane-1-amine (0.008 mmol) in dichloromethane (30 mL) and trifluoroacetic acid (10 mL) at room temperature. After 30 minutes, water was added and the mixture extracted with dichloromethane three times. The organic layers were combined, washed with brine and dried over sodium sulfate. Evaporation of volatiles under reduced pressure afforded the title compound as a colorless oil in 98% yield.

Step 3: (S)-8-((2-(2-(dimethylamino)ethoxy)-3-hydroxypropyl)thio)-7-(4-fluorophenyl)-6-(trifluoromethyl)quinazoline-2,4(1H,3H)-dione

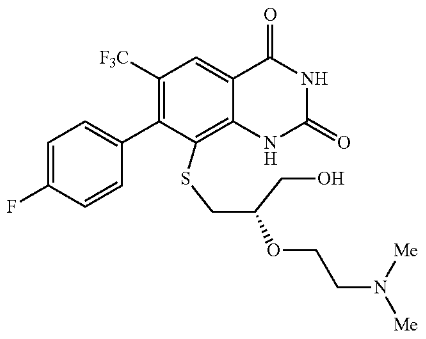 [SMILES: CN(C)CCO[C@@H](CO)CSc1c(-c2ccc(F)cc2)c(C(F)(F)F)cc2c(=O)[nH]c(=O)[nH]c12]

The title compound was synthesized analogously to example 100, step 9 where 7-(4-fluorophenyl)-8-iodo-6-(trifluoromethyl)quinazoline-2,4(1H,3H)-dione and (S)-2-(2-(dimethylamino)ethoxy)-3-mercaptopropan-1-ol were substituted in place of 7-(2,4-difluorophenyl)-8-iodo-6-(trifluoromethyl)quinazoline-2,4(1H,3H)-dione and 2-mercaptoethan-1-ol. The title compound was isolated in 67% yield as a yellow solid. m/z (ESI, +ve)=502.1 [M+H]$^+$ Step 4: (S)-3-(2-(dimethylamino)ethoxy)-11-(4-fluorophenyl)-10-(trifluoromethyl)-3,4-dihydro-2H,6H-[1,4]thiazepino[2,3,4-ij]quinazoline-6,8(7H)-dione

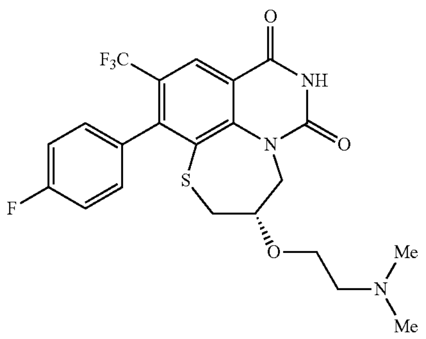 [SMILES: CN(C)CCO[C@@H]1CSc2c(-c3ccc(F)cc3)c(C(F)(F)F)cc3c(=O)[nH]c(=O)n(c23)C1]

The title compound was prepared analogously to Example 100, step 10 where (S)-8-((2-(2-(dimethylamino)ethoxy)-3-hydroxypropyl)thio)-7-(4-fluorophenyl)-6-(trifluoromethyl)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 71% yield as a yellow solid. m/z (ESI, +ve)=484.1 [M+H]$^+$ Step 5: (S)-3-(2-(dimethylamino)ethoxy)-8-((3S,5R)-3,5-dimethylpiperazin-1-yl)-11-(4-fluorophenyl)-10-(trifluoromethyl)-3,4-dihydro-2H,6H-[1,4]thiazepino[2,3,4-ij]quinazolin-6-one

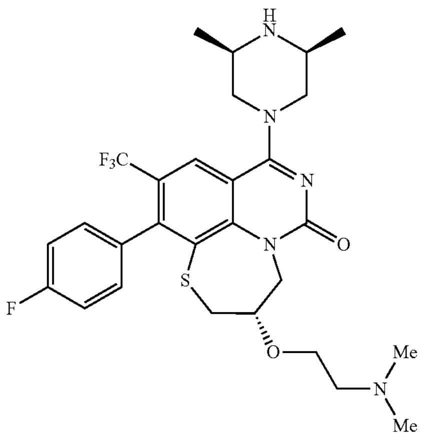 [SMILES: C[C@@H]1CN(c2nc(=O)n3c4c(c(-c5ccc(F)cc5)c(C(F)(F)F)cc24)SC[C@@H](OCCN(C)C)C3)C[C@H](C)N1]

The title compound was prepared analogously to Example 100, step 21 where (S)-3-(2-(dimethylamino)ethoxy)-11-(4-fluorophenyl)-10-(trifluoromethyl)-3,4-dihydro-2H,6H-[1,4]thiazepino[2,3,4-ij]quinazoline-6,8(7H)-dione and (2S,6R)-2,6-dimethylpiperazine were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 4% yield as a yellow solid. m/z (ESI, +ve)=580.3 [M+H]$^+$ Example 1034: (3S)-8-((3S,5R)-4-acryloyl-3,5-dimethylpiperazin-1-yl)-11-(2,4-difluorophenyl)-3-(2-(dimethylamino)ethoxy)-10-(trifluoromethyl)-3,4-dihydro-2H,6H-[1,4]thiazepino[2,3,4-ij]quinazolin-6-one

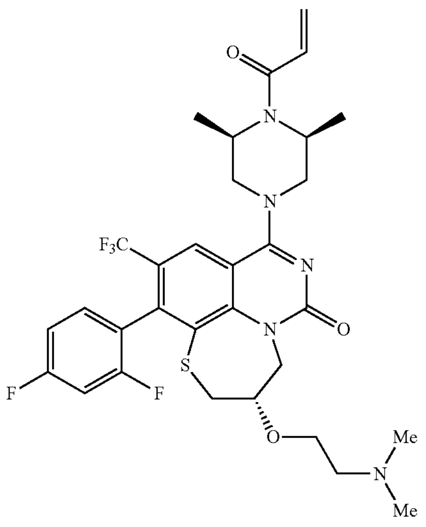 [SMILES: C=CC(=O)N1[C@H](C)CN(c2nc(=O)n3c4c(c(-c5ccc(F)cc5F)c(C(F)(F)F)cc24)SC[C@@H](OCCN(C)C)C3)C[C@@H]1C]

The title compound was prepared analogously to Example 84 where (3S)-11-(2,4-difluorophenyl)-3-(2-(dimethylamino)ethoxy)-8-((3S,5R)-3,5-dimethylpiperazin-1-yl)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 4% yield as a yellow solid. m/z (ESI, +ve)=652.2 $[M+H]^+$ 1H NMR (400 MHz, DMSO-$d_6$) δ 8.05 (s, 1H), 7.52-7.33 (m, 2H), 7.32-7.22 (m, 1H), 6.81 (dd, J=16.0, 8.0 Hz, 1H), 6.20 (dd, J=16.0, 4.0 Hz, 1H), 5.75 (dd, J=16.0, 4.0 Hz, 1H), 4.72-4.36 (m, 3H), 4.17-3.83 (m, 3H), 3.62-3.43 (m, 3H), 3.28-3.05 (m, 4H), 2.43-2.35 (m, 2H), 2.18-2.10 (m, 6H), 1.51-1.29 (m, 6H).

Step 1: 7-(2,4-difluorophenyl)-8-(((S)-2-(2-(dimethylamino)ethoxy)-3-hydroxypropyl)thio)-6-(trifluoromethyl)quinazoline-2,4(1H,3H)-dione

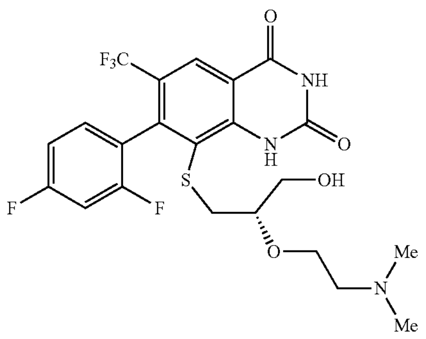 [SMILES: CN(C)CCO[C@@H](CO)CSc1c(-c2ccc(F)cc2F)c(C(F)(F)F)cc2c(=O)[nH]c(=O)[nH]c12]

The title compound was synthesized analogously to example 100, step 9 where 7-(2,4-difluorophenyl)-8-iodo-6-(trifluoromethyl)quinazoline-2,4(1H,3H)-dione and (S)-2-(2-(dimethylamino)ethoxy)-3-mercaptopropan-1-ol were substituted in place of 7-(2,4-difluorophenyl)-8-iodo-6-(trifluoromethyl)quinazoline-2,4(1H,3H)-dione and 2-mercaptoethan-1-ol. The title compound was isolated in 90% yield as a yellow solid after purification by reverse phase silica gel chromatography (36% acetonitrile in water with 0.1% TFA). m/z (ESI, +ve)=520.1 $[M+H]^+$ Step 2: (3S)-11-(2,4-difluorophenyl)-3-(2-(dimethylamino)ethoxy)-10-(trifluoromethyl)-3,4-dihydro-2H,6H-[1,4]thiazepino[2,3,4-ij]quinazoline-6,8(7H)-dione

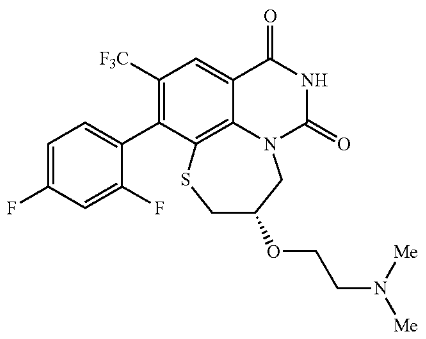 [SMILES: CN(C)CCO[C@@H]1CSc2c(-c3ccc(F)cc3F)c(C(F)(F)F)cc3c(=O)[nH]c(=O)n(c23)C1]

The title compound was prepared analogously to Example 100, step 10 where 7-(2,4-difluorophenyl)-8-(((S)-2-(2-(dimethylamino)ethoxy)-3-hydroxypropyl)thio)-6-(trifluoromethyl)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 20% yield as a yellow solid after purification by reverse phase silica gel chromatography (29% acetonitrile in water with 0.1% TFA). m/z (ESI, +ve)=502.1 $[M+H]^+$ Step 3: (3S)-11-(2,4-difluorophenyl)-3-(2-(dimethylamino)ethoxy)-8-((3S,5R)-3,5-dimethylpiperazin-1-yl)-10-(trifluoromethyl)-3,4-dihydro-2H,6H-[1,4]thiazepino[2,3,4-ij]quinazolin-6-one

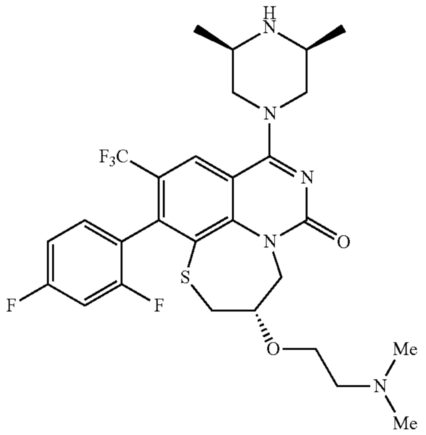 [SMILES: C[C@@H]1CN(c2nc(=O)n3c4c(c(-c5ccc(F)cc5F)c(C(F)(F)F)cc24)SC[C@@H](OCCN(C)C)C3)C[C@H](C)N1]

The title compound was prepared analogously to Example 100, step 21 where (3S)-11-(2,4-difluorophenyl)-3-(2-(dimethylamino)ethoxy)-10-(trifluoromethyl)-3,4-dihydro-2H,6H-[1,4]thiazepino[2,3,4-ij]quinazoline-6,8(7H)-dione and (2S,6R)-2,6-dimethylpiperazine were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 53% yield as a yellow solid after purification by reverse phase silica gel chromatography (27% acetonitrile in water with 0.1% TFA). m/z (ESI, +ve)=598.2 $[M+H]^+$ Example 1035: (S)-8-((3S,5R)-4-acryloyl-3,5-dimethylpiperazin-1-yl)-11-(3-chloro-4-fluorophenyl)-3-(2-(dimethylamino)ethoxy)-10-(trifluoromethyl)-3,4-dihydro-2H,6H-[1,4]thiazepino[2,3,4-ij]quinazolin-6-one

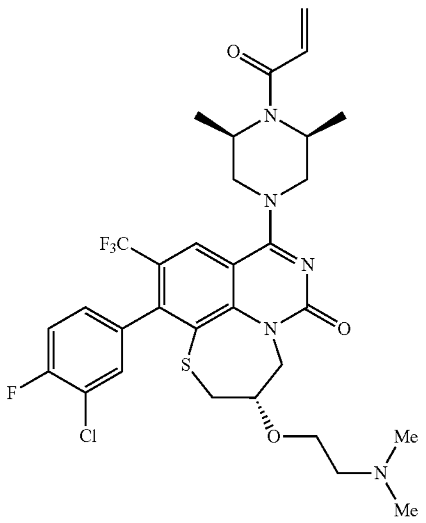 [SMILES: C=CC(=O)N1[C@H](C)CN(c2nc(=O)n3c4c(c(-c5ccc(F)c(Cl)c5)c(C(F)(F)F)cc24)SC[C@@H](OCCN(C)C)C3)C[C@@H]1C]

The title compound was prepared analogously to Example 84 where (S)-11-(3-chloro-4-fluorophenyl)-3-(2-(dimethylamino)ethoxy)-8-((3S,5R)-3,5-dimethylpiperazin-1-yl)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 16% yield as a yellow solid. m/z (ESI, +ve)=668.1 [M+H]$^+$ $^1$H NMR (400 MHz, DMSO-$d_6$) δ 8.01 (s, 1H), 7.58-7.56 (m, 2H), 7.34-7.30 (m, 1H), 6.82 (dd, J=16.0, 8.0 Hz, 1H), 6.19 (dd, J=16.0, 4.0 Hz, 1H), 5.74 (dd, J=16.0, 4.0 Hz, 1H), 4.63-4.55 (m, 2H), 4.50-4.46 (m, 1H), 4.10-4.02 (m, 2H), 3.96-3.94 (m, 1H), 3.54-3.51 (m, 1H), 3.30-3.24 (m, 2H), 3.17-3.08 (m, 2H), 2.57-2.53 (m, 1H), 2.46-2.43 (m, 1H), 2.39-2.36 (m, 2H), 2.13 (s, 6H), 1.40 (s, 6H).

Step 1: (S)-7-(3-chloro-4-fluorophenyl)-8-((2-(2-(dimethylamino)ethoxy)-3-hydroxypropyl)thio)-6-(trifluoromethyl)quinazoline-2,4(1H,3H)-dione

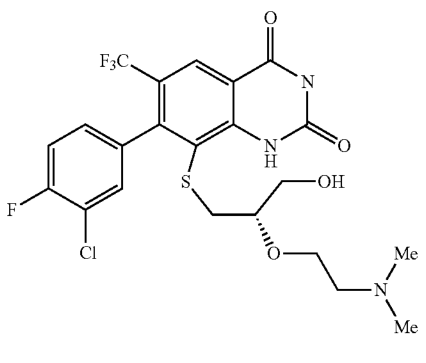 [SMILES: CN(C)CCO[C@@H](CO)CSc1c(-c2ccc(F)c(Cl)c2)c(C(F)(F)F)cc2c(=O)[nH]c(=O)[nH]c12]

The title compound was synthesized analogously to example 100, step 9 where 7-(3-chloro-4-fluorophenyl)-8- iodo-6-(trifluoromethyl)quinazoline-2,4(1H,3H)-dione and (S)-2-(2-(dimethylamino)ethoxy)-3-mercaptopropan-1-ol were substituted in place of 7-(2,4-difluorophenyl)-8-iodo-6-(trifluoromethyl)quinazoline-2,4(1H,3H)-dione and 2-mercaptoethan-1-ol. The title compound was isolated in 71% yield as a white solid. m/z (ESI, +ve)=536.1 [M+H]$^+$ Step 2: (S)-11-(3-chloro-4-fluorophenyl)-3-(2-(dimethylamino)ethoxy)-10-(trifluoromethyl)-3,4-dihydro-2H,6H-[1,4]thiazepino[2,3,4-ij]quinazoline-6,8(7H)-dione

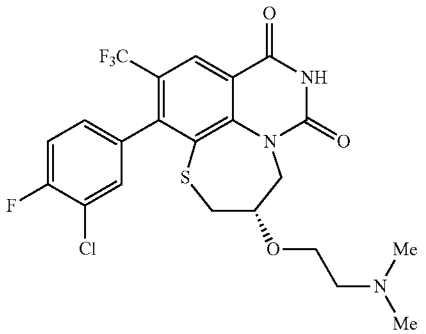 [SMILES: CN(C)CCO[C@@H]1CSc2c(-c3ccc(F)c(Cl)c3)c(C(F)(F)F)cc3c(=O)[nH]c(=O)n(c23)C1]

The title compound was prepared analogously to Example 100, step 10 where (S)-7-(3-chloro-4-fluorophenyl)-8-((2-(2-(dimethylamino)ethoxy)-3-hydroxypropyl)thio)-6-(trifluoromethyl)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 87% yield as a yellow solid. m/z (ESI, +ve)=518.1 [M+H]$^+$ Step 3: (S)-11-(3-chloro-4-fluorophenyl)-3-(2-(dimethylamino)ethoxy)-8-((3S,5R)-3,5-dimethylpiperazin-1-yl)-10-(trifluoromethyl)-3,4-dihydro-2H,6H-[1,4]thiazepino[2,3,4-ij]quinazolin-6-one

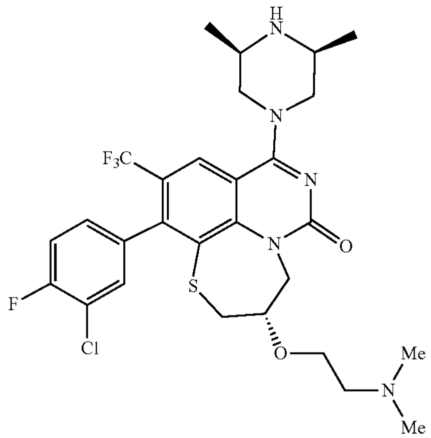 [SMILES: C[C@@H]1CN(c2nc(=O)n3c4c(c(-c5ccc(F)c(Cl)c5)c(C(F)(F)F)cc24)SC[C@@H](OCCN(C)C)C3)C[C@H](C)N1]

The title compound was prepared analogously to Example 100, step 21 where (S)-11-(3-chloro-4-fluorophenyl)-3-(2-(dimethylamino)ethoxy)-10-(trifluoromethyl)-3,4-dihydro-2H,6H-[1,4]thiazepino[2,3,4-ij]quinazoline-6,8(7H)-dione and (2S,6R)-2,6-dimethylpiperazine were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 23% yield as a yellow solid. m/z (ESI, +ve)=614.2 [M+H]$^+$ Example 1036: (3S)-8-((3S,5R)-4-acryloyl-3,5-dimethylpiperazin-1-yl)-11-(5-chloro-2,4-difluorophenyl)-3-(2-(dimethylamino)ethoxy)-10-(trifluoromethyl)-3,4-dihydro-2H,6H-[1,4]thiazepino[2,3,4-ij]quinazolin-6-one

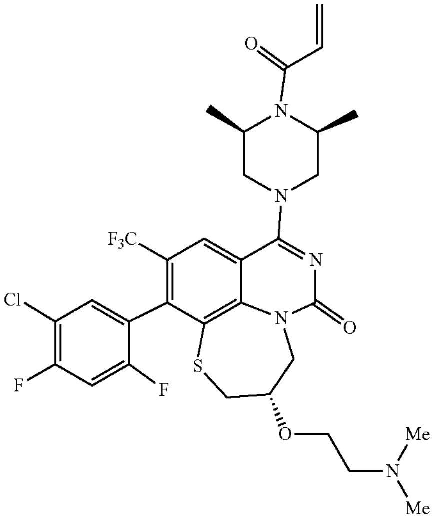 [SMILES: C=CC(=O)N1[C@H](C)CN(c2nc(=O)n3c4c(c(-c5cc(Cl)c(F)cc5F)c(C(F)(F)F)cc24)SC[C@@H](OCCN(C)C)C3)C[C@@H]1C]

The title compound was prepared analogously to Example 84 where (3S)-11-(5-chloro-2,4-difluorophenyl)-3-(2-(dimethylamino)ethoxy)-8-((3S,5R)-3,5-dimethylpiperazin-1-yl)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 8% yield as a yellow solid. m/z (ESI, +ve)=686.2 [M+H]$^+$ 1H NMR (400 MHz, dmso) δ=8.04 (s, 1H), 7.81-7.75 (m, 2H), 6.81 (dd, J=16.6, 8.0 Hz, 1H), 6.19 (dd, J=16.0, 4.0 Hz, 1H), 5.74 (dd, J=16.0, 4.0 Hz, 1H), 4.59 (m, 2H), 4.49-4.46 (m, 1H), 4.13-3.92 (m, 4H), 3.59 (m, 2H), 3.28-3.12 (m, 3H), 2.52-2.51 (m, 1H), 2.40-2.36 (m, 2H), 2.14 (s, 6H), 1.43-1.39 (m, 6H).

Step 1: 7-(5-chloro-2,4-difluorophenyl)-8-(((S)-2-(2-(dimethylamino)ethoxy)-3-hydroxypropyl)thio)-6-(trifluoromethyl)quinazoline-2,4(1H,3H)-dione

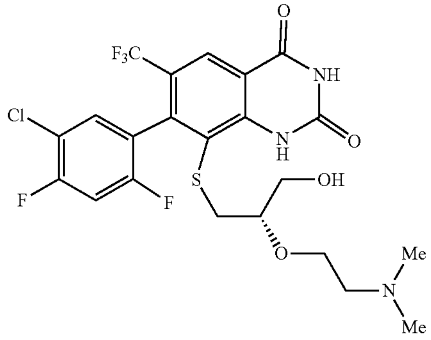 [SMILES: CN(C)CCO[C@@H](CO)CSc1c(-c2cc(Cl)c(F)cc2F)c(C(F)(F)F)cc2c(=O)[nH]c(=O)[nH]c12]

The title compound was synthesized analogously to example 100, step 9 where 7-(5-chloro-2,4-difluorophenyl)-8-iodo-6-(trifluoromethyl)quinazoline-2,4(1H,3H)-dione and (S)-2-(2-(dimethylamino)ethoxy)-3-mercaptopropan-1-ol were substituted in place of 7-(2,4-difluorophenyl)-8-iodo-6-(trifluoromethyl)quinazoline-2,4(1H,3H)-dione and 2-mercaptoethan-1-ol. The title compound was isolated in 91% yield as a white solid. m/z (ESI, +ve)=554.1 [M+H]$^+$ Step 2: (3S)-11-(5-chloro-2,4-difluorophenyl)-3-(2-(dimethylamino)ethoxy)-10-trifluoromethyl)-3,4-dihydro-2H,6H-[1,4]thiazepino[2,3,4-ij]quinazoline-6,8(7H)-dione

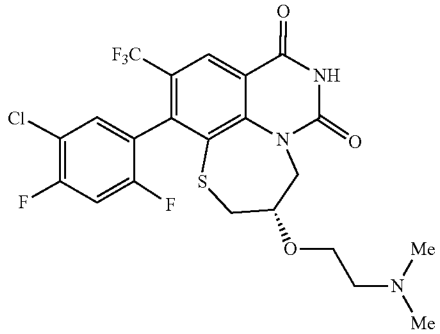 [SMILES: CN(C)CCO[C@@H]1CSc2c(-c3cc(Cl)c(F)cc3F)c(C(F)(F)F)cc3c(=O)[nH]c(=O)n(c23)C1]

The title compound was prepared analogously to Example 100, step 10 where 7-(5-chloro-2,4-difluorophenyl)-8-(((S)-2-(2-(dimethylamino)ethoxy)-3-hydroxypropyl)thio)-6-(trifluoromethyl)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 47% yield as a yellow solid. m/z (ESI, +ve)=536.0 [M+H]$^+$ Step 3: (3S)-11-(5-chloro-2,4-difluorophenyl)-3-(2-(dimethylamino)ethoxy)-8-((3S,5R)-3,5-dimethylpiperazin-1-yl)-10-(trifluoromethyl)-3,4-dihydro-2H,6H-[1,4]thiazepino[2,3,4-ij]quinazolin-6-one

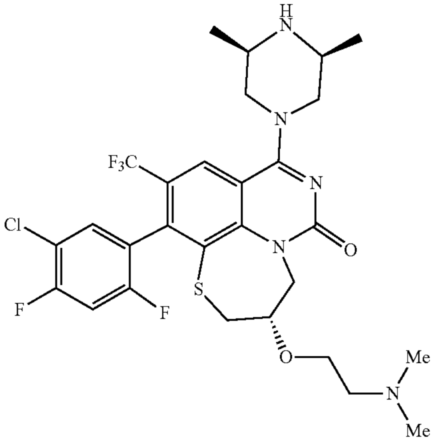 [SMILES: C[C@@H]1CN(c2nc(=O)n3c4c(c(-c5cc(Cl)c(F)cc5F)c(C(F)(F)F)cc24)SC[C@@H](OCCN(C)C)C3)C[C@H](C)N1]

The title compound was prepared analogously to Example 100, step 21 where (3S)-11-(5-chloro-2,4-difluorophenyl)-3-(2-(dimethylamino)ethoxy)-10-(trifluoromethyl)-3,4-dihydro-2H,6H-[1,4]thiazepino[2,3,4-ij]quinazoline-6,8(7H)-dione and (2S,6R)-2,6-dimethylpiperazine were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 47% yield as a yellow solid. m/z (ESI, +ve)=536.0 $[M+H]^+$ Example 1037: (R)-8-(4-acryloylpiperazin-1-yl)-11-(4-fluorophenyl)-3-methoxy-10-(trifluoromethyl)-3,4-dihydro-2H,6H-[1,4]thiazepino[2,3,4-ij]quinazolin-6-one

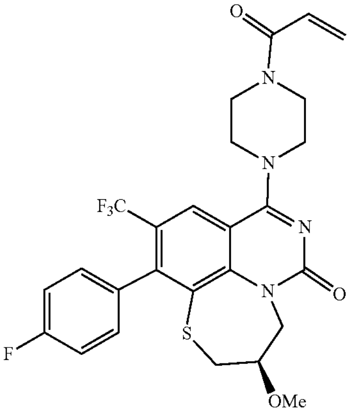 [SMILES: C=CC(=O)N1CCN(c2nc(=O)n3c4c(c(-c5ccc(F)cc5)c(C(F)(F)F)cc24)SC[C@H](OC)C3)CC1]

The title compound was prepared analogously to Example 84 where (R)-10-chloro-8-((3S,5R)-3,5-dimethylpiperazin-1-yl)-11-(4-fluorophenyl)-3-methoxy-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 25% yield as a yellow solid. Mass Spectrum (ESI) m/z=549.1 $[M+H]^+$ Step 1: tert-butyl (R)-4-(11-(4-fluorophenyl)-3-methoxy-6-oxo-10-(trifluoromethyl)-3,4-dihydro-2H,6H-[1,4]thiazepino[2,3,4-ij]quinazolin-8-yl)piperazine-1-carboxylate

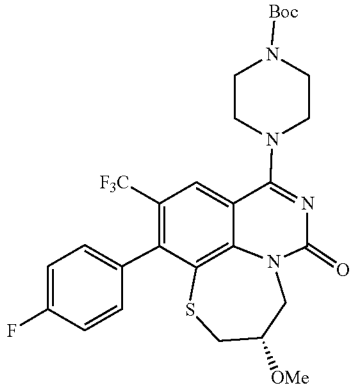

The title compound was prepared analogously to Example 100, step 21 where (R)-11-(4-fluorophenyl)-3-methoxy-10-(trifluoromethyl)-3,4-dihydro-2H,6H-[1,4]thiazepino[2,3,4-ij]quinazoline-6,8(7H)-dione and tert-butyl piperazine-1-carboxylate were substituted in place of 10-(2,4-difluorophenyl)-9-(trifluoromethyl)-2,3-dihydro-5H-[1,4] thiazino[2,3,4-ij]quinazoline-5,7(6H)-dione and octahydrothieno[3,4-b]pyrazine 6,6-dioxide. The title compound was isolated in 60% yield as a yellow solid. m/z (ESI, +ve)=595.2 $[M+H]^+$ Step 2: (R)-11-(4-fluorophenyl)-3-methoxy-8-(piperazin-1-yl)-10-(trifluoromethyl)-3,4-dihydro-2H,6H-[1,4]thiazepino[2,3,4-ij]quinazolin-6-one

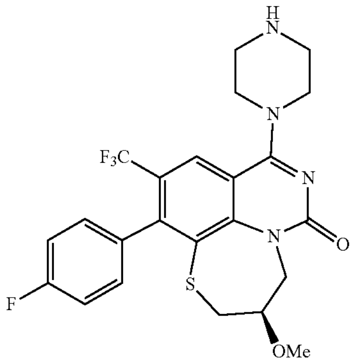 [SMILES: CO[C@H]1CSc2c(-c3ccc(F)cc3)c(C(F)(F)F)cc3c(N4CCNCC4)nc(=O)n(c23)C1]

The title compound was prepared analogously to Example 102, step 4, where tert-butyl (R)-4-(11-(4-fluorophenyl)-3-methoxy-6-oxo-10-(trifluoromethyl)-3,4-dihydro-2H,6H-[1,4]thiazepino[2,3,4-ij]quinazolin-8-yl)piperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3- methylpiperazine-1-carboxylate. The title compound was isolated in 95% yield as a yellow solid. m/z (ESI, +ve)= 494.9 [M+H]+

Example 1038: (S)-8-(4-acryloylpiperazin-1-yl)-11-(4-fluorophenyl)-3-methoxy-10-(trifluoromethyl)-3,4-dihydro-2H,6H-[1,4]thiazepino[2,3,4-ij]quinazolin-6-one

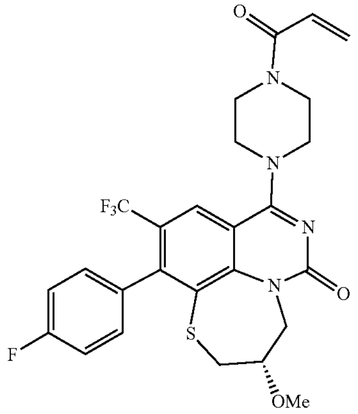 [SMILES: C=CC(=O)N1CCN(c2nc(=O)n3c4c(c(-c5ccc(F)cc5)c(C(F)(F)F)cc24)SC[C@@H](OC)C3)CC1]

The title compound was prepared analogously to Example 84 where (S)-10-chloro-8-((3S,5R)-3,5-dimethylpiperazin-1-yl)-11-(4-fluorophenyl)-3-methoxy-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 28% yield as a yellow solid. Mass Spectrum (ESI) m/z=549.1 [M+H]+

1H NMR (400 MHz, DMSO-d6) δ 7.86 (s, 1H), 7.36-7.32 (m, 4H), 6.83 (dd, J=16.0, 8.0 Hz, 1H), 6.17 (dd, J=16.0, 4.0 Hz, 1H), 5.74 (dd, J=16.0, 4.0 Hz, 1H), 4.57-4.45 (m, 1H), 3.99-3.61 (m, 9H), 3.39-3.33 (m, 5H), 3.16-3.03 (m, 1H).

Step 1: tert-butyl (S)-4-(11-(4-fluorophenyl)-3-methoxy-6-oxo-10-(trifluoromethyl)-3,4-dihydro-2H,6H-[1,4]thiazepino[2,3,4-ij]quinazolin-8-yl)piperazine-1-carboxylate

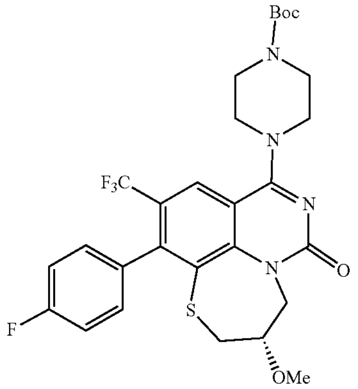 [SMILES: CO[C@@H]1CSc2c(-c3ccc(F)cc3)c(C(F)(F)F)cc3c(N4CCN(C(=O)OC(C)(C)C)CC4)nc(=O)n(c23)C1]

The title compound was prepared analogously to Example 100, step 21 where (S)-11-(4-fluorophenyl)-3-methoxy-10-(trifluoromethyl)-3,4-dihydro-2H,6H-[1,4]thiazepino[2,3,4-ij]quinazoline-6,8(7H)-dione and tert-butyl piperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 56% yield as a yellow solid. m/z (ESI, +ve)=595.2 [M+H]+

1H NMR (400 MHz, DMSO-d6) δ 7.83 (s, 1H), 7.46-7.32 (m, 4H), 4.54-4.45 (m, 1H), 3.83-3.72 (m, 6H), 3.55-3.45 (m, 4H), 3.29-3.24 (m, 3H), 3.12-3.04 (m, 1H), 3.03-2.96 (m, 1H), 1.43 (s, 9H).

Step 2: (S)-11-(4-fluorophenyl)-3-methoxy-8-(piperazin-1-yl)-10-(trifluoromethyl)-3,4-dihydro-2H,6H-[1,4]thiazepino[2,3,4-ij]quinazolin-6-one

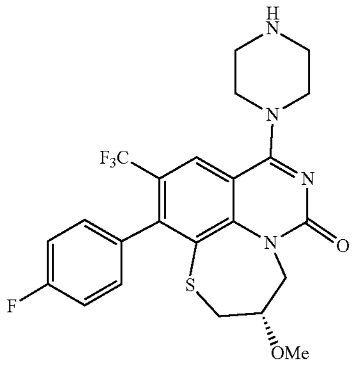 [SMILES: CO[C@@H]1CSc2c(-c3ccc(F)cc3)c(C(F)(F)F)cc3c(N4CCNCC4)nc(=O)n(c23)C1]

The title compound was prepared analogously to Example 102, step 4, where tert-butyl (S)-4-(11-(4-fluorophenyl)-3-methoxy-6-oxo-10-(trifluoromethyl)-3,4-dihydro-2H,6H-[1,4]thiazepino[2,3,4-ij]quinazolin-8-yl)piperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 97% yield as a yellow solid. m/z (ESI, +ve)= 494.9 [M+H]+

Example 1039: (R)-8-((3S,5R)-4-acryloyl-3,5-dimethylpiperazin-1-yl)-10-chloro-11-(4-fluorophenyl)-3-methoxy-3,4-dihydro-2H,6H-[1,4]thiazepino[2,3,4-ij]quinazolin-6-one

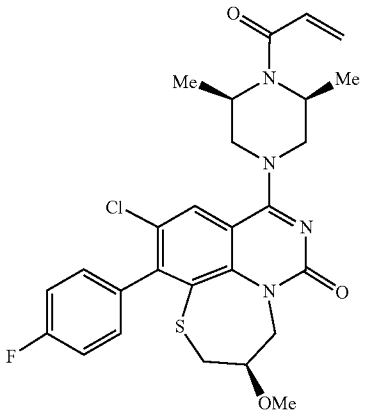 [SMILES: C=CC(=O)N1[C@H](C)CN(c2nc(=O)n3c4c(c(-c5ccc(F)cc5)c(Cl)cc24)SC[C@H](OC)C3)C[C@@H]1C]

The title compound was prepared analogously to Example 84 where (R)-10-chloro-8-((3S,5R)-3,5-dimethylpiperazin-1-yl)-11-(4-fluorophenyl)-3-methoxy-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 35% yield as a yellow solid. Mass Spectrum (ESI) m/z=543.2 $[M+H]^+$ 1H NMR (400 MHz, DMSO) δ7.79 (s, 1H), 7.37-7.34 (m, 4H), 6.81 (dd, J=16.0 Hz, 8.0 Hz, 1H), 6.19 (dd, J=16.0, 4.0 Hz, 1H), 5.74 (dd, J=16.0, 4.0 Hz, 1H), 4.62-4.41 (m, 3H), 4.07-4.02 (m, 2H), 3.88-3.80 (m, 1H), 3.33-3.28 (m, 7H), 3.10-3.06 (m, 1H), 1.41-1.36 (m, 6H).

Step 1: (R)-10-chloro-8-((3S,5R)-3,5-dimethylpiperazin-1-yl)-11-(4-fluorophenyl)-3-methoxy-3,4-dihydro-2H,6H-[1,4]thiazepino[2,3,4-ij]quinazolin-6-one

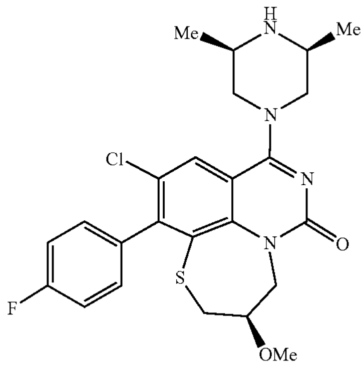 [SMILES: CO[C@H]1CSc2c(-c3ccc(F)cc3)c(Cl)cc3c(N4C[C@@H](C)N[C@@H](C)C4)nc(=O)n(c23)C1]

The title compound was prepared analogously to Example 100, step 21 where (R)-10-chloro-11-(4-fluorophenyl)-3-methoxy-3,4-dihydro-2H,6H-[1,4]thiazepino[2,3,4-ij]quinazoline-6,8(7H)-dione and (2R,6S)-2,6-dimethylpiperazine were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 90% yield as a yellow solid. Mass Spectrum (ESI) m/z=489.2 $[M+H]^+$ Example 1040: (S)-8-((3S,5R)-4-acryloyl-3,5-dimethylpiperazin-1-yl)-10-chloro-11-(4-fluorophenyl)-3-methoxy-3,4-dihydro-2H,6H-[1,4]thiazepino[2,3,4-ij]quinazolin-6-one

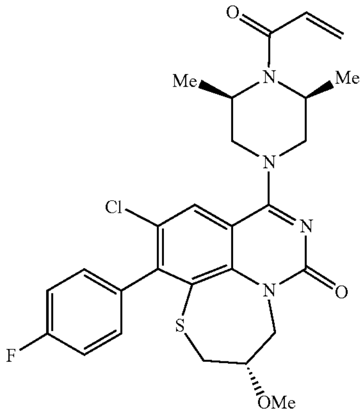 [SMILES: C=CC(=O)N1[C@H](C)CN(c2nc(=O)n3c4c(c(-c5ccc(F)cc5)c(Cl)cc24)SC[C@@H](OC)C3)C[C@@H]1C]

The title compound was prepared analogously to Example 84 where (S)-10-chloro-8-((3S,5R)-3,5-dimethylpiperazin-1-yl)-11-(4-fluorophenyl)-3-methoxy-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 28% yield as a yellow solid. m/z (ESI, +ve)=543.2 $[M+H]^+$ 1H NMR (400 MHz, DMSO) δ 7.79 (s, 1H), 7.37-7.35 (m, 3H), 6.81 (dd, J=16.0, 8.0 Hz, 1H), 6.19 (dd, J=16.0, 4.0 Hz, 1H), 5.74 (dd, J=16.0, 4.0 Hz, 1H), 4.58-4.54 (m, 2H), 4.47-4.44 (m, 1H), 4.04-4.02 (m, 2H), 3.86-3.83 (m, 1H), 3.30-3.28 (m, 3H), 3.09-3.05 (m, 1H), 2.49-2.36 (m, 4H), 1.41-1.36 (m, 6H).

Step 1: (S)-10-chloro-8-((3S,5R)-3,5-dimethylpiperazin-1-yl)-11-(4-fluorophenyl)-3-methoxy-3,4-dihydro-2H,6H-[1,4]thiazepino[2,3,4-ij]quinazolin-6-one

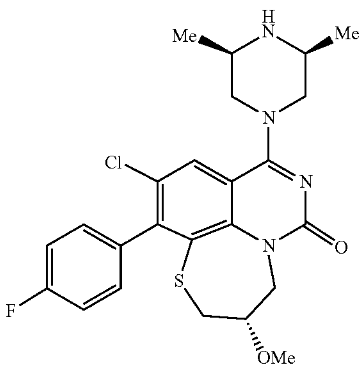 [SMILES: CO[C@@H]1CSc2c(-c3ccc(F)cc3)c(Cl)cc3c(N4C[C@@H](C)N[C@@H](C)C4)nc(=O)n(c23)C1]

The title compound was prepared analogously to Example 100, step 21 where (S)-10-chloro-11-(4-fluorophenyl)-3-methoxy-3,4-dihydro-2H,6H-[1,4]thiazepino[2,3,4-ij]quinazoline-6,8(7H)-dione and (2S,6R)-2,6-dimethylpiperazine were substituted in place of 10-(2,4-difluorophenyl)-9-

(trifluoromethyl)-2,3-dihydro-5H-[1,4]thiazino[2,3,4-ij] quinazoline-5,7(6H)-dione and octahydrothieno[3,4-b] pyrazine 6,6-dioxide. The title compound was isolated in 82% yield as a yellow solid. m/z (ESI, +ve)=489.2 $[M+H]^+$ Example 1041: (R)-8-(4-acryloylpiperazin-1-yl)-11-(3-chloro-4-fluorophenyl)-3-methoxy-10-(trifluoromethyl)-3,4-dihydro-2H,6H-[1,4]thiazepino[2,3,4-ij]quinazolin-6-one

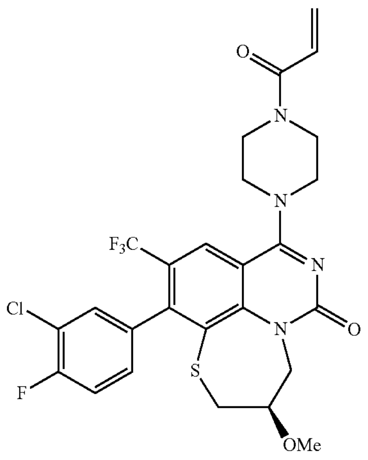 [SMILES: C=CC(=O)N1CCN(c2nc(=O)n3c4c(c(-c5ccc(F)c(Cl)c5)c(C(F)(F)F)cc24)SC[C@H](OC)C3)CC1]

The title compound was prepared analogously to Example 84 where (R)-11-(3-chloro-4-fluorophenyl)-3-methoxy-8-(piperazin-1-yl)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 48% yield as a yellow solid. m/z (ESI, +ve)=583.1 $[M+H]^+$ 1H NMR (400 MHz, DMSO) δ=7.87 (s, 1H), 7.71-7.48 (m, 2H), 7.42-7.27 (m, 1H), 6.83 (dd, J=16.0, 8.0 Hz, 1H), 6.17 (dd, J=16.0, 4.0 Hz, 1H), 5.74 (dd, J=16.0, 4.0 Hz, 1H), 4.62-4.46 (m, 1H), 4.12-3.50 (m, 9H), 3.48-3.30 (m, 5H), 3.21-3.04 (m, 1H).

Step 1: (R)-7-(3-chloro-4-fluorophenyl)-8-((3-hydroxy-2-methoxypropyl)thio)-6-(trifluoromethyl) quinazoline-2,4(1H,3H)-dione

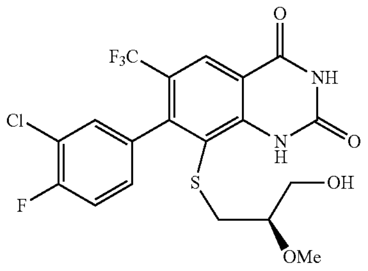 [SMILES: CO[C@H](CO)CSc1c(-c2ccc(F)c(Cl)c2)c(C(F)(F)F)cc2c(=O)[nH]c(=O)[nH]c12]

The title compound was synthesized analogously to example 100, step 9 where 7-(3-chloro-4-fluorophenyl)-8-iodo-6-(trifluoromethyl)quinazoline-2,4(1H,3H)-dione and (R)-3-mercapto-2-methoxypropan-1-ol were substituted in place of 7-(2,4-difluorophenyl)-8-iodo-6-(trifluoromethyl) quinazoline-2,4(1H,3H)-dione and 2-mercaptoethan-1-ol. The title compound was isolated in 74% yield as a white solid. m/z (ESI, +ve)=479.0 $[M+H]^+$ Step 2: (R)-11-(3-chloro-4-fluorophenyl)-3-methoxy-10-(trifluoromethyl)-3,4-dihydro-2H,6H-[1,4]thiazepino[2,3,4-ij]quinazoline-6,8(7H)-dione

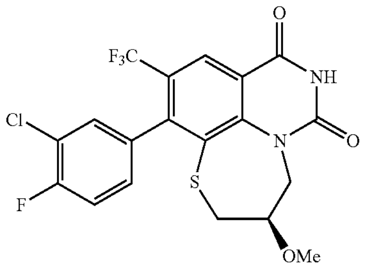 [SMILES: CO[C@H]1CSc2c(-c3ccc(F)c(Cl)c3)c(C(F)(F)F)cc3c(=O)[nH]c(=O)n(c23)C1]

The title compound was prepared analogously to Example 100, step 10 where (R)-7-(3-chloro-4-fluorophenyl)-8-((3-hydroxy-2-methoxypropyl)thio)-6-(trifluoromethyl)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 74% yield as a yellow solid. m/z (ESI, +ve)=461.1 $[M+H]^+$ Step 3: tert-butyl (R)-4-(11-(3-chloro-4-fluorophenyl)-3-methoxy-6-oxo-10-(trifluoromethyl)-3,4-dihydro-2H,6H-[1,4]thiazepino[2,3,4-ij]quinazolin-8-yl)piperazine-1-carboxylate

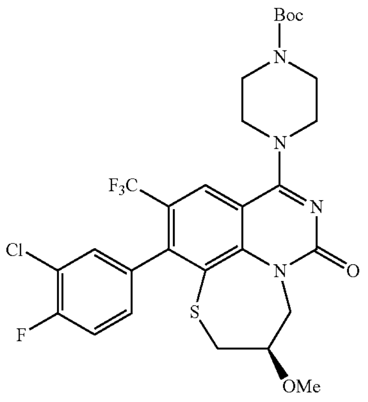 [SMILES: CO[C@H]1CSc2c(-c3ccc(F)c(Cl)c3)c(C(F)(F)F)cc3c(N4CCN(C(=O)OC(C)(C)C)CC4)nc(=O)n(c23)C1]

The title compound was prepared analogously to Example 100, step 21 where (R)-11-(3-chloro-4-fluorophenyl)-3-methoxy-10-(trifluoromethyl)-3,4-dihydro-2H,6H-[1,4]thiazepino[2,3,4-ij]quinazoline-6,8(7H)-dione and tert-butyl piperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 87% yield as a yellow solid. m/z (ESI, +ve)=629.2 $[M+H]^+$ Step 4: (R)-11-(3-chloro-4-fluorophenyl)-3-methoxy-8-(piperazin-1-yl)-10-(trifluoromethyl)-3,4-dihydro-2H,6H-[1,4]thiazepino[2,3,4-ij]quinazolin-6-one

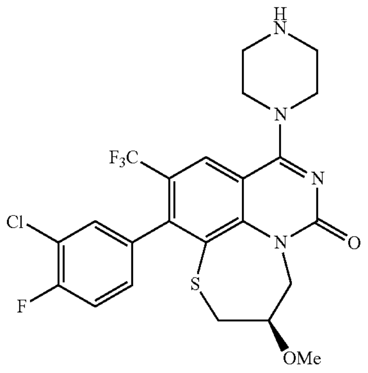 [SMILES: CO[C@H]1CSc2c(-c3ccc(F)c(Cl)c3)c(C(F)(F)F)cc3c(N4CCNCC4)nc(=O)n(c23)C1]

The title compound was prepared analogously to Example 102, step 4, where tert-butyl (R)-4-(11-(3-chloro-4-fluorophenyl)-3-methoxy-6-oxo-10-(trifluoromethyl)-3,4-dihydro-2H,6H-[1,4]thiazepino[2,3,4-ij]quinazolin-8-yl)piperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated as a yellow solid and used in the next step without further purification. m/z (ESI, +ve)=529.2 $[M+H]^+$ Example 1042: (S)-8-(4-acryloylpiperazin-1-yl)-11-(3-chloro-4-fluorophenyl)-3-methoxy-10-(trifluoromethyl)-3,4-dihydro-2H,6H-[1,4]thiazepino[2,3,4-ij]quinazolin-6-one

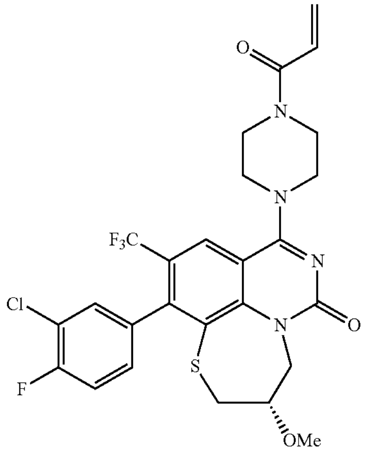 [SMILES: C=CC(=O)N1CCN(c2nc(=O)n3c4c(c(-c5ccc(F)c(Cl)c5)c(C(F)(F)F)cc24)SC[C@@H](OC)C3)CC1]

The title compound was prepared analogously to Example 84 where (S)-11-(3-chloro-4-fluorophenyl)-3-methoxy-8-(piperazin-1-yl)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 39% yield as a yellow solid. m/z (ESI, +ve)=583.1 $[M+H]^+$ 1H NMR (400 MHz, DMSO-$d_6$) δ 7.87 (s, 1H), 7.67-7.51 (m, 2H), 7.46-7.35 (m, 1H), 6.83 (dd, J=16.0, 8.0 Hz, 1H), 6.17 (dd, J=16.0, 4.0 Hz, 1H), 5.74 (dd, J=16.0, 4.0 Hz, 1H), 4.53-4.49 (m, 1H), 3.92-3.53 (m, 9H), 3.49-3.34 (m, 5H), 3.16-3.01 (m, 1H).

Step 1: (S)-7-(3-chloro-4-fluorophenyl)-8-((3-hydroxy-2-methoxypropyl)thio)-6-(trifluoromethyl)quinazoline-2,4(1H,3H)-dione

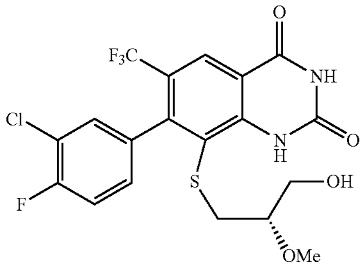 [SMILES: CO[C@@H](CO)CSc1c(-c2ccc(F)c(Cl)c2)c(C(F)(F)F)cc2c(=O)[nH]c(=O)[nH]c12]

The title compound was synthesized analogously to example 100, step 9 where 7-(3-chloro-4-fluorophenyl)-8-iodo-6-(trifluoromethyl)quinazoline-2,4(1H,3H)-dione and (S)-3-mercapto-2-methoxypropan-1-ol were substituted in place of 7-(2,4-difluorophenyl)-8-iodo-6-(trifluoromethyl)quinazoline-2,4(1H,3H)-dione and 2-mercaptoethan-1-ol. The title compound was isolated in 74% yield as a white solid. m/z (ESI, +ve)=479.1 $[M+H]^+$ Step 2: (S)-11-(3-chloro-4-fluorophenyl)-3-methoxy-10-(trifluoromethyl)-3,4-dihydro-2H,6H-[1,4]thiazepino[2,3,4-ij]quinazoline-6,8(7H)-dione

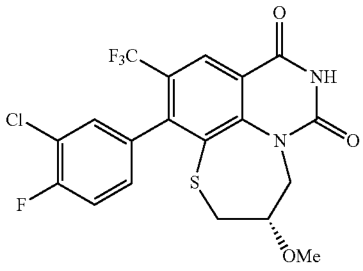 [SMILES: CO[C@@H]1CSc2c(-c3ccc(F)c(Cl)c3)c(C(F)(F)F)cc3c(=O)[nH]c(=O)n(c23)C1]

The title compound was prepared analogously to Example 100, step 10 where (S)-7-(3-chloro-4-fluorophenyl)-8-((3-hydroxy-2-methoxypropyl)thio)-6-(trifluoromethyl)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 83% yield as a yellow solid. m/z (ESI, +ve)=461.1 $[M+H]^+$ Step 3: tert-butyl (S)-4-(11-(3-chloro-4-fluorophenyl)-3-methoxy-6-oxo-10-(trifluoromethyl)-3,4-dihydro-2H,6H-[1,4]thiazepino[2,3,4-ij]quinazolin-8-yl)piperazine-1-carboxylate

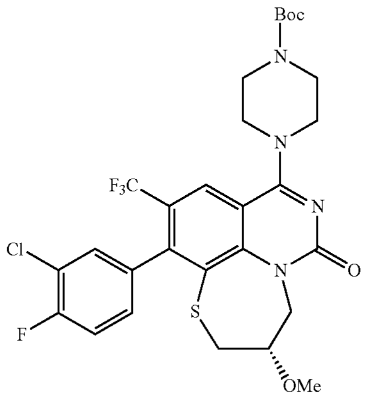 [SMILES: CO[C@@H]1CSc2c(-c3ccc(F)c(Cl)c3)c(C(F)(F)F)cc3c(N4CCN(C(=O)OC(C)(C)C)CC4)nc(=O)n(c23)C1]

The title compound was prepared analogously to Example 100, step 21 where (S)-11-(3-chloro-4-fluorophenyl)-3-methoxy-10-(trifluoromethyl)-3,4-dihydro-2H,6H-[1,4]thiazepino[2,3,4-ij]quinazoline-6,8(7H)-dione and tert-butyl piperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 87% yield as a yellow solid. m/z (ESI, +ve)=629.2 [M+H]$^+$ Step 4: (S)-11-(3-chloro-4-fluorophenyl)-3-methoxy-8-(piperazin-1-yl)-10-(trifluoromethyl)-3,4-dihydro-2H,6H-[1,4]thiazepino[2,3,4-ij]quinazolin-6-one

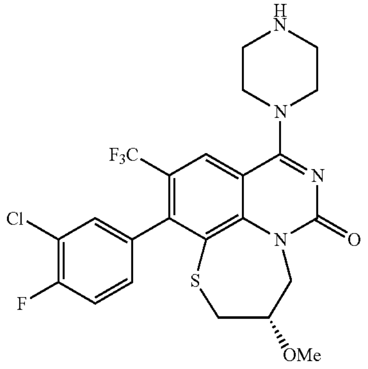 [SMILES: CO[C@@H]1CSc2c(-c3ccc(F)c(Cl)c3)c(C(F)(F)F)cc3c(N4CCNCC4)nc(=O)n(c23)C1]

The title compound was prepared analogously to Example 102, step 4, where tert-butyl (S)-4-(11-(3-chloro-4-fluorophenyl)-3-methoxy-6-oxo-10-(trifluoromethyl)-3,4-dihydro-2H,6H-[1,4]thiazepino[2,3,4-ij]quinazolin-8-yl)piperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated as a yellow solid and used in the next step without further purification. m/z (ESI, +ve)=529.1 [M+H]$^+$ Example 1043: (R)-8-(4-acryloylpiperazin-1-yl)-11-(3-chloro-4-fluorophenyl)-3-methoxy-10-(trifluoromethyl)-3,4-dihydro-2H,6H-[1,4]thiazepino[2,3,4-ij]quinazolin-6-one

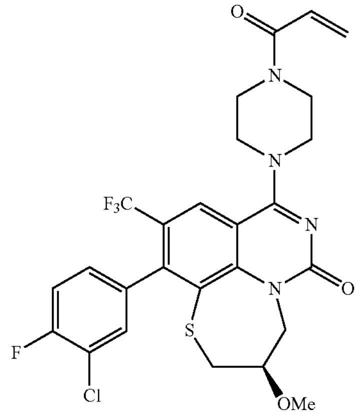 [SMILES: C=CC(=O)N1CCN(c2nc(=O)n3c4c(c(-c5ccc(F)c(Cl)c5)c(C(F)(F)F)cc24)SC[C@H](OC)C3)CC1]

The title compound was prepared analogously to Example 84 where (R)-11-(3-chloro-4-fluorophenyl)-3-methoxy-8-(piperazin-1-yl)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 48% yield as a yellow solid. m/z (ESI, +ve)=583.1 [M+H]$^+$ 1H NMR (400 MHz, DMSO) δ=7.87 (s, 1H), 7.71-7.48 (m, 2H), 7.42-7.27 (m, 1H), 6.83 (dd, J=16.0, 8.0 Hz, 1H), 6.17 (dd, J=16.0, 4.0 Hz, 1H), 5.74 (dd, J=16.0, 4.0 Hz, 1H), 4.62-4.46 (m, 1H), 4.12-3.50 (m, 9H), 3.48-3.30 (m, 5H), 3.21-3.04 (m, 1H).

Step 1: tert-butyl (R)-4-(11-(3-chloro-4-fluorophenyl)-3-methoxy-6-oxo-10-(trifluoromethyl)-3,4-dihydro-2H,6H-[1,4]thiazepino[2,3,4-ij]quinazolin-8-yl)piperazine-1-carboxylate

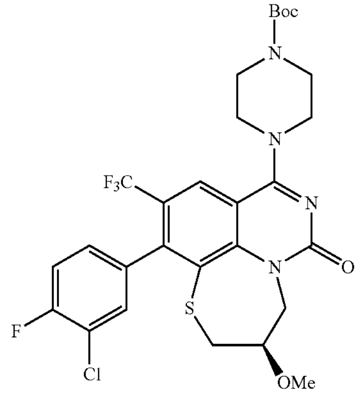 [SMILES: CO[C@H]1CSc2c(-c3ccc(F)c(Cl)c3)c(C(F)(F)F)cc3c(N4CCN(C(=O)OC(C)(C)C)CC4)nc(=O)n(c23)C1]

The title compound was prepared analogously to Example 100, step 21 where (R)-11-(3-chloro-4-fluorophenyl)-3-methoxy-10-(trifluoromethyl)-3,4-dihydro-2H,6H-[1,4]thiazepino[2,3,4-ij]quinazoline-6,8(7H)-dione and tert-butyl piperazine-1-carboxylate were substituted in place of 10-(2, 4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 87% yield as a yellow solid. m/z (ESI, +ve)=629.2 [M+H]$^+$ Step 2: (R)-11-(3-chloro-4-fluorophenyl)-3-methoxy-8-(piperazin-1-yl)-10-(trifluoromethyl)-3,4-dihydro-2H,6H-[1,4]thiazepino[2,3,4-ij]quinazolin-6-one

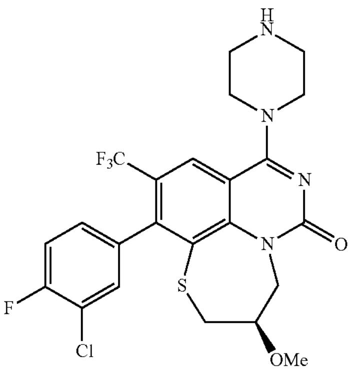 [SMILES: CO[C@H]1CSc2c(-c3ccc(F)c(Cl)c3)c(C(F)(F)F)cc3c(N4CCNCC4)nc(=O)n(c23)C1]

The title compound was prepared analogously to Example 102, step 4, where tert-butyl (R)-4-(11-(3-chloro-4-fluorophenyl)-3-methoxy-6-oxo-10-(trifluoromethyl)-3,4-dihydro-2H,6H-[1,4]thiazepino[2,3,4-ij]quinazolin-8-yl)piperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated as a yellow solid. m/z (ESI, +ve)=529.2 [M+H]$^+$ Example 1044: (S)-8-(4-acryloylpiperazin-1-yl)-11-(3-chloro-4-fluorophenyl)-3-methoxy-10-(trifluoromethyl)-3,4-dihydro-2H,6H-[1,4]thiazepino[2,3,4-ij]quinazolin-6-one

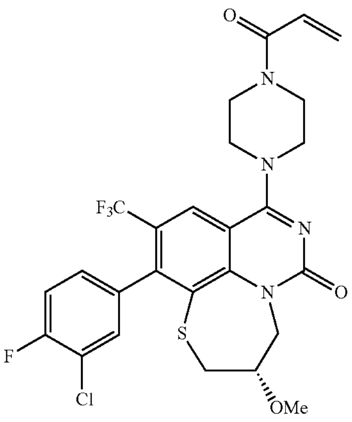 [SMILES: C=CC(=O)N1CCN(c2nc(=O)n3c4c(c(-c5ccc(F)c(Cl)c5)c(C(F)(F)F)cc24)SC[C@@H](OC)C3)CC1]

The title compound was prepared analogously to Example 84 where (S)-11-(3-chloro-4-fluorophenyl)-3-methoxy-8-(piperazin-1-yl)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 39% yield as a yellow solid. m/z (ESI, +ve)=583.1 [M+H]$^+$ 1H NMR (400 MHz, DMSO-$d_6$) δ 7.87 (s, 1H), 7.67-7.51 (m, 2H), 7.46-7.35 (m, 1H), 6.83 (dd, J=16.0, 8.0 Hz, 1H), 6.17 (dd, J=16.0, 4.0 Hz, 1H), 5.74 (dd, J=16.0, 4.0 Hz, 1H), 4.53-4.49 (m, 1H), 3.92-3.53 (m, 9H), 3.49-3.34 (m, 5H), 3.16-3.01 (m, 1H).

Step 1: tert-butyl (S)-4-(11-(3-chloro-4-fluorophenyl)-3-methoxy-6-oxo-10-(trifluoromethyl)-3,4-dihydro-2H,6H-[1,4]thiazepino[2,3,4-ij]quinazolin-8-yl)piperazine-1-carboxylate

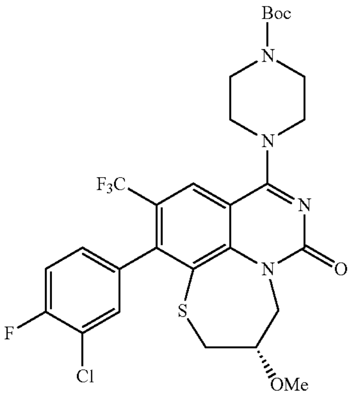 [SMILES: CO[C@@H]1CSc2c(-c3ccc(F)c(Cl)c3)c(C(F)(F)F)cc3c(N4CCN(C(=O)OC(C)(C)C)CC4)nc(=O)n(c23)C1]

The title compound was prepared analogously to Example 100, step 21 where (S)-11-(3-chloro-4-fluorophenyl)-3-methoxy-10-(trifluoromethyl)-3,4-dihydro-2H,6H-[1,4]thiazepino[2,3,4-ij]quinazoline-6,8(7H)-dione and tert-butyl piperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in XX % yield as a yellow solid. m/z (ESI, +ve)=629.1 [M+H]$^+$ Step 2: (S)-11-(3-chloro-4-fluorophenyl)-3-methoxy-8-(piperazin-1-yl)-10-(trifluoromethyl)-3,4-dihydro-2H,6H-[1,4]thiazepino[2,3,4-ij]quinazolin-6-one

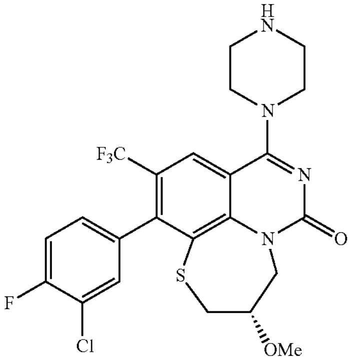 [SMILES: CO[C@@H]1CSc2c(-c3ccc(F)c(Cl)c3)c(C(F)(F)F)cc3c(N4CCNCC4)nc(=O)n(c23)C1]

The title compound was prepared analogously to Example 102, step 4, where tert-butyl (S)-4-(11-(3-chloro-4-fluorophenyl)-3-methoxy-6-oxo-10-(trifluoromethyl)-3,4-dihydro-2H,6H-[1,4]thiazepino[2,3,4-ij]quinazolin-8-yl)piperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 99% yield as a yellow solid. m/z (ESI, +ve)=529.1 [M+H]$^+$ Example 1045: (R)-8-((3S,5R)-4-acryloyl-3,5-dimethylpiperazin-1-yl)-11-(3-chloro-4-fluorophenyl)-3-methoxy-10-(trifluoromethyl)-3,4-dihydro-2H,6H-[1,4]thiazepino[2,3,4-ij]quinazolin-6-one Step 1: (R)-11-(3-chloro-4-fluorophenyl)-8-((3S,5R)-3,5-dimethylpiperazin-1-yl)-3-methoxy-10-(trifluoromethyl)-3,4-dihydro-2H,6H-[1,4]thiazepino[2,3,4-ij]quinazolin-6-one

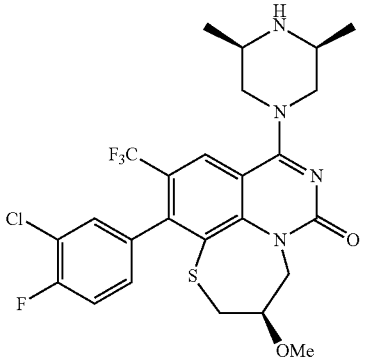

The title compound was prepared analogously to Example 100, step 21 where (R)-11-(3-chloro-4-fluorophenyl)-3-methoxy-10-(trifluoromethyl)-3,4-dihydro-2H,6H-[1,4]thiazepino[2,3,4-ij]quinazoline-6,8(7H)-dione and (2R,6S)-2,6-dimethylpiperazine were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 25% yield as a yellow solid. m/z (ESI, +ve)=557.1 [M+H]$^+$

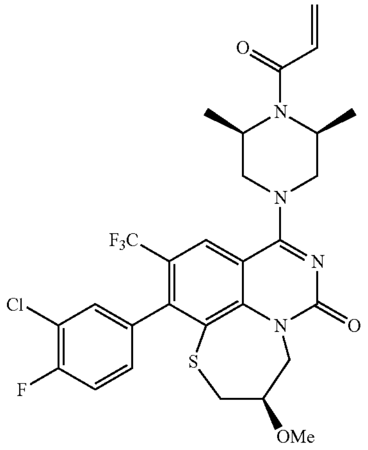 [SMILES: C=CC(=O)N1[C@H](C)CN(c2nc(=O)n3c4c(c(-c5ccc(F)c(Cl)c5)c(C(F)(F)F)cc24)SC[C@H](OC)C3)C[C@@H]1C]

The title compound was prepared analogously to Example 84 where (R)-11-(3-chloro-4-fluorophenyl)-3-methoxy-10-(trifluoromethyl)-3,4-dihydro-2H,6H-[1,4]thiazepino[2,3,4-ij]quinazoline-6,8(7H)-dione was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 39% yield as a yellow solid. m/z (ESI, +ve)=611.2 [M+H]$^+$ 1H NMR (400 MHz, DMSO) δ=8.02 (s, 1H), 7.74-7.48 (m, 2H), 7.43-7.25 (m, 1H), 6.81 (dd, J=16.0, 8.0 Hz, 1H), 6.19 (dd, J=16.0, 4.0 Hz, 1H), 5.74 (dd, J=16.0, 4.0 Hz, 1H), 4.73-4.39 (m, 3H), 4.21-4.00 (m, 2H), 3.93-3.76 (m, 1H), 3.55-3.31 (m, 5H), 3.30-3.19 (m, 2H), 3.18-3.05 (m, 1H), 1.71-1.10 (m, 6H).

Example 1046: (S)-8-((3S,5R)-4-acryloyl-3,5-dimethylpiperazin-1-yl)-11-(3-chloro-4-fluorophenyl)-3-methoxy-10-(trifluoromethyl)-3,4-dihydro-2H,6H-[1,4]thiazepino[2,3,4-ij]quinazolin-6-one

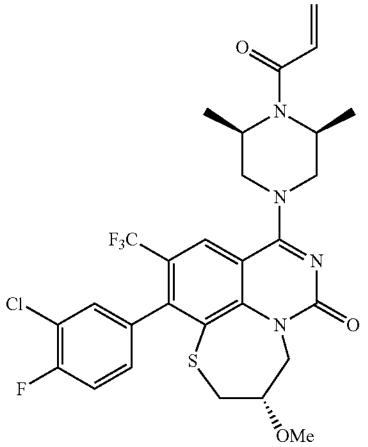 [SMILES: C=CC(=O)N1[C@H](C)CN(c2nc(=O)n3c4c(c(-c5ccc(F)c(Cl)c5)c(C(F)(F)F)cc24)SC[C@@H](OC)C3)C[C@@H]1C]

The title compound was prepared analogously to Example 84 where (S)-11-(3-chloro-4-fluorophenyl)-8-((3S,5R)-3,5-dimethylpiperazin-1-yl)-3-methoxy-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 26% yield as a yellow solid. m/z (ESI, +ve)=611.1 [M+H]$^+$ $^1$H NMR (400 MHz, DMSO-$d_6$) δ 8.02 (s, 1H), 7.60-7.56 (m, 2H), 7.37-7.33 (m, 1H), 6.82 (dd, J=16.0, 8.0 Hz, 1H), 6.19 (dd, J=16.0, 4.0 Hz, 1H), 5.74 (dd, J=16.0, 4.0 Hz, 1H), 4.66-4.47 (m, 3H), 4.09-4.05 (m, 2H), 3.86-3.82 (m, 1H), 3.35-3.31 (m, 7H), 3.15-3.11 (m, 1H), 1.40 (s, 6H).

Step 1: (S)-11-(3-chloro-4-fluorophenyl)-8-((3S, 5R)-3,5-dimethylpiperazin-1-yl)-3-methoxy-10-(trifluoromethyl)-3,4-dihydro-2H,6H-[1,4]thiazepino[2,3,4-ij]quinazolin-6-one

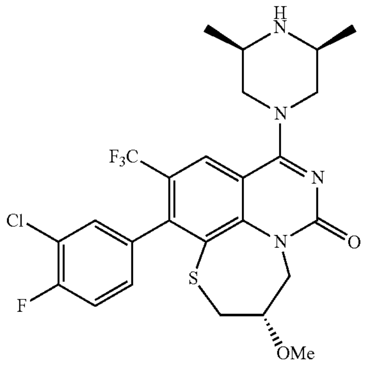 [SMILES: CO[C@@H]1CSc2c(-c3ccc(F)c(Cl)c3)c(C(F)(F)F)cc3c(N4C[C@@H](C)N[C@@H](C)C4)nc(=O)n(c23)C1]

The title compound was prepared analogously to Example 100, step 21 where (S)-11-(3-chloro-4-fluorophenyl)-3-methoxy-10-(trifluoromethyl)-3,4-dihydro-2H,6H-[1,4]thiazepino[2,3,4-ij]quinazoline-6,8(7H)-dione and (2R,6S)-2,6-dimethylpiperazine were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 82% yield as a yellow solid; m/z (ESI, +ve)=557.1 [M+H]$^+$.

TABLE 9

| Example Number | CAF (% binding after 60 min) |
|---|---|
| 1001 | 84 |
| 1002 | 97 |
| 1003 | 95 |
| 1004 | 97 |
| 1005 | 97 |
| 1006 | 90 |
| 1007 | 97 |
| 1008 | 92 |
| 1009 | 96 |
| 1010 | 96 |
| 1011 | 97 |
| 1012 | 95 |
| 1013 | 95 |
| 1014 | 96 |
| 1015 | 84 |
| 1016 | 98 |
| 1017 | 98 |
| 1018 | 96 |
| 1019 | 97 |
| 1020 | 97 |
| 1021 | 97 |
| 1022 | 85 |
| 1023 | 97 |
| 1024 | 97 |
| 1025 | 96 |
| 1026 | 95 |
| 1027 | 96 |
| 1028 | 96 |
| 1029 | 96 |

TABLE 9-continued

| Example Number | CAF (% binding after 60 min) |
|---|---|
| 1030 | 96 |
| 1031 | 95 |
| 1032 | 92 |
| 1033 | 96 |
| 1034 | 97 |
| 1035 | 97 |
| 1036 | 97 |
| 1037 | 96 |
| 1038 | 97 |
| 1039 | 96 |
| 1040 | 96 |
| 1041 | 97 |
| 1042 | 97 |
| 1043 | 97 |
| 1044 | 97 |
| 1045 | 96 |
| 1046 | 96 |

Example 1200: (E)-11-(2,4-difluorophenyl)-8-(9-(4-fluorobut-2-enoyl)-7-oxo-3,9-diazabicyclo[3.3.1]nonan-3-yl)-10-(trifluoromethyl)-3,4-dihydro-2H,6H-[1,4]thiazepino[2,3,4-ij]quinazolin-6-one

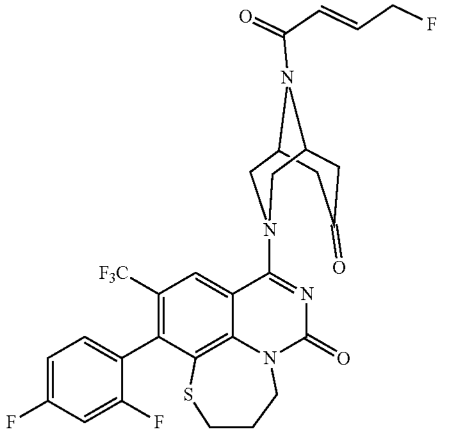 [SMILES: O=C1CC2CN(c3nc(=O)n4c5c(c(-c6ccc(F)cc6F)c(C(F)(F)F)cc35)SCCC4)CC(C1)N2C(=O)/C=C/CF]

The title compound was prepared analogously to Example 84 where 11-(2,4-difluorophenyl)-8-(7-oxo-3,9-diazabicyclo[3.3.1]nonan-3-yl)-10-(trifluoromethyl)-3,4-dihydro-2H,6H-[1,4]thiazepino[2,3,4-ij]quinazolin-6-one and (E)-4-fluorobut-2-enoyl chloride were substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one and acryloyl chloride. The title compound was isolated in 10% yield as a yellow solid. m/z (ESI, +ve)=623.1 [M+H]$^+$. $^1$H NMR (400 MHz, DMSO) δ 7.85-7.81 (m, 1H), 7.49-7.34 (m, 2H), 7.27 (s, 1H), 6.98-6.56 (m, 2H), 5.26-5.08 (m, 2H), 4.76-4.72 (m, 1H), 4.55-4.49 (m, 2H), 4.09-3.85 (m, 2H), 3.53-3.40 (m, 2H), 3.23-3.19 (m, 2H), 3.08-2.89 (m, 3H), 2.75-2.68 (m, 2H), 2.06-1.97 (m, 2H). $^1$H NMR (400 MHz, DMSO) δ 7.85-7.81 (m, 1H), 7.49-7.34 (m, 2H), 7.27 (s, 1H), 6.98-6.56 (m, 2H), 5.26-5.08 (m, 2H), 4.76-4.72 (m, 1H), 4.55-4.49 (m, 2H), 4.09-3.85 (m, 2H), 3.53-3.40 (m, 2H), 3.23-3.19 (m, 2H), 3.08-2.89 (m, 3H), 2.75-2.68 (m, 2H), 2.06-1.97 (m, 2H).

Example 1201: (S)-8-((2S,5R)-4-acryloyl-2,5-dimethylpiperazin-1-yl)-11-(3-chloro-4-fluorophenyl)-3-methoxy-10-(trifluoromethyl)-3,4-dihydro-2H,6H-[1,4]thiazepino[2,3,4-ij]quinazolin-6-one

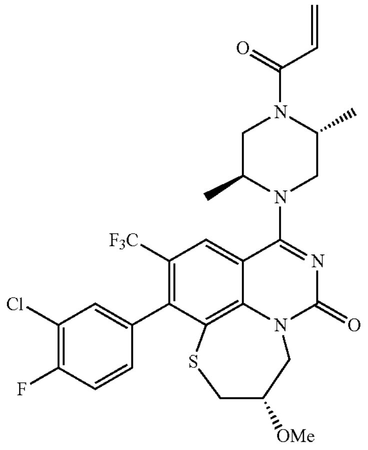 [SMILES: C=CC(=O)N1C[C@H](C)N(c2nc(=O)n3c4c(c(-c5ccc(F)c(Cl)c5)c(C(F)(F)F)cc24)SC[C@@H](OC)C3)C[C@H]1C]

The title compound was prepared analogously to Example 84 where (S)-11-(3-chloro-4-fluorophenyl)-8-((2S,5R)-2,5-dimethylpiperazin-1-yl)-3-methoxy-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 32% yield as a yellow solid. m/z (ESI, +ve)=611.2 [M+H]+. $^1$H NMR (400 MHz, DMSO-$d_6$) δ 7.83 (s, 1H), 7.60-7.56 (m, 2H), 7.35 (s, 1H), 6.81 (dd, J=16.0, 8.0 Hz, 1H), 6.18 (dd, J=16.0, 4.0 Hz, 1H), 5.74 (dd, J=16.0, 4.0 Hz, 1H), 4.78-4.74 (m, 1H), 4.51-4.48 (m, 3H), 4.11-3.72 (m, 5H), 3.28-3.13 (m, 5H), 1.27 (s, 6H).

Step 1: tert-butyl (2R,5S)-4-((S)-11-(3-chloro-4-fluorophenyl)-3-methoxy-6-oxo-10-(trifluoromethyl)-3,4-dihydro-2H,6H-[1,4]thiazepino[2,3,4-ij]quinazolin-8-yl)-2,5-dimethylpiperazine-1-carboxylate

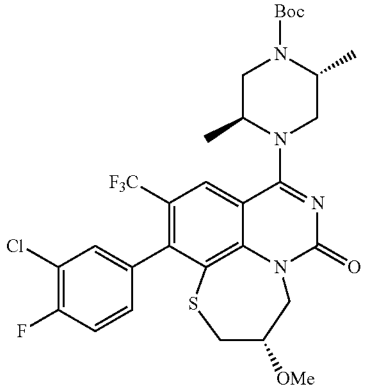 [SMILES: CO[C@@H]1CSc2c(-c3ccc(F)c(Cl)c3)c(C(F)(F)F)cc3c(N4C[C@@H](C)N(C(=O)OC(C)(C)C)C[C@@H]4C)nc(=O)n(c23)C1]

The title compound was prepared analogously to Example 100, step 21 where (S)-11-(3-chloro-4-fluorophenyl)-3-methoxy-10-(trifluoromethyl)-3,4-dihydro-2H,6H-[1,4]thiazepino[2,3,4-ij]quinazoline-6,8(7H)-dione and tert-butyl (2R,5S)-2,5-dimethylpiperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 81% yield as a yellow solid. m/z (ESI, +ve)=657.2 [M+H]$^+$.

Step 2: (S)-11-(3-chloro-4-fluorophenyl)-8-((2S,5R)-2,5-dimethylpiperazin-1-yl)-3-methoxy-10-(trifluoromethyl)-3,4-dihydro-2H,6H-[1,4]thiazepino[2,3,4-ij]quinazolin-6-one

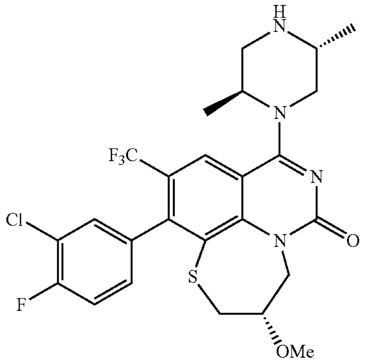 [SMILES: CO[C@@H]1CSc2c(-c3ccc(F)c(Cl)c3)c(C(F)(F)F)cc3c(N4C[C@@H](C)NC[C@@H]4C)nc(=O)n(c23)C1]

The title compound was prepared analogously to Example 102, step 4, where tert-butyl (2R,5S)-4-((S)-11-(3-chloro-4-fluorophenyl)-3-methoxy-6-oxo-10-(trifluoromethyl)-3,4-dihydro-2H,6H-[1,4]thiazepino[2,3,4-ij]quinazolin-8-yl)-2,5-dimethylpiperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 94% yield as a yellow solid. m/z (ESI, +ve)=557.1 [M+H]+.

Example 1202: (S)-8-((2S,5R)-4-acryloyl-2,5-dimethylpiperazin-1-yl)-11-(4-fluorophenyl)-3-methoxy-10-(trifluoromethyl)-3,4-dihydro-2H,6H-[1,4]thiazepino[2,3,4-ij]quinazolin-6-one

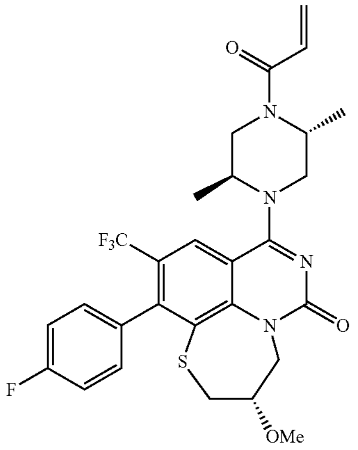 [SMILES: C=CC(=O)N1C[C@H](C)N(c2nc(=O)n3c4c(c(-c5ccc(F)cc5)c(C(F)(F)F)cc24)SC[C@@H](OC)C3)C[C@H]1C]

The title compound was prepared analogously to Example 84 where (S)-8-((2S,5R)-2,5-dimethylpiperazin-1-yl)-11-(4- fluorophenyl)-3-methoxy-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 54% yield as a yellow solid. m/z (ESI, +ve)=577.2 [M+H]+. $^1$H NMR (400 MHz, DMSO-$d_6$) δ 7.83 (s, 1H), 7.34 (d, J=8.0 Hz, 4H), 6.89-6.72 (m, 1H), 6.18 (dd, J=16.0 Hz, 4.0 Hz, 1H), 5.76-5.72 (m, 1H), 4.76 (s, 1H), 4.66-4.39 (m, 3H), 4.14-3.72 (m, 5H), 3.42-3.34 (m, 4H), 3.12 (m 1H), 1.26 (s, 6H).

Step 1: tert-butyl (2R,5S)-4-((S)-11-(4-fluorophenyl)-3-methoxy-6-oxo-10-(trifluoromethyl)-3,4-dihydro-2H,6H-[1,4]thiazepino[2,3,4-ij]quinazolin-8-yl)-2,5-dimethylpiperazine-1-carboxylate

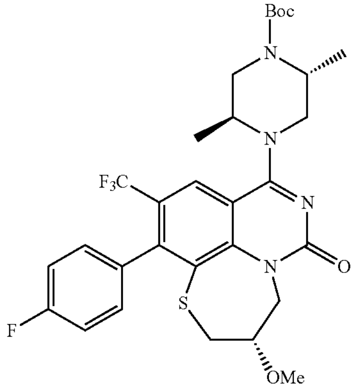 [SMILES: CO[C@@H]1CSc2c(-c3ccc(F)cc3)c(C(F)(F)F)cc3c(N4C[C@@H](C)N(C(=O)OC(C)(C)C)C[C@@H]4C)nc(=O)n(c23)C1]

The title compound was prepared analogously to Example 100, step 21 where (S)-11-(4-fluorophenyl)-3-methoxy-10-(trifluoromethyl)-3,4-dihydro-2H,6H-[1,4]thiazepino[2,3,4-ij]quinazoline-6,8(7H)-dione and tert-butyl (2R,5S)-2,5-dimethylpiperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 88% yield as a yellow solid. m/z (ESI, +ve)=623.2 [M+H]+.

Step 2: (S)-8-((2S,5R)-2,5-dimethylpiperazin-1-yl)-11-(4-fluorophenyl)-3-methoxy-10-(trifluoromethyl)-3,4-dihydro-2H,6H-[1,4]thiazepino[2,3,4-ij]quinazolin-6-one

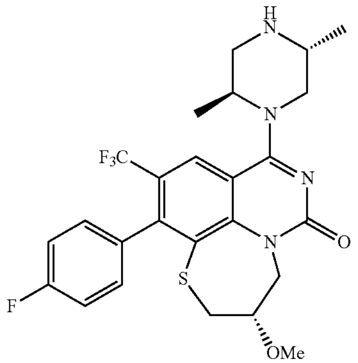 [SMILES: CO[C@@H]1CSc2c(-c3ccc(F)cc3)c(C(F)(F)F)cc3c(N4C[C@@H](C)NC[C@@H]4C)nc(=O)n(c23)C1]

The title compound was prepared analogously to Example 102, step 4, where tert-butyl (2R,5S)-4-((S)-11-(4-fluorophenyl)-3-methoxy-6-oxo-10-(trifluoromethyl)-3,4-dihydro-2H,6H-[1,4]thiazepino[2,3,4-ij]quinazolin-8-yl)-2,5-dimethylpiperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 88% yield as a yellow solid. m/z (ESI, +ve)=523.1 [M+H]+.

Example 1203: (S)-8-((3S,5R)-4-acryloyl-3,5-dimethylpiperazin-1-yl)-3-ethoxy-11-(4-fluorophenyl)-10-(trifluoromethyl)-3,4-dihydro-2H,6H-[1,4]thiazepino[2,3,4-ij]quinazolin-6-one

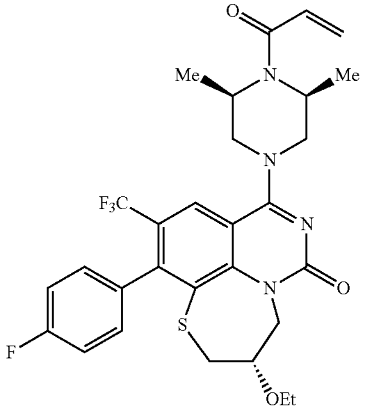 [SMILES: C=CC(=O)N1[C@H](C)CN(c2nc(=O)n3c4c(c(-c5ccc(F)cc5)c(C(F)(F)F)cc24)SC[C@@H](OCC)C3)C[C@@H]1C]

The title compound was prepared analogously to Example 84 where (S)-8-((3S,5R)-3,5-dimethylpiperazin-1-yl)-3-ethoxy-11-(4-fluorophenyl)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 28% yield as a yellow solid. m/z (ESI, +ve)=591.2 [M+H]+.

$^1$H NMR (400 MHz, DMSO-d6) δ 8.02 (s, 1H), 7.44-7.24 (m, 4H), 6.82 (dd, J=16.0 Hz, 8.0 Hz, 1H), 6.19 (dd, J=16.0, 4.0 Hz, 1H), 5.74 (dd, J=16.0, 4.0 Hz, 1H), 4.71-4.53 (m, 2H), 4.49-4.43 (m, 1H), 4.15-4.00 (m, 2H), 3.93-3.88 (m, 1H), 3.59-3.28 (m, 2H), 3.33-3.17 (m, 4H), 3.09-3.01 (m, 1H), 1.52-1.22 (m, 6H), 1.10 (t, J=8.0 Hz, 3H).

Step 1: (S)-3-mercapto-2-methoxypropan-1-ol

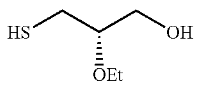

The title compound was synthesized analogously to example 464, steps 1 to 3, where in step 3 ethyl iodide was used in place of methyl iodide. m/z (ESI, +ve)=137.1 [M+H]+.

Step 2: (S)-8-((2-ethoxy-3-hydroxypropyl)thio)-7-(4-fluorophenyl)-6-(trifluoromethyl)quinazoline-2,4(1H,3H)-dione

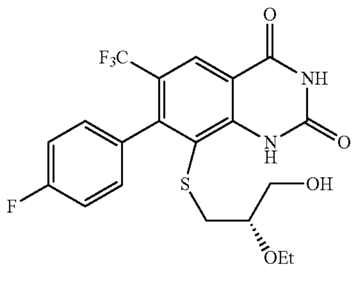 [SMILES: CCO[C@@H](CO)CSc1c(-c2ccc(F)cc2)c(C(F)(F)F)cc2c(=O)[nH]c(=O)[nH]c12]

The title compound was synthesized analogously to example 100, step 9 where 7-(4-fluorophenyl)-8-iodo-6-(trifluoromethyl)quinazoline-2,4(1H,3H)-dione and (S)-2-ethoxy-3-mercaptopropan-1-ol were substituted in place of 7-(2,4-difluorophenyl)-8-iodo-6-(trifluoromethyl)quinazoline-2,4(1H,3H)-dione and 2-mercaptoethan-1-ol. The title compound was isolated in 88% yield as a white solid. m/z (ESI, +ve)=459.0 [M+H]+

Step 3: (S)-3-ethoxy-11-(4-fluorophenyl)-10-(trifluoromethyl)-3,4-dihydro-2H,6H-[1,4]thiazepino[2,3,4-ij]quinazoline-6,8(7H)-dione

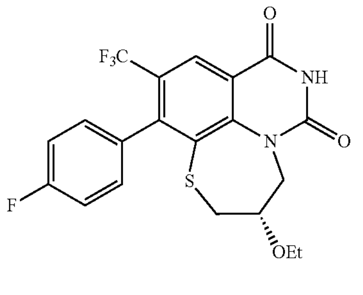 [SMILES: CCO[C@@H]1CSc2c(-c3ccc(F)cc3)c(C(F)(F)F)cc3c(=O)[nH]c(=O)n(c23)C1]

The title compound was prepared analogously to Example 100, step 10 where (S)-8-((2-ethoxy-3-hydroxypropyl)thio)-7-(4-fluorophenyl)-6-(trifluoromethyl)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 90% yield as a yellow solid. m/z (ESI, +ve)=441.0 [M+H]+.

Step 4: (S)-8-((3S,5R)-3,5-dimethylpiperazin-1-yl)-3-ethoxy-11-(4-fluorophenyl)-10-(trifluoromethyl)-3,4-dihydro-2H,6H-[1,4]thiazepino[2,3,4-ij]quinazolin-6-one

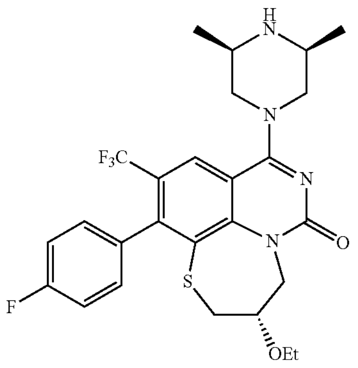 [SMILES: CCO[C@@H]1CSc2c(-c3ccc(F)cc3)c(C(F)(F)F)cc3c(N4C[C@@H](C)N[C@@H](C)C4)nc(=O)n(c23)C1]

The title compound was prepared analogously to Example 100, step 21 where (S)-3-ethoxy-11-(4-fluorophenyl)-10-(trifluoromethyl)-3,4-dihydro-2H,6H-[1,4]thiazepino[2,3,4-ij]quinazoline-6,8(7H)-dione and (2R,6S)-2,6-dimethylpiperazine were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 90% yield as a yellow solid. m/z (ESI, +ve)=537.2 [M+H]+.

Example 1204: (S)-8-((3S,5R)-4-acryloyl-3,5-dimethylpiperazin-1-yl)-11-(3-chloro-4-fluorophenyl)-3-ethoxy-10-(trifluoromethyl)-3,4-dihydro-2H,6H-[1,4]thiazepino[2,3,4-ij]quinazolin-6-one

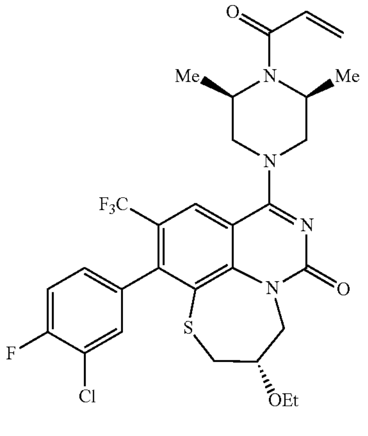 [SMILES: C=CC(=O)N1[C@H](C)CN(c2nc(=O)n3c4c(c(-c5ccc(F)c(Cl)c5)c(C(F)(F)F)cc24)SC[C@@H](OCC)C3)C[C@@H]1C]

The title compound was prepared analogously to Example 84 where (S)-11-(3-chloro-4-fluorophenyl)-8-((3S,5R)-3,5-dimethylpiperazin-1-yl)-3-ethoxy-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 24% yield as a yellow solid. m/z (ESI, +ve)=625.2 [M+H]+. $^1$H NMR (400 MHz, DMSO) δ 8.02 (s, 1H), 7.60-7.56 (m, 2H), 7.36-7.28 (m, 1H), 6.81 (dd, J=16.0, 8.0 Hz, 1H), 6.19 (dd, J=16.0, 4.0 Hz, 1H), 5.74 (dd, J=16.0, 4.0 Hz, 1H), 4.59 (s, 2H), 4.50-4.47 (m, 1H), 4.09-4.03 (m, 2H), 3.96-3.93 (m, 1H), 3.54 (s, 1H), 3.36-3.31 (m, 2H), 3.30-3.20 (m, 3H), 3.16-3.14 (m, 1H), 1.40 (s, 6H), 1.10 (t, J=8.0 Hz, 3H).

Step 1: (S)-7-(3-chloro-4-fluorophenyl)-8-((2-ethoxy-3-hydroxypropyl)thio)-6-(trifluoromethyl) quinazoline-2,4(1H,3H)-dione

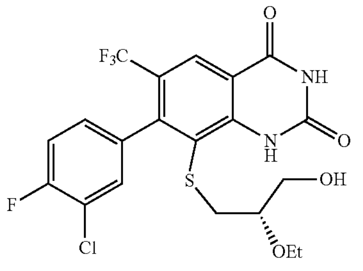 [SMILES: CCO[C@@H](CO)CSc1c(-c2ccc(F)c(Cl)c2)c(C(F)(F)F)cc2c(=O)[nH]c(=O)[nH]c12]

The title compound was synthesized analogously to example 100, step 9 where 7-(3-chloro-4-fluorophenyl)-8-iodo-6-(trifluoromethyl)quinazoline-2,4(1H,3H)-dione and (S)-2-ethoxy-3-mercaptopropan-1-ol were substituted in place of 7-(2,4-difluorophenyl)-8-iodo-6-(trifluoromethyl) quinazoline-2,4(1H,3H)-dione and 2-mercaptoethan-1-ol. The title compound was isolated in 71% yield as a white solid. m/z (ESI, +ve)=493.0 [M+H]+

Step 2: (S)-11-(3-chloro-4-fluorophenyl)-3-ethoxy-10-(trifluoromethyl)-3,4-dihydro-2H,6H-[1,4]thiazepino[2,3,4-ij]quinazoline-6,8(7H)-dione

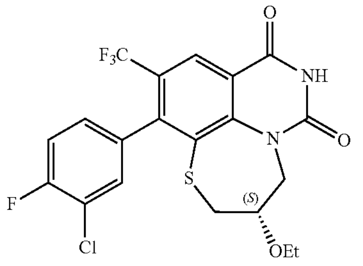

The title compound was prepared analogously to Example 100, step 10 where (S)-7-(3-chloro-4-fluorophenyl)-8-((2-ethoxy-3-hydroxypropyl)thio)-6-(trifluoromethyl)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 67% yield as a yellow solid. m/z (ESI, +ve)=475.0 [M+H]+

Step 3: (S)-11-(3-chloro-4-fluorophenyl)-8-((3S,5R)-3,5-dimethylpiperazin-1-yl)-3-ethoxy-10-(trifluoromethyl)-3,4-dihydro-2H,6H-[1,4]thiazepino[2,3,4-ij]quinazolin-6-one

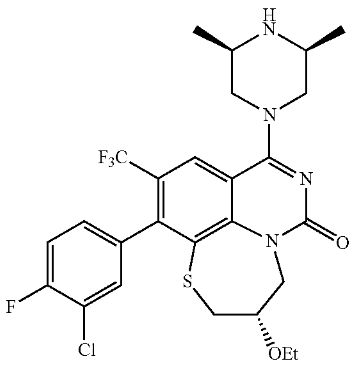 [SMILES: CCO[C@@H]1CSc2c(-c3ccc(F)c(Cl)c3)c(C(F)(F)F)cc3c(N4C[C@@H](C)N[C@@H](C)C4)nc(=O)n(c23)C1]

The title compound was prepared analogously to Example 100, step 21 where (S)-11-(3-chloro-4-fluorophenyl)-3-ethoxy-10-(trifluoromethyl)-3,4-dihydro-2H,6H-[1,4]thiazepino[2,3,4-ij]quinazoline-6,8(7H)-dione and (2R,6S)-2,6-dimethylpiperazine were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 69% yield as a yellow solid. m/z (ESI, +ve)=571.0 [M+H]+.

Example 1205: (3S)-8-((3S,5R)-4-acryloyl-3,5-dimethylpiperazin-1-yl)-11-(2,4-difluorophenyl)-3-ethoxy-10-(trifluoromethyl)-3,4-dihydro-2H,6H-[1,4]thiazepino[2,3,4-ij]quinazolin-6-one

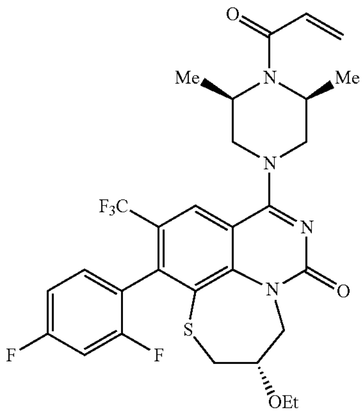 [SMILES: C=CC(=O)N1[C@H](C)CN(c2nc(=O)n3c4c(c(-c5ccc(F)cc5F)c(C(F)(F)F)cc24)SC[C@@H](OCC)C3)C[C@@H]1C]

The title compound was prepared analogously to Example 84 where (3S)-11-(2,4-difluorophenyl)-8-((3S,5R)-3,5-dimethylpiperazin-1-yl)-3-ethoxy-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 47 yield as a yellow solid. m/z (ESI, +ve)=609.2 [M+H]+. $^1$H NMR (400 MHz, DMSO) δ=8.04 (s, 1H), 7.45-7.41 (m, 2H), 7.26 (t, J=8.0

Hz, 1H), 6.81 (dd, J=16.0, 8.0 Hz, 1H), 6.19 (dd, J=16.0, 4.0 Hz, 1H), 5.74 (dd, J=16.0, 4.0 Hz, 1H), 4.59 (s, 2H), 4.48-4.44 (m, 1H), 4.08-4.04 (m, 2H), 3.97-3.93 (m, 1H), 3.49-3.43 (m, 3H), 3.28-3.24 (m, 3H), 3.17-3.06 (m, 1H), 1.53-1.32 (m, 6H), 1.10 (t, J=8.0 Hz, 3H).

Step 1: 7-(2,4-difluorophenyl)-8-(((S)-2-ethoxy-3-hydroxypropyl)thio)-6-(trifluoromethyl)quinazoline-2,4(1H,3H)-dione

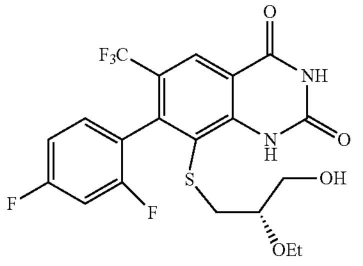 [SMILES: CCO[C@@H](CO)CSc1c(-c2ccc(F)cc2F)c(C(F)(F)F)cc2c(=O)[nH]c(=O)[nH]c12]

The title compound was synthesized analogously to example 100, step 9 where 7-(2,4-difluorophenyl)-8-iodo-6-(trifluoromethyl)quinazoline-2,4(1H,3H)-dione and (S)-2-ethoxy-3-mercaptopropan-1-ol were substituted in place of 7-(2,4-difluorophenyl)-8-iodo-6-(trifluoromethyl)quinazoline-2,4(1H,3H)-dione and 2-mercaptoethan-1-ol. The title compound was isolated in 93% yield as a white solid. m/z (ESI, +ve)=477.1 [M+H]+.

Step 2: (3S)-11-(2,4-difluorophenyl)-3-ethoxy-10-(trifluoromethyl)-3,4-dihydro-2H,6H-[1,4]thiazepino[2,3,4-ij]quinazoline-6,8(7H)-dione

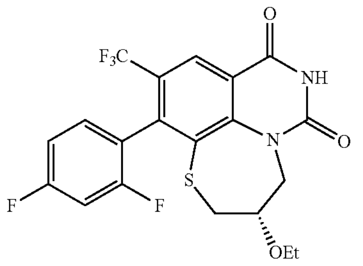 [SMILES: CCO[C@@H]1CSc2c(-c3ccc(F)cc3F)c(C(F)(F)F)cc3c(=O)[nH]c(=O)n(c23)C1]

The title compound was prepared analogously to Example 100, step 10 where 7-(2,4-difluorophenyl)-8-(((S)-2-ethoxy-3-hydroxypropyl)thio)-6-(trifluoromethyl)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 75% yield as a yellow solid. m/z (ESI, +ve)=459.1 [M+H]+.

Step 3: (3S)-11-(2,4-difluorophenyl)-8-((3S,5R)-3,5-dimethylpiperazin-1-yl)-3-ethoxy-10-(trifluoromethyl)-3,4-dihydro-2H,6H-[1,4]thiazepino[2,3,4-ij]quinazolin-6-one

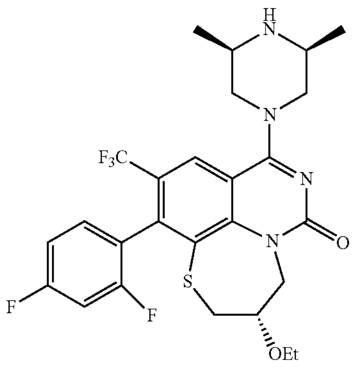 [SMILES: CCO[C@@H]1CSc2c(-c3ccc(F)cc3F)c(C(F)(F)F)cc3c(N4C[C@@H](C)N[C@@H](C)C4)nc(=O)n(c23)C1]

The title compound was prepared analogously to Example 100, step 21 where (3S)-11-(2,4-difluorophenyl)-3-ethoxy-10-(trifluoromethyl)-3,4-dihydro-2H,6H-[1,4]thiazepino[2,3,4-ij]quinazoline-6,8(7H)-dione and (2R,6S)-2,6-dimethylpiperazine were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 74% yield as a yellow solid. m/z (ESI, +ve)=555.2 [M+H]+.

Example 1206: (3S)-8-((3S,5R)-4-acryloyl-3,5-dimethylpiperazin-1-yl)-11-(5-chloro-2,4-difluorophenyl)-3-ethoxy-10-(trifluoromethyl)-3,4-dihydro-2H,6H-[1,4]thiazepino[2,3,4-ij]quinazolin-6-one

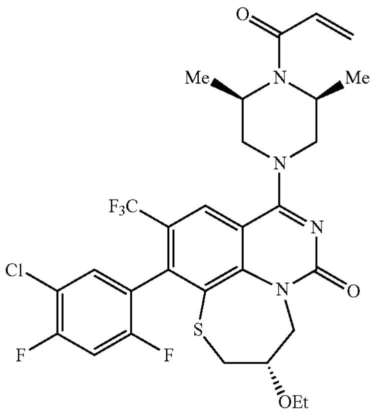 [SMILES: C=CC(=O)N1[C@H](C)CN(c2nc(=O)n3c4c(c(-c5cc(Cl)c(F)cc5F)c(C(F)(F)F)cc24)SC[C@@H](OCC)C3)C[C@@H]1C]

The title compound was prepared analogously to Example 84 where (3S)-11-(5-chloro-2,4-difluorophenyl)-8-((3S,5R)-3,5-dimethylpiperazin-1-yl)-3-ethoxy-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 34% yield as a yellow solid. m/z (ESI, +ve)=643.2 [M+H]+. $^1$H NMR (400 MHz, DMSO) δ 8.05 (s, 1H), 7.80-7.76 (m, 2H), 6.81 (dd, J=16.0, 8.0 Hz, 1H), 6.19 (dd, J=16.0, 4.0 Hz, 1H), 5.75 (dd, J=16.0, 4.0 Hz, 1H), 4.76-4.28 (m, 4H), 4.12-3.90 (m, 3H), 3.57-3.53 (m, 3H), 3.31-3.12 (m, 3H), 1.50-1.25 (m, 6H), 1.11 (t, J=8.0 Hz, 3H).

Step 1: 7-(5-chloro-2,4-difluorophenyl)-8-(((S)-2-ethoxy-3-hydroxypropyl)thio)-6-(trifluoromethyl) quinazoline-2,4(1H,3H)-dione

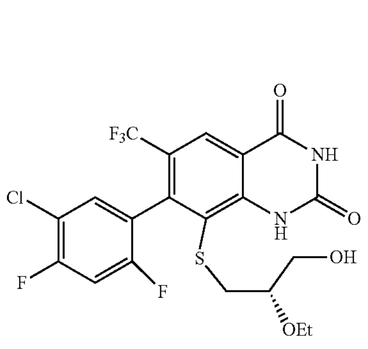 [SMILES: CCO[C@@H](CO)CSc1c(-c2cc(Cl)c(F)cc2F)c(C(F)(F)F)cc2c(=O)[nH]c(=O)[nH]c12]

The title compound was synthesized analogously to example 100, step 9 where 7-(5-chloro-2,4-difluorophenyl)-8-iodo-6-(trifluoromethyl)quinazoline-2,4(1H,3H)-dione and (S)-2-ethoxy-3-mercaptopropan-1-ol were substituted in place of 7-(2,4-difluorophenyl)-8-iodo-6-(trifluoromethyl)quinazoline-2,4(1H,3H)-dione and 2-mercaptoethan-1-ol. The title compound was isolated in 82% yield as a white solid. m/z (ESI, +ve)=511.0 [M+H]+

Step 2: (3S)-11-(5-chloro-2,4-difluorophenyl)-3-ethoxy-10-(trifluoromethyl)-3,4-dihydro-2H,6H-[1,4]thiazepino[2,3,4-ij]quinazoline-6,8(7H)-dione

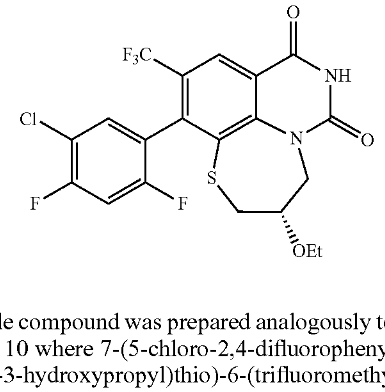

The title compound was prepared analogously to Example 100, step 10 where 7-(5-chloro-2,4-difluorophenyl)-8-(((S)-2-ethoxy-3-hydroxypropyl)thio)-6-(trifluoromethyl)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 97% yield as a yellow solid. m/z (ESI, +ve)=493.0 [M+H]+.

Step 3: (3S)-11-(5-chloro-2,4-difluorophenyl)-8-((3S,5R)-3,5-dimethylpiperazin-1-yl)-3-ethoxy-10-(trifluoromethyl)-3,4-dihydro-2H,6H-[1,4]thiazepino [2,3,4-ij]quinazolin-6-one

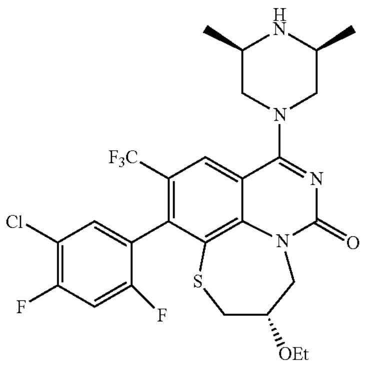 [SMILES: CCO[C@@H]1CSc2c(-c3cc(Cl)c(F)cc3F)c(C(F)(F)F)cc3c(N4C[C@@H](C)N[C@@H](C)C4)nc(=O)n(c23)C1]

The title compound was prepared analogously to Example 100, step 21 where (3S)-11-(5-chloro-2,4-difluorophenyl)-3-ethoxy-10-(trifluoromethyl)-3,4-dihydro-2H,6H-[1,4]thiazepino[2,3,4-ij]quinazoline-6,8(7H)-dione and (2R,6S)-2,6-dimethylpiperazine were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 77% yield as a yellow solid. m/z (ESI, +ve)=589.2 [M+H]+.

Example 1207: (S)-8-((3S,5R)-4-acryloyl-3,5-dimethylpiperazin-1-yl)-11-(5-fluoropyridin-2-yl)-3-methoxy-10-(trifluoromethyl)-3,4-dihydro-2H,6H-[1,4]thiazepino[2,3,4-ij]quinazolin-6-one

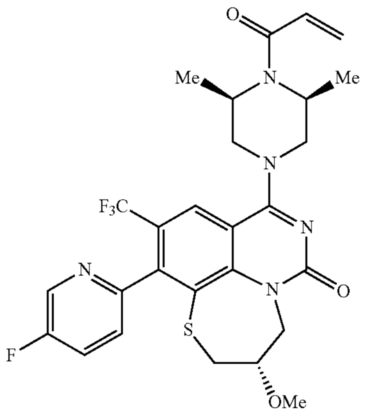 [SMILES: C=CC(=O)N1[C@H](C)CN(c2nc(=O)n3c4c(c(-c5ccc(F)cn5)c(C(F)(F)F)cc24)SC[C@@H](OC)C3)C[C@@H]1C]

The title compound was prepared analogously to Example 84 where (S)-8-((3S,5R)-3,5-dimethylpiperazin-1-yl)-11-(5-fluoropyridin-2-yl)-3-methoxy-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 14% yield as a yellow solid. m/z (ESI, +ve)=578.2 [M+H]+. $^1$H NMR (400 MHz, DMSO) δ=8.73 (s, 1H), 8.04 (s, 1H), 7.92 (t, J=4.0 Hz, 1H), 7.61-7.57 (m, 1H), 6.82 (dd, J=16.0, 8.0 Hz, 1H), 6.19 (dd, J=16.0, 4.0 Hz, 1H), 5.74 (dd, J=16.0, 4.0 Hz, 1H), 4.69-4.46 (m, 3H), 4.08-4.04 (m, 2H), 3.88-3.84 (m, 1H), 3.37-3.33 (m, 5H), 3.29-3.26 (m, 2H), 3.13-3.09 (m, 1H), 1.40 (m, 6H). Step 1: methyl 2-amino-4-(4,4,5,5-tetramethyl-1,3,2-dioxaborolan-2-yl)benzoate.

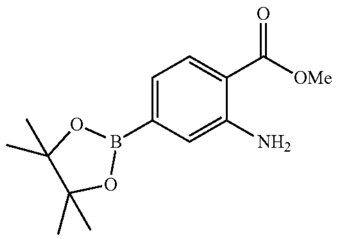 [SMILES: COC(=O)c1ccc(B2OC(C)(C)C(C)(C)O2)cc1N]

A mixture of methyl 2-amino-4-bromobenzoate (0.17 mol), 4,4,4',4',5,5,5',5'-octamethyl-2,2'-bi(1,3,2-dioxaborolane) (0.26 mol), Pd(dppf)$Cl_2$ (17.4 mmol) and KOAc (0.52 mol) in 1,4-dioxane (500 mL) was stirred at 100° C. for 16 hours. The mixture was filtered and concentrated to afford a residue that was purified by silica gel chromatography (0-10% ethyl acetate in hexanes). The title compound was isolated in quantitative yield as a yellow solid. m/z (ESI, +ve)=278.2 [M+H]+.

Step 2: methyl 2-amino-4-(5-fluoropyridin-2-yl)benzoate

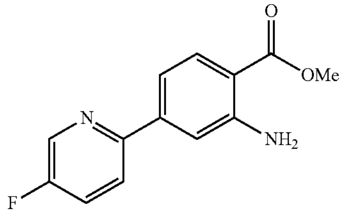 [SMILES: COC(=O)c1ccc(-c2ccc(F)cn2)cc1N]

A mixture of methyl 2-amino-4-(4,4,5,5-tetramethyl-1,3,2-dioxaborolan-2-yl)benzoate (0.14 mol), 2-bromo-5-fluoropyridine (0.11 mol), Pd(dppf)$Cl_2$ (24.5 mmol) and $K_3PO_4$ (0.37 mol) in 1,4-dioxane:$H_2O$ (300 mL:30 mL) was stirred at 100° C. for 16 hours. The mixture was cooled to room temperature and the solids filtered. The filtrate was concentrated to afford a residue that was purified by silica gel column (0-8% ethyl acetate in hexanes) to afford the title compound in 83% yield as a white solid. m/z (ESI, +ve) =247.1 $[M+H]^+$.

Step 3: methyl 2-amino-4-(5-fluoropyridin-2-yl)-5-iodobenzoate

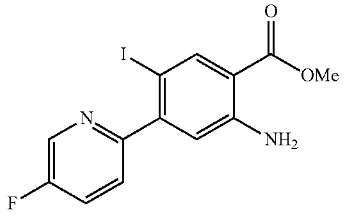 [SMILES: COC(=O)c1cc(I)c(-c2ccc(F)cn2)cc1N]

NIS (0.13 mol) was added over a solution of methyl 2-amino-4-(5-fluoropyridin-2-yl)benzoate (0.13 mol) in DMF (150 mL) and the reaction was stirred at room temperature for 16 hours. The reaction was quenched with water and extracted with ethyl acetate three times. The organic layers were dried over sodium sulfate and concentrated. Purification of the crude material by silica gel chromatography (0-15% ethyl acetate in hexanes) afforded the title compound in 90% yield as a yellow solid. m/z (ESI, +ve) =373.0 [M+H]+.

Step 4: methyl 2-acetamido-4-(5-fluoropyridin-2-yl)-5-iodobenzoate

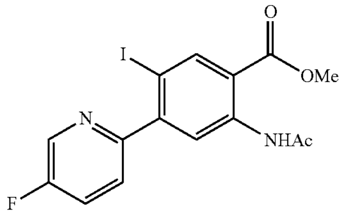 [SMILES: COC(=O)c1cc(I)c(-c2ccc(F)cn2)cc1NC(C)=O]

To a mixture of methyl 2-amino-4-(5-fluoropyridin-2-yl)-5-iodobenzoate (0.055 mol) in AcOH (150 mL) was added acetic anhydride (0.082 mol) and the reaction was stirred at 100° C. for 2 hours. The mixture was cooled to room temperature, diluted with water and filtered. The filtrate cake was dried under reduced pressure to afford the title compound in 99% yield as a white solid. m/z (ESI, +ve)=415.0 [M+H]+.

Step 5: methyl 2-acetamido-4-(5-fluoropyridin-2-yl)-5-(trifluoromethyl)benzoate

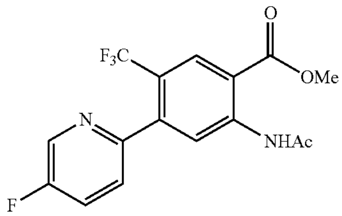 [SMILES: COC(=O)c1cc(C(F)(F)F)c(-c2ccc(F)cn2)cc1NC(C)=O]

To a mixture of methyl 2-acetamido-4-(5-fluoropyridin-2-yl)-5-iodobenzoate (26.5 mmol), CuI (36.8 mmol) and tetrabutylammonium iodide (10.6 mmol) in HMPA (50 mL) was slowly added methyl 2,2-difluoro-2-(fluorosulfonyl) acetate (260.4 mmol). The mixture was stirred at 90° C. for 1.5 hours and cooled down to room temperature, quenched with water and filtered. The filtrate was extracted with ethyl acetate three times and the combined organic layers were washed with water, brine, dried over sodium sulfate and concentrated to afford a residue that was purified by silica gel chromatography (0-15% ethyl acetate in hexanes) to afford the title compound in 53% yield as a yellow solid. m/z (ESI, +ve)=357.1 [M+H]+.

Step 6: methyl 2-amino-4-(5-fluoropyridin-2-yl)-5-(trifluoromethyl)benzoate

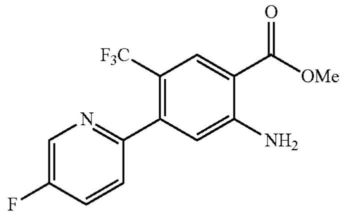 [SMILES: COC(=O)c1cc(C(F)(F)F)c(-c2ccc(F)cn2)cc1N]

A mixture of methyl 2-acetamido-4-(5-fluoropyridin-2-yl)-5-(trifluoromethyl)benzoate (28.1 mmol) in MeOH (50 mL) and concentrated aqueous HCl (50 mL) was stirred at 80° C. for 2 hours. The mixture was cooled down to room temperature and the pH adjusted to 7 by the addition of sodium carbonate. The mixture was extracted with ethyl acetate three times and the combined organic layers were washed with water, brine, dried over sodium sulfate and concentrated to afford the title compound in 97% yield as a yellow oil. m/z (ESI, +ve)=315.0 [M+H]+.

Step 7: methyl 2-amino-4-(5-fluoropyridin-2-yl)-3-iodo-5-(trifluoromethyl)benzoate

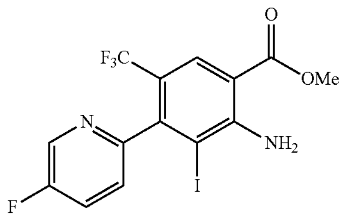 [SMILES: COC(=O)c1cc(C(F)(F)F)c(-c2ccc(F)cn2)c(I)c1N]

To a mixture of methyl 2-amino-4-(5-fluoropyridin-2-yl)-5-(trifluoromethyl)benzoate (27.1 mmol) in AcOH (100 mL) was added N-iodosuccinamide (44.4 mol). The reaction was stirred at room temperature for 36 hours and the volatiles removed under reduced pressure. The resulting residue was redissolved in ethyl acetate and sequentially washed with saturated aqueous $Na_2S_2O_3$, water and brine. The organic layer was dried over sodium sulfate and concentrated to afford a residue that was purified by silica gel chromatography (0-15% ethyl acetate in hexanes) affording the title compound in 88% yield as a yellow solid. m/z (ESI, +ve)=441.0 [M+H]+.

Step 8: 2-amino-4-(5-fluoropyridin-2-yl)-3-iodo-5-(trifluoromethyl)benzoic acid

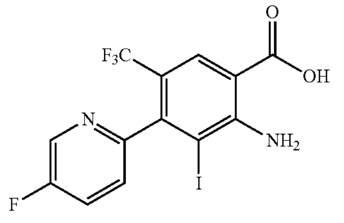

To a mixture of methyl 2-amino-4-(5-fluoropyridin-2-yl)-3-iodo-5-(trifluoromethyl)benzoate (23.8 mmol) in MeOH:THF (30 mL:30 mL) was added aqueous 0.01M NaOH (0.238 mol) and the reaction was stirred at room temperature for 30 minutes. The pH of the mixture was adjusted to 5 by the addition of 6M HCl and the solution was extracted with ethyl acetate three times. The combined organic layers were washed with water, brine, dried over sodium sulfate and concentrated to afford the title compound in 99% yield as a yellow oil. m/z (ESI, +ve)=427.0 [M+H]+.

Step 9: 7-(5-fluoropyridin-2-yl)-8-iodo-6-(trifluoromethyl)quinazoline-2,4(1H,3H)-dione

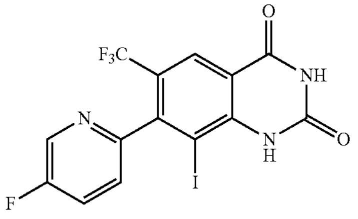

A mixture of 2-amino-4-(5-fluoropyridin-2-yl)-3-iodo-5-(trifluoromethyl)benzoic acid (20.4 mmol) and urea (1.67 mol) was heated at 200° C. for 2 hours. The reaction was cooled down to 90° C. and diluted with 600 mL of methanol:ethyl acetate (1:1). The mixture was allowed to cool down to room temperature slowly and stirred for another 3 hours. After filtration, the volatiles were removed under reduced pressure and the crude material purified by reverse phase silica gel chromatography to afford the title compound as a white solid in 20% yield. m/z (ESI, +ve)=452.0 [M+H]+.

Step 10: (S)-7-(5-fluoropyridin-2-yl)-8-((3-hydroxy-2-methoxypropyl)thio)-6-(trifluoromethyl)quinazoline-2,4(1H,3H)-dione

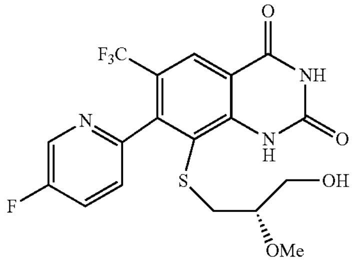 [SMILES: CO[C@@H](CO)CSc1c(-c2ccc(F)cn2)c(C(F)(F)F)cc2c(=O)[nH]c(=O)[nH]c12]

The title compound was synthesized analogously to example 100, step 9 where 7-(5-fluoropyridin-2-yl)-8-iodo-6-(trifluoromethyl)quinazoline-2,4(1H,3H)-dione and (S)-3-mercapto-2-methoxypropan-1-ol were substituted in place of 7-(2,4-difluorophenyl)-8-iodo-6-(trifluoromethyl)quinazoline-2,4(1H,3H)-dione and 2-mercaptoethan-1-ol. The title compound was isolated in 94% yield as a yellow solid. m/z (ESI, +ve)=446.0 [M+H]+.

Step 11: (S)-11-(5-fluoropyridin-2-yl)-3-methoxy-10-(trifluoromethyl)-3,4-dihydro-2H,6H-[1,4]thiazepino[2,3,4-ij]quinazoline-6,8(7H)-dione

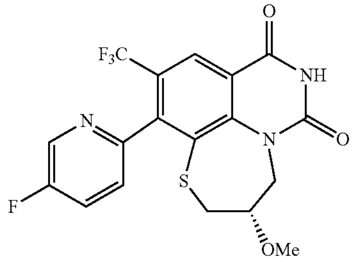 [SMILES: CO[C@@H]1CSc2c(-c3ccc(F)cn3)c(C(F)(F)F)cc3c(=O)[nH]c(=O)n(c23)C1]

The title compound was prepared analogously to Example 100, step 10 where (S)-7-(5-fluoropyridin-2-yl)-8-((3-hydroxy-2-methoxypropyl)thio)-6-(trifluoromethyl)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 14% yield as a yellow solid. m/z (ESI, +ve)=428.0 [M+H]+.

Step 12: (S)-8-((3S,5R)-3,5-dimethylpiperazin-1-yl)-11-(5-fluoropyridin-2-yl)-3-methoxy-10-(trifluoromethyl)-3,4-dihydro-2H,6H-[1,4]thiazepino[2,3,4-ij]quinazolin-6-one

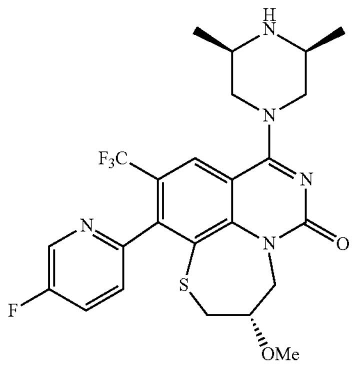 [SMILES: CO[C@@H]1CSc2c(-c3ccc(F)cn3)c(C(F)(F)F)cc3c(N4C[C@@H](C)N[C@@H](C)C4)nc(=O)n(c23)C1]

The title compound was prepared analogously to Example 100, step 21 where (S)-11-(5-fluoropyridin-2-yl)-3-methoxy-10-(trifluoromethyl)-3,4-dihydro-2H,6H-[1,4]thiazepino[2,3,4-ij]quinazoline-6,8(7H)-dione and (2R,6S)-2,6-dimethylpiperazine were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 85% yield as a yellow solid. m/z (ESI, +ve)=524.1 $[M+H]^+$.

Example 1208: (S)-8-((3S,5R)-4-acryloyl-3,5-dimethylpiperazin-1-yl)-3-methoxy-10-(trifluoromethyl)-11-(4-(trifluoromethyl)thiazol-2-yl)-3,4-dihydro-2H,6H-[1,4]thiazepino[2,3,4-ij]quinazolin-6-one

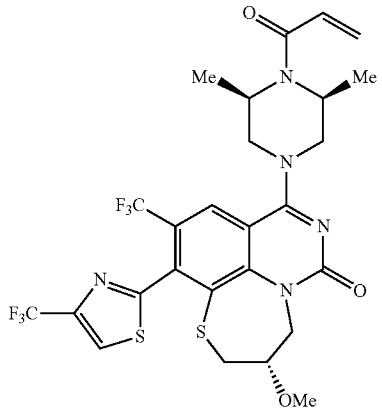 [SMILES: C=CC(=O)N1[C@H](C)CN(c2nc(=O)n3c4c(c(-c5nc(C(F)(F)F)cs5)c(C(F)(F)F)cc24)SC[C@@H](OC)C3)C[C@@H]1C]

The title compound was prepared analogously to Example 84 where (S)-8-((3S,5R)-3,5-dimethylpiperazin-1-yl)-3-methoxy-10-(trifluoromethyl)-11-(4-(trifluoromethyl)thiazol-2-yl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 50% yield as a yellow solid. m/z (ESI, +ve)=634.0 $[M+H]^+$. 1H NMR (400 MHz, DMSO-d6) δ 8.88 (s, 1H), 8.05 (s, 1H), 6.81 (dd, J=16.0, 8.0 Hz, 1H), 6.19 (dd, J=16.0, 4.0 Hz, 1H), 5.74 (d, J=16.0, 4.0 Hz, 1H), 4.58-4.51 (m, 3H), 4.08-4.04 (m, 2H), 3.91-3.83 (m, 1H), 3.55-3.43 (m, 1H), 3.33-3.28 (m, 6H), 3.23-3.19 (m, 1H), 1.40 (s, 6H).

Step 1: 2-bromo-4-(trifluoromethyl)thiazole

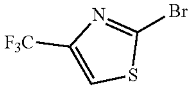

To a 0° C. mixture of 4-(trifluoromethyl)thiazol-2-amine (0.089 mol) and $CuBr_2$ (0.18 mol) in acetonitrile (150 mL) was slowly added tert-butyl nitrite (0.18 mol). After 30 minutes at 0° C., the reaction was stirred at room temperature for 2.5 hours. The mixture was quenched with water extracted with dichloromethane three times and the combined organic layers were washed with brine, dried over sodium sulfate and concentrated under reduced pressure to afford the title compound as a yellow oil that was used in the next step without further purification.

Step 2: methyl 2-amino-4-(4-(trifluoromethyl)thiazol-2-yl)benzoate

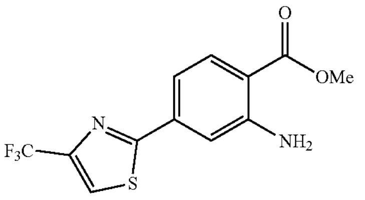 [SMILES: COC(=O)c1ccc(-c2nc(C(F)(F)F)cs2)cc1N]

The title compound was prepared analogously to Example 1207, step 2, where 2-bromo-4-(trifluoromethyl)thiazole was substituted in place of 2-bromo-5-fluoropyridine. The title compound was isolated in 22% yield (last two steps) as a yellow solid. m/z (ESI, +ve)=303.0 [M+H]+.

Step 3: methyl 2-amino-5-iodo-4-(4-(trifluoromethyl)thiazol-2-yl)benzoate

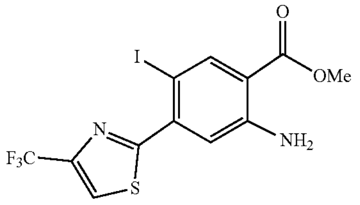 [SMILES: COC(=O)c1cc(I)c(-c2nc(C(F)(F)F)cs2)cc1N]

The title compound was prepared analogously to Example 207, step 3, where methyl 2-amino-4-(4-(trifluoromethyl)thiazol-2-yl)benzoate was substituted in place of methyl 2-amino-4-(5-fluoropyridin-2-yl)benzoate. The title compound was isolated in 90% yield as a yellow solid. m/z (ESI, +ve)=428.9 $[M+H]^+$.

Step 4: methyl 2-acetamido-5-iodo-4-(4-(trifluoromethyl)thiazol-2-yl)benzoate

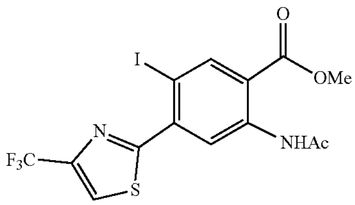 [SMILES: COC(=O)c1cc(I)c(-c2nc(C(F)(F)F)cs2)cc1NC(C)=O]

The title compound was prepared analogously to Example 207, step 4, where methyl 2-amino-5-iodo-4-(4-(trifluoromethyl)thiazol-2-yl)benzoate was substituted in place of methyl 2-amino-4-(5-fluoropyridin-2-yl)-5-iodobenzoate. The title compound was isolated in 97% yield as a yellow solid. m/z (ESI, +ve)=470.9 $[M+H]^+$.

Step 5: methyl 2-acetamido-5-(trifluoromethyl)-4-(4-(trifluoromethyl)thiazol-2-yl)benzoate

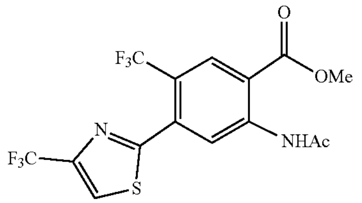 [SMILES: COC(=O)c1cc(C(F)(F)F)c(-c2nc(C(F)(F)F)cs2)cc1NC(C)=O]

The title compound was prepared analogously to Example 207, step 5, where methyl 2-acetamido-5-iodo-4-(4-(trifluoromethyl)thiazol-2-yl)benzoate was substituted in place of methyl 2-acetamido-4-(5-fluoropyridin-2-yl)-5-iodobenzoate. The title compound was isolated in 79% yield as a yellow solid. m/z (ESI, +ve)=413.0 [M+H]+.

Step 6: methyl 2-amino-5-(trifluoromethyl)-4-(4-(trifluoromethyl)thiazol-2-yl)benzoate

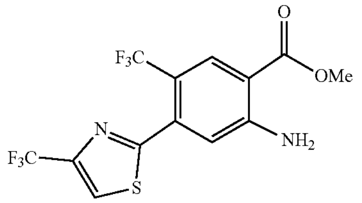 [SMILES: COC(=O)c1cc(C(F)(F)F)c(-c2nc(C(F)(F)F)cs2)cc1N]

The title compound was prepared analogously to Example 207, step 6, where methyl 2-acetamido-5-(trifluoromethyl)-4-(4-(trifluoromethyl)thiazol-2-yl)benzoate was substituted in place of methyl 2-acetamido-4-(5-fluoropyridin-2-yl)-5-(trifluoromethyl)benzoate. The title compound was isolated in 94% yield as a yellow solid. m/z (ESI, +ve)=371.0 [M+H]+.

Step 7: methyl 2-amino-3-iodo-5-(trifluoromethyl)-4-(4-(trifluoromethyl)thiazol-2-yl)benzoate

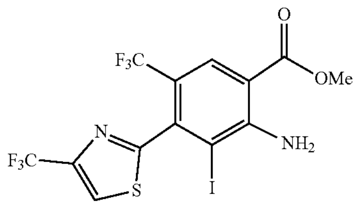 [SMILES: COC(=O)c1cc(C(F)(F)F)c(-c2nc(C(F)(F)F)cs2)c(I)c1N]

The title compound was prepared analogously to Example 207, step 7, where methyl 2-amino-5-(trifluoromethyl)-4-(4-(trifluoromethyl)thiazol-2-yl)benzoate was substituted in place of methyl 2-amino-4-(5-fluoropyridin-2-yl)-5-(trifluoromethyl)benzoate. The title compound was isolated in 89% yield as a yellow solid. m/z (ESI, +ve)=496.9 [M+H]+.

Step 8: 2-amino-3-iodo-5-(trifluoromethyl)-4-(4-(trifluoromethyl)thiazol-2-yl)benzoic acid

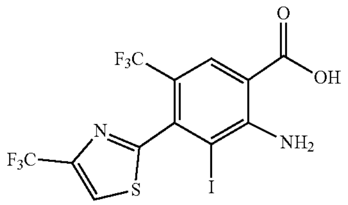 [SMILES: Nc1c(C(=O)O)cc(C(F)(F)F)c(-c2nc(C(F)(F)F)cs2)c1I]

The title compound was prepared analogously to Example 207, step 8, where methyl 2-amino-3-iodo-5-(trifluoromethyl)-4-(4-(trifluoromethyl)thiazol-2-yl)benzoate was substituted in place of methyl 2-amino-4-(5-fluoropyridin-2-yl)-3-iodo-5-(trifluoromethyl)benzoate. The title compound was isolated in 97% yield as a yellow solid. m/z (ESI, +ve)=482.9 [M+H]+

Step 9: 8-iodo-6-(trifluoromethyl)-7-(4-(trifluoromethyl)thiazol-2-yl)quinazoline-2,4(1H,3H)-dione

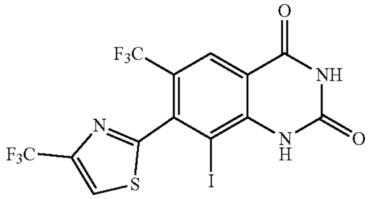 [SMILES: O=c1[nH]c(=O)c2cc(C(F)(F)F)c(-c3nc(C(F)(F)F)cs3)c(I)c2[nH]1]

The title compound was prepared analogously to Example 207, step 9, where 2-amino-3-iodo-5-(trifluoromethyl)-4-(4-(trifluoromethyl)thiazol-2-yl)benzoic acid was substituted in place of 2-amino-4-(5-fluoropyridin-2-yl)-3-iodo-5-(trifluoromethyl)benzoic acid. The title compound was isolated in 48% yield as a yellow solid. m/z (ESI, +ve)=507.9 [M+H]+.

Step 10: (S)-8-((3-hydroxy-2-methoxypropyl)thio)-6-(trifluoromethyl)-7-(4-(trifluoromethyl)thiazol-2-yl)quinazoline-2,4(1H,3H)-dione

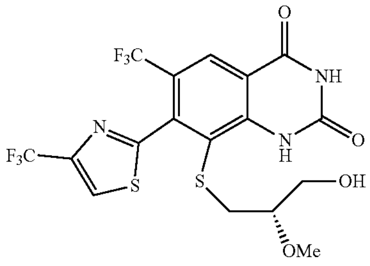 [SMILES: CO[C@@H](CO)CSc1c(-c2nc(C(F)(F)F)cs2)c(C(F)(F)F)cc2c(=O)[nH]c(=O)[nH]c12]

The title compound was synthesized analogously to example 100, step 9 where 8-iodo-6-(trifluoromethyl)-7-(4-(trifluoromethyl)thiazol-2-yl)quinazoline-2,4(1H,3H)-dione and (S)-3-mercapto-2-methoxypropan-1-ol were substituted in place of 7-(2,4-difluorophenyl)-8-iodo-6-(trifluoromethyl)quinazoline-2,4(1H,3H)-dione and 2-mercaptoethan-1-ol. The title compound was isolated in 69% yield as a yellow solid. m/z (ESI, +ve)=502.1 [M+H]+.

Step 11: (S)-3-methoxy-10-(trifluoromethyl)-11-(4-(trifluoromethyl)thiazol-2-yl)-3,4-dihydro-2H,6H-[1,4]thiazepino[2,3,4-ij]quinazoline-6,8(7H)-dione

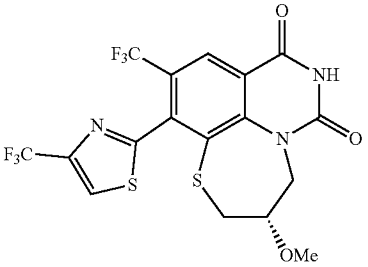 [SMILES: CO[C@@H]1CSc2c(-c3nc(C(F)(F)F)cs3)c(C(F)(F)F)cc3c(=O)[nH]c(=O)n(c23)C1]

The title compound was prepared analogously to Example 100, step 10 where (S)-8-((3-hydroxy-2-methoxypropyl)thio)-6-(trifluoromethyl)-7-(4-(trifluoromethyl)thiazol-2-yl)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 62% yield as a yellow solid. m/z (ESI, +ve)=484.0 [M+H]+.

Step 12: (S)-8-((3S,5R)-3,5-dimethylpiperazin-1-yl)-3-methoxy-10-(trifluoromethyl)-11-(4-(trifluoromethyl)thiazol-2-yl)-3,4-dihydro-2H,6H-[1,4]thiazepino[2,3,4-ij]quinazolin-6-one

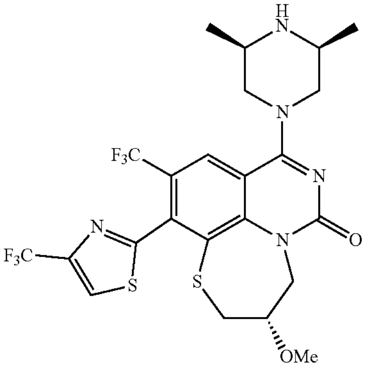 [SMILES: CO[C@@H]1CSc2c(-c3nc(C(F)(F)F)cs3)c(C(F)(F)F)cc3c(N4C[C@@H](C)N[C@@H](C)C4)nc(=O)n(c23)C1]

The title compound was prepared analogously to Example 100, step 21 where (S)-3-methoxy-10-(trifluoromethyl)-11-(4-(trifluoromethyl)thiazol-2-yl)-3,4-dihydro-2H,6H-[1,4]thiazepino[2,3,4-ij]quinazoline-6,8(7H)-dione and (2R,6S)-2,6-dimethylpiperazine were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 79% yield as a yellow solid. m/z (ESI, +ve)=580.1 [M+H]+.

Example 1209: (S)-8-((3S,5R)-4-acryloyl-3,5-dimethylpiperazin-1-yl)-11-(5-fluoro-4-methylpyridin-2-yl)-3-methoxy-10-(trifluoromethyl)-3,4-dihydro-2H,6H-[1,4]thiazepino[2,3,4-ij]quinazolin-6-one

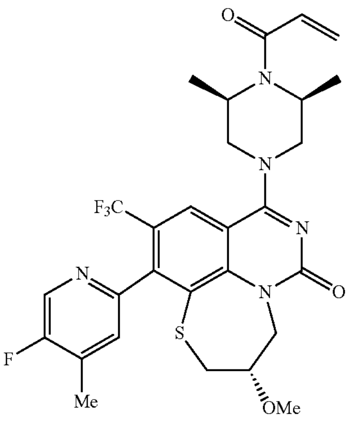 [SMILES: C=CC(=O)N1[C@H](C)CN(c2nc(=O)n3c4c(c(-c5cc(C)c(F)cn5)c(C(F)(F)F)cc24)SC[C@@H](OC)C3)C[C@@H]1C]

The title compound was prepared analogously to Example 84 where (S)-8-((3S,5R)-3,5-dimethylpiperazin-1-yl)-11-(5-fluoro-4-methylpyridin-2-yl)-3-methoxy-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 25% yield as a yellow solid. m/z (ESI, +ve)=592.0 [M+H]+. $^1$H NMR (400 MHz, DMSO-d6) δ 8.60 (s, 1H), 8.03 (s, 1H), 7.52-7.45 (m, 1H), 6.82 (dd, J=16.0, 8.0 Hz, 1H), 6.19 (dd, J=16.0, 4.0 Hz, 1H), 5.74 (dd, J=16.0, 4.0 Hz, 1H), 4.62-4.47 (m, 4H), 4.08-4.02 (m, 2H), 3.85-3.84 (m, 1H), 3.33-3.25 (m, 6H), 3.12-3.09 (m, 1H), 2.36 (s, 3H), 1.40 (s, 6H).

Step 1: methyl 2-amino-4-(5-fluoro-4-methylpyridin-2-yl)benzoate

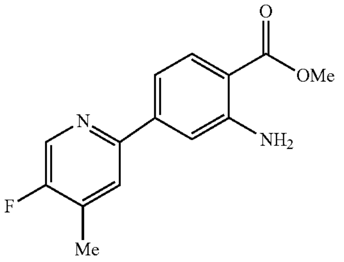 [SMILES: COC(=O)c1ccc(-c2cc(C)c(F)cn2)cc1N]

The title compound was prepared analogously to Example 1207, step 2, where 2-bromo-4-(trifluoromethyl)thiazole was substituted in place of 2-bromo-5-fluoro-4-methylpyridine. The title compound was isolated in 88% yield (last two steps) as a yellow solid. m/z (ESI, +ve)=261.1 [M+H]+.

Step 2: methyl 2-amino-4-(5-fluoro-4-methylpyridin-2-yl)-5-iodobenzoate

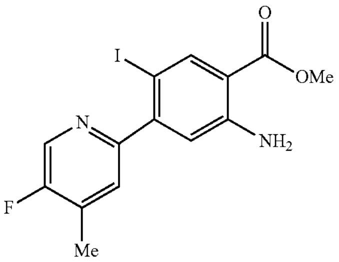 [SMILES: COC(=O)c1cc(I)c(-c2cc(C)c(F)cn2)cc1N]

The title compound was prepared analogously to Example 1207, step 3, where methyl 2-amino-4-(5-fluoro-4-methylpyridin-2-yl)benzoate was substituted in place of methyl 2-amino-4-(5-fluoropyridin-2-yl)benzoate. The title compound was isolated in 53% yield as a yellow solid. m/z (ESI, +ve)=387.0 [M+H]+.

Step 3: methyl 2-acetamido-4-(5-fluoro-4-methylpyridin-2-yl)-5-iodobenzoate

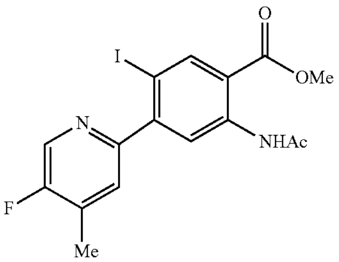 [SMILES: COC(=O)c1cc(I)c(-c2cc(C)c(F)cn2)cc1NC(C)=O]

The title compound was prepared analogously to Example 1207, step 4, where methyl 2-amino-4-(5-fluoro-4-methylpyridin-2-yl)-5-iodobenzoate was substituted in place of methyl 2-amino-4-(5-fluoropyridin-2-yl)-5-iodobenzoate. The title compound was isolated in 98% yield as a yellow solid. m/z (ESI, +ve)=429.0 [M+H]+.

Step 4: methyl 2-acetamido-4-(5-fluoro-4-methylpyridin-2-yl)-5-(trifluoromethyl)benzoate

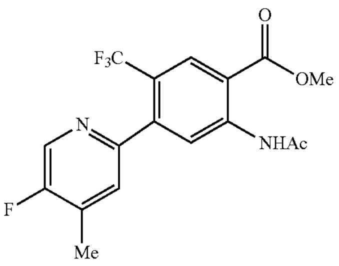 [SMILES: COC(=O)c1cc(C(F)(F)F)c(-c2cc(C)c(F)cn2)cc1NC(C)=O]

The title compound was prepared analogously to Example 1207, step 5, where methyl 2-acetamido-4-(5-fluoro-4-methylpyridin-2-yl)-5-iodobenzoate was substituted in place of methyl 2-acetamido-4-(5-fluoropyridin-2-yl)-5-iodobenzoate. The title compound was isolated in 56% yield as a yellow solid. m/z (ESI, +ve)=371.1 [M+H]+.

Step 5: methyl 2-amino-4-(5-fluoro-4-methylpyridin-2-yl)-5-(trifluoromethyl)benzoate

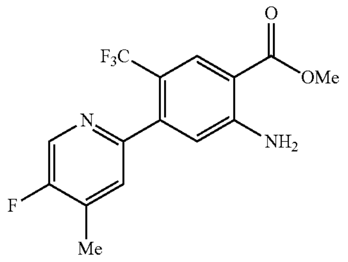 [SMILES: COC(=O)c1cc(C(F)(F)F)c(-c2cc(C)c(F)cn2)cc1N]

The title compound was prepared analogously to Example 1207, step 6, where methyl 2-acetamido-4-(5-fluoro-4-methylpyridin-2-yl)-5-(trifluoromethyl)benzoate was substituted in place of methyl 2-acetamido-4-(5-fluoropyridin-2-yl)-5-(trifluoromethyl)benzoate. The title compound was isolated in 78% yield as a yellow solid. m/z (ESI, +ve) =329.1 [M+H]+.

Step 6: methyl 2-amino-4-(5-fluoro-4-methylpyridin-2-yl)-3-iodo-5-(trifluoromethyl)benzoate

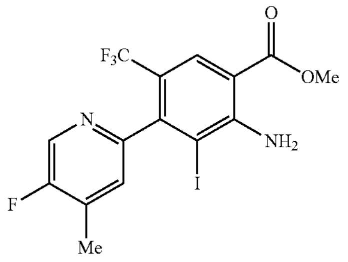 [SMILES: COC(=O)c1cc(C(F)(F)F)c(-c2cc(C)c(F)cn2)c(I)c1N]

The title compound was prepared analogously to Example 1207, step 7, where methyl 2-amino-4-(5-fluoro-4-methylpyridin-2-yl)-5-(trifluoromethyl)benzoate was substituted in place of methyl 2-amino-4-(5-fluoropyridin-2-yl)-5-(trifluoromethyl)benzoate. The title compound was isolated in 75% yield as a yellow solid. m/z (ESI, +ve)=455.0 [M+H]+.

Step 7: 2-amino-4-(5-fluoro-4-methylpyridin-2-yl)-3-iodo-5-(trifluoromethyl)benzoic acid

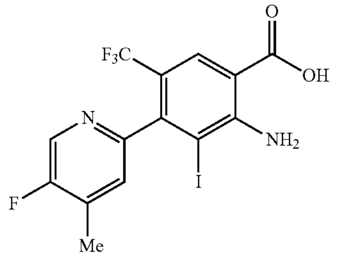 [SMILES: Cc1cc(-c2c(C(F)(F)F)cc(C(=O)O)c(N)c2I)ncc1F]

The title compound was prepared analogously to Example 1207, step 8, where methyl 2-amino-4-(5-fluoro-4-methylpyridin-2-yl)-3-iodo-5-(trifluoromethyl)benzoate was substituted in place of methyl 2-amino-4-(5-fluoropyridin-2-yl)-3-iodo-5-(trifluoromethyl)benzoate. The title compound was isolated in 97% yield as a yellow solid. m/z (ESI, +ve)=441.0 [M+H]+.

Step 8: 7-(5-fluoro-4-methylpyridin-2-yl)-8-iodo-6-(trifluoromethyl)quinazoline-2,4(1H,3H)-dione

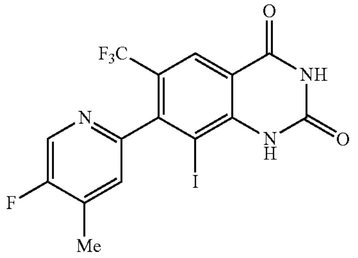 [SMILES: Cc1cc(-c2c(C(F)(F)F)cc3c(=O)[nH]c(=O)[nH]c3c2I)ncc1F]

The title compound was prepared analogously to Example 1207, step 9, where 2-amino-4-(5-fluoro-4-methylpyridin-2-yl)-3-iodo-5-(trifluoromethyl)benzoic acid was substituted in place of 2-amino-4-(5-fluoropyridin-2-yl)-3-iodo-5-(trifluoromethyl)benzoic acid. The title compound was isolated in 14% yield as a yellow solid. m/z (ESI, +ve) =466.0 [M+H]+.

Step 9: (S)-7-(5-fluoro-4-methylpyridin-2-yl)-8-((3-hydroxy-2-methoxypropyl)thio)-6-(trifluoromethyl) quinazoline-2,4(1H,3H)-dione

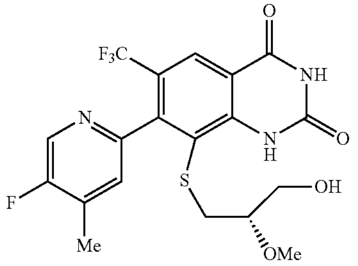 [SMILES: CO[C@@H](CO)CSc1c(-c2cc(C)c(F)cn2)c(C(F)(F)F)cc2c(=O)[nH]c(=O)[nH]c12]

The title compound was synthesized analogously to example 100, step 9 where 7-(5-fluoro-4-methylpyridin-2-yl)-8-iodo-6-(trifluoromethyl)quinazoline-2,4(1H,3H)-dione and (S)-3-mercapto-2-methoxypropan-1-ol were substituted in place of 7-(2,4-difluorophenyl)-8-iodo-6-(trifluoromethyl)quinazoline-2,4(1H,3H)-dione and 2-mercaptoethan-1-ol. The title compound was isolated in 87% yield as a yellow solid. m/z (ESI, +ve)=460.0 [M+H]+.

Step 10: (S)-11-(5-fluoro-4-methylpyridin-2-yl)-3-methoxy-10-(trifluoromethyl)-3,4-dihydro-2H,6H-[1,4]thiazepino[2,3,4-ij]quinazoline-6,8(7H)-dione

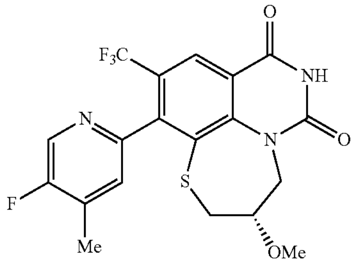 [SMILES: CO[C@@H]1CSc2c(-c3cc(C)c(F)cn3)c(C(F)(F)F)cc3c(=O)[nH]c(=O)n(c23)C1]

The title compound was prepared analogously to Example 100, step 10 where (S)-7-(5-fluoro-4-methylpyridin-2-yl)-8-((3-hydroxy-2-methoxypropyl)thio)-6-(trifluoromethyl)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 60% yield as a yellow solid. m/z (ESI, +ve)=442.0 [M+H]+.

Step 11: (S)-8-((3S,5R)-3,5-dimethylpiperazin-1-yl)-11-(5-fluoro-4-methylpyridin-2-yl)-3-methoxy-10-(trifluoromethyl)-3,4-dihydro-2H,6H-[1,4]thiazepino[2,3,4-ij]quinazolin-6-one The title compound was prepared analogously to Example 100, step 21 where (S)-11-(5-fluoro-4-methylpyridin-2-yl)-3-methoxy-10-(trifluoromethyl)-3,4-dihydro-2H,6H-[1,4]thiazepino[2,3,4-ij]quinazoline-6,8(7H)-dione and (2R,6S)-2,6-dimethylpiperazine were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 75% yield as a yellow solid. m/z (ESI, +ve)=538.0 [M+H]+.

Example 1210: (3S)-8-(9-acryloyl-3-oxa-7,9-diazabicyclo[3.3.1]nonan-7-yl)-11-(5-chloro-2,4-difluorophenyl)-3-methoxy-10-(trifluoromethyl)-3,4-dihydro-2H,6H-[1,4]thiazepino[2,3,4-ij]quinazolin-6-one

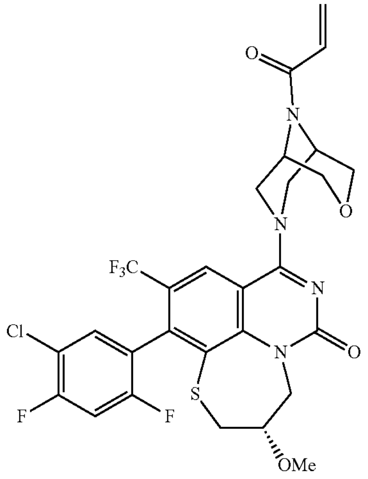 [SMILES: C=CC(=O)N1C2COCC1CN(c1nc(=O)n3c4c(c(-c5cc(Cl)c(F)cc5F)c(C(F)(F)F)cc14)SC[C@@H](OC)C3)C2]

The title compound was prepared analogously to Example 84 where (3S)-8-(3-oxa-7,9-diazabicyclo[3.3.1]nonan-7-yl)-11-(5-chloro-2,4-difluorophenyl)-3-methoxy-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 38% yield as a yellow solid. m/z (ESI, +ve)=624.9 [M+H]+. $^1$H NMR (400 MHz, DMSO-d6) δ 7.94 (s, 1H), 7.80-7.73 (m, 2H), 6.90-6.78 (dd, J=16.0, 8.0 Hz, 1H), 6.25 (dd, J=16.0 Hz, 4.0 Hz, 1H), 5.80 (dd, J=16.0 Hz, 4.0 Hz, 1H), 4.74-4.23 (m, 6H), 4.10-3.92 (m, 2H), 3.88-3.84 (m, 1H), 3.77-3.58 (m, 3H), 3.57-3.35 (m, 4H), 3.20-3.16 (m, 2H).

Step 1: tert-butyl 7-((3S)-11-(5-chloro-2,4-difluorophenyl)-3-methoxy-6-oxo-10-(trifluoromethyl)-3,4-dihydro-2H,6H-[1,4]thiazepino[2,3,4-ij]quinazolin-8-yl)-3-oxa-7,9-diazabicyclo[3.3.1]nonane-9-carboxylate

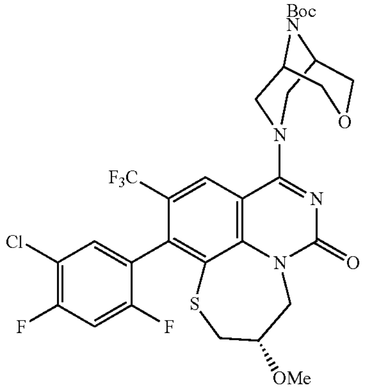 [SMILES: CO[C@@H]1CSc2c(-c3cc(Cl)c(F)cc3F)c(C(F)(F)F)cc3c(N4CC5COCC(C4)N5C(=O)OC(C)(C)C)nc(=O)n(c23)C1]

The title compound was prepared analogously to Example 100, step 21 where (3S)-11-(5-chloro-2,4-difluorophenyl)-3-methoxy-10-(trifluoromethyl)-3,4-dihydro-2H,6H-[1,4]thiazepino[2,3,4-ij]quinazoline-6,8(7H)-dione and tert-butyl 3-oxa-7,9-diazabicyclo[3.3.1]nonane-9-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 82% yield as a yellow solid. m/z (ESI, +ve)=688.9 [M+H]+.

Step 2: (3S)-8-(3-oxa-7,9-diazabicyclo[3.3.1]nonan-7-yl)-11-(5-chloro-2,4-difluorophenyl)-3-methoxy-10-(trifluoromethyl)-3,4-dihydro-2H,6H-[1,4]thiazepino[2,3,4-ij]quinazolin-6-one

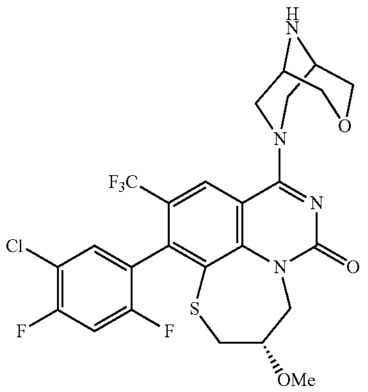 [SMILES: CO[C@@H]1CSc2c(-c3cc(Cl)c(F)cc3F)c(C(F)(F)F)cc3c(N4CC5COCC(C4)N5)nc(=O)n(c23)C1]

The title compound was prepared analogously to Example 102, step 4, where tert-butyl 7-((3S)-11-(5-chloro-2,4-difluorophenyl)-3-methoxy-6-oxo-10-(trifluoromethyl)-3,4-dihydro-2H,6H-[1,4]thiazepino[2,3,4-ij]quinazolin-8-yl)-3-oxa-7,9-diazabicyclo[3.3.1]nonane-9-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 88% yield as a yellow solid. m/z (ESI, +ve)=588.9 [M+H]+.

Example 1211: (3S)-8-((4aR,7aS)-4-acryloyl-6,6-dioxidohexahydrothieno[3,4-b]pyrazin-1(2H)-yl)-11-(5-chloro-2,4-difluorophenyl)-3-methoxy-10-(trifluoromethyl)-3,4-dihydro-2H,6H-[1,4]thiazepino[2,3,4-ij]quinazolin-6-one

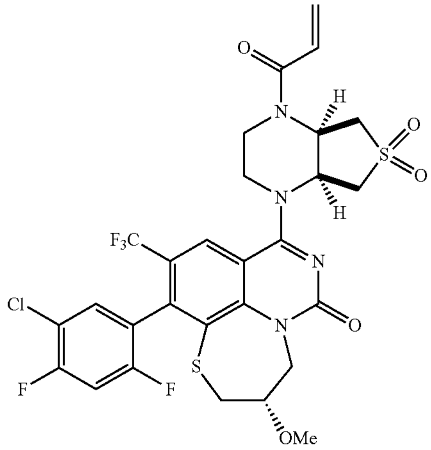

The title compound was prepared analogously to Example 84 where (3S)-11-(5-chloro-2,4-difluorophenyl)-8-((4aR,7aS)-6,6-dioxidohexahydrothieno[3,4-b]pyrazin-1(2H)-yl)-3-methoxy-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 40% yield as a yellow solid. m/z (ESI, +ve)=690.8 [M+H]+. $^1$H NMR (400 MHz, DMSO-d6) δ 8.04-8.00 (m, 1H), 7.82-7.78 (m, 1H), 7.76-7.62 (m, 1H), 6.80 (dd, J=16.0, 8.0 Hz, 1H), 6.24 (dd, J=16.0, 4.0 Hz, 1H), 5.82 (d, J=16.0, 4.0 Hz, 1H), 5.35-5.26 (m, 1H), 4.88-4.84 (m, 1H), 4.57-4.32 (m, 2H), 4.20-3.76 (m, 5H), 3.75-3.42 (m, 5H), 3.38-3.36 (m, 2H), 3.30-3.15 (m, 2H).

Step 1: (3S)-11-(5-chloro-2,4-difluorophenyl)-8-((4aR,7aS)-6,6-dioxidohexahydrothieno[3,4-b]pyrazin-1(2H)-yl)-3-methoxy-10-(trifluoromethyl)-3,4-dihydro-2H,6H-[1,4]thiazepino[2,3,4-ij]quinazolin-6-one

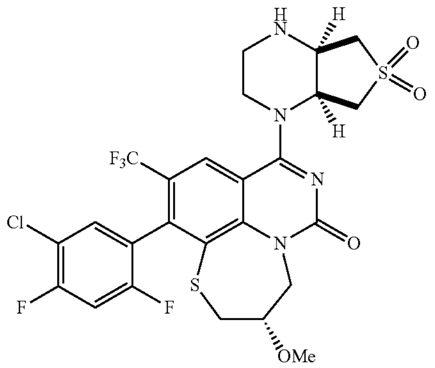

The title compound was prepared analogously to Example 100, step 21 where (3S)-11-(5-chloro-2,4-difluorophenyl)-3-methoxy-10-(trifluoromethyl)-3,4-dihydro-2H,6H-[1,4]thiazepino[2,3,4-ij]quinazoline-6,8(7H)-dione and (4aR,7aS)-octahydrothieno[3,4-b]pyrazine 6,6-dioxide were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 63% yield as a yellow solid. m/z (ESI, +ve)=636.9 [M+H]+.

Example 1212: (3S)-8-((4aS,7aR)-4-acryloyl-6-(methylsulfonyl)octahydro-1H-pyrrolo[3,4-b]pyrazin-1-yl)-11-(5-chloro-2,4-difluorophenyl)-3-methoxy-10-(trifluoromethyl)-3,4-dihydro-2H,6H-[1,4]thiazepino[2,3,4-ij]quinazolin-6-one

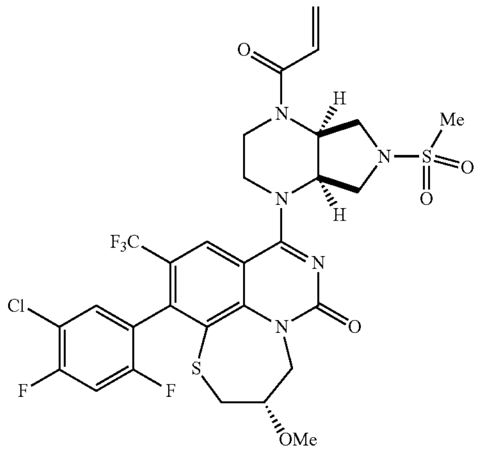

The title compound was prepared analogously to Example 84 where (3S)-11-(5-chloro-2,4-difluorophenyl)-3-methoxy-8-((4aS,7aR)-6-(methylsulfonyl)octahydro-1H-pyrrolo[3,4-b]pyrazin-1-yl)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 13% yield as a yellow solid.

m/z (ESI, +ve)=719.8 [M+H]+. $^1$H NMR (400 MHz, DMSO) δ=7.95 (d, J=8.0 Hz, 1H), 7.82-7.71 (m, 2H), 6.84 (s, 1H), 6.22 (dd, J=16.0, 4.0 Hz, 1H), 5.79 (d, J=16.0, 4.0 Hz, 1H), 4.97 (s, 1H), 4.65-4.37 (m, 3H), 4.22-3.43 (m, 10H), 3.25-3.16 (m, 4H), 3.05-2.84 (m, 3H).

Step 1: (3S)-11-(5-chloro-2,4-difluorophenyl)-3-methoxy-8-((4aS,7aR)-6-(methylsulfonyl)octahydro-1H-pyrrolo[3,4-b]pyrazin-1-yl)-10-(trifluoromethyl)-3,4-dihydro-2H,6H-[1,4]thiazepino[2,3,4-ij]quinazolin-6-one

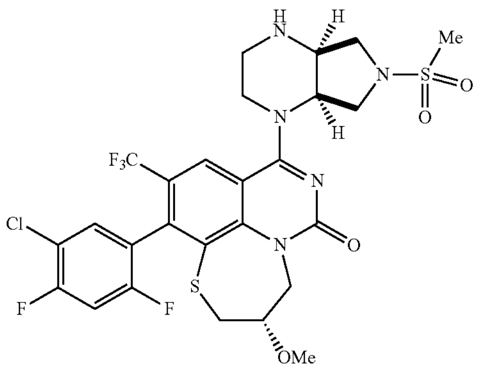

The title compound was prepared analogously to Example 100, step 21 where (3S)-11-(5-chloro-2,4-difluorophenyl)-3-methoxy-10-(trifluoromethyl)-3,4-dihydro-2H,6H-[1,4]thiazepino[2,3,4-ij]quinazoline-6,8(7H)-dione and (4aR,7aS)-6-(methylsulfonyl)octahydro-1H-pyrrolo[3,4-b]pyrazine-methane (1/1) were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 44% yield as a yellow solid. m/z (ESI, +ve)=665.9 [M+H]+.

Example 1213: (3S)-8-((4aR,7aS)-4-acryloylhexahydrofuro[3,4-b]pyrazin-1(2H)-yl)-11-(5-chloro-2,4-difluorophenyl)-3-methoxy-10-(trifluoromethyl)-3,4-dihydro-2H,6H-[1,4]thiazepino[2,3,4-ij]quinazolin-6-one

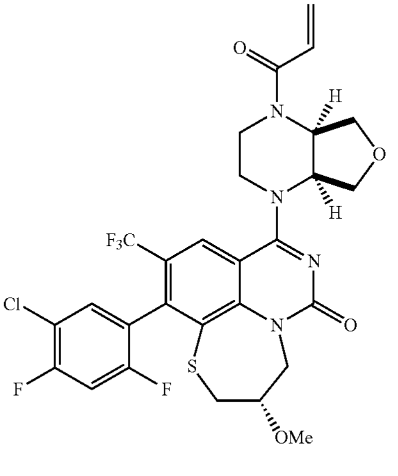

The title compound was prepared analogously to Example 84 where (3S)-11-(5-chloro-2,4-difluorophenyl)-8-((4aR,7aS)-hexahydrofuro[3,4-b]pyrazin-1(2H)-yl)-3-methoxy-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 8% yield as a yellow solid. m/z (ESI, +ve)=642.9 [M+H]+. $^1$H NMR (400 MHz, DMSO-d6) δ 7.98-7.62 (m, 3H), 6.81 (dd, J=16.0, 8.0 Hz, 1H), 6.19 (dd, J=16.0, 4.0 Hz, 1H), 5.75 (dd, J=16.0, 4.0 Hz, 1H), 4.87-4.85 (m, 2H), 4.54-4.40 (m, 1H), 4.19-4.16 (m, 2H), 4.02-3.97 (m, 3H), 3.86-3.57 (m, 4H), 3.36-3.34 (m, 4H), 3.22-3.14 (m, 2H).

Step 1: (3S)-11-(5-chloro-2,4-difluorophenyl)-8-((4aR,7aS)-hexahydrofuro[3,4-b]pyrazin-1(2H)-yl)-3-methoxy-10-(trifluoromethyl)-3,4-dihydro-2H,6H-[1,4]thiazepino[2,3,4-ij]quinazolin-6-one

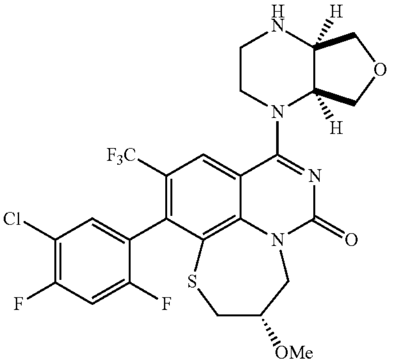

The title compound was prepared analogously to Example 100, step 21 where (3S)-11-(5-chloro-2,4-difluorophenyl)-3-methoxy-10-(trifluoromethyl)-3,4-dihydro-2H,6H-[1,4]thiazepino[2,3,4-ij]quinazoline-6,8(7H)-dione and (4aR,7aS)-octahydrofuro[3,4-b]pyrazine-methane (1/1) were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. m/z (ESI, +ve)=589.1 [M+H]+.

Example 1214: (3S)-8-((4aR,7aS)-4-acryloylhexahydrothieno[3,4-b]pyrazin-1(2H)-yl)-11-(5-chloro-2,4-difluorophenyl)-3-methoxy-10-(trifluoromethyl)-3,4-dihydro-2H,6H-[1,4]thiazepino[2,3,4-ij]quinazolin-6-one

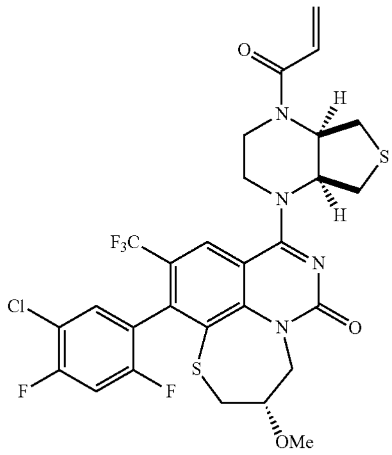

The title compound was prepared analogously to Example 84 where (3S)-11-(5-chloro-2,4-difluorophenyl)-8-((4aR,7aS)-hexahydrothieno[3,4-b]pyrazin-1(2H)-yl)-3-methoxy-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 4% yield as a yellow solid. m/z (ESI, +ve)=659.0 [M+H]+. $^1$H NMR (400 MHz, DMSO-$d_6$) δ=8.00-7.91 (m, 1H), 7.83-7.64 (m, 2H), 6.80-6.76 (m, 1H), 6.20 (dd, J=16.0, 4.0 Hz, 1H), 5.76 (dd, J=8.0, 4.0 Hz, 1H), 4.98-4.84 (m, 2H), 4.57-4.52 (m, 1H), 3.90-3.67 (m, 4H), 3.58-3.38 (m, 5H), 3.29-3.06 (m, 6H).

Step 1: (3S)-11-(5-chloro-2,4-difluorophenyl)-8-((4aR,7aS)-hexahydrothieno[3,4-b]pyrazin-1(2H)-yl)-3-methoxy-10-(trifluoromethyl)-3,4-dihydro-2H,6H-[1,4]thiazepino[2,3,4-ij]quinazolin-6-one

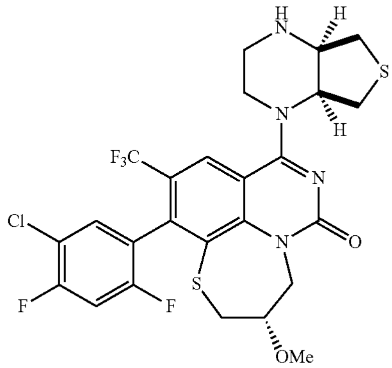

The title compound was prepared analogously to Example 100, step 21 where (3S)-11-(5-chloro-2,4-difluorophenyl)-3-methoxy-10-(trifluoromethyl)-3,4-dihydro-2H,6H-[1,4]thiazepino[2,3,4-ij]quinazoline-6,8(7H)-dione and (4aR,7aS)-octahydrothieno[3,4-b]pyrazine-methane (1/1) were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 50% yield as a yellow solid. m/z (ESI, +ve)=605.0 [M+H]+.

Example 1215: (S)-8-((3S,5R)-4-acryloyl-3,5-dimethylpiperazin-1-yl)-3-methoxy-10-(trifluoromethyl)-11-(3-(trifluoromethyl)isothiazol-5-yl)-3,4-dihydro-2H,6H-[1,4]thiazepino[2,3,4-ij]quinazolin-6-one

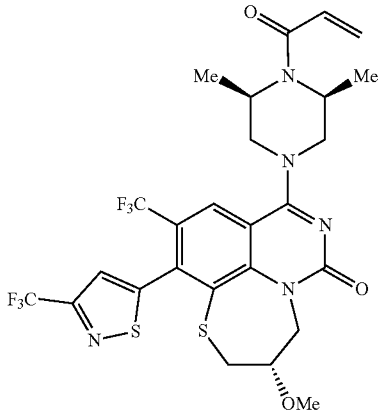 [SMILES: C=CC(=O)N1[C@H](C)CN(c2nc(=O)n3c4c(c(-c5cc(C(F)(F)F)ns5)c(C(F)(F)F)cc24)SC[C@@H](OC)C3)C[C@@H]1C]

The title compound was prepared analogously to Example 84 where (S)-8-((3S,5R)-3,5-dimethylpiperazin-1-yl)-3-methoxy-10-(trifluoromethyl)-11-(3-(trifluoromethyl)isothiazol-5-yl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 15% yield as a yellow solid. m/z (ESI, +ve)=634.1 [M+H]+. 1H NMR (400 MHz, DMSO-d6) δ 8.09 (s, 1H), 8.05 (s, 1H), 6.19 (dd, J=16.0 Hz, 8.0 Hz, 1H), 6.19 (dd, J=16.0, 4.0 Hz, 1H), 5.74 (dd, J=8.0, 4.0 Hz, 1H), 4.70-4.46 (m, 3H), 4.08-4.03 (m, 2H), 3.89-3.84 (m, 1H), 3.58-3.35 (m, 5H), 3.31-3.17 (m, 3H), 1.39 (s, 6H).

Step 1: Methyl 4-amino-2-nitrobenzoate

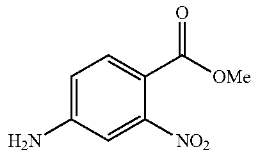 [SMILES: COC(=O)c1ccc(N)cc1[N+](=O)[O-]]

A mixture of 4-amino-2-nitrobenzoic acid (0.092 mol) in thionyl chloride (1.10 mol) was stirred at 85° C. for 2 hours. The mixture was concentrated under reduced pressure to afford a residue that was dissolved in dichloromethane (200 mL), cooled to 0° C. and treated with methanol (220 mL). After 30 minutes at 0° C., the volatiles were removed under reduced pressure and saturated aqueous sodium bicarbonate was added over the residue. The resulting suspension was filtered and the filter cake was washed with water and dried under reduced pressure to afford the title compound in 58% yield as a yellow solid. m/z (ESI, +ve)=197.1 [M+H]+.

Step 2: methyl 4-amino-5-iodo-2-nitrobenzoate

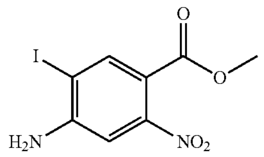

To a solution of methyl 4-amino-2-nitrobenzoate (0.083 mol) in AcOH (125 mL) was added N-iodosuccinimide (0.083 mol). The mixture was stirred at 100° C. for 16 hours, diluted with water and extracted with ethyl acetate three times. The combined organic layers were washed with brine, dried over sodium sulfate, filtered and concentrated under reduced pressure to afford a residue that was triturated with methanol. The title compound was isolated by filtration in 72% yield as a pale brown solid. m/z (ESI, +ve)=322.9 [M+H]+.

Step 3: Methyl 4-acetamido-5-iodo-2-nitrobenzoate

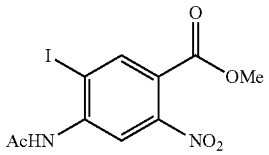 [SMILES: COC(=O)c1cc(I)c(NC(C)=O)cc1[N+](=O)[O-]]

To a mixture of methyl 4-amino-5-iodo-2-nitrobenzoate (0.047 mol) in acetic acid (150 mL) was added acetic anhydride (0.051 mol). The mixture was stirred at 100° C. for 2 hours and the volatiles were removed under reduced pressure. The residue was taken up in ethyl acetate and washed with brine, dried over sodium sulfate and concentrated under reduced pressure to afford a residue that was recrystallized in methanol to afford the title compound in 85% yield as a white solid. m/z (ESI, +ve)=364.9 [M+H]+.

Step 4: Methyl 4-acetamido-2-nitro-5-(trifluoromethyl)benzoate

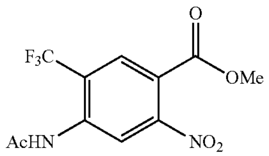 [SMILES: COC(=O)c1cc(C(F)(F)F)c(NC(C)=O)cc1[N+](=O)[O-]]

To a solution of methyl 4-acetamido-5-iodo-2-nitrobenzoate (0.027 mol) in HMPA (50 mL) was added copper (I) iodide (0.038 mol) and tetrabutylammonium iodide (0.014 mol). The mixture was stirred at 50° C. for 30 minutes and methyl 2,2-difluoro-2-(fluorosulfonyl)acetate (0.27 mol) was added slowly. The reaction mixture was stirred at 50° C. for one additional hour, quenched with ice-water and diluted with ethyl acetate. The insoluble materials were filtered off and the organic layer separated. The aqueous layer was extracted with ethyl acetate three times, the combined organic layers were washed with brine, dried over sodium sulfate, filtered and concentrated under reduced pressure to afford a residue that was purified by silica gel chromatography (0-15% ethyl acetate in hexanes). The title compound was isolated in quantitative yield as a white solid. $^1$H NMR (400 MHz, DMSO) δ 10.03 (s, 1H), 8.37 (s, 1H), 8.23 (s, 1H), 3.87 (s, 3H), 2.15 (s, 3H).

Step 5: Methyl 4-amino-2-nitro-5-(trifluoromethyl)benzoate

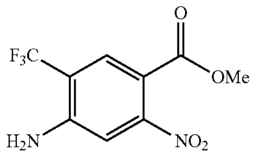 [SMILES: COC(=O)c1cc(C(F)(F)F)c(N)cc1[N+](=O)[O-]]

A mixture of methyl 4-acetamido-2-nitro-5-(trifluoromethyl) benzoate (33 mmol) in 175 mL of HCl:MeOH (1:2.5 ratio) was stirred at 80° C. for 2 hours. The mixture was diluted with water and filtered. The filter cake was dried under reduced pressure to afford the title compound in 86% yield as a pale green solid. 1H NMR (400 MHz, DMSO) δ 7.90 (s, 1H), 7.14-7.12 (m, 3H), 3.76 (s, 3H).

Step 6: Methyl 4-bromo-2-nitro-5-(trifluoromethyl)benzoate

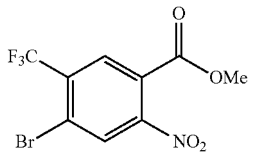 [SMILES: COC(=O)c1cc(C(F)(F)F)c(Br)cc1[N+](=O)[O-]]

To a mixture of methyl 4-amino-2-nitro-5-(trifluoromethyl) benzoate (0.0585 mol) and $CuBr_2$ (0.12 mol) in anhydrous acetonitrile (150 mL) at 0° C., was added t-$BuNO_2$ (0.12 mol). The mixture was stirred at 70° C. for 1.5 hours, diluted with water and extracted with ethyl acetate three times. The combined organic layers were washed with brine, dried over sodium sulfate, filtered and concentrated under reduced pressure to afford a residue that was purified by silica gel chromatography (0-15% ethyl acetate in hexanes). The title compound was isolated in 94% yield as a white solid. m/z (ESI, +ve)=328.0 [M+H]+.

Step 7: Methyl 2-amino-4-bromo-5-(trifluoromethyl)benzoate

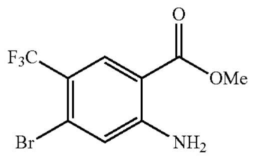 [SMILES: COC(=O)c1cc(C(F)(F)F)c(Br)cc1N]

To a mixture of methyl 4-bromo-2-nitro-5-(trifluoromethyl) benzoate (0.056 mol) in THF/MeOH/$H_2O$ (60 mL:60 mL:60 mL) was added ammonium chloride (0.113 mol) and iron (0.28 mol). The mixture was stirred at 80° C. for 2 hours, cooled down to room temperature and the solids filtered off and rinsed with ethyl acetate. Evaporation of volatiles under reduced pressure afforded a residue that was purified by silica gel chromatography (0-17% ethyl acetate in hexanes). The title compound was isolated in 83% yield as a white solid. m/z (ESI, +ve)=298.0 [M+H]+.

Step 8: Methyl 2-amino-4-(4,4,5,5-tetramethyl-1,3,2-dioxaborolan-2-yl)-5-(trifluoromethyl)benzoate

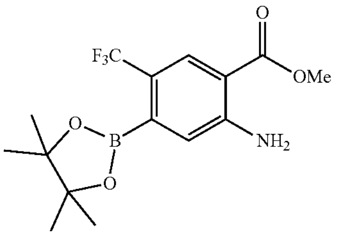 [SMILES: COC(=O)c1cc(C(F)(F)F)c(B2OC(C)(C)C(C)(C)O2)cc1N]

A mixture of methyl 2-amino-4-bromo-5-(trifluoromethyl) benzoate (48 mmol), bis(pinacolato)diboron (58 mmol), Pd(dppf)$Cl_2$ (9.6 mmol) and potassium acetate (0.15 mol) in 1,4-dioxane (150 mL) was stirred at 100° C. for 4 hours. The mixture was cooled down and concentrated to afford a residue that was purified by silica gel chromatography (25% ethyl acetate in hexanes). The title compound was isolated in 90% yield as a yellow solid. m/z (ESI, +ve)=346.2 [M+H]+. $^1$H NMR (400 MHz, DMSO) δ 7.96 (s, 1H), 7.22 (s, 2H), 7.15 (s, 1H), 3.83 (s, 3H), 1.30 (s, 12H).

Step 9: 5-Iodo-3-(trifluoromethyl)isothiazole

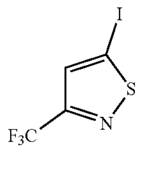

Sodium nitrite (4.47 mmol) was added over a 0° C. solution of 3-(trifluoromethyl)isothiazol-5-amine (3.73 mmol) in 50% aqueous sulfuric acid (4 mL). After one hour, KI (4.47 mmol) was added and the reaction mixture heated at 80° C. for one hour. The reaction was cooled down to room temperature and extracted with diethyl ether three times. The combined organic layers were dried over sodium sulfate and the volatiles were removed under reduced pressure to afford the title compound as a brown oil which was used in the next step without further purification.

Step 10: Methyl 2-amino-5-(trifluoromethyl)-4-(3-(trifluoromethyl)isothiazol-5-yl)benzoate

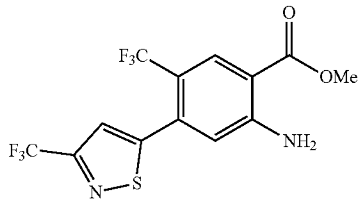 [SMILES: COC(=O)c1cc(C(F)(F)F)c(-c2cc(C(F)(F)F)ns2)cc1N]

The title compound was prepared analogously to Example 207, step 2, where 5-iodo-3-(trifluoromethyl)isothiazole and methyl 2-amino-4-(4,4,5,5-tetramethyl-1,3,2-dioxaborolan-2-yl)-5-(trifluoromethyl)benzoate were substituted in place of 2-bromo-5-fluoro-4-methylpyridine and methyl 2-amino-4-(4,4,5,5-tetramethyl-1,3,2-dioxaborolan-2-yl)benzoate. The title compound was isolated in 21% yield (for the last two steps) as a white solid. m/z (ESI, +ve)=371.0 [M+H]+.

Step 11: Methyl 2-amino-3-iodo-5-(trifluoromethyl)-4-(3-(trifluoromethyl)isothiazol-5-yl)benzoate

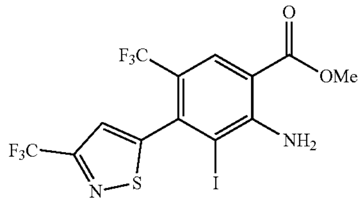 [SMILES: COC(=O)c1cc(C(F)(F)F)c(-c2cc(C(F)(F)F)ns2)c(I)c1N]

The title compound was prepared analogously to Example 207, step 3, where methyl 2-amino-5-(trifluoromethyl)-4-(3-(trifluoromethyl)isothiazol-5-yl)benzoate was substituted in place of methyl 2-amino-4-(5-fluoropyridin-2-yl)benzoate. The title compound was isolated in 90% yield as a yellow solid. m/z (ESI, +ve)=496.8 [M+H]+.

Step 12: 2-Amino-3-iodo-5-(trifluoromethyl)-4-(3-(trifluoromethyl)isothiazol-5-yl)benzoic acid

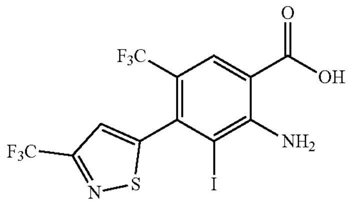 [SMILES: Nc1c(C(=O)O)cc(C(F)(F)F)c(-c2cc(C(F)(F)F)ns2)c1I]

The title compound was prepared analogously to Example 207, step 8, where methyl 2-amino-3-iodo-5-(trifluoromethyl)-4-(3-(trifluoromethyl)isothiazol-5-yl)benzoate was substituted in place of methyl 2-amino-4-(5-fluoropyridin-2-yl)-3-iodo-5-(trifluoromethyl)benzoate. The title compound was isolated in 810% yield as a yellow solid.

m/z (ESI, +ve)=482.8 [M+H]+.

Step 13: 8-Iodo-6-(trifluoromethyl)-7-(3-(trifluoromethyl)isothiazol-5-yl)quinazoline-2,4(1H,3H)-dione

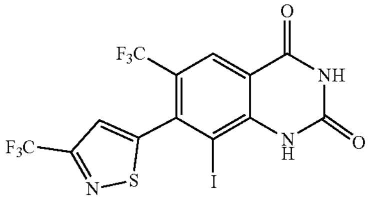 [SMILES: O=c1[nH]c(=O)c2cc(C(F)(F)F)c(-c3cc(C(F)(F)F)ns3)c(I)c2[nH]1]

The title compound was prepared analogously to Example 207, step 9, where 2-amino-3-iodo-5-(trifluoromethyl)-4-(3-(trifluoromethyl)isothiazol-5-yl)benzoic acid was substituted in place of 2-amino-4-(5-fluoropyridin-2-yl)-3-iodo-5-(trifluoromethyl)benzoic acid. The title compound was isolated in 73% yield as a yellow solid. m/z (ESI, +ve)=508.0 [M+H]+

Step 14: (S)-8-((3-Hydroxy-2-methoxypropyl)thio)-6-(trifluoromethyl)-7-(3-(trifluoromethyl)isothiazol-5-yl)quinazoline-2,4(1H,3H)-dione

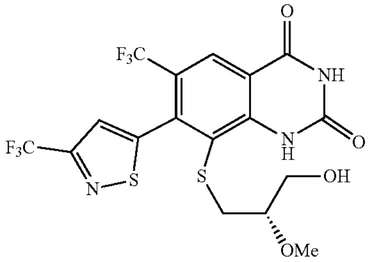 [SMILES: CO[C@@H](CO)CSc1c(-c2cc(C(F)(F)F)ns2)c(C(F)(F)F)cc2c(=O)[nH]c(=O)[nH]c12]

The title compound was synthesized analogously to example 100, step 9 where 8-iodo-6-(trifluoromethyl)-7-(3-(trifluoromethyl)isothiazol-5-yl)quinazoline-2,4(1H,3H)-dione and (S)-3-mercapto-2-methoxypropan-1-ol were substituted in place of 7-(2,4-difluorophenyl)-8-iodo-6-(trifluoromethyl)quinazoline-2,4(1H,3H)-dione and 2-mercaptoethan-1-ol. The title compound was isolated in 70% yield as a yellow solid. m/z (ESI, +ve)=502.0 [M+H]+

Step 15: (S)-3-methoxy-10-(trifluoromethyl)-11-(3-(trifluoromethyl)isothiazol-5-yl)-3,4-dihydro-2H,6H-[1,4]thiazepino[2,3,4-ij]quinazoline-6,8(7H)-dione

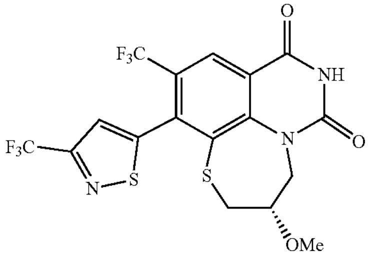 [SMILES: CO[C@@H]1CSc2c(-c3cc(C(F)(F)F)ns3)c(C(F)(F)F)cc3c(=O)[nH]c(=O)n(c23)C1]

The title compound was prepared analogously to Example 100, step 10 where (S)-8-((3-hydroxy-2-methoxypropyl)thio)-6-(trifluoromethyl)-7-(3-(trifluoromethyl)isothiazol-5-yl)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 55% yield as a yellow solid. m/z (ESI, +ve)=484.0 [M+H]+.

Step 16: (S)-8-((3S,5R)-3,5-dimethylpiperazin-1-yl)-3-methoxy-10-(trifluoromethyl)-11-(3-(trifluoromethyl)isothiazol-5-yl)-3,4-dihydro-2H,6H-[1,4]thiazepino[2,3,4-ij]quinazolin-6-one

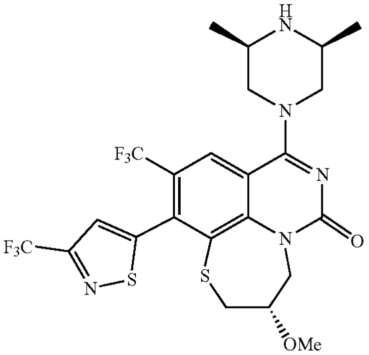 [SMILES: CO[C@@H]1CSc2c(-c3cc(C(F)(F)F)ns3)c(C(F)(F)F)cc3c(N4C[C@@H](C)N[C@@H](C)C4)nc(=O)n(c23)C1]

The title compound was prepared analogously to Example 100, step 21 where (S)-3-methoxy-10-(trifluoromethyl)-11-(3-(trifluoromethyl)isothiazol-5-yl)-3,4-dihydro-2H,6H-[1,4]thiazepino[2,3,4-ij]quinazoline-6,8(7H)-dione and (2R,6S)-2,6-dimethylpiperazine were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 75% yield as a yellow solid. m/z (ESI, +ve)=580.1 [M+H]+.

Example 1216: (S)-8-((3S,5R)-4-acryloyl-3,5-dimethylpiperazin-1-yl)-3-methoxy-10-(trifluoromethyl)-11-(5-(trifluoromethyl)thiazol-2-yl)-3,4-dihydro-2H,6H-[1,4]thiazepino[2,3,4-ij]quinazolin-6-one

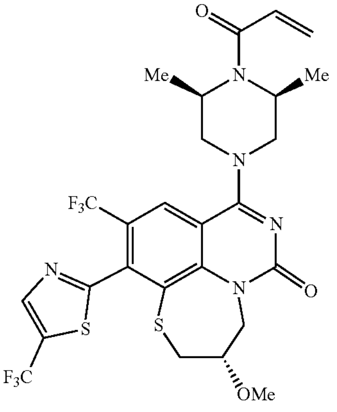 [SMILES: C=CC(=O)N1[C@H](C)CN(c2nc(=O)n3c4c(c(-c5ncc(C(F)(F)F)s5)c(C(F)(F)F)cc24)SC[C@@H](OC)C3)C[C@@H]1C]

The title compound was prepared analogously to Example 84 where (S)-8-((3S,5R)-3,5-dimethylpiperazin-1-yl)-3- methoxy-10-(trifluoromethyl)-11-(5-(trifluoromethyl)thiazol-2-yl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 7% yield as a yellow solid. m/z (ESI, +ve)=634.1 [M+H]+. $^1$H NMR (400 MHz, DMSO-d6) δ 8.76 (s, 1H), 8.06 (s, 1H), 6.81 (dd, J=16.0, 8.0 Hz, 1H), 6.19 (dd, J=16.0, 4.0 Hz, 1H), 5.74 (dd, J=8.0, 4.0 Hz, 1H), 4.65-4.45 (m, 4H), 4.07-4.04 (m, 2H), 3.89-3.85 (m, 1H), 3.54-3.33 (m, 4H), 3.24-3.20 (m, 3H), 1.39 (s, 6H).

Step 1: Methyl 2-amino-5-(trifluoromethyl)-4-(5-(trifluoromethyl)thiazol-2-yl)benzoate

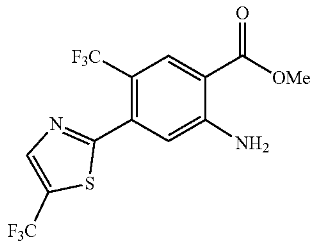 [SMILES: COC(=O)c1cc(C(F)(F)F)c(-c2ncc(C(F)(F)F)s2)cc1N]

The title compound was prepared analogously to Example 207, step 2, where 2-bromo-5-(trifluoromethyl)thiazole and methyl 2-amino-4-(4,4,5,5-tetramethyl-1,3,2-dioxaborolan-2-yl)-5-(trifluoromethyl)benzoate were substituted in place of 2-bromo-5-fluoro-4-methylpyridine and methyl 2-amino-4-(4,4,5,5-tetramethyl-1,3,2-dioxaborolan-2-yl)benzoate. The title compound was isolated in 21% yield as a white solid. m/z (ESI, +ve)=370.9 [M+H]+.

Step 2: methyl 2-amino-3-iodo-5-(trifluoromethyl)-4-(5-(trifluoromethyl)thiazol-2-yl)benzoate

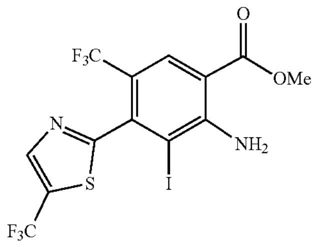 [SMILES: COC(=O)c1cc(C(F)(F)F)c(-c2ncc(C(F)(F)F)s2)c(I)c1N]

The title compound was prepared analogously to Example 1207, step 3, where methyl 2-amino-5-(trifluoromethyl)-4-(5-(trifluoromethyl)thiazol-2-yl)benzoate was substituted in place of methyl 2-amino-4-(5-fluoropyridin-2-yl)benzoate. The title compound was isolated in 79% yield as a yellow solid. m/z (ESI, +ve)=496.8 [M+H]+.

Step 3: 2-amino-3-iodo-5-(trifluoromethyl)-4-(5-(trifluoromethyl)thiazol-2-yl)benzoic acid

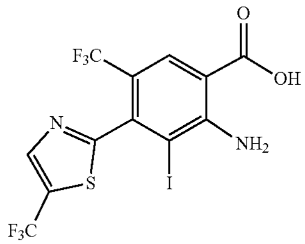

The title compound was prepared analogously to Example 1207, step 8, where methyl 2-amino-4-(5-fluoro-4-methylpyridin-2-yl)-3-iodo-5-(trifluoromethyl)benzoate was substituted in place of methyl 2-amino-4-(5-fluoropyridin-2-yl)-3-iodo-5-(trifluoromethyl)benzoate. The title compound was isolated in 86% yield as a yellow solid. m/z (ESI, +ve)=483.1 [M+H]+

Step 4: 8-Iodo-6-(trifluoromethyl)-7-(5-(trifluoromethyl)thiazol-2-yl)quinazoline-2,4(1H,3H)-dione

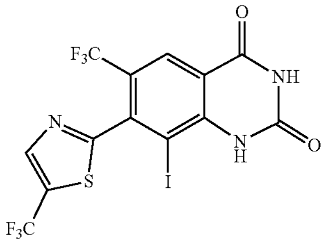 [SMILES: O=c1[nH]c(=O)c2cc(C(F)(F)F)c(-c3ncc(C(F)(F)F)s3)c(I)c2[nH]1]

The title compound was prepared analogously to Example 1207, step 9, where 2-amino-3-iodo-5-(trifluoromethyl)-4-(5-(trifluoromethyl)thiazol-2-yl)benzoic acid was substituted in place of 2-amino-4-(5-fluoropyridin-2-yl)-3-iodo-5-(trifluoromethyl)benzoic acid. The title compound was isolated in 55% yield as a brown solid. m/z (ESI, +ve)=507.9 [M+H]+.

Step 5: (S)-8-((3-Hydroxy-2-methoxypropyl)thio)-6-(trifluoromethyl)-7-(5-(trifluoromethyl)thiazol-2-yl)quinazoline-2,4(1H,3H)-dione

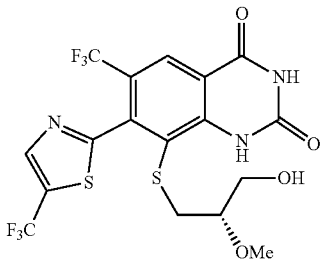 [SMILES: CO[C@@H](CO)CSc1c(-c2ncc(C(F)(F)F)s2)c(C(F)(F)F)cc2c(=O)[nH]c(=O)[nH]c12]

The title compound was synthesized analogously to example 100, step 9 where 8-iodo-6-(trifluoromethyl)-7-(5-(trifluoromethyl)thiazol-2-yl)quinazoline-2,4(1H,3H)-dione and (S)-3-mercapto-2-methoxypropan-1-ol were substituted in place of 7-(2,4-difluorophenyl)-8-iodo-6-(trifluoromethyl)quinazoline-2,4(1H,3H)-dione and 2-mercaptoethan-1-ol. The title compound was isolated in 50% yield as a yellow solid. m/z (ESI, +ve)=502.1 [M+H]+.

Step 6: (S)-3-Methoxy-10-(trifluoromethyl)-11-(5-(trifluoromethyl)thiazol-2-yl)-3,4-dihydro-2H,6H-[1,4]thiazepino[2,3,4-ij]quinazoline-6,8(7H)-dione

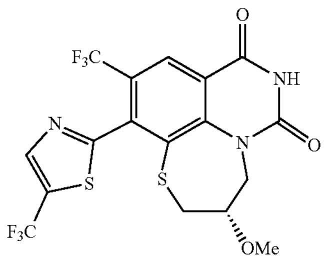 [SMILES: CO[C@@H]1CSc2c(-c3ncc(C(F)(F)F)s3)c(C(F)(F)F)cc3c(=O)[nH]c(=O)n(c23)C1]

The title compound was prepared analogously to Example 100, step 10 where (S)-8-((3-hydroxy-2-methoxypropyl)thio)-6-(trifluoromethyl)-7-(5-(trifluoromethyl)thiazol-2-yl)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 41% yield as a yellow solid. m/z (ESI, +ve)=484.0 [M+H]+.

Step 7: (S)-8-((3S,5R)-3,5-Dimethylpiperazin-1-yl)-3-methoxy-10-(trifluoromethyl)-11-(5-(trifluoromethyl)thiazol-2-yl)-3,4-dihydro-2H,6H-[1,4]thiazepino[2,3,4-ij]quinazolin-6-one

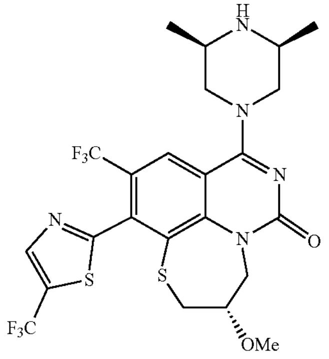 [SMILES: CO[C@@H]1CSc2c(-c3ncc(C(F)(F)F)s3)c(C(F)(F)F)cc3c(N4C[C@@H](C)N[C@@H](C)C4)nc(=O)n(c23)C1]

The title compound was prepared analogously to Example 100, step 21 where (S)-3-methoxy-10-(trifluoromethyl)-11-(5-(trifluoromethyl)thiazol-2-yl)-3,4-dihydro-2H,6H-[1,4]thiazepino[2,3,4-ij]quinazoline-6,8(7H)-dione and (2R,6S)-2,6-dimethylpiperazine were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 43% yield as a yellow solid. m/z (ESI, +ve)=580.1 [M+H]+.

Example 1217: (S)-8-((3S,5R)-4-acryloyl-3,5-dimethylpiperazin-1-yl)-3-(fluoromethoxy)-11-(4-fluorophenyl)-10-(trifluoromethyl)-3,4-dihydro-2H,6H-[1,4]thiazepino[2,3,4-ij]quinazolin-6-one

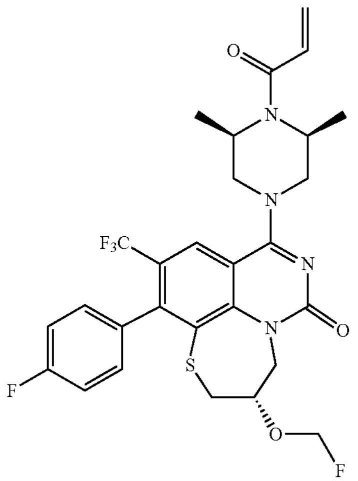 [SMILES: C=CC(=O)N1[C@H](C)CN(c2nc(=O)n3c4c(c(-c5ccc(F)cc5)c(C(F)(F)F)cc24)SC[C@@H](OCF)C3)C[C@@H]1C]

The title compound was prepared analogously to Example 84 where (S)-8-((3S,5R)-3,5-dimethylpiperazin-1-yl)-3-(fluoromethoxy)-11-(4-fluorophenyl)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 9% yield as a yellow solid. m/z (ESI, +ve)=595.2 [M+H]+.

Step 1: tert-Butyl (2S,6R)-4-((S)-3-(fluoromethoxy)-11-(4-fluorophenyl)-6-oxo-10-(trifluoromethyl)-3,4-dihydro-2H,6H-[1,4]thiazepino[2,3,4-ij]quinazolin-8-yl)-2,6-dimethylpiperazine-1-carboxylate

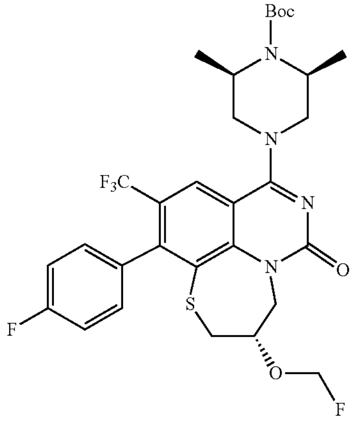 [SMILES: C[C@@H]1CN(c2nc(=O)n3c4c(c(-c5ccc(F)cc5)c(C(F)(F)F)cc24)SC[C@@H](OCF)C3)C[C@H](C)N1C(=O)OC(C)(C)C]

Sodium hydride (0.47 mmol) was added over a 0° C. solution of tert-butyl (2S,6R)-4-((S)-11-(4-fluorophenyl)-3-hydroxy-6-oxo-10-(trifluoromethyl)-3,4-dihydro-2H,6H-[1,4]thiazepino[2,3,4-ij]quinazolin-8-yl)-2,6-dimethylpiperazine-1-carboxylate (0.16 mmol) in THF (2 mL) and after 15 minutes the cooling bath was removed and the reaction was stirred at room temperature for another 15 additional minutes. The reaction mixture was cooled again to 0° C. and a solution of fluoromethyl-(2-methoxy-1-methoxycarbonyl-2-oxo-ethyl)-phenyl-sulfonium (0.39 mmol) in 500 mL of THF was added slowly. After one hour the reaction was quenched by addition of water and ethyl acetate. The organic layer was separated and the aqueous layer extracted three times with ethyl acetate. The combined organic layers were dried over sodium sulfate and concentrated. The resulting residue was purified by silica gel chromatography (20-80% ethyl acetate in hexanes) to afford the title compound in 65% yield as a pale yellow solid. m/z (ESI, +ve)=641.2 [M+H]+.

Step 2: (S)-8-((3S,5R)-3,5-dimethylpiperazin-1-yl)-3-(fluoromethoxy)-11-(4-fluorophenyl)-10-(trifluoromethyl)-3,4-dihydro-2H,6H-[1,4]thiazepino[2,3,4-ij]quinazolin-6-one

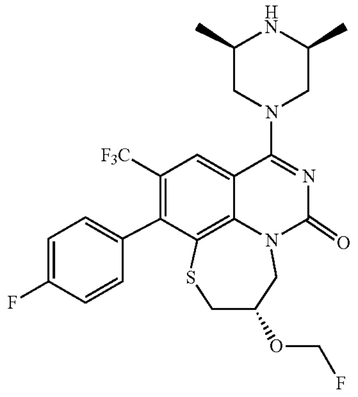 [SMILES: C[C@@H]1CN(c2nc(=O)n3c4c(c(-c5ccc(F)cc5)c(C(F)(F)F)cc24)SC[C@@H](OCF)C3)C[C@H](C)N1]

The title compound was prepared analogously to Example 102, step 4, where tert-butyl (2S,6R)-4-((S)-3-(fluoromethoxy)-11-(4-fluorophenyl)-6-oxo-10-(trifluoromethyl)-3,4-dihydro-2H,6H-[1,4]thiazepino[2,3,4-ij]quinazolin-8-yl)-2,6-dimethylpiperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. m/z (ESI, +ve)=541.2 [M+H]+.

Example 1218: (3S)-11-(5-Chloro-2,4-difluorophenyl)-8-((3S,5R)-4-(2-fluoroacryloyl)-3,5-dimethylpiperazin-1-yl)-3-methoxy-10-(trifluoromethyl)-3,4-dihydro-2H,6H-[1,4]thiazepino[2,3,4-ij]quinazolin-6-one

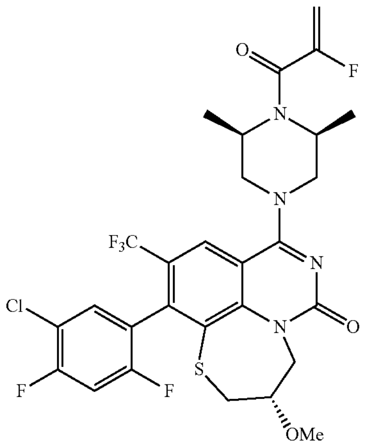 [SMILES: C=C(F)C(=O)N1[C@H](C)CN(c2nc(=O)n3c4c(c(-c5cc(Cl)c(F)cc5F)c(C(F)(F)F)cc24)SC[C@@H](OC)C3)C[C@@H]1C]

The title compound was prepared analogously to Example 418 where (3S)-11-(5-chloro-2,4-difluorophenyl)-8-((3S,5R)-3,5-dimethylpiperazin-1-yl)-3-methoxy-10-(trifluoromethyl)-3,4-dihydro-2H,6H-[1,4]thiazepino[2,3,4-ij]quinazolin-6-one was substituted in place of 10-(2,4-difluorophenyl)-7-(7-oxo-3,9-diazabicyclo[3.3.1]nonan-3-yl)-9-(trifluoromethyl)-2,3-dihydro-5H-[1,4]thiazino[2,3,4-ij]quinazolin-5-one. The title compound was isolated in 33% yield as a yellow solid. m/z (ESI, +ve)=647.1 [M+H]+. $^1$H NMR (400 MHz, DMSO-d6) δ=8.03 (s, 1H), 7.82-7.70 (m, 2H), 5.34-5.29 (m, 1H), 5.23 (dd, J=32.0, 4.0 Hz, 1H), 4.53-4.41 (m, 3H), 4.89-4.02 (m, 2H), 3.88-3.84 (m, 1H), 3.43-3.34 (m, 5H), 3.33-3.28 (m, 2H), 3.22-3.15 (m, 1H), 1.52-1.36 (m, 6H).

Example 1219: (3S)-11-(5-Chloro-2,4-difluorophenyl)-8-(4-(2-fluoroacryloyl)piperazin-1-yl)-3-methoxy-10-(trifluoromethyl)-3,4-dihydro-2H,6H-[1,4]thiazepino[2,3,4-ij]quinazolin-6-one

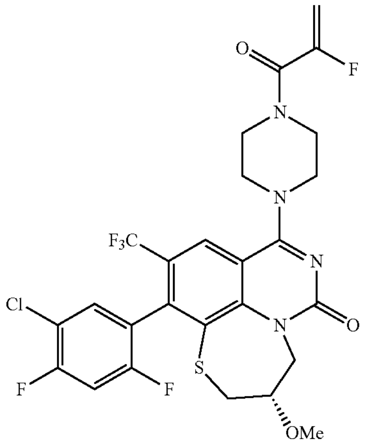 [SMILES: C=C(F)C(=O)N1CCN(c2nc(=O)n3c4c(c(-c5cc(Cl)c(F)cc5F)c(C(F)(F)F)cc24)SC[C@@H](OC)C3)CC1]

The title compound was prepared analogously to Example 418 where (3S)-11-(5-chloro-2,4-difluorophenyl)-3-methoxy-8-(piperazin-1-yl)-10-(trifluoromethyl)-3,4-dihydro-2H,6H-[1,4]thiazepino[2,3,4-ij]quinazolin-6-one was substituted in place of 10-(2,4-difluorophenyl)-7-(7-oxo-3,9-diazabicyclo[3.3.1]nonan-3-yl)-9-(trifluoromethyl)-2,3-dihydro-5H-[1,4]thiazino[2,3,4-ij]quinazolin-5-one. The title compound was isolated in 30% yield as a yellow solid. m/z (ESI, +ve)=619.0 [M+H]+. $^1$H NMR (400 MHz, DMSO-d6) δ 7.90 (s, 1H), 7.80-7.75 (m, 2H), 5.35-5.31 (m, 1H), 5.29 (dd, J=64.0, 4.0 Hz, 1H), 4.50-4.48 (m, 1H), 3.95-3.70 (m, 9H), 3.55-3.36 (m, 3H), 3.31-3.12 (m, 3H).

Example 1220: (3S)-11-(2,4-Difluorophenyl)-8-((3S,5R)-4-(2-fluoroacryloyl)-3,5-dimethylpiperazin-1-yl)-3-methoxy-10-(trifluoromethyl)-3,4-dihydro-2H,6H-[1,4]thiazepino[2,3,4-ij]quinazolin-6-one

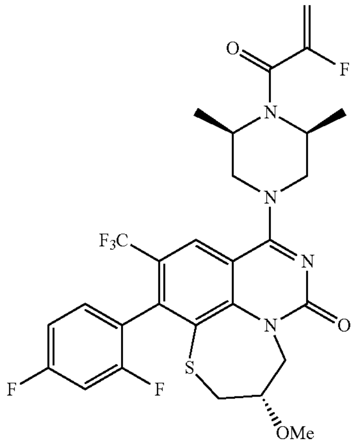 [SMILES: C=C(F)C(=O)N1[C@H](C)CN(c2nc(=O)n3c4c(c(-c5ccc(F)cc5F)c(C(F)(F)F)cc24)SC[C@@H](OC)C3)C[C@@H]1C]

The title compound was prepared analogously to Example 418 where (3S)-11-(2,4-difluorophenyl)-8-((3S,5R)-3,5-dimethylpiperazin-1-yl)-3-methoxy-10-(trifluoromethyl)-3,4-dihydro-2H,6H-[1,4]thiazepino[2,3,4-ij]quinazolin-6-one was substituted in place of 10-(2,4-difluorophenyl)-7-(7-oxo-3,9-diazabicyclo[3.3.1]nonan-3-yl)-9-(trifluoromethyl)-2,3-dihydro-5H-[1,4]thiazino[2,3,4-ij]quinazolin-5-one. The title compound was isolated in 34% yield as a yellow solid. m/z (ESI, +ve)=613.2 [M+H]+. $^1$H NMR (400 MHz, DMSO-d6) δ=8.03 (s, 1H), 7.49-7.35 (m, 2H), 7.30-7.23 (m, 1H), 5.33-5.29 (m, 1H), 5.22 (dd, J=32.0, 4.0 Hz, 1H), 4.52-4.41 (m, 3H), 4.08-4.04 (m, 2H), 3.87-3.81 (m, 1H), 3.40-3.33 (m, 6H), 3.32-3.31 (m, 1H), 3.21-3.09 (m, 1H), 1.50-1.38 (m, 6H).

Example 1221: (3S)-11-(2,4-Difluorophenyl)-8-(4-(2-fluoroacryloyl)piperazin-1-yl)-3-methoxy-10-(trifluoromethyl)-3,4-dihydro-2H,6H-[1,4]thiazepino[2,3,4-ij]quinazolin-6-one

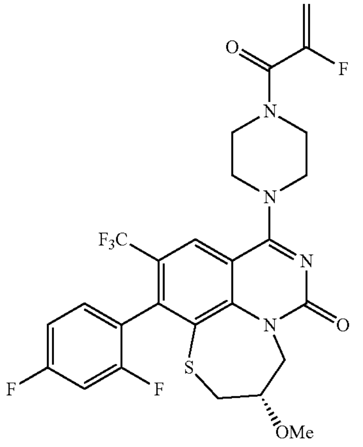 [SMILES: C=C(F)C(=O)N1CCN(c2nc(=O)n3c4c(c(-c5ccc(F)cc5F)c(C(F)(F)F)cc24)SC[C@@H](OC)C3)CC1]

The title compound was prepared analogously to Example 418 where (3S)-11-(2,4-difluorophenyl)-3-methoxy-8-(piperazin-1-yl)-10-(trifluoromethyl)-3,4-dihydro-2H,6H-[1,4]thiazepino[2,3,4-ij]quinazolin-6-one was substituted in place of 10-(2,4-difluorophenyl)-7-(7-oxo-3,9-diazabicyclo[3.3.1]nonan-3-yl)-9-(trifluoromethyl)-2,3-dihydro-5H-[1,4]thiazino[2,3,4-ij]quinazolin-5-one. The title compound was isolated in 33% yield as a yellow solid. m/z (ESI, +ve)=585.2 [M+H]+. $^1$H NMR (400 MHz, DMSO-d6) δ=7.86 (s, 1H), 7.47-7.35 (m, 2H), 7.27-7.19 (m, 1H), 5.34-5.29 (m, 1H), 5.27 (dd, J=64, 4 Hz, 1H), 4.50-4.42 (m, 1H), 3.88-3.76 (m, 6H), 3.34-3.30 (m, 8H), 3.19-3.07 (m, 1H).

Example 1222: (S)-8-((3S,5R)-4-(2-Fluoroacryloyl)-3,5-dimethylpiperazin-1-yl)-11-(4-fluorophenyl)-3-methoxy-10-(trifluoromethyl)-3,4-dihydro-2H,6H-[1,4]thiazepino[2,3,4-ij]quinazolin-6-one

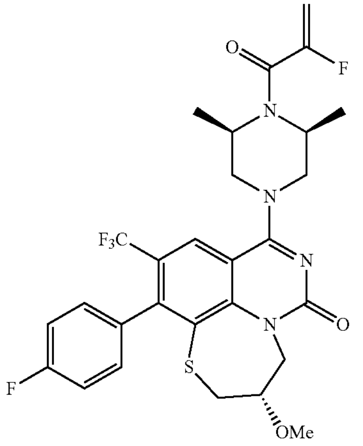 [SMILES: C=C(F)C(=O)N1[C@H](C)CN(c2nc(=O)n3c4c(c(-c5ccc(F)cc5)c(C(F)(F)F)cc24)SC[C@@H](OC)C3)C[C@@H]1C]

The title compound was prepared analogously to Example 418 where (S)-8-((3S,5R)-3,5-dimethylpiperazin-1-yl)-11-(4-fluorophenyl)-3-methoxy-10-(trifluoromethyl)-3,4-dihydro-2H,6H-[1,4]thiazepino[2,3,4-ij]quinazolin-6-one was substituted in place of 10-(2,4-difluorophenyl)-7-(7-oxo-3,9-diazabicyclo[3.3.1]nonan-3-yl)-9-(trifluoromethyl)-2,3-dihydro-5H-[1,4]thiazino[2,3,4-ij]quinazolin-5-one. The title compound was isolated in 33% yield as a yellow solid. m/z (ESI, +ve)=595.2 [M+H]+. $^1$H NMR (400 MHz, DMSO-d6) δ 8.00 (s, 1H), 7.41-7.22 (m, 4H), 5.33-5.29 (m, 1H), 5.23 (dd, J=28.0, 4.0 Hz, 1H), 4.56-4.39 (m, 3H), 4.14-4.02 (m, 2H), 3.84-3.78 (m, 1H), 3.43-3.34 (m, 7H), 3.16-3.04 (m, 1H), 1.58-1.24 (m, 6H).

Example 1223: (S)-8-(4-(2-Fluoroacryloyl)piperazin-1-yl)-11-(4-fluorophenyl)-3-methoxy-10-(trifluoromethyl)-3,4-dihydro-2H,6H-[1,4]thiazepino[2,3,4-ij]quinazolin-6-one

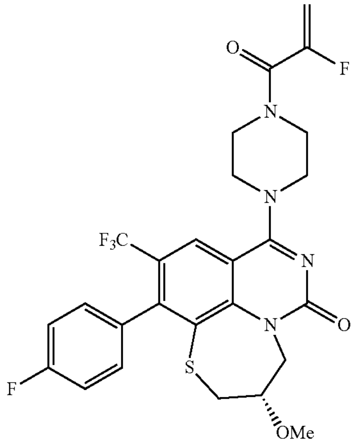 [SMILES: C=C(F)C(=O)N1CCN(c2nc(=O)n3c4c(c(-c5ccc(F)cc5)c(C(F)(F)F)cc24)SC[C@@H](OC)C3)CC1]

The title compound was prepared analogously to Example 418 where (S)-11-(4-fluorophenyl)-3-methoxy-8-(piperazin-1-yl)-10-(trifluoromethyl)-3,4-dihydro-2H,6H-[1,4]thiazepino[2,3,4-ij]quinazolin-6-one was substituted in place of 10-(2,4-difluorophenyl)-7-(7-oxo-3,9-diazabicyclo[3.3.1]nonan-3-yl)-9-(trifluoromethyl)-2,3-dihydro-5H-[1,4]thiazino[2,3,4-ij]quinazolin-5-one. The title compound was isolated in 40% yield as a yellow solid. m/z (ESI, +ve)=567.0 [M+H]+. $^1$H NMR (400 MHz, DMSO-$d_6$) δ 7.86 (s, 1H), 7.42-7.22 (m, 4H), 5.35-5.31 (m, 1H), 5.29 (dd, J=64.0 Hz, 4.0 Hz, 1H), 4.54-4.50 (m, 1H), 3.96-3.62 (m, 9H), 3.41-3.34 (m, 5H), 3.14-3.07 (m, 1H).

Example 1224: N—((S)-8-((3S,5R)-4-Acryloyl-3,5-dimethylpiperazin-1-yl)-11-(4-fluorophenyl)-6-oxo-10-(trifluoromethyl)-3,4-dihydro-2H,6H-[1,4]thiazepino[2,3,4-ij]quinazolin-3-yl)methanesulfonamide

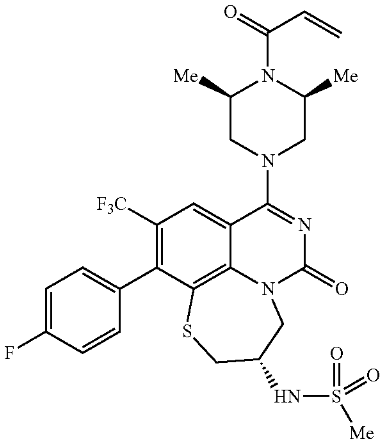 [SMILES: C=CC(=O)N1[C@H](C)CN(c2nc(=O)n3c4c(c(-c5ccc(F)cc5)c(C(F)(F)F)cc24)SC[C@@H](NS(C)(=O)=O)C3)C[C@@H]1C]

To a solution of (S)-8-((3S,5R)-4-acryloyl-3,5-dimethylpiperazin-1-yl)-3-amino-11-(4-fluorophenyl)-10-(trifluoromethyl)-3,4-dihydro-2H,6H-[1,4]thiazepino[2,3,4-ij]quinazolin-6-one (0.020 mmol) in dichloromethane (1 mL) were added triethylamine (0.059 mmol) and methanesulfonyl chloride (0.04 mmol) at 0° C. The reaction mixture was stirred at room temperature for 1 hour. The volatiles were removed under reduced pressure and the resulting residue purified by preparative HPLC to afford the title compound in 51% yield as a light yellow solid. m/z (ESI, +ve)=640.0 [M+H]+. $^1$H NMR (400 MHz, DMSO-$d_6$) δ 8.04 (s, 1H), 7.35 (m, 4H), 6.82 (dd, J=16.0, 8.0 Hz, 1H), 6.19 (dd, J=16.0, 4.0 Hz, 1H), 5.75 (dd, J=8.0, 4.0 Hz, 1H), 4.86-4.33 (m, 6H), 4.15-3.90 (m, 3H), 3.73-3.56 (m, 1H), 3.27-3.15 (m, 2H), 3.01 (s, 3H), 1.40 (s, 6H).

Example 1225: (3S)-8-((3S,5R)-4-Acryloyl-3,5-dimethylpiperazin-1-yl)-11-(3,5-difluoropyridin-2-yl)-3-methoxy-10-(trifluoromethyl)-3,4-dihydro-2H,6H-[1,4]thiazepino[2,3,4-ij]quinazolin-6-one

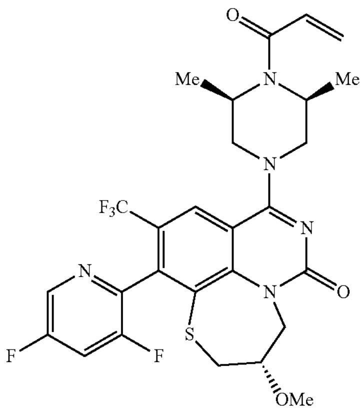 [SMILES: C=CC(=O)N1[C@H](C)CN(c2nc(=O)n3c4c(c(-c5ncc(F)cc5F)c(C(F)(F)F)cc24)SC[C@@H](OC)C3)C[C@@H]1C]

The title compound was prepared analogously to Example 84 where (3S)-11-(3,5-difluoropyridin-2-yl)-8-((3S,5R)-3, 5-dimethylpiperazin-1-yl)-3-methoxy-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 23% yield as a yellow solid. m/z (ESI, +ve)=596.2 [M+H]+. 1H NMR (400 MHz, DMSO) δ 8.73 (s, 1H), 8.24-8.18 (m, 1H), 8.08-8.07 (m, 1H), 6.81 (dd, J=16.0, 8.0 Hz, 1H), 6.19 (dd, J=16.0, 4.0 Hz, 1H), 5.74 (dd, J=8.0, 4.0 Hz, 1H), 4.65-4.55 (m, 2H), 4.50-4.43 (m, 2H), 4.09-4.03 (m, 2H), 3.87-3.85 (m, 1H), 3.65-3.35 (m, 3H), 3.32-3.08 (m, 4H), 1.50-1.35 (m, 6H).

Step 1: Methyl 2-amino-4-(3,5-difluoropyridin-2-yl)-5-(trifluoromethyl)benzoate

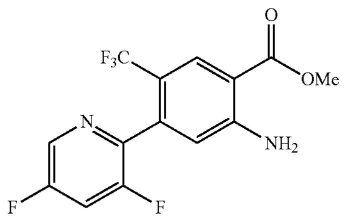 [SMILES: COC(=O)c1cc(C(F)(F)F)c(-c2ncc(F)cc2F)cc1N]

The title compound was prepared analogously to Example 1207, step 2, where 2-bromo-3,5-difluoropyridine and methyl 2-amino-4-(4,4,5,5-tetramethyl-1,3,2-dioxaborolan-2-yl)-5-(trifluoromethyl)benzoate were substituted in place of 2-bromo-5-fluoropyridine and methyl 2-amino-4-(4,4,5,5-tetramethyl-1,3,2-dioxaborolan-2-yl)benzoate. The title compound was isolated in 72% yield as a yellow solid. m/z (ESI, +ve)=333.1 [M+H]+.

Step 2: Methyl 2-amino-4-(3,5-difluoropyridin-2-yl)-3-iodo-5-(trifluoromethyl)benzoate

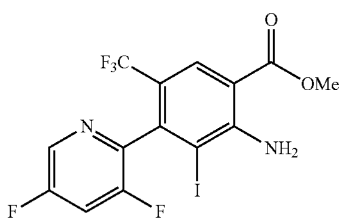 [SMILES: COC(=O)c1cc(C(F)(F)F)c(-c2ncc(F)cc2F)c(I)c1N]

The title compound was prepared analogously to Example 1207, step 7, where methyl 2-amino-4-(3,5-difluoropyridin-2-yl)-5-(trifluoromethyl)benzoate was substituted in place of methyl 2-amino-4-(5-fluoropyridin-2-yl)-5-(trifluoromethyl)benzoate. The title compound was isolated in 73% yield as a yellow solid. m/z (ESI, +ve)=459.0 [M+H]+.

Step 3: 2-Amino-4-(3,5-difluoropyridin-2-yl)-3-iodo-5-(trifluoromethyl)benzoic acid

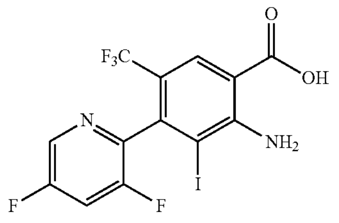

The title compound was prepared analogously to Example 1207, step 8, where methyl 2-amino-4-(3,5-difluoropyridin-2-yl)-3-iodo-5-(trifluoromethyl)benzoate was substituted in place of methyl 2-amino-4-(5-fluoropyridin-2-yl)-3-iodo-5-(trifluoromethyl)benzoate. The title compound was isolated in 96% yield as a yellow solid. m/z (ESI, +ve)=444.9 [M+H]+.

Step 4: 7-(3,5-Difluoropyridin-2-yl)-8-iodo-6-(trifluoromethyl)quinazoline-2,4(1H,3H)-dione

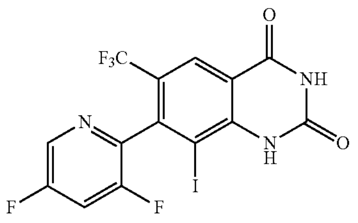 [SMILES: O=c1[nH]c(=O)c2cc(C(F)(F)F)c(-c3ncc(F)cc3F)c(I)c2[nH]1]

The title compound was prepared analogously to Example 1207, step 9, where 2-amino-4-(3,5-difluoropyridin-2-yl)-3-iodo-5-(trifluoromethyl)benzoic acid was substituted in place of 2-amino-4-(5-fluoropyridin-2-yl)-3-iodo-5-(trifluoromethyl)benzoic acid. The title compound was isolated in 36% yield as a yellow solid. m/z (ESI, +ve)=470.0 [M+H]+

Step 5: 7-(3,5-Difluoropyridin-2-yl)-8-(((S)-3-hydroxy-2-methoxypropyl)thio)-6-(trifluoromethyl)quinazoline-2,4(1H,3H)-dione

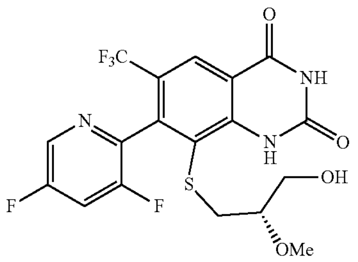 [SMILES: CO[C@@H](CO)CSc1c(-c2ncc(F)cc2F)c(C(F)(F)F)cc2c(=O)[nH]c(=O)[nH]c12]

The title compound was synthesized analogously to example 100, step 9 where 7-(3,5-difluoropyridin-2-yl)-8-iodo-6-(trifluoromethyl)quinazoline-2,4(1H,3H)-dione and (S)-3-mercapto-2-methoxypropan-1-ol were substituted in place of 7-(2,4-difluorophenyl)-8-iodo-6-(trifluoromethyl)quinazoline-2,4(1H,3H)-dione and 2-mercaptoethan-1-ol.

The title compound was isolated in 75% yield as a yellow solid. m/z (ESI, +ve)=464.0 [M+H]+.

Step 6: (3S)-11-(3,5-Difluoropyridin-2-yl)-3-methoxy-10-(trifluoromethyl)-3,4-dihydro-2H,6H-[1,4]thiazepino[2,3,4-ij]quinazoline-6,8(7H)-dione

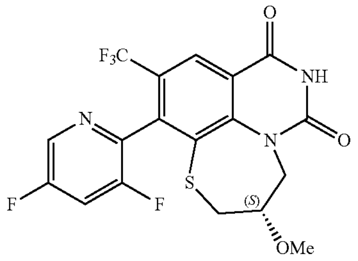

The title compound was prepared analogously to Example 100, step 10 where 7-(3,5-difluoropyridin-2-yl)-8-(((S)-3-hydroxy-2-methoxypropyl)thio)-6-(trifluoromethyl)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione. m/z (ESI, +ve)=446.0 [M+H]+.

Step 7: (3S)-11-(3,5-Difluoropyridin-2-yl)-8-((3S,5R)-3,5-dimethylpiperazin-1-yl)-3-methoxy-10-(trifluoromethyl)-3,4-dihydro-2H,6H-[1,4]thiazepino[2,3,4-ij]quinazolin-6-one

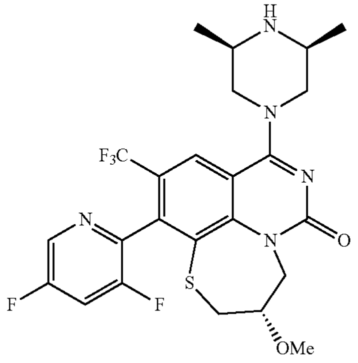 [SMILES: CO[C@@H]1CSc2c(-c3ncc(F)cc3F)c(C(F)(F)F)cc3c(N4C[C@@H](C)N[C@@H](C)C4)nc(=O)n(c23)C1]

The title compound was prepared analogously to Example 100, step 21 where (3S)-11-(3,5-difluoropyridin-2-yl)-3-methoxy-10-(trifluoromethyl)-3,4-dihydro-2H,6H-[1,4]thiazepino[2,3,4-ij]quinazoline-6,8(7H)-dione and (2R,6S)-2,6-dimethylpiperazine were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 67% yield (last two steps) as a yellow solid. m/z (ESI, +ve)=542.2 [M+H]+.

Example 1226: 2-((3S)-8-((3S,5R)-4-Acryloyl-3,5-dimethylpiperazin-1-yl)-3-methoxy-6-oxo-10-(trifluoromethyl)-3,4-dihydro-2H,6H-[1,4]thiazepino[2,3,4-ij]quinazolin-11-yl)-5-fluorobenzonitrile

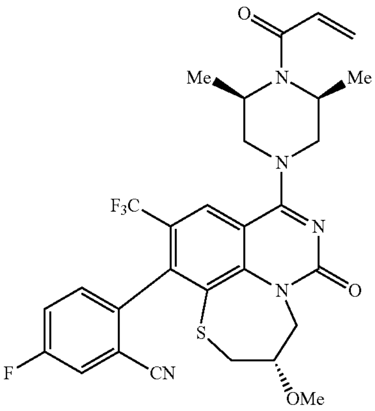 [SMILES: C=CC(=O)N1[C@H](C)CN(c2nc(=O)n3c4c(c(-c5ccc(F)cc5C#N)c(C(F)(F)F)cc24)SC[C@@H](OC)C3)C[C@@H]1C]

The title compound was prepared analogously to Example 84 where 2-((3S)-8-((3S,5R)-3,5-dimethylpiperazin-1-yl)-3-methoxy-6-oxo-10-(trifluoromethyl)-3,4-dihydro-2H,6H-[1,4]thiazepino[2,3,4-ij]quinolin-11-yl)-5-fluorobenzonitrile was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 45% yield as a yellow solid. m/z (ESI, +ve)=602.2 [M+H]+. $^1$H NMR (400 MHz, DMSO) δ 8.17-8.06 (m, 2H), 7.83-7.76 (m, 1H), 7.65-7.53 (m, 1H), 6.81 (dd, J=16.0, 8.0 Hz, 1H), 6.19 (dd, J=16.0, 4.0 Hz, 1H), 5.74 (dd, J=8.0, 4.0 Hz, 1H), 4.64-4.37 (m, 3H), 4.11-4.07 (m, 2H), 3.90-3.86 (m, 1H), 3.56-3.43 (m, 1H), 3.39-3.33 (m, 4H), 3.33-3.25 (m, 2H), 3.23-3.11 (m, 1H), 1.40 (s, 6H).

Step 1: Methyl 5-amino-2'-cyano-4'-fluoro-2-(trifluoromethyl)-[1,1'-biphenyl]-4-carboxylate

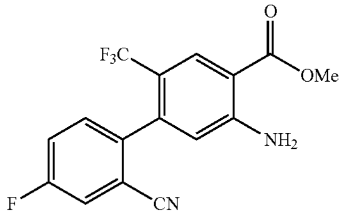 [SMILES: COC(=O)c1cc(C(F)(F)F)c(-c2ccc(F)cc2C#N)cc1N]

The title compound was prepared analogously to Example 1207, step 2, where 2-bromo-5-fluorobenzonitrile and methyl 2-amino-4-(4,4,5,5-tetramethyl-1,3,2-dioxaborolan-2-yl)-5-(trifluoromethyl)benzoate were substituted in place of 2-bromo-5-fluoropyridine and methyl 2-amino-4-(4,4,5,5-tetramethyl-1,3,2-dioxaborolan-2-yl)benzoate. The title compound was isolated in 77% yield as a white solid. m/z (ESI, +ve)=339.0 [M+H]+.

Step 2: Methyl 3-amino-2'-cyano-4'-fluoro-2-iodo-6-(trifluoromethyl)-[1,1'-biphenyl]-4-carboxylate

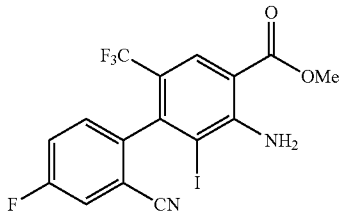 [SMILES: COC(=O)c1cc(C(F)(F)F)c(-c2ccc(F)cc2C#N)c(I)c1N]

The title compound was prepared analogously to Example 1207, step 7, where methyl 5-amino-2'-cyano-4'-fluoro-2-(trifluoromethyl)-[1,1'-biphenyl]-4-carboxylate was substituted in place of methyl 2-amino-4-(5-fluoropyridin-2-yl)-5-(trifluoromethyl)benzoate. The title compound was isolated in 94% yield as a white solid. m/z (ESI, +ve)=465.0 [M+H]+.

Step 3: 3-Amino-2'-cyano-4'-fluoro-2-iodo-6-(trifluoromethyl)-[1,1'-biphenyl]-4-carboxylic acid

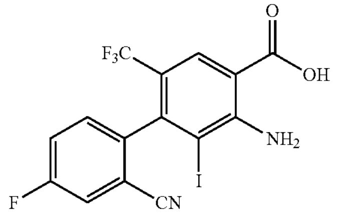 [SMILES: N#Cc1cc(F)ccc1-c1c(C(F)(F)F)cc(C(=O)O)c(N)c1I]

The title compound was prepared analogously to Example 1207, step 8, where methyl 3-amino-2'-cyano-4'-fluoro-2-iodo-6-(trifluoromethyl)-[1,1'-biphenyl]-4-carboxylate was substituted in place of methyl 2-amino-4-(5-fluoropyridin-2-yl)-3-iodo-5-(trifluoromethyl)benzoate. The title compound was isolated in 95% yield as a white solid. m/z (ESI, +ve)=451.0 [M+H]+.

Step 4: 5-Fluoro-2-(8-iodo-2,4-dioxo-6-(trifluoromethyl)-1,2,3,4-tetrahydroquinazolin-7-yl)benzonitrile

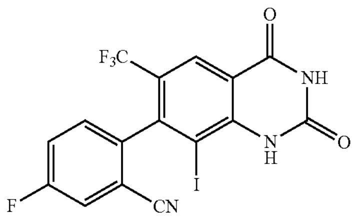 [SMILES: N#Cc1cc(F)ccc1-c1c(C(F)(F)F)cc2c(=O)[nH]c(=O)[nH]c2c1I]

The title compound was prepared analogously to Example 1207, step 9, where 3-amino-2'-cyano-4'-fluoro-2-iodo-6-(trifluoromethyl)-[1,1'-biphenyl]-4-carboxylic acid was substituted in place of 2-amino-4-(5-fluoropyridin-2-yl)-3-iodo-5-(trifluoromethyl)benzoic acid. The title compound was isolated in 50% yield as a yellow solid. m/z (ESI, +ve)=475.9 [M+H]+

Step 5: 5-Fluoro-2-(8-(((S)-3-hydroxy-2-methoxypropyl)thio)-2,4-dioxo-6-(trifluoromethyl)-1,2,3,4-tetrahydroquinazolin-7-yl)benzonitrile

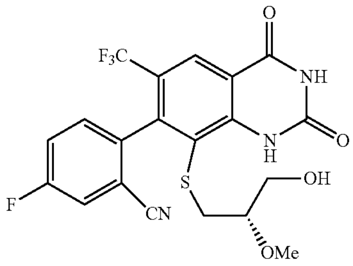 [SMILES: CO[C@@H](CO)CSc1c(-c2ccc(F)cc2C#N)c(C(F)(F)F)cc2c(=O)[nH]c(=O)[nH]c12]

The title compound was synthesized analogously to example 100, step 9 where 5-fluoro-2-(8-iodo-2,4-dioxo-6-(trifluoromethyl)-1,2,3,4-tetrahydroquinazolin-7-yl)benzonitrile and (S)-3-mercapto-2-methoxypropan-1-ol were substituted in place of 7-(2,4-difluorophenyl)-8-iodo-6-(trifluoromethyl)quinazoline-2,4(1H,3H)-dione and 2-mercaptoethan-1-ol. The title compound was isolated in 82% yield as a white solid. m/z (ESI, +ve)=470.0 [M+H]+.

Step 6: 5-Fluoro-2-((3S)-3-methoxy-6,8-dioxo-10-(trifluoromethyl)-3,4,7,8-tetrahydro-2H,6H-[1,4]thiazepino[2,3,4-ij]quinazolin-11-yl)benzonitrile

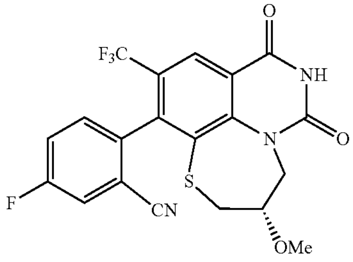 [SMILES: CO[C@@H]1CSc2c(-c3ccc(F)cc3C#N)c(C(F)(F)F)cc3c(=O)[nH]c(=O)n(c23)C1]

The title compound was prepared analogously to Example 100, step 10 where 5-fluoro-2-(8-(((S)-3-hydroxy-2-methoxypropyl)thio)-2,4-dioxo-6-(trifluoromethyl)-1,2,3,4-tetrahydroquinazolin-7-yl)benzonitrile was substituted in place of 7-(2,4-difluorophenyl)-8-((2-hydroxyethyl)thio)-6-(trifluoromethyl)quinazoline-2,4(1H,3H)-dione in 91% yield as a yellow solid. m/z (ESI, +ve)=452.0 [M+H]+.

Step 7: 2-((3S)-8-((3S,5R)-3,5-dimethylpiperazin-1-yl)-3-methoxy-6-oxo-10-(trifluoromethyl)-3,4-dihydro-2H,6H-[1,4]thiazepino[2,3,4-ij]quinazolin-11-yl)-5-fluorobenzonitrile

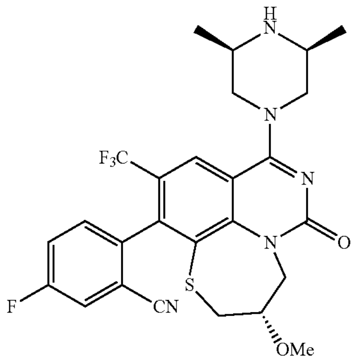 [SMILES: CO[C@@H]1CSc2c(-c3ccc(F)cc3C#N)c(C(F)(F)F)cc3c(N4C[C@@H](C)N[C@@H](C)C4)nc(=O)n(c23)C1]

The title compound was prepared analogously to Example 100, step 21 where 5-fluoro-2-((3S)-3-methoxy-6,8-dioxo-10-(trifluoromethyl)-3,4-dihydro-2H,6H,8H-712-[1,4]thiazepino[2,3,4-ij]quinazolin-11-yl)benzonitrile and (2S,6R)-2,6-dimethylpiperazine were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 83% yield as a yellow solid. m/z (ESI, +ve)=548.1 [M+H]+.

Example 1227: 8-((3S,5R)-4-acryloyl-3,5-dimethylpiperazin-1-yl)-11-(2,4-difluorophenyl)-10-(trifluoromethyl)-3,4-dihydro-2H,6H-[1,4]thiazepino[2,3,4-ij]quinazolin-6-one

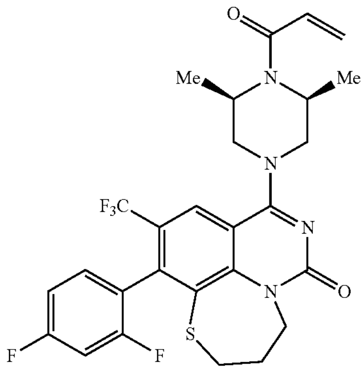 [SMILES: C=CC(=O)N1[C@H](C)CN(c2nc(=O)n3c4c(c(-c5ccc(F)cc5F)c(C(F)(F)F)cc24)SCCC3)C[C@@H]1C]

The title compound was prepared analogously to Example 84 where 11-(2,4-difluorophenyl)-8-((3S,5R)-3,5-dimethylpiperazin-1-yl)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 5% yield as a yellow solid. m/z (ESI, +ve)=565.2 [M+H]+. $^{1}$H NMR (400 MHz, MeOD) δ 8.45 (s, 1H), 8.06 (s, 1H), 7.24-7.16 (m, 1H), 7.05-6.97 (m, 1H), 6.74 (dd, J=16.7, 10.7 Hz, 1H), 6.19 (dd, J=16.7, 2.0 Hz, 1H), 5.70 (dd, J=10.6, 2.0 Hz, 1H), 4.69-4.49 (m, 3H), 4.14 (d, J=13.5 Hz, 2H), 3.38-3.24 (m, 3H), 2.18-2.00 (m, 2H), 1.47-1.08 (m, 6H).

Step 1: tert-butyl (2S,6R)-4-(11-(2,4-difluorophenyl)-6-oxo-10-(trifluoromethyl)-3,4-dihydro-2H,6H-[1,4]thiazepino[2,3,4-ij]quinazolin-8-yl)-2,6-dimethylpiperazine-1-carboxylate

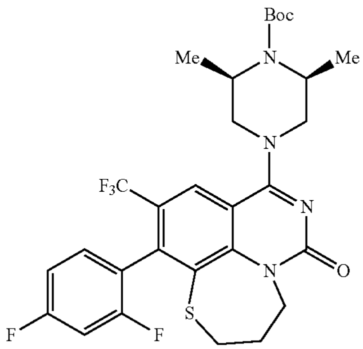 [SMILES: C[C@@H]1CN(c2nc(=O)n3c4c(c(-c5ccc(F)cc5F)c(C(F)(F)F)cc24)SCCC3)C[C@H](C)N1C(=O)OC(C)(C)C]

The title compound was prepared analogously to Example 100, step 21 where 11-(2,4-difluorophenyl)-10-(trifluoromethyl)-3,4-dihydro-2H,6H-[1,4]thiazepino[2,3,4-ij]quinazoline-6,8(7H)-dione and tert-butyl (2S,6R)-2,6-dimethylpiperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 22% yield as a yellow solid. m/z (ESI, +ve)=611.2 [M+H]+.

Step 2: 11-(2,4-difluorophenyl)-8-((3S,5R)-3,5-dimethylpiperazin-1-yl)-10-(trifluoromethyl)-3,4-dihydro-2H,6H-[1,4]thiazepino[2,3,4-ij]quinazolin-6-one

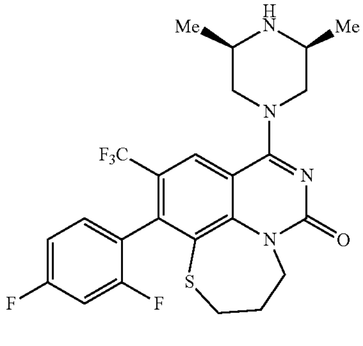 [SMILES: C[C@@H]1CN(c2nc(=O)n3c4c(c(-c5ccc(F)cc5F)c(C(F)(F)F)cc24)SCCC3)C[C@H](C)N1]

The title compound was prepared analogously to Example 102, step 4, where tert-butyl (2S,6R)-4-(11-(2,4-difluorophenyl)-6-oxo-10-(trifluoromethyl)-3,4-dihydro-2H,6H-[1,4]thiazepino[2,3,4-ij]quinazolin-8-yl)-2,6-dimethylpiperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated as a yellow solid and used in the next step without further purification. m/z (ESI, +ve)=511.2 [M+H]+.

Example 1228: (S)-8-((3S,5R)-4-(acryloyl-d3)-3,5-dimethylpiperazin-1-yl)-11-(4-fluorophenyl)-3-methoxy-10-(trifluoromethyl)-3,4-dihydro-2H,6H-[1,4]thiazepino[2,3,4-ij]quinazolin-6-one

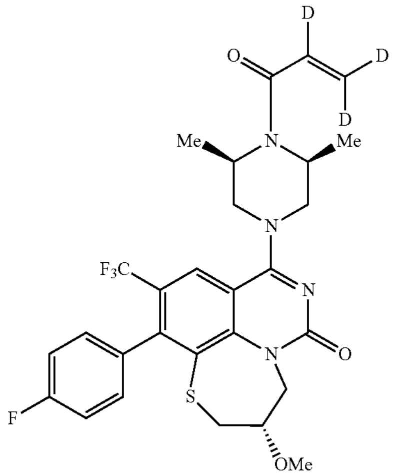 [SMILES: [2H]C([2H])=C([2H])C(=O)N1[C@H](C)CN(c2nc(=O)n3c4c(c(-c5ccc(F)cc5)c(C(F)(F)F)cc24)SC[C@@H](OC)C3)C[C@@H]1C]

Oxalyl chloride (0.19 mmol) was added over a 0° C. solution of acrylic-2,3,3-d3 acid and two drops of DMF in dichloromethane (0.4 mL). After 10 minutes the mixture was stirred at room temperature for 1 hour, cooled down to 0° C. and added to a freshly prepared 0° C. solution of (S)-8-((3S,5R)-3,5-dimethylpiperazin-1-yl)-11-(4-fluorophenyl)-3-methoxy-10-(trifluoromethyl)-3,4-dihydro-2H,6H-[1,4]thiazepino[2,3,4-ij]quinazolin-6-one (0.09 mmol) and diisopropylethylamine (0.35 mmol) in 0.6 mL of THF. After 10 minutes, the reaction was quenched with water and extracted with ethyl acetate, dried over sodium sulfate and concentrated to afford a residue that was purified by HPLC to afford the title compound in 57% yield as a yellow solid. m/z (ESI, +ve)=580.2 [M+H]+. $^1$H NMR (400 MHz, MeOD) δ 8.03 (s, 1H), 7.21-7.18 (m, 2H), 7.14-7.10 (m, 2H), 4.56 (m, 3H), 4.17 (m, 2H), 3.83 (bs, 1H), 3.35 (m, 5H), 2.98 (dd, J=15, 5.2 Hz, 1H), 1.40 (m, 6H).

Example 229: (S)-8-((3S,5R)-4-acryloyl-3,5-dimethylpiperazin-1-yl)-11-(4-fluorophenyl)-3-(methoxy-d3)-10-(trifluoromethyl)-3,4-dihydro-2H,6H-[1,4]thiazepino[2,3,4-ij]quinazolin-6-one

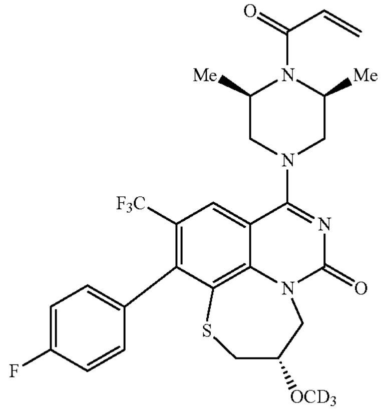

The title compound was prepared analogously to Example 84 where (S)-8-((3S,5R)-3,5-dimethylpiperazin-1-yl)-11-(4-fluorophenyl)-3-(methoxy-d3)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 38% yield as a yellow solid. m/z (ESI, +ve)=580.2 [M+H]+. $^1$H NMR (400 MHz, MeOD) δ 8.03 (s, 1H), 7.21-7.18 (m, 2H), 7.14-7.10 (m, 2H), 6.74 (dd, J=16.7, 10.6 Hz), 6.19 (dd, J=16.7, 2.0 HZ, 1H), 5.71 (dd, J=10.6, 2.0 Hz, 1H), 4.57 (dd, J=13.9, 3.9 Hz, 2H), 4.17 (m, 2H), 3.84 (m, 1H), 3.34 (m, 2H), 2.98 (dd, J=15.0, 5.3 Hz, 1H), 1.41 (m, 6H).

Step 1: tert-butyl (2S,6R)-4-((S)-11-(4-fluorophenyl)-3-(methoxy-d3)-6-oxo-10-(trifluoromethyl)-3,4-dihydro-2H,6H-[1,4]thiazepino[2,3,4-ij]quinazolin-8-yl)-2,6-dimethylpiperazine-1-carboxylate

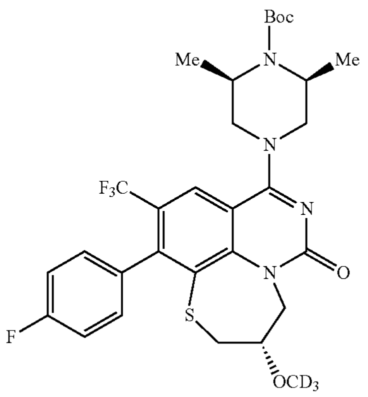

NaH (0.33 mmol) was added over a 0° C. solution of tert-butyl (2S,6R)-4-((S)-11-(4-fluorophenyl)-3-hydroxy-6-oxo-10-(trifluoromethyl)-3,4-dihydro-2H,6H-[1,4]thiazepino[2,3,4-ij]quinazolin-8-yl)-2,6-dimethylpiperazine-1-carboxylate (0.16 mmol) in THF (2 mL). After 15 minutes, iodomethane-d3 was added and the reaction was stirred for 30 additional minutes, quenched with water and extracted with ethyl acetate three times. The combined organic layers were dried over sodium sulfate, filtered and concentrated to afford a residue that was purified by HPLC. The title compound was isolated in quantitative yield as a white solid. m/z (ESI, +ve)=626.2 [M+H]+.

Step 2: (S)-8-((3S,5R)-3,5-dimethylpiperazin-1-yl)-11-(4-fluorophenyl)-3-(methoxy-d3)-10-(trifluoromethyl)-3,4-dihydro-2H,6H-[1,4]thiazepino[2,3,4-ij]quinazolin-6-one

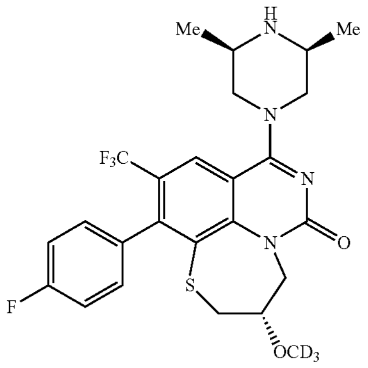

The title compound was prepared analogously to Example 102, step 4, where tert-butyl (2S,6R)-4-((S)-11-(4-fluorophenyl)-3-(methoxy-d3)-6-oxo-10-(trifluoromethyl)-3,4-dihydro-2H,6H-[1,4]thiazepino[2,3,4-ij]quinazolin-8-yl)-2,6-dimethylpiperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in quantitative yield as a yellow solid. m/z (ESI, +ve)=526.2 [M+H]+.

Examples 1230 and 1231: (3S,11R)-8-((3S,5R)-4-acryloyl-3,5-dimethylpiperazin-1-yl)-11-(5-chloro-2,4-difluorophenyl)-3-((5-methylisoxazol-3-yl)oxy)-10-(trifluoromethyl)-3,4-dihydro-2H,6H-[1,4]thiazepino[2,3,4-ij]quinazolin-6-one and (3S,11S)-8-((3S,5R)-4-acryloyl-3,5-dimethylpiperazin-1-yl)-11-(5-chloro-2,4-difluorophenyl)-3-((5-methylisoxazol-3-yl)oxy)-10-(trifluoromethyl)-3,4-dihydro-2H,6H-[1,4]thiazepino[2,3,4-ij]quinazolin-6-one example 230

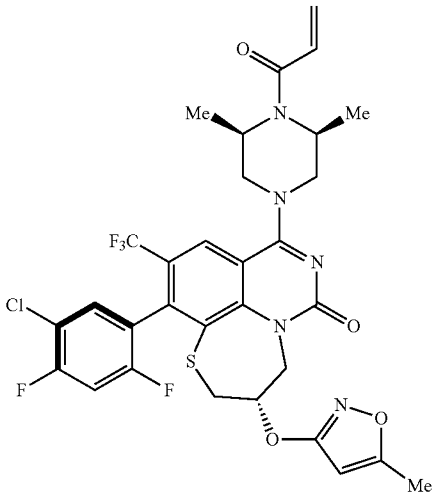

-continued example 231

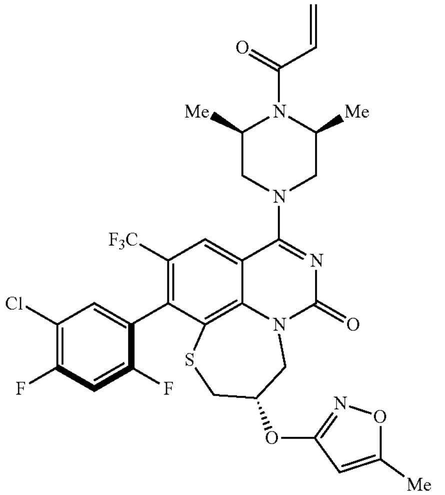

The title compounds were prepared analogously to Example 84 where (3S,11R)-11-(5-chloro-2,4-difluorophenyl)-8-((3S,5R)-3,5-dimethylpiperazin-1-yl)-3-((5-methylisoxazol-3-yl)oxy)-10-(trifluoromethyl)-3,4-dihydro-2H,6H-[1,4]thiazepino[2,3,4-ij]quinazolin-6-one and (3S,11S)-11-(5-chloro-2,4-difluorophenyl)-8-((3S,5R)-3,5-dimethylpiperazin-1-yl)-3-((5-methylisoxazol-3-yl)oxy)-10-(trifluoromethyl)-3,4-dihydro-2H,6H-[1,4]thiazepino[2,3,4-ij]quinazolin-6-one were substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one, respectively. The title compounds were isolated in 16% and 26% yield, respectively, as a yellow solids. Example 1230: m/z (ESI, +ve)=696.2 [M+H]+; 1H NMR (400 MHz, MeOD) δ 8.07 (s, 1H), 7.43 (m, 1H), 7.25 (m, 1H), 6.75 (dd, J=16.7, 2.0 Hz, 1H), 6.20 (d, J=16.7, 2.0 Hz, 1H), 5.71 (dd, J=10.6, 2.0 Hz, 1H), 5.49 (d, J=2.0 Hz, 1H), 4.57 (m, 3H), 4.25 (m, 2H), 4.10-3.88 (m, 4H), 3.45-3.34 (m, 2H), 2.15 (d, J=3.6 Hz, 3H), 1.47 (d, J=4 Hz, 3H), 1.30 (d, J=4 Hz, 3H). Example 1231: m/z (ESI, +ve)=696.2 [M+H]+; 1H NMR (400 MHz, MeOD) δ 8.07 (s, 1H), 7.43-7.39 (m, 1H), 7.31-7.25 (m, 1H), 6.75 (dd, J=16.7, 2.0 Hz, 1H), 6.20 (d, J=16.7, 2.0 Hz, 1H), 5.71 (dd, J=10.6, 2.0 Hz, 1H), 5.49 (d, J=2.0 Hz, 1H), 4.60-4.48 (m, 3H), 4.25 (m, 2H), 4.10-3.88 (m, 4H), 3.45-3.34 (m, 2H), 2.15 (s, 3H), 1.47 (d, J=4 Hz, 3H), 1.30 (d, J=4 Hz, 3H).

Step 1: tert-butyl (2S,6R)-4-((3S)-11-(5-chloro-2,4-difluorophenyl)-3-((5-methylisoxazol-3-yl)oxy)-6-oxo-10-(trifluoromethyl)-3,4-dihydro-2H,6H-[1,4]thiazepino[2,3,4-ij]quinazolin-8-yl)-2,6-dimethylpiperazine-1-carboxylate

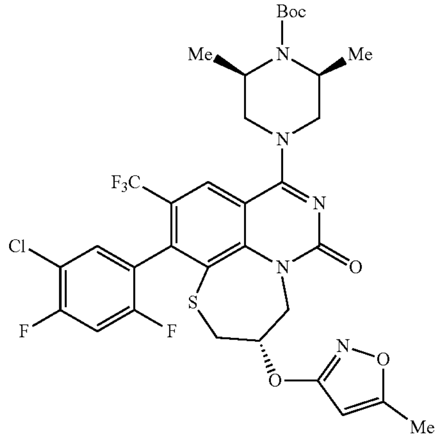 [SMILES: Cc1cc(O[C@@H]2CSc3c(-c4cc(Cl)c(F)cc4F)c(C(F)(F)F)cc4c(N5C[C@@H](C)N(C(=O)OC(C)(C)C)[C@@H](C)C5)nc(=O)n(c34)C2)no1]

A solution of triphenylphosphine (0.45 mmol) and DIAD (0.45 mmol) in THF (5 mL) was stirred at 0° C. for 5 minutes. A solution of 5-methylisoxazol-3-ol (0.45 mmol) and tert-butyl (2S,6R)-4-((3R)-11-(5-chloro-2,4-difluorophenyl)-3-hydroxy-6-oxo-10-(trifluoromethyl)-3,4-dihydro-2H,6H-[1,4]thiazepino[2,3,4-ij]quinazolin-8-yl)-2,6-dimethylpiperazine-1-carboxylate (0.15 mmol) was added and the resulting mixture was stirred at room temperature for 3 hours. The reaction was diluted with ethyl acetate and washed with brine. The organic layer was dried over sodium sulfate, filtered and concentrated to afford a residue that was purified by preparative thin layer chromatography (10% methanol in ethyl acetate). The title compound was isolated in 27% yield as a white solid. m/z (ESI, +ve)=742.2 [M+H]+.

Step 2: (3S)-11-(5-chloro-2,4-difluorophenyl)-8-((3S,5R)-3,5-dimethylpiperazin-1-yl)-3-((5-methylisoxazol-3-yl)oxy)-10-(trifluoromethyl)-3,4-dihydro-2H,6H-[1,4]thiazepino[2,3,4-ij]quinazolin-6-one

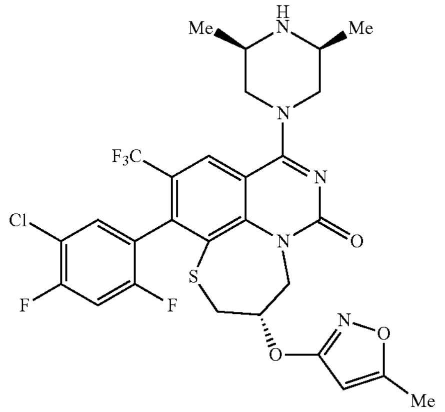 [SMILES: Cc1cc(O[C@@H]2CSc3c(-c4cc(Cl)c(F)cc4F)c(C(F)(F)F)cc4c(N5C[C@@H](C)N[C@@H](C)C5)nc(=O)n(c34)C2)no1]

The title compound was prepared analogously to Example 102, step 4, where tert-butyl (2S,6R)-4-((3S)-11-(5-chloro-2,4-difluorophenyl)-3-((5-methylisoxazol-3-yl)oxy)-6-oxo-10-(trifluoromethyl)-3,4-dihydro-2H,6H-[1,4]thiazepino[2,3,4-ij]quinazolin-8-yl)-2,6-dimethylpiperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. m/z (ESI, +ve)=642.1 [M+H]+.

Example 1232: 2-(((S)-8-((3S,5R)-4-acryloyl-3,5-dimethylpiperazin-1-yl)-11-(4-fluorophenyl)-6-oxo-10-(trifluoromethyl)-3,4-dihydro-2H,6H-[1,4]thiazepino[2,3,4-ij]quinazolin-3-yl)oxy)-N,N-dimethylacetamide

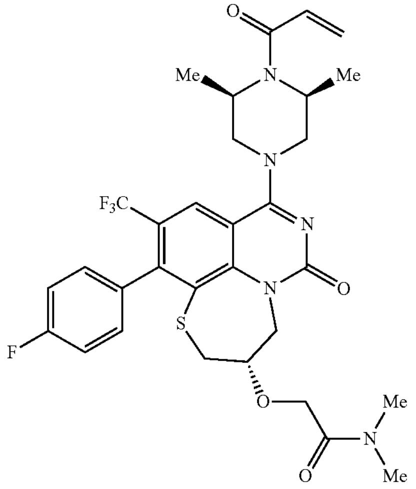 [SMILES: C=CC(=O)N1[C@H](C)CN(c2nc(=O)n3c4c(c(-c5ccc(F)cc5)c(C(F)(F)F)cc24)SC[C@@H](OCC(=O)N(C)C)C3)C[C@@H]1C]

The title compound was prepared analogously to Example 84 where 2-(((S)-8-((3S,5R)-3,5-dimethylpiperazin-1-yl)-11-(4-fluorophenyl)-6-oxo-10-(trifluoromethyl)-3,4-dihydro-2H,6H-[1,4]thiazepino[2,3,4-ij]quinazolin-3-yl)oxy)-N,N-dimethylacetamide was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 59% yield as a yellow solid. m/z (ESI, +ve) =648.2 [M+H]+. 1H NMR (400 MHz, CDCl3) δ 8.00 (s, 1H), 7.28-7.07 (m, 4H), 6.55 (dd, J=16.7, 10.4 Hz, 1H), 6.34 (dd, J=16.7, 1.9 Hz, 1H), 5.70 (dd, J=10.3, 1.9 Hz, 1H), 4.80-4.02 (m, 8H), 3.34-3.12 (m, 3H), 2.90 (s, 3H), 2.68 (s, 3H), 1.66-1.20 (m, 6H). Step 1: tert-butyl (2S,6R)-4-((S)-3-(2-(dimethylamino)-2-oxoethoxy)-11-(4-fluorophenyl)-6-oxo-10-(trifluoromethyl)-3,4-dihydro-2H,6H-[1,4]thiazepino[2,3,4-ij]quinazolin-8-yl)-2,6-dimethylpiperazine-1-carboxylate.

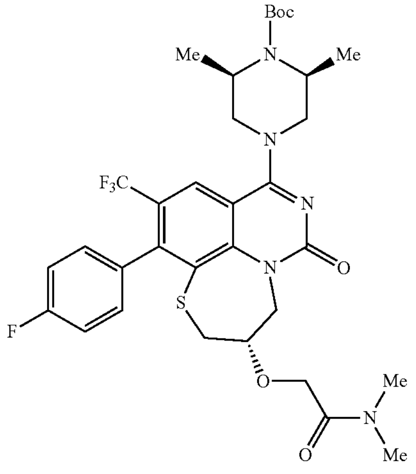 [SMILES: C[C@@H]1CN(c2nc(=O)n3c4c(c(-c5ccc(F)cc5)c(C(F)(F)F)cc24)SC[C@@H](OCC(=O)N(C)C)C3)C[C@H](C)N1C(=O)OC(C)(C)C]

Sodium hydride (0.08 mmol) was added over a 0° C. solution of tert-butyl (2S,6R)-4-((S)-11-(4-fluorophenyl)-3-hydroxy-6-oxo-10-(trifluoromethyl)-3,4-dihydro-2H,6H-[1,4]thiazepino[2,3,4-ij]quinazolin-8-yl)-2,6-dimethylpiperazine-1-carboxylate (0.07 mmol) in THF (2 mL). After 15 minutes, 2-bromo-N,N-dimethylacetamide (0.08 mmol) was added and the mixture stirred at room temperature for 45 minutes. The reaction was quenched by addition of water, extracted with ethyl acetate and the organic layer dried over sodium sulfate, filtered and concentrated to afford a residue that was purified by preparative HPLC. The title compound was isolated as a white solid in 710% yield. m/z (ESI, +ve)=694.2 [M+H]+.

Step 2: 2-(((S)-8-((3S,5R)-3,5-dimethylpiperazin-1-yl)-11-(4-fluorophenyl)-6-oxo-10-(trifluoromethyl)-3,4-dihydro-2H,6H-[1,4]thiazepino[2,3,4-ij]quinazolin-3-yl)oxy)-N,N-dimethylacetamide

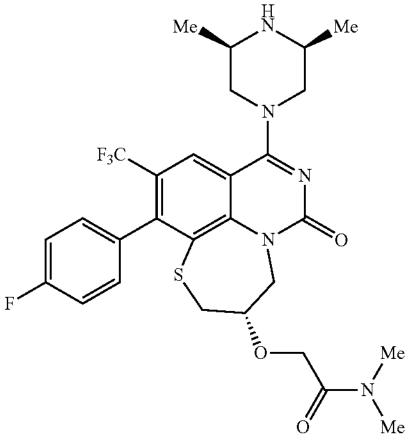 [SMILES: C[C@@H]1CN(c2nc(=O)n3c4c(c(-c5ccc(F)cc5)c(C(F)(F)F)cc24)SC[C@@H](OCC(=O)N(C)C)C3)C[C@H](C)N1]

The title compound was prepared analogously to Example 102, step 4, where tert-butyl (2S,6R)-4-((S)-3-(2-(dimethylamino)-2-oxoethoxy)-11-(4-fluorophenyl)-6-oxo-10-(trifluoromethyl)-3,4-dihydro-2H,6H-[1,4]thiazepino[2,3,4-ij]quinazolin-8-yl)-2,6-dimethylpiperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in quantitative yield as a yellow solid. m/z (ESI, +ve)=594.2 [M+H]+.

Example 1233: 2-(((S)-8-((3S,5R)-4-acryloyl-3,5-dimethylpiperazin-1-yl)-11-(4-fluorophenyl)-6-oxo-10-(trifluoromethyl)-3,4-dihydro-2H,6H-[1,4]thiazepino[2,3,4-ij]quinazolin-3-yl)oxy)acetamide

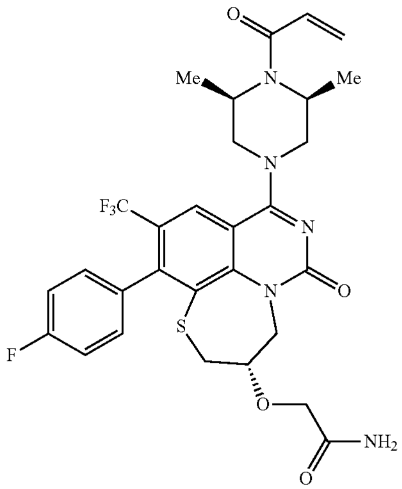 [SMILES: C=CC(=O)N1[C@H](C)CN(c2nc(=O)n3c4c(c(-c5ccc(F)cc5)c(C(F)(F)F)cc24)SC[C@@H](OCC(N)=O)C3)C[C@@H]1C]

The title compound was prepared analogously to Example 84 where 2-(((S)-8-((3S,5R)-3,5-dimethylpiperazin-1-yl)-11-(4-fluorophenyl)-6-oxo-10-(trifluoromethyl)-3,4-dihydro-2H,6H-[1,4]thiazepino[2,3,4-ij]quinazolin-3-yl)oxy)acetamide was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 51% yield as a yellow solid. m/z (ESI, +ve)=620.2 [M+H]+. 1H NMR (400 MHz, CDCl3) δ 8.02 (s, 1H), 7.11 (q, J=8.9, 6.8 Hz, 3H), 6.55 (dd, J=16.6, 10.4 Hz, 1H), 6.34 (dd, J=16.6, 1.9 Hz, 1H), 5.71 (dd, J=10.4, 1.9 Hz, 1H), 5.54 (s, 1H), 5.37-3.58 (m, 9H), 3.50-2.67 (m, 4H), 1.40 (d, J=6.1 Hz, 8H).

Step 1: tert-butyl (2S,6R)-4-((S)-3-(2-amino-2-oxoethoxy)-11-(4-fluorophenyl)-6-oxo-10-(trifluoromethyl)-3,4-dihydro-2H,6H-[1,4]thiazepino[2,3,4-ij]quinazolin-8-yl)-2,6-dimethylpiperazine-1-carboxylate

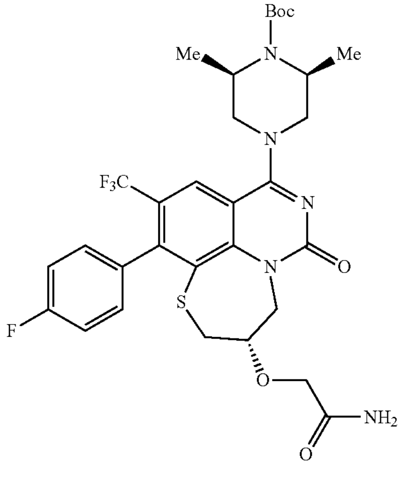 [SMILES: C[C@@H]1CN(c2nc(=O)n3c4c(c(-c5ccc(F)cc5)c(C(F)(F)F)cc24)SC[C@@H](OCC(N)=O)C3)C[C@H](C)N1C(=O)OC(C)(C)C]

The title compound was prepared analogously to Example 1232, step 1, where 2-bromoacetamide was substituted in place of 2-bromo-N,N-dimethylacetamide. The title compound was isolated in 44% yield as a yellow solid. m/z (ESI, +ve)=666.2 [M+H]+. Step 2: 2-(((S)-8-((3S,5R)-3,5-dimethylpiperazin-1-yl)-11-(4-fluorophenyl)-6-oxo-10-(trifluoromethyl)-3,4-dihydro-2H,6H-[1,4]thiazepino[2,3,4-ij]quinazolin-3-yl)oxy)acetamide

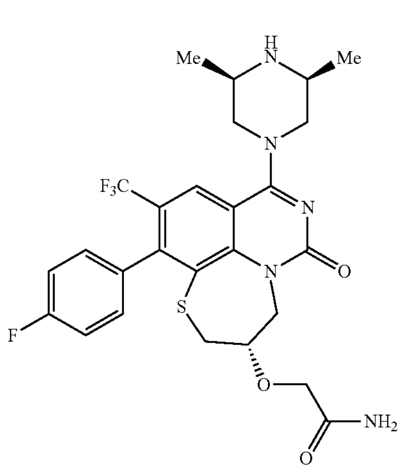 [SMILES: C[C@@H]1CN(c2nc(=O)n3c4c(c(-c5ccc(F)cc5)c(C(F)(F)F)cc24)SC[C@@H](OCC(N)=O)C3)C[C@H](C)N1]

The title compound was prepared analogously to Example 102, step 4, where tert-butyl (2S,6R)-4-((S)-3-(2-amino-2-oxoethoxy)-11-(4-fluorophenyl)-6-oxo-10-(trifluoromethyl)-3,4-dihydro-2H,6H-[1,4]thiazepino[2,3,4-ij]quinazolin-8-yl)-2,6-dimethylpiperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in quantitative yield as a yellow solid. m/z (ESI, +ve)=566.2 [M+H]+.

Example 1234: (3S)-8-((3S,5R)-4-acryloyl-3,5-dimethylpiperazin-1-yl)-11-(5-chloro-2,4-difluorophenyl)-3-(pyridin-4-yloxy)-10-(trifluoromethyl)-3,4-dihydro-2H,6H-[1,4]thiazepino[2,3,4-ij]quinazolin-6-one

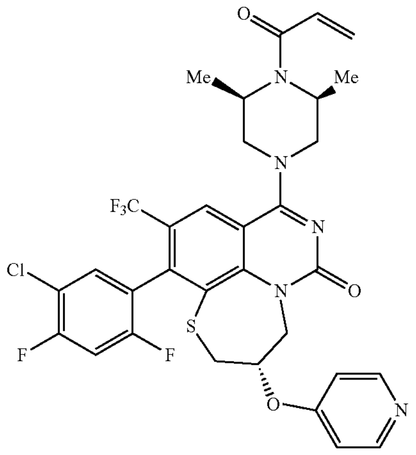 [SMILES: C=CC(=O)N1[C@H](C)CN(c2nc(=O)n3c4c(c(-c5cc(Cl)c(F)cc5F)c(C(F)(F)F)cc24)SC[C@@H](Oc2ccncc2)C3)C[C@@H]1C]

The title compound was prepared analogously to Example 84 where (3S)-11-(5-chloro-2,4-difluorophenyl)-8-((3S,5R)-3,5-dimethylpiperazin-1-yl)-3-(pyridin-4-yloxy)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 9% yield as a white solid. m/z (ESI, +ve)=692.1 (M+H)+. $^1$H NMR (400 MHz, dmso) δ 8.46-8.34 (m, 2H), 8.08 (s, 1H), 7.86-7.67 (m, 2H), 7.04-7.01 (m, 2H), 6.81 (dd, J=16.0, 8.0 Hz, 1H), 6.19 (dd, J=16.0, 4.0 Hz, 1H), 5.75 (dd, J=8.0, 4.0 Hz, 1H), 5.34-5.26 (m, 1H), 4.62-4.58 (m, 2H), 4.46-3.97 (m, 4H), 3.49-3.45 (m, 1H), 3.40-3.36 (m, 2H), 3.26-3.22 (m, 1H), 1.42-1.37 (m, 6H).

Step 1: (S)-4-((1-((tert-butyldiphenylsilyl)oxy)-3-(tritylthio)propan-2-yl)oxy)pyridine

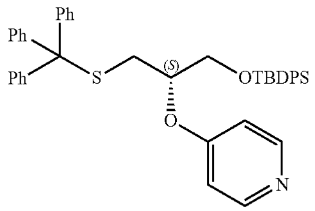

DIAD (0.02 mol) was added over a 0° C. solution of (R)-1-((tert-butyldiphenylsilyl)oxy)-3-(tritylthio)propan-2-ol (0.01 mol) and PPh3 (0.02 mol) in THF (75 mL). The mixture was allowed to reach room temperature slowly and after 16 hours the volatiles were removed under reduced pressure to afford a residue that was purified by silica gel chromatography. The title compound was isolated in 64% yield as a colorless oil. m/z (ESI, +ve)=666.3 (M+H)+.

Step 2: (S)-3-((tert-butyldiphenylsilyl)oxy)-2-(pyridin-4-yloxy)propane-1-thiol

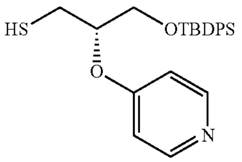

Triethylsilane (0.02 mol) was added over a 0° C. solution of (S)-4-((1-((tert-butyldiphenylsilyl)oxy)-3-(tritylthio)propan-2-yl)oxy)pyridine (0.01 mol) in dichloromethane:trifluoroacetic acid (45 mL:15 mL). After 30 minutes, the reaction was quenched with water and extracted with dichloromethane five times. The combined organic layers were dried over sodium sulfate, filtered and concentrated to afford a residue that was purified by chromatography in silica gel. The title compound was isolated as a colorless oil in 78% yield. m/z (ESI, +ve)=424.2 [M+H]+.

Step 3: 8-(((S)-3-((tert-butyldiphenylsilyl)oxy)-2-(pyridin-4-yloxy)propyl)thio)-7-(5-chloro-2,4-difluorophenyl)-6-(trifluoromethyl)quinazoline-2,4(1H,3H)-dione

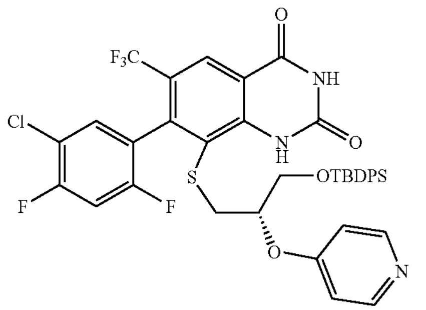

The title compound was synthesized analogously to example 100, step 9 where 7-(5-chloro-2,4-difluorophenyl)-8-iodo-6-(trifluoromethyl)quinazoline-2,4(1H,3H)-dione and (S)-3-((tert-butyldiphenylsilyl)oxy)-2-(pyridin-4-yloxy)propane-1-thiol were substituted in place of 7-(2,4-difluorophenyl)-8-iodo-6-(trifluoromethyl)quinazoline-2,4(1H,3H)-dione and 2-mercaptoethan-1-ol. The title compound was isolated in 33% yield as a yellow solid. m/z (ESI, +ve)=798.0 [M+H]+.

Step 4: 7-(5-chloro-2,4-difluorophenyl)-8-(((S)-3-hydroxy-2-(pyridin-4-yloxy)propyl)thio)-6-(trifluoromethyl)quinazoline-2,4(1H,3H)-dione

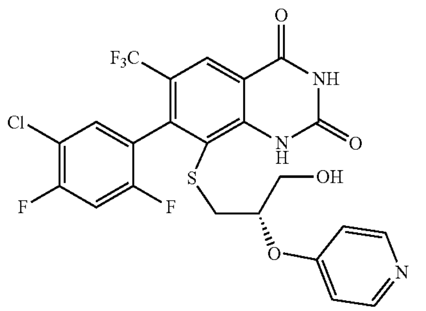 [SMILES: O=c1[nH]c(=O)c2cc(C(F)(F)F)c(-c3cc(Cl)c(F)cc3F)c(SC[C@H](CO)Oc3ccncc3)c2[nH]1]

TBAF (3 mmol) was added over a solution of 8-(((S)-3-((tert-butyldiphenylsilyl)oxy)-2-(pyridin-4-yloxy)propyl)thio)-7-(5-chloro-2,4-difluorophenyl)-6-(trifluoromethyl)quinazoline-2,4(1H,3H)-dione (1 mmol) in THF (10 mL). After 3 hours, the reaction was quenched with water and extracted with ethyl acetate three times. The combined organic layers were dried over sodium sulfate, filtered and concentrated to afford a residue that was purified by silica gel chromatography. The title compound was isolated in 71% yield as a yellow solid. m/z (ESI, +ve)=560.0 [M+H]+.

Step 5: (3S)-11-(5-chloro-2,4-difluorophenyl)-3-(pyridin-4-yloxy)-10-(trifluoromethyl)-3,4-dihydro-2H,6H-[1,4]thiazepino[2,3,4-ij]quinazoline-6,8(7H)-dione

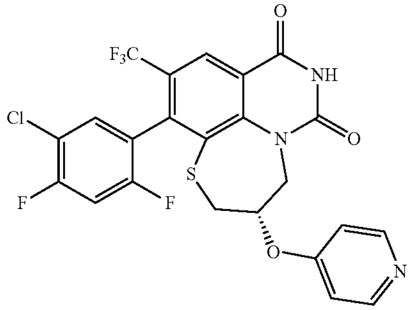 [SMILES: O=c1[nH]c(=O)n2c3c(c(-c4cc(Cl)c(F)cc4F)c(C(F)(F)F)cc13)SC[C@@H](Oc1ccncc1)C2]

The title compound was prepared analogously to Example 100, step 10 where 7-(5-chloro-2,4-difluorophenyl)-8-(((S)-3-hydroxy-2-(pyridin-4-yloxy)propyl)thio)-6-(trifluoromethyl)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 51% yield as a yellow solid. m/z (ESI, +ve)=542.0 [M+H]+.

Step 6: (3S)-11-(5-chloro-2,4-difluorophenyl)-8-((3S,5R)-3,5-dimethylpiperazin-1-yl)-3-(pyridin-4-yloxy)-10-(trifluoromethyl)-3,4-dihydro-2H,6H-[1,4]thiazepino[2,3,4-ij]quinazolin-6-one

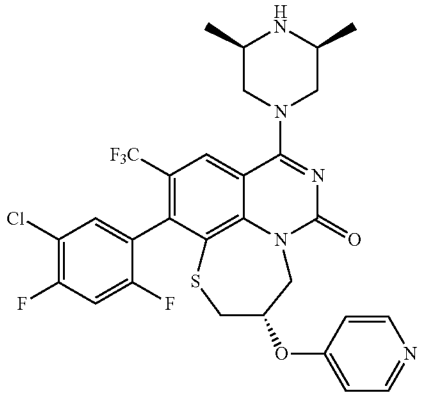 [SMILES: C[C@@H]1CN(c2nc(=O)n3c4c(c(-c5cc(Cl)c(F)cc5F)c(C(F)(F)F)cc24)SC[C@@H](Oc2ccncc2)C3)C[C@H](C)N1]

The title compound was prepared analogously to Example 100, step 21 where (3S)-11-(5-chloro-2,4-difluorophenyl)-3-(pyridin-4-yloxy)-10-(trifluoromethyl)-3,4-dihydro-2H,6H-[1,4]thiazepino[2,3,4-ij]quinazoline-6,8(7H)-dione and (2S,6R)-2,6-dimethylpiperazine were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 42% yield as a yellow solid. m/z (ESI, +ve)=638 [M+H]+.

Example 1235: 2-((3S)-8-((3S,5R)-4-acryloyl-3,5-dimethylpiperazin-1-yl)-3-methoxy-6-oxo-10-(trifluoromethyl)-3,4-dihydro-2H,6H-[1,4]thiazepino[2,3,4-ij]quinazolin-11-yl)-5-fluorobenzamide

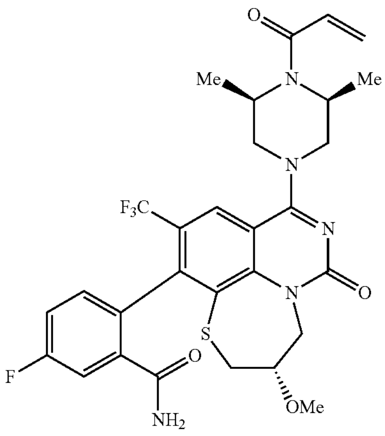 [SMILES: C=CC(=O)N1[C@H](C)CN(c2nc(=O)n3c4c(c(-c5ccc(F)cc5C(N)=O)c(C(F)(F)F)cc24)SC[C@@H](OC)C3)C[C@@H]1C]

The title compound was prepared analogously to Example 100, step 21 where 5-fluoro-2-((3S)-3-methoxy-6,8-dioxo-10-(trifluoromethyl)-3,4,7,8-tetrahydro-2H,6H-[1,4]thiazepino[2,3,4-ij]quinazolin-11-yl)benzamide and 1-((2S,6R)-2,6-dimethylpiperazin-1-yl)prop-2-en-1-one were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 10% yield as a yellow solid. m/z (ESI, +ve)=620.2 [M+H]+. $^1$H NMR (400 MHz, DMSO-d$_6$) δ 8.0-7.96 (m, 1H), 7.84-7.76 (m, 1H), 7.72-7.62 (m, 1H), 7.50-7.46 (m, 1H), 7.29-7.23 (m, 2H), 6.82 (dd, J=16.0, 8.0 Hz, 1H), 6.19 (dd, J=16.0, 4.0 Hz, 1H), 5.74 (dd, J=8.0, 4.0 Hz, 1H), 4.74-4.36 (m, 4H), 4.07-4.04 (m, 2H), 3.86-3.82 (m, 1H), 3.32-3.26 (m, 6H), 3.09-3.06 (m, 1H), 1.40 (s, 6H).

Step 1: 5-fluoro-2-((3S)-3-methoxy-6,8-dioxo-10-(trifluoromethyl)-3,4,7,8-tetrahydro-2H,6H-[1,4]thiazepino[2,3,4-ij]quinazolin-11-yl)benzamide

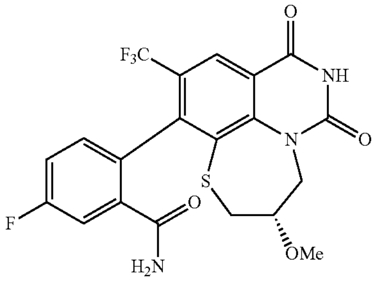 [SMILES: CO[C@@H]1CSc2c(-c3ccc(F)cc3C(N)=O)c(C(F)(F)F)cc3c(=O)[nH]c(=O)n(c23)C1]

An aqueous 0.6M solution of potassium hydroxide (2 mL) was added over a solution of 5-fluoro-2-((3S)-3-methoxy-6,8-dioxo-10-(trifluoromethyl)-3,4,7,8-tetrahydro-2H,6H-[1,4]thiazepino[2,3,4-ij]quinazolin-11-yl)benzonitrile (0.44 mmol) in ethanol (20 mL). The mixture was heated at 80° C. for 16 hours, cooled down to room temperature and the pH adjusted to 3 by addition of a 3M solution of HCl. The resulting mixture was extracted with ethyl acetate three times and the combined organic layers dried over sodium sulfate, filtered and concentrated to afford the title compound as a yellow solid in 43% yield. m/z (ESI, +ve)=492.0 [M+H]+.

Example 1236: (3S)-8-((3S,5R)-4-acryloyl-3,5-dimethylpiperazin-1-yl)-11-(5-chloro-2,4-difluorophenyl)-3-(2-(diethylamino)ethoxy)-10-(trifluoromethyl)-3,4-dihydro-2H,6H-[1,4]thiazepino[2,3,4-ij]quinazolin-6-one

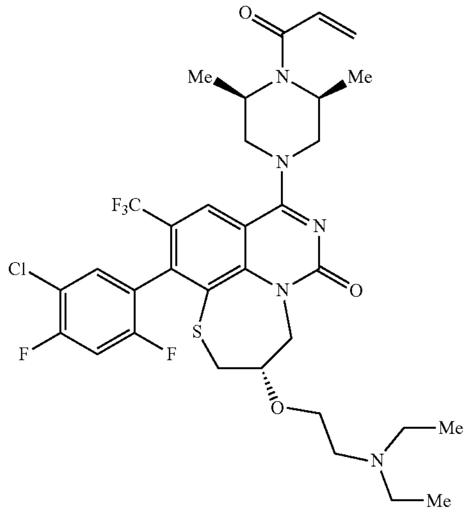 [SMILES: C=CC(=O)N1[C@H](C)CN(c2nc(=O)n3c4c(c(-c5cc(Cl)c(F)cc5F)c(C(F)(F)F)cc24)SC[C@@H](OCCN(CC)CC)C3)C[C@@H]1C]

The title compound was prepared analogously to Example 84 where (3S)-11-(5-chloro-2,4-difluorophenyl)-3-(2-(diethylamino)ethoxy)-8-((3S,5R)-3,5-dimethylpiperazin-1-yl)-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 38% yield as a yellow solid. m/z (ESI, +ve)=714.2 [M+H]+. $^1$H NMR (400 MHz, DMSO-d$_6$) δ=9.08 (s, 1H), 8.07 (s, 1H), 7.82-7.78 (m, 1H), 6.81 (dd, J=16.0, 8.0 Hz, 1H), 6.20 (dd, J=16.0, 4.0 Hz, 1H), 5.75 (dd, J=8.0, 4.0 Hz, 1H), 4.73-4.42 (m, 3H), 4.12-4.05 (m, 3H), 3.85-3.81 (m, 1H), 3.36-3.32 (m, 6H), 3.19-3.15 (m, 4H), 1.40-1.30 (m, 6H), 1.19-1.17 (m, 6H).

Step 1: (S)-2-((1-((tert-butyldimethylsilyl)oxy)-3-(tritylthio)propan-2-yl)oxy)-N,N-diethylacetamide

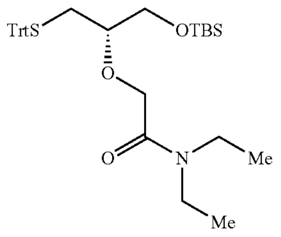

A solution of (S)-1-((tert-butyldimethylsilyl)oxy)-3-(tritylthio)propan-2-ol (24.1 mmol) in THF (30 mL) was added over a suspension of NaH in THF (20 mL) at 0° C. After 30 minutes, a solution of 2-chloro-N,N'-diethylacetamide (28.7 mmol) in DMF (50 mL) was added and the reaction stirred at room temperature for 1 hour. The reaction was quenched with water, extracted with ethyl acetate and washed with brine, dried over sodium sulfate and filtered. Evaporation of volatiles afforded a residue that was purified by silica gel chromatography (ethyl acetate with 0.10% NH4OH) to afford the title compound in 80% yield as a yellow oil. m/z (ESI, +ve)=600.3 [M+H]+.

Step 2: (S)-2-((1-((tert-butyldimethylsilyl)oxy)-3-(tritylthio)propan-2-yl)oxy)-N,N-diethylethane-1-amine

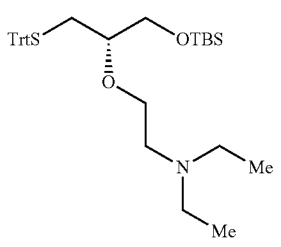

$LiAlH_4$ (26.3 mmol) was added over a 0° C. solution of (S)-2-((1-((tert-butyldimethylsilyl)oxy)-3-(tritylthio)propan-2-yl)oxy)-N,N-diethylacetamide (19 mmol) in THF (80 mL). The mixture was stirred at 60° C. for 1 hour, cooled down to room temperature and quenched with sodium sulfate decahydrate. The solids were filtered and the resulting solution concentrated to afford the title compound as a yellow oil in 84% yield. m/z (ESI, +ve)=564.4 [M+H]+.

Step 3: (S)-2-(2-(diethylamino)ethoxy)-3-mercaptopropan-1-ol

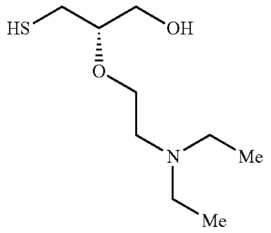 [SMILES: CCN(CC)CCO[C@@H](CO)CS]

Triethylsilane (47.6 mmol) was added over a solution of (S)-2-((1-((tert-butyldimethylsilyl)oxy)-3-(tritylthio)propan-2-yl)oxy)-N,N-diethylethane-1-amine (16 mmol) in dichloromethane:trifluoroacetic acid (60 mL:15 mL). After 20 minutes water was added and the mixture extracted with dichloromethane. Evaporation of volatiles afforded the title compound as a yellow oil in quantitative yield. m/z (ESI, +ve)=208.2 [M+H]+.

Step 4: 7-(5-chloro-2,4-difluorophenyl)-8-(((S)-2-(2-(diethylamino)ethoxy)-3-hydroxypropyl)thio)-6-(trifluoromethyl)quinazoline-2,4(1H,3H)-dione

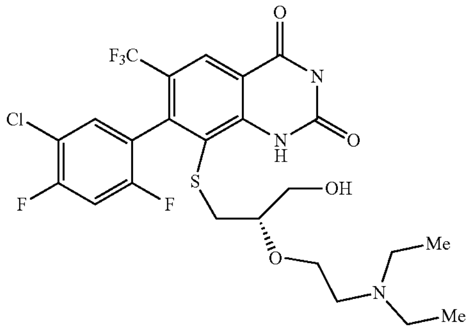 [SMILES: CCN(CC)CCO[C@@H](CO)CSc1c(-c2cc(Cl)c(F)cc2F)c(C(F)(F)F)cc2c(=O)[nH]c(=O)[nH]c12]

The title compound was synthesized analogously to example 100, step 9 where 7-(5-chloro-2,4-difluorophenyl)-8-iodo-6-(trifluoromethyl)quinazoline-2,4(1H,3H)-dione and (S)-2-(2-(diethylamino)ethoxy)-3-mercaptopropan-1-ol were substituted in place of 7-(2,4-difluorophenyl)-8-iodo-6-(trifluoromethyl)quinazoline-2,4(1H,3H)-dione and 2-mercaptoethan-1-ol. The title compound was isolated in 74% yield as a white solid. m/z (ESI, +ve)=582.1 [M+H]+.

Step 5: (3S)-11-(5-chloro-2,4-difluorophenyl)-3-(2-(diethylamino)ethoxy)-10-(trifluoromethyl)-3,4-dihydro-2H,6H-[1,4]thiazepino[2,3,4-ij]quinazoline-6,8(7H)-dione

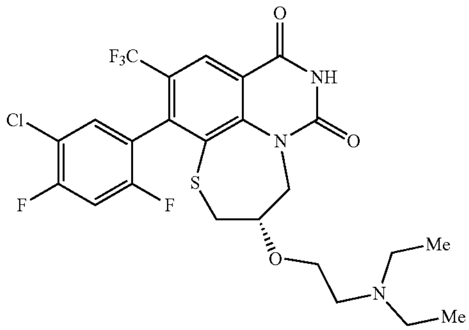 [SMILES: CCN(CC)CCO[C@@H]1CSc2c(-c3cc(Cl)c(F)cc3F)c(C(F)(F)F)cc3c(=O)[nH]c(=O)n(c23)C1]

The title compound was prepared analogously to Example 100, step 10 where 7-(5-chloro-2,4-difluorophenyl)-8-(((S)-2-(2-(diethylamino)ethoxy)-3-hydroxypropyl)thio)-6-(trifluoromethyl)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 97% yield as a yellow solid. m/z (ESI, +ve)=564.0 [M+H]+.

Step 6: tert-butyl (2S,6R)-4-((3S)-11-(5-chloro-2,4-difluorophenyl)-3-(2-(diethylamino)ethoxy)-6-oxo-10-(trifluoromethyl)-3,4-dihydro-2H,6H-[1,4]thiazepino[2,3,4-ij]quinazolin-8-yl)-2,6-dimethylpiperazine-1-carboxylate

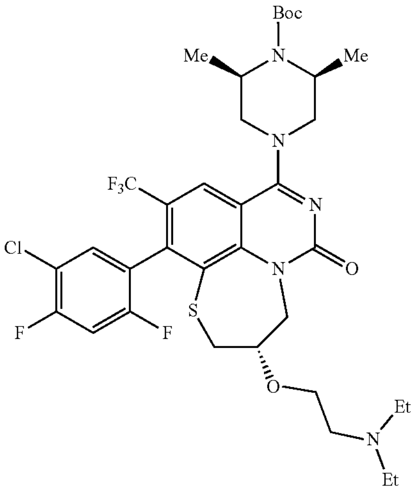 [SMILES: CCN(CC)CCO[C@@H]1CSc2c(-c3cc(Cl)c(F)cc3F)c(C(F)(F)F)cc3c(N4C[C@@H](C)N(C(=O)OC(C)(C)C)[C@@H](C)C4)nc(=O)n(c23)C1]

The title compound was prepared analogously to Example 100, step 21 where (3S)-11-(5-chloro-2,4-difluorophenyl)-3-(2-(diethylamino)ethoxy)-10-(trifluoromethyl)-3,4-dihydro-2H,6H-[1,4]thiazepino[2,3,4-ij]quinazoline-6,8(7H)-dione and tert-butyl (2S,6R)-2,6-dimethylpiperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 50% yield as a yellow solid. m/z (ESI, +ve)=760.2 [M+H]+.

Step 7: (3S)-11-(5-chloro-2,4-difluorophenyl)-3-(2-(diethylamino)ethoxy)-8-((3S,5R)-3,5-dimethylpiperazin-1-yl)-10-(trifluoromethyl)-3,4-dihydro-2H,6H-[1,4]thiazepino[2,3,4-ij]quinazolin-6-one The title compound was prepared analogously to Example 102, step 4, where tert-butyl (2S,6R)-4-((3S)-11-(5-chloro-2,4-difluorophenyl)-3-(2-(diethylamino)ethoxy)-6-oxo-10-(trifluoromethyl)-3,4-dihydro-2H,6H-[1,4]thiazepino[2,3,4-ij]quinazolin-8-yl)-2,6-dimethylpiperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in quantitative yield as a brown oil. m/z (ESI, +ve)=660.2 [M+H]+.

Example 1237: 8'-((3S,5R)-4-acryloyl-3,5-dimethylpiperazin-1-yl)-11'-(5-chloro-2,4-difluorophenyl)-10'-(trifluoromethyl)-2'H,4'H,6'H-spiro[cyclopropane-1,3'-[1,4]thiazepino[2,3,4-ij]quinazolin]-6'-one

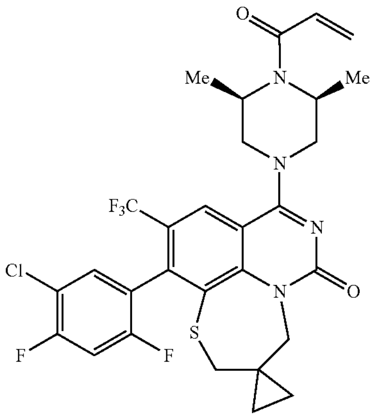 [SMILES: C=CC(=O)N1[C@H](C)CN(c2nc(=O)n3c4c(c(-c5cc(Cl)c(F)cc5F)c(C(F)(F)F)cc24)SCC2(CC2)C3)C[C@@H]1C]

The title compound was prepared analogously to Example 100, step 21 where 11'-(5-chloro-2,4-difluorophenyl)-10'-(trifluoromethyl)-2'H,4'H,6'H-spiro[cyclopropane-1,3'-[1,4]thiazepino[2,3,4-ij]quinazoline]-6',8'(7'H)-dione and 1-((2R,6S)-2,6-dimethylpiperazin-1-yl)prop-2-en-1-one were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 37% yield as a yellow solid. m/z (ESI, +ve)=625.2 [M+H]+. $^1H$ NMR (400 MHz, DMSO) δ 8.06 (s, 1H), 7.80-7.76 (m, 2H), 6.82 (dd, J=16.0, 8.0 Hz, 1H), 6.19 (dd, J=16.0, 4.0 Hz, 1H), 5.75 (dd, J=8.0, 4.0 Hz, 1H), 4.62-4.56 (m, 3H), 4.27-4.23 (m, 1H), 4.20-4.0 (m, 2H), 3.34-3.20 (m, 4H), 1.44-1.37 (m, 6H), 0.90-0.55 (m, 4H).

Step 1: (1-(((tert-butyldiphenylsilyl)oxy)methyl)cyclopropyl)methanol

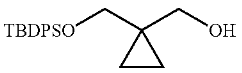

To a mixture of cyclopropane-1,1-diyldimethanol (0.15 mol) and imidazole (0.37 mol) in DMF (150 mL) was added TBDPSCl (0.15 mol) and the reaction mixture was stirred at room temperature for 16 hours. The reaction was quenched by addition of water and the mixture extracted with ethyl acetate, dried over sodium sulfate and filtered. Evaporation of volatiles afforded a residue that was purified by silica gel chromatography (0-5% ethyl acetate in hexanes). The title compound was isolated in 47% yield as a colorless oil. m/z (ESI, +ve)=363.1 $(M+H)^+$.

Step 2: S-((1-(((tert-butyldiphenylsilyl)oxy)methyl) cyclopropyl)methyl) ethanethioate

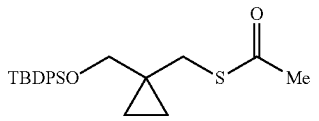

To a 0° C. solution of $PPh_3$ (5.8 mmol) in THF (15 mL) was added DIAD (5.8 mmol) and the mixture was stirred 10 minutes. A solution of (1-(((tert-butyldiphenylsilyl)oxy) methyl)cyclopropyl)methanol (2.9 mmol) and ethanethioic S-acid (5.8 mmol) in THF (10 mL) was added and the reaction stirred at 0° C. for an addition hour. Evaporation of volatiles and purification of the resulting residue by reverse phase chromatography afforded the title compound in 86% yield as a colorless oil. m/z (ESI, +ve)=421.1 $[M+Na]^+$.

Step 3: (1-(((tert-butyldiphenylsilyl)oxy)methyl) cyclopropyl)methanethiol

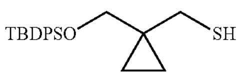

Hydrazine hydrate (19.8 mmol) was added over a solution of S-((1-(((tert-butyldiphenylsilyl)oxy)methyl)cyclopropyl) methyl) ethanethioate (1.25 mmol) in methanol (10 mL). The reaction was stirred at room temperature for one hour and quenched with a mixture of water and ethyl acetate. The organic layer was separated, dried over sodium sulfate, filtered and concentrated to afford a residue that was purified by chromatography in silica gel (hexanes). The title compound was isolated in 85% yield as a colorless oil. m/z (ESI, +ve)=379.2 [M+Na]+.

Step 4: 8-(((1-(((tert-butyldiphenylsilyl)oxy)methyl) cyclopropyl)methyl)thio)-7-(5-chloro-2,4-difluorophenyl)-6-(trifluoromethyl)quinazoline-2,4(1H,3H)-dione

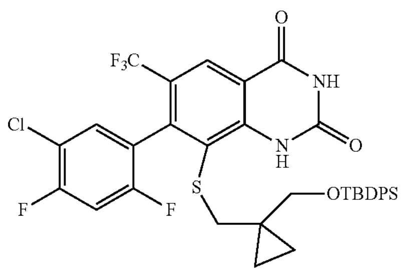

The title compound was synthesized analogously to example 100, step 9 where 7-(5-chloro-2,4-difluorophenyl)-8-iodo-6-(trifluoromethyl)quinazoline-2,4(1H,3H)-dione and (1-(((tert-butyldiphenylsilyl)oxy)methyl)cyclopropyl) methanethiol were substituted in place of 7-(2,4-difluorophenyl)-8-iodo-6-(trifluoromethyl)quinazoline-2,4(1H,3H)-dione and 2-mercaptoethan-1-ol. The title compound was isolated in 68% yield as a white solid. m/z (ESI, +ve)=753.0 [M+H]+.

Step 5: 7-(5-chloro-2,4-difluorophenyl)-8-(((1-(hydroxymethyl)cyclopropyl)methyl)thio)-6-(trifluoromethyl)quinazoline-2,4(1H,3H)-dione

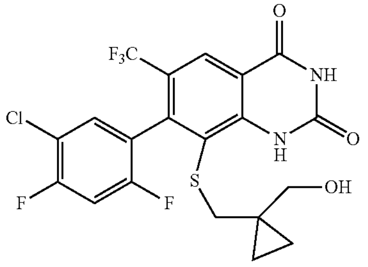 [SMILES: O=c1[nH]c(=O)c2cc(C(F)(F)F)c(-c3cc(Cl)c(F)cc3F)c(SCC3(CO)CC3)c2[nH]1]

TBAF (1.84 mL) was added over a solution of 8-(((1-(((tert-butyldiphenylsilyl)oxy)methyl)cyclopropyl)methyl) thio)-7-(5-chloro-2,4-difluorophenyl)-6-(trifluoromethyl) quinazoline-2,4(1H,3H)-dione (0.61 mmol) in THF (20 mL). After three hours the reaction was concentrated under reduced pressure and the crude material purified by reverse phase chromatography. The title compound was isolated in 93% yield as a white solid. m/z (ESI, +ve)=493.0 [M+H]+.

Step 6: 11'-(5-chloro-2,4-difluorophenyl)-10'-(trifluoromethyl)-2'H,4'H,6'H-spiro[cyclopropane-1,3'-[1,4]thiazepino[2,3,4-ij]quinazoline]-6',8'(7'H)-dione

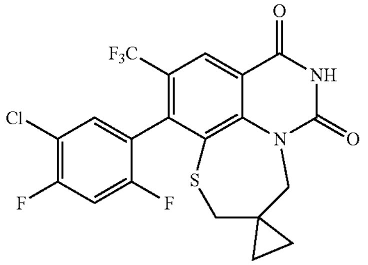 [SMILES: O=c1[nH]c(=O)n2c3c(c(-c4cc(Cl)c(F)cc4F)c(C(F)(F)F)cc13)SCC1(CC1)C2]

The title compound was prepared analogously to Example 100, step 10 where 7-(5-chloro-2,4-difluorophenyl)-8-(((1-(hydroxymethyl)cyclopropyl)methyl)thio)-6-(trifluoromethyl)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 87% yield as a yellow solid. m/z (ESI, +ve)=475.0 [M+H]+.

Example 238: 8'-((3S,5R)-4-acryloyl-3,5-dimethylpiperazin-1-yl)-11'-(5-chloro-2,4-difluorophenyl)-10'-(trifluoromethyl)-2'H,4'H,6'H-spiro[cyclobutane-1,3'-[1,4]thiazepino[2,3,4-ij]quinazolin]-6'-one

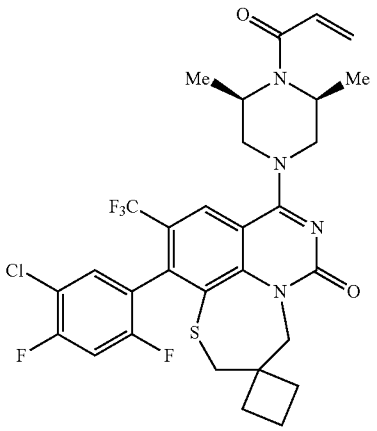 [SMILES: C=CC(=O)N1[C@H](C)CN(c2nc(=O)n3c4c(c(-c5cc(Cl)c(F)cc5F)c(C(F)(F)F)cc24)SCC2(CCC2)C3)C[C@@H]1C]

The title compound was prepared analogously to Example 84 where 11'-(5-chloro-2,4-difluorophenyl)-8'-((3S,5R)-3,5-dimethylpiperazin-1-yl)-10'-(trifluoromethyl)-2'H,4'H,6'H-spiro[cyclobutane-1,3'-[1,4]thiazepino[2,3,4-ij]quinazolin]-6'-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 30% yield as a yellow solid. m/z (ESI, +ve)=639.2 [M+H]+. $^{1}$H NMR (400 MHz, DMSO-d6) δ 8.03 (s, 1H), 7.81-7.66 (m, 2H), 6.82 (dd, J=16.0, 8.0 Hz, 1H), 6.20 (dd, J=16.0, 4.0 Hz, 1H), 5.75 (dd, J=8.0, 4.0 Hz, 1H), 4.08-4.04 (m, 2H), 3.42-3.36 (m, 3H), 3.35-3.31 (m, 2H), 3.28-3.18 (m, 3H), 2.02-1.67 (m, 6H), 1.56-1.05 (m, 6H).

Step 1: Cyclobutane-1,1-diyldimethanol

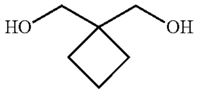

To a solution of cyclobutane-1,1-dicarboxylic acid (0.069 mol) in THF (100 mL) at 0° C. was added $LiAlH_4$ (0.28 mol). The resulting mixture was stirred at room temperature for 4 hours, quenched with $Na_2SO_4 \cdot 10H_2O$ (100 g) and filtered. The filtrate was dried over sodium sulfate and concentrated under reduced pressure to afford the title compound as colorless oil in 51% yield. m/z (ESI, +ve) =139.0 $[M+Na]^+$.

Step 2: (1-(((tert-butyldiphenylsilyl)oxy)methyl)cyclobutyl)methanol

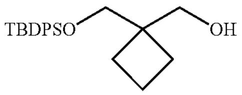

To a mixture of cyclobutane-1,1-diyldimethanol (0.037 mol) and imidazole (0.074 mol) in DMF (60 mL) was added TBDPSCl (0.030 mol). The reaction mixture was stirred at room temperature for 4 hours. The reaction mixture was quenched with water, extracted with ethyl acetate three times and the combined organic layers were washed with water, dried over sodium sulfate and filtered. The filtrate was concentrated under reduced pressure to afford a residue that was purified by silica gel column chromatography (10% ethyl acetate in hexanes) to afford the title compound in 36% yield as colorless oil. m/z (ESI, +ve)=377 $[M+Na]^+$.

Step 3: S-((1-(((tert-butyldiphenylsilyl)oxy)methyl)cyclobutyl)methyl) ethanethioate

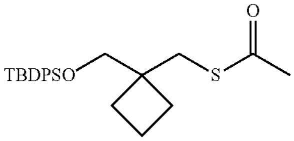

To a 0° C. solution of triphenylphosphine (48 mmol) in THF (100 mL) was added DIAD (60 mmol) and after 20 minutes a solution of (1-(((tert-butyldiphenylsilyl)oxy)methyl)cyclobutyl)methanol (24 mmol) and ethanethioic S-acid (72 mmol) in THF (10 mL) was added. The reaction was stirred for another 40 minutes and quenched with water and extracted with ethyl acetate three times. The combined organic layers were washed with water, dried over $Na_2SO_4$ and filtered. The filtrate was concentrated under reduced pressure to afford a residue that was purified by silica gel column chromatography (10% ethyl acetate in hexanes) to afford the title compound in 59% yield as a colorless oil. m/z (ESI, +ve)=413.0 [M+H]+.

Step 4: (1-(((tert-butyldiphenylsilyl)oxy)methyl)cyclobutyl)methanethiol

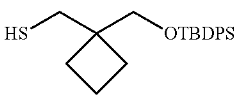

To a 0° C. mixture of S-((1-(((tert-butyldiphenylsilyl)oxy)methyl)cyclobutyl)methyl) ethanethioate (2.4 mmol) in MeOH (20 mL):$H_2O$ (2 mL) was added $K_2CO_3$ (11.9 mmol). After one hour, the reaction mixture was diluted with water (10 mL) and extracted with ethyl acetate three times. The combined organic layers were washed with water, dried over $Na_2SO_4$ and filtered. The filtrate was concentrated under reduced pressure to afford a residue that was purified by silica gel column chromatography (10% ethyl acetate in hexanes) to afford the title compound in 50% yield as colorless oil. m/z (ESI, +ve)=393.1 [M+H]+.

Step 5: 8-(((1-(((tert-butyldiphenylsilyl)oxy)methyl)cyclobutyl)methyl)thio)-7-(5-chloro-2,4-difluorophenyl)-6-(trifluoromethyl)quinazoline-2,4(1H,3H)-dione

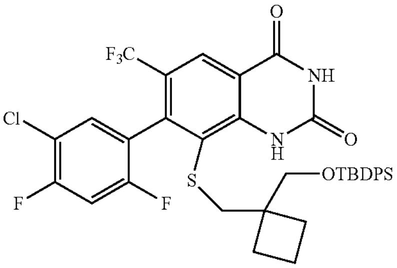

The title compound was synthesized analogously to example 100, step 9 where 7-(5-chloro-2,4-difluorophenyl)-8-iodo-6-(trifluoromethyl)quinazoline-2,4(1H,3H)-dione and (1-(((tert-butyldiphenylsilyl)oxy)methyl)cyclobutyl)methanethiol were substituted in place of 7-(2,4-difluorophenyl)-8-iodo-6-(trifluoromethyl)quinazoline-2,4(1H,3H)-dione and 2-mercaptoethan-1-ol. The title compound was isolated in 72% yield as a yellow solid. m/z (ESI, +ve) =767.1 [M+Na]+.

Step 6: 7-(5-chloro-2,4-difluorophenyl)-8-(((1-(hydroxymethyl)cyclobutyl)methyl)thio)-6-(trifluoromethyl)quinazoline-2,4(1H,3H)-dione

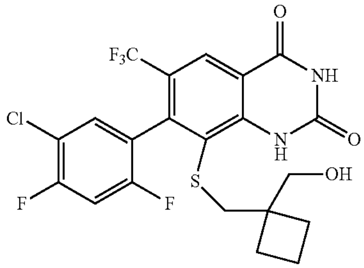 [SMILES: O=c1[nH]c(=O)c2cc(C(F)(F)F)c(-c3cc(Cl)c(F)cc3F)c(SCC3(CO)CCC3)c2[nH]1]

A 1M solution of TBAF in THF (20 mL) was added over a solution of 8-(((1-(((tert-butyldiphenylsilyl)oxy)methyl)cyclopropyl)methyl)thio)-7-(5-chloro-2,4-difluorophenyl)-6-(trifluoromethyl)quinazoline-2,4(1H,3H)-dione (1.60 mmol) in THF (10 mL). After 16 hours the reaction was concentrated under reduced pressure and the crude material purified by reverse phase chromatography. The title compound was isolated in 62% yield as a yellow solid. m/z (ESI, +ve)=507.0 [M+H]+.

Step 7: 11'-(5-chloro-2,4-difluorophenyl)-10'-(trifluoromethyl)-2'H,4'H,6'H-spiro[cyclobutane-1,3'-[1,4]thiazepino[2,3,4-ij]quinazoline]-6',8'(7'H)-dione

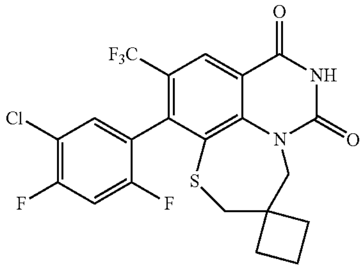 [SMILES: O=c1[nH]c(=O)n2c3c(c(-c4cc(Cl)c(F)cc4F)c(C(F)(F)F)cc13)SCC1(CCC1)C2]

The title compound was prepared analogously to Example 100, step 10 where 7-(5-chloro-2,4-difluorophenyl)-8-(((1-(hydroxymethyl)cyclobutyl)methyl)thio)-6-(trifluoromethyl)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 83% yield as a yellow solid. m/z (ESI, +ve)=489.0 [M+H]+.

Step 8: 11'-(5-chloro-2,4-difluorophenyl)-8'-((3S,5R)-3,5-dimethylpiperazin-1-yl)-10'-(trifluoromethyl)-2'H,4'H,6'H-spiro[cyclobutane-1,3'-[1,4]thiazepino[2,3,4-ij]quinazolin]-6'-one

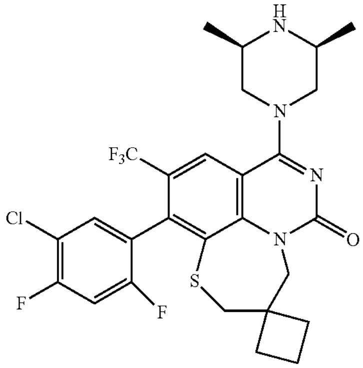 [SMILES: C[C@@H]1CN(c2nc(=O)n3c4c(c(-c5cc(Cl)c(F)cc5F)c(C(F)(F)F)cc24)SCC2(CCC2)C3)C[C@H](C)N1]

The title compound was prepared analogously to Example 100, step 21 where 11'-(5-chloro-2,4-difluorophenyl)-10'-(trifluoromethyl)-2'H,4'H,6'H-spiro[cyclobutane-1,3'-[1,4]thiazepino[2,3,4-ij]quinazoline]-6',8'(7'H)-dione and (2S,6R)-2,6-dimethylpiperazine were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in quantitative yield as a yellow solid. m/z (ESI, +ve)=585.1 [M+H]+.

Example 1239: (3S)-8-((3S,5R)-4-acryloyl-3,5-dimethylpiperazin-1-yl)-11-(5-bromo-2,4-difluorophenyl)-3-methoxy-10-(trifluoromethyl)-3,4-dihydro-2H,6H-[1,4]thiazepino[2,3,4-ij]quinazolin-6-one

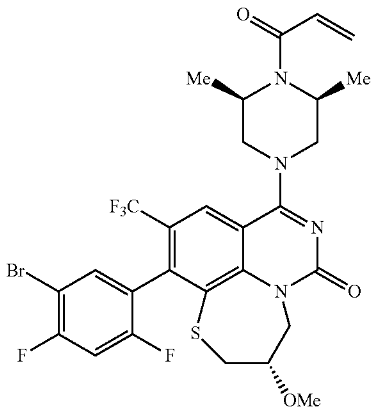 [SMILES: C=CC(=O)N1[C@H](C)CN(c2nc(=O)n3c4c(c(-c5cc(Br)c(F)cc5F)c(C(F)(F)F)cc24)SC[C@@H](OC)C3)C[C@@H]1C]

The title compound was prepared analogously to Example 84 where (3S)-11-(5-bromo-2,4-difluorophenyl)-8-((3S,5R)-3,5-dimethylpiperazin-1-yl)-3-methoxy-10-(trifluoromethyl)-3,4-dihydro-2H,6H-[1,4]thiazepino[2,3,4-ij]quinazolin-6-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 50% yield as a yellow solid. m/z (ESI, +ve)=673.0 [M+H]+. $^1$H NMR (400 MHz, DMSO-$d_6$) δ 8.04-8.03 (m, 1H), 7.85-7.71 (m, 2H), 6.81 (dd, J=16.0, 8.0 Hz, 1H), 6.19 (dd, J=16.0, 4.0 Hz, 1H), 5.74 (dd, J=8.0, 4.0 Hz, 1H), 4.61-4.57 (m, 2H), 4.51-4.48 (m, 1H), 4.08-4.04 (m, 2H), 3.90-3.83 (m, 1H), 3.37-3.35 (m, 2H), 3.32-3.17 (m, 6H), 1.43-1.37 (m, 6H).

Step 1: 2,4-difluoro-5-(4,4,5,5-tetramethyl-1,3,2-dioxaborolan-2-yl)aniline

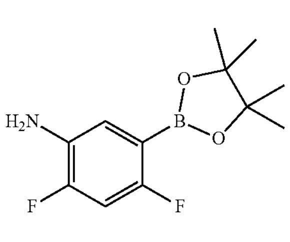 [SMILES: CC1(C)OB(c2cc(N)c(F)cc2F)OC1(C)C]

To a solution of 5-bromo-2,4-difluoroaniline (7.2 mmol) in DMF (30 mL) were added 1,1'-bis(diphenylphosphino)ferrocenepalladiumdichloride (1.4 mmol), bis(pinacolato)diboron (11 mmol) and potassium acetate (21.6 mmol). The reaction mixture was stirred at 85° C. for 2 hours. The mixture was cooled to room temperature and filtered. The filtrate was concentrated to afford a residue that was purified by silica gel chromatography (0-10% ethyl acetate in hexanes) to afford the title compound in 65% yield as a yellow oil. m/z (ESI, +ve)=256.1 [M+H]+.

Step 2: tert-butyl (2S,6R)-4-((3S)-11-(5-amino-2,4-difluorophenyl)-3-methoxy-6-oxo-10-(trifluoromethyl)-3,4-dihydro-2H,6H-[1,4]thiazepino[2,3,4-ij]quinazolin-8-yl)-2,6-dimethylpiperazine-1-carboxylate

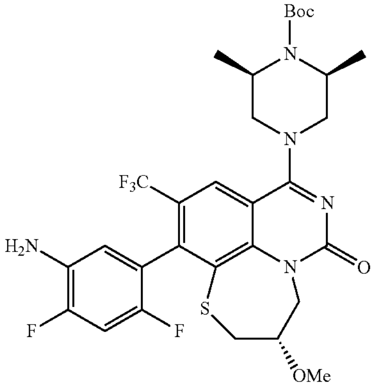 [SMILES: CO[C@@H]1CSc2c(-c3cc(N)c(F)cc3F)c(C(F)(F)F)cc3c(N4C[C@@H](C)N(C(=O)OC(C)(C)C)[C@@H](C)C4)nc(=O)n(c23)C1]

To a mixture of tert-butyl (2S,6R)-4-((S)-11-chloro-3-methoxy-6-oxo-10-(trifluoromethyl)-3,4-dihydro-2H,6H-[1,4]thiazepino[2,3,4-ij]quinazolin-8-yl)-2,6-dimethylpiperazine-1-carboxylate (0.53 mmol), Ruphos-Pd G2 (0.053 mmol) and potassium phosphate (1.6 mmol) in dioxane/$H_2O$ (16 mL/4 mL) was added 2,4-difluoro-5-(4,4,5,5-tetramethyl-1,3,2-dioxaborolan-2-yl)aniline (1.60 mmol). The reaction mixture was stirred at 80° C. for 2 hours, cooled to room temperature and filtered. The filtrate was concentrated to afford a residue that was purified by reverse phase chromatography (5-75% acetonitrile in water with 0.1% TFA) to afford the title compound in 52% yield as a yellow solid. m/z (ESI, +ve)=656.2 [M+H]+.

Step 3: tert-butyl (2S,6R)-4-((3S)-11-(5-bromo-2,4-difluorophenyl)-3-methoxy-6-oxo-10-(trifluoromethyl)-3,4-dihydro-2H,6H-[1,4]thiazepino[2,3,4-ij]quinazolin-8-yl)-2,6-dimethylpiperazine-1-carboxylate

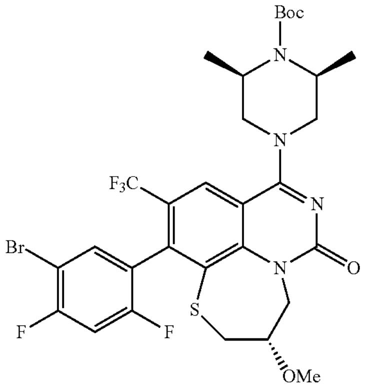 [SMILES: CO[C@@H]1CSc2c(-c3cc(Br)c(F)cc3F)c(C(F)(F)F)cc3c(N4C[C@@H](C)N(C(=O)OC(C)(C)C)[C@@H](C)C4)nc(=O)n(c23)C1]

To a mixture of tert-butyl (2S,6R)-4-((3S)-11-(5-amino-2,4-difluorophenyl)-3-methoxy-6-oxo-10-(trifluoromethyl)-3,4-dihydro-2H,6H-[1,4]thiazepino[2,3,4-ij]quinazolin-8-yl)-2,6-dimethylpiperazine-1-carboxylate (0.30 mmol) in acetonitrile (10 mL) were added tert-butyl nitrite (0.61 mmol) and cupric bromide (0.61 mmol). The mixture was stirred at room temperature for 2 hours and concentrated under reduced pressure. The crude was purified by reverse phase chromatography (5-75% acetonitrile in water with 0.1% TFA) to afford the title compound in 82% yield as a white solid. m/z (ESI, +ve)=720.1 [M+H]+.

Step 4: (3S)-11-(5-bromo-2,4-difluorophenyl)-8-((3S,5R)-3,5-dimethylpiperazin-1-yl)-3-methoxy-10-(trifluoromethyl)-3,4-dihydro-2H,6H-[1,4]thiazepino[2,3,4-ij]quinazolin-6-one

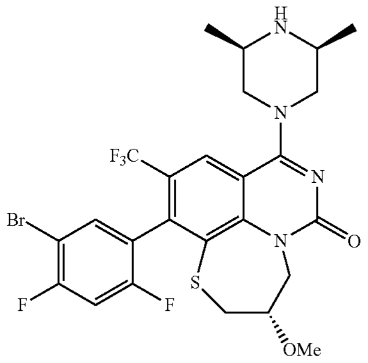 [SMILES: CO[C@@H]1CSc2c(-c3cc(Br)c(F)cc3F)c(C(F)(F)F)cc3c(N4C[C@@H](C)N[C@@H](C)C4)nc(=O)n(c23)C1]

The title compound was prepared analogously to Example 102, step 4, where tert-butyl (2S,6R)-4-((3S)-11-(5-bromo-2,4-difluorophenyl)-3-methoxy-6-oxo-10-(trifluoromethyl)-3,4-dihydro-2H,6H-[1,4]thiazepino[2,3,4-ij]quinazolin-8-yl)-2,6-dimethylpiperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 99% yield as a yellow solid. m/z (ESI, +ve)=620.0 [M+H]+.

Example 1240: (3S)-8-((3S,5R)-4-acryloyl-3,5-dimethylpiperazin-1-yl)-11-(5-chloro-2,4-difluorophenyl)-3-((2,2,2-trifluoroethyl)amino)-10-(trifluoromethyl)-3,4-dihydro-2H,6H-[1,4]thiazepino[2,3,4-ij]quinazolin-6-one

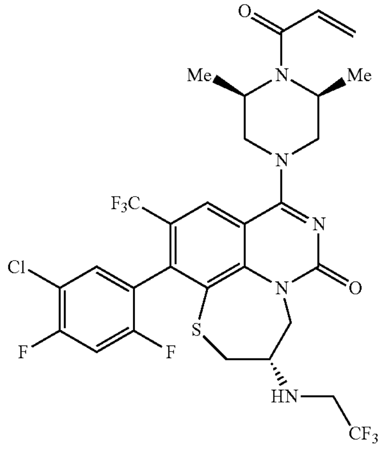 [SMILES: C=CC(=O)N1[C@H](C)CN(c2nc(=O)n3c4c(c(-c5cc(Cl)c(F)cc5F)c(C(F)(F)F)cc24)SC[C@@H](NCC(F)(F)F)C3)C[C@@H]1C]

To a 0° C. solution of (3S)-8-((3S,5R)-4-acryloyl-3,5-dimethylpiperazin-1-yl)-3-amino-11-(5-chloro-2,4-difluorophenyl)-10-(trifluoromethyl)-3,4-dihydro-2H,6H-[1,4]thiazepino[2,3,4-ij]quinazolin-6-one (0.065 mmol) in DMF (1 mL) were added N,N-diisopropylethylamine (0.13 mmol) and 2,2,2-trifluoroethyl trifluoromethanesulfonate (0.13 mmol). The reaction mixture was stirred at room temperature for 16 hours. The solvent was removed under reduced pressure and the resulting crude material was purified by preparative HPLC to afford the title compound as a yellow solid in 7% yield. m/z (ESI, +ve)=696.1 [M+H]+. $^1$H NMR (400 MHz, methanol-d4) δ 8.46 (s, 1H), 8.06 (s, 1H), 7.80-7.75 (m, 1H), 6.81 (dd, J=16.0, 8.0 Hz, 1H), 6.19 (dd, J=16.0, 4.0 Hz, 1H), 5.75 (dd, J=8.0, 4.0 Hz, 1H), 4.75-4.38 (m, 4H), 4.16-3.98 (m, 2H), 3.19-2.93 (m, 7H), 1.51-1.32 (m, 6H).

Step 1: (S)-(2-azido-3-(tritylthio)propoxy)(tert-butyl)diphenylsilane

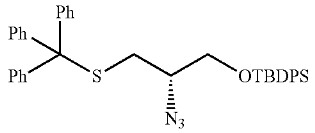

To a 0° C. solution of tert-butyl[(2R)-2-hydroxy-3-[(triphenylmethyl)sulfanyl]propoxy]diphenylsilane (74.7 mmol) and PPh3 (749 mmol) in THF (300 mL) was slowly added DEAD (149 mmol). After 20 minutes, DPPA (97.1 mmol) was added to the solution and stirred at room temperature 16 hours. The solution was quenched with water and concentrated to afford a residue that was purified by silica gel chromatography (0-10% ethyl acetate in hexanes) to afford the title compound in 93% yield as colorless oil.

Step 2: (S)-2-azido-3-((tert-butyldiphenylsilyl)oxy)propane-1-thiol

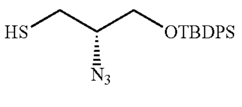

To a solution of [(2S)-2-azido-3-[(triphenylmethyl)sulfanyl]propoxy](tert-butyl)diphenylsilane (48.9 mmol) in dichloromethane/TFA (150 mL/35 mL) was added triethylsilane (147 mmol) and the solution was stirred for 20 minutes. The reaction was diluted with water and extracted with dichloromethane three times. The combined organic layers were washed with brine and dried over sodium sulfate. The organic layer was concentrated to afford a residue that was purified by silica gel chromatography (0-8% methanol in dichloromethane) to afford the title compound in 50% yield as yellow oil.

Step 3: tert-butyl ((2S)-1-((tert-butyldiphenylsilyl)oxy)-3-((7-(5-chloro-2,4-difluorophenyl)-2,4-dioxo-6-(trifluoromethyl)-1,2,3,4-tetrahydroquinazolin-8-yl)thio)propan-2-yl)carbamate

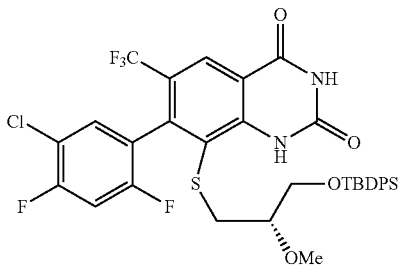

The title compound was synthesized analogously to example 100, step 9 where 7-(5-chloro-2,4-difluorophenyl)-8-iodo-6-(trifluoromethyl)quinazoline-2,4(1H,3H)-dione and (S)-2-azido-3-((tert-butyldiphenylsilyl)oxy)propane-1-thiol were substituted in place of 7-(2,4-difluorophenyl)-8-iodo-6-(trifluoromethyl)quinazoline-2,4(1H,3H)-dione and 2-mercaptoethan-1-ol. The title compound was isolated in 50% yield as a yellow solid. m/z (ESI, +ve)=721.1 [M+H]+.

Step 4: tert-butyl ((2S)-1-((7-(5-chloro-2,4-difluorophenyl)-2,4-dioxo-6-(trifluoromethyl)-1,2,3,4-tetrahydroquinazolin-8-yl)thio)-3-hydroxypropan-2-yl)carbamate

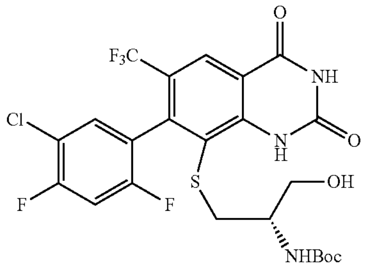 [SMILES: CC(C)(C)OC(=O)N[C@@H](CO)CCSc1c(-c2cc(Cl)c(F)cc2F)c(C(F)(F)F)cc2c(=O)[nH]c(=O)[nH]c12]

To a solution of tert-butyl ((2S)-1-((tert-butyldiphenylsilyl)oxy)-3-((7-(5-chloro-2,4-difluorophenyl)-2,4-dioxo-6-(trifluoromethyl)-1,2,3,4-tetrahydroquinazolin-8-yl)thio)propan-2-yl)carbamate (9.50 mmol) in THF (50 mL) was added 1M solution of TBAF in THF (14.2 mmol). The solution was stirred at room temperature for 30 minutes, concentrated and purified by reversed phase chromatography (40-70% acetonitrile in water with 0.1% TFA) to afford the title compound in 93% yield as a white solid. m/z (ESI, +ve)=526.0 [M+H]+.

Step 5: tert-butyl ((3S)-11-(5-chloro-2,4-difluorophenyl)-6,8-dioxo-10-(trifluoromethyl)-3,4,7,8-tetrahydro-2H,6H-[1,4]thiazepino[2,3,4-ij]quinazolin-3-yl)carbamate

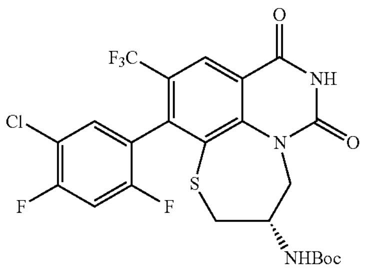 [SMILES: CC(C)(C)OC(=O)N[C@@H]1CCSc2c(-c3cc(Cl)c(F)cc3F)c(C(F)(F)F)cc3c(=O)[nH]c(=O)n(c23)C1]

The title compound was prepared analogously to Example 100, step 10 where tert-butyl ((2S)-1-((7-(5-chloro-2,4-difluorophenyl)-2,4-dioxo-6-(trifluoromethyl)-1,2,3,4-tetrahydroquinazolin-8-yl)thio)-3-hydroxypropan-2-yl)carbamate was substituted in place of 7-(2,4-difluorophenyl)-8-((2-hydroxyethyl)thio)-6-(trifluoromethyl)quinazoline-2,4(1H,3H)-dione in 83% yield as a white solid. $^1$H NMR (400 MHz, DMSO-d6) δ=11.97 (s, 2H), 8.13-8.10 (m, 1H), 7.81-7.64 (m, 2H), 4.25 (m, 2H), 3.20 (m, 2H), 2.94 (m, 1H), 1.40-1.38 (m, 9H).

Step 6: tert-butyl ((3S)-8-((3S,5R)-4-acryloyl-3,5-dimethylpiperazin-1-yl)-11-(5-chloro-2,4-difluorophenyl)-6-oxo-10-(trifluoromethyl)-3,4-dihydro-2H,6H-[1,4]thiazepino[2,3,4-ij]quinazolin-3-yl)carbamate

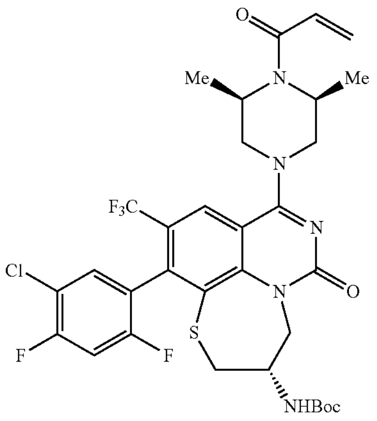 [SMILES: C=CC(=O)N1[C@H](C)CN(c2nc(=O)n3c4c(c(-c5cc(Cl)c(F)cc5F)c(C(F)(F)F)cc24)SCC[C@@H](NC(=O)OC(C)(C)C)C3)C[C@@H]1C]

To a 0° C. solution of tert-butyl ((3S)-11-(5-chloro-2,4-difluorophenyl)-6,8-dioxo-10-(trifluoromethyl)-3,4,7,8-tetrahydro-2H,6H-[1,4]thiazepino[2,3,4-ij]quinazolin-3-yl)carbamate (0.98 mmol) in acetonitrile (10 mL) were added potassium carbonate (13.3 mmol) and tosyl chloride (8.8 mmol). The reaction mixture was stirred at room temperature for 16 hours and 1-((2R,6S)-2,6-dimethylpiperazin-1-yl)prop-2-en-1-one (8.85 mmol) in acetonitrile (10 mL) was added. After 1 hour the suspension was filtered through a pad of celite and the filtrate was concentrated under reduced pressure to afford a residue that was purified by C18 chromatography using 30-70% acetonitrile in water (with 0.05% aq $NH_3$) as eluent. The title compound was isolated in 12% yield as a white solid. m/z (ESI, +ve)=736.1 [M+Na]+.

Step 7: (3S)-8-((3S,5R)-4-acryloyl-3,5-dimethylpiperazin-1-yl)-3-amino-11-(5-chloro-2,4-difluorophenyl)-10-(trifluoromethyl)-3,4-dihydro-2H,6H-[1,4]thiazepino[2,3,4-ij]quinazolin-6-one

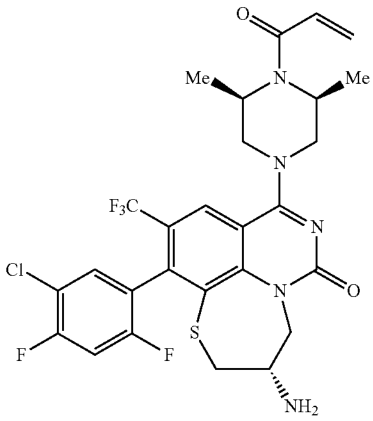 [SMILES: C=CC(=O)N1[C@H](C)CN(c2nc(=O)n3c4c(c(-c5cc(Cl)c(F)cc5F)c(C(F)(F)F)cc24)SCC[C@@H](N)C3)C[C@@H]1C]

To a 0° C. solution of tert-butyl ((3S)-8-((3S,5R)-4-acryloyl-3,5-dimethylpiperazin-1-yl)-11-(5-chloro-2,4-difluorophenyl)-6-oxo-10-(trifluoromethyl)-3,4-dihydro-2H,6H-[1,4]thiazepino[2,3,4-ij]quinazolin-3-yl)carbamate (0.056 mmol) in dichloromethane (1 mL) was added TFA (0.3 mL). The reaction mixture was stirred at room temperature for 2 hours and concentrated under reduced pressure to afford the title compound in 98% yield as a yellow solid. m/z (ESI, +ve)=614.0 [M+H]+.

Example 1241: 8'-((3S,5R)-4-acryloyl-3,5-dimethylpiperazin-1-yl)-11'-(5-chloro-2,4-difluorophenyl)-1-(2,2,2-trifluoroethyl)-10'-(trifluoromethyl)-2'H,4'H,6'H-spiro[azetidine-3,3'-[1,4]thiazepino[2,3,4-ij]quinazolin]-6'-one

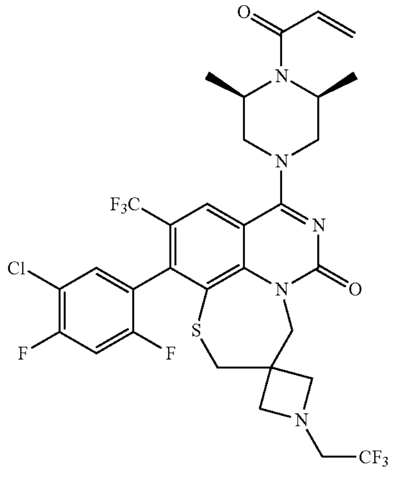 [SMILES: C=CC(=O)N1[C@H](C)CN(c2nc(=O)n3c4c(c(-c5cc(Cl)c(F)cc5F)c(C(F)(F)F)cc24)SCCC2(CN(CC(F)(F)F)C2)C3)C[C@@H]1C]

The title compound was prepared analogously to Example 84 where 11'-(5-chloro-2,4-difluorophenyl)-8'-((3S,5R)-3,5-dimethylpiperazin-1-yl)-1-(2,2,2-trifluoroethyl)-10'-(trifluoromethyl)-2'H,4'H,6'H-spiro[azetidine-3,3'-[1,4]thiazepino[2,3,4-ij]quinazolin]-6'-one was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]quinazolin-5-one. The title compound was isolated in 29% yield as a yellow solid. m/z (ESI, +ve) =722.0 [M+H]+. $^1H$ NMR (400 MHz, DMSO) δ=8.11 (s, 1H), 7.87-7.72 (m, 2H), 6.87 (dd, J=16.0, 8.0 Hz, 1H), 6.25 (dd, J=16.0, 4.0 Hz, 1H), 5.80 (dd, J=8.0, 4.0 Hz, 1H), 4.66-4.62 (m, 2H), 4.17-4.07 (m, 2H), 3.47-3.42 (m, 4H), 3.37-3.19 (m, 8H), 1.60-1.35 (m, 6H).

Step 1: benzyl 2-oxa-6-azaspiro[3.3]heptane-6-carboxylate

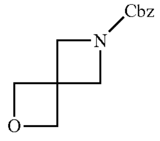 [SMILES: O=C(OCc1ccccc1)N1CC2(COC2)C1]

To a 0° C. mixture of 2-oxa-6-azaspiro[3.3]heptane (0.10 mol) and triethylamine (0.30 mol) in THF (100 mL) was added Cbz-Cl (0.15 mol). The resulting solution was warmed to room temperature and stirred for 16 hours, quenched with water, extracted with ethyl acetate, washed with brine and dried over $Na_2SO_4$ to afford after evaporation of volatiles under reduced pressure a residue that was purified by silica gel column chromatography (0-80% ethyl acetate in hexanes). The title compound was isolated in 52% yield as a colorless oil. m/z (ESI, +ve)=234.1 [M+H]+.

Step 2: benzyl 3-(bromomethyl)-3-(hydroxymethyl)azetidine-1-carboxylate

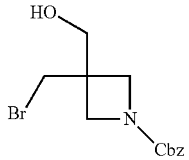 [SMILES: O=C(OCc1ccccc1)N1CC(CO)(CBr)C1]

To a solution of benzyl 2-oxa-6-azaspiro[3.3]heptane-6-carboxylate (0.11 mol) in dichloromethane (150 mL) was added HBr (40% in water, 15 mL). The reaction mixture was stirred for 2 hours and the pH of the mixture was adjusted to 6-7 by the addition of aqueous saturated $NaHCO_3$ (200 mL) and extracted with dichloromethane three times. The combined organic layers were washed with brine, dried over $Na_2SO_4$ and concentrated to afford a residue that was purified by silica gel column chromatography (0-10% methanol in dichloromethane) to afford the title compound in 95% yield as a yellow oil. m/z (ESI, +ve)=314.0 [M+H]+.

Step 3: benzyl 3-(hydroxymethyl)-3-(mercaptomethyl)azetidine-1-carboxylate

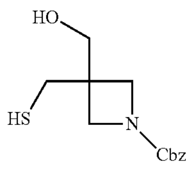 [SMILES: O=C(OCc1ccccc1)N1CC(CO)(CS)C1]

To a mixture of benzyl 3-(bromomethyl)-3-(hydroxymethyl)azetidine-1-carboxylate (0.64 mol) in MeOH (200 mL) was added NaSH (0.32 mol). The reaction mixture was stirred for 16 hours and concentrated under reduced pressure to afford a residue that was purified by silica gel column chromatography (0-10% methanol in dichloromethane) to afford the title compound in 76% yield as a yellow oil. m/z (ESI, +ve)=314.0 [M+H]+.

Step 4: benzyl 3-(((7-(5-chloro-2,4-difluorophenyl)-2,4-dioxo-6-(trifluoromethyl)-1,2,3,4-tetrahydroquinazolin-8-yl)thio)methyl)-3-(hydroxymethyl)azetidine-1-carboxylate

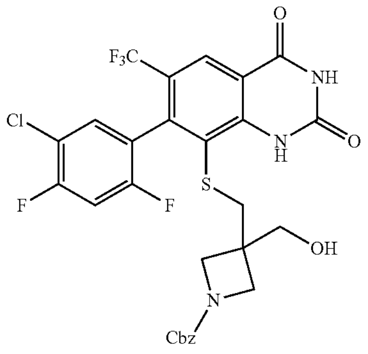 [SMILES: O=C(OCc1ccccc1)N1CC(CO)(CSc2c(-c3cc(Cl)c(F)cc3F)c(C(F)(F)F)cc3c(=O)[nH]c(=O)[nH]c23)C1]

The title compound was synthesized analogously to example 100, step 9 where 7-(5-chloro-2,4-difluorophenyl)-8-iodo-6-(trifluoromethyl)quinazoline-2,4(1H,3H)-dione and benzyl 3-(hydroxymethyl)-3-(mercaptomethyl)azetidine-1-carboxylate were substituted in place of 7-(2,4-difluorophenyl)-8-iodo-6-(trifluoromethyl)quinazoline-2,4(1H,3H)-dione and 2-mercaptoethan-1-ol. The title compound was isolated in 66% yield as a yellow solid. m/z (ESI, +ve)=642.0 [M+H]+.

Step 5: benzyl 11'-(5-chloro-2,4-difluorophenyl)-6',8'-dioxo-10'-(trifluoromethyl)-7',8'-dihydro-2'H,4'H,6'H-spiro[azetidine-3,3'-[1,4]thiazepino[2,3,4-ij]quinazoline]-1-carboxylate

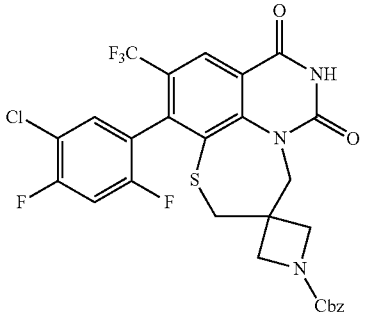 [SMILES: O=C(OCc1ccccc1)N1CC2(CSc3c(-c4cc(Cl)c(F)cc4F)c(C(F)(F)F)cc4c(=O)[nH]c(=O)n(c34)C2)C1]

The title compound was prepared analogously to Example 100, step 10 where benzyl 3-(((7-(5-chloro-2,4-difluorophenyl)-2,4-dioxo-6-(trifluoromethyl)-1,2,3,4-tetrahydroquinazolin-8-yl)thio)methyl)-3-(hydroxymethyl)azetidine-1-carboxylate was substituted in place of 7-(2,4-difluorophenyl)-8-((2-hydroxyethyl)thio)-6-(trifluoromethyl)quinazoline-2,4(1H,3H)-dione in 90% yield as a yellow solid. m/z (ESI, +ve)=624.0 [M+H]+.

Step 6: benzyl 8'-((3S,5R)-4-(tert-butoxycarbonyl)-3,5-dimethylpiperazin-1-yl)-11'-(5-chloro-2,4-difluorophenyl)-6'-oxo-10'-(trifluoromethyl)-2'H,4'H,6'H-spiro[azetidine-3,3'-[1,4]thiazepino[2,3,4-ij]quinazoline]-1-carboxylate

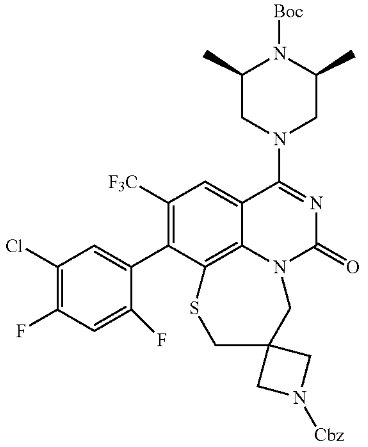 [SMILES: C[C@@H]1CN(c2nc(=O)n3c4c(c(-c5cc(Cl)c(F)cc5F)c(C(F)(F)F)cc24)SCC2(CN(C(=O)OCc4ccccc4)C2)C3)C[C@H](C)N1C(=O)OC(C)(C)C]

The title compound was prepared analogously to Example 100, step 21 where benzyl 11'-(5-chloro-2,4-difluorophenyl)-6',8'-dioxo-10'-(trifluoromethyl)-7',8'-dihydro-2'H,4'H,6'H-spiro[azetidine-3,3'-[1,4]thiazepino[2,3,4-ij]quinazoline]-1-carboxylate and tert-butyl (2S,6R)-2,6-dimethylpiperazine-1-carboxylate were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 49% yield as a yellow solid. m/z (ESI, +ve)=820.0 [M+H]+.

Step 7: tert-butyl (2S,6R)-4-(11'-(5-chloro-2,4-difluorophenyl)-6'-oxo-10'-(trifluoromethyl)-2'H,4'H,6'H-spiro[azetidine-3,3'-[1,4]thiazepino[2,3,4-ij]quinazolin]-8'-yl)-2,6-dimethylpiperazine-1-carboxylate

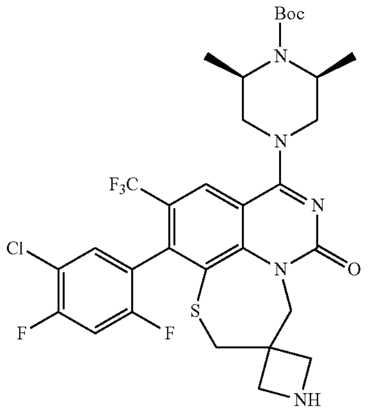 [SMILES: C[C@@H]1CN(c2nc(=O)n3c4c(c(-c5cc(Cl)c(F)cc5F)c(C(F)(F)F)cc24)SCC2(CNC2)C3)C[C@H](C)N1C(=O)OC(C)(C)C]

A mixture of benzyl 8'-((3S,5R)-4-(tert-butoxycarbonyl)-3,5-dimethylpiperazin-1-yl)-11'-(5-chloro-2,4-difluorophenyl)-6'-oxo-10'-(trifluoromethyl)-2'H,4'H,6'H-spiro[azetidine-3,3'-[1,4]thiazepino[2,3,4-ij]quinazoline]-1-carboxylate (0.37 mmol) and 10% Pd on carbon (100 mg) in isopropyl alcohol (5 mL) was hydrogenated for 16 hours. The solids were filtered out and the filtrate was concentrated under reduced pressure to afford a residue that was purified by reversed phase chromatography (30-50% acetonitrile in water with 0.10% TFA) to afford the title compound in 36% yield as a light yellow solid. m/z (ESI, +ve)=686.2 [M+H]+.

Step 8: tert-butyl (2S,6R)-4-(11'-(5-chloro-2,4-difluorophenyl)-6'-oxo-1-(2,2,2-trifluoroethyl)-10'-(trifluoromethyl)-2'H,4'H,6'H-spiro[azetidine-3,3'-[1,4]thiazepino[2,3,4-ij]quinazolin]-8'-yl)-2,6-dimethylpiperazine-1-carboxylate

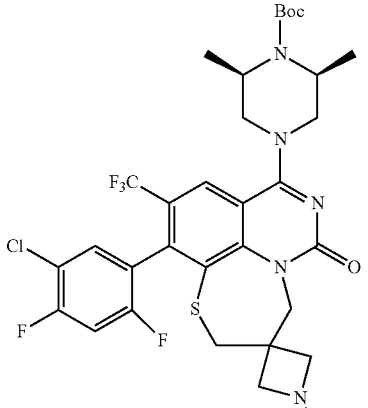

To a mixture of tert-butyl (2S,6R)-4-(11'-(5-chloro-2,4-difluorophenyl)-6'-oxo-10'-(trifluoromethyl)-2'H,4'H,6'H-spiro[azetidine-3,3'-[1,4]thiazepino[2,3,4-ij]quinazolin]-8'-yl)-2,6-dimethylpiperazine-1-carboxylate (0.64 mmol) in DMF (5 mL) were added diisopropylethylamine (1.92 mmol) and 2,2,2-trifluoroethyl trifluoromethanesulfonate (0.64 mmol). The reaction mixture was stirred at room temperature for 2 hours and the volatiles removed under reduced pressure to afford a residue that was purified by reversed phase chromatography (40-80% acetonitrile in water with 0.10% TFA). The title compound was isolated in 53% yield as a light yellow solid. m/z (ESI, +ve)=768.0 [M+H]+.

Step 9: 11'-(5-chloro-2,4-difluorophenyl)-8'-((3S,5R)-3,5-dimethylpiperazin-1-yl)-1-(2,2,2-trifluoroethyl)-10'-(trifluoromethyl)-2'H,4'H,6'H-spiro[azetidine-3,3'-[1,4]thiazepino[2,3,4-ij]quinazolin]-6'-one

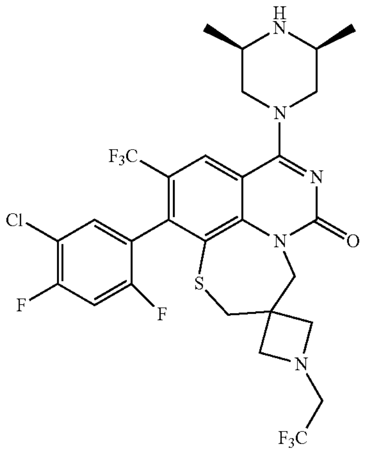 [SMILES: C[C@@H]1CN(c2nc(=O)n3c4c(c(-c5cc(Cl)c(F)cc5F)c(C(F)(F)F)cc24)SCC2(CN(CC(F)(F)F)C2)C3)C[C@H](C)N1]

The title compound was prepared analogously to Example 102, step 4, where tert-butyl (2S,6R)-4-(11'-(5-chloro-2,4-difluorophenyl)-6'-oxo-1-(2,2,2-trifluoroethyl)-10'-(trifluoromethyl)-2'H,4'H,6'H-spiro[azetidine-3,3'-[1,4]thiazepino[2,3,4-ij]quinazolin]-8'-yl)-2,6-dimethylpiperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in 97% yield as a yellow solid. m/z (ESI, +ve)=668.0 [M+H]+.

Example 1242: (3S)-8-((3S,5R)-4-acryloyl-3,5-dimethylpiperazin-1-yl)-11-(6-amino-3,5-difluoropyridin-2-yl)-3-methoxy-10-(trifluoromethyl)-3,4-dihydro-2H,6H-[1,4]thiazepino[2,3,4-ij]quinazolin-6-one

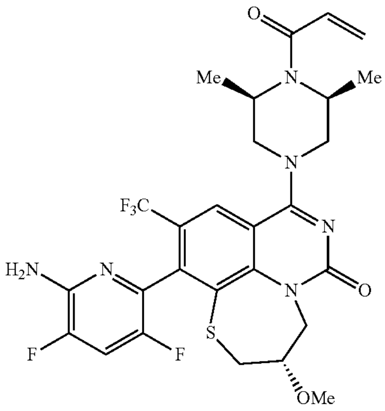 [SMILES: C=CC(=O)N1[C@H](C)CN(c2nc(=O)n3c4c(c(-c5nc(N)c(F)cc5F)c(C(F)(F)F)cc24)SC[C@@H](OC)C3)C[C@@H]1C]

The title compound was prepared analogously to Example 84 where (3S)-11-(6-amino-3,5-difluoropyridin-2-yl)-8-((3S,5R)-3,5-dimethylpiperazin-1-yl)-3-methoxy-10-(trifluoromethyl)-3,4-dihydro-2H,6H-[1,4]thiazepino[2,3,4-ij] quinazolin-6-one was substituted in place of 9-chloro-10-(2,4-difluorophenyl)-7-(3,3-dioxido-3-thia-7,9-diazabicyclo [3.3.1]nonan-7-yl)-2,3-dihydro-5H-[1,4]thiazino[2,3,4-ij] quinazolin-5-one. The title compound was isolated in 33% yield as a white solid. m/z (ESI, +ve)=611.2 [M+H]+. $^1$H NMR (400 MHz, DMSO) δ=8.02 (s, 1H), 7.88-7.67 (m, 1H), 6.81 (dd, J=16.0, 8.0 Hz, 1H), 6.58-6.34 (m, 2H), 6.19 (dd, J=16.0, 4.0 Hz, 1H), 5.74 (dd, J=8.0, 4.0 Hz, 1H), 4.88-4.23 (m, 4H), 4.16-3.96 (m, 2H), 3.92-3.78 (m, 1H), 3.37-3.32 (m, 3H), 3.31-3.01 (m, 4H), 1.39 (s, 6H).

Step 1: 2-(6-amino-3,5-difluoropyridin-2-yl)isoindoline-1,3-dione

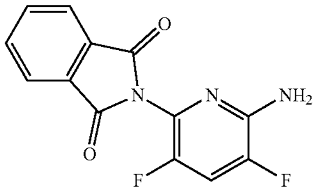 [SMILES: Nc1nc(N2C(=O)c3ccccc3C2=O)c(F)cc1F]

To a solution of 3,5-difluoropyridine-2,6-diamine (0.031 mol) in acetic acid (50 mL) was added isobenzofuran-1,3-dione (0.031 mol). The reaction mixture was stirred at 100° C. for 3 hours and quenched with water. The resulting suspension was filtered through a pad of celite and the filter cake was washed with water. The filtrate was concentrated under reduced pressure to afford the title compound in 82% yield as a light yellow solid. m/z (ESI, +ve)=276.0 [M+H]+.

Step 2: 2-(6-bromo-3,5-difluoropyridin-2-yl)isoindoline-1,3-dione

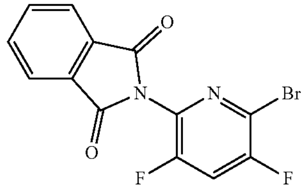 [SMILES: O=C1c2ccccc2C(=O)N1c1nc(Br)c(F)cc1F]

To a 0° C. solution of 2-(6-amino-3,5-difluoropyridin-2-yl)isoindoline-1,3-dione (0.011 mol) in acetonitrile (20 mL) were added $CuBr_2$ (0.0218 mol) and t-BuONO (0.0218 mol). The reaction mixture was stirred at room temperature for 2 hours. The solvent was removed and the residue taken up in water. The mixture was extracted with ehylacetate, washed with brine, dried over sodium sulfate and concentrated to afford a residue that was purified by silica gel chromatography (0-10% ethyl acetate in hexanes) to afford the title compound in 76% yield as a white solid. m/z (ESI, +ve)=341.0 [M+H]+.

Step 3: 6-bromo-3,5-difluoropyridin-2-amine

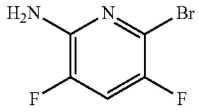

2-(6-bromo-3,5-difluoropyridin-2-yl)isoindoline-1,3-dione (1.47 mmol) was dissolved in a solution of $NH_3$ in MeOH (5 mL) and stirred at room temperature for 1 hour. The solvent was removed to afford a residue that was purified by silica gel chromatograph (0-10% ethyl acetate in hexanes) to afford 6-bromo-3,5-difluoropyridin-2-amine (84%) as a white solid. m/z (ESI, +ve)=211.0 [M+H]+.

Step 4: 6-bromo-3,5-difluoro-N,N-bis(4-methoxybenzyl)pyridin-2-amine

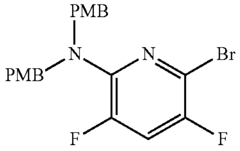

To a 0° C. solution of 6-bromo-3,5-difluoropyridin-2-amine (4.8 mmol) in DMA (10 ml) was added NaH (10.5 mmol). The resulting suspension was stirred for 30 min at 0° C., and then 1-(chloromethyl)-4-methoxybenzene (1.8 g, 0.0115 mol) was added. The reaction was stirred for 1 hour at room temperature and quenched by the addition of saturated aqueous $NH_4Cl$. The mixture was extracted with ethyl acetate, washed with water, dried over sodium sulfate and filtered. The filtrate was concentrated under reduced pressure to afford a residue that was purified by silica gel chromatography (10% ethyl acetate in hexanes) to afford the title compound in 97% yield as a white solid. m/z (ESI, +ve)=449.0 [M+H]+.

Step 5: 3,5-difluoro-N,N-bis(4-methoxybenzyl)-6-(tributylstannyl)pyridin-2-amine

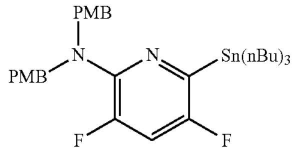

To a mixture of 6-bromo-3,5-difluoro-N,N-bis(4-methoxybenzyl)pyridin-2-amine (4.7 mmol), LiCl (23.5 mmol), $PCy_3$ (0.023.5 mmol) and $Pd_2(dba)_3$ (0.4 mmol) in 1,4-dioxane (20 mL) was added hexabutylditin (7.0 mmol). The resulting mixture was stirred at 80° C. for 3 hours, the solids were filtered out and the filtrate concentrated under reduced pressure to afford a residue that was purified by silica gel chromatography (10% ethyl acetate in hexanes). The title compound was isolated in 87% yield as a yellow oil. m/z (ESI, +ve)=661.2 [M+H]+.

Step 6: tert-butyl (2S,6R)-4-((3S)-11-(6-(bis(4-methoxybenzyl)amino)-3,5-difluoropyridin-2-yl)-3-methoxy-6-oxo-10-(trifluoromethyl)-3,4-dihydro-2H,6H-[1,4]thiazepino[2,3,4-ij]quinazolin-8-yl)-2,6-dimethylpiperazine-1-carboxylate

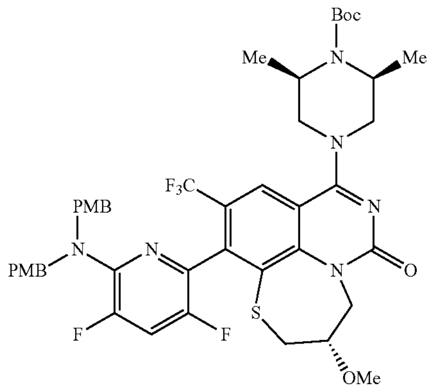

To a mixture of tert-butyl (2S,6R)-4-((S)-11-chloro-3-methoxy-6-oxo-10-(trifluoromethyl)-3,4-dihydro-2H,6H-[1,4]thiazepino[2,3,4-ij]quinazolin-8-yl)-2,6-dimethylpiperazine-1-carboxylate (2.7 mmol) and 3,5-difluoro-N,N-bis(4-methoxybenzyl)-6-(tributylstannyl)pyridin-2-amine (3.2 mmol) in 1,4-dioxane (20 mL) were added CsF (5.9 mol) and bis(tri-tert-butylphosphine)palladium(0) (0.2 mmol). The resulting mixture was stirred at 110° C. for 16 hours, the solid was filtered out and the filtrate was concentrated under reduced pressure to afford a residue that was purified by reversed phase chromatography (85% acetonitrile in water with 0.05% TFA) to afford the title compound in 23% yield as a yellow solid. m/z (ESI, +ve)=897.2 [M+H]+.

Step 7: (3S)-11-(6-amino-3,5-difluoropyridin-2-yl)-8-((3S,5R)-3,5-dimethylpiperazin-1-yl)-3-methoxy-10-(trifluoromethyl)-3,4-dihydro-2H,6H-[1,4]thiazepino[2,3,4-ij]quinazolin-6-one

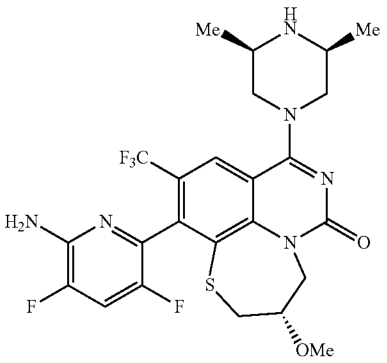 [SMILES: CO[C@@H]1CSc2c(-c3nc(N)c(F)cc3F)c(C(F)(F)F)cc3c(N4C[C@@H](C)N[C@@H](C)C4)nc(=O)n(c23)C1]

The title compound was prepared analogously to Example 102, step 4, where tert-butyl (2S,6R)-4-((3S)-11-(6-(bis(4-methoxybenzyl)amino)-3,5-difluoropyridin-2-yl)-3-methoxy-6-oxo-10-(trifluoromethyl)-3,4-dihydro-2H,6H-[1,4]thiazepino[2,3,4-ij]quinazolin-8-yl)-2,6-dimethylpiperazine-1-carboxylate was substituted in place of tert-butyl (3S)-4-(10-chloro-11-(2,4-difluorophenyl)-6-oxo-3,4-dihydro-2H,6H-[1,4]thiazepino[2,3,4-ij]quinazolin-8-yl)-3-methylpiperazine-1-carboxylate. The title compound was isolated in quantitative yield as a yellow solid. m/z (ESI, +ve)=557.1 [M+H]+.

Example 1243: 8'-((3S,5R)-4-acryloyl-3,5-dimethylpiperazin-1-yl)-11'-(5-chloro-2,4-difluorophenyl)-10'-(trifluoromethyl)-2'H,4'H,6'H-spiro[cyclobutane-1,3'-[1,4]thiazepino[2,3,4-ij]quinazoline]-3,6'-dione

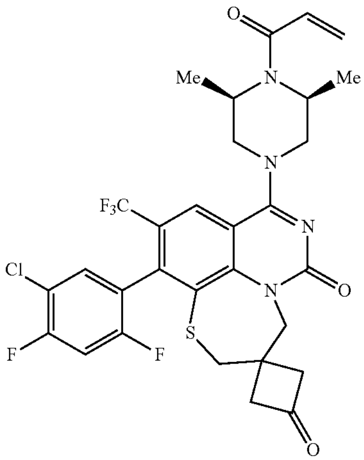 [SMILES: C=CC(=O)N1[C@H](C)CN(c2nc(=O)n3c4c(c(-c5cc(Cl)c(F)cc5F)c(C(F)(F)F)cc24)SCC2(CC(=O)C2)C3)C[C@@H]1C]

The title compound was prepared analogously to Example 84 where 11'-(5-chloro-2,4-difluorophenyl)-8'-((3S,5R)-3,5-dimethylpiperazin-1-yl)-10'-(trifluoromethyl)-2'H,4'H,6'H-spiro[cyclobutane-1,3'-[1,4]thiazepino[2,3,4-ij]quinazoline]-3,6'-dione was substituted in place of 9-chloro-10-(2,4-difluorophenyl)-7-(3,3-dioxido-3-thia-7,9-diazabicyclo[3.3.1]nonan-7-yl)-2,3-dihydro-5H-[1,4]thiazino[2,3,4-ij]

quinazolin-5-one. The title compound was isolated in 24% yield as a yellow solid. m/z (ESI, +ve)=653.1 [M+H]+. $^{1}H$ NMR (400 MHz, DMSO-$d_6$) δ 8.07 (s, 1H), 7.79 (t, J=9.2 Hz, 2H), 6.82 (dd, J=16.0, 8.0 Hz, 1H), 6.19 (dd, J=16.0, 4.0 Hz, 1H), 5.75 (dd, J=16.0, 4.0 Hz, 1H), 4.95-4.44 (m, 5H), 4.16-4.08 (m, 2H), 3.82-3.41 (m, 3H), 3.31-3.19 (m, 2H), 3.09-2.84 (m, 2H), 1.49-1.24 (m, 6H).

Step 1: S-((1-(((tert-butyldiphenylsilyl)oxy)methyl)-3,3-dimethoxycyclobutyl)methyl) ethanethioate

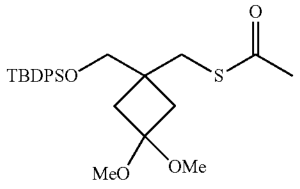

Over a 0° C. solution of $PPh_3$ (0.019 mol) in THF (50 mL) was added DIAD (0.021 mol) and after 20 minutes (1-(((tert-butyldiphenylsilyl)oxy)methyl)-3,3-dimethoxycyclobutyl) methanol (0.010 mol) and ethanethioic S-acid (28.9 mmol) were added. After 1 hour the volatiles were removed under reduced pressure and the resulting residue was purified by reverse phase chromatography (95% acetonitrile in water with 0.1% TFA) to afford the title compound in 90% yield as a colorless oil. m/z (ESI, +ve)=495.1 [M+Na]+.

Step 2: (1-(((tert-butyldiphenylsilyl)oxy)methyl)-3,3-dimethoxycyclobutyl)methanethiol

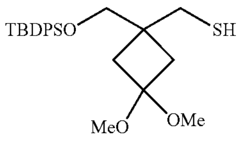

To a mixture of S-((1-(((tert-butyldiphenylsilyl)oxy) methyl)-3,3-dimethoxycyclobutyl)methyl) ethanethioate (5.81 mmol) in THF (10 mL) and MeOH (10 mL) was added hydrazine hydrate (116.10 mmol). The reaction mixture was stirred at room temperature for 1 hour. The reaction mixture was quenched with water and extracted with ethyl acetate three times. The organic layers were combined, washed with water (20 mL), dried over $Na_2SO_4$ and filtered. The filtrate was concentrated under reduced pressure to afford residue which was purified by silica gel chromatograph (PE/EA=8/1) to afford (1-(((tert-butyldiphenylsilyl)oxy)methyl)-3,3-dimethoxycyclobutyl)methanethiol (1.8 g, 64%) as colorless oil. m/z (ESI, +ve)=453.1 [M+Na]$^+$.

Step 3: 8-(((1-(((tert-butyldiphenylsilyl)oxy) methyl)-3,3-dimethoxycyclobutyl)methyl)thio)-7-(5-chloro-2,4-difluorophenyl)-6-(trifluoromethyl)quinazoline-2,4(1H,3H)-dione

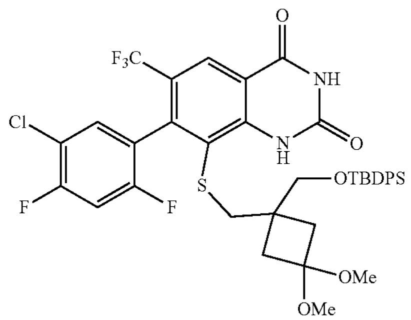

The title compound was synthesized analogously to example 100, step 9 where 7-(5-chloro-2,4-difluorophenyl)-8-iodo-6-(trifluoromethyl)quinazoline-2,4(1H,3H)-dione and (1-(((tert-butyldiphenylsilyl)oxy)methyl)-3,3-dimethoxycyclobutyl)methanethiol were substituted in place of 7-(2,4-difluorophenyl)-8-iodo-6-(trifluoromethyl)quinazoline-2,4(1H,3H)-dione and 2-mercaptoethan-1-ol. The title compound was isolated in 40% yield as a white solid. m/z (ESI, +ve)=827.1 [M+Na]$^+$.

Step 4: 7-(5-chloro-2,4-difluorophenyl)-8-(((1-(hydroxymethyl)-3,3-dimethoxycyclobutyl)methyl) thio)-6-(trifluoromethyl)quinazoline-2,4(1H,3H)-dione

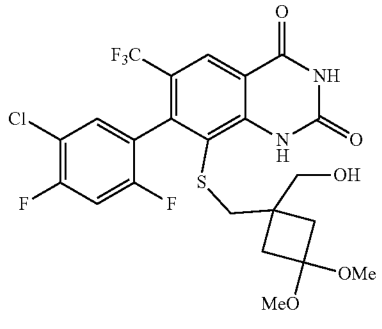 [SMILES: COC1(OC)CC(CO)(CSc2c(-c3cc(Cl)c(F)cc3F)c(C(F)(F)F)cc3c(=O)[nH]c(=O)[nH]c23)C1]

To a solution of 8-(((1-(((tert-butyldiphenylsilyl)oxy) methyl)-3,3-dimethoxycyclobutyl)methyl)thio)-7-(5-chloro-2,4-difluorophenyl)-6-(trifluoromethyl)quinazoline-2,4(1H,3H)-dione (1.4 mmol) in THF (15 mL) was added TBAF (2.8 mmol) and the reaction was stirred at room temperature for 16 hours. The mixture was concentrated under reduced pressure to afford a residue that was purified by reversed phase chromatography (65% acetonitrile in water with 0.1% TFA) to afford the title compound in 92% yield as a colorless oil. m/z (ESI, +ve)=567.1 [M+H]+.

Step 5: 11'-(5-chloro-2,4-difluorophenyl)-3,3-dimethoxy-10'-(trifluoromethyl)-2'H,4'H,6'H-spiro[cyclobutane-1,3'-[1,4]thiazepino[2,3,4-ij]quinazoline]-6',8'(7'H)-dione

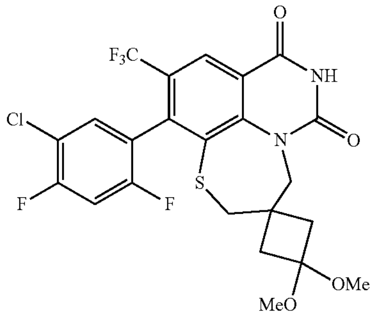 [SMILES: COC1(OC)CC2(CSc3c(-c4cc(Cl)c(F)cc4F)c(C(F)(F)F)cc4c(=O)[nH]c(=O)n(c34)C2)C1]

The title compound was prepared analogously to Example 100, step 10 where 7-(5-chloro-2,4-difluorophenyl)-8-(((1-(hydroxymethyl)-3,3-dimethoxycyclobutyl)methyl)thio)-6-(trifluoromethyl)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione in 30% yield as a colorless oil. m/z (ESI, +ve)=549.1 [M+H]+.

Step 6: 11'-(5-chloro-2,4-difluorophenyl)-10'-(trifluoromethyl)-2'H,4'H,6'H-spiro[cyclobutane-1,3'-[1,4]thiazepino[2,3,4-ij]quinazoline]-3,6',8'(7'H)-trione

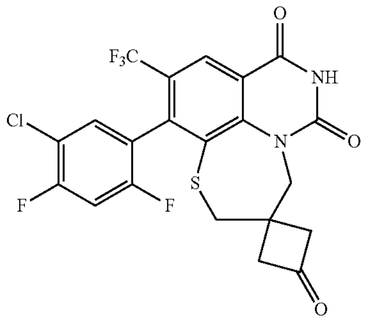 [SMILES: O=C1CC2(CSc3c(-c4cc(Cl)c(F)cc4F)c(C(F)(F)F)cc4c(=O)[nH]c(=O)n(c34)C2)C1]

To a mixture of 11'-(5-chloro-2,4-difluorophenyl)-3,3-dimethoxy-10'-(trifluoromethyl)-2'H,4'H,6'H-spiro[cyclobutane-1,3'-[1,4]thiazepino[2,3,4-ij]quinazoline]-6',8'(7'H)-dione (0.382 mmol) in acetonitrile (5 mL) was added TFA (1 mL). The reaction mixture was stirred at room temperature for 1 hour. And after that time the volatiles were removed under reduced pressure to afford the title compound in 75% yield as an off-white solid. m/z (ESI, +ve)=502.9 [M+H]+.

Step 7: 11'-(5-chloro-2,4-difluorophenyl)-8'-((3S,5R)-3,5-dimethylpiperazin-1-yl)-10'-(trifluoromethyl)-2'H,4'H,6'H-spiro[cyclobutane-1,3'-[1,4]thiazepino[2,3,4-ij]quinazoline]-3,6'-dione

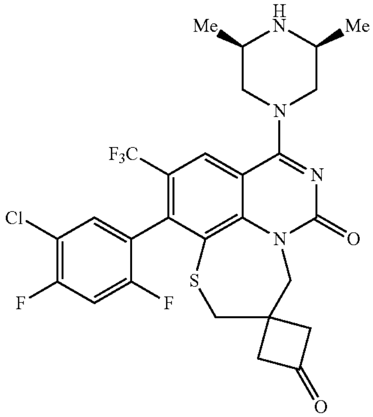 [SMILES: C[C@@H]1CN(c2nc(=O)n3c4c(c(-c5cc(Cl)c(F)cc5F)c(C(F)(F)F)cc24)SCC2(CC(=O)C2)C3)C[C@H](C)N1]

The title compound was prepared analogously to Example 100, step 21 where 11'-(5-chloro-2,4-difluorophenyl)-10'-(trifluoromethyl)-2'H,4'H,6'H-spiro[cyclobutane-1,3'-[1,4]thiazepino[2,3,4-ij]quinazoline]-3,6',8'(7'H)-trione and (2S,6R)-2,6-dimethylpiperazine were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 25% yield as a brown solid. m/z (ESI, +ve)=599.1 [M+H]+.

Example 1301: (3S)-3-((1S,4S)-2-oxa-5-azabicyclo[2.2.1]heptan-5-ylmethyl)-7-((3S,5R)-4-acryloyl-3,5-dimethylpiperazin-1-yl)-10-(2,4-difluorophenyl)-9-(trifluoromethyl)-2H-[1,4]thiazino[2,3,4-ij]quinazolin-5(3H)-one

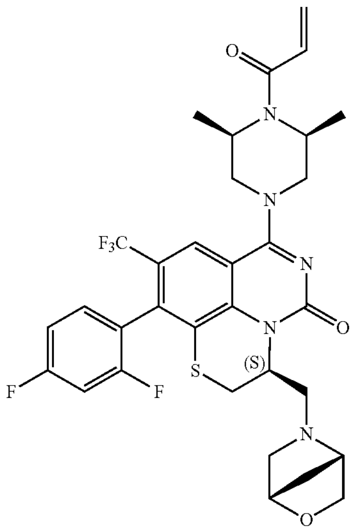

The title compound was prepared according to the scheme below.

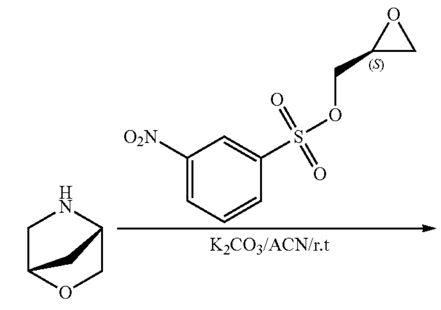
1
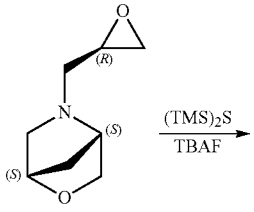
2
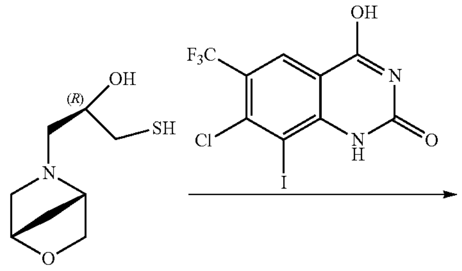
3
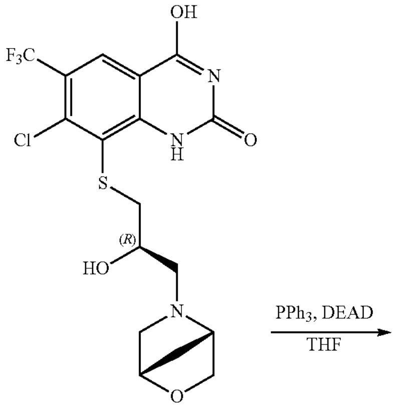
4
-continued
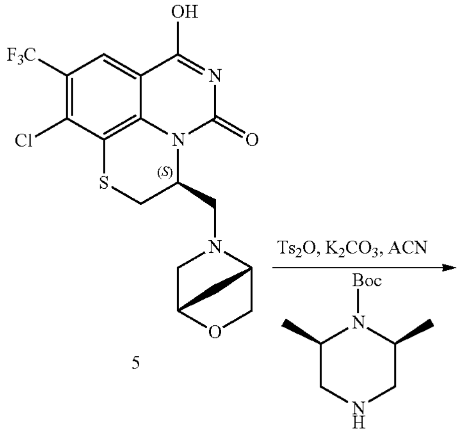
5
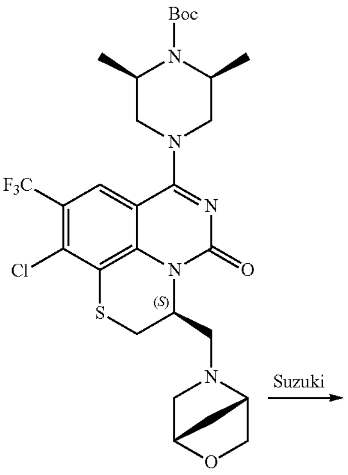
6
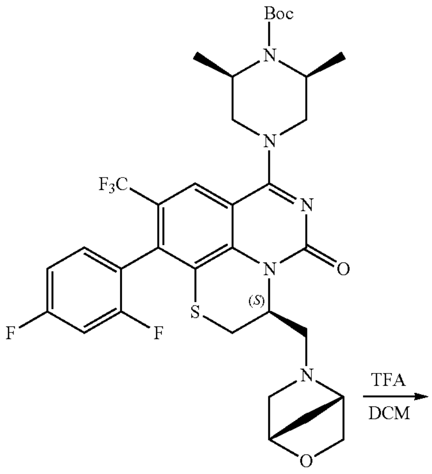
7

-continued

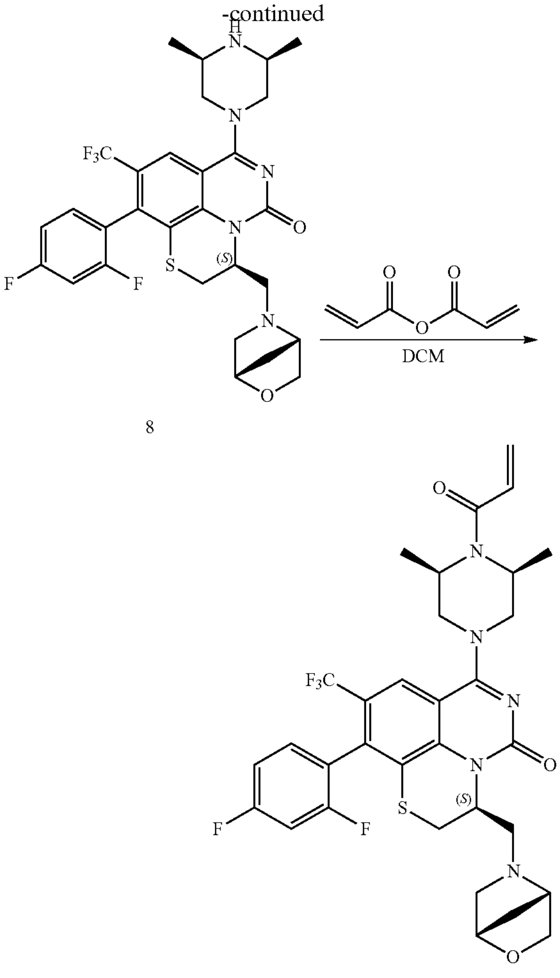

8

9

Step 1: (1S,4S)-5-((R)-oxiran-2-ylmethyl)-2-oxa-5-azabicyclo[2.2.1]heptanes

The solution of (S)-oxiran-2-ylmethyl 3-nitrobenzenesulfonate (38.2 g, 147.5 mmol) in acetonitrile (300 mL) was added (1S,4S)-2-oxa-5-azabicyclo[2.2.1]heptane (1) (20.0 g, 147.5 mmol) and potassium carbonate (61 g, 442.5 mmol) at 0° C. under nitrogen atmosphere. The mixture was stirred under nitrogen atmosphere at room temperature for 16 hours. After completion, the mixture was concentrated and the residue was purified by silica gel column with dichloromethane/methanol=20/1 to afford the product (2) (15.0 g, yield: 66%) as a yellow oil. MS (ESI) m/z 156.1 $[M+H]^+$.

Step 2: (R)-1-((1S,4S)-2-oxa-5-azabicyclo[2.2.1]heptan-5-yl)-3-mercaptopropan-2-ol (3)

To a mixture of (1S,4S)-5-((R)-oxiran-2-ylmethyl)-2-oxa-5-azabicyclo[2.2.1]heptane (2) (6 g, 38.7 mmol) in tetrahydrofuran (60 mL) were added 1,1,1,3,3,3-hexamethyldisilathiane (8.9 g, 50.3 mmol) and tetrabutylammonium fluoride (1.0 M in tetrahydrofuran, 11.6 mL, 11.6 mmol) at 0° C. The mixture was stirred at room temperature for 2 hours. After completion, the mixture was poured into water (60 mL), extracted with ethyl acetate (3×100 mL). The organic phase was washed with brine (200 mL) and dried over anhydrous sodium sulfate. After filtration and concentration, the residue was purified by silica gel column with dichloromethane/methanol=50/1 to afford (R)-1-((1S,4S)-2-oxa-5-azabicyclo[2.2.1]heptan-5-yl)-3-mercaptopropan-2-ol (3) (2.6 g, yield: 35%) as a colorless oil. MS (ESI) m/z 190.1 [M+H]+.

Step 3: 8-(((R)-3-((1S,4S)-2-oxa-5-azabicyclo[2.2.1]heptan-5-yl)-2-hydroxypropyl)thio)-7-chloro-4-hydroxy-6-(trifluoromethyl)quinazolin-2(1H)-one (4)

To a solution of 7-chloro-4-hydroxy-8-iodo-6-(trifluoromethyl)quinazolin-2(1H)-one (4.00 g, 9.10 mmol) in dioxane (100 mL) were added potassium carbonate (3.70 g, 27.3 mmol), (R)-1-((1S,4S)-2-oxa-5-azabicyclo[2.2.1]heptan-5-yl)-3-mercaptopropan-2-ol (3) (2.57 g, 13.6 mmol), 4,5-bis(diphenyl-phosphino)-9,9-dimethylxanthene (1.05 g, 1.82 mmol) and tris(dibenzylideneacetone) dipalladium (0.823 g, 0.91 mmol). The mixture was stirred at 55° C. under nitrogen atmosphere for 8 hours. After completion, the mixture was diluted with tetrahydrofuran (200 mL) and insoluble was filtered out. The filtrate was concentrated and the residue was purified by silica gel column chromatography (dichloromethane/methanol=100/1 to 20/1) to afford 8-(((R)-3-((1S,4S)-2-oxa-5-azabicyclo[2.2.1]heptan-5-yl)-2-hydroxypropyl)thio)-7-chloro-4-hydroxy-6-(trifluoromethyl)quinazolin-2(1H)-one (4) (4.00 g, yield: 97%) as a yellow solid. MS (ESI) m/z 452.5 $[M+H]^+$.

Step 4: (S)-3-((1S,4S)-2-oxa-5-azabicyclo[2.2.1]heptan-5-ylmethyl)-10-chloro-7-hydroxy-9-(trifluoromethyl)-2H-[1,4]thiazino[2,3,4-ij]quinazolin-5(3H)-one (5)

To a mixture of 8-(((R)-3-((1S,4S)-2-oxa-5-azabicyclo[2.2.1]heptan-5-yl)-2-hydroxypropyl)thio)-7-chloro-4-hydroxy-6-(trifluoromethyl)quinazolin-2(1H)-one (4) (3.50 g, 7.70 mmol) and triphenylphosphine (3.00 g, 11.6 mmol) in tetrahydrofuran (50 mL) was added diethyl azodicarboxylate (2.60 g, 15.4 mmol) at 0° C. The mixture was stirred at 0° C. for 45 min. After completion, the mixture was poured into ice-water (200 mL) and extracted with ethyl acetate (3×200 mL). Concentrated and the residue was purified by flash chromatography column (C18, acetonitrile/water=30% to 95%) to afford (S)-3-((1S,4S)-2-oxa-5-azabicyclo[2.2.1]heptan-5-ylmethyl)-10-chloro-7-hydroxy-9-(trifluoromethyl)-2H-[1,4]thiazino[2,3,4-ij]quinazolin-5(3H)-one (5) (3.14 g, yield: 70%) as a white solid. MS (ESI) m/z 434.4 $[M+H]^+$ Step 5: (2S,6R)-tert-butyl 4-((S)-3-((1S,4S)-2-oxa-5-azabicyclo[2.2.1]heptan-5-ylmethyl)-10-chloro-5-oxo-9-(trifluoromethyl)-3,5-dihydro-2H-[1,4]thiazino[2,3,4-ij]quinazolin-7-yl)-2,6-dimethylpiperazine-1-carboxylate (6)

To a mixture of (S)-3-((1S,4S)-2-oxa-5-azabicyclo[2.2.1]heptan-5-ylmethyl)-10-chloro-7-hydroxy-9-(trifluoromethyl)-2H-[1,4]thiazino[2,3,4-ij]quinazolin-5(3H)-one (5) (700 mg, 1.60 mmol) and potassium carbonate (2.20 g, 16.0 mmol) in acetonitrile (20 mL) was added 4-methylbenzenesulfonic anhydride (782 mg, 2.40 mmol) at 25° C. The mixture was stirred at 25° C. for 3 hours. (2R,6S)-tert-butyl 2,6-dimethylpiperazine-1-carboxylate (684 mg, 3.20 mmol) was added into the reaction solution. The reaction mixture was stirred at 25° C. for 1 hour. After completion, the mixture was poured into ice-water (50 mL) and extracted with ethyl acetate (3×50 mL). The mixture was concentrated and the residue was purified by flash chromatography column (C18, acetonitrile/water=20% to 95%) to afford (2S,6R)-tert-butyl 4-((S)-3-((1S,4S)-2-oxa-5-azabicyclo[2.2.1]heptan-5-ylmethyl)-10-chloro-5-oxo-9-(trifluoromethyl)-3,5-dihydro-2H-[1,4]thiazino[2,3,4-ij]quinazolin-7-yl)-2,6-dimethylpiperazine-1-carboxylate (6) (800 mg, yield: 80%) as a yellow solid. MS (ESI) m/z 630.6 $[M+H]^+$.

Step 6: (2S,6R)-tert-butyl 4-((3S)-3-((1S,4S)-2-oxa-5-azabicyclo[2.2.1]heptan-5-ylmethyl)-10-(2,4-difluorophenyl)-5-oxo-9-(trifluoromethyl)-3,5-dihydro-2H-[1,4]thiazino[2,3,4-ij]quinazolin-7-yl)-2,6-dimethylpiperazine-1-carboxylate (7)

To a solution of (2S,6R)-tert-butyl 4-((S)-3-((1S,4S)-2-oxa-5-azabicyclo[2.2.1]heptan-5-ylmethyl)-10-chloro-5-oxo-9-(trifluoromethyl)-3,5-dihydro-2H-[1,4]thiazino[2,3,4-ij]quinazolin-7-yl)-2,6-dimethylpiperazine-1-carboxylate (6) (300 mg, 0.476 mmol) in 1,4-dioxane (10 mL) and water (2 mL) were added tripotassium phosphate (404 mg, 1.90 mmol), (2,4-difluorophenyl)boronic acid (602 mg, 3.81 mmol), and chloro(2-dicyclohexylphosphino-2', 6'-diisopropoxy-1,1'-biphenyl)[2-(2'-amino-1,1'-biphenyl)]palladium(II) (74 mg, 0.095 mmol). The mixture was stirred at 85° C. under nitrogen atmosphere for 4 hours. After completion, the mixture was diluted with tetrahydrofuran (50 mL) and insoluble was filtered out. The filtrate was concentrated and the residue was purified by silica gel column chromatography (dichloromethane/methanol=100/1 to 30/1) to afford (2S,6R)-tert-butyl 4-((3S)-3-((1S,4S)-2-oxa-5-azabicyclo[2.2.1]heptan-5-ylmethyl)-10-(2,4-difluorophenyl)-5-oxo-9-(trifluoromethyl)-3,5-dihydro-2H-[1,4]thiazino[2,3,4-ij]quinazolin-7-yl)-2,6-dimethylpiperazine-1-carboxylate (7) (252 mg, yield: 75%) as a yellow solid. MS (ESI) m/z 708.4 $[M+H]^+$.

Step 7: (3S)-3-((1S,4S)-2-oxa-5-azabicyclo[2.2.1]heptan-5-ylmethyl)-10-(2,4-difluorophenyl)-7-((3S,5R)-3,5-dimethylpiperazin-1-yl)-9-(trifluoromethyl)-2H-[1,4]thiazino[2,3,4-ij]quinazolin-5(3H)-one (8)

To a cooled mixture of (2S,6R)-tert-butyl 4-((3S)-3-((1S,4S)-2-oxa-5-azabicyclo[2.2.1]heptan-5-ylmethyl)-10-(2,4-difluorophenyl)-5-oxo-9-(trifluoromethyl)-3,5-dihydro-2H-[1,4]thiazino[2,3,4-ij]quinazolin-7-yl)-2,6-dimethylpiperazine-1-carboxylate (7) (252 mg, 0.36 mmol) in dichloromethane (5 mL) was added trifluoroacetic acid (1 mL) at 0° C. The reaction solution was stirred at room temperature for 1 hour. After completion, the mixture was concentrated. The residue was redissolved in dichloromethane and washed with saturated $NaHCO_3$. The organic layer was dried over $Na_2SO_4$ and concentrated. The residue was purified by silica gel column chromatography (dichloromethane/methanol=15:1) to afford (3S)-3-((1S,4S)-2-oxa-5-azabicyclo[2.2.1]heptan-5-ylmethyl)-10-(2,4-difluorophenyl)-7-((3S,5R)-3,5-dimethylpiperazin-1-yl)-9-(trifluoromethyl)-2H-[1,4]thiazino[2,3,4-ij]quinazolin-5(3H)-one (8) (185 mg, yield: 85%) as a yellow solid. MS (ESI) m/z 608.1 [M+H]+.

Step 8: (3S)-3-((1S,4S)-2-oxa-5-azabicyclo[2.2.1]heptan-5-ylmethyl)-7-((3S,5R)-4-acryloyl-3,5-dimethylpiperazin-1-yl)-10-(2,4-difluorophenyl)-9-(trifluoromethyl)-2H-[1,4]thiazino[2,3,4-ij]quinazolin-5(3H)-one (9)

To a mixture of (3S)-3-((1S,4S)-2-oxa-5-azabicyclo[2.2.1]heptan-5-ylmethyl)-10-(2,4-difluorophenyl)-7-((3S,5R)-3,5-dimethylpiperazin-1-yl)-9-(trifluoromethyl)-2H-[1,4]thiazino[2,3,4-ij]quinazolin-5(3H)-one (8) (160 mg, 0.26 mmol) and triethyl amine (40 mg, 0.39 mmol) in dichloromethane (5 mL) was added acrylic anhydride (40 mg, 0.31 mmol) at 0° C. The mixture was stirred at 0° C. for 1 hour. After completion, the mixture was poured into ice-water (50 mL) and extracted with ethyl acetate (3×20 mL). The mixture was concentrated and the residue was purified by preparative high performance liquid chromatography (20% to 95% acetonitrile in water) to afford (3S)-3-((1S,4S)-2-oxa-5-azabicyclo[2.2.1]heptan-5-ylmethyl)-7-((3S,5R)-4-acryloyl-3,5-dimethylpiperazin-1-yl)-10-(2,4-difluorophenyl)-9-(trifluoromethyl)-2H-[1,4]thiazino[2,3,4-ij]quinazolin-5(3H)-one (9) (103 mg, yield: 59%) as a white solid. MS (ESI) m/z 662.1 $[M+H]^+$. $^1H$ NMR (400 MHz, $CDCl_3$) δ 8.07 (s, 1H), 7.21-7.14 (m, 1H), 7.06-6.93 (m, 2H), 6.66-6.59 (m, 1H), 6.43-6.38 (m, 1H), 5.77 (d, J=12.0 Hz, 1H), 5.28-5.24 (m, 1H), 4.74-4.60 (m, 2H), 4.43-4.37 (m, 1H), 4.19 (d, J=13.6 Hz, 2H), 3.91-3.84 (m, 1H), 3.69-3.31 (m, 5.5H), 2.99-2.85 (m, 4.5H), 1.75-1.66 (m, 2H), 1.60-1.58 (m, 3H), 1.49-1.41 (m, 3H).

Example 1309: 8'-(4-acryloylpiperazin-1-yl-2,2,3,3,5,5,6,6-$d_8$)-11'-(5-chloro-2,4-difluorophenyl)-10'-(trifluoromethyl)-2'H,4'H,6'H-spiro[oxetane-3,3'-[1,4]thiazepino[2,3,4-ij]quinazolin]-6'-one

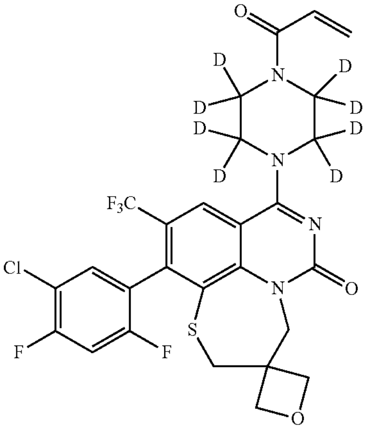 [SMILES: [2H]C1([2H])N(C(=O)C=C)C([2H])([2H])C([2H])([2H])N(c2nc(=O)n3c4c(c(-c5cc(Cl)c(F)cc5F)c(C(F)(F)F)cc24)SCC2(COC2)C3)C1([2H])[2H]]

The title compound was prepared according to the scheme below.

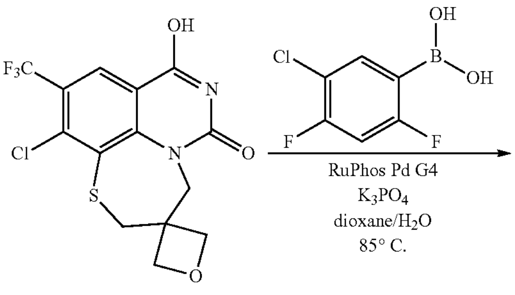

1

-continued

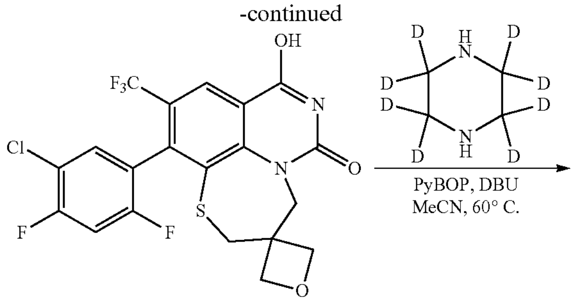

2

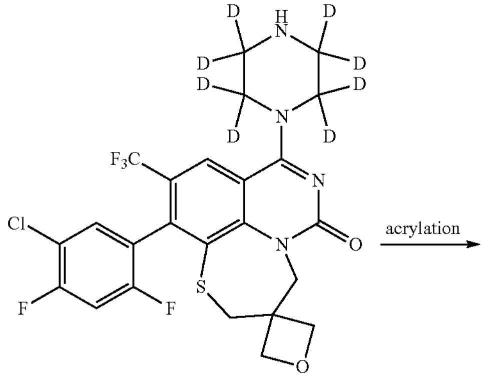

3

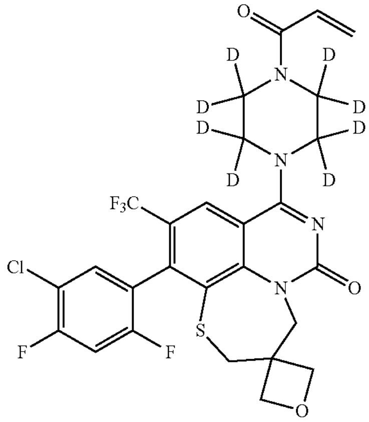

4

Step 1: 11'-(5-chloro-2,4-difluorophenyl)-8'-hydroxy-10'-(trifluoromethyl)-2'H,4'H,6'H-spiro[oxetane-3,3'-[1,4]thiazepino[2,3,4-ij/]quinazolin]-6'-one (2)

Compound 1 (25 mg, 0.066 mmol, 1 equiv) was dissolved in 1,4-dioxane and $H_2O$ (1.3 mL, 0.3 mL, respectively, 0.04M). The resulting mixture was purged with $N_2$ for 30 min prior to the addition of RuPhos Pd G4 (5.6 mg, 0.0066 mmol, 10 mol %), $K_3PO_4$ (42 mg, 0.20 mmol, 3 equiv), and (5-chloro-2,4-difluorophenyl)boronic acid (63.5 mg, 0.33 mmol, 5 equiv). The microwave vial was fitted with a crimp-top cap, bubbled with $N_2$ for an additional 5 min, and placed on a heated block at 80° C. The resulting reaction mixture was homogenous and orange. After 1 h, the vial was removed from the heating block, allowed to cool, and the solvent was removed by rotary evaporation (95% conversion; determined by LC-MS). The crude material was filtered through a pad of silica gel using 3% MeOH/DCM (50 mL), and the solvent was removed by rotary evaporation. The material was used as is in the subsequent step: TLC (3% $MeOH/CH_2Cl_2$) $R_f$=0.24; LRMS-ESI (m/z) $[M-H]^+$ calculated for $C_{20}H_{11}ClF_5N_2O_3S$ 489.01, found 489.1.

Step 2: 11'-(5-chloro-2,4-difluorophenyl)-8'-(piperazin-1-yl-2,2,3,3,5,5,6,6-$d_8$)-10'-(trifluoromethyl)-2'H,4'H,6'H-spiro[oxetane-3,3'-[1,4]thiazepino[2,3,4-ij]quinazolin]-6'-one (3)

Compound 2 (32.4 mg, 0.066 mmol, 1 equiv) was dissolved in MeCN (0.5 mL) under a $N_2$ atmosphere in a 20 dr vial containing 3 Å molecular sieves. 1,8-Diazabicyclo[5.4.0]undec-7-ene (19.7 μL, 0.132 mmol, 2 equiv) was added by syringe to the reaction mixture followed by PYBOP (52 mg, 0.1 mmol, 1.5 equiv) at room temperature. The orange solution was stirred for 15 minutes, piperazine-2,2,3,3,5,5,6,6-$d_8$ (18.6 mg, 0.2 mmol, 3 equiv) was added at room temperature and the reaction mixture was heated at 60° C. After 2 hours, additional 1,8-diazabicyclo[5.4.0]undec-7-ene (19.7 μL, 0.132 mmol, 2 equiv) and PYBOP (52 mg, 0.1 mmol, 1.5 equiv) was added and heated at 60° C. for 2.5 h (full conversion by LC-MS). After allowing the reaction mixture to cool to room temperature, the solvent was removed and the residue was dissolved in MeOH, loaded onto a HyperSep SCX plug, and flushed with MeOH (ca. 30 mL). Next, the desired product was eluted with 1N $NH_3$ in MeOH (ca. 30 mL) and collected. The solvent was removed by rotary evaporation and used as is in the subsequent step: $^1H$ NMR (400 MHz, MeOH-$d_4$) δ 7.94 (s, 1H), 7.48 (t, J=7.8 Hz, 1H), 7.34 (t, J=9.1 Hz, 1H), 4.88-4.54 (m, 2H), 4.43 (dd, J=6.3, 1.7 Hz, 2H), 3.56 (d, J=6.7 Hz, 2H), 3.16 (sextet, J=3.7 Hz, 2H); LRMS-ESI (m/z) $[M+H]^+$ calculated for $C_{24}H_{13}D_8ClF_5N_4O_2S$ 567.15, found 567.2.

Step 3: 8'-(4-acryloylpiperazin-1-yl-2,2,3,3,5,5,6,6-$d_8$)-11'-(5-chloro-2,4-difluorophenyl)-10'-(trifluoromethyl)-2'H,4'H,6'H-spiro[oxetane-3,3'-[1,4]thiazepino[2,3,4-ij]quinazolin]-6'-one (4)

The acrylation was carried out by using the same procedure described as in other examples. 7.04 mg (yield: 17%) of title compound 4 was obtained as white solid. $^1H$ NMR (400 MHz, MeOH-$d_4$) δ 8.01 (s, 1H), 7.49 (t, J=7.5 Hz, 1H), 7.34 (t, J=9.1 Hz, 1H), 6.80 (dd, J=16.8, 10.6 Hz, 1H), 6.27 (dd, J=16.8, 2.0 Hz, 1H), 5.80 (dd, J=10.6, 1.9 Hz, 1H), 4.88-4.58 (m, 4H), 4.44 (dd, J=6.3, 2.8 Hz, 2H), 3.66-3.47 (m, 2H); LRMS-ESI (m/z) $[M+H]^+$ calculated for $C_{27}H_{15}D_8ClF_5N_4O_3S$ 621.16, found 621.2.

Examples 1312 and 1313: (3S,10S)-3-((2-oxa-7-azaspiro[3.5]nonan-7-yl)methyl)-7-((2S,5R)-4-acryloyl-2,5-dimethylpiperazin-1-yl)-10-(5-chloro-2,4-difluorophenyl)-9-(trifluoromethyl)-2,3-dihydro-5H-[1,4]thiazino[2,3,4-ij]quinazolin-5-one (P1) and (3S,10R)-3-((2-oxa-7-azaspiro[3.5]nonan-7-yl)methyl)-7-((2S,5R)-4-acryloyl-2,5-dimethylpiperazin-1-yl)-10-(5-chloro-2,4-difluorophenyl)-9-(trifluoromethyl)-2,3-dihydro-5H-[1,4]thiazino[2,3,4-ij]quinazolin-5-one

P1

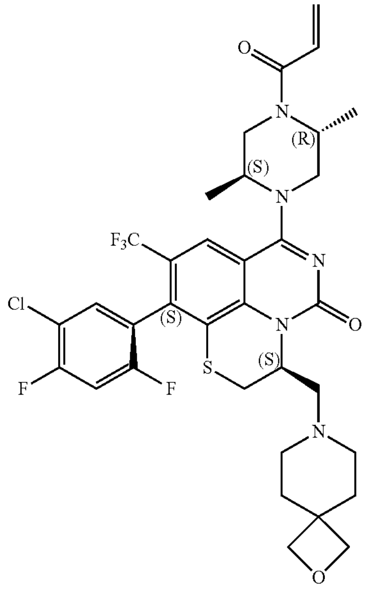

P2

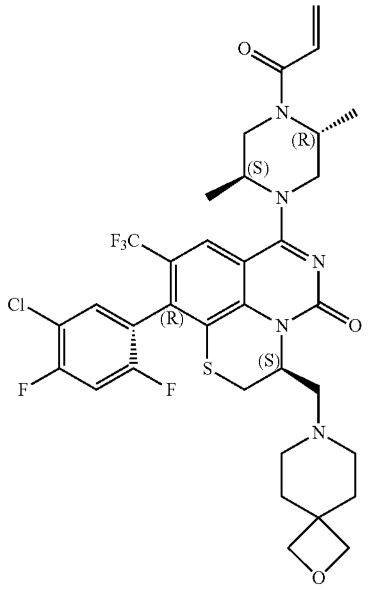

The title compound was prepared according to the scheme below.

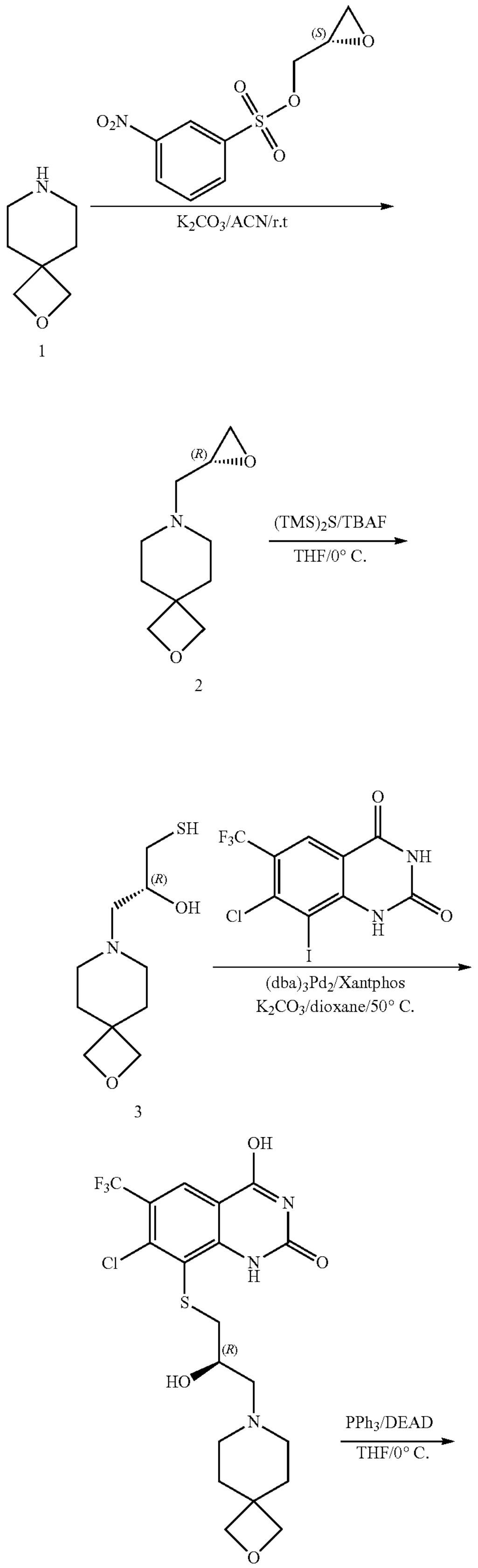

1

2

3

4

-continued
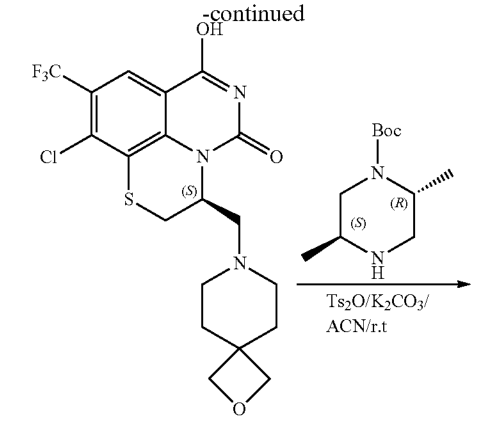
5
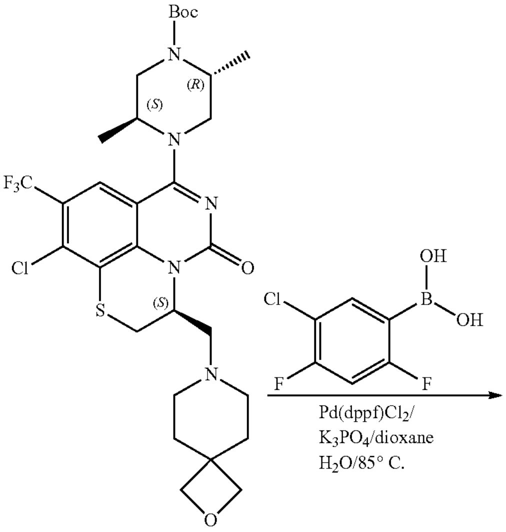
6
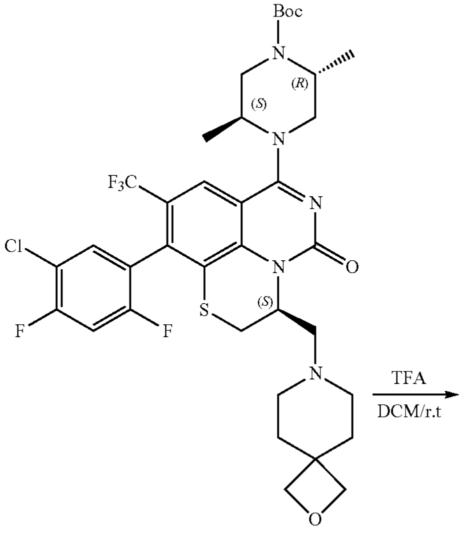
7
-continued
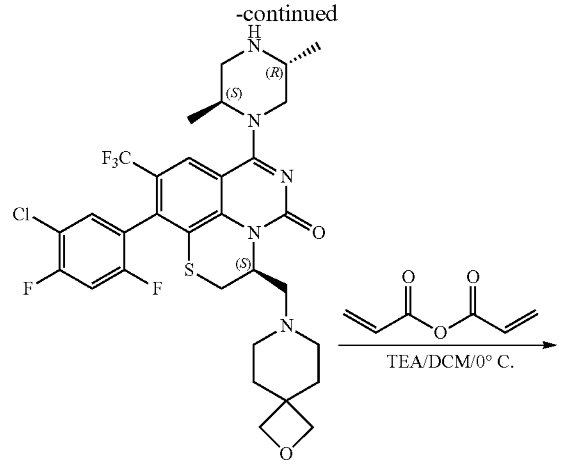
8
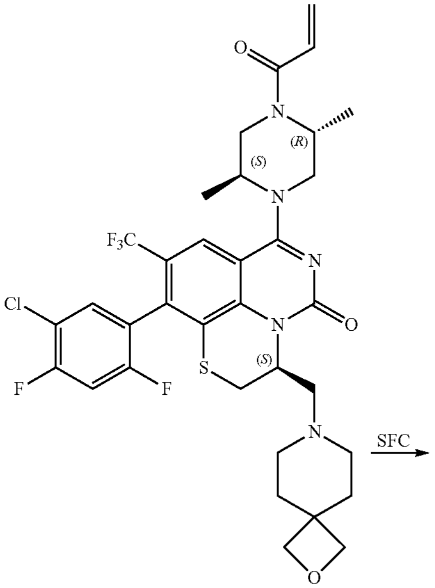
9
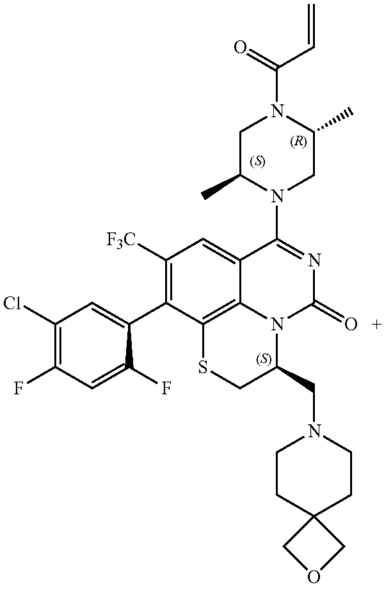
P1

-continued

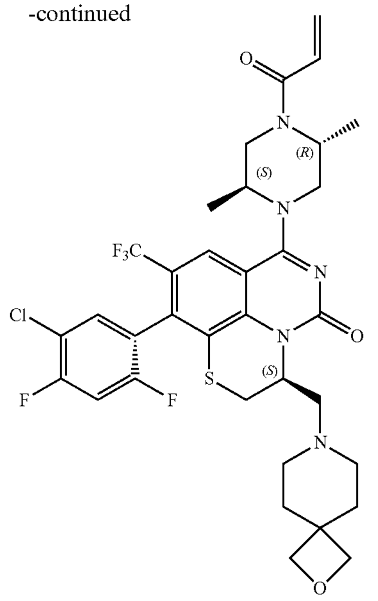

P2

Step 1: (R)-7-(oxiran-2-ylmethyl)-2-oxa-7-azaspiro[3.5]nonane (2)

A solution of (S)-oxiran-2-ylmethyl 3-nitrobenzenesulfonate (5.9 g, 22.8 mmol) in acetonitrile (60 mL) was added 2-oxa-7-azaspiro[3.5]nonane oxalate (1) (4.5 g, 20.7 mmol) and potassium carbonate (14.3 g, 103.6 mmol) at 0° C. under nitrogen atmosphere. The mixture was stirred under nitrogen atmosphere at room temperature for 16 hours. After completion, the mixture was concentrated and the residue was purified by silica gel column with dichloromethane/methanol=20/1 to afford (R)-7-(oxiran-2-ylmethyl)-2-oxa-7-azaspiro[3.5]nonane (2) (3.45 g, yield: 91%) as a brown oil. MS (ESI) m/z 180.1 [M+H]+.

Step 2: (R)-1-mercapto-3-(2-oxa-7-azaspiro[3.5]nonan-7-yl)propan-2-ol (3)

To a mixture of (R)-7-(oxiran-2-ylmethyl)-2-oxa-7-azaspiro[3.5]nonane (2) (3.74 g, 20.4 mmol) in tetrahydrofuran (70 mL) was added 1,1,1,3,3,3-hexamethyldisilathiane (5.45 g, 30.6 mmol) and tetrabutylammonium fluoride (1.0 M in tetrahydrofuran, 6.1 mL, 6.1 mmol) at 0° C. The mixture was stirred at room temperature for 6 hours. After completion, the mixture was concentrated. The residue was purified by silica gel column with dichloromethane/methanol=20/1 to afford (R)-1-mercapto-3-(2-oxa-7-azaspiro[3.5]nonan-7-yl)propan-2-ol (3) (3.47 g, yield: 78%) as a brown oil. MS (ESI) m/z 218.2 [M+H]+.

Step 3: (R)-7-chloro-4-hydroxy-8-((2-hydroxy-3-(2-oxa-7-azaspiro[3.5]nonan-7-yl)propyl)thio)-6-(trifluoromethyl)quinazolin-2(1H)-one (4)

To a solution of 7-chloro-8-iodo-6-(trifluoromethyl)quinazoline-2,4(1H,3H)-dione (2 g, 4.59 mmol) in dioxane (50 mL) were added potassium carbonate (2.5 g, 18.36 mmol), (R)-1-mercapto-3-(2-oxa-7-azaspiro[3.5]nonan-7-yl)propan-2-ol (3) (3.2 g, 6.88 mmol), 4,5-bis(diphenyl-phosphino)-9,9-dimethylxanthene (526 g, 0.91 mmol) and tris (dibenzylideneacetone) dipalladium (421 mg, 0.46 mmol). The mixture was stirred at 50° C. under nitrogen atmosphere for 16 hours. After completion, the mixture was concentrated. The residue was purified by silica gel column with dichloromethane/methanol=20/1 to afford (R)-7-chloro-4-hydroxy-8-((2-hydroxy-3-(2-oxa-7-azaspiro[3.5]nonan-7-yl)propyl)thio)-6-(trifluoromethyl)quinazolin-2(1H)-one (4) (2.2 g, yield: 89%) as an orange solid. MS (ESI) m/z 480.9 [M+H]+.

Step 4: (S)-3-(2-oxa-7-azaspiro[3.5]nonan-7-ylmethyl)-10-chloro-7-hydroxy-9-(trifluoromethyl)-2H-[1,4]thiazino[2,3,4-ij]quinazolin-5(3H)-one (5)

To a mixture of (R)-7-bromo-6-chloro-4-hydroxy-8-((2-hydroxy-3-(2-oxa-7-azaspiro[3.5]nonan-7-yl)propyl)thio)quinazolin-2(1H)-one (4) (2.16 g, 4.5 mmol) and triphenylphosphine (1.77 g, 6.75 mmol) in tetrahydrofuran (70 mL) was added diethyl azodicarboxylate (1.18 g, 6.75 mmol). The mixture was stirred at room temperature for 2 hours. After completion, the mixture was poured into ice-water (100 mL) and extracted with ethyl acetate (3×100 mL). The mixture was concentrated and the residue was purified by silica gel column with dichloromethane/methanol=50/1 to afford (S)-3-(2-oxa-7-azaspiro[3.5]nonan-7-ylmethyl)-10-chloro-7-hydroxy-9-(trifluoromethyl)-2H-[1,4]thiazino[2,3,4-ij]quinazolin-5(3H)-one (5) (1.8 g, yield: 87%) as a light yellow solid. MS (ESI) m/z 462.3 [M+H]+.

Step 5: (2R,5S)-tert-butyl 4-((S)-3-(2-oxa-7-azaspiro[3.5]nonan-7-ylmethyl)-10-bromo-9-chloro-5-oxo-3,5-dihydro-2H-[1,4]thiazino[2,3,4-ij]quinazolin-7-yl)-2,5-dimethylpiperazine-1-carboxylate (6)

To a mixture of (S)-3-(2-oxa-7-azaspiro[3.5]nonan-7-ylmethyl)-10-bromo-9-chloro-7-hydroxy-2H-[1,4]thiazino[2,3,4-ij]quinazolin-5(3H)-one (5) (0.7 g, 1.52 mmol) and potassium carbonate (2.1 g, 15.2 mmol) in acetonitrile (60 mL) was added 4-methylbenzenesulfonic anhydride (992 mg, 3.04 mmol) at 0° C. The mixture was stirred at 0° C. for 30 min and at 30° C. for 1 hour. After completion, (2R,5S)-tert-butyl 2,5-dimethylpiperazine-1-carboxylate (977 mg, 4.56 mmol) was added into the reaction solution. The reaction mixture was stirred at 0° C. for 1 hour. After completion, the mixture was poured into ice-water (300 mL) and extracted with ethyl acetate (3×200 mL). The mixture was concentrated and the residue was purified by flash chromatography column (C18, acetonitrile/water=20% to 95%) to afford (2R,5S)-tert-butyl 4-((S)-3-(2-oxa-7-azaspiro[3.5]nonan-7-ylmethyl)-10-bromo-9-chloro-5-oxo-3,5-dihydro-2H-[1,4]thiazino[2,3,4-ij]quinazolin-7-yl)-2,5-dimethylpiperazine-1-carboxylate (6) (650 mg, yield: 65%) as a pale-white solid. MS (ESI) m/z 658.2 [M+H]+.

Step 6: (2R,5S)-tert-butyl 4-((3S)-3-(2-oxa-7-azaspiro[3.5]nonan-7-ylmethyl)-10-(5-chloro-2,4-difluorophenyl)-5-oxo-9-(trifluoromethyl)-3,5-dihydro-2H-[1,4]thiazino[2,3,4-ij]quinazolin-7-yl)-2,5-dimethylpiperazine-1-carboxylate (7)

To a mixture of (2R,5S)-tert-butyl 4-((S)-3-(2-oxa-7-azaspiro[3.5]nonan-7-ylmethyl)-10-bromo-9-chloro-5-oxo-3,5-dihydro-2H-[1,4]thiazino[2,3,4-ij]quinazolin-7-yl)-2,5-dimethylpiperazine-1-carboxylate (6) (300 mg, 0.46 mmol) and tripotassium orthophosphate (297 mg, 1.4 mmol) in 1,4-dioxane (5 mL) and water (1 mL) was added [1,1'-bis (diphenylphosphino)ferrocene]dichloropalladium(II) (36 mg, 0.05 mmol) and (5-chloro-2,4-difluorophenyl)boronic acid (631 mg, 2.3 mmol). The mixture was stirred at 85° C. for 2 hours. After completion, the mixture was purified by silica gel column with dichloromethane/methanol=50/1 to afford (2R,5S)-tert-butyl 4-((3S)-3-(2-oxa-7-azaspiro[3.5]nonan-7-ylmethyl)-10-(5-chloro-2,4-difluorophenyl)-5-oxo-9-(trifluoromethyl)-3,5-dihydro-2H-[1,4]thiazino[2,3,4-ij]quinazolin-7-yl)-2,5-dimethylpiperazine-1-carboxylate (7) (260 mg, crude) as a light yellow oil. MS (ESI) m/z 770.2 $[M+H]^+$.

Step 7: (3S)-3-(2-oxa-7-azaspiro[3.5]nonan-7-ylmethyl)-10-(5-chloro-2,4-difluorophenyl)-7-((2S,5R)-2,5-dimethylpiperazin-1-yl)-9-(trifluoromethyl)-2H-[1,4]thiazino[2,3,4-ij]quinazolin-5(3H)-one (8)

To a mixture of (2R,5S)-tert-butyl 4-((3S)-3-(2-oxa-7-azaspiro[3.5]nonan-7-ylmethyl)-10-(5-chloro-2,4-difluorophenyl)-5-oxo-9-(trifluoromethyl)-3,5-dihydro-2H-[1,4]thiazino[2,3,4-ij]quinazolin-7-yl)-2,5-dimethylpiperazine-1-carboxylate (7) (260 mg, 0.33 mmol) in dichloromethane (3 mL) was added trifluoroacetic acid (1 mL). The mixture was stirred at room temperature for 30 min. After completion, the solvent was removed under pressure. The residue was redissolved in dichloromethane and washed with saturated $NaHCO_3$. The organic layer was dried over $Na_2SO_4$ and concentrated. The mixture was purified by silica gel column with dichloromethane/methanol=50/1 to afford (3S)-3-(2-oxa-7-azaspiro[3.5]nonan-7-ylmethyl)-10-(5-chloro-2,4-difluorophenyl)-7-((2S,5R)-2,5-dimethylpiperazin-1-yl)-9-(trifluoromethyl)-2H-[1,4]thiazino[2,3,4-ij]quinazolin-5(3H)-one (8) (225 mg, yield: 99%) as a yellow solid. MS (ESI) m/z 670.2 $[M+H]^+$.

Step 8: (3S)-3-(2-oxa-7-azaspiro[3.5]nonan-7-ylmethyl)-7-((2S,5R)-4-acryloyl-2,5-dimethylpiperazin-1-yl)-10-(5-chloro-2,4-difluorophenyl)-9-(trifluoromethyl)-2H-[1,4]thiazino[2,3,4-ij]quinazolin-5(3H)-one (9)

To a mixture of (3S)-3-(2-oxa-7-azaspiro[3.5]nonan-7-ylmethyl)-10-(5-chloro-2,4-difluorophenyl)-7-((2S,5R)-2,5-dimethylpiperazin-1-yl)-9-(trifluoromethyl)-2H-[1,4]thiazino[2,3,4-ij]quinazolin-5(3H)-one (8) (225 mg, 0.34 mmol) and triethylamine (61 mg, 0.68 mmol) in dichloromethane (5 mL) was added acrylic anhydride (43 mg, 0.34 mmol) at 0° C. The mixture was stirred at 0° C. for 1 hour. After completion, the mixture was purified by preparative high performance liquid chromatography (20% to 95% acetonitrile in water) to afford the product (110 mg, yield: 45%) as a light yellow solid. MS (ESI) m/z 724.2 $[M+H]^+$.

The above racemate (110 mg) was separated by chiral supercritical fluid chromatography (separation condition: Column:Chiralpak AD-H 5 μm 20×250 mm; Mobile Phase: $CO_2$:IPA=70:30 at 25 mL/min; Temp: 25° C.; Wavelength: 254 nm) to afford the compound P1 (20 mg of white powder) and compound P2 (70 mg of white powder)); Chiral HPLC Analytical: on CHIRALPAK® AD-H was using 5 μm 4.6×250 mm column, Mobile Phase: $CO_2$:IPA=70:30 at 2.5 mL/min; Temp: 25° C.; Wavelength: 254 nm). P1: $^1H$ NMR (400 MHz, $CDCl_3$) δ 7.84-7.82 (m, 1H), 7.26-7.23 (m, 1H), 7.07 (t, J=8.4 Hz, 1H), 6.66-6.53 (m, 1H), 6.41-6.33 (m, 1H), 5.80-5.75 (m, 1H), 5.34-5.32 (m, 1H), 5.05-5.04 (m, 0.5H), 4.83-4.79 (m, 1H), 4.42-4.33 (m, 5.5H), 4.06-4.02 (m, 0.5H), 3.76-3.64 (m, 2H), 3.42-3.38 (m, 1H), 3.28-3.25 (m, 0.5H), 3.01-2.98 (m, 1H), 2.72-2.66 (m, 1H), 2.55-2.35 (m, 5H), 1.82-1.80 (m, 4H), 1.47-1.38 (m, 6H). Chiral SFC fraction 1: e.e. =100%, Rt=5.35 min. P2: δ 7.83 (s, 1H), 7.30-7.26 (m, 1H), 7.07 (t, J=8.8 Hz, 1H), 6.66-6.50 (m, 1H), 6.41-6.33 (m, 1H), 5.80-5.75 (m, 1H), 5.36-5.34 (m, 1H), 5.03-4.99 (m, 0.5H), 4.79-4.77 (m, 0.5H), 4.67-4.65 (m, 0.5H), 4.43-4.34 (m, 5.5H), 4.09-4.06 (m, 0.5H), 3.76-3.63 (m, 2H), 3.45-3.42 (m, 1H), 3.28-3.25 (m, 0.5H), 3.04-3.00 (m, 1H), 2.91-2.31 (m, 6H), 1.90-1.87 (m, 4H), 1.48-1.37 (m, 6H). Chiral SFC fraction 1: e.e. =99.84%, Rt=6.34 min.

Example 1321

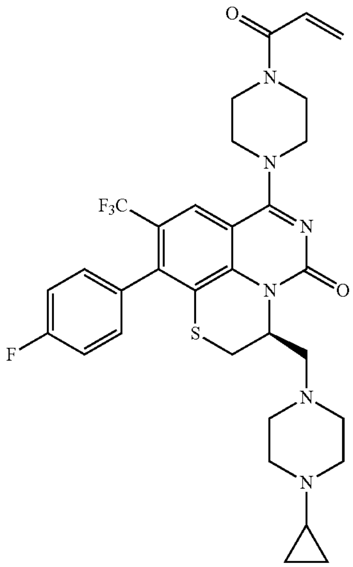 [SMILES: C=CC(=O)N1CCN(c2nc(=O)n3c4c(c(-c5ccc(F)cc5)c(C(F)(F)F)cc24)SC[C@@H]3CN2CCN(C3CC3)CC2)CC1]

The title compound was prepared according to the scheme below.

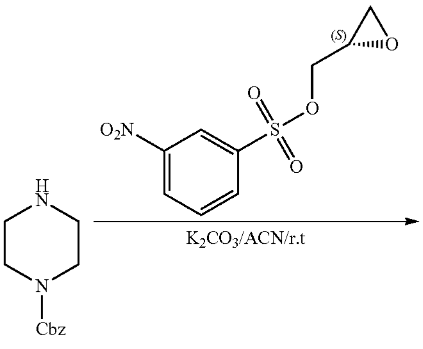

1

-continued
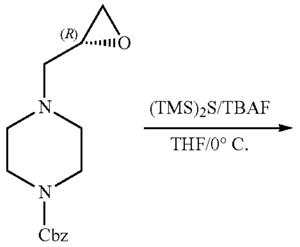
2
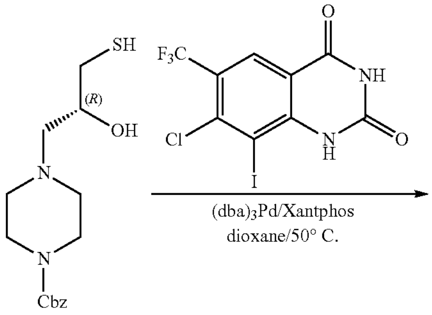
3
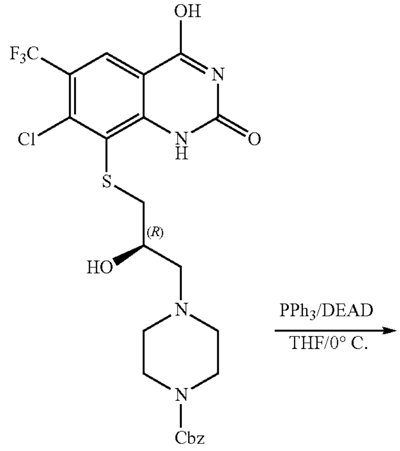
4
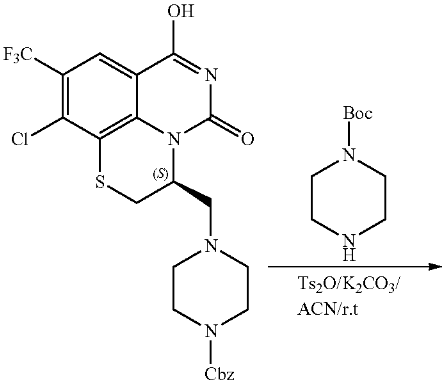
5
-continued
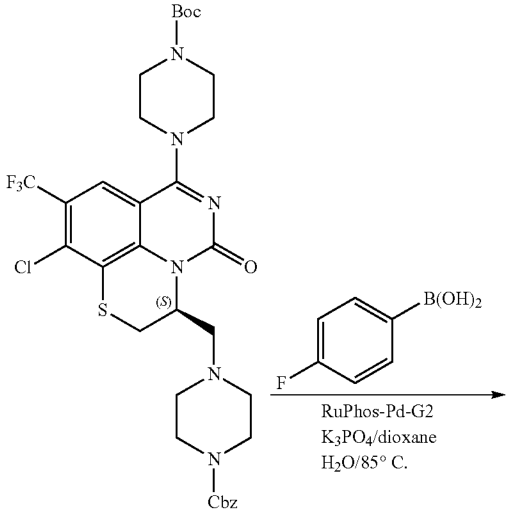
6
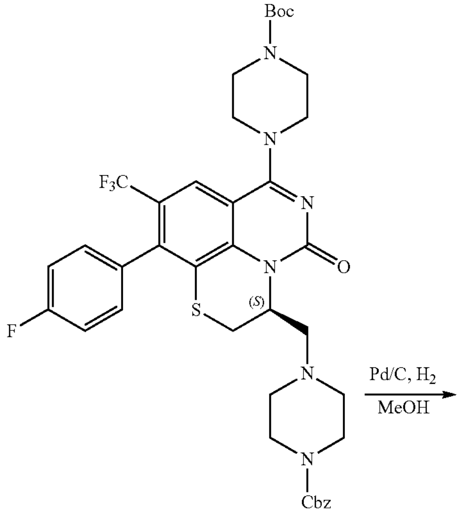
7
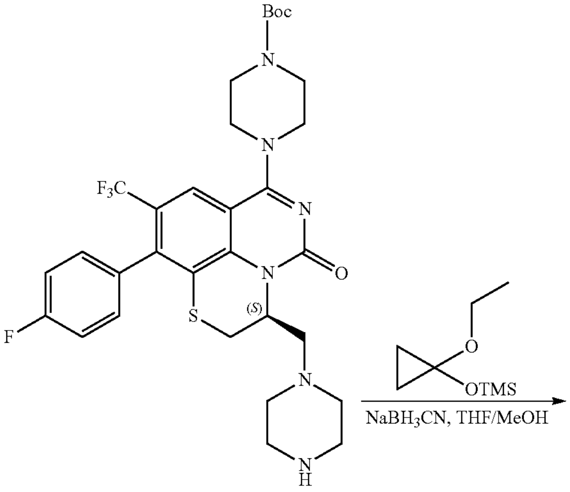
8

-continued

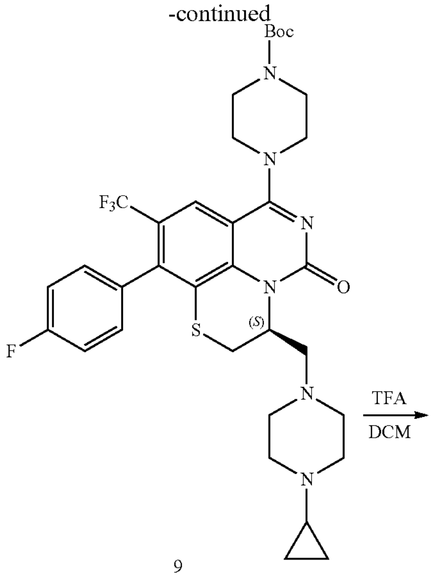

9

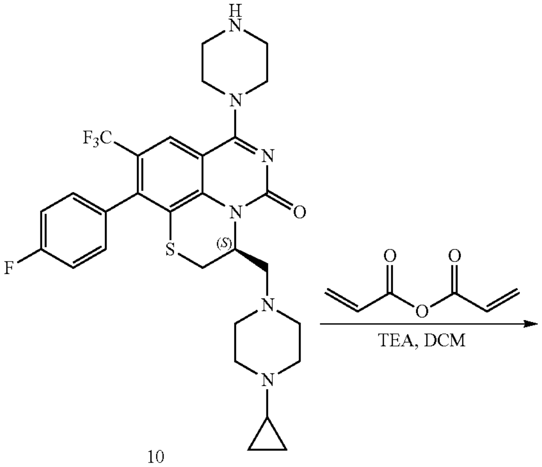

10

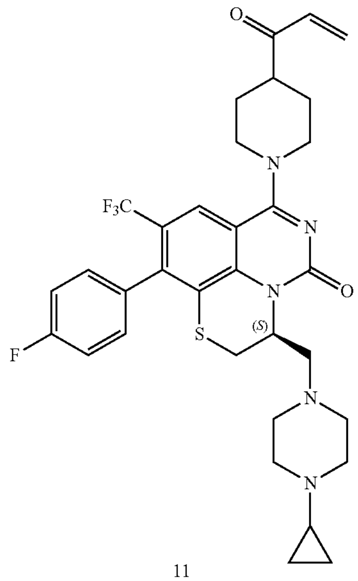

11

Step 1: (R)-benzyl 4-(oxiran-2-ylmethyl)piperazine-1-carboxylate (2)

To a solution of (S)-oxiran-2-ylmethyl 3-nitrobenzene-sulfonate (25.0 g, 96.5 mmol) in acetonitrile (150 mL) was added benzyl piperazine-1-carboxylate (1) (19.3 g, 75.8 mmol) and potassium carbonate (24.0 g, 176 mmol) at 0° C. The mixture was stirred under nitrogen atmosphere at room temperature for 22 hours. After completion, the mixture was concentrated and the residue was purified by silica gel column with dichloromethane/methanol=50/1 to afford (R)-benzyl 4-(oxiran-2-ylmethyl)piperazine-1-carboxylate (2) (24.5 g, crude) as a light yellow oil. MS (ESI) m/z 277.4 $[M+H]^+$.

Step 2: (R)-benzyl 4-(3-hydroxy-2-mercaptopropyl) piperazine-1-carboxylate (3)

To a mixture of (R)-benzyl 4-(oxiran-2-ylmethyl)piperazine-1-carboxylate (2) (24.5 g, 88.7 mmol) in tetrahydrofuran (300 mL) were added 1,1,1,3,3,3-hexamethyldisilathiane (17.4 g, 97.5 mmol) and tetrabutylammonium fluoride (1.0 M in tetrahydrofuran, 26.7 mL, 26.7 mmol) at 0° C. The mixture was stirred at room temperature for 2 hours. After completion, the mixture was poured into water (300 mL), extracted with ethyl acetate (3×200 mL). The organic phase was washed with brine (300 mL) and dried over anhydrous sodium sulfate. After filtration and concentration, the residue was purified by silica gel column with dichloromethane/methanol=50/1 to afford (R)-benzyl 4-(3-hydroxy-2-mercaptopropyl)piperazine-1-carboxylate (3) (20.8 g, yield: 76%) as a colorless oil. MS (ESI) m/z 311.5 $[M+H]^+$. $^1H$ NMR (400 MHz, $CDCl_3$) δ 7.36-7.31 (m, 5H), 5.13 (s, 2H), 3.80-3.78 (m, 1H), 3.54-3.50 (m, 4H), 3.39 (s, 1H), 2.66-2.57 (m, 4H), 2.46-2.40 (m, 4H), 1.57-1.52 (m, 1H).

Step 3: (R)-benzyl 4-(3-((7-chloro-4-hydroxy-2-oxo-6-(trifluoromethyl)-1,2-dihydroquinazolin-8-yl) thio)-2-hydroxypropyl)piperazine-1-carboxylate (4)

To a solution of 7-chloro-8-iodo-6-(trifluoromethyl)quinazoline-2,4(1H,3H)-dione (5.00 g, 12.8 mmol) in dioxane (128 mL) were added potassium carbonate (5.29 g, 38.4 mmol), (R)-benzyl 4-(2-hydroxy-3-mercaptopropyl)piperazine-1-carboxylate (3) (3.97 g, 12.8 mmol), 4,5-bis(diphenyl-phosphino)-9,9-dimethylxanthene (1.47 g, 2.56 mmol) and tris(dibenzylideneacetone) dipalladium (1.20 g, 1.28 mmol). The mixture was stirred at 55° C. under nitrogen atmosphere for 8 hours. After completion, the mixture was diluted with tetrahydrofuran (300 mL) and filtered. The filtrate was concentrated and the residue was purified by silica gel column chromatography (dichloromethane/methanol=100/1 to 20/1) to afford (R)-benzyl 4-(3-((7-chloro-4-hydroxy-2-oxo-6-(trifluoromethyl)-1,2-dihydroquinazolin-8-yl)thio)-2-hydroxypropyl)piperazine-1-carboxylate (4) (5.70 g, yield: 78%) as a yellow solid. MS (ESI) m/z 573.5 $[M+H]^+$.

Step 4: (S)-benzyl 4-((10-chloro-7-hydroxy-5-oxo-9-(trifluoromethyl)-3,5-dihydro-2H-[1,4]thiazino[2,3,4-ij]quinazolin-3-yl)methyl)piperazine-1-carboxylate (5)

To a mixture of (R)-benzyl 4-(3-((7-chloro-4-hydroxy-2-oxo-6-(trifluoromethyl)-1,2-dihydroquinazolin-8-yl)thio)-2-hydroxypropyl)piperazine-1-carboxylate (4) (4.66 g, 8.1 mmol) and triphenylphosphine (4.26 g, 16.2 mmol) in tetrahydrofuran (81 mL) was added diethyl azodicarboxylate (2.81 g, 16.2 mmol) at 0° C. The mixture was stirred at 0° C. for 45 min. After completion, the mixture was poured into ice-water (300 mL) and extracted with ethyl acetate (3×200 mL). After concentration, the residue was purified by flash chromatography column (C18, acetonitrile/water=30% to 95%) to afford (S)-benzyl 4-((10-chloro-7-hydroxy-5-oxo-9-(trifluoromethyl)-3,5-dihydro-2H-[1,4]thiazino[2,3,4-ij]quinazolin-3-yl)methyl)piperazine-1-carboxylate (5) (3.14 g, yield: 70%) as a white solid. MS (ESI) m/z 555.5 $[M+H]^+$.

Step 5: (S)-benzyl 4-((7-(4-(tert-butoxycarbonyl)piperazin-1-yl)-10-chloro-5-oxo-9-(trifluoromethyl)-3,5-dihydro-2H-[1,4]thiazino[2,3,4-ij]quinazolin-3-yl)methyl)piperazine-1-carboxylate (6)

To a mixture of (S)-benzyl 4-((10-chloro-7-hydroxy-5-oxo-9-(trifluoromethyl)-3,5-dihydro-2H-[1,4]thiazino[2,3,4-ij]quinazolin-3-yl)methyl)piperazine-1-carboxylate (5) (1.77 g, 3.19 mmol) and potassium carbonate (2.20 g, 15.9 mmol) in acetonitrile (106 mL) was added 4-methylbenzenesulfonic anhydride (2.08 g, 6.38 mmol) at 25° C. The mixture was stirred at 25° C. for 3 hours. After completion, tert-butyl piperazine-1-carboxylate (1.18 g, 6.38 mmol) was added into the reaction solution. The reaction mixture was stirred at 25° C. for 1 hour. The mixture was poured into ice-water (300 mL) and extracted with ethyl acetate (3×200 mL). Concentrated and the residue was purified by flash chromatography column (C18, acetonitrile/water=20% to 95%) to afford (S)-benzyl 4-((7-(4-(tert-butoxycarbonyl)piperazin-1-yl)-10-chloro-5-oxo-9-(trifluoromethyl)-3,5-dihydro-2H-[1,4]thiazino[2,3,4-ij]quinazolin-3-yl)methyl)piperazine-1-carboxylate (6) (1.43 g, yield: 63%) as a pale-white solid. MS (ESI) m/z 723.1 $[M+H]^+$.

Step 6: (S)-benzyl 4-((7-(4-(tert-butoxycarbonyl)piperazin-1-yl)-10-(4-fluorophenyl)-5-oxo-9-(trifluoromethyl)-3,5-dihydro-2H-[1,4]thiazino[2,3,4-ij]quinazolin-3-yl)methyl)piperazine-1-carboxylate (7)

To a solution of ((S)-benzyl 4-((7-(4-(tert-butoxycarbonyl)piperazin-1-yl)-10-chloro-5-oxo-9-(trifluoromethyl)-3,5-dihydro-2H-[1,4]thiazino[2,3,4-ij]quinazolin-3-yl)methyl)piperazine-1-carboxylate (6) (1 g, 1.3 mmol) in 1,4-dioxane (15 mL) and water (3 mL) were added tripotassium phosphate (1.1 g, 5.2 mmol), (4-fluorophenyl)boronic acid (546 mg, 3.9 mmol), and chloro(2-dicyclohexylphosphino-2', 6'-diisopropoxy-1,1'-biphenyl)[2-(2'-amino-1,1'-biphenyl)]palladium(II) (202 mg, 0.26 mmol). The mixture was stirred at 85° C. under nitrogen atmosphere for 4 hours. After completion, the mixture was diluted with tetrahydrofuran (300 mL) and the insoluble was filtered out. The filtrate was concentrated and the residue was purified by silica gel column chromatography (dichloromethane/methanol=100/1 to 30/1) to afford (S)-benzyl 4-((7-(4-(tert-butoxycarbonyl)piperazin-1-yl)-10-(4-fluorophenyl)-5-oxo-9-(trifluoromethyl)-3,5-dihydro-2H-[1,4]thiazino[2,3,4-ij]quinazolin-3-yl)methyl)piperazine-1-carboxylate (7) (1.00 g, crude) as a yellow solid. MS (ESI) m/z 783.3 $[M+H]^+$.

Step 7: (S)-tert-butyl 4-(10-(4-fluorophenyl)-5-oxo-3-(piperazin-1-ylmethyl)-9-(trifluoromethyl)-3,5-dihydro-2H-[1,4]thiazino[2,3,4-ij]quinazolin-7-yl)piperazine-1-carboxylate (8)

To a mixture of (S)-benzyl 4-((7-(4-(tert-butoxycarbonyl)piperazin-1-yl)-10-(4-fluorophenyl)-5-oxo-9-(trifluoromethyl)-3,5-dihydro-2H-[1,4]thiazino[2,3,4-ij]quinazolin-3-yl)methyl)piperazine-1-carboxylate (7) (1.00 g, 1.20 mmol) in ethanol (15 ml) was added Pd/C (0.300 g, 30% w/w) at 25° C. The reaction solution was stirred at room temperature under hydrogen atmosphere for 1 hour. The mixture was filtered and concentrated. The residue was purified by silica gel column chromatography (dichloromethane/methanol=15/1) to afford (S)-tert-butyl 4-(10-(4-fluorophenyl)-5-oxo-3-(piperazin-1-ylmethyl)-9-(trifluoromethyl)-3,5-dihydro-2H-[1,4]thiazino[2,3,4-ij]quinazolin-7-yl)piperazine-1-carboxylate (8) (600 mg, yield: 77%) as a yellow solid. MS (ESI) m/z 649.7 $[M+H]^+$.

Step 8: (S)-tert-butyl 4-(3-((4-cyclopropylpiperazin-1-yl)methyl)-10-(4-fluorophenyl)-5-oxo-9-(trifluoromethyl)-3,5-dihydro-2H-[1,4]thiazino[2,3,4-ij]quinazolin-7-yl)piperazine-1-carboxylate (9)

To a mixture of (S)-tert-butyl 4-(10-(4-fluorophenyl)-5-oxo-3-(piperazin-1-ylmethyl)-9-(trifluoromethyl)-3,5-dihydro-2H-[1,4]thiazino[2,3,4-ij]quinazolin-7-yl)piperazine-1-carboxylate (8) (600 mg, 0.93 mmol) and sodium cyanoborohydride (805 mg, 4.63 mmol) in tetrahydrofuran (5 mL) and methanol (5 mL) was added (1-ethoxycyclopropoxy)trimethylsilane (991 mg, 5.70 mmol) at 25° C. under nitrogen atmosphere. The reaction solution was heated to 85° C. for 12 hours. After completion, the mixture was filtered and concentrated. The residue was purified by silica gel column chromatography (dichloromethane/methanol=30/1) to afford ((S)-tert-butyl 4-(3-((4-cyclopropylpiperazin-1-yl)methyl)-10-(4-fluorophenyl)-5-oxo-9-(trifluoromethyl)-3,5-dihydro-2H-[1,4]thiazino[2,3,4-ij]quinazolin-7-yl)piperazine-1-carboxylate (9) (300 mg, yield: 46%) as a yellow solid. MS (ESI) m/z 689.9 $[M+H]^+$.

Step 9: (S)-3-((4-cyclopropylpiperazin-1-yl)methyl)-10-(4-fluorophenyl)-7-(piperazin-1-yl)-9-(trifluoromethyl)-2H-[1,4]thiazino[2,3,4-ij]quinazolin-5(3H)-one (10)

To a cooled mixture of ((S)-tert-butyl 4-(3-((4-cyclopropylpiperazin-1-yl)methyl)-10-(4-fluorophenyl)-5-oxo-9-(trifluoromethyl)-3,5-dihydro-2H-[1,4]thiazino[2,3,4-ij]quinazolin-7-yl)piperazine-1-carboxylate (9) (300 mg, 0.43 mmol) in dichloromethane (5 mL) was added trifluoroacetic acid (1 mL) at 0° C. The reaction solution was stirred at room temperature for 1 hour. The mixture was concentrated. The residue was redissolved in dichloromethane and washed with saturated $NaHCO_3$. The organic layer was dried over $Na_2SO_4$ and concentrated. The residue was purified by silica gel column chromatography (dichloromethane/methanol=15/1) to afford (S)-3-((4-cyclopropylpiperazin-1-yl)methyl)-10-(4-fluorophenyl)-7-(piperazin-1-yl)-9-(trifluoromethyl)-2H-[1,4]thiazino[2,3,4-ij]quinazolin-5(3H)-one (10) (200 mg, yield: 79%) as a yellow solid. MS (ESI) m/z 589.8 $[M+H]^+$.

Step 10: ((S)-7-(4-acryloylpiperazin-1-yl)-3-((4-cyclopropylpiperazin-1-yl)methyl)-10-(4-fluorophenyl)-9-(trifluoromethyl)-2H-[1,4]thiazino[2,3,4-ij]quinazolin-5(3H)-one (11)

To a mixture of (S)-3-((4-cyclopropylpiperazin-1-yl)methyl)-10-(4-fluorophenyl)-7-(piperazin-1-yl)-9-(trifluoromethyl)-2H-[1,4]thiazino[2,3,4-ij]quinazolin-5(3H)-one (10) (180 mg, 0.30 mmol) and triethyl amine (56 mg, 0.56 mmol) in dichloromethane (5 mL) was added acrylic anhydride (70 mg, 0.56 mmol) at 0° C. The mixture was stirred at 0° C. for 1 hour. After completion, the mixture was poured into ice-water (50 mL) and extracted with ethyl acetate (3×20 mL). Concentrated and the residue was purified by preparative high performance liquid chromatography (20% to 95% acetonitrile in water) to afford (S)-7-(4-acryloylpiperazin-1-yl)-3-((4-cyclopropylpiperazin-1-yl)methyl)-10-(4-fluorophenyl)-9-(trifluoromethyl)-2H-[1,4]thiazino[2,3,4-ij]quinazolin-5(3H)-one (11) (100 mg, yield:52%) as a white solid. MS (ESI) m/z 643.8 [M+H]+. $^1$H NMR (400 MHz, $CDCl_3$) δ 7.80 (s, 1H), 7.21-7.17 (m, 4H), 6.62-6.54 (m, 1H), 6.41-6.31 (m, 1H), 5.82-5.76 (m, 1H), 5.35-5.29 (m, 1H), 3.97-3.73 (m, 9H), 3.47-3.35 (m, 1H), 2.98-2.93 (m, 1H), 2.86-2.46 (m, 10H), 0.59-0.37 (m, 4H).

Example 1357

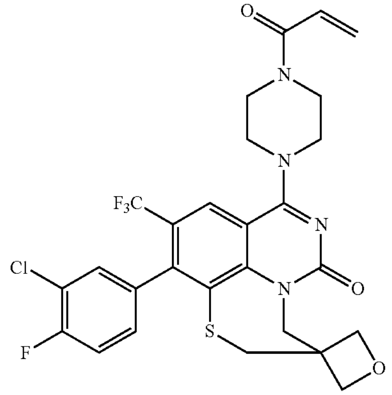 [SMILES: C=CC(=O)N1CCN(c2nc(=O)n3c4c(c(-c5ccc(F)c(Cl)c5)c(C(F)(F)F)cc24)SCC2(COC2)C3)CC1]

The title compound was prepared according to the scheme below.

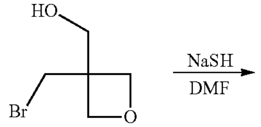

1

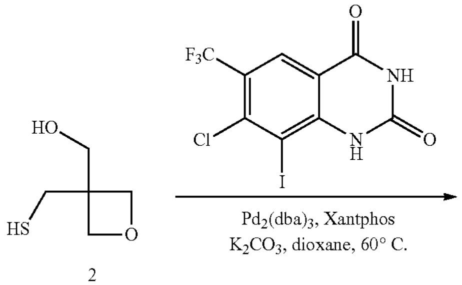

2

-continued

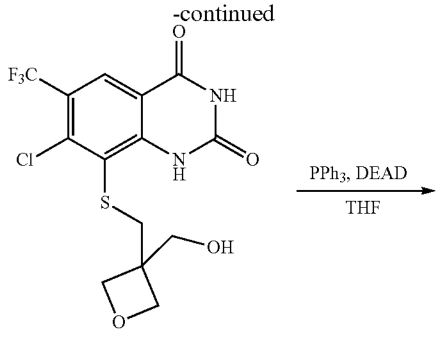

3

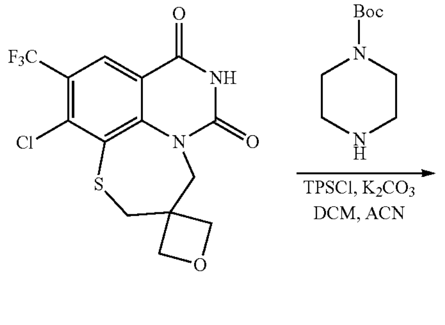

4

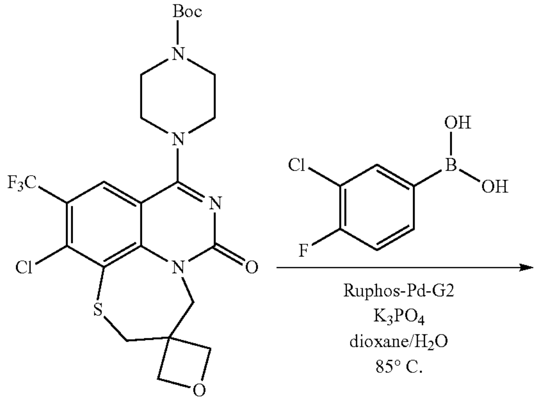

5

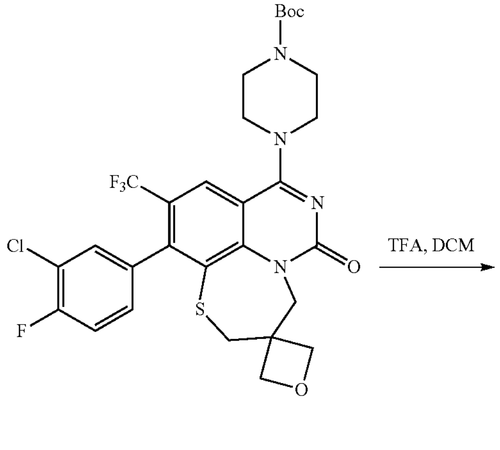

6

-continued

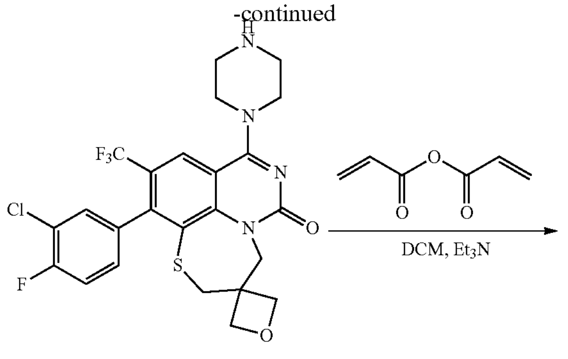

7

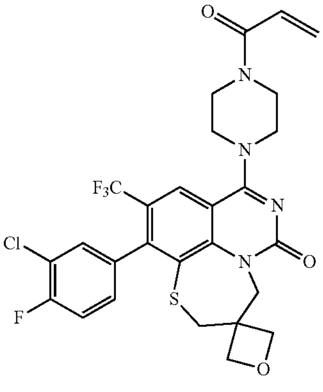

8

Step 1: (3-(mercaptomethyl)oxetan-3-yl)methanol (2)

To a solution of (3-(bromomethyl)oxetan-3-yl)methanol (1) (200 g, 1.105 mmol) in ethanol (1.8 L) was added sodium hydrosulfide (176.8 g, 2.210 mmol, 70% purity) at 0° C. The mixture was stirred at room temperature under nitrogen atmosphere for 2 hours. After completion, the mixture was filtered and the filtrate was concentrated to afford the crude product which was purified by silica gel column with dichloromethane/methanol=100/1 to afford (3-(mercaptomethyl)oxetan-3-yl) methanol (2) (64.2 g, yield: 43%) as a pale yellow oil. $^1$H NMR (400 MHz, $CDCl_3$) δ 4.49-4.41 (m, 4H), 3.95 (s, 2H), 2.96 (d, J=8.4 Hz, 2H), 2.06 (brs, 1H), 1.36 (t, J=8.4 Hz, 1H).

Step 2: 7-chloro-8-(((3-(hydroxymethyl)oxetan-3-yl) methyl)thio)-6-(trifluoromethyl)quinazoline-2,4(1H, 3H)-dione (3)

To a solution of 7-chloro-8-iodo-6-(trifluoromethyl)quinazoline-2,4(1H,3H)-dione (71.40 g, 182.85 mmol) in dioxane (2200 mL) were added potassium carbonate (75.82 g, 548.56 mmol), (3-(mercaptomethyl)oxetan-3-yl)methanol (2) (49.08 g, 365.70 mmol), 4,5-bis(diphenyl-phosphino)-9,9-dimethylxanthene (15.87 g, 27.43 mmol) and tris(dibenzylideneacetone) dipalladium (16.75 g, 18.29 mmol). The mixture was stirred at 65° C. under nitrogen atmosphere for 16 hours. After completion, the mixture was filtered and the solid was washed with dichloromethane (1 L). (CAUTION! The organic phase contained only little product.) Then the solid was washed with tetrahydrofuran until the product was little by TLC. The tetrahydrofuran phase was concentrated and the residue was heated with tetrahydrofuran/petroleum ether (200 mL/50 mL) to afford the crude product 7-chloro-8-(((3-(hydroxymethyl)oxetan-3-yl) methyl)thio)-6-(trifluoromethyl)quinazoline-2,4(1H, 3H)-dione (3) (72.7 g, crude) as a pale yellow solid. MS (ESI) m/z 397.0 $[M+H]^+$.

Step 3: 11-chloro-10-(trifluoromethyl)-2H-spiro[[1, 4]thiazepino[2,3,4-ij]quinazoline-3,3'-oxetane]-6,8 (4H,7H)-dione (4)

To a mixture of 7-chloro-8-(((3-(hydroxymethyl)oxetan-3-yl)methyl)thio)-6-(trifluoromethyl)quinazoline-2,4(1H, 3H)-dione (3) (72.7 g, 183.23 mmol) and tributylphosphine (96.12 g, 366.46 mmol) in tetrahydrofuran (7000 mL) was added diisopropylazodicarboxylate (74.10 g, 366.46 mmol) at 0° C. under nitrogen atmosphere. The mixture was stirred at room temperature for 18 hours. After completion, the mixture was poured into ice-water (7000 mL) and extracted with ethyl acetate (3×7000 mL). The organic phase was concentrated and the residue was purified by silica column (with 0.2%-1% methanol in dichloromethane) to afford the crude product 11-chloro-10-(trifluoromethyl)-2H-spiro[[1, 4]thiazepino[2,3,4-ij] quinazoline-3,3'-oxetane]-6,8(4H, 7H)-dione (4) (34.10 g, yield:49%) as a pale yellow solid. MS (ESI) m/z 376.9 $[M-H]^-$.

Step 4: tert-butyl 4-(11-chloro-6-oxo-10-(trifluoromethyl)-4,6-dihydro-2H-spiro[[1,4]thiazepino[2,3, 4-ij]quinazoline-3,3'-oxetan]-8-yl)piperazine-1-carboxylate (5)

To a mixture of 11-chloro-10-(trifluoromethyl)-2H-spiro [[1,4]thiazepino[2,3,4-ij]quinazoline-3,3'-oxetane]-6,8(4H, 7H)-dione (4) (700 mg, 1.85 mmol) and potassium carbonate (2.55 g, 18.48 mmol) in acetonitrile (40 mL) and dichloromethane (10 mL) was added 2,4,6-triisopropylbenzenesulfonyl chloride (839 mg, 2.77 mmol) at 25° C. The mixture was stirred at 25° C. for 6 hours. tert-butyl piperazine-1-carboxylate (516 mg, 2.77 mmol) was added into the reaction solution. The reaction mixture was stirred at 25° C. for 1 hour. The mixture was poured into ice-water (50 mL) and extracted with ethyl acetate (3×50 mL). The organic phase was concentrated and the residue was purified by flash silica column (with 0.2%-1% methanol in dichloromethane) to afford tert-butyl 4-(11-chloro-6-oxo-10-(trifluoromethyl)-4,6-dihydro-2H-spiro[[1,4]thiazepino[2,3,4-ij]quinazoline-3,3'-oxetan]-8-yl)piperazine-1-carboxylate (5) (600 mg, yield: 59%) as a pale-yellow solid. MS (ESI) m/z 547.99 [M+H]+.

Step 5: tert-butyl 4-(11-(3-chloro-4-fluorophenyl)-6-oxo-10-(trifluoromethyl)-4,6-dihydro-2H-spiro[[1,4] thiazepino[2,3,4-ij]quinazoline-3,3'-oxetan]-8-yl) piperazine-1-carboxylate (6)

To a solution of tert-butyl 4-(11-chloro-6-oxo-10-(trifluoromethyl)-4,6-dihydro-2H-spiro[[1,4]thiazepino[2,3,4-ij] quinazoline-3,3'-oxetan]-8-yl)piperazine-1-carboxylate (5) (150 mg, 0.27 mmol) in 1,4-dioxane (20 mL) and water (5 mL) were added tripotassium phosphate trihydrate (219 mg, 0.82 mmol), (3-chloro-4-fluorophenyl)boronic acid (190 mg, 1.10 mmol), and chloro(2-dicyclohexylphosphino-2',6'-diisopropoxy-1,1'-biphenyl)[2-(2'-amino-1,1'-biphenyl)] palladium(II) (21 mg, 0.03 mmol). The mixture was stirred at 85° C. under nitrogen atmosphere for 3 hours. After completion, the mixture was concentrated and the residue was purified by silica gel column chromatography (with 1%-3% methanol in dichloromethane) to afford tert-butyl 4-(11-(3-chloro-4-fluorophenyl)-6-oxo-10-(trifluoromethyl)-4,6-dihydro-2H-spiro[[1,4]thiazepino[2,3,4-ij]quinazoline-3,3'-oxetan]-8-yl)piperazine-1-carboxylate (6) (148 mg, yield: 84%) as a yellow solid. MS (ESI) m/z 642.1 $[M+H]^+$.

Step 6: 11-(3-chloro-4-fluorophenyl)-8-(piperazin-1-yl)-10-(trifluoromethyl)-2H-spiro[[1,4]thiazepino[2,3,4-ij]quinazoline-3,3'-oxetan]-6(4H)-one (7)

To a cooled mixture of tert-butyl 4-(11-(3-chloro-4-fluorophenyl)-6-oxo-10-(trifluoromethyl)-4,6-dihydro-2H-spiro[[1,4]thiazepino[2,3,4-ij]quinazoline-3,3'-oxetan]-8-yl)piperazine-1-carboxylate (6) (148 mg, 0.27 mmol) in dichloromethane (5 mL) was added trifluoroacetic acid (1 mL) at 0° C. The reaction solution was stirred at room temperature for 1 hour. The mixture was concentrated. The residue was redissolved in dichloromethane and washed with saturated $NaHCO_3$. The organic layer was dried over $Na_2SO_4$ and concentrated. The mixture was concentrated and the residue was purified by silica gel column chromatography (with 7% methanol in dichloromethane) to afford 11-(3-chloro-4-fluorophenyl)-8-(piperazin-1-yl)-10-(trifluoromethyl)-2H-spiro[[1,4]thiazepino[2,3,4-ij]quinazoline-3,3'-oxetan]-6(4H)-one (7) (97 mg, yield: 78%) as a yellow solid. MS (ESI) m/z 542.1 $[M+H]^+$.

Step 7: 8-(4-acryloylpiperazin-1-yl)-11-(3-chloro-4-fluorophenyl)-10-(trifluoromethyl)-2H-spiro[[1,4]thiazepino[2,3,4-ij]quinazoline-3,3'-oxetan]-6(4H)-one (8)

To a mixture of 11-(3-chloro-4-fluorophenyl)-8-(piperazin-1-yl)-10-(trifluoromethyl)-2H-spiro[[1,4]thiazepino[2,3,4-ij]quinazoline-3,3'-oxetan]-6(4H)-one (7) (81 mg, 0.15 mmol) and triethyl amine (23 g, 0.22 mmol) in dichloromethane (2 mL) was added acrylic anhydride (22 mg, 0.18 mmol) at 0° C. The mixture was stirred at 0° C. for 1 hour. The mixture was poured into ice-water (2 mL) and extracted with ethyl acetate (3×2 mL). The organic phase was concentrated and the residue was purified by silica gel column chromatography (with 2% methanol in dichloromethane) to afford 8-(4-acryloylpiperazin-1-yl)-11-(3-chloro-4-fluorophenyl)-10-(trifluoromethyl)-2H-spiro[[1,4]thiazepino[2,3,4-ij]quinazoline-3,3'-oxetan]-6(4H)-one (8) (69 mg, yield: 78%) as a pale-white solid. MS (ESI) m/z 596.1.0 $[M+H]^+$; $^1H$ NMR (400 MHz, $CDCl_3$) δ 7.81 (s, 1H), 7.30-7.23 (m, 2H), 7.11-7.09 (m, 1H), 6.62-6.55 (m, 1H), 6.39-6.35 (m, 1H), 5.82-5.78 (m, 1H), 5.14-4.64 (m, 3.5H), 4.36-4.33 (m, 2H), 4.00-3.73 (m, 8.5H), 3.42-3.39 (m, 2H).

Example 1358: (S)-7-(4-acryloylpiperazin-1-yl)-10-(4-fluorophenyl)-3-((methoxymethoxy)methyl)-9-(trifluoromethyl)-2H-[1,4]thiazino[2,3,4-ij]quinazolin-5(3H)-one

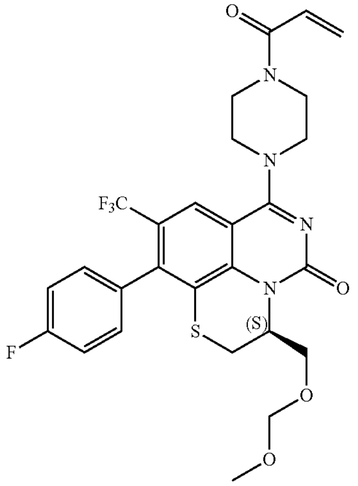

The title compound was prepared according to the scheme below.

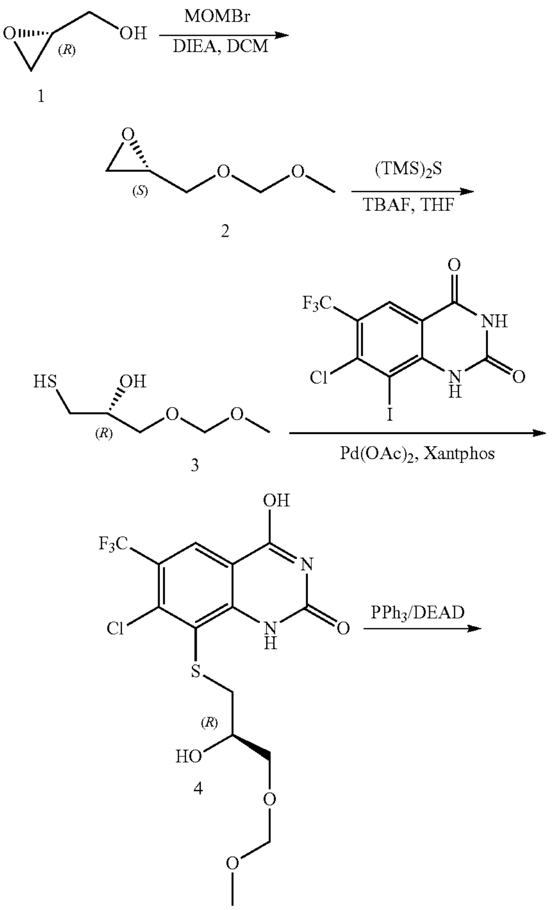

-continued

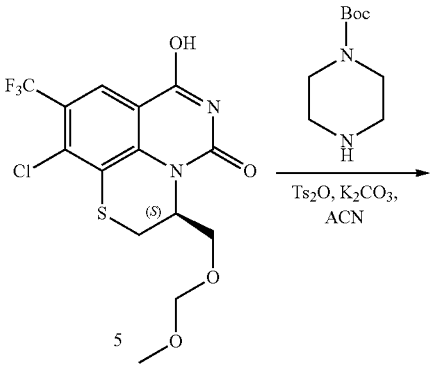

5

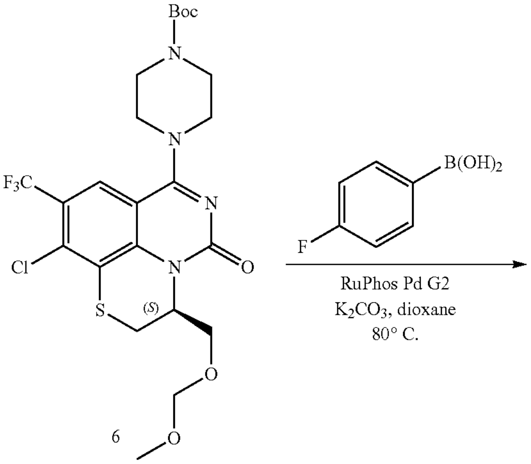

6

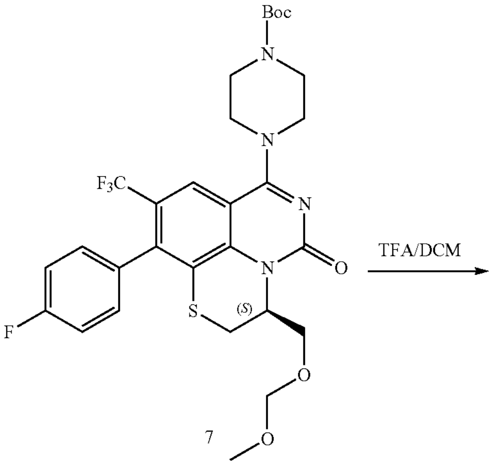

7

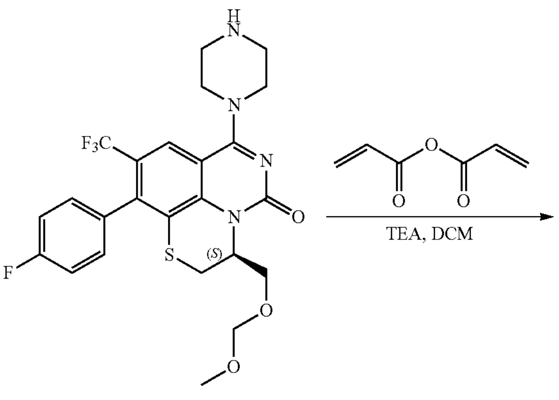

8

-continued

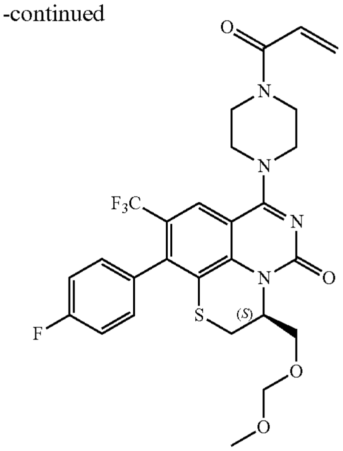

9

Step 1: (S)-2-((methoxymethoxy)methyl)oxirane (2)

To a mixture of (R)-oxiran-2-ylmethanol (1) (15 g, 202.7 mmol) and N,N-diisopropylethylamine (52.3 g, 405.4 mmol) in dichloromethane (200 mL) was added bromo (methoxy)methane (32.7 g, 263.5 mmol). The mixture was stirred at 0° C. to room temperature for 5 hours. After completion, the mixture was poured into dichloromethane (300 mL), washed with water (3×200 mL). The organic phase was washed with brine (100 mL) and dried over anhydrous sodium sulfate. After filtration and concentration, the residue was purified by silica gel column with petroleum ether to afford (S)-2-((methoxymethoxy)methyl)oxirane (2) (25.00 g, crude) as colorless oil; $^1$H NMR (400 MHz, $CDCl_3$) δ 4.66 (d, J=1.2 Hz, 2H), 3.79 (dd, J=11.6 Hz, 3.2 Hz, 1H), 3.51 (dd, J=11.6 Hz, 2.0 Hz, 1H), 3.38 (s, 3H), 3.20-3.16 (m, 1H), 2.83-2.80 (m, 1H), 2.64 (dd, J=5.2 Hz, 2.8 Hz, 1H).

Step 2: (R)-1-mercapto-3-(methoxymethoxy)propan-2-ol (3)

To a mixture of (S)-2-((methoxymethoxy)methyl)oxirane (2) (10 g, 84.7 mmol) in tetrahydrofuran (250 mL) was added 1,1,1,3,3,3-hexamethyldisilathiane (16.63 g, 93.2 mmol) and tetrabutylammonium fluoride (1.0 M in tetrahydrofuran, 25 mL, 25 mmol) at 0° C. The mixture was stirred at room temperature for 2 hours. After completion, the mixture concentrated under reduced pressure, the residue was purified by silica gel column with petroleum ether/ethyl acetate=4/1 to afford (R)-1-mercapto-3-(methoxymethoxy) propan-2-ol (3) (2 g, yield: 16%) as a colorless oil. $^1$H NMR (400 MHz, $CDCl_3$) δ 4.66 (s, 2H), 3.85-3.82 (m, 1H), 3.69-3.60 (m, 2H), 3.39 (s, 3H), 2.88 (brs, 1H), 2.71-2.65 (m, 2H), 1.51 (t, J 8.8 Hz, 1H).

Step 3: (R)-7-chloro-4-hydroxy-8-((2-hydroxy-3-(methoxymethoxy)propyl)thio)-6-(trifluoromethyl) quinazolin-2(1H)-one (4)

To a solution of 7-chloro-8-iodo-6-(trifluoromethyl)quinazoline-2,4(1H,3H)-dione (1.86 g, 4.77 mmol) in dioxane (40 mL) were added potassium carbonate (1.32 g, 9.54 mmol), (R)-1-mercapto-3-(methoxymethoxy)propan-2-ol (3) (1.09 g, 7.15 mmol), 4,5-bis(diphenyl-phosphino)-9,9-dimethylxanthene (413 mg, 0.72 mmol) and tris(dibenzylideneacetone) dipalladium (439 g, 0.48 mmol). The mixture was stirred at 60° C. under nitrogen atmosphere for 18 hours. After completion, the mixture was concentrated under reduced pressure. The residue was purified by silica gel column chromatography (dichloromethane/methanol=60/1) to afford (R)-7-chloro-4-hydroxy-8-((2-hydroxy-3-(methoxymethoxy)propyl)thio)-6-(trifluoromethyl)quinazolin-2(1H)-one (4) (1.33 g, yield: 67%) as pale yellow solid. MS (ESI) m/z 415.0 $[M+H]^+$.

Step 4: (S)-10-chloro-7-hydroxy-3-((methoxymethoxy)methyl)-9-(trifluoromethyl)-2H-[1,4]thiazino[2,3,4-ij]quinazolin-5(3H)-one (5)

To a mixture of (R)-7-chloro-4-hydroxy-8-((2-hydroxy-3-(methoxymethoxy)propyl)thio)-6-(trifluoromethyl)quinazolin-2(1H)-one (4) (1.33 g, 3.21 mmol) and triphenylphosphine (3.37 g, 12.85 mmol) in tetrahydrofuran (500 ml) was added diethyl azodicarboxylate (4.71 g, 12.85 mmol) at 0° C. The mixture was stirred at 0° C. for 45 min. After completion, the mixture was poured into ice-water (200 mL) and extracted with ethyl acetate (3×200 mL). Concentrated and the residue was purified by C18 with 30-95% acetonitrile in water to afford (S)-10-chloro-7-hydroxy-3-((methoxymethoxy)methyl)-9-(trifluoromethyl)-2H-[1,4]thiazino[2,3,4-ij]quinazolin-5(3H)-one (5) (1.1 g, yield: 87%) as a pale yellow solid. MS (ESI) m/z 397.0 $[M+H]^+$.

Step 5: (S)-tert-butyl 4-(10-chloro-3-((methoxymethoxy)methyl)-5-oxo-9-(trifluoromethyl)-3,5-dihydro-2H-[1,4]thiazino[2,3,4-ij]quinazolin-7-yl)piperazine-1-carboxylate (6)

To a mixture of (S)-10-chloro-7-hydroxy-3-((methoxymethoxy)methyl)-9-(trifluoromethyl)-2H-[1,4]thiazino[2,3,4-ij]quinazolin-5(3H)-one (5) (1.5 g, 3.78 mmol) and potassium carbonate (5.21 g, 37.8 mmol) in acetonitrile (35 mL) was added 4-methylbenzenesulfonic anhydride (3.08 g, 9.45 mmol) at 0° C. The mixture was stirred at room temperature for 4 hours. After completion, tert-butyl piperazine-1-carboxylate (2.82 g, 15.12 mmol) was added into the reaction solution. The reaction mixture was stirred at 0° C. for 1 hour. After completion, the mixture was poured into ice-water (50 mL) and extracted with ethyl acetate (3×50 mL). After concentration, the residue was purified by C18 column with 20-95% acetonitrile in water to afford (S)-tert-butyl 4-(10-chloro-3-((methoxymethoxy)methyl)-5-oxo-9-(trifluoromethyl)-3,5-dihydro-2H-[1,4]thiazino[2,3,4-ij]quinazolin-7-yl)piperazine-1-carboxylate (6) (1.7 g, yield: 81%) as a white solid. MS (ESI) m/z 565.2 $[M+H]^+$.

Step 6: (S)-tert-butyl 4-(10-(4-fluorophenyl)-3-((methoxymethoxy)methyl)-5-oxo-9-(trifluoromethyl)-3,5-dihydro-2H-[1,4]thiazino[2,3,4-ij]quinazolin-7-yl)piperazine-1-carboxylate (7)

To a solution of (S)-tert-butyl 4-(10-chloro-3-((methoxymethoxy)methyl)-5-oxo-9-(trifluoromethyl)-3,5-dihydro-2H-[1,4]thiazino[2,3,4-ij]quinazolin-7-yl)piperazine-1-carboxylate (6) (300 mg, 0.53 mmol) in 1,4-dioxane (10 mL) and water (2 mL) was added tripotassium phosphate (423 mg, 1.59 mmol), (4-fluorophenyl)boronic acid (418 mg, 2.65 mmol) and chloro(2-dicyclohexylphosphino-2', 6'-diisopropoxy-1,1'-biphenyl)[2-(2'-amino-1,1'-biphenyl)]palladium(II) (41 mg, 0.05 mmol). The mixture was stirred at 80° C. under nitrogen atmosphere for 2 hours. After completion, the mixture was concentrated under reduced pressure. The residue was purified by silica gel column chromatography (dichloromethane/methanol=100/1) to afford (S)-tert-butyl 4-(10-(4-fluorophenyl)-3-((methoxymethoxy)methyl)-5-oxo-9-(trifluoromethyl)-3,5-dihydro-2H-[1,4]thiazino[2,3,4-ij]quinazolin-7-yl)piperazine-1-carboxylate (7) (350 mg, crude) as a yellow solid. MS (ESI) m/z 625.3 $[M+H]^+$.

Step 7: (S)-10-(4-fluorophenyl)-3-((methoxymethoxy)methyl)-7-(piperazin-1-yl)-9-(trifluoromethyl)-2H-[1,4]thiazino[2,3,4-ij]quinazolin-5(3H)-one (8)

To a cooled mixture of (S)-tert-butyl 4-(10-(4-fluorophenyl)-3-((methoxymethoxy)methyl)-5-oxo-9-(trifluoromethyl)-3,5-dihydro-2H-[1,4]thiazino[2,3,4-ij]quinazolin-7-yl)piperazine-1-carboxylate (7) (350 mg, 0.56 mmol) in dichloromethane (8 mL) was added trifluoroacetic acid (2 mL) at 0° C. The reaction solution was stirred at room temperature for 1 hour. The solvent was removed under pressure. The residue was redissolved in dichloromethane and washed with saturated $NaHCO_3$. The organic layer was dried over $Na_2SO_4$ and concentrated. The residue was purified by silica gel column chromatography (dichloromethane/methanol=10/1) to afford (S)-10-(4-fluorophenyl)-3-((methoxymethoxy)methyl)-7-(piperazin-1-yl)-9-(trifluoromethyl)-2H-[1,4]thiazino[2,3,4-ij]quinazolin-5(3H)-one (8) (180 mg, three steps yield: 61%) as a yellow solid. MS (ESI) m/z 525.2 $[M+H]^+$.

Step 8: (S)-7-(4-acryloylpiperazin-1-yl)-10-(4-fluorophenyl)-3-((methoxymethoxy)methyl)-9-(trifluoromethyl)-2H-[1,4]thiazino[2,3,4-ij]quinazolin-5(3H)-one (9)

To a mixture of (S)-10-(4-fluorophenyl)-3-((methoxymethoxy)methyl)-7-(piperazin-1-yl)-9-(trifluoromethyl)-2H-[1,4]thiazino[2,3,4-ij]quinazolin-5(3H)-one (8) (180 mg, 0.34 mmol) and triethyl amine (104 mg, 1.03 mmol) in dichloromethane (5 ml) was added acrylic anhydride (64 mg, 0.51 mmol) at 0° C. The mixture was stirred at 0° C. for 1 hour. After completion, the mixture was poured into ice-water (30 mL) and extracted with dichloromethane (3×30 mL). After concentration, the residue was purified by preparative High Performance Liquid Chromatography (20% to 95% acetonitrile in water) to afford (S)-7-(4-acryloylpiperazin-1-yl)-10-(4-fluorophenyl)-3-((methoxymethoxy)methyl)-9-(trifluoromethyl)-2H-[1,4]thiazino[2,3,4-ij]quinazolin-5(3H)-one (9) (80 mg, yield: 41%) as a white solid. MS (ESI) m/z 579.2 $[M+H]^+$. $^1H$ NMR (400 MHz, $CDCl_3$) δ 7.80 (s, 1H), 7.24-7.15 (m, 4H), 6.63-6.56 (m, 1H), 6.39 (d, J=16.4 Hz, 1H), 5.80 (d, J=10.4 Hz, 1H), 5.46-5.45 (m, 1H), 4.67-4.62 (m, 2H), 4.02-3.95 (m, 3H), 3.81-3.79 (m, 7H), 3.35-3.33 (m, 4H), 3.01-2.98 (m, 1H).

Example 1366a: (3S,10S)-7-((3S,5R)-4-acryloyl-3,5-dimethylpiperazin-1-yl)-10-(4-fluoro-1-methyl-1H-indazol-7-yl)-3-(methoxymethyl)-9-(trifluoromethyl)-2,3-dihydro-5H-[1,4]thiazino[2,3,4-ij]quinazolin-5-one

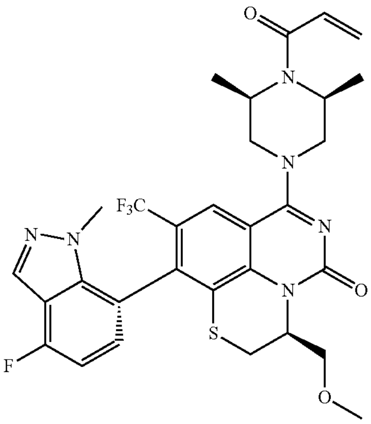

The title compound was prepared according to the scheme below.

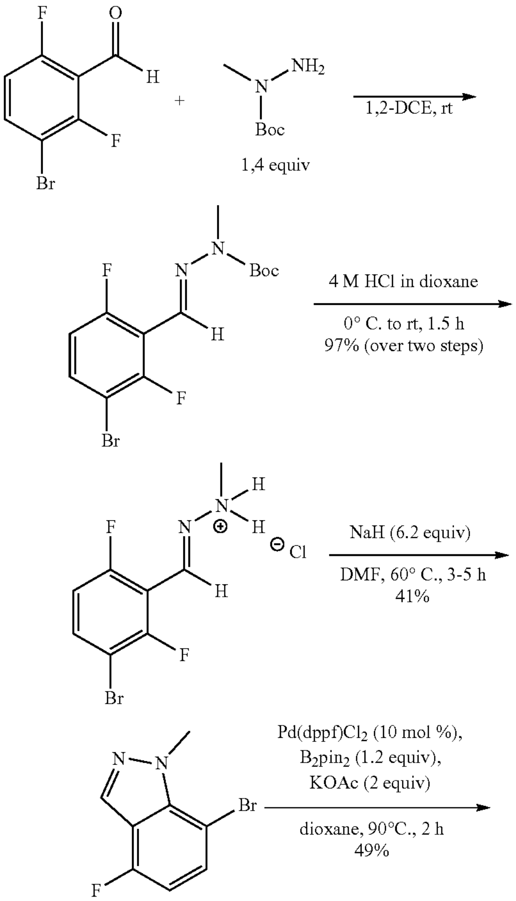

-continued

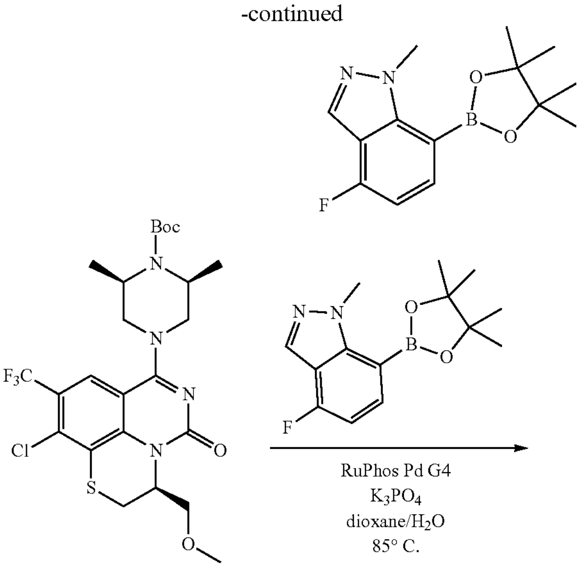

1

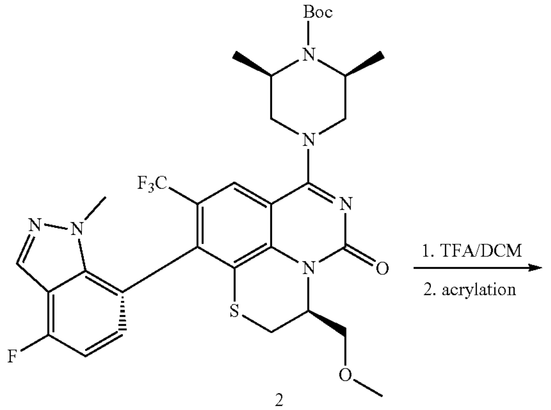

2

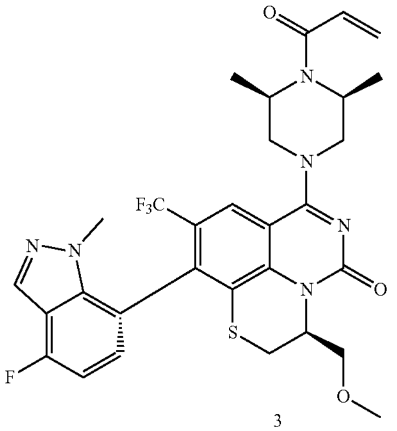

3

Step 1: (E)-2-(3-Bromo-2,6-difluorobenzylidene)-1-methylhydrazin-1-ium chloride

3-Bromo-2,6-difluorobenzaldehyde (5.5 g, 24.9 mmol, 1 equiv) was added to a 250 mL round-bottom flask under a $N_2$ atmosphere and dissolved in 1,2-dichloroethane (260 mL). Next, tert-butyl 1-methylhydrazine-1-carboxylate (5.2 mL, 34.86 mmol, 1.4 equiv, den. 0.985 g/mL) was added by syringe and the reaction mixture was stirred at room temperature. After 16 hours, the solvent was removed by rotary evaporation (full conversion determined by LC-MS). The resulting orange liquid was cooled to 0° C. and 4N HCl in 1,4-dioxane (60 mL) was added in portions (ca. 10 min). After 30 minutes, the ice-bath was removed, and the reaction mixture was stirred at room temperature for 1 hour. The resulting white precipitate was collected using a Buchner funnel, washed with $Et_2O$ (150 mL) and dried under high vacuum to afford (E)-2-(3-bromo-2,6-difluorobenzylidene)-1-methylhydrazin-1-ium chloride as an off-white solid (6.9 g, 97%): $^1$H NMR (400 MHz, DMSO-$d_6$) δ 8.89-8.27 (br s, 1H), 7.60-7.51 (m, 1H), 7.35-7.24 (m, 1H), 7.10 (t, J=10.0 Hz, 1H), 2.84 (s, 2H), 2.59 (s, 1H); LRMS-ESI (m/z) $[M+H]^+$ calculated for $C_8H_8BrF_2N_2$ 248.98, found 249.0.

Step 2: 7-Bromo-4-fluoro-1-methyl-1H-indazole

Sodium hydride (60 wt % in mineral oil, 2.2 g, 54.6 mmol, 5.2 equiv) was added to a 100 mL round-bottom flask under a $N_2$ atmosphere and purged with $N_2$ for 30 min prior to the addition of DMF (40 mL). Next, (E)-2-(3-bromo-2,6-difluorobenzylidene)-1-methylhydrazin-1-ium chloride (3.0 g, 10.5 mmol, 1 equiv) was added to the flask at room temperature in two portions and the resulting mixture was placed in a 60° C. oil bath and stirred. After 1 hour, additional sodium hydride (60 wt % in mineral oil, 420 mg, 10.5 mmol, 1 equiv) was added at 60° C. After 3 h, the flask was removed from the oil bath, cooled 0° C., and saturated aqueous $NH_4Cl$ (ca. 2 mL) was slowly added to the mixture. The resulting solution was transferred to a separatory funnel using EtOAc (300 mL). The organic layer was washed with saturated aqueous $NH_4Cl$ (50 mL), $H_2O$ (3×50 mL), and the solvent was removed by rotary evaporation. The crude material was purified by flash column chromatography using an Isolera One Biotage instrument (0-5% EtOAc/hexanes, 50 g column, 0% (5 CV), 0-5% (10 CV), 5% (5 CV)), to provide the title compound (1 g, 41%) as an orange solid: TLC (5% EtOAc/hexanes) $R_f$=0.28; $^1$H NMR (400 MHz, $CDCl_3$) δ 8.03 (s, 1H), 7.44 (dd, J=8.2, 4.5 Hz, 1H), 6.65 (t, J=8.6 Hz, 1H), 4.42 (s, 3H); LRMS-ESI (m/z) $[M+H]^+$ calculated for $C_8H_7BrFN_2$ 228.98, found 229.1.

Step 3: 4-Fluoro-1-methyl-7-(4,4,5,5-tetramethyl-1,3,2-dioxaborolan-2-yl)-1H-indazole 7-Bromo-4-fluoro-1-methyl-1H-indazole (200 mg, 0.87 mmol, 1 equiv) was dissolved in 1,4-dioxane (12 mL, 0.07 M) in a 50 mL bomb-flask. The resulting mixture was purged with $N_2$ for 30 min prior to the addition of Pd(dppf)$Cl_2$ (64 mg, 0.087 mmol, 10 mol %), KOAc (171 mg, 1.74 mmol, 2 equiv), and $B_2(pin)_2$ (265 mg, 1.044 mmol, 1.2 equiv), and then bubbled with $N_2$ for an additional 5 min. The flask placed on a heated block at 90° C. An additional 200 mg batch was set up using the same procedure. After 2 h, both batches were combined and filtered through Celite 545 using THF (50 mL) and the solvent was removed by rotary evaporation. The crude material was purified by flash column chromatography using an Isolera One Biotage instrument (0-5% EtOAc/hexanes, 25 g column, 0% (5 CV), 0-5% (10 CV), 5% (5 CV)), to provide the title compound (155 mg, 49%) as an orange solid: TLC (5% EtOAc/hexanes) $R_f$=0.32; $^1$H NMR (400 MHz, $CDCl_3$) δ 8.08 (s, 1H), 7.87 (dd, J=7.8, 5.8 Hz, 1H), 6.77 (dd, J=9.9, 8.1 Hz, 1H), 4.33 (s, 3H), 1.40 (s, 12H); LRMS-ESI (m/z) $[M+H]^+$ calculated for $C_{14}H_{19}BFN_2O_2$ 277.15, found 277.2.

Step 4: tert-butyl (2S,6R)-4-((3S,10S)-10-(4-fluoro-1-methyl-1H-indazol-7-yl)-3-(methoxymethyl)-5-oxo-9-(trifluoromethyl)-2,3-dihydro-5H-[1,4]thiazino[2,3,4-ij]quinazolin-7-yl)-2,6-dimethylpiperazine-1-carboxylate (2)

Compound 1 (25 mg, 0.044 mmol, 1 equiv) was dissolved in 1,4-dioxane and $H_2O$ (0.45 mL, 0.05 mL, respectively, 0.09 M). The resulting mixture was purged with $N_2$ for 30 min prior to the addition of RuPhos Pd G2 (5.1 mg, 0.0066 mmol, 15 mol %), $K_3PO_4$ (28 mg, 0.132 mmol, 3 equiv), and 4-fluoro-1-methyl-7-(4,4,5,5-tetramethyl-1,3,2-dioxaborolan-2-yl)-1H-indazole (36.4 mg, 0.132 mmol, 3 equiv). The microwave vial was fitted with a crimp-top cap, bubbled with $N_2$ for an additional 5 min, and placed on a heated block at 85° C. The resulting reaction mixture was homogenous. After 5 hours, the vial was removed from the heating block, allowed to cool, and the solvent was removed by rotary evaporation. The crude material was purified by preparative thin-layer chromatography (Silica Gel 60 $F_{254}$, 0.5 mm, 20×20 cm, 2 plates) using 3% MeOH/$CH_2Cl_2$ to provide 15 mg of compound 2 as a yellow oil in decent purity. The material was used in the subsequent step: TLC (3% MeOH/$CH_2Cl_2$) $R_f$=0.27; $^1$H NMR (400 MHz, MeOH-$d_4$) δ 8.21 (s, 1H), 8.16 (s, 1H), 7.18 (dd, J=8.0, 4.7 Hz, 1H), 6.97 (dd, J=9.7, 8.0 Hz, 1H), 5.39-5.32 (m, 1H), 4.45-4.14 (m, 4H), 3.73-3.60 (m, 2H), 3.56 (s, 3H), 3.49-3.33 (m, 3H), 3.36 (s, 3H), 3.15 (dd, J=13.6, 3.0 Hz, 1H), 1.53 (d, J=7.0 Hz, 3H), 1.51 (s, 9H), 1.35 (d, J=6.8 Hz, 3H); LRMS-ESI (m/z) $[M+H]^+$ calculated for $C_{32}H_{37}F_4N_6O_4S$ 677.25, found 677.3.

Step 5: (3S,10S)-7-((3S,5R)-4-acryloyl-3,5-dimethylpiperazin-1-yl)-10-(4-fluoro-1-methyl-1H-indazol-7-yl)-3-(methoxymethyl)-9-(trifluoromethyl)-2,3-dihydro-5H-[1,4]thiazino[2,3,4-ij]quinazolin-5-one (3)

The reactions of deBoc and acrylation were carried out by using the same procedures described in other examples. 2.5 mg (yield: 19%) of title compound 3 was obtained as white solid. $^1$H NMR (400 MHz, MeOH-$d_4$) δ 8.22 (s, 1H), 8.16 (s, 1H), 7.18 (dd, J=8.0, 4.8 Hz, 1H), 6.98 (dd, J=9.7, 7.9 Hz, 1H), 6.85 (dd, J=16.7, 10.6 Hz, 1H), 6.30 (dd, J=16.6, 2.0 Hz, 1H), 5.81 (dd, J=10.6, 2.0 Hz, 1H), 5.41-5.31 (m, 1H), 4.84-4.55 (m, 2H), 4.39 (d, J=13.6 Hz, 1H), 4.30 (d, J=13.6 Hz, 1H), 3.74-3.60 (m, 3H), 3.56 (s, 3H), 3.55-3.37 (m, 3H), 3.36 (s, 3H), 3.35-3.33 (m, 1H), 3.15 (dd, J=13.7, 3.0 Hz, 1H), 1.60 (d, J=6.9 Hz, 3H), 1.42 (d, J=7.0 Hz, 3H); LRMS-ESI (m/z) $[M+H]^+$ calculated for $C_{30}H_{31}F_4N_6O_3S$ 631.21, found 631.3.

Example 1375 and 1376: (3S,10R)-7-((3S,5R)-4-acryloyl-3,5-dimethylpiperazin-1-yl)-10-(5-chloro-2,4-difluorophenyl)-3-((dimethylamino)methyl)-9-(trifluoromethyl)-2,3-dihydro-5H-[1,4]thiazino[2,3,4-ij]quinazolin-5-one (P1) and (3S,10S)-7-((3S,5R)-4-acryloyl-3,5-dimethylpiperazin-1-yl)-10-(5-chloro-2,4-difluorophenyl)-3-((dimethylamino)methyl)-9-(trifluoromethyl)-2,3-dihydro-5H-[1,4]thiazino[2,3,4-ij]quinazolin-5-one (P2)

P1

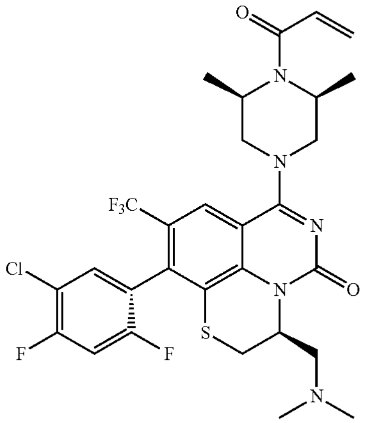

P2

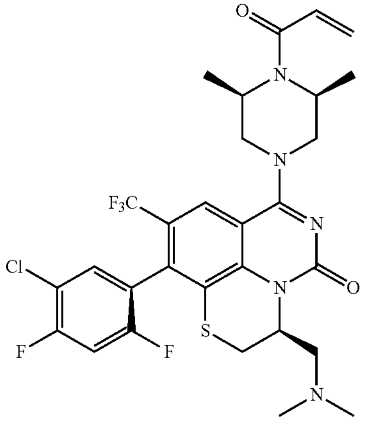

The title compounds were prepared according the scheme below.

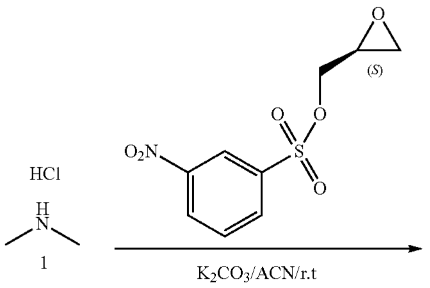

-continued

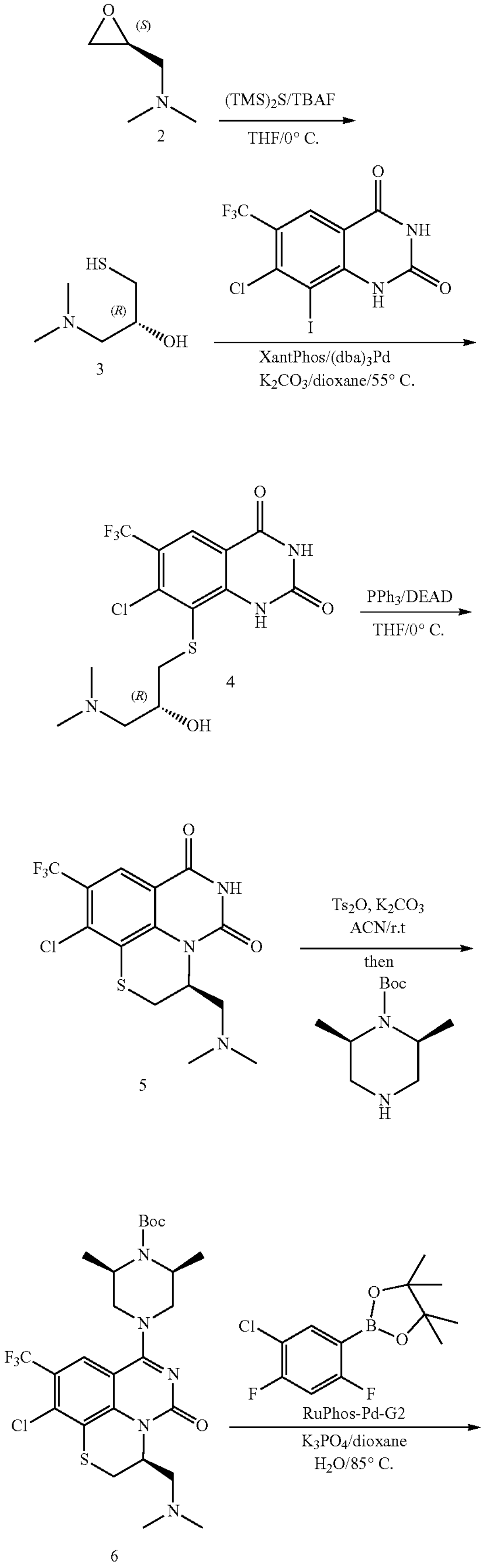

-continued

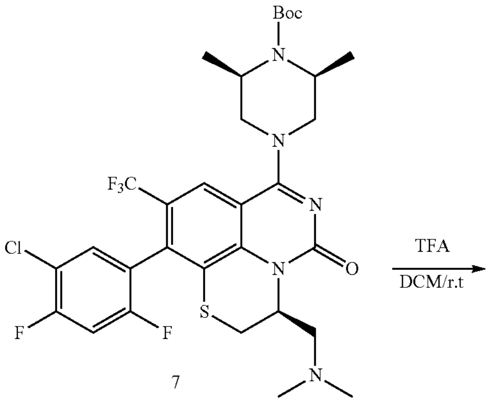

7

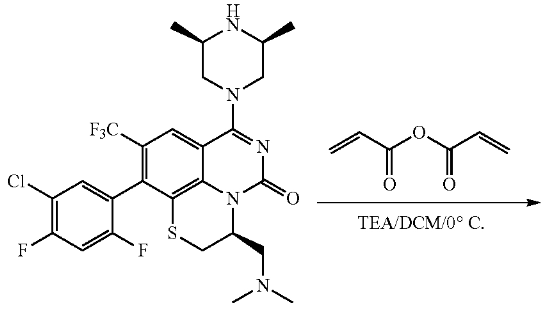

8

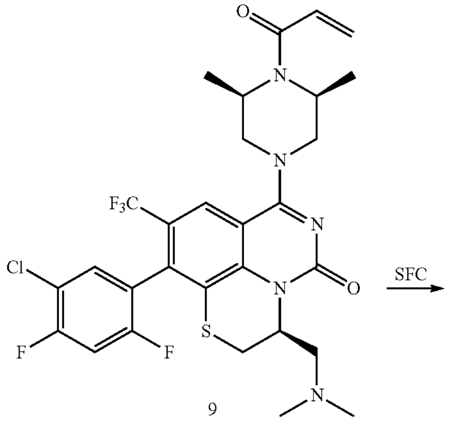

9

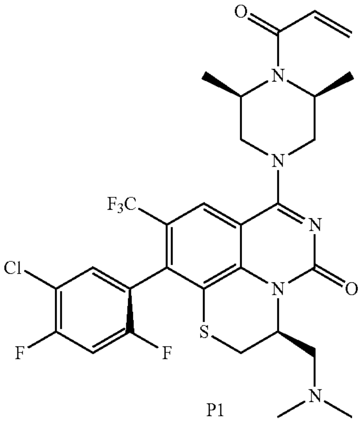

P1

+

-continued

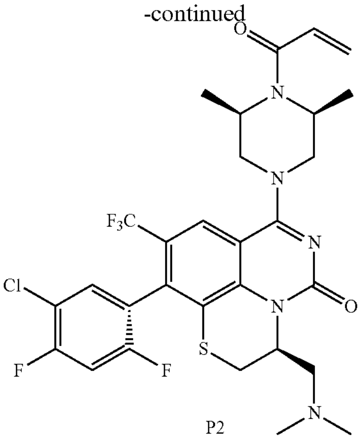

P2

Step 1: (S)—N,N-dimethyl-1-(oxiran-2-yl)methanamine (2)

The solution of (S)-oxiran-2-ylmethyl 3-nitrobenzenesulfonate (35 g, 135 mmol) in acetonitrile (150 mL) was added dimethylamine hydrochloride (10.0 g, 122.7 mmol) and potassium carbonate (50.8 g, 368.1 mmol) at 0° C. under nitrogen atmosphere. The mixture was stirred under nitrogen atmosphere at room temperature for 16 hours. After completion, the mixture was concentrated and the residue was purified by silica gel column with dichloromethane/methanol=30/1 to afford the product (2) (3.5 g, yield: 28%) as a colorless oil. $^{1}H$ NMR (400 MHz, $CDCl_3$) δ 3.10-3.06 (m, 1H), 2.78 (t, J=4.8 Hz, 1H), 2.68-2.63 (m, 1H), 2.50-2.48 (m, 1H), 2.33 (s, 6H), 2.27-2.22 (m, 1H).

Step 2: (R)-1-(dimethylamino)-3-mercaptopropan-2-ol (3)

To a mixture of (S)—N,N-dimethyl-1-(oxiran-2-yl)methanamine (2) (3 g, 29.7 mmol) in tetrahydrofuran (30 mL) were added 1,1,1,3,3,3-hexamethyldisilathiane (5.3 g, 29.7 mmol) and tetrabutylammonium fluoride (1.0 M in tetrahydrofuran, 9 mL, 8.9 mmol) at 0° C. The mixture was stirred at room temperature for 2 hours. After completion, the mixture was concentrated under reduced pressure to afford crude (R)-1-(dimethylamino)-3-mercaptopropan-2-ol (3) (4.5 g, crude) as yellow solid.

Step 3: (R)-7-chloro-8-((3-(dimethylamino)-2-hydroxypropyl)thio)-6-(trifluoromethyl)quinazoline-2,4(1H,3H)-dione (4)

To a solution of 7-chloro-4-hydroxy-8-iodo-6-(trifluoromethyl)quinazolin-2(1H)-one (3.86 g, 9.90 mmol) in dioxane (120 mL) were added potassium carbonate (4.1 g, 29.7 mmol), crude (R)-1-(dimethylamino)-3-mercaptopropan-2-ol (4.5 g), 4,5-bis(diphenyl-phosphino)-9,9-dimethylxanthene (858 mg, 1.48 mmol) and tris(dibenzylideneacetone) dipalladium (905 mg, 0.99 mmol). The mixture was stirred at 60° C. under nitrogen atmosphere for 18 hours. After completion, the mixture was diluted with tetrahydrofuran (200 mL) and the insoluble was filtered out. The filtrate was concentrated and the residue was purified by silica gel column chromatography (dichloromethane/ammonia methanol=20/1) to afford (R)-7-chloro-8-((3-(dimethylamino)-2-hydroxypropyl)thio)-6-(trifluoromethyl)quinazoline-2,4(1H,3H)-dione (4) (1.8 g, yield: 46%) as a yellow solid. MS (ESI) m/z 398.1 $[M+H]^+$.

Step 4: (S)-10-chloro-3-((dimethylamino)methyl)-9-(trifluoromethyl)-2H-[1,4]thiazino[2,3,4-ij]quinazoline-5,7(3H,6H)-dione (5)

To a mixture of (R)-7-chloro-8-((3-(dimethylamino)-2-hydroxypropyl)thio)-6-(trifluoromethyl)quinazoline-2,4(1H,3H)-dione (1.7 g, 4.28 mmol) and triphenylphosphine (3.36 g, 12.84 mmol) in tetrahydrofuran (420 mL) was added diethyl azodicarboxylate (2.23 g, 12.84 mmol) at 0° C. The mixture was stirred at 0° C. for 45 min. After completion, the mixture was poured into ice-water (200 mL) and extracted with ethyl acetate (3×200 mL). Concentrated and the residue was purified by flash chromatography column (C18, acetonitrile/water=30% to 95%) to afford (S)-10-chloro-3-((dimethylamino)methyl)-9-(trifluoromethyl)-2H-[1,4]thiazino[2,3,4-ij]quinazoline-5,7(3H,6H)-dione (5) (1.08 g, yield: 67%) as a pale yellow solid. MS (ESI) m/z 380.2 $[M+H]^+$.

Step 5: (2S,6R)-tert-butyl 4-((S)-10-chloro-3-((dimethylamino)methyl)-5-oxo-9-(trifluoromethyl)-3,5-dihydro-2H-[1,4]thiazino[2,3,4-ij]quinazolin-7-yl)-2,6-dimethylpiperazine-1-carboxylate (6)

To a mixture of (S)-10-chloro-3-((dimethylamino)methyl)-9-(trifluoromethyl)-2H-[1,4]thiazino[2,3,4-ij]quinazoline-5,7(3H,6H)-dione (5) (600 mg, 1.58 mmol) and potassium carbonate (2.18 g, 15.8 mmol) in acetonitrile (15 mL) was added 4-methylbenzenesulfonic anhydride (1.03 g, 3.16 mmol) at 25° C. The mixture was stirred at 25° C. for 3 hours. (2R,6S)-tert-butyl 2,6-dimethylpiperazine-1-carboxylate (1 g, 4.75 mmol) was added into the reaction solution. The reaction mixture was stirred at 25° C. for 1 hour. After completion, the mixture was poured into ice-water (50 mL) and extracted with ethyl acetate (3×50 mL). The mixture was concentrated and the residue was purified by flash chromatography column (C18, acetonitrile/water=20% to 95%) to afford (2S,6R)-tert-butyl 4-((S)-10-chloro-3-((dimethylamino)methyl)-5-oxo-9-(trifluoromethyl)-3,5-dihydro-2H-[1,4]thiazino[2,3,4-ij]quinazolin-7-yl)-2,6-dimethylpiperazine-1-carboxylate (6) (600 mg, yield: 66%) as a pale yellow solid. MS (ESI) m/z 576.3 $[M+H]^+$.

Step 6: (2S,6R)-tert-butyl 4-((3S)-10-(5-chloro-2,4-difluorophenyl)-3-((dimethylamino)methyl)-5-oxo-9-(trifluoromethyl)-3,5-dihydro-2H-[1,4]thiazino[2,3,4-ij]quinazolin-7-yl)-2,6-dimethylpiperazine-1-carboxylate (7)

To a solution of (2S,6R)-tert-butyl 4-((S)-10-chloro-3-((dimethylamino)methyl)-5-oxo-9-(trifluoromethyl)-3,5-dihydro-2H-[1,4]thiazino[2,3,4-ij]quinazolin-7-yl)-2,6-dimethylpiperazine-1-carboxylate (6) (400 mg, 0.7 mmol) in 1,4-dioxane (7 mL) and water (1 mL) were added tripotassium phosphate (559 mg, 2.1 mmol), 2-(5-chloro-2,4-difluorophenyl)-4,4,5,5-tetramethyl-1,3,2-dioxaborolane (955 mg, 3.48 mmol), and chloro(2-dicyclohexylphosphino-2',6'-diisopropoxy-1,1'-biphenyl)[2-(2'-amino-1,1'-biphenyl)]palladium(II) (54 mg, 0.07 mmol). The mixture was stirred at 85° C. under nitrogen atmosphere for 4 hours. After completion, the mixture was concentrated and the residue was purified by silica gel column chromatography (dichloromethane/methanol=60/1) to afford (2S,6R)-tert-butyl 4-((3S)-10-(5-chloro-2,4-difluorophenyl)-3-((dimethylamino)methyl)-5-oxo-9-(trifluoromethyl)-3,5-dihydro-2H-[1,4]thiazino[2,3,4-ij]quinazolin-7-yl)-2,6-dimethylpiperazine-1-carboxylate (7) (400 mg, yield: 83%) as a yellow solid. MS (ESI) m/z 688.1 $[M+H]^+$.

Step 7: (3S)-10-(5-chloro-2,4-difluorophenyl)-3-((dimethylamino)methyl)-7-((3S,5R)-3,5-dimethylpiperazin-1-yl)-9-(trifluoromethyl)-2H-[1,4]thiazino[2,3,4-ij]quinazolin-5(3H)-one (8)

To a cooled mixture of (2S,6R)-tert-butyl 4-((3S)-10-(5-chloro-2,4-difluorophenyl)-3-((dimethylamino)methyl)-5-oxo-9-(trifluoromethyl)-3,5-dihydro-2H-[1,4]thiazino[2,3,4-ij]quinazolin-7-yl)-2,6-dimethylpiperazine-1-carboxylate (7) (400 mg, 0.58 mmol) in dichloromethane (4 mL) was added trifluoroacetic acid (2 mL) at 0° C. The reaction solution was stirred at room temperature for 1 hour. After completion, the mixture was concentrated. The residue was redissolved in dichloromethane and washed with saturated $NaHCO_3$. The organic layer was dried over $Na_2SO_4$ and concentrated. The residue was purified by silica gel column chromatography (dichloromethane/ammonia methanol=30/1) to afford (3S)-10-(5-chloro-2,4-difluorophenyl)-3-((dimethylamino)methyl)-7-((3S,5R)-3,5-dimethylpiperazin-1-yl)-9-(trifluoromethyl)-2H-[1,4]thiazino[2,3,4-ij]quinazolin-5(3H)-one (8) (309 mg, yield: 91%) as a yellow solid. MS (ESI) m/z 588.1 [M+H]+.

Step 8: (3S)-7-((3S,5R)-4-acryloyl-3,5-dimethylpiperazin-1-yl)-10-(5-chloro-2,4-difluorophenyl)-3-((dimethylamino)methyl)-9-(trifluoromethyl)-2H-[1,4]thiazino[2,3,4-ij]quinazolin-5(3H)-one (9)

To a mixture of (3S)-10-(5-chloro-2,4-difluorophenyl)-3-((dimethylamino)methyl)-7-((3S,5R)-3,5-dimethylpiperazin-1-yl)-9-(trifluoromethyl)-2H-[1,4]thiazino[2,3,4-ij]quinazolin-5(3H)-one (309 mg, 0.526 mmol) and triethyl amine (8) (159 mg, 1.578 mmol) in dichloromethane (5 mL) was added acrylic anhydride (66 mg, 0.526 mmol) at 0° C. The mixture was stirred at 0° C. for 1 hour. After completion, the mixture was poured into ice-water (50 mL) and extracted with dichloromethane (3×30 mL). The mixture was concentrated and the residue was purified by preparative high performance liquid chromatography (20% to 95% acetonitrile in water) to afford (3S)-7-((3S,5R)-4-acryloyl-3,5-dimethylpiperazin-1-yl)-10-(5-chloro-2,4-difluorophenyl)-3-((dimethylamino)methyl)-9-(trifluoromethyl)-2H-[1,4]thiazino[2,3,4-ij]quinazolin-5(3H)-one (9) (152 mg, yield: 45%) as a white solid. MS (ESI) m/z 642.1 $[M+H]^+$.

The above racemate (152 mg) was dissolved in EtOH (5 mL) and separated by chiral supercritical fluid chromatography (separation condition: Column:Chiralpak IH 5 μm 20×250 mm; Mobile Phase: Hex:EtOH=80:20 at 25 mL/min; Temp: 25° C.; Wavelength: 254 nm) to afford Compound P1 (70 mg, 47% yield, 100% ee) and Compound P2 (35 mg, 23% yield, 99.3% ee); Chiral HPLC Analytical: on CHIRALPAK® IH was using 5 μm 4.6×250 mm column, Mobile Phase: Hex:EtOH=80:20 at 2.5 mL/min; Temp: 25° C.; Wavelength: 254 nm). P1: $^1H$ NMR (400 MHz, $CDCl_3$) δ 8.07 (s, 1H), 7.29-7.25 (m, 1H), 7.08 (t, J=8.8 Hz, 1H), 6.66-6.59 (m, 1H), 6.43-6.39 (m, 1H), 5.78 (dd, J=10.4 Hz, 2.0 Hz, 1H), 5.38-5.35 (m, 1H), 4.71-4.59 (m, 2H), 4.20-4.16 (m, 2H), 3.50-3.30 (m, 3H), 3.04-3.00 (m, 1H), 2.85-2.83 (m, 1H), 2.43-2.37 (m, 7H), 1.60 (d, J=7.2 Hz, 3H), 1.49 (d, J=7.2 Hz, 3H); Chiral SFC fraction 1: e.e. =100%, Rt=6.511 min. P2: $^1H$ NMR (400 MHz, $CDCl_3$) δ 8.07 (s, 1H), 7.29-7.25 (m, 1H), 7.07 (t, J=8.8 Hz, 1H), 6.66-6.59 (m, 1H), 6.43-6.39 (m, 1H), 5.78 (dd, J=10.0 Hz, 2.0 Hz, 1H), 5.40-5.38 (m, 1H), 4.69-4.58 (m, 2H), 4.20-4.17 (m, 2H), 3.51-3.30 (m, 3H), 3.02-2.78 (m, 2H), 2.37-2.23 (m, 7H), 1.61 (d, J=7.2 Hz, 3H), 1.48 (d, J=7.2 Hz, 3H); Chiral SFC fraction 1: e.e. =99.3%, Rt=11.174 min.

Example 1383: (3S)-7-(7-acryloyl-3-oxa-7,9-diazabicyclo[3.3.1]nonan-9-yl)-10-(4-fluorophenyl)-3-(methoxymethyl)-9-(trifluoromethyl)-2,3-dihydro-5H-[1,4]thiazino[2,3,4-ij]quinazolin-5-one

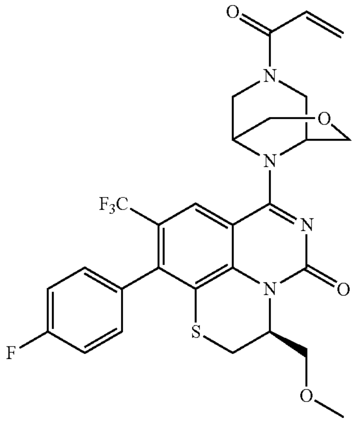 [SMILES: C=CC(=O)N1CC2COCC(C1)N2c1nc(=O)n2c3c(c(-c4ccc(F)cc4)c(C(F)(F)F)cc13)SC[C@@H]2COC]

The title compound was prepared according to the scheme below.

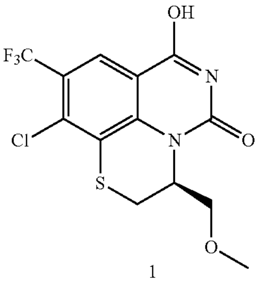

1

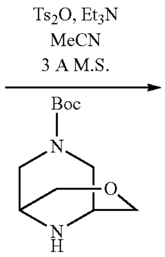

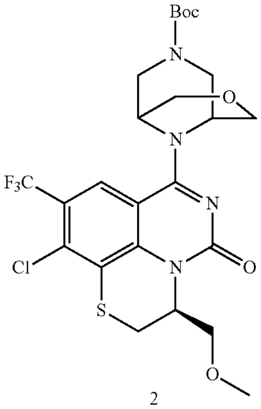

2

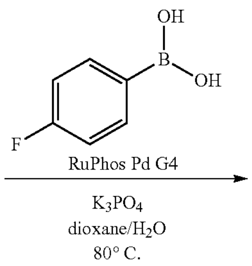

-continued

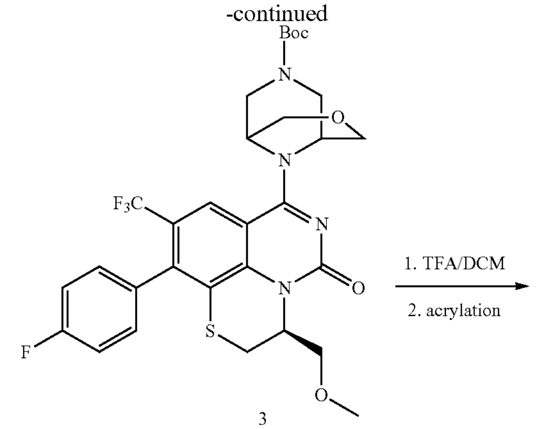

3

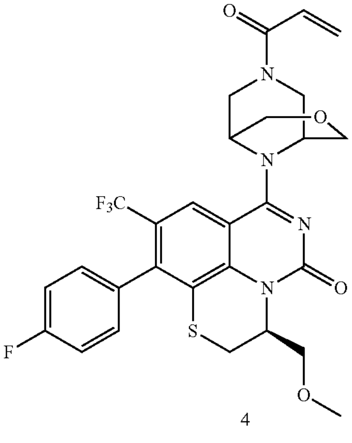

4

Step 1: tert-butyl 9-((S)-10-chloro-3-(methoxymethyl)-5-oxo-9-(trifluoromethyl)-2,3-dihydro-5H-[1,4]thiazino[2,3,4-ij]quinazolin-7-yl)-3-oxa-7,9-diazabicyclo[3.3.1]nonane-7-carboxylate (2)

Compound 1 (100 mg, 0.273 mmol, 1 equiv) was dissolved in MeCN (2.7 mL, 0.1 M) under a $N_2$ atmosphere in a 25 mL round bottom flask containing 3 Å molecular sieves. The resulting solution was stirred for ca. 30 min at room temperature. Next, $Et_3N$ (114 μL, 0.819 mmol, 3 equiv) was added by syringe followed by $Ts_2O$ (178 mg, 0.546 mmol, 2 equiv). The mixture was allowed to stir at room temperature for 19 hours. LCMS showed 90% conversion. Next, tert-butyl 3-oxa-7,9-diazabicyclo[3.3.1]nonane-7-carboxylate (125 mg, 0.546 mmol, 2 equiv) and $Et_3N$ (76 μL, 0.546 mmol, 2 equiv) was dissolved in MeCN (2 mL) under a $N_2$ atmosphere in a 10 mL round bottom flask containing 3 Å molecular sieves. The resulting solution was stirred for ca. 30 min at room temperature. This solution was then added to the reaction mixture and stirred for an additional 1 hour. The intermediate was determined to be fully consumed by LC-MS and the solvent was removed by rotary evaporation.

The crude material was purified by flash column chromatography using an Isolera One Biotage instrument (0-75% EtOAc/hexanes, 10 g column, 0% (5 CV), 0-50% (10 CV), 50-75% (5 CV), 75% (10 CV)), to provide compound 2 (109 mg) as a pale-yellow solid: TLC (50% EtOAc/hexanes) $R_f$=0.05; $^1$H NMR (400 MHz, $CDCl_3$) δ 7.61 (s, 1H), 5.43 (tt, J=5.7, 2.9 Hz, 1H), 4.48 (dd, J=29.7, 13.7 Hz, 1H), 4.37-3.96 (m, 6H), 3.95-3.81 (m, 1H), 3.74-3.46 (m, 4H), 3.42 (s, 3H), 3.41-3.16 (m, 1H), 3.10 (dd, J=13.6, 2.9 Hz, 1H), 1.49 (s, 9H); LRMS-ESI (m/z) $[M+H]^+$ calculated for $C_{24}H_{29}ClF_3N_4O_5S$ 577.15, found 577.2.

Step 2: tert-butyl 9-((S)-10-(4-fluorophenyl)-3-(methoxymethyl)-5-oxo-9-(trifluoromethyl)-2,3-dihydro-5H-[1,4]thiazino[2,3,4-ij]quinazolin-7-yl)-3-oxa-7,9-diazabicyclo[3.3.1]nonane-7-carboxylate (3)

Compound 2 (50 mg, 0.087 mmol, 1 equiv) was dissolved in 1,4-dioxane and $H_2O$ (2.6 mL, 0.6 mL, respectively, 0.03 M). The resulting mixture was purged with $N_2$ for 30 min prior to the addition of RuPhos Pd G4 (7.4 mg, 0.0087 mmol, 10 mol %), $K_3PO_4$ (55 mg, 0.261 mmol, 3 equiv), and 4-fluorophenylboronic acid (61 mg, 0.435 mmol, 5 equiv). The microwave vial was fitted with a crimp-top cap, bubbled with $N_2$ for an additional 5 min, and placed on a heated block at 80° C. The resulting reaction mixture was homogenous. LCMS showed full conversion after 1 hour. The vial was removed from the heating block, allowed to cool, and the solvent was removed by rotary evaporation. The crude material was purified by flash column chromatography using an Isolera One Biotage instrument (0-100% EtOAc/hexanes, 10 g column, 0% (5 CV), 0-75% (10 CV), 75% (5 CV), 75-100% (2 CV), 100% (5 CV)), to provide title compound 3 (30 mg, 55%) as a white solid: TLC (50% EtOAc/hexanes) $R_f$=0.06; $^1$H NMR (400 MHz, $CDCl_3$) δ 7.67 (s, 1H), 7.24-7.12 (m, 2H), 5.42-5.30 (m, 1H), 4.60-4.26 (m, 5H), 4.26-3.84 (m, 5H), 3.79-3.52 (m, 4H), 3.39 (s, 3H), 3.48-3.20 (m, 3H), 2.97 (dd, J=13.5, 2.9 Hz, 1H), 1.48 (s, 9H); LRMS-ESI (m/z) $[M+H]^+$ calculated for $C_{30}H_{33}F_4N_4O_5S$ 637.21, found 637.3.

Step 3: (3S)-7-(7-acryloyl-3-oxa-7,9-diazabicyclo[3.3.1]nonan-9-yl)-10-(4-fluorophenyl)-3-(methoxymethyl)-9-(trifluoromethyl)-2,3-dihydro-5H-[1,4]thiazino[2,3,4-ij]quinazolin-5-one (4)

The reactions of deBoc and acrylation were carried out by using same procedure described in other examples. 22 mg (yield: 79%) of title compound 4 was obtained as white solid. $^1$H NMR (400 MHz, MeOH-$d_4$) δ 7.85 (d, J=3.2 Hz, 1H), 7.35-7.19 (m, 4H), 6.84 (ddd, J=17.3, 10.7, 7.0 Hz, 1H), 6.21 (d, J=16.7, 1H), 5.77 (d, J=10.7 Hz, 1H), 5.36-5.26 (m, 1H), 4.89-4.76 (m, 1H), 4.57-4.36 (m, 3H), 4.25-4.16 (m, 1H), 4.13-3.89 (m, 4H), 3.81-3.69 (m, 2H), 3.65-3.53 (m, 2H), 3.40 (s, 3H), 3.39-3.24 (m, 4H), 3.09 (dd, J=13.7, 2.8 Hz, 1H); LRMS-ESI (m/z) $[M+H]^+$ calculated for $C_{28}H_{27}F_4N_4O_4S$ 591.17, found 591.2.

Example 1407 and 1408: (R)-8-((3S,5R)-4-acryloyl-3,5-dimethylpiperazin-1-yl)-11-(4-fluorophenyl)-3-(methoxymethyl)-10-(trifluoromethyl)-3,4-dihydro-2H,6H-[1,4]thiazepino[2,3,4-ij]quinazolin-6-one (P1) and (S)-8-((3S,5R)-4-acryloyl-3,5-dimethylpiperazin-1-yl)-11-(4-fluorophenyl)-3-(methoxymethyl)-10-(trifluoromethyl)-3,4-dihydro-2H,6H-[1,4]thiazepino[2,3,4-ij]quinazolin-6-one (P2)

P1

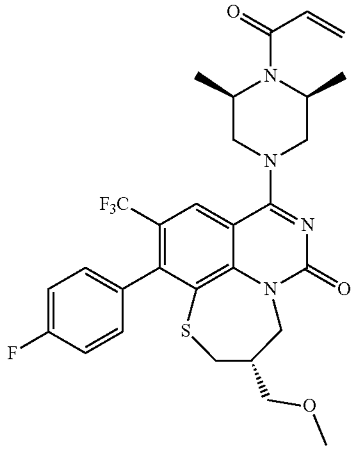

P2

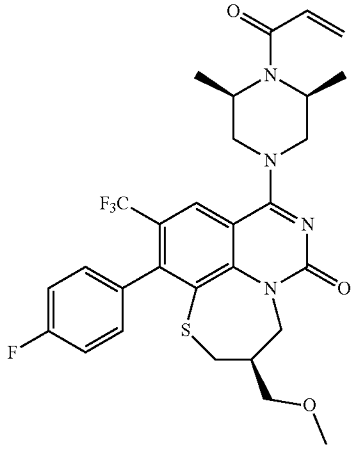

Step 1: 5-(methoxymethyl)-2,2-dimethyl-1,3-dioxane (2)

To a solution of (2,2-dimethyl-1,3-dioxan-5-yl)methanol (1) (14.6 g, 100 mmol) in tetrahydrofuran (200 mL) was added sodium hydride (12.2 g, 300 mmol) at 0° C. The mixture was stirred at room temperature for 0.5 hour. Then, iodomethane (71.1 g, 500 mmol) was added to the mixture. The mixture was stirred at room temperature for 2 hours. After completion, the mixture was poured into water (100 mL), extracted with ethyl acetate (3×200 mL). The combined organic phases were washed with brine (200 mL) and dried over anhydrous sodium sulfate. After filtration and concentration, the residue was purified by silica gel column with petroleum ether/ethyl acetate=3/1 to afford 5-(methoxymethyl)-2,2-dimethyl-1,3-dioxane (2) (12.9 g, 80%) as a yellow oil. $^1$H NMR (300 MHz, $CDCl_3$) δ 3.95

(dd, J=4.0 Hz, J=11.6 Hz, 2H), 3.74 (dd, J=6.4 Hz, J=11.6 Hz, 2H), 3.42 (d, J=6.8 Hz, 2H), 3.33 (s, 3H), 2.11-1.94 (m, 1H), 1.42 (s, 3H), 1.40 (s, 3H).

Step 2: 2-(methoxymethyl)propane-1,3-diol (3)

To a solution of 5-(methoxymethyl)-2,2-dimethyl-1,3-dioxane (2) (12.9 g, 80 mmol) in methanol (160 mL) was added p-toluenesulfonic acid (1.37 g, 8 mmol) at room temperature. The mixture was stirred at room temperature for 48 hours. After completion, The mixture was concentrated, the residue was purified by silica gel column with dichloromethane/methanol=10/1 to afford 2-(methoxymethyl)propane-1,3-diol (3) (9.58 g, 99%) as a yellow oil.

Step 3: 3-hydroxy-2-(methoxymethyl)propyl 4-methylbenzenesulfonate (4)

To a solution of 2-(methoxymethyl)propane-1,3-diol (3) (9.6 g, 80 mmol) in dichloromethane (160 mL) was added triethylamine (12.1 g, 120 mmol) and p-Toluenesulfonyl chloride (12.2 g, 64 mmol). The mixture was stirred at room temperature for 12 hours. After completion, the mixture was concentrated, the residue was purified by silica gel column with dichloromethane/methanol=30/1 to afford 3-hydroxy-2-(methoxymethyl)propyl 4-methylbenzenesulfonate (4) (8.59 g, crude) as a yellow oil.

Step 4: 3-mercapto-2-(methoxymethyl)propan-1-ol (5)

To a solution of 3-hydroxy-2-(methoxymethyl)propyl 4-methylbenzenesulfonate (4) (4.0 g, 14.6 mmol) in ethanol (70 mL) was added sodium hydrosulfide (3.5 g, 43.8 mmol). The mixture was stirred at room temperature for 6 hours. After completion, the mixture was concentrated, the residue was purified by silica gel column with dichloromethane/methanol=20/1 to afford 3-mercapto-2-(methoxymethyl) propan-1-ol (5) (1.8 g, crude) as a colorless oil.

Step 5: 7-chloro-8-((3-hydroxy-2-(methoxymethyl) propyl)thio)-6-(trifluoromethyl)quinazoline-2,4(1H, 3H)-dione (7)

To a solution of 7-chloro-8-iodo-6-(trifluoromethyl)quinazoline-2,4(1H,3H)-dione (6) (1.0 g, 2.5 mmol) in dioxane (50 mL) was added 3-mercapto-2-(methoxymethyl)propan-1-ol (5) (523 mg, 3.8 mmol), potassium carbonate (1.03 g, 7.5 mmol), 4,5-bis(diphenyl-phosphino)-9,9-dimethylxanthene (289 mg, 0.5 mmol) and tris(dibenzylideneacetone) dipalladium (229 mg, 0.25 mmol). The mixture was stirred at 55° C. for 4 hours. After completion, the mixture was concentrated, the residue was purified by silica gel column with dichloromethane/methanol=50/1 to afford 7-chloro-8-((3-hydroxy-2-(methoxymethyl)propyl)thio)-6-(trifluoromethyl)quinazoline-2,4(1H,3H)-dione (7) (400 mg, crude) as a white solid. MS (ESI): m/z 399.2 $[M+H]^+$.

Step 6: 11-chloro-3-(methoxymethyl)-10-(trifluoromethyl)-3,4-dihydro-[1,4]thiazepino[2,3,4-ij]quinazoline-6,8(2H,7H)-dione (8)

To a mixture of 7-chloro-8-((3-hydroxy-2-(methoxymethyl)propyl)thio)-6-(trifluoromethyl)quinazoline-2,4(1H, 3H)-dion (7) (400 mg, 1.0 mmol) and triphenylphosphine (420 mg, 1.5 mmol) in tetrahydrofuran (5 mL) was added diethyl azodicarboxylate (348 mg, 2.0 mmol) at 0° C. The mixture was stirred at 0° C. for 45 min. After completion, the mixture was concentrated and the residue was purified by reverse column (C18 with 5-95% ACN in H2O) to afford 11-chloro-3-(methoxymethyl)-10-(trifluoromethyl)-3,4-dihydro-[1,4]thiazepino[2,3,4-ij]quinazoline-6,8(2H,7H)-dione (8) (200 mg, crude) as a yellow solid. MS (ESI): m/z 381.1 $[M+H]^+$.

Step 7: (2S,6R)-tert-butyl 4-(11-chloro-3-(methoxymethyl)-6-oxo-10-(trifluoromethyl)-2,3,4,6-tetrahydro-[1,4]thiazepino[2,3,4-ij]quinazolin-8-yl)-2,6-dimethylpiperazine-1-carboxylate (9)

To a solution of (11-chloro-3-(methoxymethyl)-10-(trifluoromethyl)-3,4-dihydro-[1,4]thiazepino[2,3,4-ij]quinazoline-6,8(2H,7H)-dione (8) (200 mg, 0.52 mmol) and $K_2CO_3$ (359 mg, 2.6 mmol) in ACN (20 mL) was added p-Toluenesulfonic anhydride (169 mg, 1.04 mmol). The mixture was stirred at room temperature for 5 hours. Then (2S,6R)-tert-butyl 2,6-dimethylpiperazine-1-carboxylate (222 mg, 1.04 mmol) was added to above mixture. The mixture was stirred at room temperature for 2 hours. After completion, the mixture was concentrated under reduced pressure, and the residue was purified by silica gel column with DCM/EA=20%-80% to afford (2S,6R)-tert-butyl 4-(11-(4-fluorophenyl)-3-(methoxymethyl)-6-oxo-10-(trifluoromethyl)-2,3,4,6-tetrahydro-[1,4]thiazepino[2,3,4-ij] quinazolin-8-yl)-2,6-dimethylpiperazine-1-carboxylate (9) (290 m g, crude) as a yellow solid. MS (ESI) m/z 577.5 $[M+H]^+$.

Step 8: (2S,6R)-tert-butyl 4-(11-(4-fluorophenyl)-3-(methoxymethyl)-6-oxo-10-(trifluoromethyl)-2,3,4,6-tetrahydro-[1,4]thiazepino[2,3,4-ij]quinazolin-8-yl)-2,6-dimethylpiperazine-1-carboxylate (10)

To a solution of (2S,6R)-tert-butyl 4-(11-(4-fluorophenyl)-3-(methoxymethyl)-6-oxo-10-(trifluoromethyl)-2,3,4,6-tetrahydro-[1,4]thiazepino[2,3,4-ij]quinazolin-8-yl)-2,6-dimethylpiperazine-1-carboxylate (9) (290 mg, 0.5 mmol) in 1,4-dioxane (5 mL) and water (1 mL) was added tripotassium phosphate (390 mg, 1.5 mmol), (4-fluorophenyl)boronic acid (189 mg, 1.2 mmol) and chloro(2-dicyclohexylphosphino-2', 6'-diisopropoxy-1,1'-biphenyl)[2-(2'-amino-1,1'-biphenyl)]palladium(II) (19 mg, 0.024 mmol). The mixture was stirred at 80° C. under nitrogen atmosphere for 2 hours. After completion, the mixture was concentrated under reduced pressure, the residue was purified by silica gel column chromatography (dichloromethane/methanol=30/1) to afford (2S,6R)-tert-butyl 4-(11-(4-fluorophenyl)-3-(methoxymethyl)-6-oxo-10-(trifluoromethyl)-2,3,4,6-tetrahydro-[1,4]thiazepino[2,3,4-ij]quinazolin-8-yl)-2,6-dimethylpiperazine-1-carboxylate (10) (248 mg) as a yellow solid. MS (ESI) m/z 653.3 $[M+H]^+$.

Step 9: 8-((3S,5R)-4-acryloyl-3,5-dimethylpiperazin-1-yl)-11-(4-fluorophenyl)-3-(methoxymethyl)-10-(trifluoromethyl)-3,4-dihydro-[1,4]thiazepino[2,3,4-ij]quinazolin-6(2H)-one (11)

To a cooled mixture of (2S,6R)-tert-butyl 4-(11-(4-fluorophenyl)-3-(methoxymethyl)-6-oxo-10-(trifluoromethyl)-2,3,4,6-tetrahydro-[1,4]thiazepino[2,3,4-ij]quinazolin-8-yl)-2,6-dimethylpiperazine-1-carboxylate (10) (248 mg, 0.38 mmol) in dichloromethane (5 mL) was added trifluoroacetic acid (1 mL) at 0° C. The reaction solution was stirred at room temperature for 1 hour. The solvent was removed under pressure. The residue was redissolved in dichloromethane and washed with saturated $NaHCO_3$. The organic layer was dried over $Na_2SO_4$ and concentrated. The residue was purified by silica gel column chromatography (with 7% methanol in dichloromethane) to afford 8-((3S,5R)-3,5-dimethylpiperazin-1-yl)-11-(4-fluorophenyl)-3-(methoxymethyl)-10-(trifluoromethyl)-3,4-dihydro-[1,4]thiazepino[2,3,4-ij]quinazolin-6(2H)-one (200 mg, yield: 97%) as a yellow solid. MS (ESI) m/z 637.3 $[M+H]^+$.

To a mixture of 8-((3S,5R)-3,5-dimethylpiperazin-1-yl)-11-(4-fluorophenyl)-3-(methoxymethyl)-10-(trifluoromethyl)-3,4-dihydro-[1,4]thiazepino[2,3,4-ij]quinazolin-6(2H)-one (200 mg, 0.37 mmol) and triethyl amine (55 mg, 0.55 mmol) in dichloromethane (3 mL) was added acrylic anhydride (70 mg, 0.55 mmol) at 0° C. The mixture was stirred at 0° C. for 1 hour. After completion, the mixture was poured into ice-water (1 mL) and extracted with ethyl acetate (3x5 mL). The organic phase was concentrated and the residue was purified by silica gel column chromatography (with 2% methanol in dichloromethane) to afford 8-((3S,5R)-4-acryloyl-3,5-dimethylpiperazin-1-yl)-11-(4-fluorophenyl)-3-(methoxymethyl)-10-(trifluoromethyl)-3,4-dihydro-[1,4]thiazepino[2,3,4-ij]quinazolin-6(2H)-one (11) (82 mg, yield: 38%) as a pale-yellow solid. MS (ESI) m/z 591.2 $[M+H]^+$.

The above racemate (82 mg) was dissolved in EtOH (150 mL) and separated by chiral supercritical fluid chromatography (separation condition: Column:Chiralpak AD-H 5 μm 20×250 mm; Mobile Phase: Hex:EtOH=45:55 at 1 mL/min; Temp: 30° C.; Wavelength: 254 nm) to afford the title compounds P1 (40 mg, 48% yield) and P2 (42 mg, 42% yield); Chiral HPLC Analytical: on CHIRALPAK® AD-H was using 5 μm 4.6×250 mm column, Mobile Phase: Hex: EtOH=45:55 at 1 mL/min; Temp: 30° C.; Wavelength: 254 nm). P1: $^1H$ NMR (400 MHz, $CDCl_3$) δ 8.06 (s, 1H), 7.23-7.15 (m, 4H), 6.63 (dd, J=2.0 Hz, J=16.4 Hz, 1H), 6.41 (dd, J=1.6 Hz, J=14.4 Hz, 1H), 5.77 (dd, J=2.0 Hz, J=10.4 Hz, 1H), 4.67-4.62 (m, 4H), 4.16 (d, J=13.2 Hz, 2H), 3.52-3.46 (m, 1H), 3.35-3.31 (m, 6H), 3.26-3.18 (m, 1H), 3.02 (dd, J=4.4 Hz, J=14.8 Hz, 1H), 2.76-2.58 (m, 1H), 1.57-1.53 (m, 6H). P2: $^1H$ NMR (400 MHz, $CDCl_3$) δ 8.06 (s, 1H), 7.23-7.15 (m, 4H), 6.62 (dd, J=10.4 Hz, J=16.8 Hz, 1H), 6.41 (dd, J=1.6 Hz, J=16.4 Hz, 1H), 5.77 (dd, J=2.0 Hz, J=10.4 Hz, 1H), 4.73-4.52 (m, 4H), 4.16 (d, J=12.8 Hz, 2H), 3.56-3.44 (m, 1H), 3.35-3.26 (m, 6H), 3.23-3.19 (m, 1H), 3.02 (dd, J=4.8 Hz, J=15.2 Hz, 1H), 2.77-2.53 (m, 1H), 1.59-1.52 (m, 6H).

Example 1409: 8-((3S,5R)-4-acryloyl-3,5-dimethylpiperazin-1-yl)-11-(4-fluorophenyl)-3,3-bis(methoxymethyl)-10-(trifluoromethyl)-3,4-dihydro-[1,4]thiazepino[2,3,4-ij]quinazolin-6(2H)-one

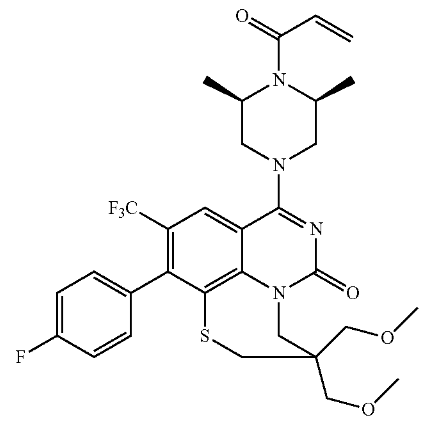 [SMILES: C=CC(=O)N1[C@H](C)CN(c2nc(=O)n3c4c(c(-c5ccc(F)cc5)c(C(F)(F)F)cc24)SCC(COC)(COC)C3)C[C@@H]1C]

The title compound was prepared according to the scheme below.

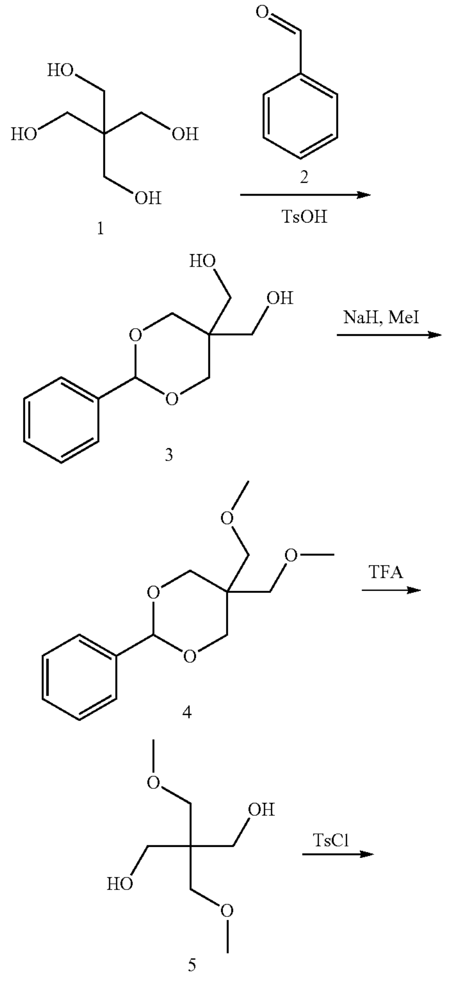

-continued

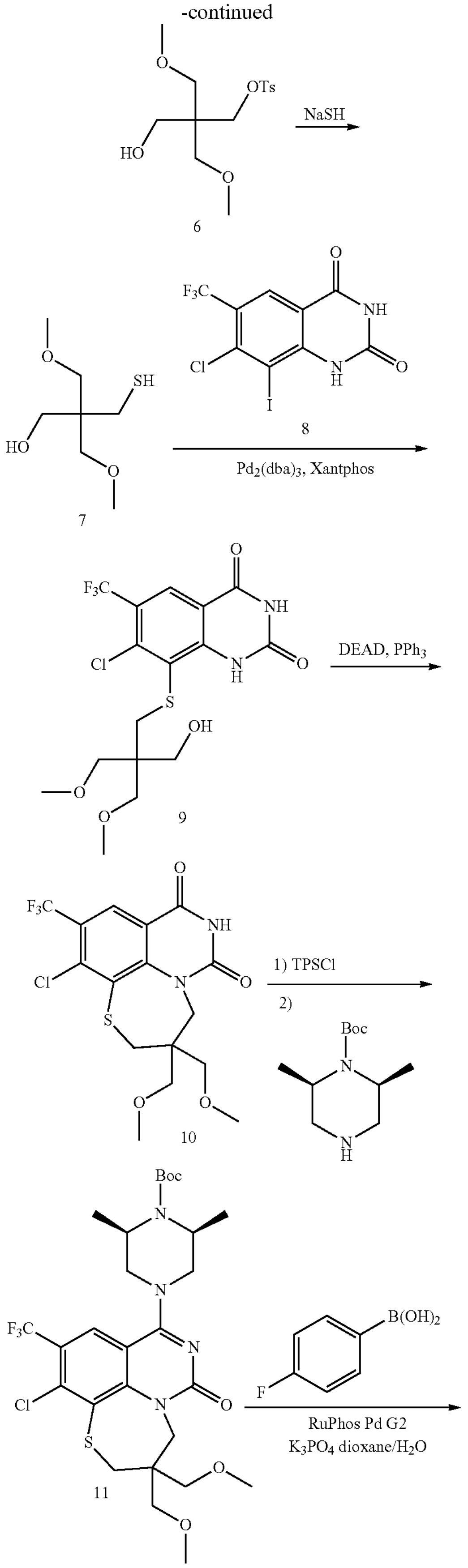

6, 7, 8, 9, 10, 11

-continued

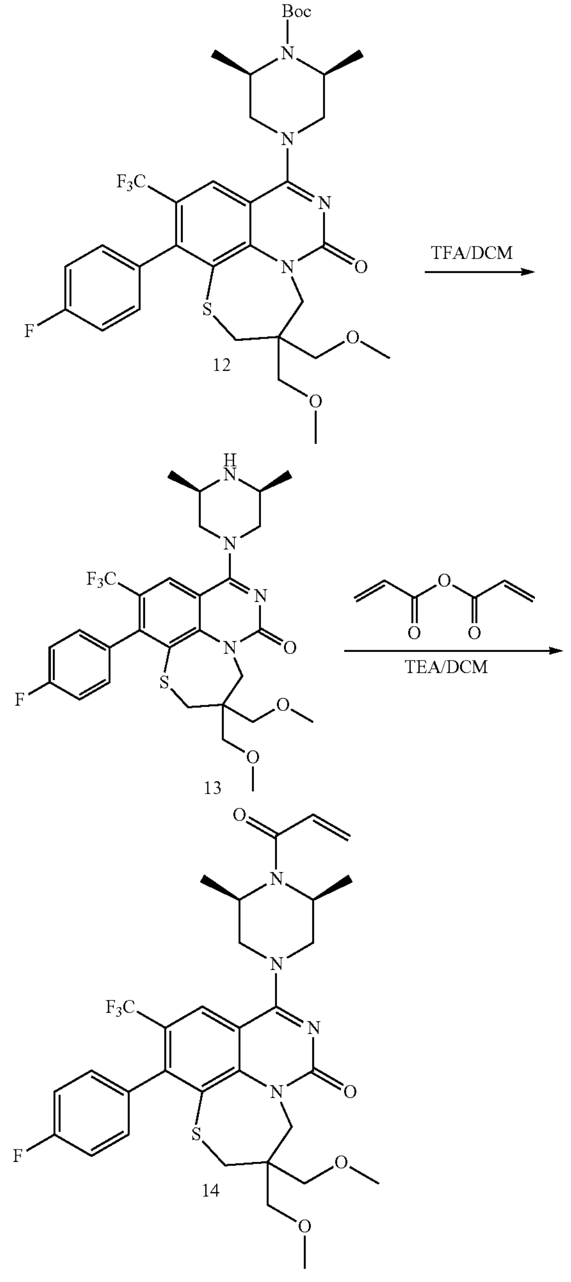

12, 13, 14

Step 1: (2-phenyl-1,3-dioxane-5,5-diyl)dimethanol (3)

Pentaerythritol (1) (54.4 g, 0.4 mol) were dissolved in water (500 mL) at 40° C. Benzaldehyde (42.4 g, 0.4 mol) and concentrated hydrochloric acid (2 mL) were added at room temperature. The reaction was stirred for 16 hours. Filtered, the filter cake was added to 800 mL of water and potassium carbonate (0.5 g). The crude product was recrystallized using toluene to afford the final product (2) (72.6 g, yield: 81%) as white solid. $^1$H NMR (300 MHz, $CDCl_3$) δ 7.52-7.44 (m, 2H), 7.42-7.33 (m, 3H), 5.43 (s, 1H), 4.21-4.10 (m, 4H), 3.76 (d, J=12.0 Hz, 2H), 3.54 (s, 2H), 2.41 (brs, 1H), 2.30 (brs, 1H).

Step 2: 5,5-bis(methoxymethyl)-2-phenyl-1,3-dioxane (4)

(2-phenyl-1,3-dioxane-5,5-diyl)dimethanol (3) (25 g, 111 mmol) was dissolved in tetrahydrofuran (500 mL) at room temperature. Sodium hydride (17.8 g, 444 mmol) was added at 0° C. and the reaction was stirred for 1 hour. Iodomethane (157.9 g, 1110 mol) was added, and the reaction was stirred at room temperature overnight. The mixture was poured into water (800 ml) and extracted with ethyl acetate (3×800 ml). The organic phase was concentrated to afford the product (4) (25 g, yield: 89%) as yellow oil. $^1$H NMR (300 MHz, $CDCl_3$) δ 7.50-7.47 (m, 2H), 7.49-7.33 (m, 3H), 5.43 (s, 1H), 4.12-4.07 (m, 2H), 3.89-3.85 (m, 2H), 3.71 (s, 2H), 3.40 (s, 3H), 3.30 (s, 3H), 3.21 (s, 2H).

Step 3: 2,2-bis(methoxymethyl)propane-1,3-diol (5)

To a solution of 5,5-bis(methoxymethyl)-2-phenyl-1,3-dioxane (1 g, 3.96 mmol) in dichloromethane (10 mL) was added trifluoroacetic acid (2.5 mL) at 0° C. The mixture was stirred at room temperature for 16 hours. After completion, the mixture was purified by silica gel column (with dichloromethane/methanol=50/1) to afford the product (5) (400 mg, yield: 60%) as pale-yellow oil. $^1$H NMR (400 MHz, $CDCl_3$) δ 3.65 (s, 4H), 3.45 (s, 4H), 3.35 (s, 6H).

Step 4: 3-hydroxy-2,2-bis(methoxymethyl)propyl 4-methylbenzenesulfonate (6)

TsCl (5.3 g, 27.86 mmol) was added to a mixture of 2,2-bis(methoxymethyl)propane-1,3-diol (4.57 g, 27.86 mmol) and triethyl amine (4.22 g, 41.79 mmol) in dichloromethane (100 mL) at 0° C. The mixture was stirred at room temperature for 16 hours. After completion, the mixture was purified by silica gel column (with petroleum ether/ethyl acetate=20/1) to afford the product (6) (2.2 g, yield: 25%) as pale-yellow oil. $^1$H NMR (400 MHz, $CDCl_3$) δ 7.78 (d, J=8.4 Hz, 2H), 7.35 (d, J=8.0 Hz, 2H), 4.07 (s, 2H), 3.62 (d, J=5.2 Hz, 2H), 3.33 (s, 4H), 3.25 (s, 6H), 2.52 (t, J=5.6 Hz, 1H), 2.45 (s, 3H).

Step 5: 3-mercapto-2,2-bis(methoxymethyl)propan-1-ol (7)

To a solution of 3-hydroxy-2,2-bis(methoxymethyl)propyl 4-methylbenzenesulfonate (6) (8 g, 25.16 mmol) in dimethylformide (50 mL) was added sodium hydrosulfide (20 g, 251.6 mmol, 70% purity) at 0° C. The mixture was stirred at 30° C. under nitrogen atmosphere for 16 hours. After completion, the mixture was filtered. The filtrate was concentrated to afford the crude product which was purified by silica gel column (with petroleum ether/ethyl acetate=4/1) to afford 3-mercapto-2,2-bis(methoxymethyl)propan-1-ol (7) (1.3 g, yield: 29%) as a pale yellow oil. $^1$H NMR (400 MHz, $CDCl_3$) δ 3.65 (s, 2H), 3.43-3.33 (m, 10H), 2.65 (d, J=9.2 Hz, 2H), 1.29 (t, J=9.2 Hz, 1H).

Step 6: 7-chloro-8-((3-hydroxy-2,2-bis(methoxymethyl)propyl)thio)-6-(trifluoromethyl)quinazoline-2,4(1H,3H)-dione (9)

To a solution of 7-chloro-8-iodo-6-(trifluoromethyl)quinazoline-2,4(1H,3H)-dione (8) (1.4 g, 3.61 mmol) in dioxane (45 mL) were added potassium carbonate (1.5 g, 10.83 mmol), 3-mercapto-2,2-bis(methoxymethyl)propan-1-ol (1.3 g, 7.22 mmol), 4,5-bis(diphenyl-phosphino)-9,9-dimethylxanthene (312 mg, 0.54 mmol) and tris(dibenzylideneacetone) dipalladium (329 mg, 0.36 mmol). The mixture was stirred at 60° C. under nitrogen atmosphere for 8 hours. After completion, the mixture was concentrated. The residue was purified by silica gel column chromatography (dichloromethane/methanol=60/1) to afford 7-chloro-8-((3-hydroxy-2,2-bis(methoxymethyl)propyl)thio)-6-(trifluoromethyl)quinazoline-2,4(1H,3H)-dione (9) (1.1 g, crude) as a yellow solid. MS (ESI) m/z 443.3 $[M+H]^+$.

Step 7: 11-chloro-3,3-bis(methoxymethyl)-10-(trifluoromethyl)-3,4-dihydro-2H,6H-[1,4]thiazepino[2,3,4-ij]quinazoline-6,8(7H)-dione (10)

To a mixture of 7-chloro-8-((3-hydroxy-2,2-bis(methoxymethyl)propyl)thio)-6-(trifluoromethyl)quinazoline-2,4(1H,3H)-dione (9) (1.07 g, 2.42 mmol) and triphenylphosphine (1.9 g, 7.26 mmol) in tetrahydrofuran (240 mL) was added diethyl azodicarboxylate (1.26 g, 7.26 mmol) at 0° C. The mixture was stirred at room temperature for 45 min. After completion, the mixture was poured into ice-water (100 mL) and extracted with ethyl acetate (3×100 mL). After concentration, the residue was purified by flash chromatography column (C18, acetonitrile/water=30% to 95%) to afford 11-chloro-3,3-bis(methoxymethyl)-10-(trifluoromethyl)-3,4-dihydro-2H,6H-[1,4]thiazepino[2,3,4-ij]quinazoline-6,8(7H)-dione (10) (590 mg, yield: 57%) as a yellow solid. MS (ESI) m/z 425.0 $[M+H]^+$.

Step 8: (2S,6R)-tert-butyl 4-(11-chloro-3,3-bis(methoxymethyl)-6-oxo-10-(trifluoromethyl)-2,3,4,6-tetrahydro-[1,4]thiazepino[2,3,4-ij]quinazolin-8-yl)-2,6-dimethylpiperazine-1-carboxylate (11)

To a mixture of 11-chloro-3,3-bis(methoxymethyl)-10-(trifluoromethyl)-3,4-dihydro-2H,6H-[1,4]thiazepino[2,3,4-ij]quinazoline-6,8(7H)-dione (10) (560 mg, 1.32 mmol) and potassium carbonate (1.82 g, 13.2 mmol) in acetonitrile (70 mL) and dichloromethane (70 mL) was added 2,4,6-triisopropylbenzenesulfonyl chloride (800 mg, 2.64 mmol) at 0° C. The mixture was stirred at room temperature for 4 hours. After completion, (2S,6R)-tert-butyl 2,6-dimethylpiperazine-1-carboxylate (565 mg, 2.64 mmol) was added into the reaction solution. The reaction mixture was stirred at 0° C. for 1 hour. After completion, the mixture was poured into ice-water (50 mL) and extracted with ethyl acetate (3×60 mL). After concentration, the residue was purified by C18 column with 20-95% acetonitrile in water to afford (2S,6R)-tert-butyl 4-(11-chloro-3,3-bis(methoxymethyl)-6-oxo-10-(trifluoromethyl)-2,3,4,6-tetrahydro-[1,4]thiazepino[2,3,4-ij]quinazolin-8-yl)-2,6-dimethylpiperazine-1-carboxylate (11) (610 mg, yield: 75%) as a yellow solid. MS (ESI) m/z 621.4 $[M+H]^+$.

Step 9: (2S,6R)-tert-butyl 4-(11-(4-fluorophenyl)-3,3-bis(methoxymethyl)-6-oxo-10-(trifluoromethyl)-2,3,4,6-tetrahydro-[1,4]thiazepino[2,3,4-ij]quinazolin-8-yl)-2,6-dimethylpiperazine-1-carboxylate (12)

To a solution of (2S,6R)-tert-butyl 4-(11-chloro-3,3-bis(methoxymethyl)-6-oxo-10-(trifluoromethyl)-2,3,4,6-tetrahydro-[1,4]thiazepino[2,3,4-ij]quinazolin-8-yl)-2,6-dimethylpiperazine-1-carboxylate (11) (150 mg, 0.24 mmol) in 1,4-dioxane (5 mL) and water (1 mL) was added tripotassium phosphate (192 mg, 0.72 mmol), (4-fluorophenyl)boronic acid (189 mg, 1.2 mmol) and Chloro(2-dicyclohexylphosphino-2', 6'-diisopropoxy-1,1'-biphenyl)[2-(2'-amino- 1,1'-biphenyl)]palladium(II) (19 mg, 0.024 mmol). The mixture was stirred at 80° C. under nitrogen atmosphere for 2 hours. After completion, the mixture was concentrated under reduced pressure, the residue was purified by silica gel column chromatography (dichloromethane/methanol=30/1) to afford (2S,6R)-tert-butyl 4-(11-(4-fluorophenyl)-3,3-bis(methoxymethyl)-6-oxo-10-(trifluoromethyl)-2,3,4,6-tetrahydro-[1,4]thiazepino[2,3,4-ij]quinazolin-8-yl)-2,6-dimethylpiperazine-1-carboxylate (12) (180 mg, crude) as a yellow solid. MS (ESI) m/z 681.5 $[M+H]^+$.

Step 10: 8-((3S,5R)-3,5-dimethylpiperazin-1-yl)-11-(4-fluorophenyl)-3,3-bis(methoxymethyl)-10-(trifluoromethyl)-3,4-dihydro-[1,4]thiazepino[2,3,4-ij]quinazolin-6(2H)-one (13)

To a cooled mixture of (2S,6R)-tert-butyl 4-(11-(4-fluorophenyl)-3,3-bis(methoxymethyl)-6-oxo-10-(trifluoromethyl)-2,3,4,6-tetrahydro-[1,4]thiazepino[2,3,4-ij]quinazolin-8-yl)-2,6-dimethylpiperazine-1-carboxylate (12) (180 mg, 0.26 mmol) in dichloromethane (5 mL) was added trifluoroacetic acid (2 mL) at 0° C. The reaction solution was stirred at room temperature for 1 hour. The solvent was removed under pressure. The residue was redissolved in dichloromethane and washed with saturated $NaHCO_3$. The organic layer was dried over $Na_2SO_4$ and concentrated. The residue was purified by silica gel column chromatography (dichloromethane/methanol=10/1) to afford 8-((3S,5R)-3,5-dimethylpiperazin-1-yl)-11-(4-fluorophenyl)-3,3-bis(methoxymethyl)-10-(trifluoromethyl)-3,4-dihydro-[1,4]thiazepino[2,3,4-ij]quinazolin-6(2H)-one (13) (100 mg, yield: 65%) as a yellow solid. MS (ESI) m/z 581.2 $[M+H]^+$.

Step 11: 8-((3S,5R)-4-acryloyl-3,5-dimethylpiperazin-1-yl)-11-(4-fluorophenyl)-3,3-bis(methoxymethyl)-10-(trifluoromethyl)-3,4-dihydro-[1,4]thiazepino[2,3,4-ij]quinazolin-6(2H)-one (14)

To a mixture of 8-((3S,5R)-3,5-dimethylpiperazin-1-yl)-11-(4-fluorophenyl)-3,3-bis(methoxymethyl)-10-(trifluoromethyl)-3,4-dihydro-[1,4]thiazepino[2,3,4-ij]quinazolin-6(2H)-one (13) (100 mg, 0.17 mmol) and triethyl amine (69 mg, 0.68 mmol) in dichloromethane (5 ml) was added acrylic anhydride (43 mg, 0.34 mmol) at 0° C. The mixture was stirred at 0° C. for 1 h. After completion, the mixture was poured into ice-water (30 mL) and extracted with dichloromethane (3×30 mL). After concentrated, the residue was purified by preparative High Performance Liquid Chromatography (20% to 95% acetonitrile in water) to afford 8-((3S,5R)-4-acryloyl-3,5-dimethylpiperazin-1-yl)-11-(4-fluorophenyl)-3,3-bis(methoxymethyl)-10-(trifluoromethyl)-3,4-dihydro-[1,4]thiazepino[2,3,4-ij]quinazolin-6(2H)-one (14) (21 mg, yield: 20%) as a white solid. MS (ESI) m/z 635.3 $[M+H]^+$. $^1H$ NMR (400 MHz, $CDCl_3$) δ 8.04 (s, 1H), 7.22-7.14 (m, 3H), 6.66-6.59 (m, 1H), 6.43 (dd, J=1.6 Hz, 16.8 Hz, 1H), 5.78 (dd, J=1.6 Hz, 10.4 Hz, 1H), 4.94-4.91 (m, 1H), 4.74-4.57 (m, 2H), 4.23-4.07 (m, 3H), 3.62-3.60 (m, 1H), 3.41-3.29 (m, 12H), 3.14-3.06 (m, 1H), 2.82-2.79 (m, 1H), 1.66 (d, J=5.2 Hz, 3H), 1.44 (d, J=4.4 Hz, 3H).

Example 1413: (S)-7-((3S,5R)-4-acryloyl-3,5-dimethylpiperazin-1-yl)-10-(4-fluorophenyl)-3-((methoxy-d3)methyl)-9-(trifluoromethyl)-2,3-dihydro-5H-[1,4]thiazino[2,3,4-ij]quinazolin-5-one

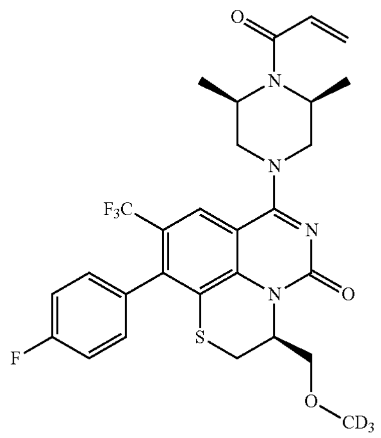 [SMILES: [2H]C([2H])([2H])OC[C@H]1CSc2c(-c3ccc(F)cc3)c(C(F)(F)F)cc3c(N4C[C@@H](C)N(C(=O)C=C)[C@@H](C)C4)nc(=O)n1c23]

The title compound was prepared according to the scheme below.

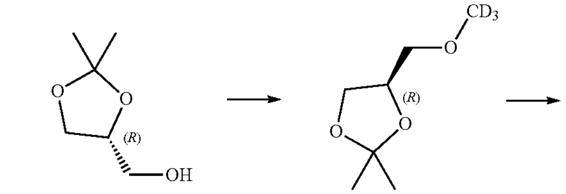

1 1

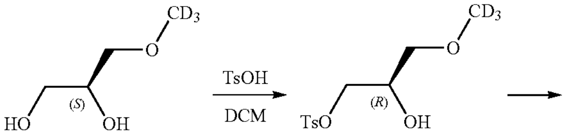

3 4

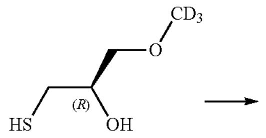

5

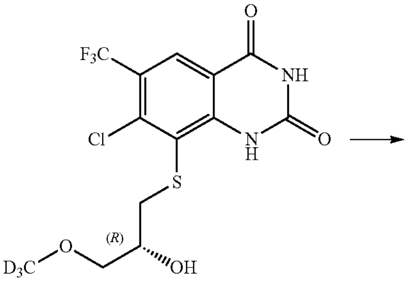

6

-continued

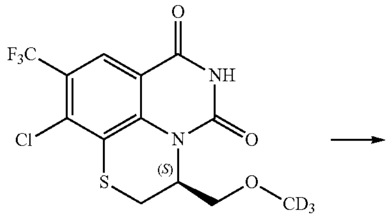

7

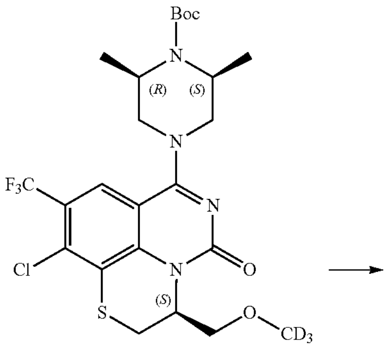

8

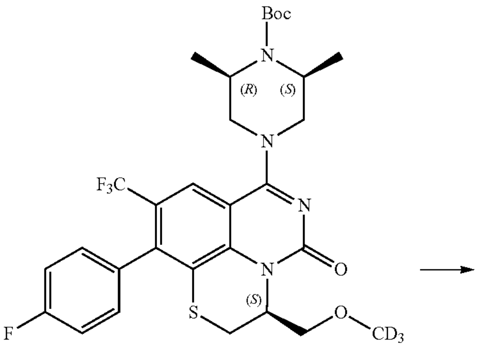

9

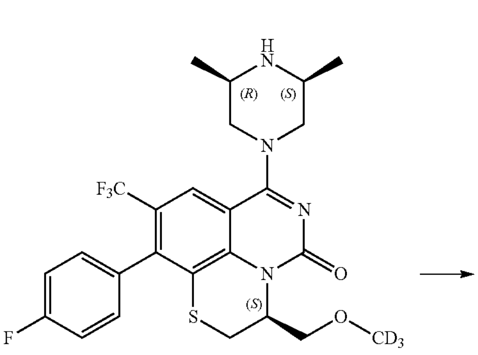

10

-continued

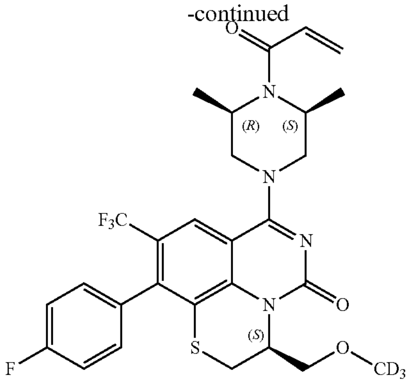

11

Step 1: (R)-2,2-dimethyl-4-((trideuteriomethoxy) methyl)-1,3-dioxolane (2)

To a mixture of (R)-(2,2-dimethyl-1,3-dioxolan-4-yl) methanol (1) (20 g, 151.4 mmol) in THF (350 mL) was added NaH (12.1 g, 302.7 mmol). The mixture was stirred at 0° C. to room temperature for 0.5 hour, followed by addition of $CD_3I$ (37.0 g, 237.2 mmol). The mixture was stirred at room temperature overnight. The mixture was poured into $NH_4Cl$ saturated solution (300 mL), extracted with ethyl acetate (3×200 mL). The organic phase was washed with water (100 mL) and dried over anhydrous sodium sulfate. After filtration, the filtrate was concentrated under reduce pressure to give the title compound (2) (13.0 g, crude) as yellow oil. $^1H$ NMR (400 MHz, $CDCl_3$) δ 4.31-4.24 (m, 1H), 4.07-4.04 (m, 1H), 3.72-3.68 (m, 1H), 3.49-3.39 (m, 2H), 1.43 (s, 3H), 1.37 (s, 3H).

Step 2: (S)-3-(trideuteriomethoxy)propane-1,2-diol (3)

The mixture of (R)-2,2-dimethyl-4-((trideuteriomethoxy) methyl)-1,3-dioxolane (2) (13.0 g, crude) and HCl (12 mL) in THF (100 mL) and water (100 mL) was stirred at room temperature overnight. The solvent was evaporated and the residue was purified by silica gel chromatography with DCM/MeOH=20/1 to afford (S)-3-(trideuteriomethoxy)propane-1,2-diol (3) (4.7 g, 49.8 mmol, 50% yield) as yellow oil. $^1H$ NMR (400 MHz, $CDCl_3$) δ 3.82-3.78 (m, 1H), 3.55 (dd, J=4.4 Hz, 11.6 Hz, 1H), 3.49-3.45 (m, 2H), 3.38 (dd, J=6.8 Hz, 10.4 Hz, 1H).

Step 3: (R)-2-hydroxy-3-(trideuteriomethoxy)propyl 4-methylbenzenesulfonate (4)

To a mixture of (S)-3-(trideuteriomethoxy)propane-1,2-diol (3) (4.7 g, 43.1 mmol) and TEA (8.9 mL, 64.6 mmol) in DCM (60 mL) was added TsCl (6.5 g, 34.4 mmol) at 0° C. The mixture was stirred at room temperature overnight. The solvent was evaporated and the residue was purified by silica gel chromatography (2% MeOH in DCM) to afford (R)-2-hydroxy-3-(trideuteriomethoxy)propyl 4-methylbenzenesulfonate (4) (7.7 g, crude) as yellow oil. $^1H$ NMR (400 MHz, $CDCl_3$) δ 7.80 (d, J=8.0 Hz, 2H), 7.35 (d, 6.4 Hz, 2H), 4.08-3.95 (m, 3H), 3.43-2.45 (m, 2H).

Step 4: (R)-1-mercapto-3-(trideuteriomethoxy)propan-2-ol (5)

The mixture of (R)-2-hydroxy-3-methoxypropyl 4-methylbenzenesulfonate (4) (7.7 g, 29.5 mmol, crude) and NaSH (7.09 g, 88.7 mmol) in EtOH (100 mL) was stirred at room temperature for 2 hours. The solvent was evaporated and the residue was purified by silica gel column by Petroleum/Ethyl Acetate=1/1 to afford (R)-1-mercapto-3-(trideuteriomethoxy)propan-2-ol (5) (2.9 g, 15.2 mmol, crude) as yellow oil; $^1$H NMR (400 MHz, $CDCl_3$) δ 3.85-3.79 (m, 1H), 3.51-3.41 (m, 2H), 2.73-2.59 (m, 2H), 1.47 (t, J=8.4 Hz, 1H).

Step 5: (R)-7-chloro-8-((2-hydroxy-3-(trideuterio methoxy)propyl)thio)-6-(trifluoromethyl)quinazoline-2,4(1H,3H)-dione (6)

To the mixture of 7-chloro-8-iodo-6-(trifluoromethyl)quinazoline-2,4(1H,3H)-dione (5.7 g, 14.8 mmol) in dioxane (300 mL) was added Pd2(dba)3 (1.3 g, 1.48 mmol), XantPhos (1.7 g, 2.96 mmol), (R)-1-mercapto-3-(trideuteriomethoxy)propan-2-ol (5) (2.7 g, 22.24 mmol) and $K_2CO_3$ (6.13 g, 44.4 mmol). The mixture was stirred at 55° C. under nitrogen atmosphere for overnight. The mixture was concentrated and the residue was purified by silica gel column with DCM/MeOH=20:1 to afford (R)-7-chloro-8-((2-hydroxy-3-(trideuterio methoxy)propyl)thio)-6-(trifluoromethyl)quinazoline-2,4(1H,3H)-dione (6) (2.8 g, crude) as a light yellow solid. LC-MS: [M+H], m/z=388.5.

Step 6: (S)-10-chloro-3-((trifluoromethoxy)methyl)-9-(trideuterio methyl)-2H-[1,4]thiazino[2,3,4-ij]quinazoline-5,7(3H,6H)-dione (7)

To a mixture of (R)-7-chloro-8-((2-hydroxy-3-(trideuterio methoxy)propyl)thio)-6-(trifluoromethyl)quinazoline-2,4(1H,3H)-dione (6) (2.8 g, 7.2 mmol) and triphenylphosphine (3.8 g, 14.4 mmol) in THF (50 mL) was added DEAD (2.5 g, 13.5 mmol) slowly at 0° C. under nitrogen atmosphere. The mixture was stirred at room temperature for 1 h. Then, the mixture was poured into ice water (50 mL) and extracted with DCM (2×30 mL). The combined organic phase was dried over $Na_2SO_4$, and concentrated. The residue was purified by silica gel column with Petroleum/Ethyl Acetate=0-50% to afford (S)-10-chloro-3-((trifluoromethoxy)methyl)-9-(trideuterio methyl)-2H-[1,4]thiazino[2,3,4-ij]quinazoline-5,7(3H,6H)-dione (7) (870 mg, 2.24 mmol, yield: 31%) as a yellow solid. LC-MS: [M+H], m/z=370.2.

Step 7: (2S,6R)-tert-butyl 4-((S)-10-chloro-5-oxo-3-((trideuteriomethoxy)methyl)-9-(trifluoromethyl)-3,5-dihydro-2H-[1,4]thiazino[2,3,4-ij]quinazolin-7-yl)-2,6-dimethylpiperazine-1-carboxylate (8)

To a mixture of (S)-10-chloro-3-((trifluoromethoxy)methyl)-9-(trideuterio methyl)-2H-[1,4]thiazino[2,3,4-ij]quinazoline-5,7(3H,6H)-dione (7) (820 mg, 2.16 mmol) and $K_2CO_3$ (2.98 g, 21.6 mmol) in ACN (20 mL) was added P-Toluenesulfonic anhydride (1.40 g, 4.32 mmol). The mixture was stirred at room temperature for 5 hours. Followed by addition of (2S,6R)-tert-butyl 2,6-dimethylpiperazine-1-carboxylate (925 mg, 4.32 mmol). The mixture was stirred for 2 hours. The mixture was concentrated under reduced pressure and purified by silica gel column with Dichloromethane/Ethyl Acetate=20%-80% to afford (2S,6R)-tert-butyl 4-((S)-10-chloro-5-oxo-3-((trideuteriomethoxy)methyl)-9-(trifluoromethyl)-3,5-dihydro-2H-[1,4]thiazino[2,3,4-ij]quinazolin-7-yl)-2,6-dimethylpiperazine-1-carboxylate (8) (680 mg, yield: 49%) as yellow solid. LC-MS: m/z 566.5 $[M+H]^+$.

Step 8: (2S,6R)-tert-butyl 4-((S)-10-(4-fluorophenyl)-5-oxo-3-((trideuteriomethoxy)methyl)-9-(trifluoromethyl)-3,5-dihydro-2H-[1,4]thiazino[2,3,4-ij]quinazolin-7-yl)-2,6-dimethylpiperazine-1-carboxylate (9)

To a solution of ((2S,6R)-tert-butyl 4-((S)-10-chloro-5-oxo-3-((trideuteriomethoxy)methyl)-9-(trifluoromethyl)-3,5-dihydro-2H-[1,4]thiazino[2,3,4-ij]quinazolin-7-yl)-2,6-dimethylpiperazine-1-carboxylate (8) (150 mg, 0.26 mmol) in dioxane (5 mL) and water (1 mL) was added (4-fluorophenyl)boronic acid (297 mg, 2.12 mmol), RuPhos Pd G2 (30 mg, 0.03 mmol) and K3PO4 (692 m g, 2.6 mmol). The mixture was stirred at 75° C. under N2 for 2 hours. The mixture was poured into water (2 mL) and extracted with EtOAc (3×5 mL). The combined organic phases were washed with brine (5 mL) and dried over Na2SO4. After filtration and concentration, the residue was purified by silica gel column using dichloromethane/methanol=50:1 to afford the (2S,6R)-tert-butyl 4-((S)-10-(4-fluorophenyl)-5-oxo-3-((trideuteriomethoxy)methyl)-9-(trifluoromethyl)-3,5-dihydro-2H-[1,4]thiazino[2,3,4-ij]quinazolin-7-yl)-2,6-dimethylpiperazine-1-carboxylate (9) (160 mg, crude) as a yellow solid. MS (ESI) m/z 626.6 $[M+H]^+$.

Step 9: (S)-7-((3S,5R)-3,5-dimethylpiperazin-1-yl)-10-(4-fluorophenyl)-3-((trideuteriomethoxy)methyl)-9-(trifluoromethyl)-2H-[1,4]thiazino[2,3,4-ij]quinazolin-5(3H)-one (10)

To a solution of (2S,6R)-tert-butyl 4-((S)-10-(4-fluorophenyl)-5-oxo-3-((trideuteriomethoxy)methyl)-9-(trifluoromethyl)-3,5-dihydro-2H-[1,4]thiazino[2,3,4-ij]quinazolin-7-yl)-2,6-dimethylpiperazine-1-carboxylate (9) (160 mg, 0.25 mmol) in DCM (3 mL) was added TFA (1 mL) at 0° C. The mixture was stirred at room temperature for 1 h. The solvent was removed under pressure. The residue was redissolved in dichloromethane and washed with saturated $NaHCO_3$. The organic layer was dried over $Na_2SO_4$. The organic solvent was concentrated under reduced pressure to afford (S)-7-((3S,5R)-3,5-dimethylpiperazin-1-yl)-10-(4-fluorophenyl)-3-((trideuteriomethoxy)methyl)-9-(trifluoromethyl)-2H-[1,4]thiazino[2,3,4-ij]quinazolin-5(3H)-one (10) (150 mg, crude) as yellow solid. LC-MS: m/z 526.3 [M+H]+. 1H NMR (400 MHz, CDCl3) δ 7.78 (s, 1H), 7.21-7.17 (m, 4H), 5.43-5.37 (m, 1H), 4.39 (d, J=12.4, 1H), 4.20 (d, J=11.6 Hz, 2H), 3.66-3.64 (m, 2H), 3.33-3.29 (m, 1H), 3.21-3.13 (m, 1H), 2.96-2.92 (m, 3H), 2.72 (t, J=11.2 Hz, 1H), 1.16-1.12 (m, 6H).

Step 10: (S)-7-((3S,5R)-4-acryloyl-3,5-dimethylpiperazin-1-yl)-10-(4-fluorophenyl)-3-((trideuteriomethoxy)methyl)-9-(trifluoromethyl)-2H-[1,4]thiazino[2,3,4-ij]quinazolin-5(3H)-one (11)

To a solution of (S)-7-((3S,5R)-3,5-dimethylpiperazin-1-yl)-10-(4-fluorophenyl)-3-((trideuteriomethoxy)methyl)-9-(trifluoromethyl)-2H-[1,4]thiazino[2,3,4-ij]quinazolin-5(3H)-one (10) (100 mg, 0.19 mmol) and Et3N (28 mg, 0.28 mmol) in DCM (3 mL) was added acrylic anhydride (36 mg, 0.28 mmol) at 0° C. The mixture was stirred at room temperature for 30 min. The mixture was quenched with 1 mL of MeOH, concentrated under reduce pressure. The residue was purified by prep-HPLC to afford (S)-7-((3S,5R)-4-acryloyl-3,5-dimethylpiperazin-1-yl)-10-(4-fluorophenyl)-3-((trideuteriomethoxy)methyl)-9-(trifluoromethyl)-2H-[1,4]thiazino[2,3,4-ij]quinazolin-5(3H)-one (11) (57 mg, 52% yield) as a white powder. LC-MS: m/z 580.2 [M+H]+; 1H NMR (400 MHz, CDCl3) δ 8.06 (s, 1H), 7.23-7.15 (m, 4H), 6.62 (dd, J=10.4 Hz, J=16.4 Hz, 1H), 6.41 (dd, J=1.6 Hz, J=16.8 Hz, 1H), 5.77 (dd, J=2.0 Hz, J=10.4 Hz, 1H), 5.43-5.41 (m, 1H), 4.82-4.54 (m, 2H), 4.21-4.16 (m, 2H), 3.69-3.62 (m, 2H), 3.39-3.29 (m, 3H), 2.98-2.94 (m, 1H), 1.62 (d, J=7.2 Hz, 3H), 1.47 (d, J=7.2 Hz, 3H).

Example 1419: (S)-7-((3S,5R)-4-acryloyl-3,5-dimethylpiperazin-1-yl)-10-(4-fluorophenyl)-3-methyl-9-(trifluoromethyl)-2H-[1,4]thiazino[2,3,4-ij]quinazolin-5(3H)-one

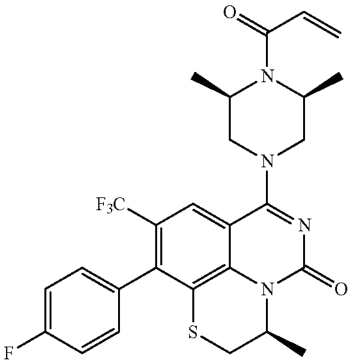

The title compound was prepared according to the scheme below.

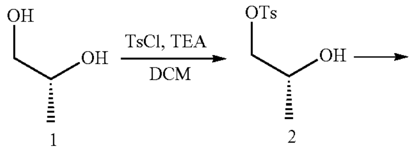

1 2

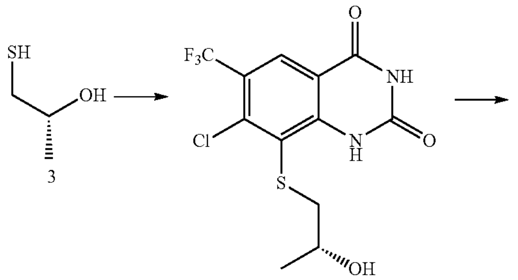

3 4

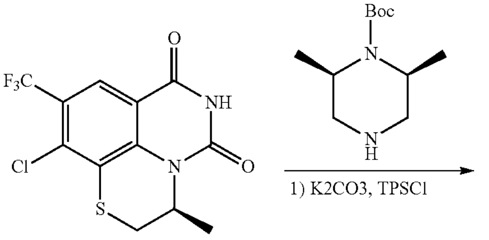

5

-continued

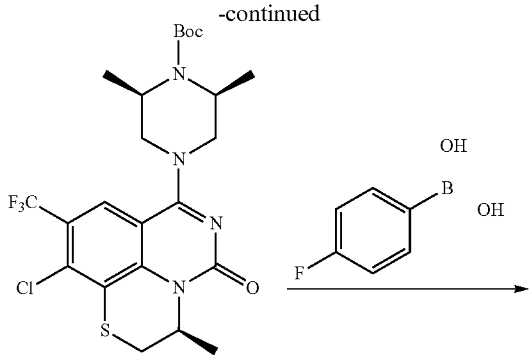

6

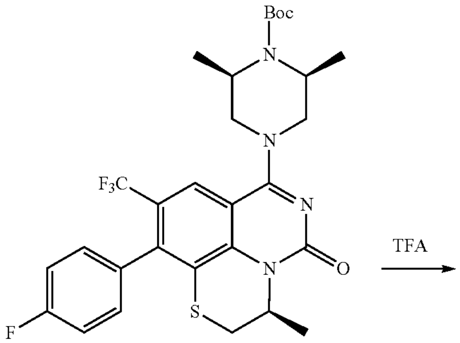

7

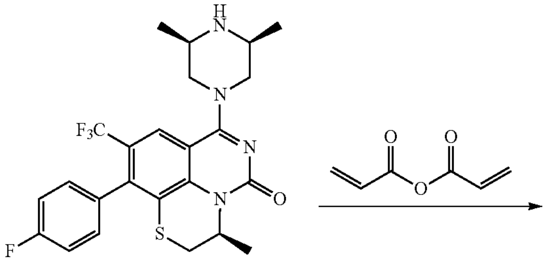

8

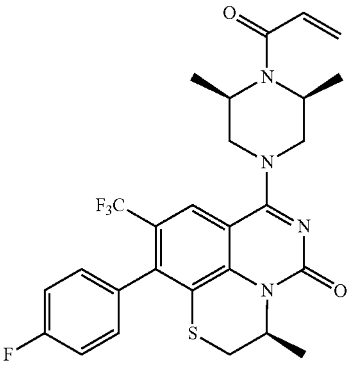 [SMILES: C=CC(=O)N1[C@H](C)CN(c2nc(=O)n3c4c(c(-c5ccc(F)cc5)c(C(F)(F)F)cc24)SC[C@@H]3C)C[C@@H]1C]

9

Step 1: (R)-2-hydroxypropyl 4-methylbenzenesulfonate (2)

To a mixture of (R)-propane-1,2-diol (1) (10 g, 0.13 mol) and TEA (20.0 mL, 0.195 mmol) in DCM (100 mL) was added TsCl (22.8 g, 0.12 mmol) at 0° C. After addition, the mixture was stirred at rt for 12 hours. The solvent was evaporated, and the residue was purified by silica gel chromatography (10-20% ethyl acetate in petroleum ether) to afford the title compound (2) (7.1 g, 0.031 mol, 31% yield) as colorless oil. MS (ESI) m/z 230.1 $[M+H]^+$.

Step 2: (R)-1-mercaptopropan-2-ol (3)

To a mixture of (R)-2-hydroxypropyl 4-methylbenzenesulfonate (2) (7.1 g, 31.0 mmol) in EtOH (100 mL) was added NaHS (2.6 g, 46.5 mmol). The mixture was stirred at 50° C. for 2.5 hours. The mixture was concentrated under reduce pressure, and the residue was purified by silica gel chromatography (30-50% ethyl acetate in petroleum ether) to afford the title compound (3) (2.6 g, 28.3 mmol) as colorless oil.

Step 3: (R)-7-chloro-8-((2-hydroxypropyl)thio)-6-(trifluoromethyl)quinazoline-2,4(1H,3H)-dione (4)

To the mixture of 7-chloro-8-iodo-6-(trifluoromethyl)quinazoline-2,4(1H,3H)-dione (3.2 g, 8.2 mmol), 4,5-bis(diphenyl-phosphino)-9,9-dimethylxanthene (910 mg, 1.6 mmol) and tris(dibenzylideneacetone) dipalladium (146.4 g, 1.6 mmol) in dioxane (15 mL) was added (R)-1-mercaptopropan-2-ol (3) (1.5 g, 16.4 mmol) and $K_2CO_3$ (3.4 g, 24.6 mmol). The mixture was stirred under nitrogen atmosphere at 60° C. for 15 hours. The mixture was concentrated and the residue was purified by silica gel column with (DCM/MeOH=50:1~30:1) to afford the product (4) (1.68 g, 4.7 mmol, yield: 57%) as a yellow solid. MS (ESI) m/z 355.1 $[M+H]^+$.

Step 4: (S)-10-chloro-3-methyl-9-(trifluoromethyl)-2H-[1,4]thiazino[2,3,4-ij]quinazoline-5,7(3H,6H)-dione (5)

To a mixture of 6-chloro-7-(2,4-difluorophenyl)-8-(((R)-2-hydroxypropyl)thio)quinazoline-2,4(1H,3H)-dione (4) (1.2 g, 3.4 mmol) and triphenylphosphine (1.4 g, 5.0 mmol) in THF (30 mL) was added DEAD (870 mg, 5.0 mmol) slowly at 0° C. under nitrogen atmosphere. The mixture was stirred at room temperature for 1 hour. The organic phase was washed with water (50 mL), dried over $Na_2SO_4$ and concentrated. The residue was purified by silica gel column with Petroleum/Ethyl Acetate=0-50% to afford the product (5) (570 mg, 1.7 mmol, yield: 50%) as a yellow solid. LC-MS: [M−H], m/z=337.2.

Step 5: (2S,6R)-tert-butyl 4-((S)-10-chloro-3-methyl-5-oxo-9-(trifluoromethyl)-3,5-dihydro-2H-[1,4]thiazino[2,3,4-ij]quinazolin-7-yl)-2,6-dimethylpiperazine-1-carboxylate (6)

To a solution of (S)-10-chloro-3-methyl-9-(trifluoromethyl)-2H-[1,4]thiazino[2,3,4-ij]quinazoline-5,7(3H,6H)-dione (5) (512 mg, 1.7 mmol) and $K_2CO_3$ (1.17 g, 8.5 mmol) in ACN (2 mL) was added 2,4,6-triisopropylbenzenesulfonyl chloride (770 mg, 2.55 mmol). The mixture was stirred at rt for 5 hours, then the (2S,6R)-tert-butyl 2,6-dimethylpiperazine-1-carboxylate (117 mg, 0.41 mmol) was added to the reaction mixture. The reaction mixture was stirred at 0° C. for 1 hour. After completion, the resulting mixture was concentrated under reduced pressure and the residue was purified by silica gel column with Petroleum/Ethyl Acetate=20%-80% to afford desired product (6) (423 mg, 0.8 mmol) as yellow solid. LC-MS: m/z 533.2 $[M+H]^+$;

Step 6: (2S,6R)-tert-butyl-((S)-10-(4-fluorophenyl)-3-methyl-5-oxo-9-(trifluoromethyl)-3,5-dihydro-2H-[1,4]thiazino[2,3,4-ij]quinazolin-7-yl)-2,6-dimethylpiperazine-1-carboxylate (7)

To a solution of (2S,6R)-tert-butyl 4-((S)-10-chloro-3-methyl-5-oxo-9-(trifluoromethyl)-3,5-dihydro-2H-[1,4]thiazino[2,3,4-ij]quinazolin-7-yl)-2,6-dimethylpiperazine-1-carboxylate (6) (180 mg, 0.34 mmol) in 1,4-dioxane (5 mL) and water (0.7 mL) were added tripotassium phosphate trihydrate (212 mg, 1 mmol), (4-fluorophenyl)boronic acid (420 g, 1.0 mmol), and chloro(2-dicyclohexylphosphino-2',6'-diisopropoxy-1,1'-biphenyl)[2-(2'-amino-1,1'-biphenyl)]palladium(II) (30 mg, 0.04 mmol). The mixture was stirred at 85° C. under nitrogen atmosphere for 3 hours. After completion, the mixture was concentrated. The residue was purified by silica gel column chromatography (with 1%-3% methanol in dichloromethane) to afford the product (7) (167 mg, crude) as a yellow solid. MS (ESI) m/z 593.2 $[M+H]^+$.

Step 7: (S)-7-((3S,5R)-3,5-dimethylpiperazin-1-yl)-10-(4-fluorophenyl)-3-methyl-9-(trifluoromethyl)-2H-[1,4]thiazino[2,3,4-ij]quinazolin-5(3H)-one (8)

To a solution of (2S,6R)-tert-butyl-((S)-10-(4-fluorophenyl)-3-methyl-5-oxo-9-(trifluoromethyl)-3,5-dihydro-2H-[1,4]thiazino[2,3,4-ij]quinazolin-7-yl)-2,6-dimethylpiperazine-1-carboxylate (7) (167 mg, crude) in dichloromethane (3 mL) was added TFA (1 mL) at 20° C. The mixture was stirred at room temperature for 1 hour. The solvent was removed under pressure. The residue was redissolved in dichloromethane and washed with saturated $NaHCO_3$. The organic layer was dried over $Na_2SO_4$ and concentrated. The residue was purified by silica gel column chromatography (with 1%-3% methanol in dichloromethane) to afford the product (8) (105 mg, 0.21 mmol). MS (ESI) m/z 493.2 $[M+H]^+$.

Step 8: (S)-7-((3S,5R)-4-acryloyl-3,5-dimethylpiperazin-1-yl)-10-(4-fluorophenyl)-3-methyl-9-(trifluoromethyl)-2H-[1,4]thiazino[2,3,4-ij]quinazolin-5(3H)-one (9)

To a mixture of (S)-7-((3S,5R)-3,5-dimethylpiperazin-1-yl)-10-(4-fluorophenyl)-3-methyl-9-(trifluoromethyl)-2H-[1,4]thiazino[2,3,4-ij]quinazolin-5(3H)-one (8) (95 mg, 0.19 mmol) and triethyl amine (57 mg, 0.57 mmol) in dichloromethane (3 mL) was added Acrylic Anhydride (47 mg, 0.38 mmol) at 0° C. The mixture was stirred at room temperature for 1 hour. The mixture was concentrated, and the residue was purified by prep-HPLC to afford the product (45 mg, 40% yield) as white solid (9). LC-MS: m/z 547.2 [M+H]+; $^1$H NMR (400 MHz, $CDCl_3$) δ 8.08 (s, 1H), 7.23-7.16 (m, 4H), 6.66-6.59 (m, 1H) 6.43-6.38 (m, 1H), 5.78-5.75 (m, 1H), 5.45-5.42 (m, 1H), 4.78-4.53 (m, 2H), 4.21-4.15 (m, 2H), 3.38-3.27 (m, 2H), 3.14-3.10 (in, TH), 2.90-2.86 (in, TH), 1.64 (d, J=5.2 Hz, 3H), 1.48-1.46 (in, 6H).

TABLE 10

Summary of Summary of % CAF at 10 μM after 1 hour for Examples 1200-1243

| Example Number | CAF (% after 1 hour) |
|---|---|
| 1200 | 73 |
| 1201 | 96 |
| 1202 | 97 |
| 1203 | 95 |
| 1204 | 95 |
| 1205 | 95 |
| 1206 | 92 |
| 1207 | 95 |
| 1208 | 95 |
| 1209 | 96 |
| 1210 | 94 |
| 1211 | 97 |
| 1212 | 50 |

TABLE 10-continued

| Summary of Summary of % CAF at 10 μM after 1 hour for Examples 1200-1243 | |
|---|---|
| Example Number | CAF (% after 1 hour) |
| 1213 | 59 |
| 1214 | 49 |
| 1215 | 95 |
| 1216 | 94 |
| 1217 | 95 |
| 1218 | 66 |
| 1219 | 64 |
| 1220 | 67 |
| 1221 | 61 |
| 1222 | 59 |
| 1223 | 57 |
| 1224 | 96 |
| 1225 | 95 |
| 1226 | 81 |
| 1227 | 93 |
| 1228 | 96 |
| 1229 | 96 |
| 1230 | 94 |
| 1231 | 38 |
| 1232 | 93 |
| 1233 | 95 |
| 1234 | 94 |
| 1235 | 69 |
| 1236 | 94 |
| 1237 | 90 |
| 1238 | 95 |
| 1239 | 95 |
| 1240 | 91 |
| 1241 | 91 |
| 1242 | 70 |
| 1243 | 92 |

TABLE 11

Summary of % CAF at 10 μM after 1 hour for Examples 1300-1455

| Ex. # | Structure | $^1$H NMR | MS (M + H)$^+$ | % CAF 10 uM @ 60 min | Name |
|---|---|---|---|---|---|
| 1300 | 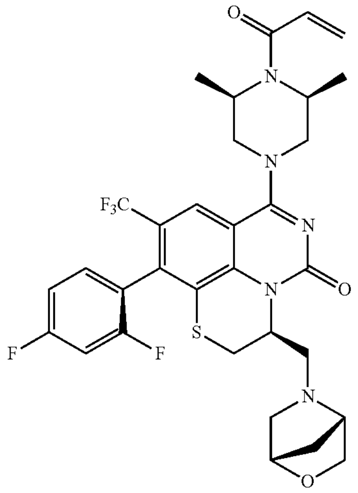 | $^1$H NMR (400 MHz, $CDCl_3$) δ: 8.07 (s, 1H), 7.21-7.15 (m, 1H), 7.06-6.93 (m, 2H), 6.66-6.59 (m, 1H), 6.43-6.38 (m, 1H), 5.78 (d, J = 12.0 Hz, 1H), 5.28-5.26 (m, 1H), 4.66-4.40 (m, 3H), 4.21-4.18 (m, 2H), 3.88-3.87 (m, 1H), 3.68-3.31 (m, 5.5H), 2.99-2.84 (m, 4.5H), 1.75-1.72 (m, 2H), 1.61 (d, J = 6.8 Hz, 3H), 1.47 (t, J = 6.8 Hz, 3H). | 662.3 | 90.8 | (3S,10S)-3-(((1S,4S)-2-oxa-5-azabicyclo[2.2.1]heptan-5-yl)methyl)-7-((3S,5R)-4-acryloyl-3,5-dimethylpiperazin-1-yl)-10-(2,4-difluorophenyl)-9-(trifluoromethyl)-2,3-dihydro-5H-[1,4]thiazino[2,3,4-ij]quinazolin-5-one |
| 1301 | 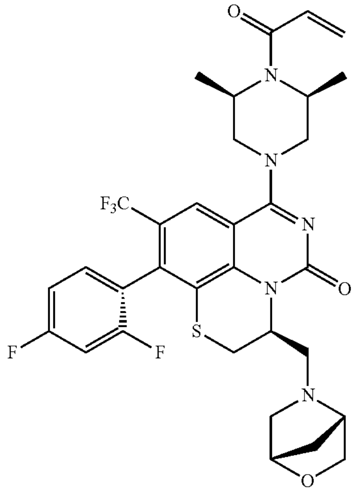 | $^1$H NMR (400 MHz, $CDCl_3$) δ: 8.07 (s, 1H), 7.26-7.14 (m, 1H), 7.04-6.95 (m, 2H), 6.66-6.59 (m, 1H), 6.43-6.38 (m, 1H), 5.77 (dd, J = 12.4 Hz, 1H), 5.24-5.22 (m, 1H), 4.68-4.61 (m, 1.5H), 4.40 (s, 1H), 4.18 (d, J = 13.2 Hz, 2H), 3.89-3.87 (m, 1H), 3.62-3.30 (m, 5.5H), 3.01-2.85 (m, 5H), 1.75-1.71 (m, 2H), 1.62-1.60 (m, 3H), 1.49 (d, J = 6.8 Hz, 3H). | 662.3 | 96.4 | (3S,10R)-3-(((1S,4S)-2-oxa-5-azabicyclo[2.2.1]heptan-5-yl)methyl)-7-((3S,5R)-4-acryloyl-3,5-dimethylpiperazin-1-yl)-10-(2,4-difluorophenyl)-9-(trifluoromethyl)-2,3-dihydro-5H-[1,4]thiazino[2,3,4-ij]quinazolin-5-one |

TABLE 11-continued

| Summary of % CAF at 10 μM after 1 hour for Examples 1300-1455 | | | | | |
|---|---|---|---|---|---|
| Ex. # | Structure | $^1$H NMR | MS (M + H)$^+$ | % CAF 10 uM @ 60 min | Name |
| 1302 | 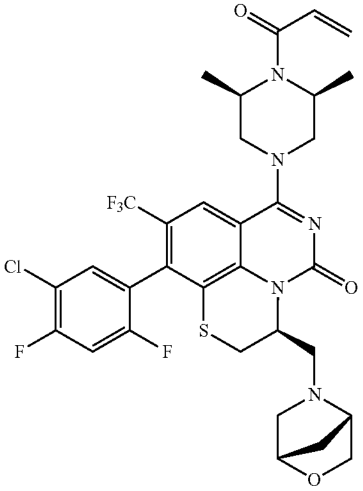 [SMILES: C=CC(=O)N1[C@H](C)CN(c2nc(=O)n3c4c(c(-c5cc(Cl)c(F)cc5F)c(C(F)(F)F)cc24)SC[C@@H]3CN2C[C@@H]3C[C@H]2CO3)C[C@@H]1C] | $^1$H NMR (400 MHz, $CDCl_3$) δ: 8.07 (s, 1H), 7.29-7.27 (m, 1H), 7.10-7.04 (m, 1H), 6.65-6.59 (m, 1H), 6.43-6.38 (m, 1H), 5.77 (dd, J = 10.4 Hz, 1.6 Hz, 1H), 5.29-5.23 (m, 1H), 4.66-4.60 (m, 2H), 4.42-4.41 (m, 1H), 4.20-4.17 (m, 2H), 3.89-3.86 (m, 1H), 3.62-3.32 (m, 5.5H), 3.01-2.85 (m, 4.5H), 1.76-1.68 (m, 2H), 1.60 (d, J = 7.2 Hz, 3H), 1.48 (d, J = 6.8 Hz, 3H). | 696.2 | 78.9 | (3S)-3-(((1S,4S)-2-oxa-5-azabicyclo[2.2.1]heptan-5-yl)methyl)-7-((3S,5R)-4-acryloyl-3,5-dimethylpiperazin-1-yl)-10-(5-chloro-2,4-difluorophenyl)-9-(trifluoromethyl)-2,3-dihydro-5H-[1,4]thiazino[2,3,4-ij]quinazolin-5-one |
| 1303 | 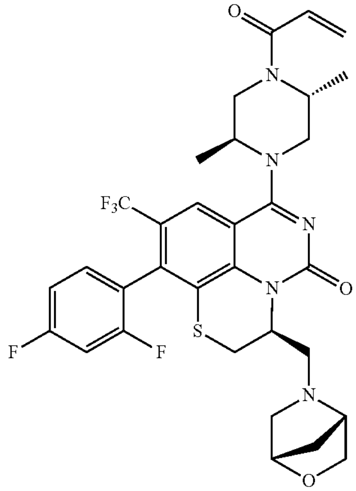 [SMILES: C=CC(=O)N1C[C@H](C)N(c2nc(=O)n3c4c(c(-c5ccc(F)cc5F)c(C(F)(F)F)cc24)SC[C@@H]3CN2C[C@@H]3C[C@H]2CO3)C[C@H]1C] | $^1$H NMR (400 MHz, $CDCl_3$) δ: 7.97 (d, J = 18.4 Hz, 1H), 7.26-7.18 (m, 1H), 7.12-6.98 (m, 2H), 6.76-6.53 (m, 1H), 6.49-6.35 (m, 1H), 5.91-5.83 (m, 1H), 5.48-5.41 (m, 1H), 5.23-5.09 (m, 1H), 4.78-4.66 (m, 3H), 4.54-4.21 (m, 4H), 3.89-3.57 (m, 7H), 3.48-3.17 (m, 2H), 2.24-2.18 (m, 1H), 1.66-1.52 (m, 6H). | 662.3 | 77.6 | (3S)-3-(((1S,4S)-2-oxa-5-azabicyclo[2.2.1]heptan-5-yl)methyl)-7-((3S,5R)-4-acryloyl-3,5-dimethylpiperazin-1-yl)-10-(2,4-difluorophenyl)-9-(trifluoromethyl)-2,3-dihydro-5H-[1,4]thiazino[2,3,4-ij]quinazolin-5-one |
| 1304 | 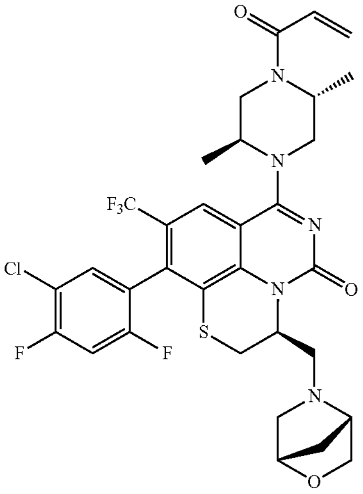 [SMILES: C=CC(=O)N1C[C@H](C)N(c2nc(=O)n3c4c(c(-c5cc(Cl)c(F)cc5F)c(C(F)(F)F)cc24)SC[C@@H]3CN2C[C@@H]3C[C@H]2CO3)C[C@H]1C] | $^1$H NMR (400 MHz, $CDCl_3$) δ: 7.90 (s, 1H), 7.39-7.34 (m, 1H), 7.16-7.10 (m, 1H), 6.74-6.56 (m, 1H), 6.50-6.39 (m, 1H), 5.88-5.81 (m, 1H), 5.33-5.22 (m, 1H), 5.14-4.67 (m, 1.5H), 4.54-4.39 (m, 2H), 4.18-4.11 (m, 0.5H), 4.02-3.95 (m, 1H), 3.77-3.49 (m, 5H), 3.38-2.86 (m, 5H), 1.86-1.71 (m, 3H), 1.55-1.42 (m, 6H). | 696.3 | 87 | (3S)-3-(((1S,4S)-2-oxa-5-azabicyclo[2.2.1]heptan-5-yl)methyl)-7-((2S,5R)-4-acryloyl-2,5-dimethylpiperazin-1-yl)-10-(5-chloro-2,4-dichlorophenyl)-9-(trifluoromethyl)-2,3-dihydro-5H-[1,4]thiazino[2,3,4-ij]quinazolin-5-one |

TABLE 11-continued

| Summary of % CAF at 10 μM after 1 hour for Examples 1300-1455 | | | | | |
|---|---|---|---|---|---|
| Ex. # | Structure | $^1$H NMR | MS (M + H)$^+$ | % CAF 10 uM @ 60 min | Name |
| 1305 | 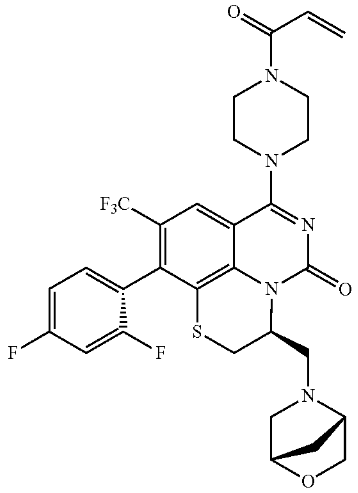 | $^1$H NMR (400 MHz, $CDCl_3$) δ 7.88 (s, 1H), 7.29-7.21 (m, 1H), 7.09-7.01 (m, 2H), 6.71-6.62 (m, 1H), 6.47-6.41 (m, 1H), 5.86 (d, J = 14.4 Hz, 1H), 5.30-5.24 (m, 1H), 4.48 (s, 1H), 4.08-3.98 (m, 4.5H), 3.96-3.81 (m, 5H), 3.60-3.56 (m, 3H), 3.09-2.86 (m, 4.5H), 1.83-1.78 (m, 2H). | 634.3 | 97.2 | (3S,10R)-3-(((1S,4S)-2-oxa-5-azabicyclo[2.2.1]heptan-5-yl)methyl)-7-(4-acryloylpiperazin-1-yl)-10-(2,4-difluorophenyl)-9-(trifluoromethyl)-2,3-dihydro-5H-[1,4]thiazino[2,3,4-ij]quinazolin-5-one |
| 1306 | 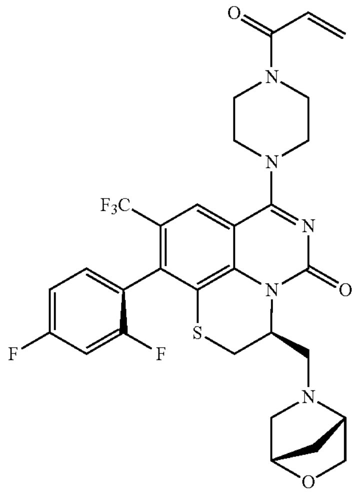 | $^1$H NMR (400 MHz, $CDCl_3$) δ 7.86 (s, 1H), 7.23-7.18 (m, 1H), 7.11-7.01 (m, 2H), 6.69-6.62 (m, 1H), 6.44-6.39 (m, 1H), 5.83 (d, J = 14.4 Hz, 1H), 5.30-5.26 (m, 1H), 4.48 (s, 1H), 4.08-3.96 (m, 4.5H), 3.96-3.85 (m, 5H), 3.67-3.52 (m, 3H), 3.04-2.86 (m, 4.5H), 1.83-1.78 (m, 2H). | 634.3 | 96.8 | (3S,10S)-3-(((1S,4S)-2-oxa-5-azabicyclo[2.2.1]heptan-5-yl)methyl)-7-(4-acryloylpiperazin-1-yl)-10-(2,4-difluorophenyl)-9-(trifluoromethyl)-2,3-dihydro-5H-[1,4]thiazino[2,3,4-ij]quinazolin-5-one |

TABLE 11-continued

Summary of % CAF at 10 μM after 1 hour for Examples 1300-1455

| Ex. # | Structure | $^1$H NMR | MS (M + H)$^+$ | % CAF 10 uM @ 60 min | Name |
|---|---|---|---|---|---|
| 1307 | 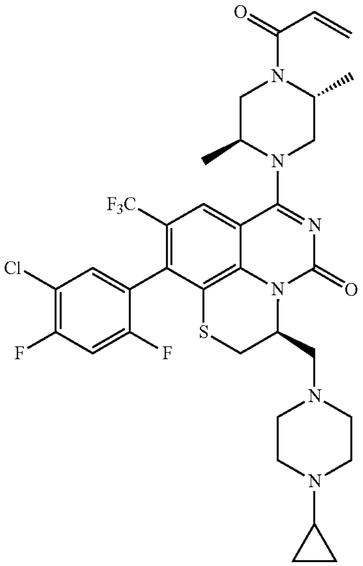 [SMILES: C=CC(=O)N1C[C@H](C)N(c2nc(=O)n3c4c(c(-c5cc(Cl)c(F)cc5F)c(C(F)(F)F)cc24)SC[C@@H]3CN2CCN(C3CC3)CC2)C[C@H]1C] | $^1$H NMR (400 MHz, $CDCl_3$) δ: 7.90 (s, 1H), 7.12 (t, J = 11.2 Hz, 1H), 6.73-6.55 (m, 1H), 6.47-6.38 (m, 1H), 5.86-5.81 (m, 1H), 5.46-5.38 (m, 1H), 5.14-4.72 (m, 2H), 4.42-4.37 (m, 2H), 4.17-4.06 (m, 1H), 3.80-3.53 (m, 5H), 3.35-2.83 (m, 10H), 2.41-2.32 (m, 1H), 1.53-1.46 (m, 6H), 1.30-1.06 (m, 1H), 0.91-0.87 (m, 2H). | 723.5 | 69.7 | (3S)-7-((2S,5R)-4-acryloyl-2,5-dimethylpiperazin-1-yl)-10-(5-chloro-2,4-difluorophenyl)-3-((4-cyclopropylpiperazin-1-yl)methyl)-9-(trifluoromethyl)-2,3-dihydro-5H-[1,4]thiazino[2,3,4-ij]quinazolin-5-one |
| 1309 | 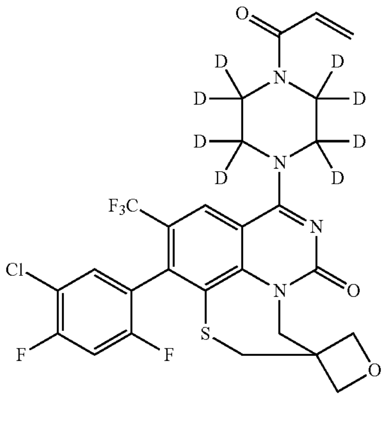 [SMILES: [2H]C1([2H])N(C(=O)C=C)C([2H])([2H])C([2H])([2H])N(c2nc(=O)n3c4c(c(-c5cc(Cl)c(F)cc5F)c(C(F)(F)F)cc24)SCC2(COC2)C3)C1([2H])[2H]] | $^1$H NMR (400 MHz, MeOH-$d_4$) δ 8.01 (s, 1H), 7.49 (t, J = 7.5 Hz, 1H), 7.34 (t, J = 9.1 Hz, 1H), 6.80 (dd, J = 16.8, 10.6 Hz, 1H), 6.27 (dd, J = 16.8, 2.0 Hz, 1H), 5.80 (dd, J = 10.6, 1.9 Hz, 1H), 4.88-4.58 (m, 4H), 4.44 (dd, J = 6.3, 2.8 Hz, 2H), 3.66-3.47 (m, 2H). | 621.2 | 97 | 8'-(4-acryloylpiperazin-1-yl-2,2,3,3,5,5,6,6-d8)-11'-(5-chloro-2,4-difluorophenyl)-10'-(trifluoromethyl)-2'H,4'H,6'H-spiro[oxetane-3,3'-[1,4]thiazepino[2,3-4-ij]quinazolin]-6'-one |

TABLE 11-continued

| Summary of % CAF at 10 μM after 1 hour for Examples 1300-1455 | | | | | |
|---|---|---|---|---|---|
| Ex. # | Structure | $^1$H NMR | MS $(M + H)^+$ | % CAF 10 uM @ 60 min | Name |
| 1310 | 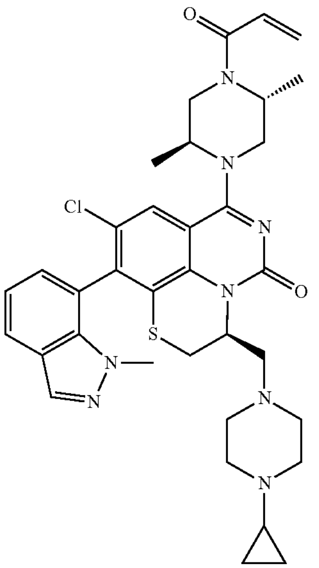 [SMILES: C=CC(=O)N1C[C@H](C)N(c2nc(=O)n3c4c(c(-c5cccc6cnn(C)c56)c(Cl)cc24)SC[C@@H]3CN2CCN(C3CC3)CC2)C[C@H]1C] | $^1$H NMR (400 MHz, $CDCl_3$) δ: 8.12 (s, 1H), 7.92 (d, J = 10.4 Hz, 1H), 7.68-7.62 (m, 1H), 7.35 (d, J = 10.0 Hz, 1H), 7.20 (d, J = 9.6 Hz, 1H), 6.75-6.58 (m, 1H), 6.47-6.39 (m, 1H), 5.86-5.81 (m, 1H), 5.44-5.35 (m, 1H), 5.14-4.73 (m, 2H), 4.51-4.16 (m, 2H), 3.79-3.71 (m, 1H), 3.67 (s, 3H), 3.55-3.29 (m, 2H), 3.11 (d, J = 16.0 Hz, 1H), 2.81-2.55 (m, 10H), 1.55-1.46 (m, 7H), 0.58-0.40 (m, 4H). | 673.4 | 95 | (3S)-7-((2S,5R)-4-acryloyl-2,5-dimethylpiperazin-1-yl)-9-chloro-3-((4-cyclopropylpiperazin-1-yl)methyl)-10-(1-methyl-1H-indazol-7-yl)-2,3-dihydro-5H-[1,4]thiazino[2,3,4-ij]quinazolin-5-one |
| 1311 | 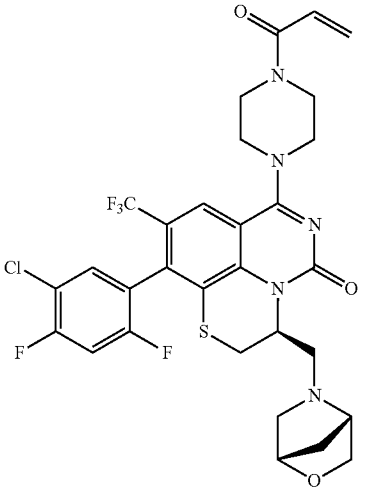 [SMILES: C=CC(=O)N1CCN(c2nc(=O)n3c4c(c(-c5cc(Cl)c(F)cc5F)c(C(F)(F)F)cc24)SC[C@@H]3CN2C[C@@H]3C[C@H]2CO3)CC1] | $^1$H NMR (400 MHz, $CDCl_3$) δ: 7.82 (s, 1H), 7.29-7.28 (m, 1H), 7.10-7.05 (m, 1H), 6.63-6.56 (m, 1H), 6.39-6.35 (m, 1H), 5.79 (d, J = 8.0 Hz, 1H), 5.23-5.21 (m, 1H), 4.43-4.41 (m, 1H), 3.96-3.89 (m, 4H), 3.80-3.78 (m, 4H), 3.64-3.50 (m, 2H), 3.02-2.86 (m, 2H), 2.80-2.78 (m, 2H), 1.78-1.69 (m, 2H), 1.61-1.60 (m, 2H), 1.26-1.24 (m, 1H). | 668.2 | 95.4 | (3S)-3-(((1S,4S)-2-oxa-5-azabicyclo[2.2.1]heptan-5-yl)methyl)-7-(4-acryloylpiperazin-1-yl)-10-(5-chloro-2,4-difluorophenyl-9-(trifluoromethyl)-2,3-dihydro-5H-[1,4]thiazino[2,3,4-ij]quinazolin-5-one |

TABLE 11-continued

| Ex. # | Structure | $^1$H NMR | MS (M + H)$^+$ | % CAF 10 uM @ 60 min | Name |
|---|---|---|---|---|---|
| 1312 | 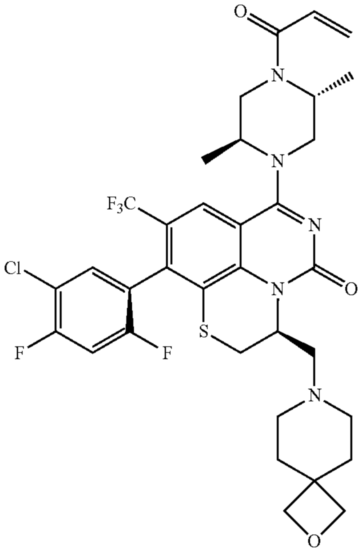 | $^1$H NMR (400 MHz, $CDCl_3$) δ: 7.84-7.82 (m, 1H), 7.26-7.23 (m, 1H), 7.07 (t, J = 8.4 Hz, 1H), 6.66-6.53 (m, 1H), 6.41-6.33 (m, 1H), 5.80-5.75 (m, 1H), 5.34-5.32 (m, 1H), 5.05-5.04 (m, 0.5H), 4.83-4.79 (m, 1H), 4.42-4.33 (m, 5.5H), 4.06-4.02 (m, 0.5H), 3.76-3.64 (m, 2H), 3.42-3.38 (m, 1H), 3.28-3.25 (m, 0.5H), 3.01-2.98 (m, 1H), 2.72-2.66 (m, 1H), 2.55-2.35 (m, 5H), 1.82-1.80 (m, 4H), 1.47-1.38 (m, 6H). | 724.3 | 72 | (3S,10S)-3-((2-oxa-7-azaspiro[3.5]nonan-7-yl)methyl)-7-((2S,5R)-4-acryloyl-2,5-dimethylpiperazin-1-yl)-10-(5-chloro-2,4-difluorophenyl)-9-(trifluoromethyl)-2,3-dihydro-5H-[1,4]thiazino[2,3,4-ij]quinazolin-5-one |
| 1313 | 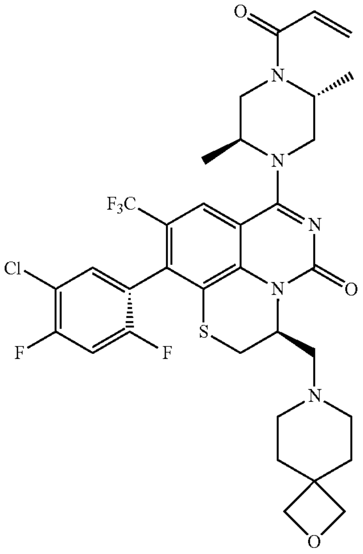 | $^1$H NMR (400 MHz, $CDCl_3$) δ: 7.83 (s, 1H), 7.30-7.26 (m, 1H), 7.07 (t, J = 8.8 Hz, 1H), 6.66-6.50 (m, 1H), 6.41-6.33 (m, 1H), 5.80-5.75 (m, 1H), 5.36-5.34 (m, 1H), 5.03-4.99 (m, 0.5H), 4.79-4.77 (m, 0.5H), 4.67-4.65 (m, 0.5H), 4.43-4.34 (m, 5.5H), 4.09-4.06 (m, 0.5H), 3.76-3.63 (m, 2H), 3.45-3.42 (m, 1H), 3.28-3.25 (m, 0.5H), 3.04-3.00 (m, 1H), 2.91-2.31 (m, 6H), 1.90-1.87 (m, 4H), 1.48-1.37 (m, 6H). | 724.3 | 96.4 | (3S,10R)-3-((2-oxa-7-azaspiro[3.5]nonan-7-yl)methyl)-7-((2S,5R)-4-acryloyl-2,5-dimethylpiperazin-1-yl)-10-(5-chloro-2,4-difluorophenyl)-9-(trifluoromethyl)-2,3-dihydro-5H-[1,4]thiazino[2,3,4-ij]quinazolin-5-one |

Summary of % CAF at 10 μM after 1 hour for Examples 1300-1455

TABLE 11-continued

| Ex. # | Structure | $^1$H NMR | MS (M + H)$^+$ | % CAF 10 uM @ 60 min | Name |
|---|---|---|---|---|---|
| Summary of % CAF at 10 μM after 1 hour for Examples 1300-1455 | | | | | |
| 1314 | 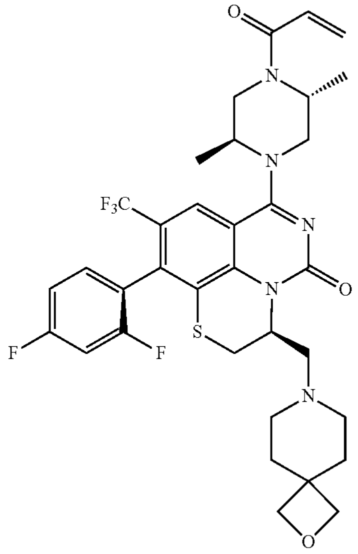 | $^1$H NMR (400 MHz, $CDCl_3$) δ 7.84-7.82 (m, 1H), 7.19-7.14 (m, 1H), 7.05-6.94 (m, 2H), 6.66-6.50 (m, 1H), 6.47 (t, J = 14.8 Hz, 1H), 5.79-5.75 (m, 1H), 5.36-5.34 (m, 1H), 5.11-4.98 (m, 0.5H), 4.80-4.68 (m, 1H), 4.41-4.33 (m, 5.5H), 4.06-4.03 (m, 0.5H), 3.77-3.64 (m, 2H), 3.39-3.25 (m, 1.5H), 3.00-2.97 (m, 1H), 2.74-2.68 (m, 1H), 2.55-2.36 (m, 5H), 1.86-1.78 (m, 4H), 1.47-1.39 (m, 6H). | 690.3 | 95.8 | (3S,10S)-3-((2-oxa-7-azaspiro[3.5]nonan-7-yl)methyl)-7-((2S,5R)-4-acryloyl-2,5-dimethylpiperazin-1-yl)-10-(2,4-difluorophenyl)-9-(trifluoromethyl)-2,3-dihydro-5H-[1,4]thiazino[2,3,4-ij]quinazolin-5-one |
| 1315 | 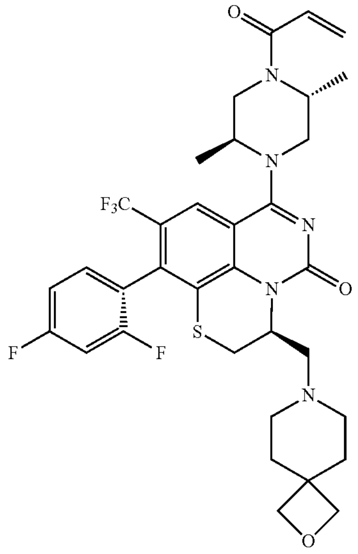 | $^1$H NMR (400 MHz, $CDCl_3$) δ: 7.83 (s, 1H), 7.21-7.16 (m, 1H), 7.04-6.94 (m, 2H), 6.66-6.50 (m, 1H), 6.41-6.33 (m, 1H), 5.79-5.75 (m, 1H), 5.32-5.30 (m, 1H), 5.03-4.99 (m, 0.5H), 4.79-4.77 (m, 1H), 4.43-4.34 (m, 5.5H), 4.10-4.06 (m, 0.5H), 3.77-3.63 (m, 2H), 3.40-3.25 (m, 1.5H), 3.02-2.98 (m, 1H), 2.74-2.69 (m, 1H), 2.57-2.34 (m, 5H), 1.86-1.79 (m, 4H), 1.47-1.37 (m, 6H). | 690.3 | 96.3 | (3S,10R)-3-((2-oxa-7-azaspiro[3.5]nonan-7-yl)methyl)-7-((2S,5R)-4-acryloyl-2,5-dimethylpiperazin-1-yl)-10-(2,4-difluorophenyl)-9-(trifluoromethyl)-2,3-dihydro-5H-[1,4]thiazino[2,3,4-ij]quinazolin-5-one |
| 1316 | 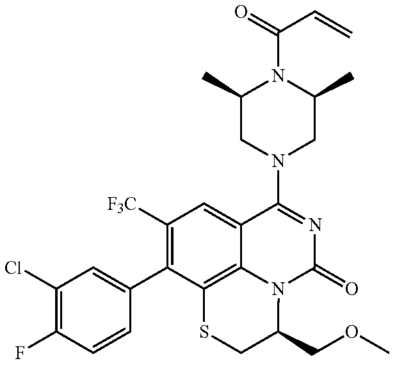 [SMILES: C=CC(=O)N1[C@H](C)CN(c2nc(=O)n3c4c(c(-c5ccc(F)c(Cl)c5)c(C(F)(F)F)cc24)SC[C@@H]3COC)C[C@@H]1C] | $^1$H NMR (400 MHz, $CDCl_3$) δ: 8.05 (s, 1H), 7.30-7.28 (m, 1H), 7.25-7.23 (m, 1H), 7.14-7.10 (m, 1H), 6.66-6.59 (m, 1H), 6.43-6.38 (m, 1H), 5.79-5.76 (m, 1H), 5.45-5.42 (m, 1H), 4.66-4.55 (m, 1H), 4.21-4.15 (m, 2H), 3.70-3.61 (m, 2H), 3.41-3.30 (m, 6H), 2.99-2.94 (m, 1H), 1.62-1.60 (m, 4H), 1.48-1.46 (m, 3H). | 611.2 | 96 | (S)-7-((3S,5R)-4-acryloyl-3,5-dimethylpiperazin-1-yl)-10-(3-chloro-4-fluorophenyl)-3-(methoxymethyl)-9-(trifluoromethyl)-2,3-dihydro-5H-[1,4]thiazino[2,3,4-ij]quinazolin-5-one |

TABLE 11-continued

| Ex. # | Structure | ¹H NMR | MS (M + H)⁺ | % CAF 10 uM @ 60 min | Name |
|---|---|---|---|---|---|
| Summary of % CAF at 10 μM after 1 hour for Examples 1300-1455 | | | | | |
| 1317 | 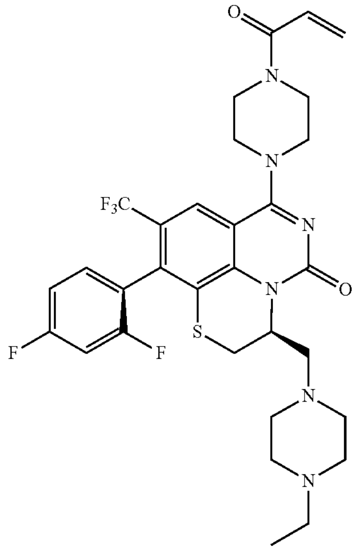 | $^1$H NMR (400 MHz, $CDCl_3$) δ 7.86 (s, 1H), 7.24-7.19 (m, 1H), 7.11-6.98 (m, 2H), 6.69-6.60 (m, 1H), 6.45-6.39 (m, 1H), 5.84 (dd, J = 14.0 Hz, 2.4 Hz, 1H), 5.47-5.43 (m, 1H), 4.00-3.85 (m, 8.5H), 3.47-3.42 (m, 1H), 3.08-3.03 (m, 1H), 2.89-2.79 (m, 3H), 2.70-2.48 (m, 8.5H), 1.19 (t, J = 9.2 Hz, 3H). | 649.2 | 98.3 | (3S,10S)-7-(4-acryloylpiperazin-1-yl)-10-(2,4-difluorophenyl)-3-((4-ethylpiperazin-1-yl)methyl)-9-(trifluoromethyl)-2,3-dihydro-5H-[1,4]thiazino[2,3,4-ij]quinazolin-5-one |
| 1318 | 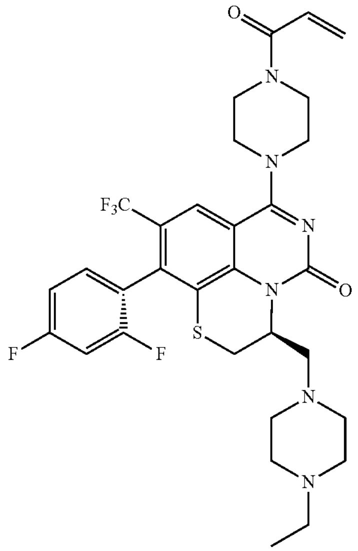 | $^1$H NMR (400 MHz, $CDCl_3$) δ 7.89 (s, 1H), 7.37-7.19 (m, 1H), 7.10-7.02 (m, 2H), 6.65-6.60 (m, 1H), 6.45-6.39 (m, 1H), 5.86-5.82 (m, 1H), 5.43-5.38 (m, 1H), 4.02-3.85 (m, 8H), 3.63-3.56 (m, 2H), 3.36-3.10 (m, 9H), 2.96-2.78 (m, 3H), 1.36 (t, J = 9.2 Hz, 3H). | 649.2 | 99.6 | (3S,10R)-7-(4-acryloylpiperazin-1-yl)-10-(2,4-difluorophenyl)-3-((4-ethylpiperazin-1-yl)methyl)-9-(trifluoromethyl)-2,3-dihydro-5H-[1,4]thiazino[2,3,4-ij]quinazolin-5-one |

TABLE 11-continued

| Ex. # | Structure | $^1$H NMR | MS (M + H)$^+$ | % CAF 10 uM @ 60 min | Name |
|---|---|---|---|---|---|
| Summary of % CAF at 10 μM after 1 hour for Examples 1300-1455 | | | | | |
| 1319 | 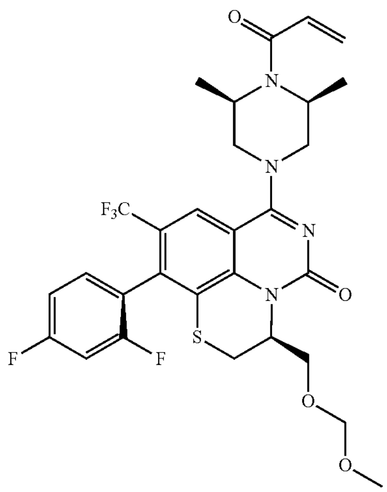 | $^1$H NMR (400 MHz, $CDCl_3$) δ: 8.07 (s, 1H), 7.21-7.15 (m, 1H), 7.06-7.01 (m, 1H), 6.98-6.93 (m, 1H), 6.66-6.59 (m, 1H), 6.42 (dd, J = 1.6 Hz, 16.8 Hz, 1H), 5.78 (dd, J = 1.2 Hz, 10.4 Hz, 1H), 5.51-5.49 (m, 1H), 4.67-4.62 (m, 4H), 4.22-4.19 (m, 2H), 3.82-3.74 (m, 2H), 3.40-3.30 (m, 6H), 3.07-3.03 (m, 1H), 1.61 (d, J = 6.8 Hz, 3H), 1.48 (d, J = 6.8 Hz, 3H). | 625.3 | 96.3 | (3S,10S)-7-((3S,5R)-4-acryloyl-3,5-dimethylpiperazin-1-yl)-10-(2,4-difluorophenyl)-3-((methoxymethoxy)methyl)-9-(trifluoromethyl)-2,3-dihydro-5H-[1,4]thiazino[2,3,4-ij]quinazolin-5-one |
| 1320 | 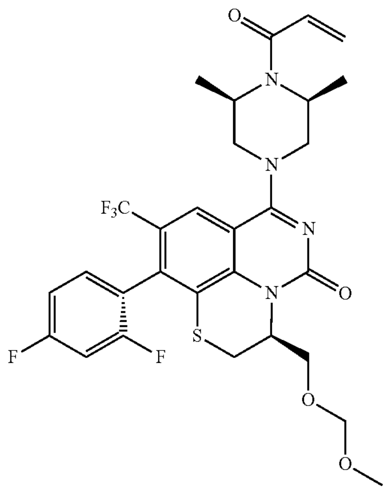 | $^1$H NMR (400 MHz, $CDCl_3$) δ: 8.07 (s, 1H), 7.20-7.15 (m, 1H), 7.04-6.94 (m, 2H), 6.66-6.59 (m, 1H), 6.42 (dd, J = 1.2 Hz, 16.4 Hz, 1H), 5.78 (dd, J = 1.2 Hz, 10.0 Hz, 1H), 5.48-5.45 (m, 1H), 4.67-4.62 (m, 4H), 4.21-4.18 (m, 2H), 3.80-3.78 (m, 2H), 3.39-3.30 (m, 6H), 3.09-3.05 (m, 1H), 1.61 (d, J = 6.8 Hz, 3H), 1.48 (d, J = 6.8 Hz, 3H). | 625.3 | 97.4 | (3S,10R)-7-((3S,5R)-4-acryloyl-3,5-dimethylpiperazin-1-yl)-10-(2,4-difluorophenyl)-3-((methoxymethoxy)methyl)-9-(trifluoromethyl)-2,3-dihydro-5H-[1,4]thiazino[2,3,4-ij]quinazolin-5-one |

TABLE 11-continued

| Summary of % CAF at 10 μM after 1 hour for Examples 1300-1455 | | | | | |
|---|---|---|---|---|---|
| Ex. # | Structure | $^1$H NMR | MS (M + H)$^+$ | % CAF 10 uM @ 60 min | Name |
| 1321 | 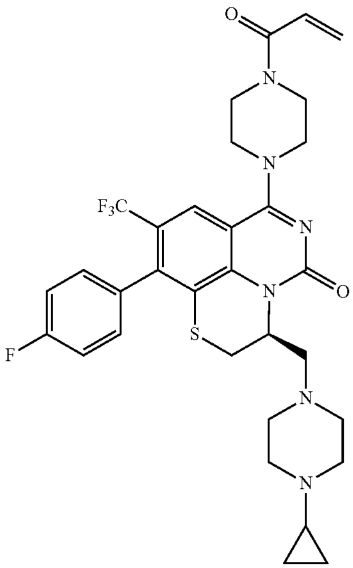 | $^1$H NMR (400 MHz, $CDCl_3$) δ: 7.80 (s, 1H), 7.21-7.17 (m, 4H), 6.62-6.54 (m, 1H), 6.41-6.31 (m, 1H), 5.82-5.76 (m, 1H), 5.35-5.29 (m, 1H), 3.97-3.73 (m, 9H), 3.47-3.35 (m, 1H), 2.98-2.93 (m, 1H), 2.86-2.46 (m, 10H), 0.59-0.37 (m, 4H). | 643.3 | 99.3 | (S)-7-(4-acryloylpiperaizn-1-yl)-3-((4-cyclopropylpiperazin-1-yl)methyl)-10-(4-fluorophenyl)-9-(trifluoromethyl)-2,3-dihydro-5H-[1,4]thiazino[2,3,4-ij]quinazolin-5-one |
| 1322 | 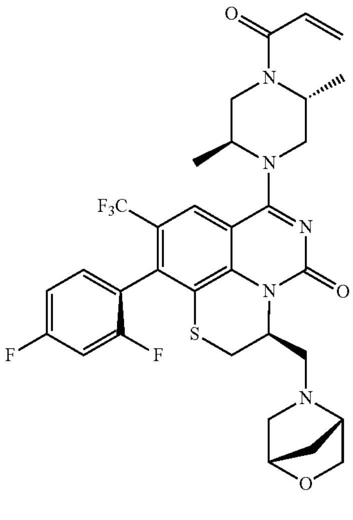 | $^1$H NMR (400 MHz, $CDCl_3$) δ: 7.85 (d, J = 10 Hz, 1H), 7.20-7.14 (m, 1H), 7.07-6.93 (m, 2H), 6.69-6.49 (m, 1H), 6.44-6.31 (m, 1H), 5.81-5.75 (m, 1H), 5.26-5.17 (m, 1H), 5.09-4.61 (m, 2H), 4.46-4.31 (m, 2H), 4.14-3.84 (m, 2H), 3.77-3.39 (m, 5H), 3.29-2.79 (m, 5H), 1.80-1.70 (m, 2H), 1.50-1.41 (m, 6H). | 662.3 | 96.2 | (3S,10S)-3-(((1S,4S)-2-oxa-5-azabicyclo[2.2.1]heptan-5-yl)methyl)-7-((2S,5R)-4-acryloyl-2,5-dimethylpiperazin-1-yl)-10-(2,4-difluorophenyl)-9-(trifluoromethyl)-2,3-dihydro-5H-[1,4]thiazino[2,3,4-ij]quinazolin-5-one |

TABLE 11-continued

| Summary of % CAF at 10 μM after 1 hour for Examples 1300-1455 | | | | | |
|---|---|---|---|---|---|
| Ex. # | Structure | $^{1}$H NMR | MS (M + H)$^{+}$ | % CAF 10 uM @ 60 min | Name |
| 1323 | 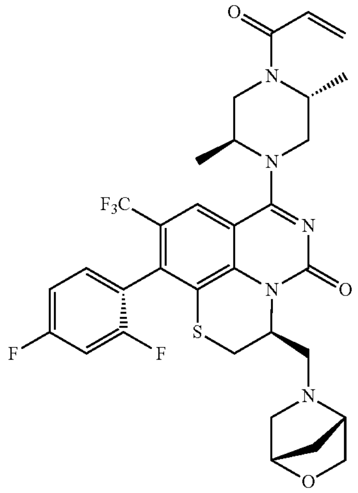 | $^{1}$H NMR (400 MHz, $CDCl_3$) δ: 7.91 (d, J = 16.8 Hz, 1H), 7.20-7.13 (m, 1H), 7.04-6.95 (m, 2H), 6.68-6.49 (m, 1H), 6.43-6.34 (m, 1H), 5.84-5.74 (m, 1H), 5.41-5.35 (m, 1H), 5.14-4.71 (m, 2H), 4.66-4.56 (m, 2H), 4.49-3.88 (m, 4H), 3.82-3.46 (m, 6H), 3.19-3.11 (m, 1H), 2.37-2.26 (m, 2H), 2.19-2.14 (m, 1H), 1.61-1.48 (m, 6H). | 662.3 | 96.1 | (3S,10R)-3-(((1S,4S)-2-oxa-5-azabicyclo[2.2.1]heptan-5-yl)methyl)-7-((2S,5R)-4-acryloyl-2,5-dimethylpiperazin-1-yl)-10-(2,4-difluorophenyl)-9-(trifluoromethyl)-2,3-dihydro-5H-[1,4]thiazino[2,3,4-ij]quinazolin-5-one |
| 1324 | 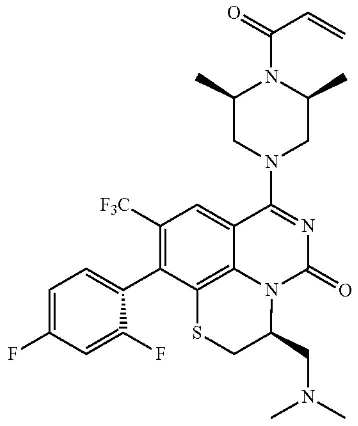 | $^{1}$H NMR (400 MHz, $CDCl_3$) δ: 8.07 (s, 1H), 7.20-7.14 (m, 1H), 7.04-6.94 (m, 2H), 6.66-6.59 (m, 1H), 6.42 (dd, J = 1.6 Hz, 16.4 Hz, 1H), 5.78 (dd, J = 1.6 Hz, 10.4 Hz, 1H), 5.37-5.35 (m, 1H), 4.73-4.60 (m, 2H), 4.20-4.17 (m, 2H), 3.39-2.75 (m, 6H), 2.43-2.31 (m, 6H), 1.61 (d, J = 7.2 Hz, 3H), 1.49 (d, J = 7.2 Hz, 3H). | 608.3 | 82.2 | (3S,10R)-7-((3S,5R)-4-acryloyl-3,5-dimethylpiperazin-1-yl)-10-(2,4-difluorophenyl)-3-((dimethylamino)methyl)-9-(trifluoromethyl)-2,3-dihydro-5H-[1,4]thiazino[2,3,4-ij]quinazolin-5-one |
| 1325 | 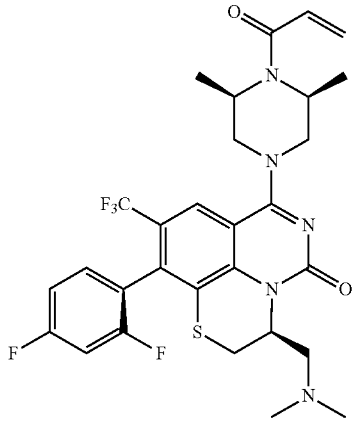 | $^{1}$H NMR (400 MHz, $CDCl_3$) δ: 8.07 (s, 1H), 7.21-7.15 (m, 1H), 7.06-6.94 (m, 2H), 6.65-6.59 (m, 1H), 6.42 (dd, J = 1.6 Hz, 16.4 Hz, 1H), 5.78 (dd, J = 2.0 Hz, 10.4 Hz, 1H), 5.41-5.38 (m, 1H), 4.77-4.58 (m, 2H), 4.21-4.18 (m, 2H), 3.41-2.99 (m, 6H), 2.45-2.32 (m, 6H), 1.61 (d, J = 6.8 Hz, 3H), 1.49 (d, J = 6.8 Hz, 3H). | 608.3 | 81.4 | (3S,10S)-7-((3S,5R)-4-acryloyl-3,5-dimethylpiperazin-1-yl)-10-(2,4-difluorophenyl)-3-((dimethylamino)methyl)-9-(trifluoromethyl)-2,3-dihydro-5H-[1,4]thiazino[2,3,4-ij]quinazolin-5-one |

TABLE 11-continued

| Summary of % CAF at 10 μM after 1 hour for Examples 1300-1455 | | | | | |
|---|---|---|---|---|---|
| Ex. # | Structure | $^1$H NMR | MS $(M + H)^+$ | % CAF 10 uM @ 60 min | Name |
| 1326 | 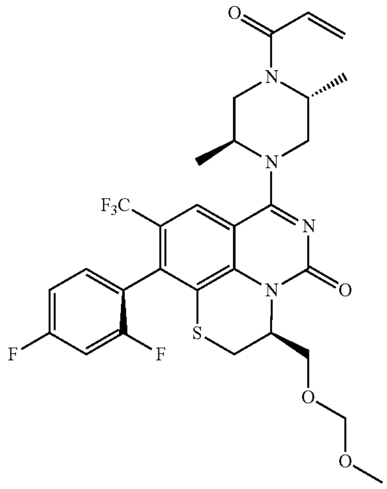 | $^1$H NMR (400 MHz, $CDCl_3$) δ: 7.86-7.83 (m, 1H), 7.19-7.14 (m, 1H), 7.05-6.93 (m, 2H), 6.66-6.50 (m, 1H), 6.37 (t, J = 14.4 Hz, 1H), 5.80-5.75 (m, 1H), 5.48-5.47 (m, 1H), 5.07-5.05 (m, 0.5H), 4.83-4.78 (m, 0.5H), 4.69-4.62 (m, 2.5H), 4.47-4.34 (m, 1.5H), 4.10-3.64 (m, 5H), 3.35 (s, 3H), 3.27-3.04 (m, 2H), 1.49-1.42 (m, 6H). | 625.2 | 82.3 | (3S,10S)-7-((2S,5R)-4-acryloyl-3,5-dimethylpiperazin-1-yl)-10-(2,4-difluorophenyl)-3-((methoxymethoxy)methyl)-9-(trifluoromethyl)-2,3-dihydro-5H-[1,4]thiazino[2,3,4-ij]quinazolin-5-one |
| 1327 | 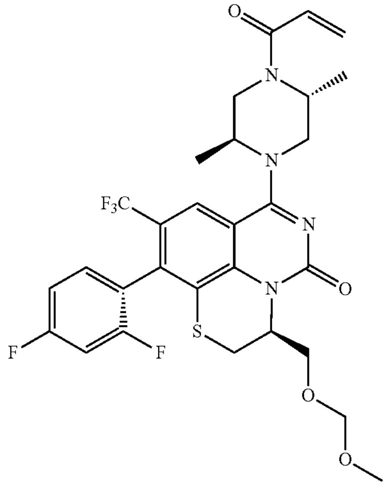 | $^1$H NMR (400 MHz, $CDCl_3$) δ: 7.85-7.83 (m, 1H), 7.22-7.16 (m, 1H), 7.04-6.94 (m, 2H), 6.66-6.50 (m, 1H), 6.37 (t, J = 14.8 Hz, 1H), 5.77 (t, J = 9.2 Hz, 1H), 5.45-5.43 (m, 1H), 5.09-5.03 (m, 0.5H), 4.80-4.78 (m, 0.5H), 4.70-4.62 (m, 2H), 4.44-4.11 (m, 2H), 3.80-3.61 (m, 4H), 3.37-3.20 (m, 4H), 3.09-3.05 (m, 1H), 1.49-1.40 (m, 6H). | 625.2 | 86.3 | (3S,10R)-7-((2S,5R)-4-acryloyl-3,5-dimethylpiperazin-1-yl)-10-(2,4-difluorophenyl)-3-((methoxymethoxy)methyl)-9-(trifluoromethyl)-2,3-dihydro-5H-[1,4]thiazino[2,3,4-ij]quinazolin-5-one |
| 1328 | 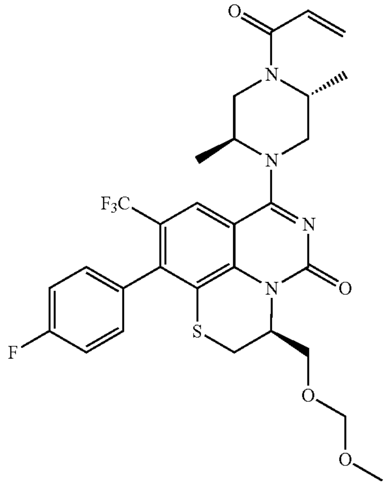 [SMILES: C=CC(=O)N1C[C@H](C)N(c2nc(=O)n3c4c(c(-c5ccc(F)cc5)c(C(F)(F)F)cc24)SC[C@@H]3COCOC)C[C@H]1C] | $^1$H NMR (400 MHz, $CDCl_3$) δ 7.85-7.83 (m, 1H), 7.22-7.14 (m, 4H), 6.67-6.50 (m, 1H), 6.37 (t, J = 15.6 Hz, 1H), 5.77 (t, J = 9.2 Hz, 1H), 5.45-5.44 (m, 1H), 5.05-4.80 (m, 1H), 4.67-4.62 (m, 2H), 4.43-4.07 (m, 2H), 3.81-3.62 (m, 4H), 3.35-3.23 (m, 5H), 3.02-2.99 (m, 1H), 1.49-1.42 (m, 6H). | 607.2 | 93.8 | (S)-7-((2S,5R)-4-acryloyl-2,5-dimethylpiperazin-1-yl)-10-(4-fluorophenyl)-3-((methoxymethoxy)methyl)-9-(trifluoromethyl)-2,3-dihydro-5H-[1,4]thiazino[2,3,4-ij]quinazolin-5-one |

TABLE 11-continued

Summary of % CAF at 10 μM after 1 hour for Examples 1300-1455

| Ex. # | Structure | $^1$H NMR | MS $(M + H)^+$ | % CAF 10 uM @ 60 min | Name |
|---|---|---|---|---|---|
| 1329 | 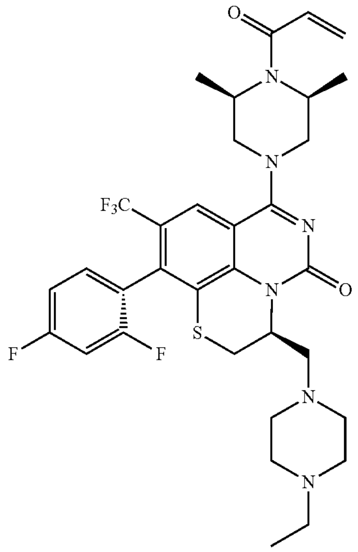 | $^1$H NMR (400 MHz, $CDCl_3$) δ 8.07 (s, 1H), 7.22-7.12 (m, 1H), 7.08-6.92 (m, 2H), 6.68-6.56 (m, 1H), 6.46-6.36 (m, 1H), 5.77 (dd, J = 9.2 Hz, 1.6 Hz, 1H), 5.40-5.32 (m, 1H), 4.90-4.54 (m, 2H), 4.18 (d, J = 12.0 Hz, 2H), 3.46-3.28 (m, 3.5H), 3.06-2.98 (m, 1H), 2.86-2.76 (m, 3H), 2.70-2.40 (m, 9.5H), 1.62-1.58 (m, 3H), 1.49 (d, J = 6.8 Hz, 3H), 1.12 (t, J = 7.0 Hz, 3H). | 677.3 | 95.4 | (3S,10R)-7-((3S,5R)-4-acryloyl-3,5-dimethylpiperazin-1-yl)-10-(2,4-difluorophenyl)-3-((4-ethylpiperazin-1-yl)methyl)-9-(trifluoromethyl)-2,3-dihydro-5H-[1,4]thiazino[2,3,4-ij]quinazolin-5-one |
| 1330 | 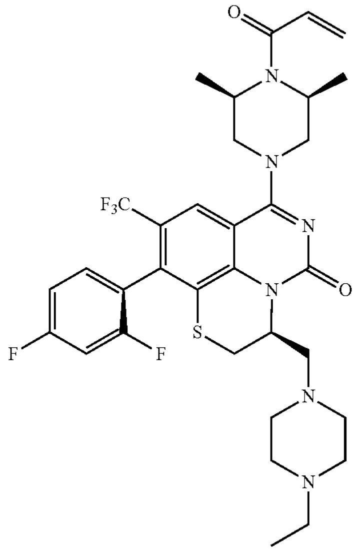 | $^1$H NMR (400 MHz, $CDCl_3$) δ: 8.07 (s, 1H), 7.24-7.14 (m, 1H), 7.08-6.92 (m, 2H), 6.68-6.56 (m, 1H), 6.46-6.36 (m, 1H), 5.77 (dd, J = 10.4 Hz, 2.0 Hz, 1H), 5.46-5.36 (m, 1H), 4.86-4.46 (m, 2H), 4.24-4.18 (m, 2H), 3.48-3.26 (m, 3.5H), 3.04-2.96 (m, 1H), 2.86-2.70 (m, 3H), 2.62-2.30 (m, 9.5H), 1.62-1.46 (m, 6H), 1.07 (t, J = 7.0 Hz, 3H). | 677.3 | 85 | (3S,10S)-7-((3S,5R)-4-acryloyl-3,5-dimethylpiperazin-1-yl)-10-(2,4-difluorophenyl)-3-((4-ethylpiperazin-1-yl)methyl)-9-(trifluoromethyl)-2,3-dihydro-5H-[1,4]thiazino[2,3,4-ij]quinazolin-5-one |

TABLE 11-continued

| Summary of % CAF at 10 μM after 1 hour for Examples 1300-1455 | | | | | |
|---|---|---|---|---|---|
| Ex. # | Structure | $^1$H NMR | MS $(M + H)^+$ | % CAF 10 uM @ 60 min | Name |
| 1331 | 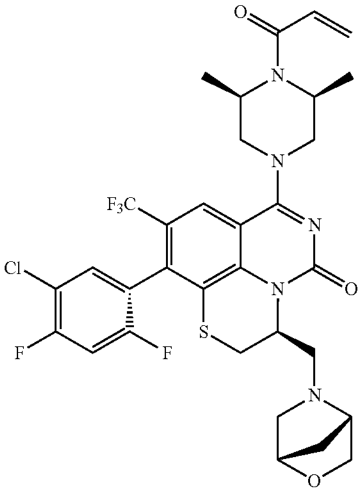 | $^1$H NMR (400 MHz, $CDCl_3$) δ 8.07 (s, 1H), 7.28-7.24 (m, 1H), 7.08 (t, J = 8.4 Hz, 1H), 6.66-6.59 (m, 1H), 6.43-6.38 (m, 1H), 5.77 (dd, J = 10.4 Hz, 1.6 Hz, 1H), 5.28-5.19 (m, 1H), 4.68-4.64 (m, 1.5H), 4.45-4.38 (m, 1H), 4.18 (m, J = 12.8 Hz, 2H), 3.91-3.88 (m, 1H), 3.63-3.31 (m, 5.5H), 3.01-2.80 (m, 5H), 1.77-1.73 (m, 2H), 1.60 (d, J = 6.8 Hz, 3H), 1.49 (d, J = 6.8 Hz, 3H). | 696.1 | 94.5 | (3S,10R)-3-(((1S,4S)-2-oxa-5-azabicyclo[2.2.1]heptan-5-yl)methyl)-7-((3S,5R)-4-acryloyl-3,5-dimethylpiperazin-1-yl)-10-(5-chloro-2,4-difluorophenyl)-9-(trifluoromethyl)-2,3-dihydro-5H-[1,4]thiazino[2,3,4-ij]quinazolin-5-one |
| 1332 | 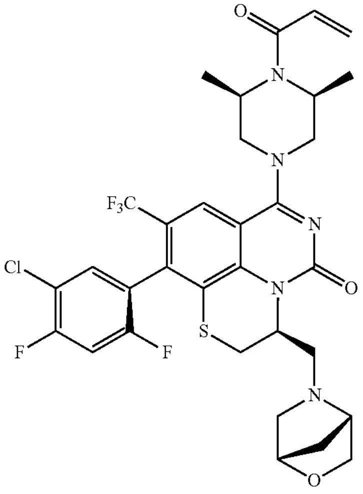 | $^1$H NMR (400 MHz, $CDCl_3$) δ 8.07 (s, 1H), 7.29-7.27 (m, 1H), 7.07 (t, J = 8 Hz, 1H), 6.66-6.59 (m, 1H), 6.43-6.38 (m, 1H), 5.79-5.76 (m, 1H), 5.26-5.24 (m, 1H), 4.72-4.60 (m, 2H), 4.41-4.39 (m, 1H), 4.19 (d, J = 13.2 Hz, 2H), 3.91-3.87 (m, 1H), 3.62-3.32 (m, 5.5H), 3.01-2.83 (m, 4.5H), 1.75-1.66 (m, 2H), 1.61 (d, J = 6.8 Hz, 3H), 1.47 (d, J = 7.2 Hz, 3H). | 696.1 | 87 | (3S,10S)-3-(((1S,4S)-2-oxa-5-azabicyclo[2.2.1]heptan-5-yl)methyl)-7-((3S,5R)-4-acryloyl-3,5-dimethylpiperazin-1-yl)-10-(5-chloro-2,4-difluorophenyl)-9-(trifluoromethyl)-2,3-dihydro-5H-[1,4]thiazino[2,3,4-ij]quinazolin-5-one |

TABLE 11-continued

| Summary of % CAF at 10 μM after 1 hour for Examples 1300-1455 | | | | | |
|---|---|---|---|---|---|
| Ex. # | Structure | $^1$H NMR | MS (M + H)$^+$ | % CAF 10 uM @ 60 min | Name |
| 1333 | 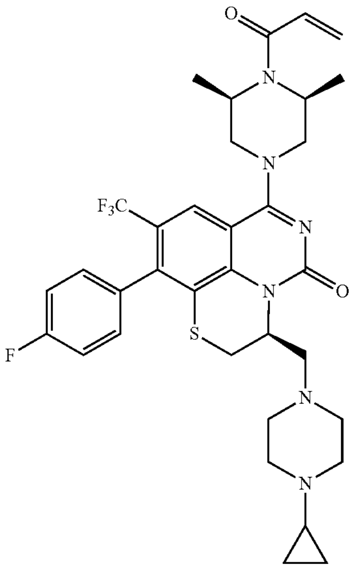 [SMILES: C=CC(=O)N1[C@H](C)CN(c2nc(=O)n3c4c(c(-c5ccc(F)cc5)c(C(F)(F)F)cc24)SC[C@@H]3CN2CCN(C3CC3)CC2)C[C@@H]1C] | $^1$H NMR (400 MHz, $CDCl_3$) δ: 8.05 (s, 1H), 7.21-7.18 (m, 4H), 6.66-6.59 (m, 1H), 6.40 (dd, J = 17.2 Hz, 1.6 Hz, 1H), 5.77 (dd, J = 10.8 Hz, 1.6 Hz, 1H), 5.36-5.35 (m, 1H), 4.72-4.55 (m, 1H), 4.20-4.17 (m, 2H), 3.38-3.29 (m, 3H), 2.97-2.94 (m, 1H), 2.83-2.47 (m, 9H), 1.60-1.59 (m, 6H), 1.49 (d, J = 7.2 Hz, 3H), 0.69-0.20 (m, 4H). | 671.5 | 61 | (S)-7-((3S,5R)-4-acryloyl-3,5-dimethylpiperazin-1-yl)-3-((4-cyclopropylpiperazin-1-yl)methyl)-10-(4-fluorophenyl)-9-(trifluoromethyl)-2,3-dihydro-5H-[1,4]thiazino[2,3,4-ij]quinazolin-5-one |
| 1334 | 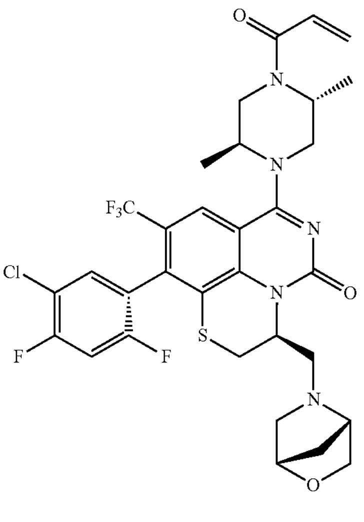 | $^1$H NMR (400 MHz, $CDCl_3$) δ: 7.84 (d, J = 4.0 Hz, 1H), 7.30-7.28 (m, 1H), 7.08 (t, J = 8.8 Hz, 1H), 6.67-6.50 (m, 1H), 6.41-6.33 (m, 1H), 5.80-5.76 (m, 1H), 5.25-5.17 (m, 1H), 5.08-5.01 (m, 0.5H), 4.82-4.66 (m, 1H), 4.44-4.35 (m, 2.5H), 4.16-3.91 (m, 2H), 3.77-3.49 (m, 5H), 3.27-2.88 (m, 5H), 1.77-1.74 (m, 2H), 1.52-1.34 (m, 6H). | 696.3 | 80 | (3S,10R)-3-(((1S,4S)-2-oxa-5-azabicyclo[2.2.1]heptan-5-yl)methyl)-7-((2S,5R)-4-acryloyl-2,5-dimethylpiperazin-1-yl)-10-(5-chloro-2,4-difluorophenyl)-9-(trifluoromethyl)-2,3-dihydro-5H-[1,4]thiazino[2,3,4-ij]quinazolin-5-one |

TABLE 11-continued

| Summary of % CAF at 10 μM after 1 hour for Examples 1300-1455 | | | | | |
|---|---|---|---|---|---|
| Ex. # | Structure | $^1$H NMR | MS $(M + H)^+$ | % CAF 10 uM @ 60 min | Name |
| 1335 | 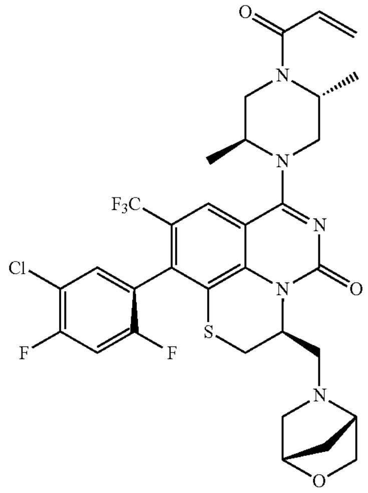 | $^1$H NMR (400 MHz, $CDCl_3$) δ: 7.84 (d, J = 10.0 Hz, 1H), 7.23-7.22 (m, 1H), 7.09-7.05 (m, 1H), 6.67-6.51 (m, 1H), 6.41-6.34 (m, 1H), 5.80-5.76 (m, 1H), 5.28-5.21 (m, 1H), 5.06-5.05 (m, 0.5H), 4.78-4.65 (m, 1H), 4.40-4.33 (m, 2.5H), 4.09-3.88 (m, 2H), 3.75-3.43 (m, 5H), 3.26-2.81 (m, 5H), 1.75-1.742 (m, 2H), 1.52-1.43 (m, 6H). | 696.3 | 29.7 | (3S,10S)-3-(((1S,4S)-2-oxa-5-azabicyclo[2.2.1]heptan-5-yl)methyl)-7-((2S,5R)-4-acryloyl-2,5-dimethylpiperazin-1-yl)-10-(5-chloro-2,4-difluorophenyl)-9-(trifluoromethyl)-2,3-dihydro-5H-[1,4]thiazino[2,3,4-ij]quinazolin-5-one |
| 1336 | 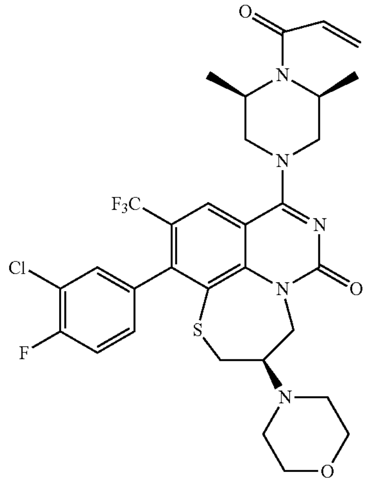 [SMILES: C=CC(=O)N1[C@H](C)CN(c2nc(=O)n3c4c(c(-c5ccc(F)c(Cl)c5)c(C(F)(F)F)cc24)SC[C@H](N2CCOCC2)C3)C[C@@H]1C] | $^1$H NMR (400 MHz, $CDCl_3$) δ: 8.05 (s, 1H), 7.30-7.23 (m, 2H), 7.11-7.10 (m, 1H), 6.65-6.59 (m, 1H), 6.43-6.38 (m, 1H), 5.79-5.76 (m, 1H), 4.74-4.60 (m, 4H), 4.17-4.15 (m, 2H), 3.76-3.66 (m, 4H), 3.37-3.11 (m, 5H), 2.80-2.43 (m, 4H), 1.58-1.54 (m, 6H). | 666.1 | 85.5 | (R)-8-((3S,5R)-4-acryloyl-3,5-dimethylpiperazin-1-yl)-11-(3-chloro-4-fluorophenyl)-3-morpholino-10-(trifluoromethyl)-3,4-dihydro-2H,6H-[1,4]thiazepino[2,3-4-ij]quinazolin-6-one |

TABLE 11-continued

| Ex. # | Structure | $^1$H NMR | MS (M + H)$^+$ | % CAF 10 uM @ 60 min | Name |
|---|---|---|---|---|---|
| Summary of % CAF at 10 μM after 1 hour for Examples 1300-1455 | | | | | |
| 1337 | 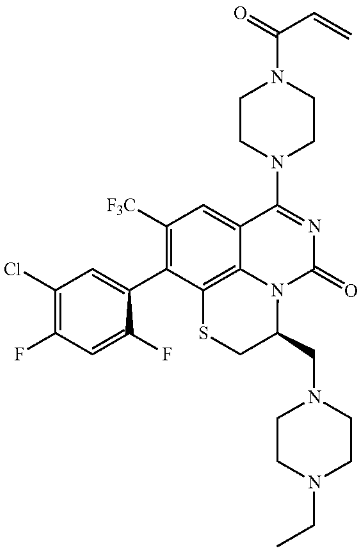 | $^1$H NMR (400 MHz, $CDCl_3$) δ: 7.80 (s, 1H), 7.28-7.26 (m, 1H), 7.08-7.04 (m, 1H), 6.62-6.56 (m, 1H), 6.39-6.34 (m, 1H), 5.80-5.77 (m, 1H), 5.41-5.37 (m, 1H), 3.94-3.79 (m, 8.5H), 3.48-3.44 (m, 1H), 3.02-2.98 (m, 1H), 2.79-2.74 (m, 3H), 2.54-2.36 (m, 8.5H), 1.07 (t, J = 6.8 Hz, 3H). | 683.3 | 96.7 | (3S,10S)-7-(4-acryloylpiperazin-1-yl)-10-(5-chloro-2,4-difluorophenyl)-3-((4-ethylpiperazin-1-yl)methyl)-9-(trifluoromethyl)-2,3-dihydro-5H-[1,4]thiazino[2,3,4-ij]quinazolin-5-one |
| 1338 | 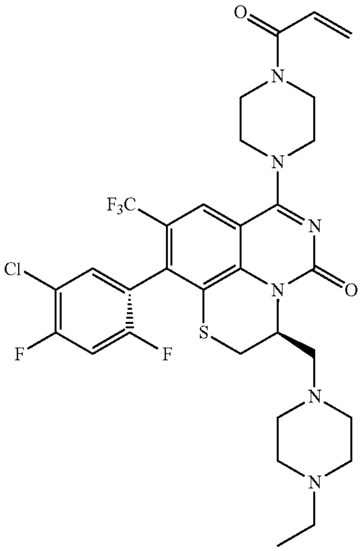 | $^1$H NMR (400 MHz, $CDCl_3$) δ: 7.80 (s, 1H), 7.29-7.26 (m, 1H), 7.09-7.04 (m, 1H), 6.62-6.55 (m, 1H), 6.39-6.34 (m, 1H), 5.79-5.76 (m, 1H), 5.37-5.33 (m, 1H), 3.94-3.78 (m, 8.5H), 3.49-3.45 (m, 1H), 3.02-2.98 (m, 1H), 2.83-2.77 (m, 3H), 2.56-2.36 (m, 8.5H), 1.09-1.05 (t, J = 6.8 Hz, 3H). | 683.3 | 99 | (3S,10R)-7-(4-acryloylpiperazin-1-yl)-10-(5-chloro-2,4-difluorophenyl)-3-((4-ethylpiperazin-1-yl)methyl)-9-(trifluoromethyl)-2,3-dihydro-5H-[1,4]thiazino[2,3,4-ij]quinazolin-5-one |

TABLE 11-continued

| Ex. # | Structure | $^1$H NMR | MS $(M + H)^+$ | % CAF 10 uM @ 60 min | Name |
|---|---|---|---|---|---|
| Summary of % CAF at 10 μM after 1 hour for Examples 1300-1455 | | | | | |
| 1339 | 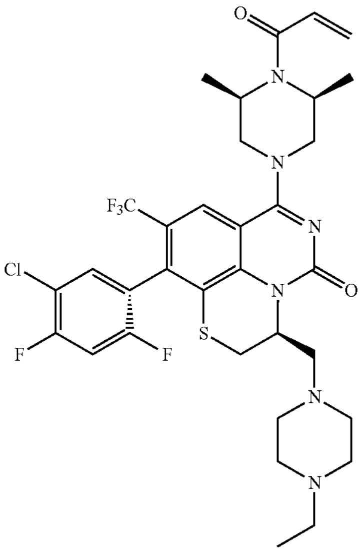 | $^1$H NMR (400 MHz, $CDCl_3$) δ: 8.06 (s, 1H), 7.28-7.24 (m, 1H), 7.07 (t, J = 8.8 Hz, 1H), 6.66-6.59 (m, 1H), 6.43-6.38 (m, 1H), 5.77 (dd, J = 10.0 Hz, 2.0 Hz, 1H), 5.39-5.35 (m, 1H), 4.71-4.59 (m, 1H), 4.20-4.15 (m, 2H), 3.48-3.44 (m, 1H), 3.37-3.29 (m, 2H), 3.03-2.99 (m, 1H), 2.82-2.72 (m, 3H), 2.55-2.32 (m, 9H), 1.59-1.58 (d, J = 6.8 Hz, 4H), 1.50-1.49 (d, J = 6.8 Hz, 3H), 1.09-1.05 (t, J = 7.2 Hz, 3H). | 711.2 | 68.7 | (3S,10R)-7-((3S,5R)-4-acryloyl-3,5-dimethylpiperazin-1-yl)-10-(5-chloro-2,4-dichlorophenyl)-3-((4-ethylpiperazin-1-yl)methyl)-9-(trifluoromethyl)-2,3-dihydro-5H-[1,4]thiazino[2,3,4-ij]quinazolin-5-one |
| 1340 | 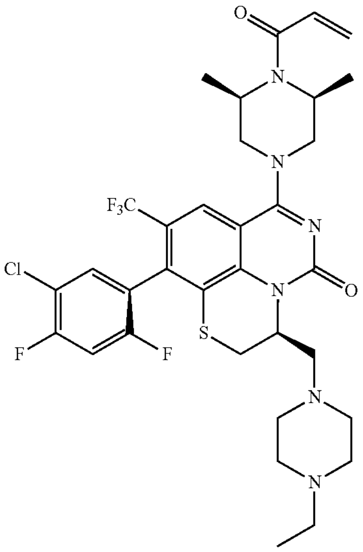 | $^1$H NMR (400 MHz, $CDCl_3$) δ: 8.06 (s, 1H), 7.29-7.26 (m, 1H), 7.07 (t, J = 8.4 Hz, 1H), 6.66-6.59 (m, 1H), 6.43-6.38 (m, 1H), 5.79-5.76 (m, 1H), 5.42-5.39 (m, 1H), 4.83-4.53 (m, 1H), 4.20-4.15 (m, 2H), 3.46-3.29 (m, 1H), 3.02-2.99 (m, 1H), 2.80-2.72 (m, 3H), 2.57-2.35 (m, 9H), 1.60-1.59 (d, J = 6.8 Hz, 4H), 1.49-1.47 (d, J = 7.2 Hz, 3H), 1.11-1.07 (t, J = 6.8 Hz, 3H). | 711.2 | 89.4 | (3S,10S)-7-((3S,5R)-4-acryloyl-3,5-dimethylpiperazin-1-yl)-10-(5-chloro-2,4-difluorophenyl)-3-((4-ethylpiperazin-1-yl)methyl)-9-(trifluoromethyl)-2,3-dihydro-5H-[1,4]thiazino[2,3,4-ij]quinazolin-5-one |

TABLE 11-continued

Summary of % CAF at 10 μM after 1 hour for Examples 1300-1455

| Ex. # | Structure | $^1H$ NMR | MS $(M + H)^+$ | % CAF 10 uM @ 60 min | Name |
|---|---|---|---|---|---|
| 1341 | 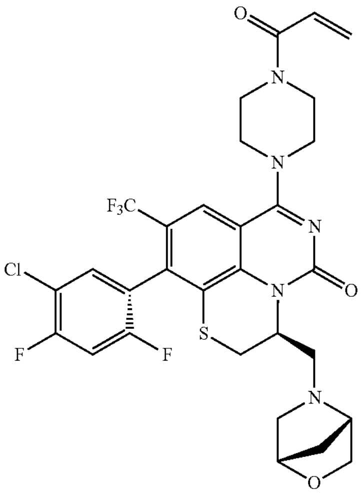 | $^1H$ NMR (400 MHz, $CDCl_3$) δ: 7.81 (s, 1H), 7.27 (m, 1H), 7.10-7.06 (t, J = 8.8 Hz, 1H), 6.63-6.56 (m, 1H), 6.37 (dd, J = 1.6 Hz, 16.8 Hz, 1H), 5.79 (dd, J = 1.6 Hz, 10.4 Hz, 1H), 5.12-5.10 (m, 1H), 4.42 (s, 1H), 3.96-3.90 (m, 4H), 3.82-3.79 (m, 5H), 3.64-3.52 (m, 3H), 3.02-2.89 (m, 5H), 1.78-1.74 (m, 2H). | 668.1 | 97.4 | (3S,10R)-3-(((1S,4S)-2-oxa-5-azabicyclo[2.2.1]heptan-5-yl)methyl)-7-(4-acryloylpiperazin-1-yl)-10-(5-chloro-2,4-difluorophenyl)-9-(trifluoromethyl)-2,3-dihydro-5H-[1,4]thiazino[2,3,4-ij]quinazolin-5-one |
| 1342 | 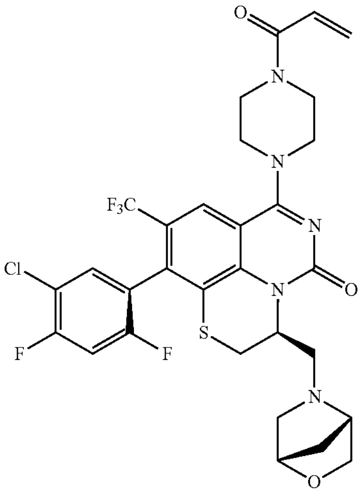 | $^1H$ NMR (400 MHz, $CDCl_3$) δ: 7.82 (s, 1H), 7.29-7.26 (m, 1H), 7.07 (t, J = 8.8 Hz, 1H), 6.63-6.56 (m, 1H), 6.37 (dd, J = 1.6 Hz, 16.8 Hz, 1H), 5.79 (dd, J = 1.6 Hz, 10.4 Hz, 1H), 5.26-5.25 (m, 1H), 4.41-4.39 (m, 1H), 3.97-3.87 (m, 4H), 3.86-3.80 (m, 5H), 3.62-3.50 (m, 3H), 3.01-2.84 (m, 5H), 1.76-1.70 (m, 2H). | 668.1 | 44.1 | (3S,10S)-3-(((1S,4S)-2-oxa-5-azabicyclo[2.2.1]heptan-5-yl)methyl)-7-(4-acryloylpiperazin-1-yl)-10-(5-chloro-2,4-difluorophenyl)-9-(trifluoromethyl)-2,3-dihydro-5H-[1,4]thiazino[2,3,4-ij]quinazolin-5-one |
| 1343 | 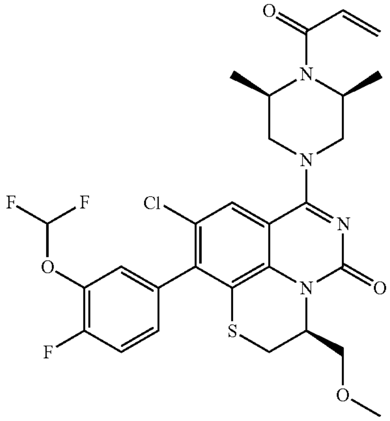 [SMILES: C=CC(=O)N1[C@H](C)CN(c2nc(=O)n3c4c(c(-c5ccc(F)c(OC(F)F)c5)c(Cl)cc24)SC[C@@H]3COC)C[C@@H]1C] | $^1H$ NMR (400 MHz, MeOH-$d_4$) δ: 7.89 (s, 1H), 7.43 (ddd, J = 10.5, 8.4, 6.2 Hz, 1H), 7.30-7.13 (m, 2H), 6.91 ($J_{HF}$ = 73.1 Hz, 1H), 6.83 (dd, J = 16.7, 10.6 Hz, 1H), 6.28 (dd, J = 16.6, 2.0 Hz, 1H), 5.80 (dd, J = 10.5, 2.0 Hz, 1H), 5.40-5.30 (m, 1H), 4.78-4.51 (m, 2H), 4.37 (d, J = 13.6 Hz, 1H), 4.25 (dt, J = 13.5, 2.2 Hz, 1H), 3.75 (td, J = 9.1, 4.9 Hz, 1H), 3.67-3.50 (m, 3H), 3.49-3.41 (m, 2H), 3.40 (d, J = 7.0 Hz, 3H), 3.38-3.34 (m, 1H), 3.11 (dt, J = 13.5, 2.6 Hz, 1H), 1.54 (d, J = 6.9 Hz, 3H), 1.39 (d, J = 7.0 Hz, 3H). | 609.06 | 96 | (S)-7-((3S,5R)-4-acryloyl-3,5-dimethylpiperazin-1-yl)-9-chloro-10-(3-(difluoromethoxy)-4-fluorophenyl)-3-(methoxymethyl)-2,3-dihydro-5H-[1,4]thiazino[2,3,4-ij]quinazolin-5-one |

TABLE 11-continued

| Ex. # | Structure | $^1$H NMR | MS (M + H)$^+$ | % CAF 10 uM @ 60 min | Name |
|---|---|---|---|---|---|
| | Summary of % CAF at 10 μM after 1 hour for Examples 1300-1455 | | | | |
| 1343a | 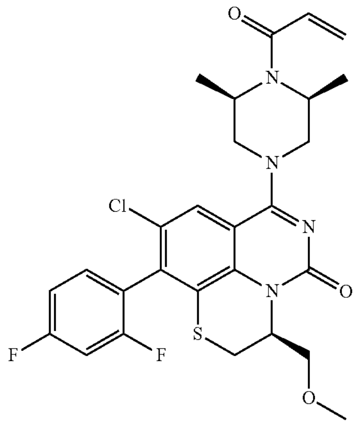 [SMILES: C=CC(=O)N1[C@H](C)CN(c2nc(=O)n3c4c(c(-c5ccc(F)cc5F)c(Cl)cc24)SC[C@@H]3COC)C[C@@H]1C] | $^1$H NMR (400 MHz, MeOH-d$_4$) δ 7.90 (s, 1H), 7.42-7.26 (m, 1H), 7.22-7.10 (m, 2H), 6.83 (dd, J = 16.7, 10.6 Hz, 1H), 6.28 (dd, J = 16.7, 2.0 Hz, 1H), 5.41-5.31 (m, 1H), 4.80-4.52 (m, 2H), 4.44-4.31 (m, 1H), 4.25 (d, J = 13.5 Hz, 1H), 3.79-3.64 (m, 1H), 3.63-3.50 (m, 2H), 3.49-3.41 (m, 2H), 3.39 (s, 3H), 3.38-3.33 (m, 1H), 3.15 (td, J = 13.2, 3.0 Hz, 1H), 1.54 (dd, J = 7.0, 2.6 Hz, 3H), 1.40 (dd, J = 7.0, 3.2 Hz, 3H). | 561.2 | 96.8 | (3S)-7-((3S,5R)-4-acryloyl-3,5-dimethylpiperazin-1-yl)-9-chloro-10-(2,4-difluorophenyl)-3-(methoxymethyl)-2,3-dihydro-5H-[1,4]thiazino[2,3,4-ij]quinazolin-5-one |
| 1344 | 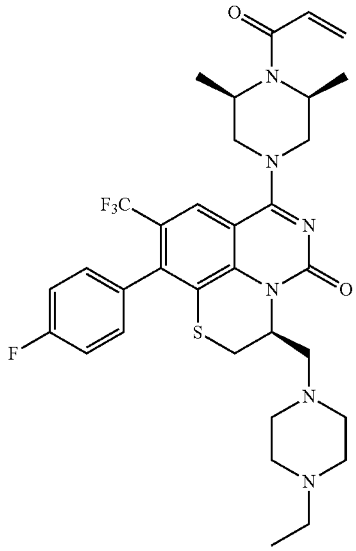 [SMILES: C=CC(=O)N1[C@H](C)CN(c2nc(=O)n3c4c(c(-c5ccc(F)cc5)c(C(F)(F)F)cc24)SC[C@@H]3CN2CCN(CC)CC2)C[C@@H]1C] | $^1$H NMR (400 MHz, CDCl$_3$) δ 8.05 (s, 1H), 7.21-7.15 (m, 4H), 6.66-6.59 (m, 1H), 6.40 (dd, J = 16.8 Hz, J = 2 Hz, 1H), 5.76 (dd, J = 8.4 Hz, J = 2 Hz, 1H), 5.37-5.34 (m, 1H), 4.67-4.63 (m, 2H), 4.20-4.15 (m, 2H), 3.42-3.29 (m, 3H), 2.96-2.92 (m, 1H), 2.83-2.77 (m, 3H), 2.54-2.37 (m, 9H), 1.60 (d, J = 6.8 Hz, 3H), 1.50 (d, J = 6.8 Hz, 3H), 1.07 (t, J = 7.2 Hz, 3H). | 659.4 | 96 | (S)-7-((3S,5R)-4-acryloyl-3,5-dimethylpiperazin-1-yl)-3-((4-ethylpiperazin-1-yl)methyl)-10-(4-fluorophenyl)-9-(trifluoromethyl)-2,3-dihydro-5H-[1,4]thiazino[2,3,4-ij]quinazolin-5-one |
| 1345 | 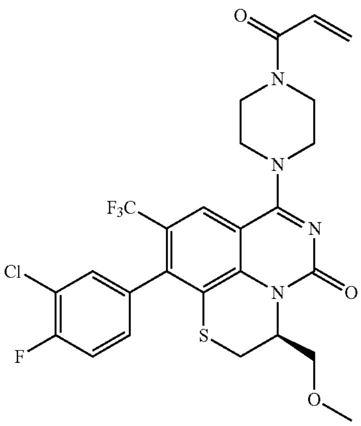 [SMILES: C=CC(=O)N1CCN(c2nc(=O)n3c4c(c(-c5ccc(F)c(Cl)c5)c(C(F)(F)F)cc24)SC[C@@H]3COC)CC1] | $^1$H NMR (400 MHz, CDCl$_3$) δ: 7.80 (s, 1H), 7.32-7.30 (m, 1H), 7.28-7.23 (m, 1H), 7.14-7.09 (m, 1H), 6.62-6.56 (m, 1H), 6.39-6.34 (m, 1H), 5.78 (dd, J = 10.4 Hz, 2.0 Hz, 1H), 5.44-5.39 (m, 1H), 3.80-3.70 (m, 8H), 3.68-3.63 (m, 2H), 3.41-3.33 (m, 4H), 2.99-2.94 (m, 1H). | 583.3 | 90 | (S)-7-(4-acryloylpiperazin-1-yl)-10-(3-chloro-4-fluorophenyl)-3-(methoxymethyl)-9-(trifluoromethyl)-2,3-dihydro-5H-[1,4]thiazino[2,3,4-ij]quinazolin-5-one |

TABLE 11-continued

| Ex. # | Structure | $^1H$ NMR | MS $(M + H)^+$ | % CAF 10 uM @ 60 min | Name |
|---|---|---|---|---|---|
| | Summary of % CAF at 10 μM after 1 hour for Examples 1300-1455 | | | | |
| 1346 | 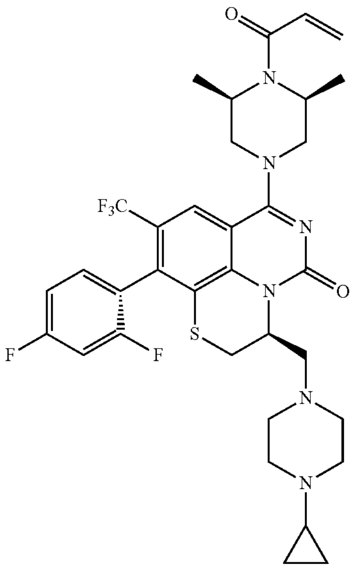 | $^1H$ NMR (400 MHz, $CDCl_3$) δ: 8.07 (s, 1H), 7.18 (q, J = 8.0 Hz, 1H), 7.05-6.94 (m, 2H), 6.62 (dd, J = 10.4 Hz, J = 16.4 Hz, 1H), 6.40 (dd, J = 2.0 Hz, J = 16.8 Hz, 1H), 5.77 (dd, J = 1.6 Hz, J = 10.4 Hz, 1H), 5.37-5.34 (m, 1H), 4.81-4.53 (m, 2H), 4.18 (d, J = 13.2 Hz, 2H), 3.46-3.40 (m, 1H), 3.37-3.30 (m, 2H), 3.02 (d, J = 12.8 Hz, 1H), 2.82-2.53 (m, 9H), 1.59 (d, J = 6.8 Hz, 5H), 1.49 (d, J = 6.8 Hz, 3H), 0.64-0.26 (m, 4H). | 689.2 | 96.9 | (3S,10R)-7-((3S,5R)-4-acryloyl-3,5-dimethylpiperazin-1-yl)-3-((4-cyclopropylpiperazin-1-yl)methyl)-10-(2,4-difluorophenyl)-9-(trifluoromethyl)-2,3-dihydro-5H-[1,4]thiazino[2,3,4-ij]quinazolin-5-one |
| 1347 | 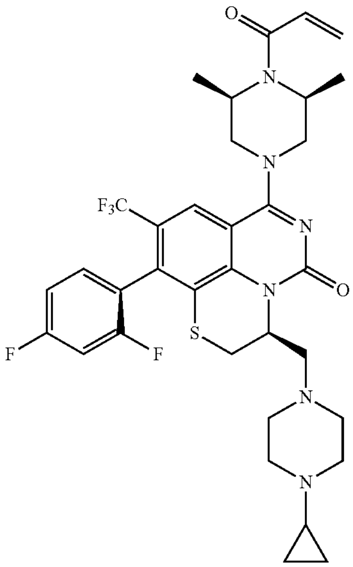 | $^1H$ NMR (400 MHz, $CDCl_3$) δ: 8.07 (s, 1H), 7.17 (q, J = 8.0 Hz, 1H), 7.06-6.94 (m, 2H), 6.62 (dd, J = 10.4 Hz, J = 16.8 Hz, 1H), 6.40 (dd, J = 1.6 Hz, J = 16.4 Hz, 1H), 5.77 (dd, J = 1.6 Hz, J = 10.4 Hz, 1H), 5.44-5.37 (m, 1H), 4.73-4.56 (m, 2H), 4.21-4.16 (m, 2H), 3.39-3.32 (m, 3H), 3.03 (d, J = 13.6 Hz, 2H), 2.83-2.31 (m, 8H), 1.60 (d, J = 6.8 Hz, 5H), 1.49 (d, J = 7.2 Hz, 3H), 1.08-0.27 (m, 4H). | 689.2 | 89.7 | (3S,10S)-7-((3S,5R)-4-acryloyl-3,5-dimethylpiperazin-1-yl)-3-((4-cyclopropylpiperazin-1-yl)methyl)-10-(2,4-difluorophenyl)-9-(trifluoromethyl)-2,3-dihydro-5H-[1,4]thiazino[2,3,4-ij]quinazolin-5-one |

TABLE 11-continued

Summary of % CAF at 10 μM after 1 hour for Examples 1300-1455

| Ex. # | Structure | $^1$H NMR | MS $(M + H)^+$ | % CAF 10 uM @ 60 min | Name |
|---|---|---|---|---|---|
| 1348 | 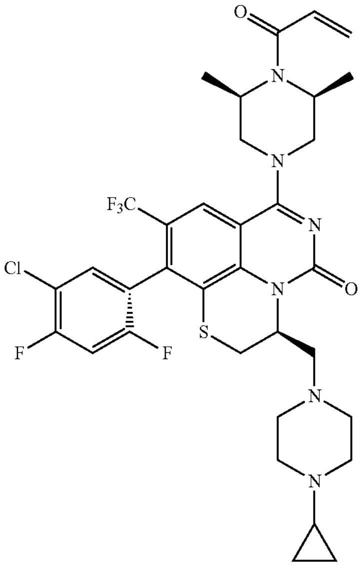 | $^1$H NMR (400 MHz, $CDCl_3$) δ: 8.06 (s, 1H), 7.28-7.24 (m, 1H), 7.07 (t, J = 8.8 Hz, H), 6.62 (dd, J = 10.8 Hz, J = 16.8 Hz, 1H), 6.40 (dd, J = 1.6 Hz, J = 16.8 Hz, 1H), 5.77 (dd, J = 2.0 Hz, J = 10.4 Hz, 1H), 5.38-5.35 (m, 1H), 4.78-4.55 (m, 2H), 4.19-4.16 (m, 2H), 3.52-3.44 (m, 1H), 3.37-3.31 (m, 2H), 3.04-3.00 (m, 1H), 2.80-2.55 (m, 9H), 1.58 (d, J = 6.8 Hz, 5H), 1.49 (d, J = 6.8 Hz, 3H), 0.64-0.35 (m, 4H). | 723.2 | 94.4 | (3S,10R)-7-((3S,5R)-4-acryloyl-3,5-dimethylpiperazin-1-yl)-10-(5-chloro-2,4-difluorophenyl)-3-((4-cyclopropylpiperazin-1-yl)methyl)-9-(trifluoromethyl)-2,3-dihydro-5H-[1,4]thiazino[2,3,4-ij]quinazolin-5-one |
| 1349 | 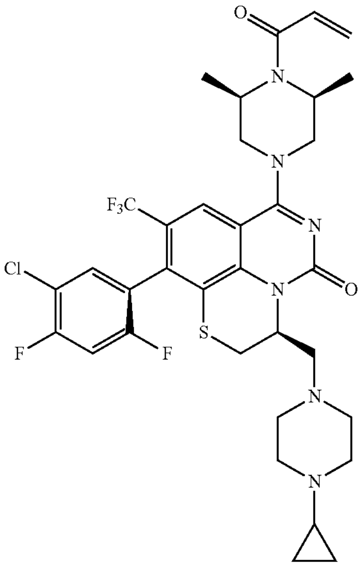 | $^1$H NMR (400 MHz, $CDCl_3$) δ: 8.06 (s, 1H), 7.29-7.26 (m, 1H), 7.07 (t, J = 8.4 Hz, 1H), 6.62 (dd, J = 10.8 Hz, J = 16.8 Hz, 1H), 6.40 (dd, J = 2.0 Hz, J = 16.8 Hz, 1H), 5.77 (dd, J = 2.0 Hz, J = 10.4 Hz, 1H), 5.41-5.39 (m, 1H), 4.74-4.56 (m, 2H), 4.20-4.15 (m, 2H), 3.47-3.31 (m, 3H), 3.02 (d, J = 12.0 Hz, 1H), 2.77-2.50 (m, 9H), 1.59 (d, J = 7.2 Hz, 5H), 1.48 (d, J = 6.8 Hz, 3H), 0.87-0.36 (m, 4H). | 723.2 | 86.9 | (3S,10S)-7-((3S,5R)-4-acryloyl-3,5-dimethylpiperazin-1-yl)-10-(5-chloro-2,4-difluorophenyl)-3-((4-cyclopropylpiperazin-1-yl)methyl)-9-(trifluoromethyl)-2,3-dihydro-5H-[1,4]thiazino[2,3,4-ij]quinazolin-5-one |

TABLE 11-continued

| Summary of % CAF at 10 μM after 1 hour for Examples 1300-1455 | | | | | |
|---|---|---|---|---|---|
| Ex. # | Structure | $^1$H NMR | MS $(M + H)^+$ | % CAF 10 uM @ 60 min | Name |
| 1350 | 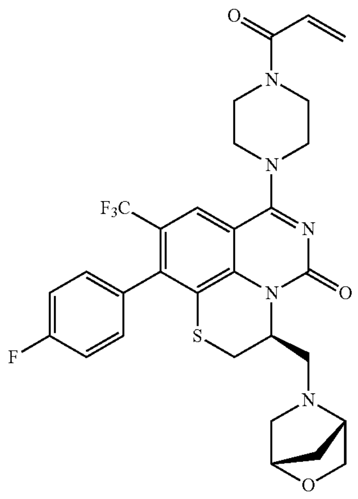 [SMILES: C=CC(=O)N1CCN(c2nc(=O)n3c4c(c(-c5ccc(F)cc5)c(C(F)(F)F)cc24)SC[C@@H]3CN2C[C@@H]3C[C@H]2CO3)CC1] | $^1$H NMR (400 MHz, $CDCl_3$) δ 7.81 (s, 1H), 7.21-7.15 (m, 4H), 6.63-6.56 (m, 1H), 6.39-3.34 (m, 1H), 5.78 (dd, J = 10.4 Hz, 1.6 Hz, 1H), 5.34-5.18 (m, 1H), 4.43-4.40 (m, 1H), 3.95-3.80 (m, 10H), 3.62-3.45 (m, 3H), 2.94-2.86 (m, 4H), 1.75-1.71 (m, 2H). | 616.1 | 81.3 | (S)-3-(((1S,4S)-2-oxa-5-azabicyclo[2.2.1]heptan-5-yl)methyl)-7-(4-acryloylpiperazin-1-yl)-10-(4-fluorophenyl)-9-(trifluoromethyl)-2,3-dihydro-5H-[1,4]thiazino[2,3,4-ij]quinazolin-5-one |
| 1351 | 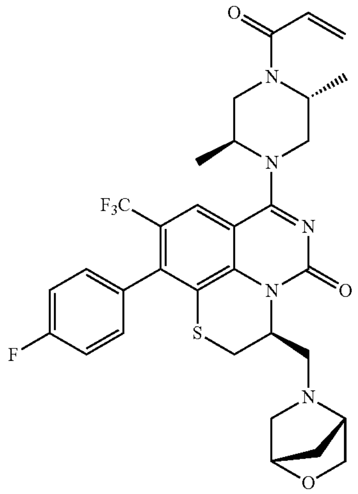 [SMILES: C=CC(=O)N1C[C@H](C)N(c2nc(=O)n3c4c(c(-c5ccc(F)cc5)c(C(F)(F)F)cc24)SC[C@@H]3CN2C[C@@H]3C[C@H]2CO3)C[C@H]1C] | $^1$H NMR (400 MHz, $CDCl_3$) δ 7.84 (d, J = 6.4 Hz, 1H), 7.25-7.17 (m, 4H), 6.67-6.50 (m, 1H), 6.41-6.33 (m, 1H), 5.80-5.75 (m, 1H), 5.25-5.17 (m, 1H), 5.09-4.65 (m, 2H), 4.43-4.35 (m, 2.5H), 4.12-4.05 (m, 0.5H), 3.95-3.87 (m, 1H), 3.76-3.39 (m, 6H) 3.28-2.93 (m, 5H), 1.82-1.70 (m, 2H), 1.49-1.40 (m, 6H). | 644.4 | 64.8 | (S)-3-(((1S,4S)-2-oxa-5-azabicyclo[2.2.1]heptan-5-yl)methyl)-7-((2S,5R)-4-acryloyl-2,5-dimethylpiperazin-1-yl)-10-(4-fluorophenyl)-9-(trifluoromethyl)-2,3-dihydro-5H-[1,4]thiazino[2,3,4-ij]quinazolin-5-one |
| 1352 | 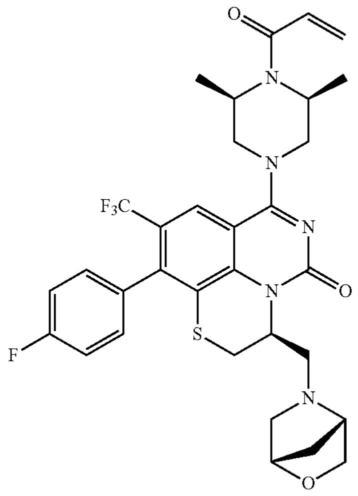 [SMILES: C=CC(=O)N1[C@H](C)CN(c2nc(=O)n3c4c(c(-c5ccc(F)cc5)c(C(F)(F)F)cc24)SC[C@@H]3CN2C[C@@H]3C[C@H]2CO3)C[C@@H]1C] | $^1$H NMR (400 MHz, $CDCl_3$) δ: 8.06 (s, 1H), 7.21-7.15 (m, 4H), 6.66-6.59 (m, 1H), 6.43-6.38 (m, 1H), 5.78-5.75 (m, 1H), 5.27-5.18 (m, 1H), 4.68-4.64 (m, 2H), 4.44-4.41 (m, 1H), 4.20-4.17 (m, 2H), 3.91-3.88 (m, 1H), 3.62-3.31 (m, 5H) 2.95-2.86 (m, 5H), 1.76-1.71 (m, 2H), 1.62-1.60 (m, 3H), 1.49-1.47 (m, 3H). | 644.4 | 96.1 | (S)-3-(((1S,4S)-2-oxa-5-azabicyclo[2.2.1]heptan-5-yl)methyl)-7-((3S,5R)-4-acryloyl-3,5-dimethylpiperazin-1-yl)-10-(4-fluorophenyl)-9-(trifluoromethyl)-2,3-dihydro-5H-[1,4]thiazino[2,3,4-ij]quinazolin-5-one |

TABLE 11-continued

Summary of % CAF at 10 μM after 1 hour for Examples 1300-1455

| Ex. # | Structure | $^1$H NMR | MS (M + H)$^+$ | % CAF 10 uM @ 60 min | Name |
|---|---|---|---|---|---|
| 1353 | 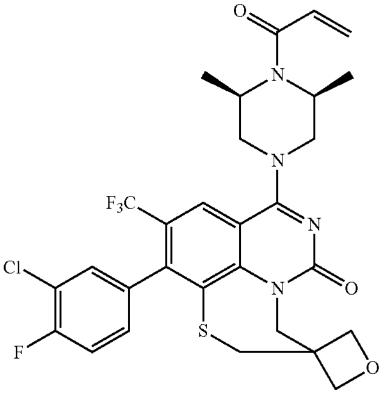 [SMILES: C=CC(=O)N1[C@H](C)CN(c2nc(=O)n3c4c(c(-c5ccc(F)c(Cl)c5)c(C(F)(F)F)cc24)SCC2(COC2)C3)C[C@@H]1C] | $^1$H NMR (400 MHz, $CDCl_3$) δ: 8.11 (s, 1H), 7.34-7.28 (m, 2H), 7.16-7.14 (m, 1H), 6.72-6.63 (m, 1H), 6.49-6.43 (m, 1H), 5.85-5.81 (m, 1H), 4.81-4.65 (m, 6H), 4.41-4.38 (m, 2H), 4.22-4.18 (m, 2H), 3.44-3.41 (m, 4H), 1.60-1.58 (m, 6H). | 623.3 | 96.4 | 8'-((3S,5R)-4-acryloyl-3,5-dimethylpiperazin-1-yl)-11'-(3-chloro-4-fluorophenyl)-10'-(trifluoromethyl)-2'H,4'H,6'H-spiro[oxetane-3,3'-[1,4]thiazepino[2,3,4-ij]quinazolin]-6'-one |
| 1354 | 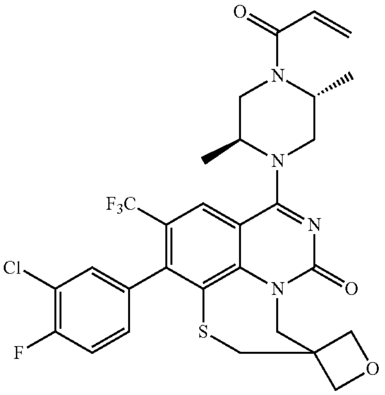 [SMILES: C=CC(=O)N1C[C@H](C)N(c2nc(=O)n3c4c(c(-c5ccc(F)c(Cl)c5)c(C(F)(F)F)cc24)SCC2(COC2)C3)C[C@H]1C] | $^1$H NMR (400 MHz, $CDCl_3$) δ: 7.79 (s, 1H), 7.31-7.24 (m, 2H), 7.11-7.08 (m, 1H), 6.66-6.51 (m, 1H), 6.42-6.34 (m, 1H), 5.80-5.76 (m, 1H), 5.09-4.67 (m, 5.5H), 4.41-4.29 (m, 3H), 3.91-3.67 (m, 3H), 3.44-3.35 (m, 2.5H), 1.39-1.32 (m, 6H). | 623.3 | 96 | 8'-((2S,5R)-4-acryloyl-2,5-dimethylpiperazin-1-yl)-11'-(3-chloro-4-fluorophenyl)-10'-(trifluoromethyl)-2'H,4'H,6'H-spiro[oxetane-3,3'-[1,4]thiazepino[2,3,4-ij]quinazolin]-6'-one |
| 1355 | 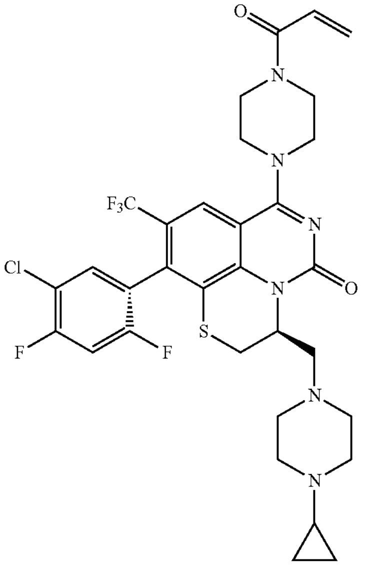 | $^1$H NMR (400 MHz, $CDCl_3$) δ: 7.80 (s, 1H), 7.29-7.25 (m, 1H), 7.07 (t, J = 8.8 Hz, 1H), 6.59 (dd, J = 10.4 Hz, 16.8 Hz, 1H), 6.36 (dd, J = 1.6 Hz, 16.8 Hz, 1H), 5.78 (dd, J = 1.6 Hz, 10.4 Hz, 1H), 5.36-5.33 (m, 1H), 3.94-3.91 (m, 3H), 3.82-3.79 (m, 5H), 3.48 (d, J = 11.2 Hz, 1H), 3.02 (d, J = 13.2 Hz, 1H), 2.80-2.54 (m, 10H), 1.39-1.25 (m, 1H), 0.55-0.36 (m, 4H). | 695.4 | 99.2 | (3S,10R)-7-(4-acryloylpiperazin-1-yl)-10-(5-chloro-2,4-difluorophenyl)-3-((4-cyclopropylpiperazin-1-yl)methyl)-9-(trifluoromethyl)-2,3-dihydro-5H-[1,4]thiazino[2,3,4-ij]quinazolin-5-one |

TABLE 11-continued

| Summary of % CAF at 10 μM after 1 hour for Examples 1300-1455 | | | | | |
|---|---|---|---|---|---|
| Ex. # | Structure | $^1$H NMR | MS (M + H)$^+$ | % CAF 10 uM @ 60 min | Name |
| 1356 | 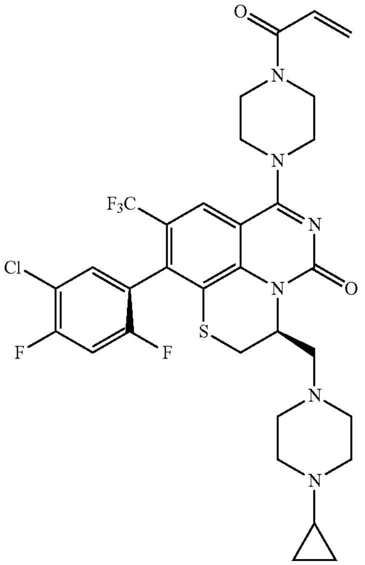 | $^1$H NMR (400 MHz, $CDCl_3$) δ: 7.81 (s, 1H), 7.28-7.26 (m, 1H), 7.07 (t, J = 8.8 Hz, 1H), 6.59 (dd, J = 10.4 Hz, 16.8 Hz, 1H), 6.37 (dd, J = 1.6 Hz, 16.8 Hz, 1H), 5.78 (dd, J = 1.6 Hz, 10.4 Hz, 1H), 5.41-5.37 (m, 1H), 3.98-3.91 (m, 3H), 3.82-3.79 (m, 5H), 3.49-3.40 (m, 1H), 3.02 (d, J = 13.6 Hz, 1H), 2.86-2.41 (m, 10H), 1.31-1.17 (m, 1H), 0.71-0.25 (m, 4H). | 695.4 | 92.8 | (3S,10S)-7-(4-acryloylpiperazin-1-yl)-10-(5-chloro-2,4-difluorophenyl)-3-((4-cyclopropylpiperazin-1-yl)methyl)-9-(trifluoromethyl)-2,3-dihydro-5H-[1,4]thiazino[2,3,4-ij]quinazolin-5-one |
| 1357a | 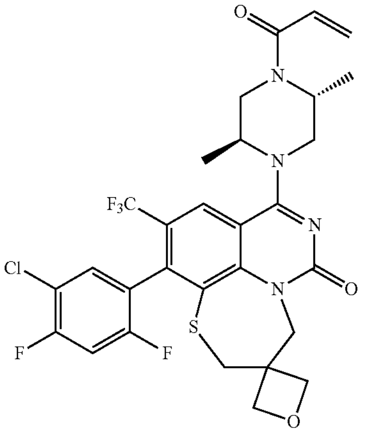 [SMILES: C=CC(=O)N1C[C@H](C)N(c2nc(=O)n3c4c(c(-c5cc(Cl)c(F)cc5F)c(C(F)(F)F)cc24)SCC2(COC2)C3)C[C@H]1C] | $^1$H NMR (400 MHz, MeOH-$d_4$) δ 7.97 (s, 1H), 7.50 (dd, J = 15.3, 7.8 Hz, 1H), 7.34 (td, J = 9.1, 3.3 Hz, 1H), 6.91-6.72 (m, 1H), 6.34-6.22 (m, 1H), 5.81 (ddd, J = 9.8, 7.3, 1.9 Hz, 1H), 4.88-4.59 (m, 3H), 4.45 (d, J = 6.3 Hz, 2H), 3.99-3.71 (m, 1H), 3.71-3.46 (m, 2H), 1.43 (dd, J = 16.2, 6.6 Hz, 3H), 1.38-1.30 (m, 3H). | 641.2 | 74.3 | 8'-((2S,5R)-4-acryloyl-2,5-dimethylpiperazin-1-yl)-11'-(5-chloro-2,4-difluorophenyl)-10'-(trifluoromethyl)-2'H,4'H,6'H-spiro[oxetane-3,3'-[1,4]thiazepino[2,3-4-ij]quinazolin-6'-one |
| 1357 | 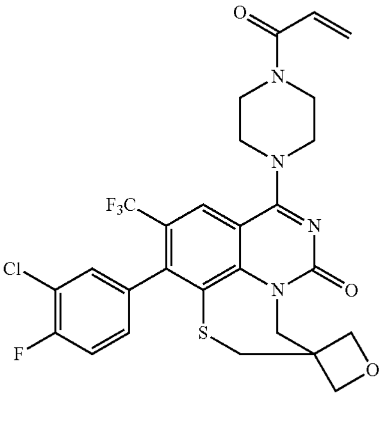 [SMILES: C=CC(=O)N1CCN(c2nc(=O)n3c4c(c(-c5ccc(F)c(Cl)c5)c(C(F)(F)F)cc24)SCC2(COC2)C3)CC1] | $^1$H NMR (400 MHz, $CDCl_3$) δ: 7.81 (s, 1H), 7.30-7.23 (m, 2H), 7.11-7.09 (m, 1H), 6.62-6.55 (m, 1H), 6.39-6.35 (m, 1H), 5.82-5.78 (m, 1H), 5.14-4.64 (m, 3.5H), 4.36-4.33 (m, 2H), 4.00-3.73 (m, 8.5H), 3.42-3.39 (m, 2H). | 595.1 | 92.4 | 8'-(4-acryloylpiperazin-1-yl)-11'-(3-chloro-4-fluorophenyl)-10'-(trifluoromethyl)-2'H,4'H,6'H-spiro[oxetane-3,3'-[1,4]thiazepino[2,3-4-ij]quinazolin]-6'-one |

TABLE 11-continued

| Ex. # | Structure | $^1$H NMR | MS (M + H)$^+$ | % CAF 10 uM @ 60 min | Name |
|---|---|---|---|---|---|
| Summary of % CAF at 10 μM after 1 hour for Examples 1300-1455 | | | | | |
| 1358 | 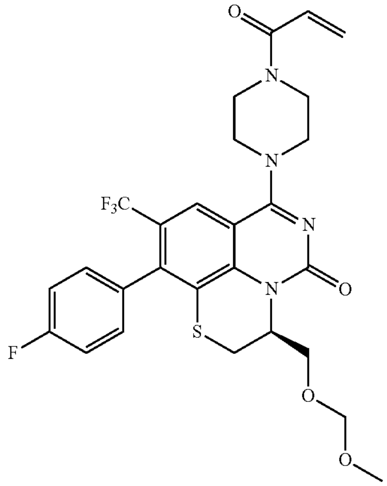 [SMILES: C=CC(=O)N1CCN(c2nc(=O)n3c4c(c(-c5ccc(F)cc5)c(C(F)(F)F)cc24)SC[C@@H]3COCOC)CC1] | $^1$H NMR (400 MHz, $CDCl_3$) δ 7.80 (s, 1H), 7.24-7.15 (m, 4H), 6.63-6.56 (m, 1H), 6.39 (d, J = 16.4 Hz, 1H), 5.80 (d, J = 10.4 Hz, 1H), 5.46-5.45 (m, 1H), 4.67-4.62 (m, 2H), 4.02-3.95 (m, 3H), 3.81-3.79 (m, 7H), 3.35-3.33 (m, 4H), 3.01-2.98 (m, 1H). | 579.2 | 96.3 | (S)-7-(4-acryloylpiperazin-1-yl)-10-(4-fluorophenyl)-3-((methoxymethoxy)methyl)-9-(trifluoromethyl)-2,3-dihydro-5H-[1,4]thiazino[2,3,4-ij]quinazolin-5-one |
| 1359 | 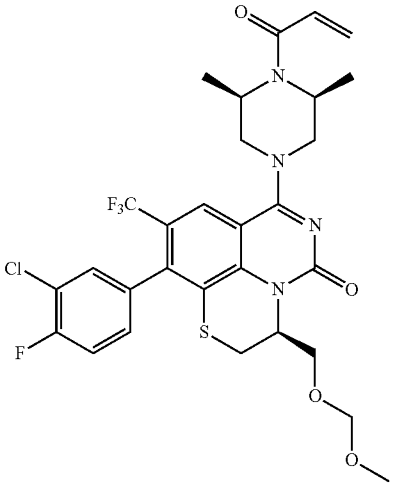 [SMILES: C=CC(=O)N1[C@H](C)CN(c2nc(=O)n3c4c(c(-c5ccc(F)c(Cl)c5)c(C(F)(F)F)cc24)SC[C@@H]3COCOC)C[C@@H]1C] | $^1$H NMR (400 MHz, $CDCl_3$) δ 8.05 (s, 1H), 7.32-7.23 (m, 2H), 7.13-7.10 (m, 1H), 6.65-6.59 (m, 1H), 6.43 (dd, J = 12.8 Hz, 2 Hz, 1H), 5.79 (dd, J = 8.4 Hz, 1.6 Hz, 1H), 5.48-5.46 (m, 1H), 4.68-4.62 (m, 3H), 4.20-4.17 (m, 2H), 3.83-3.77 (m, 2H), 3.39-3.30 (m, 6H), 3.03-2.98 (m, 1H), 1.62-1.60 (m, 4H), 1.48-1.46 (m, 3H). | 641.1 | 74.6 | (S)-7-((3S,5R)-4-acryloyl-3,5-dimethylpiperazin-1-yl)-10-(3-chloro-4-fluorophenyl)-3-((methoxymethoxy)methyl)-9-(trifluoromethyl)-2,3-dihydro-5H-[1,4]thiazino[2,3,4-ij]quinazolin-5-one |

TABLE 11-continued

Summary of % CAF at 10 μM after 1 hour for Examples 1300-1455

| Ex. # | Structure | $^1$H NMR | MS (M + H)$^+$ | % CAF 10 uM @ 60 min | Name |
|---|---|---|---|---|---|
| 1360 | 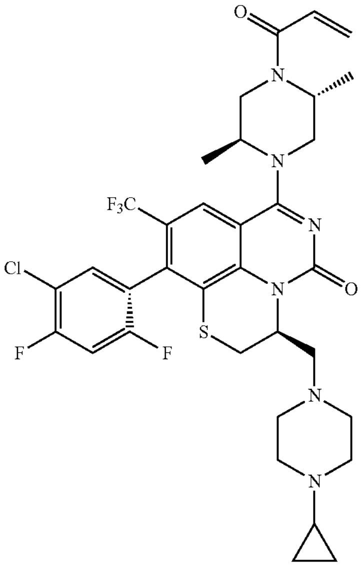 | $^1$H NMR (400 MHz, $CDCl_3$) δ: 7.52 (s, 1H), 7.30 (t, J = 7.2 Hz, 1H), 7.10 (t, J = 8.8 Hz, 1H), 6.66-6.50 (m, 1H), 6.37 (t, J = 14.4 Hz, 1H), 5.79-5.75 (m, 1H), 5.45-5.41 (m, 1H), 4.98-4.86 (m, 1H), 4.72-4.71 (m, 0.5H), 4.44-4.36 (m, 0.5H), 4.33-4.29 (m, 0.5H), 4.23-4.19 (m, 0.5H), 3.99-3.96 (m, 0.5H), 3.83-3.77 (m, 1H), 3.72-3.65 (m, 1H), 3.49-3.35 (m, 1.5H), 3.06-3.02 (m, 1H), 2.84-2.46 (m, 10H), 1.39-1.22 (m, 7H), 0.69-0.27 (m, 4H). | 689.2 | 92.8 | (3S,10R)-7-((2S,5R)-4-acryloyl-2,5-dimethylpiperazin-1-yl)-10-(5-chloro-2,4-difluorophenyl)-3-((4-cyclopropylpiperazin-1-yl)methyl)-9-(trifluoromethyl)-2,3-dihydro-5H-[1,4]thiazino[2,3,4-ij]quinazolin-5-one |
| 1361 | 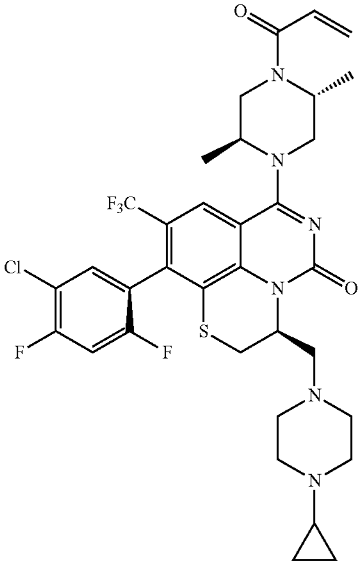 | $^1$H NMR (400 MHz, $CDCl_3$) δ: 7.53 (s, 1H), 7.30 (t, J = 7.6 Hz, 1H), 7.09 (t, J = 8.4 Hz, 1H), 6.63-6.51 (m, 1H), 6.37 (t, J = 22.0 Hz, 1H), 5.79-5.75 (m, 1H), 5.48-5.40 (m, 1H), 5.00 (m, 0.5H), 4.84 (m, 0.5H), 4.71-4.70 (m, 0.5H), 4.38 (m, 0.5H), 4.31 (m, 0.5H), 4.22 (m, 0.5H), 3.99-3.96 (m, 0.5H), 3.82-3.65 (m, 2H), 3.49-3.48 (m, 0.5H), 3.36-3.33 (m, 1H), 3.07-3.04 (m, 1H), 2.79-2.45 (m, 10H), 1.45-1.22 (m, 7H), 0.97-0.13 (m, 4H). | 689.2 | 29.8 | (3S,10S)-7-((2S,5R)-4-acryloyl-2,5-dimethylpiperazin-1-yl)-10-(5-chloro-2,4-difluorophenyl)-3-((4-cyclopropylpiperazin-1-yl)methyl)-9-(trifluoromethyl)-2,3-dihydro-5H-[1,4]thiazino[2,3,4-ij]quinazolin-5-one |

TABLE 11-continued

| Summary of % CAF at 10 μM after 1 hour for Examples 1300-1455 | | | | | |
|---|---|---|---|---|---|
| Ex. # | Structure | $^1$H NMR | MS (M + H)$^+$ | % CAF 10 uM @ 60 min | Name |
| 1361a | 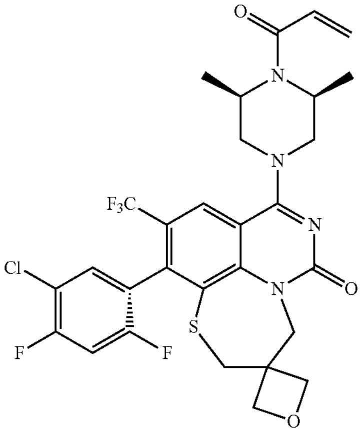 | $^1$H NMR (400 MHz, MeOH-d$_4$) δ 8.18 (s, 1H), 7.52 (t, J = 7.5 Hz, 1H), 7.37 (t, J = 9.1 Hz, 1H), 6.85 (dd, J = 16.7, 10.6 Hz, 1H), 6.31 (dd, J = 16.7, 2.0 Hz, 1H), 5.82 (dd, J = 10.6, 2.0 Hz, 1H), 4.88-4.58 (m, 4H), 4.46 (dd, J = 6.4, 2.4 Hz, 2H), 4.27 (d, J = 13.5 Hz, 2H), 3.58 (d, J = 6.6 Hz, 2H), 3.46 (dt, J = 13.7, 4.5 Hz, 2H), 1.59-1.46 (m, 6H). | 641.1 | 93.3 | (R)-8'-((3S,5R)-4-acryloyl-3,5-dimethylpiperazin-1-yl)-11'-(5-chloro-2,4-difluorophenyl)-10'-(trifluoromethyl)-2'H,4'H,6'H-spiro[oxetane-3,3'-[1,4]thiazepino[2,3,4-ij]quinazolin]-6'-one |
| 1361b | 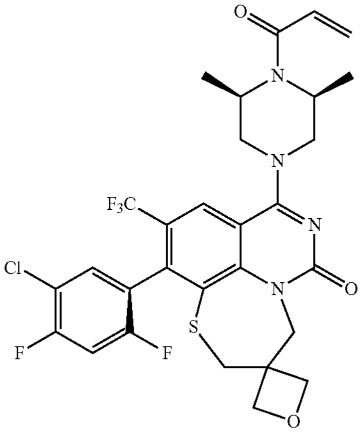 | $^1$H NMR (400 MHz, MeOH-d$_4$) δ 8.16 (s, 1H), 7.50 (t, J = 7.7 Hz, 1H), 7.34 (t, J = 9.1 Hz, 1H), 6.83 (dd, J = 16.7, 10.6 Hz, 1H), 6.29 (dd, J = 16.6, 2.0 Hz, 1H), 5.80 (dd, J = 10.6, 2.0 Hz, 1H), 4.88-4.54 (m, 4H), 4.44 (dd, J = 6.4, 2.4 Hz, 2H), 4.25 (d, J = 13.5 Hz, 2H), 3.56 (d, J = 6.6 Hz, 2H), 3.44 (dt, J = 13.9, 4.5 Hz, 2H), 1.55-1.41 (m, 6H). | 641.1 | 71.4 | (S)-8'-((3S,5R)-4-acryloyl-3,5-dimethylpiperazin-1-yl)-11'-(5-chloro-2,4-difluorophenyl)-10'-(trifluoromethyl)-2'H,4'H,6'H-spiro[oxetane-3,3'-[1,4]thiazepino[2,3,4-ij]quinazolin-6'-one |
| 1362 | 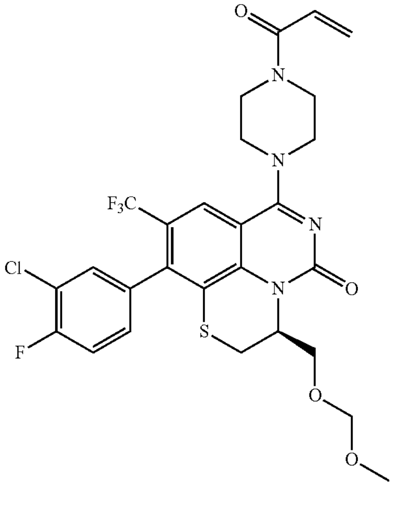 [SMILES: C=CC(=O)N1CCN(c2nc(=O)n3c4c(c(-c5ccc(F)c(Cl)c5)c(C(F)(F)F)cc24)SC[C@@H]3COCOC)CC1] | $^1$H NMR (400 MHz, CDCl$_3$) δ 7.80 (s, 1H), 7.32-7.23 (m, 2H), 7.14-7.11 (m, 1H), 6.59 (dd, J = 10.4 Hz, 16.8 Hz, 1H), 6.39 (dd, J = 1.6 Hz, 16.8 Hz, 1H), 5.80 (dd, J = 1.2 Hz, 10.0 Hz, 1H), 5.47-5.43 (m, 1H), 4.68-4.62 (m, 2H), 4.05-3.94 (m, 3H), 3.81-3.78 (m, 7H), 3.37-3.35 (m, 4H), 3.02-2.99 (m, 1H). | 613.02 | 96.2 | (S)-7-(4-acryloylpiperazin-1-yl)-10-(3-chloro-4-fluorophenyl)-3-((methoxymethoxy)methyl)-9-(trifluoromethyl)-2,3-dihydro-5H-[1,4]thiazino[2,3,4-ij]quinazolin-5-one |

TABLE 11-continued

Summary of % CAF at 10 μM after 1 hour for Examples 1300-1455

| Ex. # | Structure | $^1$H NMR | MS (M + H)$^+$ | % CAF 10 uM @ 60 min | Name |
|---|---|---|---|---|---|
| 1363 | 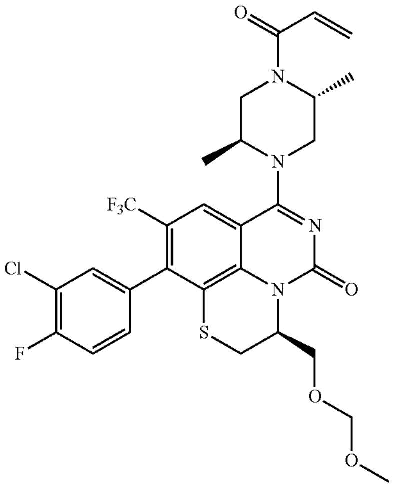 [SMILES: C=CC(=O)N1C[C@H](C)N(c2nc(=O)n3c4c(c(-c5ccc(F)c(Cl)c5)c(C(F)(F)F)cc24)SC[C@@H]3COCOC)C[C@H]1C] | $^1$H NMR (400 MHz, $CDCl_3$) δ 7.84-7.82 (m, 1H), 7.34-7.23 (m, 2H), 7.15-7.09 (m, 1H), 6.66-6.50 (m, 1H), 6.41-6.33 (m, 1H), 5.80-5.75 (m, 1H), 5.45-5.44 (m, 1H), 5.06-4.80 (m, 1H), 4.68-4.62 (m, 2H), 4.43-4.05 (m, 2H), 3.81-3.62 (m, 4H), 3.37-3.22 (m, 5H), 3.03-3.00 (m, 1H), 1.49-1.41 (m, 6H). | 641.08 | 92.1 | (S)-7-((2S,5R)-4-acryloyl-2,5-dimethylpiperazin-1-yl)-10-(3-chloro-4-fluorophenyl)-3-((methoxymethoxy)methyl)-9-(trifluoromethyl)-2,3-dihydro-5H-[1,4]thiazino[2,3,4-ij]quinazolin-5-one |
| 1364 | 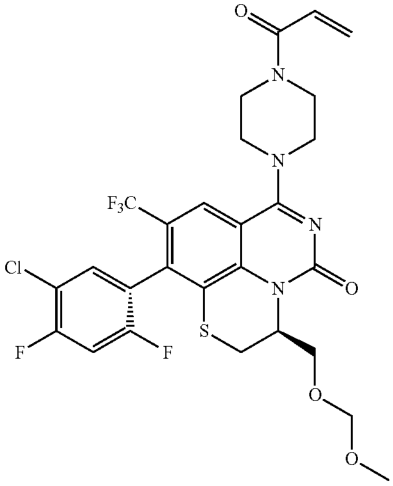 | $^1$H NMR (400 MHz, $CDCl_3$) δ 7.81 (s, 1H), 7.30-7.26 (m, 1H), 7.07 (t, J = 8.8 Hz, 1H), 6.59 (dd, J = 10.4 Hz, 16.8 Hz, 1H), 6.37 (dd, J = 1.6 Hz, 16.8 Hz, 1H), 5.79 (dd, J = 1.2 Hz, 10.4 Hz, 1H), 5.48-5.44 (m, 1H), 4.68-4.63 (m, 2H), 3.97-3.82 (m, 3H), 3.80-3.78 (m, 7H), 3.42-3.36 (m, 4H), 3.0-3.05 (m, 1H). | 631.1 | 98 | (3S,10R)-7-(4-acryloylpiperazin-1-yl)-10-(5-chloro-2,4-dichlorophenyl)-3-((methoxymethoxy)methyl)-9-(trifluoromethyl)-2,3-dihydro-5H-[1,4]thiazino[2,3,4-ij]quinazolin-5-one |
| 1365 | 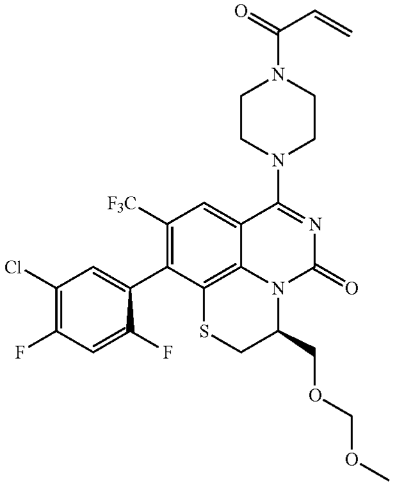 | $^1$H NMR (400 MHz, $CDCl_3$) δ 7.81 (s, 1H), 7.28-7.25 (m, 1H), 7.06 (t, J = 8.8 Hz, 1H), 6.59 (dd, J = 10.4 Hz, 16.8 Hz, 1H), 6.37 (dd, J = 1.6 Hz, 16.8 Hz, 1H), 5.79 (dd, J = 1.6 Hz, 10.4 Hz, 1H), 5.52-5.47 (m, 1H), 4.67-4.62 (m, 2H), 3.97-3.84 (m, 3H), 3.81-3.76 (m, 7H), 3.42-3.35 (m, 4H), 3.07-3.04 (m, 1H). | 631.1 | 83.7 | (3S,10S)-7-(4-acryloylpiperazin-1-yl)-10-(5-chloro-2,4-dichlorophenyl)-3-((methoxymethoxy)methyl)-9-(trifluoromethyl)-2,3-dihydro-5H-[1,4]thiazino[2,3,4-ij]quinazolin-5-one |

TABLE 11-continued

Summary of % CAF at 10 μM after 1 hour for Examples 1300-1455

| Ex. # | Structure | $^1$H NMR | MS (M + H)$^+$ | % CAF 10 uM @ 60 min | Name |
|---|---|---|---|---|---|
| 1366 | 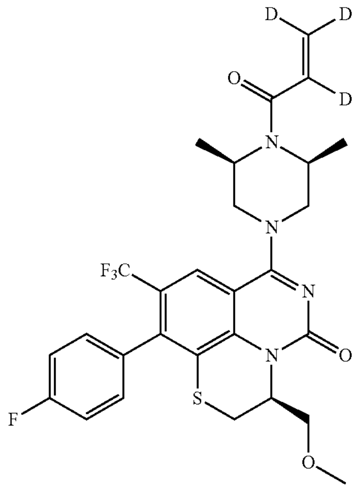 [SMILES: [2H]C([2H])=C([2H])C(=O)N1[C@H](C)CN(c2nc(=O)n3c4c(c(-c5ccc(F)cc5)c(C(F)(F)F)cc24)SC[C@@H]3COC)C[C@@H]1C] | $^1$H NMR (400 MHz, MeOH-$d_4$) δ 8.13 (s, 1H), 7.34-7.19 (m, 4H), 5.38-5.30 (m, 1H), 4.81-4.57 (br s, 2H), 4.39-4.22 (m, 2H), 3.73 (t, J = 9.2 Hz, 1H), 3.60 (dd, J = 9.2, 4.8 Hz, 1H), 3.49 (dd, J = 9.2, 4.8 Hz, 1H), 1H), 3.39 (s, 3H), 3.45-3.33 (m, 2H), 3.09 (dd, J = 13.6, 2.9 Hz, 1H), 1.57 (d, J = 7.0 Hz, 3H), 1.42 (d, J = 7.0 Hz, 3H). | 580.3 | 96.8 | (S)-7-((3S,5R)-4-(Acryloyl)-$d_3$)-3,5 dimethylpiperazin-1-yl)-10-(4-fluorophenyl)-3-(methoxymethyl)-9-(trifluoromethyl)-2,3-dihydro-5H-[1,4]thiazino[2,3,4-ij]quinazolin-5-one |
| 1366a | 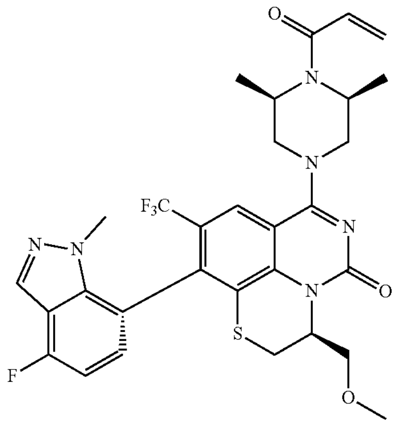 | $^1$H NMR (400 MHz, MeOH-$d_4$) δ 8.22 (s, 1H), 8.16 (s, 1H), 7.18 (dd, J = 8.0, 4.8 Hz, 1H), 6.98 (dd, J = 9.7, 7.9 Hz, 1H), 6.85 (dd, J = 16.7, 10.6 Hz, 1H), 6.30 (dd, J = 16.6, 2.0 Hz, 1H), 5.81 (dd, J = 10.6, 2.0 Hz, 1H), 5.41-5.31 (m, 1H), 4.84-4.55 (m, 2H), 4.39 (d, J = 13.6 Hz, 1H), 4.30 (d, J = 13.6 Hz, 1H), 3.74-3.60 (m, 3H), 3.56 (s, 3H), 3.55-3.37 (m, 3H), 3.36 (s, 3H), 3.35-3.33 (m, 1H), 3.15 (dd, J = 13.7, 3.0 Hz, 1H), 1.60 (d, J = 6.9 Hz, 3H), 1.42 (d, J = 7.0 Hz, 3H). | 631.3 | 46.8 | (3S,10S)-7-((3S,5R)-4-acryloyl-3,5-dimethylpiperazin-1-yl)-10-(4-fluoro-1-methyl-1H-indazol-7-yl)-3-(methoxymethyl)-9-(trifluoromethyl)-2,3-dihydro-5H-[1,4]thiazino[2,3,4-ij]quinazolin-5-one |
| 1367 | 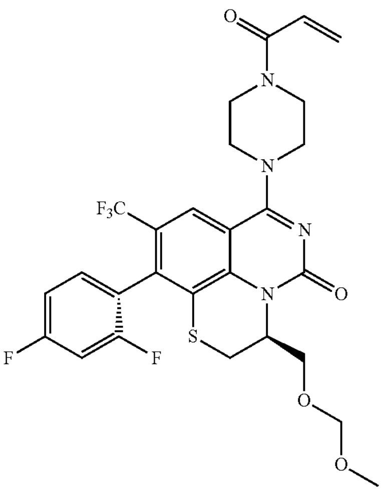 | $^1$H NMR (400 MHz, $CDCl_3$) δ 7.81 (s, 1H), 7.21-7.15 (m, 1H), 7.04-6.94 (m, 2H), 6.62-6.55 (m, 1H), 6.39 (dd, J = 17.2 Hz, 2.0 Hz, 1H), 5.79 (dd, J = 10.4 Hz, 2.0 Hz, 1H), 5.47-5.42 (m, 1H), 4.67-4.62 (m, 2H), 4.05-3.97 (m, 3H), 3.80-3.78 (m, 7H), 3.40-3.35 (m, 1H), 3.34 (s, 3H), 3.07 (dd, J = 13.6 Hz, 2.8 Hz, 1H). | 597.2 | 92.4 | (3S,10R)-7-(4-acryloylpiperazin-1-yl)-10-(2,4-difluorophenyl)-3-((methoxymethoxy) methyl)-9-(trifluoromethyl)-2,3-dihydro-5H-[1,4]thiazino[2,3,4-ij]quinazolin-5-one |

TABLE 11-continued

Summary of % CAF at 10 μM after 1 hour for Examples 1300-1455

| Ex. # | Structure | $^1$H NMR | MS (M + H)$^+$ | % CAF 10 uM @ 60 min | Name |
|---|---|---|---|---|---|
| 1368 | 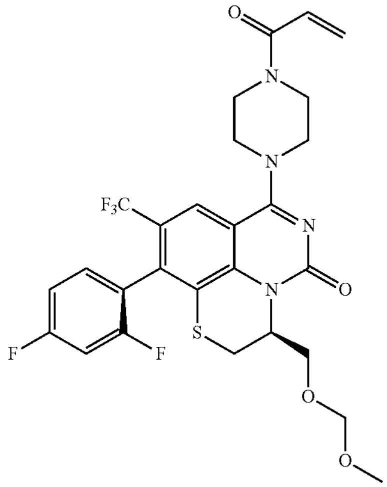 | $^1$H NMR (400 MHz, $CDCl_3$) δ 7.81 (s, 1H), 7.20-7.15 (m, 1H), 7.05-6.93 (m, 2H), 6.62-6.56 (m, 1H), 6.39 (dd, J = 16.8 Hz, 1.6 Hz, 1H), 5.79 (dd, J = 10.8 Hz, 2.0 Hz, 1H), 5.51-5.46 (m, 1H), 4.67-4.62 (m, 2H), 4.04-3.91 (m, 3H), 3.82-3.74 (m, 7H), 3.39-3.36 (m, 4H), 3.05 (dd, J = 13.6 Hz, 2.8 Hz, 1H). | 597.2 | 92.4 | (3S,10S)-7-(4-acryloylpiperazin-1-yl)-10-(2,4-difluorophenyl)-3-((methoxymethoxy)methyl)-9-(trifluoromethyl)-2,3-dihydro-5H-[1,4]thiazino[2,3,4-ij]quinazolin-5-one |
| 1369 | 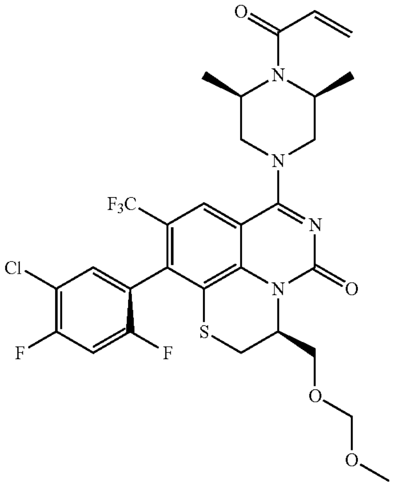 | $^1$H NMR (400 MHz, $CDCl_3$) δ 8.07 (s, 1H), 7.29-7.26 (m, 1H), 7.08-7.04 (m, 1H), 6.65-6.59 (m, 1H), 6.43 (dd, J = 16.8 Hz, 2 Hz, 1H), 5.79 (dd, J = 10 Hz, 1.6 Hz, 1H), 5.52-5.48 (m, 1H), 4.68-4.62 (m, 3H), 4.21-4.17 (m, 2H), 3.81-3.76 (m, 2H), 3.42-3.30 (m, 6H), 3.08-3.04 (m, 1H), 1.62-1.57 (m, 4H), 1.47 (d, J = 6.8 Hz, 3H). | 659.3 | 64.6 | (3S,10S)-7-((3S,5R)-4-acryloyl-3,5-dimethylpiperazin-1-yl)-10-(5-chloro-2,4-dichlorophenyl)-3-((methoxymethoxy)methyl)-9-(trifluoromethyl)-2,3-dihydro-5H-[1,4]thiazino[2,3,4-ij]quinazolin-5-one |
| 1370 | 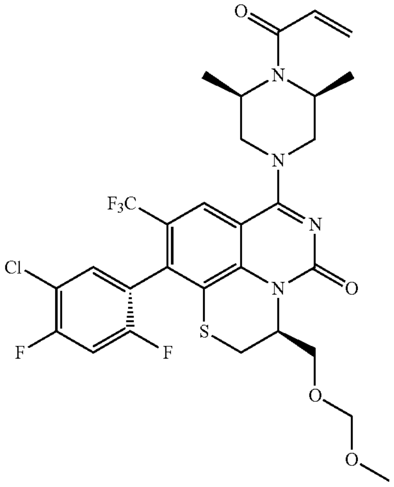 | $^1$H NMR (400 MHz, $CDCl_3$) δ: 8.06 (s, 1H), 7.29-7.26 (m, 1H), 7.10-7.05 (m, 1H), 6.65-6.58 (m, 1H), 6.43 (dd, J = 16.4 Hz, 2 Hz, 1H), 5.79 (dd, J = 10.8 Hz, 2 Hz, 1H), 5.50-5.46 (m, 1H), 4.68-4.63 (m, 3H), 4.21-4.17 (m, 2H), 3.80-3.78 (m, 2H), 3.42-3.31 (m, 6H), 3.09-3.05 (m, 1H), 1.61-1.60 (m, 4H), 1.48 (d, J = 6.8 Hz, 3H). | 659.3 | 94.4 | (3S,10R)-7-((3S,5R)-4-acryloyl-3,5-dimethylpiperazin-1-yl)-10-(5-chloro-2,4-difluorophenyl)-3-((methoxymethoxy)methyl)-9-(trifluoromethyl)-2,3-dihydro-5H-[1,4]thiazino[2,3,4-ij]quinazolin-5-one |

TABLE 11-continued

| Summary of % CAF at 10 μM after 1 hour for Examples 1300-1455 | | | | | |
|---|---|---|---|---|---|
| Ex. # | Structure | $^1$H NMR | MS $(M + H)^+$ | % CAF 10 uM @ 60 min | Name |
| 1371 | 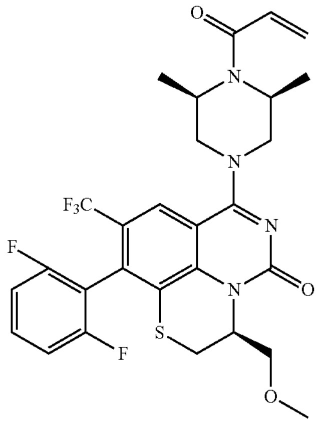 [SMILES: C=CC(=O)N1[C@H](C)CN(c2nc(=O)n3c4c(c(-c5c(F)cccc5F)c(C(F)(F)F)cc24)SC[C@@H]3COC)C[C@@H]1C] | $^1$H NMR (400 MHz, $CDCl_3$) δ: 8.10 (s, 1H), 7.55-7.45 (m, 1H), 7.05 (t, J = 8.0 Hz, 2H), 6.63 (dd, J = 16.8 Hz, 10.4 Hz, 1H), 6.41 (dd, J = 16.8 Hz, 2.0 Hz, 1H), 5.78 (dd, J = 10.4 Hz, 2.0 Hz, 1H), 5.50-5.45 (m, 1H), 4.70-4.61 (m, 2H), 4.29-4.11 (m, 2H), 3.70-3.61 (m, 2H), 3.40 (s, 3H), 3.38-3.30 (m, 3H), 3.07 (dd, J = 13.5, 2.7 Hz, 1H), 1.63 (d, J = 7.2 Hz, 3H), 1.48 (d, J = 7.2 Hz, 3H). | 595.2 | 60.6 | (S)-7-((3S,5R)-4-acryloyl-3,5-dimethylpiperazin-1-yl)-10-(2,6-difluorophenyl)-3-(methoxymethyl)-9-(trifluoromethyl)-2,3-dihydro-5H-[1,4]thiazino[2,3,4-ij]quinazolin-5-one |
| 1372 | 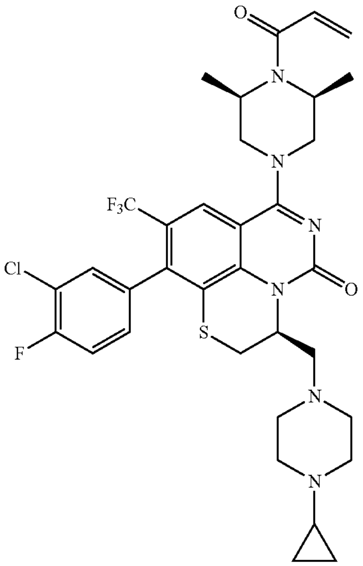 [SMILES: C=CC(=O)N1[C@H](C)CN(c2nc(=O)n3c4c(c(-c5ccc(F)c(Cl)c5)c(C(F)(F)F)cc24)SC[C@@H]3CN2CCN(C3CC3)CC2)C[C@@H]1C] | $^1$H NMR (400 MHz, $CDCl_3$) δ: 8.04 (s, 1H), 7.35-7.24 (m, 2H), 7.13-7.10 (m, 1H), 6.62 (dd, J = 10.4 Hz, J = 16.4 Hz, 1H), 6.40 (dd, J = 2.0 Hz, J = 16.8 Hz, 1H), 5.77 (dd, J = 1.6 Hz, J = 10.4 Hz, 1H), 5.37-5.34 (m, 1H), 4.85-4.45 (m, 2H), 4.19-4.15 (m, 2H), 3.44 (d, J = 12.0 Hz, 1H), 3.38-3.29 (m, 2H), 2.96 (d, J = 13.2 Hz, 1H), 2.80-2.50 (m, 10H), 1.59 (dd, J = 3.2 Hz, J = 6.8 Hz, 4H), 1.49 (q, J = 3.6 Hz, 3H), 0.50-0.37 (m, 4H). | 705.2 | 77.2 | (S)-7-((3S,5R)-4-acryloyl-3,5-dimethylpiperazin-1-yl)-10-(3-chloro-4-fluorophenyl)-3-((4-cyclopropylpiperazin-1-yl)methyl)-9-(trifluoromethyl)-2,3-dihydro-5H-[1,4]thiazino[2,3,4-ij]quinazolin-5-one |

TABLE 11-continued

| Summary of % CAF at 10 μM after 1 hour for Examples 1300-1455 | | | | | |
|---|---|---|---|---|---|
| Ex. # | Structure | $^1$H NMR | MS (M + H)$^+$ | % CAF 10 uM @ 60 min | Name |
| 1373 | 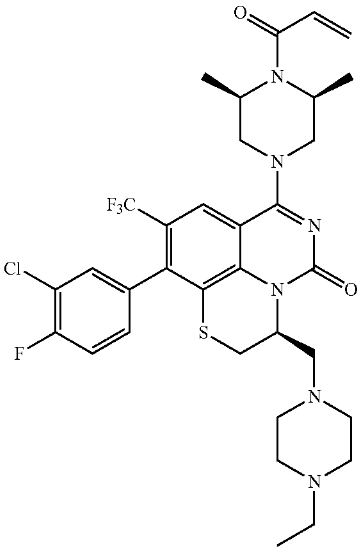 [SMILES: C=CC(=O)N1[C@H](C)CN(c2nc(=O)n3c4c(c(-c5ccc(F)c(Cl)c5)c(C(F)(F)F)cc24)SC[C@@H]3CN2CCN(CC)CC2)C[C@@H]1C] | $^1$H NMR (400 MHz, $CDCl_3$) δ: 8.07 (s, 1H), 7.30-7.25 (m, 2H), 7.14-7.09 (m, 1H), 6.62 (dd, J = 10.8 Hz, J = 16.8 Hz, 1H), 6.40 (dd, J = 1.6 Hz, J = 16.4 Hz, 1H), 5.77 (dd, J = 1.6 Hz, J = 10.4 Hz, 1H), 5.38-5.30 (m, 1H), 4.76-4.56 (m, 2H), 4.19-4.14 (m, 2H), 3.43-3.35 (m, 3H), 3.25-2.99 (m, 9H), 2.89-2.72 (m, 3H), 1.59 (dd, J = 3.2 Hz, J = 6.8 Hz, 4H), 1.49 (q, J = 3.6 Hz, 3H), 1.44 (t, J = 7.2 Hz, 3H). | 693.3 | 66.2 | (S)-7-((3S,5R)-4-acryloyl-3,5-dimethylpiperazin-1-yl)-10-(3-chloro-4-fluorophenyl)-3-((4ethylpiperazin-1-yl)methyl)-9-(trifluoromethyl)-2,3-dihydro-5H-[1,4]thiazino[2,3,4-ij]quinazolin-5-one |
| 1374 | 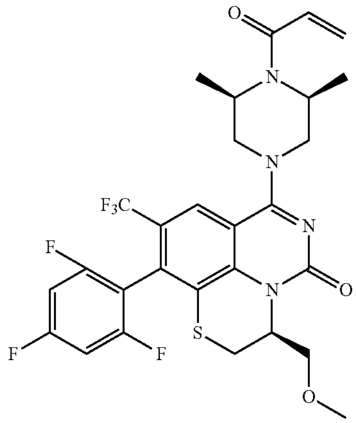 [SMILES: C=CC(=O)N1[C@H](C)CN(c2nc(=O)n3c4c(c(-c5c(F)cc(F)cc5F)c(C(F)(F)F)cc24)SC[C@@H]3COC)C[C@@H]1C] | $^1$H NMR (400 MHz, $CDCl_3$) δ: 8.09 (s, 1H), 6.82 (t, J = 7.2 Hz, 2H), 6.62 (dd, J = 10.8 Hz, J = 16.8 Hz, 1H), 6.40 (dd, J = 1.6 Hz, J = 16.4 Hz, 1H), 5.77 (dd, J = 1.6 Hz, J = 10.4 Hz, 1H), 5.50-5.45 (m, 1H), 4.85-4.52 (m, 2H), 4.22-4.16 (m, 2H), 3.67-3.60 (m, 2H), 3.40 (s, 3H), 3.37-3.30 (m, 3H), 3.07 (dd, J = 2.8 Hz, J = 13.2 Hz, 1H), 1.62 (d, J = 6.8 Hz, 3H), 1.47 (d, J = 7.2 Hz, 3H). | 613.2 | 88.5 | (S)-7-((3S,5R)-4-acryloyl-3,5-dimethylpiperazin-1-yl)-3-(methoxymethyl)-9-(trifluoromethyl)-10-(2,4,6-trifluorophenyl)-2,3-dihydro-5H-[1,4]thiazino[2,3,4-ij]quinazolin-5-one |
| 1375 | 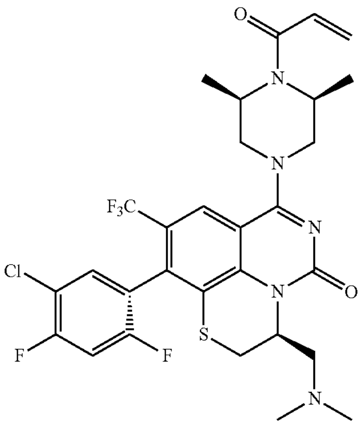 | $^1$H NMR (400 MHz, $CDCl_3$) δ: 8.07 (s, 1H), 7.29-7.25 (m, 1H), 7.08 (t, J = 8.8 Hz, 1H), 6.66-6.59 (m, 1H), 6.43-6.39 (m, 1H), 5.78 (dd, J = 10.4 Hz, 2.0 Hz, 1H), 5.38-5.35 (m, 1H), 4.71-4.59 (m, 2H), 4.20-4.16 (m, 2H), 3.50-3.30 (m, 3H), 3.04-3.00 (m, 1H), 2.85-2.83 (m, 1H), 2.43-2.37 (m, 7H), 1.60 (d, J = 7.2 Hz, 3H), 1.49 (d, J = 7.2 Hz, 3H). | 642.3 | 93.9 | (3S,10R)-7-((3S,5R)-4-acryloyl-3,5-dimethylpiperazin-1-yl)-10-(5-chloro-2,4-difluorophenyl)-3-((dimethylamino) methyl)-9-(trifluoromethyl)-2,3-dihydro-5H-[1,4]thiazino[2,3,4-ij]quinazolin-5-one |

TABLE 11-continued

| Ex. # | Structure | $^1$H NMR | MS (M + H)$^+$ | % CAF 10 uM @ 60 min | Name |
|---|---|---|---|---|---|
| Summary of % CAF at 10 µM after 1 hour for Examples 1300-1455 | | | | | |
| 1376 | 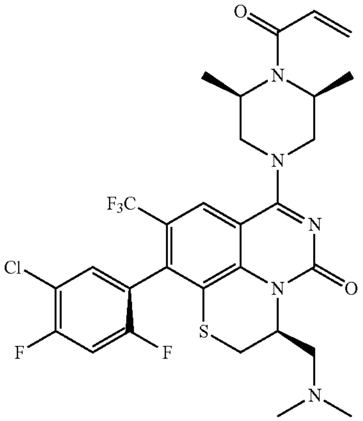 | $^1$H NMR (400 MHz, $CDCl_3$) δ: 8.07 (s, 1H), 7.29-7.25 (m, 1H), 7.07 (t, J = 8.8 Hz, 1H), 6.66-6.59 (m, 1H), 6.43-6.39 (m, 1H), 5.78 (dd, J = 10.0 Hz, 2.0 Hz, 1H), 5.40-5.38 (m, 1H), 4.69-4.58 (m, 2H), 4.20-4.17 (m, 2H), 3.51-3.30 (m, 3H), 3.02-2.78 (m, 2H), 2.37-2.23 (m, 7H), 1.61 (d, J = 7.2 Hz, 3H), 1.48 (d, J = 7.2 Hz, 3H). | 642.3 | 83.9 | (3S,10S)-7-((3S,5R)-4-acryloyl-3,5-dimethylpiperazin-1-yl)-10-(5-chloro-2,4-difluorophenyl)-3-((dimethylamino)methyl)-9-(trifluoromethyl)-2,3-dihydro-5H-[1,4]thiazino[2,3,4-ij]quinazolin-5-one |
| 1377 | 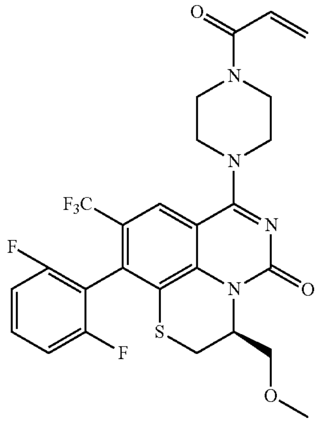 [SMILES: C=CC(=O)N1CCN(c2nc(=O)n3c4c(c(-c5c(F)cccc5F)c(C(F)(F)F)cc24)SC[C@@H]3COC)CC1] | $^1$H NMR (400 MHz, $CDCl_3$) δ: 7.83 (s, 1H), 7.52-7.46 (m, 1H), 7.05 (d, J = 8.0 Hz, 1H), 6.63-6.56 (m, 1H), 6.39-6.34 (m, 1H), 5.78 (dd, J = 10.4 Hz, 1.6 Hz, 1H), 5.47-5.44 (m, 1H), 3.98-3.90 (m, 3H), 3.82-3.79 (m, 5H), 3.70-3.62 (m, 2H), 3.40 (m, 3H), 3.36 (dd, J = 13.6 Hz, 2.8 Hz, 1H), 3.06 (dd, J = 13.2 Hz, 2.8 Hz, 1H). | 567.2 | 95.5 | (S)-7-(4-acryloylpiperazin-1-yl)-10-(2,6-difluorophenyl)-3-(methoxymethyl)-9-(trifluoromethyl)-2,3-dihydro-5H-[1,4]thiazino[2,3,4-ij]quinazolin-5-one |
| 1378 | 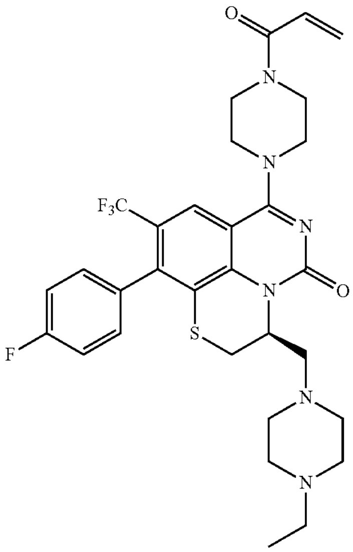 [SMILES: C=CC(=O)N1CCN(c2nc(=O)n3c4c(c(-c5ccc(F)cc5)c(C(F)(F)F)cc24)SC[C@@H]3CN2CCN(CC)CC2)CC1] | $^1$H NMR (400 MHz, $CDCl_3$) δ: 7.80 (s, 1H), 7.23-7.15 (m, 4H), 6.63-6.56 (m, 1H), 6.39-6.34 (m, 1H), 5.78 (dd, J = 10.4 Hz, 2.0 Hz, 1H), 5.36-5.32 (m, 1H), 3.93-3.80 (m, 8H), 3.40-3.37 (m, 1H), 2.97-2.93 (m, 1H), 2.84-2.79 (m, 3H), 2.60-2.45 (m, 9H), 1.31-1.09 (t, J = 8 Hz, 3H). | 631.3 | 78.9 | (S)-7-(4-acryloylpiperazin-1-yl)-3-((4-ethylpiperazin-1-yl)methyl)-10-(4-fluorophenyl)-9-(trifluoromethyl)-2,3-dihydro-5H-[1,4]thiazino[2,3,4-ij]quinazolin-5-one |

TABLE 11-continued

Summary of % CAF at 10 μM after 1 hour for Examples 1300-1455

| Ex. # | Structure | $^1$H NMR | MS (M + H)$^+$ | % CAF 10 uM @ 60 min | Name |
|---|---|---|---|---|---|
| 1379 | 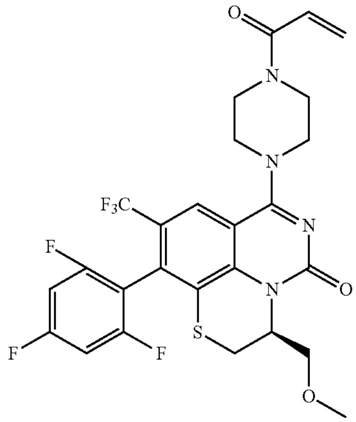 [SMILES: C=CC(=O)N1CCN(c2nc(=O)n3c4c(c(-c5c(F)cc(F)cc5F)c(C(F)(F)F)cc24)SC[C@@H]3COC)CC1] | $^1$H NMR (400 MHz, $CDCl_3$) δ: 7.82 (s, 1H), 6.83 (t, J = 8.4 Hz, 2H), 6.59 (dd, J = 16.8 Hz, 10.4 Hz, 1H), 6.37 (dd, J = 16.8 Hz, 1.6 Hz, 1H), 5.79 (dd, J = 10.8 Hz, 2 Hz, 1H), 5.48-5.44 (m, 1H), 3.97-3.95 (m, 3H), 3.81-3.79 (m, 5H), 3.69-3.63 (m, 2H), 3.44-3.35 (m, 4H), 3.07 (dd, J = 13.6 Hz, 2.8 Hz, 1H). | 585.3 | 96.7 | (S)-7-(4-acryloylpiperazin-1-yl)-3-(methoxymethyl)-9-(trifluoromethyl)-10-(2,4,6-trifluorophenyl)-2,3-dihydro-5H-[1,4]thiazino[2,3,4-ij]quinazolin-5-one |
| 1380 | 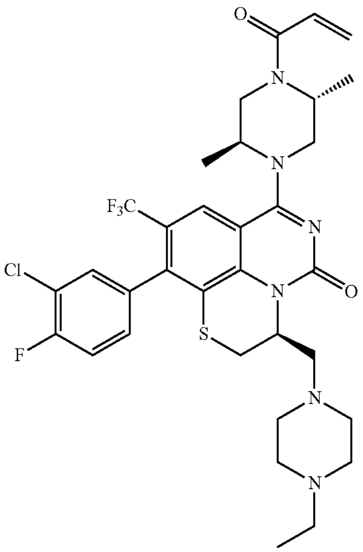 [SMILES: C=CC(=O)N1C[C@H](C)N(c2nc(=O)n3c4c(c(-c5ccc(F)c(Cl)c5)c(C(F)(F)F)cc24)SC[C@@H]3CN2CCN(CC)CC2)C[C@H]1C] | $^1$H NMR (400 MHz, $CDCl_3$) δ: 7.81 (s, 1H), 7.35-7.24 (m, 2H), 7.15-7.08 (m, 1H), 6.67-6.51 (m, 1H), 6.38 (t, J = 14.0 Hz, 1H), 5.80-5.76 (m, 1H), 5.40-5.32 (m, 1H), 5.06-5.00 (m, 0.5H), 4.86-4.65 (m, 1H), 4.44-4.28 (m, 1.5H), 4.05-3.99 (m, 0.5H), 3.76-3.67 (m, 2H), 3.40-3.29 (m, 1.5H), 2.99-2.96 (m, 1H), 2.82-2.77 (m, 3H), 2.71-2.42 (m, 9H), 1.47-1.36 (m, 6H), 1.09 (t, J = 6.8 Hz, 3H). | 693.3 | 88.4 | (S)-7-((2S,5R)-4-acryloyl-2,5-dimethylpiperazin-1-yl)-10-(3-chloro-4-fluorophenyl)-3-((4-ethylpiperazin-1-yl)methyl)-9-(trifluoromethyl)-2,3-dihydro-5H-[1,4]thiazino[2,3,4-ij]quinazolin-5-one |

TABLE 11-continued

| Ex. # | Structure | $^1$H NMR | MS (M + H)$^+$ | % CAF 10 uM @ 60 min | Name |
|---|---|---|---|---|---|
| Summary of % CAF at 10 μM after 1 hour for Examples 1300-1455 | | | | | |
| 1381 | 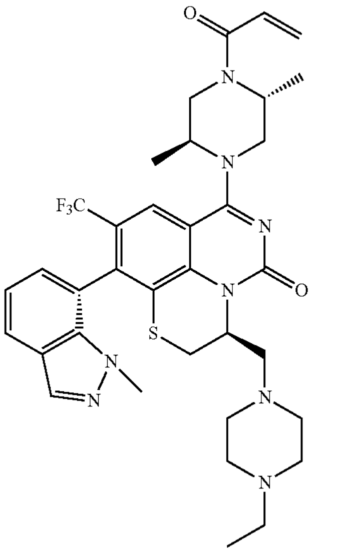 | | 695.4 | 19.1 | (3S,10R)-7-((2S,5R)-4-acryloyl-2,5-dimethylpiperazin-1-yl)-3-((4-ethylpiperazin-1-yl)methyl)-10-(1-methyl-1H-indazol-7-yl)-9-(trifluoromethyl)-2,3-dihydro-5H-[1,4]thiazino[2,3,4-ij]quinazolin-5-one |
| 1382 | 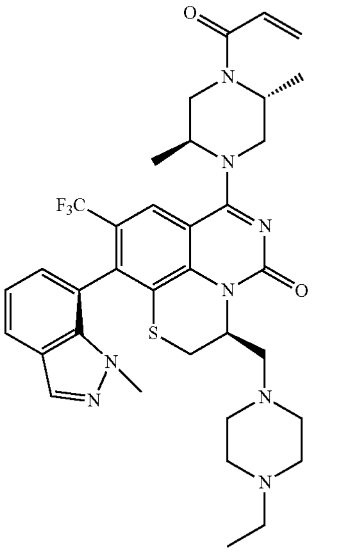 | | 695.4 | 49.1 | (3S,10S)-7-((2S,5R)-4-acryloyl-2,5-dimethylpiperazin-1-yl)-3-((4-ethylpiperazin-1-yl)methyl)-10-(1-methyl-1H-indazol-7-yl)-9-(trifluoromethyl)-2,3-dihydro-5H-[1,4]thiazino[2,3,4-ij]quinazolin-5-one |
| 1383 | 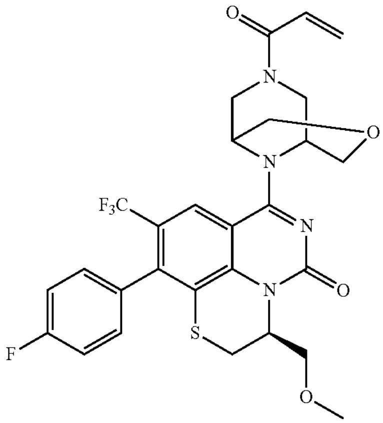 [SMILES: C=CC(=O)N1CC2COCC(C1)N2c1nc(=O)n2c3c(c(-c4ccc(F)cc4)c(C(F)(F)F)cc13)SC[C@@H]2COC] | $^1$H NMR (400 MHz, MeOH-d$_4$) δ 7.85 (d, J = 3.2 Hz, 1H), 7.35-7.19 (m, 4H), 6.84 (ddd, J = 17.3, 10.7, 7.0 Hz, 1H), 6.21 (d, J = 16.7, 1H), 5.77 (d, J = 10.7 Hz, 1H), 5.36-5.26 (m, 1H), 4.89-4.76 (m, 1H), 4.57-4.36 (m, 3H), 4.25-4.16 (m, 1H), 4.13-3.89 (m, 4H), 3.81-3.69 (m, 2H), 3.65-3.53 (m, 2H), 3.40 (s, 3H), 3.39-3.24 (m, 4H), 3.09 (dd, J = 13.7, 2.8 Hz, 1H). | 591.2 | 66 | (3S)-7-(7-acryloyl-3-oxa-7,9-diazabicyclo[3.3.1]nonan-9-yl)-10-(4-fluorophenyl)-3-(methoxymethyl)-9-(trifluoromethyl)-2,3-dihydro-5H-[1,4]thiazino[2,3,4-ij]quinazolin-5-one |

TABLE 11-continued

| Summary of % CAF at 10 μM after 1 hour for Examples 1300-1455 | | | | | |
|---|---|---|---|---|---|
| Ex. # | Structure | $^{1}$H NMR | MS (M + H)$^{+}$ | % CAF 10 uM @ 60 min | Name |
| 1384 | 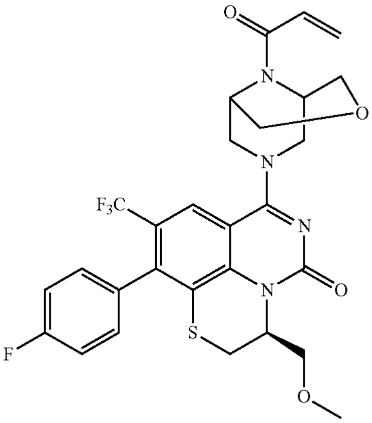 [SMILES: C=CC(=O)N1C2COCC1CN(c1nc(=O)n3c4c(c(-c5ccc(F)cc5)c(C(F)(F)F)cc14)SC[C@@H]3COC)C2] | $^{1}$H NMR (400 MHz, MeOH-d$_4$) δ 7.85 (d, J = 3.2 Hz, 1H), 7.34-7.17 (m, 4H), 6.84 (ddd, J = 17.4, 10.7, 7.1 Hz, 1H), 6.21 (d, J = 16.8, 1H), 5.77 (d, J = 10.7 Hz, 1H), 5.37-5.27 (m, 1H), 4.89-4.75 (m, 1H), 4.57-4.36 (m, 3H), 4.26-4.15 (m, 1H), 4.14-3.89 (m, 4H), 3.81-3.69 (m, 2H), 3.67-3.52 (m, 2H), 3.40 (s, 3H), 3.38-3.24 (m, 2H), 3.09 (dd, J = 13.7, 2.9 Hz, 1H). | 591.2 | 77.8 | (3S)-7-(9-acryloyl-3-oxa-7,9-diazabicyclo[3.3.1]nonan-7-yl)-10-(4-fluorophenyl)-3-(methoxymethyl)-9-(trifluoromethyl)-2,3-dihydro-5H-[1,4]thiazino[2,3,4-ij]quinazolin-5-one |
| 1385 | 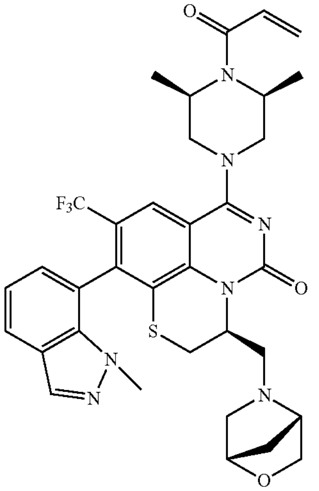 [SMILES: C=CC(=O)N1[C@H](C)CN(c2nc(=O)n3c4c(c(-c5cccc6cnn(C)c56)c(C(F)(F)F)cc24)SC[C@@H]3CN2C[C@@H]3C[C@H]2CO3)C[C@@H]1C] | $^{1}$H NMR (400 MHz, CDCl$_3$) δ: 8.13 (s, 1H), 8.06 (s, 1H), 7.87 (dd, J = 0.8 Hz, 8.0 Hz, 1H), 7.28-7.24 (m, 1H), 7.15 (d, J = 6.8 Hz, 1H), 6.66-6.59 (m, 1H), 6.43-6.39 (m, 1H), 5.78 (dd, J = 2.0 Hz, 10.4 Hz, 1H), 5.21-5.18 (m, 1H), 4.77-4.60 (m, 2H), 4.39 (s, 1H), 4.22 (d, J = 13.6 H, 2H), 3.95-3.92 (m, 1H), 3.65-3.63 (m, 1H), 3.58 (s, 3H), 3.45-3.38 (m, 4H), 3.02-2.98 (m, 3H), 2.93-2.86 (m, 1H), 2.75-2.71 (m, 1H), 1.75-1.71 (m, 2H), 1.64 (d, J = 7.2 Hz, 3H), 1.48 (d, J = 7.2 Hz, 3H). | 680.4 | 92.5 | (3S)-3-(((1S,4S)-2-oxa-5-azabicyclo[2.2.1]heptan-5-yl)methyl)-7-((3S,5R)-4-acryloyl-3,5-dimethylpiperazin-1-yl)-10-(1-methyl-1H-indazol-7-yl)-9-(trifluoromethyl)-2,3-dihydro-5H-[1,4]thiazino[2,3,4-ij]quinazolin-5-one |
| 1386 | 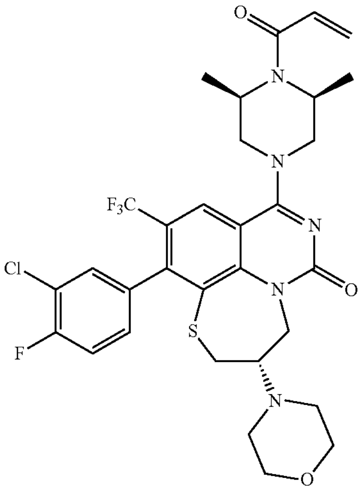 [SMILES: C=CC(=O)N1[C@H](C)CN(c2nc(=O)n3c4c(c(-c5ccc(F)c(Cl)c5)c(C(F)(F)F)cc24)SC[C@@H](N2CCOCC2)C3)C[C@@H]1C] | $^{1}$H NMR (400 MHz, CDCl$_3$) δ: 8.05 (s, 1H), 7.30-7.27 (m, 1H), 7.26-7.23 (m, 1H), 7.13-7.08 (m, 1H), 6.65-6.59 (m, 1H), 6.42 (dd, J = 2.0 Hz, 16.8 Hz, 1H), 5.78 (dd, J = 1.6 Hz, 10.0 Hz, 1H), 4.76-4.58 (m, 4H), 4.17-4.11 (m, 2H), 3.72-3.69 (m, 4H), 3.38-3.10 (m, 5H), 2.72-2.60 (m, 4H), 1.57-1.50 (m, 6H). | 666.3 | 71.6 | (S)-8-((3S,5R)-4-acryloyl-3,5-dimethylpiperazin-1-yl)-11-(3-chloro-4-fluorophenyl)-3-morpholino-10-(trifluoromethyl)-3,4-dihydro-2H,6H-[1,4]thiazepino[2,3-4-ij]quinazolin-6-one |

TABLE 11-continued

| Ex. # | Structure | $^1$H NMR | MS $(M + H)^+$ | % CAF 10 uM @ 60 min | Name |
|---|---|---|---|---|---|
| Summary of % CAF at 10 μM after 1 hour for Examples 1300-1455 | | | | | |
| 1387 | 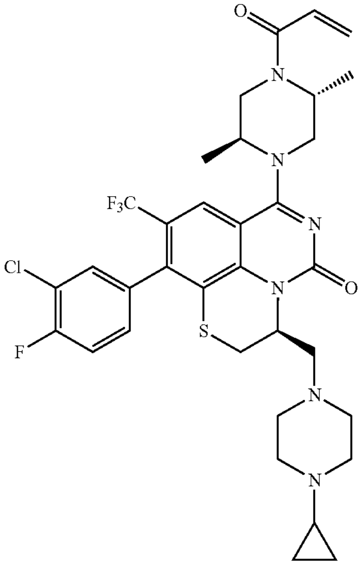 [SMILES: C=CC(=O)N1C[C@H](C)N(c2nc(=O)n3c4c(c(-c5ccc(F)c(Cl)c5)c(C(F)(F)F)cc24)SC[C@@H]3CN2CCN(C3CC3)CC2)C[C@H]1C] | $^1$H NMR (400 MHz, CDCl3) δ: 7.81 (s, 1H), 7.32-7.23 (m, 2H), 7.15-7.09 (m, 1H), 6.66-6.50 (m, 1H), 6.37 (t, J = 14.8 Hz, 1H), 5.77 (t, J = 8.4 Hz, 1H), 5.41-5.29 (m, 1H), 5.05-4.63 (m, 1.5H), 4.41-4.25 (m, 1H), 4.04-3.97 (m, 0.5H), 3.79-3.66 (m, 2H), 3.42-3.37 (m, 1H), 2.76 (d, J = 18.4 Hz, 1H), 2.60-2.51 (m, 11H), 1.46-1.36 (m, 7H), 0.45-0.39 (m, 4H). | 705.3 | 71 | (S)-7-((2S,5R)-4-acryloyl-2,5-dimethylpiperazin-1-yl)-10-(3-chloro-4-fluorophenyl)-3-((4-cyclopropylpiperazin-1-yl)methyl)-9-(trifluoromethyl)-2,3-dihydro-5H-[1,4]thiazino[2,3,4-ij]quinazolin-5-one |
| 1388 | 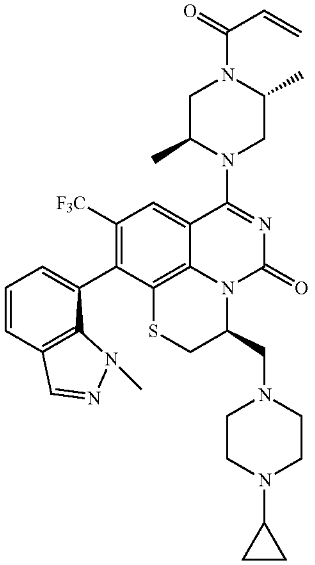 | $^1$H NMR (400 MHz, $CDCl_3$) δ 8.06 (s, 1H), 7.94-7.86 (m, 2H), 7.26-7.24 (m, 1H), 7.14-7.12 (m, 1H), 6.65-6.54 (m, 1H), 6.41-6.34 (m, 1H), 5.80-5.76 (m, 1H), 5.35-5.32 (m, 1H), 5.09-5.08 (m, 0.5H), 4.80-4.68 (m, 1H), 4.49-4.35 (m, 1.5H), 4.17-4.13 (m, 0.5H), 3.72-3.57 (m, 5H), 3.39-3.22 (m, 1.5H), 3.02-2.98 (m, 1H), 2.71-2.45 (m, 10H), 1.53-1.46 (m, 4H), 1.39-1.25 (m, 3H), 0.42-0.38 (m, 4H). | 707.4 | 95.3 | (3S,10S)-7-((2S,5R)-4-acryloyl-2,5-dimethylpiperazin-1-yl)-3-((4-cyclopropylpiperazin-1-yl)methyl)-10-(1-methyl-1H-indazol-7-yl)-9-(trifluoromethyl)-2,3-dihydro-5H-[1,4]thiazino[2,3,4-ij]quinazolin-5-one |

TABLE 11-continued

Summary of % CAF at 10 μM after 1 hour for Examples 1300-1455

| Ex. # | Structure | $^1$H NMR | MS $(M + H)^+$ | % CAF 10 uM @ 60 min | Name |
|---|---|---|---|---|---|
| 1389 | 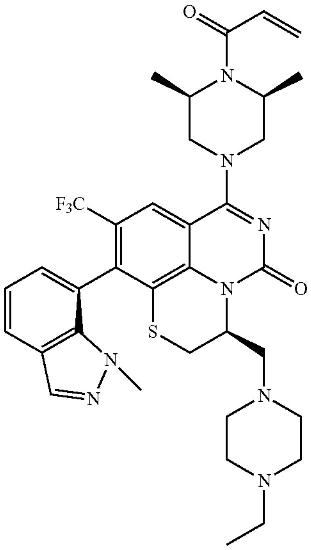 | $^1$H NMR (400 MHz, $CDCl_3$) δ: 8.17 (s, 1H), 8.08 (s, 1H), 7.90 (d, J = 8.8 Hz, 1H), 7.26-7.24 (m, 1H), 7.15 (d, J = 7.2 Hz, 1H), 6.67-6.60 (m, 1H), 6.44-6.39 (m, 1H), 5.81 (d, J = 12.4 Hz, 1H), 5.47 (s, 1H), 4.27 (d, J = 13.6 Hz, 2H), 3.57-3.39 (m, 5H), 3.22-3.07 (m, 5H), 3.01-3.96 (m, 11H), 1.66 (d, J = 6.8 Hz, 3H), 1.49 (d, J = 6.8 Hz, 3H), 1.36 (t, J = 7.2 Hz, 3H). | 695.4 | 69.1 | (3S,10S)-7-((3S,5R)-4-acryloyl-3,5-dimethylpiperazin-1-yl)-3-((4-ethylpiperazin-1-yl)methyl)-10-(1-methyl-1H-indazol-7-yl)-9-(trifluoromethyl)-2,3-dihydro-5H-[1,4]thiazino[2,3,4-ij]quinazolin-5-one |
| 1390 | 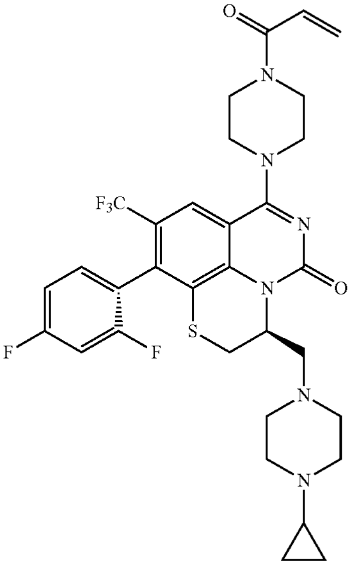 | $^1$H NMR (400 MHz, $CDCl_3$) δ: 7.80 (s, 1H), 7.21-7.15 (m, 1H), 7.05-6.90 (m, 2H), 6.63-6.50 (m, 1H), 6.40-6.30 (dd, J = 2 Hz, 16.8 Hz, 1H), 5.80-5.75 (m, 1H), 5.36-5.30 (m, 1H), 3.95-3.93 (m, 3H), 3.80-3.75 (m, 5H), 3.50-3.40 (m, 1H), 3.03-2.90 (m, 1H), 2.85-2.45 (m, 11H), 0.44-0.39 (m, 4H). | 661.3 | 96.7 | (3S,10R)-7-(4-acryloylpiperazin-1-yl)-3-((4-cyclopropylpiperazin-1-yl)methyl)-10-(2,4-difluorophenyl)-9-(trifluoromethyl)-2,3-dihydro-5H-[1,4]thiazino[2,3,4-ij]quinazolin-5-one |

TABLE 11-continued

Summary of % CAF at 10 μM after 1 hour for Examples 1300-1455

| Ex. # | Structure | $^1H$ NMR | MS $(M + H)^+$ | % CAF 10 uM @ 60 min | Name |
|---|---|---|---|---|---|
| 1391 | 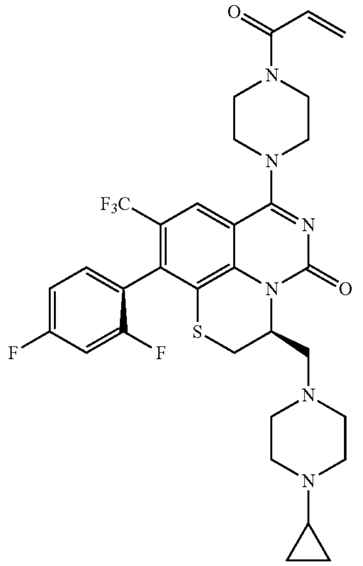 | $^1H$ NMR (400 MHz, $CDCl_3$) δ: 7.80 (s, 1H), 7.21-7.15 (m, 1H), 7.06-6.90 (m, 2H), 6.63-6.50 (m, 1H), 6.40-6.30 (m, 1H), 5.80-5.75 (m, 1H), 5.41-5.35 (m, 1H), 3.94-3.92 (s, 3H), 3.83-3.75 (m, 5H), 3.48-3.40 (m, 1H), 3.02-2.90 (m, 1H), 2.81-2.45 (m, 11H), 0.44-0.39 (m, 4H). | 661.3 | 95.9 | (3S,10S)-7-(4-acryloylpiperazin-1-yl)-3-((4-cyclopropylpiperazin-1-yl)methyl)-10-(2,4-difluorophenyl)-9-(trifluoromethyl)-2,3-dihydro-5H-[1,4]thiazino[2,3,4-ij]quinazolin-5-one |
| 1392a | 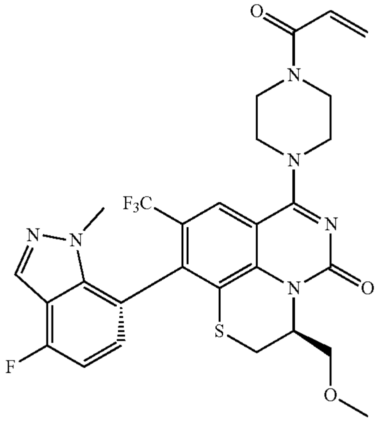 | $^1H$ NMR (400 MHz, MeOH-$d_4$) δ 8.16 (s, 1H), 8.06 (s, 1H), 7.16 (dd, J = 8.0, 4.8 Hz, 1H), 6.97 (dd, J = 9.7, 7.9 Hz, 1H), 6.82 (dd, J = 16.8, 10.6 Hz, 1H), 6.28 (dd, J = 16.8, 1.9 Hz, 1H), 5.81 (dd, J = 10.6, 1.9 Hz, 1H), 5.35 (ddt, J = 8.3, 5.3, 3.1 Hz, 1H), 4.16-4.04 (m, 2H), 4.00-3.74 (m, 6H), 3.73-3.60 (m, 2H), 3.57 (s, 3H), 3.36 (s, 3H), 3.35-3.33 (m, 1H), 3.13 (dd, J = 13.7, 3.0 Hz, 1H). | 603.2 | 97.2 | (3S,10S)-7-(4-acryloylpiperazin-1-yl)-10-(4-fluoro-1-methyl-1H-indazol-7-yl)-3-(methoxymethyl)-9-(trifluoromethyl)-2,3-dihydro-5H-[1,4]thiazino[2,3,4-ij]quinazolin-5-one |
| 1392 | 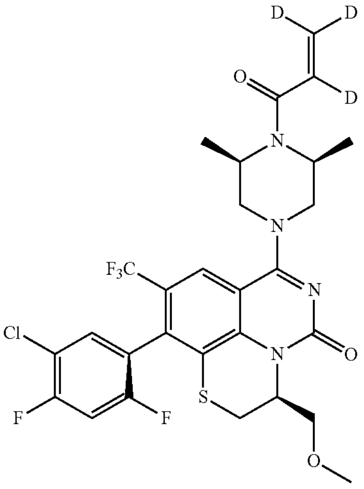 | $^1H$ NMR (400 MHz, MeOH-$d_4$) δ 8.15 (s, 1H), 7.48 (t, J = 7.6 Hz, 1H), 7.38 (t, J = 9.1 Hz, 1H), 5.42-5.34 (m, 1H), 4.83-4.56 (br s, 2H), 4.41-4.21 (m, 2H), 3.73-3.40 (m, 5H), 3.39 (s, 3H), 3.17 (dd, J = 13.6, 3.0 Hz, 1H), 1.56 (d, J = 6.9 Hz, 3H), 1.42 (d, J = 6.9 Hz, 3H). | 632.2 | 64.9 | (3S,10S)-7-((3S,5R)-4-(acryloyl-d3)-3,5-dimethylpiperazin-1-yl)-10-(5-chloro-2,4-difluorophenyl)-3-(methoxymethyl)-9-(trifluoromethyl)-2,3-dihydro-5H-[1,4]thiazino[2,3,4-ij]quinazolin-5-one |

TABLE 11-continued

| Ex. # | Structure | $^1$H NMR | MS (M + H)$^+$ | % CAF 10 uM @ 60 min | Name |
|---|---|---|---|---|---|
| Summary of % CAF at 10 μM after 1 hour for Examples 1300-1455 | | | | | |
| 1393 | 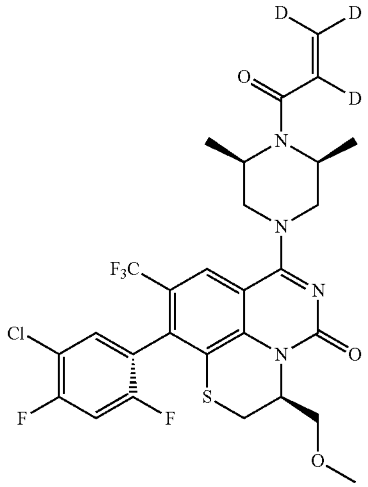 | $^1$H NMR (400 MHz, MeOH-$d_4$) δ 8.15 (s, 1H), 7.53 (t, J = 7.6 Hz, 1H), 7.37 (t, J = 9.1 Hz, 1H), 5.41-5.31 (m, 1H), 4.83-4.54 (br s, 2H), 4.39-4.29 (m, 2H), 3.74 (t, J = 9.2 Hz, 1H), 3.62 (dd, J = 9.2, 4.8 Hz, 1H), 3.49 (dd, J = 13.5, 4.7 Hz, 1H), 3.45-3.37 (m, 2H), 3.40 (s, 3H), 3.15 (dd, J = 13.7, 3.0 Hz, 1H), 1.57 (d, J = 7.0 Hz, 3H), 1.42 (d, J = 7.0 Hz, 3H). | 632.2 | 95.4 | (3S,10R)-7-((3S,5R)-4-(acryloyl-d3)-3,5-dimethylpiperazin-1-yl)-10-(5-chloro-2,4-difluorophenyl)-3-(methoxymethyl)-9-(trifluoromethyl)-2,3-dihydro-5H-[1,4]thiazino[2,3,4-ij]quinazolin-5-one |
| 1394 | 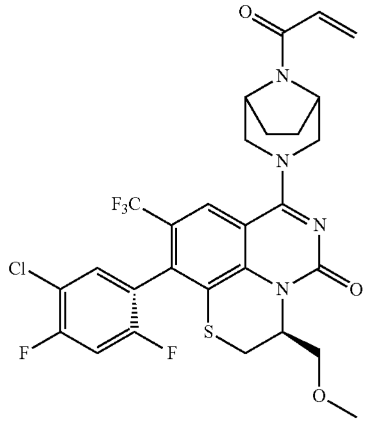 | $^1$H NMR (400 MHz, $CDCl_3$) δ: 7.74 (s, 1H), 7.29-7.25 (m, 1H), 7.07 (t, J = 8.4 Hz, 1H), 6.58-6.45 (m, 2H), 5.82 (d, J = 10 Hz, 1H), 5.44-5.38 (m, 1H), 5.03-4.61 (m, 2H), 4.44-4.42 (m, 1H), 4.23-3.64 (m, 4H), 3.54-3.25 (m, 5H), 3.05 (d, J = 13.6 Hz, 1H), 2.22-1.66 (m, 4H). | 627.2 | 93.5 | (3S,10R)-7-((1R,5S)-8-acryloyl-3,8-diazabicyclo[3.2.1]octan-3-yl)-10-(5-chloro-2,4-difluorophenyl)-3-(methoxymethyl)-9-(trifluoromethyl)-2,3-dihydro-5H-[1,4]thiazino[2,3,4-ij]quinazolin-5-one |
| 1395 | 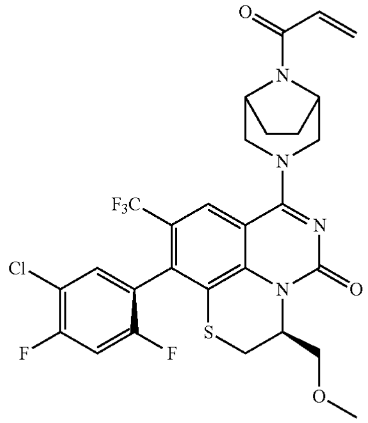 | $^1$H NMR (400 MHz, $CDCl_3$) δ: 7.76-7.32 (m, 1H), 7.29-7.25 (m, 1H), 7.07 (t, J = 8.4 Hz, 1H), 6.58-6.45 (m, 2H), 5.82 (d, J = 10 Hz, 1H), 5.45-5.41 (m, 1H), 5.05-4.57 (m, 2H), 4.44-4.42 (m, 1H), 4.21-3.62 (m, 4H), 3.54-3.24 (m, 5H), 3.05 (d, J = 15.6 Hz, 1H), 2.27-1.64 (m, 4H). | 627.2 | 17.3 | (3S,10S)-7-((1R,5S)-8-acryloyl-3,8-diazabicyclo[3.2.1]octan-3-yl)-10-(5-chloro-2,4-difluorophenyl)-3-(methoxymethyl)-9-(trifluoromethyl)-2,3-dihydro-5H-[1,4]thiazino[2,3,4-ij]quinazolin-5-one |

TABLE 11-continued

| Summary of % CAF at 10 μM after 1 hour for Examples 1300-1455 | | | | | |
|---|---|---|---|---|---|
| Ex. # | Structure | $^1$H NMR | MS (M + H)$^+$ | % CAF 10 uM @ 60 min | Name |
| 1396 | 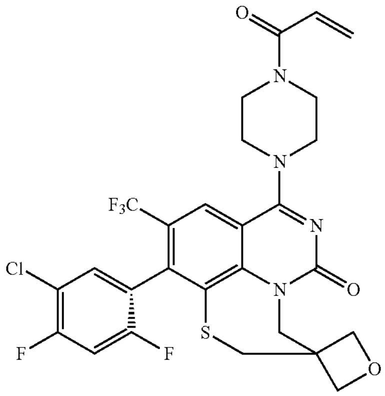 | $^1$H NMR (400 MHz, $CDCl_3$) δ: 7.82 (s, 1H), 7.25-7.23 (m, 1H), 7.05 (t, J = 8.8 Hz, 1H), 6.62-6.55 (m, 1H), 6.39 (dd, J = 16.4 Hz, 1.6 Hz, 1H), 5.80 (dd, J = 10.8 Hz, 2.0 Hz, 1H), 5.14-4.70 (m, 4H), 4.37-4.34 (m, 2H), 3.87-3.75 (m, 8H), 3.48-3.39 (m, 2H). | 613.2 | 95.1 | (R)-8'-(4-acryloylpiperazin-1-yl)-11'-(5-chloro-2,4-difluorophenyl)-10'-(trifluoromethyl)-2'H,4'H,6'H-spiro[oxetane-3,3'-[1,4]thiazepino[2,3-4-ij]quinazolin-6'-one |
| 1397 | 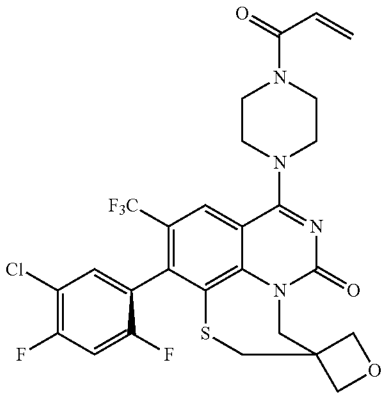 | $^1$H NMR (400 MHz, $CDCl_3$) δ: 7.82 (s, 1H), 7.25-7.23 (m, 1H), 7.05 (t, J = 8.8 Hz, 1H), 6.62-6.55 (m, 1H), 6.39 (dd, J = 16.8 Hz, 1.6 Hz, 1H), 5.80 (dd, J = 10.4 Hz, 2.0 Hz, 1H), 5.16-4.70 (m, 4H), 4.37-4.34 (m, 2H), 3.94-3.81 (m, 8H), 3.48-3.40 (m, 2H). | 613.2 | 78.2 | (S)-8'-(4-acryloylpiperazin-1-yl)-11'-(5-chloro-2,4-difluorophenyl)-10'-(trifluoromethyl)-2'H,4'H,6'H-spiro[oxetane-3,3'-[1,4]thiazepino[2,3,4-ij]quinazolin]-6'-one |
| 1398 | 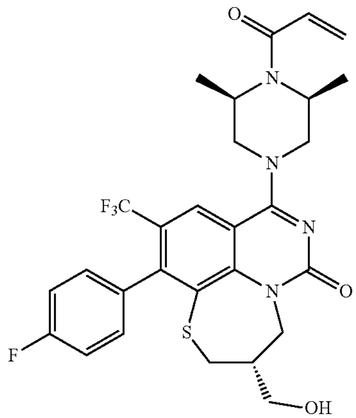 [SMILES: C=CC(=O)N1[C@H](C)CN(c2nc(=O)n3c4c(c(-c5ccc(F)cc5)c(C(F)(F)F)cc24)SC[C@@H](CO)C3)C[C@@H]1C] | $^1$H NMR (400 MHz, $CDCl_3$) δ: 8.10 (s, 1H), 7.24-7.15 (m, 4H), 6.66-6.59 (m, 1H), 6.43-6.39 (m, 1H), 5.78 (dd, J = 10.4 Hz, 2.0 Hz, 1H), 4.77-4.64 (m, 3H), 4.30-4.13 (m, 3H), 3.49-3.37 (m, 3H), 2.95-2.84 (m, 2H), 2.52-2.26 (m, 3H), 0.89-0.85 (m, 6H). | 577.2 | 44.2 | (R)-8-((3S,5R)-4-acryloyl-3,5-dimethylpiperazin-1-yl)-11-(4-fluorophenyl)-3-(hydroxymethyl)-10-(trifluoromethyl)-3,4-dihydro-2H,6H-[1,4]thiazepino[2,3,4-ij]quinazolin-6-one |

TABLE 11-continued

Summary of % CAF at 10 μM after 1 hour for Examples 1300-1455

| Ex. # | Structure | $^1$H NMR | MS (M + H)$^+$ | % CAF 10 uM @ 60 min | Name |
| --- | --- | --- | --- | --- | --- |
| 1399 | 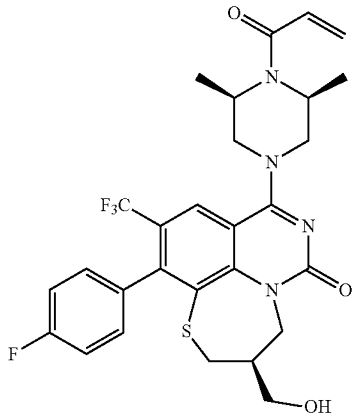 [SMILES: C=CC(=O)N1[C@H](C)CN(c2nc(=O)n3c4c(c(-c5ccc(F)cc5)c(C(F)(F)F)cc24)SC[C@H](CO)C3)C[C@@H]1C] | $^1$H NMR (400 MHz, $CDCl_3$) δ: 8.10 (s, 1H), 7.24-7.15 (m, 4H), 6.66-6.59 (m, 1H), 6.43-6.39 (m, 1H), 5.78 (dd, J = 10.4 Hz, 2.0 Hz, 1H), 4.78-4.77 (m, 3H), 4.21-4.13 (m, 3H), 3.69-3.67 (m, 1H), 3.47-3.35 (m, 3H), 2.91-2.89 (m, 2H), 2.51-2.38 (m, 2H), 0.89-0.83 (m, 6H). | 577.2 | 95.5 | (S)-8-((3S,5R)-4-acryloyl-3,5-dimethylpiperazin-1-yl)-11-(4-fluorophenyl)-3-(hydroxymethyl)-10-(trifluoromethyl)-3,4-dihydro-2H,6H-[1,4]thiazepino[2,3,4-ij]quinazolin-6-one |
| 1400 | 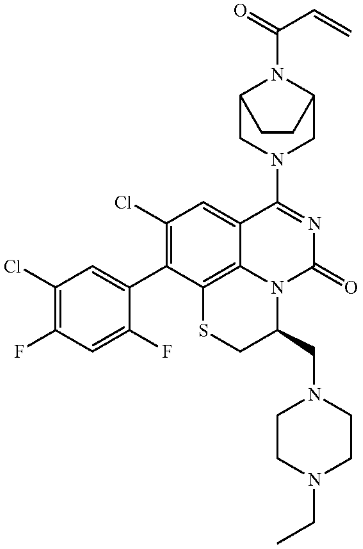 [SMILES: C=CC(=O)N1C2CCC1CN(c1nc(=O)n3c4c(c(-c5cc(Cl)c(F)cc5F)c(Cl)cc14)SC[C@@H]3CN1CCN(CC)CC1)C2] | $^1$H NMR (400 MHz, $CDCl_3$) δ: 7.47 (s, 1H), 7.32-7.28 (m, 1H), 7.11-7.06 (m, 1H), 6.57-6.42 (m, 2H), 5.79 (dd, J = 10.0 Hz, 2.4 Hz, 1H), 5.43-5.31 (m, 1H), 4.85-4.79 (m, 1.5H), 4.50-4.41 (m, 2H), 4.15-4.12 (m, 0.5H), 3.83-3.80 (m, 0.5H), 3.64-3.61 (m, 0.5H), 3.47-3.30 (m, 2H), 3.07-3.02 (m, 1H), 2.77-2.39 (m, 12H), 2.22-2.14 (m, 1H), 2.05-1.92 (m, 3H), 1.09-1.05 (m, 3H). | 675.62 | 43.7 | (3S)-7-((1R,5S)-8-acryloyl-3,8-diazabicyclo[3.2.1]octan-3-yl)-9-chloro-10-(5-chloro-2,4-difluorophenyl)-3-((4-ethylpiperazin-1-yl)methyl)-2,3-dihydro-5H-[1,4]thiazino[2,3,4-ij]quinazolin-5-one |
| 1401 | 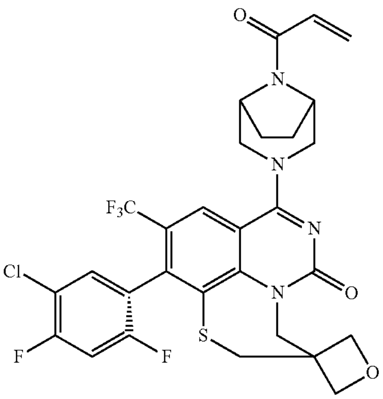 | $^1$H NMR (400 MHz, $CDCl_3$) δ: 7.77 (s, 1H), 7.24-7.22 (m, 1H), 7.05 (t, J = 8.8 Hz, 1H), 6.57-6.43 (m, 2H), 5.81 (dd, J = 10.0 Hz, 2.4 Hz, 1H), 5.05-4.80 (m, 5H), 4.43-4.35 (m, 4H), 4.16-3.71 (m, 2H), 3.47-3.39 (m, 3H), 2.06-1.83 (m, 4H). | 639.2 | 76.6 | (R)-8'-((1R,5S)-8-acryloyl-3,8-diazabicyclo[3.2.1]octan-3-yl)-11'-(5-chloro-2,4-difluorophenyl)-10'-(trifluoromethyl)-2'H,4'H,6'H-spiro[oxetane-3,3'-[1,4]thiazepino[2,3,4-ij]quinazolin]-6'-one |

TABLE 11-continued

Summary of % CAF at 10 μM after 1 hour for Examples 1300-1455

| Ex. # | Structure | $^1$H NMR | MS (M + H)$^+$ | % CAF 10 uM @ 60 min | Name |
|---|---|---|---|---|---|
| 1402 | 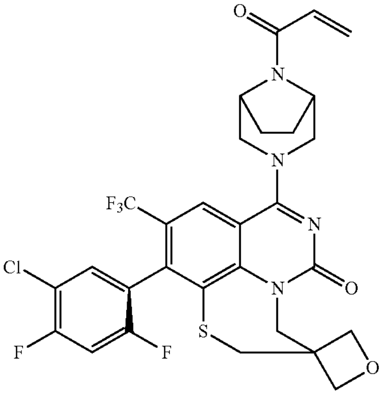 | $^1$H NMR (400 MHz, $CDCl_3$) δ: 7.77 (s, 1H), 7.24-7.22 (m, 1H), 7.05 (t, J = 8.4 Hz, 1H), 6.57-6.43 (m, 2H), 5.81 (dd, J = 9.6 Hz, 2.4 Hz, 1H), 5.08-4.71 (m, 5H), 4.48-4.35 (m, 4H), 4.19-3.70 (m, 2H), 3.47-3.35 (m, 3H), 2.14-1.78 (m, 4H). | 639.2 | 6.8 | (S)-8'-((1R,5S)-8-acryloyl-3,8-diazabicyclo[3.2.1]octan-3-yl)-11'-(5-chloro-2,4-difluorophenyl)-10'-(trifluoromethyl)-2'H,4'H,6'H-spiro[oxetane-3,3'-[1,4]thiazepino[2,3,4-ij]quinazolin-6'-one |
| 1403 | 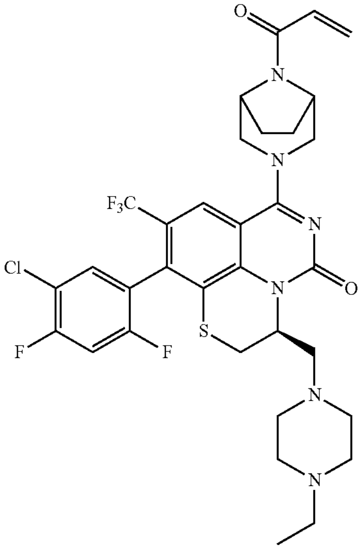 [SMILES: C=CC(=O)N1C2CCC1CN(c1nc(=O)n3c4c(c(-c5cc(Cl)c(F)cc5F)c(C(F)(F)F)cc14)SC[C@@H]3CN1CCN(CC)CC1)C2] | $^1$H NMR (400 MHz, $CDCl_3$) δ: 7.74 (s, 1H), 7.09-7.05 (m, 1H), 6.60-6.45 (m, 2H), 5.80 (d, J = 11.6 Hz, 1H), 5.46-5.30 (m, 1H), 4.90-4.86 (m, 1.5H), 4.43 (m, 2H), 4.09-3.88 (m, 1H), 3.66-3.51 (m, 1H), 3.40-3.32 (m, 1.5H), 3.04 (d, J = 15.2 Hz, 1H), 2.92-2.05 (m, 13H), 1.98-1.82 (m, 4H), 1.16 (m, 3H). | 709.3 | 80.3 | (3S)-7-((1R,5S)-8-acryloyl-3,8-diazabicyclo[3.2.1]octan-3-yl)-10-(5-chloro-2,4-difluorophenyl)-3-((4-ethylpiperazin-1-yl)methyl)-9-(trifluoromethyl)-2,3-dihydro-5H-[1,4]thiazino[2,3,4-ij]quinazolin-5-one |
| 1404 | 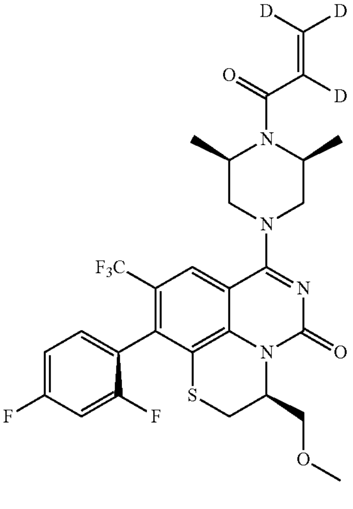 | $^1$H NMR (400 MHz, MeOH-$d_4$) δ 8.14 (s, 1H), 7.30 (q, J = 8.0 Hz, 1H), 7.14 (t, J = 9.1 Hz, 2H), 5.42-5.33 (m, 1H), 4.81-4.52 (m, 2H), 4.40-4.20 (m, 2H), 3.70 (t, J = 9.1 Hz, 1H), 3.59 (dd, J = 9.2, 4.9 Hz, 1H), 3.51 (dd, J = 13.5, 4.7 Hz, 1H), 3.45-3.40 (m, 1H), 3.39 (s, 3H), 3.38-3.33 (m, 1H), 3.15 (dd, J = 13.6, 2.9 Hz, 1H), 1.57 (d, J = 7.0 Hz, 3H), 1.42 (d, J = 6.9 Hz, 3H). | 598.2 | 80.9 | (3S,10S)-7-((3S,5R)-4-(acryloyl-d3)-3,5-dimethylpiperazin-1-yl)-10-(2,4-difluorophenyl)-3-(methoxymethyl)-9-(trifluoromethyl)-2,3-dihydro-5H-[1,4]thiazino[2,3,4-ij]quinazolin-5-one |

TABLE 11-continued

| Summary of % CAF at 10 μM after 1 hour for Examples 1300-1455 | | | | | |
|---|---|---|---|---|---|
| Ex. # | Structure | $^1$H NMR | MS (M + H)$^+$ | % CAF 10 uM @ 60 min | Name |
| 1405 | 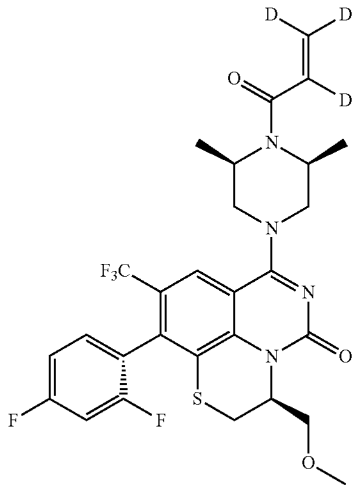 | $^1$H NMR (400 MHz, MeOH-$d_4$) δ 8.15 (s, 1H), 7.33 (q, J = 7.4 Hz, 1H), 7.14 (t, J = 7.5 Hz, 2H), 5.41-5.29 (m, 1H), 4.82-4.53 (br s, 2H), 4.39-4.19 (m, 2H), 3.72 (t, J = 9.2 Hz, 1H), 3.61 (dd, J = 9.2, 4.8 Hz, 1H), 3.48 (dd, J = 13.5, 4.7 Hz, 1H), 3.44-3.33 (m, 2H), 3.39 (s, 3H), 3.14 (dd, J = 13.6, 2.9 Hz, 1H), 1.58 (d, J = 6.9 Hz, 3H), 1.42 (d, J = 7.0 Hz, 3H). | 598.2 | 88.6 | (3S,10R)-7-((3S,5R)-4-(acryloyl-d3)-3,5-dimethylpiperazin-1-yl)-10-(2,4-difluorophenyl)-3-(methoxymethyl)-9-(trifluoromethyl)-2,3-dihydro-5H-[1,4]thiazino[2,3,4-ij]quinazolin-5-one |
| 1406 | 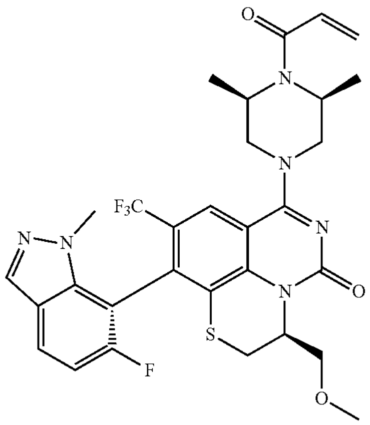 | $^1$H NMR (400 MHz, MeOH-$d_4$) δ 8.22 (s, 1H), 8.16 (s, 1H), 7.18 (dd, J = 8.0, 4.8 Hz, 1H), 6.97 (dd, J = 9.7, 8.0 Hz, 1H), 6.85 (dd, J = 16.7, 10.5 Hz, 1H), 6.30 (dd, J = 16.6, 2.0 Hz, 1H), 5.81 (dd, J = 10.6, 2.0 Hz, 1H), 5.39-5.31 (m, 1H), 4.84-4.46 (m, 3H), 4.39 (d, J = 13.8 Hz, 1H), 4.30 (d, J = 13.6 Hz, 1H), 3.73-3.60 (m, 2H), 3.56 (s, 3H), 3.55-3.38 (m, 3H), 3.36 (s, 2H), 3.35-3.33 (m, 1H), 3.15 (dd, J = 13.7, 3.0 Hz, 1H), 1.60 (d, J = 7.0 Hz, 3H), 1.47-1.39 (m, 3H). | 631.2 | 75.9 | (3S,10R)-7-((3S,5R)-4-acryloyl-3,5-dimethylpiperazin-1-yl)-10-(6-fluoro-1-methyl-1H-indazol-7-yl)-3-(methoxymethyl)-9-(trifluoromethyl)-2,3-dihydro-5H-[1,4]thiazino[2,3,4-ij]quinazolin-5-one |
| 1407 | 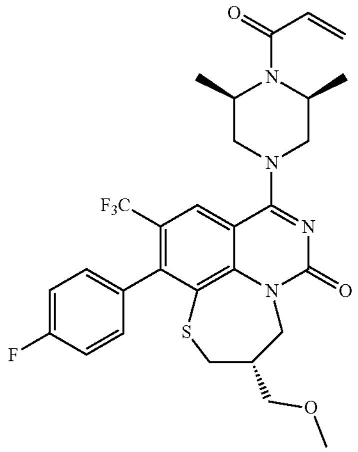 [SMILES: C=CC(=O)N1[C@H](C)CN(c2nc(=O)n3c4c(c(-c5ccc(F)cc5)c(C(F)(F)F)cc24)SC[C@@H](COC)C3)C[C@@H]1C] | $^1$H NMR (400 MHz, $CDCl_3$) δ: 8.06 (s, 1H), 7.23-7.15 (m, 4H), 6.63 (dd, J = 2.0 Hz, J = 16.4 Hz, 1H), 6.41 (dd, J = 1.6 Hz, J = 14.4 Hz, 1H), 5.77 (dd, J = 2.0 Hz, J = 10.4 Hz, 1H), 4.67-4.62 (m, 4H), 4.16 (d, J = 13.2 Hz, 2H), 3.52-3.46 (m, 1H), 3.35-3.31 (m, 6H), 3.26-3.18 (m, 1H), 3.02 (dd, J = 4.4 Hz, J = 14.8 Hz, 1H), 2.76-2.58 (m, 1H), 1.57-1.53 (m, 6H). | 591.2 | 92.7 | (R)-8-((3S,5R)-4-acryloyl-3,5-dimethylpiperazin-1-yl)-11-(4-fluorophenyl)-3-(methoxymethyl)-10-(trifluoromethyl)-3,4-dihydro-2H,6H-[1,4]thiazepino[2,3,4-ij]quinazolin-6-one |

TABLE 11-continued

| Ex. # | Structure | $^1$H NMR | MS (M + H)$^+$ | % CAF 10 uM @ 60 min | Name |
|---|---|---|---|---|---|
| Summary of % CAF at 10 μM after 1 hour for Examples 1300-1455 | | | | | |
| 1408 | 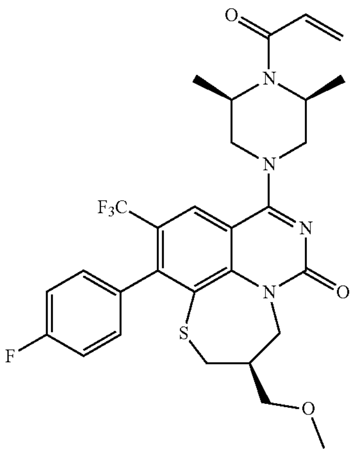 [SMILES: C=CC(=O)N1[C@H](C)CN(c2nc(=O)n3c4c(c(-c5ccc(F)cc5)c(C(F)(F)F)cc24)SC[C@H](COC)C3)C[C@@H]1C] | $^1$H NMR (400 MHz, $CDCl_3$) δ 8.06 (s, 1H), 7.23-7.15 (m, 4H), 6.62 (dd, J = 10.4 Hz, J = 16.8 Hz, 1H), 6.41 (dd, J = 1.6 Hz, J = 16.4 Hz, 1H), 5.77 (dd, J = 2.0 Hz, J = 10.4 Hz, 1H), 4.73-4.52 (m, 4H), 4.16 (d, J = 12.8 Hz, 2H), 3.56-3.44 (m, 1H), 3.35-3.26 (m, 6H), 3.23-3.19 (m, 1H), 3.02 (dd, J = 4.8 Hz, J = 15.2 Hz, 1H), 2.77-2.53 (m, 1H), 1.59-1.52 (m, 6H). | 591.2 | 83.7 | (S)-8-((3S,5R)-4-acryloyl-3,5-dimethylpiperazin-1-yl)-11-(4-fluorophenyl)-3-(methoxymethyl)-10-(trifluoromethyl)-3,4-dihydro-2H,6H-[1,4]thiazepino[2,3,4-ij]quinazolin-6-one |
| 1409 | 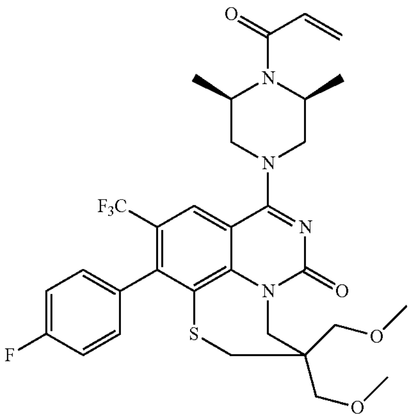 [SMILES: C=CC(=O)N1[C@H](C)CN(c2nc(=O)n3c4c(c(-c5ccc(F)cc5)c(C(F)(F)F)cc24)SCC(COC)(COC)C3)C[C@@H]1C] | $^1$H NMR (400 MHz, $CDCl_3$) δ 8.04 (s, 1H), 7.22-7.14 (m, 3H), 6.66-6.59 (m, 1H), 6.43 (dd, J = 1.6 Hz, 16.8 Hz, 1H), 5.78 (dd, J = 1.6 Hz, 10.4 Hz, 1H), 4.94-4.91 (m, 1H), 4.74-4.57 (m, 2H), 4.23-4.07 (m, 3H), 3.62-3.60 (m, 1H), 3.41-3.29 (m, 12H), 3.14-3.06 (m, 1H), 2.82-2.79 (m, 1H), 1.66 (d, J = 5.2 Hz, 3H), 1.44 (d, J = 4.4 Hz, 3H). | 635.3 | 96.5 | 8-((3S,5R)-4-acryloyl-3,5-dimethylpiperazin-1-yl)-11-(4-fluorophenyl)-3,3-bis(methoxymethyl)-10-(trifluoromethyl)-3,4-dihydro-2H,6H-[1,4]thiazepino[2,3,4-ij]quinazolin-6-one |
| 1410 | 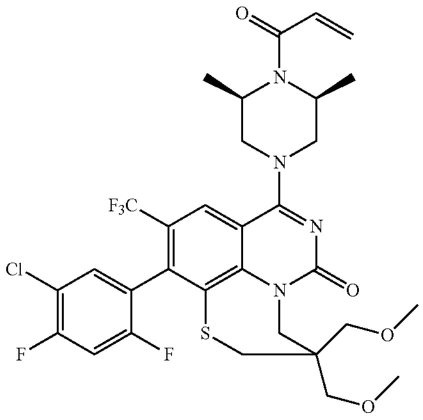 | $^1$H NMR (400 MHz, $CDCl_3$) δ: 8.05 (s, 1H), 7.32-7.26 (m, 1H), 7.07-7.02 (m, 1H), 6.66-6.59 (m, 1H), 6.43 (dd, J = 1.6 Hz, 16.8 Hz, 1H), 5.78 (dd, J = 1.2 Hz, 10.0 Hz, 1H), 4.95-4.92 (m, 1H), 4.77-4.54 (m, 2H), 4.22-4.06 (m, 3H), 3.62-3.57 (m, 1H), 3.38-3.34 (m, 11H), 3.21-3.11 (m, 1H), 2.90-2.86 (m, 1H), 1.64-1.63 (m, 3H), 1.44-1.43 (m, 3H). | 687.3 | 95.3 | 8-((3S,5R)-4-acryloyl-3,5-dimethylpiperazin-1-yl)-11-(5-chloro-2,4-difluorophenyl)-3,3-bis(methoxymethyl)-10-(trifluoromethyl)-3,4-dihydro-2H,6H-[1,4]thiazepino[2,3,4-ij]quinazolin-6-one |

TABLE 11-continued

Summary of % CAF at 10 μM after 1 hour for Examples 1300-1455

| Ex. # | Structure | $^1H$ NMR | MS $(M + H)^+$ | % CAF 10 uM @ 60 min | Name |
|---|---|---|---|---|---|
| 1411 | 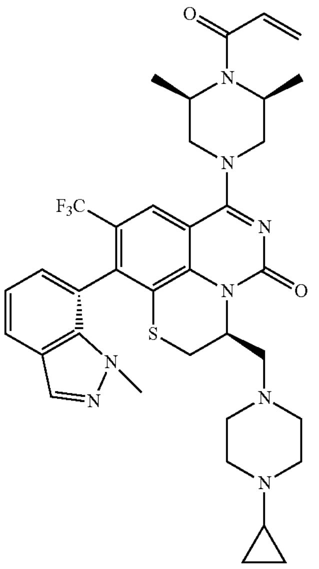 | $^1H$ NMR (400 MHz, $CDCl_3$) δ: 8.12 (s, 1H), 8.05 (s, 1H), 7.89 (d, J = 7.6 Hz, 1H), 7.22 (d, J = 7.6 Hz, 1H), 7.12 (d, J = 5.6 Hz, 1H), 6.67-6.59 (m, 1H), 6.41 (d, J = 16.4 Hz, 1H), 5.77 (d, J = 12 Hz, 1H), 5.40-5.36 (m, 1H), 4.77-4.59 (m, 2H), 4.20 (t, J = 12.4 Hz, 2H), 3.55 (s, 3H), 3.40-3.35 (m, 3H), 2.96 (d, J = 14.4 Hz, 1H), 2.82-2.50 (m, 10H), 1.59 (m, 3H), 1.53-1.51 (m, 3H), 1.25 (s, 1H), 0.43-0.42 (m, 4H). | 707.4 | 0 | (3S,10R)-7-((3S,5R)-4-acryloyl-3,5-dimethylpiperazin-1-yl)-3-((4-cyclopropylpiperazin-1-yl)methyl)-10-(1-methyl-1H-indazol-7-yl)-9-(trifluoromethyl)-2,3-dihydro-5H-[1,4]thiazino[2,3,4-ij]quinazolin-5-one |
| 1412 | 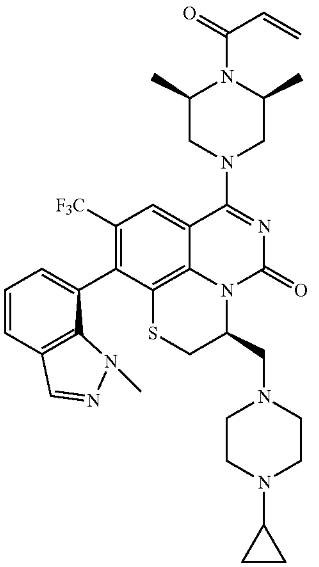 | $^1H$ NMR (400 MHz, $CDCl_3$) δ: 8.13 (s, 1H), 8.06 (s, 1H), 7.87 (d, J = 8 Hz, 1H), 7.28-7.24 (m, 1H), 7.14 (d, J = 6.8 Hz, 1H), 6.67-6.60 (m, 1H), 6.42 (d, J = 16.8 Hz, 1H), 5.77 (d, J = 10.8 Hz, 1H), 5.38-5.35 (m, 1H), 4.86-4.50 (m, 2H), 4.20 (t, J = 13.6 Hz, 2H), 3.57 (s, 3H), 3.43-3.33 (m, 3H), 2.99 (d, J = 15.6 Hz, 1H), 2.73-2.44 (m, 10H), 1.64-1.62 (m, 3H), 1.50-1.48 (m, 3H), 1.25 (s, 1H), 0.44-0.41 (m, 4H). | 707.4 | 85.4 | (3S,10S)-7-((3S,5R)-4-acryloyl-3,5-dimethylpiperazin-1-yl)-3-((4-cyclopropylpiperazin-1-yl)methyl)-10-(1-methyl-1H-indazol-7-yl)-9-(trifluoromethyl)-2,3-dihydro-5H-[1,4]thiazino[2,3,4-ij]quinazolin-5-one |

TABLE 11-continued

| Summary of % CAF at 10 μM after 1 hour for Examples 1300-1455 | | | | | |
|---|---|---|---|---|---|
| Ex. # | Structure | $^1H$ NMR | MS $(M + H)^+$ | % CAF 10 uM @ 60 min | Name |
| 1413 | 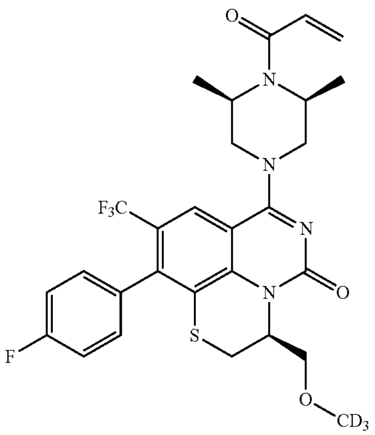 [SMILES: [2H]C([2H])([2H])OC[C@H]1CSc2c(-c3ccc(F)cc3)c(C(F)(F)F)cc3c(N4C[C@@H](C)N(C(=O)C=C)[C@@H](C)C4)nc(=O)n1c23] | $^1H$ NMR (400 MHz, $CDCl_3$) δ: 8.06 (s, 1H), 7.23-7.15 (m, 4H), 6.62 (dd, J = 10.4 Hz, J = 16.4 Hz, 1H), 6.41 (dd, J = 1.6 Hz, J = 16.8 Hz, 1H), 5.77 (dd, J = 2.0 Hz, J = 10.4 Hz, 1H), 5.43-5.41 (m, 1H), 4.82-4.54 (m, 2H), 4.21-4.16 (m, 2H), 3.69-3.62 (m, 2H), 3.39-3.29 (m, 3H), 2.98-2.94 (m, 1H), 1.62 (d, J = 7.2 Hz, 3H), 1.47 (d, J = 7.2 Hz, 3H). | 580.2 | 95.1 | (S)-7-((3S,5R)-4-acryloyl-3,5-dimethylpiperazin-1-yl)-10-(4-fluorophenyl)-3-((methoxy-d3)methyl)-9-(trifluoromethyl)-2,3-dihydro-5H-[1,4]thiazino[2,3,4-ij]quinazolin-5-one |
| 1414 | 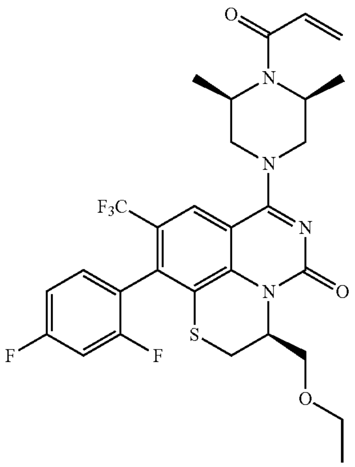 [SMILES: C=CC(=O)N1[C@H](C)CN(c2nc(=O)n3c4c(c(-c5ccc(F)cc5F)c(C(F)(F)F)cc24)SC[C@@H]3COCC)C[C@@H]1C] | $^1H$ NMR (400 MHz, $CDCl_3$) δ: 8.07 (s, 1H), 7.23-7.13 (m, 1H), 7.08-6.92 (m, 2H), 6.63 (dd, J = 16.8 Hz, 6.0 Hz, 1H), 6.41 (dd, J = 16.8 Hz, 1.6 Hz, 1H), 5.78 (dd, J = 10.8 Hz, 1.6 Hz, 1H), 5.51-5.38 (m, 1H), 5.00-4.40 (m, 2H), 4.25-4.14 (m, 2H), 3.74-3.47 (m, 4H), 3.43-3.28 (m, 3H), 3.07-2.97 (m, 1H), 1.63 (d, J = 7.2 Hz, 3H), 1.48 (d, J = 6.4 Hz, 3H), 1.18 (t, J = 6.8 Hz, 3H). | 609.2 | 91.8 | (3S)-7-((3S,5R)-4-acryloyl-3,5-dimethylpiperazin-1-yl)-10-(2,4-difluorophenyl)-3-(ethoxymethyl)-9-(trifluoromethyl)-2,3-dihydro-5H-[1,4]thiazino[2,3,4-ij]quinazolin-5-one |
| 1415 | 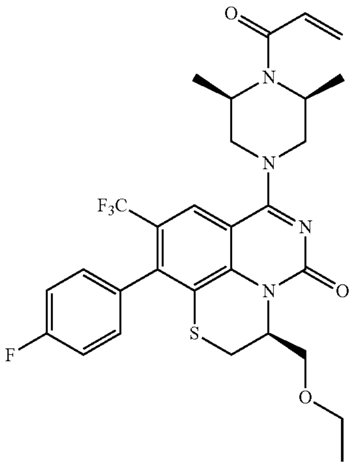 [SMILES: C=CC(=O)N1[C@H](C)CN(c2nc(=O)n3c4c(c(-c5ccc(F)cc5)c(C(F)(F)F)cc24)SC[C@@H]3COCC)C[C@@H]1C] | $^1H$ NMR (400 MHz, $CDCl_3$) δ: 8.06 (s, 1H), 7.25-7.14 (m, 4H), 6.63 (dd, J = 16.4 Hz, 10.8 Hz, 1H), 6.41 (dd, J = 16.8 Hz, 1.6 Hz, 1H), 5.78 (dd, J = 10.4 Hz, 2.0 Hz, 1H), 5.47-5.37 (m, 1H), 4.90-4.40 (m, 2H), 4.25-4.13 (m, 2H), 3.75-3.47 (m, 4H), 3.43-3.26 (m, 3H), 2.96 (dd, J = 13.6 Hz, 2.8 Hz, 1H), 1.62 (d, J = 7.2 Hz, 3H), 1.47 (d, J = 6.8 Hz, 3H), 1.18 (t, J = 6.8 Hz, 3H). | 591.3 | 90.1 | (S)-7-((3S,5R)-4-acryloyl-3,5-dimethylpiperazin-1-yl)-3-(ethoxymethyl)-10-(4-fluorophenyl)-9-(trifluoromethyl)-2,3-dihydro-5H-[1,4]thiazino[2,3,4-ij]quinazolin-5-one |

TABLE 11-continued

| Summary of % CAF at 10 μM after 1 hour for Examples 1300-1455 | | | | | |
|---|---|---|---|---|---|
| Ex. # | Structure | $^1$H NMR | MS (M + H)$^+$ | % CAF 10 uM @ 60 min | Name |
| 1416 | 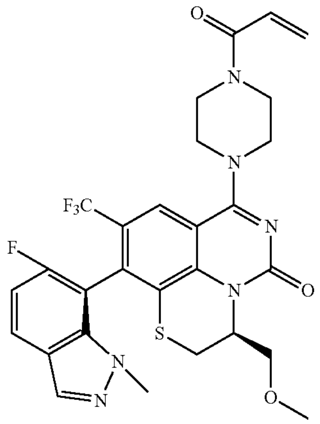 | $^1$H NMR (400 MHz, MeOH-$d_4$) δ 8.16 (s, 1H), 8.06 (s, 1H), 7.16 (dd, J = 8.0, 4.8 Hz, 1H), 6.97 (dd, J = 9.6, 7.9 Hz, 1H), 6.82 (dd, J = 16.8, 10.6 Hz, 1H), 6.28 (dd, J = 16.8, 1.9 Hz, 1H), 5.81 (dd, J = 10.6, 1.9 Hz, 1H), 5.38-5.29 (m, 1H), 4.16-4.04 (m, 2H), 4.00-3.75 (m, 5H), 3.73-3.59 (m, 3H), 3.56 (s, 3H), 3.35 (s, 3H), 3.35-3.23 (m, 1H), 3.13 (dd, J = 13.6, 3.0 Hz, 1H). | 603.1 | 71.3 | (3S,10R)-7-(4-acryloylpiperazin-1-yl)-10-(6-fluoro-1-methyl-1H-indazol-7-yl)-3-(methoxymethyl)-9-(trifluoromethyl)-2,3-dihydro-5H-[1,4]thiazino[2,3,4-ij]quinazolin-5-one |
| 1417 | 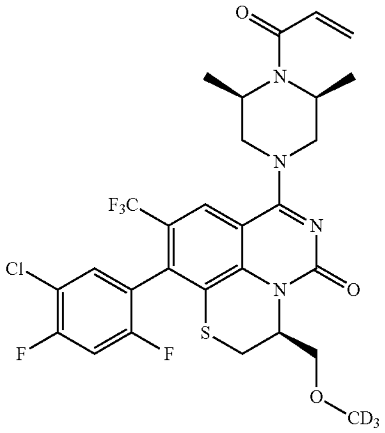 [SMILES: [2H]C([2H])([2H])OC[C@H]1CSc2c(-c3cc(Cl)c(F)cc3F)c(C(F)(F)F)cc3c(N4C[C@@H](C)N(C(=O)C=C)[C@@H](C)C4)nc(=O)n1c23] | $^1$H NMR (400 MHz, $CDCl_3$) δ: 8.11 (s, 1H), 7.35-7.27 (m, 1H), 7.15-7.09 (m, 1H), 6.72-6.63 (m, 1H), 6.49-6.42 (m, 1H), 5.84-5.80 (m, 1H), 5.52-5.47 (m, 1H), 4.75-4.64 (m, 2H), 4.26-4.22 (m, 2H), 3.75-3.66 (m, 2H), 3.45-3.34 (m, 3H), 3.10-3.05 (m, 1H), 1.69-1.67 (m, 3H), 1.54-1.50 (m, 3H). | 632.3 | 92.5 | (3S)-7-((3S,5R)-4-acryloyl-3,5-dimethylpiperazin-1-yl)-10-(5-chloro-2,4-difluorophenyl)-3-((methoxy-d3)methyl)-9-(trifluoromethyl)-2,3-dihydro-5H-[1,4]thiazino[2,3,4-ij]quinazolin-5-one |
| 1418 | 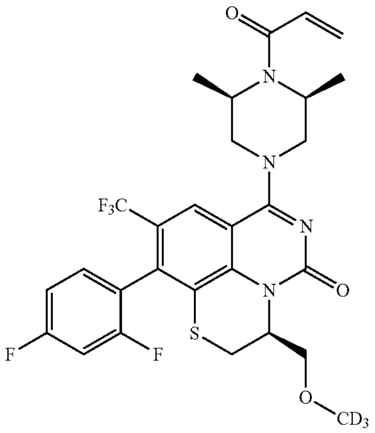 [SMILES: [2H]C([2H])([2H])OC[C@H]1CSc2c(-c3ccc(F)cc3F)c(C(F)(F)F)cc3c(N4C[C@@H](C)N(C(=O)C=C)[C@@H](C)C4)nc(=O)n1c23] | $^1$H NMR (400 MHz, $CD_3OD$) δ 8.08 (s, 1H), 7.21-7.15 (m, 1H), 7.00-6.94 (m, 2H), 6.65-5.58 (m, 1H), 6.44-6.38 (m, 1H), 5.80-5.76 (m, 1H), 5.48-5.45 (m, 1H), 4.74-4.57 (m, 2H), 4.19-4.17 (m, 2H), 3.65-3.58 (m, 2H), 3.40-3.34 (m, 3H), 3.06-2.98 (m, 1H), 1.63-1.60 (m, 3H), 1.47 (d, J = 7.2 Hz, 3H). | 598.3 | 95.4 | (3S)-7-((3S,5R)-4-acryloyl-3,5-dimethylpiperazin-1-yl)-10-(2,4-difluorophenyl)-3-((methoxy-d3)methyl)-9-(trifluoromethyl)-2,3-dihydro-5H-[1,4]thiazino[2,3,4-ij]quinazolin-5-one |

TABLE 11-continued

| Summary of % CAF at 10 μM after 1 hour for Examples 1300-1455 | | | | | |
|---|---|---|---|---|---|
| Ex. # | Structure | $^1$H NMR | MS (M + H)$^+$ | % CAF 10 uM @ 60 min | Name |
| 1419 | 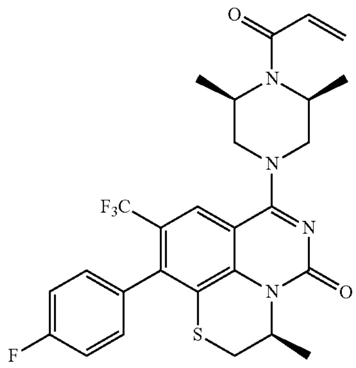 [SMILES: C=CC(=O)N1[C@H](C)CN(c2nc(=O)n3c4c(c(-c5ccc(F)cc5)c(C(F)(F)F)cc24)SC[C@@H]3C)C[C@@H]1C] | $^1$H NMR (400 MHz, $CDCl_3$) δ 8.08 (s, 1H), 7.23-7.16 (m, 4H), 6.66-6.59 (m, 1H) 6.43-6.38 (m, 1H), 5.78-5.75 (m, 1H), 5.45-5.42 (m, 1H), 4.78-4.53 (m, 2H), 4.21-4.15 (m, 2H), 3.38-3.27 (m, 2H), 3.14-3.10 (m, 1H), 2.90-2.86 (m, 1H), 1.64 (d, J = 5.2 Hz, 3H), 1.48-1.45 (m, 6H). | 547.2 | 95.7 | (S)-7-((3S,5R)-4-acryloyl-3,5-dimethylpiperazin-1-yl)-10-(4-fluorophenyl)-3-methyl-9-(trifluoromethyl)-2,3-dihydro-5H-[1,4]thiazino[2,3,4-ij]quinazolin-5-one |
| 1420 | 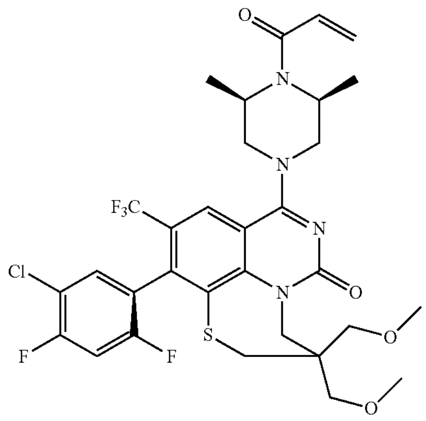 | $^1$H NMR (400 MHz, $CDCl_3$) δ: 8.05 (s, 1H), 7.32-7.26 (m, 1H), 7.05 (t, J = 8.4 Hz, 1H), 6.66-6.59 (m, 1H), 6.43 (dd, J = 2.0 Hz, 16.8 Hz, 1H), 5.78 (dd, J = 1.6 Hz, 10.4 Hz, 1H), 4.96-4.59 (m, 3H), 4.21-4.06 (m, 3H), 3.63-3.59 (m, 1H), 3.39-3.34 (m, 11H), 3.20-3.10 (m, 1H), 2.92-2.85 (m, 1H), 1.71-1.61 (m, 3H), 1.51-1.38 (m, 3H). | 687.3 | 93 | (S)-8-((3S,5R)-4-acryloyl-3,5-dimethylpiperazin-1yl)-11-(5-chloro-2,4-difluorophenyl)-3,3-bis(methoxymethyl)-10-(trifluoromethyl)-3,4-dihydro-2H,6H-[1,4]thiazepino[2,3,4-ij]quinazolin-6-one |
| 1421 | 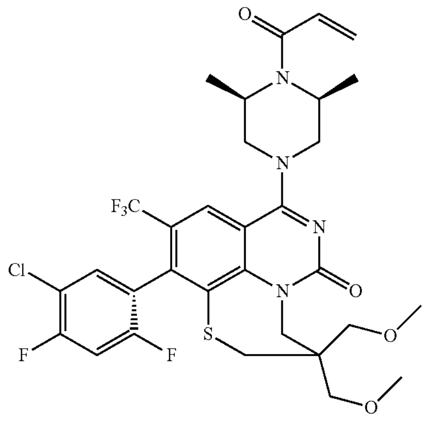 | $^1$H NMR (400 MHz, $CDCl_3$) δ: 8.10 (s, 1H), 7.37-7.34 (m, 1H), 7.10 (t, J = 11.2 Hz, 1H), 6.72-6.63 (m, 1H), 6.48 (dd, J = 2.4 Hz, 22.0 Hz, 1H), 5.84 (dd, J = 2.4 Hz, 14.0 Hz, 1H), 5.00-4.58 (m, 3H), 4.27-4.11 (m, 3H), 3.69-3.62 (m, 1H), 3.43-3.35 (m, 11H), 3.25-3.14 (m, 1H), 2.95-2.90 (m, 1H), 1.75-1.69 (m, 3H), 1.50-1.48 (m, 3H). | 687.3 | 91 | (R)-8-((3S,5R)-4-acryloyl-3,5-dimethylpiperazin-1-yl)-11-(5-chloro-2,4-difluorophenyl)-3,3-bis(methoxymethyl)-10-(trifluoromethyl)-3,4-dihydro-2H,6H-[1,4]thiazepino[2,3,4-ij]quinazolin-6-one |

TABLE 11-continued

| Ex. # | Structure | $^1$H NMR | MS (M + H)$^+$ | % CAF 10 uM @ 60 min | Name |
|---|---|---|---|---|---|
| Summary of % CAF at 10 μM after 1 hour for Examples 1300-1455 | | | | | |
| 1422 | 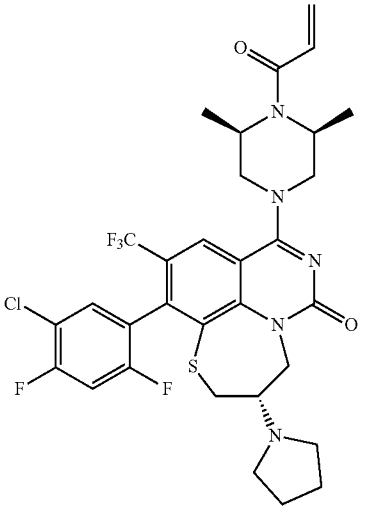 [SMILES: C=CC(=O)N1[C@H](C)CN(c2nc(=O)n3c4c(c(-c5cc(Cl)c(F)cc5F)c(C(F)(F)F)cc24)SC[C@@H](N2CCCC2)C3)C[C@@H]1C] | $^1$H NMR (400 MHz, $CDCl_3$) δ 8.06 (s, 1H), 7.26-7.24 (m, 1H), 7.04 (t, J = 8.8 Hz, 1H), 6.66-6.59 (m, 1H), 6.40 (d, J = 16.0 Hz, 1H), 5.76 (d, J = 20 Hz, 1H), 4.89-4.45 (m, 4H), 4.14-4.13 (m, 2H), 3.42-3.15 (m, 5H), 2.86-2.53 (m, 4H), 1.90-1.73 (m, 4H), 1.55-1.43 (m, 6H). | 668.3 | 94.1 | (3S)-8-((3S,5R)-4-acryloyl-3,5-dimethylpiperazin-1-yl)-11-(5-chloro-2,4-difluorophenyl)-3-(pyrrolidin-1-yl)-10-(trifluoromethyl)-3,4-dihydro-2H,6H-[1,4]thiazepino[2,3,4-ij]quinazolin-6-one |
| 1423 | 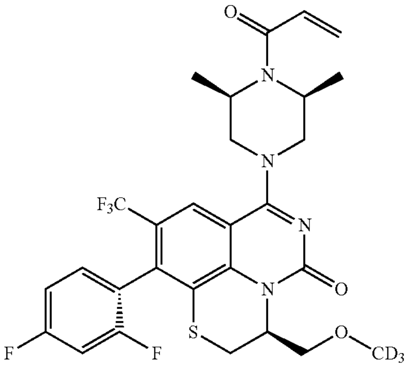 | $^1$H NMR (400 MHz, $CDCl_3$) δ 8.08 (s, 1H), 7.22-7.17 (m, 1H), 7.06-6.93 (m, 2H), 6.64-6.59 (m, 1H), 6.44-6.38 (m, 1H), 5.78 (dd, J = 10.4 Hz, 2.0 Hz, 1H), 5.48-5.45 (m, 1H), 4.66-4.63 (m, 2H), 4.23-4.19 (m, 2H), 3.70-3.60 (m, 2H), 3.40-3.30 (m, 3H), 3.04-2.99 (m, 1H), 1.63-1.61 (m, 3H), 1.47 (d, J = 6.8 Hz, 3H). | 598.2 | 95.1 | (3S,10R)-7-((3S,5R)-4-acryloyl-3,5-dimethylpiperazin-1-yl)-10-(2,4-difluorophenyl)-3-((methoxy-d3)methyl)-9-(trifluoromethyl)-2,3-dihydro-5H-[1,4]thiazino[2,3,4-ij]quinazolin-5-one |
| 1424 | 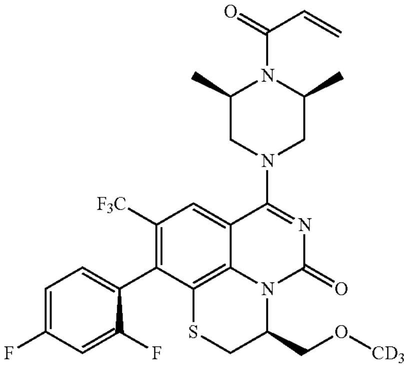 | $^1$H NMR (400 MHz, $CDCl_3$) δ 8.08 (s, 1H), 7.19-7.17 (m, 1H), 7.03-6.94 (m, 2H), 6.64-6.59 (m, 1H), 6.44-6.39 (m, 1H), 5.78 (dd, J = 12.4 Hz, 2.0 Hz, 1H), 5.46-5.43 (m, 1H), 4.76-4.64 (m, 2H), 4.21-4.16 (m, 2H), 3.67-3.65 (m, 2H), 3.40-3.32 (m, 3H), 3.06-3.01 (m, 1H), 1.63-1.61 (m, 3H), 1.52-1.46 (m, 3H). | 598.2 | 95.4 | (3S,10S)-7-((3S,5R)-4-acryloyl-3,5-dimethylpiperazin-1-yl)-10-(2,4-difluorophenyl)-3-((methoxy-d3)methyl)-9-(trifluoromethyl)-2,3-dihydro-5H-[1,4]thiazino[2,3,4-ij]quinazolin-5-one |

TABLE 11-continued

Summary of % CAF at 10 μM after 1 hour for Examples 1300-1455

| Ex. # | Structure | $^1$H NMR | MS $(M + H)^+$ | % CAF 10 uM @ 60 min | Name |
|---|---|---|---|---|---|
| 1425 | 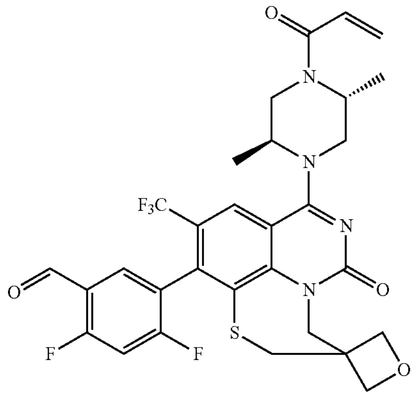 [SMILES: C=CC(=O)N1C[C@H](C)N(c2nc(=O)n3c4c(c(-c5cc(C=O)c(F)cc5F)c(C(F)(F)F)cc24)SCC2(COC2)C3)C[C@H]1C] | $^1$H NMR (400 MHz, MeOH-$d_4$) δ 10.28 (s, 1H), 8.01-7.94 (m, 1H), 7.49 (q, J = 8.4 Hz, 1H), 7.37 (td, J = 9.8, 3.1 Hz, 1H), 7.09 (td, J = 9.8, 2.7 Hz, 1H), 6.90-6.71 (m, 1H), 6.33-6.22 (m, 1H), 5.81 (q, J = 6.8 Hz, 2H), 4.84-4.57 (m, 2H), 4.55-4.36 (m, 3H), 4.35-4.17 (m, 1H), 3.95-3.68 (m, 2H), 3.67-3.35 (m, 4H), 1.45-1.25 (m, 6H). | 635.2 | 69.2 | 5-(8'-((2S,5R)-4-acryloyl-2,5-dimethylpiperazin-1-yl)-6'-oxo-10'-(trifluoromethyl)-2'H,4'H,6'H-spiro[oxetane-3,3'-[1,4]thiazepino[2,3,4-ij]quinazolin]-11'-yl)-2,4-difluorobenzaldehyde |
| 1426 | 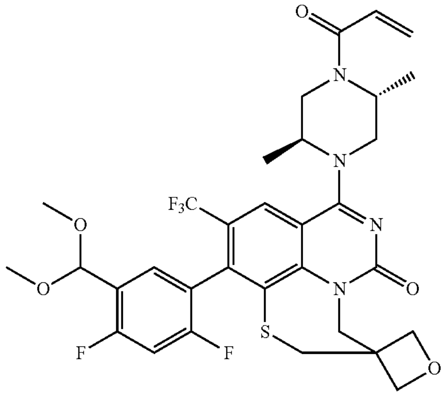 [SMILES: C=CC(=O)N1C[C@H](C)N(c2nc(=O)n3c4c(c(-c5cc(C(OC)OC)c(F)cc5F)c(C(F)(F)F)cc24)SCC2(COC2)C3)C[C@H]1C] | $^1$H NMR (400 MHz, MeOH-$d_4$) δ 7.97 (d, J = 2.5 Hz, 1H), 7.44 (q, J = 8.7 Hz, 1H), 7.13 (td, J = 9.7, 3.0 Hz, 1H), 6.90-6.70 (m, 1H), 6.32-6.22 (m, 1H), 5.85-5.76 (m, 1H), 5.65 (s, 1H), 4.85-4.59 (m, 3H), 4.54-4.15 (m, 3H), 3.95-3.70 (m, 2H), 3.63-3.45 (m, 2H), 3.37 (s, 3H), 3.30 (s, 3H), 1.48-1.27 (m, 6H). | 681.2 | 76 | 8'-((2S,5R)-4-acryloyl-2,5-dimethylpiperazin-1-yl)-11'-(5-(dimethoxymethyl)-2,4-difluorophenyl)-10'-(trifluoromethyl)-2'H,4'H,6'H-spiro[oxetane-3,3'-[1,4]thiazepino[2,3,4-ij]quinazolin]-6'-one |
| 1427 | 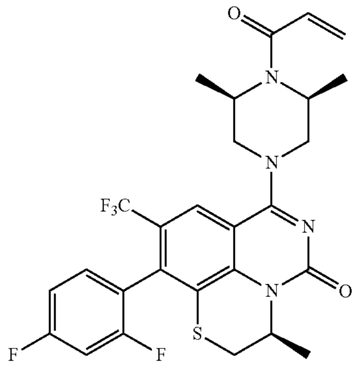 | $^1$H NMR (400 MHz, $CDCl_3$) δ 8.09 (s, 1H), 7.20-7.16 (m, 1H), 7.08-6.95 (m, 2H), 6.66-6.59 (m, 1H), 6.43-6.39 (m, 1H), 5.78 (d, J = 10.4 Hz, 1H), 5.48-5.43 (m, 1H), 4.66-4.57 (m, 2H), 4.19 (t, J = 13.6 Hz, 2H), 3.38-3.29 (m, 2H), 3.21-3.15 (m, 1H), 2.92-2.89 (m, 1H), 1.64 (d, J = 7.2 Hz, 3H), 1.48-1.46 (m, 6H). | 565.2 | 95 | (3S)-7-((3S,5R)-4-acryloyl-3,5-dimethylpiperazin-1-yl)-10-(2,4-difluorophenyl)-3-methyl-9-(trifluoromethyl)-2,3-dihydro-5H-[1,4]thiazino[2,3,4-ij]quinazolin-5-one |

TABLE 11-continued

| Summary of % CAF at 10 μM after 1 hour for Examples 1300-1455 | | | | | |
|---|---|---|---|---|---|
| Ex. # | Structure | $^1$H NMR | MS (M + H)$^+$ | % CAF 10 uM @ 60 min | Name |
| 1428 | 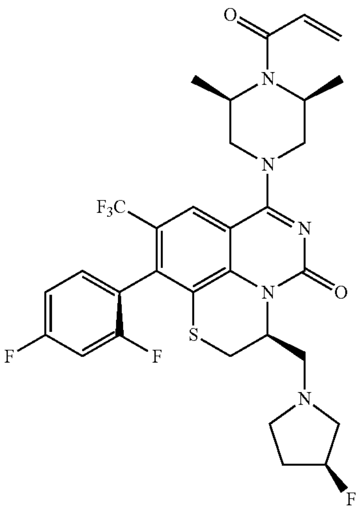 | $^1$H NMR (400 MHz, $CDCl_3$) δ 8.07 (s, 1H), 7.21-7.15 (m, 1H), 7.06-6.94 (m, 2H), 6.66-6.59 (m, 1H), 6.40 (dd, J = 1.6 Hz, J = 16.4 Hz, 1H), 5.77 (dd, J = 2.0 Hz, J = 10.8 Hz, 1H), 5.41-5.37 (m, 1H), 5.21-5.04 (m, 1H), 4.79-4.53 (m, 2H), 4.21-4.17 (m, 2H), 3.47-3.45 (m, 1H), 3.39-3.30 (m, 2H), 3.12-2.97 (m, 4H), 2.91-2.82 (m, 1H), 2.61-2.55 (m, 2H), 2.18-1.96 (m, 2H), 1.61 (m, 3H), 1.48 (d, J = 7.2 Hz, 3H). | 652.3 | 72 | (3S,10S)-7-((3S,5R)-4-acryloyl-3,5-dimethylpiperazin-1-yl)-10-(2,4-difluorophenyl)-3-(((S)-3-fluoropyrrolidin-1-yl)methyl)-9-(trifluoromethyl)-2,3-dihydro-5H-[1,4]thiazino[2,3,4-ij]quinazolin-5-one |
| 1429 | 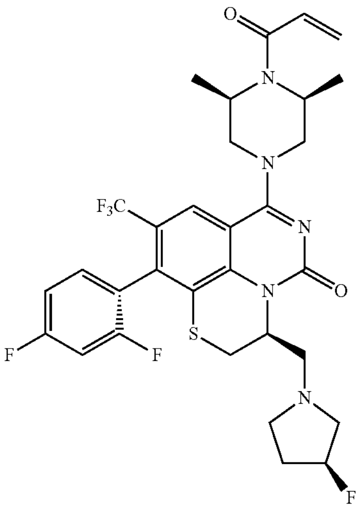 | $^1$H NMR (400 MHz, $CDCl_3$) δ 8.06 (s, 1H), 7.21-7.15 (m, 1H), 7.06-6.94 (m, 2H), 6.66-6.59 (m, 1H), 6.50 (dd, J = 2.0 Hz, J = 16.8 Hz, 1H), 5.77 (dd, J = 2.0 Hz, J = 10.4 Hz, 1H), 5.37-5.33 (m, 1H), 5.21-5.04 (m, 1H), 4.78-4.52 (m, 2H), 4.18 (d, J = 12.8 Hz, 2H), 3.48-3.44 (m, 1H), 3.38-3.30 (m, 2H), 3.12-2.95 (m, 4H), 2.88-2.83 (m, 1H), 2.60-2.58 (m, 2H), 2.17-1.98 (m, 2H), 1.61 (m, 3H), 1.48 (d, J = 7.2 Hz, 3H). | 652.3 | 79 | (3S,10R)-7-((3S,5R)-4-acryloyl-3,5-dimethylpiperazin-1-yl)-10-(2,4-difluorophenyl)-3-(((S)-3-fluoropyrrolidin-1-yl)methyl)-9-(trifluoromethyl)-2,3-dihydro-5H-[1,4]thiazino[2,3,4-ij]quinazolin-5-one |
| 1430 | 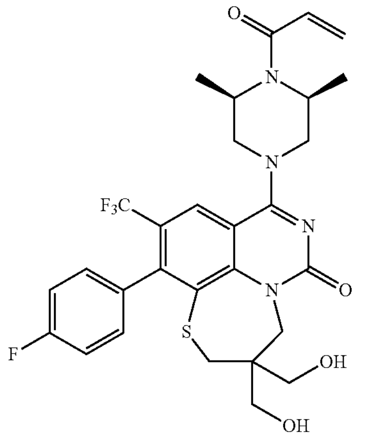 [SMILES: C=CC(=O)N1[C@H](C)CN(c2nc(=O)n3c4c(c(-c5ccc(F)cc5)c(C(F)(F)F)cc24)SCC(CO)(CO)C3)C[C@@H]1C] | $^1$H NMR (400 MHz, $CDCl_3$) δ 8.13 (s, 1H), 7.26-7.13 (m, 4H), 6.63 (dd, J = 10.8 Hz, 16.8 Hz, 1H), 6.45-6.38 (m, 1H), 5.78 (d, J = 11.2 Hz, 1H), 4.84-4.53 (m, 4H), 4.39-4.32 (m, 1H), 4.25-4.11 (m, 2H), 3.82-3.74 (m, 1H), 3.69-3.58 (m, 2H), 3.55-3.36 (m, 3H), 2.84 (brs, 1H), 2.75-2.69 (m, 1H), 2.64-2.58 (m, 1H), 1.65 (d, J = 7.2 Hz, 3H), 1.47 (d, J = 6.8 Hz, 3H). | 607.3 | 93 | 8-((3S,5R)-4-acryloyl-3,5-dimethylpiperazin-1-yl)-11-(4-fluorophenyl)-3,3-bis(hydroxymethyl)-10-(trifluoromethyl)-3,4-dihydro-2H,6H-[1,4]thiazepino[2,3,4-ij]quinazolin-6-one |

TABLE 11-continued

Summary of % CAF at 10 μM after 1 hour for Examples 1300-1455

| Ex. # | Structure | $^1$H NMR | MS (M + H)$^+$ | % CAF 10 uM @ 60 min | Name |
|---|---|---|---|---|---|
| 1431 | 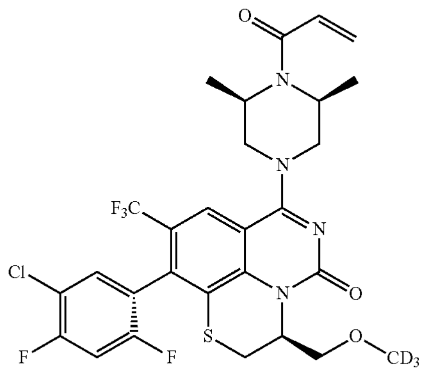 | $^1$H NMR (400 MHz, $CDCl_3$) δ 8.06 (s, 1H), 7.28-7.24 (m, 1H), 7.07 (t, J = 8.8 Hz, 1H), 6.65-6.59 (m, 1H), 6.43-6.38 (m, 1H), 5.78 (dd, J = 10.4 Hz, 1.6 Hz, 1H), 5.46-5.43 (m, 1H), 4.73-4.58 (m, 2H), 4.21-4.16 (m, 2H), 3.69-3.63 (m, 2H), 3.40-3.31 (m, 3H), 3.05-3.01 (m, 1H), 1.61 (d, J = 6.8 Hz, 3H), 1.48 (d, J = 6.8 Hz, 3H). | 632.3 | 96 | (3S,10R)-7-((3S,5R)-4-acryloyl-3,5-dimethylpiperazin-1-yl)-10-(2,4-difluoro-5-methylphenyl)-3-((methoxy-d3)methyl)-9-(trifluoromethyl)-2,3-dihydro-5H-[1,4]thiazino[2,3,4-ij]quinazolin-5-one |
| 1432 | 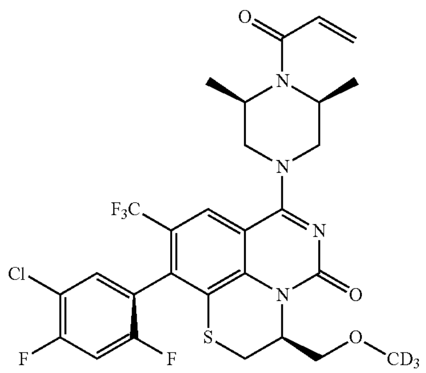 | $^1$H NMR (400 MHz, $CDCl_3$) δ 8.06 (s, 1H), 7.28-7.25 (m, 1H), 7.07 (t, J = 8.8 Hz, 1H), 6.65-6.59 (m, 1H), 6.43-6.38 (m, 1H), 5.78 (dd, J = 10.4 Hz, 1.6 Hz, 1H), 5.48-5.45 (m, 1H), 4.80-4.43 (m, 2H), 4.21-4.16 (m, 2H), 3.67-3.59 (m, 2H), 3.41-3.30 (m, 3H), 3.04-3.00 (m, 1H), 1.52-1.61 (m, 3H), 1.46 (d, J = 6.8 Hz, 3H). | 632.3 | 55 | (3S,10S)-7-((3S,5R)-4-acryloyl-3,5-dimethylpiperazin-1-yl)-10-(2,4-difluoro-5-methylphenyl)-3-((methoxy-d3)methyl)-9-(trifluoromethyl)-2,3-dihydro-5H-[1,4]thiazino[2,3,4-ij]quinazolin-5-one |
| 1433 | 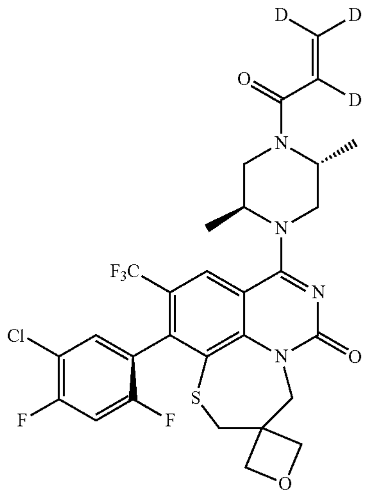 | $^1$H NMR (400 MHz, $CDCl_3$) δ 7.82 (s, 1H), 7.25-7.21 (m, 1H), 7.06 (t, J = 8.8 Hz, 1H), 5.05-4.63 (m, 5H), 4.36 (d, J = 5.6 Hz, 3H), 3.89-3.64 (m, 4H), 3.43-3.27 (m, 5H), 2.55-2.42 (m, 1H), 1.39-1.16 (m, 9H). | 644.2 | 70 | (S)-8'-((2S,5R)-4-(Acryloyl-$d_3$)-2,5-dimethylpiperazin-1-yl)-11'-(5-chloro-2,4-difluorophenyl)-10'-(trifluoromethyl)-2'H,4'H,6'H-spiro[oxetane-3,3'-[1,4]thiazepino[2,3,4-ij]quinazolin]-6'-one |

TABLE 11-continued

Summary of % CAF at 10 μM after 1 hour for Examples 1300-1455

| Ex. # | Structure | $^1$H NMR | MS (M + H)$^+$ | % CAF 10 uM @ 60 min | Name |
|---|---|---|---|---|---|
| 1434 | 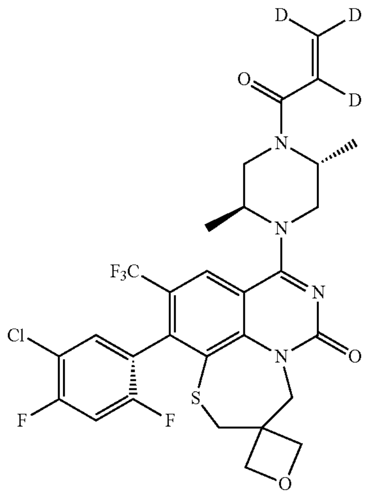 | $^1$H NMR (400 MHz, $CDCl_3$) δ 7.83 (s, 1H), 7.28-7.25 (m, 1H), 7.05 (t, J = 8.8 Hz, 1H), 5.08-4.62 (m, 5H), 4.36 (d, J = 6.4 Hz, 3H), 3.93-3.59 (m, 4H), 3.45-3.32 (m, 5H), 2.57-2.44 (m, 1H), 1.40-1.25 (m, 9H). | 644.2 | 82 | (R)-8'-((2S,5R)-4-(Acryloyl-$d_3$)-2,5-dimethylpiperazin-1-yl)-11'-(5-chloro-2,4-difluorophenyl)-10'-(trifluoromethyl)-2'H,4'H,6'H-spiro[oxetane-3,3'-[1,4]thiazepino[2,3,4-ij]quinazolin]-6'-one |
| 1435 | 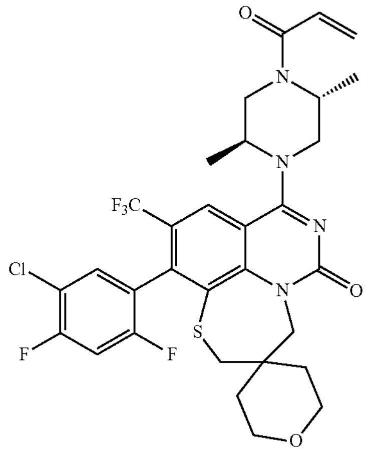 [SMILES: C=CC(=O)N1C[C@H](C)N(c2nc(=O)n3c4c(c(-c5cc(Cl)c(F)cc5F)c(C(F)(F)F)cc24)SCC2(CCOCC2)C3)C[C@H]1C] | $^1$H NMR (400 MHz, MeOH-$d_4$) δ 8.08-7.83 (m, 1H), 7.67-7.22 (m, 2H), 6.96-6.68 (m, 1H), 6.28 (dd, J = 16.6, 4.9 Hz, 1H), 5.81 (t, J = 8.9 Hz, 1H), 5.12-4.93 (m, 1H), 4.85-4.14 (m, 4H), 4.14-3.46 (m, 7H), 3.30-3.13 (m, 1H), 3.04-2.81 (m, 1H), 1.90-1.64 (m, 2H), 1.63-1.31 (m, 6H). | 669.2 | 84 | 8'-((2S,5R)-4-acryloyl-2,5-dimethylpiperazin-1-yl)-11'-(5-chloro-2,4-difluorophenyl)-10'-(trifluoromethyl)-2,3,5,6-tetrahydro-2'H,4'H,6'H-spiro[pyran-4,3'-[1,4]thiazepino[2,3,4-ij]quinazolin]-6'-one |
| 1436 | 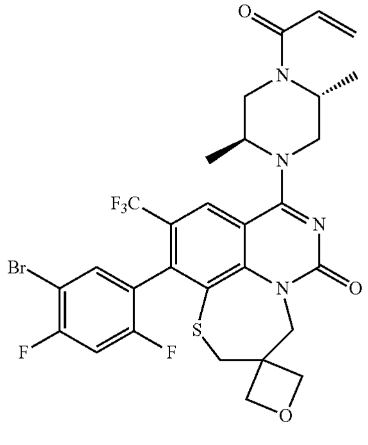 [SMILES: C=CC(=O)N1C[C@H](C)N(c2nc(=O)n3c4c(c(-c5cc(Br)c(F)cc5F)c(C(F)(F)F)cc24)SCC2(COC2)C3)C[C@H]1C] | | 685.0 | 81 | 8'-((2S,5R)-4-acryloyl-2,5-dimethylpiperazin-1-yl)-11'-(5-bromo-2,4-difluorophenyl)-10'-(trifluoromethyl)-2'H,4'H,6'H-spiro[oxetane-3,3'-[1,4]thiazepino[2,3,4-ij]quinazolin]-6'-one |

TABLE 11-continued

| Ex. # | Structure | $^1$H NMR | MS (M + H)+ | % CAF 10 uM @ 60 min | Name |
|---|---|---|---|---|---|
| Summary of % CAF at 10 μM after 1 hour for Examples 1300-1455 | | | | | |
| 1437 | 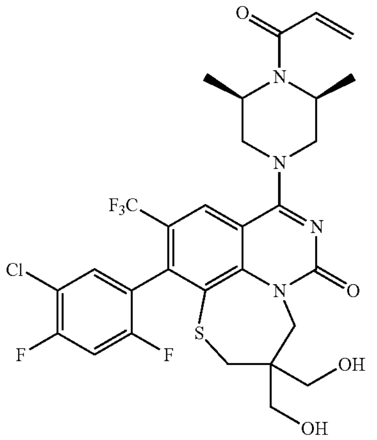 [SMILES: C=CC(=O)N1[C@H](C)CN(c2nc(=O)n3c4c(c(-c5cc(Cl)c(F)cc5F)c(C(F)(F)F)cc24)SCC(CO)(CO)C3)C[C@@H]1C] | $^1$H NMR (400 MHz, $CDCl_3$) δ 8.17-8.15 (m, 1H), 7.30-7.21 (m, 1H), 7.08-7.03 (m, 1H), 6.62 (dd, J = 16.8 Hz, 10.4 Hz, 1H), 6.44-6.40 (m, 1H), 5.79 (d, J = 10.4 Hz, 1H), 4.75-4.58 (m, 4H), 4.38-4.32 (m, 1H), 4.23-4.13 (m, 2H), 3.82-3.78 (m, 1H), 3.67-3.61 (m, 2H), 3.54-3.39 (m, 3H), 2.83-2.69 (m, 3H), 1.65-1.62 (m, 3H), 1.49-1.46 (m, 3H). | 659.3 | 87 | 8-((3S,5R)-4-acryloyl-3,5-dimethylpiperazin-1-yl)-11-(5-chloro-2,4-difluorophenyl)-3,3-bis(hydroxymethyl)-10-(trifluoromethyl)-3,4-dihydro-2H,6H-[1,4]thiazepino[2,3,4-ij]quinazolin-6-one |
| 1438 | 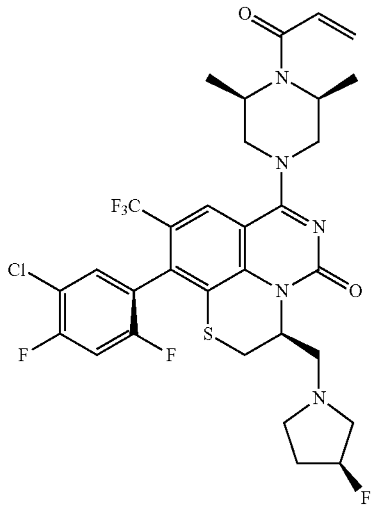 | $^1$H NMR (400 MHz, $CDCl_3$) δ 8.06 (s, 1H), 7.28-7.27 (m, 1H), 7.07 (t, J = 8.8 Hz, 1H), 6.65-6.59 (m, 1H), 6.40 (dd, J = 2.0 Hz, J = 16.8 Hz, 1H), 5.77 (dd, J = 2.0 Hz, J = 10.4 Hz, 1H), 5.40-5.37 (m, 1H), 5.20-5.06 (m, 1H), 4.79-4.56 (m, 2H), 4.20-4.17 (m, 2H), 3.50-3.46 (m, 1H), 3.40-3.30 (m, 2H) 3.10-2.96 (m, 4H), 2.92-2.78 (m, 1H), 2.66-2.47 (m, 2H), 2.18-1.98 (m, 2H), 1.60 (d, J = 7.2 Hz, 3H), 1.47 (d, J = 6.8 Hz, 3H). | 686.2 | 54 | (3S,10S)-7-((3S,5R)-4-acryloyl-3,5-dimethylpiperazin-1-yl)-10-(5-chloro-2,4-difluorophenyl)-3-(((S)-3-fluoropyrrolidin-1-yl)methyl)-9-(trifluoromethyl)-2,3-dihydro-5H-[1,4]thiazino[2,3,4-ij]quinazolin-5-one |
| 1439 | 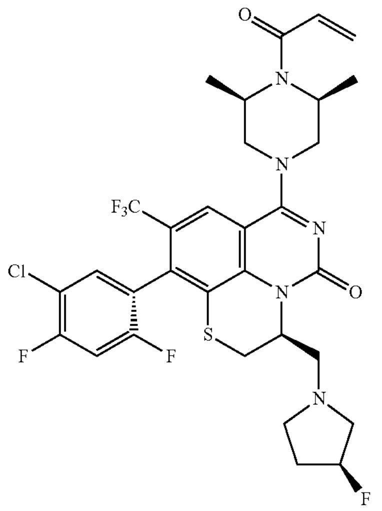 | $^1$H NMR (400 MHz, $CDCl_3$) δ 8.06 (s, 1H), 7.29-7.27 (m, 1H), 7.07 (t, J = 8.8 Hz, 1H), 6.65-6.59 (m, 1H), 6.40 (dd, J = 2.0 Hz, J = 16.8 Hz, 1H), 5.77 (dd, J = 2.0 Hz, J = 10.4 Hz, 1H), 5.41-5.34 (m, 1H), 5.20-5.06 (m, 1H), 4.80-4.52 (m, 2H), 4.20-4.16 (m, 2H), 3.50-3.47 (m, 1H), 3.38-3.30 (m, 2H), 3.13-3.00 (m, 4H), 2.95-2.84 (m, 1H), 2.60-2.58 (m, 2H), 2.17-1.99 (m, 2H), 1.60 (d, J = 6.8 Hz, 3H), 1.48 (d, J = 6.8 Hz, 3H). | 686.2 | 73 | (3S,10R)-7-((3S,5R)-4-acryloyl-3,5-dimethylpiperazin-1-yl)-10-(5-chloro-2,4-difluorophenyl)-3-(((S)-3-fluoropyrrolidin-1-yl)methyl)-9-(trifluoromethyl)-2,3-dihydro-5H-[1,4]thiazino[2,3,4-ij]quinazolin-5-one |

TABLE 11-continued

Summary of % CAF at 10 μM after 1 hour for Examples 1300-1455

| Ex. # | Structure | $^1$H NMR | MS (M + H)$^+$ | % CAF 10 uM @ 60 min | Name |
|---|---|---|---|---|---|
| 1440 | 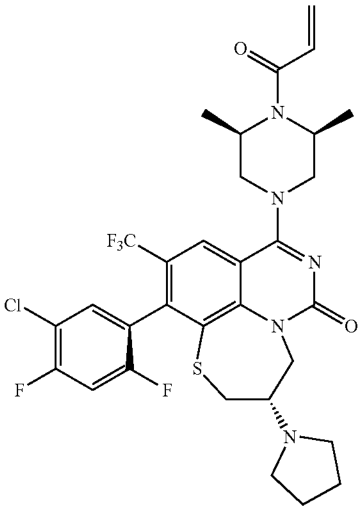 | $^1$H NMR (400 MHz, $CDCl_3$) δ 8.06 (s, 1H), 7.28-7.25 (m, 1H), 7.03 (t, J = 8.8 Hz, 1H), 6.66-6.59 (m, 1H), 6.40 (dd, J = 2.0 Hz, J = 16.4 Hz, 1H), 5.76 (dd, J = 2.0 Hz, J = 10.4 Hz, 1H), 4.80-4.52 (m, 4H), 4.17-4.14 (m, 2H), 3.34-3.08 (m, 5H), 2.73-2.72 (m, 4H), 1.91-1.73 (m, 4H), 1.57-1.48 (m, 6H). | 668.3 | 51 | (3S,11S)-8-((3S,5R)-4-acryloyl-3,5-dimethylpiperazin-1-yl)-11-(5-chloro-2,4-difluorophenyl)-3-(pyrrolidin-1-yl) 10-(trifluoromethyl)-3,4-dihydro-[1,4]thiazepino[2,3,4-ij]quinazolin-6-one |
| 1441 | 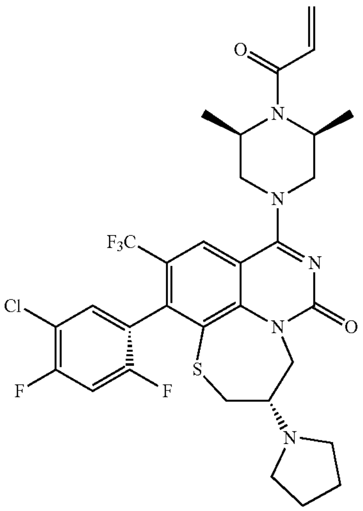 | $^1$H NMR (400 MHz, $CDCl_3$) δ 8.06 (s, 1H), 7.26-7.24 (m, 1H), 7.04 (t, J = 8.8 Hz, 1H), 6.66-6.59 (m, 1H), 6.40 (d, J = 16.0 Hz, 1H), 5.76 (d, J = 20 Hz, 1H), 4.89-4.45 (m, 4H), 4.14-4.13 (m, 2H), 3.42-3.15 (m, 5H), 2.86-2.53 (m, 4H), 1.90-1.73 (m, 4H), 1.55-1.43 (m, 6H). | 668.3 | 79 | (3S,11R)-8-((3S,5R)-4-acryloyl-3,5-dimethylpiperazin-1-yl)-11-(5-chloro-2,4-difluorophenyl)-3-(pyrrolidin-1-yl) 10-(trifluoromethyl)-3,4-dihydro-2H,6H-[1,4]thiazepino[2,3,4-ij]quinazolin-6-one |
| 1442 | 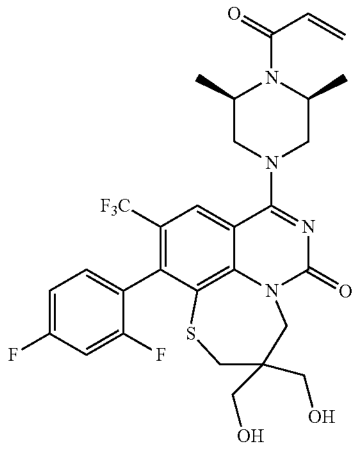 [SMILES: C=CC(=O)N1[C@H](C)CN(c2nc(=O)n3c4c(c(-c5ccc(F)cc5F)c(C(F)(F)F)cc24)SCC(CO)(CO)C3)C[C@@H]1C] | $^1$H NMR (400 MHz, $CDCl_3$) δ 8.16-8.14 (m, 1H), 7.22-7.12 (m, 1H), 7.06-6.92 (m, 2H), 6.66-6.60 (m, 1H), 6.44-6.40 (m, 1H), 5.81-5.78 (m, 1H), 4.76-4.70 (m, 1H), 4.66-4.63 (m, 1H), 4.39-4.34 (m, 1H), 4.24-4.14 (m, 2H), 3.80-3.76 (m, 1H), 3.67-3.60 (m, 2H), 3.54-3.39 (m, 3H), 2.90-2.65 (m, 3H), 1.65-1.63 (m, 3H), 1.49-1.46 (m, 3H). | 625.2 | 93 | 8-((3S,5R)-4-acryloyl-3,5-dimethylpiperazin-1-yl)-11-(2,4-difluorophenyl)-3,3-bis(hydroxymethyl)-10-(trifluoromethyl)-3,4-dihydro-2H,6H-[1,4]thiazepino[2,3,4-ij]quinazolin-6-one |

TABLE 11-continued

| Summary of % CAF at 10 μM after 1 hour for Examples 1300-1455 | | | | | |
|---|---|---|---|---|---|
| Ex. # | Structure | $^1$H NMR | MS (M + H)$^+$ | % CAF 10 uM @ 60 min | Name |
| 1443 | 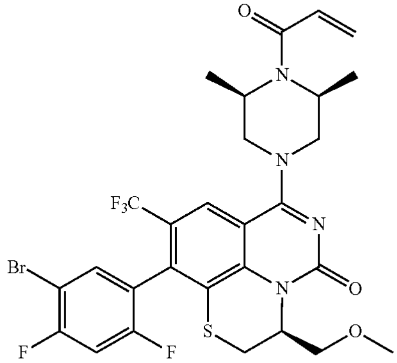 [SMILES: C=CC(=O)N1[C@H](C)CN(c2nc(=O)n3c4c(c(-c5cc(Br)c(F)cc5F)c(C(F)(F)F)cc24)SC[C@@H]3COC)C[C@@H]1C] | | 673.2 | 85 | (3S)-7-((3S,5R)-4-acryloyl-3,5-dimethylpiperazin-1-yl)-10-(5-bromo-2,4-difluorophenyl)-3-(methoxymethyl)-9-(trifluoromethyl)-2,3-dihydro-5H-[1,4]thiazino[2,3,4-ij]quinazolin-5-one |
| 1444 | 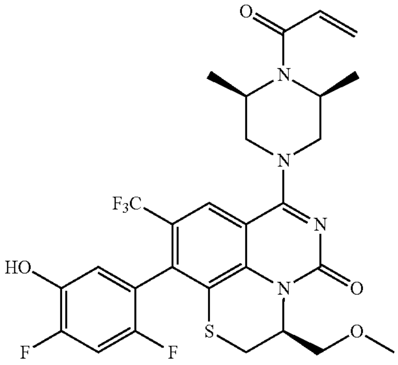 [SMILES: C=CC(=O)N1[C@H](C)CN(c2nc(=O)n3c4c(c(-c5cc(O)c(F)cc5F)c(C(F)(F)F)cc24)SC[C@@H]3COC)C[C@@H]1C] | $^1$H NMR and NOESY analysis: $^1$H NMR (400 MHz, MeOH-d$_4$) δ 8.13 (s, 1H), 7.08 (t, J = 10.0 Hz, 1H), 6.90-6.72 (m, 2H), 6.29 (dd, J = 16.6, 2.0 Hz, 1H), 5.80 (dd, J = 10.5, 2.0 Hz, 1H), 5.41-5.28 (m, 1H), 4.83-4.50 (m, 2H), 4.33 (d, J = 13.8 Hz, 1H), 4.25 (d, J = 13.6 Hz, 1H), 3.73 (t, J = 9.2 Hz, 1H), 3.61 (dd, J = 9.2, 4.7 Hz, 1H), 3.48 (dd, J = 13.5, 4.8 Hz, 1H), 3.44-3.33 (m, 2H), 3.40 (s, 3H), 3.13 (dd, J = 13.8, 2.9 Hz, 1H), 1.58 (d, J = 6.9 Hz, 3H), 1.42 (d, J = 6.9 Hz, 3H); | 611.2 | 90 | (3S)-7-((3S,5R)-4-acryloyl-3,5-dimethylpiperazin-1-yl)-10-(2,4-difluoro-5-hydroxyphenyl)-3-(methoxymethyl)-9-(trifluoromethyl)-2,3-dihydro-5H-[1,4]thiazino[2,3,4-ij]quinazolin-5-one |
| 1445 | 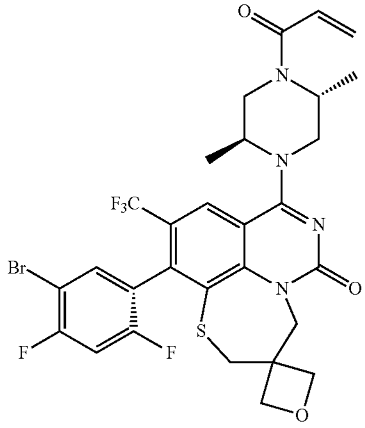 | $^1$H NMR (400 MHz, MeOH-d$_4$) δ 7.97 (d, J = 2.9 Hz, 1H), 7.64 (t, J = 7.5 Hz, 1H), 7.31 (t, J = 8.9 Hz, 1H), 6.81 (ddd, J = 30.6, 16.7, 10.6 Hz, 1H), 6.28 (ddd, J = 16.7, 5.6, 1.9 Hz, 1H), 5.81 (ddd, J = 10.2, 7.7, 1.9 Hz, 1H), 4.86-4.60 (m, 3H), 4.55-4.46 (m, 1H), 4.45 (dd, J = 6.4, 2.6 Hz, 2H), 4.39-4.15 (m, 1H), 3.96-3.33 (m, 6H), 1.49-1.30 (m, 6H); | 685.0 | 95 | (R)-8'-((2S,5R)-4-Acryloyl-2,5-dimethylpiperazin-1-yl)-11'-(5-bromo-2,4-difluorophenyl)-10'-(trifluoromethyl)-2'H,4'H,6'H-spiro[oxetane-3,3'-[1,4]thiazepino[2,3,4-ij]quinazolin]-6'-one |

TABLE 11-continued

Summary of % CAF at 10 μM after 1 hour for Examples 1300-1455

| Ex. # | Structure | $^1$H NMR | MS (M + H)$^+$ | % CAF 10 uM @ 60 min | Name |
|---|---|---|---|---|---|
| 1446 | 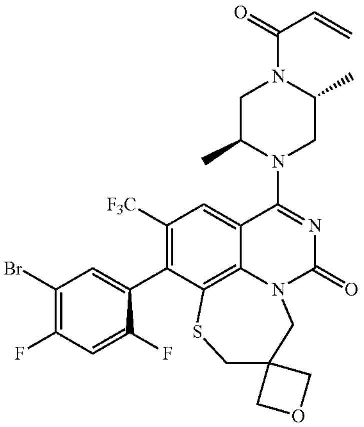 | $^1$H NMR (400 MHz, MeOH-d$_4$) δ 7.96 (s, 1H), 7.69-7.53 (m, 1H), 7.32 (t, J = 9.0 Hz, 1H), 6.81 (ddd, J = 21.5, 16.7, 10.7 Hz, 1H), 6.28 (ddd, J = 16.7, 7.5, 2.0 Hz, 1H), 5.81 (ddd, J = 10.7, 6.6, 1.9 Hz, 1H), 4.87-4.59 (m, 3H), 4.55-4.46 (m, 1H), 4.45 (d, J = 6.4 Hz, 2H), 4.33-4.15 (m, 1H), 3.97-3.72 (m, 2H), 3.69-3.44 (m, 3H), 1.47-1.30 (m, 6H); | 685.0 | 45 | (S)-8'-((2S,5R)-4-Acryloyl-2,5-dimethylpiperazin-1-yl)-11'-(5-bromo-2,4-difluorophenyl)-10'-(trifluoromethyl)-2'H,4'H,6'H-spiro[oxetane-3,3'-[1,4]thiazepino[2,3,4-ij]quinazolin]-6'-one |
| 1447 | 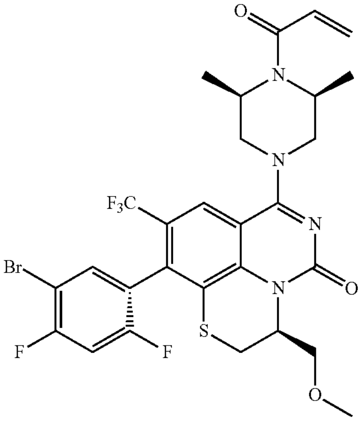 | $^1$H NMR (400 MHz, MeOH-d$_4$) δ 8.15 (s, 1H), 7.60 (t, J = 7.5 Hz, 1H), 7.35 (t, J = 8.9 Hz, 1H), 6.84 (dd, J = 16.7, 10.6 Hz, 1H), 6.29 (dd, J = 16.7, 2.0 Hz, 1H), 5.80 (dd, J = 10.6, 2.0 Hz, 1H), 5.43-5.32 (m, 1H), 4.86-4.52 (m, 2H), 4.35 (d, J = 13.6 Hz, 1H), 4.26 (d, J = 13.6 Hz, 1H), 3.69 (t, J = 9.1 Hz, 1H), 3.60 (dd, J = 9.2, 4.9 Hz, 1H), 3.52 (dd, J = 13.6, 4.7 Hz, 1H), 3.47-3.35 (m, 2H), 3.39 (s, 3H), 3.17 (dd, J = 13.7, 3.0 Hz, 1H), 1.56 (d, J = 6.9 Hz, 3H), 1.42 (d, J = 6.9 Hz, 3H). | 673.2 | 97 | (3S,10R)-7-((3S,5R)-4-Acryloyl-3,5-dimethylpiperazin-1-yl)-10-(5-bromo-2,4-difluorophenyl)-3-(methoxymethyl)-9-(trifluoromethyl)-2,3-dihydro-5H-[1,4]thiazino[2,3,4-ij]quinazolin-5-one |
| 1448 | 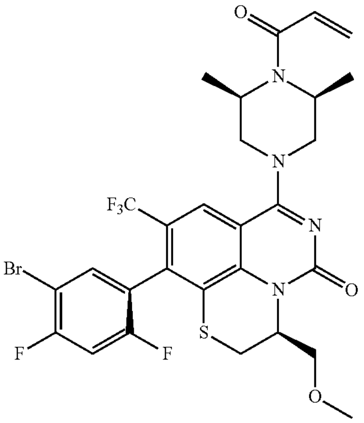 | $^1$H NMR (400 MHz, MeOH-d$_4$) δ 8.15 (s, 1H), 7.66 (t, J = 7.4 Hz, 1H), 7.34 (t, J = 9.0 Hz, 1H), 6.84 (dd, J = 16.7, 10.6 Hz, 1H), 6.29 (dd, J = 16.7, 2.0 Hz, 1H), 5.80 (dd, J = 10.6, 2.0 Hz, 1H), 5.41-5.31 (m, 1H), 4.86-4.51 (m, 2H), 4.33 (d, J = 13.7 Hz, 1H), 4.26 (d, J = 13.4 Hz, 1H), 3.75 (t, J = 9.2 Hz, 1H), 3.62 (dd, J = 9.2, 4.8 Hz, 1H), 3.49 (dd, J = 13.5, 4.7 Hz, 1H), 3.45-3.36 (m, 2H), 3.40 (s, 3H), 3.15 (dd, J = 13.7, 2.9 Hz, 1H), 1.57 (d, J = 7.1 Hz, 3H), 1.42 (d, J = 7.0 Hz, 3H). | 673.2 | 95 | (3S,10S)-7-((3S,5R)-4-Acryloyl-3,5-dimethylpiperazin-1-yl)-10-(5-bromo-2,4-difluorophenyl)-3-(methoxymethyl)-9-(trifluoromethyl)-2,3-dihydro-5H-[1,4]thiazino[2,3,4-ij]quinazolin-5-one |

TABLE 11-continued

| Ex. # | Structure | $^1$H NMR | MS $(M + H)^+$ | % CAF 10 uM @ 60 min | Name |
|---|---|---|---|---|---|
| Summary of % CAF at 10 μM after 1 hour for Examples 1300-1455 | | | | | |
| 1449 | 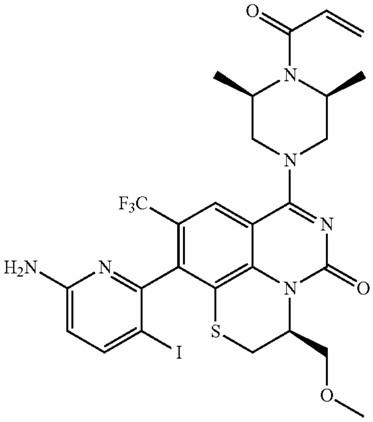 [SMILES: C=CC(=O)N1[C@H](C)CN(c2nc(=O)n3c4c(c(-c5nc(N)ccc5I)c(C(F)(F)F)cc24)SC[C@@H]3COC)C[C@@H]1C] | $^1$H NMR (400 MHz, $CDCl_3$) δ 8.03-8.01 (m, 2H), 6.65-6.58 (m, 1H), 6.49-6.38 (m, 2H), 5.79-5.75 (m, 1H), 5.41-5.38 (m, 1H), 5.08 (s, 2H), 4.77-4.45 (m, 2H), 4.18-4.15 (m, 2H), 3.76-3.64 (m, 2H), 3.40-3.28 (m, 6H), 2.99-2.90 (m, 1H), 1.50-1.42 (m, 6H). | 701.1 | 94 | (3S)-7-((3S,5R)-4-acryloyl-3,5-dimethylpiperazin-1-yl)-10-(6-amino-3-iodopyridin-2-yl)-3-(methoxymethyl)-9-(trifluoromethyl)-2,3-dihydro-5H-[1,4]thiazino[2,3,4-ij]quinazolin-5-one |
| 1450 | 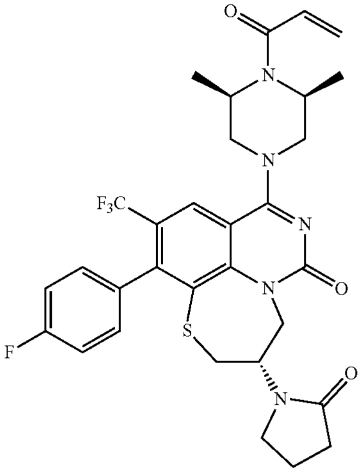 [SMILES: C=CC(=O)N1[C@H](C)CN(c2nc(=O)n3c4c(c(-c5ccc(F)cc5)c(C(F)(F)F)cc24)SC[C@@H](N2CCCC2=O)C3)C[C@@H]1C] | $^1$H NMR (400 MHz, $CDCl_3$) δ 8.08 (s, 1H), 7.22-7.18 (m, 4H), 6.66-6.59 (m, 1H), 6.41 (d, J = 16.8 Hz, 1H), 5.78 (d, J = 10.8 Hz, 1H), 5.06-4.87 (m, 1H), 4.87-4.50 (m, 4H), 4.17 (t, J = 14.8 Hz, 2H), 3.57-2.90 (m, 6H), 2.41-2.33 (m, 2H), 2.14-1.90 (m, 2H), 1.56-1.52 (m, 6H). | 630.3 | 96 | (S)-8-((3S,5R)-4-acryloyl-3,5-dimethylpiperazin-1-yl)-11-(4-fluorophenyl)-3-(2-oxopyrrolidin-1-yl)-10-(trifluoromethyl)-3,4-dihydro-2H,6H-[1,4]thiazepino[2,3,4-ij]quinazolin-6-one |
| 1451 | 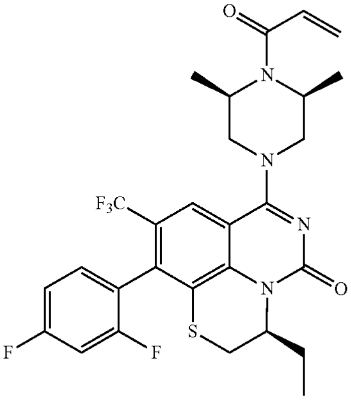 [SMILES: C=CC(=O)N1[C@H](C)CN(c2nc(=O)n3c4c(c(-c5ccc(F)cc5F)c(C(F)(F)F)cc24)SC[C@@H]3CC)C[C@@H]1C] | $^1$H NMR (400 MHz, $CDCl_3$) δ 8.13-8.07 (m, 1H), 7.19 (q, J = 8.4 Hz, 1H), 7.08-6.93 (m, 2H), 6.64 (dd, J = 16.8 Hz, 10.8 Hz, 1H), 6.41 (dd, J = 16.8 Hz, 1.6 Hz, 1H), 5.78 (dd, J = 10.8 Hz, 1.6 Hz, 1H), 5.29-5.18 (m, 1H), 4.92-4.42 (m, 2H), 4.27-4.12 (m, 2H), 3.40-3.24 (m, 2H), 3.15-3.02 (m, 2H), 1.95-1.78 (m, 2H), 1.63 (d, J = 7.2 Hz, 3H), 1.49 (d, J = 7.2 Hz, 3H), 0.97 (t, J = 7.2 Hz, 3H). | 579 | 95 | (3S)-7-((3S,5R)-4-acryloyl-3,5-dimethylpiperazin-1-yl)-10-(2,4-difluorophenyl)-3-ethyl-9-(trifluoromethyl)-2,3-dihydro-5H-[1,4]thiazino[2,3,4-ij]quinazolin-5-one |

TABLE 11-continued

| Summary of % CAF at 10 μM after 1 hour for Examples 1300-1455 | | | | | |
|---|---|---|---|---|---|
| Ex. # | Structure | $^1$H NMR | MS $(M + H)^+$ | % CAF 10 uM @ 60 min | Name |
| 1452 | 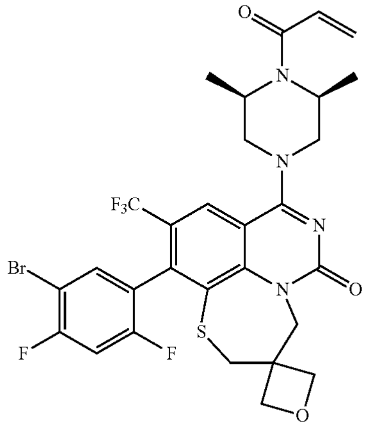 [SMILES: C=CC(=O)N1[C@H](C)CN(c2nc(=O)n3c4c(c(-c5cc(Br)c(F)cc5F)c(C(F)(F)F)cc24)SCC2(COC2)C3)C[C@@H]1C] | $^1$H NMR (400 MHz, MeOH-$d_4$) δ 8.16 (s, 1H), 7.62 (t, J = 7.6 Hz, 1H), 7.31 (t, J = 8.9 Hz, 1H), 6.83 (dd, J = 16.7, 10.6 Hz, 1H), 6.29 (dd, J = 16.7, 2.0 Hz, 1H), 5.80 (dd, J = 10.6, 2.0 Hz, 1H), 5.18-4.92 (m, 1H), 4.88-4.51 (m, 4H), 4.44 (dd, J = 6.4, 3.0 Hz, 2H), 4.25 (d, J = 13.5 Hz, 2H), 3.65-3.50 (m, 2H), 3.49-3.33 (m, 3H), 1.50 (dd, J = 19.2, 6.8 Hz, 6H). | 685 | 97 | 8'-((3S,5R)-4-acryloyl-3,5-dimethylpiperazin-1-yl)-11'-(5-bromo-2,4-difluorophenyl)-10'-(trifluoromethyl)-2'H,4'H,6'H-spiro[oxetane-3,3'-[1,4]thiazepino[2,3,4-ij]quinazolin]-6'-one |
| 1453 | 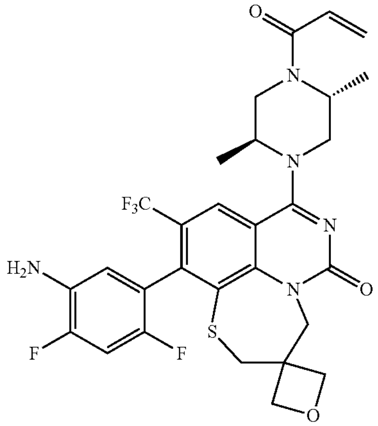 [SMILES: C=CC(=O)N1C[C@H](C)N(c2nc(=O)n3c4c(c(-c5cc(N)c(F)cc5F)c(C(F)(F)F)cc24)SCC2(COC2)C3)C[C@H]1C] | $^1$H NMR (400 MHz, MeOH-$d_4$) δ 7.94 (s, 1H), 6.95 (ddd, J = 11.5, 9.1, 2.8 Hz, 1H), 6.90-6.73 (m, 1H), 6.69 (q, J = 10.2, 9.6 Hz, 1H), 6.28 (dd, J = 16.9, 5.8 Hz, 1H), 5.87-5.74 (m, 1H), 4.86-4.57 (m, 3H), 4.56-3.98 (m, 5H), 3.97-3.37 (m, 5H), 1.54-1.22 (m, 6H). | 622.1 | 95 | 8'-((3S,5R)-4-acryloyl-3,5-dimethylpiperazin-1-yl)-11'-(5-amino-2,4-difluorophenyl)-10'-(trifluoromethyl)-2'H,4'H,6'H-spiro[oxetane-3,3'-[1,4]thiazepino[2,3,4-ij]quinazolin]-6'-one |

TABLE 11-continued

| Summary of % CAF at 10 μM after 1 hour for Examples 1300-1455 | | | | | |
|---|---|---|---|---|---|
| Ex. # | Structure | $^1$H NMR | MS (M + H)$^+$ | % CAF 10 uM @ 60 min | Name |
| 1454 | 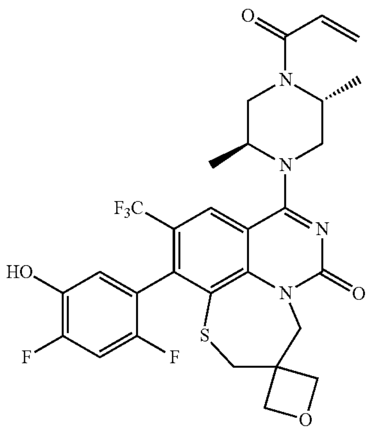 [SMILES: C=CC(=O)N1C[C@H](C)N(c2nc(=O)n3c4c(c(-c5cc(O)c(F)cc5F)c(C(F)(F)F)cc24)SCC2(COC2)C3)C[C@H]1C] | $^1$H NMR (400 MHz, MeOH-$d_4$) δ 7.95 (s, 1H), 7.04 (ddd, J = 11.4, 9.1, 3.0 Hz, 1H), 6.90-6.68 (m, 2H), 6.34-6.20 (m, 1H), 5.80 (ddd, J = 9.8, 7.2, 1.9 Hz, 1H), 4.87-4.56 (m, 4H), 4.55-4.38 (m, 3H), 4.37-3.96 (m, 2H), 3.95-3.36 (m, 5H), 1.53-1.19 (m, 6H). | 623.1 | 92 | 8'-((2S,5R)-4-acryloyl-2,5-dimethylpiperazin-1-yl)-11'-(2,4-difluoro-5-hydroxyphenyl)-10'-(trifluoromethyl)-2'H,4'H,6'H-spiro[oxetane-3,3'-[1,4]thiazepino[2,3,4-ij]quinazolin]-6'-one |
| 1455 | 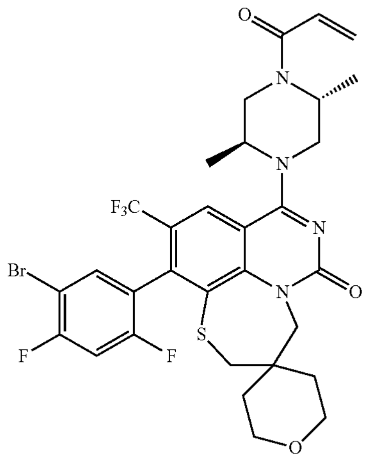 [SMILES: C=CC(=O)N1C[C@H](C)N(c2nc(=O)n3c4c(c(-c5cc(Br)c(F)cc5F)c(C(F)(F)F)cc24)SCC2(CCOCC2)C3)C[C@H]1C] | $^1$H NMR (400 MHz, MeOH-$d_4$) δ 8.52 (br s, 0.5H), 8.05-7.84 (m, 1H), 7.77-7.64 (m, 0.5H), 7.40-7.22 (m, 1H), 6.94-6.68 (m, 1H), 6.28 (dd, J = 16.7, 6.2 Hz, 1H), 5.81 (dd, J = 10.7, 7.3 Hz, 1H), 5.11-5.00 (m, 1H), 4.71-3.50 (m, 12H), 3.04-2.84 (m, 1H), 1.88-1.67 (m, 2H), 1.66-1.30 (m, 8H). | 713.0 | 66 | 8'-((2S,5R)-4-Acryloyl-2,5-dimethylpiperazin-1-yl)-11'-(5-bromo-2,4-difluorophenyl)-10'-(trifluoromethyl)-2,3,5,6-tetrahydro-2'H,4'H,6'H-spiro[pyran-4,3'-[1,4]thiazepino[2,3-4-ij]quinazolin]-6'-one |

Z. Select Experimental Procedures for Compounds 2000 to 2109

Example 2044a: (3S,11R)-8-((3S,5R)-4-acryloyl-3,5-dimethylpiperazin-1-yl)-11-(5-chloro-2,4-difluorophenyl)-3-(pyrimidin-2-yloxy)-10-(trifluoromethyl)-3,4-dihydro-2H,6H-[1,4]thiazepino[2,3,4-ij]quinazolin-6-one Example 2044b: (3S,11S)-8-((3S,5R)-4-acryloyl-3,5-dimethylpiperazin-1-yl)-11-(5-chloro-2,4-difluorophenyl)-3-(pyrimidin-2-yloxy)-10-(trifluoromethyl)-3,4-dihydro-2H,6H-[1,4]thiazepino[2,3,4-ij]quinazolin-6-one 2044a

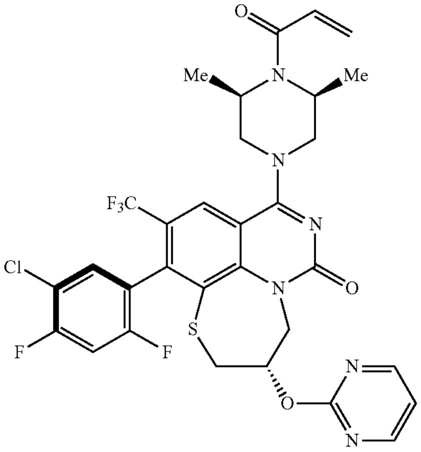

2044b

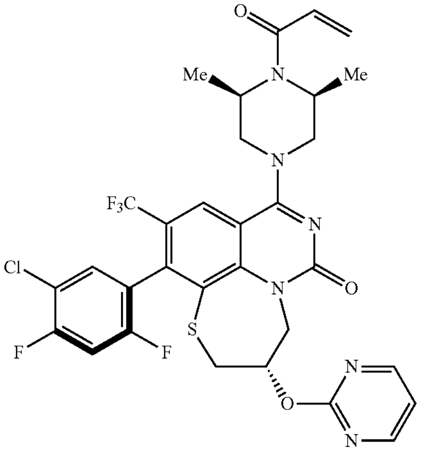

Step 1: tert-butyl (2S,6R)-4-((S)-11-chloro-3-hydroxy-6-oxo-10-(trifluoromethyl)-3,4-dihydro-2H,6H-[1,4]thiazepino[2,3,4-ij]quinazolin-8-yl)-2,6-dimethylpiperazine-1-carboxylate

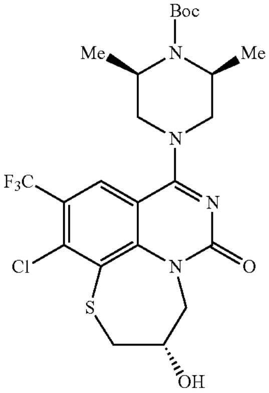 [SMILES: C[C@@H]1CN(c2nc(=O)n3c4c(c(Cl)c(C(F)(F)F)cc24)SC[C@@H](O)C3)C[C@H](C)N1C(=O)OC(C)(C)C]

To a solution of tert-butyl (2S,6R)-4-((S)-3-(benzyloxy)-11-chloro-6-oxo-10-(trifluoromethyl)-3,4-dihydro-2H,6H-[1,4]thiazepino[2,3,4-ij]quinazolin-8-yl)-2,6-dimethylpiperazine-1-carboxylate (1.17 mmol) in dichloromethane (10 mL) was added trifluoroacetic acid (5 mL) and trifluoromethanesulfonic acid (11.7 mmol). The mixture was stirred at 25° C. for 2 hours and the volatiles were removed under reduced pressure to afford a residue that was redissolved in dichloromethane (10 mL) and treated with di-tert-butyl dicarbonate (5.87 mmol) and diisopropylethylamine (11.7 mmol). The reaction was stirred at room temperature for 24 hours, the insoluble materials were filtered off and the solvent removed under reduced pressure. Purification of this crude by preparative-TLC (65% ethyl acetate in hexanes) afforded the title compound as light yellow solid in 56% yield.

MS (ESI) m/z=549.0 [M+H]+

Step 2: tert-butyl (2S,6R)-4-((S)-11-chloro-6-oxo-3-(pyrimidin-2-yloxy)-10-(trifluoromethyl)-3,4-dihydro-2H,6H-[1,4]thiazepino[2,3,4-ij]quinazolin-8-yl)-2,6-dimethylpiperazine-1-carboxylate

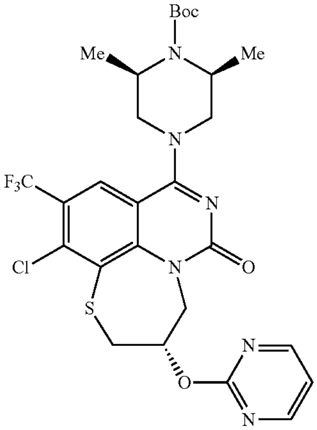 [SMILES: C[C@@H]1CN(c2nc(=O)n3c4c(c(Cl)c(C(F)(F)F)cc24)SC[C@@H](Oc2ncccn2)C3)C[C@H](C)N1C(=O)OC(C)(C)C]

To a 0° C. solution of tert-butyl (2S,6R)-4-((S)-11-chloro-3-hydroxy-6-oxo-10-(trifluoromethyl)-3,4-dihydro-2H,6H-[1,4]thiazepino[2,3,4-ij]quinazolin-8-yl)-2,6-dimethylpiperazine-1-carboxylate (0.31 mmol) and 2-fluoropyrimidine (0.62 mmol) in tetrahydrofuran (2 mL) was added cesium carbonate (0.62 mmol). The mixture was stirred at 60° C. for 2 hours and quenched by the addition of water. The aqueous layer was extracted with ethyl acetate three times and the combined organic layers were washed with brine and dried over anhydrous sodium sulfate, filtered and concentrated under reduced pressure. The resulting residue was purified by preparative-TLC (65% ethyl acetate in hexanes) to afford the title compound in 65% yield as a colorless semisolid.

MS (ESI) m/z=627.0 [M+H]+

Step 3: tert-Butyl (2S,6R)-4-((3S)-11-(5-chloro-2,4-difluorophenyl)-6-oxo-3-(pyrimidin-2-yloxy)-10-(trifluoromethyl)-3,4-dihydro-2H,6H-[1,4]thiazepino[2,3,4-ij]quinazolin-8-yl)-2,6-dimethylpiperazine-1-carboxylate

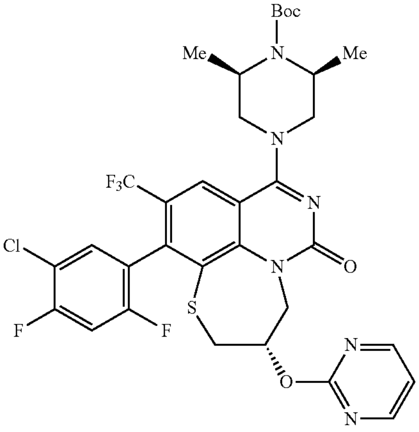 [SMILES: C[C@@H]1CN(c2nc(=O)n3c4c(c(-c5cc(Cl)c(F)cc5F)c(C(F)(F)F)cc24)SC[C@@H](Oc2ncccn2)C3)C[C@H](C)N1C(=O)OC(C)(C)C]

A solution of tert-butyl (2S,6R)-4-((S)-11-chloro-6-oxo-3-(pyrimidin-2-yloxy)-10-(trifluoromethyl)-3,4-dihydro-2H,6H-[1,4]thiazepino[2,3,4-ij]quinazolin-8-yl)-2,6-dimethylpiperazine-1-carboxylate (0.19 mmol), (5-chloro-2,4-difluorophenyl)boronic acid (0.48 mmol), tetrakis(triphenylphosphine) palladium(0) (0.02 mmol) and potassium phosphate (0.57 mmol) in toluene (5 mL) and water (0.1 mL) was stirred at 100° C. for 12 hours. The reaction was quenched with water and extracted with ethyl acetate twice. The combined organic layers were concentrated under reduced pressure to afford a residue that was purified by semi-preparative reverse phase HPLC. The title compound was isolated in 42% yield as a white solid.

MS (ESI) m/z=739.0 [M+H]+

Step 4: (3S)-11-(5-chloro-2,4-difluorophenyl)-8-((3S,5R)-3,5-dimethylpiperazin-1-yl)-3-(pyrimidin-2-yloxy)-10-(trifluoromethyl)-3,4-dihydro-2H,6H-[1,4]thiazepino[2,3,4-ij]quinazolin-6-one

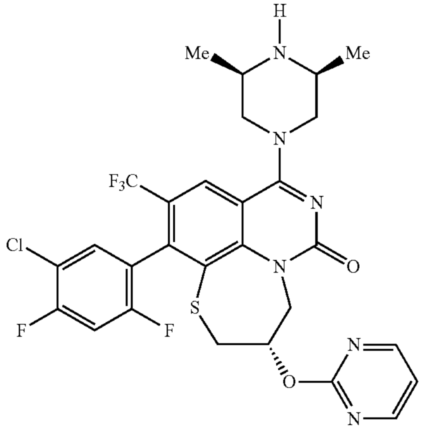 [SMILES: C[C@@H]1CN(c2nc(=O)n3c4c(c(-c5cc(Cl)c(F)cc5F)c(C(F)(F)F)cc24)SC[C@@H](Oc2ncccn2)C3)C[C@H](C)N1]

A solution of tert-butyl (2S,6R)-4-((3S)-11-(5-chloro-2,4-difluorophenyl)-6-oxo-3-(pyrimidin-2-yloxy)-10-(trifluoromethyl)-3,4-dihydro-2H,6H-[1,4]thiazepino[2,3,4-ij]quinazolin-8-yl)-2,6-dimethylpiperazine-1-carboxylate (0.04 mmol) in dichloromethane (2 mL) was treated with trifluoroacetic acid (0.5 mL). After 1 hour the volatiles were removed under reduced pressure to afford the title compound in 96% yield as a yellow oil. This material was used in the next step without further purification.

MS (ESI) m/z=639.0 [M+H]+

Step 5: (3S,11R)-8-((3S,5R)-4-acryloyl-3,5-dimethylpiperazin-1-yl)-11-(5-chloro-2,4-difluorophenyl)-3-(pyrimidin-2-yloxy)-10-(trifluoromethyl)-3,4-dihydro-2H,6H-[1,4]thiazepino[2,3,4-ij]quinazolin-6-one (2044a) and (3S,11S)-8-((3S,5R)-4-acryloyl-3,5-dimethylpiperazin-1-yl)-11-(5-chloro-2,4-difluorophenyl)-3-(pyrimidin-2-yloxy)-10-(trifluoromethyl)-3,4-dihydro-2H,6H-[1,4]thiazepino[2,3,4-ij]quinazolin-6-one (2044b)

2044a

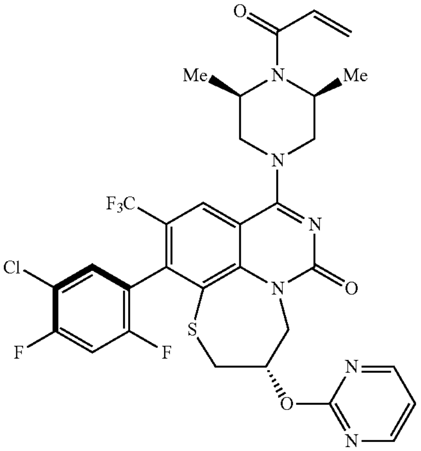

-continued

2044b

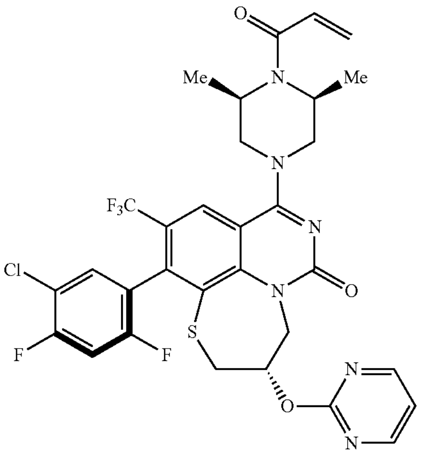

To a solution of (3S)-11-(5-chloro-2,4-difluorophenyl)-8-((3S,5R)-3,5-dimethylpiperazin-1-yl)-3-(pyrimidin-2-yloxy)-10-(trifluoromethyl)-3,4-dihydro-2H,6H-[1,4]thiazepino[2,3,4-ij]quinazolin-6-one (0.04 mmol) in dichloromethane (2 mL) was added triethylamine (0.012 mmol) and prop-2-enoyl chloride (0.06 mmol). The mixture was stirred at room temperature for 30 minutes and was concentrated under reduced pressure. The resulting residue was purified by semi-preparative reverse phase HPLC to afford compounds 2044a and 2044b as a 1:1 mixture of diastereomers. The separation of these diastereomers was carried out by SFC (DAICEL CHIRALPAK AD (250 mm*30 mm, 10 um), 35% ethanol in CO2, 3 mL/min using a photodiode-array detector).

Compound 2044a: Rt=0.53 min. MS (ESI) m/z=693.0 [M+H]+

$^{1}$H NMR (400 MHz, $CDCl_3$) δ 8.53 (d, J=4.8 Hz, 2H), 8.10 (s, 1H), 7.31 (t, J=7.6 Hz, 1H), 7.04 (t, J=8.8 Hz, 1H), 6.99 (t, J=4.8 Hz, 1H), 6.63 (dd, J=10.4, 16.8 Hz, 1H), 6.42 (dd, J=1.6, 16.4 Hz, 1H), 5.83-5.67 (m, 2H), 5.22-4.44 (m, 4H), 4.18 (d, J=13.2 Hz, 2H), 3.68-3.47 (m, 1H), 3.46-3.24 (m, 3H), 1.64-1.54 (m, 6H).

Compound 2044b: Rt=0.73 min. MS (ESI) m/z=693.0 [M+H]+

$^{1}$H NMR (400 MHz, $CDCl_3$) δ 8.54 (d, J=4.8 Hz, 2H), 8.10 (s, 1H), 7.31-7.27 (m, 1H), 7.07 (t, J=8.8 Hz, 1H), 6.99 (t, J=4.8 Hz, 1H), 6.63 (dd, J=10.4, 16.8 Hz, 1H), 6.42 (dd, J=2.0, 16.8 Hz, 1H), 5.82-5.62 (m, 2H), 5.07-4.40 (m, 4H), 4.18 (d, J=13.2 Hz, 2H), 3.57-3.31 (m, 4H), 1.91-1.54 (m, 6H).

Example 2066: (3S)-8-((3S,5R)-4-acryloyl-3,5-dimethylpiperazin-1-yl)-11-(5-bromo-2,4-difluorophenyl)-3-(pyrimidin-2-yloxy)-10-(trifluoromethyl)-3,4-dihydro-2H,6H-[1,4]thiazepino[2,3,4-ij]quinazolin-6-one

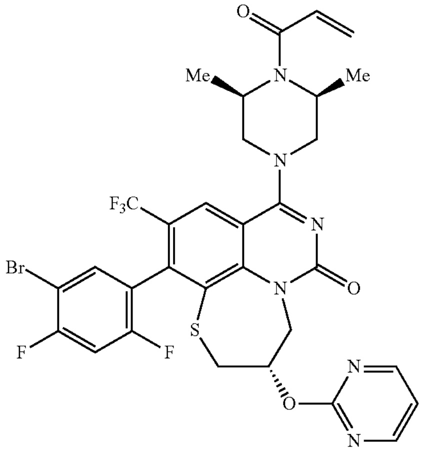 [SMILES: C=CC(=O)N1[C@H](C)CN(c2nc(=O)n3c4c(c(-c5cc(Br)c(F)cc5F)c(C(F)(F)F)cc24)SC[C@@H](Oc2ncccn2)C3)C[C@@H]1C]

Step 1: (S)-2-((1-((tert-butyldiphenylsilyl)oxy)-3-(tritylthio)propan-2-yl)oxy)pyrimidine

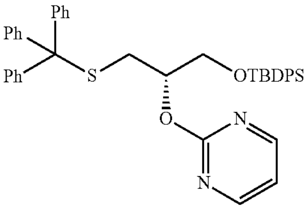

(S)-1-((tert-butyldiphenylsilyl)oxy)-3-(tritylthio)propan-2-ol (25.5 mmol) was added to a 0° C. suspension of NaH (30.8 mmol) in THF (30 mL). After 30 minutes, 2-chloropyrimidine (30.6 mmol) was added and the mixture was stirred at room temperature for 6 hours. The reaction was quenched with water and extracted with ethyl acetate three times. The combined organic layers were washed with brine, dried over sodium sulfate and concentrated to afford a residue that was purified by silica gel column chromatography (0-30% ethyl acetate in hexanes) to afford the title compound in 98% yield as a yellow oil.

MS (ESI) m/z=689.2 [M+H]+

Step 2: (S)-3-((tert-butyldiphenylsilyl)oxy)-2-(pyrimidin-2-yloxy)propane-1-thiol

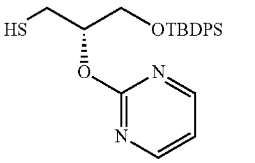

To a 0° C. mixture of (S)-2-((1-((tert-butyldiphenylsilyl)oxy)-3-(tritylthio)propan-2-yl)oxy)pyrimidine (39 mmol) in dichloromethane (120 mL) and trifluoroacetic acid (30 mL), $Et_3SiH$ (78 mmol) was added and after 5 minutes the reaction was stopped by the addition of water. The mixture was extracted with dichloromethane three times and the combined organic layers were dried over sodium sulfate, concentrated and the resulting residue was purified by silica gel column chromatography (0-2% methanol in dichloromethane). The title compound was isolated in 59% yield as a colorless oil.

MS (ESI) m/z=447.1 [M+Na]+

Step 3: (S)-8-((3-((tert-butyldiphenylsilyl)oxy)-2-(pyrimidin-2-yloxy)propyl)thio)-7-chloro-6-(trifluoromethyl)quinazoline-2,4(1H,3H)-dione

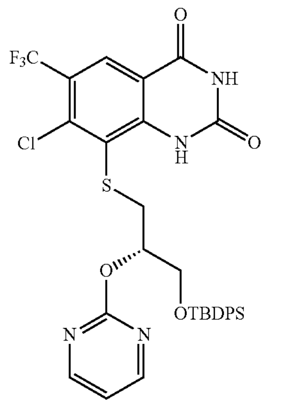

The title compound was prepared analogously to Example 100, step 9 of PCT/US2020/065966 where (S)-3-((tert-butyldiphenylsilyl)oxy)-2-(pyrimidin-2-yloxy)propane-1-thiol was substituted in place of 2-mercaptoethan-1-ol. The title compound was isolated in 65% yield as a white solid.

MS (ESI) m/z=687.1 [M+H]+

Step 4: (S)-7-Chloro-8-((3-hydroxy-2-(pyrimidin-2-yloxy)propyl)thio)-6-(trifluoromethyl)quinazoline-2,4(1H,3H)-dione

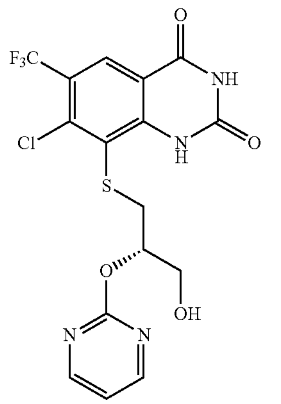 [SMILES: O=c1[nH]c(=O)c2cc(C(F)(F)F)c(Cl)c(SC[C@H](CO)Oc3ncccn3)c2[nH]1]

To a mixture of (S)-8-((3-((tert-butyldiphenylsilyl)oxy)-2-(pyrimidin-2-yloxy)propyl)thio)-7-chloro-6-(trifluoromethyl)quinazoline-2,4(1H,3H)-dione (8 g) in THF (80 mL) was added a 1M solution of tetrabutylammonium fluoride in THF (35 mmol) and the mixture was stirred at room temperature for 4 hours. Evaporation of volatiles under reduced pressure afforded a residue that was washed with water and filtered. The filter cake was washed with ethyl acetate. The title compound was isolated in 57% yield as an off-white solid.

MS (ESI) m/z=449.0 [M+H]+

Step 5: (S)-11-Chloro-3-(pyrimidin-2-yloxy)-10-(trifluoromethyl)-3,4-dihydro-2H,6H-[1,4]thiazepino[2,3,4-ij]quinazoline-6,8(7H)-dione

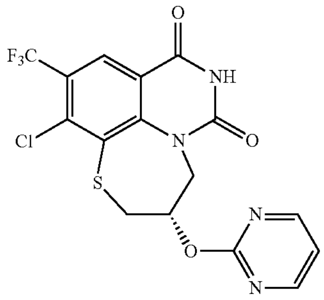 [SMILES: O=c1[nH]c(=O)n2c3c(c(Cl)c(C(F)(F)F)cc13)SC[C@@H](Oc1ncccn1)C2]

The title compound was prepared analogously to Example 100, step 10 of PCT/US2020/065966 where (S)-7-chloro-8-((3-hydroxy-2-(pyrimidin-2-yloxy)propyl)thio)-6-(trifluoromethyl)quinazoline-2,4(1H,3H)-dione was substituted in place of 7-(2,4-difluorophenyl)-8-((2-hydroxyethyl)thio)-6-(trifluoromethyl)quinazoline-2,4(1H,3H)-dione. The title compound was isolated in 72% yield as a white solid.

MS (ESI) m/z=431.0 [M+H]+

Step 6: tert-Butyl (2S,6R)-4-((S)-11-chloro-6-oxo-3-(pyrimidin-2-yloxy)-10-(trifluoromethyl)-3,4-dihydro-2H,6H-[1,4]thiazepino[2,3,4-ij]quinazolin-8-yl)-2,6-dimethylpiperazine-1-carboxylate

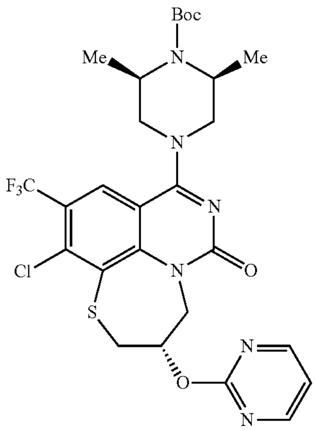 [SMILES: C[C@@H]1CN(c2nc(=O)n3c4c(c(Cl)c(C(F)(F)F)cc24)SC[C@@H](Oc2ncccn2)C3)C[C@H](C)N1C(=O)OC(C)(C)C]

The title compound was prepared analogously to Example 100, step 21 of PCT/US2020/065966 where (S)-11-chloro-3-(pyrimidin-2-yloxy)-10-(trifluoromethyl)-3,4-dihydro-2H,6H-[1,4]thiazepino[2,3,4-ij]quinazoline-6,8(7H)-dione and (2R,6S)-2,6-dimethyl piperazine were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 87% yield as a yellow solid.

MS (ESI) m/z=627.1 [M+H]+

Step 7: tert-Butyl (2S,6R)-4-((3S)-11-(5-amino-2,4-difluorophenyl)-6-oxo-3-(pyrimidin-2-yloxy)-10-(trifluoromethyl)-3,4-dihydro-2H,6H-[1,4]thiazepino [2,3,4-ij]quinazolin-8-yl)-2,6-dimethylpiperazine-1-carboxylate

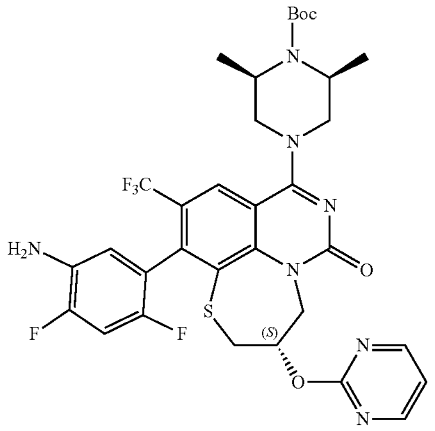

A mixture of tert-butyl (2S,6R)-4-((S)-11-chloro-6-oxo-3-(pyrimidin-2-yloxy)-10-(trifluoromethyl)-3,4-dihydro-2H,6H-[1,4]thiazepino[2,3,4-ij]quinazolin-8-yl)-2,6-dimethylpiperazine-1-carboxylate (0.64 mmol), 2,4-difluoro-5-(4,4,5,5-tetramethyl-1,3,2-dioxaborolan-2-yl)aniline (1.15 mmol), RuPhos Pd G4 (0.19 mmol) and $K_3PO_4$ (1.91 mmol) in dioxane (5 mL) and water (0.5 mL) was stirred at 80° C. for 1 hour. The reaction was diluted with ethyl acetate and washed with brine, the organic layer was separated and dried over sodium sulfate, filtered and concentrated to afford a crude that was purified by reverse phase chromatography. The title compound was isolated in 30% yield as a yellow solid.

MS (ESI) m/z=720.0 [M+H]+

Step 8: tert-Butyl (2S,6R)-4-((3S)-11-(5-bromo-2,4-difluorophenyl)-6-oxo-3-(pyrimidin-2-yloxy)-10-(trifluoromethyl)-3,4-dihydro-2H,6H-[1,4]thiazepino [2,3,4-ij]quinazolin-8-yl)-2,6-dimethylpiperazine-1-carboxylate

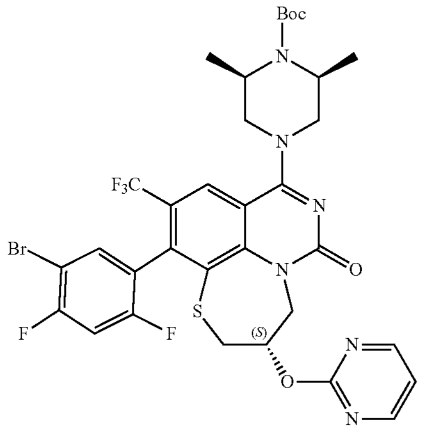

A mixture of tert-butyl (2S,6R)-4-((3S)-11-(5-amino-2,4-difluorophenyl)-6-oxo-3-(pyrimidin-2-yloxy)-10-(trifluoromethyl)-3,4-dihydro-2H,6H-[1,4]thiazepino[2,3,4-ij]quinazolin-8-yl)-2,6-dimethylpiperazine-1-carboxylate (0.17 mmol) and BuBr2 (0.22 mmol) in acetonitrile (2.5 mL) was treated with tert-butyl nitrite (0.22 mmol) and the reaction was stirred for 30 minutes. The reaction was diluted with ethyl acetate and washed with brine, the organic layer was separated and dried over sodium sulfate, filtered and concentrated to afford a crude that was purified by reverse phase chromatography. The title compound was isolated in 54% yield as a yellow solid.

MS (ESI) m/z=783.0 [M+H]+

Step 9: (3S)-11-(5-bromo-2,4-difluorophenyl)-8-((3S,5R)-3,5-dimethylpiperazin-1-yl)-3-(pyrimidin-2-yloxy)-10-(trifluoromethyl)-3,4-dihydro-2H,6H-[1,4]thiazepino[2,3,4-ij]quinazolin-6-one

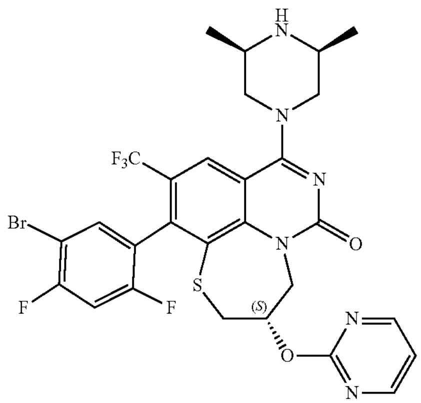

The title compound was prepared analogously to Example 1, step 4 where tert-Butyl (2S,6R)-4-((3S)-11-(5-bromo-2,4-difluorophenyl)-6-oxo-3-(pyrimidin-2-yloxy)-10-(trifluoromethyl)-3,4-dihydro-2H,6H-[1,4]thiazepino[2,3,4-ij]quinazolin-8-yl)-2,6-dimethylpiperazine-1-carboxylate was substituted in place of tert-butyl (2S,6R)-4-((3S)-11-(5-chloro-2,4-difluorophenyl)-6-oxo-3-(pyrimidin-2-yloxy)-10-(trifluoromethyl)-3,4-dihydro-2H,6H-[1,4]thiazepino[2,3,4-ij]quinazolin-8-yl)-2,6-dimethylpiperazine-1-carboxylate. The title compound was isolated in 95% yield as a white solid MS (ESI) m/z=682.9/685.0 [M+H]+

Step 10: (3S)-8-((3S,5R)-4-acryloyl-3,5-dimethylpiperazin-1-yl)-11-(5-bromo-2,4-difluorophenyl)-3-(pyrimidin-2-yloxy)-10-(trifluoromethyl)-3,4-dihydro-2H,6H-[1,4]thiazepino[2,3,4-ij]quinazolin-6-one

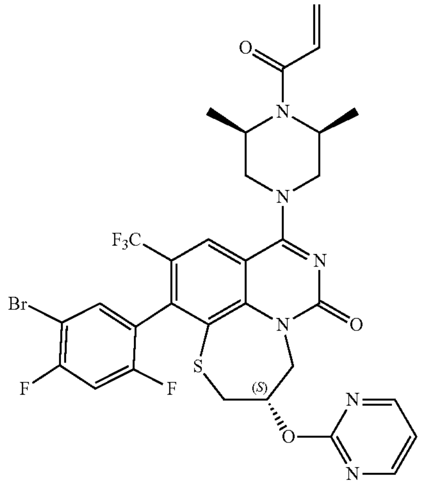

The title compound was prepared analogously to Example 1, step 4 where (3S)-11-(5-bromo-2,4-difluorophenyl)-8-((3S,5R)-3,5-dimethylpiperazin-1-yl)-3-(pyrimidin-2-yloxy)-10-(trifluoromethyl)-3,4-dihydro-2H,6H-[1,4]thiazepino[2,3,4-ij]quinazolin-6-one was substituted in place of (3S)-11-(5-chloro-2,4-difluorophenyl)-8-((3S,5R)-3,5-dimethylpiperazin-1-yl)-3-(pyrimidin-2-yloxy)-10-(trifluoromethyl)-3,4-dihydro-2H,6H-[1,4]thiazepino[2,3,4-ij]quinazolin-6-one. The title compound was isolated in 31% yield as a white solid.

MS (ESI) m/z=736.9/739.0 [M+H]+

Example 2048 (also Example 2055): (3S,11R)-8-((3S,5R)-4-acryloyl-3,5-dimethylpiperazin-1-yl)-11-(5-chloro-2,4-difluorophenyl)-3-(pyrimidin-2-ylamino)-10-(trifluoromethyl)-3,4-dihydro-2H,6H-[1,4]thiazepino[2,3,4-ij]quinazolin-6-one Compound 2055

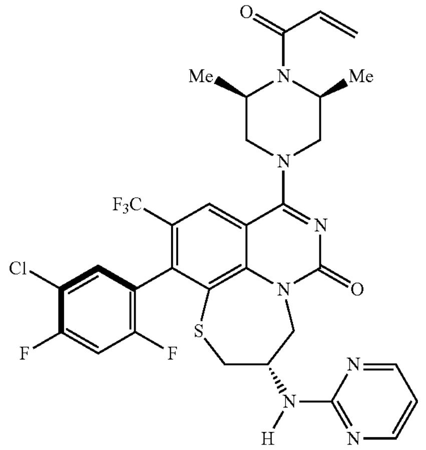

Step 1: tert-Butyl (2S,6R)-4-((S)-3-(((benzyloxy)carbonyl)amino)-11-chloro-6-oxo-10-(trifluoromethyl)-3,4-dihydro-2H,6H-[1,4]thiazepino[2,3,4-ij]quinazolin-8-yl)-2,6-dimethylpiperazine-1-carboxylate

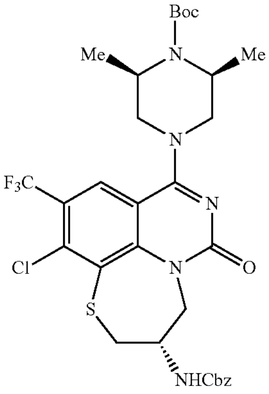 [SMILES: C[C@@H]1CN(c2nc(=O)n3c4c(c(Cl)c(C(F)(F)F)cc24)SC[C@@H](NC(=O)OCc2ccccc2)C3)C[C@H](C)N1C(=O)OC(C)(C)C]

The title compound was prepared analogously to Example 100, step 21 of PCT/US2020/065966 where benzyl (S)-(11-chloro-6,8-dioxo-10-(trifluoromethyl)-3,4,7,8-tetrahydro-2H,6H-[1,4]thiazepino[2,3,4-ij]quinazolin-3-yl)carbamate and (2R,6S)-2,6-dimethyl piperazine were substituted in place of 10-(2,4-difluorophenyl)-9-(trifluoromethyl)-2,3-dihydro-5H-[1,4]thiazino[2,3,4-ij]quinazoline-5,7(6H)-dione and octahydrothieno[3,4-b]pyrazine 6,6-dioxide. The title compound was isolated in 64% yield as a yellow solid.

MS (ESI) m/z=682.1 [M+H]+

Step 2: (S)-3-Amino-11-chloro-8-((3S,5R)-3,5-dimethylpiperazin-1-yl)-10-(trifluoromethyl)-3,4-dihydro-2H,6H-[1,4]thiazepino[2,3,4-ij]quinazolin-6-one

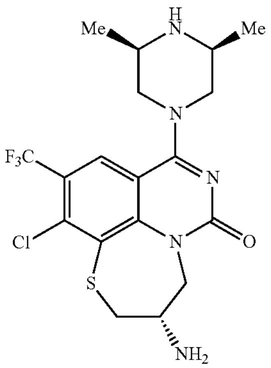 [SMILES: C[C@@H]1CN(c2nc(=O)n3c4c(c(Cl)c(C(F)(F)F)cc24)SC[C@@H](N)C3)C[C@H](C)N1]

To a solution of tert-butyl (2S,6R)-4-((S)-3-(((benzyloxy) carbonyl)amino)-11-chloro-6-oxo-10-(trifluoromethyl)-3,4-dihydro-2H,6H-[1,4]thiazepino[2,3,4-ij]quinazolin-8-yl)-2,6-dimethylpiperazine-1-carboxylate (1.61 mmol) in dichloromethane (5 mL) was added trifluoroacetic acid (67.5 mmol) and trifluoromethanesulfonic acid (8.06 mmol) at 0° C. The mixture was stirred at room temperature for two hours. The mixture was filtered and the filtrate was concentrated under reduced pressure to afford a residue that was purified by silica gel chromatography (10-50% ethyl acetate in hexanes). The title compound was isolated in 99% yield and was used into the next step without further purification.

MS (ESI) m/z=448.0 [M+H]+

Step 3: (S)-11-Chloro-8-((3S,5R)-3,5-dimethylpiperazin-1-yl)-3-(pyrimidin-2-ylamino)-10-(trifluoromethyl)-3,4-dihydro-2H,6H-[1,4]thiazepino[2,3,4-ij]quinazolin-6-one

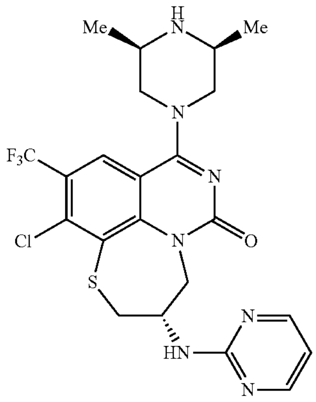 [SMILES: C[C@@H]1CN(c2nc(=O)n3c4c(c(Cl)c(C(F)(F)F)cc24)SC[C@@H](Nc2ncccn2)C3)C[C@H](C)N1]

To a solution of (S)-3-amino-11-chloro-8-((3S,5R)-3,5-dimethylpiperazin-1-yl)-10-(trifluoromethyl)-3,4-dihydro-2H,6H-[1,4]thiazepino[2,3,4-ij]quinazolin-6-one (0.22 mmol) in DMF (1 mL) was added diisopropylethylamine (0.67 mmol) and 2-fluoropyrimidine (0.31 mmol). The mixture was stirred at room temperature for 24 hours and it was diluted with ethyl acetate and water. The organic layer was washed with water and brine, dried over sodium sulfate and concentrated to afford a residue that was purified by preparative HPLC. The title compound was isolated in 34% yield as a yellow solid.

MS (ESI) m/z=526.0 [M+H]+

Step 4: (3S)-11-(5-chloro-2,4-difluorophenyl)-8-((3S,5R)-3,5-dimethylpiperazin-1-yl)-3-(pyrimidin-2-ylamino)-10-(trifluoromethyl)-3,4-dihydro-2H,6H-[1,4]thiazepino[2,3,4-ij]quinazolin-6-one

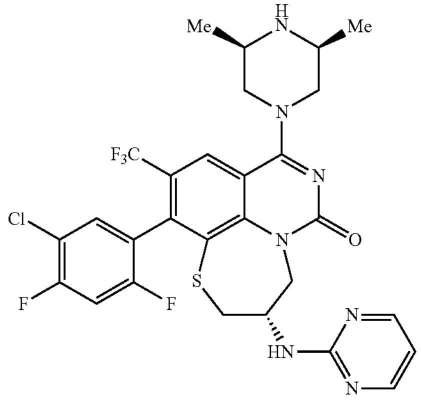 [SMILES: C[C@@H]1CN(c2nc(=O)n3c4c(c(-c5cc(Cl)c(F)cc5F)c(C(F)(F)F)cc24)SC[C@@H](Nc2ncccn2)C3)C[C@H](C)N1]

The title compound was prepared analogously to Example 1, step 3 where (S)-11-chloro-8-((3S,5R)-3,5-dimethylpiperazin-1-yl)-3-(pyrimidin-2-ylamino)-10-(trifluoromethyl)-3,4-dihydro-2H,6H-[1,4]thiazepino[2,3,4-ij]quinazolin-6-one was substituted in place of tert-butyl (2S,6R)-4-((S)-11-chloro-6-oxo-3-(pyrimidin-2-yloxy)-10-(trifluoromethyl)-3,4-dihydro-2H,6H-[1,4]thiazepino[2,3,4-ij]quinazolin-8-yl)-2,6-dimethylpiperazine-1-carboxylate. The title compound was isolated in 99% yield as a yellow solid MS (ESI) m/z=638.0 [M+H]+

Step 5: (3S)-8-((3S,5R)-4-acryloyl-3,5-dimethylpiperazin-1-yl)-11-(5-chloro-2,4-difluorophenyl)-3-(pyrimidin-2-ylamino)-10-(trifluoromethyl)-3,4-dihydro-2H,6H-[1,4]thiazepino[2,3,4-ij]quinazolin-6-one

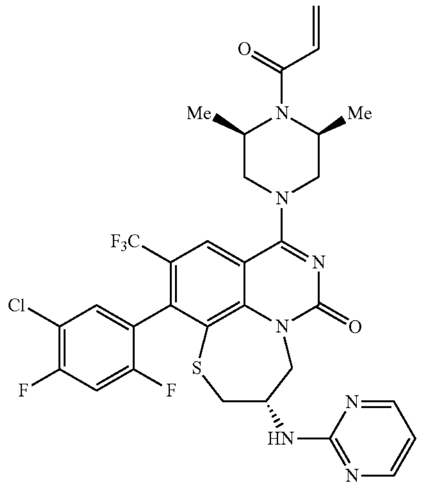 [SMILES: C=CC(=O)N1[C@H](C)CN(c2nc(=O)n3c4c(c(-c5cc(Cl)c(F)cc5F)c(C(F)(F)F)cc24)SC[C@@H](Nc2ncccn2)C3)C[C@@H]1C]

The title compound was prepared analogously to Example 1, step 5 where (3S)-11-(5-chloro-2,4-difluorophenyl)-8-((3S,5R)-3,5-dimethylpiperazin-1-yl)-3-(pyrimidin-2-ylamino)-10-(trifluoromethyl)-3,4-dihydro-2H,6H-[1,4]thiazepino[2,3,4-ij]quinazolin-6-one was substituted in place of (3S)-11-(5-chloro-2,4-difluorophenyl)-8-((3S,5R)-3,5-dimethylpiperazin-1-yl)-3-(pyrimidin-2-yloxy)-10-(trifluoromethyl)-3,4-dihydro-2H,6H-[1,4]thiazepino[2,3,4-ij]quinazolin-6-one. The separation of this diastereomer was carried out by SFC (DAICEL CHIRALPAK AD (250 mm*30 mm, 10 um), 40% isopropanol in CO2, 3 mL/min using a photodiode-array detector) in 15% yield as a white solid. Rt=1.28 min. MS (ESI) m/z=692.0 [M+H]+

1H NMR (400 MHz, CDCl3) δ, 8.44-8.19 (m, 2H), 8.12 (s, 1H), 7.27-7.23 (m, 2H), 7.06 (br t, J=8.8 Hz, 1H), 6.80-6.59 (m, 2H), 6.42 (dd, J=1.6, 16.8 Hz, 1H), 5.79 (dd, J=1.6, 10.4 Hz, 1H), 5.12-4.61 (m, 4H), 4.59-4.34 (m, 1H), 4.27-4.15 (m, 2H), 3.77-3.57 (m, 1H), 3.46-3.35 (m, 2H), 3.32-3.13 (m, 1H), 1.55 (br s, 6H).

Example 2065: (3S)-8-((3S,5R)-4-acryloyl-3,5-dimethylpiperazin-1-yl)-11-(5-bromo-2,4-difluorophenyl)-3-(pyrazin-2-yloxy)-10-(trifluoromethyl)-3,4-dihydro-2H,6H-[1,4]thiazepino[2,3,4-ij]quinazolin-6-one

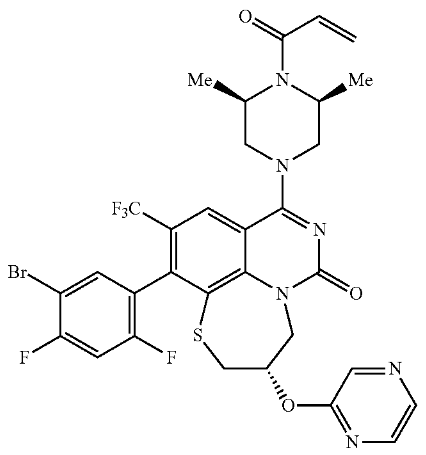 [SMILES: C=CC(=O)N1[C@H](C)CN(c2nc(=O)n3c4c(c(-c5cc(Br)c(F)cc5F)c(C(F)(F)F)cc24)SC[C@@H](Oc2cnccn2)C3)C[C@@H]1C]

The title compound was prepared analogously to Example 2066, steps 1-10 where 2-fluoropyrazine was substituted in place of 2-chloropyrimidine during step 1.

MS (ESI) m/z=737.1 [M+H]+

1H NMR (400 MHz, $CDCl_3$) δ 8.25 (s, 1H), 8.15 (s, 1H), 8.11-8.07 (m, 2H), 7.46-74.42 (m, 1H), 7.26 (m, 1H), 6.63 (dd, J=10.4, 16.8 Hz, 1H), 6.42 (dd, J=1.6, 16.4 Hz, 1H), 5.83-5.67 (d, J=10.4 Hz, 2H), 4.90-4.50 (m, 4H), 4.25 (m, 2H), 3.68-3.24 (m, 4H), 1.75-1.30 (m, 6H).

Example 2064: (3S)-8-((3S,5R)-4-acryloyl-3,5-dimethylpiperazin-1-yl)-11-(5-bromo-2,4-difluorophenyl)-3-(pyridin-2-yloxy)-10-(trifluoromethyl)-3,4-dihydro-2H,6H-[1,4]thiazepino[2,3,4-ij]quinazolin-6-one

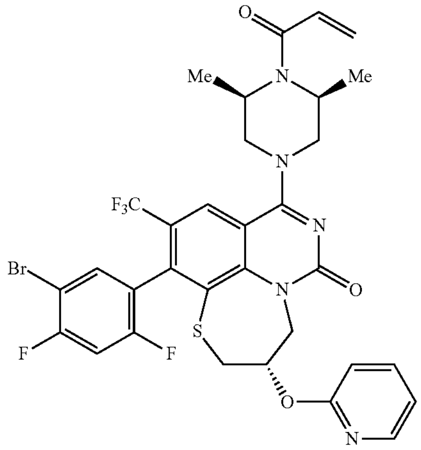 [SMILES: C=CC(=O)N1[C@H](C)CN(c2nc(=O)n3c4c(c(-c5cc(Br)c(F)cc5F)c(C(F)(F)F)cc24)SC[C@@H](Oc2ccccn2)C3)C[C@@H]1C]

The title compound was prepare analogously to example 2066, steps 1-10 where 2-chloropyridine was substituted in place of 2-chloropyrimidine during step 1.

MS (ESI) m/z=736.0 [M+H]+

1H NMR (400 MHz, CDCl3) δ=8.25-8.01 (m, 2H), 7.75-7.59 (m, 1H), 7.48-7.36 (m, 1H), 7.10-6.91 (m, 2H), 6.89-6.75 (m, 1H), 6.63 (dd, J=16.6, 10.6, 1H), 6.42 (dd, J=16.6, 2.0, 1H), 5.93-5.71 (m, 2H), 5.04-4.48 (m, 4H), 4.28-4.06 (m, 2H), 3.67-3.25 (m, 4H), 1.71-1.36 (m, 6H).

Example 2009: (S)-7-((3S,5R)-4-acryloyl-3,5-dimethylpiperazin-1-yl)-3-(methoxymethyl)-9-(trifluoromethyl)-10-(2,4,6-trifluorophenyl)-2H-[1,4]thiazino[2,3,4-ij]quinazolin-5(3H)-one

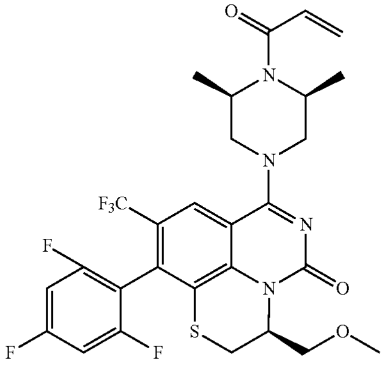 [SMILES: C=CC(=O)N1[C@H](C)CN(c2nc(=O)n3c4c(c(-c5c(F)cc(F)cc5F)c(C(F)(F)F)cc24)SC[C@@H]3COC)C[C@@H]1C]

Reaction Scheme
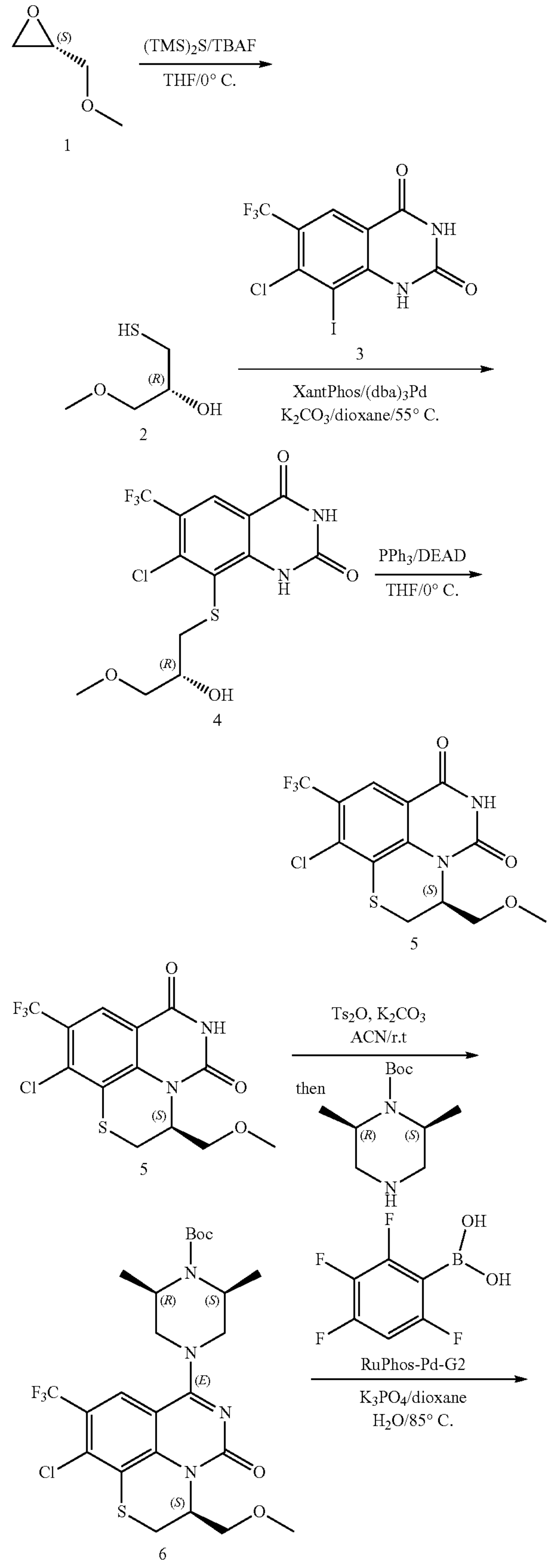
-continued
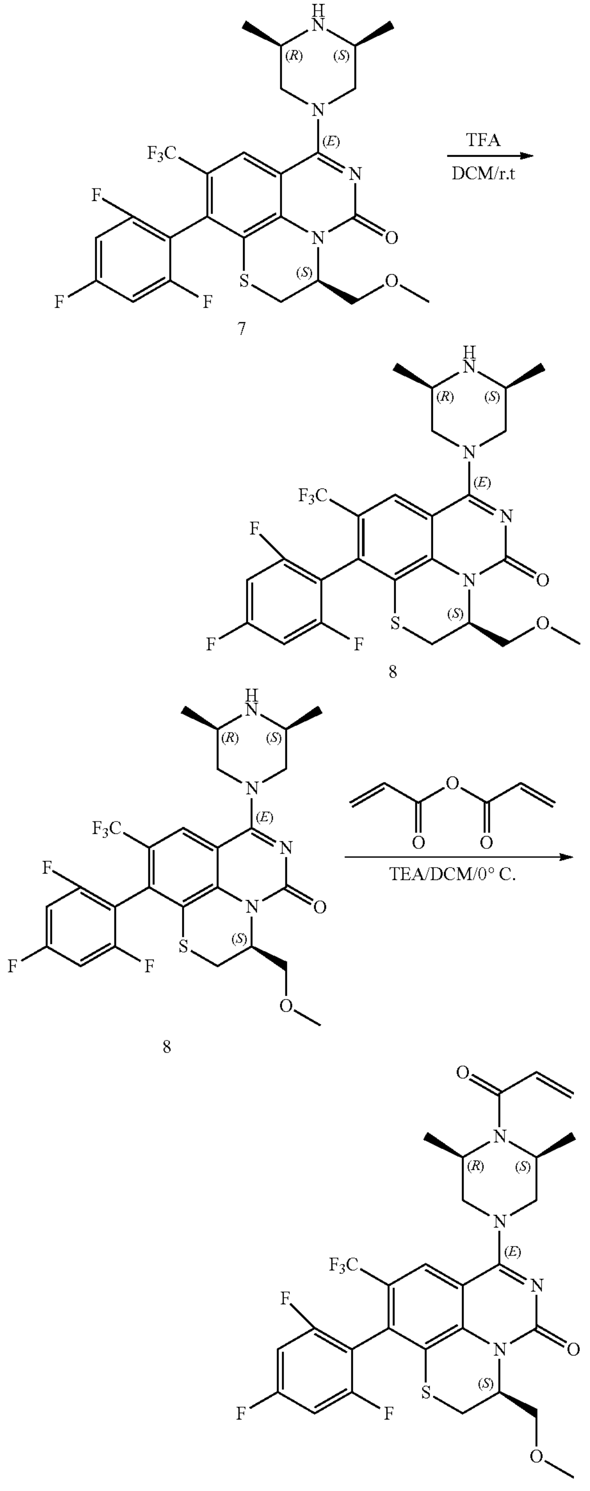
(R)-1-mercapto-3-methoxypropan-2-ol (2)
To a mixture of (S)-2-(methoxymethyl)oxirane (50 g, 568.2 mmol) in tetrahydrofuran (800 mL) was added 1,1,1,3,3,3-hexamethyldisilathiane (119.4 g, 681.8 mmol) and tetrabutylammonium fluoride (1.0 M in tetrahydrofuran, 170.6 mL, 170.5 mmol) at 0° C. The mixture was stirred at room temperature for 2 hours. After completion, the mixture was poured into water (3000 mL), extracted with ethyl acetate (800 mL×3). The combined organic phases were washed with brine (800 mL) and dried over anhydrous sodium sulfate. After filtration and concentration, the residue was purified by silica gel column with petroleum ether/ethyl acetate=3/1 to afford (R)-1-mercapto-3-methoxypropan-2-ol (2) (70.0 g, crude) as a colorless oil.

1H NMR (300 MHz, CDCl3) δ 3.86-3.82 (m, 1H), 3.49-3.46 (m, 1H), 3.41-3.37 (m, 4H), 2.71-2.64 (m, 1H), 1.55-1.50 (m, 1H).

(R)-7-chloro-8-((2-hydroxy-3-methoxypropyl)thio)-6-(trifluoromethyl)quinazoline-2,4(1H,3H)-dione (4)

To a solution of 7-chloro-8-iodo-6-(trifluoromethyl)quinazoline-2,4(1H,3H)-dione (20 g, 51.2 mmol) in dioxane (800 mL), potassium carbonate (21.2 g, 153.6 mmol), (R)-1-mercapto-3-methoxypropan-2-ol (11.26 g, 92.1 mmol), 4,5-Bis(diphenyl-phosphino)-9,9-dimethylxanthene (5.93 g, 10.24 mmol) and Tris(dibenzylideneacetone) dipalladium (4.7 g, 5.1 mmol) were added. The mixture was stirred at 55° C. under nitrogen atmosphere for 18 hours. After completion, the insoluble was filtered out. After concentration, the residue was adjusted to PH=4 with acetic acid and extracted with ethyl acetate (1000 mL), washed with brine (500 mL). The organic phase was concentrated and recrystallized (dichloromethane/methanol=1/10). The mixture was filtered and collected filter cake to afford (R)-7-chloro-8-((2-hydroxy-3-methoxypropyl)thio)-6-(trifluoromethyl)quinazoline-2,4(1H,3H)-dione (14 g, yield: 71%) as a white solid. MS (ESI) m/z 385.0 [M+H]+.

(S)-10-chloro-3-(methoxymethyl)-9-(trifluoromethyl)-2H-[1,4]thiazino[2,3,4-ij]quinazoline-5,7(3H,6H)-dione (5)

To a mixture of (R)-7-chloro-8-((2-hydroxy-3-methoxypropyl)thio)-6-(trifluoromethyl)quinazoline-2,4(1H,3H)-dione (4) (34.4 g, 89.5 mmol) and triphenylphosphine (35.2 g, 134.3 mmol) in tetrahydrofuran (500 mL) was added diethyl azodicarboxylate (23.3 g, 134.3 mmol) at 0° C. The mixture was stirred at 0° C. for 45 min. After completion, the mixture was poured into ice-water (300 mL) and extracted with ethyl acetate (500 mL×3). Concentrated and the residue was recrystallized (dichloromethane/methanol=1/10), the mixture was filtered and collected filter cake to afford (S)-10-chloro-3-(methoxymethyl)-9-(trifluoromethyl)-2H-[1,4]thiazino[2,3,4-ij]quinazoline-5,7(3H,6H)-dione (5) (24.0 g, 73% yield) as a white solid. MS (ESI): m/z 367.0 $[M+H]^+$.

(2S,6R)-tert-butyl 4-((S)-10-chloro-3-(methoxymethyl)-5-oxo-9-(trifluoromethyl)-3,5-dihydro-2H-[1,4]thiazino[2,3,4-ij]quinazolin-7-yl)-2,6-dimethylpiperazine-1-carboxylate (6)

To a mixture of (S)-10-chloro-3-(methoxymethyl)-9-(trifluoromethyl)-2H-[1,4]thiazino[2,3,4-ij]quinazoline-5,7(3H,6H)-dione (5) (10 g, 27.32 mmol) and potassium carbonate (37.7 g, 273.2 mmol) in acetonitrile (500 mL) was added 4-methylbenzenesulfonic anhydride (13.4 g, 40.98 mmol) at 0° C. The mixture was stirred at 0° C. for 30 min and at 30° C. for 4 hours. After completion, (2S,6R)-tert-butyl 2,6-dimethylpiperazine-1-carboxylate (11.7 g, 54.64 mmol) was added into the reaction solution. The reaction mixture was stirred at 0° C. for 2 hours. After completion, the mixture was filtered through a Celite pad, and the filtrate was purified by chromatography column (dichloromethane/methanol=100/1 to 30/1) to afford (2S,6R)-tert-butyl 4-((S)-10-chloro-3-(methoxymethyl)-5-oxo-9-(trifluoromethyl)-3,5-dihydro-2H-thiazino[2,3,4-ij]quinazolin-7-yl)-2,6-dimethylpiperazine-1-carboxylate (6) (15 g, crude) as a pale-white solid. MS (ESI) m/z 563.5 $[M+H]^+$.

(2S,6R)-tert-butyl 4-((S)-3-(methoxymethyl)-5-oxo-9-(trifluoromethyl)-10-(2,4,6-trifluorophenyl)-3,5-dihydro-2H-[1,4]thiazino[2,3,4-ij]quinazolin-7-yl)-2,6-dimethylpiperazine-1-carboxylate (7)

To a solution of (2S,6R)-tert-butyl 4-((S)-10-chloro-3-(methoxymethyl)-5-oxo-9-(trifluoromethyl)-3,5-dihydro-2H-[1,4]thiazino[2,3,4-ij]quinazolin-7-yl)-2,6-dimethylpiperazine-1-carboxylate (6) (280 mg, 0.5 mmol), tripotassium phosphate (400 mg, 1.5 mmol) and Chloro(2-dicyclohexylphosphino-2', 6'-diisopropoxy-1,1'-biphenyl)[2-(2'-amino-1,1'-biphenyl)]palladium(II) (80 mg, 0.1 mmol) in 1,4-dioxane (5 mL) and water (1 mL) was added another solution of (2,4,6-trifluorophenyl)boronic acid (1.58 g, 10 mmol) and Chloro(2-dicyclohexylphosphino-2', 6'-diisopropoxy-1,1'-biphenyl)[2-(2'-amino-1,1'-biphenyl)]palladium(II) (80 mg, 0.1 mmol) in 1,4-dioxane(5 mL) at 85° C. under nitrogen atmosphere. After completion, the mixture was diluted with tetrahydrofuran (50 mL) and filtered. After concentration, the residue was purified by silica gel column chromatography (dichloromethane/methanol=100/1 to 30/1) to afford (2S,6R)-tert-butyl 4-((S)-3-(methoxymethyl)-5-oxo-9-(trifluoromethyl)-10-(2,4,6-trifluorophenyl)-3,5-dihydro-2H-[1,4]thiazino[2,3,4-ij]quinazolin-7-yl)-2,6-dimethylpiperazine-1-carboxylate (7) (64 mg, yield: 20%) as a yellow solid. MS (ESI) m/z 659.6 $[M+H]^+$.

(S)-7-((3S,5R)-3,5-dimethylpiperazin-1-yl)-3-(methoxymethyl)-9-(trifluoromethyl)-10-(2,4,6-trifluorophenyl)-2H-[1,4]thiazino[2,3,4-ij]quinazolin-5(3H)-one (8)

To a cooled mixture of (2S,6R)-tert-butyl 4-((S)-3-(methoxymethyl)-5-oxo-9-(trifluoromethyl)-10-(2,4,6-trifluorophenyl)-3,5-dihydro-2H-[1,4]thiazino[2,3,4-ij]quinazolin-7-yl)-2,6-dimethylpiperazine-1-carboxylate (7) (64 mg, 0.1 mmol) in dichloromethane (4 ml) was added trifluoroacetic acid (2 mL) at 0° C. The reaction solution was stirred at room temperature for 3 hours. After completion, the mixture was concentrated, the residue was purified by column (dichloromethane/methanol=15:1) to afford (S)-7-((3S,5R)-3,5-dimethylpiperazin-1-yl)-3-(methoxymethyl)-9-(trifluoromethyl)-10-(2,4,6-trifluorophenyl)-2H-[1,4]thiazino[2,3,4-ij]quinazolin-5(3H)-one (54 mg, yield: 90%) as a yellow solid. MS (ESI) m/z 559.6 $[M+H]^+$.

(S)-7-((3S,5R)-4-acryloyl-3,5-dimethylpiperazin-1-yl)-3-(methoxymethyl)-9-(trifluoromethyl)-10-(2,4,6-trifluorophenyl)-2H-[1,4]thiazino[2,3,4-ij]quinazolin-5(3H)-one (9)

To a mixture of (S)-7-((3S,5R)-3,5-dimethylpiperazin-1-yl)-3-(methoxymethyl)-9-(trifluoromethyl)-10-(2,4,6-trifluorophenyl)-2H-[1,4]thiazino[2,3,4-ij]quinazolin-5(3H)-one (8) (54 mg, 0.1 mmol) and triethyl amine (30 mg, 0.3 mmol) in dichloromethane (2 ml) was added acrylic anhydride (13 mg, 0.1 mmol) at 0° C. The mixture was stirred at 0° C. for 3 hours. After completion, the mixture was poured into ice-water (30 mL) and extracted with ethyl acetate (20 mL×3). After Concentration and the residue was purified by chromatography column (dichloromethane/methanol=60/1 to 30/1) to afford (S)-7-((3S,5R)-4-acryloyl-3,5-dimethylpiperazin-1-yl)-3-(methoxymethyl)-9-(trifluoromethyl)-10-(2,4,6-trifluorophenyl)-2H-[1,4]thiazino[2,3,4-ij]quinazolin-5(3H)-one (9) (6 mg, yield: 10%) as a white solid. MS (ESI) m/z 613.6 [M+H]+.

$^1$H NMR (400 MHz, CDCl3) δ 8.09 (s, 1H), 6.82 (t, J=7.2 Hz, 2H), 6.62 (dd, J=10.8 Hz, J=16.8 Hz, 1H), 6.40 (dd, J=1.6 Hz, J=16.4 Hz, 1H), 5.77 (dd, J=1.6 Hz, J=10.4 Hz, 1H), 5.50-5.45 (m, 1H), 4.85-4.52 (m, 2H), 4.22-4.16 (m, 2H), 3.67-3.60 (m, 2H), 3.40 (s, 3H), 3.37-3.30 (m, 3H), 3.07 (dd, J=2.8 Hz, J=13.2 Hz, 1H), 1.62 (d, J=6.8 Hz, 3H), 1.47 (d, J=7.2 Hz, 3H).

Example 2014: (3S,10R)-7-((3S,5R)-4-acryloyl-3,5-dimethylpiperazin-1-yl)-10-(6-fluoro-1-methyl-1H-indazol-7-yl)-3-(methoxymethyl)-9-(trifluoromethyl)-2,3-dihydro-5H-[1,4]thiazino[2,3,4-ij]quinazolin-5-one (6)

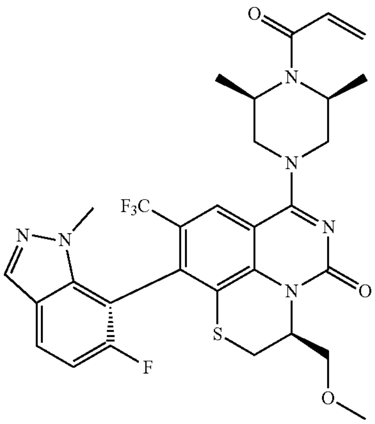

Reaction Scheme

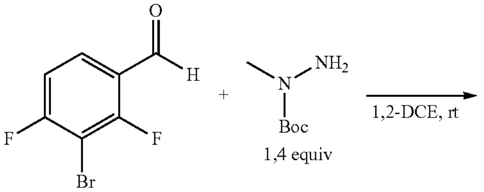

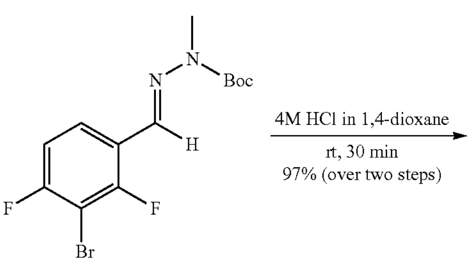

-continued

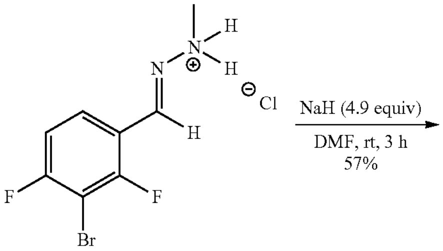

1

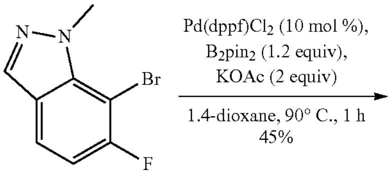

2

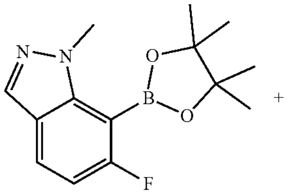

3

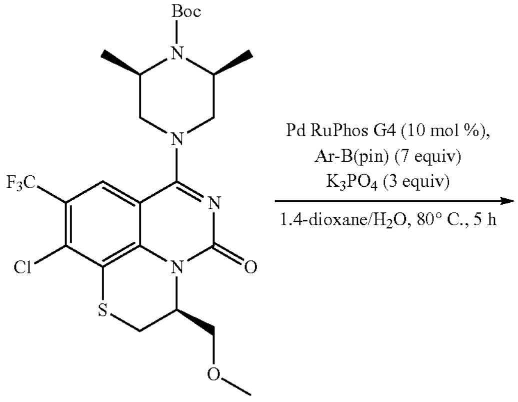

4

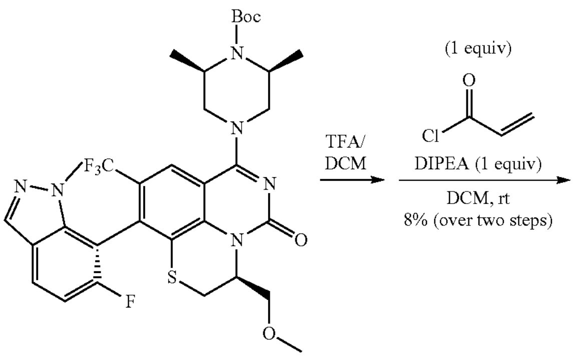

5

-continued

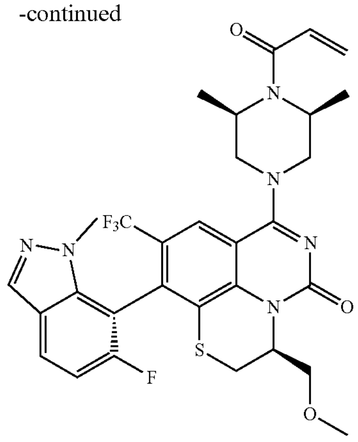

6

(E)-2-(3-Bromo-2,4-difluorobenzylidene)-1-methylhydrazin-1-ium chloride (1)

3-Bromo-2,4-difluorobenzaldehyde (4.0 g, 18.1 mmol, 1 equiv) was added to a 250 mL round-bottom flask under a $N_2$ atmosphere and dissolved in 1,2-dichloroethane (180 mL). Next, tert-butyl 1-methylhydrazine-1-carboxylate (3.8 mL, 25.34 mmol, 1.4 equiv, den. 0.985 g/mL) was added by syringe and the reaction mixture was stirred at room temperature. After 2.5 h, the solvent was removed by rotary evaporation (full conversion determined by LC-MS). Next, 4N HCl in 1,4-dioxane (45 mL) was added in portions (ca. 10 min) to the resulting colorless liquid. The reaction mixture was stirred at room temperature for 1 h. The white precipitate was collected using a Büchner funnel, washed with THF (100 mL) and dried under high vacuum to afford (E)-2-(3-bromo-2,4-difluorobenzylidene)-1-methylhydrazin-1-ium chloride as a pale-yellow solid (1) (6.13 g, 97%): $^1$H NMR (400 MHz, DMSO-$d_6$) δ 8.91-8.30 (br s, 1H), 7.61-7.51 (m, 1H), 7.35-7.24 (m, 1H), 7.14-7.05 (m, 1H), 2.84 (s, 2H), 2.59 (s, 1H); LRMS-ESI (m/z) $[M+H]^+$ calculated for $C_8H_8BrF_2N_2$ 248.98, found 249.0.

7-Bromo-6-fluoro-1-methyl-1H-indazole (2)

Sodium hydride (60 wt % in mineral oil, 756 mg, 18.9 mmol, 3.6 equiv) was added to a 100 mL round-bottom flask under a $N_2$ atmosphere and purged with $N_2$ for 30 min prior to the addition of DMF (20 mL). Next, (E)-2-(3-bromo-2,4-difluorobenzylidene)-1-methylhydrazin-1-ium chloride (1) (1.5 g, 5.25 mmol, 1 equiv) was added to the flask at room temperature in two portions. After 2.5 h, additional sodium hydride (60 wt % in mineral oil, 210 mg, 5.25 mmol, 1 equiv) was added. After another 1 h, additional sodium hydride (60 wt % in mineral oil, 53 mg, 1.31 mmol, 0.25 equiv) was added. After 30 min, the reaction mixture was cooled 0° C. and saturated aqueous $NH_4Cl$ (ca. 1 mL) was slowly added to the mixture. The resulting solution was transferred to a separatory funnel using EtOAc (200 mL) and the organic layer was washed with $H_2O$ (50 mL, 2×). The aqueous phases were combined and extracted with EtOAc (200 mL). The organic layers were combined and dried over $Na_2SO_4$ and the solvent was removed by rotary evaporation. The crude material was purified by flash column chromatography using an Isolera One Biotage instrument (0-25% EtOAc/hexanes, 25 g column, 0% (5 CV), 0-5% (10 CV), 5-25% (1 CV), 25% (10 CV), to provide 2 (760 mg, 63%) as an orange/yellow solid: TLC (5% EtOAc/hexanes) $R_f$=0.31; $^1$H NMR (400 MHz, $CDCl_3$) δ 8.04 (s, 1H), 7.44 (dd, J=8.1, 4.5 Hz, 1H), 6.65 (t, J=8.6 Hz, 1H), 4.42 (s, 3H); LRMS-ESI (m/z) $[M+H]^+$ calculated for $C_8H_7BrFN_2$ 228.98, found 229.0.

6-Fluoro-1-methyl-7-(4,4,5,5-tetramethyl-1,3,2-dioxaborolan-2-yl)-1H-indazole (3)

Compound 2 (200 mg, 0.87 mmol, 1 equiv) was dissolved in 1,4-dioxane (12.5 mL, 0.07 M) in a 50 mL bomb-flask. The resulting mixture was purged with $N_2$ for 30 min prior to the addition of Pd(dppf)$Cl_2$ (64 mg, 0.087 mmol, 10 mol %), KOAc (171 mg, 1.74 mmol, 2 equiv), and $B_2(pin)_2$ (265 mg, 1.044 mmol, 1.2 equiv), and then bubbled with $N_2$ for an additional 5 min. The flask placed on a heated block at 90° C. An additional 200 mg batch was set up using the same procedure. After 1 h, both batches were combined and filtered through Celite 545 using DCM (ca. 50 mL) and the solvent was removed by rotary evaporation. The crude material was purified by flash column chromatography using an Isolera One Biotage instrument (0-20% EtOAc/hexanes, 25 g column, 0% (5 CV), 0-5% (10 CV), 5% (5 CV), 5-20% (1 CV), 20% (5 CV)), to provide 3 (215 mg, 45%) as a yellow solid: TLC (10% EtOAc/hexanes) $R_f$=0.22; $^1$H NMR (400 MHz, $CDCl_3$) δ 8.07 (s, 1H), 7.86 (dd, J=7.8, 5.8 Hz, 1H), 6.77 (dd, J=9.6, 7.8 Hz, 1H), 4.32 (s, 3H), 1.40 (s, 12H); LRMS-ESI (m/z) $[M+H]^+$ calculated for $C_{14}H_{19}BFN_2O_2$ 277.15, found 277.2.

tert-Butyl (2S,6R)-4-((3S,10R)-10-(6-fluoro-1-methyl-1H-indazol-7-yl)-3-(methoxymethyl)-5-oxo-9-(trifluoromethyl)-2,3-dihydro-5H-[1,4]thiazino[2,3,4-ij]quinazolin-7-yl)-2,6-dimethylpiperazine-1-carboxylate (5)

Compound 4 (50 mg, 0.089 mmol, 1 equiv) was dissolved in 1,4-dioxane and $H_2O$ (3.2 mL, 0.8 mL, respectively, 0.02 M). The resulting mixture was purged with $N_2$ for 30 min prior to the addition of RuPhos Pd G4 (7.6 mg, 0.0089 mmol, 10 mol %), $K_3PO_4$ (57 mg, 0.267 mmol, 3 equiv), and 6-fluoro-1-methyl-7-(4,4,5,5-tetramethyl-1,3,2-dioxaborolan-2-yl)-1H-indazole (3) (174 mg, 0.63 mmol, 7 equiv). The microwave vial was fitted with a crimp-top cap, bubbled with $N_2$ for an additional 5 min, and placed on a heated block at 80° C. The resulting reaction mixture was homogenous. After 5 h, the vial was removed from the heating block, allowed to cool, and the solvent was removed by rotary evaporation. The crude material was purified by preparative thin-layer chromatography (Silica Gel 60 $F_{254}$, 0.5 mm, 20×20 cm, 2 plates) using 3% MeOH/$CH_2Cl_2$ to provide 30 mg of 5 as a yellow oil in decent purity. The material was used in the subsequent step: LRMS-ESI (m/z) $[M+H]^+$ calculated for $C_{32}H_{37}F_4N_6O_4S$ 677.25, found 677.3.

(3S,10R)-7-((3S,5R)-4-acryloyl-3,5-dimethylpiperazin-1-yl)-10-(6-fluoro-1-methyl-1H-indazol-7-yl)-3-(methoxymethyl)-9-(trifluoromethyl)-2,3-dihydro-5H-[1,4]thiazino[2,3,4-ij]quinazolin-5-one (6)

Boc deprotection and acrylation were carried out using the same procedures described in other examples. The title compound 6 was obtained as a yellow solid (1.53 mg, 5% over two-steps).

$^1$H NMR (400 MHz, MeOH-$d_4$) δ 8.22 (s, 1H), 8.16 (s, 1H), 7.18 (dd, J=8.0, 4.8 Hz, 1H), 6.97 (dd, J=9.7, 8.0 Hz,

1H), 6.85 (dd, J=16.7, 10.5 Hz, 1H), 6.30 (dd, J=16.6, 2.0 Hz, 1H), 5.81 (dd, J=10.6, 2.0 Hz, 1H), 5.39-5.31 (m, 1H), 4.84-4.46 (m, 3H), 4.39 (d, J=13.8 Hz, 1H), 4.30 (d, J=13.6 Hz, 1H), 3.73-3.60 (m, 2H), 3.56 (s, 3H), 3.55-3.38 (m, 3H), 3.36 (s, 2H), 3.35-3.33 (m, 1H), 3.15 (dd, J=13.7, 3.0 Hz, 1H), 1.60 (d, J=7.0 Hz, 3H), 1.47-1.39 (m, 3H); LRMS-ESI (m/z) $[M+H]^+$ calculated for $C_{30}H_{31}F_4N_6O_3S$ 631.21, found 631.2.

Example 2018 (also Example 2027): (3S)-7-((3S, 5R)-4-Acryloyl-3,5-dimethylpiperazin-1-yl)-10-(2,4-difluoro-5-hydroxyphenyl)-3-(methoxymethyl)-9-(trifluoromethyl)-2,3-dihydro-5H-[1,4]thiazino[2,3,4-ij]quinazolin-5-one (3)

3

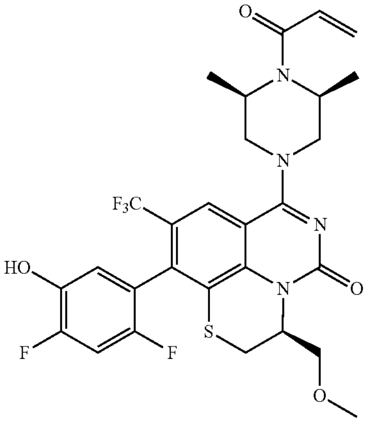

Reaction Scheme

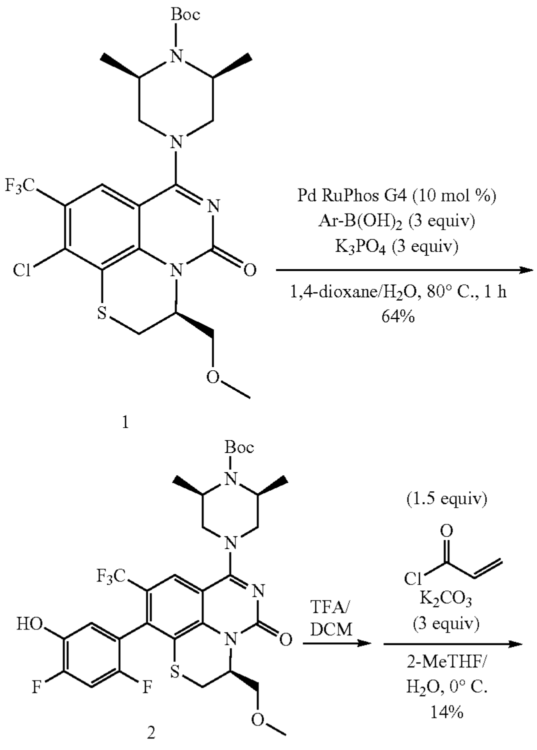

-continued

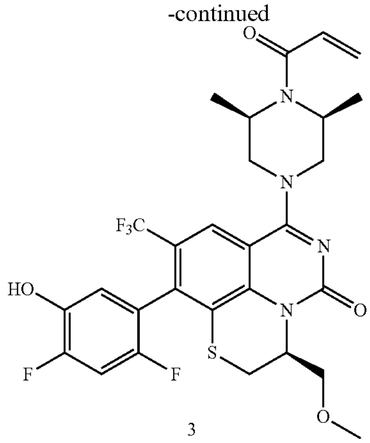

3 tert-Butyl (2S,6R)-4-((3S)-10-(2,4-difluoro-5-hydroxyphenyl)-3-(methoxymethyl)-5-oxo-9-(trifluoromethyl)-2,3-dihydro-5H-[1,4]thiazino[2,3,4-ij]quinazolin-7-yl)-2,6-dimethylpiperazine-1-carboxylate (2)

Compound 1 (50 mg, 0.089 mmol, 1 equiv) was dissolved in 1,4-dioxane and $H_2O$ (3.2 mL, 0.8 mL, respectively, 0.022 M). The resulting mixture was purged with $N_2$ for 30 min prior to the addition of RuPhos Pd G4 (7.6 mg, 0.0089 mmol, 10 mol %), $K_3PO_4$ (56.7 mg, 0.267 mmol, 3 equiv), and (2,4-difluoro-5-hydroxyphenyl)boronic acid (46.4 mg, 0.267 mmol, 3 equiv). The microwave vial was fitted with a crimp-top cap, bubbled with $N_2$ for an additional 5 min, and placed on a heated block at 80° C. The resulting reaction mixture was homogenous. After 1 h, the vial was removed from the heating block, allowed to cool, and the solvent was removed by rotary evaporation (full conversion determined by LC-MS). The crude material was purified by flash column chromatography using an Isolera One Biotage instrument (0-75% EtOAc/hexanes, 10 g column, 0% (5 CV), 0-50% (10 CV), 50% (5 CV), 50-75% (2 CV), 75% (10 CV)) to afford the desired product 2 as a yellow solid (36 mg, 62%): TLC (50% EtOAc/hexanes) $R_f$=0.15/0.08 (atropisomers); $^1H$ NMR (400 MHz, $CDCl_3$, mixture of both atropisomers) δ 8.05 (s, 0.5H), 8.00 (s, 0.5H), 6.98 (ddd, J=10.2, 8.6, 4.7 Hz, 1H), 6.85 (dd, J=9.3, 6.8 Hz, 0.5H), 6.72 (t, J=8.1 Hz, 0.5H), 5.53-5.37 (m, 1H), 4.47-4.25 (m, 2H), 4.23-3.92 (m, 2H), 3.75-3.50 (m, 2H), 3.45-2.98 (m, 4H), 3.38 (s, 3H), 1.54 (t, J=7.0 Hz, 3H), 1.50 (s, 9H), 1.35 (dd, J=9.7, 6.9 Hz, 3H); LRMS-ESI (m/z) $[M+H]^+$ calculated for $C_{30}H_{34}F_5N_4O_5S$ 657.22, found 657.2.

(3S)-7-((3S,5R)-4-Acryloyl-3,5-dimethylpiperazin-1-yl)-10-(2,4-difluoro-5-hydroxyphenyl)-3-(methoxymethyl)-9-(trifluoromethyl)-2,3-dihydro-5H-[1,4]thiazino[2,3,4-ij]quinazolin-5-one (3)

Compound 2 (33 mg, 0.05 mmol, 1 equiv) was dissolved in anhydrous $CH_2Cl_2$ (3 mL) in a 20 dr vial followed by the addition of $CF_3COOH$ (1 mL) at room temperature and capped. After 30 min, the reaction was determined to be complete by LC-MS and the solvent was removed by rotary evaporation. The resulting solid was dissolved in MeOH, loaded onto a HyperSep SCX plug, and flushed with MeOH (ca. 30 mL). Next, the desired product was eluted with 1N $NH_3$ in MeOH (ca. 30 mL) and collected. The solvent was removed by rotary evaporation and the solid was dissolved in 2-MeTHF (2.5 mL) and $H_2O$ (2.5 mL). The reaction mixture was cooled to 0° C. and $K_2CO_3$ (21 mg, 0.15 mmol, 3 equiv) was added. Next, acryloyl chloride (6.1 μL, 0.075 mmol, 1.5 equiv) was added by syringe in ca. 3 portions at 0° C. over 1 h. After 1.5 h, the solvent was removed by rotary evaporation. The crude material was dissolved in MeOH, filtered with a 0.45 μM PTFE plug, and purified by preparative RP-HPLC (Luna 5 μM C18(2) 100 Å, 100×30 mm, 5-95% MeCN+0.1% (v/v) HCOOH and $H_2O$+0.1% (v/v) HCOOH). The product fractions were collected, and the solvent was removed by rotary evaporation, followed by lyophilization (−91 to −71° C.; <0.01 mbar) in deionized water to afford 3 (4.2 mg, 14%) as a white solid. Note: Regioselectivity and acrylamide formation was confirmed by $^1$H NMR and NOESY analysis: $^1$H NMR (400 MHz, MeOH-$d_4$) δ 8.13 (s, 1H), 7.08 (t, J=10.0 Hz, 1H), 6.90-6.72 (m, 2H), 6.29 (dd, J=16.6, 2.0 Hz, 1H), 5.80 (dd, J=10.5, 2.0 Hz, 1H), 5.41-5.28 (m, 1H), 4.83-4.50 (m, 2H), 4.33 (d, J=13.8 Hz, 1H), 4.25 (d, J=13.6 Hz, 1H), 3.73 (t, J=9.2 Hz, 1H), 3.61 (dd, J=9.2, 4.7 Hz, 1H), 3.48 (dd, J=13.5, 4.8 Hz, 1H), 3.44-3.33 (m, 2H), 3.40 (s, 3H), 3.13 (dd, J=13.8, 2.9 Hz, 1H), 1.58 (d, J=6.9 Hz, 3H), 1.42 (d, J=6.9 Hz, 3H); LRMS-ESI (m/z) $[M+H]^+$ calculated for $C_{28}H_{28}F_5N_4O_4S$ 611.18, found 611.2.

Example 2028 and 2029: (3S,10R)-7-((3S,5R)-4-Acryloyl-3,5-dimethylpiperazin-1-yl)-10-(5-bromo-2,4-difluorophenyl)-3-(methoxymethyl)-9-(trifluoromethyl)-2,3-dihydro-5H-[1,4]thiazino[2,3,4-ij]quinazolin-5-one (P1) and (3S,10S)-7-((3S,5R)-4-Acryloyl-3,5-dimethylpiperazin-1-yl)-10-(5-bromo-2,4-difluorophenyl)-3-(methoxymethyl)-9-(trifluoromethyl)-2,3-dihydro-5H-[1,4]thiazino[2,3,4-ij]quinazolin-5-one (P2)

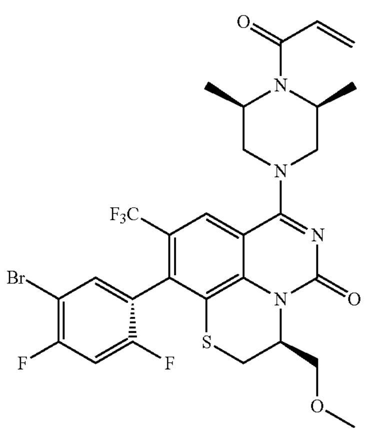

-continued

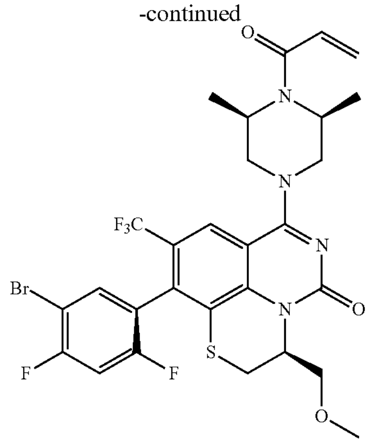

Reaction Scheme

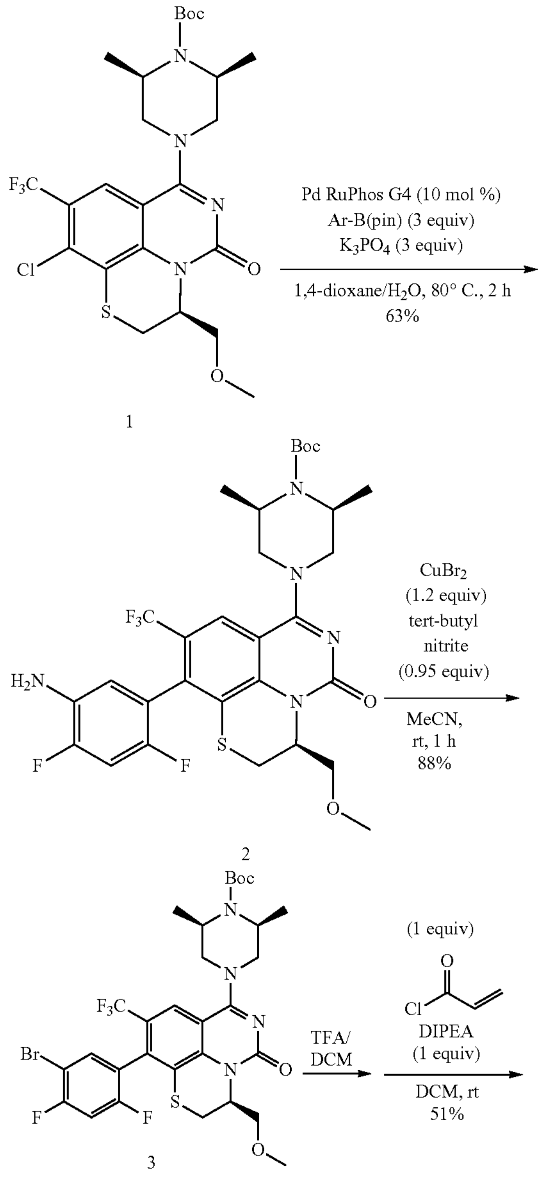

-continued

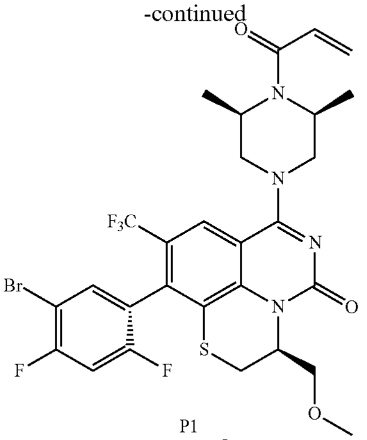

P1

+

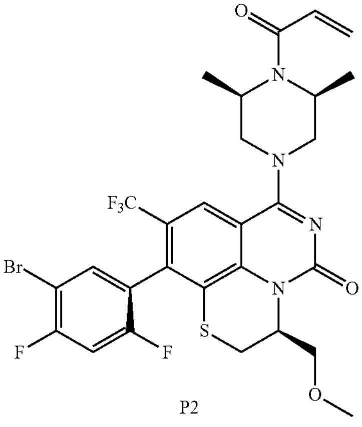

P2 tert-Butyl (2S,6R)-4-((3S)-10-(5-amino-2,4-difluorophenyl)-3-(methoxymethyl)-5-oxo-9-(trifluoromethyl)-2,3-dihydro-5H-[1,4]thiazino[2,3,4-ij]quinazolin-7-yl)-2,6-dimethylpiperazine-1-carboxylate (2)

Compound 1 (73 mg, 0.13 mmol, 1 equiv) was dissolved in 1,4-dioxane and $H_2O$ (3.0 mL, 0.75 mL, respectively, 0.035 M). The resulting mixture was purged with $N_2$ for 30 min prior to the addition of RuPhos Pd G4 (11 mg, 0.013 mmol, 10 mol %), $K_3PO_4$ (83 mg, 0.39 mmol, 3 equiv), and 2,4-difluoro-5-(4,4,5,5-tetramethyl-1,3,2-dioxaborolan-2-yl)aniline (99 mg, 0.39 mmol, 3 equiv). The microwave vial was fitted with a crimp-top cap, bubbled with $N_2$ for an additional 5 min, and placed on a heated block at 80° C. The resulting reaction mixture was homogenous. After 2 h, the vial was removed from the heating block, allowed to cool, and the solvent was removed by rotary evaporation (full conversion determined by LC-MS). The crude material was purified by flash column chromatography using an Isolera One Biotage instrument (0-100% EtOAc/hexanes, 10 g column, 0% (5 CV), 0-75% (10 CV), 75% (5 CV), 75-100% (1 CV), 100% (5 CV)), to provide 2 (53.4 mg, 63%) as a beige solid: TLC (50% EtOAc/hexanes) $R_f$=0.17/0.11 (both atropisomers); $^1H$ NMR (400 MHz, $CDCl_3$) δ 8.05 (s, 1H), 6.97-6.87 (m, 1H), 6.63 (t, J=8.1 Hz, 1H), 5.56-5.36 (m, 1H), 4.49-4.28 (m, 2H), 4.23-4.03 (m, 2H), 3.73-3.52 (m, 2H), 3.44-3.14 (m, 7H), 3.01 (d, J=13.6 Hz, 1H), 1.53 (d, J=7.1 Hz, 3H), 1.49 (s, 9H), 1.36 (d, J=6.8 Hz, 3H); LRMS-ESI (m/z) $[M+H]^+$ calculated for $C_{30}H_{35}F_5N_5O_4S$ 656.23, found 656.2.

tert-Butyl (2S,6R)-4-((3S)-10-(5-bromo-2,4-difluorophenyl)-3-(methoxymethyl)-5-oxo-9-(trifluoromethyl)-2,3-dihydro-5H-[1,4]thiazino[2,3,4-ij]quinazolin-7-yl)-2,6-dimethylpiperazine-1-carboxylate (3)

$CuBr_2$ (23 mg, 0.099 mmol, 1.2 equiv) was added to a 5 mL microwave vial, purged with $N_2$ for 30 min, and dissolved in MeCN (600 μL). Next, tert-butyl nitrite (8.5 μL, 0.078 mmol, 0.95 equiv, den. 0.867 g/mL) was added at room temperature resulting in a green/blue solution. Compound 2 (54 mg, 0.082 mmol, 1 equiv) as a solution in MeCN (2.0 mL) under a $N_2$ atmosphere was then added by syringe to the copper solution over ca. 5 min. After 1 h, the reaction mixture was diluted with EtOAc and filtered through Celite 545 using EtOAc (50 mL). The solvent was removed by rotary evaporation and the crude material was purified by flash column chromatography using an Isolera One Biotage instrument (0-6% MeOH/$CH_2Cl_2$, 10 g column, 0% (5 CV), 0-3% (10 CV), 3% (5 CV), 3-4% (1 CV), 4% (5 CV), 4-6% (1 CV), 6% (5 CV)), to provide 3 (49 mg, 88%) as a yellow solid: TLC (3% MeOH/$CH_2Cl_2$) $R_f$=0.34; $^1H$ NMR (400 MHz, $CDCl_3$) δ 8.07 (s, 1H), 7.41 (t, J=7.3 Hz, 1H), 7.05 (td, J=8.5, 2.7 Hz, 1H), 5.52-5.39 (m, 1H), 4.44-4.31 (m, 2H), 4.22-4.05 (m, 2H), 3.71-3.56 (m, 2H), 3.45-3.33 (m, 4H), 3.32-3.18 (m, 2H), 3.01 (dt, J=13.7, 3.7 Hz, 1H), 1.53 (d, J=7.0 Hz, 3H), 1.50 (s, 9H), 1.37 (t, J=6.4 Hz, 3H); LRMS-ESI (m/z) $[M+H]^+$ calculated for $C_{30}H_{33}BrF_5N_4O_4S$ 719.13, found 719.2.

(3S,10R)-7-((3S,5R)-4-Acryloyl-3,5-dimethylpiperazin-1-yl)-10-(5-bromo-2,4-difluorophenyl)-3-(methoxymethyl)-9-(trifluoromethyl)-2,3-dihydro-5H-[1,4]thiazino[2,3,4-ij]quinazolin-5-one (P1) and (3S,10S)-7-((3S,5R)-4-Acryloyl-3,5-dimethylpiperazin-1-yl)-10-(5-bromo-2,4-difluorophenyl)-3-(methoxymethyl)-9-(trifluoromethyl)-2,3-dihydro-5H-[1,4]thiazino[2,3,4-ij]quinazolin-5-one (P2)

Compound 3 (49 mg, 0.068 mmol, 1 equiv) was dissolved in anhydrous $CH_2Cl_2$ (3 mL) in a 20 dr vial followed by the addition of $CF_3COOH$ (1 mL) at room temperature and capped. After 30 min the solvent was removed by rotary evaporation. The reaction mixture was dissolved in MeOH, loaded onto a HyperSep SCX plug, and flushed with MeOH (ca. 30 mL). Next, the desired intermediate was eluted with 1N $NH_3$ in MeOH (ca. 30 mL) and collected. The solvent was removed by rotary evaporation and the crude material was dissolved in anhydrous $CH_2Cl_2$ (6 mL) in a 20 dr vial and capped. Next, DIPEA (11.8 μL, 0.068 mmol, 1 equiv) was added by syringe to the reaction at room temperature followed by acryloyl chloride (5.5 μL, 0.068 mmol, 1 equiv) and capped. After 10 min, the reaction was determined to be complete by LC-MS and the solvent was removed by rotary evaporation. The crude material was dissolved in MeOH, filtered with a 0.45 μM PTFE plug, and purified by preparative RP-HPLC (Luna 5 μM C18(2) 100 Å, 100×30 mm, 5-95% MeCN+0.1% (v/v) HCOOH and $H_2O$+0.1% (v/v) HCOOH). The product fractions were collected, and the solvent was removed by rotary evaporation, followed by lyophilization (−91 to −71° C.; <0.01 mbar) in deionized water to afford 23.2 mg (51% yield) of P1 and P2 as a beige solid. The atropisomers were separated by chiral preparative HPLC on a CHIRALPAK® AD-H column to afford P1 (10.3 mg, 22%) and P2 (11.0 mg, 24%) as white solids.

P1: $^1H$ NMR (400 MHz, MeOH-$d_4$) δ 8.15 (s, 1H), 7.66 (t, J=7.4 Hz, 1H), 7.34 (t, J=9.0 Hz, 1H), 6.84 (dd, J=16.7, 10.6 Hz, 1H), 6.29 (dd, J=16.7, 2.0 Hz, 1H), 5.80 (dd, J=10.6, 2.0 Hz, 1H), 5.41-5.31 (m, 1H), 4.86-4.51 (m, 2H), 4.33 (d, J=13.7 Hz, 1H), 4.26 (d, J=13.4 Hz, 1H), 3.75 (t, J=9.2 Hz, 1H), 3.62 (dd, J=9.2, 4.8 Hz, 1H), 3.49 (dd, J=13.5, 4.7 Hz, 1H), 3.45-3.36 (m, 2H), 3.40 (s, 3H), 3.15 (dd, J=13.7, 2.9 Hz, 1H), 1.57 (d, J=7.1 Hz, 3H), 1.42 (d, J=7.0 Hz, 3H); LRMS-ESI (m/z) $[M+H]^+$ calculated for $C_{28}H_{27}BrF_5N_4O_3S$ 673.09, found 673.2.

P2: $^1H$ NMR (400 MHz, MeOH-$d_4$) δ 8.15 (s, 1H), 7.60 (t, J=7.5 Hz, 1H), 7.35 (t, J=8.9 Hz, 1H), 6.84 (dd, J=16.7, 10.6 Hz, 1H), 6.29 (dd, J=16.7, 2.0 Hz, 1H), 5.80 (dd, J=10.6, 2.0 Hz, 1H), 5.43-5.32 (m, 1H), 4.86-4.52 (m, 2H), 4.35 (d, J=13.6 Hz, 1H), 4.26 (d, J=13.6 Hz, 1H), 3.69 (t, J=9.1 Hz, 1H), 3.60 (dd, J=9.2, 4.9 Hz, 1H), 3.52 (dd, J=13.6, 4.7 Hz, 1H), 3.47-3.35 (m, 2H), 3.39 (s, 3H), 3.17 (dd, J=13.7, 3.0 Hz, 1H), 1.56 (d, J=6.9 Hz, 3H), 1.42 (d, J=6.9 Hz, 3H); LRMS-ESI (m/z) $[M+H]^+$ calculated for $C_{28}H_{27}BrF_5N_4O_3S$ 673.09, found 673.2.

Example 2030 and 2031: (3S,10R)-7-((3S,5R)-4-Acryloyl-3,5-dimethylpiperazin-1-yl)-10-(5-amino-2,4-difluorophenyl)-3-(methoxymethyl)-9-(trifluoromethyl)-2,3-dihydro-5H-[1,4]thiazino[2,3,4-ij]quinazolin-5-one, formate salt (P1) and (3S,10S)-7-((3S,5R)-4-Acryloyl-3,5-dimethylpiperazin-1-yl)-10-(5-amino-2,4-difluorophenyl)-3-(methoxymethyl)-9-(trifluoromethyl)-2,3-dihydro-5H-[1,4]thiazino[2,3,4-ij]quinazolin-5-one, formate salt (P2)

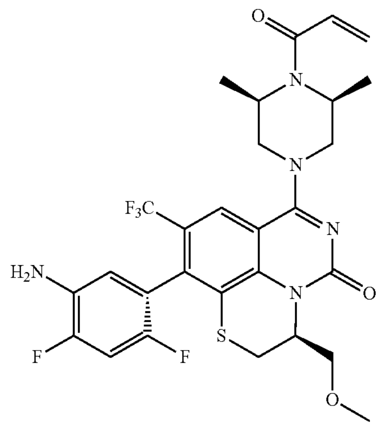

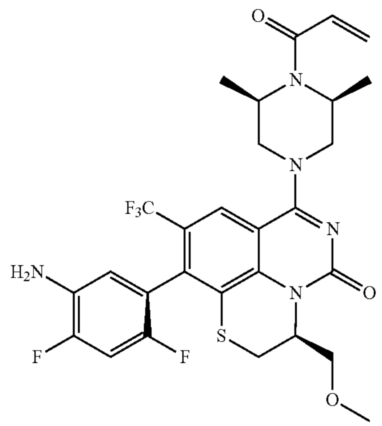

Reaction Scheme

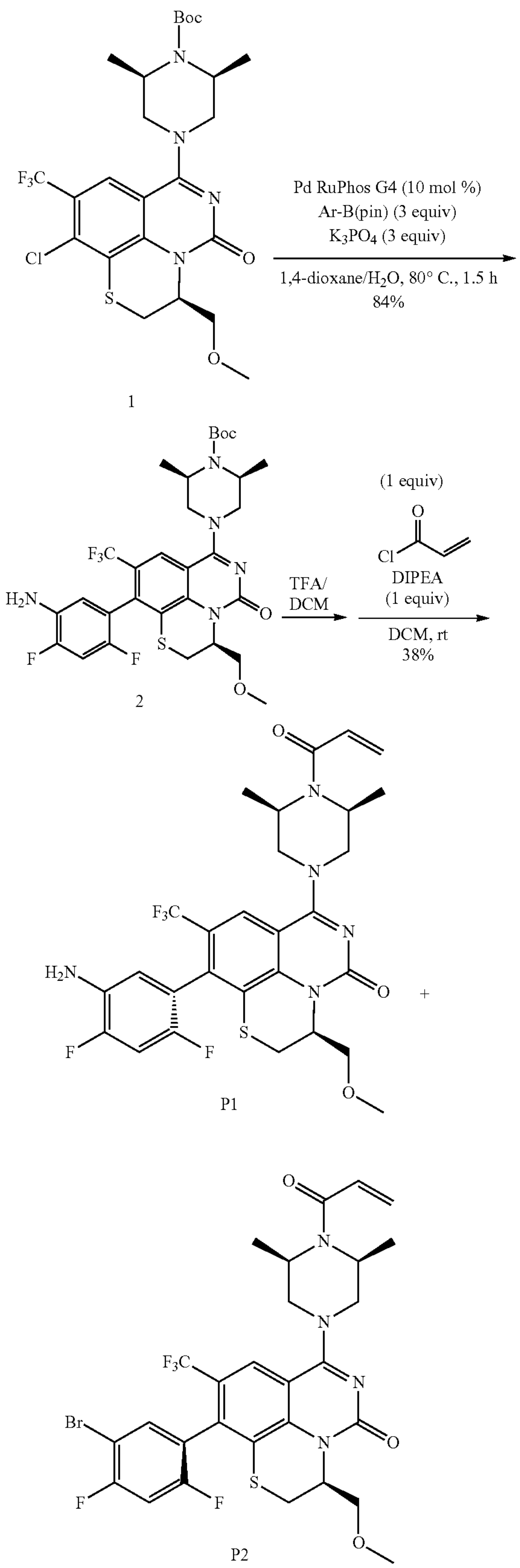

1

2

P1

P2 tert-Butyl (2S,6R)-4-((3S)-10-(5-amino-2,4-difluorophenyl)-3-(methoxymethyl)-5-oxo-9-(trifluoromethyl)-2,3-dihydro-5H-[1,4]thiazino[2,3,4-ij]quinazolin-7-yl)-2,6-dimethylpiperazine-1-carboxylate (2)

Compound 1 (50 mg, 0.089 mmol, 1 equiv) was dissolved in 1,4-dioxane and $H_2O$ (2.5 mL, 0.5 mL, respectively, 0.030 M). The resulting mixture was purged with $N_2$ for 30 min prior to the addition of RuPhos Pd G4 (7.6 mg, 0.0089 mmol, 10 mol %), $K_3PO_4$ (57 mg, 0.267 mmol, 3 equiv), and 2,4-difluoro-5-(4,4,5,5-tetramethyl-1,3,2-dioxaborolan-2-yl)aniline (68 mg, 0.267 mmol, 3 equiv). The microwave vial was fitted with a crimp-top cap, bubbled with $N_2$ for an additional 5 min, and placed on a heated block at 80° C. The resulting reaction mixture was homogenous. After 1.5 h, the vial was removed from the heating block, allowed to cool, and the solvent was removed by rotary evaporation (full conversion determined by LC-MS). The crude material was purified by flash column chromatography using an Isolera One Biotage instrument (0-100% EtOAc/hexanes, 10 g column, 0% (5 CV), 0-50% (10 CV), 50% (5 CV), 50-100 (5 CV), 100% (5 CV) to afford the desired product (2) as a yellow solid (49 mg, 84%): TLC (50% EtOAc/hexanes) $R_f$=0.18, 0.10 (atropisomers); $^1$H NMR (400 MHz, $CDCl_3$) δ 8.06 (s, 1H), 6.96 (t, J=9.5 Hz, 1H), 6.91-6.75 (m, 1H), 5.52-5.38 (m, 1H), 4.46-4.28 (m, 2H), 4.21-4.14 (m, 2H), 3.73-3.53 (m, 2H), 3.45-3.37 (m, 3H), 3.37-3.17 (m, 3H), 3.07-2.92 (m, 1H), 1.53 (d, J=6.9 Hz, 3H), 1.50 (s, 9H), 1.37 (dd, J=6.9, 4.3 Hz, 3H); LRMS-ESI (m/z) $[M+H]^+$ calculated for $C_{30}H_{35}F_5N_5O_4S$ 656.23, found 656.3.

(3S,10R)-7-((3S,5R)-4-Acryloyl-3,5-dimethylpiperazin-1-yl)-10-(5-amino-2,4-difluorophenyl)-3-(methoxymethyl)-9-(trifluoromethyl)-2,3-dihydro-5H-[1,4]thiazino[2,3,4-ij]quinazolin-5-one, formate salt (P1) and (3S,10S)-7-((3S,5R)-4-Acryloyl-3,5-dimethylpiperazin-1-yl)-10-(5-amino-2,4-difluorophenyl)-3-(methoxymethyl)-9-(trifluoromethyl)-2,3-dihydro-5H-[1,4]thiazino[2,3,4-ij]quinazolin-5-one, formate salt (P2)

Compound 2 (49 mg, 0.075 mmol, 1 equiv) was dissolved in anhydrous $CH_2Cl_2$ (3 mL) in a 20 dr vial followed by the addition of $CF_3COOH$ (1 mL) at room temperature and capped. After 20 min, the solvent was removed by rotary evaporation. The reaction mixture was dissolved in MeOH, loaded onto a HyperSep SCX plug, and flushed with MeOH (ca. 30 mL). Next, the desired intermediate was eluted with 1N $NH_3$ in MeOH (ca. 30 mL) and collected. The solvent was removed by rotary evaporation and the crude material was dissolved in anhydrous $CH_2Cl_2$ (3 mL) in a 20 dr vial and capped. Next, DIPEA (13.1 μL, 0.075 mmol, 1 equiv) was added by syringe to the reaction at room temperature followed by acryloyl chloride (6.1 μL, 0.075 mmol, 1 equiv) as a DCM (1 mL) solution over (ca. 20 min) and capped. After 10 min, the reaction was determined to be complete by LC-MS and the solvent was removed by rotary evaporation. The crude material was dissolved in MeOH, filtered with a 0.45 μM PTFE plug, and purified by preparative RP-HPLC (Luna 5 μM C18(2) 100 Å, 100×30 mm, 25-95% MeCN+0.1% (v/v) HCOOH and $H_2O$+0.1% (v/v) HCOOH). The product fractions were collected, and the solvent was removed by rotary evaporation, followed by lyophilization (−91 to −71° C.; <0.01 mbar) in deionized water to afford 9.6 mg (20% yield) of P1 and 8.8 mg (18% yield) of P2. Note: Regioselectivity and acrylamide formation was confirmed by $^1$H NMR and NOESY analysis.

P1: $^1$H NMR (400 MHz, MeOH-$d_4$) δ 8.12 (s, 1H), 6.98 (dd, J=11.1, 9.1 Hz, 1H), 6.84 (dd, J=16.7, 10.6 Hz, 1H), 6.71 (dd, J=9.5, 7.1 Hz, 1H), 6.29 (dd, J=16.7, 2.0 Hz, 1H), 5.84-5.76 (m, 1H), 5.41-5.29 (m, 1H), 4.85-4.47 (m, 2H), 4.32 (d, J=13.8 Hz, 1H), 4.25 (d, J=13.7 Hz, 1H), 3.72 (d, J=9.1 Hz, 1H), 3.61 (dd, J=9.1, 4.7 Hz, 1H), 3.47 (dd, J=13.6, 4.6 Hz, 1H), 3.43-3.33 (m, 2H), 3.39 (s, 3H), 3.12 (dd, J=13.7, 2.9 Hz, 1H), 1.58 (d, J=6.9 Hz, 3H), 1.42 (d, J=6.9 Hz, 3H); LRMS-ESI (m/z) $[M+H]^+$ calculated for $C_{28}H_{29}F_5N_5O_3S$ 610.19, found 610.2.

P2: $^1$H NMR (400 MHz, MeOH-$d_4$) δ 8.12 (s, 1H), 6.98 (dd, J=11.0, 9.1 Hz, 1H), 6.84 (dd, J=16.6, 10.6 Hz, 1H), 6.67 (dd, J=9.5, 7.1 Hz, 1H), 6.29 (dd, J=16.6, 2.1 Hz, 1H), 5.80 (dd, J=10.5, 2.0 Hz, 1H), 5.43-5.31 (m, 1H), 4.85-4.50 (m, 2H), 4.33 (d, J=13.6 Hz, 1H), 4.25 (d, J=13.6 Hz, 1H), 3.70 (t, J=9.1 Hz, 1H), 3.58 (dd, J=9.2, 4.9 Hz, 1H), 3.48 (dd, J=13.5, 4.7 Hz, 1H), 3.43-3.33 (m, 2H), 3.39 (s, 3H), 3.14 (dd, J=13.6, 2.9 Hz, 1H), 1.57 (d, J=6.9 Hz, 3H), 1.42 (d, J=6.9 Hz, 3H); LRMS-ESI (m/z) $[M+H]^+$ calculated for $C_{28}H_{29}F_5N_5O_3S$ 610.19, found 610.2.

Example 2056 and 2057: (3S,10R)-7-((3S,5R)-4-acryloyl-3,5-dimethylpiperazin-1-yl)-10-(2,4-difluoro-5-iodophenyl)-3-(methoxymethyl)-9-(trifluoromethyl)-2,3-dihydro-5H-[1,4]thiazino[2,3,4-ij]quinazolin-5-one (P1) and (3S,10S)-7-((3S,5R)-4-acryloyl-3,5-dimethylpiperazin-1-yl)-10-(2,4-difluoro-5-iodophenyl)-3-(methoxymethyl)-9-(trifluoromethyl)-2,3-dihydro-5H-[1,4]thiazino[2,3,4-ij]quinazolin-5-one (P2)

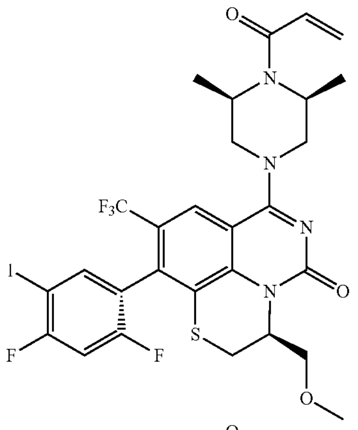

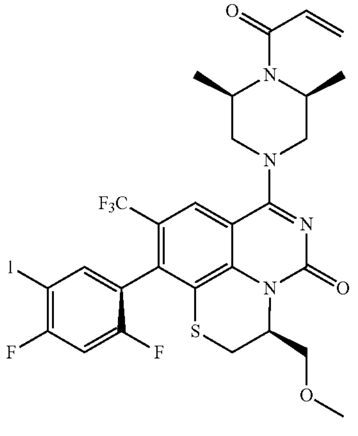

Reaction Scheme

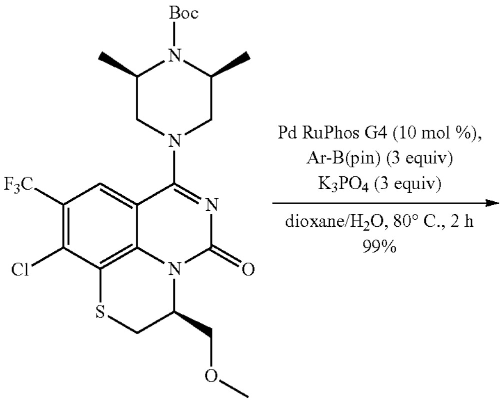

1

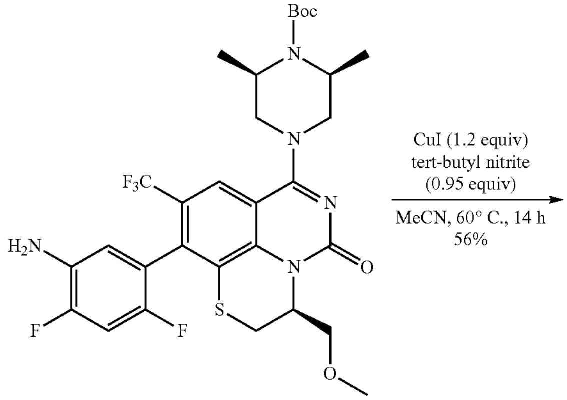

2

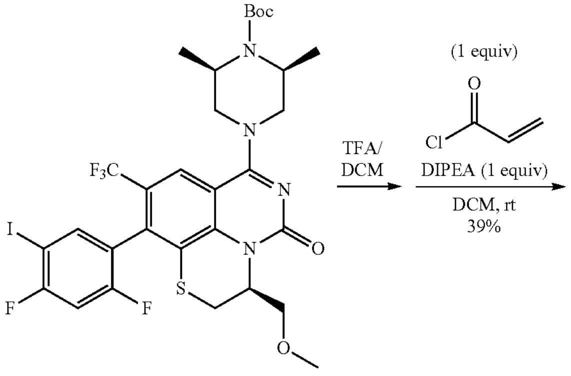

3

-continued

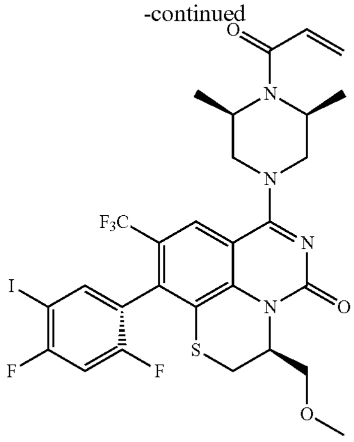

+

P1

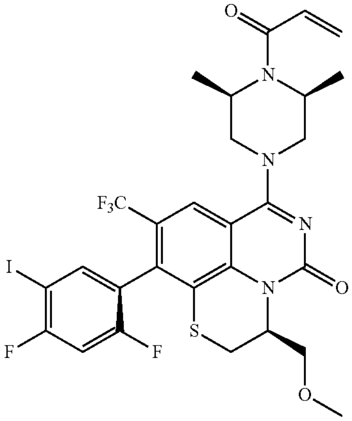

P2 tert-Butyl (2S,6R)-4-((3S)-10-(5-amino-2,4-difluorophenyl)-3-(methoxymethyl)-5-oxo-9-(trifluoromethyl)-2,3-dihydro-5H-[1,4]thiazino[2,3,4-ij]quinazolin-7-yl)-2,6-dimethylpiperazine-1-carboxylate (2)

Compound 1 (60 mg, 0.107 mmol, 1 equiv) was dissolved in 1,4-dioxane and $H_2O$ (2.5 mL, 0.5 mL, respectively, 0.036 M). The resulting mixture was purged with $N_2$ for 30 min prior to the addition of RuPhos Pd G4 (9.1 mg, 0.0107 mmol, 10 mol %), $K_3PO_4$ (68 mg, 0.321 mmol, 3 equiv), and 2,4-difluoro-5-(4,4,5,5-tetramethyl-1,3,2-dioxaborolan-2-yl)aniline (82 mg, 0.321 mmol, 3 equiv). The microwave vial was fitted with a crimp-top cap, bubbled with $N_2$ for an additional 5 min, and placed on a heated block at 80° C. The resulting reaction mixture was homogenous. After 2 h, the vial was removed from the heating block, allowed to cool, and the solvent was removed by rotary evaporation (full conversion determined by LC-MS). The crude material was purified by flash column chromatography using an Isolera One Biotage instrument (0-100% EtOAc/hexanes, 10 g column, 0% (5 CV), 0-75% (10 CV), 75% (5 CV), 75-100% (1 CV), 100% (5 CV)), to provide 2 (70 mg, 99%) as an orange/brown oil: TLC (50% EtOAc/hexanes) $R_f$=0.17/0.11 (atropisomers); $^1$H NMR (400 MHz, $CDCl_3$) δ 8.05 (s, 1H), 6.97-6.87 (m, 1H), 6.63 (t, J=8.1 Hz, 1H), 5.56-5.36 (m, 1H), 4.49-4.28 (m, 2H), 4.23-4.03 (m, 2H), 3.73-3.52 (m, 2H), 3.44-3.14 (m, 7H), 3.01 (d, J=13.6 Hz, 1H), 1.53 (d, J=7.1 Hz, 3H), 1.49 (s, 9H), 1.36 (d, J=6.8 Hz, 3H); LRMS-ESI (m/z) $[M+H]^+$ calculated for $C_{30}H_{35}F_5N_5O_4S$ 656.23, found 656.2.

tert-butyl (2S,6R)-4-((3S)-10-(2,4-difluoro-5-iodophenyl)-3-(methoxymethyl)-5-oxo-9-(trifluoromethyl)-2,3-dihydro-5H-[1,4]thiazino[2,3,4-ij]quinazolin-7-yl)-2,6-dimethylpiperazine-1-carboxylate (3)

CuI (24.4 mg, 0.128 mmol, 1.2 equiv) was added to a 5 mL microwave vial, purged with $N_2$ for 30 min, and dissolved in MeCN (0.5 mL). Next, tert-butyl nitrite (12.1 µL, 0.102 mmol, 0.95 equiv, den. 0.867 g/mL) was added at room temperature resulting in a yellow solution. Compound 2 (70 mg, 0.107 mmol, 1 equiv) as a solution in MeCN (2.0 mL) under a $N_2$ atmosphere was then added by syringe to the copper solution over ca. 5 min. The reaction mixture was placed on a heated block at 60° C. and heated for 14 h. Next, the solution was diluted with EtOAc and filtered through Celite 545 using EtOAc (50 mL). The solvent was removed by rotary evaporation and the crude material was purified by flash column chromatography using an Isolera One Biotage instrument (0-75% EtOAc/hexanes, 10 g column, 0% (5 CV), 0-50% (10 CV), 50% (5 CV), 50-75% (1 CV), 75% (5 CV)), to provide 3 (46 mg, 56%) as a yellow solid: TLC (50% EtOAc/hexanes) $R_f$=0.34/0.26 (atropisomers); $^1H$ NMR (400 MHz, $CDCl_3$) δ 8.07 (s, 1H), 7.62-7.54 (m, 1H), 7.06-6.93 (m, 1H), 5.54-5.39 (m, 1H), 4.45-4.29 (m, 2H), 4.22-4.02 (m, 2H), 3.71-3.53 (m, 2H), 3.44-3.40 (m, 1H), 3.39 (s, 3H), 3.38-3.21 (m, 3H), 3.07-2.95 (m, 1H), 1.57-1.52 (m, 3H), 1.50 (s, 9H), 1.42-1.33 (m, 3H); LRMS-ESI (m/z) $[M+H]^+$ calculated for $C_{30}H_{33}F_5IN_4O_4S$ 767.12, found 767.2.

(3S,10R)-7-((3S,5R)-4-acryloyl-3,5-dimethylpiperazin-1-yl)-10-(2,4-difluoro-5-iodophenyl)-3-(methoxymethyl)-9-(trifluoromethyl)-2,3-dihydro-5H-[1,4]thiazino[2,3,4-U]quinazolin-5-one (P1) and (3S,10S)-7-((3S,5R)-4-acryloyl-3,5-dimethylpiperazin-1-yl)-10-(2,4-difluoro-5-iodophenyl)-3-(methoxymethyl)-9-(trifluoromethyl)-2,3-dihydro-5H-[1,4]thiazino[2,3,4-U]quinazolin-5-one (P2)

Compound 3 (54 mg, 0.07 mmol, 1 equiv) was dissolved in anhydrous $CH_2Cl_2$ (3 mL) in a 20 dr vial followed by the addition of $CF_3COOH$ (1 mL) at room temperature and capped. After 45 min the solvent was removed by rotary evaporation. The reaction mixture was dissolved in MeOH, loaded onto a HyperSep SCX plug, and flushed with MeOH (ca. 30 mL). Next, the desired intermediate was eluted with 1N $NH_3$ in MeOH (ca. 30 mL) and collected. The solvent was removed by rotary evaporation and the crude material was dissolved in anhydrous $CH_2Cl_2$ (3 mL) in a 20 dr vial and capped. Next, DIPEA (12.2 µL, 0.07 mmol, 1 equiv) was added by syringe to the reaction at room temperature followed by acryloyl chloride (5.7 µL, 0.07 mmol, 1 equiv) and capped. After 15 min, the reaction was determined to be complete by LC-MS and the solvent was removed by rotary evaporation. The crude material was dissolved in MeOH, filtered with a 0.45 µM PTFE plug, and purified by preparative RP-HPLC (Luna 5 µM C18(2) 100 Å, 100×30 mm, 25-95% MeCN+0.1% (v/v) HCOOH and $H_2O$+0.1% (v/v) HCOOH). The product fractions were collected, and the solvent was removed by rotary evaporation, followed by lyophilization (−91 to −71° C.; <0.01 mbar) in deionized water to afford 11 mg (22% yield) of P1 and 8.5 mg (17% yield) of P2. P1 and P2 were further purified by chiral preparative HPLC on a CHIRALPAK® AD-H column (30% 2-isopropanol/heptane).

P1: $^1H$ NMR (400 MHz, MeOH-$d_4$) δ 8.14 (s, 1H), 7.78 (t, J=7.3 Hz, 1H), 7.24 (t, J=8.8 Hz, 1H), 6.84 (dd, J=16.7, 10.6 Hz, 1H), 6.29 (d, J=16.0 Hz, 1H), 5.80 (dd, J=10.5, 2.0 Hz, 1H), 5.42-5.30 (m, 1H), 4.84-4.51 (br s, 2H), 4.33 (d, J=13.3 Hz, 1H), 4.26 (d, J=13.5 Hz, 1H), 4.20 (s, 1H), 3.80-3.66 (m, 1H), 3.65-3.56 (m, 1H), 3.55-3.42 (m, 2H), 3.41 (s, 3H), 3.40-3.35 (m, 2H), 3.20-3.10 (m, 1H), 1.57 (d, J=6.8 Hz, 3H), 1.42 (d, J=6.9 Hz, 3H); LRMS-ESI (m/z) $[M+H]^+$ calculated for $C_{28}H_{27}F_5IN_4O_3S$ 721.08, found 721.2.

P2: $^1H$ NMR (400 MHz, MeOH-$d_4$) δ 8.14 (s, 1H), 7.73 (t, J=7.4 Hz, 1H), 7.25 (dd, J=9.4, 8.1 Hz, 1H), 6.84 (dd, J=16.7, 10.6 Hz, 1H), 6.29 (dd, J=16.7, 2.0 Hz, 1H), 5.80 (dd, J=10.6, 2.0 Hz, 1H), 5.43-5.31 (m, 1H), 4.84-4.55 (m, 2H), 4.35 (d, J=13.5 Hz, 1H), 4.26 (d, J=13.5 Hz, 1H), 4.18 (s, 1H), 3.69 (t, J=9.2 Hz, 1H), 3.59 (dd, J=9.3, 4.9 Hz, 1H), 3.51 (dd, J=13.5, 4.8 Hz, 1H), 3.46-3.38 (m, 1H), 3.39 (s, 3H), 3.38-3.35 (m, 1H), 3.17 (dd, J=13.6, 3.0 Hz, 1H), 1.57 (d, J=6.9 Hz, 3H), 1.42 (d, J=6.9 Hz, 3H); LRMS-ESI (m/z) $[M+H]^+$ calculated for $C_{28}H_{27}F_5IN_4O_3S$ 721.08, found 721.2.

Example 2015: (S)-7-((3S,5R)-4-acryloyl-3,5-dimethylpiperazin-1-yl)-10-(4-fluorophenyl)-3-((trideuteriomethoxy)methyl)-9-(trifluoromethyl)-2H-[1,4]thiazino[2,3,4-ij]quinazolin-5(3H)-one

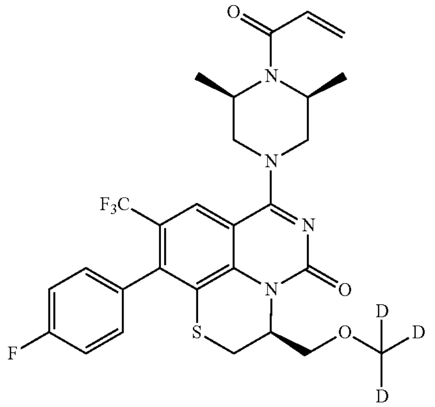 [SMILES: [2H]C([2H])([2H])OC[C@H]1CSc2c(-c3ccc(F)cc3)c(C(F)(F)F)cc3c(N4C[C@@H](C)N(C(=O)C=C)[C@@H](C)C4)nc(=O)n1c23]

Reaction Scheme

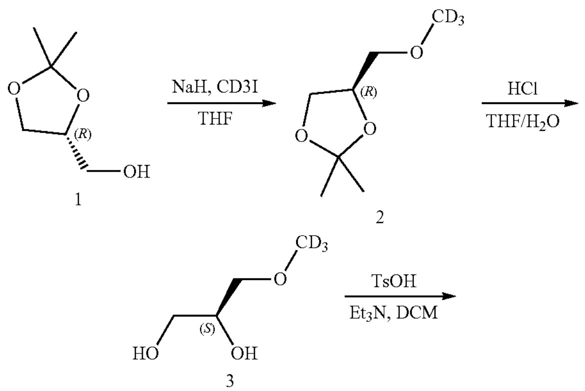

1

2

3

-continued

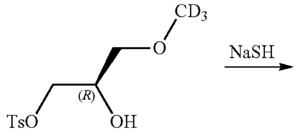

4

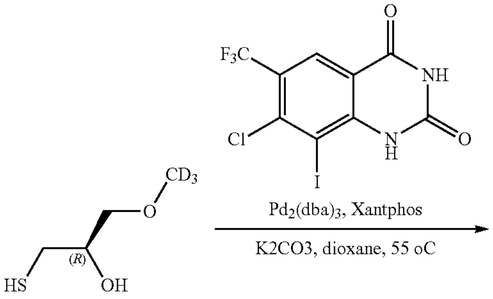

5

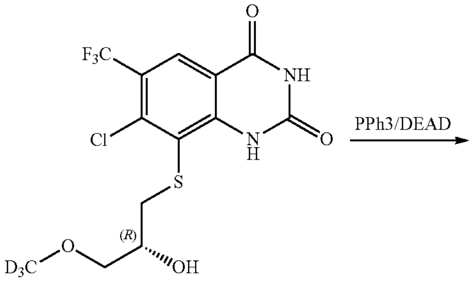

6

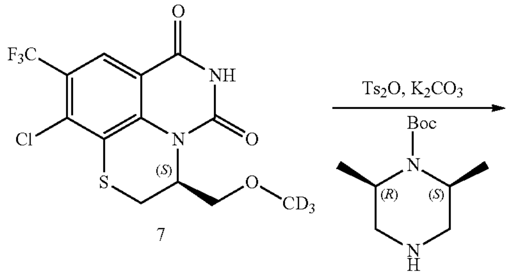

7

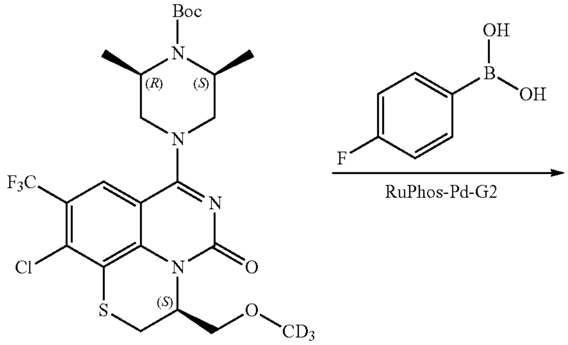

8

-continued

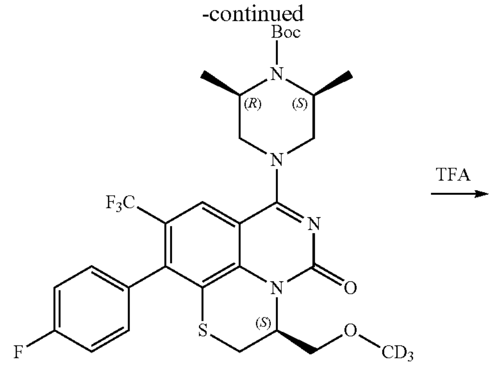

9

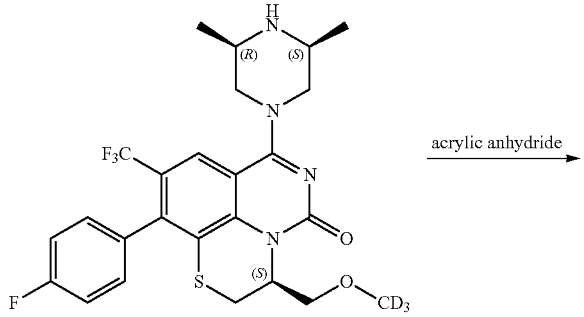

10

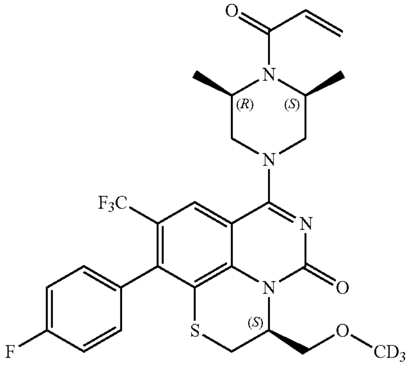

11

(R)-2,2-dimethyl-4-((trideuteriomethoxy)methyl)-1,3-dioxolane (2)

To a mixture of (R)-(2,2-dimethyl-1,3-dioxolan-4-yl) methanol (20 g, 151.4 mmol) in THF (350 mL) was added NaH (12.1 g, 302.7 mmol). The mixture was stirred at 0° C. to room temperature for 0.5 hour. Consequently, $CD_3I$ (37.0 g, 237.2 mmol) was added. The mixture was stirred at room temperature overnight. After completion, the mixture was poured into $NH_4Cl$ (300 mL), washed with ethyl acetate (200 mL×3). The organic phase was washed with water (100 mL) and dried over anhydrous sodium sulfate, After filtration and concentration under reduce pressure, compound (2) (13.0 g, crude) was obtained as yellow oil. $^1H$ NMR (400 MHz, $CDCl_3$) δ 4.31-4.24 (m, 1H), 4.07-4.04 (m, 1H), 3.72-3.68 (m, 1H), 3.49-3.39 (m, 2H), 1.43 (s, 3H), 1.37 (s, 3H).

(S)-3-(trideuteriomethoxy)propane-1,2-diol (3)

The mixture of (R)-2,2-dimethyl-4-((trideuteriomethoxy) methyl)-1,3-dioxolane (2) (13.0 g, 89.0 mmol, crude) and HCl (1200 mmol) in THF (100 mL) and water (100 mL) was stirred at room temperature overnight. The solvent was evaporated and the residue was purified by silica gel chromatography with DCM/MEOH=20/1 to afford (S)-3-(trideuteriomethoxy)propane-1,2-diol (3) (4.7 g, 49.8 mmol, 50% yield) as yellow oil; $^{1}$H NMR (400 MHz, $CDCl_3$) δ 3.82-3.78 (m, 1H), 3.55 (dd, J=4.4 Hz, 11.6 Hz, 1H), 3.49-3.45 (m, 2H), 3.38 (dd, J=6.8 Hz, 10.4 Hz, 1H).

(R)-2-hydroxy-3-(trideuteriomethoxy)propyl 4-methylbenzenesulfonate (4)

To a mixture of (S)-3-methoxypropane-1,2-diol (3) (4.7 g, 43.1 mmol) and TEA (8.9 mL, 64.6 mmol) in DCM (60 mL) was added TsCl (6.5 g, 34.4 mmol) at 0° C. The mixture was stirred at room temperature overnight. The solvent was evaporated and the residue was purified by silica gel chromatography (2% MeOH in DCM) to afford t(R)-2-hydroxy-3-(trideuteriomethoxy)propyl 4-methylbenzenesulfonate (4) (7.7 g, crude) as yellow oil. $^{1}$H NMR (400 MHz, $CDCl_3$) δ 7.80 (d, J=8.0 Hz, 2H), 7.35 (d, 6.4 Hz, 2H), 4.08-3.95 (m, 3H), 3.43-2.45 (m, 2H).

(R)-1-mercapto-3-(trideuteriomethoxy)propan-2-ol (5)

The mixture of (R)-2-hydroxy-3-methoxypropyl 4-methylbenzenesulfonate (4) (7.7 g, 29.5 mmol, crude) and NaSH (7.09 g, 88.7 mmol) in EtOH (100 mL) was stirred at room temperature 2 hours. The solvent was evaporated and the residue was purified by silica gel column by PE/EA=1/1 to afford (R)-1-mercapto-3-(trideuteriomethoxy)propan-2-ol (5) (2.9 g, 15.2 mmol, crude) as yellow oil; $^{1}$H NMR (400 MHz, $CDCl_3$) δ 3.85-3.79 (m, 1H), 3.51-3.41 (m, 2H), 2.73-2.59 (m, 2H), 1.47 (t, J=8.4 Hz, 1H).

(R)-7-chloro-8-((2-hydroxy-3-(trideuterio methoxy) propyl)thio)-6-(trifluoromethyl)quinazoline-2,4(1H, 3H)-dione (6)

The mixture of 7-chloro-8-iodo-6-(trifluoromethyl)quinazoline-2,4(1H,3H)-dione (5.7 g, 14.8 mmol), Pd2(dba)3 (1.3 g, 1.48 mmol), XantPhos (1.7 g, 2.96 mmol), (R)-1-mercapto-3-(trideuteriomethoxy)propan-2-ol (2.7 g, 22.24 mmol) and $K_2CO_3$ (6.13 g, 44.4 mmol) in dioxane (300 mL) was stirred under nitrogen atmosphere at 55° C. for overnight. After completion, the mixture was concentrated and the residue was purified by silica gel column with DCM/MeOH=20:1 to afford (R)-7-chloro-8-((2-hydroxy-3-(trideuterio methoxy)propyl)thio)-6-(trifluoromethyl)quinazoline-2,4(1H,3H)-dione (6) (2.8 g, crude) as a light yellow solid. LC-MS: [M+H], m/z=388.5

(S)-10-chloro-3-((trifluoromethoxy)methyl)-9-(trideuterio methyl)-2H-[1,4]thiazino[2,3,4-ij]quinazoline-5,7(3H,6H)-dione (7)

To a mixture of (R)-7-chloro-8-((2-hydroxy-3-(trideuterio methoxy)propyl)thio)-6-(trifluoromethyl)quinazoline-2,4 (1H,3H)-dione (6) (2.8 g, 7.2 mmol) and triphenylphosphine (3.8 g, 14.4 mmol) in THF (50 mL) was slowly added DEAD (2.5 g, 13.5 mmol) at 0° C. under nitrogen atmosphere. The mixture was stirred at room temperature for 1 hour. DCM (50 mL) was added. The organic phase was washed with water (50 mL×2). Dried over $Na_2SO_4$. the mixture was concentrated and the residue was purified by silica gel column with PE/EA=0-50% to afford (S)-10-chloro-3-((trifluoromethoxy)methyl)-9-(trideuterio methyl)-2H-[1,4]thiazino[2,3,4-ij]quinazoline-5,7(3H,6H)-dione (7) (870 mg, 2.24 mmol, yield: 31%) as a yellow solid. LC-MS: [M+H], m/z=370.2.

(2S,6R)-tert-butyl 4-((S)-10-chloro-5-oxo-3-((trideuteriomethoxy)methyl)-9-(trifluoromethyl)-3,5-dihydro-2H-[1,4]thiazino[2,3,4-ij]quinazolin-7-yl)-2,6-dimethylpiperazine-1-carboxylate (8)

To a solution of (S)-10-chloro-3-((trifluoromethoxy) methyl)-9-(trideuterio methyl)-2H-[1,4]thiazino[2,3,4-ij] quinazoline-5,7(3H,6H)-dione (7) (820 mg, 2.16 mmol) and $K_2CO_3$(2.98 g, 21.6 mmol) in ACN (20 mL) and DCM (20 mL) was added P-Toluenesulfonic anhydride (1.40 g, 4.32 mmol). The mixture was stirred at room temperature for 5 hours. To the mixture was added (2S,6R)-tert-butyl 2,6-dimethylpiperazine-1-carboxylate (925 mg, 4.32 mmol). The mixture was stirred at room temperature for 2 hours. After completion, the mixture was concentrated under reduced pressure and purified by silica gel column with DCM/EA=20%-80% to afford (2S,6R)-tert-butyl 4-((S)-10-chloro-5-oxo-3-((trideuteriomethoxy)methyl)-9-(trifluoromethyl)-3,5-dihydro-2H-[1,4]thiazino[2,3,4-ij]quinazolin-7-yl)-2,6-dimethylpiperazine-1-carboxylate (8) (680 mg, yield: 49%) as yellow solid. LC-MS: m/z 566.5 $[M+H]^+$;

(2S,6R)-tert-butyl 4-((S)-10-(4-fluorophenyl)-5-oxo-3-((trideuteriomethoxy)methyl)-9-(trifluoromethyl)-3,5-dihydro-2H-[1,4]thiazino[2,3,4-ij]quinazolin-7-yl)-2,6-dimethylpiperazine-1-carboxylate (9)

To a solution of ((2S,6R)-tert-butyl 4-((S)-10-chloro-5-oxo-3-((trideuteriomethoxy)methyl)-9-(trifluoromethyl)-3,5-dihydro-2H-[1,4]thiazino[2,3,4-ij]quinazolin-7-yl)-2,6-dimethylpiperazine-1-carboxylate (8) (150 mg, 0.26 mmol) in dioxane (5 mL) and water (1 mL) was added (4-fluorophenyl)boronic acid (297 mg, 2.12 mmol), RuPhos Pd G2 (30 mg, 0.03 mmol) and K3PO4 (692 m g, 2.6 mmol). The mixture was stirred at 75° C. under N2 for 2 hours. After completion, the mixture was poured into water (2 mL), extracted with EtOAc (5 mL×3). The combined organic phases were washed with brine (5 mL) and dried over $Na_2SO_4$. After filtration and concentration, the residue was purified by silica gel column using dichloromethane/methanol=50:1 to afford the (2S,6R)-tert-butyl 4-((S)-10-(4-fluorophenyl)-5-oxo-3-((trideuteriomethoxy)methyl)-9-(trifluoromethyl)-3,5-dihydro-2H-[1,4]thiazino[2,3,4-ij] quinazolin-7-yl)-2,6-dimethylpiperazine-1-carboxylate (9) (160 mg, crude) as a yellow solid. MS (ESI) m/z 626.6 [M+H]+

(S)-7-((3S,5R)-3,5-dimethylpiperazin-1-yl)-10-(4-fluorophenyl)-3-((trideuteriomethoxy)methyl)-9-(trifluoromethyl)-2H-[1,4]thiazino[2,3,4-ij]quinazolin-5(3H)-one (10)

To a solution of (2S,6R)-tert-butyl 4-((S)-10-(4-fluorophenyl)-5-oxo-3-((trideuteriomethoxy)methyl)-9-(trifluoromethyl)-3,5-dihydro-2H-[1,4]thiazino[2,3,4-ij]quinazolin-7-yl)-2,6-dimethylpiperazine-1-carboxylate (9) (160 mg, 0.25 mmol) in DCM (3 mL) was added TFA (1 mL) at 0° C. The mixture was stirred at room temperature for 1 hour. After completion, the mixture was concentrated under reduced pressure to afford (S)-7-((3S,5R)-3,5-dimethylpiperazin-1-yl)-10-(4-fluorophenyl)-3-((trideuteriomethoxy) methyl)-9-(trifluoromethyl)-2H-[1,4]thiazino[2,3,4-ij]quinazolin-5(3H)-one (10) (150 mg, crude) as yellow solid. LC-MS: m/z 526.3 [M+H]+. 1H NMR (400 MHz, CDCl3) δ 7.78 (s, 1H), 7.21-7.17 (m, 4H), 5.43-5.37 (m, 1H), 4.39 (d, J=12.4, 1H), 4.20 (d, J=11.6 Hz, 2H), 3.66-3.64 (m, 2H), 3.33-3.29 (m, 1H), 3.21-3.13 (m, 1H), 2.96-2.92 (m, 3H), 2.72 (t, J=11.2 Hz, 1H), 1.16-1.12 (m, 6H).

(S)-7-((3S,5R)-4-acryloyl-3,5-dimethylpiperazin-1-yl)-10-(4-fluorophenyl)-3-((trideuteriomethoxy)methyl)-9-(trifluoromethyl)-2H-[1,4]thiazino[2,3,4-ij]quinazolin-5(3H)-one (11)

To a solution of (S)-7-((3S,5R)-3,5-dimethylpiperazin-1-yl)-10-(4-fluorophenyl)-3-((trideuteriomethoxy)methyl)-9-(trifluoromethyl)-2H-[1,4]thiazino[2,3,4-ij]quinazolin-5(3H)-one (10) (100 mg, 0.19 mmol) and $Et_3N$ (28 mg, 0.28 mmol) in DCM (3 mL) was added acrylic anhydride (36 mg, 0.28 mmol) at 0° C. The mixture was stirred at room temperature for 30 min. After completion, the mixture was quenched with 1 mL of MeOH, concentrated under reduced pressure and purified by C18 with 5-95% ACN in H2O to afford (S)-7-((3S,5R)-4-acryloyl-3,5-dimethylpiperazin-1-yl)-10-(4-fluorophenyl)-3-((trideuteriomethoxy)methyl)-9-(trifluoromethyl)-2H-[1,4]thiazino[2,3,4-ij]quinazolin-5(3H)-one (11) (57 mg, 52% yield) as a white powder. LC-MS: m/z 580.2 [M+H]+; 1H NMR (400 MHz, CDCl3) δ 8.06 (s, 1H), 7.23-7.15 (m, 4H), 6.62 (dd, J=10.4 Hz, J=16.4 Hz, 1H), 6.41 (dd, J=1.6 Hz, J=16.8 Hz, 1H), 5.77 (dd, J=2.0 Hz, J=10.4 Hz, 1H), 5.43-5.41 (m, 1H), 4.82-4.54 (m, 2H), 4.21-4.16 (m, 2H), 3.69-3.62 (m, 2H), 3.39-3.29 (m, 3H), 2.98-2.94 (m, 1H), 1.62 (d, J=7.2 Hz, 3H), 1.47 (d, J=7.2 Hz, 3H).

Example 2004: (S)-7-((3S,5R)-4-acryloyl-3,5-dimethylpiperazin-1-yl)-10-(3-chloro-4-fluorophenyl)-3-((methoxymethoxy)methyl)-9-(trifluoromethyl)-2H-[1,4]thiazino[2,3,4-ij]quinazolin-5(3H)-one

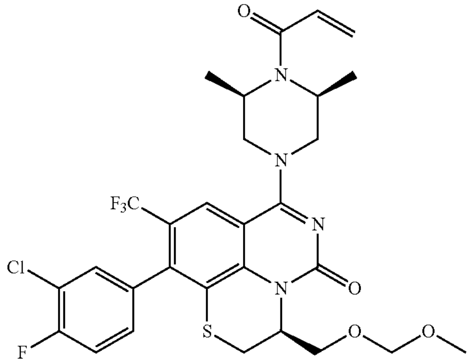 [SMILES: C=CC(=O)N1[C@H](C)CN(c2nc(=O)n3c4c(c(-c5ccc(F)c(Cl)c5)c(C(F)(F)F)cc24)SC[C@@H]3COCOC)C[C@@H]1C]

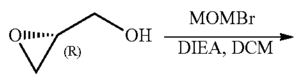

1

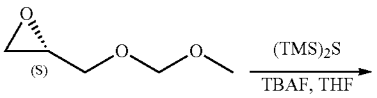

2

-continued

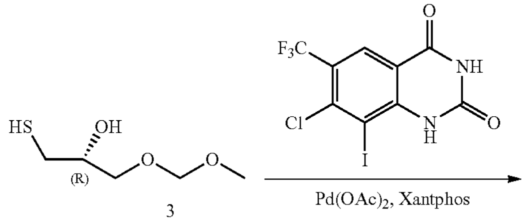

3

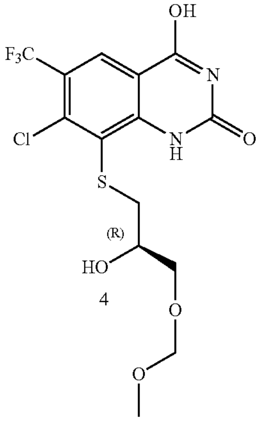

4

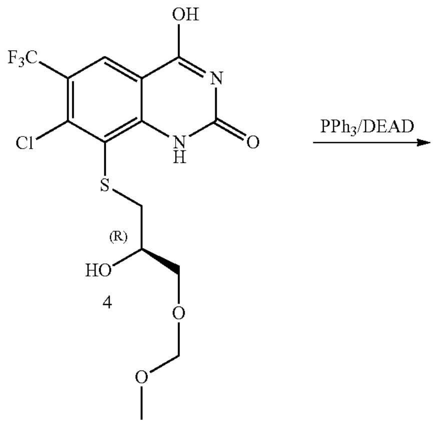

4

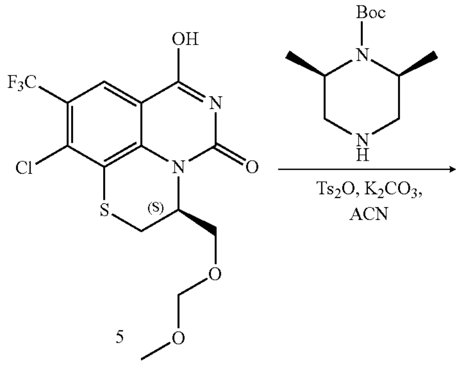

5

-continued

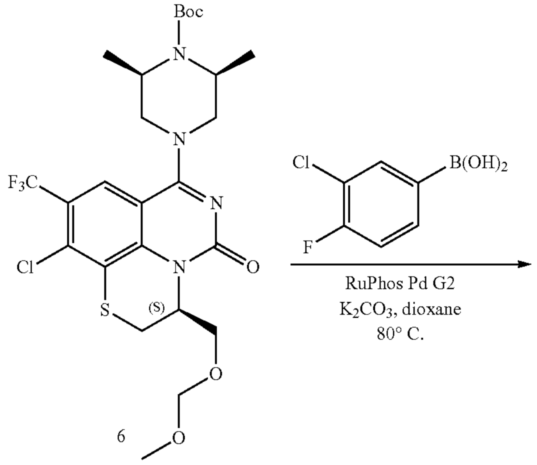

6

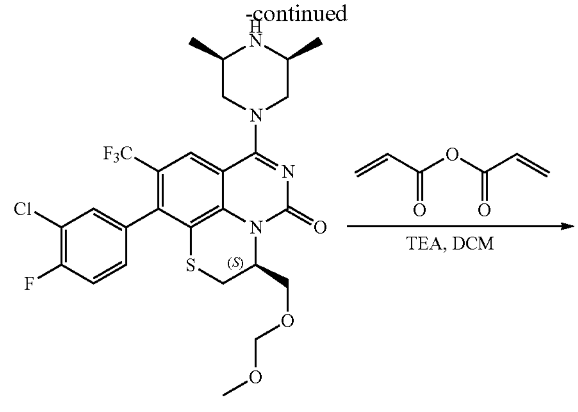

8

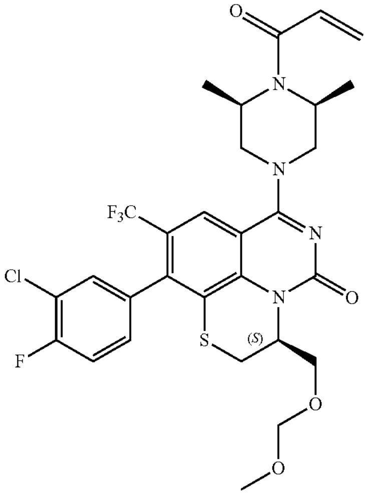

9

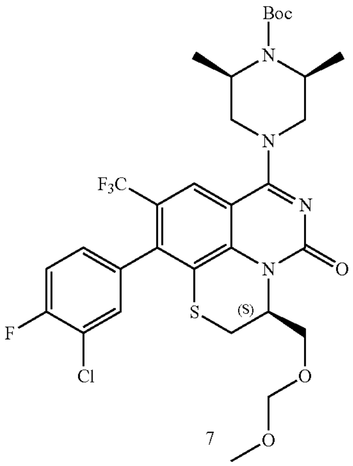

7

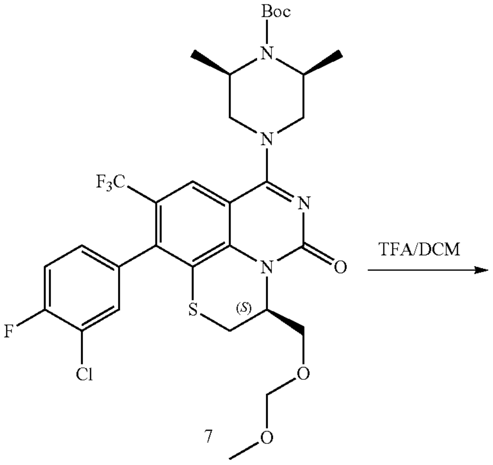

7

(S)-2-((methoxymethoxy)methyl)oxirane (2)

To a mixture of (R)-oxiran-2-ylmethanol (15 g, 202.7 mmol) and N,N-diisopropylethylamine (52.3 g, 405.4 mmol) in dichloromethane (200 mL) was added bromo (methoxy)methane (32.7 g, 263.5 mmol). The mixture was stirred at 0° C. to room temperature for 5 hours. After completion, the mixture was poured into dichloromethane (300 mL), washed with water (200 mL×3). The organic phase was washed with brine (100 mL) and dried over anhydrous sodium sulfate, After filtration and concentration, the residue was purified by silica gel column with petroleum ether to afford (S)-2-((methoxymethoxy)methyl)oxirane (2) (25.00 g, crude) as colorless oil; $^1$H NMR (400 MHz, $CDCl_3$) δ 4.66 (d, J=1.2 Hz, 2H), 3.79 (dd, J=11.6 Hz, 3.2 Hz, 1H), 3.51 (dd, J=11.6 Hz, 2.0 Hz, 1H), 3.38 (s, 3H), 3.20-3.16 (m, 1H), 2.83-2.80 (m, 1H), 2.64 (dd, J=5.2 Hz, 2.8 Hz, 1H).

(R)-1-mercapto-3-(methoxymethoxy)propan-2-ol (3)

To a mixture of (S)-2-((methoxymethoxy)methyl)oxirane (2) (10 g, 84.7 mmol) in tetrahydrofuran (250 mL) was added 1,1,1,3,3,3-hexamethyldisilathiane (16.63 g, 93.2 mmol) and tetrabutylammonium fluoride (1.0 M in tetrahydrofuran, 25 mL, 25 mmol) at 0° C. The mixture was stirred at room temperature for 2 hours. After completion, the mixture was concentrated under reduced pressure. The residue was purified by silica gel column with petroleum ether/ethyl acetate=4/1 to afford (R)-1-mercapto-3-(methoxymethoxy)propan-2-ol (3) (2 g, yield: 16%) as a colorless oil. $^1$H NMR (400 MHz, $CDCl_3$) δ 4.66 (s, 2H), 3.85-3.82 (m, 1H), 3.69-3.60 (m, 2H), 3.39 (s, 3H), 2.88 (brs, 1H), 2.71-2.65 (m, 2H), 1.51 (t, J 8.8 Hz, 1H).

(R)-7-chloro-4-hydroxy-8-((2-hydroxy-3-(methoxymethoxy)propyl)thio)-6-(trifluoromethyl)quinazolin-2(1H)-one (4)

To a solution of 7-chloro-8-iodo-6-(trifluoromethyl)quinazoline-2,4(1H,3H)-dione (1.86 g, 4.77 mmol) in dioxane (40 mL) was added potassium carbonate (1.32 g, 9.54 mmol), (R)-1-mercapto-3-(methoxymethoxy)propan-2-ol (1.09 g, 7.15 mmol), 4,5-Bis(diphenyl-phosphino)-9,9-dimethylxanthene (413 mg, 0.72 mmol) and Tris(dibenzylideneacetone) dipalladium (439 g, 0.48 mmol). The mixture was stirred at 60° C. under nitrogen atmosphere for 18 hours. After completion, the mixture was concentrated under reduced pressure. The residue was purified by silica gel column chromatography (dichloromethane/methanol=60/1) to afford (R)-7-chloro-4-hydroxy-8-((2-hydroxy-3-(methoxymethoxy)propyl)thio)-6-(trifluoromethyl)quinazolin-2(1H)-one (4) (1.33 g, yield: 67%) as pale yellow solid. MS (ESI) m/z 415.0 [M+H]$^+$.

(S)-10-chloro-7-hydroxy-3-((methoxymethoxy)methyl)-9-(trifluoromethyl)-2H-[1,4]thiazino[2,3,4-ij]quinazolin-5(3H)-one (5)

To a mixture of (R)-7-chloro-4-hydroxy-8-((2-hydroxy-3-(methoxymethoxy)propyl)thio)-6-(trifluoromethyl)quinazolin-2(1H)-one (4) (1.33 g, 3.21 mmol) and triphenylphosphine (3.37 g, 12.85 mmol) in tetrahydrofuran (500 ml) was added diethyl azodicarboxylate (2.23 g, 12.85 mmol) at 0° C. The mixture was stirred at 0° C. for 45 min. After completion, the mixture was poured into ice-water (200 mL) and extracted with ethyl acetate (200 mL×3). Concentrated and the residue was purified by C18 with 30-95% acetonitrile in water to afford (S)-10-chloro-7-hydroxy-3-((methoxymethoxy)methyl)-9-(trifluoromethyl)-2H-[1,4]thiazino[2,3,4-ij]quinazolin-5(3H)-one (5) (1.1 g, yield: 87%) as a pale yellow solid. MS (ESI) m/z 397.0 [M+H]$^+$.

(2S,6R)-tert-butyl 4-((S)-10-chloro-3-((methoxymethoxy)methyl)-5-oxo-9-(trifluoromethyl)-3,5-dihydro-2H-[1,4]thiazino[2,3,4-ij]quinazolin-7-yl)-2,6-dimethylpiperazine-1-carboxylate (6)

To a mixture of (S)-10-chloro-7-hydroxy-3-((methoxymethoxy)methyl)-9-(trifluoromethyl)-2H-[1,4]thiazino[2,3,4-ij]quinazolin-5(3H)-one (5) (300 mg, 0.76 mmol) and potassium carbonate (1.05 g, 7.6 mmol) in acetonitrile (10 mL) was added 4-methylbenzenesulfonic anhydride (620 mg, 1.9 mmol) at 0° C. The mixture was stirred at room temperature for 4 hours. After completion, (2R,6S)-tert-butyl 2,6-dimethylpiperazine-1-carboxylate (650 mg, 3.04 mmol) was added into the reaction solution. The reaction mixture was stirred at room temperature for 1 hour. After completion, the mixture was poured into ice-water (50 mL) and extracted with ethyl acetate (50 mL×3). Concentrated and the residue was purified by C18 column with 20-95% acetonitrile in water to afford (2S,6R)-tert-butyl 4-((S)-10-chloro-3-((methoxymethoxy)methyl)-5-oxo-9-(trifluoromethyl)-3,5-dihydro-2H-[1,4]thiazino[2,3,4-ij]quinazolin-7-yl)-2,6-dimethylpiperazine-1-carboxylate (6) (345 mg, yield: 77%) as a yellow solid. MS (ESI) m/z 593.2 [M+H]$^+$.

(2S,6R)-tert-butyl 4-((S)-10-(3-chloro-4-fluorophenyl)-3-((methoxymethoxy)methyl)-5-oxo-9-(trifluoromethyl)-3,5-dihydro-2H-[1,4]thiazino[2,3,4-ij]quinazolin-7-yl)-2,6-dimethylpiperazine-1-carboxylate (7)

To a solution of (2S,6R)-tert-butyl 4-((S)-10-chloro-3-((methoxymethoxy)methyl)-5-oxo-9-(trifluoromethyl)-3,5-dihydro-2H-[1,4]thiazino[2,3,4-ij]quinazolin-7-yl)-2,6-dimethylpiperazine-1-carboxylate (6) (200 mg, 0.34 mmol) in 1,4-dioxane (3 mL) and water (0.5 mL) were added tripotassium phosphate (269 mg, 1.01 mmol), (4-fluorophenyl) boronic acid (176 mg, 1.01 mmol) and chloro(2-dicyclohexylphosphino-2', 6'-diisopropoxy-1,1'-biphenyl)[2-(2'-amino-1,1'-biphenyl)]palladium(II) (26 mg, 0.034 mmol). The mixture was stirred at 80° C. under nitrogen atmosphere for 2 hours. After completion, the mixture was concentrated under reduced pressure. the residue was purified by silica gel column chromatography (dichloromethane/methanol=100/1) to afford (2S,6R)-tert-butyl 4-((S)-10-(3-chloro-4-fluorophenyl)-3-((methoxymethoxy)methyl)-5-oxo-9-(trifluoromethyl)-3,5-dihydro-2H-[1,4]thiazino[2,3,4-ij]quinazolin-7-yl)-2,6-dimethylpiperazine-1-carboxylate (7) (150 mg, yield: 64%) as a yellow solid. MS (ESI) m/z 687.3 [M+H]$^+$.

(S)-10-(3-chloro-4-fluorophenyl)-7-((3S,5R)-3,5-dimethylpiperazin-1-yl)-3-((methoxymethoxy)methyl)-9-(trifluoromethyl)-2H-[1,4]thiazino[2,3,4-ij]quinazolin-5(3H)-one (8)

To a cooled mixture of (2S,6R)-tert-butyl 4-((S)-10-(3-chloro-4-fluorophenyl)-3-((methoxymethoxy)methyl)-5-oxo-9-(trifluoromethyl)-3,5-dihydro-2H-[1,4]thiazino[2,3,4-ij]quinazolin-7-yl)-2,6-dimethylpiperazine-1-carboxylate (7) (150 mg, 0.22 mmol) in dichloromethane (2 mL) was added trifluoroacetic acid (2 mL) at 0° C. The reaction solution was stirred at room temperature for 1 hour. After completion, the mixture was adjusted PH=7~8 with sodium bicarbonate solution. After extraction and concentration, the residue was purified by silica gel column chromatography (dichloromethane/methanol=10/1) to afford (S)-10-(3-chloro-4-fluorophenyl)-7-((3S,5R)-3,5-dimethylpiperazin-1-yl)-3-((methoxymethoxy)methyl)-9-(trifluoromethyl)-2H-[1,4]thiazino[2,3,4-ij]quinazolin-5(3H)-one (8) (90 mg, yield: 70%) as a yellow solid. MS (ESI) m/z 587.2 [M+H]$^+$.

(S)-7-((3S,5R)-4-acryloyl-3,5-dimethylpiperazin-1-yl)-10-(3-chloro-4-fluorophenyl)-3-((methoxymethoxy)methyl)-9-(trifluoromethyl)-2H-[1,4]thiazino[2,3,4-ij]quinazolin-5(3H)-one (9)

To a mixture of (S)-10-(3-chloro-4-fluorophenyl)-7-((3S,5R)-3,5-dimethylpiperazin-1-yl)-3-((methoxymethoxy)methyl)-9-(trifluoromethyl)-2H-[1,4]thiazino[2,3,4-ij]quinazolin-5(3H)-one (7) (90 mg, 0.15 mmol) and triethyl amine (45 mg, 0.45 mmol) in dichloromethane (2 ml) was added acrylic anhydride (28 mg, 0.23 mmol) at 0° C. The mixture was stirred at room temperature for 1 hour. After completion, the mixture was poured into ice-water (20 mL) and extracted with dichloromethane (20 mL×3). Concentrated and the residue was purified by preparative High Performance Liquid Chromatography (20% to 95% acetonitrile in water) to afford (S)-7-((3S,5R)-4-acryloyl-3,5-dimethylpiperazin-1-yl)-10-(3-chloro-4-fluorophenyl)-3-((methoxymethoxy)methyl)-9-(trifluoromethyl)-2H-[1,4]thiazino[2,3,4-ij]quinazolin-5(3H)-one (8) (20 mg, yield: 21%) as a white solid. MS (ESI) m/z 641.1 $[M+H]^+$.

$^1H$ NMR (400 MHz, $CDCl_3$) δ 7.80 (s, 1H), 7.24-7.15 (m, 4H), 6.63-6.56 (m, 1H), 6.39 (d, J=16.4 Hz, 1H), 5.80 (d, J=10.4 Hz, 1H), 5.46-5.45 (m, 1H), 4.67-4.62 (m, 2H), 4.02-3.95 (m, 3H), 3.81-3.79 (m, 7H), 3.35-3.33 (m, 4H), 3.01-2.98 (m, 1H).

Example 2016: (3S)-7-((3S,5R)-4-acryloyl-3,5-dimethylpiperazin-1-yl)-10-(2,4-difluorophenyl)-3-(ethoxymethyl)-9-(trifluoromethyl)-2H-[1,4]thiazino[2,3,4-ij]quinazolin-5(3H)-one

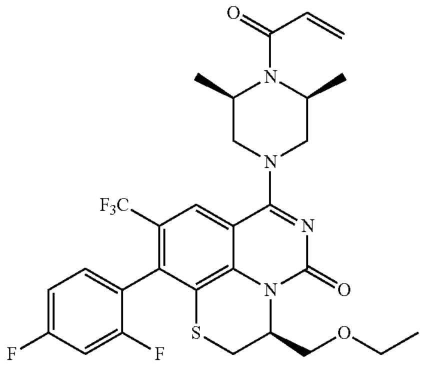 [SMILES: C=CC(=O)N1[C@H](C)CN(c2nc(=O)n3c4c(c(-c5ccc(F)cc5F)c(C(F)(F)F)cc24)SC[C@@H]3COCC)C[C@@H]1C]

Reaction Scheme

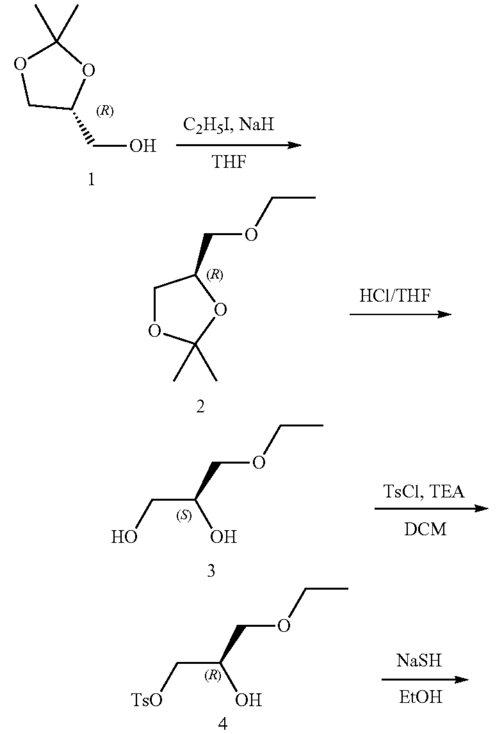

-continued

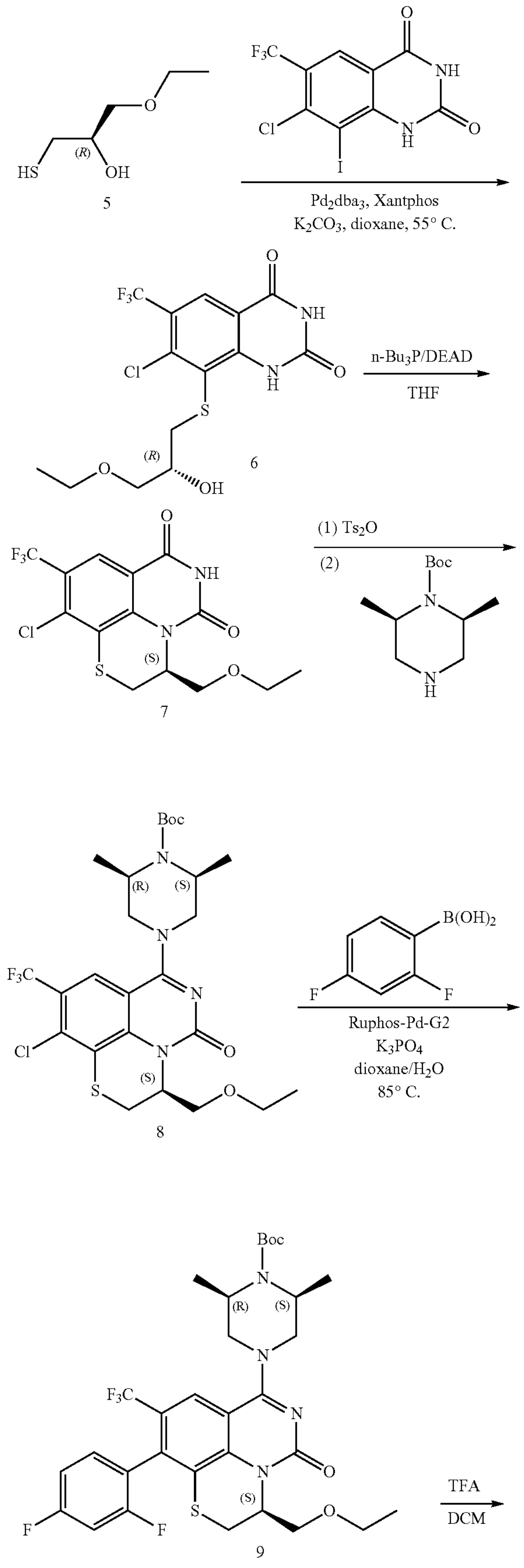

-continued

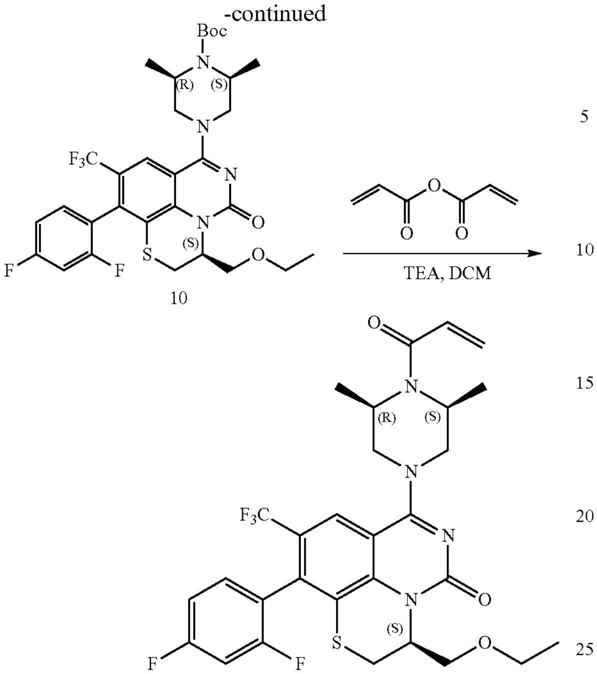

10

11

(R)-4-(ethoxymethyl)-2,2-dimethyl-1,3-dioxolane (2)

To a mixture of (R)-(2,2-dimethyl-1,3-dioxolan-4-yl) methanol (25 g, 189.2 mmol) in dimethylformamide (350 mL) was added sodium hydride (16.8 g, 492.0 mmol). The mixture was stirred at 0° C. to room temperature for 0.5 hour. Consequently, iodoethane (37.0 g, 237.2 mmol) was added. The mixture was stirred at room temperature overnight. After completion, the mixture was poured into saturated ammonium chloride solution (200 mL), washed with ethyl acetate (200 mL×3). The organic phase was washed with water (100 mL) and dried over anhydrous sodium sulfate. After filtration and concentration under reduce pressure, the title compound (2) was obtained (19.9 g, 124.2 mmol, crude) as a yellow oil.

$^1$H NMR (400 MHz, $CDCl_3$) δ 4.32-4.23 (m, 1H), 4.06 (dd, J=8.4 Hz, 6.8 Hz, 1H), 3.72 (dd, J=8.4 Hz, 6.4 Hz, 1H), 3.38-3.53 (m, 3H), 3.43 (dd, J=10.4 Hz, 5.6 Hz, 1H), 1.43 (s, 3H), 1.37 (s, 3H), 1.21 (t, 6.8 Hz, 3H).

(S)-3-ethoxypropane-1,2-diol (3)

The mixture of (R)-4-(ethoxymethyl)-2,2-dimethyl-1,3-dioxolane (2) (19.9 g, 124.2 mmol, crude) and hydrogen chloride (1200 mmol) in tetrahydrofuran (100 mL) and water (100 mL) was stirred at room temperature overnight. The solvent was evaporated, and the residue was purified by silica gel chromatography (dichloromethane/methanol=100/1 to 30/1) to afford the title compound (3) (5.9 g, 49.1 mmol, 40% yield) as a yellow oil.

$^1$H NMR (400 MHz, $CDCl_3$) δ 3.91-3.85 (m, 1H), 3.69 (dd, J=11.2 Hz, 3.6 Hz, 1H), 3.60 (dd, J=11.6 Hz, 6.0 Hz, 1H), 3.58-3.43 (m, 5H), 3.19 (s, 1H), 1.21 (t, 7.2 Hz, 3H).

(R)-3-ethoxy-2-hydroxypropyl 4-methylbenzenesulfonate (4)

To a mixture of (S)-3-ethoxypropane-1,2-diol (3) (5.9 g, 49.1 mmol) and triethylamine (8.6 mL, 61.4 mmol) in dichloromethane (60 mL) was added p-toluenesulfonyl chloride (5.9 g, 36.8 mmol) at 0° C. The mixture was stirred at room temperature overnight. The solvent was evaporated, and the residue was purified by silica gel chromatography (dichloromethane/methanol=200/1 to 50/1) to afford the title compound (4) (5.5 g, 20 mmol, 38% yield) as a yellow oil.

$^1$H NMR (400 MHz, $CDCl_3$) δ 7.83-7.78 (m, 2H), 7.38-7.33 (m, 2H), 4.17-3.92 (m, 3H), 3.52-3.39 (m, 4H), 2.50 (d, 5.6 Hz, 1H), 2.45 (s, 3H), 1.15 (t, 7.2 Hz, 3H).

(R)-1-ethoxy-3-mercaptopropan-2-ol (5)

To a mixture of (R)-3-ethoxy-2-hydroxypropyl 4-methylbenzenesulfonate (4)(5.5 g, 20.0 mmol) in ethanol (60 mL) was added sodium hydrosulfide (2.8 g, 50.1 mmol). The mixture was stirred at 30° C. for 2 hours. After concentration under reduce pressure, the residue was washed with dichloromethane. After filtration and concentration, the residue was purified by silica gel chromatography (dichloromethane/methanol=200/1 to 60/1) to give the title compound (5) (2.01 g, 14.76 mmol, crude) as a yellow oil.

(R)-7-chloro-8-((3-ethoxy-2-hydroxypropyl)thio)-6-(trifluoromethyl)quinazoline-2,4(1H,3H)-dione (6)

The mixture of 7-chloro-8-iodo-6-(trifluoromethyl)quinazoline-2,4(1H,3H)-dione (2.89 g, 7.40 mmol), potassium carbonate (3.07 g, 22.2 mmol), 4,5-Bis(diphenyl-phosphino)-9,9-dimethylxanthene (0.64 g, 1.11 mmol), (R)-1-ethoxy-3-mercaptopropan-2-ol (2.01 g, 14.76 mmol) and Tris(dibenzylideneacetone) dipalladium (1.01 g, 1.11 mmol) in dioxane (40 mL) was stirred under nitrogen atmosphere at 55° C. overnight. After completion, the mixture was washed with dichloromethane and filtrated. After concentration, the residue was purified by silica gel column with (dichloromethane/methanol=200/1 to 30/1) to afford the product (6) (1.70 g, 4.26 mmol, yield: 58%) as a yellow solid. LC-MS: [M−H], m/z=397.1.

(S)-10-chloro-3-(ethoxymethyl)-9-(trifluoromethyl)-2H-[1,4]thiazino[2,3,4-ij]quinazoline-5,7(3H,6H)-dione (7)

To a mixture of (R)-7-chloro-8-((3-ethoxy-2-hydroxypropyl)thio)-6-(trifluoromethyl)quinazoline-2,4(1H,3H)-dione (6) (1.70 g, 4.26 mmol) and triphenylphosphine (2.23 g, 8.53 mmol) in tetrahydrofuran (320 mL) was slowly added Diethyl azodicarboxylate (1.45 g, 8.53 mmol) at 0° C. under nitrogen atmosphere. The mixture was stirred at room temperature for 2 hour. dichloromethane (200 mL) was added. The organic phase was washed with water (200 mL×2), dried over anhydrous sodium sulfate. The mixture was concentrated, and the residue was purified by flash chromatography column (C18, acetonitrile/water=20% to 95%) to afford the product (7) (1.10 g, 2.89 mmol, yield: 72%) as a white solid. LC-MS: [M−H], m/z=378.9.

(2S,6R)-tert-butyl 4-((S)-10-chloro-3-(ethoxymethyl)-5-oxo-9-(trifluoromethyl)-3,5-dihydro-2H-[1,4]thiazino[2,3,4-ij]quinazolin-7-yl)-2,6-dimethylpiperazine-1-carboxylate (8)

To a solution of (S)-10-chloro-3-(ethoxymethyl)-9-(trifluoromethyl)-2H-[1,4]thiazino[2,3,4-ij]quinazoline-5,7(3H,6H)-dione (7) (1.10 g, 2.89 mmol) in acetonitrile (110 mL) were added potassium carbonate (3.99 g, 28.89 mmol) and 4-methylbenzenesulfonic anhydride (2.83 g, 8.67 mmol).

The mixture was stirred at room temperature for 7 hours. The mixture was added (2S,6R)-tert-butyl 2,6-dimethylpiperazine-1-carboxylate (2.48 g, 11.56 mmol) to the mixture and then stirred at room temperature overnight. After completion, the mixture was poured into ice-water (300 mL) and extracted with ethyl acetate (200 mL×3). Concentrated and the residue was purified by flash chromatography column (C18, acetonitrile/water=20% to 95%) to afford desired (8) product (1.45 g, yield: 87%) as a yellow solid. LC-MS: m/z 577.5 [M+H]+;

(2S,6R)-tert-butyl 4-((3S)-10-(2,4-difluorophenyl)-3-(ethoxymethyl)-5-oxo-9-(trifluoromethyl)-3,5-dihydro-2H-[1,4]thiazino[2,3,4-ij]quinazolin-7-yl)-2,6-dimethylpiperazine-1-carboxylate (9)

Chloro(2-dicyclohexylphosphino-2', 6'-diisopropoxy-1,1'-biphenyl)[2-(2'-amino-1,1'-biphenyl)]palladium(II) (27 mg, 0.04 mmol) was added to a mixture of (2S,6R)-tert-butyl 4-((S)-10-chloro-3-(ethoxymethyl)-5-oxo-9-(trifluoromethyl)-3,5-dihydro-2H-[1,4]thiazino[2,3,4-ij]quinazolin-7-yl)-2,6-dimethylpiperazine-1-carboxylate (200 mg, 0.35 mmol), (2,4-difluorophenyl)boronic acid (274 mg, 1.73 mmol) and tripotassium phosphate (441 mg, 2.08 mmol) in 1,4-dioxane (5 mL) and water (1 mL) at 85° C. under nitrogen atmosphere. The mixture was stirred at 85° C. for 2 hours. The mixture was washed with dichloromethane and filtrated. After concentration, the residue was purified by flash chromatography column (C18, acetonitrile/water=20% to 95%) to afford the product (9) (197 mg, 0.30 mmol, yield: 86%) as a white solid. LC-MS: m/z 655.6 [M+H]+.

(3S)-10-(2,4-difluorophenyl)-7-((3S,5R)-3,5-dimethylpiperazin-1-yl)-3-(ethoxymethyl)-9-(trifluoromethyl)-2H-[1,4]thiazino[2,3,4-ij]quinazolin-5(3H)-one (10)

To a solution of (2S,6R)-tert-butyl 4-((3S)-10-(2,4-difluorophenyl)-3-(ethoxymethyl)-5-oxo-9-(trifluoromethyl)-3,5-dihydro-2H-[1,4]thiazino[2,3,4-ij]quinazolin-7-yl)-2,6-dimethylpiperazine-1-carboxylate (197 mg, 0.30 mmol) in dichloromethane (2 mL) was added Trifluoroacetic acid (2 mL) at 0° C. The mixture was stirred at room temperature for 1 hour. The mixture was concentrated, and the residue was purified by silica gel column (dichloromethane/methanol=100/1 to 20/1) to afford the product (10) (135 mg, 0.24 mmol, crude) as a yellow solid. LC-MS: m/z 555.5 [M+H]+.

(3S)-7-((3S,5R)-4-acryloyl-3,5-dimethylpiperazin-1-yl)-10-(2,4-difluorophenyl)-3-(ethoxymethyl)-9-(trifluoromethyl)-2H-[1,4]thiazino[2,3,4-ij]quinazolin-5(3H)-one (11)

To a mixture of (3S)-10-(2,4-difluorophenyl)-7-((3S,5R)-3,5-dimethylpiperazin-1-yl)-3-(ethoxymethyl)-9-(trifluoromethyl)-2H-[1,4]thiazino[2,3,4-ij]quinazolin-5(3H)-one (10) (135 mg, 0.24 mmol) and triethyl amine (74 mg, 0.73 mmol) in dichloromethane (5 mL) was added Acrylic anhydride (31 mg, 0.24 mmol) at 0° C. The mixture was stirred at room temperature for 2 hours. After concentration, the residue was purified by prep-HPLC to afford the product (11) (37 mg, 0.06 mmol, 25% yield) as a white solid. LC-MS: m/z 609.2 [M+H]+.

$^1$H NMR (400 MHz, $CDCl_3$) δ 8.07 (s, 1H), 7.23-7.13 (m, 1H), 7.08-6.92 (m, 2H), 6.63 (dd, J=16.8 Hz, 6.0 Hz, 1H), 6.41 (dd, J 16.8 Hz, 1.6 Hz, 1H), 5.78 (dd, J=10.8 Hz, 1.6 Hz, 1H), 5.51-5.38 (m, 1H), 5.00-4.40 (m, 2H), 4.25-4.14 (m, 2H), 3.74-3.47 (m, 4H), 3.43-3.28 (m, 3H), 3.07-2.97 (m, 1H), 1.63 (d, J=7.2 Hz, 3H), 1.48 (d, J=6.4 Hz, 3H), 1.18 (t, J=6.8 Hz, 3H).

Examples 2034 and 2035: 8-((3S,5R)-4-acryloyl-3,5-dimethylpiperazin-1-yl)-3-((dimethylamino)methyl)-11-(4-fluorophenyl)-10-(trifluoromethyl)-3,4-dihydro-[1,4]thiazepino[2,3,4-ij]quinazolin-6(2H)-one Reaction Scheme

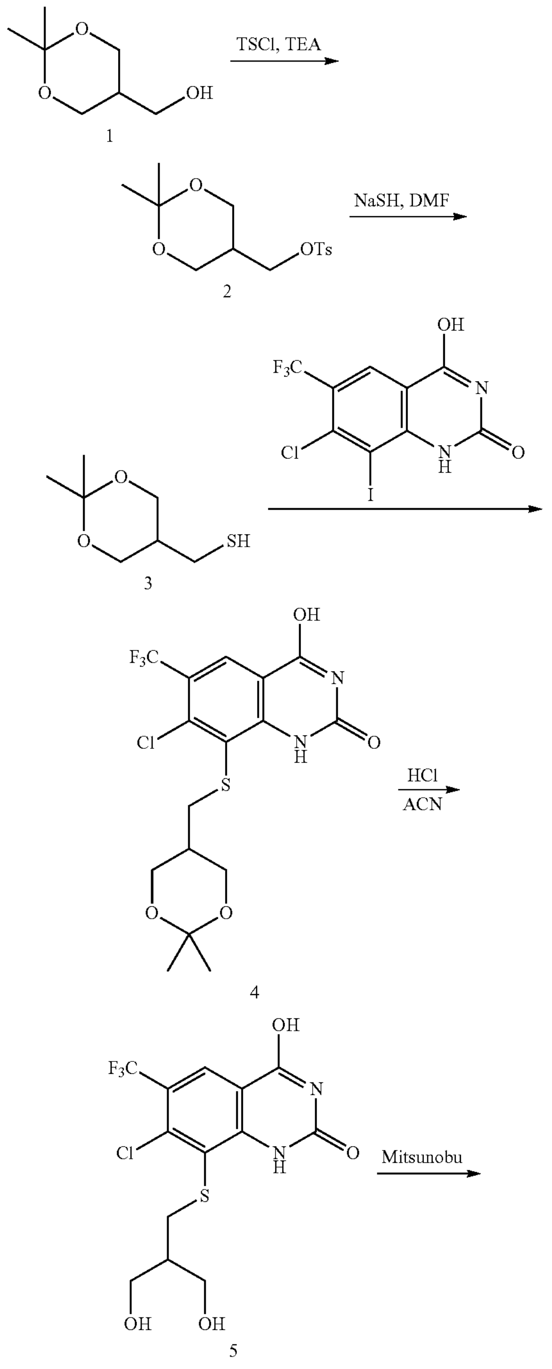

-continued
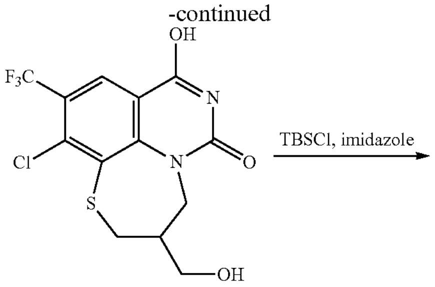
6
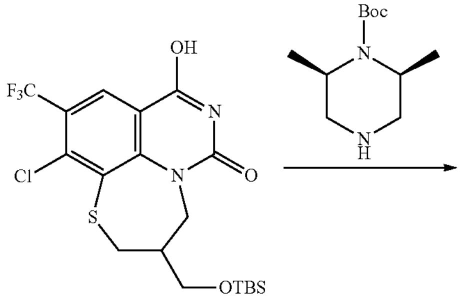
7
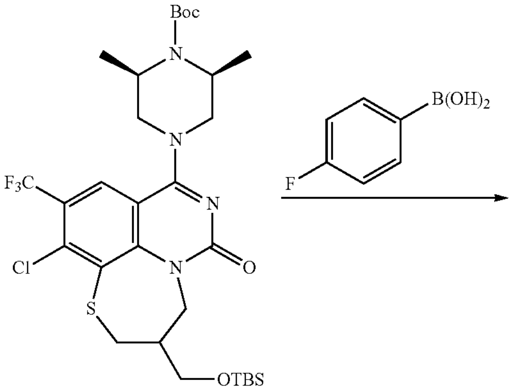
8
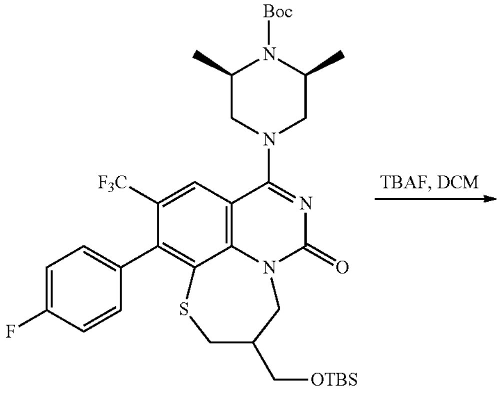
9
-continued
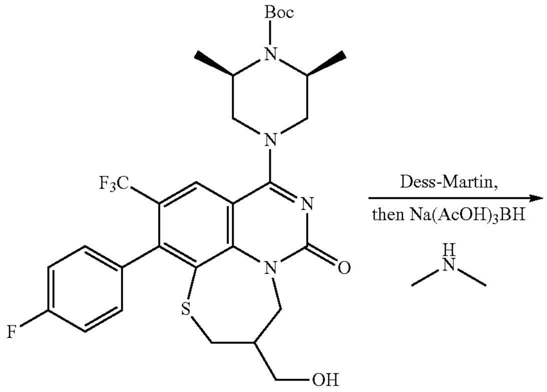
10
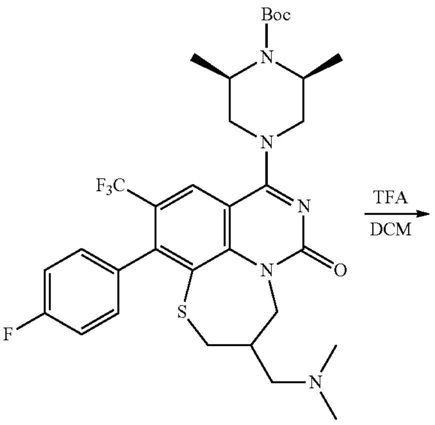
11
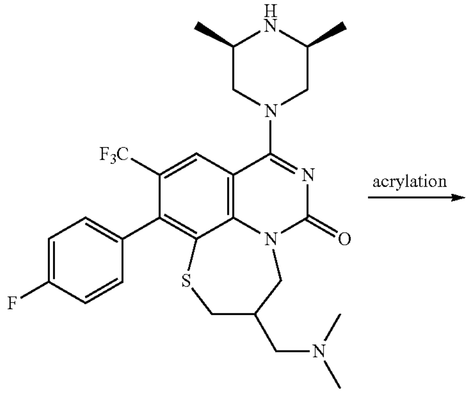
12

-continued

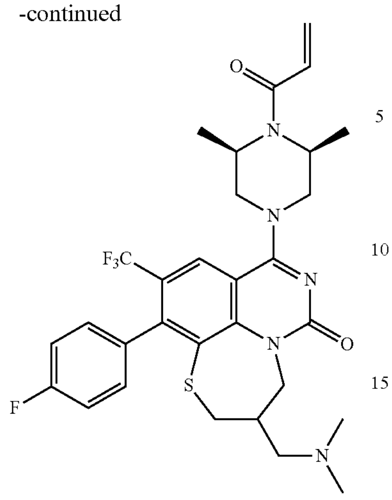

13

(2,2-dimethyl-1,3-dioxan-5-yl)methyl 4-methylbenzenesulfonate (2)

To a mixture of (2,2-dimethyl-1,3-dioxan-5-yl)methanol (10.5 g, 71.9 mmol) in dichloromethane (200 mL) was added triethylamine (21.8 g, 215.7 mmol) and tosyl chloride (20.5 g, 107.9 mmol) at 0° C. The mixture was stirred at room temperature for 2 hours. After completion, the mixture was concentrated and the residue was purified by silica gel column (dichloromethane/methanol=90/1) to afford (2,2-dimethyl-1,3-dioxan-5-yl)methyl 4-methylbenzenesulfonate (2) (22.2 g, crude) as a white solid. MS (ESI) m/z 301 $[M+H]^+$.

(2,2-dimethyl-1,3-dioxan-5-yl)methanethiol (3)

To a solution of (2,2-dimethyl-1,3-dioxan-5-yl)methyl 4-methylbenzenesulfonate (12.0 g, crude) in N,N-dimethylformamide (100 mL) was added sodium hydrosulfide (9.6 g, 120.0 mmol) at room temperature. The mixture was stirred at room temperature for 2 hours. After completion, the mixture was extracted with ethyl acetate and the organic phase was concentrated under reduce pressure. The residue was purified by silica gel column (dichloromethane/methanol=90/1) to afford (2,2-dimethyl-1,3-dioxan-5-yl)methanethiol (3) (3.4 g, yield: 52%) as a yellow oil. MS (ESI) m/z 163.0 $[M+H]^+$.

7-chloro-8-(((2,2-dimethyl-1,3-dioxan-5-yl)methyl)thio)-4-hydroxy-6-(trifluoromethyl)quinazolin-2(1H)-one (4)

To a mixture of 7-chloro-4-hydroxy-8-iodo-6-(trifluoromethyl)quinazolin-2(1H)-one (5.3 g, 13.6 mmol) and 4,5-bis(diphenylphosphino)-9,9-dimethylxanthene (1.6 g, 2.7 mmol) in 1,4-dioxane (600 mL) was added tris(dibenzylideneacetone)dipalladium (1.3 g, 1.3 mmol), potassium carbonate (5.6 g, 40.7 mmol) and (2,2-dimethyl-1,3-dioxan-5-yl)methanethiol (2.9 g, 17.9 mmol) at room temperature. The mixture was stirred at 60° C. overnight. After filtration and concentration, the residue was purified by silica gel chromatography (dichloromethane/methanol=1/10) to afford 7-chloro-8-(((2,2-dimethyl-1,3-dioxan-5-yl)methyl)thio)-4-hydroxy-6-(trifluoromethyl)quinazolin-2(1H)-one (4) (4.21 g, 9.9 mmol) as a white solid. MS (ESI) m/z 425.0 $[M+H]^+$.

7-chloro-4-hydroxy-8-((3-hydroxy-2-(hydroxymethyl)propyl)thio)-6-(trifluoromethyl)quinazolin-2(1H)-one (5)

The mixture of 7-chloro-8-(((2,2-dimethyl-1,3-dioxan-5-yl)methyl)thio)-4-hydroxy-6-(trifluoromethyl)quinazolin-2(1H)-one (4.2 g, 9.9 mmol) in acetonitrile was added hydrochloric acid (20 mL, 5N). The mixture was stirred at room temperature for 1 hour. After completion, the mixture was filtered. The filter cake was dried under reduce pressure to afford 7-chloro-4-hydroxy-8-((3-hydroxy-2-(hydroxymethyl)propyl)thio)-6-(trifluoromethyl)quinazolin-2(1H)-one (5) (4.17 g, 10.8 mmol, crude) as a white solid. MS (ESI) m/z 385.0 $[M+H]^+$.

11-chloro-8-hydroxy-3-(hydroxymethyl)-10-(trifluoromethyl)-3,4-dihydro-[1,4]thiazepino[2,3,4-ij]quinazolin-6(2H)-one (6)

To a mixture of 7-chloro-4-hydroxy-8-((3-hydroxy-2-(hydroxymethyl)propyl)thio)-6-(trifluoromethyl)quinazolin-2(1H)-one (5) (4.0 g, 10.4 mmol) and triphenylphosphine (4.09 g, 15.6 mmol) in tetrahydrofuran and N,N-dimethylformamide was added diethyl azodicarboxylate (2.72 g, 15.6 mmol) at 0° C. under nitrogen atmosphere. The mixture was stirred at room temperature for 1 hour. After completion, the mixture was concentrated and the residue was purified by flash chromatography column (C18, acetonitrile/water=20% to 95%) to afford 11-chloro-8-hydroxy-3-(hydroxymethyl)-10-(trifluoromethyl)-3,4-dihydro-[1,4]thiazepino[2,3,4-ij]quinazolin-6(2H)-one (6) (2.8 g, 7.65 mmol, yield: 73%) as a white solid. MS (ESI) m/z 367.3 $[M+H]^+$.

3-(((tert-butyldimethylsilyl)oxy)methyl)-11-chloro-8-hydroxy-10-(trifluoromethyl)-3,4-dihydro-[1,4]thiazepino[2,3,4-ij]quinazolin-6(2H)-one (7)

To a mixture of 11-chloro-8-hydroxy-3-(hydroxymethyl)-10-(trifluoromethyl)-3,4-dihydro-[1,4]thiazepino[2,3,4-ij]quinazolin-6(2H)-one (2.8 g, 7.65 mmol) and imidazole (2.08 g, 30.6 mmol) in N,N-dimethylformamide (30 mL) was added tert-butyldimethylsilyl chloride (2.31 g, 15.3 mmol) at 25° C. The mixture was stirred at 25° C. for 1 hour. After completion, the mixture was extracted with ethyl acetate. Concentrated and the residue was purified by silica gel column (petroleum ether/ethyl acetate=7/1) to give the title product (7) (3.7 g, crude) as yellow solid. MS (ESI) m/z 481.2 $[M+H]^+$.

(2S,6R)-tert-butyl 4-(3-(((tert-butyldimethylsilyl)oxy)methyl)-11-chloro-6-oxo-10-(trifluoromethyl)-2,3,4,6-tetrahydro-[1,4]thiazepino[2,3,4-ij]quinazolin-8-yl)-2,6-dimethylpiperazine-1-carboxylate (8)

To a solution of 3-(((tert-butyldimethylsilyl)oxy)methyl)-11-chloro-8-hydroxy-10-(trifluoromethyl)-3,4-dihydro-[1,4]thiazepino[2,3,4-ij]quinazolin-6(2H)-one (7) (3.7 g, 7.7 mmol) in acetonitrile were added potassium carbonate (5.3 g, 38.5 mmol) and 2,4,6-triisopropylbenzenesulfonyl chloride (3.5 g, 11.55 mmol). The mixture was stirred at 25° C. under nitrogen atmosphere for 5 hours. Above mixture was added (2S,6R)-tert-butyl 2,6-dimethylpiperazine-1-carboxylate (2.64 g, 12.3 mmol) at room temperature and stirred at 25° C. under nitrogen atmosphere overnight. After completion, the mixture was filtered. The filtration was concentrated under reduce pressure and extracted with ethyl acetate. After concentration, the residue was purified by silica gel column (dichloromethane/methanol=80/1) to afford the title product (8) (4.3 g, 6.36 mmol, yield: 82%) as a yellow solid. (ESI) m/z 677.2 [M+H]$^+$.

(2S,6R)-tert-butyl 4-(3-(((tert-butyldimethylsilyl)oxy)methyl)-11-(4-fluorophenyl)-6-oxo-10-(trifluoromethyl)-2,3,4,6-tetrahydro-[1,4]thiazepino[2,3,4-ij]quinazolin-8-yl)-2,6-dimethylpiperazine-1-carboxylate (9)

To a mixture of (2S,6R)-tert-butyl 4-(3-(((tert-butyldimethylsilyl)oxy)methyl)-11-chloro-6-oxo-10-(trifluoromethyl)-2,3,4,6-tetrahydro-[1,4]thiazepino[2,3,4-ij]quinazolin-8-yl)-2,6-dimethylpiperazine-1-carboxylate (8) (1.1 g, 1.62 mmol) in 1,4-dioxane and water was added [2'-(Amino)[1,1'-biphenyl]-2-yl][[2',6'-bis(1-methylethoxy)[1,1'-biphenyl]-2-yl]dicyclohexylphosphine]chloropalladium (253 mg, 0.325 mmol), potassium phosphate trihydrate (2.16 g, 8.13 mmol) and (4-fluorophenyl)boronic acid (1.14 g, 8.13 mmol) at 25° C. The mixture was stirred at 85° C. for 2 hours. After completion, the mixture was concentrated and the residue was purified by silica gel column chromatography (dichloromethane/ethyl acetate=80/1) to afford (2S,6R)-tert-butyl 4-(3-(((tert-butyldimethylsilyl)oxy)methyl)-11-(4-fluorophenyl)-6-oxo-10-(trifluoromethyl)-2,3,4,6-tetrahydro-[1,4]thiazepino[2,3,4-ij]quinazolin-8-yl)-2,6-dimethylpiperazine-1-carboxylate (9) (1.5 g, crude) as a yellow solid. (ESI) m/z 737.2 [M+H]$^+$.

(2S,6R)-tert-butyl 4-(11-(4-fluorophenyl)-3-(hydroxymethyl)-6-oxo-10-(trifluoromethyl)-2,3,4,6-tetrahydro-[1,4]thiazepino[2,3,4-ij]quinazolin-8-yl)-2,6-dimethylpiperazine-1-carboxylate (10)

To a mixture of (2S,6R)-tert-butyl 4-(3-(((tert-butyldimethylsilyl)oxy)methyl)-11-(4-fluorophenyl)-6-oxo-10-(trifluoromethyl)-2,3,4,6-tetrahydro-[1,4]thiazepino[2,3,4-ij]quinazolin-8-yl)-2,6-dimethylpiperazine-1-carboxylate (9) (1.42 g, 1.93 mmol) in dichloromethane (10 mL) was added tetrabutylammonium fluoride (20 mL, 1N in tetrahydrofuran) at 25° C. The mixture was stirred at 25° C. for 1 hour. After completion, the mixture was extracted with dichloromethane. After concentration, the residue was purified by silica gel column chromatography (dichloromethane/methanol=83/1) to afford (2S,6R)-tert-butyl 4-(11-(4-fluorophenyl)-3-(hydroxymethyl)-6-oxo-10-(trifluoromethyl)-2,3,4,6-tetrahydro-[1,4]thiazepino[2,3,4-ij]quinazolin-8-yl)-2,6-dimethylpiperazine-1-carboxylate (10) (1.0 g, 0.013 mmol, yield: 83%) as yellow solid. MS (ESI) m/z 623.2 [M+H]$^+$.

(2S,6R)-tert-butyl 4-(3-((dimethylamino)methyl)-11-(4-fluorophenyl)-6-oxo-10-(trifluoromethyl)-2,3,4,6-tetrahydro-[1,4]thiazepino[2,3,4-ij]quinazolin-8-yl)-2,6-dimethylpiperazine-1-carboxylate (11)

To a mixture of (2S,6R)-tert-butyl 4-(11-(4-fluorophenyl)-3-(hydroxymethyl)-6-oxo-10-(trifluoromethyl)-2,3,4,6-tetrahydro-[1,4]thiazepino[2,3,4-ij]quinazolin-8-yl)-2,6-dimethylpiperazine-1-carboxylate (10) (500 mg, 0.8 mmol) in dichloromethane (4 mL) was added Dess-martin reagent (511 mg, 1.2 mmol) at 25° C. The mixture was stirred at 25° C. for 1 hour. After completion, a solution of dimethylamine (0.6 mL, 2N in tetrahydrofuran) and sodium triacetoxyborohydride (256 mg, 1.2 mmol) in dichloromethane (4 mL) was added to above mixture at 25° C. The mixture was stirred at 25° C. for 1 hour. After completion, the mixture was concentrated and the residue was purified by silica gel column chromatography (dichloromethane/methanol=21/1) to afford (2S,6R)-tert-butyl 4-(3-((dimethylamino)methyl)-11-(4-fluorophenyl)-6-oxo-10-(trifluoromethyl)-2,3,4,6-tetrahydro-[1,4]thiazepino[2,3,4-ij]quinazolin-8-yl)-2,6-dimethylpiperazine-1-carboxylate (11) (468 mg, 0.72 mmol, yield: 89%) as yellow solid. MS (ESI) m/z 650.2 [M+H]$^+$.

3-((dimethylamino)methyl)-8-((3S,5R)-3,5-dimethylpiperazin-1-yl)-11-(4-fluorophenyl)-10-(trifluoromethyl)-3,4-dihydro-[1,4]thiazepino[2,3,4-ij]quinazolin-6(2H)-one (12)

To a mixture of (2S,6R)-tert-butyl 4-(3-((dimethylamino)methyl)-11-(4-fluorophenyl)-6-oxo-10-(trifluoromethyl)-2,3,4,6-tetrahydro-[1,4]thiazepino[2,3,4-ij]quinazolin-8-yl)-2,6-dimethylpiperazine-1-carboxylate (11) (468 mg, 0.72 mmol) in dichloromethane (6 mL) was added trifluoroacetic acid (3 mL) at 25° C. The mixture was stirred at 25° C. for 1 hour. After completion, the mixture was concentrated and adjusted PH to 8 with ammonia in methanol at 0° C. The mixture was concentrated and purified by silica gel column chromatography (dichloromethane/methanol=30/1) to afford 3-((dimethylamino)methyl)-8-((3S,5R)-3,5-dimethylpiperazin-1-yl)-11-(4-fluorophenyl)-10-(trifluoromethyl)-3,4-dihydro-[1,4]thiazepino[2,3,4-ij]quinazolin-6(2H)-one (12) (264 mg, 0.48 mmol, yield: 66%) as yellow solid. MS (ESI) m/z 550.2 [M+H]$^+$.

8-((3S,5R)-4-acryloyl-3,5-dimethylpiperazin-1-yl)-3-((dimethylamino)methyl)-11-(4-fluorophenyl)-10-(trifluoromethyl)-3,4-dihydro-[1,4]thiazepino[2,3,4-ij]quinazolin-6(2H)-one (13)

To a mixture of 3-((dimethylamino)methyl)-8-((3S,5R)-3,5-dimethylpiperazin-1-yl)-11-(4-fluorophenyl)-10-(trifluoromethyl)-3,4-dihydro-[1,4]thiazepino[2,3,4-ij]quinazolin-6(2H)-one (12) (244 mg, 0.44 mmol) in dichloromethane (4 mL) was added triethylamine (135 mg, 1.32 mmol) and acrylic anhydride (84 mg, 0.66 mmol) at 5° C. The mixture was stirred at 25° C. for 1 hour. After completion, the mixture was added methanol at 25° C. and concentrated. The mixture was purified by preparative high performance liquid chromatography (20% to 95% acetonitrile in water) to afford 8-((3S,5R)-4-acryloyl-3,5-dimethylpiperazin-1-yl)-3-((dimethylamino)methyl)-11-(4-fluorophenyl)-10-(trifluoromethyl)-3,4-dihydro-[1,4]thiazepino[2,3,4-ij]quinazolin-6(2H)-one (13) (124 mg, 0.2 mmol, yield: 46%) as a pale yellow powder.

MS (ESI) m/z 603.6 [M+H]$^+$. $^1$H NMR (400 MHz, CDCl3) δ 8.06 (s, 1H), 7.22-7.15 (m, 4H), 6.66-6.59 (m, 1H), 6.41 (d, J=16.4 Hz, 1H), 5.77 (d, J=10.4 Hz, 1H), 4.84-4.44 (m, 3H), 4.27-3.99 (m, 3H), 3.37-3.19 (m, 3H), 3.09-2.97 (m, 1H), 2.68-2.44 (m, 1H), 2.30-2.21 (m, 8H), 1.59-1.51 (m, 6H).

Examples 2038 and 2039: 8-((3S,5R)-4-acryloyl-3,5-dimethylpiperazin-1-yl)-11-(4-fluorophenyl)-3-(((S)-3-fluoropyrrolidin-1-yl)methyl)-10-(trifluoromethyl)-3,4-dihydro-[1,4]thiazepino[2,3,4-ij]quinazolin-6(2H)-one

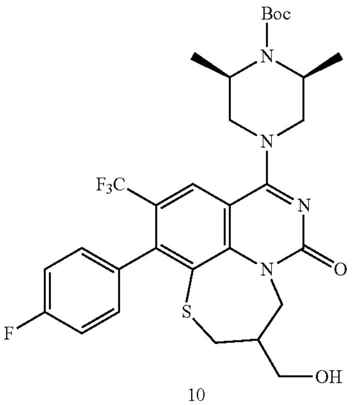

10

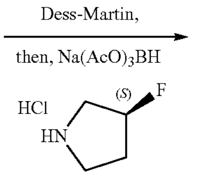

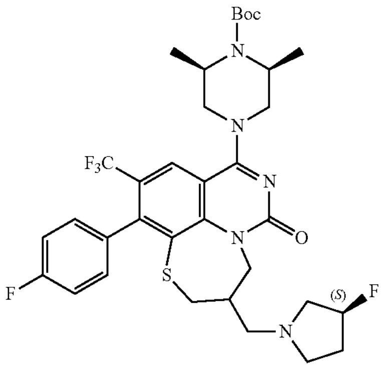

14

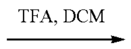

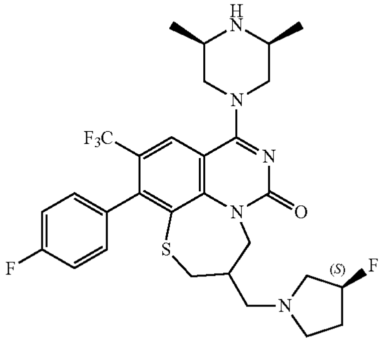

15

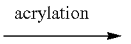

-continued

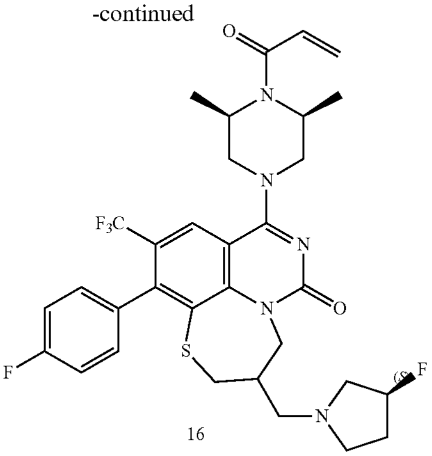

16

(2S,6R)-tert-butyl 4-(11-(4-fluorophenyl)-3-(((S)-3-fluoropyrrolidin-1-yl)methyl)-6-oxo-10-(trifluoromethyl)-2,3,4,6-tetrahydro-[1,4]thiazepino[2,3,4-ij]quinazolin-8-yl)-2,6-dimethylpiperazine-1-carboxylate (14)

To a mixture of (2S,6R)-tert-butyl 4-(11-(4-fluorophenyl)-3-(hydroxymethyl)-6-oxo-10-(trifluoromethyl)-2,3,4,6-tetrahydro-[1,4]thiazepino[2,3,4-ij]quinazolin-8-yl)-2,6-dimethylpiperazine-1-carboxylate (400 mg, 0.64 mmol) in dichloromethane (6 mL) was added Dess-martin (409 mg, 0.96 mmol) at 25° C. The mixture was stirred at 25° C. for 1 hour. After completion, a solution of (S)-3-fluoropyrrolidine hydrochloride (121 mg, 0.96 mmol) and sodium triacetoxyborohydride (205 mg, 0.96 mmol) in dichloromethane (4 mL) was added to above mixture at 25° C. The mixture was stirred at 25° C. for 1 hour. After completion, the mixture was concentrated and the residue was purified by silica gel column chromatography (dichloromethane/methanol=21/1) to afford (2S,6R)-tert-butyl 4-(11-(4-fluorophenyl)-3-(((S)-3-fluoropyrrolidin-1-yl)methyl)-6-oxo-10-(trifluoromethyl)-2,3,4,6-tetrahydro-[1,4]thiazepino[2,3,4-ij]quinazolin-8-yl)-2,6-dimethylpiperazine-1-carboxylate (14) (400 mg, 0.58 mmol, yield: 89%) as yellow solid. MS (ESI) m/z 694.2 $[M+H]^+$.

8-((3S,5R)-3,5-dimethylpiperazin-1-yl)-11-(4-fluorophenyl)-3-(((S)-3-fluoropyrrolidin-1-yl)methyl)-10-(trifluoromethyl)-3,4-dihydro-[1,4]thiazepino[2,3,4-ij]quinazolin-6(2H)-one (15)

To a mixture of (2S,6R)-tert-butyl 4-(11-(4-fluorophenyl)-3-(((S)-3-fluoropyrrolidin-1-yl)methyl)-6-oxo-10-(trifluoromethyl)-2,3,4,6-tetrahydro-[1,4]thiazepino[2,3,4-ij]quinazolin-8-yl)-2,6-dimethylpiperazine-1-carboxylate (14) (400 mg, 0.58 mmol) in dichloromethane (6 mL) was added trifluoroacetic acid (3 mL) at 25° C. The mixture was stirred at 25° C. for 1 hour. After completion, the mixture was concentrated and adjusted PH to 8 with ammonia in methanol at 0° C. The mixture was concentrated and purified by silica gel column chromatography (dichloromethane/methanol=30/1) to afford 8-((3S,5R)-3,5-dimethylpiperazin-1-yl)-11-(4-fluorophenyl)-3-(((S)-3-fluoropyrrolidin-1-yl)methyl)-10-(trifluoromethyl)-3,4-dihydro-[1,4]thiazepino[2,3,4-ij]quinazolin-6(2H)-one (15) (216 mg, 0.36 mmol, yield: 63%) as yellow solid. MS (ESI) m/z 594.2 $[M+H]^+$.

8-((3S,5R)-4-acryloyl-3,5-dimethylpiperazin-1-yl)-11-(4-fluorophenyl)-3-(((S)-3-fluoropyrrolidin-1-yl)methyl)-10-(trifluoromethyl)-3,4-dihydro-[1,4]thiazepino[2,3,4-ij]quinazolin-6(2H)-one (16)

To a mixture of 8-((3S,5R)-3,5-dimethylpiperazin-1-yl)-11-(4-fluorophenyl)-3-(((S)-3-fluoropyrrolidin-1-yl)methyl)-10-(trifluoromethyl)-3,4-dihydro-[1,4]thiazepino[2,3,4-ij]quinazolin-6(2H)-one (15) (216 mg, 0.36 mmol) in dichloromethane (4 mL) was added triethylamine (110 mg, 1.09 mmol) and acrylic anhydride (69 mg, 0.55 mmol) at 5° C. The mixture was stirred at 25° C. for 1 hour. After completion, the mixture was added methanol at 25° C. and concentrated. The mixture was purified by preparative high performance liquid chromatography (20% to 95% acetonitrile in water) to afford 8-((3S,5R)-4-acryloyl-3,5-dimethylpiperazin-1-yl)-11-(4-fluorophenyl)-3-(((S)-3-fluoropyrrolidin-1-yl)methyl)-10-(trifluoromethyl)-3,4-dihydro-[1,4]thiazepino[2,3,4-ij]quinazolin-6(2H)-one (16) (119 mg, 0.18 mmol, yield: 50%) as a pale yellow powder. MS (ESI) m/z 648.6 $[M+H]^+$. $^1H$ NMR (400 MHz, CDCl3) δ 8.06 (s, 1H), 7.21-7.15 (m, 4H), 6.66-6.59 (m, 1H), 6.41 (d, J=16.4 Hz, 1H), 5.78 (d, J=10.8 Hz, 1H), 5.18-5.04 (m, 1H), 4.80-4.41 (m, 3H), 4.26-4.05 (m, 3H), 3.37-3.22 (m, 3H), 3.13-3.02 (m, 1H), 2.86-2.72 (m, 3H), 2.64-2.53 (m, 2H), 2.43-2.26 (m, 2H), 2.16-1.91 (m, 2H), 1.59-1.51 (m, 6H).

Example 2084: (S)-8-((3S,5R)-4-acryloyl-3,5-dimethylpiperazin-1-yl)-3-(4-fluorophenoxy)-11-(4-fluorophenyl)-10-(trifluoromethyl)-3,4-dihydro-2H,6H-[1,4]thiazepino[2,3,4-ij]quinazolin-6-one

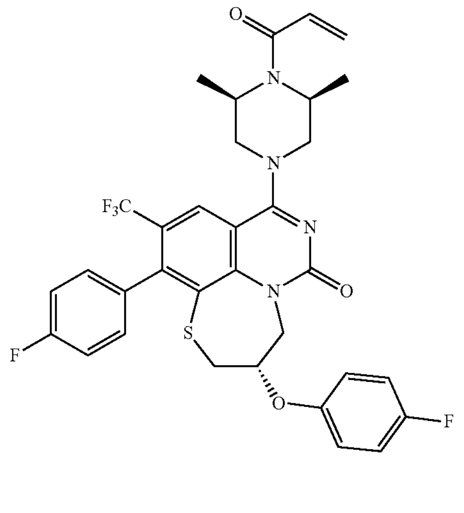 [SMILES: C=CC(=O)N1[C@H](C)CN(c2nc(=O)n3c4c(c(-c5ccc(F)cc5)c(C(F)(F)F)cc24)SC[C@@H](Oc2ccc(F)cc2)C3)C[C@@H]1C]

Reaction Scheme

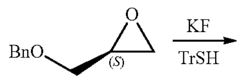

1

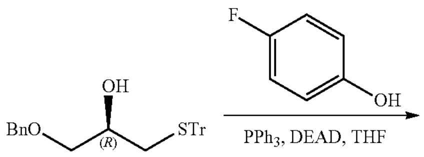

2

-continued

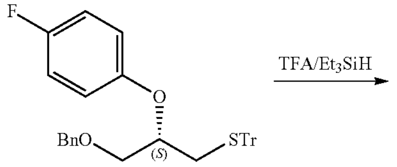

3

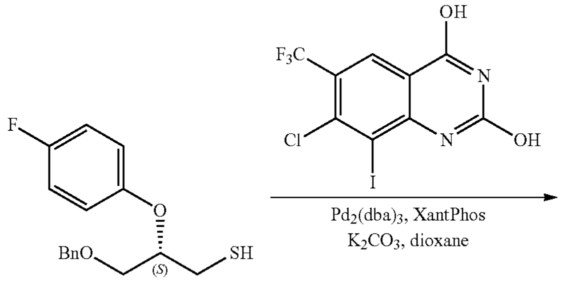

4

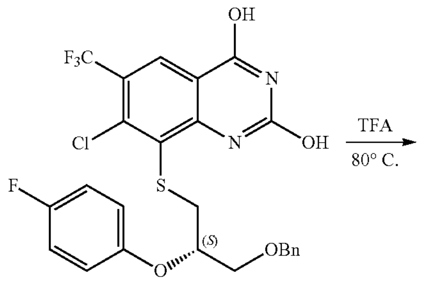

5

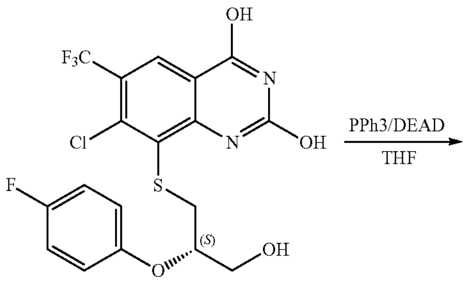

6

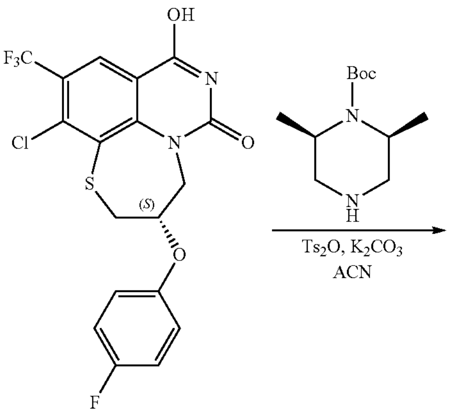

7

-continued

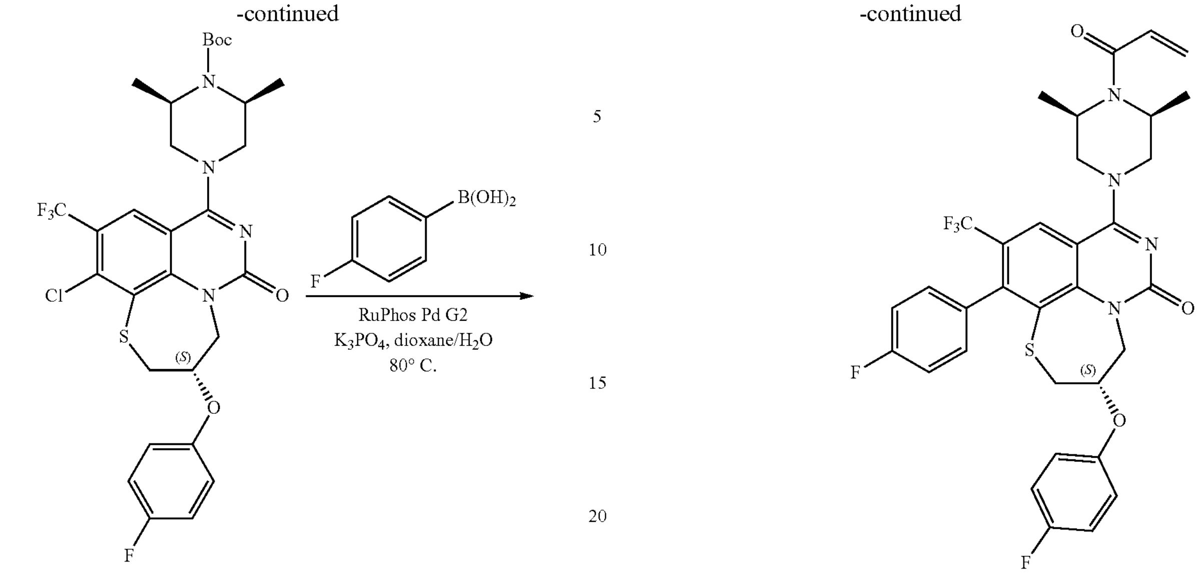

8

11

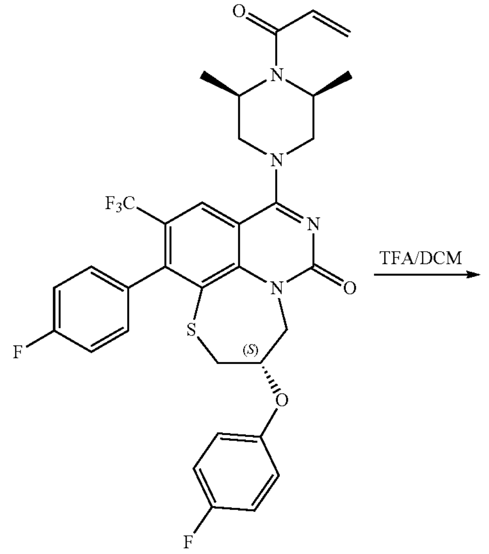

9

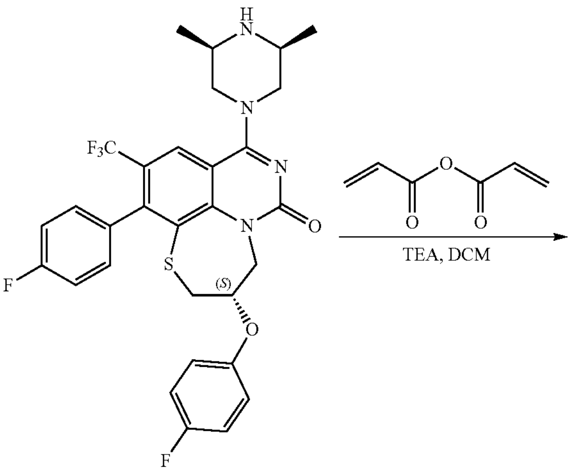

10

(R)-1-(benzyloxy)-3-(tritylthio)propan-2-ol (2)

To a mixture of (S)-2-((benzyloxy)methyl)oxirane (25 g, 152.4 mmol) and potassium fluoride (17.7 g, 304.8 mmol) in methonal (250 mL) was added triphenylmethanethiol (42 g, 152.4 mmol). The mixture was stirred at room temperature for 18 hours. After completion, the mixture was concentrated under reduced pressure. The residue was purified by silica gel column with petroleum ether/ethyl acetate=5/1 to afford (R)-1-(benzyloxy)-3-(tritylthio)propan-2-ol (2) (60 g, 90% yield) as a colorless oil.

$^1$H NMR (400 MHz, $CDCl_3$) δ 7.44-7.38 (m, 6H), 7.35-7.18 (m, 14H), 4.46 (s, 2H), 3.58-3.48 (m, 1H), 3.37-3.26 (m, 2H), 2.45-2.35 (m, 2H).

(S)-(3-(benzyloxy)-2-(4-fluorophenoxy)propyl)(trityl)sulfane (3)

To a mixture of 4-fluorophenol (5.1 g, 45.45 mmol) and triphenylphosphine (14.3 g, 54.54 mmol) in tetrahydrofuran (400 mL) was added diethyl azodicarboxylate (9.5 g, 54.54 mmol) at 0° C. under nitrogen atmosphere. The mixture was stirred at room temperature for 10 min, then was added (R)-1-(benzyloxy)-3-(tritylthio)propan-2-ol (20 g, 45.45 mmol). The mixture was stirred for 2 hours. After completion, the mixture was poured into ice-water (300 mL) and extracted with ethyl acetate (150 mL×3). After concentration, the residue was purified by silica gel column with petroleum ether/ethyl acetate=50/1 to afford to afford crude (S)-(3-(benzyloxy)-2-(4-fluorophenoxy)propyl)(trityl)sulfane (3) (17.8 g, crude) as a yellow oil. $^1$H NMR (400 MHz, $CDCl_3$) δ 7.43-7.41 (m, 6H), 7.37-7.17 (m, 14H), 6.89-6.84 (m, 2H), 6.66-6.62 (m, 2H), 4.48 (s, 2H), 3.97-3.94 (m, 1H), 3.53-3.49 (m, 2H), 2.66-2.53 (m, 2H).

(S)-3-(benzyloxy)-2-(4-fluorophenoxy)propane-1-thiol (4)

To a mixture of (S)-(3-(benzyloxy)-2-(4-fluorophenoxy)propyl)(trityl)sulfane (17.8 g, 33.3 mmol) and triethylsilane (9.7 g, 83.3 mmol) in dichloromethane (100 mL) was added trifluoroacetic acid (38 g, 333 mmol). The mixture was stirred at room temperature for 2 hours. After completion, the mixture was concentrated and adjusted pH=7~8 at 0° C. After concentration, the residue was purified by silica gel column with petroleum ether/ethyl acetate=15/1 to afford (S)-3-(benzyloxy)-2-(4-fluorophenoxy)propane-1-thiol (4) (5 g, 51% yield) as a yellow oil. $^1$H NMR (400 MHz, $CDCl_3$) δ 7.30-7.21 (m, 4H), 7.05-7.04 (m, 1H), 6.91-6.81 (m, 4H), 4.49 (d, J=4.8 Hz, 2H), 4.31-4.28 (m, 1H), 3.65-3.60 (m, 2H), 2.86-2.71 (m, 2H), 1.46 (t, J=9.2 Hz, 1H).

(S)-8-((3-(benzyloxy)-2-(4-fluorophenoxy)propyl)thio)-7-chloro-6-(trifluoromethyl)quinazoline-2,4-diol (5)

To a solution of 7-chloro-8-iodo-6-(trifluoromethyl)quinazoline-2,4-diol (2.67 g, 6.85 mmol) in 1,4-dioxane (100 mL) was added potassium carbonate (2.36 g, 17.1 mmol), (S)-3-(benzyloxy)-2-(4-fluorophenoxy)propane-1-thiol (5 g, 17.1 mmol), 4,5-Bis(diphenyl-phosphino)-9,9-dimethylxanthene (594 mg, 1.03 mmol) and Tris(dibenzylideneacetone)dipalladium (630 mg, 0.685 mmol). The mixture was stirred at 60° C. under nitrogen atmosphere for 18 hours. After completion, the mixture was concentrated under reduced pressure, the residue was purified by silica gel column chromatography (dichloromethane/ethyl acetate=3/1) to afford (S)-8-((3-(benzyloxy)-2-(4-fluorophenoxy)propyl)thio)-7-chloro-6-(trifluoromethyl)quinazoline-2,4-diol (5) (2.4 g, yield: 63%) as pale yellow solid. MS (ESI) m/z 553.3 $[M-H]^+$.

(S)-7-chloro-8-((2-(4-fluorophenoxy)-3-hydroxypropyl)thio)-6-(trifluoromethyl)quinazoline-2,4-diol (6)

A solution of (S)-8-((3-(benzyloxy)-2-(4-fluorophenoxy)propyl)thio)-7-chloro-6-(trifluoromethyl)quinazoline-2,4-diol (2.4 g, 4.33 mmol) in trifluoroacetic acid (12 mL) was stirred at 80° C. for 18 hrs. After completion, the mixture was concentrated and adjusted pH=7~8 at 0° C. After concentration, the residue was purified by silica gel column with dichloromethane/ethyl acetate=1/2 to afford (S)-7-chloro-8-((2-(4-fluorophenoxy)-3-hydroxypropyl)thio)-6-(trifluoromethyl)quinazoline-2,4-diol (6) (1.8 g, yield: 90%) as a yellow solid. MS (ESI): m/z 463 $[M-H]^+$.

(S)-11-chloro-3-(4-fluorophenoxy)-8-hydroxy-10-(trifluoromethyl)-3,4-dihydro-2H,6H-[1,4]thiazepino[2,3,4-ij]quinazolin-6-one (7)

To a mixture of (S)-7-chloro-8-((2-(4-fluorophenoxy)-3-hydroxypropyl)thio)-6-(trifluoromethyl)quinazoline-2,4-diol (1.7 g, 3.66 mmol) and triphenylphosphine (2.87 g, 10.95 mmol) in tetrahydrofuran (100 mL) was added diethyl azodicarboxylate (1.91 g, 10.95 mmol) at 0° C. The mixture was stirred at 0° C. for 45 min. After completion, the mixture was poured into ice-water (100 mL) and extracted with ethyl acetate (100 mL×3). Concentrated and the residue was purified by C18 with 30-95% acetonitrile in water to afford (S)-11-chloro-3-(4-fluorophenoxy)-8-hydroxy-10-(trifluoromethyl)-3,4-dihydro-2H,6H-[1,4]thiazepino[2,3,4-ij]quinazolin-6-one (7) (1.27 g, 78% yield) as a yellow solid. MS (ESI) m/z 445.2 $[M-H]^+$.

tert-butyl (2S,6R)-4-((S)-11-chloro-3-(4-fluorophenoxy)-6-oxo-10-(trifluoromethyl)-3,4-dihydro-2H,6H-[1,4]thiazepino[2,3,4-ij]quinazolin-8-yl)-2,6-dimethylpiperazine-1-carboxylate (8)

To a mixture of (S)-11-chloro-3-(4-fluorophenoxy)-8-hydroxy-10-(trifluoromethyl)-3,4-dihydro-2H,6H-[1,4]thiazepino[2,3,4-ij]quinazolin-6-one (7) (1.24 g, 2.78 mmol) and potassium carbonate (3.84 g, 27.8 mmol) in acetonitrile (50 mL) was added 4-methylbenzenesulfonic anhydride (1.81 g, 5.55 mmol). The mixture was stirred at 35° C. for 4 hours. After completion, (2S,6R)-tert-butyl 2,6-dimethylpiperazine-1-carboxylate (1.78 g, 8.32 mmol) was added into the reaction solution. The reaction mixture was stirred at 35° C. for 1 hour. After completion, the mixture was poured into ice-water (200 mL) and extracted with ethyl acetate (100 mL×3). Concentrated and the residue was purified by C18 column with 20-95% acetonitrile in water to afford tert-butyl (2S,6R)-4-((S)-11-chloro-3-(4-fluorophenoxy)-6-oxo-10-(trifluoromethyl)-3,4-dihydro-2H,6H-[1,4]thiazepino[2,3,4-ij]quinazolin-8-yl)-2,6-dimethylpiperazine-1-carboxylate (8) (930 mg, yield: 52%) as a pale yellow solid. MS (ESI) m/z 643.4 $[M+H]^+$.

(S)-8-((3S,5R)-4-acryloyl-3,5-dimethylpiperazin-1-yl)-3-(4-fluorophenoxy)-11-(4-fluorophenyl)-10-(trifluoromethyl)-3,4-dihydro-2H,6H-[1,4]thiazepino[2,3,4-ij]quinazolin-6-one (9)

To a solution of tert-butyl (2S,6R)-4-((S)-11-chloro-3-(4-fluorophenoxy)-6-oxo-10-(trifluoromethyl)-3,4-dihydro-2H,6H-[1,4]thiazepino[2,3,4-ij]quinazolin-8-yl)-2,6-dimethylpiperazine-1-carboxylate (8) (200 mg, 0.31 mmol) in 1,4-dioxane (3 mL) and water (0.5 mL) was added tripotassium phosphate (206 mg, 0.775 mmol), (4-fluorophenyl)boronic acid (131 mg, 0.93 mmol), and Chloro(2-dicyclohexylphosphino-2', 6'-diisopropoxy-1,1'-biphenyl)[2-(2'-amino-1,1'-biphenyl)]palladium(II) (36 mg, 0.046 mmol). The mixture was stirred at 80° C. under nitrogen atmosphere for 1 hour. After completion, the mixture was concentrated under reduced pressure, the residue was purified by silica gel column chromatography (dichloromethane/methanol=60/1) to afford (S)-8-((3S,5R)-4-acryloyl-3,5-dimethylpiperazin- 1-yl)-3-(4-fluorophenoxy)-11-(4-fluorophenyl)-10-(trifluoromethyl)-3,4-dihydro-2H,6H-[1,4]thiazepino[2,3,4-ij]quinazolin-6-one (9) (240 mg, crude) as a yellow solid. MS (ESI) m/z 703.6 [M+H]$^+$.

(S)-8-((3S,5R)-3,5-dimethylpiperazin-1-yl)-3-(4-fluorophenoxy)-11-(4-fluorophenyl)-10-(trifluoromethyl)-3,4-dihydro-2H,6H-[1,4]thiazepino[2,3,4-ij]quinazolin-6-one (10)

To a mixture of (S)-8-((3S,5R)-4-acryloyl-3,5-dimethylpiperazin-1-yl)-3-(4-fluorophenoxy)-11-(4-fluorophenyl)-10-(trifluoromethyl)-3,4-dihydro-2H,6H-[1,4]thiazepino[2,3,4-ij]quinazolin-6-one (9) (240 mg, crude) in dichloromethane (2 mL) was added trifluoroacetic acid (2 mL) at 0° C. The reaction solution was stirred at room temperature for 1 hour. After completion, the mixture was concentrated and the residue was purified by silica gel column chromatography (dichloromethane/methanol=15/1) to afford (S)-8-((3S,5R)-4-acryloyl-3,5-dimethylpiperazin-1-yl)-3-(4-fluorophenoxy)-11-(4-fluorophenyl)-10-(trifluoromethyl)-3,4-dihydro-2H,6H-[1,4]thiazepino[2,3,4-ij]quinazolin-6-one (10) (135 mg, yield: 66%) as a pale yellow solid. MS (ESI) m/z 603.2 [M+H]$^+$.

(S)-8-((3S,5R)-4-acryloyl-3,5-dimethylpiperazin-1-yl)-3-(4-fluorophenoxy)-11-(4-fluorophenyl)-10-(trifluoromethyl)-3,4-dihydro-2H,6H-[1,4]thiazepino[2,3,4-ij]quinazolin-6-one (11)

To a mixture of (S)-8-((3S,5R)-4-acryloyl-3,5-dimethylpiperazin-1-yl)-3-(4-fluorophenoxy)-11-(4-fluorophenyl)-10-(trifluoromethyl)-3,4-dihydro-2H,6H-[1,4]thiazepino[2,3,4-ij]quinazolin-6-one (10) (135 mg, 0.224 mmol) and triethyl amine (45 mg, 0.448 mmol) in dichloromethane (3 ml) was added acrylic anhydride (42 mg, 0.336 mmol) at 0° C. The mixture was stirred at 0° C. for 1 hour. After completion, the mixture was poured into ice-water (30 mL) and extracted with dichloromethane (30 mL×3). Concentrated and the residue was purified by preparative High Performance Liquid Chromatography (20% to 95% acetonitrile in water) to afford (S)-8-((3S,5R)-4-acryloyl-3,5-dimethylpiperazin-1-yl)-3-(4-fluorophenoxy)-11-(4-fluorophenyl)-10-(trifluoromethyl)-3,4-dihydro-2H,6H-[1,4]thiazepino[2,3,4-ij]quinazolin-6-one (11) (50 mg, yield: 34%) as a white solid. MS (ESI) m/z 657.2 [M+H]$^+$.

$^1$H NMR (400 MHz, $CDCl_3$) δ 8.09 (s, 1H), 7.26-7.24 (m, 1H), 7.20-7.16 (m, 3H), 7.00-6.93 (m, 4H), 6.66-6.60 (m, 1H), 6.42 (dd, J 16.4 Hz, 1.6 Hz, 1H), 5.78 (dd, J 10.4 Hz, 2.0 Hz, 1H), 4.96-4.60 (m, 5H), 4.18 (d, J=13.2 Hz, 2H), 3.43-3.35 (m, 3H), 3.17-3.13 (m, 1H), 1.55 (d, J 6.8 Hz, 3H), 1.53 (d, J 6.4 Hz, 3H).

Example 2010 and 2011: (3S,10S)-7-((3S,5R)-4-(Acryloyl-d3)-3,5-dimethylpiperazin-1-yl)-10-(5-chloro-2,4-difluorophenyl)-3-(methoxymethyl)-9-(trifluoromethyl)-2,3-dihydro-5H-[1,4]thiazino[2,3,4-ij]quinazolin-5-one (P1) and (3S,10R)-7-((3S,5R)-4-(Acryloyl-$d_3$)-3,5-dimethylpiperazin-1-yl)-10-(5-chloro-2,4-difluorophenyl)-3-(methoxymethyl)-9-(trifluoromethyl)-2,3-dihydro-5H-[1,4]thiazino[2,3,4-ij]quinazolin-5-one (P2)

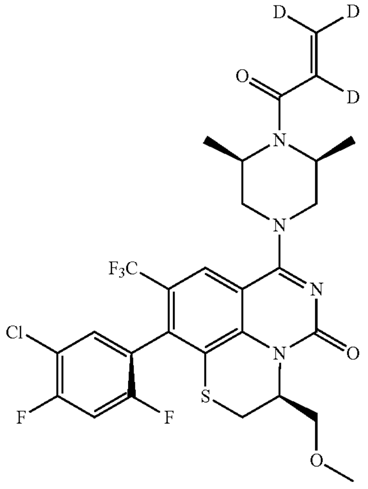

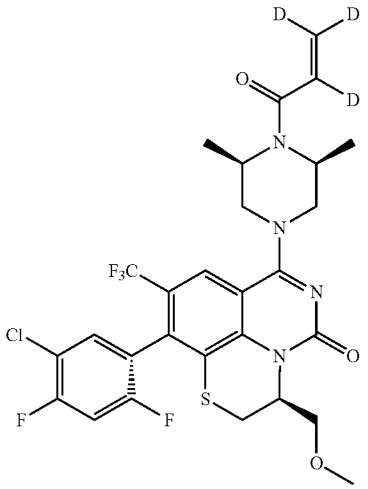

Reaction Scheme

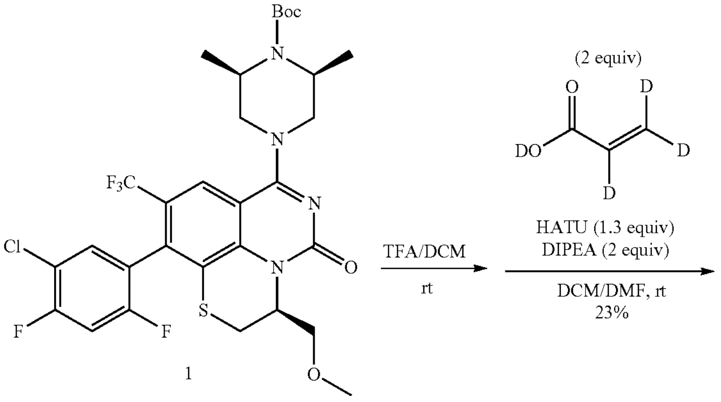

1

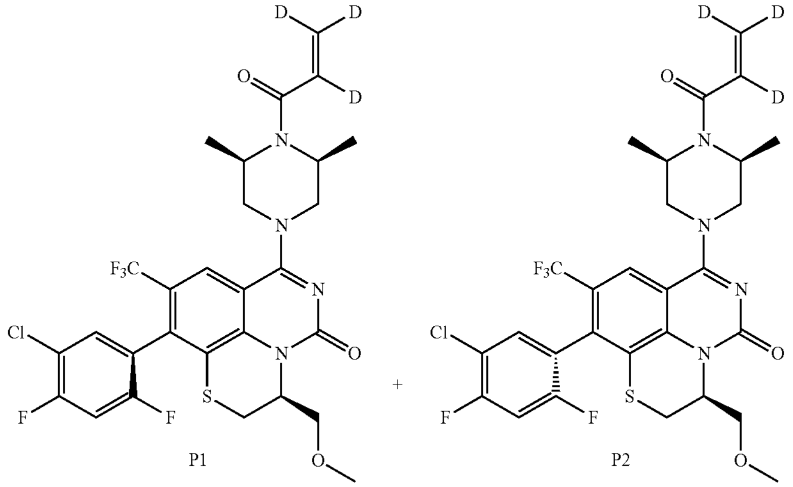

P1 + P2

Compound 1 (190 mg, 0.28 mmol, 1 equiv) was dissolved in anhydrous $CH_2Cl_2$ (7 mL) in a 20 dr vial followed by the addition of $CF_3COOH$ (3 mL) at room temperature and capped. After 15 min, the reaction was determined to be complete by LC-MS and the solvent was removed by rotary evaporation. Acrylic acid-$d_4$ (43 mg, 0.56 mmol, 2.0 equiv) in a 25 mL round-bottom flask under nitrogen was dissolved in anhydrous $CH_2Cl_2$ (12 mL). DIPEA (98 μL, 0.56 mmol, 2.0 equiv followed by HATU (138 mg, 0.364 mmol, 1.3 equiv) were added. Next, the deprotected amine dissolved in DMF (2 mL) was added and the resulting reaction mixture was stirred at room temperature. After 21 h, the solvent was removed by rotary evaporation. The mixture was transferred to a separatory funnel with EtOAc (200 mL) and washed with $H_2O$ (30 mL, 3×). The organic layer was dried over $Na_2SO_4$ and the solvent was removed by rotary evaporation. The crude material was dissolved in MeOH, filtered with a 0.45 μM PTFE plug, and purified by preparative RP-HPLC (Luna 5 μM C18(2) 100 Å, 100×30 mm, 5-95% MeCN+ 0.1% (v/v) HCOOH and $H_2O$+0.1% (v/v) HCOOH). The product fractions were collected, and the solvent was removed by rotary evaporation, followed by lyophilization (−91 to −71° C.; <0.01 mbar) in deionized water to afford P1 and P2 (41 mg, 23%) as a white solid. The atropisomers were separated by chiral preparative HPLC on a CHIRALPAK® AD-H column to afford P1 (10.1 mg, 6% yield) and P2 (18 mg, 10% yield) as white solids.

P1: $^1H$ NMR (400 MHz, MeOH-$d_4$) δ 8.15 (s, 1H), 7.48 (t, J=7.6 Hz, 1H), 7.38 (t, J=9.1 Hz, 1H), 5.42-5.34 (m, 1H), 4.83-4.56 (br s, 2H), 4.41-4.21 (m, 2H), 3.73-3.40 (m, 5H), 3.39 (s, 3H), 3.17 (dd, J=13.6, 3.0 Hz, 1H), 1.56 (d, J=6.9 Hz, 3H), 1.42 (d, J=6.9 Hz, 3H); LRMS-ESI (m/z) $[M+H]^+$ calculated for $C_{28}H_{24}D_3ClF_5N_4O_3S$ 632.16, found 632.2.

P2: $^1H$ NMR (400 MHz, MeOH-$d_4$) δ 8.15 (s, 1H), 7.53 (t, J=7.6 Hz, 1H), 7.37 (t, J=9.1 Hz, 1H), 5.41-5.31 (m, 1H), 4.83-4.54 (br s, 2H), 4.39-4.29 (m, 2H), 3.74 (t, J=9.2 Hz, 1H), 3.62 (dd, J=9.2, 4.8 Hz, 1H), 3.49 (dd, J=13.5, 4.7 Hz, 1H), 3.45-3.37 (m, 2H), 3.40 (s, 3H), 3.15 (dd, J=13.7, 3.0 Hz, 1H), 1.57 (d, J=7.0 Hz, 3H), 1.42 (d, J=7.0 Hz, 3H); LRMS-ESI (m/z) $[M+H]^+$ calculated for $C_{28}H_{24}D3ClF_5N_4O_3S$ 632.16, found 632.2.

Example 2082: 8'-((2S,5R)-4-acryloyl-2,5-dimethylpiperazin-1-yl)-11'-(5-chloro-2,4-difluorophenyl)-3,3-difluoro-10'-(trifluoromethyl)-2'H,4'H,6'H-spiro[cyclobutane-1,3'-[1,4]thiazepino[2,3,4-ij]quinazolin]-6'-one
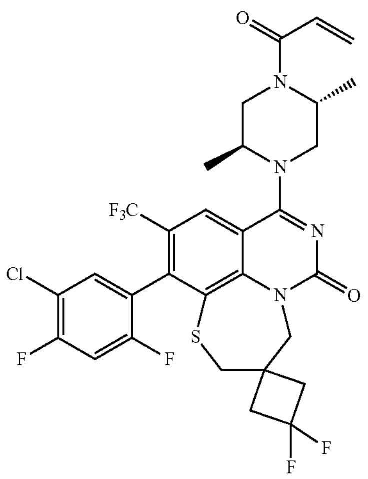 [SMILES: C=CC(=O)N1C[C@H](C)N(c2nc(=O)n3c4c(c(-c5cc(Cl)c(F)cc5F)c(C(F)(F)F)cc24)SCC2(C3)CC(F)(F)C2)C[C@H]1C]
Reaction Scheme
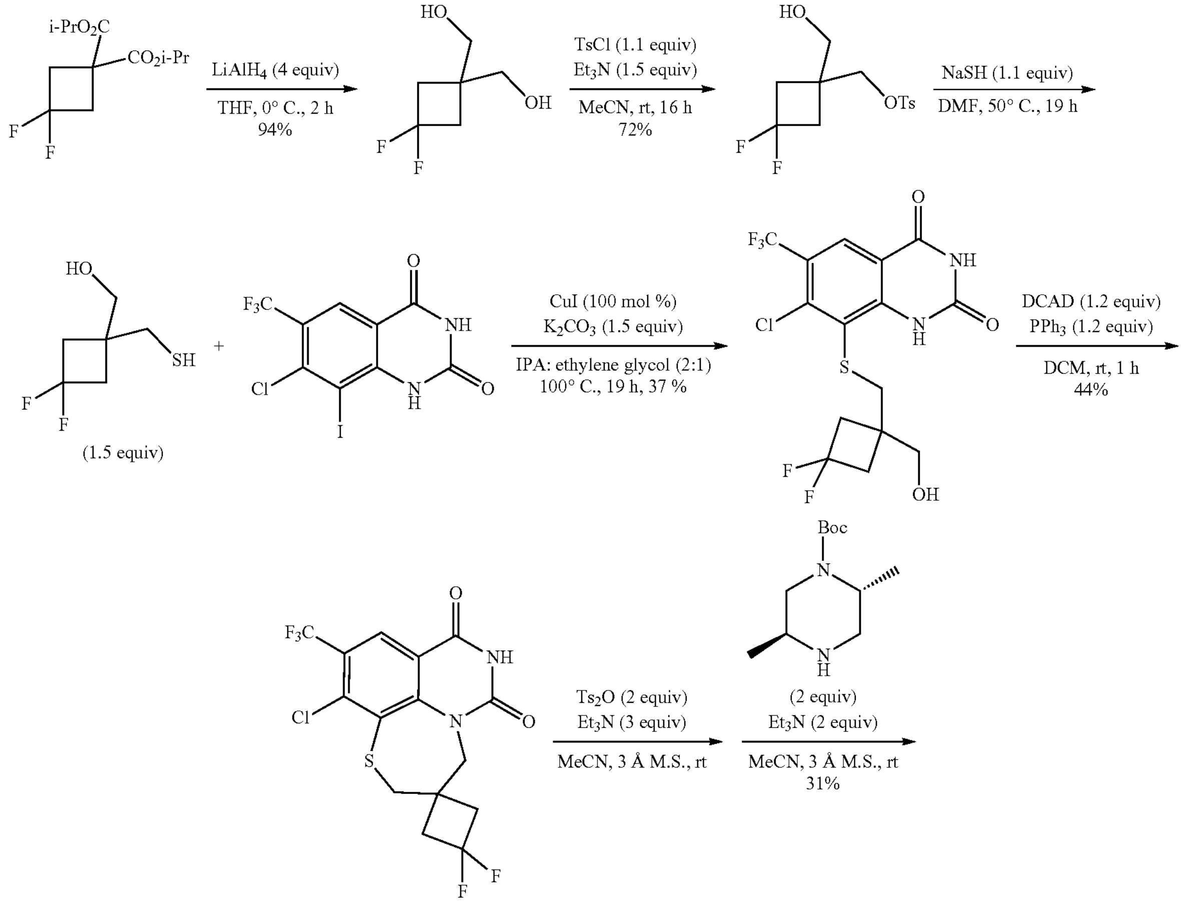

-continued

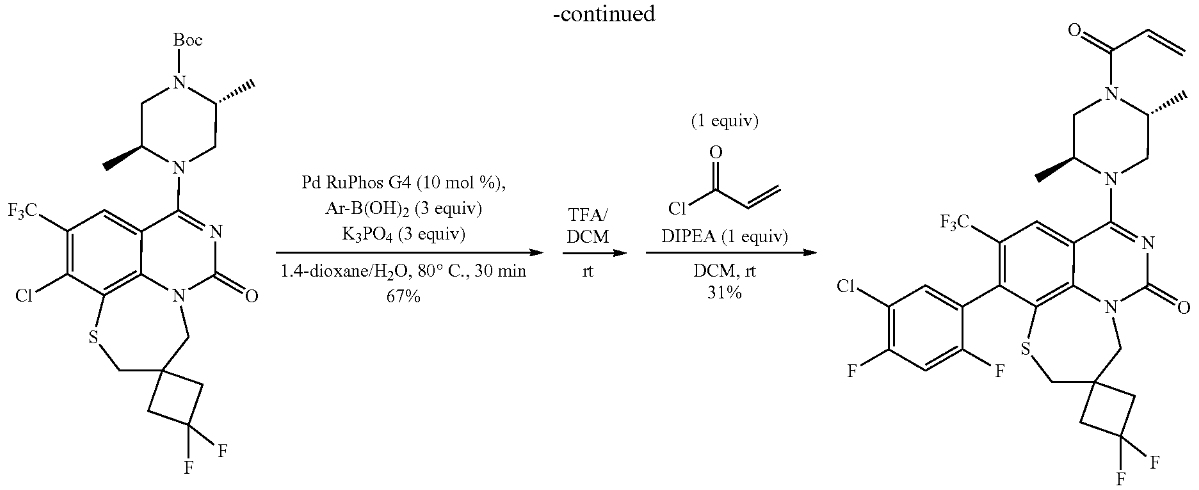

The title compound was synthesized through the route shown above using similar procedures as described in other examples.

$^1$H NMR (400 MHz, MeOH-$d_4$) δ 7.96 (s, 1H), 7.61-7.41 (m, 1H), 7.34 (td, J=9.2, 3.7 Hz, 1H), 6.92-6.71 (m, 1H), 6.37-6.21 (m, 1H), 5.81 (ddd, J=9.9, 7.2, 1.9 Hz, 1H), 4.87-4.38 (m, 4H), 4.37-3.33 (m, 10H), 2.60-2.37 (m, 2H), 1.59-1.20 (m, 6H); LRMS-ESI (m/z) [M+H]$^+$ calculated for $C_{30}H_{27}ClF_7N_4O_2S$ 675.14, found 675.2.

TABLE 12

Summary of Compounds 2000 to 2109

| Ex.# | Structure | Name | $^1$H NMR | MS + 1 |
|---|---|---|---|---|
| 2001 | 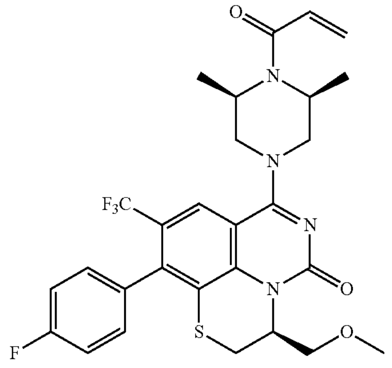 | (S)-7-((3S,5R)-4-acryloyl-3,5-dimethylpiperazin-1-yl)-10-(4-fluorophenyl)-3-(methoxymethyl)-9-(trifluoromethyl)-2H-[1,4]thiazino[2,3,4-ij]quinazolin-5(3H)-one | $^1$H NMR (400 MHz, $CDCl_3$) δ 8.06 (s, 1H), 7.21-7.15 (m, 4H), 6.67-6.59 (m, 1H), 6.44-6.37 (m, 1H), 5.79-5.76 (m, 1H), 5.47-5.52 (m, 1H), 4.76-4.55 (m, 2H), 4.24-4.16 (m, 2H), 3.71-3.61 (m, 2H), 3.40-3.30 (m, 6H), 2.99-2.91 (m, 1H), 1.63-1.61 (m, 3H), 21.48-1.46 (m, 3H). | 577.3 |
| 2001 | 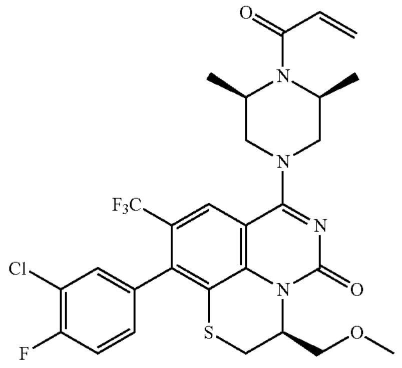 [SMILES: C=CC(=O)N1[C@H](C)CN(c2nc(=O)n3c4c(c(-c5ccc(F)c(Cl)c5)c(C(F)(F)F)cc24)SC[C@@H]3COC)C[C@@H]1C] | (S)-7-((3S,5R)-4-acryloyl-3,5-dimethylpiperazin-1-yl)-10-(3-chloro-4-fluorophenyl)-3-(methoxymethyl)-9-(trifluoromethyl)-2H-[1,4]thiazino[2,3,4-ij]quinazolin-5(3H)-one | $^1$H NMR (400 MHz, $CDCl_3$) δ 8.05 (s, 1H), 7.30-7.28 (m, 1H), 7.25-7.23 (m, 1H), 7.14-7.10 (m, 1H), 6.66-6.59 (m, 1H), 6.43-6.38 (m, 1H), 5.79-5.76 (m, 1H), 5.45-5.42 (m, 1H), 4.66-4.55 (m, 1H), 4.21-4.15 (m, 2H), 3.70-3.61 (m, 2H), 3.41-3.30 (m, 6H), 2.99-2.94 (m, 1H), 1.62-1.60 (m, 4H), 1.48-1.46 (m, 3H). | 611.2 |

TABLE 12-continued

| Summary of Compounds 2000 to 2109 | | | | |
|---|---|---|---|---|
| Ex.# | Structure | Name | $^1$H NMR | MS + 1 |
| 2002 | 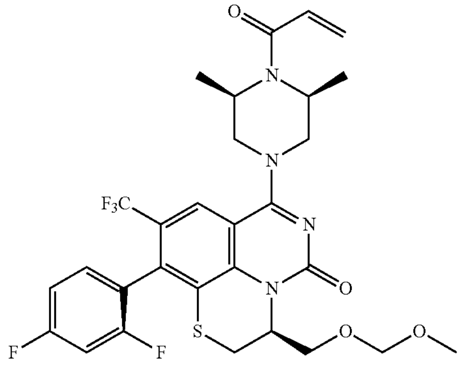 | (3S,10S)-7-((3S,5R)-4-acryloyl-3,5-dimethylpiperazin-1-yl)-10-(2,4-difluorophenyl)-3-((methoxymethoxy)methyl)-9-(trifluoromethyl)-2H-[1,4]thiazino[2,3,4-ij]quinazolin-5(3H)-one | $^1$H NMR (400 MHz, $CDCl_3$) δ 8.07 (s, 1H), 7.21-7.15 (m, 1H), 7.06-7.01 (m, 1H), 6.98-6.93 (m, 1H), 6.66-6.59 (m, 1H), 6.42 (dd, J = 1.6 Hz, 16.8 Hz, 1H), 5.78 (dd, J = 1.2 Hz, 10.4 Hz, 1H), 5.51-5.49 (m, 1H), 4.67-4.62 (m, 4H), 4.22-4.19 (m, 2H), 3.82-3.74 (m, 2H), 3.40-3.3 (m, 6H), 3.07-3.03 (m, 1H), 1.61 (d, J = 6.8 Hz, 3H), 1.48 (d, J = 6.8 Hz, 3H). | 625.2 |
| 2003 | 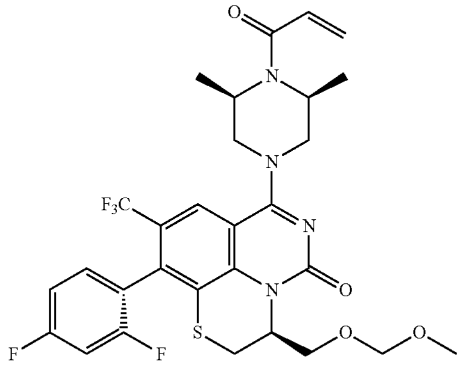 | (3S,10S)-7-((3S,5R)-4-acryloyl-3,5-dimethylpiperazin-1-yl)-10-(2,4-difluorophenyl)-3-((methoxymethoxy)methyl)-9-(trifluoromethyl)-2H-[1,4]thiazino[2,3,4-ij]quinazolin-5(3H)-one | $^1$H NMR (400 MHz, $CDCl_3$) δ 8.07 (s, 1H), 7.20-7.15 (m, 1H), 7.04-6.94 (m, 2H), 6.66-6.59 (m, 1H), 6.42 (dd, J = 1.2 Hz, 16.4 Hz, 1H), 5.78 (dd, J = 1.2 Hz, 10.0 Hz, 1H), 5.48-5.45 (m, 1H), 4.67-4.62 (m, 4H), 4.21-4.18 (m, 2H), 3.80-3.78 (m, 2H), 3.39-3.30 (m, 6H), 3.09-3.05 (m, 1H), 1.61 (d, J = 6.8 Hz, 3H), 1.48 (d, J = 6.8 Hz, 3H). | 625.2 |
| 2004 | 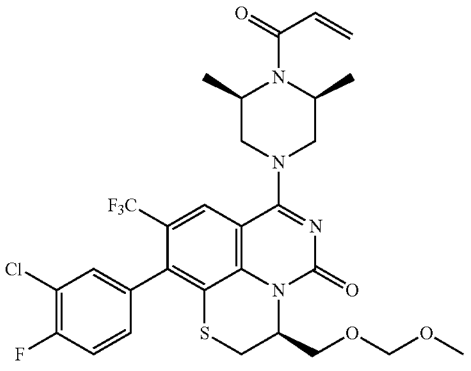 [SMILES: C=CC(=O)N1[C@H](C)CN(c2nc(=O)n3c4c(c(-c5ccc(F)c(Cl)c5)c(C(F)(F)F)cc24)SC[C@@H]3COCOC)C[C@@H]1C] | (S)-7-((3S,5R)-4-acryloyl-3,5-dimethylpiperazin-1-yl)-10-(3-chloro-4-fluorophenyl)-3-((methoxymethoxy)methyl)-9-(trifluoromethyl)-2H-[1,4]thiazino[2,3,4-ij]quinazolin-5(3H)-one | $^1$H NMR (400 MHz, $CDCl_3$) δ 8.05 (s, 1H), 7.32-7.23 (m, 2H), 7.13-7.10 (m, 1H), 6.65-6.59 (m, 1H), 6.43 (dd, J = 12.8 Hz, 2 Hz, 1H), 5.79 (dd, J = 8.4 Hz, 1.6 Hz, 1H), 5.48-5.46 (m, 1H), 4.68-4.62 (m, 3H), 4.20-4.17 (m, 2H), 3.83-3.77 (m, 2H), 3.39-3.30 (m, 6H), 3.03-2.98 (m, 1H), 1.62-1.60 (m, 4H), 1.48-1.46 (m, 3H). | 641.1 |

TABLE 12-continued

| Summary of Compounds 2000 to 2109 | | | | |
|---|---|---|---|---|
| Ex.# | Structure | Name | $^1$H NMR | MS + 1 |
| 2005 | 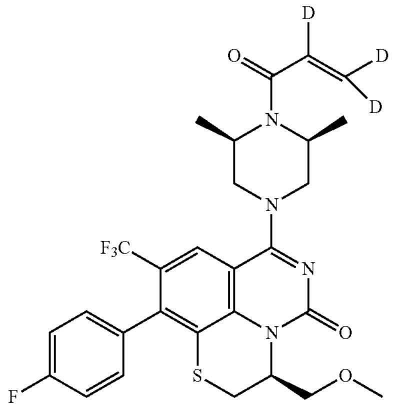 [SMILES: [2H]C([2H])=C([2H])C(=O)N1[C@H](C)CN(c2nc(=O)n3c4c(c(-c5ccc(F)cc5)c(C(F)(F)F)cc24)SC[C@@H]3COC)C[C@@H]1C] | (S)-7-((3S,5R)-4-(Acryloyl-$d_3$)-3,5-dimethylpiperazin-1-yl)-10-(4-fluorophenyl)-3-(methoxymethyl)-9-(trifluoromethyl)-2,3-dihydro-5H-[1,4]thiazino[2,3,4-ij]quinazolin-5-one | $^1$H NMR (400 MHz, MeOH-$d_4$) δ 8.13 (s, 1H), 7.34-7.19 (m, 4H), 5.38-5.30 (m, 1H), 4.81-4.57 (br s, 2H), 4.39-4.22 (m, 2H), 3.73 (t, J = 9.2 Hz, 1H), 3.60 (dd, J = 9.2, 4.8 Hz, 1H), 3.49 (dd, J = 13.5, 4.7 Hz, 1H), 3.39 (s, 3H), 3.45-3.33 (m, 2H), 3.09 (dd, J = 13.6, 2.9 Hz, 1H), 1.57 (d, J = 7.0 Hz, 3H), 1.42 (d, J = 7.0 Hz, 3H). | 580.3 |
| 2006 | 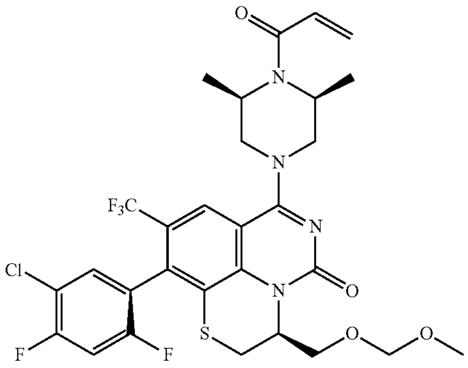 | (3S,10S)-7-((3S,5R)-4-acryloyl-3,5-dimethylpiperazin-1-yl)-10-(5-chloro-2,4-difluorophenyl)-3-((methoxymethoxy)methyl)-9-(trifluoromethyl)-2H-[1,4]thiazino[2,3,4-ij]quinazolin-5(3H)-one | 1H NMR (400 MHz, $CDCl_3$) δ 8.07 (s, 1H), 7.29-7.26 (m, 1H), 7.08-7.04 (m, 1H), 6.65-6.59 (m, 1H), 6.43 (dd, J = 16.8 Hz, 2 Hz, 1H), 5.79 (dd, J = 10 Hz, 1.6 Hz, 1H), 5.52-5.48 (m, 1H), 4.68-4.62 (m, 3H), 4.21-4.17 (m, 2H), 3.81-3.76 (m, 2H), 3.42-3.30 (m, 6H), 3.08-3.04 (m, 1H), 1.62-1.57 (m, 4H), 1.47 (d, J = 6.8 Hz, 3H). | 659.3 |
| 2007 | 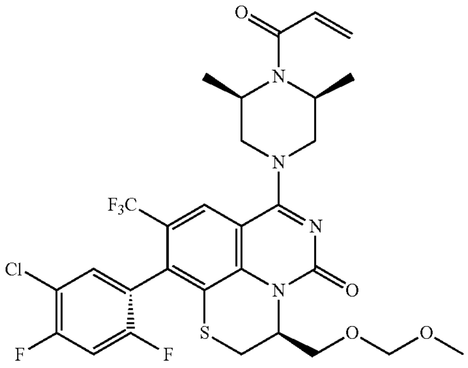 | (3S,10S)-7-((3S,5R)-4-acryloyl-3,5-dimethylpiperazin-1-yl)-10-(5-chloro-2,4-difluorophenyl)-3-((methoxymethoxy)methyl)-9-(trifluoromethyl)-2H-[1,4]thiazino[2,3,4-ij]quinazolin-5(3H)-one | MHz, $CDCl_3$) δ 8.06 (s, 1H), 7.29-7.26 (m, 1H), 7.10-7.05 (m, 1H), 6.65-6.58 (m, 1H), 6.43 (dd, J = 16.4 Hz, 2 Hz, 1H), 5.79 (dd, J = 10.8 Hz, 2 Hz, 1H), 5.50-5.46 (m, 1H), 4.68-4.63 (m, 3H), 4.21-4.17 (m, 2H), 3.80-3.78 (m, 2H), 3.42-3.31 (m, 6H), 3.09-3.05 (m, 1H), 1.61-1.60 (m, 4H), 1.48 (d, J = 6.8 Hz, 3H). | 659.3 |

TABLE 12-continued

Summary of Compounds 2000 to 2109

| Ex.# | Structure | Name | $^1$H NMR | MS + 1 |
|---|---|---|---|---|
| 2008 | 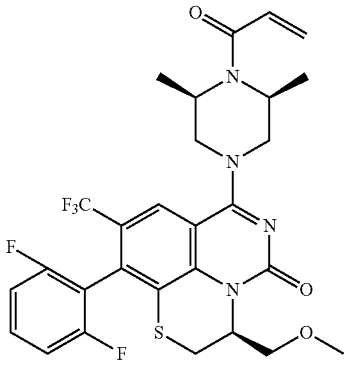 [SMILES: C=CC(=O)N1[C@H](C)CN(c2nc(=O)n3c4c(c(-c5c(F)cccc5F)c(C(F)(F)F)cc24)SC[C@@H]3COC)C[C@@H]1C] | (S)-7-((3S,5R)-4-acryloyl-3,5-dimethylpiperazin-1-yl)-10-(2,6-difluorophenyl)-3-(methoxymethyl)-9-(trifluoromethyl)-2H-[1,4]thiazino[2,3,4-ij]quinazolin-5(3H)-one | $^1$H NMR (400 MHz, $CDCl_3$) δ 8.10 (s, 1H), 7.55-7.45 (m, 1H), 7.05 (t, J = 8.0 Hz, 2H), 6.63 (dd, J = 16.8 Hz, 10.4 Hz, 1H), 6.41 (dd, J = 16.8 Hz, 2.0 Hz, 1H), 5.78 (dd, J = 10.4 Hz, 2.0 Hz, 1H), 5.50-5.45 (m, 1H), 4.70-4.61 (m, 2H), 4.29-4.11 (m, 2H), 3.70-3.61 (m, 2H), 3.40 (s, 3H), 3.38-3.30 (m, 3H), 3.07 (dd, J = 13.5, 2.7 Hz, 1H), 1.63 (d, J = 7.2 Hz, 3H), 1.48 (d, J = 7.2 Hz, 3H). | 595.2 |
| 2009 | 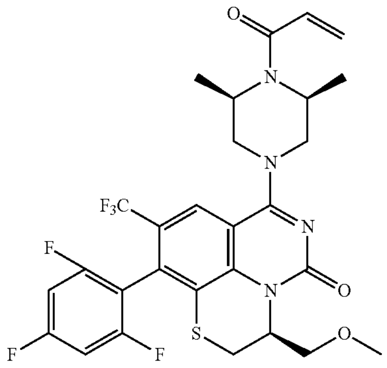 [SMILES: C=CC(=O)N1[C@H](C)CN(c2nc(=O)n3c4c(c(-c5c(F)cc(F)cc5F)c(C(F)(F)F)cc24)SC[C@@H]3COC)C[C@@H]1C] | (S)-7-((3S,5R)-4-acryloyl-3,5-dimethylpiperazin-1-yl)-3-(methoxymethyl)-9-(trifluoromethyl)-10-(2,4,6-trifluorophenyl)-2H-[1,4]thiazino[2,3,4-ij]quinazolin-5(3H)-one | $^1$H NMR (400 MHz, $CDCl_3$) δ 8.09 (s, 1H), 6.82 (t, J = 7.2 Hz, 2H), 6.62 (dd, J = 10.8 Hz, J = 16.8 Hz, 1H), 6.40 (dd, J = 1.6 Hz, J = 16.4 Hz, 1H), 5.77 (dd, J = 1.6 Hz, J = 10.4 Hz, 1H), 5.50-5.45 (m, 1H), 4.85-4.52 (m, 2H), 4.22-4.16 (m, 2H), 3.67-3.60 (m, 2H), 3.40 (s, 3H), 3.37-3.30 (m, 3H), 3.07 (dd, J = 2.8 Hz, J = 13.2 Hz, 1H), 1.62 (d, J = 6.8 Hz, 3H), 1.47 (d, J = 7.2 Hz, 3H). | |
| 2010 | 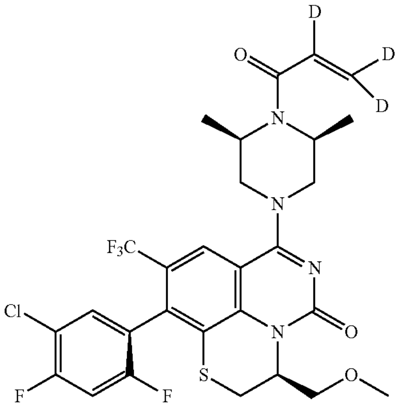 | (3S,10S)-7-((3S,5R)-4-(Acryloyl-$d_3$)-3,5-dimethylpiperazin-1-yl)-10-(5-chloro-2,4-difluorophenyl)-3-(methoxymethyl)-9-(trifluoromethyl)-2,3-dihydro-5H-[1,4]thiazino[2,3,4-ij]quinazolin-5-one | $^1$H NMR (400 MHz, MeOH-$d_4$) δ 8.15 (s, 1H), 7.48 (t, J = 7.6 Hz, 1H), 7.38 (t, J = 9.1 Hz, 1H), 5.42-5.34 (m, 1H), 4.83-4.56 (br s, 2H), 4.41-4.21 (m, 2H), 3.73-3.40 (m, 5H), 3.39 (s, 3H), 3.17 (dd, J = 13.6, 3.0 Hz, 1H), 1.56 (d, J = 6.9 Hz, 3H), 1.42 (d, J = 6.9 Hz, 3H); | 632.2 |

TABLE 12-continued

| Summary of Compounds 2000 to 2109 | | | | |
|---|---|---|---|---|
| Ex.# | Structure | Name | $^1$H NMR | MS + 1 |
| 2011 | 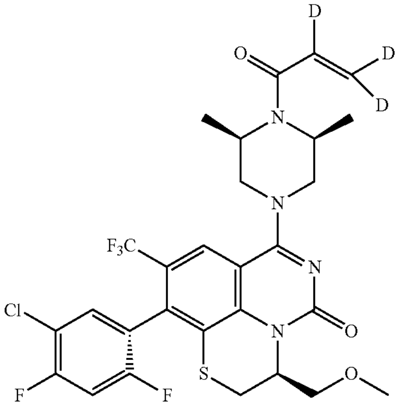 | (3S,10R)-7-((3S,5R)-4-(Acryloyl-$d_3$)-3,5-dimethylpiperazin-1-yl)-10-(5-chloro-2,4-difluorophenyl)-3-(methoxymethyl)-9-(trifluoromethyl)-2,3-dihydro-5H-[1,4]thiazino[2,3,4-ij]quinazolin-5-one | $^1$H NMR (400 MHz, MeOH-$d_4$) δ 8.15 (s, 1H), 7.53 (t, J = 7.6 Hz, 1H), 7.37 (t, J = 9.1 Hz, 1H), 5.41-5.31 (m, 1H), 4.83-4.54 (br s, 2H), 4.39-4.29 (m, 2H), 3.74 (t, J = 9.2 Hz, 1H), 3.62 (dd, J = 9.2, 4.8 Hz, 1H), 3.49 (dd, J = 13.5, 4.7 Hz, 1H), 3.45-3.37 (m, 2H), 3.40 (s, 3H), 3.15 (dd, J = 13.7, 3.0 Hz, 1H), 1.57 (d, J = 7.0 Hz, 3H), 1.42 (d, J = 7.0 Hz, 3H); | 632.2 |
| 2012 | 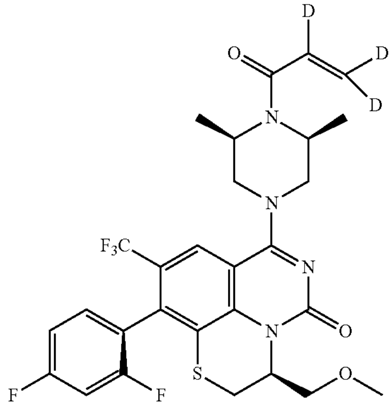 | (3S,10S)-7-((3S,5R)-4-(Acryloyl-$d_3$)-3,5-dimethylpiperazin-1-yl)-10-(2,4-difluorophenyl)-3-(methoxymethyl)-9-(trifluoromethyl)-2,3-dihydro-5H-[1,4]thiazino[2,3,4-ij]quinazolin-5-one | 1H NMR (400 MHz, MeOH-$d_4$) δ 8.14 (s, 1H), 7.30 (q, J = 8.0 Hz, 1H), 7.14 (t, J = 9.1 Hz, 2H), 5.42-5.33 (m, 1H), 4.81-4.52 (m, 2H), 4.40-4.2 (m, 2H), 3.70 (t, J = 9.1 Hz, 1H), 3.59 (dd, J = 9.2, 4.9 Hz, 1H), 3.51 (dd, J = 13.5, 4.7 Hz, 1H), 3.45-3.40 (m, 1H), 3.39 (s, 3H), 3.38-3.33 (m, 1H), 3.15 (dd, J = 13.6, 2.9 Hz, 1H), 1.57 (d, J = 7.0 Hz, 3H), 1.42 (d, J = 6.9 Hz, 3H). | 598.2 |
| 2013 | 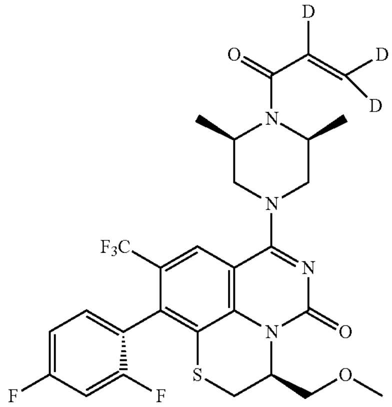 | (3S,10R)-7-((3S,5R)-4-(Acryloyl-$d_3$)-3,5-dimethylpiperazin-1-yl)-10-(2,4-difluorophenyl)-3-(methoxymethyl)-9-(trifluoromethyl)-2,3-Hz, dihydro-5H-[1,4]thiazino[2,3,4-ij]quinazolin-5-one | $^1$H NMR (400 MHz, MeOH-$d_4$) δ 8.15 (s, 1H), 7.33 (q, J = 7.4 Hz, 1H), 7.14 (t, J = 7.5 2H), 5.41-5.29 (m, 1H), 4.82-4.53 (br s, 2H), 4.39-4.19 (m, 2H), 3.72 (t, J = 9.2 Hz, 1H), 3.61 (dd, J = 9.2, 4.8 Hz, 1H), 3.48 (dd, J = 13.5, 4.7 Hz, 1H), 3.44-3.33 (m, 2H), 3.39 (s, 3H), 3.14 (dd, J = 13.6, 2.9 Hz, 1H), 1.58 (d, J = | 598.2 |

TABLE 12-continued

| Summary of Compounds 2000 to 2109 | | | | |
|---|---|---|---|---|
| Ex.# | Structure | Name | $^1$H NMR | MS + 1 |
| | | | 6.9 Hz, 3H), 1.42 (d, J = 7.0 Hz, 3H). | |
| 2014 | 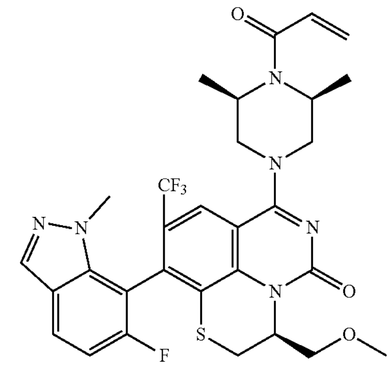 [SMILES: C=CC(=O)N1[C@H](C)CN(c2nc(=O)n3c4c(c(-c5c(F)ccc6cnn(C)c56)c(C(F)(F)F)cc24)SC[C@@H]3COC)C[C@@H]1C] | (3S,10R)-7-((3S,5R)-4-acryloyl-3,5-dimethylpiperazin-1-yl)-10-(6-fluoro-1-methyl-1H-indazol-7-yl)-3-(methoxymethyl)-9-(trifluoromethyl)-2,3-dihydro-5H-[1,4]t1iazino[2,3,4-ij]quinazolin-5-one | $^1$H NMR (400 MHz, MeOH-$d_4$) δ 8.22 (s, 1H), 8.16 (s, 1H), 7.18 (dd, J = 8.0, 4.8 Hz, 1H), 6.97 (dd, J = 9.7, 8.0 Hz, 1H), 6.85 (dd, J = 16.7, 10.5 Hz, 1H), 6.30 (dd, J = 16.6, 2.0 Hz, 1H), 5.81 (dd, J = 10.6, 2.0 Hz, 1H), 5.39-5.31 (m, 1H), 4.84-4.46 (m, 3H), 4.39 (d, J = 13.8 Hz, 1H), 4.3 (d, J = 13.6 Hz, 1H), 3.73-3.60 (m, 2H), 3.56 (s, 3H), 3.55-3.38 (m, 3H), 3.36 (s, 2H), 3.35-3.33 (m, 1H), 3.15 (dd, J = 13.7, 3.0 Hz, 1H), 1.60 (d, J = 7.0 Hz, 3H), 1.47-1.39 (m, 3H); | 631.2 |
| 2015 | 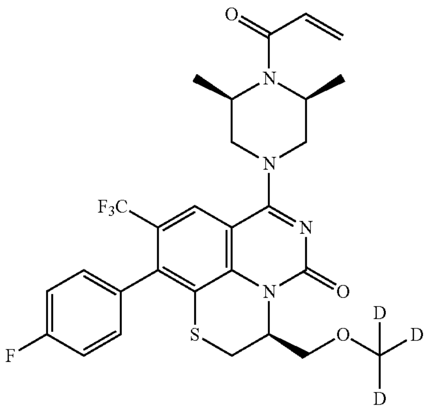 [SMILES: [2H]C([2H])([2H])OC[C@H]1CSc2c(-c3ccc(F)cc3)c(C(F)(F)F)cc3c(N4C[C@@H](C)N(C(=O)C=C)[C@@H](C)C4)nc(=O)n1c23] | (S)-7-((3S,5R)-4-acryloyl-3,5-dimethylpiperazin-1-yl)-10-(4-fluorophenyl)-3-((trideuteriomethoxy) methyl)-9-(trifluoromethyl)-2H-[1,4]thiazino[2,3,4-ij]quinazolin-5(3H)-one | $^1$H NMR (400 MHz, CDCl3) δ 8.06 (s, 1H), 7.23-7.15 (m, 4H), 6.62 (dd, J = 10.4 Hz, J = 16.4 Hz, 1H), 6.41 (dd, J = 1.6 Hz, J = 16.8 Hz, 1H), 5.77 (dd, J = 2.0 Hz, J = 10.4 Hz, 1H), 5.43-5.41 (m, 1H), 4.82-4.54 (m, 2H), 4.21-4.16 (m, 2H), 3.69-3.62 (m, 2H), 3.39-3.29 (m, 3H), 2.98-2.94 (m, 1H), 1.62 (d, J = 7.2Hz, 3H), 1.47 (d, J = 7.2 Hz, 3H). | 580.2 |

TABLE 12-continued

| Summary of Compounds 2000 to 2109 | | | | |
|---|---|---|---|---|
| Ex.# | Structure | Name | $^1$H NMR | MS + 1 |
| 2016 | 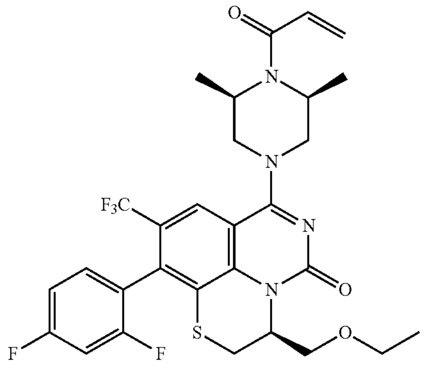 [SMILES: C=CC(=O)N1[C@H](C)CN(c2nc(=O)n3c4c(c(-c5ccc(F)cc5F)c(C(F)(F)F)cc24)SC[C@@H]3COCC)C[C@@H]1C] | (3S)-7-((3S,5R)-4-acryloyl-3,5-dimethylpiperazin-1-yl)-10-(2,4-difluorophenyl)-3-(ethoxymethyl)-9-(trifluoromethyl)-2H-[1,4]thiazino[2,3,4-ij]quinazolin-5(3H)-one | $^1$H NMR (400 MHz, CDCl3) δ 8.07 (s, 1H), 7.23-7.13 (m, 1H), 7.08-6.92 (m, 2H), 6.63 (dd, J = 16.8 Hz, 6.0 Hz, 1H), 6.41 (dd, J = 16.8 Hz, 1.6 Hz, 1H), 5.78 (dd, J = 10.8 Hz, 1.6 Hz, 1H), 5.51-5.38 (m, 1H), 5.00-4.40 (m, 2H), 4.25-4.14 (m, 2H), 3.74-3.47 (m, 4H), 3.43-3.28 (m, 3H), 3.07-2.97 (m, 1H), 1.63 (d, J = 7.2 Hz, 3H), 1.48 (d, J = 6.4 Hz, 3H), 1.18 (t, J = 6.8 Hz, 3H). | 609.2 |
| 2017 | 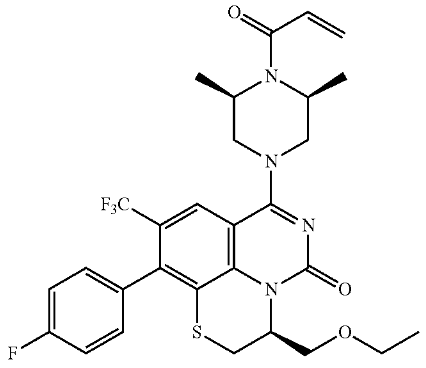 [SMILES: C=CC(=O)N1[C@H](C)CN(c2nc(=O)n3c4c(c(-c5ccc(F)cc5)c(C(F)(F)F)cc24)SC[C@@H]3COCC)C[C@@H]1C] | (S)-7-((3S,5R)-4-acryloyl-3,5-dimethylpiperazin-1-yl)-3-(ethoxymethyl)-10-(4-fluorophenyl)-9-(trifluoromethyl)-2H-[1,4]thiazino[2,3,4-ij]quinazolin-5(3H)-one | $^1$H NMR (400 MHz, CDCl3) δ 8.06 (s, 1H), 7.25-7.14 (m, 4H), 6.63 (dd, J = 16.4 Hz, 10.8 Hz, 1H), 6.41 (dd, J = 16.8 Hz, 1.6 Hz, 1H), 5.78 (dd, J = 10.4 Hz, 2.0 Hz, 1H), 5.47-5.37 (m, 1H), 4.90-4.40 (m, 2H), 4.25-4.13 (m, 2H), 3.75-3.47 (m, 4H), 3.43-3.26 (m, 3H), 2.96 (dd, J = 13.6 Hz, 2.8 Hz, 1H), 1.62 (d, J = 7.2 Hz, 3H), 1.47 (d, J = 6.8 Hz, 3H), 1.18 (t, J = 6.8 Hz, 3H). | 591.3 |
| 2018 | 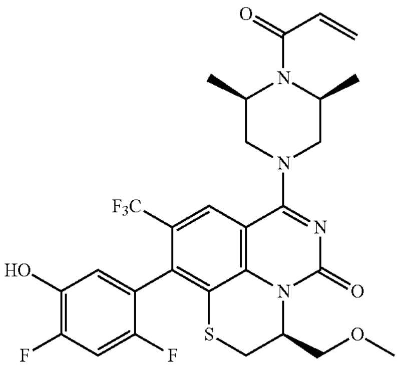 [SMILES: C=CC(=O)N1[C@H](C)CN(c2nc(=O)n3c4c(c(-c5cc(O)c(F)cc5F)c(C(F)(F)F)cc24)SC[C@@H]3COC)C[C@@H]1C] | (3S)-7-((3S,5R)-4-Acryloyl-3,5-dimethylpiperazin-1-yl)-10-(2,4-difluoro-5-hydroxyphenyl)-3-(methoxymethyl)-9-(trifluoromethyl)-2,3-dihydro-5H-[1,4]thiazino[2,3,4-ij]quinazolin-5-one | $^1$H NMR (400 MHz, MeOH-$d_4$) δ 8.13 (s, 1H), 7.08 (t, J = 10.0 Hz, 1H), 6.90-6.72 (m, 2H), 6.29 (dd, J = 16.6, 2.0 Hz, 1H), 5.80 (dd, J = 10.5, 2.0 Hz, 1H), 5.41-5.28 (m, 1H), 4.83-4.50 (m, 2H), 4.33 (d, J = 13.8 Hz, 1H), 4.25 (d, J = 13.6 Hz, 1H), 3.73 (t, J = 9.2 Hz, 1H), 3.61 (dd, J = 9.2, 4.7 Hz, 1H), 3.48 (dd, J = 13.5, 4.8 Hz, 1H), 3.44-3.33 | 611.2 |

TABLE 12-continued

| Summary of Compounds 2000 to 2109 | | | | |
|---|---|---|---|---|
| Ex.# | Structure | Name | $^1$H NMR | MS + 1 |
| | | | (m, 2H), 3.40 (s, 3H), 3.13 (dd, J = 13.8, 2.9 Hz, 1H), 1.58 (d, J = 6.9 Hz, 3H), 1.42 (d, J = 6.9 Hz, 3H); | |
| 2019 | 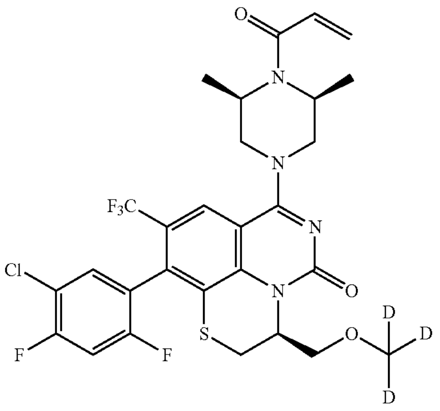 [SMILES: [2H]C([2H])([2H])OC[C@H]1CSc2c(-c3cc(Cl)c(F)cc3F)c(C(F)(F)F)cc3c(N4C[C@@H](C)N(C(=O)C=C)[C@@H](C)C4)nc(=O)n1c23] | (3S)-7-((3S,5R)-4-acryloyl-3,5-dimethylpiperazin-1-yl)-10-(5-chloro-2,4-difluorophenyl)-3-(trideuteriomethoxy)(methoxymethyl)-9-(trifluoromethyl)-2H-[1,4]thiazino[2,3,4-ij]quinazolin-5(3H)-one | $^1$H NMR (400 MHz, $CDCl_3$) δ 8.11 (s, 1H), 7.35-7.27 (m, 1H), 7.15-7.09 (m, 1H), 6.72-6.63 (m, 1H), 6.49-6.42 (m, 1H), 5.84-5.80 (m, 1H), 5.52-5.47 (m, 1H), 4.75-4.64 (m, 2H), 4.26-4.22 (m, 2H), 3.75-3.66 (m, 2H), 3.45-3.34 (m, 3H), 3.10-3.05 (m, 1H), 1.69-1.67 (m, 3H), 1.54-1.50 (m, 3H). | 632.06 |
| 2020 | 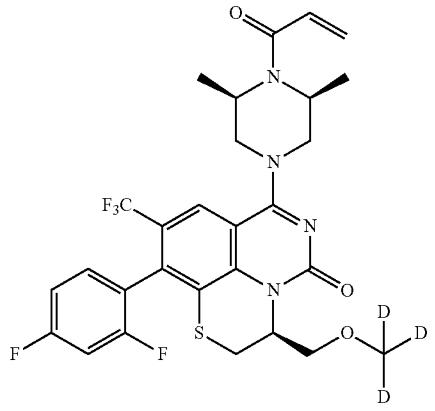 [SMILES: [2H]C([2H])([2H])OC[C@H]1CSc2c(-c3ccc(F)cc3F)c(C(F)(F)F)cc3c(N4C[C@@H](C)N(C(=O)C=C)[C@@H](C)C4)nc(=O)n1c23] | (3S)-7-((3S,5R)-4-acryloyl-3,5-dimethylpiperazin-1-yl)-10-(2,4-difluorophenyl)-3-((trideuteriomethoxy)methyl)-9-(trifluoromethyl)-2H-[1,4]thiazino[2,3,4-ij]quinazolin-5(3H)-one | $^1$H NMR (400 MHz, $CD_3OD$) δ 8.08 (s, 1H), 7.21-7.15 (m, 1H), 7.00-6.94 (m, 2H), 6.65-5.58 (m, 1H), 6.44-6.38 (m, 1H), 5.80-5.76 (m, 1H), 5.48-5.45 (m, 1H), 4.74-4.57 (m, 2H), 4.19-4.17 (m, 2H), 3.65-3.58 (m, 2H), 3.40-3.34 (m, 3H), 3.06-2.98 (m, 1H), 1.63-1.60 (m, 3H), 1.47 (d, J = 7.2 Hz, 3H). | 598.2 |
| 2021 | 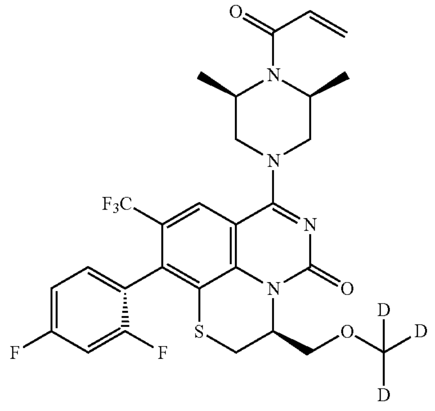 | (3S,10R)-7-((3S,5R)-4-acryloyl-3,5-dimethylpiperazin-1-yl)-10-(2,4-difluorophenyl)-3-((trideuteriomethoxy)methyl)-9-(trifluoromethyl)-2H-[1,4]thiazino[2,3,4-ij]quinazolin-5(3H)-one | $^1$H NMR (400 MHz, $CDCl_3$) δ 8.08 (s, 1H), 7.22-7.17 (m, 1H), 7.06-6.93 (m, 2H), 6.64-6.59 (m, 1H), 6.44-6.38 (m, 1H), 5.78 (dd, J = 10.4 Hz, 2.0 Hz, 1H), 5.48-5.45 (m, 1H), 4.66-4.63 (m, 2H), 4.23-4.19 (m, 2H), 3.70-3.60 (m, 2H), 3.40-3.30 (m, 3H), 3.04-2.99 (m, 1H), 1.63-1.61 (m, 3H), 1.47 (d, J = 6.8 Hz, 3H). | 598.2 |

TABLE 12-continued

Summary of Compounds 2000 to 2109

| Ex.# | Structure | Name | $^{1}$H NMR | MS + 1 |
|---|---|---|---|---|
| 2022 | 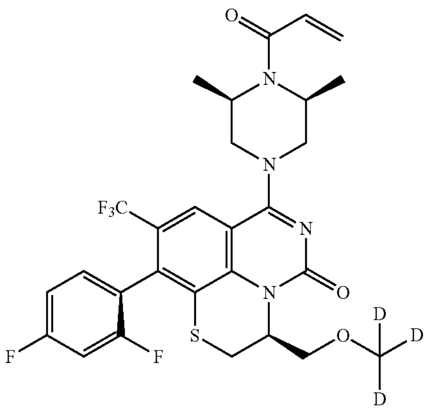 | (3S,10S)-7-((3S,5R)-4-acryloyl-3,5-dimethylpiperazin-1-yl)-10-(2,4-difluorophenyl)-3-((trideuteriomethoxy)methyl)-9-(trifluoromethyl)-2H-[1,4]thiazino[2,3,4-ij]quinazolin-5(3H)-one | $^{1}$H NMR (400 MHz, $CDCl_3$) δ 8.08 (s, 1H), 7.19-7.17 (m, 1H), 7.03-6.94 (m, 2H), 6.64-6.59 (m, 1H), 6.44-6.39 (m, 1H), 5.78 (dd, J = 12.4 Hz, 2.0 Hz, 1H), 5.46-5.43 (m, 1H), 4.76-4.64 (m, 2H), 4.21-4.16 (m, 2H), 3.67-3.65 (m, 2H), 3.40-3.32 (m, 3H), 3.06-3.01 (m, 1H), 1.63-1.61 (m, 3H), 1.52-1.46 (m, 3H). | 598.2 |
| 2023 | 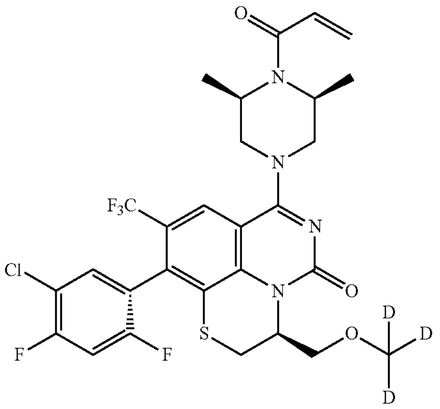 | (3S,10R)-7-((3S,5R)-4-acryloyl-3,5-dimethylpiperazin-1-yl)-10-(5-chloro-2,4-difluorophenyl)-3-((methoxy-$d_3$)methyl)-9-(trifluoromethyl)-2,3-dihydro-5H-[1,4]thiazino[2,3,4-ij]quinazolin-5-one | $^{1}$H NMR (400 MHz, $CDCl_3$) δ 8.06 (s, 1H), 7.28-7.24 (m, 1H), 7.07 (t, J = 8.8 Hz, 1H), 6.65-6.59 (m, 1H), 6.43-6.38 (m, 1H), 5.78 (dd, J = 10.4 Hz, 1.6 Hz, 1H), 5.46-5.43 (m, 1H), 4.73-4.58 (m, 2H), 4.21-4.16 (m, 2H), 3.69-3.63 (m, 2H), 3.40-3.31 (m, 3H), 3.05-3.01 (m, 1H), 1.61 (d, J = 6.8 Hz, 3H), 1.48 (d, J = 6.8 Hz, 3H). | 632.06 |
| 2024 | 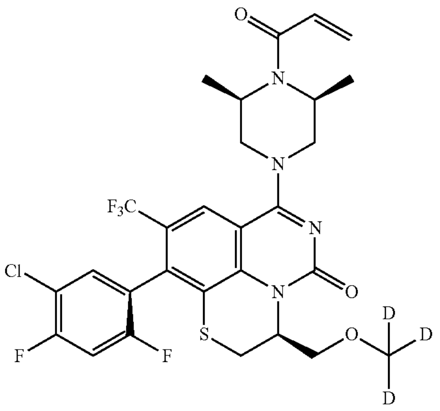 | (3S,10S)-7-((3S,5R)-4-acryloyl-3,5-dimethylpiperazin-1-yl)-10-(5-chloro-2,4-difluorophenyl)-3-(trideuteriomethoxy)(methoxymethyl)-9-(trifluoromethyl)-2H-[1,4]thiazino[2,3,4-ij]quinazolin-5(3H)-one | $^{1}$H NMR (400 MHz, $CDCl_3$) δ 8.06 (s, 1H), 7.28-7.25 (m, 1H), 7.07 (t, J = 8.8 Hz, 1H), 6.65-6.59 (m, 1H), 6.43-6.38 (m, 1H), 5.78 (dd, J = 10.4 Hz, 1.6 Hz, 1H), 5.48-5.45 (m, 1H), 4.80-4.43 (m, 2H), 4.21-4.16 (m, 2H), 3.67-3.59 (m, 2H), 3.41-3.3 (m, 3H), 3.04-3.00 (m, 1H), 1.62-1.61 (m, 3H), 1.46 (d, J = 6.8 Hz, 3H). | 632.06 |

TABLE 12-continued

| Ex.# | Structure | Name | $^1$H NMR | MS + 1 |
|---|---|---|---|---|
| Summary of Compounds 2000 to 2109 | | | | |
| 2025 | 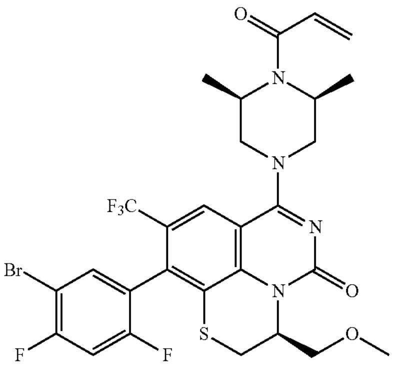 [SMILES: C=CC(=O)N1[C@H](C)CN(c2nc(=O)n3c4c(c(-c5cc(Br)c(F)cc5F)c(C(F)(F)F)cc24)SC[C@@H]3COC)C[C@@H]1C] | (3S)-7-((3S,5R)-4-acryloyl-3,5-dimethylpiperazin-1-yl)-10-(5-bromo-2,4-difluorophenyl)-3-(methoxymethyl)-9-(trifluoromethyl)-2,3-dihydro-5H-[1,4]thiazino[2,3,4-ij]quinazolin-5-one | $^1$H NMR (400 MHz, MeOH-$d_4$) δ 8.15 (s, 1H), 7.63 (dt, J = 22.3, 7.4 Hz, 1H), 7.34 (td, J = 8.9, 4.4 Hz, 1H), 6.84 (dd, J = 16.6, 10.6 Hz, 1H), 6.29 (dd, J 16.7, 2.0 Hz, 1H), 5.80 (d, J = 10.5 Hz, 1H), 5.44-5.30 (m, 1H), 4.86-4.48 (m, 2H), 4.34 (t, J = 11.6 Hz, 1H), 4.26 (d, J = 13.6 Hz, 1H), 3.80-3.65 (m, 1H), 3.60 (td, J = 8.9, 4.8 Hz, 1H), 3.50 (td, J = 12.8, 4.6 Hz, 1H), 3.45-3.35 (m, 5H), 3.16 (ddd, J = 13.7, 5.8, 3.0 Hz, 1H), 1.63-1.52 (m, 3H), 1.42 (d, J = 6.9 Hz, 3H). | 673.2 |
| 2026 | 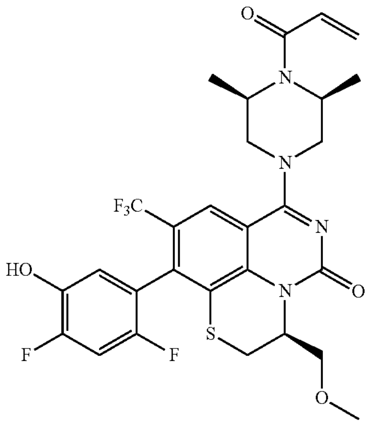 [SMILES: C=CC(=O)N1[C@H](C)CN(c2nc(=O)n3c4c(c(-c5cc(O)c(F)cc5F)c(C(F)(F)F)cc24)SC[C@@H]3COC)C[C@@H]1C] | (3S)-7-((3S,5R)-4-Acryloyl-3,5-dimethylpiperazin-1-yl)-10-(2,4-difluoro-5-hydroxyphenyl)-3-(methoxymethyl)-9-(trifluoromethyl)-2,3-dihydro-5H-[1,4]thiazino[2,3,4-ij]quinazolin-5-one | $^1$H NMR (400 MHz, MeOH-$d_4$) δ 8.13 (s, 1H), 7.08 (t, J = 10.0 Hz, 1H), 6.90-6.72 (m, 2H), 6.29 (dd, J = 16.6, 2.0 Hz, 1H), 5.80 (dd, J = 10.5, 2.0 Hz, 1H), 5.41-5.28 (m, 1H), 4.83-4.50 (m, 2H), 4.33 (d, J = 13.8 Hz, 1H), 4.25 (d, J = 13.6 Hz, 1H), 3.73 (t, J = 9.2 Hz, 1H), 3.61 (dd, J = 9.2, 4.7 Hz, 1H), 3.48 (dd, J = 13.5, 4.8 Hz, 1H), 3.44-3.33 (m, 2H), 3.40 (s, 3H), 3.13 (dd, J = 13.8, 2.9 Hz, 1H), 1.58 (d, J = 6.9 Hz, 3H), 1.42 (d, J = 6.9 Hz, 3H); | 611.2 |

TABLE 12-continued

| Summary of Compounds 2000 to 2109 | | | | |
|---|---|---|---|---|
| Ex.# | Structure | Name | $^1$H NMR | MS + 1 |
| 2028 | 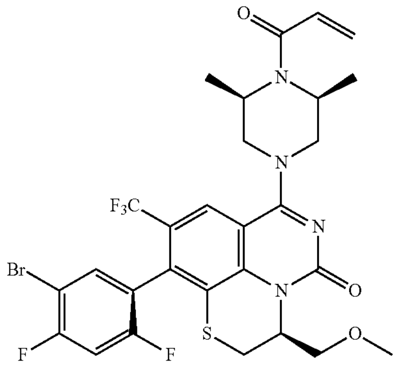 | (3S,10R)-7-((3S,5R)-4-Acryloyl-3,5-dimethylpiperazin-1-yl)-10-(5-bromo-2,4-difluorophenyl)-3-(methoxymethyl)-9-(trifluoromethyl)-2,3-dihydro-5H-[1,4]thiazino[2,3,4-ij]quinazolin-5-one | $^1$H NMR (400 MHz, MeOH-$d_4$) δ 8.15 (s, 1H), 7.66 (t, J = 7.4 Hz, 1H), 7.34 (t, J = 9.0 Hz, 1H), 6.84 (dd, J = 16.7, 10.6 Hz, 1H), 6.29 (dd, J = 16.7, 2.0 Hz, 1H), 5.80 (dd, J = 10.6, 2.0 Hz, 1H), 5.41-5.31 (m, 1H), 4.86-4.51 (m, 2H), 4.33 (d, J = 13.7 Hz, 1H), 4.26 (d, J = 13.4 Hz, 1H), 3.75 (t, J = 9.2 Hz, 1H), 3.62 (dd, J = 9.2, 4.8 Hz, 1H), 3.49 (dd, J = 13.5, 4.7 Hz, 1H), 3.45-3.36 (m, 2H), 3.40 (s, 3H), 3.15 (dd, J = 13.7, 2.9 Hz, 1H), 1.57 (d, J = 7.1 Hz, 3H), 1.42 (d, J = 7.0 Hz, 3H). | 673.2 |
| 2029 | 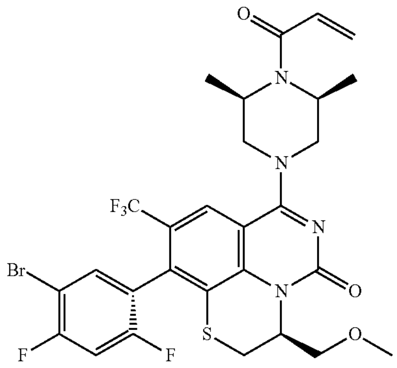 | (3S,10S)-7-((3S,5R)-4-Acryloyl-3,5-dimethylpiperazin-1-yl)-10-(5-bromo-2,4-difluorophenyl)-3-(methoxymethyl)-9-(trifluoromethyl)-2,3-dihydro-5H-[1,4]thiazino[2,3,4-ij]quinazolin-5-one | $^1$H NMR (400 MHz, MeOH-$d_4$) δ 8.15 (s, 1H), 7.60 (t, J = 7.5 Hz, 1H), 7.35 (t, J = 8.9 Hz, 1H), 6.84 (dd, J = 16.7, 10.6 Hz, 1H), 6.29 (dd, J = 16.7, 2.0 Hz, 1H), 5.80 (dd, J = 10.6, 2.0 Hz, 1H), 5.43-5.32 (m, 1H), 4.86-4.52 (m, 2H), 4.35 (d, J = 13.6 Hz, 1H), 4.26 (d, J = 13.6 Hz, 1H), 3.69 (t, J = 9.1 Hz, 1H), 3.60 (dd, J = 9.2, 4.9 Hz, 1H), 3.52 (dd, J = 13.6, 4.7 Hz, 1H), 3.47-3.35 (m, 2H), 3.39 (s, 3H), 3.17 (dd, J = 13.7, 3.0 Hz, 1H), 1.56 (d, J = 6.9 Hz, 3H), 1.42 (d, J = 6.9 Hz, 3H). | 673.2 |

TABLE 12-continued

| Summary of Compounds 2000 to 2109 | | | | |
|---|---|---|---|---|
| Ex.# | Structure | Name | $^1$H NMR | MS + 1 |
| 2030 | 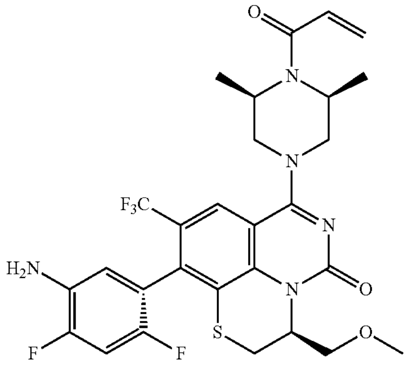 | (3S,10R)-7-((3S,5R)-4-Acryloyl-3,5-dimethylpiperazin-1-yl)-10-(5-amino-2,4-difluorophenyl)-3-(methoxymethyl)-9-(trifluoromethyl)-2,3-dihydro-5H-[1,4]thiazino[2,3,4-ij]quinazolin-5-one | 1H NMR (400 MHz, MeOH-$d_4$) δ 8.12 (s, 1H), 6.98 (dd, J = 11.1, 9.1 Hz, 1H), 6.84 (dd, J = 16.7, 10.6 Hz, 1H), 6.71 (dd, J = 9.5, 7.1 Hz, 1H), 6.29 (dd, J = 16.7, 2.0 Hz, 1H), 5.84-5.76 (m, 1H), 5.41-5.29 (m, 1H), 4.85-4.47 (m, 2H), 4.32 (d, J = 13.8 Hz, 1H), 4.25 (d, J = 13.7 Hz, 1H), 3.72 (d, J = 9.1 Hz, 1H), 3.61 (dd, J = 9.1, 4.7 Hz, 1H), 3.47 (dd, J = 13.6, 4.6 Hz, 1H), 3.43-3.33 (m, 2H), 3.39 (s, 3H), 3.12 (dd, J 13.7, 2.9 Hz, 1H), 1.58 (d, J = 6.9 Hz, 3H), 1.42 (d, J = 6.9 Hz, 3H). | 610.2 |
| 2031 | 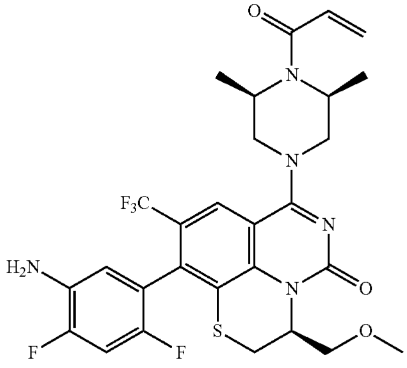 | (3S,10S)-7-((3S,5R)-4-Acryloyl-3,5-dimethylpiperazin-1-yl)-10-(5-amino-2,4-difluorophenyl)-3-(methoxymethyl)-9-(trifluoromethyl)-2,3-dihydro-5H-[1,4]thiazino[2,3,4-ij]quinazolin-5-one | $^1$H NMR (400 MHz, MeOH-$d_4$) δ 8.12 (s, 1H), 6.98 (dd, J = 11.0, 9.1 Hz, 1H), 6.84 (dd, J = 16.6, 10.6 Hz, 1H), 6.67 (dd, J = 9.5, 7.1 Hz, 1H), 6.29 (dd, J = 16.6, 2.1 Hz, 1H), 5.80 (dd, J = 10.5, 2.0 Hz, 1H), 5.43-5.31 (m, 1H), 4.85-4.50 (m, 2H), 4.33 (d, J = 13.6 Hz, 1H), 4.25 (d, J = 13.6 Hz, 1H), 3.70 (t, J = 9.1 Hz, 1H), 3.58 (dd, J = 9.2, 4.9 Hz, 1H), 3.48 (dd, J = 13.5, 4.7 Hz, 1H), 3.43-3.33 (m, 2H), 3.39 (s, 3H), 3.14 (dd, J = 13.6, 2.9 Hz, 1H), 1.57 (d, J = 6.9 Hz, 3H), 1.42 (d, J = 6.9 Hz, 3H). | 610.2 |

TABLE 12-continued

| Summary of Compounds 2000 to 2109 | | | | |
|---|---|---|---|---|
| Ex.# | Structure | Name | $^1$H NMR | MS + 1 |
| 2033 | 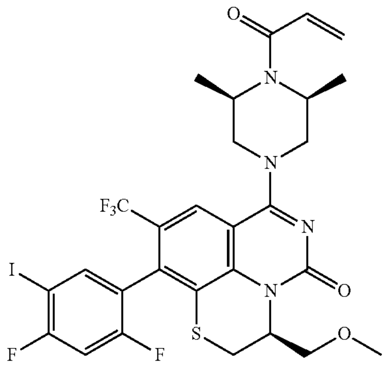 [SMILES: C=CC(=O)N1[C@H](C)CN(c2nc(=O)n3c4c(c(-c5cc(I)c(F)cc5F)c(C(F)(F)F)cc24)SC[C@@H]3COC)C[C@@H]1C] | (3S)-7-((3S,5R)-4-acryloyl-3,5-dimethylpiperazin-1-yl)-10-(2,4-difluoro-5-iodophenyl)-3-(methoxymethyl)-9-(trifluoromethyl)-2,3-dihydro-5H-[1,4]thiazino[2,3,4-ij]quinazolin-5-one | $^1$H NMR (400 MHz, MeOH-$d_4$) δ 8.14 (s, 1H), 7.76 (dt, J = 18.4, 7.3 Hz, 1H), 7.25 (td, J = 8.7, 4.1 Hz, 1H), 6.84 (dd, J = 16.7, 10.6 Hz, 1H), 6.29 (dd, J = 16.7, 2.0 Hz, 1H), 5.80 (dd, J = 10.6, 1.9 Hz, 1H), 5.44-5.3 (m, 1H), 4.86-4.46 (m, 2H), 4.41-4.30 (m, 1H), 4.26 (d, J = 13.5 Hz, 1H), 3.72 (dt, J = 22.6, 9.2 Hz, 1H), 3.60 (td, J = 9.6, 4.8 Hz, 1H), 3.50 (td, J = 12.7, 4.7 Hz, 1H), 3.45-3.42 (m, 1H), 3.41-3.35 (m, 4H), 3.16 (ddd, J = 13.7, 7.9, 2.9 Hz, 1H), 1.57 (dd, J = 7.1, 3.2 Hz, 3H), 1.42 (d, J = 6.9 Hz, 3H). | 721.2 |
| 2034 | 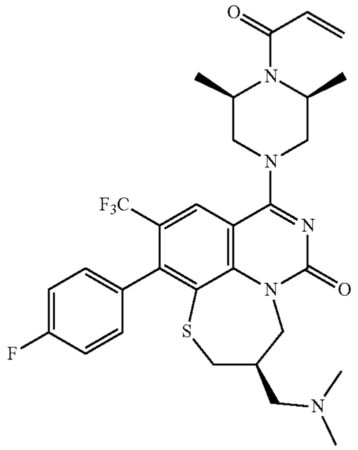 [SMILES: C=CC(=O)N1[C@H](C)CN(c2nc(=O)n3c4c(c(-c5ccc(F)cc5)c(C(F)(F)F)cc24)SC[C@H](CN(C)C)C3)C[C@@H]1C] | (R)-8-((3S,5R)-4-acryloyl-3,5-dimethylpiperazin-1-yl)-3-((dimethylamino) methyl)-11-(4-fluorophenyl)-10-(trifluoromethyl)-3,4-dihydro-[1,4]thiazepino[2,3,4-ij]quinazolin-6(2H)-one | $^1$H NMR (400 MHz, $CDCl_3$) δ 8.06 (s, 1H), 7.22-7.15 (m, 4H), 6.66-6.59 (m, 1H), 6.41 (d, J = 16.4 Hz, 1H), 5.77 (d, J = 10.4 Hz, 1H), 4.84-4.44 (m, 3H), 4.27-3.99 (m, 3H), 3.37-3.19 (m, 3H), 3.09-2.97 (m, 1H), 2.68-2.44 (m, 1H), 2.30-2.21 (m, 8H), 1.59-1.51 (m, 6H) | 603.2 |

TABLE 12-continued

| Summary of Compounds 2000 to 2109 | | | | |
|---|---|---|---|---|
| Ex.# | Structure | Name | $^1$H NMR | MS + 1 |
| 2035 | 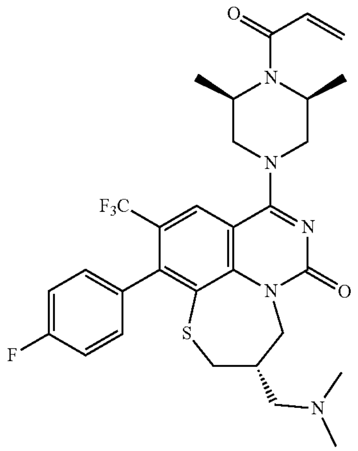 [SMILES: C=CC(=O)N1[C@H](C)CN(c2nc(=O)n3c4c(c(-c5ccc(F)cc5)c(C(F)(F)F)cc24)SC[C@@H](CN(C)C)C3)C[C@@H]1C] | (S)-8-((3S,5R)-4-acryloyl-3,5-dimethylpiperazin-1-yl)-3-((dimethylamino)methyl)-11-(4-fluorophenyl)-10-(trifluoromethyl)-3,4-dihydro-[1,4]thiazepino[2,3,4-ij]quinazolin-6(2H)-one | $^1$H NMR (400 MHz, $CDCl_3$) δ 8.06 (s, 1H), 7.22-7.15 (m, 4H), 6.66-6.59 (m, 1H), 6.41 (d, J = 16.8 Hz, 1H), 5.77 (d, J = 10.4 Hz, 1H), 4.86-4.45 (m, 3H), 4.32-3.95 (m, 3H), 3.41-3.20 (m, 3H), 3.05-3.02 (m, 1H), 2.67-2.42 (m, 1H), 2.30-2.21 (m, 8H), 1.58-1.51 (m, 6H). | 603.2 |
| 2036 | 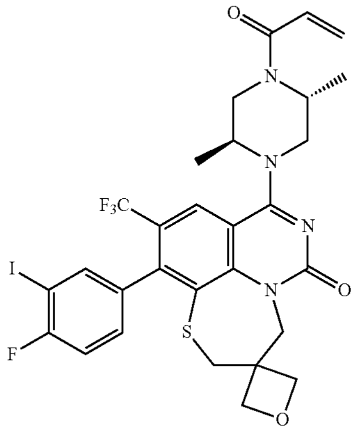 [SMILES: C=CC(=O)N1C[C@H](C)N(c2nc(=O)n3c4c(c(-c5ccc(F)c(I)c5)c(C(F)(F)F)cc24)SCC2(COC2)C3)C[C@H]1C] | 8'-((2S,5R)-4-acryloyl-2,5-dimethylpiperazin-1-yl)-11'-(2,4-difluoro-5-iodophenyl)-10'(trifluoromethyl)-2'H,4'H,6'H-spiro[oxetane-3,3'-[1,4]thiazepino[2,3,4-ij]quinazolin]-6'-one | $^1$H NMR (400 MHz, MeOH-$d_4$) δ 7.96 (s, 1H), 7.82-7.65 (m, 1H), 7.21 (td, J = 8.7, 3.1 Hz, 1H), 6.91-6.70 (m, 1H), 6.34-6.21 (m, 1H), 5.80 (ddd, J = 9.7, 7.2, 2.0 Hz, 1H), 4.86-4.58 (m, 3H), 4.57-4.36 (m, 3H), 4.35-3.99 (m, 2H), 3.98-3.68 (m, 2H), 3.67-3.36 (m, 3H), 1.53-1.2 0 (m, 6H). | 733.1 |
| 2037 | 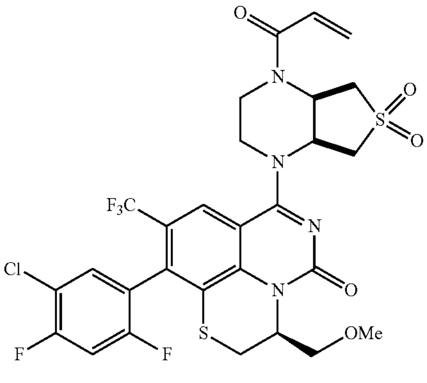 | (3S)-7-((4aR,7aS)-4-Acryloyl-6,6-dioxidohexahydro-thieno[3,4-b]pyrazin-1(2H)-yl)-10-(5-chloro-2,4-difluorophenyl)-3-(methoxymethyl)-9-(trifluoromethyl)-2,3-dihydro-5H-[1,4]thiazino[2,3,4-ij]quinazolin-5-one | $^1$H NMR (400 MHz, $CDCl_3$) δ 7.95 (s, 1H), 7.25-7.16 (m, 1H), 7.13-7.04 (m, 1H), 6.60-6.41 (m, 2H), 5.89 (dd, J = 16.0, 4.0 Hz, 1H), 5.72-5.20 (m, 3H), 4.85-4.75 (m, 1H), 4.20-3.86 (m, 3H), 3.83-3.71 (m, 2H), 3.70-3.60 (m, 2H), 3.60-3.45 (m, 3H), 3.43-3.30 (m, 3H), 3.11-2.97 (m, 1H) | 691.0 |

TABLE 12-continued

| Summary of Compounds 2000 to 2109 | | | | |
|---|---|---|---|---|
| Ex.# | Structure | Name | $^1$H NMR | MS + 1 |
| 2038 | 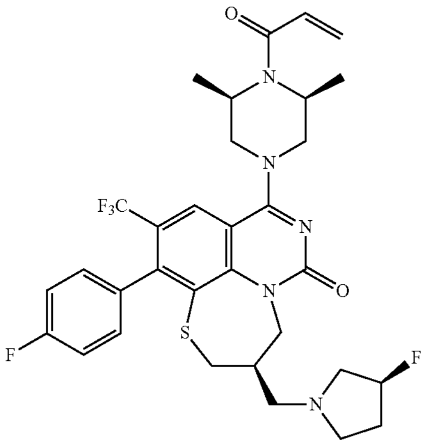 [SMILES: C=CC(=O)N1[C@H](C)CN(c2nc(=O)n3c4c(c(-c5ccc(F)cc5)c(C(F)(F)F)cc24)SC[C@H](CN2CC[C@H](F)C2)C3)C[C@@H]1C] | (R)-8-((3S,5R)-4-acryloyl-3,5-dimethylpiperazin-1-yl)-11-(4-fluorophenyl)-3-(((S)-3-fluoropyrrolidin-1-yl)methyl)-10-(trifluoromethyl)-3,4-dihydro-[1,4]thiazepino[2,3,4-ij]quinazolin-6(2H)-one | $^1$H NMR (400 MHz, $CDCl_3$) δ 8.06 (s, 1H), 7.22-7.15 (m, 4H), 6.66-6.59 (m, 1H), 6.41 (d, J = 16.4 Hz, 1H), 5.78 (d, J = 10.4 Hz, 1H), 5.20-5.06 (m, 1H), 4.84-4.45 (m, 3H), 4.24-4.14 (m, 3H), 3.37-3.21 (m, 3H), 3.12-3.03 (m, 1H), 2.91-2.80 (m, 2H), 2.72-2.54 (m, 3H), 2.46-2.33 (m, 2H), 2.16-1.93 (m, 2H), 1.62-1.51 (m, 6H). | 647.2 |
| 2039 | 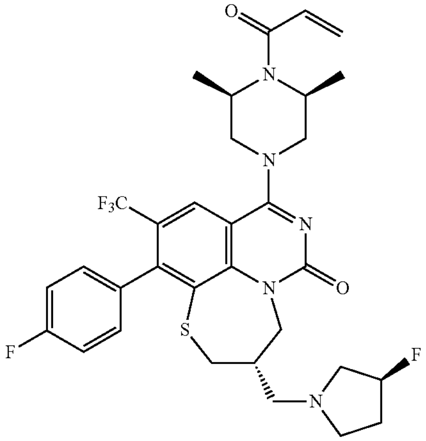 [SMILES: C=CC(=O)N1[C@H](C)CN(c2nc(=O)n3c4c(c(-c5ccc(F)cc5)c(C(F)(F)F)cc24)SC[C@@H](CN2CC[C@H](F)C2)C3)C[C@@H]1C] | (S)-8-((3S,5R)-4-acryloyl-3,5-dimethylpiperazin-1-yl)-11-(4-fluorophenyl)-3-(((S)-3-fluoropyrrolidin-1-yl)methyl)-10-(trifluoromethyl)-3,4-dihydro-[1,4]thiazepino[2,3,4-ij]quinazolin-6(2H)-one | $^1$H NMR (400 MHz, $CDCl_3$) δ 8.06 (s, 1H), 7.21-7.15 (m, 4H), 6.66-6.59 (m, 1H), 6.41 (d, J = 16.4 Hz, 1H), 5.78 (d, J = 10.8 Hz, 1H), 5.18-5.04 (m, 1H), 4.80-4.41 (m, 3H), 4.26-4.05 (m, 3H), 3.37-3.22 (m, 3H), 3.13-3.02 (m, 1H), 2.86-2.72 (m, 3H), 2.64-2.53 (m, 2H), 2.43-2.26 (m, 2H), 2.16-1.91 (m, 2H), 1.59-1.51 (m, 6H). | 647.2 |
| 2040 | 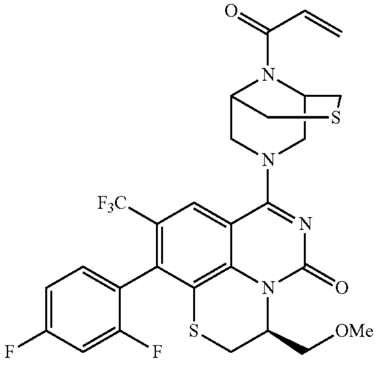 [SMILES: C=CC(=O)N1C2CCSCC1CN(c1nc(=O)n3c4c(c(-c5ccc(F)cc5F)c(C(F)(F)F)cc14)SC[C@@H]3COC)C2] | (3S)-7-(9-Acryloyl-3-thia-7,9-diazabicyclo[3.3.1]nonan-7-yl)-10-(2,4-difluorophenyl)-3-(methoxymethyl)-9-(trifluoromethyl)-2,3-dihydro-5H-[1,4]thiazino[2,3,4-ij]quinazolin-5-one | $^1$H NMR (400 MHz, CDCl3) δ 8.01-7.94 (m, 1H), 7.21-7.17 (m, 1H), 7.07-6.93 (m, 2H), 6.63-6.54 (m, 1H), 6.42-6.36 (m, 1H), 5.86-5.81 (m, 1H), 5.49-5.31 (m, 1H), 5.20-5.08 (m, 1H), 4.97-4.64 (m, 1H), 4.59-4.38 (m, 2H), 3.95-3.82 (m, 1H), 3.75-3.55 (m, 3H), 3.45-3.25 (m, 6H), 3.08-2.95 (m, 1H), 2.84-2.68 (m, 1H), 2.62-2.51 (m, 1H) | 625.1 |

TABLE 12-continued

| Summary of Compounds 2000 to 2109 | | | | |
|---|---|---|---|---|
| Ex.# | Structure | Name | $^1$H NMR | MS + 1 |
| 2041 | 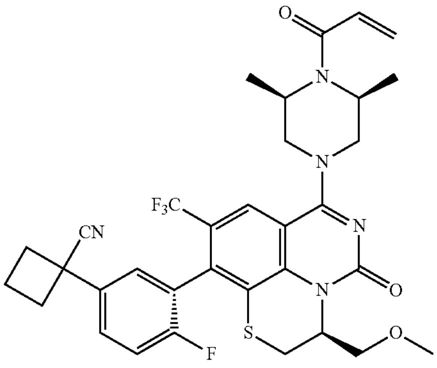 | 1-(3-((3S,10R)-7-((3S,5R)-4-acryloyl-3,5-dimethylpiperazin-1-yl)-3-(methoxymethyl)-5-oxo-9-(trifluoromethyl)-2,3-dihydro-5H-[1,4]thiazino[2,3,4-ij]quinazolin-10-yl)-4-fluorophenyl)cyclo-butane-1-carbonitrile | $^1$H NMR (400 MHz, MeOH-$d_4$) δ 8.16 (s, 1H), 7.72-7.63 (m, 1H), 7.41 (dd, J = 6.5, 2.5 Hz, 1H), 7.32 (t, J = 8.9 Hz, 1H), 6.84 (dd, J = 16.7, 10.6 Hz, 1H), 6.29 (dd, J = 16.7, 2.0 Hz, 1H), 5.80 (dd, J = 10.6, 2.0 Hz, 1H), 5.42-5.3 (m, 1H), 4.84-4.51 (br s, 2H), 4.33 (d, J = 13.9 Hz, 1H), 4.27 (d, J = 13.6 Hz, 1H), 3.75 (t, J = 9.2 Hz, 1H), 3.61 (dd, J = 9.3, 4.8 Hz, 1H), 3.52-3.4 (m, 2H), 3.39 (s, 3H), 3.38-3.33 (m, 1H), 3.15 (dd, J = 13.7, 3.0 Hz, 1H), 2.88-2.75 (m, 2H), 2.74-2.61 (m, 2H), 2.49-2.32 (m, 1H), 2.18-2.04 (m, 1H), 1.58 (d, J = 6.9 Hz, 3H), 1.43 (d, J = 6.9 Hz, 3H). | 656.3 |
| 2042 | 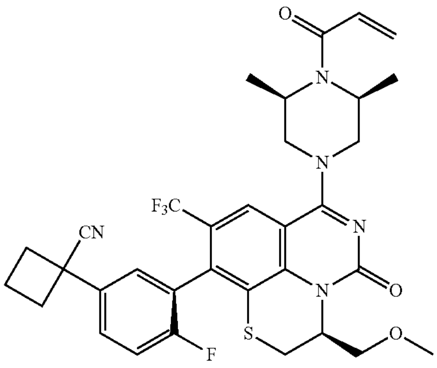 | 1-(3-((3S,10S)-7-((3S,5R)-4-acryloyl-3,5-dimethylpiperazin-1-yl)-3-(methoxymethyl)-5-oxo-9-(trifluoromethyl)-2,3-dihydro-5H-[1,4]thiazino[2,3,4-ij]quinazolin-10-yl)-4-fluorophenyl)cyclo-butane-1-carbonitrile | 1H NMR (400 MHz, MeOH-$d_4$) δ 8.16 (s, 1H), 7.73-7.63 (m, 1H), 7.39-7.28 (m, 2H), 6.84 (dd, J = 16.7, 10.6 Hz, 1H), 6.29 (dd, J = 16.7, 1.9 Hz, 1H), 5.80 (dd, J = 10.5, 2.0 Hz, 1H), 5.43-5.31 (m, 1H), 4.84-4.52 (m, 2H), 4.36 (d, J = 13.5 Hz, 1H), 4.27 (d, J = 13.5 Hz, 1H), 3.71 (t, J = 9.1 Hz, 1H), 3.60 (dd, J = 9.2, 4.9 Hz, 1H), 3.52 (dd, J = 13.5, 4.7 Hz, 1H), 3.46-3.4 (m, 1H), 3.39 (s, 3H), 3.38-3.33 (m, 1H), 3.16 (dd, J = 13.7, 3.0 Hz, 1H), 2.87-2.76 (m, 2H), 2.74-2.62 (m, 2H), 2.48-2.33 (m, 1H), 2.18-2.04 (m, 1H), 1.57 (d, J = | 656.3 |

TABLE 12-continued

Summary of Compounds 2000 to 2109

| Ex.# | Structure | Name | $^1$H NMR | MS + 1 |
|---|---|---|---|---|
| | | | 6.9 Hz, 3H), 1.42 (d, J = 6.8 Hz, 3H). | |
| 2043 | 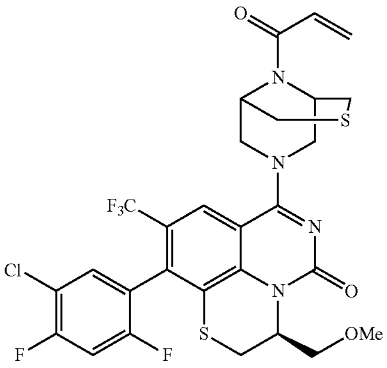 [SMILES: C=CC(=O)N1C2CCSCC1CN(c1nc(=O)n3c4c(c(-c5cc(Cl)c(F)cc5F)c(C(F)(F)F)cc14)SC[C@@H]3COC)C2] | (3S)-7-(9-Acryloyl-3-thia-7,9-diazabicyclo[3.3.1] nonan-7-yl)-10-(5-chloro-2.4-difluorophenyl)-3-(methoxymethyl)-9-(trifluoromethyl)-2,3-dihydro-5H-[1,4]thiazino[2,3,4-ij]quinazolin-5-one | $^1$H NMR (400 MHz, $CDCl_3$) δ 8.05-7.91 (m, 1H), 7.32-7.28 (m, 1H), 7.10-7.02 (m, 1H), 6.64-6.52 (m, 1H), 6.47-6.34 (m, 1H), 5.88-5.83 (m, 1H), 5.45-5.39 (m, 1H), 5.13-5.09 (m, 1H), 4.94-4.87 (m, 1H), 4.72-4.39 (m, 3H), 3.92-3.86 (m, 1H), 3.69-3.62 (m, 3H), 3.42-3.39 (m, 2H), 3.37-3.35 (m, 1H), 3.30-3.23 (m, 1H), 3.08-3.03 (m, 1H), 2.89-2.46 (m, 3H) | 659.0 |
| 2044a | 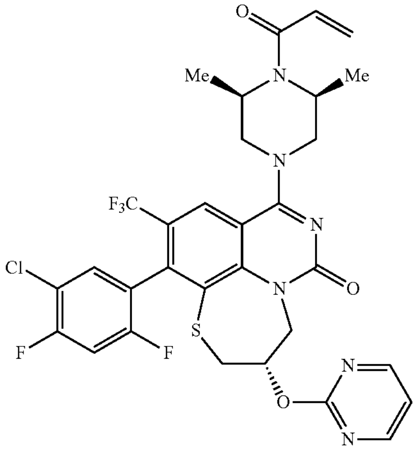 [SMILES: C=CC(=O)N1[C@H](C)CN(c2nc(=O)n3c4c(c(-c5cc(Cl)c(F)cc5F)c(C(F)(F)F)cc24)SC[C@@H](Oc2ncccn2)C3)C[C@@H]1C] | (3S)-8-((3S,5R)-4-acryloyl-3,5-dimethylpiperazin-1-yl)-11-(5-chloro-2,4-difluorophenyl)-3-(pyrimidin-2-yloxy)-10-(trifluoromethyl)-3,4-dihydro-2H,6H-[1,4]thiazepino[2,3,4-ij]quinazolin-6-one | 1H NMR (400 MHz, $CDCl_3$) δ 8.53 (d, J = 4.8 Hz, 2H), 8.10 (s, 1H), 7.31 (t, J = 7.6 Hz, 1H), 7.04 (t, J = 8.8 Hz, 1H), 6.99 (t, J = 4.8 Hz, 1H), 6.63 (dd, J = 10.4, 16.8 Hz, 1H), 6.42 (dd, J = 1.6, 16.4 Hz, 1H), 5.83-5.67 (m, 2H), 5.22-4.44 (m, 4H), 4.18 (d, J = 13.2 Hz, 2H), 3.68-3.47 (m, 1H), 3.46-3.24 (m, 3H), 1.64-1.54 (m, 6H) | 693.0 |
| 2045 | 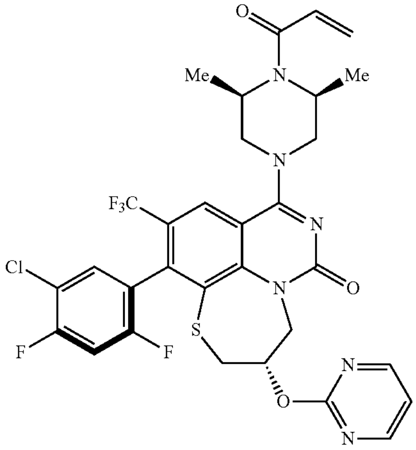 | (3S,11S)-8-((3S,5R)-4-acryloyl-3,5-dimethylpiperazin-1-yl)-11-(5-chloro-2,4-difluorophenyl)-3-(pyrimidin-2-yloxy)-10-(trifluoromethyl)-3,4-dihydro-2H,6H-[1,4]thiazepino[2,3,4-ij]quinazolin-6-one | $^1$H NMR (400 MHz, $CDCl_3$) δ 8.53 (d, J = 4.8 Hz, 2H), 8.10 (s, 1H), 7.31 (t, J = 7.6 Hz, 1H), 7.04 (t, J = 8.8 Hz, 1H), 6.99 (t, J = 4.8 Hz, 1H), 6.63 (dd, J = 10.4, 16.8 Hz, 1H), 6.42 (dd, J = 1.6, 16.4 Hz, 1H), 5.83-5.67 (m, 2H), 5.22-4.44 (m, 4H), 4.18 (d, J = 13.2 Hz, 2H), 3.68-3.47 (m, 1H), 3.46-3.24 (m, 3H), 1.64-1.54 (m, 6H) | 693.0 |

TABLE 12-continued

| Summary of Compounds 2000 to 2109 | | | | |
|---|---|---|---|---|
| Ex.# | Structure | Name | $^1$H NMR | MS + 1 |
| 2046 | 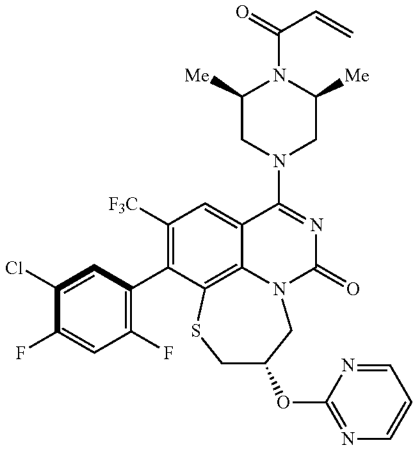 | (3S,11R)-8-((3S,5R)-4-acryloyl-3,5-dimethylpiperazin-1-yl)-11-(5-chloro-2,4-difluorophenyl)-3-(pyrimidin-2-yloxy)-10-(trifluoromethyl)-3,4-dihydro-2H,6H-[1,4]thiazepino[2,3,4-ij]quinazolin-6-one | $^1$H NMR (400 MHz, $CDCl_3$) δ 8.54 (d, J = 4.8 Hz, 2H), 8.10 (s, 1H), 7.31-7.27 (m, 1H), 7.07 (t, J = 8.8 Hz, 1H), 6.99 (t, J = 4.8 Hz, 1H), 6.63 (dd, J = 10.4, 16.8 Hz, 1H), 6.42 (dd, J = 2.0, 16.8 Hz, 1H), 5.82-5.62 (m, 2H), 5.07-4.40 (m, 4H), 4.18 (d, J = 13.2 Hz, 2H), 3.57-3.31 (m, 4H), 1.91-1.54 (m, 6H) | 693.0 |
| 2047 | 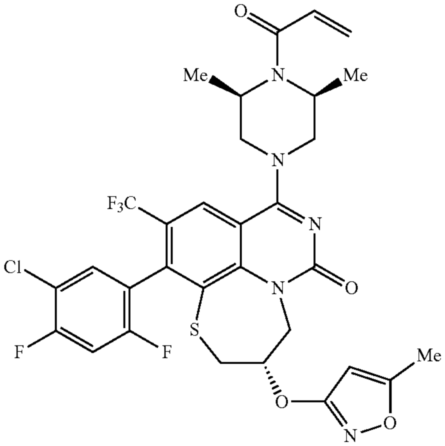 [SMILES: C=CC(=O)N1[C@H](C)CN(c2nc(=O)n3c4c(c(-c5cc(Cl)c(F)cc5F)c(C(F)(F)F)cc24)SC[C@@H](Oc2cc(C)on2)C3)C[C@@H]1C] | (3S)-8-((3S,5R)-4-acryloyl-3,5-dimethylpiperazin-1-yl)-11-(5-chloro-2,4-difluorophenyl)-3-((5-methylisoxazol-3-yl)oxy)-10-(trifluoromethyl)-3,4-dihydro-2H,6H-[1,4]thiazepino[2,3,4-ij]quinazolin-6-one | $^1$H NMR (400 MHz, $CDCl_3$) δ 8.08 (s, 1H), 7.25 (m, 1H), 7.06 (m, 1H), 6.63 (dd, $J_1$ = 17.2 Hz, $J_2$ = 10.8 Hz, 1H), 6.42 (dd, $J_1$ = 2.0 Hz, $J_2$ = 16.8 Hz, 1H), 5.79 (dd, $J_1$ = 2.0 Hz, $J_2$ = 10.4 Hz, 1H), 5.70 (s, 1H), 5.67 (s, 1H), 4.95~4.32 (m, 4H), 4.24~4.21 (m, 2H), 3.43~3.36 (m, 3H), 3.17~3.14 (m, 1H), 2.32 (s, 3H), 1.62-1.58 (m, 3H), 1.52-1.49 (s, 3H) | 696.2 |
| 2048 | 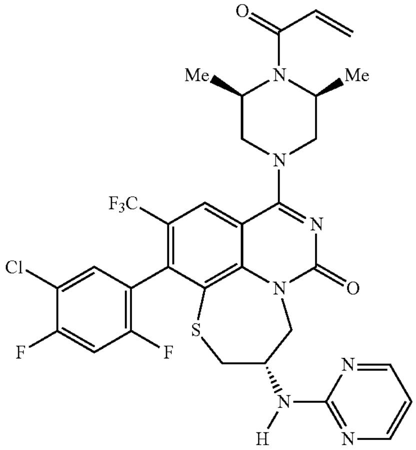 [SMILES: C=CC(=O)N1[C@H](C)CN(c2nc(=O)n3c4c(c(-c5cc(Cl)c(F)cc5F)c(C(F)(F)F)cc24)SC[C@@H](Nc2ncccn2)C3)C[C@@H]1C] | (3S,11R)-8-((3S,5R)-4-acryloyl-3,5-dimethylpiperazin-1-yl)-11-(5-chloro-2,4-difluorophenyl)-3-(pyrimidin-2-ylamino)-10-(trifluoromethyl)-3,4-dihydro-2H,6H-[1,4]thiazepino[2,3,4-ij]quinazolin-6-one | $^1$H NMR (400 MHz, CDCl3) δ 8.44-8.19 (m, 2H), 8.12 (s, 1H), 7.27-7.23 (m, 2H), 7.06 (br t, J = 8.8 Hz, 1H), 6.80-6.59 (m, 2H), 6.42 (dd, J = 1.6, 16.8 Hz, 1H), 5.79 (dd, J = 1.6, 10.4 Hz, 1H), 5.12-4.61 (m, 4H), 4.59-4.34 (m, 1H), 4.27-4.15 (m, 2H), 3.77-3.57 (m, 1H), 3.46-3.35 (m, 2H), 3.32-3.13 (m, 1H), 1.55 (br s, 6H) | 692.0 |

TABLE 12-continued

Summary of Compounds 2000 to 2109

| Ex.# | Structure | Name | $^1$H NMR | MS + 1 |
|---|---|---|---|---|
| 2049 | 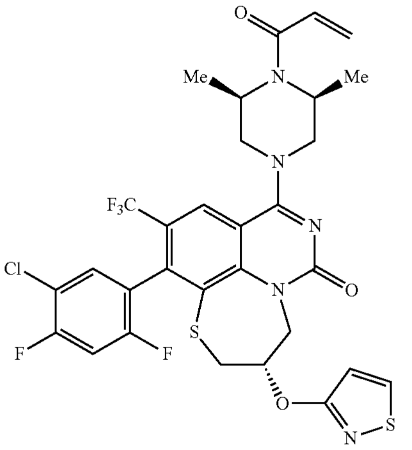 [SMILES: C=CC(=O)N1[C@H](C)CN(c2nc(=O)n3c4c(c(-c5cc(Cl)c(F)cc5F)c(C(F)(F)F)cc24)SC[C@@H](Oc2ccsn2)C3)C[C@@H]1C] | (3S)-8-((3S,5R)-4-acryloyl-3,5-dimethylpiperazin-1-yl)-11-(5-chloro-2,4-difluorophenyl)-3-(isothiazol-3-yloxy)-10-(trifluoromethyl)-3,4-dihydro-2H,6H-[1,4]thiazepino[2,3,4-ij]quinazolin-6-one | $^1$H NMR (400 MHz, DMSO-d6) δ ppm 1.41 (br s, 6H) 3.21-3.31 (m, 4H) 4.07 (br d, J = 12.60 Hz, 2H) 4.30-4.99 (m, 4H) 5.46 (br d, J = 5.20 Hz, 1H) 5.69-5.80 (m, 1H) 6.15-6.30 (m, 1H) 6.67-6.90 (m, 2H) 7.69-7.87 (m, 2H) 8.07 (br s, 1H) 8.45-8.52 (m, 1H) 8.92 (dd, J = 4.80, 2.40 Hz, 1H) | 698.1 |
| 2050 | 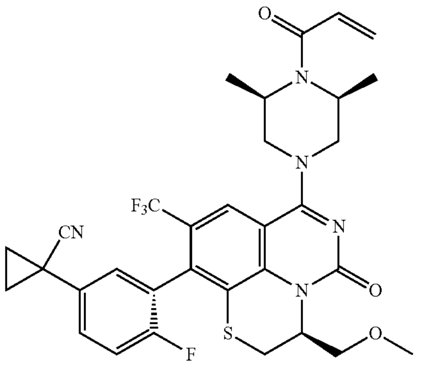 | 1-(5-((3S,10R)-7-((3S,5R)-4-acryloyl-3,5-dimethylpiperazin-1-yl)-3-(methoxymethyl)-5-oxo-9-(trifluoromethyl)-2,3-dihydro-5H-[1,4]thiazino[2,3,4-ij]quinazolin-10-yl)-2,4-difluorophenyl)cyclopropane-1-carbonitrile | $^1$H NMR (400 MHz, MeOH-$d_4$) δ 8.15 (s, 1H), 7.48 (t, J = 7.8 Hz, 1H), 7.27 (t, J = 9.7 Hz, 1H), 6.84 (dd, J = 16.7, 10.6 Hz, 1H), 6.29 (dd, J = 16.7, 2.0 Hz, 1H), 5.80 (dd, J = 10.6, 2.0 Hz, 1H), 5.41-5.30 (m, 1H), 4.85-4.52 (br s, 2H), 4.33 (d, J = 13.6 Hz, 1H), 4.26 (d, J = 13.6 Hz, 1H), 3.75 (t, J = 9.2 Hz, 1H), 3.62 (dd, J = 9.3, 4.8 Hz, 1H), 3.49 (dd, J = 13.5, 4.7 Hz, 1H), 3.46-3.4 (m, 1H), 3.40 (s, 3H), 3.39-3.34 (m, 1H), 3.15 (dd, J = 13.7, 3.0 Hz, 1H), 1.78-1.69 (m, 2H), 1.57 (d, J = 7.0 Hz, 3H), 1.49-1.36 (m, 5H). | 660.2 |
| 2051 | 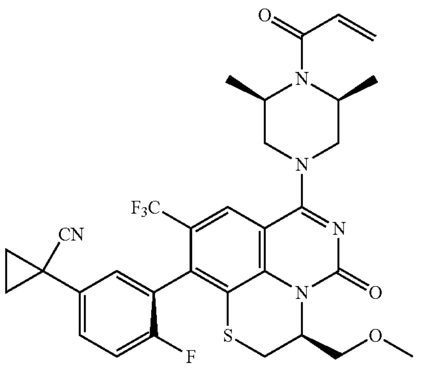 | 1-(5-((3S,10S)-7-((3S,5R)-4-acryloyl-3,5-dimethylpiperazin-1-yl)-3-(methoxymethyl)-5-oxo-9-(trifluoromethyl)-2,3-dihydro-5H-[1,4]t1iazino[2,3,4-ij]quinazolin-10-yl)-2,4-difluorophenyl)cyclopropane-1-carbonitrile | $^1$H NMR (400 MHz, MeOH-$d_4$) δ 8.14 (s, 1H), 7.42 (t, J = 7.9 Hz, 1H), 7.28 (t, J = 9.7 Hz, 1H), 6.84 (dd, J = 16.7, 10.6 Hz, 1H), 6.29 (dd, J = 16.7, 2.0 Hz, 1H), 5.80 (d, J = 11.4 Hz, 1H), 5.44-5.30 (m, 1H), 4.84-4.54 (m, 2H), 4.36 | 660.2 |

TABLE 12-continued

| Summary of Compounds 2000 to 2109 | | | | |
|---|---|---|---|---|
| Ex.# | Structure | Name | $^1$H NMR | MS + 1 |
| | | | (d, J = 13.4 Hz, 1H), 4.26 (d, J = 13.5 Hz, 1H), 3.70 (t, J = 9.1 Hz, 1H), 3.59 (dd, J = 9.3, 4.9 Hz, 1H), 3.52 (dd, J = 13.6, 4.7 Hz, 1H), 3.49-3.40 (m, 1H), 3.39 (s, 3H), 3.38-3.33 (m, 1H), 3.15 (dd, J = 13.8, 3.1 Hz, 1H), 1.77-1.69 (m, 2H), 1.56 (d, J = 6.9 Hz, 3H), 1.48-1.36 (m, 5H). | |
| 2053 | 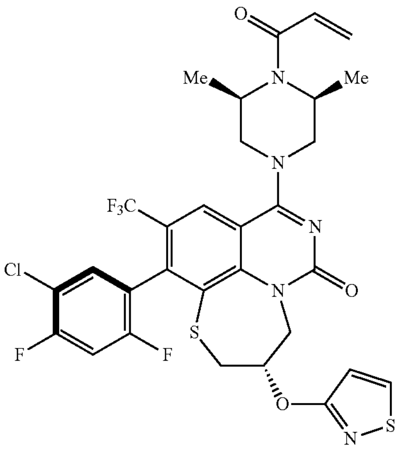 | (3S,11R)-8-((3S,5R)-4-acryloyl-3,5-dimethylpiperazin-1-yl)-11-(5-chloro-2,4-difluorophenyl)-3-(isothiazol-3-yloxy)-10-(trifluoromethyl)-3,4-dihydro-2H,6H-[1,4]thiazepino[2,3,4-ij]quinazolin-6-one | $^1$H NMR (400 MHz, CDCl3) δ: 8.38 (d, J = 4.8 Hz, 1H), 8.04 (s, 1H), 7.28-7.19 (m, 1H), 6.99 (t, J = 8.8 Hz, 1H), 6.63-6.50 (m, 2H), 6.42-6.27 (m, 1H), 5.71 (br d, J = 10.8 Hz, 1H), 5.55 (br s, 1H), 4.81 (br d, J = 10.4 Hz, 1H), 4.68-4.56 (m, 1H), 4.10 (br t, J = 13.2 Hz, 2H), 3.53-3.27 (m, 4H), 1.68 (br d, J = 1.2 Hz, 2H), 1.48 (br s, 6H) | 697.8 |
| 2054 | 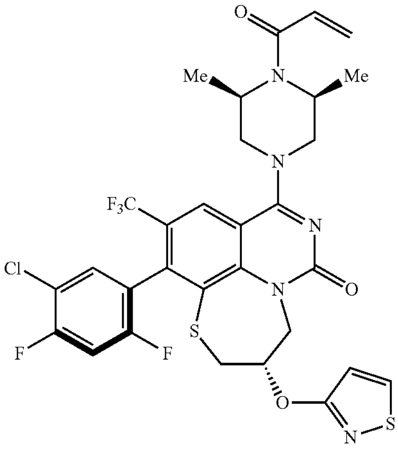 | (3S,11R)-8-((3S,5R)-4-acryloyl-3,5-dimethylpiperazin-1-yl)-11-(5-chloro-2,4-difluorophenyl)-3-(isothiazol-3-yloxy)-10-(trifluoromethyl)-3,4-dihydro-2H,6H-[1,4]thiazepino[2,3,4-ij]quinazolin-6-one | 1H NMR (400 MHz, CHLOROFORM-d) δ: 8.38 (d, J = 4.8 Hz, 1H), 8.03 (s, 1H), 7.26-7.20 (m, 1H), 7.03-6.93 (m, 1H), 6.69-6.50 (m, 2H), 6.34 (dd, J = 2.0, 16.8 Hz, 1H), 5.72 (dd, J = 2.0, 10.4 Hz, 1H), 5.58 (br s, 1H), 4.83 (br d, J = 1.2 Hz, 1H), 4.67-4.57 (m, 1H), 4.14-4.08 (m, 2H), 3.42-3.24 (m, 4H), 1.64 (br s, 2H), 1.48 (br t, J = 5.6 Hz, 6H) | 697.8 |

TABLE 12-continued

Summary of Compounds 2000 to 2109

| Ex.# | Structure | Name | $^1$H NMR | MS + 1 |
|---|---|---|---|---|
| 2055 | 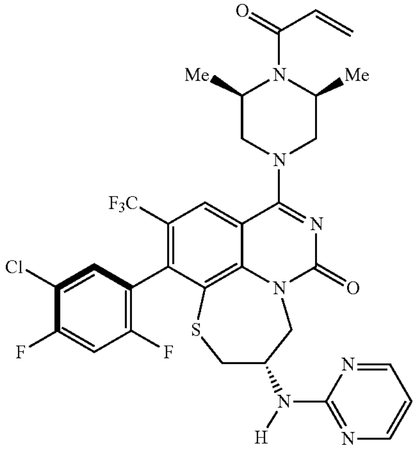 | (3S,11R)-8-((3S,5R)-4-acryloyl-3,5-dimethylpiperazin-1-yl)-11-(5-chloro-2,4-difluorophenyl)-3-(pyrimidin-2-ylamino)-10-(trifluoromethyl)-3,4-dihydro-2H,6H-[1,4]thiazepino[2,3,4-ij]quinazolin-6-one | $^1$H NMR (400 MHz, CDCl3) δ, 8.44-8.19 (m, 2H), 8.12 (s, 1H), 7.27-7.23 (m, 2H), 7.06 (br t, J = 8.8 Hz, 1H), 6.80-6.59 (m, 2H), 6.42 (dd, J = 1.6, 16.8 Hz, 1H), 5.79 (dd, J = 1.6, 10.4 Hz, 1H), 5.12-4.61 (m, 4H), 4.59-4.34 (m, 1H), 4.27-4.15 (m, 2H), 3.77-3.57 (m, 1H), 3.46-3.35 (m, 2H), 3.32-3.13 (m, 1H), 1.55 (br s, 6H) | 692.0 |
| 2056 | 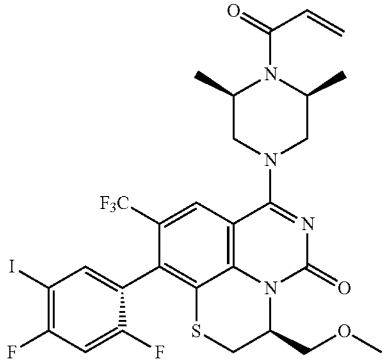 | (3S,10R)-7-((3S,5R)-4-acryloyl-3,5-dimethylpiperazin-1-yl)-10-(2,4-difluoro-5-iodophenyl)-3-(methoxymethyl)-9-(trifluoromethyl)-2,3-dihydro-5H-[1,4]thiazino[2,3,4-ij]quinazolin-5-one | $^1$H NMR (400 MHz, MeOH-$d_4$) δ 8.14 (s, 1H), 7.78 (t, J = 7.3 Hz, 1H), 7.24 (t, J = 8.8 Hz, 1H), 6.84 (dd, J = 16.7, 10.6 Hz, 1H), 6.29 (d, J = 16.0 Hz, 1H), 5.8 (dd, J = 10.5, 2.0 Hz, 1H), 5.42-5.30 (m, 1H), 4.84-4.51 (br s, 2H), 4.33 (d, J = 13.3 Hz, 1H), 4.26 (d, J = 13.5 Hz, 1H), 4.20 (s, 1H), 3.80-3.66 (m, 1H), 3.65-3.56 (m, 1H), 3.55-3.42 (m, 2H), 3.41 (s, 3H), 3.40-3.35 (m, 2H), 3.20-3.1 (m, 1H), 1.57 (d, J = 6.8 Hz, 3H), 1.42 (d, J = 6.9 Hz, 3H). | 721.2 |
| 2057 | 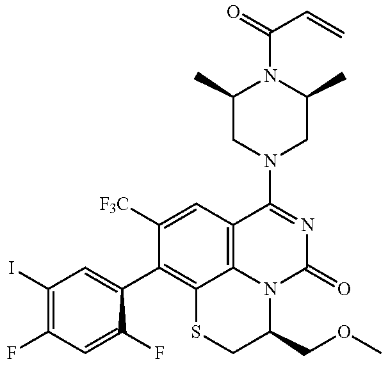 | (3S,10S)-7-((3S,5R)-4-acryloyl-3,5-dimethylpiperazin-1-yl)-10-(2,4-difluoro-5-iodophenyl)-3-(methoxymethyl)-9-(trifluoromethyl)-2,3-dihydro-5H-[1,4]thiazino[2,3,4-ij]quinazolin-5-one | $^1$H NMR (400 MHz, MeOH-$d_4$) δ 8.14 (s, 1H), 7.73 (t, J = 7.4 Hz, 1H), 7.25 (dd, J = 9.4, 8.1 Hz, 1H), 6.84 (dd, J = 16.7, 10.6 Hz, 1H), 6.29 (dd, J = 16.7, 2.0 Hz, 1H), 5.80 (dd, J = 10.6, 2.0 Hz, 1H), 5.43-5.31 (m, 1H), 4.84-4.55 (m, 2H), 4.35 (d, J = 13.5 Hz, 1H), 4.26 (d, J = 13.5 Hz, 1H), 4.18 (s, | 721.2 |

TABLE 12-continued

| Summary of Compounds 2000 to 2109 | | | | |
|---|---|---|---|---|
| Ex.# | Structure | Name | $^1$H NMR | MS + 1 |
| | | | 1H), 3.69 (t, J = 9.2 Hz, 1H), 3.59 (dd, J = 9.3, 4.9 Hz, 1H), 3.51 (dd, J = 13.5, 4.8 Hz, 1H), 3.46-3.38 (m, 1H), 3.39 (s, 3H), 3.38-3.35 (m, 1H), 3.17 (dd, J = 13.6, 3.0 Hz, 1H), 1.57 (d, J = 6.9 Hz, 3H), 1.42 (d, J = 6.9 Hz, 3H). | |
| 2058 | 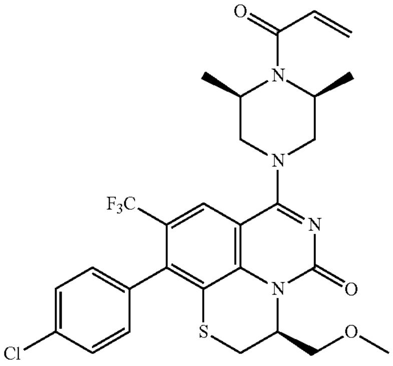 [SMILES: C=CC(=O)N1[C@H](C)CN(c2nc(=O)n3c4c(c(-c5ccc(Cl)cc5)c(C(F)(F)F)cc24)SC[C@@H]3COC)C[C@@H]1C] | (S)-7-((3S,5R)-4-acryloyl-3,5-dimethylpiperazin-1-yl)-10-(4-chlorophenyl)-3-(methoxymethyl)-9-(trifluoromethyl)-2,3-dihydro-5H-[1,4]thiazino[2,3,4-ij]quinazolin-5-one | $^1$H NMR (400 MHz, MeOH-$d_4$) δ 8.13 (s, 1H), 7.57-7.44 (m, 2H), 7.32-7.17 (m, 2H), 6.84 (dd, J = 16.7, 10.6 Hz, 1H), 6.29 (dd, J = 16.6, 2.0 Hz, 1H), 5.80 (dd, J = 10.7, 2.0 Hz, 1H), 5.40-5.28 (m, 1H), 4.85-4.50 (br s, 2H), 4.34 (d, J = 13.6 Hz, 1H), 4.26 (d, J = 13.6 Hz, 1H), 3.73 (t, J = 9.2 Hz, 1H), 3.60 (dd, J = 9.2, 4.8 Hz, 1H), 3.49 (dd, J = 13.5, 4.7 Hz, 1H), 3.44-3.33 (m, 1H), 3.39 (s, 3H), 3.09 (dd, J = 13.6, 2.9 Hz, 1H), 1.57 (d, J = 6.9 Hz, 3H), 1.42 (d, J = 6.9 Hz, 3H). | 593.2 |
| 2059 | 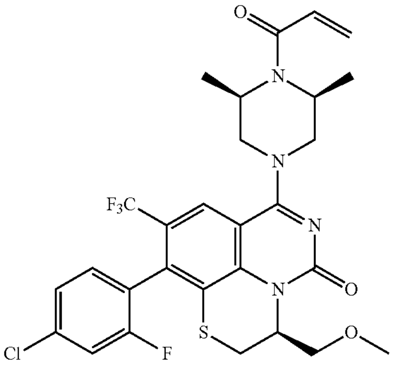 | (3S)-7-((3S,5R)-4-acryloyl-3,5-dimethylpiperazin-1-yl)-10-(4-chloro-2-fluorophenyl)-3-(methoxymethyl)-9-(trifluoromethyl)-2,3-dihydro-5H-[1,4]thiazino[2,3,4-ij]quinazolin-5-one | 1H NMR (400 MHz, MeOH-$d_4$) δ 8.15 (s, 1H), 7.45-7.35 (m, 2H), 7.34-7.22 (m, 1H), 6.84 (dd, J = 16.7, 10.6 Hz, 1H), 6.29 (dd, J = 16.7, 2.0 Hz, 1H), 5.80 (dd, J = 10.6, 2.0 Hz, 1H), 5.44-5.3 (m, 1H), 4.84-4.47 (br s, 2H), 4.42-4.30 (m, 1H), 4.26 (d, J = 13.5 Hz, 1H), 3.71 (q, J = 9.0 Hz, 1H), 3.65-3.55 (m, 1H), 3.55-3.45 (m, 1H), 3.45-3.34 (m, 2H), 3.39 (s, 1H), 3.20-3.10 (m, 1H), 1.57 | 611.2 |

TABLE 12-continued

| Summary of Compounds 2000 to 2109 | | | | |
|---|---|---|---|---|
| Ex.# | Structure | Name | $^1$H NMR | MS + 1 |
| | | | (dd, J = 7.0, 3.4 Hz, 3H), 1.42 (d, J = 6.9 Hz, 3H). | |
| 2060 | 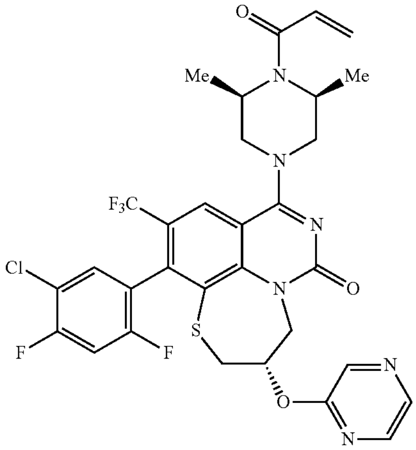 [SMILES: C=CC(=O)N1[C@H](C)CN(c2nc(=O)n3c4c(c(-c5cc(Cl)c(F)cc5F)c(C(F)(F)F)cc24)SC[C@@H](Oc2cnccn2)C3)C[C@@H]1C] | (3S)-8-((3S,5R)-4-acryloyl-3,5-dimethylpiperazin-1-yl)-11-(5-chloro-2,4-difluorophenyl)-3-(pyrazin-2-yloxy)-10-(trifluoromethyl)-3,4-dihydro-2H,6H-[1,4]thiazepino[2,3,4-ij]quinazolin-6-one | $^1$H NMR (400 MHz, CHLOROFORM-d) δ ppm 1.50 (d, J = 6.8 Hz, 3H) 1.63 (d, J = 6.8 Hz, 3H) 3.19-3.39 (m, 1H) 3.40-3.49 (m, 4H) 4.20-4.23 (m, 2H) 4.59-4.60 (m, 2H) 4.61-4.62 (m, 1H) 5.78-5.81 (m, 2H) 6.40-6.45 (m, 1H) 6.60-6.67 (m, 1H) 7.06-7.08 (m, 1H) 7.27 (s, 1H) 8.07-8.19 (m, 4H) | 693.2 |
| 2061 | 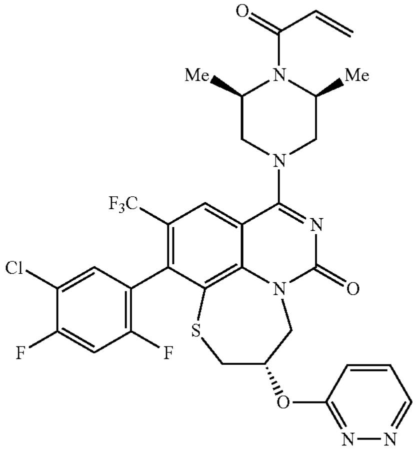 [SMILES: C=CC(=O)N1[C@H](C)CN(c2nc(=O)n3c4c(c(-c5cc(Cl)c(F)cc5F)c(C(F)(F)F)cc24)SC[C@@H](Oc2cccnn2)C3)C[C@@H]1C] | (3S)-8-((3S,5R)-4-acryloyl-3,5-dimethylpiperazin-1-yl)-11-(5-chloro-2,4-difluorophenyl)-3-(pyridazin-3-yloxy)-10-(trifluoromethyl)-3,4-dihydro-2H,6H-[1,4]thiazepino[2,3,4-ij]quinazolin-6-one | $^1$H NMR (400 MHz, CDCl3) δ 8.86 (dd, J = 1.2, 4.4 Hz, 1H), 8.12-8.08 (m, 1H), 7.40 (dd, J = 4.4, 8.8 Hz, 1H), 7.31-7.28 (m, 1H), 7.07 (t, J = 8.8 Hz, 1H), 7.03-6.97 (m, 1H), 6.68-6.59 (m, 1H), 6.43 (dd, J = 2.0, 16.8 Hz, 1H), 5.90-5.82 (m, 1H), 5.79 (dd, J = 2.0, 10.0 Hz, 1H), 4.90-4.85 (m, 1H), 4.81-4.56 (m, 3H), 4.26-4.19 (m, 2H), 3.48-3.39 (m, 2H), 3.35 (dd, J = 4.4, 13.6 Hz, 1H), 3.25-3.18 (m, 1H), 1.61 (d, J = 6.8 Hz, 3H), 1.52 (d, J = 6.8 Hz, 3H) | 693.0 |

TABLE 12-continued

| Summary of Compounds 2000 to 2109 | | | | |
|---|---|---|---|---|
| Ex.# | Structure | Name | $^1$H NMR | MS + 1 |
| 2062 | 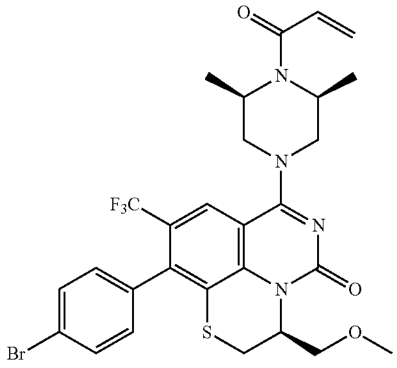 | (S)-7-((3S,5R)-4-acryloyl-3,5-dimethylpiperazin-1-yl)-10-(4-bromophenyl)-3-(methoxymethyl)-9-(trifluoromethyl)-2,3-dihydro-5H-[1,4]thiazino[2,3,4-ij]quinazolin-5-one | $^1$H NMR (400 MHz, MeOH-$d_4$) δ 8.13 (s, 1H), 7.72-7.61 (m, 2H), 7.26-7.12 (m, 2H), 6.84 (dd, J = 16.6, 10.6 Hz, 1H), 6.29 (dd, J = 16.7, 2.0 Hz, 1H), 5.80 (dd, J = 10.6, 2.0 Hz, 1H), 5.40-5.29 (m, 1H), 4.86-4.49 (br s, 2H), 4.34 (d, J = 13.6 Hz, 1H), 4.26 (d, J = 13.6 Hz, 1H), 3.73 (t, J = 9.2 Hz, 1H), 3.60 (dd, J = 9.2, 4.8 Hz, 1H), 3.49 (dd, J = 13.6, 4.7 Hz, 1H), 3.44-3.32 (m, 2H), 3.39 (s, 3H), 3.09 (dd, J = 13.7, 2.9 Hz, 1H), 1.57 (d, J = 6.9 Hz, 3H), 1.41 (d, J = 6.9 Hz, 3H). | 637.2 |
| 2063 | 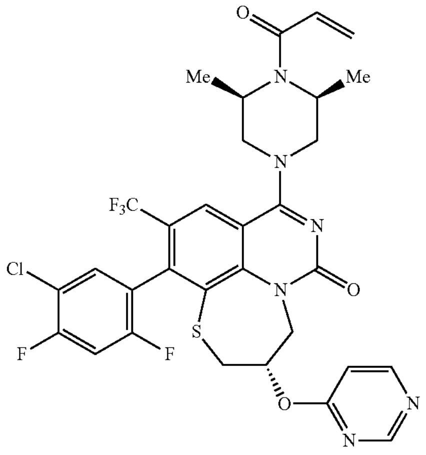 [SMILES: C=CC(=O)N1[C@H](C)CN(c2nc(=O)n3c4c(c(-c5cc(Cl)c(F)cc5F)c(C(F)(F)F)cc24)SC[C@@H](Oc2ccncn2)C3)C[C@@H]1C] | (3S)-8-((3S,5R)-4-acryloyl-3,5-dimethylpiperazin-1-yl)-11-(5-chloro-2,4-difluorophenyl)-3-(pyrimidin-4-yloxy)-10-(trifluoromethyl)-3,4-dihydro-2H,6H-[1,4]thiazepino[2,3,4-ij]quinazolin-6-one | $^1$H NMR (400 MHz, $CDCl_3$) δ, 8.90 (s, 1H), 8.61-8.49 (m, 1H), 8.09 (s, 1H), 7.27 (br s, 2H), 7.12-7.03 (m, 1H), 6.96 (q, J = 5.6 Hz, 1H), 6.68-6.57 (m, 1H), 6.41 (dd, J = 1.6, 16.8 Hz, 1H), 5.84-5.73 (m, 2H), 4.81-4.72 (m, 2H), 4.71-4.59 (m, 1H), 4.27-4.14 (m, 2H), 3.53-3.31 (m, 3H), 3.25-3.13 (m, 1H), 1.61 (d, J = 6.8 Hz, 3H), 1.49-1.44 (m, 3H) | 693.2 |

TABLE 12-continued

Summary of Compounds 2000 to 2109

| Ex.# | Structure | Name | $^1$H NMR | MS + 1 |
|---|---|---|---|---|
| 2064 | 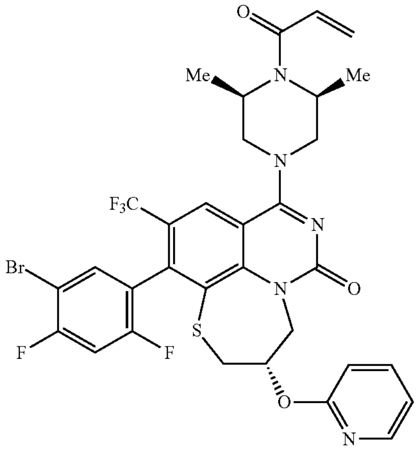 [SMILES: C=CC(=O)N1[C@H](C)CN(c2nc(=O)n3c4c(c(-c5cc(Br)c(F)cc5F)c(C(F)(F)F)cc24)SC[C@@H](Oc2ccccn2)C3)C[C@@H]1C] | (3S)-8-((3S,5R)-4-acryloyl-3,5-dimethylpiperazin-1-yl)-11-(5-bromo-2,4-difluorophenyl)-3-(pyridin-2-yloxy)-10-(trifluoromethyl)-3,4-dihydro-2H,6H-[1,4]thiazepino[2,3,4-ij]quinazolin-6-one | $^1$H NMR (400 MHz, CDCl3) δ = 8.25-8.01 (m, 2H), 7.75-7.59 (m, 1H), 7.48-7.36 (m, 1H), 7.10-6.91 (m, 2H), 6.89-6.75 (m, 1H), 6.63 (dd, J = 16.6, 10.6, 1H), 6.42 (dd, J = 16.6, 2.0, 1H), 5.93-5.71 (m, 2H), 5.04-4.48 (m, 4H), 4.28-4.06 (m, 2H), 3.67-3.25 (m, 4H), 1.71-1.36 (m, 6H) | 736.0 |
| 2065 | 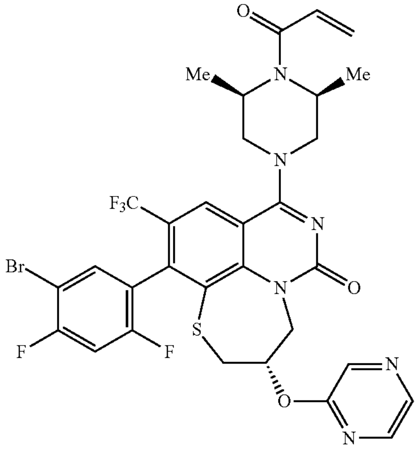 | (3S)-8-((3S,5R)-4-acryloyl-3,5-dimethylpiperazin-1-yl)-11-(5-bromo-2,4-difluorophenyl)-3-(pyrazin-2-yloxy)-10-(trifluoromethyl)-3,4-dihydro-2H,6H-[1,4]thiazepino[2,3,4-ij]quinazolin-6-one | $^1$H NMR (400 MHz, CDCl3) δ 8.25 (s, 1H), 8.15 (s, 1H), 8.11-8.07 (m, 2H), 7.46-74.42 (m, 1H), 7.26 (m, 1H), 6.63 (dd, J = 10.4, 16.8 Hz, 1H), 6.42 (dd, J = 1.6, 16.4 Hz, 1H), 5.83-5.67 (d, J = 10.4 Hz, 2H), 4.90-4.50 (m, 4H), 4.25 (m, 2H), 3.68-3.24 (m, 4H), 1.75-1.30 (m, 6H) | 737.1 |
| 2066 | 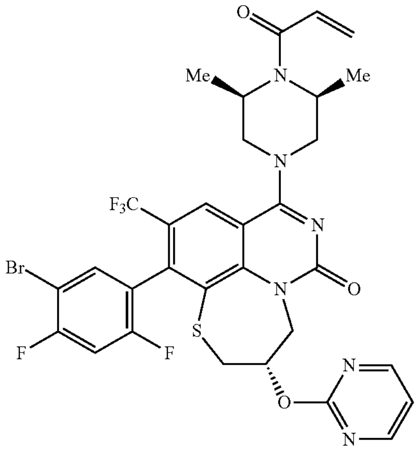 [SMILES: C=CC(=O)N1[C@H](C)CN(c2nc(=O)n3c4c(c(-c5cc(Br)c(F)cc5F)c(C(F)(F)F)cc24)SC[C@@H](Oc2ncccn2)C3)C[C@@H]1C] | (3S)-8-((3S,5R)-4-acryloyl-3,5-dimethylpiperazin-1-yl)-11-(5-bromo-2,4-difluorophenyl)-3-(pyrimidin-2-yloxy)-10-(trifluoromethyl)-3,4-dihydro-2H,6H-[1,4]thiazepino[2,3,4-ij]quinazolin-6-one | $^1$H NMR (400 MHz, CDCl3) δ = 8.54 (d, J = 4.0, 2H), 8.10 (s, 1H), 7.49-7.36 (m, 1H), 7.07-6.98 (m, 2H), 6.63 (dd, J = 16.4, 10.4, 1H), 6.42 (d, J = 16.0, 1H), 5.79 (d, J = 10.0, 1H), 5.74 (m, 1H), 4.93-4.67 (m, 4H), 4.19-4.15 (m, 2H), 3.66-3.36 (m, 4H), 1.75 (m, 3H), 1.55 (m, 3H). | 736.9/ 739.0 |

TABLE 12-continued

Summary of Compounds 2000 to 2109

| Ex.# | Structure | Name | $^1$H NMR | MS + 1 |
|---|---|---|---|---|
| 2067 | 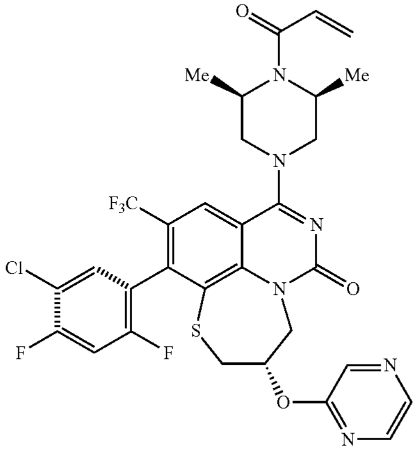 | (3S,11S)-8-((3S,5R)-4-acryloyl-3,5-dimethylpiperazin-1-yl)-11-(5-chloro-2,4-difluorophenyl)-3-(pyrazin-2-yloxy)-10-(trifluoromethyl)-3,4-dihydro-2H,6H-[1,4]thiazepino[2,3,4-ij]quinazolin-6-one | $^1$H NMR (400 MHz, CDCl3) δ ppm 1.50 (d, J = 7.2 Hz, 3H) 1.62 (s, 3H) 3.18-3.23 (m, 1H) 3.36-3.48 (m, 3H) 3.70-3.75 (m, 1H) 4.22 (d, J = 12.4 Hz, 2H) 4.57 4.61 (m, 2H) 4.67 (d, J = 10.4 Hz, 1H) 5.76 (d, J = 2.8 Hz, 1H) 5.78-5.81 (m, 1H) 6.40-6.45 (m, 1H) 6.60-6.67 (m, 1H) 7.08 (t, J = 8.8 Hz, 1H) 7.23-7.27 (m, 1H) 8.06 (s, 1H) 8.09 (s, 1H) 8.17 (d, J = 2.8 Hz, 1H) 8.25 (s, 1H) | 693.2 |
| 2068 | 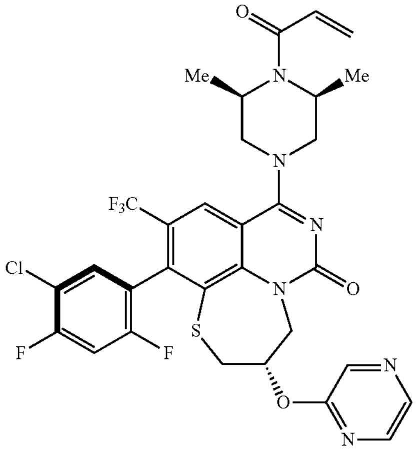 | (3S,11R)-8-((3S,5R)-4-acryloyl-3,5-dimethylpiperazin-1-yl)-11-(5-chloro-2,4-difluorophenyl)-3-(pyrazin-2-yloxy)-10-(trifluoromethyl)-3,4-dihydro-2H,6H-[1,4]thiazepino[2,3,4-ij]quinazolin-6-one | $^1$H NMR (400 MHz, CDCl3) δ ppm 1.50 (d, J = 6.8 Hz, 3H) 1.63 (d, J = 6.8 Hz, 3H) 3.19-3.39 (m, 1H) 3.40-3.49 (m, 4H) 4.20-4.23 (m, 2H) 4.59-4.60 (m, 2H) 4.61-4.62 (m, 1H) 5.78-5.81 (m, 2H) 6.40-6.45 (m, 1H) 6.60-6.67 (m, 1H) 7.06-7.08 (m, 1H) 7.27 (s, 1H) 8.07-8.19 (m, 4H) | 693.2 |
| 2069 | 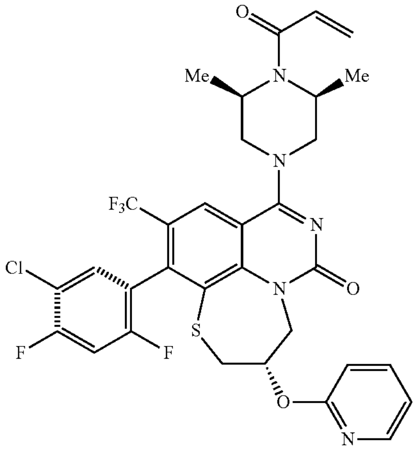 | (3S,11S)-8-((3S,5R)-4-acryloyl-3,5-dimethylpiperazin-1-yl)-11-(5-chloro-2,4-difluorophenyl)-3-(pyridin-2-yloxy)-10-(trifluoromethyl)-3,4-dihydro-2H,6H-[1,4]thiazepino[2,3,4-ij]quinazolin-6-one | $^1$H NMR (400 MHz, $CDCl_3$) δ, 8.12 (m, 2H), 7.58 (ddd, J = 4.0, 8.0, 8.0 Hz), 7.27 (s, 1H), 7.06 (J = 8.8, 8.8 Hz, 1H), 6.89 (m, 1H), 6.76 (d, J = 10.8 Hz), 6.63 (dd, J = 10.8, 16.4 Hz), 6.41 (dd, J = 1.6, 16.4 Hz, 1H), 5.78 (dd, J = 1.6, 10.8 Hz, 1H), 5.74 (m, 1H), 4.91-4.58 (m, 4H), 4.17 (m, 2H), 3.56-3.33 (m, 4H), 1.57 (m, 6H) | 692.1 |

TABLE 12-continued

| Summary of Compounds 2000 to 2109 | | | | |
|---|---|---|---|---|
| Ex.# | Structure | Name | $^1$H NMR | MS + 1 |
| 2070 | 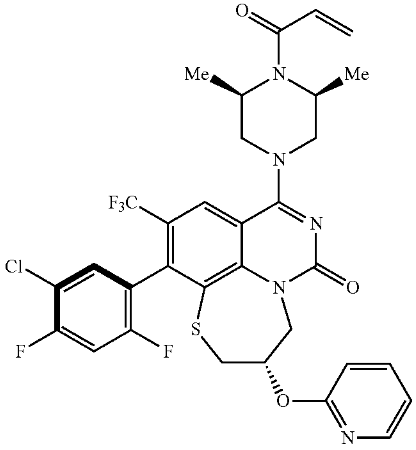 | (3S,11R)-8-((3S,5R)-4-acryloyl-3,5-dimethylpiperazin-1-yl)-11-(5-chloro-2,4-difluorophenyl)-3-(pyridin-2-yloxy)-10-(trifluoromethyl)-3,4-dihydro-2H,6H-[1,4]thiazepino[2,3,4-ij]quinazolin-6-one | $^1$H NMR (400 MHz, $CDCl_3$) δ 8.12 (m, 2H), 7.58 (ddd, J = 4.0, 8.0, 8.0 Hz), 7.27 (s, 1H), 7.06 (J = 8.8, 8.8 Hz, 1H), 6.89 (m, 1H), 6.76 (d, J = 10.8 Hz), 6.63 (dd, J = 10.8, 16.4 Hz), 6.41 (dd, J = 1.6, 16.4 Hz, 1H), 5.78 (dd, J = 1.6, 10.8 Hz, 1H), 5.74 (m, 1H), 4.91-4.58 (m, 4H), 4.17 (m, 2H), 3.56-3.33 (m, 4H), 1.57 (m, 6H) | 692.1 |
| 2071 | 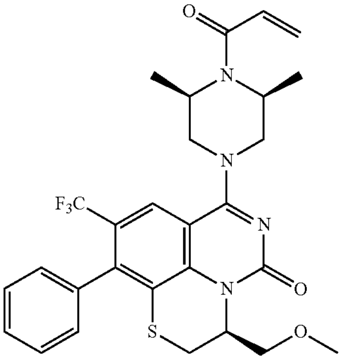 [SMILES: C=CC(=O)N1[C@H](C)CN(c2nc(=O)n3c4c(c(-c5ccccc5)c(C(F)(F)F)cc24)SC[C@@H]3COC)C[C@@H]1C] | (S)-7-((3S,5R)-4-acryloyl-3,5-dimethylpiperazin-1-yl)-3-(methoxymethyl)-10-phenyl-9-(trifluoromethyl)-2,3-dihydro-5H-[1,4]thiazino[2,3,4-ij]quinazolin-5-one | 1H NMR (400 MHz, MeOH-$d_4$) δ 8.13 (s, 1H), 7.56-7.43 (m, 3H), 7.31-7.16 (m, 2H), 6.84 (dd, J = 16.7, 10.6 Hz, 1H), 6.29 (dd, J = 16.7, 1.9 Hz, 1H), 5.80 (dd, J = 10.5, 2.0 Hz, 1H), 5.40-5.28 (m, 1H), 4.86-4.47 (br s, 2H), 4.34 (d, J = 13.7 Hz, 1H), 4.26 (d, J = 13.5 Hz, 1H), 3.73 (t, J = 9.2 Hz, 1H), 3.60 (dd, J = 9.2, 4.8 Hz, 1H), 3.47 (dd, J = 13.5, 4.7 Hz, 1H), 3.43-3.33 (m, 2H), 3.39 (s, 3H), 3.08 (dd, J = 13.7, 2.9 Hz, 1H), 1.58 (d, J = 6.9 Hz, 3H), 1.42 (d, J = 7.0 Hz, 3H). | 559.2 |
| 2072 | 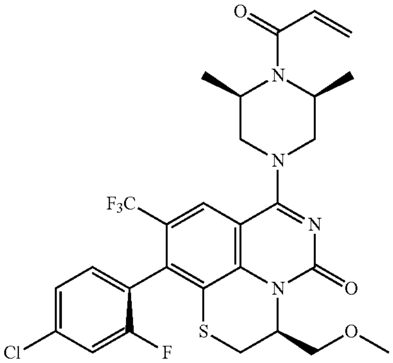 | (3S,10S)-7-((3S,5R)-4-acryloyl-3,5-dimethylpiperazin-1-yl)-10-(4-chloro-2-fluorophenyl)-3-(methoxymethyl)-9-(trifluoromethyl)-2,3-dihydro-5H-[1,4]thiazino[2,3,4-ij]quinazolin-5-one | $^1$H NMR (400 MHz, MeOH-$d_4$) δ 8.14 (s, 1H), 7.46-7.35 (m, 2H), 7.27 (t, J = 8.1 Hz, 1H), 6.84 (dd, J = 16.6, 10.6 Hz, 1H), 6.29 (dd, J = 16.6, 2.0 Hz, 1H), 5.80 (dd, J = 10.6, 2.0 Hz, 1H), 5.43-5.3 (m, 1H), 4.84-4.48 (br s, 2H), 4.35 (d, J = 13.7 Hz, 1H), 4.26 (d, J = 13.6 Hz, 1H), 3.70 (t, J = | 611.2 |

TABLE 12-continued

| Summary of Compounds 2000 to 2109 | | | | |
|---|---|---|---|---|
| Ex.# | Structure | Name | $^1$H NMR | MS + 1 |
| | | | 9.1 Hz, 1H), 3.59 (dd, J = 9.2, 4.9 Hz, 1H), 3.51 (dd, J = 13.6, 4.7 Hz, 1H), 3.46-3.33 (m, 2H), 3.39 (s, 3H), 3.15 (dd, J = 13.7, 2.9 Hz, 1H), 1.61-1.52 (m, 3H), 1.42 (d, J = 6.9 Hz, 3H). | |
| 2073 | 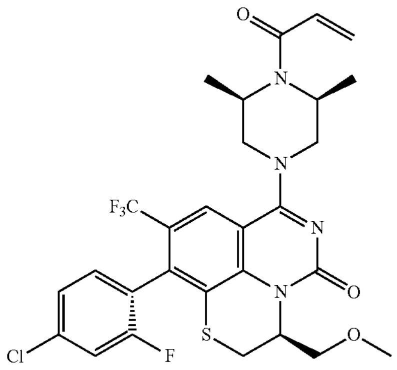 | (3S,10R)-7-((3S,5R)-4-acryloyl-3,5-dimethylpiperazin-1-yl)-10-(4-chloro-2-fluorophenyl)-3-(methoxymethyl)-9-(trifluoromethyl)-2,3-dihydro-5H-[1,4]thiazino[2,3,4-ij]quinazolin-5-one | $^1$H NMR (400 MHz, MeOH-$d_4$) δ 8.15 (s, 1H), 7.43-7.35 (m, 2H), 7.30 (t, J = 7.7 Hz, 1H), 6.84 (dd, J = 16.7, 10.6 Hz, 1H), 6.29 (dd, J = 16.7, 2.0 Hz, 1H), 5.80 (dd, J = 10.6, 2.0 Hz, 1H), 5.43-5.29 (m, 1H), 4.86-4.49 (br s, 2H), 4.33 (d, J = 13.7 Hz, 1H), 4.26 (d, J = 13.5 Hz, 1H), 3.72 (t, J = 9.2 Hz, 1H), 3.61 (dd, J = 9.2, 4.8 Hz, 1H), 3.48 (dd, J = 13.5, 4.7 Hz, 1H), 3.45-3.33 (m, 2H), 3.39 (s, 3H), 3.14 (dd, J = 13.6, 2.9 Hz, 1H), 1.58 (d, J = 6.7 Hz, 3H), 1.42 (d, J = 6.9 Hz, 3H). | 611.2 |
| 2074 | 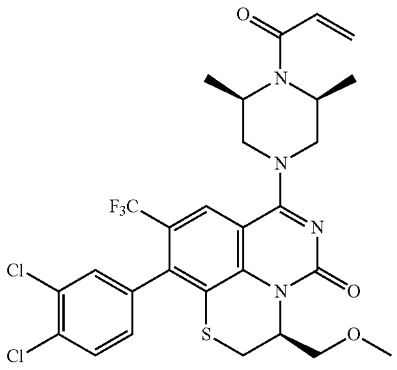 [SMILES: C=CC(=O)N1[C@H](C)CN(c2nc(=O)n3c4c(c(-c5ccc(Cl)c(Cl)c5)c(C(F)(F)F)cc24)SC[C@@H]3COC)C[C@@H]1C] | 7-((3S,5R)-4-acryloyl-3,5-dimethylpiperazin-1-yl)-10-(3,4-dichlorophenyl)-3-(methoxymethyl)-9-(trifluoromethyl)-2,3-dihydro-5H-[1,4]thiazino[2,3,4-ij]quinazolin-5-one | $^1$H NMR (400 MHz, $CDCl_3$) δ 8.05 (s, 1H), 7.57 (t, J = 8.0 Hz, 1H), 7.34 (s, 1H), 7.10-7.07 (m, 1H), 6.65-6.59 (m, 1H), 6.41 (dd, J = 1.6 Hz, 16.4 Hz, 1H), 5.77 (dd, J = 2.0 Hz, 10.4 Hz, 1H), 5.45-5.42 (m, 1H), 4.68-4.66 (m, 1H), 4.17 (t, J = 12.0 Hz, 2H), 3.69-3.63 (m, 2H), 3.40 (d, J = 8.0 Hz, 4H), 3.37-3.30 (m, 3H), 2.99-2.94 (m, 1H), 1.62-1.60 (m, 3H), 1.48-1.45 (m, 3H). | 627.3 |

TABLE 12-continued

| Summary of Compounds 2000 to 2109 | | | | |
|---|---|---|---|---|
| Ex.# | Structure | Name | $^1$H NMR | MS + 1 |
| 2075 | 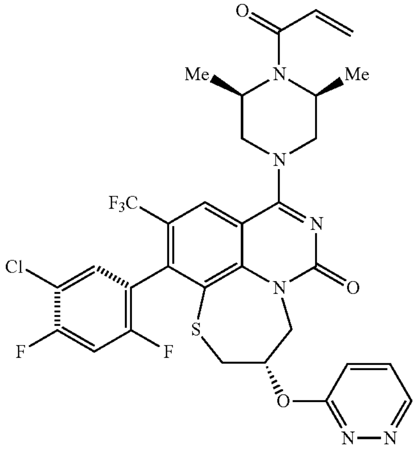 | (3S,11S)-8-((3S,5R)-4-acryloyl-3,5-dimethylpiperazin-1-yl)-11-(5-chloro-2,4-difluorophenyl)-3-(pyridazin-3-yloxy)-10-(trifluoromethyl)-3,4-dihydro-2H,6H-[1,4]thiazepino[2,3,4-ij]quinazolin-6-one | $^1$H NMR (400 MHz, $CDCl_3$) δ 8.90-8.83 (m, 1H), 8.10 (s, 1H), 7.41 (dd, J = 4.4, 8.8 Hz, 1H), 7.32-7.27 (m, 1H), 7.07 (t, J = 8.8 Hz, 1H), 7.02 (dd, J = 1.2, 8.8 Hz, 1H), 6.68-6.59 (m, 1H), 6.43 (dd, J = 2.0, 16.8 Hz, 1H), 5.88-5.75 (m, 2H), 4.92-4.84 (m, 1H), 4.72 (dd, J = 5.2, 10.0 Hz, 3H), 4.22 (br t, J = 11.6 Hz, 2H), 3.51-3.29 (m, 3H), 3.22 (dd, J = 2.8, 13.6 Hz, 1H), 1.63-1.61 (m, 3H), 1.52 (d, J = 7.2 Hz, 3H) | 693.0 |
| 2076 | 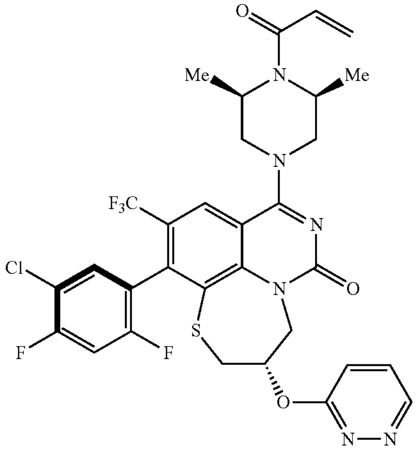 | (3S,11R)-8-((3S,5R)-4-acryloyl-3,5-dimethylpiperazin-1-yl)-11-(5-chloro-2,4-difluorophenyl)-3-(pyridazin-3-yloxy)-10-(trifluoromethyl)-3,4-dihydro-2H,6H-[1,4]thiazepino[2,3,4-ij]quinazolin-6-one | 1H NMR (400 MHz, $CDCl_3$) δ 8.86 (d, J = 4.4 Hz, 1H), 8.12 (s, 1H), 7.4 (dd, J = 4.4, 8.8 Hz, 1H), 7.31-7.28 (m, 1H), 7.05 (t, J = 8.8 Hz, 1H), 7.00 (d, J = 8.8 Hz, 1H), 6.69-6.58 (m, 1H), 6.47-6.38 (m, 1H), 5.90-5.76 (m, 2H), 4.89 (dd, J = 8.0, 10.4 Hz, 1H), 4.71 (dd, J = 5.2, 10.4 Hz, 3H), 4.28-4.15 (m, 2H), 3.48-3.31 (m, 3H), 3.20 (dd, J = 2.8, 13.6 Hz, 1H), 1.62 (s, 3H), 1.52 (d, J = 7.2 Hz, 3H) | 693.0 |
| 2077 | 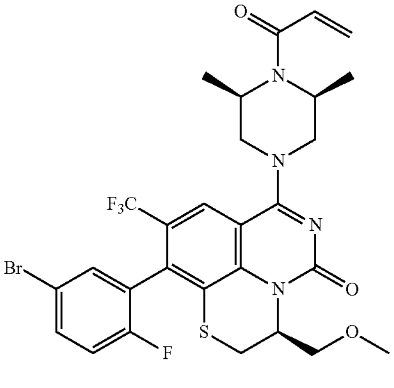 [SMILES: C=CC(=O)N1[C@H](C)CN(c2nc(=O)n3c4c(c(-c5cc(Br)ccc5F)c(C(F)(F)F)cc24)SC[C@@H]3COC)C[C@@H]1C] | (3S)-7-((3S,5R)-4-acryloyl-3,5-dimethylpiperazin-1-yl)-10-(5-bromo-2-fluorophenyl)-3-(methoxymethyl)-9-(trifluoromethyl)-2,3-dihydro-5H-[1,4]thiazepino[2,3,4-ij]quinazolin-5-one | $^1$H NMR (400 MHz, MeOH-$d_4$) δ 8.15 (s, 1H), 7.78-7.65 (m, 1H), 7.46 (ddd, J = 19.1, 6.4, 2.5 Hz, 1H), 7.23 (td, J = 8.9, 3.9 Hz, 1H), 6.84 (dd, J = 16.7, 10.6 Hz, 1H), 6.29 (dd, J = 16.6, 2.0 Hz, 1H), 5.80 (dd, J = 10.5, 2.0 Hz, 1H), 5.45-5.29 (m, 1H), 4.86- | 655.1 |

TABLE 12-continued

| Ex.# | Structure | Name | $^1$H NMR | MS + 1 |
|---|---|---|---|---|
| Summary of Compounds 2000 to 2109 | | | | |
| | | | 4.52 (br s, 2H), 4.34 (t, J = 11.3 Hz, 1H), 4.26 (d, J = 13.6 Hz, 1H), 3.72 (dt, J = 18.8, 9.2 Hz, 1H), 3.66-3.56 (m, 1H), 3.55-3.46 (m, 1H), 3.45-3.33 (m, 2H), 3.40 (d, J = 6.3 Hz, 3H), 3.21-3.09 (m, 1H), 1.63-1.51 (m, 3H), 1.42 (d, J = 7.0 Hz, 3H). | |
| 2078 | 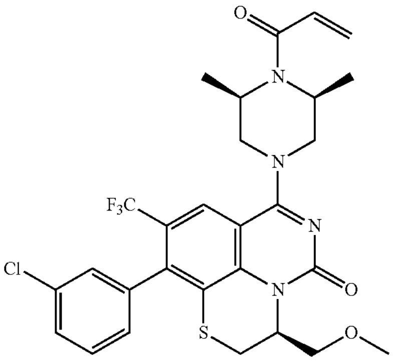 | (S)-7-((3S,5R)-4-acryloyl-3,5-dimethylpiperazin-1-yl)-10-(3-chlorophenyl)-3-(methoxymethyl)-9-(trifluoromethyl)-2,3-J = dihydro-5H-[1,4]thiazino[2,3,4-ij]quinazolin-5-one | $^1$H NMR (400 MHz, $CDCl_3$) δ 8.06 (s, 1H), 7.48-7.40 (m, 2H), 7.25-7.22 (m, 1H), 7.12 (t, 7.2 Hz, 1H), 6.66-6.59 (m, 1H), 6.40 (dd, J = 1.6 Hz, 16.4 Hz, 1H), 5.77 (dd, J = 2.0 Hz, 10.4 Hz, 1H), 5.44-5.41 (m, 1H), 4.77-4.57 (m, 2H), 4.21-4.16 (m, 2H), 3.71-3.61 (m, 2H), 3.41-3.30 (m, 6H), 2.99-2.94 (m, 1H), 1.62 (dd, J = 1.6 Hz, 6.8 Hz, 3H), 1.49-1.46 (m, 3H). | 593.1 |
| 2079 | 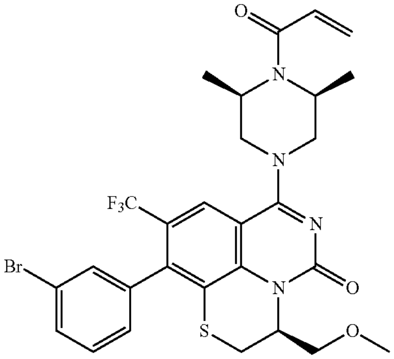 [SMILES: C=CC(=O)N1[C@H](C)CN(c2nc(=O)n3c4c(c(-c5cccc(Cl)c5)c(C(F)(F)F)cc24)SC[C@@H]3COC)C[C@@H]1C] | (S)-7-((3S,5R)-4-acryloyl-3,5-dimethylpiperazin-1-yl)-10-(3-bromophenyl)-3-(methoxymethyl)-9-(trifluoromethyl)-2,3-dihydro-5H-[1,4]thiazino[2,3,4-ij]quinazolin-5-one | $^1$H NMR (400 MHz, MeOH-$d_4$) δ 8.13 (s, 1H), 7.67 (d, J = 7.9 Hz, 1H), 7.50-7.37 (m, 2H), 7.25 (dd, J = 15.8, 7.7 Hz, 1H), 6.84 (dd, J = 16.7, 10.6 Hz, 1H), 6.29 (dd, J = 16.6, 2.0 Hz, 1H), 5.80 (dd, J = 10.5, 2.0 Hz, 1H), 5.41-5.28 (m, 1H), 4.86-4.48 (br s, 2H), 4.34 (d, J = 13.7 Hz, 1H), 4.26 (d, J = 13.5 Hz, 1H), 3.74 (dt, J = 11.2, 9.2 Hz, 1H), 3.61 (dt, J = 9.1, 4.5 Hz, 1H), 3.49 (dd, J = 13.6, 4.7 Hz, 1H), 3.46-3.32 (m, 2H), 3.4 (d, J = 6.6 Hz, 3H), 3.10 (ddd, J = 13.7, 5.4, 3.1 Hz, 1H), | 637.1 |

TABLE 12-continued

| Summary of Compounds 2000 to 2109 | | | | |
|---|---|---|---|---|
| Ex.# | Structure | Name | $^1$H NMR | MS + 1 |
| | | | 1.57 (d, J = 6.9 Hz, 3H), 1.42 (d, J = 6.9 Hz, 3H). | |
| 2080 | 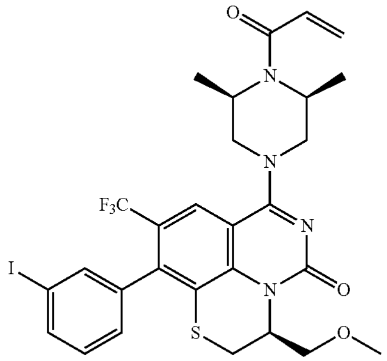 [SMILES: C=CC(=O)N1[C@H](C)CN(c2nc(=O)n3c4c(c(-c5cccc(I)c5)c(C(F)(F)F)cc24)SC[C@@H]3COC)C[C@@H]1C] | (S)-7-((3S,5R)-4-acryloyl-3,5-dimethylpiperazin-1-yl)-10-(3-iodophenyl)-3-(methoxymethyl)-9-(trifluoromethyl)-2,3-dihydro-5H-[1,4]thiazino[2,3,4-ij]quinazolin-5-one | $^1$H NMR (400 MHz, MeOH-$d_4$) δ 8.13 (s, 1H), 7.86 (d, J = 7.1 Hz, 1H), 7.63 (d, J = 13.9 Hz, 1H), 7.35-7.21 (m, 2H), 6.84 (dd, J = 16.6, 10.6 Hz, 1H), 6.29 (dd, J = 16.7, 2.0 Hz, 1H), 5.80 (dd, J = 10.6, 2.0 Hz, 1H), 5.40-5.28 (m, 1H), 4.87-4.50 (br s, 2H), 4.34 (d, J = 13.7 Hz, 1H), 4.26 (d, J = 13.5 Hz, 1H), 3.74 (dt, J = 12.7, 9.2 Hz, 1H), 3.61 (dt, J = 9.5, 5.0 Hz, 1H), 3.49 (dd, J = 13.6, 4.7 Hz, 1H), 3.45-3.33 (m, 2H), 3.4 (d, J = 8.4 Hz, 1H), 3.09 (ddd, J = 13.6, 7.0, 3.0 Hz, 1H), 1.57 (d, J = 6.9 Hz, 3H), 1.42 (d, J = 6.9 Hz, 3H). | 685.1 |
| 2081 | 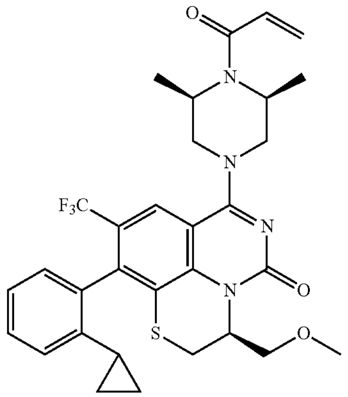 [SMILES: C=CC(=O)N1[C@H](C)CN(c2nc(=O)n3c4c(c(-c5ccccc5C5CC5)c(C(F)(F)F)cc24)SC[C@@H]3COC)C[C@@H]1C] | (3S)-7-((3S,5R)-4-acryloyl-3,5-dimethylpiperazin-1-yl)-10-(2-cyclopropylphenyl)-3-(methoxymethyl)-9-(trifluoromethyl)-2,3-dihydro-5H-[1,4]thiazino[2,3,4-ij]quinazolin-5-one | $^1$H NMR (400 MHz, MeOH-$d_4$) δ 8.16 (s, 1H), 7.38 (t, J = 7.7 Hz, 1H), 7.24 (t, J = 7.5 Hz, 1H), 7.04 (dd, J = 7.8, 4.3 Hz, 1H), 6.96 (t, J = 7.1 Hz, 1H), 6.84 (dd, J = 16.6, 10.6 Hz, 1H), 6.29 (d, J = 16.6 Hz, 1H), 5.80 (d, J = 10.6 Hz, 1H), 5.42-5.28 (m, 1H), 4.86-4.44 (br s, 2H), 4.42-4.30 (m, 1H), 4.27 (dd, J = 13.7, 2.2 Hz, 1H), 3.79-3.65 (m, 1H), 3.65-3.53 (m, 1H), 3.52-3.43 (m, 1H), 3.43-3.35 (m, 1H), 3.38 (s, 3H), 3.34-3.26 (m, 1H), 3.10 (td, J = 14.4, 13.7, 2.9 Hz, 1H), 1.59 (d, J = | 599.3 |

TABLE 12-continued

| Summary of Compounds 2000 to 2109 | | | | |
|---|---|---|---|---|
| Ex.# | Structure | Name | $^1$H NMR | MS + 1 |
| | | | 6.9 Hz, 3H), 1.48-1.33 (m, 4H), 0.86-0.65 (m, 3H). | |
| 2082 | 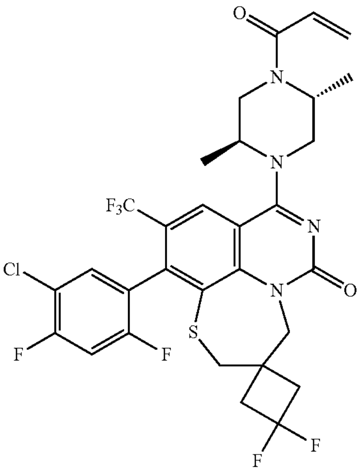 [SMILES: C=CC(=O)N1C[C@H](C)N(c2nc(=O)n3c4c(c(-c5cc(Cl)c(F)cc5F)c(C(F)(F)F)cc24)SCC2(C3)CC(F)(F)C2)C[C@H]1C] | 8'-((2S,5R)-4-acryloyl-2,5-dimethylpiperazin-1-yl)-11'-(5-chloro-2,4-difluorophenyl)-3,3-difluoro-10'-(trifluoromethyl)-2'H,4'H,6'H-spiro[cyclobutane-1,3'-[1,4]thiazepino[2,3,4-ij]quinazolin]-6'-one | $^1$H NMR (400 MHz, MeOH-$d_4$) δ 7.96 (s, 1H), 7.61-7.41 (m, 1H), 7.34 (td, J = 9.2, 3.7 Hz, 1H), 6.92-6.71 (m, 1H), 6.37-6.21 (m, 1H), 5.81 (ddd, J = 9.9, 7.2, 1.9 Hz, 1H), 4.87-4.38 (m, 4H), 4.37-3.33 (m, 10H), 2.60-2.37 (m, 2H), 1.59-1.20 (m, 6H); | 675.2 |
| 2083 | 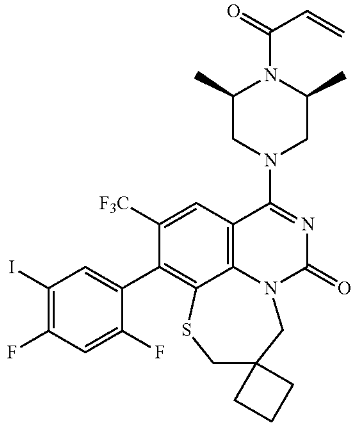 | 8'-((3S,5R)-4-acryloyl-3,5-dimethylpiperazin-1-yl)-11'-(2,4-difluoro-5-iodophenyl)-10'-(trifluoromethyl)-2'H,4'H,6'H-spiro[cyclobutane-1,3'-[1,4]thiazepino[2,3,4-ij]quinazolin]-6'-one | $^1$H NMR (400 MHz, MeOH-$d_4$) δ 8.12 (s, 1H), 7.83-7.67 (m, 1H), 7.21 (t, J = 8.7 Hz, 1H), 6.84 (dd, J = 16.7, 10.6 Hz, 1H), 6.29 (dd, J = 16.7, 1.9 Hz, 1H), 5.80 (dd, J = 10.6, 2.0 Hz, 1H), 4.86-4.37 (m, 4H), 4.24 (d, J = 13.5 Hz, 2H), 3.50-3.36 (m, 3H), 3.30-3.18 (m, 1H), 2.08-1.75 (m, 5H), 1.70-1.37 (m, 6H). | 731.1 |
| 2084 | 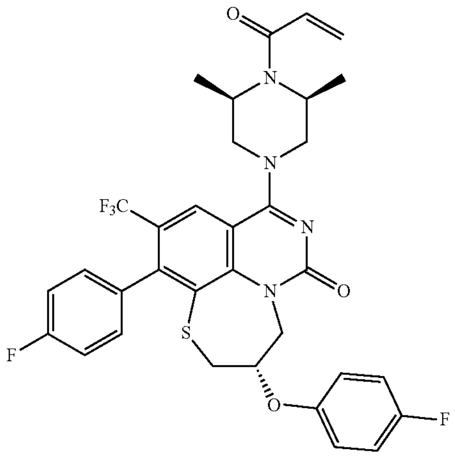 [SMILES: C=CC(=O)N1[C@H](C)CN(c2nc(=O)n3c4c(c(-c5ccc(F)cc5)c(C(F)(F)F)cc24)SC[C@@H](Oc2ccc(F)cc2)C3)C[C@@H]1C] | (S)-8-((3S,5R)-4-acryloyl-3,5-dimethylpiperazin-1-yl)-3-(4-fluorophenoxy)-11-(4-fluorophenyl)-10-(trifluoromethyl)-3,4-dihydro-2H,6H-[1,4]thiazepino[2,3,4-ij]quinazolin-6-one | $^1$H NMR (400 MHz, $CDCl_3$) δ 8.09 (s, 1H), 7.26-7.24 (m, 1H), 7.20-7.16 (m, 3H), 7.00-6.93 (m, 4H), 6.66-6.60 (m, 1H), 6.42 (dd, J = 16.4 Hz, 1.6 Hz, 1H), 5.78 (dd, J = 10.4 Hz, 2.0 Hz, 1H), 4.96-4.60 (m, 5H), 4.18 (d, J = 13.2 Hz, 2H), 3.43-3.35 (m, 3H), 3.17-3.13 (m, 1H), 1.55 (d, J = 6.8 Hz, 3H), 1.53 (d, J = 6.4 Hz, 3H). | 657.2 |

TABLE 12-continued

| Summary of Compounds 2000 to 2109 | | | | |
|---|---|---|---|---|
| Ex.# | Structure | Name | $^1$H NMR | MS + 1 |
| 2085 | 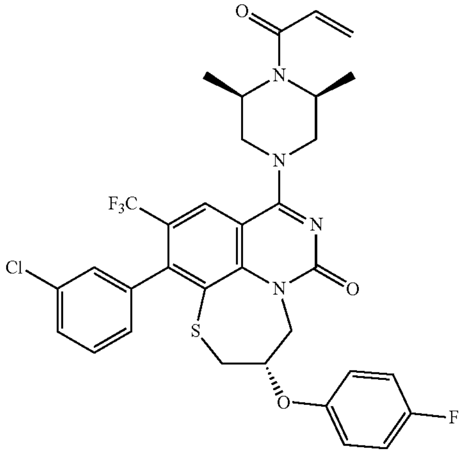 [SMILES: C=CC(=O)N1[C@H](C)CN(c2nc(=O)n3c4c(c(-c5cccc(Cl)c5)c(C(F)(F)F)cc24)SC[C@@H](Oc2ccc(F)cc2)C3)C[C@@H]1C] | (S)-8-((3R,5S)-4-acryloyl-3,5-dimethylpiperazin-1-yl)-11-(3-chlorophenyl)-3-(4-fluorophenoxy)-10-(trifluoromethyl)-3,4-dihydro-2H,6H-[1,4]thiazepino[2,3,4-ij]quinazolin-6-one | $^1$H NMR (400 MHz, $CDCl_3$) δ 8.09 (s, 1H), 7.48-7.43 (m, 2H), 7.28-7.26 (m, 1H), 7.18-7.10 (m, 1H), 6.99-6.94 (m, 4H), 6.66-6.59 (m, 1H), 6.42 (dd, J = 15.6 Hz, 1.6 Hz, 1H), 5.78 (dd, J = 10.4 Hz, 2.0 Hz, 1H), 4.96-4.6 (m, 5H), 4.18 (d, J = 13.2 Hz, 2H), 3.42-3.35 (m, 3H), 3.19-3.15 (m, 1H), 1.54-1.53 (m, 6H). | 673.1 |
| 2086 | 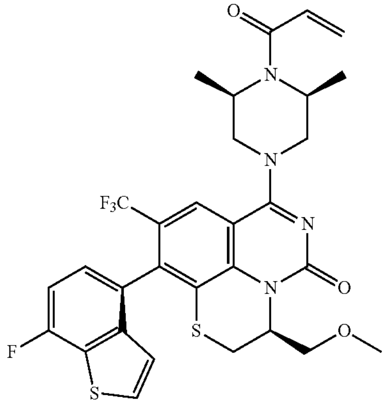 | (3S)-7-((3S,5R)-4-acryloyl-3,5-dimethylpiperazin-1-yl)-10-(7-fluorobenzo[b]thiophen-4-yl)-3-(methoxymethyl)-9-(trifluoromethyl)-2,3-dihydro-5H-[1,4]thiazepino[2,3,4-ij]quinazolin-5-one | $^1$H NMR (400 MHz, $CDCl_3$) δ 8.12 (s, 1H), 7.48 (d, J = 5.6 Hz, 1H), 7.18 (d, J = 7.2 Hz, 2H), 6.79-6.77 (m, 1H), 6.66-6.60 (m, 1H), 6.41 (dd, J = 1.6 Hz, 16.8 Hz, 1H), 5.78 (dd, J = 2.0 Hz, 10.4 Hz, 1H), 5.47-5.42 (m, 1H), 4.87-4.46 (m, 2H), 4.24-4.21 (m, 2H), 3.64-3.57 (m, 2H), 3.43-3.33 (m, 5H), 3.23 (dd, J = 2.8 Hz, 13.6 Hz, 1H), 2.97 (dd, J = 3.2 Hz, 13.6 Hz, 1H), 1.64 (d, J = 6.8 Hz, 3H), 1.48 (d, J = 7.2 Hz, 3H). | 633.2 |
| 2087 | 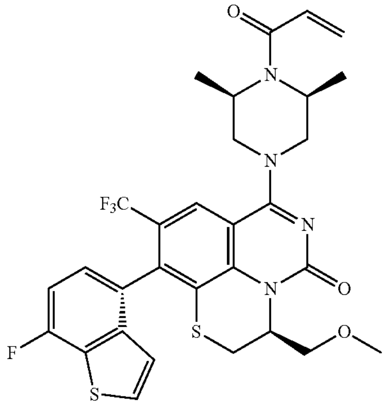 | (3S,10S)-7-((3S,5R)-4-acryloyl-3,5-dimethylpiperazin-1-yl)-10-(7-fluorobenzo[b]thiophen-4-yl)-3-(methoxymethyl)-9-(trifluoromethyl)-2,3-dihydro-5H-[1,4]thiazino[2,3,4-ij]quinazolin-5-one | $^1$H NMR (400 MHz, $CDCl_3$) δ 8.12 (s, 1H), 7.48 (d, J = 5.6 Hz, 1H), 7.18-7,16 (m, 2H), 6.80-6.77 (m, 1H), 6.66-6.60 (m, 1H), 6.41 (dd, J = 2.0 Hz, 16.8 Hz, 1H), 5.78 (dd, J = 2.0 Hz, 10.4 Hz, 1H), 5.47-5.39 (m, 1H), 4.89-4.49 (m, 2H), 4.22-4.19 (m, 2H), 3.69-3.6 (m, 2H), 3.44-3.34 (m, 5H), 3.24 (dd, J = 3.2 Hz, 13.2 Hz, | |

TABLE 12-continued

Summary of Compounds 2000 to 2109

| Ex.# | Structure | Name | $^1$H NMR | MS + 1 |
| --- | --- | --- | --- | --- |
| | | | 1H), 2.92 (dd, J = 2.4 Hz, 13.6 Hz, 1H), 1.63 (d, J = 7.2 Hz, 3H), 1.49 (d, J = 6.8 Hz, 3H). | |
| 2088 | 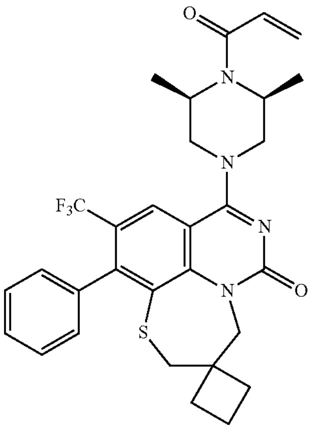 [SMILES: C=CC(=O)N1[C@H](C)CN(c2nc(=O)n3c4c(c(-c5ccccc5)c(C(F)(F)F)cc24)SCC2(CCC2)C3)C[C@@H]1C] | 8'-((3S,5R)-4-acryloyl-3,5-dimethylpiperazin-1-yl)-11'-phenyl-10'-(trifluoromethyl)-2,'H,4'H,6'H-spiro[cyclobutane-1,3'-[1,4]thiazepino[2,3,4-ij]quinazolin]-6'-one | $^1$H NMR (400 MHz, MeOH-$d_4$) δ 8.11 (s, 1H), 7.52-7.41 (m, 3H), 7.33-7.14 (m, 2H), 6.84 (dd, J = 16.7, 10.6 Hz, 1H), 6.29 (dd, J = 16.7, 1.9 Hz, 1H), 5.80 (dd, J = 10.7, 1.9 Hz, 1H), 4.86-4.4 (m, 4H), 4.25 (d, J = 13.5 Hz, 2H), 3.39 (dd, J = 13.8, 4.6 Hz, 2H), 3.27-3.00 (m, 2H), 2.09-1.72 (m, 5H), 1.67-1.36 (m, 6H). | 569.3 |
| 2089 | 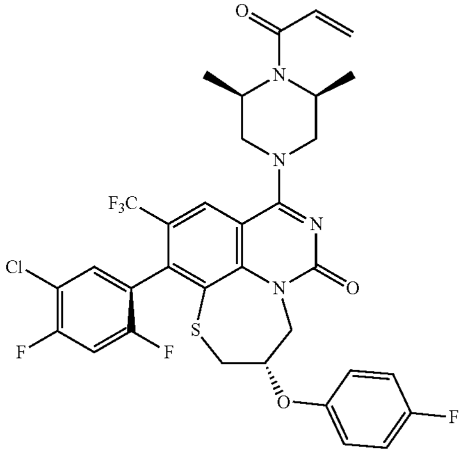 | (3S,11R)-8-((3S,5R)-4-acryloyl-3,5-dimethylpiperazin-1-yl)-11-(5-chloro-2,4-difluorophenyl)-3-(4-fluorophenoxy)-10-(trifluoromethyl)-3,4-dihydro-2H,6H-[1,4]thiazepino[2,3,4-ij]quinazolin-6-one | $^1$H NMR (400 MHz, $CDCl_3$) δ 8.10 (s, 1H), 7.31-7.27 (m, 1H), 7.06-7.01 (m, 1H), 7.04-6.94 (m 4H), 6.66-6.59 (dd, J = 16.4 Hz, 10.4 Hz, 1H), 6.44-6.39 (dd, J = 16.4 Hz, 2.0 Hz, 1H), 5.80-5.77 (dd, J = 10.4 Hz, 1.6 Hz, 1H), 5.00-4.63 (m, 5H), 4.17 (d, J = 13.2 Hz, 2H), 3.52 (d, J = 15.6 Hz, 1H), 3.43-3.36 (m, 2H), 3.22 (d, J = 16.0 Hz, 1H), 1.56-1.52 (m, 6H). | 709.2 |

TABLE 12-continued

| Ex.# | Structure | Name | $^1H$ NMR | MS + 1 |
|---|---|---|---|---|
| Summary of Compounds 2000 to 2109 | | | | |
| 2090 | 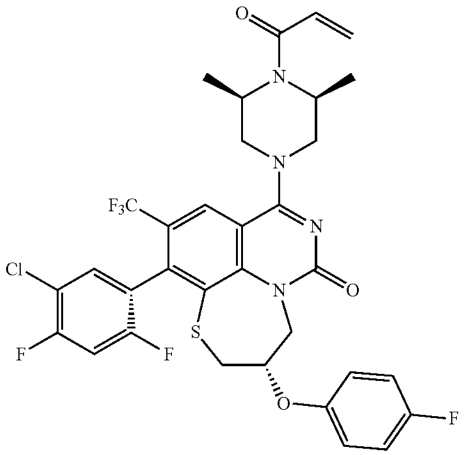 | (3S)-8-((3S,5R)-4-acryloyl-3,5-dimethylpiperazin-1-yl)-11-(5-chloro-2,4-difluorophenyl)-3-(4-fluorophenoxy)-10-(trifluoromethyl)-3,4-dihydro-2H,6H-[1,4]thiazepino[2,3,4-ij]quinazolin-6-one | $^1H$ NMR (400 MHz, $CDCl_3$) δ 8.11 (s, 1H), 7.26-7.23 (m, 1H), 7.09-7.05 (t, J = 8.8 Hz 1H), 6.99-6.97 (m, 4H), 6.66-6.59 (dd, J = 16.8 Hz, 10.8 1H), 6.43-6.39 (dd, J = 16.8 Hz, 1.6 Hz, 1H), 5.80-5.77 (dd, J = 10.4 Hz, 1.6 Hz, 1H), 5.09-4.34 (m, 5H), 4.17 (d, J = 13.2 Hz, 2H), 3.43-3.36 (m, 3H), 3.26-3.18 (m, 1H), 1.56-1.52 (m, 6H). | 709.2 |
| 2091 | 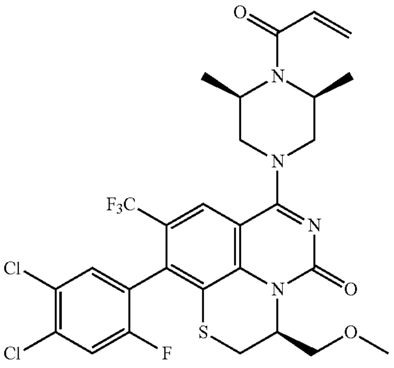 | (3S)-7-((3S,5R)-4-acryloyl-3,5-dimethylpiperazin-1-yl)-10-(4,5-dichloro-2-fluorophenyl)-3-(methoxymethyl)-9-(trifluoromethyl)-2,3-dihydro-5H-[1,4]thiazino[2,3,4-ij]quinazolin-5-one | $^1H$ NMR (400 MHz, $CDCl_3$) δ 8.06 (s, 1H), 7.36 (dd, J = 1.6 Hz, 8.4 Hz, 1H), 7.30 (d, J = 6.8 Hz, 1H), 6.65-6.59 (m, 1H), 6.41 (dd, J = 1.6 Hz, 16.8 Hz, 1H), 5.77 (dd, J = 1.6 Hz, 10.4 Hz, 1H), 5.46-5.42 (m, 1H), 4.72-4.57 (m, 2H), 4.18 (t, J = 11.2 Hz, 2H), 3.66-3.61 (m, 2H), 3.41-3.30 (m, 6H), 3.05-3.00 (m, 1H), 1.61 (d, J = 7.2 Hz, 3H), 1.48-1.45 (m, 3H). | 645.1 |
| 2092 | 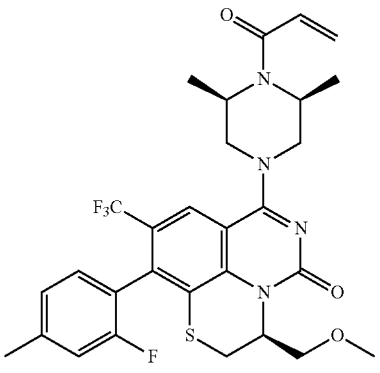 | (3S)-7-((3S,5R)-4-acryloyl-3,5-dimethylpiperazin-1-yl)-10-(2-fluoro-4-methylphenyl)-3-(methoxymethyl)-9-(trifluoromethyl)-2,3-dihydro-5H-[1,4]thiazino[2,3,4-ij]quinazolin-5-one | $^1H$ NMR (400 MHz, MeOH-$d_4$) δ 8.13 (s, 1H), 7.18-7.02 (m, 3H), 6.84 (dd, J = 16.7, 10.6 Hz, 1H), 6.29 (dd, J = 16.7, 1.9 Hz, 1H), 5.80 (dd, J = 10.6, 2.0 Hz, 1H), 5.42-5.28 (m, 1H), 4.87-4.46 (br s, 2H), 4.33 (dd, J = 13.7, 5.6 Hz, 1H), 4.25 (d, J = 13.6 Hz, 1H), 3.71 (td, J = 9.2, 5.6 Hz, 1H), 3.59 (dt, J = 9.6, 5.1 Hz, 1H), 3.47 (ddd, J = 13.4, 8.5, 4.7 Hz, 1H), 3.42-3.33 (m, 1H), | 591.3 |

TABLE 12-continued

| Summary of Compounds 2000 to 2109 | | | | |
|---|---|---|---|---|
| Ex.# | Structure | Name | $^1$H NMR | MS + 1 |
| | | | 3.39 (s, 3H), 3.13 (dt, J = 13.7, 3.2 Hz, 1H), 2.45 (s, 3H), 1.58 (dd, J = 7.1, 3.4 Hz, 3H), 1.42 (d, J = 6.9 Hz, 3H). | |
| 2093 | 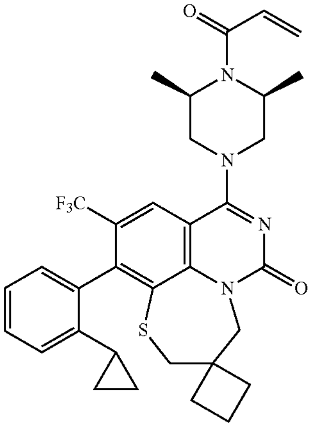 [SMILES: C=CC(=O)N1[C@H](C)CN(c2nc(=O)n3c4c(c(-c5ccccc5C5CC5)c(C(F)(F)F)cc24)SCC2(CCC2)C3)C[C@@H]1C] | 8'-((3S,5R)-4-acryloyl-3,5-dimethylpiperazin-1-yl)-11'-(2-cyclopropylphenyl)-10'-(trifluoromethyl)-2'H,4'H,6'H-spiro[cyclobutane-1,3-[1,4]thiazepino[2,3,4-ij]quinazolin]-6'-one | $^1$H NMR (400 MHz, MeOH-$d_4$) δ 8.14 (s, 1H), 7.35 (t, J = 6.6 Hz, 1H), 7.22 (t, J = 7.5 Hz, 1H), 7.04 (d, J = 7.6 Hz, 1H), 6.95 (d, J = 7.9 Hz, 1H), 6.84 (dd, J = 16.7, 10.6 Hz, 1H), 6.29 (dd, J = 16.7, 2.0 Hz, 1H), 5.80 (dd, J = 10.6, 2.0 Hz, 1H), 4.85-4.38 (m, 5H), 4.35-4.13 (m, 2H), 3.39 (dd, J = 13.7, 4.6 Hz, 2H), 3.27-3.0 (m, 2H), 2.18-1.72 (m, 5H), 1.68-1.32 (m, 6H), 0.89-0.62 (m, 4H). | 609.3 |
| 2094 | 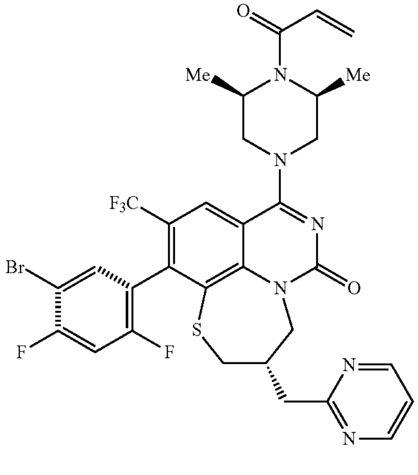 | (3S,11S)-8-((3S,5R)-4-acryloyl-3,5-dimethylpiperazin-1-yl)-11-(5-bromo-2,4-difluorophenyl)-3-(pyrimidin-2-yloxy)-10-(trifluoromethyl)-3,4-dihydro-2H,6H-[1,4]thiazepino[2,3,4-ij]quinazolin-6-one | $^1$H NMR (400 MHz, CDCl3) δ 8.54 (d, J = 4.8 Hz, 2H), 8.10 (s, 1H), 7.46 (t, J = 7.2 Hz, 1H), 7.07-6.96 (m, 2H), 6.64 (dd, J = 10.4, 16.8 Hz, 1H), 6.48-6.38 (m, 1H), 5.86-5.68 (m, 2H), 5.18-4.42 (m, 4H), 4.21-4.14 (m, 2H), 3.61-3.34 (m, 4H), 1.56-1.53 (m, 6H) | 739.2 |

TABLE 12-continued

Summary of Compounds 2000 to 2109

| Ex.# | Structure | Name | $^1$H NMR | MS + 1 |
|---|---|---|---|---|
| 2095 | 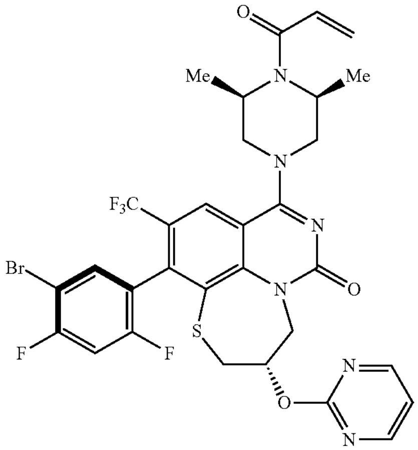 | (3S,11R)-8-((3S,5R)-4-acryloyl-3,5-dimethylpiperazin-1-yl)-11-(5-bromo-2,4-difluorophenyl)-3-(pyrimidin-2-yloxy)-10-(trifluoromethyl)-3,4-dihydro-2H,6H-[1,4]thiazepino[2,3,4-ij]quinazolin-6-one | 1H NMR (400 MHz, CDCl3) δ 8.54 (d, J = 4.8 Hz, 2H), 8.10 (s, 1H), 7.49-7.30 (m, 1H), 7.05 (t, J = 8.4 Hz, 1H), 6.99 (t, J = 4.8 Hz, 1H), 6.69-6.57 (m, 1H), 6.42 (dd, J = 2.0, 16.8 Hz, 1H), 5.84-5.58 (m, 2H), 5.18-4.42 (m, 4H), 4.23-4.09 (m, 2H), 3.67-3.25 (m, 4H), 1.57-1.48 (m, 6H) | 739.2 |
| 2096 | 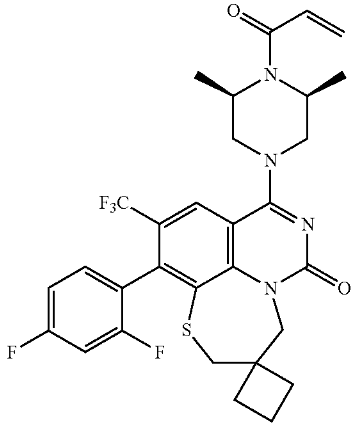 [SMILES: C=CC(=O)N1[C@H](C)CN(c2nc(=O)n3c4c(c(-c5ccc(F)cc5F)c(C(F)(F)F)cc24)SCC2(CCC2)C3)C[C@@H]1C] | 8'-((3S,5R)-4-acryloyl-3,5-dimethylpiperazin-1-yl)-11'-(2,4-difluorophenyl)-10'-(trifluoromethyl)-2'H,4'H,6'H-spiro[cyclobutane-1,3'-[1,4]thiazepino[2,3,4-ij]quinazolin]-6'-one | $^1$H NMR (400 MHz, MeOH-$d_4$) δ 8.13 (s, 1H), 7.39-7.23 (m, 1H), 7.18-7.04 (m, 2H), 6.84 (dd, J = 16.7, 10.6 Hz, 1H), 6.29 (dd, J = 16.7, 2.1 Hz, 1H), 5.80 (dd, J = 10.5, 2.1 Hz, 1H), 4.87-4.37 (m, 4H), 4.24 (d, J = 13.5 Hz, 2H), 3.50-3.33 (m, 3H), 3.29-3.14 (m, 1H), 2.15-1.74 (m, 6H), 1.69-1.35 (m, 6H). | 605.2 |
| 2097 | 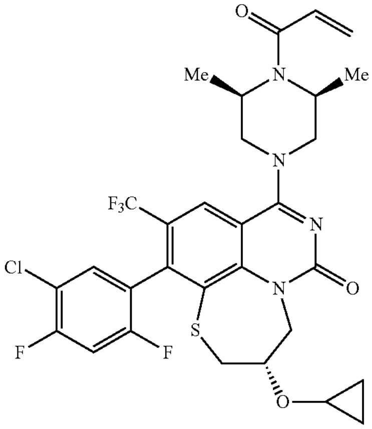 [SMILES: C=CC(=O)N1[C@H](C)CN(c2nc(=O)n3c4c(c(-c5cc(Cl)c(F)cc5F)c(C(F)(F)F)cc24)SC[C@@H](OC2CC2)C3)C[C@@H]1C] | (3S)-7-((3S,5R)-4-acryloyl-3,5-dimethylpiperazin-1-yl)-10-(4,5-dichloro-2-fluorophenyl)-3-(methoxymethyl)-9-(trfluoromethyl)-2,3-dihydro-5H-[1,4]thiazino[2,3,4-ij]quinazolin-5-one | $^1$H NMR (400 MHz, CDCl3) δ ppm 0.48-0.74 (m, 4H) 1.55 (br s, 6H) 3.17 (br d, J = 15.0 Hz, 1H) 3.21-3.65 (m, 4H) 4.00-4.54 (m, 4H) 4.56-4.90 (m, 3H) 5.79 (dd, J = 10.4, 2.0 Hz, 1H) 6.42 (dd, J = 16.8, 2.0 Hz, 1H) 6.63 (dd, J = 16.8, 10.4 Hz, 1H) 7.05 (t, J = 8.8 Hz, 1H) 7.26 (br s, 1H) 8.08 (s, 1H) | 655.2 |

TABLE 12-continued

Summary of Compounds 2000 to 2109

| Ex.# | Structure | Name | $^1$H NMR | MS + 1 |
|---|---|---|---|---|
| 2098 | 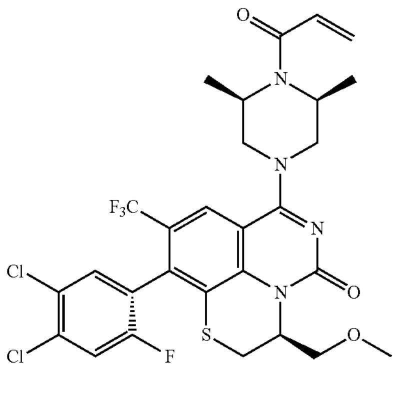 | (3S,10R)-7-((3S,5R)-4-acryloyl-3,5-dimethylpiperazin-1-yl)-10-(4,5-dichloro-2-fluorophenyl)-3-(methoxymethyl)-9-(trifluoromethyl)-2,3-dihydro-5H-[1,4]thiazino[2,3,4-ij]quinazolin-5-one | $^1$H NMR (400 MHz, $CDCl_3$) δ 8.06 (s, 1H), 7.36 (d, J = 8.4 Hz, 1H),7.31 (d, J = 6.8 Hz, 1H), 6.66-6.59 (m, 1H), 6.41 (dd, J = 2.0 Hz, 16.8 Hz, 1H), 5.77 (dd, J = 1.6 Hz, 10.4 Hz, 1H), 5.47-5.42 (m, 1H), 4.76-4.53 (m, 2H), 4.21-4.15 (m, 2H), 3.66-3.64 (m, 2H), 3.41-3.30 (m, 6H), 3.05-3.01 (m, 1H), 1.61 (d, J = 6.8 Hz, 3H), 1.48 (d, J = 7.2 Hz, 3H). | 645.1 |
| 2099 | 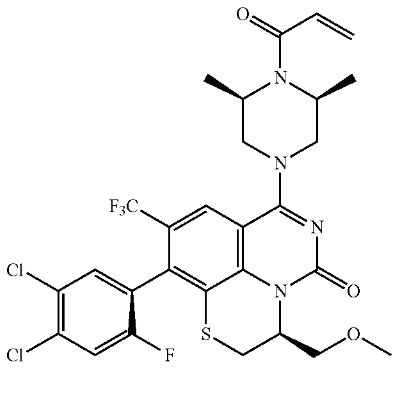 | (3S,10S)-7-((3S,5R)-4-acryloyl-3,5-dimethylpiperazin-1-yl)-10-(4,5-dichloro-2-fluorophenyl)-3-(methoxymethyl)-9-(trifluoromethyl)-2,3-dihydro-5H-[1,4]thiazino[2,3,4-ij]quinazolin-5-one | $^1$H NMR (400 MHz, $CDCl_3$) δ 8.07 (s, 1H), 7.36 (d, J = 8.0 Hz, 1H),7.30 (d, J = 6.8 Hz, 1H), 6.66-6.59 (m, 1H), 6.41 (dd, J = 2.0 Hz, 17.2 Hz, 1H), 5.78 (dd, J = 2.0 Hz, 10.4 Hz, 1H), 5.48-5.44 (m, 1H), 4.71-4.62 (m, 2H), 4.21-4.16 (m, 2H), 3.67-3.62 (m, 2H), 3.39-3.30 (m, 6H), 3.04-3.00 (m, 1H), 1.61 (d, J = 6.8 Hz, 3H), 1.46 (d, J = 6.8 Hz, 3H). | 645.1 |
| 2100 | 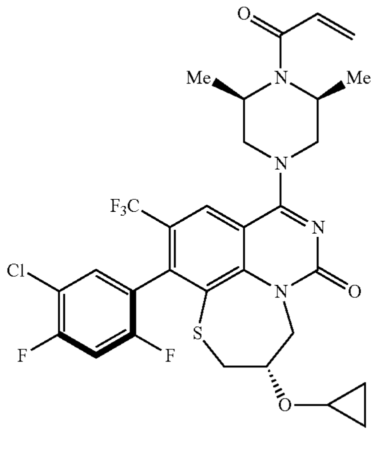 | (3S,11S)-7-((3S,5R)-4-acryloyl-3,5-dimethylpiperazin-1-yl)-10-(4,5-dichloro-2-fluorophenyl)-3-(methoxymethyl)-9-(trifluoromethyl)-2,3-dihydro-5H-[1,4]thiazino[2,3,4-ij]quinazolin-5-one | $^1$H NMR (400 MHz, CDCl3) δ ppm 0.52-0.71 (m, 4H) 1.48-1.58 (m, 6H) 3.17 (br d, J = 14.8 Hz, 1H) 3.26-3.55 (m, 4H) 4.08-4.46 (m, 4H) 4.54-4.87 (m, 3H) 5.79 (dd, J = 10.4, 2.0 Hz, 1H) 6.42 (dd, J = 16.8, 2.0 Hz, 1H) 6.63 (dd, J = 16.8, 10.4 Hz, 1H) H) 7.05 (t, J = 8.8 Hz, 1H) 7.29 (br s, 1H) 8.07 (s, 1H) | 655.2 |

TABLE 12-continued

| Summary of Compounds 2000 to 2109 | | | | |
|---|---|---|---|---|
| Ex.# | Structure | Name | $^1$H NMR | MS + 1 |
| 2101 | 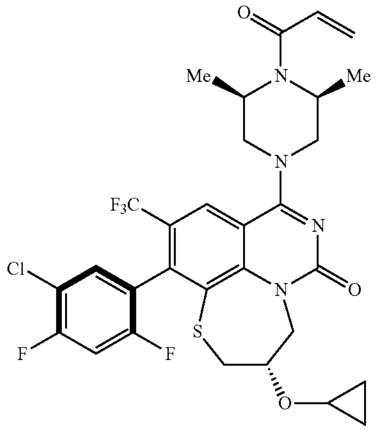 | (3S)-8-((3S,5R)-4-Acryloyl-3,5-dimethylpiperazin-1-yl)-11-(5-chloro-2,4-difluorophenyl)-3-cyclopropoxy-10-(trifluoromethyl)-3,4-dihydro-2H,6H-[1,4]thiazepino[2,3,4-ij]quinazolin-6-one | $^1$H NMR (400 MHz, CDCl3) δ ppm 0.51-0.77 (m, 4H) 1.55 (br s, 6H) 3.10-3.59 (m, 5H) 3.97-4.52 (m, 4H) 4.55-4.97 (m, 3H) 5.72-5.87 (m, 1H) 6.42 (dd, J = 16.8, 2.0 Hz, 1H) 6.63 (dd, J = 16.8, 10.4 Hz, 1H) 7.06 (t, J = 8.8 Hz, 1H) 7.22-7.27 (m, 1H) 8.08 (s, 1H) H) | 655.2 |
| 2102 | 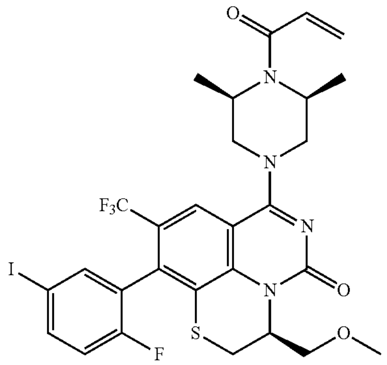 [SMILES: C=CC(=O)N1[C@H](C)CN(c2nc(=O)n3c4c(c(-c5cc(I)ccc5F)c(C(F)(F)F)cc24)SC[C@@H]3COC)C[C@@H]1C] | (3S)-7-((3S,5R)-4-acryloyl-3,5-dimethylpiperazin-1-yl)-10-(2-fluoro-5-iodophenyl)-3-(methoxymethyl)-9-(trifluoromethyl)-2,3-dihydro-5H-[1,4]thiazino[2,3,4-ij]quinazolin-5-one | 1H NMR (400 MHz, MeOH-$d_4$) δ 8.14 (s, 1H), 7.93-7.83 (m, 1H), 7.61 (ddd, J = 16.3, 6.7, 2.2 Hz, 1H), 7.09 (td, J = 9.0, 4.1 Hz, 1H), 6.84 (dd, J = 16.7, 10.6 Hz, 1H), 6.29 (dd, J = 16.7, 1.9 Hz, 1H), 5.80 (dd, J = 10.6, 1.9 Hz, 1H), 5.43-5.27 (m, 1H), 4.87-4.46 (br s, 2H), 4.42-4.30 (m, 1H), 4.26 (d, J = 13.6 Hz, 1H), 3.72 (dt, J = 20.7, 9.2 Hz, 1H), 3.61 (td, J = 9.5, 4.8 Hz, 1H), 3.49 (ddd, J = 13.4, 11.3, 4.7 Hz, 1H), 3.45-3.33 (m, 2H), 3.40 (d, J = 8.1 Hz, 4H), 3.15 (ddd, J = 13.7, 8.3, 3.0 Hz, 1H), 1.57 (dd, J = 7.0, 3.3 Hz, 3H), 1.42 (d, J = 6.9 Hz, 3H). | 703.0 |

TABLE 12-continued

| Ex.# | Structure | Name | $^1$H NMR | MS + 1 |
|---|---|---|---|---|
| Summary of Compounds 2000 to 2109 | | | | |
| 2103 | 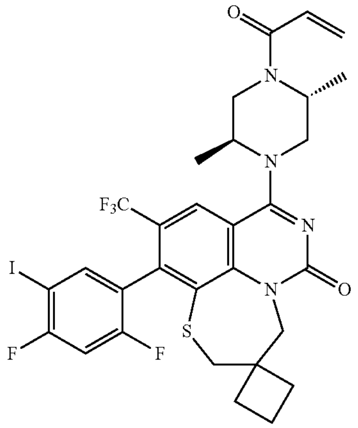 [SMILES: C=CC(=O)N1C[C@H](C)N(c2nc(=O)n3c4c(c(-c5cc(I)c(F)cc5F)c(C(F)(F)F)cc24)SCC2(CCC2)C3)C[C@H]1C] | 8'-((2S,5R)-4-acryloyl-2,5-dimethylpiperazin-1-yl)-11'-(2,4-difluoro-5-iodophenyl)-10'-(trifluoromethyl)-2'H,4'H,6'H-spiro[cyclobutane-1,3'-[1,4]thiazepino[2,3,4-ij]quinazolin]-6'-one | $^1$H NMR (400 MHz, MeOH-$d_4$) δ 7.92 (s, 1H), 7.83-7.63 (m, 1H), 7.21 (td, J = 8.8, 3.5 Hz, 1H), 6.93-6.70 (m, 1H), 6.28 (dd, J = 16.8, 5.5 Hz, 1H), 5.89-5.74 (m, 1H), 4.87-4.03 (m, 5H), 3.97-3.64 (m, 2H), 3.49-3.33 (m, 1H), 3.29-3.10 (m, 1H), 2.16-1.74 (m, 6H), 1.61-1.13 (m, 6H). | 731.1 |
| 2104 | 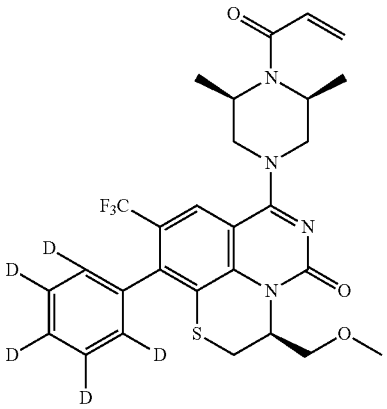 [SMILES: [2H]c1c([2H])c([2H])c(-c2c(C(F)(F)F)cc3c(N4C[C@@H](C)N(C(=O)C=C)[C@@H](C)C4)nc(=O)n4c3c2SC[C@@H]4COC)c([2H])c1[2H]] | (S)-7-((3S,5R)-4-acryloyl-3,5-dimethylpiperazin-1-yl)-3-(methoxymethyl)-10-(phenyl-$d_5$)-9-(trifluoromethyl)-2,3-dihydro-5H-[1,4]thiazino[2,3,4-ij]quinazolin-5-one | $^1$H NMR (400 MHz, MeOH-$d_4$) δ 8.13 (s, 1H), 6.84 (dd, J = 16.6, 10.6 Hz, 1H), 6.29 (dd, J = 16.7, 1.9 Hz, 1H), 5.80 (dd, J = 10.6, 1.9 Hz, 1H), 5.40-5.27 (m, 1H), 4.85-4.47 (br s, 2H), 4.34 (d, J = 13.7 Hz, 1H), 4.26 (d, J = 13.5 Hz, 1H), 3.73 (t, J = 9.2 Hz, 1H), 3.60 (dd, J = 9.2, 4.7 Hz, 1H), 3.47 (dd, J = 13.5, 4.7 Hz, 1H), 3.42-3.34 (m, 1H), 3.39 (s, 3H), 3.28 (d, J = 3.1 Hz, 1H), 3.08 (dd, J = 13.7, 2.9 Hz, 1H), 1.58 (d, J = 6.9 Hz, 3H), 1.42 (d, J = 6.9 Hz, 3H). | 564.2 |
| 2105 | 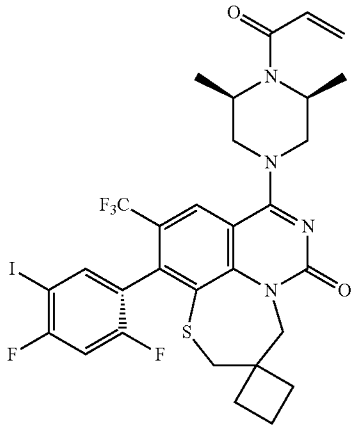 | (S)-8'-((3S,5R)-4-acryloyl-3,5-dimethylpiperazin-1-yl)-11'-(2,4-difluoro-5-iodophenyl)-10'-(trifluoromethyl)-2'H,4'H,6'H-spiro[cyclobutane-1,3'-[1,4]thiazepino[2,3,4-ij]quinazolin]-6'-one | $^1$H NMR (400 MHz, MeOH-$d_4$) δ 8.12 (s, 1H), 7.82-7.67 (m, 1H), 7.21 (t, J = 8.7 Hz, 1H), 6.84 (dd, J = 16.7, 10.6 Hz, 1H), 6.29 (dd, J = 16.7, 2.0 Hz, 1H), 5.80 (dd, J = 10.6, 2.0 Hz, 1H), 4.88-4.38 (m, 4H), 4.24 (d, J = 13.5 Hz, 2H), 3.51-3.34 (m, 3H), 3.29-3.13 (m, 1H), 2.15-1.70 (m, 6H), 1.68-1.39 (m, 6H). | 731.1 |

TABLE 12-continued

| Summary of Compounds 2000 to 2109 | | | | |
|---|---|---|---|---|
| Ex.# | Structure | Name | $^1$H NMR | MS + 1 |
| 2105 | 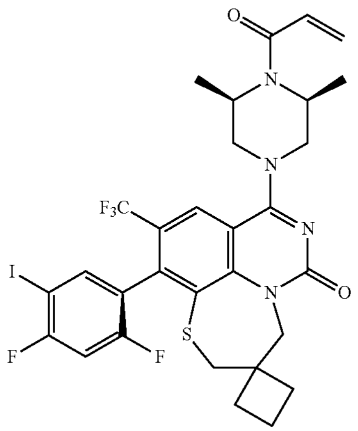 | (R)-8'-((3S,5R)-4-acryloyl-3,5-dimethylpiperazin-1-yl)-11'-(2,4-difluoro-5-iodophenyl)-10'-(trifluoromethyl)-2'H,4'H,6'H-spiro[cyclobutane-1,3'-[1,4]thiazepino[2,3,4-ij]quinazolin]-6'-one | $^1$H NMR (400 MHz, MeOH-$d_4$) δ 8.12 (s, 1H), 7.82-7.67 (m, 1H), 7.21 (t, J = 8.7 Hz, 1H), 6.84 (dd, J = 16.7, 10.6 Hz, 1H), 6.29 (dd, J = 16.7, 2.0 Hz, 1H), 5.80 (dd, J = 10.5, 2.0 Hz, 1H), 4.88-4.38 (m, 4H), 4.24 (d, J = 13.5 Hz, 2H), 3.49-3.33 (m, 3H), 3.29-3.13 (m, 1H), 2.13-1.73 (m, 6H), 1.69-1.38 (m, 6H). | 731.1 |
| 2106 | 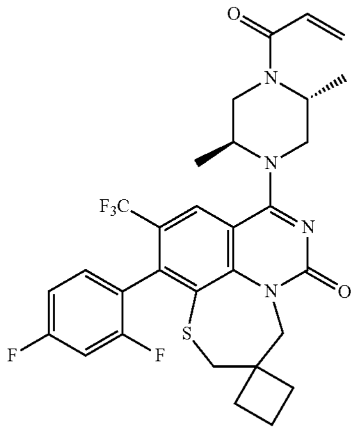 [SMILES: C=CC(=O)N1C[C@H](C)N(c2nc(=O)n3c4c(c(-c5ccc(F)cc5F)c(C(F)(F)F)cc24)SCC2(CCC2)C3)C[C@H]1C] | 8'-((2S,5R)-4-acryloyl-2,5-dimethylpiperazin-1-yl)-11'-(2,4-difluorophenyl)-10'-(trifluoromethyl)-2'H,4'H,6'H-spiro[cyclobutane-1,3-[1,4]thiazepino[2,3,4-ij]quinazolin]-6'-one | $^1$H NMR (400 MHz, MeOH-$d_4$) δ 7.93 (s, 1H), 7.40-7.23 (m, 1H), 7.18-7.04 (m, 2H), 6.93-6.70 (m, 1H), 6.28 (dd, J = 16.5, 6.0 Hz, 1H), 5.88-5.72 (m, 1H), 4.88-4.15 (m, 5H), 4.00-3.68 (m, 2H), 3.54-3.34 (m, 1H), 3.29-3.09 (m, 1H), 2.13-1.74 (m, 5H), 1.55-1.18 (m, 6H). | 605.2 |
| 2107 | 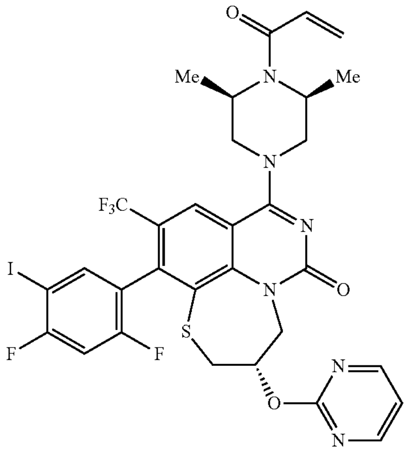 [SMILES: C=CC(=O)N1[C@H](C)CN(c2nc(=O)n3c4c(c(-c5cc(I)c(F)cc5F)c(C(F)(F)F)cc24)SC[C@@H](Oc2ncccn2)C3)C[C@@H]1C] | (3S)-8-((3S,5R)-4-acryloyl-3,5-dimethylpiperazin-1-yl)-11-(2,4-difluoro-5-iodophenyl)-3-(pyrimidin-2-yloxy)-10-(trifluoromethyl)-3,4-dihydro-2H,6H-[1,4]thiazepino[2,3,4-ij]quinazolin-6-one | 1H NMR (400 MHz, $CDCl_3$) δ = 8.52 (d, J = 4.0, 2H), 8.09 (s, 1H), 7.60-7.52 (m, 1H), 7.00-6.90 (m, 2H), 6.63 (dd, J = 16.4, 10.4, 1H), 6.40 (d, J = 16.0, 1H), 5.7 8 (d, J = 10.0, 1H), 5.75 (bs (1H), 4.92-4.50 (m, 4H), 4.19-4.15 (m, 2H), 3.60-3.25 (m, 4H), 1.58 (bs, 3H), 1.45 (bs, 3H). | 785.0 |

TABLE 12-continued

| Summary of Compounds 2000 to 2109 | | | | |
|---|---|---|---|---|
| Ex.# | Structure | Name | $^1$H NMR | MS + 1 |
| 2108 | 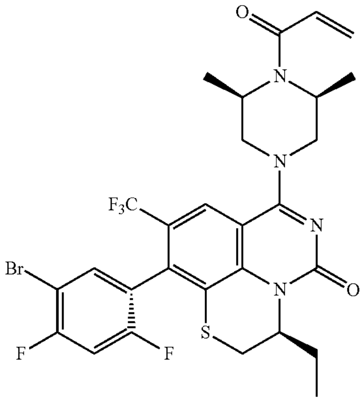 | (3S,10R)-7-((3S,5R)-4-acryloyl-3,5-dimethylpiperazin-1-yl)-10-(5-bromo-2,4-difluorophenyl)-3-ethyl-9-(trifluoromethyl)-2,3-dihydro-5H-[1,41thiazino[2,3,4-ijlquinazolin-5-one | $^1$H NMR (400 MHz, MeOH-$d_4$) δ 8.15 (s, 1H), 7.65 (t, J = 7.4 Hz, 1H), 7.34 (t, J = 8.9 Hz, 1H), 6.84 (dd, J = 16.7, 10.6 Hz, 1H), 6.29 (dd, J = 16.6, 1.9 Hz, 1H), 5.80 (dd, J = 10.7, 2.0 Hz, 1H), 5.18-5.05 (m, 1H), 4.86-4.52 (br s, 2H), 4.28 (dd, J = 23.1, 13.5 Hz, 2H), 3.44 (ddd, J = 24.4, 13.5, 4.6 Hz, 2H), 3.35-3.25 (m, 2H), 3.16 (dd, J = 13.9, 2.9 Hz, 1H), 1.57 (d, J = 6.7 Hz, 3H), 1.43 (d, J = 6.9 Hz, 3H). | 657.1 |
| 2109 | 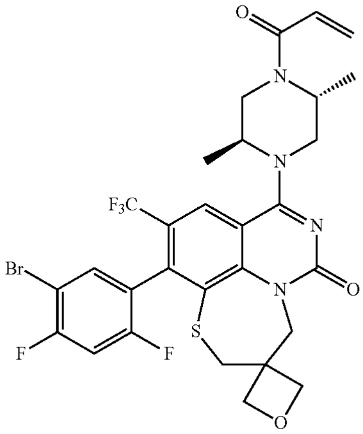 [SMILES: C=CC(=O)N1C[C@H](C)N(c2nc(=O)n3c4c(c(-c5cc(Br)c(F)cc5F)c(C(F)(F)F)cc24)SCC2(COC2)C3)C[C@H]1C] | 8'-((2S,5R)-4-acryloyl-2,5-dimethylpiperazin-1-yl)-11'-(5-bromo-2,4-difluorophenyl)-10'-(trifluoromethyl)-2'H,4'1,6'H-spiro[oxetane-3,3'-[1,4]thiazepino[2,3,4-ij]quinazolin]-6'-one | $^1$H NMR (400 MHz, MeOH-$d_4$) δ 7.96 (s, 1H), 7.71-7.51 (m, 1H), 7.31 (td, J = 9.0, 3.3 Hz, 1H), 6.91-6.70 (m, 1H), 6.35-6.20 (m, 1H), 5.87-5.72 (m, 1H), 4.88-4.56 (m, 4H), 4.55-4.37 (m, 3H), 4.36-4.01 (m, 2H), 4.00-3.35 (m, 5H), 1.43 (dd, J = 16.2, 6.5 Hz, 3H), 1.38-1.23 (m, 3H). | 685.0 |
| 2110 | 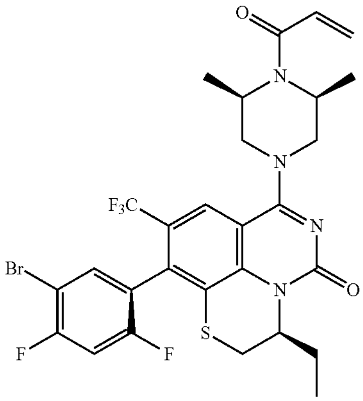 | (3S,10S)-7-((3S,5R)-4-acryloyl-3,5-dimethylpiperazin-1-yl)-10-(5-bromo-2,4-difluorophenyl)-3-ethyl-9-(trifluoromethyl)-2,3-dihydro-5H-[1,4]thiazepino[2,3,4-ij]quinazolin-5-one | 1H NMR (400 MHz, MeOH-$d_4$) δ 8.15 (s, 1H), 7.60 (t, J = 7.5 Hz, 1H), 7.35 (t, J = 8.9 Hz, 1H), 6.84 (dd, J = 16.7, 10.6 Hz, 1H), 6.29 (dd, J = 16.6, 2.0 Hz, 1H), 5.80 (dd, J = 10.6, 2.0 Hz, 1H), 5.20-5.06 (m, 1H), 4.86-4.53 (br s, 2H), 4.30 (dd, J = 31.5, 13.6 Hz, 2H), 3.46 (ddd, J = 32.4, 13.6, 4.7 Hz, 2H), 3.36-3.24 (m, 2H), 3.18 (dd, J = 13.9, 2.9 Hz, | 657.1 |

TABLE 12-continued
| Summary of Compounds 2000 to 2109 | | | | |
|---|---|---|---|---|
| Ex.# | Structure | Name | $^1$H NMR | MS + 1 |
| | | | 1H), 1.57 (d, J = 7.0 Hz, 3H), 1.42 (d, J = 6.9 Hz, 3H). | |
In certain embodiments, compounds of the various embodiments disclosed herein may be:
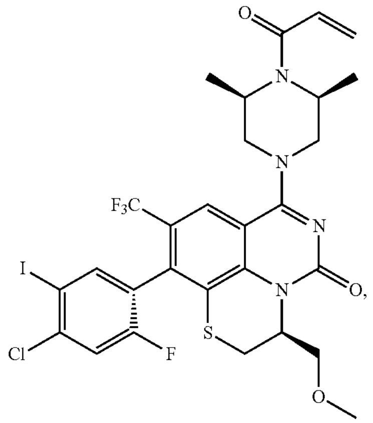
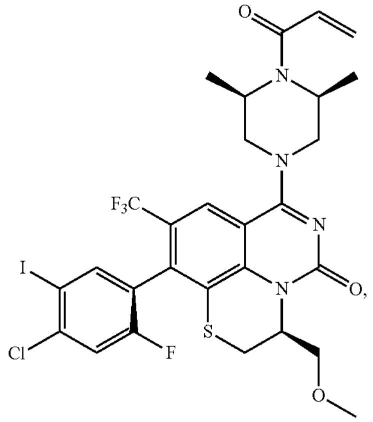
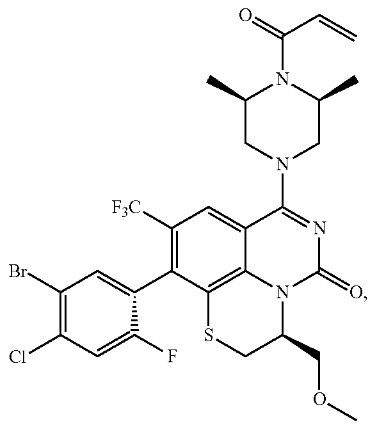
-continued
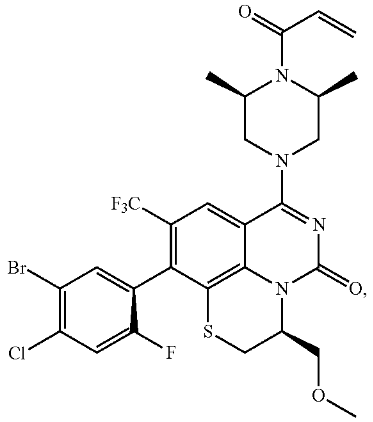
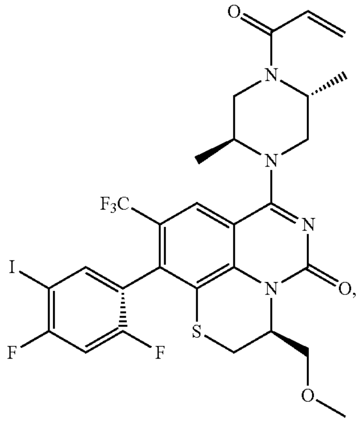
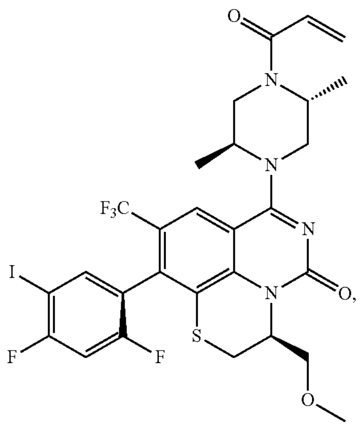

-continued
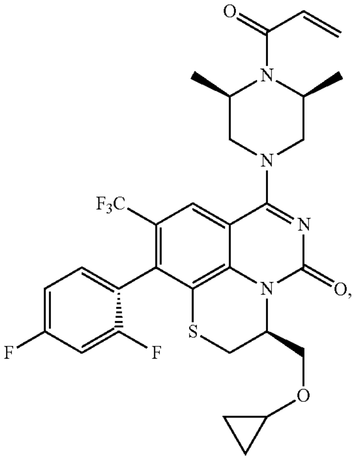
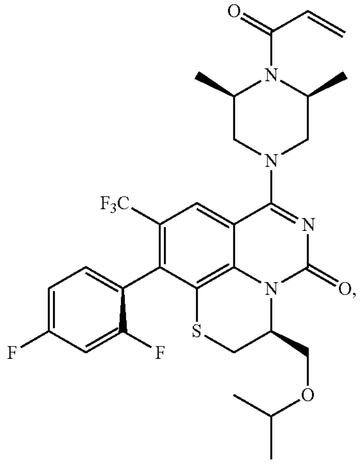
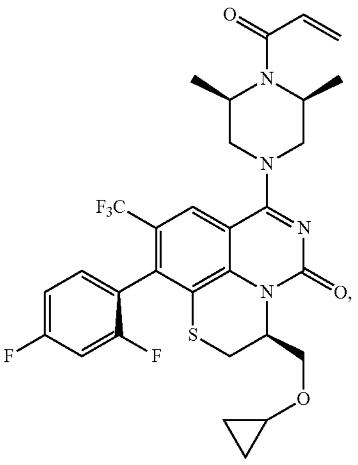
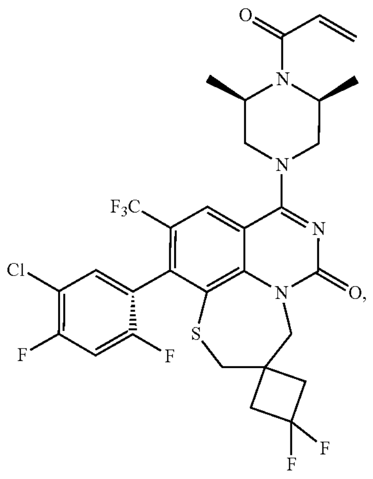
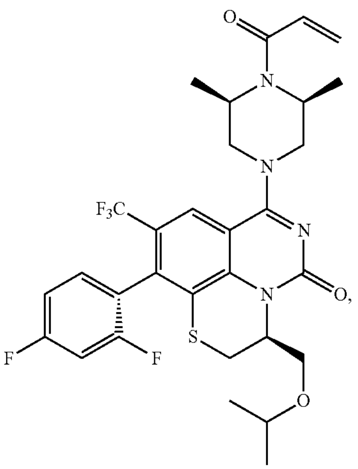
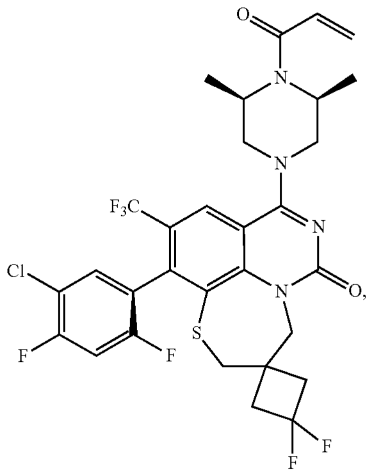

-continued
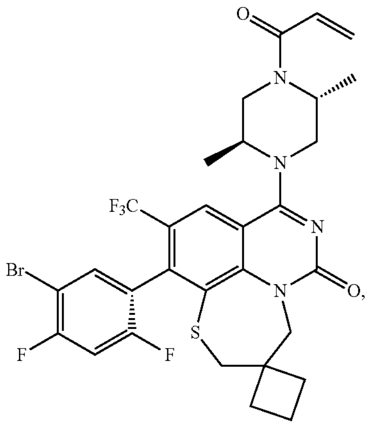
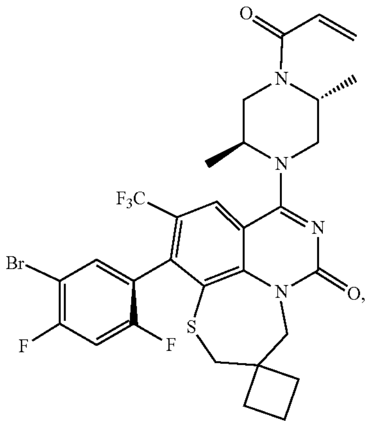
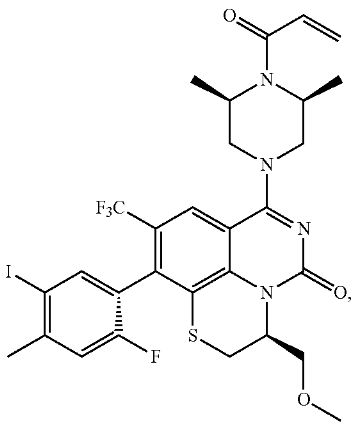
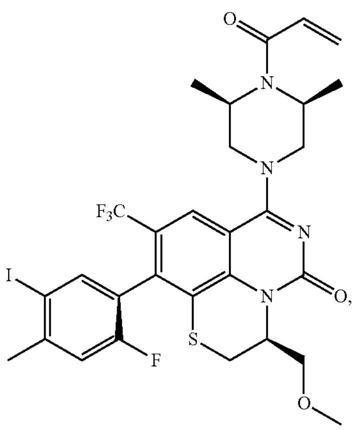
-continued
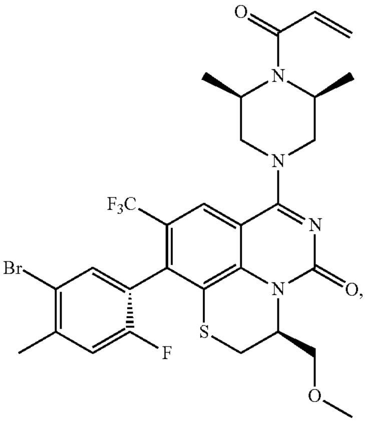
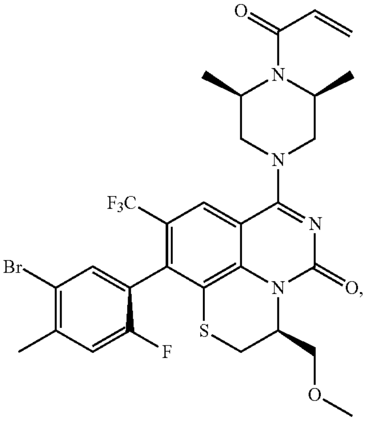
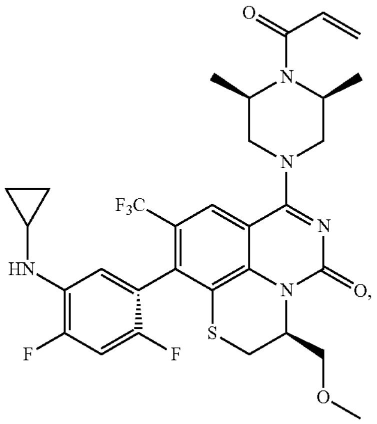
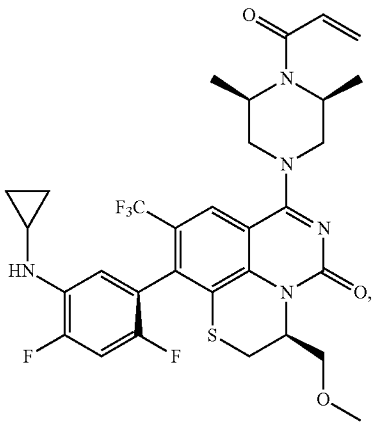

-continued

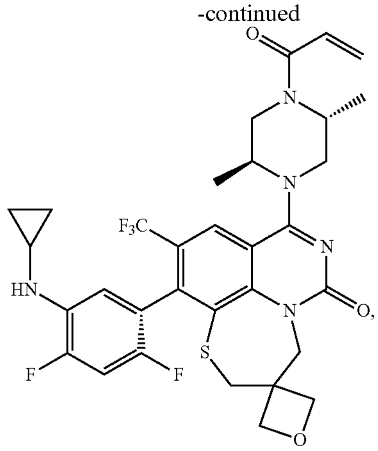

O, and

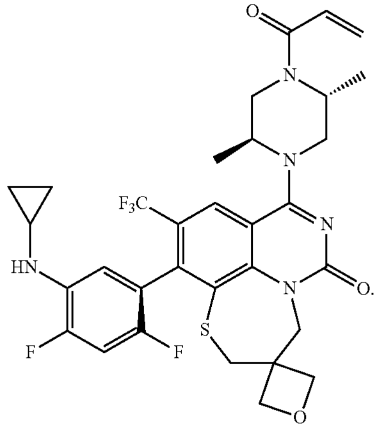

O.

AA. Example 7 CAF Assay

This Example provides a protocol for assessing covalent adduct formation (CAF) between the compounds of the present application and KRAS.

In vitro covalent adduct formation assay: Covalent adduct formation (CAF) reactions between Cys12 of the KRAS 4B G12C protein and some of the compounds of Tables 1 to 4 were measured in vitro using liquid chromatography-mass spectrometry (LC-MS).

Recombinant Human KRAS 4B protein containing the G12C mutation was used in compound screening experiments. This protein contained 188 amino acids in total, including an N-terminal 6-Histidine tag, followed by a Tobacco Etch Virus (TEV) tag, followed by residues 1-169 of the native KRAS 4B sequence. The exact mass of the protein was 21,310 Da as determined by mass spectrometry. The full amino acid sequence is shown below:

```
                                       (SEQ ID NO.: 4)
MAHHHHHHAG GAENLYFQSM TEYKLVVVGA CGVGKSALTI

QLIQNHFVDE YDPTIEDSYR KQVVIDGETC LLDILDTAGQ

EEYSAMRDQY MRTGEGFLCV FAINNTKSFE DIHHYREQIK

RVKDSEDVPM VLVGNKCDLP SRTVDTKQAQ DLARSYGIPF

IETSAKTRQG VDDAFYTLVR EIRKHKEK
```

In an alternative screen, the assay can be conducted using a KRAS 4b G12C protein having 170 amino acids, a mass of 19,336 Da, and the amino acid sequence

```
                                       (SEQ ID NO.: 5)
SMTEYKLVVVGA CGVGKSALTI QLIQNHFVDE YDPTIEDSYR

KQVVIDGETC LLDILDTAGQ EEYSAMRDQY MRTGEGFLCV

FAINNTKSFE DIHHYREQIK RVKDSEDVPM VLVGNKCDLP

SRTVDTKQAQ DLARSYGIPF IETSAKTRQG VDDAFYTLVR

EIRKHKEK.
```

The recombinant protein was expressed in *E. coli* BL21 cells and purified using affinity chromatography via a Ni-NTA column. Protein stocks were nucleotide-exchanged to >95% GDP, concentrated to 4 mg/mL, and stored at −80° C. in storage buffer (50 mM HEPES pH 7.4, 50 mM NaCl, 5 mM MgC12, 1 mM DTT). Pure KRAS 4B G12C protein was diluted to a concentration of 5 μM in Tris Buffered Saline, pH 7.4. The compounds were dissolved in DMSO and added to the diluted protein to make a 10 μM concentration. The total DMSO concentration in the reaction was 4%. The reaction was mixed by pipetting and incubated at 22° C. for one hour. Aliquots of the reaction were taken over time and diluted 2:1 in 0.1% formic acid. The intact mass of the protein samples was measured by LC-MS using a QExactive+ mass spectrometer (Thermo Scientific). An amount of 500 ng total protein was injected onto a C8 reverse phase column, eluted with a seven-minute gradient of 30%-90% acetonitrile/0.10% formic acid, and analyzed for intact mass by the mass spectrometer. Adducts identified were confirmed to be within 1 Dalton of the expected mass, and the relative ratios of free:adduct protein were used to quantify the percentage of protein bound by the compound. CAF reactions were run in duplicate, with a typical variability of ±5%.

BB. Example 9: Determination of Total Drug Concentration in Rat Brain

In Vivo Experimental Procedures

Infuse male SD rat at 2 mg/kg dose for 4 hours through IV administration route. Collect brain tissues at the end of 4 hours.

Sample Preparation Procedures

Dilute brain tissue by adding homogenization solvent (1:4, w/v). Homogenize diluted brain tissue samples. Extract analyte by adding organic solvent (1:4, v/v) with spiked internal standard. Vortex and centrifuge the samples. Remove supernatant and dilute with HPLC compatible solvent (1:3, v/v).

Analytical Procedures

Inject diluted extract into LC-MS/MS system using reversed phase high performance liquid chromatography coupled with electrospray ionization and selected reaction monitoring. Determine the total drug concentration in brain samples by quantitating against the standard curve prepared using the same matrix.

The following data provides blood brain barrier (BBB) penetration activity for a selection of inventive compounds where were directly compared to sotorasib and adagrasib (concentration in brain measured in ng/g).

TABLE 13
| BBB activity | | |
|---|---|---|
| Entry # | Structure | BBB activity |
| 13-1 | 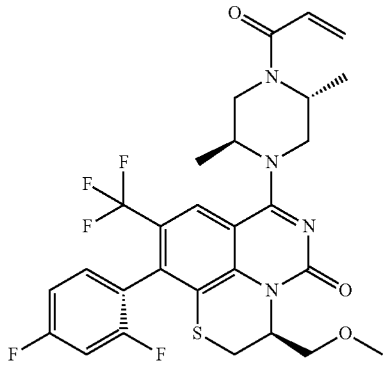 | + |
| 13-2 | 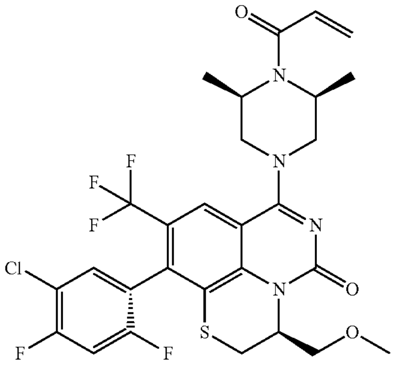 | + |
| 13-3 | 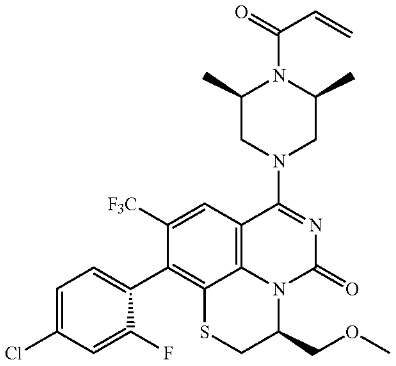 | + |
| 13-4 | 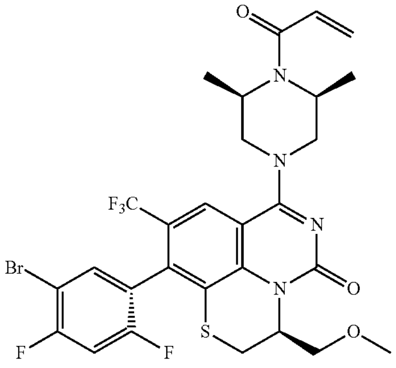 | + |

TABLE 13-continued
| BBB activity | | |
|---|---|---|
| Entry # | Structure | BBB activity |
| 13-5 | 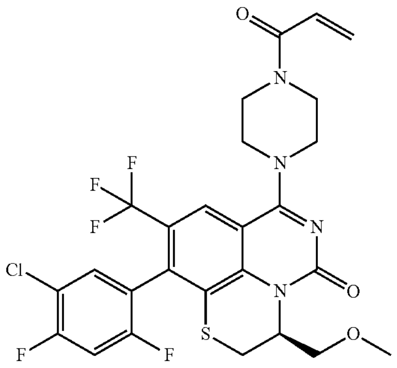 [SMILES: C=CC(=O)N1CCN(c2nc(=O)n3c4c(c(-c5cc(Cl)c(F)cc5F)c(C(F)(F)F)cc24)SC[C@@H]3COC)CC1] | + |
| 13-6 | 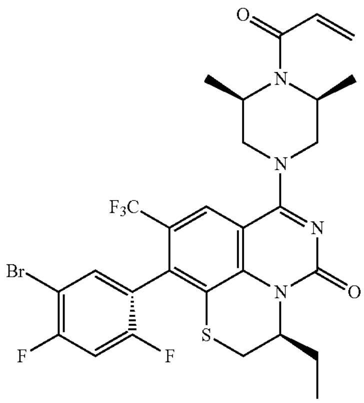 | + |
| 13-7 | 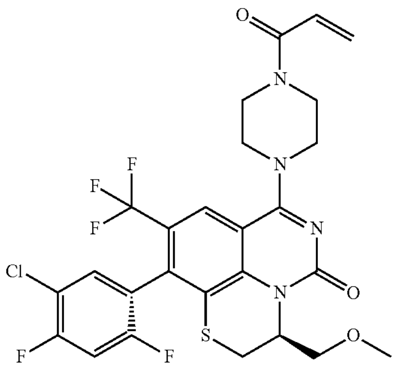 | + |
| 13-8 | 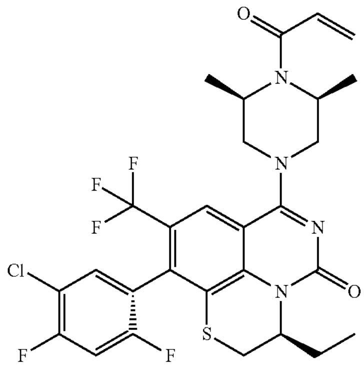 | + |

TABLE 13-continued
| BBB activity | | |
|---|---|---|
| Entry # | Structure | BBB activity |
| 13-9 | 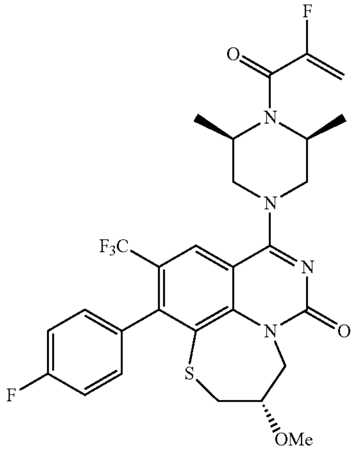 [SMILES: C=C(F)C(=O)N1[C@H](C)CN(c2nc(=O)n3c4c(c(-c5ccc(F)cc5)c(C(F)(F)F)cc24)SC[C@@H](OC)C3)C[C@@H]1C] | + |
| 13-10 | 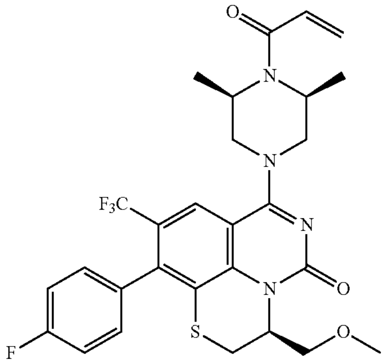 [SMILES: C=CC(=O)N1[C@H](C)CN(c2nc(=O)n3c4c(c(-c5ccc(F)cc5)c(C(F)(F)F)cc24)SC[C@@H]3COC)C[C@@H]1C] | + |
| 13-12 | 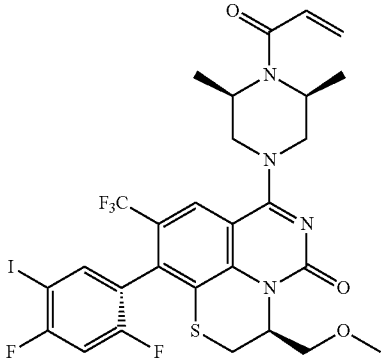 | + |
| 13-13 | 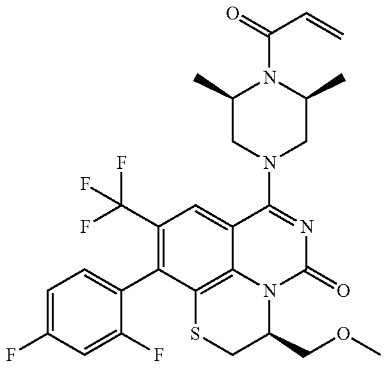 [SMILES: C=CC(=O)N1[C@H](C)CN(c2nc(=O)n3c4c(c(-c5ccc(F)cc5F)c(C(F)(F)F)cc24)SC[C@@H]3COC)C[C@@H]1C] | + |

TABLE 13-continued
| BBB activity | | |
|---|---|---|
| Entry # | Structure | BBB activity |
| 13-14 | 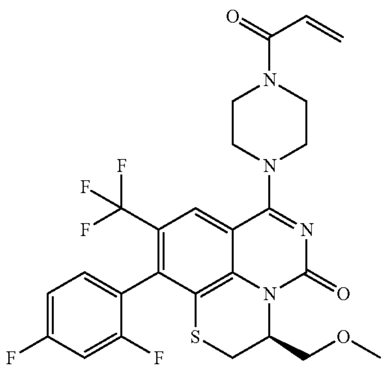 [SMILES: C=CC(=O)N1CCN(c2nc(=O)n3c4c(c(-c5ccc(F)cc5F)c(C(F)(F)F)cc24)SC[C@@H]3COC)CC1] | + |
| 13-15 | 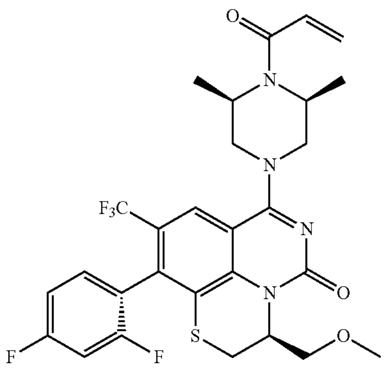 | + |
| 13-16 | 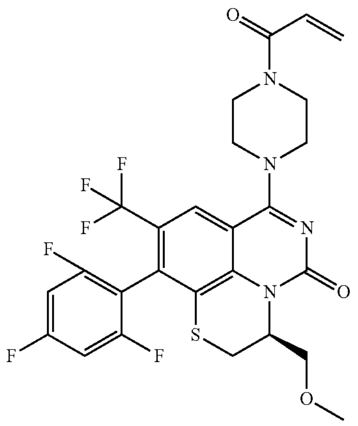 [SMILES: C=CC(=O)N1CCN(c2nc(=O)n3c4c(c(-c5c(F)cc(F)cc5F)c(C(F)(F)F)cc24)SC[C@@H]3COC)CC1] | + |
| 13-17 | 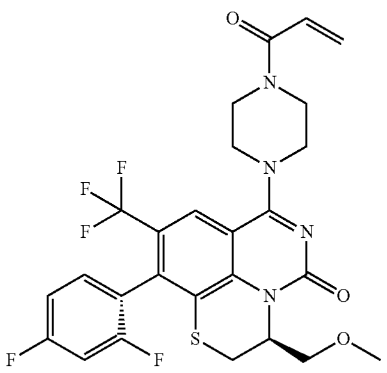 | + |

TABLE 13-continued
| BBB activity | | |
|---|---|---|
| Entry # | Structure | BBB activity |
| 13-18 | 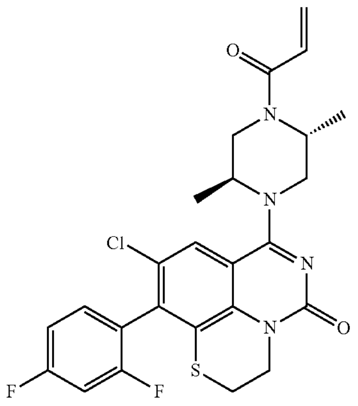 [SMILES: C=CC(=O)N1C[C@H](C)N(c2nc(=O)n3c4c(c(-c5ccc(F)cc5F)c(Cl)cc24)SCC3)C[C@H]1C] | + |
| 13-19 | 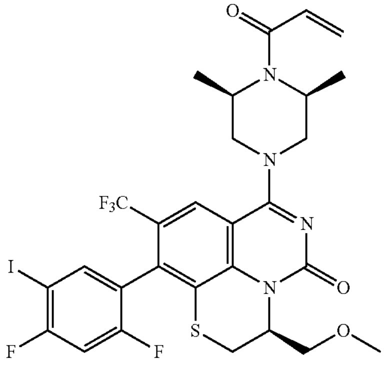 [SMILES: C=CC(=O)N1[C@H](C)CN(c2nc(=O)n3c4c(c(-c5cc(I)c(F)cc5F)c(C(F)(F)F)cc24)SC[C@@H]3COC)C[C@@H]1C] | + |
| 13-20 | 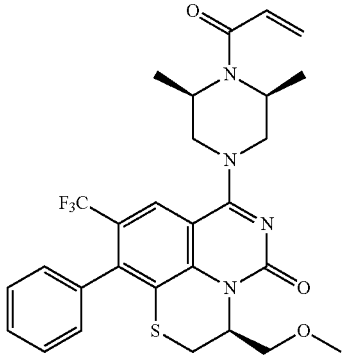 [SMILES: C=CC(=O)N1[C@H](C)CN(c2nc(=O)n3c4c(c(-c5ccccc5)c(C(F)(F)F)cc24)SC[C@@H]3COC)C[C@@H]1C] | + |

TABLE 13-continued
| BBB activity | | |
|---|---|---|
| Entry # | Structure | BBB activity |
| 13-21 | 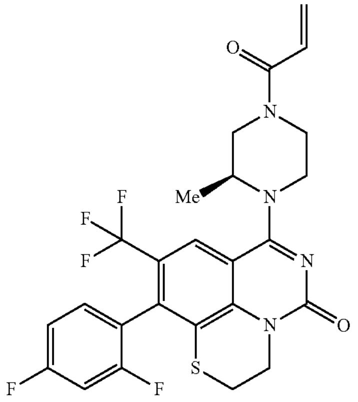 [SMILES: C=CC(=O)N1CCN(c2nc(=O)n3c4c(c(-c5ccc(F)cc5F)c(C(F)(F)F)cc24)SCC3)[C@@H](C)C1] | + |
| 13-22 | 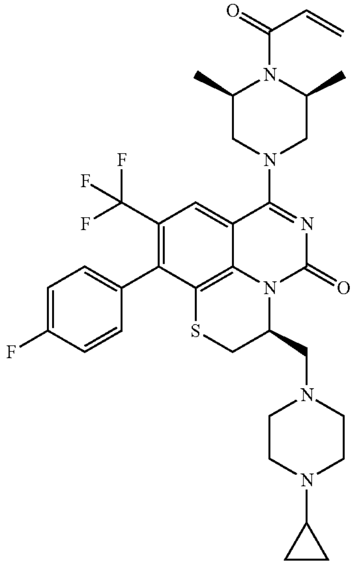 [SMILES: C=CC(=O)N1[C@H](C)CN(c2nc(=O)n3c4c(c(-c5ccc(F)cc5)c(C(F)(F)F)cc24)SC[C@@H]3CN2CCN(C3CC3)CC2)C[C@@H]1C] | + |
| 13-23 | 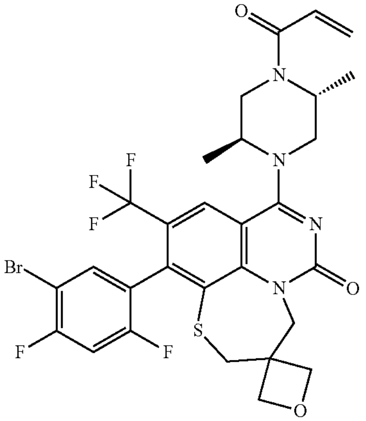 | + |

TABLE 13-continued
| BBB activity | | |
|---|---|---|
| Entry # | Structure | BBB activity |
| 13-24 | 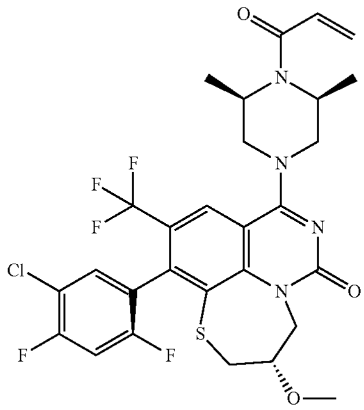 | + |
| 13-25 | 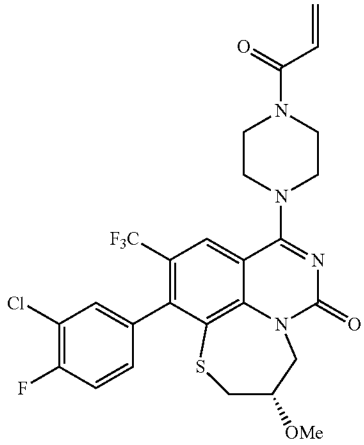 [SMILES: C=CC(=O)N1CCN(c2nc(=O)n3c4c(c(-c5ccc(F)c(Cl)c5)c(C(F)(F)F)cc24)SC[C@@H](OC)C3)CC1] | + |
| 13-26 | 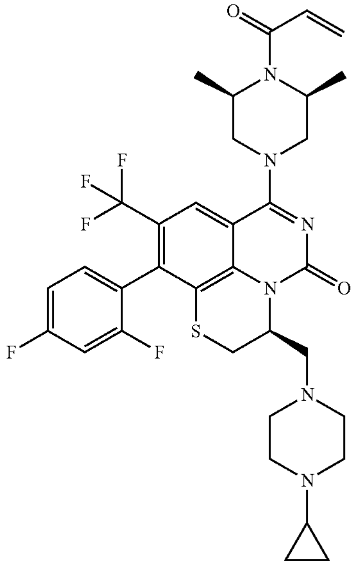 [SMILES: C=CC(=O)N1[C@H](C)CN(c2nc(=O)n3c4c(c(-c5ccc(F)cc5F)c(C(F)(F)F)cc24)SC[C@@H]3CN2CCN(C3CC3)CC2)C[C@@H]1C] | + |

TABLE 13-continued
| BBB activity | | |
|---|---|---|
| Entry # | Structure | BBB activity |
| 13-27 | 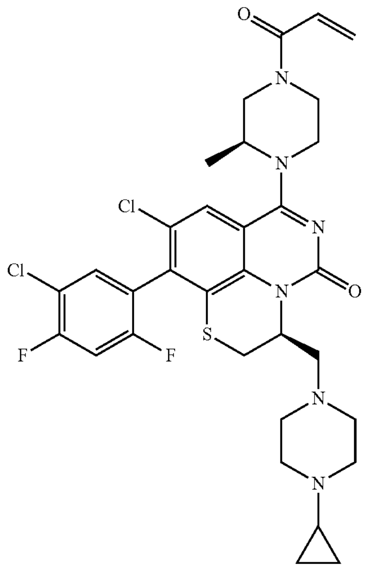 [SMILES: C=CC(=O)N1CCN(c2nc(=O)n3c4c(c(-c5cc(Cl)c(F)cc5F)c(Cl)cc24)SC[C@@H]3CN2CCN(C3CC3)CC2)[C@@H](C)C1] | + |
| 13-28 | 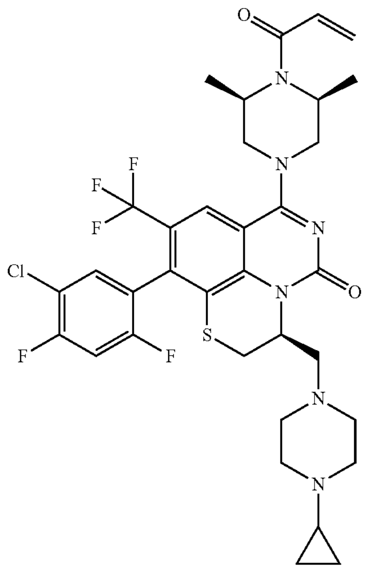 [SMILES: C=CC(=O)N1[C@H](C)CN(c2nc(=O)n3c4c(c(-c5cc(Cl)c(F)cc5F)c(C(F)(F)F)cc24)SC[C@@H]3CN2CCN(C3CC3)CC2)C[C@@H]1C] | + |

TABLE 13-continued
| BBB activity | | |
|---|---|---|
| Entry # | Structure | BBB activity |
| 13-29 | 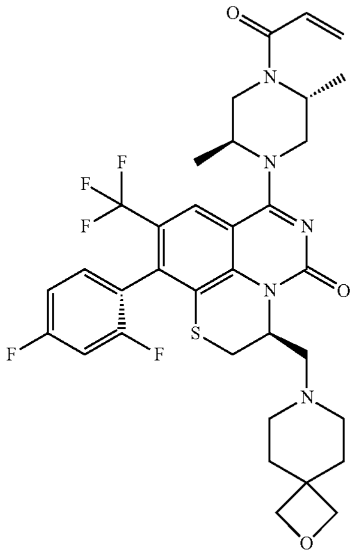 | + |
| 13-30 | 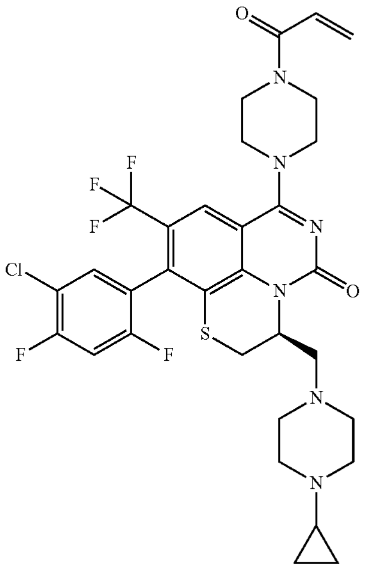 [SMILES: C=CC(=O)N1CCN(c2nc(=O)n3c4c(c(-c5cc(Cl)c(F)cc5F)c(C(F)(F)F)cc24)SC[C@@H]3CN2CCN(C3CC3)CC2)CC1] | + |
| 13-31 | 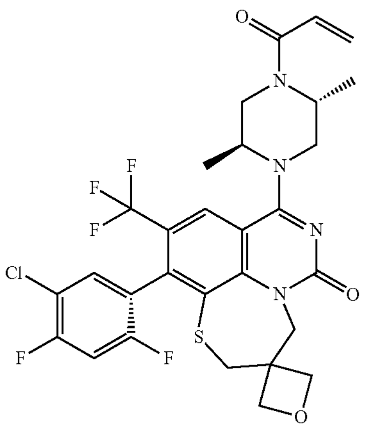 | + |

TABLE 13-continued
| BBB activity | | |
|---|---|---|
| Entry # | Structure | BBB activity |
| 13-32 | 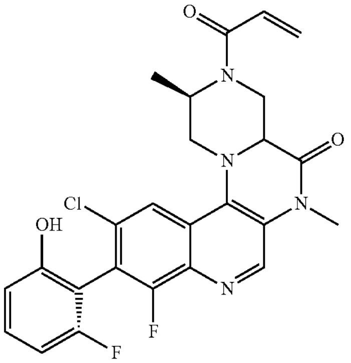 | + |
| 13-33 | 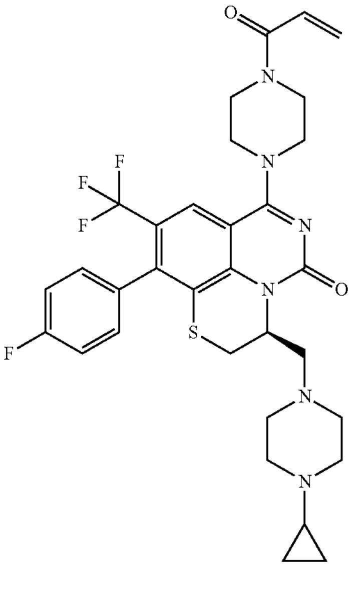 [SMILES: C=CC(=O)N1CCN(c2nc(=O)n3c4c(c(-c5ccc(F)cc5)c(C(F)(F)F)cc24)SC[C@@H]3CN2CCN(C3CC3)CC2)CC1] | + |
| 13-34 | 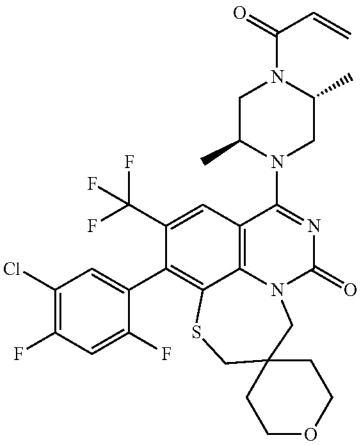 [SMILES: C=CC(=O)N1C[C@H](C)N(c2nc(=O)n3c4c(c(-c5cc(Cl)c(F)cc5F)c(C(F)(F)F)cc24)SCC2(CCOCC2)C3)C[C@H]1C] | + |

TABLE 13-continued
| BBB activity | | |
|---|---|---|
| Entry # | Structure | BBB activity |
| 13-35 | 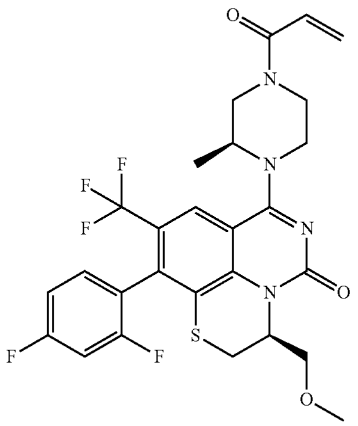 [SMILES: C=CC(=O)N1CCN(c2nc(=O)n3c4c(c(-c5ccc(F)cc5F)c(C(F)(F)F)cc24)SC[C@@H]3COC)[C@@H](C)C1] | + |
| 13-36 | 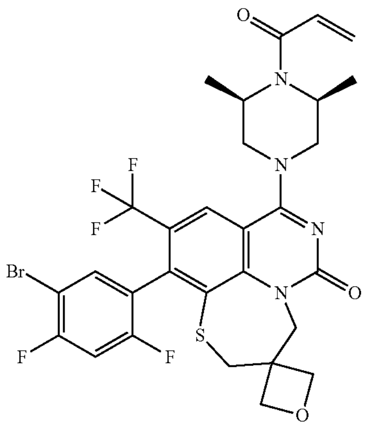 [SMILES: C=CC(=O)N1[C@H](C)CN(c2nc(=O)n3c4c(c(-c5cc(Br)c(F)cc5F)c(C(F)(F)F)cc24)SCC2(COC2)C3)C[C@@H]1C] | + |
| 13-37 | 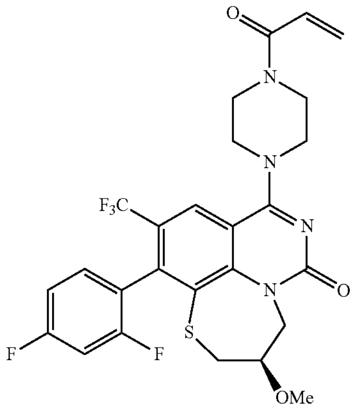 [SMILES: C=CC(=O)N1CCN(c2nc(=O)n3c4c(c(-c5ccc(F)cc5F)c(C(F)(F)F)cc24)SC[C@H](OC)C3)CC1] | + |

TABLE 13-continued
| BBB activity | | |
|---|---|---|
| Entry # | Structure | BBB activity |
| 13-38 | 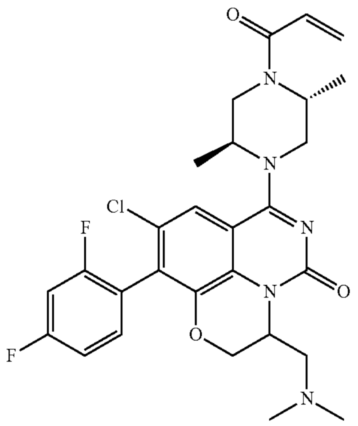 [SMILES: C=CC(=O)N1C[C@H](C)N(c2nc(=O)n3c4c(c(-c5ccc(F)cc5F)c(Cl)cc24)OCC3CN(C)C)C[C@H]1C] | + |
| 13-39 | 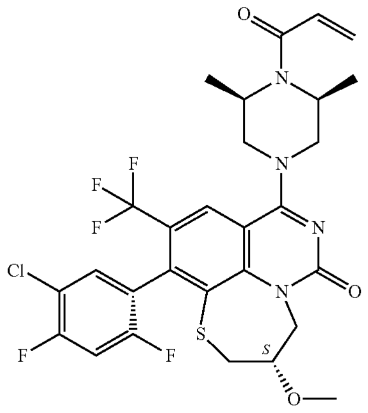 | + |
| 13-40 | 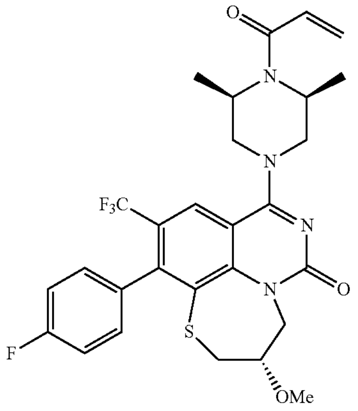 [SMILES: C=CC(=O)N1[C@H](C)CN(c2nc(=O)n3c4c(c(-c5ccc(F)cc5)c(C(F)(F)F)cc24)SC[C@@H](OC)C3)C[C@@H]1C] | + |

TABLE 13-continued
| BBB activity | | |
|---|---|---|
| Entry # | Structure | BBB activity |
| 13-41 | 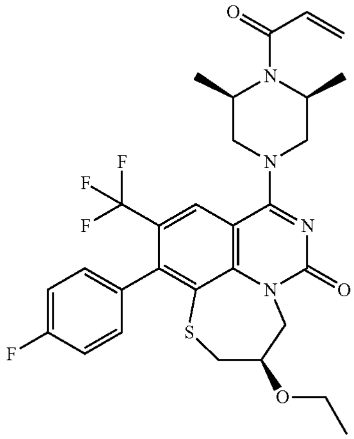 [SMILES: C=CC(=O)N1[C@H](C)CN(c2nc(=O)n3c4c(c(-c5ccc(F)cc5)c(C(F)(F)F)cc24)SC[C@H](OCC)C3)C[C@@H]1C] | + |
| 13-42 | 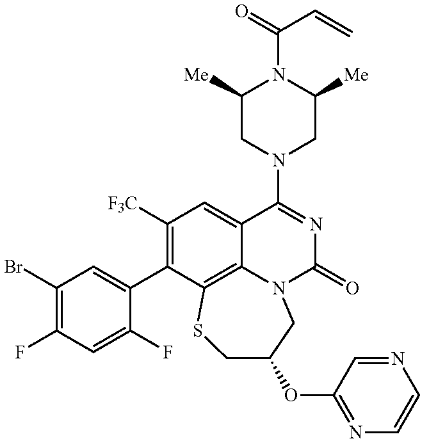 [SMILES: C=CC(=O)N1[C@H](C)CN(c2nc(=O)n3c4c(c(-c5cc(Br)c(F)cc5F)c(C(F)(F)F)cc24)SC[C@@H](Oc2cnccn2)C3)C[C@@H]1C] | + |
| 13-43 | 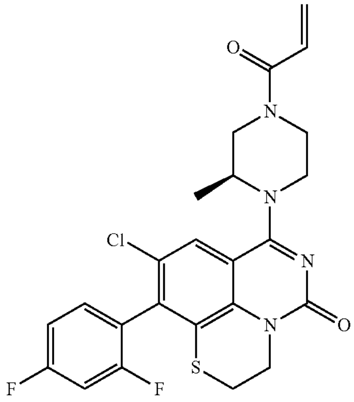 [SMILES: C=CC(=O)N1CCN(c2nc(=O)n3c4c(c(-c5ccc(F)cc5F)c(Cl)cc24)SCC3)[C@@H](C)C1] | + |

TABLE 13-continued
| BBB activity | | |
|---|---|---|
| Entry # | Structure | BBB activity |
| 13-44 | 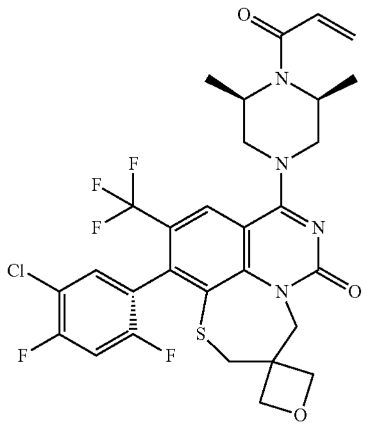 | + |
| 13-45 | 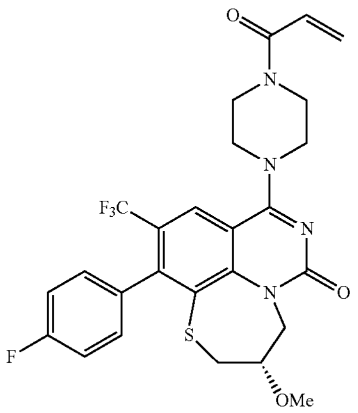 [SMILES: C=CC(=O)N1CCN(c2nc(=O)n3c4c(c(-c5ccc(F)cc5)c(C(F)(F)F)cc24)SC[C@@H](OC)C3)CC1] | + |
| 13-46 | 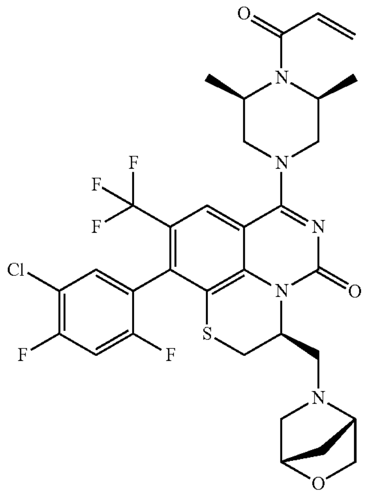 [SMILES: C=CC(=O)N1[C@H](C)CN(c2nc(=O)n3c4c(c(-c5cc(Cl)c(F)cc5F)c(C(F)(F)F)cc24)SC[C@@H]3CN2C[C@@H]3C[C@H]2CO3)C[C@@H]1C] | + |

TABLE 13-continued
BBB activity
| Entry # | Structure | BBB activity |
| --- | --- | --- |
| 13-47 | 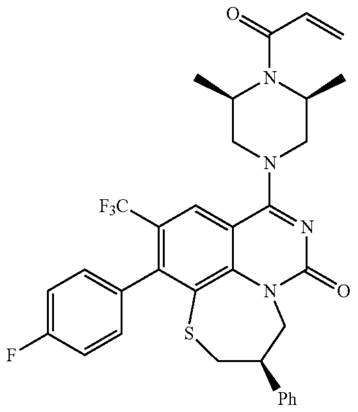 [SMILES: C=CC(=O)N1[C@H](C)CN(c2nc(=O)n3c4c(c(-c5ccc(F)cc5)c(C(F)(F)F)cc24)SC[C@H](c2ccccc2)C3)C[C@@H]1C] | – |
| 13-48 | 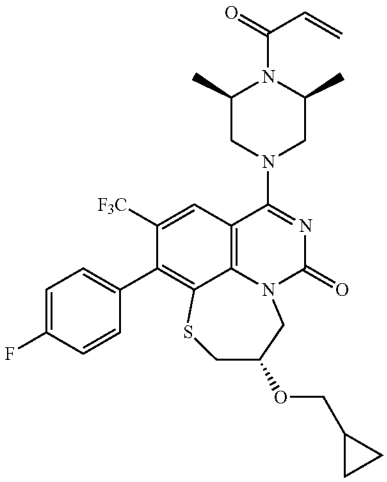 [SMILES: C=CC(=O)N1[C@H](C)CN(c2nc(=O)n3c4c(c(-c5ccc(F)cc5)c(C(F)(F)F)cc24)SC[C@@H](OCC2CC2)C3)C[C@@H]1C] | – |
| 13-49 | 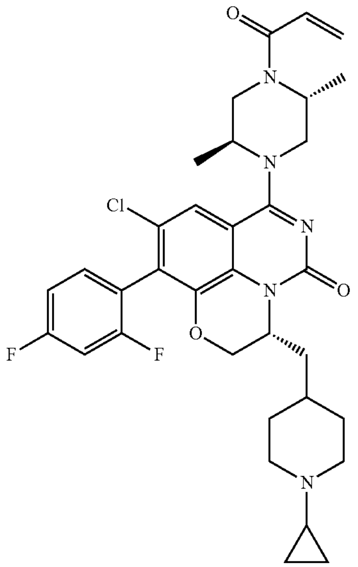 [SMILES: C=CC(=O)N1C[C@H](C)N(c2nc(=O)n3c4c(c(-c5ccc(F)cc5F)c(Cl)cc24)OC[C@H]3CC2CCN(C3CC3)CC2)C[C@H]1C] | – |

TABLE 13-continued
| BBB activity | | |
|---|---|---|
| Entry # | Structure | BBB activity |
| 13-50 | 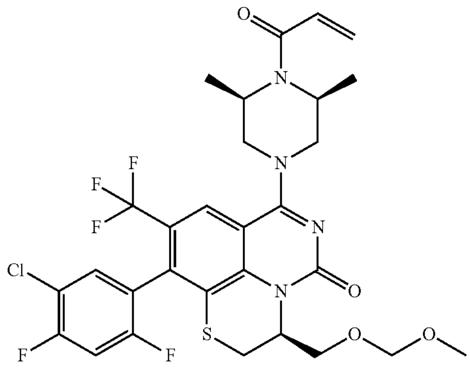 [SMILES: C=CC(=O)N1[C@H](C)CN(c2nc(=O)n3c4c(c(-c5cc(Cl)c(F)cc5F)c(C(F)(F)F)cc24)SC[C@@H]3COCOC)C[C@@H]1C] | – |
| 13-51 | 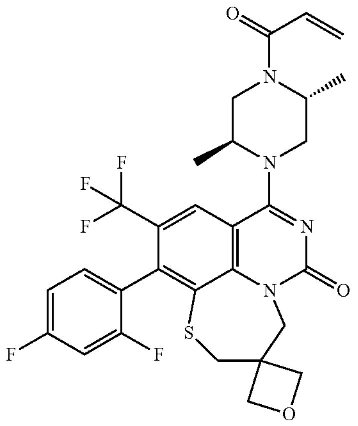 [SMILES: C=CC(=O)N1C[C@H](C)N(c2nc(=O)n3c4c(c(-c5ccc(F)cc5F)c(C(F)(F)F)cc24)SCC2(COC2)C3)C[C@H]1C] | – |
| 13-52 | 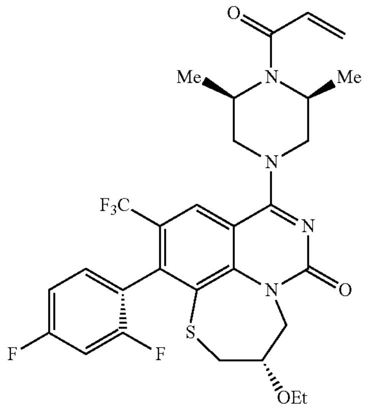 | – |

TABLE 13-continued
| BBB activity | | |
|---|---|---|
| Entry # | Structure | BBB activity |
| 13-53 | 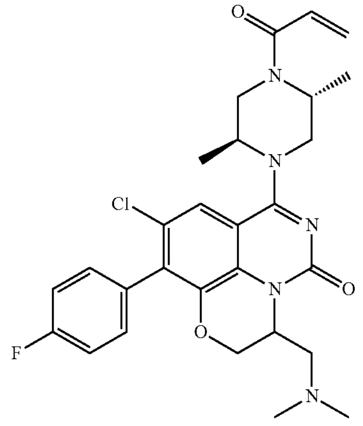 [SMILES: C=CC(=O)N1C[C@H](C)N(c2nc(=O)n3c4c(c(-c5ccc(F)cc5)c(Cl)cc24)OCC3CN(C)C)C[C@H]1C] | – |
| 13-54 | 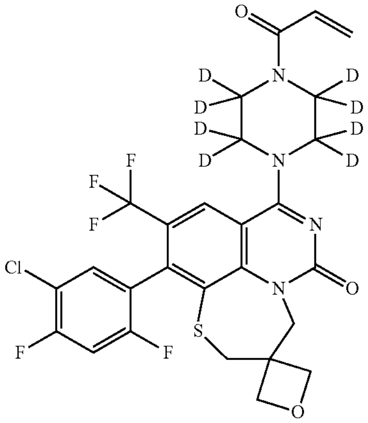 [SMILES: [2H]C1([2H])N(C(=O)C=C)C([2H])([2H])C([2H])([2H])N(c2nc(=O)n3c4c(c(-c5cc(Cl)c(F)cc5F)c(C(F)(F)F)cc24)SCC2(COC2)C3)C1([2H])[2H]] | – |
| 13-55 | 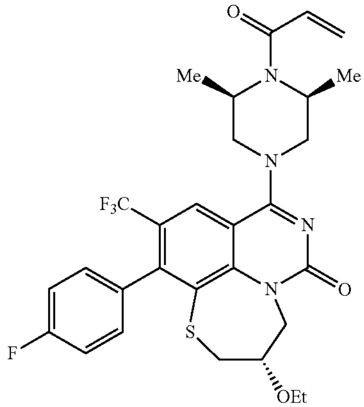 [SMILES: C=CC(=O)N1[C@H](C)CN(c2nc(=O)n3c4c(c(-c5ccc(F)cc5)c(C(F)(F)F)cc24)SC[C@@H](OCC)C3)C[C@@H]1C] | – |

TABLE 13-continued
| BBB activity | | |
|---|---|---|
| Entry # | Structure | BBB activity |
| 13-56 | 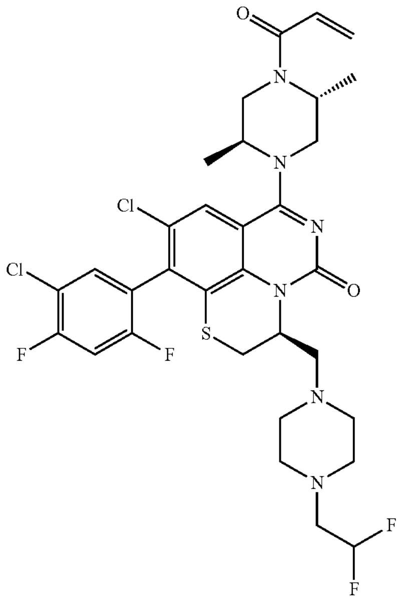 [SMILES: C=CC(=O)N1C[C@H](C)N(c2nc(=O)n3c4c(c(-c5cc(Cl)c(F)cc5F)c(Cl)cc24)SC[C@@H]3CN2CCN(CC(F)F)CC2)C[C@H]1C] | – |
| 13-57 | 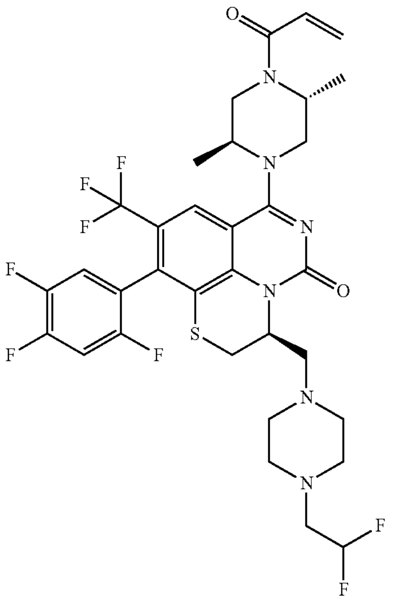 [SMILES: C=CC(=O)N1C[C@H](C)N(c2nc(=O)n3c4c(c(-c5cc(F)c(F)cc5F)c(C(F)(F)F)cc24)SC[C@@H]3CN2CCN(CC(F)F)CC2)C[C@H]1C] | – |

TABLE 13-continued
| BBB activity | | |
|---|---|---|
| Entry # | Structure | BBB activity |
| 13-58 | 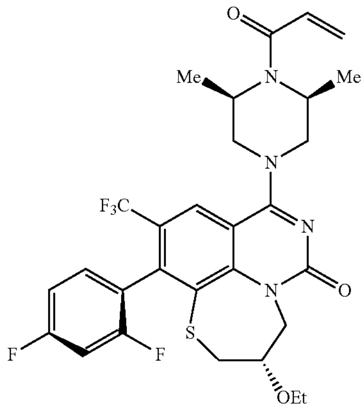 | – |
| 13-59 | 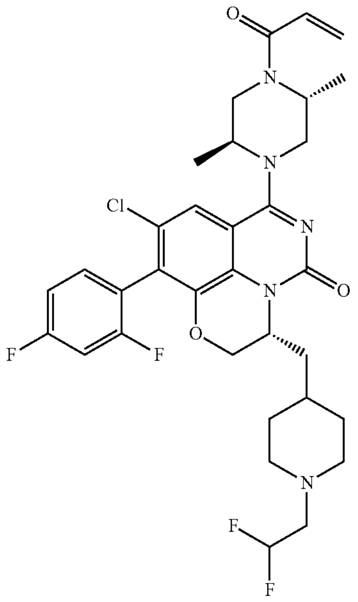 [SMILES: C=CC(=O)N1C[C@H](C)N(c2nc(=O)n3c4c(c(-c5ccc(F)cc5F)c(Cl)cc24)OC[C@H]3CC2CCN(CC(F)F)CC2)C[C@H]1C] | – |
| 13-60 | 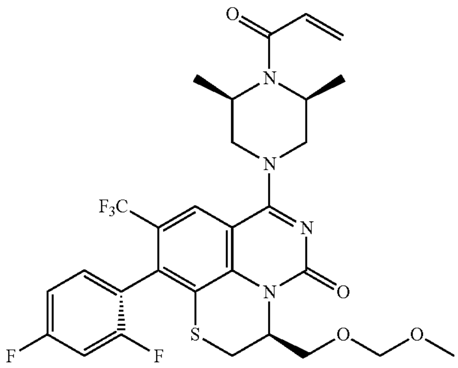 | – |

TABLE 13-continued
| BBB activity | | |
|---|---|---|
| Entry # | Structure | BBB activity |
| 13-61 | 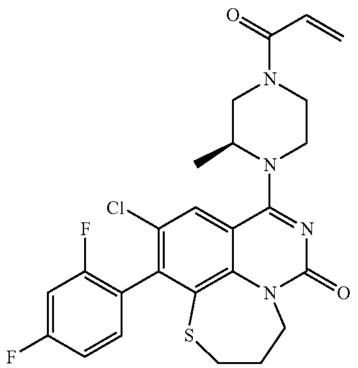 [SMILES: C=CC(=O)N1CCN(c2nc(=O)n3c4c(c(-c5ccc(F)cc5F)c(Cl)cc24)SCCC3)[C@@H](C)C1] | – |
| 13-62 | 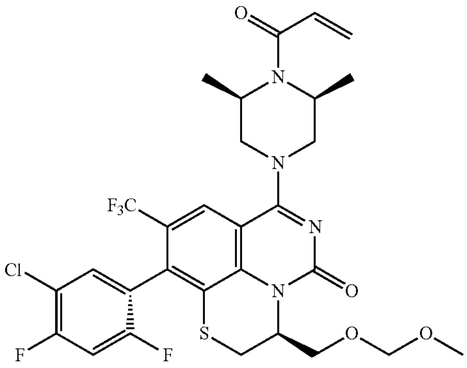 | – |
| 13-63 | 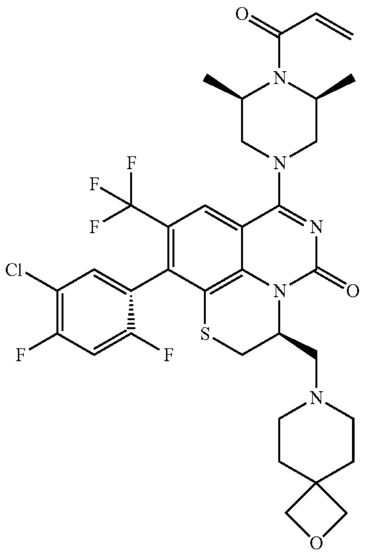 | – |

TABLE 13-continued
| BBB activity | | |
|---|---|---|
| Entry # | Structure | BBB activity |
| 13-64 | 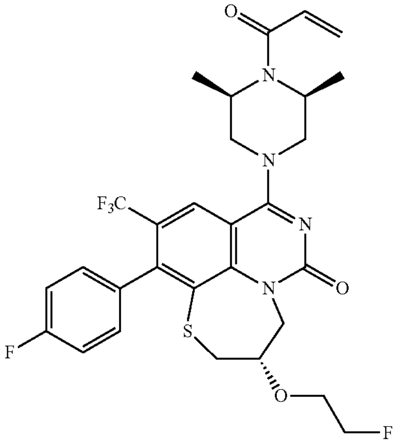 [SMILES: C=CC(=O)N1[C@H](C)CN(c2nc(=O)n3c4c(c(-c5ccc(F)cc5)c(C(F)(F)F)cc24)SC[C@@H](OCCF)C3)C[C@@H]1C] | – |
| 13-65 | 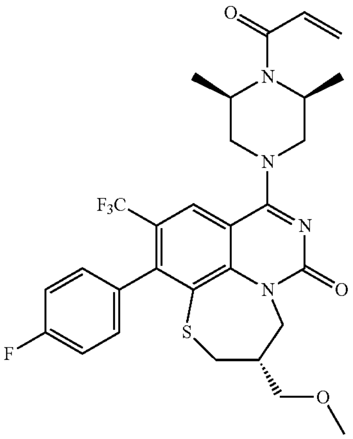 [SMILES: C=CC(=O)N1[C@H](C)CN(c2nc(=O)n3c4c(c(-c5ccc(F)cc5)c(C(F)(F)F)cc24)SC[C@@H](COC)C3)C[C@@H]1C] | – |
| 13-66 | 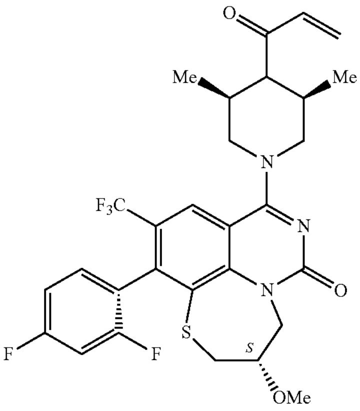 | – |

TABLE 13-continued
| BBB activity | | |
|---|---|---|
| Entry # | Structure | BBB activity |
| 13-67 | 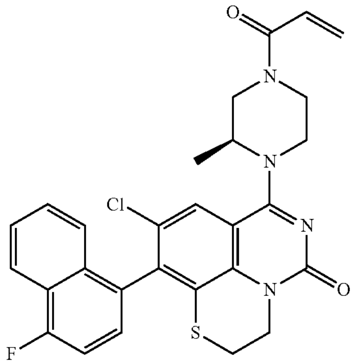 [SMILES: C=CC(=O)N1CCN(c2nc(=O)n3c4c(c(-c5ccc(F)c6ccccc56)c(Cl)cc24)SCC3)[C@@H](C)C1] | – |
| 13-68 | 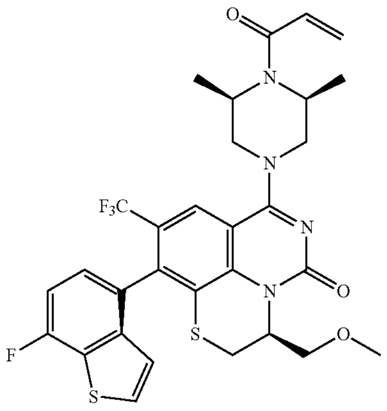 | – |
| 13-69 | 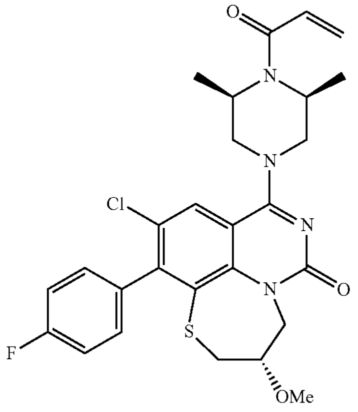 [SMILES: C=CC(=O)N1[C@H](C)CN(c2nc(=O)n3c4c(c(-c5ccc(F)cc5)c(Cl)cc24)SC[C@@H](OC)C3)C[C@@H]1C] | – |

TABLE 13-continued
| BBB activity | | |
|---|---|---|
| Entry # | Structure | BBB activity |
| 13-70 | 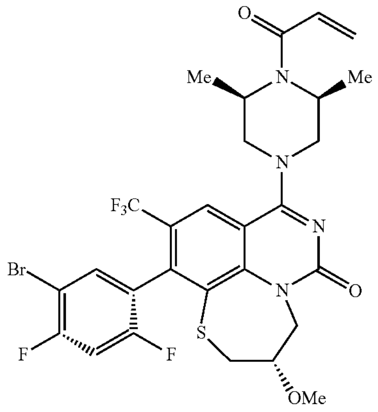 | – |
| 13-71 | 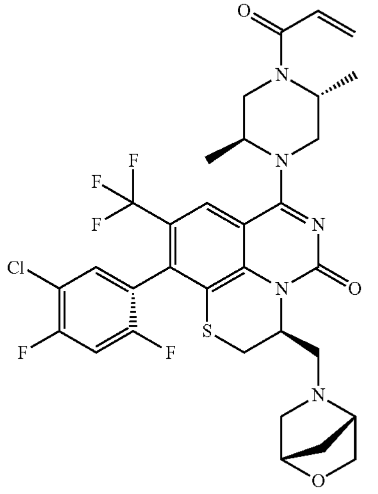 | – |
| 13-72 | 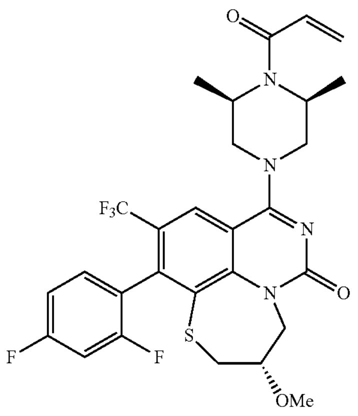 [SMILES: C=CC(=O)N1[C@H](C)CN(c2nc(=O)n3c4c(c(-c5ccc(F)cc5F)c(C(F)(F)F)cc24)SC[C@@H](OC)C3)C[C@@H]1C] | – |

TABLE 13-continued
| BBB activity | | |
|---|---|---|
| Entry # | Structure | BBB activity |
| 13-73 | 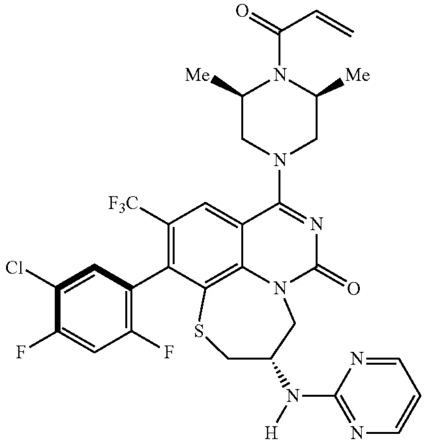 | – |
| 13-74 | 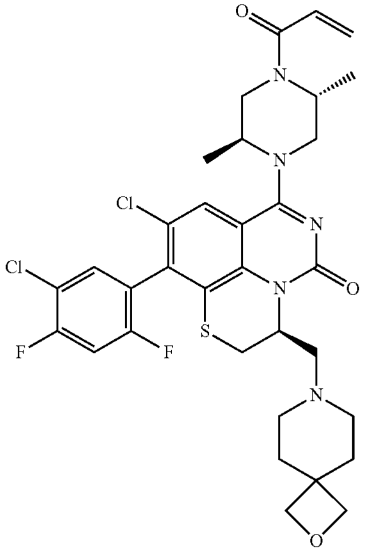 [SMILES: C=CC(=O)N1C[C@H](C)N(c2nc(=O)n3c4c(c(-c5cc(Cl)c(F)cc5F)c(Cl)cc24)SC[C@@H]3CN2CCC3(CC2)COC3)C[C@H]1C] | – |
| 13-75 | 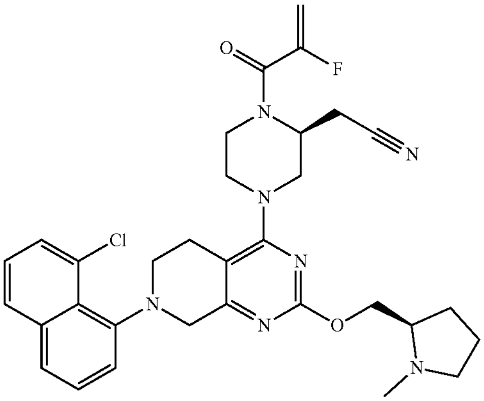 adagrasib | – |

TABLE 13-continued
| BBB activity | | |
|---|---|---|
| Entry # | Structure | BBB activity |
| 13-76 | 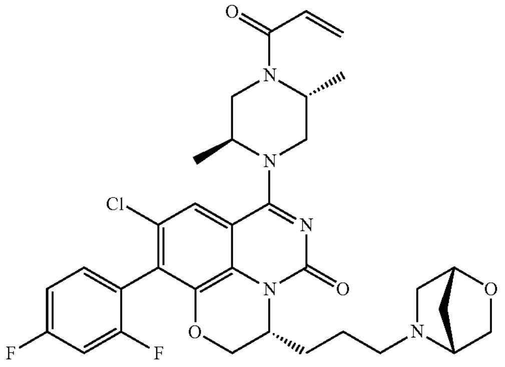 [SMILES: C=CC(=O)N1C[C@H](C)N(c2nc(=O)n3c4c(c(-c5ccc(F)cc5F)c(Cl)cc24)OC[C@H]3CCCN2C[C@H]3C[C@@H]2CO3)C[C@H]1C] | – |
| 13-77 | 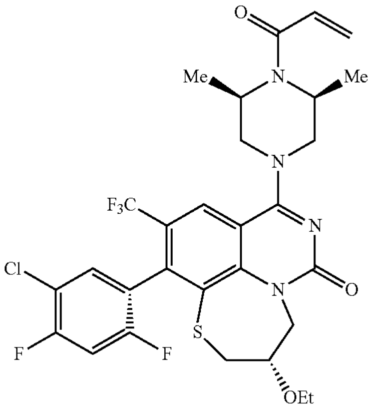 | – |
| 13-78 | 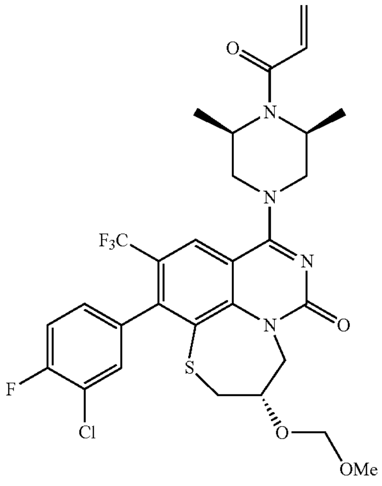 [SMILES: C=CC(=O)N1[C@H](C)CN(c2nc(=O)n3c4c(c(-c5ccc(F)c(Cl)c5)c(C(F)(F)F)cc24)SC[C@@H](OCOC)C3)C[C@@H]1C] | – |

TABLE 13-continued
| Entry # | Structure | BBB activity |
|---|---|---|
| 13-79 | 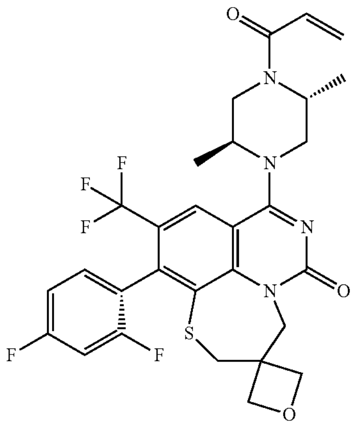 | – |
| 13-80 | 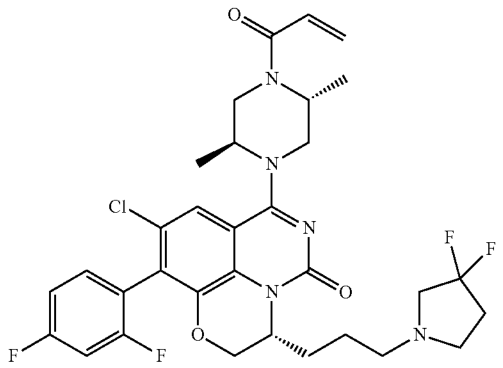 [SMILES: C=CC(=O)N1C[C@H](C)N(c2nc(=O)n3c4c(c(-c5ccc(F)cc5F)c(Cl)cc24)OC[C@H]3CCCN2CCC(F)(F)C2)C[C@H]1C] | – |
| 13-81 | 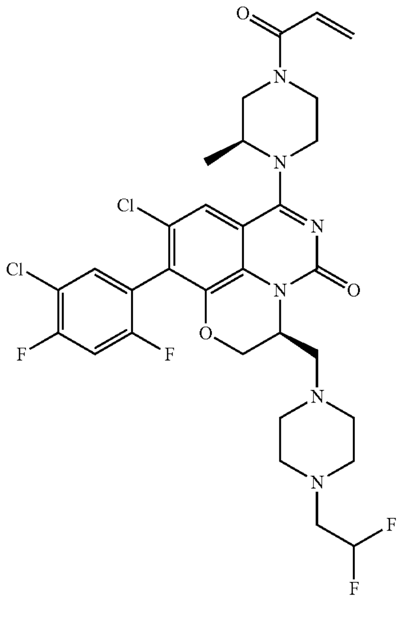 [SMILES: C=CC(=O)N1CCN(c2nc(=O)n3c4c(c(-c5cc(Cl)c(F)cc5F)c(Cl)cc24)OC[C@@H]3CN2CCN(CC(F)F)CC2)[C@@H](C)C1] | – |

TABLE 13-continued
| BBB activity | | |
|---|---|---|
| Entry # | Structure | BBB activity |
| 13-82 | 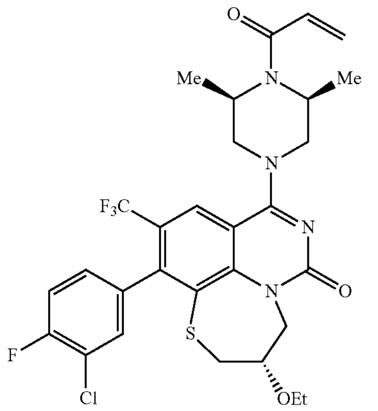 [SMILES: C=CC(=O)N1[C@H](C)CN(c2nc(=O)n3c4c(c(-c5ccc(F)c(Cl)c5)c(C(F)(F)F)cc24)SC[C@@H](OCC)C3)C[C@@H]1C] | – |
| 13-83 | 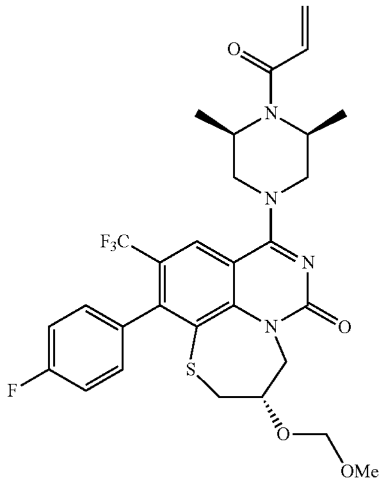 [SMILES: C=CC(=O)N1[C@H](C)CN(c2nc(=O)n3c4c(c(-c5ccc(F)cc5)c(C(F)(F)F)cc24)SC[C@@H](OCOC)C3)C[C@@H]1C] | – |
| 13-84 | 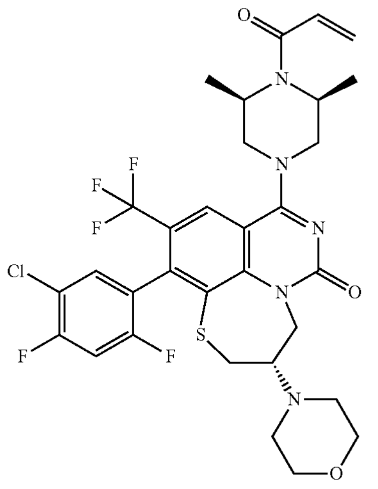 [SMILES: C=CC(=O)N1[C@H](C)CN(c2nc(=O)n3c4c(c(-c5cc(Cl)c(F)cc5F)c(C(F)(F)F)cc24)SC[C@@H](N2CCOCC2)C3)C[C@@H]1C] | – |

TABLE 13-continued
| BBB activity | | |
|---|---|---|
| Entry # | Structure | BBB activity |
| 13-85 | 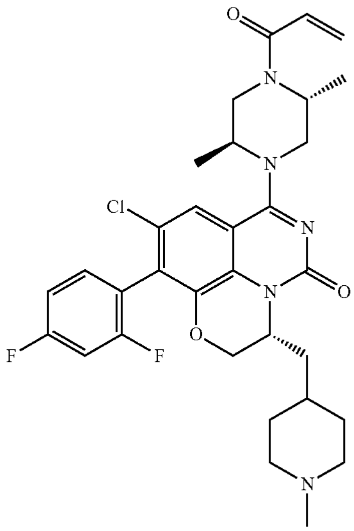 [SMILES: C=CC(=O)N1C[C@H](C)N(c2nc(=O)n3c4c(c(-c5ccc(F)cc5F)c(Cl)cc24)OC[C@H]3CC2CCN(C)CC2)C[C@H]1C] | – |
| 13-86 | 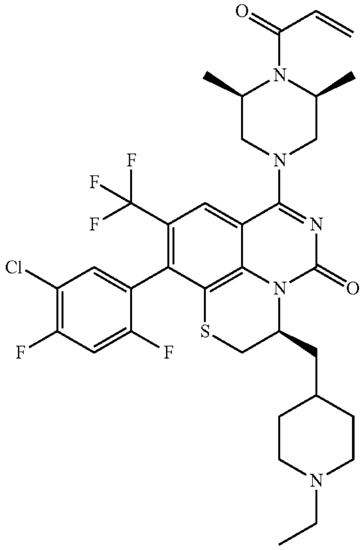 [SMILES: C=CC(=O)N1[C@H](C)CN(c2nc(=O)n3c4c(c(-c5cc(Cl)c(F)cc5F)c(C(F)(F)F)cc24)SC[C@@H]3CC2CCN(CC)CC2)C[C@@H]1C] | – |
| 13-87 | 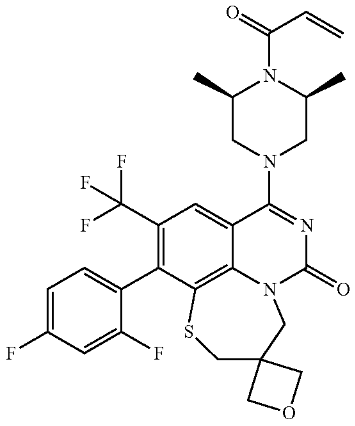 [SMILES: C=CC(=O)N1[C@H](C)CN(c2nc(=O)n3c4c(c(-c5ccc(F)cc5F)c(C(F)(F)F)cc24)SCC2(COC2)C3)C[C@@H]1C] | – |

TABLE 13-continued
| Entry # | Structure | BBB activity |
|---|---|---|
| 13-88 | 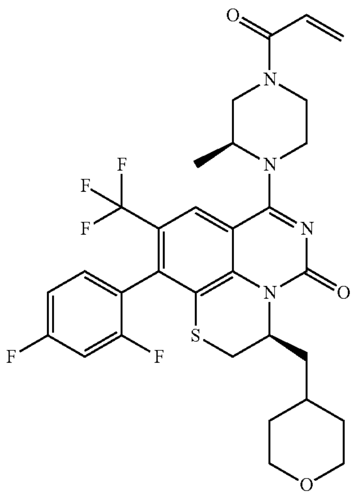 [SMILES: C=CC(=O)N1CCN(c2nc(=O)n3c4c(c(-c5ccc(F)cc5F)c(C(F)(F)F)cc24)SC[C@@H]3CC2CCOCC2)[C@@H](C)C1] | – |
| 13-89 | 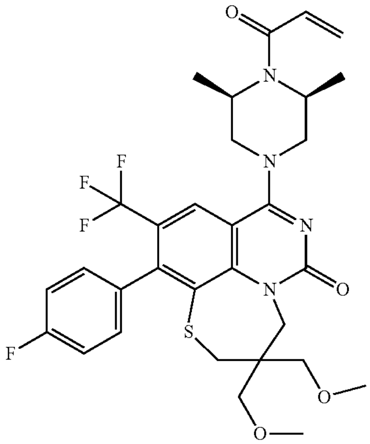 [SMILES: C=CC(=O)N1[C@H](C)CN(c2nc(=O)n3c4c(c(-c5ccc(F)cc5)c(C(F)(F)F)cc24)SCC(COC)(COC)C3)C[C@@H]1C] | – |
| 13-90 | 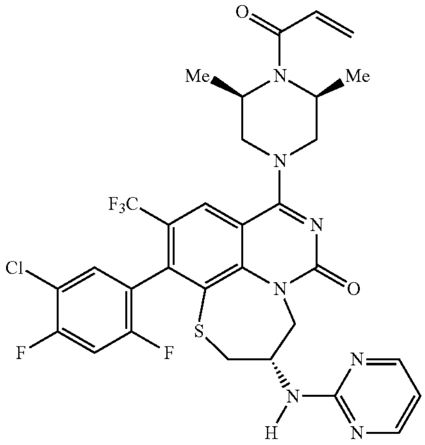 [SMILES: C=CC(=O)N1[C@H](C)CN(c2nc(=O)n3c4c(c(-c5cc(Cl)c(F)cc5F)c(C(F)(F)F)cc24)SC[C@@H](Nc2ncccn2)C3)C[C@@H]1C] | – |

TABLE 13-continued

| BBB activity | | |
| --- | --- | --- |
| Entry # | Structure | BBB activity |
| 13-91 | 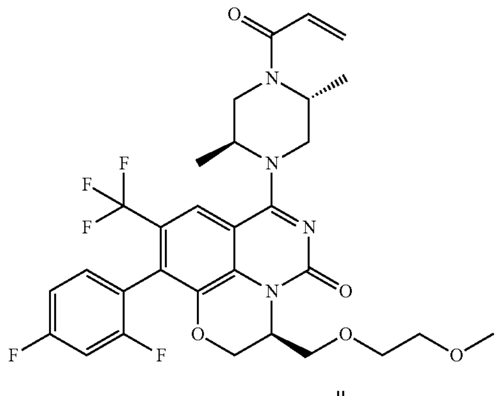 | – |
| 13-92 | 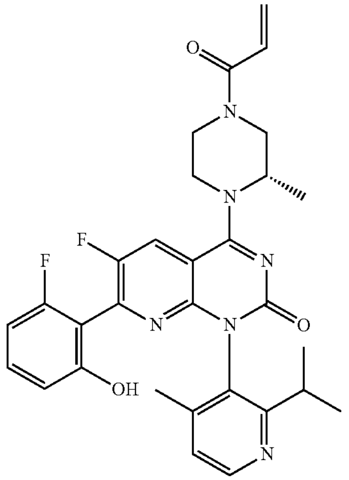 sotorasib | – |

Compounds that were measured as having a total concentration in the brain of at least 60 ng/g are indicated as "+". Compounds that did not meet this threshold are indicated as "–". The data from the table clearly indicates that the compounds have superior brain penetration than sotorasib and adagrasib, two clinical candidates.

Embodiments herein relate to methods of using compounds and classes of compounds described herein, including those set forth in Table 13, to treat CNS cancers, due at least in part, to the surprising brain penetration capacity of the compounds. Those CNS cancers can include any, including those described herein. The cancers can be RAS related in some embodiments. The cancers can be primary and/or secondary CNS cancers, including those described herein. The compounds can serve to prevent or reduce metastatic spread via the CNS.

What is claimed is:

1. A compound selected from:

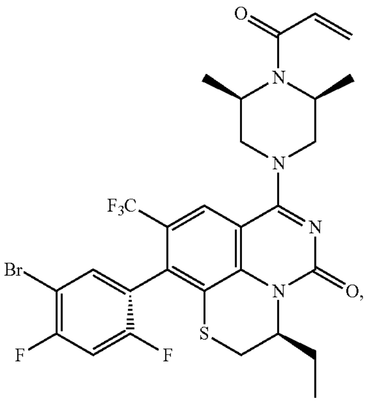

(3*S*, 10*R*)-7-((3*S*, 5*R*)-4-acryloyl-3,5-dimethylpiperazin-1-yl)-10-(5-bromo-2,4-difluorophenyl)-3-ethyl-9-(trifluoromethyl)-2,3-dihydro-5H-[1,4]thiazino[2,3,4-ij]quinazolin-5-one -continued

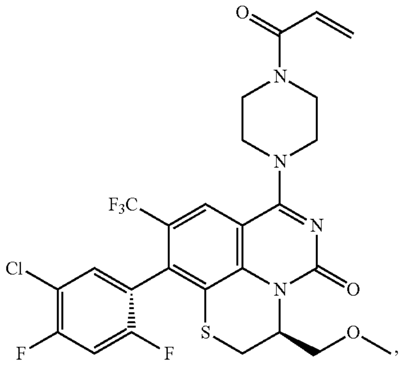

(3*S*, 10*R*)-7-(4-acryloylpiperazin-1-yl)-10-(5-chloro-2,4-difluorophenyl)-3-(methoxymethyl)-9-(trifluoromethyl)-2,3-dihydro-5H-[1,4]thiazino[2,3,4-ij]quinazolin-5-one -continued

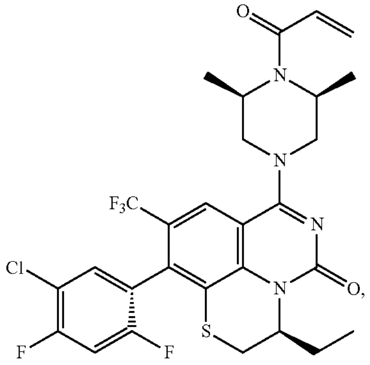

(3*S*, 10*R*)-7-((3*S*, 5*R*)-4-acryloyl-3,5-dimethylpiperazin-1-yl)-10-(5-chloro-2,4-difluorophenyl)-3-ethyl-9-(trifluoromethyl)-2,3-dihydro-5H-[1,4]thiazino[2,3,4-ij]quinazolin-5-one

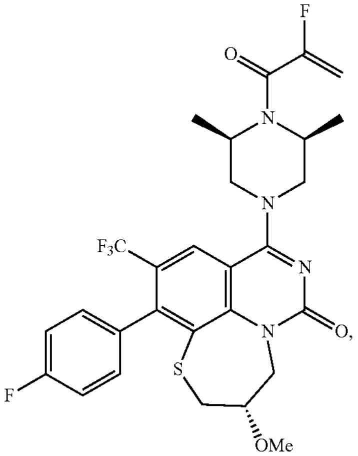

(*S*)-8-((3*S*, 5*R*)-4-(2-fluoroacryloyl-3,5-dimethylpiperazin-1-yl)-11-(4-fluorophenyl)-3-methoxy-10-(trifluoromethyl)-3,4-dihydro-2H,6H-[1,4]thiazino[2,3,4-ij]quinazolin-6-one

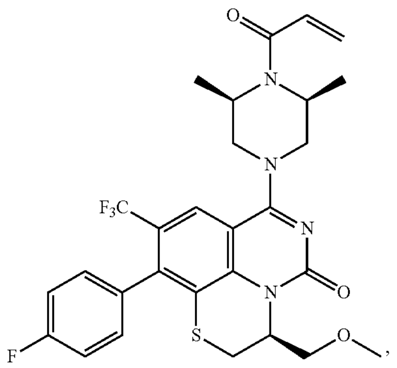

(*S*)-7-((3*S*, 5*R*)-4-acryloyl-3,5-dimethylpiperazin-1-yl)-10-(4-fluorophenyl)-3-methoxymethyl-9-(trifluoromethyl)-2,3-dihydro-5H-[1,4]thiazino[2,3,4-ij]quinazolin-5-one -continued

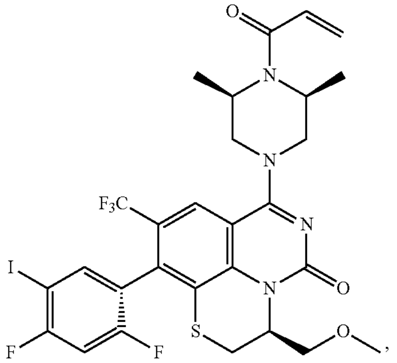

(3*S*, 10*R*)-7-((3*S*, 5*R*)-4-acryloyl-3,5-dimethylpiperazin-1-yl)-10-(2,4-difluoro-5-iodophenyl)-3-methoxymethyl-9-(trifluoromethyl)-2,3-dihydro-5H-[1,4]thiazino[2,3,4-ij]quinazolin-5-one

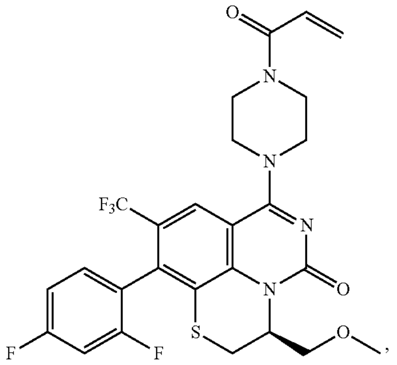

(3*S*)-7-(4-acryloylpiperazin-1-yl)-10-(2,4-difluorophenyl)-3-(methoxymethyl)-9-(trifluoromethyl)-2,3-dihydro-5H-[1,4]thiazino[2,3,4-ij]quinazolin-5-one

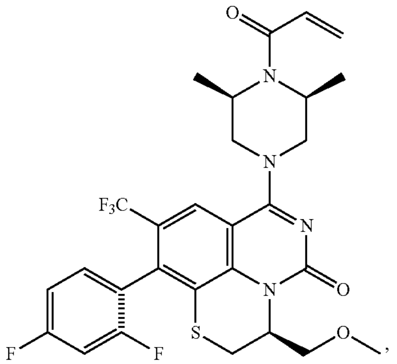

(3*S*, 10*R*)-7-((3*S*, 5*R*)-4-acryloyl-3,5-dimethylpiperazin-1-yl)-10-(2,4-difluorophenyl)-3-(methoxymethyl)-9-(trifluoromethyl)-2,3-dihydro-5H-[1,4]thiazino[2,3,4-ij]quinazolin-5-one -continued

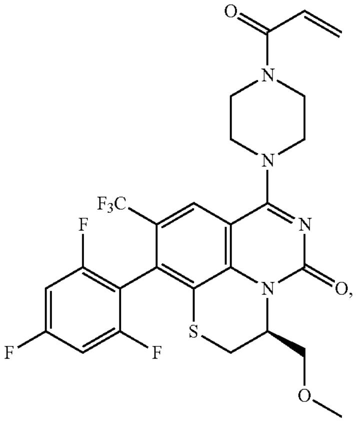

(*S*)-7-(4-acryloylpiperazin-1-yl)-3-(methoxymethyl)-9-(trifluoromethyl)-10-(2,4,6-trifluorophenyl)-2,3-dihydro-5H-[1,4]thiazino[2,3,4-ij]quinazolin-5-one

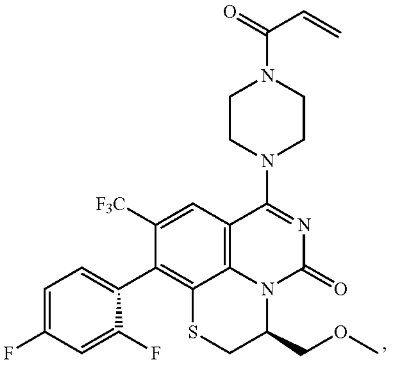

(3*S*, 10*R*)-7-(4-acryloylpiperazin-1-yl)-10-(2,4-difluorophenyl)-3-(methoxymethyl)-9-(trifluoromethyl)-2,3-dihydro-5H-[1,4]thiazino[2,3,4-ij]quinazolin-5-one

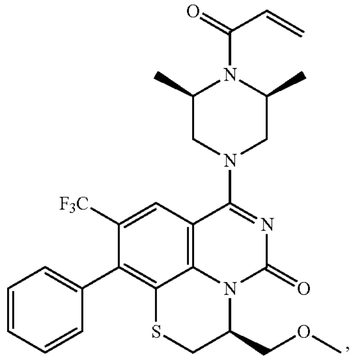

(*S*)-7-((3*S*,5*R*)-4-acryloyl-3,5-dimethylpiperazin-1-yl)-3-(methoxymethyl)-10-phenyl-9-(trifluoromethyl)-2,3-dihydro-5H-[1,4]thiazino[2,3,4-ij]quinazolin-5-one -continued

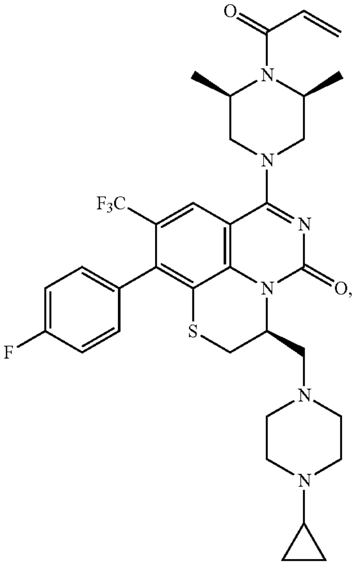

(*S*)-7-((3*S*,5*R*)-4-acryloyl-3,5-dimethylpiperazin-1-yl)-3-((4-cyclopropylpiperazin-1-yl)methyl)-10-(4-fluorophenyl)-9-(trifluoromethyl)-2,3-dihydro-5H-[1,4]thiazino[2,3,4-ij]quinazolin-5-one

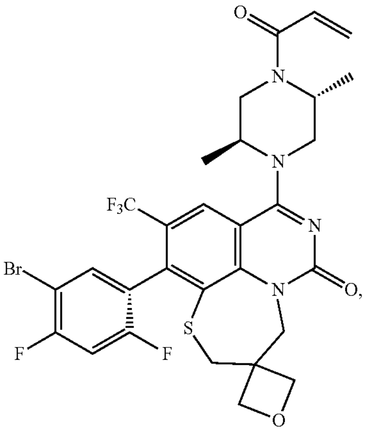

(*R*)-8′-((2*S*, 5*R*)-4-acryloyl-2,5-dimethylpiperazin-1-yl)-11′-(5-bromo-2,4-difluorophenyl)-10′-(trifluoromethyl)-2′H,4′H,6′H-spiro[oxetane-3,3′-[1,4]thiazepino[2,3,4-ij]quinazolin-6′-one

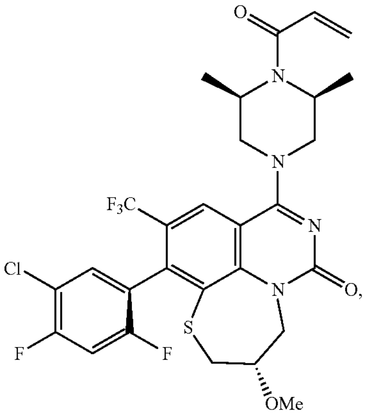

(3*S*, 11*S*)-8-((3*S*, 5*R*)-4-acryloyl-3,5-dimethylpiperazin-1-yl)-11-(5-chloro-2,4-difluorophenyl)-3-methoxy-10-(trifluoromethyl)-3,4-dihydro-2H,6H-[1,4]thiazepino[2,3,4-ij]quinazolin-6-one -continued

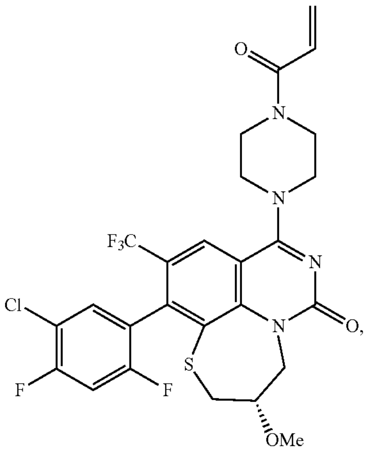

(*S*)-8-(4-acryloylpiperazin-1-yl)-11-(3-chloro-4-fluorophenyl)-3-methoxy-10-(trifluoromethyl)-3,4-dihydro-2H,6H-[1,4]thiazepino[2,3,4-ij]quinazolin-6-one

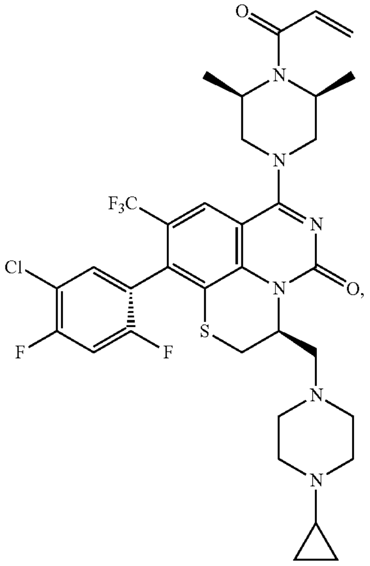

(3*S*, 10*R*)-7-((3*S*,5*R*)-4-acryloyl-3,5-dimethylpiperazin-1-yl)-10-(5-chloro-2,4-difluorophenyl)-3-((4-cyclopropylpiperazin-1-yl)methyl)-9-(trifluoromethyl)-2,3-dihydro-5H-[1,4]thiazino[2,3,4-ij]quinazolin-5-one

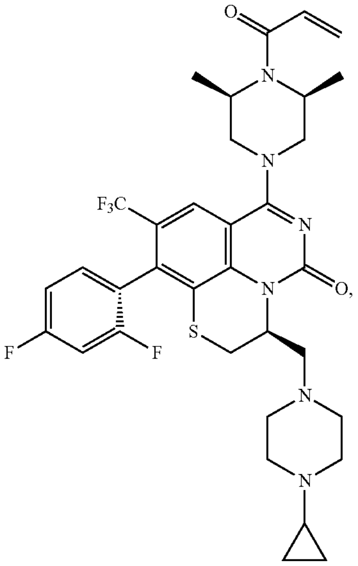

(3*S*, 10*R*)-7-((3*S*,5*R*)-4-acryloyl-3,5-dimethylpiperazin-1-yl)-3-((4-cyclopropylpiperazin-1-yl)methyl)-10-(2,4-difluorophenyl)-9-(trifluoromethyl)-2,3-dihydro-5H-[1,4]thiazino[2,3,4-ij]quinazolin-5-one

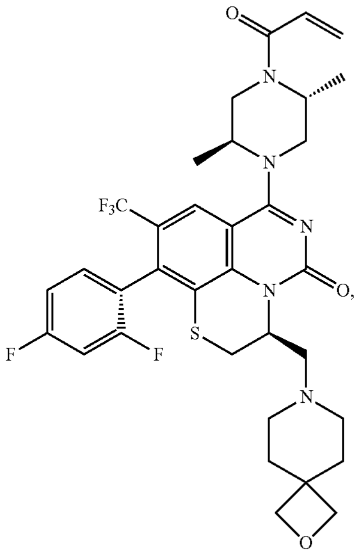

(3*S*, 10*R*)-3-((2-oxa-7-azaspiro[3.5]nonan-7-yl)methyl-7-((2*S*, 5*R*)-4-acryloyl-2,5-dimethylpiperazin-1-yl)-10-(2,4-difluorophenyl)-9-(trifluoromethyl)-2,3-dihydro-5H-[1,4]thiazino[2,3,4-ij]quinazolin-5-one -continued

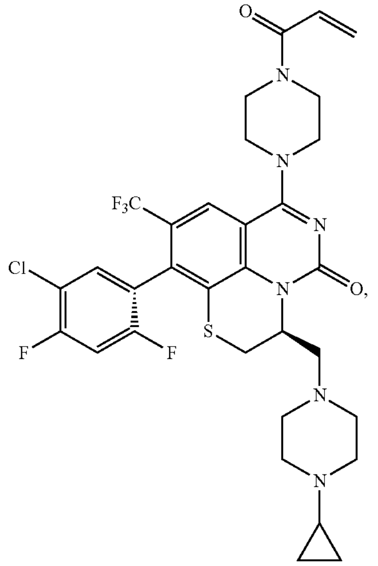

(3*S*, 10*R*)-7-(4-acryloylpiperazin-1-yl)-10-(5-chloro-2,4-difluorophenyl)-3-((4-cyclopropylpiperazin-1-yl)methyl)-9-(trifluoromethyl)-2,3-dihydro-5H-[1,4]thiazino[2,3,4-ij]quinazolin-5-one

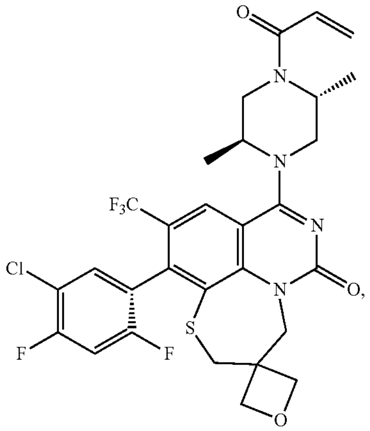

(*R*)-8′-((2*S*, 5*R*)-4-acryloyl-2,5-dimethylpiperazin-1-yl)-11′-(5-chloro-2,4-difluorophenyl)-10′-(trifluoromethyl)-2′H,4′H,6′H-spiro[oxetane-3,3′-[1,4]thiazepino[2,3,4-ij]quinazolin-6′-one -continued

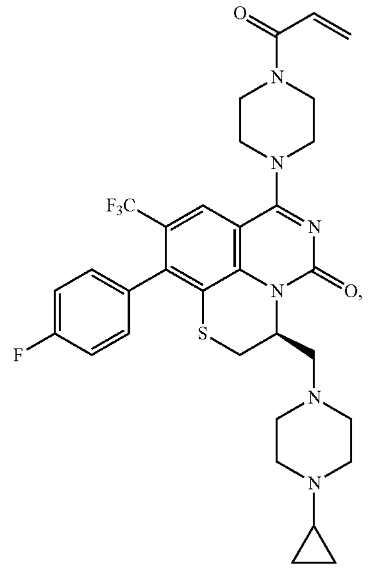

(*S*)-7-(4-acryloylpiperazin-1-yl)-3-((4-cyclopropylpiperazin-1-yl)methyl)-10-(4-fluorophenyl)-9-(trifluoromethyl)-2,3-dihydro-5H-[1,4]thiazino[2,3,4-ij]quinazolin-5-one

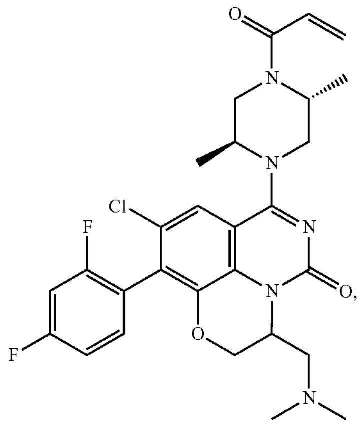

7-((2*S*, 5*R*)-4-acryloyl-2,5-dimethylpiperazin-1-yl)-9-chloro-10-(2,4-difluorophenyl)-3-((dimethylamino)methyl)-2,3-dihydro-5H-[1,4]oxazino[2,3,4-ij]quinazolin-6′-one

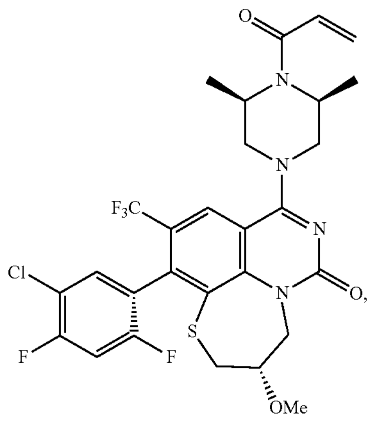

(3*S*, 11*R*)-8-((3*S*, 5*R*)-4-acryloyl-3,5-dimethylpiperazin-1-yl)-11-(5-chloro-2,4-difluorophenyl)-3-methoxy-10-(trifluoromethyl)-3,4-dihydro-2H,6H-[1,4]thiazepino[2,3,4-ij]quinazolin-6-one -continued

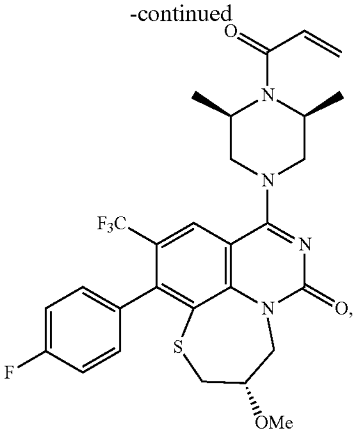

(*S*)-8-((3*S*, 5*R*)-4-acryloyl-3,5-dimethylpiperazin-1-yl)-11-(4-fluorophenyl)-3-methoxy-10-(trifluoromethyl)-3,4-dihydro-2H,6H-[1,4]thiazepino[2,3,4-ij]quinazolin-6-one

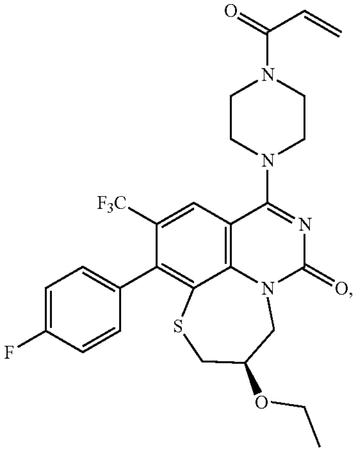

(*R*)-8-(-4-acryloylpiperazin-1-yl)-3-ethoxy-11-(4-fluorophenyl)-10-(trifluoromethyl)-3,4-dihydro-2H,6H-[1,4]thiazepino[2,3,4-ij]quinazolin-6-one

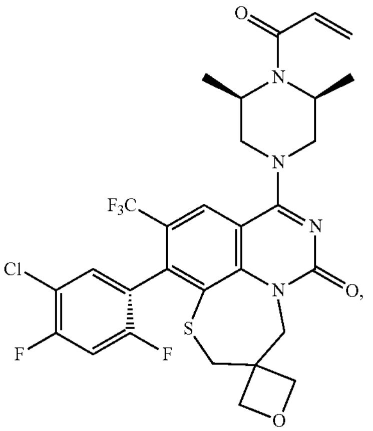

(*R*)-8′-((3*S*, 5*R*)-4-acryloylpiperazin-1-yl)-3,5-dimethylpiperazin-1-yl)-11′-(5-chloro-2,4-difluorophenyl)-10′-(trifluoromethyl)-2′H,4′H,6′H-spiro[oxetane-3,3′-[1,4]thiazepino[2,3,4-ij]quinazolin-6-one -continued

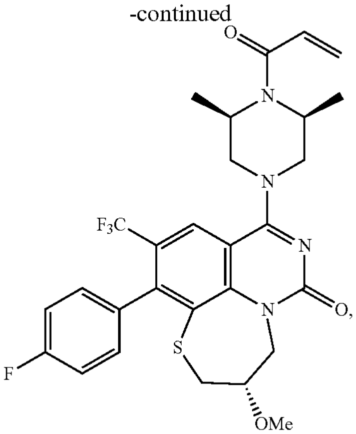

and (*S*)-8-(4-acryloylpiperazin-1-yl)-11-(4-fluorophenyl)-3-methoxy-10-(trifluoromethyl)-3,4-dihydro-2H,6H-[1,4]thiazepino[2,3,4-ij]quinazolin-6-one

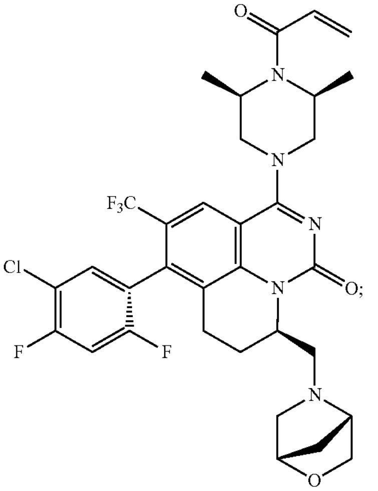

(3*S*, 10*R*)-3-(((1*S*, 4*S*)-2-oxa-5-azabicyclo[2.2.1]heptan-5-yl)methyl)-7-((3*S*, 5*R*)-4-acryloyl-3,5-dimethylpiperazin-1-yl)-10-(5-chloro-2,4-difluorophenyl)-9-(trifluoromethyl)-2,3-dihydro-5H-[1,4]thiazepino[2,3,4-ij]quinazolin-6-one or a pharmaceutically acceptable salt thereof.

2. The compound of claim 1 having the structure:

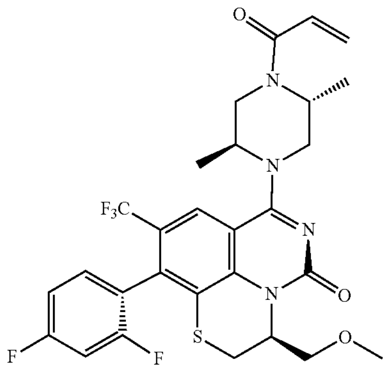

(3S,10R)-7-((2S,5R)-4-acryloyl-2,5-dimethylpiperazin-1-yl)-10-(2,4-difluorophenyl)-3-(methoxymethyl)-9-(trifluoromethyl)-2,3-dihydro-5H-[1,4]thiazino[2,3,4-ij]quinazolin-5-one, or a pharmaceutically acceptable salt thereof.

3. The compound of claim 1 having the structure:

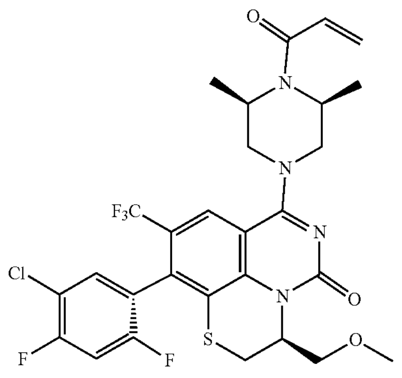

(3S,10R)-7-((3S,5R)-4-acryloyl-3,5-dimethylpiperazin-1-yl)-10-(5-chloro-2,4-difluorophenyl)-3-(methoxymethyl)-9-(trifluoromethyl)-2,3-dihydro-5H-[1,4]thiazino[2,3,4-ij]quinazolin-5-one, or a pharmaceutically acceptable salt thereof.

4. The compound of claim 1 having the structure:

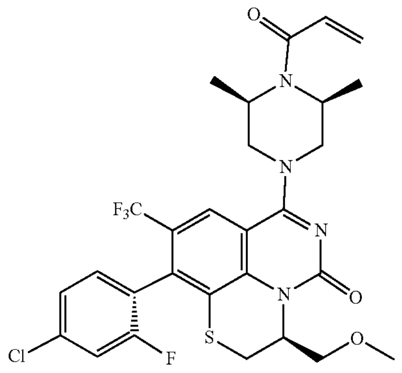

(3S,10R)-7-((3S,5R)-4-acryloyl-3,5-dimethylpiperazin-1-yl)-10-(4-chloro-2-fluorophenyl)-3-(methoxymethyl)-9-(trifluoromethyl)-2,3-dihydro-5H-[1,4]thiazino[2,3,4-ij]quinazolin-5-one, or a pharmaceutically acceptable salt thereof.

5. The compound of claim 1 having the structure:

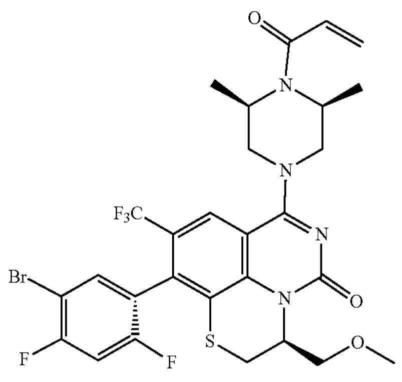

(3S,10R)-7-((3S,5R)-4-acryloyl-3,5-dimethylpiperazin-1-yl)-10-(5-bromo-2,4-difluorophenyl)-3-(methoxymethyl)-9-(trifluoromethyl)-2,3-dihydro-5H-[1,4]thiazino[2,3,4-ij]quinazolin-5-one, or a pharmaceutically acceptable salt thereof.

6. The compound of claim 1 having the structure:

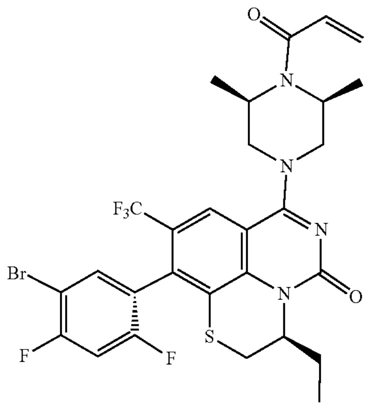

(3S,10R)-7-((3S,5R)-4-acryloyl-3,5-dimethylpiperazin-1-yl)-10-(5-bromo-2,4-difluorophenyl)-3-ethyl-9-(trifluoromethyl)-2,3-dihydro-5H-[1,4]thiazino[2,3,4-ij]quinazolin-5-one, or a pharmaceutically acceptable salt thereof.

7. The compound of claim 1 having the structure:

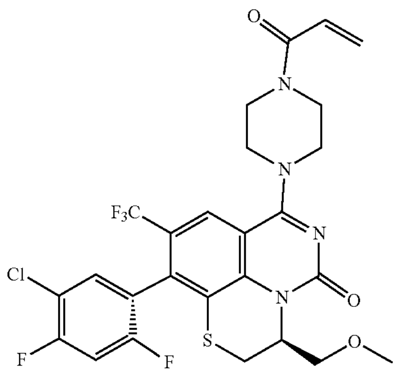

(3S,10R)-7-(4-acryloylpiperazin-1-yl)-10-(5-chloro-2,4-difluorophenyl)-3-(methoxymethyl)-9-(trifluoromethyl)-2,3-dihydro-5H-[1,4]thiazino[2,3,4-ij]quinazolin-5-one, or a pharmaceutically acceptable salt thereof.

8. The compound of claim 1 having the structure:

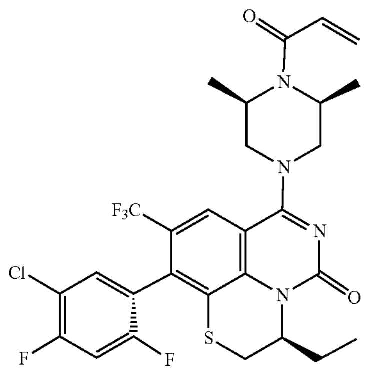

(3S,10R)-7-((3S,5R)-4-acryloyl-3,5-dimethylpiperazin-1-yl)-10-(5-chloro-2,4-difluorophenyl)-3-ethyl-9-(trifluoromethyl)-2,3-dihydro-5H-[1,4]thiazino[2,3,4-ij]quinazolin-5-one, or a pharmaceutically acceptable salt thereof.

9. The compound of claim 1 having the structure:

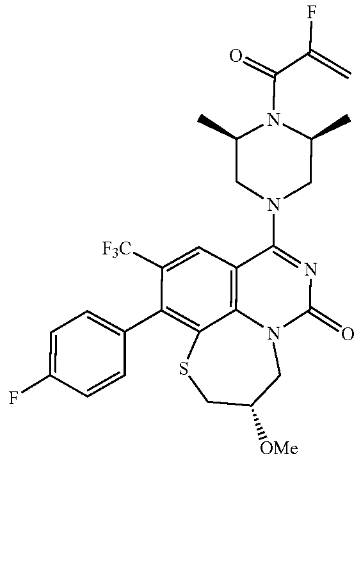 [SMILES: C=C(F)C(=O)N1[C@H](C)CN(c2nc(=O)n3c4c(c(-c5ccc(F)cc5)c(C(F)(F)F)cc24)SC[C@@H](OC)C3)C[C@@H]1C]

(S)-8-((3S,5R)-4-(2-fluoroacryloyl)-3,5-dimethylpiperazin-1-yl)-11-(4-fluorophenyl)-3-methoxy-10-(trifluoromethyl)-3,4-dihydro-2H,6H-[1,4]thiazepino[2,3,4-ij]quinazolin-6-one, or a pharmaceutically acceptable salt thereof.

10. The compound of claim 1 having the structure:

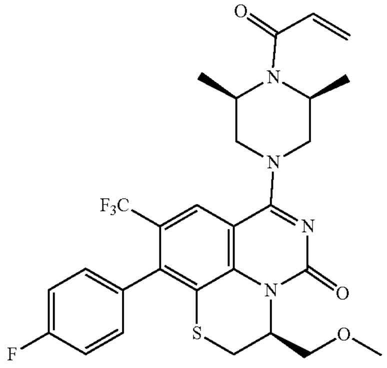 [SMILES: C=CC(=O)N1[C@H](C)CN(c2nc(=O)n3c4c(c(-c5ccc(F)cc5)c(C(F)(F)F)cc24)SC[C@@H]3COC)C[C@@H]1C]

(S)-7-((3S,5R)-4-acryloyl-3,5-dimethylpiperazin-1-yl)-10-(4-fluorophenyl)-3-(methoxymethyl)-9-(trifluoromethyl)-2,3-dihydro-5H-[1,4]thiazino[2,3,4-ij]quinazolin-5-one, or a pharmaceutically acceptable salt thereof.

11. The compound of claim 1 having the structure:

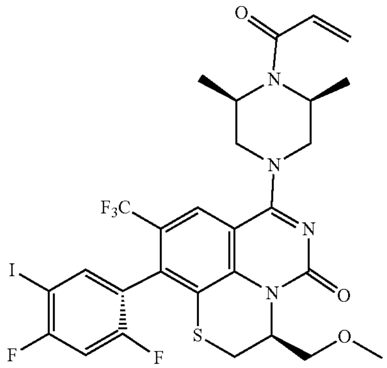

(3S,10R)-7-((3S,5R)-4-acryloyl-3,5-dimethylpiperazin-1-yl)-10-(2,4-difluoro-5-iodophenyl)-3-(methoxymethyl)-9-(trifluoromethyl)-2,3-dihydro-5H-[1,4]thiazino[2,3,4-ij]quinazolin-5-one, or a pharmaceutically acceptable salt thereof.

12. The compound of claim 1 having the structure:

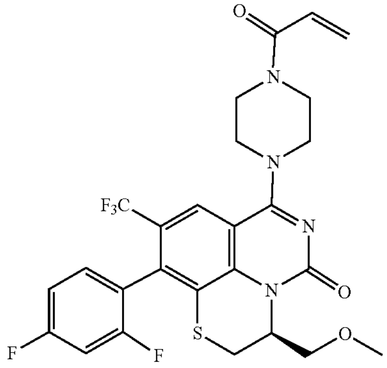 [SMILES: C=CC(=O)N1CCN(c2nc(=O)n3c4c(c(-c5ccc(F)cc5F)c(C(F)(F)F)cc24)SC[C@@H]3COC)CC1]

(3S)-7-(4-acryloylpiperazin-1-yl)-10-(2,4-difluorophenyl)-3-(methoxymethyl)-9-(trifluoromethyl)-2,3-dihydro-5H-[1,4]thiazino[2,3,4-ij]quinazolin-5-one, or a pharmaceutically acceptable salt thereof.

13. The compound of claim 1 having the structure:

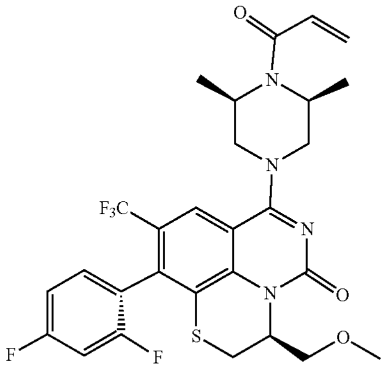

(3S,10R)-7-((3S,5R)-4-acryloyl-3,5-dimethylpiperazin-1-yl)-10-(2,4-difluorophenyl)-3-(methoxymethyl)-9-(trifluoromethyl)-2,3-dihydro-5H-[1,4]thiazino[2,3,4-ij]quinazolin-5-one, or a pharmaceutically acceptable salt thereof.

14. The compound of claim 1 having the structure:

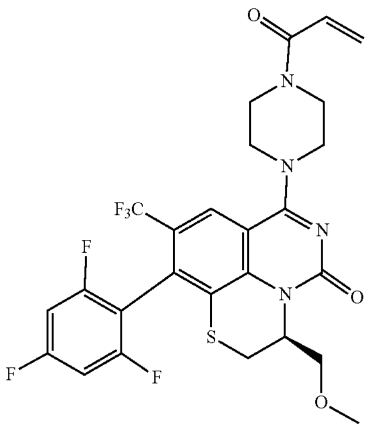 [SMILES: C=CC(=O)N1CCN(c2nc(=O)n3c4c(c(-c5c(F)cc(F)cc5F)c(C(F)(F)F)cc24)SC[C@@H]3COC)CC1]

(S)-7-(4-acryloylpiperazin-1-yl)-3-(methoxymethyl)-9-(trifluoromethyl)-10-(2,4,6-trifluorophenyl)-2,3-dihydro-5H-[1,4]thiazino[2,3,4-ij]quinazolin-5-one, or a pharmaceutically acceptable salt thereof.

15. The compound of claim 1 having the structure:

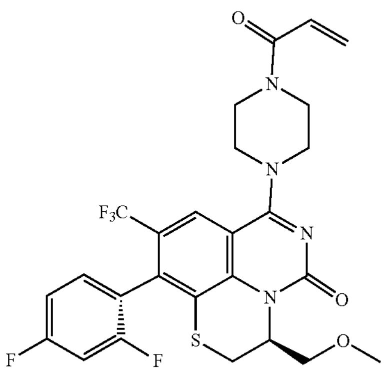

(3S,10R)-7-(4-acryloylpiperazin-1-yl)-10-(2,4-difluorophenyl)-3-(methoxymethyl)-9-(trifluoromethyl)-2,3-dihydro-5H-[1,4]thiazino[2,3,4-ij]quinazolin-5-one, or a pharmaceutically acceptable salt thereof.

16. The compound of claim 1 having the structure:

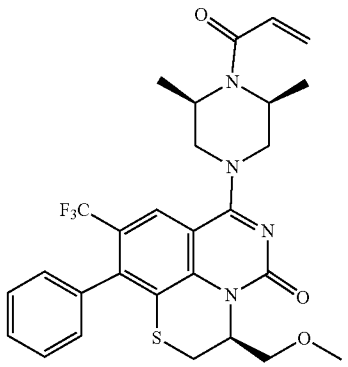 [SMILES: C=CC(=O)N1[C@H](C)CN(c2nc(=O)n3c4c(c(-c5ccccc5)c(C(F)(F)F)cc24)SC[C@@H]3COC)C[C@@H]1C]

(S)-7-((3S,5R)-4-acryloyl-3,5-dimethylpiperazin-1-yl)-3-(methoxymethyl)-10-phenyl-9-(trifluoromethyl)-2,3-dihydro-5H-[1,4]thiazino[2,3,4-ij]quinazolin-5-one, or a pharmaceutically acceptable salt thereof.

17. The compound of claim 1 having the structure:

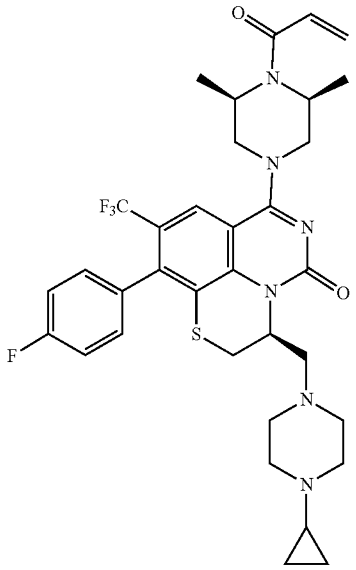

(S)-7-((3S,5R)-4-acryloyl-3,5-dimethylpiperazin-1-yl)-3-((4-cyclopropylpiperazin-1-yl)methyl)-10-(4-fluorophenyl)-9-(trifluoromethyl)-2,3-dihydro-5H-[1,4]thiazino[2,3,4-ij]quinazolin-5-one, or a pharmaceutically acceptable salt thereof.

18. The compound of claim 1 having the structure:

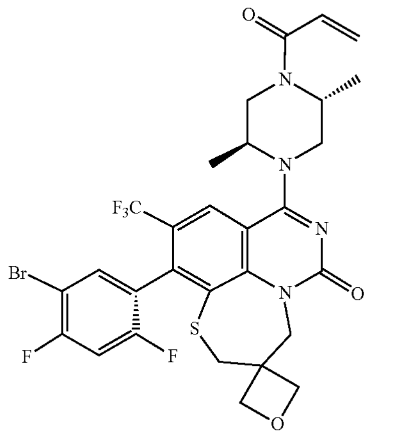

(R)-8'-((2S,5R)-4-acryloyl-2,5-dimethylpiperazin-1-yl)-11'-(5-bromo-2,4-difluorophenyl)-10'-(trifluoromethyl)-2'H,4'H,6'H-spiro[oxetane-3,3'-[1,4]thiazepino[2,3,4-ij]quinazolin]-6'-one, or a pharmaceutically acceptable salt thereof.

19. The compound of claim 1 having the structure:

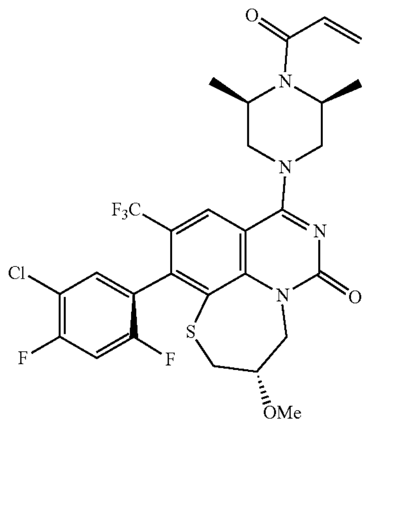

(3S,11S)-8-((3S,5R)-4-acryloyl-3,5-dimethylpiperazin-1-yl)-11-(5-chloro-2,4-difluorophenyl)-3-methoxy-10-(trifluoromethyl)-3,4-dihydro-2H,6H-[1,4]thiazepino[2,3,4-ij]quinazolin-6-one, or a pharmaceutically acceptable salt thereof.

20. The compound of claim 1 having the structure:

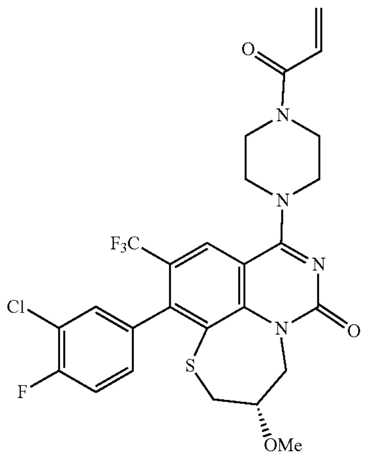 [SMILES: C=CC(=O)N1CCN(c2nc(=O)n3c4c(c(-c5ccc(F)c(Cl)c5)c(C(F)(F)F)cc24)SC[C@@H](OC)C3)CC1]

(S)-8-(4-acryloylpiperazin-1-yl)-11-(3-chloro-4-fluorophenyl)-3-methoxy-10-(trifluoromethyl)-3,4-dihydro-2H,6H-[1,4]thiazepino[2,3,4-ij]quinazolin-6-one, or a pharmaceutically acceptable salt thereof.

21. The compound of claim 1 having the structure:

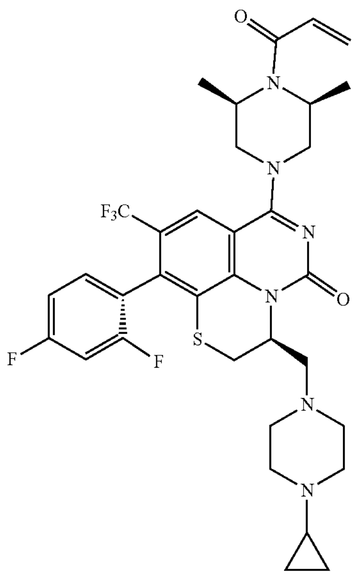

(3S,10R)-7-((3S,5R)-4-acryloyl-3,5-dimethylpiperazin-1-yl)-3-((4-cyclopropylpiperazin-1-yl)methyl)-10-(2,4-difluorophenyl)-9-(trifluoromethyl)-2,3-dihydro-5H-[1,4]thiazino[2,3,4-ij]quinazolin-5-one, or a pharmaceutically acceptable salt thereof.

22. The compound of claim 1 having the structure:

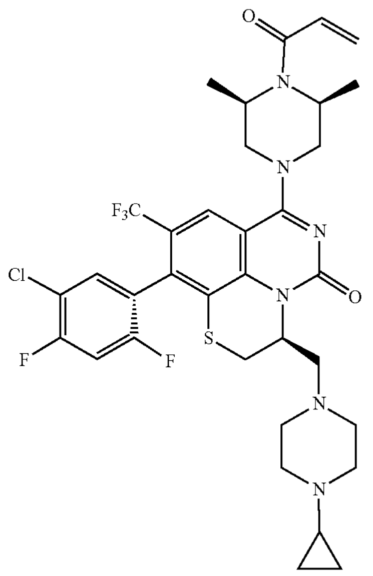

(3S,10R)-7-((3S,5R)-4-acryloyl-3,5-dimethylpiperazin-1-yl)-10-(5-chloro-2,4-difluorophenyl)-3-((4-cyclopropylpiperazin-1-yl)methyl)-9-(trifluoromethyl)-2,3-dihydro-5H-[1,4]thiazino[2,3,4-ij]quinazolin-5-one, or a pharmaceutically acceptable salt thereof.

23. The compound of claim 1 having the structure:

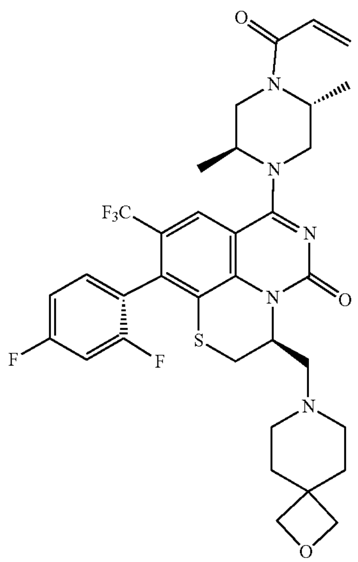

(3S,10R)-3-((2-oxa-7-azaspiro[3.5]nonan-7-yl)methyl)-7-((2S,5R)-4-acryloyl-2,5-dimethylpiperazin-1-yl)-10-(2,4-difluorophenyl)-9-(trifluoromethyl)-2,3-dihydro-5H-[1,4]thiazino[2,3,4-ij]quinazolin-5-one, or a pharmaceutically acceptable salt thereof.

24. The compound of claim 1 having the structure:

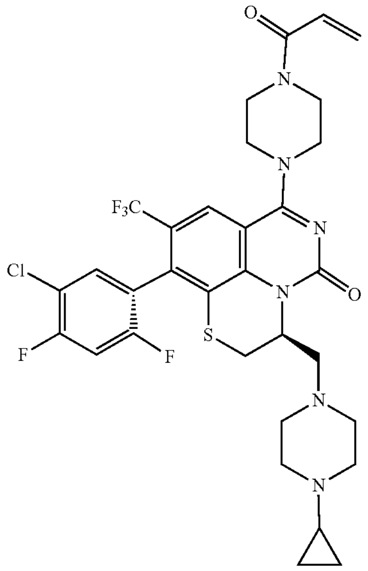

(3S,1R)-7-(4-acryloylpiperazin-1-yl)-10-(5-chloro-2,4-difluorophenyl)-3-((4-cyclopropylpiperazin-1-yl)methyl)-9-(trifluoromethyl)-2,3-dihydro-5H-[1,4]thiazino[2,3,4-ij]quinazolin-5-one, or a pharmaceutically acceptable salt thereof.

25. The compound of claim 1 having the structure:

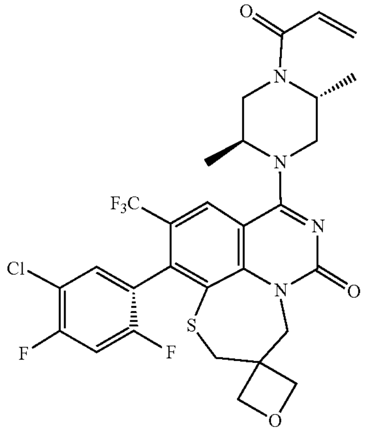

(R)-8'-((2S,5R)-4-acryloyl-2,5-dimethylpiperazin-1-yl)-11'-(5-chloro-2,4-difluorophenyl)-10'-(trifluoromethyl)-2'H,4'H,6'H-spiro[oxetane-3,3'-[1,4]thiazepino[2,3,4-ij]quinazolin]-6'-one, or a pharmaceutically acceptable salt thereof.

26. The compound of claim 1 having the structure:

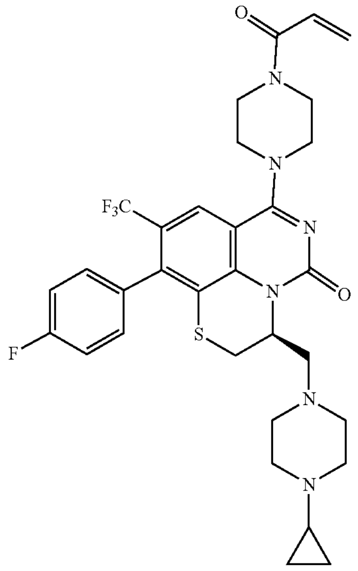 [SMILES: C=CC(=O)N1CCN(c2nc(=O)n3c4c(c(-c5ccc(F)cc5)c(C(F)(F)F)cc24)SC[C@@H]3CN2CCN(C3CC3)CC2)CC1]

(S)-7-(4-acryloylpiperazin-1-yl)-3-((4-cyclopropylpiperazin-1-yl)methyl)-10-(4-fluorophenyl)-9-(trifluoromethyl)-2,3-dihydro-5H-[1,4]thiazino[2,3,4-ij]quinazolin-5-one, or a pharmaceutically acceptable salt thereof.

27. The compound of claim 1 having the structure:

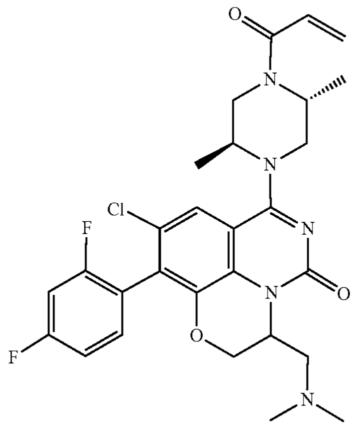 [SMILES: C=CC(=O)N1C[C@H](C)N(c2nc(=O)n3c4c(c(-c5ccc(F)cc5F)c(Cl)cc24)OCC3CN(C)C)C[C@H]1C]

7-((2S,5R)-4-acryloyl-2,5-dimethylpiperazin-1-yl)-9-chloro-10-(2,4-difluorophenyl)-3-((dimethylamino)methyl)-2,3-dihydro-5H-[1,4]oxazino[2,3,4-ij]quinazolin-5-one, or a pharmaceutically acceptable salt thereof.

28. The compound of claim 1 having the structure:

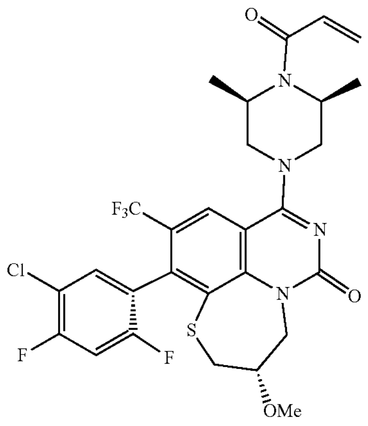

(3S,11R)-8-((3S,5R)-4-acryloyl-3,5-dimethylpiperazin-1-yl)-11-(5-chloro-2,4-difluorophenyl)-3-methoxy-10-(trifluoromethyl)-3,4-dihydro-2H,6H-[1,4]thiazepino[2,3,4-ij]quinazolin-6-one, or a pharmaceutically acceptable salt thereof.

29. The compound of claim 1 having the structure:

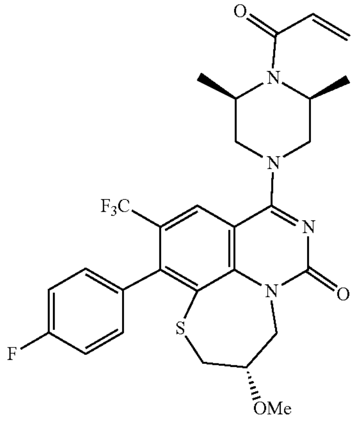 [SMILES: C=CC(=O)N1[C@H](C)CN(c2nc(=O)n3c4c(c(-c5ccc(F)cc5)c(C(F)(F)F)cc24)SC[C@@H](OC)C3)C[C@@H]1C]

(S)-8-((3S,5R)-4-acryloyl-3,5-dimethylpiperazin-1-yl)-11-(4-fluorophenyl)-3-methoxy-10-(trifluoromethyl)-3,4-dihydro-2H,6H-[1,4]thiazepino[2,3,4-ij]quinazolin-6-one, or a pharmaceutically acceptable salt thereof.

30. The compound of claim 1 having the structure:
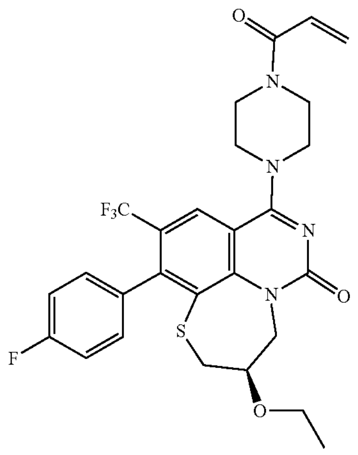 [SMILES: C=CC(=O)N1CCN(c2nc(=O)n3c4c(c(-c5ccc(F)cc5)c(C(F)(F)F)cc24)SC[C@H](OCC)C3)CC1]
(R)-8-(4-acryloylpiperazin-1-yl)-3-ethoxy-11-(4-fluorophenyl)-10-(trifluoromethyl)-3,4-dihydro-2H,6H-[1,4]thiazepino[2,3,4-ij]quinazolin-6-one,
or a pharmaceutically acceptable salt thereof.
* * * * *